(12) United States Patent
Wiles et al.

(10) Patent No.: US 12,091,402 B2
(45) Date of Patent: Sep. 17, 2024

(54) POTENT ASGPR-BINDING COMPOUNDS FOR THE DEGRADATION OF IMMUNOGLOBULINS AND OTHER PROTEINS

(71) Applicant: Avilar Therapeutics, Inc., Waltham, MA (US)

(72) Inventors: Jason Allan Wiles, Madison, CT (US); Srinivasa Karra, Pembrooke, MA (US); Mark George Saulnier, Higganum, CT (US); Jesse Jingyang Chen, Lexington, MA (US); Kevin Tyler Sprott, Needham, MA (US); Soumya Ray, Quincy, MA (US)

(73) Assignee: Avilar Therapeutics, Inc., Waltham, MA (US)

( * ) Notice: Subject to any disclaimer, the term of this patent is extended or adjusted under 35 U.S.C. 154(b) by 0 days.

(21) Appl. No.: 18/220,737

(22) Filed: Jul. 11, 2023

(65) Prior Publication Data
US 2024/0101539 A1    Mar. 28, 2024

Related U.S. Application Data

(63) Continuation of application No. PCT/US2022/027513, filed on May 3, 2022.

(60) Provisional application No. 63/331,592, filed on Apr. 15, 2022, provisional application No. 63/293,447, filed on Dec. 23, 2021, provisional application No. 63/228,067, filed on Jul. 31, 2021, provisional application No. 63/183,450, filed on May 3, 2021.

(51) Int. Cl.
| | | |
|---|---|---|
| C07D 405/12 | (2006.01) | |
| C07D 405/14 | (2006.01) | |
| C07D 417/12 | (2006.01) | |
| C07H 17/00 | (2006.01) | |
| C07H 17/02 | (2006.01) | |

(52) U.S. Cl.
CPC ......... *C07D 405/12* (2013.01); *C07D 405/14* (2013.01); *C07D 417/12* (2013.01); *C07H 17/00* (2013.01); *C07H 17/02* (2013.01)

(58) Field of Classification Search
CPC .............................. C07D 405/12; C07D 405/14
See application file for complete search history.

(56) References Cited

U.S. PATENT DOCUMENTS

| | | |
|---|---|---|
| 4,344,894 A | 8/1982 | Laidler et al. |
| 5,047,518 A | 9/1991 | Furneaux et al. |
| 5,554,386 A | 9/1996 | Groman et al. |
| 5,571,796 A | 11/1996 | Srivastava |
| 5,624,896 A | 4/1997 | Axworthy et al. |
| 5,958,408 A | 9/1999 | Griffiths et al. |
| 5,985,826 A | 11/1999 | Theodore et al. |
| 6,172,045 B1 | 1/2001 | Theodore et al. |
| 7,737,287 B2 | 6/2010 | Meutermans et al. |
| 7,989,422 B2 | 8/2011 | Meutermans et al. |
| 9,340,553 B2 | 5/2016 | Liras et al. |
| 9,617,293 B2 | 4/2017 | Liras et al. |
| 10,039,778 B2 | 8/2018 | Liras et al. |
| 10,376,531 B2 | 8/2019 | Liras et al. |
| 10,813,942 B2 | 10/2020 | Liras et al. |
| 10,821,157 B2 | 11/2020 | Hubbell et al. |
| 11,819,551 B2 | 11/2023 | Saulier et al. |
| 2009/0317381 A1 | 12/2009 | Plaut et al. |
| 2014/0356322 A1 | 12/2014 | Crews et al. |
| 2015/0299313 A1 | 10/2015 | Igawa et al. |
| 2016/0058872 A1 | 3/2016 | Crew et al. |
| 2016/0082112 A1 | 3/2016 | Spiegel et al. |
| 2016/0136299 A1 | 5/2016 | Avila et al. |
| 2017/0137801 A1 | 5/2017 | Liras et al. |
| 2019/0321382 A1 | 10/2019 | Liras et al. |
| 2023/0083388 A1 | 3/2023 | Spiegel et al. |
| 2023/0087994 A1 | 3/2023 | Spiegel et al. |
| 2023/0090282 A1 | 3/2023 | Spiegel et al. |
| 2023/0097887 A1 | 3/2023 | Spiegel et al. |
| 2024/0050578 A1 | 2/2024 | Spiegel et al. |

FOREIGN PATENT DOCUMENTS

| | | |
|---|---|---|
| EP | 2191849 A1 | 6/2010 |
| WO | WO 89/10140 A1 | 11/1989 |
| WO | WO 1993/25240 A2 | 12/1993 |
| WO | WO 2002/032915 A1 | 4/2002 |
| WO | WO 2003/082846 A1 | 10/2003 |
| WO | WO 2011/036457 A1 | 3/2011 |
| WO | WO 2014/025805 A1 | 2/2014 |
| WO | WO 2015/140648 A2 | 9/2015 |
| WO | WO 2015/143091 A2 | 9/2015 |
| WO | WO 2015/160845 A1 | 10/2015 |
| WO | WO 2015/177668 A1 | 11/2015 |

(Continued)

OTHER PUBLICATIONS

U.S. Pat. No. 11/819,551 B2, U.S. Appl. No. 17/877,538, Saulnier et al., Nov. 21, 2023.
U.S. Appl. No. 18/220,708, filed Jul. 11, 2023, Saulnier et al.
U.S. Appl. No. 18/584,914, filed Feb. 22, 2024, Saulnier et al.
U.S. Appl. No. 18/590,713, filed Feb. 28, 2024, Wiles et al.
U.S. Appl. No. 18/586,086, filed Feb. 23, 2024, Wiles et al.
Baenziger, J. U. "Galactose and N-Acetylgalactosamine-Specific Endocytosis of Glycopeptides by Isolated Rat Hepatocytes" Cell, 22, 611-620, Nov. 1980.
Bagshawe, K.D. et al. Antibody directed enzyme prodrug therapy (ADEPT), Annals of Oncology 5: 879-891, Dec. 1994.
Banik, Steven M. et al. "Lysosome-targeting chimaeras for degradation of extracellular proteins"; Nature 584, Jul. 29, 2020, 291-297.

(Continued)

Primary Examiner — Jeffrey S Lundgren
Assistant Examiner — Chris E Simmons
(74) Attorney, Agent, or Firm — Knowles Intellectual Property Strategies, LLC

(57) ABSTRACT

Extracellular protein degraders and compositions are provided that have a potent asialoglycoprotein receptor (ASGPR) Binding Ligand bound to an Extracellular Protein Targeting Ligand for the selective degradation of the Target Extracellular Protein, for example immunoglobulin in vivo to treat disorders mediated by the extracellular protein.

29 Claims, 149 Drawing Sheets

Specification includes a Sequence Listing.

(56) References Cited

FOREIGN PATENT DOCUMENTS

| WO | WO 2015/179693 A1 | 11/2015 |
|---|---|---|
| WO | WO 2016/057769 A2 | 4/2016 |
| WO | WO 2017/083368 A1 | 5/2017 |
| WO | WO 2007/070947 A1 | 6/2017 |
| WO | WO 2017/212019 A1 | 12/2017 |
| WO | WO 2018/146199 A1 | 8/2018 |
| WO | WO 2018/223056 A1 | 12/2018 |
| WO | WO 2018/223073 A1 | 12/2018 |
| WO | WO 2018/223081 A1 | 12/2018 |
| WO | WO 2019/075357 A1 | 4/2019 |
| WO | WO 2019/199621 A1 | 10/2019 |
| WO | WO 2019/199634 A1 | 10/2019 |
| WO | WO 2020/132100 A1 | 6/2020 |
| WO | WO 2021/072269 A1 | 4/2021 |
| WO | WO 2021/142377 A2 | 7/2021 |
| WO | WO 2021/156792 A1 | 8/2021 |
| WO | WO 2021/219077 A1 | 11/2021 |
| WO | WO 2021/234459 A2 | 11/2021 |
| WO | WO 2021/263060 A1 | 12/2021 |
| WO | WO 2021/263061 A2 | 12/2021 |
| WO | WO 2022/084331 A2 | 4/2022 |

OTHER PUBLICATIONS

Banik, Steven M. et al. "Lysosome targeting chimaeras (LYTACs) for degradation of secreted and membrane proteins," Chemrxiv, Mar. 29, 2019.

Baynes, John W. et al. Effect of glycosylation on the in vivo circulating half-life of ribonuclease, The Journal of Biological Chemistry, vol. 251, No. 19, Issue of Oct. 10, pp. 6016-6024, 1976.

Bernini, Franco, et al. Lactosaminated fab fragments specific for low density lipoproteins/hepatocyte targeting and hypolipoproteinemic activity, Arteriosclerosis, vol. 8, No. 6, Nov./Dec. 1988.

Bernini, Franco, et al. Enhanced catabolism of low density lipoproteins in rat by lactosaminated fab fragment, The Journal of Biological Chemistry, vol. 261, No. 20, issue of Jul. 15, pp. 9294-9299, 1986.

Biessen, Erick A.L. et al. The cholesterol derivative of a triantennary galactoside with high affinity for the hepatic asialoglycoprotein receptor: a potent cholesterol lowering agent, J Med. Chem., 38, 1846-1852, 1995.

Biessen, Erick A.L. et al. Induction of hepatic uptake of lipoprotein(a) by cholesterol-derivatized cluster galactosides, Arterioscler Thromb Vasc Biol., vol. 16, No. 12, 1552-1558, Dec. 1996.

Biessen, Erick A.L. et al. Cholesterol derivative of a new triantennary cluster galactoside directs low- and high-density lipoproteins to the parenchymal liver cell, Biochem. J. 302, 283-289, 1994.

Biessen, Erick A.L. et al. Synthesis of cluster galactoside with high affinity for the hepatic asialoglycoprotein receptor, J. Med. Chem., 38, 1538-1546, 1995.

Bergeron, J. J. M. et al. "Subcellular Biochemistry, vol. 19, Endocytic Components: Identification and Characterization" ISBN 978-1-4615-3026-8, Springer Science, 1993.

Bider, M.D. et al., Ligand-induced endocytosis of the asialoglycoprotein receptor: evidence for heterogeneity in subunit oligomerization, FEBS Letters, 1998, 434, 37-41.

Blakey, D.C. Antibody-directed enzyme prodrug therapy (ADEPT) for treatment of major solid tumor disease, Biochemical Society Transactions Therapeutic Monoclonals, vol. 23, 1047-1050, Nov. 1, 1995.

Bijsterbosch, Martin K. et al. Enhanced Hepatic Update and Processing of Cholesterol Esters From Low Density Lipoprotein by Specific Lactosaminated Fab Fragments, Ateriosclerosis and Thrombosis vol. 11, No. 6, 1806-1813, Nov./Dec. 1991.

Brown, William R. et al. The liver and IgA: Immunological, cell biological and clinical implications, Hepatology, vol. 9, No. 5, pp. 763-784, 1989.

Bon, Charlotte, et al. "Capacity limits of asialoglycoprotein receptor-mediated liver targeting," vol. 9, No. 8, 1360-1369, Nov. 23, 2017.

Buckley, Dennis L., et al. "Targeting the von Hippel-Lindau E3 Ubiquitin Ligase Using Small Molecules to Disrupt the VHL/HIF-1α Interaction,"; J. Am. Chem. Soc. 134, 4465-4468; Feb. 27, 2012.

Connolly, Daniel T. et al. Binding and endocytosis of cluster glycosides by rabbit hepatocytes; Evidence for short-circuit pathway that does not lead to degradation, The Journal of Biological Chemistry, vol. 257, No. 2, issue of Jan. 25, pp. 939-945, 1982.

Dalpiaz, A. et al. "Molecular mechanism involved in the transport of a prodrug dopamine gycosyl conjugate, International Journal of Pharmaceutics," 336; 133-139; May 4, 2007.

Dancygier, Henryk, et al. Clinical Hepatology, Chapter 6 "Hepatic Metabolism," Springer Berlin, Heidelberg, pp. 75-102, Oct. 27, 2009.

D'Souza, Anisha A. et al. "Asialogycoprotein receptor mediated hepatocyte targeting—strategies and applications," Journal of Controlled Release, 203, 126-139, Feb. 18, 2015.

Day, James F. et al. Carbohydrate-mediated clearance of antibody—antigen complexes from the circulation, The Journal of Biological Chemistry, vol. 255, No. 6, Issue of Mar. 25, pp. 2360-2368, 1980.

Eldeeb, Mohamed A., et al. "Extracellular protein degradation via the lysosome," Communications Chemistry, 3:149, Oct. 30, 2020.

Gregoriadis, G. et al. "Catabolism of Desialylated Ceruloplasmin in the Liver" J. Biol. Chem. 245(21), 5833-5837, Nov. 10, 1970.

Harford, J. et al. "Intracellular Dissociation of Receptor-Bound Asialoglycoproteins in Cultured Hepatocytes" J. Biol. Chem. 258(5) 3191-3197, Mar. 10, 1983.

Huang, Xiangang et al. Well-Defined Multivalent Ligands for Hepatocytes Targeting via Asialoglycoprotein Receptor, Bioconjugate Chem. 2017, 28, 283-295, Dec. 14, 2016.

International Search Report and Written Opinion for PCT/US2022/027513, dated Oct. 25, 2022; 14 pages.

Inamoto, Takashi, et al. "IgG is associated with the asialoglycoprotein receptor in the human liver," Hepatology vol. 14(6), 1070-1075, Dec. 1991.

Iobst, Susanne, et al. Selective sugar binding to the carbohydrate recognition domains of the rat hepatic and macrophage asialoglycoprotein receptors, the Journal of Biological Chemistry, vol. 271, No. 12, Issue of Mar. 22, pp. 6686-6693, 1996.

Janas, Maja M. et al. "The nonclinical safety profile of GalNAc-conjugated RNAi therapeutics in subacute studies: Toxicologic Pathology," vol. 46(7) 735-745, Aug. 23, 2018.

Kempen, Herman J. et al. Effect of infusion of "tris-galactosyl-cholesterol" on plasma cholesterol, clearance of lipoprotein cholesteryl esters, and biliary secretion in the rat, Journal of Lipid Research, vol. 28, 659-666, 1987.

Kempen, Herman J. et al. A Water-soluble cholesteryl-containing trisgalactoside: synthesis, properties, and use in directing lipid-containing particles to the liver, J. Med. Chem. 27, 1306-1312, 1984.

Kudo, Masatoshi, et al. "Quantitative assessment of hepatocellular function through in vivo radiorespector imaging with technetium 99m galactosyl human serum albumin," Hepatology vol. 17, No. 5, 814-819, May 17, 1993.

Kolset, S.O. et al. "The Effects of Colchicine and Cytochalasin B on Uptake and Degradation of Asialo-Glycoproteins in Isolated Rat Hepatocytes" Exp Cell Res, 159-167, 1979.

Li, Yan et al. "Targeted delivery of macromolecular drugs: Asialoglycoprotein Receptor (ASGPR) Expression by Selected Hepatoma Cell Lines used in Antiviral Drug Development," Current Drug Delivery, 5, 299-302, Sep. 30, 2008.

Lu, Jing et al. "Hijacking the E3 Ubiquitin Ligase Cereblon to Efficiently Target BRD4," Chem. Biol. 22(6): 755-763; Jun. 18, 2015.

Mamidyala, Sreeman K. et al. "Glycomimetric ligands for the human asialoglycoprotein receptor," Journal of the American Chemical Society, 134, 1978-1981, Jan. 24, 2012.

Meir, Markus, et al. "Crystal Structure of the Carbohydrate Recognition Domain of the H1 Subunit of the Asialoglycoprotein Receptor," J. Mol. Biol., 300, 857-865, Jul. 21, 2000.

Miki, Kenji et al. "Receptor measurements via Tc-GSA Kinetic Modeling are Proportional to Functional Hepatocellular Mass," J Nucl Med 2001; 42:733-737; Japan, Jan. 10, 2001.

(56) References Cited

OTHER PUBLICATIONS

Morell, Anatol G. et al. The Role of Sialic Acid in Determining the Survival of Glycoproteins in the Circulation, The Journal of Biological Chemistry, vol. 246, No. 5, issue of Mar. 10, pp. 1461-1467, 1971.
Nandakumar, Kutty Selva, et al. Therapeutic cleavage of IgG: new avenues for treating inflammation, Cell Press, 173, Trends in Immunology vol. 29 No. 4, 2008.
Nandakumar, Kutty Selva, Targeting IgG in arthritis: Disease pathways and therapeutic avenues, International Journal of Molecular Sciences, 19, 677, 2018.
Nalawansha, Dhanusha, et al. "Targeted protein internalization and degradation by ENDosome TArgeting Chimeras (ENDTACs)," ACS Central Science 5, 1079-1084, May 9, 2019.
Napier, M.P. et al. Antibody-directed enzyme prodrug therapy: efficacy and mechanism of action in colorectal carcinoma, Clinical Cancer Research vol. 6, 765-772, Mar. 2000.
Nioi, P. et al. "Variant ASGR1 Associated with a Reduced Risk of Coronary Artery Disease," The New England Journal of Medicine, 374:2131-41, May 18, 2016.
Oka, J. A. et al. "Microtubule-Depolymerizing Agents Inhibit Asialo-Orosomucoid Delivery to Lysosomes but Not Its Endocytosis or Degradation in Isolated Rat Hepatocytes" Biochim Biophys Acta 763, 368-378, Dec. 19, 1983.
Ong, Gaik Lin et al. Galactose-conjugated antibodies in cancer therapy: properties and principles of action, Cancer Research 1991;51:1619-1626. Published online Mar. 1, 1991.
Park, Jung-Hyun et al. "Detection of surface asialoglycoprotein receptor expression in hepatic and extra-hepatic cells using a novel monoclonal antibody," Biotechnol Lett 28:1061-1069, Jun. 24, 2006.
Petrov, Rostislav A. et al. "Synthesis and biological evaluation of novel mono- and bivalent ASGP-R-targeted drug-conjugates," Bioorganic and Medicinal Chemistry Letters 28, 382-387, Dec. 14, 2017.
Pimstone, Neville R. et al. "Evaluation of Hepatocellular Function by Way of Receptor-mediated Uptake of a Technetium-99m-labeled Asialoglycoprotein Analog," Symposium on Bile Acids. Hepatology, 917-923, Oct. 1994.
PrabhuDas, Mercy R. et al. "A Consensus Definitive Classification of Scavenger Receptors and Their Roles in Health and Disease," The Journal of Immunology 198(10) 3775-3789, May 15, 2017.
Pubchem CID 28862057 Create Date: Dec. 5, 2007; Date Accessed May 20, 2021.
Rensen, Patrick C.N. et al. Determination of the upper size limit for uptake and processing of ligands by the asialoglycoprotein receptor on hepatocytes in vitro and in vivo, The Journal of Biological Chemistry, vol. 276, No. 40, issue of Oct. 5, pp. 37577-37584, 2001.
Rensen, Patrick C.N., et al., "Design and Synthesis of Novel N-Acetylgalactosamine-Terminated Glycolipids for Targeting of Lipoproteins to the Hepatic Asialoglycoprotein Receptor," J. Med. Chem., 47, 5798-5808, Oct. 6, 2004.
Rensen, Patrick C.N. Stimulation of liver-directed cholesterol flux in mice by novel N-acetylgalactosamine-Terminated Glycolipds with high affinity for the asialoglycoprotein receptor, Arterioscler Thromb Vasc Biol., 26, 169-175, Jan. 2006.
Roelen, Harlof C.P.F. et al. Water-soluble cholesteryl-containing phosphorothioate monogalactosides: synthesis, properties, and use in lowering blood cholesterol by directing plasma lipoproteins to the liver, J. Med. Chem. 34, 1036-1042, 1991.
Rogers, GT et al. Plasma clearance of an antibody—enzyme conjugate in ADEPT by monoclonal anti-enzyme: its effect on prodrug activation in vivo, British Journal of Cancer 72, 1357-1363, Dec. 1, 1995.
Rogers, John C. et al. Hepatic uptake of proteins coupled to fetuin glycopeptide, Biochemical and biophysical research communications, vol. 45, No. 3, 1971.

Roggenbuck, Dirk et al. "Asialoglycoprotein receptor (ASGPR): a peculiar target of liver-specific autoimmunity," Autoimmun Highlights 3:119-125, Oct. 30, 2012.
Roy, Marc et al. "Characterization of Asialoglycoprotein Receptor (ASGPR) directed hepatocellular delivery using a Pfizer developed targeting ligand PF-06853291," The FASEB Journal, 31: 938.7-938.7, Oct. 3, 2018.
Sanhueza, Carlos A. et al. Efficient Liver Targeting by Polyvalent Display of a Compact Ligand for the Asialoglycoprotein Receptor; JACS, 2017, 139, 3528, Feb. 23, 2017.
Seymour, Leonard W., et al. "Hepatic drug targeting: phase I evaluation of polymer-bound doxorubicin," J. Clin. Oncol. 20(6):1668-76; Mar. 15, 2002.
Schmidt, Karsten et al. "Characterizing the effect of GalNAc and phosphorothioate backbone on binding of antisense obligonucleotides to the asalogycoprotein receptor," Nucleic Acids Research, vol. 45(5) 2294-2306, Feb. 3, 2017.
Sharma, Surinder K. Galactosylated Antibodies and Antibody-enzyme conjugates in antibody-directed enzyme prodrug therapy, Cancer Supplemental vol. 73, No. 3, 1114-1120, Feb. 1, 1994.
Spiess, M. "The Asialoglycoprotein Receptor: A Model for Endocytic Transport Receptors" Biochemistry, 29(43), 10009-10018, Oct. 30, 1990.
Sliedregt, Leo A. J. et al. "Design and synthesis of novel amphiphilic dendritic galactosides for selective targeting of liposomes to the hepatic asialoglycoprotein receptor," J. Med. Chem., 42, 609-618, Feb. 5, 1999.
Sockolosky, Jonathan T. et al. "Fusion of a short peptide that binds immunoglobulin G to a recombinant protein substantially increases its plasma half-life in mice," PLos One Jul. 24, 2014, 1-16.
Springer, Aaron D. et al. "GalNAc-siRNA Conjugates: Leading the Way for Delivery of RNAi Therapeutics," Nucleic Acid Therapeutics vol. 28(3) 109-118, May 24, 2018.
Stockert, Richard J. et al. Hepatic binding protein: The protective role of its sialic acid residues, Science, vol. 197, 667-668, Aug. 12, 1977.
Stokmaier, Daniela, et al. "Design, synthesis and evaluation of monovalent ligands for the asialoglycoprotein receptor (ASGP-R)," Bioorganic & Medicinal Chemistry, 7254-7264, 17, vol. 17920), Aug. 29, 2009.
Thornburg, Robert W. et al. Carbohydrate-mediated clearance of immune complexes from the circulation, The Journal of Biological Chemistry vol. 255, No. 14 issue of Jul. 25, pp. 6820-6825, 1980.
Tolleshaug, H. Et Al. "Uptake and Degradation of 125-I Labeled Asialo-Fetuin by Isolated Rat Hepatocytes" Biochim. Biophys. Acta, 499, 73-84, Aug. 25, 1977.
Toure et al. "Small-Molecule Protacs: New Approaches to Protein Degradation" Angew. Chem. Int. Ed. 2016, 55(6), 2-10, Jan. 12, 2016.
Van Berkel, Theo J.C. et al. The effect of a water-soluble tris tris-galactoside-terminated cholesterol derivative on the fate of low-density lipoproteins and liposomes, The Journal of Biological Chemistry, vol. 260, No. 5, issue of Mar. 10, pp. 2694-2699, 1985.
Winter et al. "Drug Development. Phthalimide Conjugation as a Strategy for in Vivo Targeted Protein Degradation," Science, 348, issue 6241, 1376-1381, May 21, 2015.
Weigel, P. H. "Rat Hepatocytes Bind to Syawnthetic Galactoside Surfaces via a Patch of Asialoglycoprotein Receptors" J. Cell Biol. 87(3), 855-861, Dec. 1, 1980.
Wong, Ting Chi et al. Synthesis of D-Galactosamine derivatives and binding studies using isolated rat hepatocytes, Carbohydrate Research, 170, 27-46, 1987.
Yoo, Barney, et al. N-Acetylgalactosamino dendrons as clearing agents to enhance liver targeting of model antibody-fusion protein, Bioconjugate Chemistry, 24, 2088-2103, 2013.
Goetze et al. "High-mannose glycans on the Fc region of therapeutic IgG antibodies increase serum clearance in humans." Glycobiology 21.7, Mar. 18, 2011, 949-959.

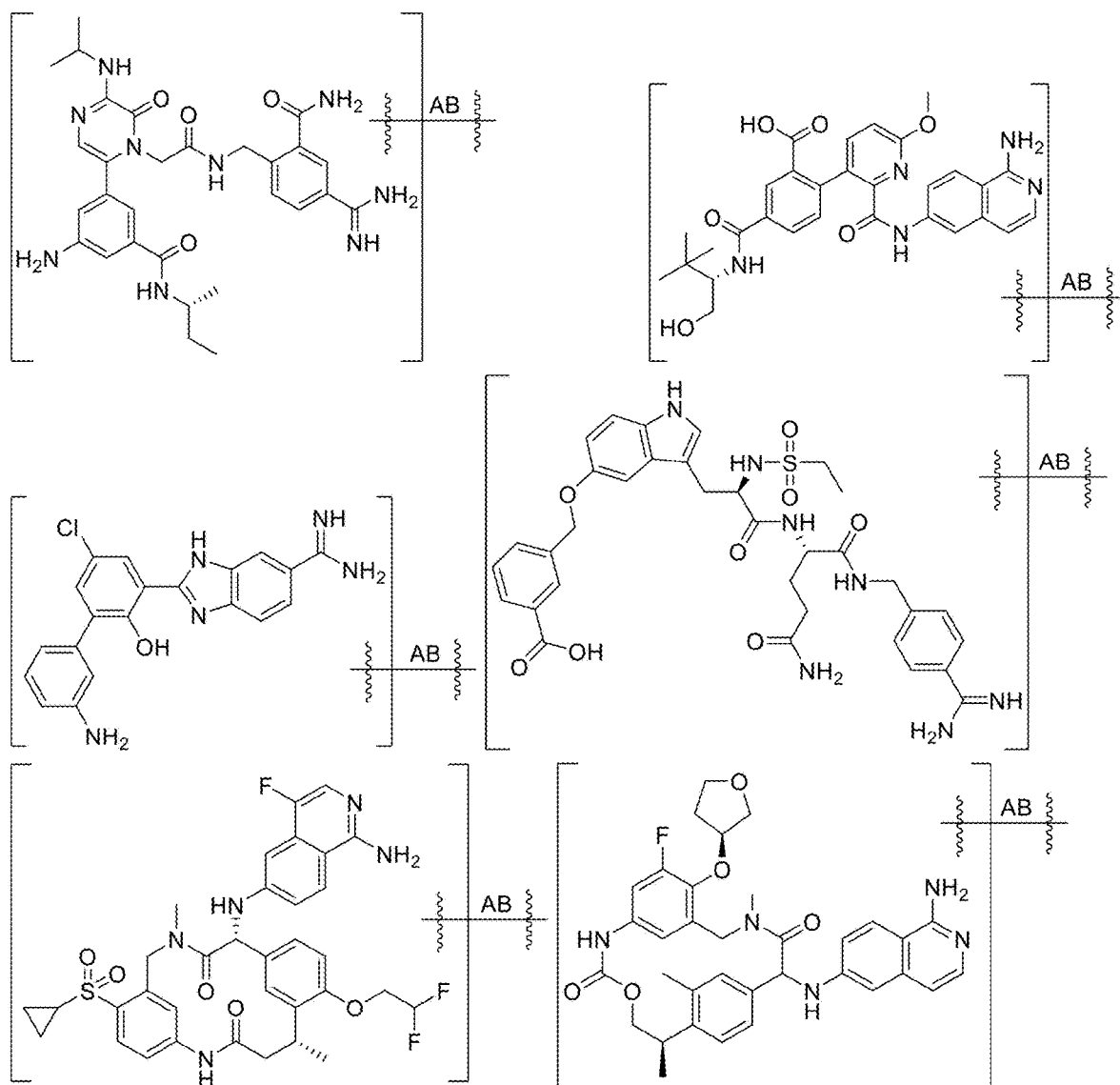
FIG. 1AAA

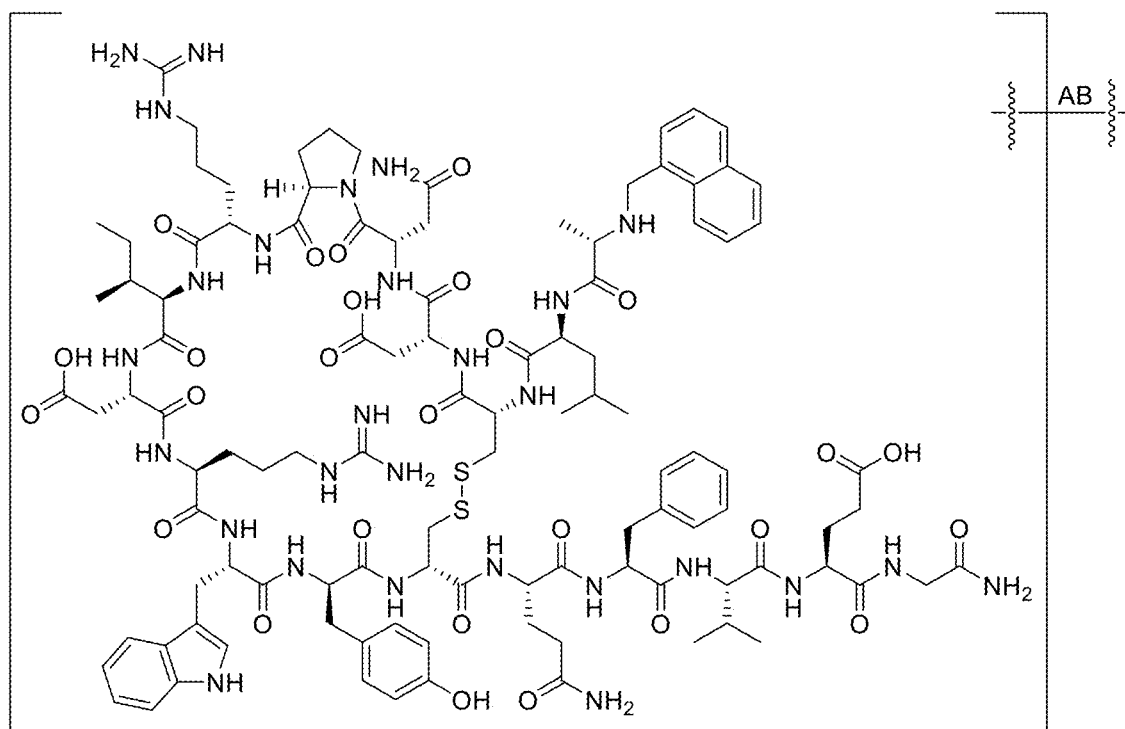
FIG. 1BBB
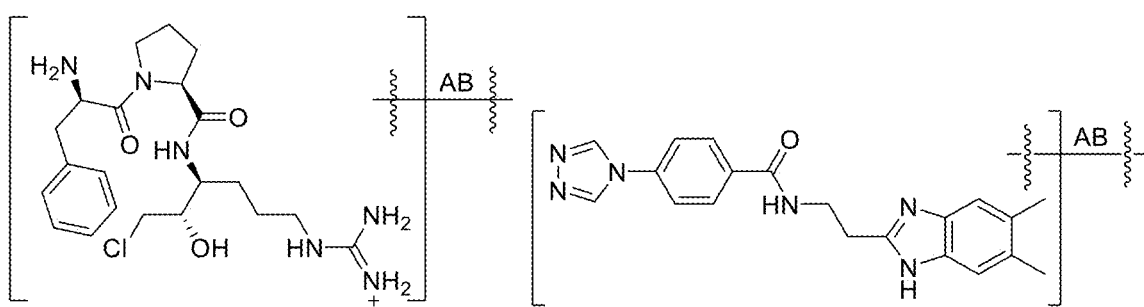
FIG. 1CCC

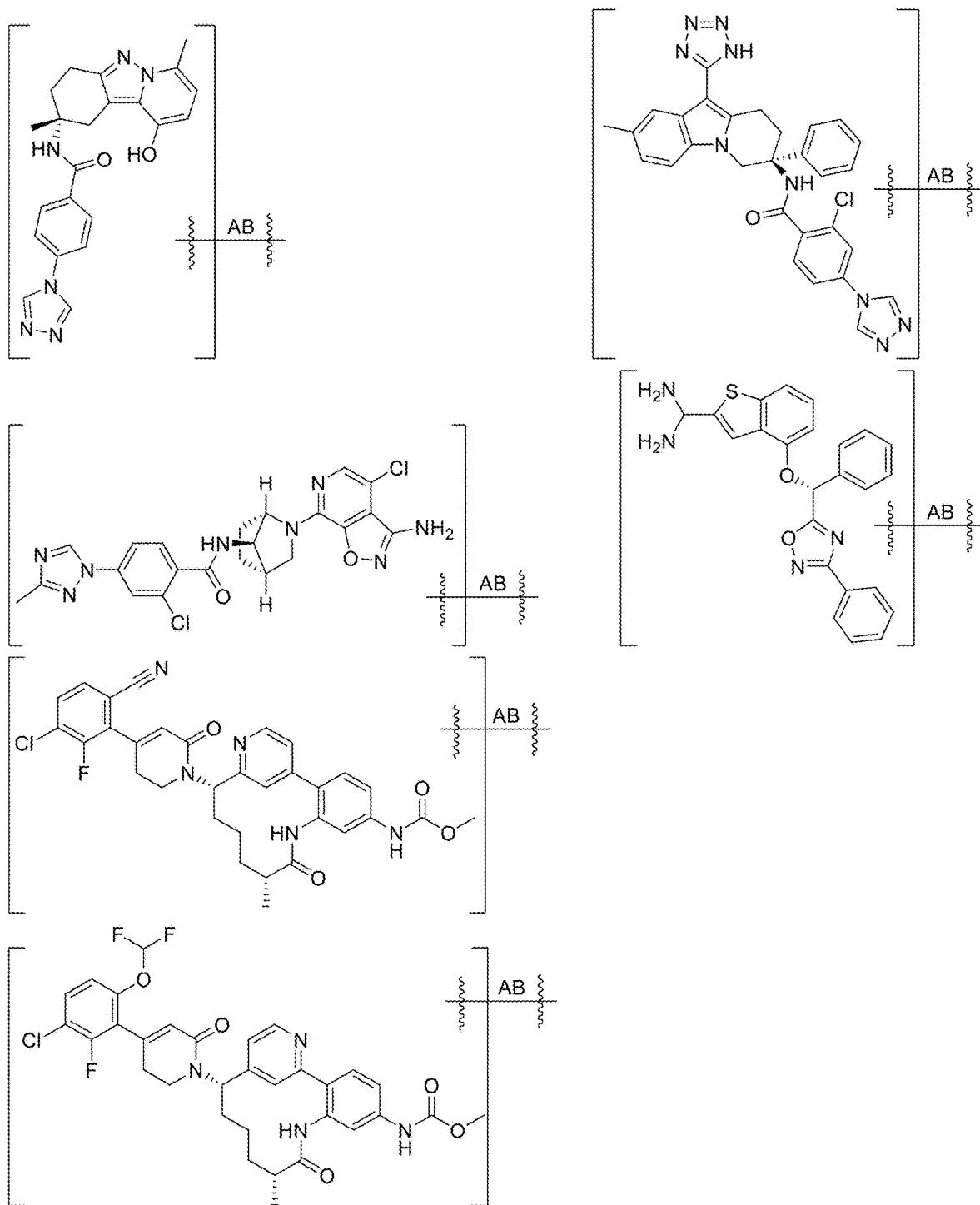
FIG. 1DDD

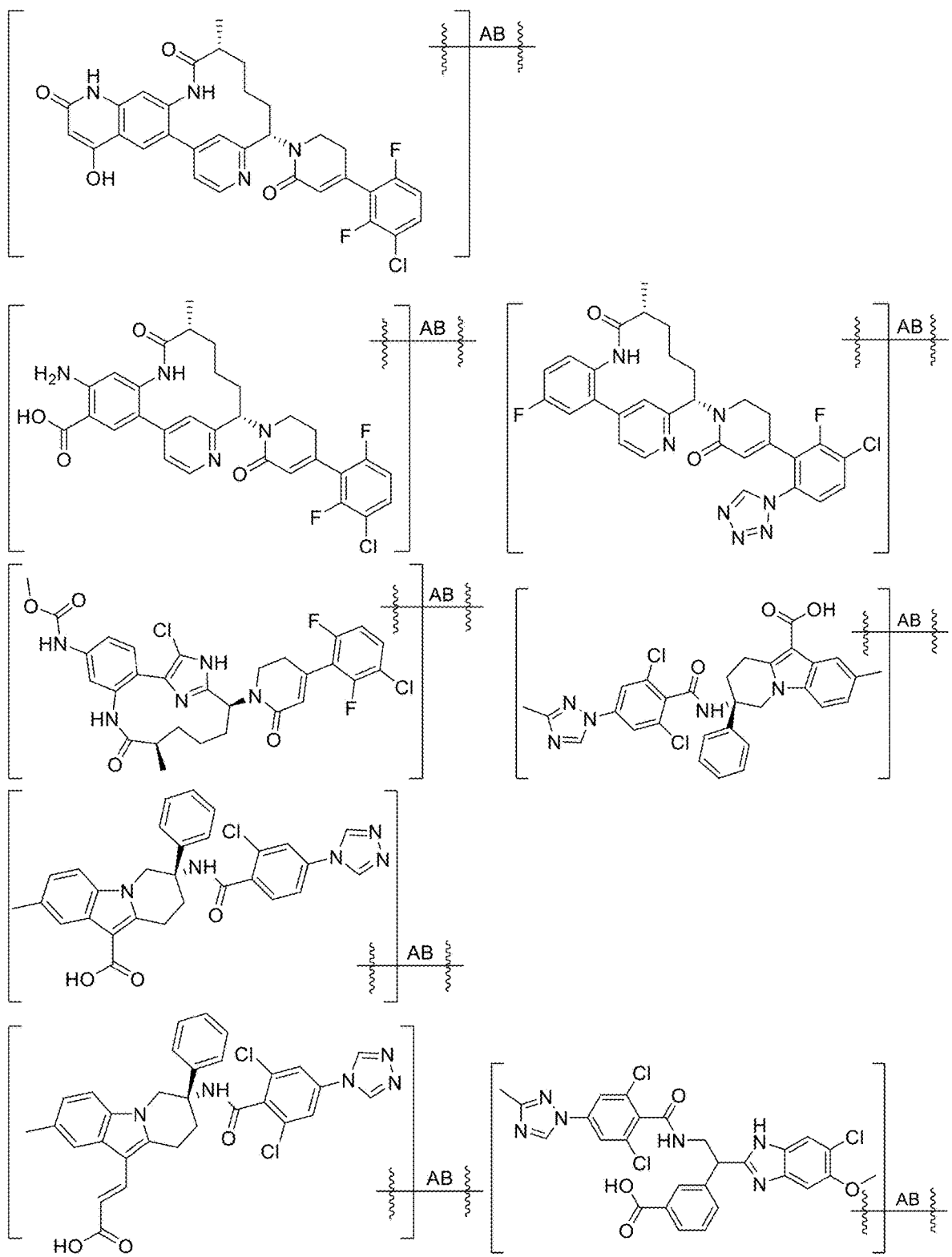
FIG. 1EEE

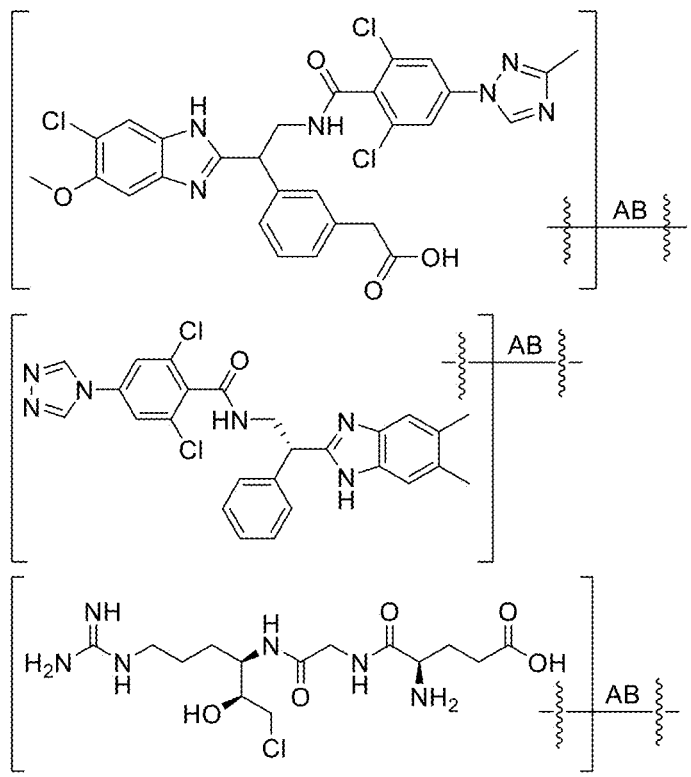
FIG. 1FFF
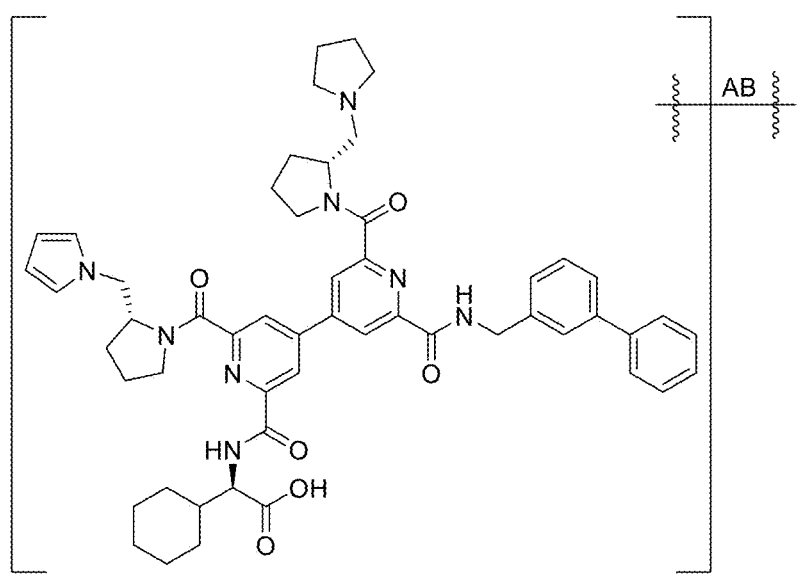
FIG. 1GGG

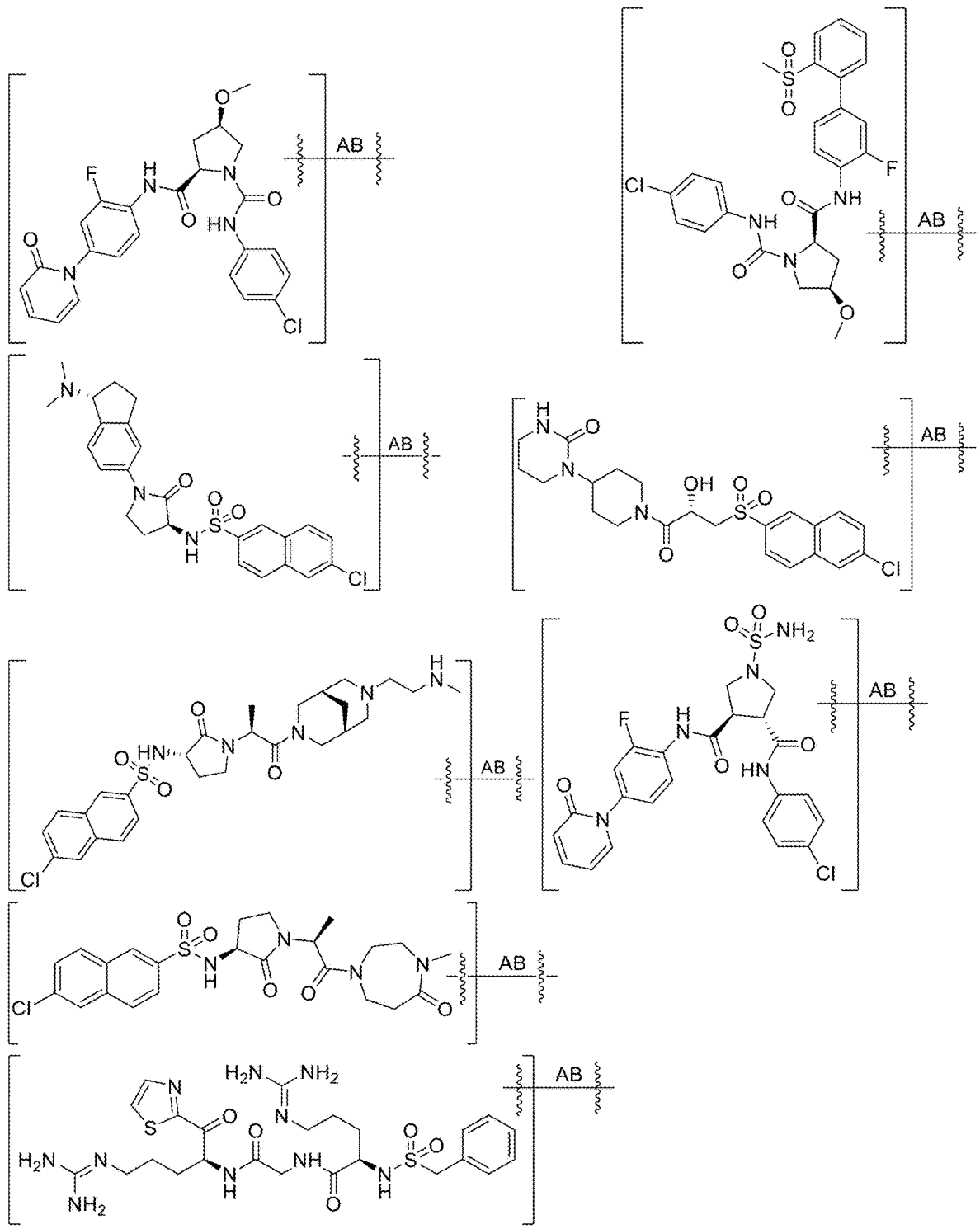
FIG. 1HHH

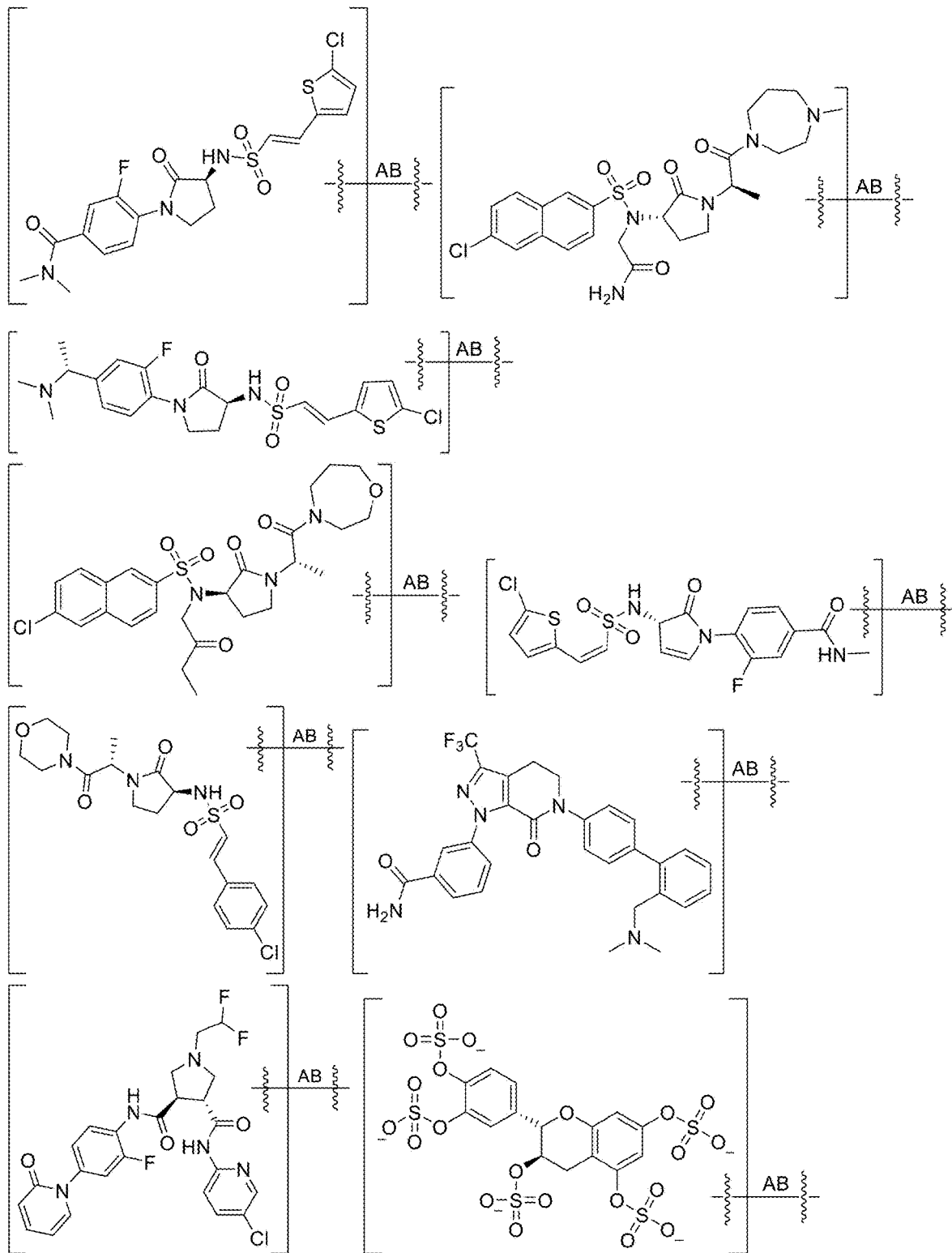
FIG. 1III

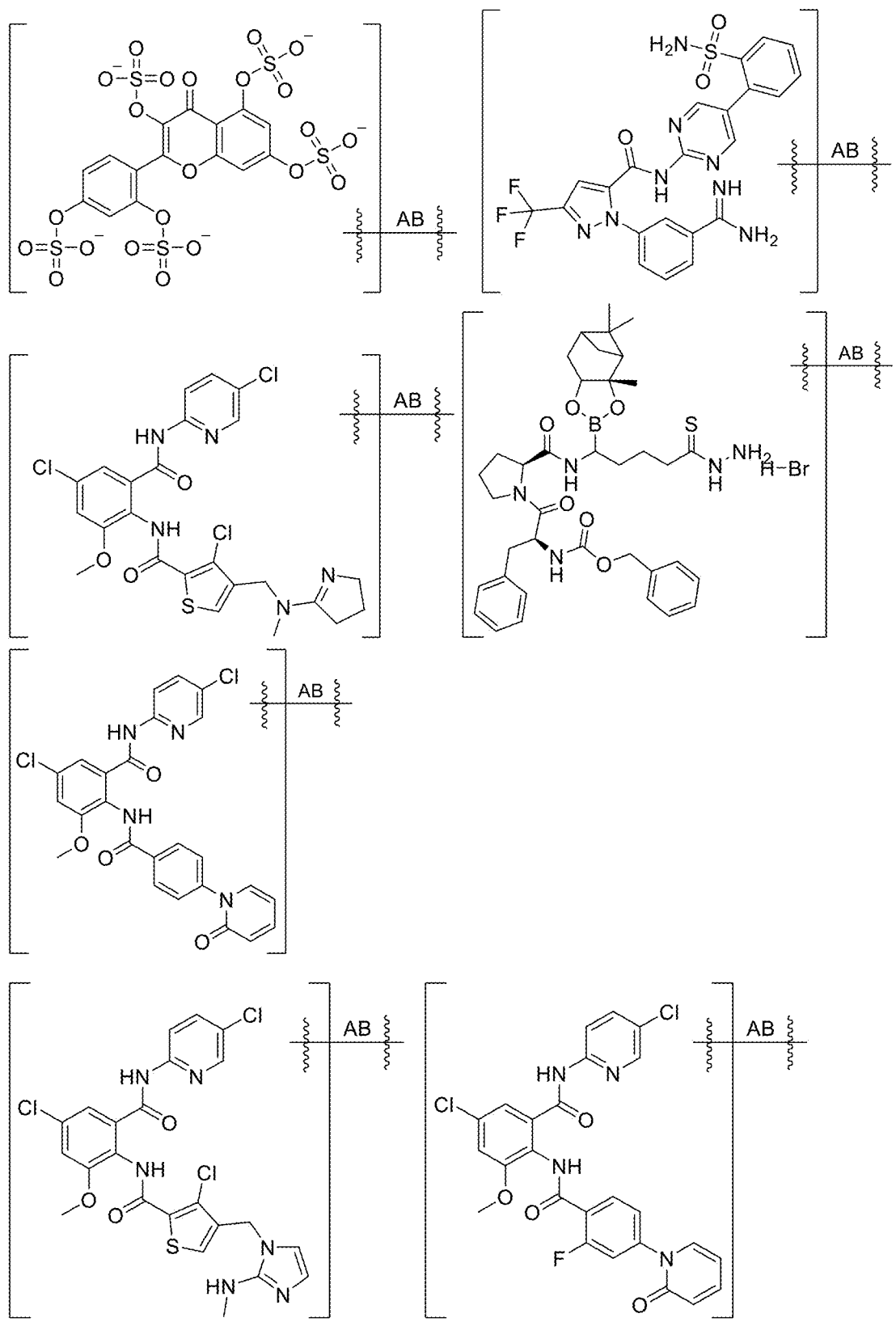
FIG. 1JJJ

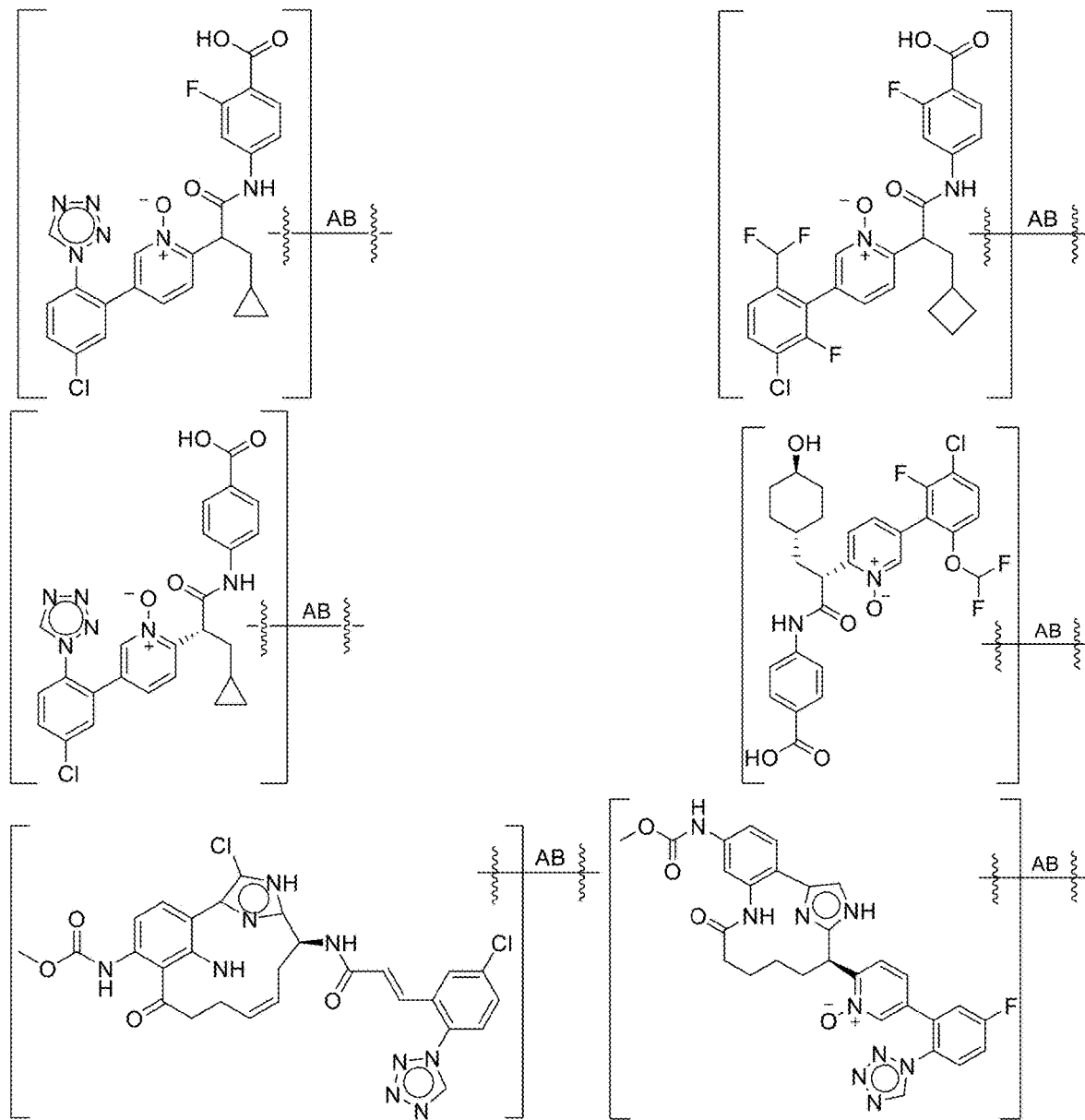
FIG. 1KKK

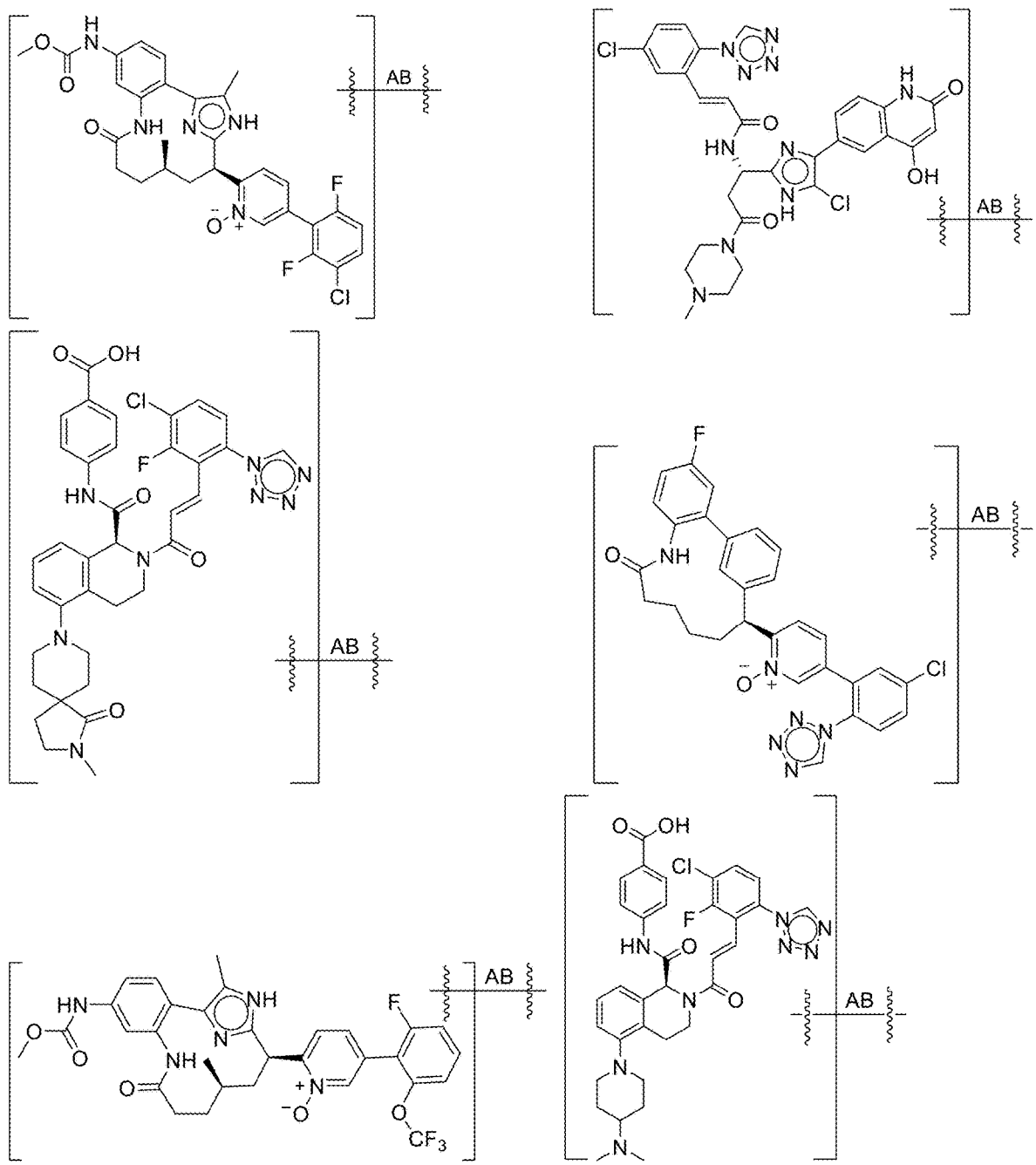
FIG. 1LLL

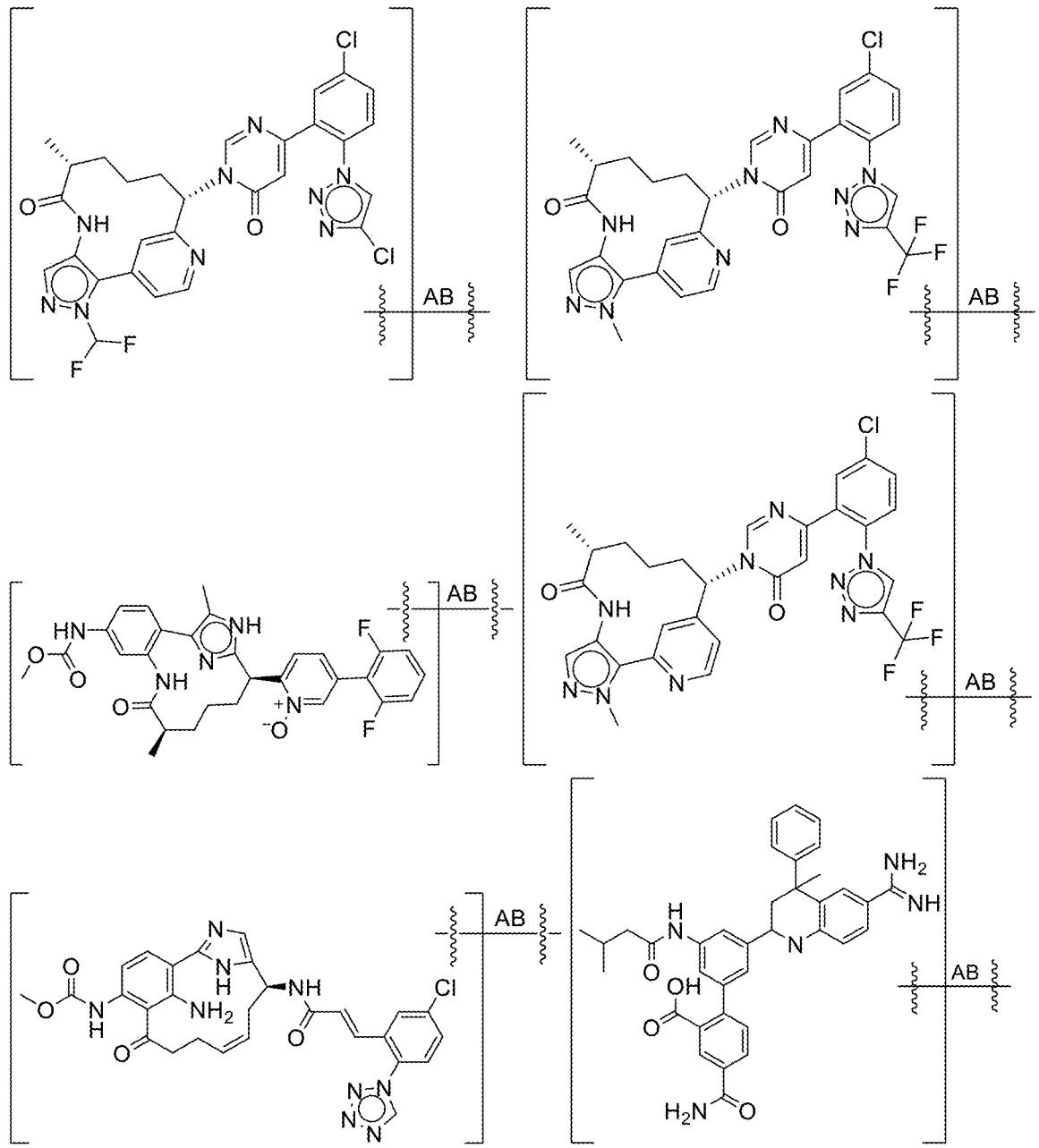
FIG. 1MMM

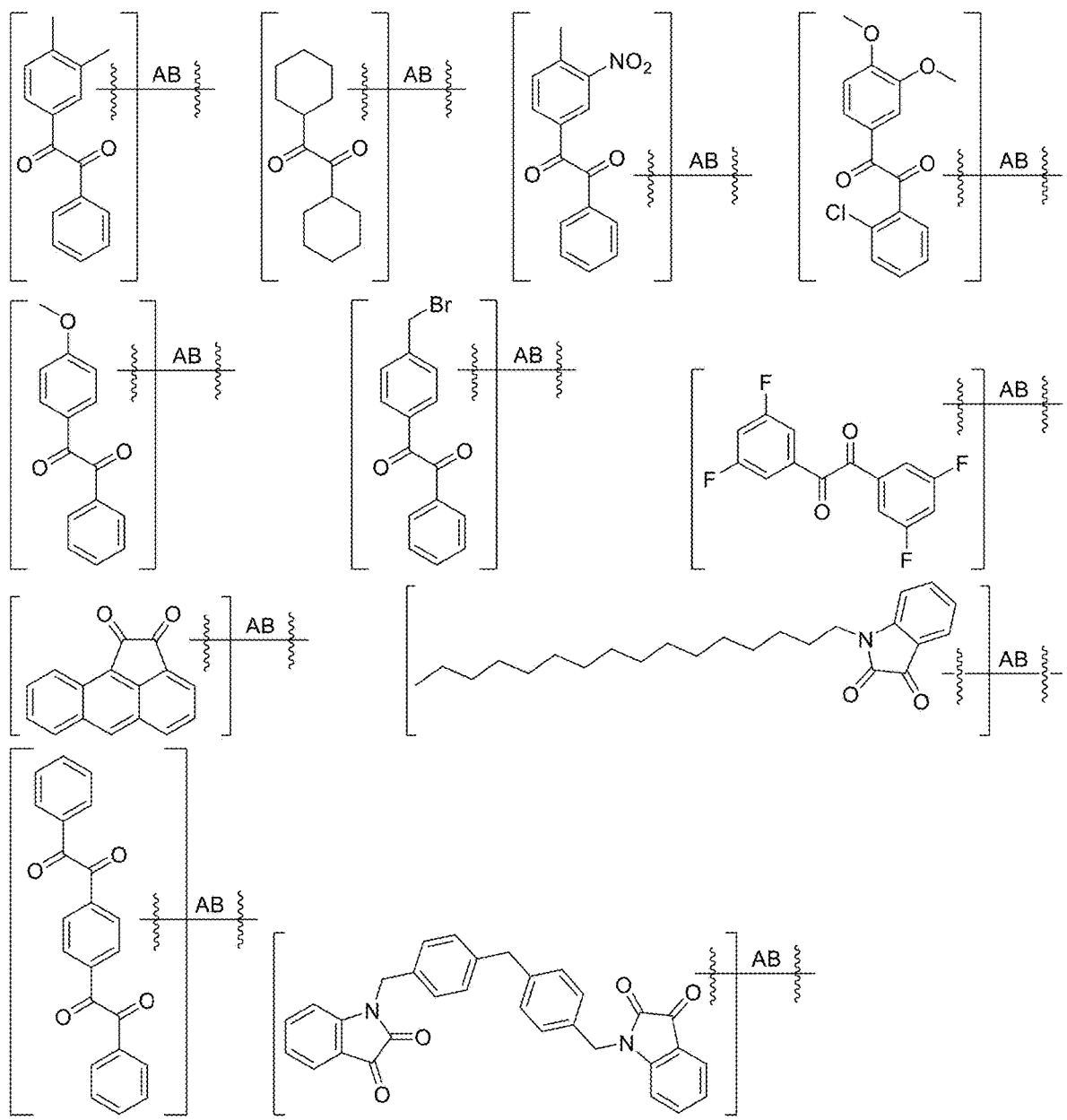
FIG. 1NNN

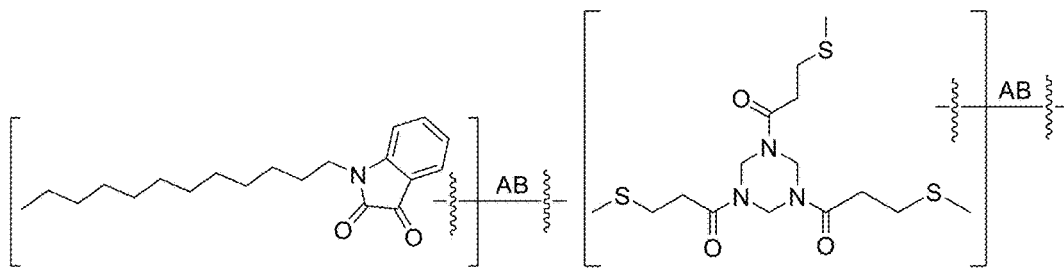
FIG. 1OOO
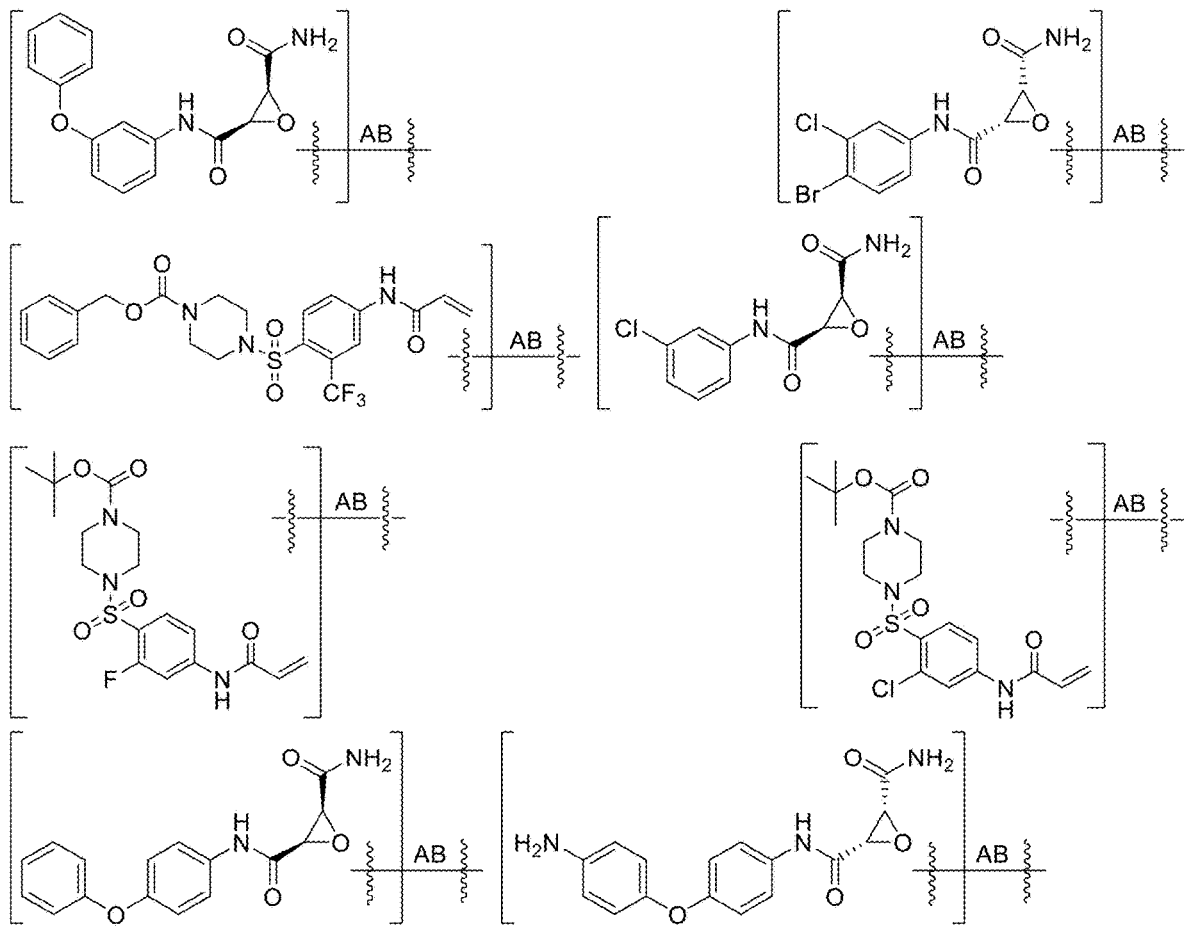
FIG. 1PPP

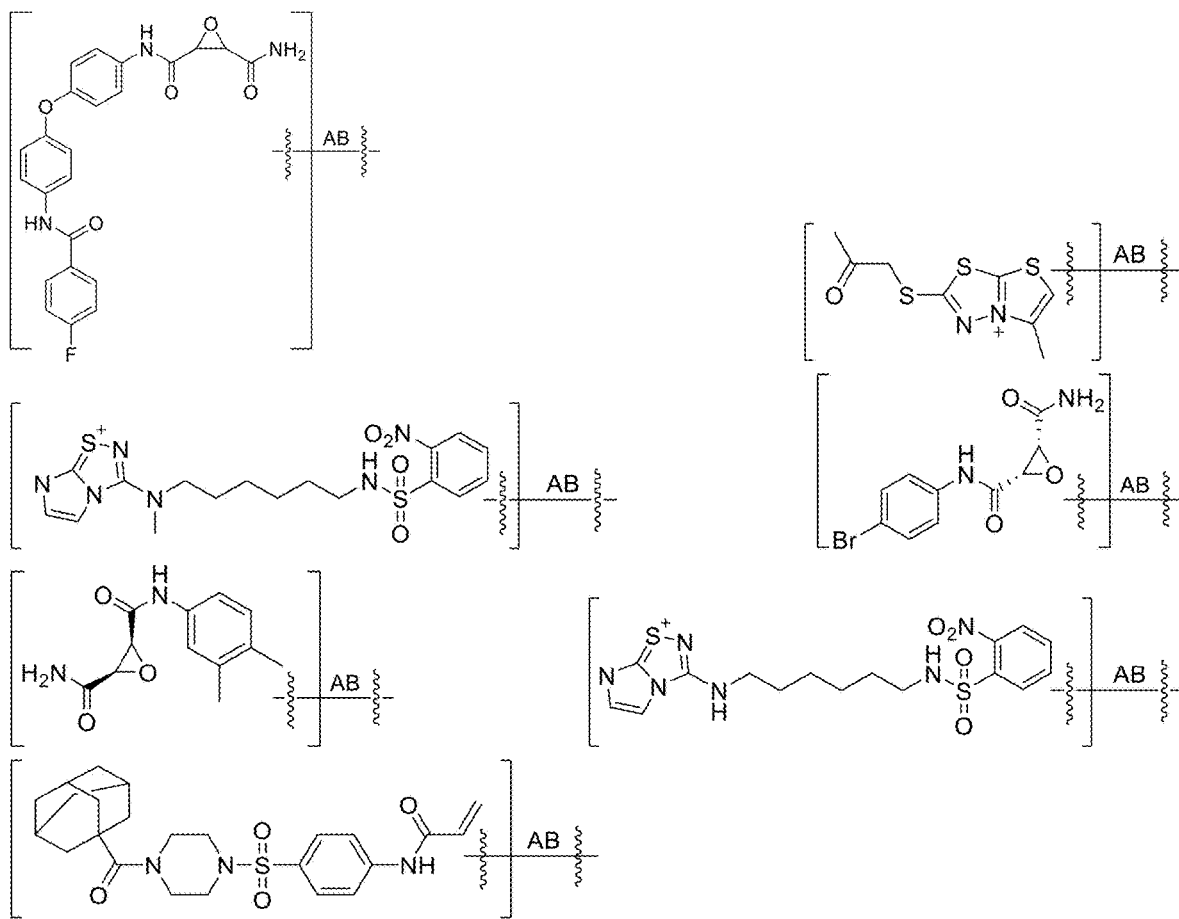
FIG. 1QQQ
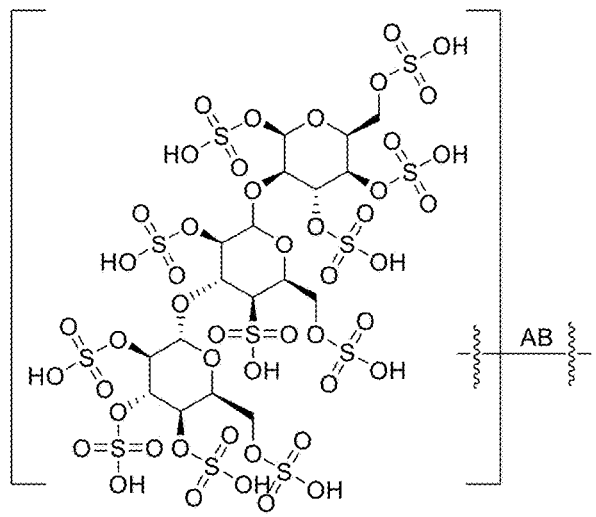
FIG. 1RRR

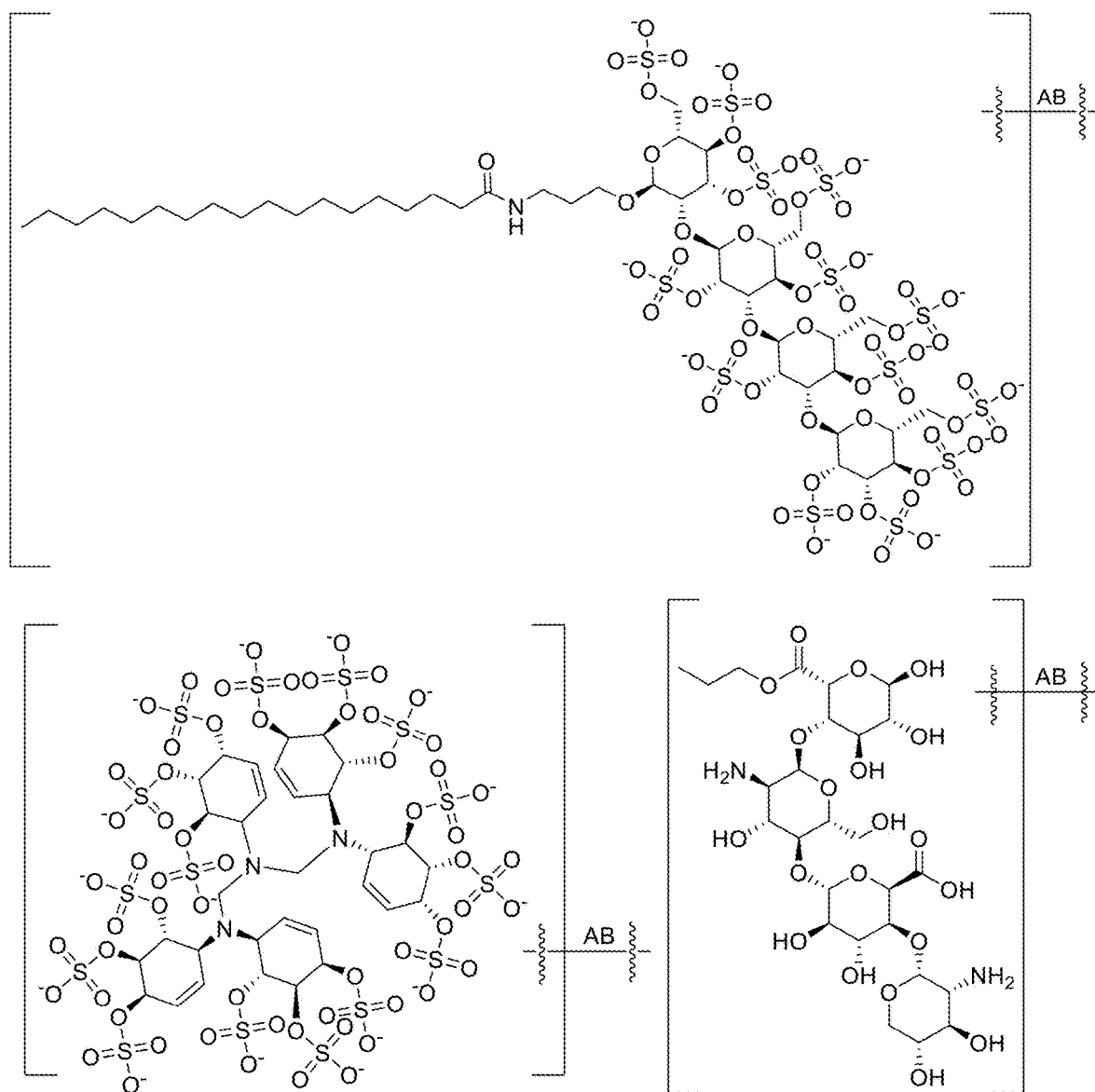
FIG. 1SSS

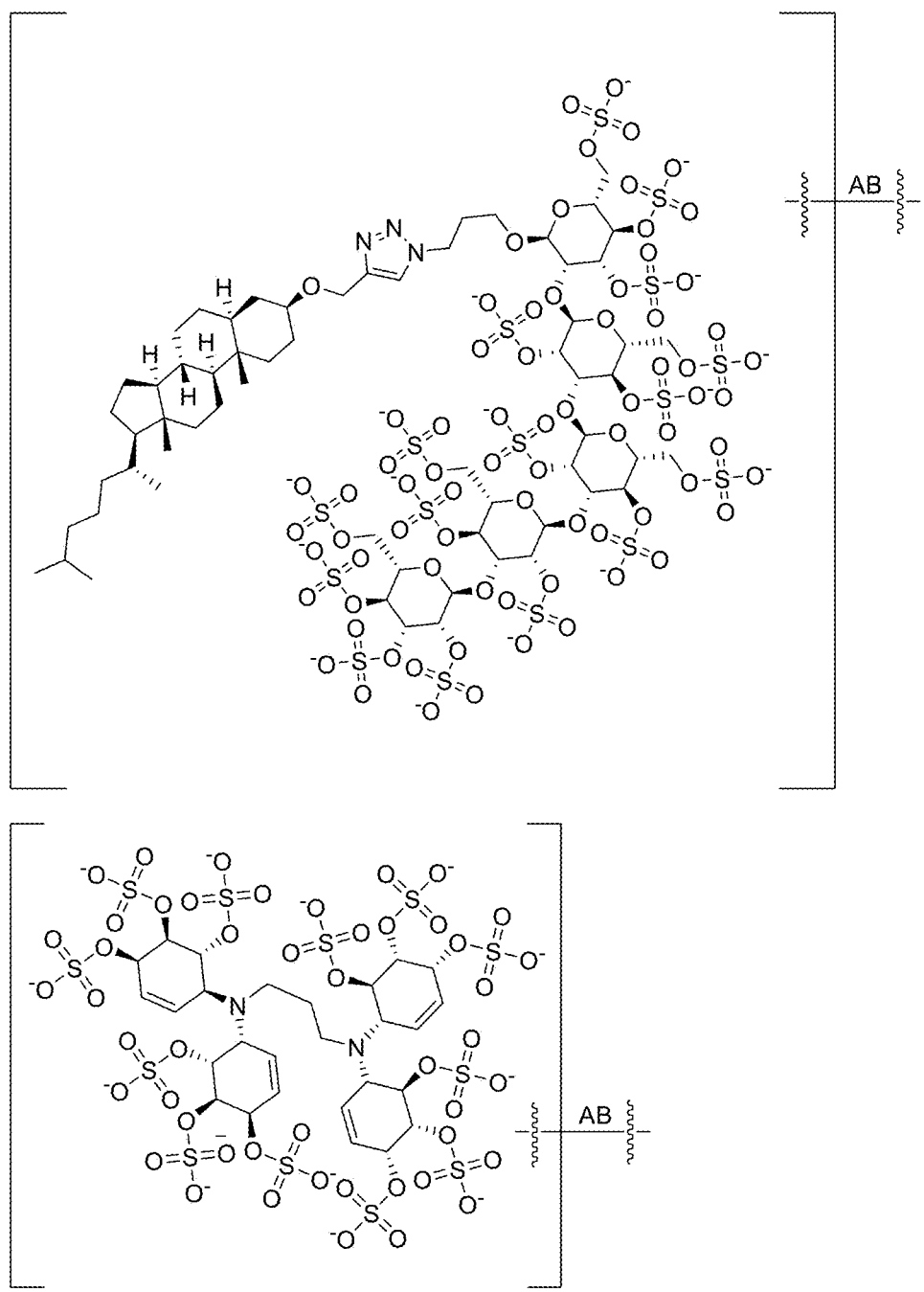
FIG. 1TTT

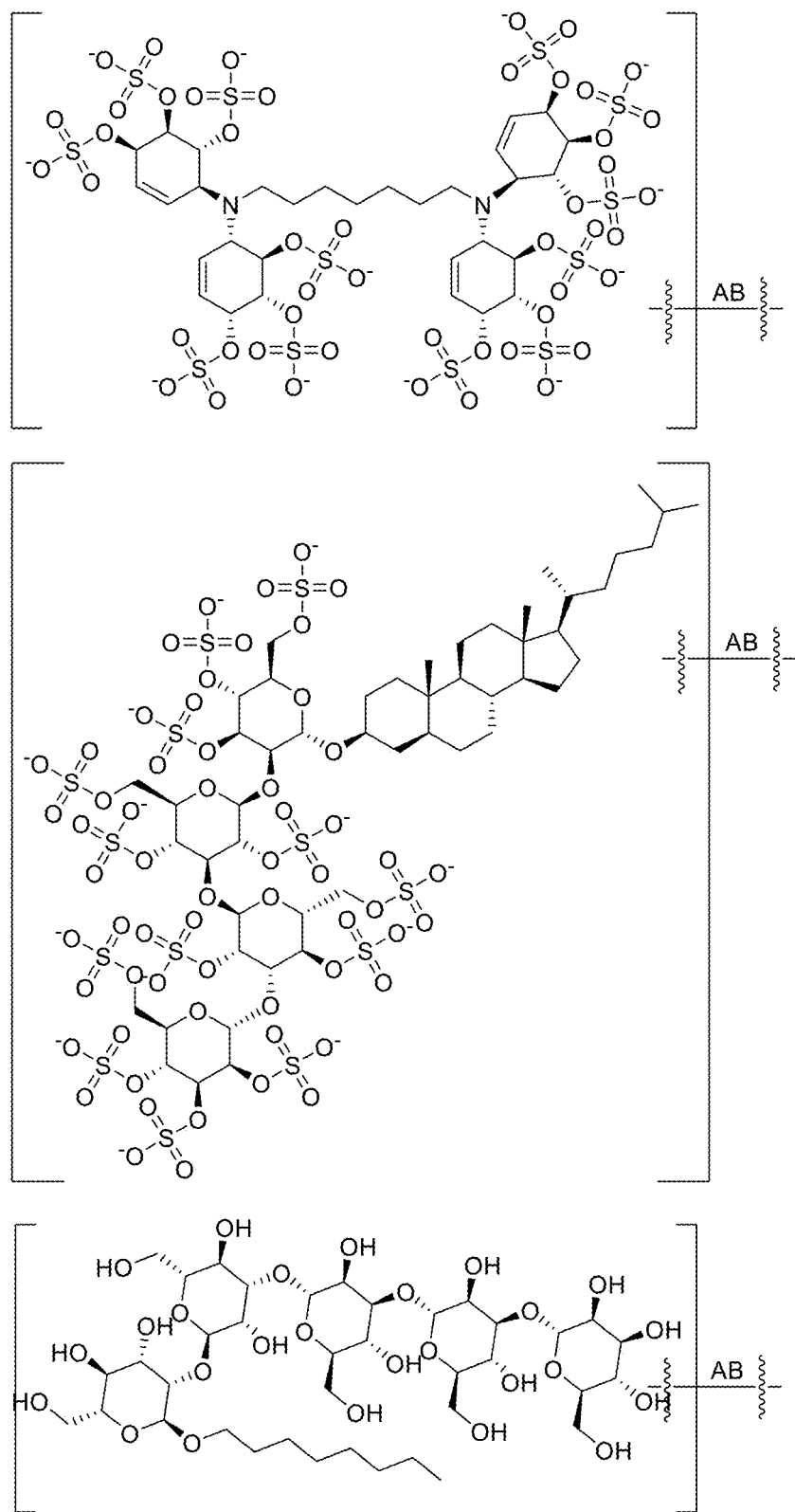
FIG. 1UUU

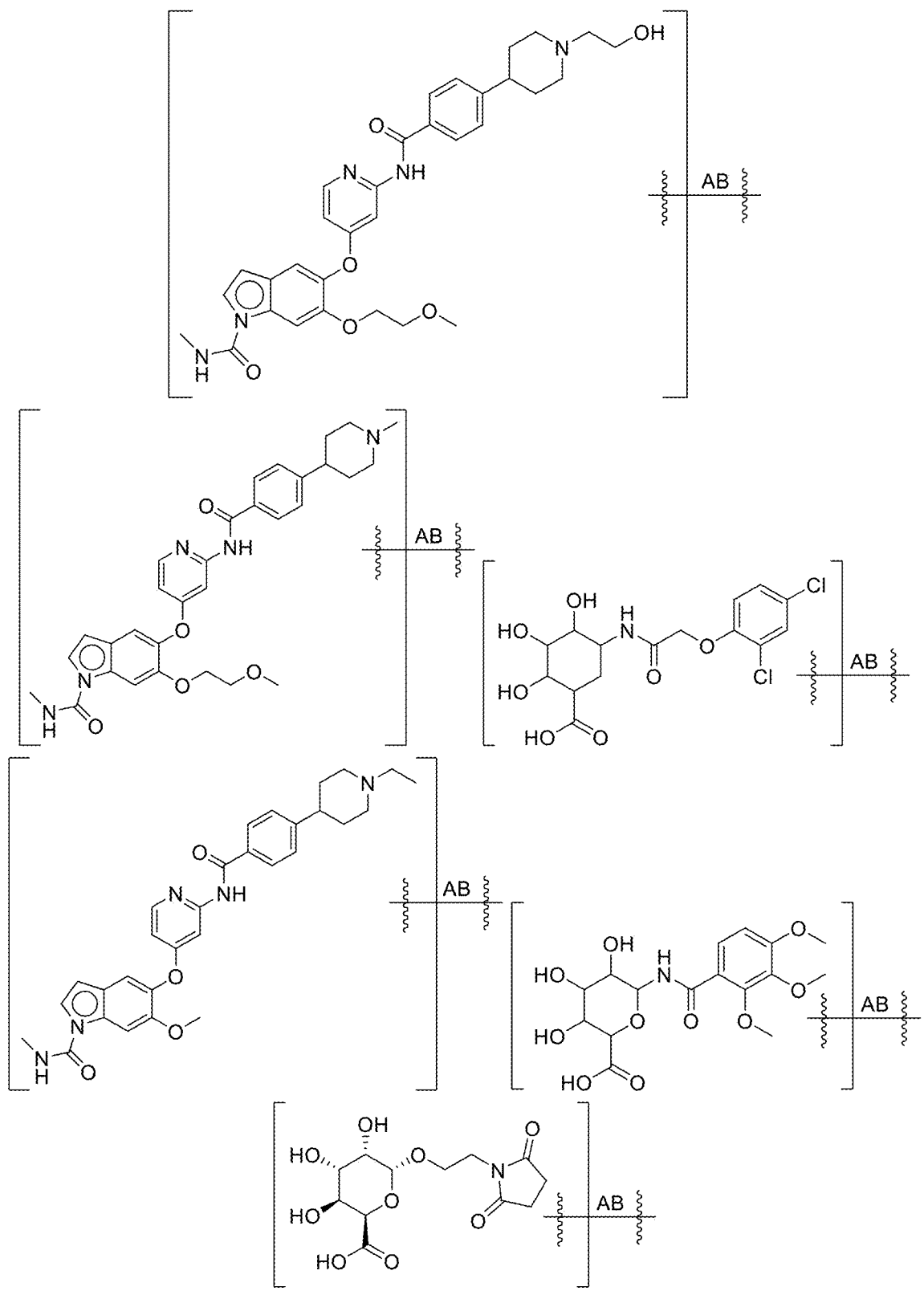
FIG. 1VVV

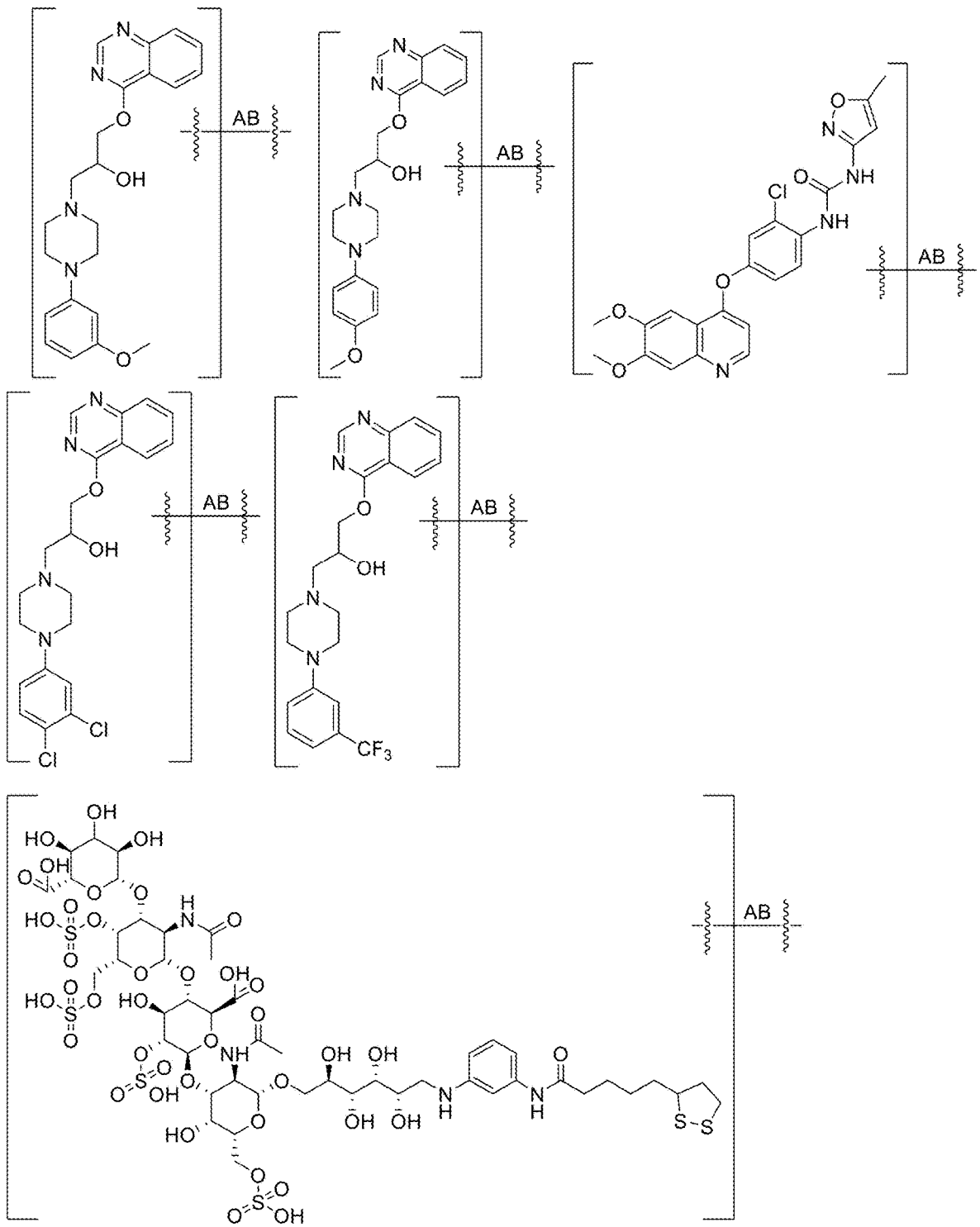
FIG. 1WWW

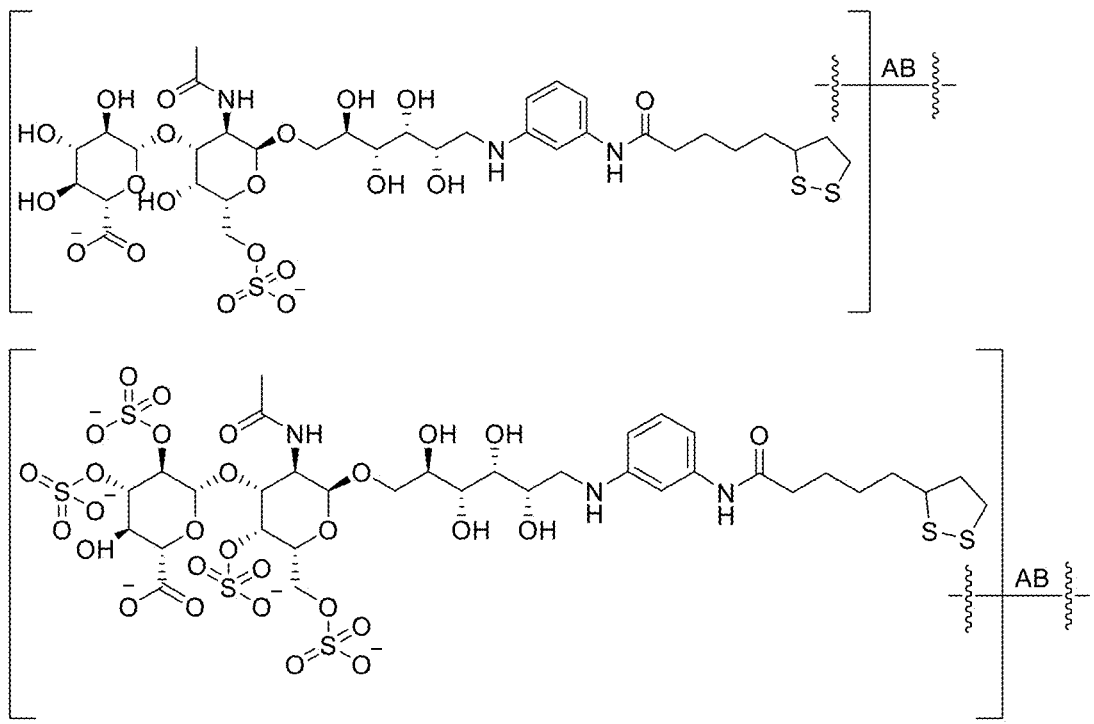
FIG. 1XXX
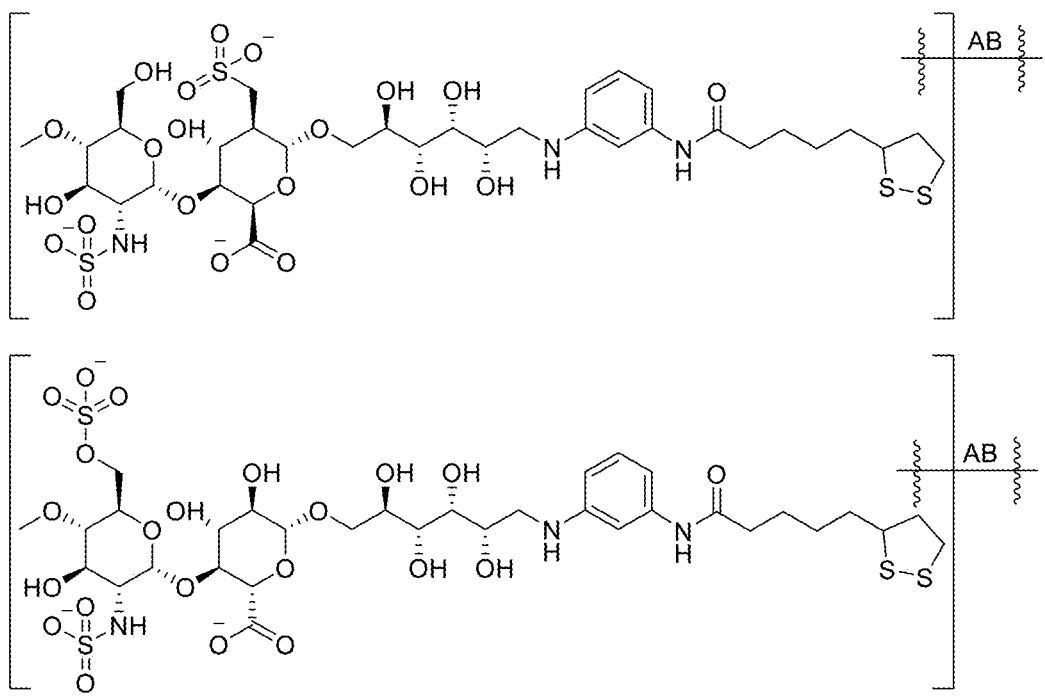
FIG. 1YYY

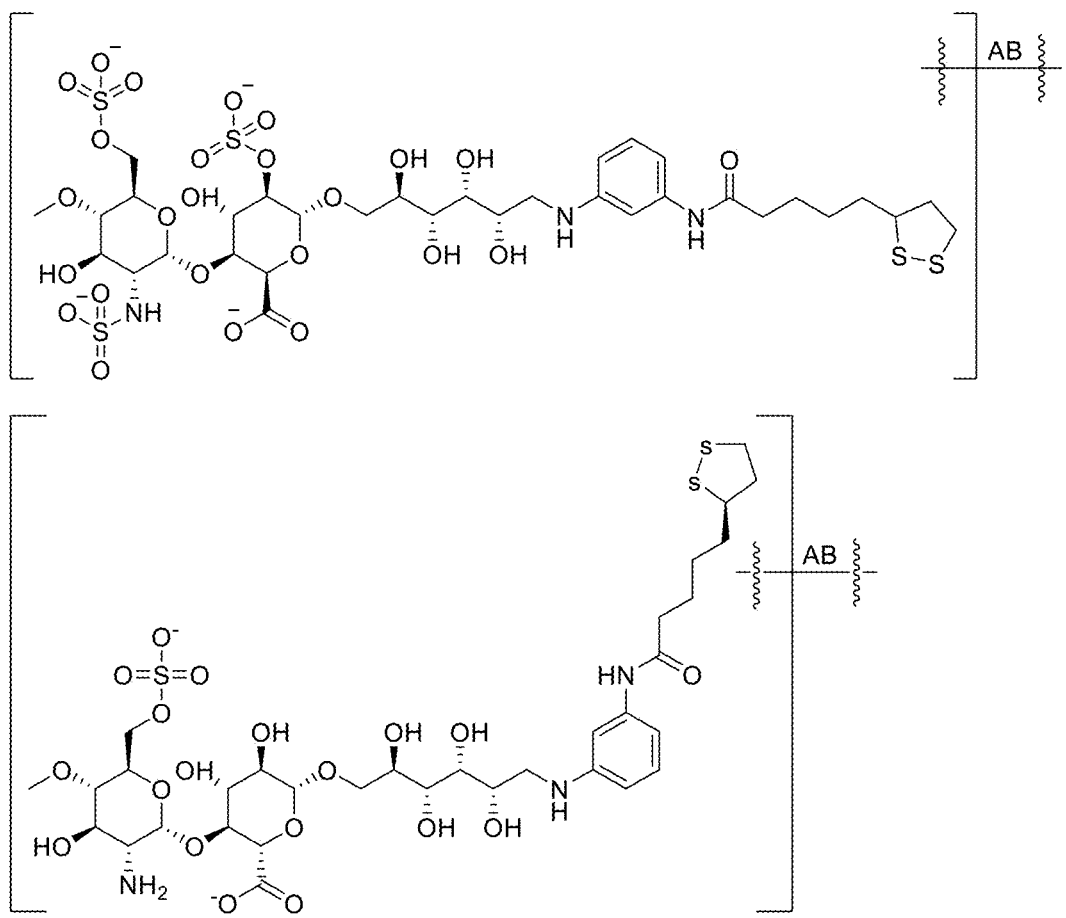
FIG. 1ZZZ
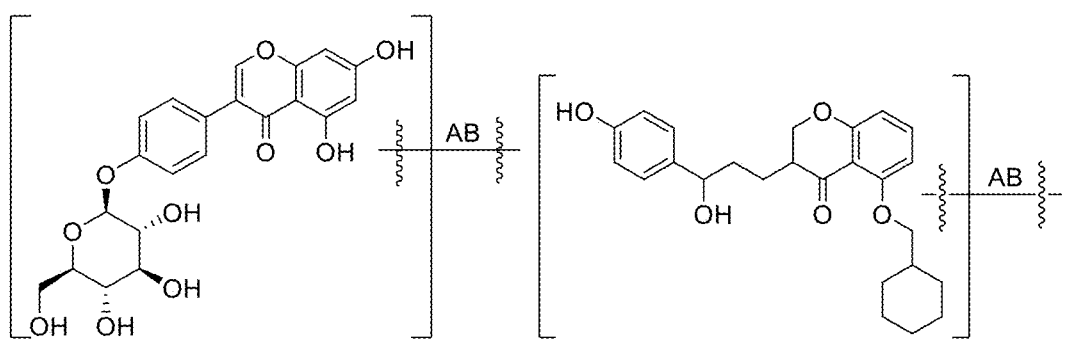
FIG. 1AAAA

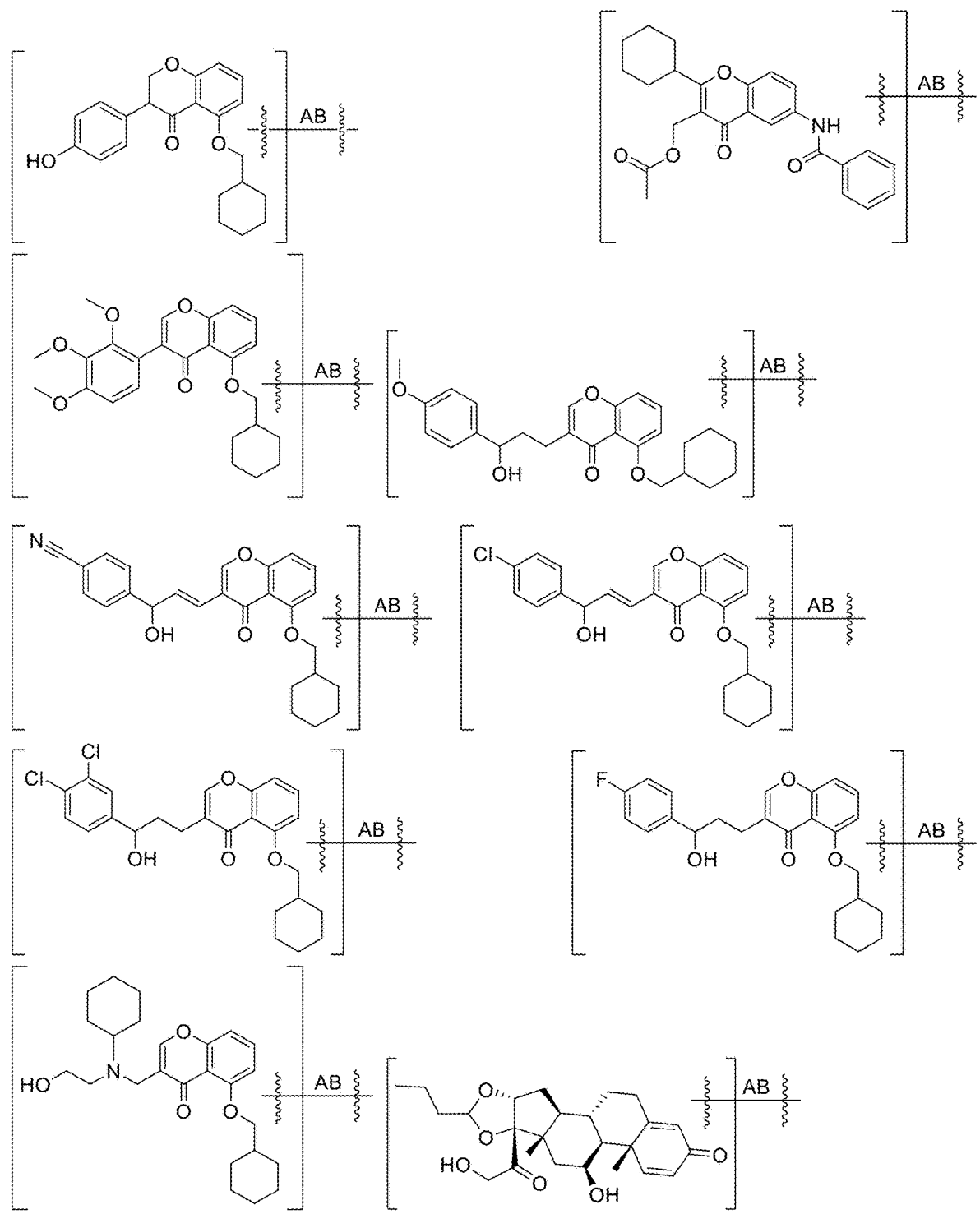
FIG. 1BBBB

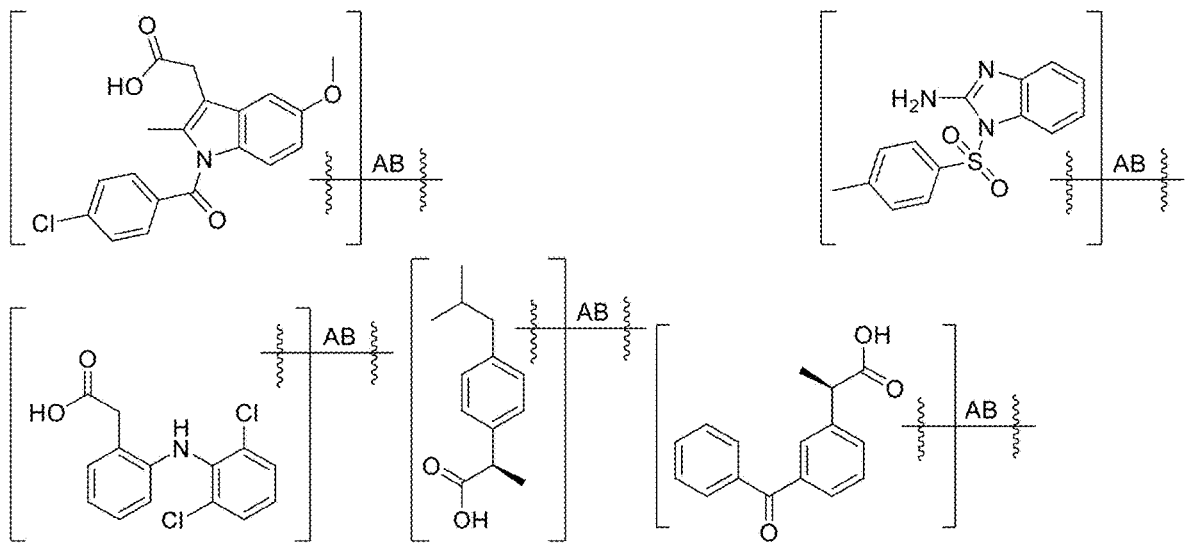
FIG. 1CCCC
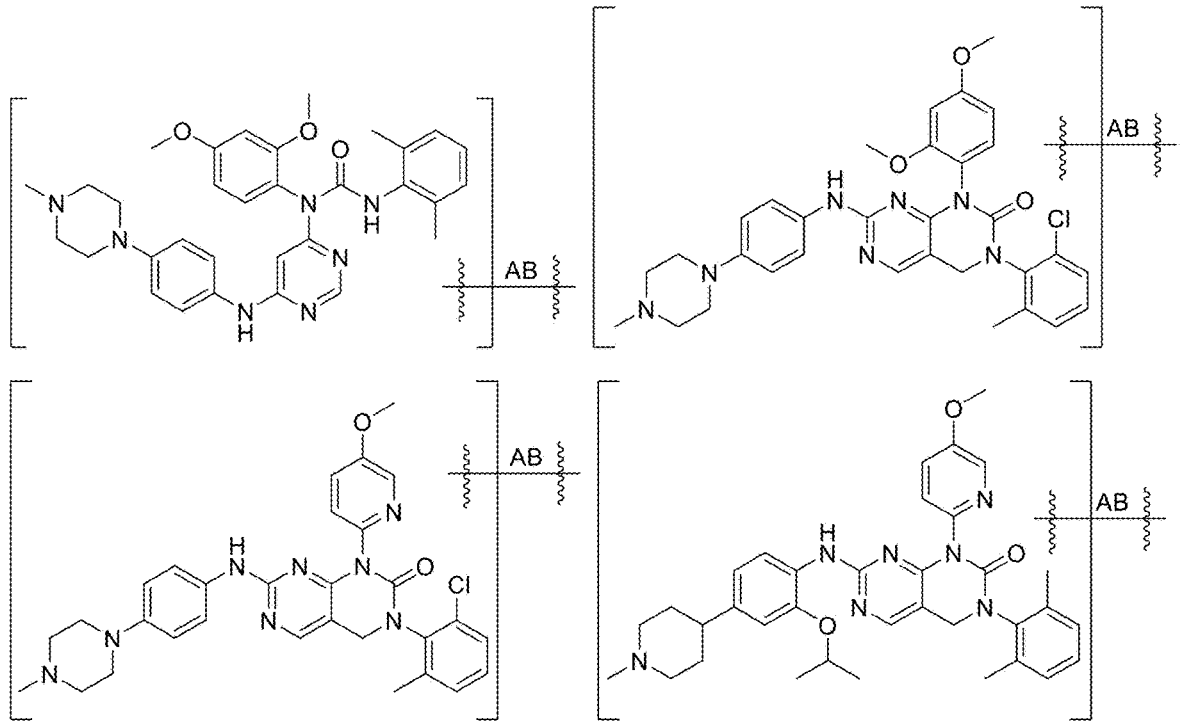
FIG. 1DDDD

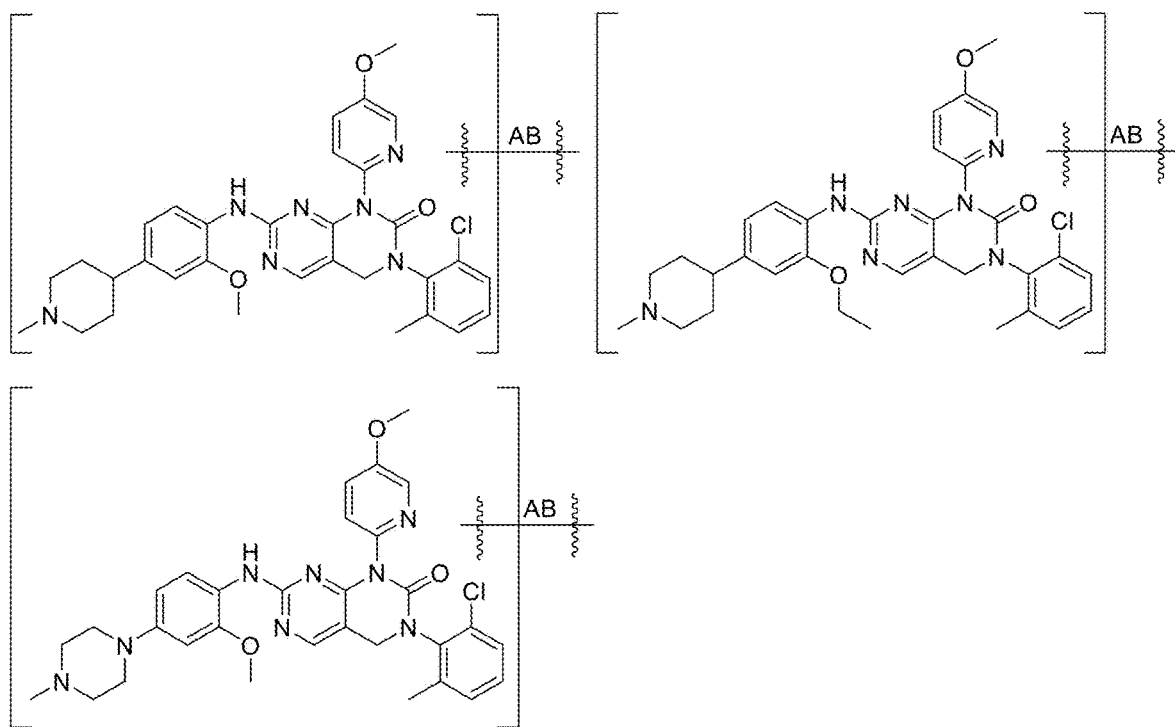
FIG. 1EEEE
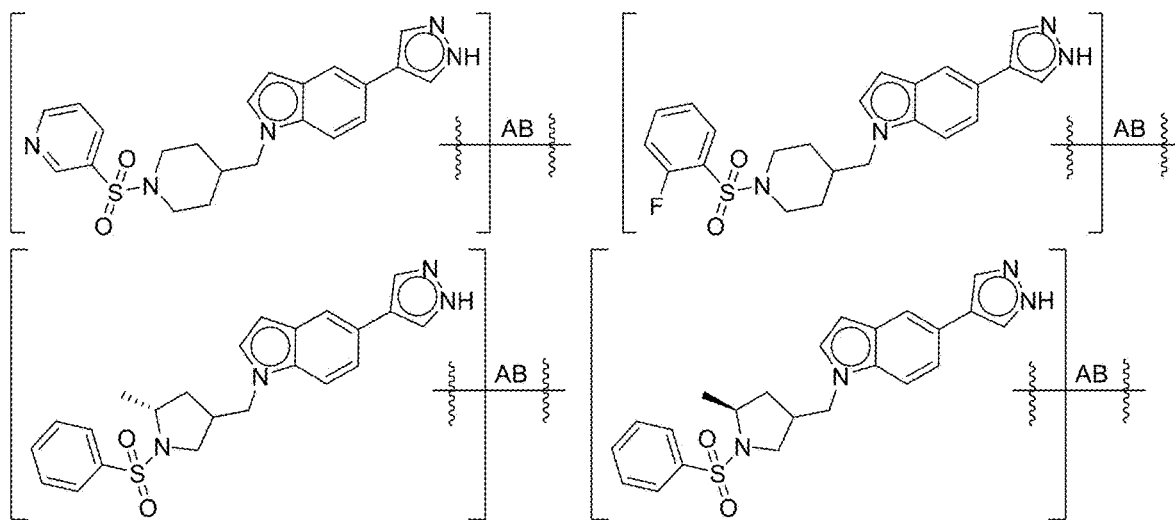
FIG. 1FFFF

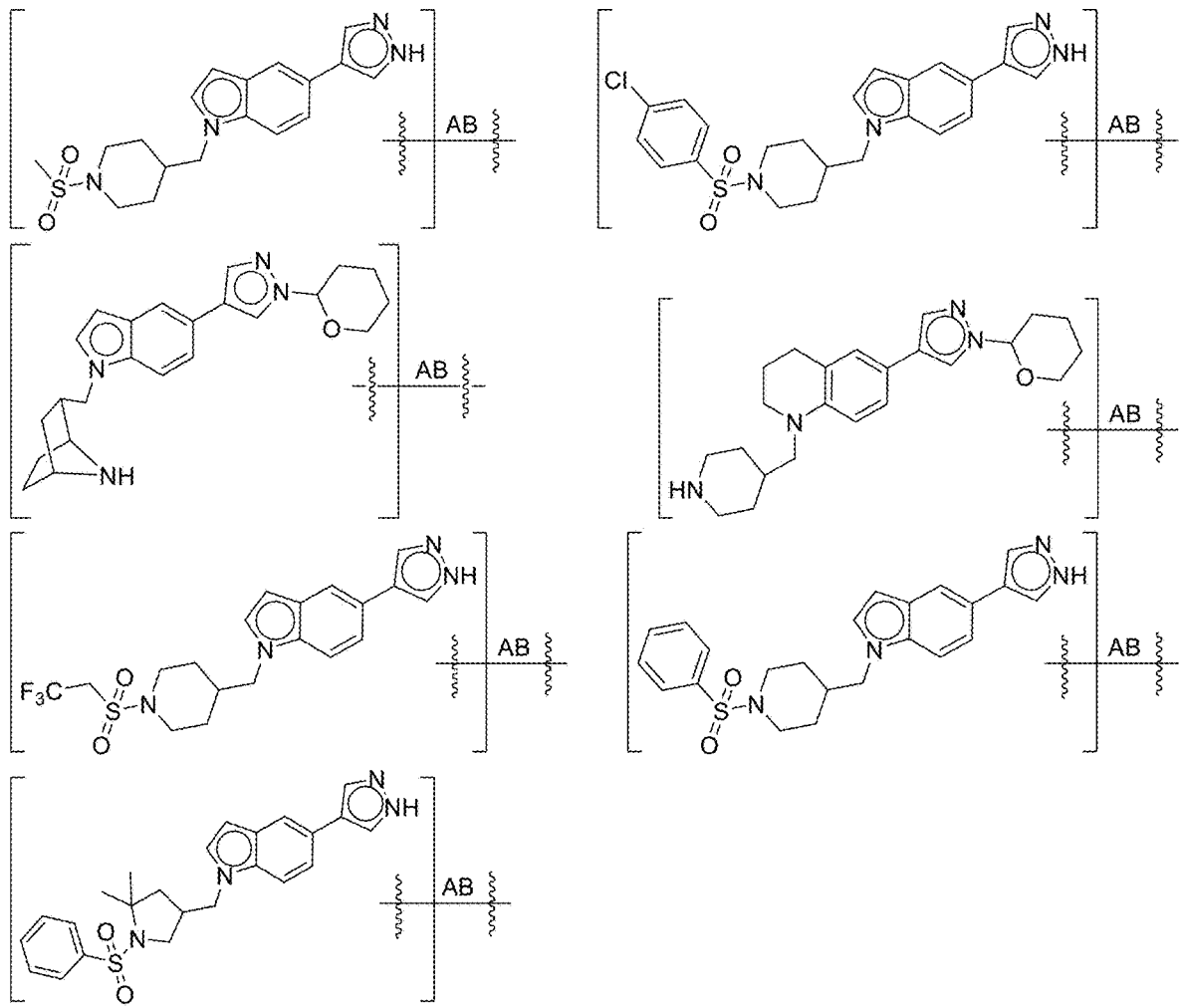
FIG. 1GGGG
FIG. 1HHHH

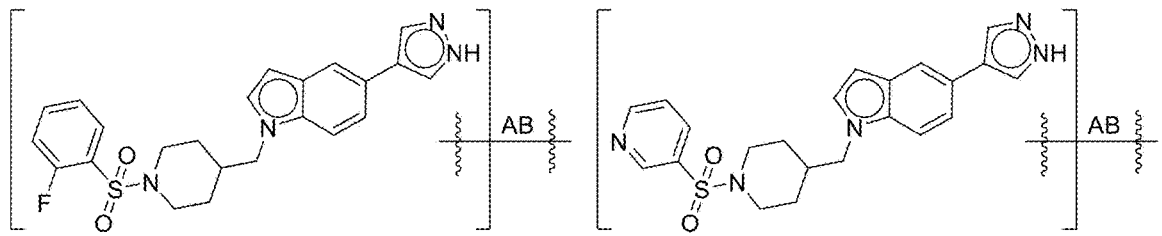
FIG 1IIII
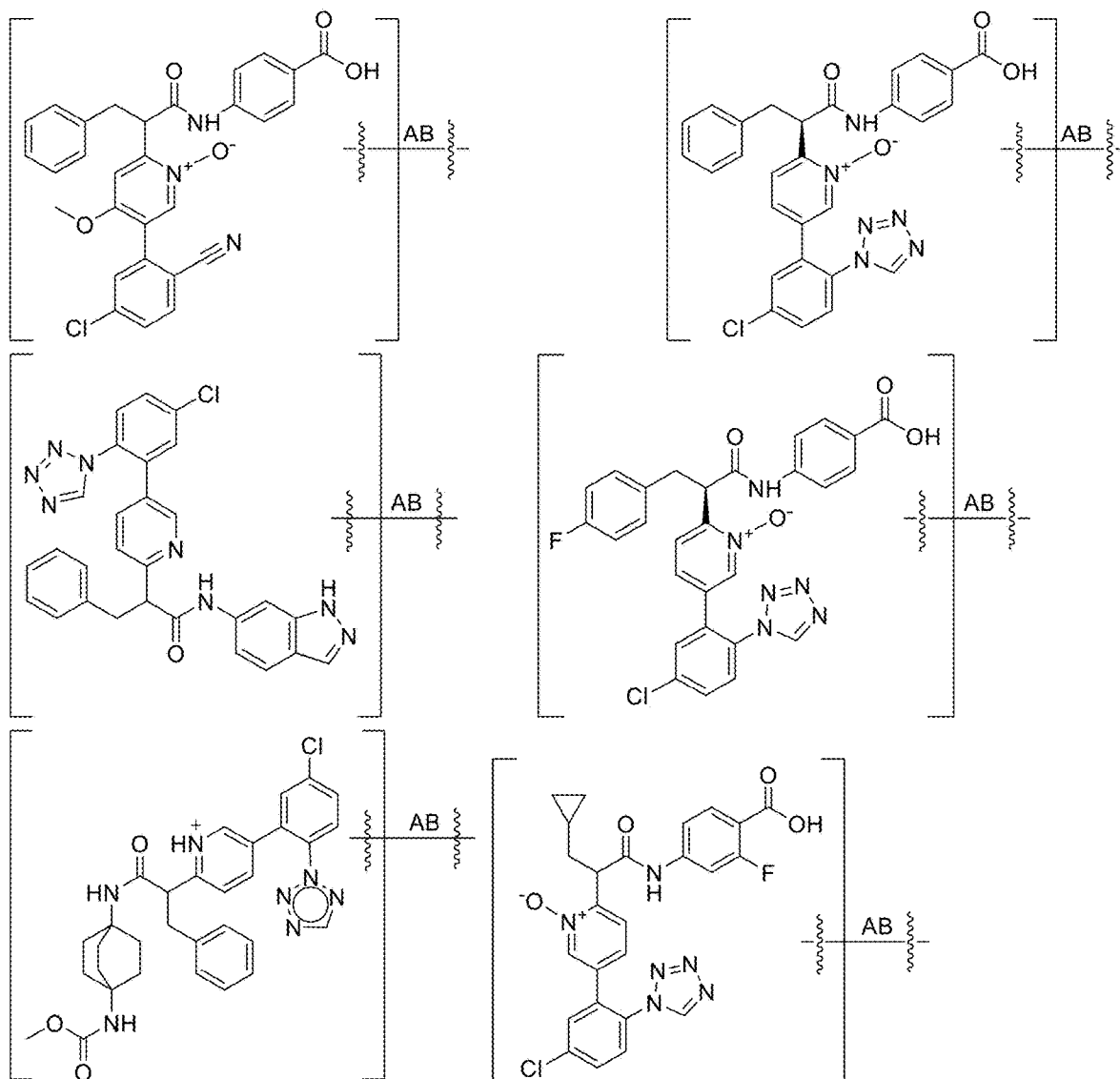
FIG. 1JJJJ

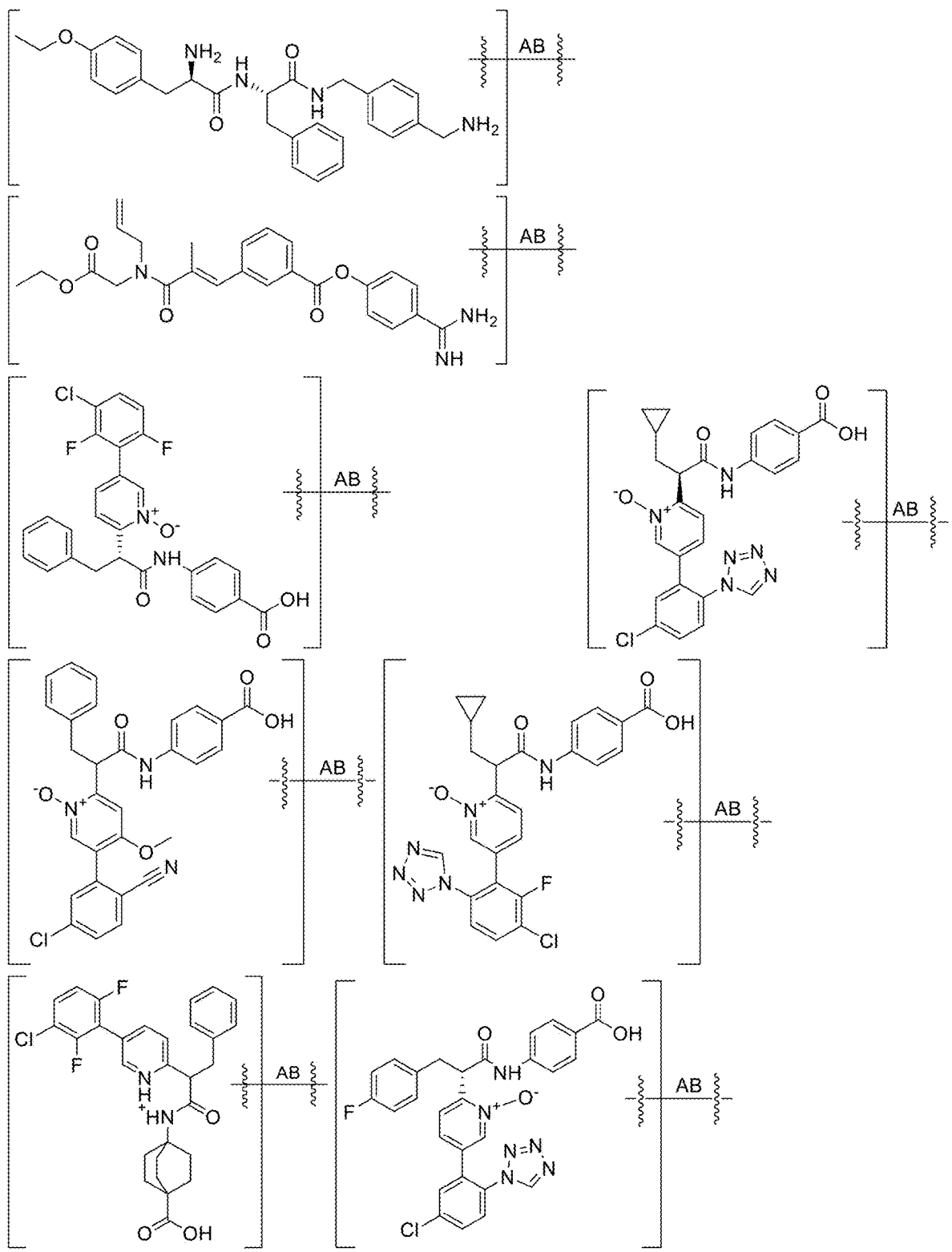
FIG. 1KKKK

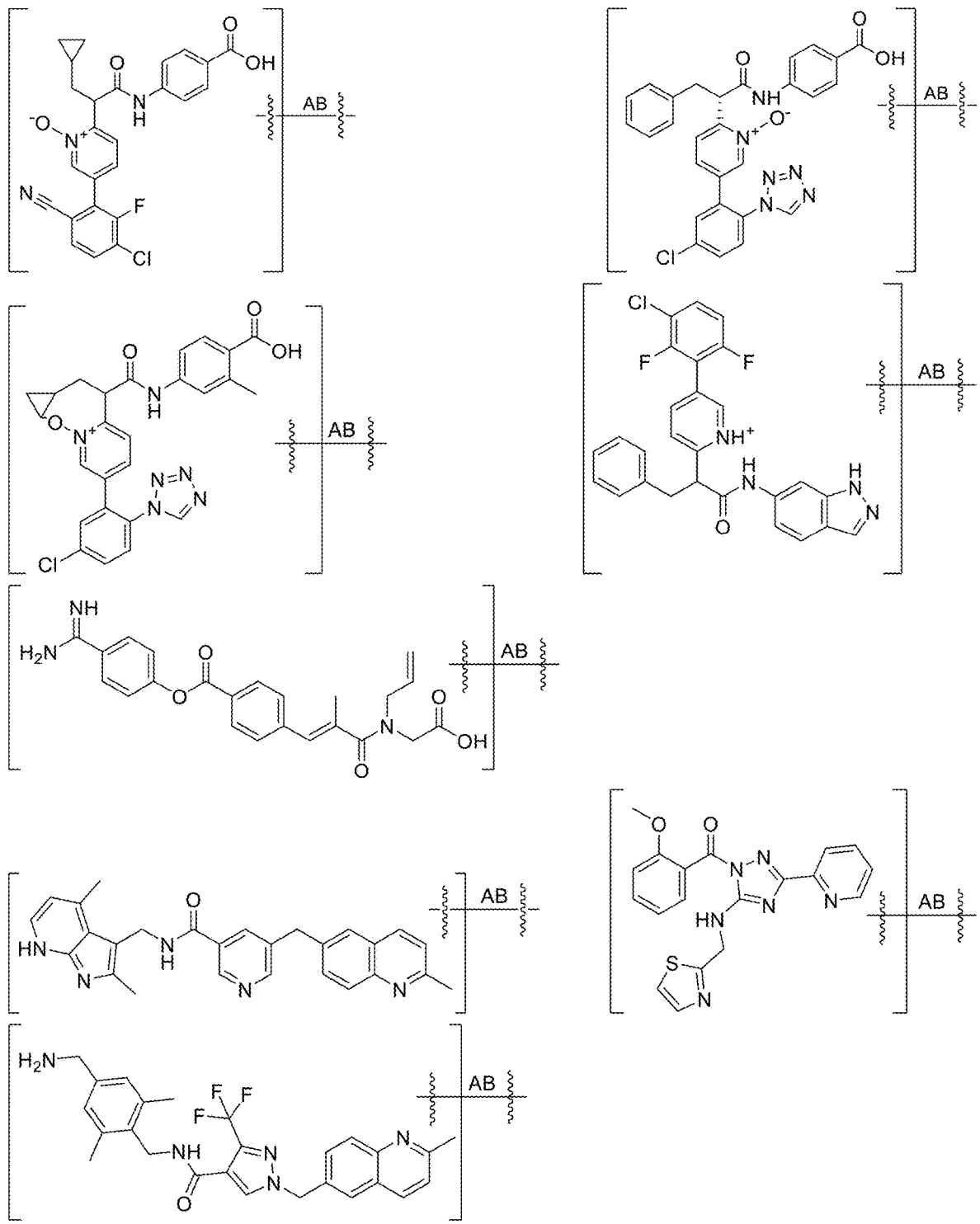
FIG. 1LLLL

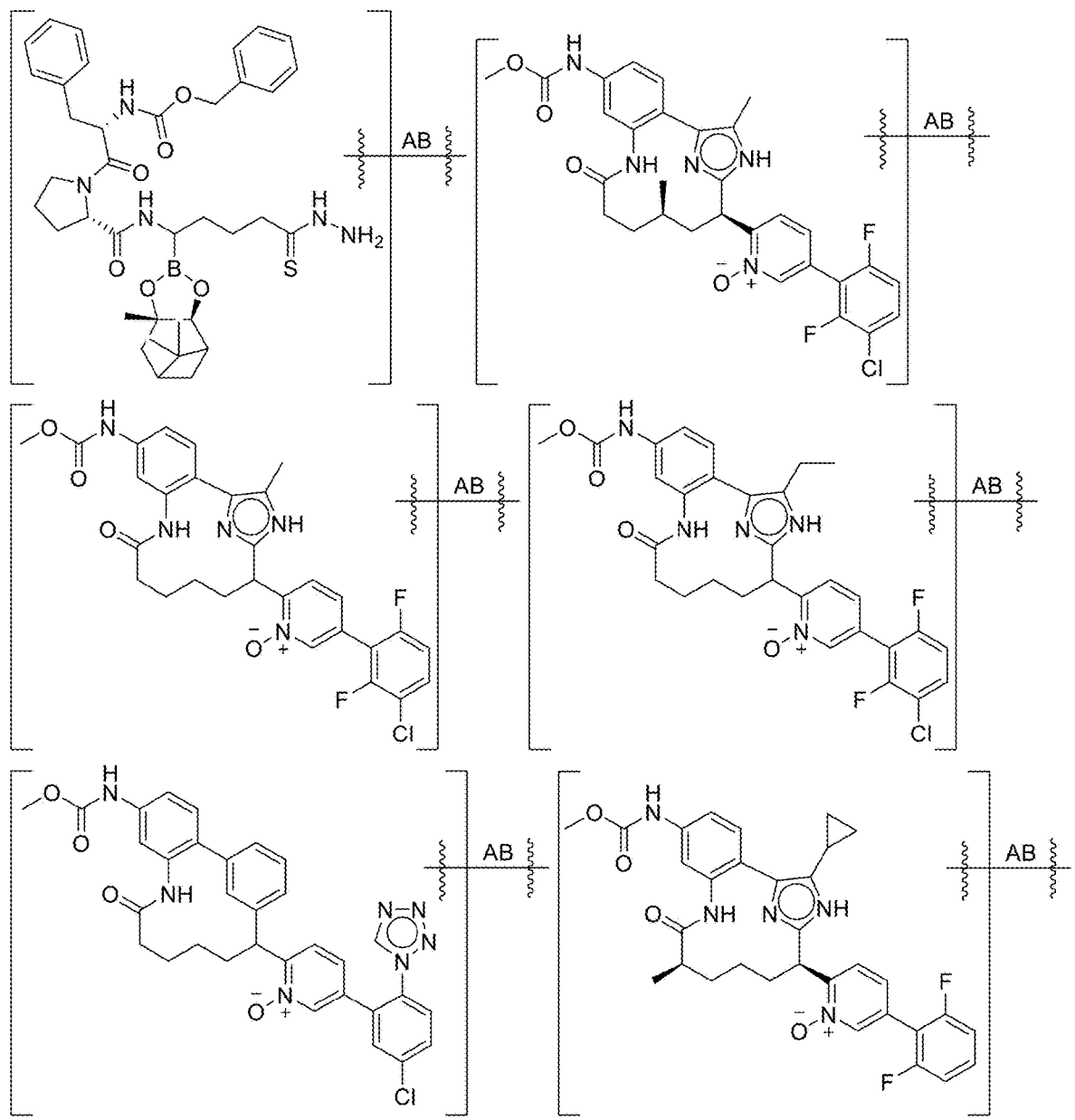
FIG. 1MMMM

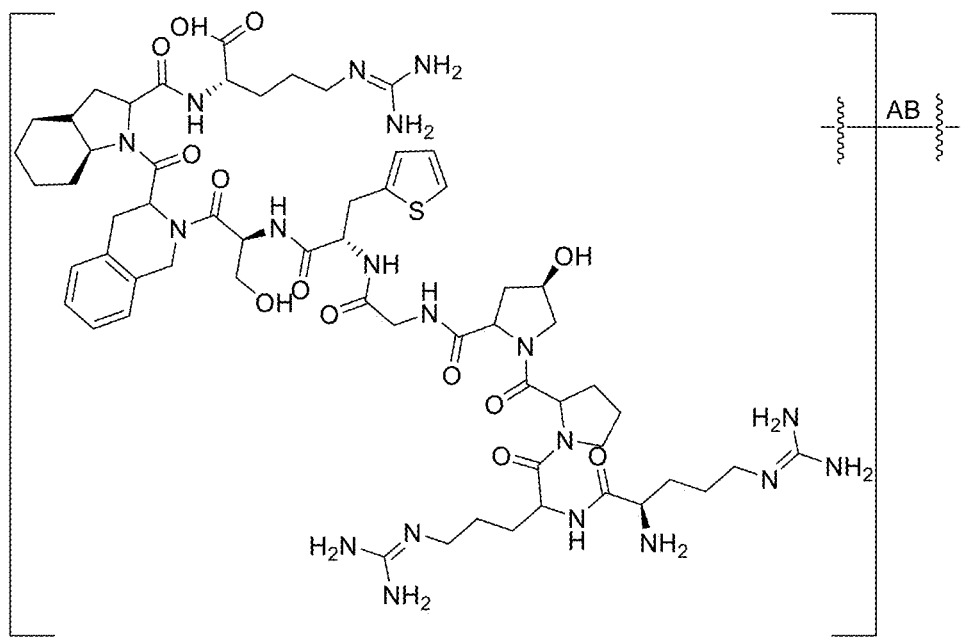
FIG. 1NNNN
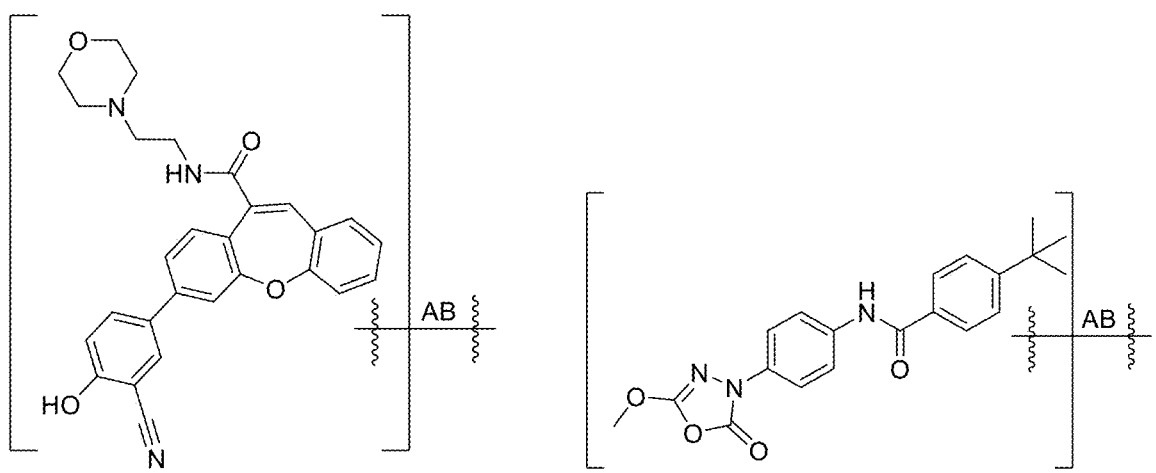
FIG 1OOOO

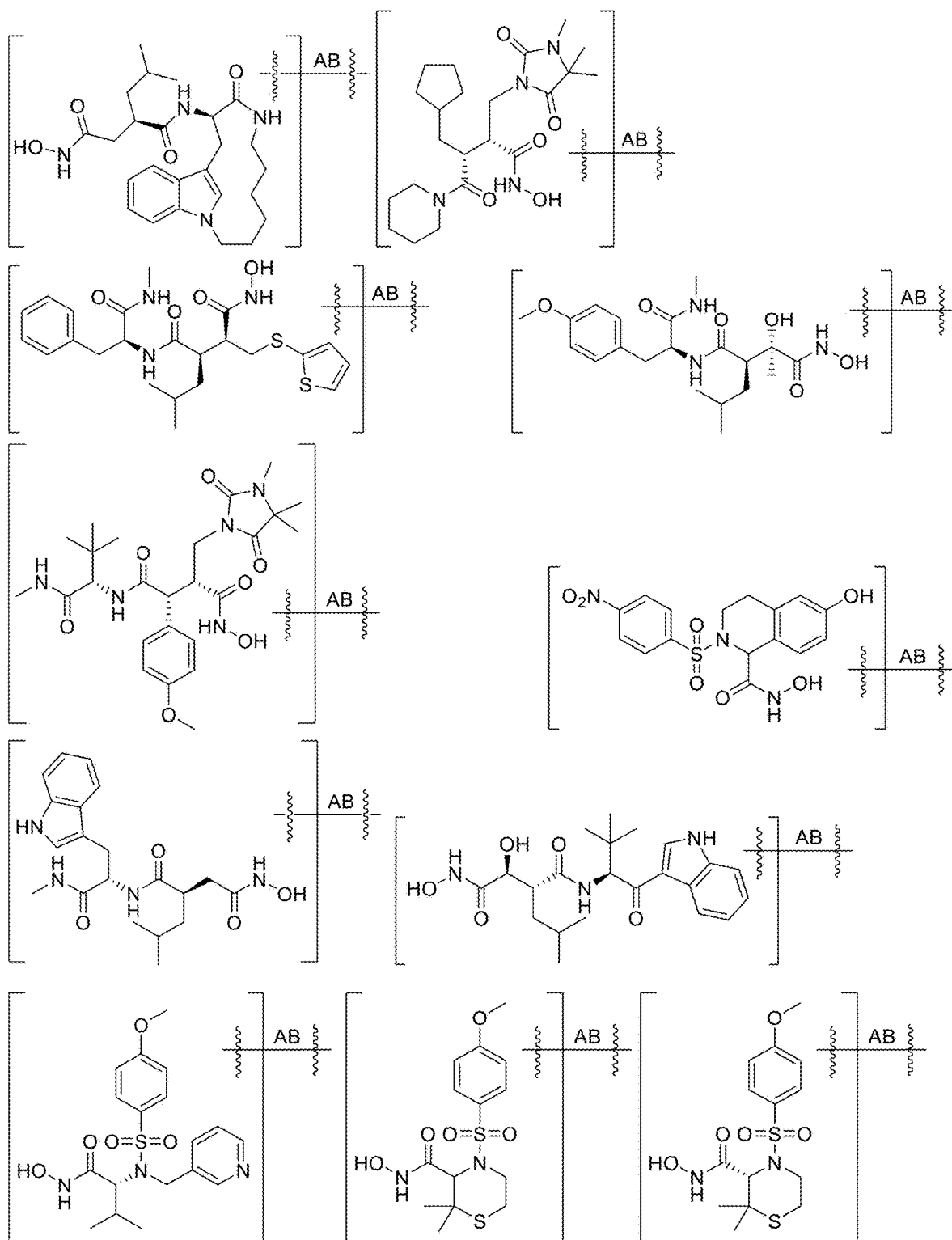
FIG. 1PPPP

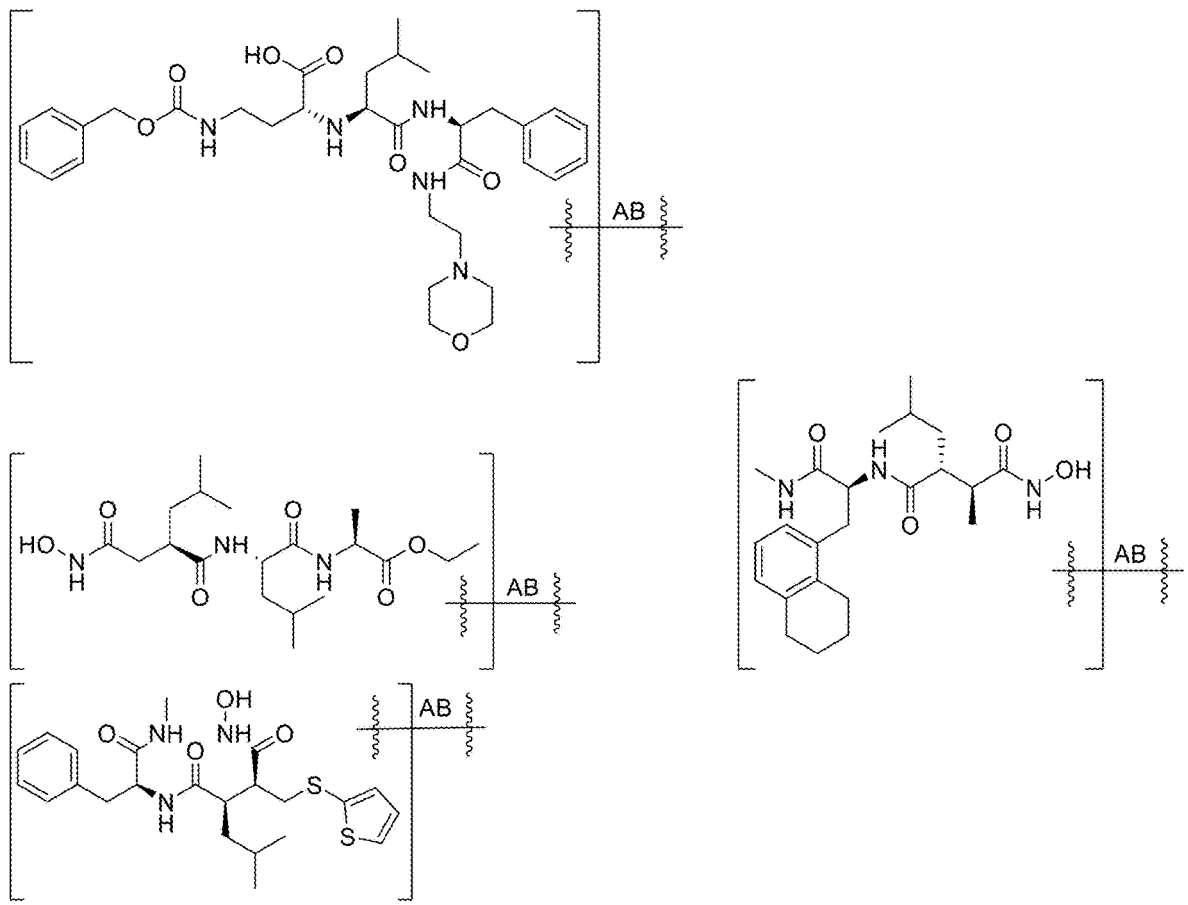
FIG. 1QQQQ
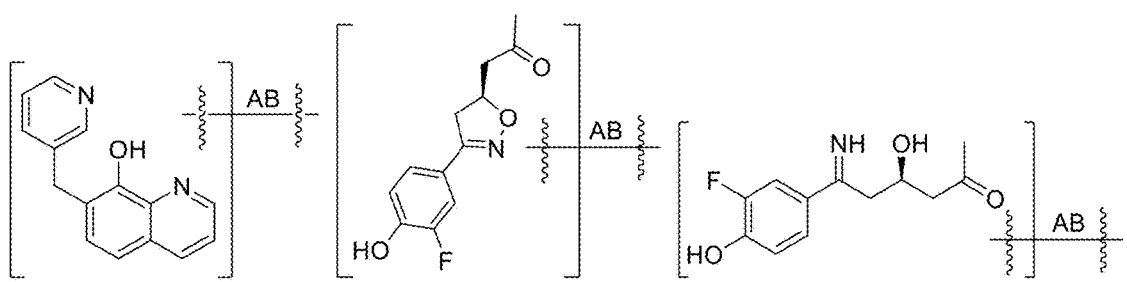
FIG. 1RRRR

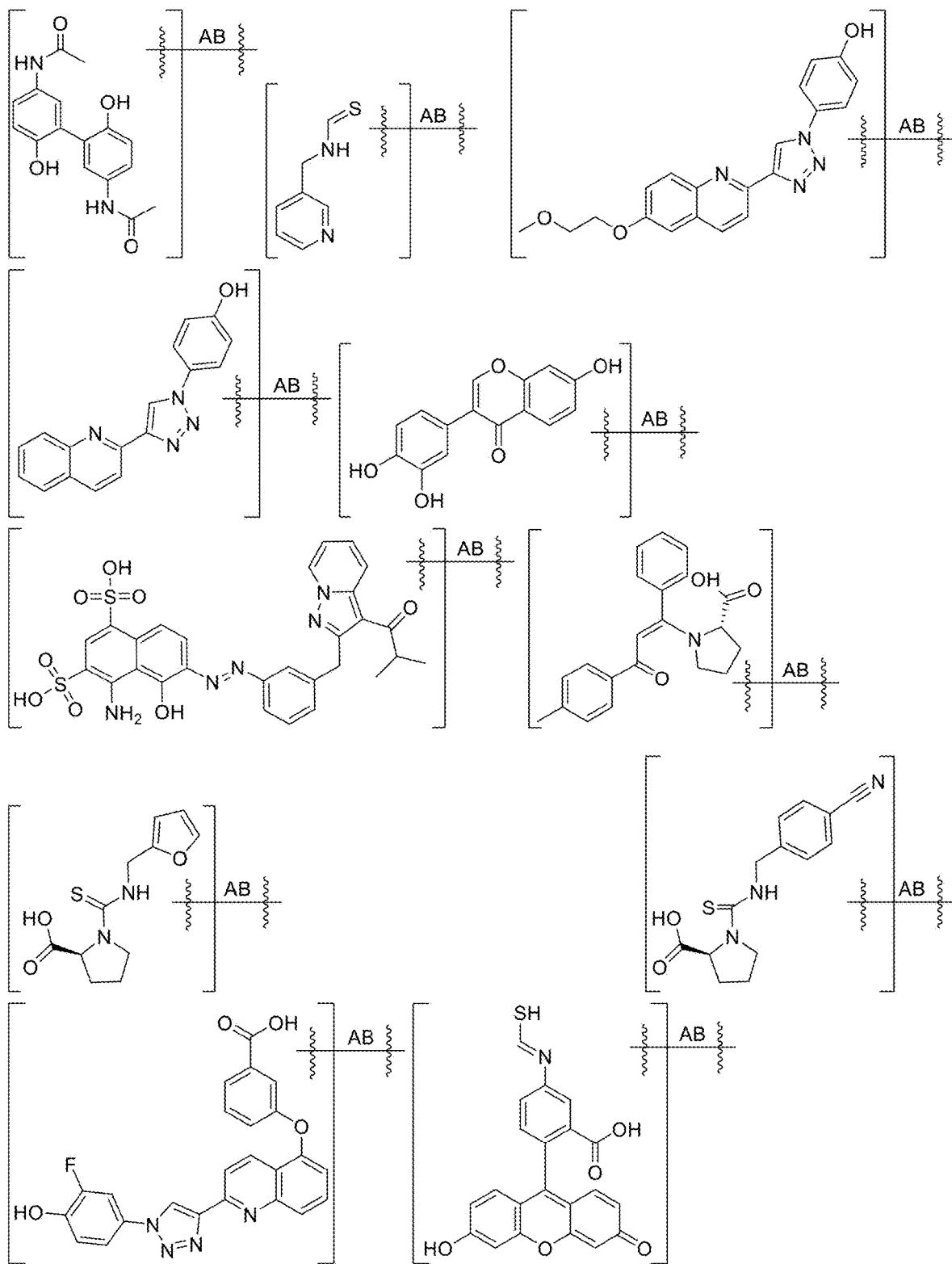
FIG. 1SSSS

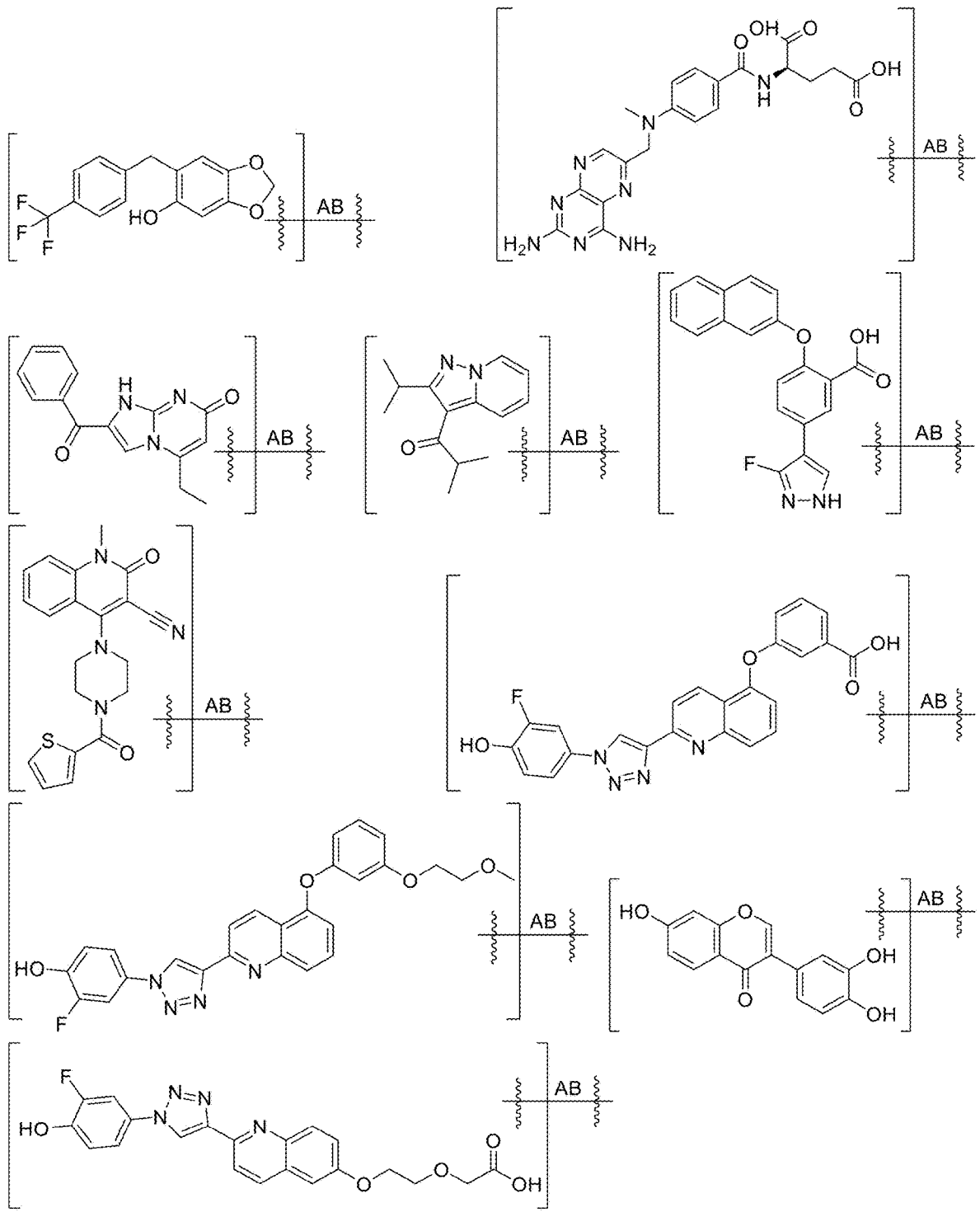
FIG. 1TTTT

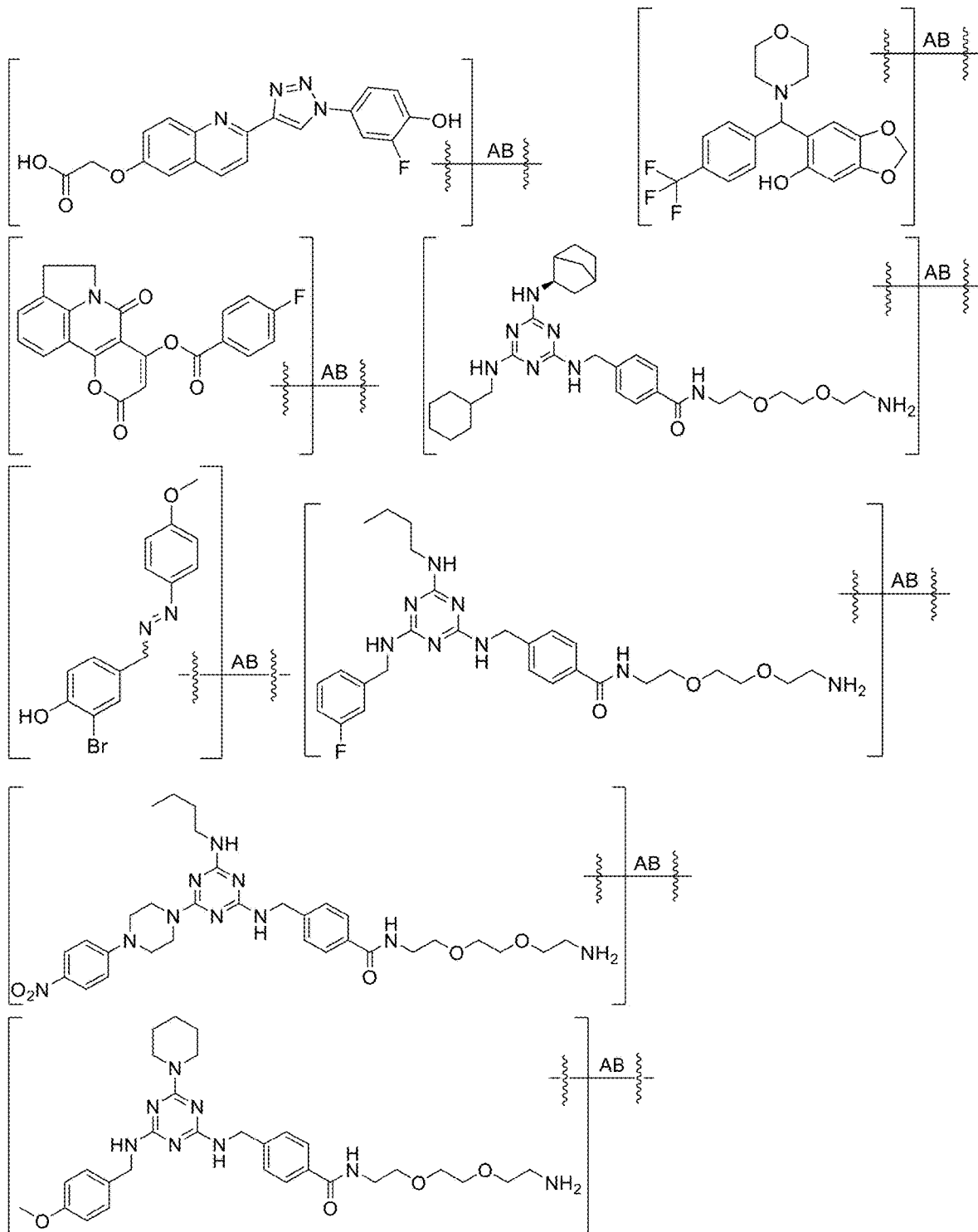
FIG. 1UUUU

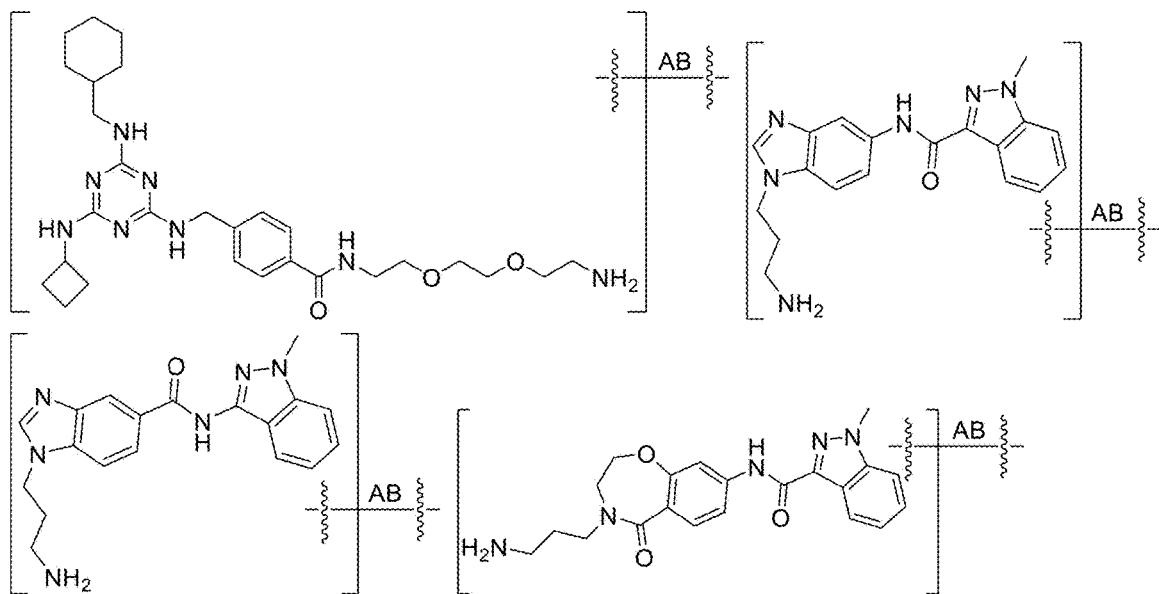
FIG. 1VVVV
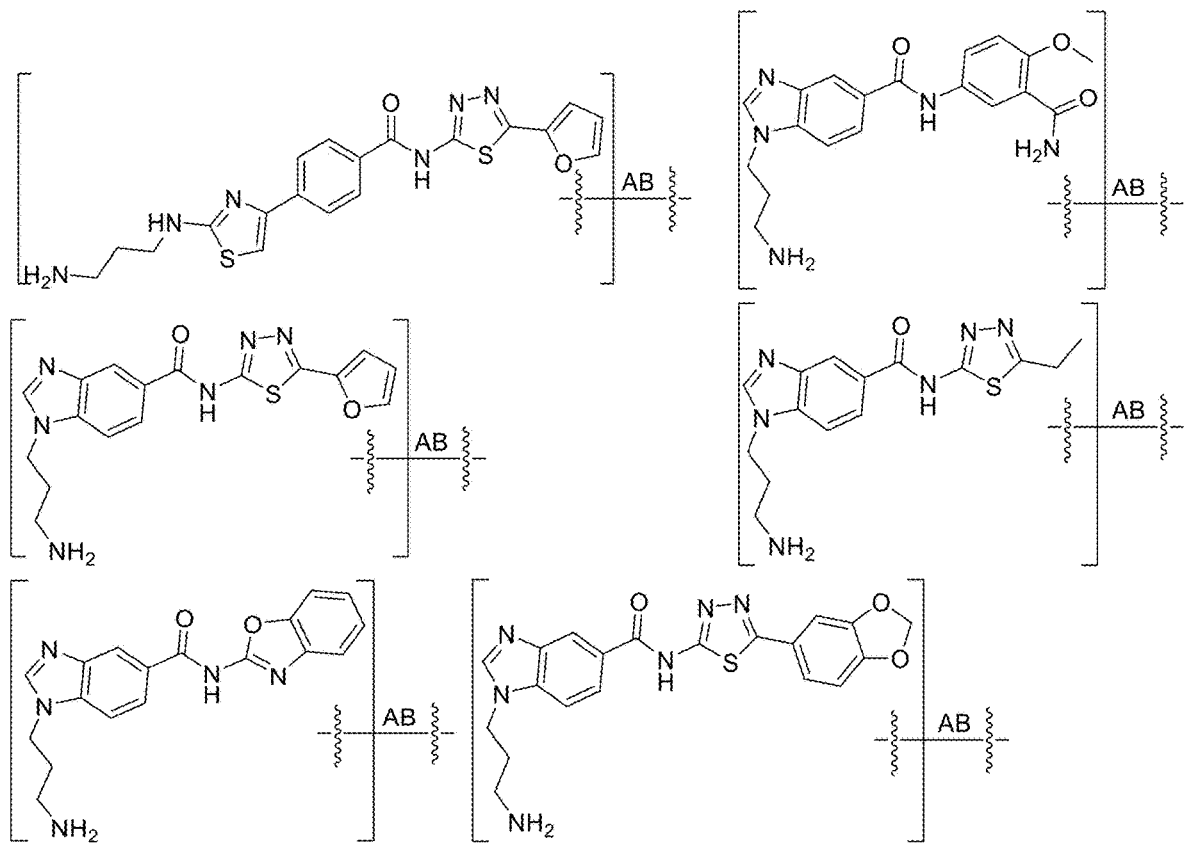
FIG. 1WWWW

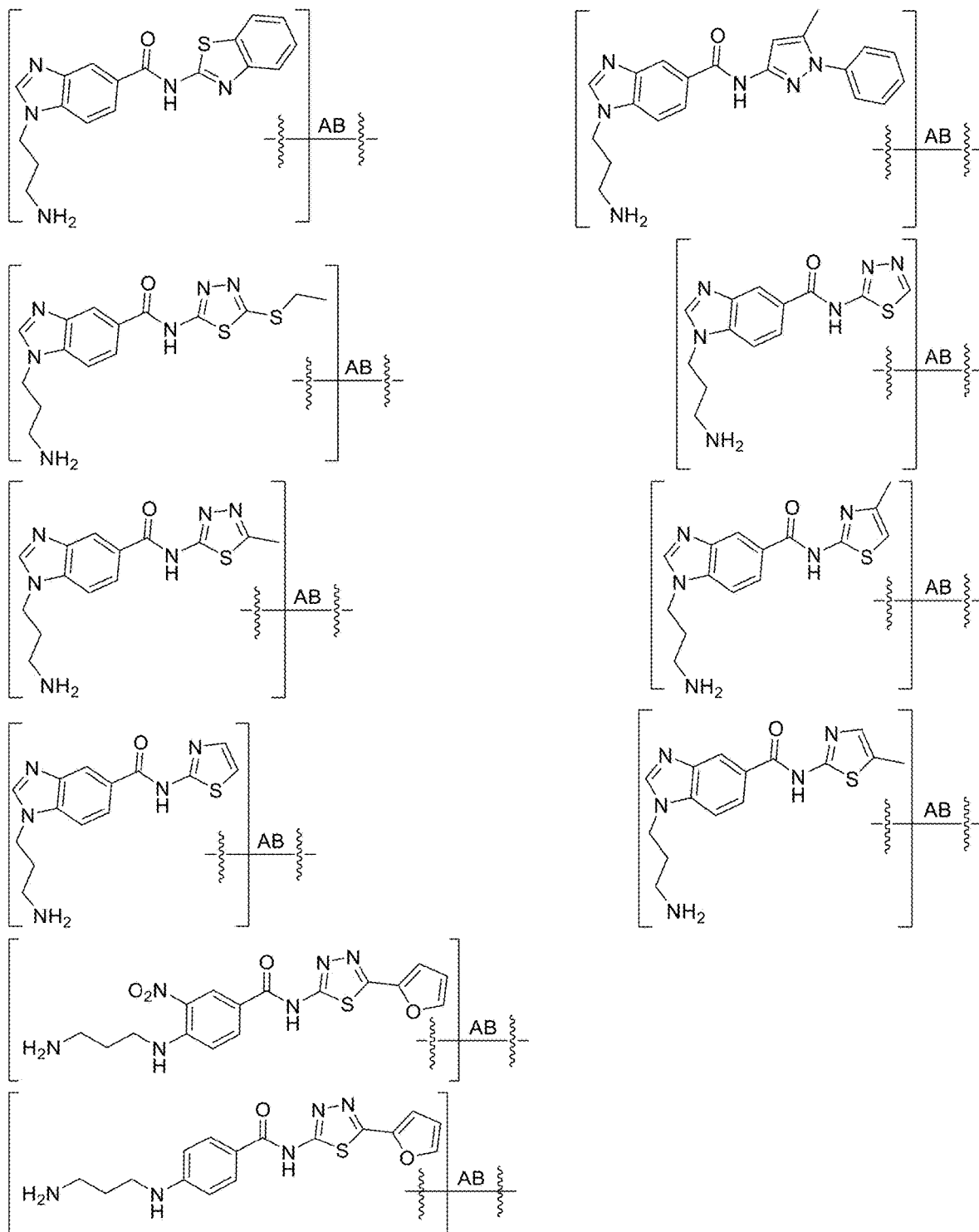
FIG. 1XXXX

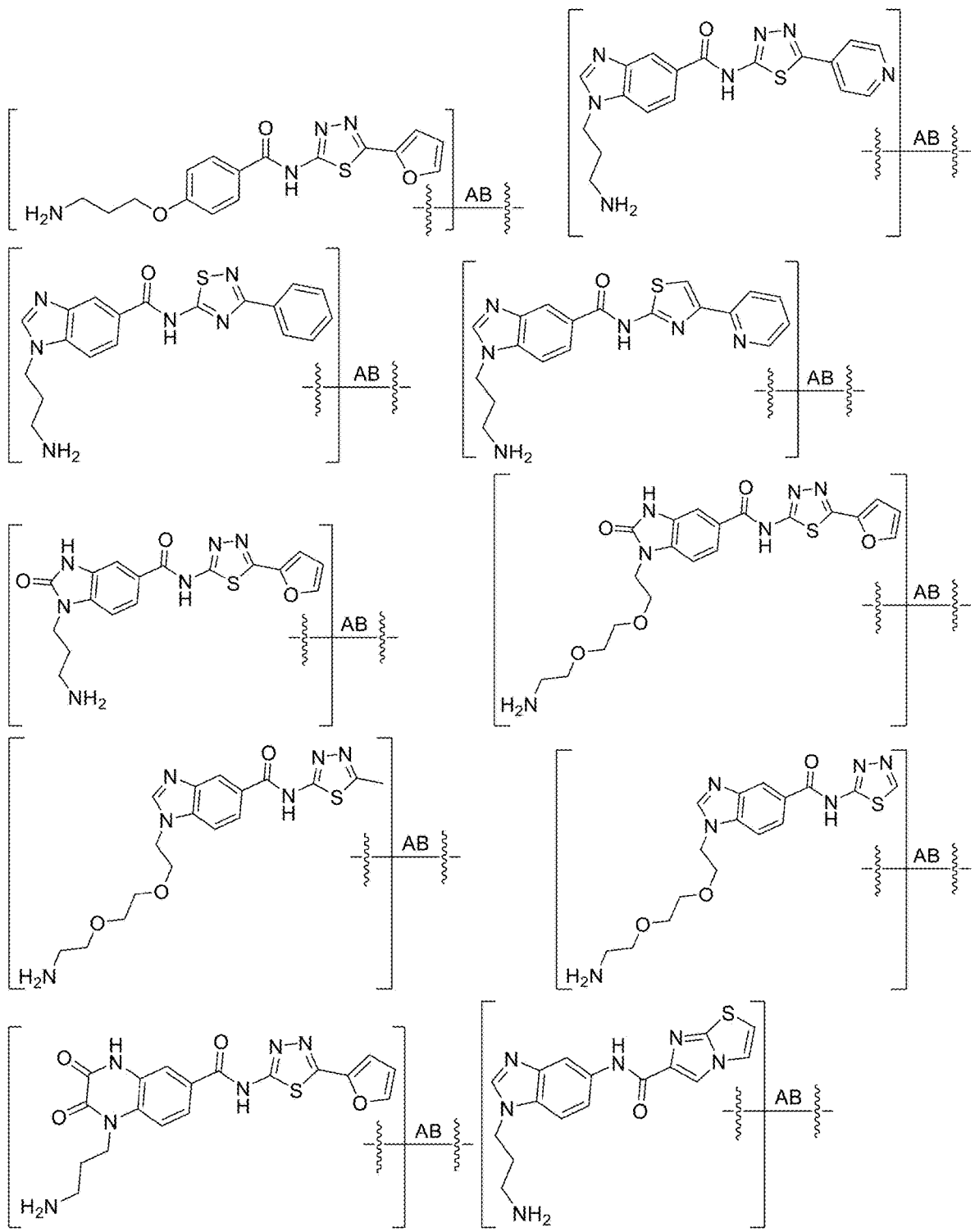
FIG. 1YYYY

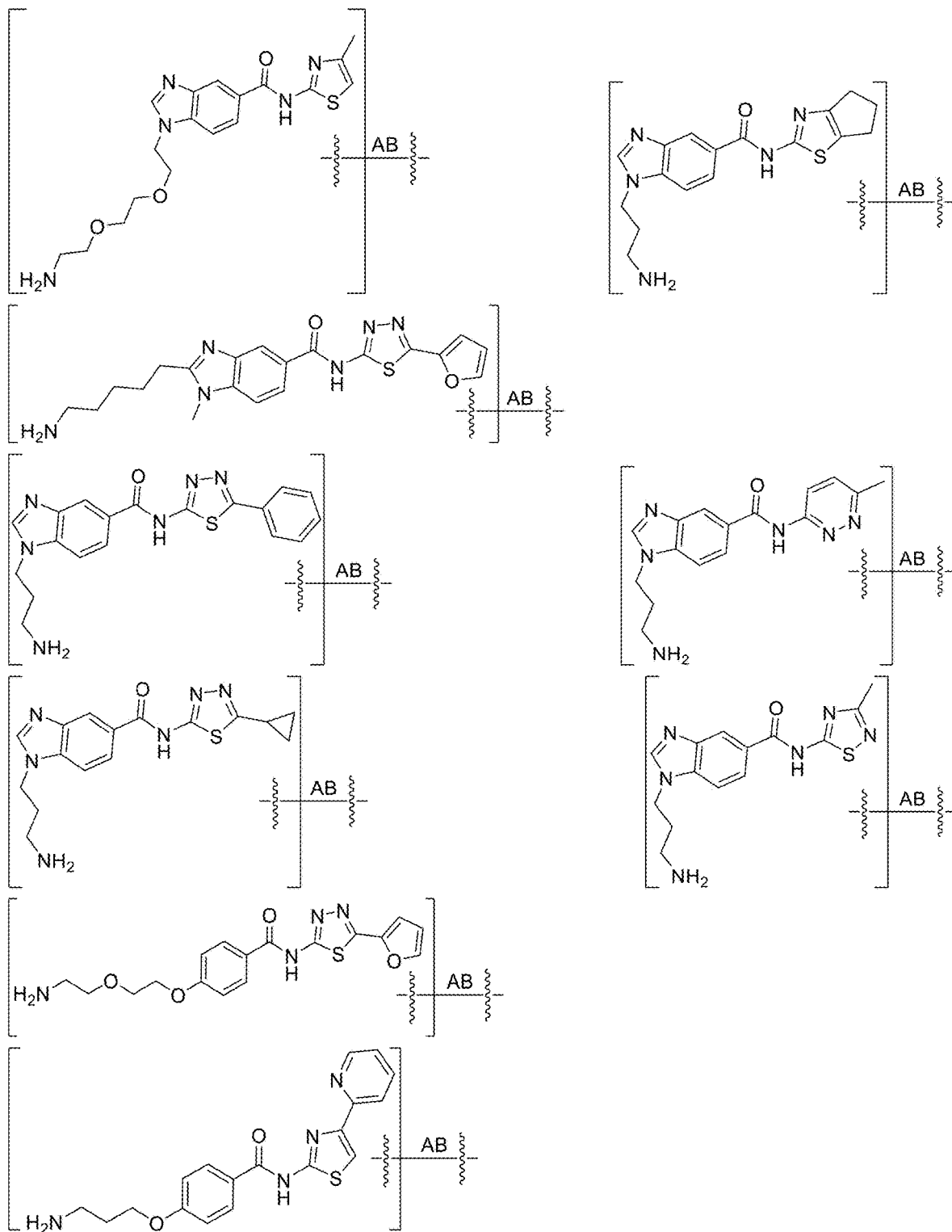
FIG. 1ZZZZ

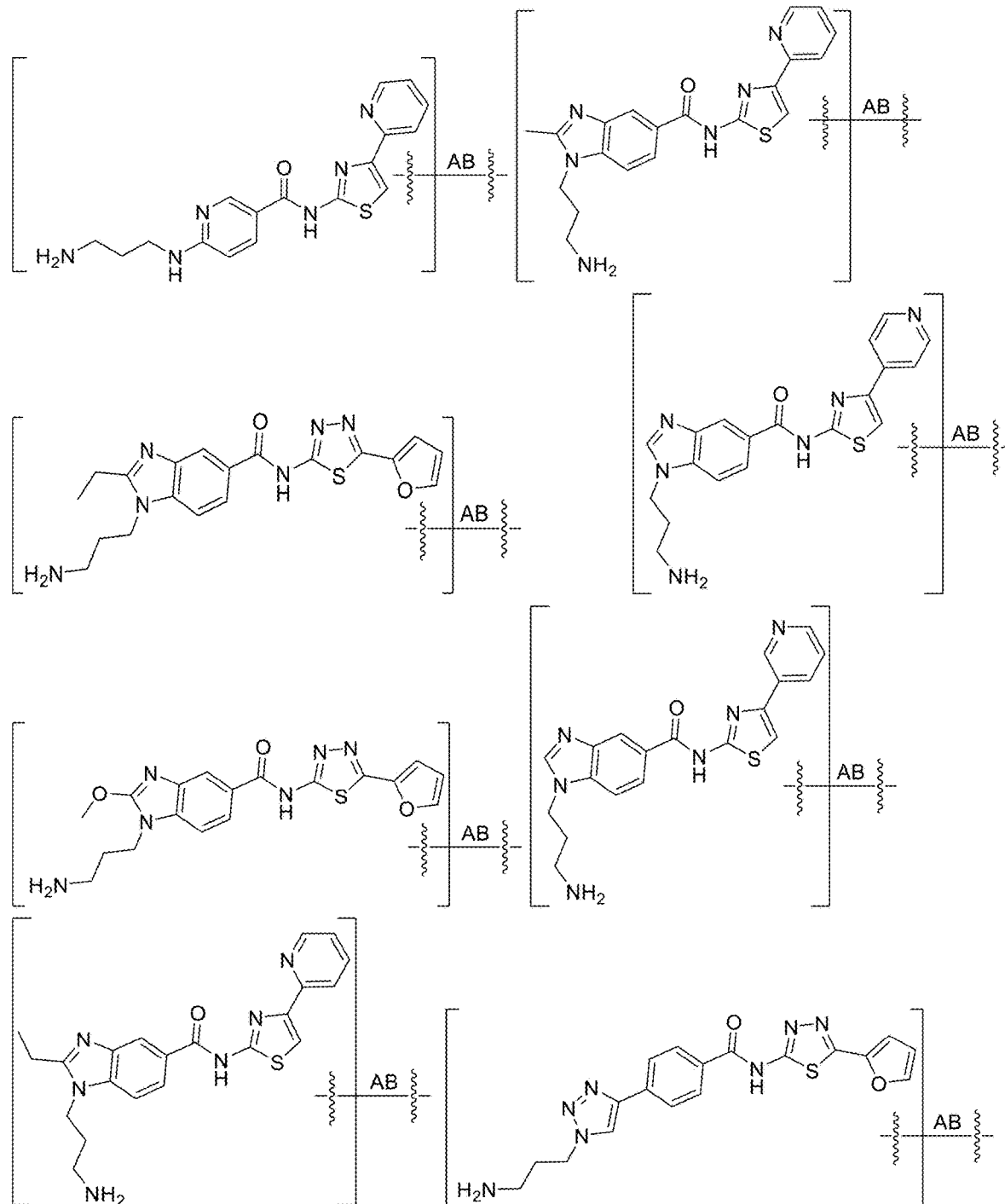
FIG. 1AAAAA

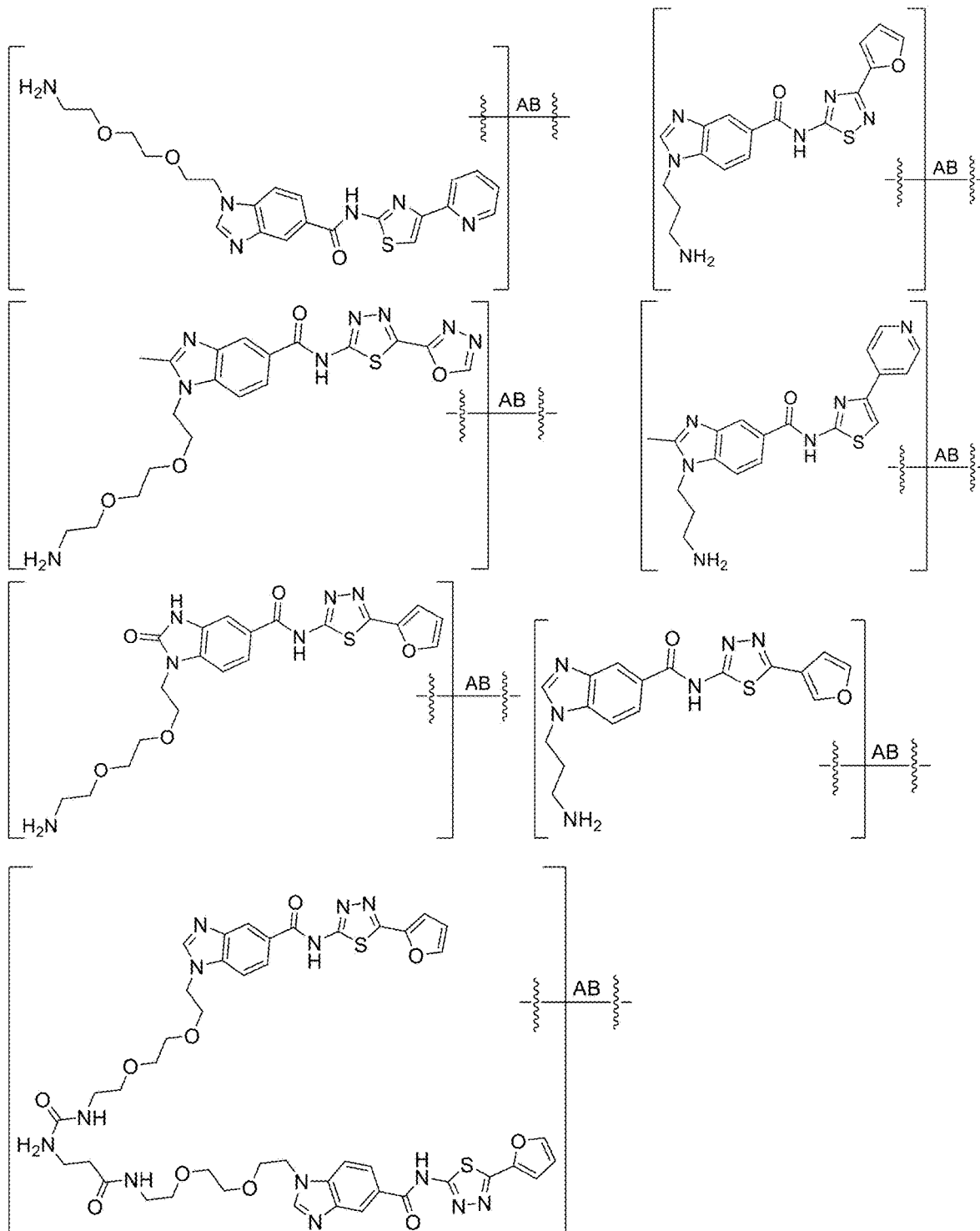
FIG. 1BBBBB

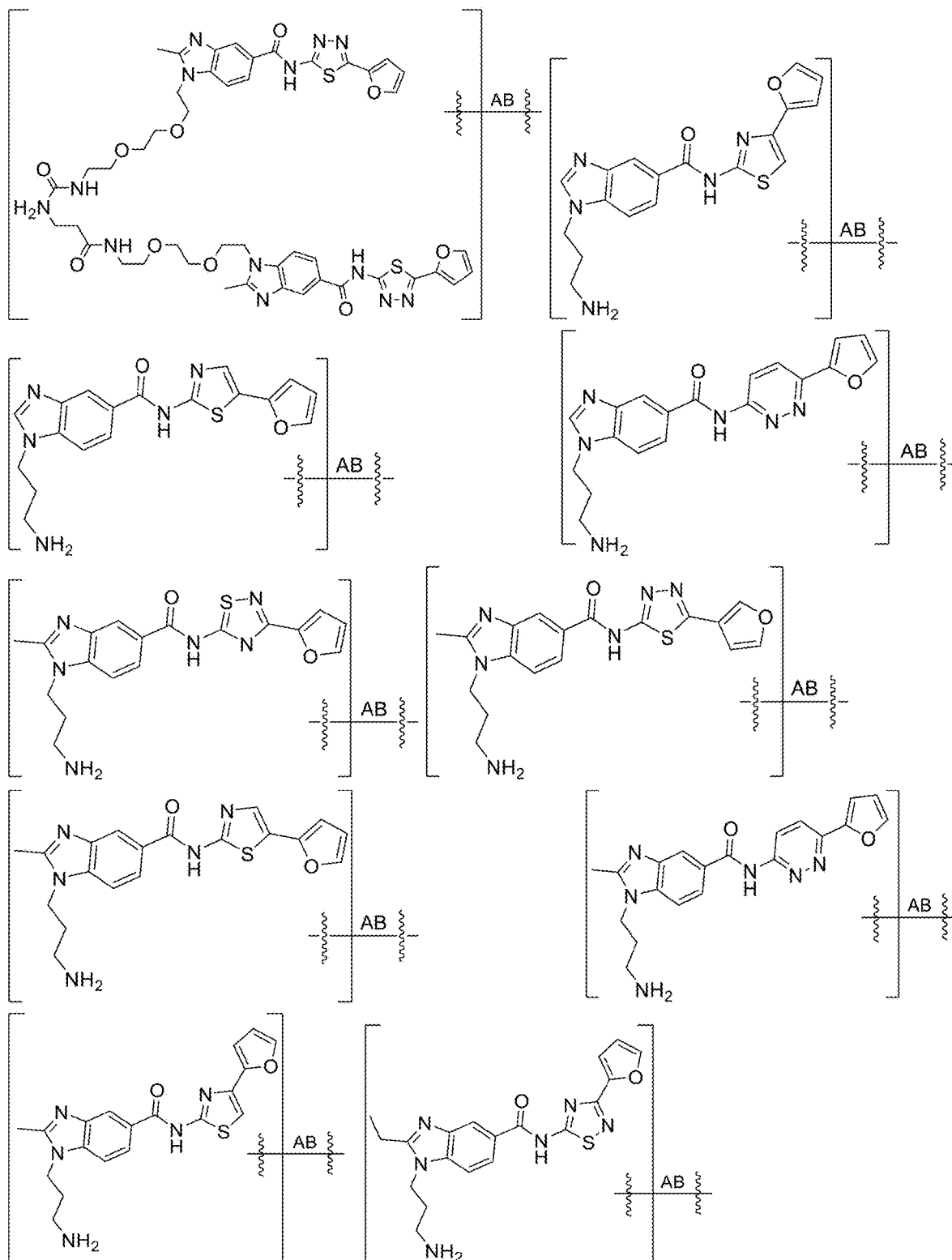
FIG. 1CCCCC

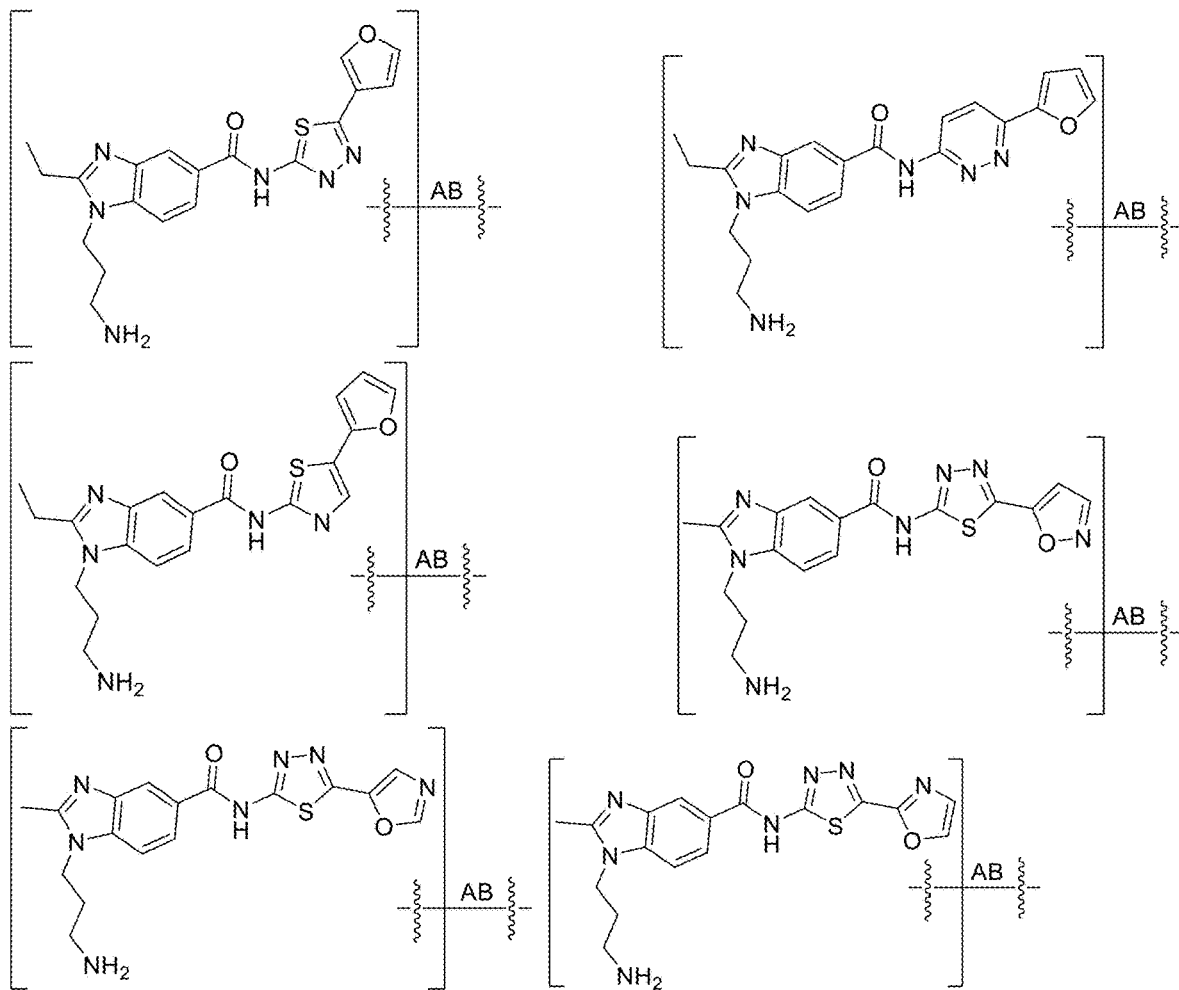
FIG. 1DDDDD

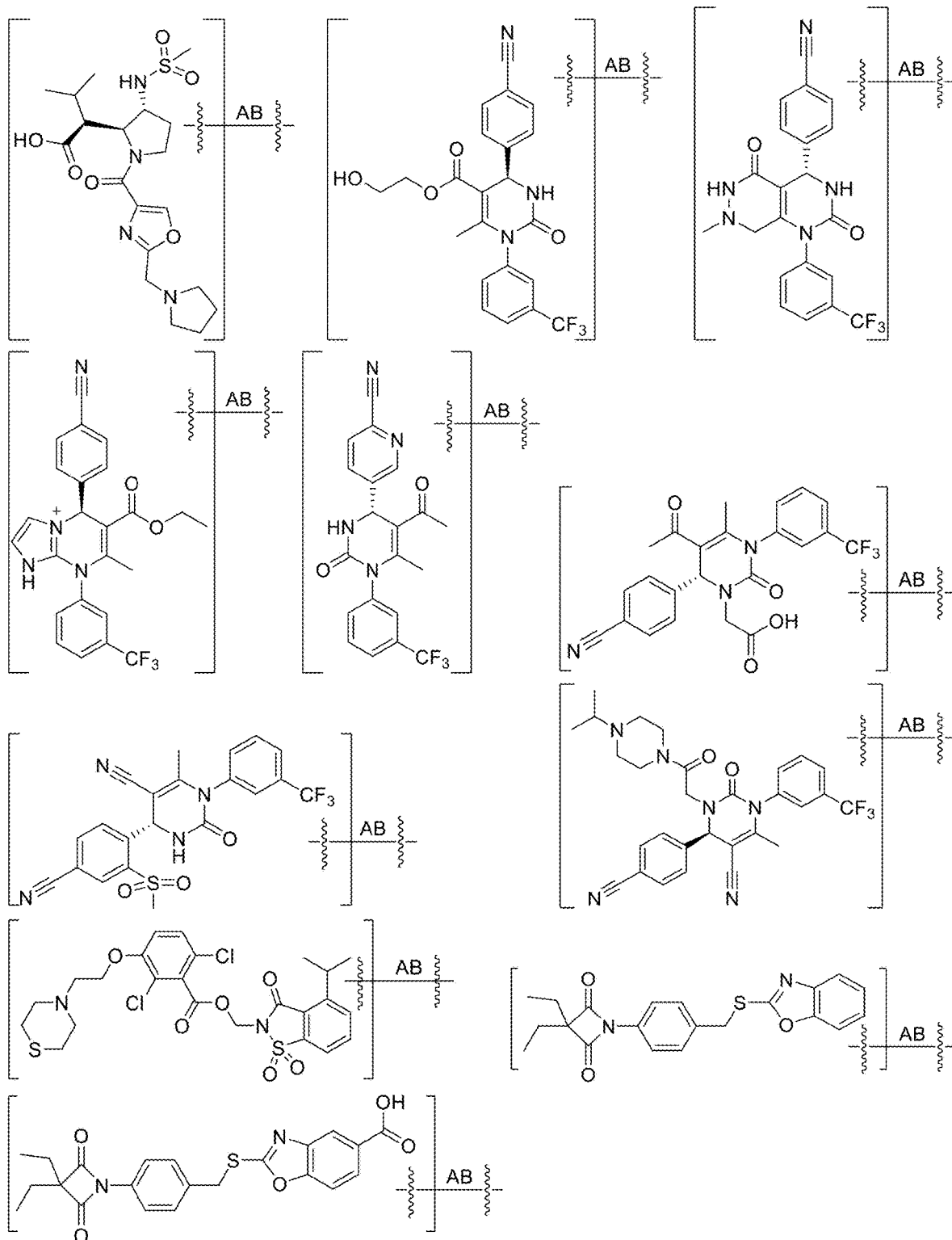
FIG. 1EEEEE

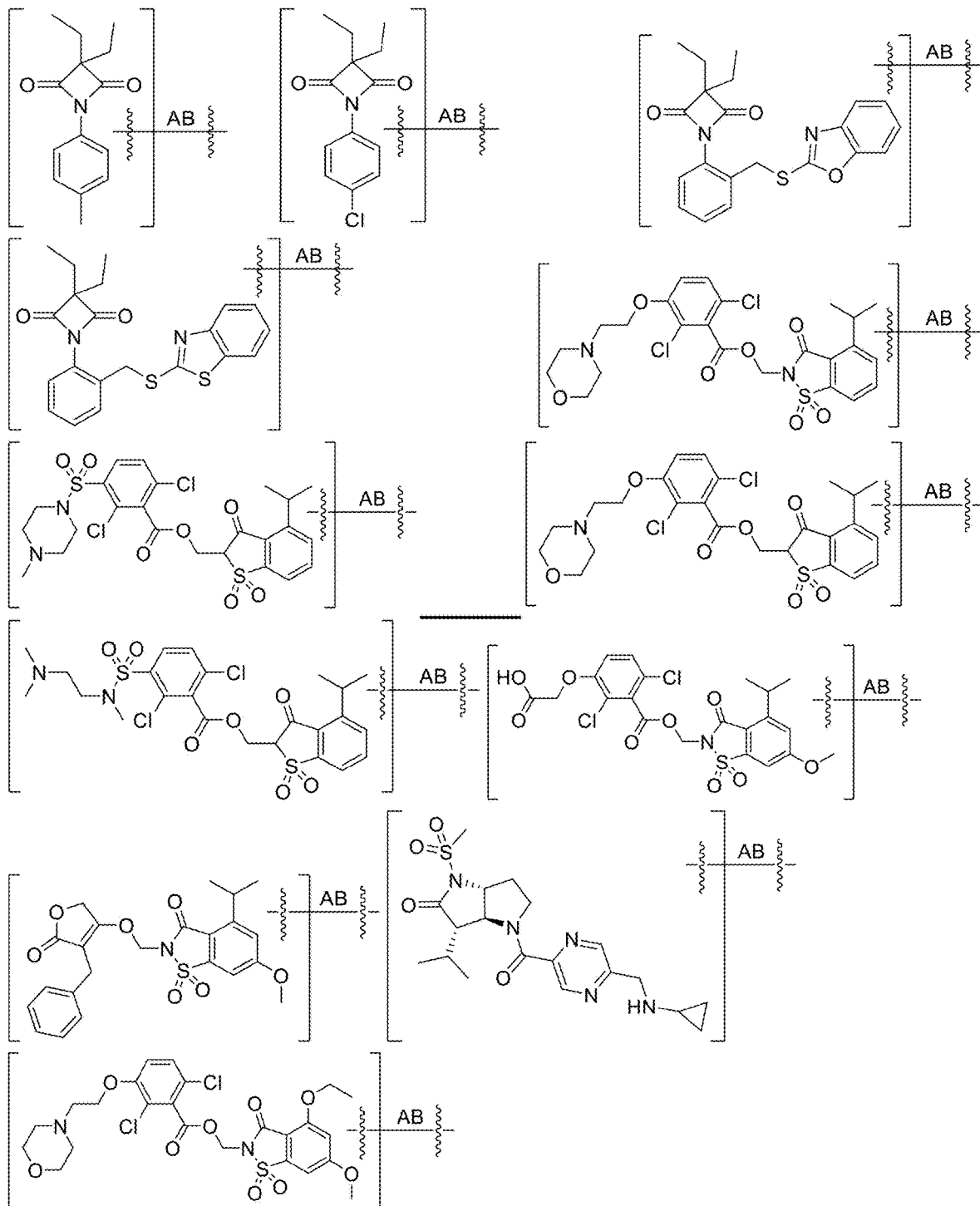
FIG. 1FFFFF

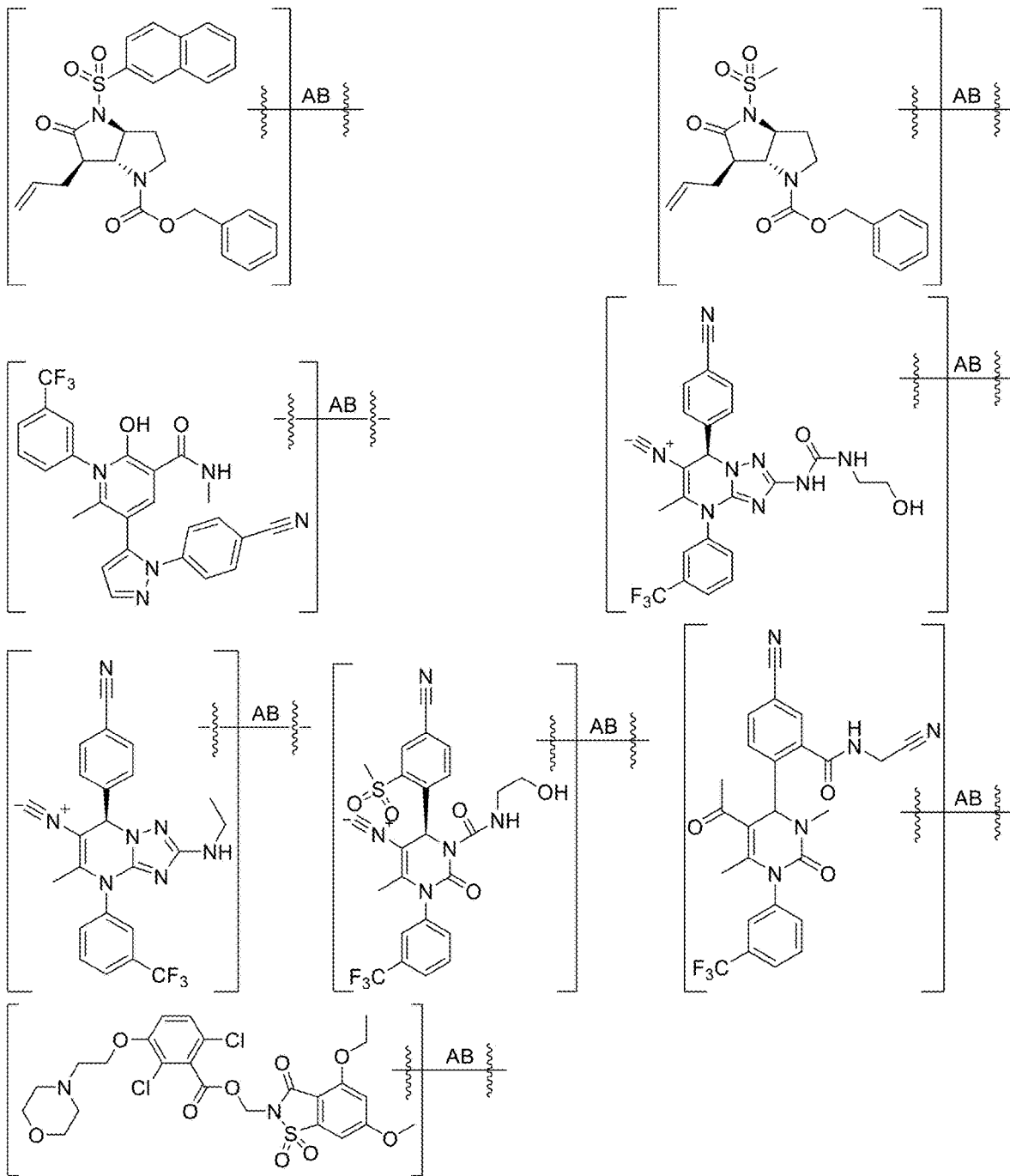
FIG. 1GGGGG

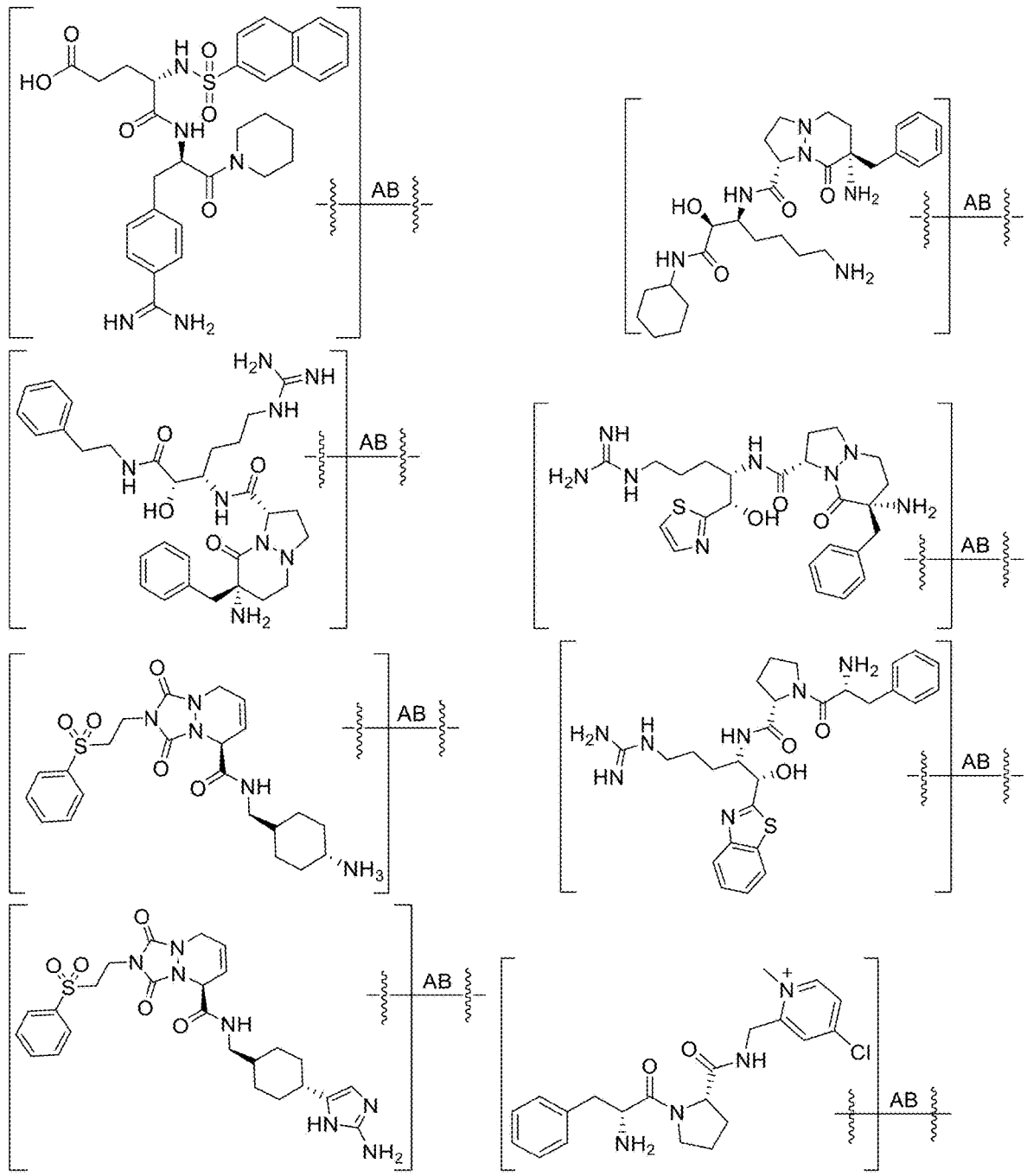
FIG. 1HHHHH

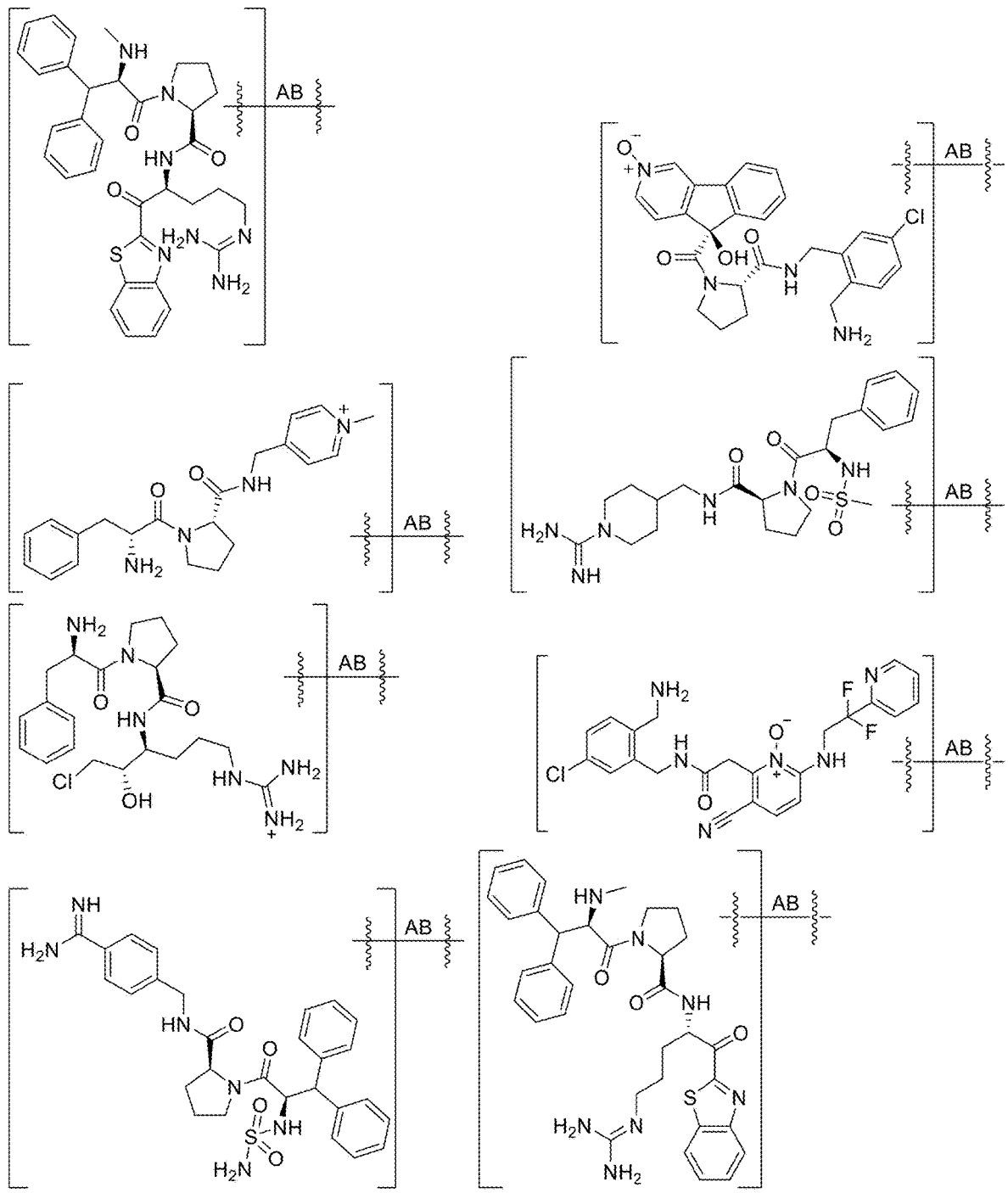
FIG. 1IIIII

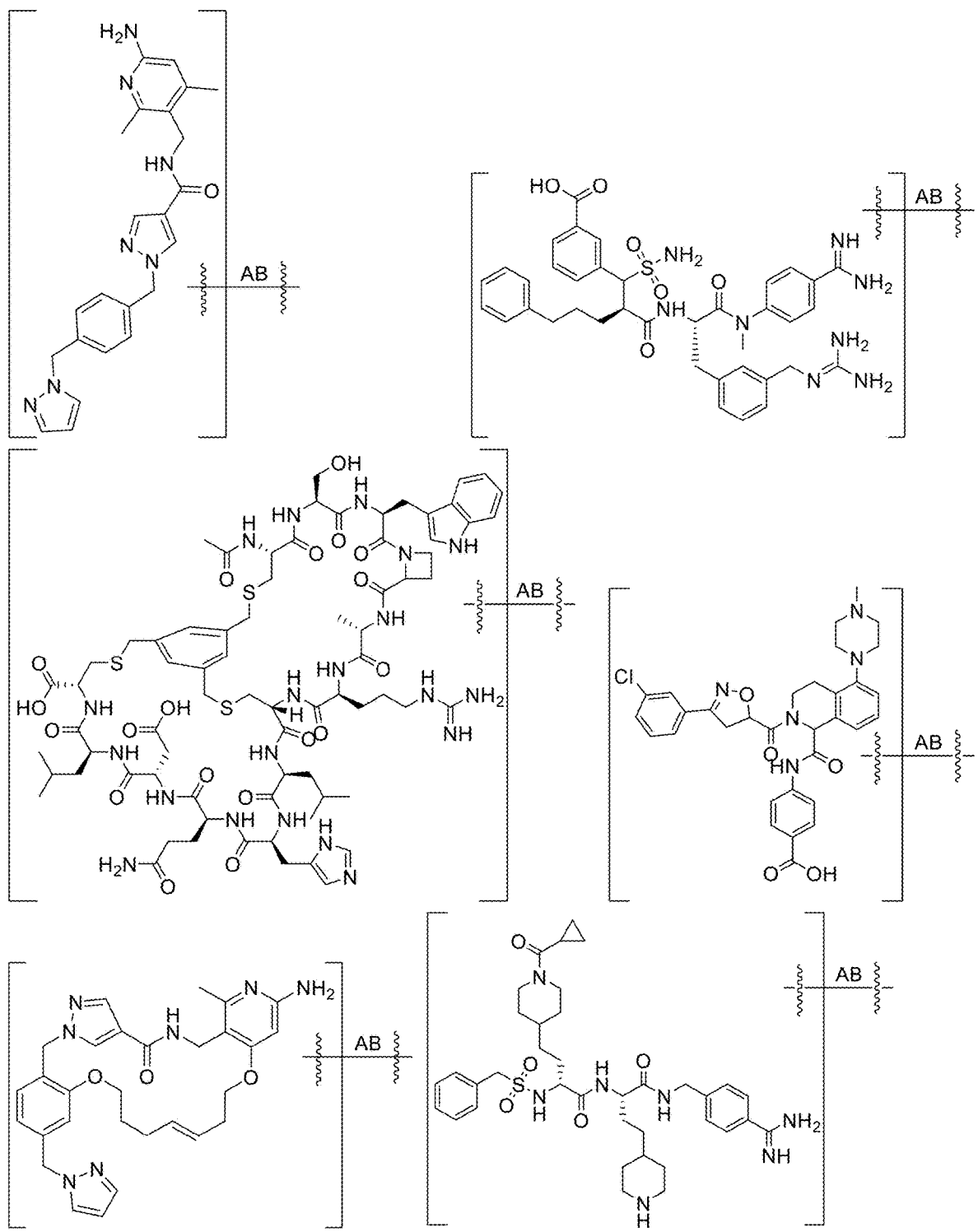
FIG. 1JJJJJ

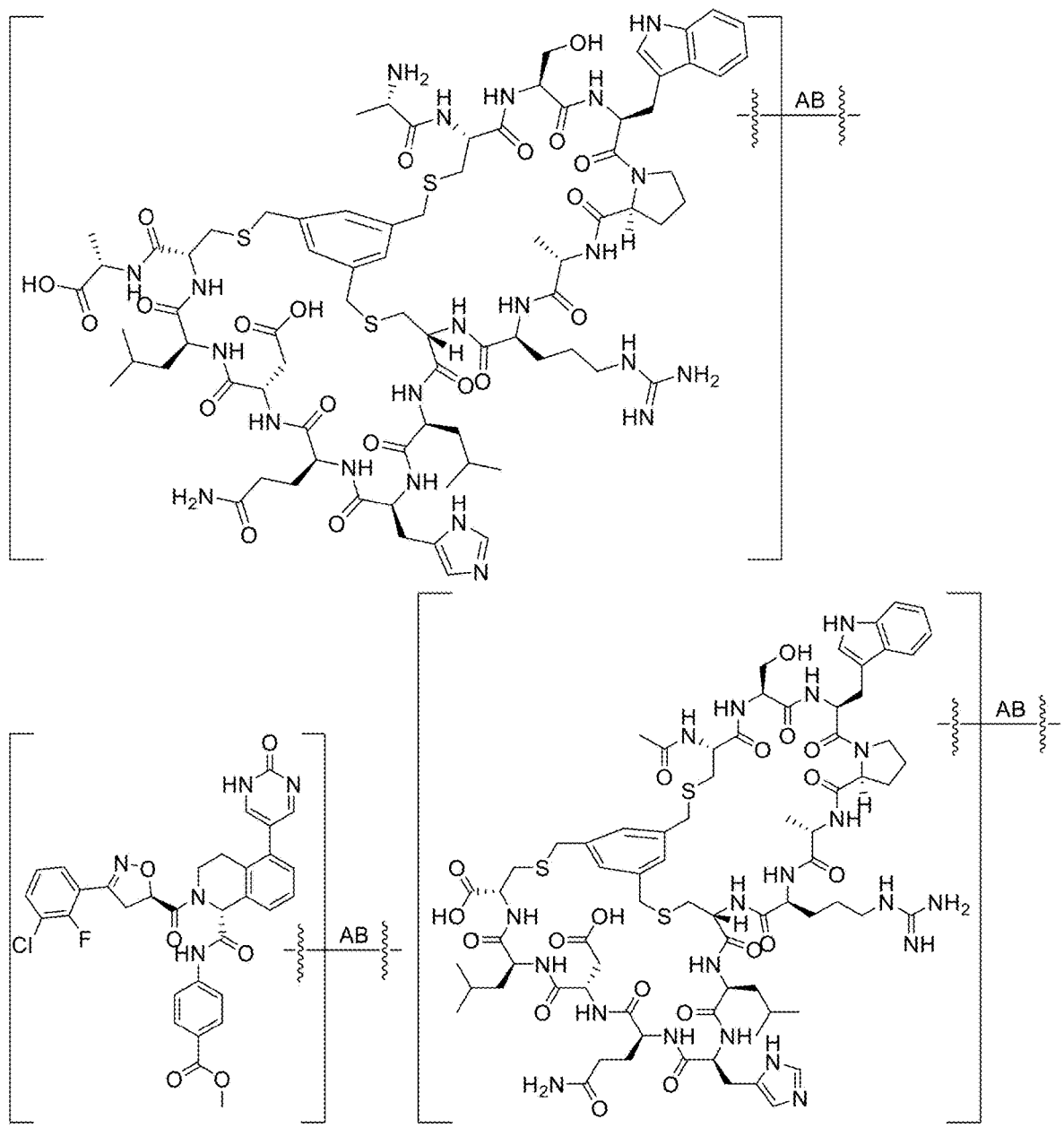
FIG. 1KKKKK

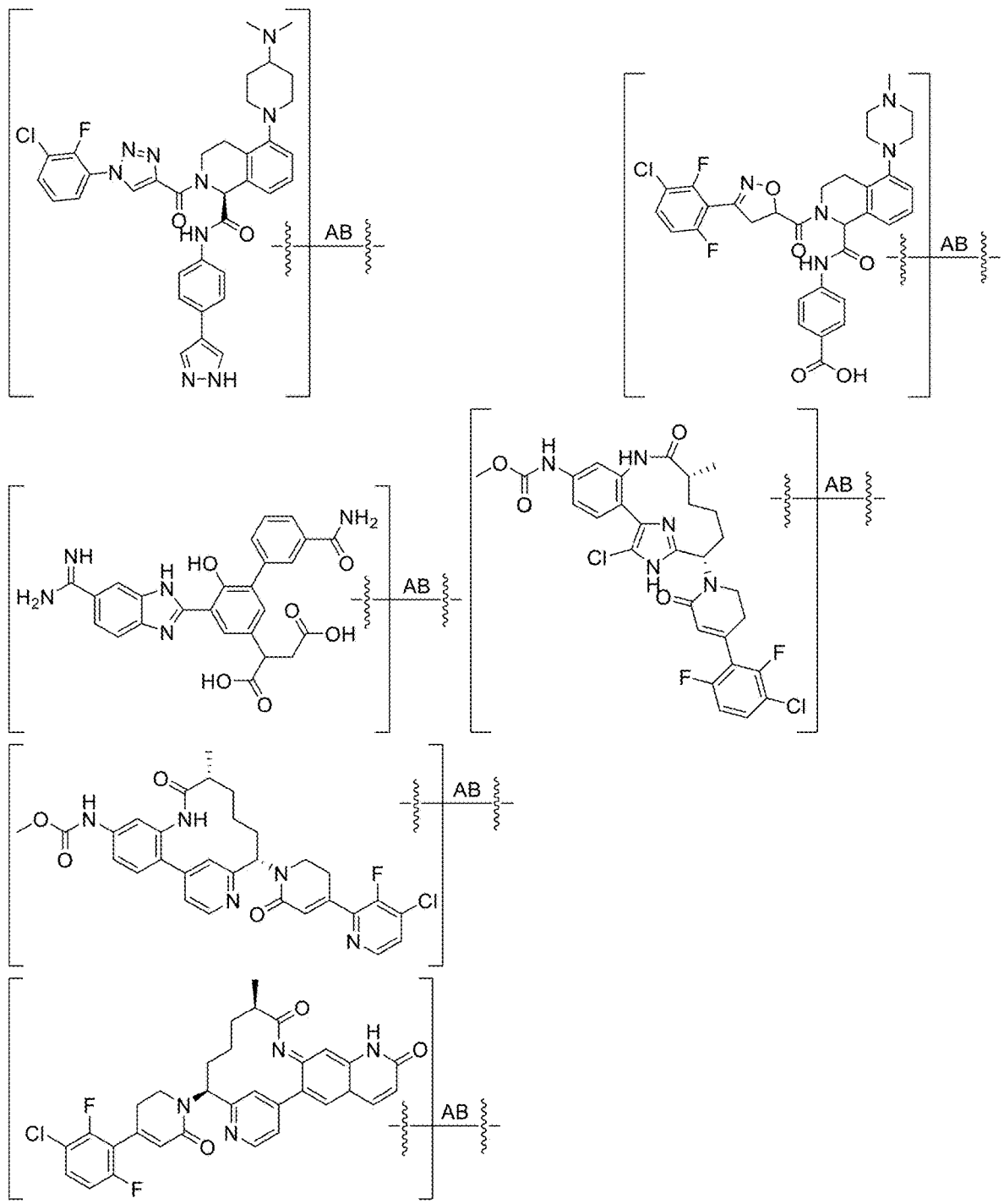
FIG. 1LLLLL

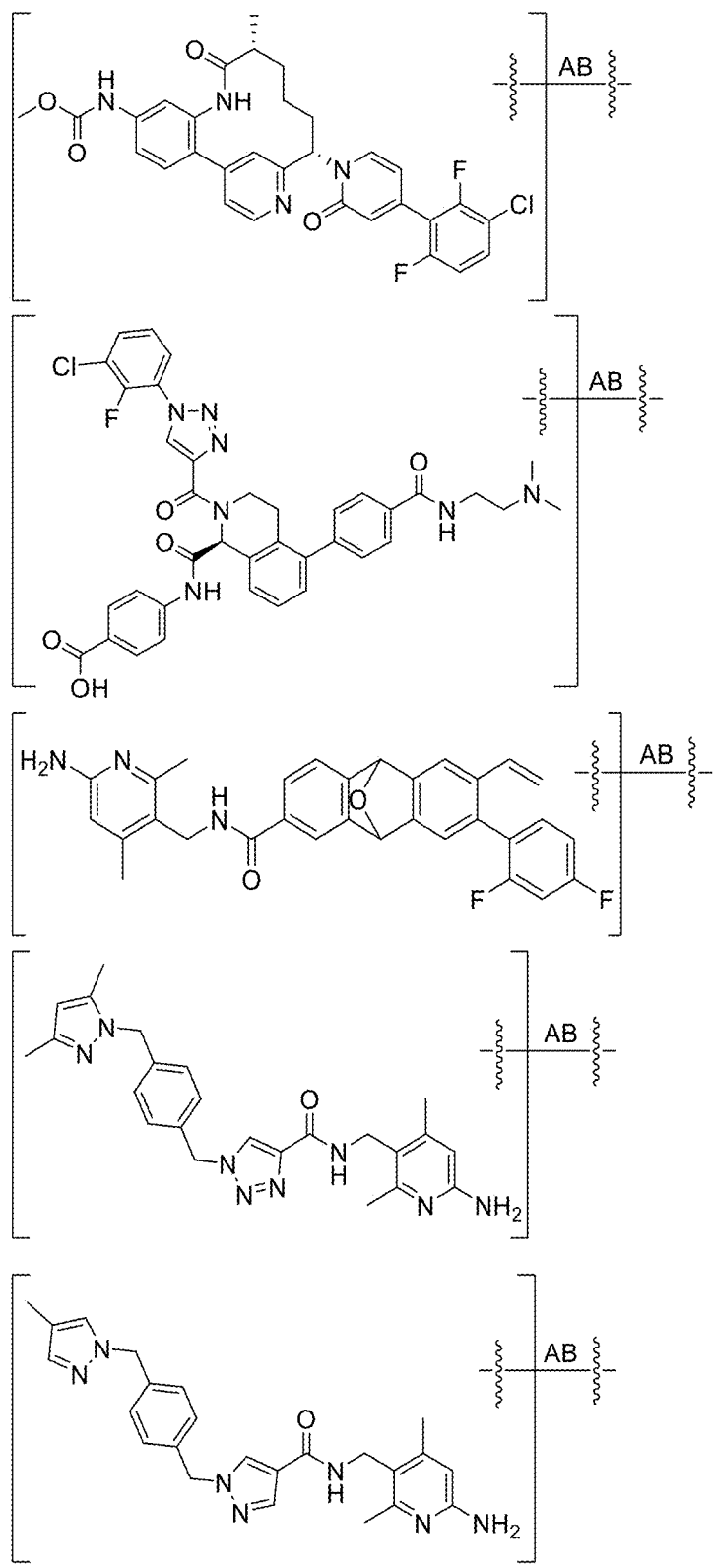
FIG. 1MMMMM

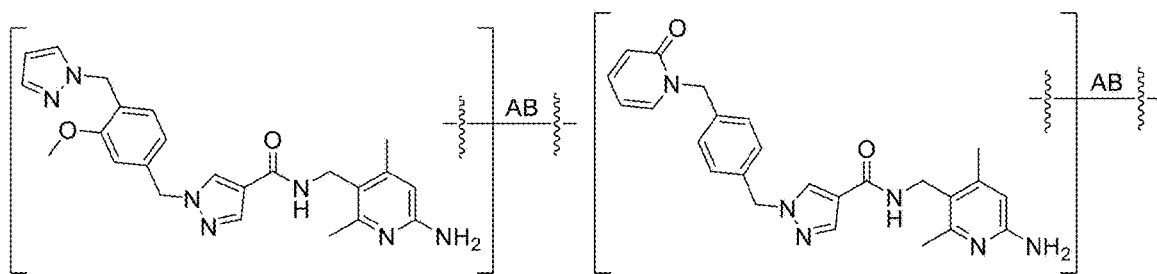
FIG. 1NNNNN
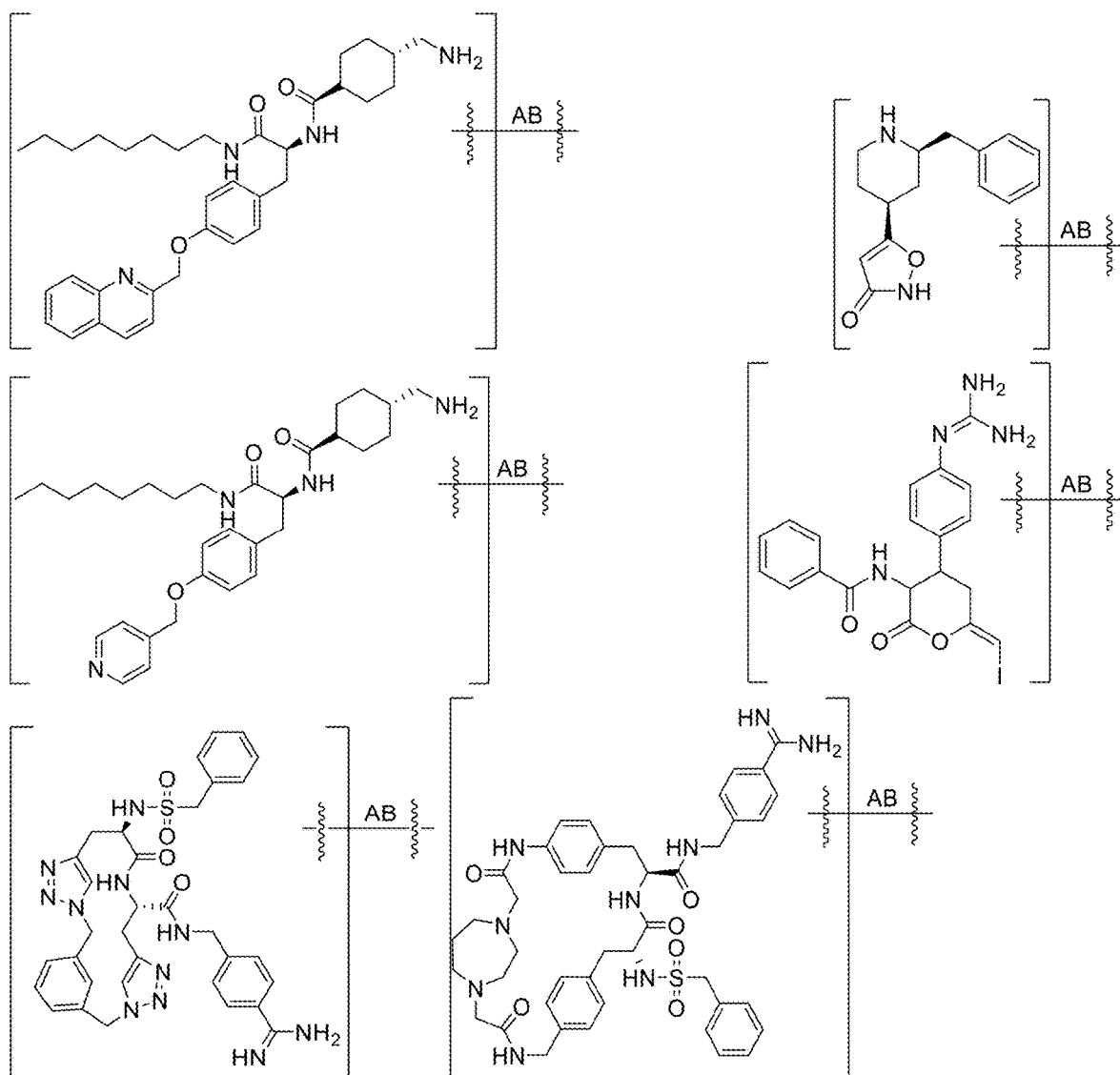
FIG. 1OOOOO

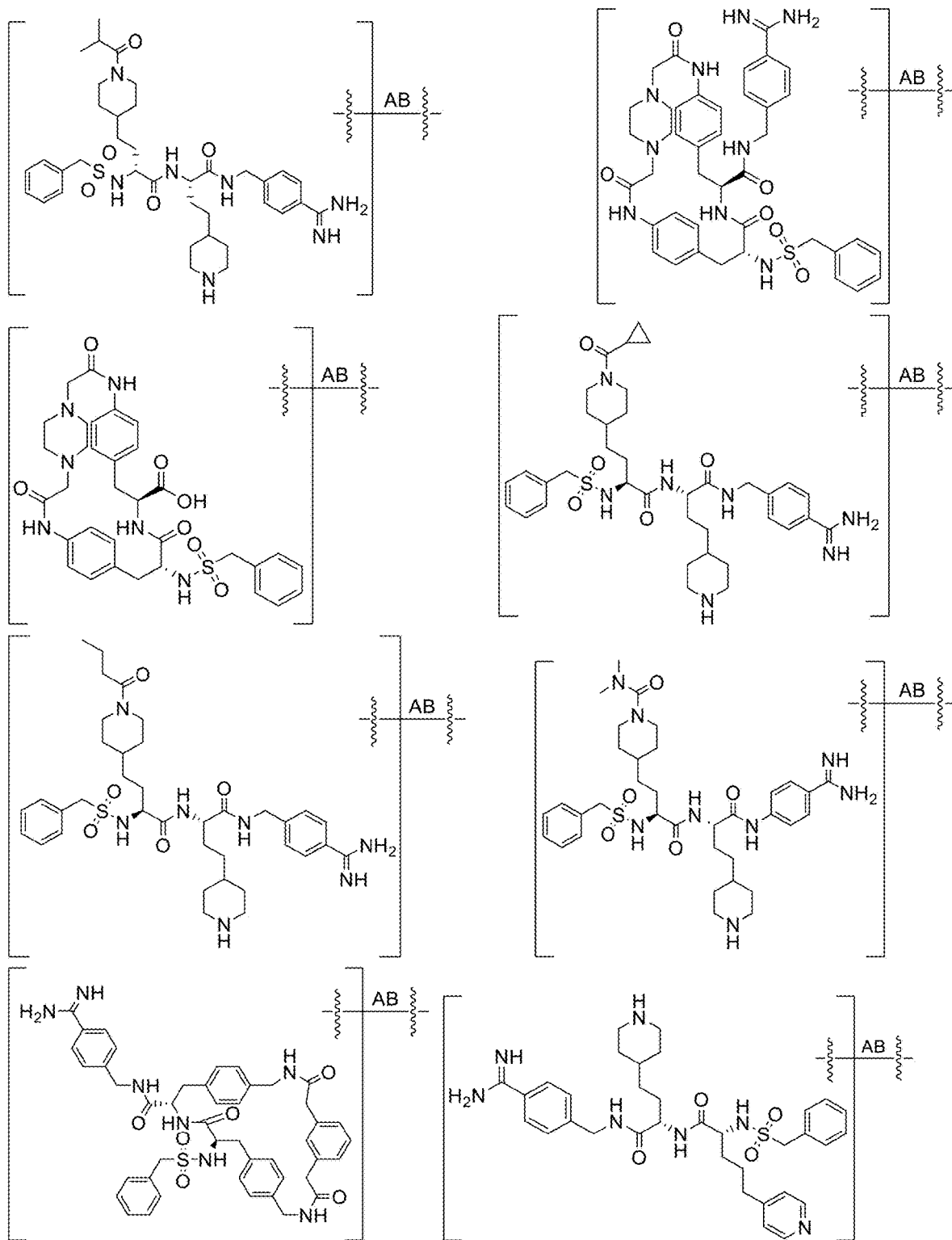
FIG. 1PPPPP

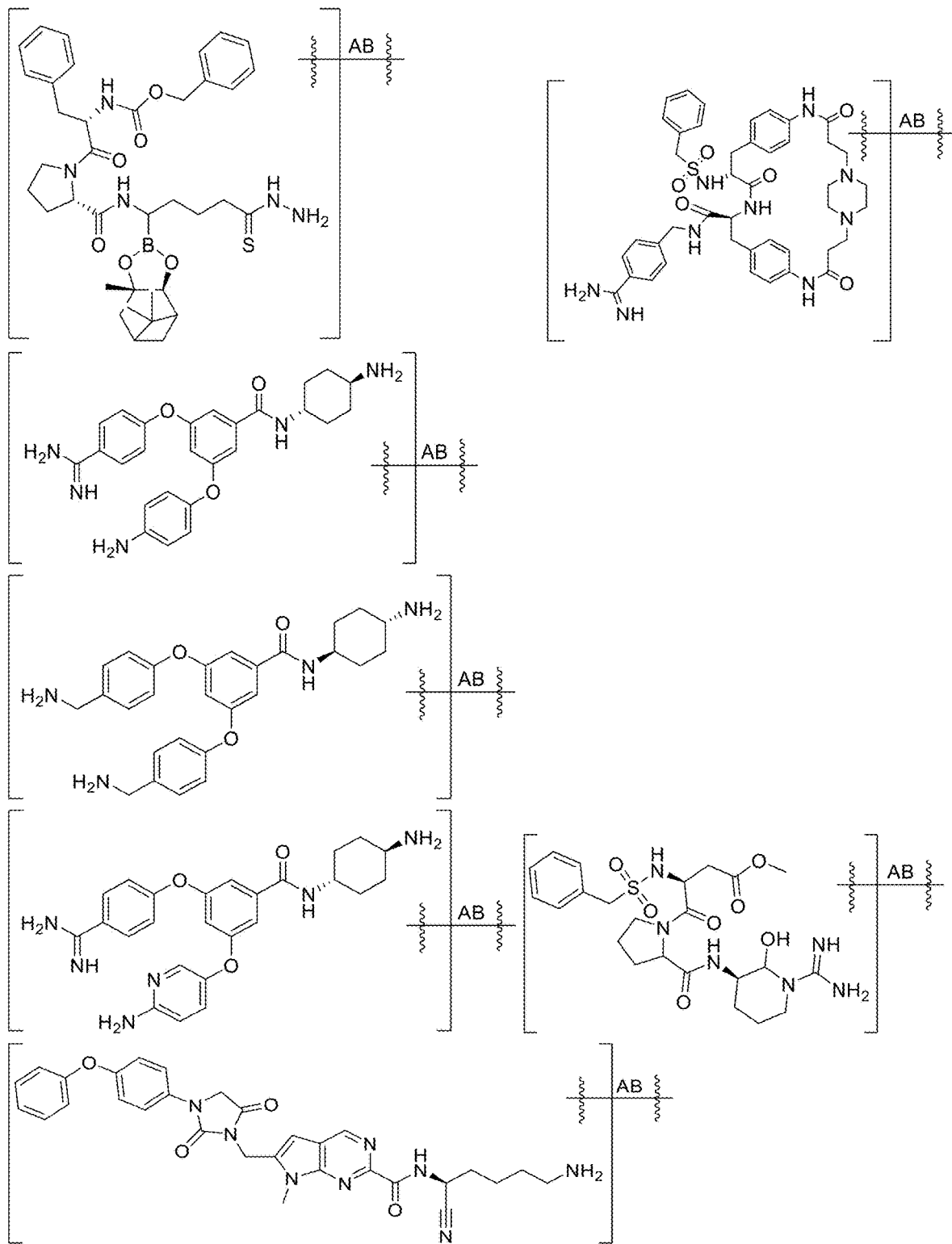
FIG. 1QQQQQ

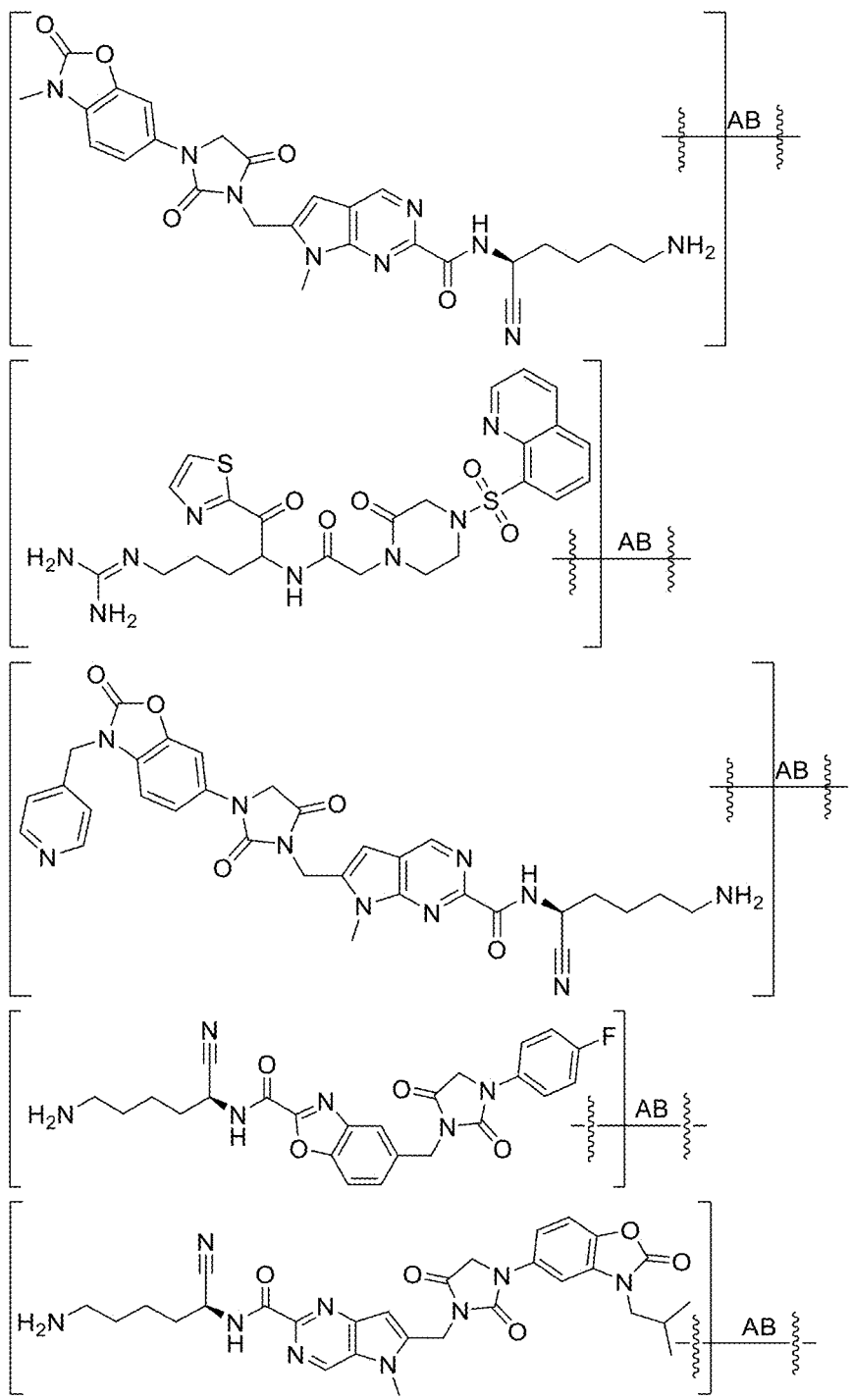
FIG. 1RRRRR

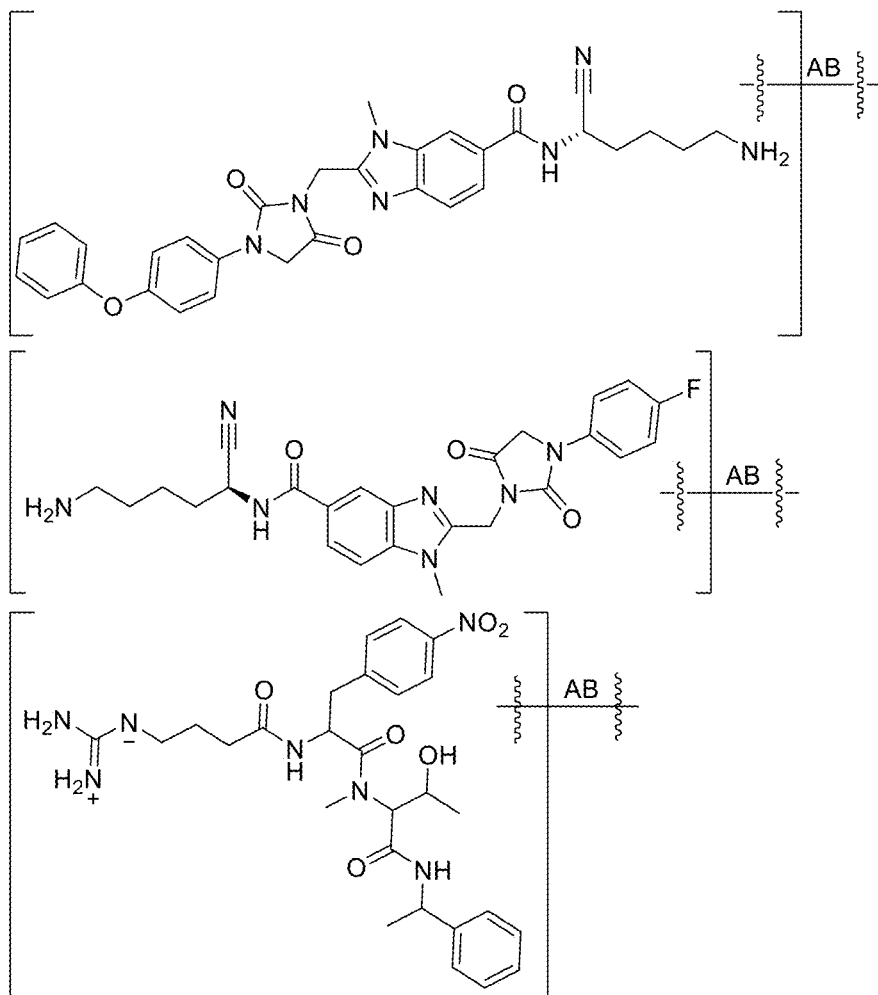
FIG. 1SSSSS
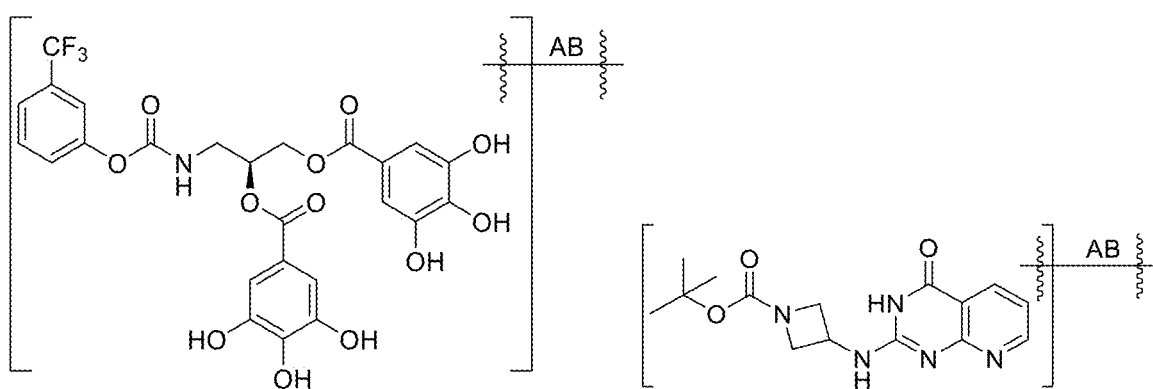
FIG. 1TTTTT

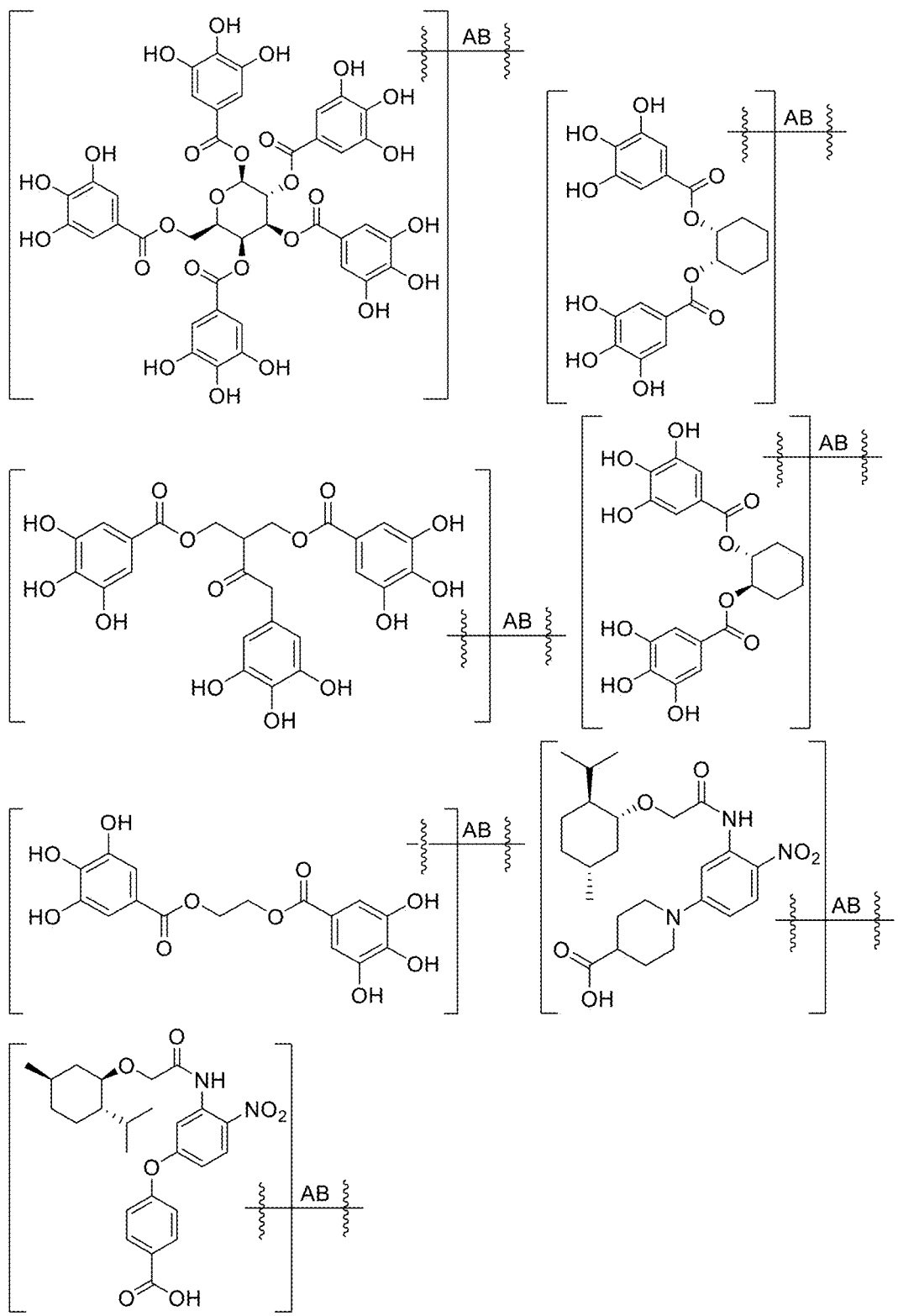
FIG. 1UUUUU

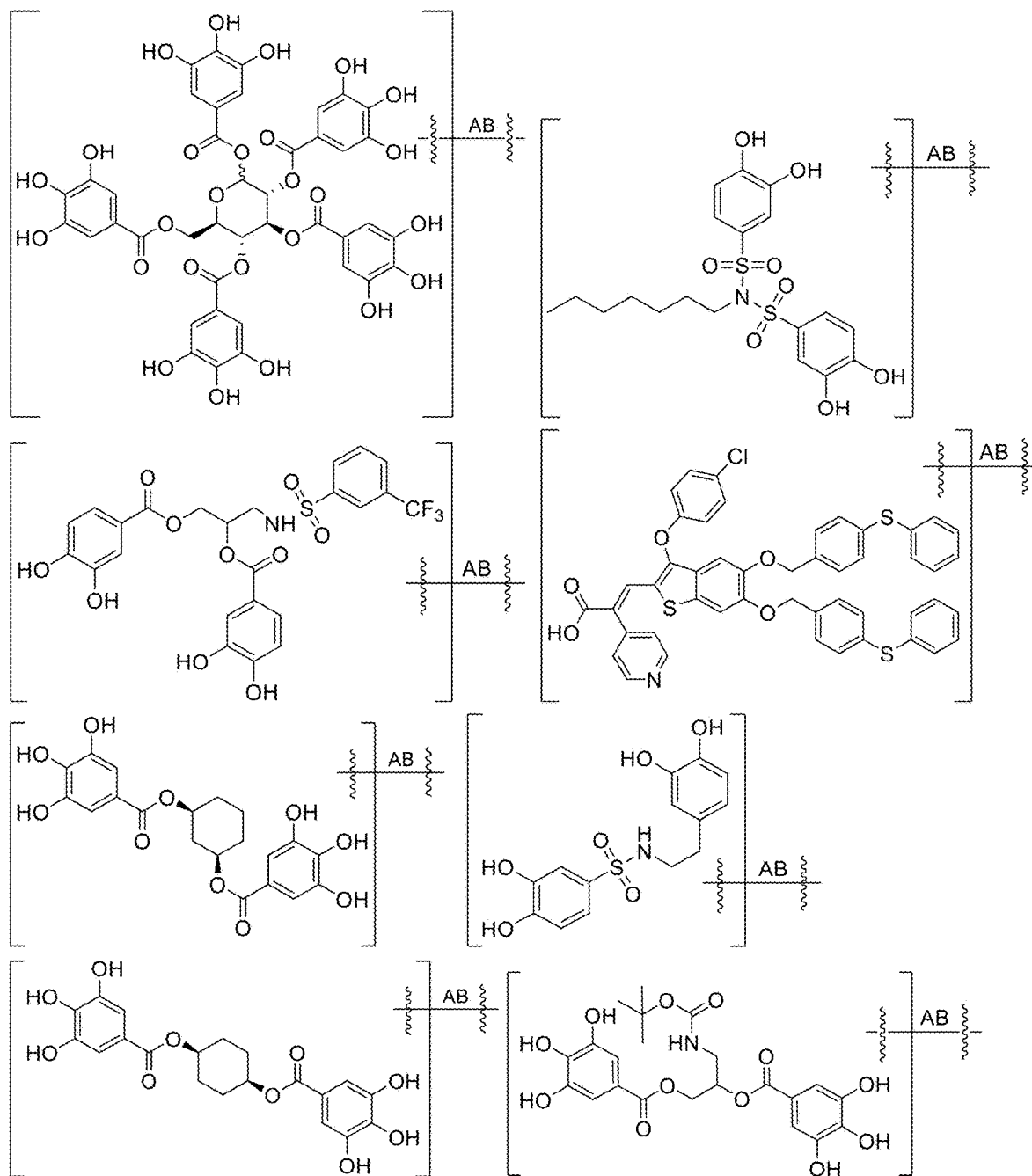
FIG. 1VVVVV

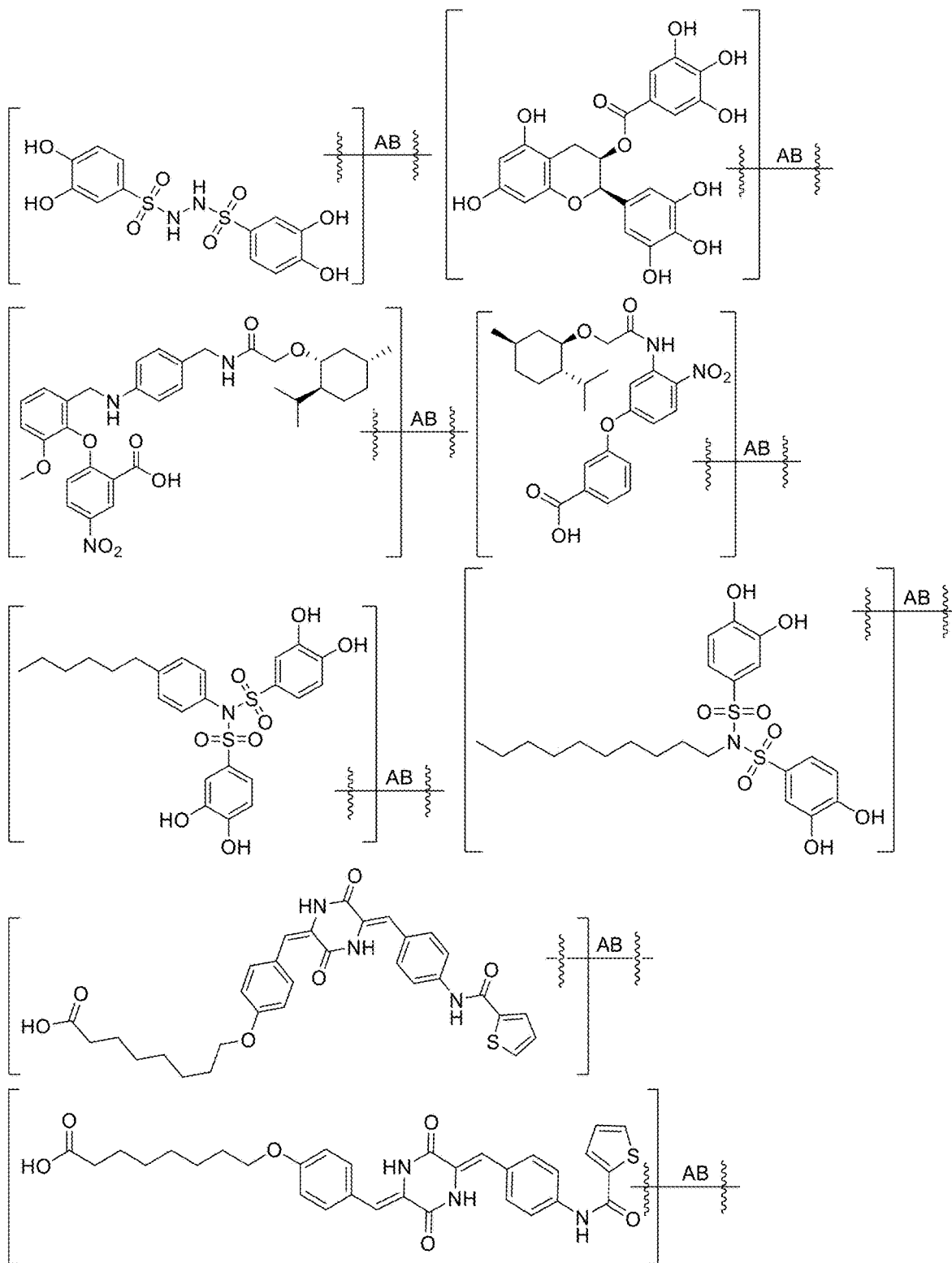
FIG. 1WWWWW

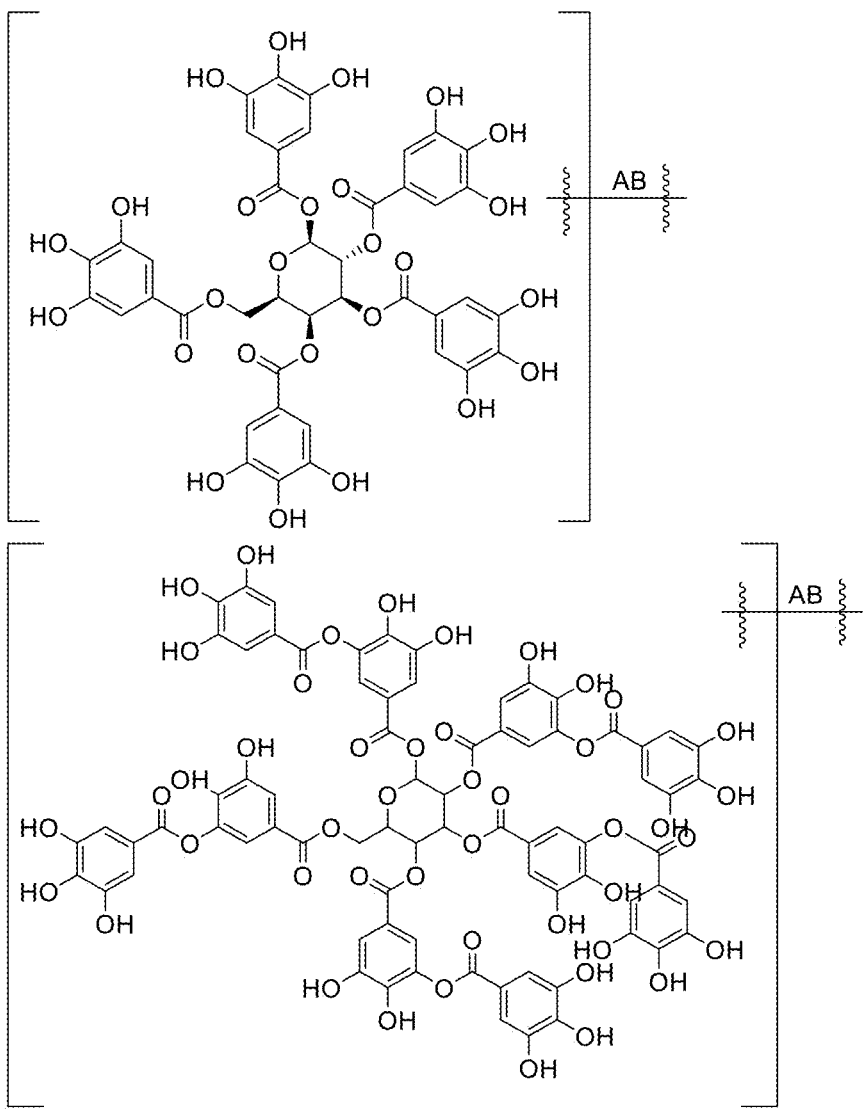
FIG. 1XXXXX
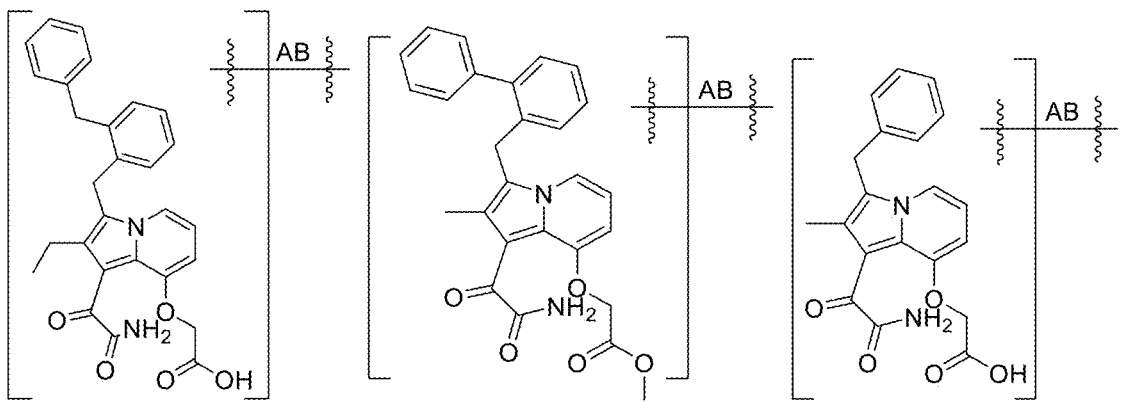
FIG. 1YYYYY

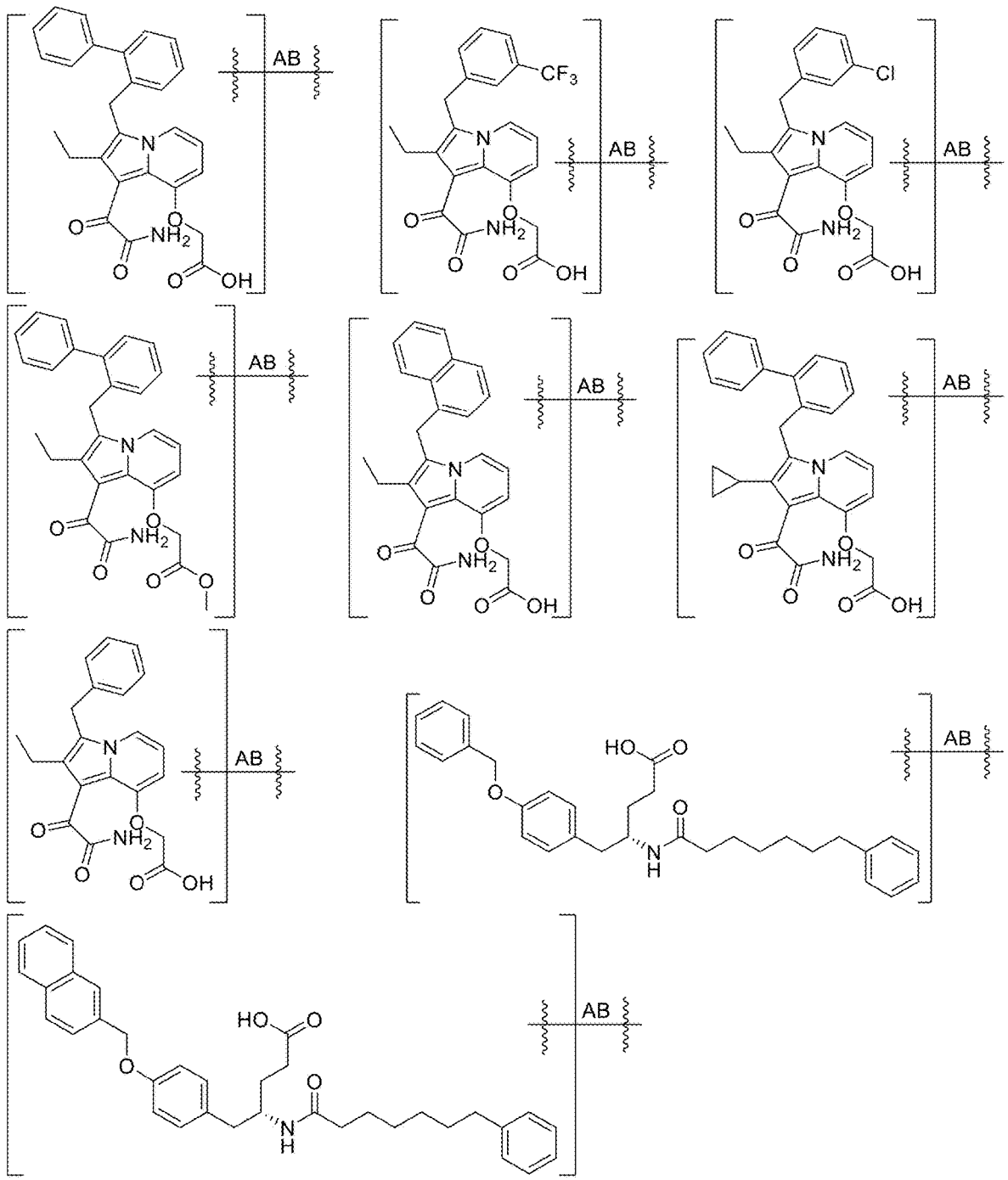
FIG. 1ZZZZZ

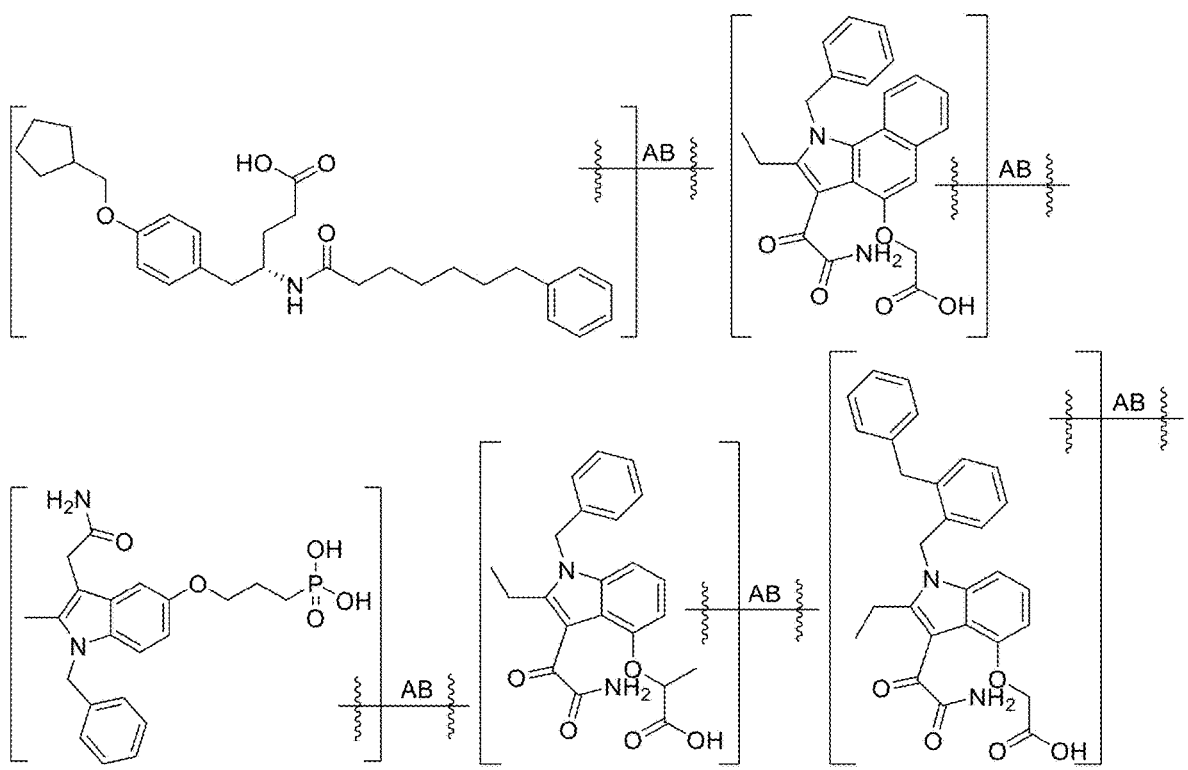
FIG. 1AAAAAA

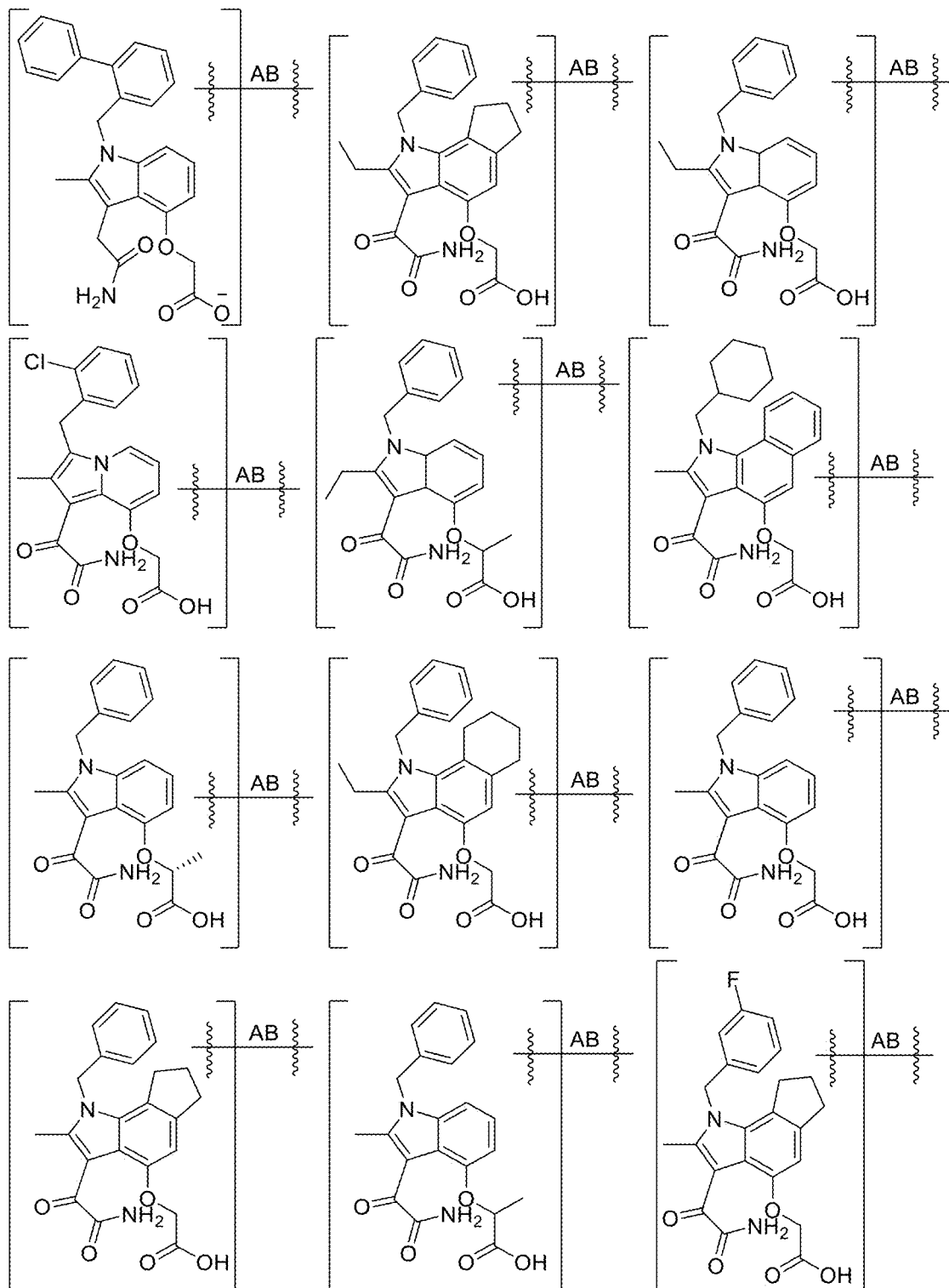
FIG. 1BBBBBB

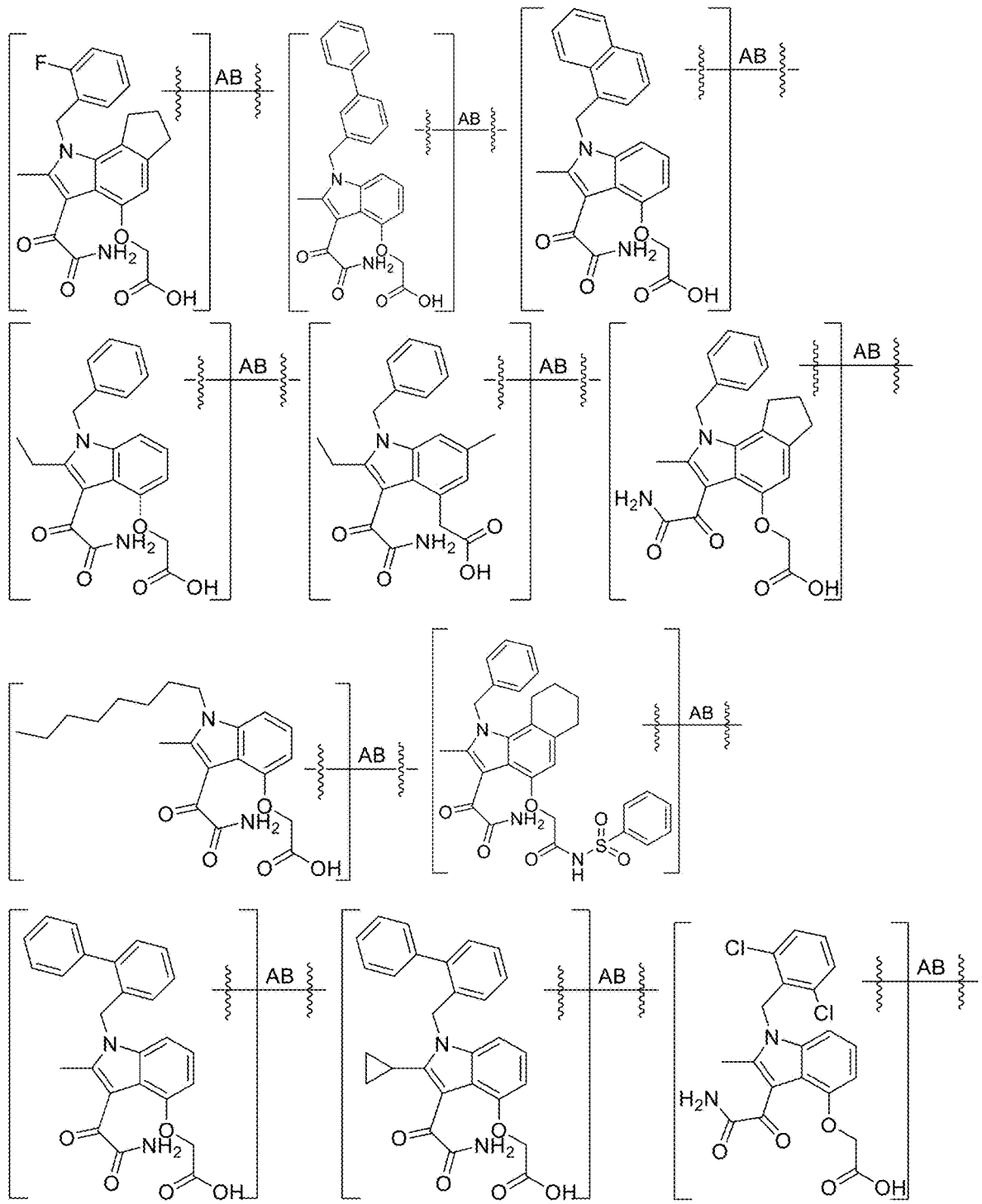
FIG. 1CCCCCC

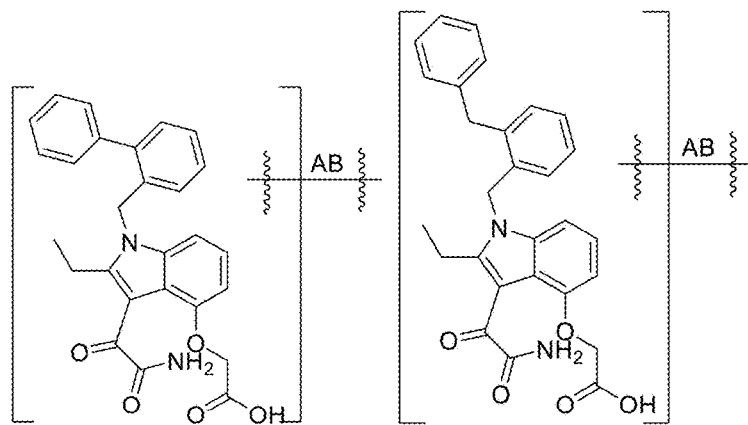
FIG. 1DDDDDD
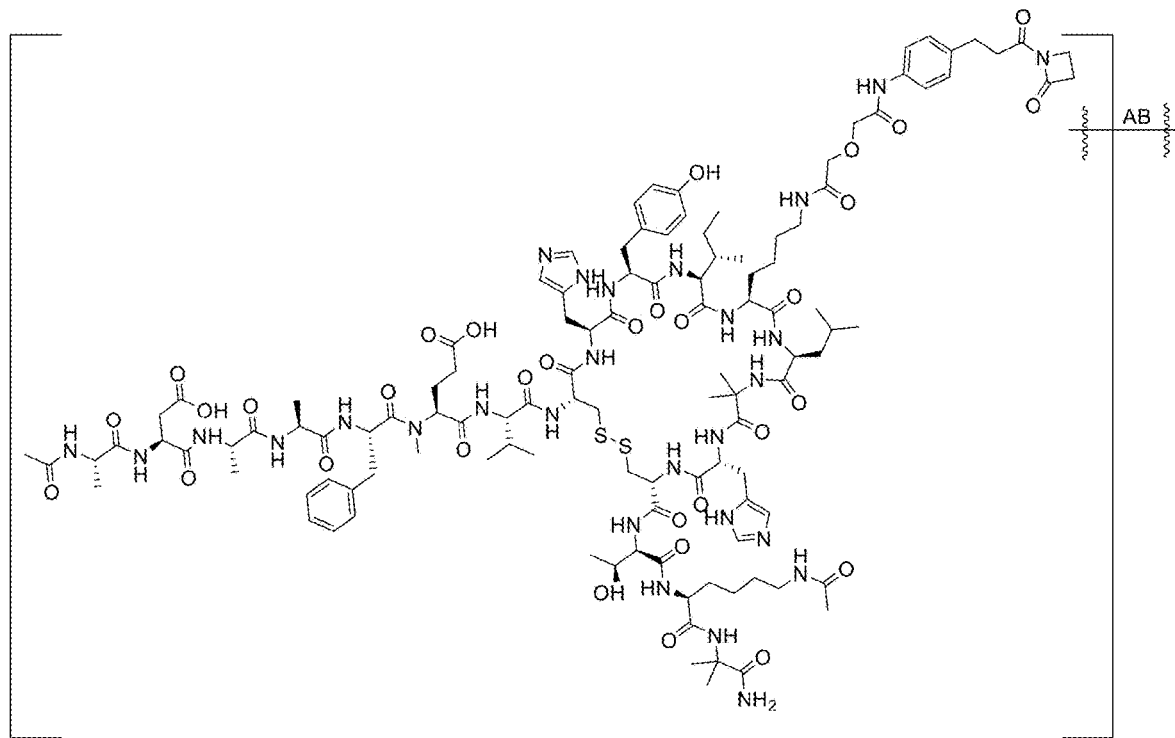
FIG. 1EEEEEE

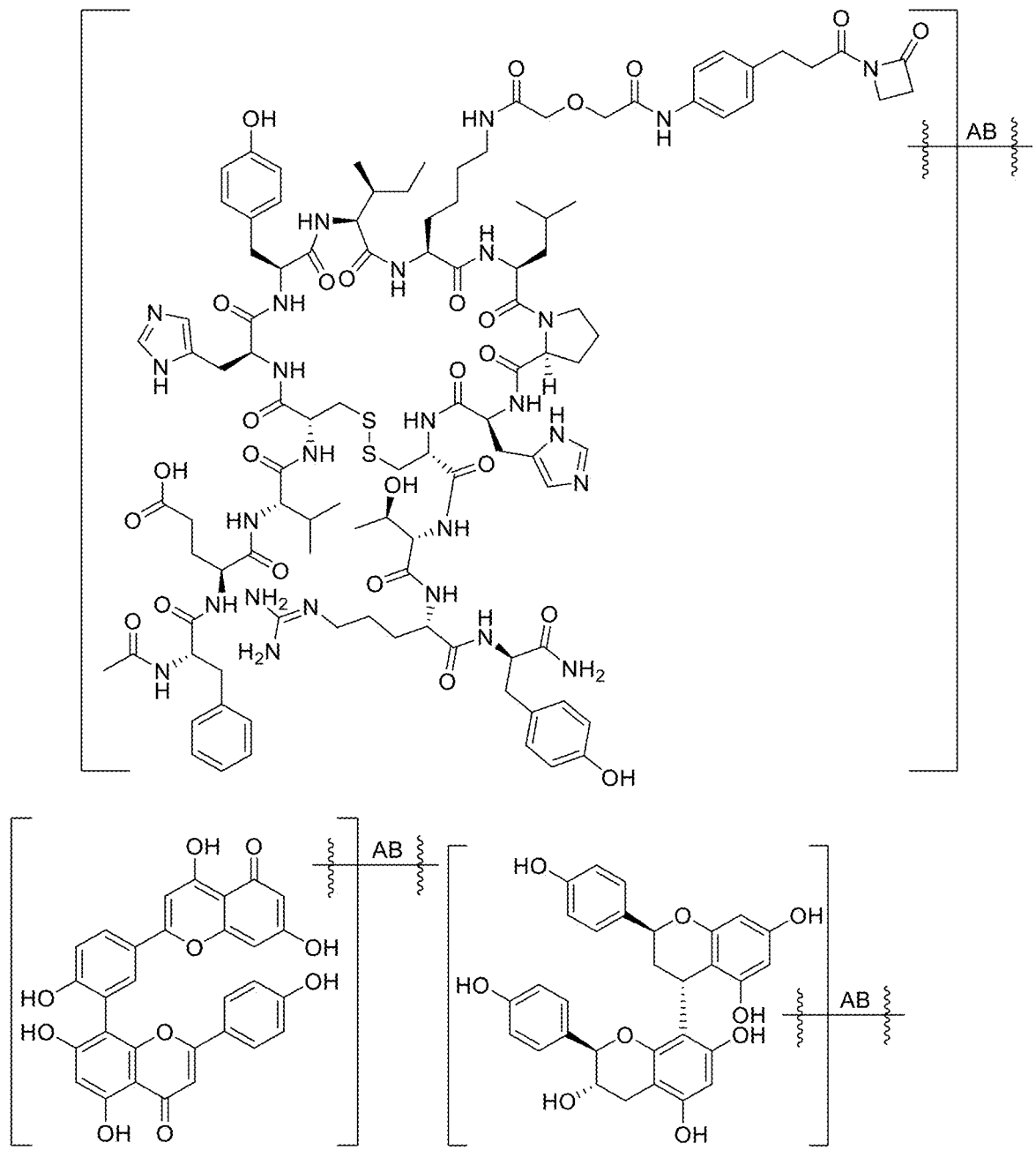
FIG. 1FFFFFF

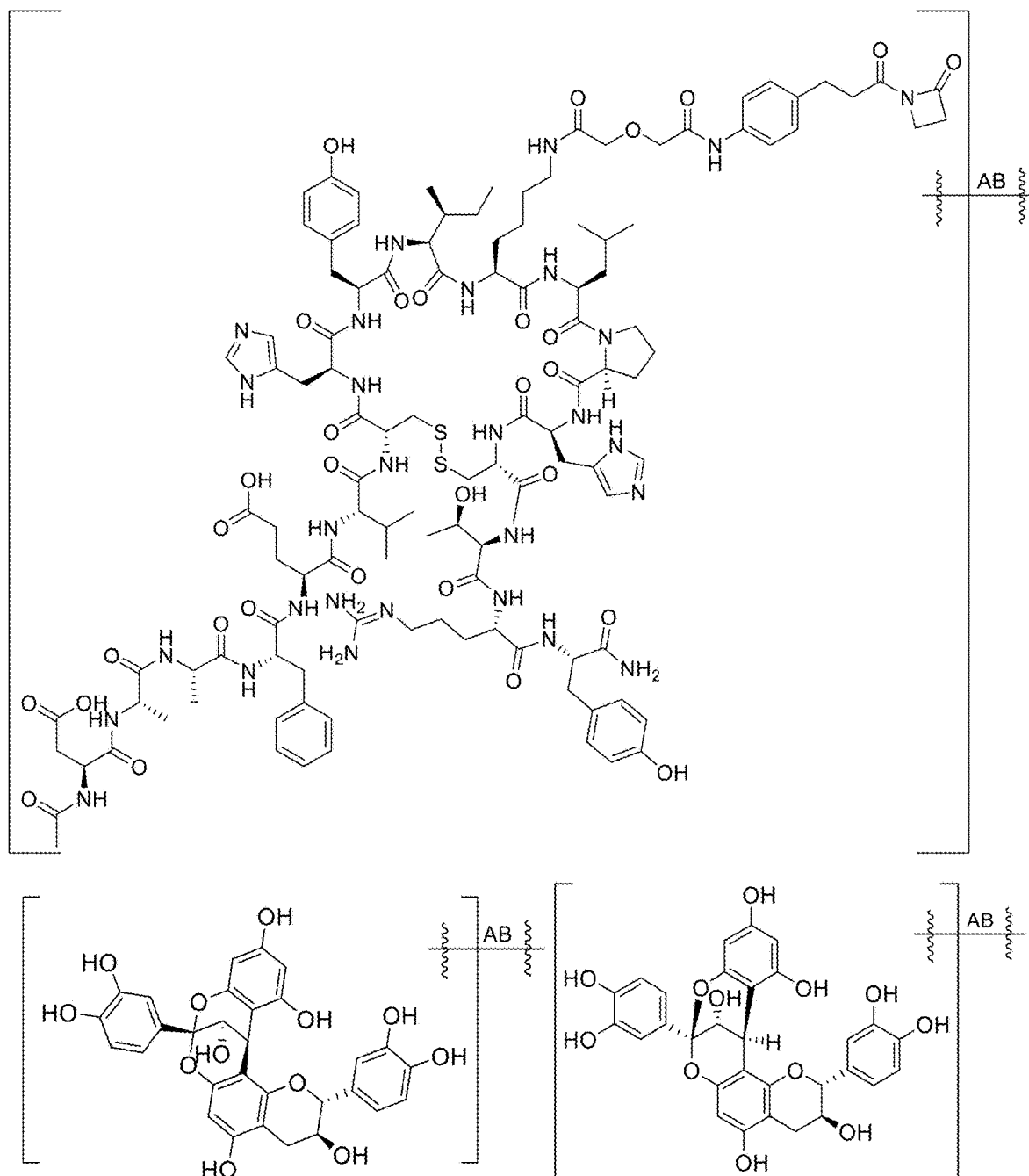
FIG. 1GGGGGG

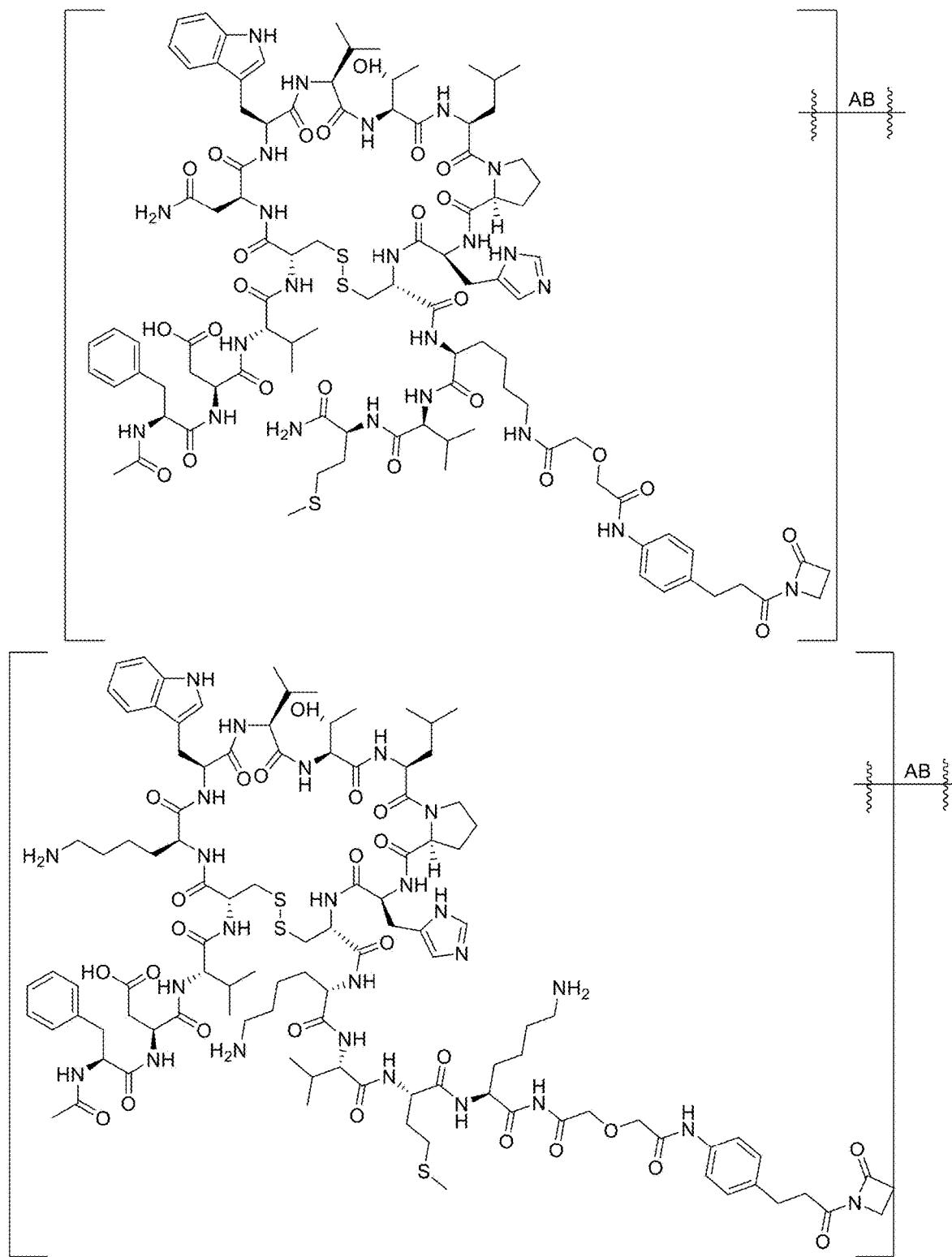
FIG. 1HHHHHH

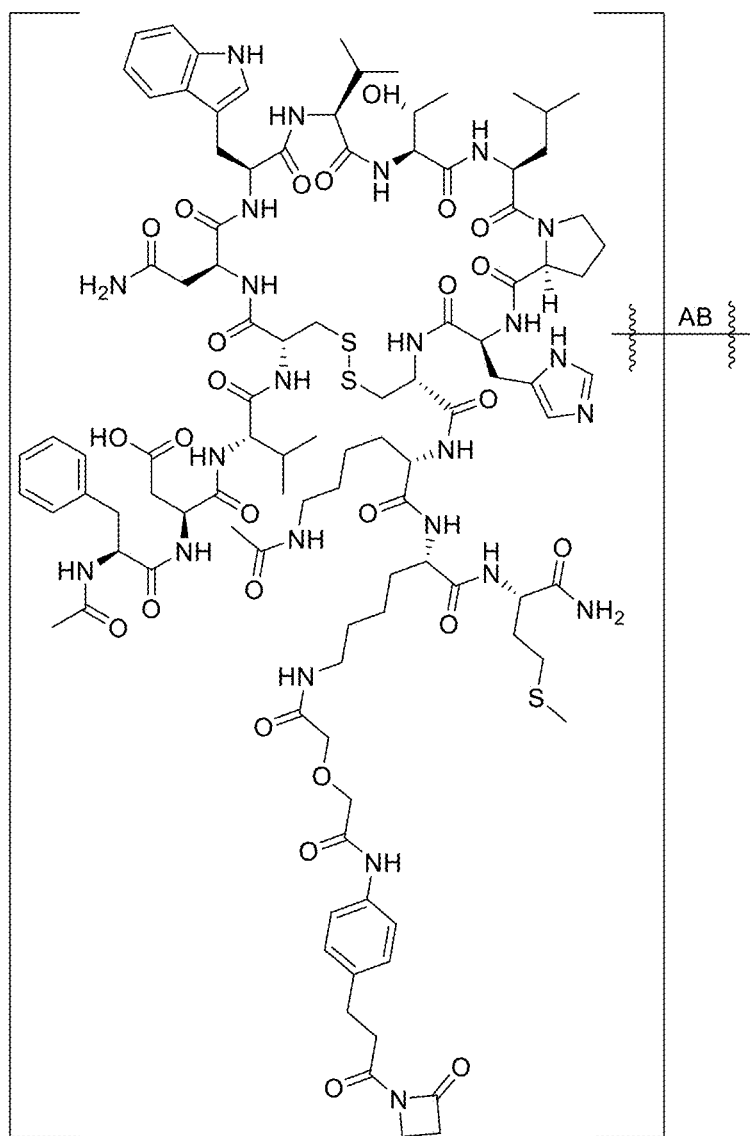
FIG. 1IIIIII

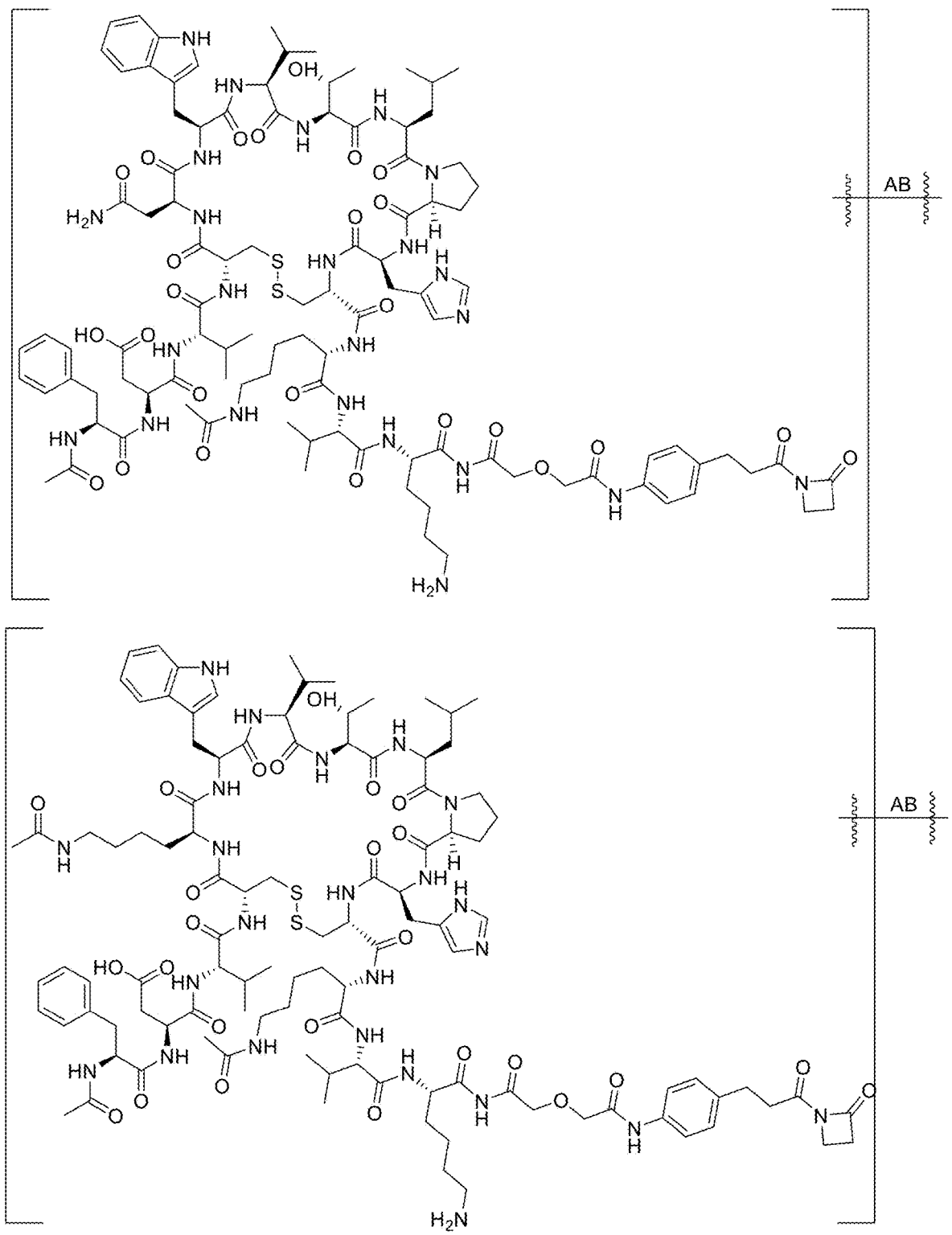
FIG. 1JJJJJJ

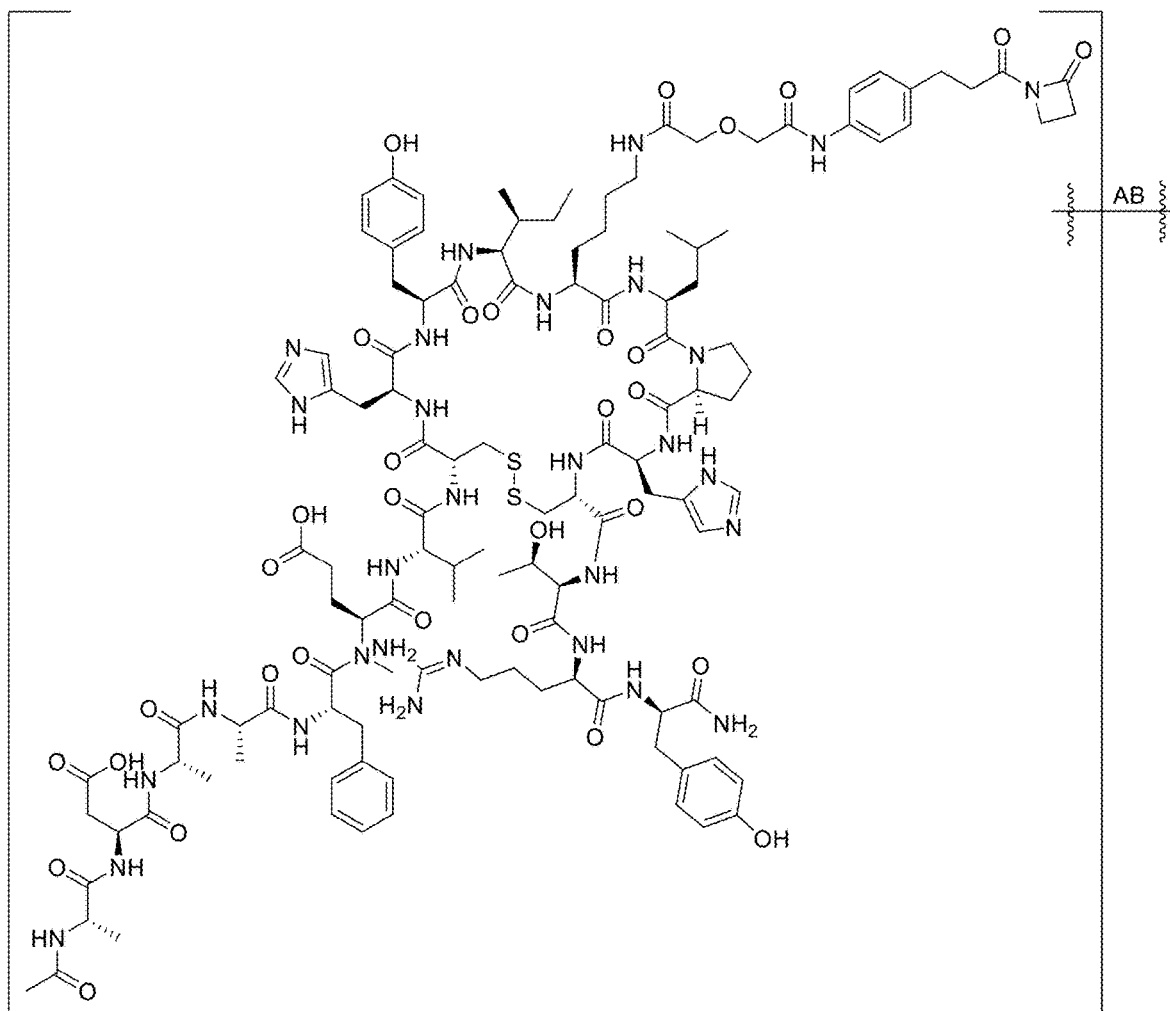
FIG. 1KKKKKK

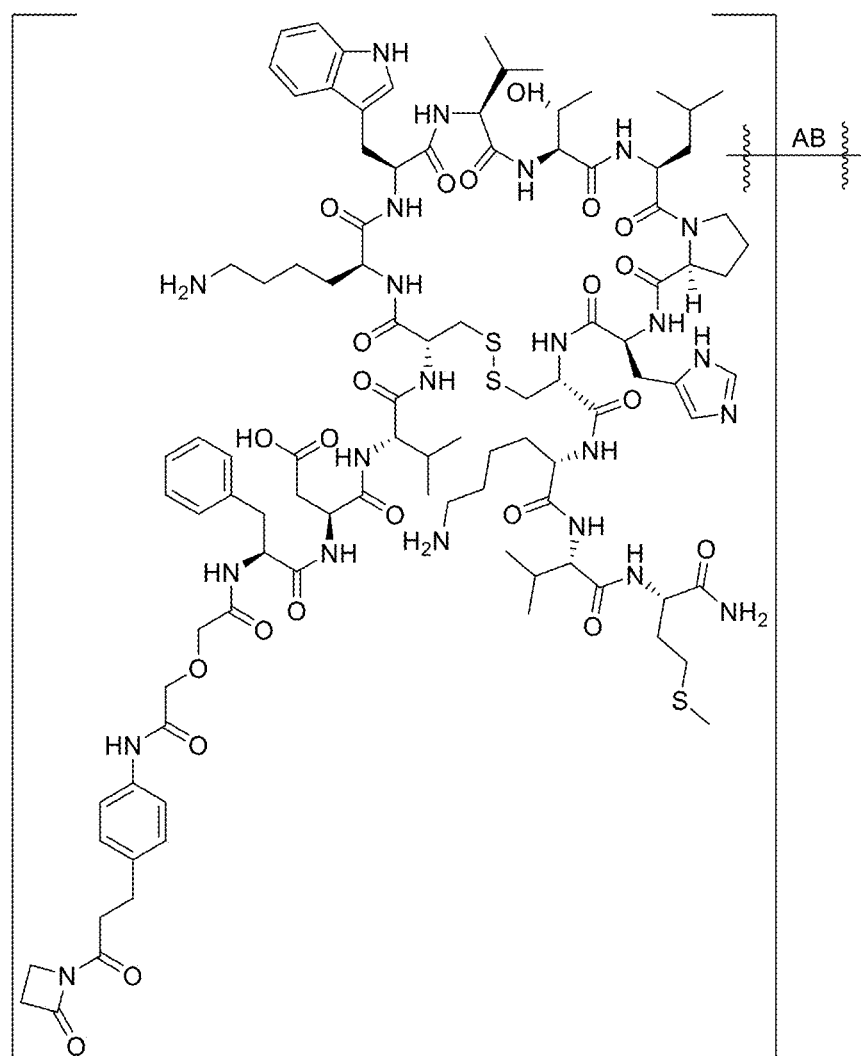
FIG. 1LLLLLL

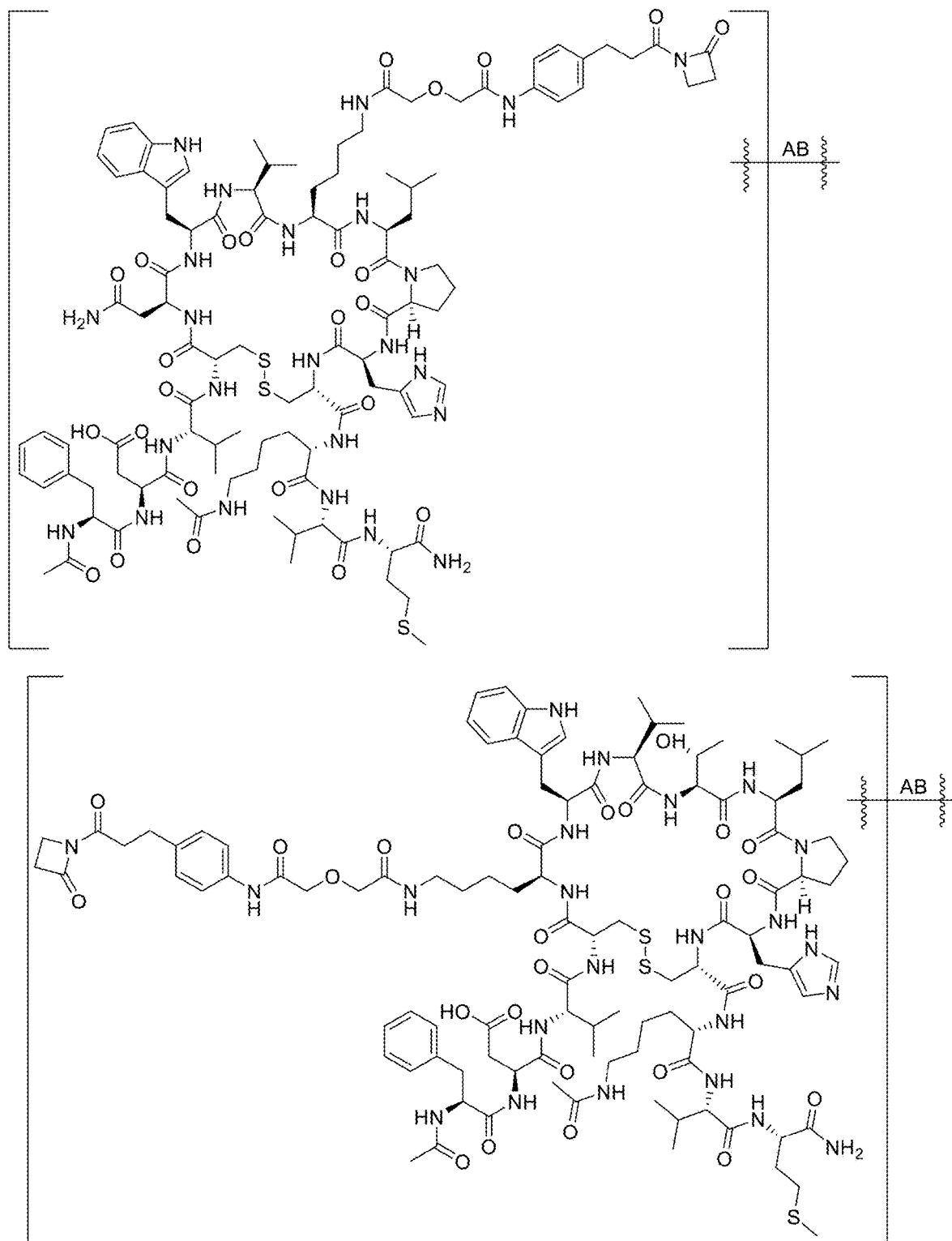
FIG. 1MMMMMM

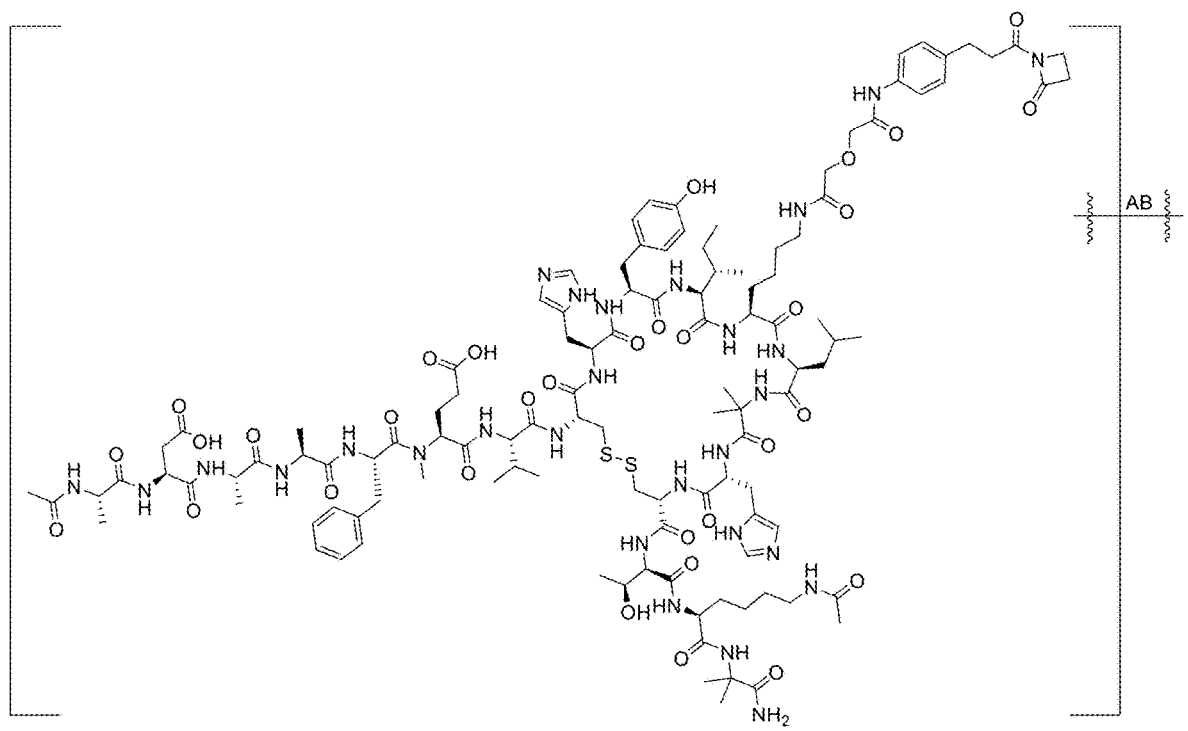
FIG. 1NNNNNN

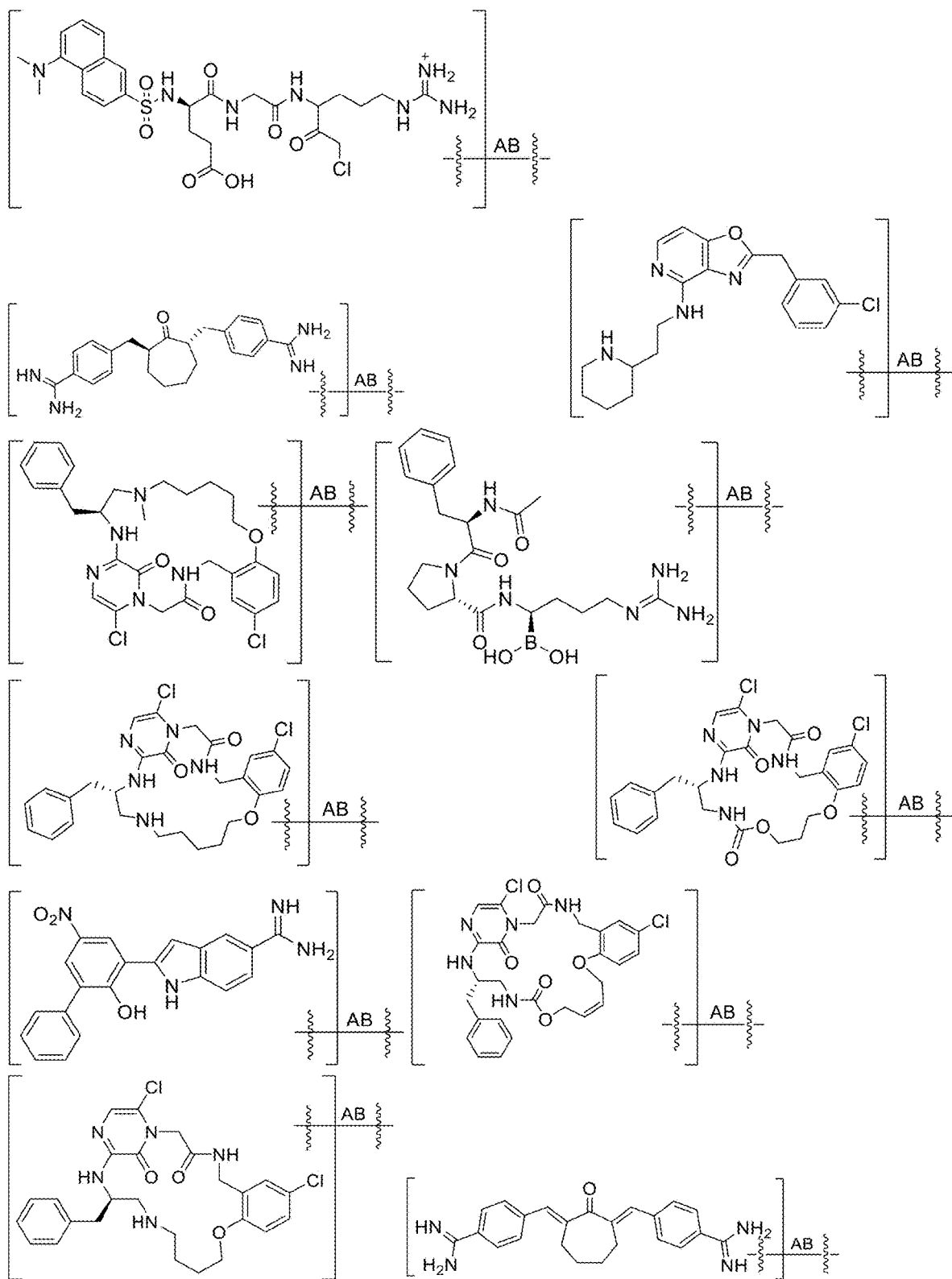
FIG. 1000000

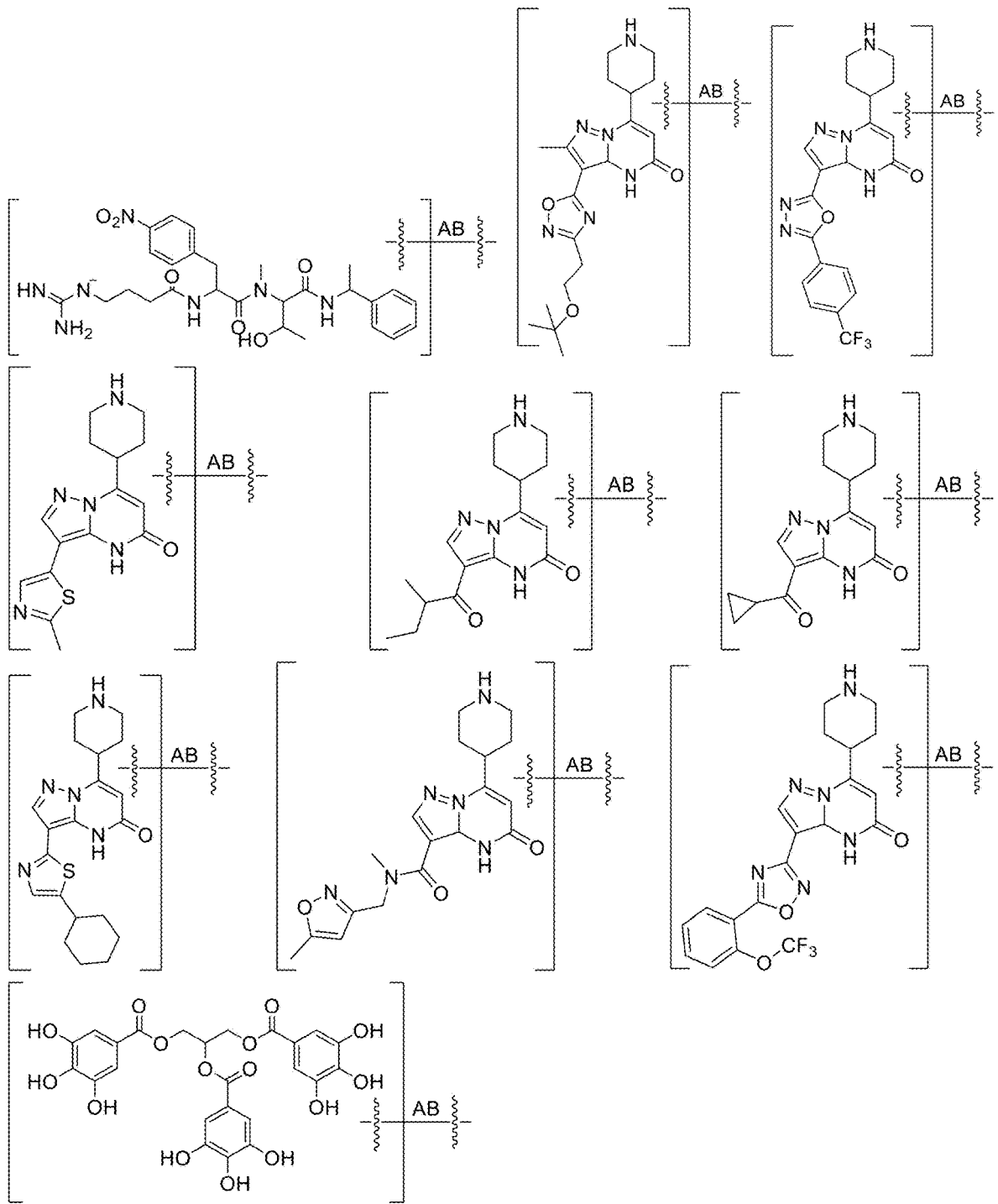
FIG. 1PPPPPP

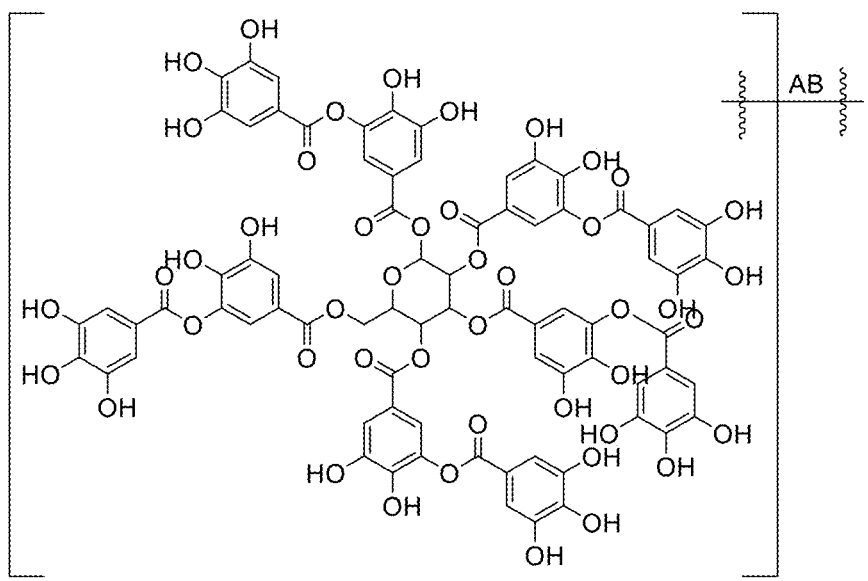
FIG. 1QQQQQQ
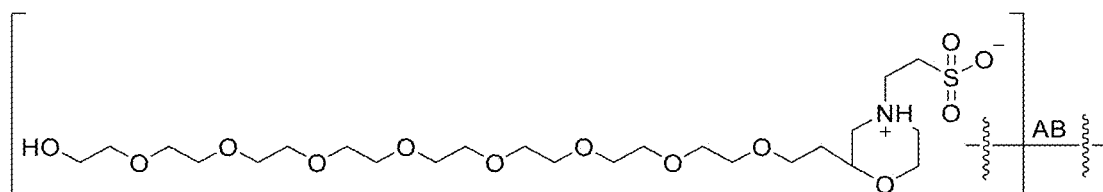
FIG. 1RRRRRR
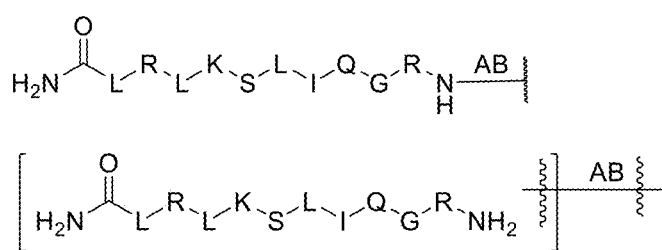
FIG. 1SSSSSS

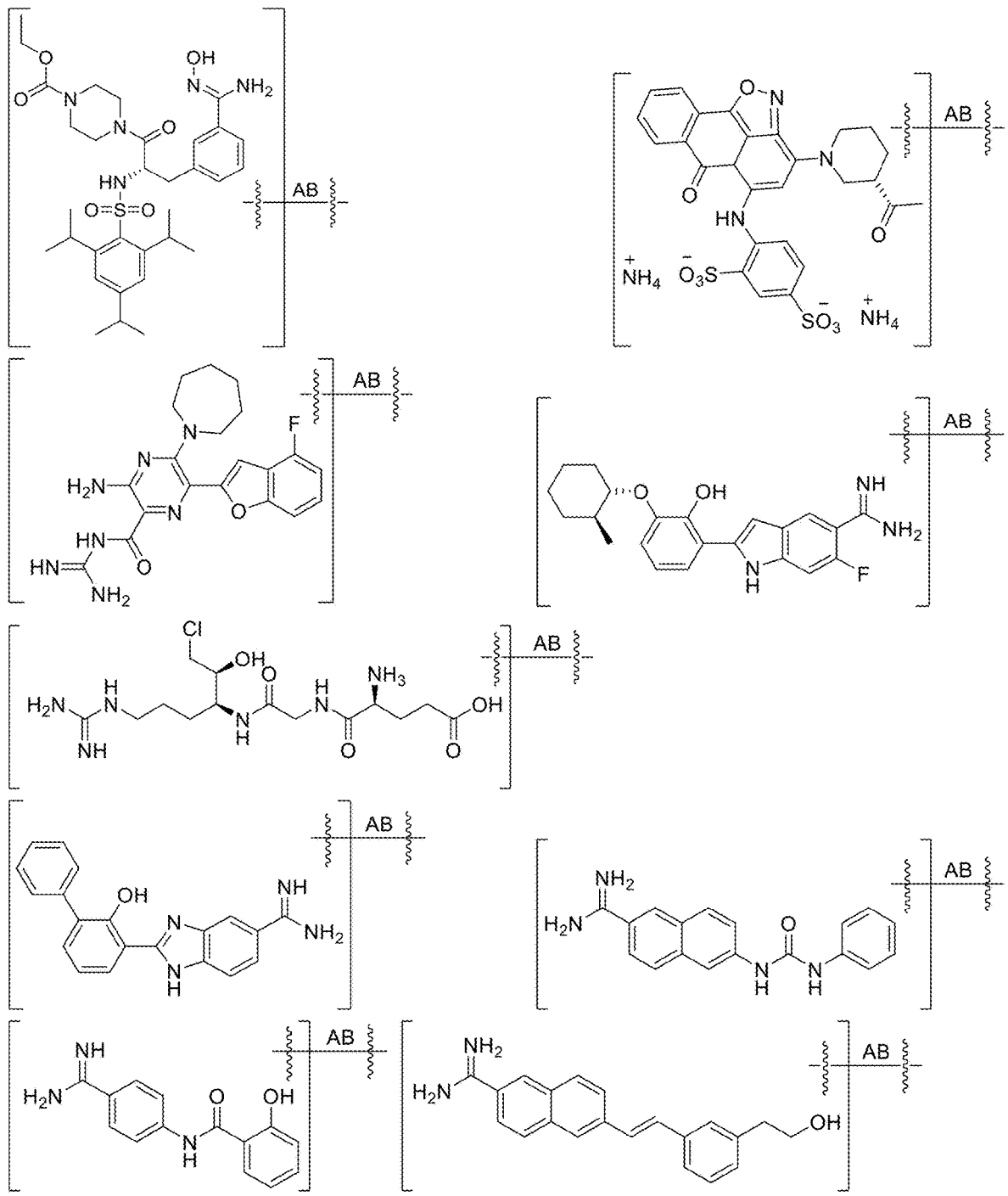
FIG. 1TTTTTT

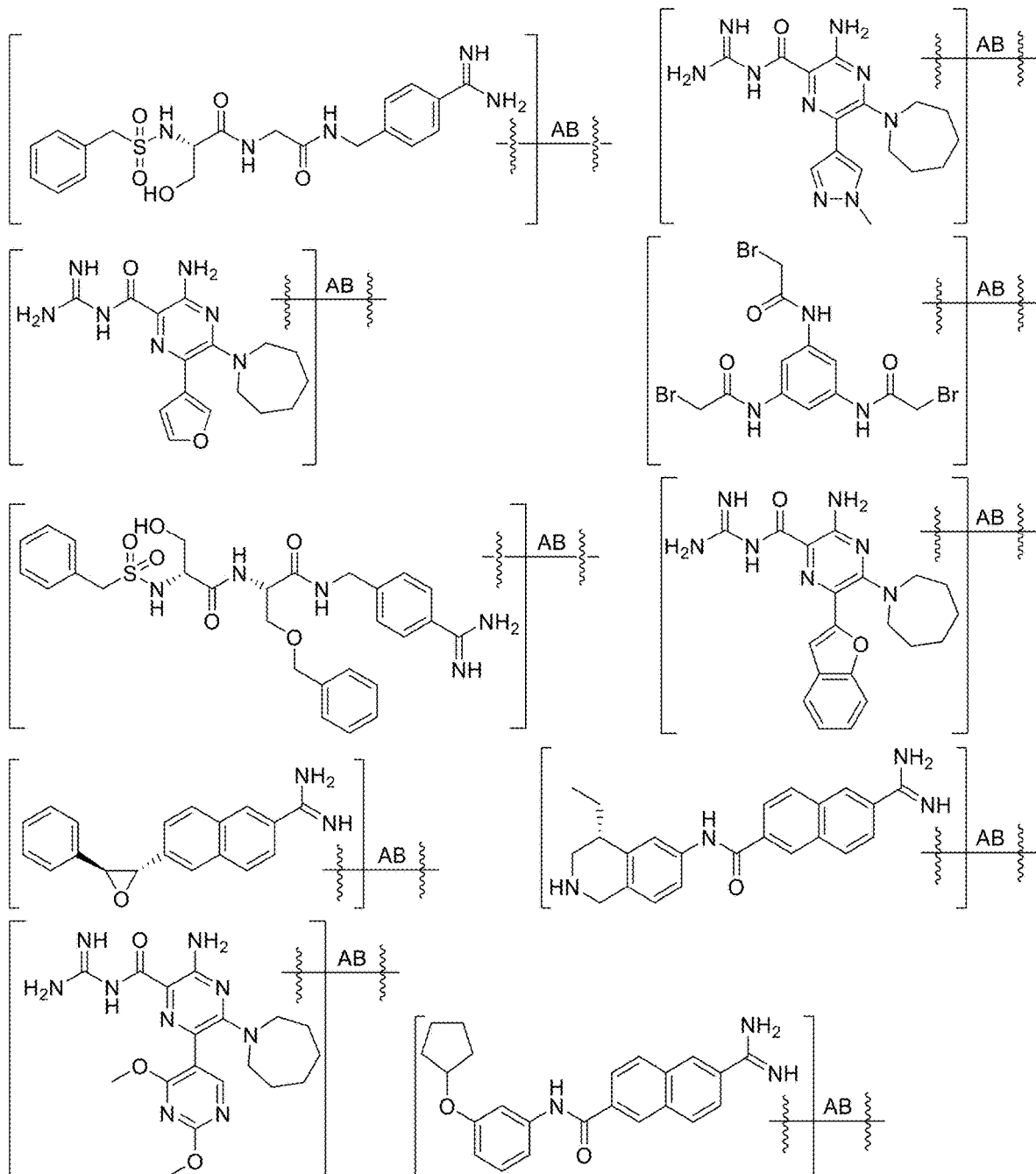
FIG. 1UUUUUU

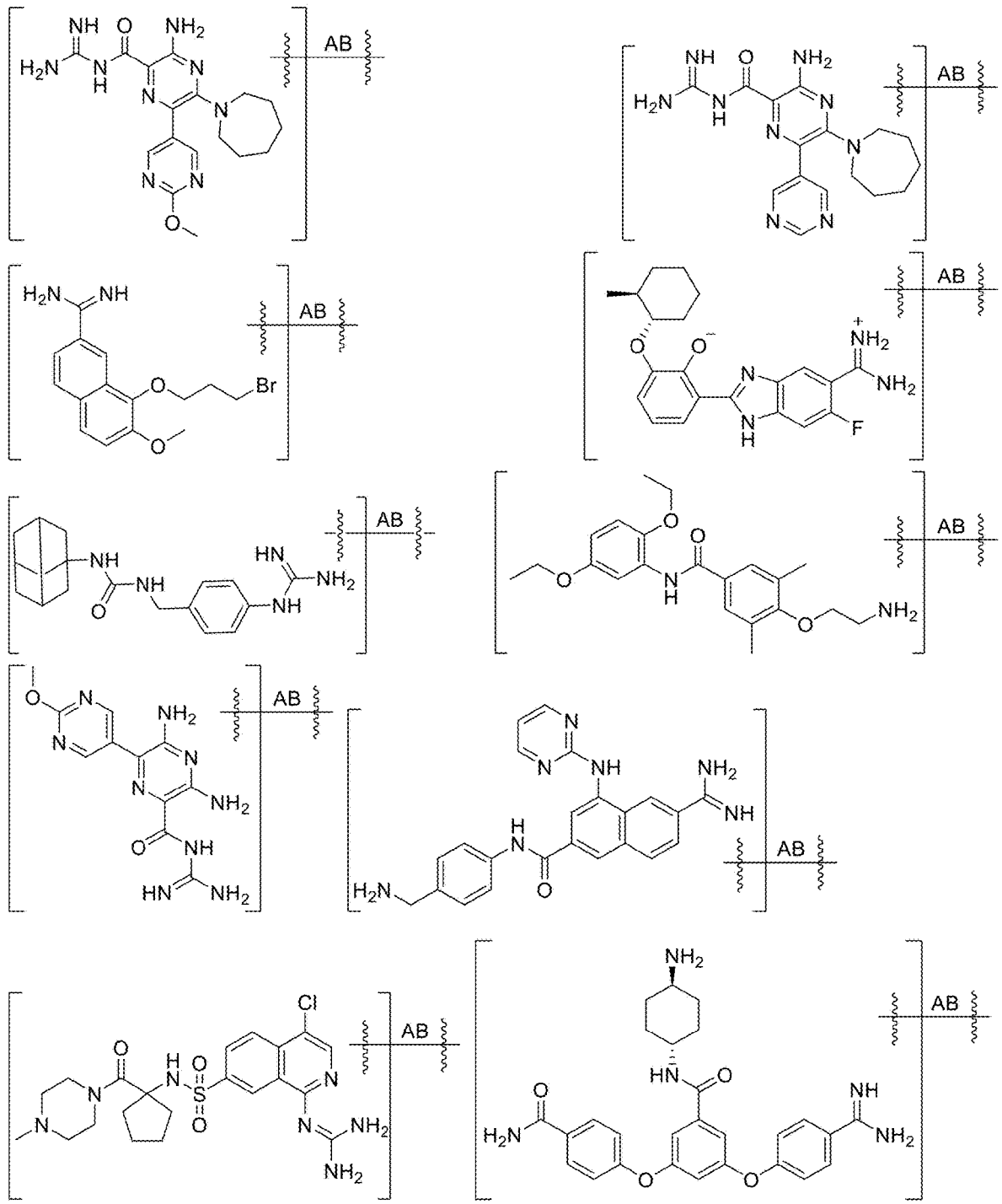
FIG. 1VVVVVV

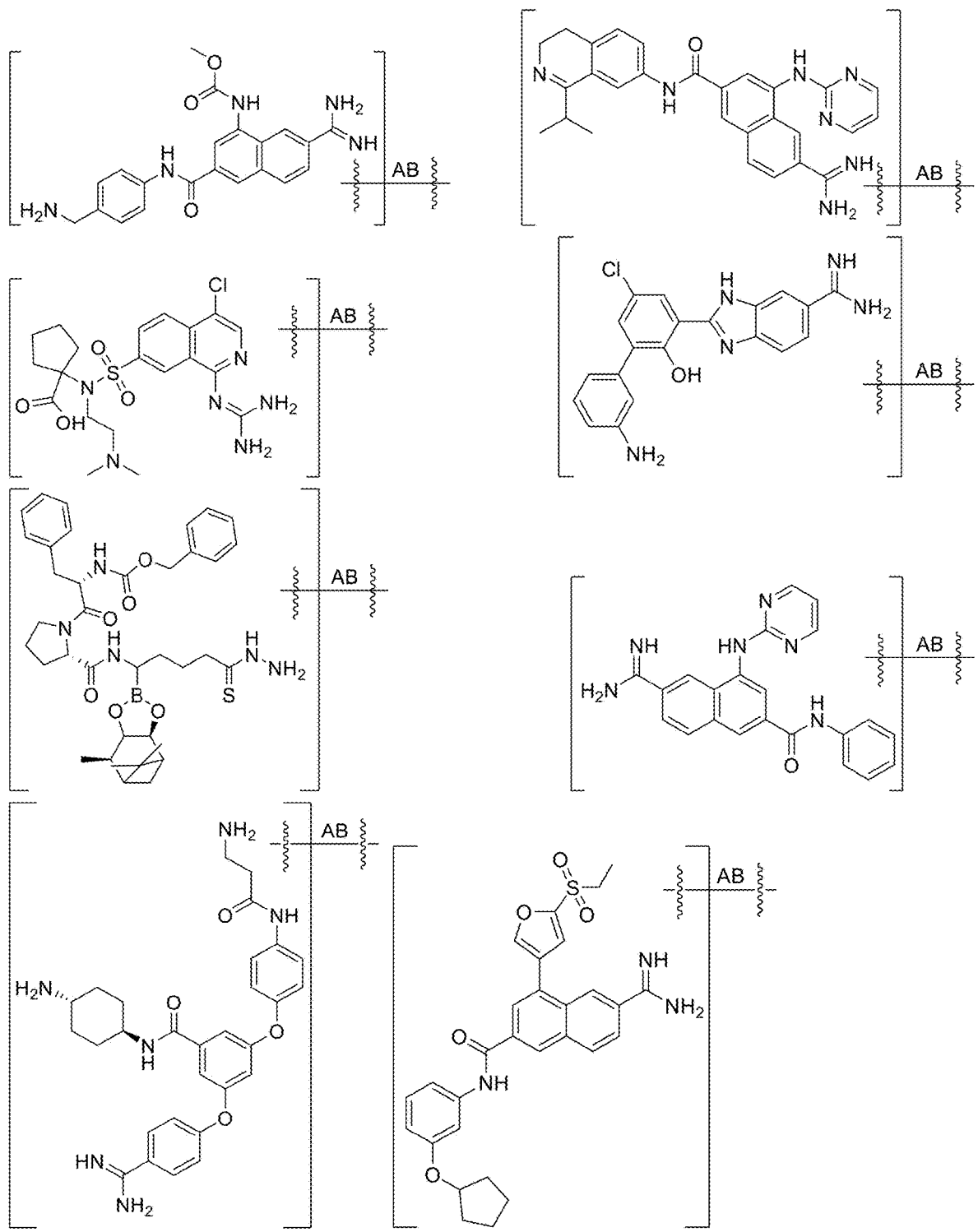
FIG. 1WWWWWW

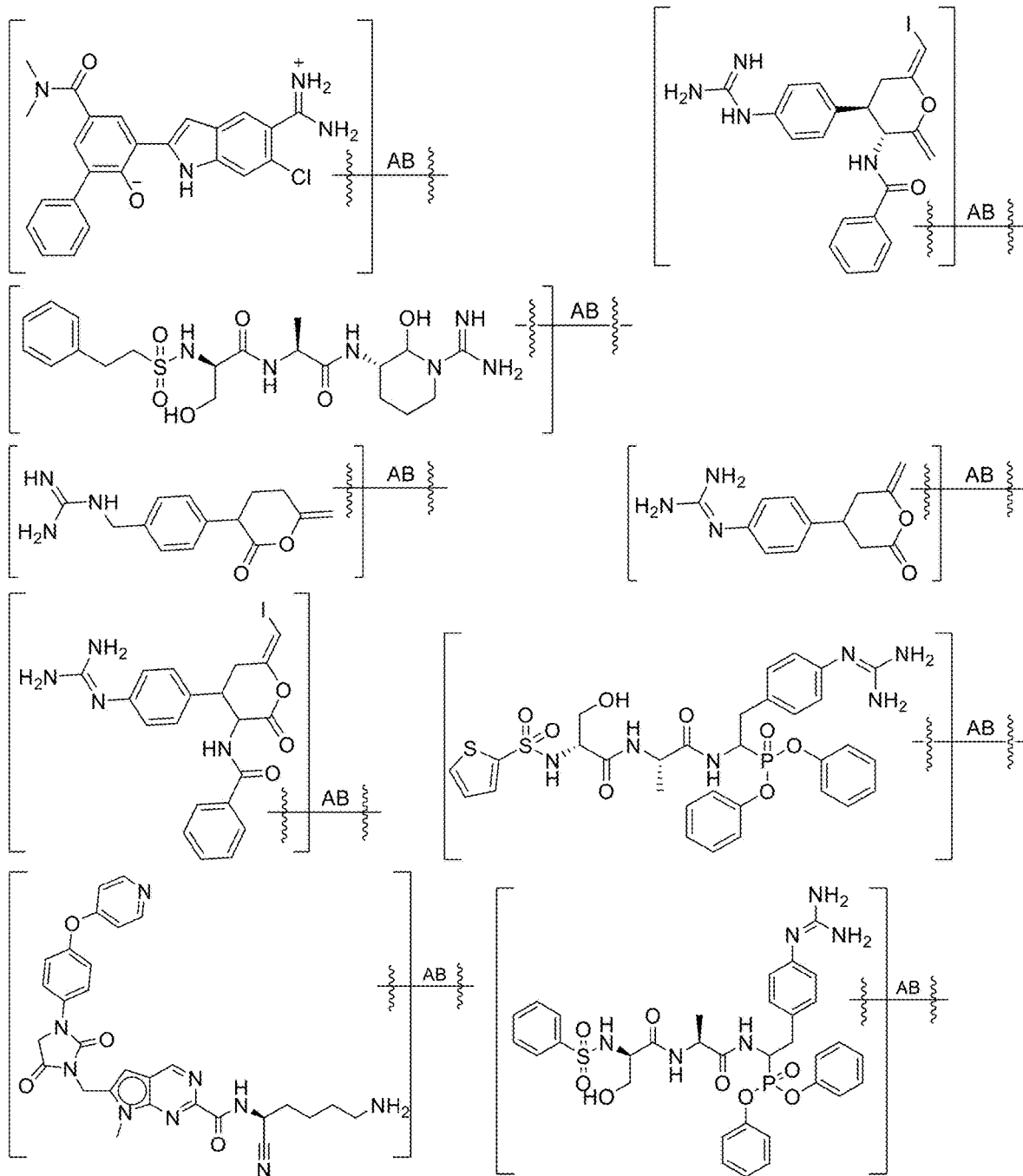
FIG. 1XXXXXX

POTENT ASGPR-BINDING COMPOUNDS FOR THE DEGRADATION OF IMMUNOGLOBULINS AND OTHER PROTEINS

CROSS REFERENCE TO RELATED APPLICATIONS

This application is a continuation of International Patent Application No. PCT/US2022/027513, filed in the U.S. Receiving Office on May 3, 2022, which claims the benefit of U.S. Provisional Application No. 63/331,592, filed Apr. 15, 2022, U.S. Provisional Application No. 63/293,447, filed Dec. 23, 2021, U.S. Provisional Application No. 63/228,067, filed Jul. 31, 2021, and U.S. Provisional Application No. 63/183,450, filed May 3, 2021. The entirety of each of these applications is hereby incorporated by reference for all purposes.

FIELD OF THE INVENTION

This invention provides extracellular protein degraders and compositions that have an asialoglycoprotein receptor (ASGPR) Binding Ligand bound to an Extracellular Protein Targeting Ligand for the selective degradation of the Target Extracellular Protein for example an immunoglobulin or other extracellular protein in vivo to treat disorders mediated by that protein.

INCORPORATION BY REFERENCE

The contents of the XML file named "19121-007WO1US2_SequenceListing_ST26.2" which was created on Sep. 19, 2023, and is 410 KB in size, are hereby incorporated by reference in their entirety.

BACKGROUND OF THE INVENTION

Historically, therapeutic strategies for the inhibition of proteins employed small molecule inhibitors which bound in an enzymatic pocket or at an allosteric position. Those proteins which are not enzymes are difficult to control, and some are considered "not druggable." However, many non-enzymatic proteins remain valuable targets for drug discovery because of their role in signaling pathways. Immunoglobulins represent an important non-enzymatic drug target because of their role in signaling immune responses throughout the body.

The asialoglycoprotein receptor (ASGPR) is a $Ca^{2+}$-dependent lectin that is primarily expressed in parenchymal hepatocyte cells. The main role of ASGPR is to help regulate serum glycoprotein levels by mediating endocytosis of desialylated glycoproteins. The receptor binds ligands with a terminal galactose or N-acetylgalactosamine. Asialoglycoproteins bind to ASGPRs and are then cleared by receptor-mediated endocytosis. The receptor and the protein are dissociated in the acidic endosomal compartment and the protein is eventually degraded by lysosomes. Publications describing various utilizations of the ASGPR mechanism include: U.S. Pat. Nos. 9,340,553; 9,617,293; 10,039,778; 10,376,531, and 10,813,942 assigned to Pfizer Inc.; Sanhueza et al. (*JACS*, 2017, 139, 3528); Petrov et al. (*Bioorganic and Medicinal Chemistry Letters*, 2018, 28, 382); WO 2018/223073 and WO2018/223081 assigned to Pfizer Inc. and Wave Life Sciences Ltd.; WO 2018/223056 assigned to Wave Sciences Ltd.; Schmidt et al. (*Nucleic Acids Research*, 2017, 45, 2294); Huang et al. (*Bioconjugate Chem.* 2017, 28, 283); WO 2019/199621, WO 2019/199634 WO 2021/072246, and WO 2021/072269 assigned to Yale University; WO2020/132100 assigned to The Board of Trustees of the Leland Stanford Junior University; Banik et al. (*Nature*, 2020, 584, 291); and an article from the Bertozzi group titled "LYTACs that engage the asialoglycoprotein receptor for targeted protein degradation," (Ahn, et al. Nat. Chem. Biol. (2021)) published in the journal Nature Chemical Biology.

While some progress has been made in the area of targeted degradation of extracellular proteins, there remains a need for additional therapeutic compounds and methods for their use and manufacture for the degradation of extracellular proteins to treat disorders mediated by those proteins.

SUMMARY OF THE INVENTION

Novel extracellular protein degraders and their pharmaceutically acceptable salts and compositions thereof that degrade a Target Extracellular Protein, for example IgG, IgA, IgE, TNF-alpha, Factor XIa, complement factor D, complement factor B or other proteins as described below as well as starting materials and intermediates for such extracellular protein degraders and their methods of use and manufacture are provided. The extracellular protein degraders of the present invention contain an ASGPR Binding Ligand covalently attached by a Linker to an Extracellular Protein Targeting Ligand. The ASGPR Binding Ligands used in the degraders described herein include derivatives of six-carbon pyranose moieties, specifically galactose and talose. These two sugars, shown below, differ only in the stereochemistry of the $C^2$ substituent. The "down" $C^2$ configuration corresponds to the stereochemistry of galactose, while the $C^2$ substituent in the "up" configuration corresponds to the stereochemistry of talose. It has been discovered that certain substituents at the $C^2$ position of these two sugars improves the binding of the ligand ASGPR.

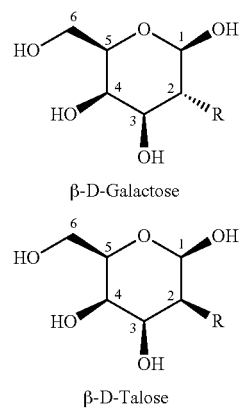

β-D-Galactose

β-D-Talose

In some aspects of the invention, the Extracellular Protein Targeting Ligand targets an immunoglobulin, for example IgG, IgA or IgE.

The immunoglobulin degrading compounds described herein degrade a target immunoglobulin, for example IgG or IgA, by linking a ligand for the selected immunoglobulin to a potent ASGPR binder through specific linking groups. In one embodiment of the present invention, the selected immunoglobulin degrader degrades IgG.

In some embodiments, other extracellular proteins can be degraded as described further below. For example, in nonlimiting illustrative embodiments, a selected Extracellular Protein described generally herein can be targeted, for example, where relevant, using a selected Targeting Ligand of FIGS. 1-7 or as otherwise known.

In some aspects of the present invention, an extracellular protein degrader uses a 3:1 or 2:1 ratio of ASGPR Binding Ligand to Extracellular Protein Targeting Ligand. By using multiple ASGPR Binding Ligands the degrader may bind ASGPR more tightly and thus may have increased degradation efficacy.

In other aspects of the present invention, an extracellular protein degrader of the present invention has a 1:1 ratio of ASGPR Binding Ligand to Extracellular Protein Targeting Ligand. In some aspects, the extracellular protein degrader includes a heteroaryl amine substituent at the $C^2$ position that has a high binding efficiency for ASGPR. With these newly discovered substituents the ligand has sufficient ASGPR binding efficacy to enable degrading molecules with a 1:1 ratio of ASGPR Binding Ligand to Extracellular Protein Targeting Ligand.

While traditional medicinal chemistry approaches to treat diseases associated with extracellular proteins have failed due to their extracellular circulation, size, and/or lack of active site, the extracellular protein degraders of the present invention can degrade a Target Extracellular Protein by trafficking the protein to the hepatocytes. In some embodiments, these immunoglobulin degraders feature select ASGPR ligands that feature high binding affinity for ASGPR (see as non-limiting examples Tables 4A and 4B). As a result of this high ASGPR binding affinity, the extracellular protein degraders of the present invention can often be administered in lower doses, have fewer side effects, decreased side effects, increased efficacy, faster therapeutic effect, longer metabolic stability, and/or longer therapeutic benefit than previously disclosed immunoglobulin degraders.

In some aspects of the present invention, selective degraders of immunoglobulin G (IgG) are provided. In certain embodiments, these immunoglobulin degraders have Fc binding peptides like Fc-III and Fc-BP2 or derivatives thereof. The Fc binding peptides bind the Fc portion of IgG and thus facilitate the selective recruitment of IgG to hepatocytes for degradation. For example, in certain embodiments the immunoglobulin degrader is:

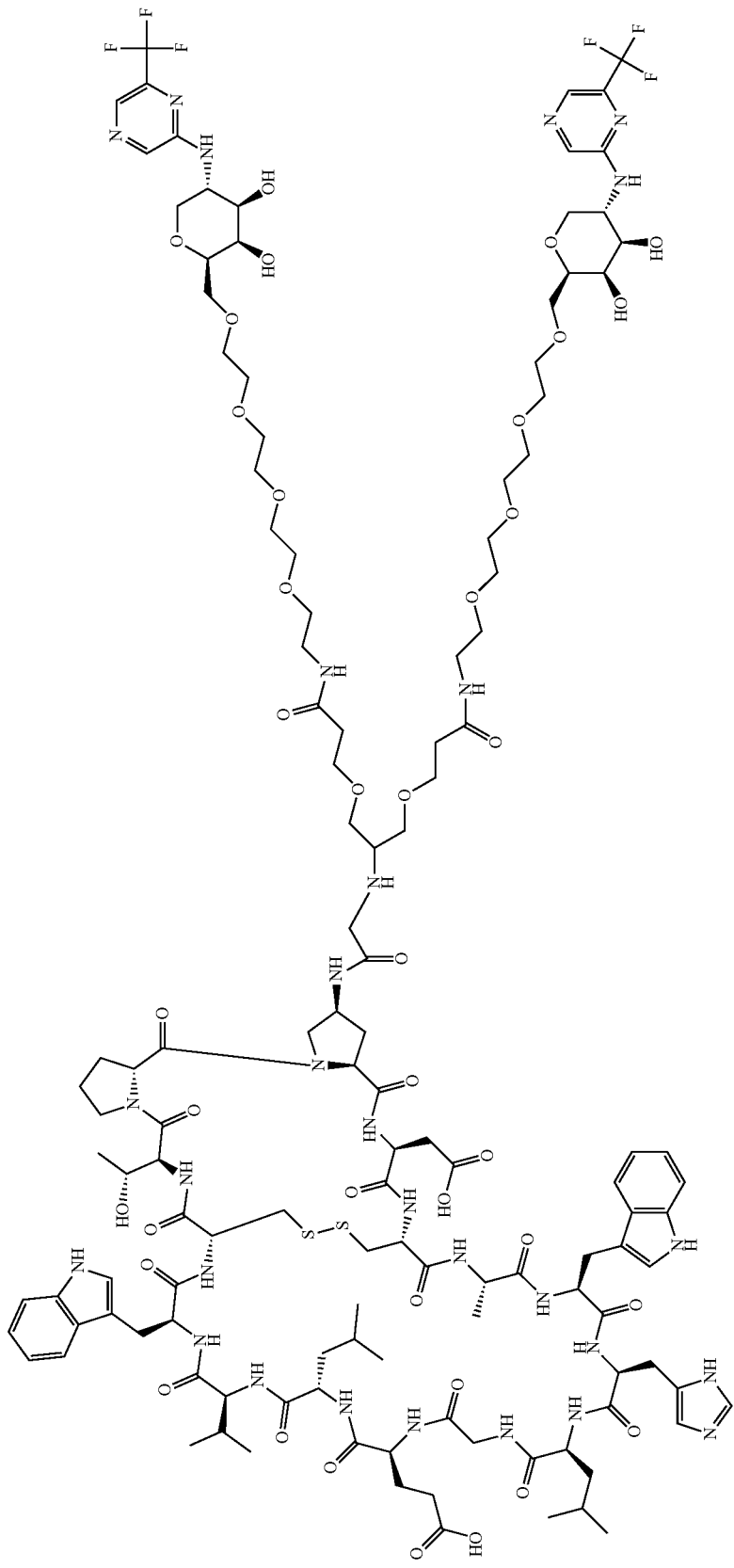

or a pharmaceutically acceptable salt thereof.

In other embodiments, these immunoglobulin degraders have a small molecule or nonpeptidic IgG targeting ligand. Non-limiting examples of small molecule IgG targeting ligands include:

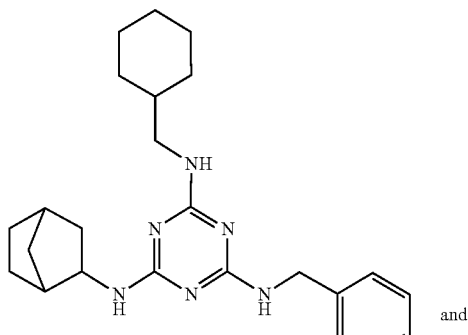

and

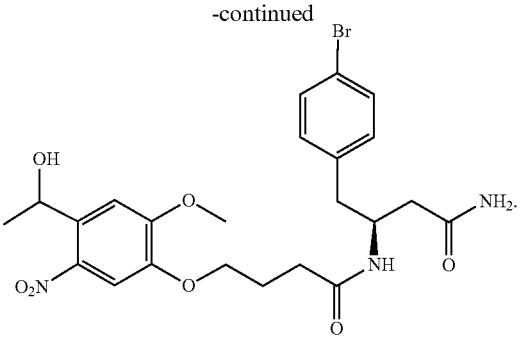

In some aspects of the present invention an IgG degrader of the present invention uses a 2:1 ratio of ASGPR Binding Ligand to Extracellular Protein Targeting Ligand.

In other aspects of the present invention an IgG degrader of the present invention has a 1:1 ratio of ASGPR Binding Ligand to IgG Binding Ligand. For example, in certain embodiments the immunoglobulin degrader is:

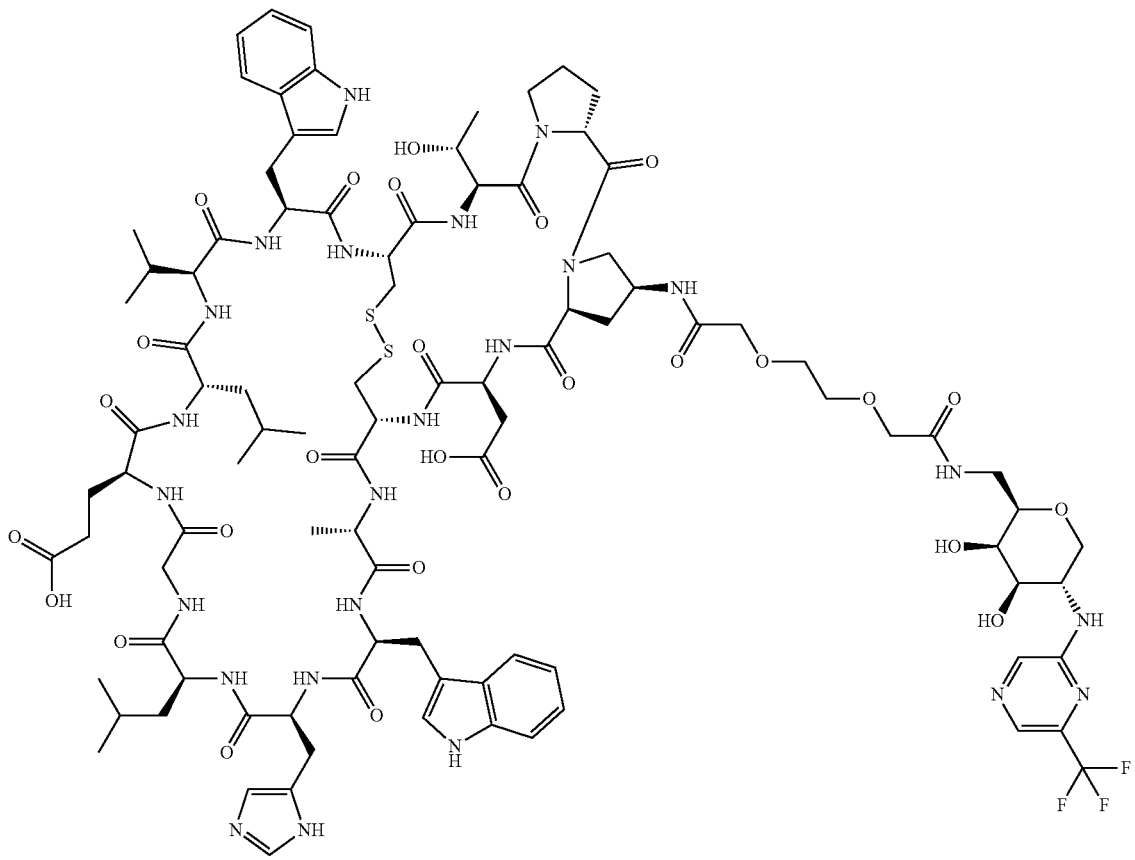 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)COCCOCC(=O)NC[C@H]3OC[C@H](Nc4cncc(C(F)(F)F)n4)[C@@H](O)[C@H]3O)C[C@H]1C(=O)N[C@@H](CC(=O)O)C(=O)N2]

or a pharmaceutically acceptable salt thereof.

The selective targeting of IgG can be particularly beneficial when the present invention is used in the treatment of a disease known to be caused primarily by IgG, such as thyroid eye disease, myasthenia gravis, chronic inflammatory demyelinating polyneuropathy, warm autoimmune hemolytic anemia, or type-1 autoimmune pancreatitis.

In certain aspects the treatment of a disorder mediated by IgG is provided comprising administering an effective amount of an IgG degrader or a pharmaceutically acceptable salt thereof to the patient. In certain embodiments the IgG disorder is selected from antiphospholipid Ab syndrome, Behcet syndrome, Hashimoto thyroiditis, MGUS, necrobiotic xanthogranuloma, rheumatoid arthritis, cancer, for example multiple myeloma or peripheral multiple myeloma, paraproteinemia, chronic urticaria, scleroderma, scleromyxedema, thrombocytopenia for example heparin-induced thrombocytopenia, cryoglobulinema, granulomatosis with polyanglititis, for example ANCA associated vasculitis, idiopathic thrombocytopenic purpura, thrombocytopenia, IgG4-RD, paroxysmal nocturnal hemoglobinuria (PNH), warm autoimmune hemolytic anemia, rhabdomyolysis, lupus nephritis, acute disseminated encephalomyelitis, Guillaine-Barre syndrome, chronic inflammatory demyelinating polyneuropathy, Miller Fisher syndrome, neuromyelitis optica spectrum disorder, opsoclonus-myoclonus syndrome, pediatric autoimmune neuropsychiatric disorder associated with streptococcal infection (PANDAS), peripheral neuropathy, transverse myelitis, fibrosis, IPF/fibrosis, and transplantation rejection.

In other aspects the present invention, a selective degrader of immunoglobulin A (IgA) is provided. In certain embodiments the immunoglobulin degrader has an IgA Targeting Ligand from the Opt class of peptides. The Opt class of ligands is highly selective for IgA and thus facilitates the selective recruitment of IgA to hepatocytes for degradation. For example, in certain embodiments the immunoglobulin degrader is:

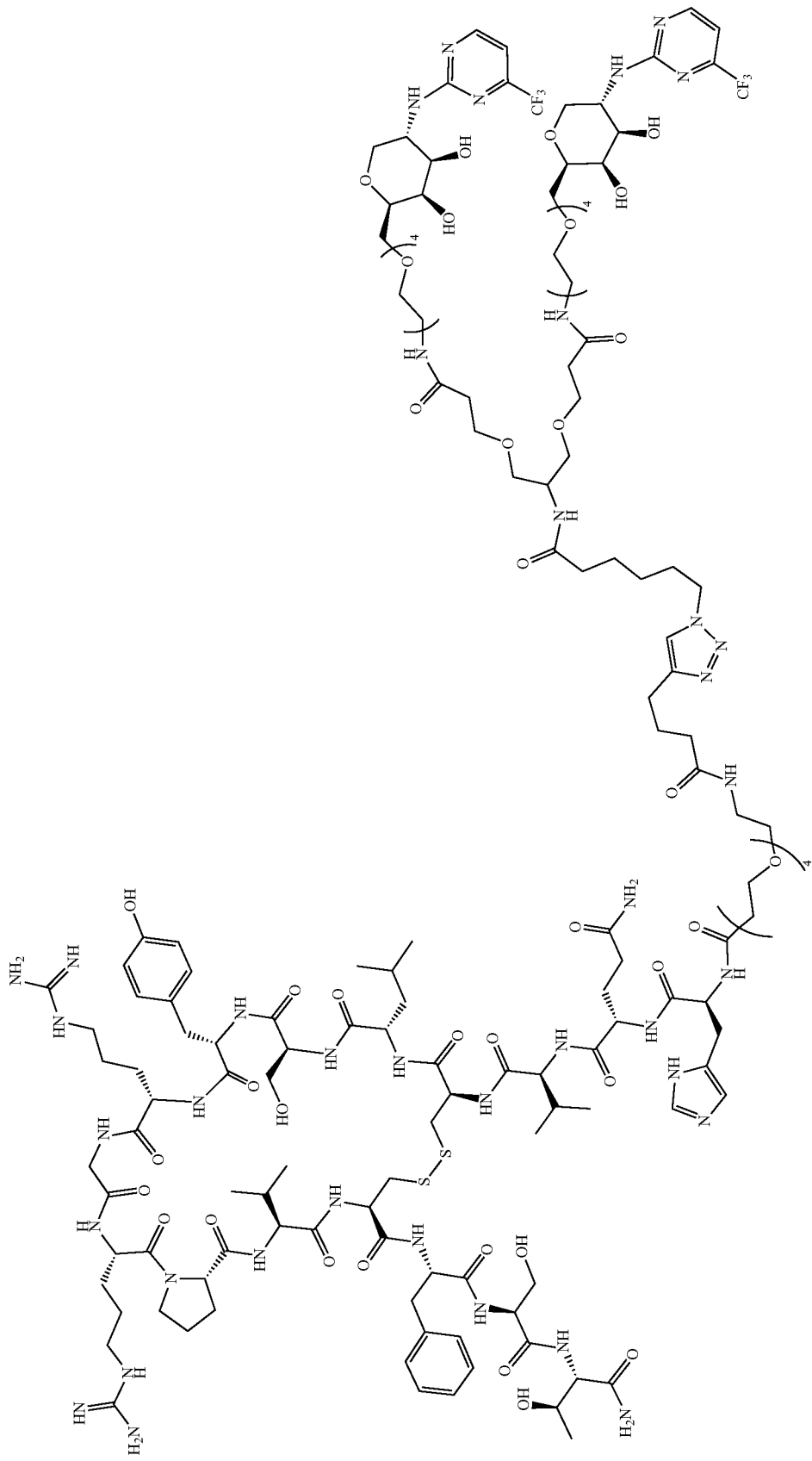

or a pharmaceutically acceptable salt thereof.

In some aspects of the present invention an IgA degrader uses a 2:1 ratio of ASGPR Binding Ligands to IgA Binding Ligand.

In other aspects of the present invention an IgA degrader of the present invention has a 1:1 ratio of ASGPR Binding Ligand to IgA Binding Ligand. For example, in certain embodiments the immunoglobulin degrader is:

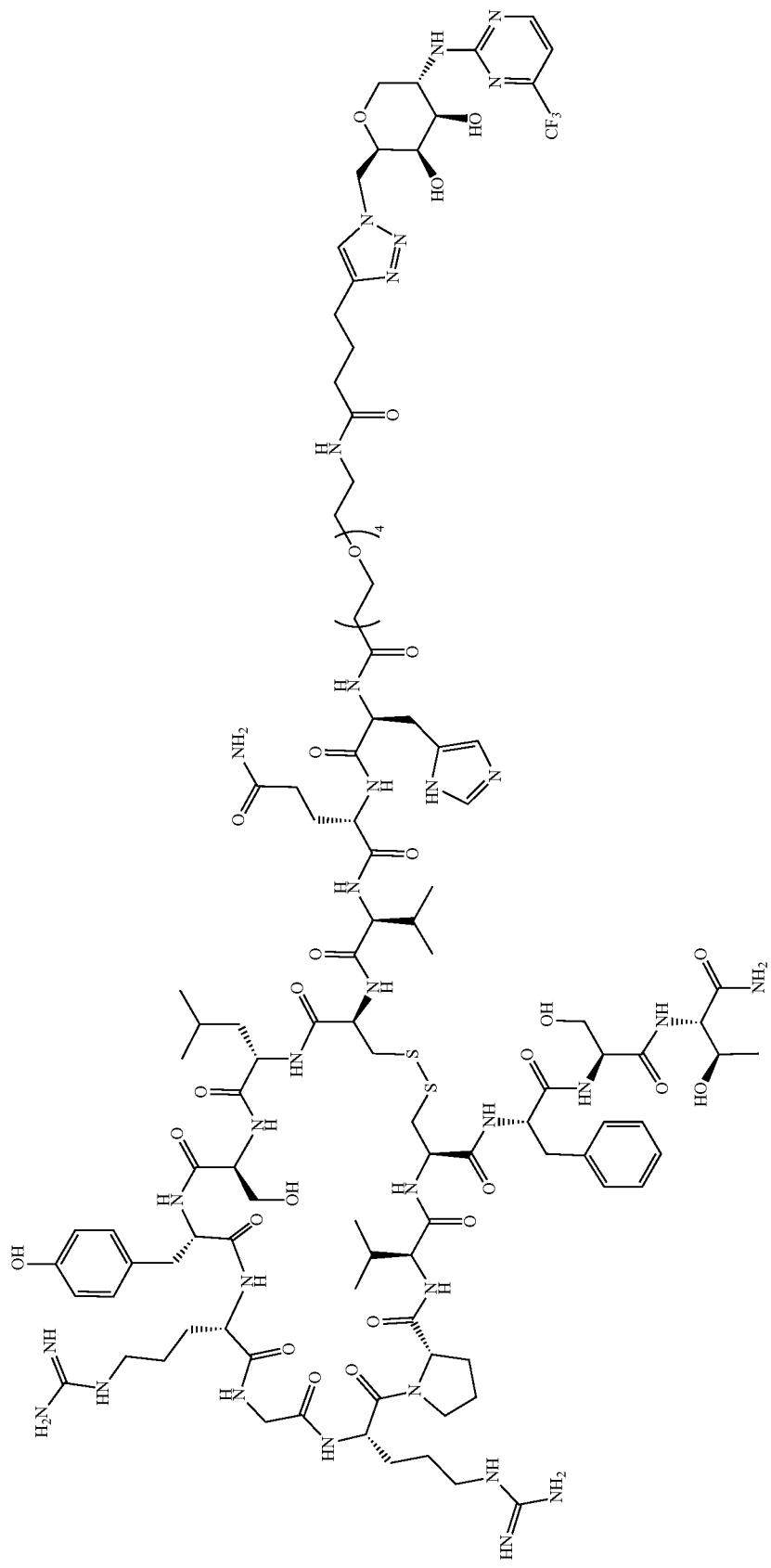

The selective targeting of IgA can be particularly beneficial when the present invention is used in the treatment of a disease known to be caused primarily by IgA, such as Henoch-Schonlein purpura, also known as IgA vasculitis. Additional disorders mediated by IgA include cryoglobulinemia, granulomatosis with polyangiitis, thrombocytopenia, peripheral neuropathy, MGUS, IgA nephropathy, Henoch Schonlein purpura.

The immunoglobulin degraders described herein can be used to treat a disorder mediated by an immunoglobulin, for example IgG or IgA, including for example an autoimmune disorder, other immune dysfunction, abnormal cellular proliferation such as tumors and cancer, hematology-related disorder, renal disorder, allergic condition, or liver disorder. In certain aspects of the invention, a method for treating a disorder mediated by an immunoglobulin is provided that includes administering to a host in need thereof an effective amount of an immunoglobulin degrader described herein, or its pharmaceutically acceptable salt, prodrug, N-oxide, and/or a pharmaceutically acceptable composition thereof optionally in a pharmaceutically acceptable carrier.

While traditional medicinal chemistry approaches to treat diseases associated with immunoglobulins have failed due to their large size, extracellular circulation, and/or lack of active site, the immunoglobulin degraders of the present invention can degrade the targeted immunoglobulin. In some embodiments, these immunoglobulin degraders feature newly discovered ASGPR ligands which feature high binding affinity for ASGPR (see Table 4). As a result of this high ASGPR binding affinity the immunoglobulin degraders of the present invention can be administered in lower doses, have fewer side effects, increased efficacy, faster therapeutic effect, longer metabolic stability, and/or decreased side effects than previously disclosed immunoglobulin degraders.

In certain aspects the extracellular protein degrading compound degrades TNF-alpha. For example, in certain embodiments the compound of the present invention is:

In certain embodiments the TNF-alpha Targeting Ligand is selected from:

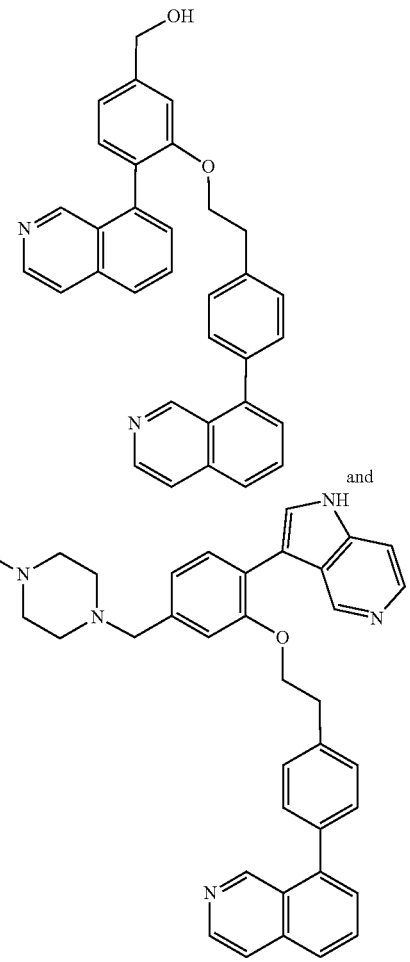

and

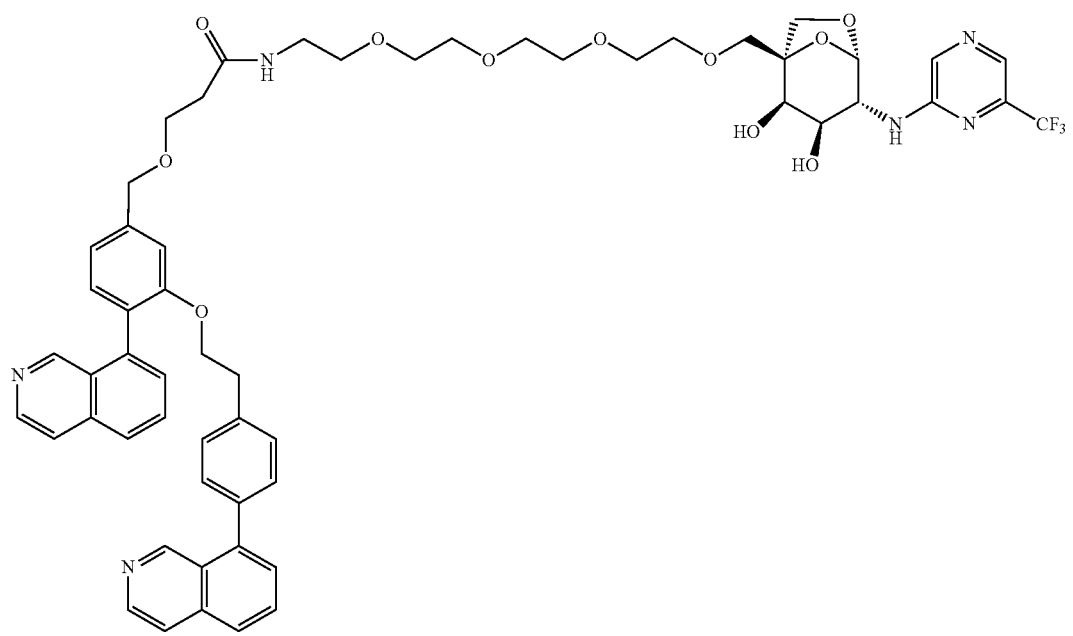 [SMILES: O=C(CCOCc1ccc(-c2cccc3ccncc23)c(OCCc2ccc(-c3cccc4ccncc34)cc2)c1)NCCOCCOCCOCCOC[C@@]12CO[C@@H](O1)[C@H](Nc1cncc(C(F)(F)F)n1)[C@@H](O)[C@H]2O]

In certain aspects the extracellular protein degrading compound degrades Factor XIa. For example, in certain embodiments the compound of the present invention is:

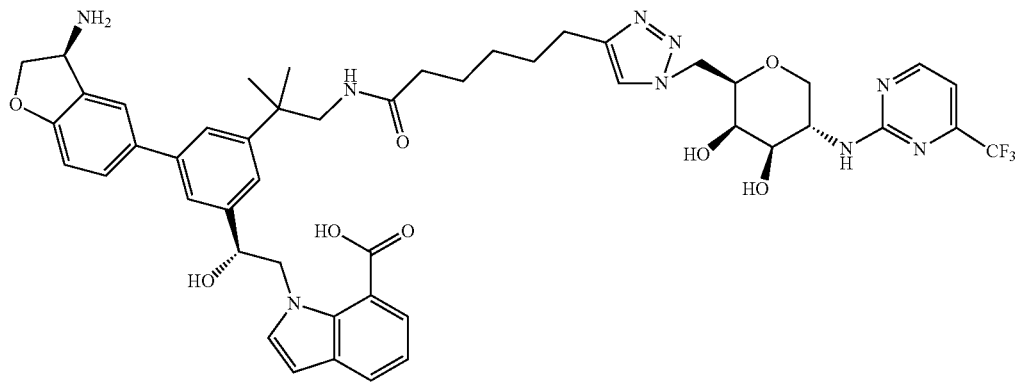

In certain embodiments the Factor XIa Targeting Ligand is selected from:

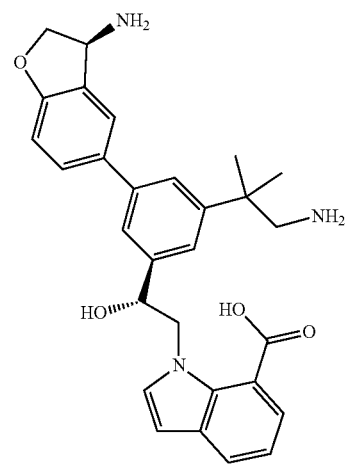

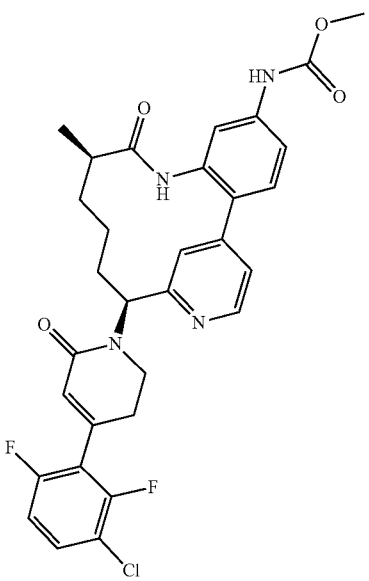

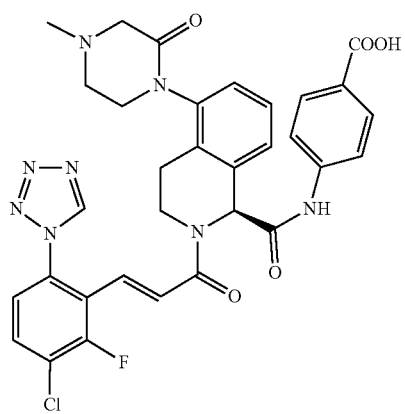

and

In another aspect an ASGPR Binding Ligand of Formula I, Formula II, Formula III, Formula IV, Formula V, Formula VI, Formula VII, or Formula VIII is provided:

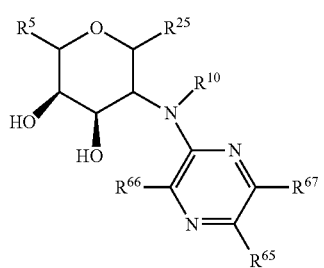

(I)

21
-continued (II)
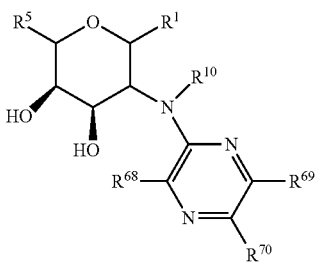

(III)
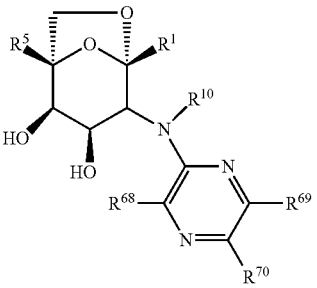

(IV)
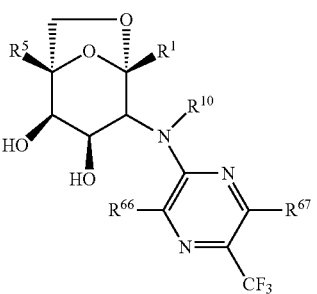

(V)
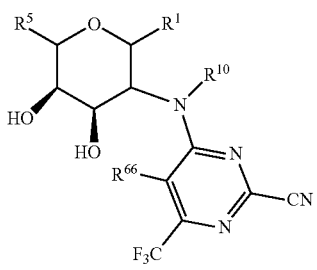

(VI)
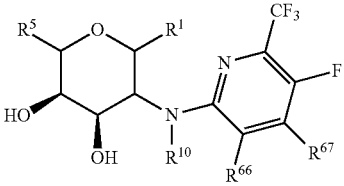

(VII)
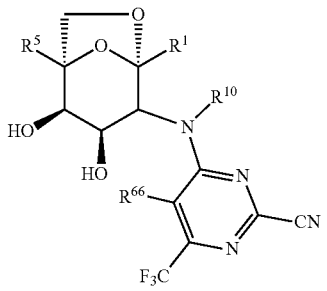

22
-continued (VIII)
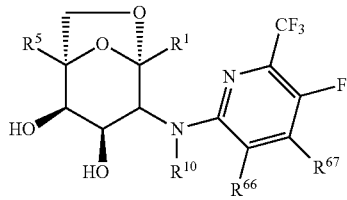

or a pharmaceutically acceptable salt thereof;
wherein:
$R^1$ and $R^5$ are independently selected from hydrogen, heteroalkyl, $C_0$-$C_6$alkyl-cyano, alkyl, alkenyl, alkynyl, haloalkyl, F, Cl, Br, I, aryl, arylalkyl, heteroaryl, heteroarylalkyl, heterocycle, heterocycloalkyl, haloalkoxy, $C_0$-$C_6$alkyl-$OR^6$, $C_0$-$C_6$alkyl-$SR^6$, $C_0$-$C_6$alkyl-$NR^6R^7$, $C_0$-$C_6$alkyl-$C(O)R^3$, $C_0$-$C_6$alkyl-S(O)$R^3$, $C_0$-$C_6$alkyl-$C(S)R^3$, $C_0$-$C_6$alkyl-S(O)$_2R^3$, $C_0$-$C_6$alkyl-$N(R^8)$—$C(O)R^3$, $C_0$-$C_6$alkyl-$N(R^8)$—S(O)$R^3$, $C_0$-$C_6$alkyl-$N(R^8)$—$C(S)R^3$, $C_0$-$C_6$alkyl-$N(R^8)$—S(O)$_2R^3$, $C_0$-$C_6$alkyl-O—$C(O)R^3$, $C_0$-$C_6$alkyl-O—S(O)$R^3$, $C_0$-$C_6$alkyl-O—$C(S)R^3$, —N=S(O)($R^3$)$_2$, $C_0$-$C_6$alkylN$_3$, and $C_0$-$C_6$alkyl-O—S(O)$_2R^3$, each of which is optionally substituted with 1, 2, 3, or 4 substituents;
$R^3$ at each occurrence is independently selected from hydrogen, alkyl, heteroalkyl, haloalkyl, arylalkyl, heteroarylalkyl, alkenyl, alkynyl, aryl, heteroaryl, heterocycle, —$OR^8$, and —$NR^8R^9$;
$R^6$ and $R^7$ are independently selected at each occurrence from hydrogen, heteroalkyl, alkyl, arylalkyl, heteroarylalkyl, alkenyl, alkynyl, aryl, haloalkyl, heteroaryl, heterocycle, -alkyl-$OR^8$, -alkyl-$NR^8R^9$, $C(O)R^3$, $S(O)R^3$, $C(S)R^3$, and $S(O)_2R^3$;
$R^8$ and $R^9$ are independently selected at each occurrence from hydrogen, heteroalkyl, alkyl, arylalkyl, heteroarylalkyl, alkenyl, alkynyl, aryl, heteroaryl, and heterocycle;
$R^{10}$ is selected from hydrogen, alkyl, heteroalkyl, haloalkyl, arylalkyl, heteroarylalkyl, alkenyl, alkynyl, aryl, heteroaryl, heterocycle, $C(O)R^3$, $S(O)R^3$, $C(S)R^3$, and $S(O)_2R^3$;
$R^{25}$ is selected from the group consisting of heteroalkyl, $C_0$-$C_6$alkyl-cyano, alkyl, alkenyl, alkynyl, haloalkyl, F, Cl, Br, I, aryl, arylalkyl, heteroaryl, heteroarylalkyl, heterocycle, heterocycloalkyl, haloalkoxy, $C_0$-$C_6$alkyl-$OR^6$, $C_0$-$C_6$alkyl-$SR^6$, $C_0$-$C_6$alkyl-$NR^6R^7$, $C_0$-$C_6$alkyl-$C(O)R^3$, $C_0$-$C_6$alkyl-$S(O)R^3$, $C_0$-$C_6$alkyl-$C(S)R^3$, $C_0$-$C_6$alkyl-$S(O)_2R^3$, $C_0$-$C_6$alkyl-$N(R^8)$—$C(O)R^3$, $C_0$-$C_6$alkyl-$N(R^8)$—$S(O)R^3$, $C_0$-$C_6$alkyl-$N(R^8)$—$C(S)R^3$, $C_0$-$C_6$alkyl-$N(R^8)$—$S(O)_2R^3$, $C_0$-$C_6$alkyl-O—$C(O)R^3$, $C_0$-$C_6$alkyl-O—$S(O)R^3$, $C_0$-$C_6$alkyl-O—$C(S)R^3$, —N=S(O)($R^3$)$_2$, $C_0$-$C_6$alkylN$_3$, and $C_0$-$C_6$alkyl-O—$S(O)_2R^3$, each of which is optionally substituted with 1, 2, 3, or 4 substituents;
$R^{65}$, $R^{66}$, and $R^{67}$ are independently selected from hydrogen, heteroalkyl, $C_0$-$C_6$alkyl-cyano, alkyl, alkenyl, alkynyl, haloalkyl, F, Cl, Br, I, heterocycle, heterocycloalkyl, haloalkoxy, $C_0$-$C_6$alkyl-$OR^6$, $C_0$-$C_6$alkyl-$SR^6$, $C_0$-$C_6$alkyl-$NR^6R^7$, $C_0$-$C_6$alkyl-$C(O)R^3$, $C_0$-$C_6$alkyl-$S(O)R^3$, $C_0$-$C_6$alkyl-$C(S)R^3$, $C_0$-$C_6$alkyl-$S(O)_2R^3$, $C_0$-$C_6$alkyl-$N(R^8)$—$C(O)R^3$, $C_0$-$C_6$alkyl-$N(R^8)$—$S(O)R^3$, $C_0$-$C_6$alkyl-$N(R^8)$—$C(S)R^3$, $C_0$-$C_6$alkyl-$N(R^8)$—$S(O)_2R^3$, $C_0$-$C_6$alkyl-O—$C(O)R^3$, $C_0$-$C_6$alkyl-O—$S(O)R^3$, $C_0$-$C_6$alkyl-O—$C(S)R^3$, —N=S(O)(R³)₂, C₀-C₆alkylN₃, and C₀-C₆alkyl-O—S(O)₂R³, each of which is optionally substituted with 1, 2, 3, or 4 substituents;

R⁶⁸, R⁶⁹, and R⁷⁰ are independently selected from hydrogen, alkyl, alkenyl, alkynyl, F, Cl, Br, I, heterocycle, heterocycloalkyl, haloalkoxy, C₀-C₆alkyl-OR⁶, C₀-C₆alkyl-SR⁶, C₀-C₆alkyl-NR⁶R⁷, C₀-C₆alkyl-C(O)R³, C₀-C₆alkyl-S(O)R³, C₀-C₆alkyl-C(S)R³, C₀-C₆alkyl-S(O)₂R³, C₀-C₆alkyl-N(R⁸)—C(O)R³, C₀-C₆alkyl-N(R⁸)—S(O)R³, C₀-C₆alkyl-N(R⁸)—C(S)R³, C₀-C₆alkyl-N(R⁸)—S(O)₂R³, C₀-C₆alkyl-O—C(O)R³, C₀-C₆alkyl-O—S(O)R³, C₀-C₆alkyl-O—C(S)R³, —N=S(O)(R³)₂, C₀-C₆alkylN₃, heteroaryl, aryl, and C₀-C₆alkyl-O—S(O)₂R³ each of which is optionally substituted with 1, 2, 3, or 4 substituents; and when a compound is "optionally substituted" it may be substituted as allowed by valence with one or more groups selected from alkyl (including C₁-C₄alkyl), alkenyl (including C₂-C₄alkenyl), alkynyl (including C₂-C₄alkynyl), haloalkyl (including C₁-C₄haloalkyl), —OR⁶, F, Cl, Br, I, —NR⁶R⁷, heteroalkyl, heterocycle, heteroaryl, aryl, cyano, nitro, hydroxyl, azide, amide, —SR³, —S(O)(NR⁶)R³, —NR⁸C(O)R³, —C(O)NR⁶R⁷, —C(O)OR³, —C(O)R³, —SF₅,

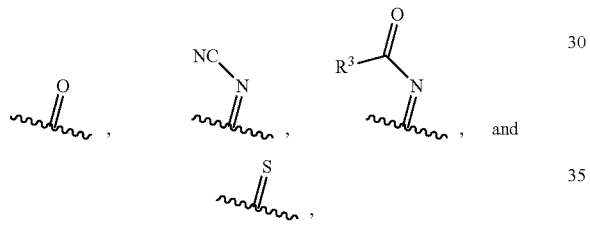

wherein the optional substituent is selected such that a stable compound results.

In certain embodiments the ASGPR Binding Ligand is selected from:

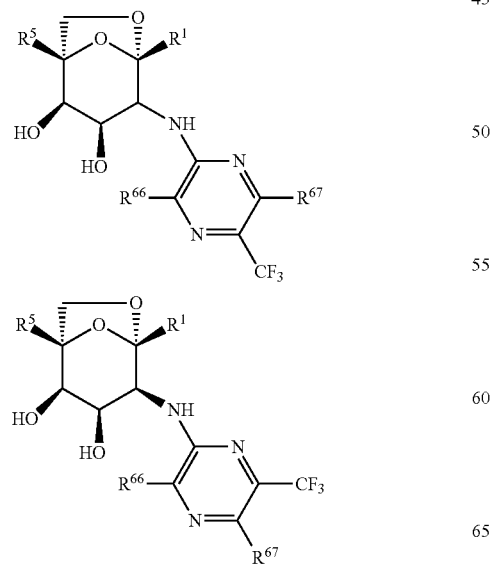

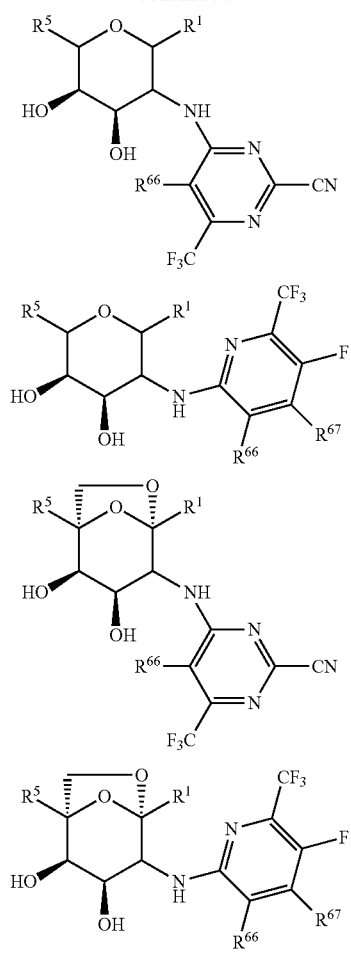

or a pharmaceutically acceptable salt thereof.

In an alternative aspect the ASGPR Binding Ligand is of Formula:

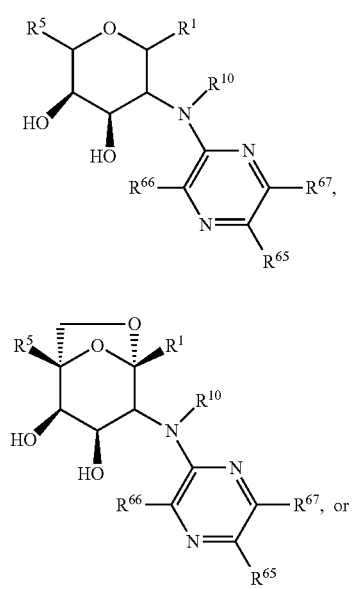

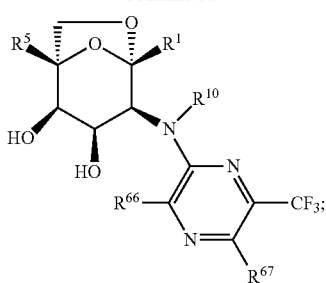
or a pharmaceutically acceptable salt thereof.
In certain aspects an extracellular protein degrading compound of Formula IX, Formula X, or Formula XI is provided:
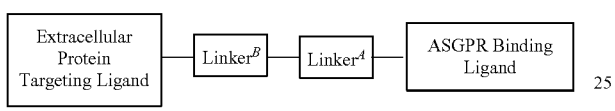
(IX)
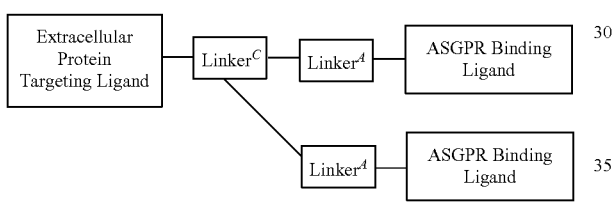
(X)
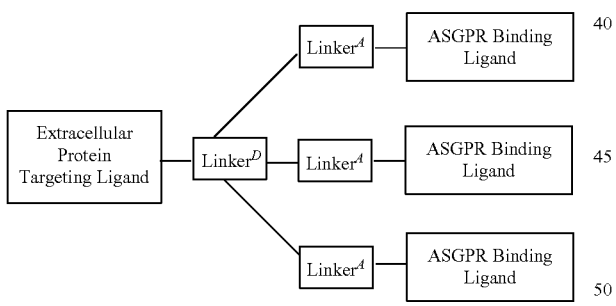
(XI)
wherein
ASPGR Binding Ligand is a compound selected from:
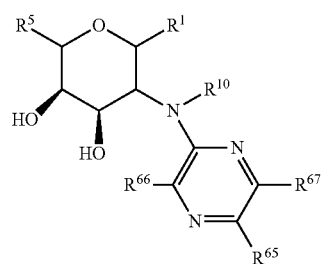
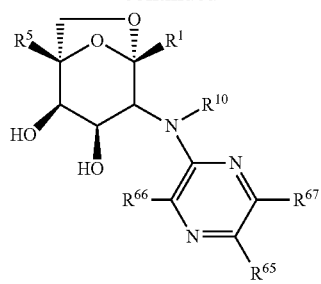
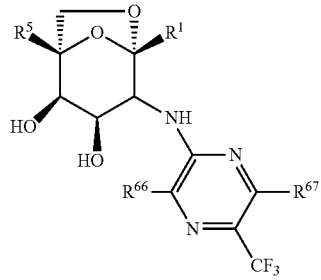
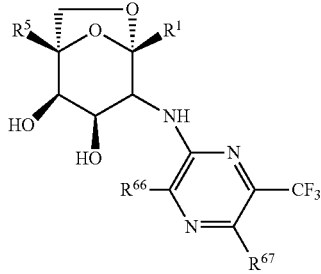
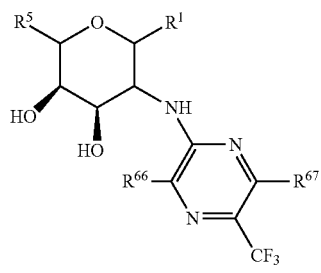
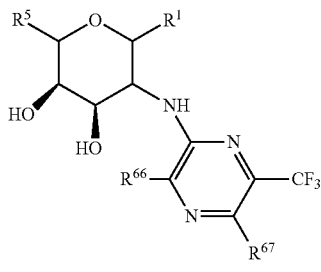
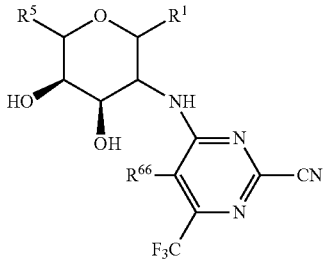

-continued

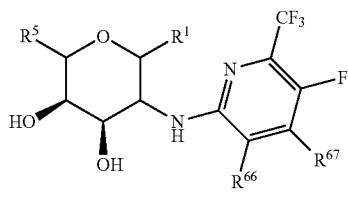

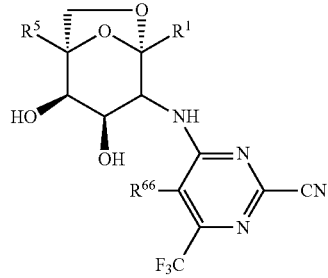

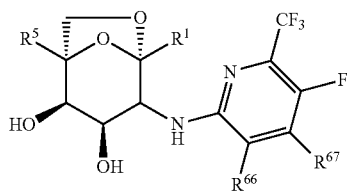

wherein R¹ or R⁵ is replaced with a bond to Linker⁴ and all other variables are as defined herein;

Linker⁴ is a bond or a moiety that covalently links Linker$^B$, Linker$^C$, or Linker$^D$ to the ASGPR Binding Ligand;

Linker$^B$ is a bond or a moiety that covalently links Linker⁴ to an Extracellular Protein Targeting Ligand;

Linker$^C$ is a chemical group that links each Linker⁴ to the Extracellular Protein Targeting Ligand;

Linker$^D$ is a chemical group that links each Linker⁴ to the Extracellular Protein Targeting Ligand; and Extracellular Protein Targeting Ligand is a Ligand that binds to an extracellular protein.

In certain aspects an immunoglobulin degrading compound of Formula IX-A, Formula X-A, or Formula XI-A is provided:

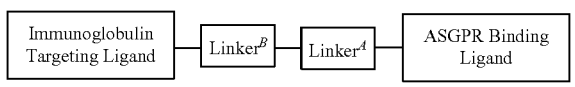
(IX-A)

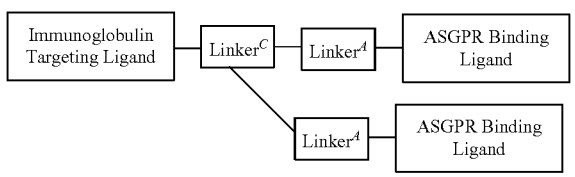
(X-A)

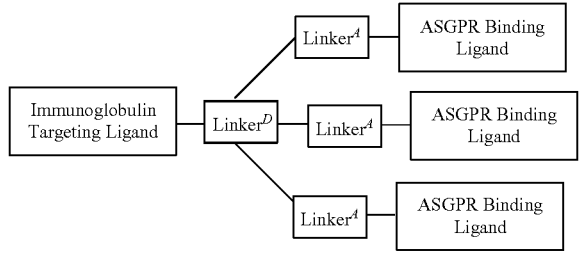
(XI-A)

or a pharmaceutically acceptable salt thereof, wherein:

Immunoglobulin Targeting Ligand is a Ligand that binds to an immunoglobulin, for example IgG or IgA.

In certain embodiments ASGPR Binding Ligand is a compound selected from:

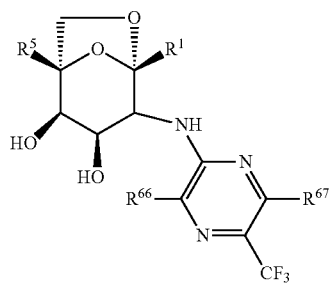

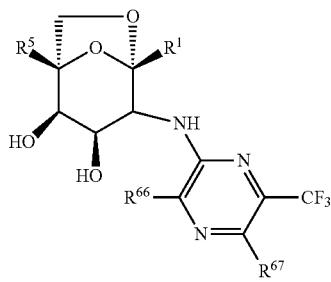

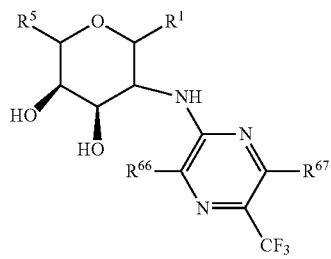

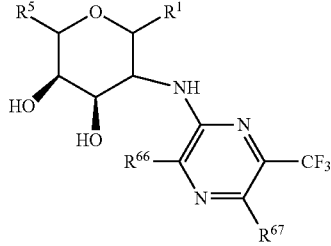

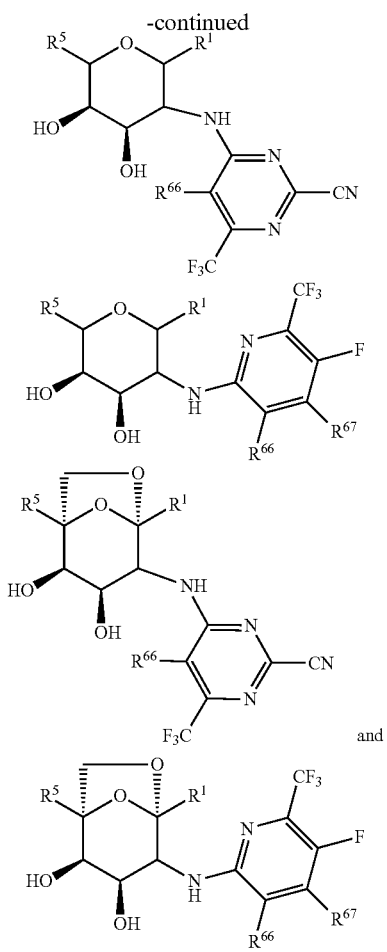

or a pharmaceutically acceptable salt thereof.

In certain embodiments the extracellular protein degrader of the present invention is provided as an isotopically enriched extracellular protein degrader, for example an immunoglobulin degrader, with at least one desired isotopic substitution of an atom, at an amount above the natural abundance of the isotope. For example, deuterium can replace one or more hydrogens in the extracellular protein degrader and $^{13}C$ can replace one or more carbon atoms. In one embodiment, the isotopic substitution is in one or more positions of the ASGPR Ligand. In another embodiment, the isotopic substitution is in one or more positions of the Linker portion of the molecule. In another embodiment, the isotopic substitution is in one or more positions of the Extracellular Protein Targeting Ligand portion of the molecule.

The present invention thus includes at least the following features:

(i) An extracellular protein degrader described herein or a pharmaceutically acceptable salt thereof, prodrug, N-oxide, and/or a pharmaceutical composition thereof as described herein;

(ii) An extracellular protein degrader described herein for use in treating a medical disorder which is associated with immunoglobulins, such as autoimmune disorders, other immune dysfunctions, hematology-related disorders, renal disorders, allergic condition, or liver disorders;

(iii) An isotopically enriched derivative of an extracellular protein degrader described herein or pharmaceutically acceptable salt, prodrug, N-oxide, and/or a pharmaceutical composition thereof;

(iv) A process for manufacturing a medicament intended for the therapeutic use for treating or preventing a disorder mediated by an extracellular protein, characterized in that an extracellular protein degrader described herein is used in the manufacture;

(v) An extracellular protein degrader described above or a salt thereof as described herein in purified or substantially pure form (e.g., at least 90, 95, 96, 97, 98, 99, 99.5, or 99.9%);

(vi) An extracellular protein degrader described herein to treat a disorder described herein;

(vii) A method for the manufacture of an extracellular protein degrader described herein;

(viii) An immunoglobulin degrader described herein or a pharmaceutically acceptable salt thereof, prodrug, N-oxide, and/or a pharmaceutical composition thereof as described herein;

(ix) An immunoglobulin degrader described herein for use in treating a medical disorder which is associated with an immunoglobulin, such as an autoimmune disorder, other immune dysfunction, hematology-related disorder, renal disorder, allergic condition, or liver disorder;

(x) An isotopically enriched derivative of an immunoglobulin degrader described herein or pharmaceutically acceptable salt, prodrug, N-oxide, and/or a pharmaceutical composition thereof;

(xi) A process for manufacturing a medicament intended for the therapeutic use for treating or preventing a disorder mediated by an immunoglobulin, characterized in that an immunoglobulin degrader described herein is used in the manufacture;

(xii) An immunoglobulin degrader described above or a salt thereof as described herein in purified or substantially pure form (e.g., at least 90, 95, 96, 97, 98, 99, 99.5, or 99.9%);

(xiii) An immunoglobulin degrader described herein to treat a disorder described herein;

(xiv) A method for the manufacture of an immunoglobulin degrader described herein; and (xv) An ASGPR Binding Ligand described herein.

BRIEF DESCRIPTION OF THE FIGURES

The Extracellular Protein Target Ligand ("EPTL") is covalently bound to Linker in the ASGPR-binding extracellular protein degrader compound through the Anchor Bond (which is the chemical bond between the EPTL and either Linker B, Linker C or Linker D). This bond can be placed at any location on the ligand that does not unacceptably disrupt the ability of the EPTL to bind to the Target Extracellular Protein. The Anchor Bond is depicted on the nonlimiting examples of Extracellular Protein Target Ligands in the figures as:

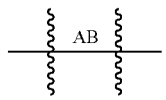

FIG. 1X-1AA provides a non-limiting list of Extracellular Protein Targeting Ligands that target Interferon gamma (IFN-γ).

FIG. 1BB-1KK provides a non-limiting list of Extracellular Protein Targeting Ligands that target Vascular endothelial growth factor (VEGF).

FIG. 1LL provides a non-limiting list of Extracellular Protein Targeting Ligands that target Transforming growth factor beta (TGF-β1).

FIG. 1MM-1PP provides a non-limiting list of Extracellular Protein Targeting Ligands that target proprotein convertase subtilisin kexin 9 (PCSK-9).

FIG. 1QQ-1SS provides a non-limiting list of Extracellular Protein Targeting Ligands that target Carboxypeptidase B2 (CPB2).

FIG. 1TT-1UU provides a non-limiting list of Extracellular Protein Targeting Ligands that target Cholinesterase (ChE).

FIG. 1VV-1WW provides a non-limiting list of Extracellular Protein Targeting Ligands that target C—C Motif Chemokine Ligand 2 (CCL2).

FIG. 1XX-1BBB provides a non-limiting list of Extracellular Protein Targeting Ligands that target coagulation factor VII (Factor VII).

FIG. 1CCC-1FFF provides a non-limiting list of Extracellular Protein Targeting Ligands that target coagulation factor IX (Factor IX).

FIG. 1GGG provides a non-limiting list of Extracellular Protein Targeting Ligands that target CD40 Ligand (CD40L).

FIG. 1HHH-1JJJ provides a non-limiting list of Extracellular Protein Targeting Ligands that target coagulation factor Xa (Factor Xa).

FIG. 1KKK-1MMM provides a non-limiting list of Extracellular Protein Targeting Ligands that target coagulation factor XI (Factor XI).

FIGS. 1NNN and 1OOO provides a non-limiting list of Extracellular Protein Targeting Ligands that target coagulation factor XII (Factor XII).

FIGS. 1PPP and 1QQQ provides a non-limiting list of Extracellular Protein Targeting Ligands that target coagulation factor XIII (Factor XIII).

FIG. 1RRR-1UUU provides a non-limiting list of Extracellular Protein Targeting Ligands that target fibroblast growth factor 1 (FGF1).

FIG. 1VVV-1XXX provides a non-limiting list of Extracellular Protein Targeting Ligands that target fibroblast growth factor 2 (FGF2).

FIGS. 1AAAA and 1BBBB provides a non-limiting list of Extracellular Protein Targeting Ligands that target Interleukin-5 (IL-5).

FIG. 1CCCC provides a non-limiting list of Extracellular Protein Targeting Ligands that target Interleukin-8 (IL-8).

FIGS. 1DDDD and 1EEEE provides a non-limiting list of Extracellular Protein Targeting Ligands that target Interleukin-10 (IL-10).

FIGS. 1FFFF and 1GGGG provides a non-limiting list of Extracellular Protein Targeting Ligands that target Interleukin-21 (IL-21).

FIGS. 1HHHH and 1IIII provides a non-limiting list of Extracellular Protein Targeting Ligands that target Interleukin-22 (IL-22).

FIG. 1JJJJ-1NNNN provides a non-limiting list of Extracellular Protein Targeting Ligands that target Kallikrein 1.

FIG. 1OOOO provides a non-limiting list of Extracellular Protein Targeting Ligands that target lipoprotein lipase (LPL).

FIGS. 1PPPP and 1QQQQ provides a non-limiting list of Extracellular Protein Targeting Ligands that target matrix metalloproteinase-1 (MMP1).

FIG. 1RRRR-1DDDDD provides a non-limiting list of Extracellular Protein Targeting Ligands that target Macrophage migration inhibitory factor (MIF), also known as glycosylation-inhibiting factor (GIF), L-dopachrome isomerase, or phenylpyruvate tautomerase.

FIG. 1EEEEE-1GGGGG provides a non-limiting list of Extracellular Protein Targeting Ligands that target neutrophil elastase (NE).

FIGS. 1HHHHHH and 1IIIII provides a non-limiting list of Extracellular Protein Targeting Ligands that target Prothrombin.

FIG. 1JJJJJ-1NNNNN provides a non-limiting list of Extracellular Protein Targeting Ligands that target Plasma kallikrein (KLKB1).

FIG. 1OOOOO-1SSSSS provides a non-limiting list of Extracellular Protein Targeting Ligands that target plasminogen (PLG).

FIG. 1TTTTT-1XXXXX provides a non-limiting list of Extracellular Protein Targeting Ligands that target Plasminogen activator inhibitor-1 (PAI-1), endothelial plasminogen activator inhibitor or serpin E1.

FIG. 1YYYYY-1AAAAAA provides a non-limiting list of Extracellular Protein Targeting Ligands that target phospholipases A2, for example type 1B or group 1B (PLA2, PA21B, PLA2G1B, PLA2-IB).

FIG. 1BBBBBB-1DDDDDD provides a non-limiting list of Extracellular Protein Targeting Ligands that target phospholipases A2, for example type IIA or group IIA (PLA2, PLA2A, PA2IIA, PLA2G2A, PLA2-IIA).

FIG. 1EEEEEE-1NNNNNN provides a non-limiting list of Extracellular Protein Targeting Ligands that target placental growth factor (PGF).

FIG. 1OOOOOO-1QQQQQQ provides a non-limiting list of Extracellular Protein Targeting Ligands that target plasminogen activator, tissue type (tPA, PLAT).

FIG. 1RRRRRR provides a non-limiting list of Extracellular Protein Targeting Ligands that target Transforming growth factor beta 2 (TGF-β2, TGFB2).

FIG. 1SSSSSS provides a non-limiting list of Extracellular Protein Targeting Ligands that target thrombospondin 1 (TSP1, TSP-1, THBS1).

FIG. 1TTTTTT-1XXXXXX provides a non-limiting list of Extracellular Protein Targeting Ligands that target Urokinase or Urokinase-type plasminogen activator (UPA, uPA).

DETAILED DESCRIPTION OF THE INVENTION

Figure 1A:
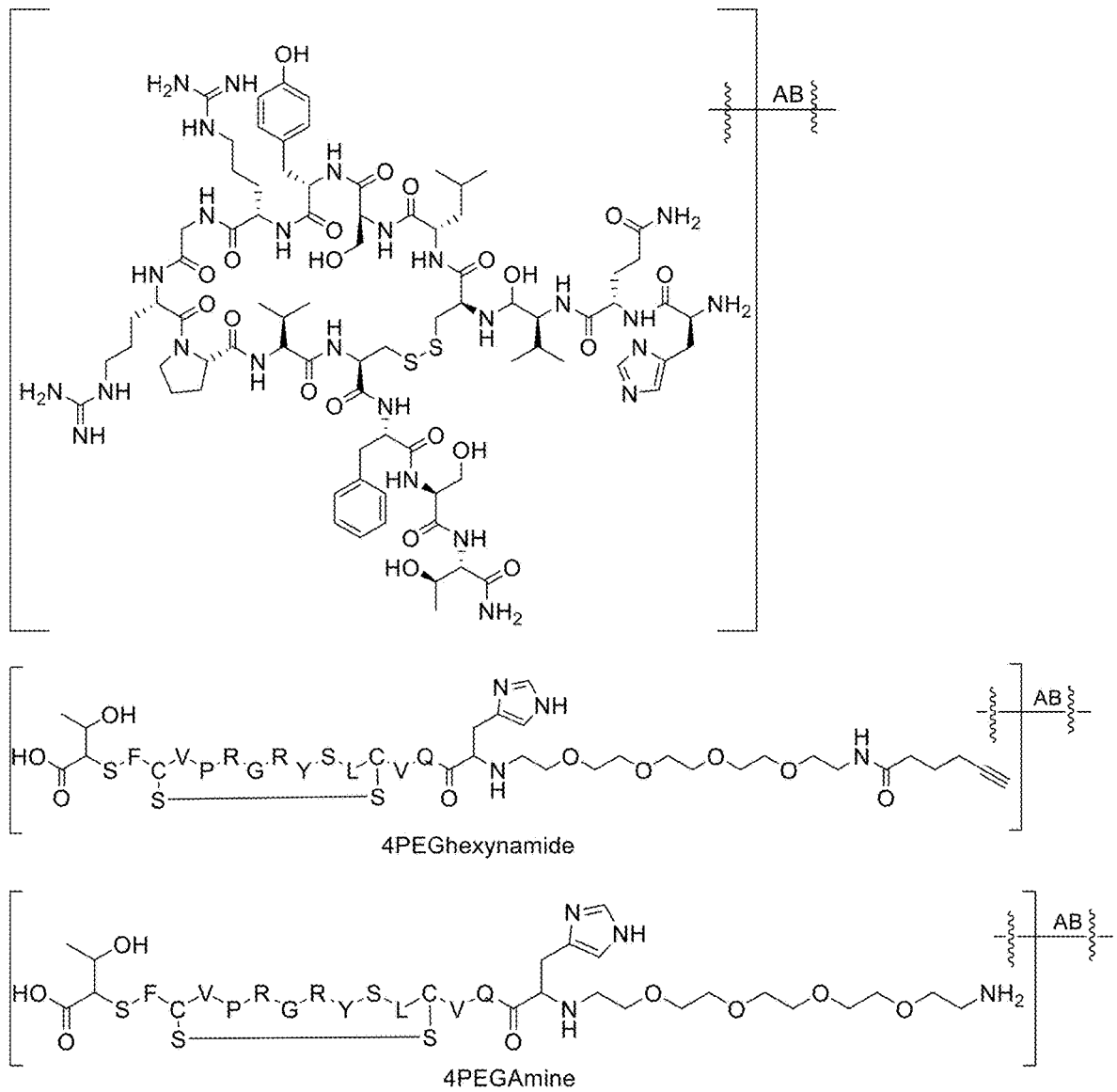
FIG. 1A provides a non-limiting list of Extracellular Protein Targeting Ligands that target Immunoglobulin A (IgA).
Figure 1B:
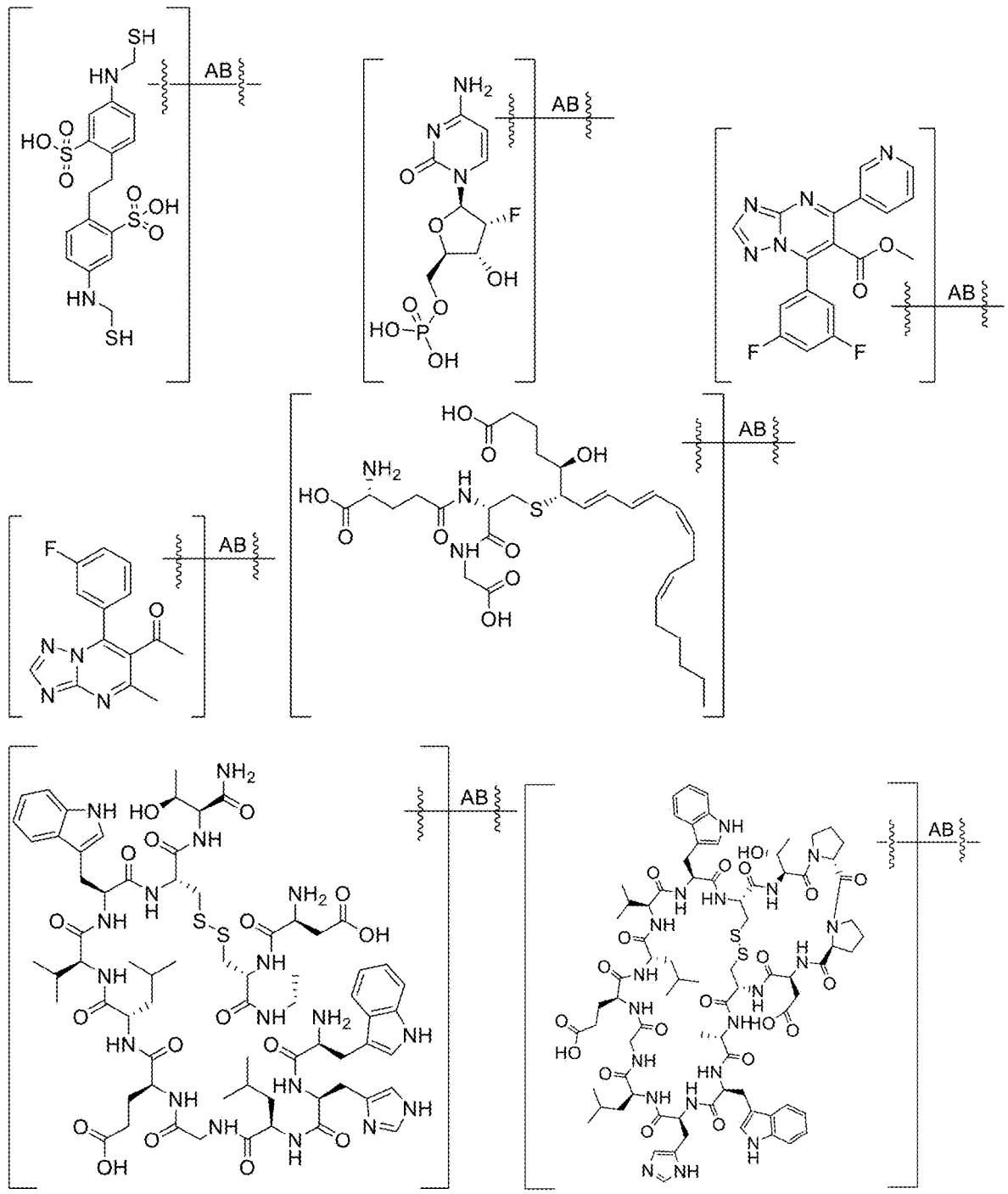
FIG. 1B provides a non-limiting list of Extracellular Protein Targeting Ligands that target Immunoglobulin G (IgG).
Figure 1C:
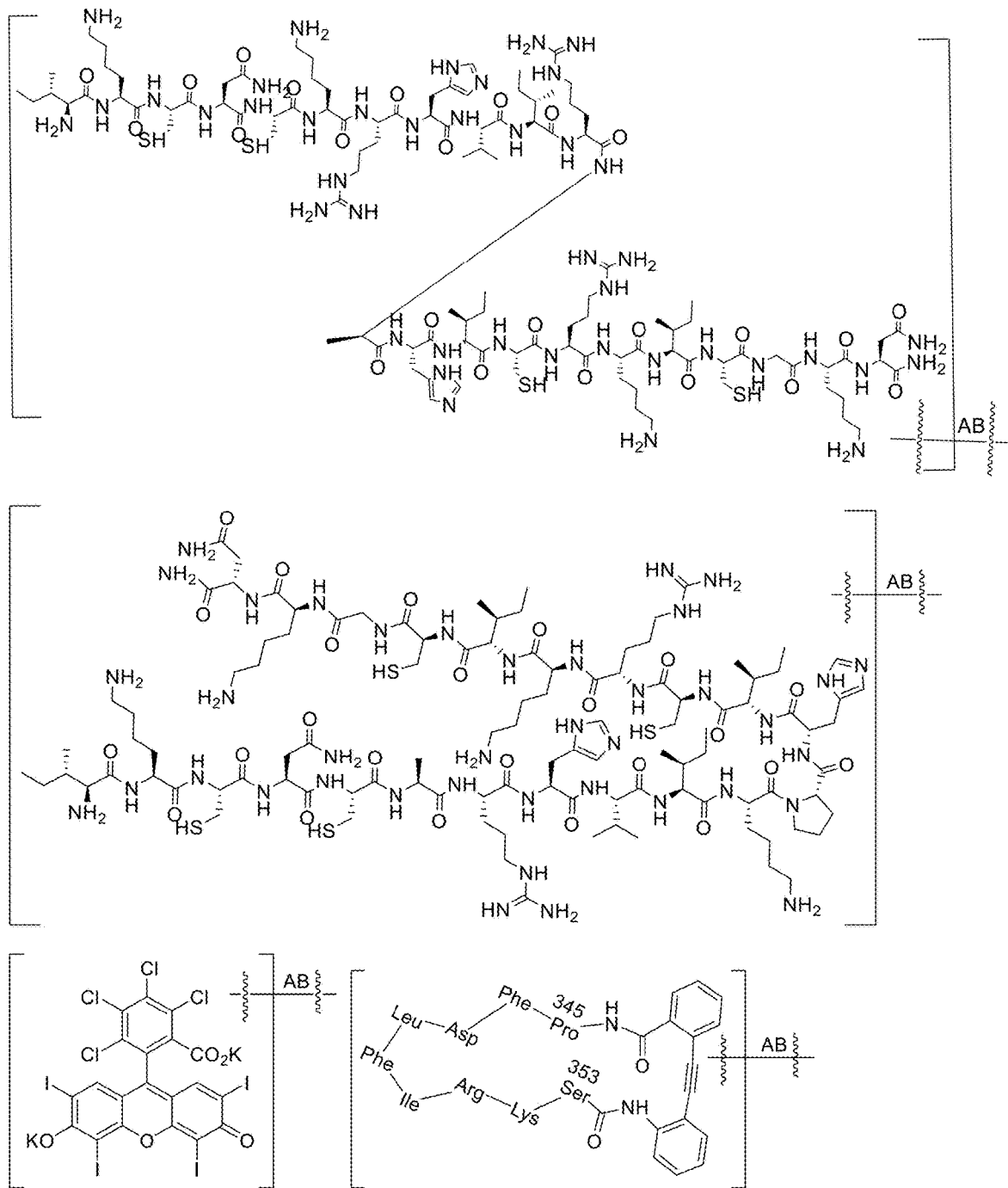
FIG. 1C-1G provides a non-limiting list of Extracellular Protein Targeting Ligands that target Immunoglobulin E (IgE).
Figure 1D:
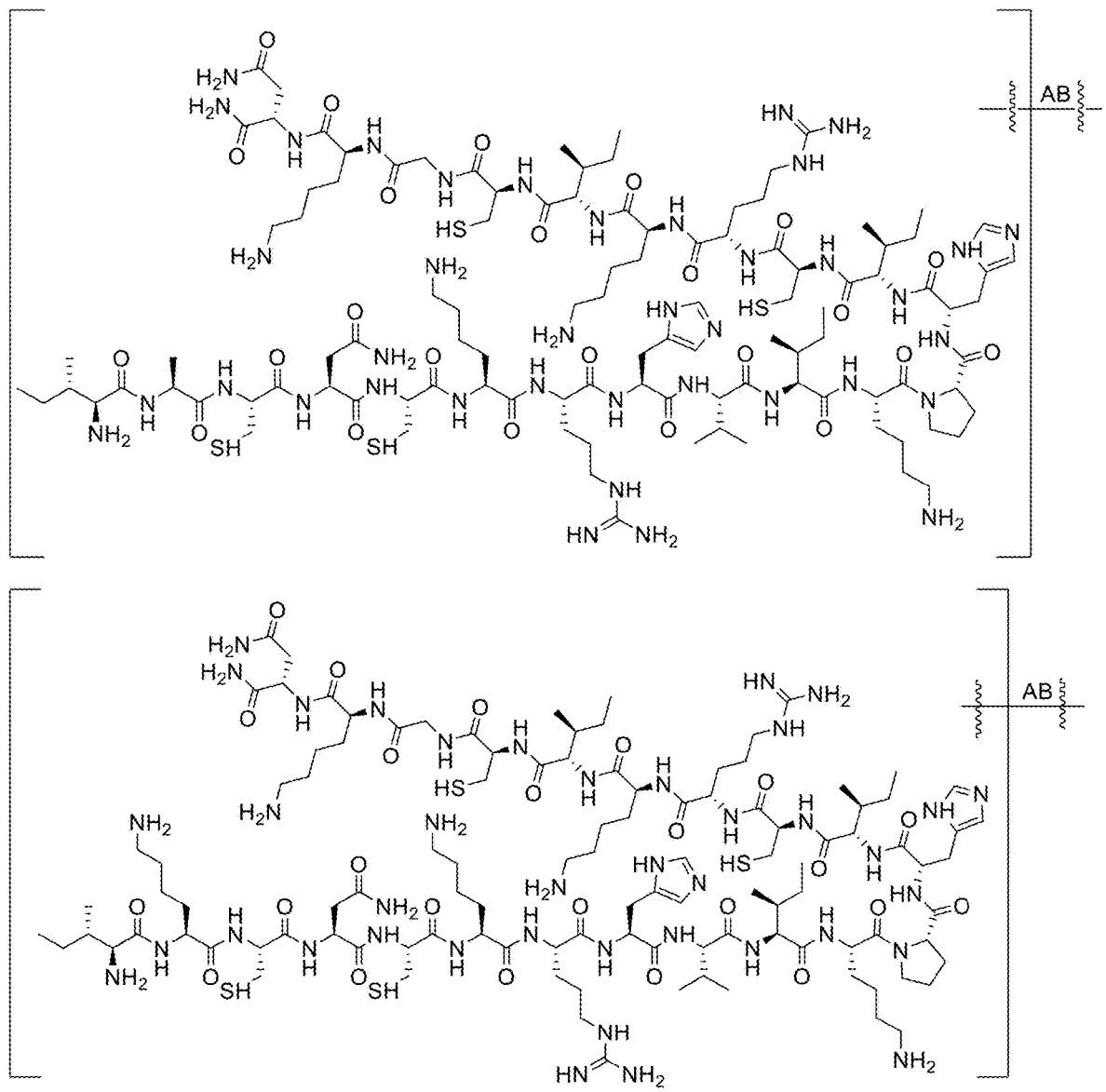
Figure 1E:
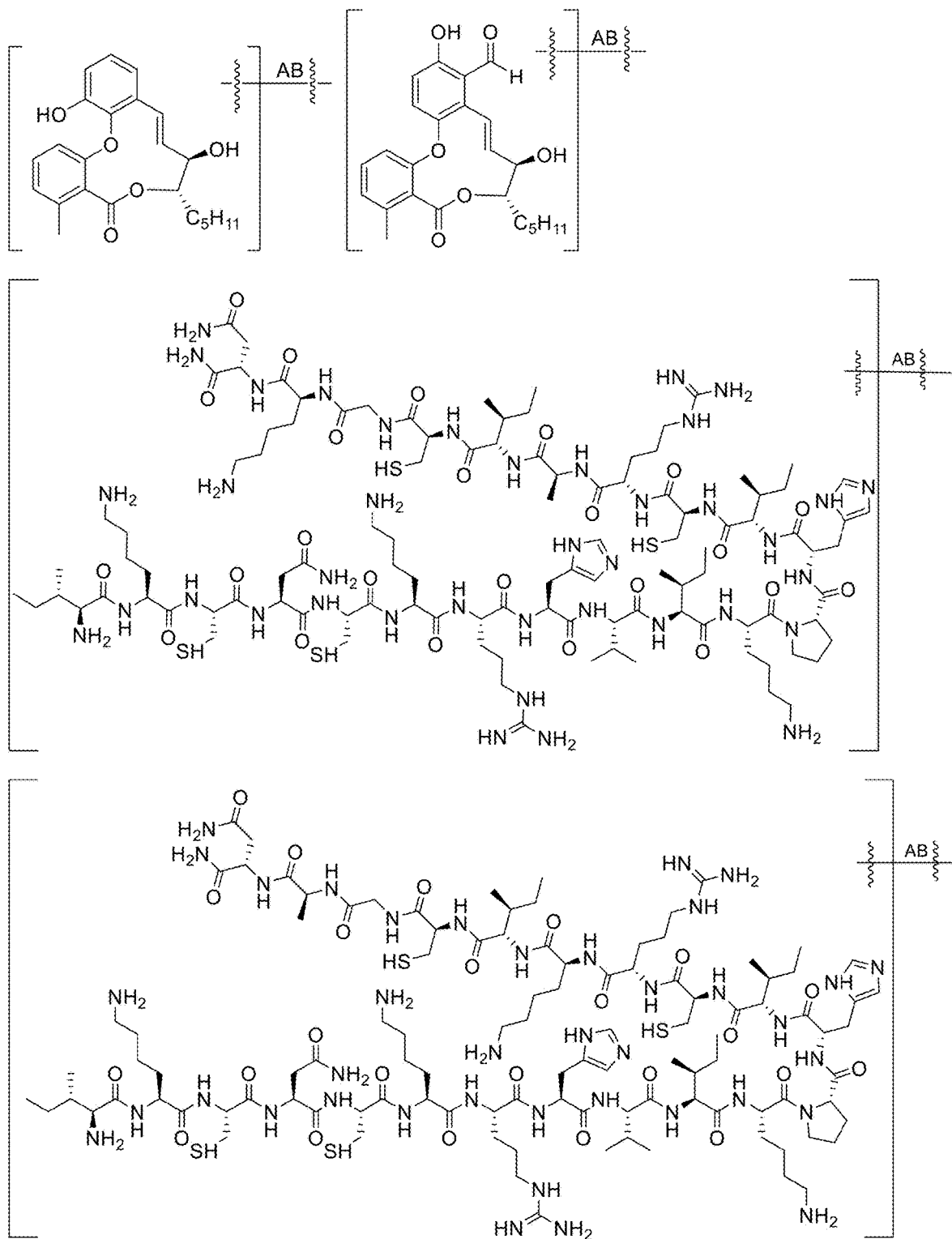
Figure 1F:
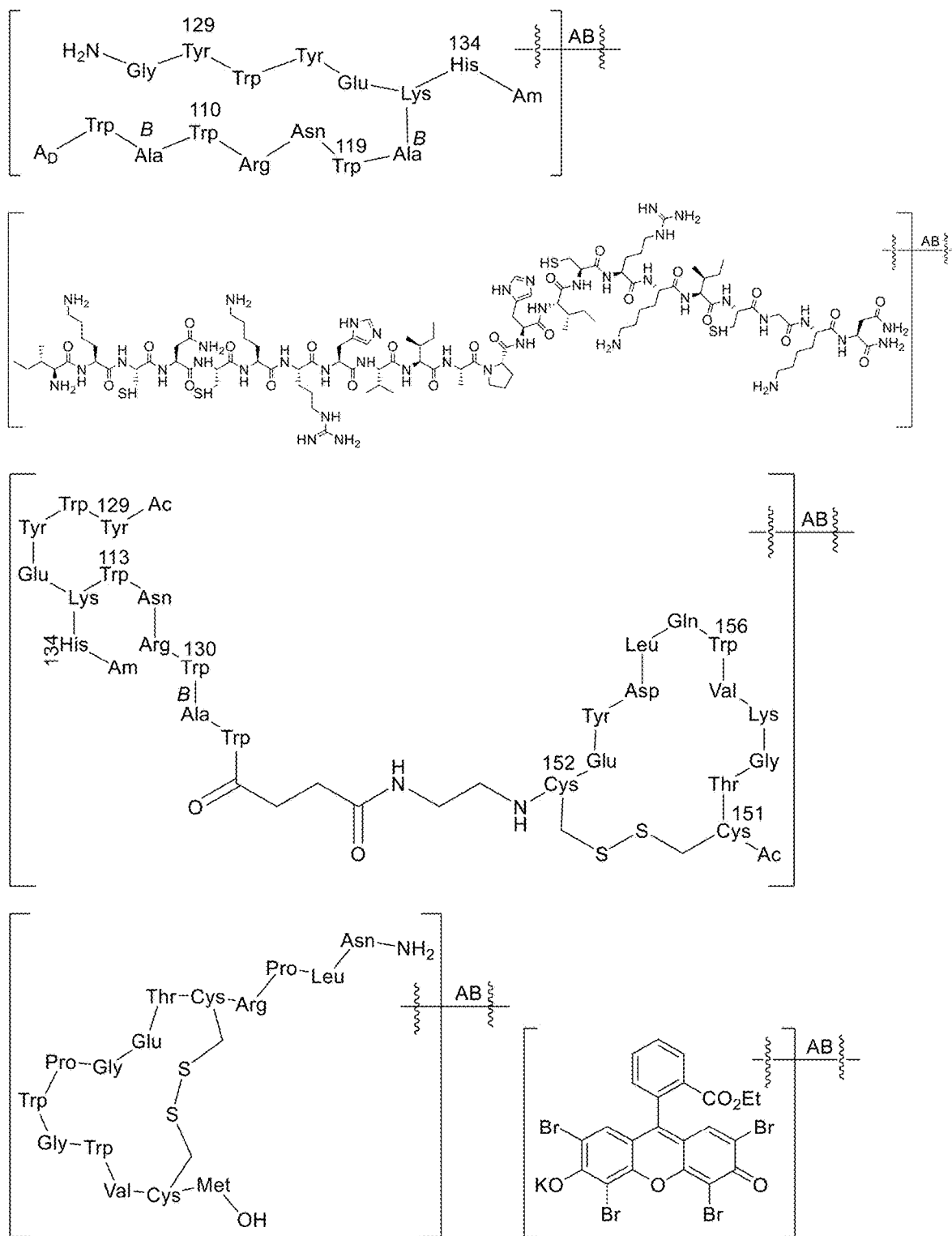
Figure 1G:
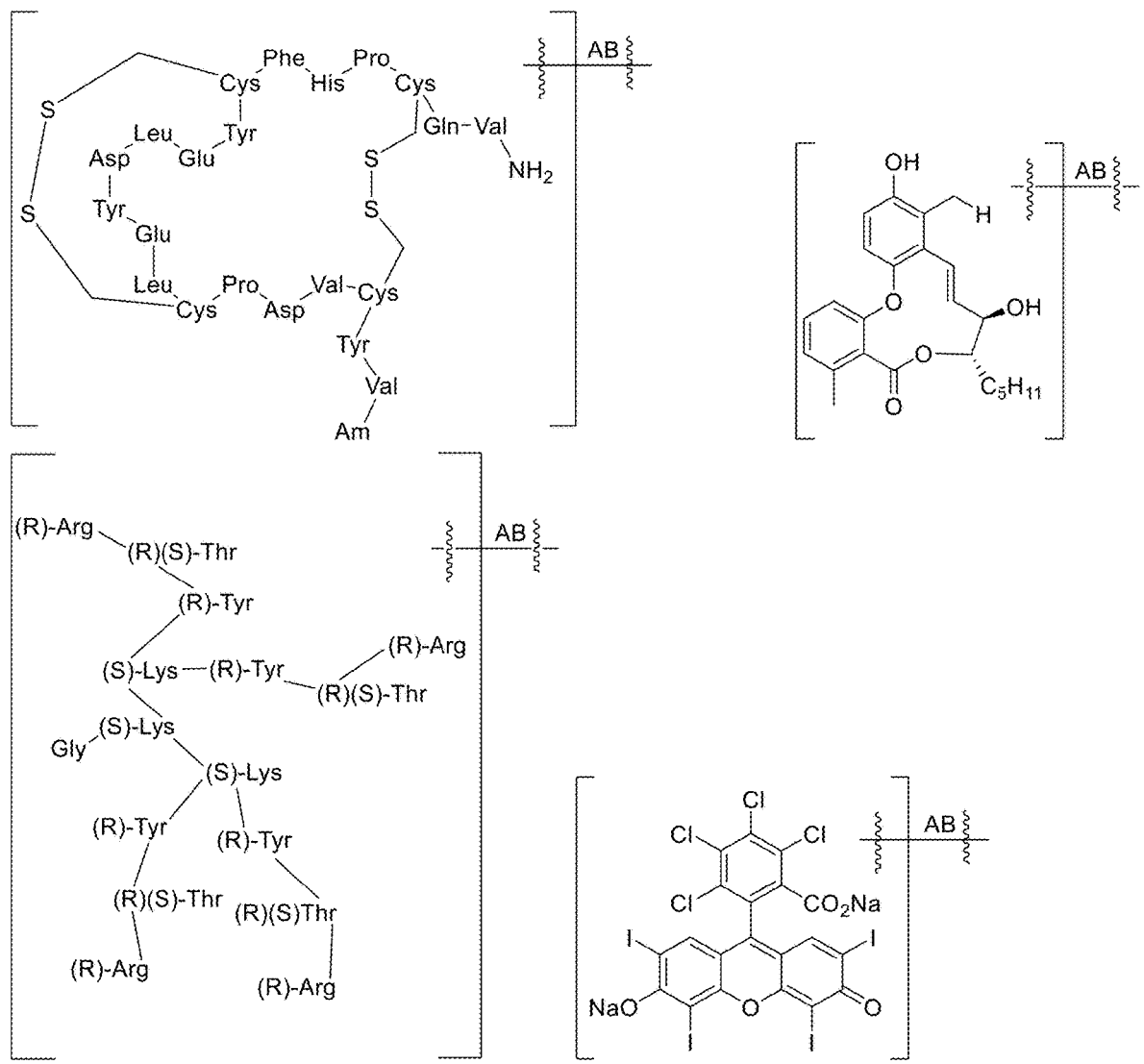
Figure 1H:
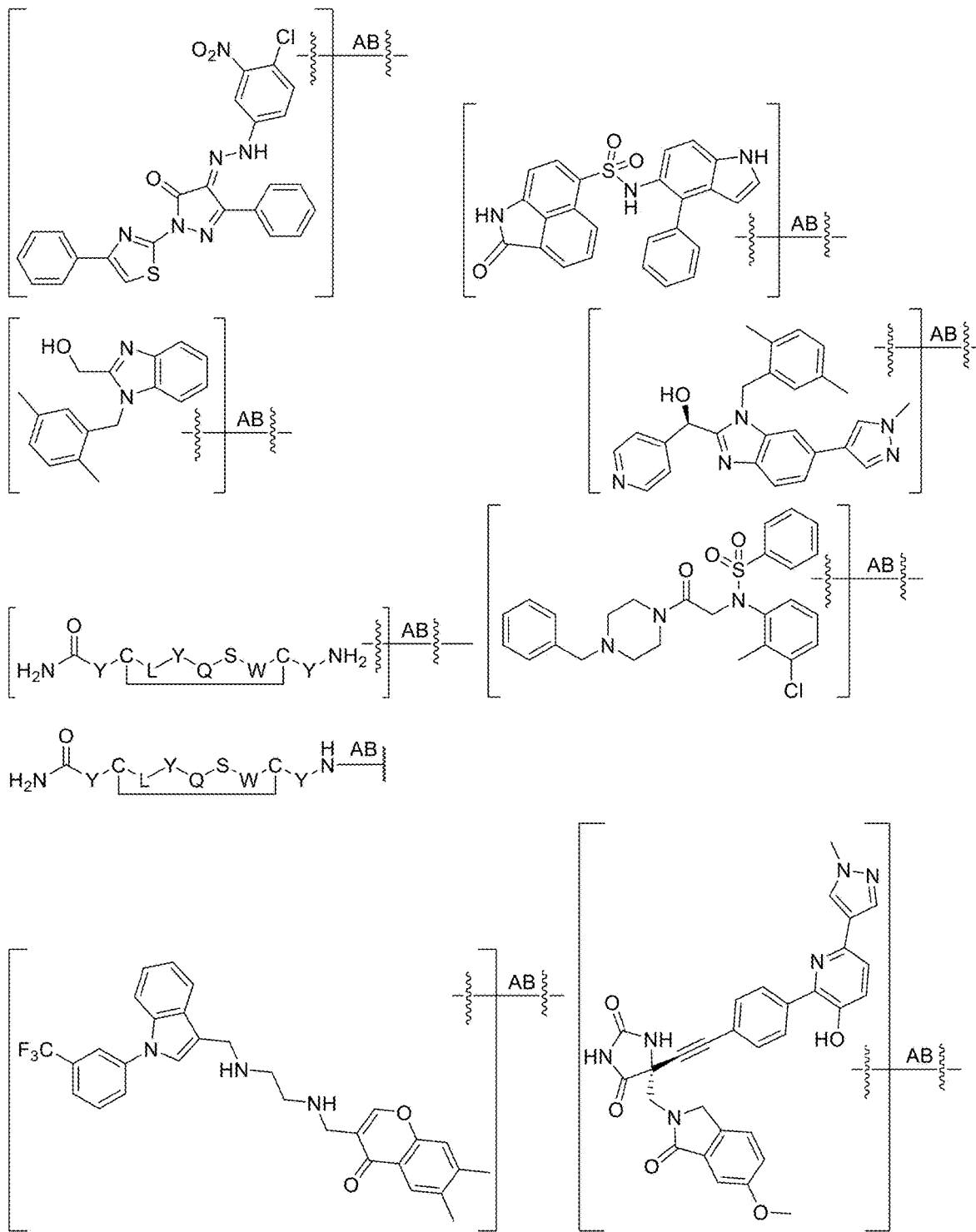
FIG. 1H-1M provides a non-limiting list of Extracellular Protein Targeting Ligands that target Tumor Necrosis Factor alpha (TNF-α).
Figure 1I:
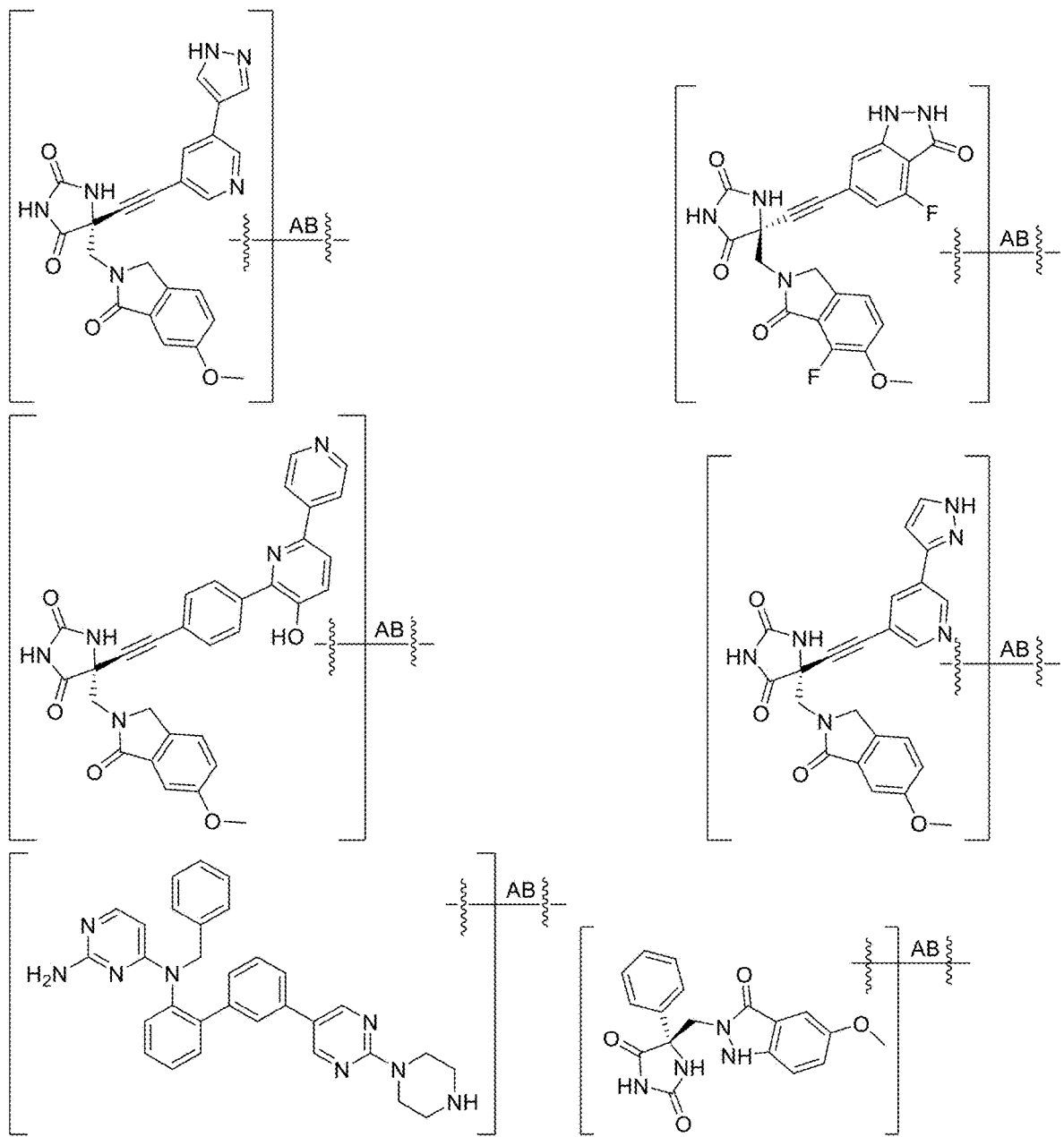
Figure 1J:
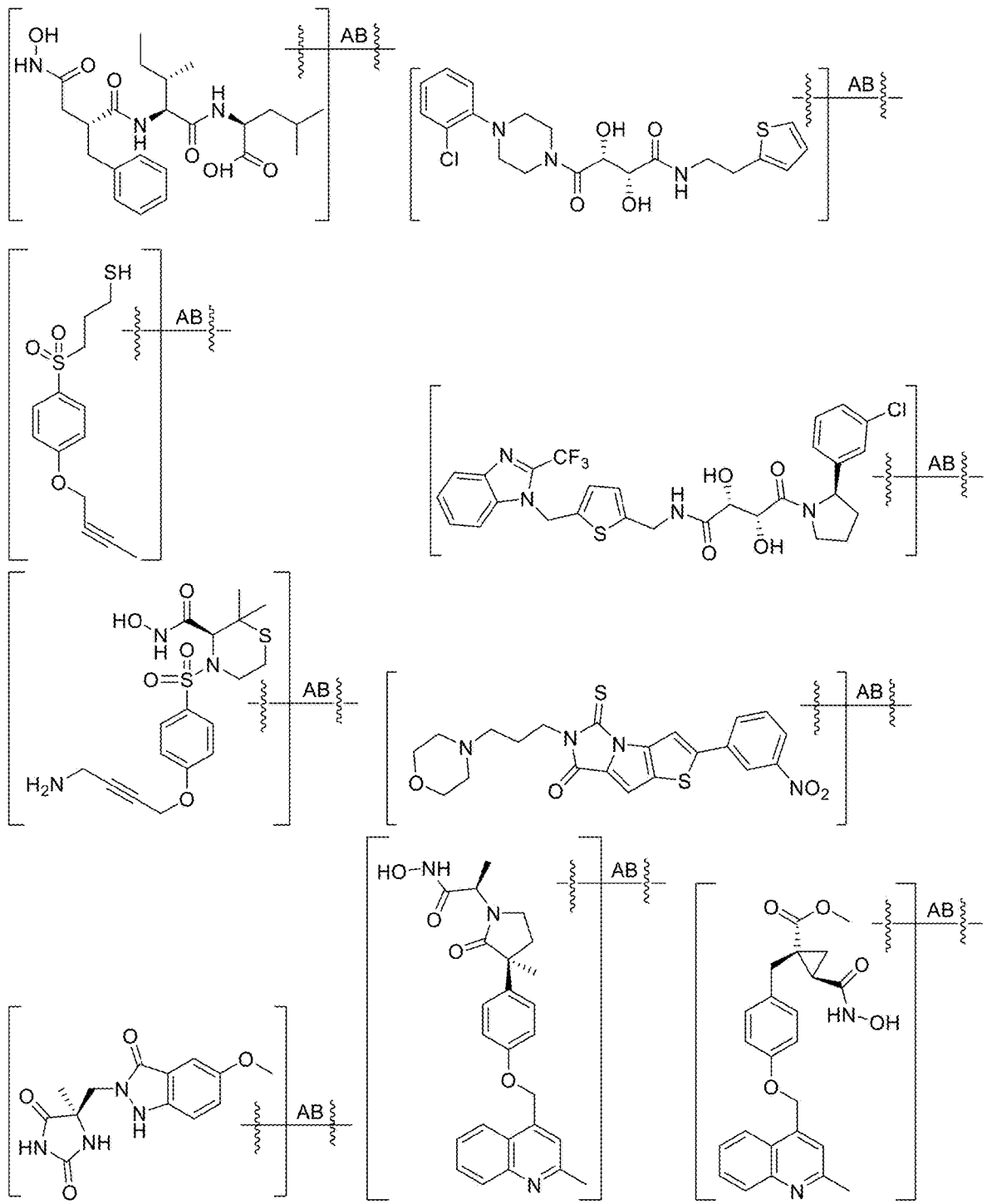
Figure 1K:
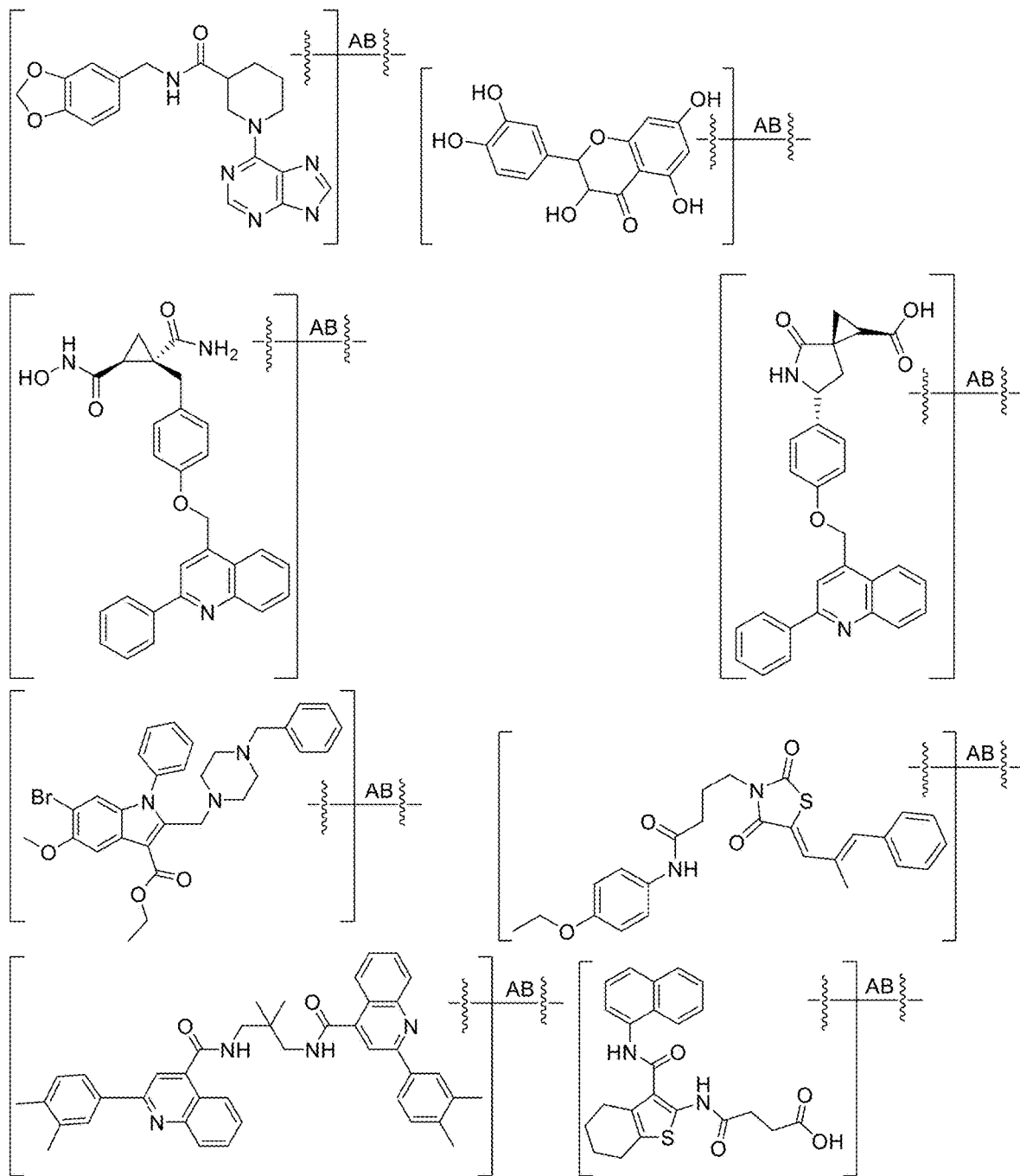
Figure 1L:
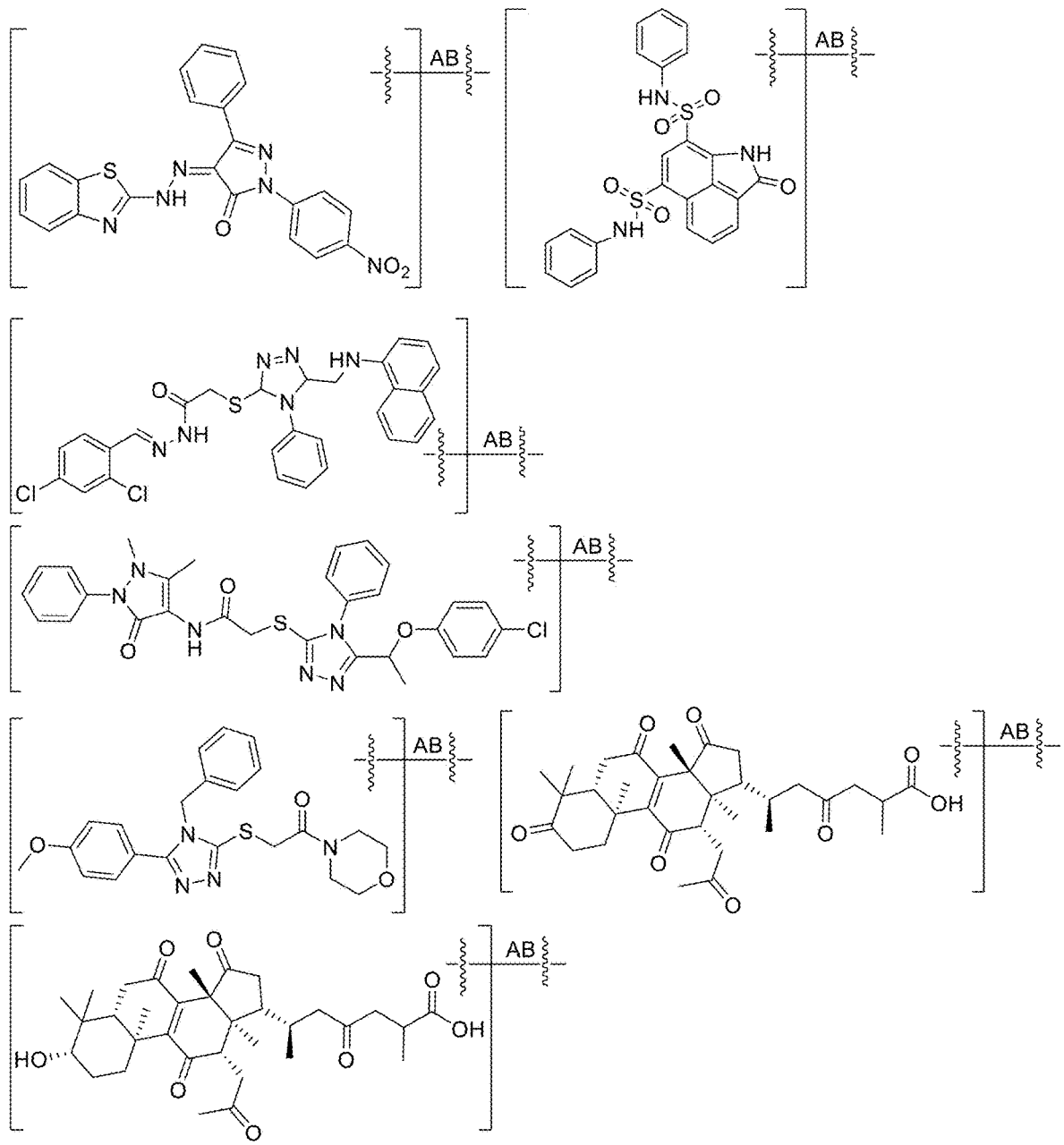
Figure 1M:
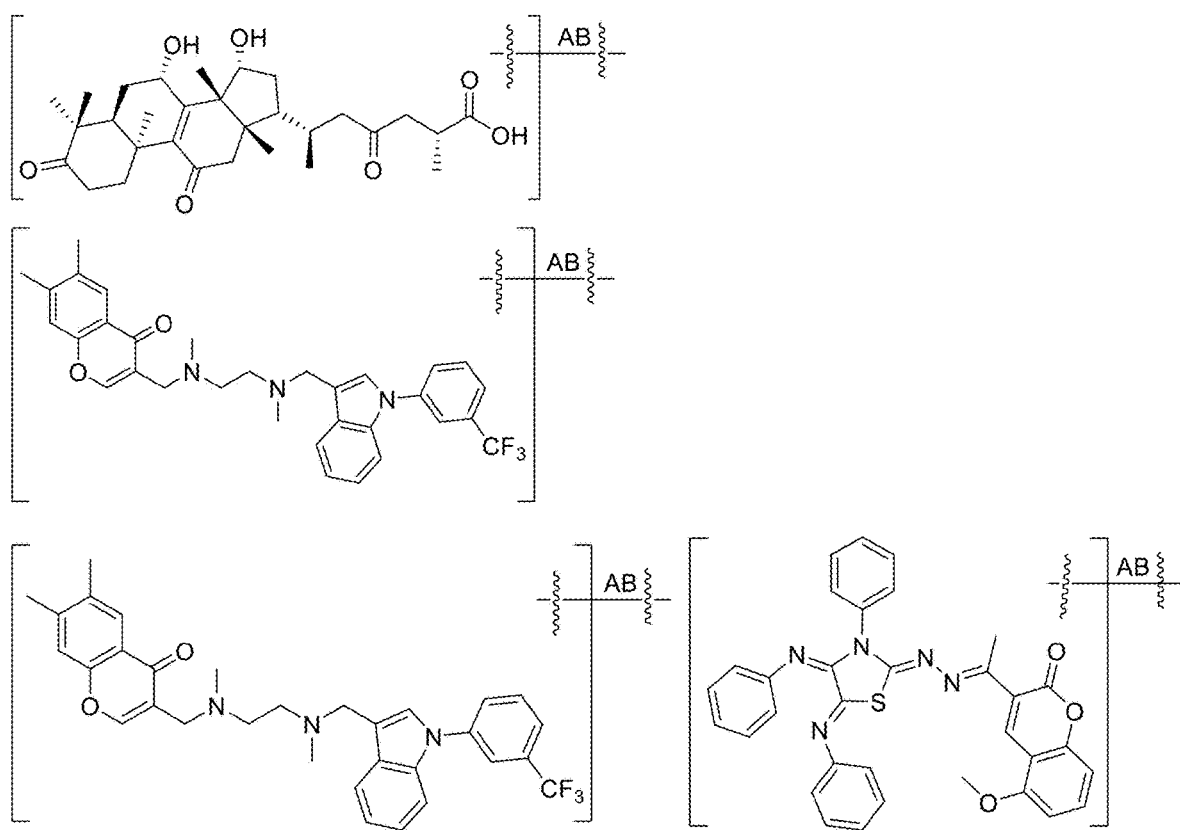
Figure 1N:
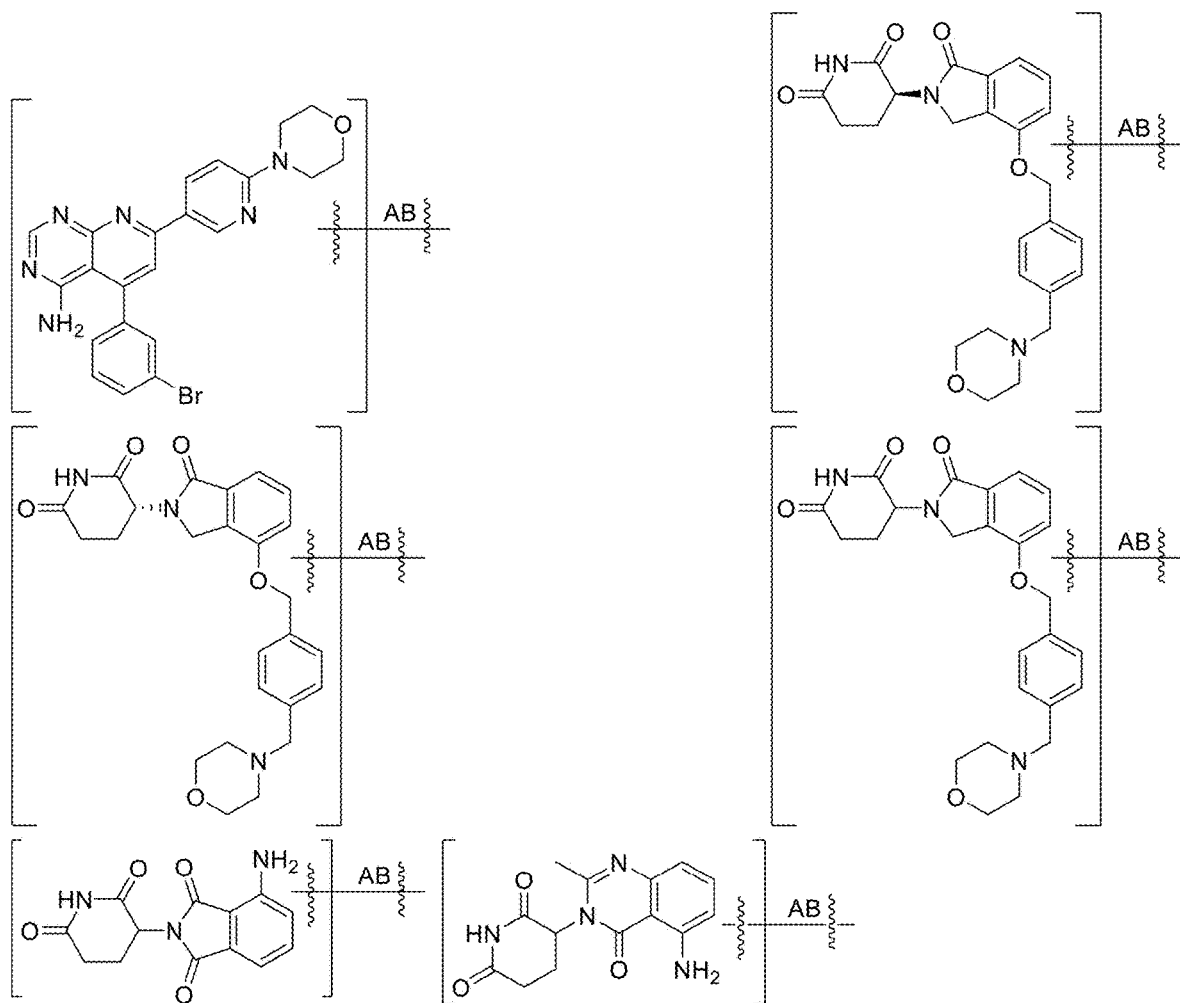
FIG. 1N provides a non-limiting list of Extracellular Protein Targeting Ligands that target Interleukin-1 (IL-1).
Figure 1O:
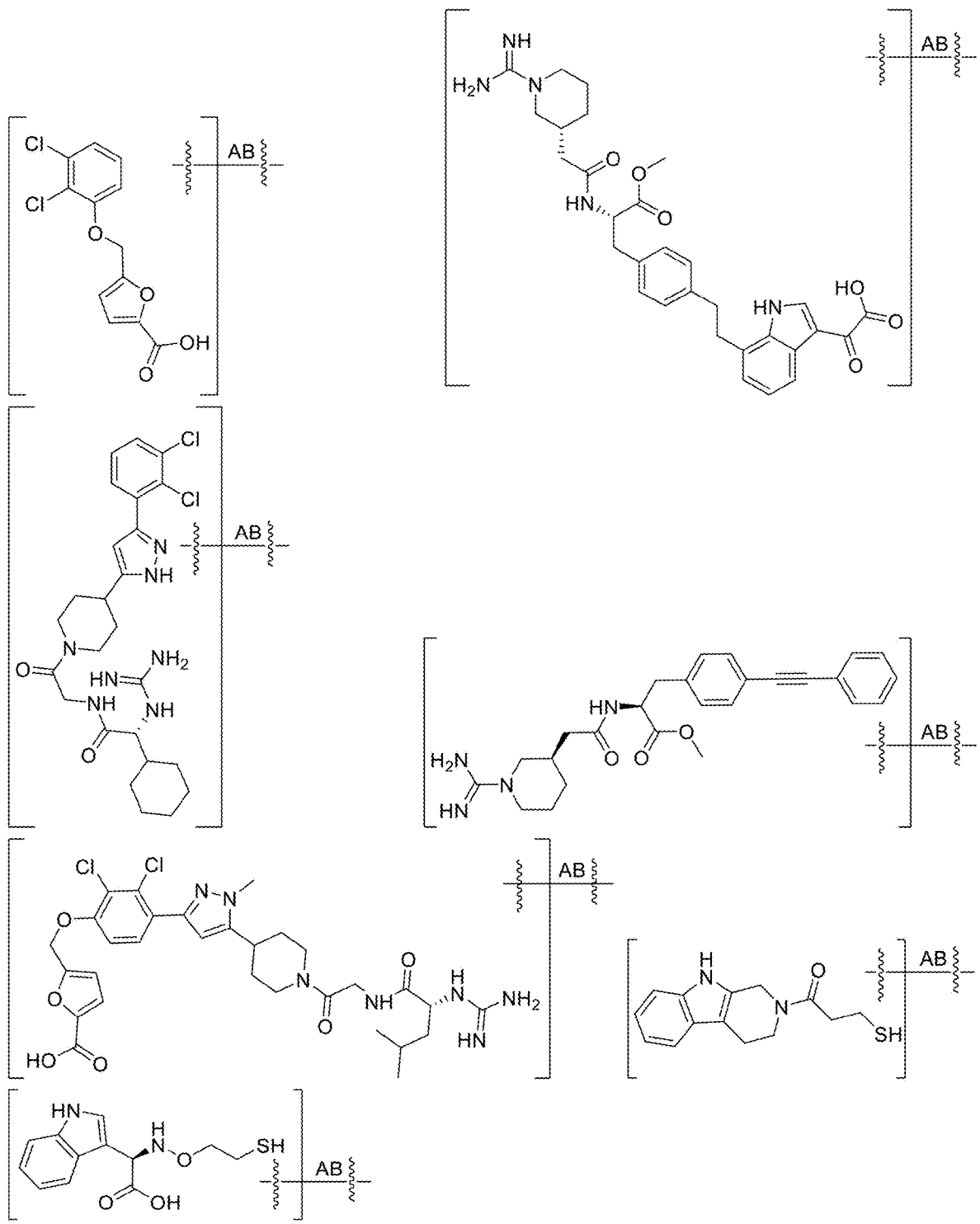
FIG. 1O-1S provides a non-limiting list of Extracellular Protein Targeting Ligands that target Interleukin-2 (IL-2).
Figure 1P:
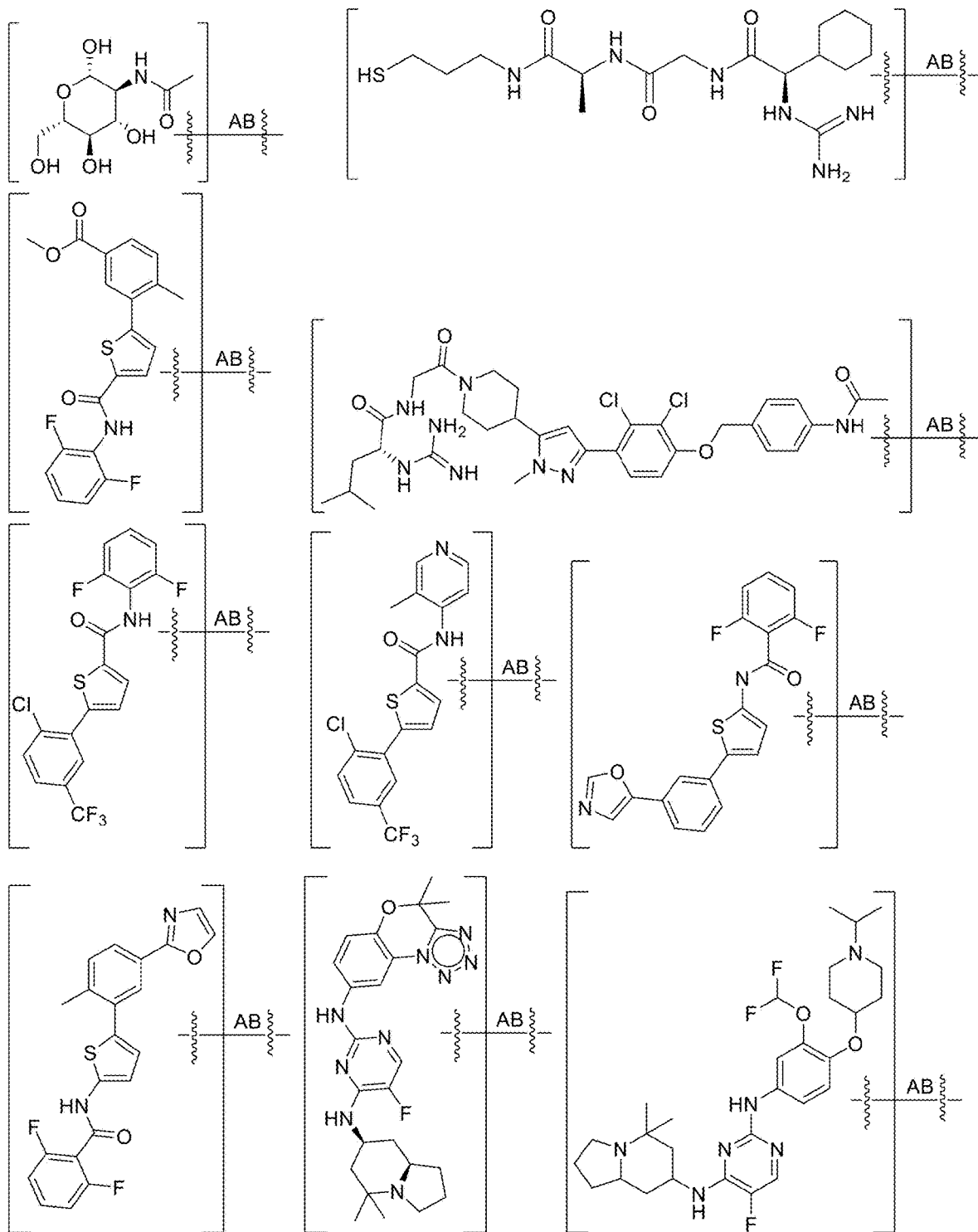
Figure 1Q:
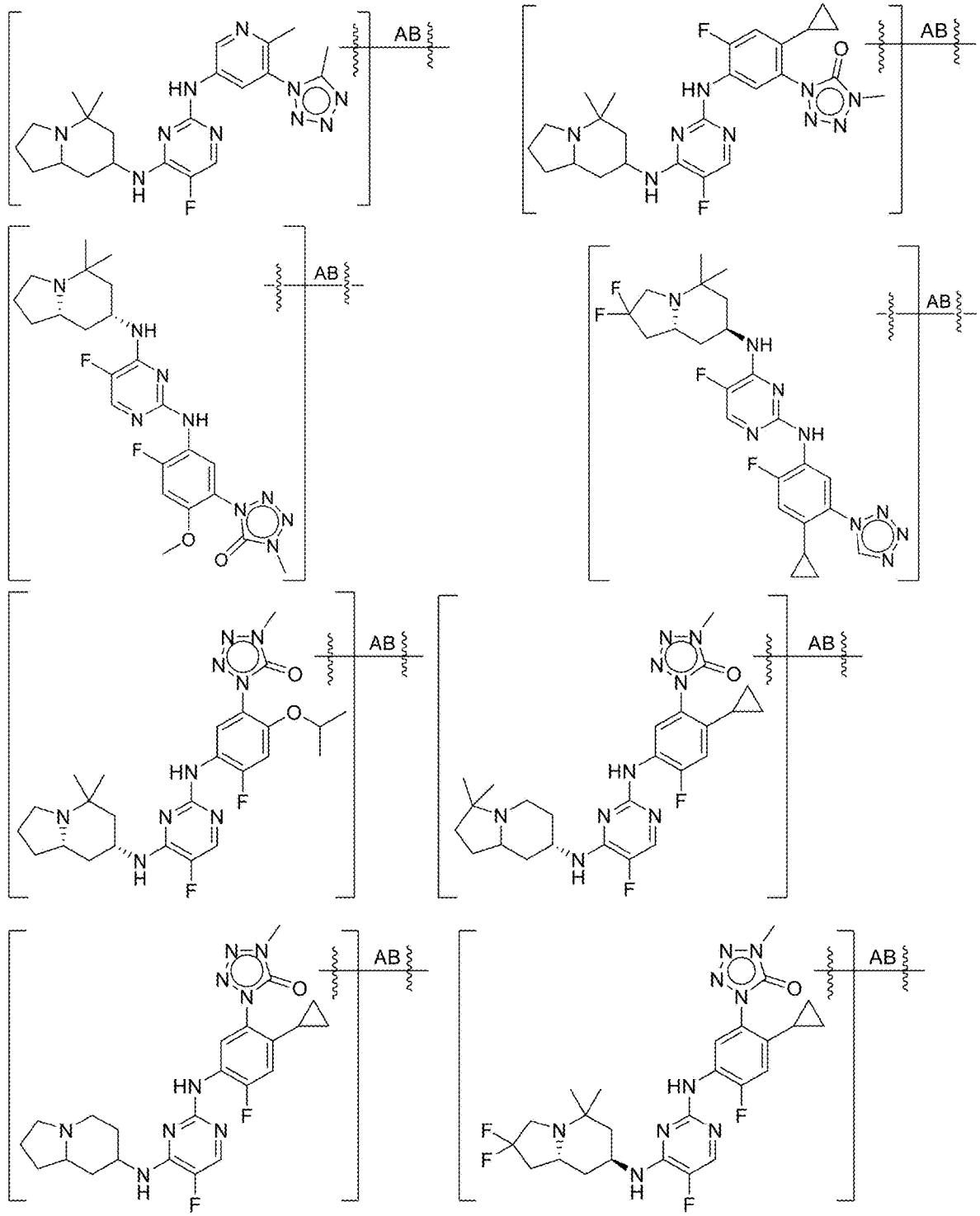
Figure 1R:
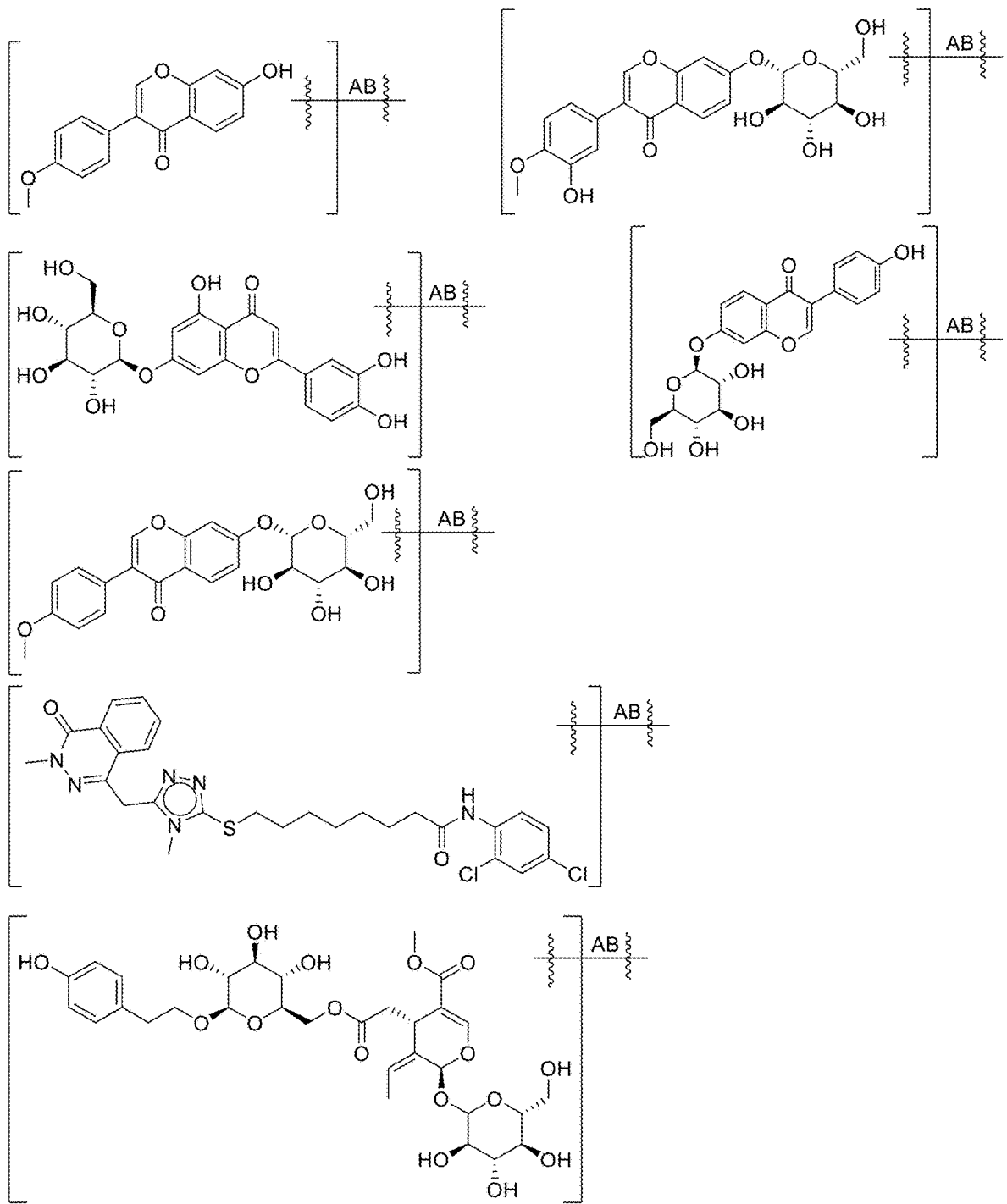
Figure 1S:
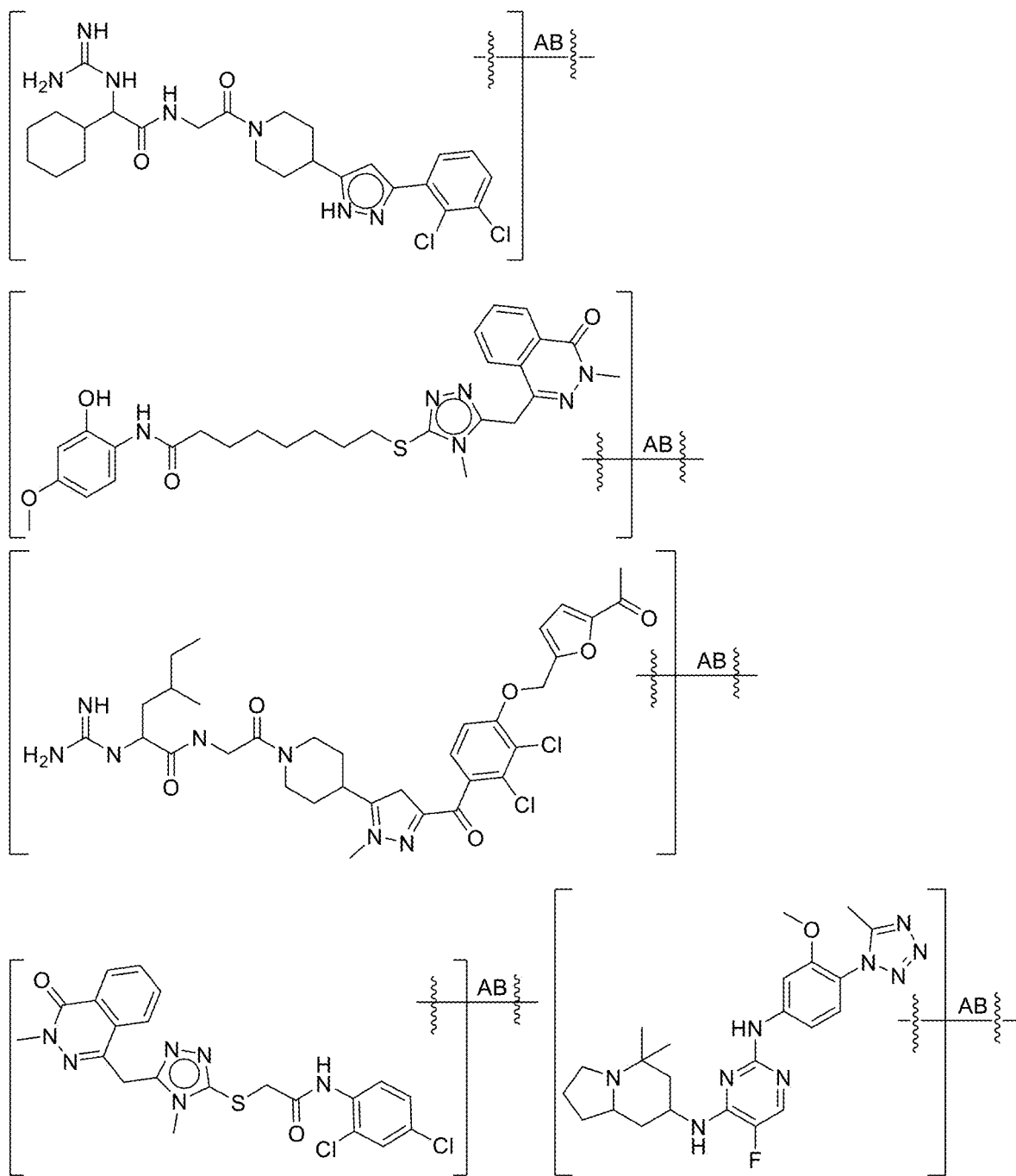
Figure 1T:
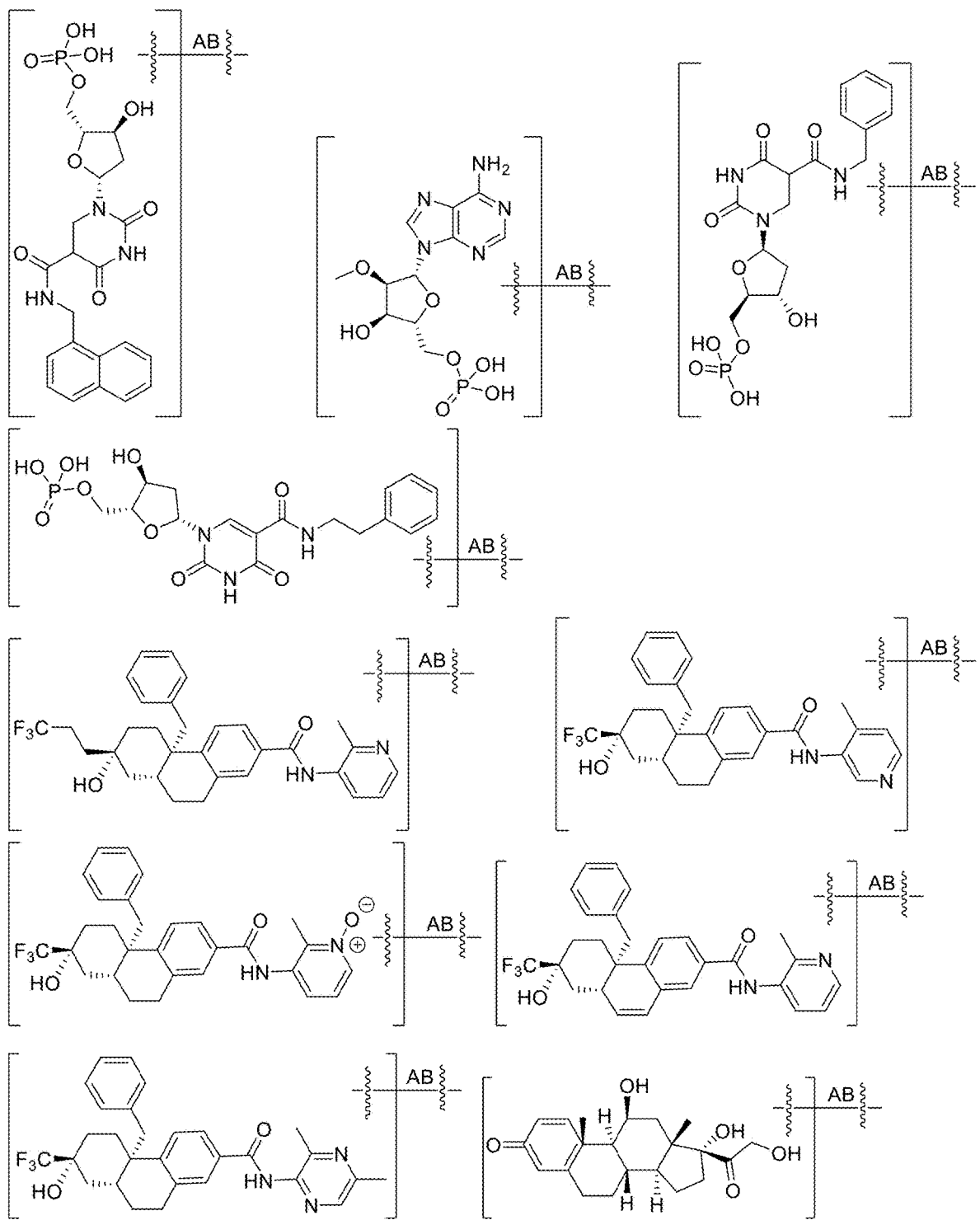
FIG. 1T-1W provides a non-limiting list of Extracellular Protein Targeting Ligands that target Interleukin-6 (IL-6).
Figure 1U:
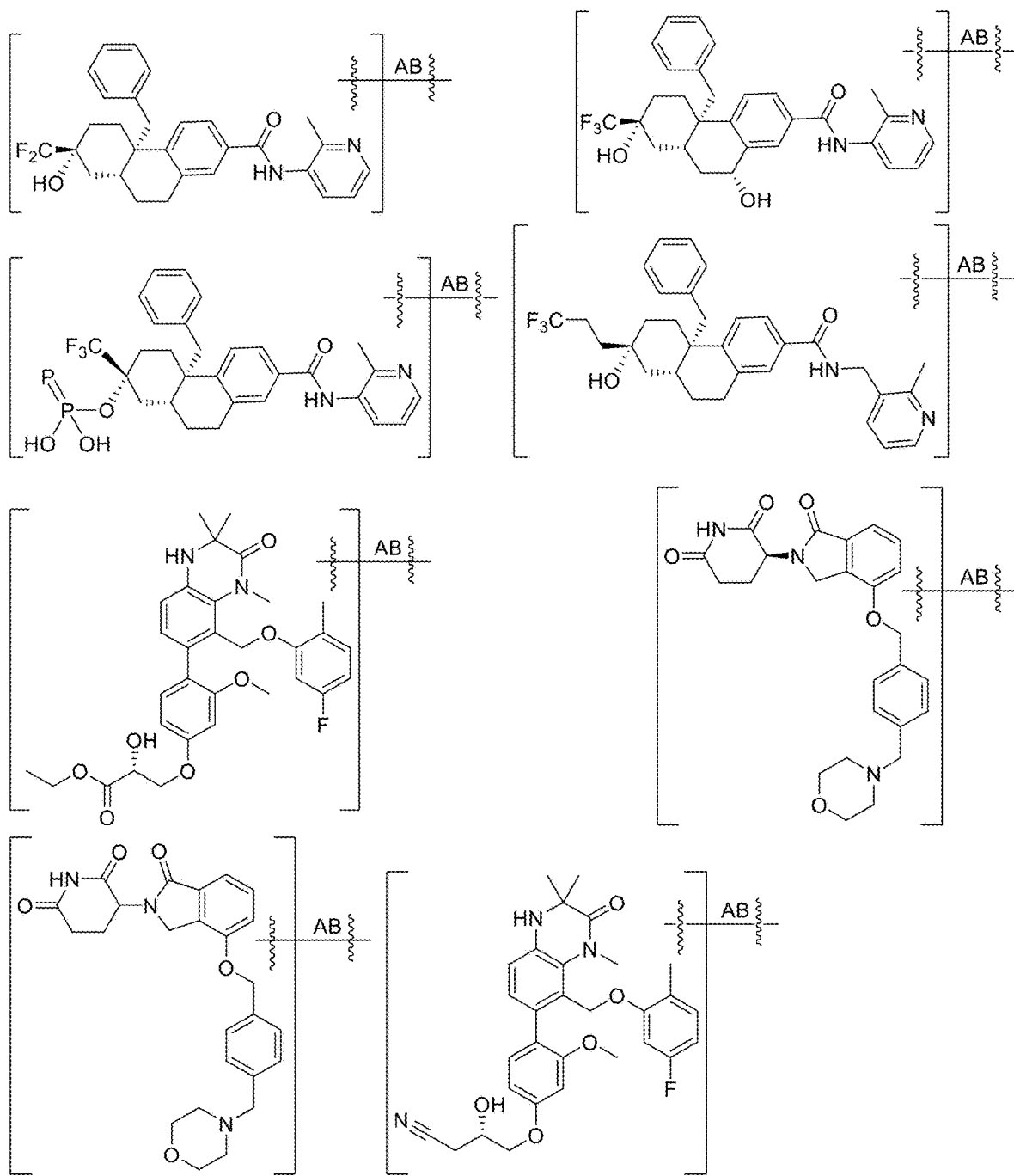
Figure 1V:
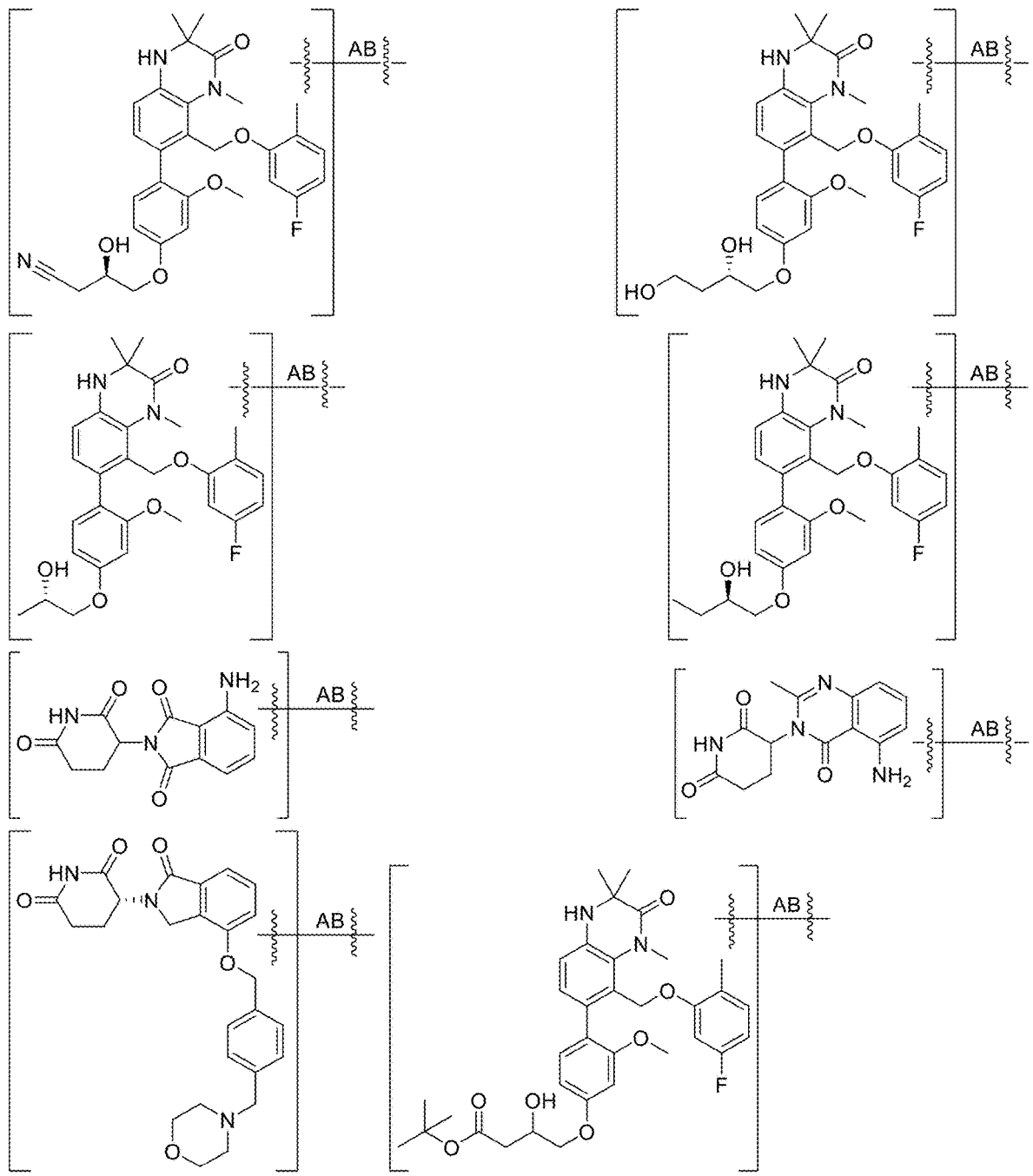
Figure 1W:
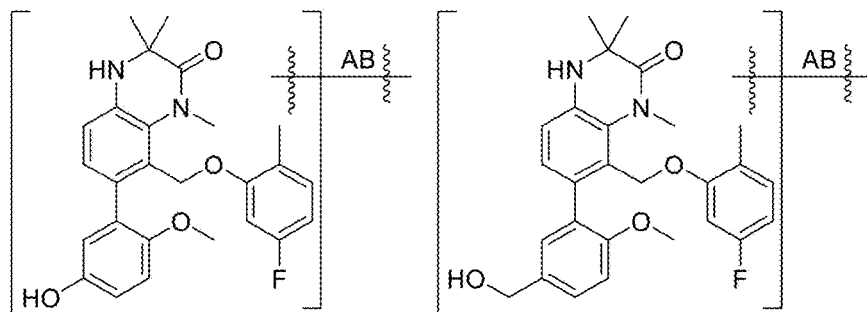
Figure 1X:
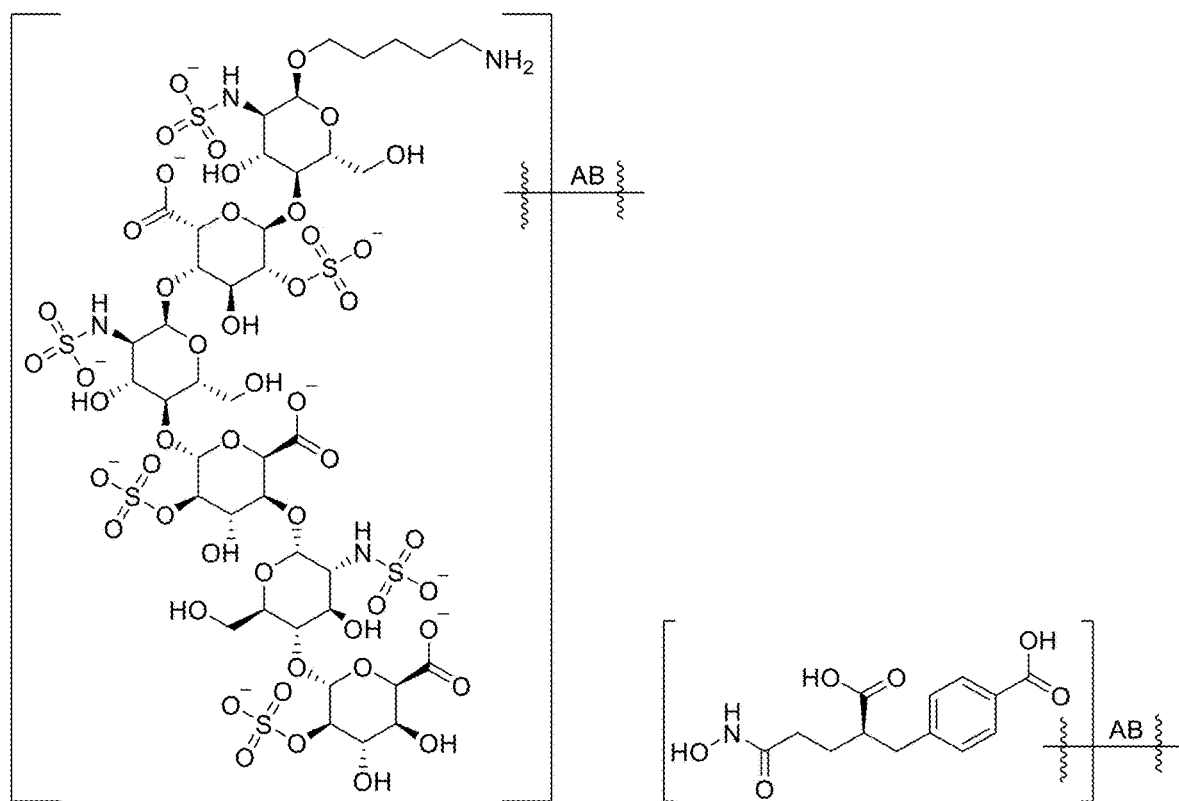
Figure 1Y:
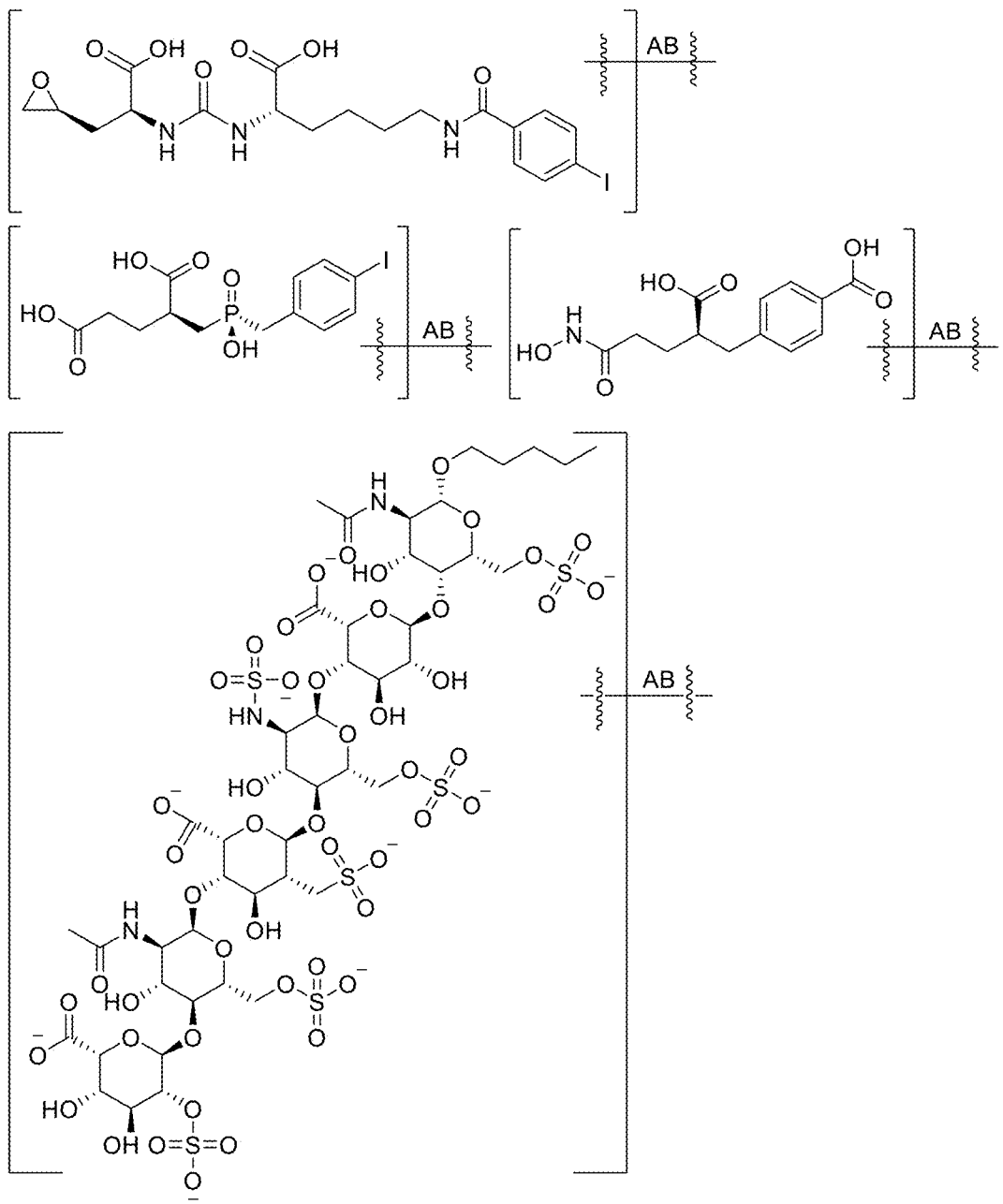
FIGS. 1YYY and 1ZZZ provides a non-limiting list of Extracellular Protein Targeting Ligands that target fibronectin (FN1).
Figure 1Z:
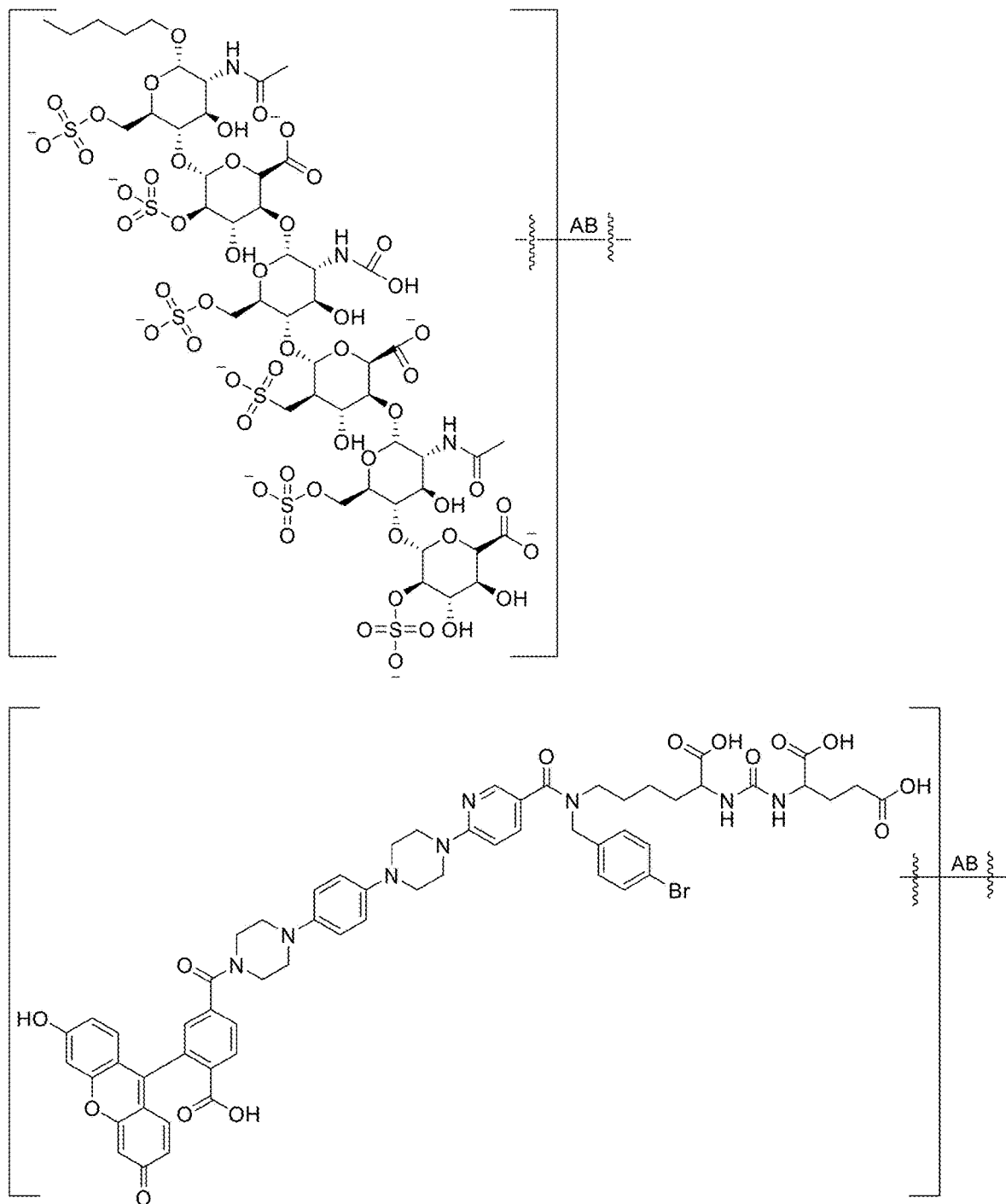
Figure 1A:
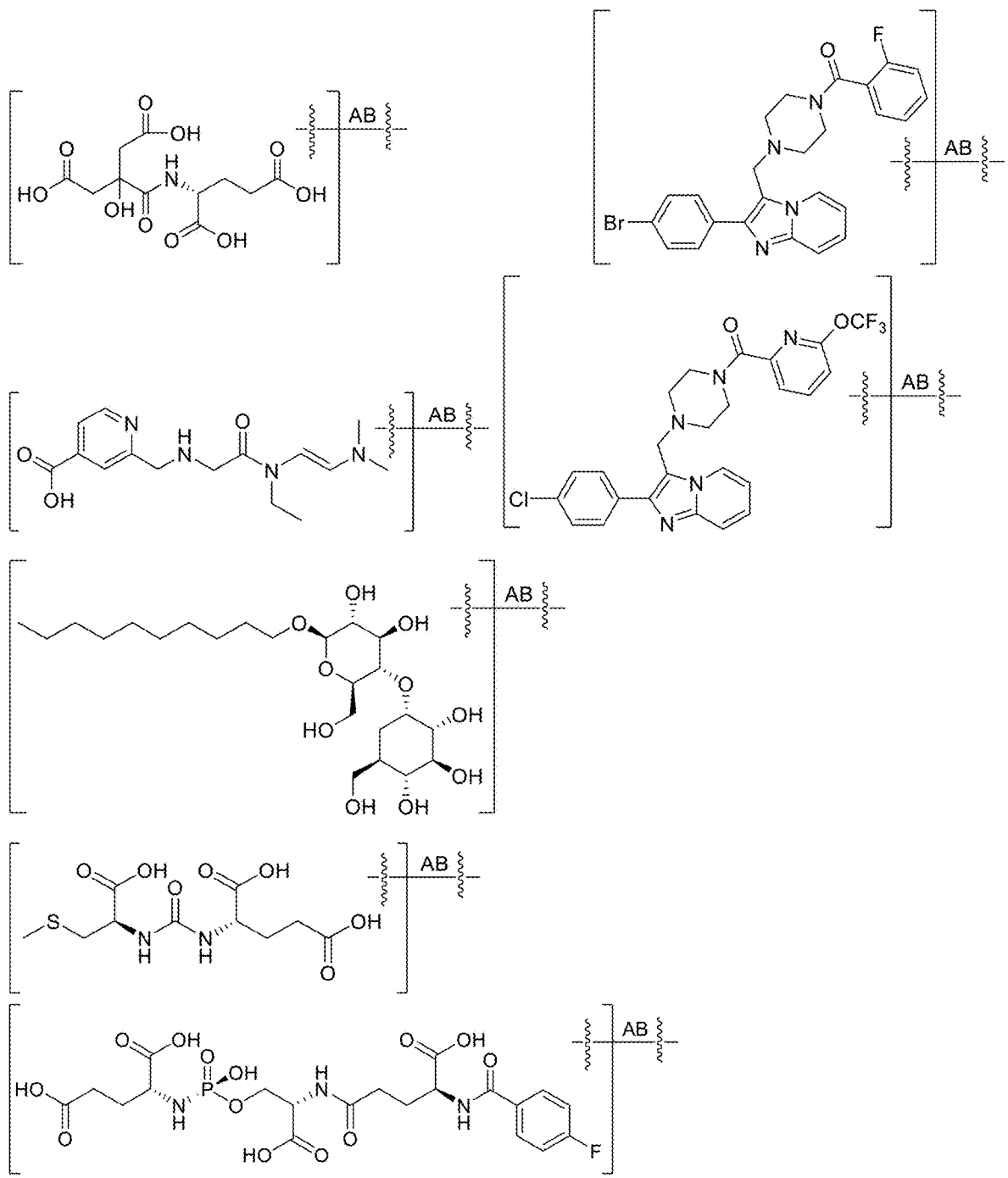
Figure 1B:
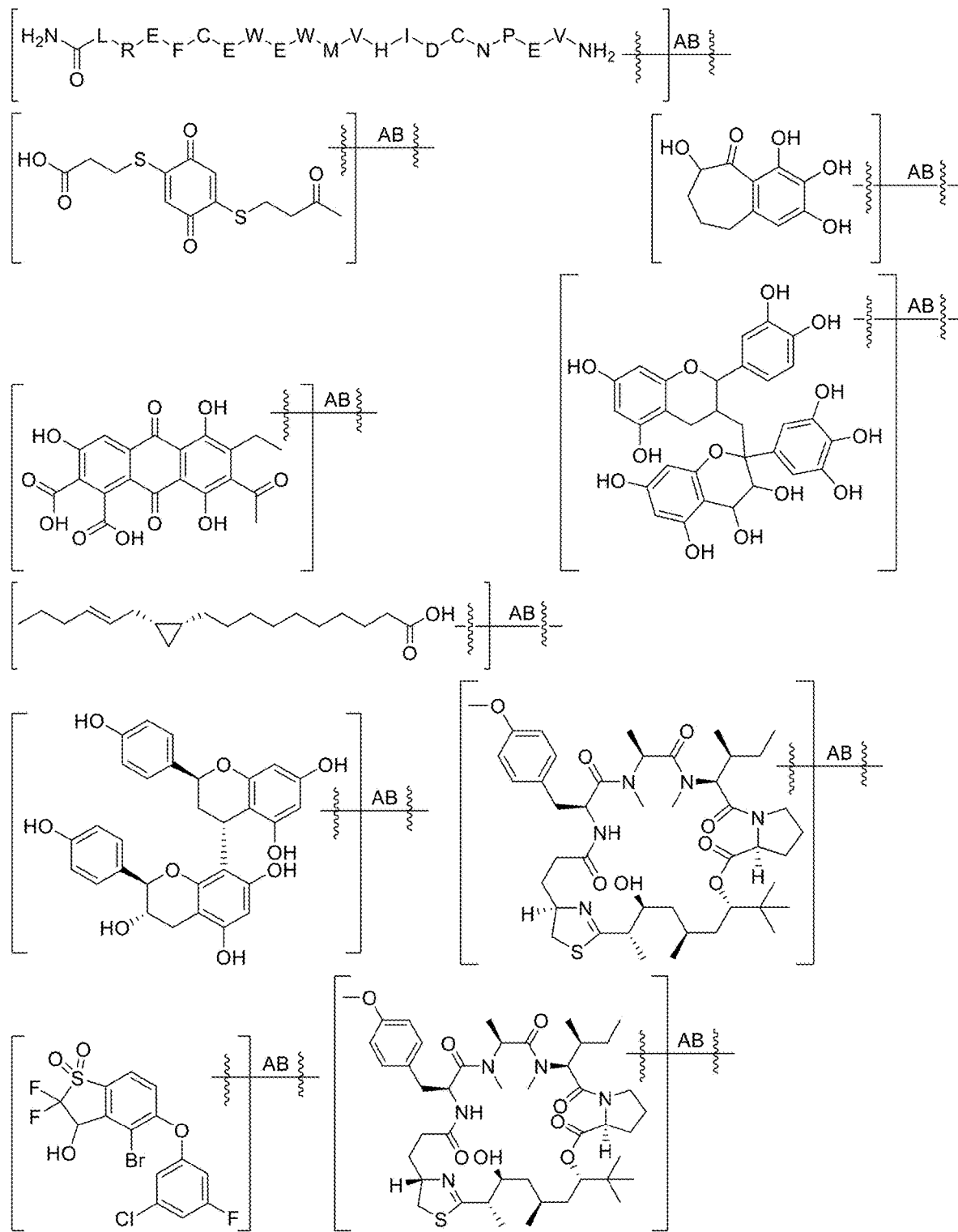
Figure 1C:
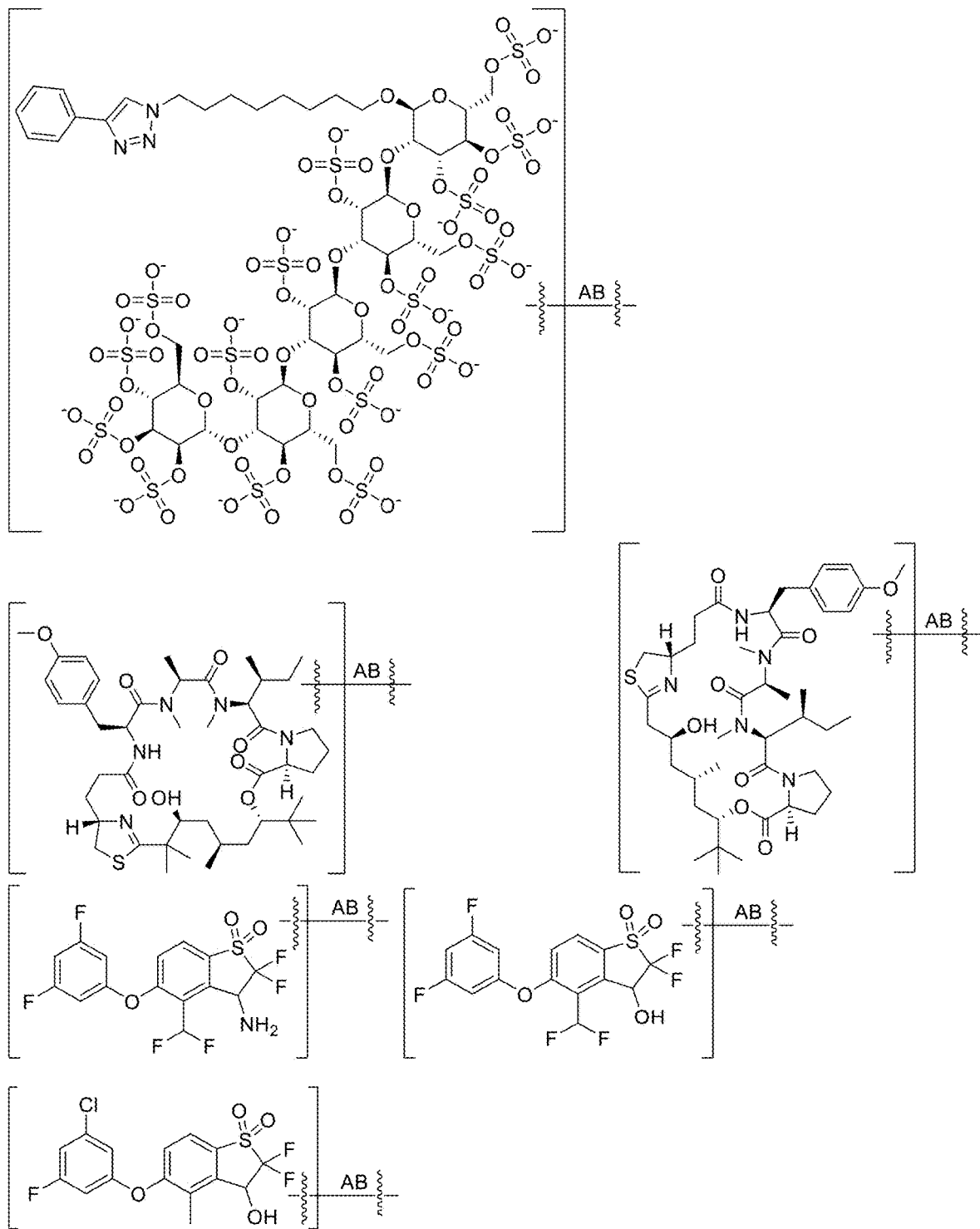
Figure 1D:
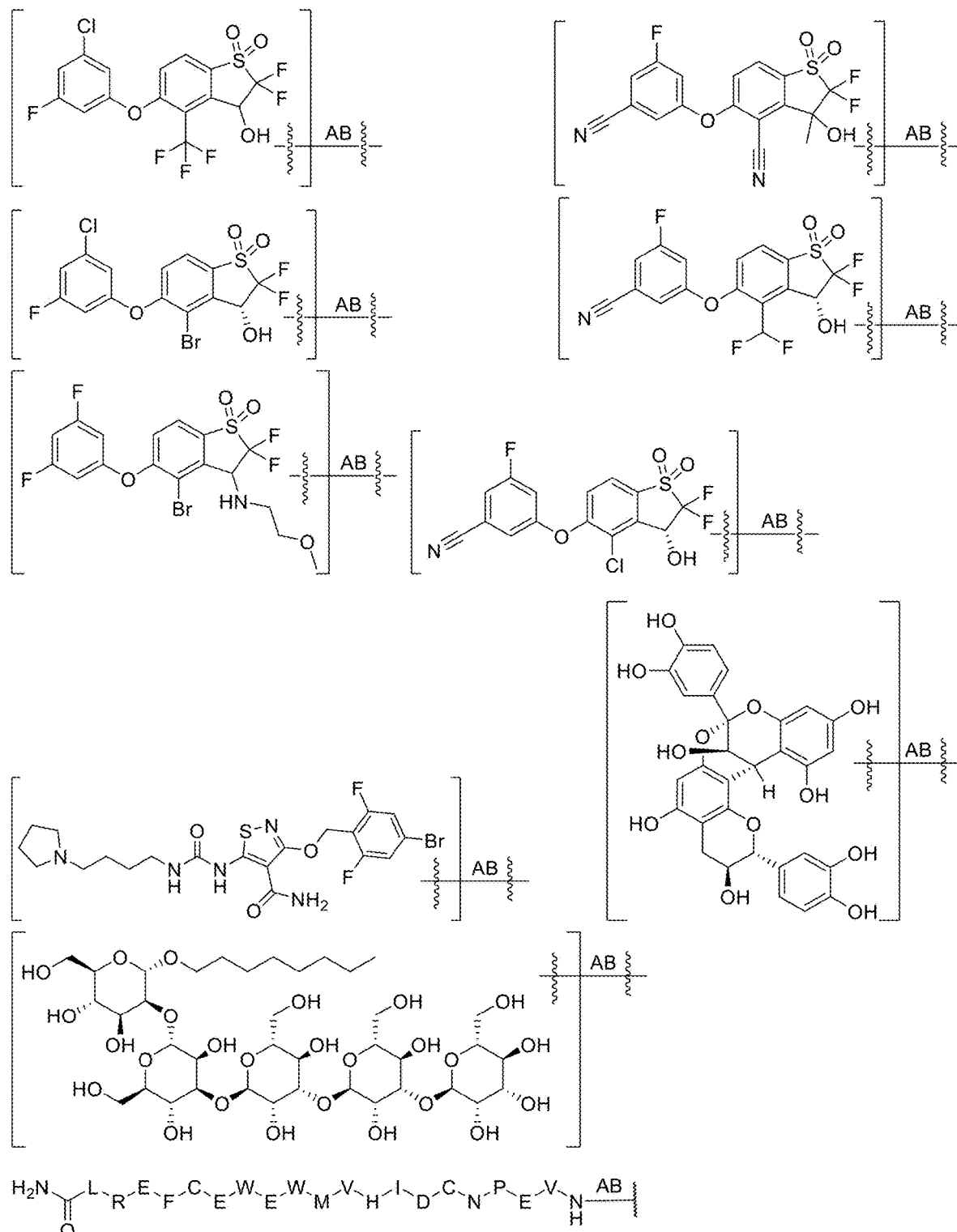
Figure 1E:
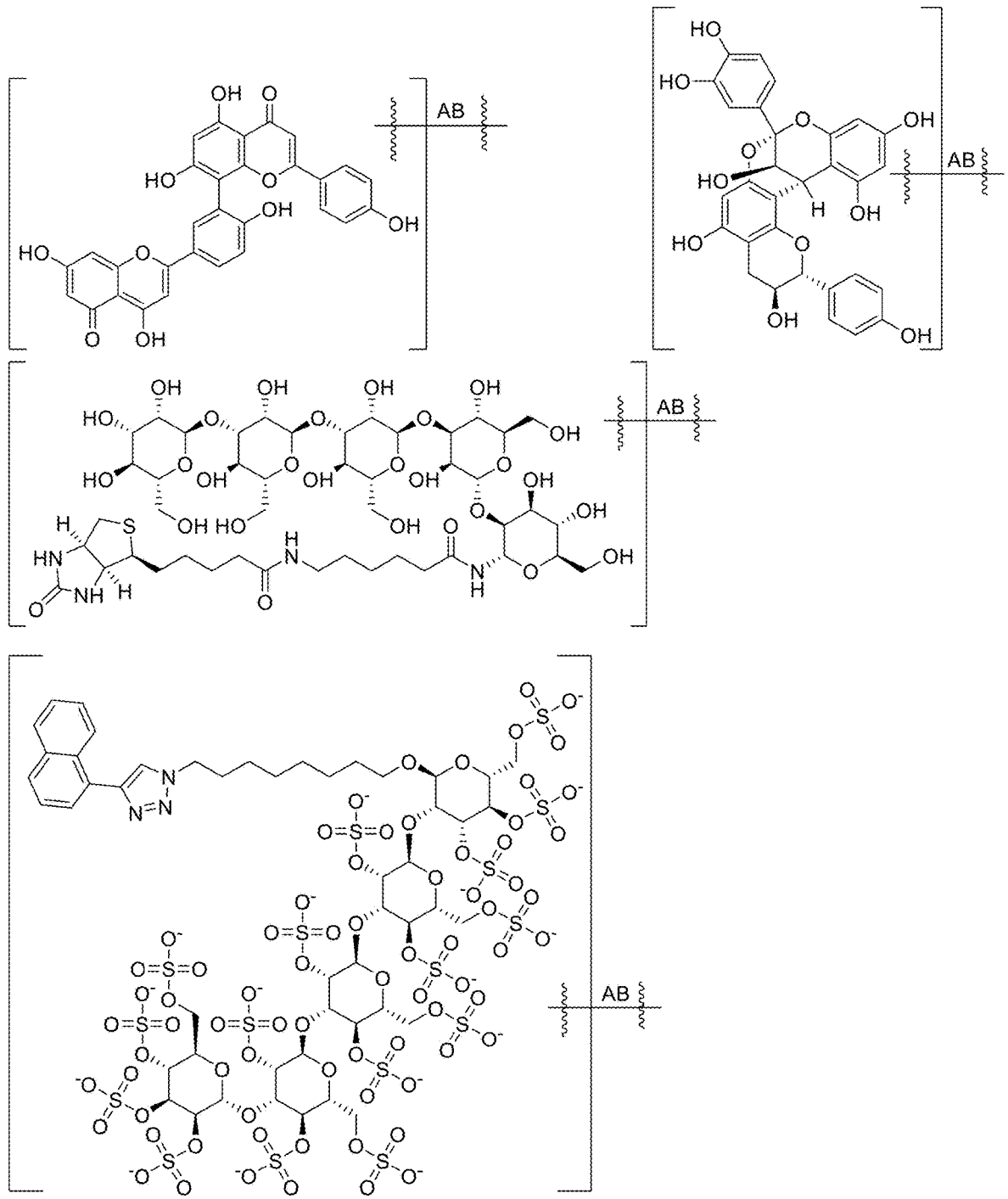
Figure 1F:
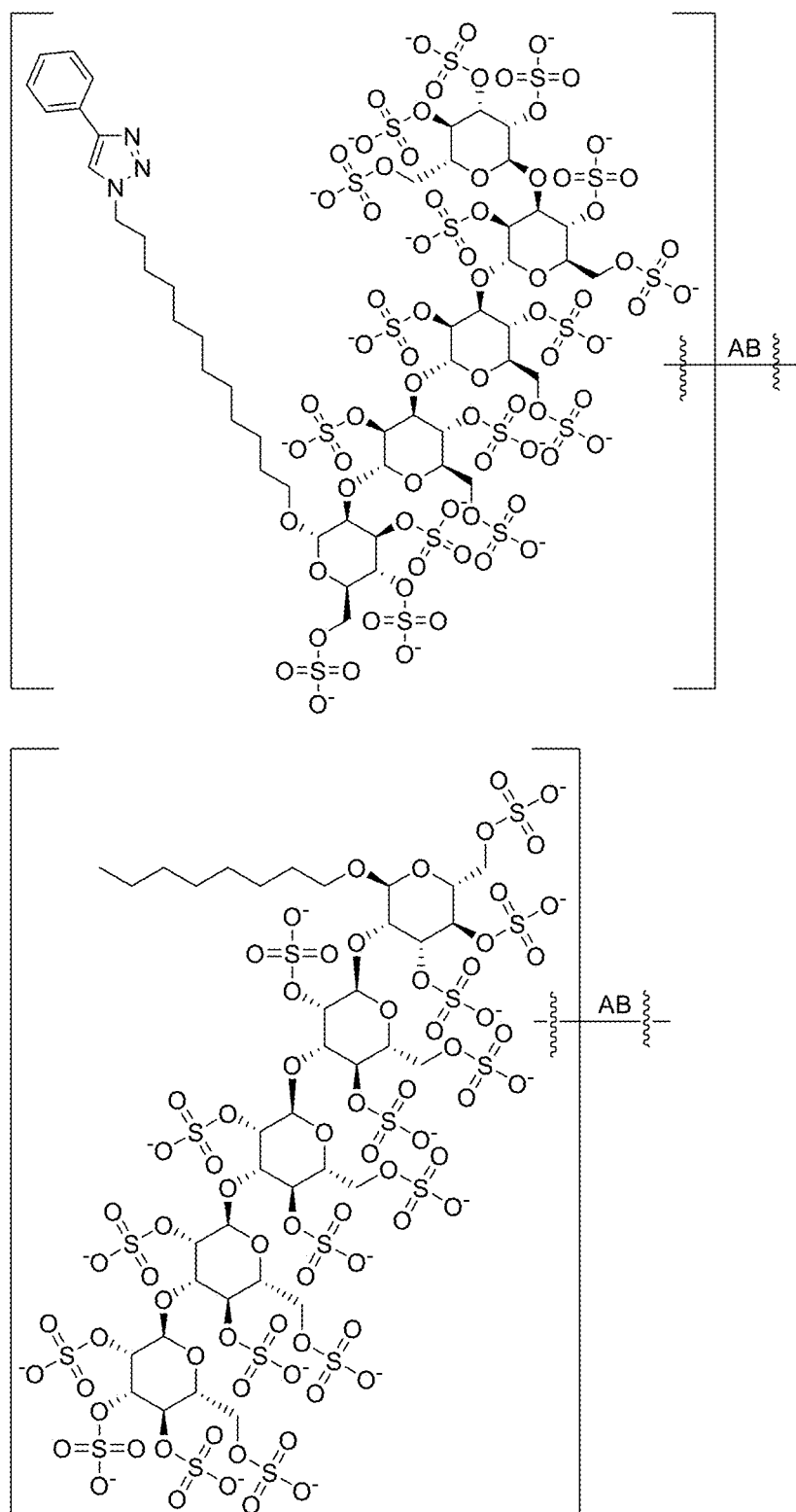
Figure 1G:
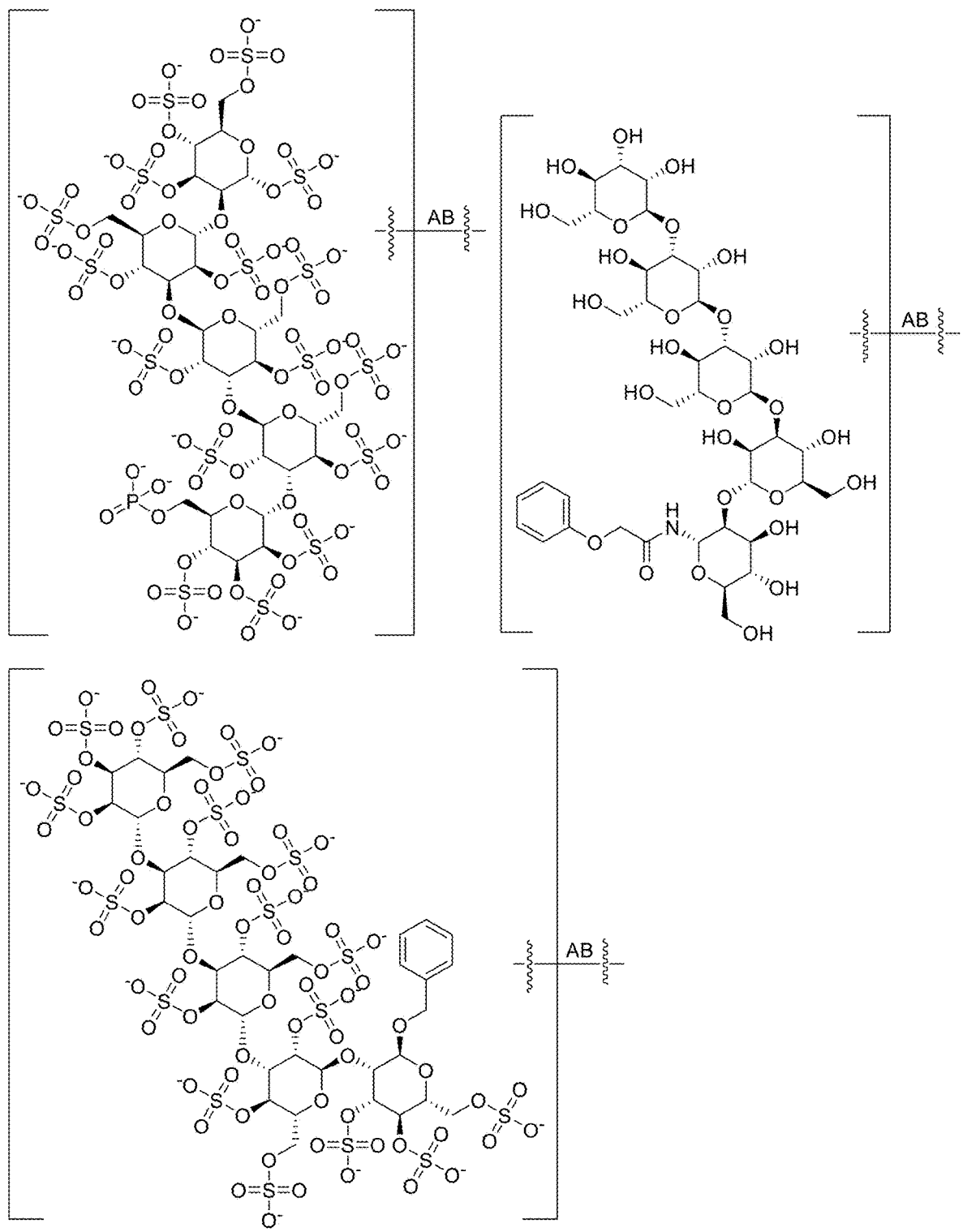
Figure 1H:
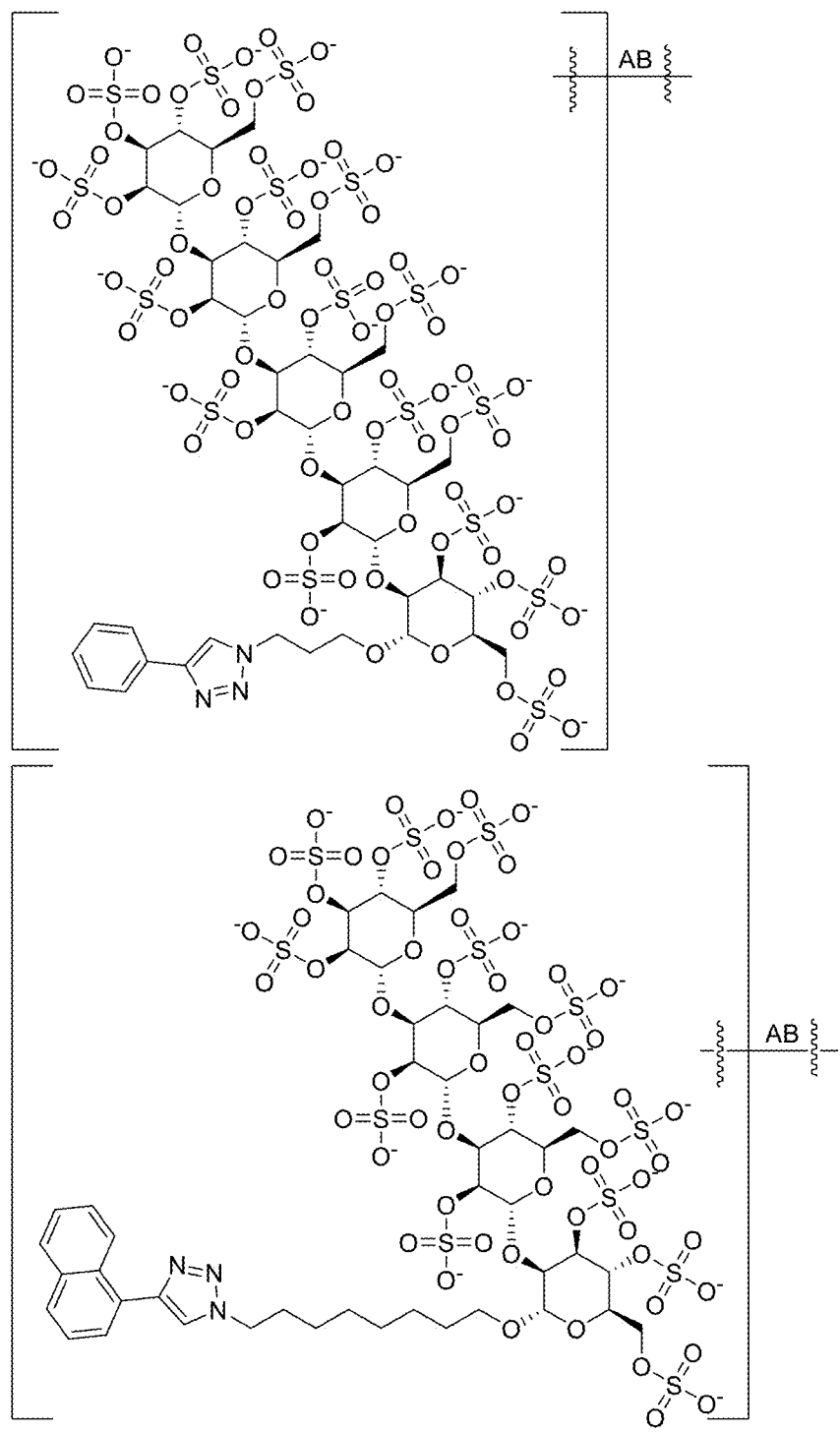
Figure 1I:
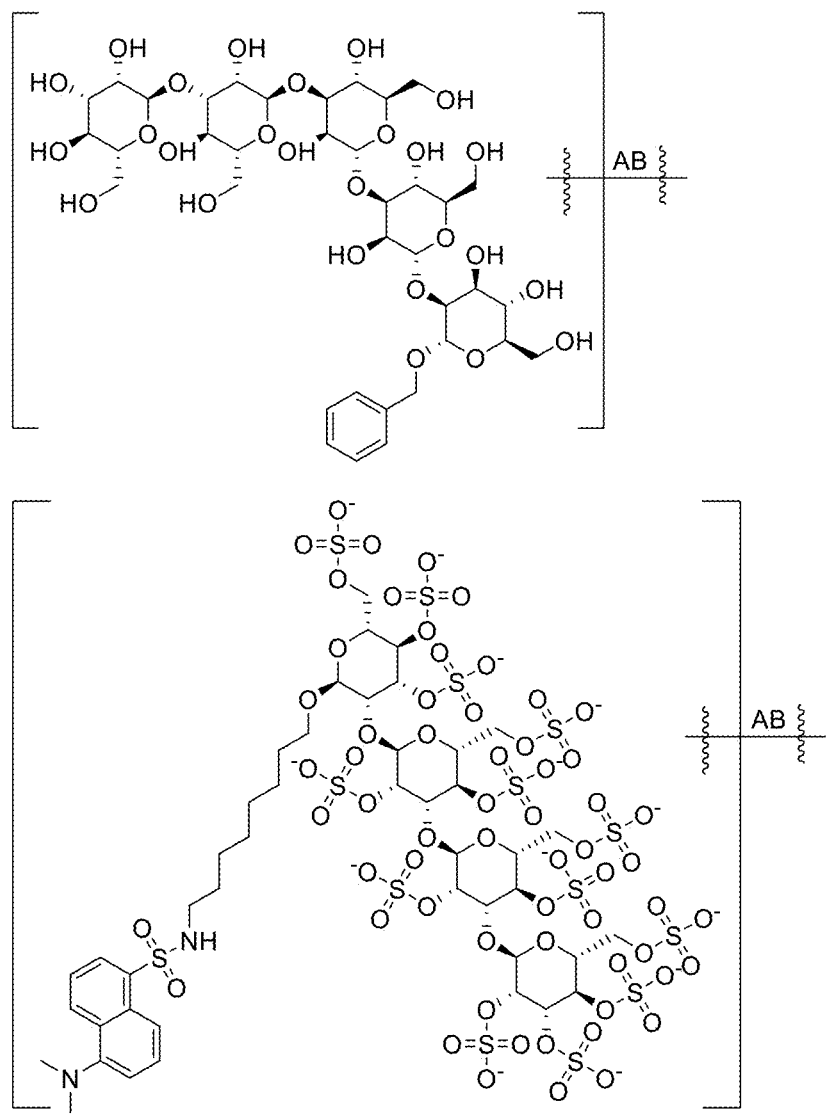
Figure 1J:
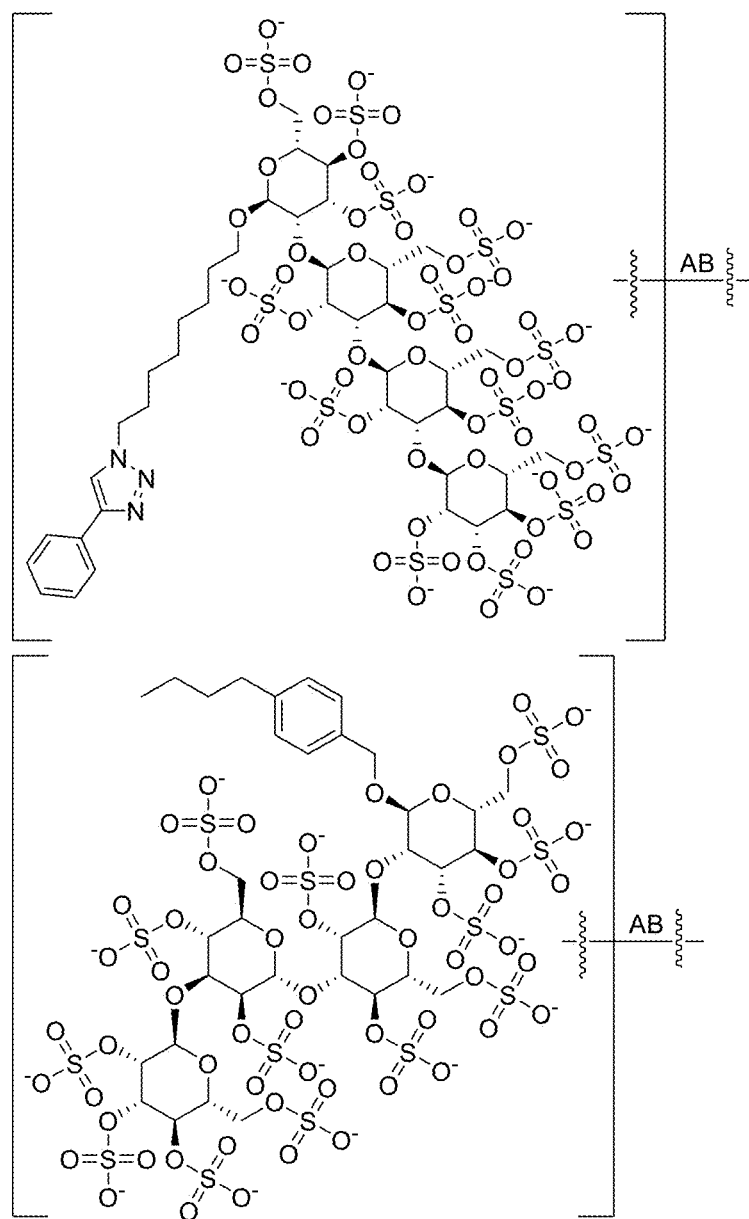
Figure 1K:
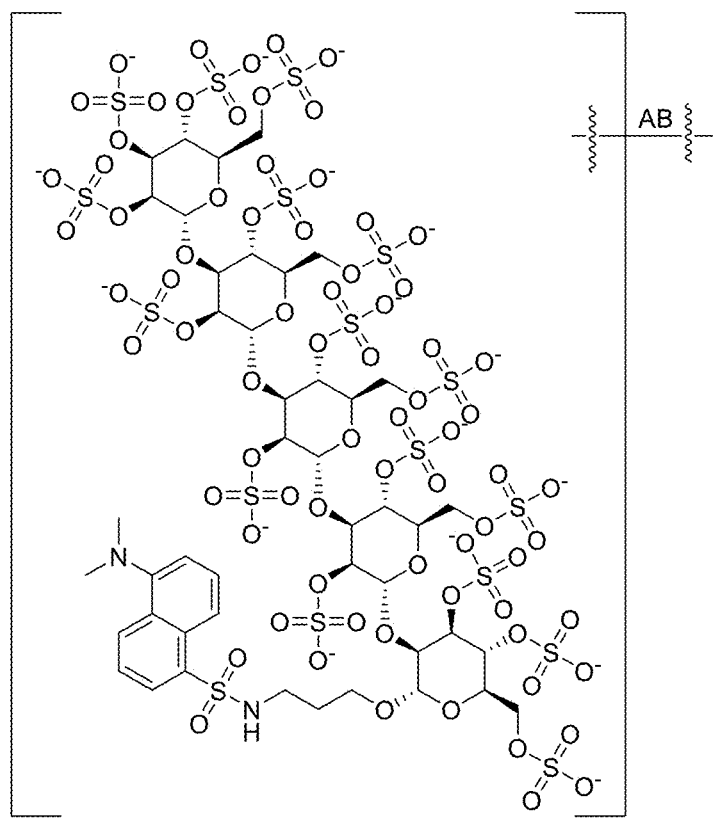
Figure 1L:
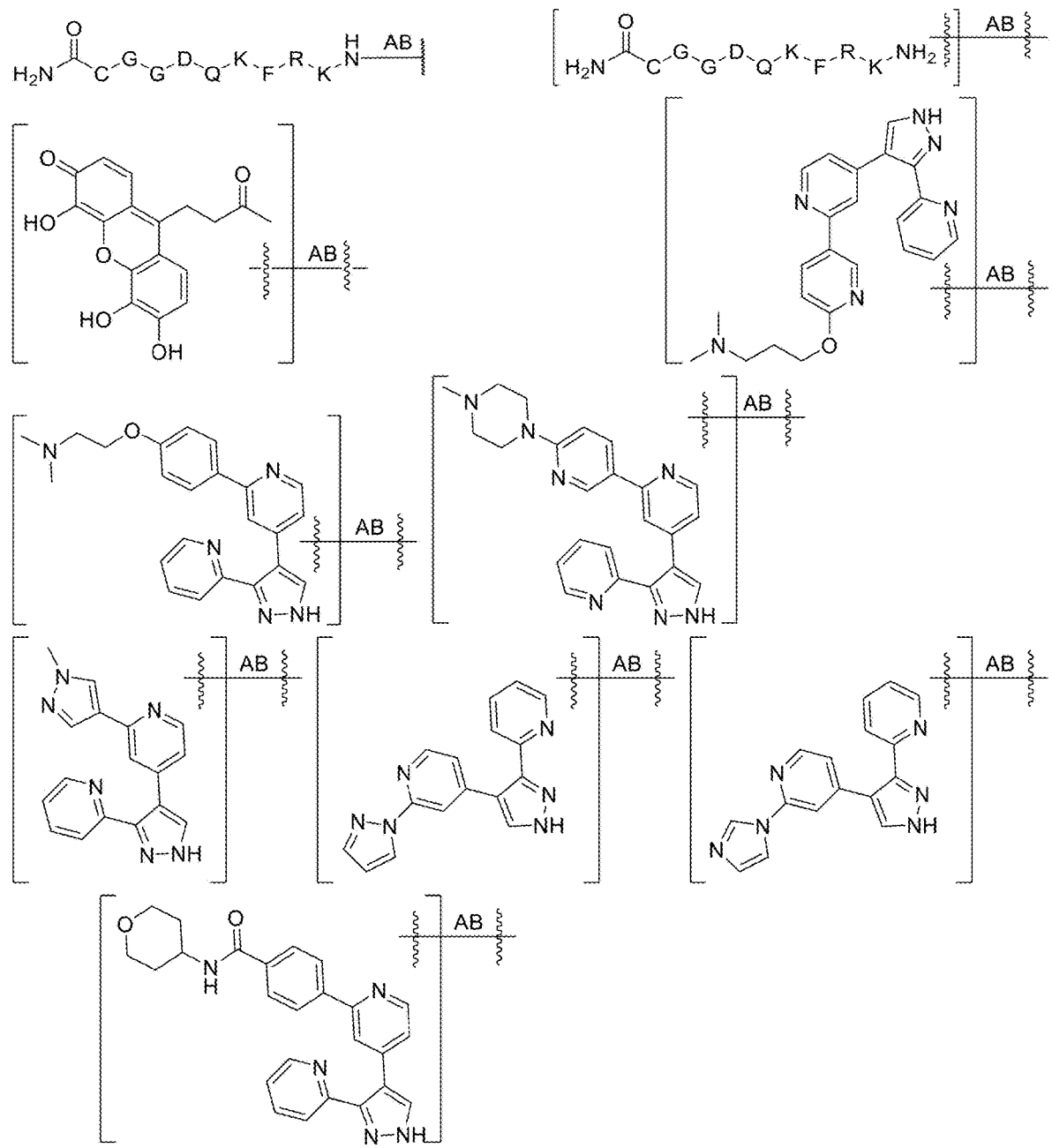
Figure 1M:
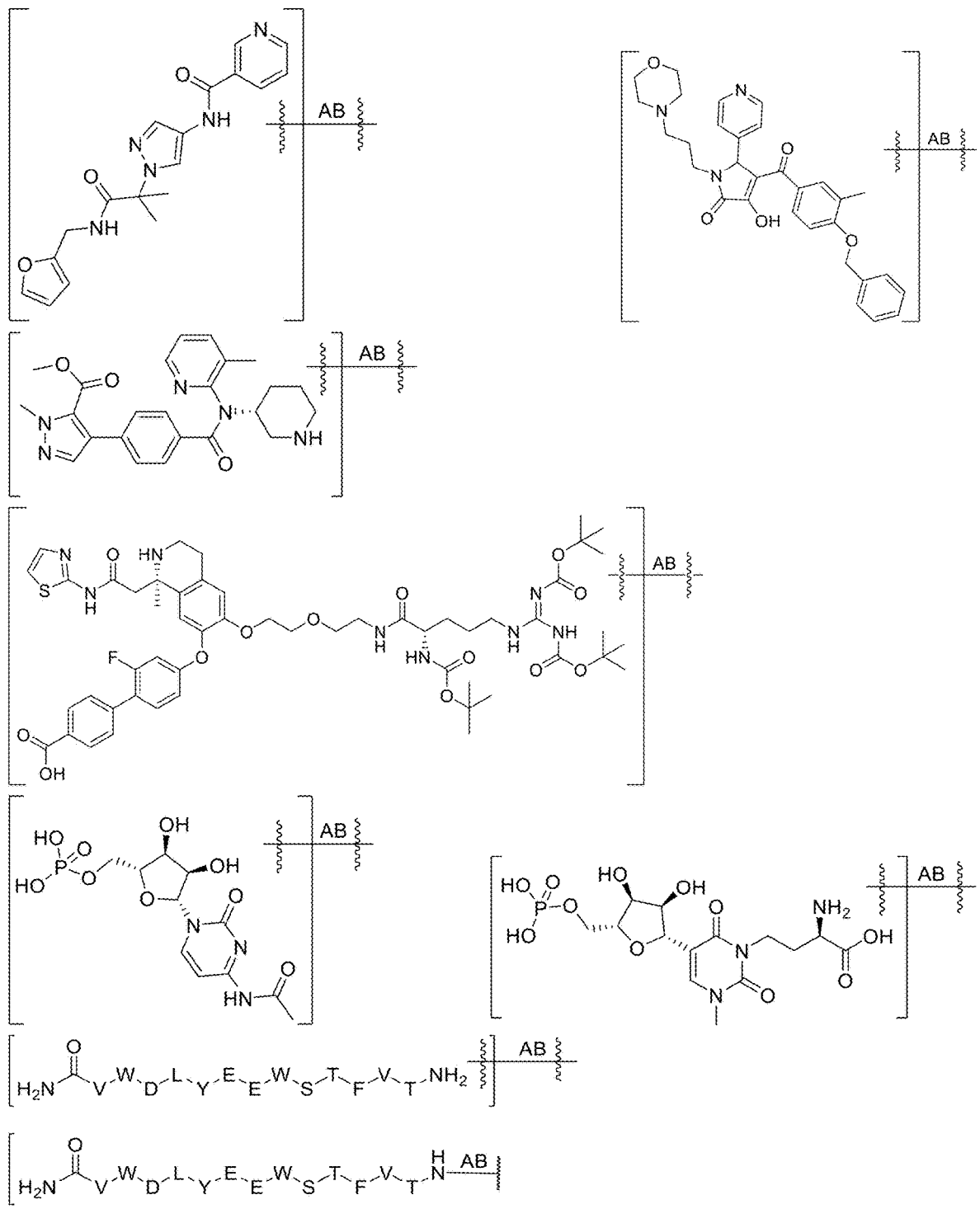
Figure 1N:
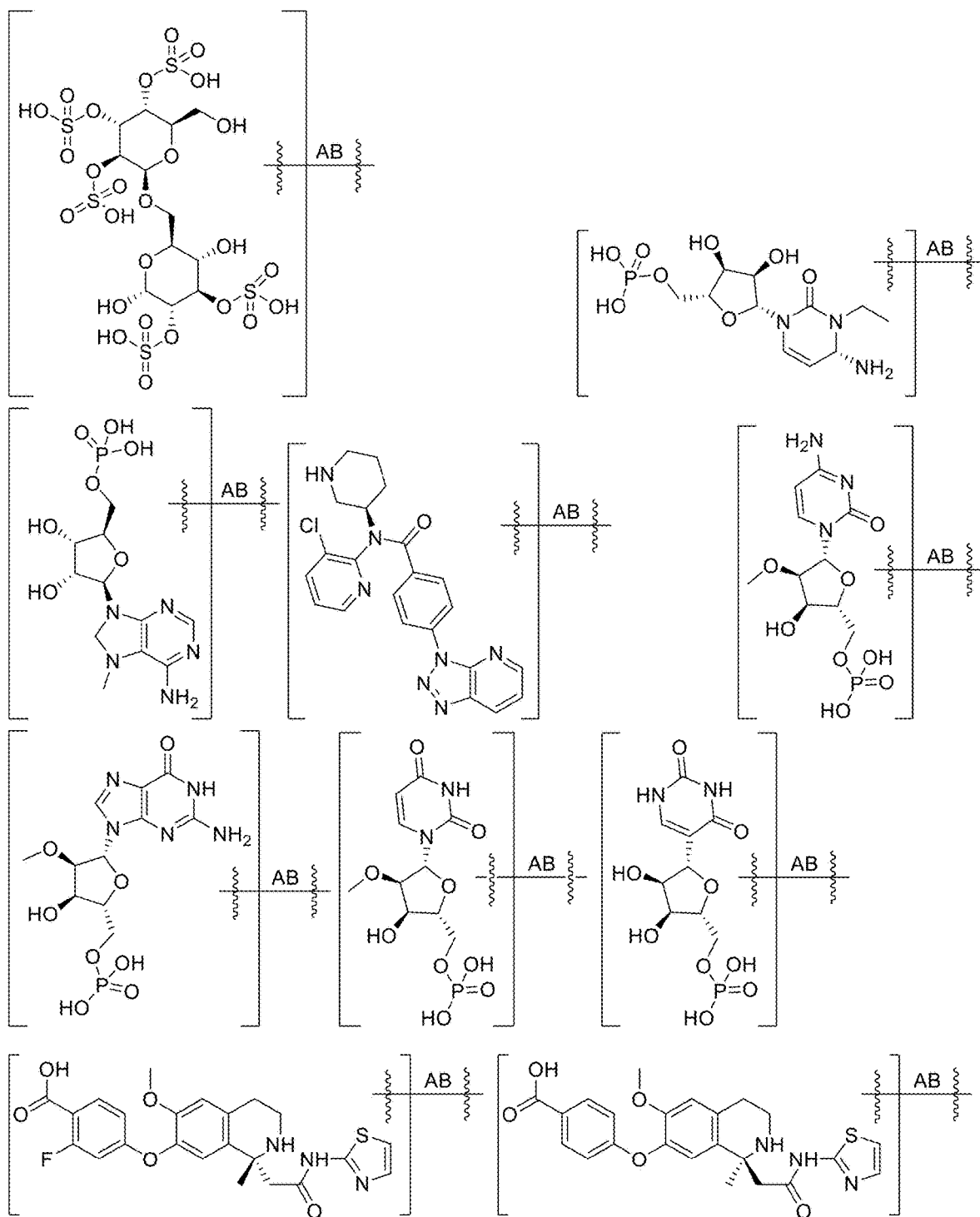
Figure 1O:
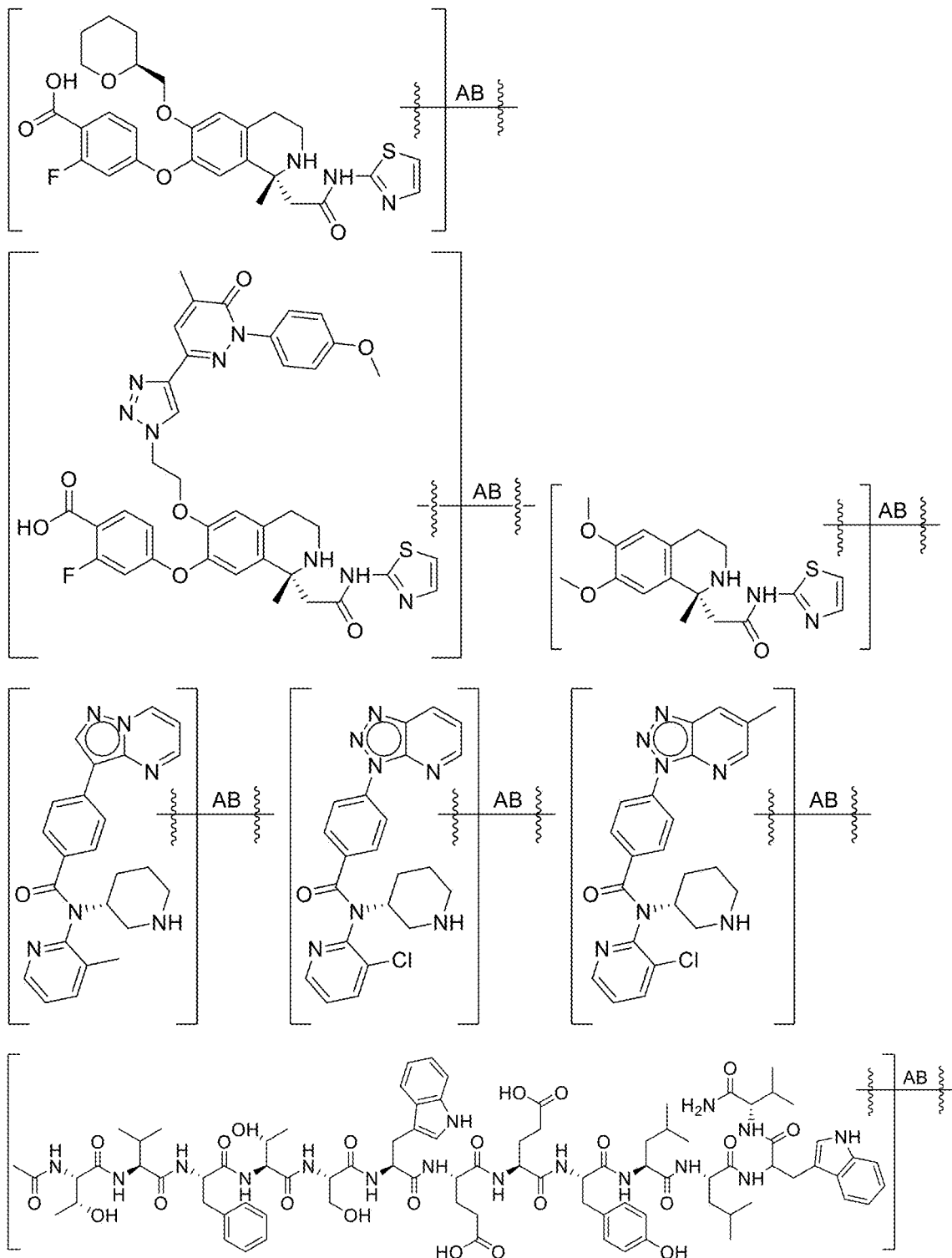
Figure 1P:
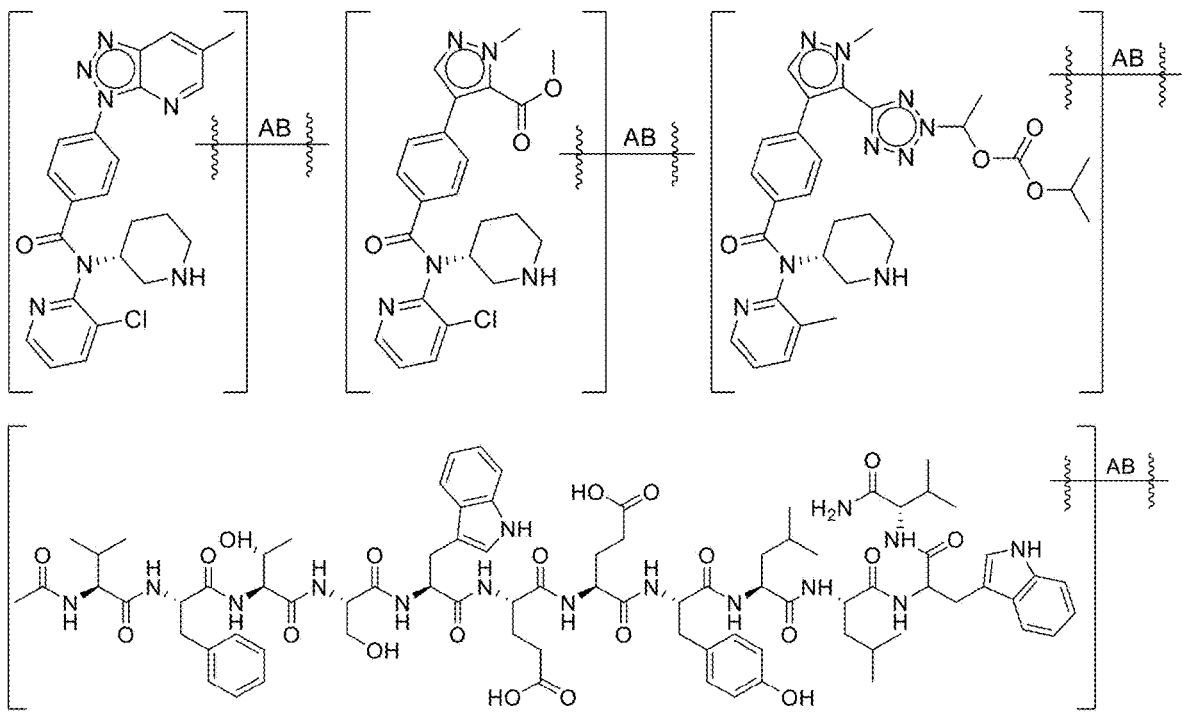
Figure 1Q:
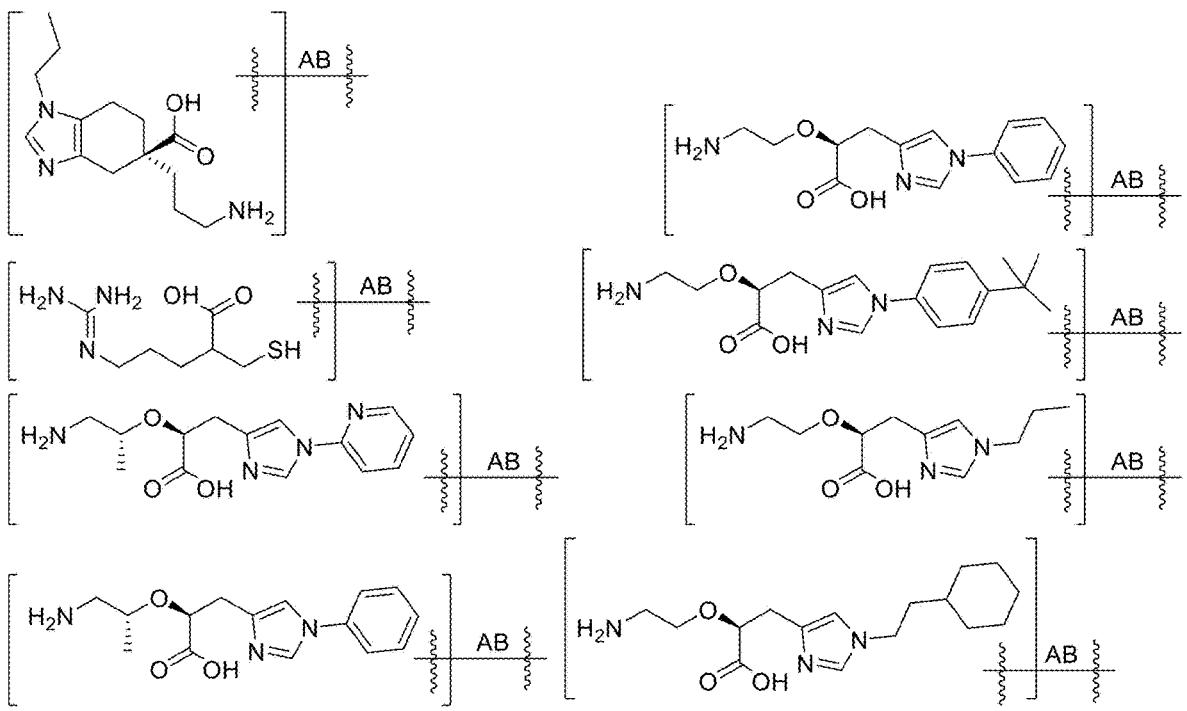
Figure 1R:
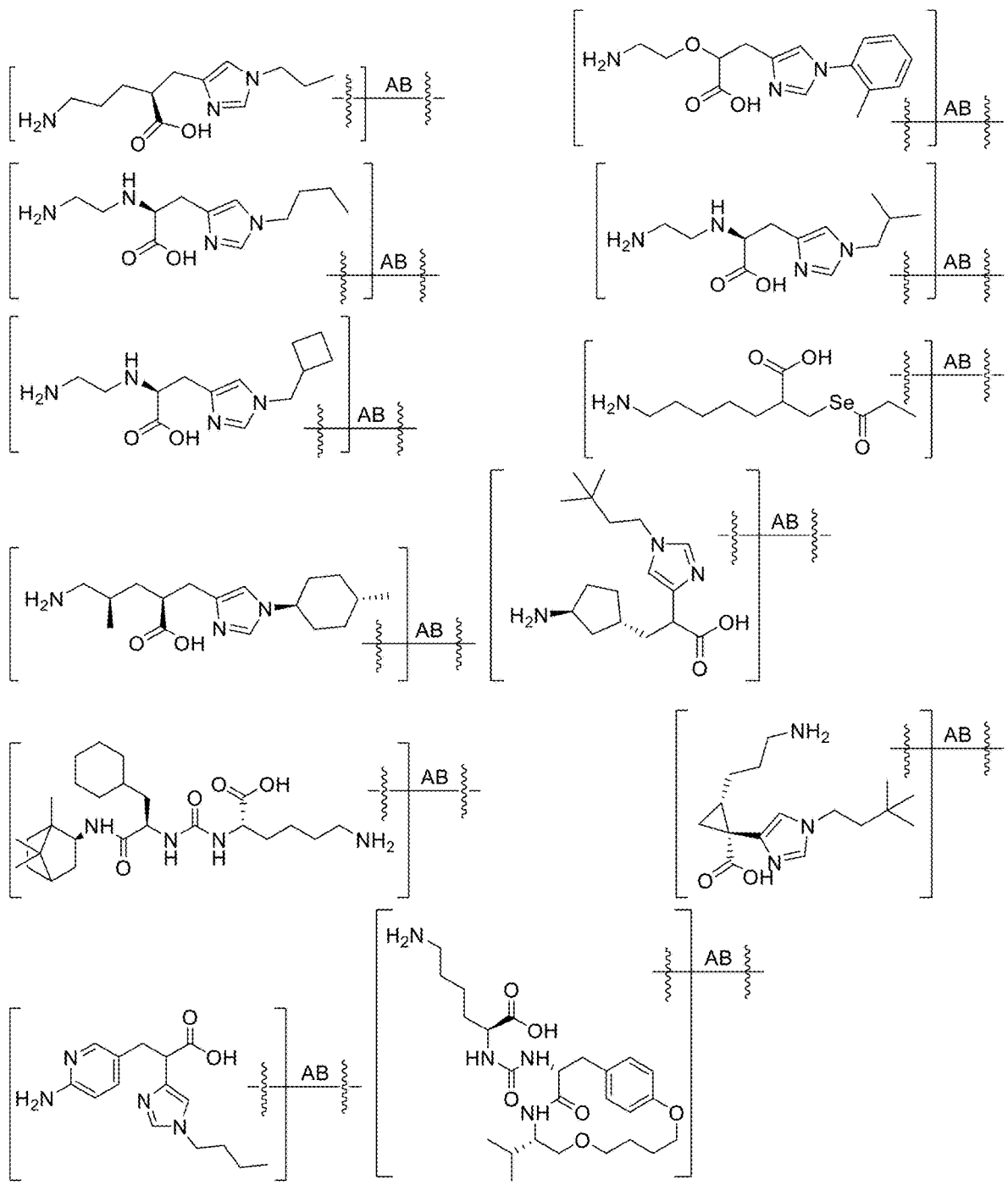
Figure 1S:
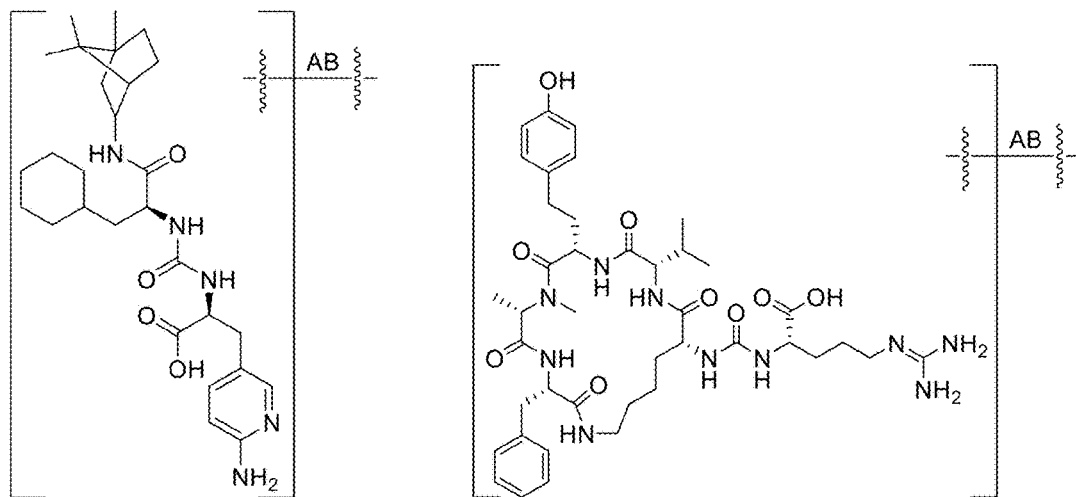
Figure 1T:
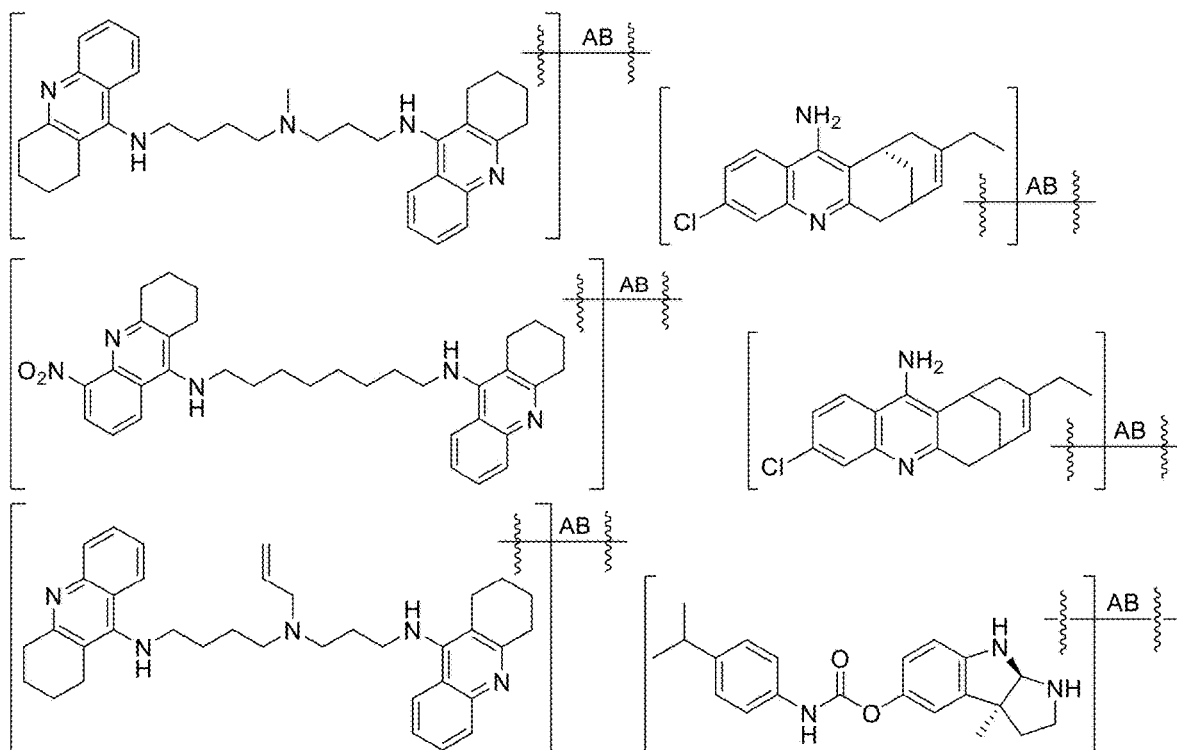
Figure 1U:
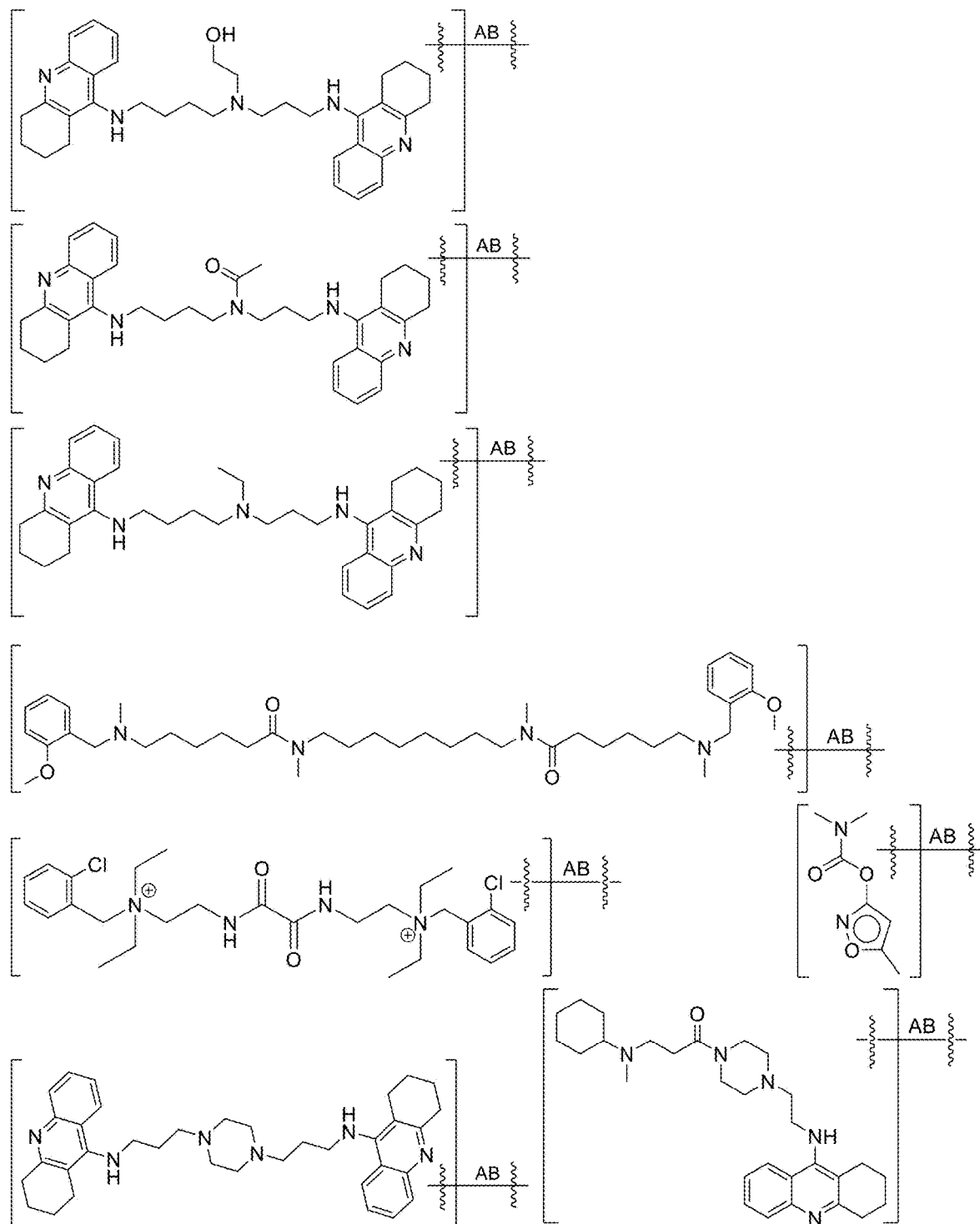
Figure 1V:
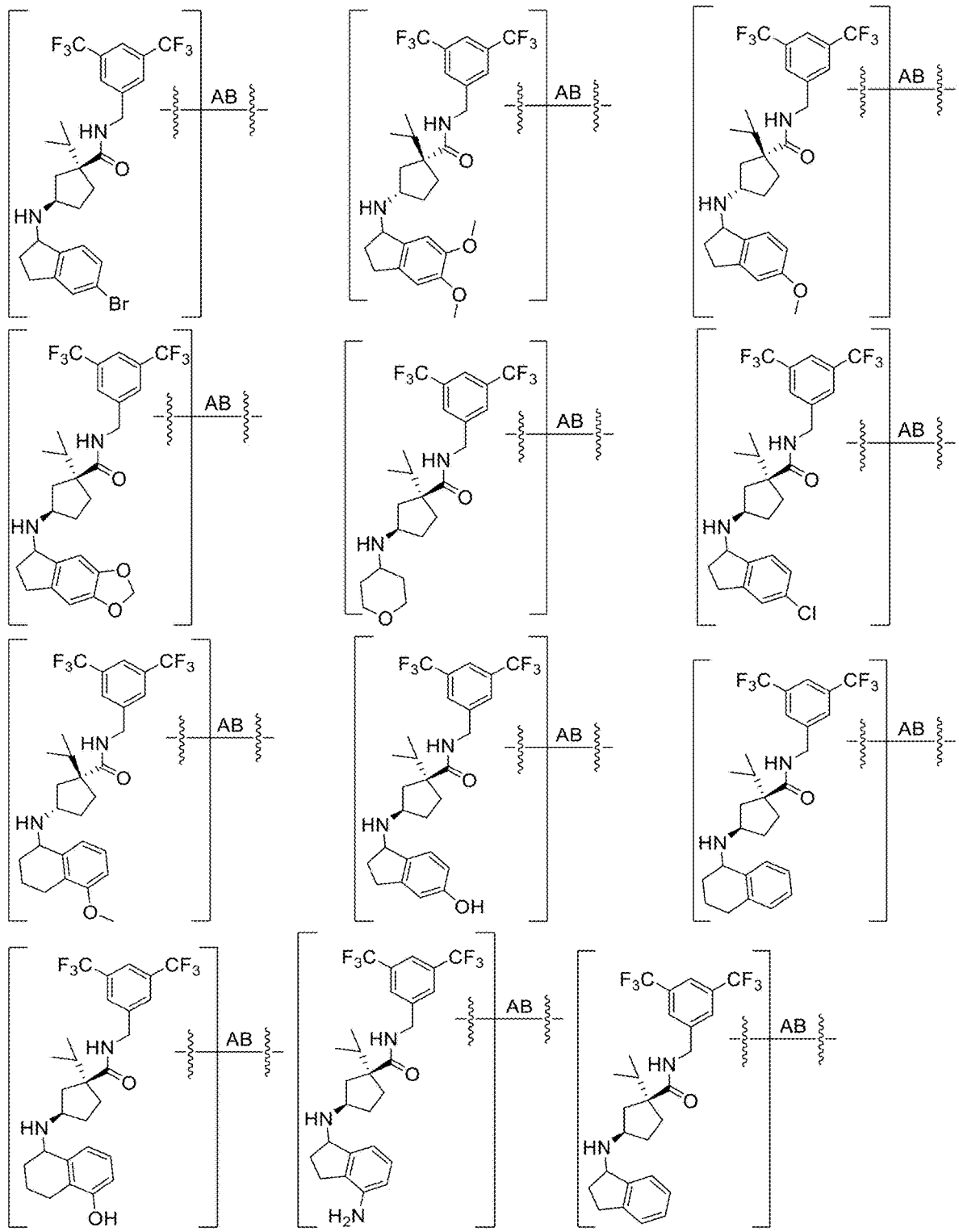
Figure 1W:
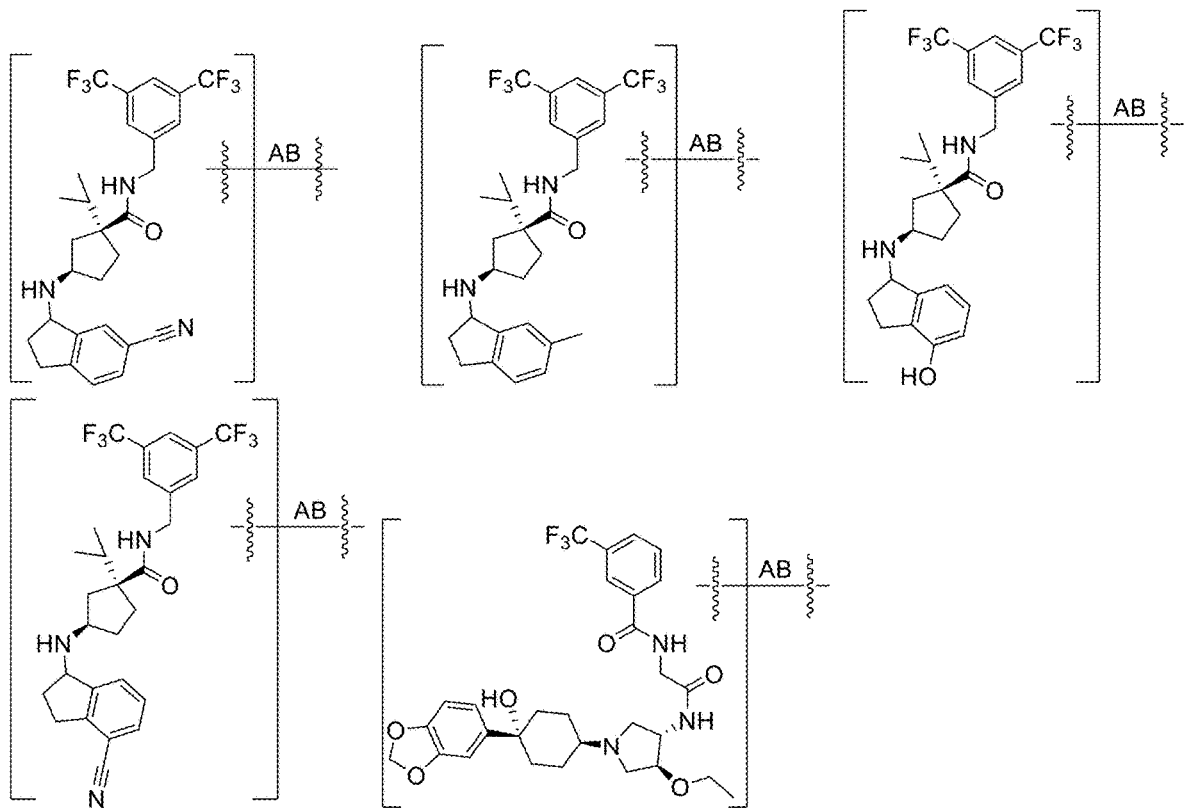
Figure 1X:
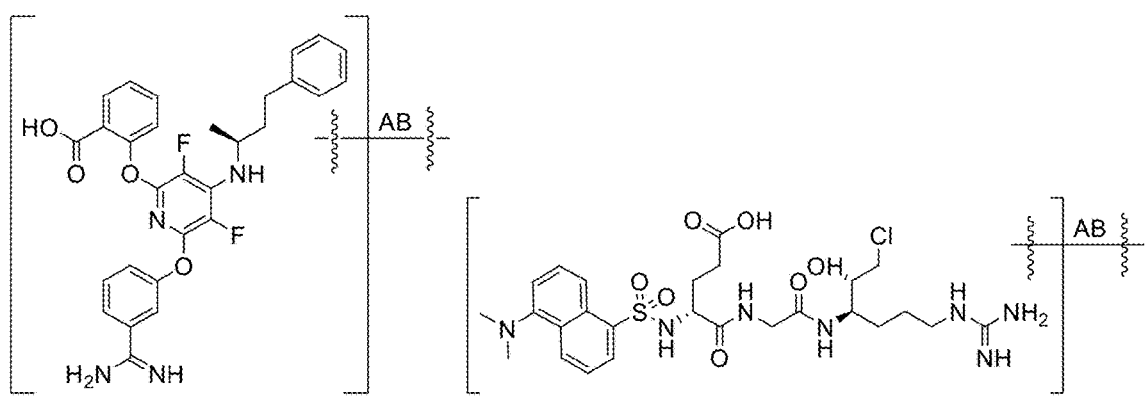
Figure 1Y:
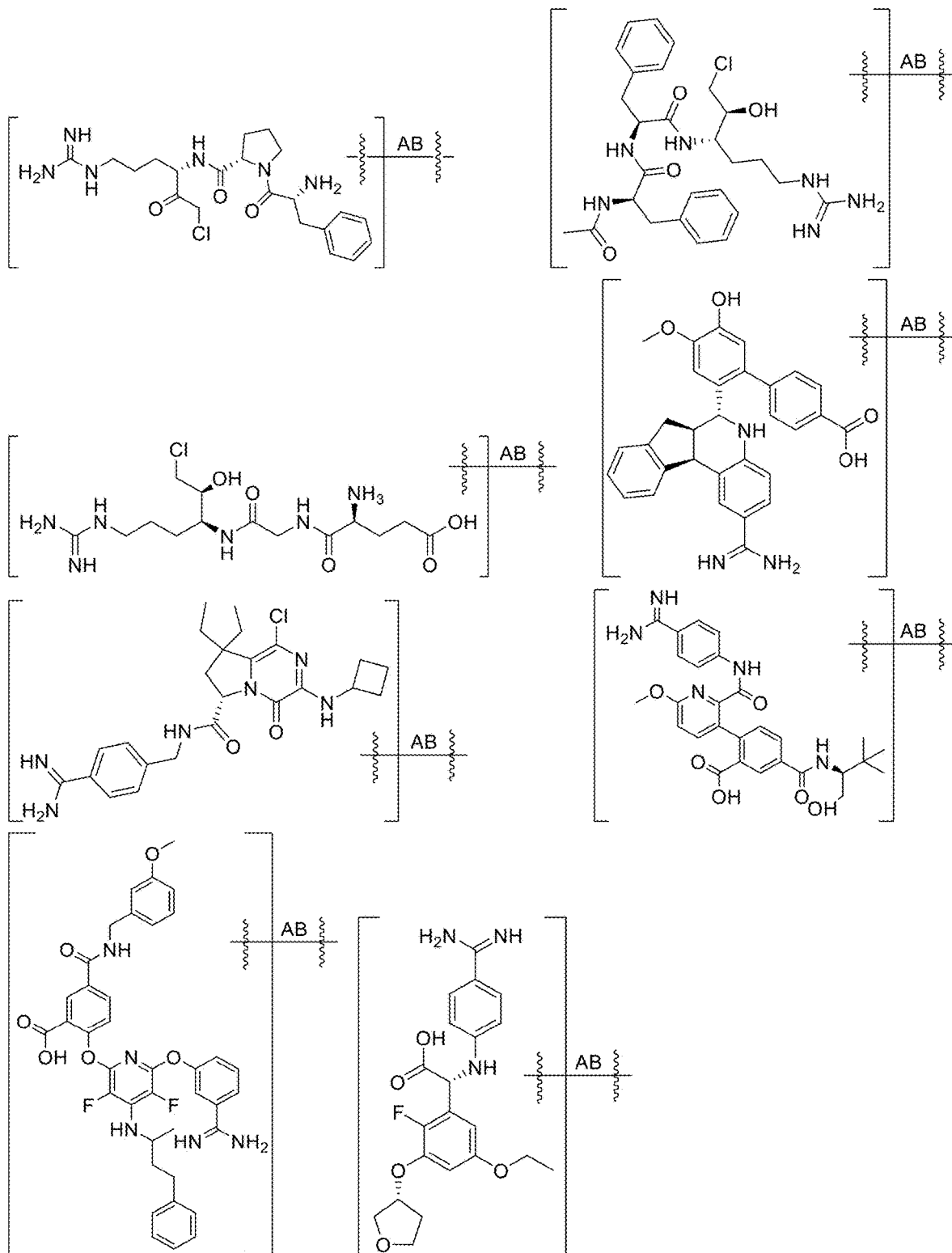
Figure 1Z:
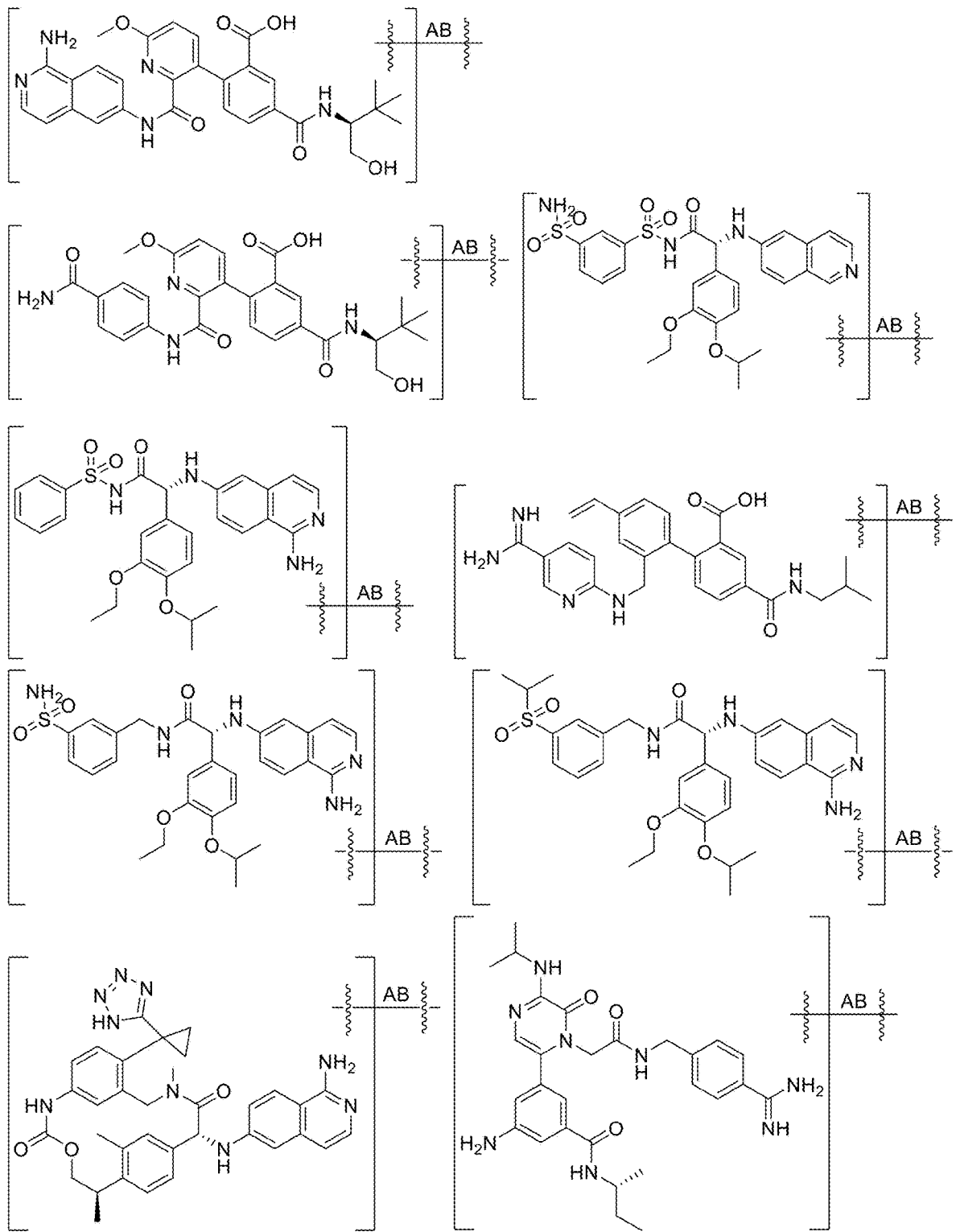

Novel extracellular protein degraders and their pharmaceutically acceptable salts and compositions thereof that degrade a Target Extracellular Protein, for example IgG, as well as starting materials and intermediates for such extracellular protein degraders and their methods of use and manufacture are provided. These extracellular protein degraders are highly potent binders of both ASGPR and their respective extracellular protein targets. Some of the extracellular protein degraders of the present invention use high binding ASGPR Binding Ligands. This increased binding affinity for ASGPR results extracellular protein degraders with various advantages over previously known extracellular protein degraders. For example, an extracellular protein degrader of the present invention can be dosed at a lower dose, less frequently, with less side effects, and/or with increased potency when compared to other extracellular protein degraders. In some embodiments, an extracellular protein degrader that incorporates one of the high binding ASGPR ligands as described herein can be sufficiently active in the form of a monodentate compound (i.e., 1:1 extracellular protein ligand to ASGPR ligand in the therapeutic molecule).

In certain embodiments, the extracellular protein degrading compound degrades an immunoglobulin. The immunoglobulin degraders described herein degrade a selected immunoglobulin by covalently binding a ligand of the selected immunoglobulin to a potent ASGPR binder through selected linking groups. The immunoglobulins that can be targeted according to the present invention include but are not limited to IgA, IgG, IgD, IgE, and IgM, and mutants thereof. In certain aspects of the present invention the selected immunoglobulin degrader degrades IgG.

I. Compound Terminology

Extracellular protein degraders are described using standard nomenclature. Unless defined otherwise, all technical and scientific terms used herein have the same meaning as is commonly understood by one of skill in the art to which this invention belongs.

All of the extracellular protein degraders described herein include independently the enantiomers, mixtures of enantiomers, diastereomers, tautomers, racemates and other isomers, such as rotamers, as if each is specifically described, unless otherwise indicated or otherwise excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes extracellular protein degraders with at least one desired isotopic substitution of an atom, at an amount above the natural abundance of the isotope, i.e., enriched.

Examples of isotopes that can be incorporated into extracellular protein degraders, of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$, and $^{125}I$ respectively. In one embodiment, isotopically labelled into extracellular protein degraders can be used in metabolic studies (with, for example $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. Isotopically labeled into extracellular protein degraders of this invention and prodrugs thereof can generally be prepared by carrying out the procedures disclosed in the schemes or in the examples and preparations described below by using a readily available isotopically labeled reagent instead of a non-isotopically labeled reagent.

By way of general example and without limitation, isotopes of hydrogen, for example, deuterium ($^{2}H$) and tritium ($^{3}H$) may optionally be used anywhere in described structures that achieves the desired result. Alternatively, or in addition, isotopes of carbon, e.g., $^{13}C$ and $^{14}C$, may be used. In one embodiment, the isotopic substitution is accomplished by replacing hydrogen with a deuterium at one or more locations on the molecule to improve the performance of the drug, for example, the pharmacodynamics, pharmacokinetics, biodistribution, half-life, stability, AUC, $T_{max}$, $C_{max}$, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial isotopic substitution means that at least one hydrogen is substituted with deuterium. In certain embodiments, the isotope is 80, 85, 90, 95 or 99% or more enriched in an isotope at any location of interest. In certain embodiments deuterium is 80, 85, 90, 95 or 99% enriched at a desired location. Unless otherwise stated, the enrichment at any point is above natural abundance, and in an embodiment is enough to alter a detectable property of the drug in a human.

The extracellular protein degraders of the present invention may form a solvate with solvents (including water). Therefore, in one embodiment, the invention includes a solvated form of the active extracellular protein degrader. The term "solvate" refers to a molecular complex of an extracellular protein degrader of the present invention (including a salt thereof) with one or more solvent molecules. Nonlimiting examples of solvents are water, ethanol, dimethyl sulfoxide, acetone and other common organic solvents. The term "hydrate" refers to a molecular complex comprising an extracellular protein degrader of the invention and water. Pharmaceutically acceptable solvates in accordance with the invention include those wherein the solvent of crystallization may be isotopically substituted, e.g. $D_2O$, $d_6$-acetone, $d_6$-DMSO. A solvate can be in a liquid or solid form.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, implant, and the like.

"Pharmaceutical compositions" are compositions comprising at least one active agent, and at least one other substance, such as a carrier. The present invention includes pharmaceutical compositions of the described extracellular protein degraders.

"Pharmaceutical combinations" are combinations of at least two active agents which may be combined in a single dosage form or provided together in separate dosage forms.

A "pharmaceutically acceptable salt" is a derivative of the disclosed extracellular protein degrader in which the parent extracellular protein degrader is modified by making inorganic and organic, pharmaceutically acceptable, acid or base addition salts thereof. The salts of the present extracellular protein degraders can be synthesized from a parent extracellular protein degrader that contains a basic or acidic moiety by conventional chemical methods. Generally, such salts can be prepared by reacting free acid forms of these extracellular protein degraders with a stoichiometric amount of the appropriate base (such as Na, Ca, Mg, or K hydroxide, carbonate, bicarbonate, or the like), or by reacting free base forms of these extracellular protein degraders with a stoichiometric amount of the appropriate acid. Such reactions are typically carried out in water or in an organic solvent, or in a mixture of the two. Salts of the present extracellular protein degraders further include solvates of the extracellular protein degraders and of the extracellular protein degrader salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include salts which are acceptable for human consumption and the quaternary ammonium salts of the parent extracellular protein degrader formed, for example, from inorganic or organic acids. Examples, of such salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_{1-4}$—COOH, and the like, or using an acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active extracellular protein degrader is provided.

A "pharmaceutically acceptable excipient" means an excipient that is useful in preparing a pharmaceutical composition/combination that is generally safe, acceptable for human consumption, and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein. Typically, the host, patient, or subject is a human. A "patient" or "host" or "subject" also refers to for example, a mammal, primate (e.g., human), cow, sheep, goat, horse, dog, cat, rabbit, rat, mice, bird, and the like.

A "therapeutically effective amount" of an extracellular protein degrader, pharmaceutical composition, or combination of this invention means an amount that when administered to a host provides a therapeutic benefit such as an amelioration of symptoms or reduction or diminution of the disease itself.

In one embodiment, the substitution of a hydrogen atom for a deuterium atom occurs within any variable group. For example, when any variable group is, or contain for example through substitution, methyl, ethyl, or methoxy, the alkyl residue may be deuterated (in nonlimiting embodiments, $CDH_2$, $CD_2H$, $CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, a variable group has a "" or an "a" designation, which in one embodiment can be deuterated. In certain other embodiments, when two substituents of the central core ring are combined to form a cyclopropyl ring, the unsubstituted methylene carbon may be deuterated.

The term "immunoglobulin," typically refers to a large Y-shaped protein (e.g. an antibody) that identifies and neutralizes a foreign compound or object such as a pathogen or disease tissue.

Non-limiting examples of immunoglobulin proteins include IgA, IgD, IgE, IgG, and IgM. An immunoglobulin as used herein may also include a binding fragment as known to the skilled worker.

A dash ("-") that is not between two letters or symbols is used to indicate a point of attachment for a substituent. For example, —(C=O)$NH_2$ is attached through carbon of the keto (C=O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., =O) then two hydrogens on the atom are replaced. For example a pyridyl group substituted by oxo is a pyridone. Combinations of substituents and/or variables are permissible only if such combinations result in stable compounds or useful synthetic intermediates.

"Alkyl" is a branched, straight chain, or cyclic saturated aliphatic hydrocarbon group. In one embodiment, the alkyl contains from 1 to about 12 carbon atoms, more generally from 1 to about 6 carbon atoms, from 1 to about 4 carbon atoms, or from 1 to 3 carbon atoms. In one embodiment, the alkyl contains from 1 to about 8 carbon atoms. In certain embodiments, the alkyl is $C_1$-$C_2$, $C_1$-$C_3$, $C_1$-$C_4$, $C_1$-$C_5$ or $C_1$-$C_6$. The specified ranges as used herein indicate an alkyl group which is considered to explicitly disclose as individual species each member of the range described as a unique species. For example, the term $C_1$-$C_6$ alkyl as used herein indicates a straight or branched alkyl group having from 1, 2, 3, 4, 5, or 6 carbon atoms and also a carbocyclic alkyl group of 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-$C_4$ alkyl, or —$C_0$-$C_4$alkyl($C_3$-$C_7$cycloalkyl), the indicated group, in this case cycloalkyl, is either directly bound by a single covalent bond ($C_0$alkyl), or attached by an alkyl chain in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, 2,3-dimethylbutane, and hexyl.

When a term is used that includes "alk" it should be understood that "cycloalkyl" or "carbocyclic" can be considered part of the definition, unless unambiguously excluded by the context. For example and without limitation, the terms alkyl, alkenyl, alkynyl, alkoxy, alkanoyl, alkenloxy, haloalkyl, etc. can all be considered to include the cyclic forms of alkyl, unless unambiguously excluded by context.

"Alkenyl" is a branched or straight chain aliphatic hydrocarbon group having one or more carbon-carbon double bonds that may occur at a stable point along the chain. Nonlimiting examples are $C_2$-$C_8$alkenyl, $C_2$-$C_7$alkenyl, $C_2$-$C_6$alkenyl, $C_2$-$C_5$alkenyl and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl.

"Alkynyl" is a branched or straight chain aliphatic hydrocarbon group having one or more carbon-carbon triple bonds that may occur at any stable point along the chain, for example, $C_2$-$C_8$alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Aryl" indicates an aromatic group containing only carbon in the aromatic ring or rings. In one embodiment, the aryl group contains 1 to 3 separate or fused rings and is 6 to 14 or 18 ring atoms, without heteroatoms as ring members. The term "aryl" includes groups where a saturated or partially unsaturated carbocycle group is fused with an aromatic ring. The term "aryl" also includes groups where a saturated or partially unsaturated heterocycle group is fused with an aromatic ring so long as the attachment point is the aromatic ring. Such compounds may include aryl rings fused to a 4 to 7 or a 5 to 7-membered saturated or partially unsaturated cyclic group that optionally contains 1, 2 or 3 heteroatoms independently selected from N, O, B, P, Si and S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group.

The term "heterocycle" refers to saturated and partially saturated heteroatom-containing ring radicals, where the heteroatoms may be selected from N, S, and O. The term "heterocycle" includes monocyclic 3-12 membered rings, as well as bicyclic 5-16 membered ring systems (which can include fused, bridged, or spiro, bicyclic ring systems). It does not include rings containing —O—O— or —S—S— portions. Examples of saturated heterocycle groups include saturated 4- to 7-membered monocyclic groups containing 1 to 4 nitrogen atoms [e.g., pyrrolidinyl, imidazolidinyl, piperidinyl, pyrrolinyl, azetidinyl, piperazinyl, and pyrazolidinyl]; saturated 4 to 6-membered monocyclic groups containing 1 to 2 oxygen atoms and 1 to 3 nitrogen atoms [e.g., morpholinyl]; saturated 3 to 6-membered heteromonocyclic group containing 1 to 2 sulfur atoms and 1 to 3 nitrogen atoms [e.g., thiazolidinyl]. Examples of partially saturated heterocycle radicals include but are not limited to, dihydrothienyl, dihydropyranyl, dihydrofuryl, and dihydrothiazolyl. Examples of partially saturated and saturated heterocycle groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]

isothiazol-6-yl, dihydropyranyl, dihydrofuryl and dihydrothiazolyl. "Bicyclic heterocycle" includes groups wherein the heterocyclic radical is fused with an aryl radical wherein the point of attachment is the heterocycle ring. "Bicyclic heterocycle" also includes heterocyclic radicals that are fused or bridged with a carbocycle radical. For example partially unsaturated condensed heterocyclic group containing 1 to 5 nitrogen atoms, for example, indoline, isoindoline, partially unsaturated condensed heterocyclic group containing 1 to 2 oxygen atoms and 1 to 3 nitrogen atoms, partially unsaturated condensed heterocyclic group containing 1 to 2 sulfur atoms and 1 to 3 nitrogen atoms, and saturated condensed heterocyclic group containing 1 to 2 oxygen or sulfur atoms.

Non-limiting examples of bicyclic heterocycles include:

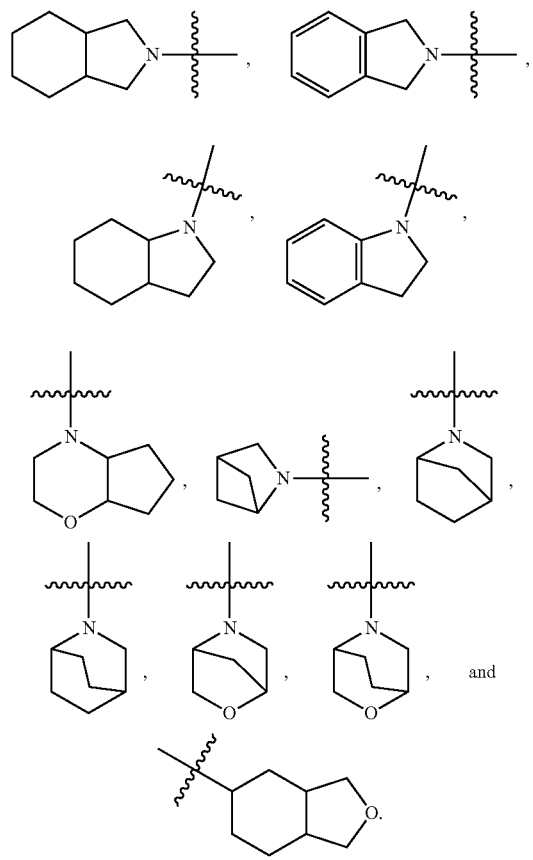

Unless otherwise drawn or clear from the context, the term "bicyclic heterocycle" includes cis and trans diastereomers. Non-limiting examples of chiral bicyclic heterocycles include:

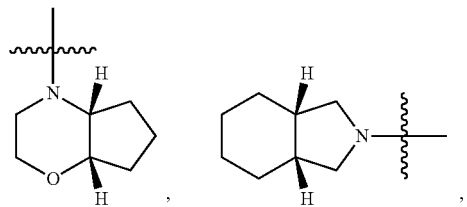

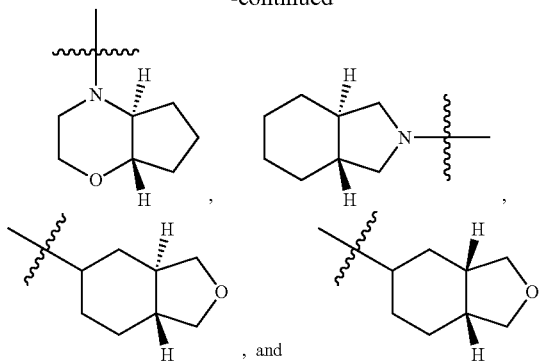

In certain alternative embodiments the term "heterocycle" refers to saturated and partially saturated heteroatom-containing ring radicals, where the heteroatoms may be selected from N, S, O, B, Si, and P.

"Heteroaryl" refers to a stable monocyclic, bicyclic, or multicyclic aromatic ring which contains from 1 to 3, or in some embodiments from 1, 2, or 3 heteroatoms selected from N, O, S, B, and P (and typically selected from N, O, and S) with remaining ring atoms being carbon, or a stable bicyclic or tricyclic system containing at least one 5, 6, or 7 membered aromatic ring which contains from 1 to 3, or in some embodiments from 1 to 2, heteroatoms selected from N, O, S, B or P with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5 or 6 ring atoms. In some embodiments bicyclic heteroaryl groups are 8- to 10-membered heteroaryl groups, that is, groups containing 8 or 10 ring atoms in which one 5, 6, or 7-member aromatic ring is fused to a second aromatic or non-aromatic ring wherein the point of attachment is the aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups are optionally substituted independently with one or more substituents described herein. "Heteroaryloxy" is a heteroaryl group as described bound to the group it substituted via an oxygen, —O—, linker.

"Heteroarylalkyl" is an alkyl group as described herein substituted with a heteroaryl group as described herein.

"Arylalkyl" is an alkyl group as described herein substituted with an aryl group as described herein.

"Heterocycloalkyl" is an alkyl group as described herein substituted with a heterocyclo group as described herein.

The term "heteroalkyl" refers to an alkyl, alkenyl, alkynyl, or haloalkyl moiety as defined herein wherein a $CH_2$ group is either replaced by a heteroatom or a carbon atom is substituted with a heteroatom for example, an amine, carbonyl, carboxy, oxo, thio, phosphate, phosphonate, nitrogen, phosphorus, silicon, or boron. In one embodiment, the only heteroatom is nitrogen. In one embodiment, the only heteroatom is oxygen. In one embodiment, the only heteroatom is sulfur. In one embodiment, "heteroalkyl" is used to indicate a heteroaliphatic group (cyclic, acyclic, substituted, unsubstituted, branched or unbranched) having 1-20 carbon atoms. Nonlimiting examples of heteroalkyl moieties include polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

When compounds are "optionally substituted" they may be substituted as allowed by valence by groups selected from alkyl (including $C_1$-$C_4$alkyl), alkenyl (including $C_2$-$C_4$alkenyl), alkynyl (including $C_2$-$C_4$alkynyl), haloalkyl (including $C_1$-$C_4$haloalkyl), —$OR^6$, F, Cl, Br, I, —$NR^6R^7$, heteroalkyl, cyano, nitro, $C(O)R^3$,

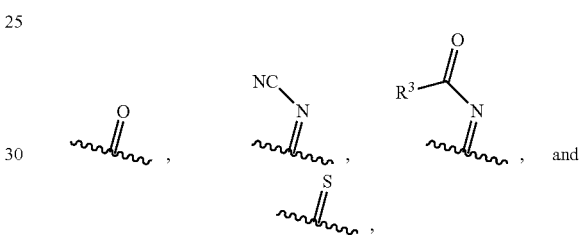

wherein the optional substituent is selected such that a stable compound results. For example

could be substituted with 1 or 2 groups independently selected from alkyl, alkenyl, alkynyl, haloalkyl, —$OR^6$, F, Cl, Br, I, —$NR^6R^7$, heteroalkyl, cyano, nitro, $C(O)R^3$ so long as a stable compound results but only one group selected from

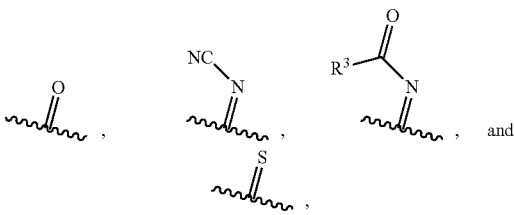

so long as a stable compound results.

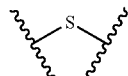

on the other hand could only be substituted with 1 or 2 groups selected from

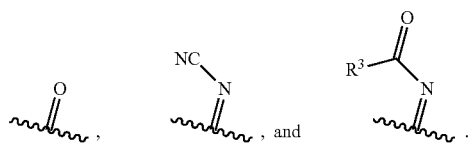

Non-limiting examples of optionally substituted CH$_2$ groups include:

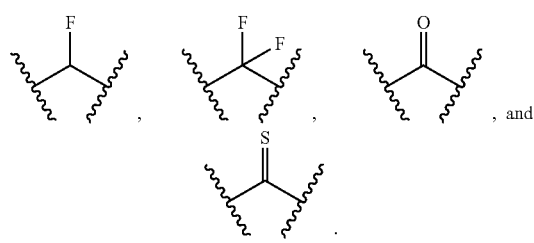

Non-limiting examples of optionally substituted —S— groups include:

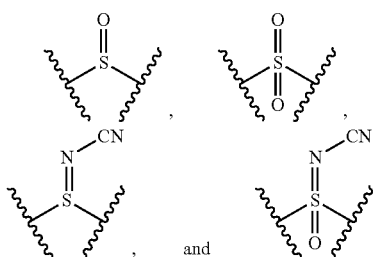

Embodiments of "Alkyl"

In one embodiment "alkyl" is a C$_1$-C$_{10}$alkyl, C$_1$-C$_9$alkyl, C$_1$-C$_8$alkyl, C$_1$-C$_7$alkyl, C$_1$-C$_6$alkyl, C$_1$-C$_5$alkyl, C$_1$-C$_4$alkyl, C$_1$-C$_3$alkyl, or C$_1$-C$_2$alkyl.

In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.
Non-limiting examples of "alkyl" include: methyl, ethyl, propyl, butyl, pentyl, and hexyl.
Additional non-limiting examples of "alkyl" include: iso-propyl, isobutyl, isopentyl, and isohexyl.
Additional non-limiting examples of "alkyl" include: sec-butyl, sec-pentyl, and sec-hexyl.
Additional non-limiting examples of "alkyl" include: tert-butyl, tert-pentyl, and tert-hexyl.
Additional non-limiting examples of "alkyl" include: neopentyl, 3-pentyl, and active pentyl.
In an alternative embodiment the "alkyl" group is optionally substituted.
In an alternative embodiment the "alkenyl" group is optionally substituted.

In an alternative embodiment the "alkynyl" group is optionally substituted.

Embodiments of "Haloalkyl"

In one embodiment "haloalkyl" is a C$_1$-C$_{10}$haloalkyl, C$_1$-C$_9$haloalkyl, C$_1$-C$_8$haloalkyl, C$_1$-C$_7$haloalkyl, C$_1$-C$_6$haloalkyl, C$_1$-C$_5$haloalkyl, C$_1$-C$_4$haloalkyl, C$_1$-C$_3$haloalkyl, and C$_1$-C$_2$haloalkyl.

In one embodiment "haloalkyl" has one carbon.
In one embodiment "haloalkyl" has one carbon and one halogen.
In one embodiment "haloalkyl" has one carbon and two halogens.
In one embodiment "haloalkyl" has one carbon and three halogens.
In one embodiment "haloalkyl" has two carbons.
In one embodiment "haloalkyl" has three carbons.
In one embodiment "haloalkyl" has four carbons.
In one embodiment "haloalkyl" has five carbons.
In one embodiment "haloalkyl" has six carbons.
Non-limiting examples of "haloalkyl" include:

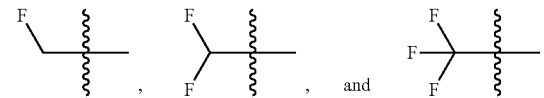

Additional non-limiting examples of "haloalkyl" include:

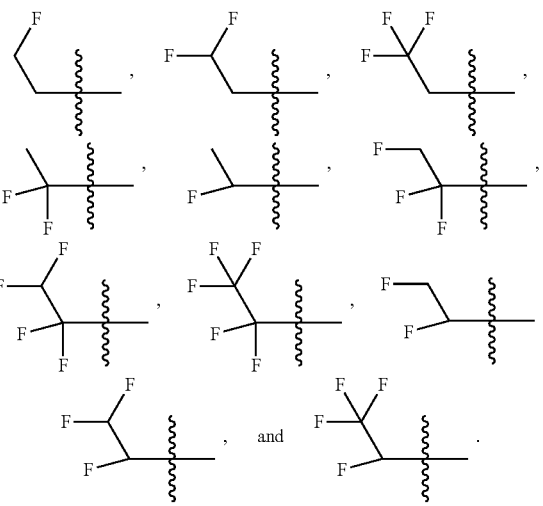

Additional non-limiting examples of "haloalkyl" include:

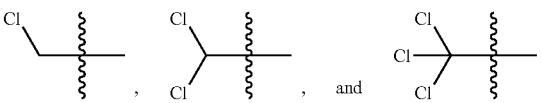

Additional non-limiting examples of "haloalkyl" include:

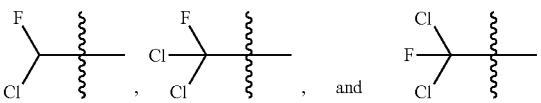

Embodiments of "Heteroaryl"

Non-limiting examples of 5 membered "heteroaryl" groups include pyrrole, furan, thiophene, pyrazole, imidazole, triazole, isoxazole, oxazole, oxadiazole, oxatriazole, isothiazole, thiazole, thiadiazole, and thiatriazole.

Additional non-limiting examples of 5 membered "heteroaryl" groups include:

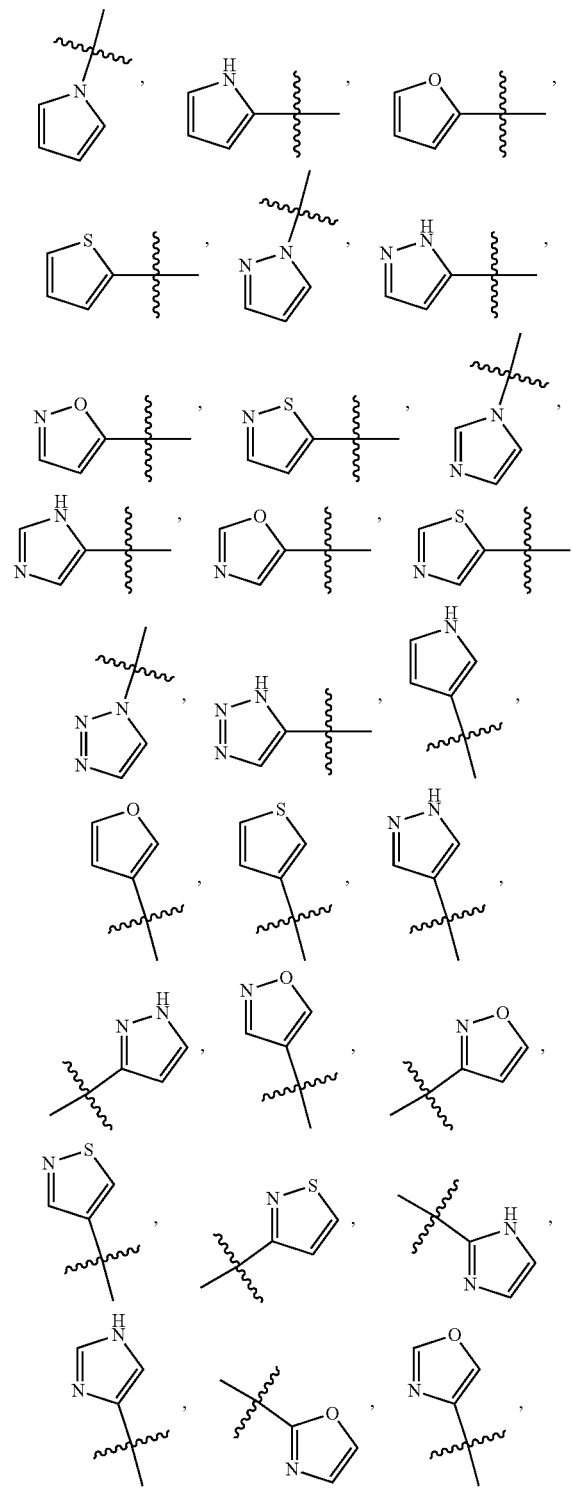

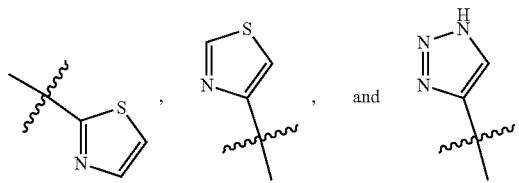

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

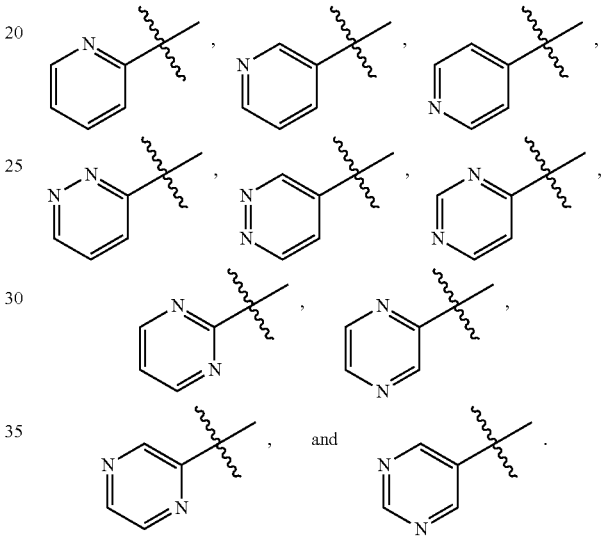

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

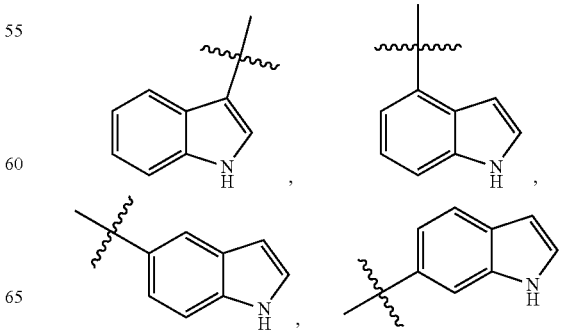

-continued

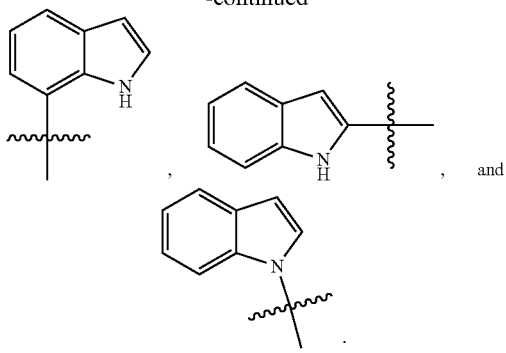

Additional non-limiting examples of "heteroaryl" groups that are bicyclic include:

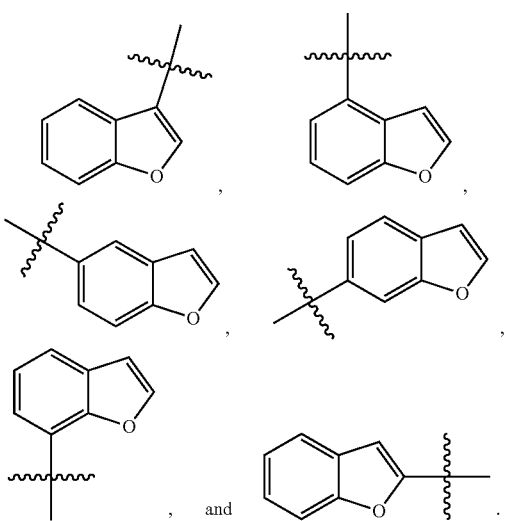

Additional non-limiting examples of "heteroaryl" groups that are bicyclic include:

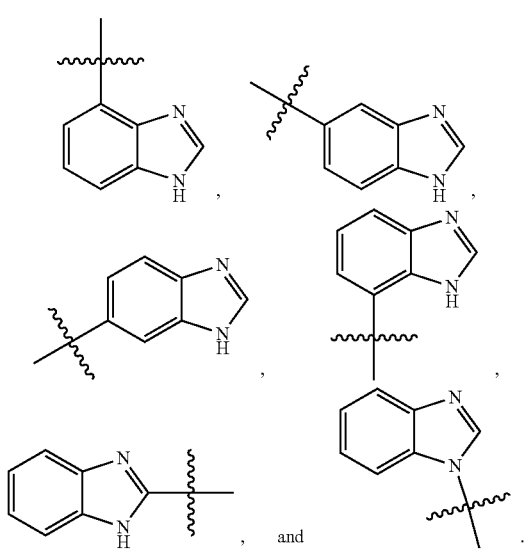

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

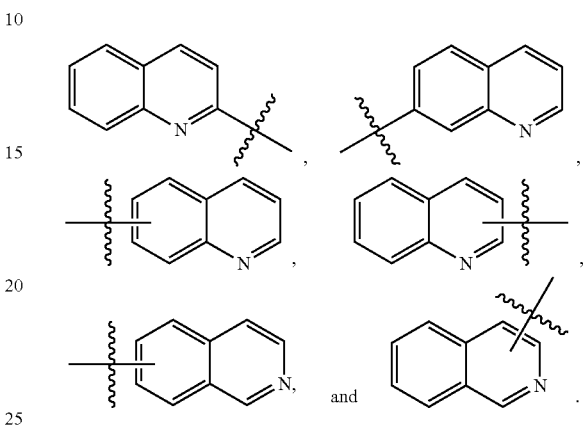

Embodiments of "Heterocycle"

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocyclic ring.

For example,

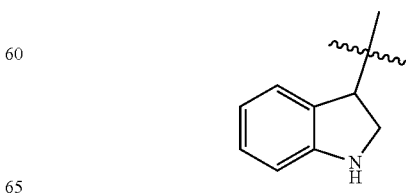

is a "heterocycle" group.

However,

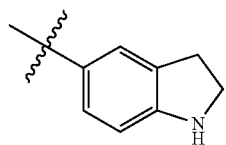 [SMILES: *c1ccc2c(c1)CCN2]

is an "aryl" group.

Non-limiting examples of "heterocycle" also include:

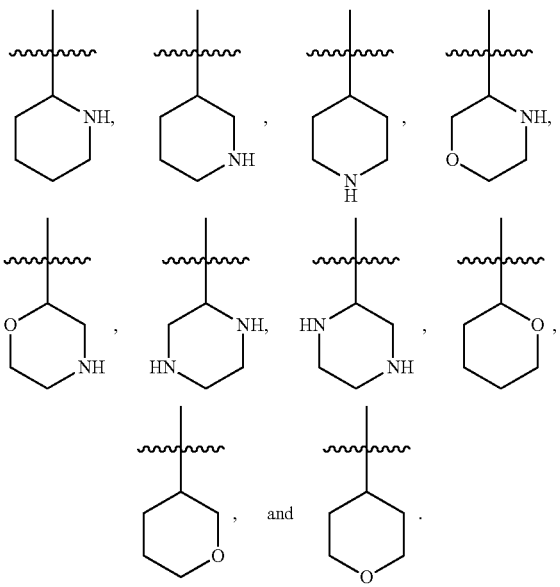

Additional non-limiting examples of "heterocycle" include:

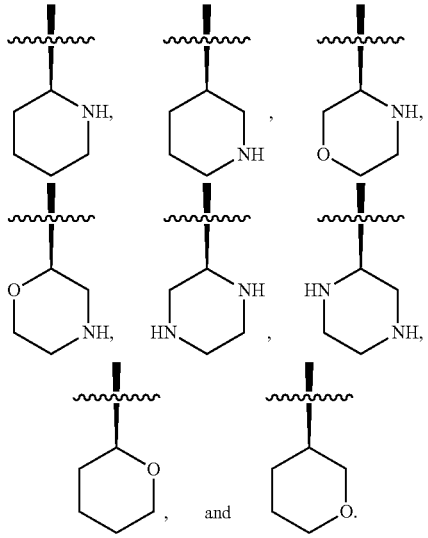

Additional non-limiting examples of "heterocycle" include:

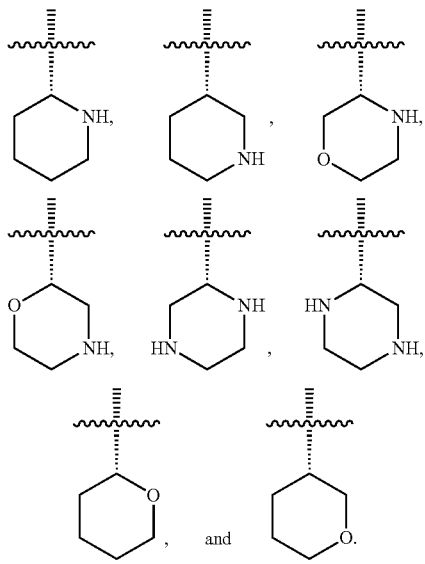

Non-limiting examples of "heterocycle" also include:

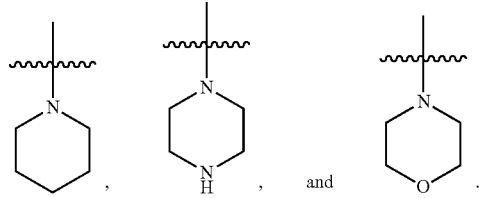 [SMILES: *N1CCCCC1 ; *N1CCNCC1 ; *N1CCOCC1]

Non-limiting examples of "heterocycle" also include:

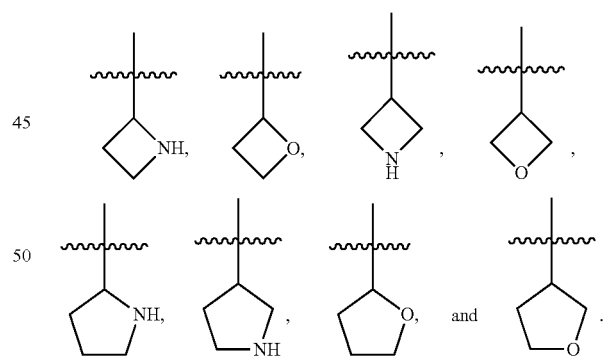

Additional non-limiting examples of "heterocycle" include:

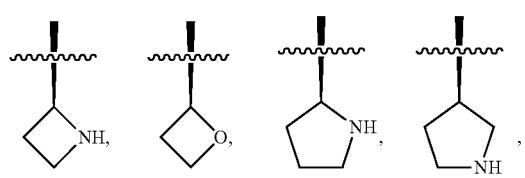

-continued

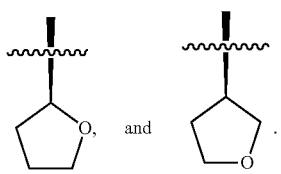

Additional non-limiting examples of "heterocycle" include:

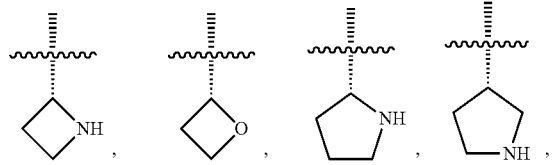

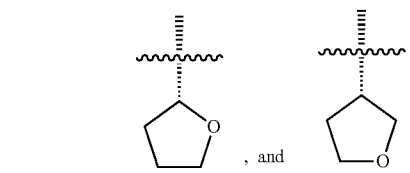

Aryl

In one embodiment "aryl" is a 6 carbon aromatic group (phenyl).

In one embodiment "aryl" is a 10 carbon aromatic group (naphthyl).

In one embodiment "aryl" is a 6 carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example

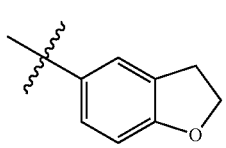 [SMILES: *c1ccc2c(c1)CCO2]

is an "aryl" group.

However,

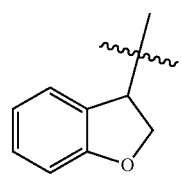 [SMILES: *C1COc2ccccc21]

is a "heterocycle" group.

Embodiments of "Arylalkyl"

Non-limiting examples of "arylalkyl" include:

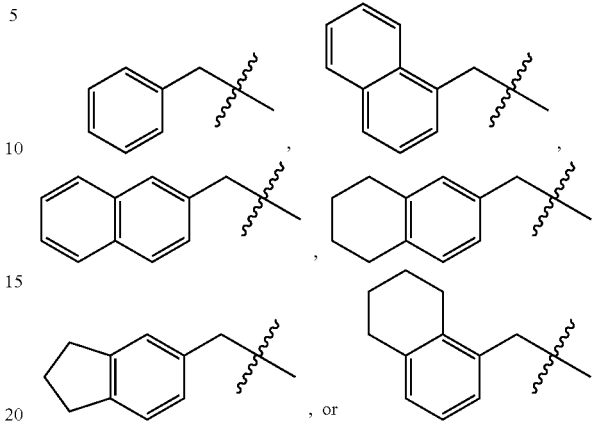

In one embodiment "arylalkyl" is

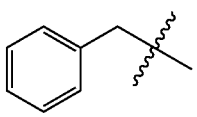

In one embodiment the "arylalkyl" refers to a 2 carbon alkyl group substituted with an aryl group.

Non-limiting examples of "arylalkyl" include:

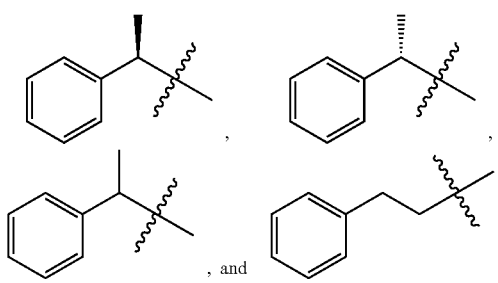

II. Extracellular Protein Degradation

A wide range of well-known and characterized extracellular proteins can cause, modulate, or amplify diseases in vivo, such as abnormal cellular proliferation such as tumors and cancer, autoimmune disorders, inflammation and aging-related diseases. For example, extracellular proteins such as growth factors, cytokines, and chemokines bind to cell surface receptors, often initiate aberrant signaling in multiple diseases such as cancer and inflammation.

An extracellular protein degrader described herein or its pharmaceutically acceptable salt and/or its pharmaceutically acceptable compositions can be used to treat a disorder which is mediated by the Target Extracellular Protein that binds to the Extracellular Protein Targeting Ligand. The described degraders are capable of targeting specific Extracellular Proteins that mediate pathological disorders for lysosomal degradation. The Target Extracellular Protein may modulate a disorder in a human via a mechanism of action such as modification of a biological pathway, pathogenic signaling, or modulation of a signal cascade or cellular entry. In one embodiment, the Target Extracellular Protein is a protein that is not druggable in the classic sense in that it does not have a binding pocket or an active site that can be inhibited or otherwise bound, and cannot be easily allosterically controlled. In another embodiment, the Target Extracellular Protein is a protein that is druggable in the classic sense, yet for therapeutic purposes, degradation of the protein is preferred to inhibition. The Target Extracellular Protein is recruited with an Extracellular Protein Targeting Ligand, which is a ligand for the Target Extracellular Protein. Typically, the Extracellular Protein Targeting Ligand binds the Target Extracellular Protein in a non-covalent fashion. In an alternative embodiment, the Target Extracellular Protein is covalently bound to the Extracellular Protein Targeting Ligand in a covalent manner that can be irreversible or reversible.

Accordingly, in some embodiments, a method to treat a host with a disorder mediated by a Target Extracellular Protein is provided that includes administering an effective amount of a degrader targeting the Target Extracellular Protein to the host, typically a human, optionally in a pharmaceutically acceptable composition.

The Target Extracellular Protein can be any amino acid sequence to which the degrader comprising an Extracellular Protein Targeting Ligand can be bound which through degradation thereof, results in a beneficial therapeutic effect. In one embodiment, the Target Extracellular Protein is a non-endogenous peptide such as that from a pathogen or toxin. In another embodiment, the Target Extracellular Protein can be an endogenous protein that mediates a disorder. The endogenous protein can be either the normal form of the protein or an aberrant form. For example, the Target Extracellular Protein can be an extracellular mutant protein, or a protein, for example, where a partial, or full, gain-of-function or loss-of-function is encoded by nucleotide polymorphisms. In some embodiments, the degrader targets the aberrant form of the protein and not the normal form of the protein.

The Extracellular Protein Targeting Ligand is a ligand which covalently or non-covalently binds to a Target Extracellular Protein which has been selected for lysosomal degradation. In certain embodiments the Extracellular Protein Targeting Ligand is a small molecule or moiety (for example a peptide, nucleotide, antibody fragment, aptamer, biomolecule, or other chemical structure) that binds to a Target Extracellular Protein, and wherein the Target Extracellular Protein is a mediator of disease in a host as described in detail below. Exemplary Extracellular Protein Targeting Ligands are provided in the Figures.

Anchor Bond

The Extracellular Protein Targeting Ligand ("EPTL") is covalently bound to Linker in the ASGPR-binding extracellular protein degrader compound through the Anchor Bond (which is the chemical bond between the EPTL and either Linker B, Linker C or Linker D). This bond can be placed at any location on the ligand that does not unacceptably disrupt the ability of the EPTL to bind to the Target Extracellular Protein. The Anchor Bond is depicted on the nonlimiting examples of Extracellular Protein Target Ligands in the figures as:

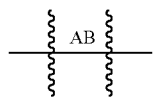 [SMILES: **]

A number of exemplary Target Extracellular Proteins for medical therapy described below have characterizing structural information in the well-known Protein Data Bank ("PDB"), which is a database for the three-dimensional structural information for large biological molecules such as proteins and nucleic acids. PDB includes x-ray crystallography and other information submitted by scientists around the world, and is freely accessible. See for example www.rcsb.org; www.wwpdb.org and www.uniprot.org. Using the PDB codes for example provided in Section ** or in the Data Bank itself, and technical references provided herein or otherwise publicly available, the skilled artisan can determine appropriate locations where the EPTL can be linked through an Anchor Bond to Linker B, Linker C or Linker D to the ASGPR-binding moiety. For many of these proteins, published references describe how a range of ligands bind to the Target Extracellular Proteins, and from this information, one can determine reasonable Anchor Bond locations.

For example, the skilled artisan can use available visualization tools, including those available on the PDB website, to determine where the Extracellular Protein Targeting Ligand docks into to the Target Extracellular Protein. The skilled artisan can also import the crystal structure and the selected Extracellular Protein Targeting Ligand of interest into modeling software (including for example PyMOL, Glide, Maestro, RasMol, Visual Molecular Dynamics, Jmol, and AutoDock) to determine what portion of the Extracellular Protein Targeting Ligand is bound to the Target Extracellular Protein. The ASGPR ligand is then bound through the Linker and the Anchor Bond at a point that does not unduly adversely affect binding to the Target Extracellular Protein.

Optional Substituents

In certain embodiments an Extracellular Protein Targeting Ligand described herein, for example in one of the figures, is optionally substituted with 1, 2, 3, or 4 optional substituents independently selected from alkyl (including $C_1$-$C_4$alkyl), alkenyl (including $C_2$-$C_4$alkenyl), alkynyl (including $C_2$-$C_4$alkynyl), haloalkyl (including $C_1$-$C_4$haloalkyl), —$OR^6$, F, Cl, Br, I, —$NR^6R^7$, heteroalkyl, cyano, nitro, $C(O)R^3$,

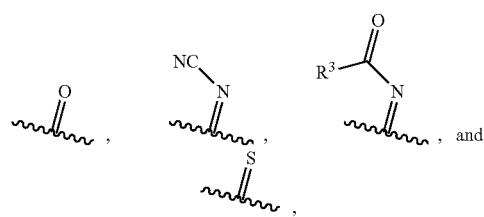

wherein the optional substituent is selected such that a stable compound results.

In certain embodiments the Target Extracellular Protein is selected from IgA, IgG, IgE, TNF-alpha, IL-1, IL-2, IL-6, IFN-γ, VEGF, TGF-β1, PCSK-9, CPB2, ChE, CCL2, Factor VII, Factor IX, CD40L, Factor Xa, Factor XI, Factor XIa, Factor XII, Factor XIII, FGF1, FGF2, FN1, IL-5, IL-8, IL-10, IL-21, IL-22, Kallikrein 1, LPL, MMP1, MIF, GIF, L-dopachrome isomerase, or phenylpyruvate tautomerase, neutrophil elastase, Prothrombin, KLKB1, PLG, PAI-1, endothelial plasminogen activator inhibitor, serpin E1, phospholipases A2, PLA2, PA21B, PLA2G1B, PLA2-IB, PLA2, PLA2A, PA2IIA, PLA2G2A, PLA2-IIA, PGF, plasminogen activator, tissue type (tPA, PLAT), Transforming growth factor beta 2 (TGF-β2, TGFB2), thrombospondin 1, Urokinase, Urokinase-type plasminogen activator, complement factor B, complement factor D, target complement factor H, and complement component 5.

In certain embodiments, where the Target Extracellular Protein has a receptor the Target Extracellular Protein can be used to degrade the receptor.

In certain embodiments the Extracellular Protein Targeting Ligand is selected from IgA, IgG, IgE, TNF-alpha, IL-1, IL-2, IL-6, IFN-γ, VEGF, TGF-β1, PCSK-9, CPB2, ChE, CCL2, Factor VII, Factor IX, CD40L, Factor Xa, Factor XI, Factor XIa, Factor XII, Factor XIII, FGF1, FGF2, FN1, IL-5, IL-8, IL-10, IL-21, IL-22, Kallikrein 1, LPL, MMP1, MIF, GIF, L-dopachrome isomerase, or phenylpyruvate tautomerase, neutrophil elastase, Prothrombin, KLKB1, PLG, PAI-1, endothelial plasminogen activator inhibitor, serpin E1, phospholipases A2, PLA2, PA21B, PLA2G1B, PLA2-IB, PLA2, PLA2A, PA2IIA, PLA2G2A, PLA2-IIA, PGF, plasminogen activator, tissue type (tPA, PLAT), Transforming growth factor beta 2 (TGF-β2, TGFB2), thrombospondin 1, Urokinase, Urokinase-type plasminogen activator, complement factor B, complement factor D, target complement factor H, and complement component 5.

Amino Acids

In certain embodiments the Extracellular Protein Targeting Ligand comprises one or more amino acids. The invention contemplates using natural amino acids, unnatural amino acids, or any combination thereof to achieve desired targeting ligand properties.

The term "natural amino acid" refers to an amino acid selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

In certain embodiments a natural amino acid is replaced with a corresponding unnatural amino acid for example substituting a phenylalanine for a 4-chloro-phenylalanine. Non-limiting examples of unnatural amino acids include: 4-chloro-phenylalanine, 3-fluoro-phenalalanine, 4-trifluoromethyl-phaenylalanine, 3,4-dichloro-phenylalanine, 4-phenyl-phenylalanine, N-methylalanine, N-methylglutamic acid, N-methylphenylalanine, and homoserine.

Additional examples of non-natural amino acids include:

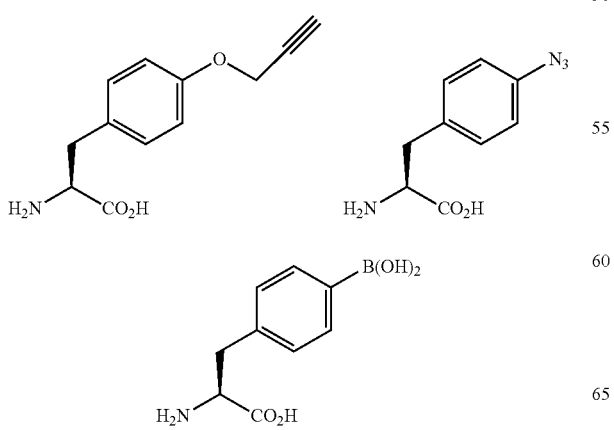

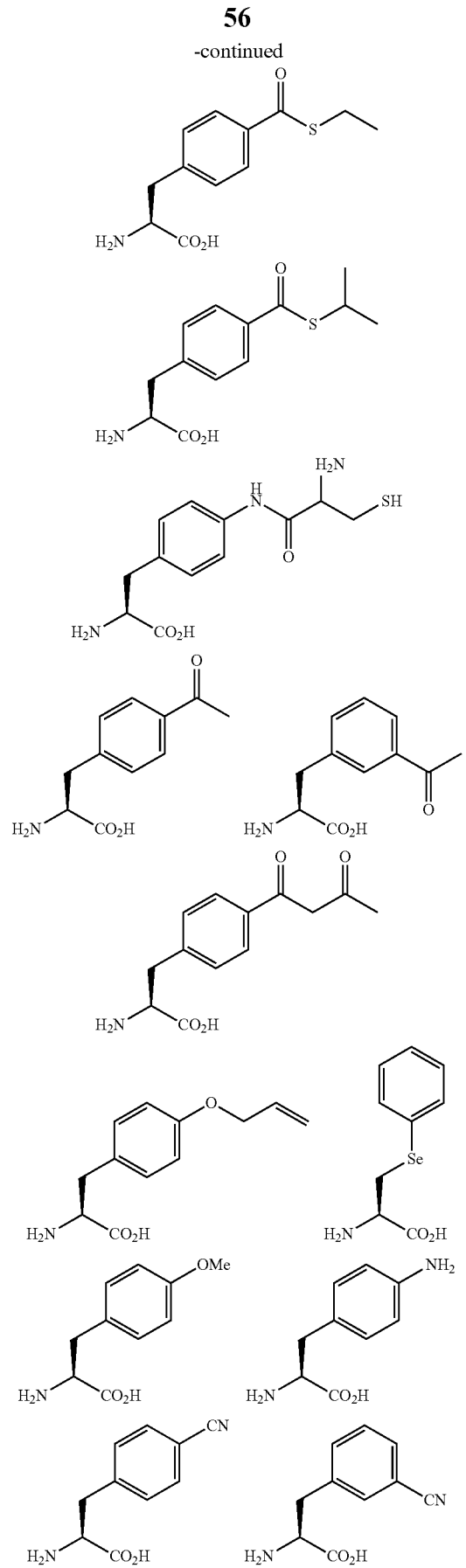

-continued
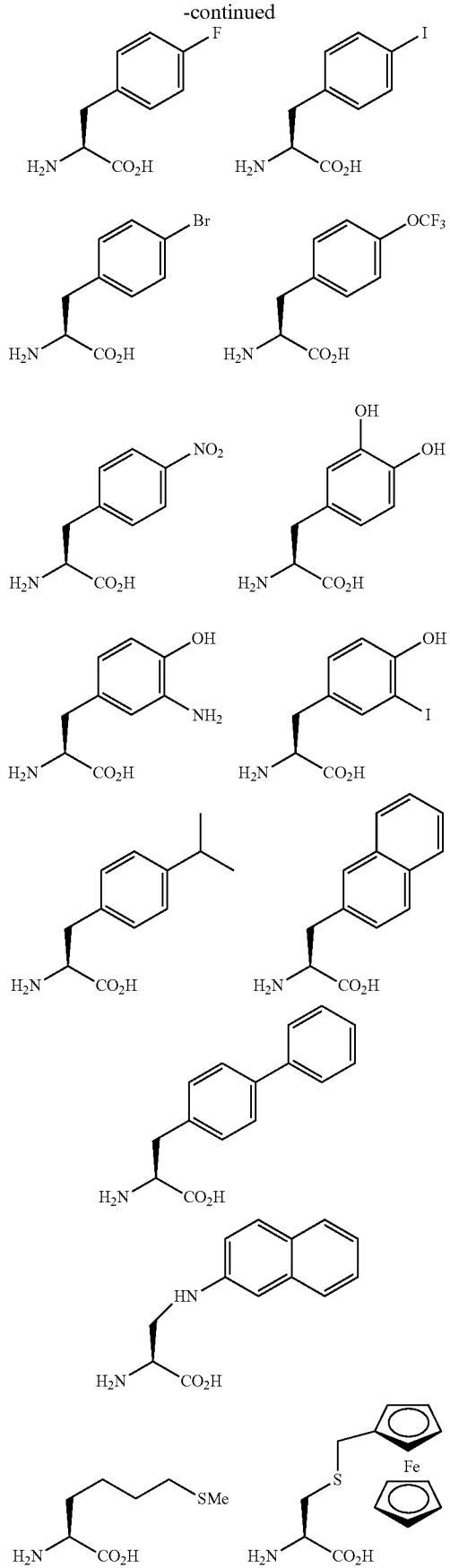
-continued
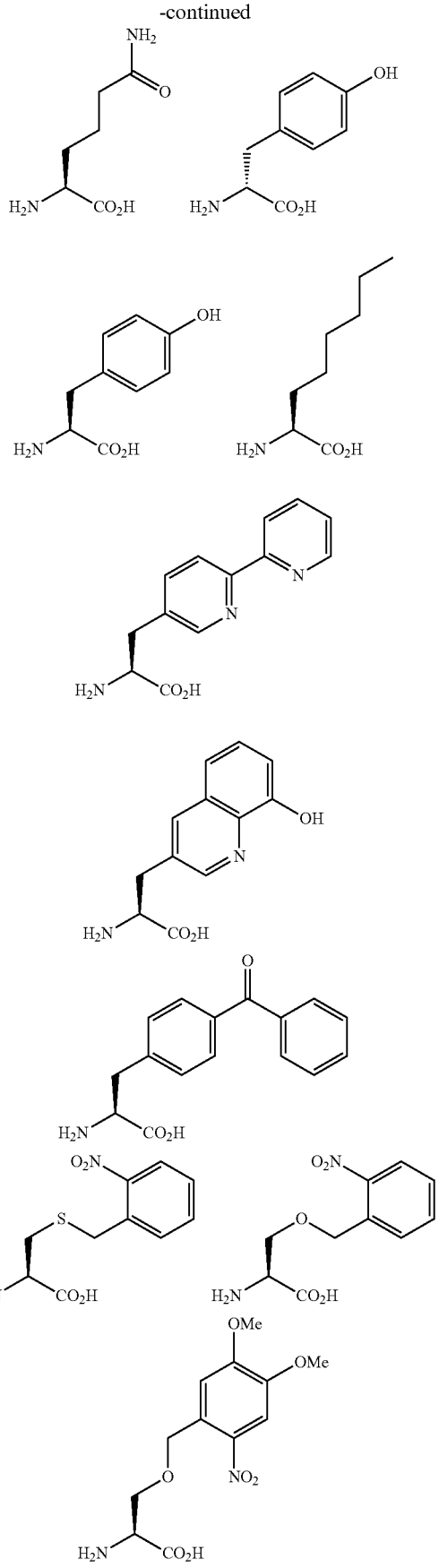

59
-continued
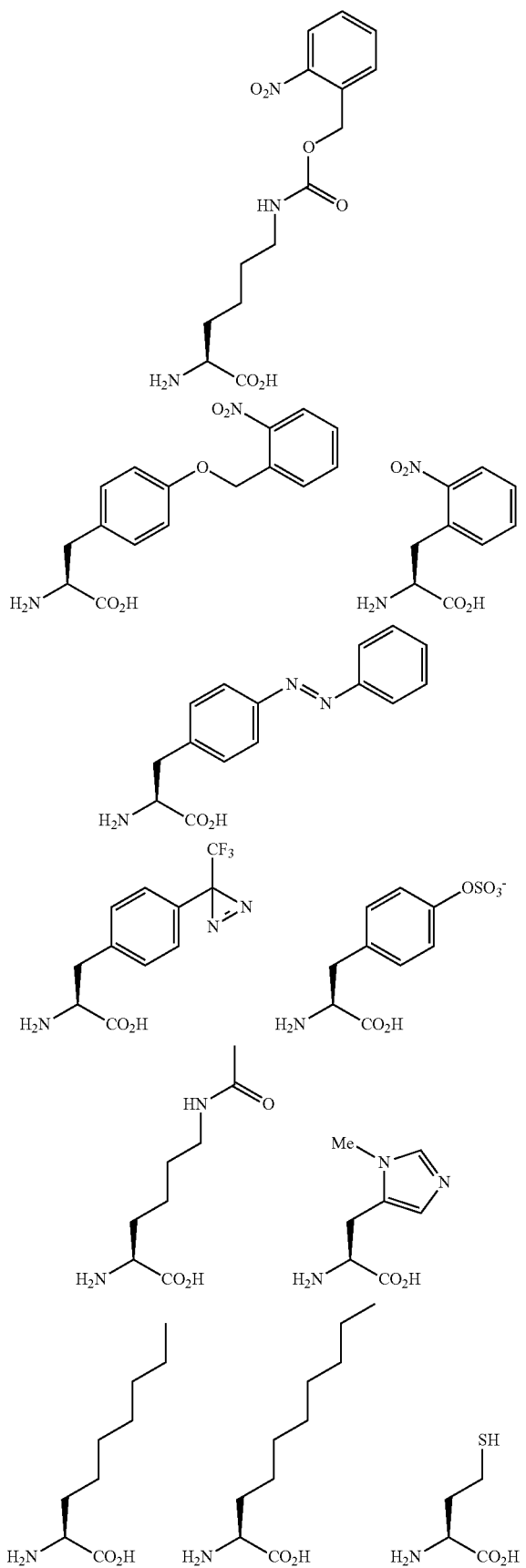
60
-continued
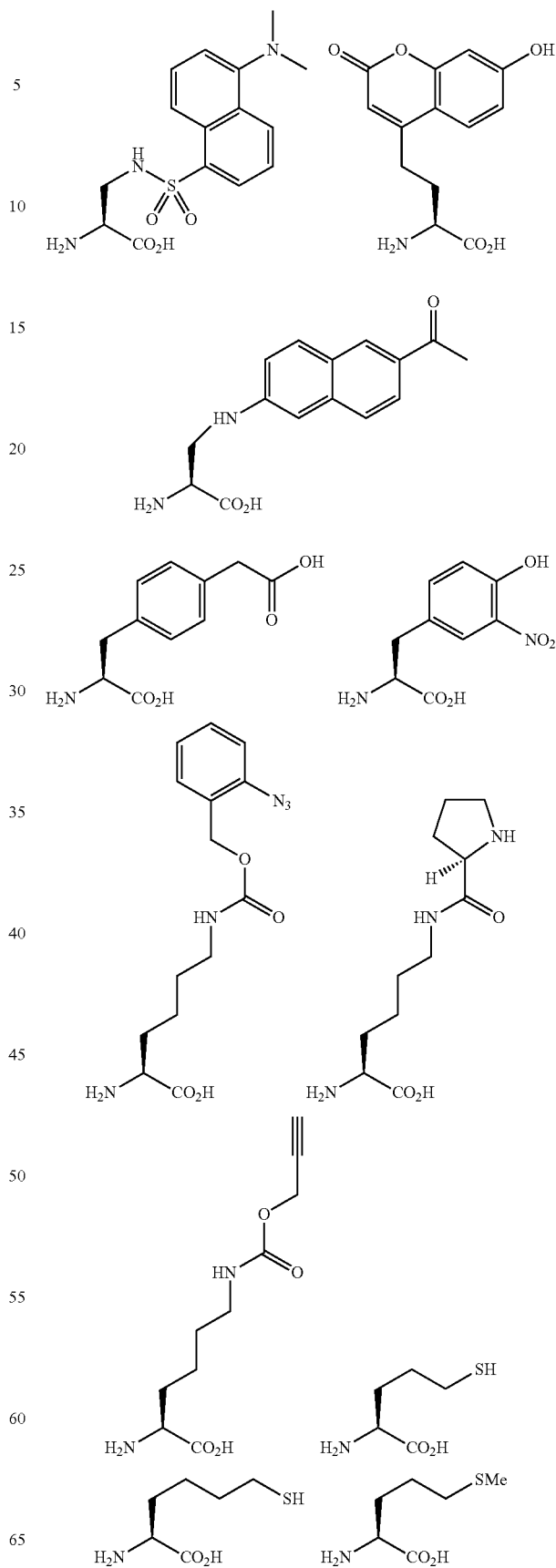

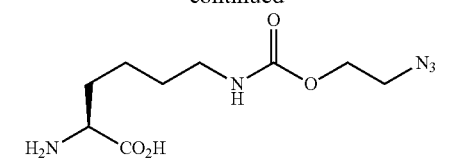

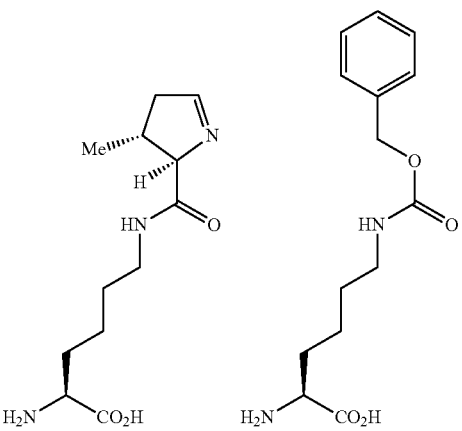

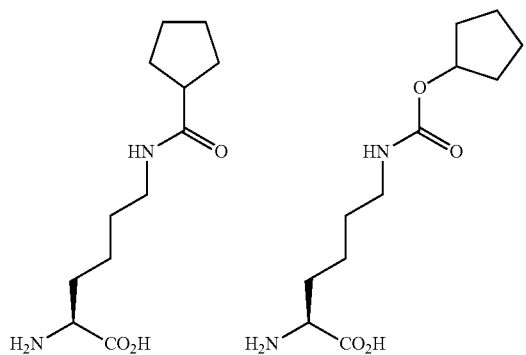

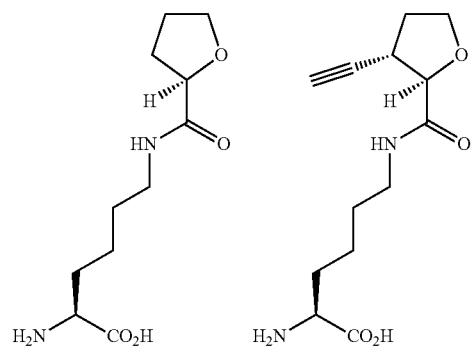

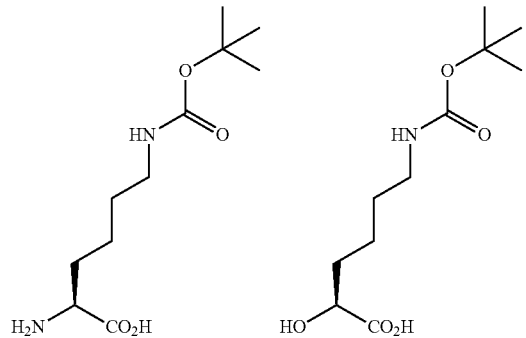

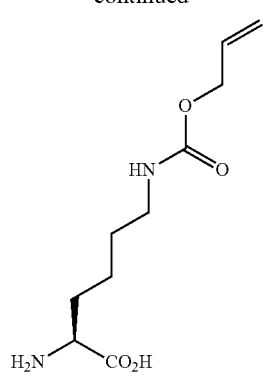

In certain embodiments the Extracellular Protein Targeting Ligand is a sequence of amino acids. In certain embodiments the amino acid sequence is connected to the Linker portion of the molecule by a bond to a terminal amine. In certain embodiments the amino acid sequence is connected to the Linker portion of the molecule by a bond to a terminal carboxylic acid (e.g. an ester or amide). In certain embodiments the peptide includes an amine, hydroxyl, or carboxylic acid side chain and the linker may be bound to one of these sidechains.

For example, when the amino acid sequence is SEQ ID NO: 1 MLKKIE non-limiting examples of locations wherein the peptide may be attached to the linker include:

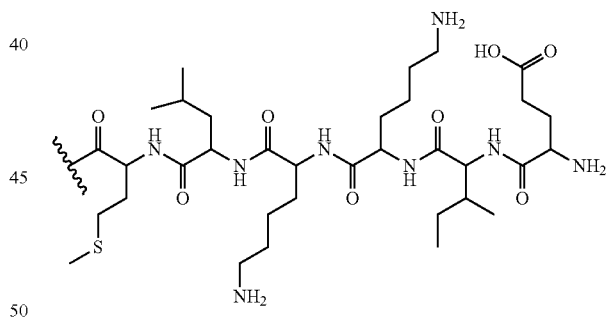

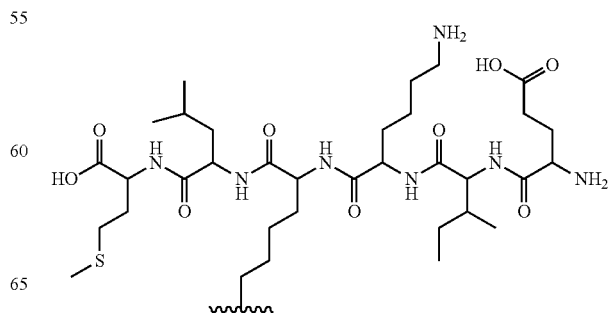

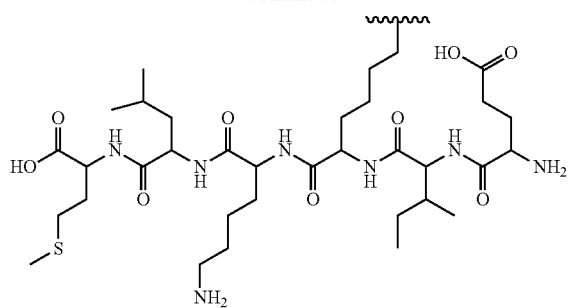

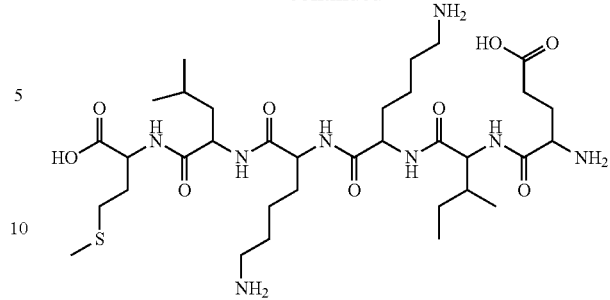

The amino acid sequence can be attached to the Linker with chemistry described herein and as otherwise known in the art. For example, when the desired linking group is an amide the linker can be presented with an amine, carboxylic acid, ester or other amide precursor and the targeting ligand can be attached with an amide coupling reaction such as a HATU or HBTU coupling reaction.

Non-limiting examples of Extracellular Protein Targeting Ligands that are a sequence of amino acids include aptamers, antibodies, and peptides. In certain embodiments the left most amino acid listed in the sequence listing is the C-terminus. In other embodiments the right most amino acid listed in the sequence listing is the C-terminus.

In certain embodiments the amino acid sequence refers to a sequence without specified chirality. In other embodiments the amino acid sequence is all D-, all L-, or a mixture of D- and L-amino acids.

When peptides are denoted by an amino acid sequence in a structure drawn herein the left side of the peptide is typically the N-terminus and the right side is typically the C-terminus unless excluded by context. For example, the proline in PIESESLK is attached through the nitrogen of the N-terminus to the linker in the structure below.

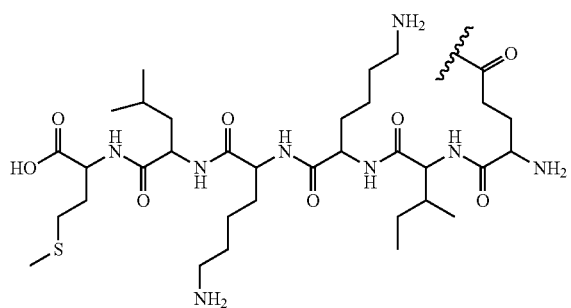

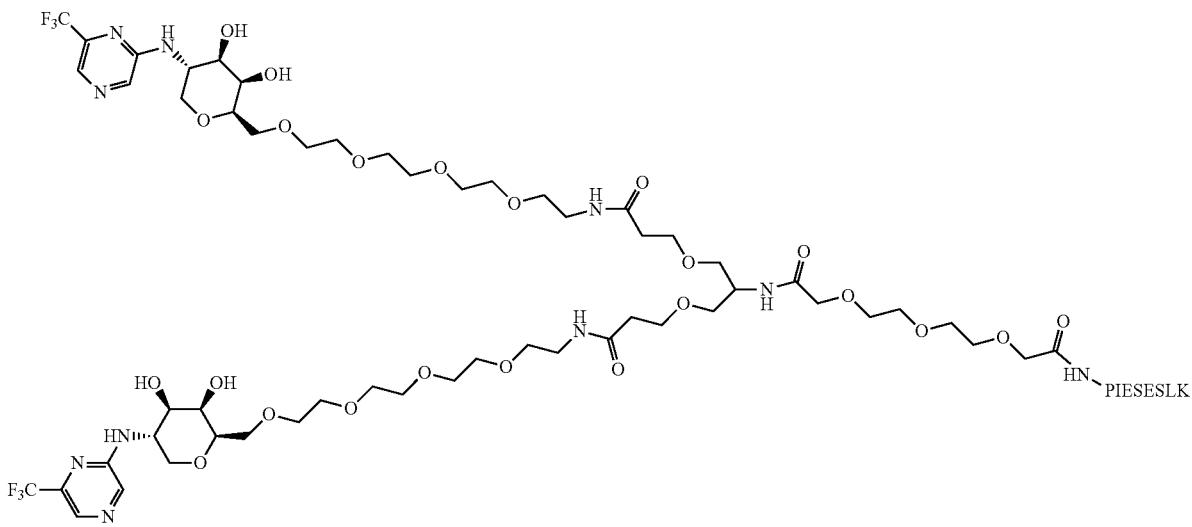

For clarity the NH that is part of the amide is part of proline and the CO is part of the linker.

When the lysine in PIESESLK is attached through the carbonyl of the C-terminus to the linker in the structure below.

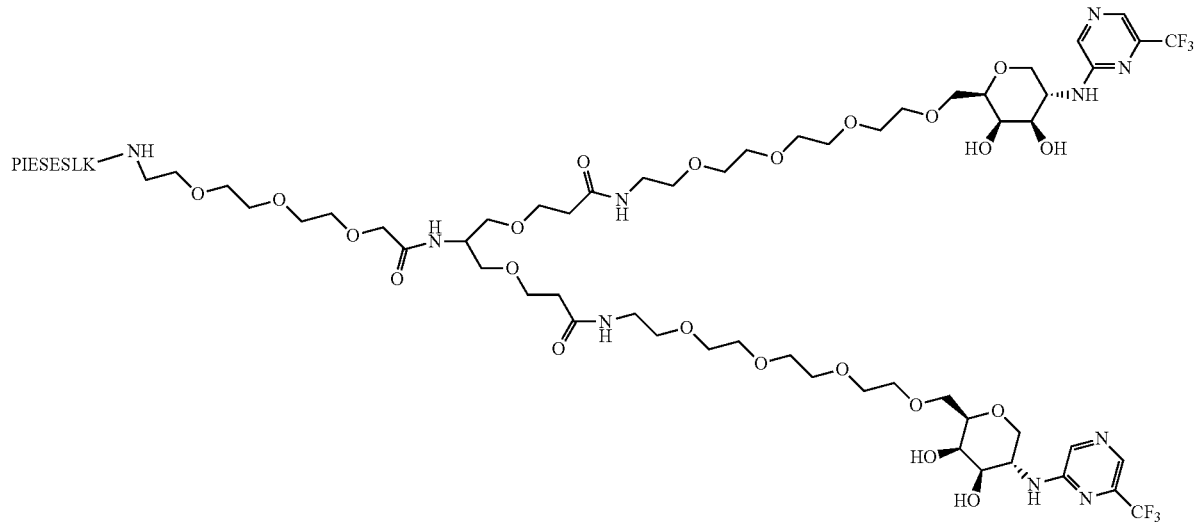

For clarity the NH that is bound to the lysine is part of the linker and the lysine is bound to the NH by the carbonyl that is part of the C-terminus.

TNF-Alpha (TNF-α)

In some embodiments, the Target Extracellular Protein is human TNF-α (UniProtKB—P01375 (TNFA_HUMAN)). TNF-α is a pro-inflammatory cytokine active in the bodily immune response and serious inflammatory diseases. TNF-α has been implicated in a number of disorders, including but not limited to rheumatoid arthritis, inflammatory bowel disease, graft-vs-host disease, ankylosing spondylitis, psoriasis, hidradenitis suppurativa, refractory asthma, systemic lupus erthyematosus, diabetes, and the induction of cachexia.

The Protein Data Bank website provides the crystal structure of TNF-α searchable by 6RMJ (Valentinis, B., et al., Int. J. Mol. Sci., 2019, 20); 5UUI (Carrington et al., Biophys J., 2017, 113 371-380); 6OOY, 6OOZ and 6OPO (O'Connell, J., et al., Nat. Commun., 2019, 10 5795-5795); and 5TSW (Cha, S. S., J Biol Chem., 1998, 273 2153-2160); as well as the crystal structure of TNF-α bound to various compounds searchable by 5YOY (Ono et al., Protein Sci., 2018, 27 1038-1046); 2AZ5 (He., M. M., et al., Science, 2005, 310: 1022-1025); 5WUX (Lee, J. U., Int J Mol Sci., 2017, 18); 5MU8 (Blevitt et al., J Med Chem., 2017, 60 3511-3517); 4Y60 (Feldman J. L., et al., Biochemistry, 2015, 54 3037-3050); 3WD5 (Hu, S., et al., J Biol Chem, 2013, 288 27059-27067); and 4G3Y (Liang, S. Y., J Biol Chem., 2013, 288 13799-13807).

Representative TNF-α Targeting Ligands are provided in FIG. 1. Additional TNF-α Targeting Ligands can be found in, for example, U.S. Pat. No. 8,541,572; J Chem Inf Model. 2017 May 22; 57(5): 1101-1111; each of which is incorporated by reference herein.

In certain embodiments the TNF-alpha Targeting Ligand is selected from:

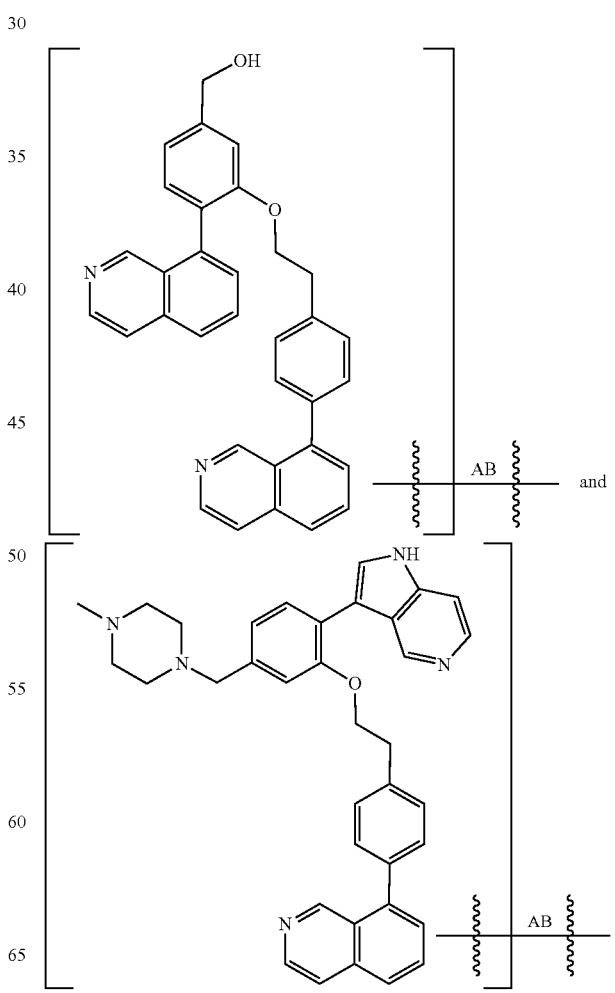

and

In certain embodiments the TNF-alpha Targeting Ligand is selected from:
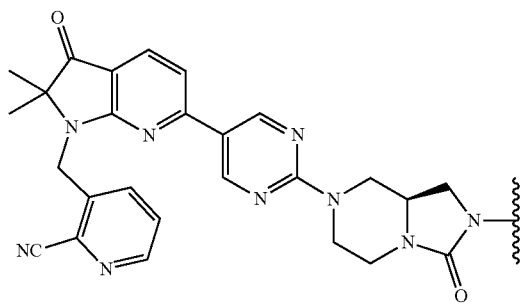
and
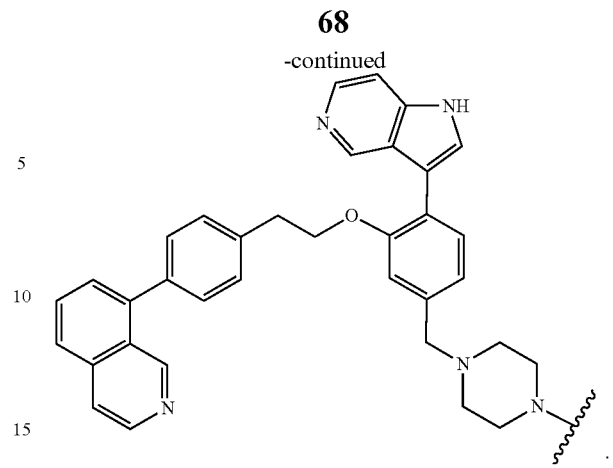
Non-limiting examples of TNFa degrading compounds include:
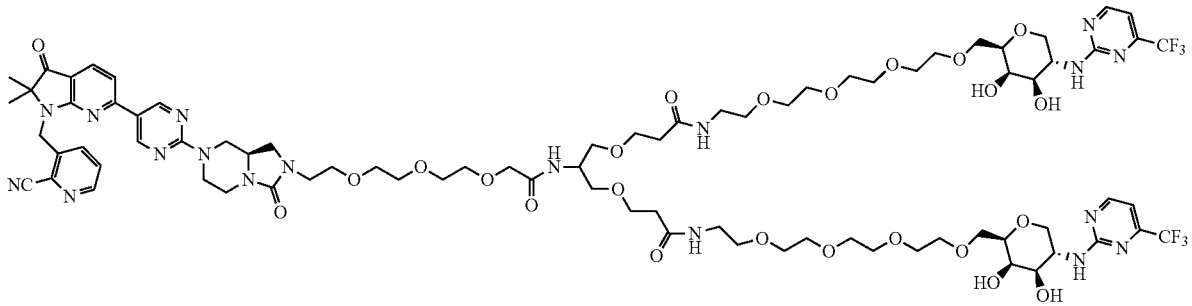
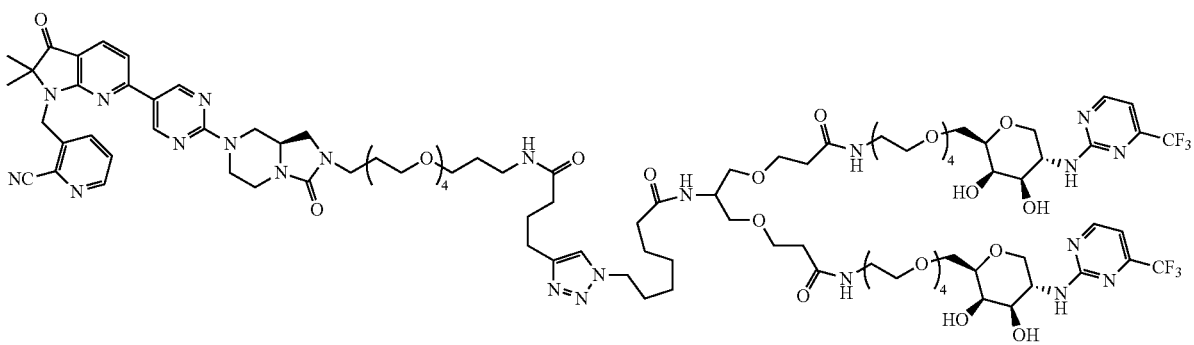
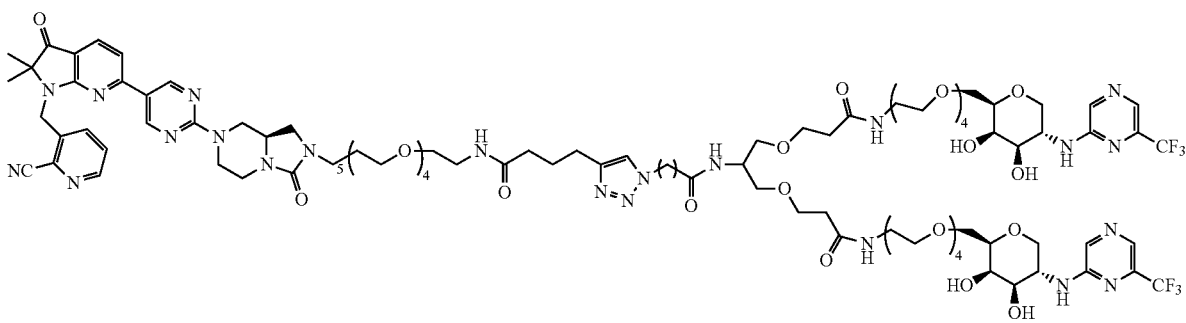

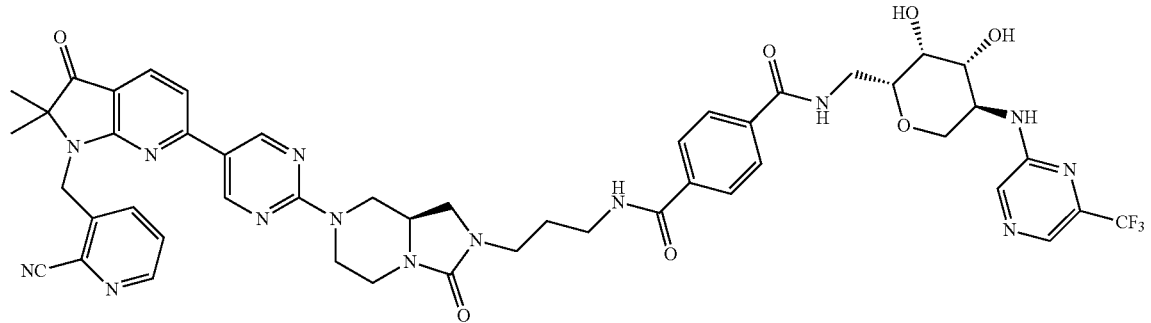
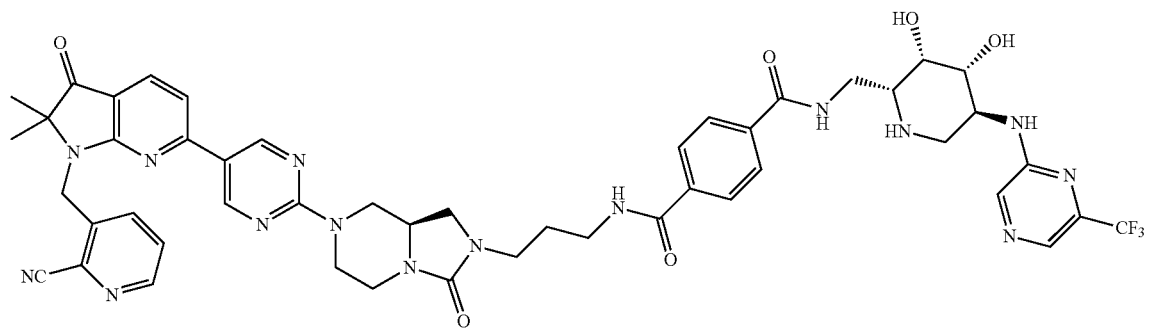
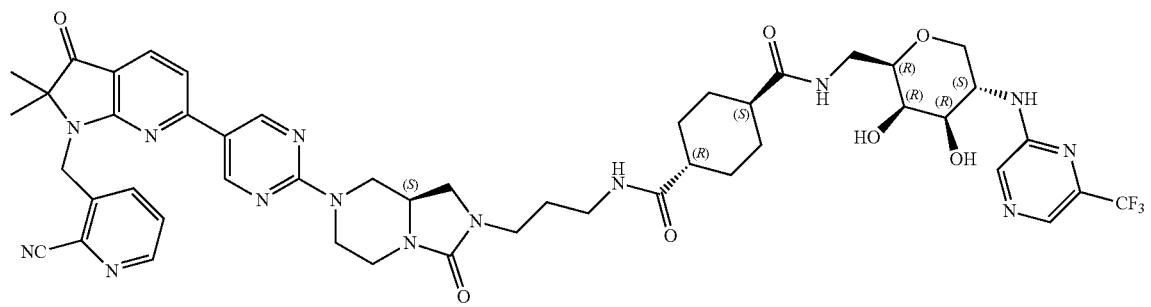
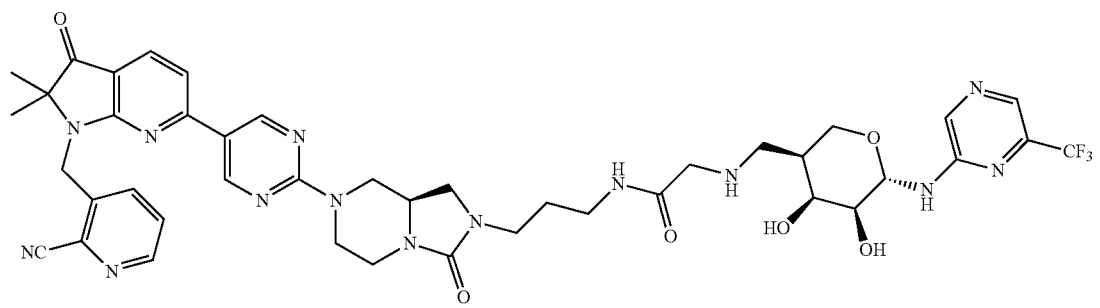
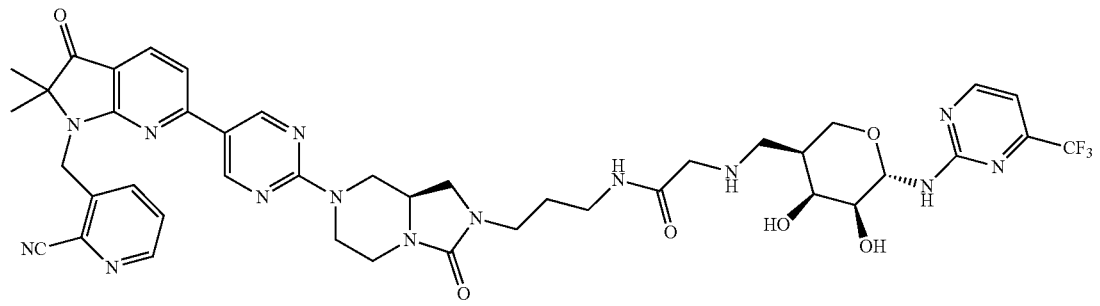

-continued
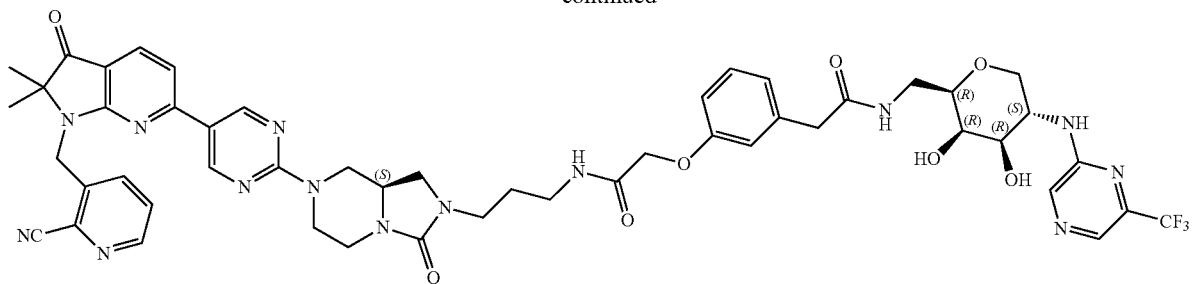
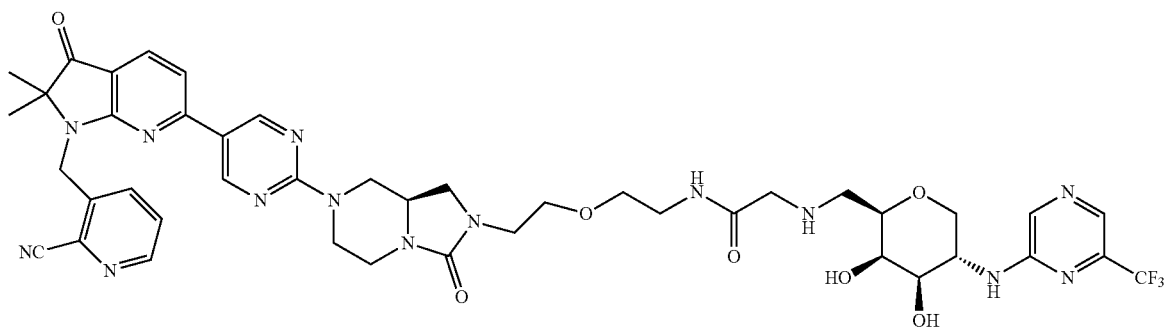
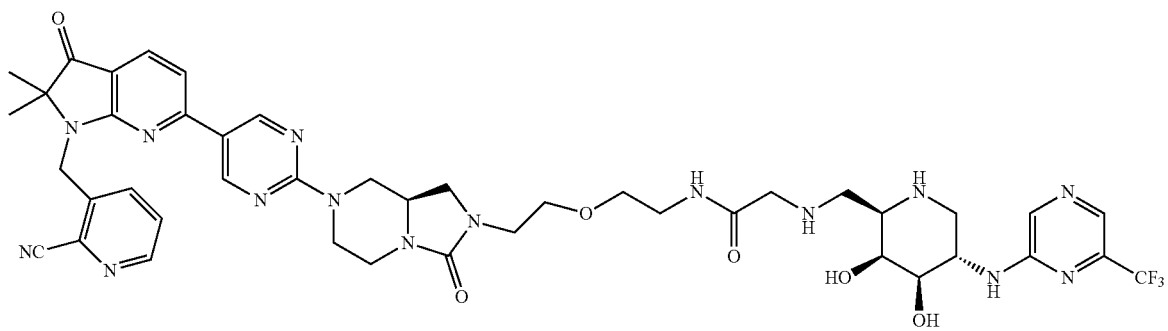
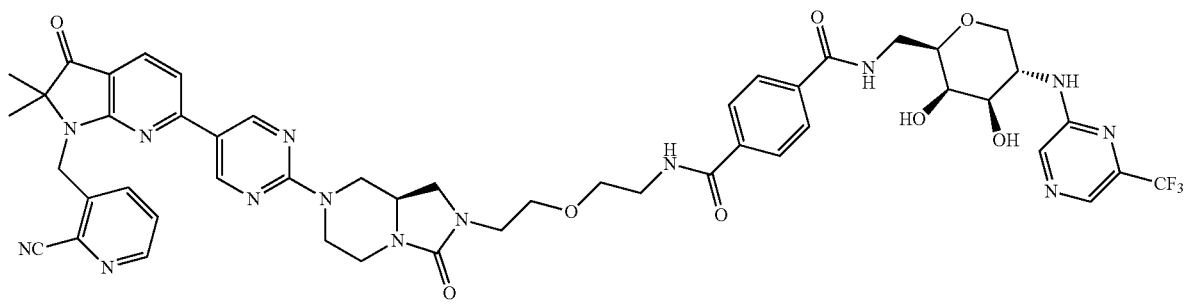
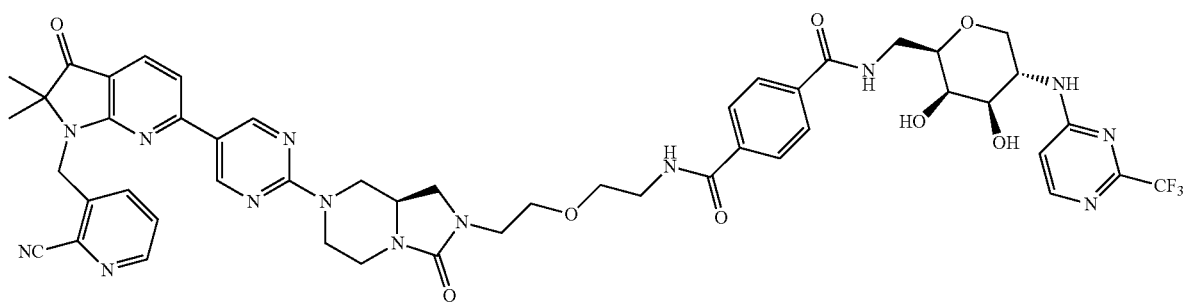

-continued
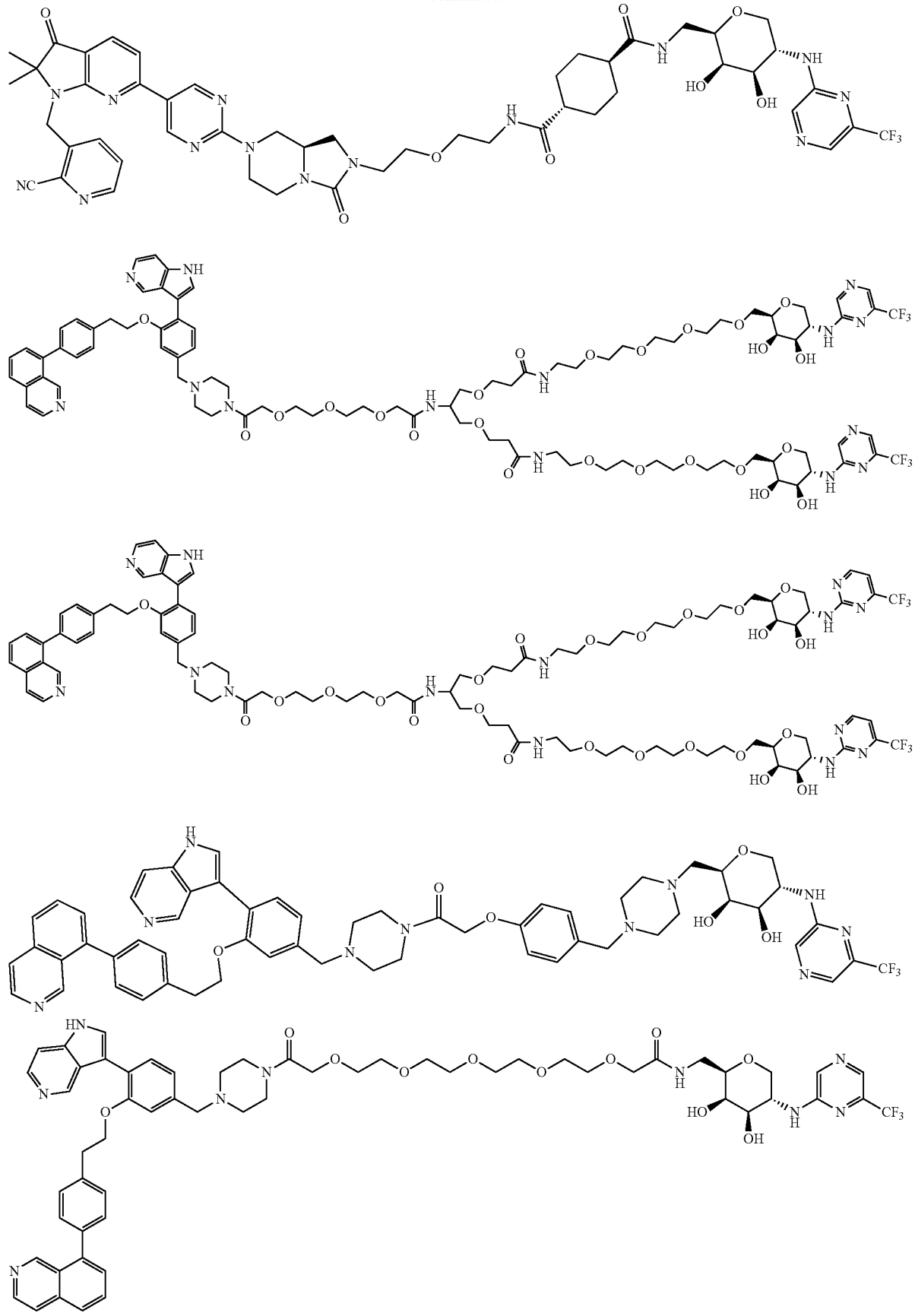

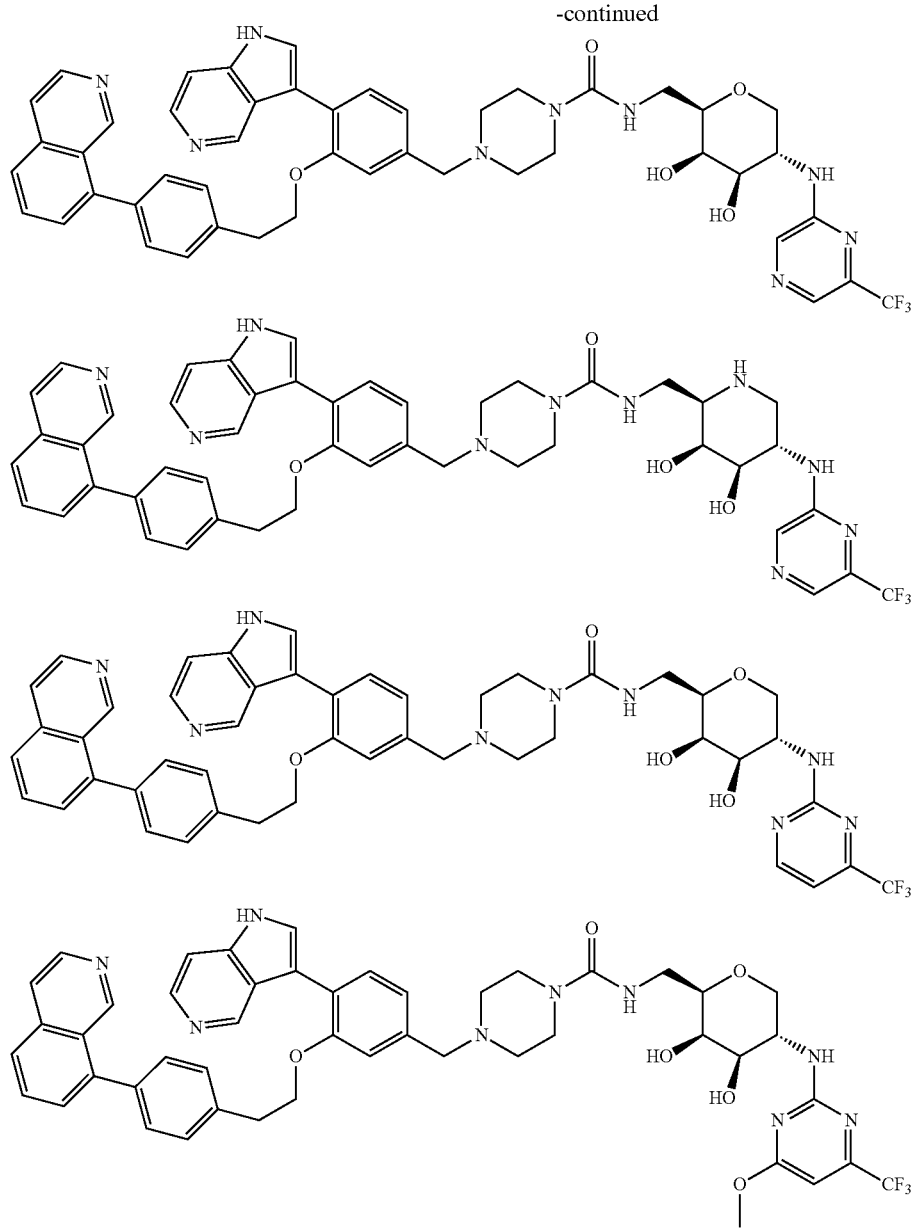

IL-1

In some embodiments, the Target Extracellular Protein is human interleukin-1 (IL-1) (UniProtKB—P01584 (IL1B_HUMAN)). IL-1 is a potent proinflammatory cytokine. Initially discovered as the major endogenous pyrogen, induces prostaglandin synthesis, neutrophil influx and activation, T-cell activation and cytokine production, B-cell activation and antibody production, and fibroblast proliferation and collagen production. IL-1 promotes Th17 differentiation of T-cells, and Synergizes with IL12/interleukin-12 to induce IFNG synthesis from T-helper 1 (Th1) cells. IL-1 has been implicated in a number of auto-inflammatory and autoimmune disorders, including, but not limited to, Blau syndrome, cryopyrin-associated periodic syndromes, familial Mediterranean fever, Majeed syndrome; mevalonate kinase deficiency syndrome, pyogenic arthritis-pyoderma gangrenosum-acne syndrome, tumor necrosis factor receptor-associated periodic syndrome, Behçet's Disease, Sjogren's Syndrome, gout and chondrocalcinosis, periodic fever, aphthous stomatitis, pharyngitis, and cervical adenitis (or PFAPA) syndrome, rheumatoid arthritis, Type 2 diabetes mellitus, acute pericarditis, Chronic interstitial lung diseases (ILDs), Still's Disease, The Protein Data Bank website provides the crystal structure of IL-1 searchable by 9ILB (Yu, B., et al., Proc Natl Acad Sci USA, 1999, 96 103-108); 1I1B (Finzel, B. C., et al., J Mol Biol., 1989, 209 779-791); and 3O4 O (Wang et al., Nat. Immunol., 2010, 11: 905-911); as well as the crystal structure of IL-1 bound to various compounds searchable by 4G6J (Blech, M., et al., J Mol Biol., 2013, 425 94-111); 5BVP (Rondeau e al., MAbs, 2015, 7 1151-1160); and 3LTQ (Barthelmes, K., et al., J Am Chem. Soc., 2011, 133 808-819). Additionally, Guy et al., provides insight into the crystal structure of a small antagonist peptide bound to interleukin-1 receptor type 1 (Guy et al., The Journal of Biological Chemistry, 2000, 275, 36927-36933).

Potential IL-1 direct or indirect inhibitors are described in FIG. 1. Additional IL-1 Targeting Ligands can be found in, for example, U.S. Pat. No. 9,694,015, each of which is incorporated herein by reference. Additional binding ligands include rilanocept or a binding fragment thereof (J Rheumatol. 2012; 39:720-727 (2012); and Canakinumab, or a binding fragment thereof (J Rheumatol. 2004; 31:1103-1111).

In certain embodiments the IL-1 Targeting Ligand is selected from

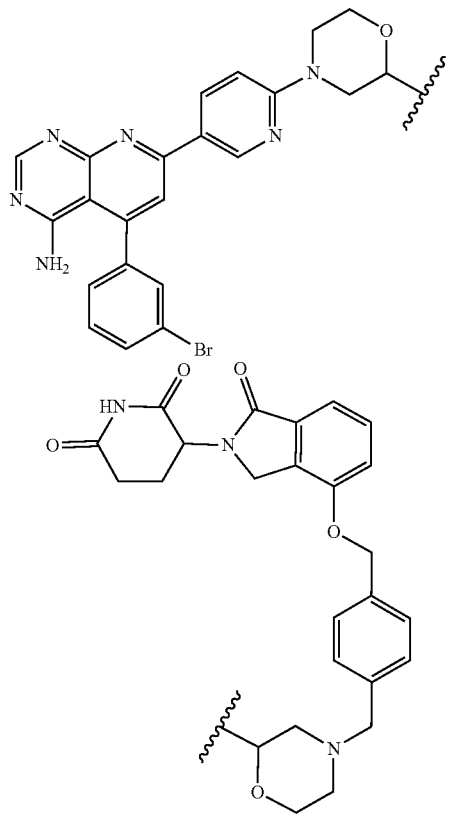

IL-2

In some embodiments, the Target Extracellular Protein is human interleukin-2 (IL-2) (UniProtKB—P60568 (IL2_HUMAN)). IL-2 is a potent pro-inflammatory cytokine. IL-2 has been implicated in host versus graft rejection and other autoimmune disorders.

The Protein Data Bank website provides the crystal structure of IL-2 searchable by 1M4C and 1M47 (Arkin, M. R., et al., Proc. Natl. Acad. Sci. USA, 2003, 100: 1603-1608); as well as the crystal structure of IL-2 bound to various compounds searchable by 4NEJ and 4NEM (Brenke, R., et al.); 1QVN (Thanos, C. D., et al., Proc Natl Acad Sci USA, 2006, 103 15422-15427); 1PW6 and 1PY2 (Thanos, C. D., et al., J Am Chem Soc., 2003, 125 15280-15281); 1NBP (Hyde, J., et al., Biochemistry, 2003, 42 6475-6483); and 1M48, 1M49, 1M4A, 1M4B, and 1M4C (Arkin, M. R., et al., Proc Natl Acad Sci USA, 2003, 100 1603-1608). Additionally, Stauber, D. J., et al, provides insight into the crystal structure of the IL-2 signaling complex: paradigm for a heterotrimeric cytokine receptor (Stauber, D. J., et al., PNAS, 2006, 103(8), 2788-2793).

Representative IL-2 Targeting Ligands are provided in FIG. 1. Additional IL-2 Targeting Ligands can be found in, for example, U.S. Pat. Nos. 8,802,721; 9,682,976, 9,708, 268; Eur J Med Chem 83: 294-306 (2014), J Med Chem 60: 6249-6272 (2017); Nature 450: 1001-1009 (2007); each of which is incorporated by reference herein.

In certain embodiments the IL-2 Targeting Ligand is selected from

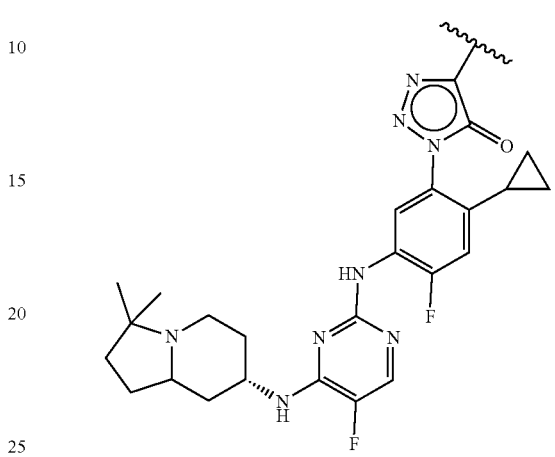

IL-6

In some embodiments, the Target Extracellular Protein is human interleukin-6 (IL-6) (UniProtKB—P05231 (IL6_HUMAN)). IL-6 is a cytokine with a wide variety of biological functions. It is a potent inducer of the acute phase response and plays an essential role in the final differentiation of B-cells into Ig-secreting cells. It is also involved in lymphocyte and monocyte differentiation. It also acts on B-cells, T-cells, hepatocytes, hematopoietic progenitor cells and cells of the CNS, and is required for the generation of T(H)17 cells. IL-6 has been implicated in a number of inflammatory diseases and cancers, including, but not limited to, Castleman's disease, metastatic castration-associated prostate cancer, renal cell carcinoma, large-cell lung carcinoma, ovarian cancer, rheumatoid arthritis, asthma.

The Protein Data Bank website provides the crystal structure of IL-6 searchable by 1P9M (Boulanger, M. J., et al., Science, 2003, 300: 2101-2104); 1ALU (Somers et al., EMBO J., 1997, 16, 989-997); 1IL6 and 2IL6 (Xu, G. Y., et al., J Mol Biol., 1997, 268 468-481) and 1N26 (Varghese et al., Proc Natl Acad Sci USA., 2002, 99 15959-15964); as well as the crystal structure of IL-6 bound to various compounds searchable by 4CNI (Shaw, S., et al., Mabs, 2014, 6: 773); and 4NI7 and 4NI9 (Gelinas et al., J Biol Chem. 2014, 289(12), 8720-8734). Additionally, Gelinas et al., provides insight into the crystal structure of interleukin-6 in complex with a modified nucleic acid ligand (Gelinas, A. D., et al., J Biol Chem. 2014, 289(12), 8720-8734); and Somers et al., provides insight into the crystal structure of interleukin 6: implications for a novel mode of receptor dimerization and signaling.

Potential IL-6 direct or indirect inhibitors are provided in FIG. 1. Additional potential IL-6 direct or indirect inhibitors can be found in, for example, U.S. Pat. No. 8,901,310; U.S. patent Ser. No. 10/189,796; U.S. Pat. No. 9,694,015; each incorporated herein by reference. In another embodiment the TL-6 Extracellular Targeting Ligand is AvimarC326 or a binding fragment thereof which is described in Nat Biotechnol 23, 1556-1561 (2005).

IFN-γ

In some embodiments, the Target Extracellular Protein is human interferon-γ (IFN-γ) (UniProtKB—Q14609 (Q14609_HUMAN)). IFN-γ is a immunoregulatory cytokine. IFN-γ has been implicated in a number of autoimmune disorders, including, but not limited to rheumatoid arthritis, multiple sclerosis (MS), corneal transplant rejection, and various autoimmune skin diseases such as psoriasis, alopecia areata, vitiligo, acne vulgaris, and others.

The Protein Data Bank website provides the crystal structure of IFN-γ searchable by 1HIG (Ealick, S. E., et al., Science 252, 1991, 698-702); as well as the crystal structure of IFN-γ bound to various compounds searchable by 6E3K and 6E3L (Mendoza, J. L., et al., Nature, 2019, 567 56-60). Additionally, Randal et al., provides insight into the structure and activity of a monomeric interferon-γ: α-chain receptor signaling complex (Randal, M., et al., Structure, 2001, 9(2), 155-163).

Representative IFN-γ Targeting Ligands are described in FIG. 1. Additional IFN-γ Targeting Ligands can be found in, for example, J Med Chem 57: 4511-20 (2014); which is incorporated by reference herein.

Vascular Epithelial Growth Factor (VEGF)

In some embodiments, the Target Extracellular Protein is human vascular epithelial growth factor (VEGF) (UniProtKB—P15692 (VEGFA_HUMAN)). VEGF is a growth factor active in angiogenesis, vasculogenesis, and endothelial cell growth. VEGF induces endothelial cell proliferation, promotes cell migration, inhibits apoptosis and induces permeabilization of blood vessels. VEGF has been implicated in the vascularization and angiogenesis of tumors.

The Protein Data Bank website provides the crystal structure of VEGF searchable by 3QTK (Mandal, K., et al., Angew Chem Int Ed Engl., 2011, 50 8029-8033); and 4KZN (Shen et al.); as well as the crystal structure of VEGF bound to various compounds searchable by 5O4E (Lobner, E., et al., MAbs, 2017, 9 1088-1104); 4QAF (Giese, T., et al.); 5DN2 (Tsai, Y. C. I., et al., FEBS, 2017, J 283 1921-1934); 4GLS (Mandal, K., et al., Proc Natl Acad Sci USA, 2012, 109 14779-14784); and 1KMX (Stauffer, M. E. et al., J Biomol NMR, 2002, 23 57-61). Additionally, Mueller, Y. A., et al, provides insight into the Crystal structure and functional mapping of the kinase domain receptor binding site of VEGF (Mueller, Y. A., et al., Proc Natl Acad Sci USA., 1997 Jul. 8; 94(14): 7192-7197).

Representative VEGF Targeting Ligands are provided in FIG. 1. Additional VEGF Targeting Ligands include, but are not limited to, (all cited referenced incorporated herein by reference) the peptide VEPNCDIHVMWEWECFERL-NH$_2$ (Biochemistry 1998, 37, 17754-177764). Additional VEGF Targeting Ligands are provided in, for example, J Med Chem 57: 3011-29 (2014), U.S. Pat. Nos. 9,884,843, 9,446,026, J Med Chem 53: 1686-99 (2010), J Med Chem 48: 8229-36 (2005), J Nat Prod 76: 29-35 (2013), each of which is incorporated herein by reference.

Transforming Growth Factor-β1 (TGF-β1)

In some embodiments, the Target Extracellular Protein is human transforming growth factor-β1 (TGF-β1) (UniProtKB—P01137 (TGFB1_HUMAN)). TGF-β1 is a multifunctional protein that regulates the growth and differentiation of various cell types and is involved in various processes, such as normal development, immune function, microglia function and responses to neurodegeneration. TGF-β1 can promote either T-helper 17 cells (Th17) or regulatory T-cells (Treg) lineage differentiation in a concentration-dependent manner. TGF-β1 expression in the tumor microenvironment has been associated with a poor prognosis, and is implicated in TGF-β1 mediated tumor suppression via T-cell exclusion. TGF-β1 expression has also been implicated in hematological malignancies and fibrosis.

The Protein Data Bank website provides the crystal structure of TGF-β1 searchable by 5E8S, 5E8T, and 5E8U (Tebben, A. J., et al., Acta Crystallogr D Struct Biol., 2016, 72 658-674); 2L5S (Zuniga, J. E., et al, J Mol Biol., 2011, 412 601-618); and 2PJY (Groppe, J., et al., Mol Cell, 2008, 29 157-168); as well as the crystal structure of TGF-β1 bound to various compounds searchable by 5QIK, 5QIL and 5QIM, (Zhang, Y., et al., ACS Med Chem Lett., 2018, 9 1117-1122); 6B8Y (Harikrishnan, L. S., et al., Bioorg Med Chem., 2018, 26 1026-1034); 5E8W, 5E8X, 5E8Z, and 5E90 (Tebben, A. J., et al., Acta Crystallogr D Struct Biol., 2016, 72 658-674); 3TZM (Ogunjimi, A. A. et al., Cell Signal, 2012, 24 476-483); 2X7O (Roth, G. J., et al., J Med Chem., 2010, 53 7287); 3KCF (Guckian, K., et al., Bioorg Med Chem Lett., 2010, 20 326-329); 3FAA (Bonafoux, D., et al., Bioorg Med Chem Lett., 2009, 19 912-916); 1VJY (Gellibert, F, J., et al., J Med Chem., 2004 47 4494-4506); and 1PY5 (Sawyer, J. S., et al., Bioorg Med Chem Lett., 2004, 14 3581-3584). Additionally, Hinck et al., provides insight into the structural studies of the TGF-βs and their receptors and further insight into evolution of the TGF-β superfamily (Hinck, A., FEBS, 2012, 586(14), 1860-1870).

Representative TGF-β1 Targeting Ligands are provided in FIG. 1. In some embodiments, the TGF-β1 Targeting Ligand is the peptide KRFK peptide (J. Biol. Chem. Vol. 274 (No. 19) pp. 13586-13593 (1999)(incorporated herein by reference). Additional TGF-β1 Targeting Ligands are provided in, for example, Bioorg Med Chem Lett 21: 5642-5 (2011), which is incorporated herein by reference.

Proprotein Convertase Subtilisin/Kexin Type 9 (PCSK-9)

In some embodiments, the Target Extracellular Protein is human proprotein convertase subtilisin/kexin type 9 (PCSK-9) (UniProtKB—Q8NBP7 (PCSK9_HUMAN)). PCSK-9 is a crucial player in the regulation of plasma cholesterol homeostasis. PCSK-9 binds to low-density lipid receptor family members: low density lipoprotein receptor (LDLR), very low-density lipoprotein receptor (VLDLR), apolipoprotein E receptor (LRP1/APOER) and apolipoprotein receptor 2 (LRP8/APOER2), and promotes their degradation in intracellular acidic compartments. It acts via a non-proteolytic mechanism to enhance the degradation of the hepatic LDLR through a clathrin LDLRAP1/ARH-mediated pathway, and may prevent the recycling of LDLR from endosomes to the cell surface or direct it to lysosomes for degradation. PCSK-9 has been implicated in high blood cholesterol and the development of cardiovascular disease.

The Protein Data Bank website provides the crystal structure of PCSK-9 searchable by 2P4E (Cunningham, D., et al., Nat Struct Mol Biol., 2007, 14 413-419); as well as the crystal structure of PCSK-9 bound to various compounds searchable by 3BPS (Kwon, H. J., et al., Proc Natl Acad Sci USA, 2008, 105 1820-1825); 6U26, 6U2N, 6U2P, 6U36, 6U38, and 6U3X (Petrilli, W. L., et al., Cell Chem Biol., 2019, 27 32-40.e3); 5OCA (Gustafsen, C., et al., Nat Commun., 2017, 8 503-503); 4NE9 (Schroeder, C. I., et al., Chem Biol., 2014, 21 284-294); 4OV6 (Mitchell, T., et al., J Pharmacol Exp Ther., 2014, 350 412-424); and 4NMX (Zhang, Y., et al., J Biol Chem., 2014, 289 942-955). Additionally, Piper et al., provides insight into the crystal structure of PCSK9 (Piper, D. E., et al., Structure, 2007, 15(5), 545-52).

Representative PCSK-9 Targeting Ligands are provided in FIG. 1. In some embodiments, the PCSK-9 Targeting Ligand is the peptide TVFTSWEEYLDWV (J. Bio. Chem.

2014 January; 289(2):942-955, incorporated herein by reference). Additional PCSK-9 Targeting Ligands are provided in, for example, U.S. Pat. No. 9,227,956, J Biol Chem 289: 942-55 (2014), each of which is incorporated by reference herein.

In certain embodiments the PCSK-9 ligand is any PCSK-9 ligand described in WO2021/156792 which is incorporated by reference.

In certain embodiments a compound is provided of Formula

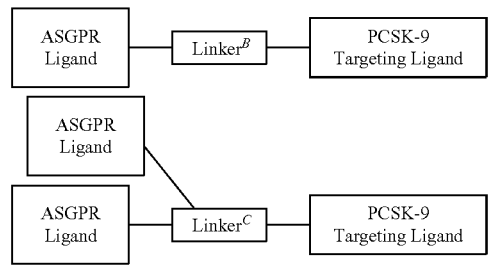

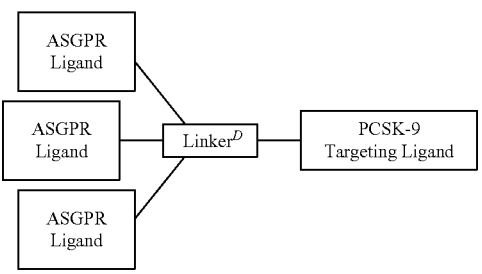

or a pharmaceutically acceptable salt thereof;
wherein
ASGPR Ligand is an ASGPR Ligand described herein;
PCSK-9 Targeting Ligand is any PCSK-9 ligand described in WO2021/156792.

Non-limiting examples of PCSK-9 Targeting Ligands that can be used in any of the formulas of the present invention include:

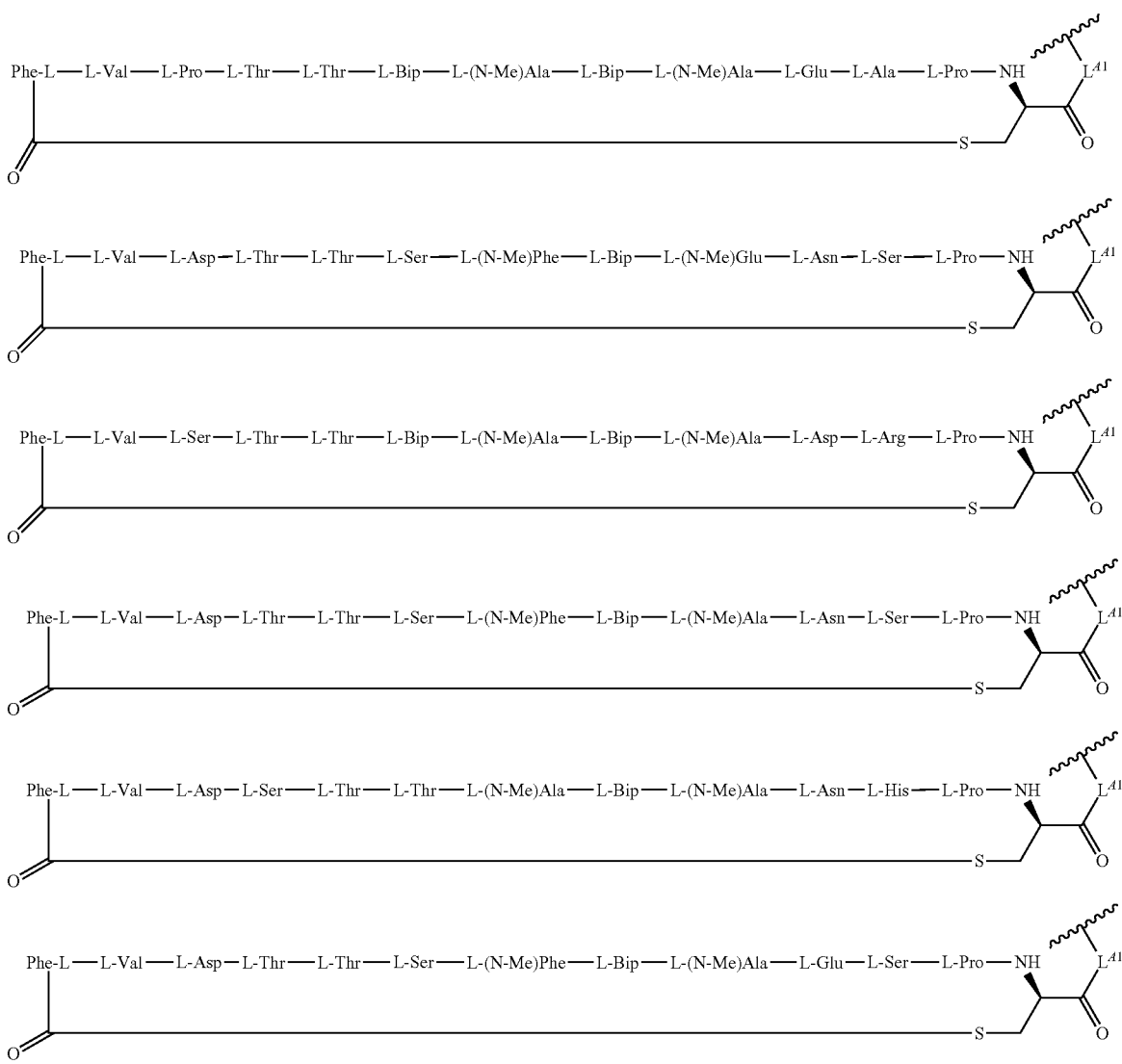

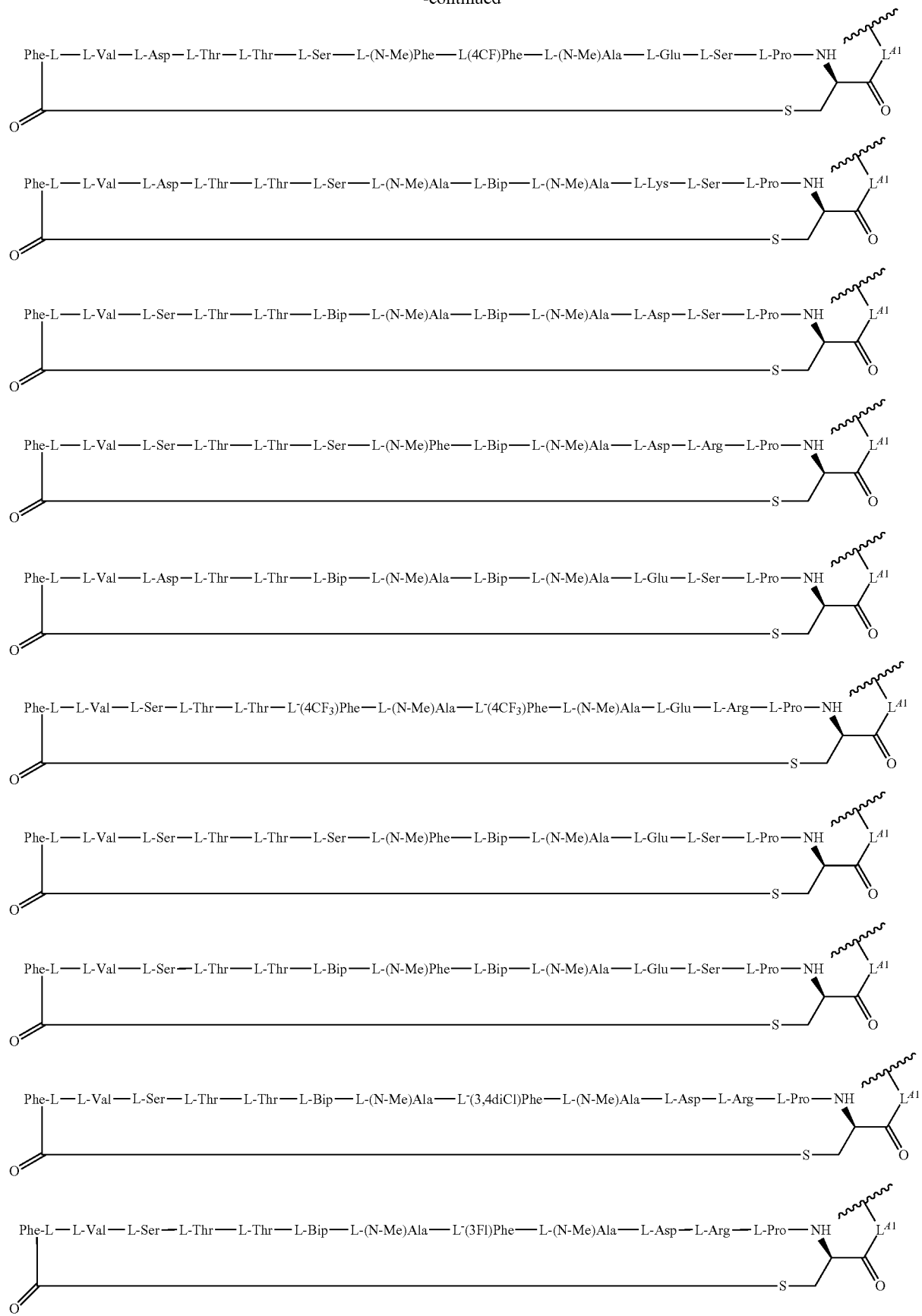

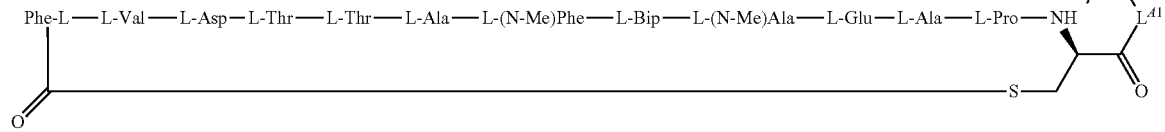
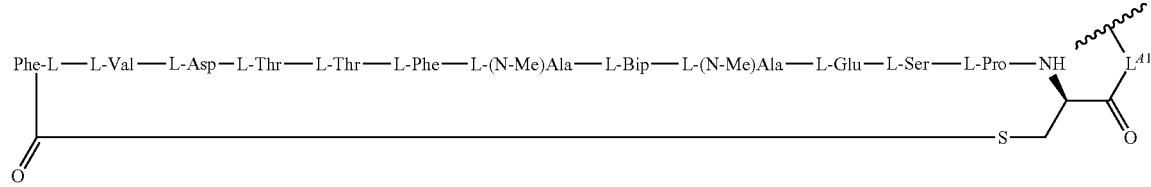
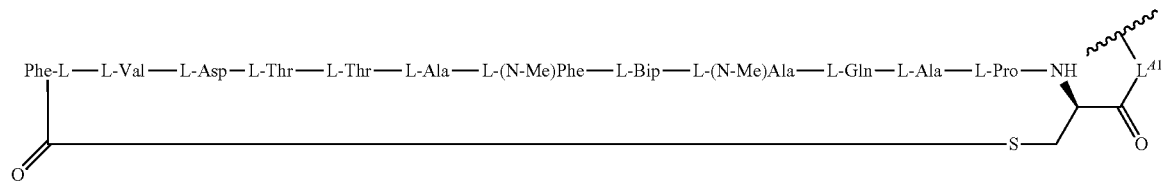
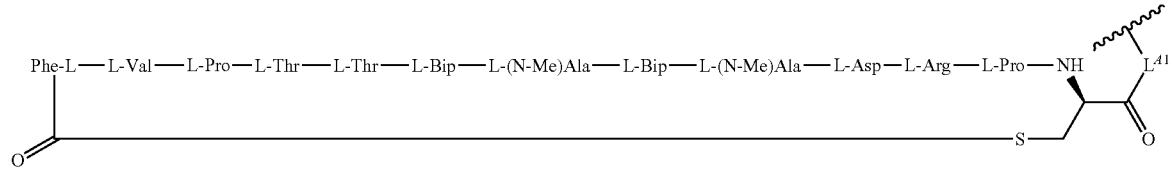
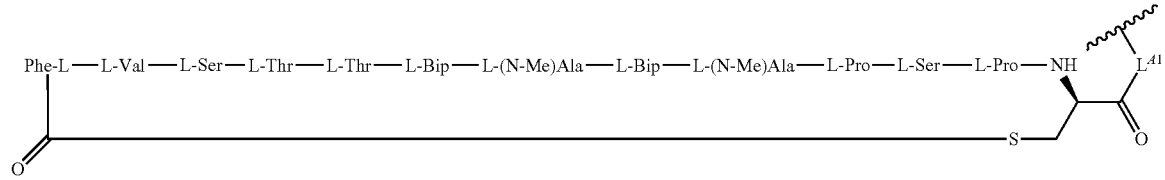
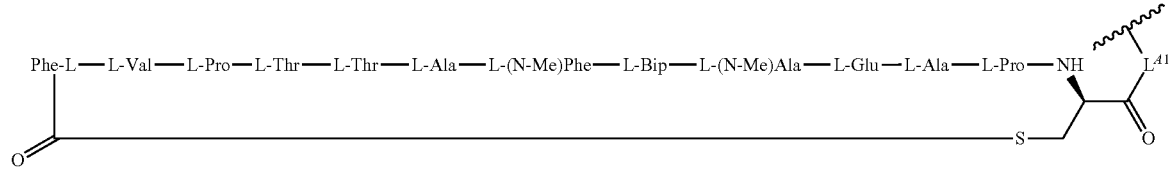
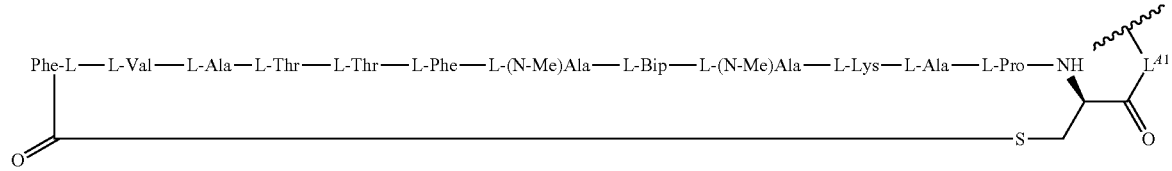
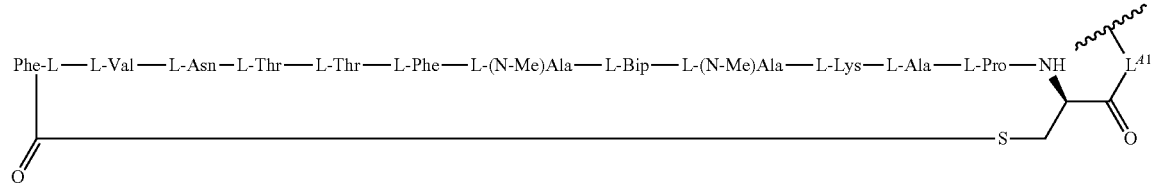
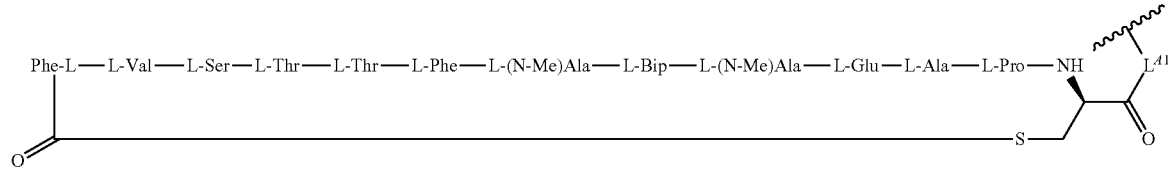

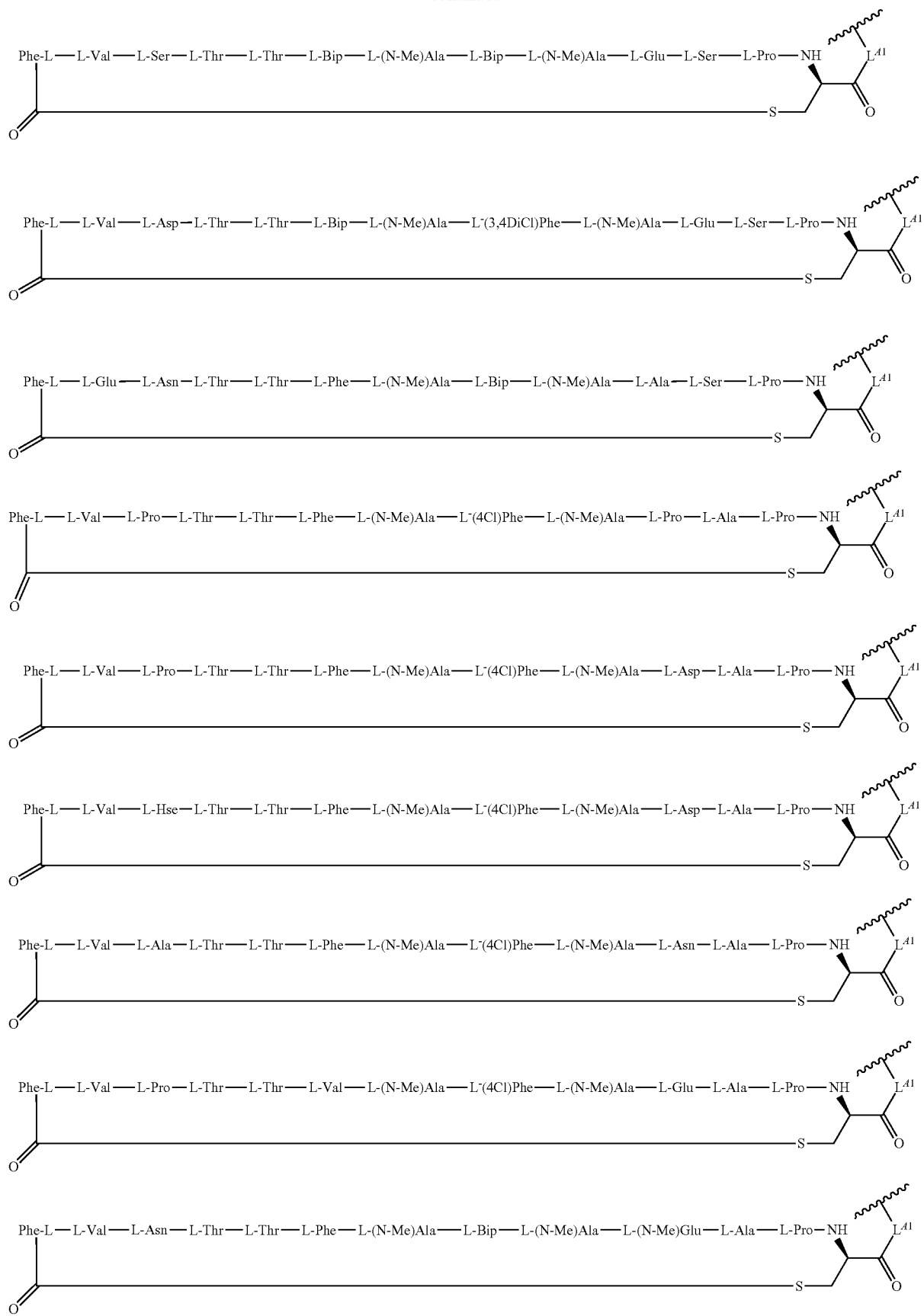

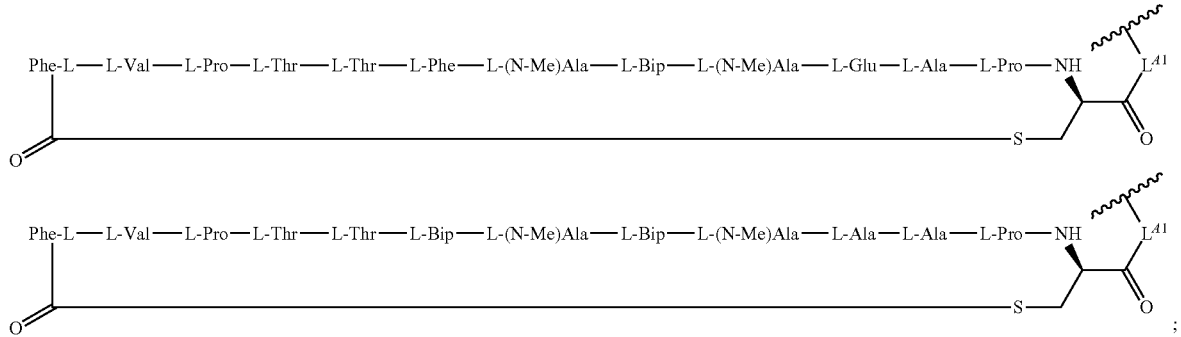

wherein $L^{A1}$ is bond, $NR^8$, or O.

In certain embodiments the PCSK9 Targeting Ligand is a compound of Formula:

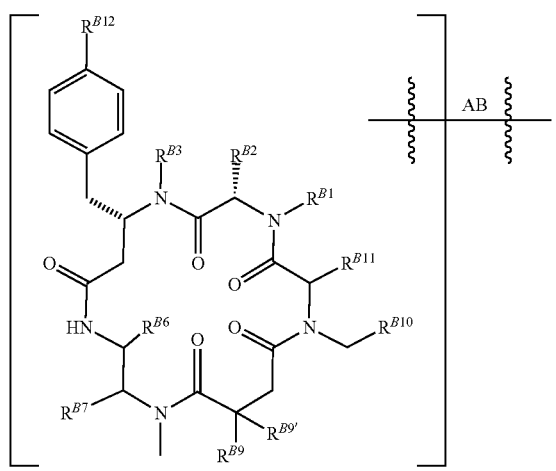

B-1 wherein,
$R^{B1}$ is H;
$R^{B2}$ is $(C_1-C_6)$alkoxy, $-L^{B1}-$, or $(C_1-C_6)$alkyl, substituted with $-C(=O)OH$;
$R^{B3}$ is H or $(C_1-C_6)$alkyl;
$R^{B6}$ is H, $(C_1-C_6)$alkyl or $L^{B1}$;
$R^{B7}$ is H, $(C_1-C_6)$alkyl or $L^{B1}$;
or $R^{B6}$ and $R^{B7}$ together with the carbon atoms to which they are attached form a $(C_3-C_7)$cycloalkyl;
$R^{B9}$ is H or $(C_1-C_6)$alkyl, optionally substituted with one or more $R^{B27}$;
$R^{B9'}$ is H or $(C_1-C_6)$alkyl;
$R^{B10}$ is $(C_6-C_{10})$aryl substituted with $OR^{B13}$ and optionally substituted with one or more $R^{B14}$;
$R^{11}$ is $(C_1-C_6)$alkyl or $L^{B1}$;
$R^{B12}$ is halogen, $(C_1-C_6)$alkyl, $(C_1-C_6)$alkoxy, $(C_1-C_6)$haloalkyl, $(C_1-C_6)$haloalkoxy, $-OH$, or CN;
$R^{B13}$ is $(C_6-C_{10})$aryl substituted with $R^{B16}$.
each $R^{B14}$ is independently at each occurrence halogen, $(C_1-C_6)$alkyl, $(C_1-C_6)$alkoxy, $(C_1-C_6)$haloalkyl, $(C_1-C_6)$haloalkoxy, oxo, $-OH$, or CN;
$R^{B16}$ is 5- to 7-membered heteroaryl comprising 1-3 heteroatoms selected from N, O, and S, optionally substituted with one or more $R^{B26}$;
each $R^{B26}$ is independently at each occurrence $(C_1-C_6)$alkyl optionally substituted with one or more $R^{B29}$.
each $R^{B27}$ is independently at each occurrence $(C_6-C_{10})$aryl;

each $R^{B29}$ is independently at each occurrence — $NR^{B31}R^{B32}$ or 4- to 7-membered heterocyclyl comprising 1-3 heteroatoms selected from N, O, and S;
each $R^{B31}$ is independently selected from H and $(C_1-C_6)$alkyl;
each $R^{B32}$ is independently selected from H and $(C_1-C_6)$alkyl;
$L^{B1}$ is $-(CH_2)_pNH-*$, where the * of $L^{B1}$ indicates the point of attachment to Linker $(L_A)$, and where at least one of $R^{B11}$, $R^{B6}$ or $R^{B7}$ is $-L^{B1}-$; and
n is 1.

In certain embodiments the PCSK9 Targeting Ligand is a compound of Formula:

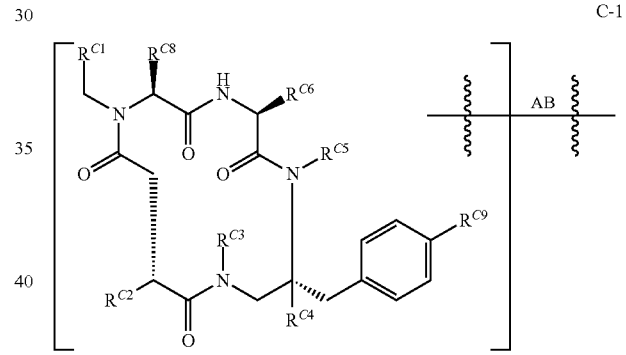

C-1 wherein,
$R^{C1}$ is $(C_6-C_{10})$aryl substituted with $-OR^{C10}$ and one or more $R^{C11}$;
$R^{C2}$ is H, $(C_1-C_6)$alkyl, $-L^{C1}$ or $(C_3-C_9)$carbocyclyl, wherein the alkyl is substituted with one $R^{C18}$, and the carbocyclyl is substituted with one or more $R^{C19}$.
$R^{C3}$ is H or $(C_1-C_6)$alkyl;
$R^{C4}$ is H or $(C_1-C_6)$alkyl; or
$R^{C3}$ and $R^{C4}$ together with the atoms to which they are attached form a 5- to 7-membered heterocyclyl ring comprising 1-3 heteroatoms selected from N, O, and S;
$R^{C5}$ is H or $(C_1-C_6)$alkyl;
$R^{C6}$ is $(C_1-C_6)$alkyl, or $-L^{C1}$, wherein the alkyl is optionally substituted with one or more substituents each independently selected from $-OH$ or $(C_1-C_6)$alkoxy;
$R^{C8}$ is H, $(C_1-C_6)$alkyl, or $-L^{C1}$,
$R^{C9}$ is halogen;
$R^{C10}$ is $(C_6-C_{10})$aryl substituted with one $R^{C22}$.
each $R^{C11}$ is independently at each occurrence halogen, $(C_1-C_6)$alkyl, $(C_1-C_6)$alkoxy, $(C_1-C_6)$haloalkyl, $(C_1-C_6)$haloalkoxy, $-OH$, or CN;
$R^{C18}$ is $(C_6-C_{10})$aryl;
each $R^{C19}$ is independently at each occurrence halogen, $(C_1-C_6)$alkyl, $(C_1-C_6)$alkoxy, $(C_1-C_6)$haloalkyl, $(C_1-C_6)$haloalkoxy, $-OH$, or CN;

$R^{C22}$ is 5- or 6-membered heteroaryl comprising 1-3 heteroatoms selected from N, O, and S, substituted with one or more $R^{C23}$.

each $R^{C23}$ is independently at each occurrence $(C_1-C_6)$ alkyl, optionally substituted with —$NR^{C24}R^{C25}$ or a 4- to 7-membered heterocyclyl comprising 1-3 heteroatoms selected from N, O, and S;

$R^{C24}$ is H, $(C_1-C_6)$alkyl;

$R^{C25}$ is H, $(C_1-C_6)$alkyl, $L^{C1}$ is —$(CH_2)_pNH$—*, where the * of $L^{C1}$ indicates the point of attachment to Linker $(L_A)$, and where at least one of $R^{C2}$, $R^{C6}$ or $R^{C8}$ is -$L^{C1}$; and p is 1, 2, 3, 4, 5, or 6.

In certain embodiments the PCSK-9 Targeting Ligands that can be used in any of the formulas of the present invention include:

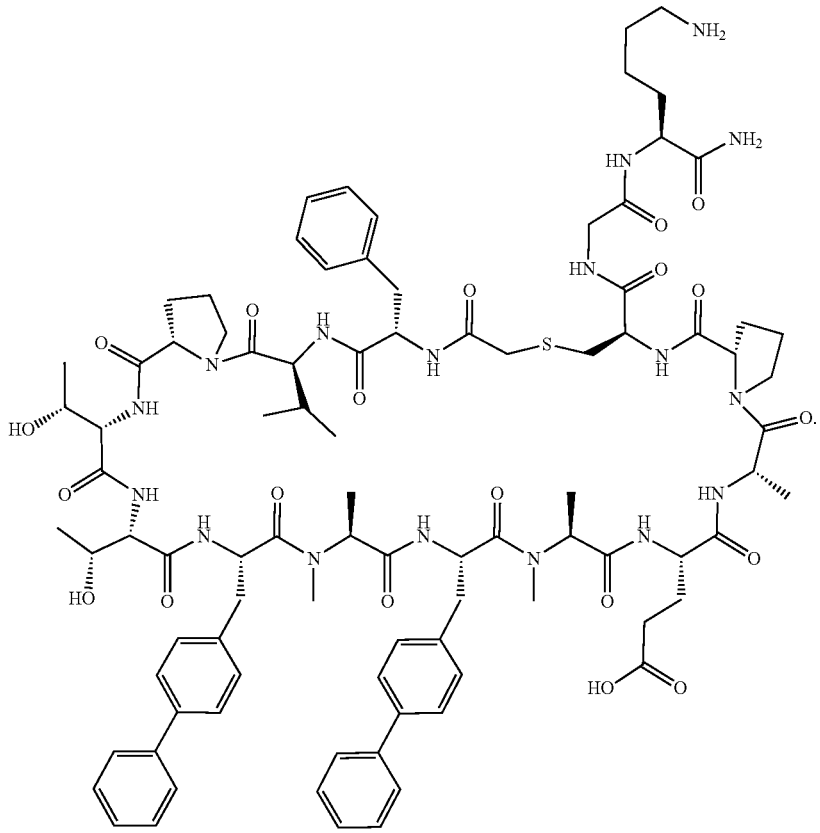 [SMILES: CC(C)[C@@H]1NC(=O)[C@H](Cc2ccccc2)NC(=O)CSC[C@@H](C(=O)NCC(=O)N[C@@H](CCCCN)C(N)=O)NC(=O)[C@@H]2CCCN2C(=O)[C@H](C)NC(=O)[C@H](CCC(=O)O)NC(=O)[C@H](C)N(C)C(=O)[C@H](Cc2ccc(-c3ccccc3)cc2)NC(=O)[C@H](C)N(C)C(=O)[C@H](Cc2ccc(-c3ccccc3)cc2)NC(=O)[C@H]([C@@H](C)O)NC(=O)[C@H]([C@@H](C)O)NC(=O)[C@@H]2CCCN2C1=O]

In certain embodiments the PCSK-9 Targeting Ligands that can be used in any of the formulas of the present invention include:

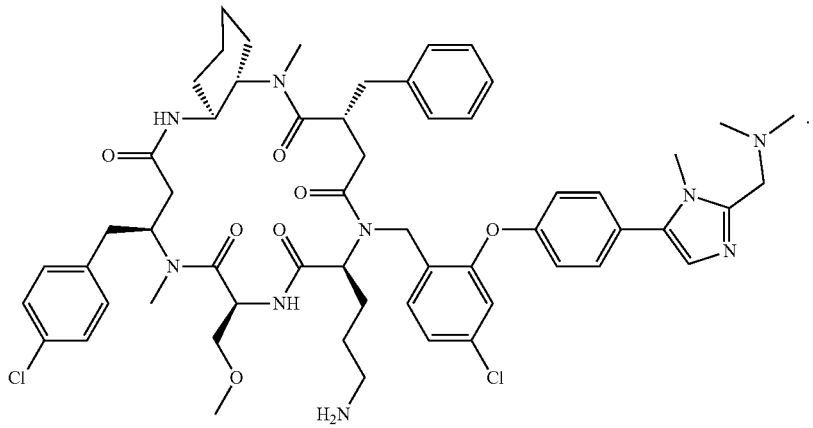

In certain embodiments the compound of the present invention is selected from
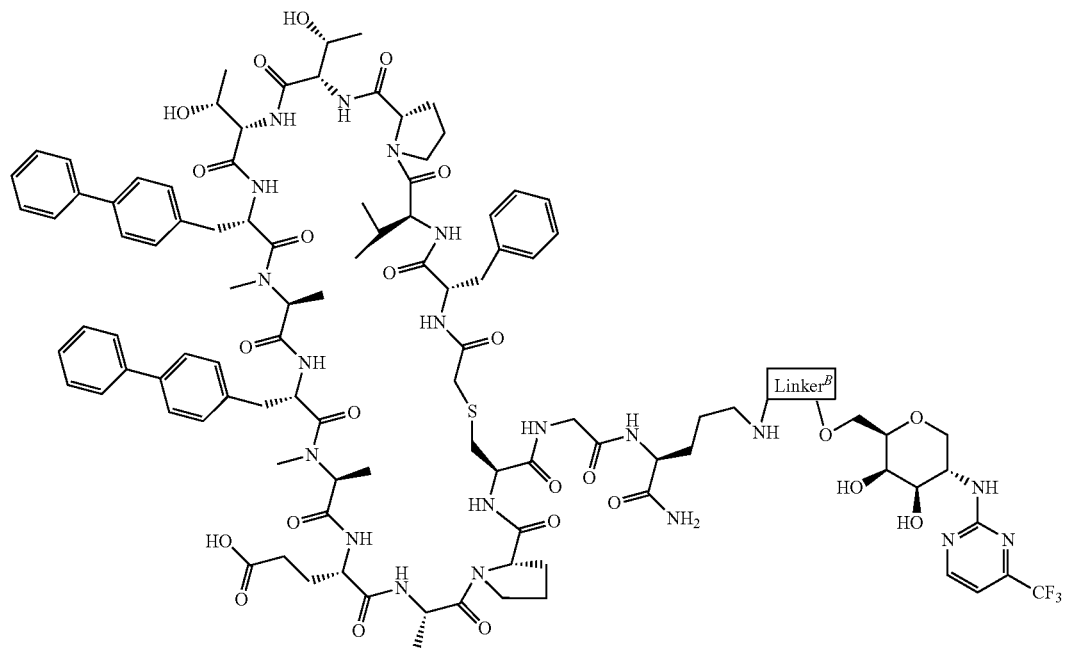
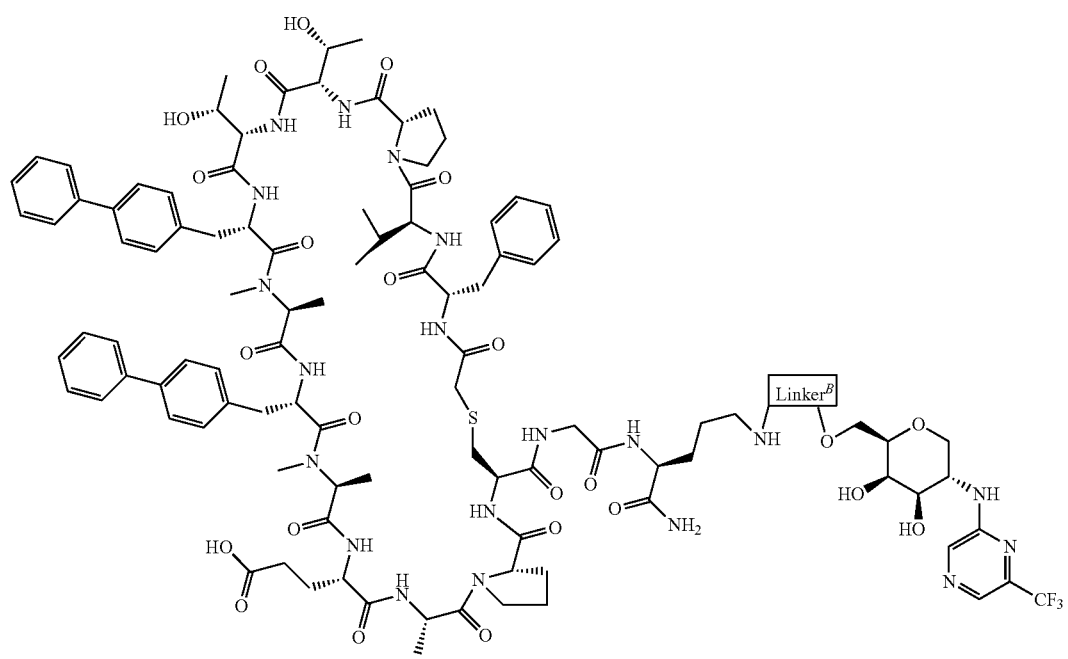

-continued
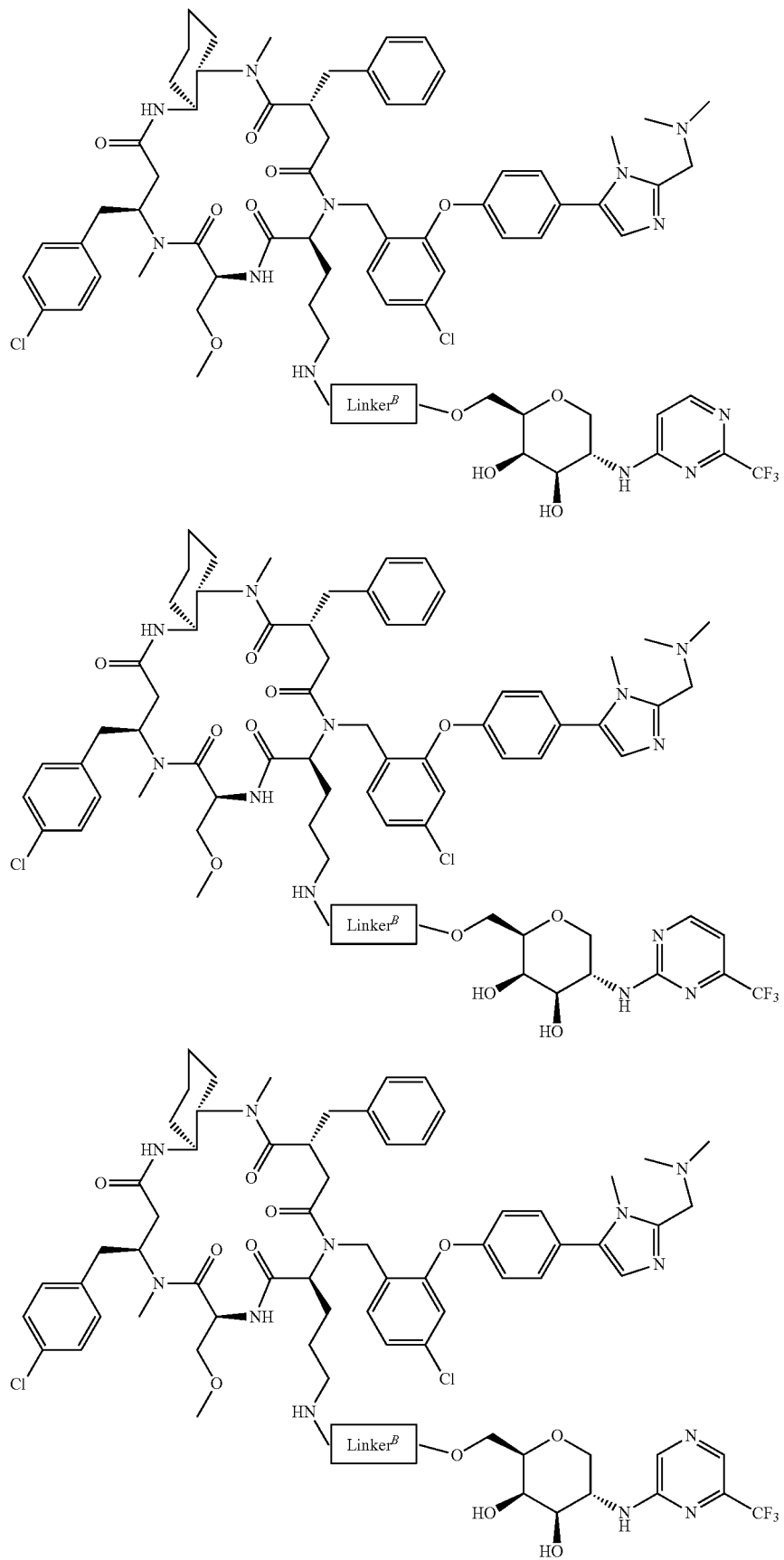

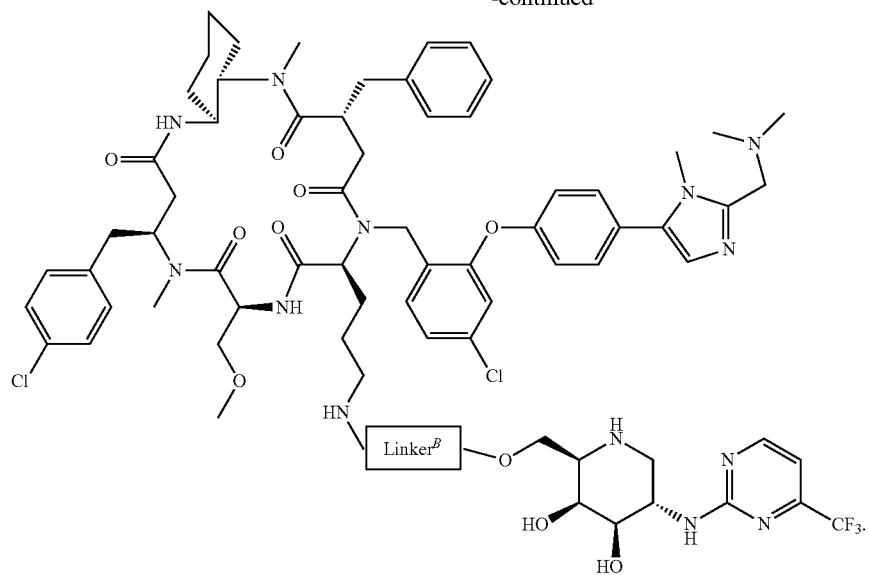
In certain embodiments the compound of the present invention is selected from
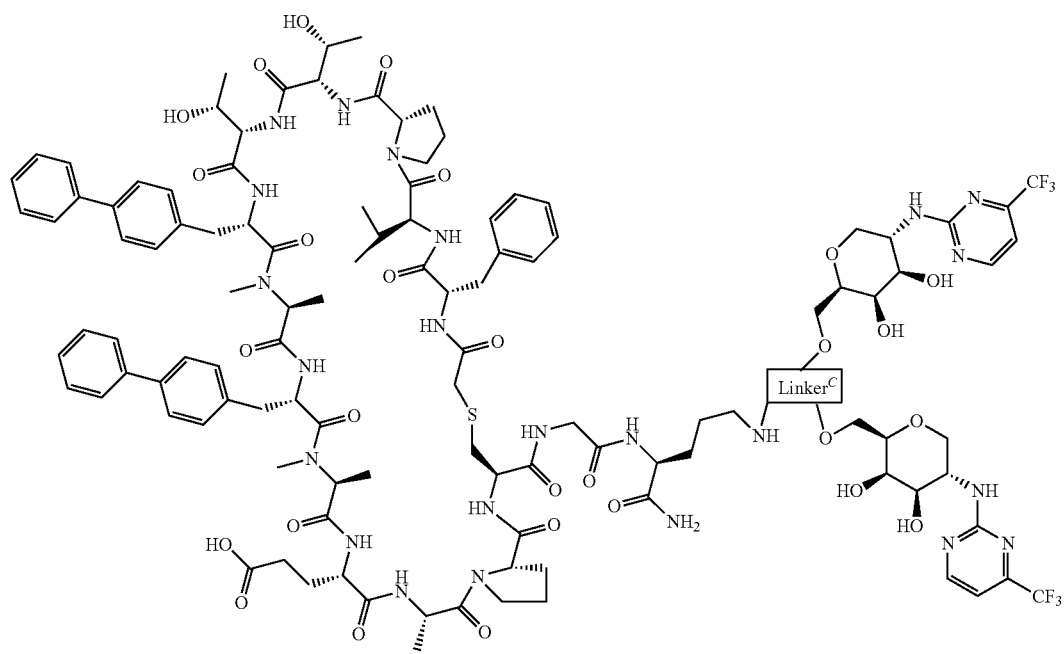

-continued
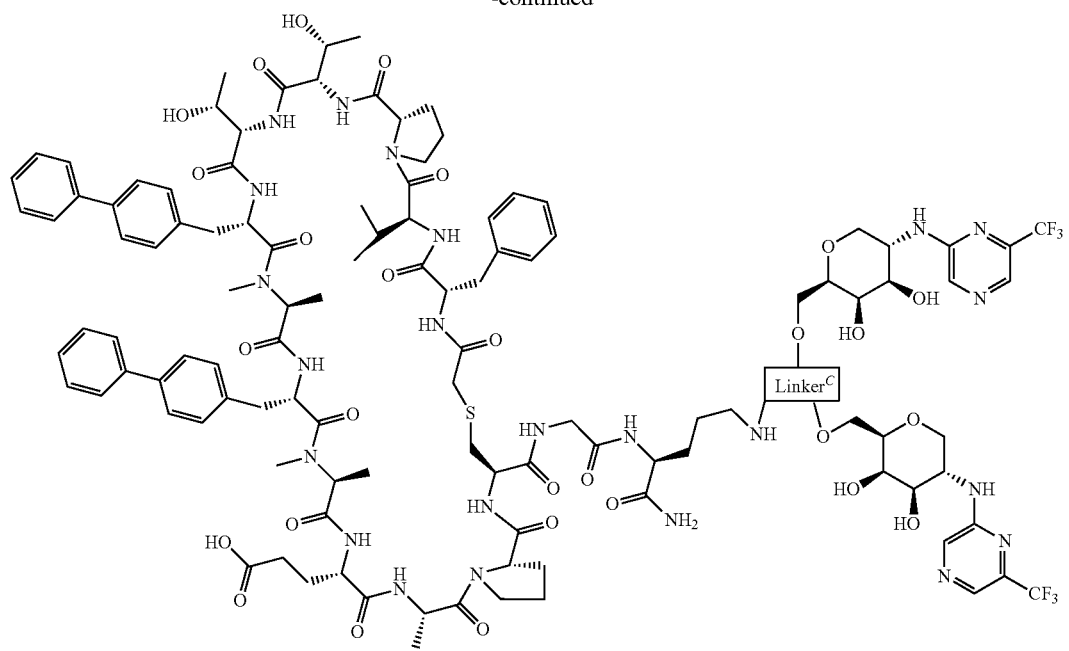
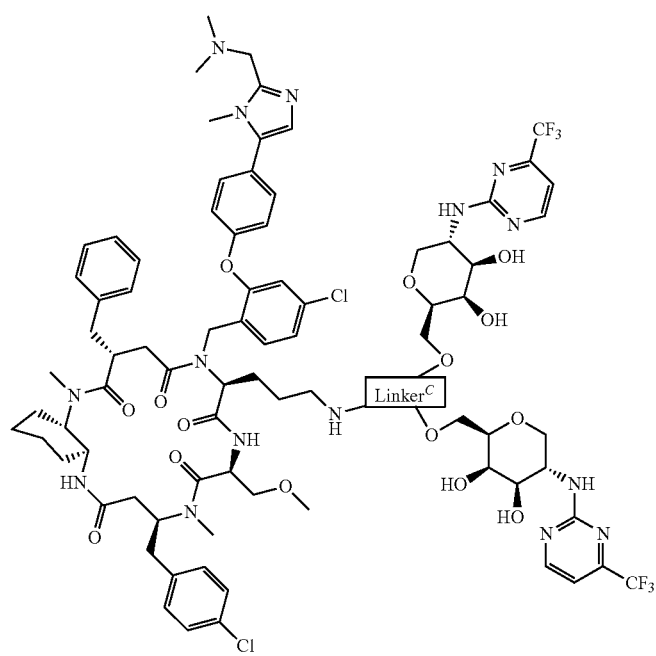

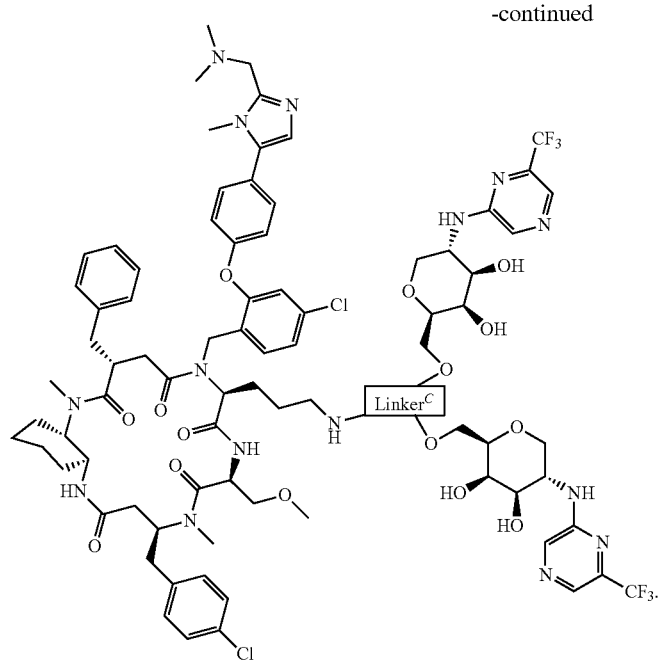
In certain embodiments the PCSK9 Targeting Ligand is selected from:
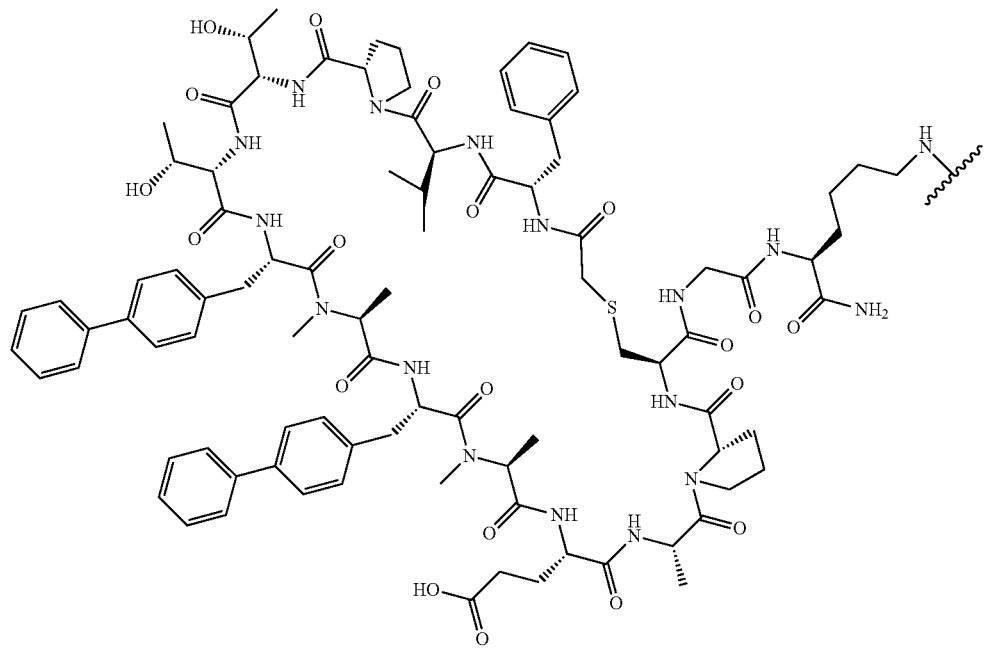

-continued
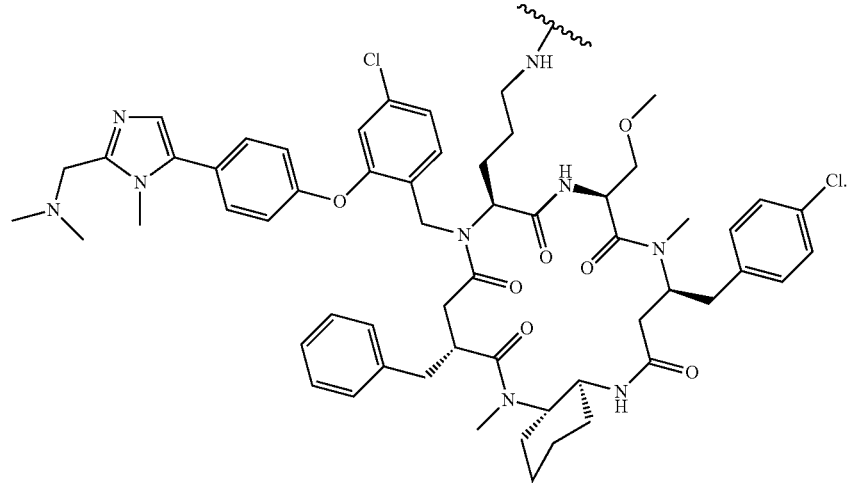
Non-limiting examples of PCSK-9 degrading compounds include:
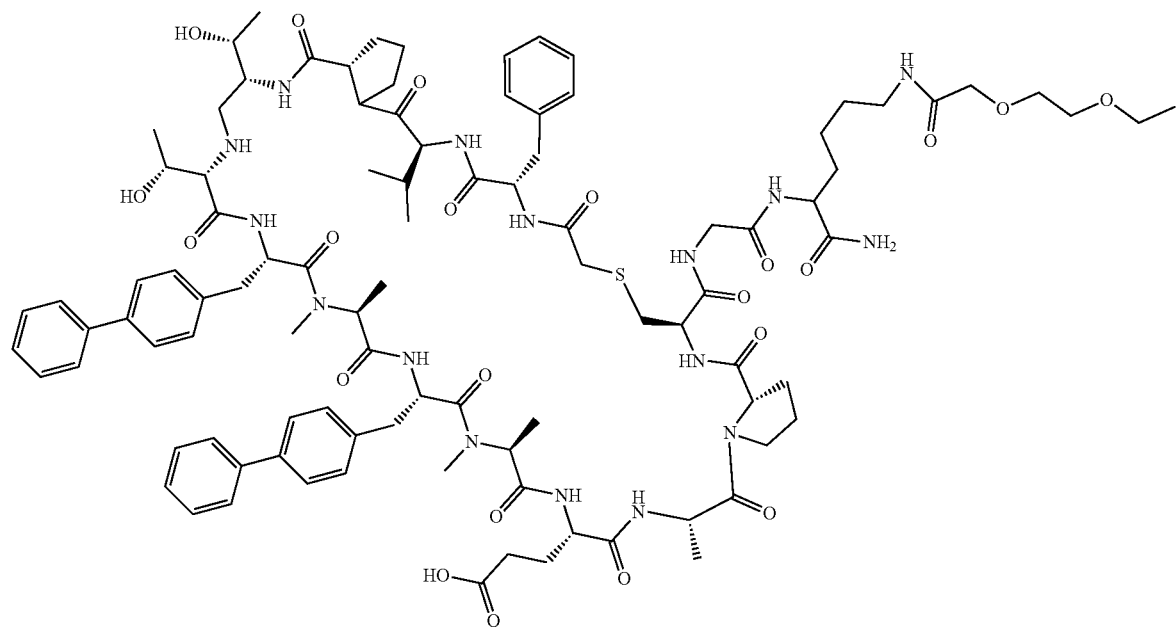

-continued
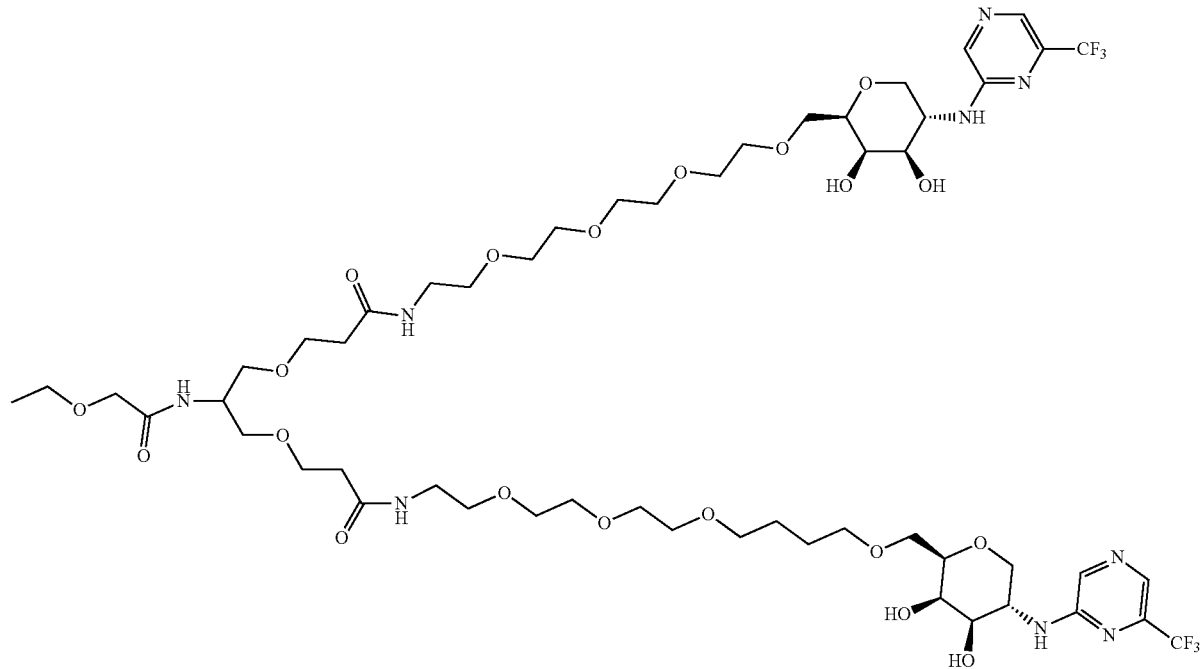
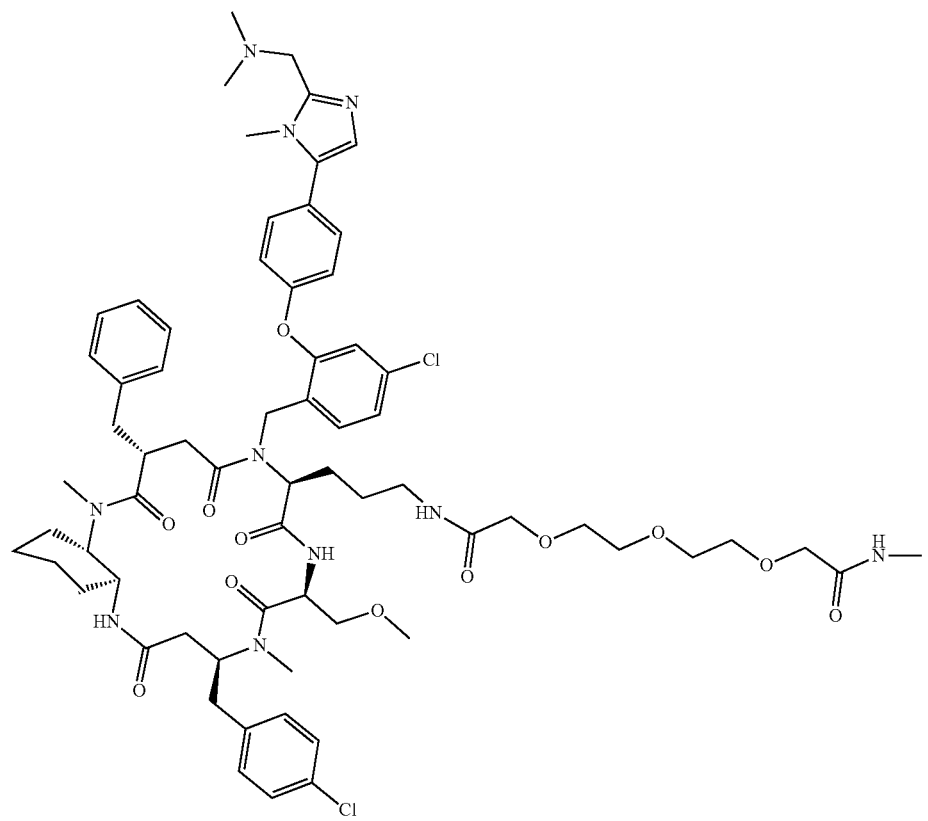

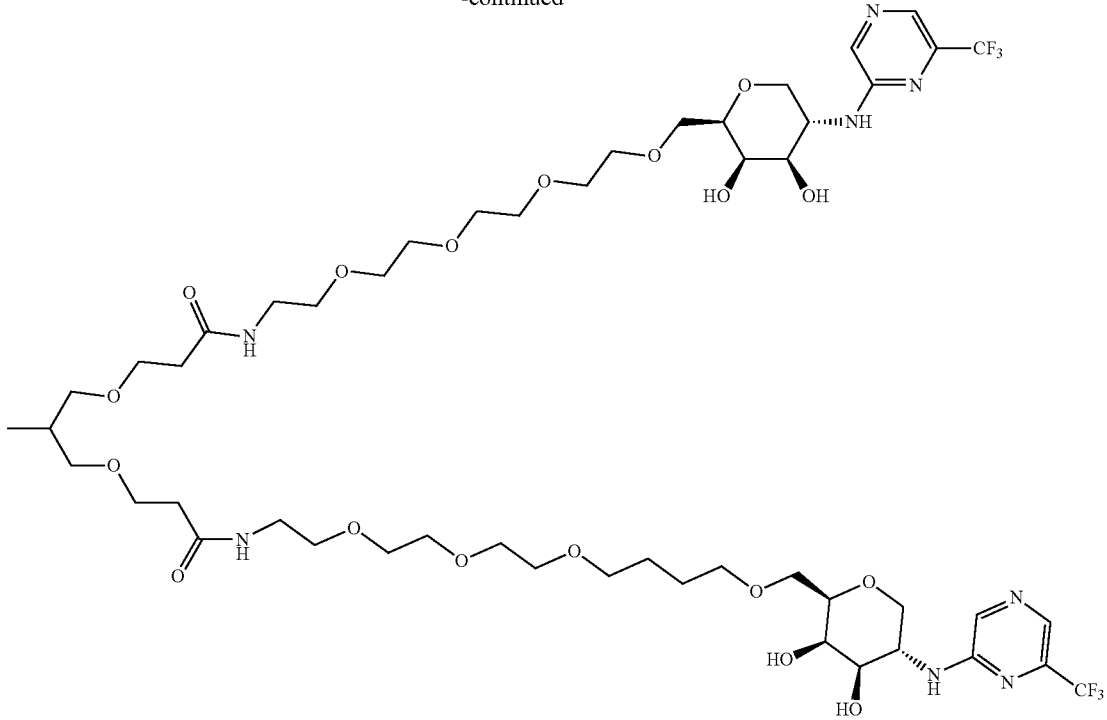

30

FHR3

The human complement factor H-related protein 3 (FHR-3) belongs to the complement factor H (FH)-family. Factor H (FH), a major negative regulator of alternative complement pathway activation, belongs to a family that also includes five other related family members thought to have arisen from nonallelic homologous recombination and inter-locus gene conversion including: complement factor H-related protein 1 (FHR1), complement factor H-related protein 2 (FHR2), complement factor H-related protein 3 (FHR3), complement factor H-related protein 4 with isoforms 4A and 4B (FHR4A and FHR4B) and complement factor H-related protein 5 (FHR5).

FHR3, unlike factor H, lacks the complement regulatory domains essential for complement inactivation and also competes with factor H, resulting in complement over-activation. Thus, the present invention provides compounds for use in modulating the concentration of complement factor H— proteins, specifically FHR3, to remove factor H's competitor and thereby restore factor H— mediated regulation to treat disorders caused by excessive complement activation.

Due to the central role that factor H plays in the regulation of complement, there are many clinical implications arising from aberrant FH activity. Loss of function mutation in factor H increase susceptibility to the renal diseases, atypical hemolytic uremic syndrome (aHUS) and dense deposit disease (ODD), whilst polymorphic variation of complement factor H has been strongly associated with important human diseases, including age-related macular degeneration (AMO) and meningococcal sepsis (Clin Exp Immunol 151 (2):210-230; Immunobiology 217(11):1034-1046).

In certain embodiment, the invention provides the use in the treatment of a FHR3 mediated disease or disorder.

In certain embodiments, the FHR3 mediated disease or disorder is a complement-related diseases, disorders of complement dysregulation, autoimmune diseases, kidney disease, retinal degenerative diseases, Rheumatic Diseases, associated degenerative diseases, autoimmune renal disease, dense deposit disease (ODD), and systemic autoimmune diseases.

In certain embodiments, nonlimiting examples of FHR3 mediated diseases or disorders include nephropathy, age-related macular degeneration, atypical hemolytic uremic syndrome (aHUS), autoimmune form of hemolytic uremic syndrome, hepatocellular carcinoma (HCC), C3 glomerulopathy, paroxysmal nocturnal hemoglobinuria, Polymyalgia rheumatica, rheumatoid arthritis, meningococcal sepsis, and SLE (Systemic lupus erythematosus).

In certain embodiments, the present invention provides compounds that utilize receptor mediated endocytosis to eliminate or decrease level of complement factor H-related protein 3 (FHR3) from the plasma.

In certain embodiments, the FHR3 Targeting Ligand is selected from:
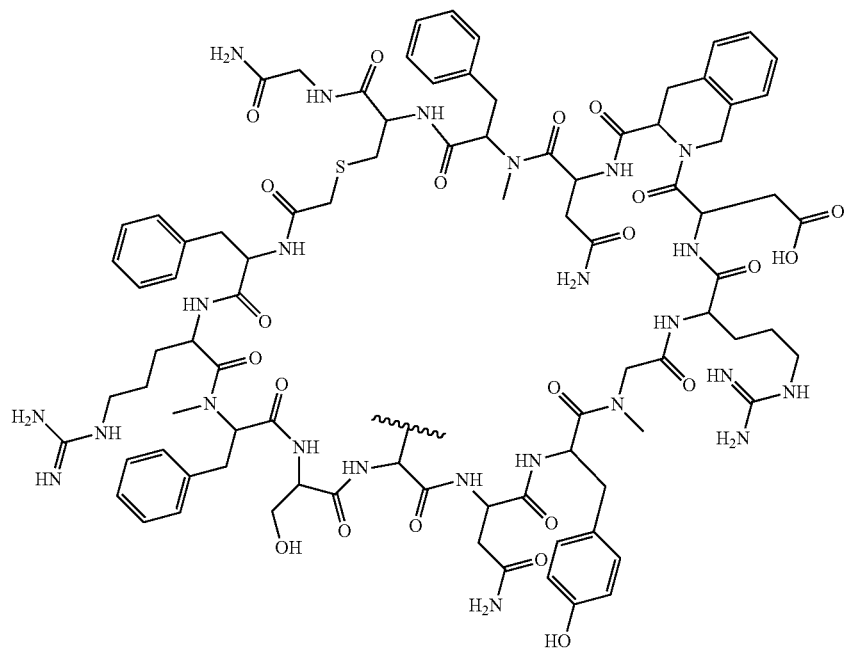
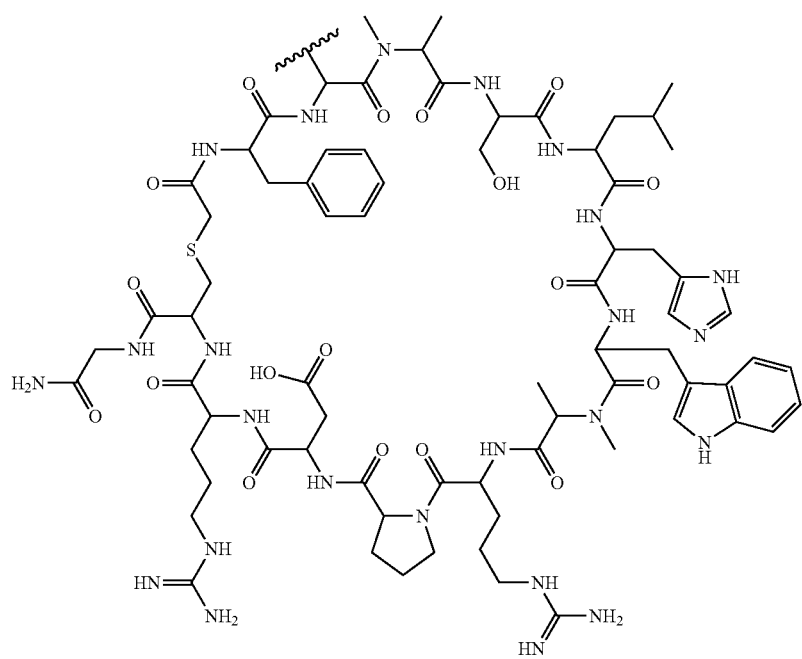

111
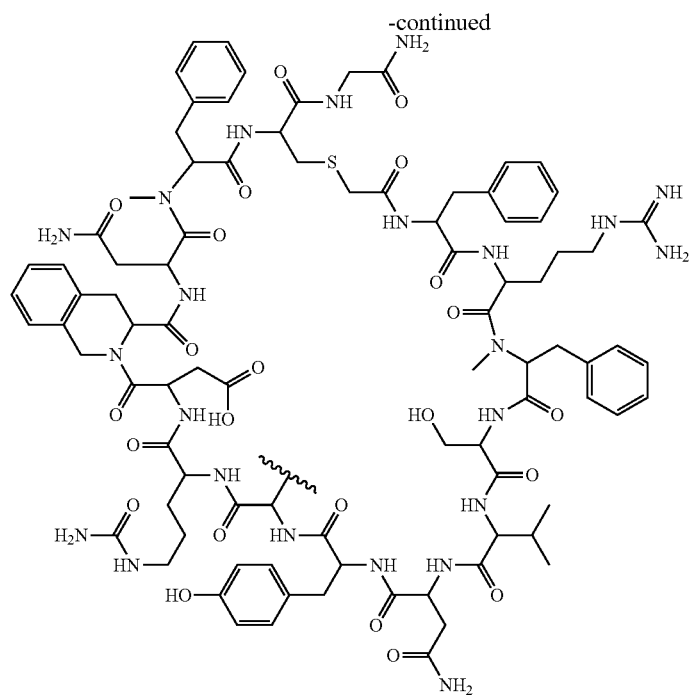
-continued
112
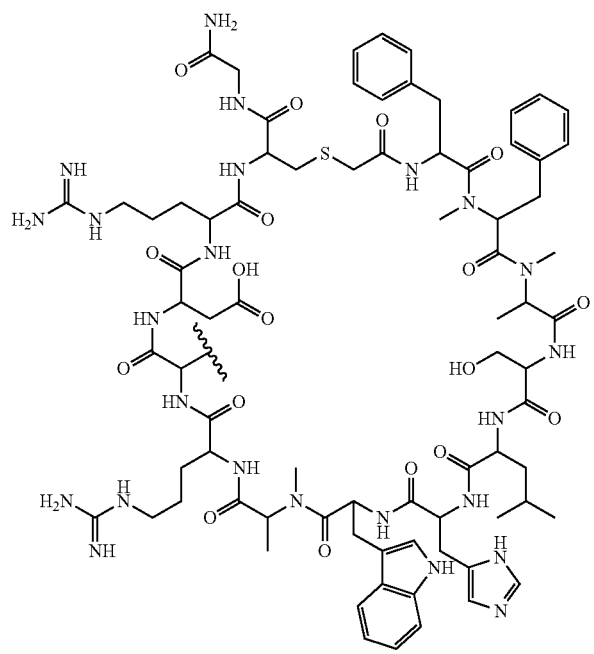

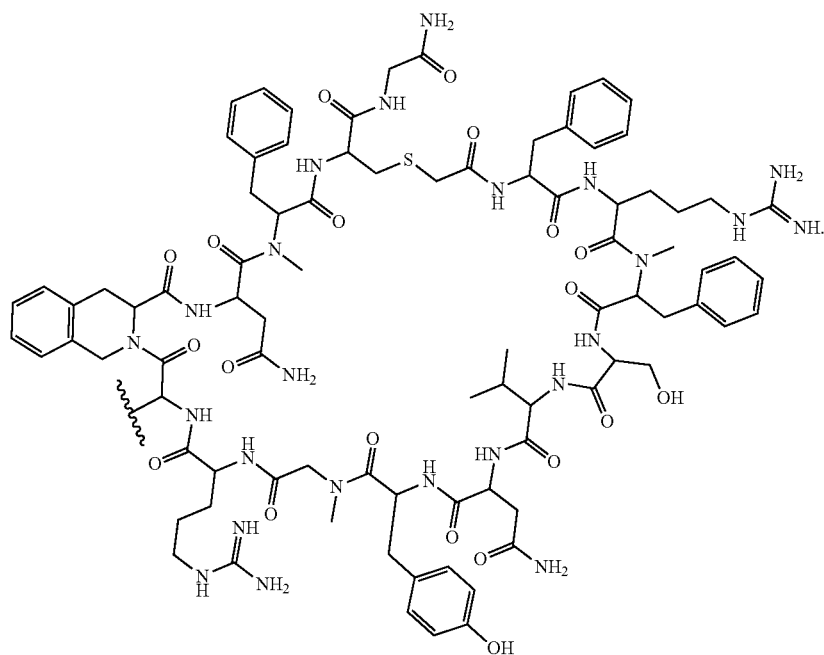 [SMILES: *C1NC(=O)C(CCCNC(=N)N)NC(=O)CN(C)C(=O)C(Cc2ccc(O)cc2)NC(=O)C(CC(N)=O)NC(=O)C(C(C)C)NC(=O)C(CO)NC(=O)C(Cc2ccccc2)N(C)C(=O)C(CCCNC(=N)N)NC(=O)C(Cc2ccccc2)NC(=O)CSCC(C(=O)NCC(N)=O)NC(=O)C(Cc2ccccc2)N(C)C(=O)C(CC(N)=O)NC(=O)C2Cc3ccccc3CN2C1=O]
In certain embodiments, the FHIR3 compound is selected from:
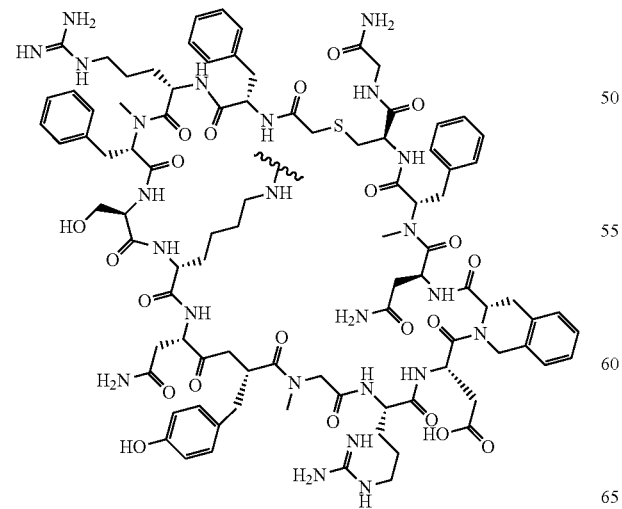

115
-continued
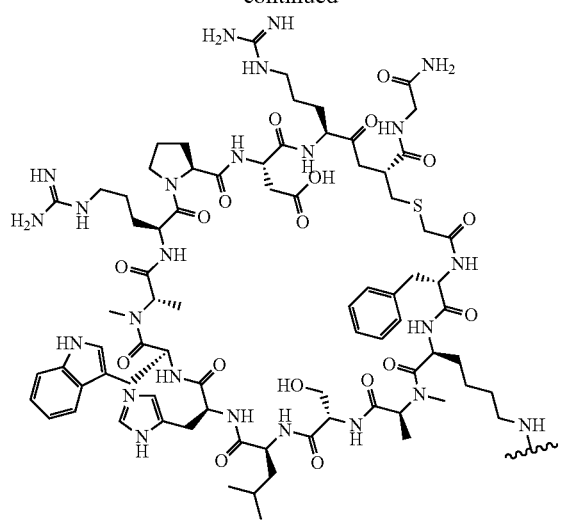
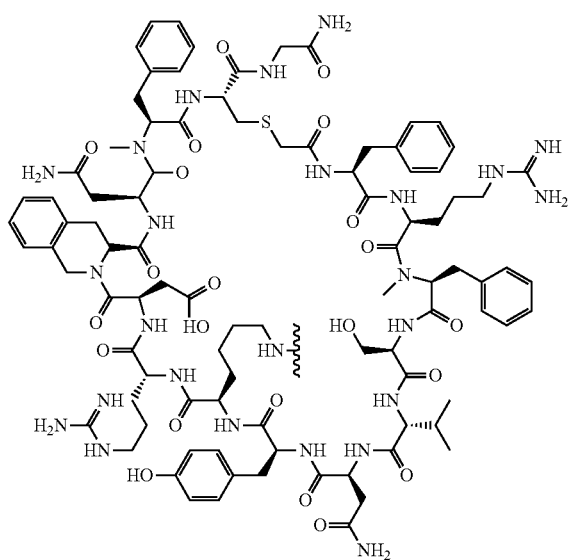
116
-continued
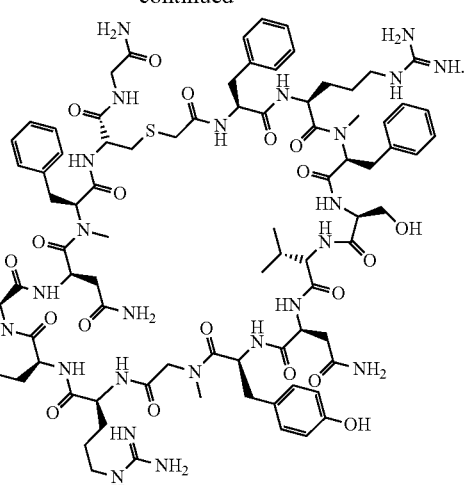
Tau Protein
In some embodiments, the Target Extracellular Protein is tau protein. The accumulation of tau in the brain causes aggregates that are associated with Alzheimer's and other tauopathies.
Non-limiting examples of Tau Protein targeting ligands include:
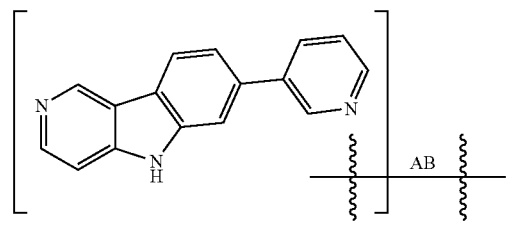
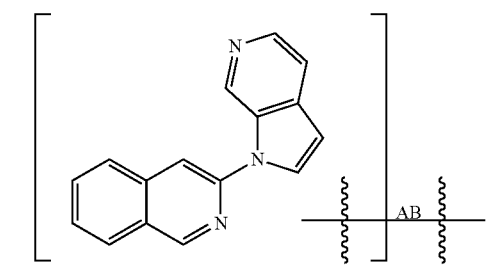
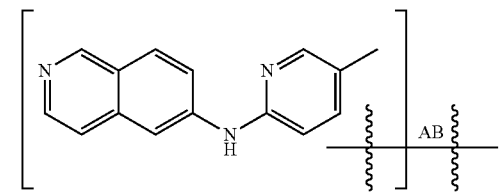
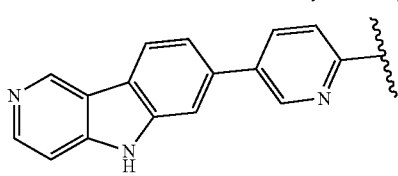

-continued

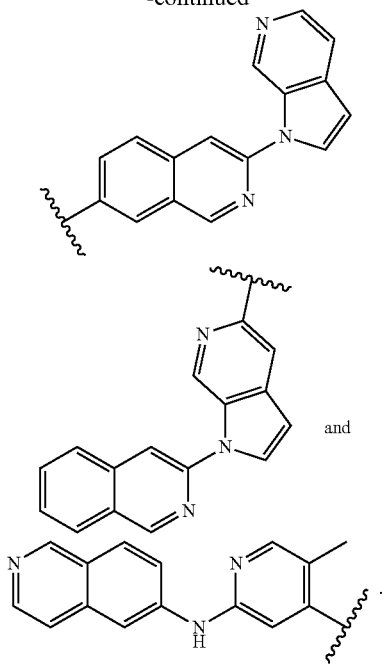

IL-21

In some embodiments, the Target Extracellular Protein is human interleukin-21 (IL-21) (UniProtKB—Q9HBE4 (IL21_HUMAN)). IL-21 is an immunoregulatory cytokine. IL-21 has been implicated in a number of autoimmune disorders, including Sjögren's syndrome, systemic lupus erythematosus, type 1 diabetes, multiple sclerosis, rheumatoid arthritis, and inflammatory bowel disease.

The Protein Data Bank website provides the crystal structure of IL-21 searchable by 2OQP (Bondensgaard, K., et al., J Biol Chem., 2007, 282 23326-23336); and 4NZD (Hamming et al.); as well as the crystal structure of IL-21 bound to various compounds searchable by 3TGX (Hamming, O. J., et al., J Biol Chem., 2012, 287(12), 9454-9460).

Representative IL-21 Targeting Ligands are described in FIG. 1. Additional IL-21 Targeting Ligands can be found in, for example, U.S. Pat. No. 9,701,663, which is incorporated herein by reference.

IL-22

In some embodiments, the Target Extracellular Protein is human interleukin-22 (IL-22) (UniProtKB—Q9GZX6 (IL22 HUMAN)). IL-22 is a member of IL-10 family cytokines that is produced by many different types of lymphocytes including both those of the innate and adaptive immune system. IL-22 has been implicated in a number of autoimmune disorders, including, but not limited to, graft versus host disease (GVHD), psoriasis, rheumatoid arthritis, atopic dermatitis, and asthma.

The Protein Data Bank website provides the crystal structure of IL-22 searchable by 1M4R (Nagem, R. A. P., et al., Structure, 2002, 10 1051-1062); as well as the crystal structure of IL-22 bound to various compounds searchable by 3DGC (Jones, B. C. et al., Structure, 2008, 16 1333-1344).

Representative IL-22 Targeting Ligands are described in FIG. 1. Additional IL-22 Targeting Ligands can be found in, for example, U.S. Pat. No. 9,701,663, which is incorporated herein by reference.

IL-10

In some embodiments, the Target Extracellular Protein is human interleukin-10 (IL-10) (UniProtKB—P22301 (IL10_HUMAN)). IL-10 is an inflammatory cytokine. IL-10 has been implicated in tumor survival and protection against cytotoxic chemotherapeutic drugs.

The Protein Data Bank website provides the crystal structure of IL-10 searchable by 2TLK (Zdanov, A et al., Protein Sci., 1996, 5 1955-1962); 1ILK (Zdanov, A. et al., Structure, 1995, 3 591-601); 2H24 (Yoon, S. I., et al., J Biol Chem., 2006, 281 35088-35096) and 3LQM (Yoon, S. I., et al., Structure, 2010, 18 638-648). Additionally, Zdanov, A., et al, provides insight into crystal structure of IL-10 (Zdanov A., Current Pharmaceutical design, 2004, 10, 3873-3884).

Representative IL-10 Targeting Ligands are provided in FIG. 1. Additional IL-10 Targeting Ligands can be found, for example, in ACS Chem Biol 11: 2105-11 (2016), which is incorporated herein by reference.

IL-5

In some embodiments, the Target Extracellular Protein is human interleukin-5 (IL-5) (UniProtKB—P05113 (IL5_HUMAN)). IL-5 is a cytokine that regulates eosinophil maturation, recruitment, and survival. IL-5 has been implicated in a number of allergic disorders, including, but not limited to, asthma, nasal polyposis, atopic dermatitis, eosinophilic esophagitis, hypereosinophilic syndrome, and Churg-Strauss syndrome.

The Protein Data Bank website provides the crystal structure of IL-5 searchable by 1HUL (Milburn, M. V., Nature, 1993, 363, 172-176) and 3VA2 (Kusano et al., Protein Sci., 2012, 21(6), 850-864); as well as the crystal structure of IL-5 bound to various compounds searchable by 1OBX and 1OBZ (Kang, B. S., et al., Structure, 2003, 11, 845).

Representative IL-5 Targeting Ligands are provided in FIG. 1. Additional IL-5 Targeting Ligands can be found, for example, in Bioorg Med Chem 18: 4441-5 (2010); Bioorg Med Chem 18: 4625-9 (2011); Bioorg Med Chem 21: 2543-50 (2013); Eur J Med Chem 59: 31-8 (2013); Bioorg Med Chem 23: 2498-504 (2015); Bioorg Med Chem 20: 5757-62 (2012); each of which is incorporated by reference herein.

IL8

In some embodiments, the Target Extracellular Protein is human interleukin-8 (IL-8) (UniProtKB—P10145 (IL8_HUMAN)). IL-8 is a chemotactic factor that attracts neutrophils, basophils, and T-cells, but not monocytes. It is also involved in neutrophil activation. It is released from several cell types in response to an inflammatory stimulus. IL-8 has been implicated in the promotion of tumor progression, immune escape, epithelial-mesenchymal transition, and recruitment of myeloid-derived suppressor cells. Studies have demonstrated that high serum IL-8 levels correlate with poor prognosis in many malignant tumors. Preclinical studies have shown that IL-8 blockade may reduce mesenchymal features in tumor cells, making them less resistant to treatment.

The Protein Data Bank website provides the crystal structure of IL-8 searchable by 3IL8 (Baldwin, E. T., et al., Proc Natl Acad Sci USA, 1991, 88, 502-506); and 1IL8 and 2IL8 (Clore, G. M., et al., Biochemistry, 1990, 29, 1689-1696); as well as the crystal structure of IL-8 bound to various compounds searchable by 1ILP and 1ILQ (Skelton, N, J., et al., Structure, 1999, 7, 157-168); and 1ROD (Sticht, H., et al., Eur J Biochem., 1996, 235, 26-35); 4XDX (Ostrov et al.,) and 5WDZ (Beckamp, S., J Biomol NMR, 2017, 69, 111-121).

Representative IL-8 Targeting Ligands are provided in FIG. 1. Additional IL-8 Targeting Ligands can be found in, for example, Bioorg Med Chem Lett 19: 4026-30 (2009), which is incorporated by reference herein.

Cholinesterase

In some embodiments, the Target Extracellular Protein is human cholinesterase (UniProtKB—P06276 (CHLE_HUMAN)). Cholinesterase contributes to the inactivation of the neurotransmitter acetylcholine. Inhibition of cholinesterase results in increased levels of acetylcholine in the synaptic cleft (the space between two nerve endings). The main use of cholinesterase inhibitors is for the treatment of dementia in patients with Alzheimer's disease. People with Alzheimer's disease have reduced levels of acetylcholine in the brain. Cholinesterase inhibitors have been shown to have an effect on dementia symptoms such as cognition.

The Protein Data Bank website provides the crystal structure of cholinesterase searchable by 1P0I and 1P0Q (Nicolet, Y., et al., J Biol Chem., 2003, 278, 41141-41147); as well as the crystal structure of cholinesterase bound to various compounds searchable by 1P0M and 1P0P (Nicolet, Y., et al., J Biol Chem., 2003, 278, 41141-41147); 2J4C (Frasco, M. F., et al., FEBS J., 2007, 274 1849); 4BDT, 4BDS (Nachon, F., et al., Biochem J, 2013, 453, 393-399); 1GQR and 1GQS (Bar-on, P., et al., Biochemistry, 2002, 41, 3555); 3DJY and 3DKK (Carletti, E., et al., J Am Chem Soc., 2008, 130, 16011-16020); 4AXB, 4B00, 4BOP, and 4BBZ (Wandhammer, M., et al., Chem Biol Interact., 2013, 203, 19); 1DX6 (Greenblatt, H. M., et al., FEBS Lett., 1999, 463 321); 1GPK and 1GPN (Dvir, H., et al., Biochemistry, 2002, 41, 10810); 6CQY (Bester, S. M., et al., Chem Res Toxicol., 2018, 31, 1405-1417); 1XLV and 1XLW (Nachon, F., et al., Biochemistry, 2005, 44, 1154-1162); 2Y1K (Carletti, E., et al., Chem Res Toxicol., 2011, 24, 797); and 2WIG, 2WIJ, 2WIK, 2WIL, and 2WSL (Carletti, E., et al., Biochem J., 2009, 421, 97-106). Additionally, Ahmad et al., provides insight into the isolation, crystal structure determination and cholinesterase inhibitory potential of isotalatizidine hydrate from delphinium denudatum (Ahmad H., et al., Journal Pharmaceutical Biology, 2016, 55(1), 680-686).

Representative cholinesterase Targeting Ligands are provided in FIG. 1. Additional Targeting Ligands can be found in, for example, ACS Med Chem Lett 4: 1178-82 (2013); J Med Chem 49: 3421-5 (2006); Eur J Med Chem 55: 23-31 (2012); J Med Chem 51: 3154-70 (2008); J Med Chem 46: 1-4 (2002); Eur J Med Chem 126: 652-668 (2017); Biochemistry 52: 7486-99 (2013); Bioorg Med Chem 23: 1321-40 (2015); which are each incorporated herein by reference.

C—C Motif Chemokine Ligand 2 (CCL2)

Grygiel et al., provides insight into the synthesis by native chemical ligation and crystal structure of human CCL2 (Grygiel, T. L., et al., Biopolymers, 2010, 94(3), 350-9).

In some embodiments, the Target Extracellular Protein is human C—C motif chemokine ligand 2 (CCL2) (UniProtKB—P13500 (CCL2_HUMAN)). CCL2 acts as a ligand for C—C chemokine receptor CCR2. CCL2 signals through binding and activation of CCR2 and induces a strong chemotactic response and mobilization of intracellular calcium ions. CCL2 exhibits a chemotactic activity for monocytes and basophils but not neutrophils or eosinophils.

CCL2 has been implicated in the recruitment of monocytes into the arterial wall during the disease process of atherosclerosis.

Representative CCL2 Targeting Ligands are provided in FIG. 1. Additional CCL2 Targeting Ligands can be found in, for example, J Med Chem 56: 7706-14 (2013), which is incorporated herein by reference.

Carboxypeptidase B2

In some embodiments, the Target Extracellular Protein is human carboxypeptidase B2 (UniProtKB—Q96IY4 (CBPB2_HUMAN)). Carboxypeptidase B2, also known as thrombin activatable fibrinolysis inhibitor (TAFIa), cleaves C-terminal arginine or lysine residues from biologically active peptides such as kinins or anaphylatoxins in the circulation thereby regulating their activities. It down-regulates fibrinolysis by removing C-terminal lysine residues from fibrin that has already been partially degraded by plasmin. Carboxypeptidase B2 has been implicated and targeted to inhibit thrombosis.

The Protein Data Bank website provides the crystal structure of carboxypeptidase B2 (also known as thrombin-activatable fibrinolysis inhibitor (TAFI)) searchable by 3D66 (Marx, P. F., et al., Blood, 2008, 112, 2803-2809); 3DGV (Anand, K., et al., JBC, 2008, 283, 29416-29423); and 1KWM (Barbosa Pereira, P. J., et al., J Mol Biol., 2002, 321, 537-547); as well as the crystal structure of TAFI bound to various compounds searchable by 3D67 (Marx, P. F., et al., Blood, 2008, 112, 2803-2809); 5HVF, 5HVG, 5HVH (Zhou, X., et al., J Thromb Haemost., 2016, 14, 1629-1638); and 3LMS (Sanglas, L., et al., J Thromb Haemost., 2010, 8, 1056-1065). Additionally, Schreuder et al., provides insight into the interaction of TAFI and anabaenopeptin, a highly potent inhibitor of TAFI (Schreuder, H., et al., Sci Rep., 2016, 6, 32958).

Representative carboxypeptidase B2 Targeting Ligands are provided in FIG. 1. Additional carboxypeptidase B2 Targeting Ligands can be found in, for example, Bioorg Med Chem Lett 20: 92-6 (2010), J Med Chem 50: 6095-103 (2007), Bioorg Med Chem Lett 14: 2141-5 (2004), J Med Chem 58: 4839-44 (2015), J Med Chem 55: 7696-705 (2012), J Med Chem 59: 9567-9573 (2016), Bioorg Med Chem Lett 17: 1349-54 (2007), U.S. Pat. Nos. 9,662,310, 8,609,710, 9,688,645, J Med Chem 46: 5294-7 (2003), each of which is incorporated herein by reference.

Neutrophil Elastase

In some embodiments, the Target Extracellular Protein is human neutrophil elastase (UniProtKB—P08246 (ELNE_HUMAN)). Neutrophil elastase modifies the functions of natural killer cells, monocytes and granulocytes. Inhibits C5a-dependent neutrophil enzyme release and chemotaxis.

Neutrophil elastase has been implicated in a number of disorders, including lung disease, chronic obstructive pulmonary disease, pneumonia, respiratory distress, and acute lung injury (ALI), and cystic fibrosis, as well as chronic kidney disease.

The Protein Data Bank website provides the crystal structure of human neutrophil elastase bound to various compounds searchable by 3Q76 and 3Q77 (Hansen, G., et al., J. Mol. Biol., 2011, 409, 681-691); 5ABW (Von Nussbaum, et al., Bioorg Med Chem Lett., 2015, 25, 4370-4381); 1B0F (Cregge, R. J., et al., J Med Chem., 1998, 41, 2461-2480); 1H1B (Macdonald, S. J. F., et al., J Med Chem., 2002, 45, 3878); 2Z7F (Koizumi, M., et al., J Synchrotron Radiat., 2008, 15 308-311); 5A09, 5A0A, 5A0B, and 5A0C (Von Nussbaum, F., et al., Chem Med Chem., 2015, 10, 1163-1173); 5A8X, 5A8Y and 5A8Z (Von Nussbaum, F., et al., ChemMedChem., 2016, 11, 199-206); 1HNE (Navia, M. A., et al., Proc Natl Acad Sci USA, 1989, 86, 7-11); 6F5M (Hochscherf, J., et al., Acta Crystallogr F Struct Biol Commun., 2018, 74, 480-489); and 4WVP (Lechtenberg, B. C., et al., ACS Chem Biol., 2015, 10, 945-951).

Representative neutrophil elastase Targeting Ligands are provided in FIG. 1. Additional neutrophil elastase Targeting Ligands can be found in, for example, J Med Chem 53:

241-53 (2010), J Med Chem 38: 739-44 (1995), J Med Chem 37: 2623-6 (1994), J Med Chem 38: 4687-92 (1995), J Med Chem 45: 3878-90 (2002), Bioorg Med Chem Lett 5: 105-109 (1995), Bioorg Med Chem Lett 11: 243-6 (2001), J Med Chem 40: 1906-18 (1997), Bioorg Med Chem Lett 25: 4370-81 (2015), U.S. Pat. Nos. 8,569,314, 9,174,997, 9,290, 457, each of which is incorporated herein by reference.

Factor Xa

In some embodiments, the Target Extracellular Protein is human Factor Xa (UniProtKB—P00742 (FA10_HUMAN)). Factor Xa is a vitamin K-dependent glycoprotein that converts prothrombin to thrombin in the presence of factor Va, calcium and phospholipid during blood clotting.

Factor X has been implicated in the development of deep vein thrombosis and acute pulmonary embolism, and the risk of stroke and embolism in people with nonvalvular atrial fibrillation.

The Protein Data Bank website provides the crystal structure of Factor Xa bound to various compounds searchable by 1G2L and 1G2M (Nar, H., et al., Structure, 2001, 9, 29-38); 2PR3 (Nan huis, C. A., et al., Chem Biol Drug Des., 2007, 69, 444-450); 2UWP (Young, R. J., et al., Bioorg Med Chem Lett., 2007, 17, 2927); 2VVC, 2VVV, 2VVU, 2VWL, 2VWM, 2VWN and 2VWO (Zbinden, K. G., et al., Eur J Med Chem., 2009, 44, 2787); 4Y6D, 4Y71, 4Y7A, 4Y7B, 4zh8, 4ZHA (Convery, M. A. et al.); 4Y76, 4Y79, 2J94 and 2J95 (Chan, C., et al., J Med Chem., 2007, 50 1546-1557); 1FAX (Brandstetter, H., et al., J Biol Chem., 1996, 271, 29988-29992); 2JKH (Salonen, L. M., et al., Angew Chem Int Ed Engl., 2009, 48, 811); 2PHB (Kohrt, J. T., et al., Chem Biol Drug Des., 2007, 70, 100-112); 2W26 (Roehrig, S., et al., J Med Chem., 2005, 48, 5900); 2Y5F, 2Y5G and 2Y5H (Salonen, L. M., et al., Chemistry, 2012, 18, 213); 3Q3K (Yoshikawa, K., et al., Bioorg Med Chem Lett., 2011, 21, 2133-2140); 2BMG (Matter, K., et al., J Med Chem., 2005, 48, 3290); 2BOH, 2BQ6 2BQ7, and 2BQW (Nazare, M., et al., J Med Chem., 2005, 48, 4511); 2CJI (Watson, N. S., et al, Bioorg Med Chem Lett., 2006, 16, 3784); 2J2U, 2J34, 2J38, 2J41 (Senger, S., et al., Bioorg Med Chem Lett., 2006, 16 5731); 3IIT (Yoshikawa, K., et al., Bioorg Med Chem., 2009, 17 8221-8233); 1EZQ, 1FOR and 1FOS (Maignan, S., et al., J Med Chem., 2000, 43, 3226-3232); 1FJS (Adler, M., et al., Biochemistry, 2000, 39, 12534-12542); 1KSN (Guertin, K. R., et al., Bioorg Med Chem Lett., 2002, 12, 1671-1674); 1NFU, 1NFW, 1NFX and 1NFY (Maignan, S., et al., J Med Chem., 2003, 46, 685-690); 2XBV, 2XBW, 2XBX, 2XBY, 2XC0, 2XC4 and 2XC5 (Anselm, L., et al., Bioorg Med Chem Lett., 2010, 20, 5313); 4A7I (Nazare, M., et al., Angew Chem Int Ed Engl., 2012, 51, 905); 4BTI, 4BTT and 4BTU (Meneyrol, L., et al., J Med Chem., 2013, 56, 9441); 3FFG, 3KQB, 3KQC, 3KQD and 3KQE (Quan, M. L., et al., Bioorg Med Chem Lett., 2010, 20, 1373-1377); 2P93, 2P94 and 2P95 (Qiao, J. X., et al., Bioorg Med Chem Lett., 2007, 17, 4419-4427); 1V3X (Haginoya, N., et al., J Med Chem., 2004, 47, 5167-5182); 2P16 (Pinto, D. J. P., et al., J Med Chem., 2007, 50, 5339-5356); 2RAO (Lee, Y. K., et al., J Med Chem., 2008, 51, 282-297); 3SW2 (Shi, Y., et al., Bioorg Med Chem Lett., 2011, 21, 7516-7521); 2VH6 (Young, R. J., et al., Bioorg Med Chem Lett., 2008, 18, 23); 2WYG and 2WYJ (Kleanthous, S., et al., Bioorg Med Chem Lett., 2010, 20, 618); 2Y7X (Watson, N. S., et al., Bioorg Med Chem Lett., 2011, 21, 1588); 2Y7Z, 2Y80, 2Y81 and 2Y82 (Young, R. J., et al., Bioorg Med Chem Lett., 2011, 21, 1582); 3KL6 (Fujimoto, T., et al., J Med Chem., 2010, 53, 3517-3531); 3LIW (Meuller, M. M., et al., Biol. Chem., 2003, 383, 1185); 5KOH (Schweinitz, A., et al., Med Chem., 2006, 2, 349-361); 1XKA and 1XKB (Kamata, K., et al., Proc Natl Acad Sci USA, 1998, 95, 6630-6635); 2EI6 and 2EI7 (Nagata, T., et al., Bioorg Med Chem Lett., 2007, 17, 4683-4688); 2P3T (Ye, B., et al., J Med Chem., 2007, 50, 2967-2980); 1MQ5 and 1MQ6 (Adler, M., et al., Biochemistry, 2002, 41, 15514-15523); 3K9X and 3HPT (Shi, Y., et al., Bioorg Med Chem Lett., 2009, 19, 6882-6889); 3CEN (Corte, J. R., et al., Bioorg Med Chem Lett., 2008, 18, 2845-2849); 2W3I and 2W3K (Van Huis, C. A., et al., Bioorg Med Chem., 2009, 17, 2501); 2H9E (Murakami, M. T., et al., J Mol Biol., 2007, 366, 602-610); 1WU1 and 2D1J (Komoriya, S., et al., Bioorg Med Chem., 2005, 13, 3927-3954); 2G00 (Pinto, D. J. P., et al., Bioorg Med Chem Lett., 2006, 16, 5584-5589); 3M36 and 3M37 (Pruitt, J. R. et al., J Med Chem., 2003, 46, 5298-5315); 3CS7 (Qiao, J. X., et al., Bioorg Med Chem Lett., 2008, 18, 4118-4123); 1Z6E (Quan, M. L., et al., J Med Chem., 2005, 48, 1729-1744); 2FZZ (Pinto, D. J. P., et al., Bioorg Med Chem Lett., 2006, 16, 4141-4147); and 3ENS (Shi, Y., et al., J Med Chem., 2008, 51, 7541-7551).

Representative Factor Xa Targeting Ligands are provided in FIG. 1. Additional Factor Xa Targeting Ligands can be found in, for example, Bioorg Med Chem Lett 20: 5313-9 (2010), Bioorg Med Chem Lett 13: 679-83 (2003), J Med Chem 44: 566-78 (2001), J Med Chem 50: 2967-80 (2007), J Med Chem 38: 1511-22 (1995), Bioorg Med Chem Lett 18: 2845-9 (2008), J Med Chem 53: 6243-74 (2010), Bioorg Med Chem Lett 18: 2845-9 (2008), Bioorg Med Chem 16: 1562-95 (2008), each of which is incorporated herein by reference.

Factor XI

In some embodiments, the Target Extracellular Protein is human Factor XI UniProtKB—P03951 (FA11_HUMAN). Factor XI triggers the middle phase of the intrinsic pathway of blood coagulation by activating factor IX.

Factor XI has been implicated in the development of deep vein thrombosis and acute pulmonary embolism, and the risk of stroke and embolism in people with nonvalvular atrial fibrillation.

The Protein Data Bank website provides the crystal structure of Factor XI bound to various compounds searchable by 1ZSL, 1ZTJ, 1ZTK, and 1ZTL (Nagafuji, P., et al.); 1ZOM (Lin, J., et al., J Med Chem., 2006, 49, 7781-7791); 5EOK and 5EOD (Wong, S. S., et al., Blood, 2016, 127, 2915-2923); 1ZHM, 1ZHP and 1ZHR (Jin, L., et al., Acta Crystallogr D Biol Crystallogr., 2005, 61, 1418-1425); 1ZMJ, 1ZLR, 1ZML and 1ZMN (Lazarova, T. I., Bioorg Med Chem Lett., 2006, 16, 5022-5027); 1ZRK, 1ZSJ and 1ZSK (Guo, Z., et al); 4CRA, 4CRB, 4CRC, 4CRD, 4CRE, 4CRF and 4CRG (Fjellstrom, O., et al., PLoS One, 2015, 10, 13705); 3SOR and 3SOS (Fradera, X., et al., Acta Crystallogr Sect F Struct Biol Cryst Commun., 2012, 68, 404-408); 1ZPB, 1ZPC, 2FDA (Deng, H., et. al., Bioorg Med Chem Lett., 2006, 16, 3049-3054); 5WB6 (Wang, C., et al., Bioorg Med Chem Lett., 2017, 27, 4056-4060); 4NA7 and 4NA8 (Quan, M. L., et al., J Med Chem., 2014, 57, 955-969); 4WXI (Corte, J. R., et al., Bioorg Med Chem Lett., 2015, 25, 925-930); 5QTV, 5QTW, 5QTX and 5QTY (Fang, T., et al., Bioorg Med Chem Lett., 2020, 126949-126949); 6COS (Hu, Z., et al., Bioorg Med Chem Lett., 28, 987-992); 5QQP and 5QQO (Clark, C. G., et al., Bioorg Med Chem Lett., 2019, 29, 126604-126604); 5QOD, 5QOE, 5QOF, 5QOG, and 5QOH (Corte, J. R., et al., Bioorg Med Chem Lett., 2017, 27, 3833-3839); 5QCK, 5QCL, 5QCM, and 5QCN (Pinto, D. J. P., et al., J Med Chem., 2017, 60, 9703-9723); 5TKS and 5TKU (Corte, J. R., et al., J Med Chem., 2017, 60, 1060-1075); 1XXD and 1XX9 (Jin, L., et al., J Biol Chem., 2005, 280, 4704-4712); 5QTT and 5QTU (Corte, J. R., et al., J Med Chem., 2019, 63, 784-803); 4TY6, 4TY7 (Hangeland, J. J., et al., J Med Chem., 2014, 57, 9915-9932); 4X6M, 4X6N, 4X6O, and 4X6P (Pinto, D. J. P., et al., Bioorg Med Chem Lett., 2015, 25, 1635-1642); and 5EXM (Corte, J. R., et al., Bioorg Med Chem., 2016, 24, 2257-2272). Additionally, Al-Horani et al., provides insight into a review of patent literature regarding Factor Xia inhibitors (Al-Horani et al., Expert Opin Ther Pat. 2016; 26(3), 323-345).

Representative Factor XI Targeting Ligands are provided in FIG. 1. Additional Factor XI Targeting Ligands can be found in, for example, U.S. Pat. No. 9,783,530, U.S. patent Ser. No. 10/143,681, U.S. patent Ser. No. 10/214,512, ACS Med Chem Lett 6: 590-5 (2015), J Med Chem 60: 9703-9723 (2017), J Med Chem 60: 9703-9723 (2017), U.S. Pat. No. 9,453,018 (2016), J Med Chem 60: 1060-1075 (2017), J Med Chem 57: 955-69 (2014), each of which is incorporated herein by reference.

In certain embodiments the Factor XI Targeting Ligand is selected from:

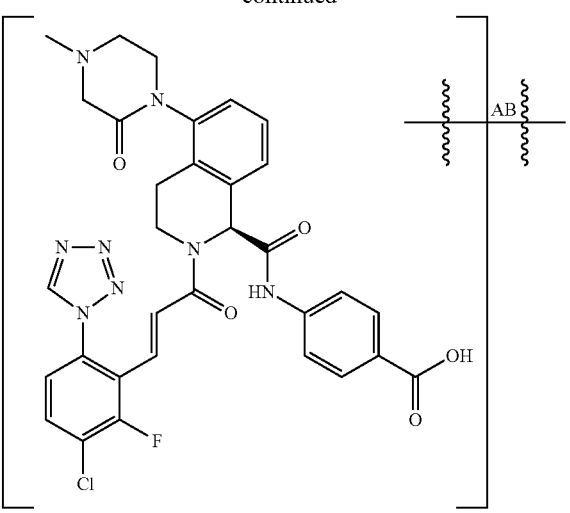

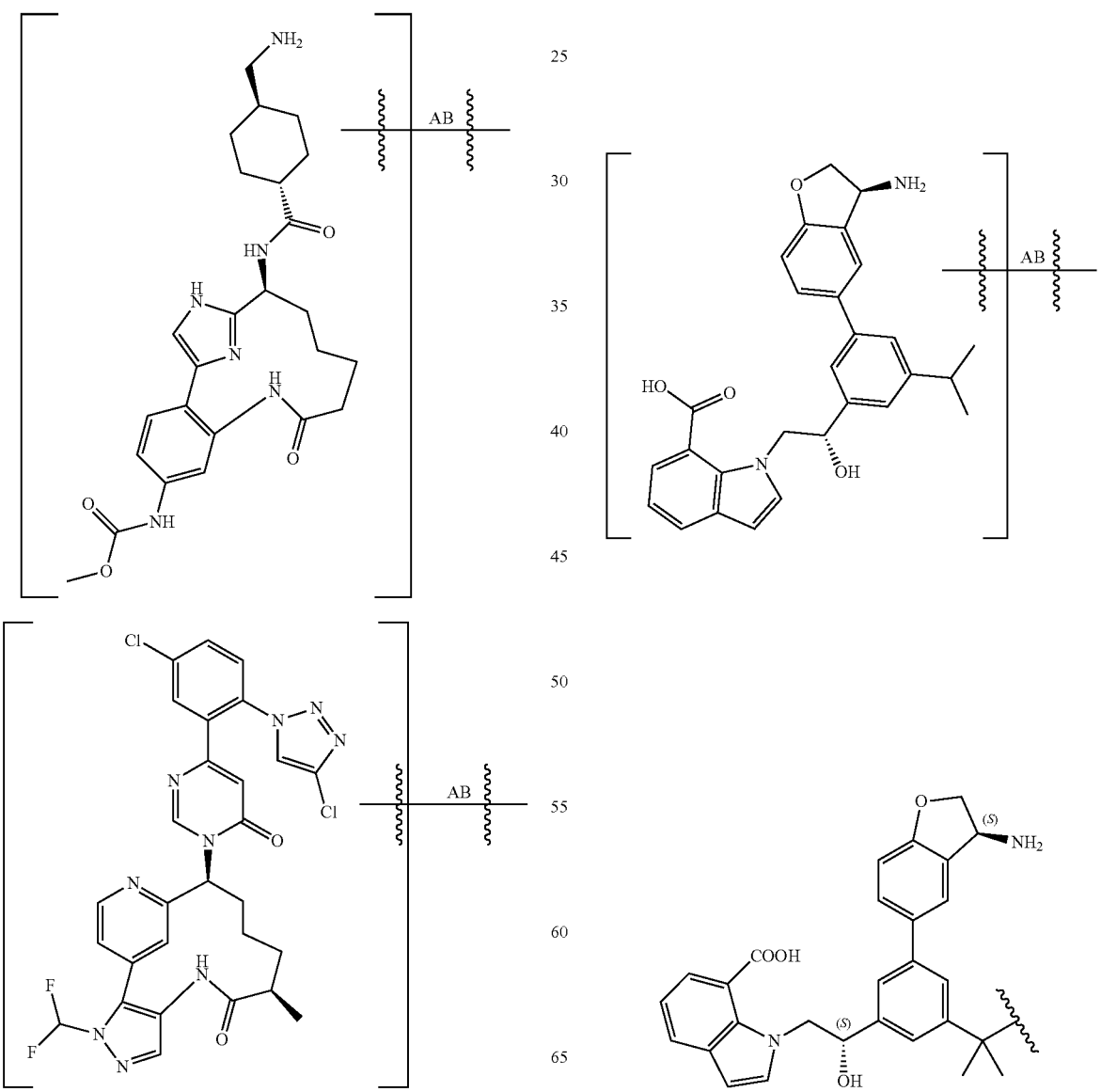

125
-continued

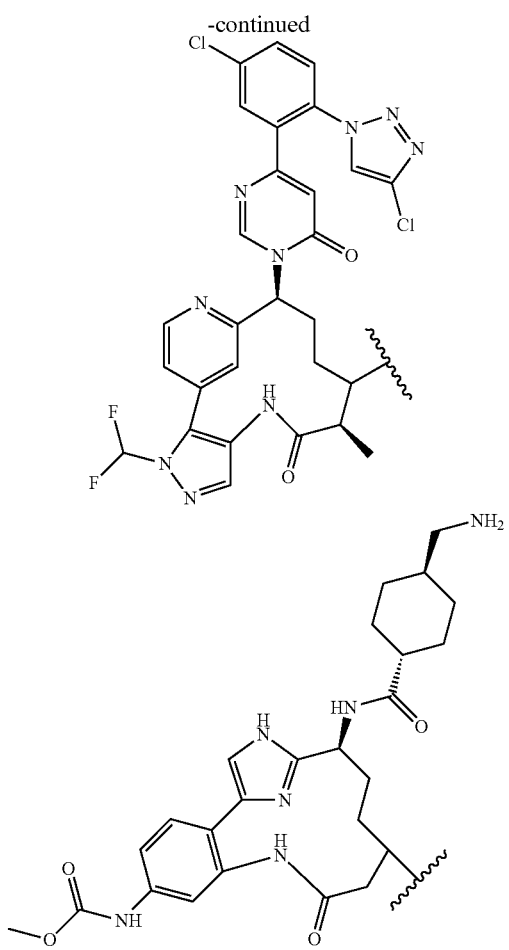

126
-continued

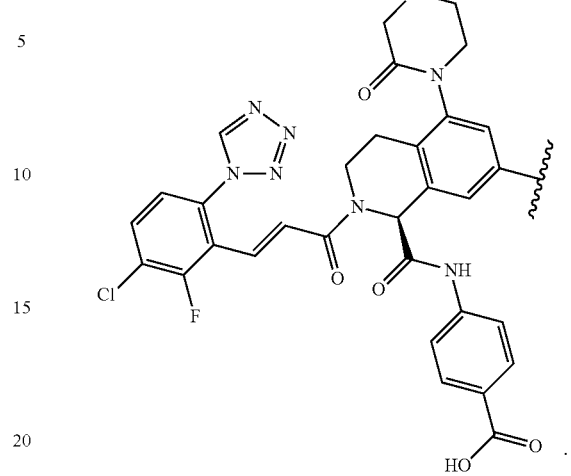

In certain embodiments the Factor XI Targeting Ligand is described in J Med Chem 61 (17), 7425-7447 (2018) or J Med Chem (2020) Structure-based design and pre-clinical characterization of selective and orally bioavailable Factor XIa inhibitors: demonstrating the power of an integrated S1 protease family approach.

Non-limiting examples of Factor XI degrading compounds include:

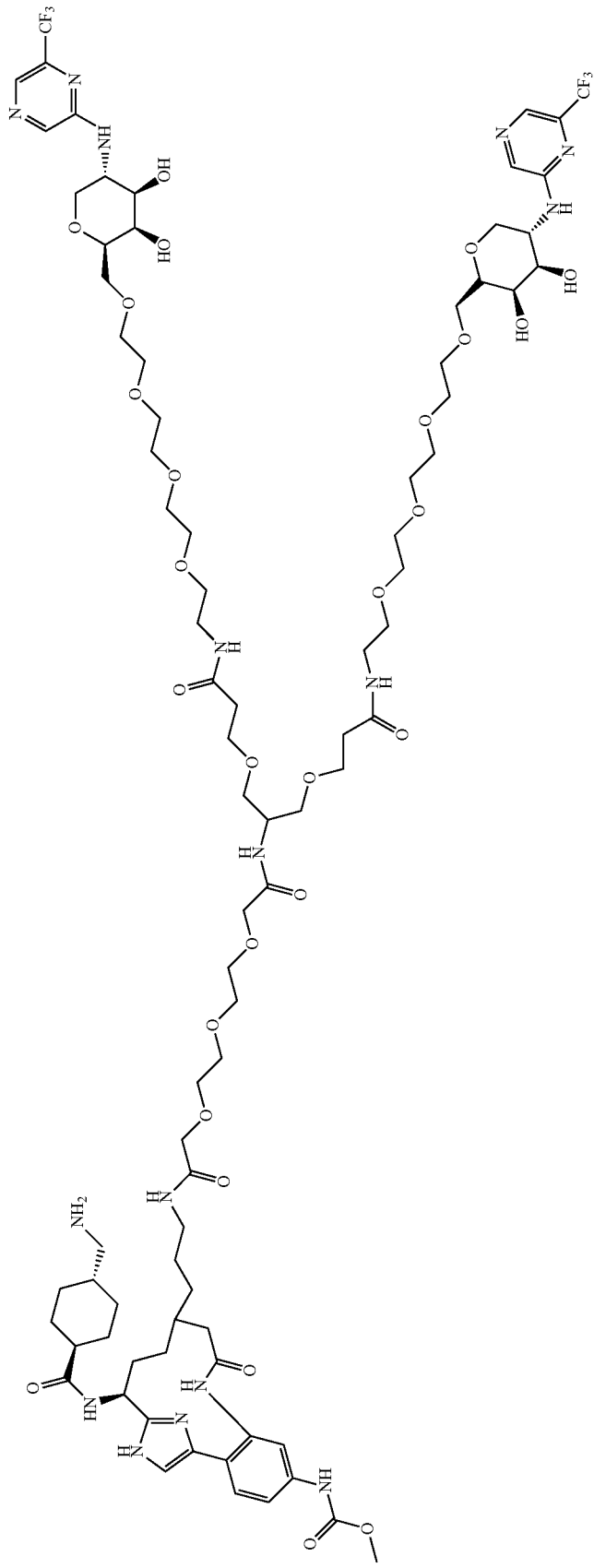

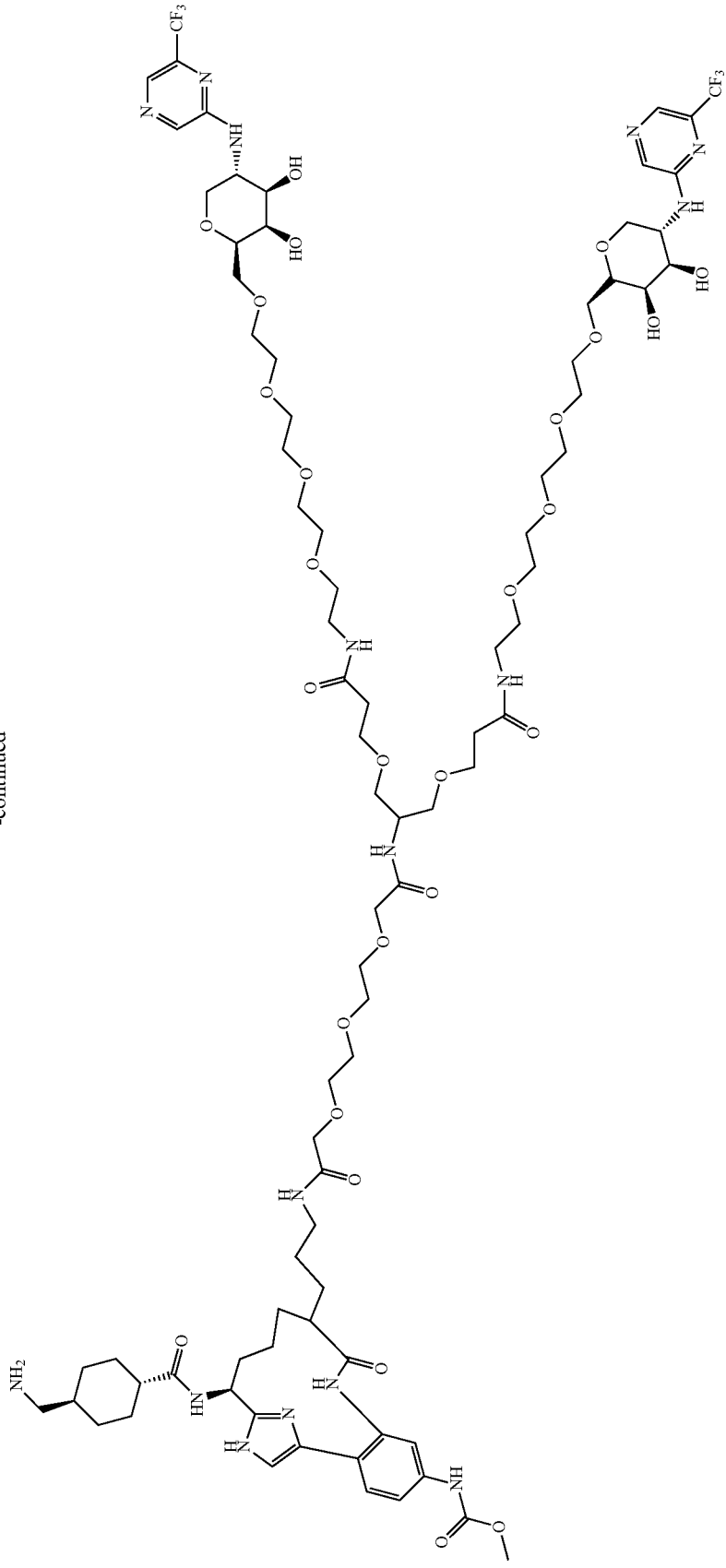

-continued
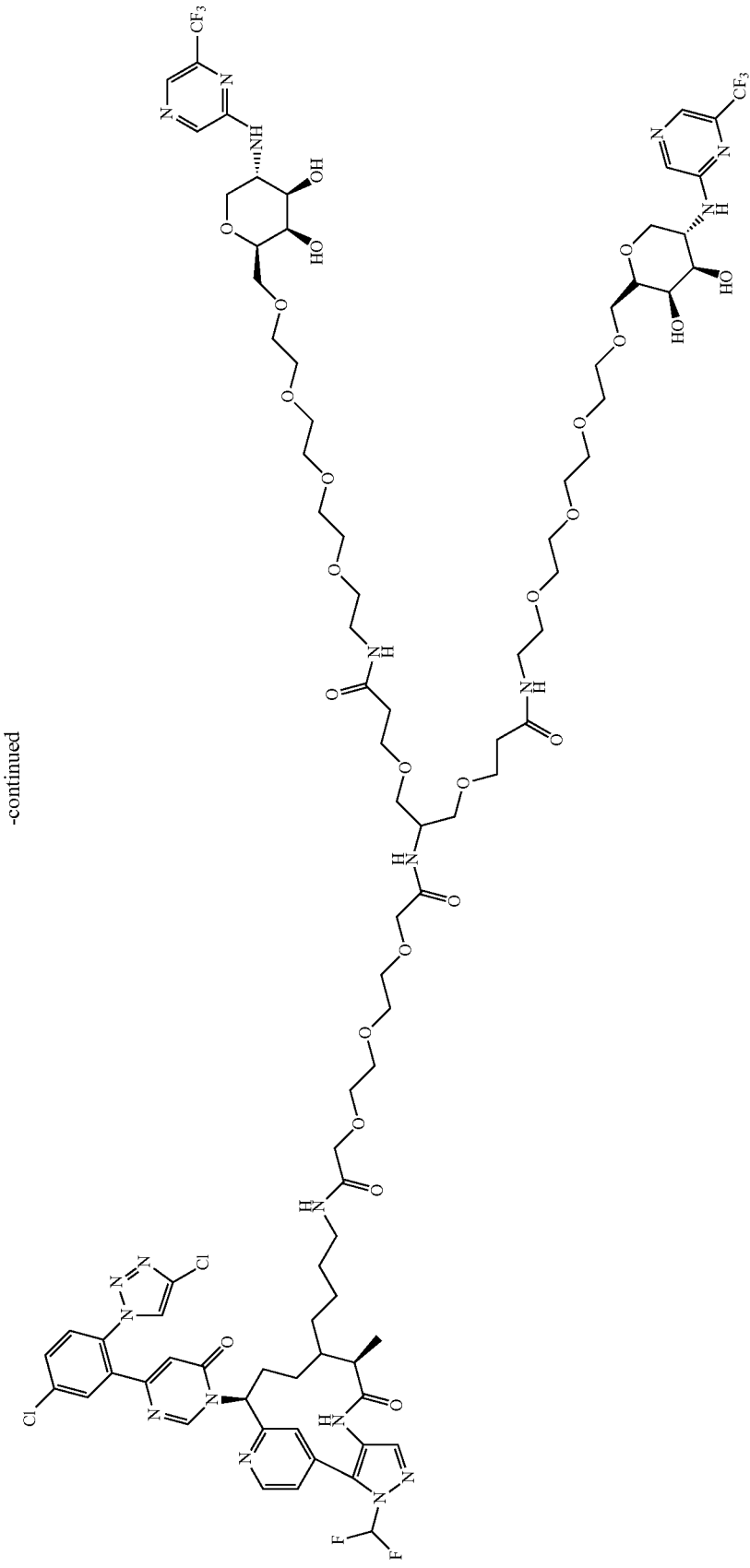

-continued
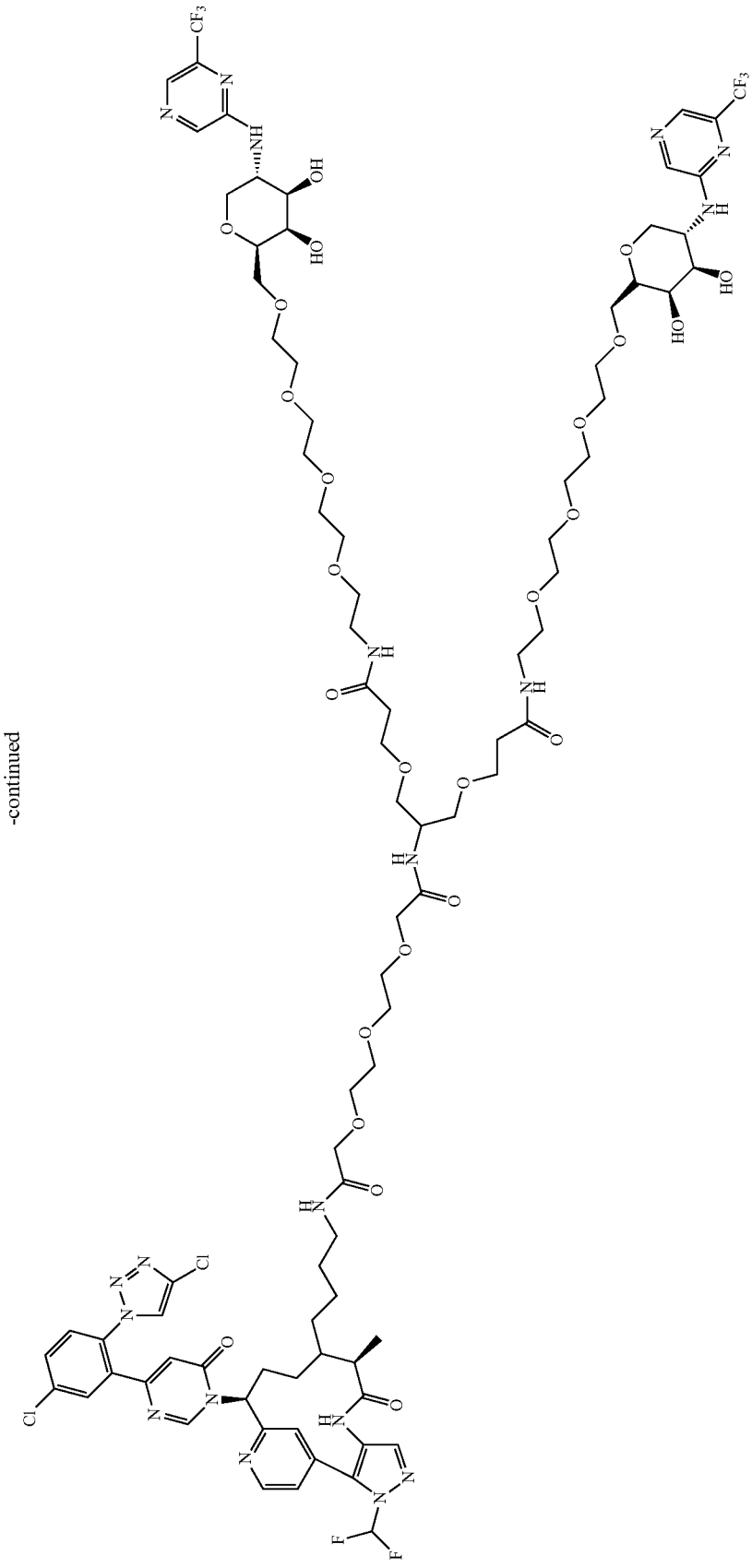

-continued
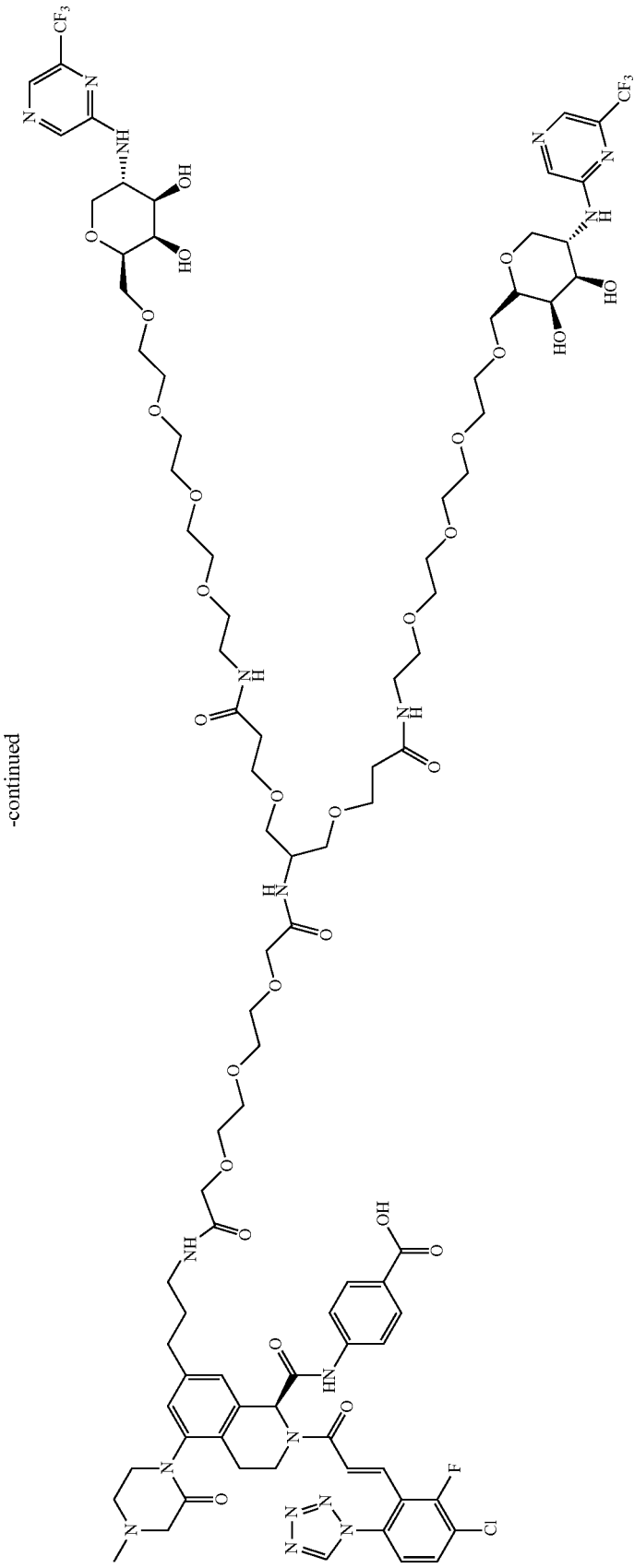

-continued
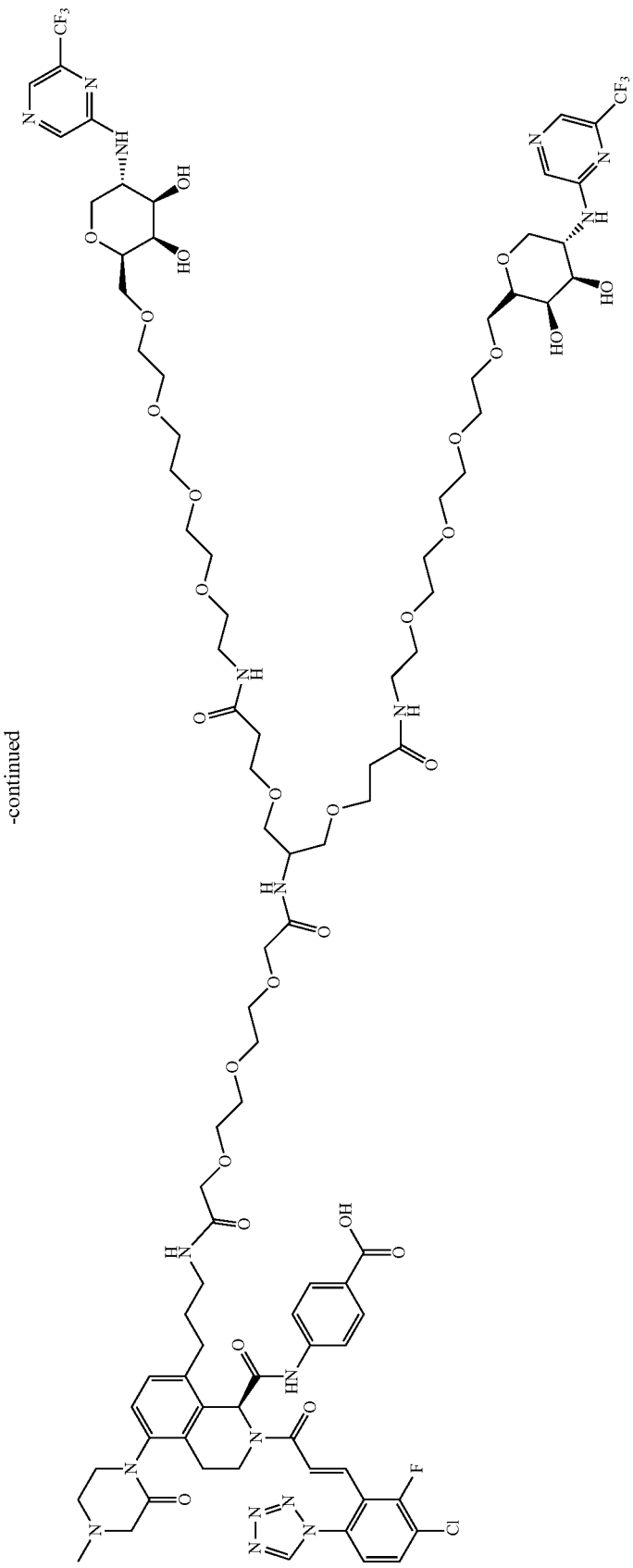

-continued
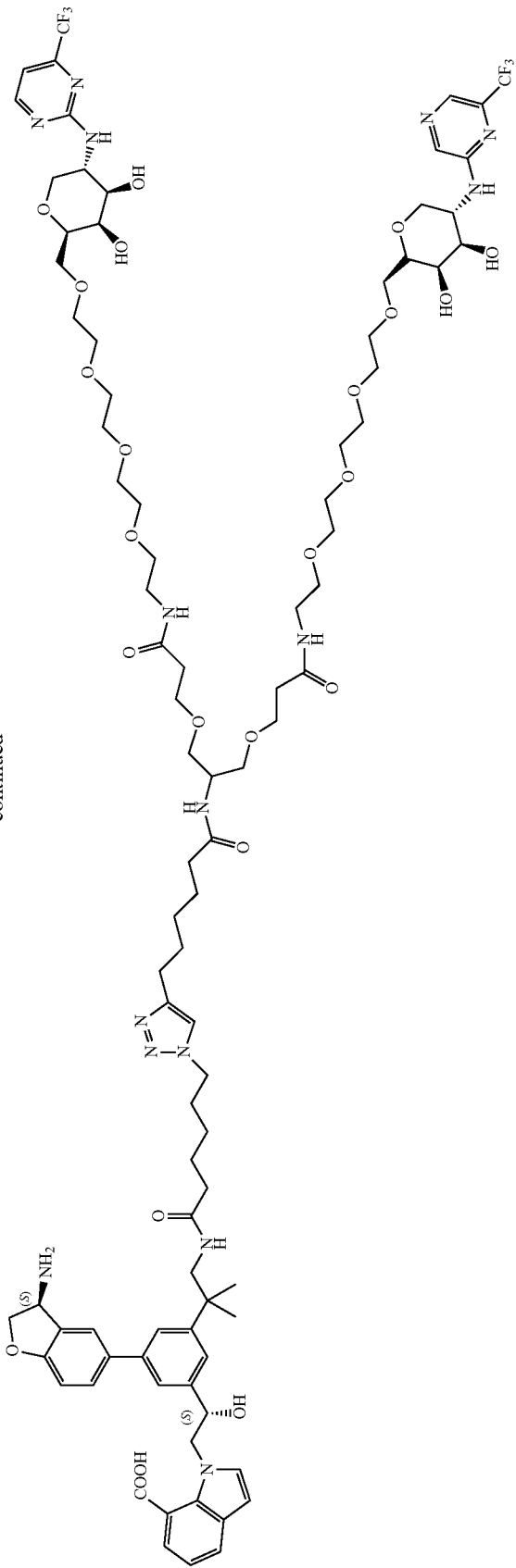

-continued
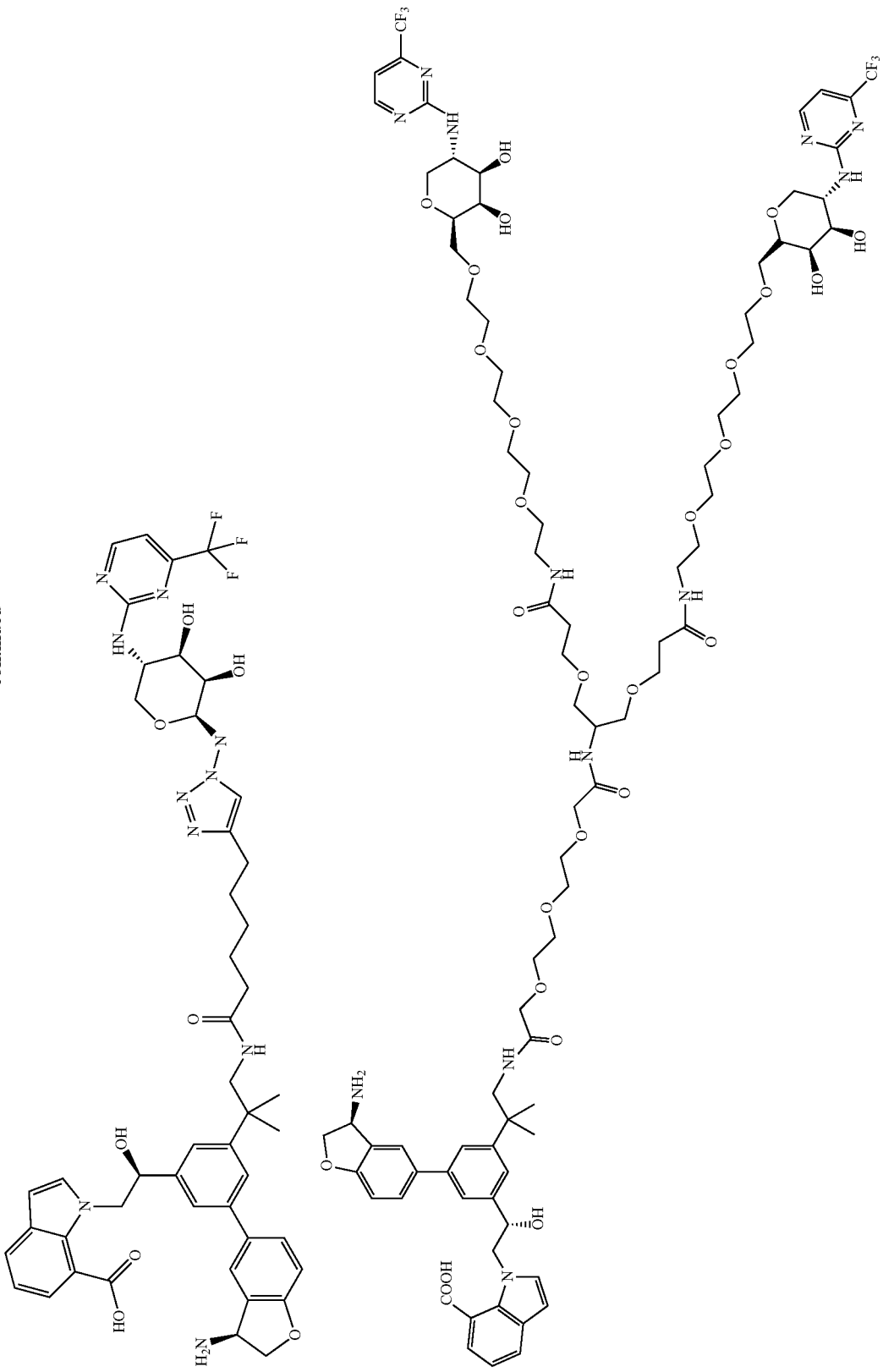

-continued
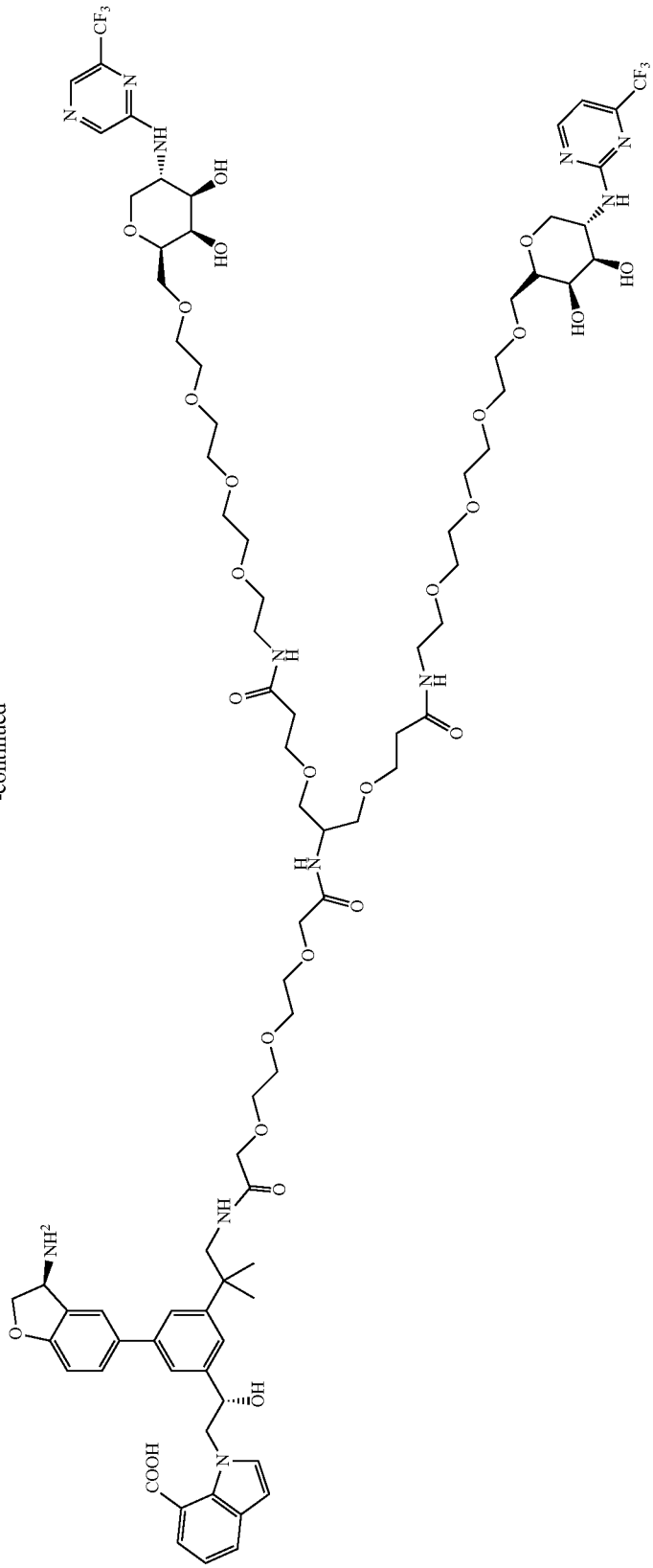

In certain non limiting embodiments, the Factor XI degrading compound of the present invention is selected from the following compounds of a bi- or tri-dentate version thereof:
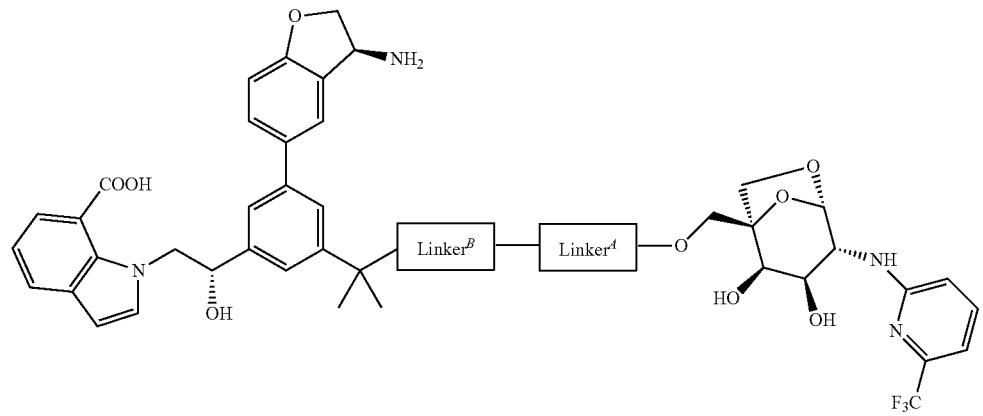
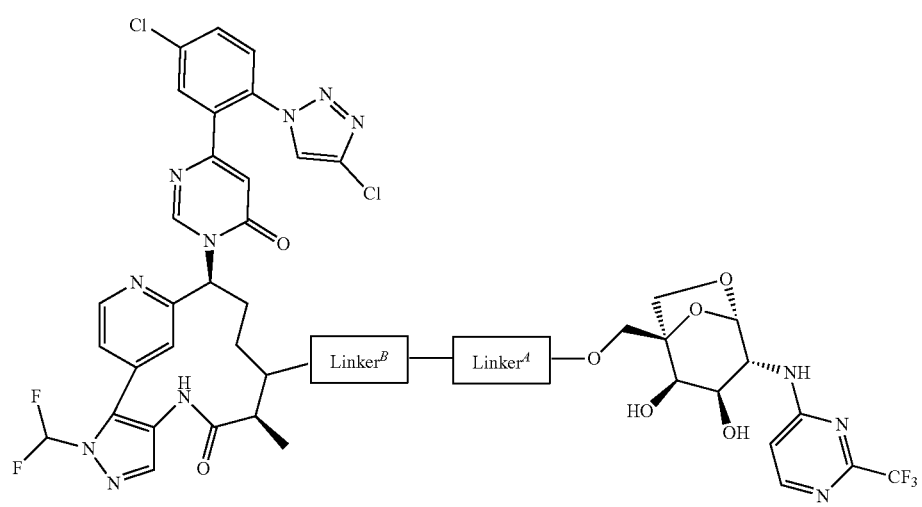
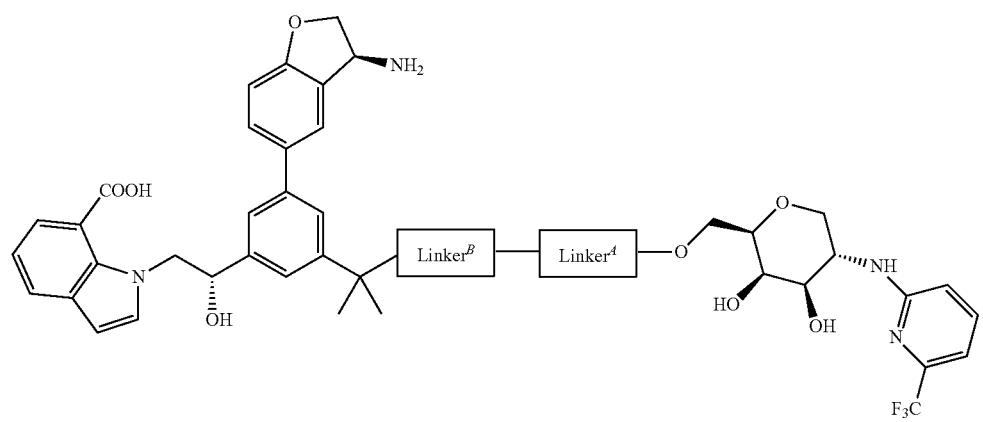

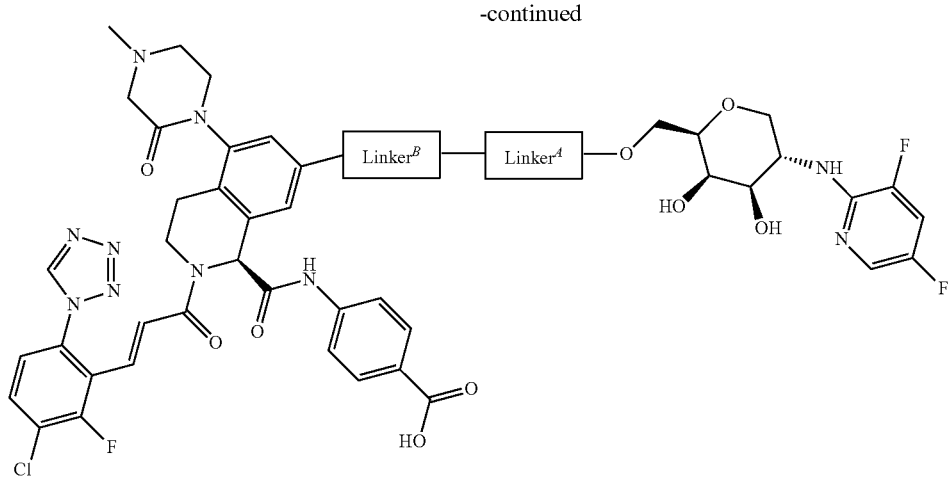
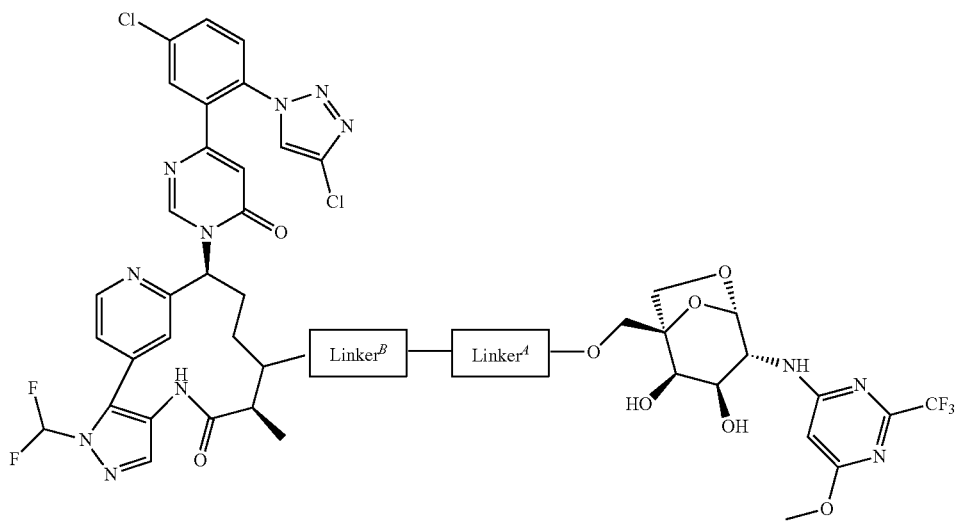
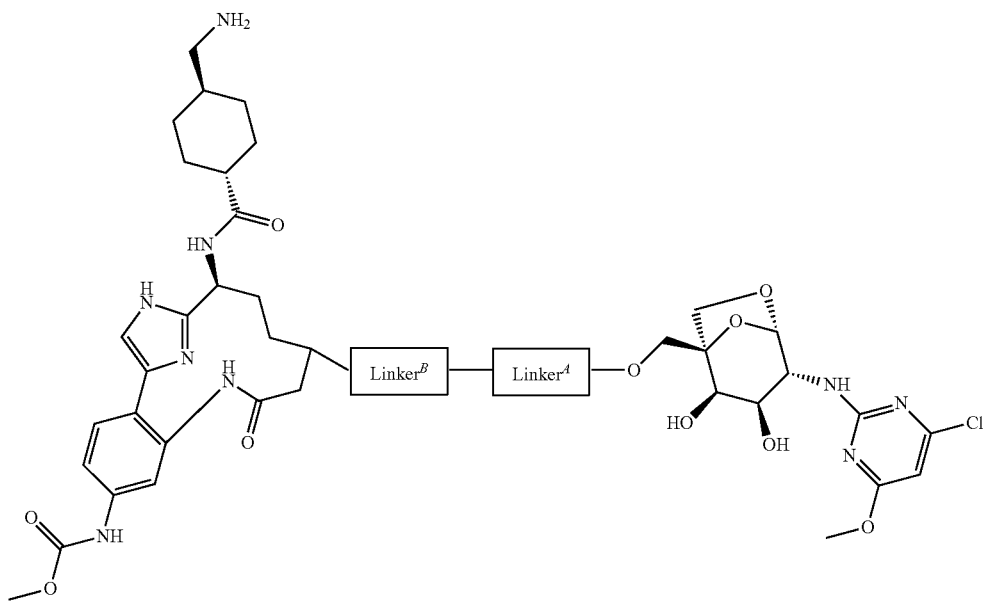

-continued
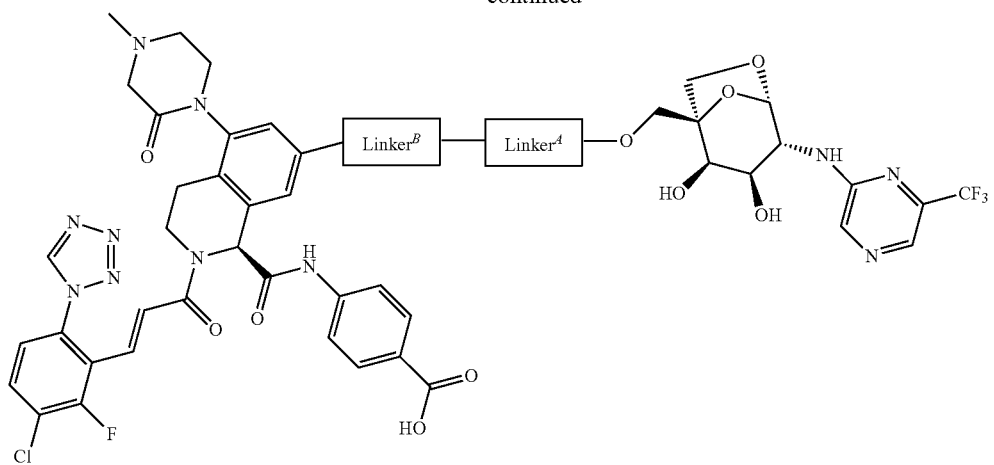
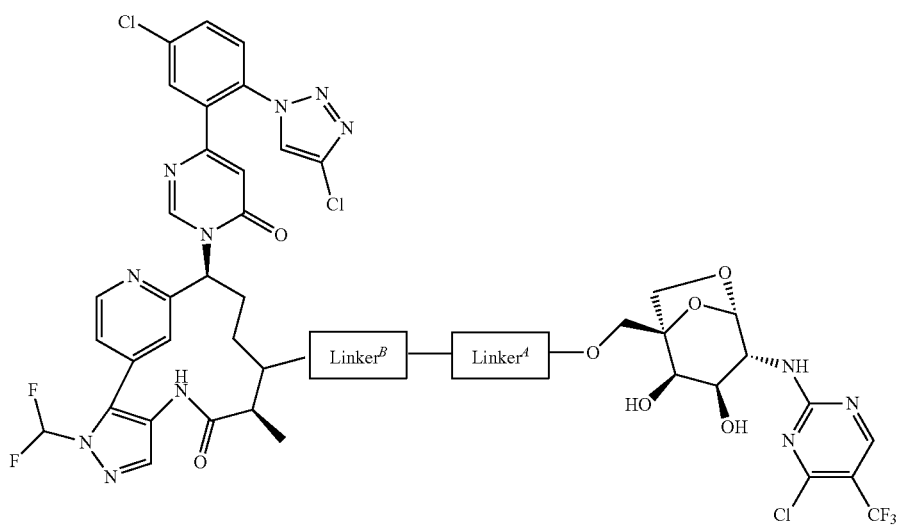
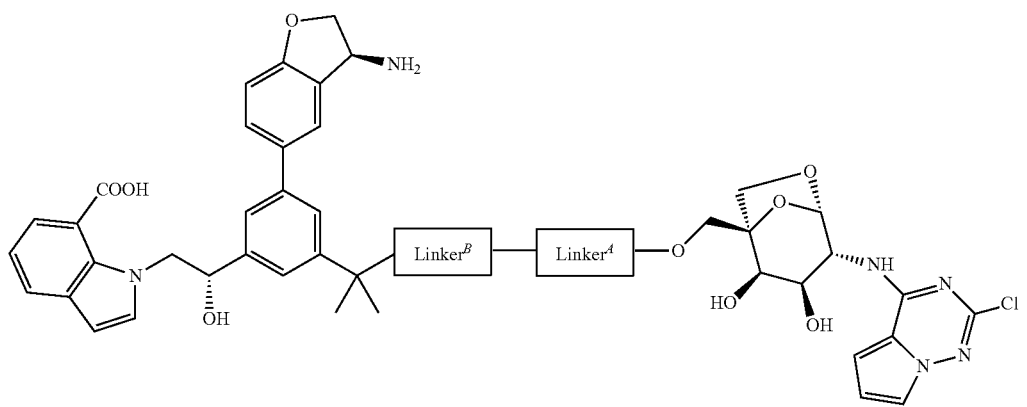

-continued
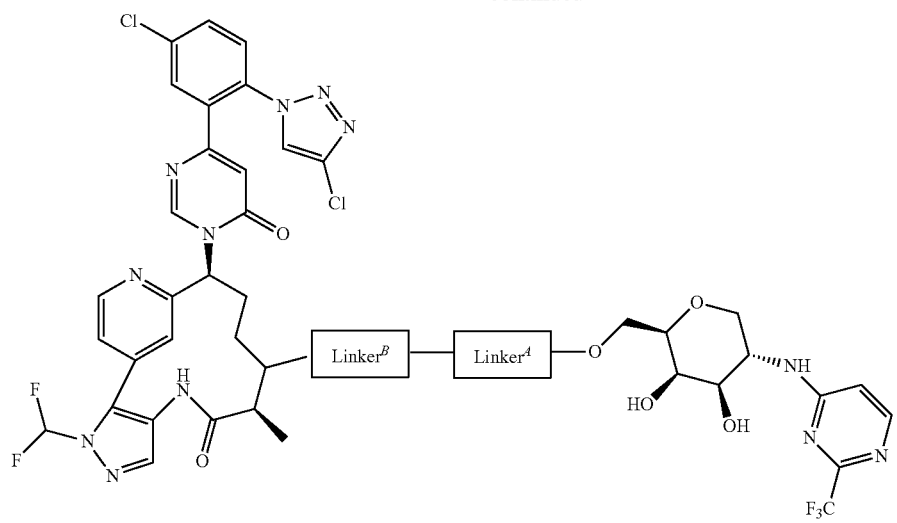
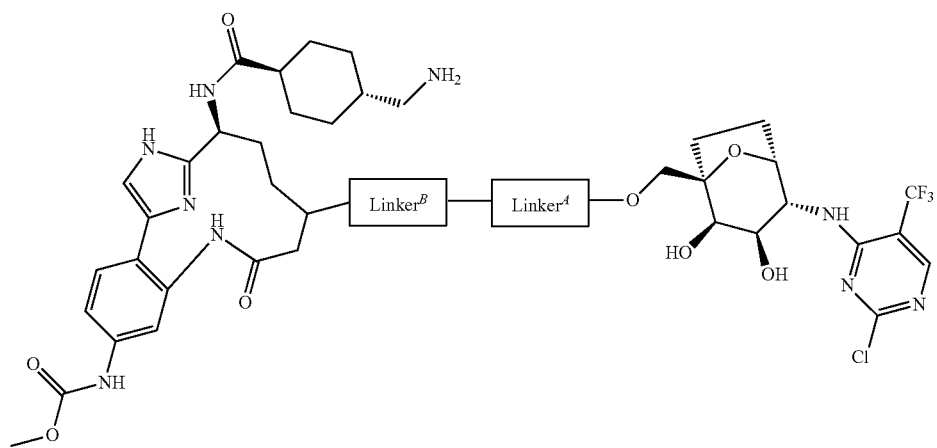
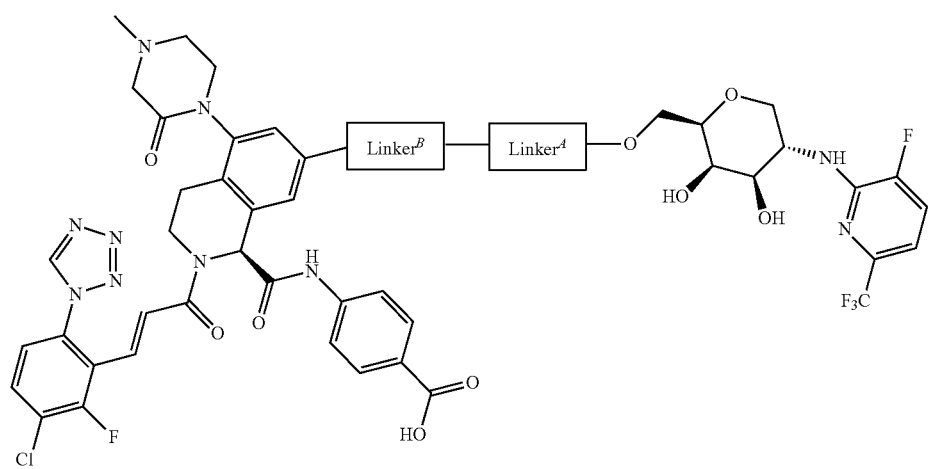

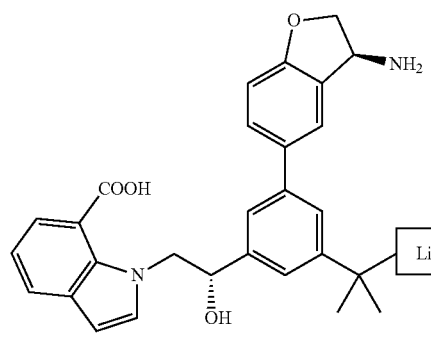
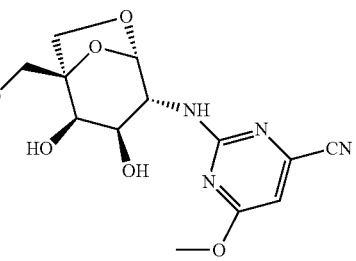

or a pharmaceutically acceptable salt thereof.

Factor XII

In some embodiments, the Target Extracellular Protein is human Factor XII (UniProtKB—P00748 (FA12_HUMAN)). Factor XII is a serum glycoprotein that participates in the initiation of blood coagulation, fibrinolysis, and the generation of bradykinin and angiotensin. Prekallikrein is cleaved by factor XII to form kallikrein, which then cleaves factor XII first to alpha-factor XIIa and then trypsin cleaves it to beta-factor XIIa. Alpha-factor XIIa activates factor XI to factor XIa.

Factor XII has been implicated in the development of deep vein thrombosis and acute pulmonary embolism, and the risk of stroke and embolism in people with nonvalvular atrial fibrillation.

The Protein Data Bank website provides the crystal structure of factor XII bound to various compounds searchable by 4XDE and 4XE4 (Pathak, M., et al., J Thromb Haemost., 2015, 13(4), 580-591); 6GT6 and 6QF7 (Pathak, M., et al., Acta Crystallogr D Struct Biol., 2019, 75, 578-591); and 6B74 and 6B77 (Dementiev, A. A., et al., Blood Adv., 2018, 2, 549-558). Additionally, Pathak et al., provides insight into the crystal structure of factor XII (Pathak, M., et al., J Thromb Haemost., 2015, 13(4), 580-591).

Representative Factor XII Targeting Ligands are provided in FIG. 1. Additional Factor XII Targeting Ligands can be found in, for example, J Med Chem 60: 1151-1158 (2017), J Med Chem 48: 2906-15 (2005), J Med Chem 50: 5727-34 (2007), J Med Chem 50: 1876-85 (2007), Chembiochem 18: 387-395 (2017), each of which is incorporated herein by reference.

Factor XIII

In some embodiments, the Target Extracellular Protein is human Factor XIII UniProtKB—P00488 (F13A_HUMAN)). Factor XIII is activated by thrombin and calcium ion to a transglutaminase that catalyzes the formation of gamma-glutamyl-epsilon-lysine cross-links between fibrin chains, thus stabilizing the fibrin clot. Also cross-link alpha-2-plasmin inhibitor, or fibronectin, to the alpha chains of fibrin.

Factor XIII has been implicated in the development of deep vein thrombosis and acute pulmonary embolism, and the risk of stroke and embolism in people with nonvalvular atrial fibrillation.

The Protein Data Bank website provides the crystal structure of factor XIII searchable by 1FIE (Yee, V. C., et al., Thromb Res., 1995, 78, 389-397); and 1F13 (Weiss, M. S., et al., FEBS Lett., 1998, 423, 291-296); as well as the crystal structure of factor XIII bound to various compounds searchable by 1DE7 (Sadasivan, C., et al., J Biol Chem., 2000, 275, 36942-36948); and 5MHL, 5MHM, 5MHN, and 5MHO (Stieler, M., et al.). Additionally, Gupta et al., provides insight into the mechanism of coagulation factor XIII activation and regulation from a structure/functional perspective (Gupta, S., et al., Sci Rep., 2016; 6, 30105); and Komaromi et al., provides insight into the novel structural and functional aspect of factor XIII (Komaromi, Z., et al., J Thromb Haemost 2011, 9, 9-20).

Representative Factor XIII Targeting Ligands are provided in FIG. 1. Additional Factor XIII Targeting Ligands can be found in, for example, Eur J Med Chem 98: 49-53 (2015), J Med Chem 55: 1021-46 (2012), J Med Chem 48: 2266-9 (2005), each of which is incorporated herein by reference.

Prothrombin

In some embodiments, the Target Extracellular Protein is human Prothrombin (UniProtKB—P00734 (THRB_HUMAN)). Thrombin, which cleaves bonds after Arg and Lys, converts fibrinogen to fibrin and activates factors V, VII, VIII, XIII, and, in complex with thrombomodulin, protein C. Functions in blood homeostasis, inflammation and wound healing.

Thrombin is involved in blood clot formation and arterial and venous thrombosis, and thromboembolism associated with atrial fibrillation.

The Protein Data Bank website provides the crystal structure of prothrombin searchable by 3NXP (Chen, Z. et al., Proc Natl Acad Sci USA, 2010, 107, 19278-19283); as well as the crystal structure of prothrombin bound to various compounds searchable by 2HIPP and 2HIPQ (Arni, R. K., et al., Biochemistry, 1993, 32, 4727-4737); 6BJR, 6C2W (Chinnaraj, M., et al., Sci Rep., 2018, 8, 2945-2945); 5EDK, 5EDM (Pozzi, N., et al., J Biol Chem., 2016, 291, 6071-6082); 3K65 (Adams, T. E., et al., Biochimie, 2016, 122, 235-242); and 6BJR and 6C2W (Chinnaraj, M. et al., Sci Rep., 2018, 8, 2945-2945). Additionally, Pozzi et al., provides insight into the mechanism and conformational flexibility for the crystal structure of prothrombin (Pozzi, N. et al., J Biol Chem., 2013, 288(31), 22734-22744); and Zhiwei et al., provides insight into the crystal structure of prothrombin-1 (Zhiwei, C. et al., PNAS, 2010, 107(45), 19278-19283).

Prothrombin is converted to thrombin, as such the Protein Data Bank website provides the crystal structure of thrombin bound to compounds searchable by 1XMN (Carter, W. J. et al., J. Biol. Chem., 2005, 280, 2745-2749); 4CH2 and 4CH8

(Lechtenberg, B. C. et al., J Mol Biol., 2014, 426, 881); 3PO1 (Karle, M. et al., Bioorg Med Chem Lett., 2012, 22, 4839-4843); 3DA9 (Nilsson, M. et al., J Med Chem., 2009, 52, 2708-2715); 2H9T and 3BF6 (Lima, L. M. T. R. et al., Biochim Biophys Acta., 2009, 1794, 873-881); 3BEF and 3BEI (Gandhi, P. S. et al., Proc Natl Acad Sci USA, 2008, 105, 1832-1837); 3BV9 (Nieman, M. T. et al., J Thromb Haemost., 2008, 6, 837-845); 2HWL (Pineda, A. O. et al., Biophys Chem., 2007, 125, 556-559); 2AFQ (Johnson, D. J. D. et al., Biochem J., 2005, 392, 21-28); 1SHH (Pineda, A. O. et al., J Biol Chem., 2004, 279, 31842-31853); 1JWT (Levesque, S. et al., Bioorg Med Chem Lett., 2001, 11, 3161-3164); 1G37 (Bachand, B. et al., Bioorg Med Chem Lett., 2001, 11, 287-290); 1EOJ and 1EOL (Slon-Usakiewicz, J. J. et al., Biochemistry, 2000, 39, 2384-2391); 1AWH (Weir, M. P. et al., Biochemistry, 1998, 37, 6645-6657); 1DIT (Krishnan, R. et al., Protein Sci., 1996, 5, 422-433); 1HAO and 1HAP (Padmanabhan, K. et al., Acta Crystallogr D Biol Crystallogr., 1996, 52, 272-282); and 1HBT (Rehse, P. H. et al., Biochemistry, 1995, 34, 11537-11544).

Representative prothrombin Targeting Ligands are provided in FIG. 1. Additional prothrombin Targeting Ligands can be found in, for example, J Med Chem 46: 3612-22 (2003), Bioorg Med Chem Lett 12: 1017-22 (2002), J Med Chem 40: 830-2 (1997), Bioorg Med Chem Lett 15: 2771-5 (2005), J Med Chem 42: 3109-15 (1999), J Med Chem 47: 2995-3008 (2004), Bioorg Med Chem 16: 1562-95 (2008), J Med Chem 42: 3109-15 (1999), each of which is incorporated herein by reference.

Coagulation Factor VII

In some embodiments, the Target Extracellular Protein is human coagulation Factor VII (UniProtKB—P08709 (FA7_HUMAN)). Factor VII initiates the extrinsic pathway of blood coagulation. It is a serine protease that circulates in the blood in a zymogen form. Factor VII is converted to Factor VIIa by Factor Xa, Factor XIIa, Factor IXa, or thrombin by minor proteolysis. In the presence of tissue factor and calcium ions, Factor VIIa then converts Factor X to Factor Xa by limited proteolysis. Factor VIIa will also convert Factor IX to Factor IXa in the presence of tissue factor and calcium.

Factor VII is involved in blood clot formation and arterial and venous thrombosis, and thromboembolism associated with atrial fibrillation.

The Protein Data Bank website provides the crystal structure of factor VII bound to various compounds searchable by 2F9B (Rai, R., et al., Bioorg Med Chem Lett., 2006, 16, 2270-2273); 5U6J (Wurtz, N. R., et al., Bioorg Med Chem Lett., 2017, 27, 2650-2654); 5L2Y, 5L2Z, and 5L30 (Ladziata, U., et al., Bioorg Med Chem Lett., 2016, 26, 5051-5057); 5I46 (Glunz, P. W., et al., J Med Chem., 2016, 59, 4007-4018); 4YLQ, 4Z6A, and 4ZMA (Sorensen, A. B., et al., J Biol Chem., 2016, 291, 4671-4683); 4YT6 and 4YT7 (Glunz, P. W., et al., Bioorg Med Chem Lett, 2015, 25, 2169-2173); 4NA9 (Quan, M. L., et al., J Med Chem., 2014, 57, 955-969); 4NG9 (hang, X., et al., ACS Med Chem Lett., 2014, 5, 188-192); 4JZD, 4JZE and 4JZF (Bolton, S. A., et al., Bioorg Med Chem Lett., 2013, 23, 5239-5243); 4JYU and 4JYV (Glunz, P. W., et al., Bioorg Med Chem Lett., 2013, 23, 5244-5248); 4ISH (Priestley, E. S., et al., Bioorg Med Chem Lett., 2013, 23, 2432-2435); 4ISI (Zhang, X., et al., Bioorg Med Chem Lett., 2013, 23, 1604-1607); 2ZZU (Shiraishi, T., et al., Chem Pharm Bull (Tokyo), 2010, 58, 38-44); 1WV7 and 1WUN (Kadono, S., et al., Biochem Biophys Res Commun., 2005, 327, 589-596); 2ZWL, 2ZP0, (Kadono, S., et al.); 2EC9 (Krishan, R., et al., Acta Crystallogr D Biol Crystallogr., 2007, 63, 689-697); 2PUQ (Larsen, K. S., et al., Biochem J., 2007, 405, 429-438); 2FLR (Riggs, J. R., et al., Bioorg Med Chem Lett., 2006, 16, 3197-3200); 2C4F (Kohrt, J. T., et al., Bioorg Med Chem Lett., 2006, 16, 1060); 2AEI (Kohrt, J. T. et al., Bioorg Med Chem Lett., 2005, 15, 4752-4756); 1WTG (Kadono, S., et al., Biochem Biophys Res Commun., 2005, 326, 859-865); 1WSS (Kadono, S., et al., Acta Crystallogr Sect F Struct Biol Cryst Commun., 2005, 61, 169-173); 1W7X and 1W8B (Zbinden, K. G., et al., Bioorg Med Chem Lett., 2005, 15, 5344); 1WQV (Kadono, S., et al., Biochem Biophys Res Commun., 2004, 324, 1227-1233); 1Z6J (Schweitzer, B. A., et al., Bioorg Med Chem Lett., 2005, 15, 3006-3011); 1YGC (Olivero, A. G., et al., J Biol Chem., 2005, 280, 9160-9169); $6R^2W$ (Sorensen, A. B., et al., J Biol Chem., 2019, 295, 517-528); 5PA8, 5PA9, 5PAA, 5PAB, 5PAC, 5PAE, 5PAF, 5PAG, 5PAI, 5PAJ, 5PAK, 5PAM, 5PAN, 5PAO, 5PAQ, 5PAR, 5PAS, 5PAT, 5PAU, 5PABV, 5PAW, 5PAX, 5PAY, 5PBO, 5PB1, 5PB2, 5PB3, 5PB4, 5PB5, and 5PB6 (Mayweg, A. V., et al.); and 5LOS (Li, Z., et al., Nat Commun., 2017, 8, 185-185). Additionally, Kemball-Cook, et al., provides insight into the crystal structure of active site-inhibited factor VIIa (Kemball-Cook, G., et al., J Struct Biol., 1999, 127(3), 213-23).

Representative Factor VII Targeting Ligands are provided in FIG. 1. Additional Factor VII Targeting Ligands can be found in, for example, U.S. Pat. No. 9,174,974, Bioorg Med Chem Lett 26: 5051-5057 (2016), Bioorg Med Chem Lett 11: 2253-6 (2001), Bioorg Med Chem Lett 15: 3006-11 (2005), Bioorg Med Chem Lett 12: 2883-6 (2002), each of which is incorporated herein by reference.

Coagulation Factor IX

In some embodiments, the Target Extracellular Protein is human coagulation Factor IX (UniProtKB—P00740 (FA9_HUMAN)). Factor IX Factor IX is a vitamin K-dependent plasma protein that participates in the intrinsic pathway of blood coagulation by converting factor X to its active form in the presence of Ca2+ ions, phospholipids, and factor VIIIa.

Factor IX is involved in blood clot formation and arterial and venous thrombosis, and thromboembolism associated with atrial fibrillation.

The Protein Data Bank website provides the crystal structure of factor IX bound to various compounds searchable by 6MV4 (Vadivel, K., et al., J Thromb Haemost., 2019, 17, 574-584); 4ZAE (Zhang, T., et al., Bioorg Med Chem Lett., 2015, 25, 4945-4949); 4YZU and 4Z0K (Parker, D. L., et al., Bioorg Med Chem Lett., 2015, 25, 2321-2325); 5TNO and 5TNT (Sakurada, I., et al., Bioorg Med Chem Lett., 2017, 27, 2622-2628); 5JB8, 5JB9, 5JBA, 5JBB and 5JBC (Kristensen, L. H., et al., Biochem J., 2016, 473, 2395-2411); 3LC3 (Wang, S., et al., J Med Chem., 2010, 53, 1465-1472); 3LC5 (Wang, S., et al., J Med Chem., 2010, 53, 1473-1482); 3KCG (Johnson, D. J. D., et al., Proc Natl Acad Sci USA, 2010, 107, 645-650); 1NLO (Huang, M., et al., J Biol Chem., 2004, 279, 14338-14346); 1RFN (Hopfner, K. P., et al., Structure, 1999, 7, 989-996); and 6RFK (Sendall, T. J., et al.).

Representative Factor IX Targeting Ligands are provided in FIG. 1. Additional Factor IX Targeting Ligands can be found in, for example, U.S. Pat. No. 9,409,908, Bioorg Med Chem Lett 25: 5437-43 (2015), U.S. patent Ser. No. 10/189,819, each of which is incorporated herein by reference.

Fibroblast Growth Factor 1 (FGF1)

In some embodiments, the Target Extracellular Protein is human fibroblast growth factor 1 (FGF1) (UniProtKB—P05230 (FGF1_HUMAN)). FGF1 plays an important role in the regulation of cell survival, cell division, angiogenesis, cell differentiation and cell migration. FGF1 acts as a ligand for FGFR1 and integrins, and binds to FGFR1 in the presence of heparin leading to FGFR1 dimerization and activation via sequential autophosphorylation on tyrosine residues which act as docking sites for interacting proteins, leading to the activation of several signaling cascades. FGF1 induces the phosphorylation and activation of FGFR1, FRS2, MAPK3/ERK1, MAPK1/ERK2 and AKT1. FGF1 can induce angiogenesis. FGF1 has been implicated in oncogenesis, cancer cell proliferation, resistance to anticancer therapies, and neoangiogenesis.

The Protein Data Bank website provides the crystal structure of FGF1 searchable by 2AFG (Blaber, M., et al., Biochemistry, 1996, 35, 2086-2094); and 1BAR (Zhu, X. et al., Science, 1991, 251, 90-93); as well as the crystal structure of FGF1 bound to various compounds searchable by 1AFC (Zhu, X., et al., Structure, 1993, 1, 27-34); 1AXM and 2AXM (DiGabriele, A. D., et al., Nature, 1998, 393, 812-817); IEVT (Plotnikov, A. N., et al., Cell, 2000, 101, 413-424); 1E0O (Pellegrini, L., et al., Nature, 2000, 407, 1029); and 2ERM (Canales, A., et al., FEBS J, 2006, 273, 4716-4727).

Representative FGF1 Targeting Ligands are provided in FIG. 1. Additional FGF1 Targeting Ligands can be found in, for example, Bioorg Med Chem Lett 18: 344-9 (2008), Chembiochem 6: 1882-90 (2005), J Med Chem 55: 3804-13 (2012), J Med Chem 47: 1683-93 (2004), J Med Chem 53: 1686-99 (2010), each of which is incorporated herein by reference.

Fibroblast Growth Factor 2 (FGF2)

In some embodiments, the Target Extracellular Protein is human fibroblast growth factor 2 (FGF2) (UniProtKB—P09038 (FGF2_HUMAN)). FGF2 acts as a ligand for FGFR1, FGFR2, FGFR3 and FGFR4. FGF2 also acts as an integrin ligand which is required for FGF2 signaling, and plays an important role in the regulation of cell survival, cell division, cell differentiation and cell migration. FGF2 also induces angiogenesis. FGF2 has been implicated in oncogenesis, cancer cell proliferation, resistance to anticancer therapies, and neoangiogenesis.

The Protein Data Bank website provides the crystal structure of FGF2 bound to various compounds searchable by 4OEE, 4OEF, and 4OEG (Li, Y. C., et al., ACS Chem Biol., 2014, 9, 1712-1717); 1EV2 (Plotnikov, A. N., et al., Cell, 2000, 101, 413-424); and 5X1O (Tsao, Y. H.).

Representative FGF2 Targeting Ligands are provided in FIG. 1. Additional FGF2 Targeting Ligands can be found in, for example, U.S. Pat. No. 8,933,099, Bioorg Med Chem Lett 12: 3287-90 (2002), Chem Biol Drug Des 86: 1323-9 (2015), Bioorg Med Chem Lett 25: 1552-5 (2015), each of which is incorporated herein by reference.

Fibronectin-1

In some embodiments, the Target Extracellular Protein is human fibronectin 1 (FN1) (UniProtKB—P02751 (FINC_HUMAN)). Fibronectin (FN) polymerization is necessary for collagen matrix deposition and is a key contributor to increased abundance of cardiac myofibroblasts (MFs) after cardiac injury. Interfering with FN polymerization may attenuate MF and fibrosis and improve cardiac function after ischemia/reperfusion (I/R) injury.

The Protein Data Bank website provides the crystal structure of fibronectin-1 bound to various compounds searchable by 3M7P (Graille, M., et al., Structure, 2010, 18, 710-718); 3MQL (Erat, M. C., et al., J Biol Chem., 2010, 285, 33764-33770); and 3EJH (Erat, M. C., et al., Proc Natl Acad Sci USA, 2009, 106, 4195-4200).

Representative FN Targeting Ligands are provided in FIG. 1. Additional FN Targeting Ligands can be found in, for example, Bioorg Med Chem Lett 18: 2499-504 (2008), which is incorporated herein by reference.

Kallikrein-1 (KLK1)

In some embodiments, the Target Extracellular Protein is human kallikrein-1 (UniProtKB—P06870 (KLK1_HUMAN)). Glandular kallikreins cleave Met-Lys and Arg-Ser bonds in kininogen to release Lys-bradykinin. Kallikrein has been implicated in adverse reactions in hereditary angioedema (HAE).

The Protein Data Bank website provides the crystal structure of KLK1 searchable by 1SPJ (Laxmikanthan, G., et al., Proteins, 2005, 58, 802-814); as well as the crystal structure of KLK1 bound to various compounds searchable by 5F8Z, 5F8T, 5F8X, (Xu, M., et al.); and 6A8O (Xu, M., et al., FEBS Lett., 2018, 592, 2658-2667). Additionally, Katz et al., provides insight into the crystal structure of kallikrein (Katz, B. A., et al., Protein Sci., 1998, 7(4), 875-85).

Representative kallikrein Targeting Ligands are provided in FIG. 1. Additional kallikrein Targeting Ligands can be found in, for example, U.S. Pat. No. 9,783,530, J Med Chem 38: 2521-3 (1995), U.S. Pat. No. 9,234,000, U.S. patent Ser. No. 10/221,161, U.S. Pat. Nos. 9,687,479, 9,670,157, 9,834,513, J Med Chem 38: 1511-22 (1995), U.S. patent Ser. No. 10/214,512, each of which is incorporated herein by reference.

Plasma Kallikrein

In some embodiments, the Target Extracellular Protein is human plasma kallikrein (UniProtKB—P03952 (KLKB1_HUMAN)). Plasma kallikrein cleaves Lys-Arg and Arg-Ser bonds. It activates, in a reciprocal reaction, factor XII after its binding to a negatively charged surface. It also releases bradykinin from HMW kininogen and may also play a role in the renin-angiotensin system by converting prorenin into renin. Plasma kallikrein has been implicated in retinal dysfunction, the development of diabetic macular edema and hereditary angioedema (HAE).

The Protein Data Bank website provides the crystal structure of plasma kallikrein bound to various compounds searchable by 5TJX (Li, Z., et al., ACS Med Chem Lett., 2017, 8, 185-190); 6O1G and 6O1S (Patridge, J. R., et al., J Struct Biol., 2019, 206, 170-182); 4OGX and 4OGY (Kenniston, J. A., et al., J Biol Chem., 2014, 289, 23596-23608); and 5F8T, 5F8X, and 5F8Z (Xu, M., et al.).

Representative plasma kallikrein Targeting Ligands are provided in FIG. 1. Additional plasma kallikrein Targeting Ligands can be found in, for example, J Med Chem 61: 2823-2836 (2018), J Med Chem 55: 1171-80 (2012), U.S. Pat. Nos. 8,598,206, 9,738,655, Bioorg Med Chem Lett 16: 2034-6 (2006), U.S. Pat. No. 9,409,908, U.S. patent Ser. No. 10/144,746, U.S. Pat. No. 9,290,485, each of which is incorporated herein by reference.

Lipoprotein Lipase

In some embodiments, the Target Extracellular Protein is human lipoprotein lipase (UniProtKB—P06858 (LIPL_HUMAN)). Lipoprotein lipase is a key enzyme in triglyceride metabolism. It catalyzes the hydrolysis of triglycerides from circulating chylomicrons and very low density lipoproteins (VLDL), and thereby plays an important role in lipid clearance from the blood stream, lipid utilization and storage. Lipoprotein lipase mediates margination of triglyceride-rich lipoprotein particles in capillaries. Lipoprotein lipase has been implicated in the development of cardiovascular disease and obesity.

The Protein Data Bank website provides the crystal structure of lipoprotein lipase bound to various compounds searchable by 6E7K (Birrane, G., et al., Proc Natl Acad Sci USA, 2018 116 1723-1732).

Representative lipoprotein lipase Targeting Ligands are provided in FIG. 1. Additional lipoprotein lipase Targeting Ligands can be found in, for example, J Med Chem 47: 400-10 (2004), which is incorporated herein by reference.

Matrix Metallopeptidase 1 (MMP-1)

In some embodiments, the Target Extracellular Protein is human matrix metallopeptidase 1 (MMP-1) (UniProtKB—P03956 (MMP1_HUMAN)). MMP-1 cleaves collagens of types I, II, and III at one site in the helical domain. It also cleaves collagens of types VII and X. MMP-1 has been implicated in cardiovascular disease.

The Protein Data Bank website provides the crystal structure of MMP-1 searchable by 3SHI (Bertini, I., et al., FEBS Lett., 2012, 586, 557-567); as well as the crystal structure of MMP-1 bound to various compounds searchable by 4AUO (Manka, S. W., et al., Proc Natl Acad Sci USA, 2012, 109, 12461); 3MA2 (Grossman, M., et al., Biochemistry, 2010, 49, 6184-6192); and 2JOT (Iyer, S., et al., J. Biol. Chem., 2007, 282, 364). Additionally, Iyer et al., provides insight into the crystal structure of an active form of MMP-1 (Iyer, S., et al., J Mol Biol., 2006, 362(1), 78-88); and Lovejoy et al., provides insight into the crystal structure of MMP1 and the selectivity of collagenase inhibitors (Lovejoy, B., et al., Nat Struct Mol Biol., 1999, 6, 217-221).

Representative MMP-1 Targeting Ligands are provided in FIG. 1. Additional MMP-1 Targeting Ligands can be found in, for example, Bioorg Med Chem Lett 5: 1415-1420 (1995), Bioorg Med Chem Lett 16: 2632-6 (2006), Bioorg Med Chem Lett 8: 837-42 (1999), Eur J Med Chem 60: 89-100 (2013), J Med Chem 54: 4350-64 (2011), Bioorg Med Chem Lett 8: 3251-6 (1999), J Med Chem 42: 4547-62 (1999), J Med Chem 61: 2166-2210 (2018), J Med Chem 41: 1209-17 (1998), which is incorporated herein by reference.

Macrophage Migration Inhibitory Factor (MIF)

In some embodiments, the Target Extracellular Protein is human macrophage migration inhibitory factor (MIF) (UniProtKB—P14174 (MIF_HUMAN)). MIF is a pro-inflammatory cytokine involved in the innate immune response to bacterial pathogens. The expression of MIF at sites of inflammation suggests a role as mediator in regulating the function of macrophages in host defense. It counteracts the anti-inflammatory activity of glucocorticoids.

MIF has been implicated in tumor progression; systemic inflammation; atherosclerosis; rheumatoid arthritis; and systemic lupus erythematosus, among others.

The Protein Data Bank website provides the crystal structure of MIF searchable by 1MIF (Sun, H-W. et al., Proc Natl Acad Sci USA, 1996, 93, 5191-5196); as well as the crystal structure of MIF bound to various compounds searchable by 6PEG (Cirillo, P. F. et al.); 5XEJ (Fukushima, K); 6FVE and 6FVH (Sokolov, A. V., et al., Biochemistry (Mosc), 2018, 83, 701-707); 6CB5, 6CBF, 6CBG, and 6CBH (Trivedi-Parmar, V., et al., ChemMedChem., 2018, 13, 1092-1097); 6B1C, 6B1K, 6B2C, (Dawson, T. K., et al., ACS Med Chem Lett., 2017, 8, 1287-1291); 4Z15, 4Z1T and 4Z1U (Singh, A. K., et al, J Cell Mol Med., 2017, 21, 142-153); 5HVS and 5HVT (Cisneros, J. A., et al., J Am Chem Soc., 2016, 138, 8630-8638); 4PKK (Pantouris, G., et al.); 5J7P and 5J7Q (Cisneros, J. A., et al., Bioorg Med Chem Lett., 2016, 26, 2764-2767); 5B40 (Kimura, H., et al., Chem Biol., 2010, 17, 1282-1294); 4PLU, 4TRF, 4P0H, and 4P0I (Pantouris, G., et al., Chem Biol., 2015, 22, 1197-1205); 4WR8 and 4WRB (Dziedzic, P., et al., J Am Chem Soc., 2015, 137 2996-3003); 4K9G (Ioannou, K., et al., Int J Oncol., 2014, 45, 1457-1468); 4OSF, 3WNR, 3WNS and 3WNT (Spencer, E. S., et al., Eur J Med Chem., 2015, 93, 501-510); 4OYQ (Spencer, E. S. et al.); 3SMB and 3SMC (Crichlow, G. V. et al., Biochemistry, 2012, 51, 7506-7514); 3U18 (Bai, F., et al., J Biol Chem., 2012, 287, 30653-30663); 4F2K (Tyndall, J. D. A., et al., Acta Crystallogr Sect F Struct Biol Cryst Commun., 2012, 68, 999-1002); 3IJG and 3IJJ (Cho, Y., et al., Proc Natl Acad Sci USA, 2010, 107, 11313-11318); 3L5P, 3L5R, 3L5S, 3L5T, 3L5U, and 3L5V (McLean, L. R. et al., Bioorg Med Chem Lett., 2010, 20, 1821-1824); 3JSF, 3JSG and 3JTU (McLean, L. R., et al., Bioorg Med Chem Lett., 2009, 19, 6717); 3HOF (Crawley, L., et al.); 3CE4 and 3DJI (Crichlow G. V., et al., Biochemistry, 2009, 48, 132-139); 3B9S (Winner, M. et al., Cancer Res., 2008, 68, 7253-7257); 2OOH, 2OOW and 2OOZ (Crichlow, G. V. et al., J Biol Chem., 2007, 282, 23089-23095); 1GCZ and 1GDO (Orita, M. et al., J Med Chem., 2001, 44, 540-547); and 1CA7, 1CGQ and 1P1G (Lubetsky, J. B. et al., Biochemistry, 1999, 38, 7346-7354). Additionally, Sun et al., provides insight into the crystal structure of MIF (Proc Natl Acad Sci USA., 1996, 28; 93(11), 5191-6).

Representative MIF Targeting Ligands are provided in FIG. 1. Additional MIF Targeting Ligands can be found in, for example, ACS Med Chem Lett 8: 124-127 (2017), J Med Chem 44: 540-7 (2001), J Med Chem 52: 416-24 (2009), J Med Chem 50: 1993-7 (2007), which is incorporated herein by reference.

Transforming Growth Factor-β2 (TGF-β2)

In some embodiments, the Target Extracellular Protein is human transforming growth factor-β2 (TGF-β2) (UniProtKB—P61812 (TGFB2_HUMAN)). TGF-β2 is a multifunctional protein that regulates various processes such as angiogenesis and heart development. Once activated following release of LAP, TGF-beta-2 acts by binding to TGF-beta receptors (TGFBR1 and TGFBR2), which transduce signal. TGF-β2 expression in the tumor microenvironment has been associated with a poor prognosis, and is implicated in TGF-β2 mediated tumor suppression via T-cell exclusion. TGF-β2 expression has also been implicated in hematological malignancies and fibrosis.

The Protein Data Bank website provides the crystal structure of TGF-β2 searchable by 6I9J (Del Amo-Maestro L. et al., Sci Rep. 2019, 9, 8660-8660); as well as the crystal structure of TGF-β2 bound to various compounds searchable by 1M9Z (Boesen, C. C., et al. Structure, 2002, 10, 913-919); 5QIN (Zhang, Y. et al., ACS Med Chem Lett., 2018, 9, 1117-1122); 5E8V, 5E8Y, 5E91 and 5E92 (Tebben, A. J. et al., Acta Crystallogr D Struct Biol., 2016, 72, 658-674); 4P7U (Wangkanont, K. et al., Protein Expr Purif, 2015, 115, 19-25); 4XJJ (Wangkanont et al.); and 1KTZ (Hart, P. J., et al., Nat Struct Biol., 2002, 9, 203-208).

Representative TGF-β2 Targeting Ligands are provided in FIG. 1.

Thrombospondin-1 (TSP-1)

In some embodiments, the Target Extracellular Protein is human thrombospondin-1 (TSP-1) (UniProtKB—P61812 (TGFB2_HUMAN)). TSP1 acts as an angiogenesis inhibitor by stimulating endothelial cell apoptosis, inhibiting endothelial cell migration and proliferation, and regulating vascular endothelial growth factor bioavailability and activity. TSP1 affects tumor immune response, tumor cell behaviors including adhesion, invasion, migration, apoptosis, and proliferation.

TSP-1 expression has been implicated in a number of diseases, including in promoting certain cancers such as breast cancer, prostate cancer, melanoma, SCLC, osteosarcoma, cutaneous squamous cell carcinoma, oral squamous cell carcinoma, papillary thyroid carcinoma, thyroid cancer, medulloblastoma, and fibrotic disorders such as diabetes, liver fibrosis, and in multiple myeloma.

The Protein Data Bank website provides the crystal structure of TSP-1 searchable by 1LSL (Tan, K. et al., J Cell Biol., 2002, 159, 373-382); 2ES3 (Tan, K., et al., J Biol Chem., 2008, 283, 3932-3941); 1Z78 and 2ERF (Tan, K., et al., Structure, 2006, 14, 33-42); and 3R6B (Klenotic, P. A., et al., Protein Expr Purif., 2011, 80, 253-259); as well as the crystal structure of TSP-1 bound to various compounds searchable by 2OUH and 2OUJ (Tan, K., et al., J Biol Chem., 2008, 283, 3932-3941); and 1ZA4 (Tan, K., et al., Structure, 2006, 14, 33-42).

Representative TSP-1 Targeting Ligands are provided in FIG. 1.

CD40 Ligand (CD40L)

In some embodiments, the Target Extracellular Protein is human CD40 ligand (CD40L) (UniProtKB—P29965 (CD40L_HUMAN)). CD40L is a cytokine that acts as a ligand to CD40/TNFRSF5. It costimulates T-cell proliferation and cytokine production. Its cross-linking on T-cells generates a costimulatory signal which enhances the production of IL4 and IL10 in conjunction with the TCR/CD3 ligation and CD28 costimulation. CD40L induces the activation of NF-kappa-B, as well as kinases MAPK8 and PAK2 in T-cells. It also induces tyrosine phosphorylation of isoform 3 of CD28. CD40L mediates B-cell proliferation in the absence of co-stimulus as well as IgE production in the presence of IL4, and is involved in immunoglobulin class switching.

The Protein Data Bank website provides the crystal structure of CD40L searchable by 1ALY (Karpusas, M., et al., Structure, 1995, 3, 1031-1039); as well as the crystal structure of CD40L bound to various compounds searchable by 3QD6 (An, H. J., et al., J Biol Chem., 2011, 286, 11226-11235); and 6BRB (Karnell, J. L., et al., Sci Transl Med., 2019, 11(489), 6584).

The expression of CD40L has been implicated in HIV-associated neurocognitive disorders and cardiovascular complications. Representative CD40L Targeting Ligands are provided in FIG. 1.

Urokinase-type Plasminogen Activator (UPA)

In some embodiments, the Target Extracellular Protein is human urokinase-type plasminogen activator (UPA) (UniProtKB—P00749 (UROK_HUMAN)). Urokinase-type plasminogen activator (uPA), is a serine protease present in the blood and in the extracellular matrix of many tissues. The primary physiological substrate of this enzyme is plasminogen, which is an inactive form (zymogen) of the serine protease plasmin. Activation of plasmin triggers a proteolytic cascade that, depending on the physiological environment, participates in thrombolysis or extracellular matrix degradation. This cascade had been involved in vascular diseases and cancer progression. Elevated expression levels of urokinase and several other components of the plasminogen activation system are found to be correlated with tumor malignancy.

The Protein Data Bank website provides the crystal structure of UPA bound to various compounds searchable by 5ZA7, 5ZAJ, 5ZA8, 5ZA9, 5ZAE, 5ZAF, 5ZAG, 5ZAH, and 5ZC5 (Buckley, B. J. et al., J Med Chem., 2018, 61, 8299-8320); 5LHP, 5LHQ, 5LHR, and 5LHS (Kromann-Hansen, T. et al., Sci Rep., 2017, 7, 3385-3385); 2VNT (Fish, P. V. et al. J Med Chem., 2007, 50, 2341); 1OWD, 1OWE, 1OWH, 1OWI, 1OWJ, and 1OWK (Wendt, M. D. et al., J Med Chem., 2004, 47, 303-324); 1SQA, 1SQO, and 1SQT (Wendt, M. D., et al., Bioorg Med Chem Lett., 2004, 14, 3063-3068); 1U6Q (Bruncko, M. et al., Bioorg Med Chem Lett., 2005, 15, 93-98); 3OX7, 3OY5 and 3OY6 (Jiang, L. G. et al., J Mol Biol., 2011, 412, 235-250); 4OS1, 4OS2, 4OS4, 4OS5, 4OS6 and 4OS7 (Chen, S. et al., Nat Chem., 2014, 6, 1009-1016); 3IG6 (West, C. W. et al., Bioorg Med Chem Lett., 2009, 19, 5712-5715); 4X0W and 4X1P (Jiang, L. et al., Int J Biochem Cell Biol., 2015, 62, 88-92); 4X1N, 4X1Q, 4X1R and 4X1S (Zhao, B. et al., PLoS One, 2014, 9, e115872-e115872); 5WXO and 5WXP (Jiang, L. et al., Biochim Biophys Acta., 2018, 1862, 2017-2023); 4MNV, 4MNW, 4MNX, and 4MNY (Chen, S., et al., Angew Chem Int Ed Engl., 2014, 53, 1602-1606); 4GLY (Chen, S., et al., J Am Chem Soc., 2013, 135, 6562-6569); 4JK5 and 4JK5 (Chen, S., et al., Chembiochem., 2013, 14, 1316-1322); 3QN7 (Angelini, A. et al., ACS Chem Biol., 2012, 7, 817-821); 2NWN (Zhao, G. et al., J Struct Biol., 2007, 160, 1-10); 6NMB (Wu, G. et al., Blood Adv., 2019, 3, 729-733); 1W0Z, 1W10, 1W11, 1W12, 1W13, and 1W14 (Zeslawska, E. et al., J Mol Biol., 2003, 328, 109); 4DVA (Jiang, L et al., Biochem J., 2013, 449, 161-166); 6A8G 6A8N (Wang, D. et al., J Med Chem., 2019, 62, 2172-2183); 2VIN, 2VIO, 2VIP, 2VIQ, 2VIV, and 2VIW (Frederickson, M. et al., J Med Chem., 2008, 51, 183); 1EJN (Speri, S., et al., Proc Natl Acad Sci USA, 2000, 97, 5113-5118); 3PB1 (Lin, Z. et al., J Biol Chem., 2011, 286, 7027-7032); 3U73 (Xu, X. et al., J Mol Biol., 2012, 416, 629-641); 1C5W, 1C5X, 1C5Y and IC5Z (Katz, B. A., et al., Chem Biol., 2000, 7, 299-312); 5XG4 (Xue, G. et al., Food Funct., 2017, 8, 2437-2443); 5WXF (Jiang, L. et al., Biochim Biophys Acta., 2018, 1862, 2017-2023); 5WXS, 4ZKS, 5WXQ, 5WXT, 5YC6, 5YC7, 5Z1C, (Jiang, L. et al.); 4H42 (Yu, H. Y. et al.); 6AG3 and 6AG9 (Buckley, B. et al); 3KGP, 3KHV, 3KID, 3M61, 3MHW, and 3MWI (Jiang, L. G. et al.); 4ZKN, 4ZKO and 4ZKR (Jiang, L. et al.); 2O8T, 2O8U, 2O8W (Zhao, G. et al.); and 4FU7, 4FU8, 4FU9, 4FUB, 4FUC, 4FUD, 4FUE, 4FUF, 4FUG, 4FUH, 4FUI, and 4FUJ (Kang, Y. N. et al.).

Representative UPA Targeting Ligands are provided in FIG. 1. Additional UPA Targeting Ligands are provided in, for example, J Med Chem 38: 1511-22 (1995), Bioorg Med Chem Lett 11: 2253-6 (2001), Bioorg Med Chem Lett 14: 3063-8 (2004), J Med Chem 52: 3159-65 (2009), CSAR 1: (2012), Bioorg Med Chem 22: 3187-203 (2014), J Med Chem 50: 2341-51 (2007), J Mol Biol 329: 93-120 (2003), Bioorg Med Chem Lett2:1399-1404 (1992), J Med Chem 35: 4297-305 (1992), J Med Chem 35: 4150-9 (1992), J Med Chem 49: 5785-93 (2006), Bioorg Med Chem 23: 3696-704 (2015), Bioorg Med Chem Lett 10: 983-7 (2000), J Med Chem 49: 5785-93 (2006), each of which is incorporated by reference herein.

Plasminogen Activator, Tissue Type (TPA)

In some embodiments, the Target Extracellular Protein is human plasminogen activator, tissue type (TPA) (UniProtKB—P00750 (TPA_HUMAN)). TPA converts the abundant, but inactive, zymogen plasminogen to plasmin by hydrolyzing a single Arg-Val bond in plasminogen. By controlling plasmin-mediated proteolysis, it plays an important role in tissue remodeling and degradation, in cell migration and many other physiopathological events. TPA plays a direct role in facilitating neuronal migration. PLA has been shown activated in various cancers including oral malignancy.

The Protein Data Bank website provides the crystal structure of TPA searchable by 1VR1 (Dekker, R. J. et al., J Mol Biol., 1999, 293, 613-627); as well as the crystal structure of TPA bound to various compounds searchable by 1RTF (Lamba, D. et al., J Mol Biol., 1996, 258, 117-135); 1A5H (Renatus, M. et al., J Biol Chem., 1997, 272, 21713-21719); and 1BDA (Renatus, M. et al., EMBO J., 1997, 16, 4797-4805).

Representative TPA Targeting Ligands are provided in FIG. 1. Additional TPA Targeting Ligands are provided in, for example, Bioorg Med Chem Lett 15: 4411-6 (2005), Bioorg Med Chem Lett 13: 2781-4 (2003), Bioorg Med Chem Lett 6: 2913-2918 (1996), J Med Chem 44: 2753-71 (2001), J Med Chem 41: 5445-56 (1999), Bioorg Med Chem Lett 12: 3183-6 (2002), U.S. patent Ser. No. 10/118,930, J Biol Chem 285: 7892-902 (2010), each of which is incorporated by reference herein.

Plasminogen (PLG)

In some embodiments, the Target Extracellular Protein is human plasminogen (PLG) (UniProtKB—P00747 (PLMN_HUMAN)). PLG dissolves the fibrin of blood clots and acts as a proteolytic factor in a variety of other processes including embryonic development, tissue remodeling, tumor invasion, and inflammation. It activates the urokinase-type plasminogen activator, collagenases and several complement zymogens, such as C1 and C5. Its role in tissue remodeling and tumor invasion may be modulated by CSPG4.

The Protein Data Bank website provides the crystal structure of PLG searchable by 1DDJ (Wang, X. et al., J. Mol. Biol., 2000, 295, 903-914); and 4DUR and 4DUU (Law, R. H. P., et al., Cell Rep., 2012, 1, 185-190).

Representative PLG Targeting Ligands are provided in FIG. 1. Additional PLG Targeting Ligands are provided in, for example, J Med Chem 35: 4297-305 (1992), J Med Chem 38: 1511-22 (1995), J Med Chem 56: 820-31 (2013), U.S. Pat. Nos. 8,598,206, 8,921,319, J Med Chem 55: 1171-80 (2012), Bioorg Med Chem Lett 12: 3183-6 (2002), Bioorg Med Chem 23: 3696-704 (2015), Bioorg Med Chem Lett 13: 723-8 (2003), Bioorg Med Chem Lett 7: 331-336 (1997), each of which is incorporated by reference herein.

Plasminogen Activator Inhibitor-1 (PAI-1)

In some embodiments, the Target Extracellular Protein is human plasminogen activator inhibitor 1 (PAI-1) (UniProtKB—P05121 (PAI1_HUMAN)). PAI-1 is a serine protease inhibitor, and a primary inhibitor of tissue-type plasminogen activator (PLAT) and urokinase-type plasminogen activator (PLAU). As PLAT inhibitor, it is required for fibrinolysis down-regulation and is responsible for the controlled degradation of blood clot. As PLAU inhibitor, it is involved in the regulation of cell adhesion and spreading, and acts as a regulator of cell migration, independently of its role as protease inhibitor. Overexpression of PAI-1 favors angiogenesis, metastasis, and poor prognosis in tumors, including, but not limited to, oral cancers and breast cancers.

The Protein Data Bank website provides the crystal structure of PAI-1 searchable by 3Q02 and 3Q03 (Jensen, J. K. et al., J Biol Chem., 2011, 286, 29709-29717); 1B3K (Sharp, A. M. et al., Structure, 1999, 7, 111-118); 1C5G (Tucker, H. M. et al., Nat Struct Biol., 1995, 2, 442-445); 1DVM (Stout, T. J. et al., Biochemistry, 2000, 39, 8460-8469); and 3UT3 (Lin, Z. H. et al.); as well as the crystal structure of PAI-1 bound to various compounds searchable by 4AQH (Fjellstrom, O. et al., J Biol Chem., 2013, 288, 873); 3R4L (Jankun, J. et al., Int J Mol Med., 2012, 29 61-64); 1A7C (Xue, Y., et al., Structure, 1998, 6, 627-636); 1OC0 (Zhou, A. et al., Nat Struct Biol., 2003, 10, 541); 6I8S (Vousden, K. A. et al., Sci Rep., 2019, 9, 1605-1605); 4G80 and 4G8R (Li, S. H. et al., Proc Natl Acad Sci USA, 2013, 110, E4941-E4949); 6GWQ, 6GWN and 6GWP (Sillen, M. et al., J Thromb Haemost, 2019); and 4ICO (Hong, Z. B. et al.).

Representative PAI-1 Targeting Ligands are provided in FIG. 1. Additional PAI-1 Targeting Ligands are provided in, for example, J Biol Chem 285: 7892-902 (2010), U.S. Pat. No. 9,120,744, Bioorg Med Chem Lett 13: 3361-5 (2003), Bioorg Med Chem Lett 12: 1063-6 (2002), Bioorg Med Chem Lett 13: 1705-8 (2003), Bioorg Med Chem Lett 11: 2589-92 (2001), U.S. Pat. No. 9,718,760, each of which is incorporated by reference herein.

Placenta Growth Factor (PlGF)

In some embodiments, the Target Extracellular Protein is human placental growth factor (PGF) (UniProtKB—P49763 (PLGF_HUMAN)). PGF is growth factor active in angiogenesis and endothelial cell growth, stimulating their proliferation and migration. It binds to the receptor FLT1/VEGFR-1. Isoform PlGF-2 binds NRP1/neuropilin-1 and NRP2/neuropilin-2 in a heparin-dependent manner. PGF also promotes cell tumor growth, and has been implicated in age-related macular degeneration (AMD) and choroidal neovascularization (CNV).

The Protein Data Bank website provides the crystal structure of PlGF searchable by 1FZV (Iyer, S. et al., J Biol Chem., 2001, 276, 12153-12161); as well as the crystal structure of PlGF bound to various compounds searchable by 1RV6 (Christinger, H. W., J Biol Chem., 2004, 279, 10382-10388). Additionally, De Falco provides insight into the discovery and biological activity of placenta growth factor (De Falco, Exp Mol Med., 2012, 44, 1-9).

Representative PGF Targeting Ligands are provided in FIG. 1. Additional PGF Targeting Ligands are provided in, for example, J Med Chem 54: 1256-65 (2011), J Nat Prod 76: 29-35 (2013), each of which is incorporated by reference herein.

Phospholipase A2, Group IB (PA21B)

In some embodiments, the Target Extracellular Protein is human phospholipase A2, Group IB (PA21B) (UniProtKB—P04054 (PA21B_HUMAN)). PA21B cleaves phospholipids preferentially at the sn-2 position, liberating free fatty acids and lysophospholipids. PA21B has been implicated in a number of diseases, including cardiovascular diseases, atherosclerosis, immune disorders and cancer.

The Protein Data Bank website provides the crystal structure of PA21B searchable by 3FVJ and 3FVI (Pan, Y. H. et al., Biochim. Biophys. Acta., 2010, 1804, 1443-1448).

Representative PA21B Targeting Ligands are provided in FIG. 1. Additional PA21B Targeting Ligands are provided in, for example, J Med Chem 39: 3636-58 (1996), Chembiochem 4: 181-5 (2003), J Med Chem 39: 5159-75 (1997), J Med Chem 51: 4708-14 (2008), each of which is incorporated by reference herein.

Phospholipase A2, Group IIA (PA2GA)

In some embodiments, the Target Extracellular Protein is human phospholipase A2, Group IIA (PA2GA) (UniProtKB—P04054 (PA21B_HUMAN)). PA2GA catalyzes the calcium-dependent hydrolysis of the 2-acyl groups in 3-sn-phosphoglycerides. It is thought to participate in the regulation of phospholipid metabolism in biomembranes including eicosanoid biosynthesis. Independent of its catalytic activity, it also acts as a ligand for integrins. PA2GA Induces cell proliferation in an integrin-dependent manner. PA2GA has been implicated in a number of diseases, including cardiovascular diseases, atherosclerosis, immune disorders, and cancer. The Protein Data Bank website provides the crystal structure of PA2GA bound to various compounds searchable by 2ARM and 1SV3 (Singh, N. et al., Proteins, 2006, 64, 89-100); 5G3M and 5G3N (Giordanetto, F., et al. ACS Med Chem Lett., 2016, 7, 884); 1KQU (Jansford, K. A., et al., Chembiochem., 2003, 4,181-185); and 1ZYX (Singh, N. et al.). Additionally, Singh et al., provides insight into the crystal structure of the complexes of a group IIA phospholipase A2 with two natural anti-inflammatory agents, anisic acid, and atropine reveal a similar mode of binding (Singh, N. et al., Proteins, 2006, 64(1):89-100); and Kitadokoro et al also provides insight into the crystal structure of human secretory phospholipase A2-IIA complex with the potent indolizine inhibitor 120-1032 (Kitadokoro, K. et al., J Biochem., 1998, 123(4), 619-23).

Representative PA2GA Targeting Ligands are provided in FIG. 1. Additional PA2GA Targeting Ligands are provided in, for example, J Med Chem 48: 893-6 (2005), J Med Chem 39: 5159-75 (1997), each of which is incorporated by reference herein.

Factor B

In some embodiments, the Target Extracellular Protein is human Complement factor B (UniProtKB—P00751 (CFAB_HUMAN)). Complement factor B, which is part of the alternate pathway of the complement system, is cleaved by factor D into 2 fragments: Ba and Bb. Bb, a serine protease, then combines with complement factor 3b to generate the C3 or C5 convertase. It has also been implicated in proliferation and differentiation of preactivated B-lymphocytes, rapid spreading of peripheral blood monocytes, stimulation of lymphocyte blastogenesis and lysis of erythrocytes. Ba inhibits the proliferation of preactivated B-lymphocytes.

The Protein Data Bank website provides the crystal structure of Complement Factor B searchable by 2OK5 (Milder, F. J., et al., Nat Struct Mol Bio 2007, 14, 224-228); as well as the crystal structure of Complement factor B bound to various compounds searchable by 6QSW, 6QSX, and 6RAV (Schubart, A., et al., Proc Natl Acad Sci 2019, 116, 7926-7931); 6T8U, 6T8W, and 6T8V (Mainolfi, N., et al, J Med Chem 2020, 63, 5697-5722); and 7JTN (Xu, X., et al., J Immunol 2021, 206, doi:10.4049/jimmunol.2001260).

Figure 5:
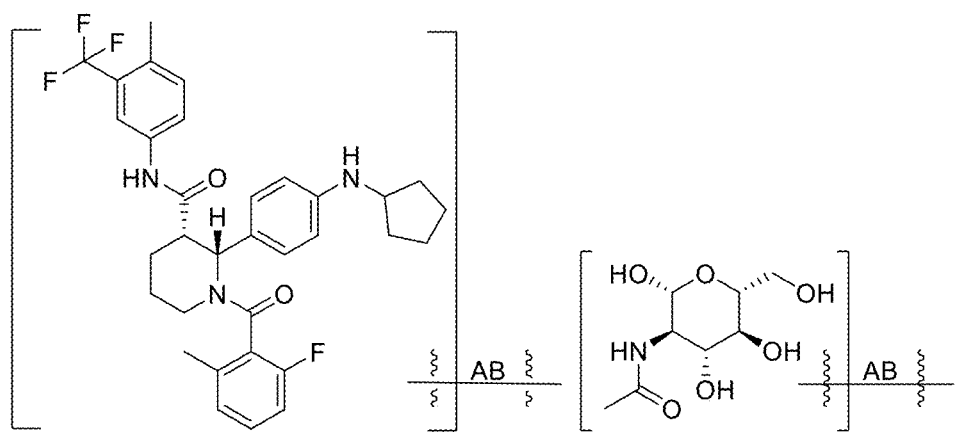
FIG. 5 provides a non-limiting list of exemplary Extracellular Protein Targeting Ligands that target complement component 5.

Representative Complement Factor B Targeting Ligands are provided in FIG. 5. Additional Complement Factor B Targeting Ligands are provided in, for example, U.S. Pat. No. 9,682,968B2, U.S. Pat. No. 9,475,806B2, U.S. Pat. No. 9,452,990B2, Proc Natl Acad Sci 116: 7926-7931 (2019), J Med Chem 52: 6042-6052 (2009), and J Med Chem 63: 5697-5722 (2020), each of which is incorporated by reference herein.

In certain embodiments the Extracellular Targeting Ligand is selected from:

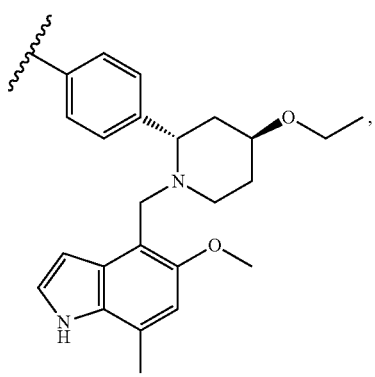

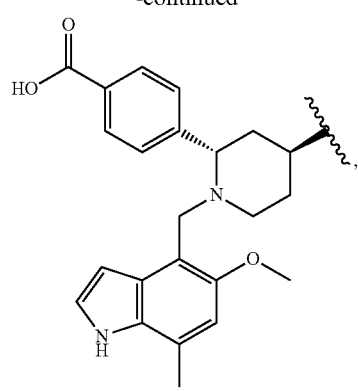

-continued

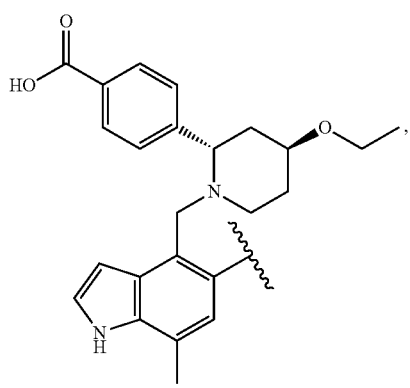

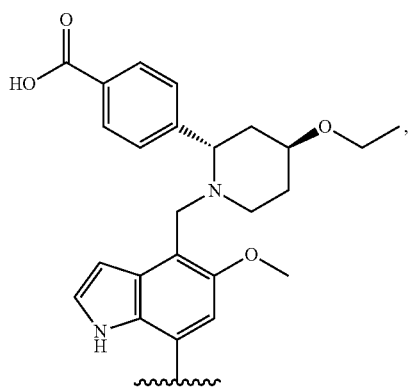

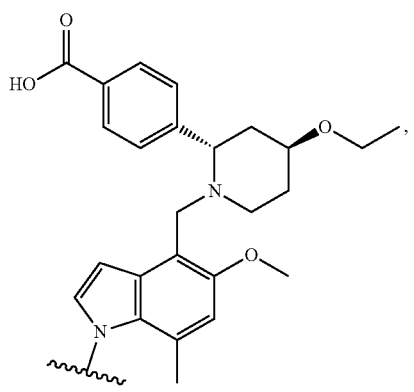

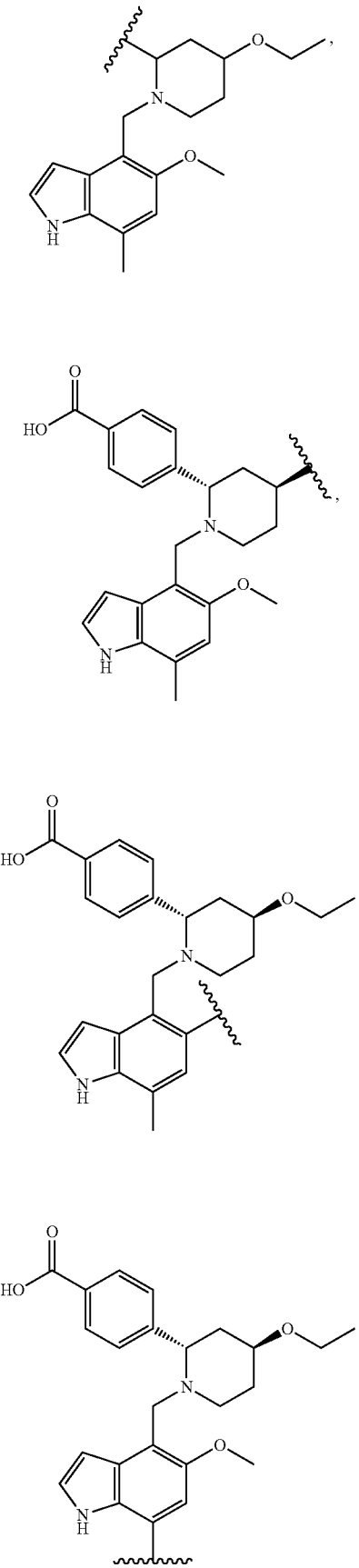
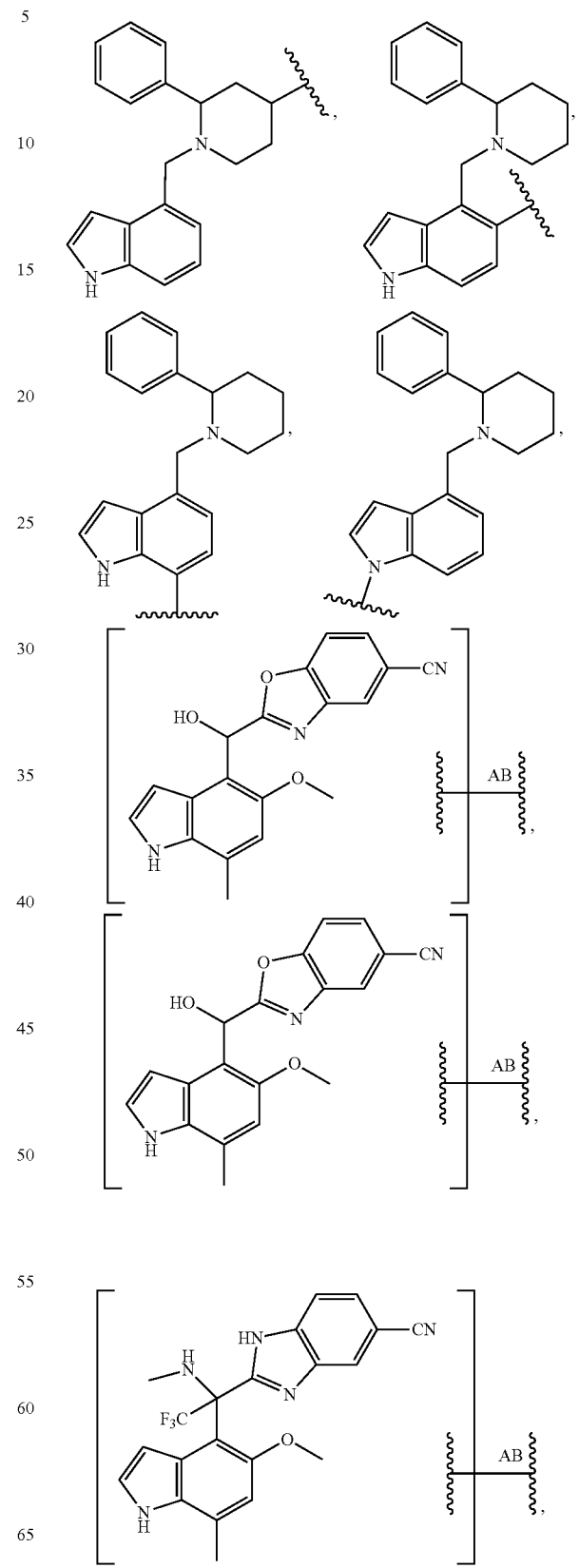

169
-continued

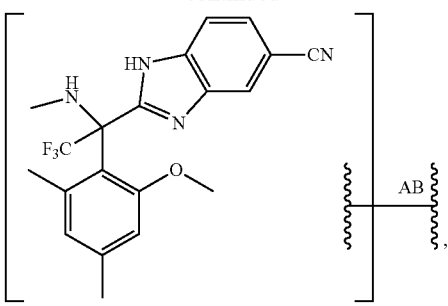

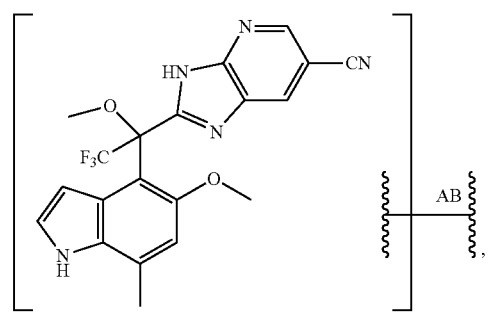

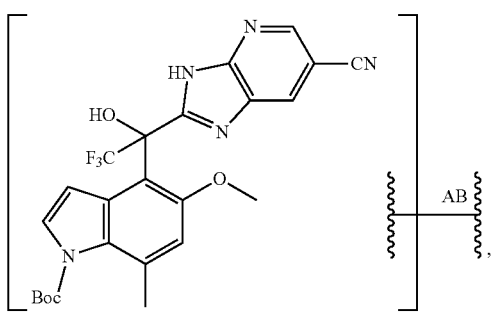

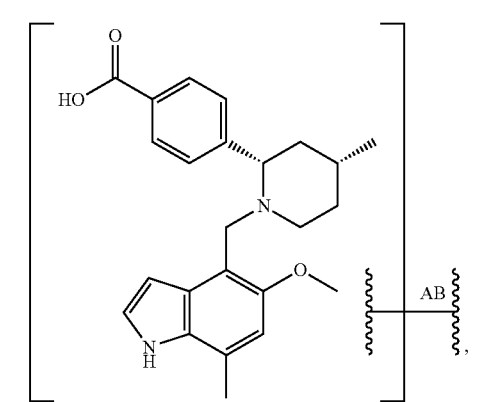

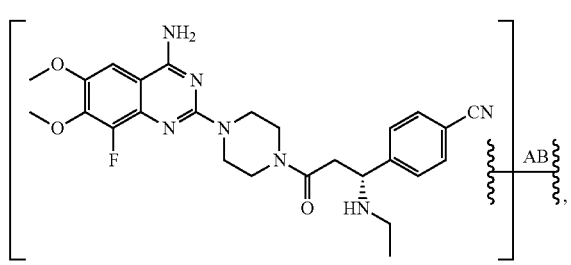

170
-continued

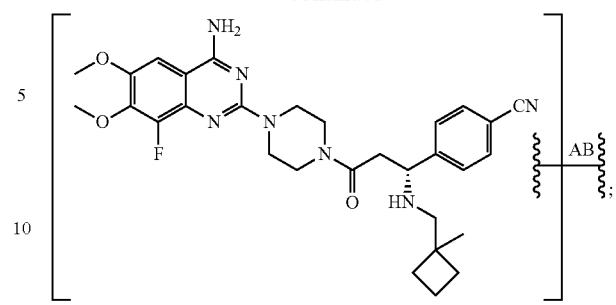

each of which is optionally substituted with 1, 2, 3, or 4 substituents independently selected from $R^{21}$.

In certain embodiments the Factor B Targeting Ligand is selected from a ligand described in: Mainolfi, N. et. al. Discovery of 4-((2S,4 S)-4-Ethoxy-1-((5-Methoxy-7-Methyl-1H-Indol-4-Yl)Methyl)Piperidin-2-Yl)Benzoic Acid (LNP023), a Factor B Inhibitor Specifically Designed To Be Applicable to Treating a Diverse Array of Complement Mediated Diseases. J. Med. Chem. 2020, 63 (11), 5697-5722; WO2020/016749; WO2018/005552; WO2013/192345; or WO2015009616.

In certain embodiments the factor B Targeting Ligand-linker is selected from:

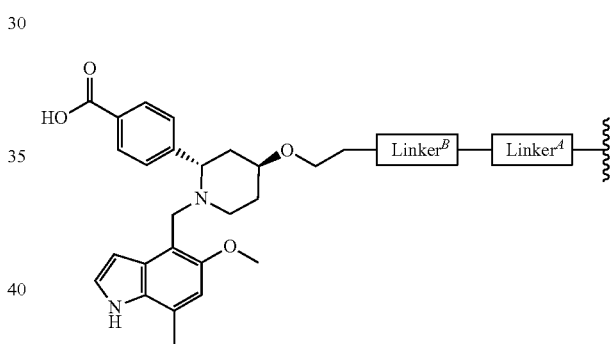

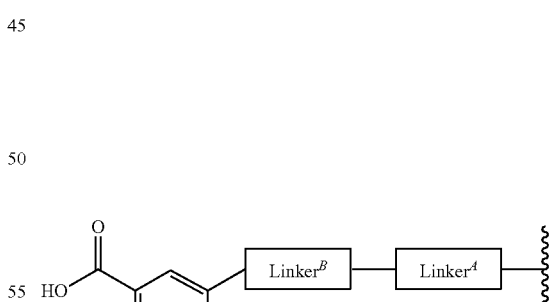

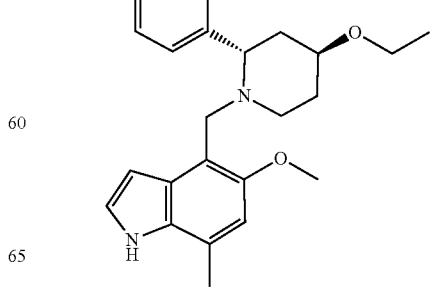

171
-continued
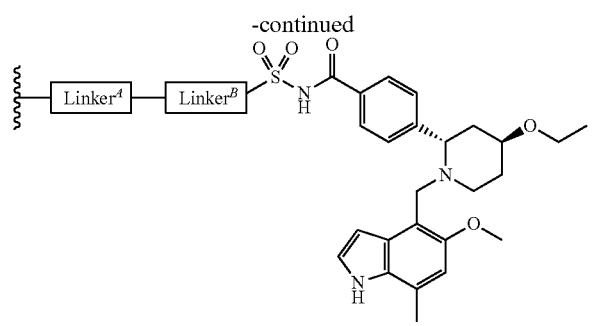
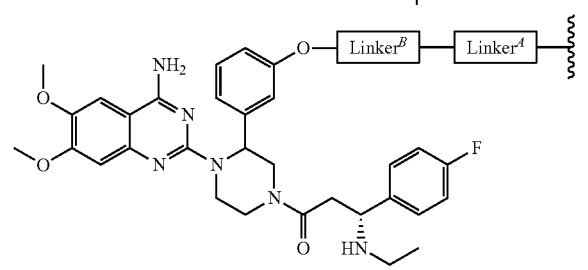
172
-continued
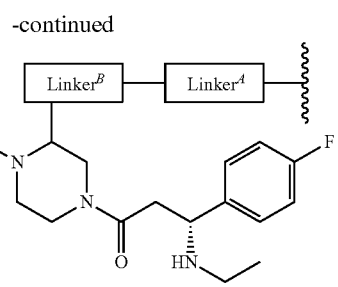
In certain embodiments the compound of the present invention is selected from the following compounds or a bi- or tri-dentate version thereof:
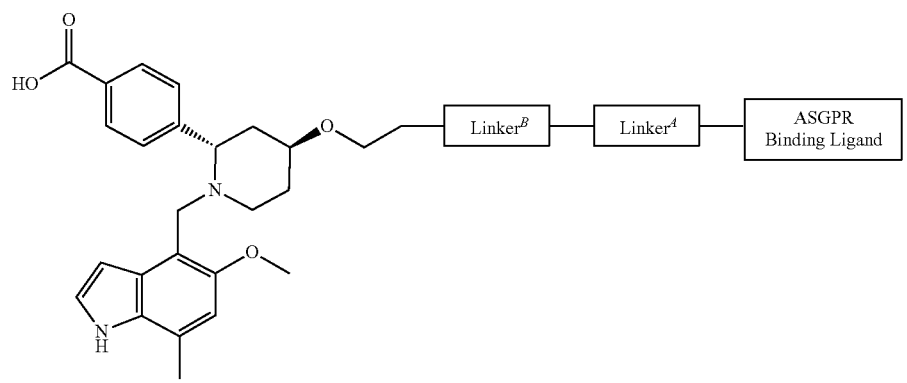
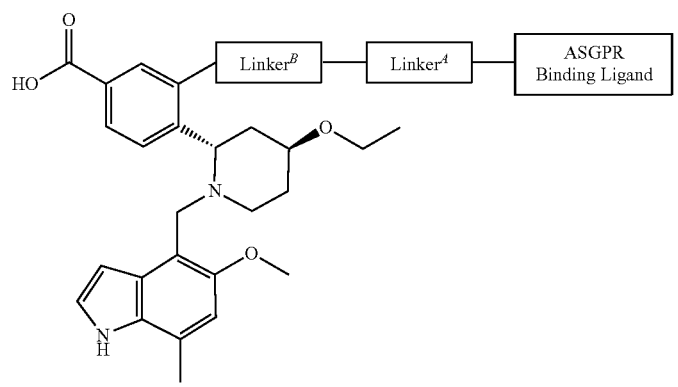

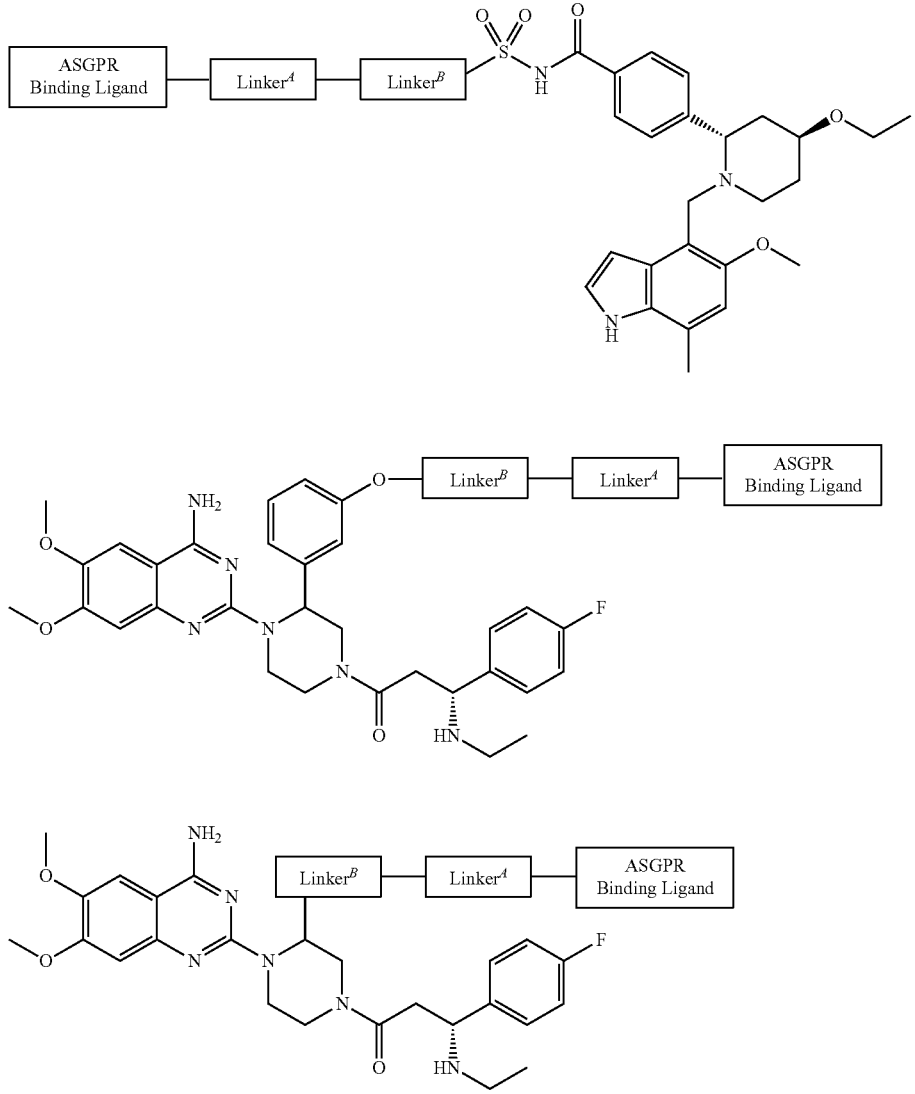

Factor D

In some embodiments, the Target Extracellular Protein is human Complement factor D (UniProtKB—P00746 (CFAD_HUMAN)). Factor D cleaves factor B when the latter is complexed with factor C3b, activating the C3bbb complex, which then becomes the C3 convertase of the alternate pathway. Its function is homologous to that of C1s in the classical pathway.

The Protein Data Bank website provides the crystal structure of Complement factor D bound to various compounds searchable by 6FTZ, 6FUT, 6FUH, 6FUG, 6FUJ, and 6FUI (Vulpetti, A., et al., ACS Med Chem Lett 2018, 9, 490-495); 5TCA and 5TCC (Yang, C. Y., et al., ACS Med Chem Lett 2016, 7, 1092-1096); 5MT4 (Vulpetti, A., et al., J Med Chem 2017, 60, 1946-1958); 1DFP (Cole, L. B., et al., Acta Crystallogr D Biol Crystallogr 1997, 53, 143-150); 1DIC (Cole, L. B., et al., Acta Crystallogr D Biol Crystallogr 1998, 54, 711-717); 6QMR and 6QMT (Karki, R. G., et al., J Med Chem 2019, 62, 4656-4668).

Figure 6:
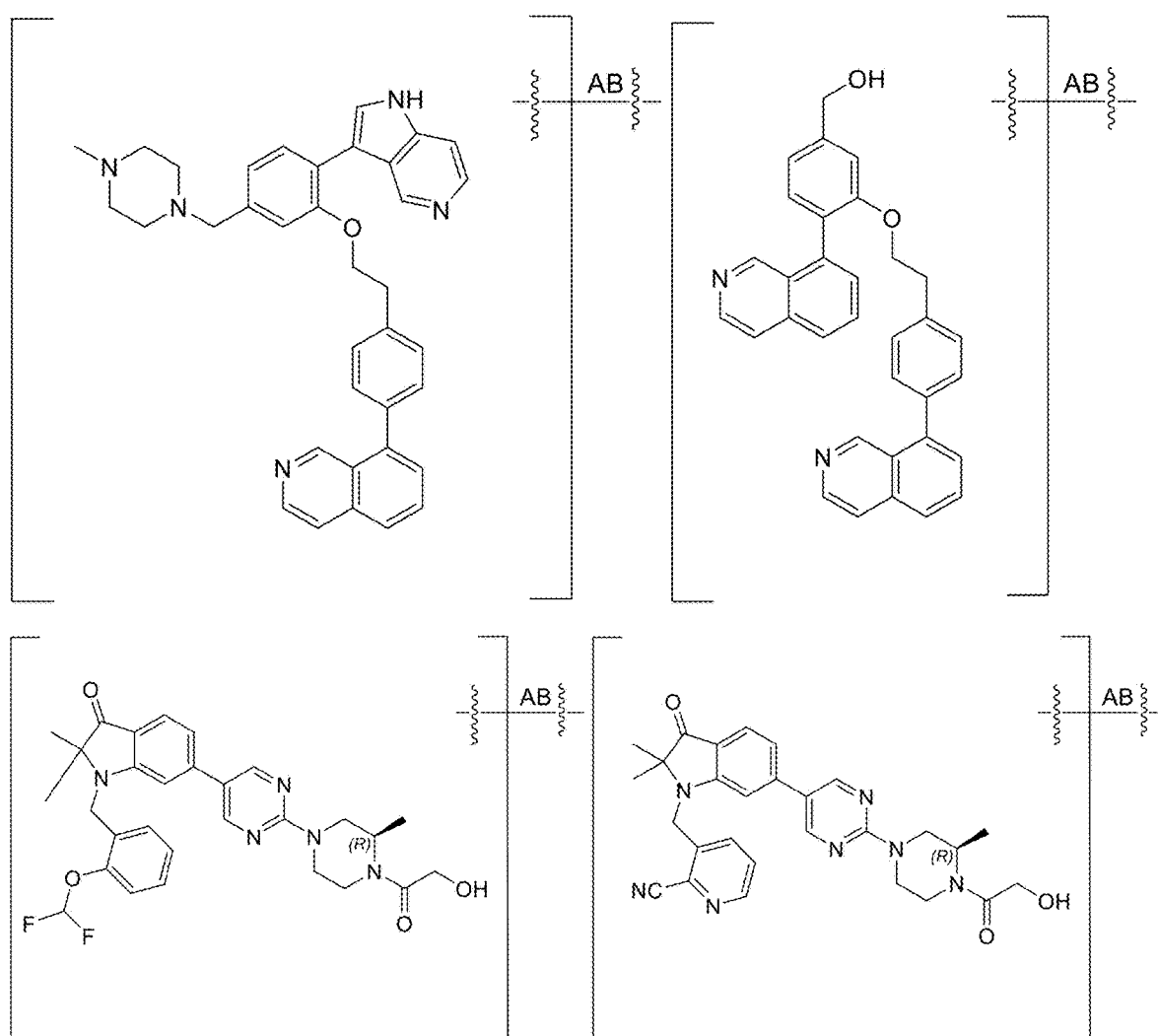
FIG. 6 provides a non-limiting list of exemplary Extracellular Protein Targeting Ligands that target TNF-alpha.

Representative Complement factor D Targeting Ligands are provided in FIG. 6. Additional Complement Factor D Targeting Ligands are provided in, for example, J Med Chem 60: 5717-5735 (2017), Nat Chem Biol 12: 1105-1110 (2016), U.S. Pat. Nos. 9,598,446B2, 9,643,986B2, 9,663,543B2, 9,695,205B2, 9,732,103B2, 9,732,104B2, 9,758,537B2, 9,796,741B2, 9,828,396B2, U.S. patent Ser. No. 10/000,516B2, U.S. patent Ser. No. 10/005,802B2, U.S. patent Ser. No. 10/011,612B2, U.S. patent Ser. No. 10/081,645B2, U.S. patent Ser. No. 10/087,203B2, U.S. patent Ser. No. 10/092,584B2, U.S. patent Ser. No. 10/100,072B2, U.S. patent Ser. No. 10/106,563B2, U.S. patent Ser. No. 10/138,225B2, U.S. patent Ser. No. 10/189,869B2, U.S. patent Ser. No. 10/253,053B2, U.S. patent Ser. No. 10/287,301B2, U.S. patent Ser. No. 10/301,336B2, U.S. patent Ser. No. 10/370,394B2, U.S. patent Ser. No. 10/385,097B2, U.S. patent Ser. No. 10/428,094B2, U.S. patent Ser. No. 10/428,095B2, U.S. patent Ser. No. 10/464,956B2, U.S. patent Ser. No. 10/550,140B2, U.S. patent Ser. No. 10/660,876B2, U.S. patent Ser. No. 10/662,175B2, U.S. patent Ser. No. 10/689,409B2, U.S. patent Ser. No. 10/807,952B2, U.S. patent Ser. No. 10/822,352B2, U.S. Pat. No. 9,464,081B2, and Hematological 102: 466-475 (2017), each of which is incorporated by reference herein.

In certain embodiments the Extracellular Targeting Ligand is selected from:

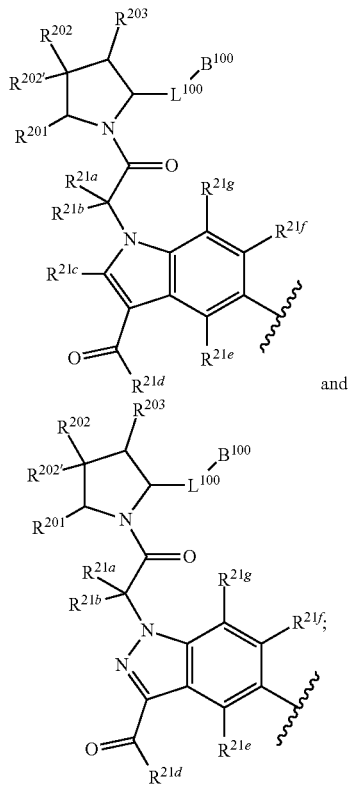

and wherein:
$R^{21a}$, $R^{21b}$, $R^{21c}$, $R^{21d}$, $R^{21e}$, $R^{21f}$, and $R^{21g}$ are independently at each occurrence selected from the group consisting of hydrogen, alkyl, alkenyl, alkynyl, F, Cl, Br, I, hydroxyl, alkoxy, azide, amino, cyano, —$NR^6R^7$, —$NR^8SO_2R^3$, —$NR^8S(O)R^3$, haloalkyl, heteroalkyl, aryl, heteroaryl, heterocyclyl, —$SR^3$, —$C(O)OR^3$, —$C(O)NR^6NR^7$, —$OR^3$, and heterocycle;

$R^{201}$, $R^{202}$, $R^{202'}$, and $R^{203}$ are independently selected from hydrogen, halogen, hydroxyl, nitro, cyano, amino, $C_1$-$C_6$alkyl, $C_2$-$C_6$alkenyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkylNR$^9$R$^{10}$, —$C(O)OR^9$, —$OC(O)R^9$, —$NR^9C(O)R^{10}$, —$C(O)NR^9R^{10}$, —$OC(O)NR^9R^{10}$, —$O$(heteroaryl), —$NR^9C(O)OR^{10}$, $C_1$-$C_2$haloalkyl, —$C_0$-$C_4$alkyl($C_3$-$C_7$cycloalkyl) and —O—$C_0$-$C_4$alkyl($C_3$-$C_7$cycloalkyl), and $C_1$-$C_2$haloalkoxy, where $R^{209}$ and $R^{210}$ are independently chosen at each occurrence from hydrogen, $C_1$-$C_6$alkyl, and ($C_3$-$C_7$cycloalkyl)$C_0$-$C_4$alkyl;

or $R^{202}$ and $R^{202'}$ may be taken together to form a 3- to 6-membered spiro ring optionally substituted with 1 or more substituents independently chosen from halogen, hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

or $R^{201}$ and $R^{202}$ may be taken together to form a 3-membered carbocyclic ring, optionally substituted with 1, 2, or 3 substituents selected from $R^{21}$.

or $R^{201}$ and $R^{202}$ may be taken together to form a 4- to 6-membered carbocyclic ring or a 4- to 6-membered heterocyclic ring containing 1 or 2 heteroatoms independently chosen from N, O, and S, optionally substituted with 1, 2, or 3 substituents selected from $R^{21}$ $R^{202}$ and $R^{203}$ may be taken together to form a 3- to 6-membered carbocyclic ring or a 3- to 6-membered heterocyclic ring optionally substituted with 1, 2, or 3 substituents selected from $R^{21}$.

$L^{100}$ is selected from

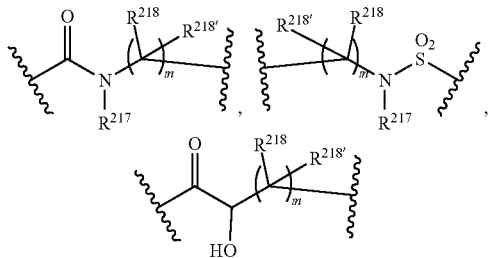

wherein $R^{217}$ is hydrogen or $C_1$-$C_6$alkyl and $R^{218}$ and $R^{218'}$ are independently chosen from hydrogen, halogen, hydroxymethyl, and methyl; and m is 0, 1, 2, or 3;

$B^{100}$ is a cycloalkyl, heterocycle group having 1, 2, 3, or 4 heteroatoms independently selected from N, O, and S, a $C_2$-$C_6$alkenyl, $C_2$-$C_6$alkynyl group, —($C_0$-$C_4$alkyl)(aryl), —($C_0$-$C_4$alkyl)(heteroaryl), or —($C_0$-$C_4$alkyl)(biphenyl), each of which is optionally substituted with 1, 2, 3, or 4 substituents independently selected from $R^{21}$.

In certain embodiments the Extracellular Targeting Ligand is selected from:

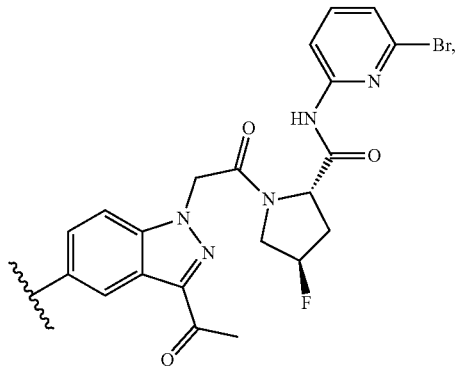

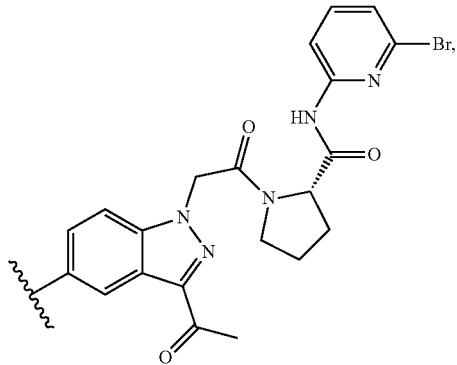

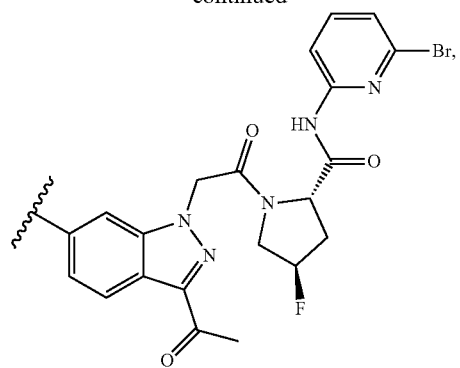
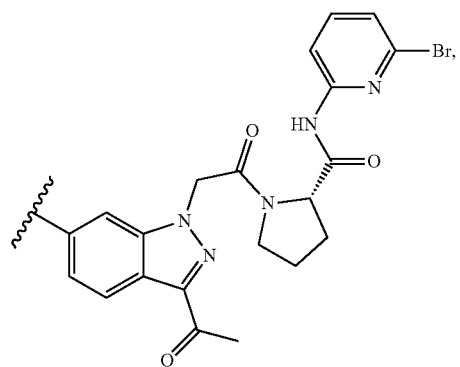
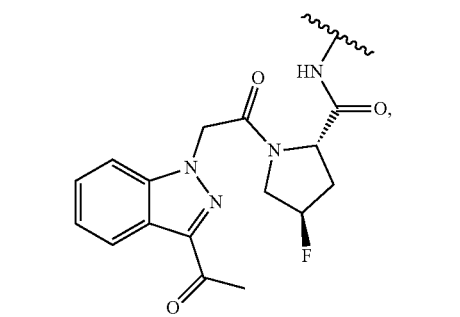
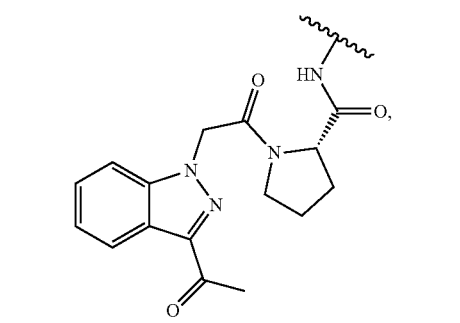
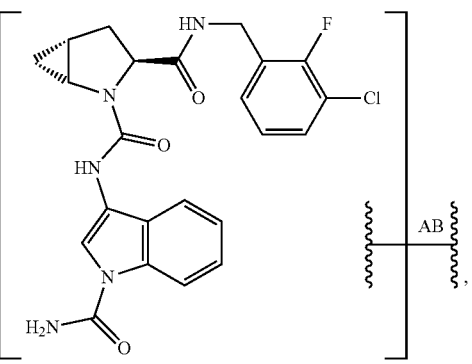
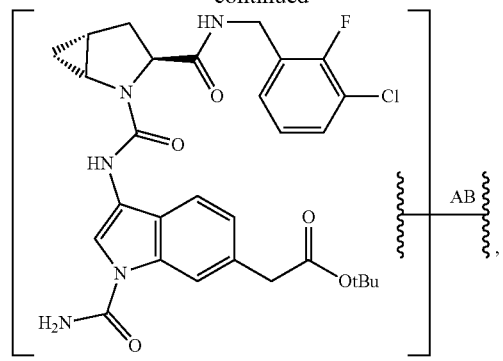
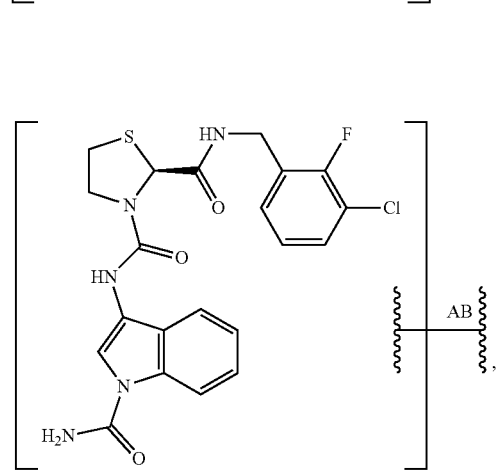
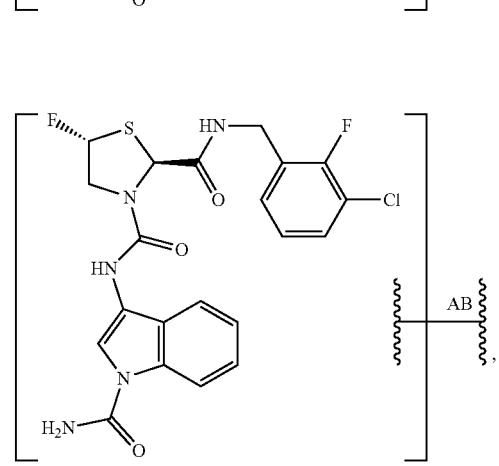
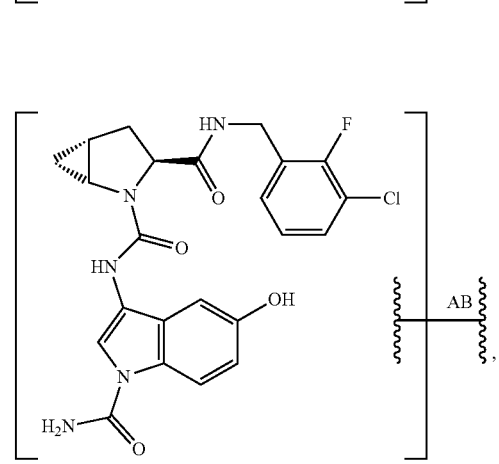

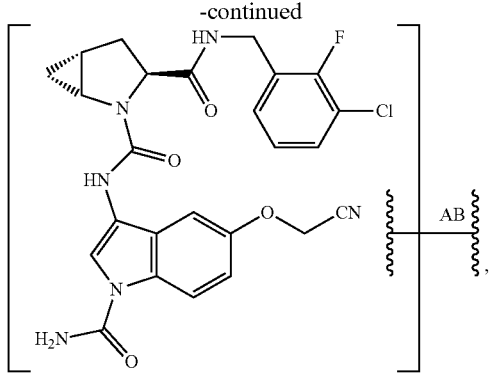
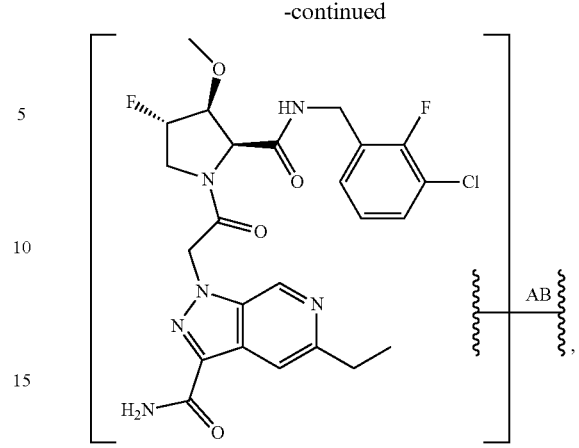
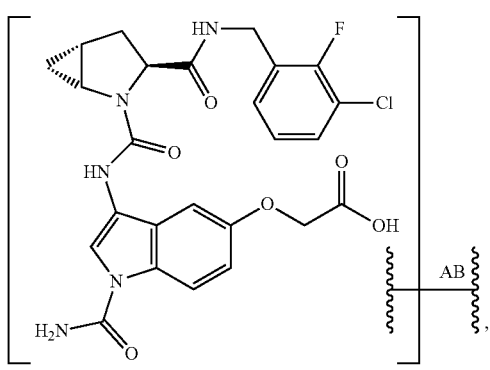
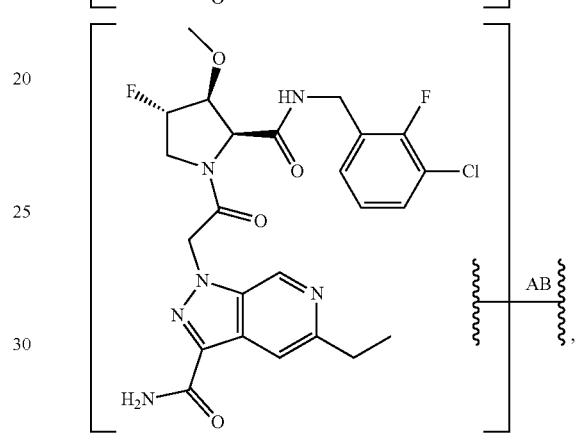
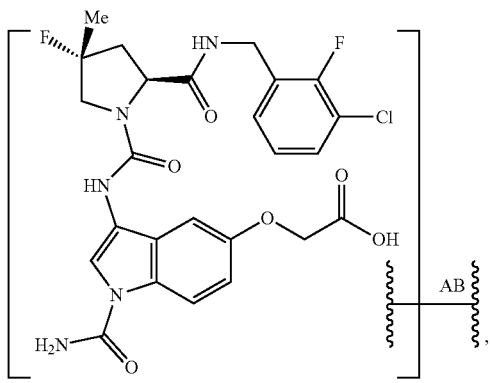
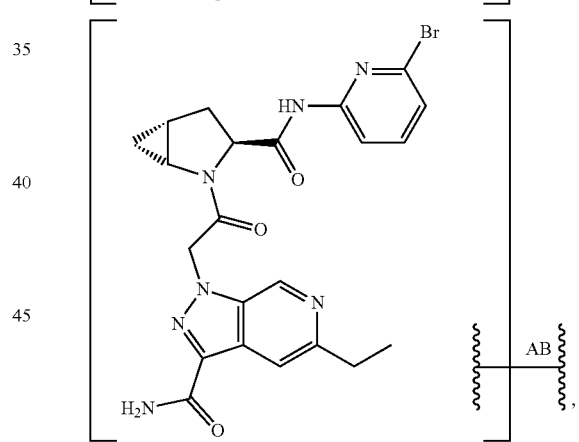
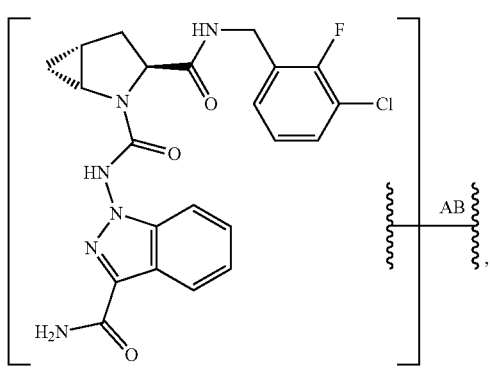
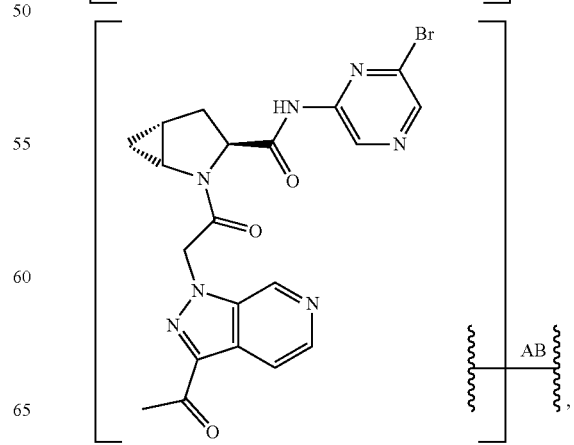

181
-continued
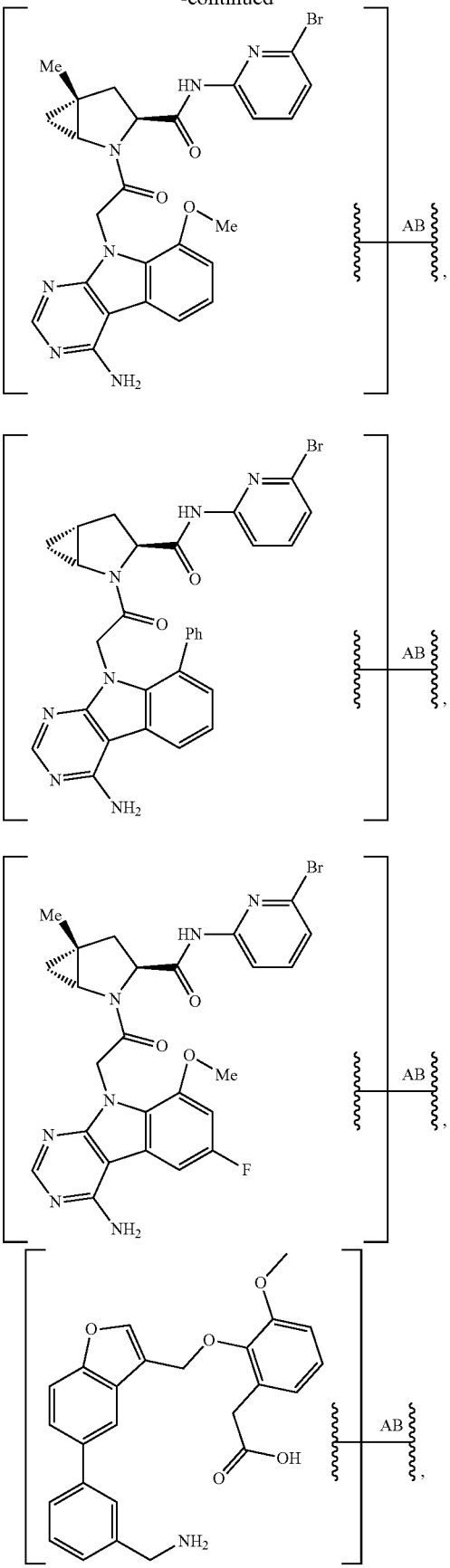
182
-continued
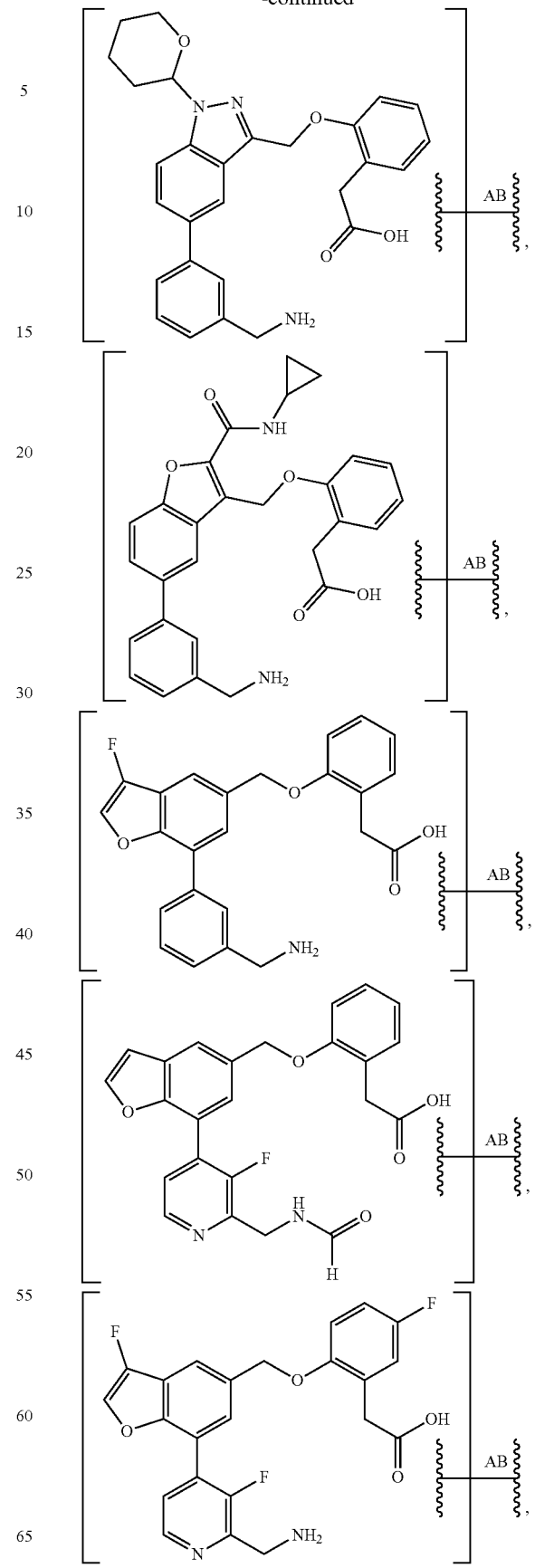

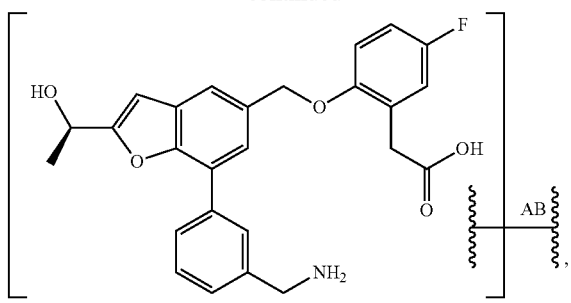
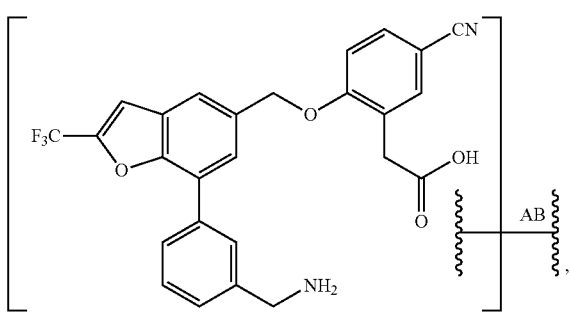

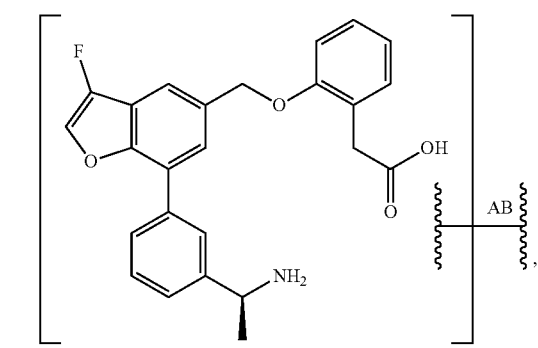
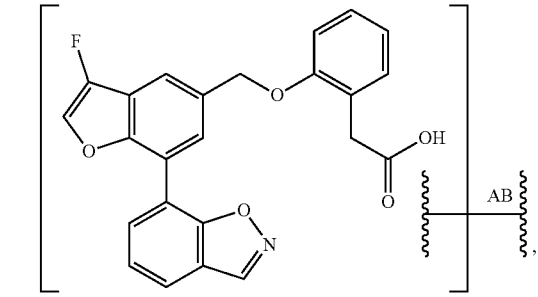
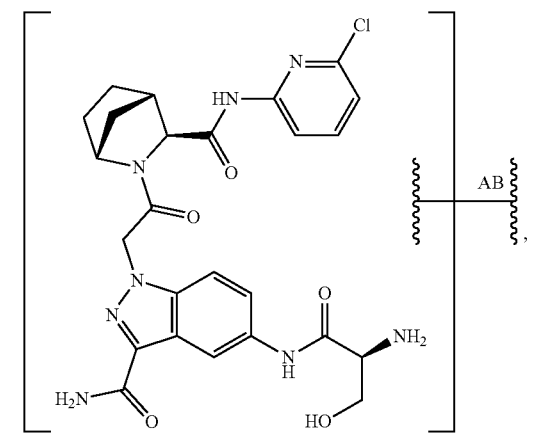
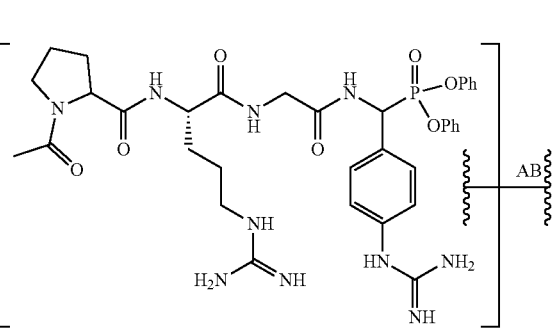
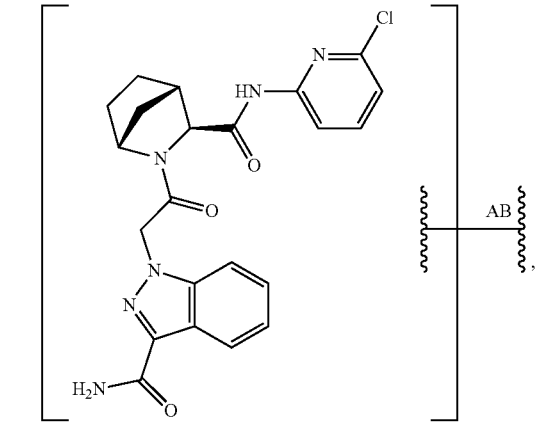
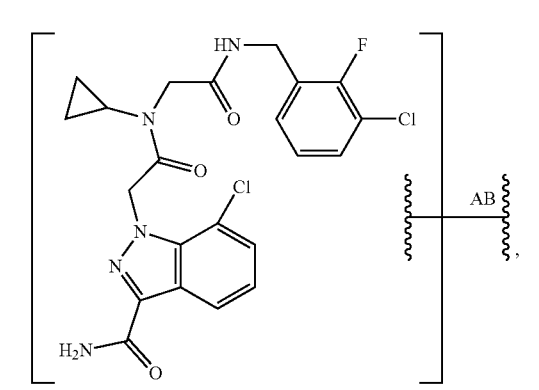

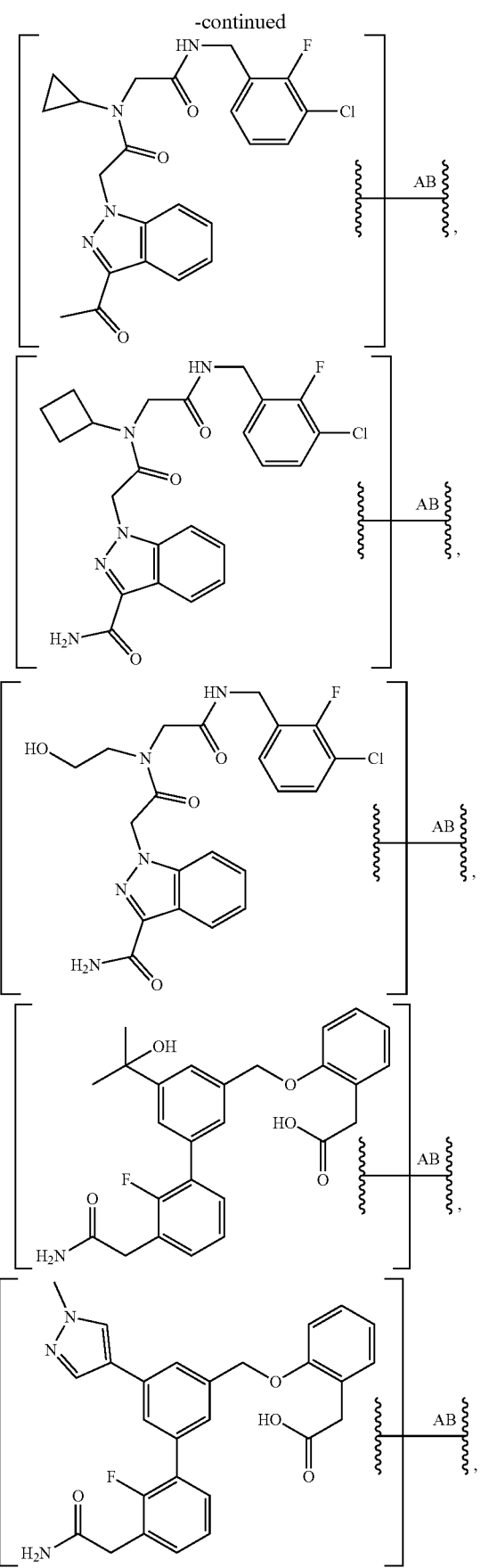
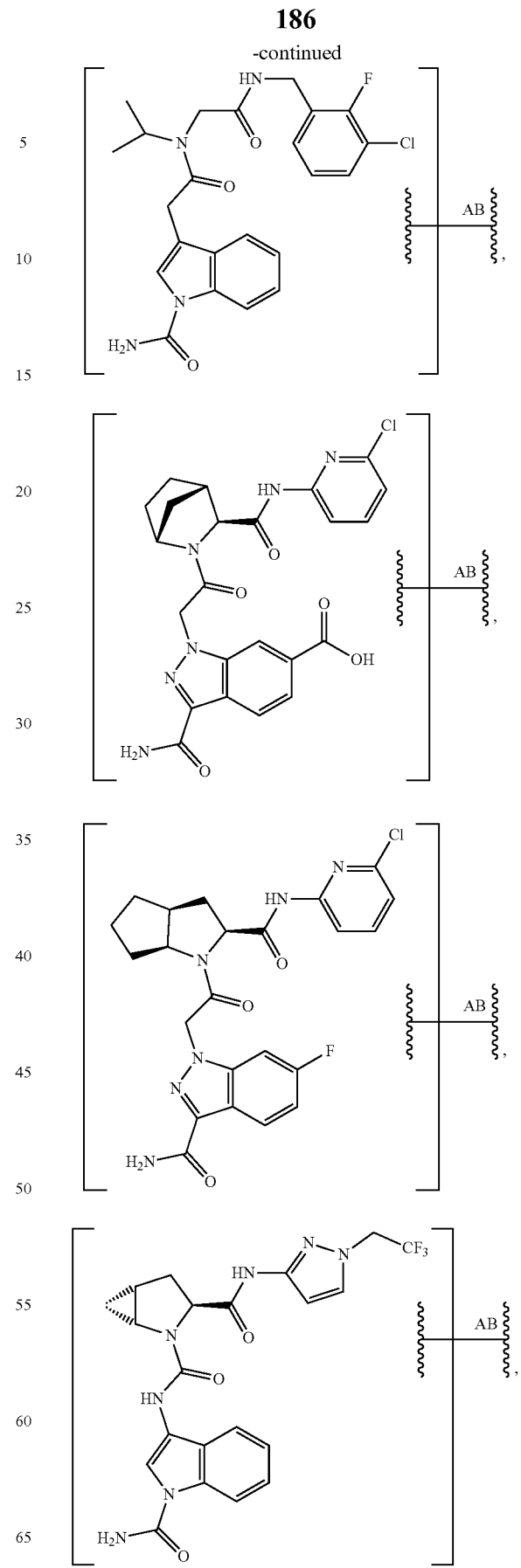

187

-continued

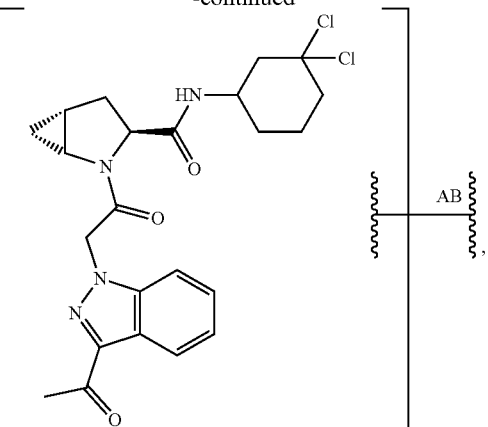

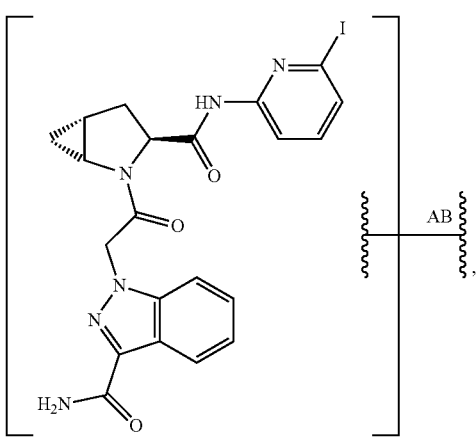

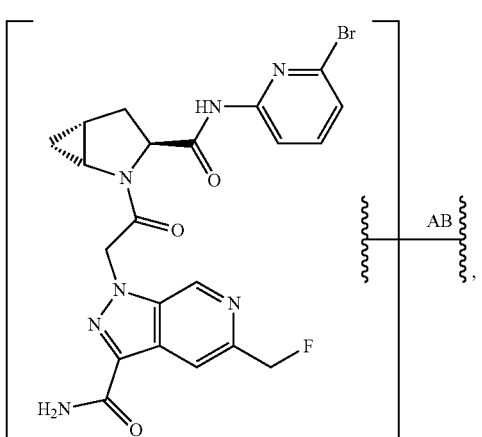

188

-continued

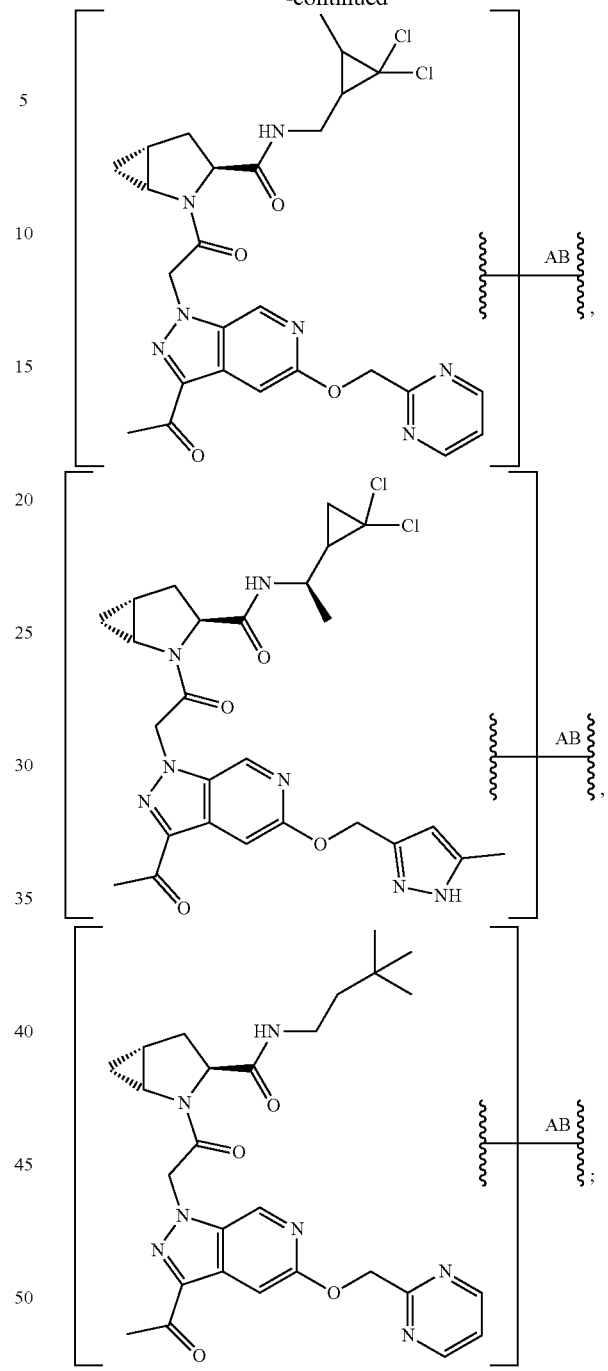

each of which is optionally substituted with 1, 2, 3, or 4 substituents independently selected from $R^{21}$.

In certain embodiments the Factor D Targeting Ligand is selected from a ligand described in U.S. Pat. Nos. 9,796,74; 10,011,612; WO2018/160889; WO2019/195720; WO2019/057946; Karki, R. G. et al. Design, Synthesis, and Preclinical Characterization of Selective Factor D Inhibitors Targeting the Alternative Complement Pathway. J. Med. Chem. 2019, 62 (9), 4656-4668; or Belanger, D. B. et al.; WO2015/009977.

In certain embodiments the complement factor D targeting ligand-linker-is selected from:

189
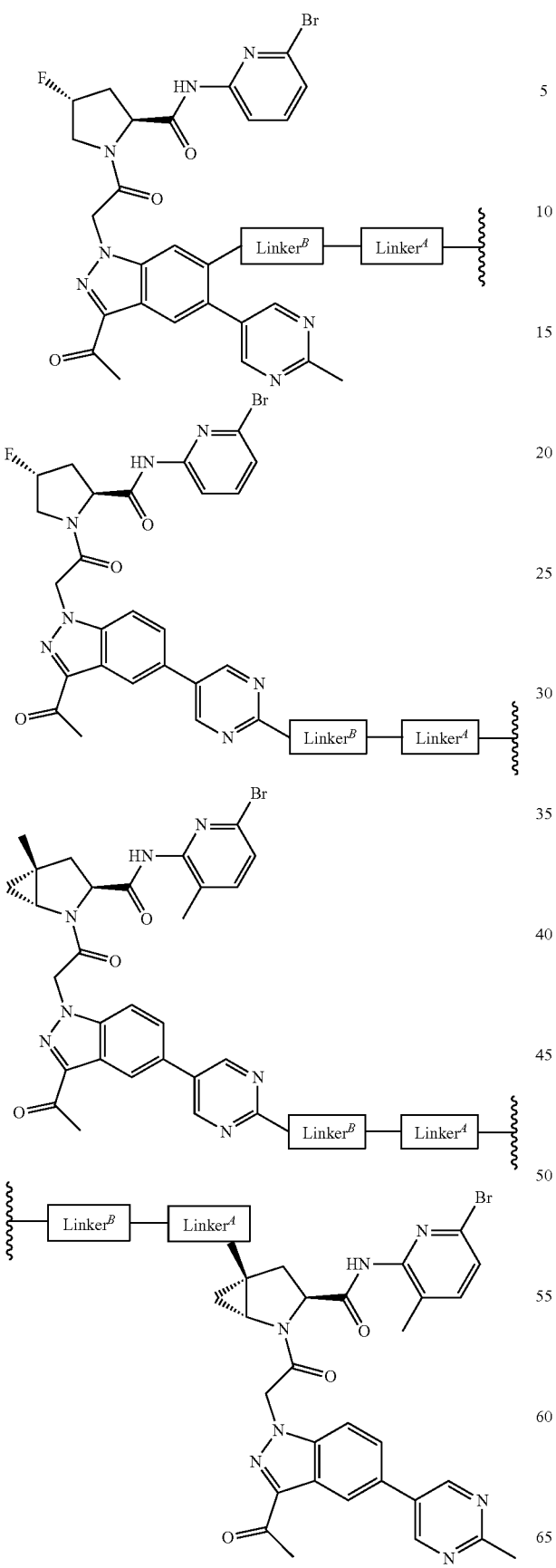
190
-continued
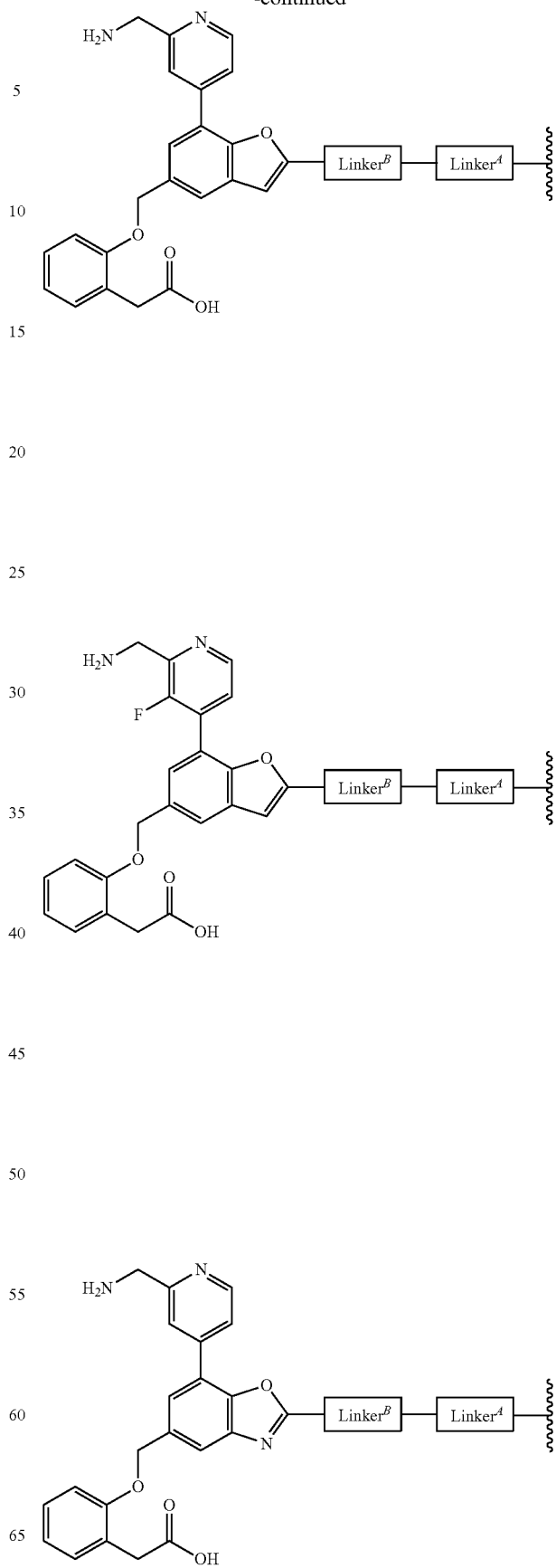

191
-continued
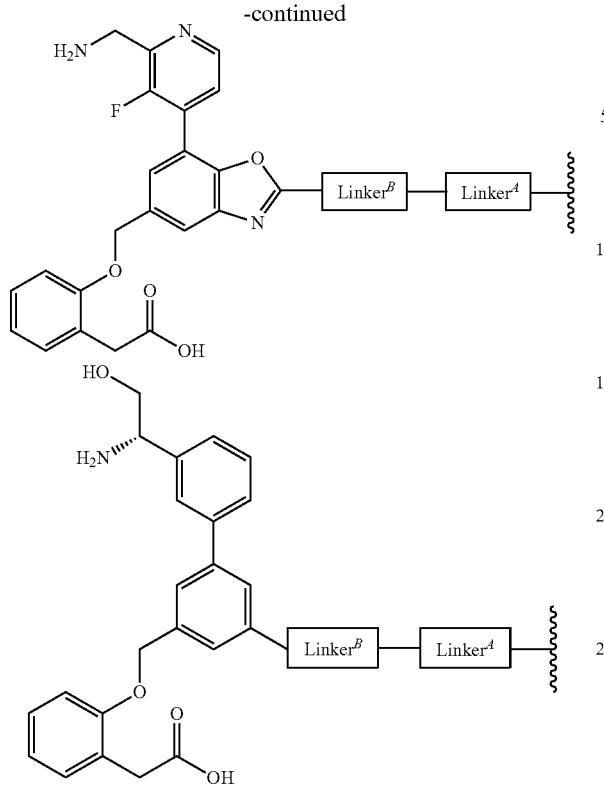
192
-continued
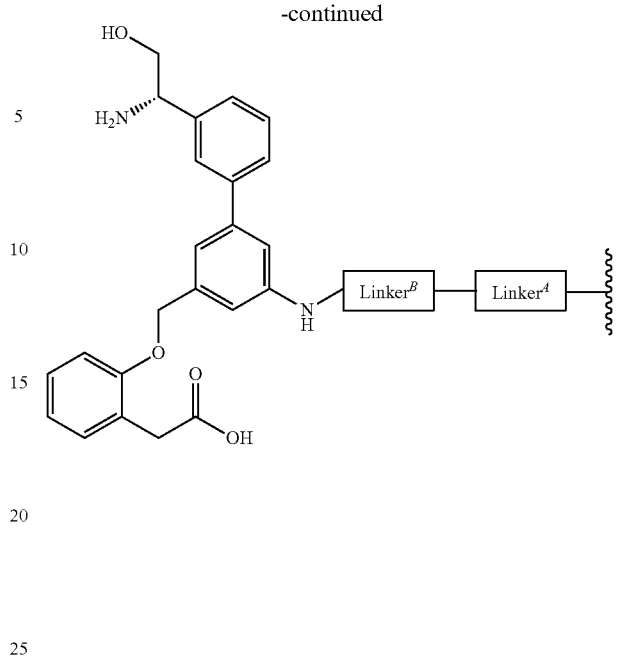
In certain embodiments the compound of the present invention is selected from the following compounds or a bi- or tri-dentate version thereof:
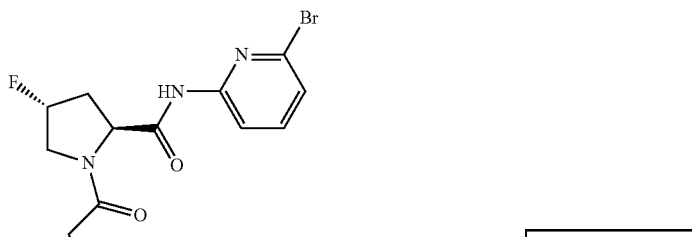
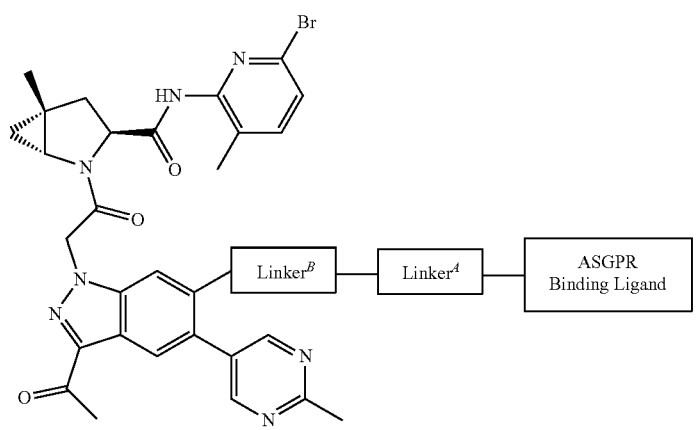

-continued
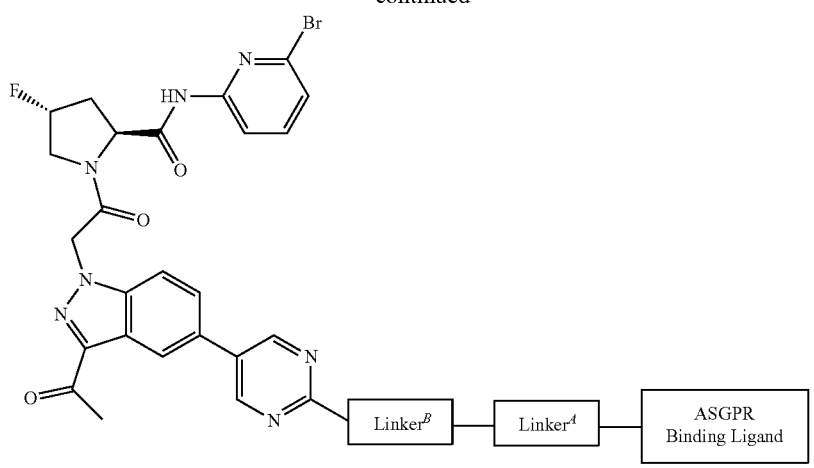
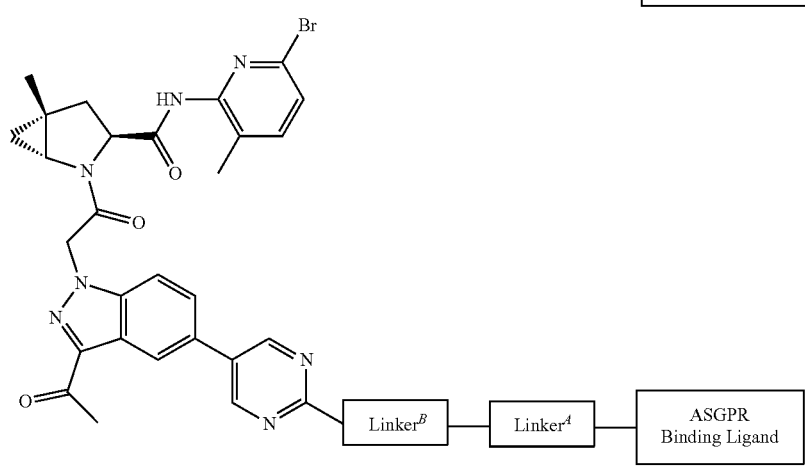
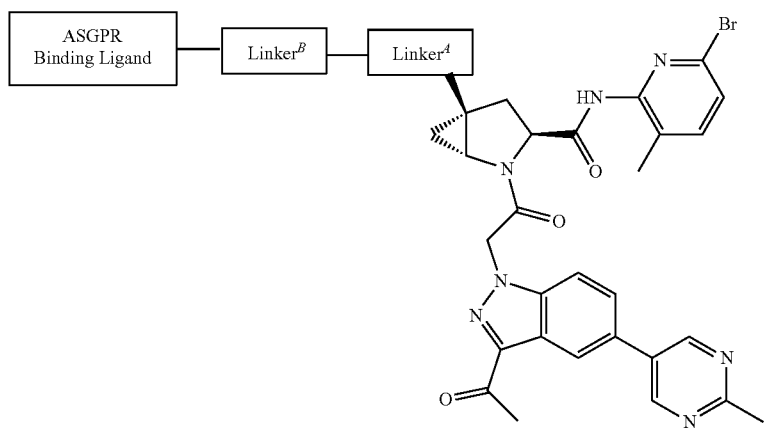
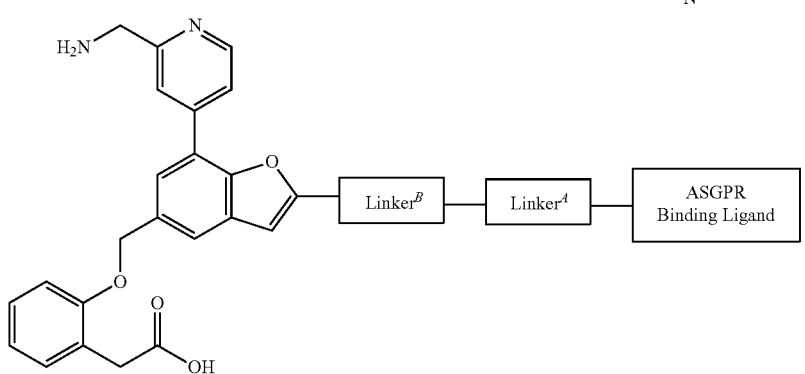

-continued
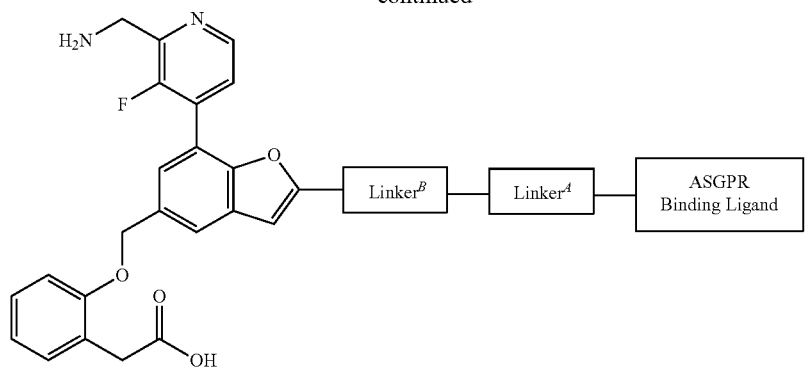
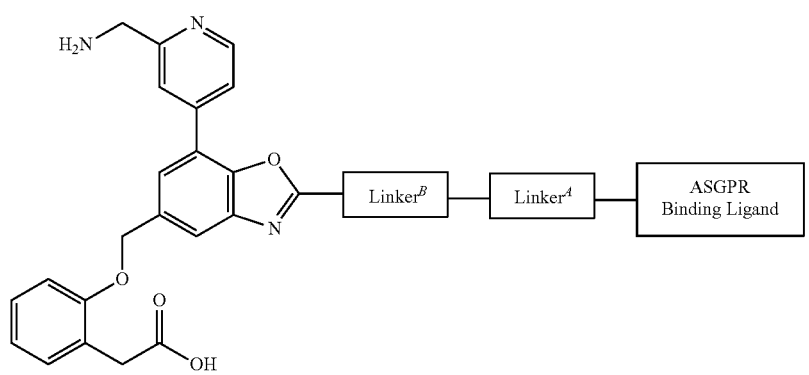
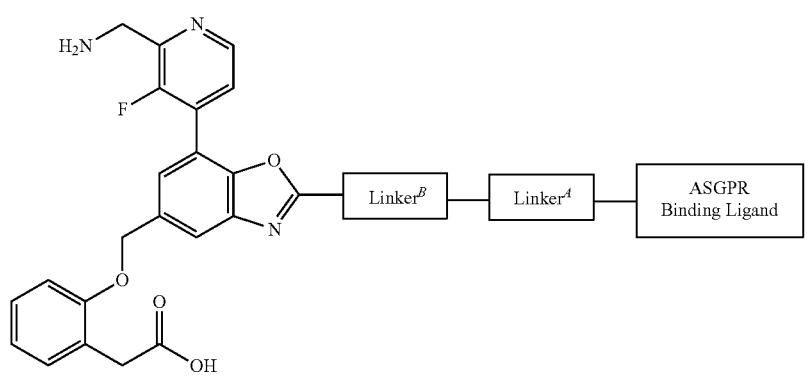
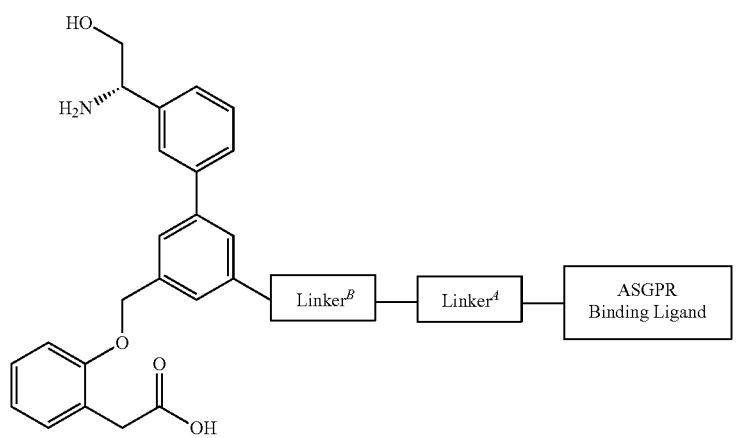

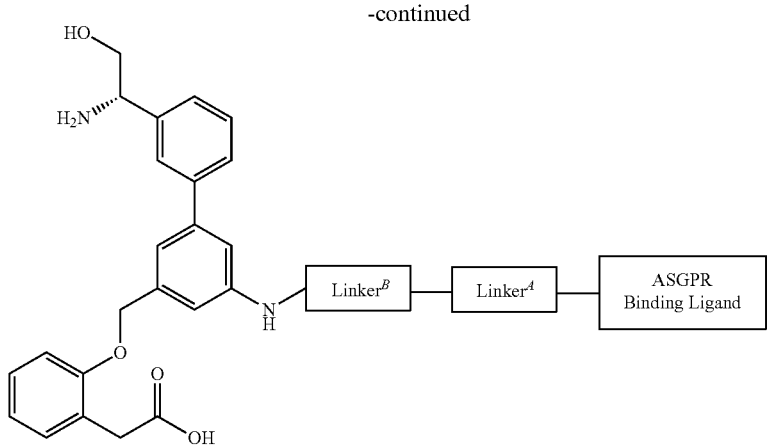

In certain embodiments the compound of the present invention is selected from the following compounds or a bi- or tri-dentate version thereof:

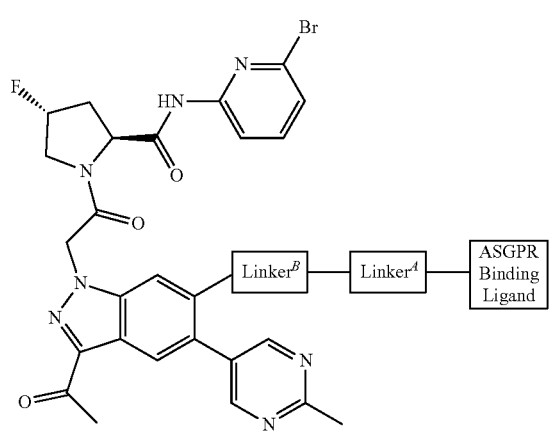

In certain embodiments the Factor D Targeting Ligand is selected from:

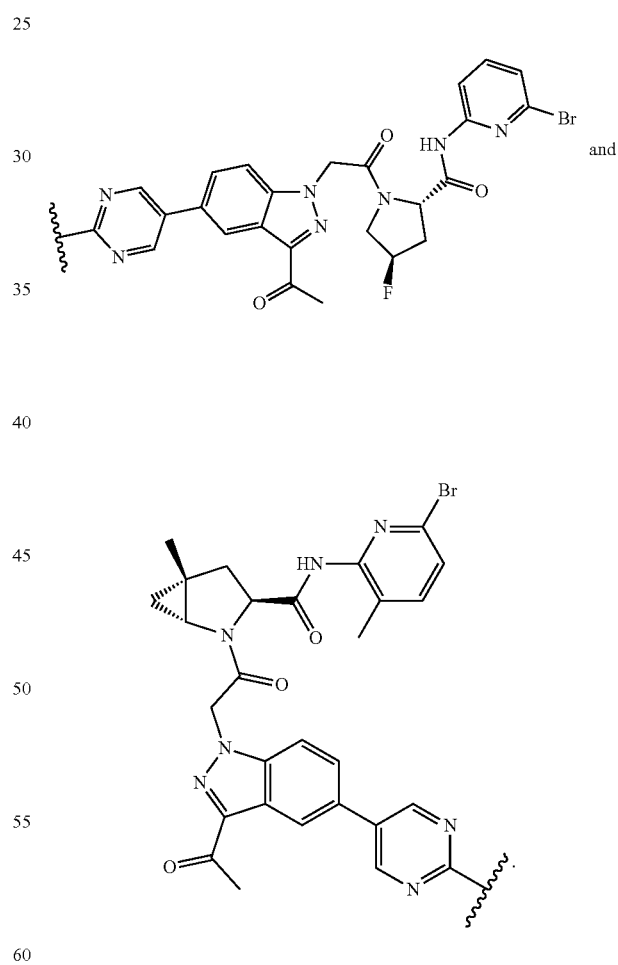

In certain non-limiting embodiments, the Factor D degrading compound of the present invention is selected from the following compounds or a bi- or tri-dentate version thereof:

199 200
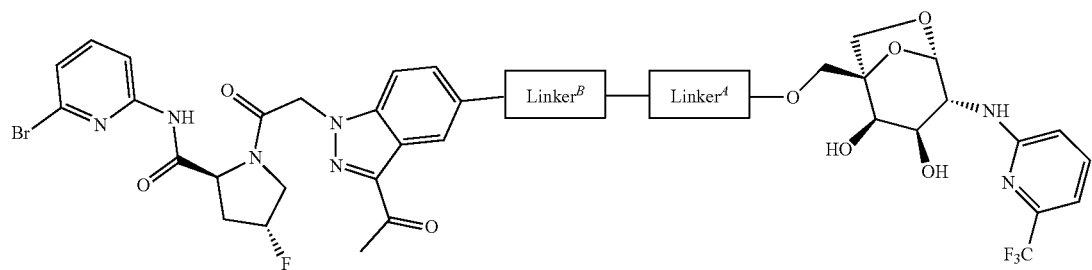
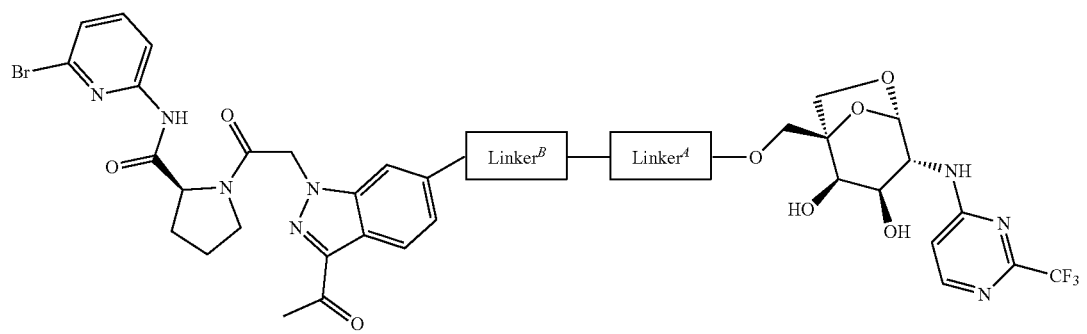
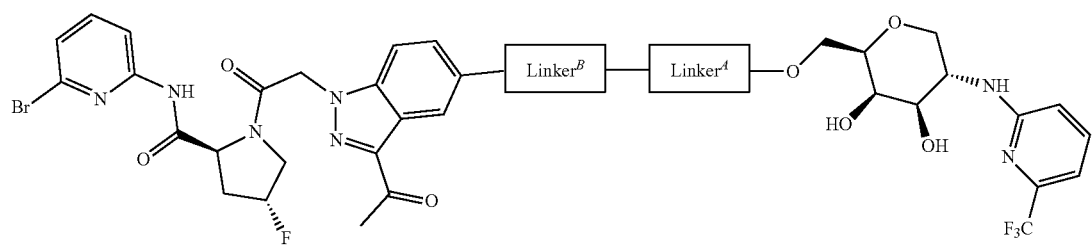
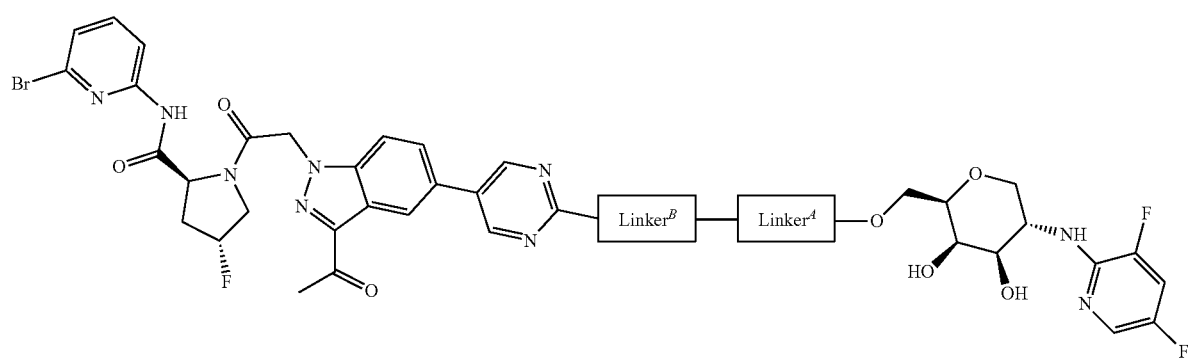
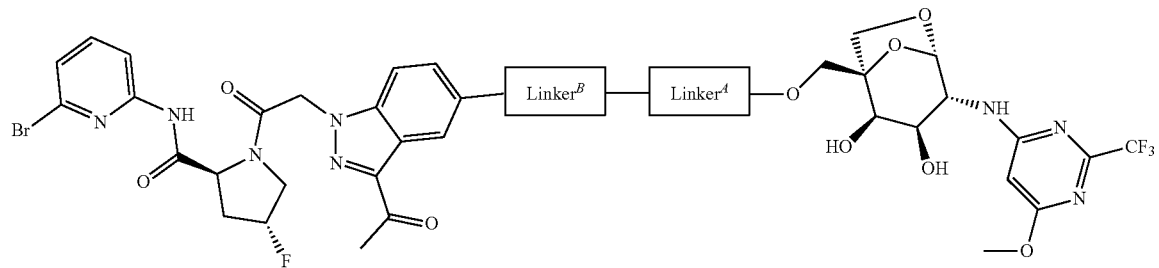

-continued
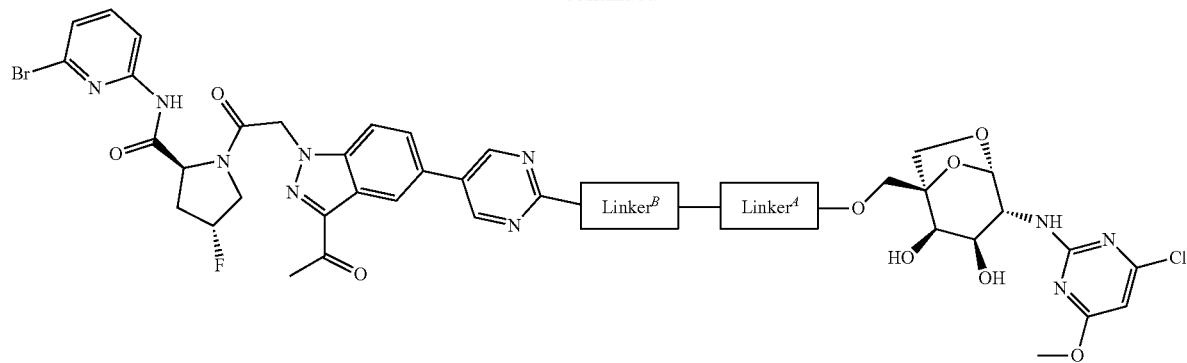
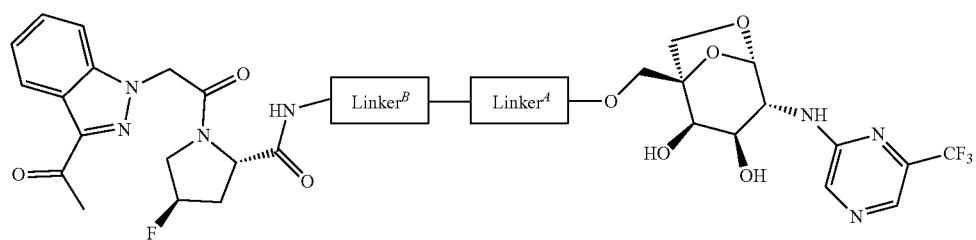
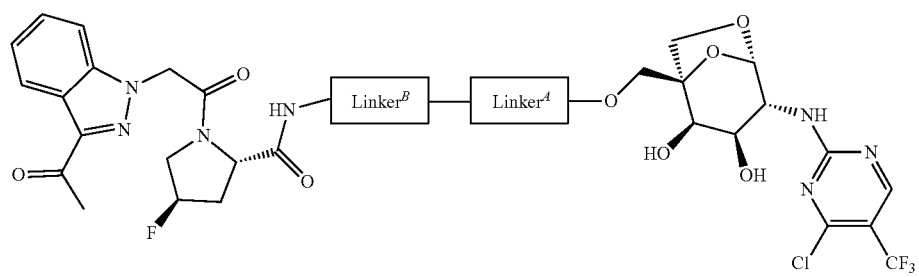
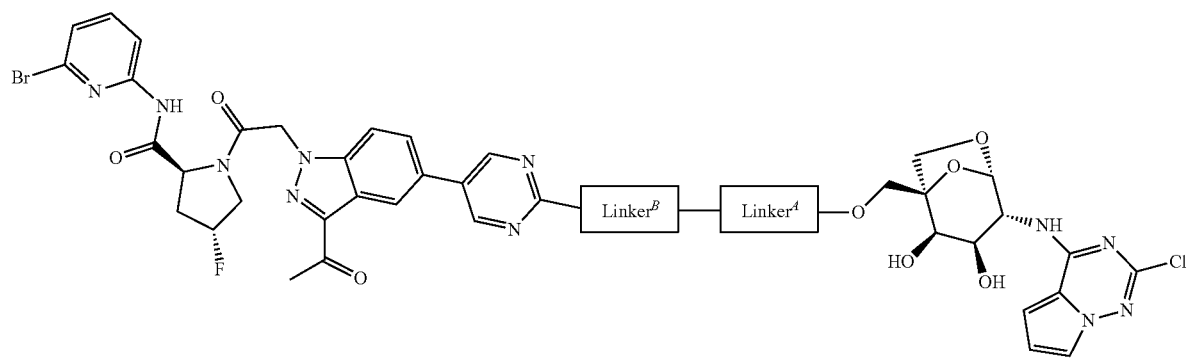
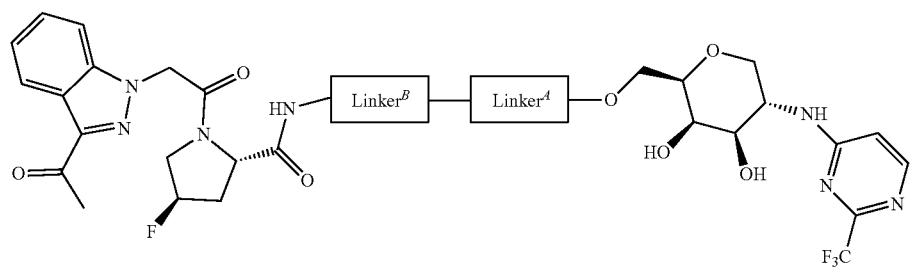

-continued
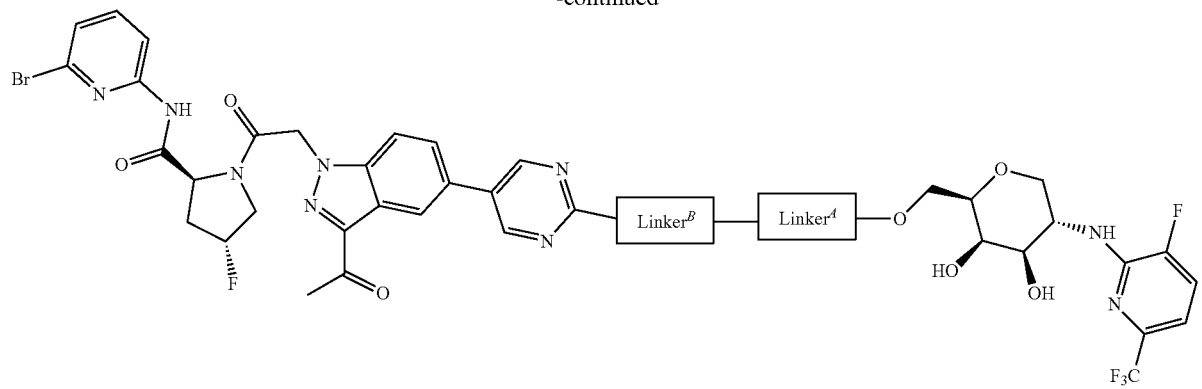
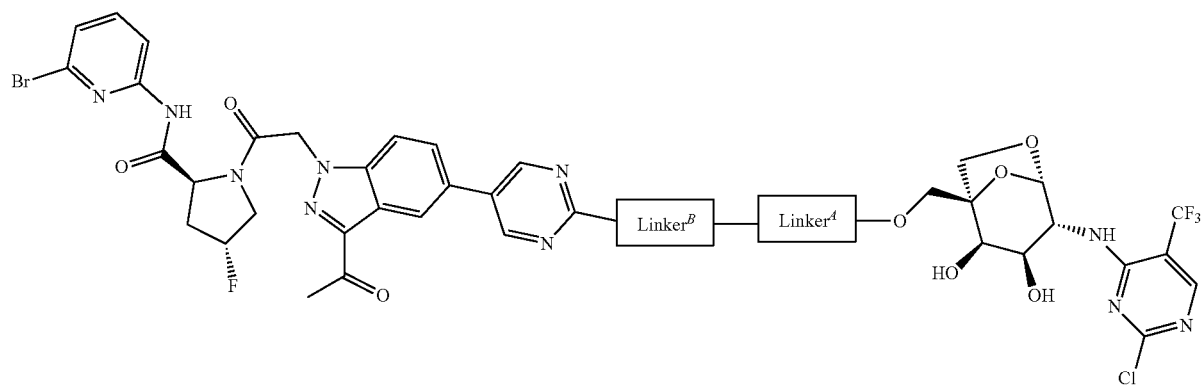
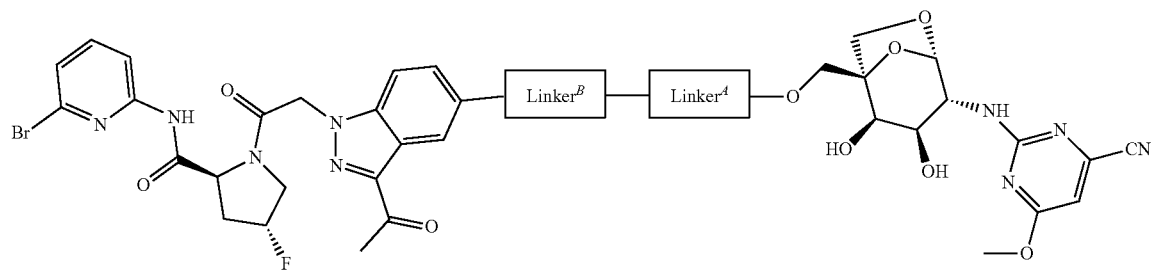

Non-limiting examples of Complement Factor D degrading compounds include:
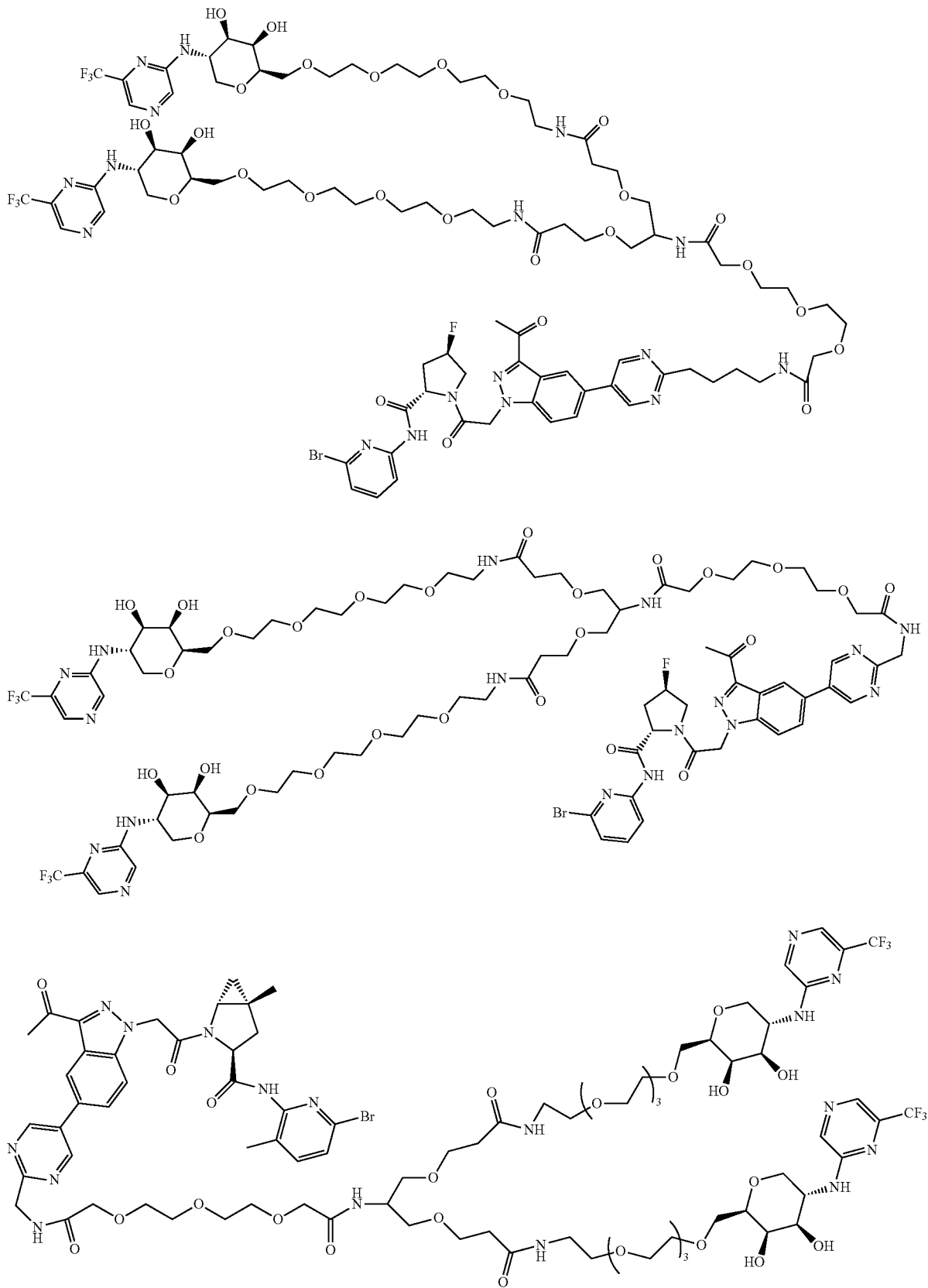

-continued

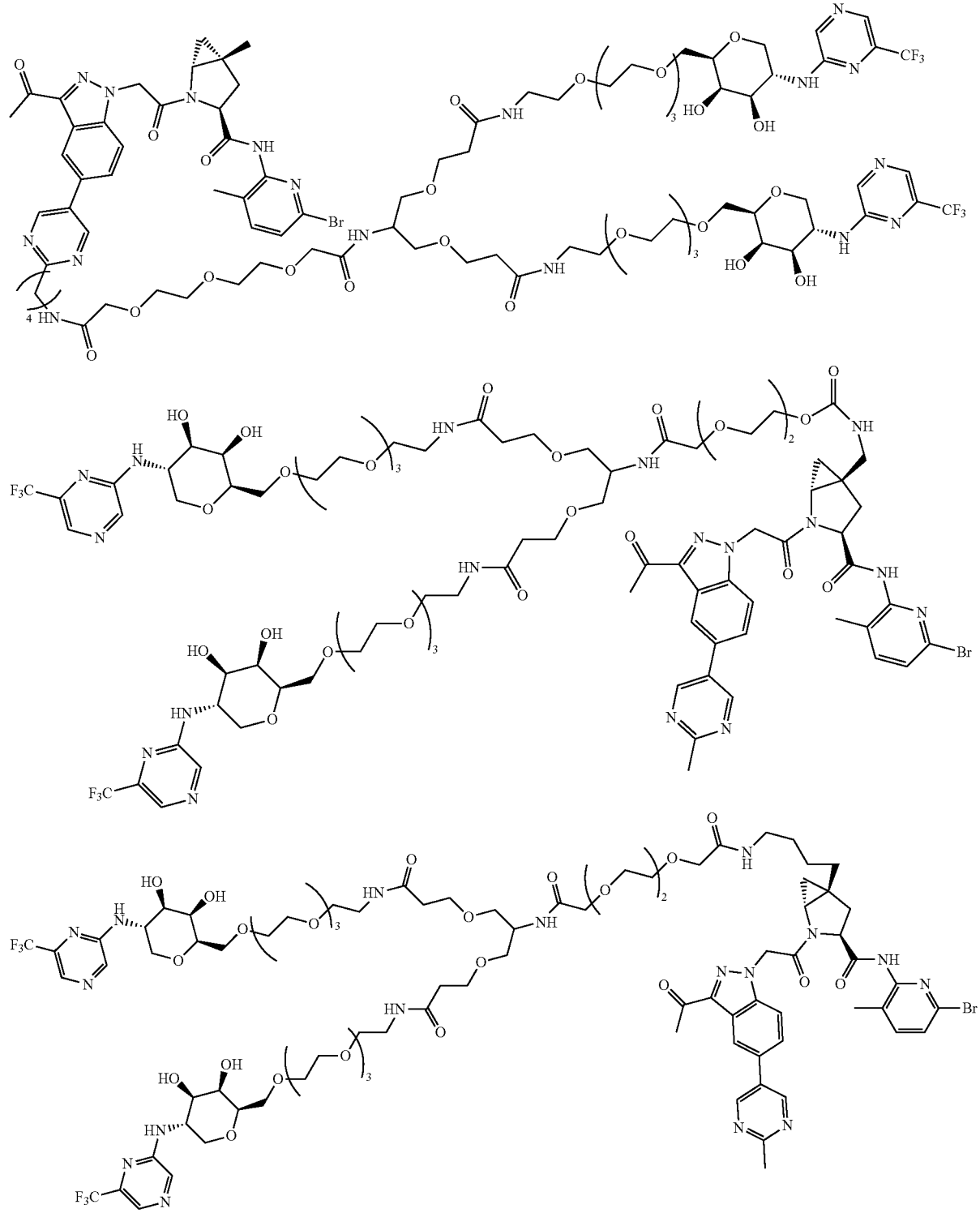

Factor H

In some embodiments, the Target Extracellular Protein is human complement factor H (UniProtKB—P08603 (CFAH_HUMAN)). Complement factor H is a glycoprotein that plays an essential role in maintaining a well-balanced immune response by modulating complement activation. Acts as a soluble inhibitor of complement, where its binding to self-markers such as glycan structures prevents complement activation and amplification on cell surfaces. Complement factor H accelerates the decay of the complement alternative pathway (AP) C3 convertase C3bBb, thus preventing local formation of more C3b, the central player of the complement amplification loop. As a cofactor of the serine protease factor I, CFH also regulates proteolytic degradation of already-deposited C3b. In addition, it mediates several cellular responses through interaction with specific receptors. For example, CFH interacts with CR3/ITGAM receptor and thereby mediates the adhesion of human neutrophils to different pathogens. In turn, these pathogens are phagocytosed and destroyed.

The Protein Data Bank website provides the crystal structure of highly similar mutants of complement factor H searchable by 3KXV and 3KZJ (Bhattacharjee, A., et al., Mol Immunol 2010, 47, 1686-1691); as well as the crystal structure of wild type complement factor H bound to various compounds searchable by 2UWN (Prosser, B. E., et al., J Exp Med 2007, 204, 2277); 5WTB (Zhang, Y., et al., Biochem J 2017, 474, 1619-1631); 5O32 and 5O35 (Xue, X., et al., Nat Struct Mol Biol 2017, 24, 643-651); 4ONT (Blaum, B. S., et al., Nat Chem Biol 2015, 11, 77-82); and 4ZH1 (Blaum, B. S., et al., Glycobiology 2016, 26, 532-539).

Figure 7:
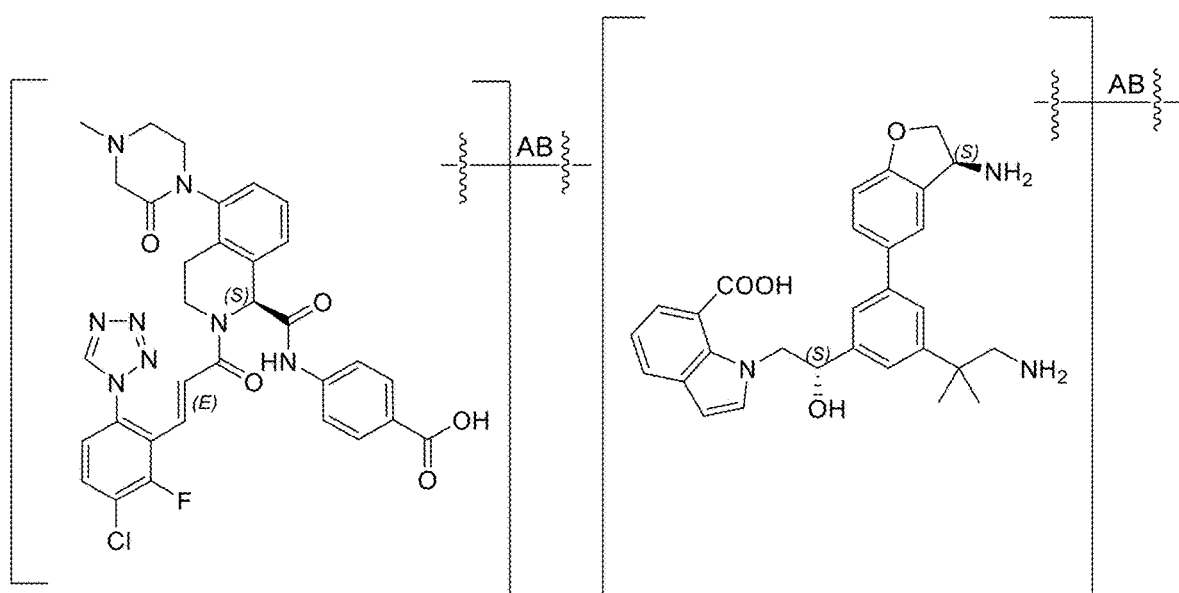
FIG. 7 provides a non-limiting list of exemplary Extracellular Protein Targeting Ligands that target factor XI.

Representative complement factor H Targeting Ligands are provided in FIG. 7. Additional complement factor H Targeting Ligands are provided in, for example, J Immunol 182: 6394-6400 (2009), PLoS Pathogens 4: e1000250 (2008), PLoS Pathogens 6: e1001027 (2010), U.S. patent Ser. No. 10/865,238B1, U.S. Pat. No. 8,962,795B2, US patent application 20160317573A1, and US patent application 20190315842A1, each of which is incorporated by reference herein.

Complement Component 5 (C5)

In some embodiments, the Target Extracellular Protein is human complement component 5 (C5) (UniProtKB—P01031 (CO5_HUMAN)). Activation of C5 by a C5 convertase initiates the spontaneous assembly of the late complement components, C5-C9, into the membrane attack complex. C5b has a transient binding site for C6. The C5b-C6 complex is the foundation upon which the lytic complex is assembled.

The Protein Data Bank website provides the crystal structure of Complement Component 5 searchable by 3CU7 (Fredslund, F., Nat Immunol 2008, 9, 753-760); as well as the crystal structure of Complement Component 5 bound to various compound searchable by 5I5K (Schatz-Jakobsen, J. A., et al, J Immunol 2016, 197, 337-344); 3PVM and 3PRX (Laursen, N. S., et al., EMBO J 2011, 30, 606-616); and 3KLS (Laursen, N. S., et al., Proc Natl Acad Sci 2010, 107, 3681-3686).

Figure 8:
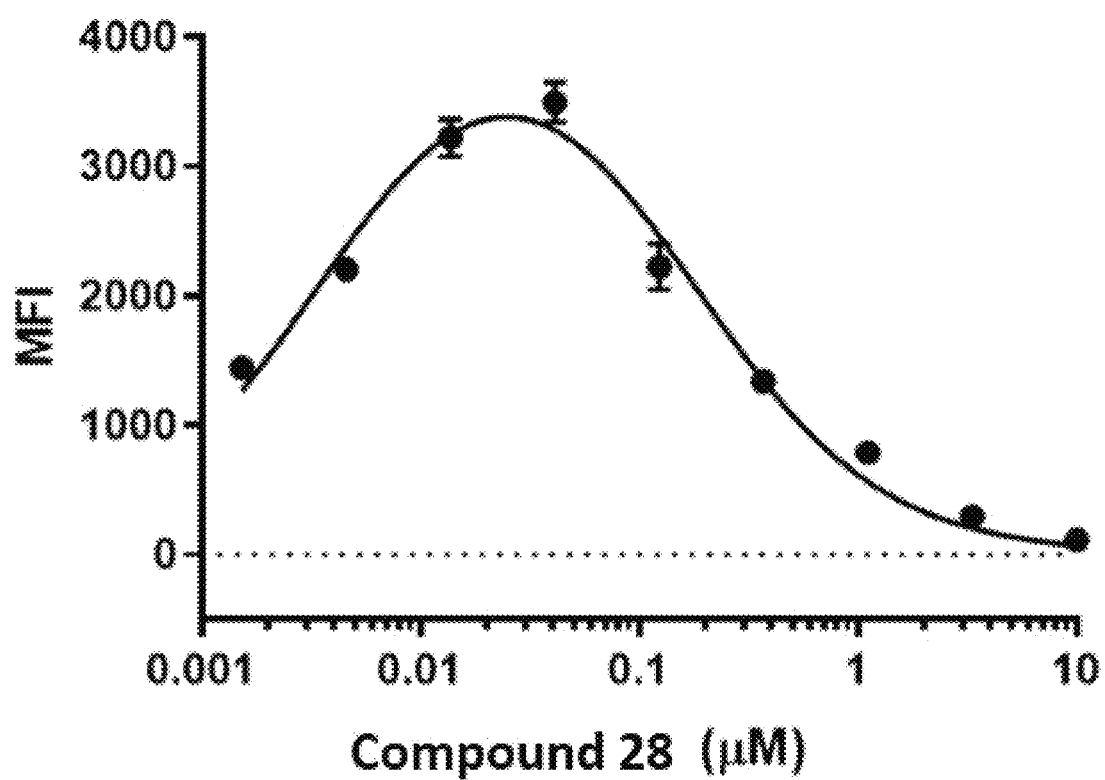
FIG. 8 is a graph of the cellular uptake of Compound 28 at various concentrations. The y-axis is mean fluorescence intensity (MFI) and the x-axis concentration of Compound 28 measured in micromolar. The experimental procedure is described in Example 3.
Figure 9:
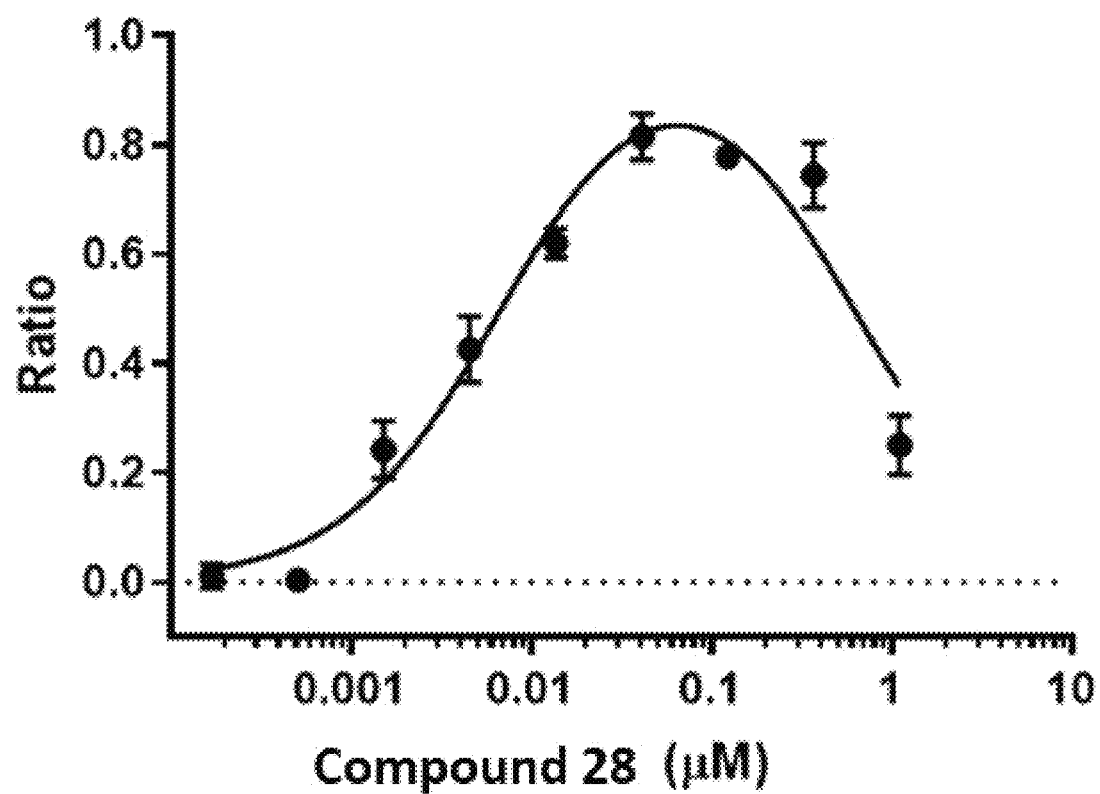
FIG. 9 is a graph of the ternary complex formation of Compound 28, IgG, and ASGPR at various concentrations of Compound 28. The y-axis is the ratio in the ternary complex and the x-axis concentration of Compound 28 measured in micromolar. The experimental procedure is described in Example 4.
Figure 10:
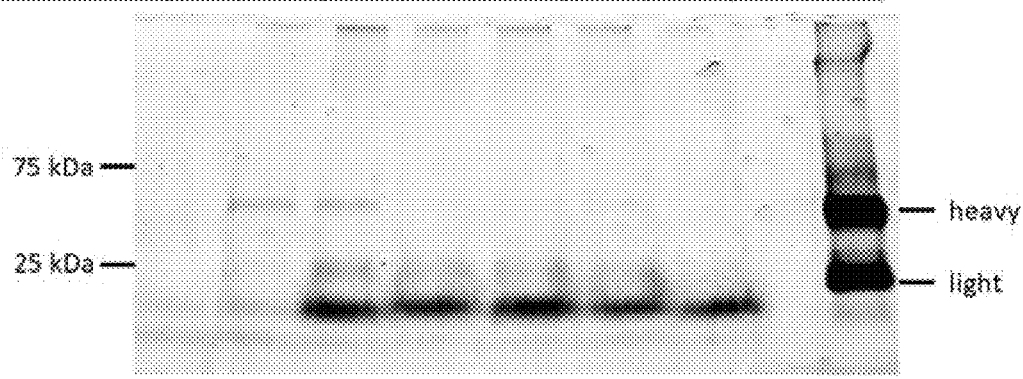
FIG. 10 is a western blot demonstrating the degradation of IgG-AF488 by Compound 28. The experimental procedure is described in Example 5.
Figure 11:
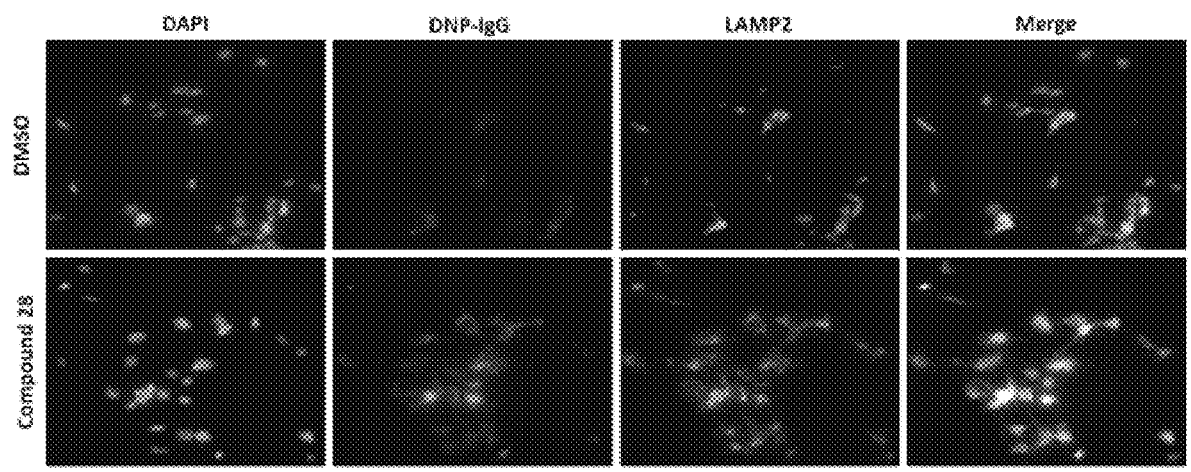
FIG. 11 is a colocalization image showing the uptake of DNP-IgG in the presence of Compound 28. The experimental procedure is described in Example 4.

Representative Complement Component 5 Targeting Ligands are provided in FIG. 8. Additional Complement Component 5 Targeting Ligands are provided in, for example, J Immunol 197: 337-344 (2016), Ther Adv Hematol 10: 1-11 (2019), BioDrugs 34: 149-158 (2020), Blood 135: 884-885 (2020), US patent application 20170342139A1, and US patent application 20200095307A1, each of which is incorporated by reference herein.

In certain embodiments the Extracellular Targeting Ligand is selected from:

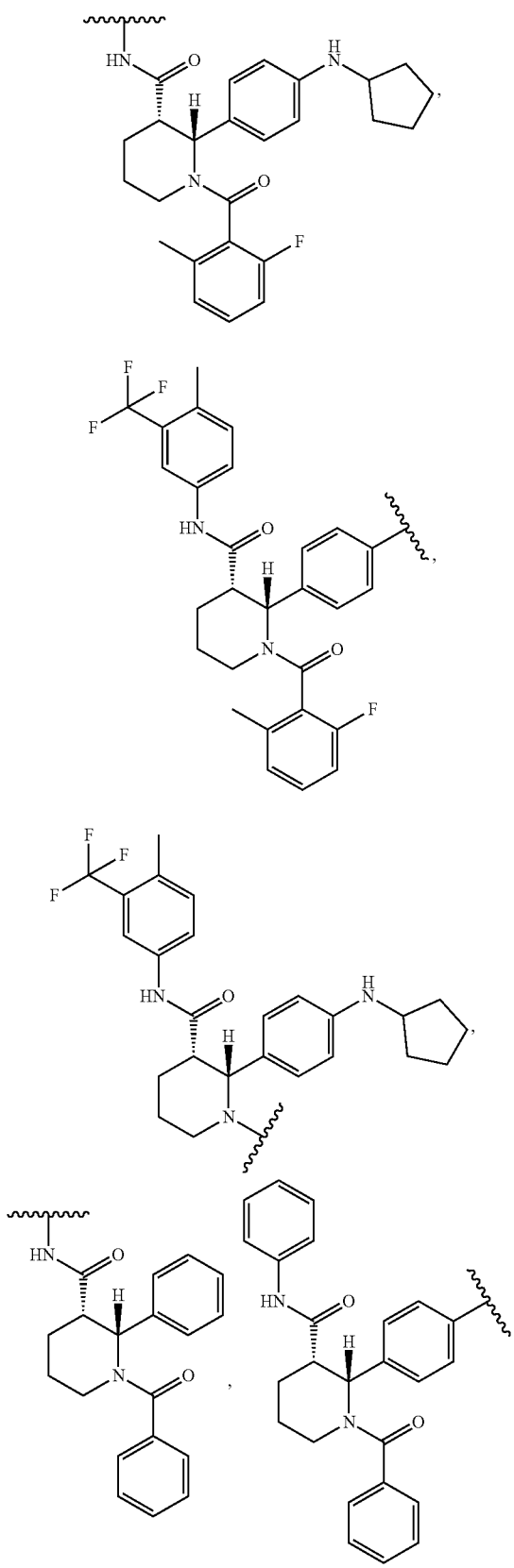

-continued

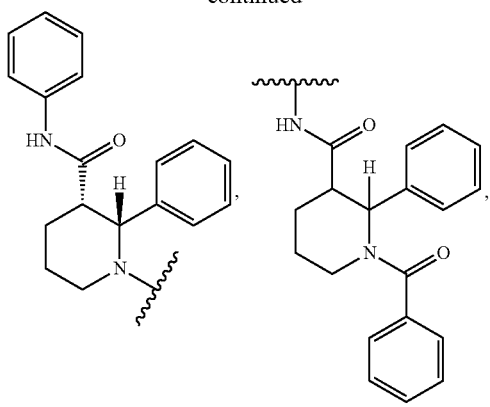

, and

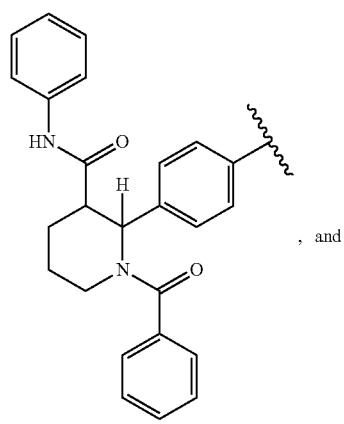

;

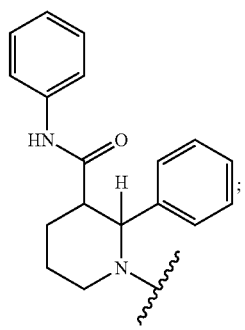

each of which is optionally substituted with 1, 2, 3, or 4 substituents independently selected from $R^{21}$.

In certain embodiments the complement C5 Targeting Ligand is selected from a ligand described in Jendza, K. et al. A Small-Molecule Inhibitor of C5 Complement Protein. Nat Chem Biol 2019, 15 (7), 666-668; or Zhang, M.; Yang, X.-Y.; Tang, W.; Groeneveld, T. W. L.; He, P.-L.; Zhu, F.-H.; Li, J.; Lu, W.; Blom, A. M.; Zuo, J.-P.; Nan, F.-J. Discovery and Structural Modification of 1-Phenyl-3-(1-Phenylethyl) Urea Derivatives as Inhibitors of Complement. ACS Med. Chem. Lett. 2012, 3 (4), 317-321.

In certain embodiments the C5 Targeting Ligand is selected from:

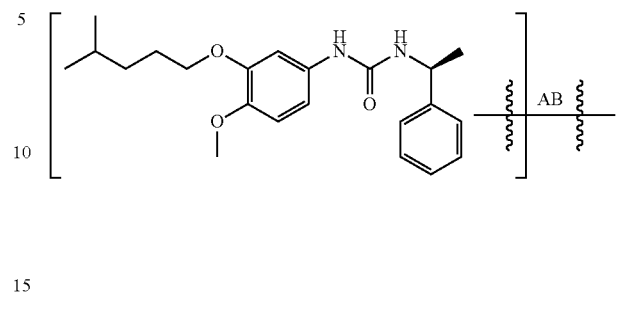

In certain embodiments the C5 Targeting Ligand is selected from:

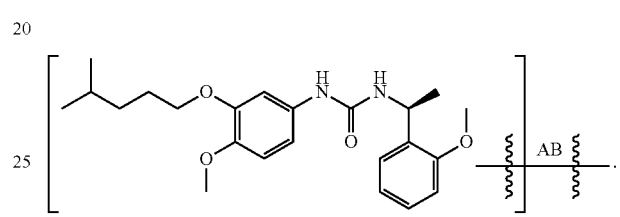

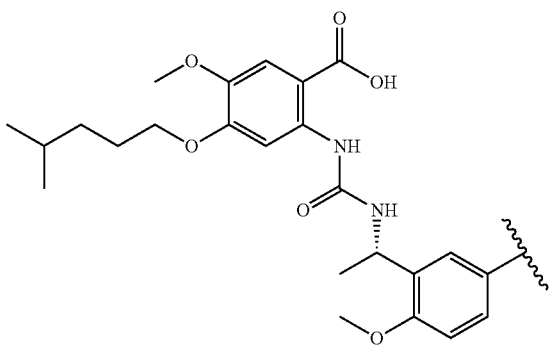

Non-limiting examples of Complement C5 degrading compounds include:
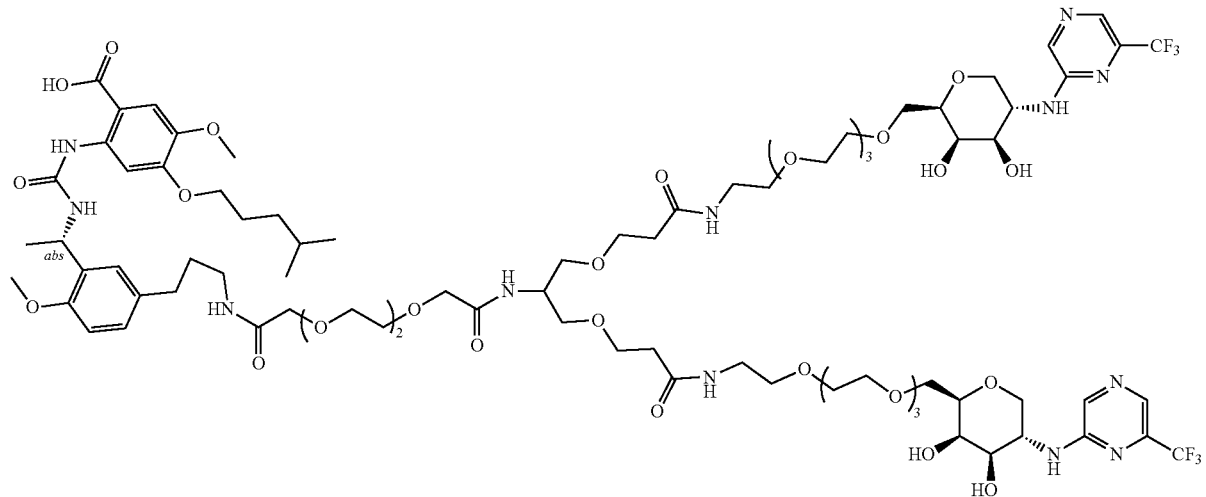
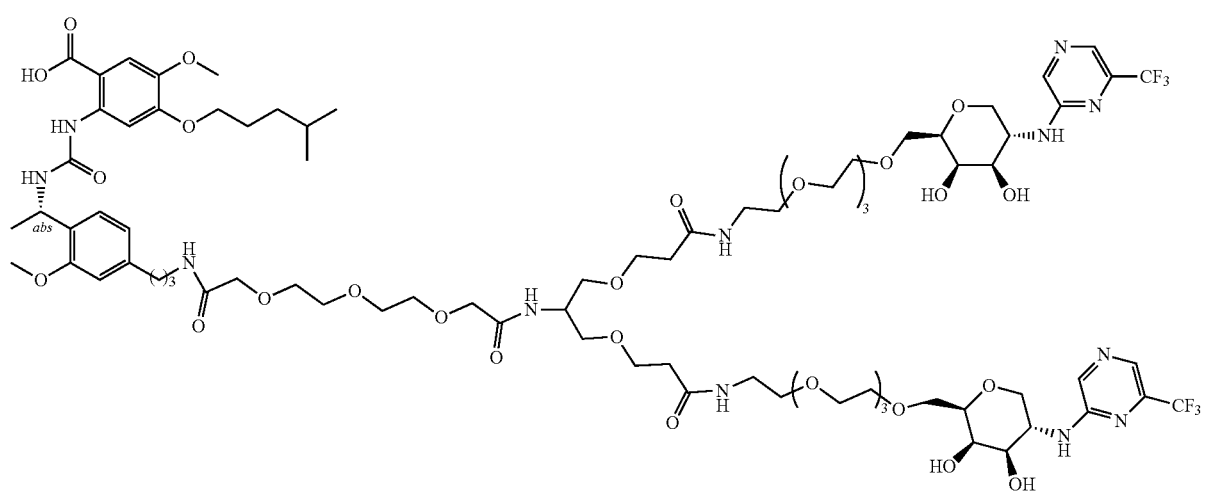

Complement C1s

In certain embodiments the extracellular targeting ligand is a C1s Targeting Ligand.

In certain embodiments the complement C1s Targeting Ligand is selected from a ligand described in WO2020/198062 or U.S. Pat. No. 6,683,055.

In certain embodiments the compound of the present invention is selected from the following compounds or a bi- or tri-dentate version thereof:

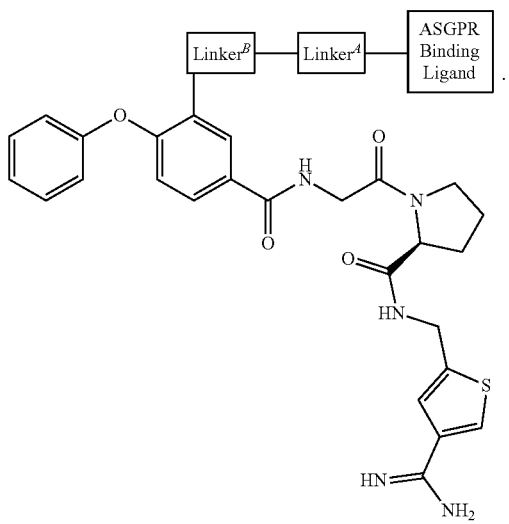

MASP

In certain embodiments the extracellular targeting ligand is a MASP Targeting Ligand.

In certain embodiments the MASP Targeting Ligand is selected from a ligand described in: Héja, D. et al. Monospecific Inhibitors Show That Both Mannan-Binding Lectin-Associated Serine Protease-1 (MASP-1) and -2 Are Essential for Lectin Pathway Activation and Reveal Structural Plasticity of MASP-2. Journal of Biological Chemistry 2012, 287 (24), 20290-20300; Dobó, J.; Kocsis, A.; Gil, P. Be on Target: Strategies of Targeting Alternative and Lectin Pathway Components in Complement-Mediated Diseases. Front. Immunol. 2018, 9, 1851; or WO 2014/144542.

In certain embodiments the MSAP-1 Targeting Ligand is SGMI-1 peptide, linked through the N- or C-terminus.

In certain embodiments the MSAP-1 Targeting Ligand is SGMI-2 peptide, linked through the N- or C-terminus.

In certain embodiments the MSAP-1 Targeting Ligand is TFMI-3 peptide, linked through the N- or C-terminus.

Factor XIa

In certain embodiments the extracellular targeting ligand is a factor XIa Targeting Ligand.

In certain embodiments the factor XIa Targeting Ligand is selected from a ligand described in: Lorthiois, E. et al. Structure-Based Design and Preclinical Characterization of Selective and Orally Bioavailable Factor XIa Inhibitors: Demonstrating the Power of an Integrated S1 Protease Family Approach. J. Med. Chem. 2020, 63 (15), 8088-8113.

In certain embodiments the factor XIa Targeting Ligand is selected from a ligand described in: Quan, M. L. et al. Factor XIa Inhibitors as New Anticoagulants. J. Med. Chem. 2018, 61 (17), 7425-7447.

In certain embodiments the factor XIa Targeting Ligand is selected from a ligand described in: Yang, W. et al. Discovery of a High Affinity, Orally Bioavailable Macrocyclic FXIa Inhibitor with Antithrombotic Activity in Preclinical Species. J. Med. Chem. 2020, 63 (13), 7226-7242.

In certain embodiments the factor XIa Targeting Ligand-Linker is:

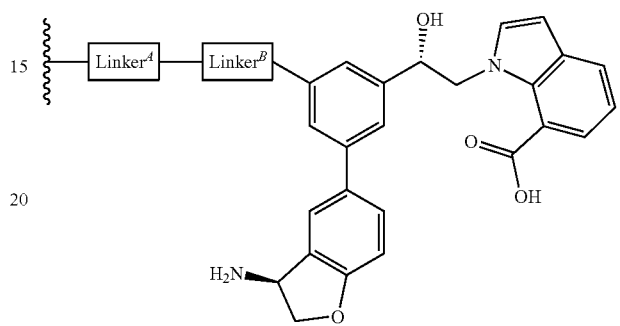

In certain embodiments the compound of the present invention is selected from the following compounds or a bi- or tri-dentate version thereof:

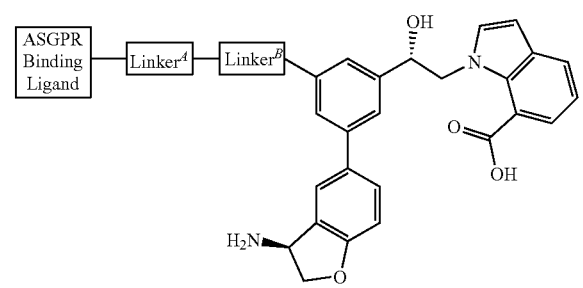

In certain embodiments the factor Xia Targeting Ligand is selected where an anchor bond is placed at any suitable location with or without functionalization.

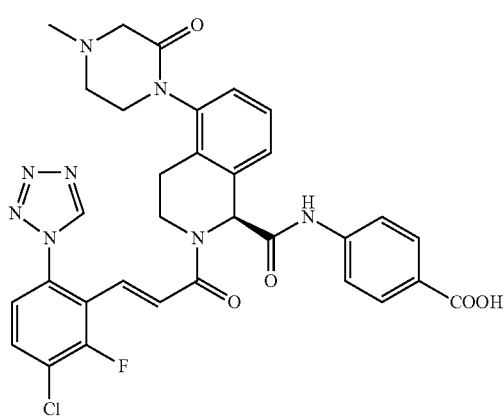

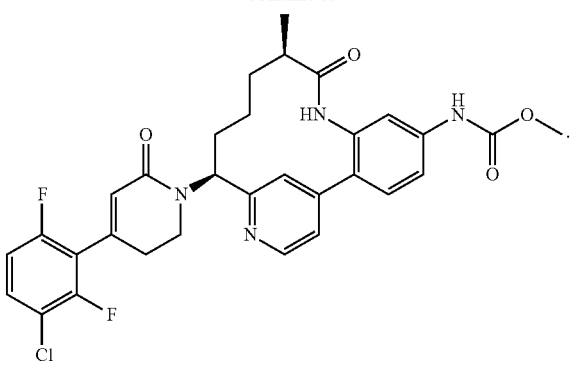

In certain embodiments the Factor XIa Targeting Ligand is selected from:

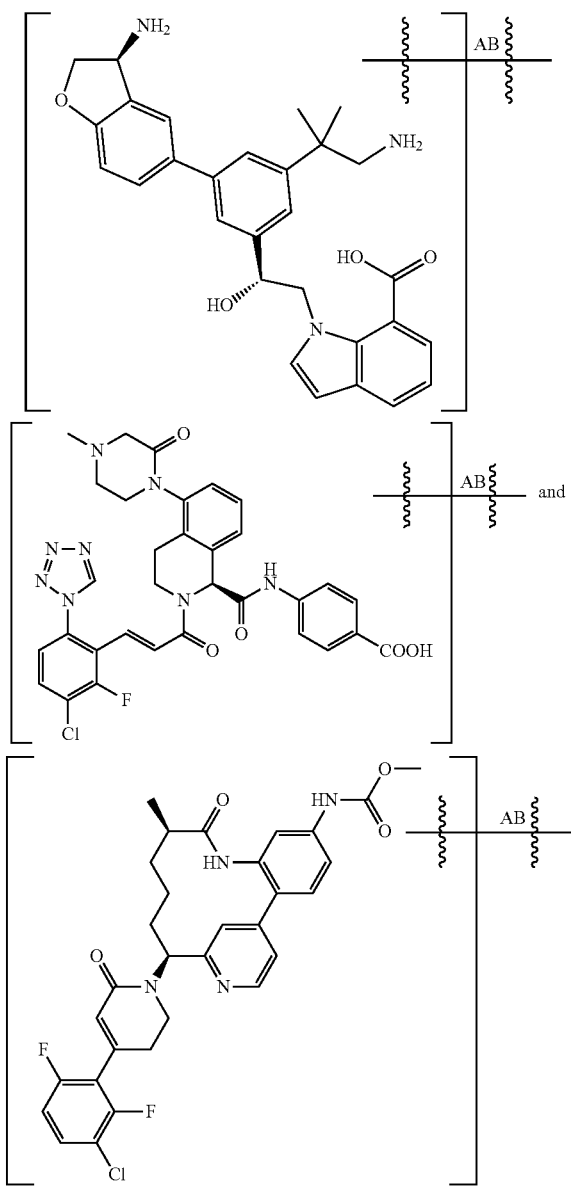

Immunoglobulin Degradation

Immunoglobulins, for example IgG, can cause, modulate, or amplify diseases in vivo, such as abnormal cellular proliferation such as tumors and cancer, autoimmune disorders, inflammation, and aging-related diseases. For example, immunoglobulins bind to cell surface receptors, often initiating aberrant signaling in multiple diseases such as cancer and inflammation.

The immunoglobulin degraders described herein or their pharmaceutically acceptable salt and/or pharmaceutically acceptable compositions thereof can be used to treat a disorder which is mediated by an immunoglobulin that binds to the Immunoglobulin Targeting Ligand. The described degraders are capable of targeting immunoglobulins that mediate pathological disorders for lysosomal degradation. The selected immunoglobulin may modulate a disorder in a human via a mechanism of action such as modification of a biological pathway, pathogenic signaling, or modulation of a signal cascade or cellular entry. The immunoglobulin is recruited with an Immunoglobulin Targeting Ligand, which is a ligand for the immunoglobulin.

Accordingly, in some embodiments, a method to treat a host with a disorder mediated by an immunoglobulin is provided that includes administering an effective amount of a degrader targeting the immunoglobulin or its pharmaceutically acceptable salt described herein to the host, typically a human, optionally in a pharmaceutically acceptable composition.

The immunoglobulin can be either the normal form of the protein or an aberrant form. For example, the immunoglobulin can be a mutant protein, or a protein, for example, where a partial, or full, gain-of-function or loss-of-function is encoded by nucleotide polymorphisms.

Targeting specific immunoglobulins is accomplished by the present invention through the use of specific Immunoglobulin Targeting Ligands. The target immunoglobulins of the current invention may include, but are not limited to, immunoglobulin G (IgG), immunoglobulin A (IgA), and immunoglobulin E (IgE). These immunoglobulins mediate a range of diseases that can be treated with an effective amount of the disclosed ASGPR-binding Immunoglobulin Degraders described herein.

Immunoglobulin A (IgA)

Aberrant expression of immunoglobulin A (IgA) mediates a range of autoimmune and immune-mediated disorders, including IgA nephropathy (also known as Berger's disease), celiac disease, Crohn's disease, Henoch-Schonlein purpura (HSP) (also known as IgA vasculitis), IgA pemphigus, dermatitis herpetiformis, inflammatory bowel disease (IBD), Sjögren's syndrome, ankylosing spondylitis, alcoholic liver cirrhosis, acquired immunodeficiency syndrome, IgA multiple myeloma, α-chain disease, IgA monoclonal gammopathy, monoclonal gammopathy of undetermined significance (MGUS), linear IgA bullous dermatosis, rheumatoid arthritis, ulcerative colitis, and primary glomerulonephritis, among others.

Specific degradation of IgA can be accomplished through the use of an IgA-specific Immunoglobulin Targeting Ligand. In certain embodiments, the Immunoglobulin Targeting Ligand used is an Opt peptide. Variations and derivatives of the IgA-specific Opt peptide suitable for use as IgA-specific Immunoglobulin Targeting Ligands are described in Hatanaka et al. *Journal of Biological Chemistry*, 287(51) 43126-43136. In certain embodiments, the IgA-specific Immunoglobulin Targeting Ligand is Opt-1. In certain embodiments, the IgA-specific Immunoglobulin Targeting Ligand is Opt-2. In certain embodiments, the IgA-specific Immunoglobulin Targeting Ligand is Opt-3.

In certain embodiments the immunoglobulin degrading compound is:
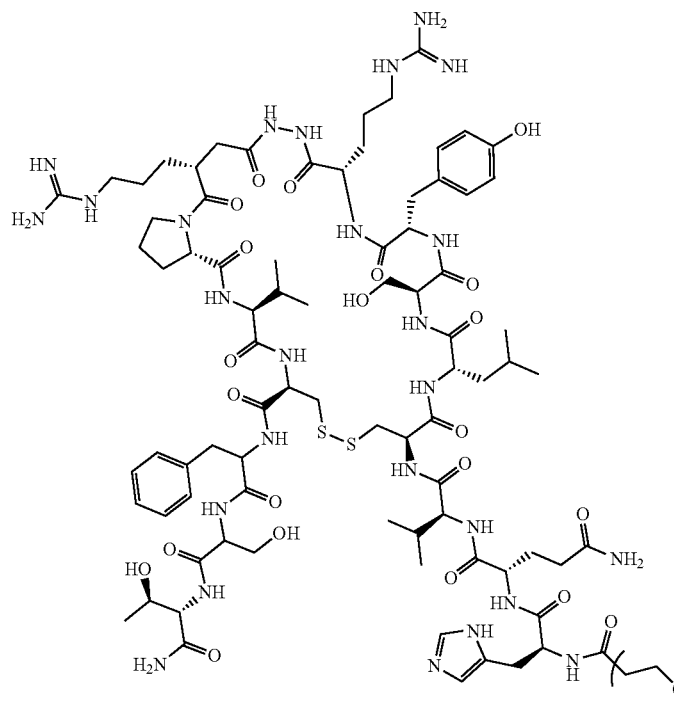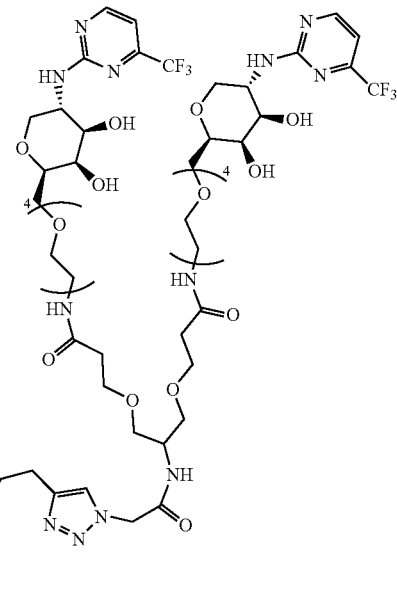
or a pharmaceutically acceptable salt thereof.
In certain embodiments the immunoglobulin degrading compound is:
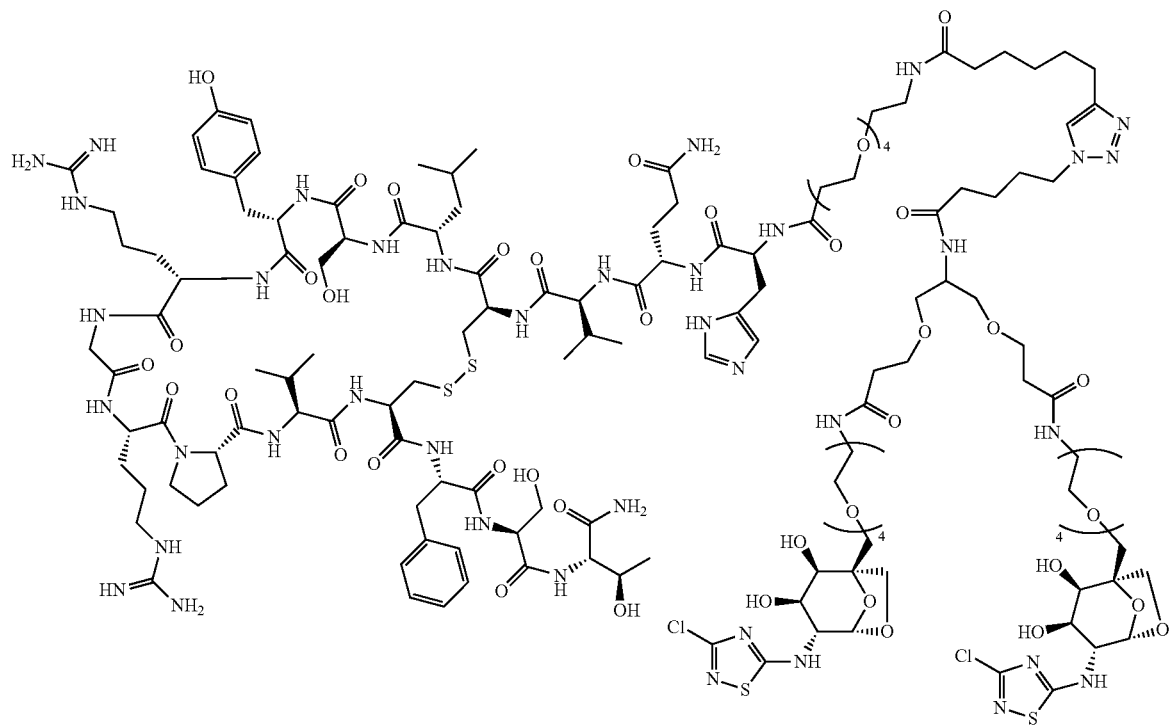
or a pharmaceutically acceptable salt thereof.

In certain embodiments the immunoglobulin degrading compound is:

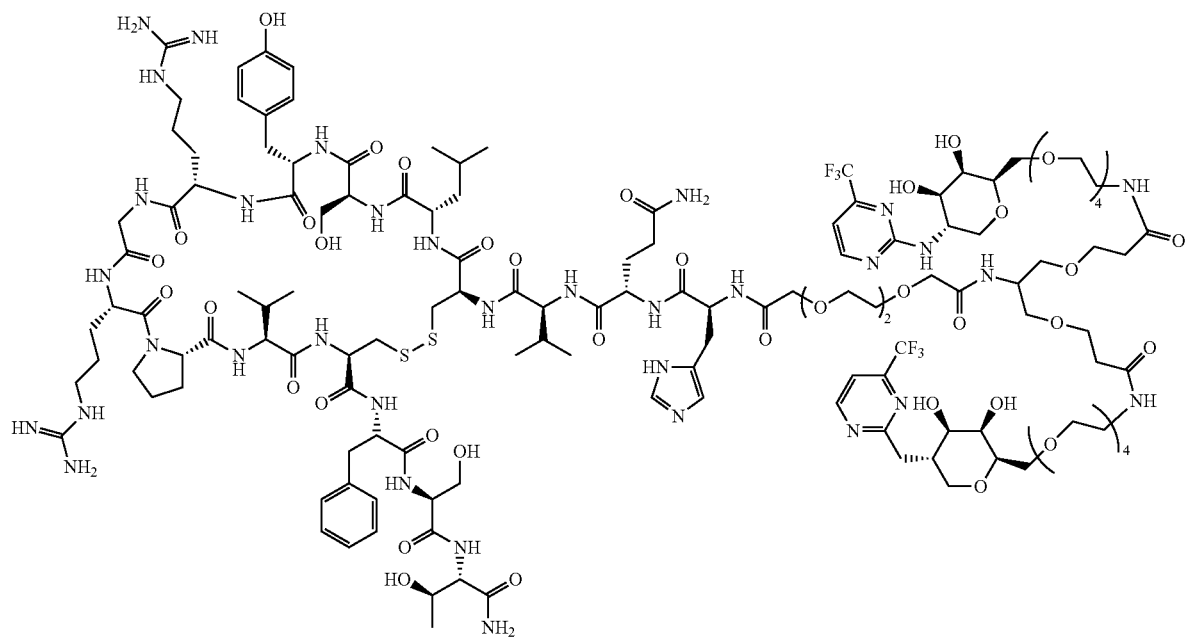

or a pharmaceutically acceptable salt thereof.

In certain embodiments the immunoglobulin degrading compound is:

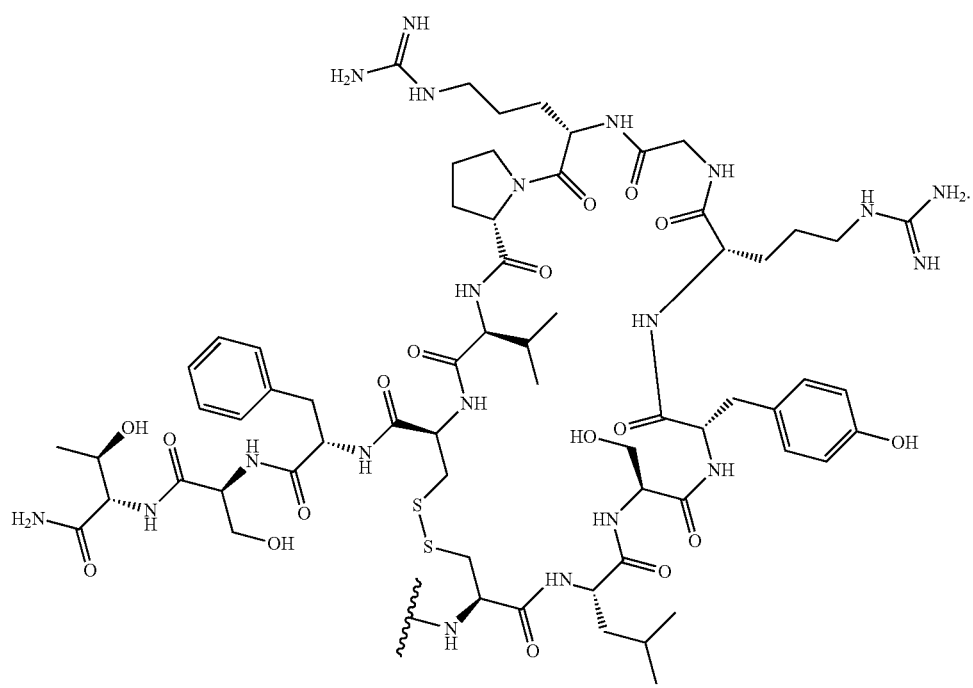 [SMILES: *N[C@H]1CSSC[C@@H](C(=O)N[C@@H](Cc2ccccc2)C(=O)N[C@@H](CO)C(=O)N[C@H](C(N)=O)[C@@H](C)O)NC(=O)[C@H](C(C)C)NC(=O)[C@@H]2CCCN2C(=O)[C@H](CCCNC(=N)N)NC(=O)CNC(=O)[C@H](CCCNC(=N)N)NC(=O)[C@H](Cc2ccc(O)cc2)NC(=O)[C@H](CO)NC(=O)[C@H](CC(C)C)NC1=O]

The Protein Data Bank website provides the crystal structure of IgA, as well as the crystal structure of IgA bound to various compounds searchable by 5E8E (Baglin, T. P., et al., J. Thromb. Haemost., 2016, 14: 137-142), and 2QTJ (Bonner, A., et al., J. Immunol., 2008, 180: 1008-1018). Additionally, Hatanaka T. et al., provides great insight into the specificity and high binding affinity of IgA to OPT-1 peptides (J Biol Chem., 2012, 287(51), 43126-43136).

Representative IgA Targeting Ligands are provided in FIG. 1.

Additional representative IgA Targeting Ligands include:

```
                                                    SEQ ID NO: 1
MLKKIE (Jerlstrom et al. Infect. Immun. 1996 July; 64(7):2787-2793;

SEQ ID NO: 2
Opt-1-HMVCLAYRGRPVCFAL (Hatanaka et al. J. Biol. Chem. Vol. 287, No.
51, pp. 43126-43136, Dec. 14, 2012)

SEQ ID NO: 3
Opt-2-HMVCLSYRGRPVCFSL (Hatanaka et al. J. Biol. Chem. Vol. 287, No.
51, pp. 43126-43136, Dec. 14, 2012)

SEQ ID NO: 4
Opt-3-HQVCLSYRGRPVCFST (Hatanaka et al. J. Biol. Chem. Vol. 287, No.
51, pp. 43126-43136, Dec. 14, 2012)

SEQ ID NO: 5
QMRCLSYKGRRVCLWL (U.S. Pat. No. 9593147)

SEQ ID NO: 6
KRLCLQYKGSKVCFRL (U.S. Pat. No. 9593147)

SEQ ID NO: 7
RMRCLTYRGRRVCLEL (U.S. Pat. No. 9593147)

SEQ ID NO: 8
SMRCLQYRGSRVCLTL (U.S. Pat. No. 9593147)

SEQ ID NO: 9
HLRCLRYKGTRVCFSL (U.S. Pat. No. 9593147)

SEQ ID NO: 10
HVRCLSYKGREVCVQL (U.S. Pat. No. 9593147)

SEQ ID NO: 11
PRMCLFIYKGRRVCIPY (U.S. Pat. No. 9593147)

SEQ ID NO: 12
HMRCLHYKGRRVCFLL (U.S. Pat. No. 9593147)

SEQ ID NO: 13
HKRCLHYRGRMVCFLI (U.S. Pat. No. 9593147)

SEQ ID NO: 14
QKRCLKYKGSRVCFFL (U.S. Pat. No. 9593147)

SEQ ID NO: 15
HVRCLRYRGKNVCFLL (U.S. Pat. No. 9593147)

SEQ ID NO: 16
SDVCLRYRGRPVCFQV (U.S. Pat. No. 9593147)

SEQ ID NO: 17
RDVCLRYRGRPVCFQV (U.S. Pat. No. 9593147)

SEQ ID NO: 18
HDVCLRYRGRPVCFQV (U.S. Pat. No. 9593147)

SEQ ID NO: 19
SMVCLRYRGRPVCFQV (U.S. Pat. No. 9593147)

SEQ ID NO: 20
SAVCLRYRGRPVCFQV (U.S. Pat. No. 9593147)

SEQ ID NO: 21
SDVCLNYRGRPVCFQV (U.S. Pat. No. 9593147)

SEQ ID NO: 22
SDVCLHYRGRPVCFQV (U.S. Pat. No. 9593147)

SEQ ID NO: 23
SDVCLAYRGRPVCFQV (U.S. Pat. No. 9593147)

SEQ ID NO: 24
SDVCLRYRGRPVCFAV (U.S. Pat. No. 9593147)

SEQ ID NO: 25
SDVCLRYRGRPVCFQL (U.S. Pat. No. 9593147)
```

-continued

SDVCLRYRGRPVCFQA (U.S. Pat. No. 9593147)  SEQ ID NO: 26

HMVCLSYRGRPVCF (US Pub. No. 20150044701)  SEQ ID NO: 27

HMVCLSYRGRPVCFS (US Pub. No. 20150044701)  SEQ ID NO: 28

HQVCLSYRGQPVCFSL (US Pub. No. 20150044701)  SEQ ID NO: 29

HQVCLSYRGRPTCFSL (US Pub. No. 20150044701)  SEQ ID NO: 30

HQVCLSYRGRPVCYSL (US Pub. No. 20150044701)  SEQ ID NO: 31

HQVCLSYRGQPVCFST (US Pub. No. 20150044701)  SEQ ID NO: 32

HQVCLSYRGRPTCFST (US Pub. No. 20150044701)  SEQ ID NO: 33

HQVCLSYRGQPTCFST (US Pub. No. 20150044701)  SEQ ID NO: 34

In certain embodiments the IgA Targeting Ligand is

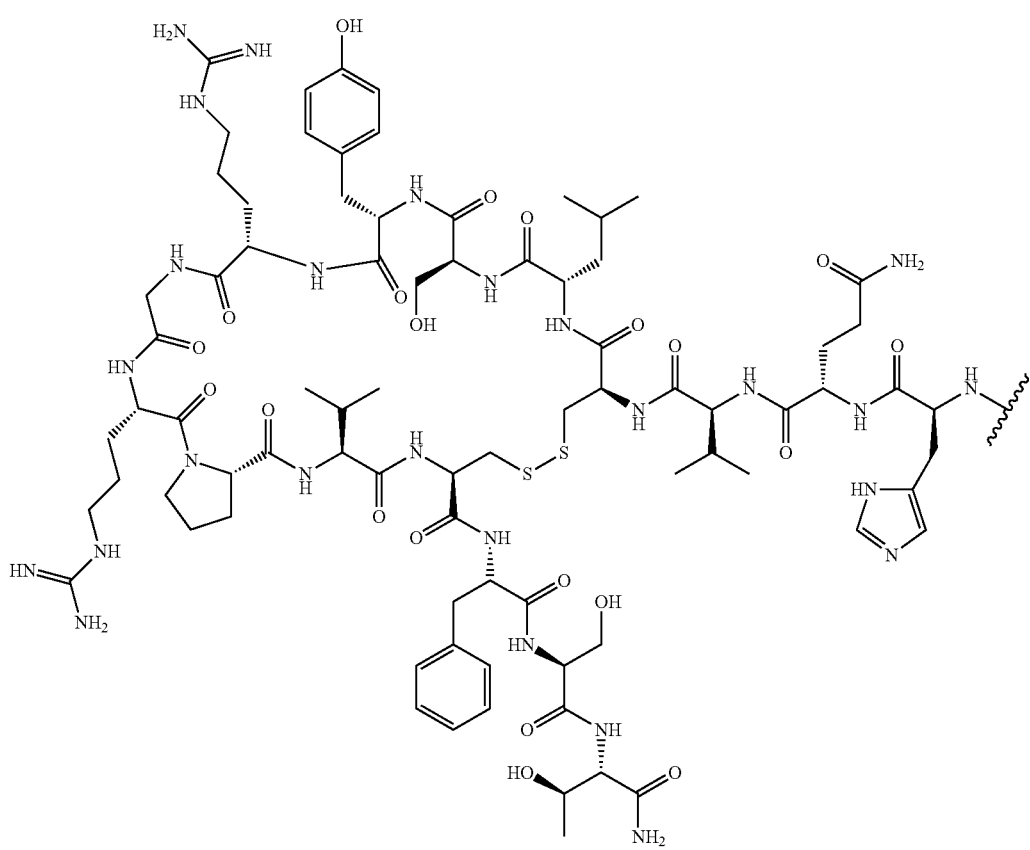

Non-limiting examples of IgA degrading compounds include
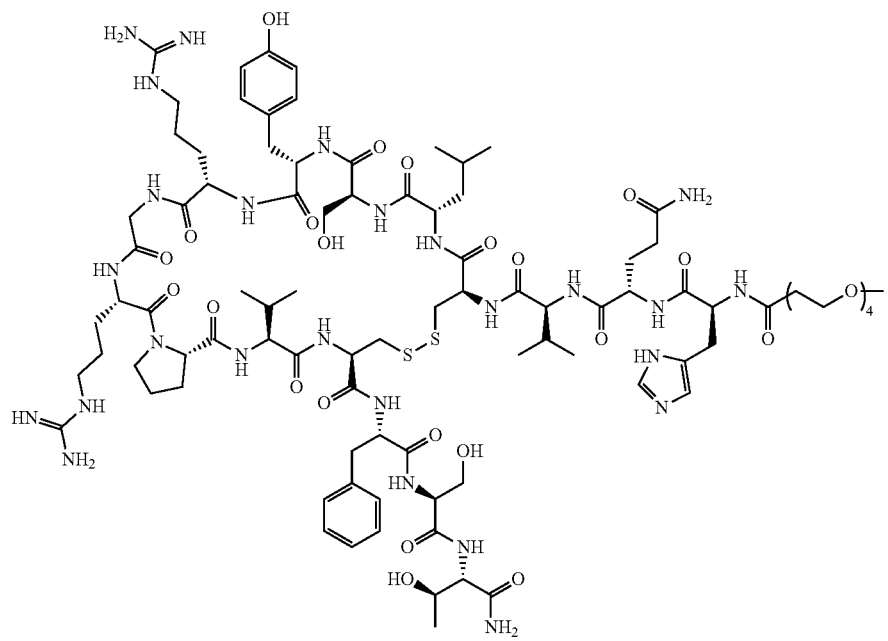
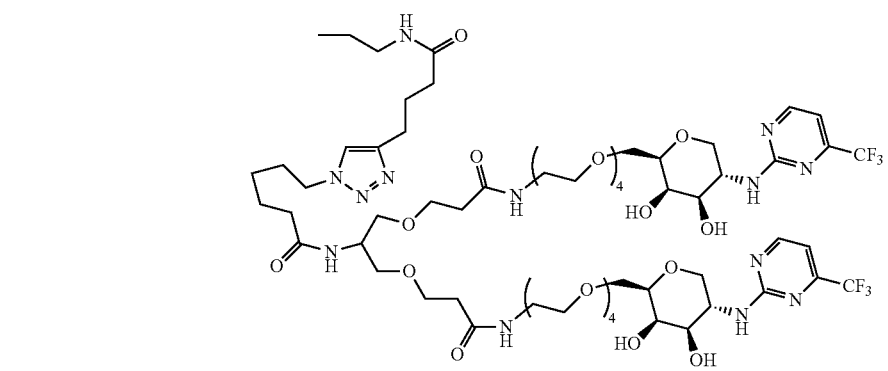
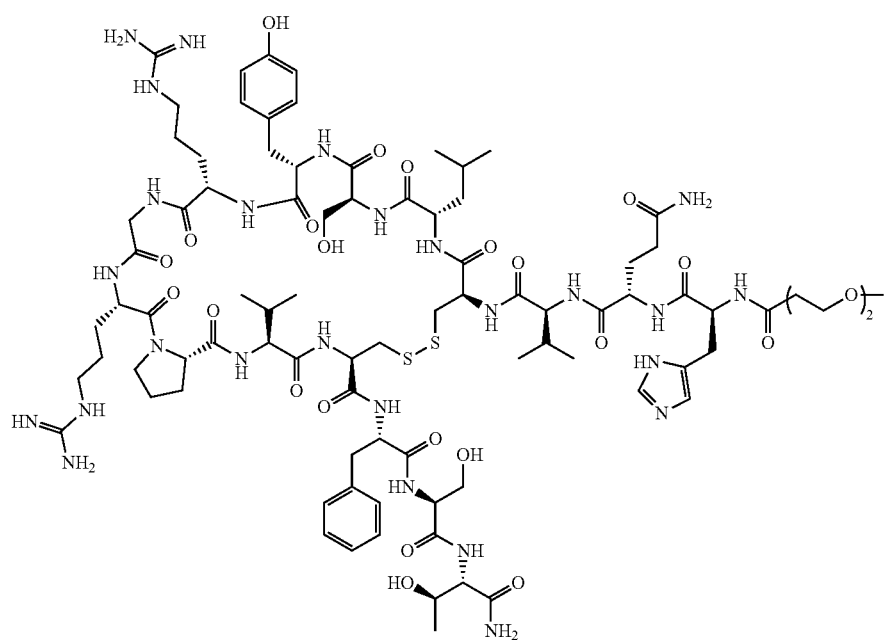

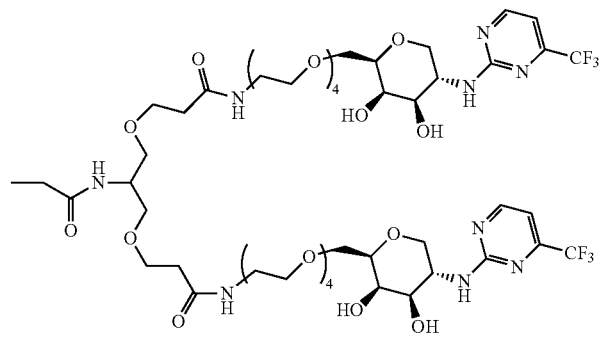
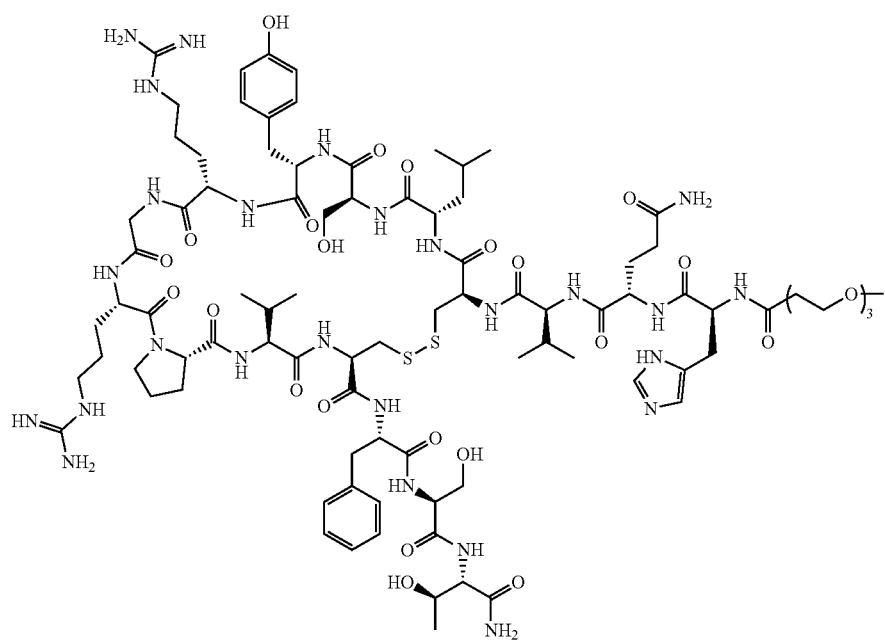
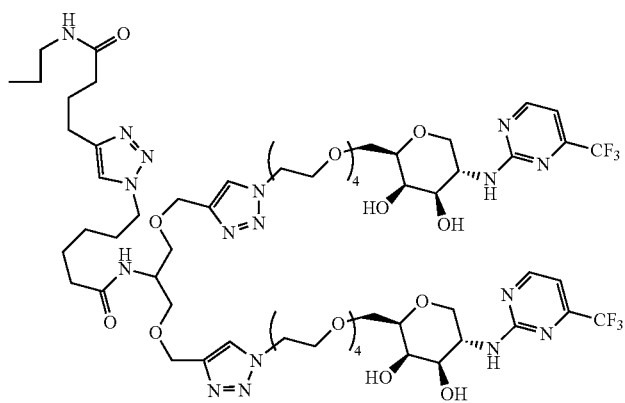

231
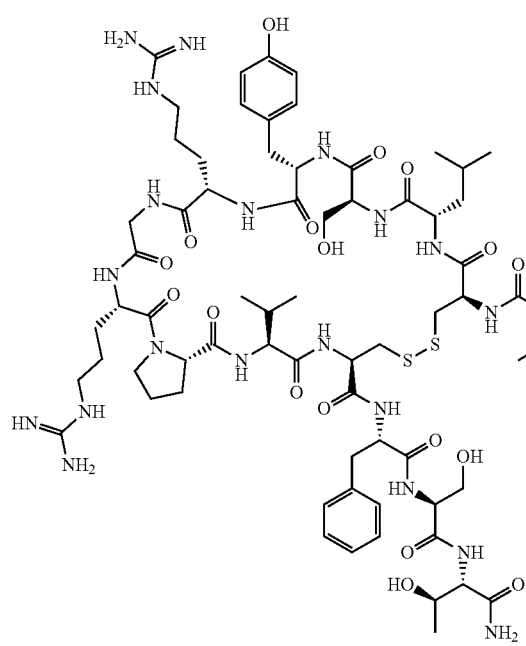
232
-continued
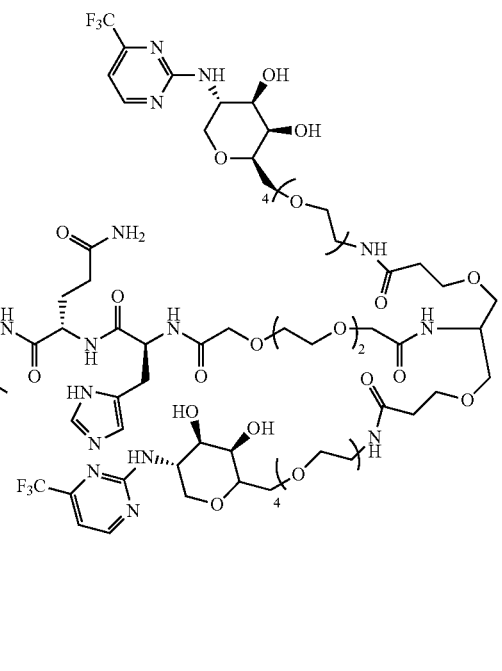
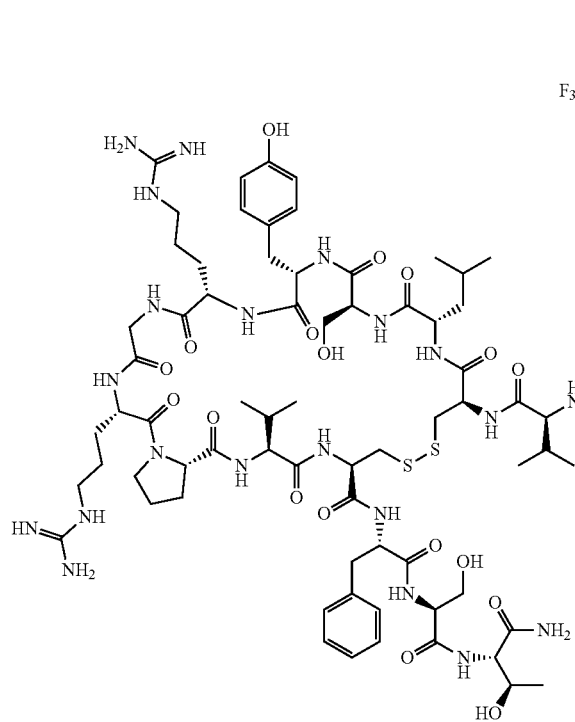
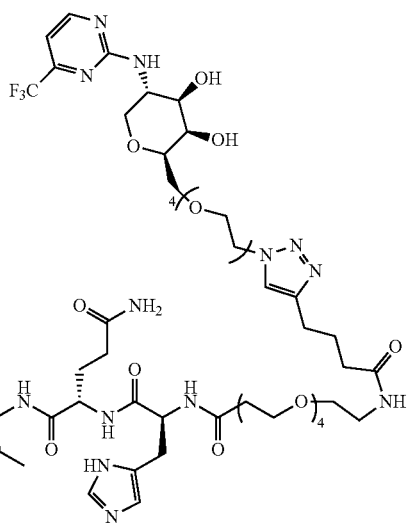

-continued
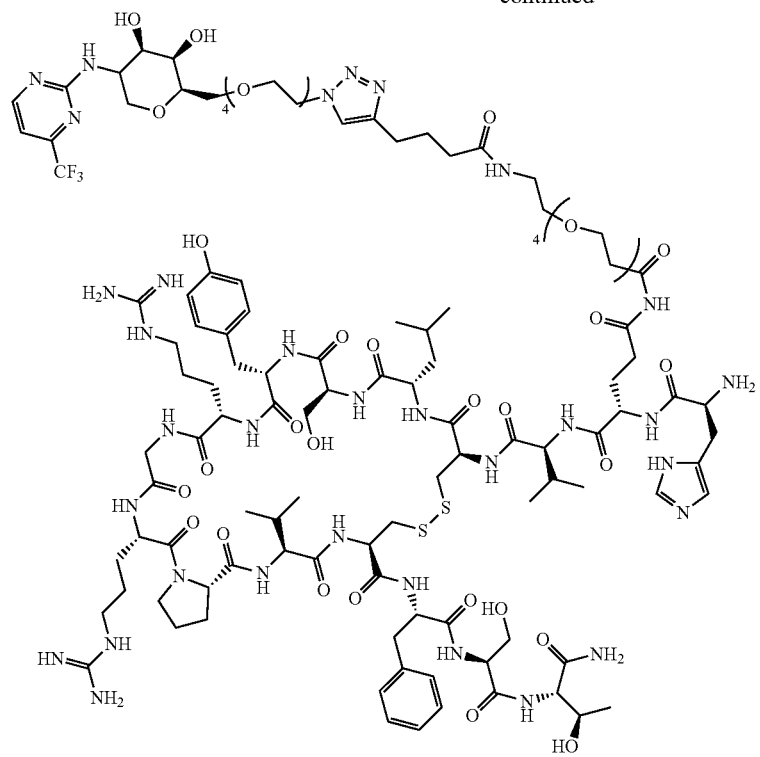
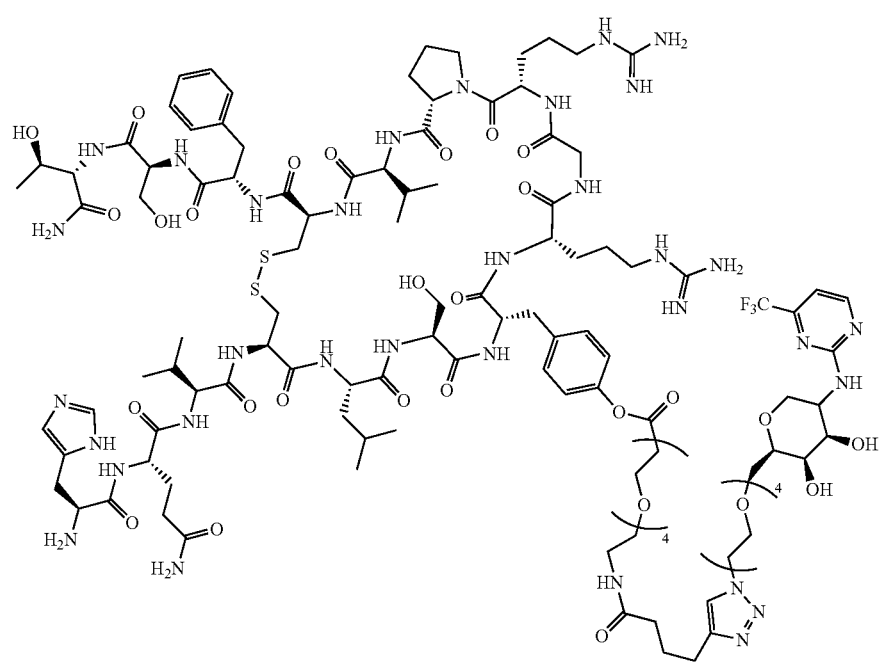

235
-continued
236
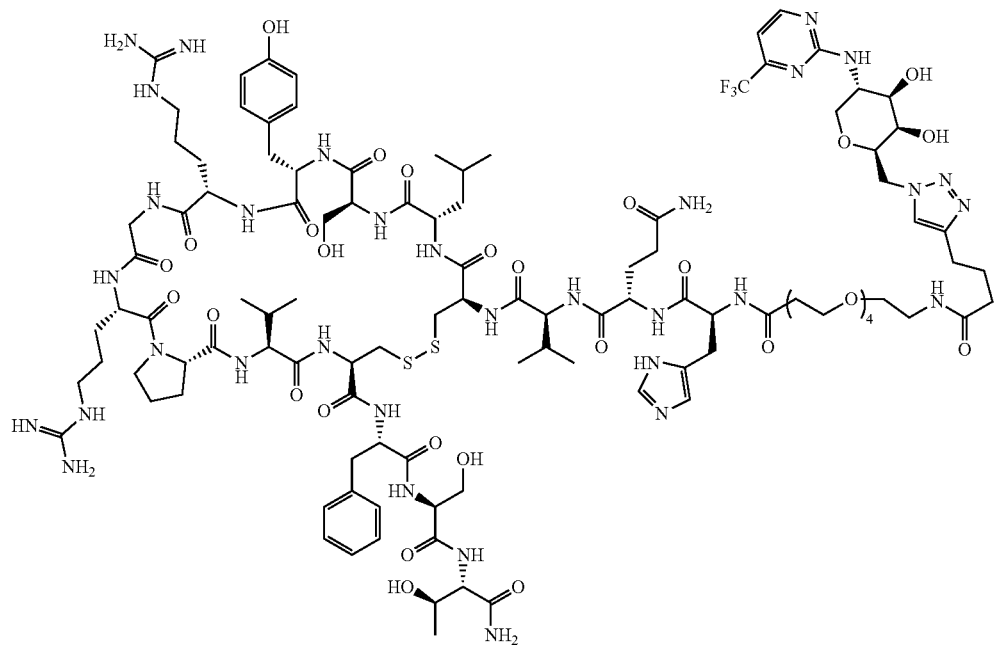
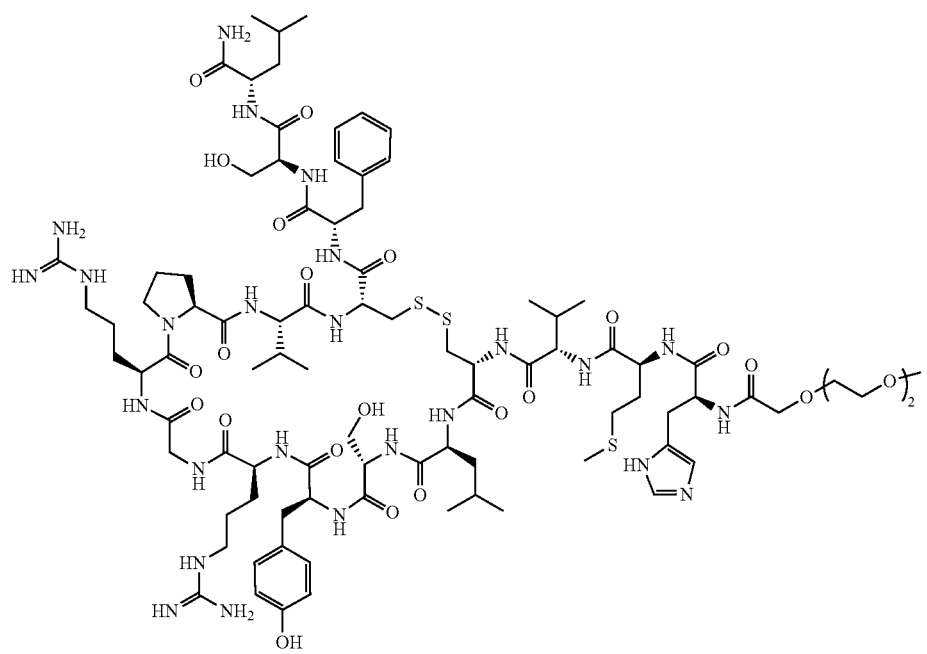

-continued

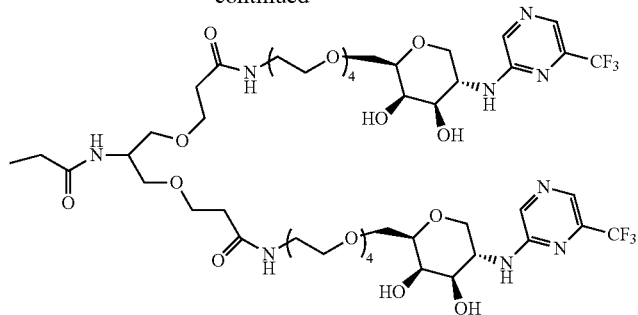

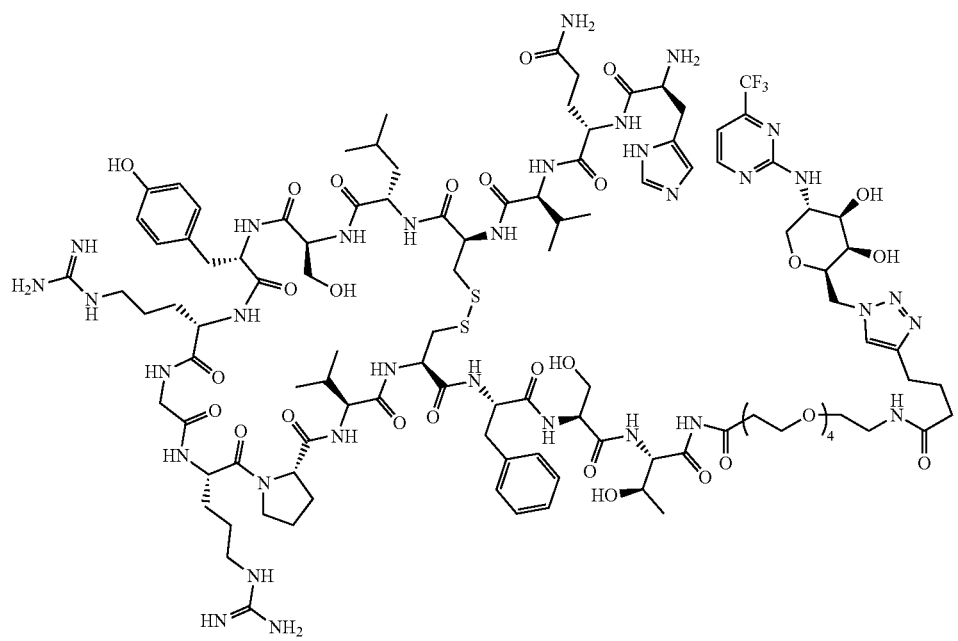

Immunoglobulin G (IgG)

Immunoglobulin G (IgG) mediates a range of autoimmune, infectious and metabolic diseases, including systemic fibroinflammatory disease. In addition, overexpression of IgG4 is associated with IgG4-related diseases, which generally include multiple organs, and disorders include type 1 autoimmune pancreatitis, interstitial nephritis, Riedel's thyroiditis, storiform fibrosis, Mikulicz's disease, Küttner's tumor, inflammatory pseudotumors (in various sites of the body), mediastinal fibrosis, retroperitoneal fibrosis (Ormond's disease), aortitis and periaortitis, proximal biliary strictures, idiopathic hypocomplementemic tubulointerstitial nephritis, multifocal fibrosclerosis, pachymeningitis, pancreatic enlargement, tumefactive lesions, pericarditis, rheumatoid arthritis (RA), inflammatory bowel disease, multiple sclerosis, myasthenia gravis, ankylosing spondylitis, primary Sjögren's syndrome, psoriatic arthritis, systemic lupus erythematosus (SLE), sclerosing cholangitis, IgG monoclonal gammopathy, monoclonal gammopathy of undetermined significance (MGUS), melanoma, bullous pemphigoid, Goodpasture disease, encephalitis, thrombotic thrombocytopenic purpura, immune thrombocytopenia, chronic inflammatory polyneuropathy, limbic encephalitis, neuromyotonia, Morvan syndrome, pemphigus foliaceus, pemphigus vulgaris, REM and non-REM parasomnia, and membranous nephropathy, multiple sclerosis, hyperthyroid Grave's disease, epidermolysis bullosa acquisita, pemphigoid gestationis, anti-p200 pemphigoid, and paraneoplastic pemphigus, among others.

Specific degradation of IgG can be accomplished through the use of an IgG-specific Immunoglobulin Targeting Ligand. In certain embodiments, the Immunoglobulin Targeting Ligand binds to the Fc region of IgG. In certain embodiments the IgG-specific Immunoglobulin Targeting Ligand is an Fc-binding peptide. In certain embodiments, the IgG-specific Immunoglobulin Targeting Ligand is Fc-BP2. In certain embodiments, the IgG-specific Immunoglobulin Targeting Ligand is Fc-III.

In certain alternative embodiments any compound drawn herein with stereochemistry drawn in the Targeting Ligand is also described herein without stereochemistry. For example, in certain embodiments:

239
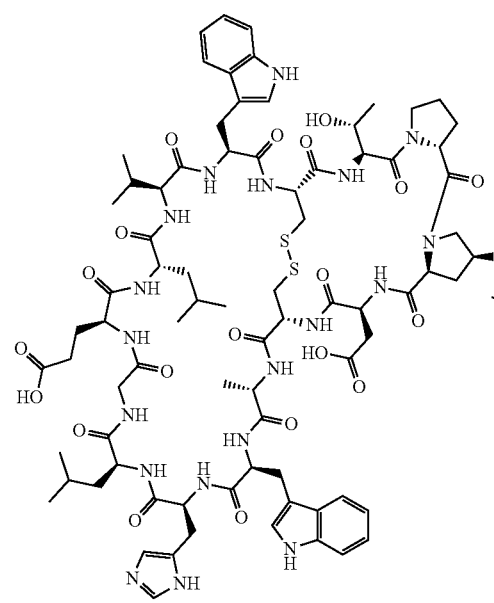
240
-continued
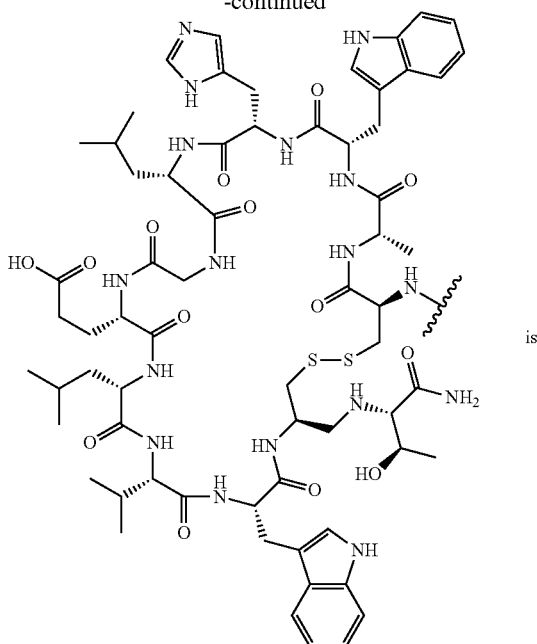
is
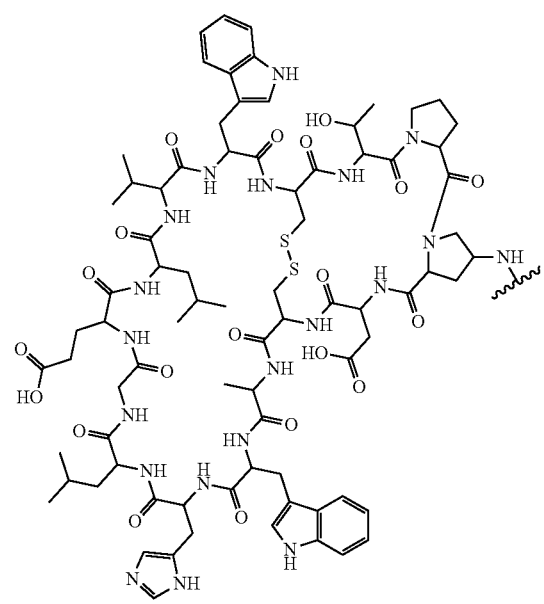 or
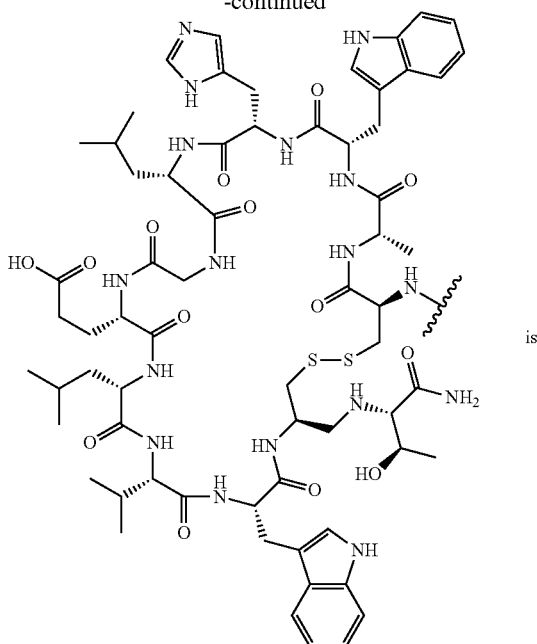
.
In certain embodiments the compound of the present invention is:
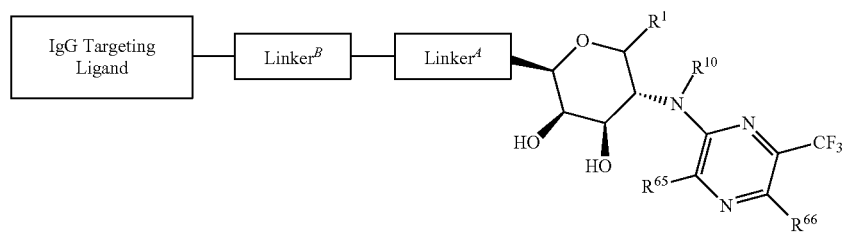

-continued
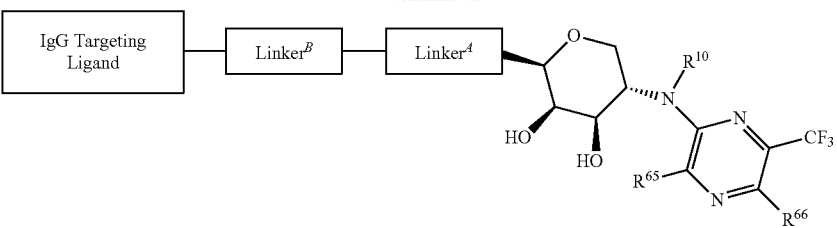
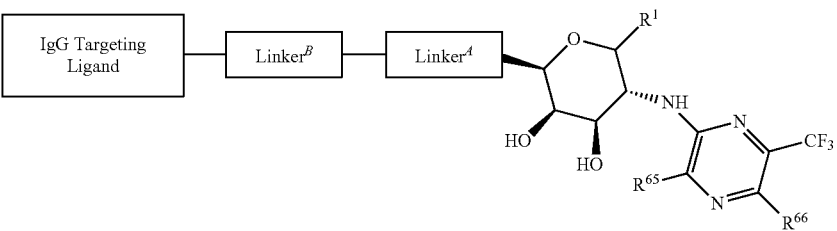
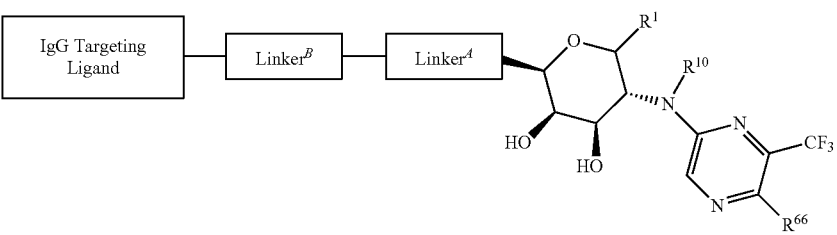
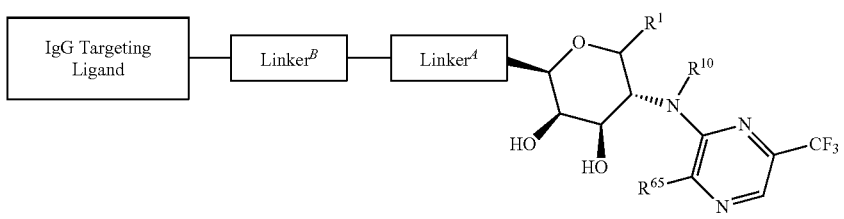
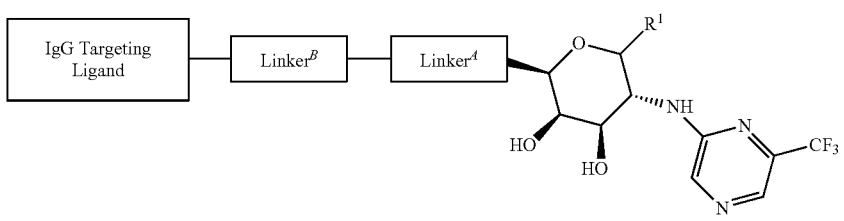
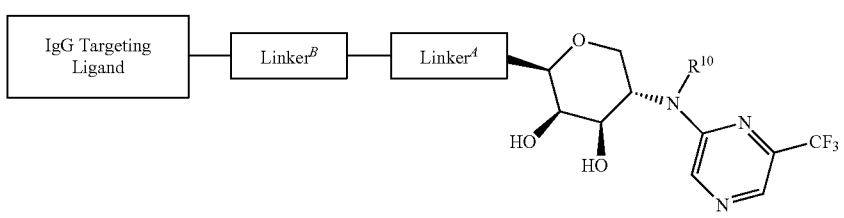
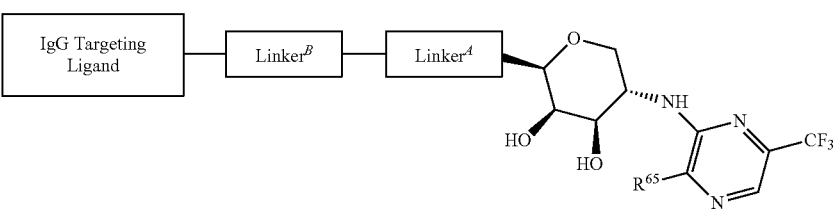

or a pharmaceutically acceptable salt thereof.

In certain embodiments the compound of the present invention is:

or a pharmaceutically acceptable salt thereof.

In certain embodiments the compound of the present invention is:

-continued
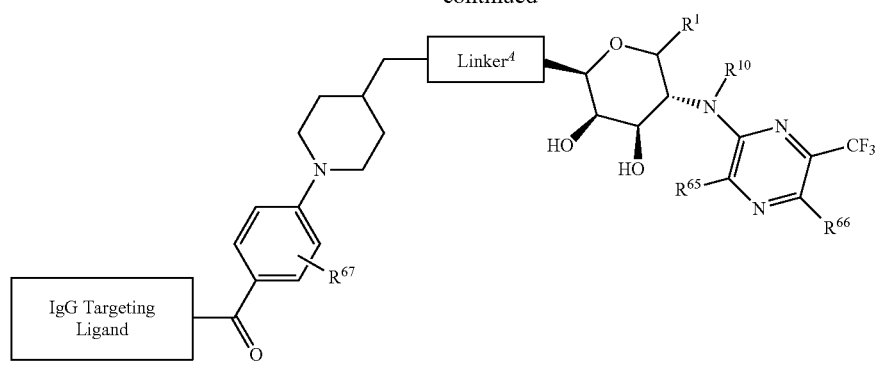
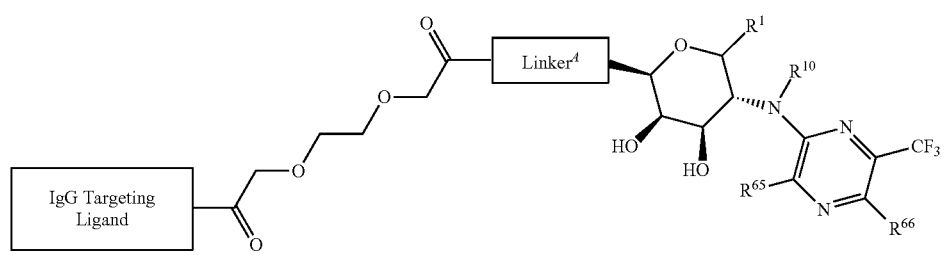
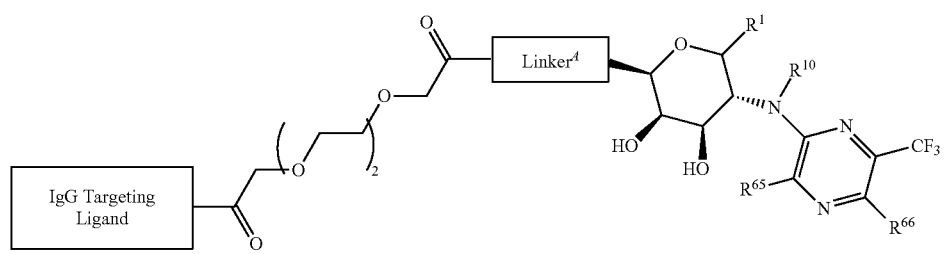
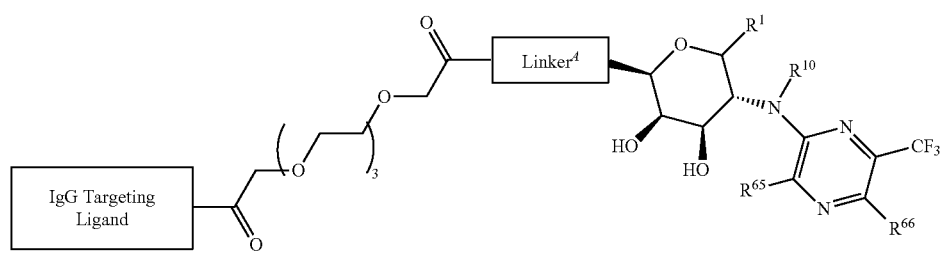
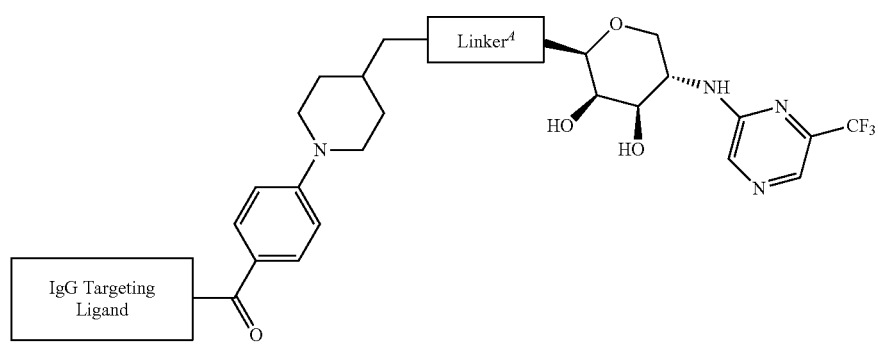

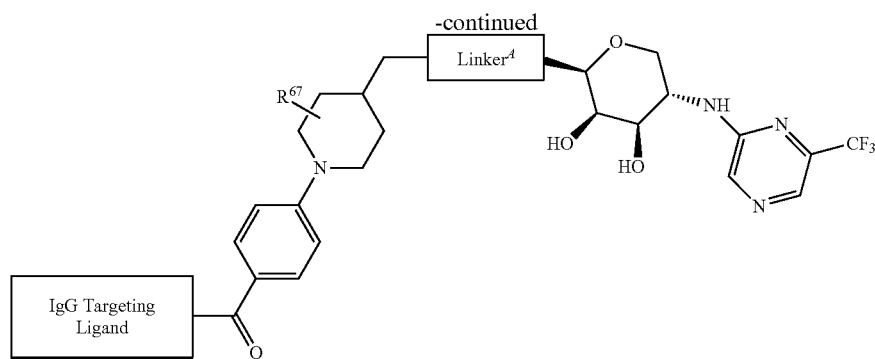
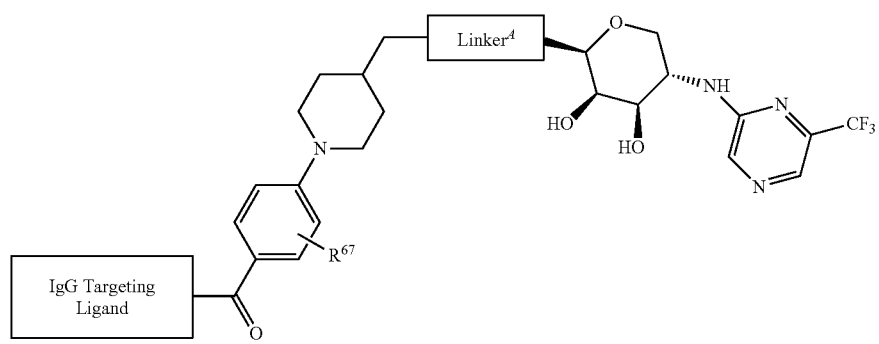
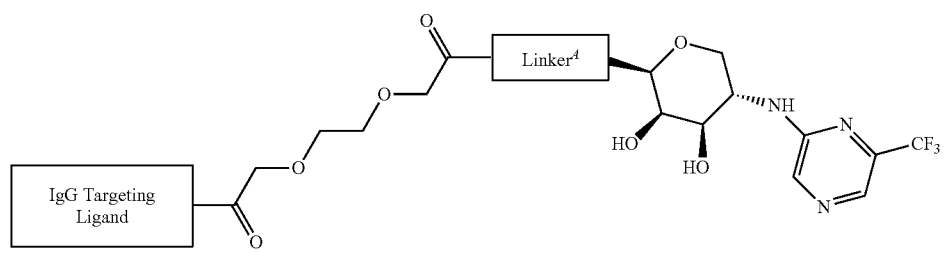
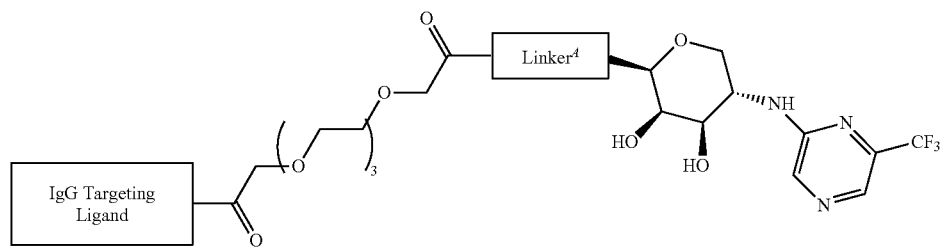
or a pharmaceutically acceptable salt thereof.

In certain embodiments the compound of the present invention is:
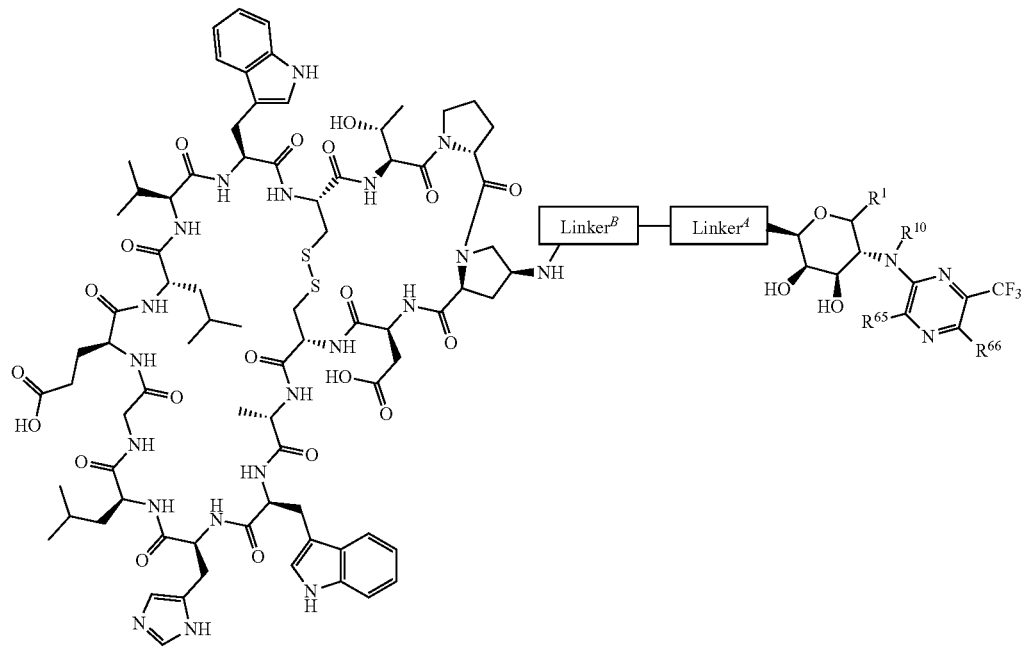
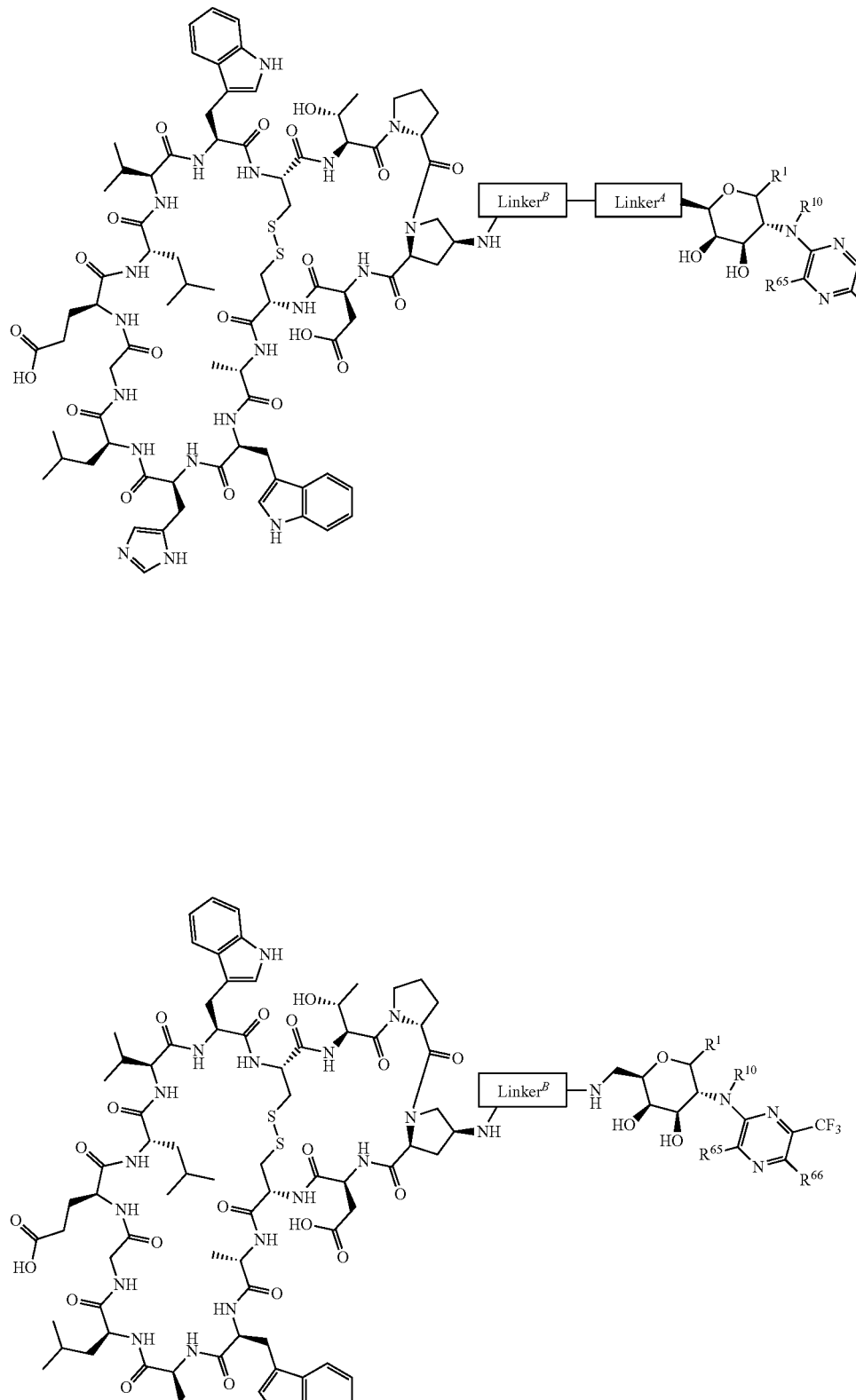

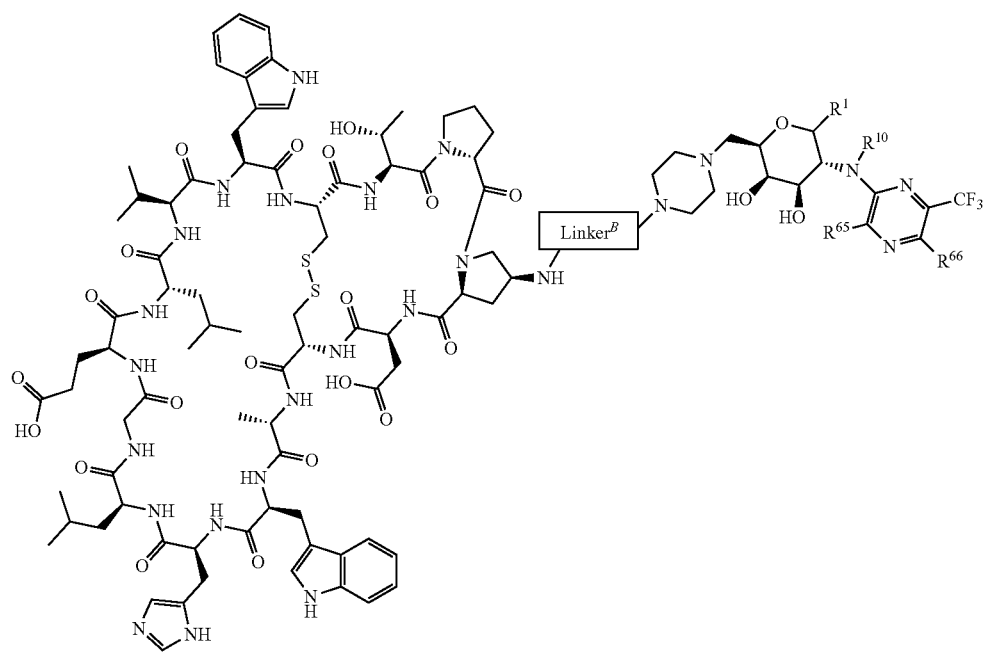
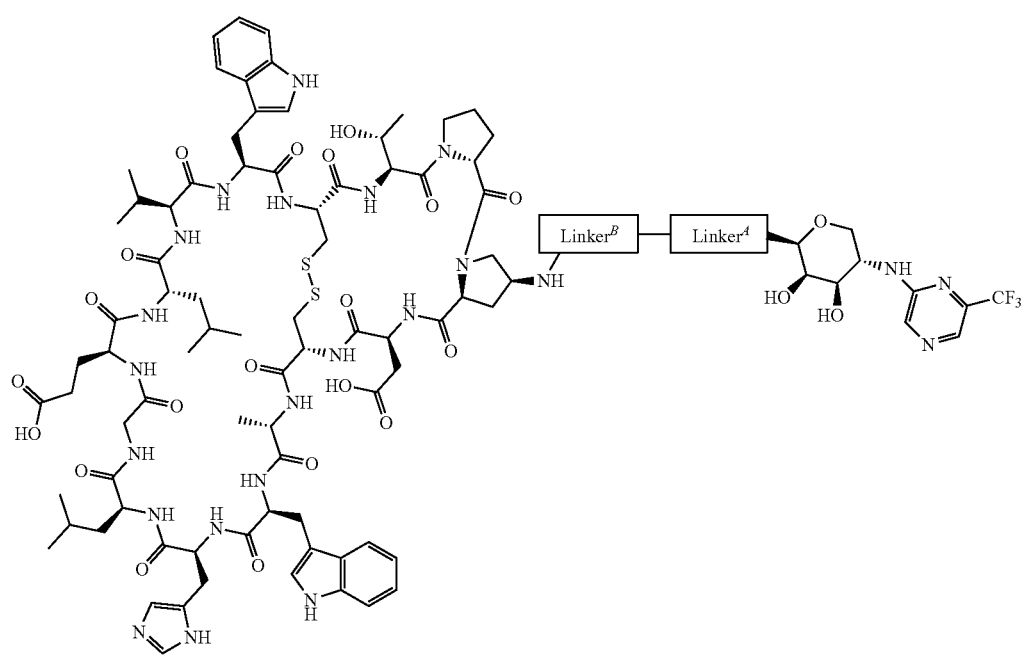

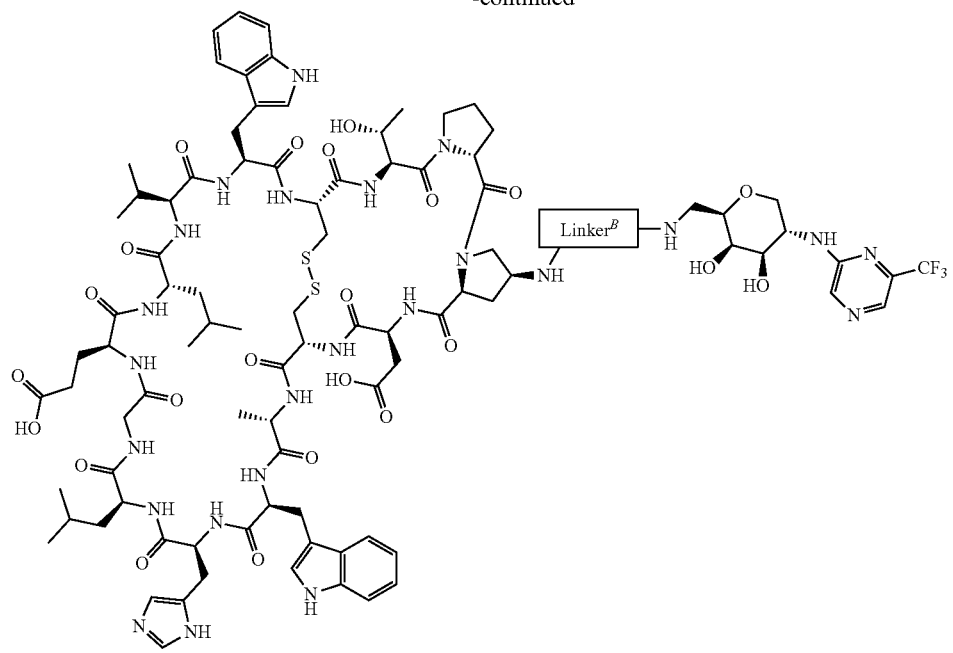
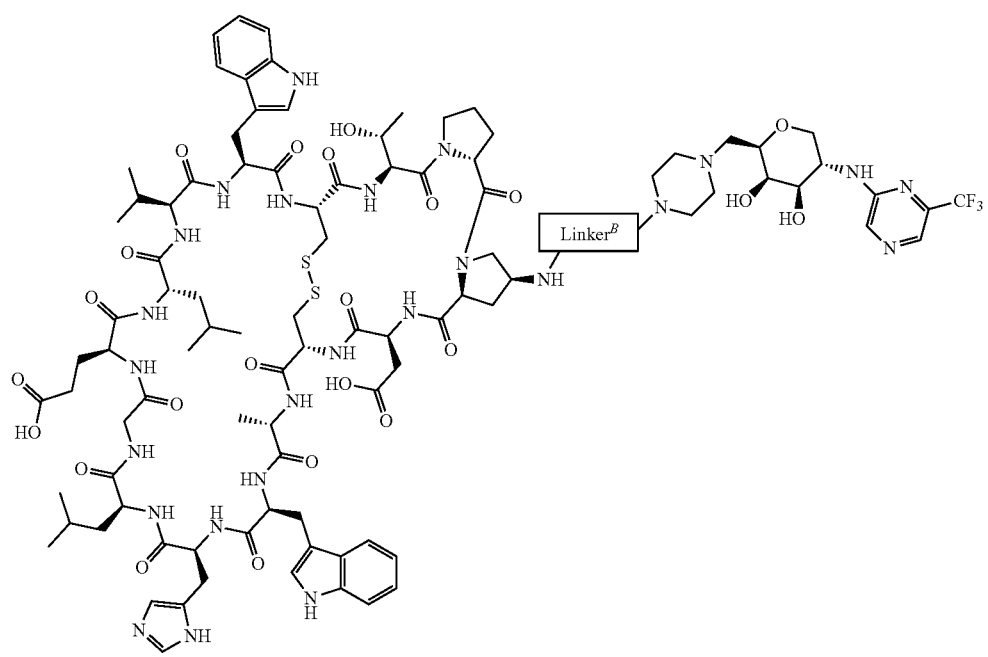
or a pharmaceutically acceptable salt thereof.
In certain embodiments the immunoglobulin degrading compound is:

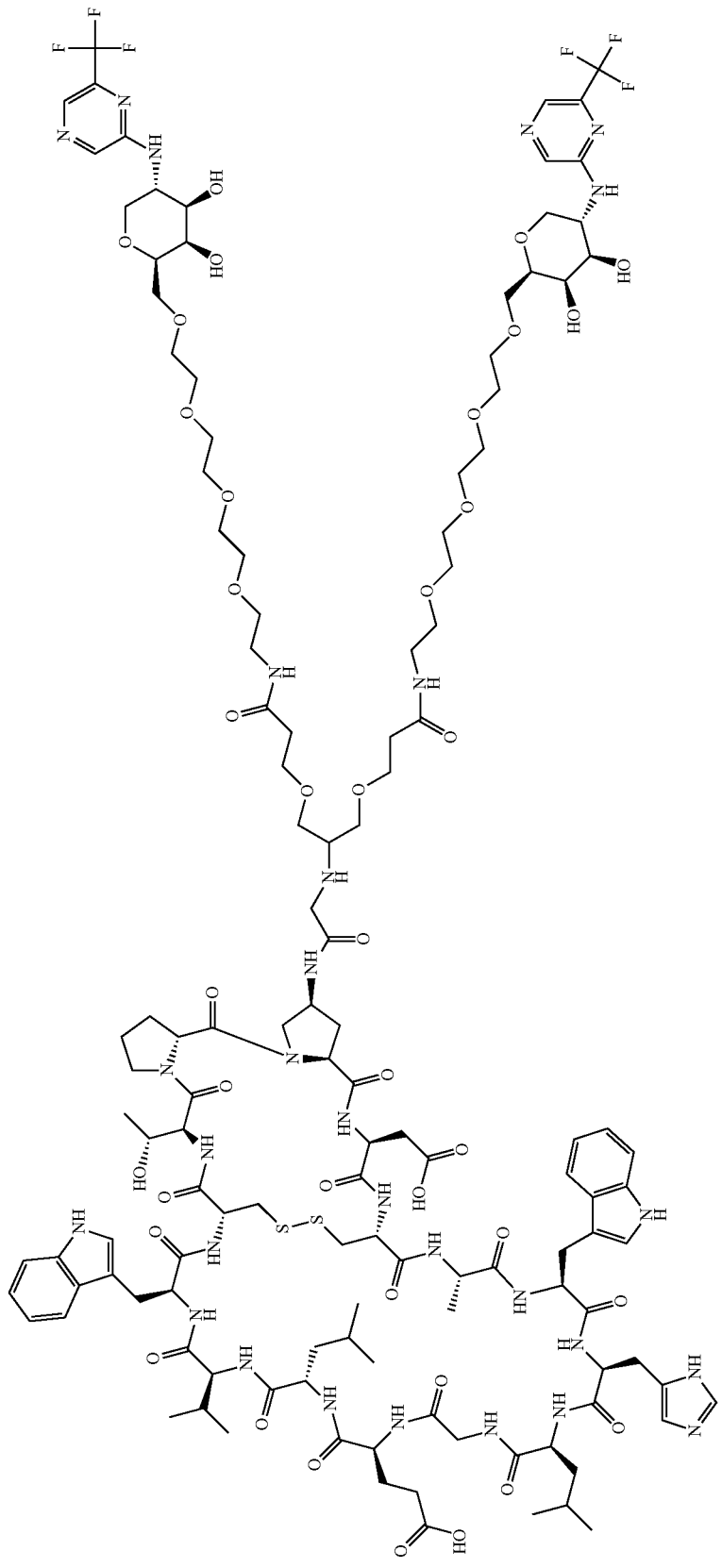

or a pharmaceutically acceptable salt thereof.
In certain embodiments the immunoglobulin degrading compound is:
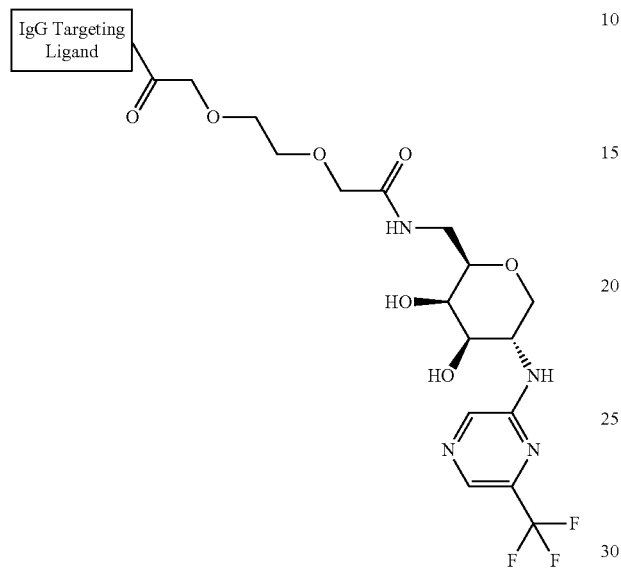
or a pharmaceutically acceptable salt thereof.
In certain embodiments the immunoglobulin degrading compound is:
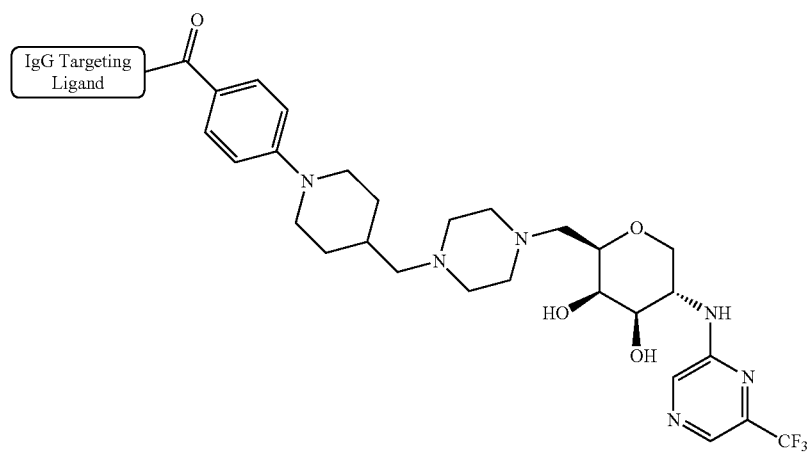 [SMILES: CC(=O)c1ccc(N2CCC(CN3CCN(C[C@H]4OC[C@H](Nc5cncc(C(F)(F)F)n5)[C@@H](O)[C@H]4O)CC3)CC2)cc1]
or a pharmaceutically acceptable salt thereof.
In certain embodiments the immunoglobulin degrading compound is:

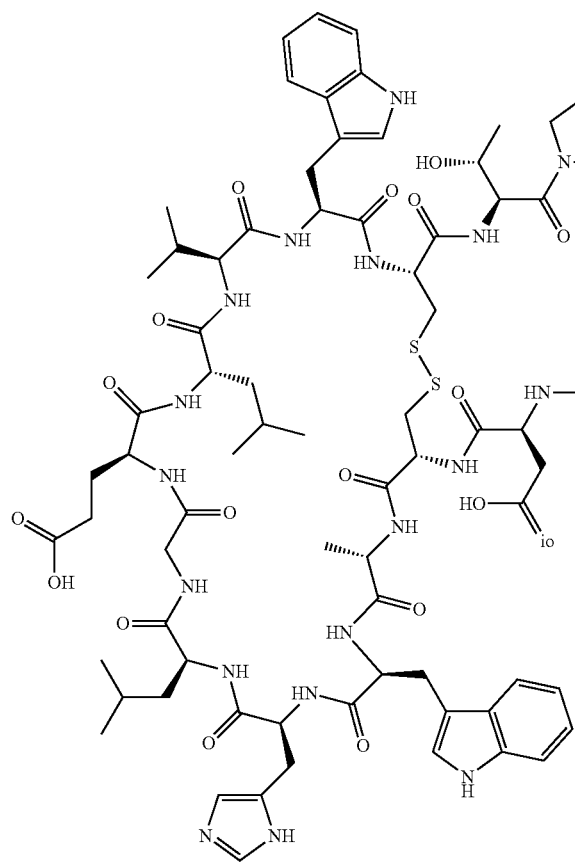
or a pharmaceutically acceptable salt thereof.
In certain embodiments the immunoglobulin degrading compound is:
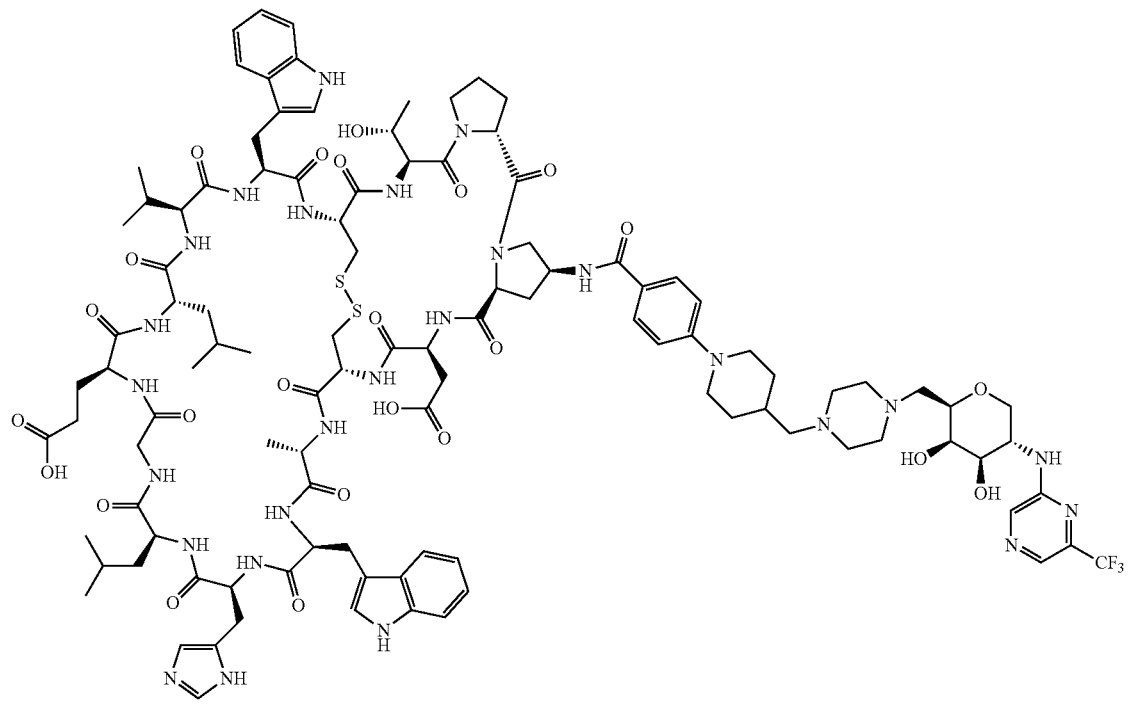 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)c3ccc(N4CCC(CN5CCN(C[C@H]6OC[C@H](Nc7cncc(C(F)(F)F)n7)[C@@H](O)[C@H]6O)CC5)CC4)cc3)C[C@H]1C(=O)N[C@@H](CC(=O)O)C(=O)N2]
or a pharmaceutically acceptable salt thereof.

In certain embodiments the immunoglobulin degrading compound is:

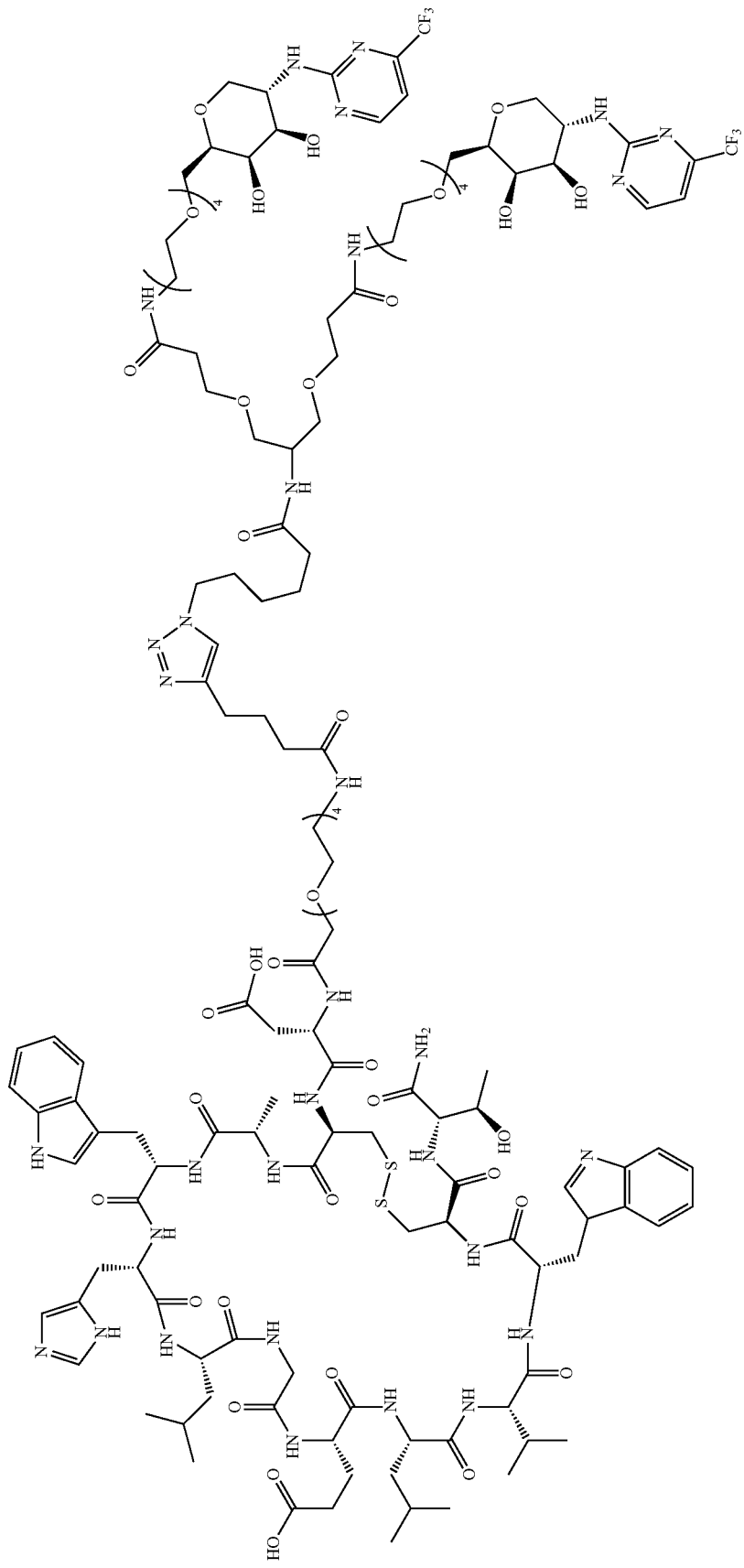

or a pharmaceutically acceptable salt thereof.

In certain embodiments the immunoglobulin degrading compound is:

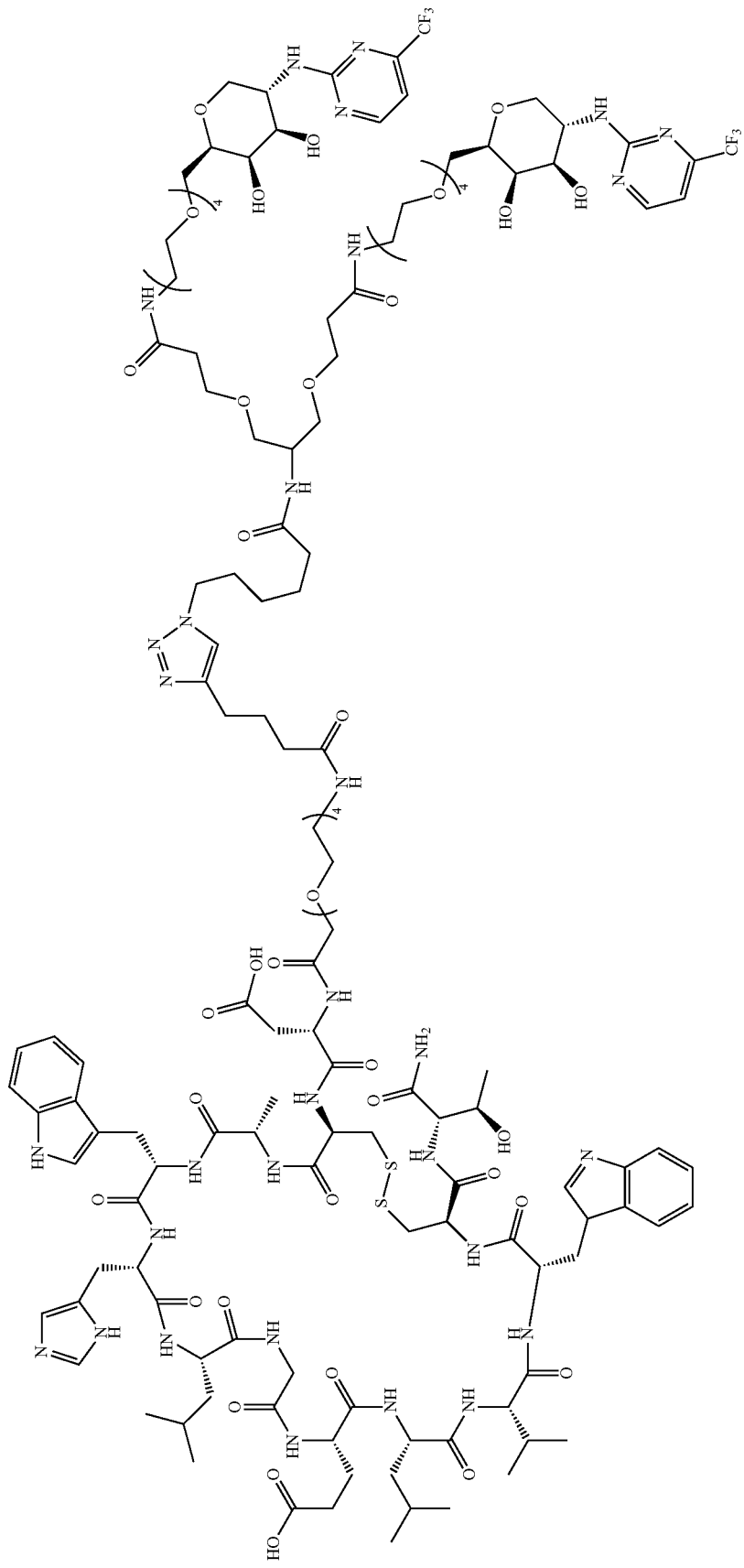

or a pharmaceutically acceptable salt thereof.

In certain embodiments the immunoglobulin degrading compound is:

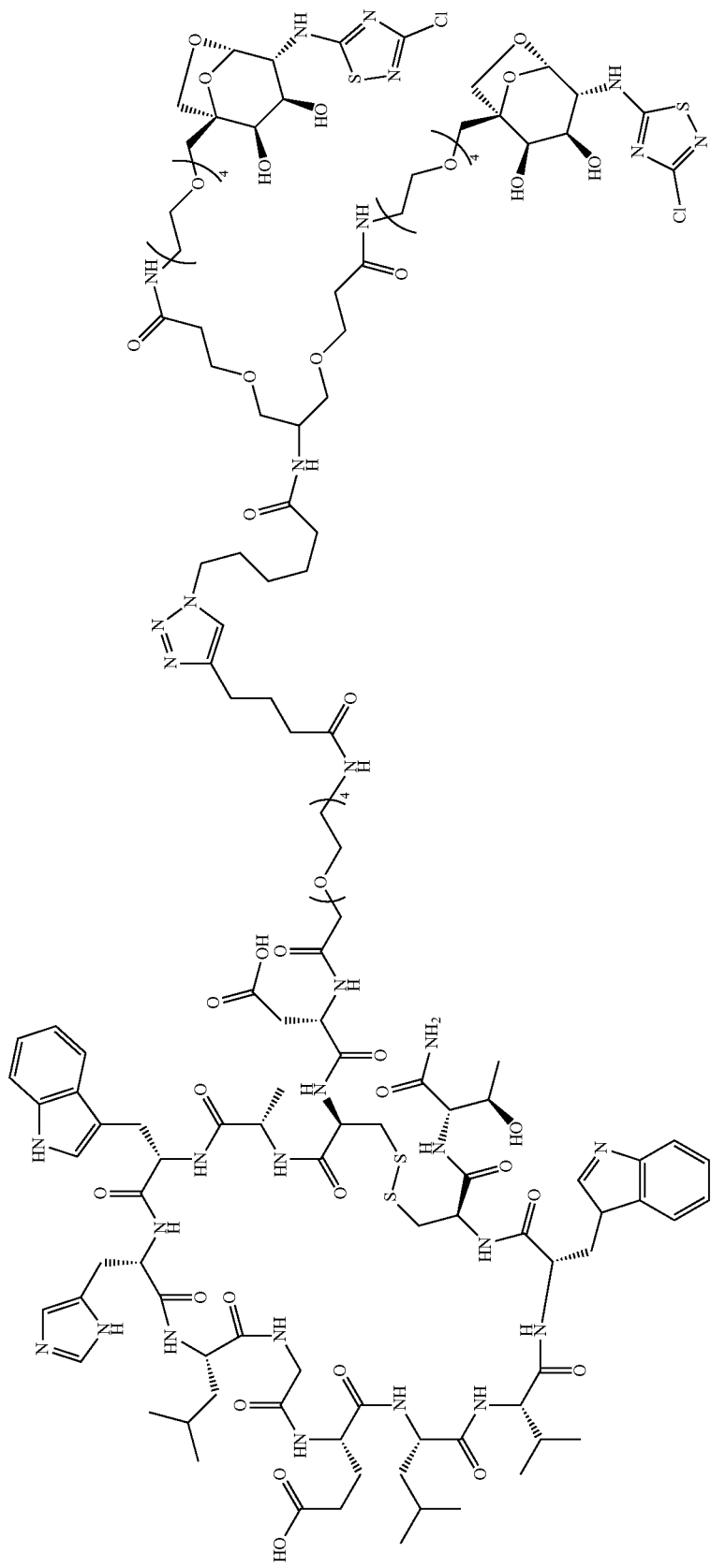

or a pharmaceutically acceptable salt thereof.

In certain embodiments the immunoglobulin degrading compound is:

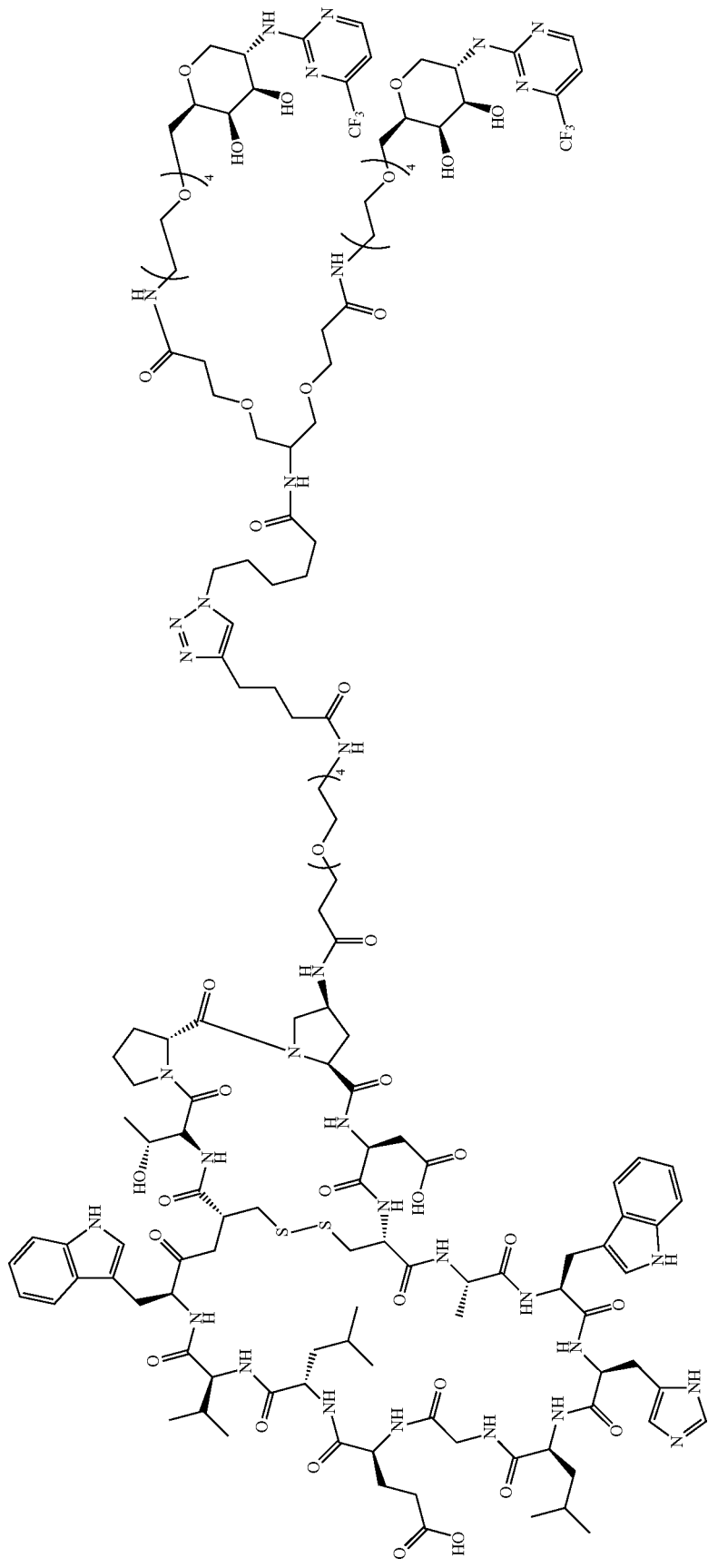

or a pharmaceutically acceptable salt thereof.
In certain embodiments the immunoglobulin degrading compound is:
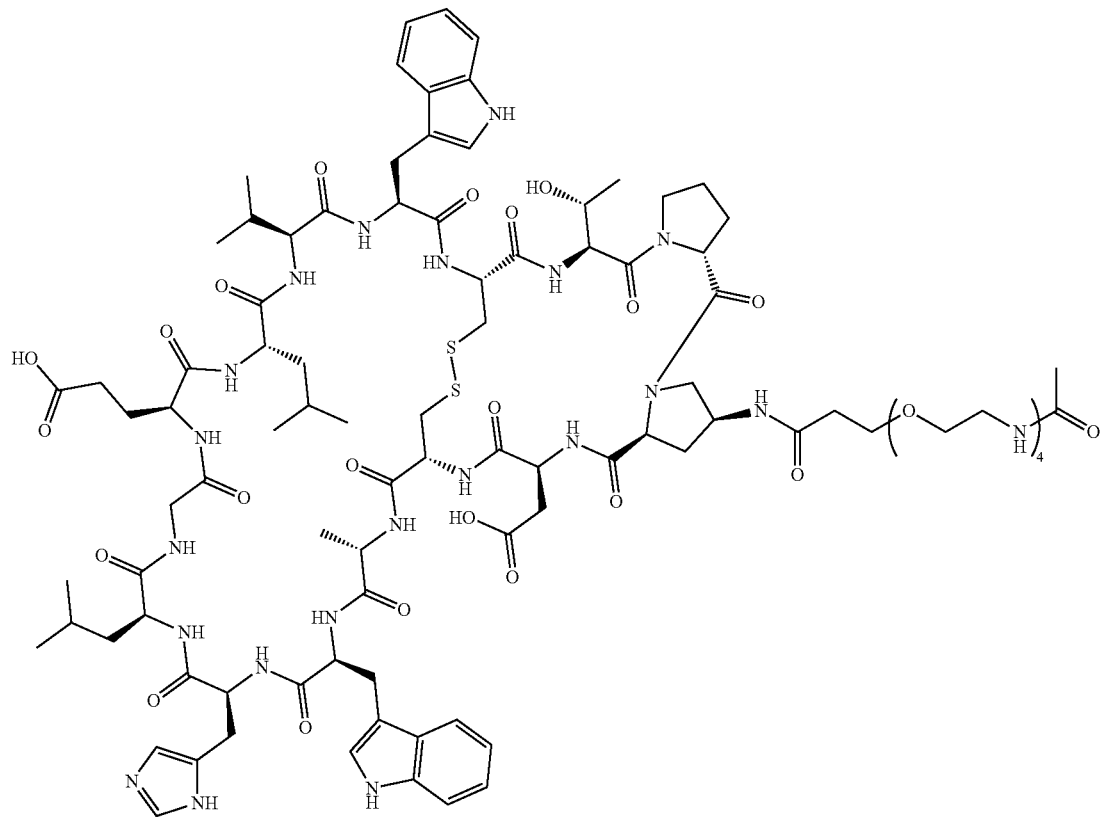
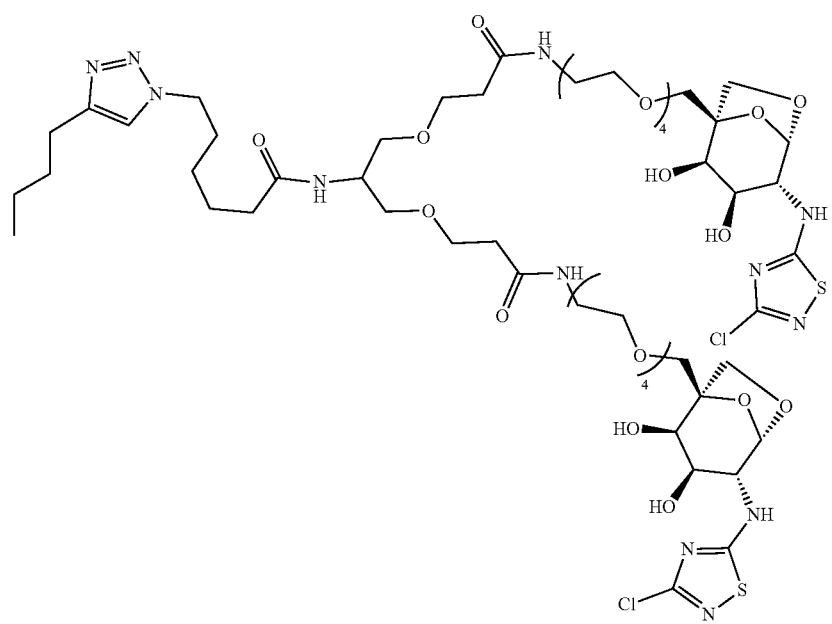
or a pharmaceutically acceptable salt thereof.
In certain embodiments the immunoglobulin degrading compound is:

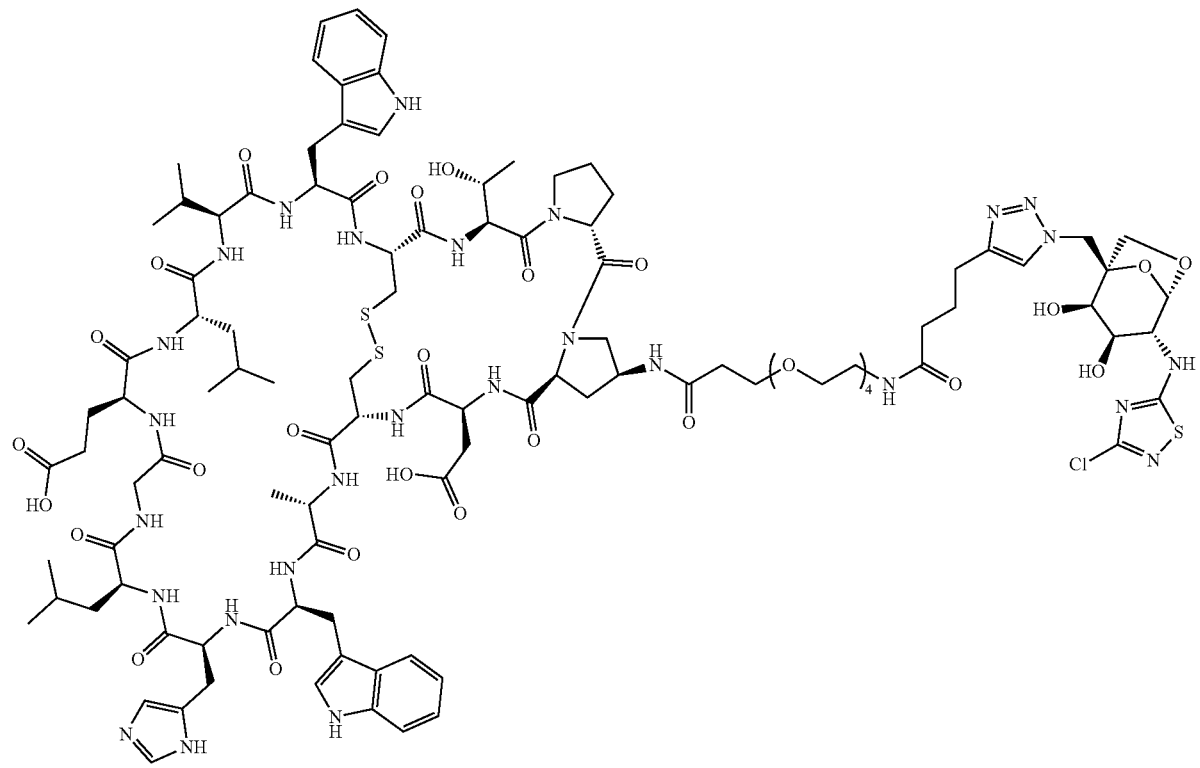
or a pharmaceutically acceptable salt thereof.
In certain embodiments the immunoglobulin degrading compound is:
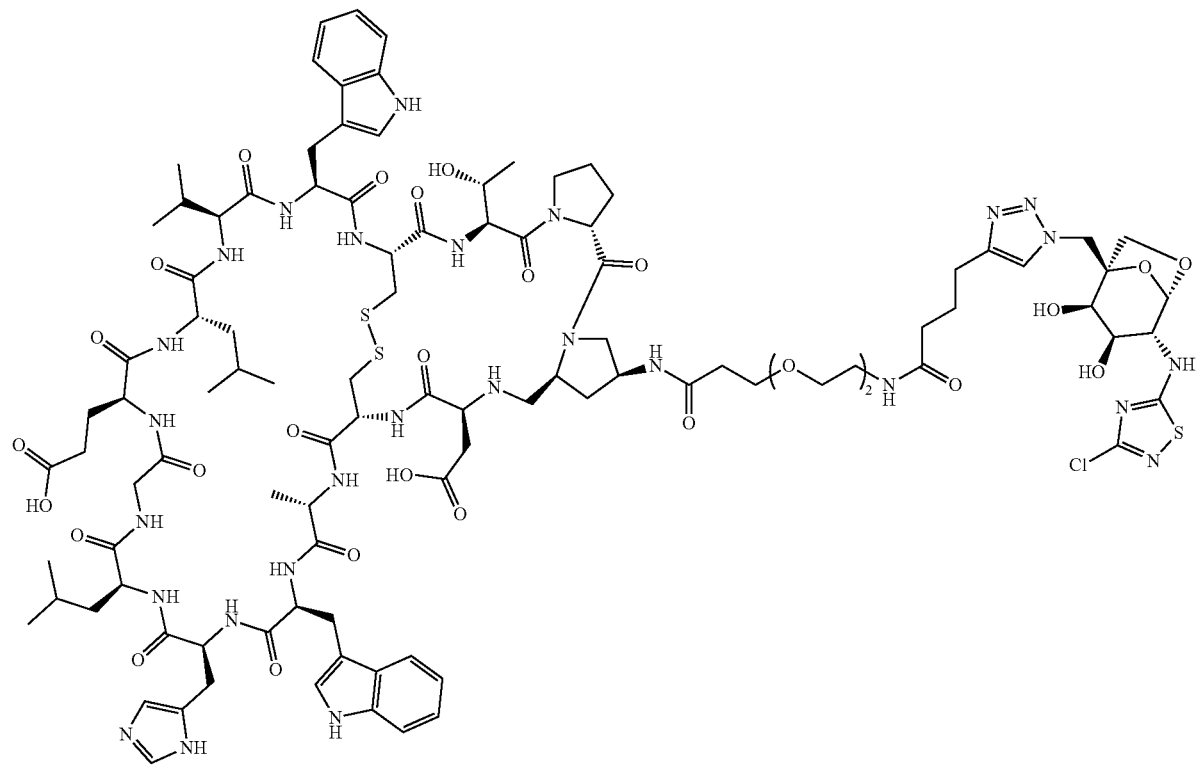
or a pharmaceutically acceptable salt thereof.

In certain embodiments the immunoglobulin degrading compound is:
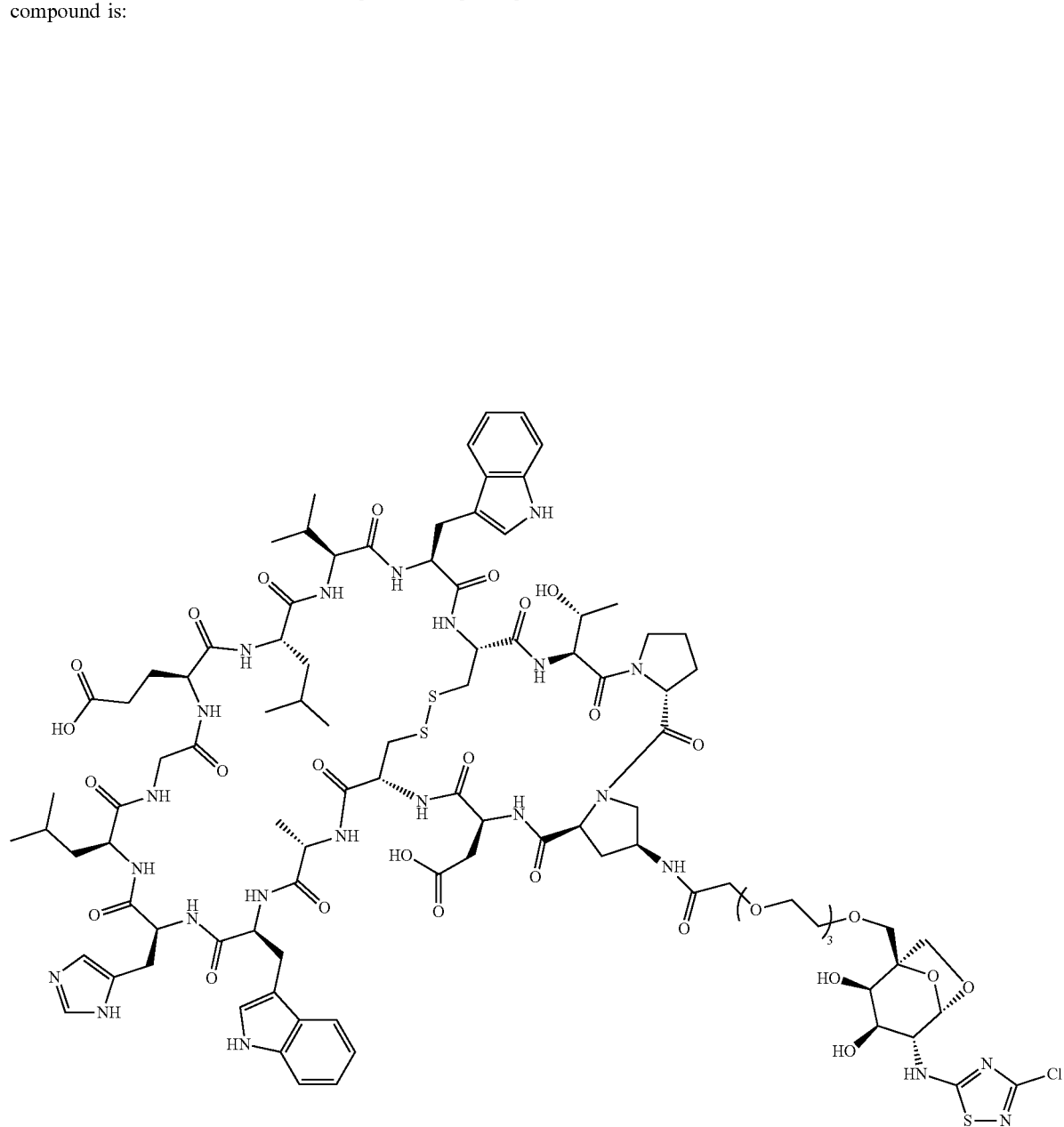
or a pharmaceutically acceptable salt thereof.

In certain embodiments the immunoglobulin degrading compound is:
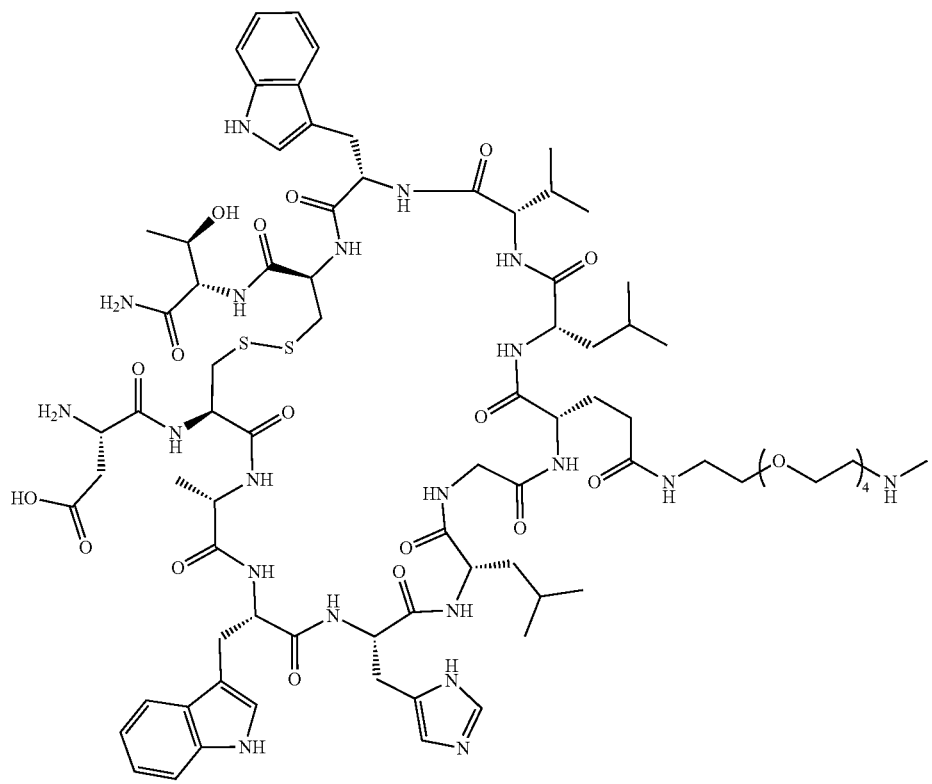
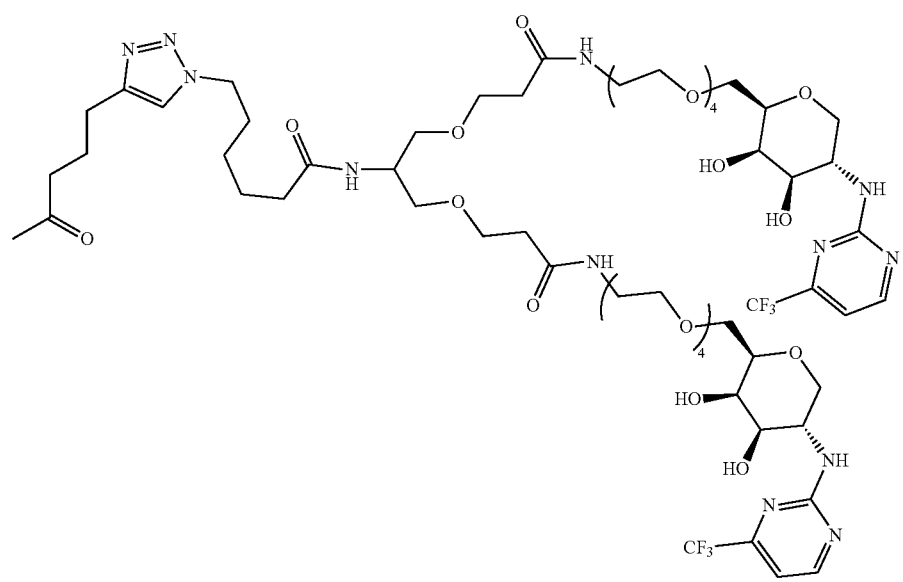
or a pharmaceutically acceptable salt thereof.

In certain embodiments the immunoglobulin degrading compound is:
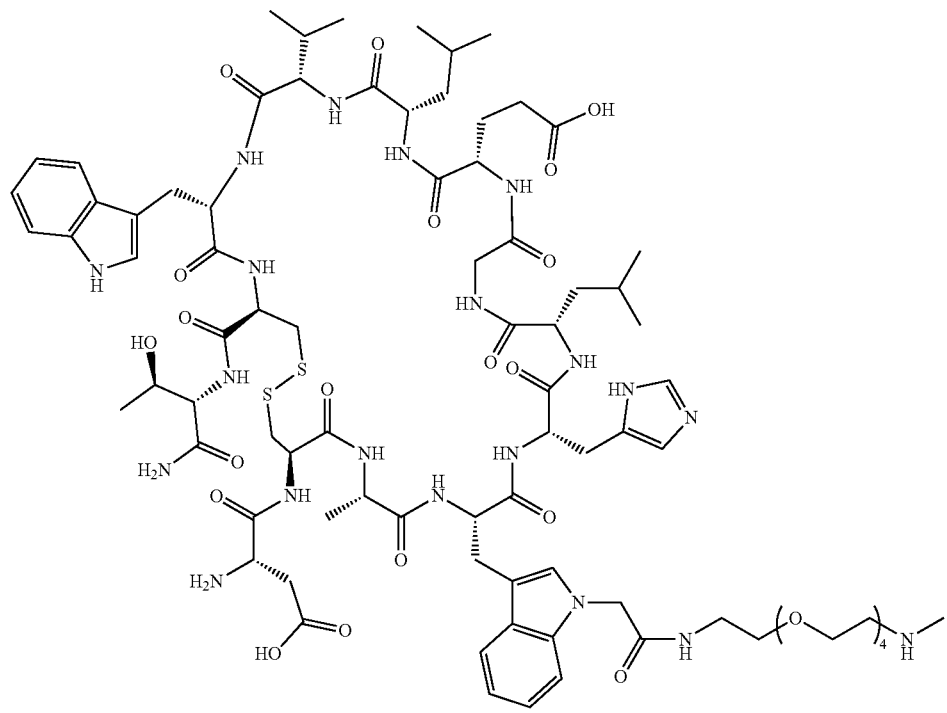
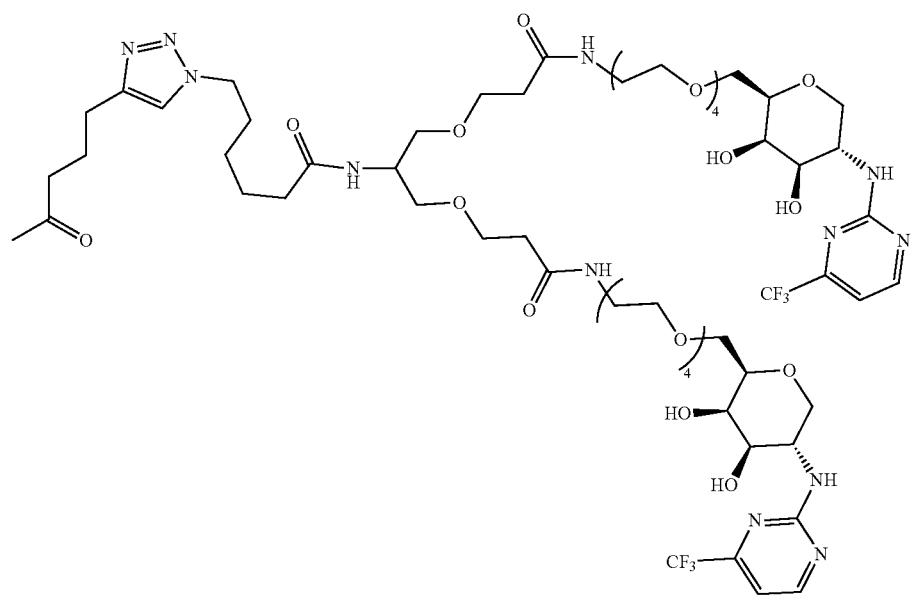
or a pharmaceutically acceptable salt thereof.

In certain embodiments the immunoglobulin degrading compound is:
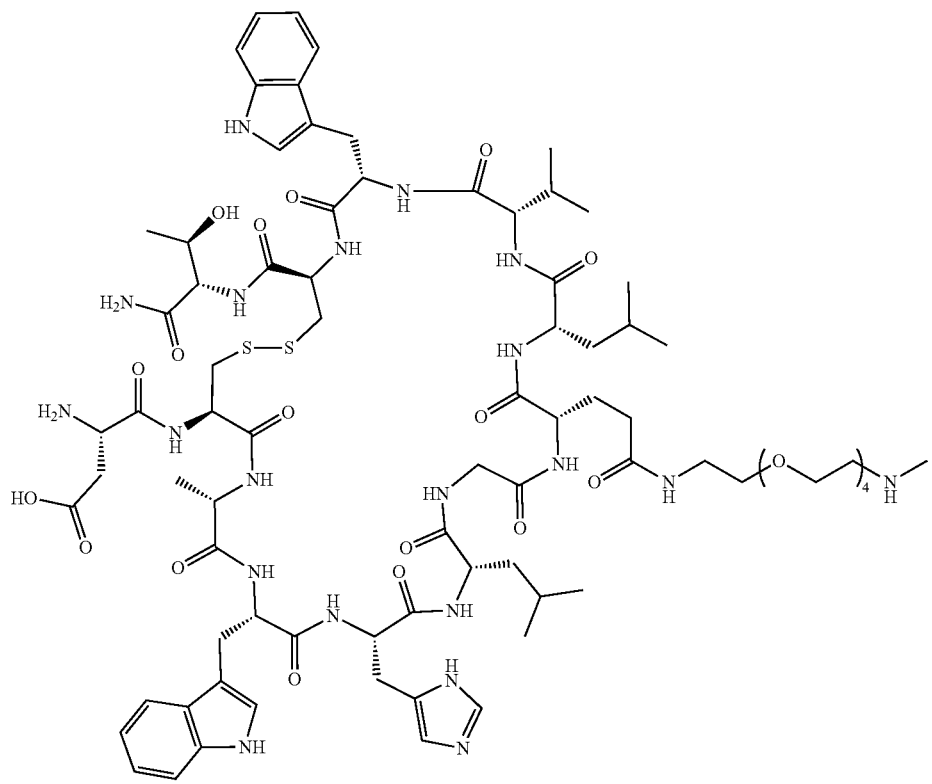
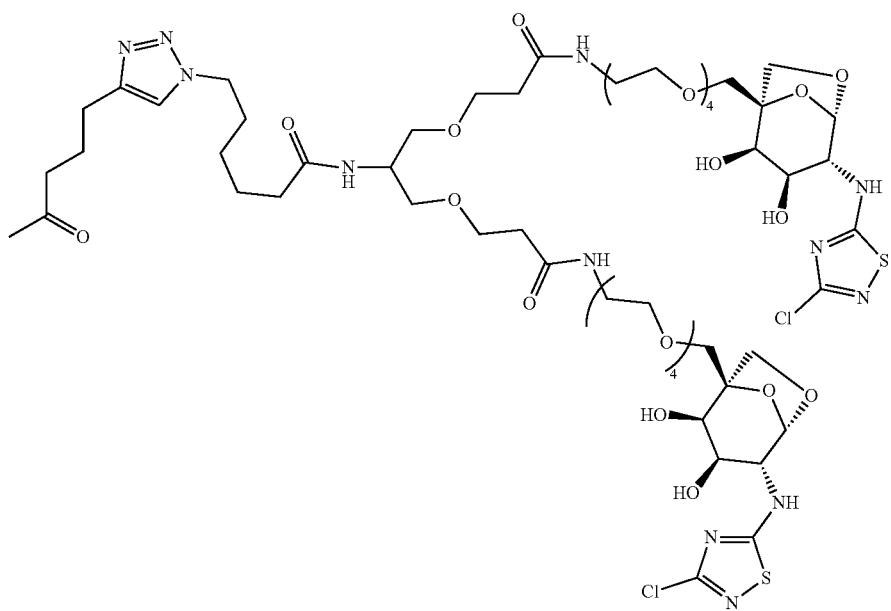
or a pharmaceutically acceptable salt thereof.

In certain embodiments the immunoglobulin degrading compound is:
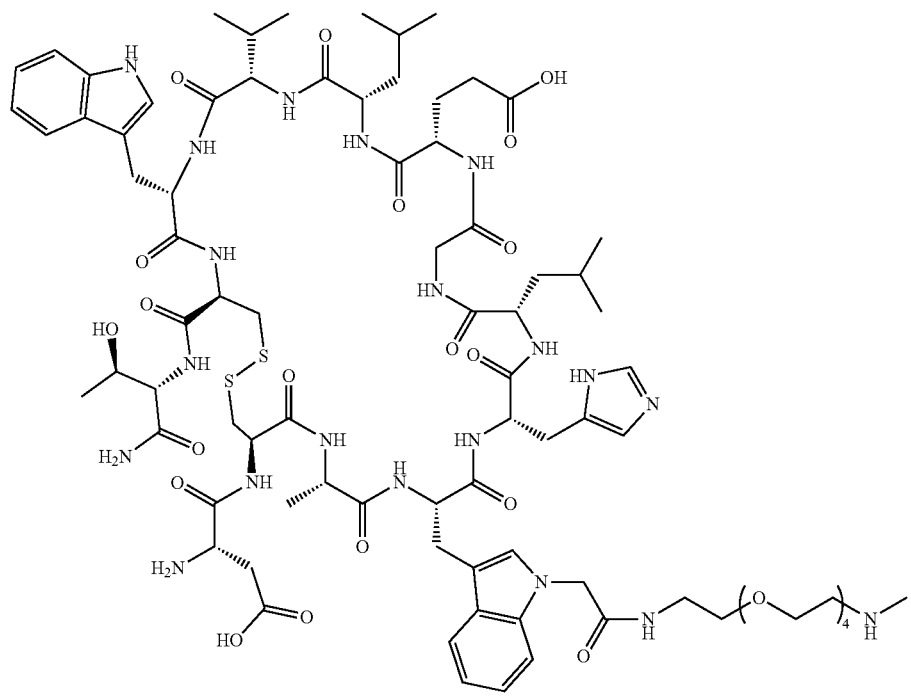
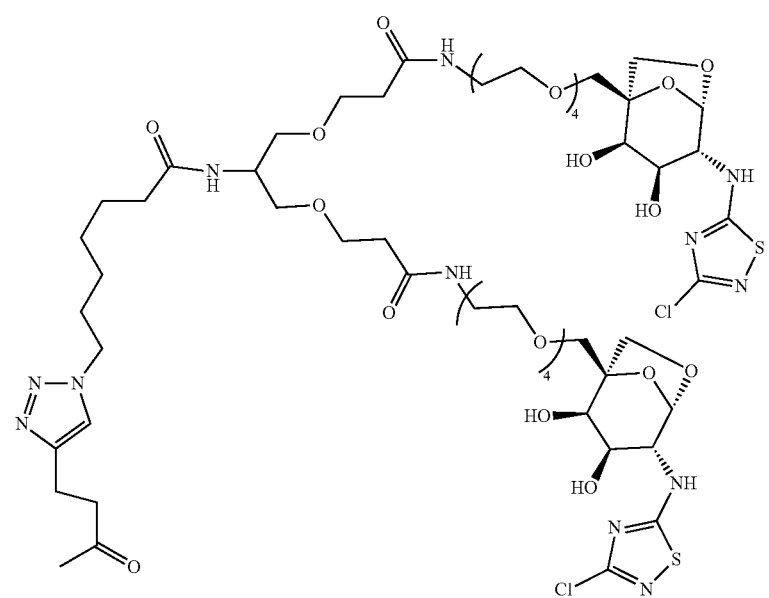
or a pharmaceutically acceptable salt thereof.

In certain embodiments the immunoglobulin degrading compound is selected from the following compounds or a bi- or tri-dentate version thereof;
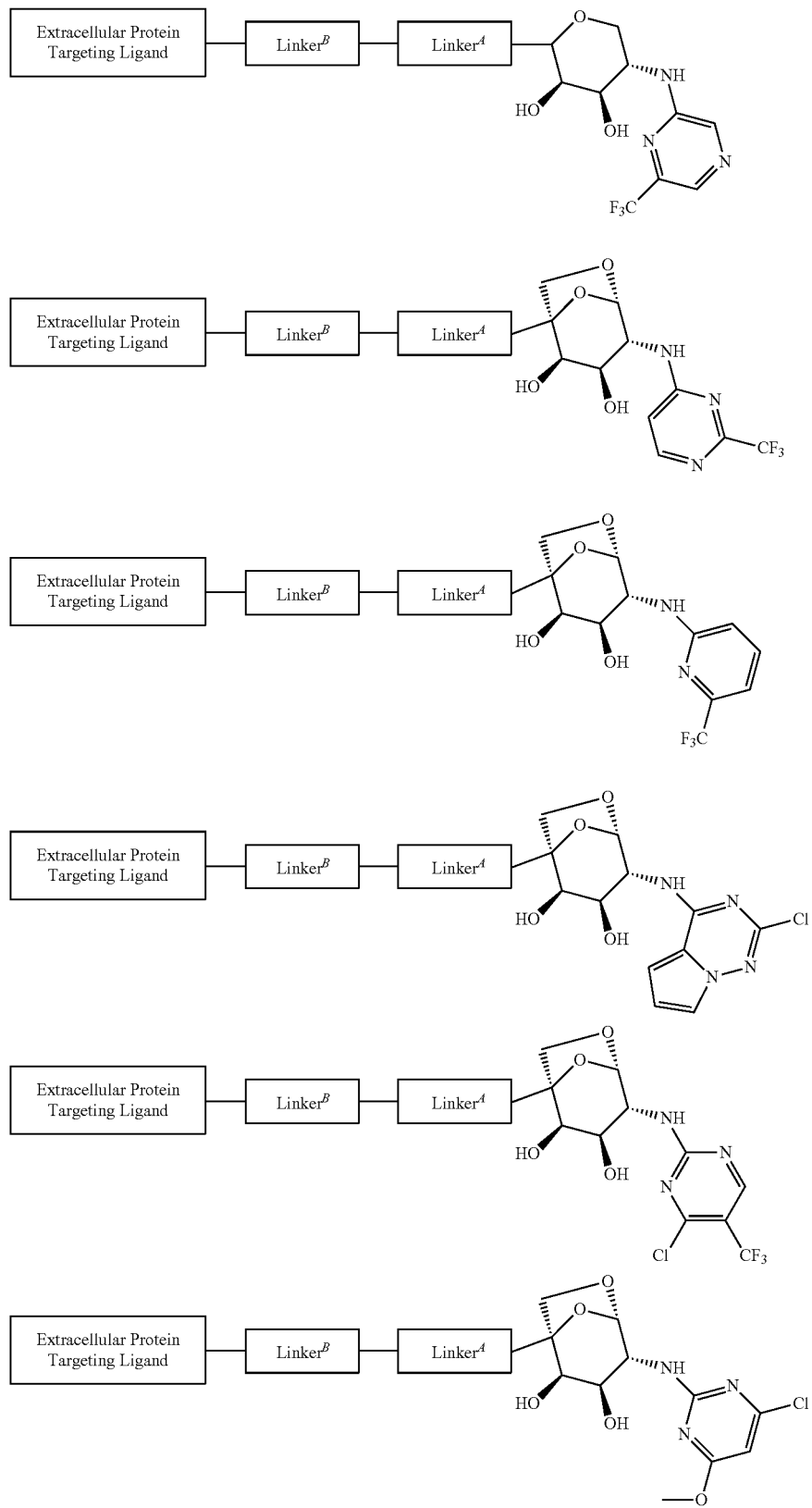

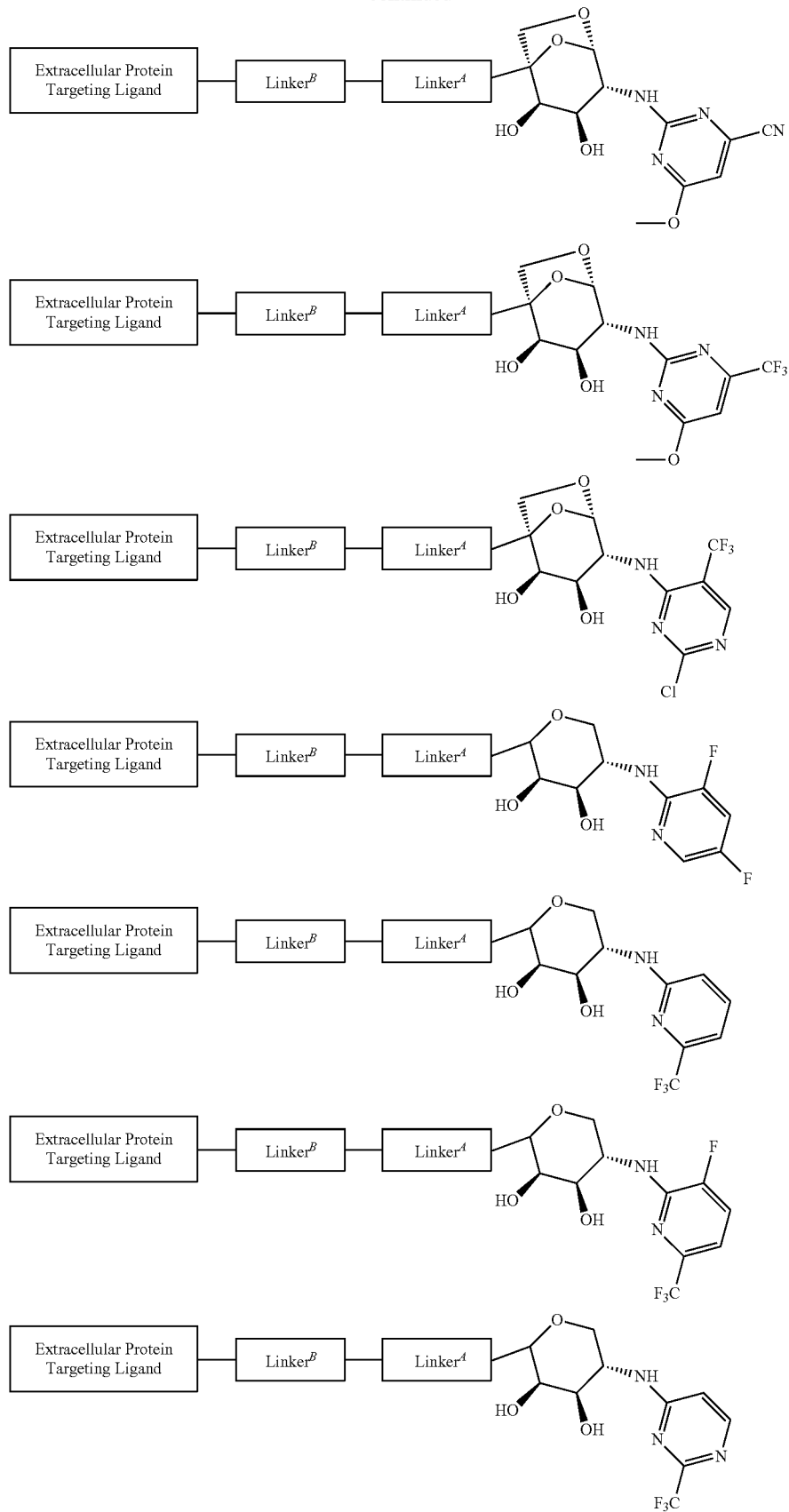

wherein the Extracellular Protein Targeting Ligand is:
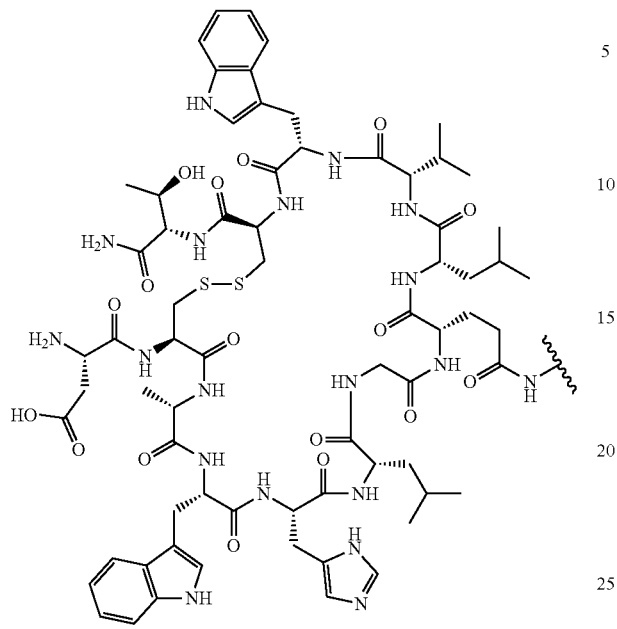
or a pharmaceutically acceptable salt thereof.
In certain embodiments the immunoglobulin degrading compound is selected from the following compounds or a bi- or tri-dentate version thereof,
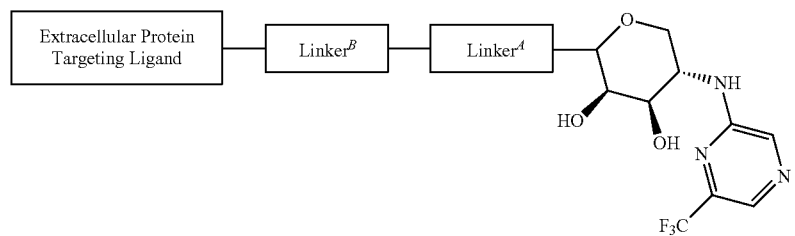
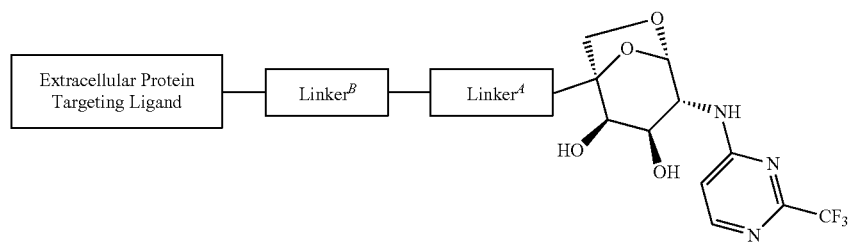
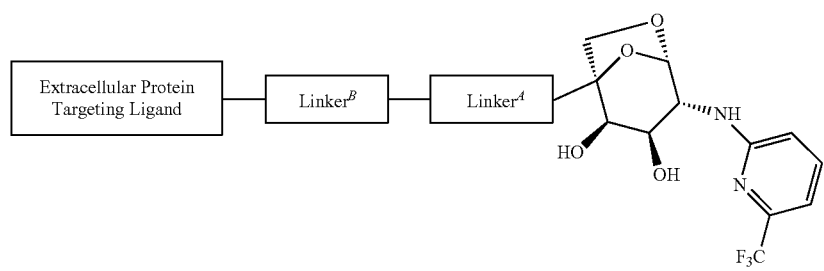

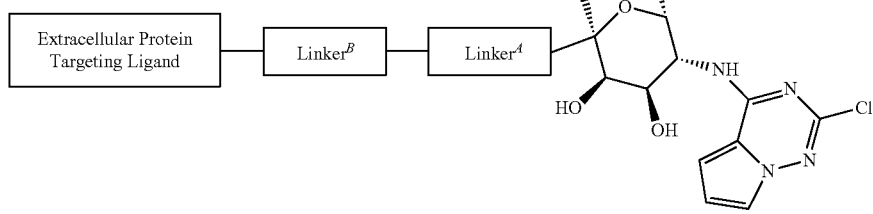
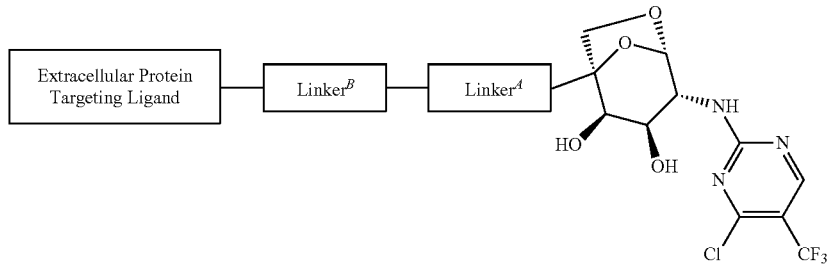
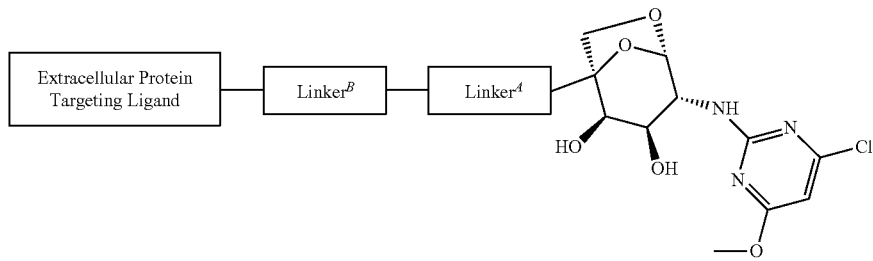
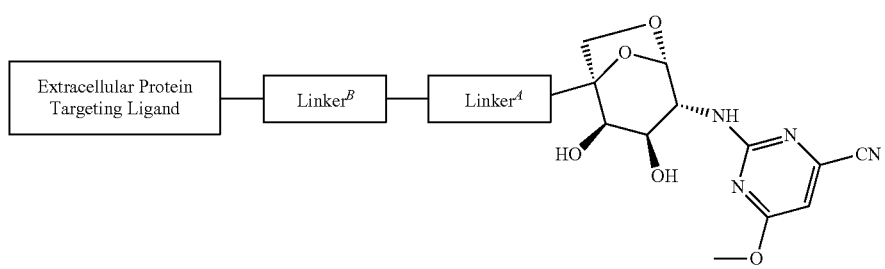
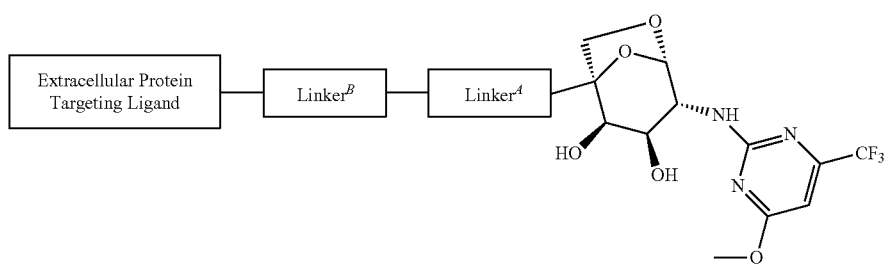
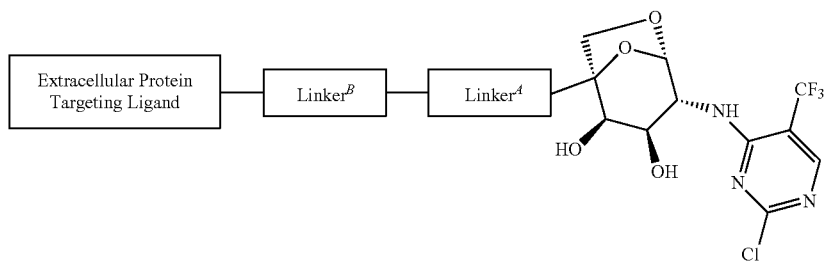

-continued
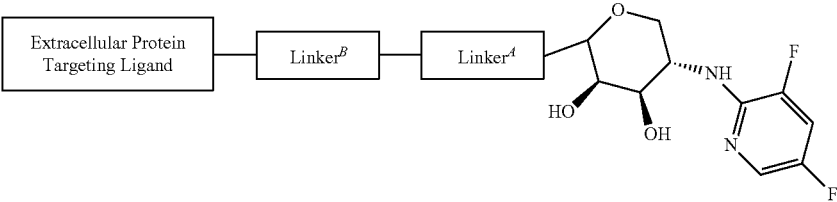
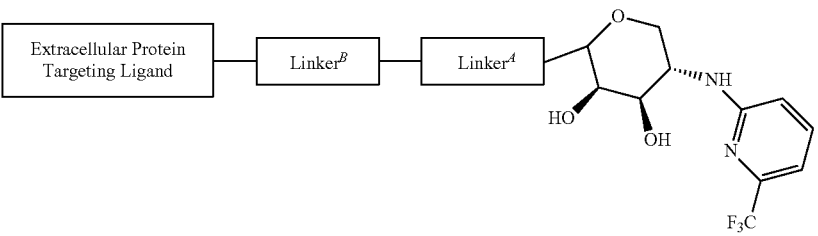
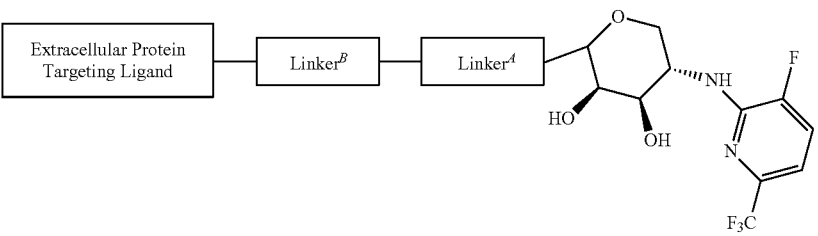
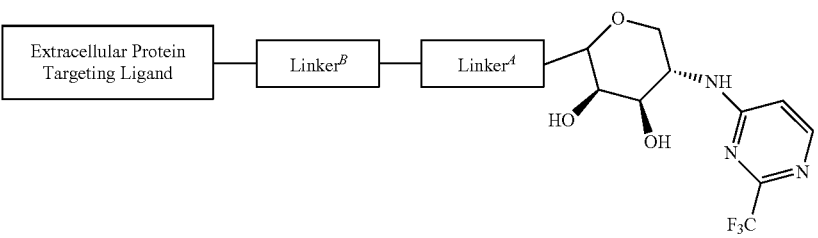
wherein the Extracellular Protein Targeting Ligand is:
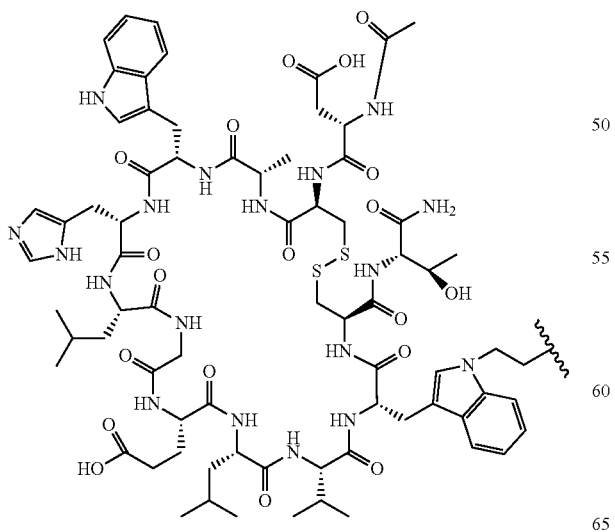
or a pharmaceutically acceptable salt thereof.

In certain embodiments the immunoglobulin degrading compound is selected from the following compounds or a bi- or tri-dentate version thereof,
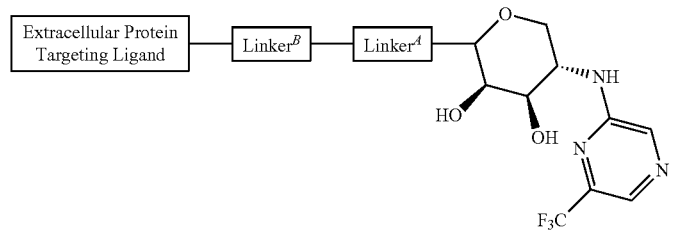
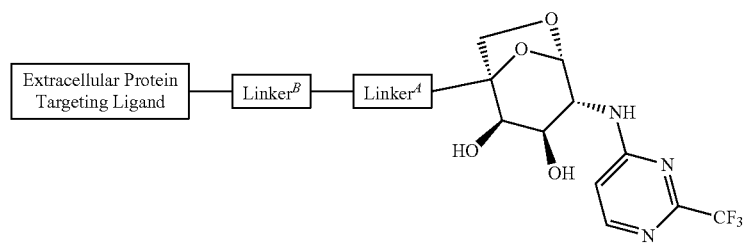
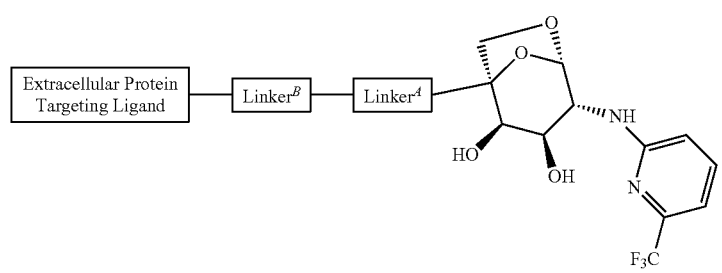
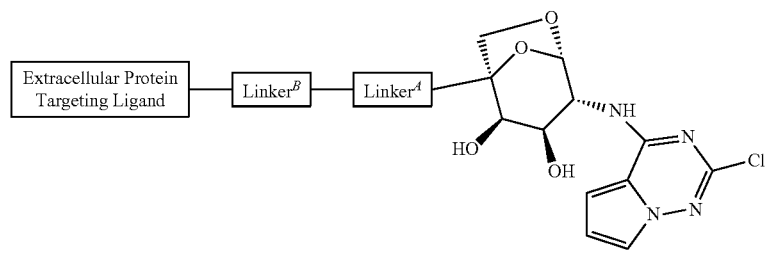
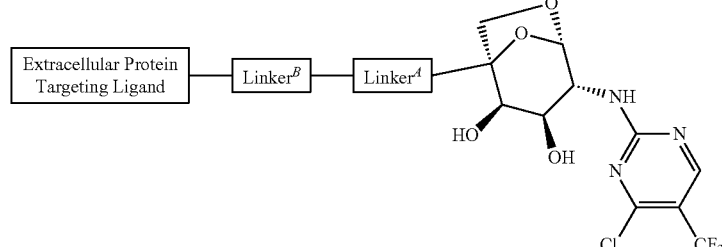
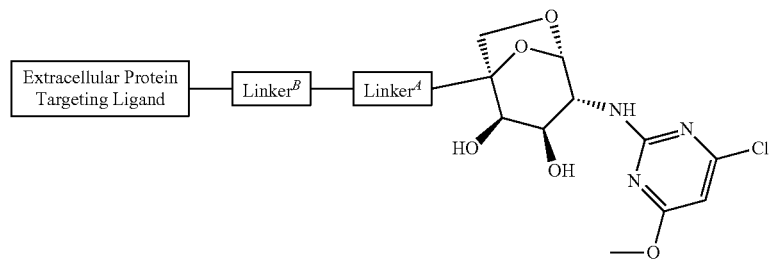

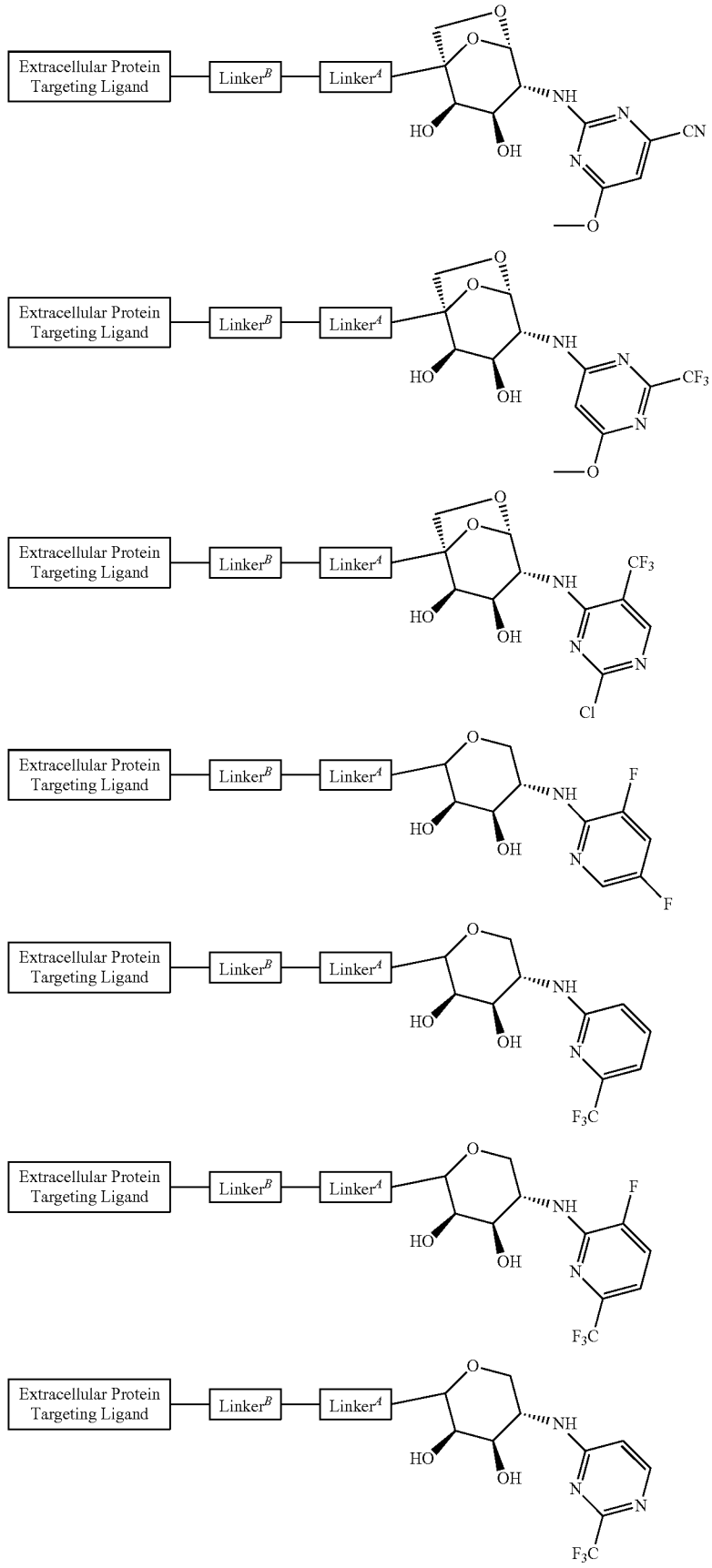

wherein the Extracellular Protein Targeting Ligand is:
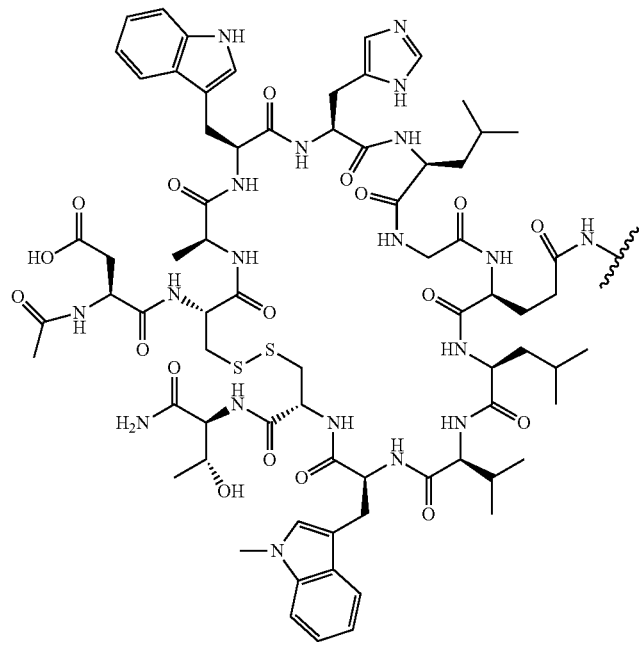
or a pharmaceutically acceptable salt thereof.
In certain embodiments the Immunoglobulin Targeting Ligand is:
In certain embodiments the Immunoglobulin Targeting Ligand is:
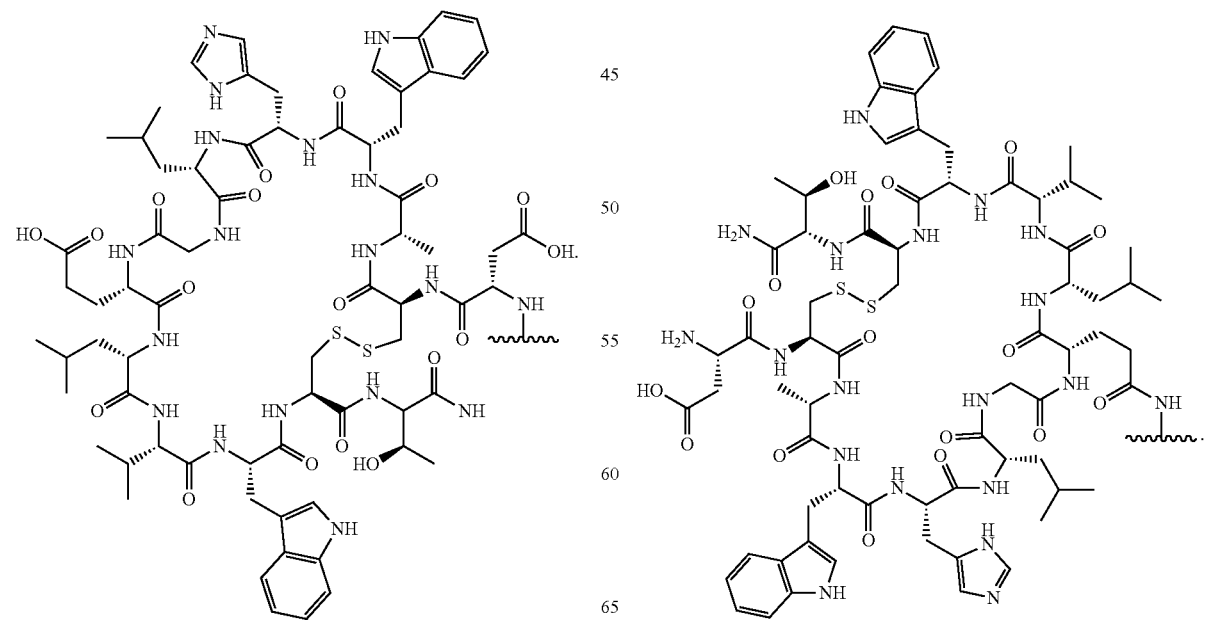

In certain embodiments the Immunoglobulin Targeting Ligand is:
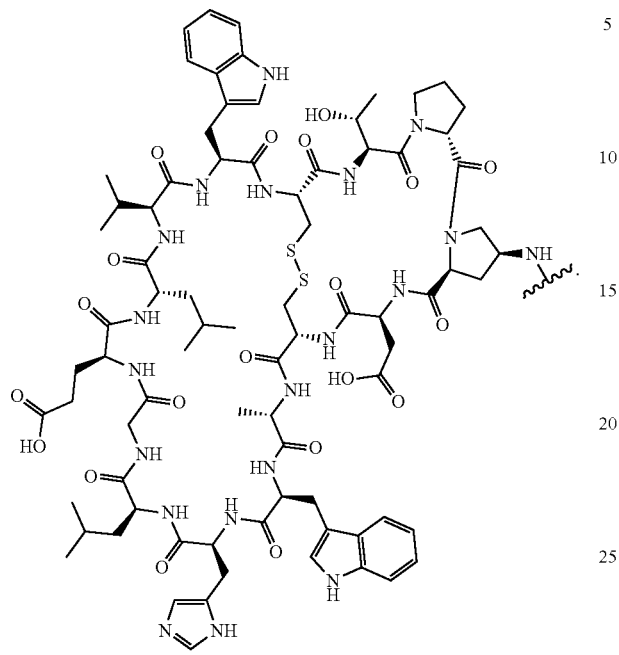
In certain embodiments the immunoglobulin degrading compound is selected from the following compounds or a bi- or tri-dentate version thereof,
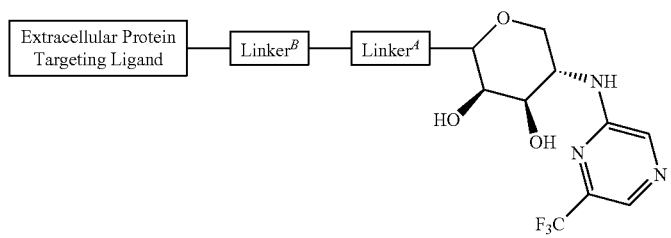
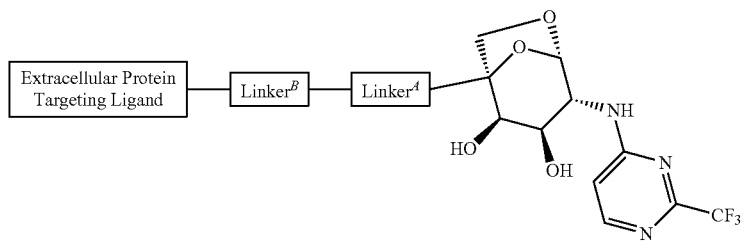
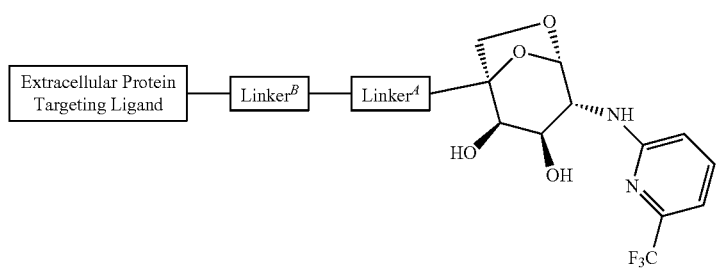

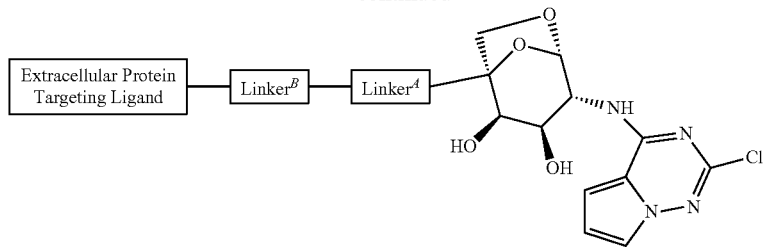
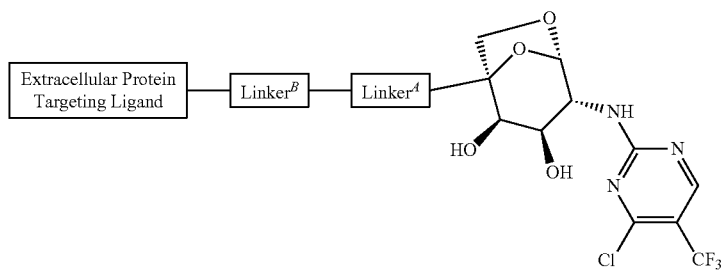
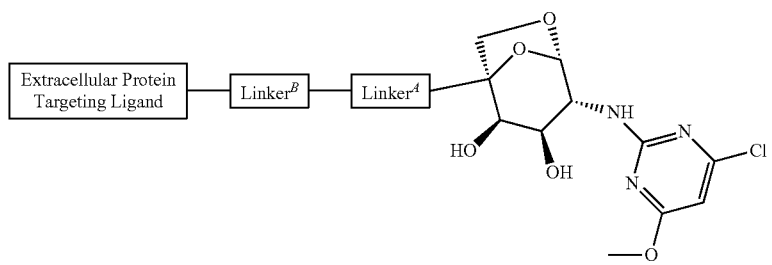
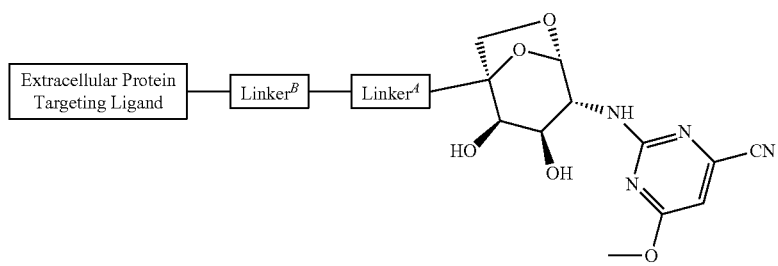
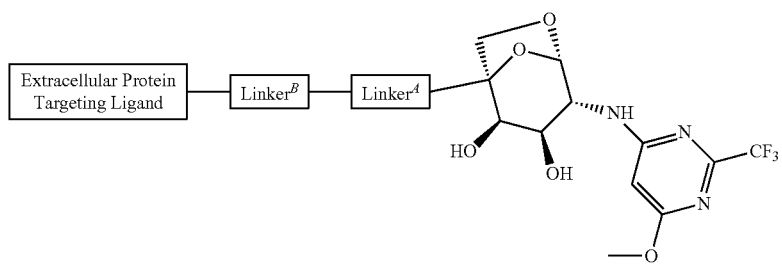
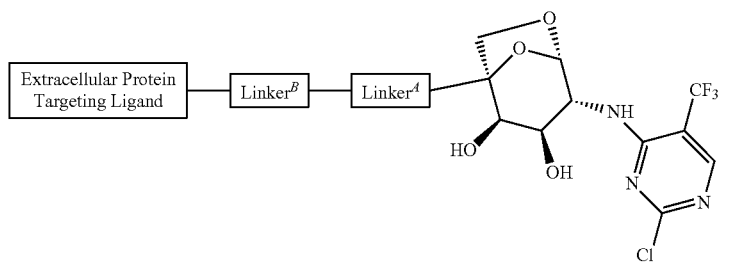

-continued
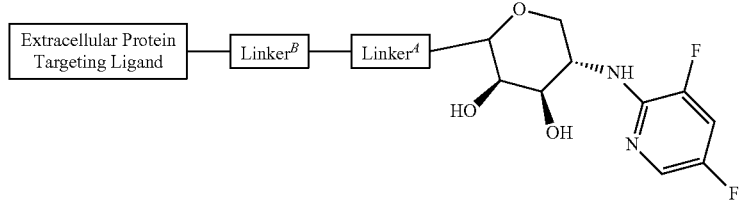
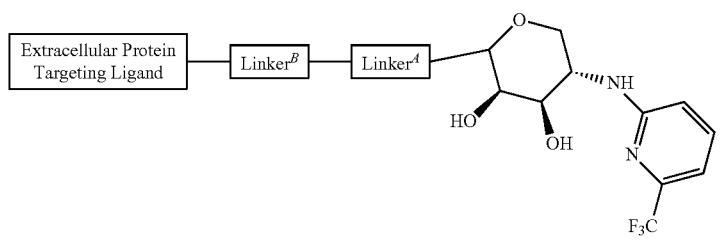
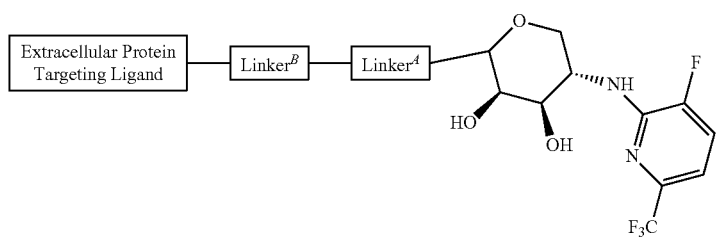
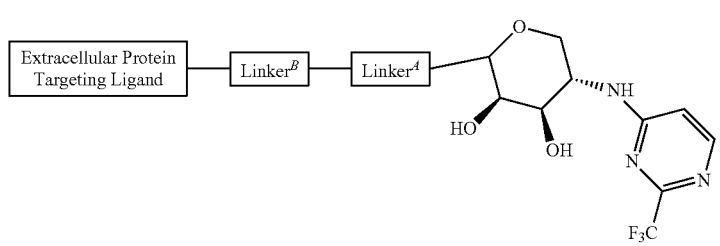

wherein the Extracellular Protein Targeting Ligand is:
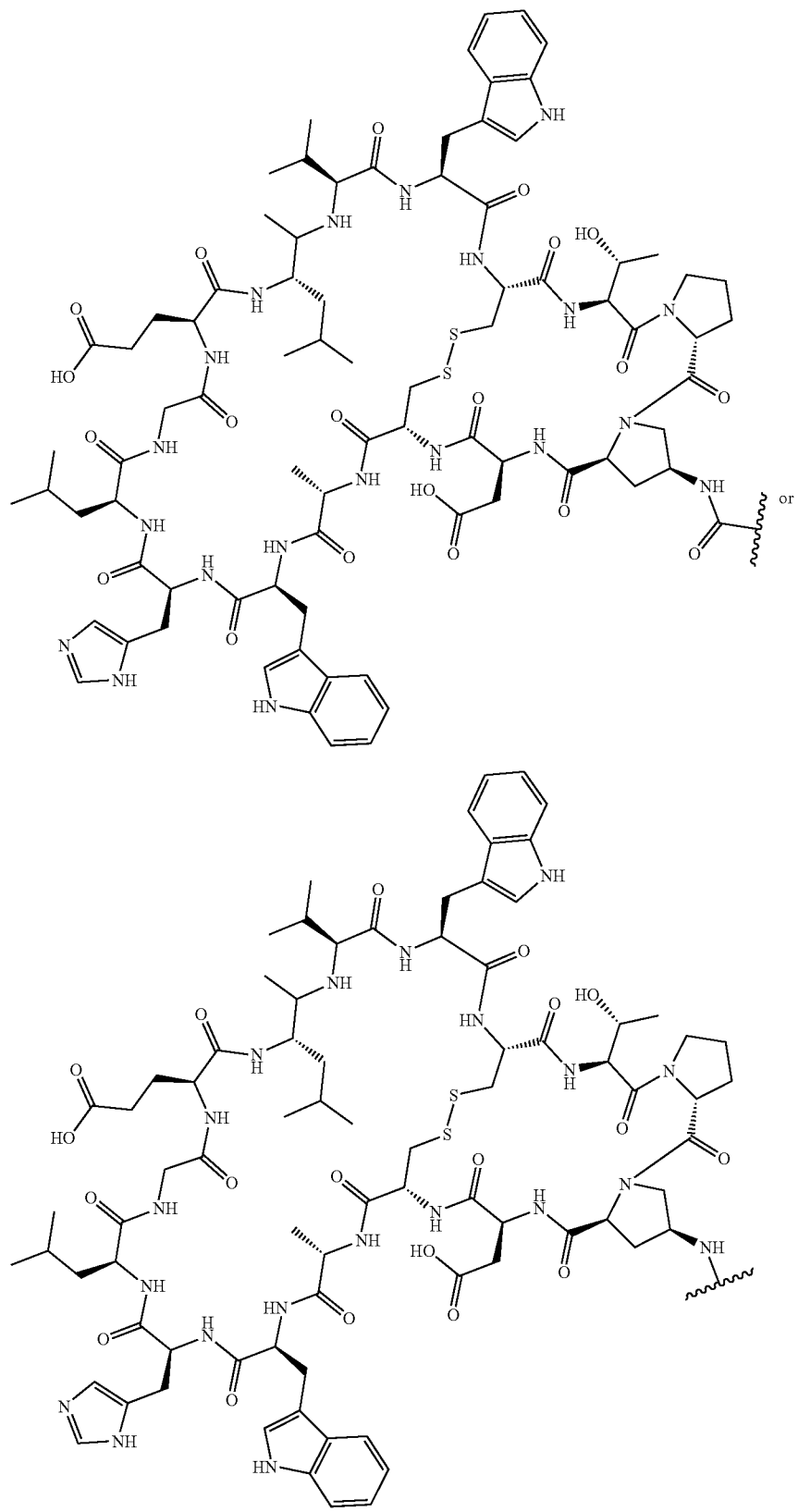
or a pharmaceutically acceptable salt thereof.

In certain embodiments the immunoglobulin degrading compound is selected from the following compounds or a bi- or tri-dentate version thereof,
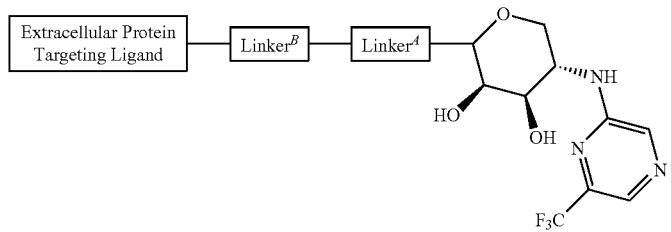
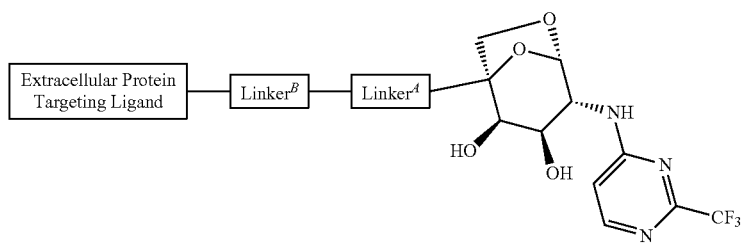
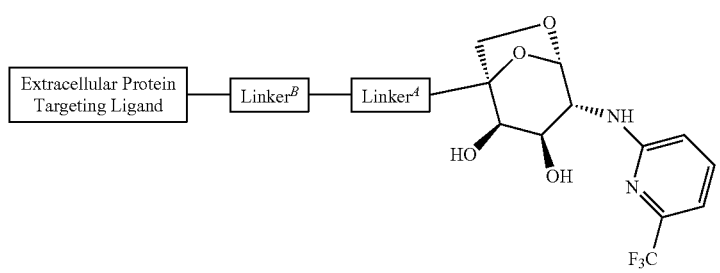
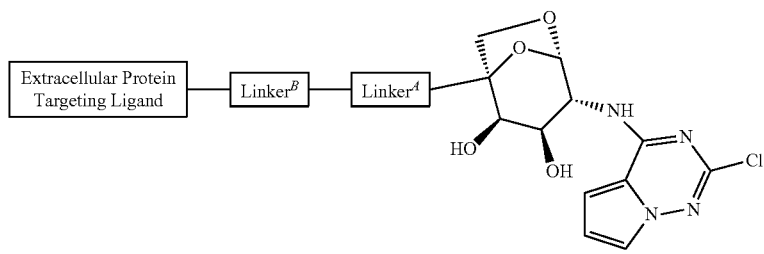
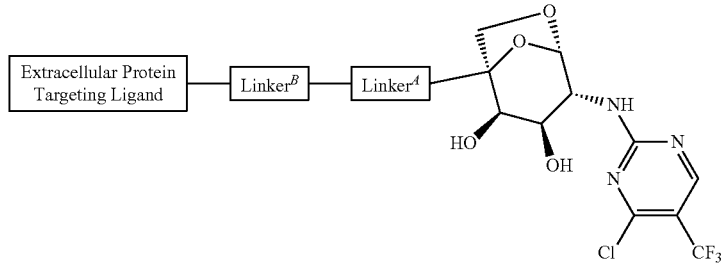
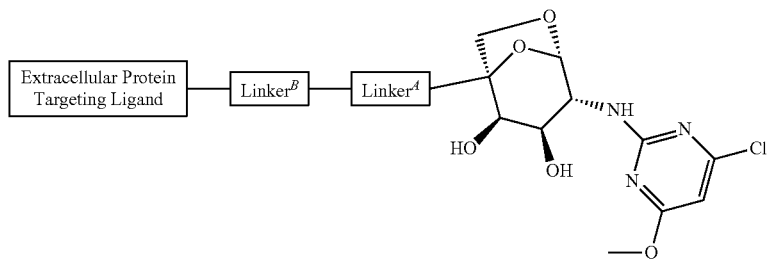

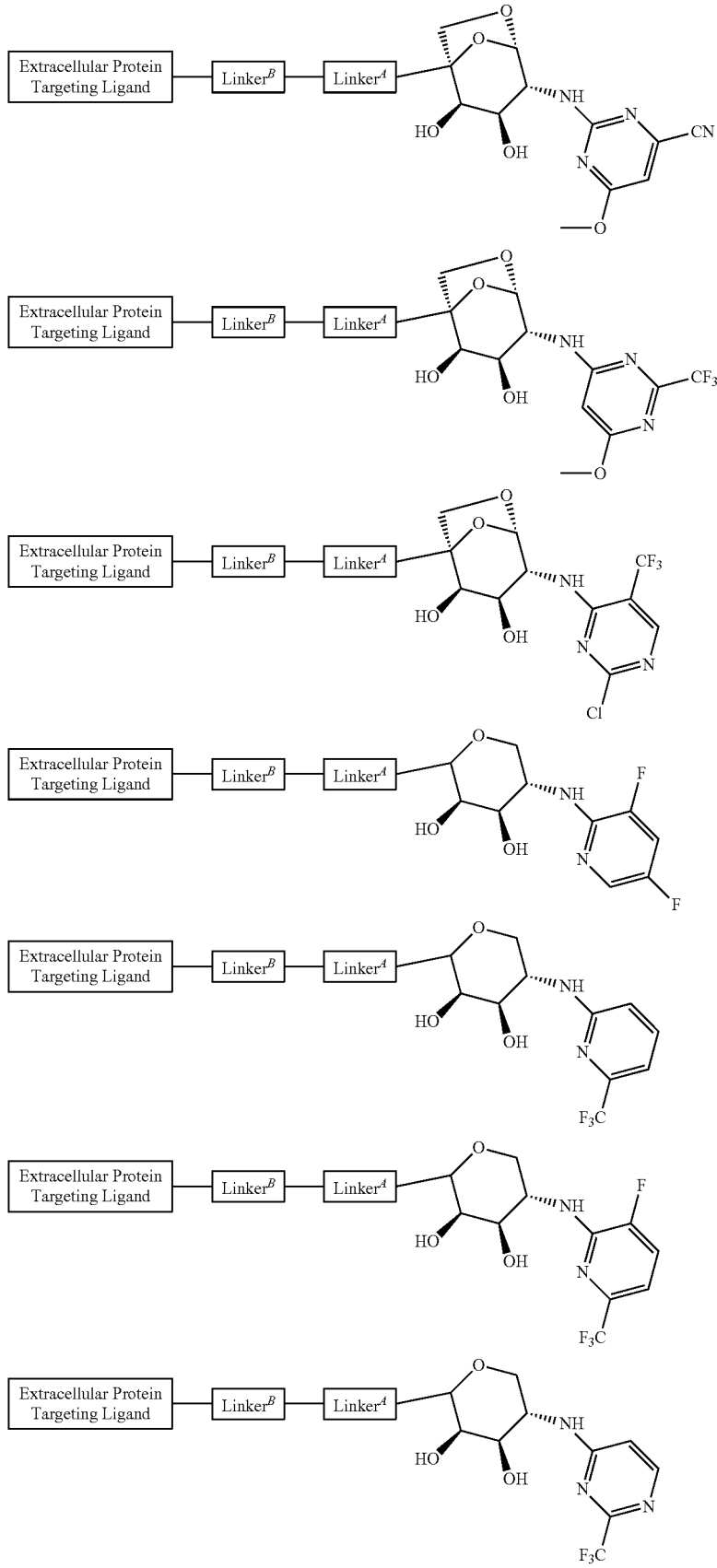

wherein the Extracellular Protein Targeting Ligand is:
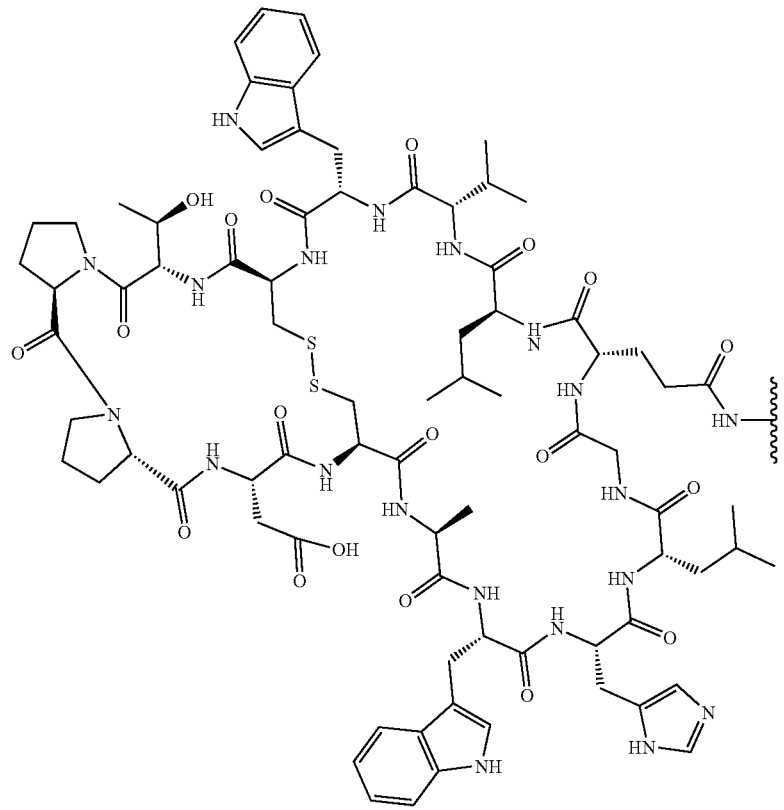 [SMILES: *NC(=O)CC[C@@H]1NC(=O)CNC(=O)[C@H](CC(C)C)NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC1=O)C(=O)N[C@@H]([C@@H](C)O)C(=O)N1CCC[C@@H]1C(=O)N1CCC[C@H]1C(=O)N[C@@H](CC(=O)O)C(=O)N2]
or a pharmaceutically acceptable salt thereof.
In certain embodiments the immunoglobulin degrading compound is selected from the following compounds or a bi- or tri-dentate version thereof;
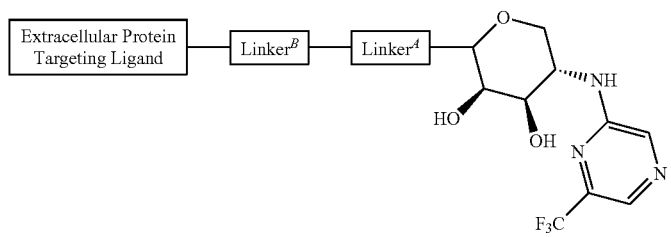
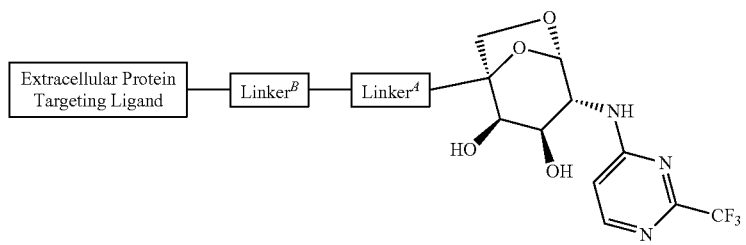

-continued
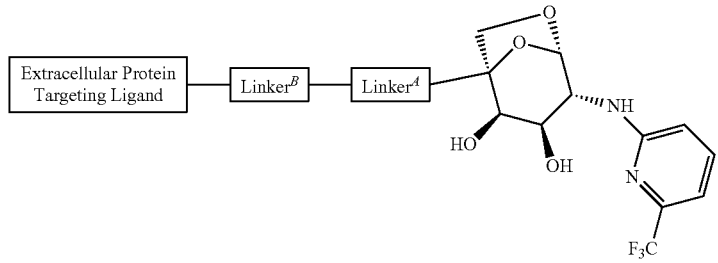
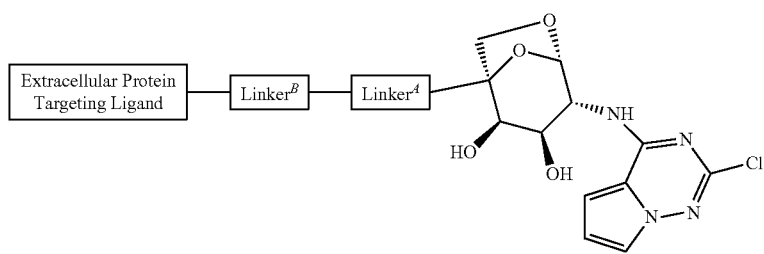
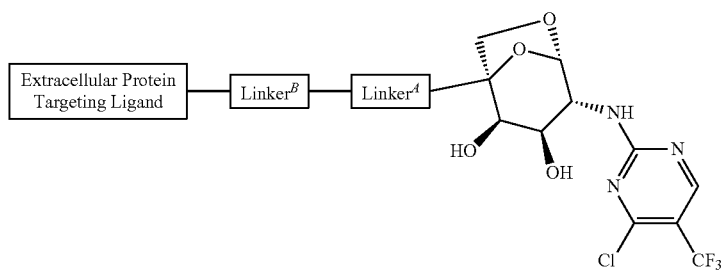
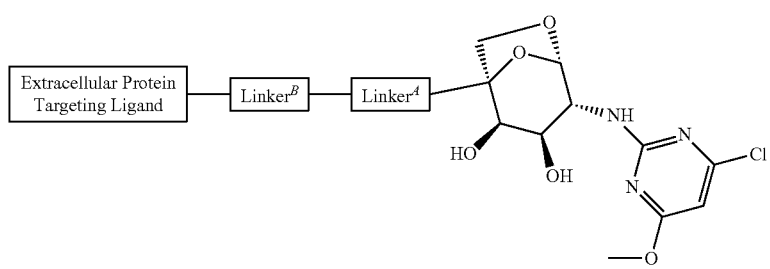
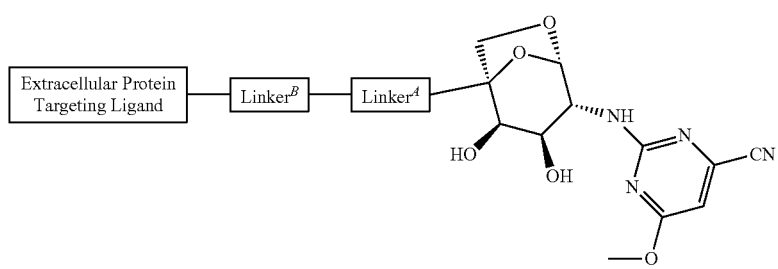
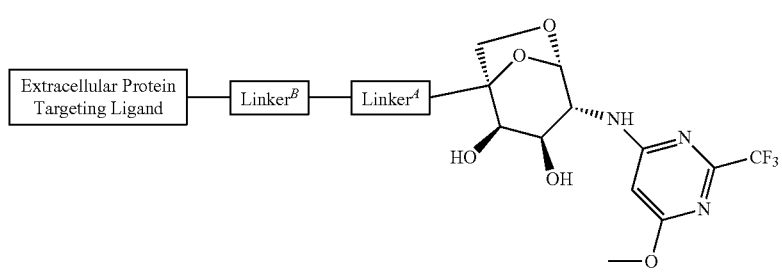

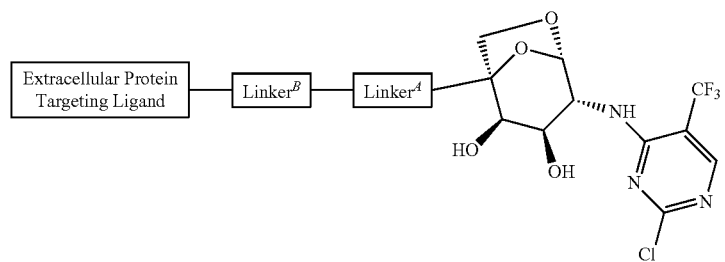
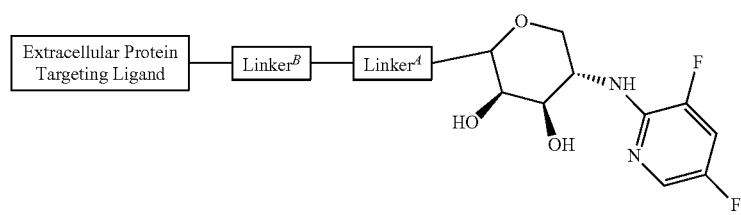
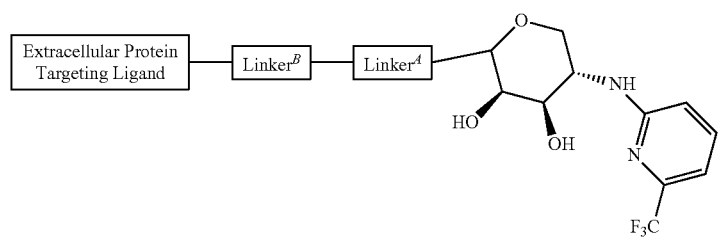
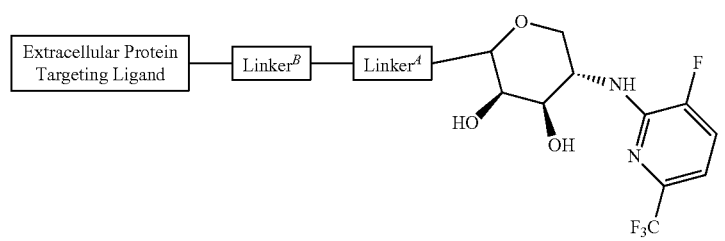
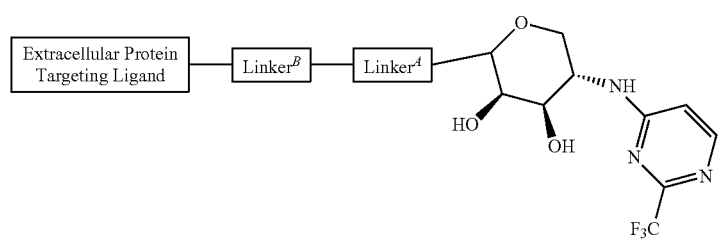

wherein the Extracellular Protein Targeting Ligand is:
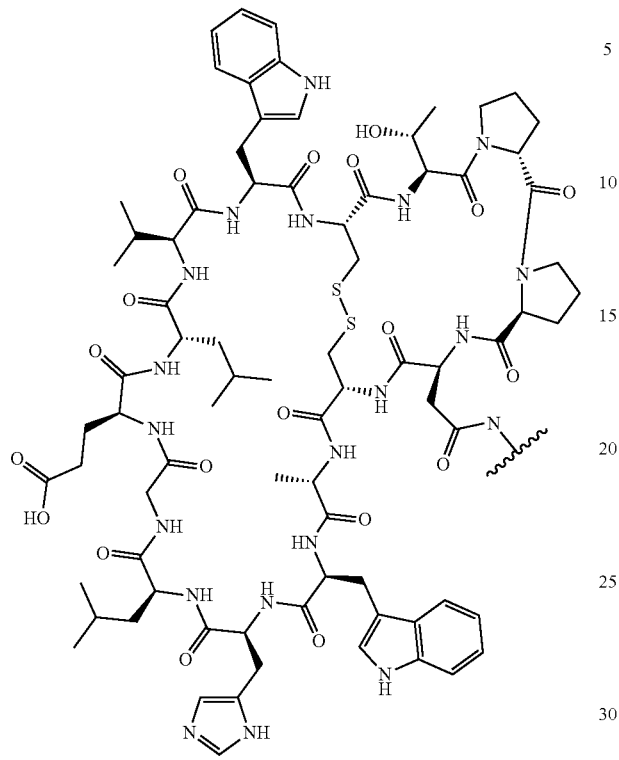
or a pharmaceutically acceptable salt thereof.
In certain embodiments the immunoglobulin degrading compound is selected from the following compounds or a bi- or tri-dentate version thereof,
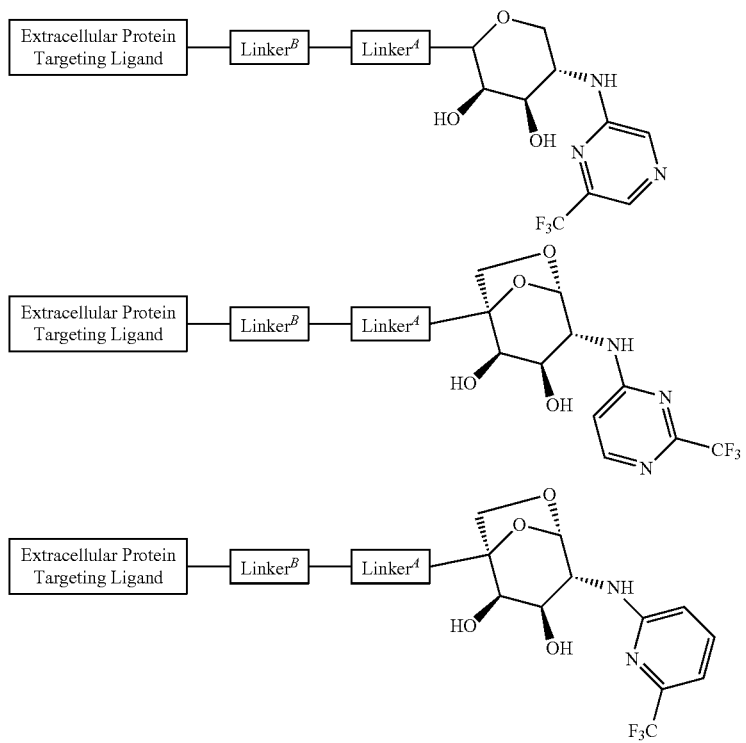

-continued
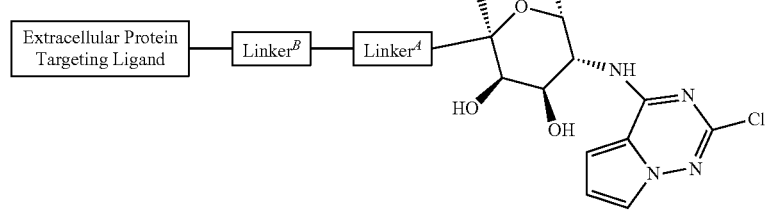
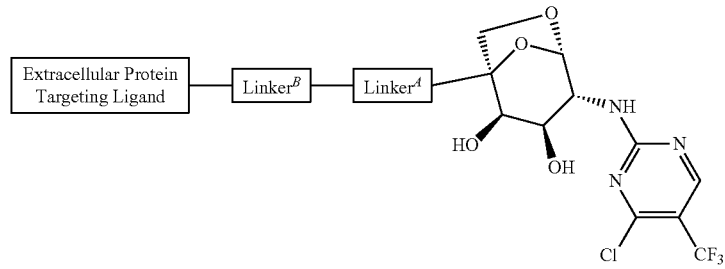
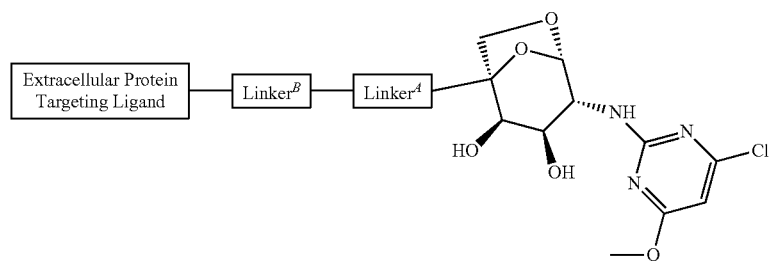
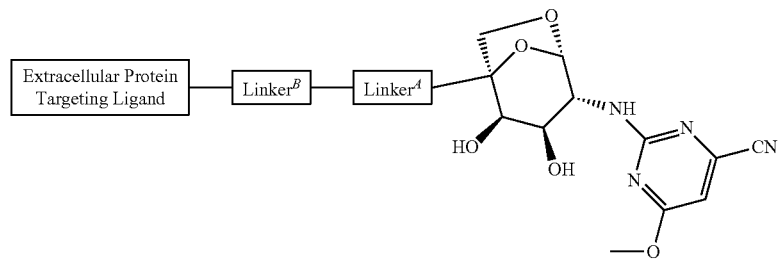
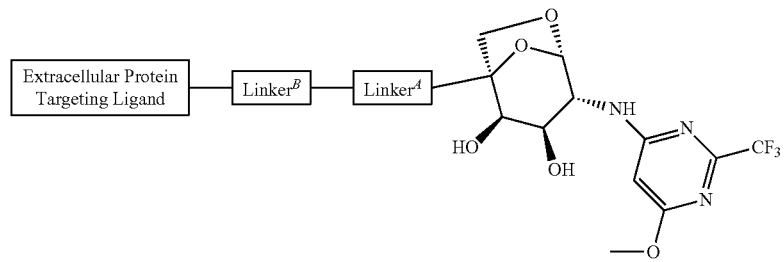
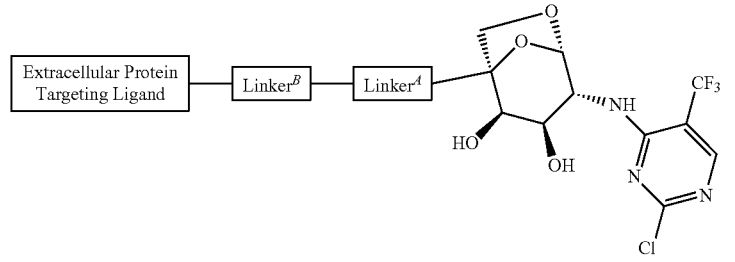

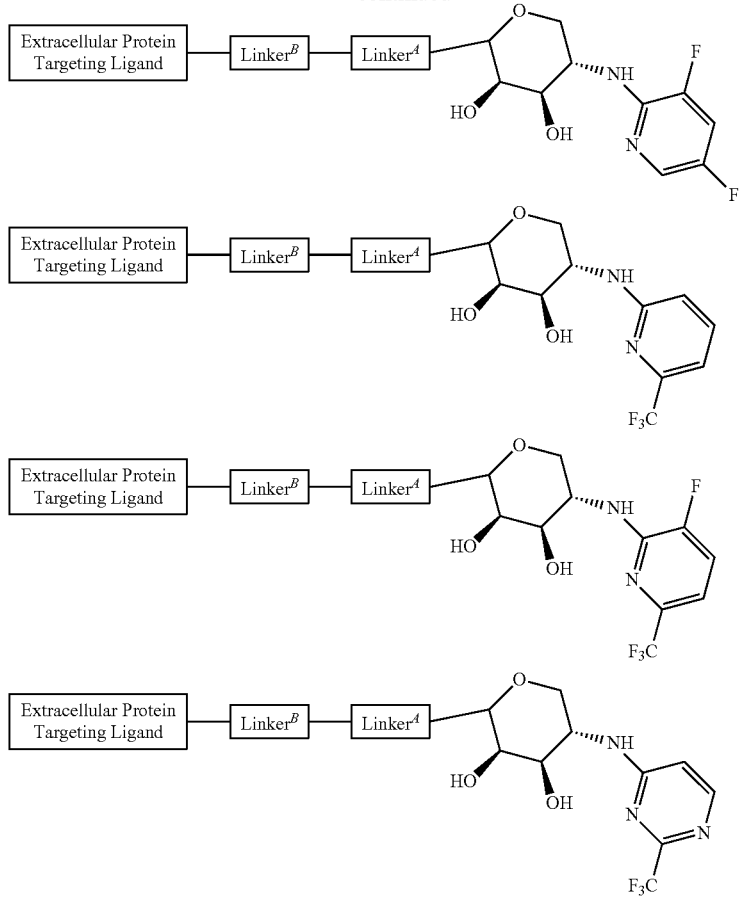
wherein the Extracellular Protein Targeting Ligand is:
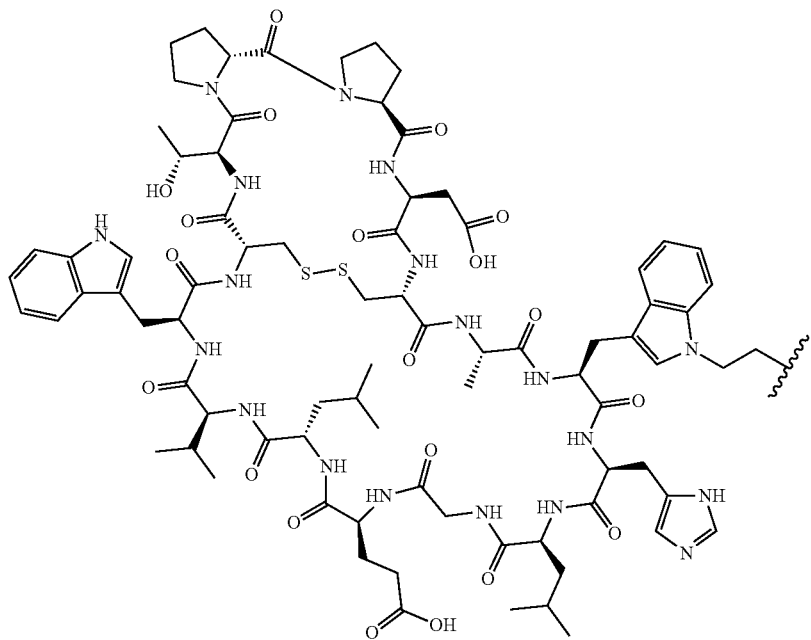 [SMILES: *CCn1cc(C[C@@H]2NC(=O)[C@H](C)NC(=O)[C@@H]3CSSC[C@H](NC(=O)[C@H](Cc4c[nH]c5ccccc45)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc4cnc[nH]4)NC2=O)C(=O)N[C@@H]([C@@H](C)O)C(=O)N2CCC[C@@H]2C(=O)N2CCC[C@H]2C(=O)N[C@@H](CC(=O)O)C(=O)N3)c2ccccc21]
or a pharmaceutically acceptable salt thereof.

In certain embodiments the immunoglobulin degrading compound is selected from the following compounds or a bi- or tri-dentate version thereof;
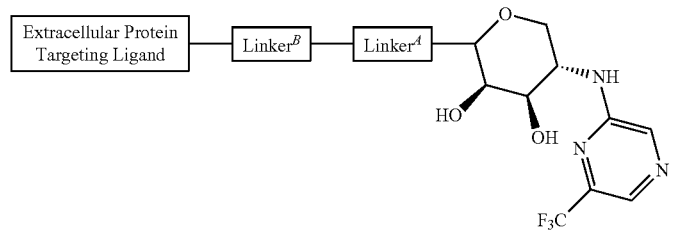
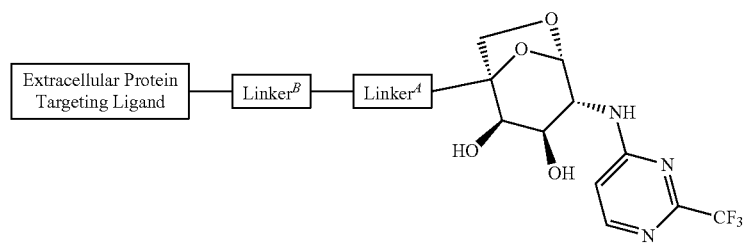
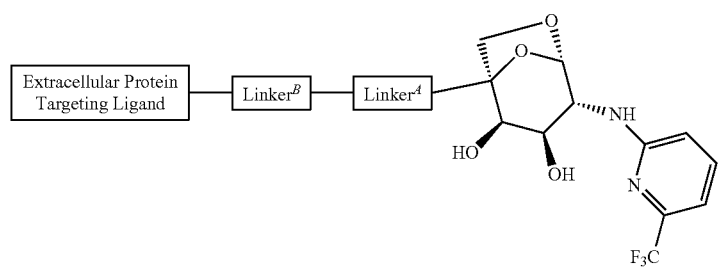
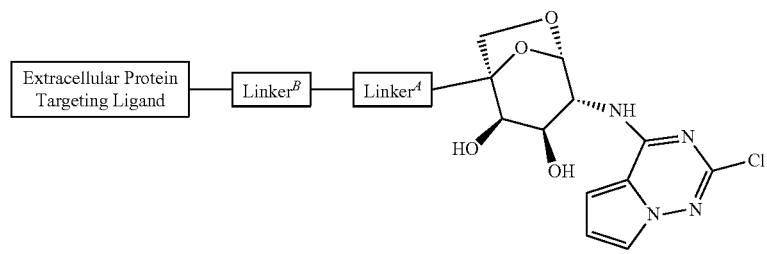
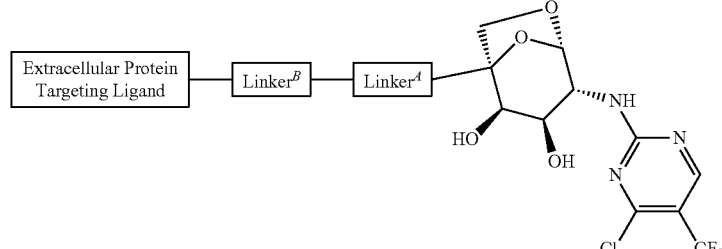
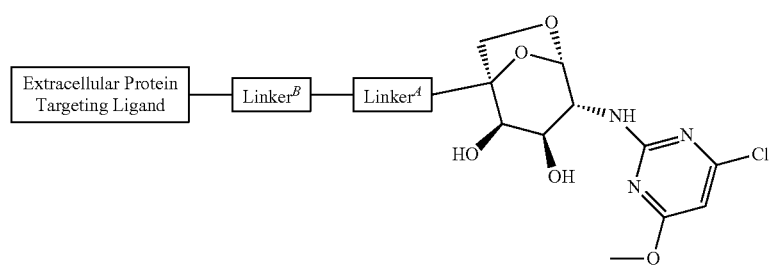

-continued
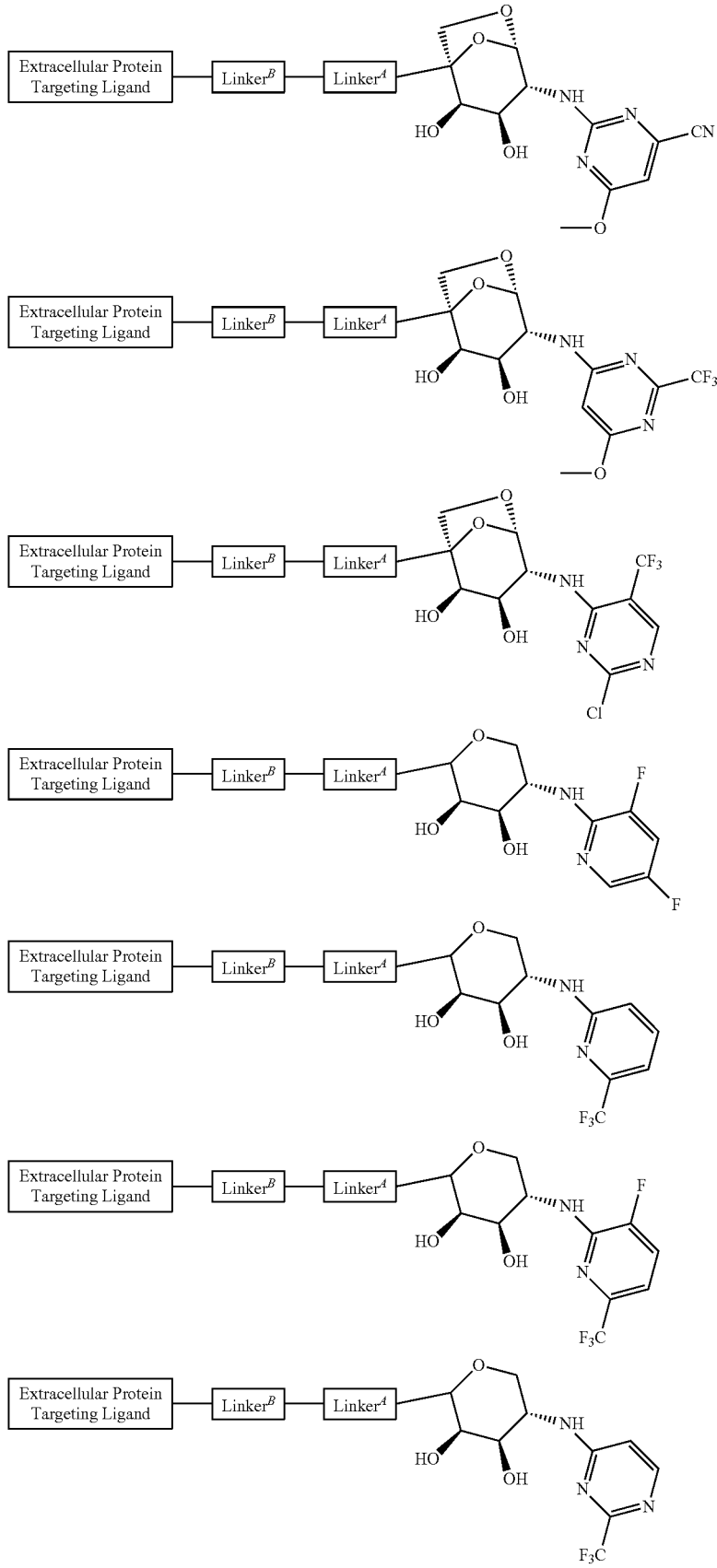

wherein the Extracellular Protein Targeting Ligand is:

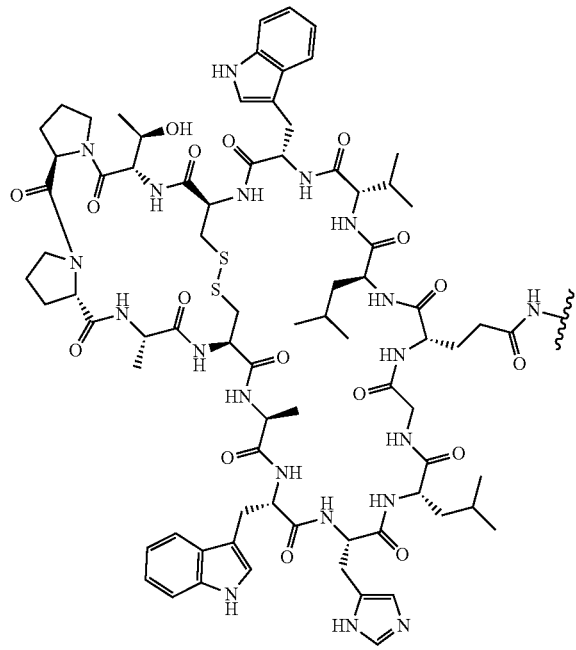 [SMILES: *NC(=O)CC[C@@H]1NC(=O)CNC(=O)[C@H](CC(C)C)NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC1=O)C(=O)N[C@@H]([C@@H](C)O)C(=O)N1CCC[C@@H]1C(=O)N1CCC[C@H]1C(=O)N[C@@H](C)C(=O)N2]

or a pharmaceutically acceptable salt thereof.

The Protein Data Bank website provides the crystal structure of IgG searchable by 1H3X (Krapp, S., et al., J. Mol. Biol., 2003, 325: 979); and 5V43 (Lee, C. H., et al., Nat. Immunol., 2017, 18: 889-898); as well as the crystal structure of IgG bound to various compounds searchable by 5YC5 (Kiyoshi M., et al., Sci. Rep., 2018, 8: 3955-3955); 5XJE (Sakae Y., et al., Sci. Rep., 2017, 7: 13780-13780); 5GSQ (Chen, C. L., et al., ACS Chem. Biol., 2017, 12: 1335-1345); and 1HZH (Saphire E. O., et al., Science, 2001, 293: 1155-1159). Additionally, Kiyoshi, M., et al., provides insight into the structural basis for binding of human IgGI to its high-affinity human receptor FcTRI. (Kiyosi M., et al., Nat Commun., 2015, 6, 6866).

Representative IgG Targeting Ligands are provided in FIG. 1.

Additional representative IgG Targeting Ligands include:

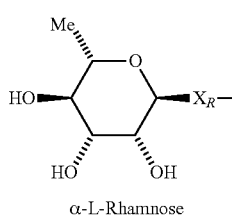 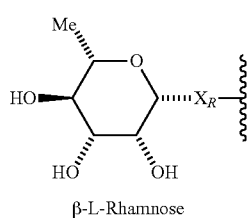

α-L-Rhamnose   β-L-Rhamnose

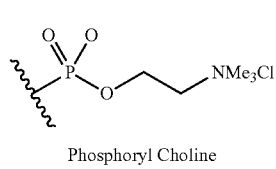 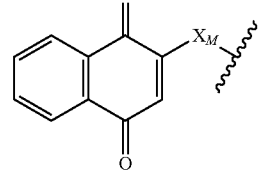

Phosphoryl Choline   Menadione

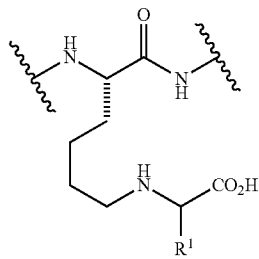

Carboxyethyl Lysine ($R^1$ = Me)

wherein $X_R$ is O, S, NH, or N—$C_1$-$C_3$ alkyl; and $X_M$ is O, S, NH, or N—$C_1$-$C_3$ alkyl.

In other embodiments the IgG Targeting Ligand is selected from:

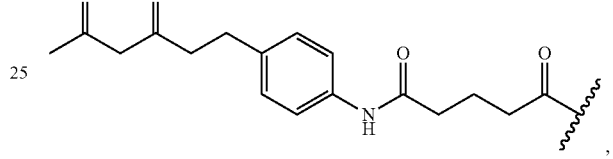

,

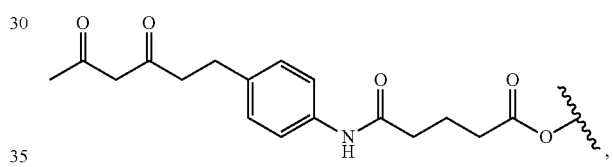

,

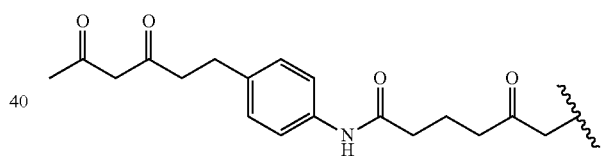

,

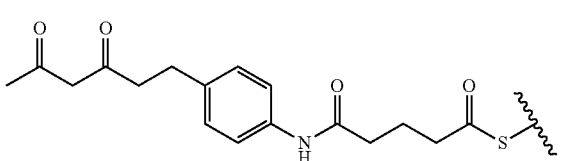

,

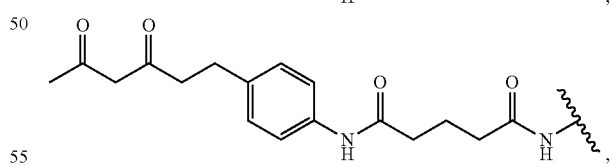

, and

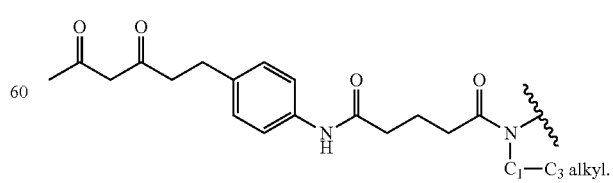

$C_1$—$C_3$ alkyl.

In some embodiments, the IgG Targeting Ligand is a group according to the chemical structure:

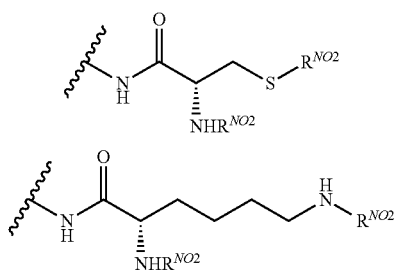

wherein $R^{NO2}$ is a dinitrophenyl group optionally linked through $CH_2$, $S(O)$, $S(O)_2$, —$S(O)_2O$, —$OS(O)_2$, or $OS(O)_2O$.

In certain embodiments the IgG Targeting Ligand is selected from:

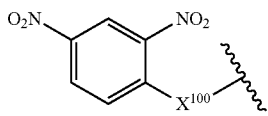

wherein $X^{100}$ is selected from O, $CH_2$, NH, N—$C_1$-$C_3$ alkyl, NC(O)$C_1$-$C_3$ alkyl, S(O), S(O)$_2$, —S(O)$_2$O, —OS(O)$_2$, or OS(O)$_2$O.

In some embodiments, the IgG Targeting Ligand is a 3-indoleacetic acid group according to the chemical structure:

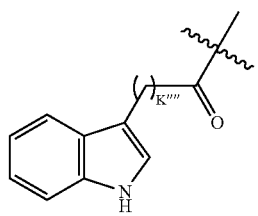

where k"" is 1-4 (preferably 2-3, most often 3) or a

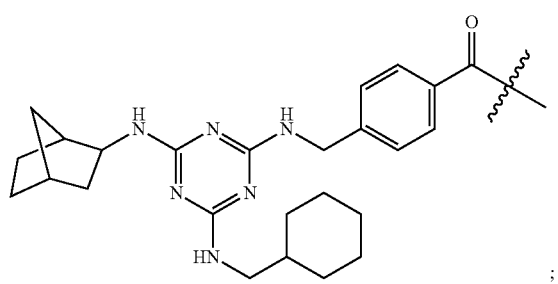 [SMILES: *C(=O)c1ccc(CNc2nc(NCC3CCCCC3)nc(NC3CC4CCC3C4)n2)cc1]

group.

In some embodiments, the IgG Targeting Ligand is a peptide. Nonlimiting examples of IgG Targeting Ligand peptides include:

SEQ ID NO: 35 PAM (RTY)$_4$K$_2$KG (Fassina, et al, J. Mol. Recognit, 1996, 9, 564-569)

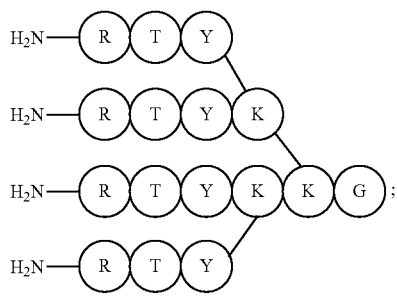

PAM; $K_d$ 0.3 μM

D-PAM, wherein the amino acids of the PAM sequence are all D-amino acids (Verdoliva, et al, J. Immunol. Methods, 2002, 271, 77-88) SEQ ID NO:36 (RTY)$_4$K$_2$KG D-PAM-Φ, wherein the amino acids of the PAM sequence are all D-amino acids with further modifications wherein the four N-terminal arginines are acetylated with phenylacetic acid (Dinon, et al J. Mol. Recognit. 2011, 24, 1087-1094) SEQ ID NO:37 (RTY)$_4$K$_2$KG SEQ ID NO:38 TWKTSRISIF (Krook, et al, J. Immunol. Methods 1998, 221, 151-157)

SEQ ID NO:39 FGRLVSSIRY (Krook, et al, J. Immunol. Methods 1998, 221, 151-157)

SEQ ID NO:40 Fc-III (DCAWHLGEL VWCT-NH2) (DeLano et al, Science 2000, 287, 1279-1283)

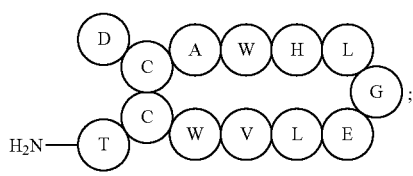

Fc-III; $K_d$ 16 nM

```
                                       SEQ ID NO: 41
FCBP-Ser DSAWHLGELWST (see WO2014010813)

SEQ ID NO: 42
DCHKRSFWADNCT (see WO2014010813)

SEQ ID NO: 43
DCRTQFRPNQTCT (see WO2014010813)

SEQ ID NO: 44
DCQLCDFWRTRCT (see WO2014010813)

SEQ ID NO: 45
DCFEDFNEQRTCT (see WO2014010813)

SEQ ID NO: 46
DCLAKFLKGKDCT (see WO2014010813)

SEQ ID NO: 47
DCWHRRTHKTFCT (see WO2014010813)

SEQ ID NO: 48
DCRTIQTRSCT (see WO2014010813)

SEQ ID NO: 49
DCIKLAQLHSVCT (see WO2014010813)

SEQ ID NO: 50
DCWRHRNATEWCT (see WO2014010813)
```

SEQ ID NO: 51
DCQNWIKDVHKCT (see WO2014010813)

SEQ ID NO: 52
DCAWHLGELVWCT (see WO2014010813)

SEQ ID NO: 53
DCAFHLGELVWCT (see WO2014010813)

SEQ ID NO: 54
DCAYHLGELVWCT (see WO2014010813)

SEQ ID NO:55 FcBP-1 PAWHLGEL VWP (Kang, et al, J. Chromatogr. A 2016, 1466, 105-112)

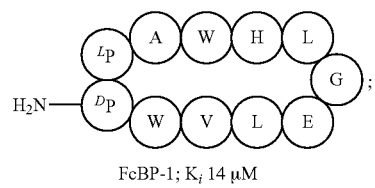

FcBP-1; $K_i$ 14 μM

SEQ ID NO:56 FcBP-2 PDCAWHLGEL VWCTP (Dias, et al, J. Am. Chem. Soc. 2006, 128, 2726-2732)

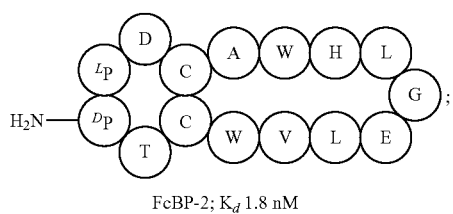

FcBP-2; $K_d$ 1.8 nM

SEQ ID NO:57 Fc-III-4c CDCA WHLGEL VWCTC (Gong, et al, Bioconjug. Chem. 2016, 27, 1569-1573)

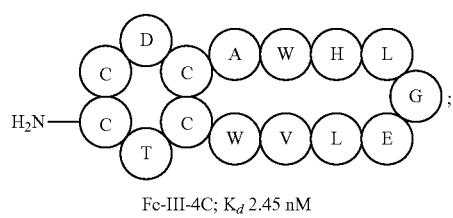

Fc-III-4C; $K_d$ 2.45 nM

SEQ ID NO: 58 EPIHRSTLTALL (Ehrlich, et al, J. Biochem. Biophys. Method 2001, 49, 443-454)

SEQ ID NO: 59 APAR (Camperi, et al, Biotechnol. Lett. 2003, 25, 1545-1548)

SEQ ID NO:60 FcRM (CFHH)$_2$KG (Fc Receptor Mimetic, Verdoliva, et al., ChemBioChem 2005, 6, 1242-1253)

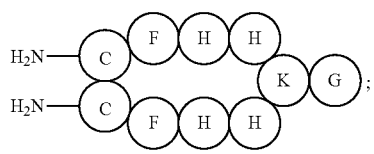

FcRM; $K_d$ 20 μM

SEQ ID NO: 61 HWRGWV (Yang, et al., J Peptide Res. 2006, 66, 110-137)

SEQ ID NO: 62 HYFKFD (Yang, et al, J. Chromatogr. A 2009, 1216, 910-918)

SEQ ID NO: 63 HFRRHL (Menegatti, et al, J. Chromatogr. A 2016, 1445, 93-104)

SEQ ID NO: 64 HWCitGWV (Menegatti, et al, J. Chromatogr. A 2016, 1445, 93-104)

SEQ ID NO:65 HWmetCitGWmetV (US10,266,566)

SEQ ID NO:66 D$_2$AAG (Small Synthetic peptide ligand, Lund, et al, J. Chromatogr. A 2012, 1225, 158-167)

SEQ ID NO:67 DAAG (Small Synthetic peptide ligand, Lund, et al, J. Chromatogr. A 2012, 1225, 158-167);

SEQ ID NO: 68 cyclo[(Nα-Ac) S(A)-RWHYFK-Lact-E] (Menegatti, et al, Anal. Chem. 2013, 85, 9229-9237);

SEQ ID NO: 69 cyclo[(Nα-Ac)-Dap(A)-RWHYFK-Lact-E] (Menegatti, et al, Anal. Chem. 2013, 85, 9229-9237);

SEQ ID NO: 70 cyclo[Link M-WFRHYK] (Menegatti, et al, Biotechnol. Bioeng, 2013, 110, 857-870);

SEQ ID NO: 71 NKFRGKYK (Sugita, et al, Biochem. Eng. J. 2013, 79, 33-40);

SEQ ID NO: 72 NARKFYKG (Sugita, et al, Biochem. Eng. J. 2013, 79, 33-40);

SEQ ID NO: 73 FYWHCLDE (Zhao, et al, Biochem. Eng. J. 2014, 88, 1-11);

SEQ ID NO: 74 FYCHWALE (Zhao, et al, J Chromatogr. A 2014, 1355, 107-114);

SEQ ID NO: 75 FYCHTIDE (Zhao, et al., Z Chromatogr. A 2014, 1359, 100-111); Dual 1/3 (FYWHCLDE-FYCHTIDE) (Zhao, et al, J. Chromatogr. A 2014, SEQ ID NO:76 Dual ⅓(FYWHCLDE-FYCHTIDE) (Zhao, et al, J. Chromatogr, A 2014, 1369, 64-72);

SEQ ID NO: 77 RRGW (Tsai, et al, Anal. Chem. 2014, 86, 2931-2938);

SEQ ID NO: 78 KHRFNKD (Yoo and Choi, BioChip J. 2015, 10, 88-94);

SEQ. ID NO: 79 CPSTHWK (Sun et al. Polymers 2018, 10, 778);

SEQ. ID NO: 80 NVQYFAV (Sun et al. Polymers 2018, 10, 778);

SEQ. ID NO: 81 ASHTQKS (Sun et al. Polymers 2018, 10, 778);

SEQ. ID NO: 82 QPQMSHM (Sun et al. Polymers 2018, 10, 778);

SEQ. ID NO: 83 TNIESLK (Sun et al. Polymers 2018, 10, 778);

SEQ. ID NO: 84 NCHKCWN (Sun et al. Polymers 2018, 10, 778);

SEQ. ID NO: 85 SHLSKNF (Sun et al. Polymers 2018, 10, 778).

In some embodiments the IgG Targeting Ligand is specific for IgG4.

In some embodiments the IgG4 specific Targeting Ligand is described in Gunnarsson et al. Biomolecular Engineering 2006, 23, 111-117.

In some embodiments the IgG4 specific targeting ligand is selected from
```
                                          SEQ ID NO: 86
FDLLEHFY
and
                                          SEQ ID NO: 87
DLLHHFDYF.
```
Additional IgG Targeting Ligands include
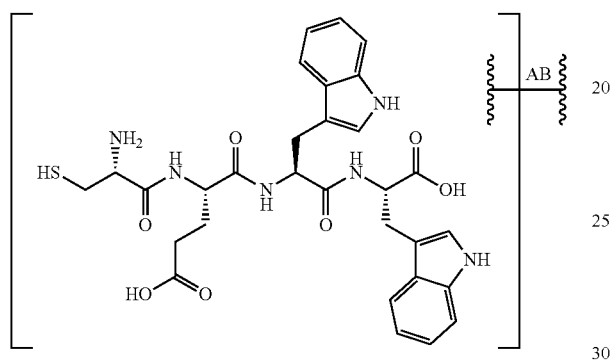
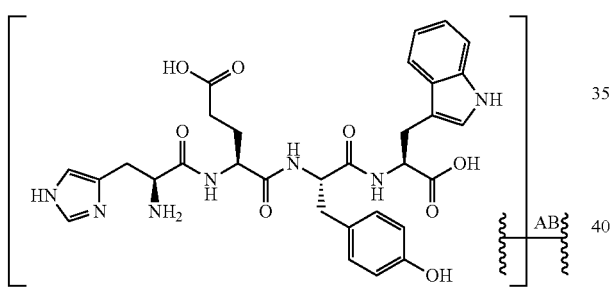
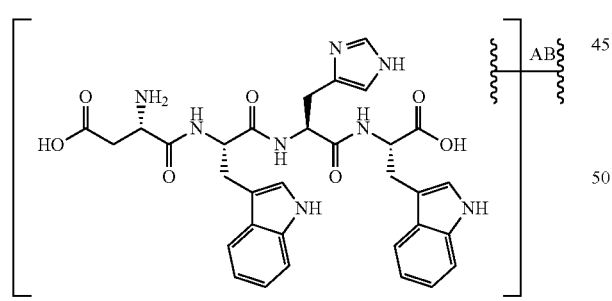
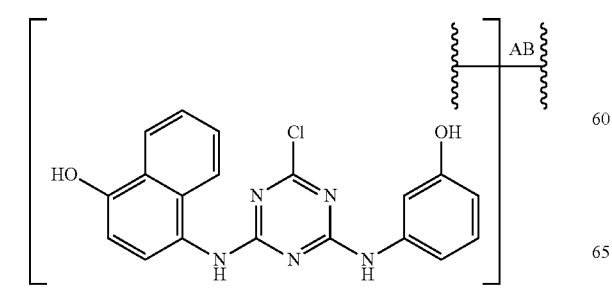
-continued
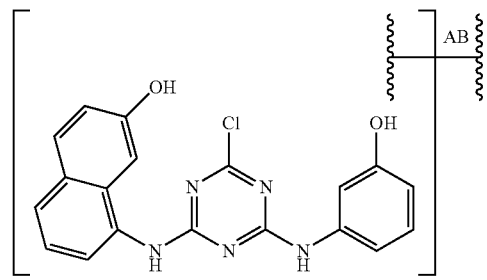
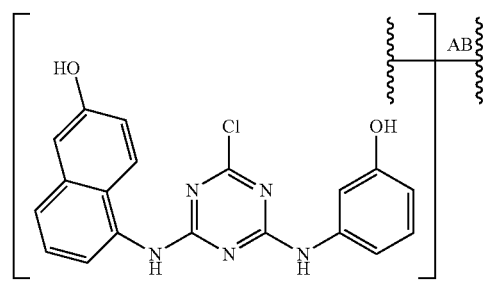
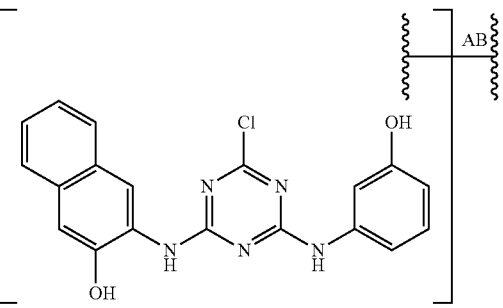

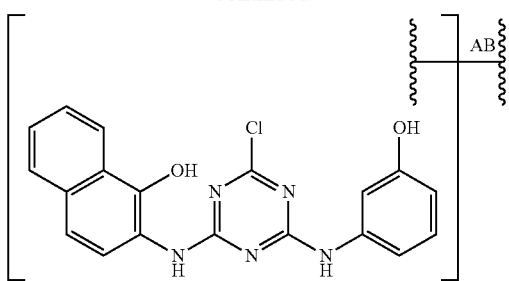
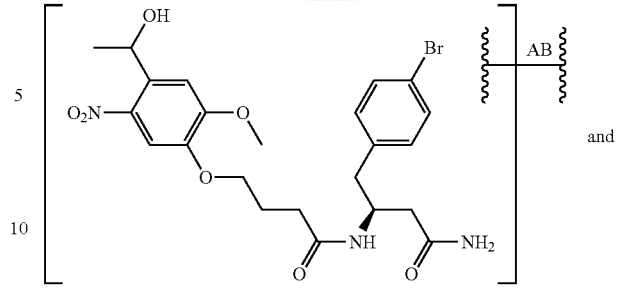
and
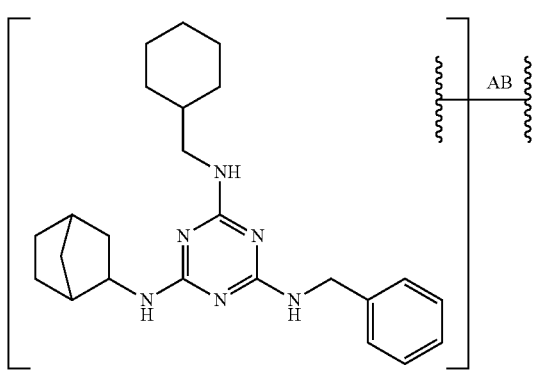
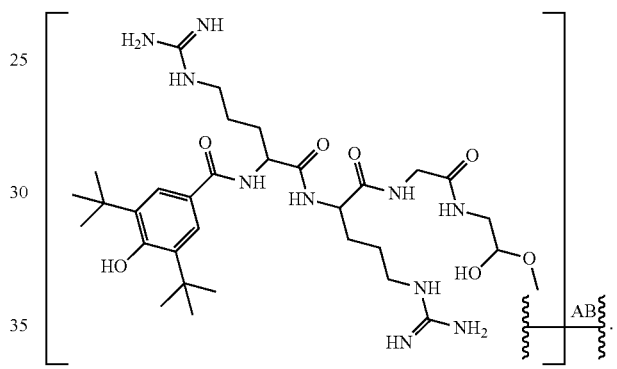
Non-limiting examples of IgG degrading compounds include:
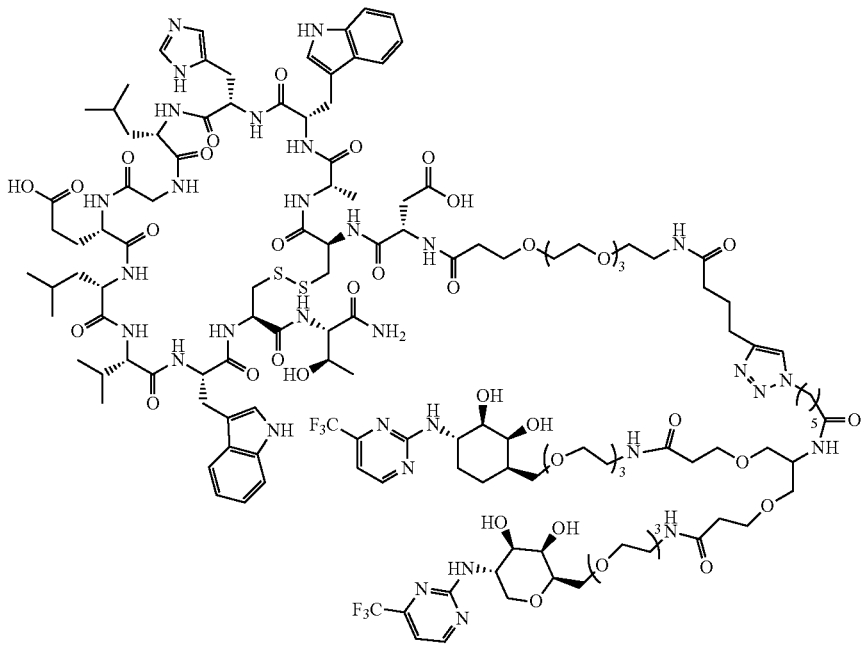

-continued
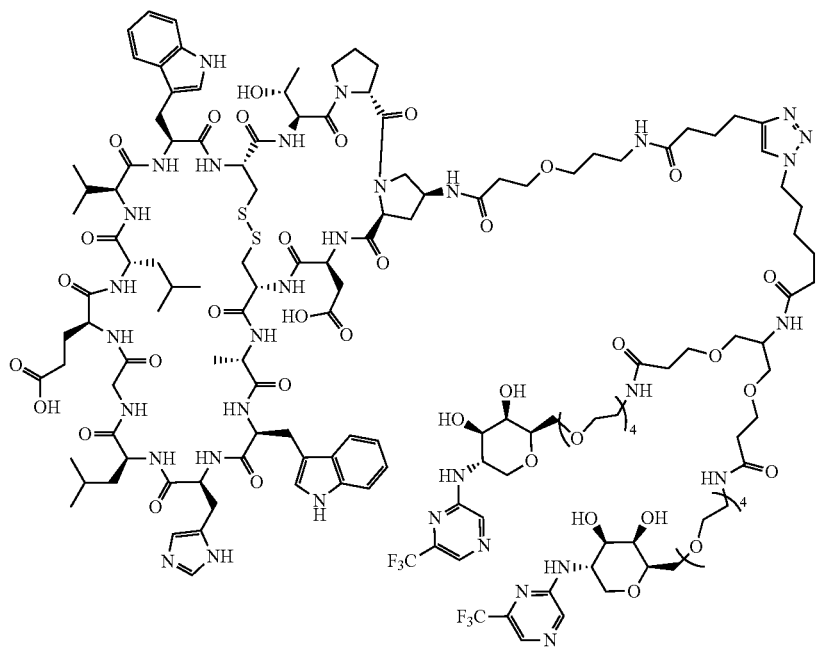
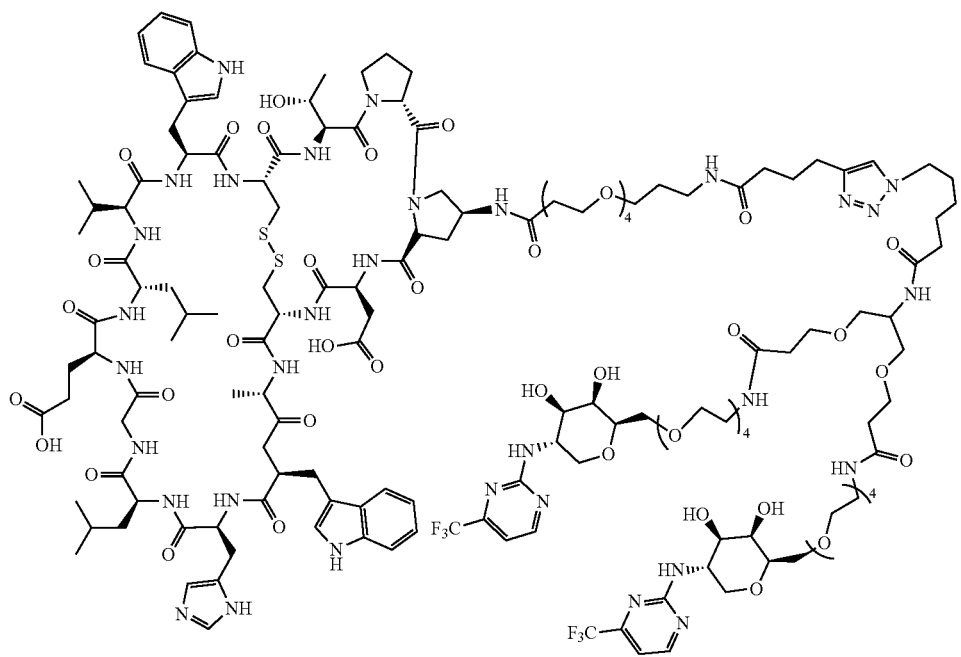

-continued
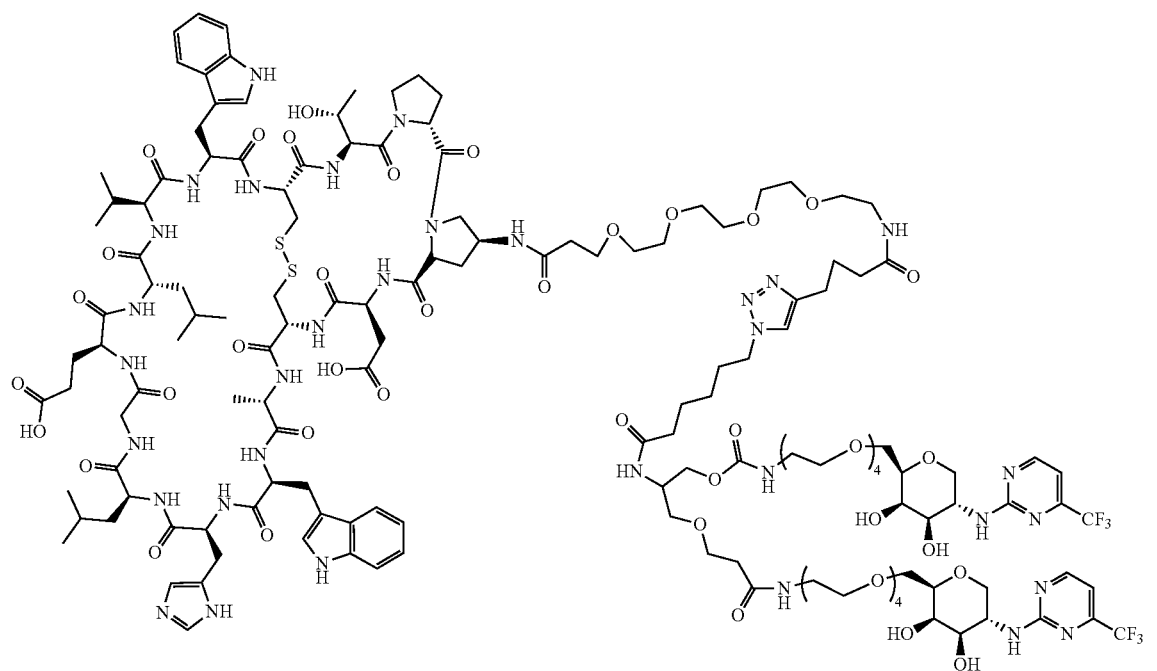
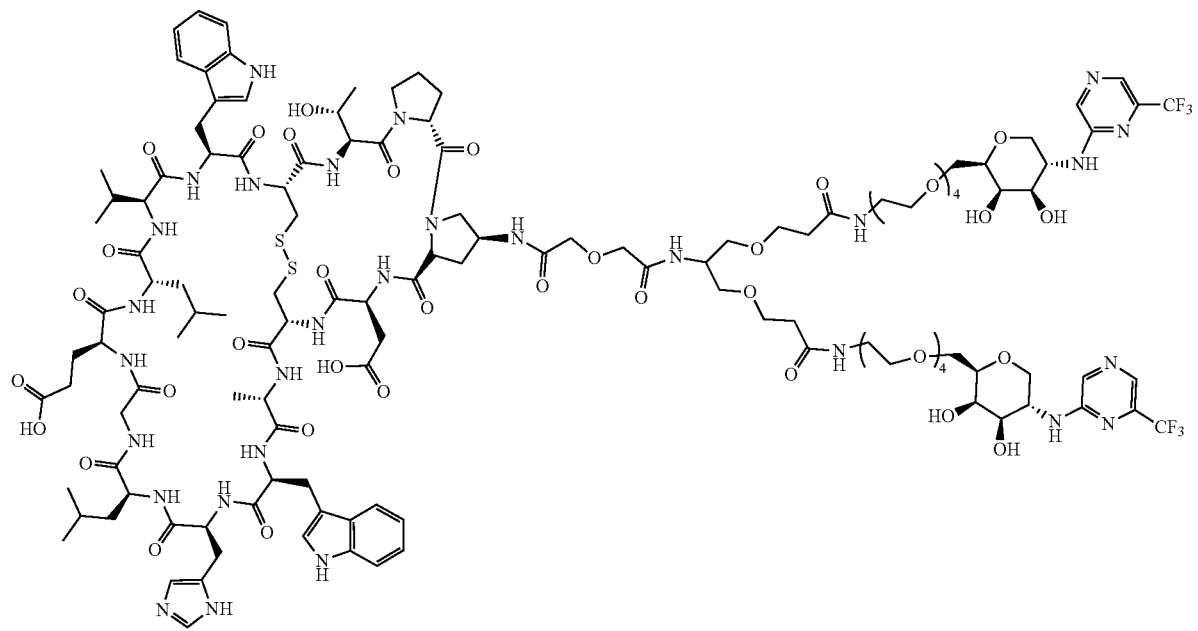

349
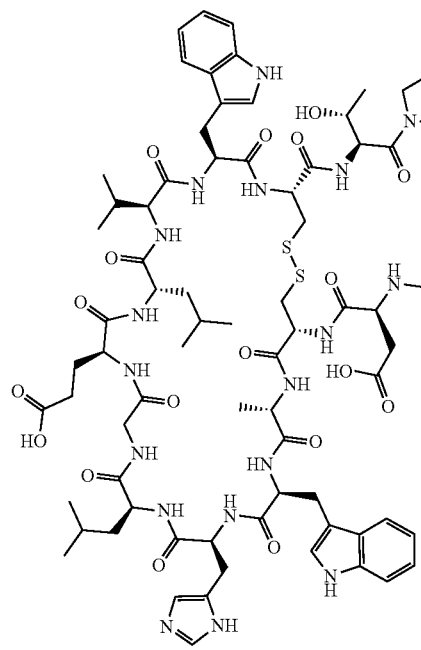
-continued
350
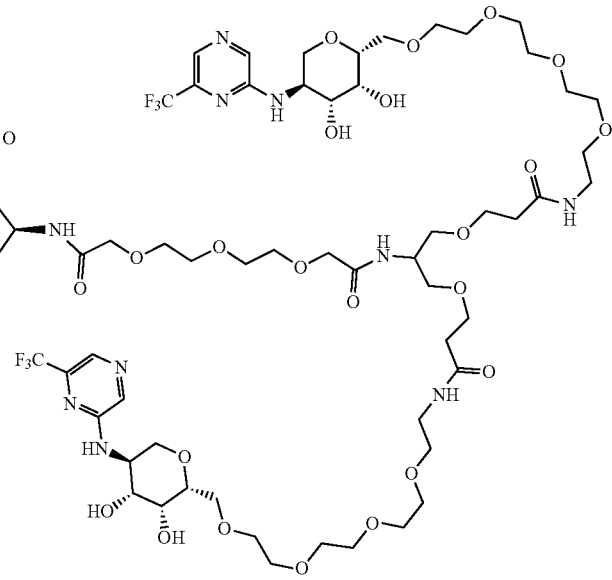
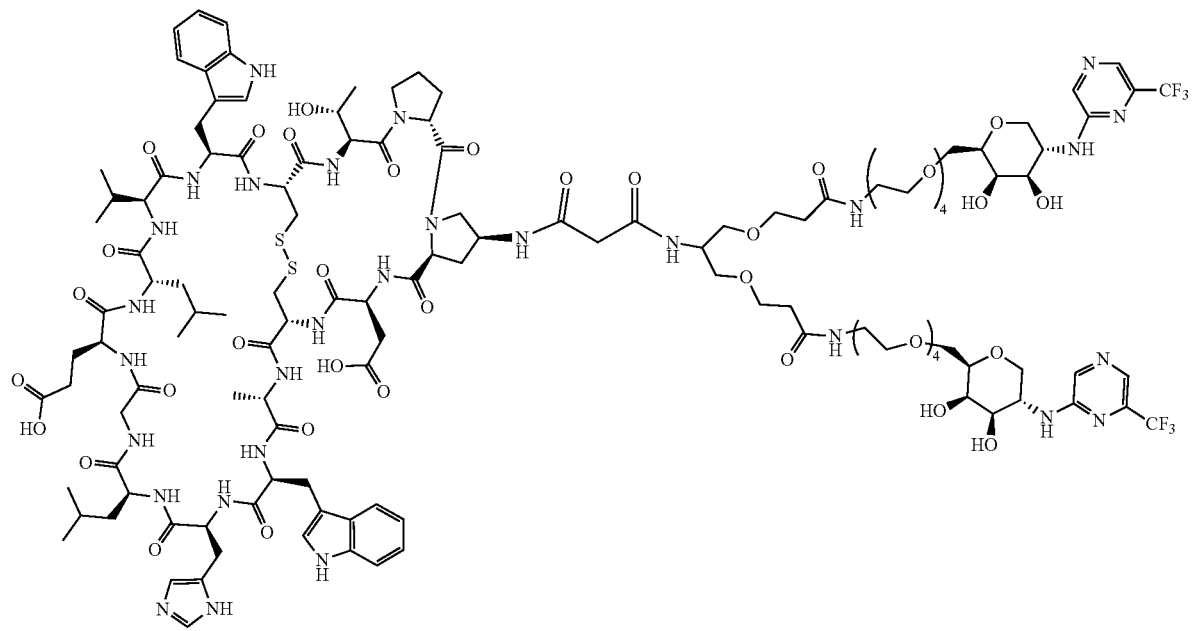

-continued
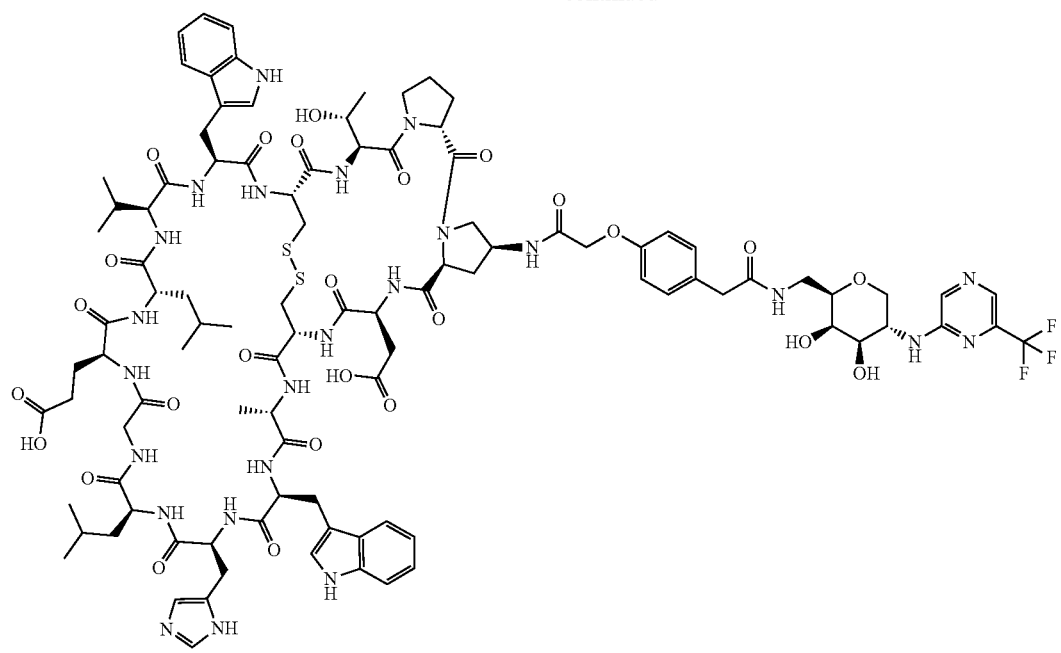
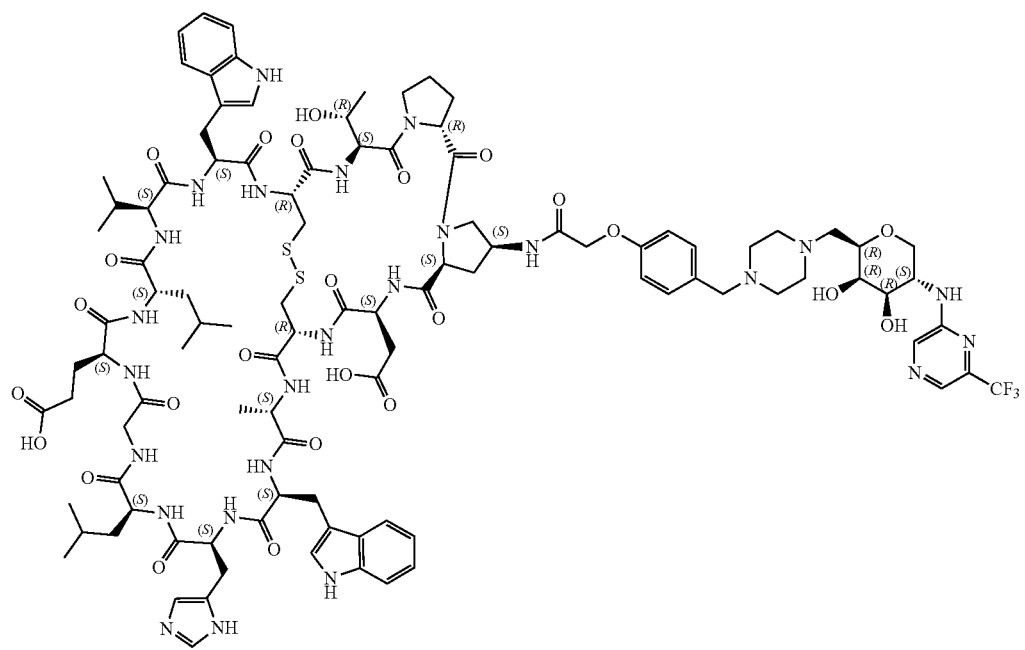

-continued
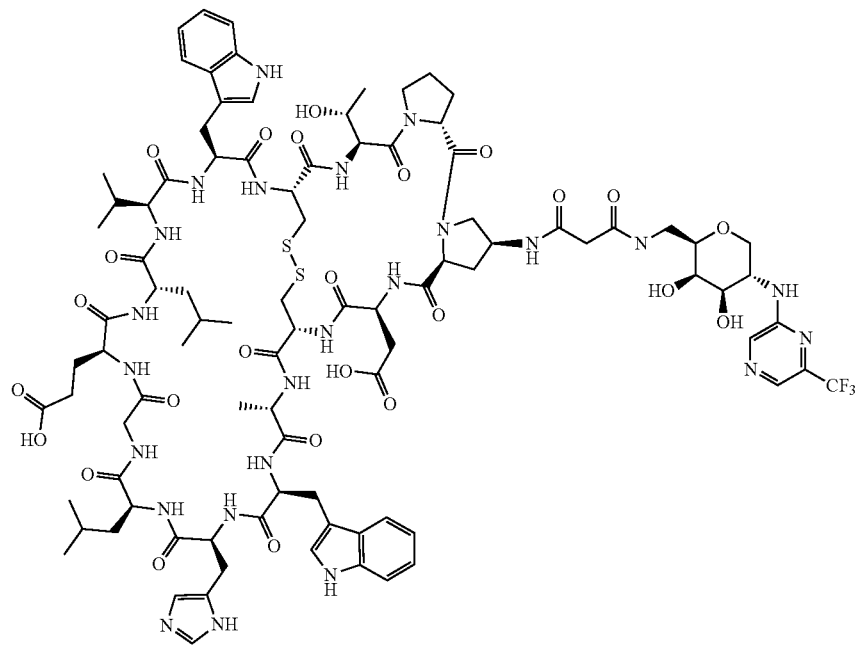
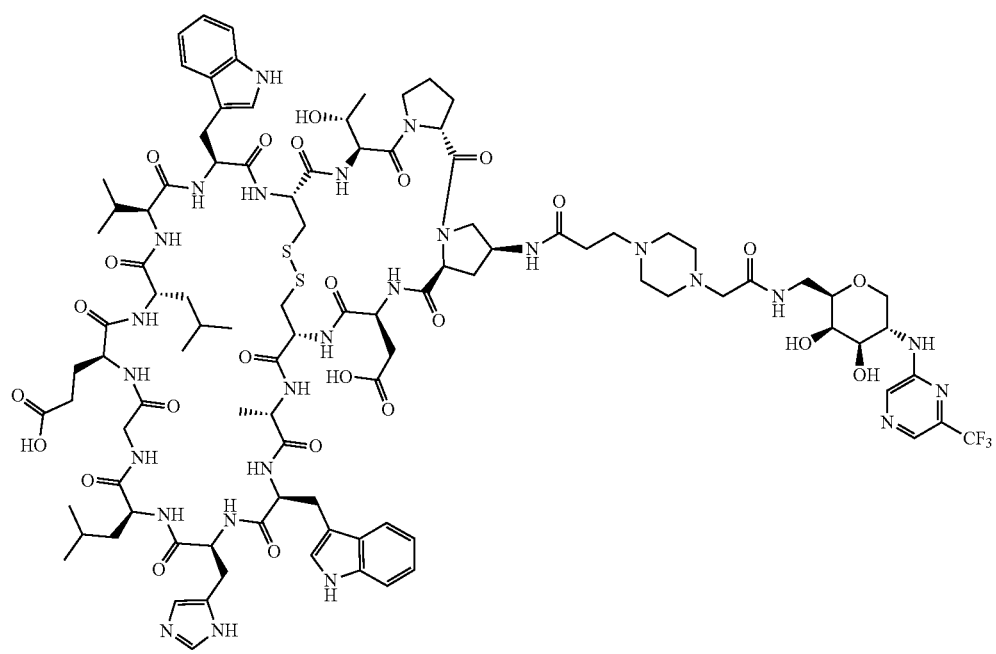

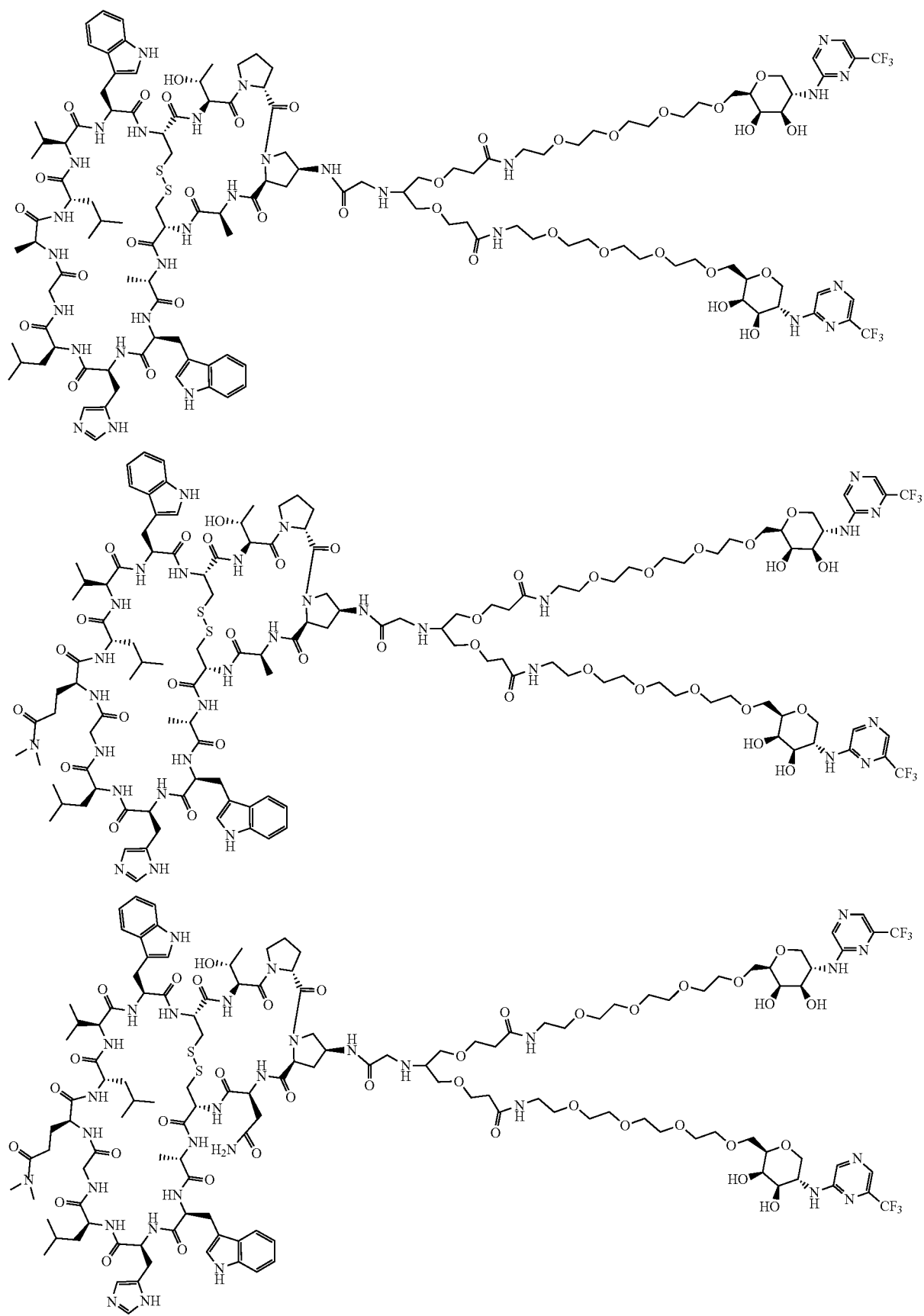

357
358
-continued
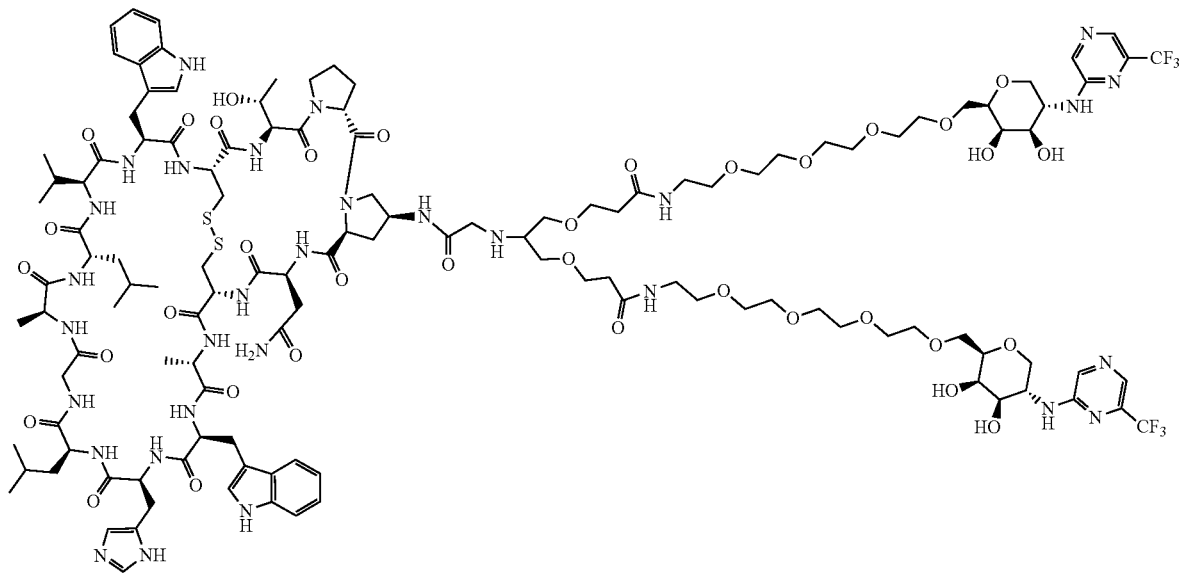
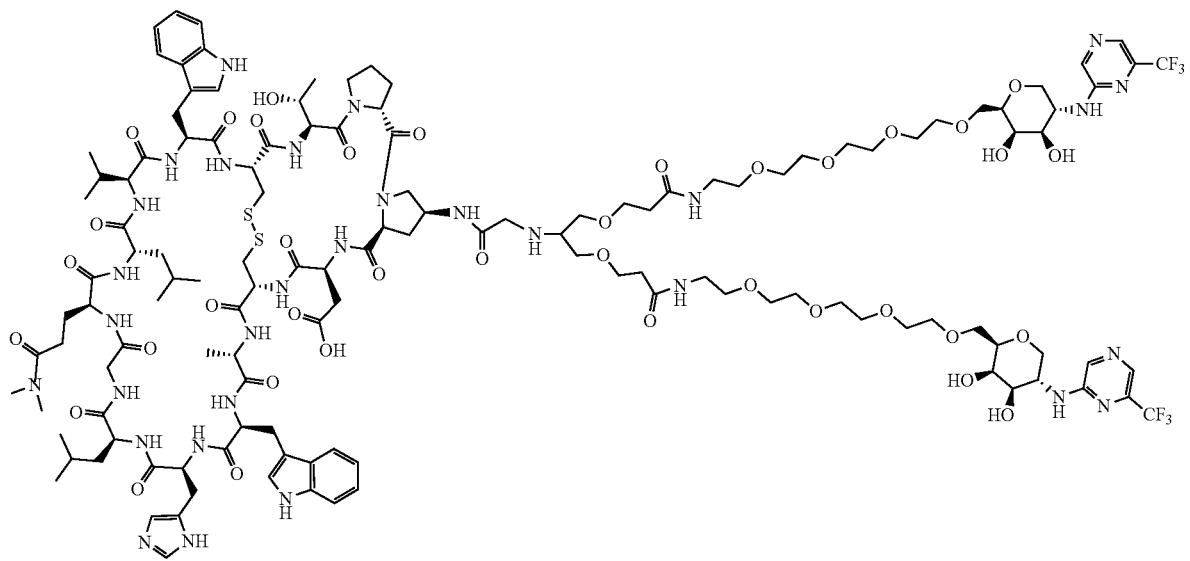

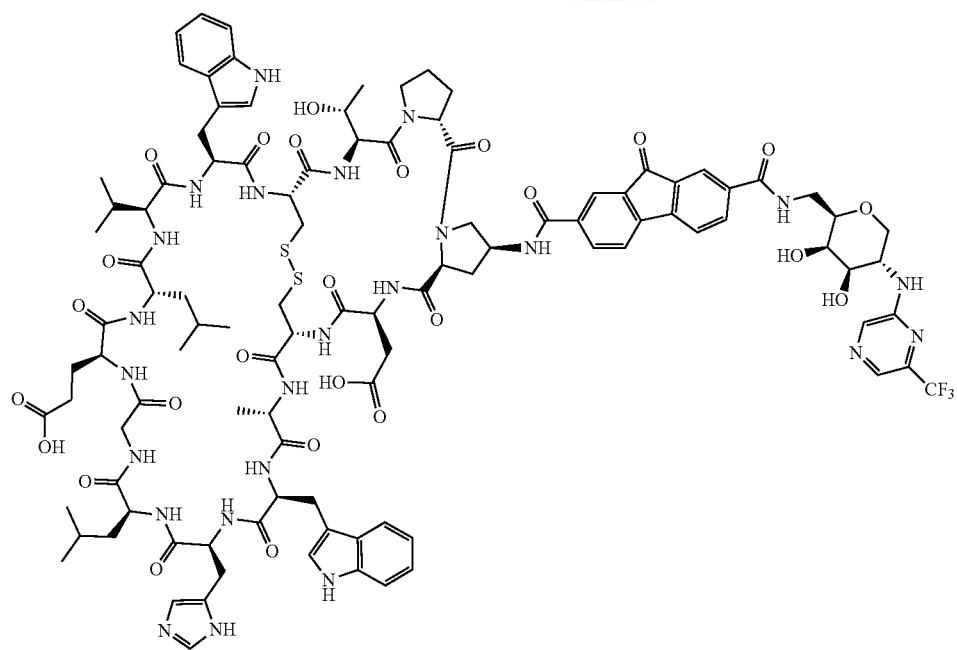
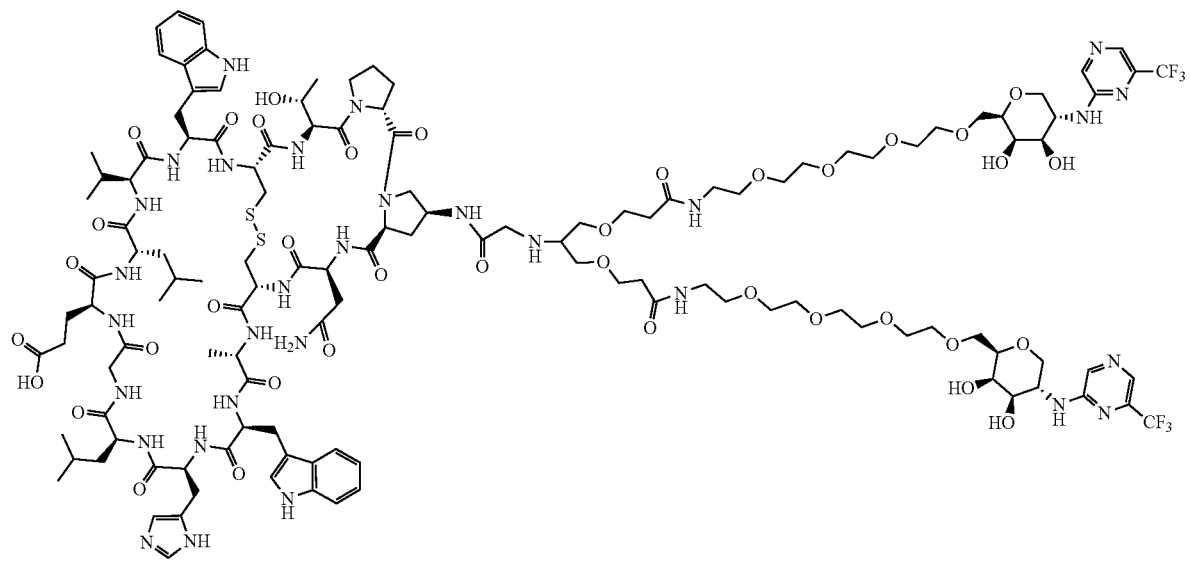

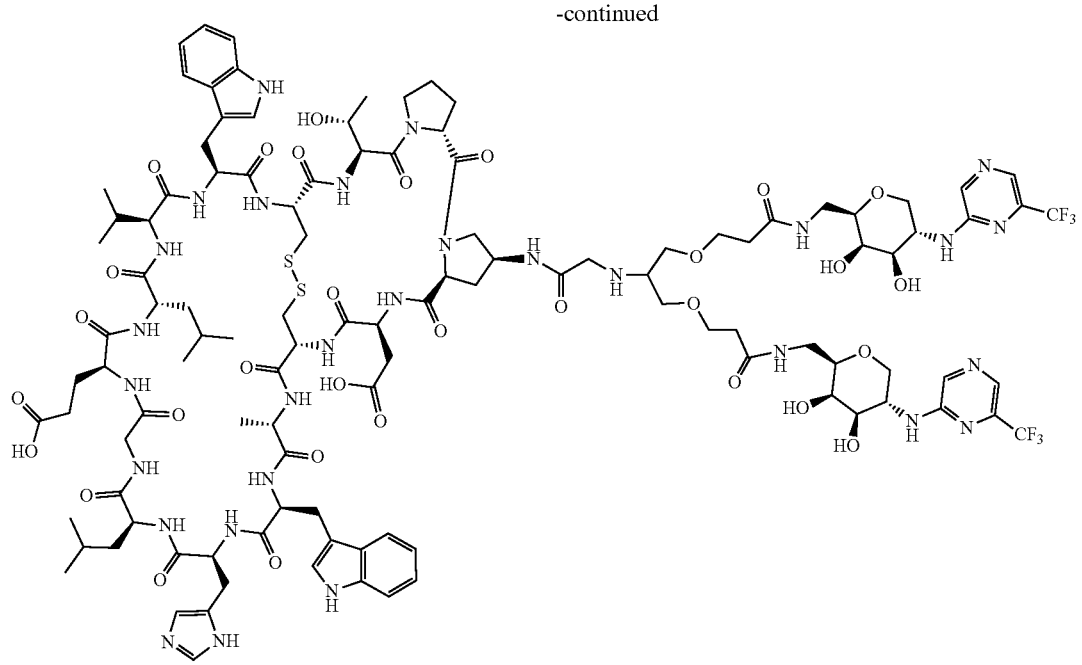
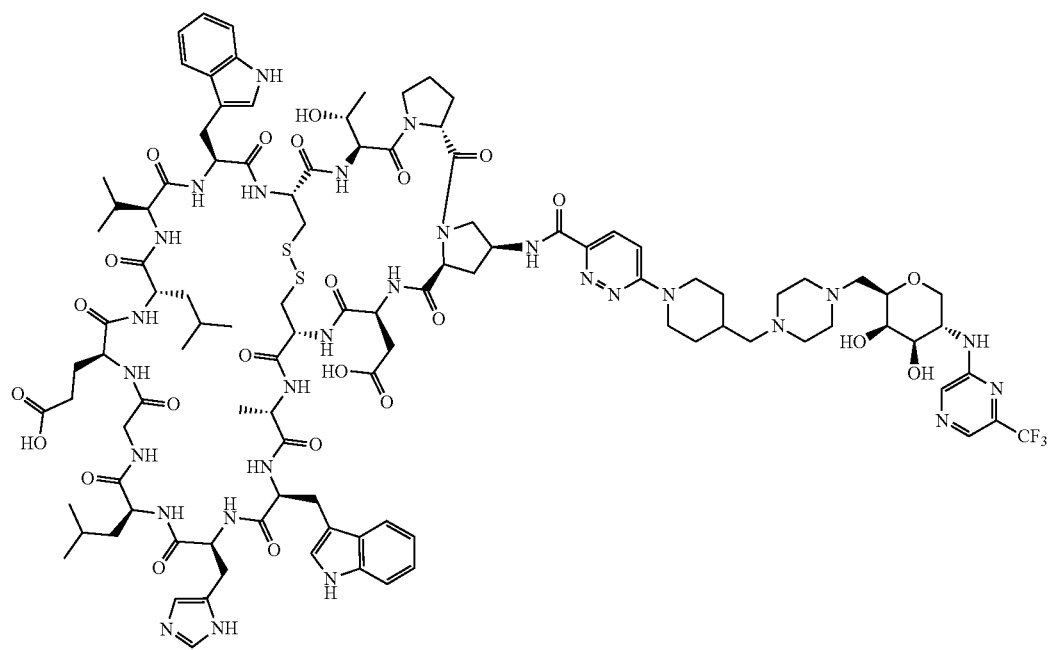

-continued
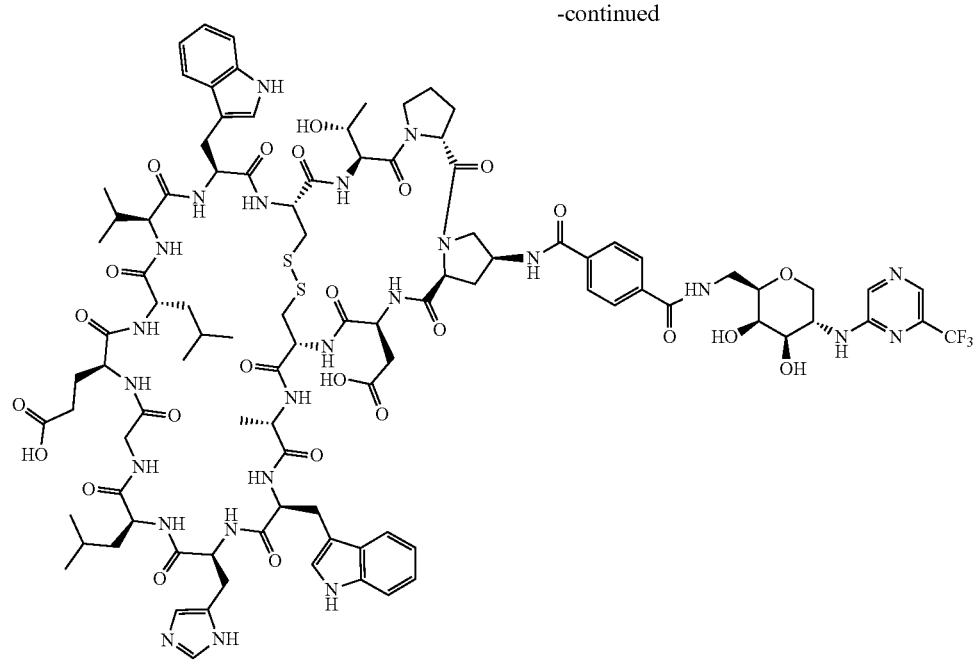
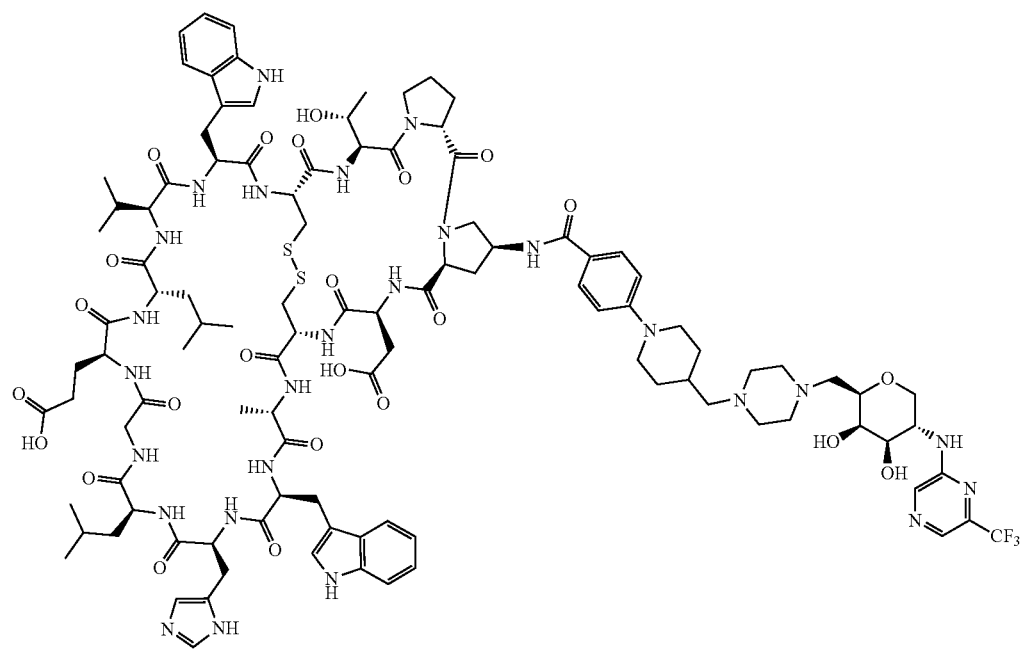

-continued
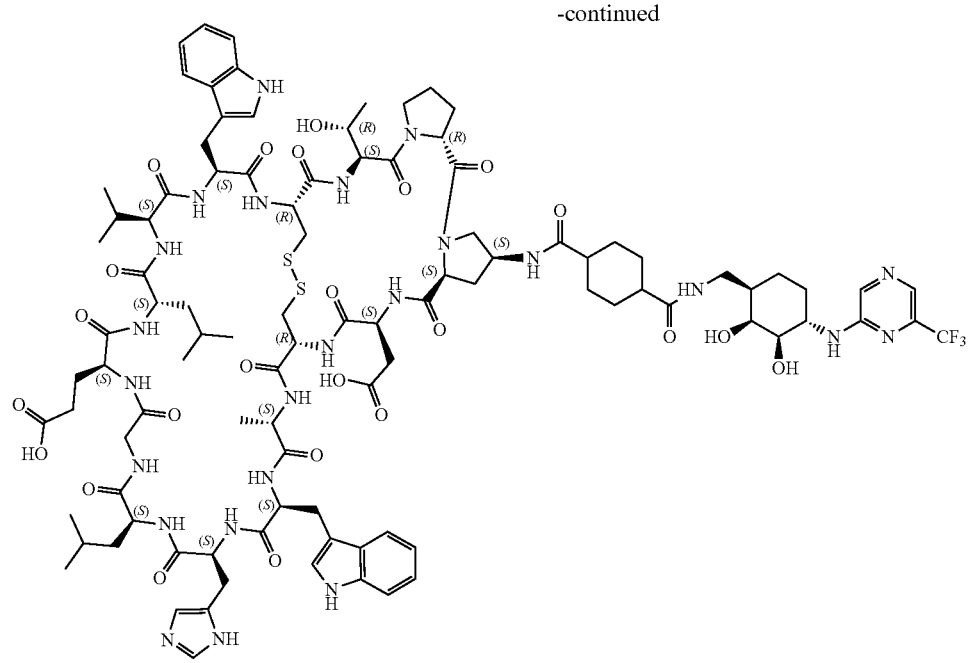
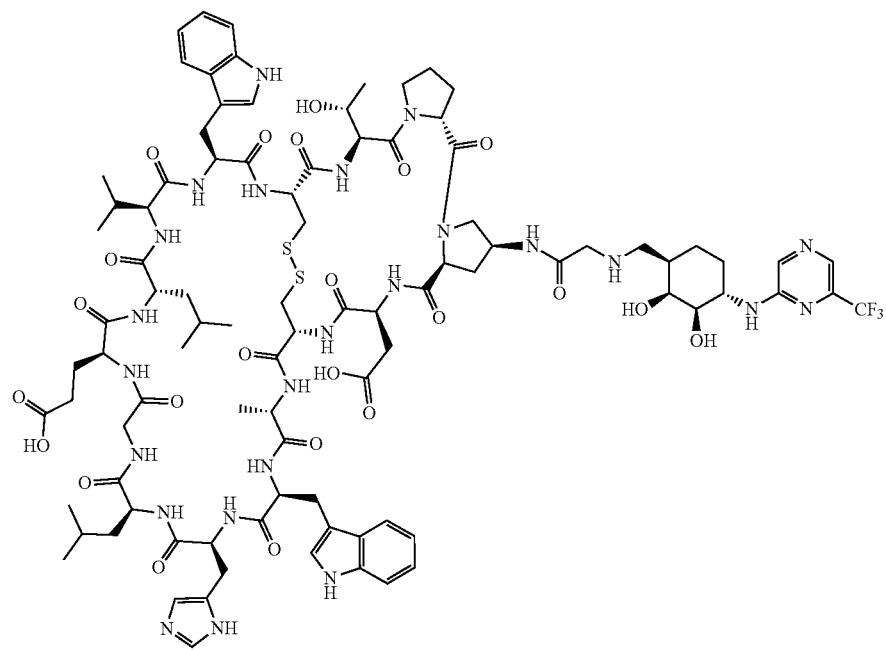

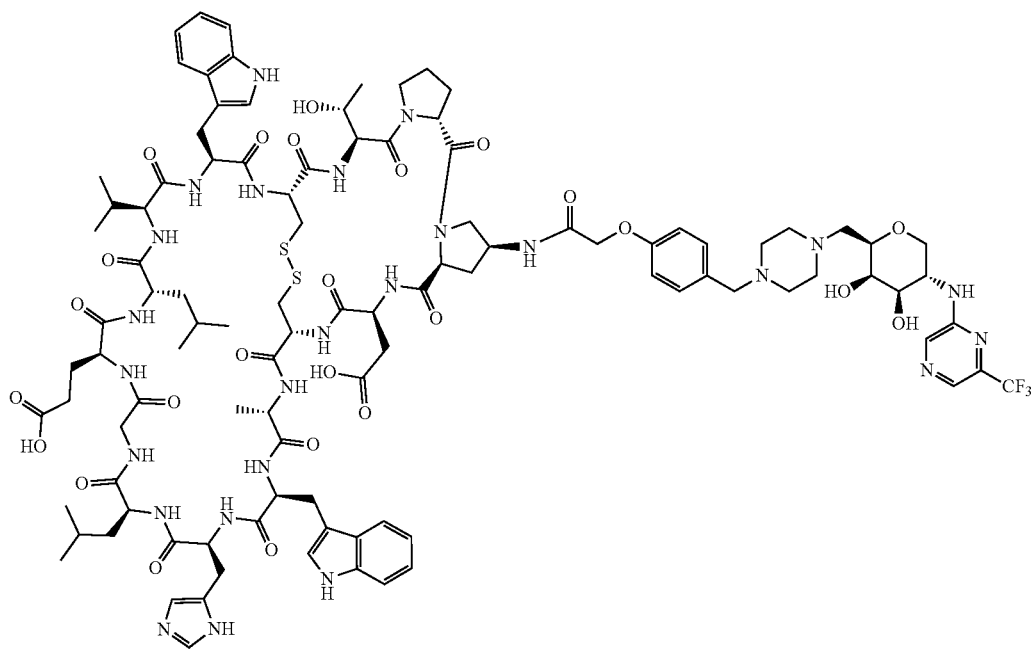
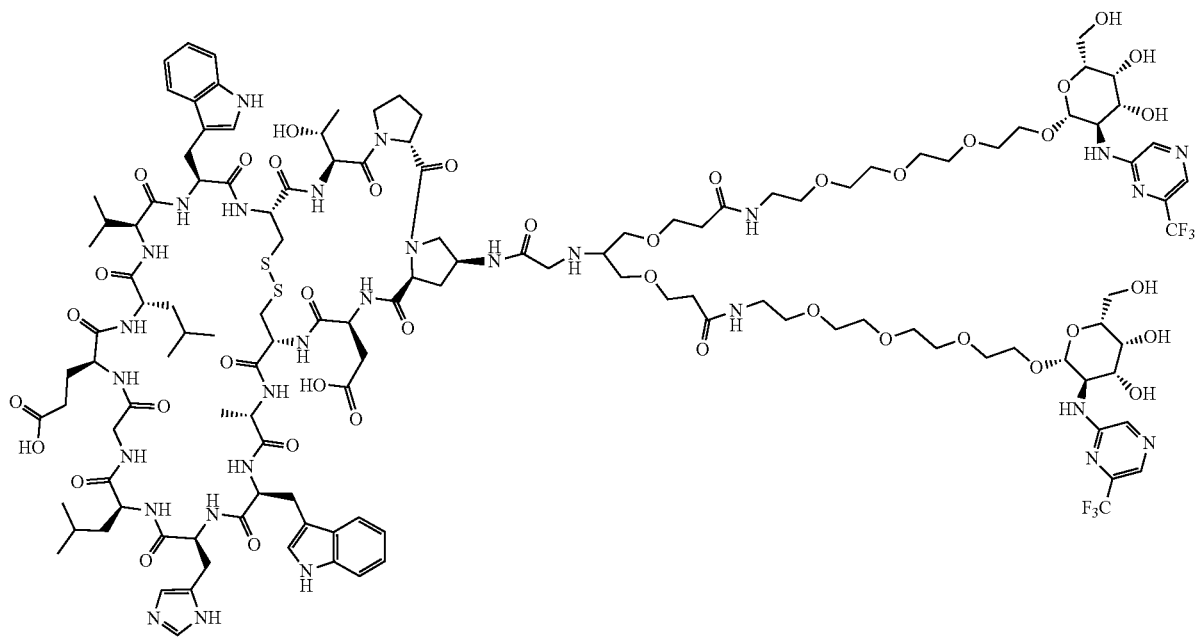

369
370
-continued
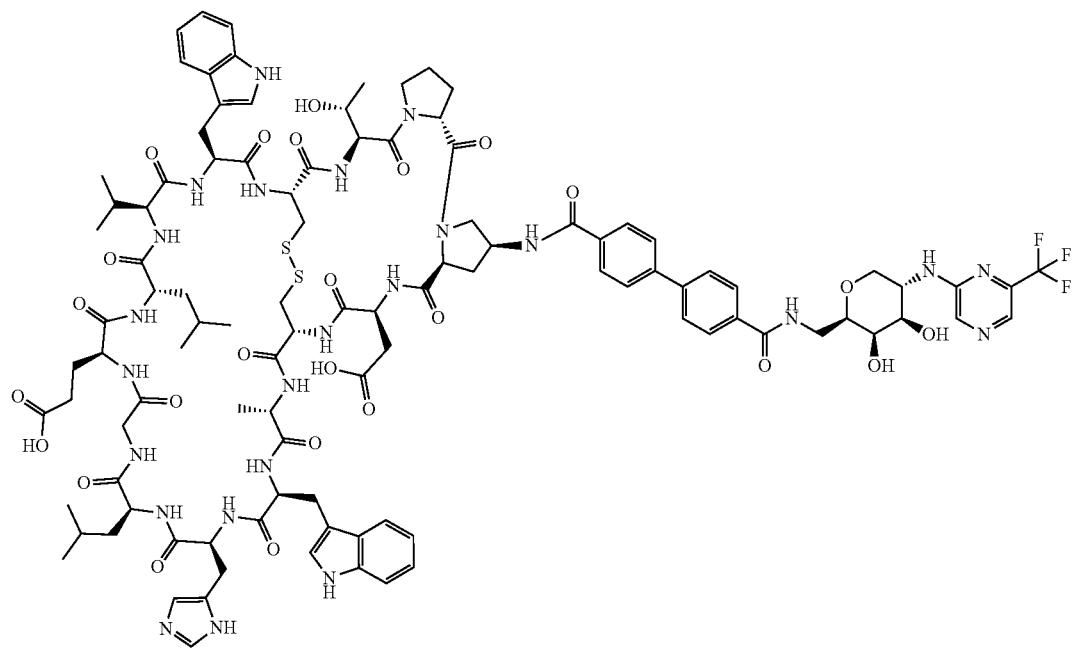
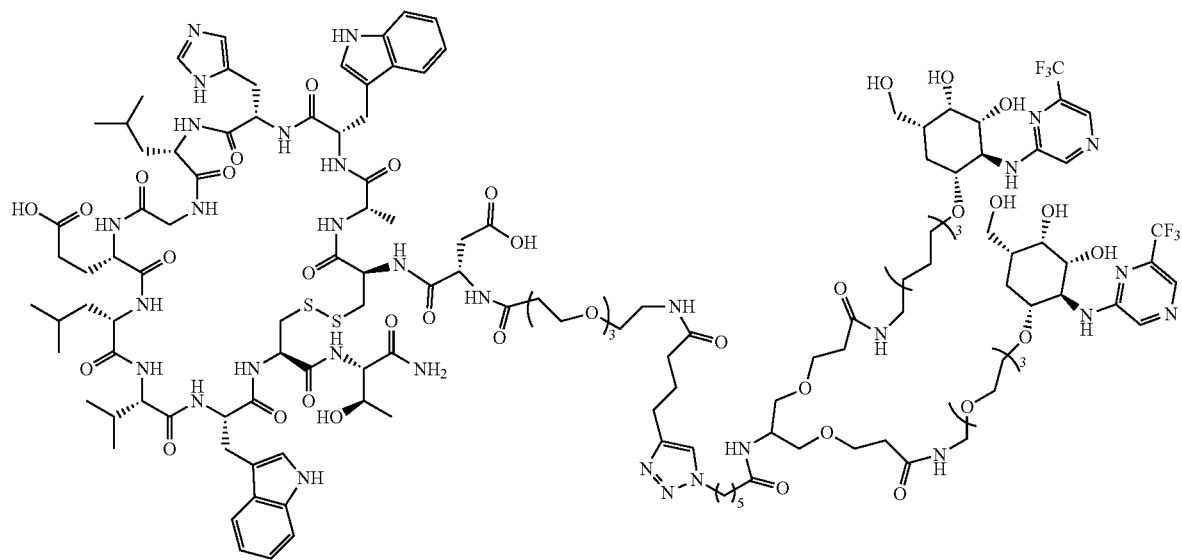

In alternative embodiments a hydroxyl, amine, amide, or carboxylic acid group in an Extracellular Protein Targeting Ligand drawn herein is capped with a protecting group. For example in this embodiment:

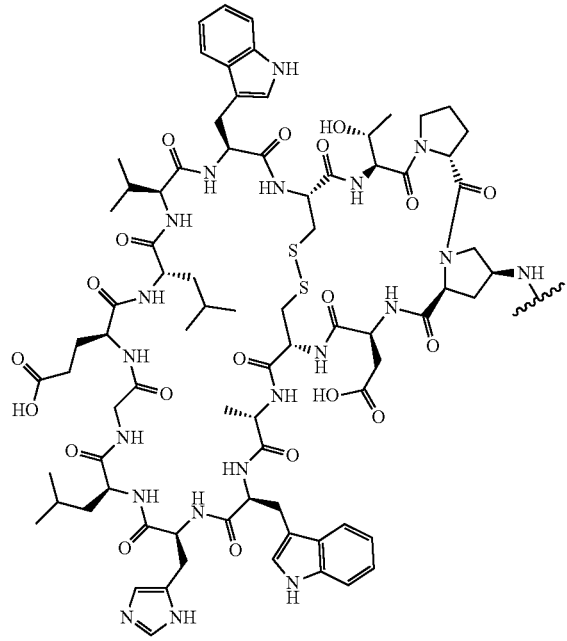 [SMILES: *N[C@H]1C[C@H]2C(=O)N[C@@H](CC(=O)O)C(=O)N[C@H]3CSSC[C@H](NC(=O)[C@H](Cc4c[nH]c5ccccc45)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc4cnc[nH]4)NC(=O)[C@H](Cc4c[nH]c5ccccc45)NC(=O)[C@H](C)NC3=O)C(=O)N[C@@H]([C@@H](C)O)C(=O)N3CCC[C@@H]3C(=O)N2C1]

can be

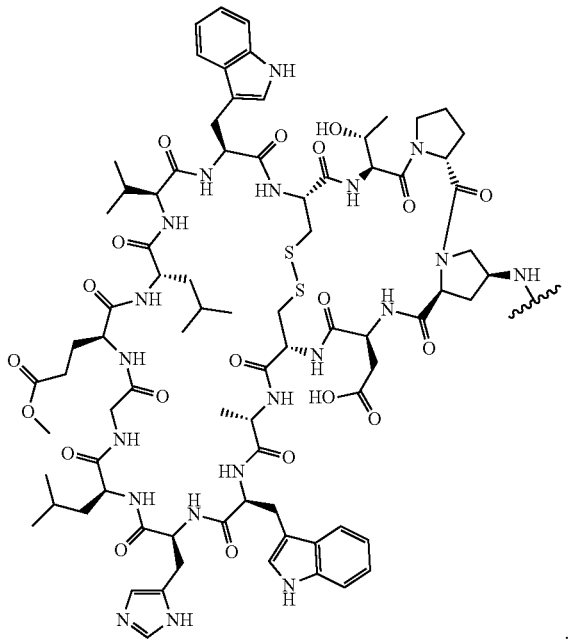 [SMILES: *N[C@H]1C[C@H]2C(=O)N[C@@H](CC(=O)O)C(=O)N[C@H]3CSSC[C@H](NC(=O)[C@H](Cc4c[nH]c5ccccc45)NC(=O)[C@H](C(C)C)NC(=O)[C@H](CC(C)C)NC(=O)[C@H](CCC(=O)OC)NC(=O)CNC(=O)[C@H](CC(C)C)NC(=O)[C@H](Cc4cnc[nH]4)NC(=O)[C@H](Cc4c[nH]c5ccccc45)NC(=O)[C@H](C)NC3=O)C(=O)N[C@@H]([C@@H](C)O)C(=O)N3CCC[C@@H]3C(=O)N2C1]

In alternative embodiments a hydroxyl, amine, amide, or carboxylic acid group in an Extracellular Protein Targeting Ligand drawn herein is used as the attachment point to Linker instead of the drawn attachment point. For example in this embodiment:

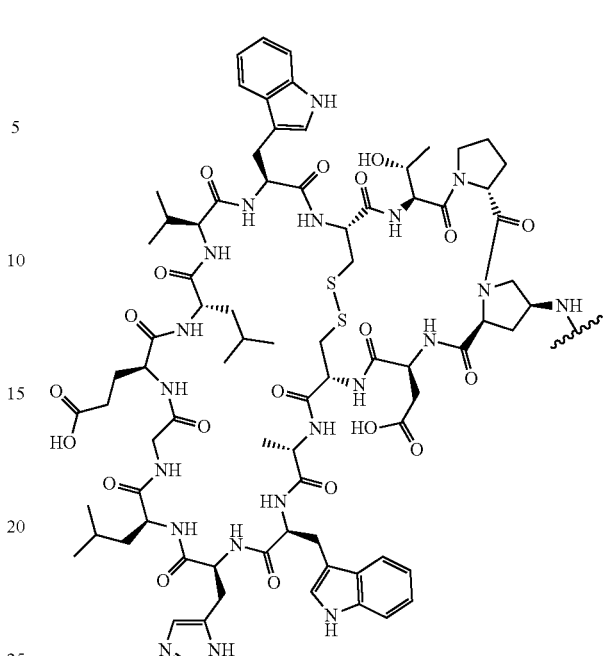

can be

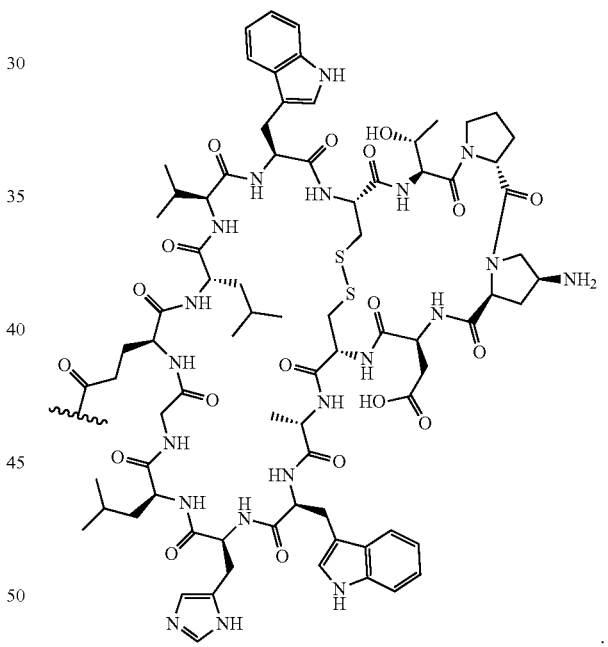

Immunoglobulin E (IgE)

Immunoglobulin E (IgE) is a strong mediator of allergic disease, including but not limited to, atopic asthma, allergic rhinitis, atopic dermatitis, cutaneous contact hypersensitivity, IgE-mediated food allergy, IgE-mediated animal allergies, allergic conjunctivitis, allergic urticaria, anaphylactic shock, nasal polyposis, keratoconjunctivitis, mastocytosis, eosinophilic gastrointestinal disease, bullous pemphigoid, chemotherapy induced hypersensitivity reaction, seasonal allergic rhinitis, interstitial cystitis, eosinophilic esophagitis, angioedema, acute interstitial nephritis, atopic eczema, eosinophilic bronchitis, chronic obstructive pulmonary disease, gastroenteritis, hyper-IgE syndrome (Job's Syndrome), IgE monoclonal gammopathy, monoclonal gammopathy of undetermined significance (MGUS), pemphigus vulgaris, mucus membrane pemphigoid, chronic urticaria, autoimmune uveitis, rheumatoid arthritis, autoimmune pancreatitis, and allergic rhinoconjunctivitis among others.

In certain embodiments the immunoglobulin degrading compound is:

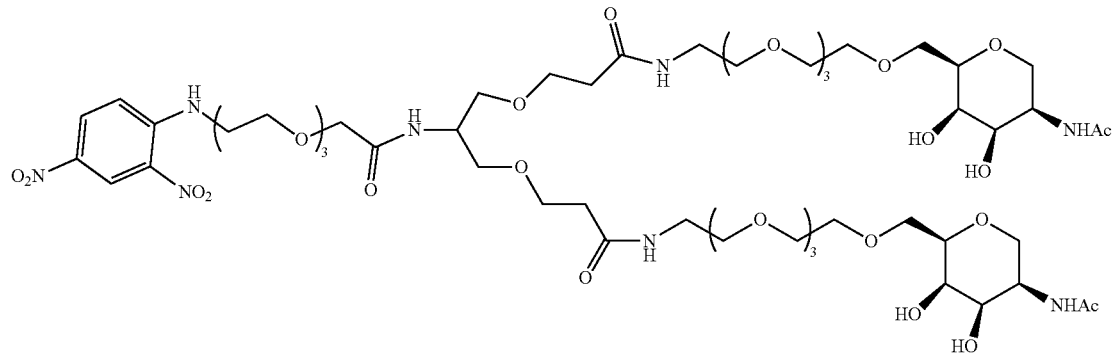

or a pharmaceutically acceptable salt thereof.

In certain embodiments the immunoglobulin degrading compound is:

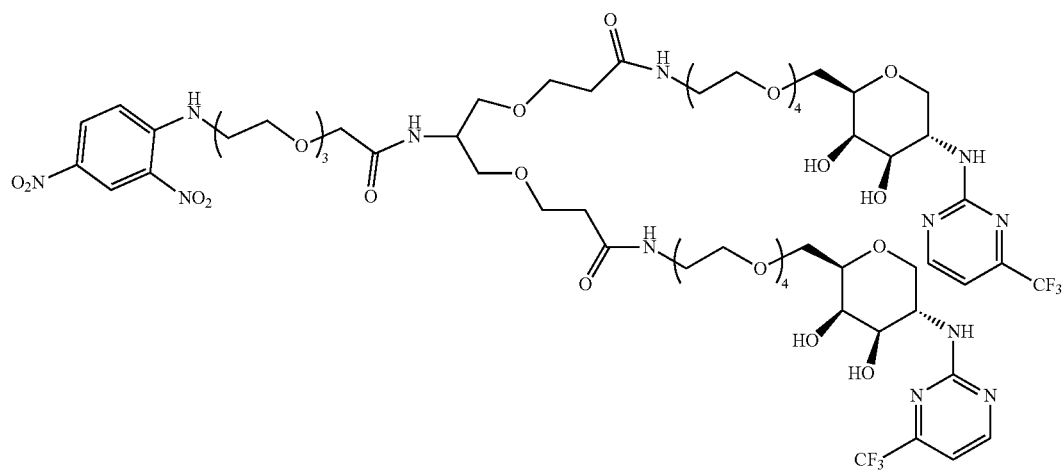

or a pharmaceutically acceptable salt thereof.

In certain embodiments the immunoglobulin degrading compound is:

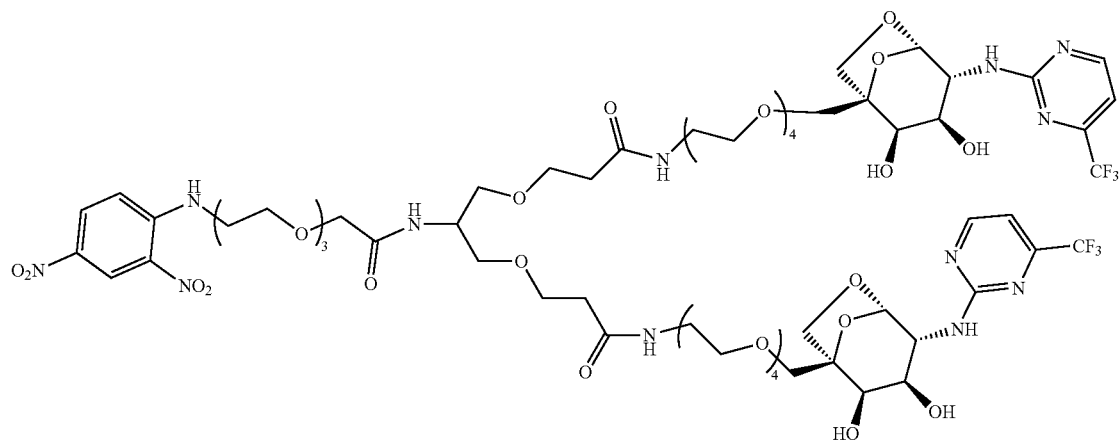

or a pharmaceutically acceptable salt thereof.

In certain embodiments the immunoglobulin degrading compound is:

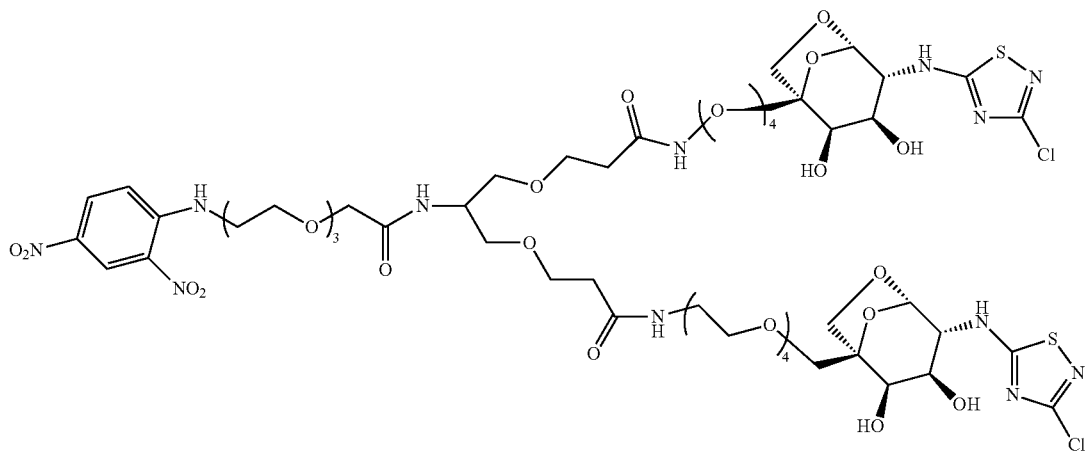

or a pharmaceutically acceptable salt thereof.

In certain embodiments the immunoglobulin degrading compound is:

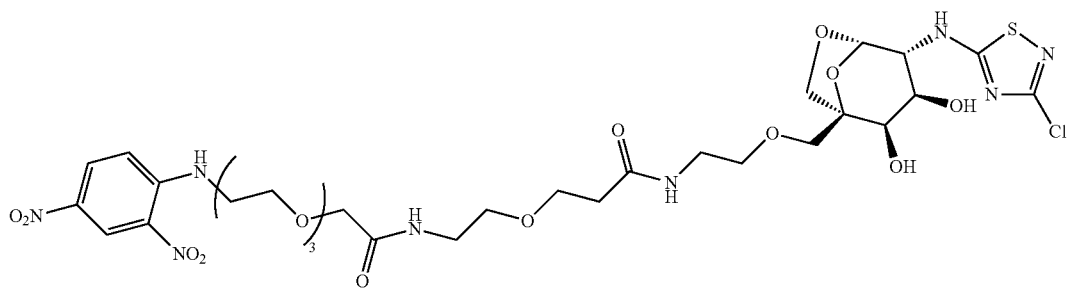

or a pharmaceutically acceptable salt thereof.

In certain embodiments the immunoglobulin degrading compound is:

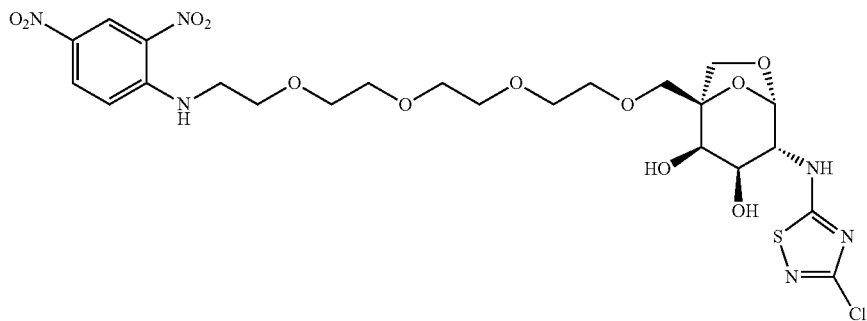 [SMILES: O=[N+]([O-])c1ccc(NCCOCCOCCOCCOC[C@@]23CO[C@@H](O2)[C@H](Nc2nc(Cl)ns2)[C@@H](O)[C@H]3O)c([N+](=O)[O-])c1]

or a pharmaceutically acceptable salt thereof.

In certain embodiments the Immunoglobulin Targeting Ligand is:

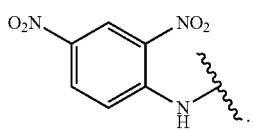 [SMILES: *Nc1ccc([N+](=O)[O-])cc1[N+](=O)[O-]]

In certain embodiments the IgE Targeting Ligand is selected from
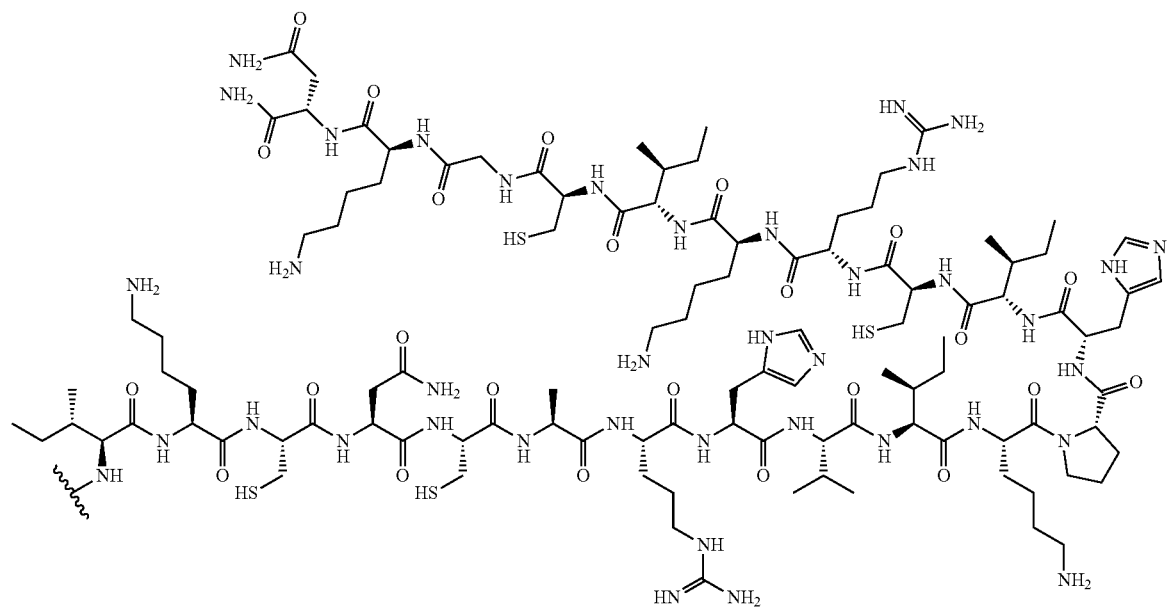
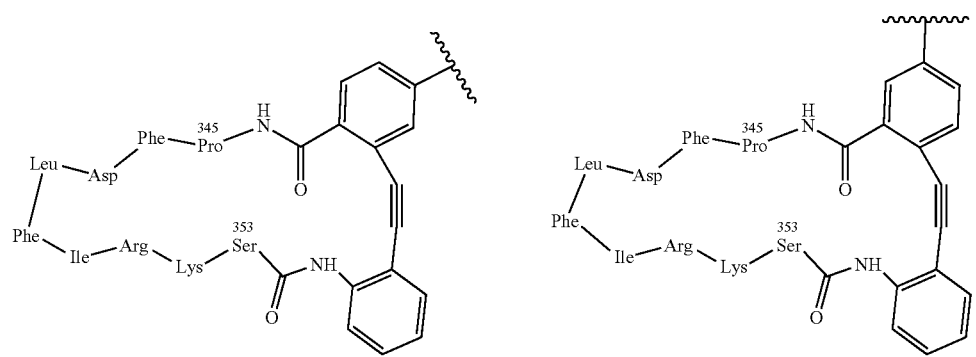
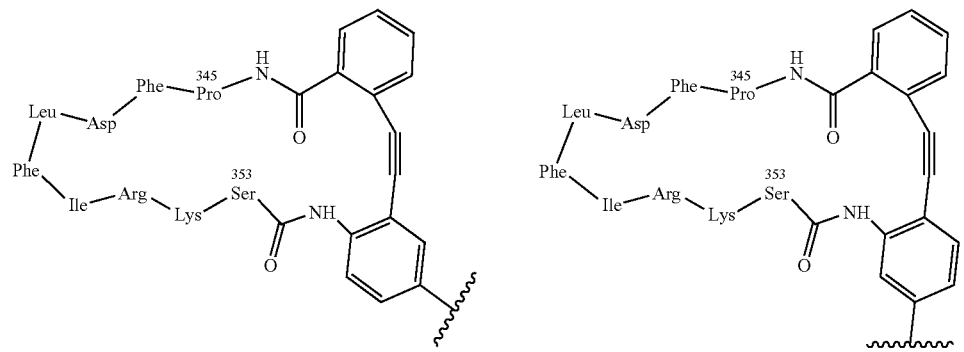

-continued
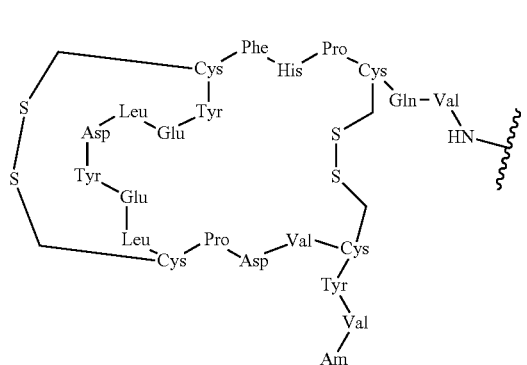
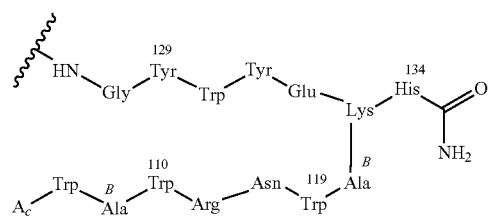
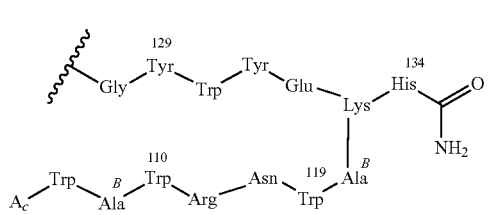
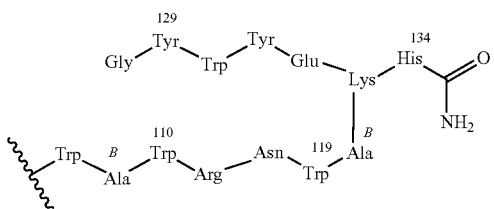
Non-limiting examples of IgE degrading compounds include:
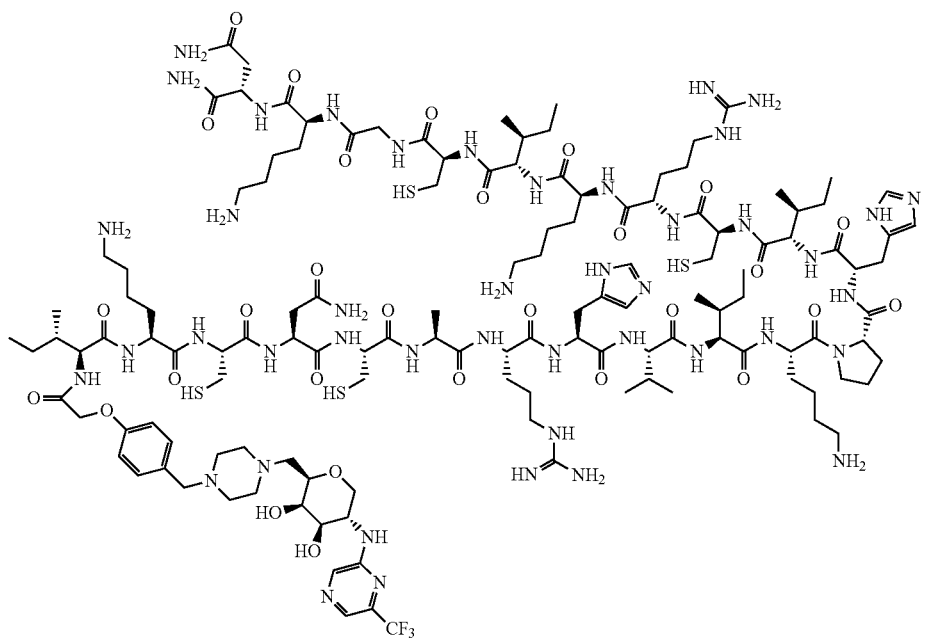

-continued
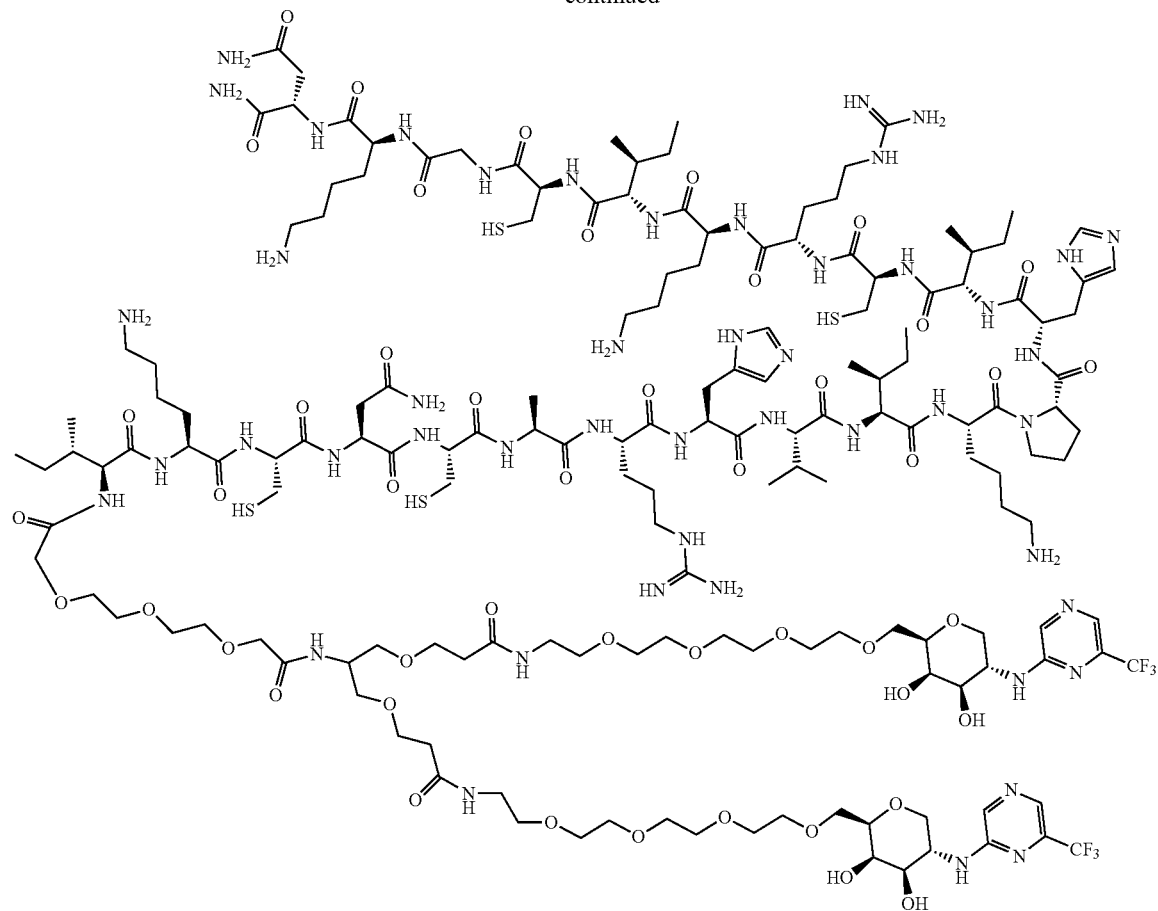
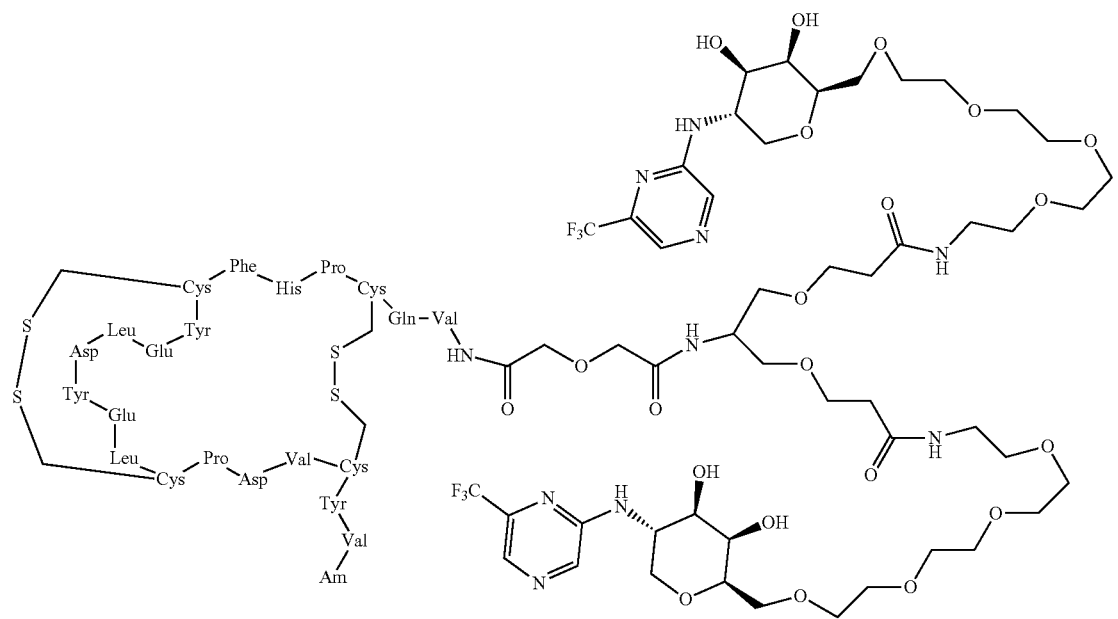

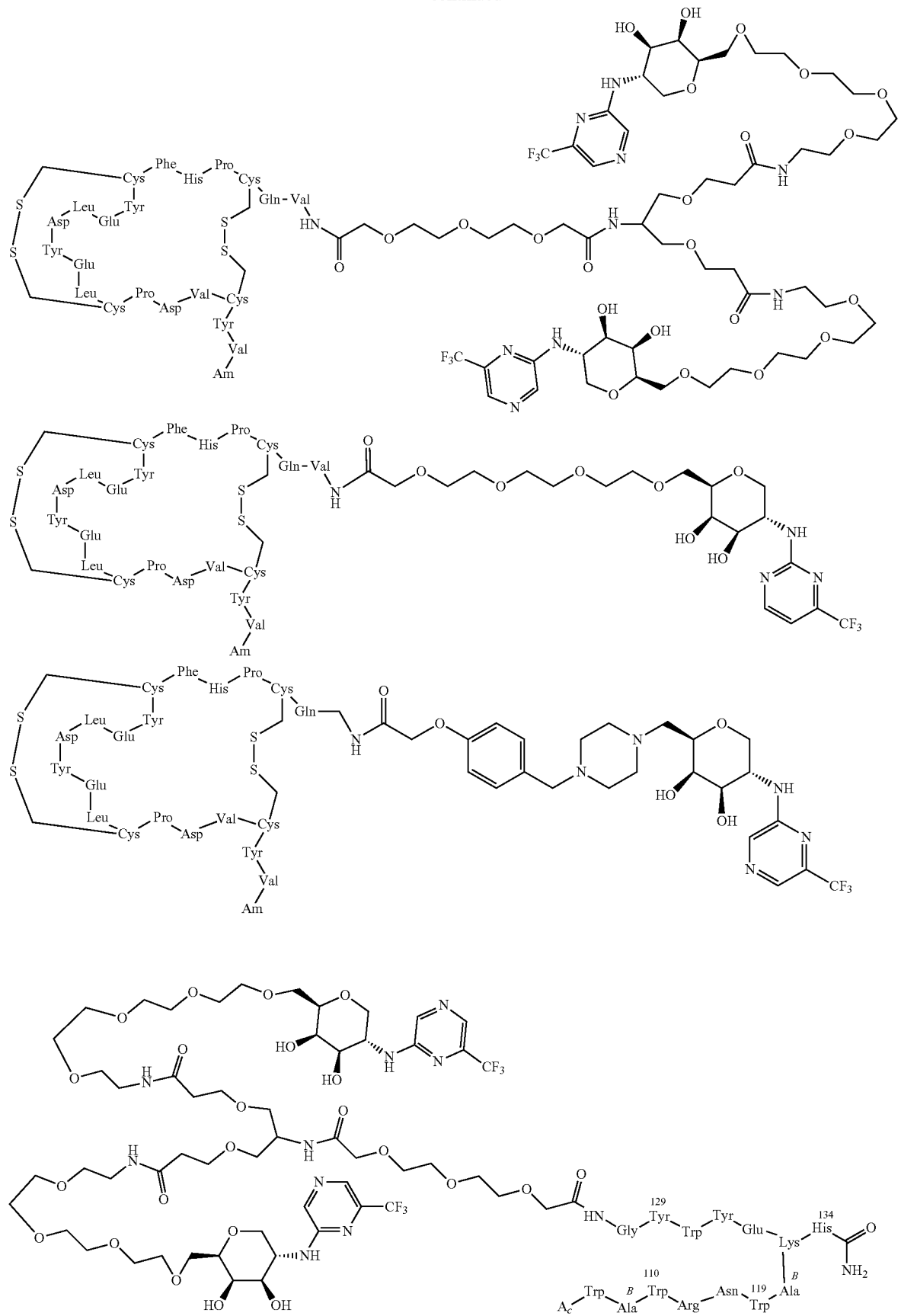

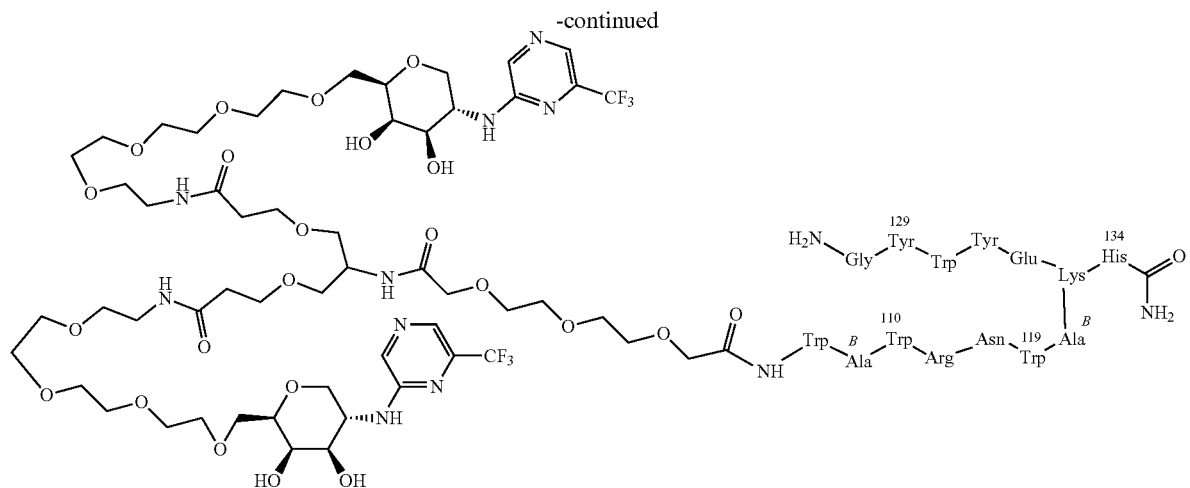

Anti-MAG IgM Autoantibodies

In some embodiments the Target Extracellular Protein is anti-MAG IgM autoantibodies. Myelin-associated glycoprotein (MAG) is a transmembrane glycoprotein that plays a role in glial-axonal interactions in the nervous system. In some patients, IgM anti-MAG antibodies develop leading to neuropathy. Antibody levels can be as high as four-fold over normal, leading to potential nephropathy. Lowering levels of anti-MAG antibodies is associated with clinical response in polyneuropathy.

Representative targeting ligands that bind to Anti-MAG IgM autoantibodies include HSO$_3$-3GlcAβ1-3Galβ1-4GlcNAcβ1-3Galβ1-4Glcβ1-Cer; HSO$_3$-3GlcAβ1-3Galβ1-4GlcNAcβ1-3Galβ1-4GlcNAcβ1-3Galβ1-4Glcβ1-Cer; HSO$_3$-3GlcAβ1-3Galβ1-4GlcNAc-X;

387
-continued
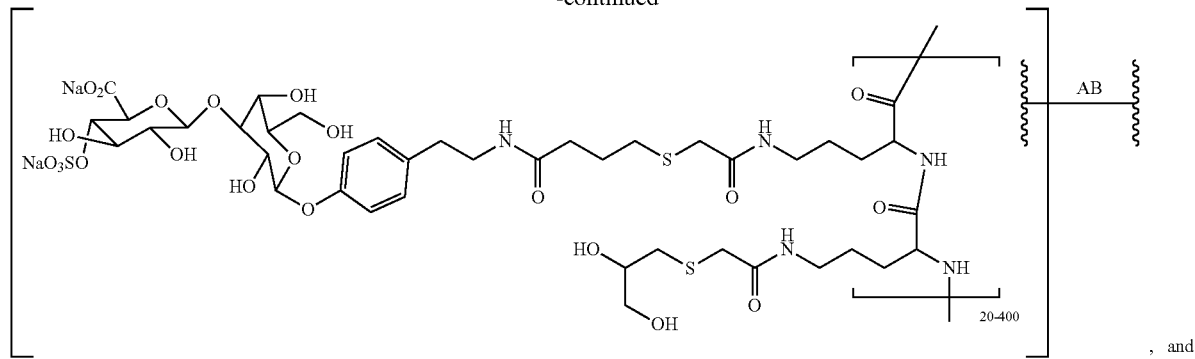
, and
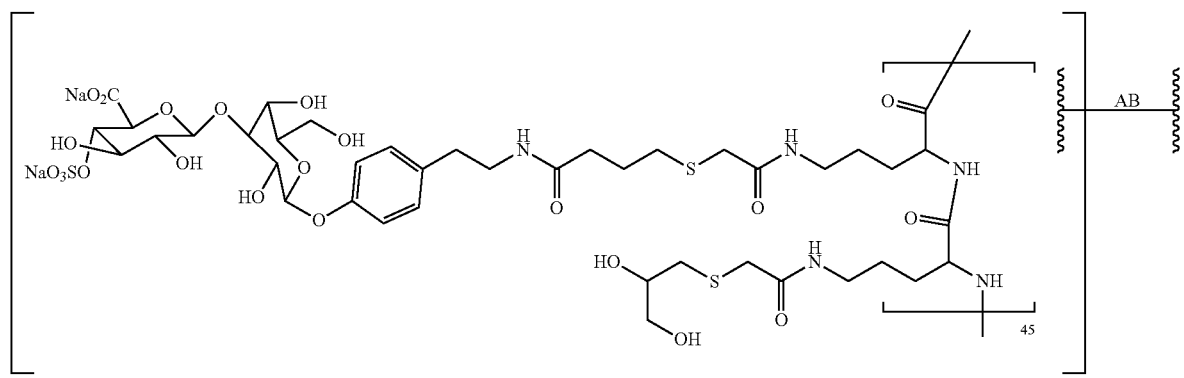
Additional IgM autoantibodies that can be used in the present invention are described in Herrendorff, R. et al. 2017 PNAS Early Edition, doi/10.1073/pnas.1619386114; and WO2018/167,230.
Non-limiting examples of IgM autoantibody degrading compounds include:
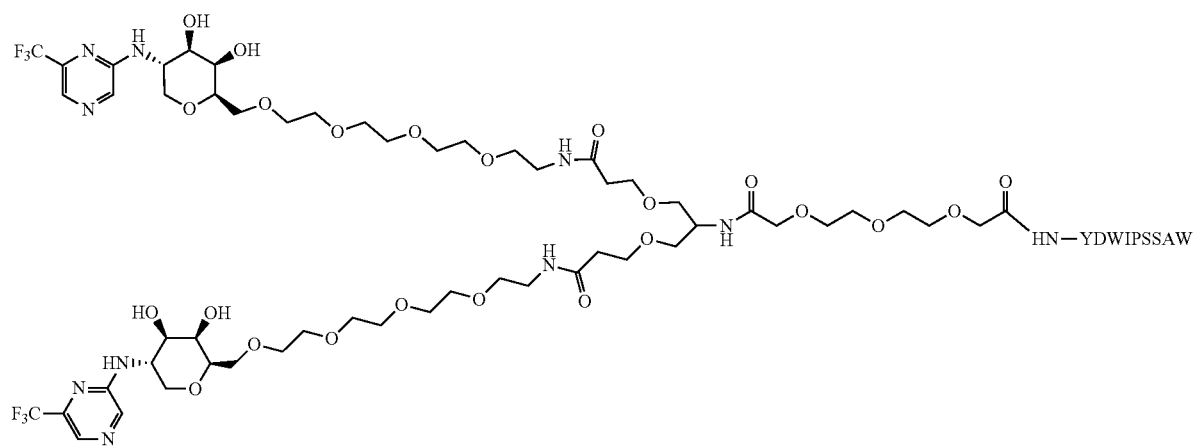

-continued
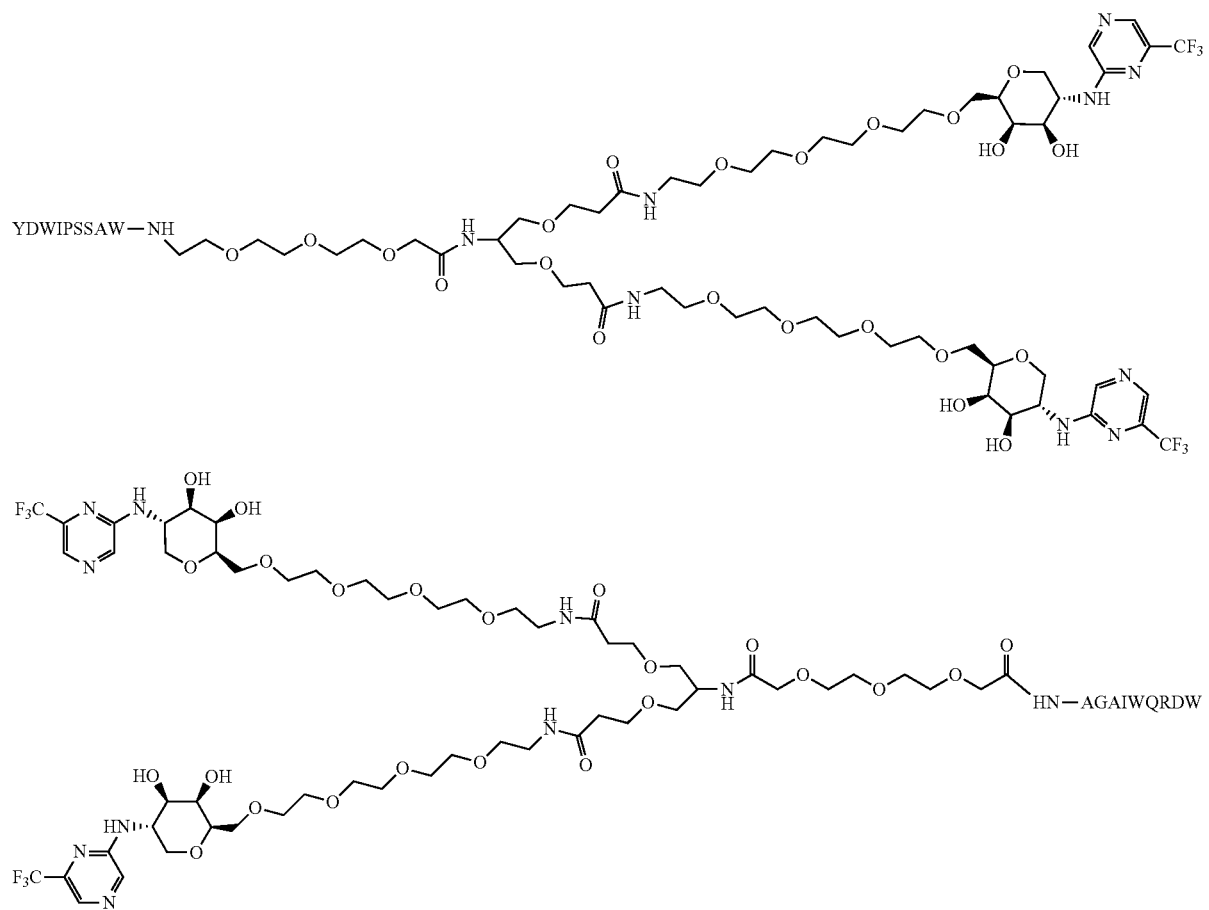
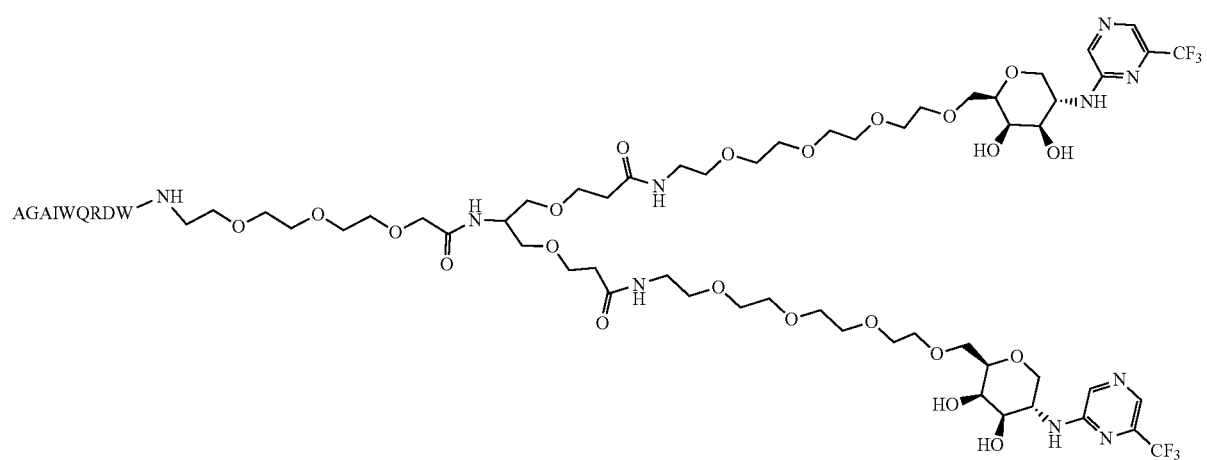

-continued
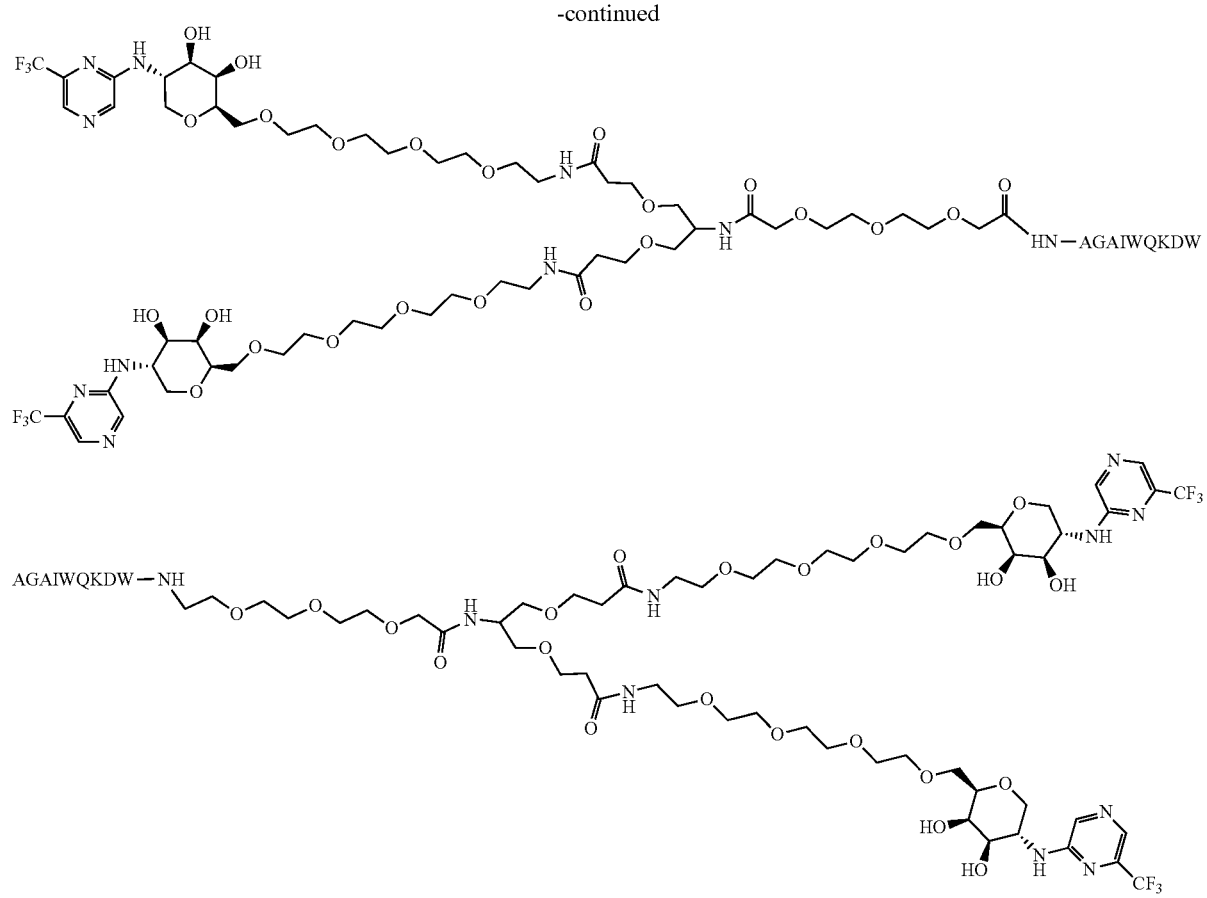
In certain non-limiting embodiments, the IgM autoantibody degrading compound is selected from the following compounds or a bi- or tri-dentate version thereof:
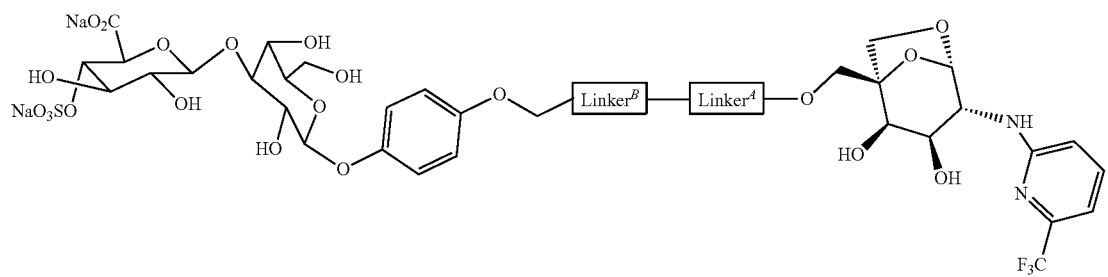
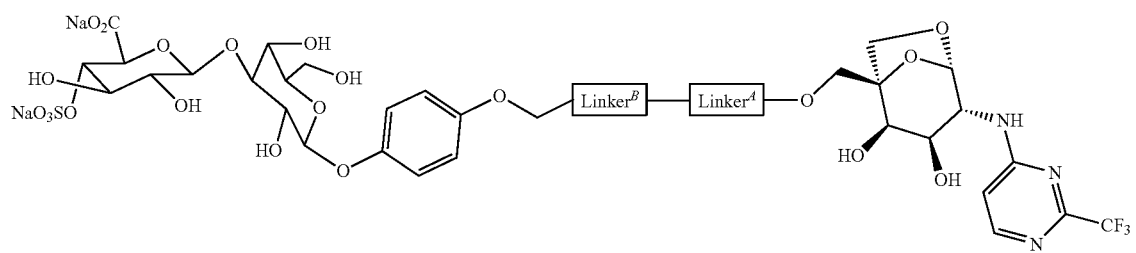

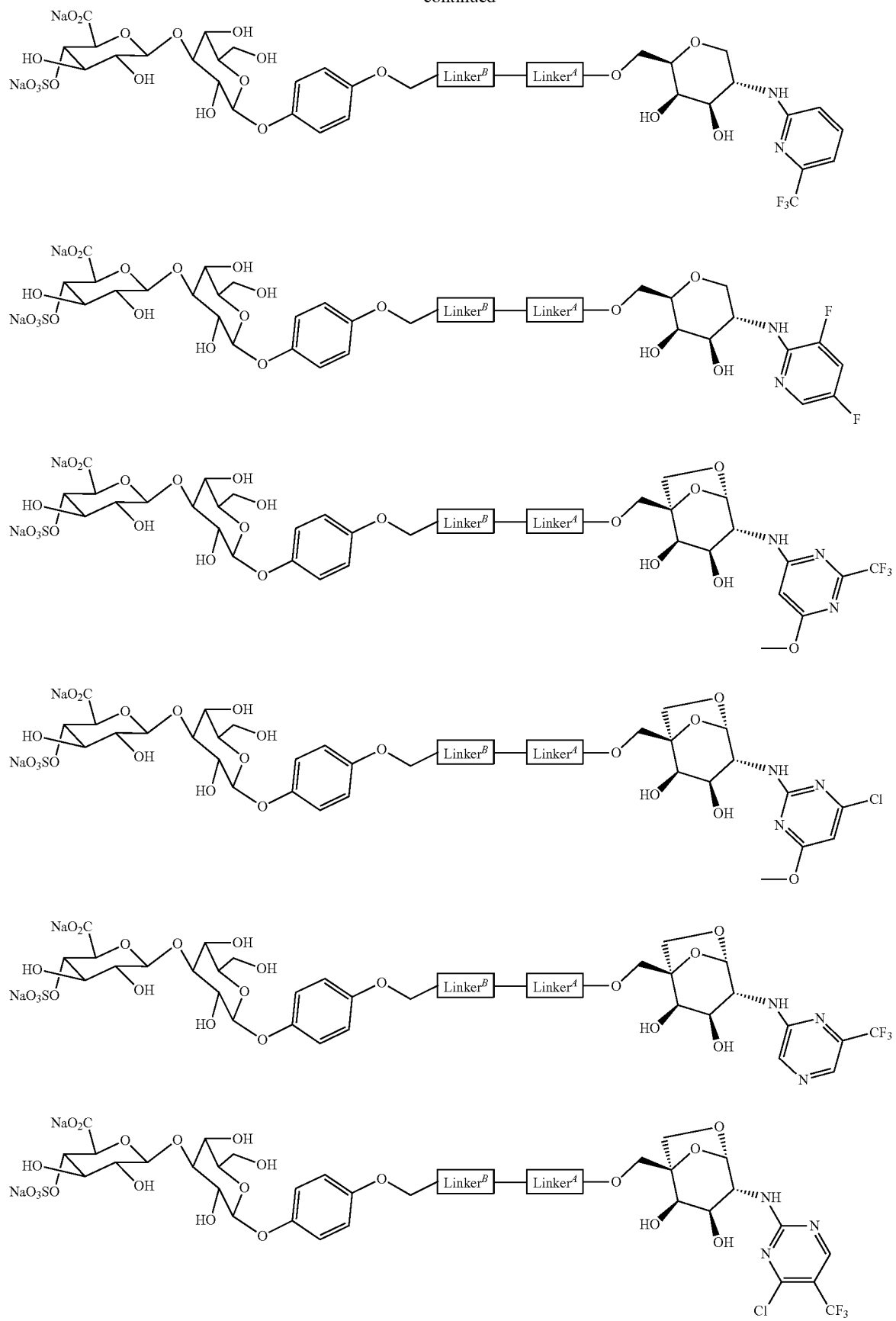

-continued
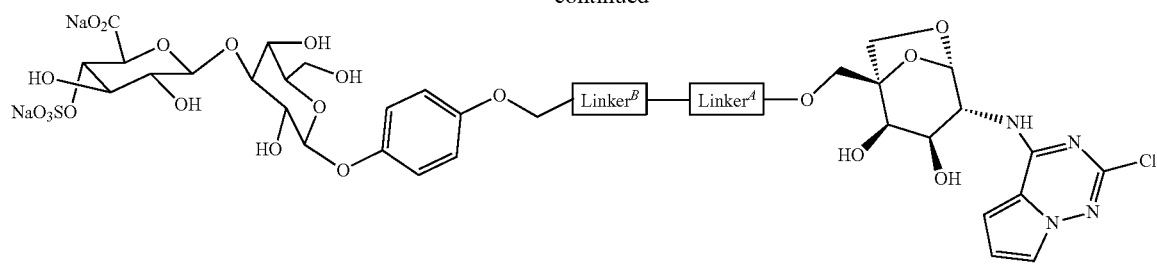
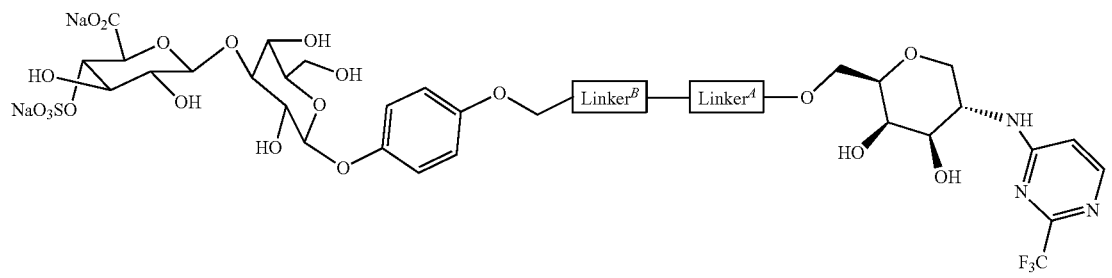
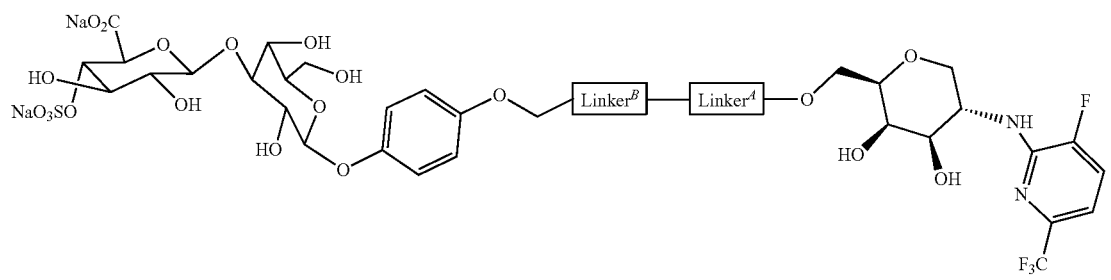
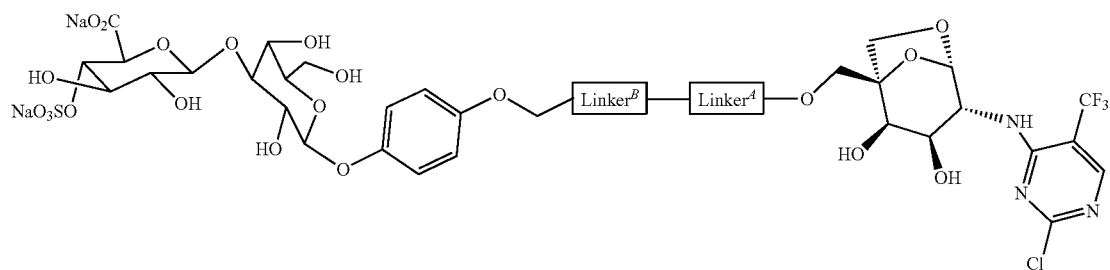
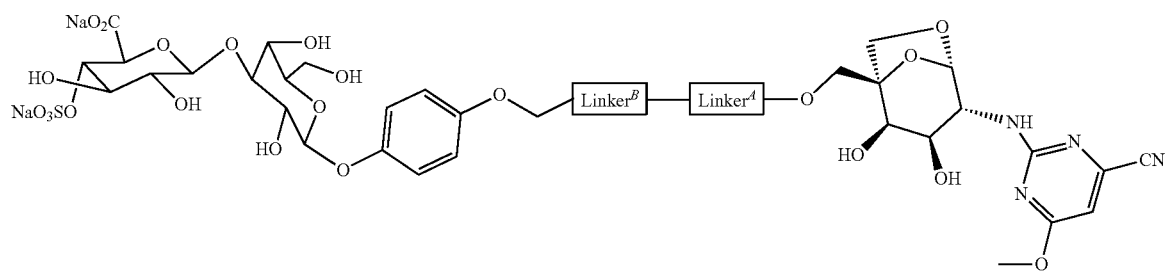
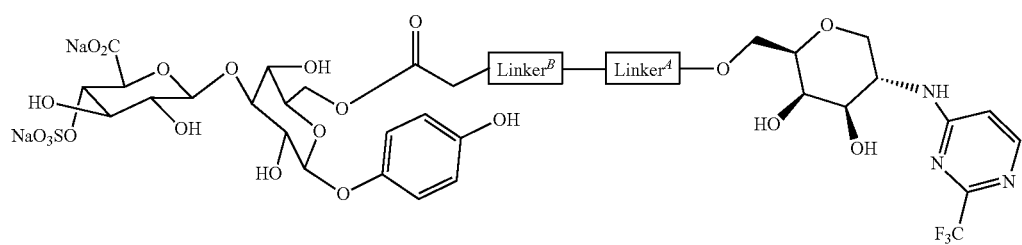

or a pharmaceutically acceptable salt thereof.

Phospholipase A2 Receptor-1 (PLA2R) Autoantibodies

In some embodiments, the Target Extracellular Protein is an autoantibody that binds PLA2R. Phospolipase A2 Receptor-1 (PLA2R) is a major target in autoimmune membranous nephropathy. Membranous nephropathy is one of the leading causes of nephrotic syndrome, with most patients progressing to end-stage renal disease. Current treatment regimes with anti-CD20 antibodies can be ineffective at generating a complete remission. PLA2R is a transmembrane glycoprotein with a cysteine-rich N-terminal extracellular domain. This domain contains the epitope where autoantibodies bind. Reduction of autoantibody levels may provide relief to patients and complete elimination of the autoantibodies could be required to produce a durable remission.

The Protein Data Bank provides the crystal structure of the CTLD7 domain of PLA2R, the region where autoantibodies bind (6JLI; Yu et al. J. Struct. Biol. 207, 295-300). Representative PLA2R autoantibody binding ligands include, but are not limited to,

```
                                                          SEQ ID NO: 88
GIFVIQSESLKKC (Fresquet et al. J. Am. Soc. Nephrol 2015, 26, 302)

SEQ. ID NO: 89
SVLTLENCK (Fresquet et al. J. Am. Soc. Nephrol 2015, 26, 302)

SEQ ID NO: 90
SVLTLENC (Brenchley et al. WO2019/081912)

SEQ ID NO: 91
SVLTLDNCK (Brenchley et al. WO2019/081912)

SEQ ID NO: 92
SVLTEENC (Brenchley et al. WO2019/081912)

SEQ ID NO: 93
SVLTEENS (Brenchley et al. WO2019/081912)

SEQ ID NO: 94
SVLTDENC (Brenchley et al. WO2019/081912)

SEQ ID NO: 95
SVLTDENS (Brenchley et al. WO2019/081912)

SEQ ID NO: 96
PIQSESLKK (Brenchley et al. WO2019/081912)

SEQ ID NO: 97
VIDSESLKK (Brenchley et al. WO2019/081912)

SEQ ID NO: 98
PIDSESLKK (Brenchley et al. WO2019/081912)

SEQ ID NO: 99
VIQSESLKK (Brenchley et al. WO2019/081912)
```

-continued

PIESES-PEG-K-PEG-SVLTEENC (Brenchley et al. WO2019/081912)  SEQ ID NO: 100

VIQSES-PEG-K-PEG-SVL TLENC (Brenchley et al. WO2019/081912)  SEQ ID NO: 101

VIQSES-PEG-K-PEG-SVL TEENC (Brenchley et al. WO2019/081912)  SEQ ID NO: 102

PIDDES-PEG-K-PEG-SVLTLENC (Brenchley et al. WO2019/081912)  SEQ ID NO: 103

PIDDES-PEG-KPEG-SVLTEENC (Brenchley et al. WO2019/081912)  SEQ ID NO: 104

VIQSESLKKCKSVLTLENC (Brenchley et al. WO2019/081912)  SEQ ID NO: 105

PIQSESLKKCKSVLTLENC (Brenchley et al. WO2019/081912)  SEQ ID NO: 106

VIESESLKKCKSVLTLENC (Brenchley et al. WO2019/081912)  SEQ ID NO: 107

VIDSESLKKCKSVLTLENC (Brenchley et al. WO2019/081912)  SEQ ID NO: 108

PIESESLKKCKSVLTLENC (Brenchley et al. WO2019/081912)  SEQ ID NO: 109

VIQSESLKKCIQAGKLENC (Brenchley et al. WO2019/081912)  SEQ ID NO: 110

PIQSESLKKCIQAGKLENC (Brenchley et al. WO2019/081912)  SEQ ID NO: 111

VIESESLKKCIQAGKLENC (Brenchley et al. WO2019/081912)  SEQ ID NO: 112

VIDSESLKKCIQAGKLENC (Brenchley et al. WO2019/081912)  SEQ ID NO: 113

PIESESLKKCIQAGKLENC (Brenchley et al. WO2019/081912)  SEQ ID NO: 114

PIQSESLKKCKSVLTLENK (Brenchley et al. WO2019/081912)  SEQ ID NO: 115

VIESESLKKCKSVLTLENK (Brenchley et al. WO2019/081912)  SEQ ID NO: 116

VIDSESLKKCKSVLTLENK (Brenchley et al. WO2019/081912)  SEQ ID NO: 117

PIESESLKKCKSVLTLENK (Brenchley et al. WO2019/081912)  SEQ ID NO: 118

VIQSESLKKCIQAGKLENK (Brenchley et al. WO2019/081912)  SEQ ID NO: 119

PIQSESLKKCIQAGKLENK (Brenchley et al. WO2019/081912)  SEQ ID NO: 120

VIESESLKKCIQAGKLENK (Brenchley et al. WO2019/081912)  SEQ ID NO: 121

VIDSESLKKCIQAGKLENK (Brenchley et al. WO2019/081912)  SEQ ID NO: 122

PIESESLKKCIQAGKLENK (Brenchley et al. WO2019/081912)  SEQ ID NO: 123

PIESESGSVLTLENCK (Brenchley et al. WO2019/081912)  SEQ ID NO: 124

PIESESGGSVLTLENCK (Brenchley et al. WO2019/081912)  SEQ ID NO: 125

PIESESGGGSVLTLENCK (Brenchley et al. WO2019/081912)  SEQ ID NO: 126

PIESESGGGGSVLTLENCK (Brenchley et al. WO2019/081912) SEQ ID NO: 127

PIESESGGGGGSVLTLENCK (Brenchley et al. WO2019/081912) SEQ ID NO: 128

VIQSESGSVLTLENCK (Brenchley et al. WO2019/081912) SEQ ID NO: 129

VIQSESGGSVLTLENCK (Brenchley et al. WO2019/081912) SEQ ID NO: 130

VIQSESGGGSVLTLENCK (Brenchley et al. WO2019/081912) SEQ ID NO: 131

VIQSESGGGGSVLTLENCK (Brenchley et al. WO2019/081912) SEQ ID NO: 132

VIQSESGGGGGSVLTLENCK (Brenchley et al. WO2019/081912) SEQ ID NO: 133

KGCFVIQSESLKKSIQAGKSVLTLENCK (Brenchley et al. WO2019/081912) WO2019/081912) SEQ ID NO: 134

LKKCIQAGKSVLTLENCKQAN (Brenchley et al. WO2019/081912) SEQ ID NO: 135

WQDKGIFVIQSESLKKCIQAGK (Brenchley et al. WO2019/081912) SEQ ID NO: 136

KGIFVIQSESLKKCIQAGKSVLTLENCK (Brenchley et al. WO2019/081912) SEQ ID NO: 137

GIFVIQSESLKKC (Brenchley et al. WO2015/185949) SEQ ID NO: 138

WSVLTLENCK (Brenchley et al. WO2015/185949) SEQ ID NO: 139

WQDKGIFVIQSESLKKCIQAGKSVLTLENCK (Brenchley et al. WO2015/185949) SEQ ID NO: 140

YDWIPSSAW (Glee et al., the journal of immunology, 1999, 163:826-833) SEQ ID NO: 141

AGAIWQRDW SEQ ID NO: 142

AGAIWQKDW SEQ ID NO: 143

VIQSESLK SEQ ID NO: 144

PIQSESLK SEQ ID NO: 145

PIESESLK SEQ ID NO: 146

SVLTEENCK SEQ ID NO: 147

In certain embodiments a compound is provided of Formula

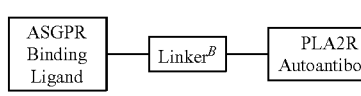

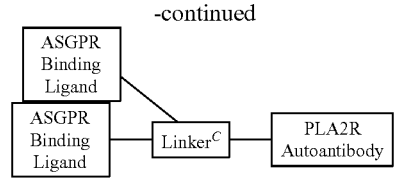

-continued

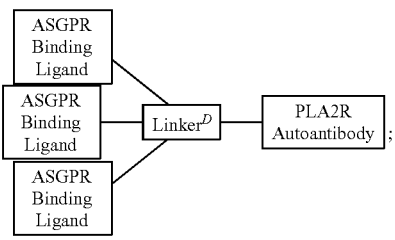

or a pharmaceutically acceptable salt thereof, wherein

PLA2R Autoantibody is any PLA2R autoantibody described in WO2019/081912.

In certain embodiments PLA2R Autoantibody is of Formula:
SEQ ID NO: 148: S-V-L-T-XH1-E-N-XH2;
SEQ ID NO: 149: XH3-I-XH4-XH5-E-XH6;
SEQ ID NO: 150: XH1-E-N-XH2-K;
SEQ ID NO: 151: S-V-L-T-XH1-E-N—C-K;
SEQ ID NO: 152: XH3-I-XH4-XH5-E-XH6-L-K; or
or a peptide of SEQ ID No: 148, 149, 150, 151, or 152 linked via a Linker-B group, in certain embodiments the linked sequences are SEQ ID: 148 and SEQ ID NO: 149 or SEQ ID NO: 148 and SEQ ID NO: 152;
wherein XH1, XH2, XH3, XH4, XH5, and XH6 are independently any natural amino acid or other amino acid described herein;
and wherein the sequence is linked to a Linker described herein at a terminal amine or carboxylic acid.

Non-limiting examples of PLA2R degrading compounds include:

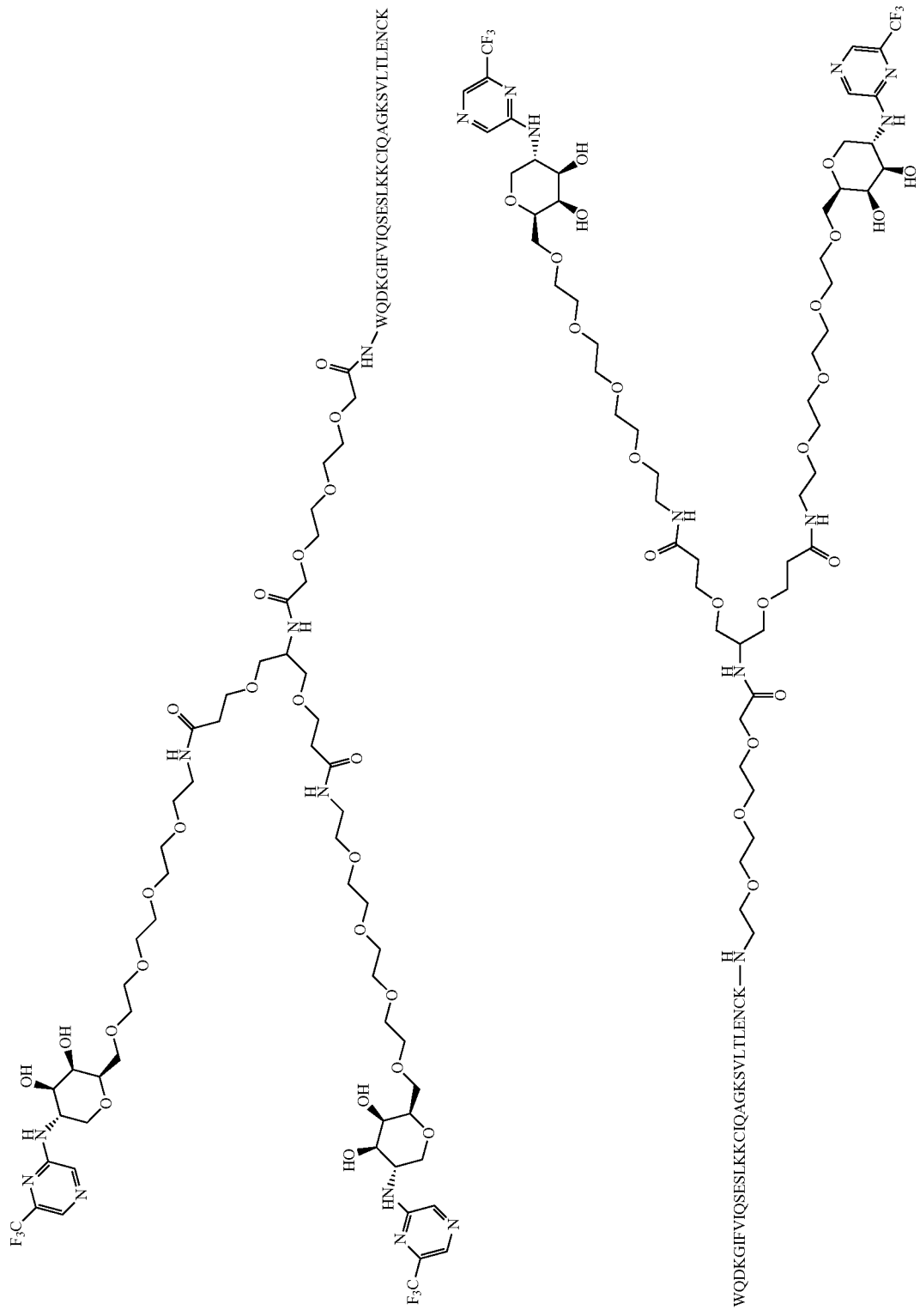

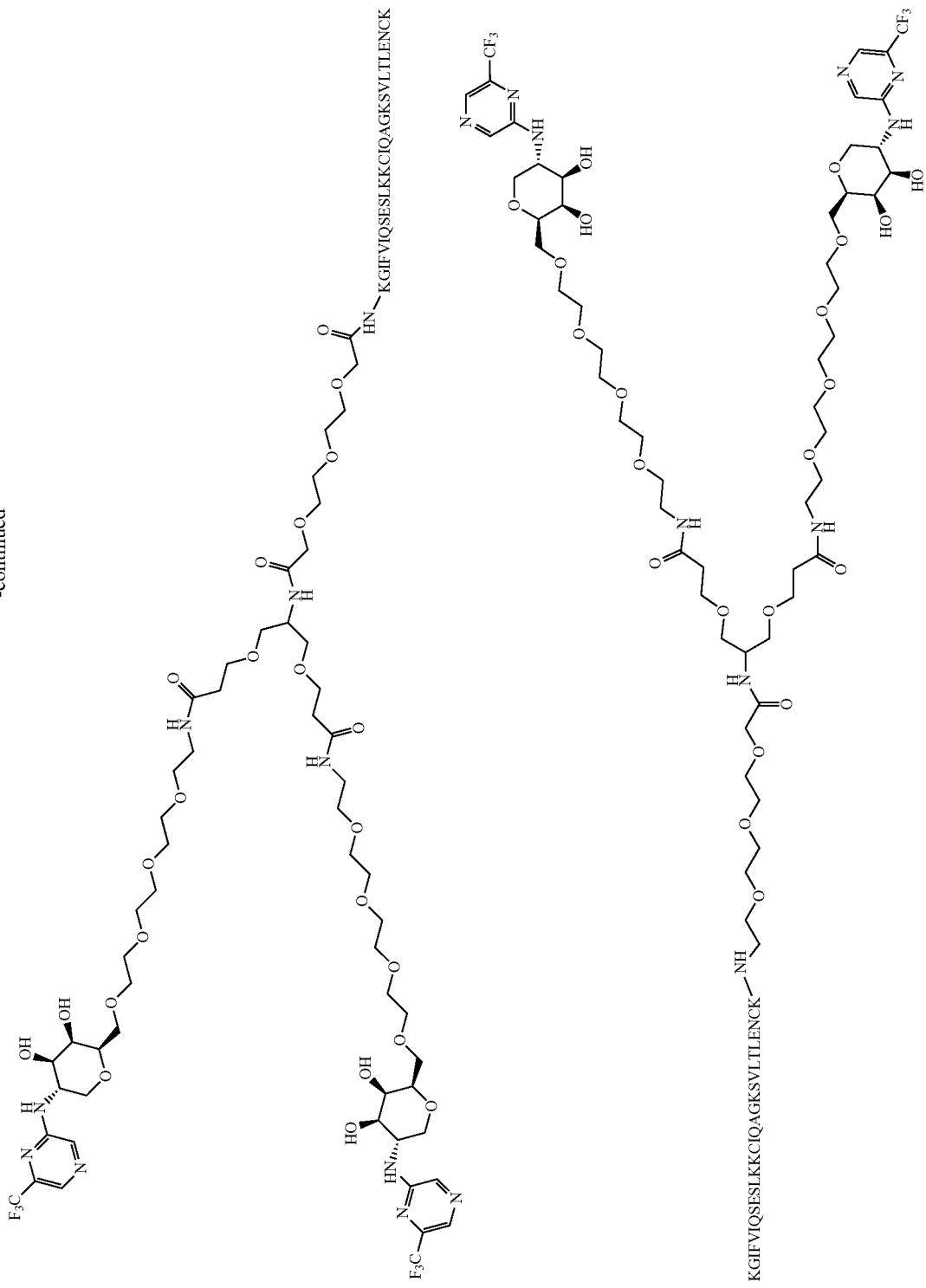

409 410
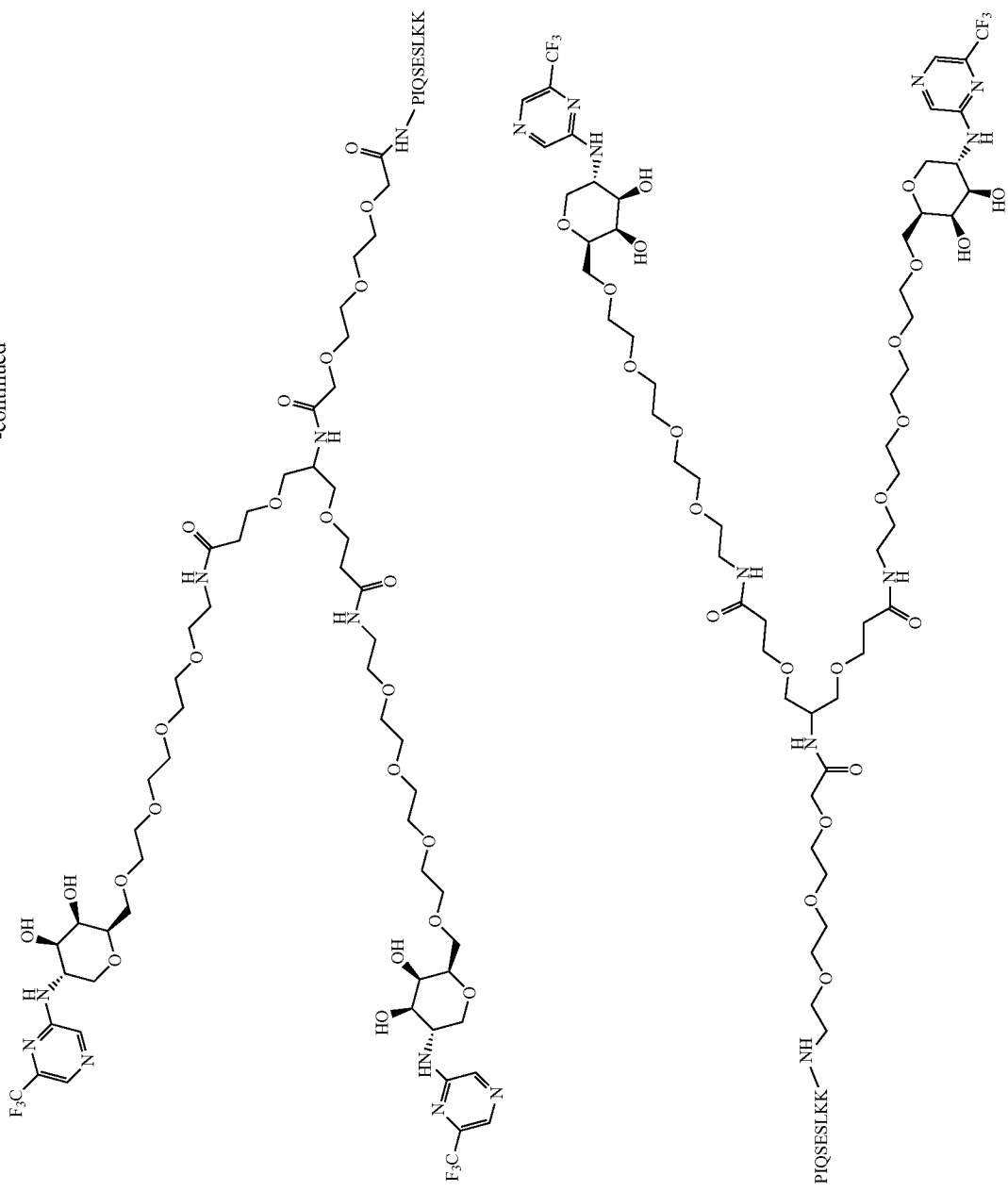

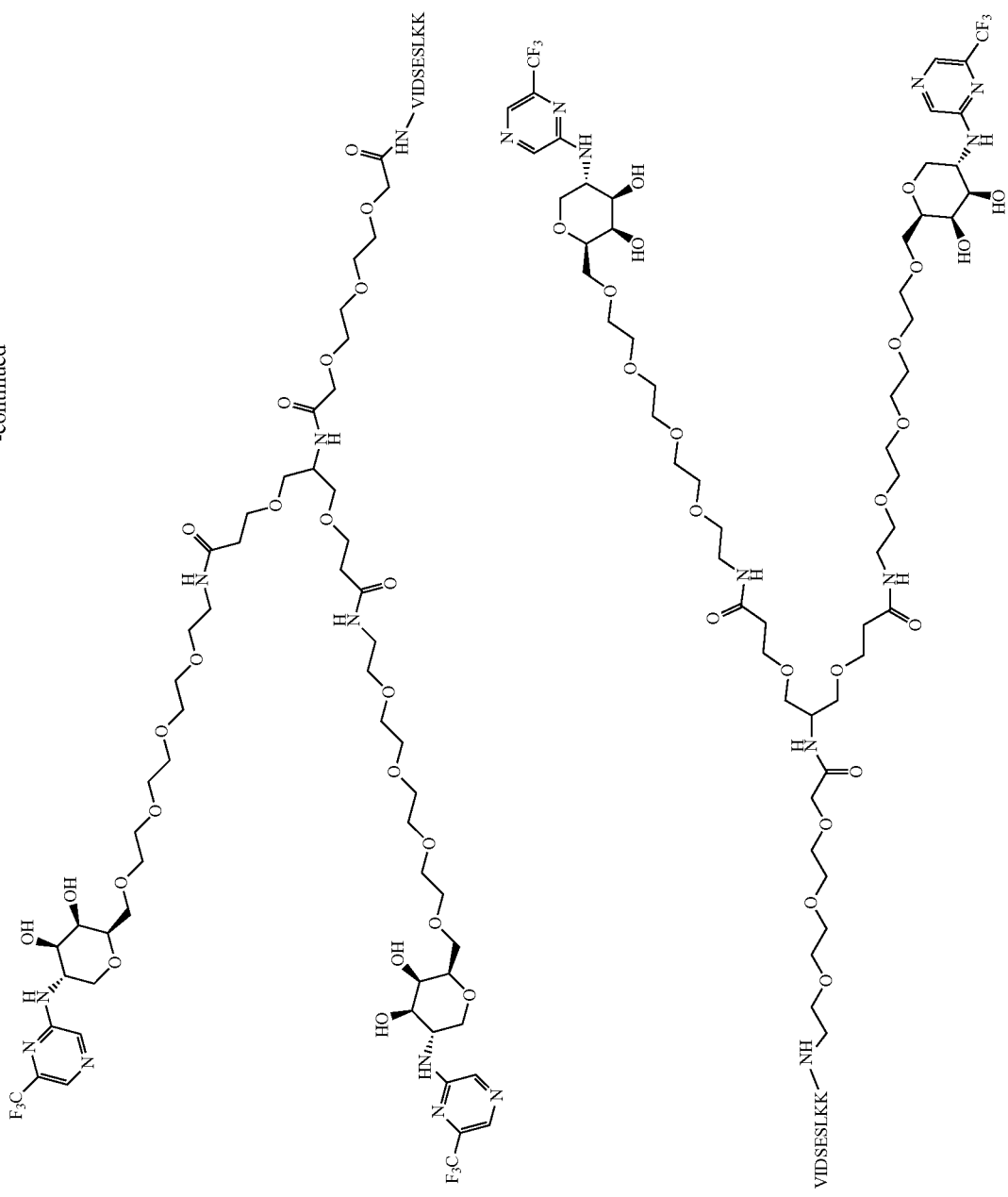

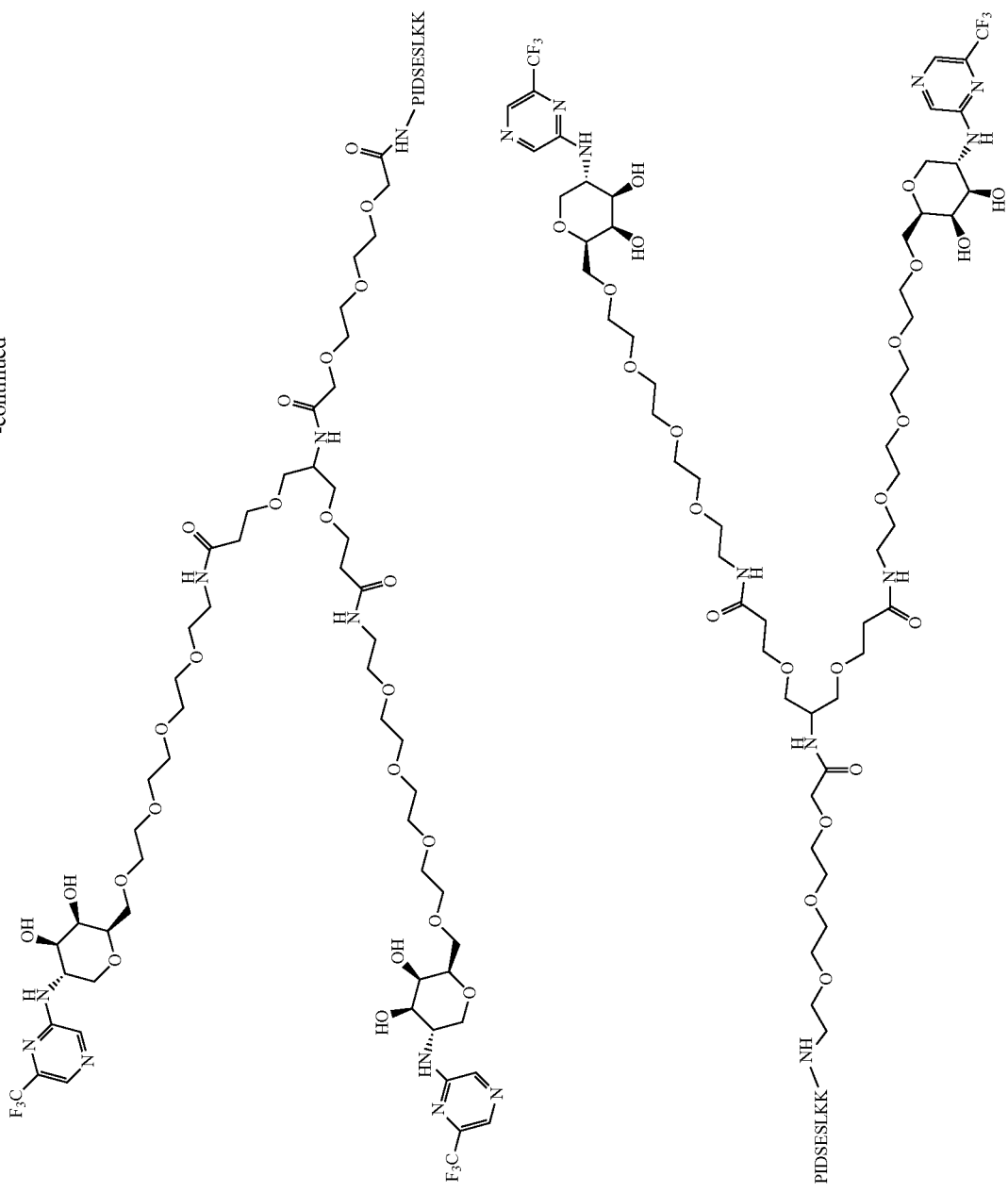

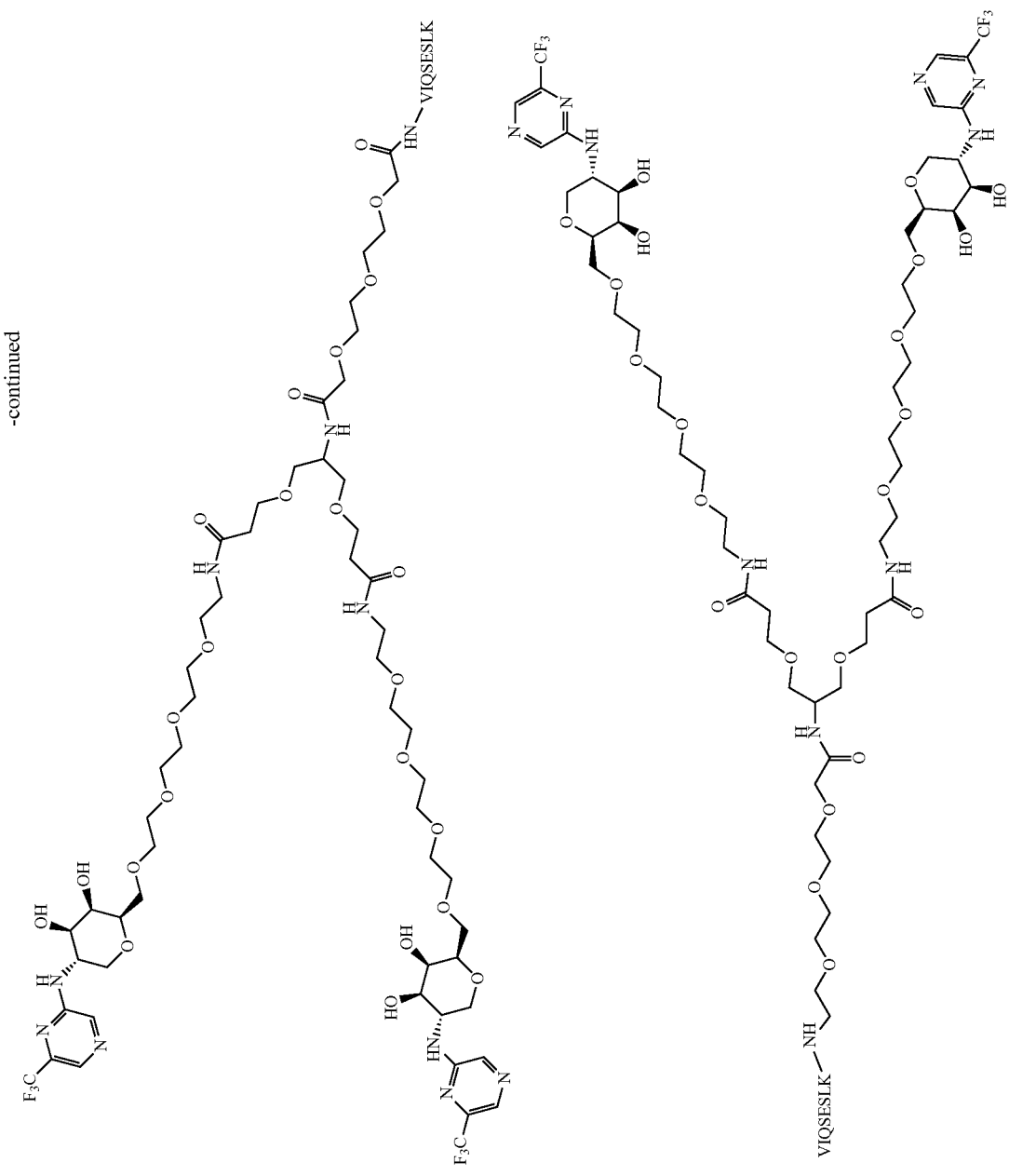

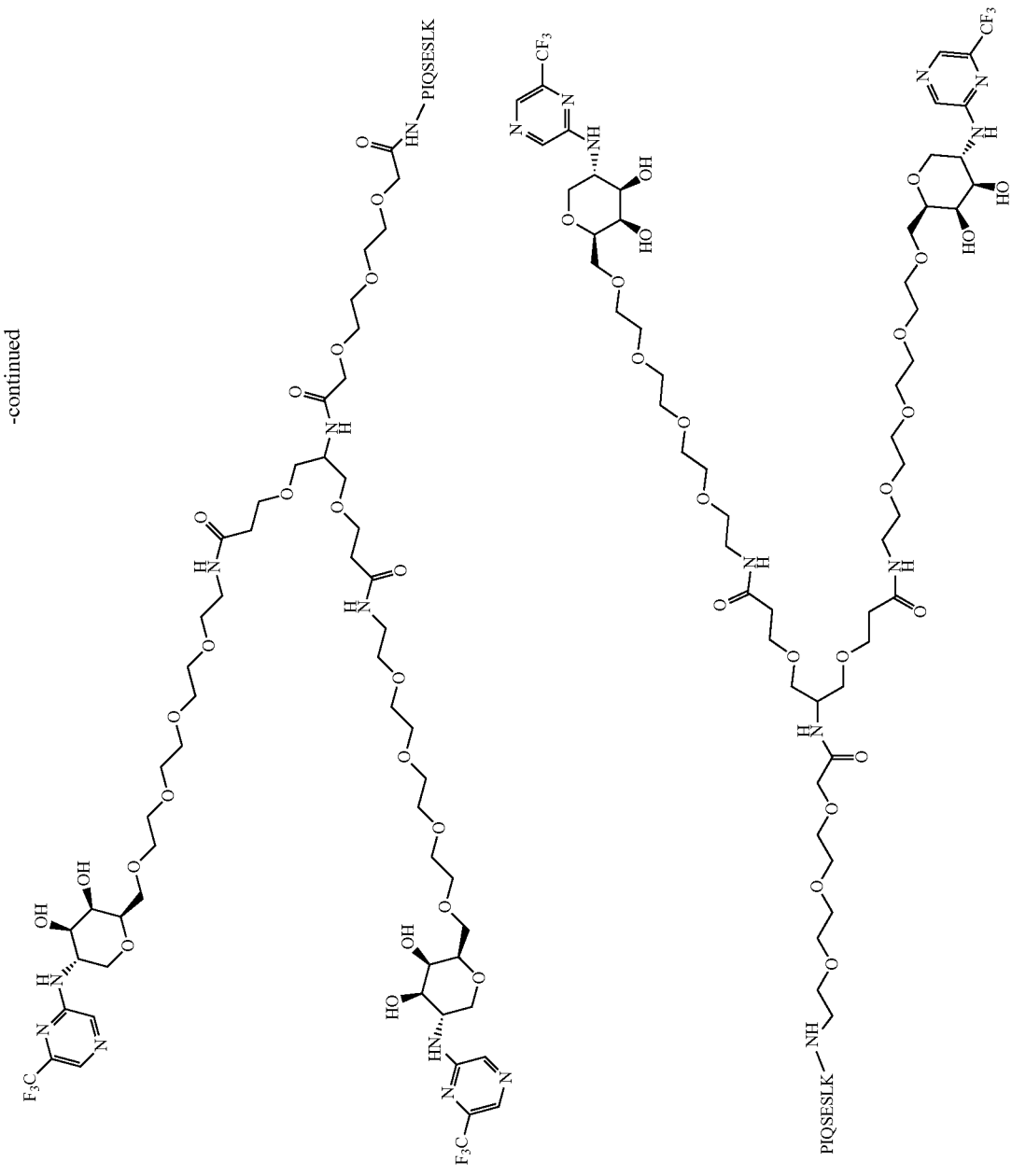

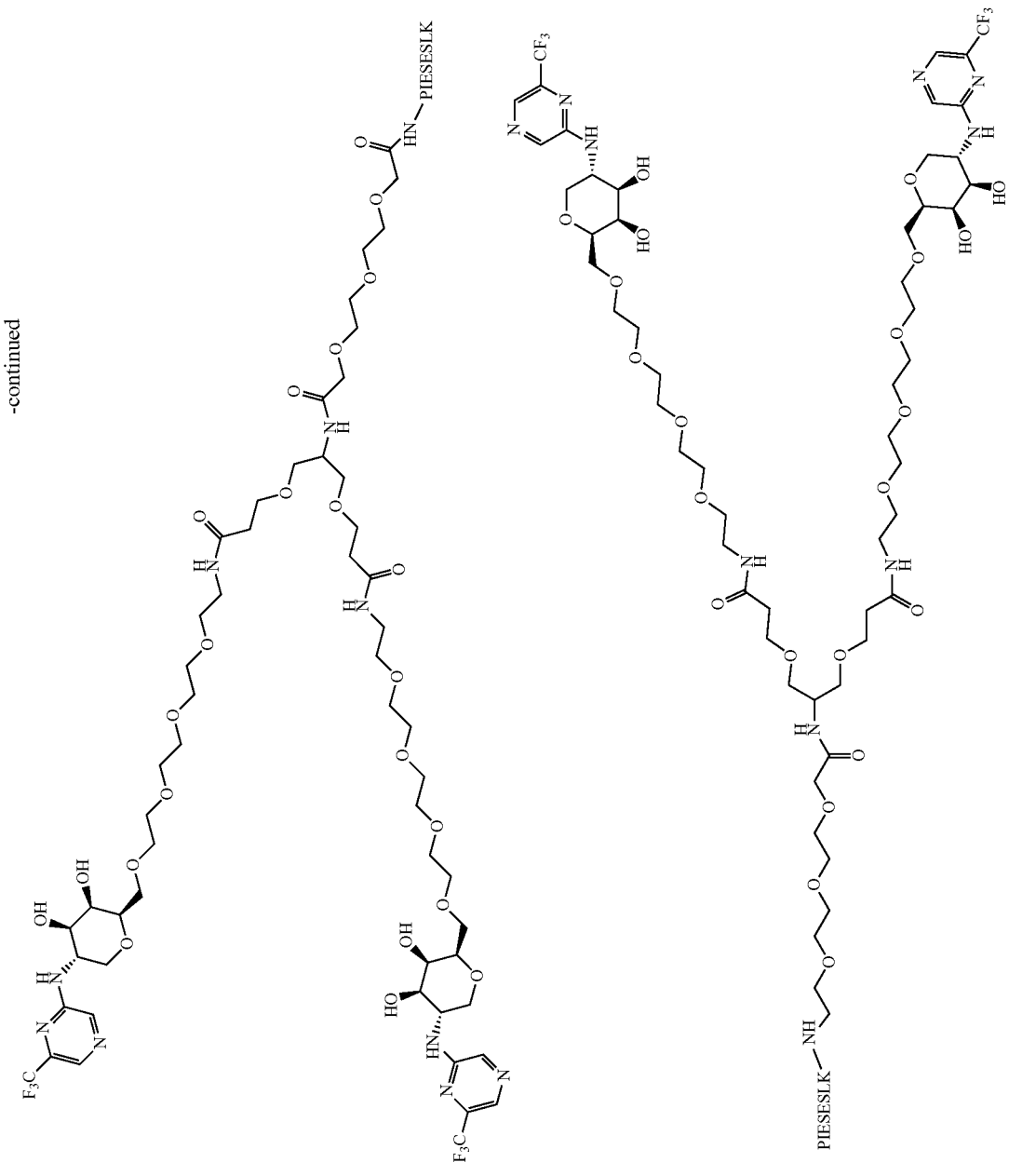

421
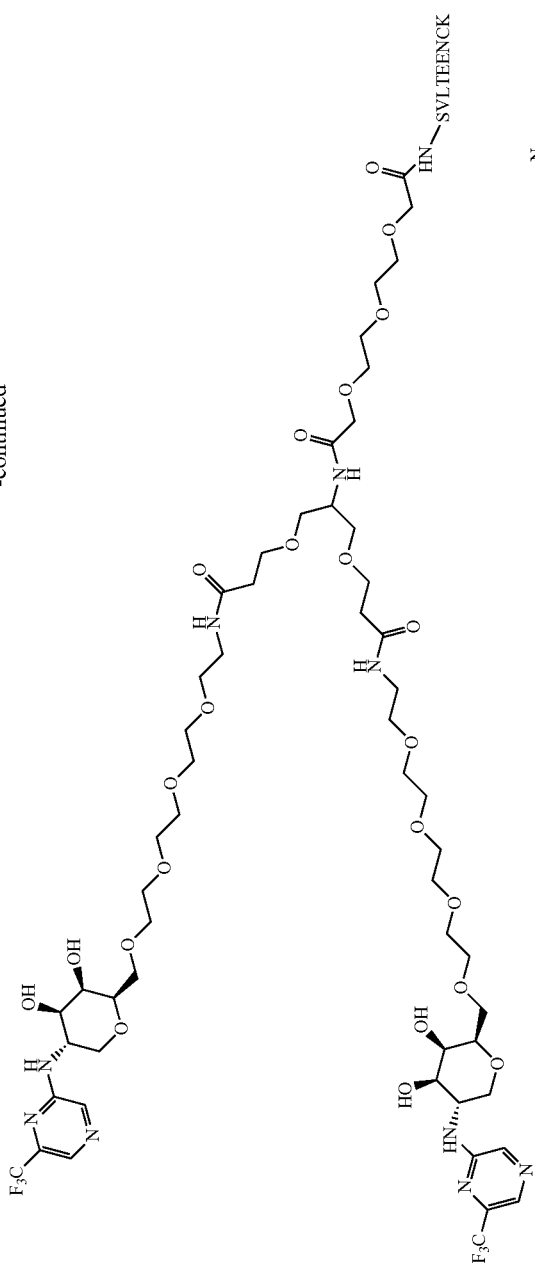
422
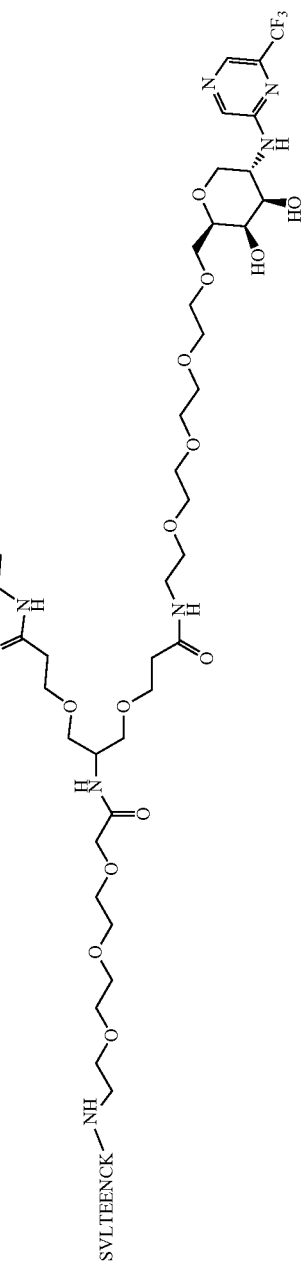

Complement C3

In some embodiments the Target Extracellular Protein is complement C3. Complement C3 is one of the major proteins involved in the complement response, a significant factor in both innate and adaptive immunity. Elevated C3 is associated with Paroxysmal nocturnal hemoglobinuria (PNH), immune complex membranoproliferative glomerulonephritis (IC-MPGN), C3 glomerulopathy (C3G), geographic (GA), age-related macular degeneration (AMD), periodontitis, amyotrophic lateral sclerosis (ALS), hematopoietic stem cell transplantation-associated thrombotic microangiopathy (HSCT-TMA), cold agglutinin disease (CAD) and host attack in gene therapies. Reduction of C3 levels may ameliorate some of the symptoms or complications that arise from these inflammatory diseases.

The Protein Data Bank website provides the crystal structure of complement C3, searchable by 2A73 (Janssen, B. J. Nature, 2005, 505-511). Complement C3 bound to a nanobody inhibitor can be found with PDB accession code 6EHG (Jensen, R. K. et al. J Biol Chem, 2018, 293, 6269-6281). Nonlimiting examples of complement C3 binding ligands include

```
                                           SEQ ID NO: 153
D-Tyr-Ile-[Cys-Val-1MeTrp-Gln-Asp-Trp-Sar-Ala-
His-Arg-Cys]-meIle (Zhang, Y. et al. 2015,
Immunobiology, 220, 993-998)

SEQ ID NO: 154
ICVVQDWGHHRCTAGMANLTSHASAI, (Sahu, A. et al. The
Journal of Immunology, 1996, 157, 884-891).

SEQ ID NO: 155
ICVVQDWGHHRCT, (Sahu, A. et al. The Journal of
Immunology, 1996, 157, 884-891).

SEQ ID NO: 156
CVVQDWGHHAC (Sahu, A. et al. The Journal of
Immunology, 1996, 157, 884-891).

SEQ ID NO: 157
Ac-ICVVQDWGHHRCT-NH₂, (Sahu, The Journal of
Immunology, 2000, 165, 2491-2499);

SEQ ID NO: 158
CVVQDWGHHRCT-NH₂, (Sahu, The Journal of
Immunology, 2000, 165, 2491-2499);

SEQ ID NO: 159
CVVQDWGHHRC-NH₂, (Sahu, The Journal of
Immunology, 2000, 165, 2491-2499);

SEQ ID NO: 160
Ac-ICVVGDWGHHRCT-NH₂, (Sahu, The Journal of
Immunology, 2000, 165, 2491-2499);

SEQ ID NO: 161
Ac-I*CVVQPWGHHRC*T-NH₂, (Sahu, The Journal of
Immunology, 2000, 165, 2491-2499);

SEQ ID NO: 162
Biotin-KYSSI*CVVQDWGHHRC*T-NH₂, (Sahu, The Journal
of Immunology, 2000, 165, 2491-2499);

SEQ ID NO: 163
Ac-I*CVVQDWGHHRC*TAGHMANLTSHASAK-Biotin, (Sahu,
The Journal of Immunology, 2000, 165, 2491-2499);

SEQ ID NO: 164
Ac-ICV(1mW)QDWGAHRCT, (Risitano et al. Blood,
2014, 123, 2094)

SEQ ID NO: 165
yICV(ImW)QDW-Sar-AHRC-mI, (Risitano et al. Blood,
2014, 123, 2094)

SEQ ID NO: 166
PEG-yICV(1mW)QDW-Sar-AHRC-mI (Risitano et al.
Blood, 2014, 123, 2094)
```

A

Ac-Cp40-K

PEG-Cp40

Ac-Cp40-K-PEG

```
Ac-Ile-[Cys-Val-Trp-Gln-Asp-Trp-Gly-Ala-His-Arg-Cys]-Thr-NH2  (Qu,     SEQ ID NO: 167
H. et al. Immunobiology (2012) http://dx.doi.org/10.1016/j.imbio.2012.06.003)

SEQ ID NO: 168
Ac-Ile-[Cys-Val-Trp(Me)-Gln-Asp-Trp-Sar-Ala-His-Arg-Cys]-Ile-NH2
(Qu, H. et al. Immunobiology (2012) http://dx.doi.org/10.1016/j.imbio.2012.06.003)

SEQ ID NO: 169
Ac-Ile-[Cys-Val-Trp(Me)-Gln-Asp-Trp-Sar-Ala-His-Arg-Cys]-mIle-NH2
(Qu, H. et al. Immunobiology (2012) http://dx.doi.org/10.1016/j.imbio.2012.06.003)

SEQ ID NO: 170
Ac-Ile-[Cys-Val-Trp(Me)-Gln-Asp-Trp-Gly-Ala-His-Arg-Cys]-Thr-NH2)
(Qu, H. et al. Molecular Immunology, 2011, 48, 481)

SEQ ID NO: 171
Ac-Xaa1-[Cys2-Val3-Xaa4-Gln5-Asp6-Trp7-Gly8-Xaa9-Xaa10-Xaa11-
Cys12]-Thr13-NH2 (Mallik et al. J. Med. Chem., 2005, 48, 274-286)

SEQ ID NO: 172
Ac-I[CVVQDWGHHRC]T-NH2 (Mallik et al. J. Med. Chem., 2005, 48,
274-286)

SEQ ID NO: 173
Ac-I[CVVQDWGAHRC]T-NH2 (Mallik et al. J. Med. Chem., 2005, 48,
274-286)

SEQ ID NO: 174
Ac-I[CVTQDWGHHRC]T-NH2 (Mallik et al. J. Med. Chem., 2005, 48,
274-286)

SEQ ID NO: 175
Ac-I[CVSQDWGHHRC]T-NH2 (Mallik et al. J. Med. Chem., 2005, 48,
274-286)

SEQ ID NO: 176
Ac-I[CVHQDWGHHRC]T-NH2, (Mallik et al. J. Med. Chem., 2005, 48,
274-286)

SEQ ID NO: 177
Ac-I[CVFQDWGHHRC]T-NH2, (Mallik et al. J. Med. Chem., 2005, 48,
274-286)

SEQ ID NO: 178
Ac-I[CVYQDWGAHRC]T-NH2, (Mallik et al. J. Med. Chem., 2005, 48,
274-286)

SEQ ID NO: 179
Ac-I[CVWQDWGWHRC]T-NH2, (Mallik et al. J. Med. Chem., 2005, 48,
274-286)

SEQ ID NO: 180
Ac-I[CVWQDWGHHRC]T-NH2, (Mallik et al. J. Med. Chem., 2005, 48,
274-286)

SEQ ID NO: 181
Ac-I[CVWQDWGAHRC]T, (Mallik et al. J. Med. Chem., 2005, 48, 274-
286)

SEQ ID NO: 182
Ac-I[CVWQDWGAHRC]T-NH2, (Mallik et al. J. Med. Chem., 2005, 48,
274-286)

SEQ ID NO: 183
Ac-I[CVWQDWGAdHRC]T, (Mallik et al. J. Med. Chem., 2005, 48, 274-
286)

SEQ ID NO: 184
Ac-I[CVWQDWGdAHRC]T, (Mallik et al. J. Med. Chem., 2005, 48, 274-
286)

SEQ ID NO: 185
Ac-dI[CVWQDWGAHRC]T, (Mallik et al. J. Med. Chem., 2005, 48, 274-
286)

SEQ ID NO: 186
Ac-I[CVWQDWGAHRC]dT, (Mallik et al. J. Med. Chem., 2005, 48, 274-
286)
```

-continued

Ac-I[CVWQDWGAHRC]T-NH$_2$, (Lopez de Victoria, A. et al. Chem Biol Drug Des 2011, 77, 431-440)
SEQ ID NO: 187

W[CVWQDWGTNRC]W-NH$_2$, (Lopez de Victoria, A. et al. Chem Biol Drug Des 2011, 77, 431-440)
SEQ ID NO: 188

Ac-D[CVWQDWGTNKC]W-NH$_2$, (Lopez de Victoria, A. et al. Chem Biol Drug Des 2011, 77, 431-440)
SEQ ID NO: 189

Q[CVWQDWGQNQC]W-NH$_2$, (Lopez de Victoria, A. et al. Chem Biol Drug Des 2011, 77, 431-440)
SEQ ID NO: 190

Ac-I[CVWQDWGAHRC]W-NH$_2$, (Lopez de Victoria, A. et al. Chem Biol Drug Des 2011, 77, 431-440)
SEQ ID NO: 191

Ac-W[CVWQDWGAHRC]T-NH$_2$, (Lopez de Victoria, A. et al. Chem Biol Drug Des 2011, 77, 431-440)
SEQ ID NO: 192

Ac-W[CVWQDWGAHRC]W-NH$_2$, (Lopez de Victoria, A. et al. Chem Biol Drug Des 2011, 77, 431-440)
SEQ ID NO: 193

Ac-Ile-[Ala-Val-Trp-Gln-Asp-Trp-Gly-Ala-His-Arg-Hcy]-Thr-NH$_2$, (Knerr, P. et al. ACS Chem. Biol., 2011, 6, 753-760)
SEQ ID NO: 194

Ac-Ile-[Cys-Val-Trp-Gln-Asp-Trp-Gly-Ala-His-Arg-Cys]-(NMeIle)-NH$_2$, (Knerr, P. et al. ACS Chem. Biol., 2011, 6, 753-760)
SEQ ID NO: 195

Ac-Ile-[Ala-Val-Trp-Gln-Asp-Trp-Gly-Ala-His-Arg-Hcy]-(NMeIle)-NH$_2$, (Knerr, P. et al. ACS Chem. Biol., 2011, 6, 753-760)
SEQ ID NO: 196

Ac-ICV(5fW)QDWGAHRCT-NH$_2$, (Katragadda et al. J. Med. Chem. 2006, 49, 4616-4622).
SEQ ID NO: 197

Ac-ICV(5MeW)QDWGAHRCT-NH$_2$, (Katragadda et al. J. Med. Chem. 2006, 49, 4616-4622).
SEQ ID NO: 198

Ac-ICV(2Nal)QDWGAHRCT-NH$_2$, (Katragadda et al. J. Med. Chem. 2006, 49, 4616-4622).
SEQ ID NO: 199

Ac-ICVWQD(5fW)GAHRCT-NH$_2$, (Katragadda et al. J. Med. Chem. 2006, 49, 4616-4622).
SEQ ID NO: 200

Ac-ICVWQD(5MeW)GAHRCT-NH$_2$, (Katragadda et al. J. Med. Chem. 2006, 49, 4616-4622).
SEQ ID NO: 201

Ac-ICVWQD(1MeW)GAHRCT-NH$_2$, (Katragadda et al. J. Med. Chem. 2006, 49, 4616-4622).
SEQ ID NO: 202

Ac-ICVYQDWGAHRCT-CONH2, (WO 2021/007, 111)
SEQ ID NO: 203

Ac-ICVWQDWGAHRCT-COOH, (WO 2021/007, 111)
SEQ ID NO: 204

Ac-ICVWQDWGAHRCT-CONH2, (WO 2021/007, 111)
SEQ ID NO: 205

Ac-ICVWQDWGAHRCdT-COOH, (WO 2021/007, 111)
SEQ ID NO: 206

-continued

| | |
|---|---|
| Ac-ICV(2-Nal)QDWGAHRCT-CONH2, (WO 2021/007, 111) | SEQ ID NO: 207 |
| Ac-ICV(2-Nal)QDWGAHRCT-COOH, (WO 2021/007, 111) | SEQ ID NO: 208 |
| Ac-ICV(1-Nal)QDWGAHRCT-COOH, (WO 2021/007, 111) | SEQ ID NO: 209 |
| Ac-ICV(2-lal)QDWGAHRCT-CONH2, (WO 2021/007, 111) | SEQ ID NO: 210 |
| Ac-ICV(2-lal)QDWGAHRCT-COOH, (WO 2021/007, 111) | SEQ ID NO: 211 |
| Ac-ICVDhtQDWGAHRCT-COOH, (WO 2021/007, 111) | SEQ ID NO: 212 |
| Ac-ICV(Boa)QDWGAHRCT-COOH, (WO 2021/007, 111) | SEQ ID NO: 213 |
| Ac-ICV(Bpa)QDWGAHRCT-CONH2, (WO 2021/007, 111) | SEQ ID NO: 214 |
| Ac-ICV(Bta)QDWGAHRCT-COOH, (WO 2021/007, 111) | SEQ ID NO: 215 |
| Ac-ICV(Bta)QDWGAHRCT-CONH2, (WO 2021/007, 111) | SEQ ID NO: 216 |
| Ac-ICVWQDWG(2-Abu)HRCT-CONH2, (WO 2021/007, 111) | SEQ ID NO: 217 |
| H-GICVWQDWGAHRCTAN-COOH, (WO 2021/007, 111) | SEQ ID NO: 218 |
| Ac-ICV(5fW)QDWGAHRCT-CONH2, (WO 2021/007, 111) | SEQ ID NO: 219 |
| Ac-ICV(5-methyl-W)QDWGAHRCT-CONH2, (WO 2021/007, 111) | SEQ ID NO: 220 |
| Ac-ICV(1-methyl-W)QDWGAHRCT-CONH2, (WO 2021/007, 111) | SEQ ID NO: 221 |
| Ac-ICVWQD(5fW)GAHRCT-CONH2, (WO 2021/007, 111) | SEQ ID NO: 222 |
| Ac-ICV(5fW)QD(5fW)GAHRCT-CONH2, (WO 2021/007, 111) | SEQ ID NO: 223 |
| Ac-ICV(5-methyl-W)QD(5fW)GAHRCT-CONH2, (WO 2021/007, 111) | SEQ ID NO: 224 |
| Ac-ICV(1-methyl-W)QD(5fW)GAHRCT-CONH2, (WO 2021/007, 111) | SEQ ID NO: 225 |
| H-GICV(6fW)QD(6fW)GAHRCTN-COOH, (WO 2021/007, 111) | SEQ ID NO: 226 |
| Ac-ICV(1-formyl-W)QDWGAHRCT-CONH2, (WO 2021/007, 111) | SEQ ID NO: 227 |
| Ac-ICV(1-methyoxy-W)QDWGAHRCT-CONH2, (WO 2021/007, 111) | SEQ ID NO: 228 |
| H-GICV(5fW)QD(5fW)GAHRCTN-COOH, (WO 2021/007, 111) | SEQ ID NO: 229 |

In certain embodiments the complement C3 targeting ligand is
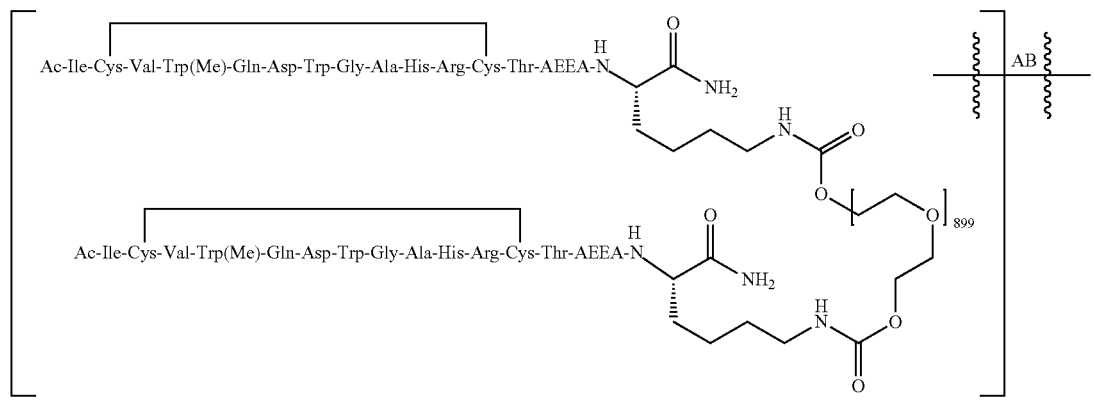
In certain embodiments the complement C3 Targeting Ligand is selected from:
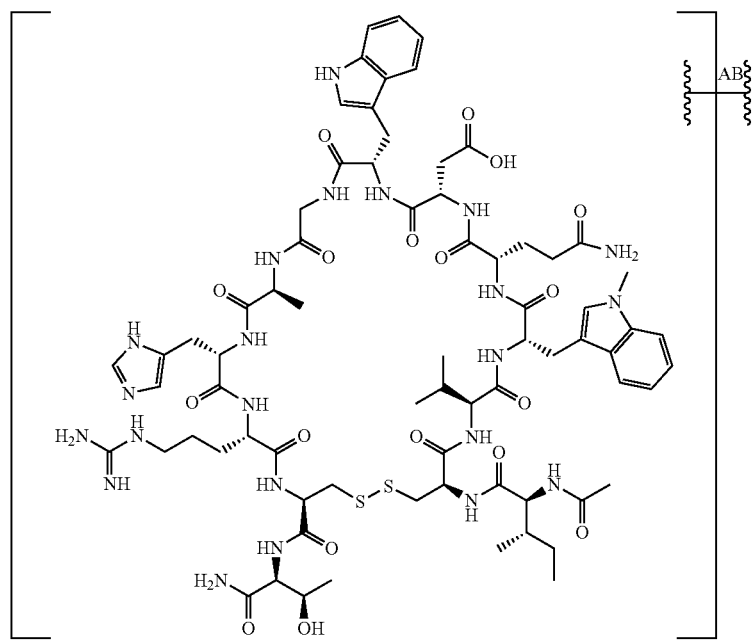

433
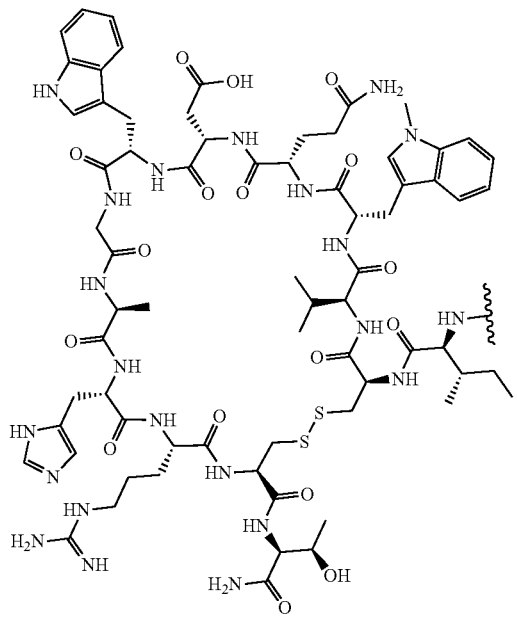
434
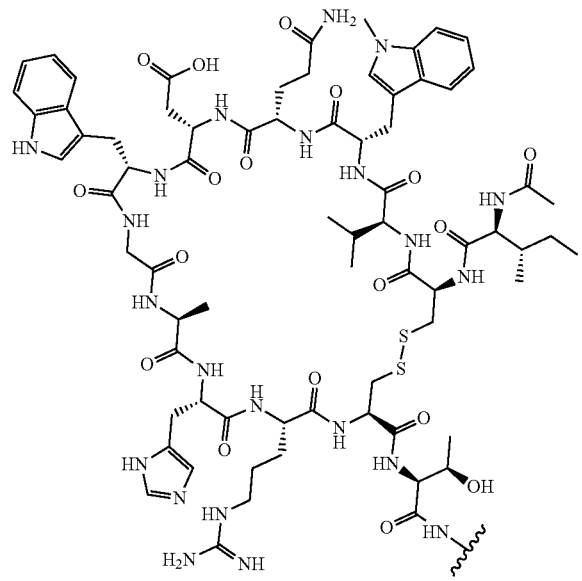
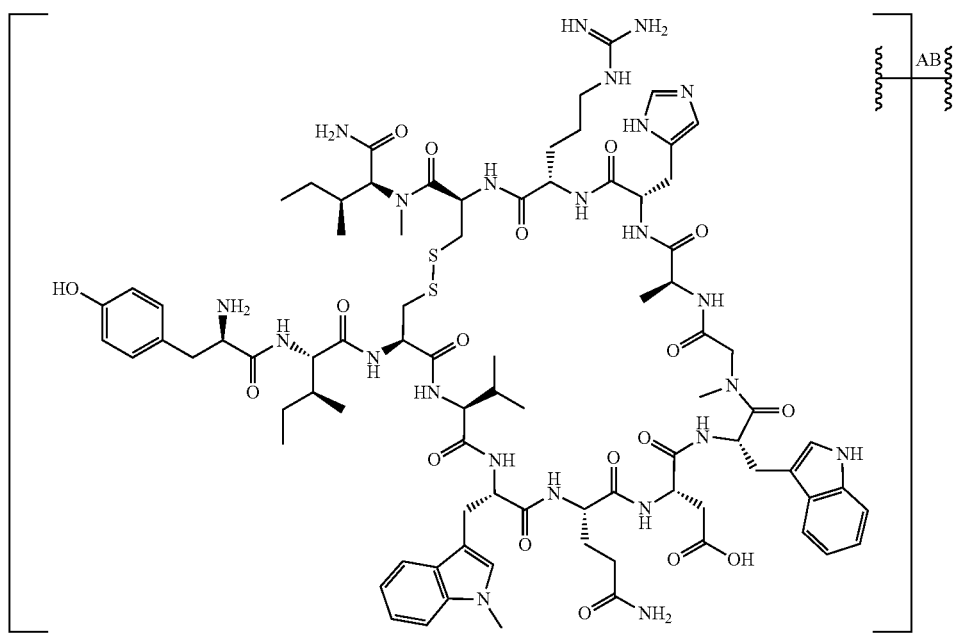

-continued
435
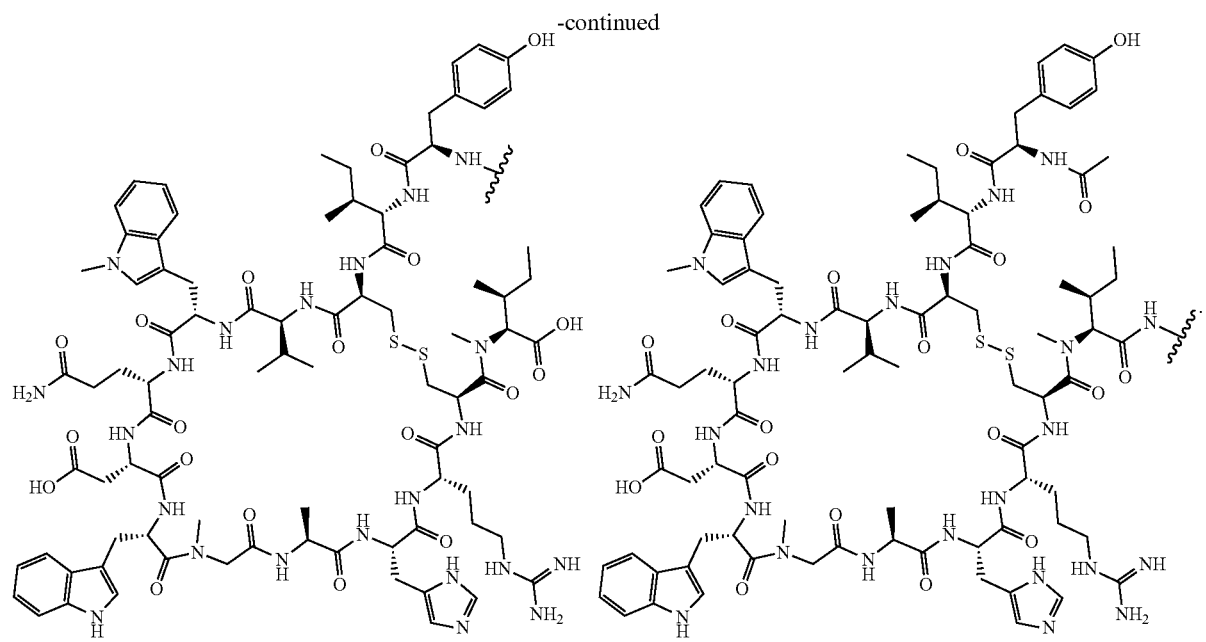
436
Non-limiting examples of Complement C3 degrading compounds include:

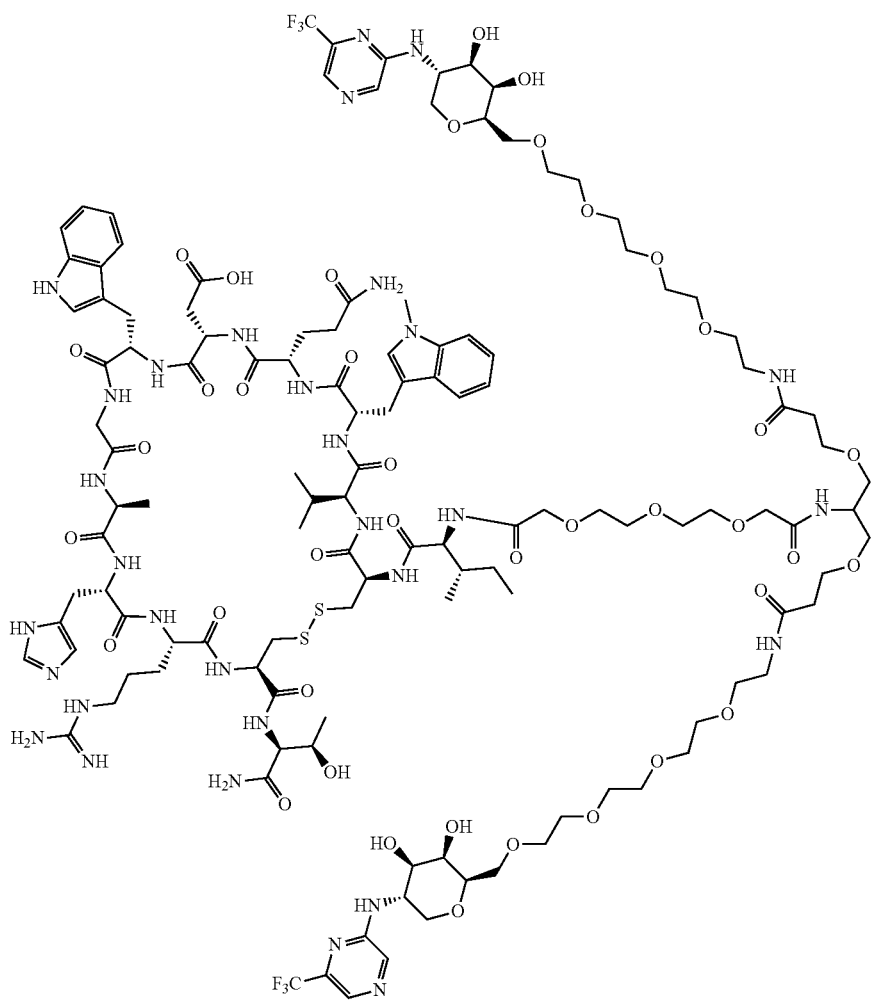

-continued
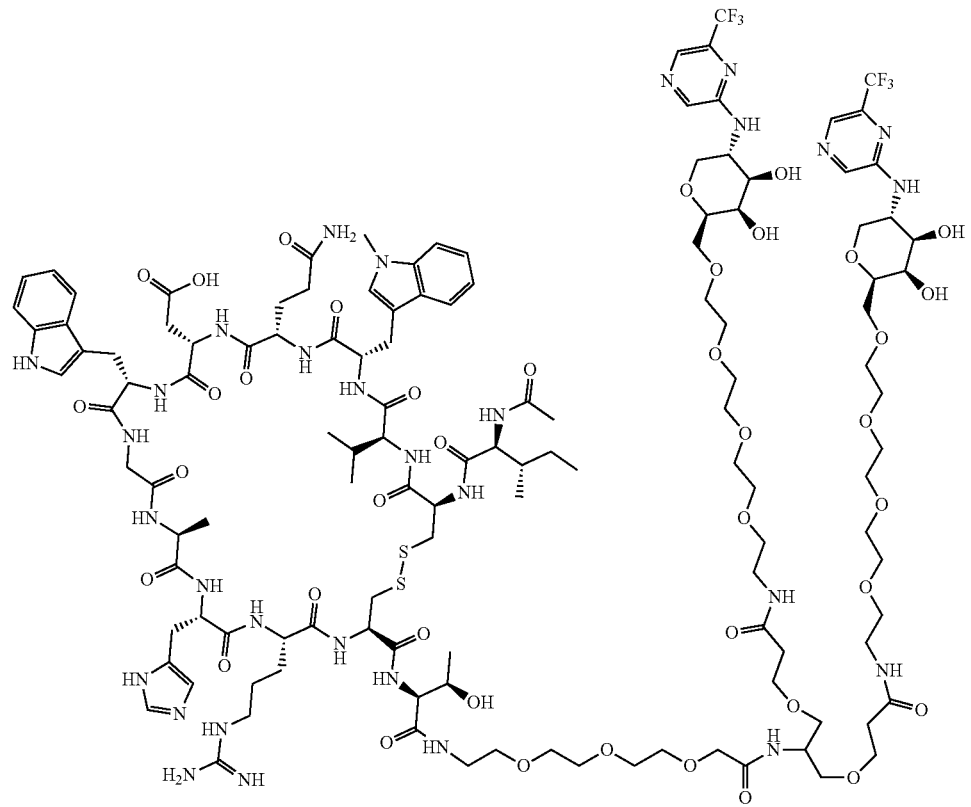
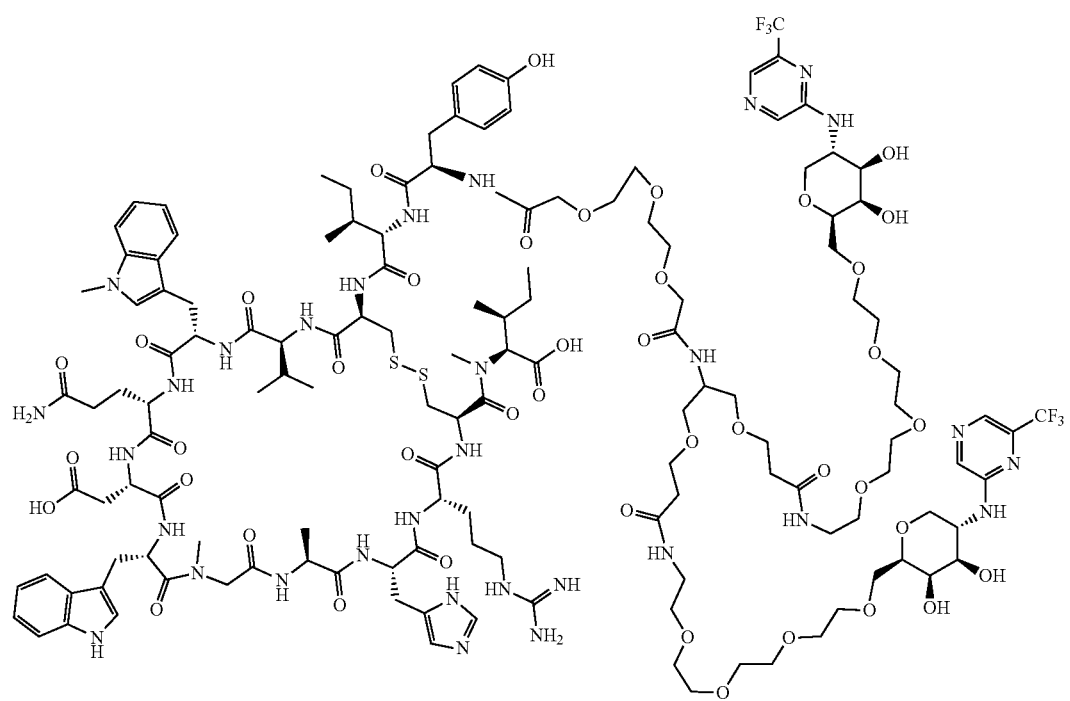

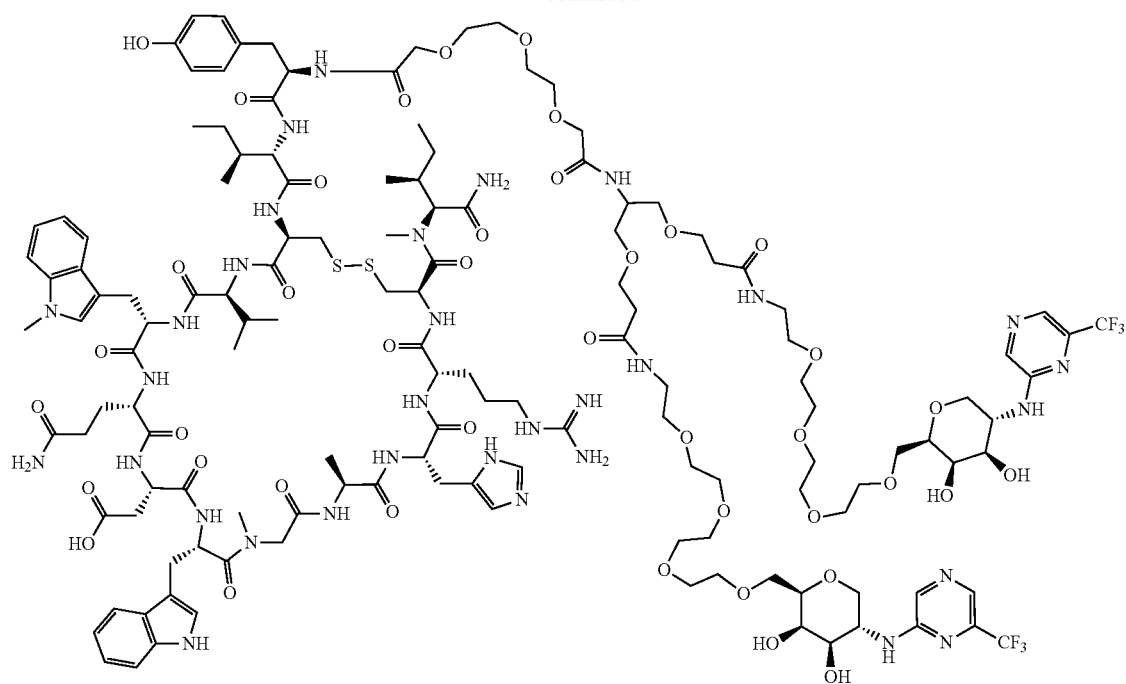
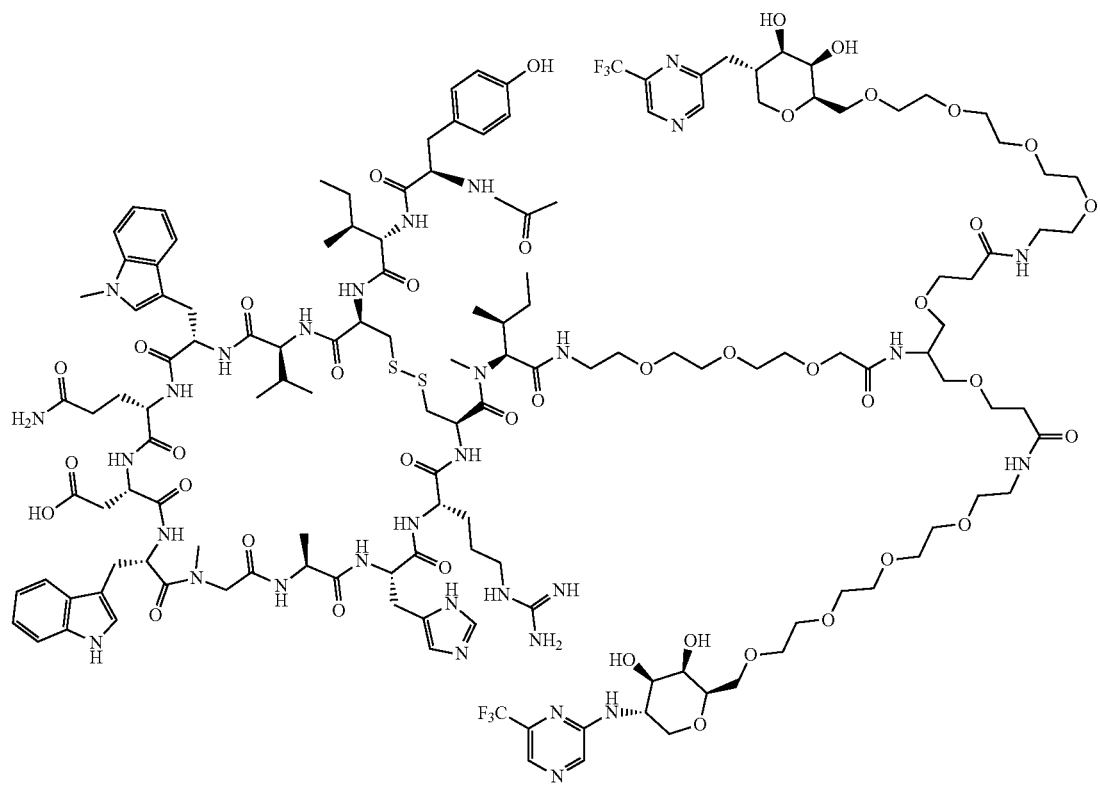

In certain non-limiting embodiments, the Complement C3 degrading compound of the present invention is selected from the following compounds or a bi- or tri-dentate version thereof:
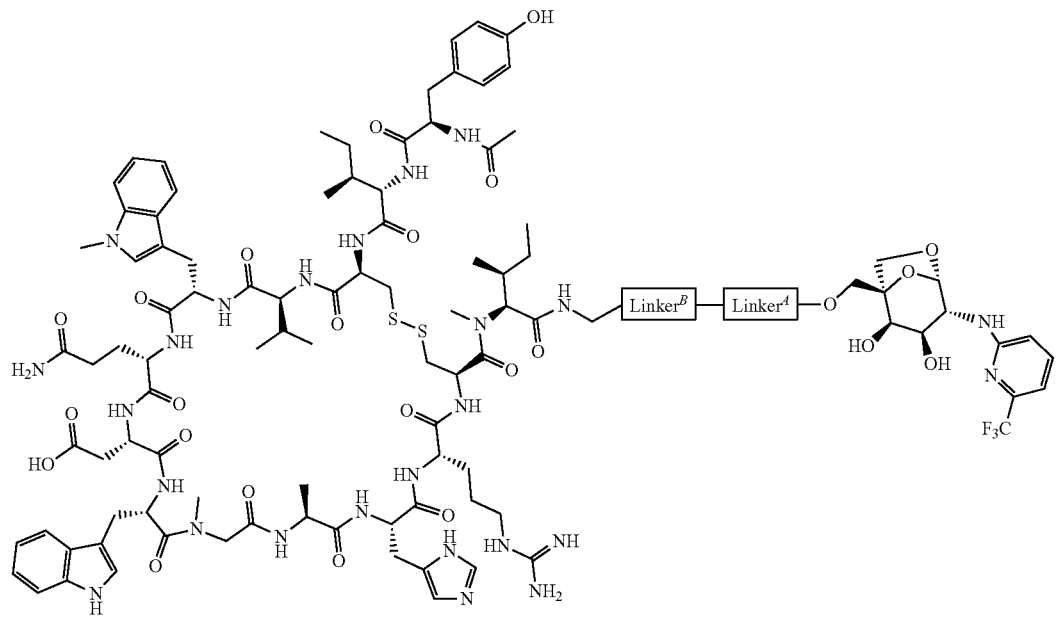
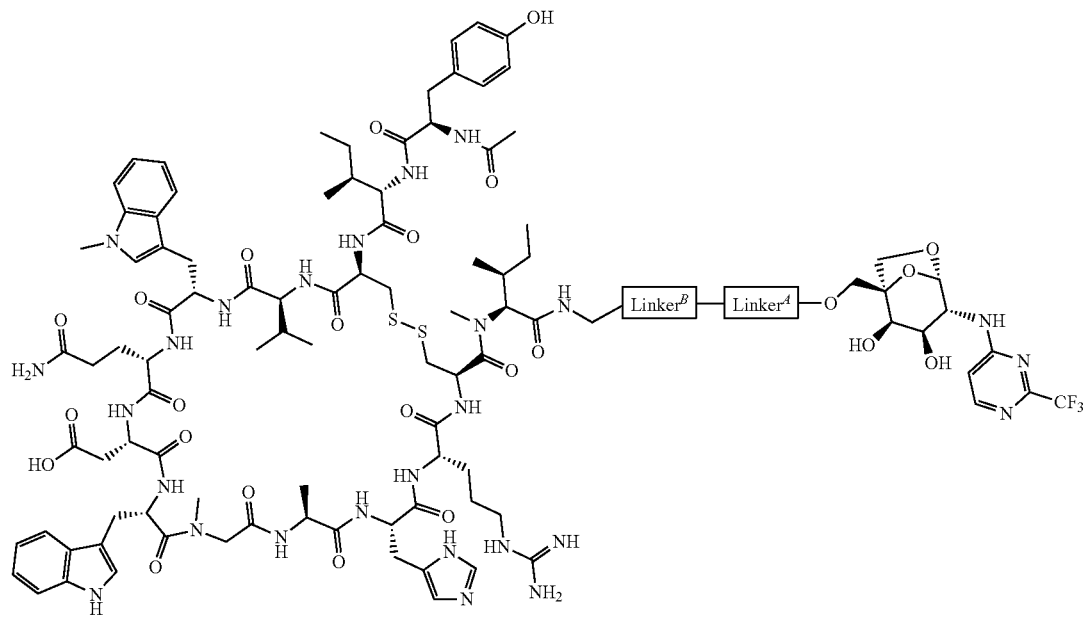

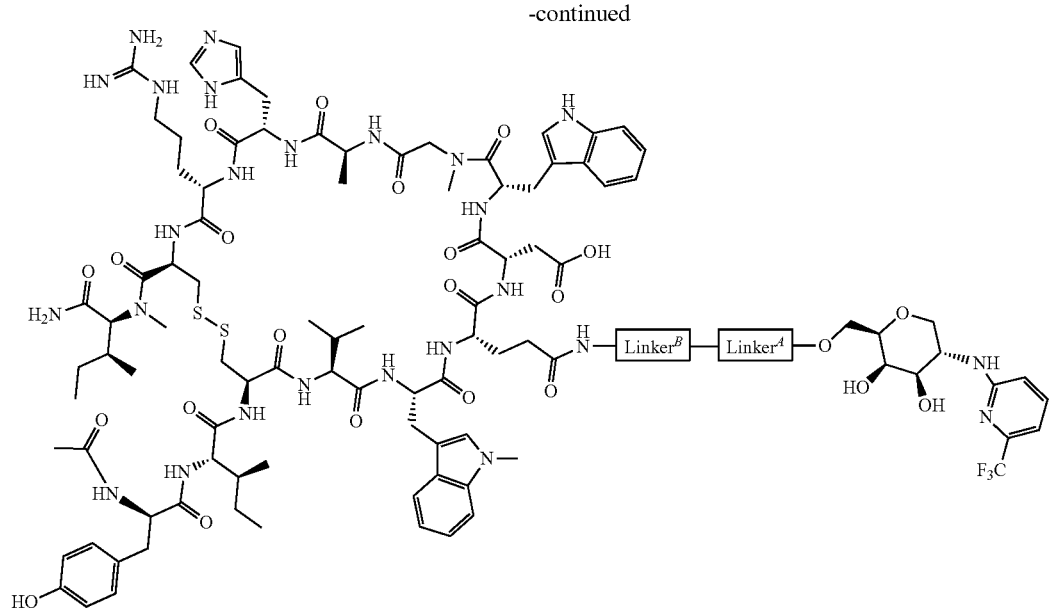
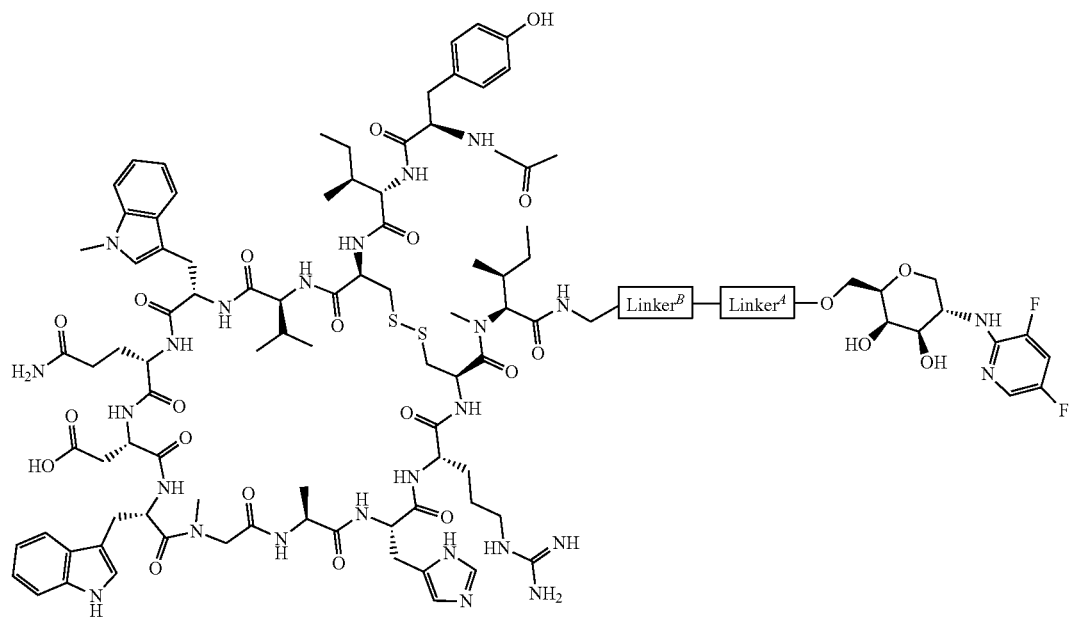

-continued
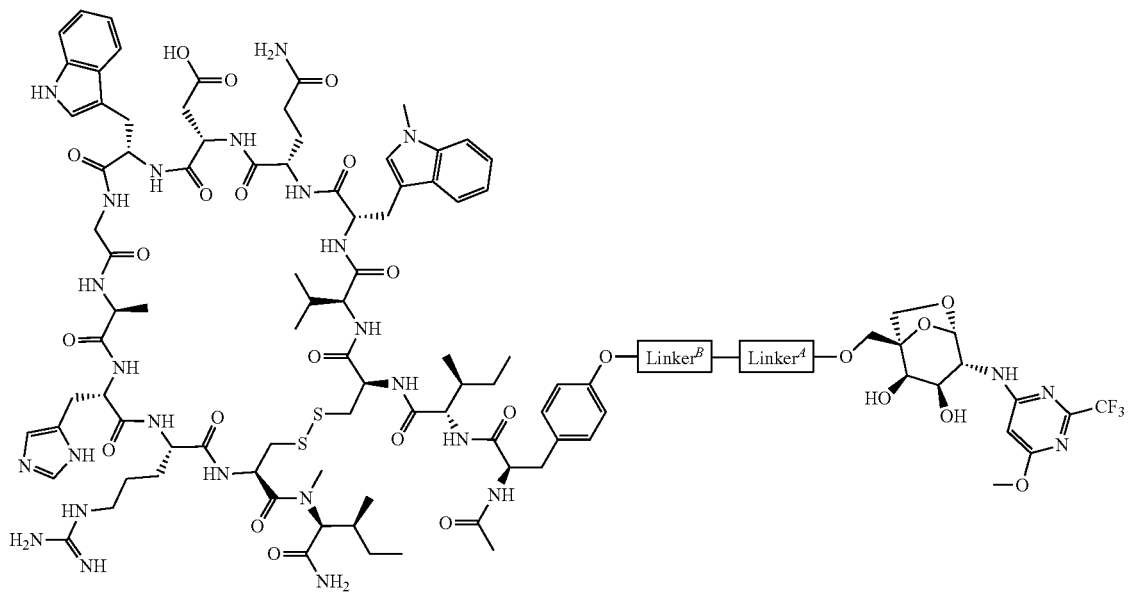
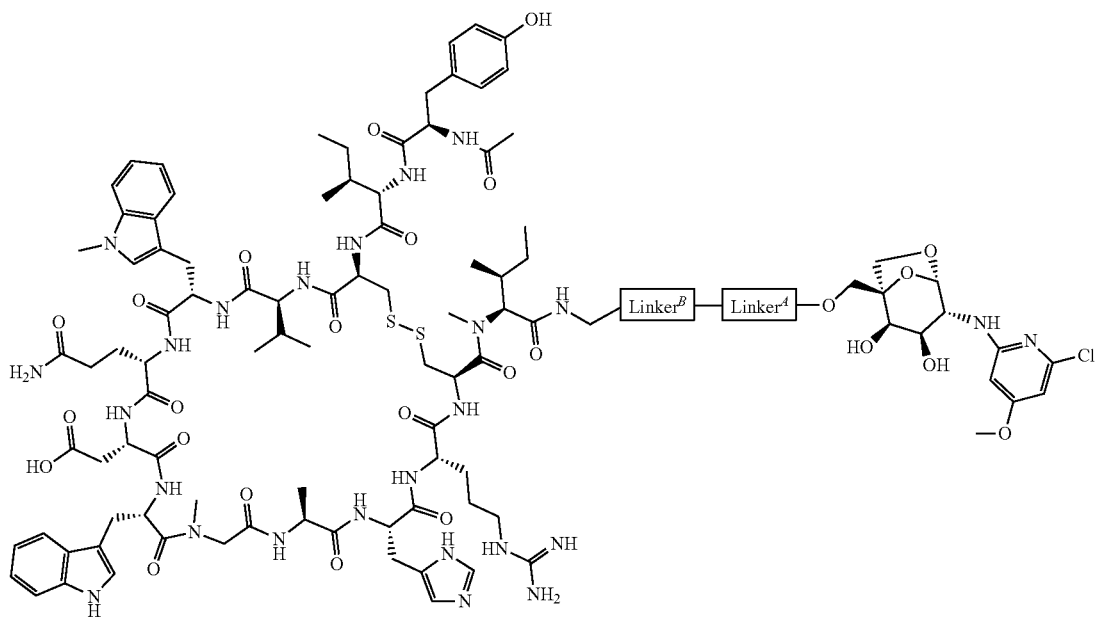

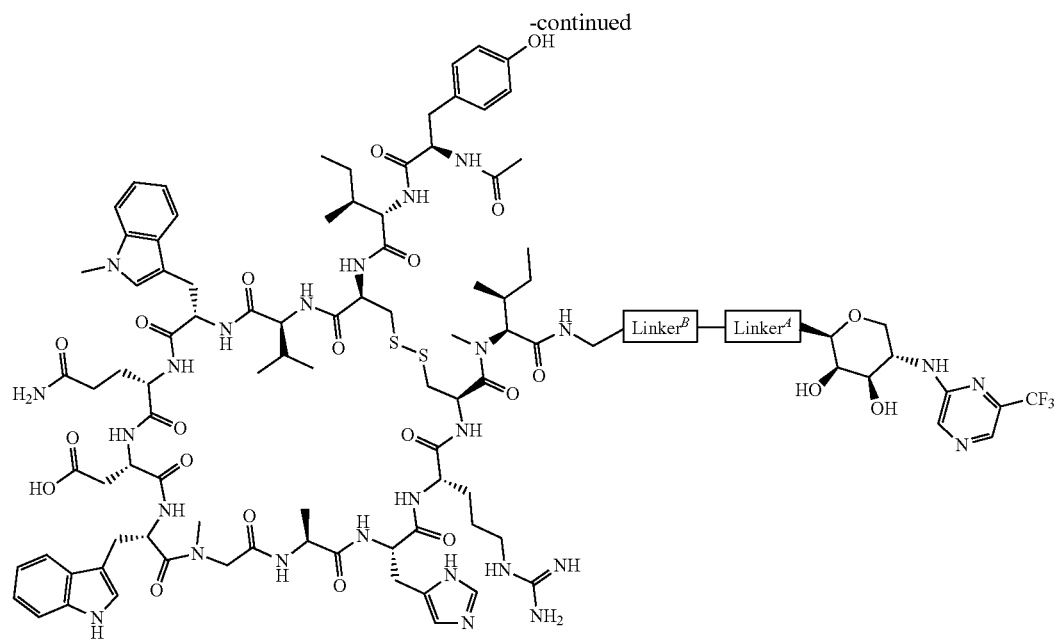
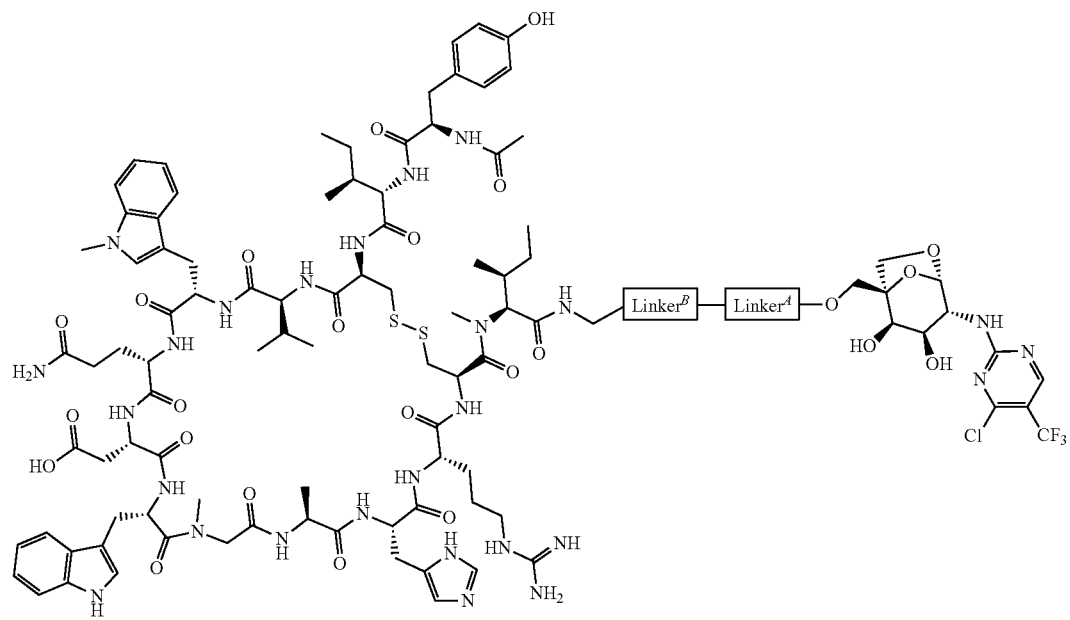

-continued
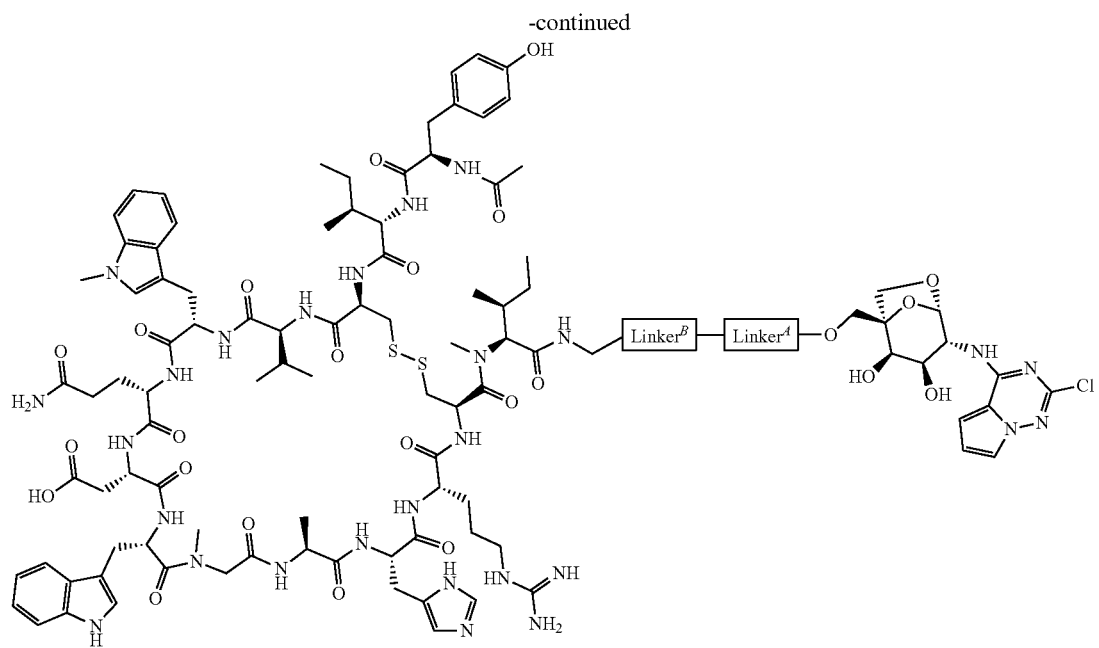
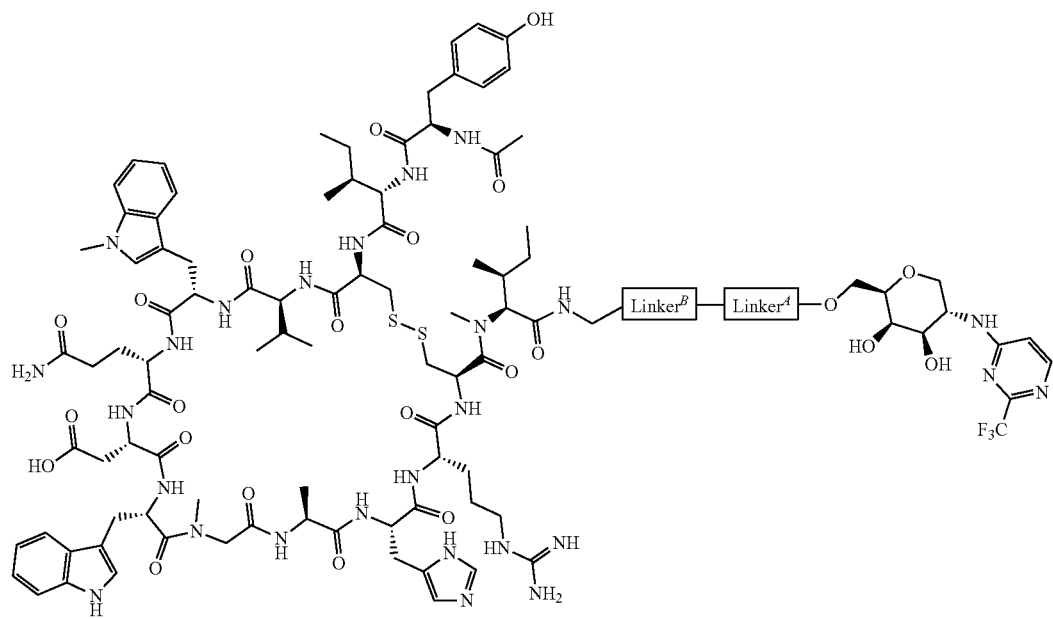

-continued
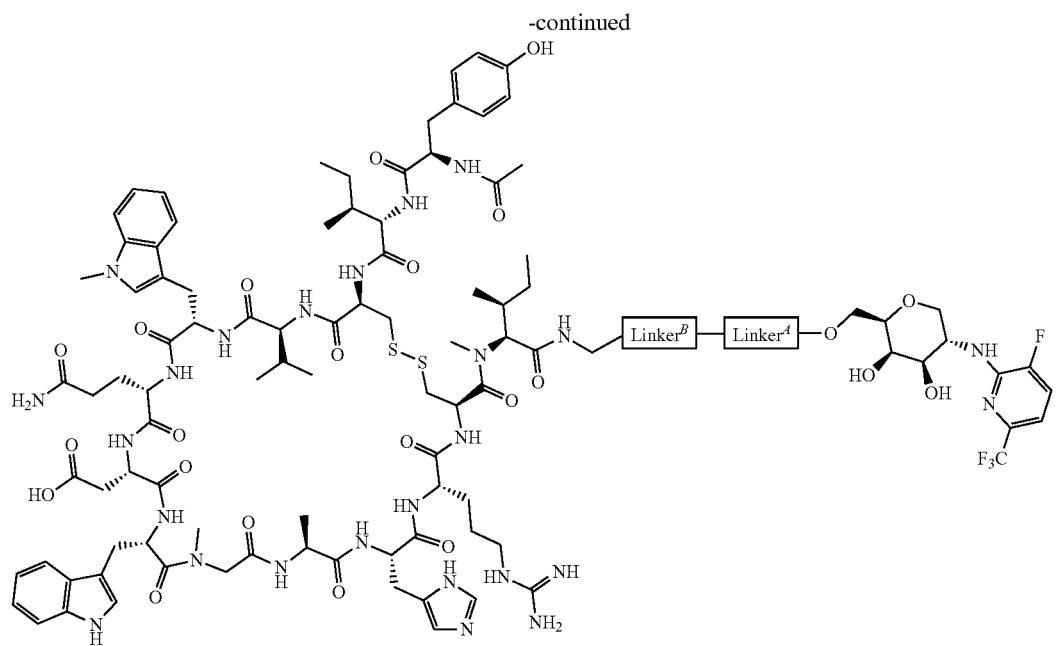
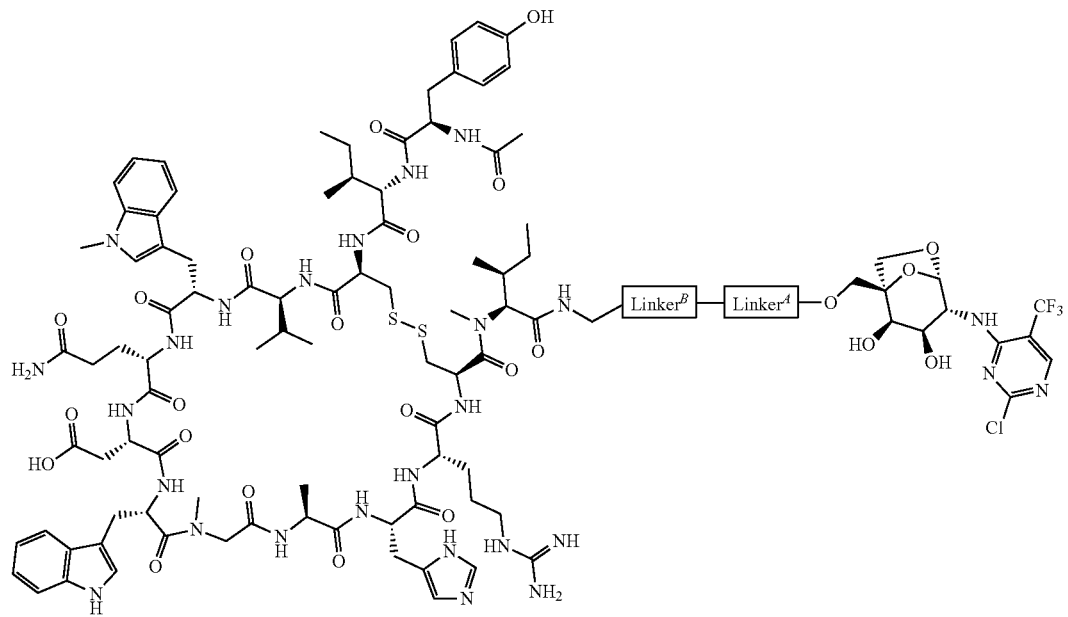

-continued

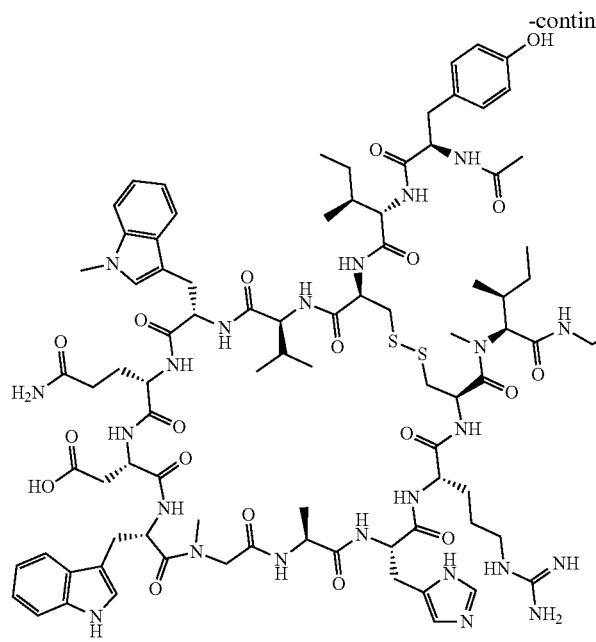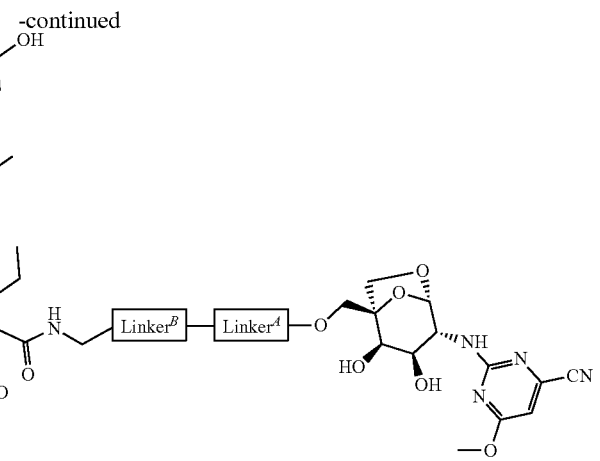

Complement C1q

In some embodiments, the Target Extracellular Protein is Complement C1q. The complement system is part of the innate immune system and clears apoptotic cells and pathogens. Activation of this pathway begins with binding the C1 complex to an immunoglobulin that has bound to an antigen. The C1 complex consists of C1q and a tetramer of proteases (C1r and C1s). C1q mediates the binding of complement to IgG or IgM. Following the binding event, the proteases are activated, and they cleave C4 which sets off the remainder of the pathway that ends in opsonization. Overactivity of this pathway can lead to a number of inflammatory pathologies including allograft rejection, neuromyelitis optica, generalized myasthenia gravis, and cold agglutinin disease. Degradation of C1q may reduce the symptoms associated with these inflammatory diseases.

The Protein Data Bank website provides the crystal structure of Complement C1q searchable by 2JG9 (Paidassi, H. et al., J. Immunol, 2008, 180, 2329-2338), 1PK6 (Gaboriaud, C., J. Biol. Chem, 2003, (278) 46974-46982), 5HZF (Moreau, C. et al., Front. Immunol, 2016, (7) 79), 2WNV and 2WNU (Garlatti, V. et. al., J. Immunol. 2010, (185), 808). Also provided on the PDB website is the structure of complement C1q with a ligand bound, searchable by 6Z67 (Laursen, N. et al. Front. Immunol., 2020, (11), 1504)

Nonlimiting examples of complement C1q binding ligands include

```
                                                         SEQ ID NO: 230
Ac-Ala-Glu-Ala-Lys-Ala-Lys-Ala-CONH2  (WO 88/07054)

SEQ ID NO: 231
IALILEPICCQERAA  (Sharp, J. A. et al. PLOS ONE 10(7), e0132446)

SEQ ID NO: 232
IALILEPICCQERAA-dPEG24  (Sharp, J. A. et al. PLOS ONE 10(7),
e0132446)

SEQ ID NO: 233
dPEG24-IALILEPICCQERAA  (Sharp, J. A. et al. PLOS ONE 10(7),
e0132446)

SEQ ID NO: 234
RALILEPICCQERAA  (Sharp, J. A. et al. PLOS ONE 10(7), e0132446)

SEQ ID NO: 235
IRLILEPICCQERAA  (Sharp, J. A. et al. PLOS ONE 10(7), e0132446)

SEQ ID NO: 236
IARILEPICCQERAA  (Sharp, J. A. et al. PLOS ONE 10(7), e0132446)

SEQ ID NO: 237
IALIREPICCQERAA  (Sharp, J. A. et al. PLOS ONE 10(7), e0132446)

SEQ ID NO: 238
IALILEPICCRERAA  (Sharp, J. A. et al. PLOS ONE 10(7), e0132446)
```

-continued

SEQ ID NO: 239
IALILEPICCORRAA (Sharp, J. A. et al. PLOS ONE 10(7), e0132446)

SEQ ID NO: 240
IELILEPICCQERAA (Sharp, J. A. et al. PLOS ONE 10(7), e0132446)

SEQ ID NO: 241
IAEILEPICCQERAA (Sharp, J. A. et al. PLOS ONE 10(7), e0132446)

SEQ ID NO: 242
IALILEPICCQEEAA (Sharp, J. A. et al. PLOS ONE 10(7), e0132446)

SEQ ID NO: 243
IALILEPICCQEREA (Sharp, J. A. et al. PLOS ONE 10(7), e0132446)

SEQ ID NO: 244
IALILEEICCQERAA (Sharp, J. A. et al. PLOS ONE 10(7), e0132446)

SEQ ID NO: 245
IALILEPECCQERAA (Sharp, J. A. et al. PLOS ONE 10(7), e0132446)

SEQ ID NO: 246
PAICQRATATLGTVGSNTSGTTAIEACILL (Sharp, J. A. et al. Frontiers in Immunology (2014) 5, 406)

SEQ ID NO: 247
CEGPFGPRHDLTFCW (Roos, A. et al. The Journal of Immunology, 2001, 167, 7052)

SEQ ID NO: 248
XbEGPFGPRHDLTFCW (Roos, A. et al. The Journal of Immunology, 2001, 167, 7052)

SEQ ID NO: 249
QYYPFSX (Messmer B.T. et al. Molecular Immunology, 2000, 37, 343)

SEQ ID NO: 250
NPFNLAR (Messmer B.T. et al. Molecular Immunology, 2000, 37, 343)

SEQ ID NO: 251
QLQDMTSSPFWL (Messmer B.T. et al. Molecular Immunology, 2000, 37, 343)

SEQ ID NO: 252
NPFVIGRWHPPH (Messmer B.T. et al. Molecular Immunology, 2000, 37, 343)

SEQ ID NO: 253
SLAKFLNPFLYR (Messmer B.T. et al. Molecular Immunology, 2000, 37, 343)

SEQ ID NO: 254
ASTPRFEPFQLD (Messmer B.T. et al. Molecular Immunology, 2000, 37, 343)

SEQ ID NO: 255
SLHSQPYSPFML (Messmer B.T. et al. Molecular Immunology, 2000, 37, 343)

SEQ ID NO: 256
NILSSWSSPFVF (Messmer B.T. et al. Molecular Immunology, 2000, 37, 343)

SEQ ID NO: 257
NLPSSWTNPFYL (Messmer B.T. et al. Molecular Immunology, 2000, 37, 343)

SEQ ID NO: 258
SPFMLHP (Messmer B.T. et al. Molecular Immunology, 2000, 37, 343)

SEQ ID NO: 259
PSPFMLT (Messmer B.T. et al. Molecular Immunology, 2000, 37, 343)

SEQ ID NO: 260
IGPFHLH (Messmer B.T. et al. Molecular Immunology, 2000, 37, 343)

SEQ ID NO: 261
TNPFMLN (Messmer B.T. et al. Molecular Immunology, 2000, 37, 343)

-continued

```
                                                 SEQ ID NO: 262
NTTFLYP (Messmer B.T. et al. Molecular Immunology, 2000, 37, 343)

SEQ ID NO: 263
SHYTQYL (Messmer B.T. et al. Molecular Immunology, 2000, 37, 343)

SEQ ID NO: 264
NHHPNYW (Messmer B.T. et al. Molecular Immunology, 2000, 37, 343)

SEQ ID NO: 265
VHYPLSW (Messmer B.T. et al. Molecular Immunology, 2000, 37, 343)

SEQ ID NO: 266
HHLKYSDTSPPI (Messmer B.T. et al. Molecular Immunology, 2000, 37,
343)

SEQ ID NO: 267
SHMHERWDTSPPI (Messmer B.T. et al. Molecular Immunology, 2000,
37, 343)

SEQ ID NO: 268
SHMHERWDTSYQ (Messmer B.T. et al. Molecular Immunology, 2000,
37, 343)

SEQ ID NO: 269
SHIHSNAAWRIT (Messmer B.T. et al. Molecular Immunology, 2000, 37,
343)

SEQ ID NO: 270
WHYPHWQ (Messmer B.T. et al. Molecular Immunology, 2000, 37, 343)

SEQ ID NO: 271
SHYLYTQ (Messmer B.T. et al. Molecular Immunology, 2000, 37, 343)

SEQ ID NO: 272
AHYSFTQ (Messmer B.T. et al. Molecular Immunology, 2000, 37, 343)

SEQ ID NO: 273
THYPTFY (Messmer B.T. et al. Molecular Immunology, 2000, 37, 343)

SEQ ID NO: 274
EHNTSFW (Messmer B.T. et al. Molecular Immunology, 2000, 37, 343)

SEQ ID NO: 275
NHYKLTW (Messmer B.T. et al. Molecular Immunology, 2000, 37, 343)

SEQ ID NO: 276
NHSPYFQ (Messmer B.T. et al. Molecular Immunology, 2000, 37, 343)

SEQ ID NO: 277
SHYQHYQ (Messmer B.T. et al. Molecular Immunology, 2000, 37, 343)

SEQ ID NO: 278
PAICQRATATLGTVGSNTSGTTEIEACILL (Gronemus, J.Q. et al.
Molecular immunology, 2010, 48, 305)

SEQ ID NO: 279
WLGLGGGYGW (Lauvrak V., Biol. Chem. 1997, 378, 1509)

SEQ ID NO: 280
FYGPFFLNDSLRGIW (Lauvrak V., Biol. Chem. 1997, 378, 1509)

SEQ ID NO: 281
LRFLNPFSLDGSGFW (Lauvrak V., Biol. Chem. 1997, 378, 1509)

SEQ ID NO: 282
HSPFCLGVLECFGLV (Lauvrak V., Biol. Chem. 1997, 378, 1509)

SEQ ID NO: 283
TCGAFYLYHDPFICG (Lauvrak V., Biol. Chem. 1997, 378, 1509)

SEQ ID NO: 284
MQHCLASHELYLPWC (Lauvrak V., Biol. Chem. 1997, 378, 1509)

SEQ ID NO: 285
FFVFGSGDAFAFSDM (Lauvrak V., Biol. Chem. 1997, 378, 1509)

SEQ ID NO: 286
PCVIIDTGSSRWCYL (Lauvrak V., Biol. Chem. 1997, 378, 1509)
```

-continued

SEQ ID NO: 287
HSPFCLGVLECFGLV (Lauvrak V., Biol. Chem. 1997, 378, 1509)

SEQ ID NO: 288
HAAFEPRGDVRHTLL (Lauvrak V., Biol. Chem. 1997, 378, 1509)

SEQ ID NO: 289
CRWDGSWGEVRC (Lauvrak V., Biol. Chem. 1997, 378, 1509)

SEQ ID NO: 290
CYWVGTWGEAVC (Lauvrak V., Biol. Chem. 1997, 378, 1509)

SEQ ID NO: 291
RWFPCPNKEGCCSISV (Lauvrak V., Biol. Chem. 1997, 378, 1509)

SEQ ID NO: 292
RSTYCNKNKDSCHIPE (Lauvrak V., Biol. Chem. 1997, 378, 1509)

SEQ ID NO: 293
QPPQCIKDGGFVICRV (Lauvrak V., Biol. Chem. 1997, 378, 1509)

SEQ ID NO: 294
KGKKCKPEEHPCNEPM (Lauvrak V., Biol. Chem. 1997, 378, 1509)

SEQ ID NO: 295
NKMTCSDDGKLCWEHL (Lauvrak V., Biol. Chem. 1997, 378, 1509)

SEQ ID NO: 296
PLGRPCPTCPLAPS (Lauvrak V., Biol. Chem. 1997, 378, 1509)

SEQ ID NO: 297
QRMRPCPSCPLAPW (Lauvrak V., Biol. Chem. 1997, 378, 1509)

SEQ ID NO: 298
WPSRPCPSCPEVPP (Lauvrak V., Biol. Chem. 1997, 378, 1509)

SEQ ID NO: 299
SCTKDCPTCPLVPV (Lauvrak V., Biol. Chem. 1997, 378, 1509)

C1qNb75 Nanobody (Laursen, N. S. et al. Frontiers in Immunology, 2020, 11, 1504)

SEQ ID NO: 300
IALILEPICCQERAA (U.S. Pat. No. 8,906,845)

SEQ ID NO: 301
PAICQRATATLGTVGSNTSGTTEIEACILL (U.S. Pat. No. 8,906,845)

SEQ ID NO: 302
PAIAQRATATLGTVGSNTSGTTEIEACILL (U.S. Pat. No. 8,906,845)

SEQ ID NO: 303
PAICQRATATLGTVGSNTSGTTEIEAAILL (U.S. Pat. No. 8,906,845)

SEQ ID NO: 304
PAICQRATATLGTVGSNTSGTTAIEACILL (U.S. Pat. No. 8,906,845)

SEQ ID NO: 305
PAICQRATATLGTVGSNTSGTTEIAACILL (U.S. Pat. No. 8,906,845)

SEQ ID NO: 306
PAICQRAEIEACILL (U.S. Pat. No. 8,906,845)

SEQ ID NO: 307
PAICQRAEIEACILL (U.S. Pat. No. 8,906,845)

SEQ ID NO: 308
PAIAQRAEIEAAILL (U.S. Pat. No. 8,906,845)

SEQ ID NO: 309
IALILEPICCQERAA (U.S. Pat. No. 8,906,845)

SEQ ID NO: 310
PAICQRATATLGTNTSGTTEIEACILL (U.S. Pat. No. 8,906,845)

SEQ ID NO: 311
PAICQRATATLSGTTEIEACILL (U.S. Pat. No. 8,906,845)

SEQ ID NO: 312
PAICQRATATTEIEACILL (U.S. Pat. No. 8,906,845)

-continued

PAICQRAEIEACILL (U.S. Pat. No. 8,906,845)
SEQ ID NO: 313

AICQRATATLGTVGSNTSGTTEIEACILL (U.S. Pat. No. 8,906,845)
SEQ ID NO: 314

ICQRATATLGTVGSNTSGTTEIEACILL (U.S. Pat. No. 8,906,845)
SEQ ID NO: 315

CQRATATLGTVGSNTSGTTEIEACILL (U.S. Pat. No. 8,906,845)
SEQ ID NO: 316

PAICQRATATLGTVGSNTSGTTEIEACIL (U.S. Pat. No. 8,906,845)
SEQ ID NO: 317

PAICQRATATLGTVGSNTSGTTEIEACI (U.S. Pat. No. 8,906,845)
SEQ ID NO: 318

PAICQRATATLGTVGSNTSGTTEIEAC (U.S. Pat. No. 8,906,845)
SEQ ID NO: 319

Ac-IALILEPICCQERAA (U.S. Pat. No. 8,906,845)
SEQ ID NO: 320

Ac-PAICQRATATLGTVGSNTSGTTEIEACILL (U.S. Pat. No. 8,906,845)
SEQ ID NO: 321

Ac-PAIAQRATATLGTVGSNTSGTTEIEACILL (U.S. Pat. No. 8,906,845)
SEQ ID NO: 322

Ac-PAICQRATATLGTVGSNTSGTTEIEAAILL (U.S. Pat. No. 8,906,845)
SEQ ID NO: 323

Ac-PAICQRATATLGTVGSNTSGTTAIEACILL (U.S. Pat. No. 8,906,845)
SEQ ID NO: 324

Ac-PAICQRATATLGTVGSNTSGTTEIAACILL (U.S. Pat. No. 8,906,845)
SEQ ID NO: 325

Ac-PAICQRAEIEACILL (U.S. Pat. No. 8,906,845)
SEQ ID NO: 326

Ac-PAICQRAEIEACILL (U.S. Pat. No. 8,906,845)
SEQ ID NO: 327

Ac-PAIAQRAEIEAAILL (U.S. Pat. No. 8,906,845)
SEQ ID NO: 328

Ac-IALILEPICCQERAA (U.S. Pat. No. 8,906,845)
SEQ ID NO: 329

Ac-PAICQRATATLGTNTSGTTEIEACILL (U.S. Pat. No. 8,906,845)
SEQ ID NO: 330

Ac-PAICQRATATLSGTTEIEACILL (U.S. Pat. No. 8,906,845)
SEQ ID NO: 331

Ac-PAICQRATATTEIEACILL (U.S. Pat. No. 8,906,845)
SEQ ID NO: 332

Ac-PAICORAEIEACILL (U.S. Pat. No. 8,906,845)
SEQ ID NO: 333

Ac-AICQRATATLGTVGSNTSGTTEIEACILL (U.S. Pat. No. 8,906,845)
SEQ ID NO: 334

Ac-ICQRATATLGTVGSNTSGTTEIBACILL (U.S. Pat. No. 8,906,845)
SEQ ID NO: 335

Ac-CQRATATLGTVGSNTSGTTEIEACILL (U.S. Pat. No. 8,906,845)
SEQ ID NO: 336

Ac-PAICQRATATLGTVGSNTSGTTEIEACIL (U.S. Pat. No. 8,906,845)
SEQ ID NO: 337

Ac-PAICQRATATLGTVGSNTSGTTEIEACI (U.S. Pat. No. 8,906,845)
SEQ ID NO: 338

Ac-PAICQRATATLGTVGSNTSGTTEIEAC (U.S. Pat. No. 8,906,845)
SEQ ID NO: 339

In certain embodiments the Linker is bound through the C-terminus of the amino acid sequence for example
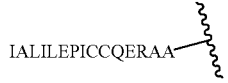
SEQ ID NO: 231
In certain embodiments the Linker is bound to the N-terminus for example
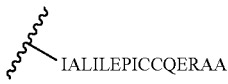
SEQ ID NO: 231
Non-limiting examples of Complement C1q degrading compounds include:
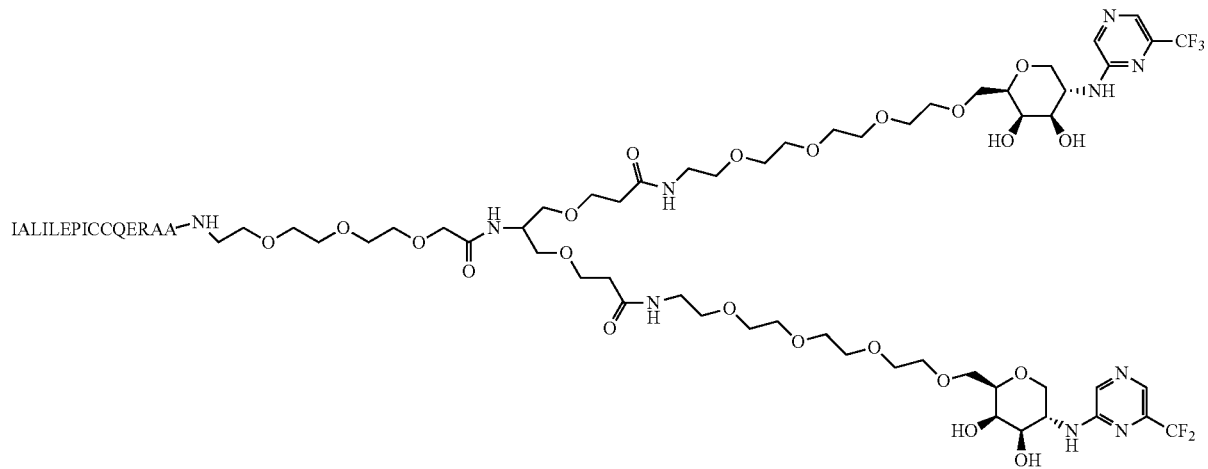
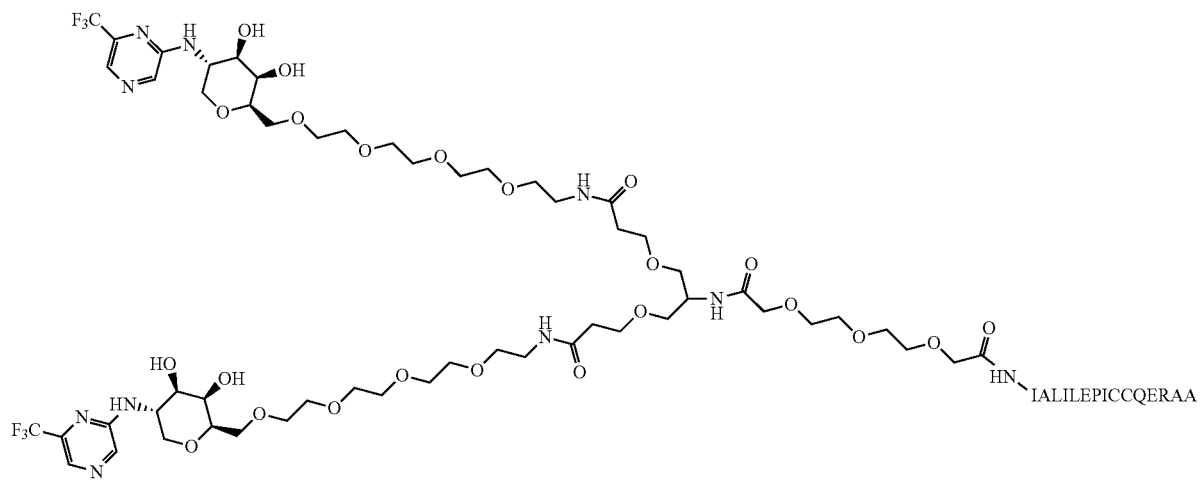

-continued

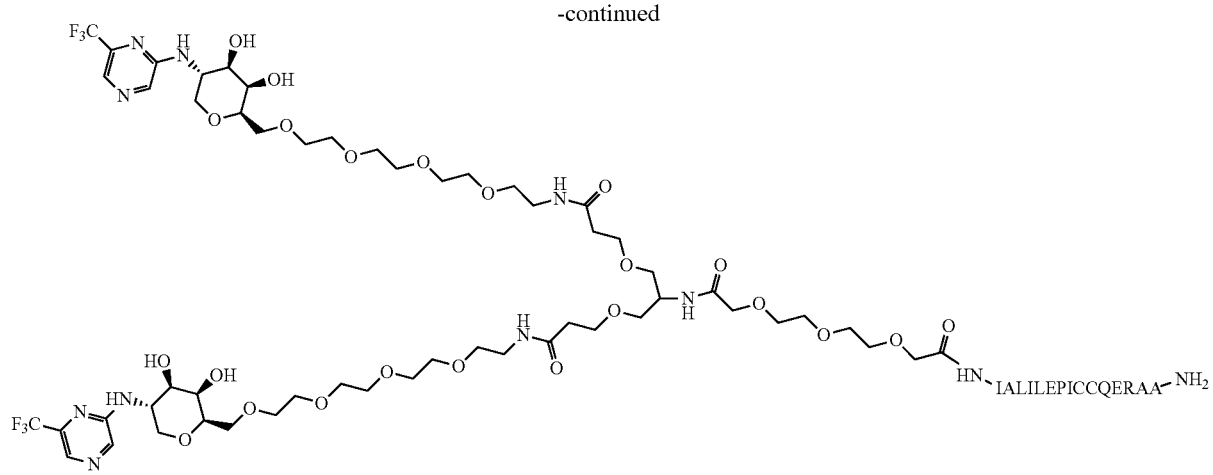

IL-17

In some embodiments, the Target Extracellular Protein is human interleukin-17 (IL-17) (UniProtKB—Q16552 (IL17_HUMAN)). Interleukin-17 is a 35 kDa homodimeric glycoprotein and is an important cytokine for the inflammatory response. IL-17 is secreted by a distinct class of Helper T cells (known as Th17 cells) which mediates tissue inflammation. A characteristic effect of IL-17 production is the expansion of neutrophils, and in healthy tissue it is responsible for neutrophil homeostasis. IL-17 has been implicated as a major factor in psoriasis as well as other autoimmune diseases. Other diseases where IL-17 therapies may be of benefit include but are not limited to asthma, rheumatoid arthritis, psoriatic arthritis, Crohn's disease, and inflammatory bowel disease. Inflammation caused by IL-17 has been shown to hamper recovery post-stroke.

The Protein Data Bank website provides the crystal structure of IL-17, searchable by 4NUX (Zhang, B. et al. (2014) Acta Crystallogr D Biol Crystallogr 70: 1476-1483), 4HSA (Liu, S. et al. (2013) Nat Commun 4: 1888-1888), 4QHU (unpublished), 6WIR (Lieu, R. et al. (2020) PLoS One 15: e0232311-e0232311), 5VB9 (Ting, J. P. et al. (2018) PLoS One 13: e0190850-e0190850), 4NUX (Zhang, et al. (2014) Acta Crystallogr D Biol Crystallogr 70: 1476-1483), 3JVF (Ely, L. K. et al. (2009) Nat Immunol 10: 1245-1251), 5N9B (unpublished), 2VXS (Gerhardt, S. et al. (2009) J Mol Biol 394: 905).

Non-limiting examples of IL-17 Targeting Ligands can be found in, for example, WO2012101263A1, WO2020-163554A1, WO2021055376A1, WO2020146194A1, WO2020127685A1, US20150005319, WO2014066726A2, WO2019223718A1, WO2020135872A1, WO2020-146194A1, WO2021027721A1, WO2021027724, WO2021027729A1, WO2021067191A1, CN104069102A, CN105601617B, CN108299256B, Liu et al. "Binding site elucidation and structure guided design of macrocyclic IL-17A antagonists" 2016, Scientific Reports, 6:30859., Liu et al. "Inhibiting complex IL-17AA and IL-17RA interactions with a linear peptide" 2016, Scientific Reports 6:26071. Wang, W. et al. "Artificial macrocycles as IL-17A/IL-17RA antagonists". Med. Chem. Comm. 2018, 9, 22. Liu, C. et al. "The flavonoid cyanidin blocks binding of the cytokine interleukin-17A to the IL-17RA subunit to alleviate inflammation in vivo" Science Signaling 10, eaaf8823 (2017).

Additional binding ligands include

```
                                                SEQ ID NO: 340
IVVTAPADLWDWIRA (Liu et al. 2016, Scientific Reports 6:26071)

SEQ ID NO: 341
ITVTMPADLWDWIRA (Liu et al. 2016, Scientific Reports 6:26071)

SEQ ID NO: 342
IVVTIPADLWDWIRA (Liu et al. 2016, Scientific Reports 6:26071)

SEQ ID NO: 343
IVVTLPADLWDWIRA (Liu et al. 2016, Scientific Reports 6:26071)

SEQ ID NO: 344
IVVTVPADLWDWIRA (Liu et al. 2016, Scientific Reports 6:26071)

SEQ ID NO: 345
IVVTMPADLWDWIMA (Liu et al. 2016, Scientific Reports 6:26071)

SEQ ID NO: 346
IVVTMPADLWDWINA (Liu et al. 2016, Scientific Reports 6:26071)

SEQ ID NO: 347
IVVTMPADLWDWIQA (Liu et al. 2016, Scientific Reports 6:26071)

SEQ ID NO: 348
IHVTIPADLWDWINK (Liu et al. 2016, Scientific Reports 6:26071)

SEQ ID NO: 349
IHVTIPADLWDWIN  (Liu et al. 2016, Scientific Reports 6:26071)
```

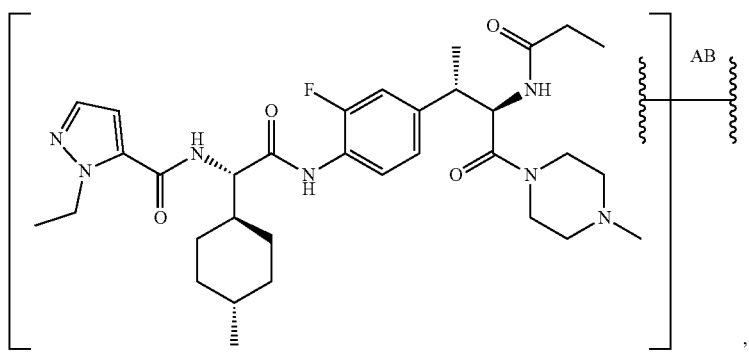
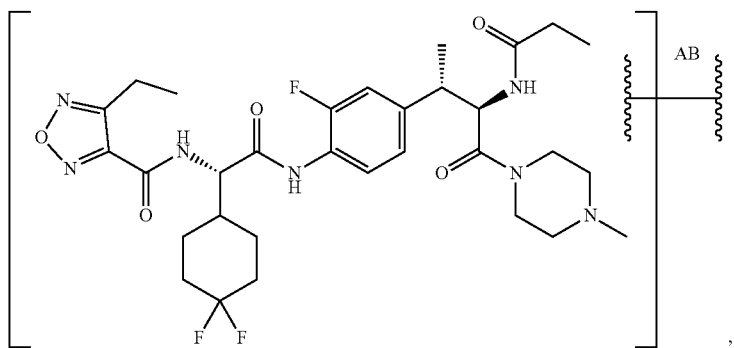
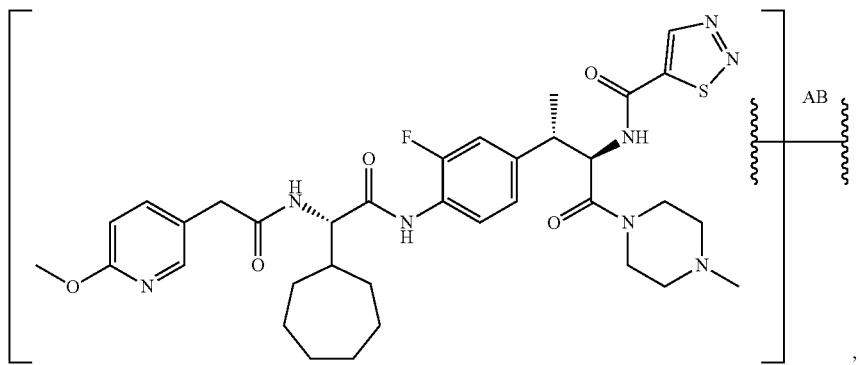
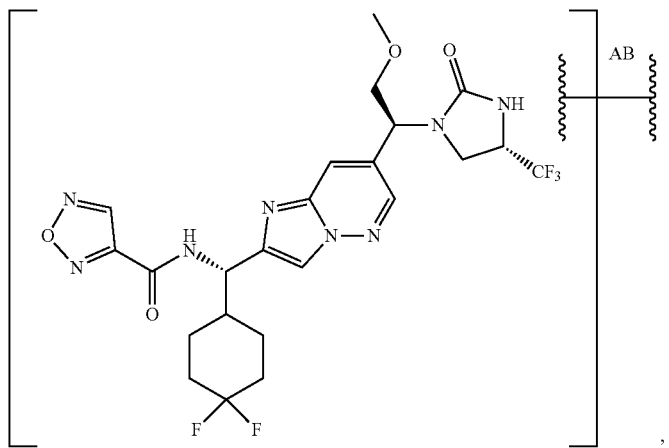

-continued
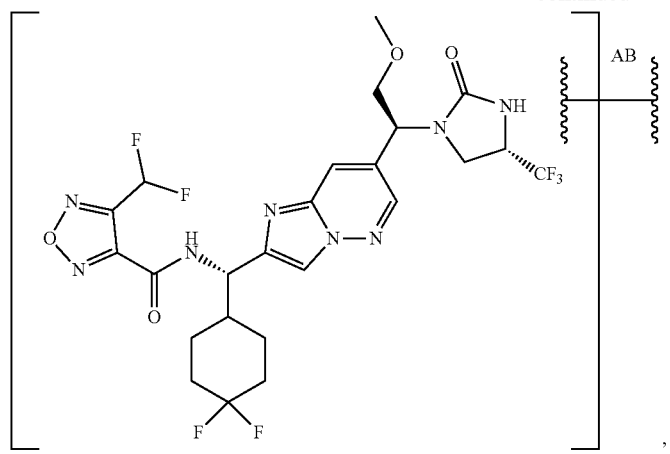
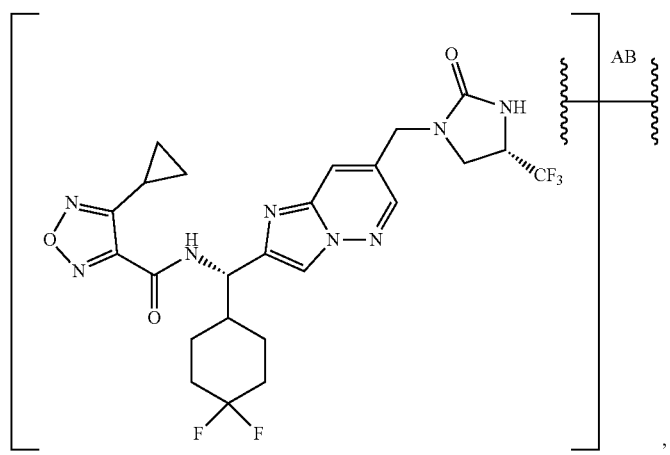
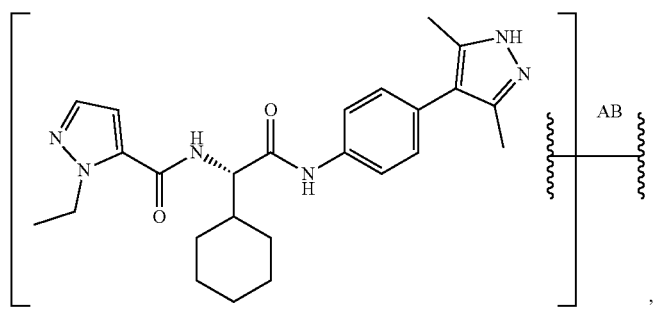
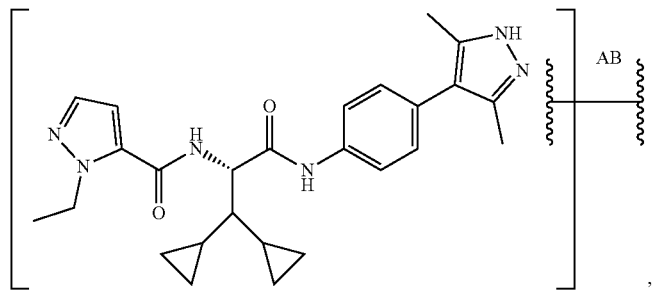

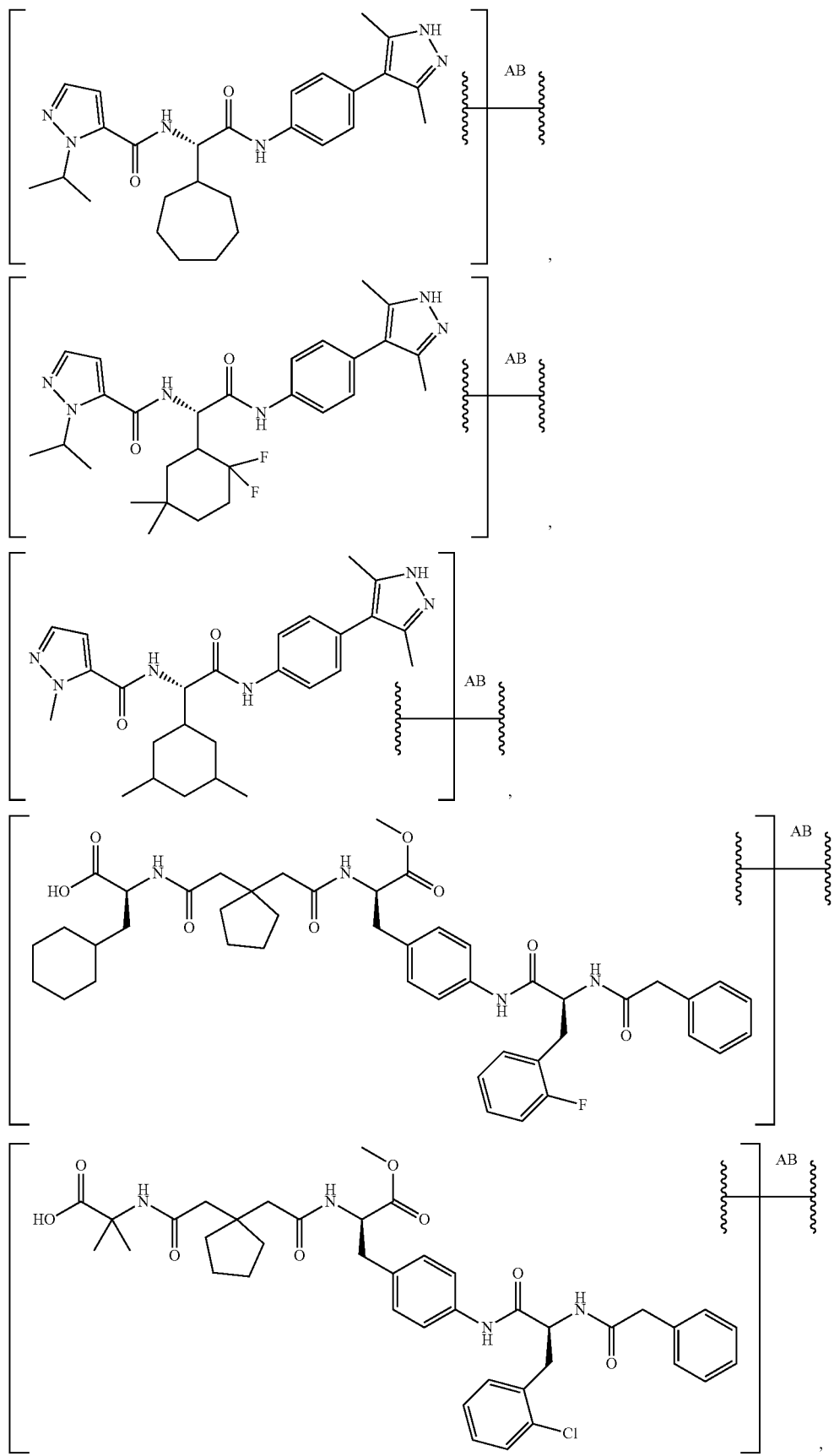

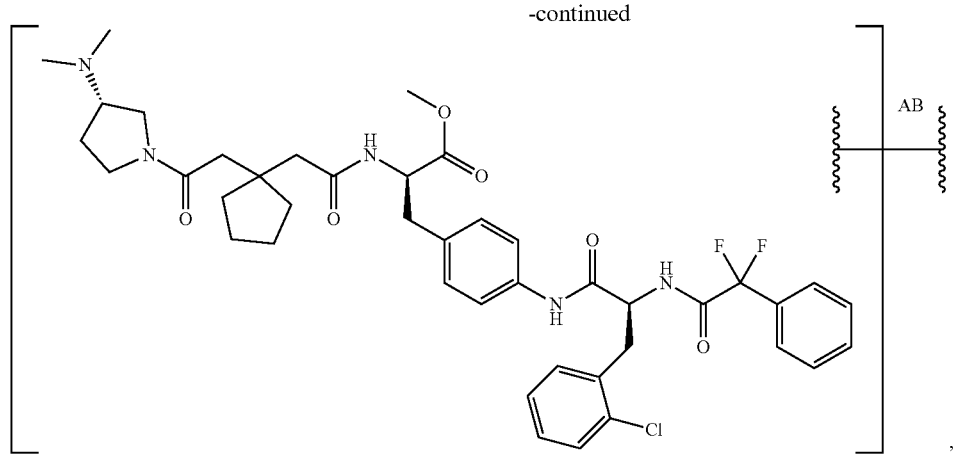
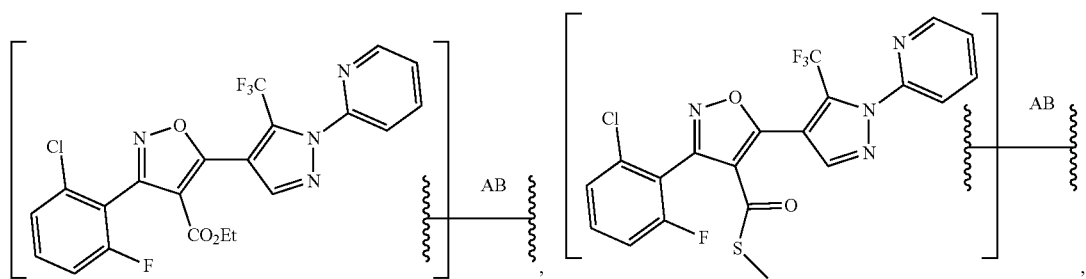
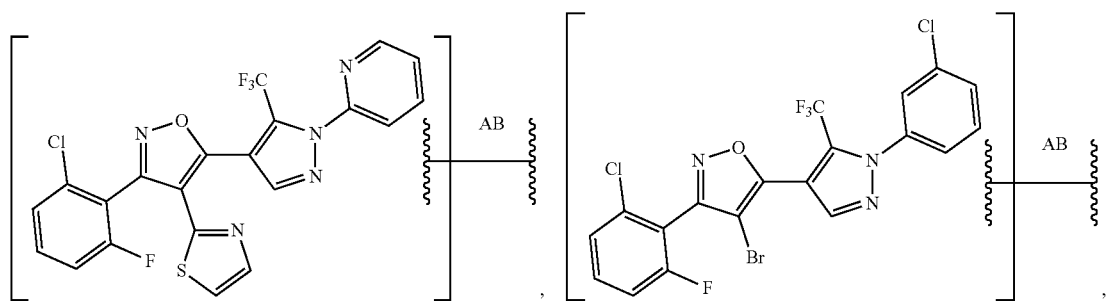
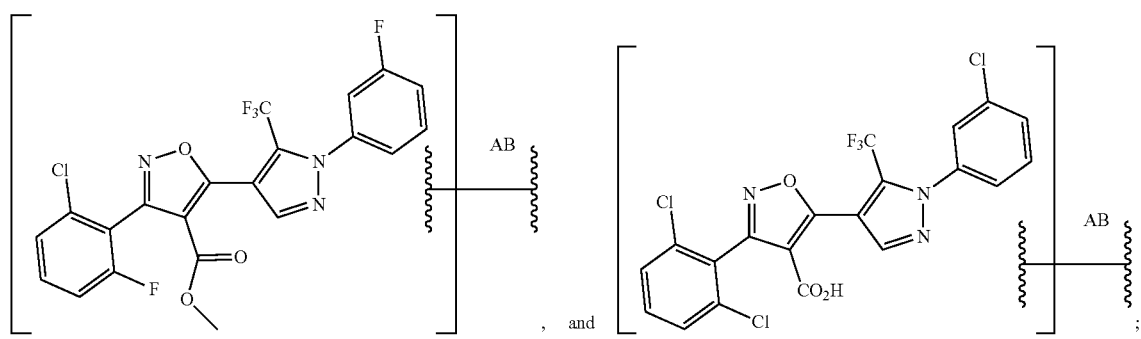
each of which is optionally substituted with 1, 2, 3, or 4 substituents independently selected from $R^{21}$.

In certain embodiments a compound is provided of Formula

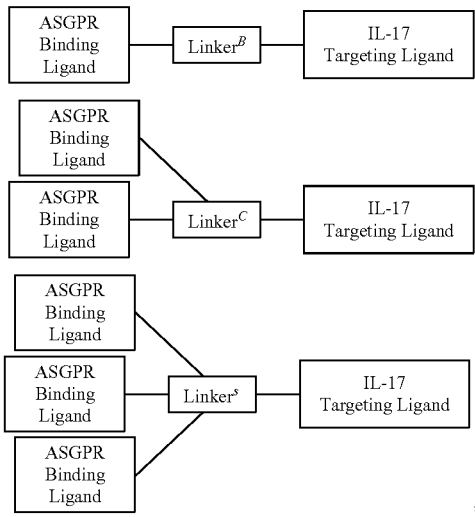

or a pharmaceutically acceptable salt thereof;

wherein
IL-17 Targeting Ligand is any IL-17 ligand described in WO2020/146,194; WO2020/163,554; WO2020/127,685; and WO2021/055,376; each of which is incorporated by reference.

In certain embodiments IL-17 Targeting Ligand is of Formula.

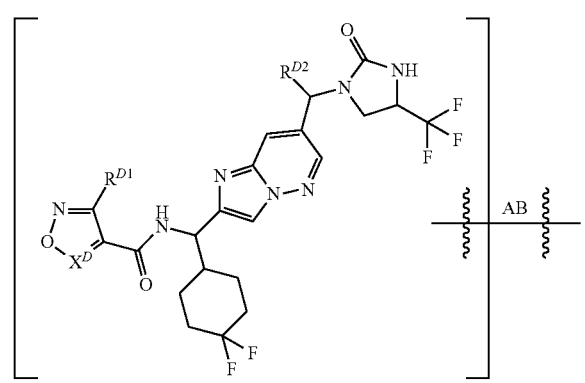

wherein,
$X^D$ is CH or N;
$R^{D1}$ is —CH$_3$, —CH$_2$F, —CHF$_2$, —CF$_3$, —CH$_2$CH$_3$, —CH$_2$CF$_3$, —CH(CH$_3$)$_2$, CH$_2$CHF$_2$, CH$_2$CH$_2$F, —CF(CH$_3$)$_2$, CF$_2$CH$_3$, —OCH$_3$,

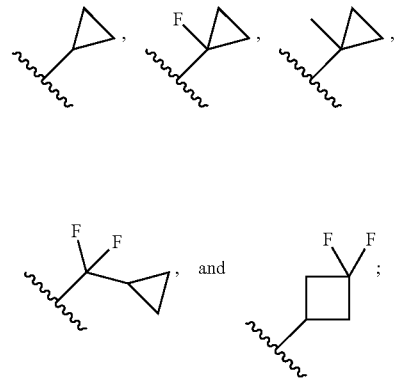

$R^{D2}$ is —H or —CH$_2$OCH$_3$.

In certain embodiments IL-17 Targeting Ligand is of Formula:

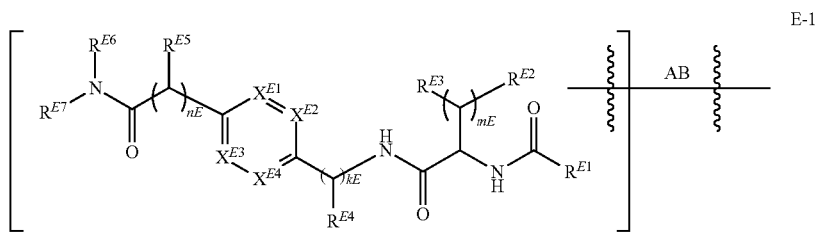

wherein,
$R^{E1}$ is alkyl, substituted alkyl, aryl, substituted aryl, heteroaryl, substituted heteroaryl, arylalkyl, substituted arylalkyl, heteroarylalkyl, substituted heteroarylalkyl —OR$^{E8}$ or —NR$^{E9}$R$^{E10}$ or an F pocket substituent;

$R^{E2}$ is alkyl, substituted alkyl, heterocycle, substituted heterocycle, aryl, substituted aryl, fused cycloalkylaryl, substituted fused cycloalkylaryl, heteroaryl, substituted heteroaryl or a D pocket substituent;

each $R^{E3}$ is independently hydrogen, (C$_1$-C$_7$) alkyl, (C$_1$-C$_7$) substituted alkyl or —OR$^{E32}$;

$m^E$ is 0, 1 or 2;

each $R^{E4}$ is independently hydrogen, (C$_1$-C$_7$) alkyl, (C$_1$-C$_7$) substituted alkyl, cycloalkyl substituted cycloalkyl, heterocycle or substituted heterocycle;

$k^E$ is 0 or 1;

$X^{E1}$, $X^{E2}$, $X^{E3}$ and $X^{E4}$ are independently —N— or —CR$^{E11}$— provided that no more than two of $X^{E1}$, $X^{E2}$, $X^{E3}$ and $X^{E4}$ are nitrogen;

each $R^{E5}$ is independently hydrogen, (C$_1$-C$_7$) alkyl, (C$_1$-C$_7$) substituted alkyl, heterocycle, substituted heterocycle, cycloalkyl, substituted cycloalkyl, heterocycleal-kyl, substituted heterocyclealkyl, —NR$^{E12}$R$^{E13}$, —NR$^{E14}$C(O)R$^{E15}$, —NHSO$_2$R$^{E31}$, OH or a B pocket substituent;

$R^{E6}$ is hydrogen or alkyl;

$R^{E7}$ is heterocycle, substituted heterocycle, —$(CR^{E16})_o$ $R^{E17}$ or —$(CHRE^{18})_p R^{E19}$ or $R^{E6}$ and $R^{E7}$ taken together with the nitrogen atom to which they are attached form piperazine, substituted piperazine, heterocycle or substituted heterocycle,

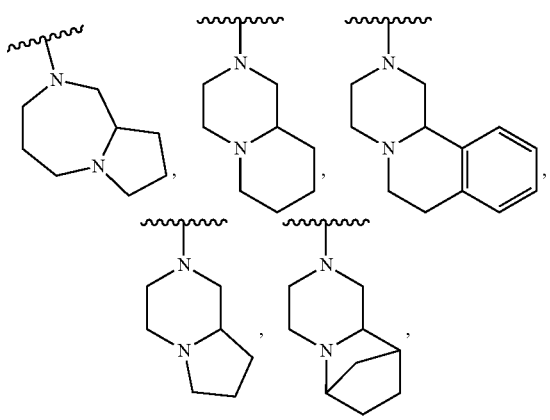

or an A pocket substituent;

$R^{E8}$ is $(C_1-C_7)$ alkyl, $(C_1-C_7)$ substituted alkyl, aryl, substituted aryl, heteroaryl or substituted heteroaryl;

each $R^{E11}$ is independently hydrogen, alkyl, substituted alkyl, —$OR^{E20}$, —$NR^{E21}R^{E22}$, halo, —CN, —$CO_2R^{E23}$, —$CONR^{E24}R^{E25}$ or —$SR^{E26}$;

$n^E$ is 1, 2 or 3;
$o^E$ is 1, 2 or 3;
$p^E$ is 1, 2 or 3;

each $R^{E16}$ is independently hydrogen, $(C_1-C_7)$ alkyl or $(C_1-C_7)$ substituted ALKYL $R^{E17}$ is

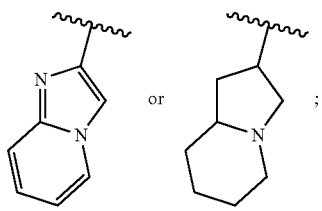 [SMILES: *c1cn2ccccc2n1 ; *C1CC2CCCCN2C1]

each $R^{E18}$ is independently hydrogen, $(C_1-C_7)$ alkyl, or $(C_1-C_7)$ substituted alkyl; $R^{E19}$ is —$NR^{E27}R^{E28}$; $R^{E27}$ and $R^{E28}$ together with the nitrogen atom to which they are attached form a heterocycle or substituted heterocycle ring or

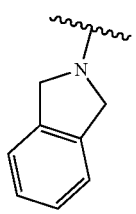 [SMILES: *N1Cc2ccccc2C1]

$R^{E9}$, $R^{E10}$, $R^{E12}$, $R^{E13}$, $R^{E14}$, $R^{E15}$, $R^{E18}$, $R^{E19}$, $R^{E20}$, $R^{E21}$, $R^{E22}$, $R^{E23}$, $R^{E24}$, $R^{E25}$, $R^{E26}$, $R^{E30}$, $R^{E31}$, and $R^{E32}$ are independently selected at each instance from hydrogen, alkyl, substituted alkyl, heterocycle, substituted heterocycle, aryl, substituted aryl, heteroaryl, substituted heteroaryl, or alternatively, independently, $R^{E9}$ and $R^{E10}$, $R^{E21}$ and $R^{E22}$ and $R^{E24}$ and $R^{E25}$ together with atom to which they are attached form a cycloalkyl, substituted cycloalkyl, cycloheteroalkyl or substituted cycloheteroalkyl ring;

$R^{E28}$ is hydrogen or alkyl;

A-pocket substituent is selected from the group consisting of

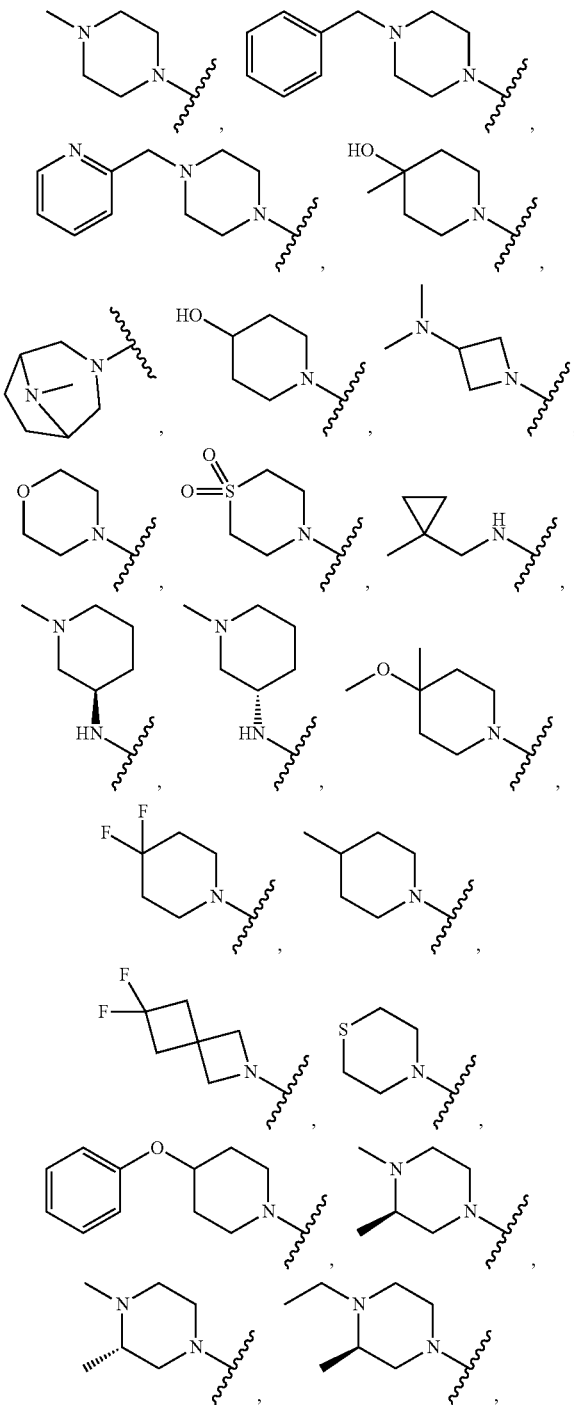

-continued
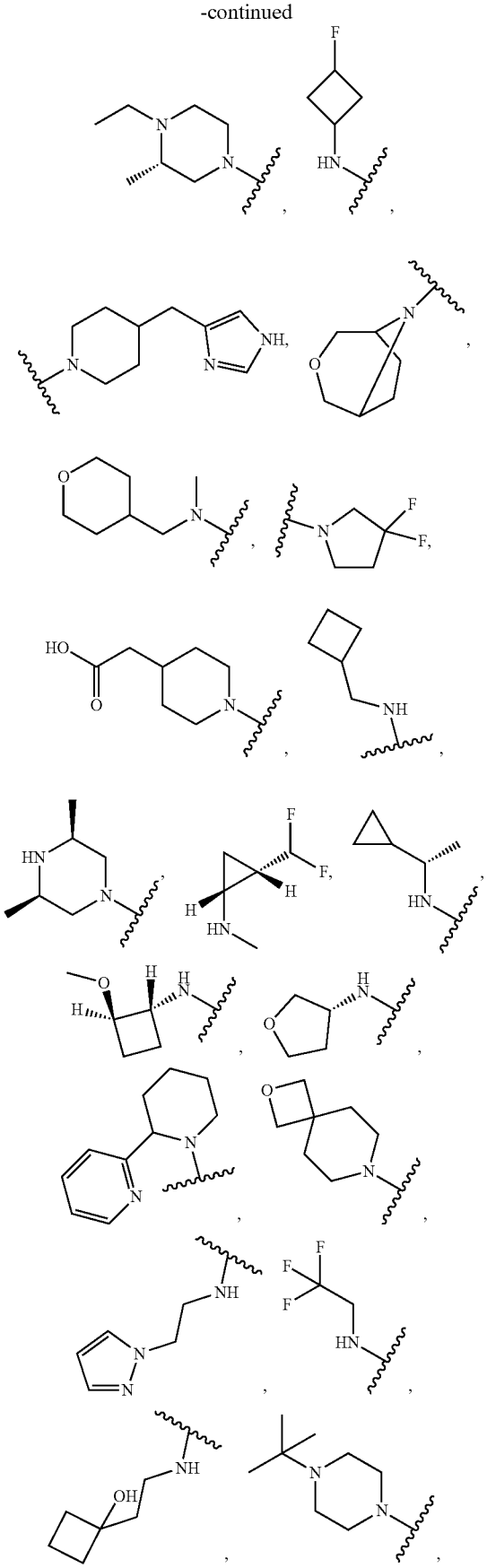
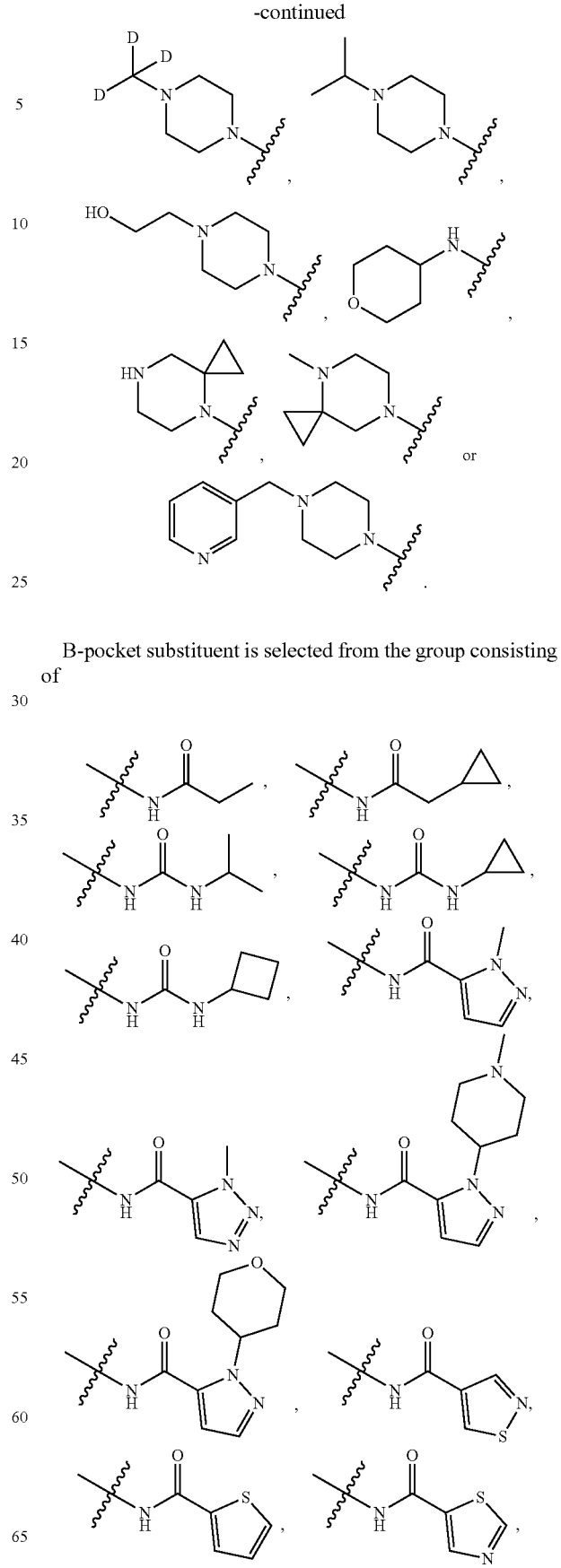
B-pocket substituent is selected from the group consisting of -continued
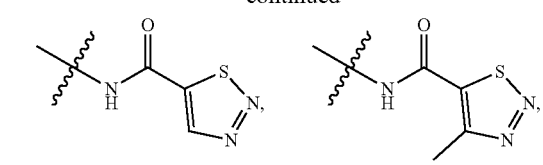
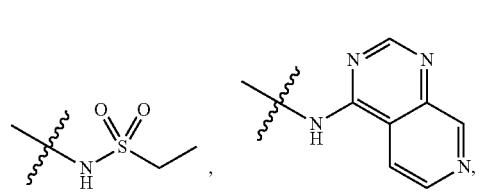
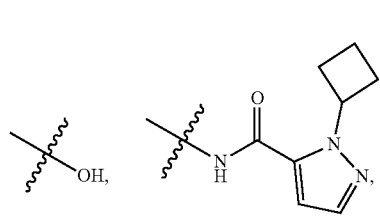
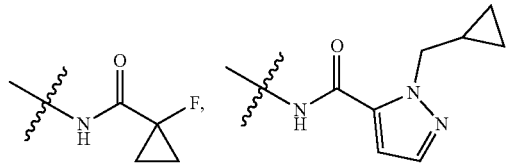
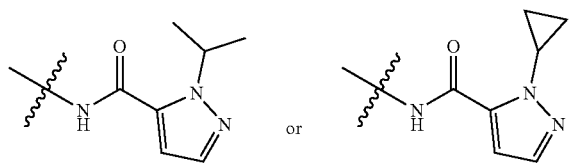 or 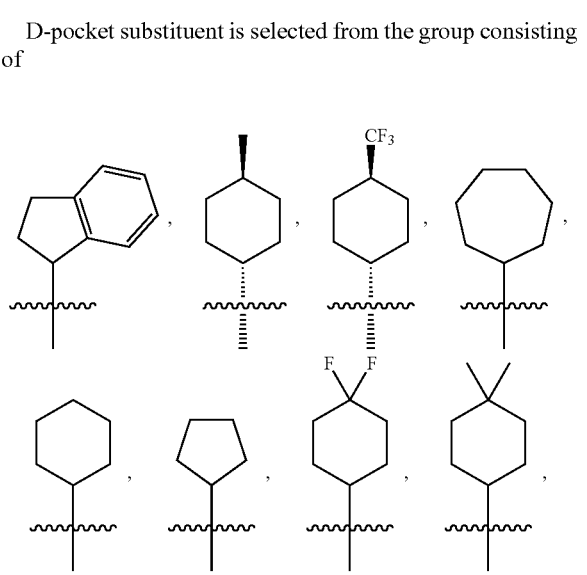
D-pocket substituent is selected from the group consisting of
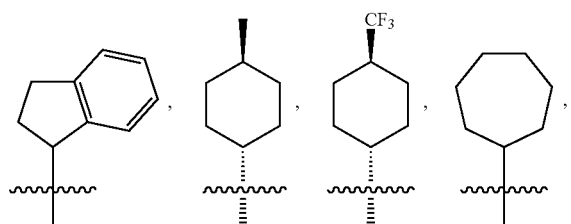
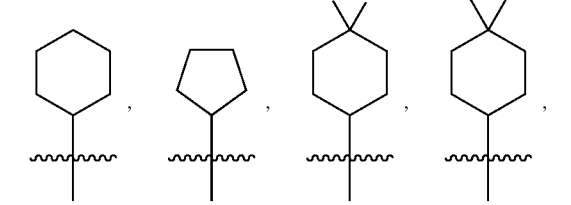
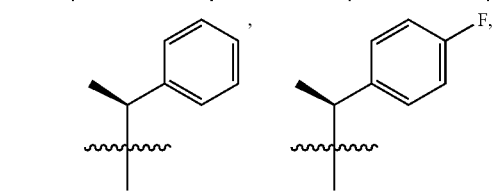
-continued
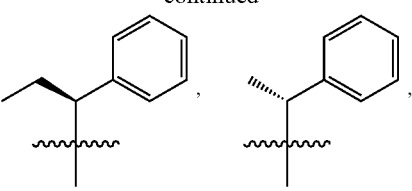
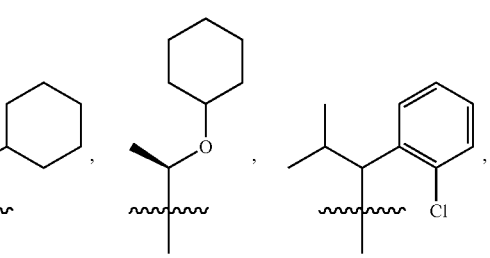
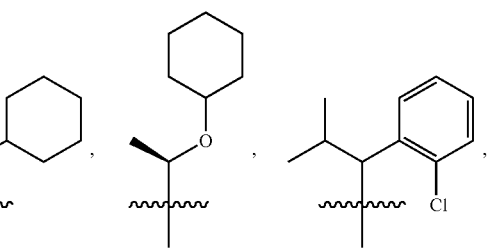
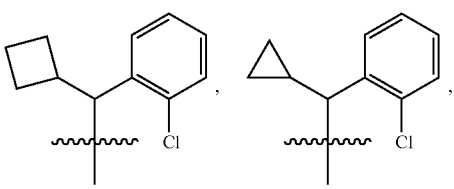
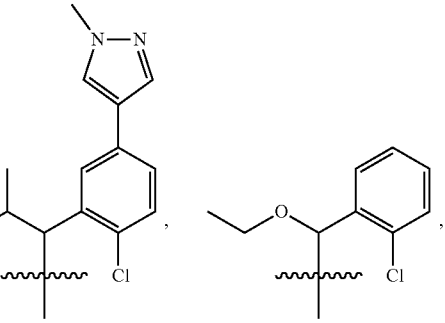
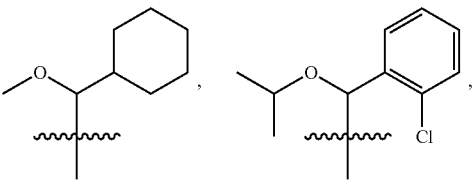 or 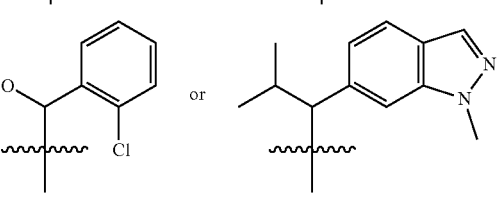
F-pocket substituent is selected from the group consisting of
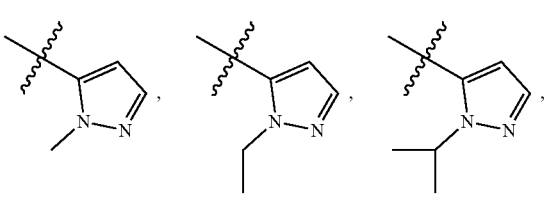

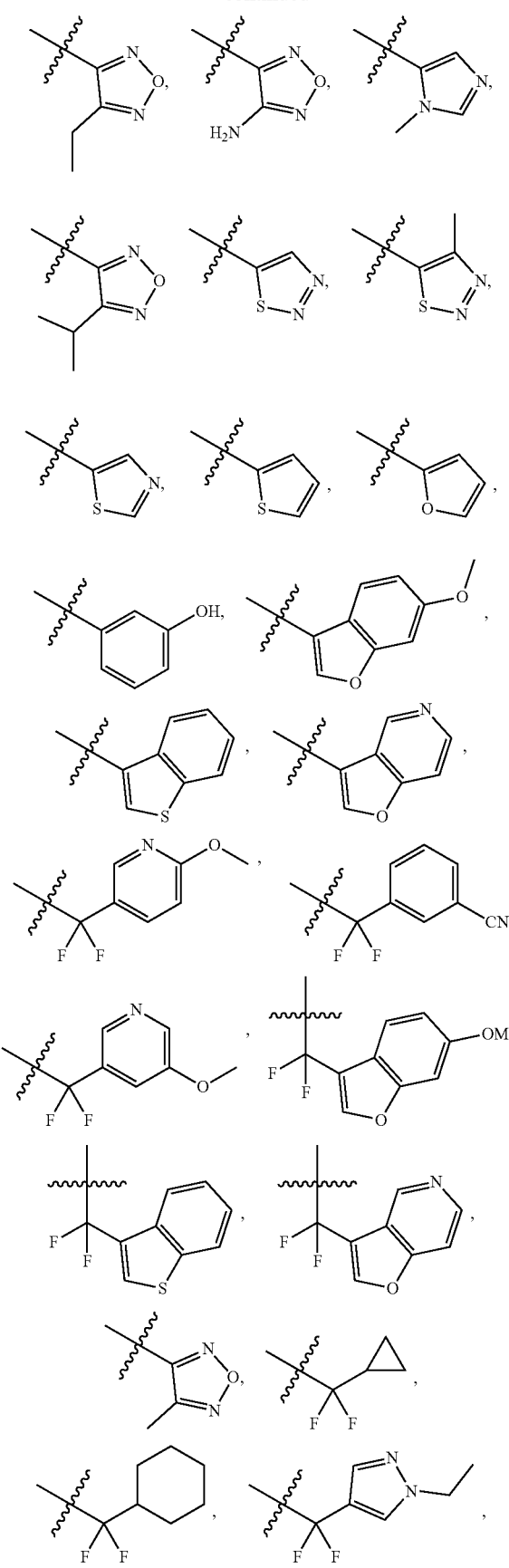
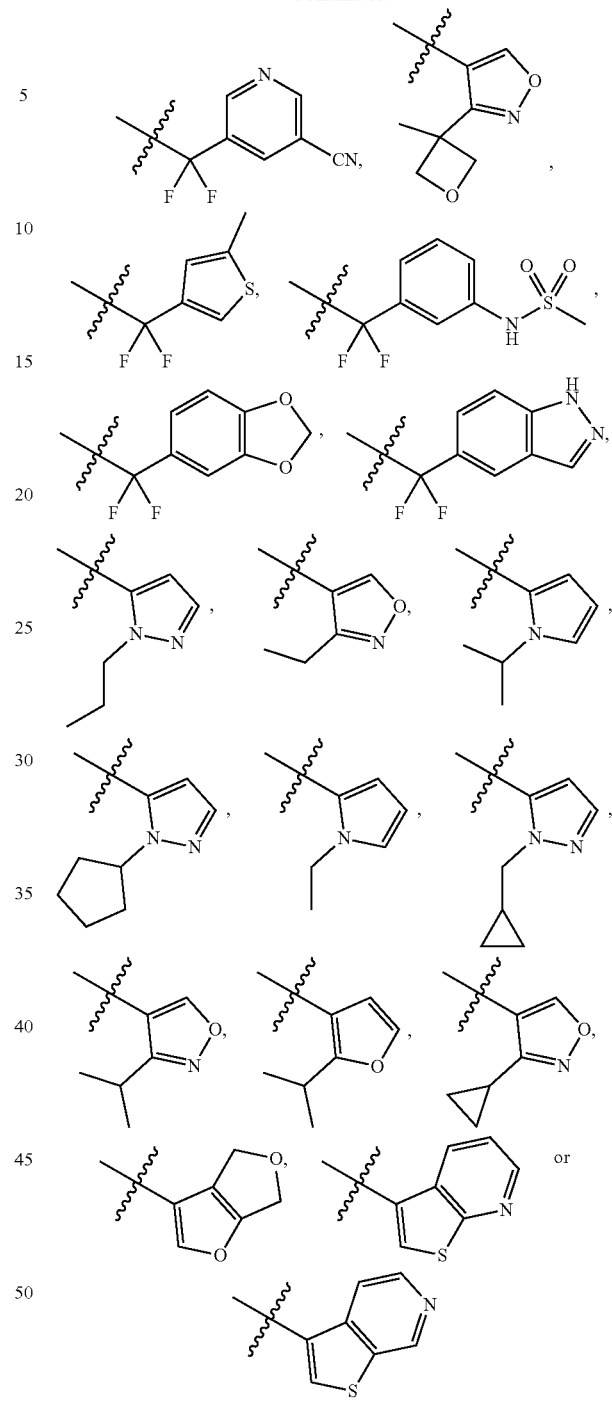

wherein each optional substituent for the above Formula is independently selected from halogen, —OR$^{F12}$, —SR$^{F12}$, —N(R$^{F12}$)$_2$, —C(O)R$^{F12}$, —C(O)N(R$^{F12}$)$_2$, N(R$^{F12}$)C(O)R$^{F12}$, —C(O)OR$^{F12}$, —OC(O)R$^{F12}$, —S(O)R$^{F12}$, —S(O)$_2$R$^{F12}$, —NO$_2$, =O, =S, =N(R$^{F12}$), —CN, C$_{3-10}$ carbocycle and 3- to 10-membered heterocycle; wherein the C$_{3-10}$ carbocycle and 3- to 10-membered heterocycle are each optionally substituted with one or more substituents selected from: halogen, —OR$^{F12}$, —N(R$^{F12}$)$_2$, —C(O)R$^{F12}$, —C(O)N(R$^{F12}$)$_2$, —N(R$^{F12}$)C(O)R$^{F12}$, —C(O)OR$^{F12}$, —OC(O)R$^{F12}$, —NO, =O, =N(R$^{F11}$) and —CN.

In certain embodiments the I-17 Targeting Ligand is of Formula:

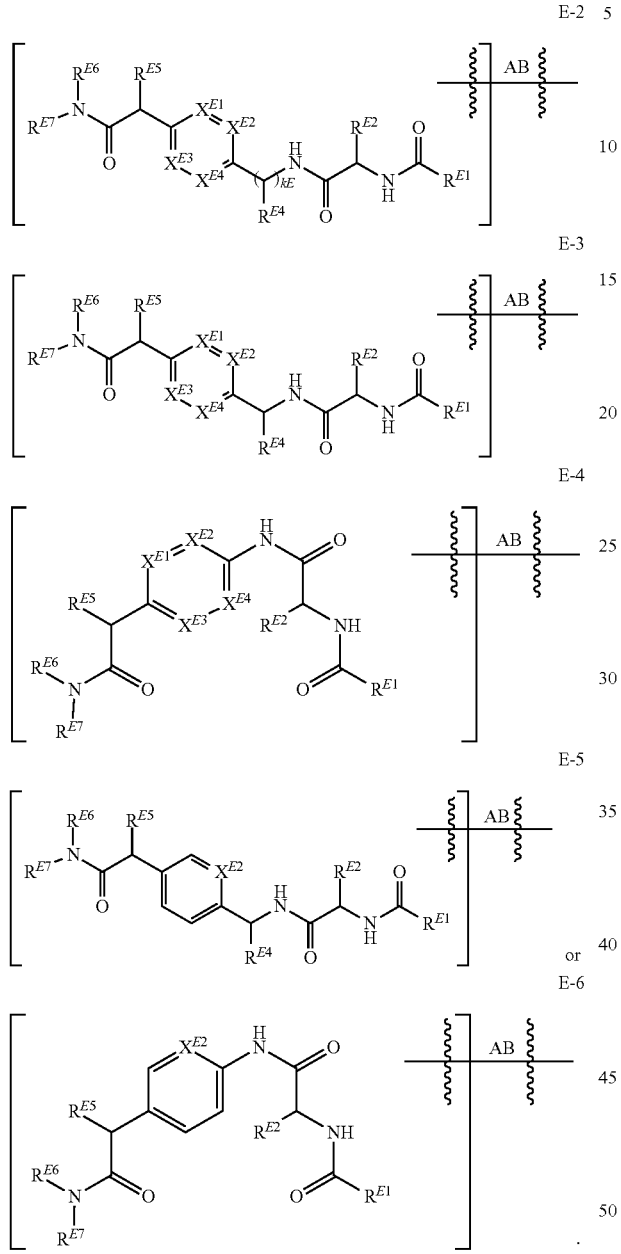

In certain embodiments IL-17 Targeting Ligand is of Formula:

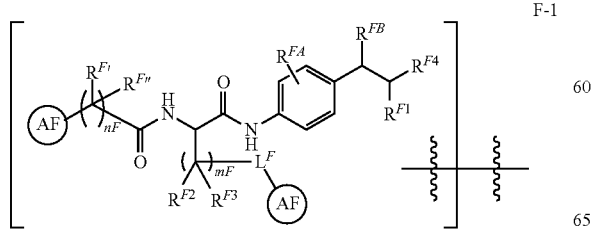

wherein,

is selected from an optionally substituted $C_{3-12}$ carbocycle and optionally substituted 3- to 12-membered heterocycle wherein substituents on Ring AF are independently selected at each occurrence from:

halogen, $-OR^{F11}$, $-SR^{F11}$, $-N(R^{F11})_2$, $-C(O)R^{F11}$, $-C(O)N(R^{F11})_2$, $N(R^{F11})C(O)R^{F11}$, $-N(R^{F11})S(O)_2R^{F11}$, $-C(O)OR^{F11}$, $-OC(O)R^{F11}$, $-S(O)R^{F11}$, $-S(O)_2R^{F11}$, $-NO_2$, $=O$, $=S$, $=N(R^{F11})$—CN; and $C_{1-10}$ alkyl, $C_{2-10}$ alkenyl, $C_{2-10}$ alkynyl, each of which is optionally substituted with one or more substituents independently selected from halogen, $-OR^{F11}$, $-SR^{F11}$, $-N(R^{F11})_2$, $-C(O)R^{F11}$, $-C(O)N(R^{F11})_2$, $N(R^{F11})C(O)R^{F11}$, $-C(O)OR^{F11}$, $-OC(O)R^{F11}$, $-S(O)R^{F11}$, $-S(O)_2R^{F11}$, $-NO_2$, $=O$, $=S$, $=N(R^{F11})$, $-CN$, $C_{3-10}$ carbocycle and 3- to 10-membered heterocycle; wherein the $C_{3-10}$ carbocycle and 3- to 10-membered heterocycle are each optionally substituted with one or more substituents selected from: halogen, $-OR^{F11}$, $-N(R^{F11})_2$—$C(O)R^{F11}$, $-C(O)N(R^{F11})_2$, $-N(R^{F11})C(O)R^{F11}$, $-C(O)OR11$, $-OC(O)R11$, $-NO2$, $=O=N(R11$ and $-CN'$ and $C_{3-12}$ carbocycle and 3- to 12-membered heterocycle, each of which is optionally substituted with one or more substituents independently selected from: halogen, $-OR^{F11}$, $-SR^{F11}$, $-N(R^{F11})_2$, $-C(O)R^{F11}$, $-C(O)N(R^{F11})_2$, $N(R^{F11})C(O)R^{F11}$, $-C(O)OR^{F11}$, $-OC(O)R^{F11}$, $-NO_2$, $-CN$, $C_{1-6}$ alkyl and $C_{1-6}$ haloalkyl;

is selected from an optionally substituted $C_{3-10}$ carbocycle and optionally substituted 3- to 12-membered heterocycle each substituent on Ring B are independently selected at each occurrence from:

halogen, $-ORF12$, $-SRF12$, $-N(RF12)_2$, $-C(O)RF12$, $-C(O)N(RF12)_2$, $-N(RF12)C(O)RF12$, $-C(O)ORF12$, $-OC(O)RF12$, $-S(O)RF12$, $-S(O)_2RF12$, $-NO2$, $=O$, $=S$, $=N(RF12)$, $-CN$; and $C_{1-10}$ alkyl, $C_{2-10}$ alkenyl, $C_{2-10}$ alkynyl, each of which is optionally substituted with one or more substituents independently selected from halogen, $-OR^{F12}$, $-SR^{F12}$, $-N(R^{F12})_2$, $-C(O)R^{F12}$, $-C(O)N(R^{F12})_2$, $N(R^{F12})C(O)R^{F12}$, $-C(O)OR^{F12}$, $-OC(O)R^{F12}$, $-S(O)R^{F12}$, $-S(O)_2R^{F12}$, $-NO_2$, $=O$, $=S$, $=N(R^{F12})$, $-CN$, $C_{3-10}$ carbocycle and 3- to 10-membered heterocycle; wherein the $C_{3-10}$ carbocycle and 3- to 10-membered heterocycle are each optionally substituted with one or more substituents selected from: halogen, $-OR^{F12}$, $-N(R^{F12})_2$, $-C(O)R^{F12}$, $-C(O)N(R^{F12})_2$, $-N(R^{F12})C(O)R^{F12}$, $-C(O)OR^{F12}$, $-OC(O)R^{F12}$, $-NO$, $=O$, $=N(R^{F11})$ and $-CN$;

$R^{F4}$ is selected from $-C(O)N(R^{F23})(R^{F24})$ and $C(O)$ heterocycle, wherein heterocycle is optionally substituted with 1, 2, 3, or 4 substituents selected from halogen, $-OR^{F13}$, $-SR^{F13}$, $-N(R^{F13})_2$, $-C(O)R^{F13}$, $-C(O)N(R^{F13})_2$, $-N(R^{F13})C(O)R^{F13}$, $-C(O)OR^{F13}$, $-OC(O)R^{F13}$, $-S(O)R^{F13}$, $-S(O)_2R^{F13}$, $-NO_2$, $=O$, $=S$, $=N(R^{F13})$—CN; and $C_{1-10}$ alkyl, $C_{2-10}$ alkenyl, $C_{2-10}$ alkynyl, each of which is optionally substituted with one or more substituents independently selected from halogen, $-OR^{F13}$, $-SR^{F13}$, $-N(R^{F13})_2$, $-C(O)R^{F13}$, $-C(O)N(R^{F13})_2$, $N(R^{F13})C(O)R^{F13}$, $-C(O)OR^{F13}$, $-OC(O)R^{F13}$, $-S(O)R^{F13}$, $-S(O)_2R^{F13}$, $-NO_2$, $=O$, $=S$, $=N(R^{F13})$, $-CN$, $C_{3-10}$ carbocycle and 3- to 10-membered heterocycle, wherein the $C_{3-10}$ carbocycle and 3- to 10-membered heterocycle are each optionally substituted with one or more substituents selected from: halogen, $-OR^{F13}$, $-N(R^{F13})_2$, $-C(O)R^{F13}$, $-C(O)N(R^{F13})_2$, $-N(R^{F13})C(O)R^{F13}$, $-C(O)OR^{F13}$, $-OC(O)R^{F13}$, $-NO_2$, $=O$, $=N(R^{F13})$, and $-CN$;

$L^F$ is bond or selected from $-O-$ and $-NH-$;

$R^{FA}$ is selected from hydrogen, halogen, $-OR^{F14}$, $-N(R^{F14})_2$, $-C(O)R^{F14}$, $-C(O)N(R^{F14})_2$, $N(R^{F14})C(O)R^{F14}$, $-C(O)O^{RF14}$, $-OC(O)R^{F14}$, $-NO_2$, $-CN$, and $C_{1-6}$ alkyl, wherein $C_{1-6}$ alkyl is optionally substituted with one or more substituents selected from: halogen, $OR^{F14}$, $-N(R^{F14})_2$, $-C(O)R^{F14}$, $NO_2$, $=O$, and $-CN$;

$R^{FB}$ is selected from hydrogen, halogen, $-OR^{F15}$, $-N(R^{F15})_2$, $-C(O)R^{F15}$, $-C(O)N(R^{F15})_2$, $N(R^{F15})C(O)R^{F15}$, $-C(O)OR^{F15}$, $-OC(O)R^{F15}$, $-NO2$, $-CN$, and $C_{1-6}$ alkyl, wherein $C_{1-6}$ alkyl is optionally substituted with one or more substituents selected from: halogen, $OR^{F15}$, $-N(R^{F15})_2$, $-C(O)R^{F15}$, $NO_2$, $=O$, and $-CN$, wherein at least one of $R^A$ or $R^B$ is not hydrogen;

$R^{F'}$ and $R^{F'''}$ are independently selected from: hydrogen, halogen, $-OR^{F16}$, and $C_{1-6}$ alkyl wherein the $C_{1-6}$ alkyl is optionally substituted with one or more substituents selected from: halogen, $-OR^{F16}$, $-N(R^{F16})_2$, $-C(O)R^{F16}$, $-NO_2$, $=O$, and $-CN$;

$R^{F1}$ is selected from $-OR^{F21}$, $-N(R^{F21})(R^{F22})$, $-N(R^{F21})C(O)R^{F22}$, $-N(R^{F21})_cC(O)OR^{F22}$, $-N(R^{F21})C(O)N(R^{F21})(R^{F22})$, $-N(R^{F21})S(=O)_2N(R^{F21})(R^{F22})$, and $-N(R^{F21})S(=O)_2(R^{F22})$;

each $R^{F2}$ and $R^{F3}$ are independently selected from: hydrogen, halogen, $-OR^{F17}$, $C_{1-6}$ alkyl, and $C_{3-6}$ cycloalkyl; wherein the $C_{1-6}$ alkyl and $C_{3-6}$ cycloalkyl are optionally substituted with one or more substituents selected from: halogen, $-OR^{F17}$, $-N(R^{F17})_2$, $-C(O)^{RF17}$, $-NO_2$, $=O$, and $-CN$; or $R^{F2}$ and $R^{F3}$ bound to the same carbon come together to form a $C_{3-6}$ cycloalkyl optionally substituted with one or more substituents selected from halogen, $-OR^{F17}$, $-N(R^{F17})_2$, $-C(O)R^{F17}$, $-NO_2$, $=O$, and $-CN$;

$R^{F21}$ is independently selected at each occurrence from hydrogen and $C_1$-$C_6$ alkyl optionally substituted by one or more substituents independently selected from halogen, $-OR^{F17}$, $-N(R^{F17})_2$, $-C(O)R^{F17}$, $-NO_2$, $=O$, and $-CN$;

$R^{F22}$ is selected from: $C_{1-10}$ alkyl, $C_{2-10}$ alkenyl, $C_{2-10}$ alkynyl, each of which is optionally substituted with one or more substituents independently selected from halogen, $-OR^{F18}$, $-SR^{18}$, $-N(R^{F18})_2$, $-C(O)R^{F18}$, $-C(O)N(R^{F18})_2$, $-N(R^{F18})C(O)R^{F18}$, $-C(O)OR^{F18}$, $-OC(O)R^{F18}$, $-S(O)R^{F18}$, $-S(O)_2R^{F18}$, $-NO_2$, $=O$, $=S$, $=N(R^{F18})$, $-CN$, $C_{3-10}$ carbocycle and 3- to 10-membered heterocycle; wherein the $C_{3-10}$ carbocycle and 3- to 10-membered heterocycle are each optionally substituted with one or more substituents selected from: halogen, $-OR^{F18}$, $-N(R^{F18})_2$, $-C(O)R^{F18}$, $-C(O)N(R^{F18})_2$, $N(R^{F18})C(O)R^{F18}$, $-C(O)OR^{F18}$, $-OC(O)R^{F18}$, $-NO_2$, $=O$, $=N(R^{F18})$, and $-CN$; and $C_{3-12}$ carbocycle and 3- to 12-membered heterocycle, each of which is optionally substituted with one or more substituents independently selected from:

halogen, $-OR^{F18}$, $-SR^{F18}$, $-N(R^{F18})_2$, $-C(O)R^{F18}$, $-C(O)N(R^{F18})_2$, $-N(R^{F18})C(O)R^{F18}$, $-C(O)OR^{F18}$, $-OC(O)R^{F18}$, $-S(O)R^{F18}$, $-S(O)_2R^{F18}$, $-NO_2$, $=O$, $=S$, $=N(R^{F18})$, $-CN$; and $C_{1-10}$ alkyl, $C_{2-10}$ alkenyl, $C_{2-10}$ alkynyl, each of which is optionally substituted with one or more substituents independently selected from halogen, $-OR^{F18}$, $-SR^{F18}$, $-N(R^{F18})_2$, $-C(O)R^{F18}$, $-C(O)N(R^{F18})_2$, $-N(R^{F18})C(O)R^{F18}$, $-C(O)OR^{F18}$, $-OC(O)R^{F18}$, $-S(O)R^{F18}$, $-S(O)_2R^{F18}$, $-NO_2$, $=O$, $=S$, $=N(R^{F18})$, $-CN$, $C_{3-10}$ carbocycle and 3- to 10-membered heterocycle; wherein the $C_{3-10}$ carbocycle and 3- to 10-membered heterocycle are each optionally substituted with one or more substituents selected from: halogen, $-OR^{F18}$, $-N(R^{F18})_2$, $-C(O)R^{F18}$, $-C(O)N(R^{F18})_2$, $-N(R^{F18})C(O)R^{F18}$, $-C(O)OR^{F18}$, $-OC(O)R^{F18}$, $-NO=O$, $=N(R^{F18})$, and $-CN$; and $C_{3-10}$ carbocycle and 3- to 10-membered heterocycle are each optionally substituted with one or more substituents selected from: halogen, $-OR^{F18}$, $-N(R^{F18})_2$, $-C(O)R^{F18}$, $-C(O)N(R^{F18})_2$, $N(R^{F18})C(O)R^{F18}$, $-C(O)OR^{F18}$, $-OC(O)R^{F18}$, $-NO_2$, $=O$, $=N(R^{F18})$, and $-CN$;

$R^{F23}$ is selected from:

$C_{1-6}$ alkyl optionally substituted with one or more substituents independently selected from halogen, $-OR^{F19}$, $-SR^{F19}$, $-N(R^{F19})_2$, $-NO_2$, $-CN$, $C_{3-10}$ carbocycle and 3- to 10-membered heterocycle; wherein the $C_{3-10}$ carbocycle and 3- to 10-membered heterocycle are each optionally substituted with one or more substituents selected from: halogen, $-OR^{F19}$, $-N(R^{F19})_2$, $=O$, $C_1$-$C_6$ alkyl, $C_1$-$C_6$ haloalkyl, and $-CN$; and $C_{3-12}$ carbocycle and 3- to 10-membered heterocycle, each of which is optionally substituted with one or more substituents independently selected from halogen, $-OR^{F19}$, $-N(R^{F19})_2$, $=O$, $C_1$-$C_6$ alkyl, $C_1$-$C_6$ haloalkyl, and $-CN$;

$R^{F24}$ is selected from hydrogen and $C_{1-6}$ alkyl optionally substituted with one or more substituents independently selected from halogen, $-OR^{F19}$, $-SR^{F19}$, $-N(R^{F19})_2$, $-NO_2$, $-CN$, $C_{3-6}$ carbocycle and 3- to 6-membered heterocycle;

$R^{F11}$, $R^{F12}$, $R^{F13}$, $R^{F14}$, $R^{F15}$, $R^{F16}$, $R^{F17}$, $R^{F18}$, and $R^{F19}$ are independently selected at each occurrence from hydrogen; and $C_{1-6}$ alkyl optionally substituted with one or more substituents independently selected from halogen, $-OH$, $-O-C_1$-$C_6$ alkyl, $-O-C_1$-$C_6$haloalkyl $-NH2$, $-NO2$, $=O$, $-CN$, $C_{3-10}$ carbocycle and 3- to 10-membered heterocycle; wherein the $C_{3-10}$ carbocycle and 3- to 10-membered heterocycle are each optionally substituted with one or more substituents selected from: halogen, $-OH$, $-O-C_1$-$C_6$ alkyl, $-O-C_1$-$C_6$ haloalkyl $-NH_2$, $-NO_2$, $=O$, and $-CN$; and $C_{3-12}$ carbocycle and 3- to 12-membered heterocycle, each of which is optionally substituted with one or more substituents independently selected from:

halogen, $-OH$, $-O-C_1$-$C_6$ alkyl, $-O-C_1$-$C_6$haloalkyl $-NH_2$, $-NO_2$, $=O$, $-CN$; and $C_{1-6}$ alkyl optionally substituted with one or more substituents independently selected from halogen, —OH, —O—$C_1$-$C_6$ alkyl, —O—$C_1$-$C_6$ haloalkyl —NH$_2$, —NO$_2$, =O, and —CN;

$n^F$ is selected from 0 and 1; and $m^F$ is selected from 0, 1, and 2.

In certain embodiments IL-17 Targeting Ligand is of Formula:

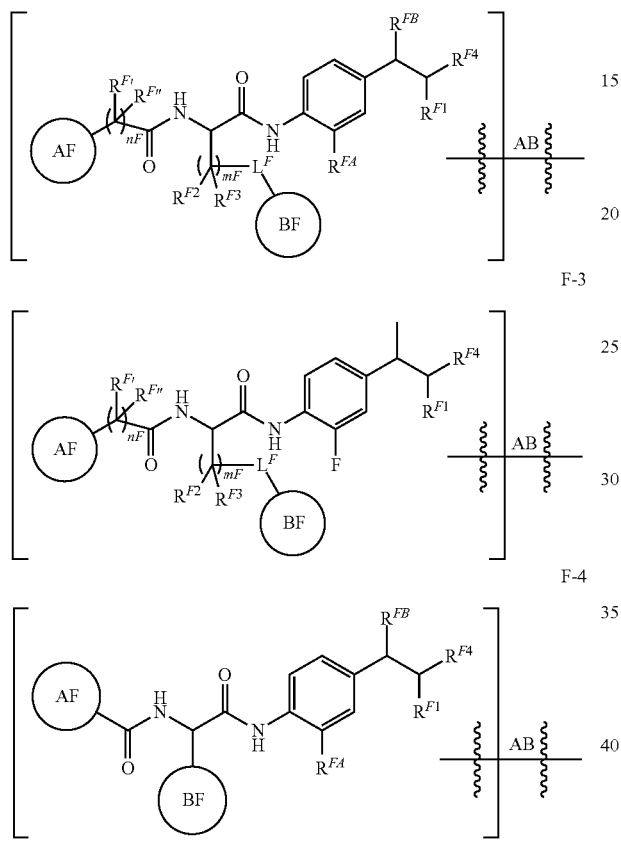

F-2

F-3

F-4

In certain embodiments IL-17 Targeting Ligand is of Formula:

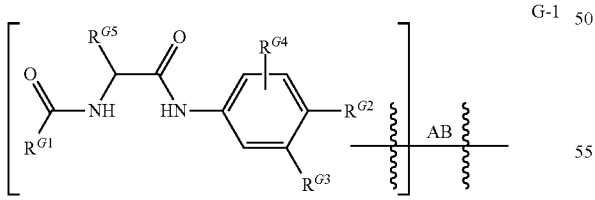

G-1 wherein,

RG1 is selected from the group consisting of 5- or 6-membered heteroaryl, 9- or 10-membered bicyclic heteroaryl, phenyl, ($C_1$-$C_6$)alkoxy, ($C_3$-$C_7$)cycloalkoxy, ($C_1$-$C_6$)alkyl, phenyl-($C_1$-$C_4$)alkyl, ($C_3$-$C_7$) cycloalkyl, 4-6-membered heterocycloalkyl and —NR$^{GC}$R$^{GD}$, wherein said 5- or 6-membered heteroaryl, 9- or 10-membered bicyclic heteroaryl, phenyl, ($C_1$-$C_6$)alkoxy, ($C_3$-$C_7$)cycloalkoxy, ($C_1$-$C_6$)alkyl, phenyl-($C_1$-$C_4$)alkyl, ($C_3$-$C_7$)cycloalkyl and 4-6-membered heterocycloalkyl is optionally substituted with one or more substituents independently selected from R$^{GA}$;

R$^{GA}$ represents deuterium, halogen, hydroxy, —NR$^{GC}$R$^{GD}$, ($C_1$-$C_6$)alkyl, ($C_1$-$C_6$)alkylcarbonyl, ($C_3$-$C_7$)cycloalkyl, phenyl, 5- or 6-membered heteroaryl or, 4-6-membered heterocycloalkyl, wherein said ($C_1$-$C_6$)alkyl, ($C_1$-$C_6$)alkylcarbonyl, ($C_3$-$C_7$)cycloalkyl, phenyl, 5- or 6-membered heteroaryl or 4-6-membered heterocycloalkyl is optionally substituted with one or more substituents independently selected from deuterium, halogen, hydroxy, cyano, ($C_1$-$C_4$)alkyl, ($C_3$-$C_7$)cycloalkyl, ($C_1$-$C_4$)alkoxy, —SO$_2$—($C_1$-$C_4$)alkyl and —NR$^{GC}$R$^{GD}$;

R$^{G2}$ is selected from the group consisting of 5- or 6-membered heteroaryl, wherein said 5- or 6-membered heteroaryl is optionally substituted with one or more substituents independently selected from R$^{GB}$, wherein said 5- or 6-membered heteroaryl may optionally contain —CO— as a ring member and wherein when said 5 membered heteroaryl contains nitrogen as a ring atom said nitrogen may optionally be substituted with a substituent selected from R$^{G8}$;

R$^{GB}$ represents deuterium, halogen, cyano, hydroxy, —NR$^{GC}$R$^{GD}$, ($C_1$-$C_6$)alkyl, ($C_1$-$C_6$)alkoxy, ($C_1$-$C_6$)alkyl-CO—O—(CH$_2$)$_n$— or ($C_3$-$C_7$)cycloalkyl, wherein n is 1-4, and wherein said ($C_1$-$C_6$)alkyl, ($C_1$-$C_6$)alkoxy or ($C_3$-$C_7$)cycloalkyl is optionally substituted with one or more substituents independently selected from deuterium, halogen, cyano, hydroxy, —NR$^{GC}$R$^{GD}$ and ($C_1$-$C_4$)alkoxy;

R$^{GC}$ and R$^{GD}$ each independently are selected from the group consisting of hydrogen and ($C_1$-$C_6$)alkyl, or R$^{GC}$ and R$^{GD}$ together form pyrrolidinyl or piperidinyl, wherein said ($C_1$-$C_6$)alkyl, pyrrolidinyl or piperidinyl is optionally substituted with one or more substituents independently selected from halogen, cyano and hydroxy;

R$^{G8}$ is selected from the group consisting of -L$^G$-PO(OH)$_2$ and —CHR$^{GG}$O—(CO-A-NR$^{GH}$))$_{0\ or\ 1}$—CO-A-NR$^{GH}$R$^{GI}$.

L$^G$ is selected from the group consisting of a bond or —CHR$^{GG}$O—;

wherein each —CO-A-NR$^{GH}$— independently represents an amino acid residue wherein the amino acid residue is selected from the natural amino acids either in D or L-form or as mixtures of the D and L form, and wherein said amino acid residue may be substituted on the a-amino group with a substituent R$^{GH}$;

R$^{GG}$, R$^{GH}$, and R$^{GI}$ are independently selected from hydrogen and ($C_1$-$C_6$) alkyl;

R$^{G3}$ is selected from the group consisting of hydrogen, deuterium, hydroxy and halogen;

R$^{G4}$ is selected from the group consisting of hydrogen, deuterium and halogen;

R$^{G5}$ is selected from the group consisting of —CHR$^{G6}$R$^{G7}$, ($C_3$-$C_{10}$)cycloalkyl and GG, wherein said ($C_3$-$C_{10}$)cycloalkyl and GG are optionally substituted with one or more substituents independently selected from deuterium, halogen, cyano, hydroxy, ($C_1$-$C_4$)alkyl and halo($C_1$-$C_4$)alkyl;

GG represents

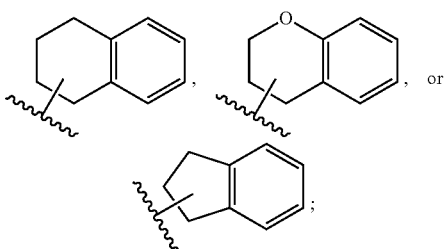

and
R$^{G6}$ and R$^{G7}$ each independently represents hydrogen, phenyl, (C$_1$-C$_6$)alkyl, or (C$_3$-C$_7$)cycloalkyl, wherein said phenyl, (C$_1$-C$_6$)alkyl or (C$_3$-C$_7$)cycloalkyl is optionally substituted with one or more substituents independently selected from halogen, cyano, hydroxy and (C$_1$-C$_4$)alkyl.

In certain embodiments IL-17 Targeting Ligand is of Formula:

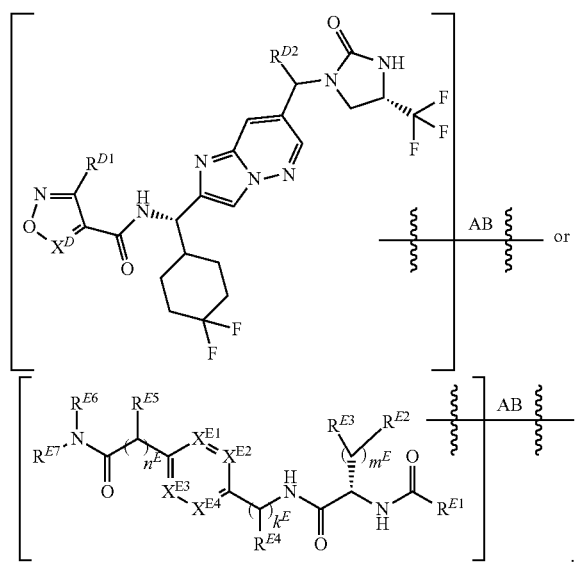

Interleukin-6 (IL-6)

In some embodiments, the Target Extracellular Protein is human interleukin-6 (IL-6) (UniProtKB—P05231 (IL6_HUMAN)). IL-6 is a cytokine with a wide variety of biological functions. It is a potent inducer of the acute phase response and plays an essential role in the final differentiation of B-cells into Ig-secreting cells. It is also involved in lymphocyte and monocyte differentiation. It also acts on B-cells, T-cells, hepatocytes, hematopoietic progenitor cells and cells of the CNS, and is required for the generation of T(H)17 cells. IL-6 has been implicated in a number of inflammatory diseases and cancers, including, but not limited to, Castleman's disease, metastatic castration-associated prostate cancer, renal cell carcinoma, large-cell lung carcinoma, ovarian cancer, rheumatoid arthritis, asthma.

The Protein Data Bank website provides the crystal structure of IL-6 searchable by 1P9M (Boulanger, M. J., et al., Science, 2003, 300: 2101-2104); 1ALU (Somers et al., EMBO J., 1997, 16, 989-997); 1IL6 and 2IL6 (Xu, G. Y., et al., J Mol Biol., 1997, 268 468-481) and 1N26 (Varghese et al., Proc Natl Acad Sci USA., 2002, 99 15959-15964); as well as the crystal structure of IL-6 bound to various compounds searchable by 4CNI (Shaw, S., et al., Mabs, 2014, 6: 773); and 4NI7 and 4NI9 (Gelinas et al., J Biol Chem. 2014, 289(12), 8720-8734). Additionally, Gelinas et al., provides insight into the crystal structure of interleukin-6 in complex with a modified nucleic acid ligand (Gelinas, A. D., et al., J Biol Chem. 2014, 289(12), 8720-8734); and Somers et al., provides insight into the crystal structure of interleukin 6: implications for a novel mode of receptor dimerization and signaling.

Non-limiting examples of IL-6 direct or indirect inhibitors are provided in FIG. 1. Additional IL-6 direct or indirect inhibitors can be found in, for example, U.S. Pat. No. 8,901,310; U.S. patent Ser. No. 10/189,796; U.S. Pat. No. 9,694,015; each incorporated herein by reference. In another embodiment the IL-6 Extracellular Targeting Ligand is AvimarC326 or a binding fragment thereof which is described in Nat Biotechnol 23, 1556-1561 (2005).

In some embodiments, the Target Extracellular Protein is Interleukin-6. Interleukin-6 (IL-6) is a cytokine that is a crucial component of the acute phase immune response. IL-6 ligand binds to IL-6 receptor, and the heterodimer then associates with IL6ST and gp130, stimulating a response. During infection certain molecules from pathogens bind to toll-like receptors, which activate macrophages to produce IL-6. In addition to stimulating differentiation of B cells and neutrophils, IL-6 mediates the fever response.

IL-6 has been implicated in many inflammatory diseases, including multiple sclerodid, neuromyelitis optica spectrum disorder, diabetes, atherosclerosis, depression, Alzheimer's disease, systemic lupus erythromatosus, multiple myeloma, prostate cancer, Behcet's disease, rheumatoid arthritis, systemic juvenile idiopathic arthritis, and Castleman's disease.

IL-6 signaling is also important to the musculoskeletal system. In bone, it interacts with VEGF stimulating angiogenesis. In muscle cells, IL-6 is produced in large amounts during exercise. In contrast to its role in stimulating the immune system, during exercise IL-6 is anti-inflammatory.

The Protein Data Bank website provides the crystal structure of Interleukin-6, searchable by 1ALU (Somers, W. S. et al. 1.9 A crystal structure of interleukin 6: implications for a novel mode of receptor dimerization and signaling. (1997) EMBO J. 16: 989-997), 1IL6 (Xu, G. Y. et al. Solution structure of recombinant human interleukin-6 (1997) J Mol Biol 268: 468-481), and the structure of IL-6 bound in the active hexameric complex searchable by 1P9M (Boulanger, M. J. et al. Hexameric Structure and Assembly of the Interleukin-6/IL-6-alpha-Receptor/gp130 Complex. (2003) Science 300: 2101-2104)

Non-limiting examples of IL-6 Targeting Ligands can be found in, for example, USP 10633423, USP 10669314, US 2004/0092720, and Ranganath, S. et al. Discovery and Characterization of a Potent Interleukin-6 Binding Peptide with Neutralizing Activity In Vivo. PLoS ONE 10(11): e0141330.

SEQ ID NO:350 QSDChaDCIHRLLEAF(4-F)LDPNL-TEEQRWEKIGlaKINDECE (Ranganath, S. et al. PLoS ONE 10(11):e0141330)

SEQ ID NO:351 QSDChaDCIHRLLEAF(4-F)LDPNL-TEEQRWERIGlaK(PEG30L)INDECE (Ranganath, S. et al. PLoS ONE 10(11):e0141330)

SEQ ID NO:352 QSDChaDCIHRLLEAF(4-F)LDPNL-TEEQRWERIGlaK(PEG20Br)INDECE (Ranganath, S. et al. PLoS ONE 10(11):e0141330)

SEQ ID NO:353 QSDChaDCIHRLLEAF(4-F)LDPNL-TEEQRWERIGlaK(PEG40Br)INDECE (Ranganath, S. et al. PLoS ONE 10(11):e0141330)

SEQ ID NO:354 FDhLDCIHRLLEAFLDPNLTEQQR-WEKIDKINDECE (Ranganath, S. et al. PLoS ONE 10(11):e0141330)

SEQ ID NO:355 QSDChaDCIHRLLEAF(4-F)LDPNL-TEEQRWERIGlaKINDECE (Ranganath, S. et al. PLoS ONE 10(11):e0141330)

SEQ ID NO:356 SWQSDChaDCIHRLLEAFLDK-AcNLTEEQRWERIDKINDECE (Ranganath, S. et al. PLoS ONE 10(11):e0141330)

SEQ ID NO:357 SWQSDChaDCIHRLLEAFLDK-PEG40BrNLTEEQRWERIDKINDECE (Ranganath, S. et al. PLoS ONE 10(11):e0141330)

In certain embodiments the IL-6 Targeting ligand is SEQ ID NO:343, bound to the linker through the PEGylated lysine residue.

SEQ ID NO:358 EEX$_3$X$_4$AWX$_7$EIHX$_{11}$LPNLX$_{16}$X$_{17}$X$_{18}$QX$_{20}$X$_{21}$AFIX$_{25}$X$_{26}$LX$_{28}$X$_{29}$ (U.S. Pat. No. 10,633,423)

wherein, independently from each other,
X$_3$ is selected from A, F, H, K, Q, R, S, W and Y:
X$_4$ is selected from A, D, E, F, H, I, K, L, M, N, Q, R, S, T, V and Y;
X$_7$ is selected from F, H, I, K, L, M, N, R, S, T, V, W and Y;
X$_{11}$ is selected from A, I, K, L, M, N, R, S, T and V;
X$_{16}$ is selected from N and T;
X$_{17}$ is selected from A, I, T and V;
X$_{18}$ is selected from D, E, G, H, K, N, Q, R, S and T;
X$_{20}$ is selected from I, L, M, R, T and V;
X$_{21}$ is selected from A, S, T and V
X$_{25}$ is selected from I, M, Q, S, T, V and W;
X$_{26}$ is selected from K and S,
X$_{28}$ is selected from F, L, M and Y; and
X$_{29}$ is selected from D and R;

SEQ ID NO: 359 EEX$_3$X$_4$AWX$_7$EIHX$_{11}$LPNLX$_{16}$X$_{17}$X$_{18}$QX$_{20}$X$_{21}$AFIX$_{25}$X$_{26}$LX$_{28}$X$_{29}$) (U.S. Pat. No. 10,669,314)

wherein, independently from each other,
X$_3$ is selected from A, F, H, K, Q, R, S, W and Y;
X$_4$ is selected from A, D, E, F, H, I, K, L, M, N, Q, R, S, T, V and Y;
X$_7$ is selected from F, H, I, K, L, M, N, R, S, T, V, W and Y;
X$_{11}$ is selected from A, I, K, L, ML N, R S, T and V;
X$_{16}$ is selected from N and T:
X$_{17}$ is selected from A, I, T and V;
X$_{18}$ is selected from D, E, G, H, K, N, Q, R, S and T;
X$_{20}$ is selected from I, L, M, R, T and V,
X$_{21}$ is selected from A, S, T and V;
X$_{25}$ is selected from I, M, Q, S, T, V and W;
X$_{26}$ is selected from K and S;
X$_{28}$ is selected from FL, M and Y; and X$_{29}$ is selected from D and R;

In certain embodiments the targeting ligand for treating an IL-6 mediated disease binds to gp130. Non-limiting examples of gp130 Targeting Ligands can be found in, for example, Ahn, S-H. et al. In vitro and in vivo pharmacokinetic characterization of LMT-28 as a novel small molecular interleukin-6 inhibitor 2020 Asian-Australas J Anim Sci. 33:670-677, Aqel, S. I. Novel small molecule IL-6 inhibitor suppresses autoreactive Th17 development and promotes Treg development. (2019) Clinical and Experimental Immunology, 196:215-225, Hong, S.-S. et al. A Novel Small-Molecule Inhibitor Targeting the IL-6 Receptor beta Subunit, Glycoprotein 130. 2015 J Immunol 195:237-245

In certain embodiments the gp130 binding Targeting Ligand is selected from

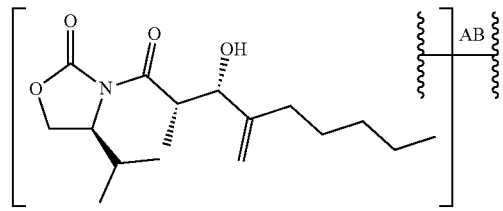

,

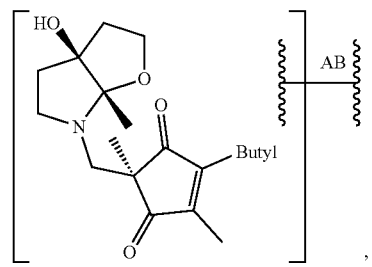

,

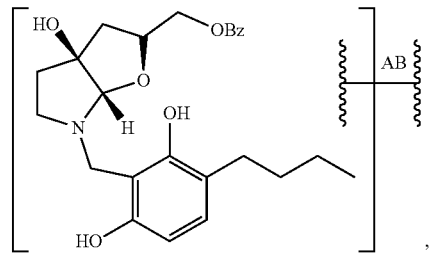

,

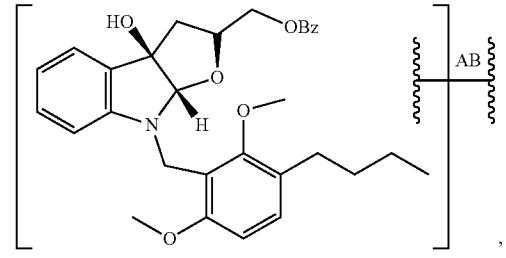

,

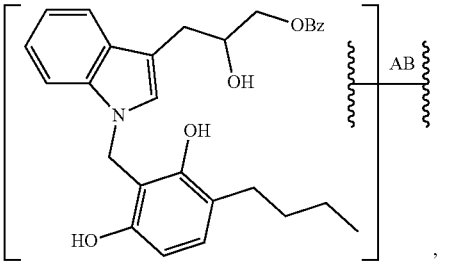

,

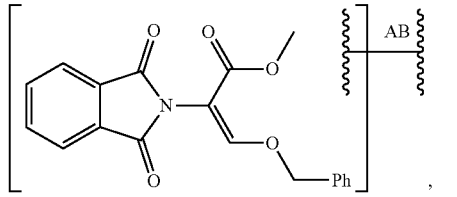

,

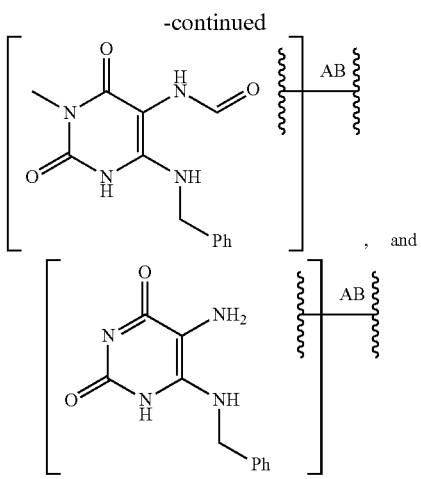
, and

Immunoglobulin A1 (IgA1)

Immunoglobulin A is a class of antibodies which is commonly found in secretions, but is also present in serum. IgA contains four heavy chains and four light chains, in a dimeric form. IgA exists in two isotypes, IgA1 and IgA2. IgA1 contains more repeats in the hinge region and is the predominant form found in serum. While production of IgA maintains strong mucosal immunity and defending against pathogens, it can become toxic. IgA nephropathy, also known as Berger's disease, is the pathological buildup of IgA antibodies which reduces kidney function. The etiology of the disease remains unclear, however it has been suggested that the glycosylation pattern on the hinge region plays a role. As proper kidney function is important for overall health, IgA nephropathy is associated with systemic diseases such as liver failure, cancer, celiac disease, systemic lupus erythematosus, rheumatoid arthritis, heart failure, reactive arthritis, and ankylosing spondylitis.

The Protein Data Bank website provides the crystal structure of IgA1, and representative example include PDB accession codes 1IGA (Boehm, M. K. 1999, J. Mol. Bio. 286 1421-1447), 2ESG (Almogren, A. 2006 J. Mol. Biol. 356, 413-431), 6XJA, 7JGJ, (Eisenmesser, E. Z. 2020, Nat. Commun, 11, 6063-6063), and 3CHN (Bonner, A. 2009, Mucosal Immunol., 2, 74-84).

Direct or indirect IgA1 binding molecules include jacalin and
SEQ ID NO:360 YYALSDAKEEEPRYKALRGENQDL-REKERKYQDKIKKLEEKEKNLEKKS.

Embodiments of the Linker

In non-limiting embodiments, Linker$^A$ and Linker$^B$ are independently selected from:

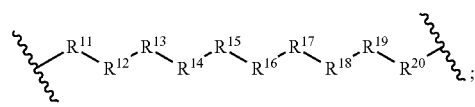

wherein:
$R^{11}$, $R^{12}$, $R^{13}$, $R^{14}$, $R^{15}$, $R^{16}$, $R^{17}$, $R^{18}$, $R^{19}$, and $R^{20}$ are independently at each occurrence selected from the group consisting of a bond, alkyl, —C(O)—, —C(O)O—, —OC(O)—, —SO$_2$—, —S(O)—, —C(S)—, —C(O)NR$^6$—, —NR$^6$C(O)—, —O—, —S—, —NR$^6$—, —C(R$^{21}$R$^{21}$)—, —P(O)(R$^3$)O—, —P(O)(R$^3$)—, a divalent residue of a natural or unnatural amino acid, alkenyl, alkynyl, haloalkyl, alkoxy, aryl, heterocycle, heteroaryl, —CH$_2$CH$_2$—[O—(CH$_2$)$_2$]$_n$—O—, —CH$_2$CH$_2$—[O—(CH$_2$)$_2$]$_n$—NR$^6$—, —CH$_2$CH$_2$—[O—(CH$_2$)$_2$]$_n$—, —[O—(CH$_2$)$_2$—O-]$_n$—, —[O—(CH$_2$)$_2$]$_n$—, —[O—CH(CH$_3$)C(O)]$_n$—, —[C(O)—CH(CH$_3$)—O]$_n$—, —[O—CH$_2$C(O)]$_n$—, —[C(O)—CH$_2$—O]$_n$—, a divalent residue of a fatty acid, a divalent residue of an unsaturated or saturated mono- or di-carboxylic acid; each of which is optionally substituted with 1, 2, 3, or 4 substituents independently selected from R$^{21}$;

n is independently selected at each instance from 0, 1, 2, 3, 4, 5, 6, 7, 8, 9, or 10;

$R^{21}$ is independently at each occurrence selected from the group consisting of hydrogen, alkyl, alkenyl, alkynyl, F, Cl, Br, I, hydroxyl, alkoxy, azide, amino, cyano, —NR$^6$R$^7$, —NR$^8$SO$_2$R$^3$, —NR$^8$S(O)R$^3$, haloalkyl, heteroalkyl, aryl, heteroaryl, and heterocycle;

and the remaining variables are as defined herein.

In one embodiment Linker$^A$ is bond and Linker$^B$ is

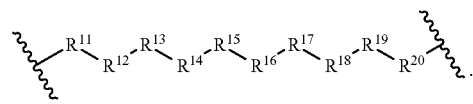

In one embodiment Linker$^B$ is bond and Linker$^A$ is

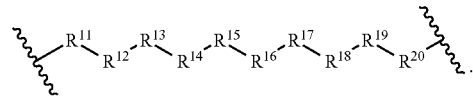

In one embodiment, a divalent residue of an amino acid is selected from

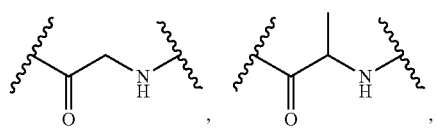

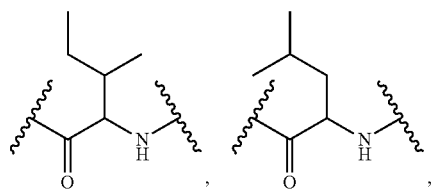

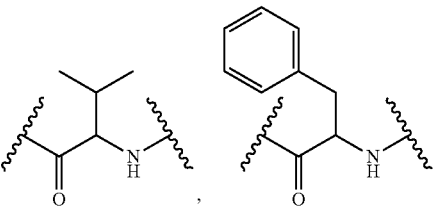

499
-continued
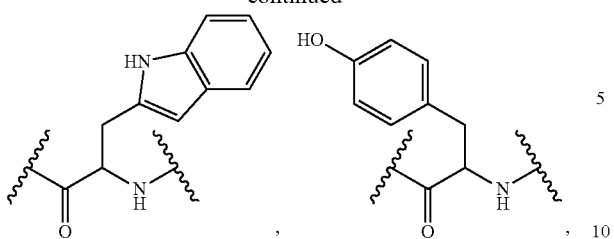
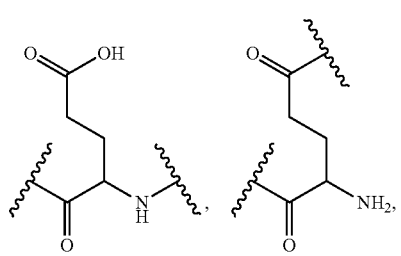
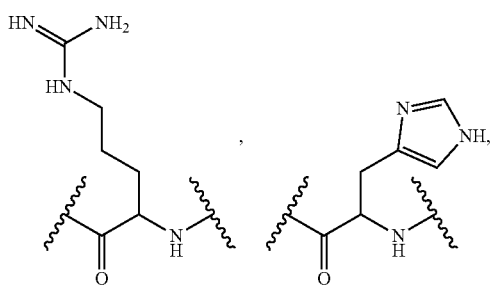
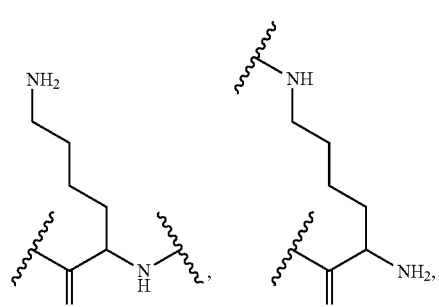
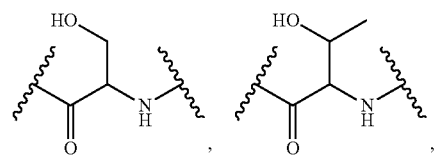
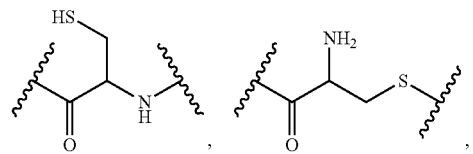
500
-continued
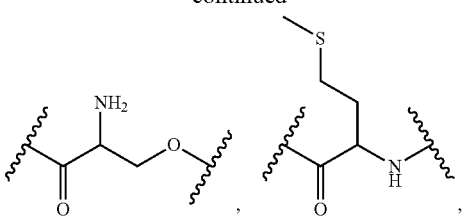
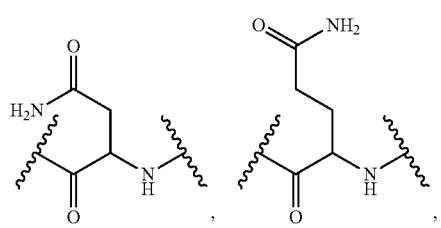
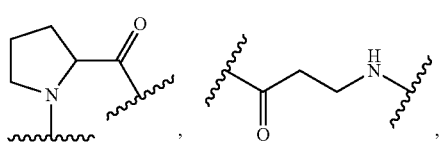
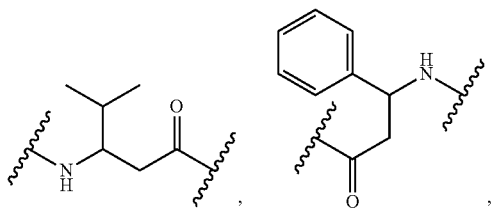
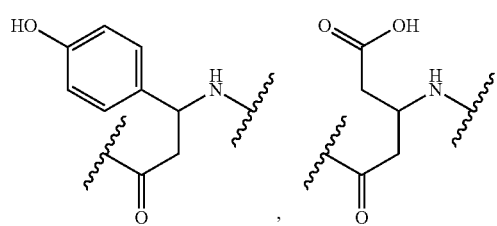
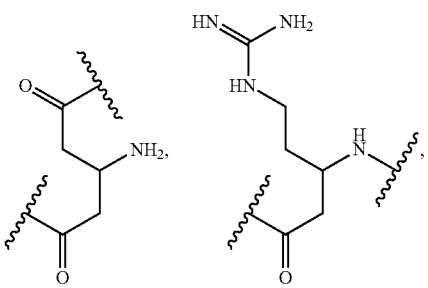
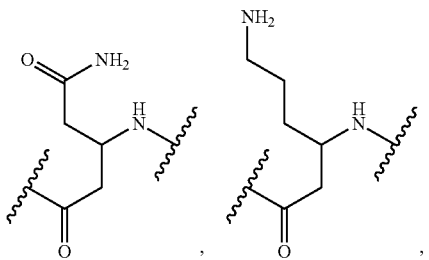
, and

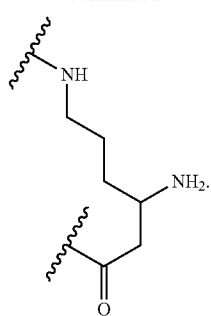

wherein the amino acid can be oriented in either direction and wherein the amino acid can be in the L- or D-form.

In one embodiment, a divalent residue of a dicarboxylic acid is generated from a nucleophilic addition reaction:

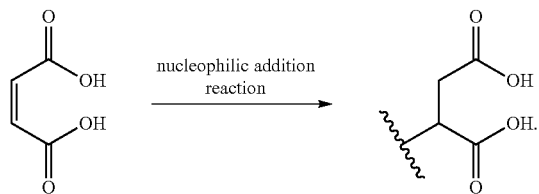 [SMILES: O=C(O)/C=C\C(=O)O ; *C(CC(=O)O)C(=O)O]

Non-limiting embodiments of a divalent residue of a dicarboxylic acid generated from a nucleophilic addition reaction include:

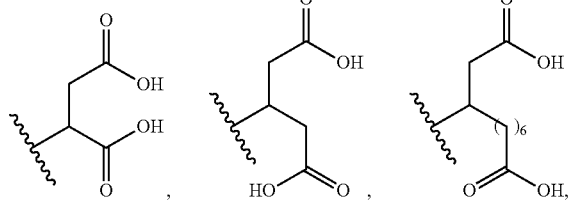

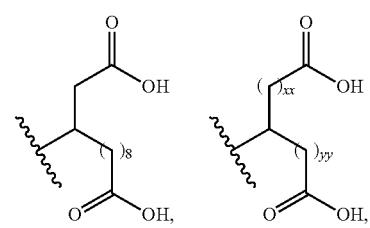

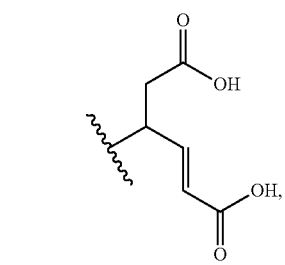

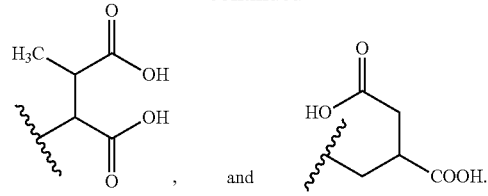

As used in the embodiments herein, xx is independently selected from 0, 1, 2, 3, 4, 5, 6, 7, 8, 9, 10, 11, 12, 13, 14, 15, 16, 17, 18, 19, 20, 21, 22, 23, 24, and 25.

As used in the embodiments herein, yy is independently selected from 0, 1, 2, 3, 4, 5, 6, 7, 8, 9, 10, 11, 12, 13, 14, 15, 16, 17, 18, 19, 20, 21, 22, 23, 24, and 25.

In one embodiment, a divalent residue of a dicarboxylic acid is generated from a condensation reaction:

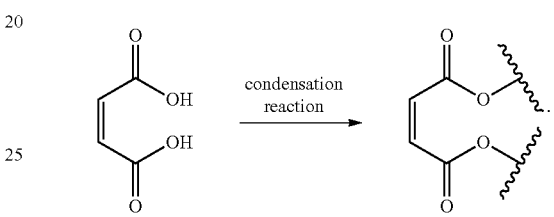

Non-limiting embodiments of a divalent residue of a dicarboxylic acid generated from a condensation include:

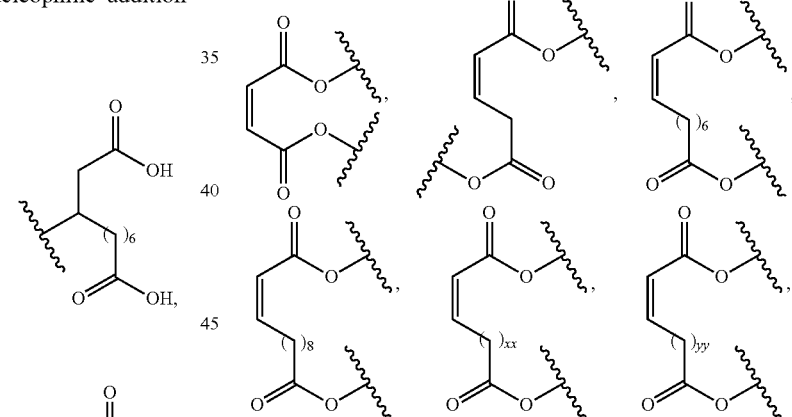

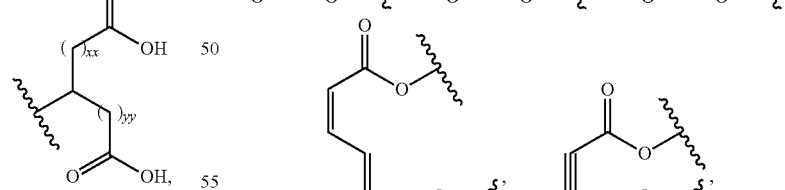

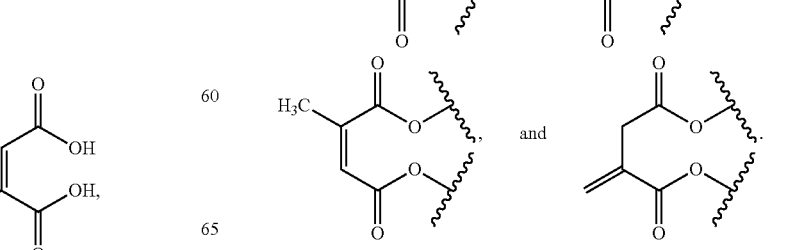

Non-limiting embodiments of a divalent residue of a saturated dicarboxylic acid include:

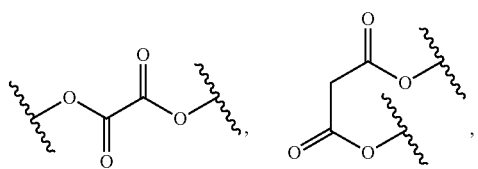

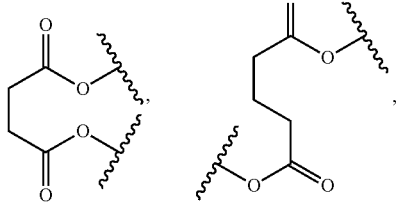

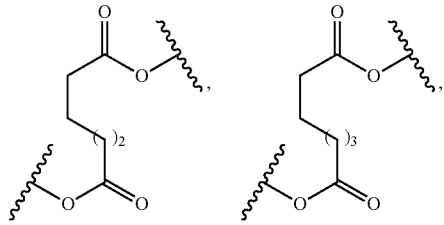

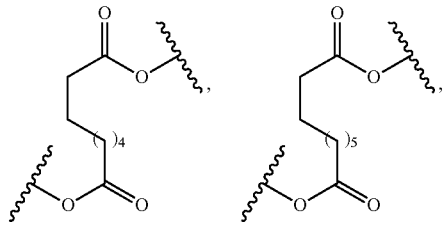

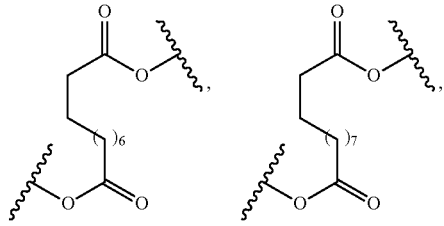

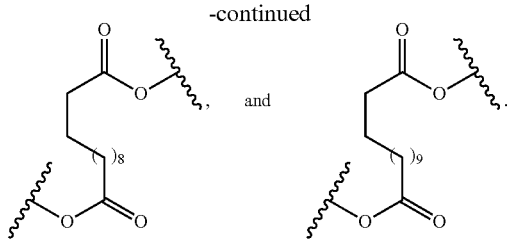

Non-limiting embodiments of a divalent residue of a saturated dicarboxylic acid include:

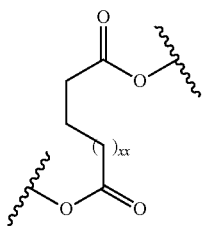

Non-limiting embodiments of a divalent residue of a saturated monocarboxylic acid is selected from butyric acid (—OC(O)(CH$_2$)$_2$CH$_2$—), caproic acid (—OC(O)(CH$_2$)$_4$CH$_2$—), caprylic acid (—OC(O)(CH$_2$)$_5$CH$_2$—), capric acid (—OC(O)(CH$_2$)$_8$CH$_2$—), lauric acid (—OC(O)(CH$_2$)$_{10}$CH$_2$—), myristic acid (—OC(O)(CH$_2$)$_{12}$CH$_2$—), pentadecanoic acid (—OC(O)(CH$_2$)$_{13}$CH$_2$—), palmitic acid (—OC(O)(CH$_2$)$_{14}$CH$_2$—), stearic acid (—OC(O)(CH$_2$)$_{16}$CH$_2$—), behenic acid (—OC(O)(CH$_2$)$_{20}$CH$_2$—), and lignoceric acid (—OC(O)(CH$_2$)$_{22}$CH$_2$—);

Non-limiting embodiments of a divalent residue of a fatty acid include residues selected from linoleic acid, palmitoleic acid, vaccenic acid, paullinic acid, oleic acid, elaidic acid, gondoic acid, gadoleic acid, nervonic acid, myristoleic acid, and erucic acid:

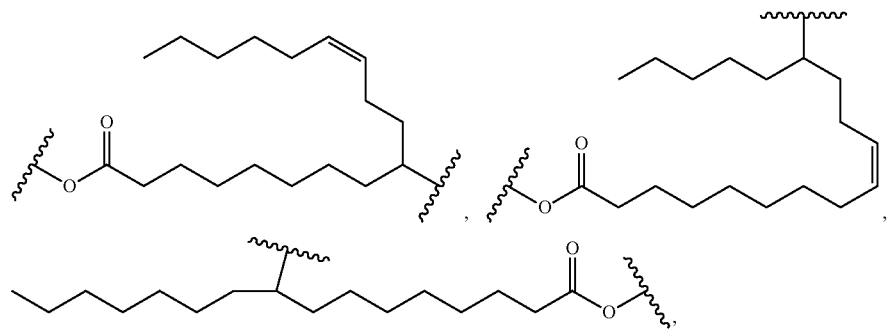

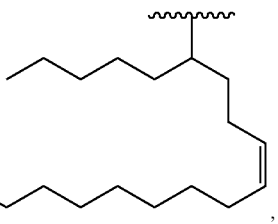

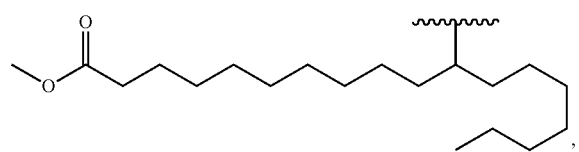

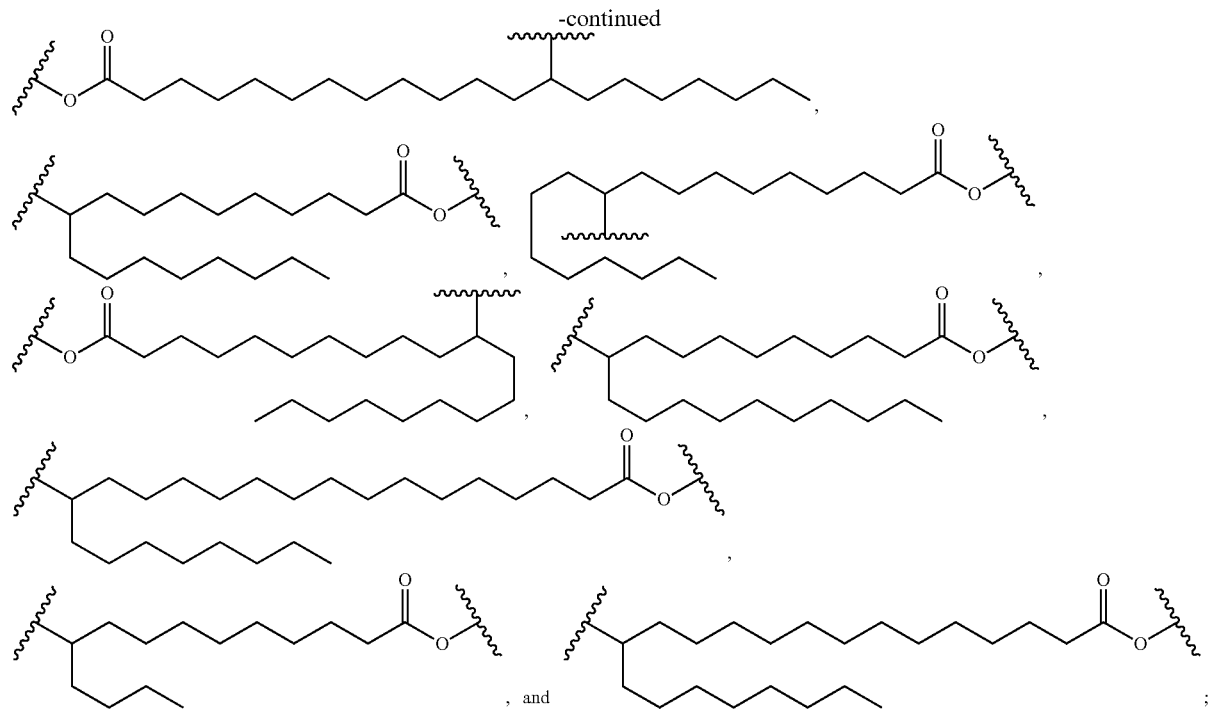
, and
;

Non-limiting embodiments of a divalent residue of a fatty acid is selected from linoleic acid (—C(O)(CH$_2$)$_7$(CH)$_2$CH$_2$(CH)$_2$(CH$_2$)$_4$CH$_2$—), docosahexaenoic acid (—C(O)(CH$_2$)$_2$(CHCHCH$_2$)$_6$CH$_2$—), eicosapentaenoic acid (—C(O)(CH$_2$)$_3$ (CHCHCH$_2$)$_5$CH$_2$—), alpha-linolenic acid (—C(O)(CH$_2$)$_7$(CHCHCH$_2$)$_3$CH$_2$—) stearidonic acid (—C(O)(CH$_2$)$_4$(CHCHCH$_2$)$_4$CH$_2$—), y-linolenic acid (—C(O)(CH$_2$)$_4$(CHCHCH$_2$)$_3$(CH$_2$)$_3$CH$_2$—), arachidonic acid (—C(O)(CH$_2$)$_3$, (CHCHCH$_2$)$_4$(CH$_2$)$_4$CH$_2$—), docosatetraenoic acid (—C(O)(CH$_2$)$_5$(CHCHCH$_2$)$_4$(CH$_2$)$_4$CH$_2$—), palmitoleic acid (—C(O)(CH$_2$)$_7$CHCH(CH$_2$)$_5$CH$_2$—), vaccenic acid (—C(O)(CH$_2$)$_9$CHCH(CH$_2$)$_5$CH$_2$—), paullinic acid (—C(O)(CH$_2$)$_{11}$CHCH(CH$_2$)$_5$CH$_2$—), oleic acid (—C(O)(CH$_2$)$_7$CHCH(CH$_2$)$_7$CH$_2$—), elaidic acid (—C(O)(CH$_2$)$_7$CHCH(CH$_2$)$_7$CH$_2$—), gondoic acid (—C(O)(CH$_2$)$_9$CHCH(CH$_2$)$_7$CH$_2$—), gadoleic acid (—C(O)(CH$_2$)$_7$CHCH(CH$_2$)$_9$CH$_2$—), nervonic acid (—C(O)(CH$_2$)$_{13}$CHCH(CH$_2$)$_7$CH$_2$—), mead acid (—C(O)(CH$_2$)$_3$(CHCHCH$_2$)$_3$(CH$_2$)$_6$CH$_2$—), myristoleic acid (—C(O)(CH$_2$)$_7$CHCH(CH$_2$)$_3$CH$_2$—), and erucic acid (—C(O)(CH$_2$)$_{11}$CHCH(CH$_2$)$_7$CH$_2$—).

In certain embodiments Linker$^C$ is selected from:

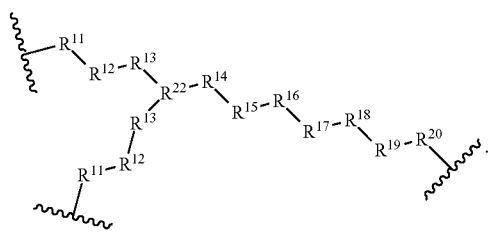

wherein:
R$^{22}$ is independently at each occurrence selected from the group consisting of alkyl, —C(O)N—, —NC(O)—, —N—, —C(R$^{21}$)—, —P(O)O—, —P(O)—, —P(O)(NR$^6$R$^7$)N—, alkenyl, haloalkyl, aryl, heterocycle, and heteroaryl, each of which is optionally substituted with 1, 2, 3, or 4 substituents independently selected from R$^{21}$;

and the remaining variables are as defined herein.

In certain embodiments Linker$^D$ is selected from:

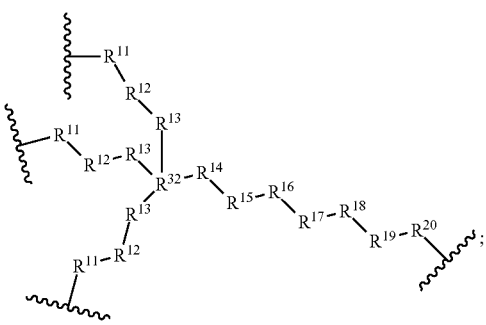

wherein:
R$^{32}$ is independently at each occurrence selected from the group consisting of alkyl, N$^+$X$^-$, —C—, alkenyl, haloalkyl, aryl, heterocycle, and heteroaryl, each of which is optionally substituted with 1, 2, 3, or 4 substituents independently selected from R$^{21}$;

X$^-$ is an anionic group, for example Br$^-$ or Cl$^-$ and all other variables are as defined herein.

In certain embodiments Linker⁴ is selected from:
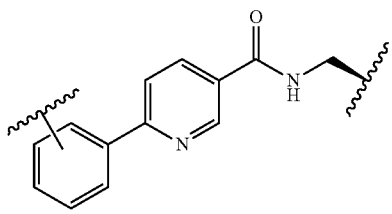
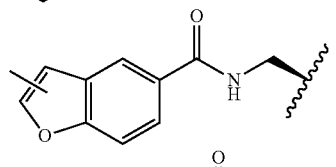
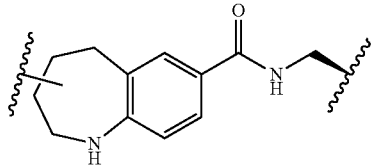
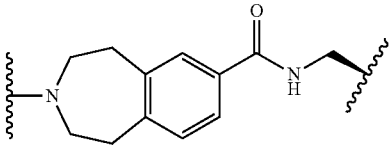
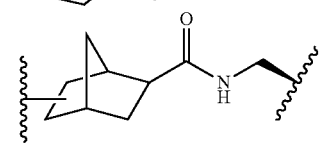
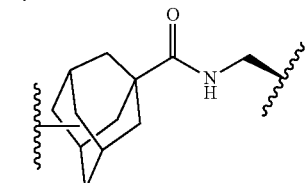
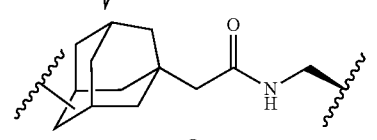
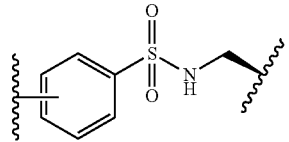
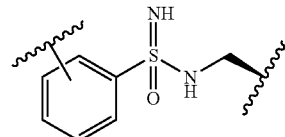
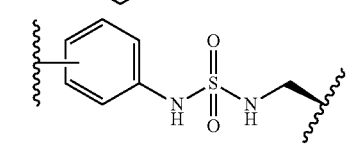
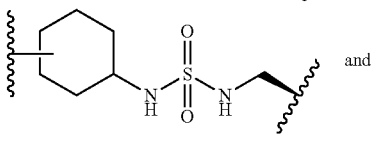 and
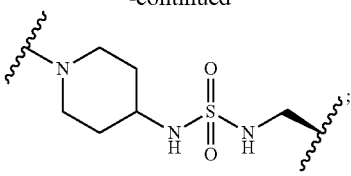
each of which is optionally substituted with 1, 2, 3, or 4 optional substituents as defined herein.
In certain embodiments Linker⁴ is selected from:
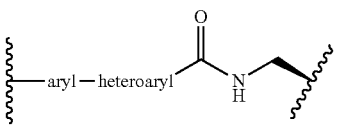
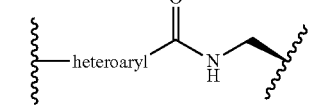
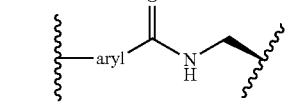
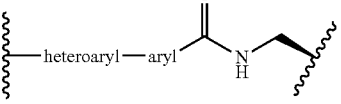
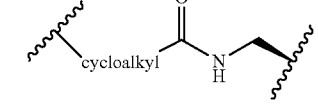
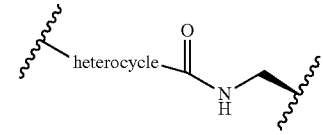
each of which is optionally substituted with 1, 2, 3, or 4 optional substituents as defined herein.
In certain embodiments Linker⁴ is selected from:
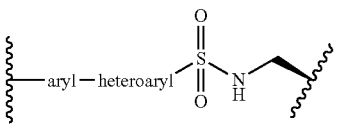
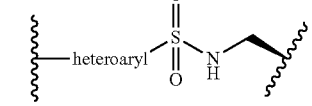
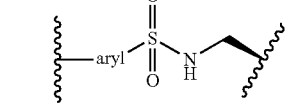
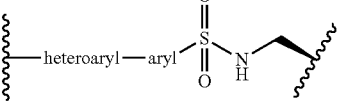

-continued

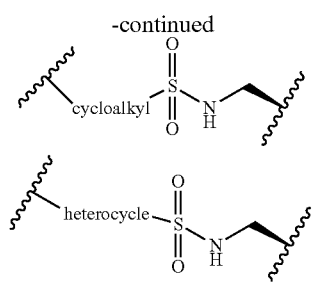

each of which is optionally substituted with 1, 2, 3, or 4 optional substituents as defined herein.

In certain embodiments Linker⁴ is selected from:

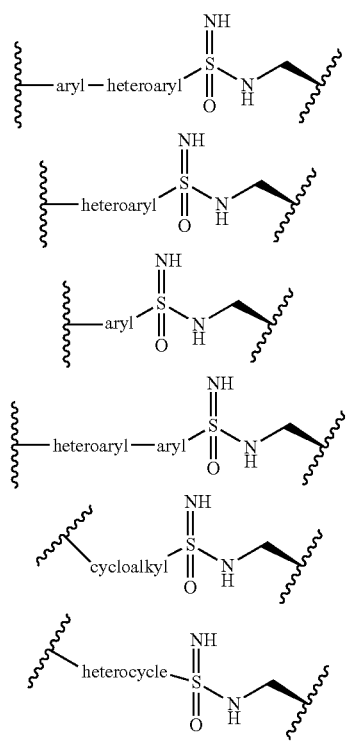

each of which is optionally substituted with 1, 2, 3, or 4 optional substituents as defined herein.

In certain embodiments Linker⁴ is selected from:

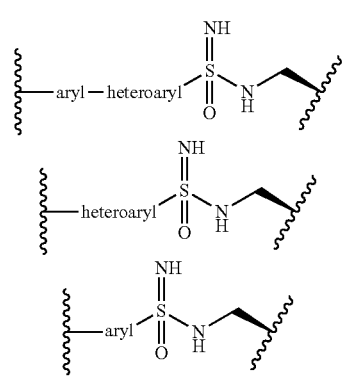

-continued

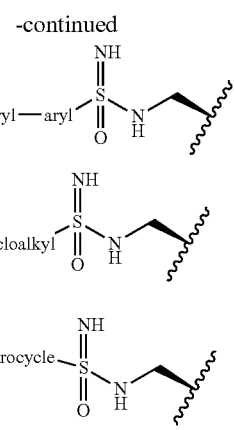

each of which is optionally substituted with 1, 2, 3, or 4 optional substituents as defined herein.

In certain embodiments Linker⁴ is selected from:

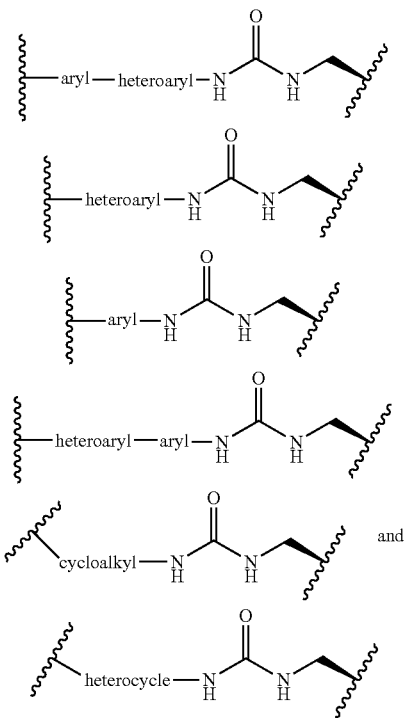

each of which is optionally substituted with 1, 2, 3, or 4 optional substituents as defined herein.

In certain embodiments Linker⁴ is selected from:

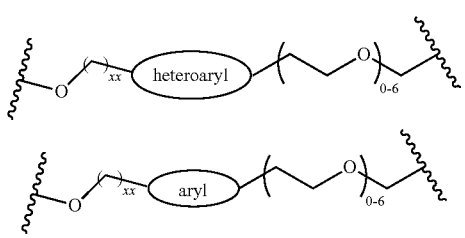

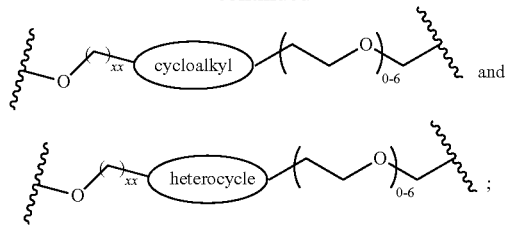

wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence.

In certain embodiments Linker$^A$ is selected from:

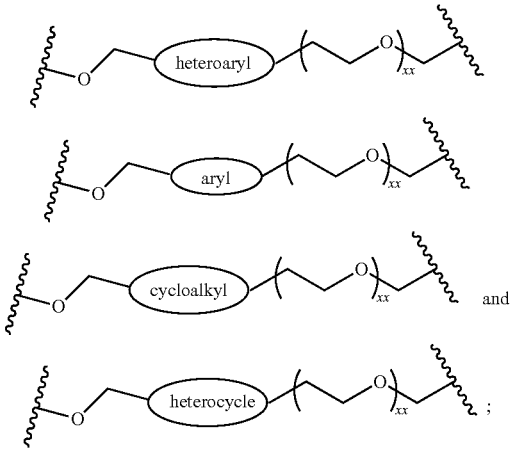

wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence.

In certain embodiments Linker$^A$ is selected from:

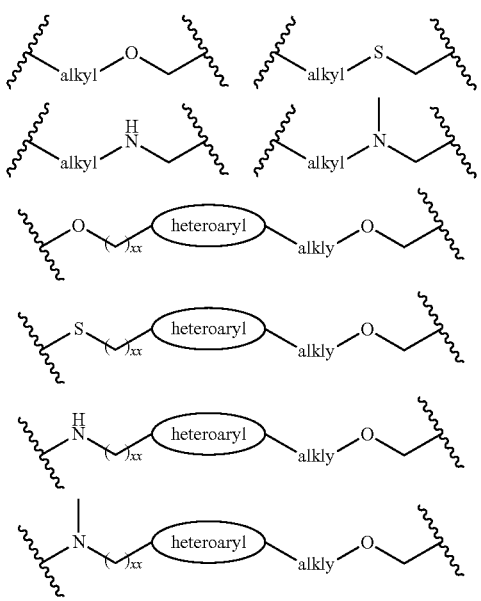

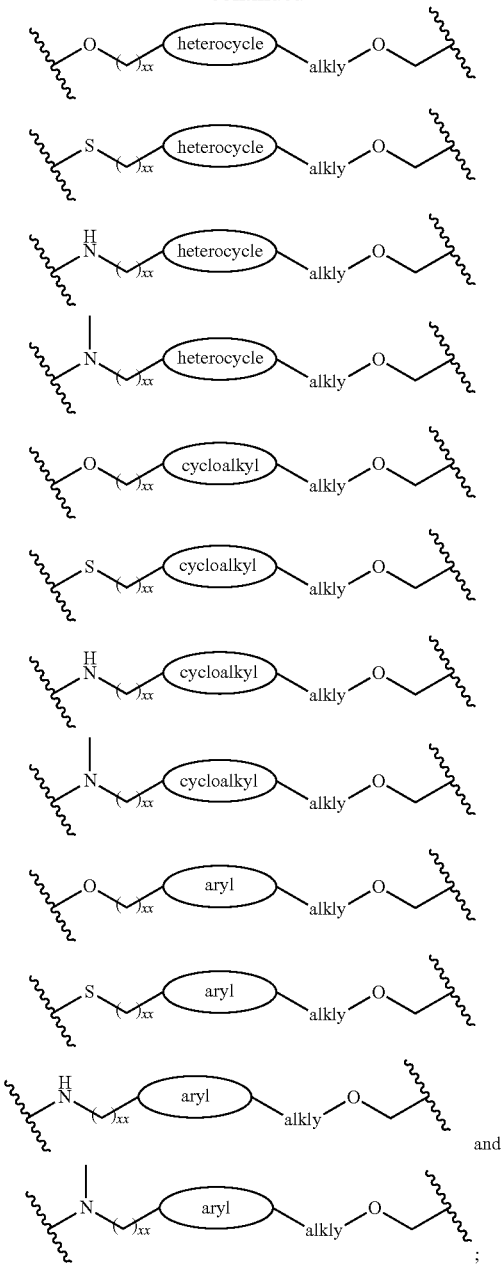

wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence.

In certain embodiments Linker$^B$ is selected from:

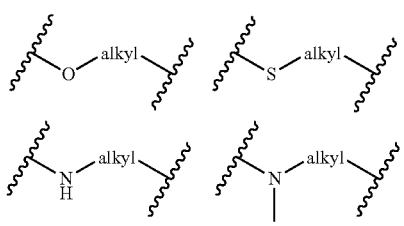

513
-continued
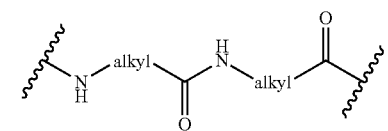
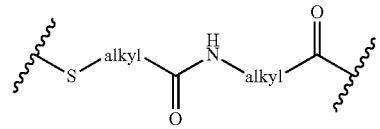
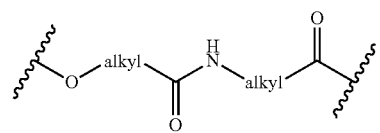
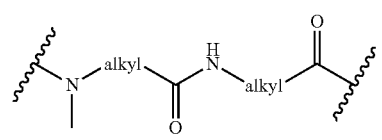
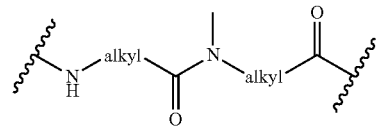
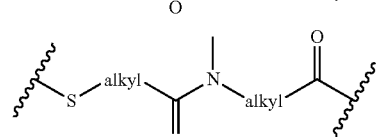
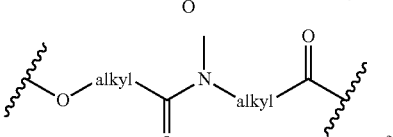
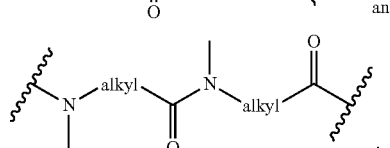
and
In certain embodiments Linker$^B$ is selected from:
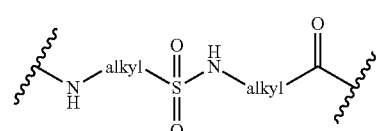
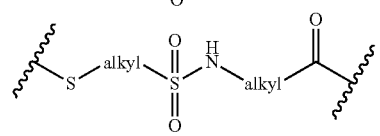
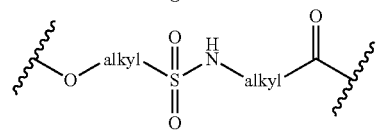
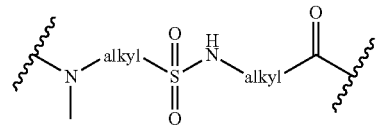
514
-continued
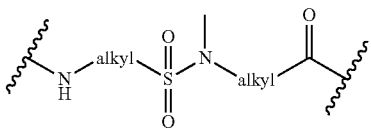
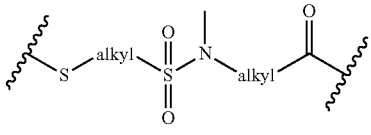
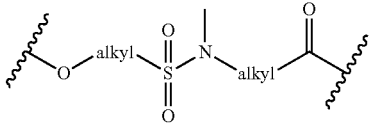
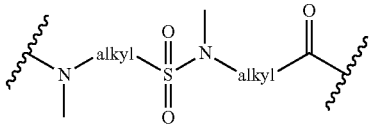
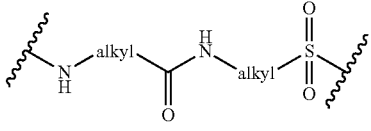
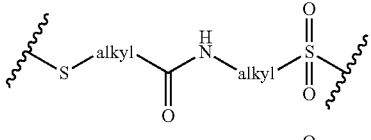
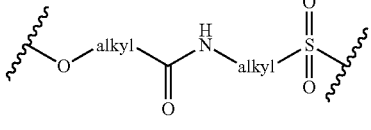
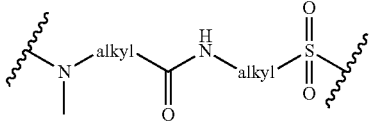
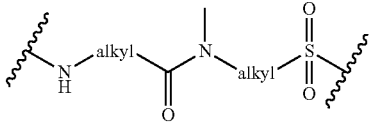
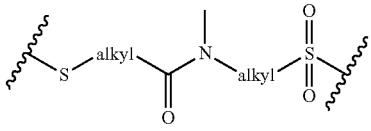
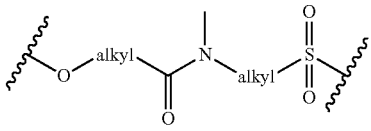
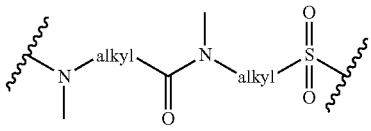
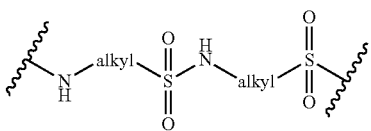

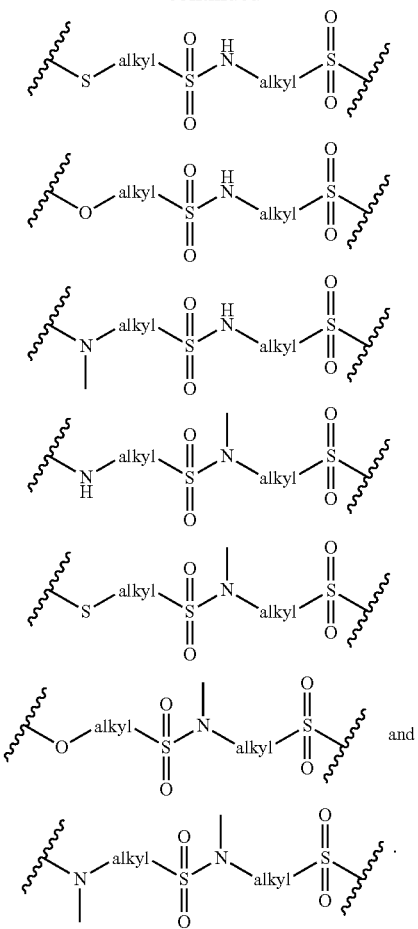
In certain embodiments Linker$^B$, Linker$^C$, or Linker$^D$ is selected from.
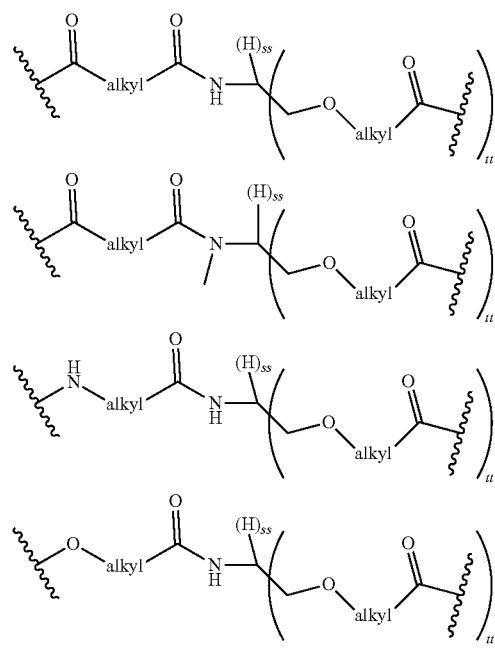
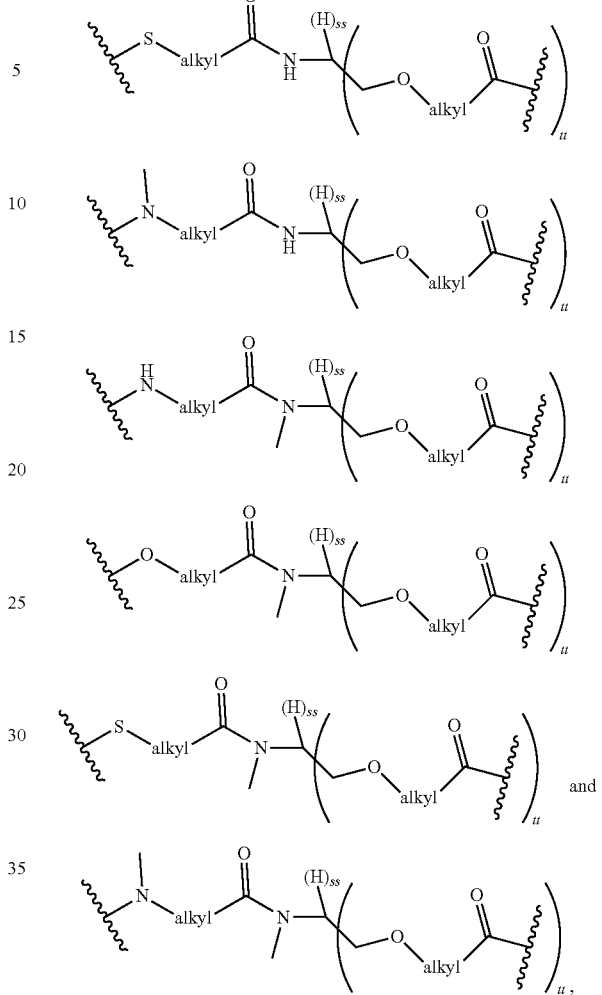
wherein tt is independently selected from 1, 2, or 3 and ss is 3 minus tt.
In certain embodiments Linker$^B$, Linker$^C$, or Linker$^D$ is selected from:
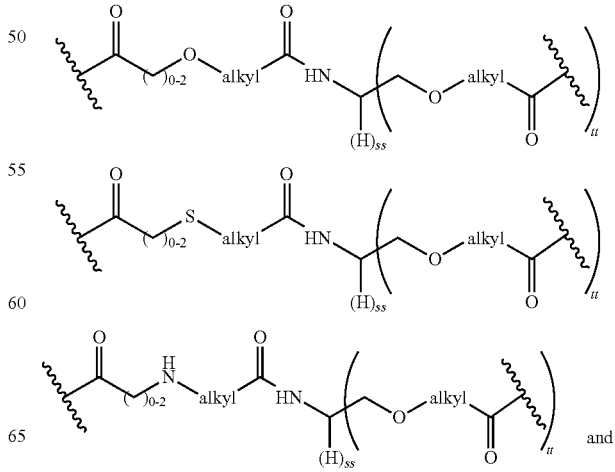

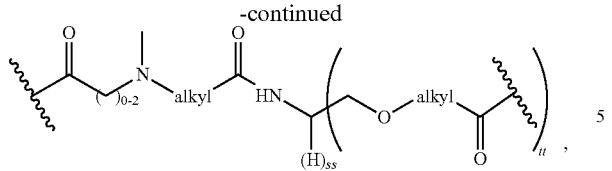
wherein tt and ss are as defined herein.
In certain embodiments Linker$^B$, Linker$^C$, or Linker$^D$ is selected from:
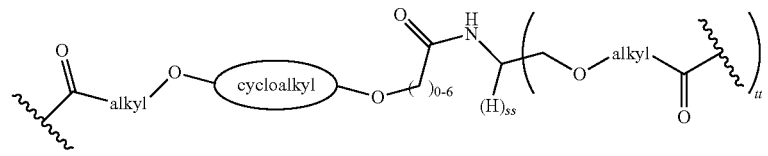
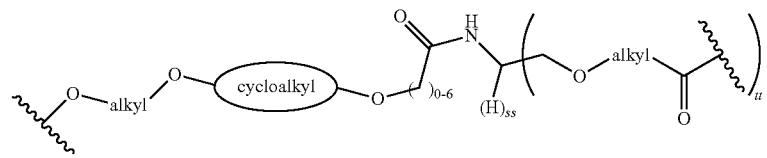
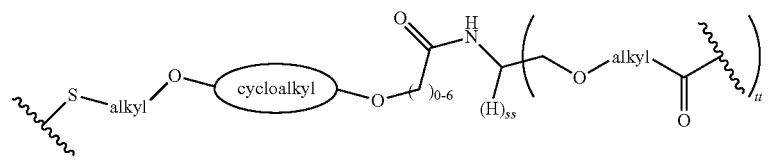
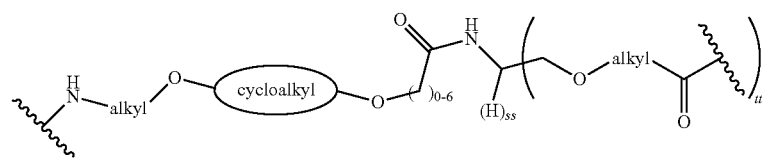
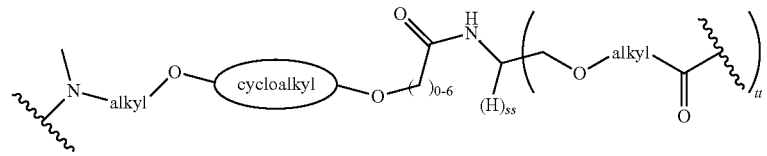
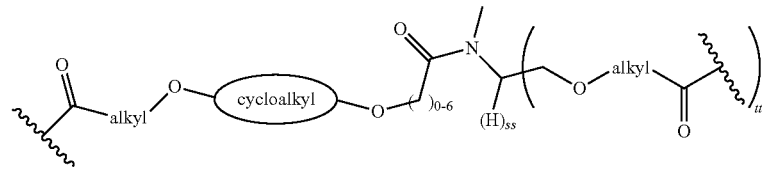
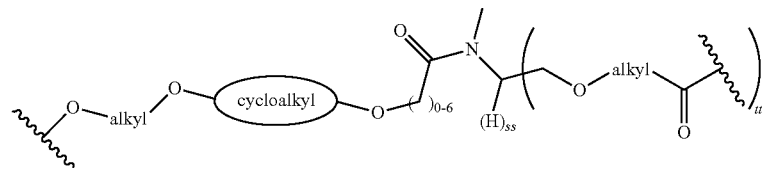
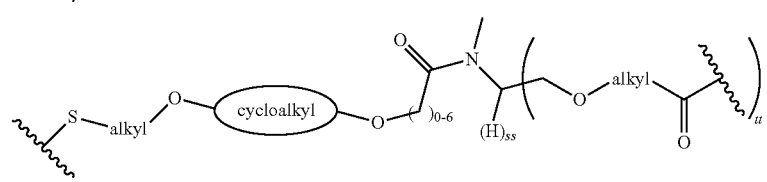

-continued
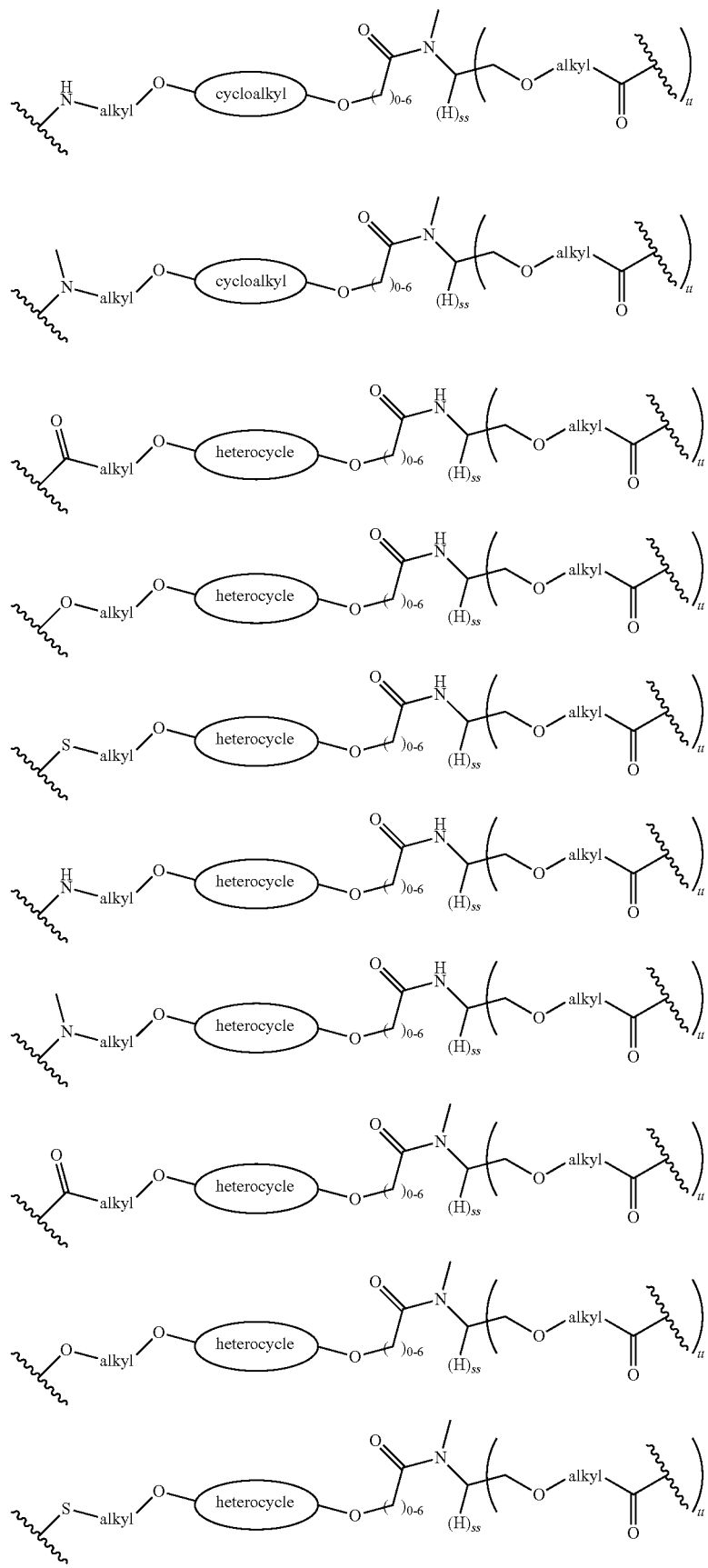

-continued
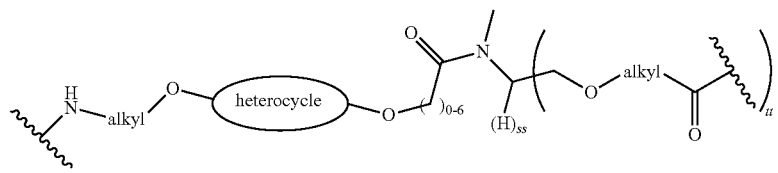
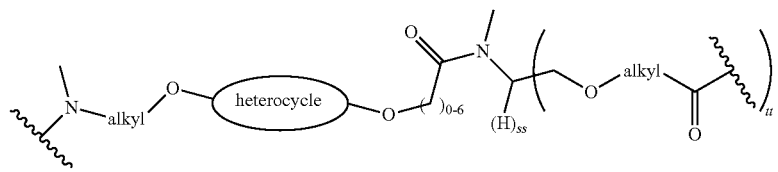
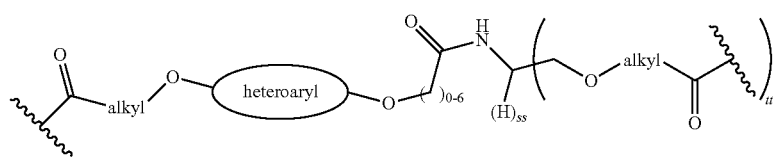
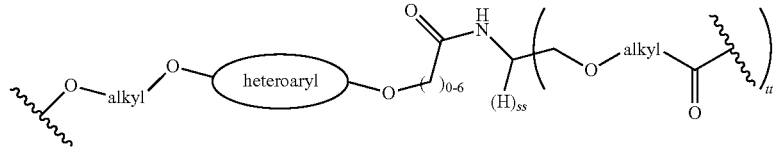
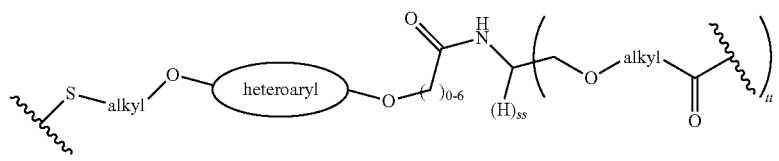
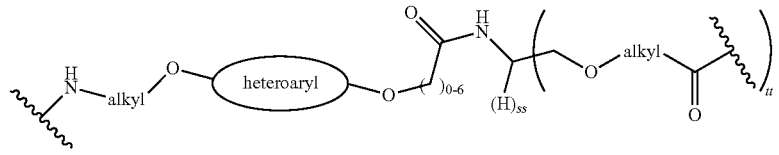
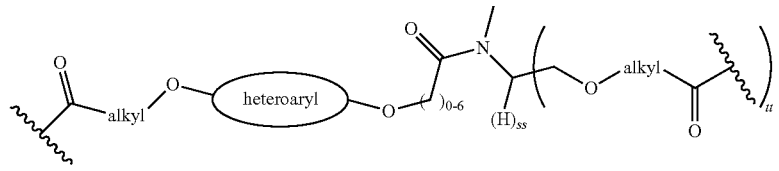
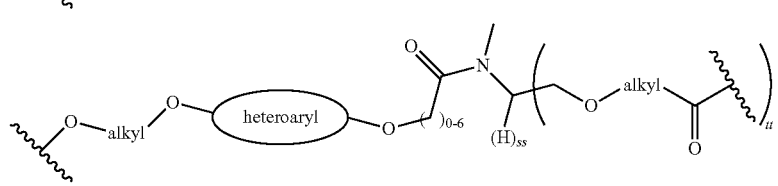
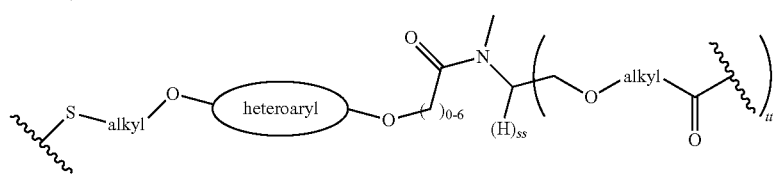

-continued
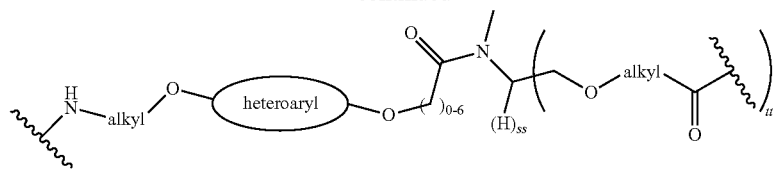
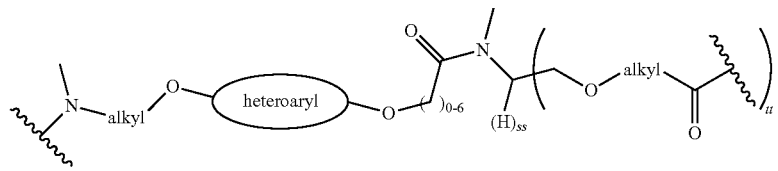
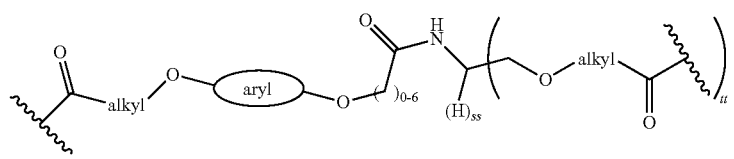
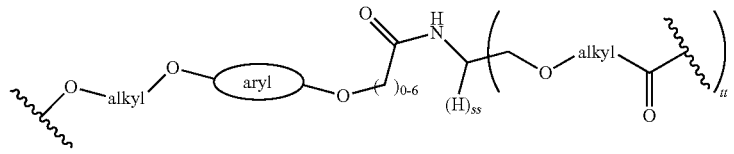
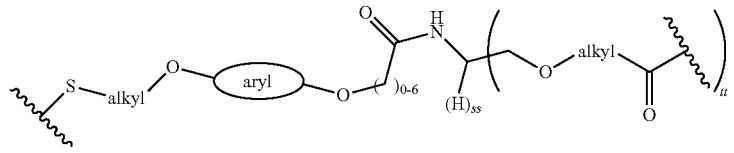
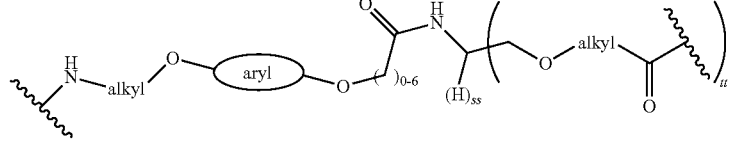
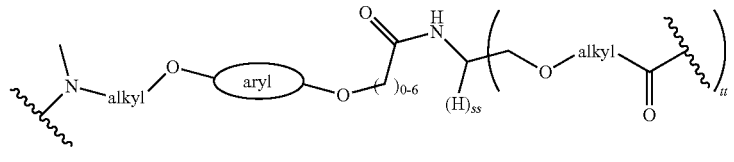
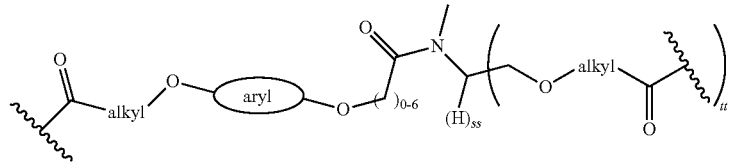
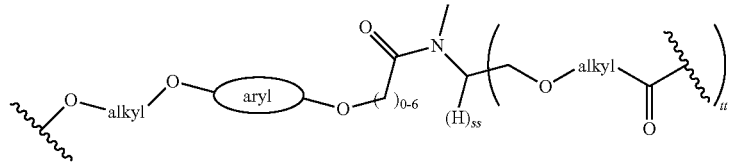
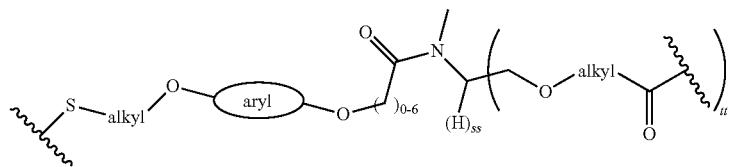

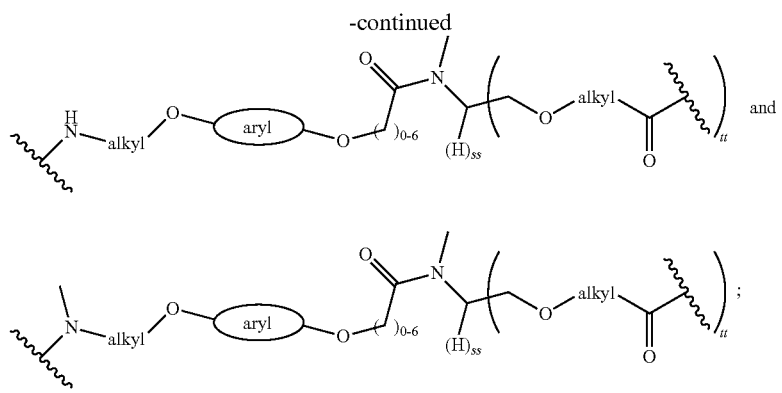
wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence; and tt and ss are as defined herein.
In certain embodiments Linker$^B$, Linker$^C$, or Linker$^D$ is selected from:
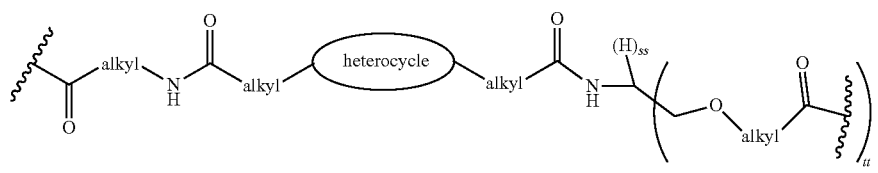
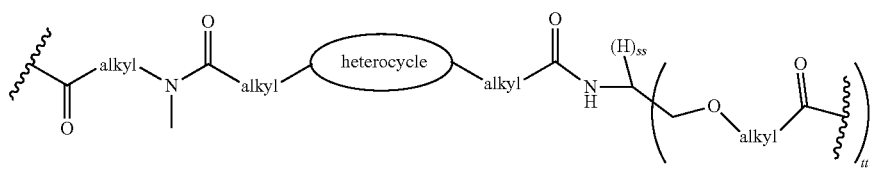
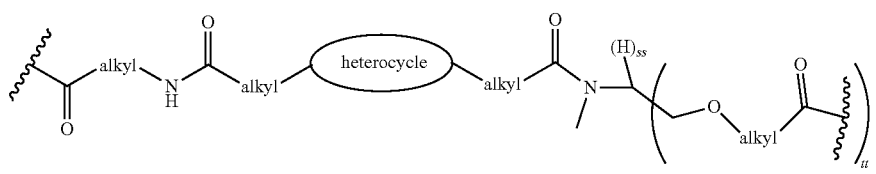
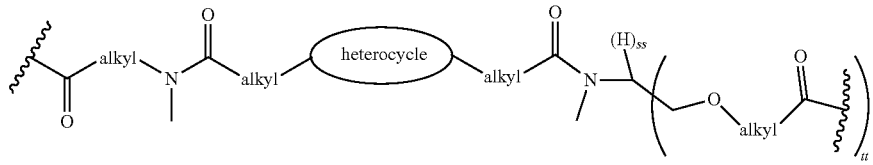
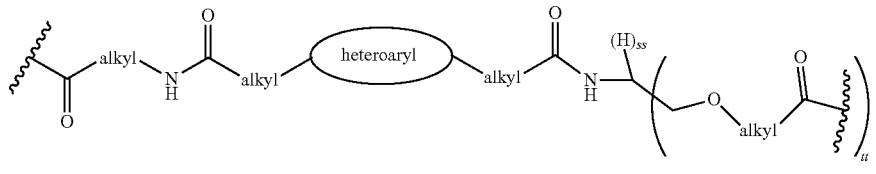
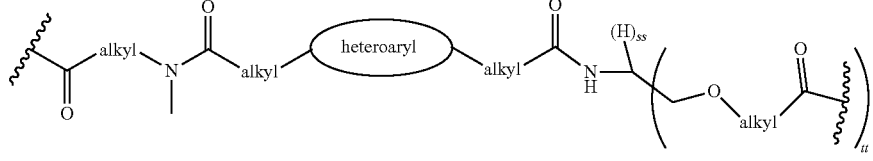

-continued
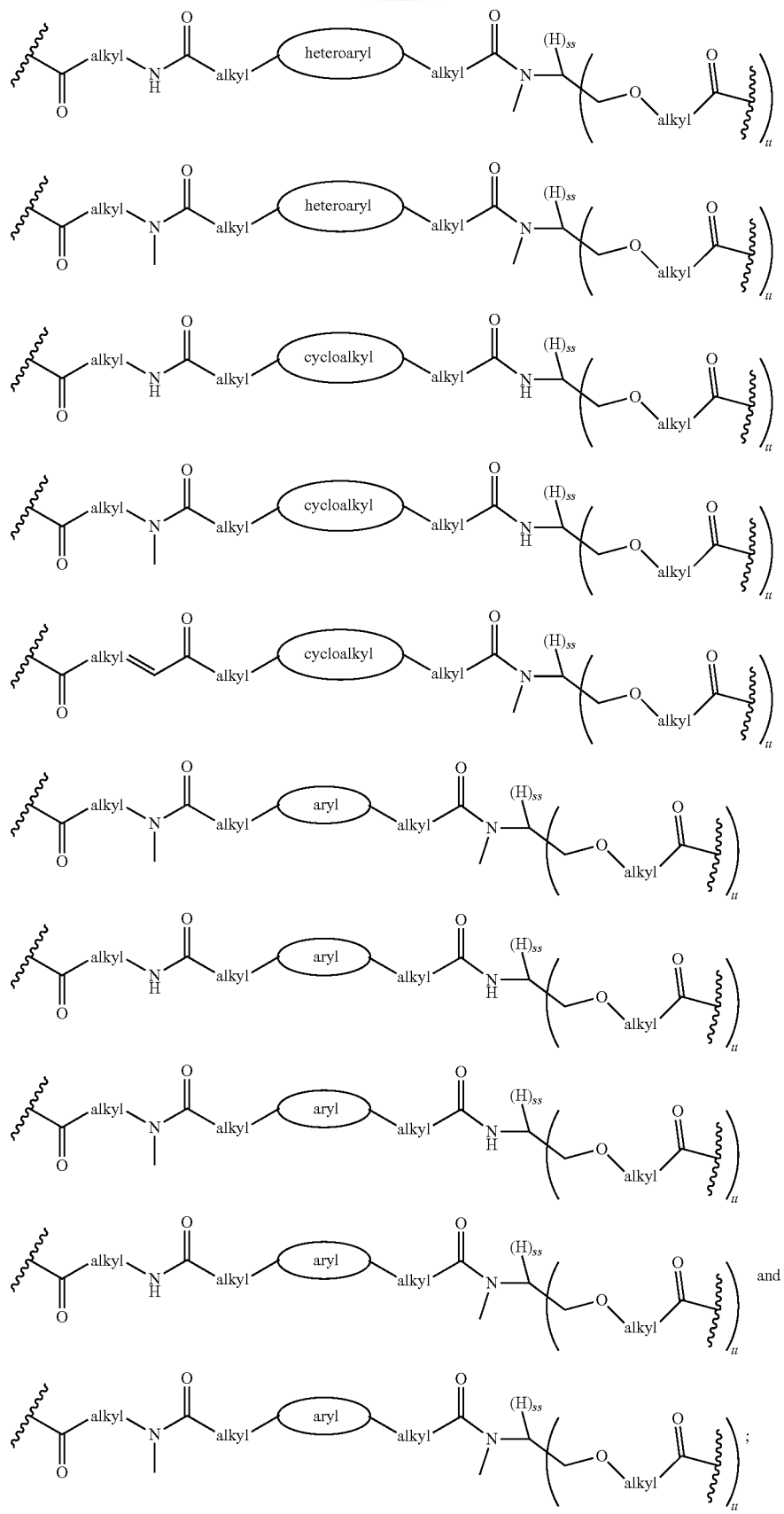

wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence; and tt and ss are as defined herein.

In certain embodiments Linker$^B$, Linker$^C$, or Linker$^D$ is selected from:

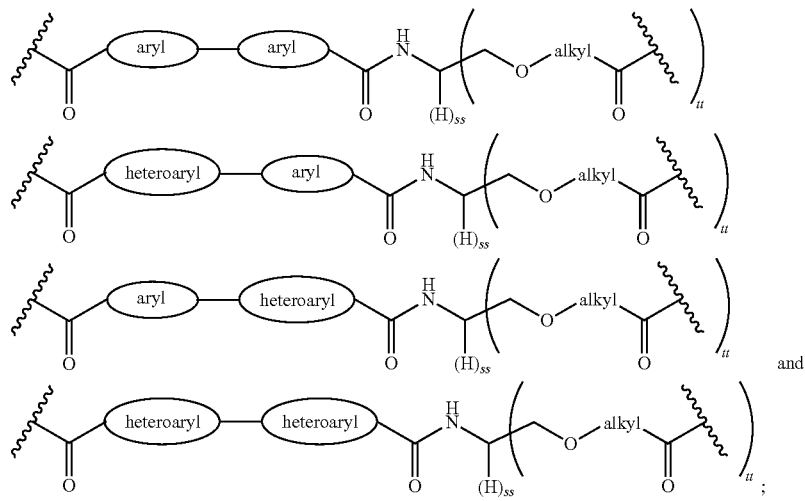

wherein each heteroaryl and aryl can optionally be substituted with 1, 2, 3, or 4 of any combination of halogen, alkyl, haloalkyl, aryl, heteroaryl, heterocycle, or cycloalkyl, as allowed by valence; and tt and ss are as defined herein.

In certain embodiments Linker$^A$ is selected from:

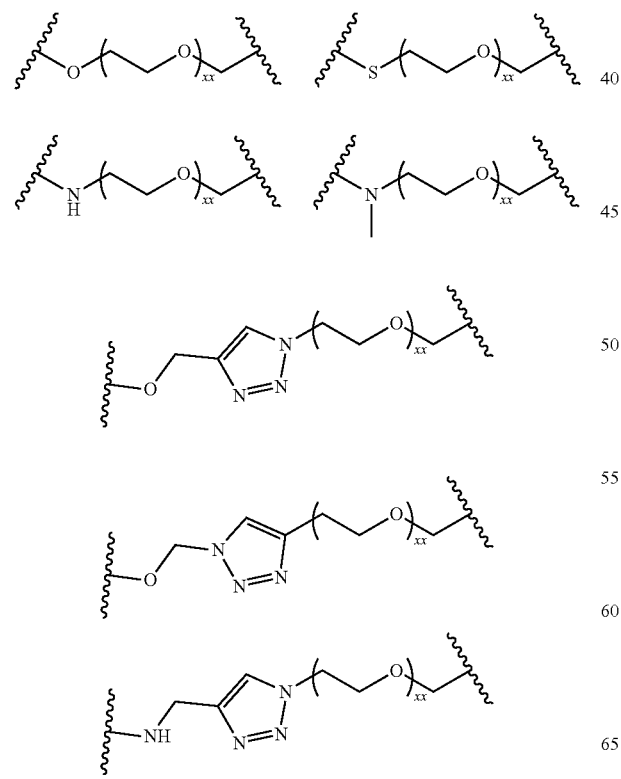

-continued

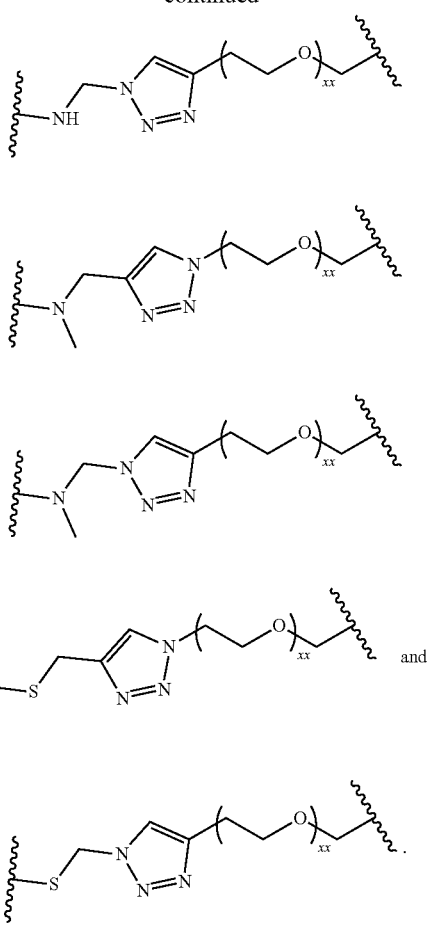

In certain embodiments Linker⁴ is selected from:
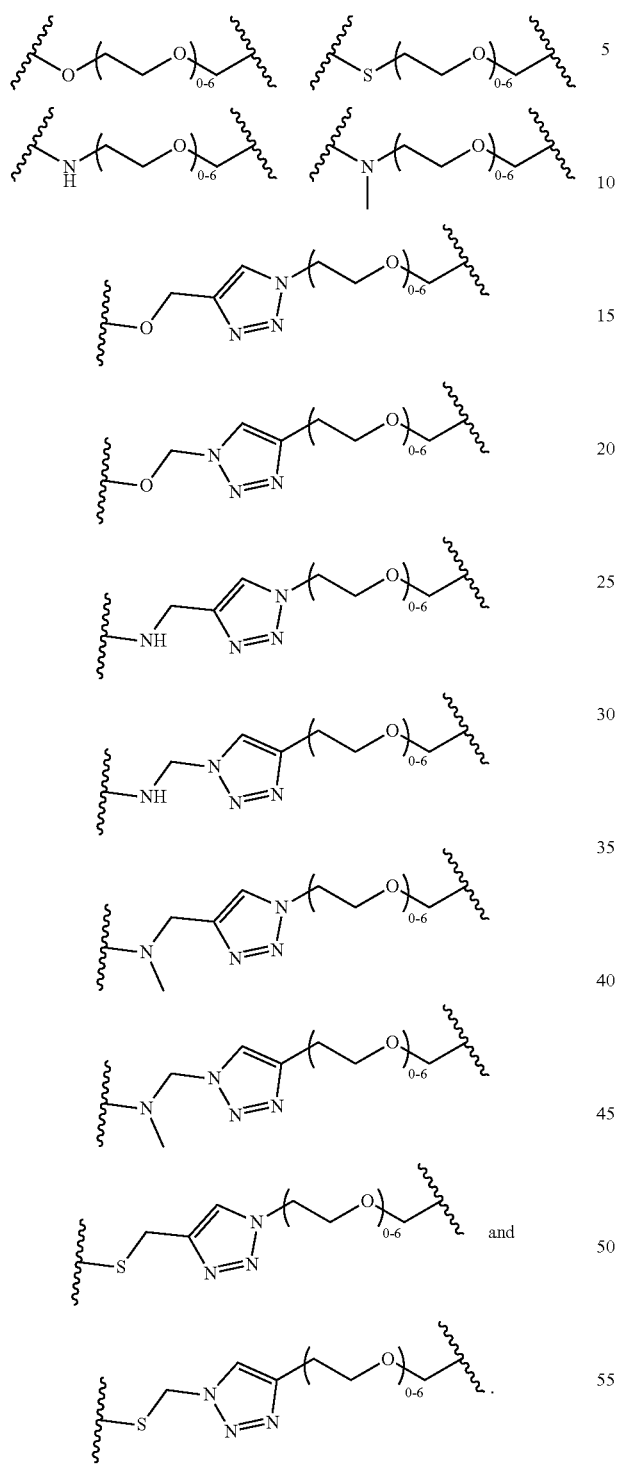
In certain embodiments Linker⁴ is selected from:
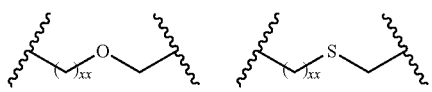
-continued
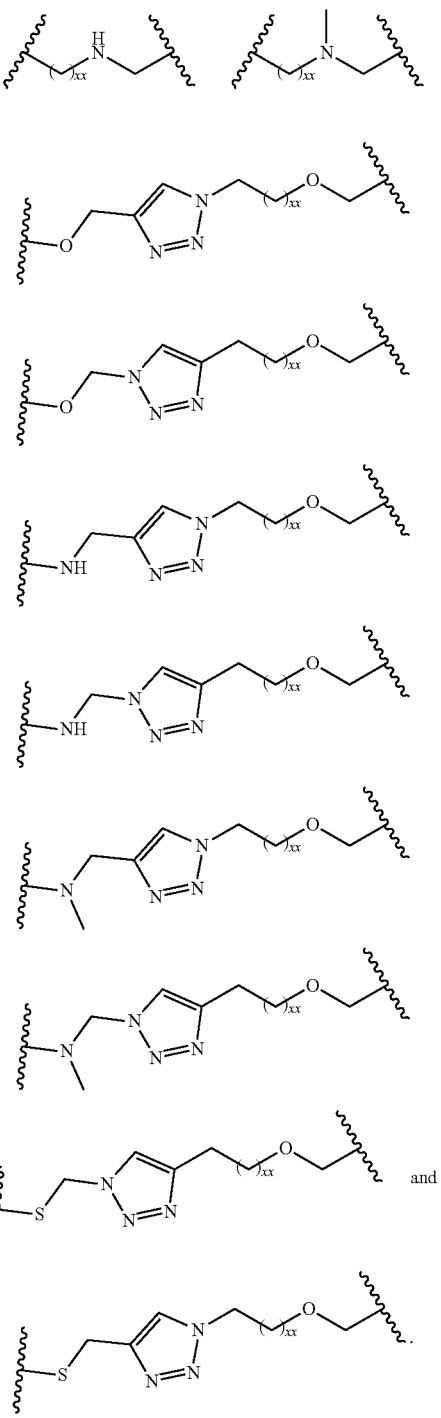
In certain embodiments Linker⁴ is selected from:
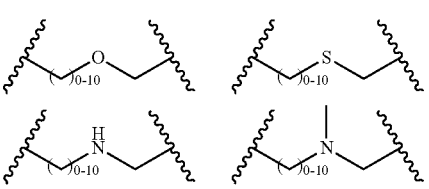

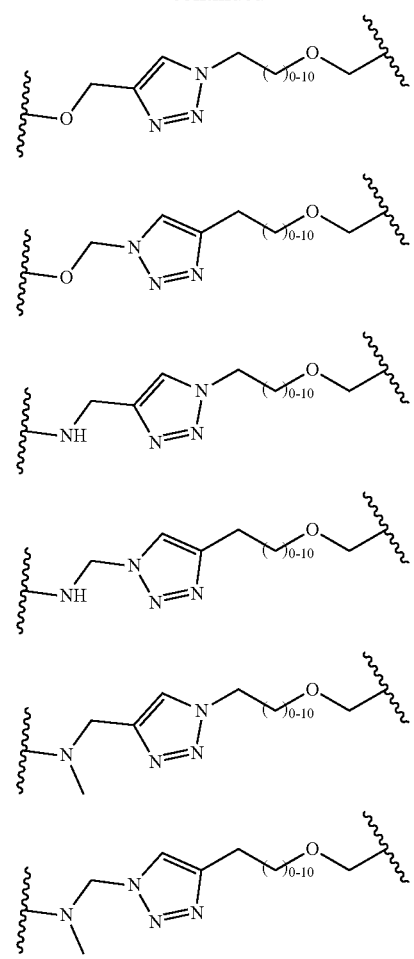
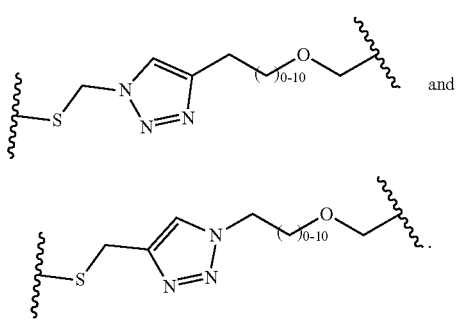
In certain embodiments Linker$^B$ is selected from:
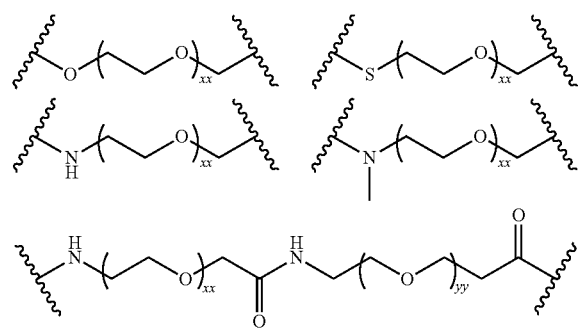
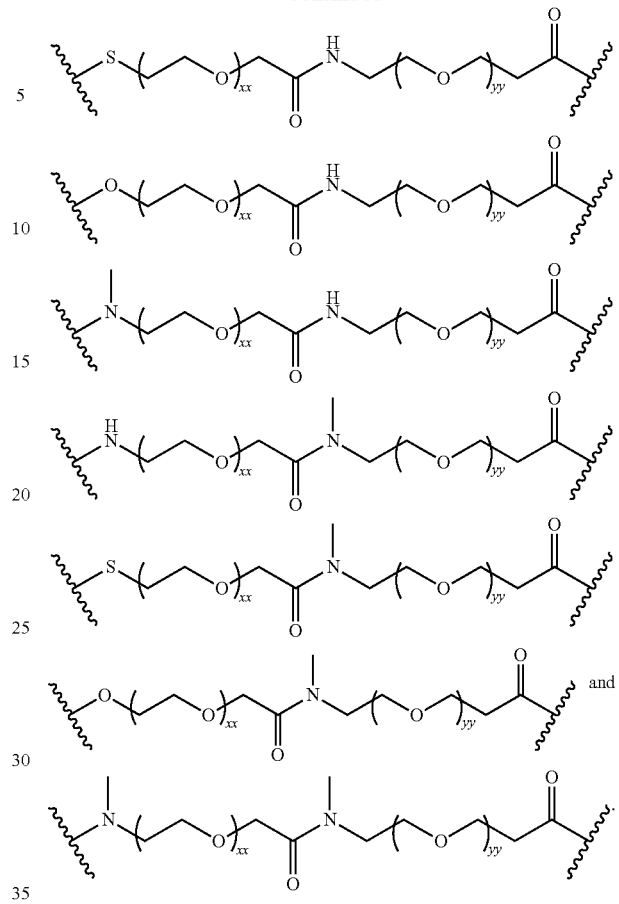
In certain embodiments Linker$^B$ is selected from:
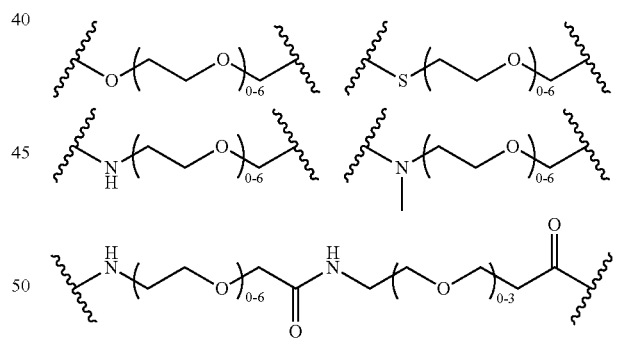
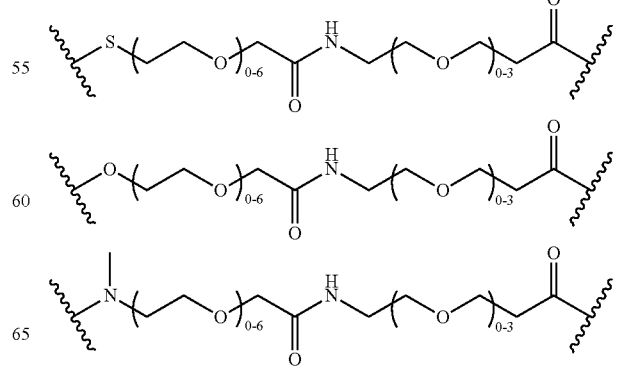

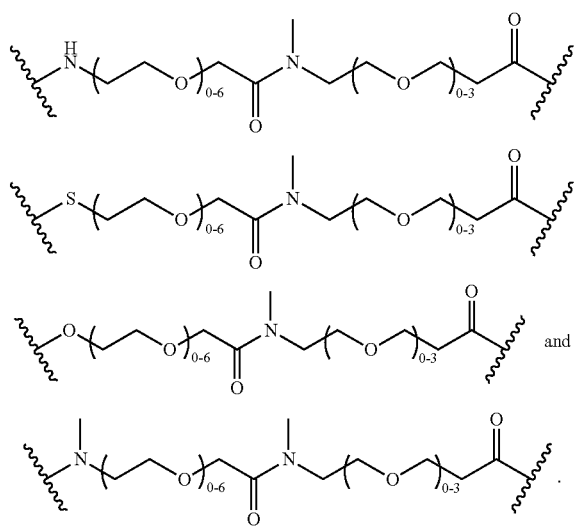
In certain embodiments Linker$^A$ is selected from:
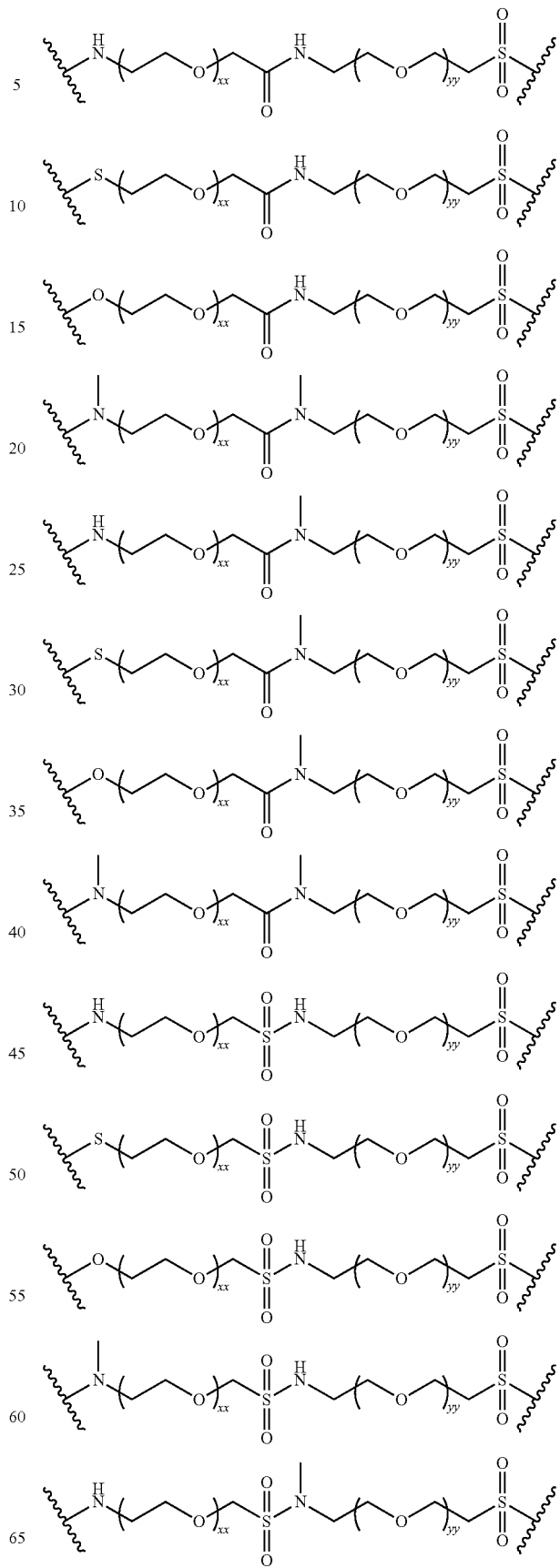

537
-continued
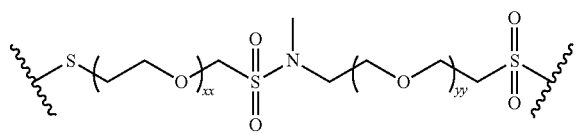
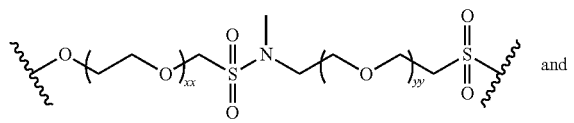 and
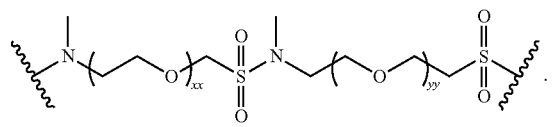
In certain embodiments Linker$^A$ is selected from:
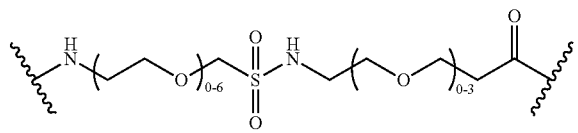
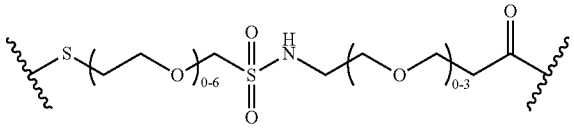
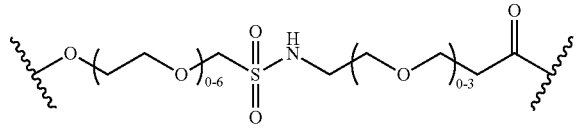
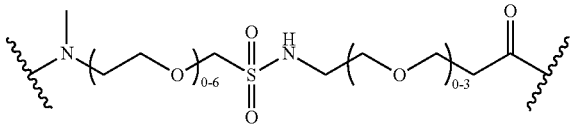
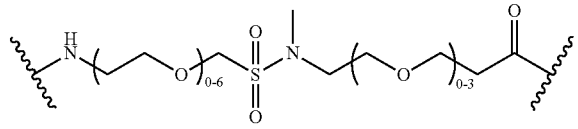
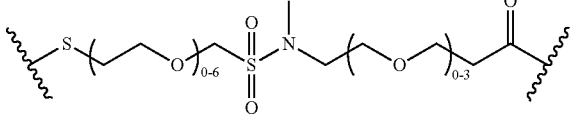
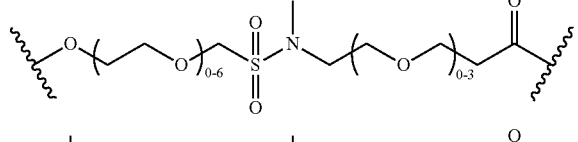
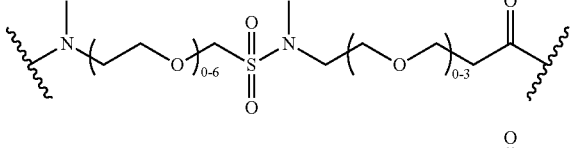
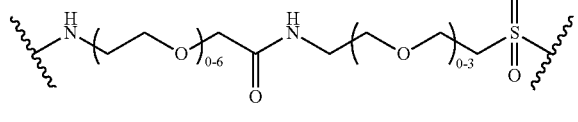
538
-continued
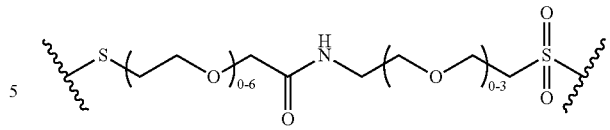
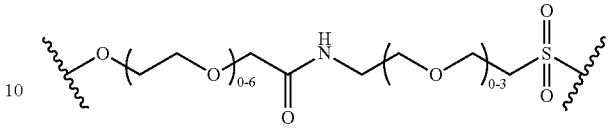
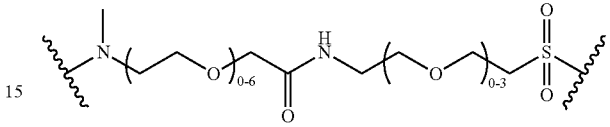
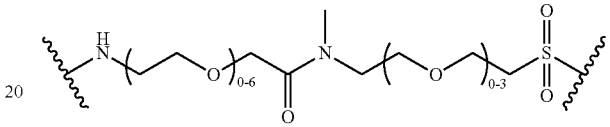
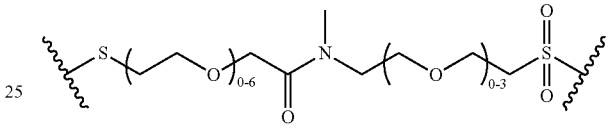
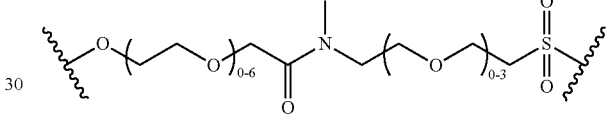
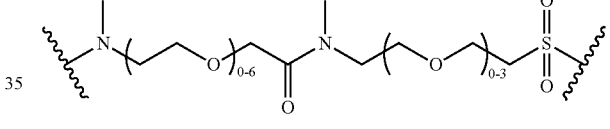
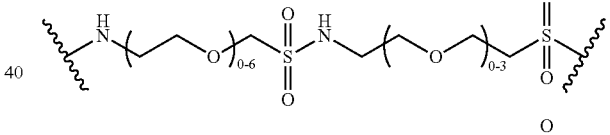
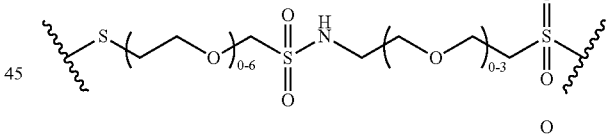
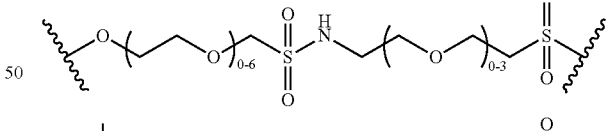
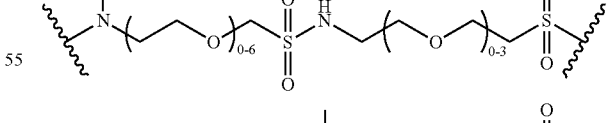
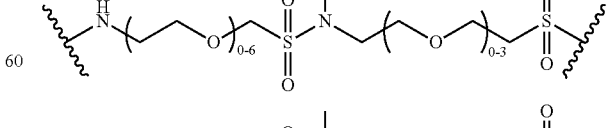
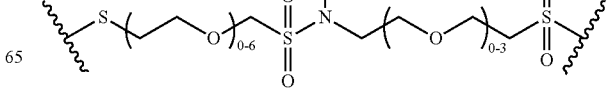

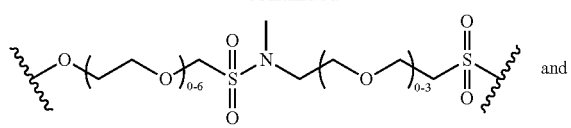
and
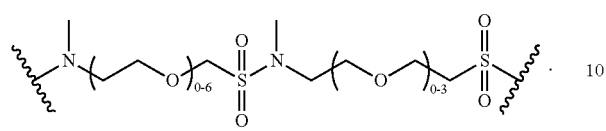
In certain embodiments Linker$^C$ is selected from:
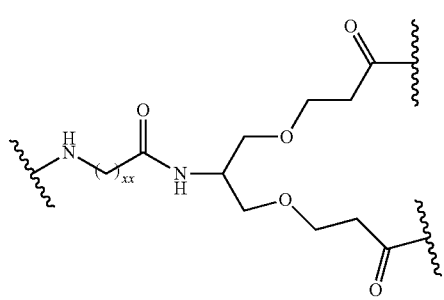
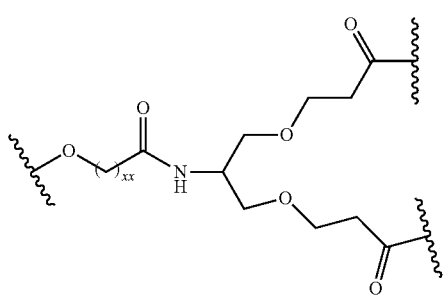
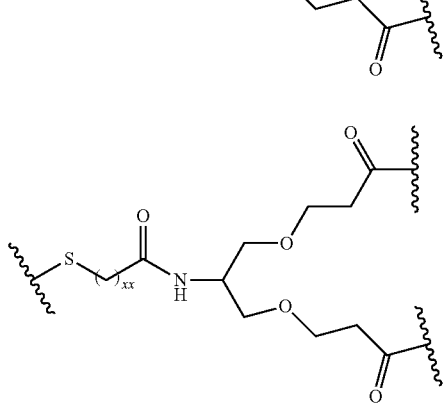
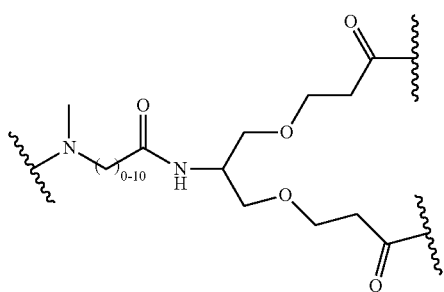
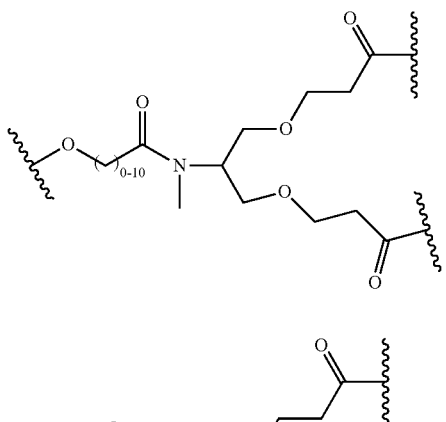
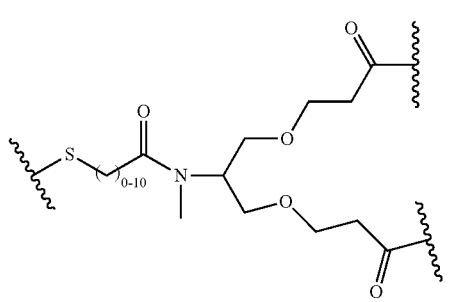
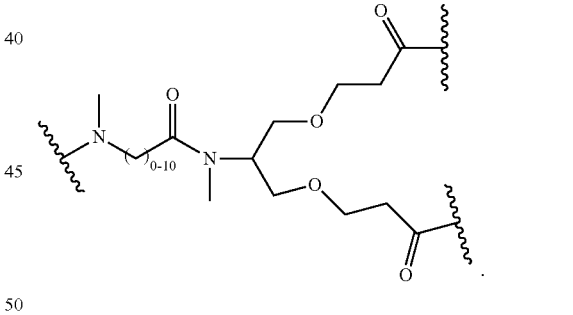
and
In certain embodiments Linker$^C$ is selected from:
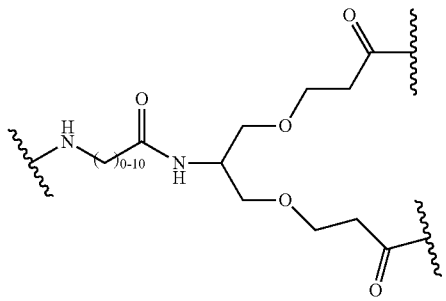

541
-continued
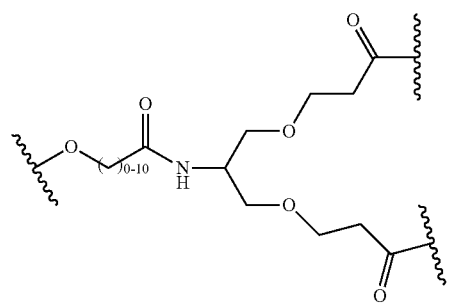
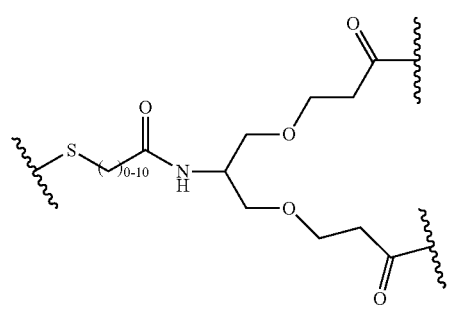
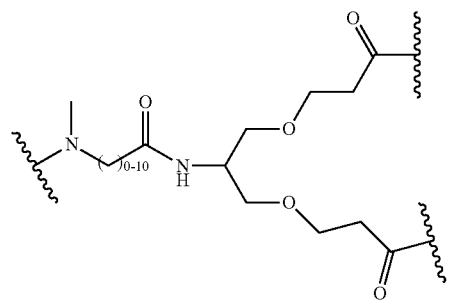
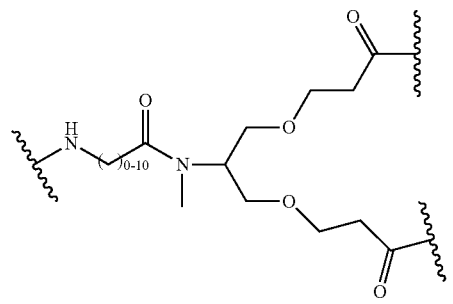
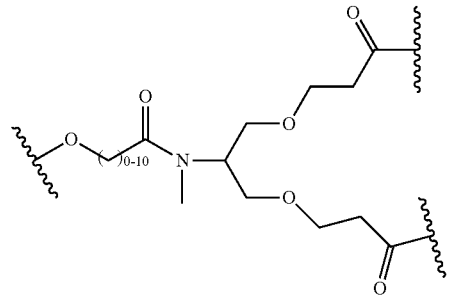
542
-continued
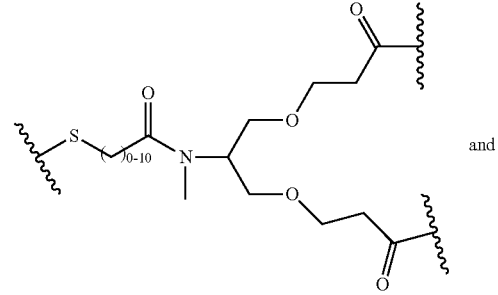
and
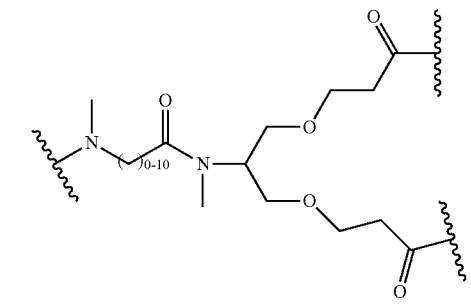
In certain embodiments Linker$^C$ is selected from:
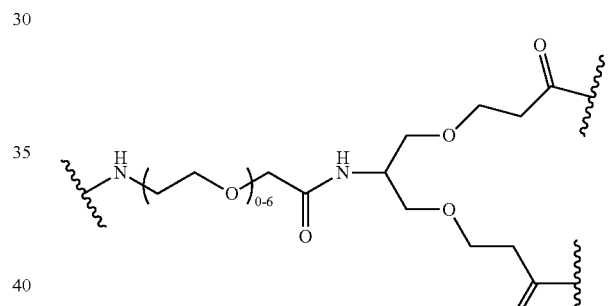
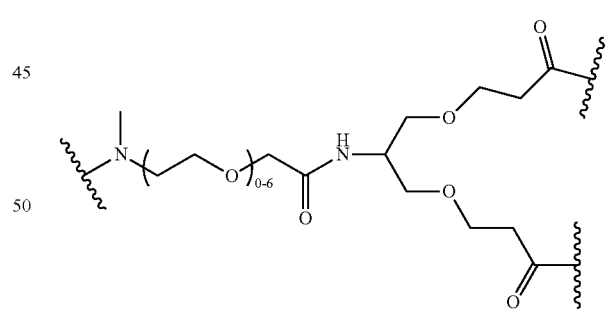
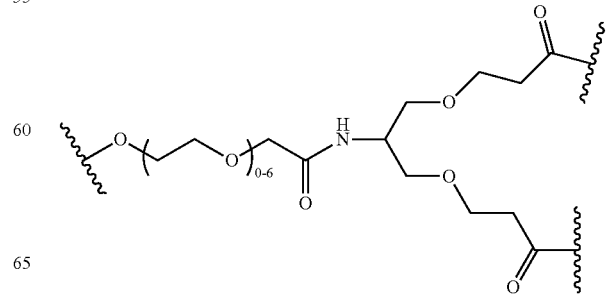

-continued
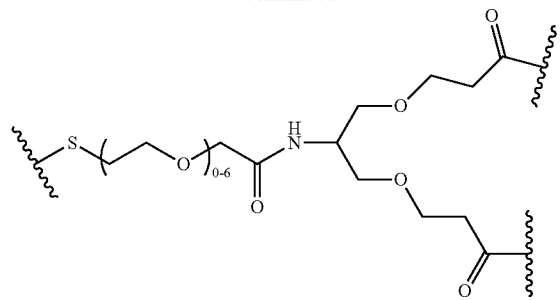
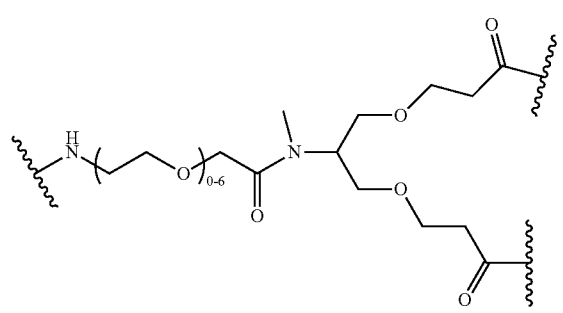
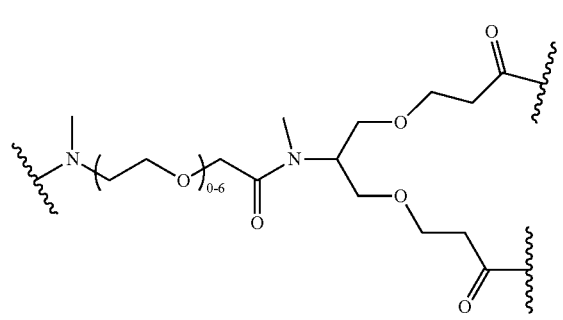
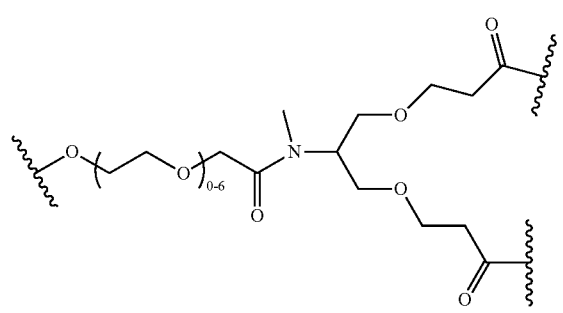
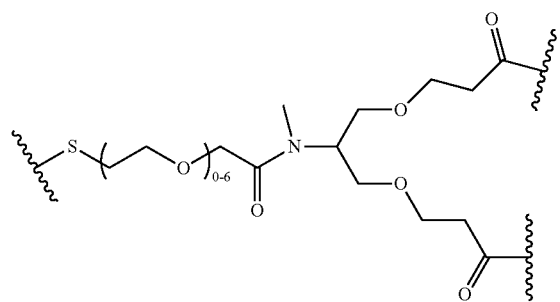
In certain embodiments Linker$^C$ is selected from:
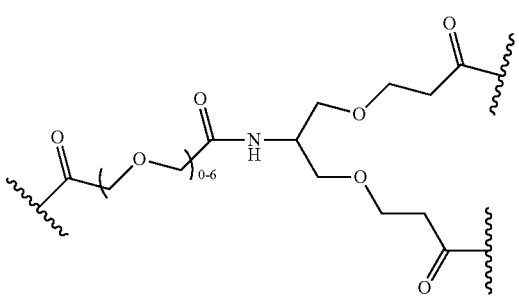
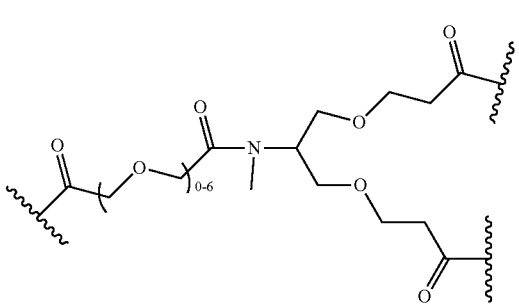
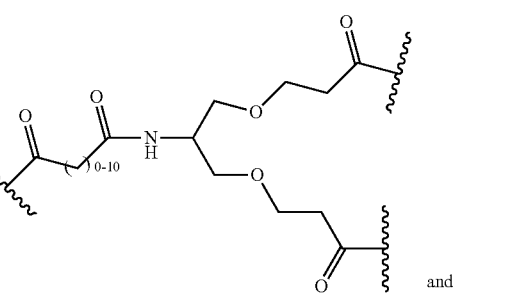
and
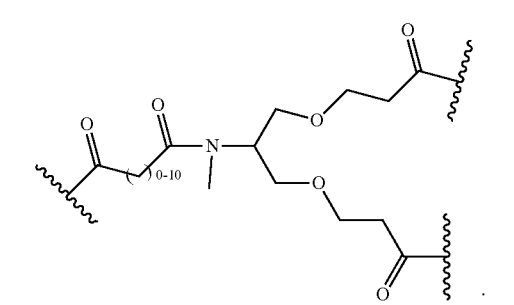
In certain embodiments Linker$^C$ is selected from:
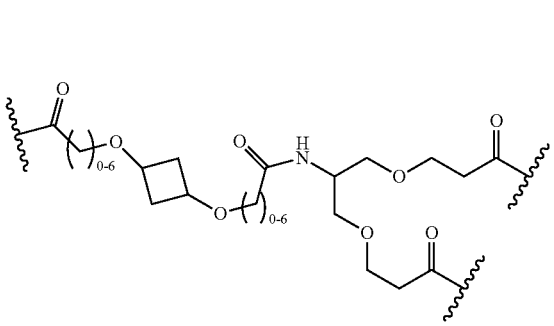

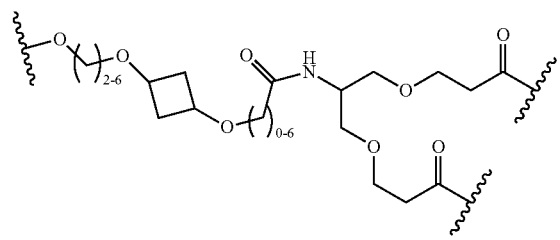
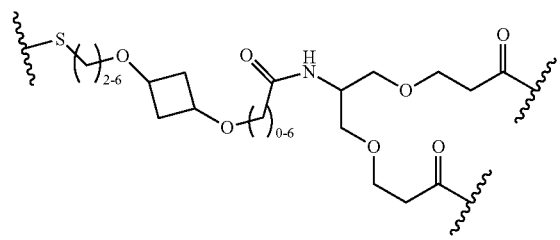

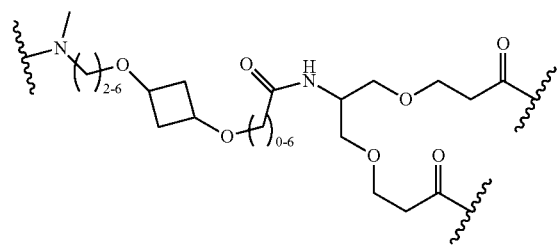
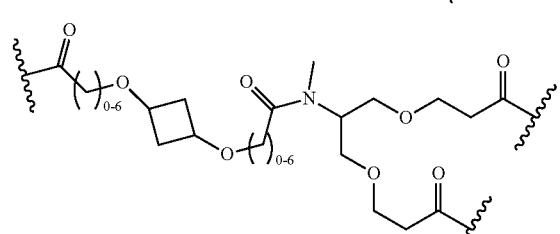
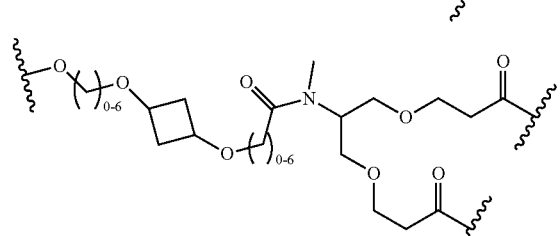
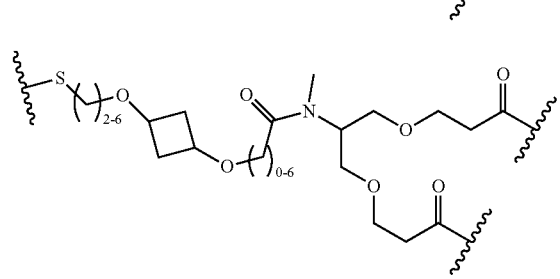
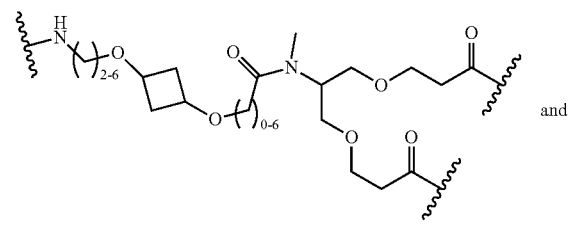
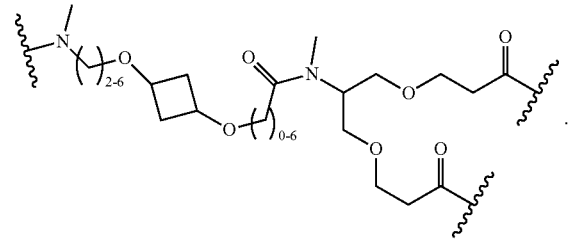
and
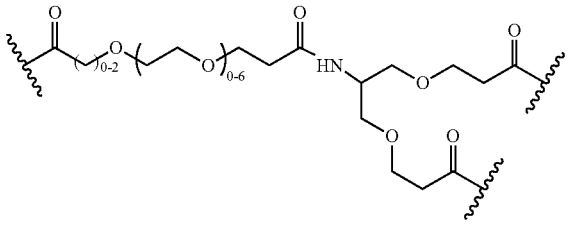
In certain embodiments Linker$^C$ is selected from:
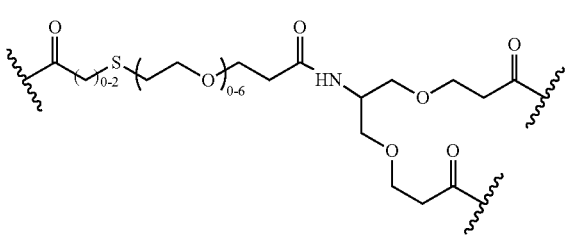
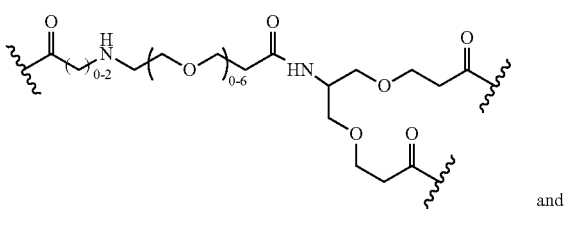
and
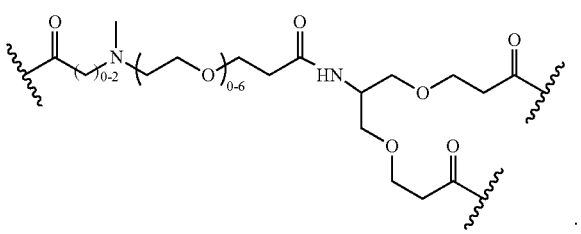

In certain embodiments Linker$^C$ is selected from:
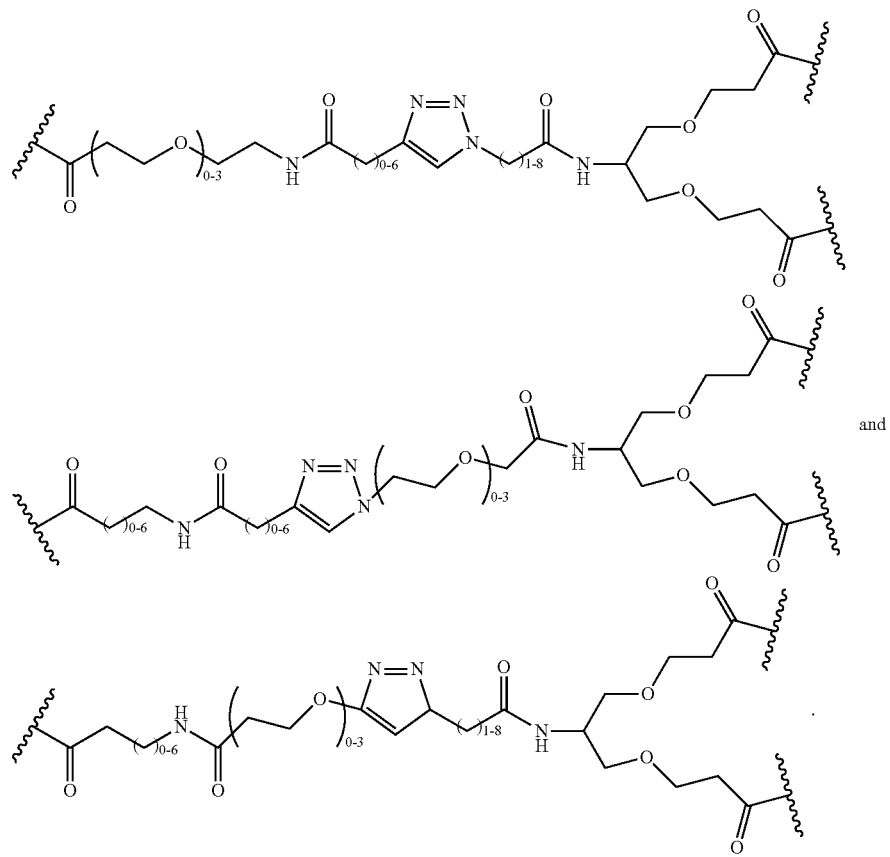
In certain embodiments Linker$^C$ is selected from:
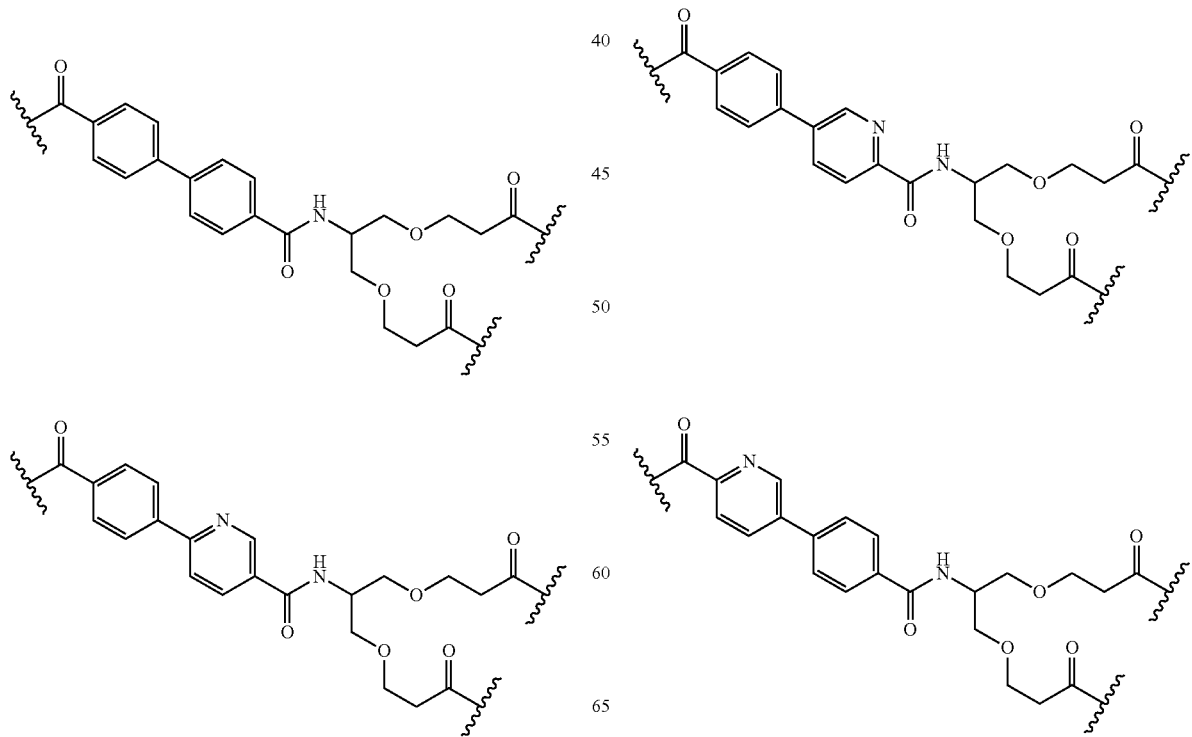

-continued
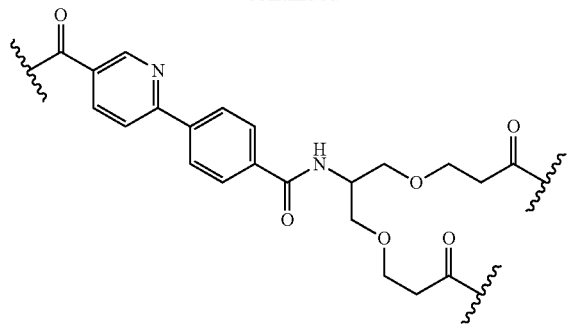
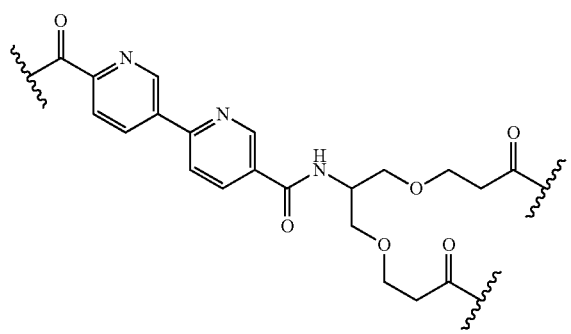
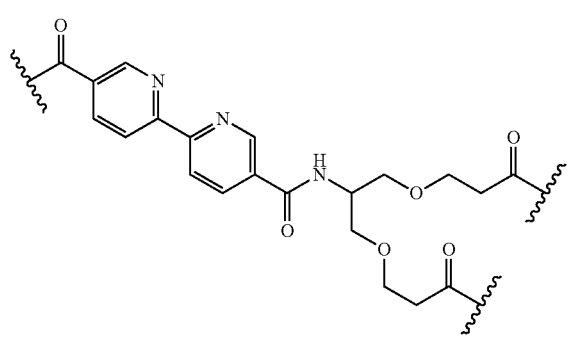

and
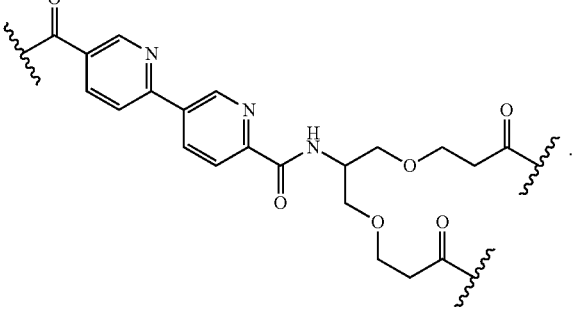
In certain embodiments Linker$^D$ is selected from:
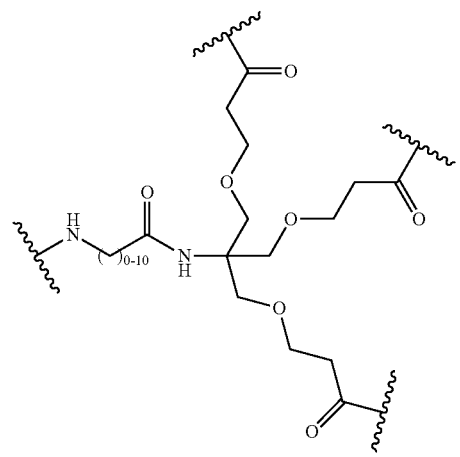
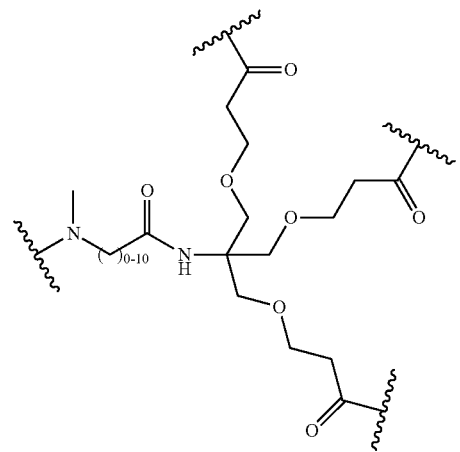
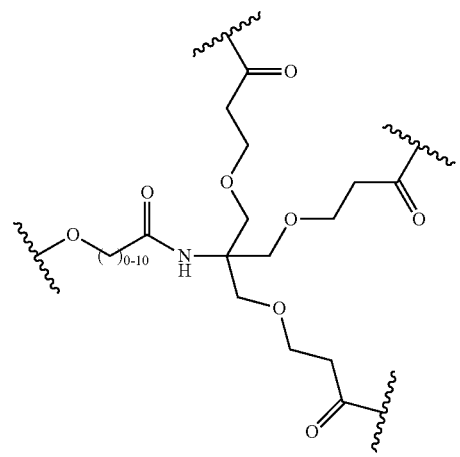

551
-continued
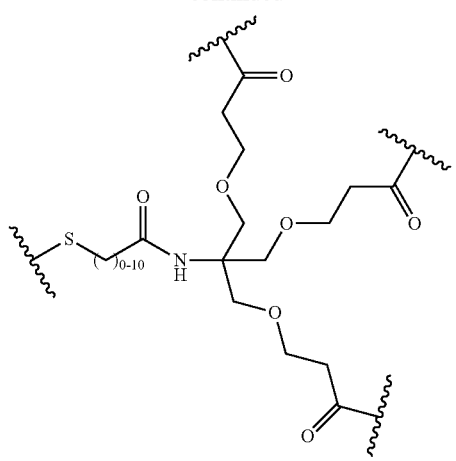
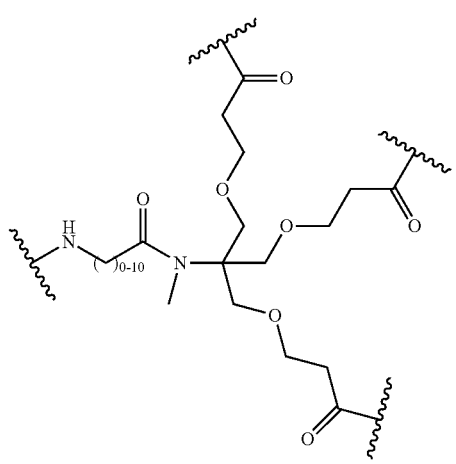
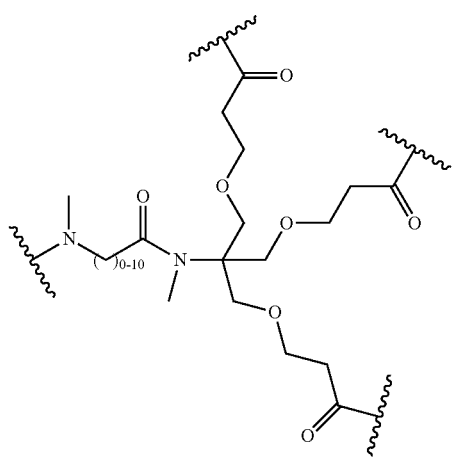
552
-continued
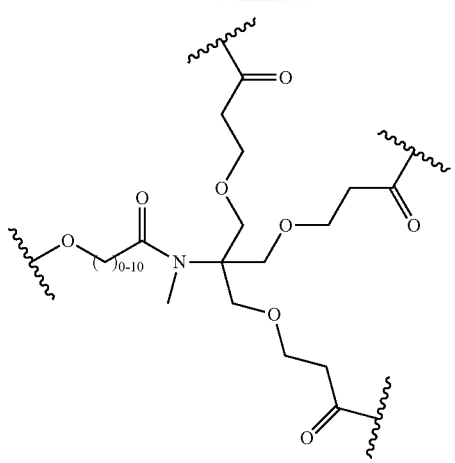
and
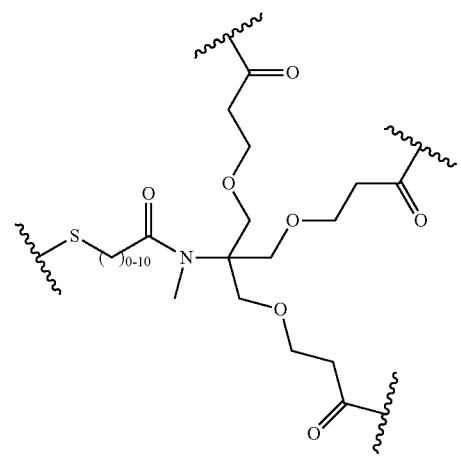
In certain embodiments Linker$^D$ is selected from:
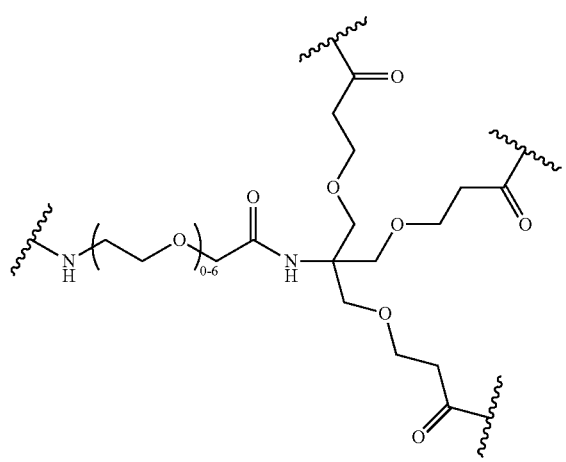

553
-continued
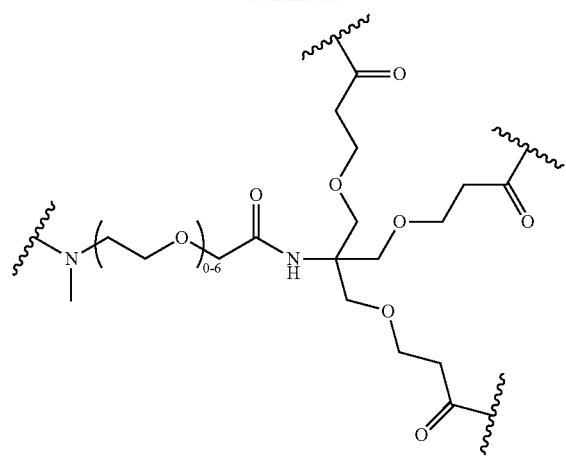
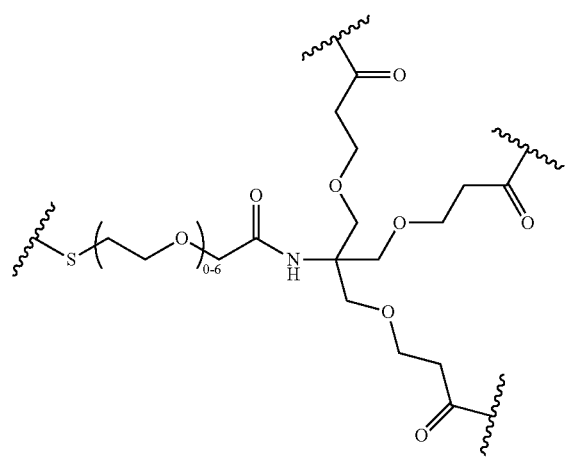
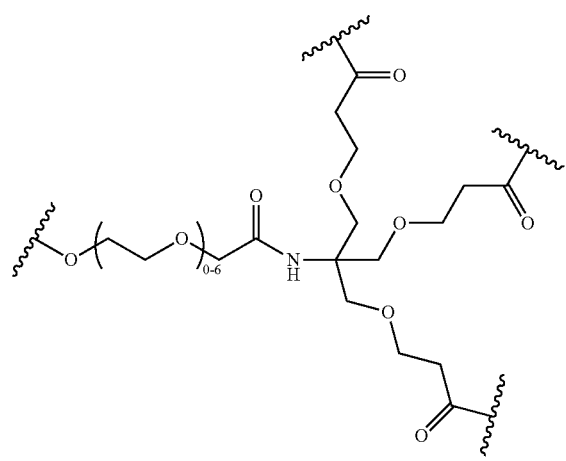
554
-continued
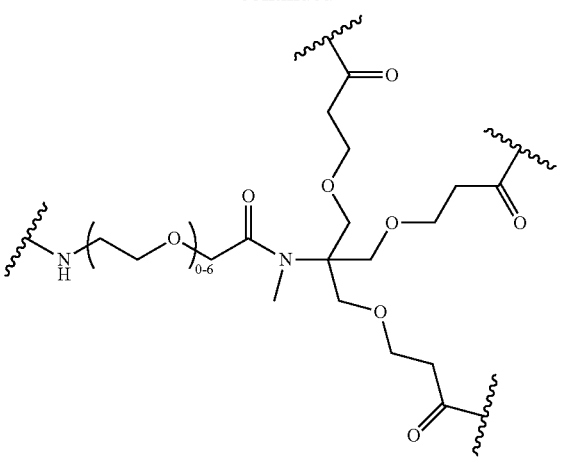
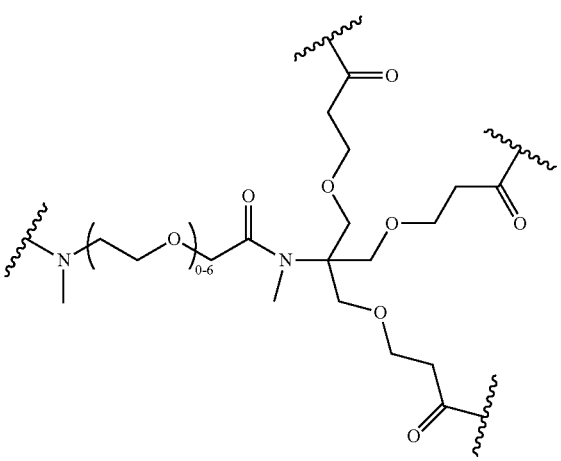
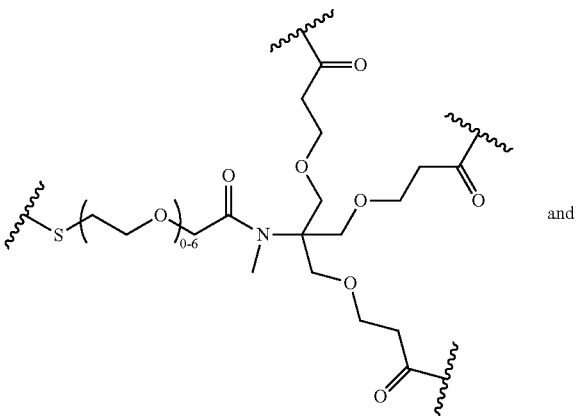
and 555
-continued
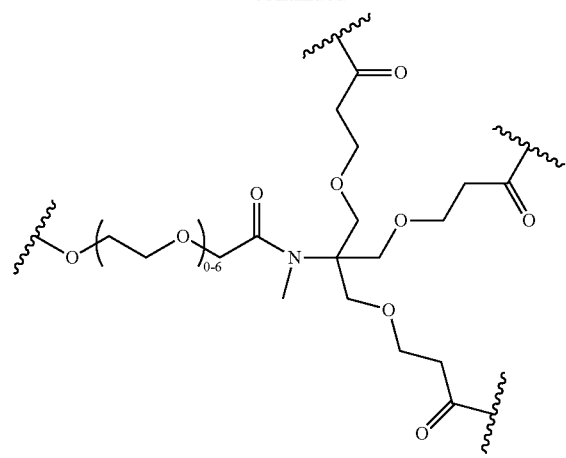
In certain embodiments Linker$^D$ is selected from:
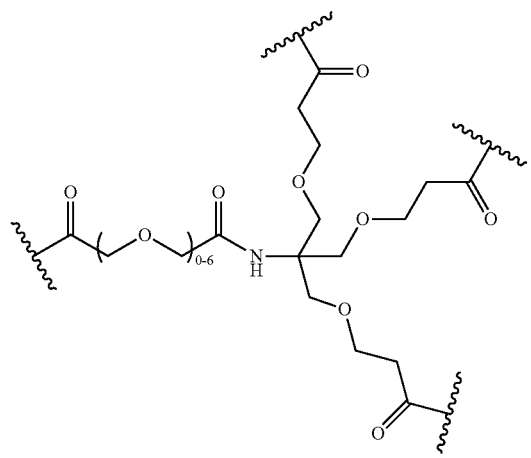
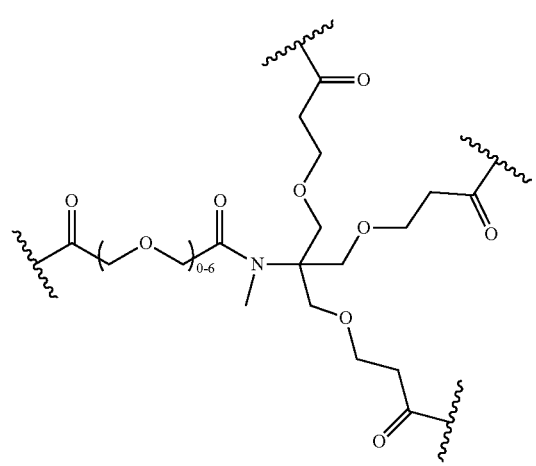
556
-continued
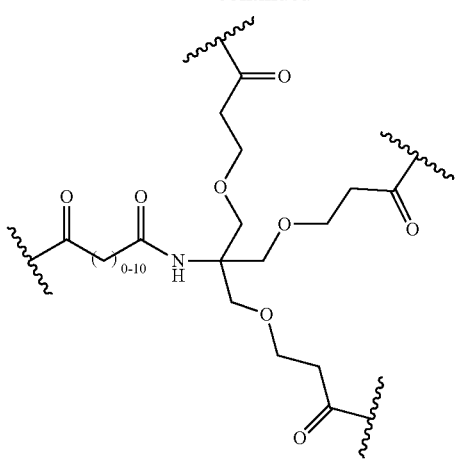
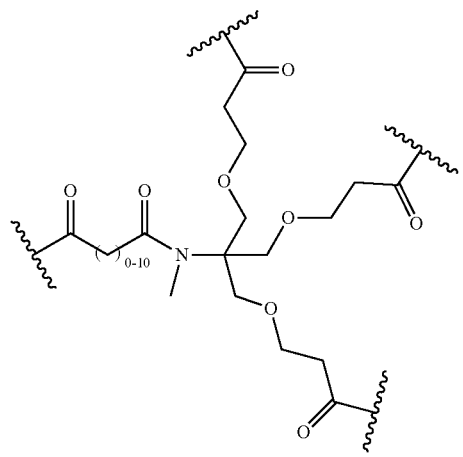
and
In certain embodiments Linker$^D$ is selected from:
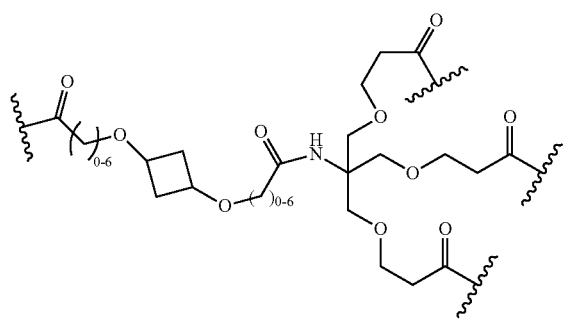
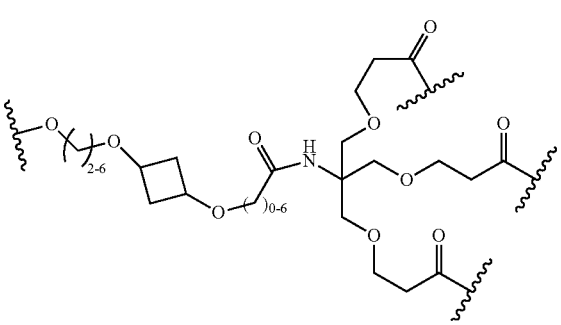

557
-continued
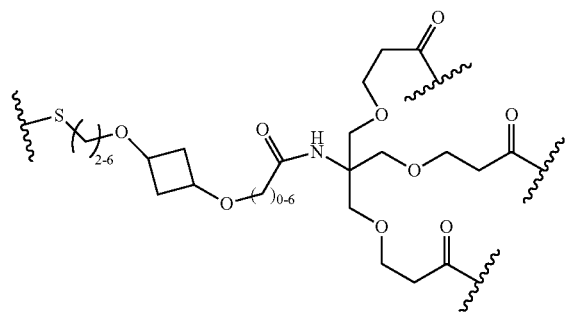
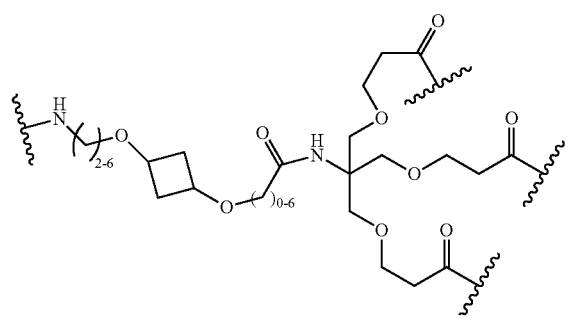
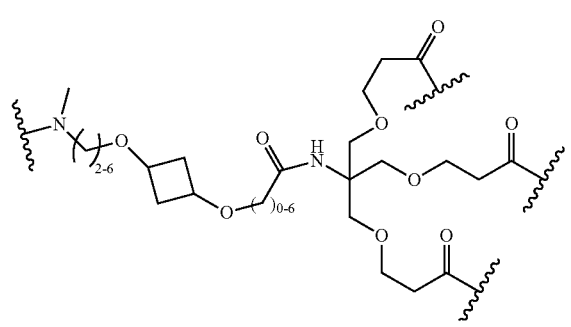
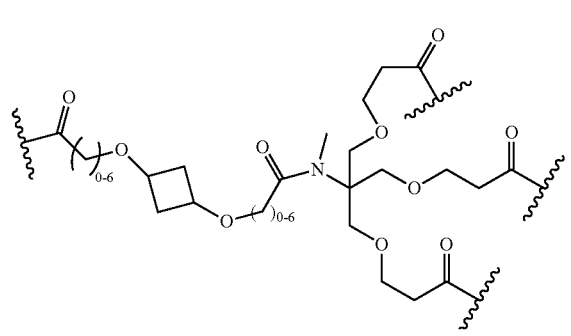
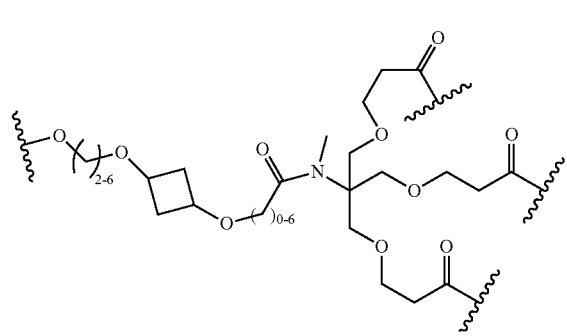
558
-continued
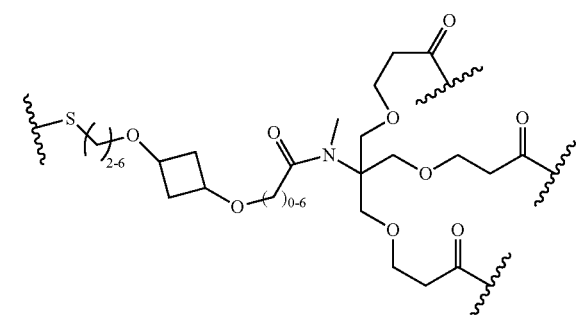
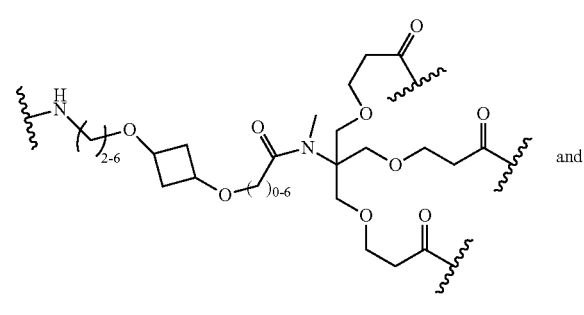
and
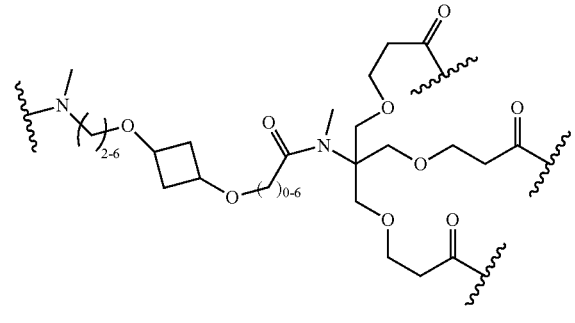
.
In certain embodiments Linker$^D$ is selected from:
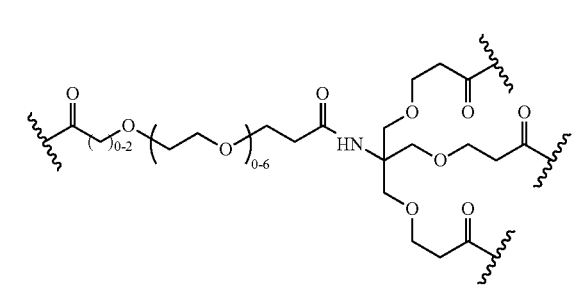
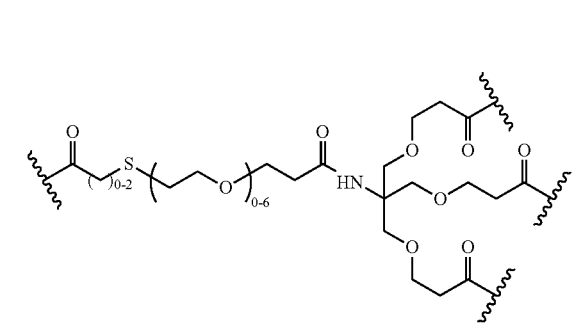

-continued
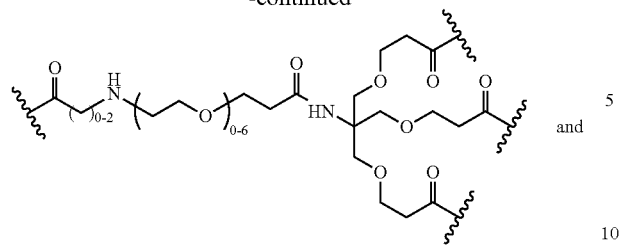
and
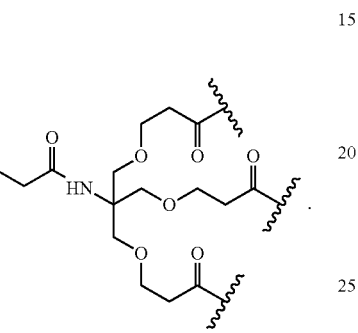
In certain embodiments Linker$^D$ is selected from:
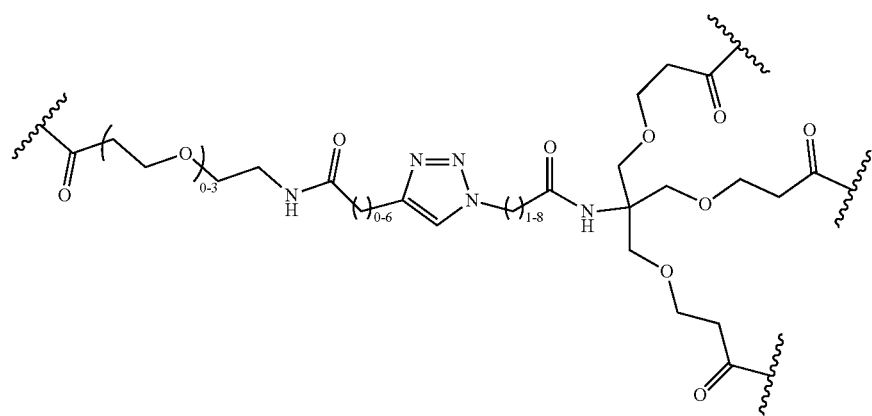
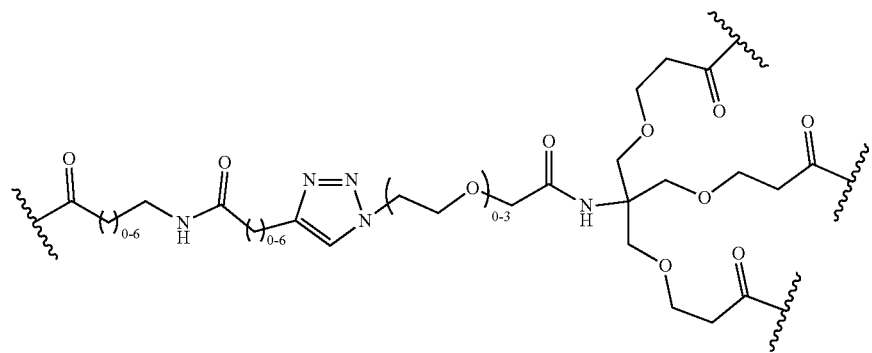
and -continued
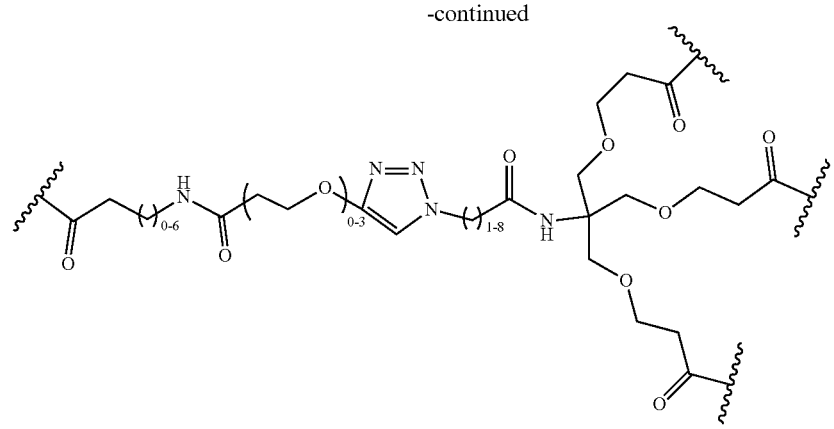
In certain embodiments Linker$^D$ is selected from:
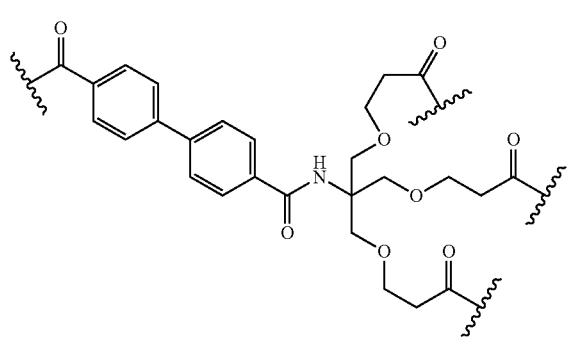
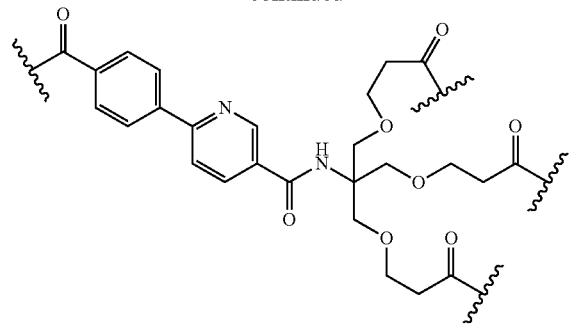
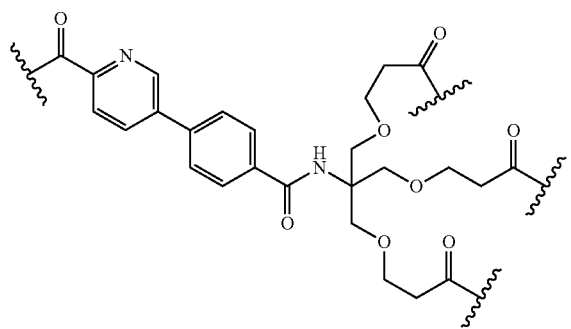
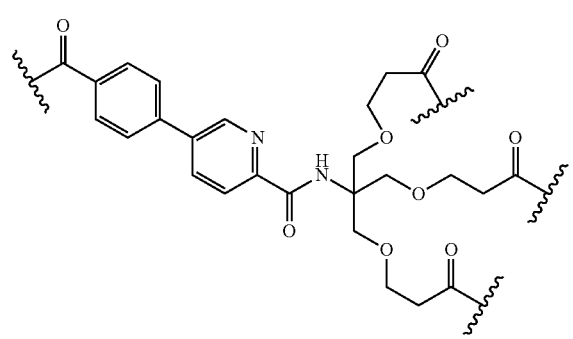
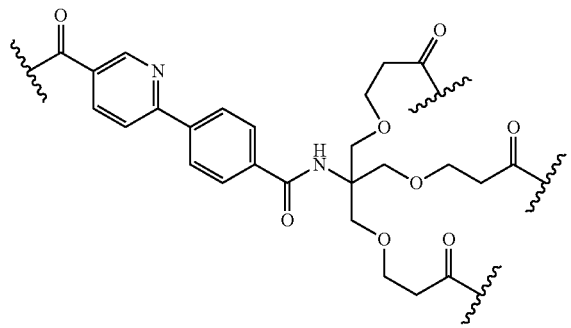
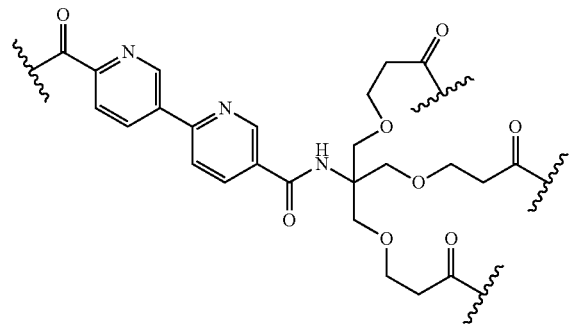

563
-continued
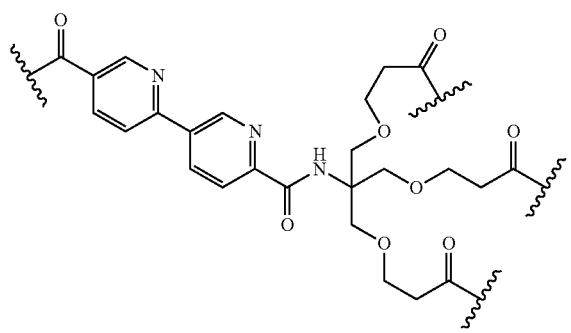
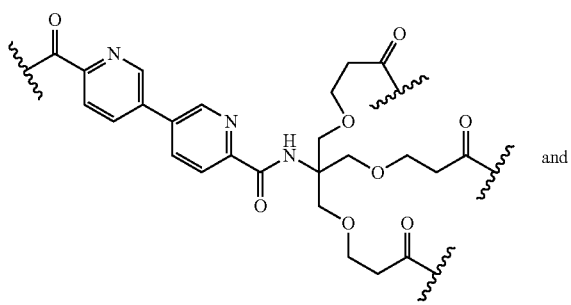
and
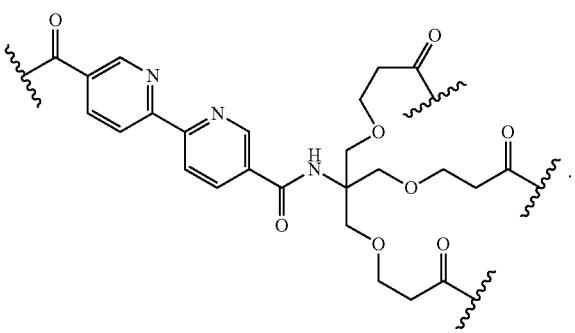
In certain embodiments, the Linker[4] is selected from
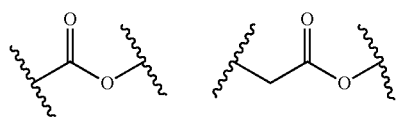
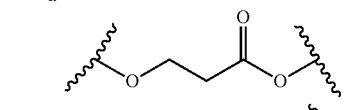
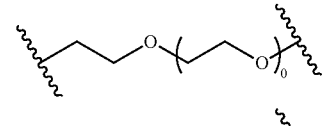
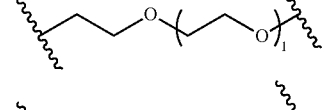
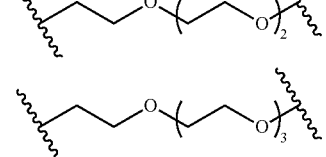
564
-continued
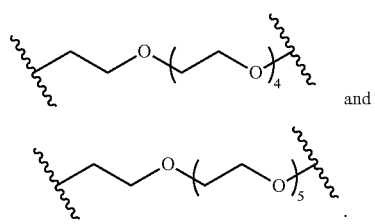
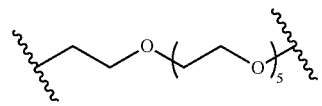
and
In certain embodiments, the Linker[4] is selected from
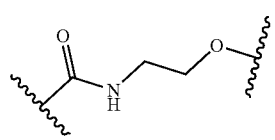
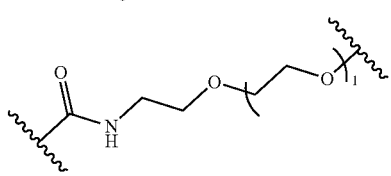
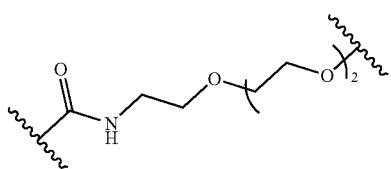
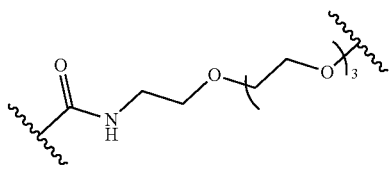
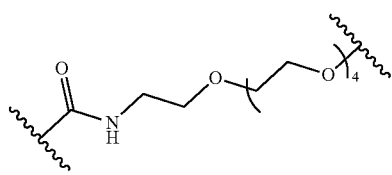
and
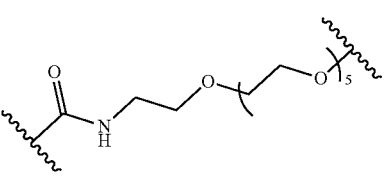
In certain embodiments, the Linker[4] is selected from
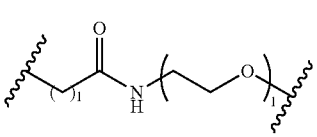
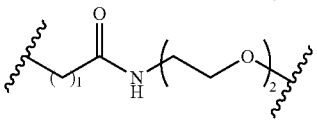

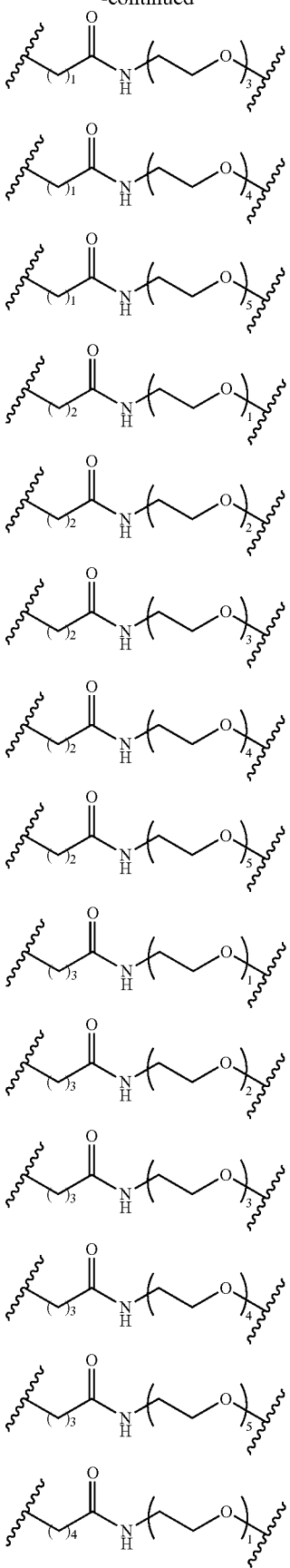
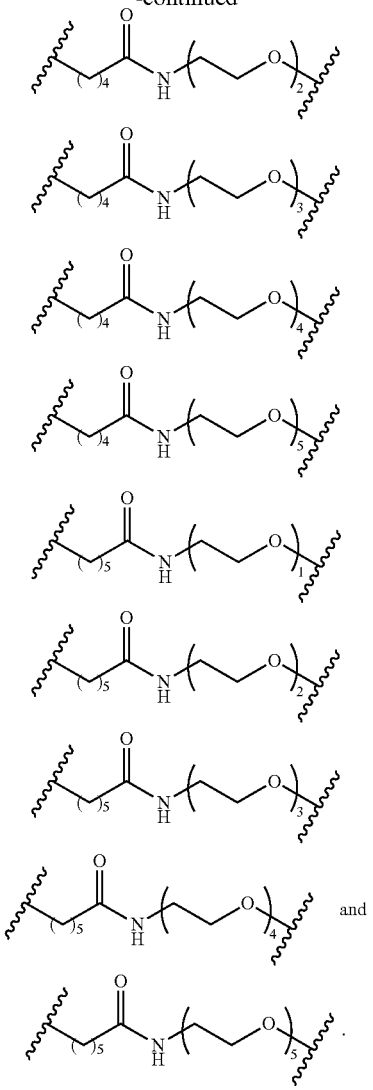
In certain embodiments, the Linker$^4$ is selected from
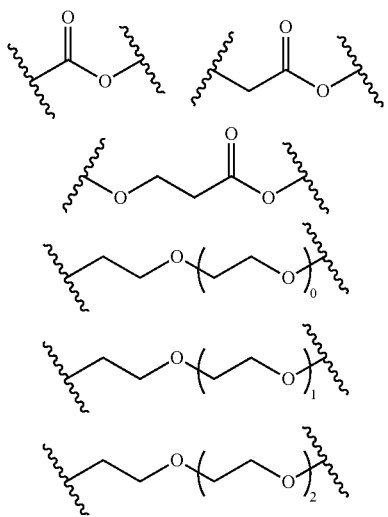

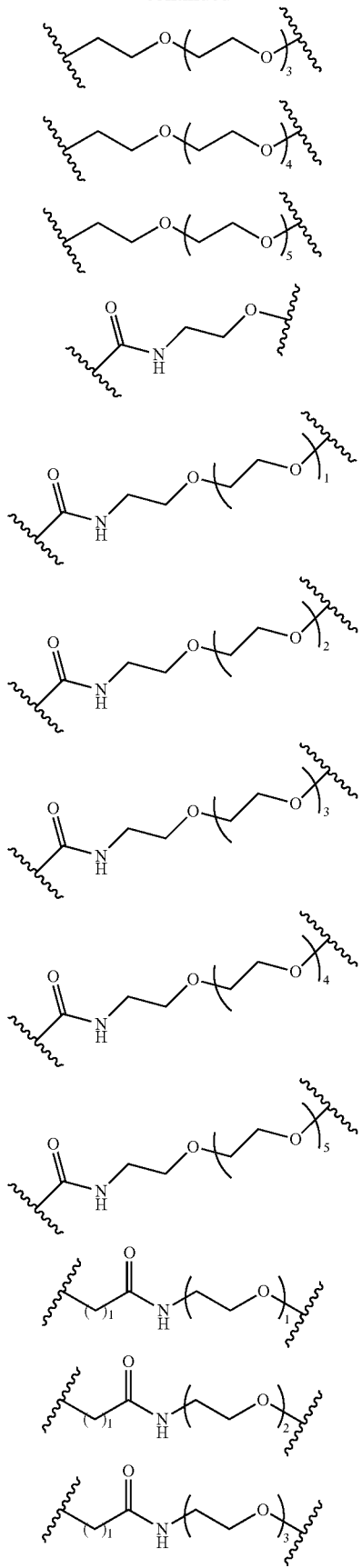
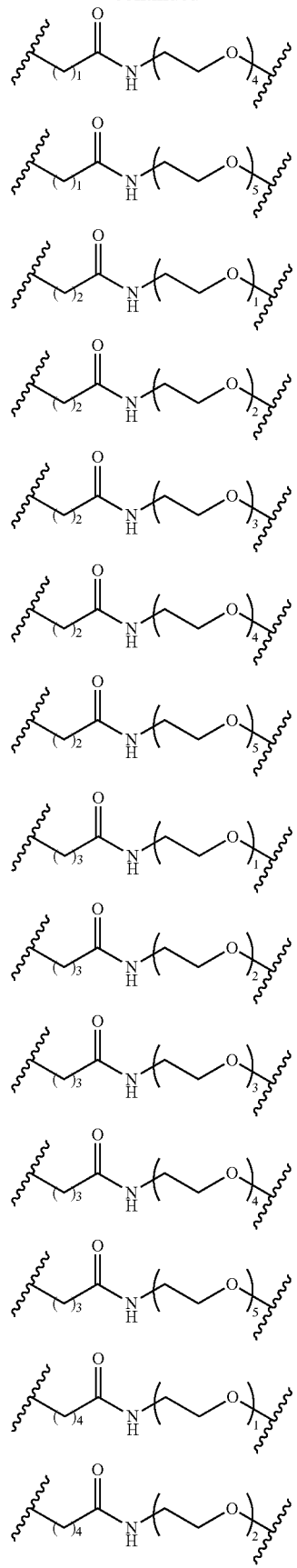

-continued
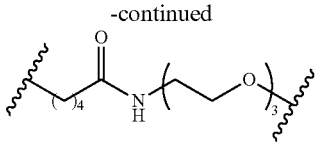
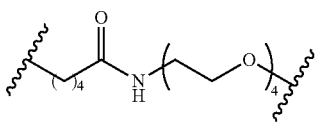
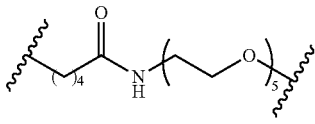
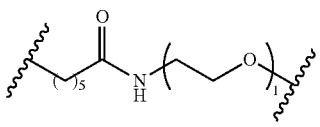
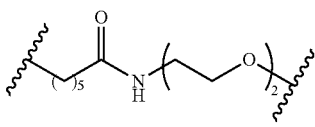
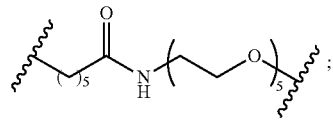 and
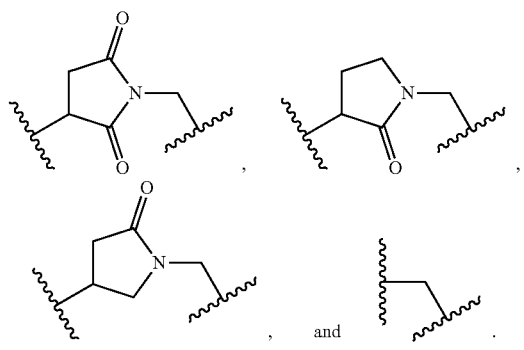;
wherein each is optionally substituted with 1, 2, 3, or 4 substituents substituent selected from R$^{21}$.
In certain embodiments Linker$^4$ is selected from:
In certain embodiments Linker$^4$ is selected from:
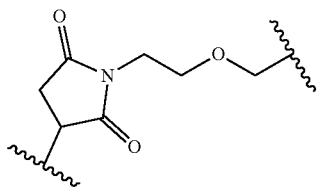,
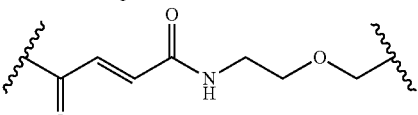,
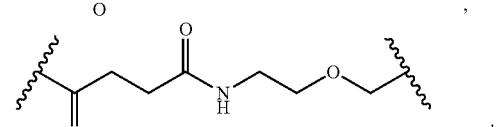, and
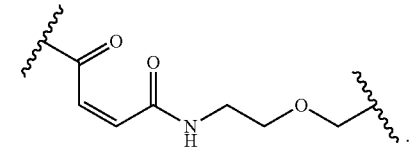.
In certain embodiments Linker$^4$ is selected from:
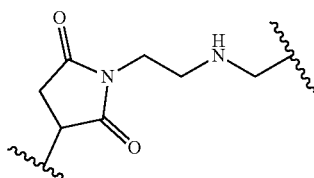,
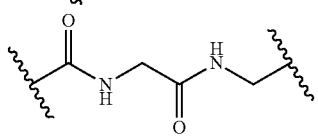,
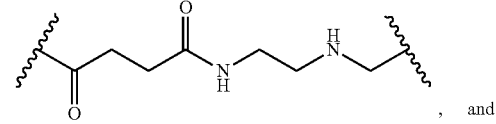, and
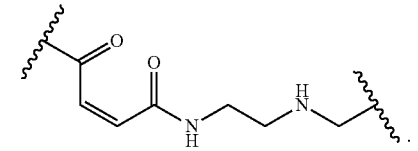.
In certain embodiments Linker$^4$ is selected from:
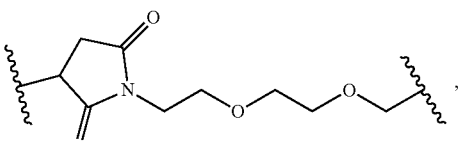,
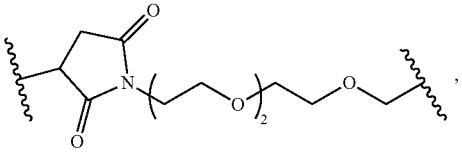, 571
-continued
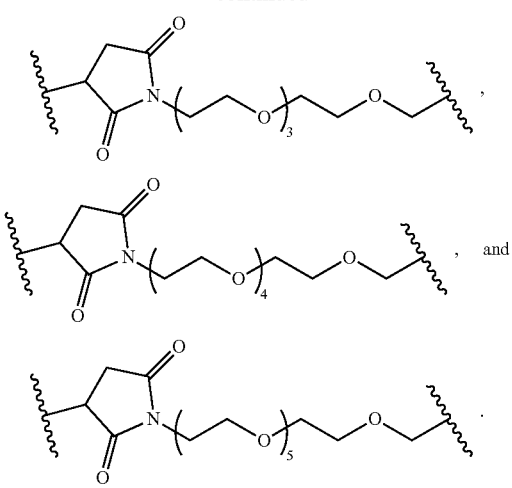
In certain embodiments Linker⁴ is selected from:
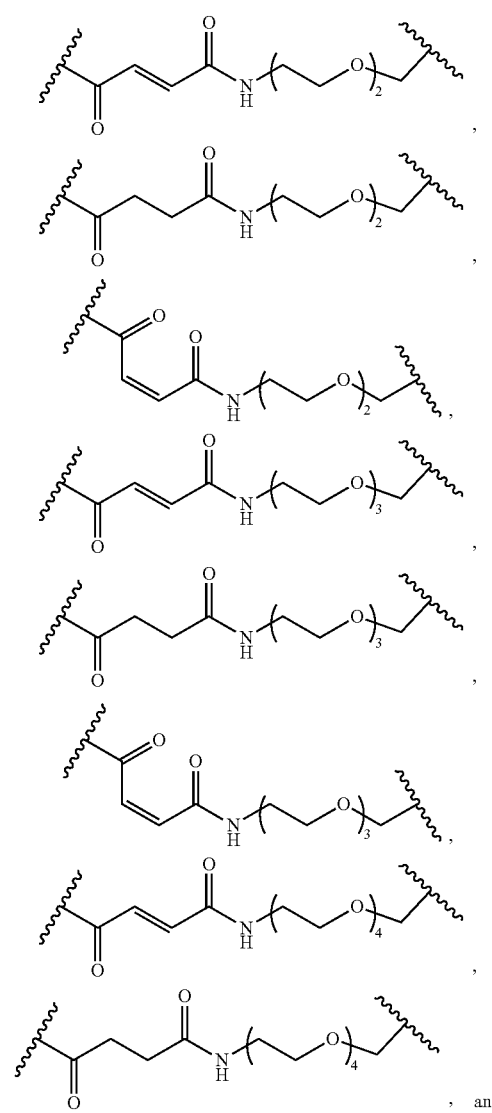
572
-continued
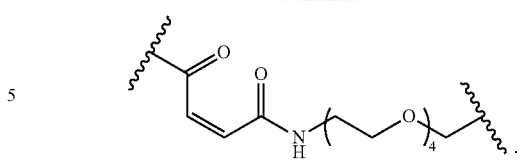
In certain embodiments Linker⁴ is selected from:
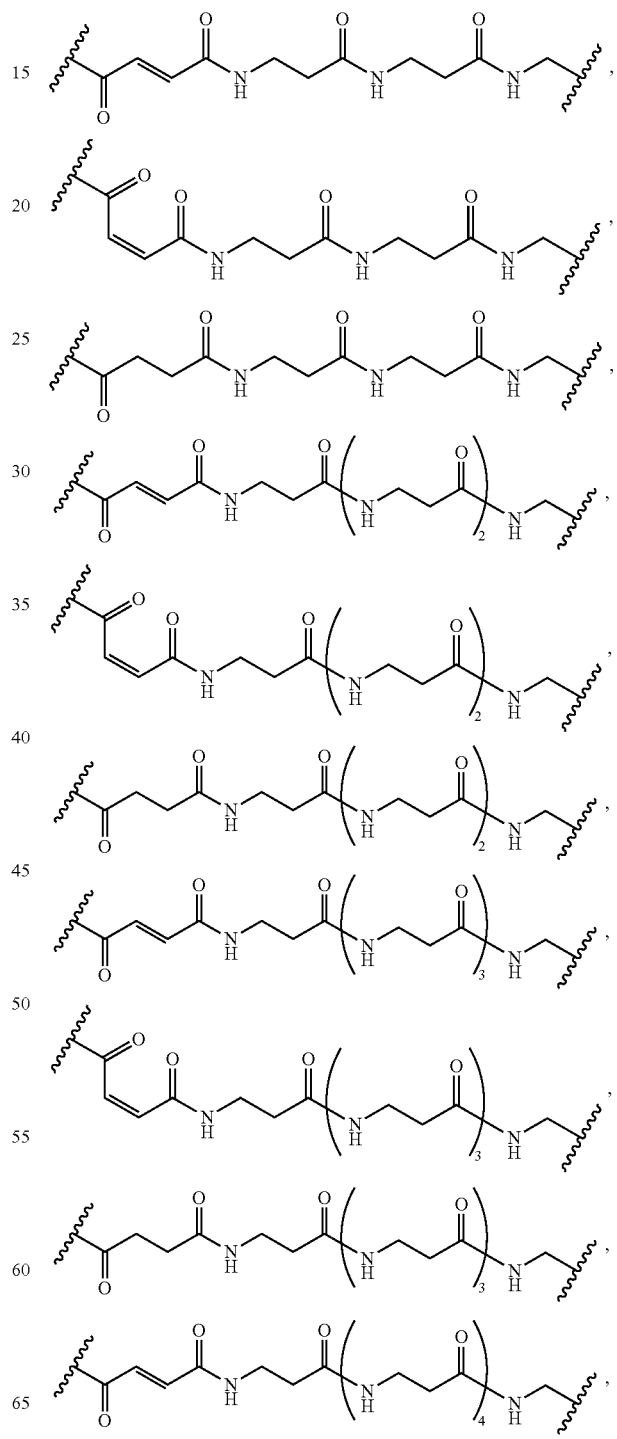

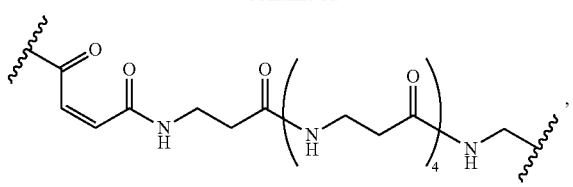
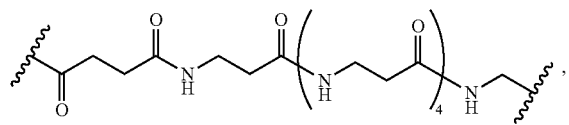
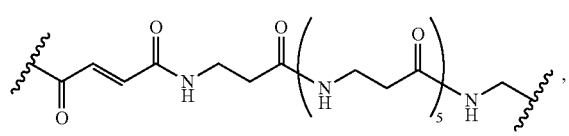

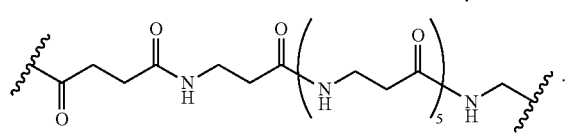, and
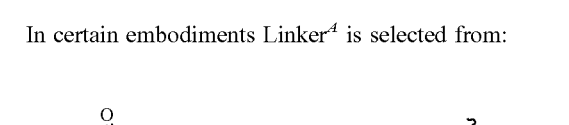.
In certain embodiments Linker[4] is selected from:
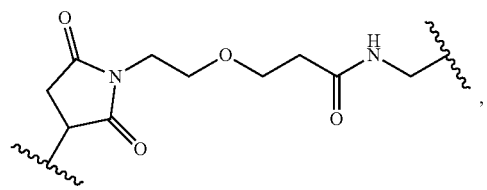,
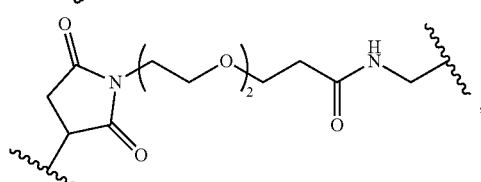,
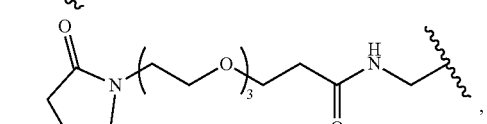,
,
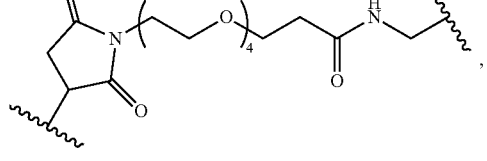,
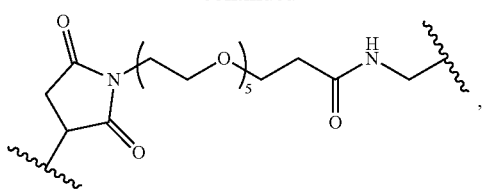,
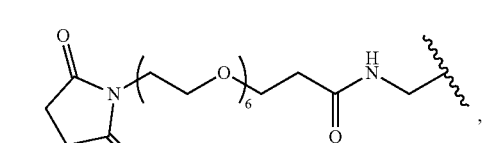,
,
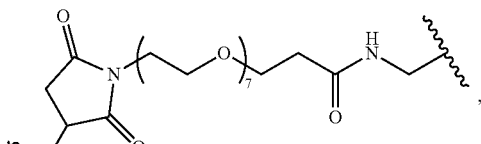,
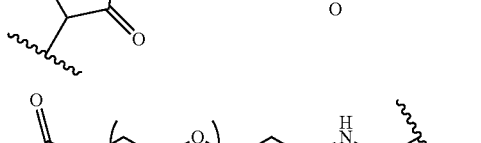, and
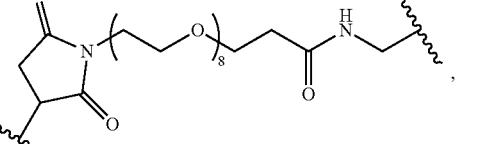
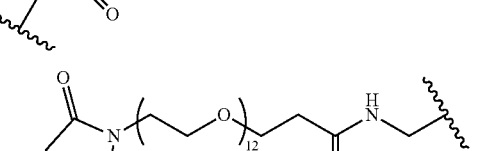.
In certain embodiments Linker[4] is selected from:
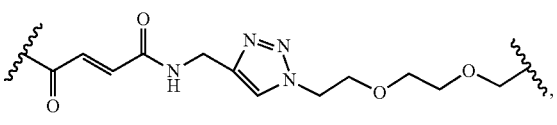,
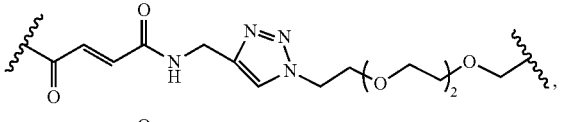,
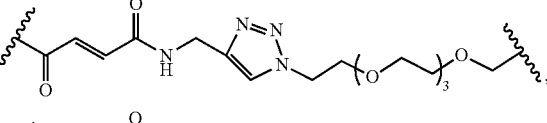,
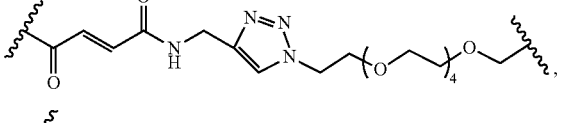,
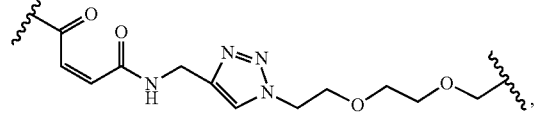, 575
-continued
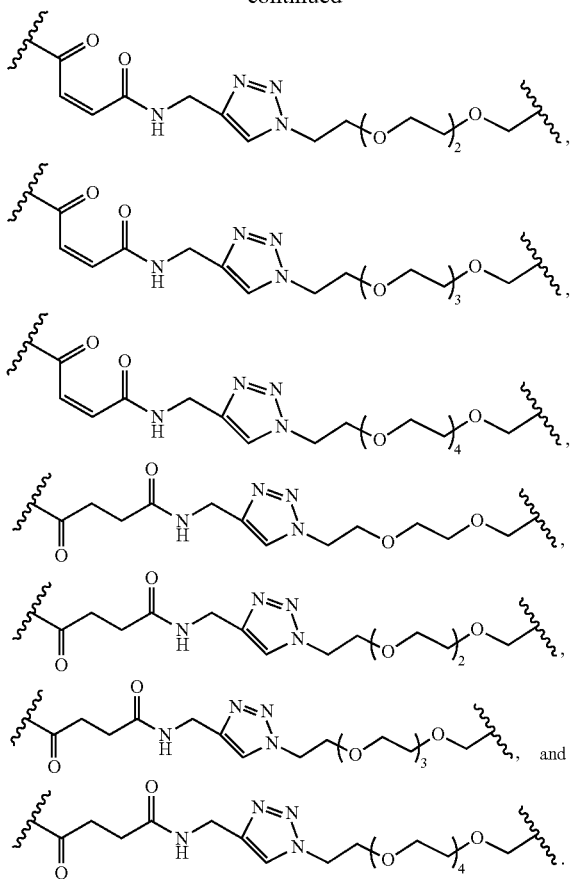
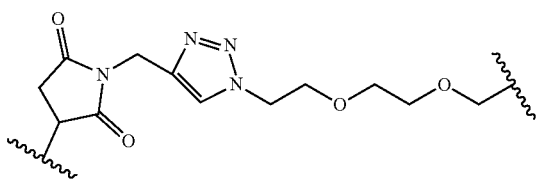
In certain embodiments Linker⁴ is selected from:
576
-continued
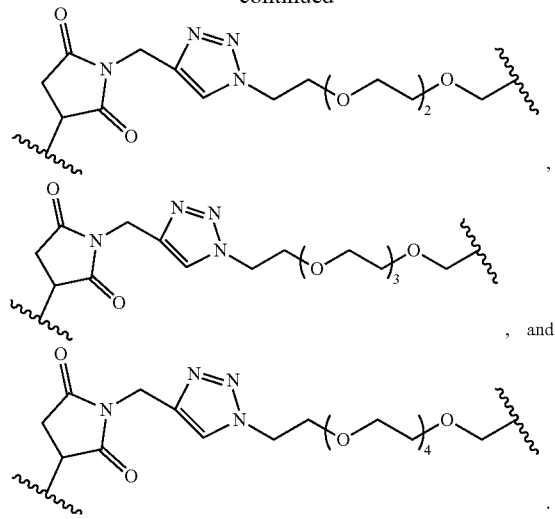
, and
In certain embodiments Linker⁴ is selected from:
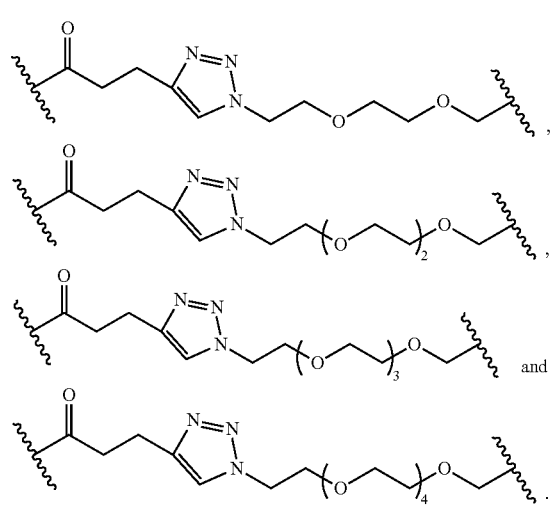
.
In certain embodiments Linker⁴ is selected from:
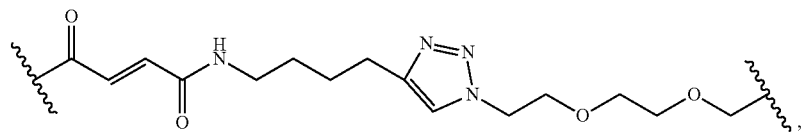
,
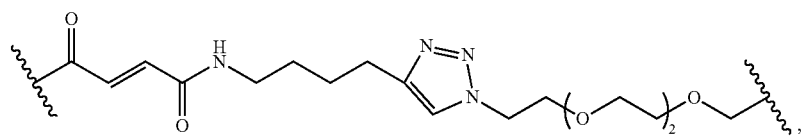
,
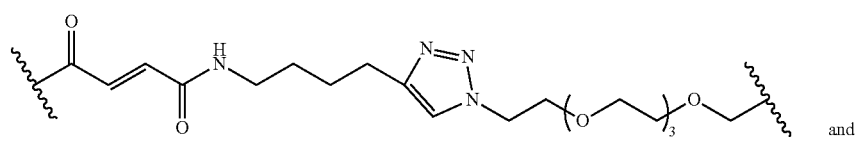
and

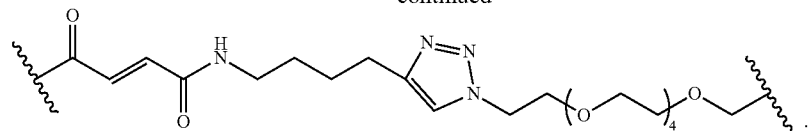
In certain embodiments Linker$^A$ is selected from:
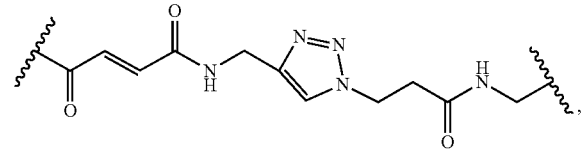
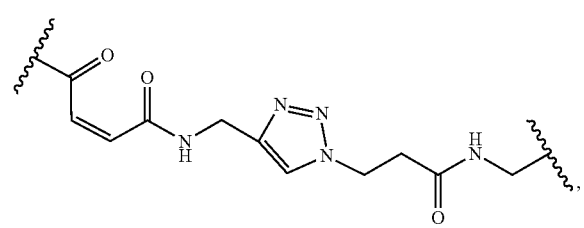
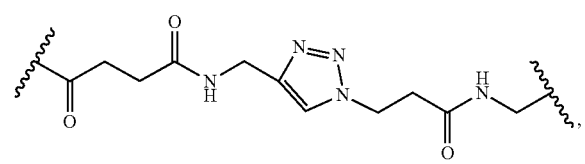
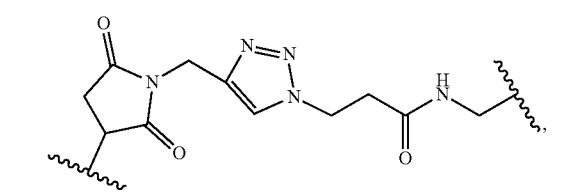
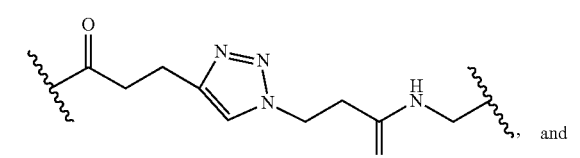
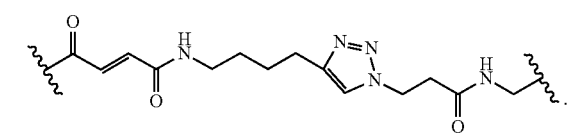
In certain embodiments Linker$^A$ is selected from:
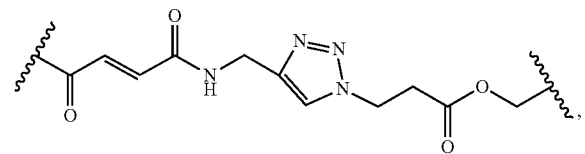
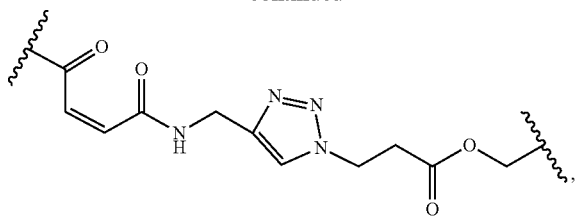
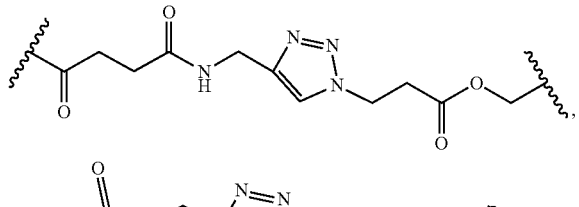
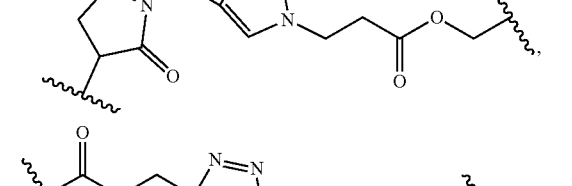
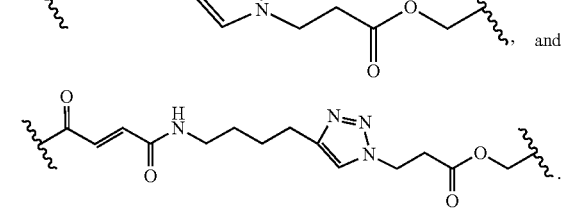
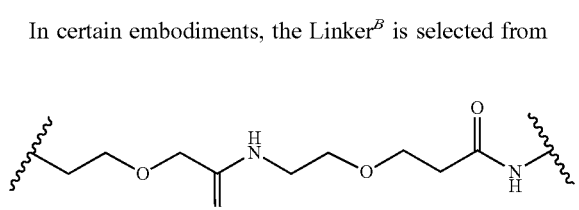
In certain embodiments, the Linker$^B$ is selected from
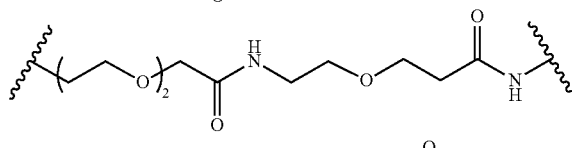
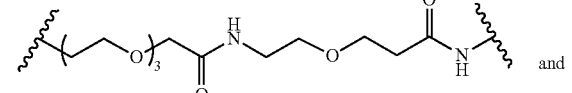
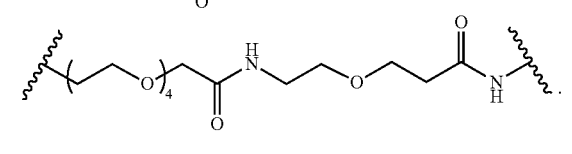

In certain embodiments, the Linker$^B$ is selected from

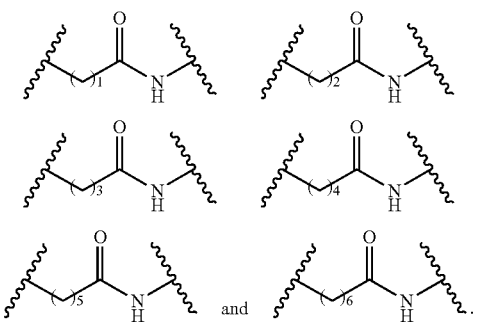

In certain embodiments, the Linker$^B$ is selected from

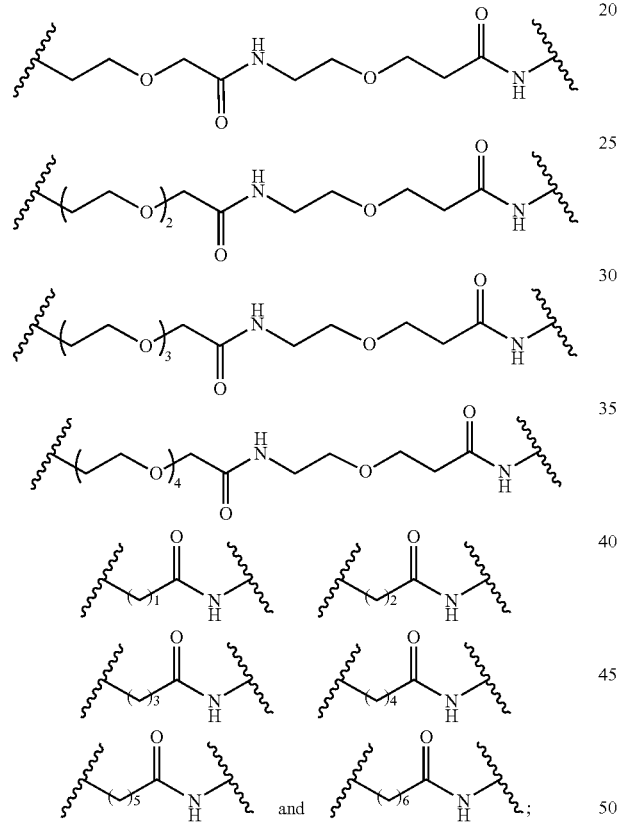

wherein each is optionally substituted with 1, 2, 3, or 4 substituents substituent selected from R$^{21}$.

In certain embodiments Linker$^B$ is selected from

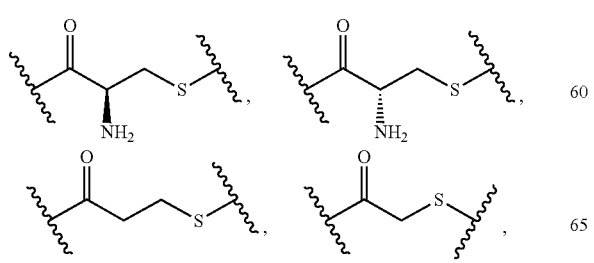

-continued

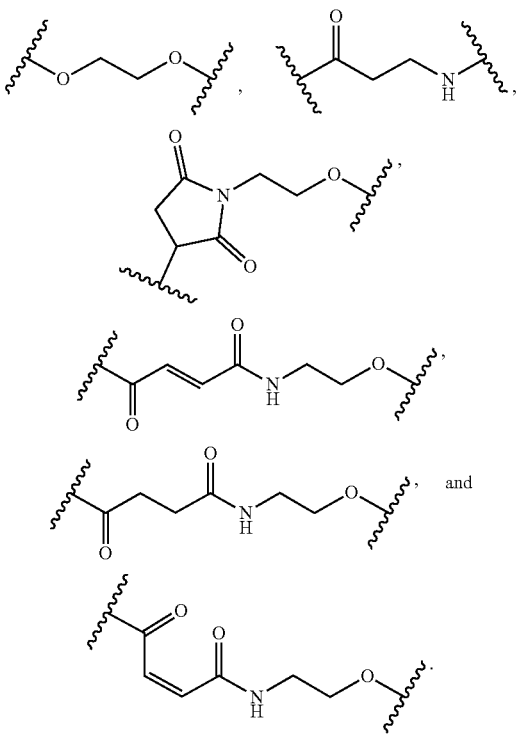

In certain embodiments Linker$^B$ is selected from:

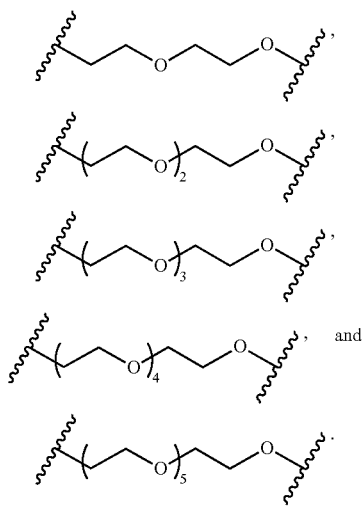

In certain embodiments Linker$^B$ is selected from:

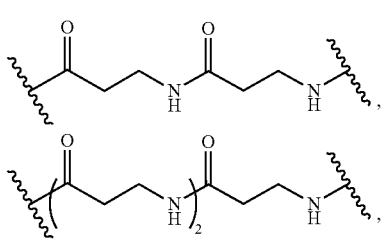

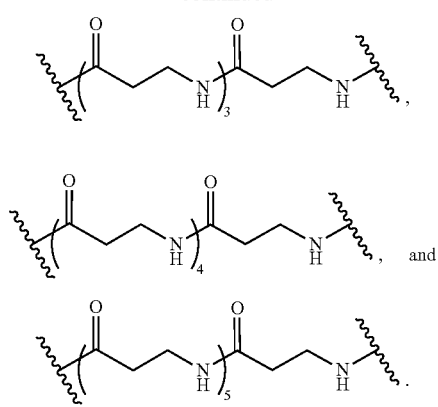
In certain embodiments Linker$^B$ is selected from:
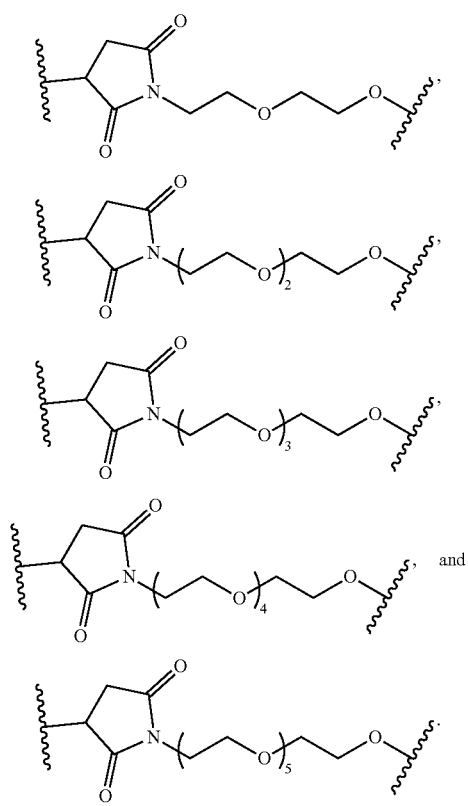
In certain embodiments Linker$^B$ is selected from:
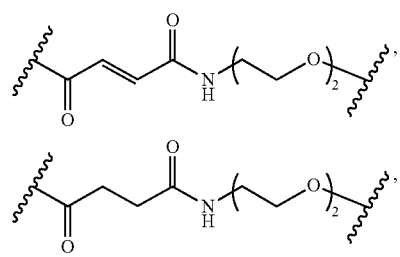
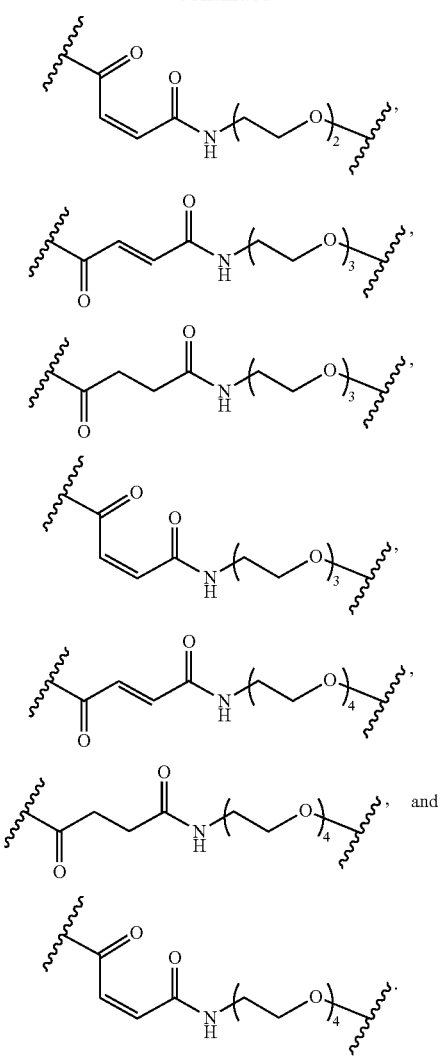
In certain embodiments Linker$^B$ is selected from:
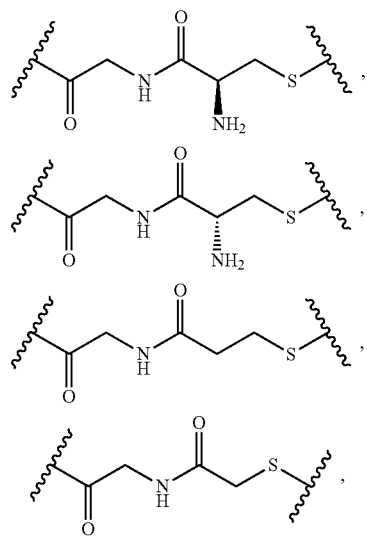

-continued
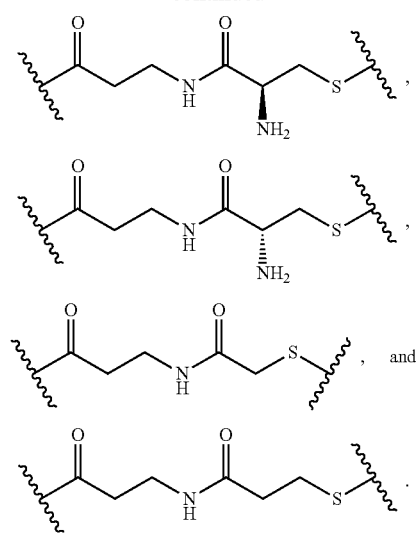
In certain embodiments Linker$^B$ is selected from:
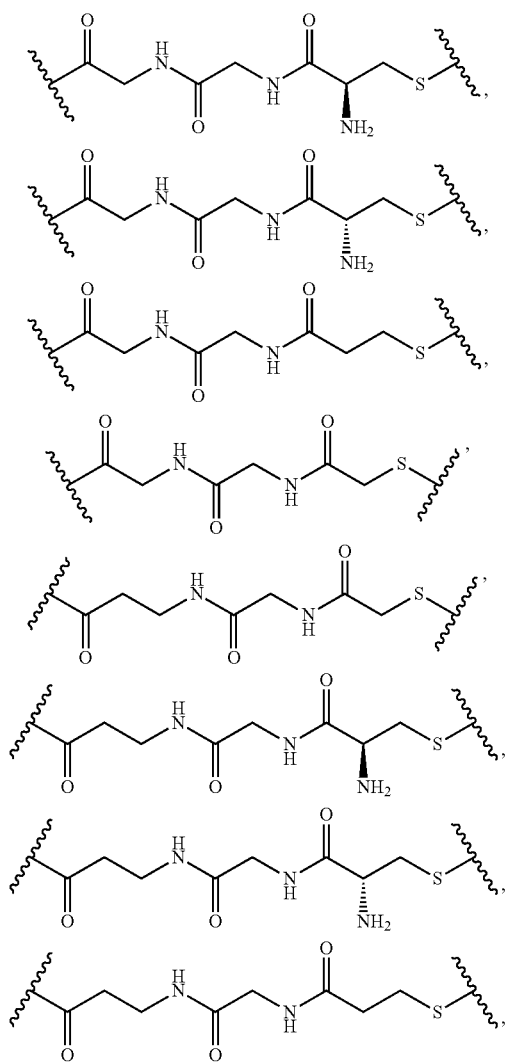
-continued
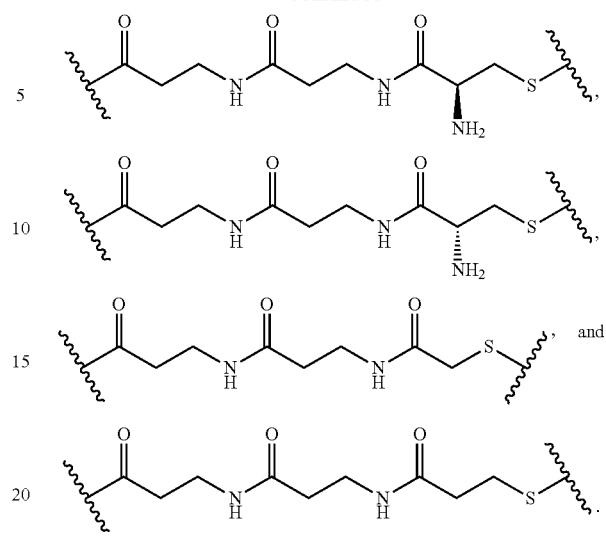
In certain embodiments Linker$^B$ is selected from:
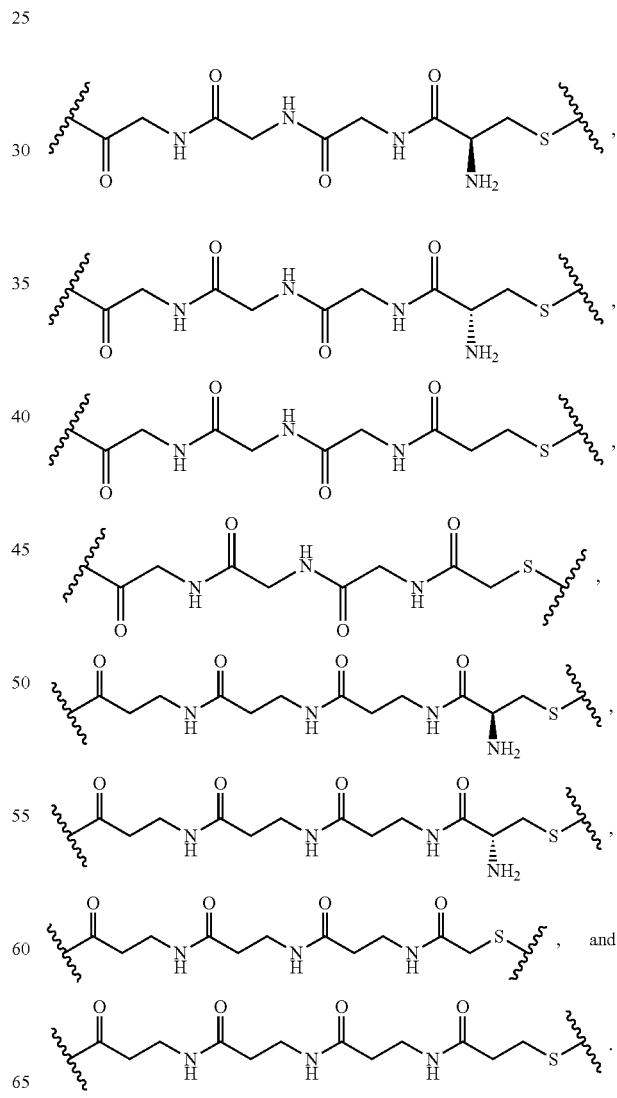

In certain embodiments Linker$^B$-Linker$^A$ is selected from:
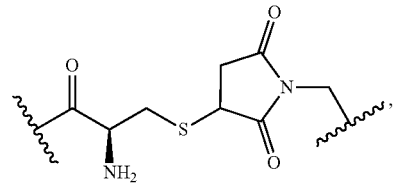
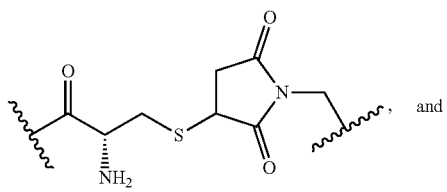, and
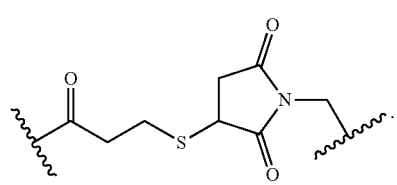
In certain embodiments Linker$^B$-Linker$^A$ is selected from:
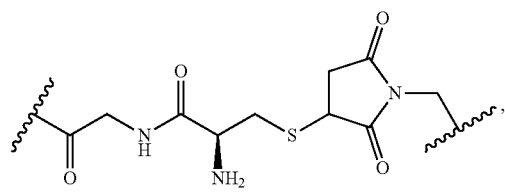
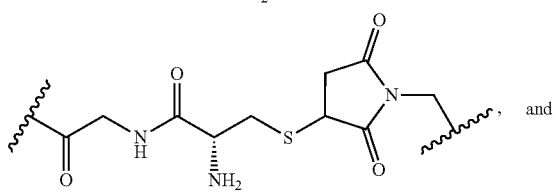, and
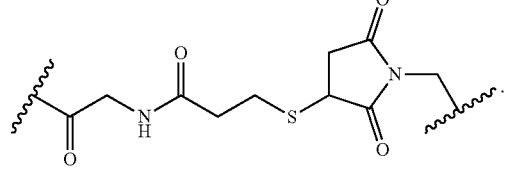
In certain embodiments, the Linker$^C$ is selected from
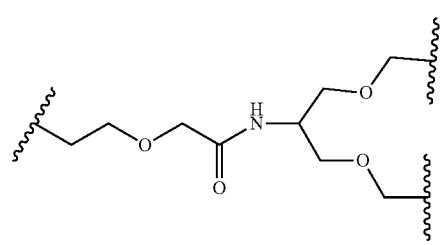
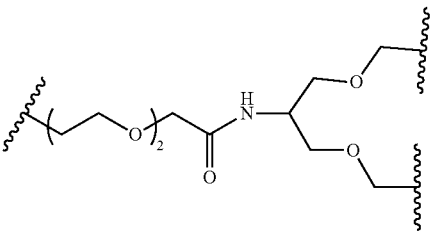
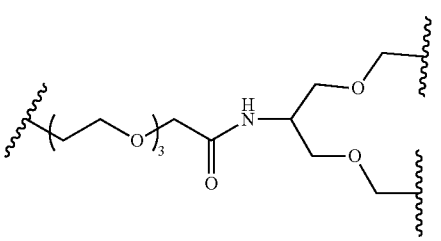, and
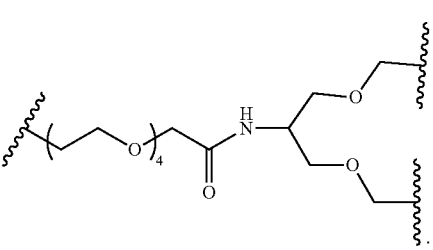
In certain embodiments, the Linker$^C$ is selected from
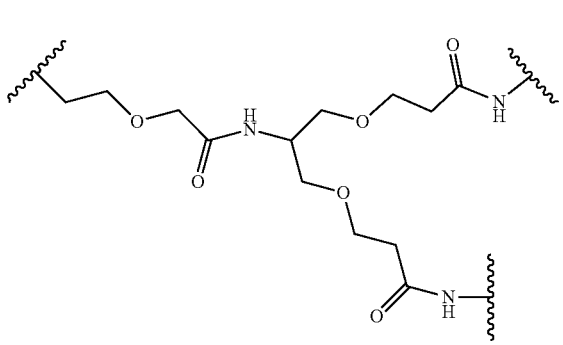
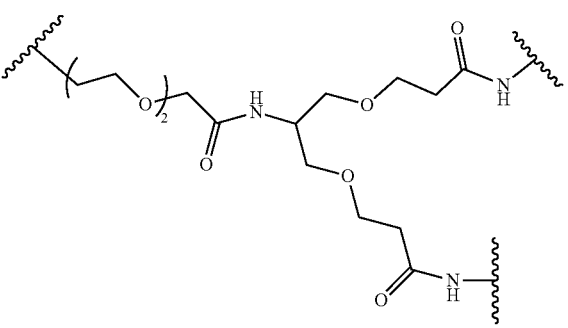

587
-continued
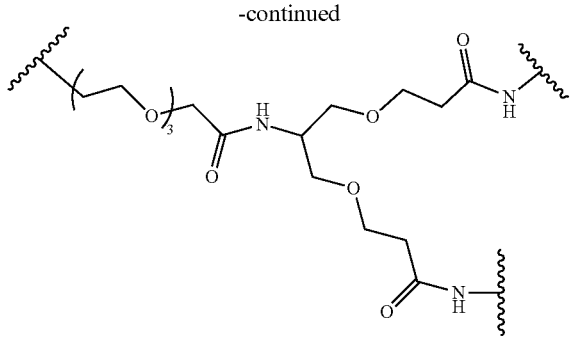
and
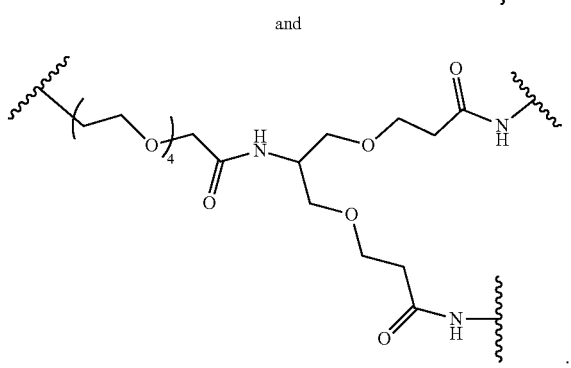
In certain embodiments, the Linker$^C$ is selected from
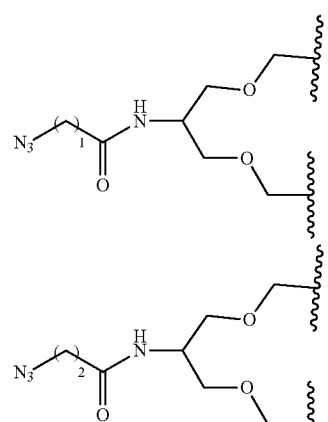
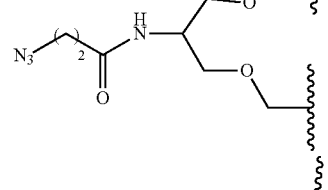
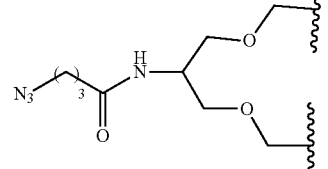
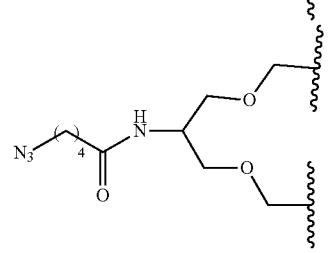
588
-continued
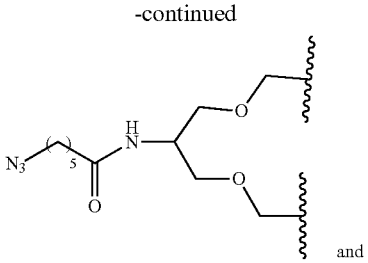
and
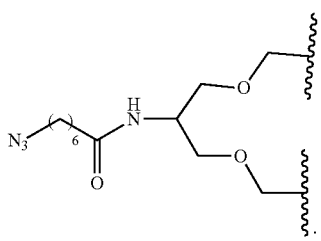
In certain embodiments, the Linker$^C$ is selected from
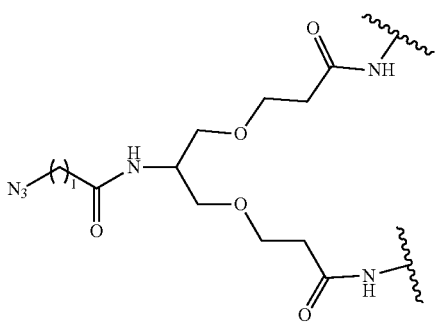
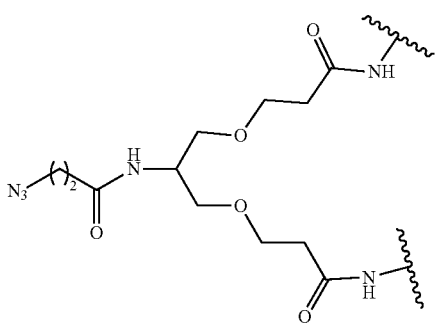

589
-continued
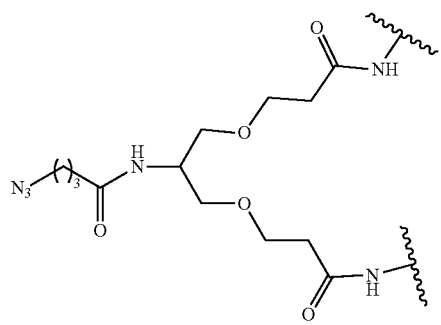
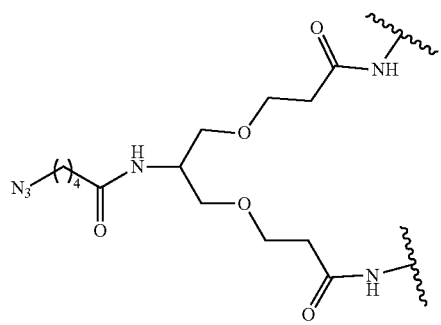
590
-continued
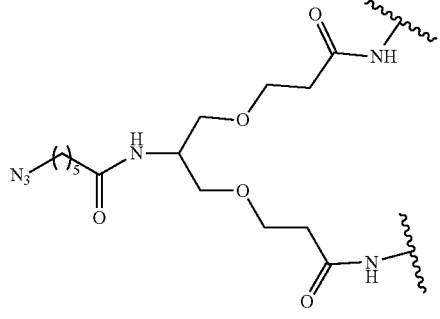
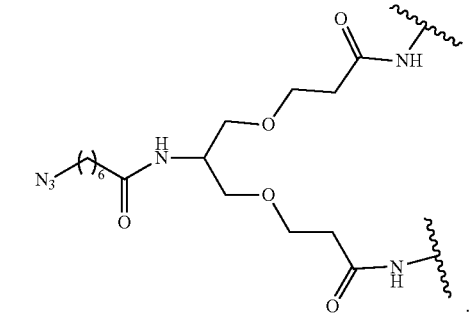
and
In certain embodiments, the Linker$^C$ is selected from
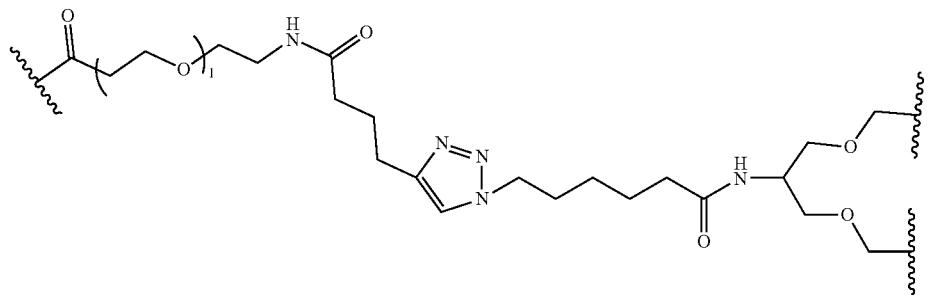
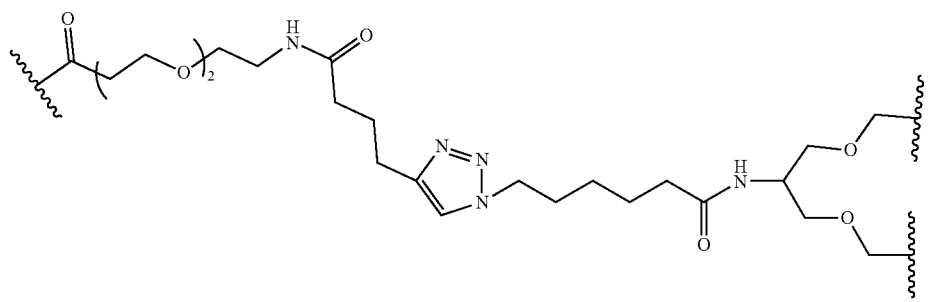
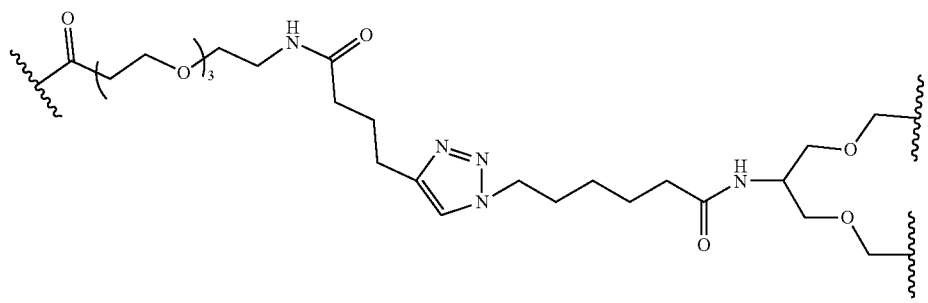

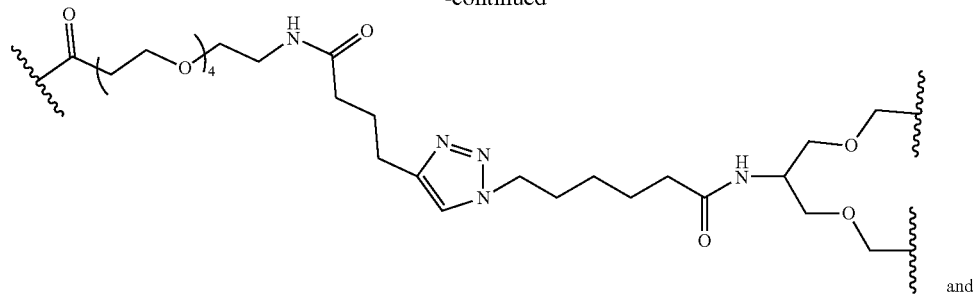
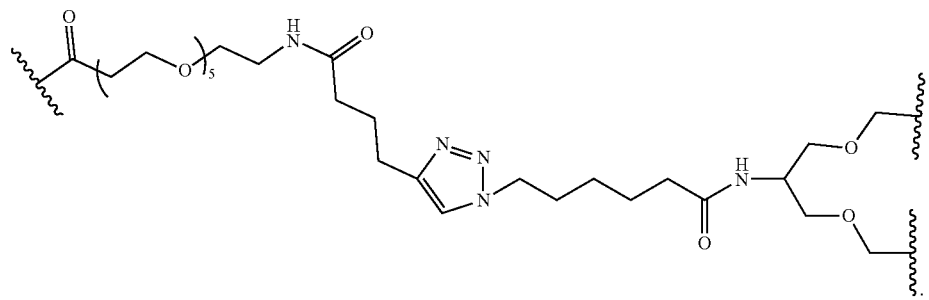
In certain embodiments, the Linker$^C$ is selected from
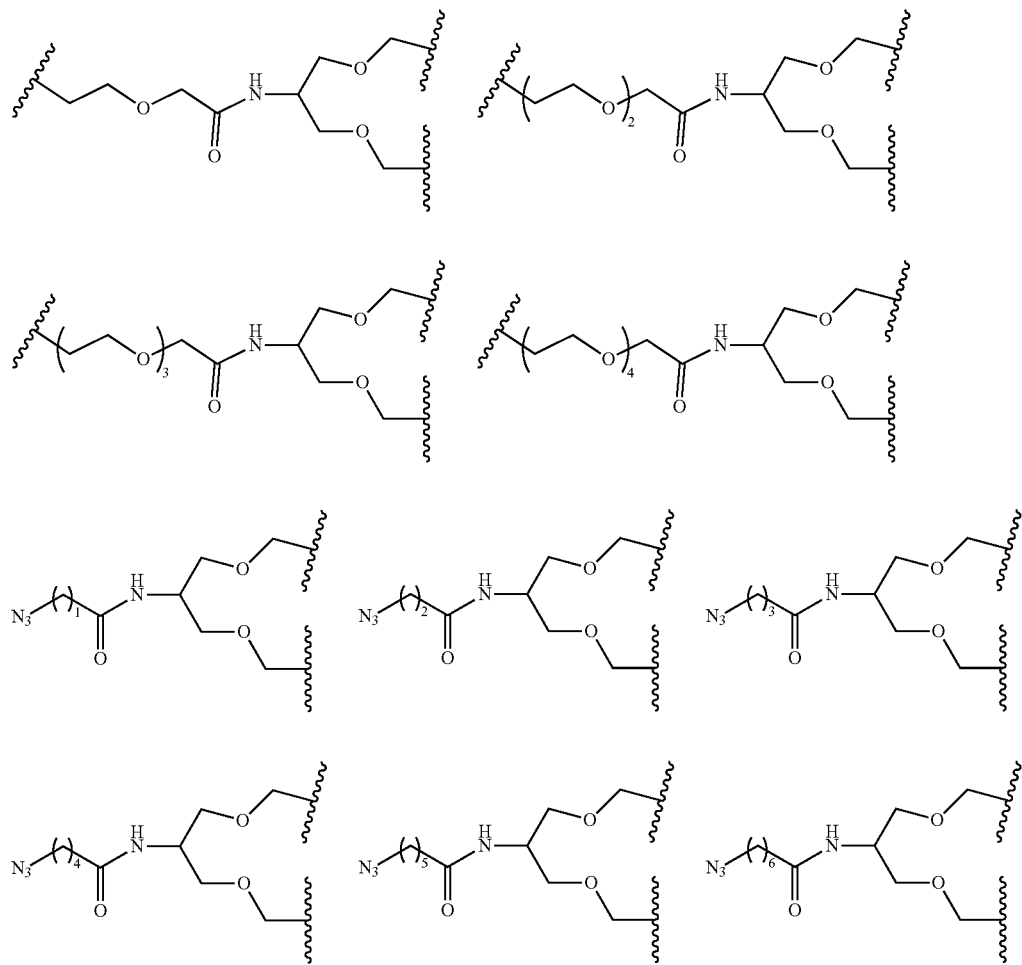

593 594
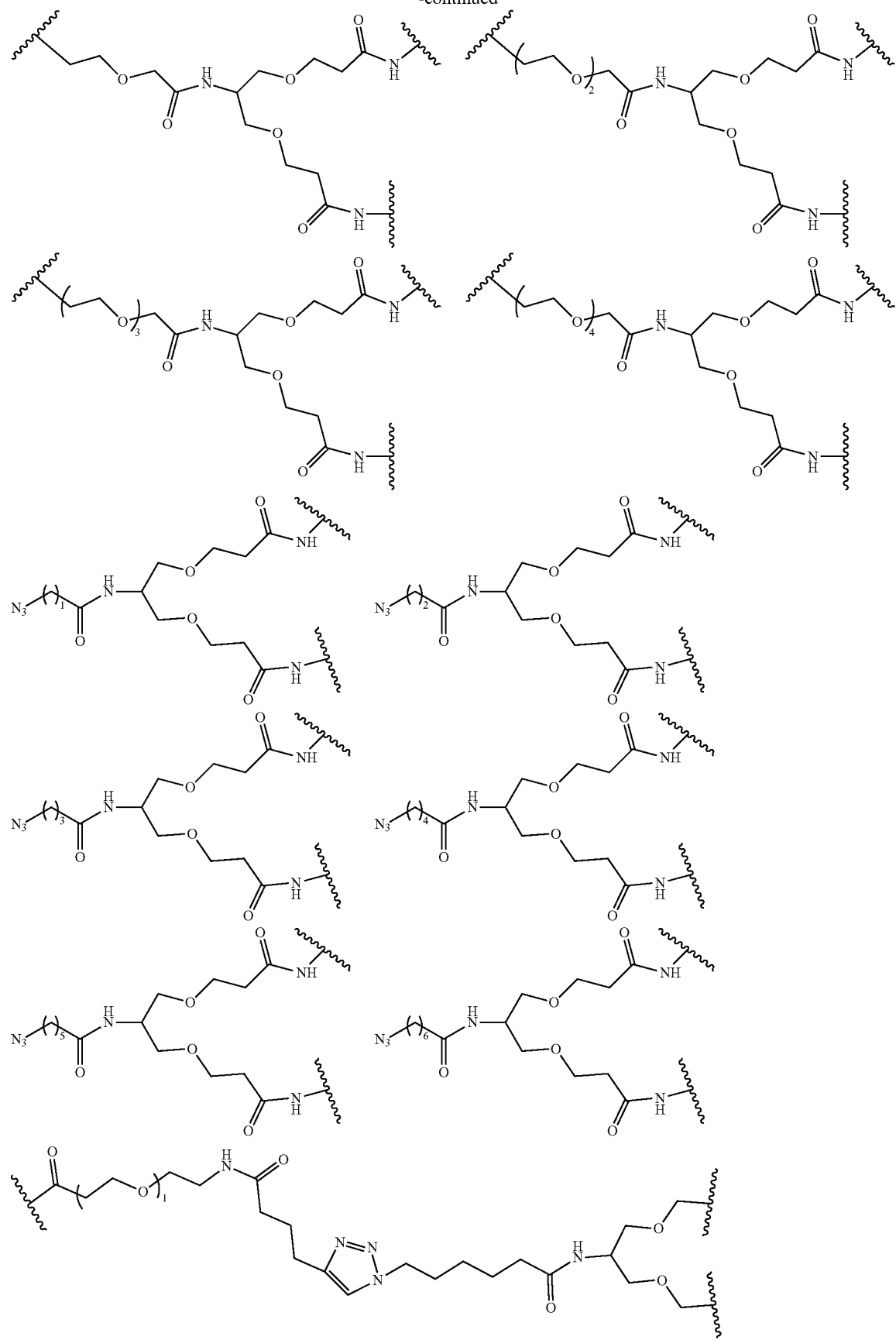

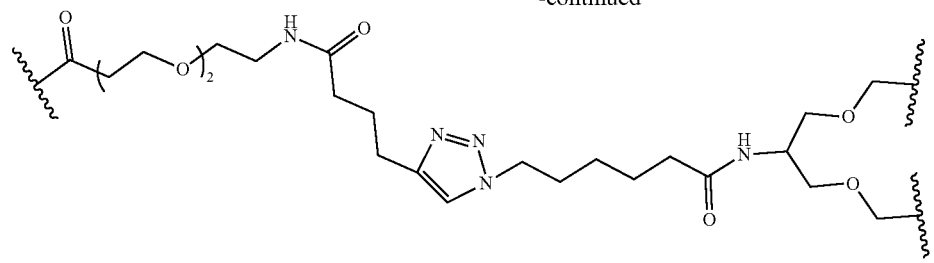
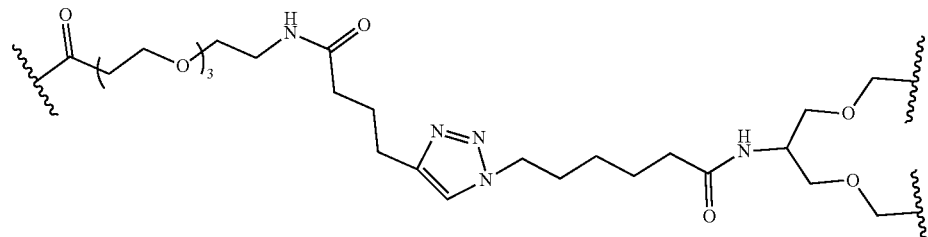
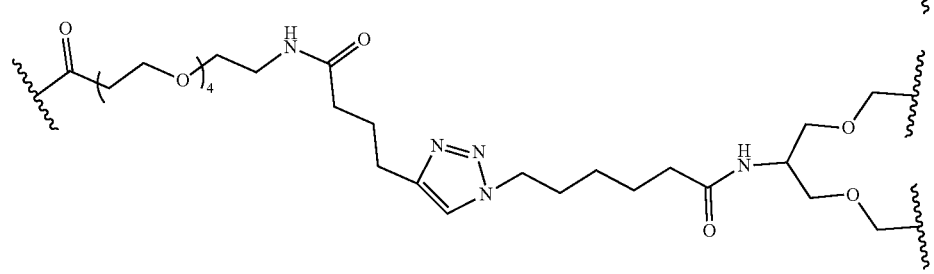
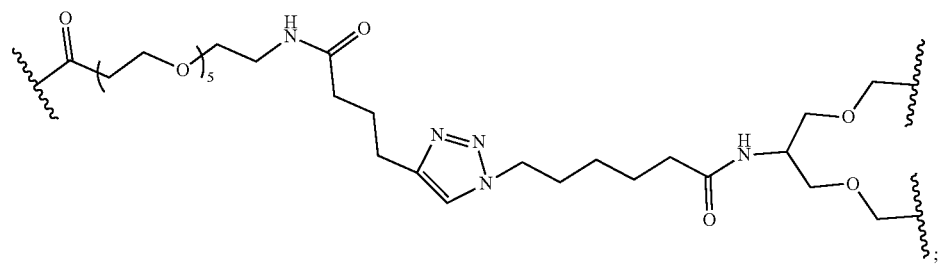
and
wherein each is optionally substituted with 1, 2, 3, or 4 substituents substituent selected from $R^{21}$.
In certain embodiments Linker$^C$ is selected from:
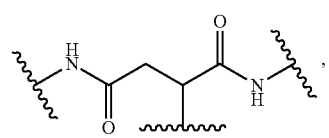
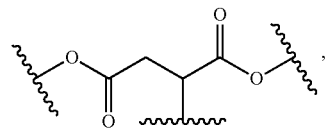
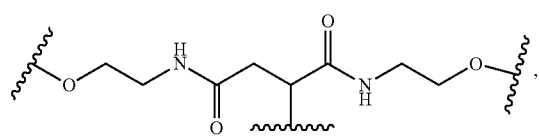
-continued
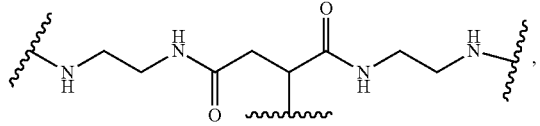
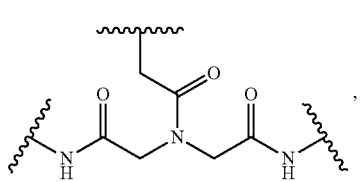
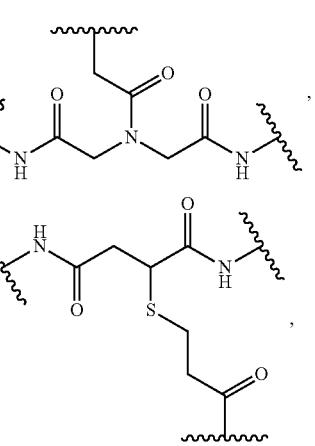

597
-continued
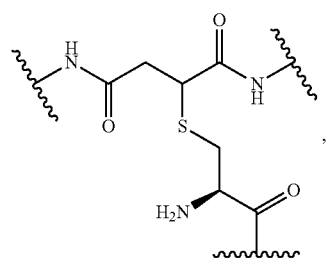
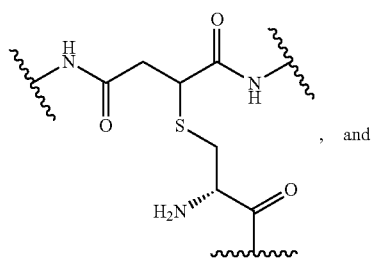
, and
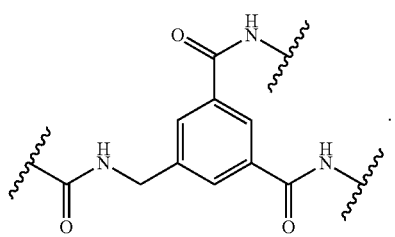 [SMILES: *NC(=O)c1cc(CNC(*)=O)cc(C(=O)N*)c1]
In certain embodiments Linker$^C$ is selected from:
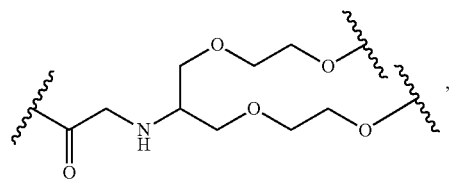
,

,
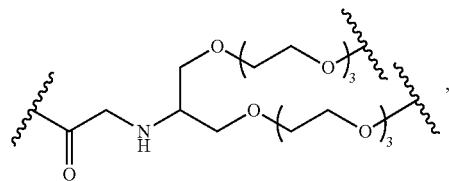
,
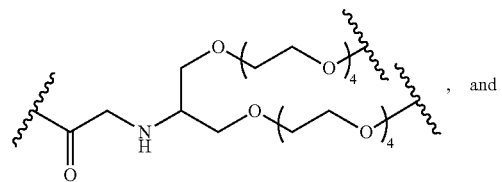
, and
598
-continued
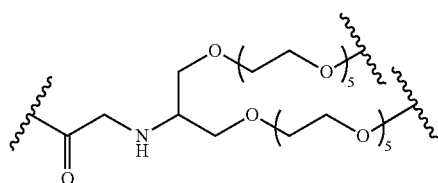
.
In certain embodiments Linker$^C$ is selected from:
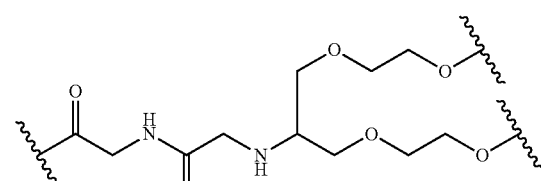
,
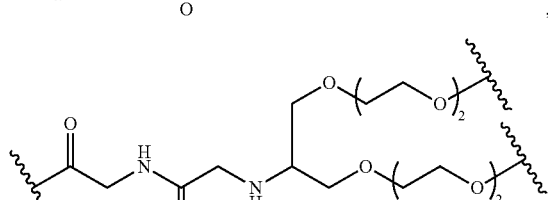
,
and
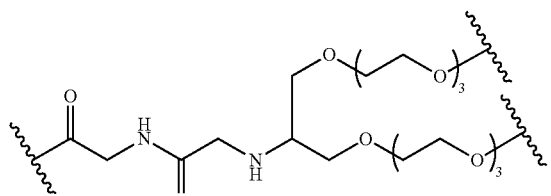
.
In certain embodiments Linker$^C$ is selected from:
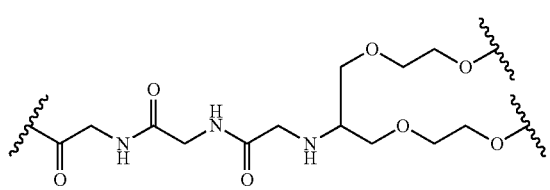
,
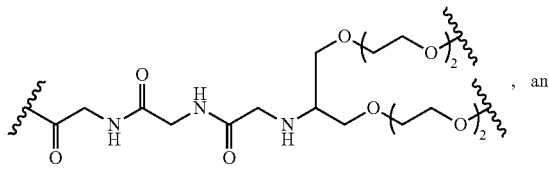
, and
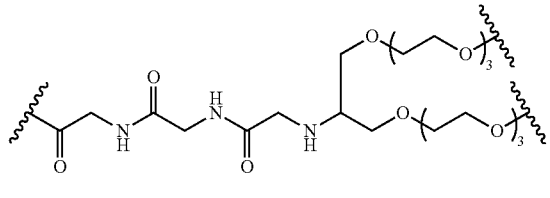
.

In certain embodiments Linker$^C$ is selected from:
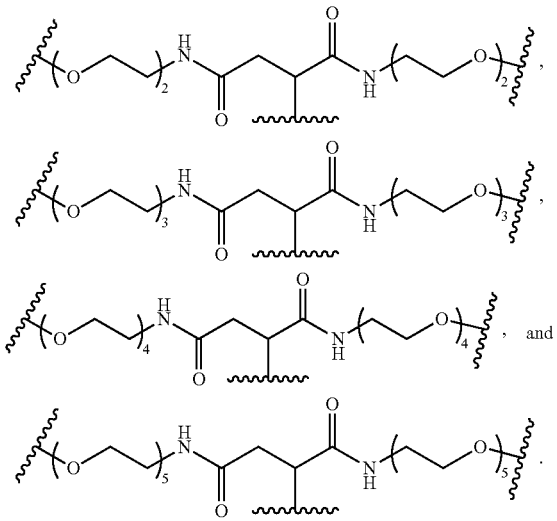
In certain embodiments Linker$^C$ is selected from:
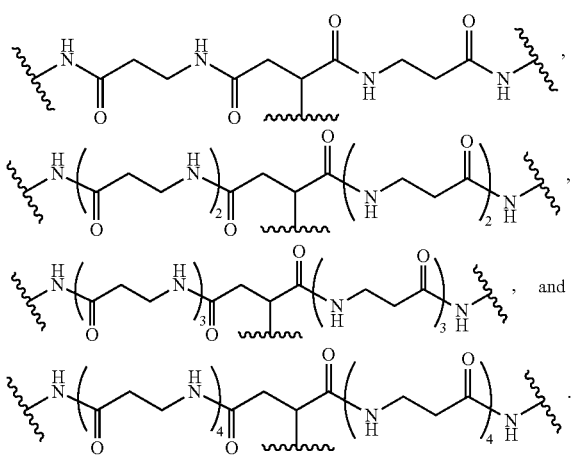
In certain embodiments Linker$^C$ is selected from:
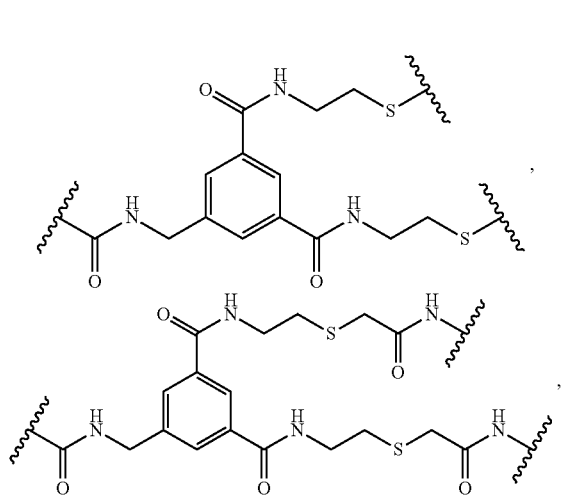
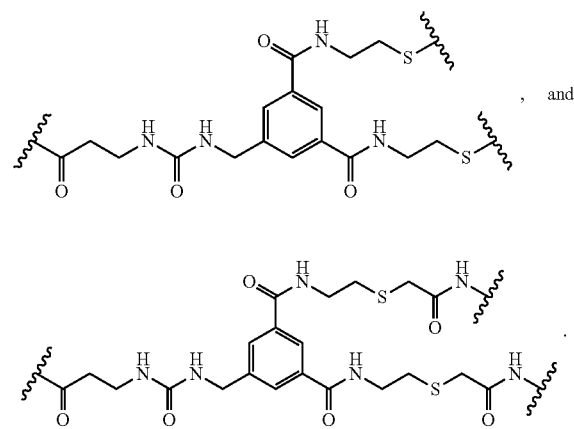
In certain embodiments Linker$^C$-(Linker$^4$)$_2$ is selected from:
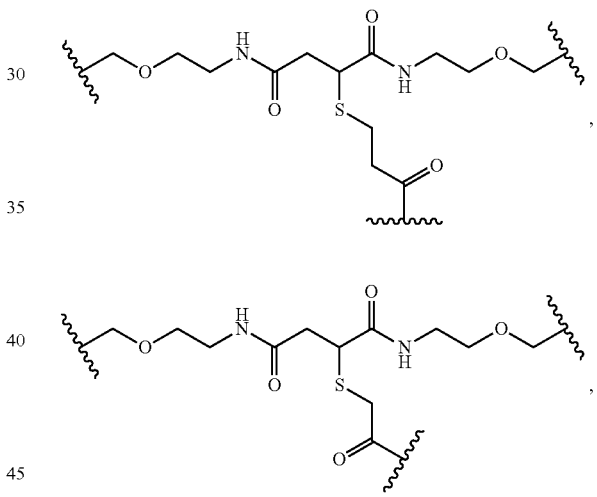
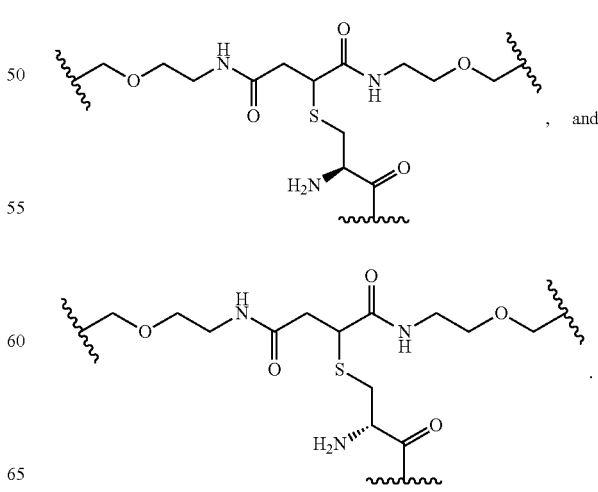

In certain embodiments Linker$^C$-(Linker$^4$)$_2$ is selected from:
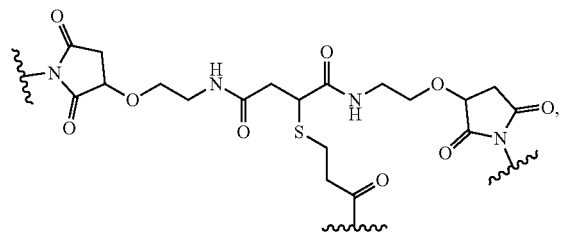
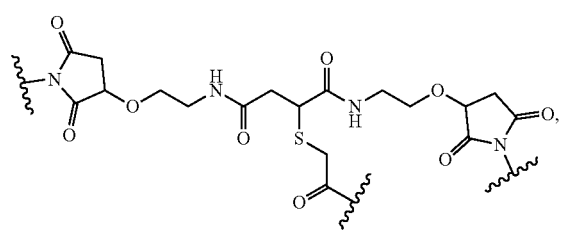
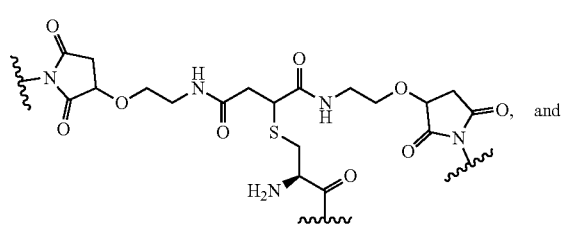
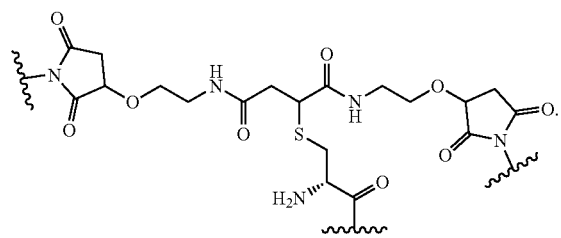
In certain embodiments Linker$^C$-(Linker$^4$)$_2$ is selected from:
In certain embodiments Linker$^A$-(Linker$^4$)$_2$ is selected from:
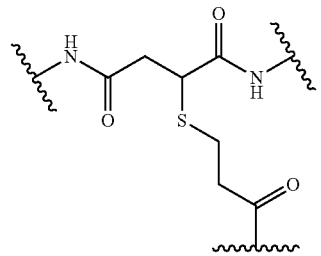
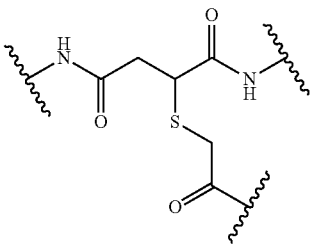
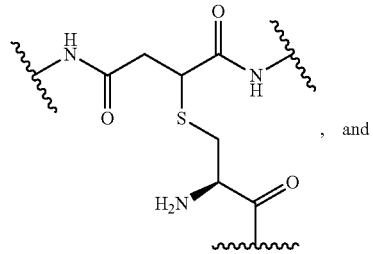
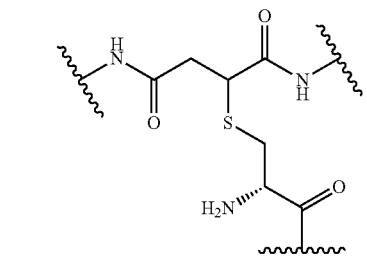
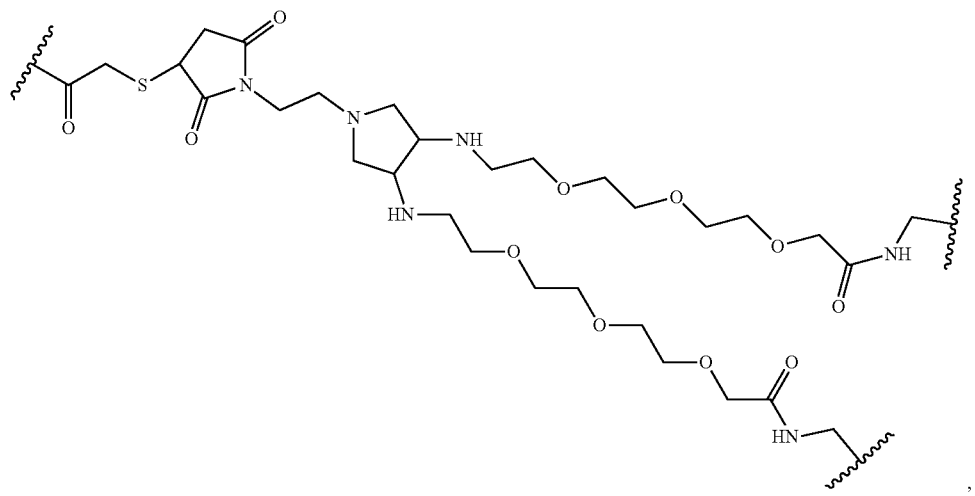

-continued
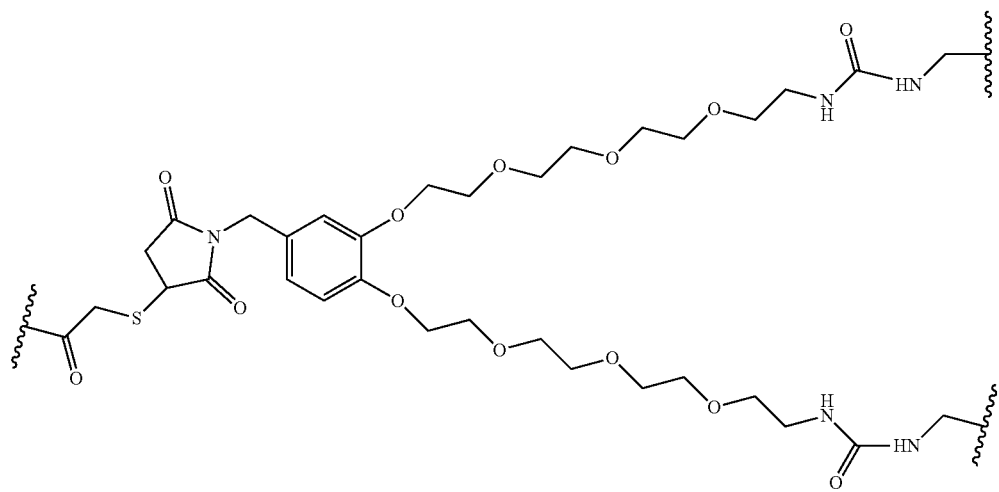
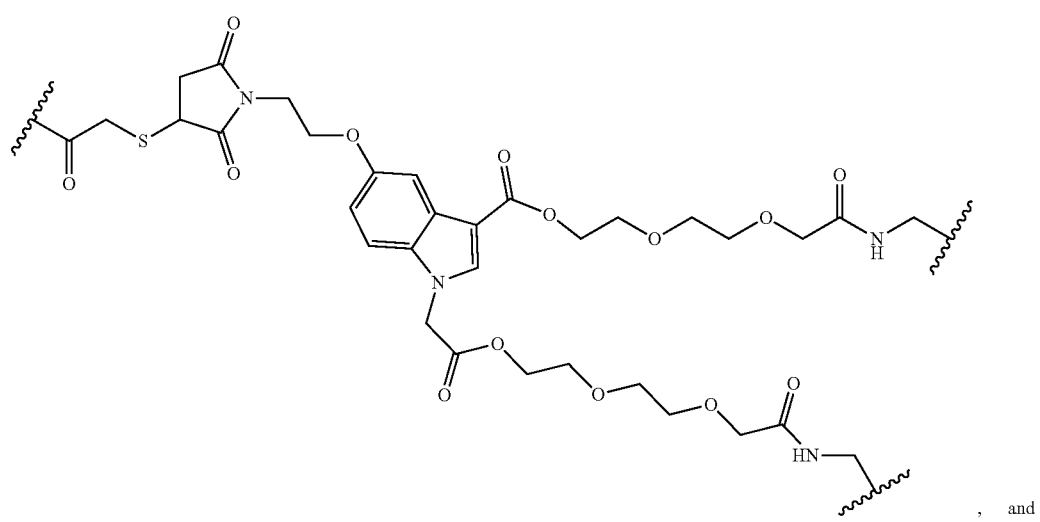
, and
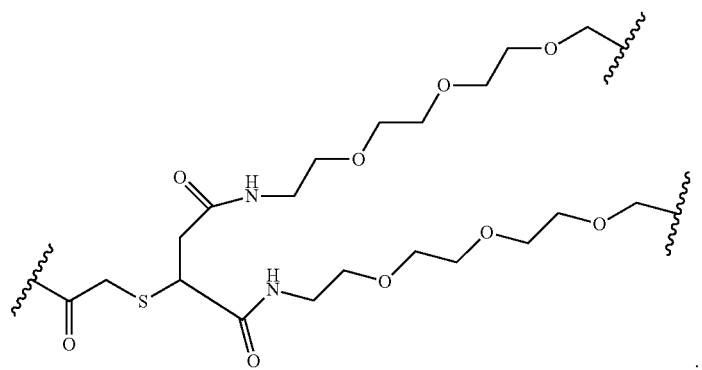 [SMILES: *COCCOCCOCCNC(=O)CC(SCC(*)=O)C(=O)NCCOCCOCCOC*]

In certain embodiments, the Linker$^D$ is selected from
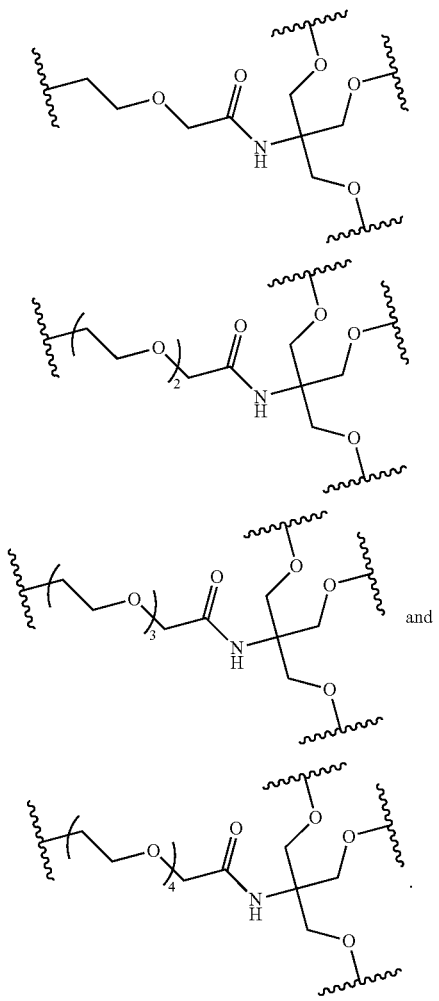
In certain embodiments, the Linker$^D$ is selected from
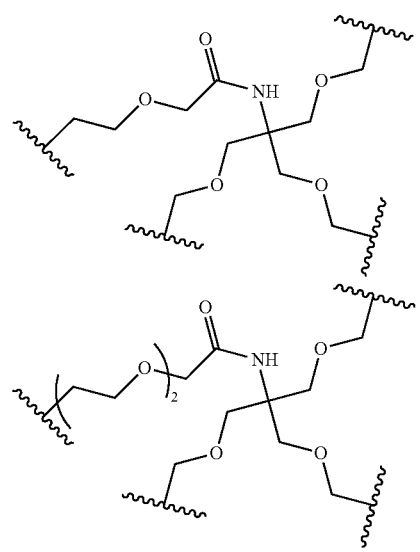
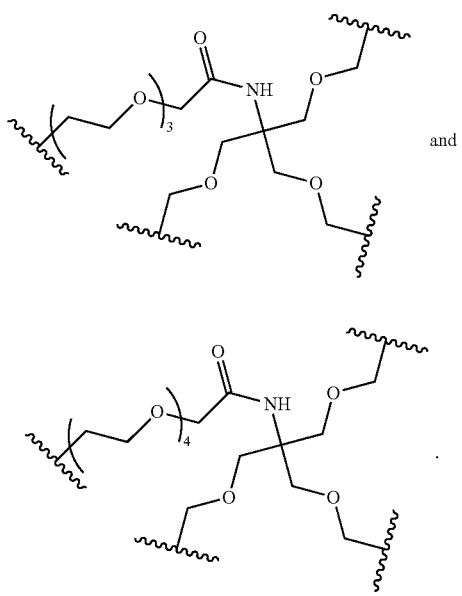
and
In certain embodiments, the Linker$^D$ is selected from
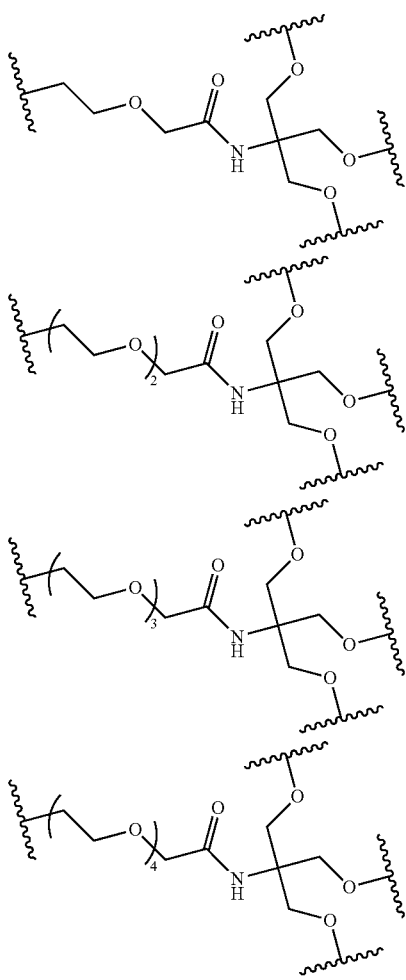

607
-continued
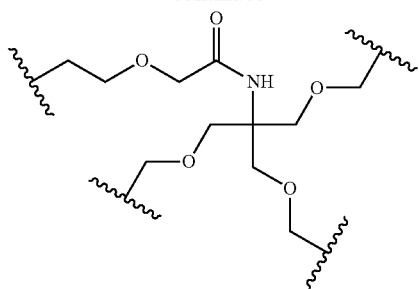
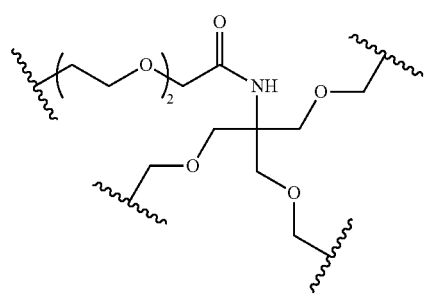
608
-continued
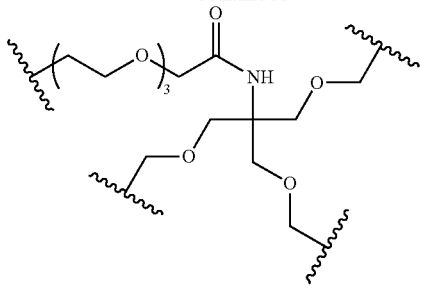
and
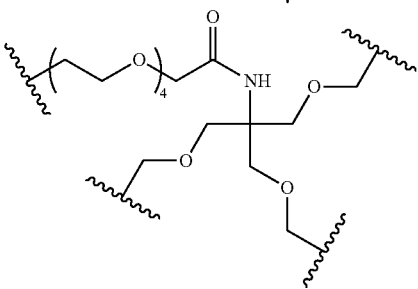
;
wherein each is optionally substituted with 1, 2, 3, or 4 substituents are selected from $R^{21}$.
In certain embodiments, $Linker^B$-$(Linker^A)$ is selected from
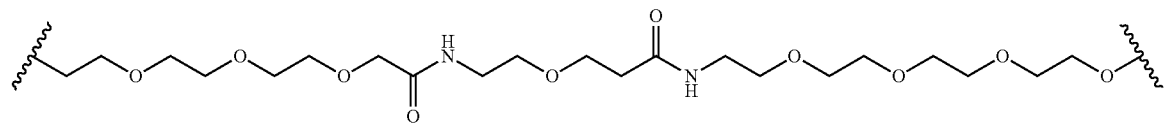
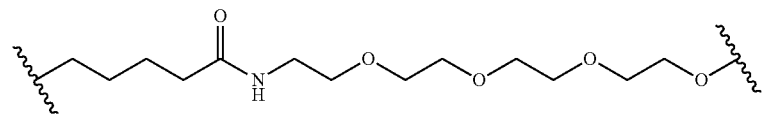
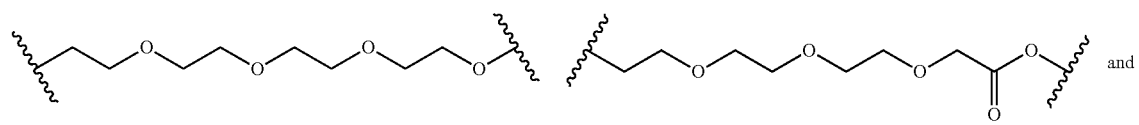
and
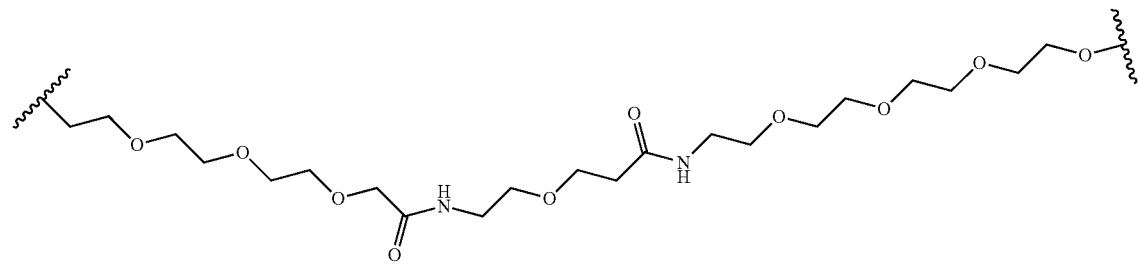
.

In certain embodiments, Linker$^C$-(Linker$^A$) is selected from
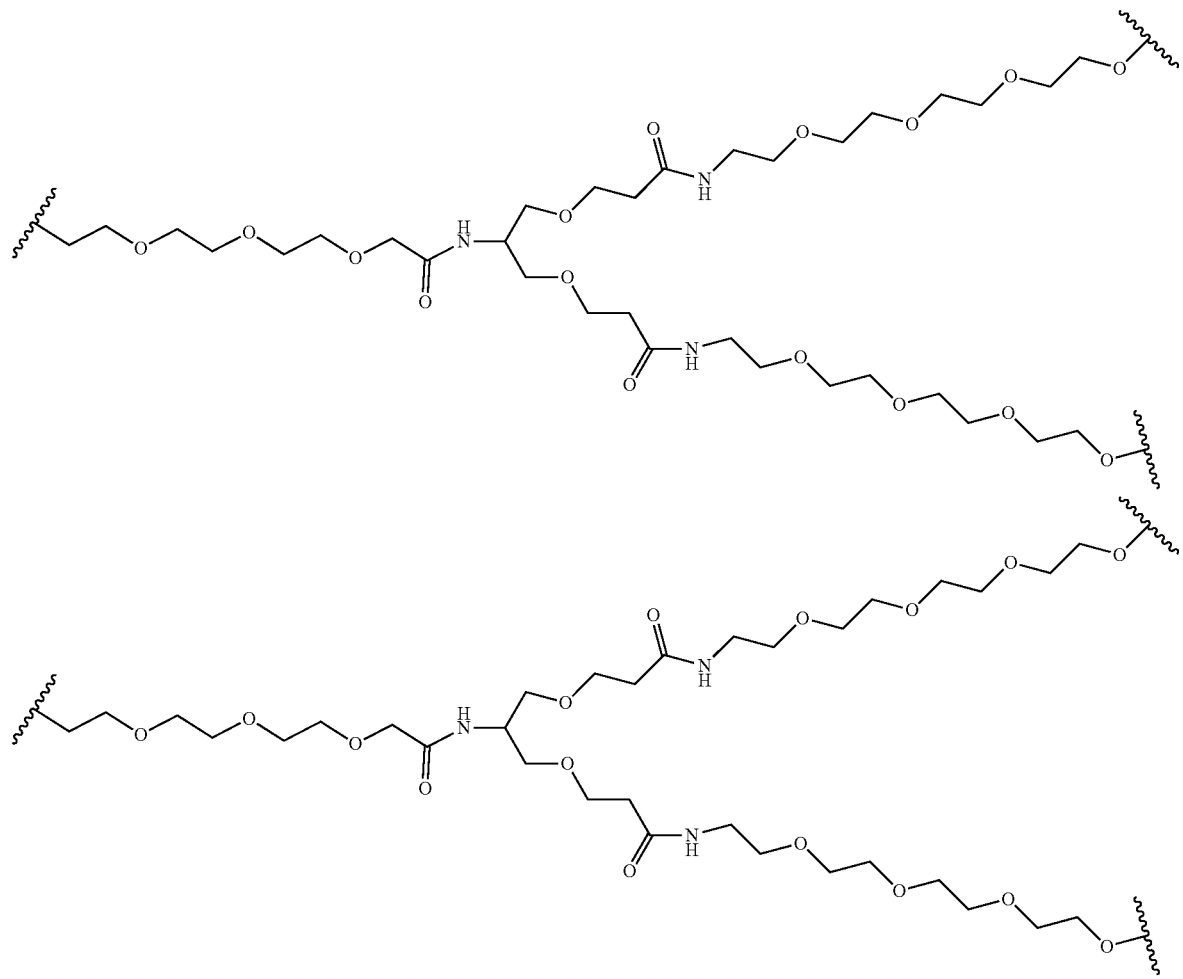
and
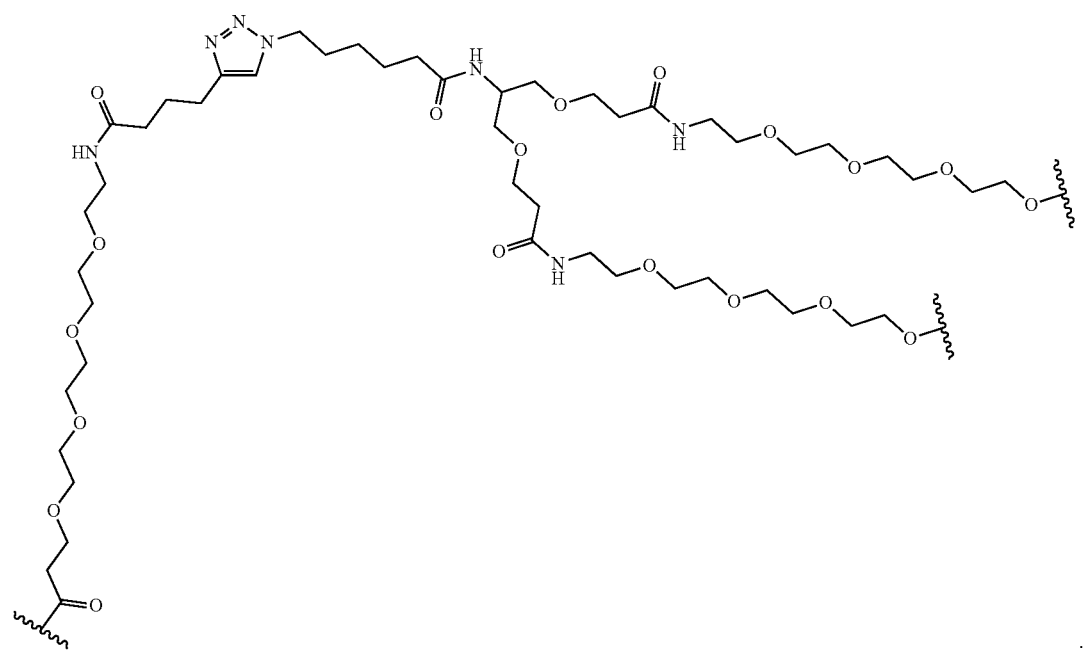 [SMILES: *OCCOCCOCCOCCNC(=O)CCOCC(COCCC(=O)NCCOCCOCCOCCO*)NC(=O)CCCCCn1cc(CCCC(=O)NCCOCCOCCOCCOCCC(*)=O)nn1]

In certain embodiments, Linker$^D$-(Linker A) is selected from

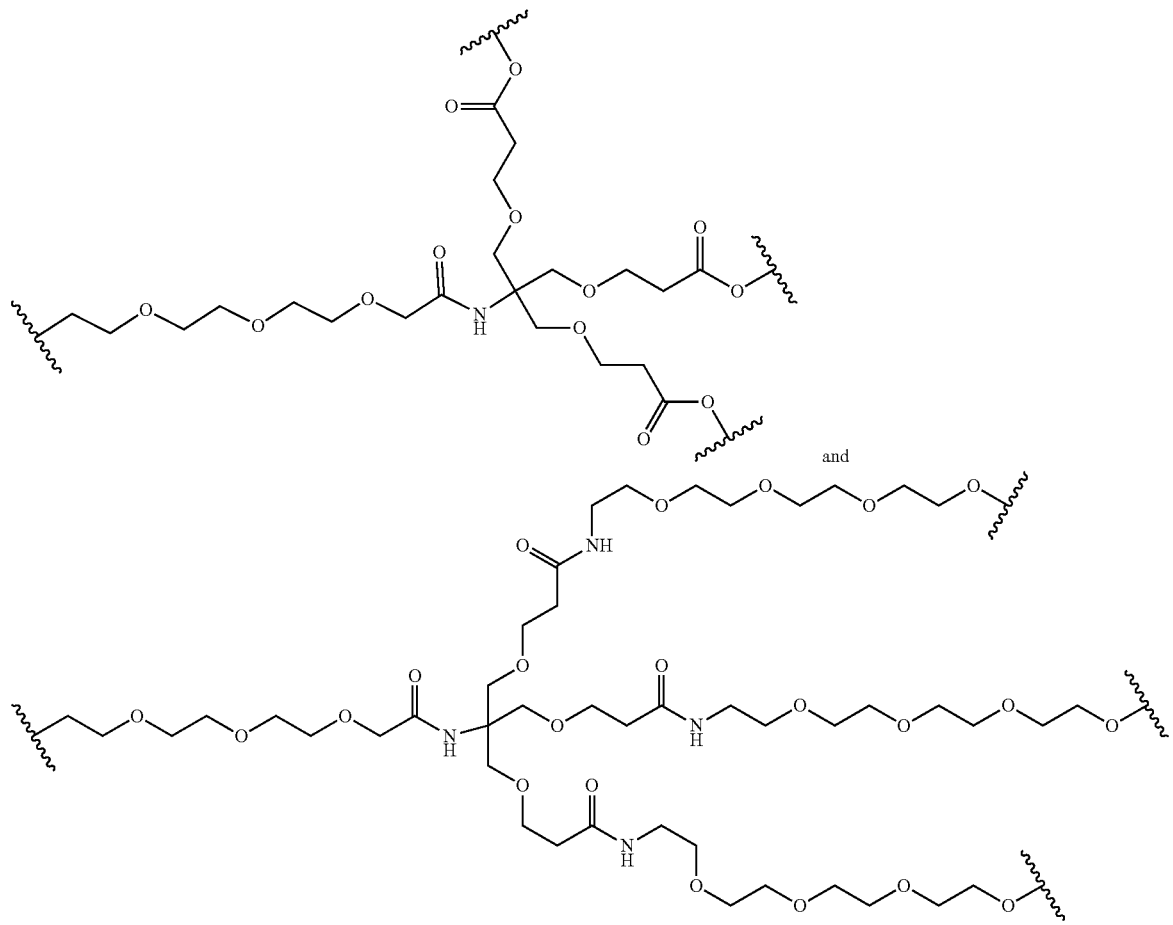

In certain embodiments Linker$^B$ is selected from:

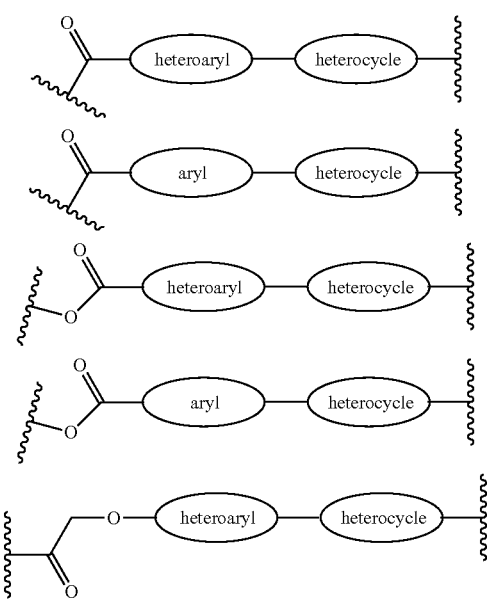

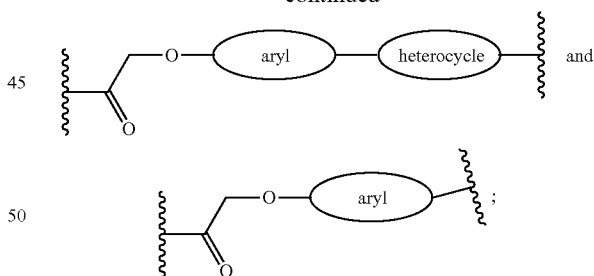

wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence.

In certain embodiments Linker$^B$ is selected from:

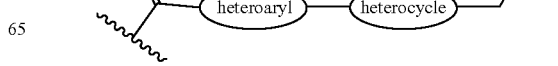

613

-continued

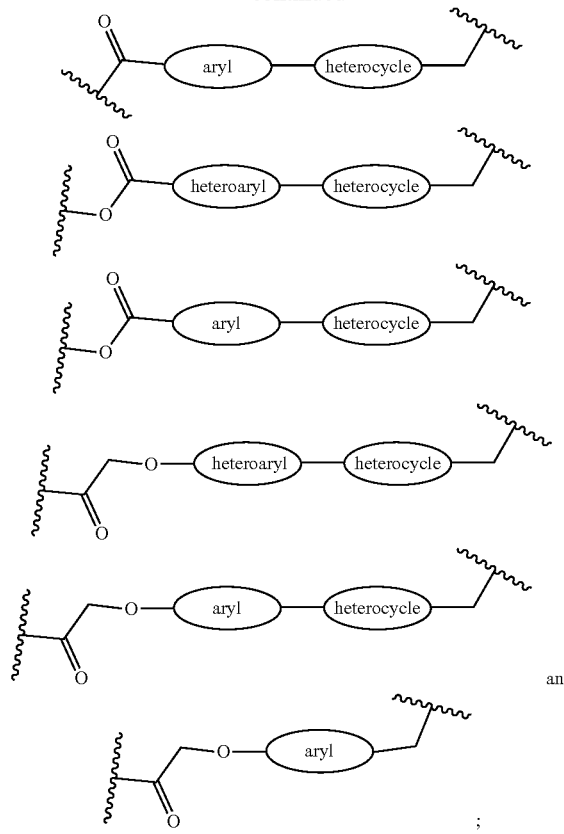

wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence.

In certain embodiments Linker$^B$ is selected from:

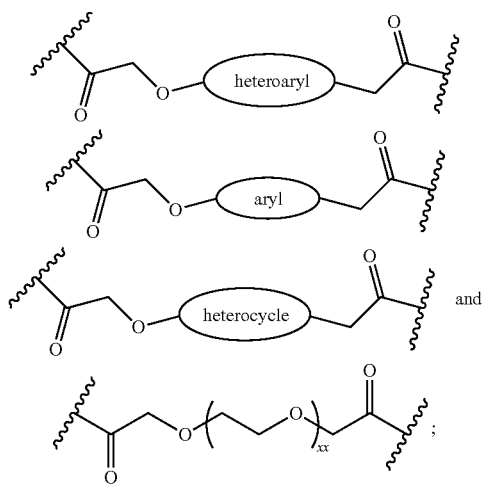

wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence.

In certain embodiments Linker$^B$, Linker$^C$, or Linker$^D$ is selected from:

614

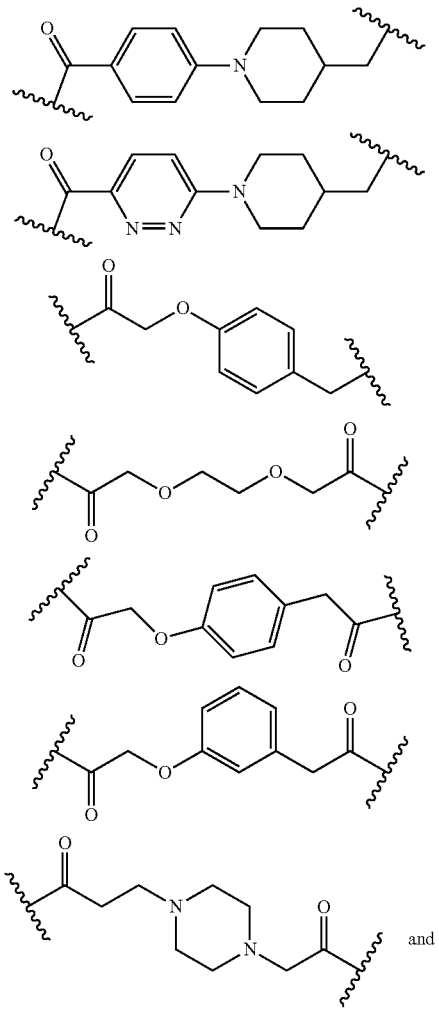

wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence.

In certain embodiments Linker$^A$ is selected from:

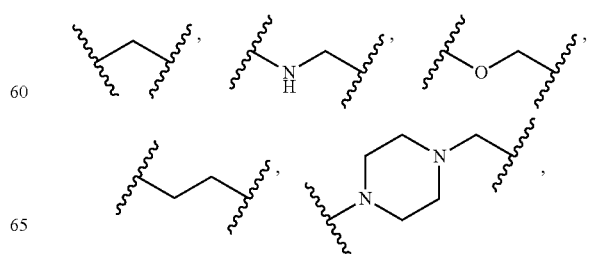

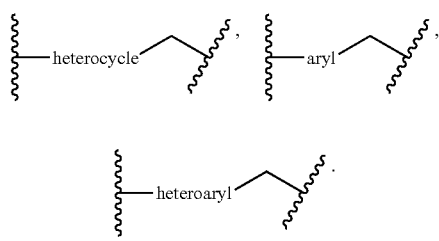

In certain embodiments Linker$^A$ is selected from:

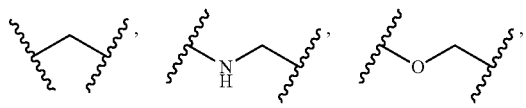

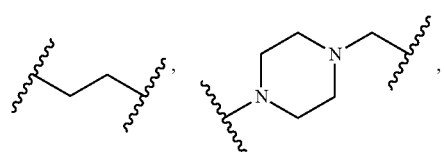

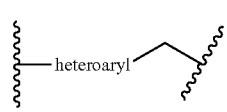

each of which is substituted with 1 or 2 optional substituents.

In certain embodiments Linker$^A$ is bond.

In certain embodiments the left side of Linker$^A$ is attached to the ASGPR Binding Ligand and the right side is attached to Linker$^B$, Linker$^C$, or Linker$^D$.

In certain embodiments the right side of Linker$^A$ is attached to the ASGPR Binding Ligand and the right side is attached to Linker$^B$, Linker$^C$, or Linker$^D$.

In certain embodiments Linker$^B$ is selected from:

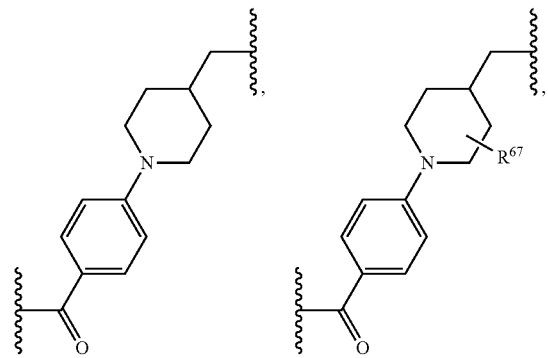

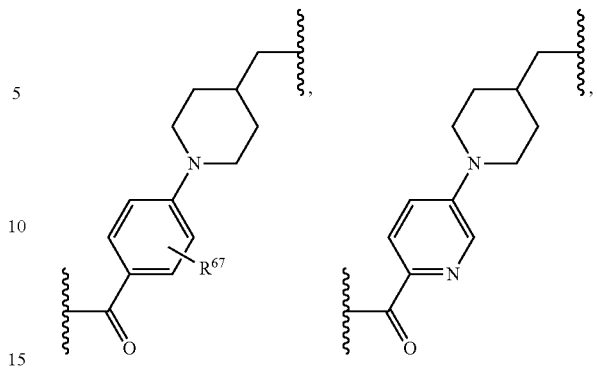

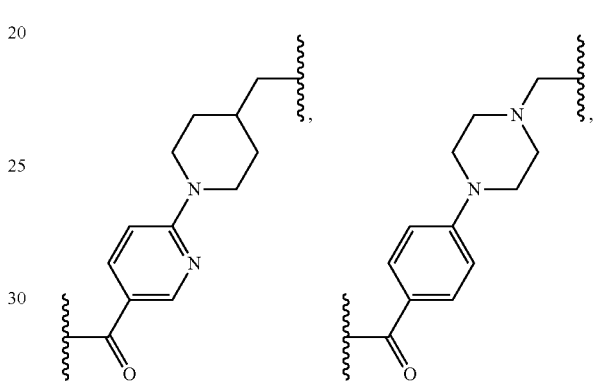

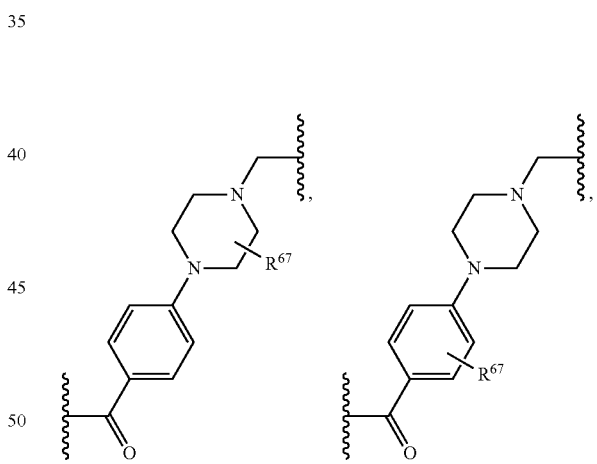

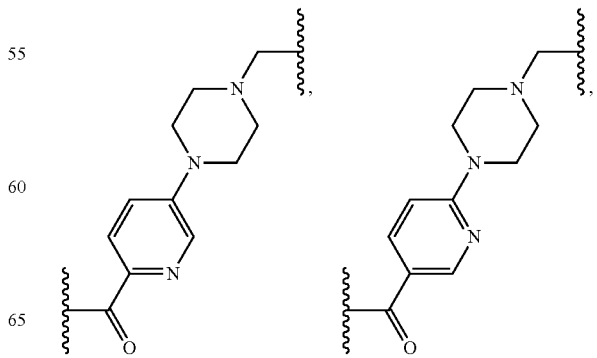

-continued

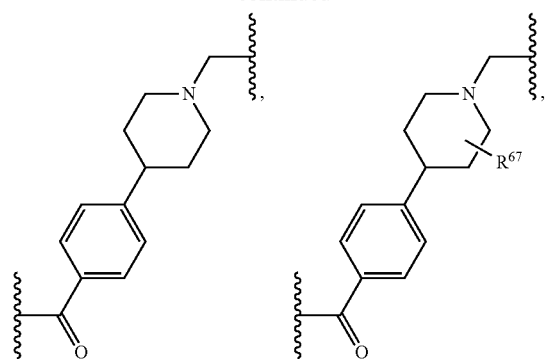

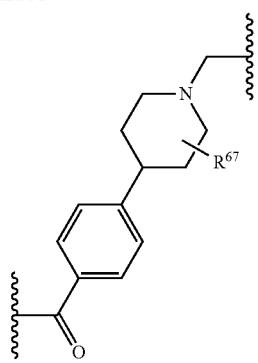 and

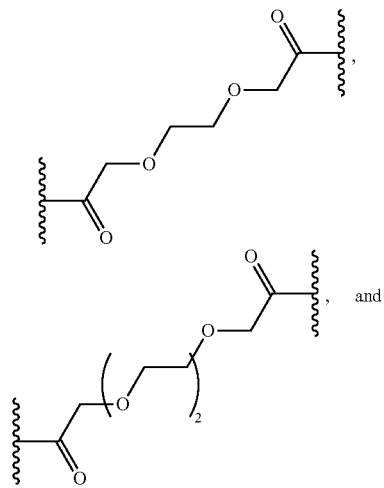

In certain embodiments Linker$^B$ is selected from:

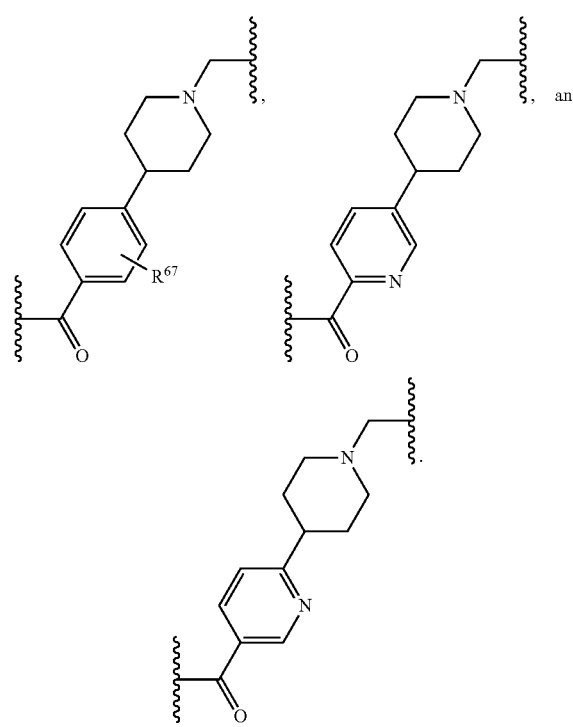

-continued

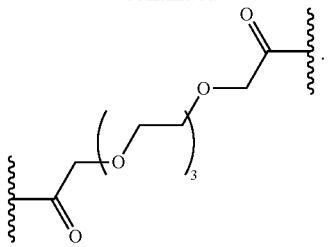

In certain embodiments the left side of Linker$^B$ is attached to the Extracellular Targeting Ligand and the right side is attached to Linker$^A$ In certain embodiments the right side of Linker$^B$ is attached to the Extracellular Targeting Ligand and the left side is attached to Linker$^A$.

In certain embodiments Linker$^B$ is bond.

In alternative embodiments a linker is provided as described above wherein a

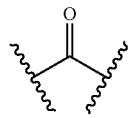 [SMILES: *C(*)=O]

is replaced with a

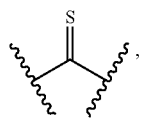 [SMILES: *C(*)=S]

for example where Linker$^B$ is drawn as

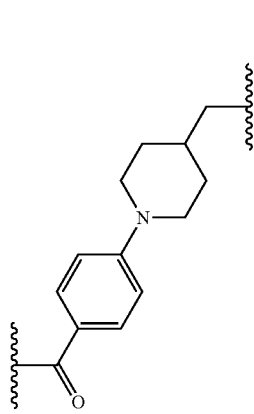 [SMILES: *CC1CCN(c2ccc(C(*)=O)cc2)CC1]

it is

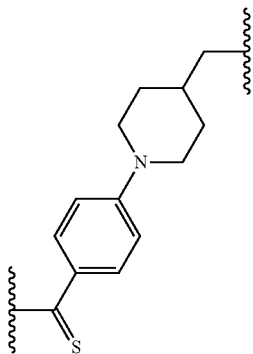 [SMILES: *CC1CCN(c2ccc(C(*)=S)cc2)CC1]

in this embodiment.

In alternative embodiments a linker is provided as described above wherein a

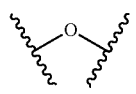

is replaced with a

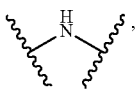

for example where Linker$^B$ is drawn as

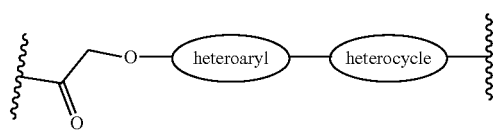

it is

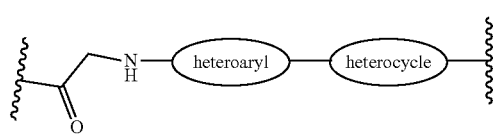

in this embodiment.

In alternative embodiments a linker is provided as described above wherein a

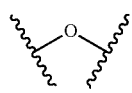

is replaced with a

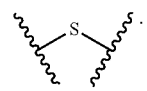

Embodiments of ASGPR Binding Ligand

In certain embodiments ASGPR Binding Ligand is of Formula:

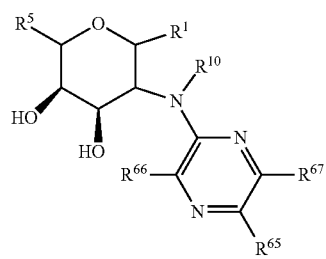

or a pharmaceutically acceptable salt thereof, wherein if the ASGPR Binding Ligand is part of an extracellular protein degrading compound then $R^5$ or $R^1$ is replaced with a bond to Linker$^A$.

In certain embodiments ASGPR Binding Ligand is of Formula:

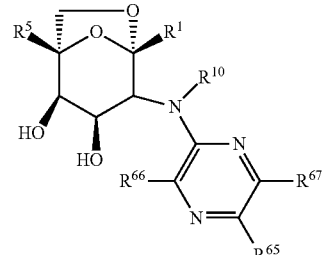

or a pharmaceutically acceptable salt thereof, wherein if the ASGPR Binding Ligand is part of an extracellular protein degrading compound then $R^5$ or $R^1$ is replaced with a bond to Linker$^A$.

In certain embodiments ASGPR Binding Ligand is of Formula:

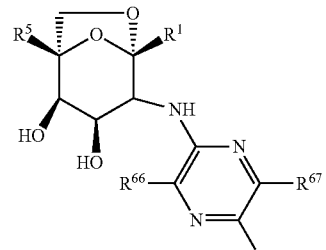

or a pharmaceutically acceptable salt thereof, wherein if the ASGPR Binding Ligand is part of an extracellular protein degrading compound then $R^5$ or $R^1$ is replaced with a bond to Linker$^A$.

In certain embodiments ASGPR Binding Ligand is of Formula:

621

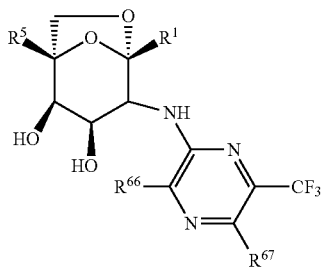

or a pharmaceutically acceptable salt thereof, wherein if the ASGPR Binding Ligand is part of an extracellular protein degrading compound then $R^5$ or $R^1$ is replaced with a bond to Linker$^4$.

In certain embodiments ASGPR Binding Ligand is of Formula:

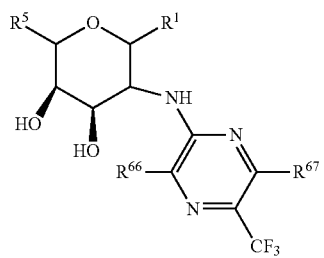

or a pharmaceutically acceptable salt thereof, wherein if the ASGPR Binding Ligand is part of an extracellular protein degrading compound then $R^5$ or $R^1$ is replaced with a bond to Linker$^4$.

In certain embodiments ASGPR Binding Ligand is of Formula:

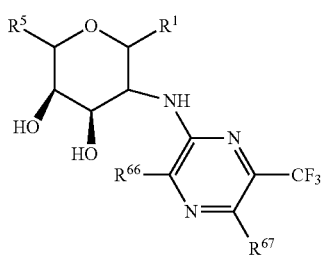

or a pharmaceutically acceptable salt thereof, wherein if the ASGPR Binding Ligand is part of an extracellular protein degrading compound then $R^5$ or $R^1$ is replaced with a bond to Linker$^4$.

In certain embodiments ASGPR Binding Ligand is of Formula:

622

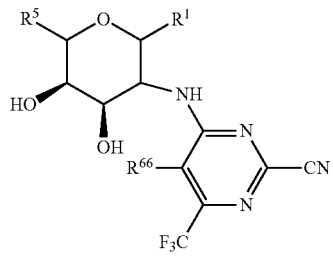

or a pharmaceutically acceptable salt thereof, wherein if the ASGPR Binding Ligand is part of an extracellular protein degrading compound then $R^5$ or $R^1$ is replaced with a bond to Linker$^4$.

In certain embodiments ASGPR Binding Ligand is of Formula:

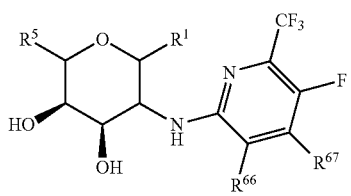

or a pharmaceutically acceptable salt thereof, wherein if the ASGPR Binding Ligand is part of an extracellular protein degrading compound then $R^5$ or $R^1$ is replaced with a bond to Linker$^4$.

In certain embodiments ASGPR Binding Ligand is of Formula:

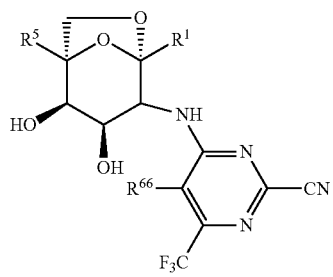

or a pharmaceutically acceptable salt thereof, wherein if the ASGPR Binding Ligand is part of an extracellular protein degrading compound then $R^5$ or $R^1$ is replaced with a bond to Linker$^4$.

In certain embodiments ASGPR Binding Ligand is of Formula:

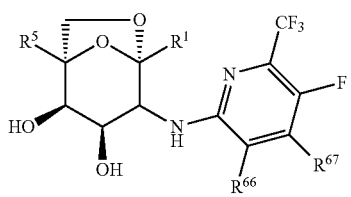

or a pharmaceutically acceptable salt thereof, wherein if the ASGPR Binding Ligand is part of an extracellular protein degrading compound then $R^5$ or $R^1$ is replaced with a bond to Linker$^A$.

In certain embodiments ASGPR Binding Ligand is of Formula:

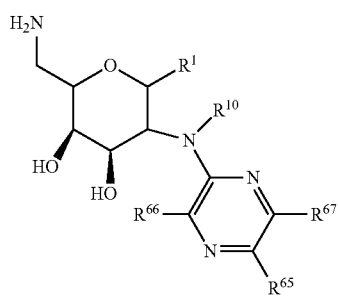

or a pharmaceutically acceptable salt thereof, wherein if the ASGPR Binding Ligand is part of an extracellular protein degrading compound then Linker$^A$ is attached to the Nitrogen at the C5 position.

In certain embodiments ASGPR Binding Ligand is of Formula:

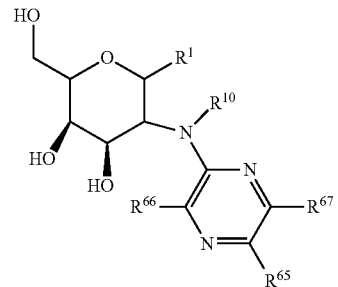

or a pharmaceutically acceptable salt thereof, wherein if the ASGPR Binding Ligand is part of an extracellular protein degrading compound then Linker$^A$ is attached to the Oxygen at the C5 position.

In certain embodiments ASGPR Binding Ligand is of Formula:

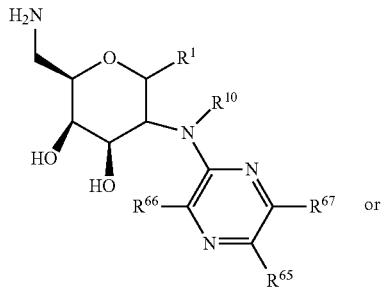

or

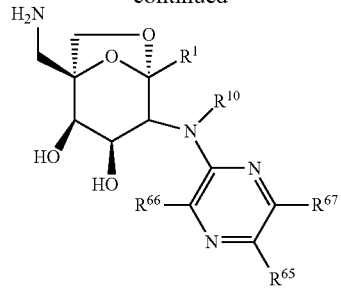

or a pharmaceutically acceptable salt thereof, wherein if the ASGPR Binding Ligand is part of an extracellular protein degrading compound then Linker$^A$ is attached to the Nitrogen at the C5 position.

In certain embodiments ASGPR Binding Ligand is of Formula:

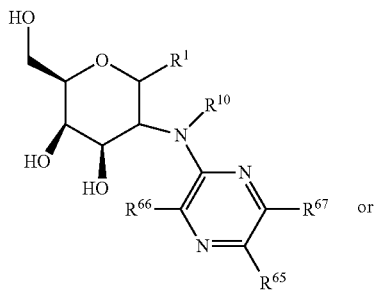

or

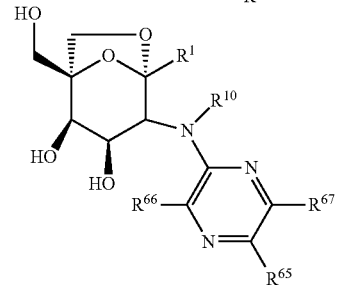

or a pharmaceutically acceptable salt thereof, wherein if the ASGPR Binding Ligand is part of an extracellular protein degrading compound then Linker$^A$ is attached to the Nitrogen at the C5 position.

In certain aspects an extracellular protein degrading compound is of Formula

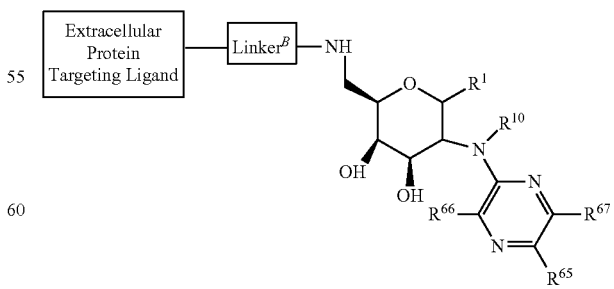

or a pharmaceutically acceptable salt thereof.

In certain aspects an extracellular protein degrading compound is of Formula

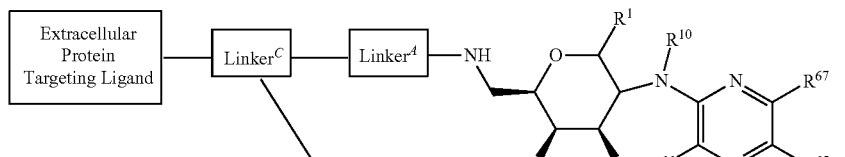
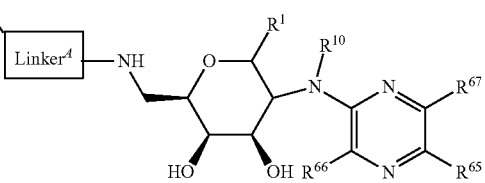
or a pharmaceutically acceptable salt thereof.
In certain aspects an extracellular protein degrading compound is of Formula
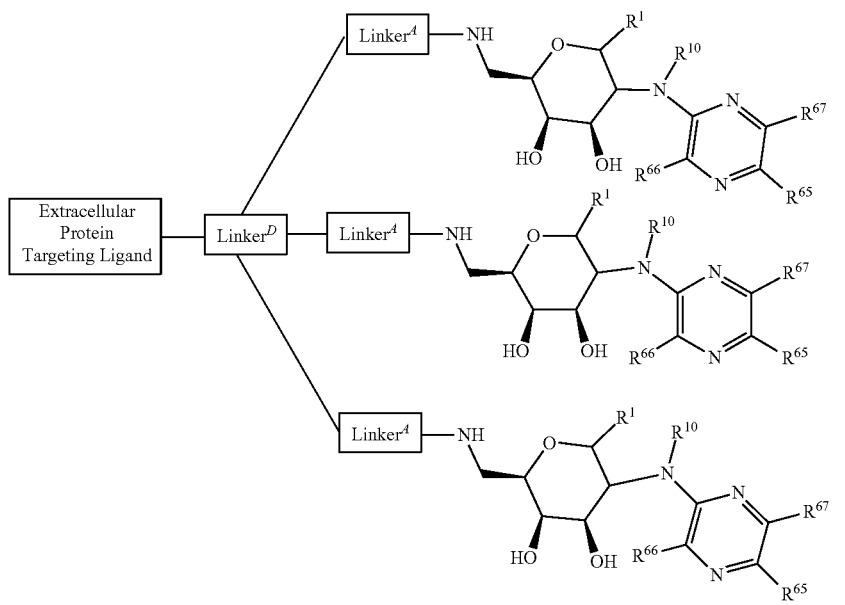
or a pharmaceutically acceptable salt thereof.
In certain aspects an extracellular protein degrading compound is of Formula
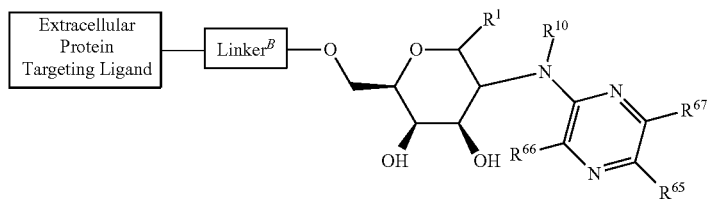
or a pharmaceutically acceptable salt thereof.

In certain aspects an extracellular protein degrading compound is of Formula

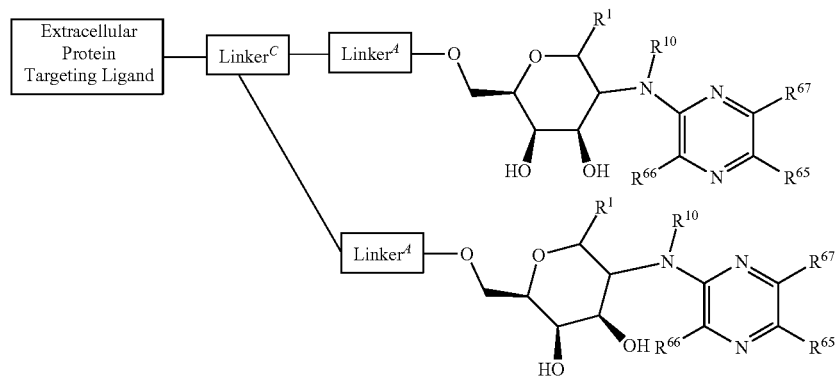

or a pharmaceutically acceptable salt thereof.

In certain aspects an extracellular protein degrading compound is of Formula

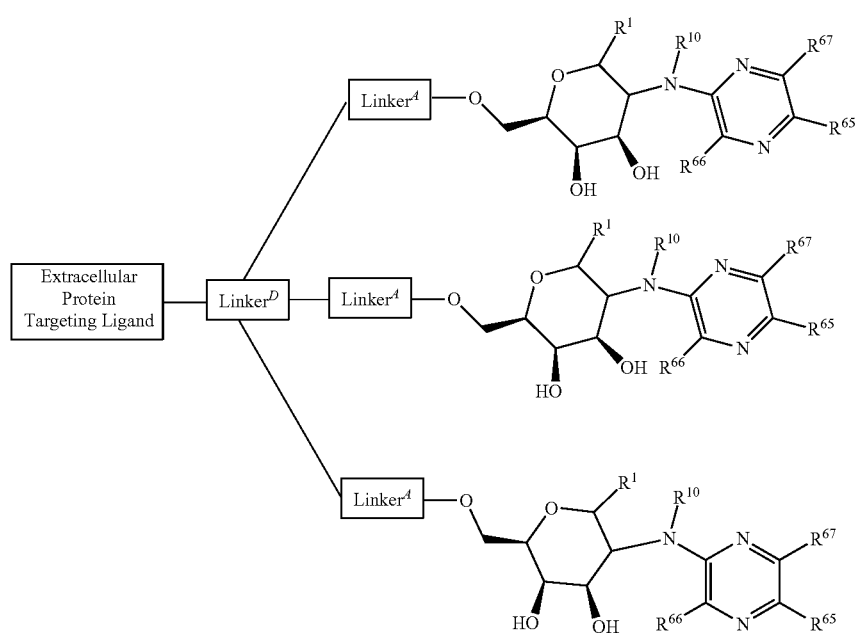

or a pharmaceutically acceptable salt thereof.

In certain embodiments ASGPR Binding Ligand is of Formula:

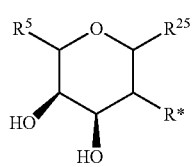 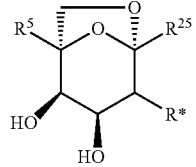

-continued

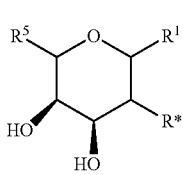 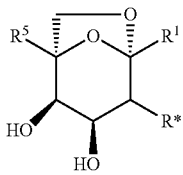

or a pharmaceutically acceptable salt thereof, wherein if the ASGPR Binding Ligand is part of an extracellular protein degrading compound then $R^5$ is replaced with a bond to Linker$^A$ and wherein R* is selected from:

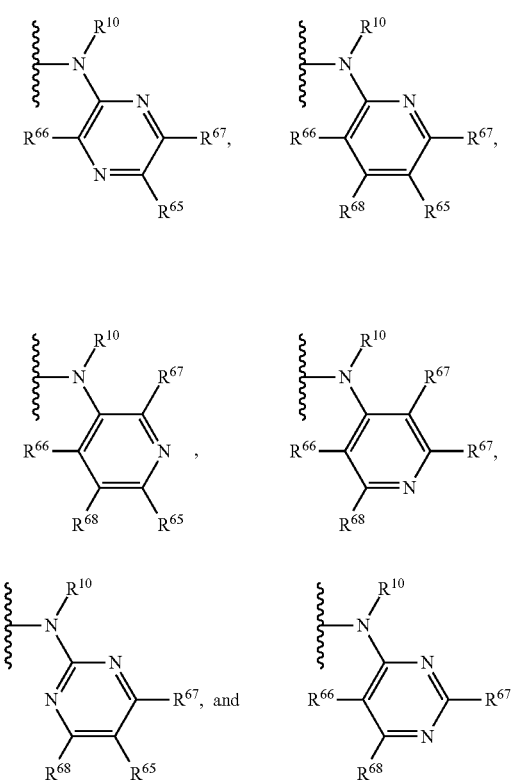

In certain embodiments ASGPR Binding Ligand is of Formula:

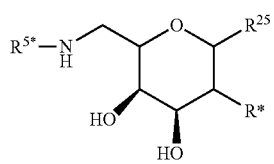

or a pharmaceutically acceptable salt thereof, wherein if the ASGPR Binding Ligand is part of an extracellular protein degrading compound then $R^{5*}$ is replaced with a bond to Linker$^4$; and $R^{5*}$ is alkyl, $C(O)R^3$, or hydrogen.

In certain embodiments the ASGPR Binding Ligand is of Formula:

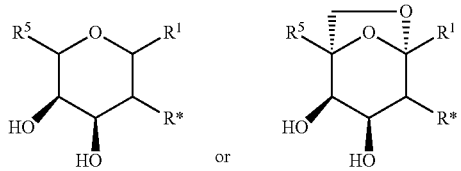

or a pharmaceutically acceptable salt thereof, wherein if the ASGPR Binding Ligand is part of an extracellular protein degrading compound then $R^1$ or $R^5$ is replaced with a bond to Linker$^4$.

In certain embodiments R* is selected from:

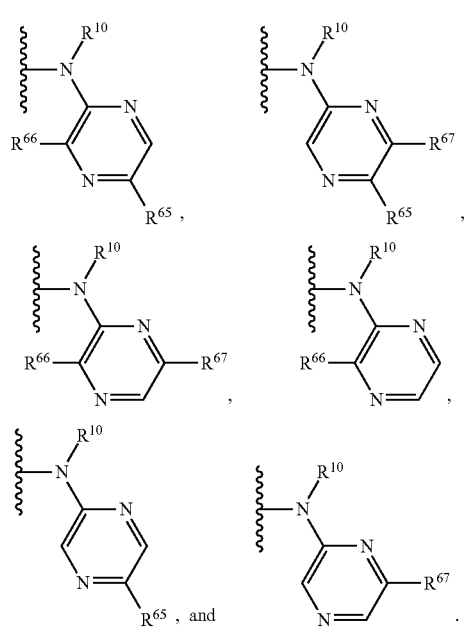

Non limiting examples of R* include:

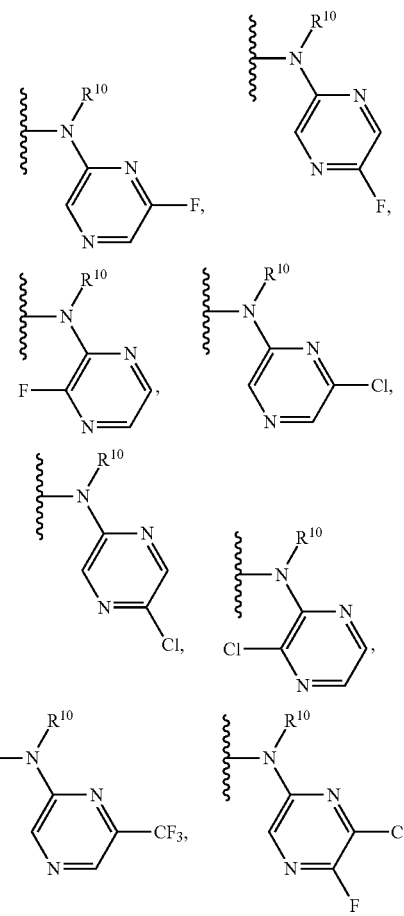

-continued
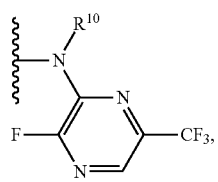 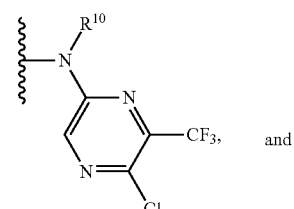 and
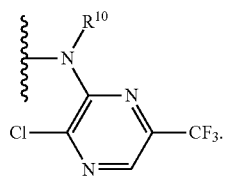
In certain embodiments the ASGPR Binding Ligand is of Formula
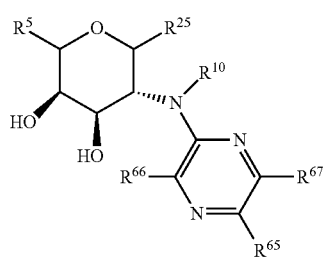
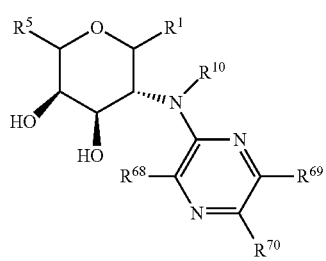
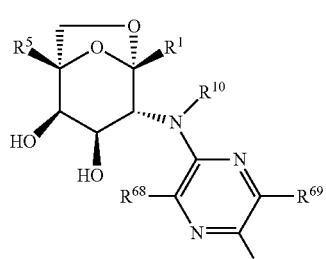
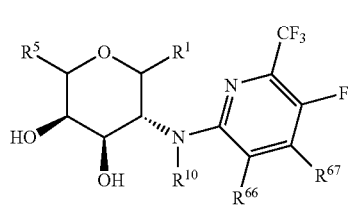
-continued
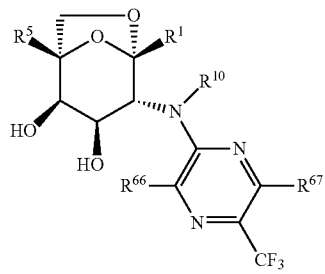
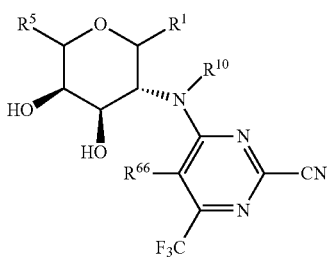
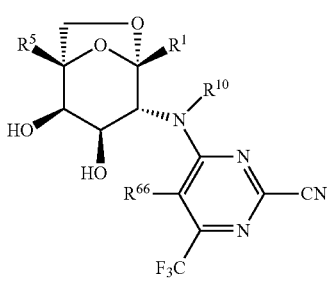
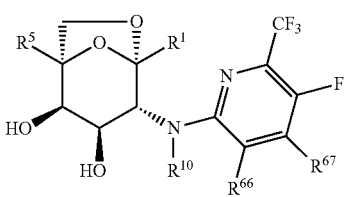
or a pharmaceutically acceptable salt thereof, wherein if the ASGPR Binding Ligand is part of an extracellular protein degrading compound then $R^5$ is replaced with a bond to Linker$^4$.
In certain embodiments the ASGPR Binding Ligand is of Formula
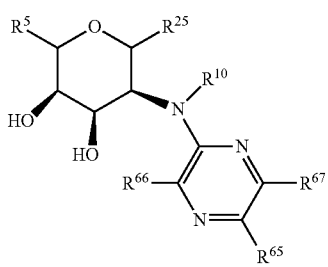

-continued
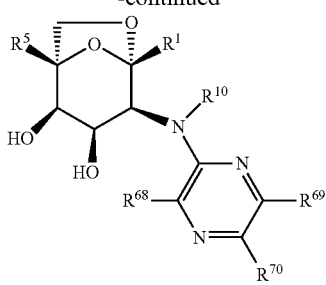
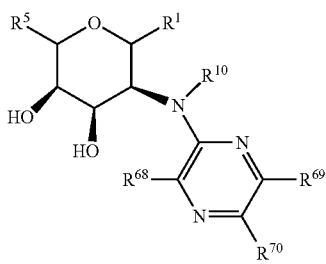
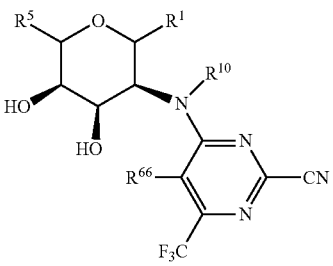
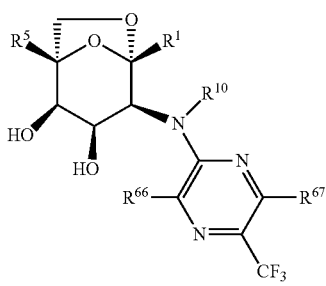
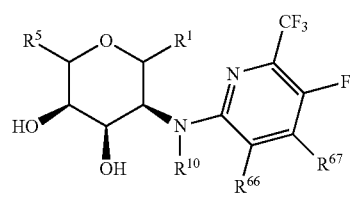
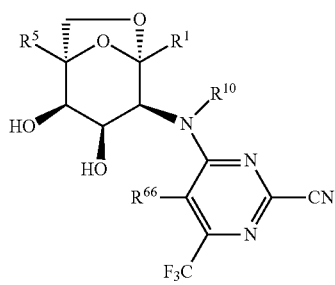
-continued
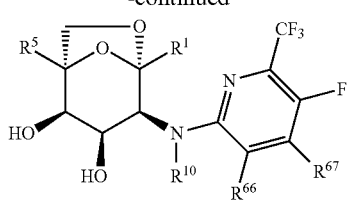
or a pharmaceutically acceptable salt thereof, wherein if the ASGPR Binding Ligand is part of an extracellular protein degrading compound then $R^5$ is replaced with a bond to Linker$^4$.
In certain embodiments, ASGPR Binding Ligand is selected from
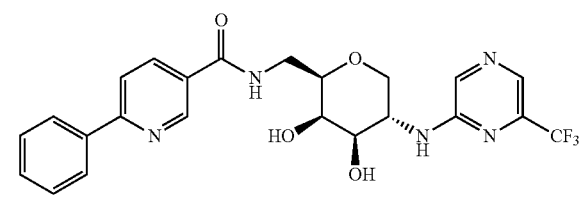
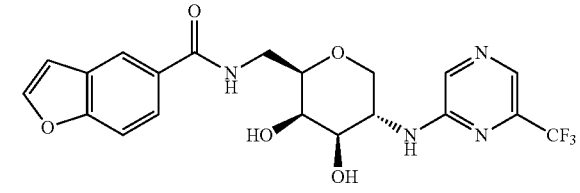
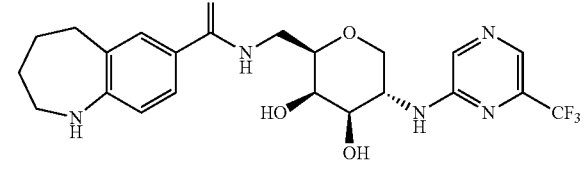
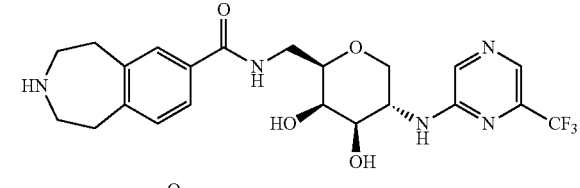
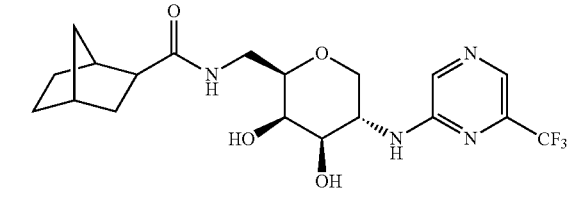
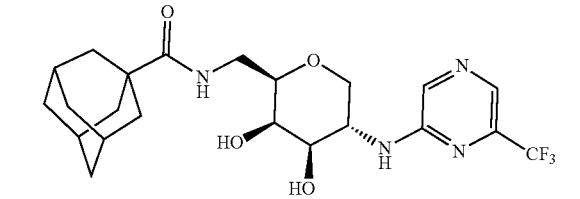

635
-continued

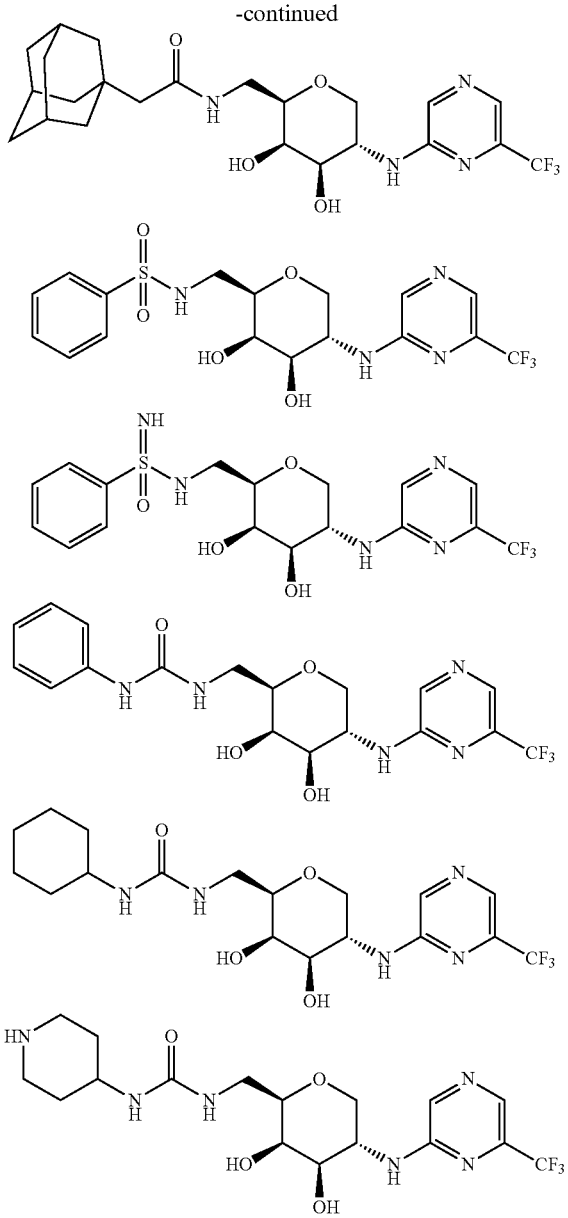

or a pharmaceutically acceptable salt thereof, wherein if the ASGPR Binding Ligand is part of an extracellular protein degrading compound then the substituent at the C1 or C5 position is bonded with Linker⁴.

In certain embodiments, ASGPR Binding Ligand is selected from

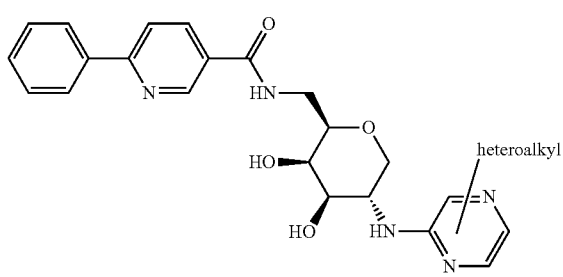

636
-continued

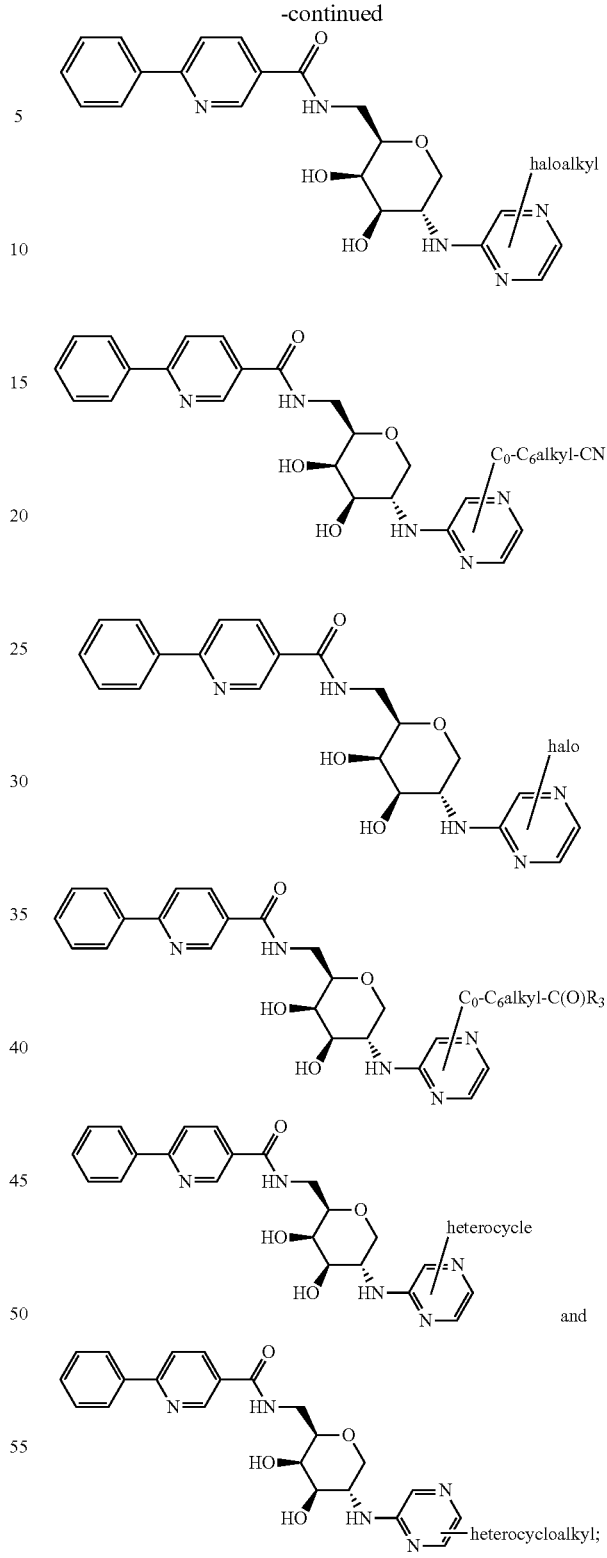

or a pharmaceutically acceptable salt thereof, wherein if the ASGPR Binding Ligand is part of an extracellular protein degrading compound then the substituent at the C1 or C5 position is bonded with Linker⁴.

In certain embodiments, ASGPR Binding Ligand is selected from:

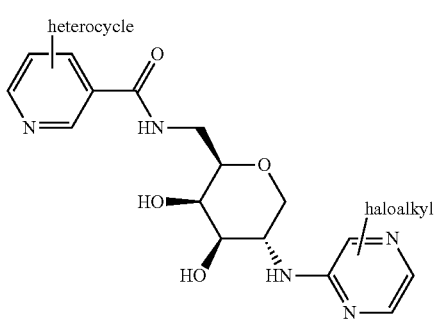
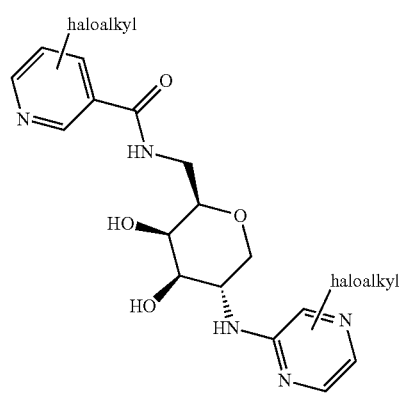
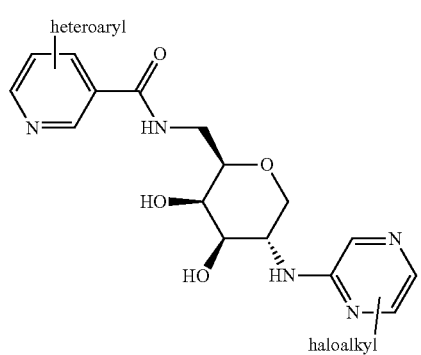
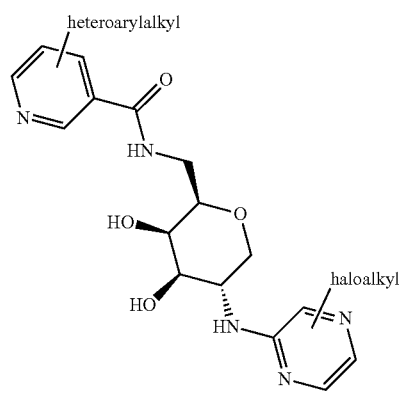
-continued
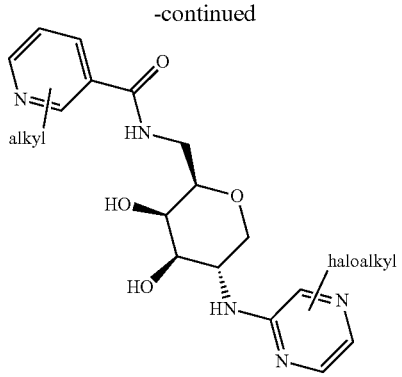
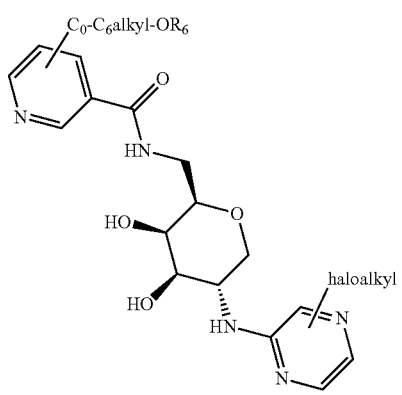
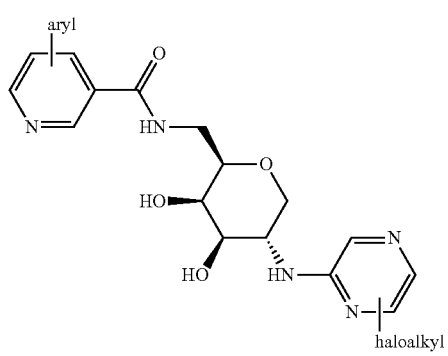
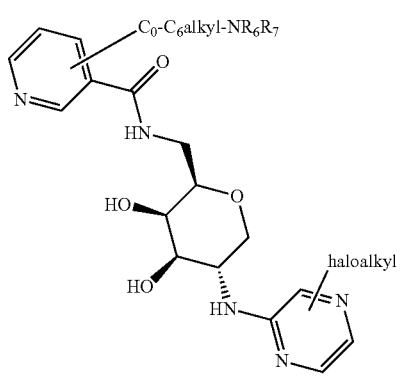

639
-continued
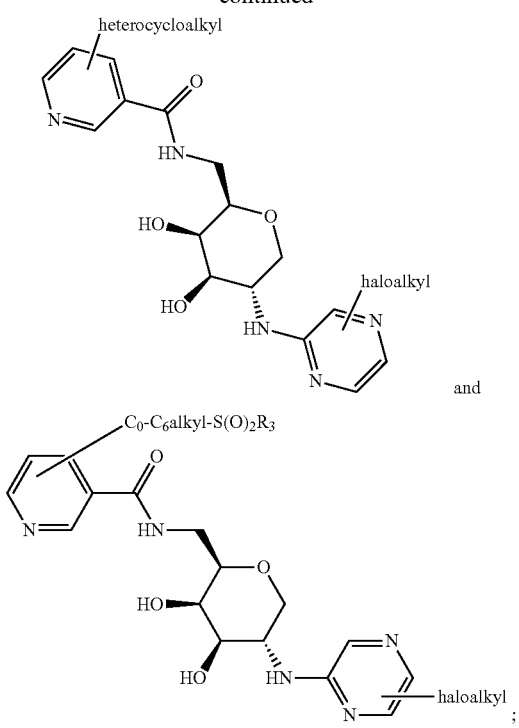
and
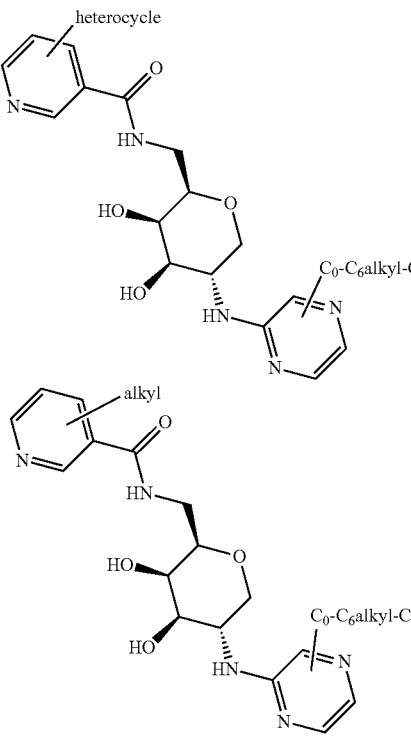
;
or a pharmaceutically acceptable salt thereof, wherein if the ASGPR Binding Ligand is part of an extracellular protein degrading compound then the substituent at the C1 or C5 position is bonded with Linker$^A$.
In certain embodiments, ASGPR Binding Ligand is selected from:
640
-continued
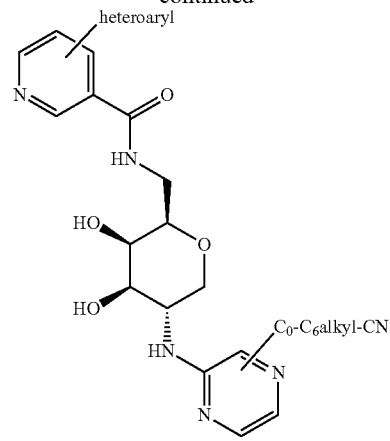
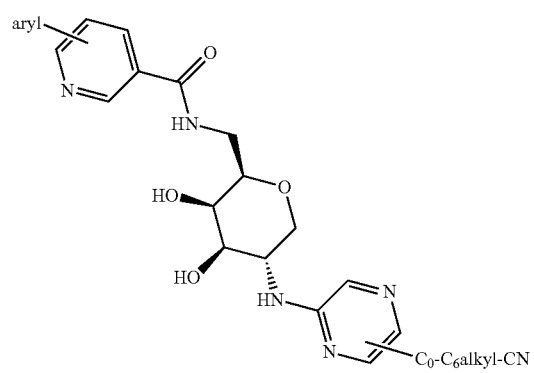
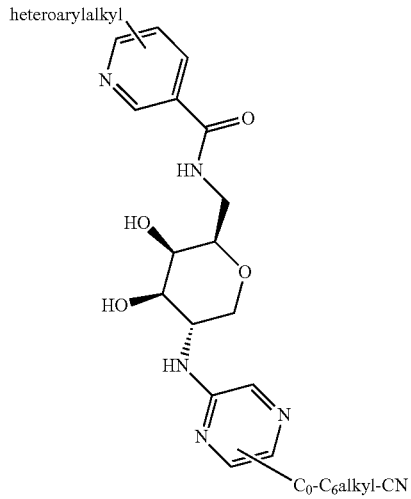

641
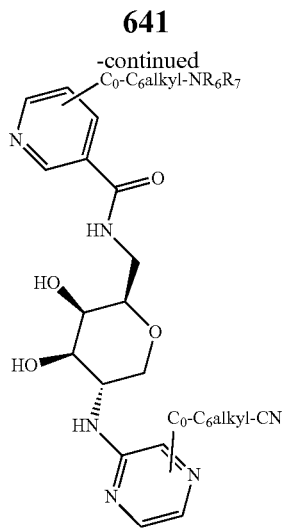
642
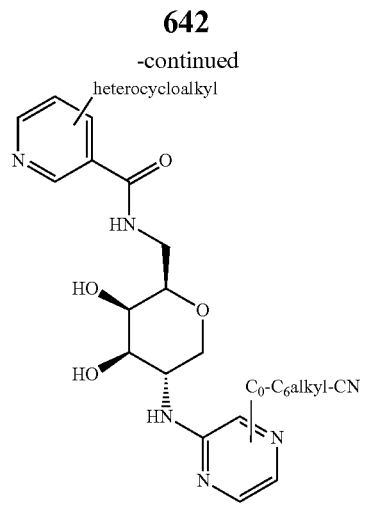
or a pharmaceutically acceptable salt thereof, wherein if the ASGPR Binding Ligand is part of an extracellular protein degrading compound then the substituent at the C1 or C5 position is bonded with Linker$^4$.
In certain embodiments the extracellular protein degrading compound is selected from:
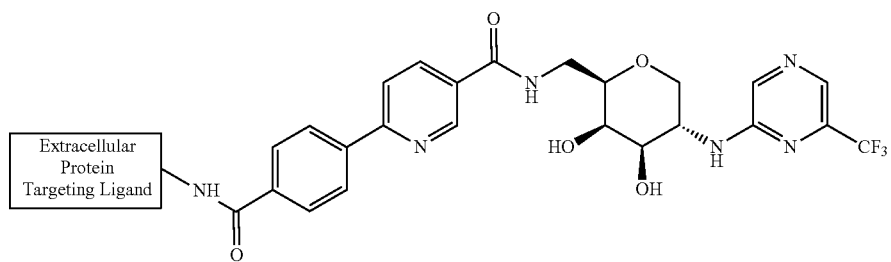

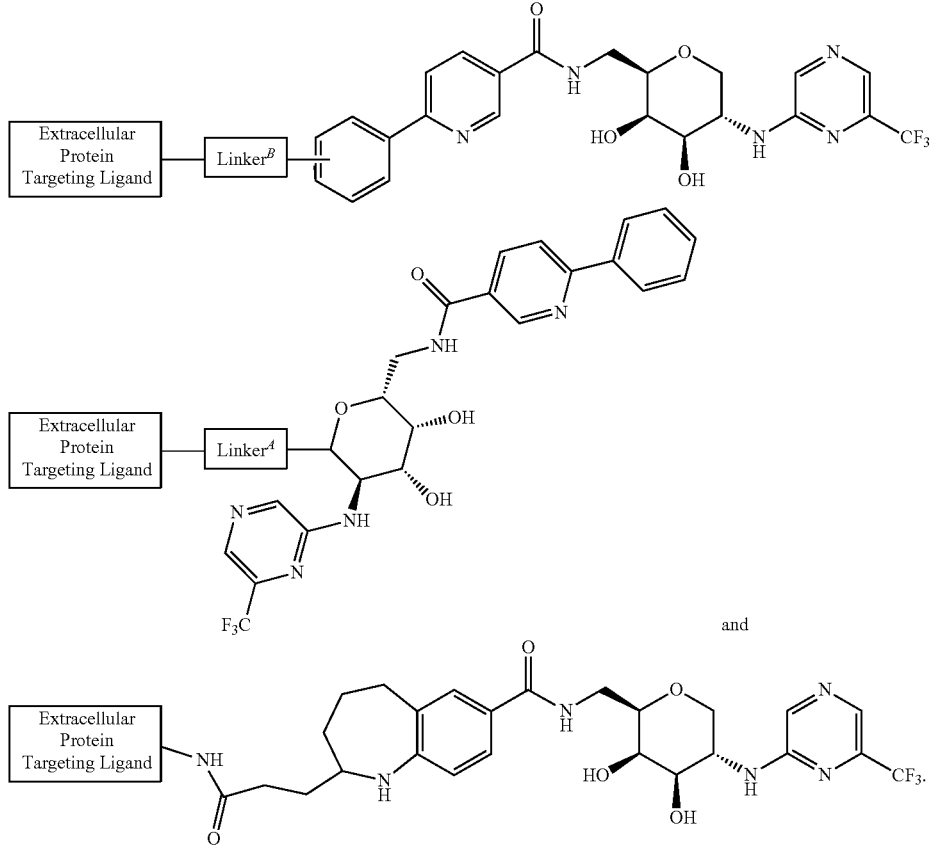

Embodiments of $R^1$

In certain embodiments $R^1$ is hydrogen.
In certain embodiments $R^1$ is

In certain embodiments $R^1$ is

In certain embodiments $R^1$ is

In certain embodiments $R^1$ is

In certain embodiments $R^1$ is

In certain embodiments $R^1$ is heteroalkyl optionally substituted with 1, 2, 3, or 4 substituents.
In certain embodiments $R^1$ is $C_0$-$C_6$alkyl-cyano optionally substituted with 1, 2, 3, or 4 substituents.
In certain embodiments $R^1$ is alkyl optionally substituted with 1, 2, 3, or 4 substituents.
In certain embodiments $R^1$ is alkenyl optionally substituted with 1, 2, 3, or 4 substituents.
In certain embodiments $R^1$ is alkynyl optionally substituted with 1, 2, 3, or 4 substituents.

In certain embodiments $R^1$ is haloalkyl optionally substituted with 1, 2, 3, or 4 substituents.

In certain embodiments $R^1$ is F.

In certain embodiments $R^1$ is Cl.

In certain embodiments $R^1$ is Br.

In certain embodiments $R^1$ is aryl optionally substituted with 1, 2, 3, or 4 substituents.

In certain embodiments $R^1$ is arylalkyl optionally substituted with 1, 2, 3, or 4 substituents.

In certain embodiments $R^1$ is heteroaryl optionally substituted with 1, 2, 3, or 4 substituents.

In certain embodiments $R^1$ is heteroarylalkyl optionally substituted with 1, 2, 3, or 4 substituents.

In certain embodiments $R^1$ is heterocycle optionally substituted with 1, 2, 3, or 4 substituents.

In certain embodiments $R^1$ is heterocycloalkyl optionally substituted with 1, 2, 3, or 4 substituents.

In certain embodiments $R^1$ is haloalkoxy optionally substituted with 1, 2, 3, or 4 substituents.

In certain embodiments $R^1$ is —O-alkenyl, —O-alkynyl, $C_0$-$C_6$alkyl-$OR^6$, $C_0$-$C_6$alkyl-$SR^6$, $C_0$-$C_6$alkyl-$NR^6R^7$, $C_0$-$C_6$alkyl-$C(O)R^3$, $C_0$-$C_6$alkyl-$S(O)R^3$, $C_0$-$C_6$alkyl-$C(S)R^3$, $C_0$-$C_6$alkyl-$S(O)_2R^3$, $C_0$-$C_6$alkyl-$N(R^8)$—$C(O)R^3$, $C_0$-$C_6$alkyl-$N(R^8)$—$S(O)R^3$, $C_0$-$C_6$alkyl-$N(R^8)$—$C(S)R^3$, $C_0$-$C_6$alkyl-$N(R^8)$—$S(O)_2R^3$, $C_0$-$C_6$alkyl-O—$C(O)R^3$, $C_0$-$C_6$alkyl-O—$S(O)R^3$, $C_0$-$C_6$alkyl-O—$C(S)R^3$, —N=S$(O)(R^3)_2$, $C_0$-$C_6$alkyl$N_3$, or $C_0$-$C_6$alkyl-O—$S(O)_2R^3$, each of which is optionally substituted with 1, 2, 3, or 4 substituents.

Embodiments of $R^5$

In certain embodiments $R^5$ is hydrogen.

In certain embodiments $R^5$ is

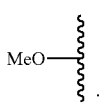

In certain embodiments $R^5$ is

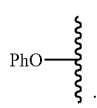

In certain embodiments $R^5$ is

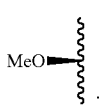

In certain embodiments $R^5$ is

In certain embodiments $R^5$ is

In certain embodiments $R^5$ is

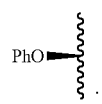

In certain embodiments $R^5$ is heteroalkyl optionally substituted with 1, 2, 3, or 4 substituents.

In certain embodiments $R^5$ is $C_0$-$C_6$alkyl-cyano optionally substituted with 1, 2, 3, or 4 substituents.

In certain embodiments $R^5$ is alkyl optionally substituted with 1, 2, 3, or 4 substituents.

In certain embodiments $R^5$ is alkenyl optionally substituted with 1, 2, 3, or 4 substituents.

In certain embodiments $R^5$ is alkynyl optionally substituted with 1, 2, 3, or 4 substituents.

In certain embodiments $R^5$ is haloalkyl optionally substituted with 1, 2, 3, or 4 substituents.

In certain embodiments $R^5$ is F.

In certain embodiments $R^5$ is Cl.

In certain embodiments $R^5$ is Br.

In certain embodiments $R^5$ is aryl optionally substituted with 1, 2, 3, or 4 substituents.

In certain embodiments $R^5$ is arylalkyl optionally substituted with 1, 2, 3, or 4 substituents.

In certain embodiments $R^5$ is heteroaryl optionally substituted with 1, 2, 3, or 4 substituents.

In certain embodiments $R^5$ is heteroarylalkyl optionally substituted with 1, 2, 3, or 4 substituents.

In certain embodiments $R^5$ is heterocycle optionally substituted with 1, 2, 3, or 4 substituents.

In certain embodiments $R^5$ is heterocycloalkyl optionally substituted with 1, 2, 3, or 4 substituents.

In certain embodiments $R^5$ is haloalkoxy optionally substituted with 1, 2, 3, or 4 substituents.

In certain embodiments $R^5$ is —O-alkenyl, —O-alkynyl, $C_0$-$C_6$alkyl-$OR^6$, $C_0$-$C_6$alkyl-$SR^6$, $C_0$-$C_6$alkyl-$NR^6R^7$, $C_0$-$C_6$alkyl-$C(O)R^3$, $C_0$-$C_6$alkyl-$S(O)R^3$, $C_0$-$C_6$alkyl-$C(S)R^3$, $C_0$-$C_6$alkyl-$S(O)_2R^3$, $C_0$-$C_6$alkyl-$N(R^8)$—$C(O)R^3$, $C_0$-$C_6$alkyl-$N(R^8)$—$S(O)R^3$, $C_0$-$C_6$alkyl-$N(R^8)$—$C(S)R^3$, $C_0$-$C_6$alkyl-$N(R^8)$—$S(O)_2R^3$, $C_0$-$C_6$alkyl-O—$C(O)R^3$, $C_0$-$C_6$alkyl-O—$S(O)R^3$, $C_0$-$C_6$alkyl-O—$C(S)R^3$, —N=S$(O)(R^3)_2$, $C_0$-$C_6$alkyl$N_3$, or $C_0$-$C_6$alkyl-O—$S(O)_2R^3$, each of which is optionally substituted with 1, 2, 3, or 4 substituents.

Embodiments of $R^{10}$

In certain embodiments $R^{10}$ is hydrogen.

In certain embodiments $R^{10}$ is alkyl.

In certain embodiments $R^{10}$ is haloalkyl.

In certain embodiments $R^{10}$ is $C(O)R^3$.

Embodiments of $R^{25}$

In certain embodiments $R^{25}$ is hydrogen.
In certain embodiments $R^{25}$ is

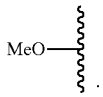

In certain embodiments $R^{25}$ is

In certain embodiments $R^{25}$ is

In certain embodiments $R^{25}$ is

In certain embodiments $R^{25}$ is

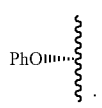

In certain embodiments $R^{25}$ is

In certain embodiments $R^{25}$ is heteroalkyl optionally substituted with 1, 2, 3, or 4 substituents.
In certain embodiments $R^{25}$ is $C_0$-$C_6$alkyl-cyano optionally substituted with 1, 2, 3, or 4 substituents.
In certain embodiments $R^{25}$ is alkyl optionally substituted with 1, 2, 3, or 4 substituents.
In certain embodiments $R^{25}$ is alkenyl optionally substituted with 1, 2, 3, or 4 substituents.
In certain embodiments $R^{25}$ is alkynyl optionally substituted with 1, 2, 3, or 4 substituents.
In certain embodiments $R^{25}$ is haloalkyl optionally substituted with 1, 2, 3, or 4 substituents.
In certain embodiments $R^{25}$ is F.
In certain embodiments $R^{25}$ is Cl.
In certain embodiments $R^{25}$ is Br.
In certain embodiments $R^{25}$ is aryl optionally substituted with 1, 2, 3, or 4 substituents.

In certain embodiments $R^{25}$ is arylalkyl optionally substituted with 1, 2, 3, or 4 substituents.
In certain embodiments $R^{25}$ is heteroaryl optionally substituted with 1, 2, 3, or 4 substituents.
In certain embodiments $R^{25}$ is heteroarylalkyl optionally substituted with 1, 2, 3, or 4 substituents.
In certain embodiments $R^{25}$ is heterocycle optionally substituted with 1, 2, 3, or 4 substituents.
In certain embodiments $R^{25}$ is heterocycloalkyl optionally substituted with 1, 2, 3, or 4 substituents.
In certain embodiments $R^{25}$ is haloalkoxy optionally substituted with 1, 2, 3, or 4 substituents.

Embodiments of $R^{65}$, $R^{66}$, and $R^{67}$

1. In certain embodiments an ASGPR binding ligand or extracellular protein degrading compound of the present invention is provided wherein $R^{65}$, $R^{66}$, and $R^{67}$ are independently selected from hydrogen, heteroalkyl, $C_0$-$C_6$alkyl-cyano, alkyl, alkenyl, alkynyl, haloalkyl, F, Cl, Br, I, heterocycle, heterocycloalkyl, haloalkoxy, $C_0$-$C_6$alkyl-$OR^6$, $C_0$-$C_6$alkyl-$SR^6$, $C_0$-$C_6$alkyl-$NR^6R^7$, $C_0$-$C_6$alkyl-$C(O)R^3$, $C_0$-$C_6$alkyl-$S(O)R^3$, $C_0$-$C_6$alkyl-$C(S)R^3$, $C_0$-$C_6$alkyl-$S(O)_2R^3$, $C_0$-$C_6$alkyl-$N(R^8)$—$C(O)R^3$, $C_0$-$C_6$alkyl-$N(R^8)$—$S(O)R^3$, $C_0$-$C_6$alkyl-$N(R^8)$—$C(S)R^3$, $C_0$-$C_6$alkyl-$N(R^8)$—$S(O)_2R^3$, $C_0$-$C_6$alkyl-$O$—$C(O)R^3$, $C_0$-$C_6$alkyl-$O$—$S(O)R^3$, $C_0$-$C_6$alkyl-$O$—$C(S)R^3$, —$N$=$S(O)(R^3)_2$, $C_0$-$C_6$alkyl$N_3$, and $C_0$-$C_6$alkyl-$O$—$S(O)_2R^3$, each of which is optionally substituted with 1, 2, or 3 substituents.
2. The ASGPR binding ligand or extracellular protein degrading compound of embodiment 1, wherein $R^{65}$ is not substituted with an optional substituent.
3. The ASGPR binding ligand or extracellular protein degrading compound of embodiment 1, wherein $R^{65}$ is substituted with 1 optional substituent.
4. The ASGPR binding ligand or extracellular protein degrading compound of embodiment 1, wherein $R^{65}$ is substituted with 2 optional substituents.
5. The ASGPR binding ligand or extracellular protein degrading compound of embodiment 1, wherein $R^{65}$ is substituted with 3 optional substituents.
6. The ASGPR binding ligand or extracellular protein degrading compound of embodiment 1, wherein $R^{65}$ is hydrogen.
7. The ASGPR binding ligand or extracellular protein degrading compound of embodiment 1, wherein $R^{65}$ is —$CF_3$.
8. The ASGPR binding ligand or extracellular protein degrading compound of embodiment 1, wherein $R^{65}$ is cyano.
9. The ASGPR binding ligand or extracellular protein degrading compound of embodiment 1, wherein $R^{65}$ is F.
10. The ASGPR binding ligand or extracellular protein degrading compound of embodiment 1, wherein $R^{65}$ is Cl.
11. The ASGPR binding ligand or extracellular protein degrading compound of embodiment 1, wherein $R^{65}$ is Br.
12. The ASGPR binding ligand or extracellular protein degrading compound of any one of embodiments 1-5, wherein $R^{65}$ is haloalkyl.
13. The ASGPR binding ligand or extracellular protein degrading compound of any one of embodiments 1-5, wherein $R^{65}$ is heterocycle.
14. The ASGPR binding ligand or extracellular protein degrading compound of any one of embodiments 1-5, wherein $R^{65}$ is haloalkoxy.

15. The ASGPR binding ligand or extracellular protein degrading compound of any one of embodiments 1-5, wherein $R^{65}$ is $C_0$-$C_6$alkyl-$OR^6$.
16. The ASGPR binding ligand or extracellular protein degrading compound of any one of embodiments 1-5, wherein $R^{65}$ is $C_0$-$C_6$alkyl-$SR^6$.
17. The ASGPR binding ligand or extracellular protein degrading compound of any one of embodiments 1-5, wherein $R^{65}$ is $C_0$-$C_6$alkyl-$NR^6R^7$.
18. The ASGPR binding ligand or extracellular protein degrading compound of any one of embodiments 1-5, wherein $R^{65}$ is $C_0$-$C_6$alkyl-$C(O)R^3$.
19. The ASGPR binding ligand or extracellular protein degrading compound of any one of embodiments 1-5, wherein $R^{65}$ is $C_0$-$C_6$alkyl-$S(O)R^3$.
20. The ASGPR binding ligand or extracellular protein degrading compound of any one of embodiments 1-5, wherein $R^{65}$ is $C_0$-$C_6$alkyl-$C(S)R^3$.
21. The ASGPR binding ligand or extracellular protein degrading compound of any one of embodiments 1-5, wherein $R^{65}$ is $C_0$-$C_6$alkyl-$S(O)_2R^3$.
22. The ASGPR binding ligand or extracellular protein degrading compound of any one of embodiments 1-5, wherein $R^{65}$ is $C_0$-$C_6$alkyl-$N(R^8)$—$C(O)R^3$.
23. The ASGPR binding ligand or extracellular protein degrading compound of any one of embodiments 1-5, wherein $R^{65}$ is $C_0$-$C_6$alkyl-$N(R^8)$—$S(O)R^3$.
24. The ASGPR binding ligand or extracellular protein degrading compound of any one of embodiments 1-5, wherein $R^{65}$ is $C_0$-$C_6$alkyl-$N(R^8)$—$C(S)R^3$.
25. The ASGPR binding ligand or extracellular protein degrading compound of any one of embodiments 1-5, wherein $R^{65}$ is $C_0$-$C_6$alkyl-$N(R^8)$—$S(O)_2R^3$.
26. The ASGPR binding ligand or extracellular protein degrading compound of any one of embodiments 1-5, wherein $R^{65}$ is $C_0$-$C_6$alkyl$N_3$.
27. The ASGPR binding ligand or extracellular protein degrading compound of any one of embodiments 1-5, wherein $R^{65}$ is $C_0$-$C_6$alkyl-cyano.
28. The ASGPR binding ligand or extracellular protein degrading compound of any one of embodiments 15-27, wherein $C_0$-$C_6$alkyl is $C_0$-alkyl (i.e. bond).
29. The ASGPR binding ligand or extracellular protein degrading compound of any one of embodiments 15-27, wherein $C_0$-$C_6$alkyl is $C_1$-alkyl.
30. The ASGPR binding ligand or extracellular protein degrading compound of any one of embodiments 15-27, wherein $C_0$-$C_6$alkyl is $C_2$-alkyl.
31. The ASGPR binding ligand or extracellular protein degrading compound of any one of embodiments 1-5, wherein $R^{65}$ is —N=S(O)$(R^3)_2$.
32. The ASGPR binding ligand or extracellular protein degrading compound of any one of embodiments 1-5, wherein $R^{65}$ is heterocycloalkyl.
33. The ASGPR binding ligand or extracellular protein degrading compound of any one of embodiments 1-5, wherein $R^{65}$ is heteroalkyl.
34. The ASGPR binding ligand or extracellular protein degrading compound of any one of embodiments 1-33, wherein $R^{66}$ is not substituted with an optional substituent.
35. The ASGPR binding ligand or extracellular protein degrading compound of any one of embodiments 1-33, wherein $R^{66}$ is substituted with 1 optional substituent.
36. The ASGPR binding ligand or extracellular protein degrading compound of any one of embodiments 1-33, wherein $R^{66}$ is substituted with 2 optional substituents.
37. The ASGPR binding ligand or extracellular protein degrading compound of any one of embodiments 1-33, wherein $R^{66}$ is substituted with 3 optional substituents.
38. The ASGPR binding ligand or extracellular protein degrading compound of any one of embodiments 1-33, wherein $R^{66}$ is hydrogen.
39. The ASGPR binding ligand or extracellular protein degrading compound of any one of embodiments 1-33, wherein $R^{66}$ is —$CF_3$.
40. The ASGPR binding ligand or extracellular protein degrading compound of any one of embodiments 1-33, wherein $R^{66}$ is cyano.
41. The ASGPR binding ligand or extracellular protein degrading compound of any one of embodiments 1-33, wherein $R^{66}$ is F.
42. The ASGPR binding ligand or extracellular protein degrading compound of any one of embodiments 1-33, wherein $R^{66}$ is Cl.
43. The ASGPR binding ligand or extracellular protein degrading compound of any one of embodiments 1-33, wherein $R^{66}$ is Br.
44. The ASGPR binding ligand or extracellular protein degrading compound of any one of embodiments 1-37, wherein $R^{66}$ is haloalkyl.
45. The ASGPR binding ligand or extracellular protein degrading compound of any one of embodiments 1-37, wherein $R^{66}$ is heterocycle.
46. The ASGPR binding ligand or extracellular protein degrading compound of any one of embodiments 1-37, wherein $R^{66}$ is haloalkoxy.
47. The ASGPR binding ligand or extracellular protein degrading compound of any one of embodiments 1-37, wherein $R^{66}$ is $C_0$-$C_6$alkyl-$OR^6$.
48. The ASGPR binding ligand or extracellular protein degrading compound of any one of embodiments 1-37, wherein $R^{66}$ is $C_0$-$C_6$alkyl-$SR^6$.
49. The ASGPR binding ligand or extracellular protein degrading compound of any one of embodiments 1-37, wherein $R^{66}$ is $C_0$-$C_6$alkyl-$NR^6R^7$.
50. The ASGPR binding ligand or extracellular protein degrading compound of any one of embodiments 1-37, wherein $R^{66}$ is $C_0$-$C_6$alkyl-$C(O)R^3$.
51. The ASGPR binding ligand or extracellular protein degrading compound of any one of embodiments 1-37, wherein $R^{66}$ is $C_0$-$C_6$alkyl-$S(O)R^3$.
52. The ASGPR binding ligand or extracellular protein degrading compound of any one of embodiments 1-37, wherein $R^{66}$ is $C_0$-$C_6$alkyl-$C(S)R^3$.
53. The ASGPR binding ligand or extracellular protein degrading compound of any one of embodiments 1-37, wherein $R^{66}$ is $C_0$-$C_6$alkyl-$S(O)_2R^3$.
54. The ASGPR binding ligand or extracellular protein degrading compound of any one of embodiments 1-37, wherein $R^{66}$ is $C_0$-$C_6$alkyl-$N(R^8)$—$C(O)R^3$.
55. The ASGPR binding ligand or extracellular protein degrading compound of any one of embodiments 1-37, wherein $R^{66}$ is $C_0$-$C_6$alkyl-$N(R^8)$—$S(O)R^3$.
56. The ASGPR binding ligand or extracellular protein degrading compound of any one of embodiments 1-37, wherein $R^{66}$ is $C_0$-$C_6$alkyl-$N(R^8)$—$C(S)R^3$.
57. The ASGPR binding ligand or extracellular protein degrading compound of any one of embodiments 1-37, wherein $R^{66}$ is $C_0$-$C_6$alkyl-$N(R^8)$—$S(O)_2R^3$.
58. The ASGPR binding ligand or extracellular protein degrading compound of any one of embodiments 1-37, wherein $R^{66}$ is $C_0$-$C_6$alkyl$N_3$.

59. The ASGPR binding ligand or extracellular protein degrading compound of any one of embodiments 1-37, wherein $R^{66}$ is $C_0$-$C_6$alkyl-cyano.
60. The ASGPR binding ligand or extracellular protein degrading compound of any one of embodiments 47-59, wherein $C_0$-$C_6$alkyl is $C_0$-alkyl (i.e. bond).
61. The ASGPR binding ligand or extracellular protein degrading compound of any one of embodiments 47-59, wherein $C_0$-$C_6$alkyl is $C_1$-alkyl.
62. The ASGPR binding ligand or extracellular protein degrading compound of any one of embodiments 47-59, wherein $C_0$-$C_6$alkyl is $C_2$-alkyl.
63. The ASGPR binding ligand or extracellular protein degrading compound of any one of embodiments 1-33, wherein $R^{66}$ is —N=S(O)(R$^3$)$_2$.
64. The ASGPR binding ligand or extracellular protein degrading compound of any one of embodiments 1-33, wherein $R^{66}$ is heterocycloalkyl.
65. The ASGPR binding ligand or extracellular protein degrading compound of any one of embodiments 1-33, wherein $R^{66}$ is heteroalkyl.
66. The ASGPR binding ligand or extracellular protein degrading compound of any one of embodiments 1-65, wherein $R^{67}$ is not substituted with an optional substituent.
67. The ASGPR binding ligand or extracellular protein degrading compound of any one of embodiments 1-65, wherein $R^{67}$ is substituted with 1 optional substituent.
68. The ASGPR binding ligand or extracellular protein degrading compound of any one of embodiments 1-65, wherein $R^{67}$ is substituted with 2 optional substituents.
69. The ASGPR binding ligand or extracellular protein degrading compound of any one of embodiments 1-65, wherein $R^{67}$ is substituted with 3 optional substituents.
70. The ASGPR binding ligand or extracellular protein degrading compound of any one of embodiments 1-65, wherein $R^{67}$ is hydrogen.
71. The ASGPR binding ligand or extracellular protein degrading compound of any one of embodiments 1-65, wherein $R^{67}$ is —CF$_3$.
72. The ASGPR binding ligand or extracellular protein degrading compound of any one of embodiments 1-65, wherein $R^{67}$ is cyano.
73. The ASGPR binding ligand or extracellular protein degrading compound of any one of embodiments 1-65, wherein $R^{67}$ is F.
74. The ASGPR binding ligand or extracellular protein degrading compound of any one of embodiments 1-65, wherein $R^{67}$ is Cl.
75. The ASGPR binding ligand or extracellular protein degrading compound of any one of embodiments 1-65, wherein $R^{67}$ is Br.
76. The ASGPR binding ligand or extracellular protein degrading compound of any one of embodiments 1-65, wherein $R^{67}$ is haloalkyl.
77. The ASGPR binding ligand or extracellular protein degrading compound of any one of embodiments 1-65, wherein $R^{67}$ is heterocycle.
78. The ASGPR binding ligand or extracellular protein degrading compound of any one of embodiments 1-65, wherein $R^{67}$ is haloalkoxy.
79. The ASGPR binding ligand or extracellular protein degrading compound of any one of embodiments 1-65, wherein $R^{67}$ is $C_0$-$C_6$alkyl-OR$^6$.
80. The ASGPR binding ligand or extracellular protein degrading compound of any one of embodiments 1-65, wherein $R^{67}$ is $C_0$-$C_6$alkyl-SR$^6$.
81. The ASGPR binding ligand or extracellular protein degrading compound of any one of embodiments 1-65, wherein $R^{67}$ is $C_0$-$C_6$alkyl-NR$^6$R$^7$.
82. The ASGPR binding ligand or extracellular protein degrading compound of any one of embodiments 1-65, wherein $R^{67}$ is $C_0$-$C_6$alkyl-C(O)R$^3$.
83. The ASGPR binding ligand or extracellular protein degrading compound of any one of embodiments 1-65, wherein $R^{67}$ is $C_0$-$C_6$alkyl-S(O)R$^3$.
84. The ASGPR binding ligand or extracellular protein degrading compound of any one of embodiments 1-65, wherein $R^{67}$ is $C_0$-$C_6$alkyl-C(S)R$^3$.
85. The ASGPR binding ligand or extracellular protein degrading compound of any one of embodiments 1-65, wherein $R^{67}$ is $C_0$-$C_6$alkyl-S(O)$_2$R$^3$.
86. The ASGPR binding ligand or extracellular protein degrading compound of any one of embodiments 1-65, wherein $R^{67}$ is $C_0$-$C_6$alkyl-N(R$^8$)—C(O)R$^3$.
87. The ASGPR binding ligand or extracellular protein degrading compound of any one of embodiments 1-65, wherein $R^{67}$ is $C_0$-$C_6$alkyl-N(R$^8$)—S(O)R$^3$.
88. The ASGPR binding ligand or extracellular protein degrading compound of any one of embodiments 1-65, wherein $R^{67}$ is $C_0$-$C_6$alkyl-N(R$^8$)—C(S)R$^3$.
89. The ASGPR binding ligand or extracellular protein degrading compound of any one of embodiments 1-65, wherein $R^{67}$ is $C_0$-$C_6$alkyl-N(R$^8$)—S(O)$_2$R$^3$.
90. The ASGPR binding ligand or extracellular protein degrading compound of any one of embodiments 1-65, wherein $R^{67}$ is $C_0$-$C_6$alkylN$_3$.
91. The ASGPR binding ligand or extracellular protein degrading compound of any one of embodiments 1-65, wherein $R^{67}$ is $C_0$-$C_6$alkyl-cyano.
92. The ASGPR binding ligand or extracellular protein degrading compound of any one of embodiments 79-91, wherein $C_0$-$C_6$alkyl is $C_0$-alkyl (i.e. bond).
93. The ASGPR binding ligand or extracellular protein degrading compound of any one of embodiments 79-91, wherein $C_0$-$C_6$alkyl is $C_1$-alkyl.
94. The ASGPR binding ligand or extracellular protein degrading compound of any one of embodiments 79-91, wherein $C_0$-$C_6$alkyl is $C_2$-alkyl.
95. The ASGPR binding ligand or extracellular protein degrading compound of any one of embodiments 1-65, wherein $R^{67}$ is —N=S(O)(R$^3$)$_2$.
96. The ASGPR binding ligand or extracellular protein degrading compound of any one of embodiments 1-65, wherein $R^{67}$ is heterocycloalkyl.
97. The ASGPR binding ligand or extracellular protein degrading compound of any one of embodiments 1-65, wherein $R^{67}$ is heteroalkyl.
98. In certain embodiments an ASGPR binding ligand or extracellular protein degrading compound of the present invention is provided wherein $R^{68}$, $R^{69}$, and $R^{70}$ are independently selected from $R^{65}$, $R^{66}$, and $R^{67}$ as described above wherein $R^{68}$, $R^{69}$, and $R^{70}$ are not cyano or CF$_3$.

In certain embodiments $R^{65}$, $R^{66}$, or $R^{67}$ is aryl.

In certain embodiments $R^{65}$, $R^{66}$, or $R^{67}$ is heteroaryl.

In certain embodiments $R^{65}$, $R^{66}$, or $R^{67}$ is heterocycle.

Additional Embodiments
1. In certain embodiments a compound selected from Table 1A or Table 1B or a pharmaceutically acceptable salt thereof is provided.
2. The compound of embodiment 1 selected from:
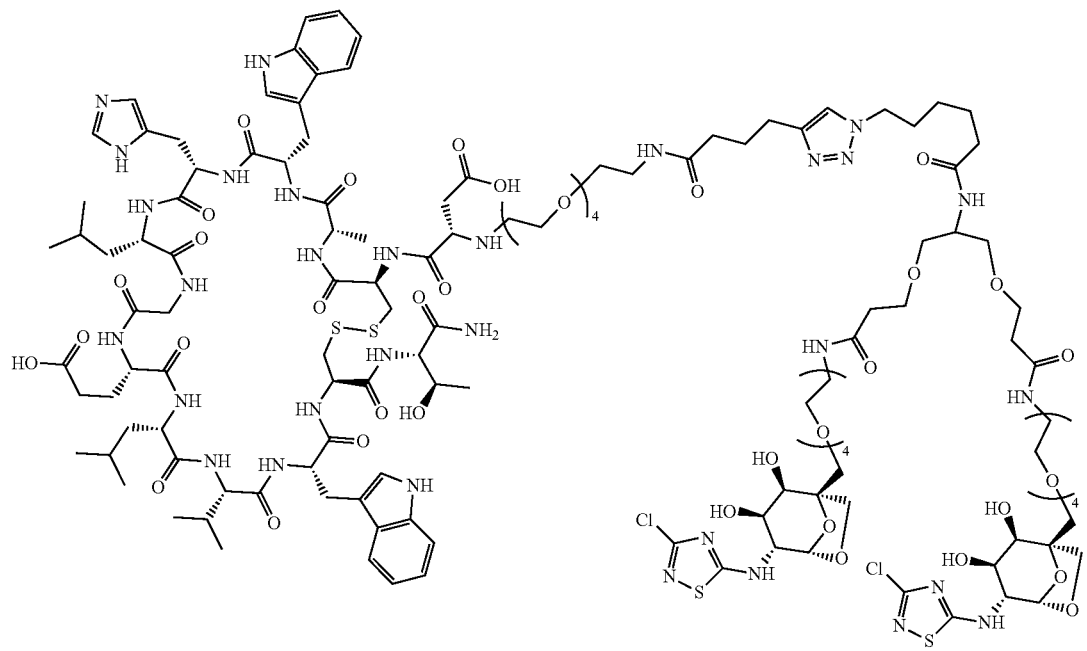
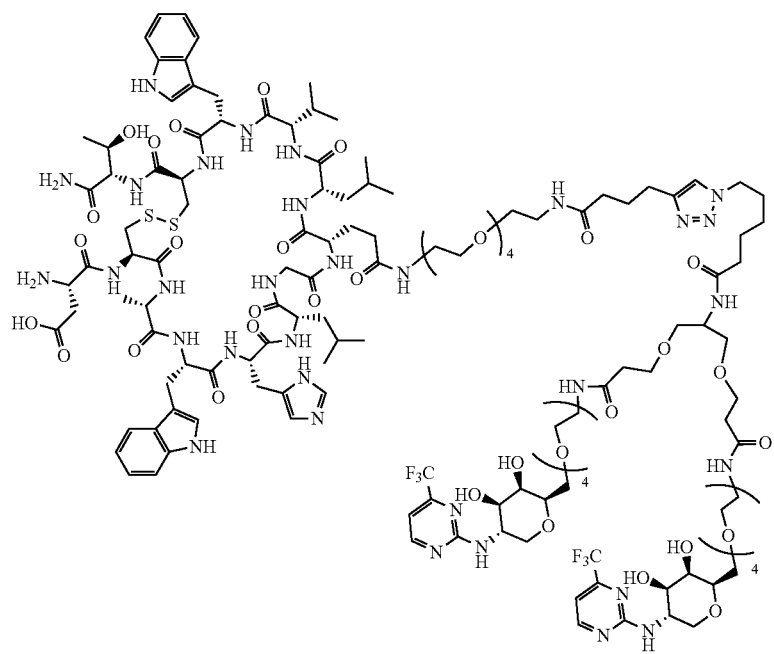

655
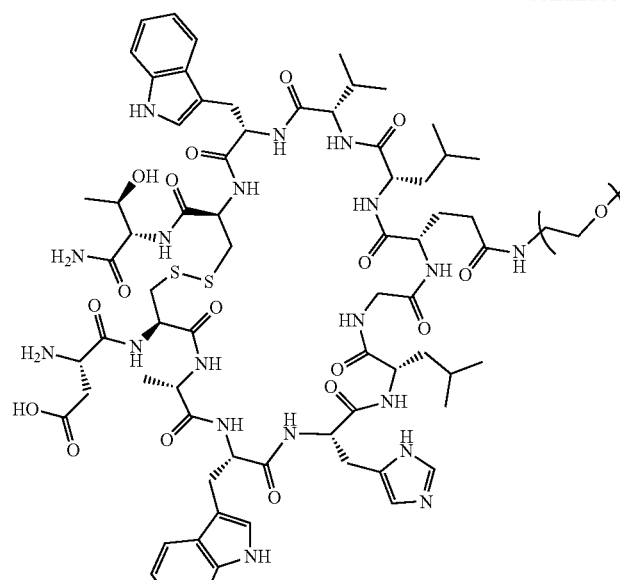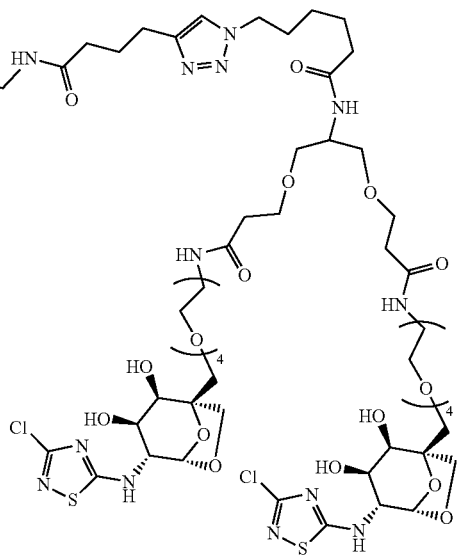
-continued
656
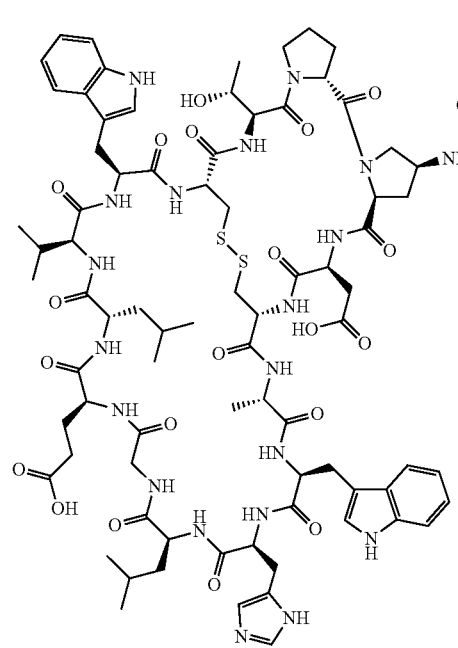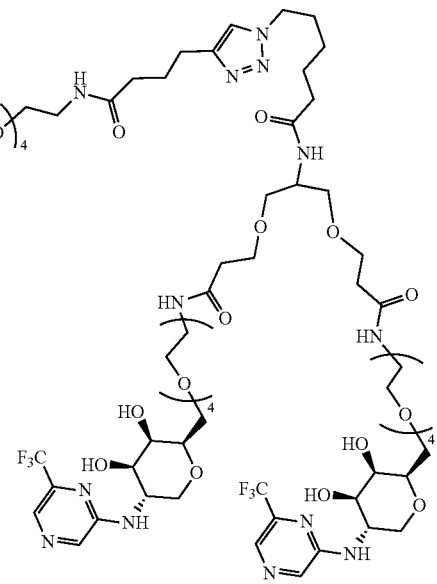

-continued
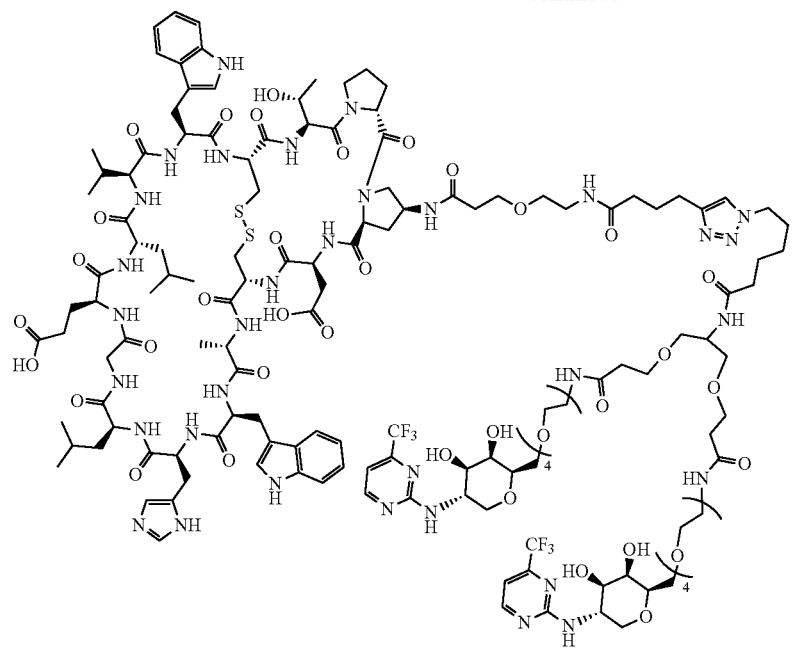

659
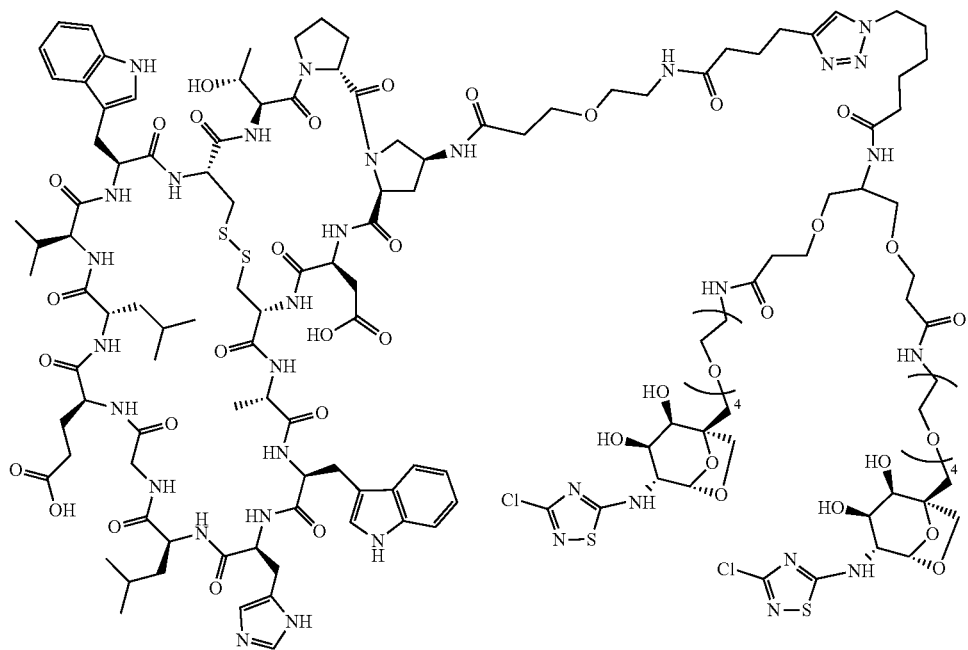
660
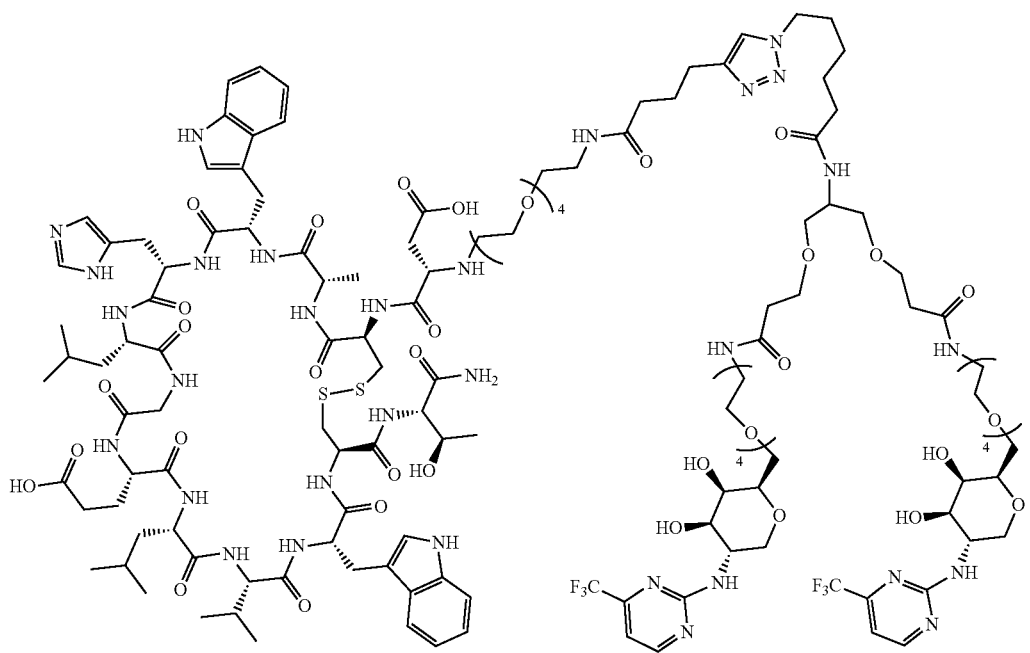

-continued
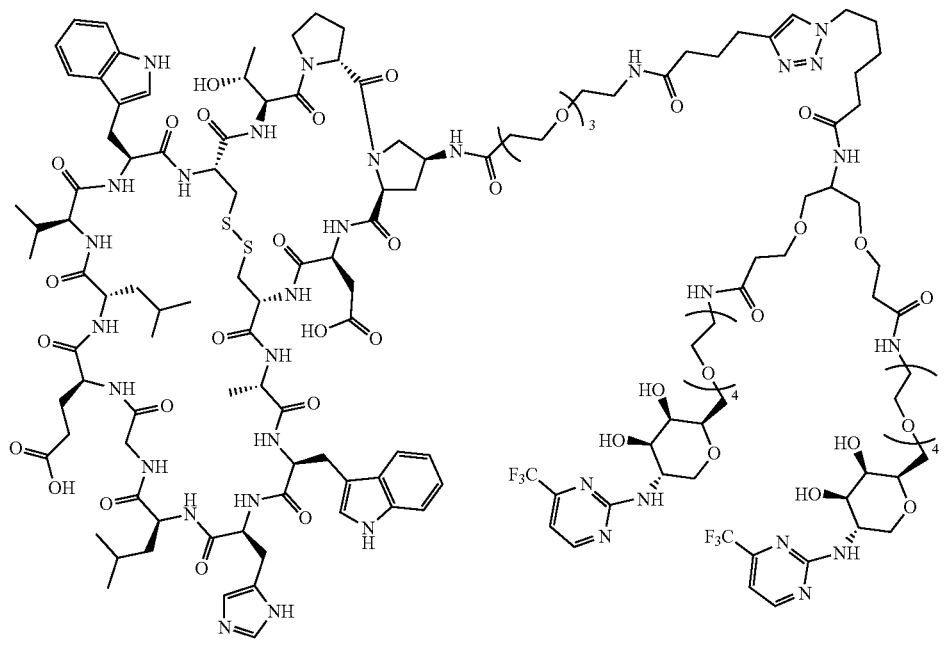
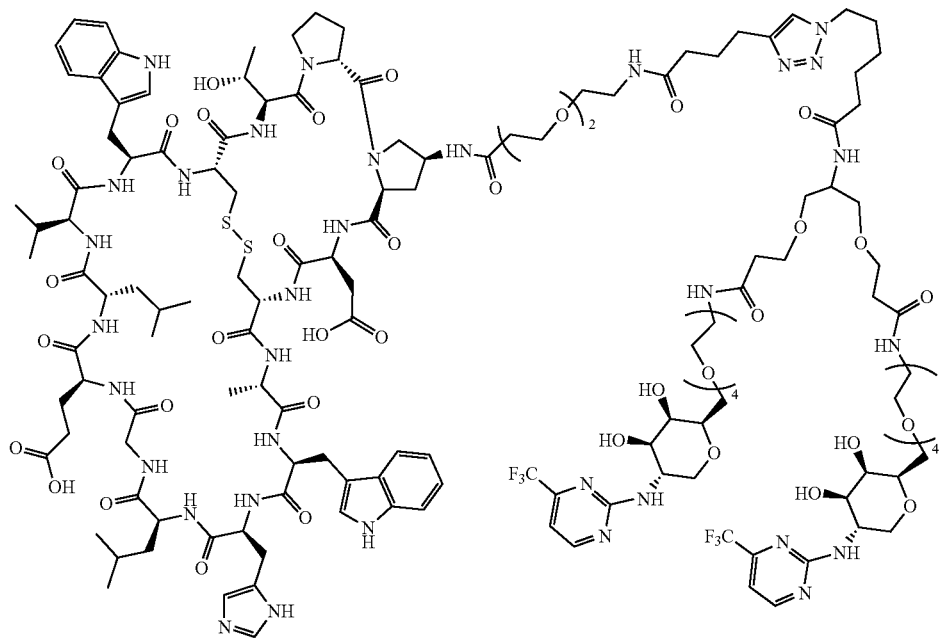

-continued
663
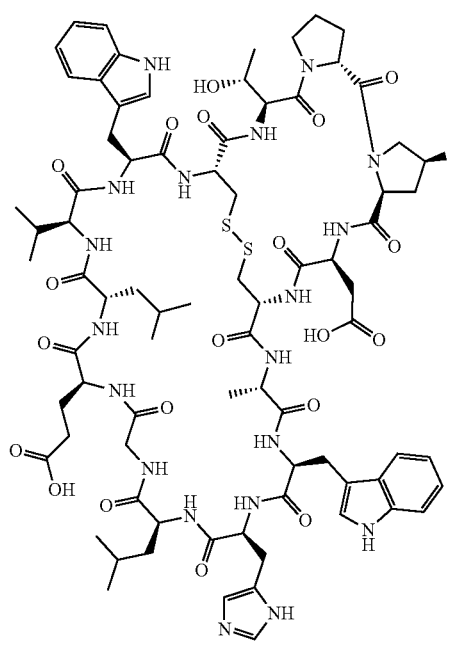
664
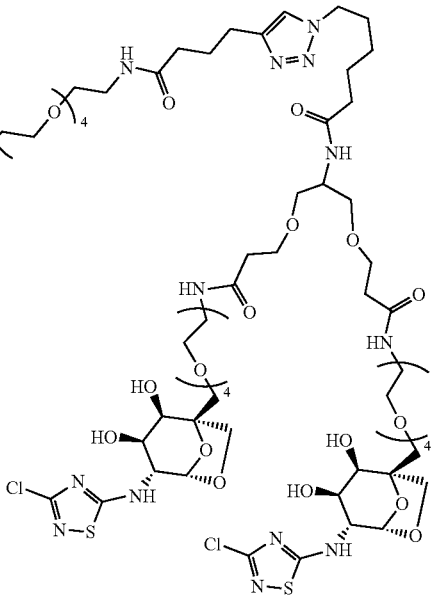
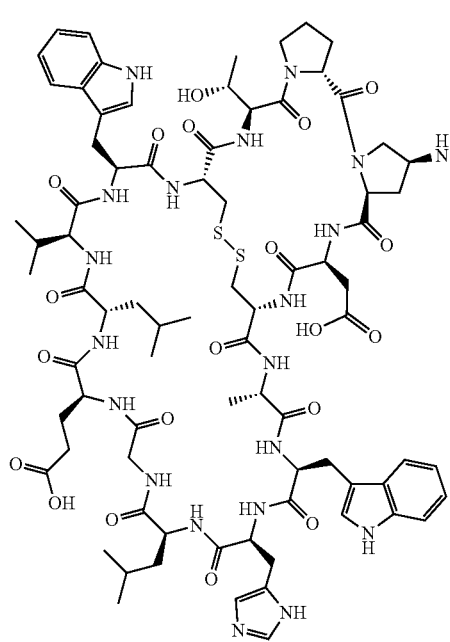
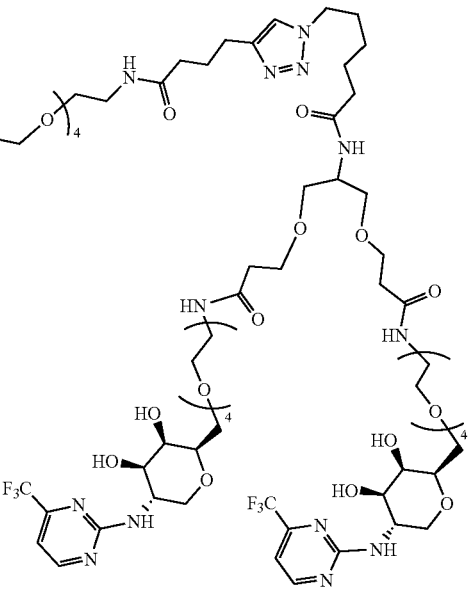

665
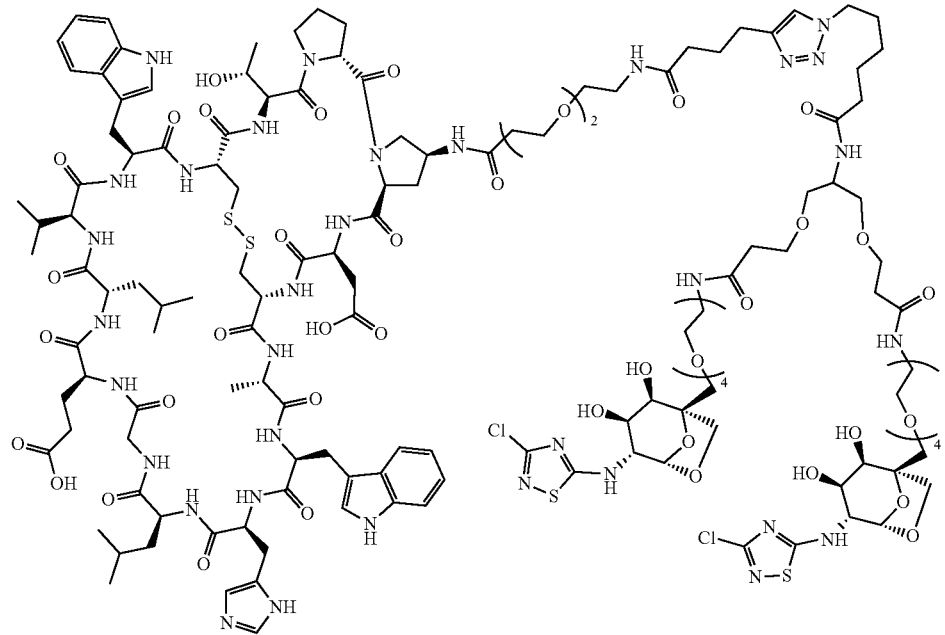
666
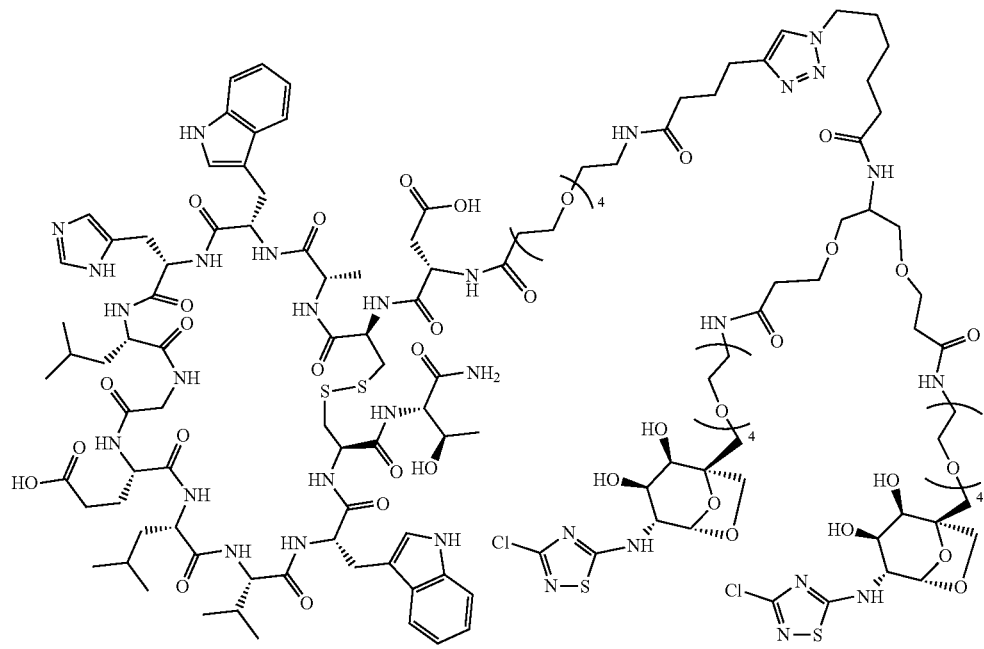

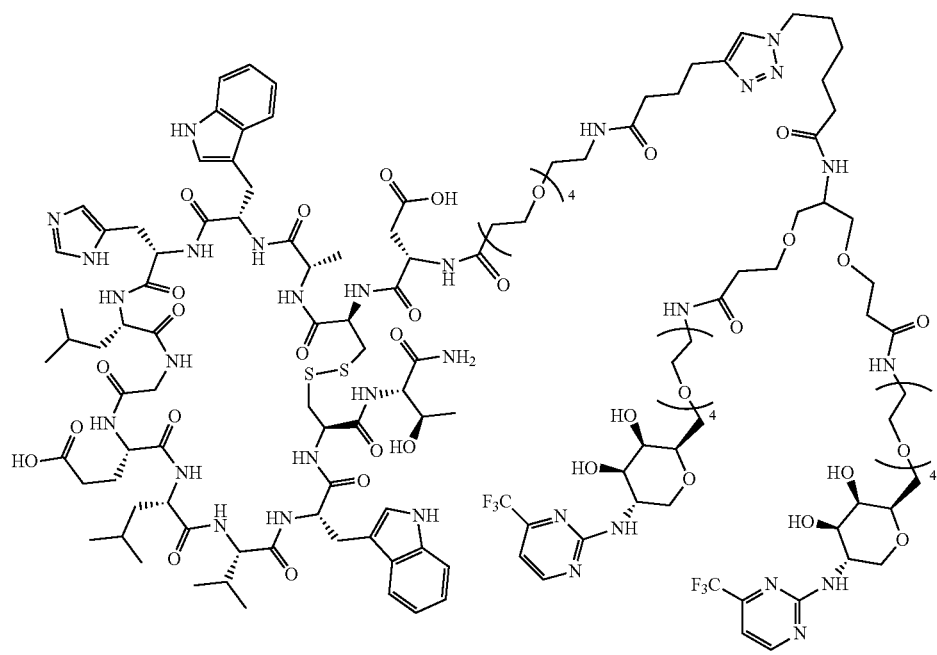
or pharmaceutically acceptable salt thereof.
3. The compound of embodiment 1 selected from:
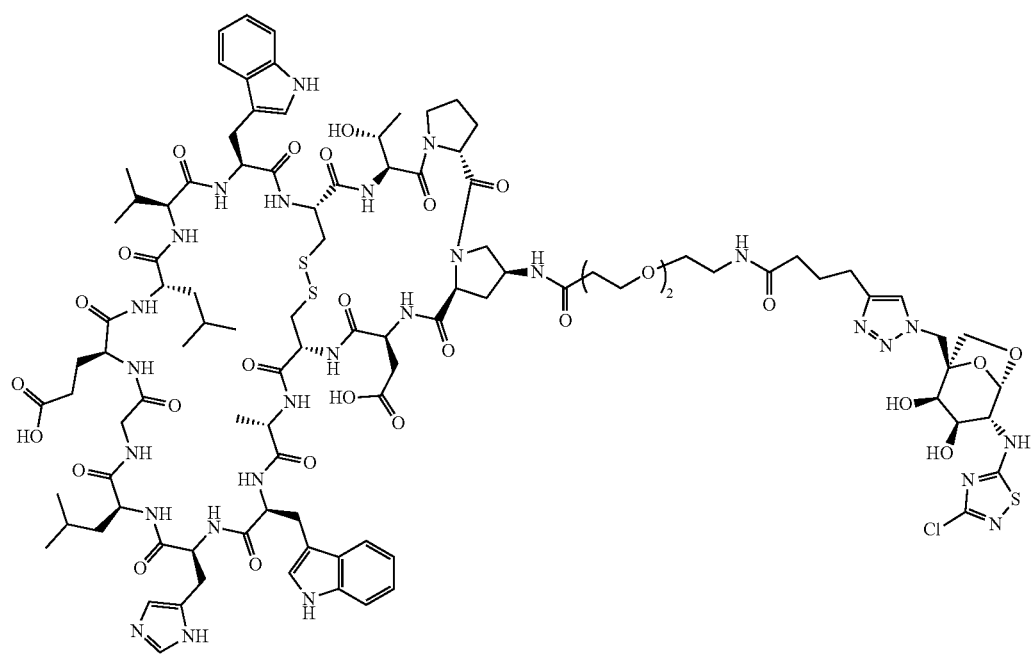

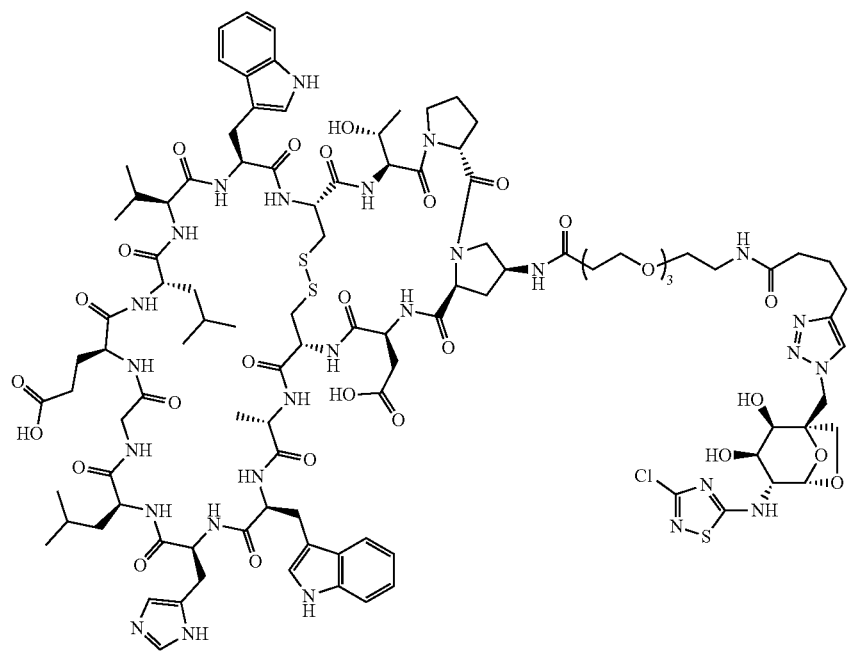
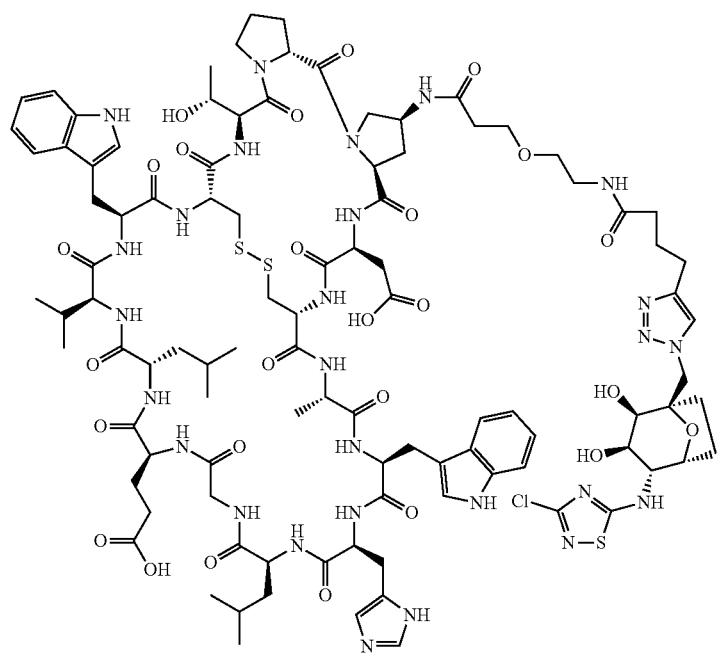

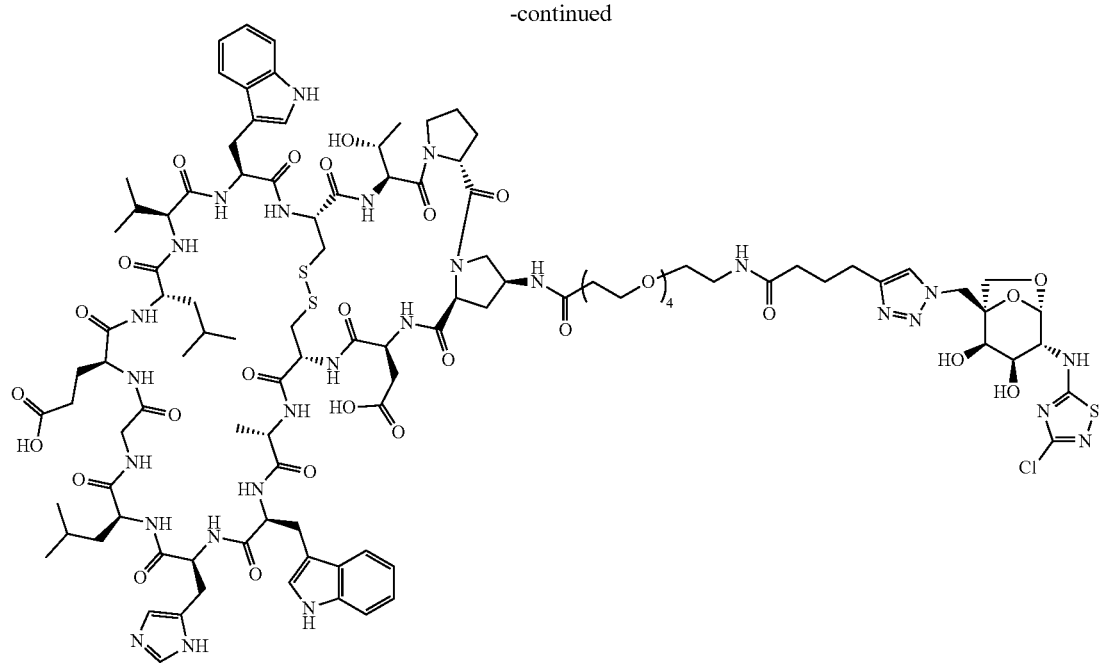
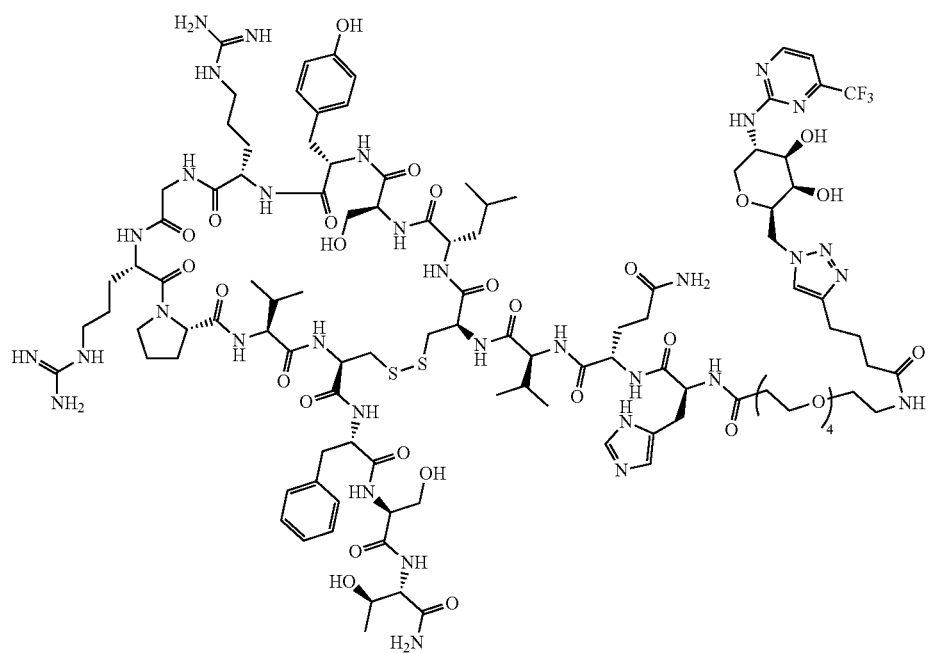
or a pharmaceutically acceptable salt thereof.

4. The compound of embodiment 1 selected from:
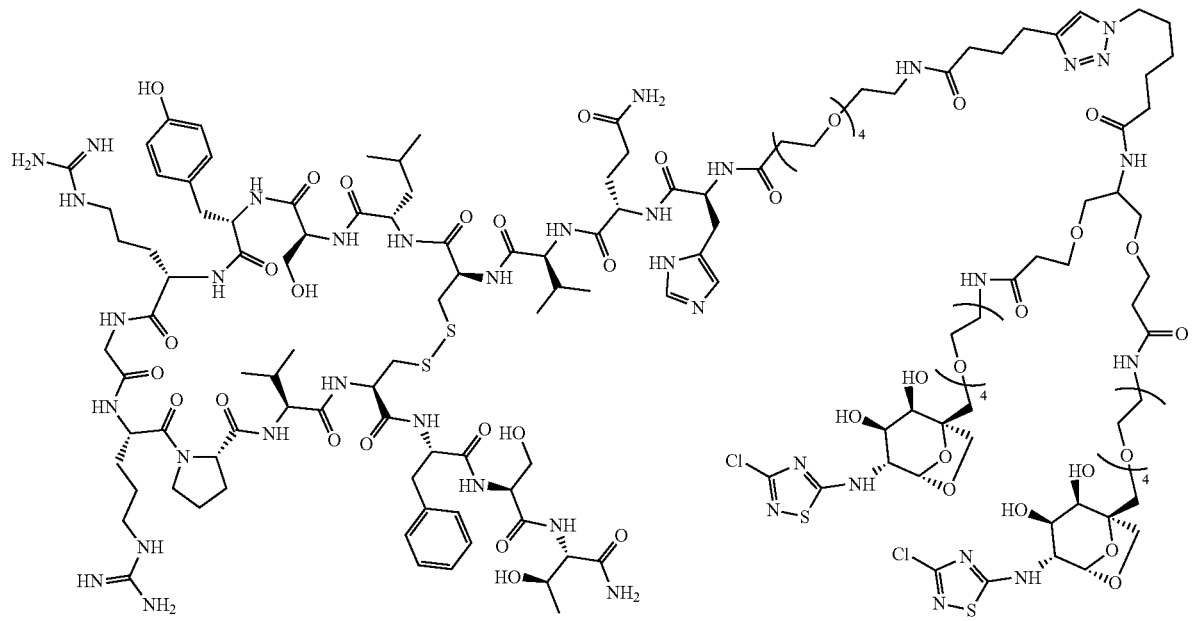
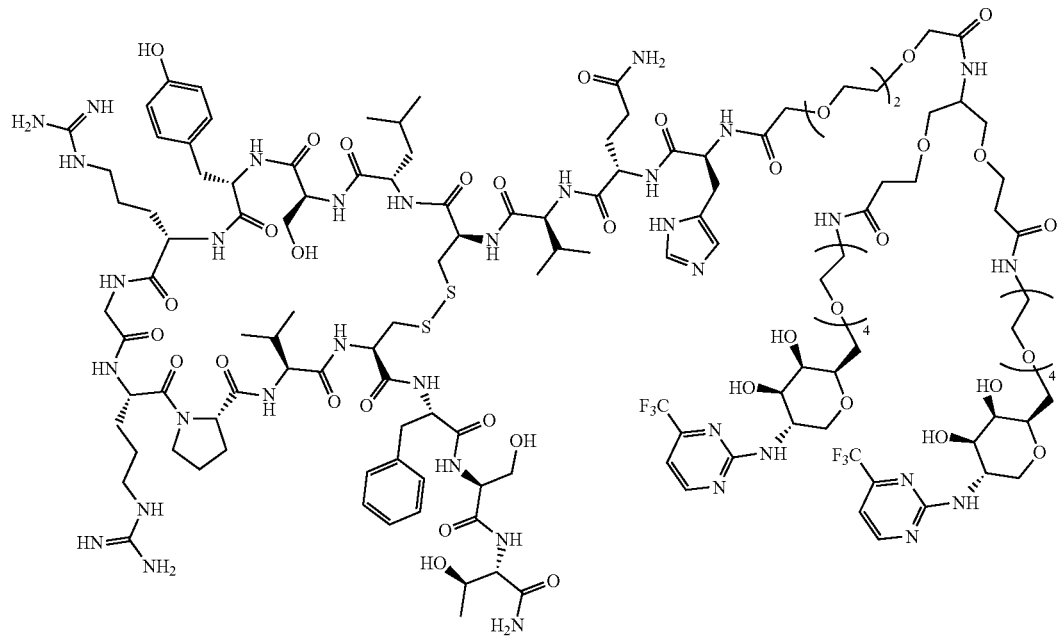

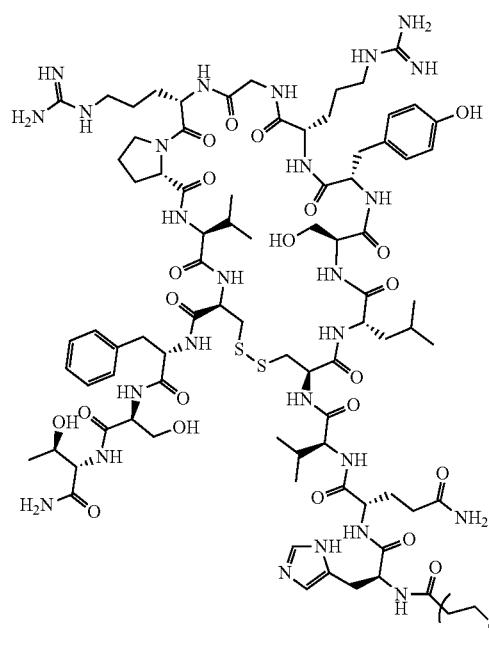
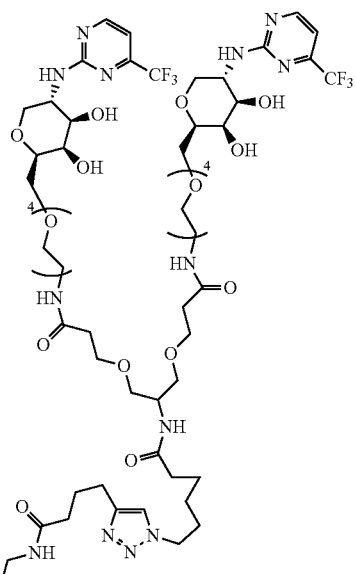
5. The compound of embodiment 1 selected from:
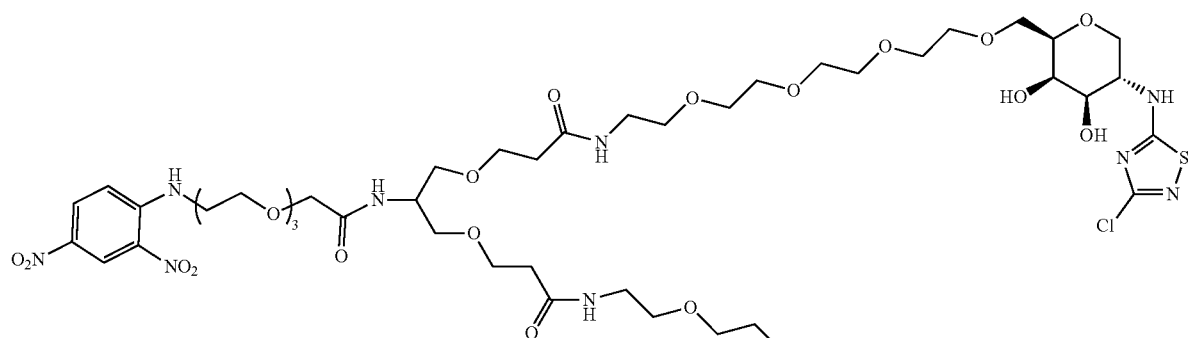
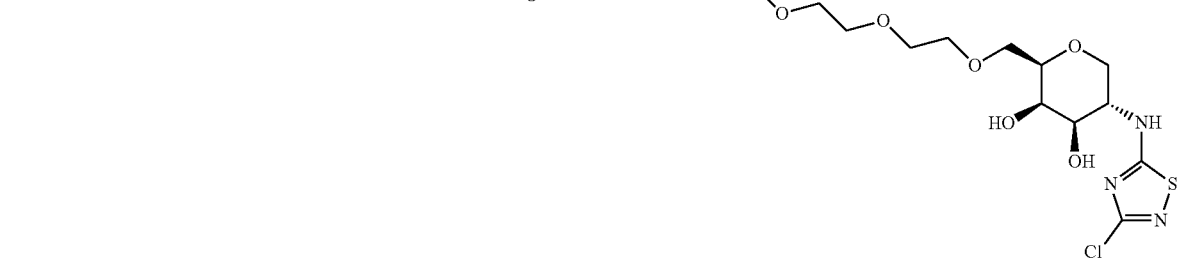
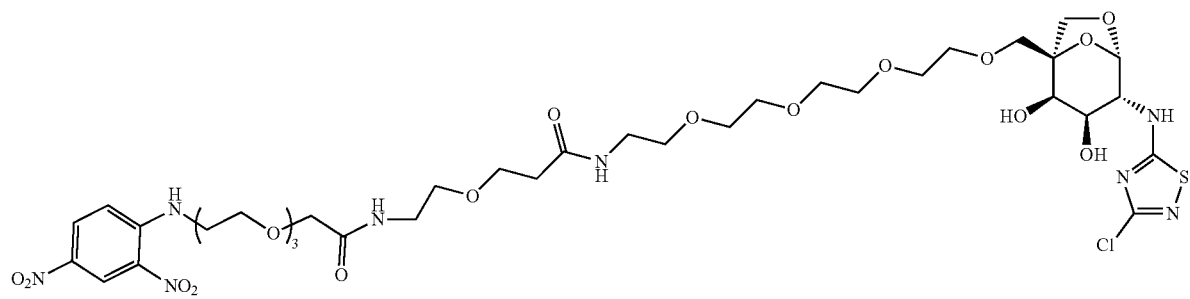

-continued
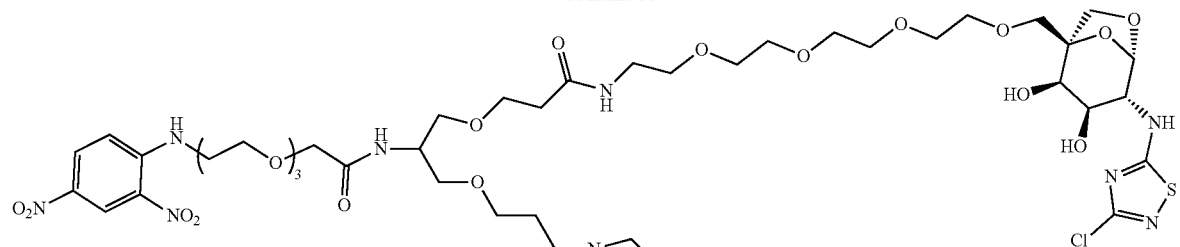
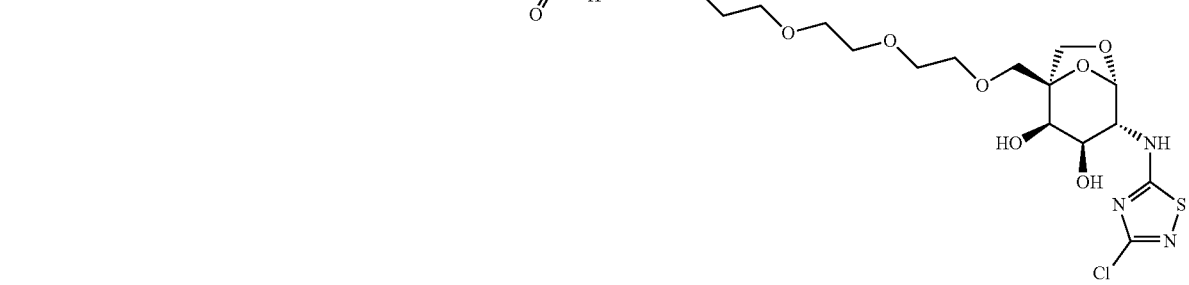
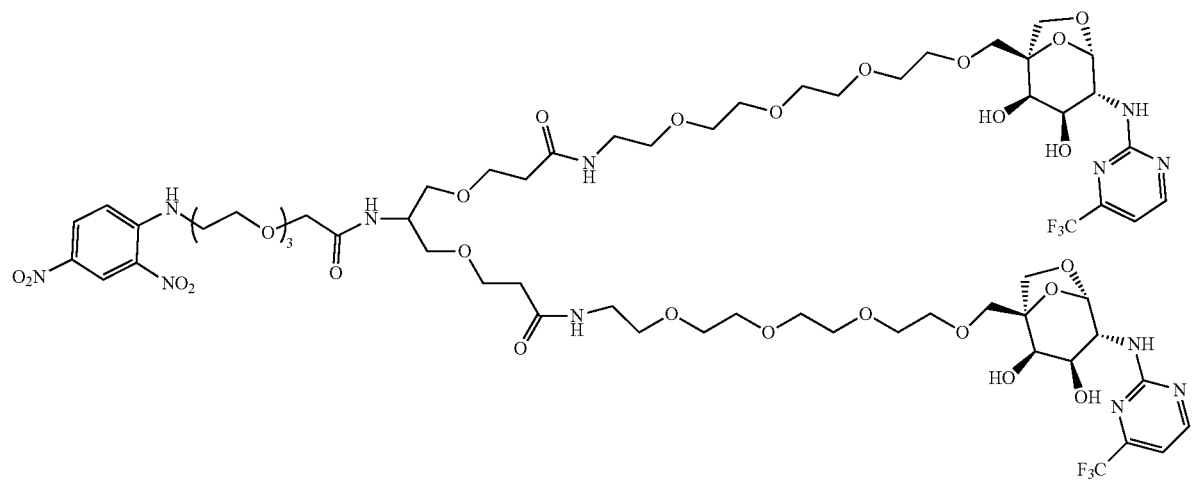
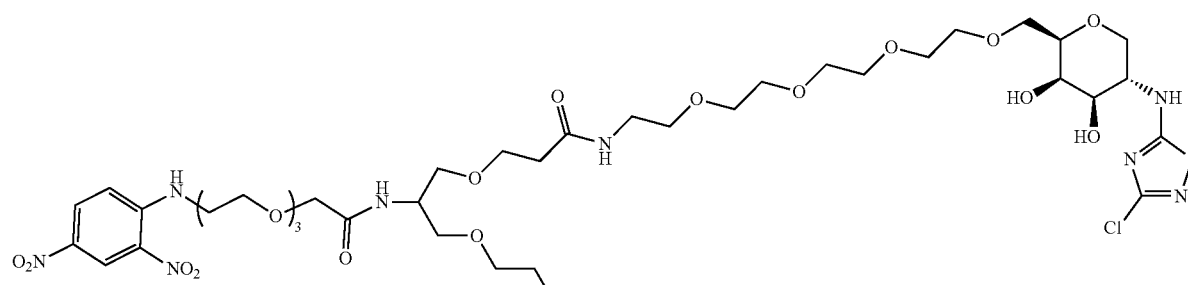
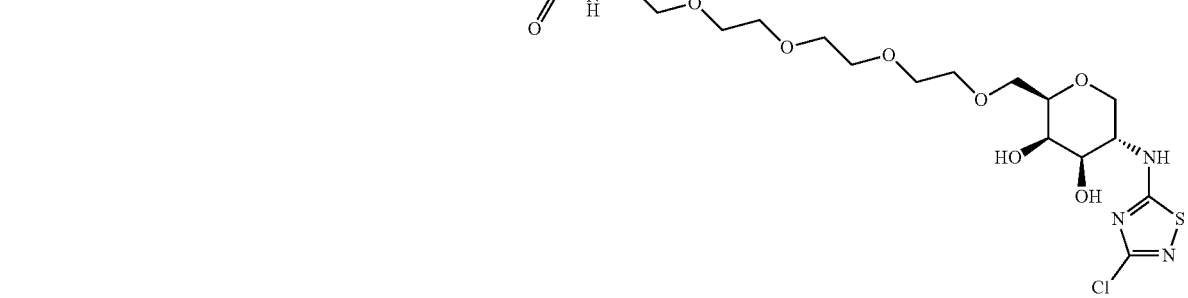

-continued
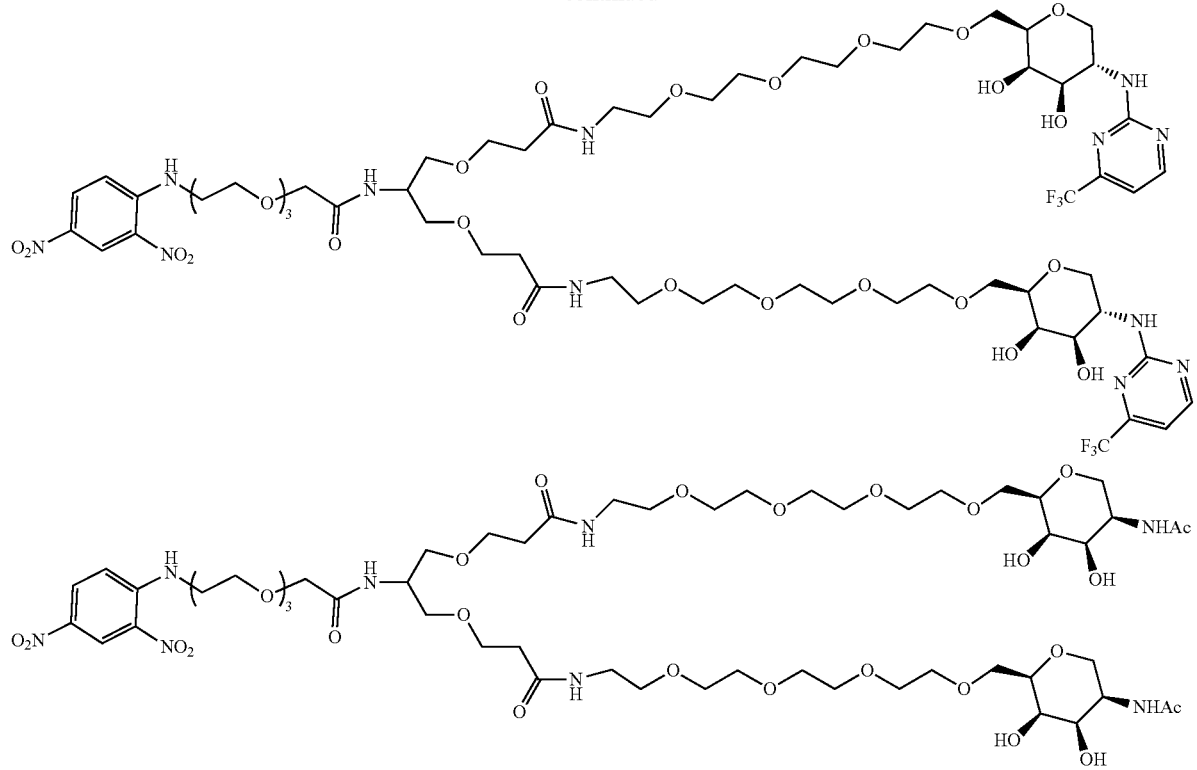
or a pharmaceutically acceptable salt thereof.
6. The compound of embodiment 1 selected from:
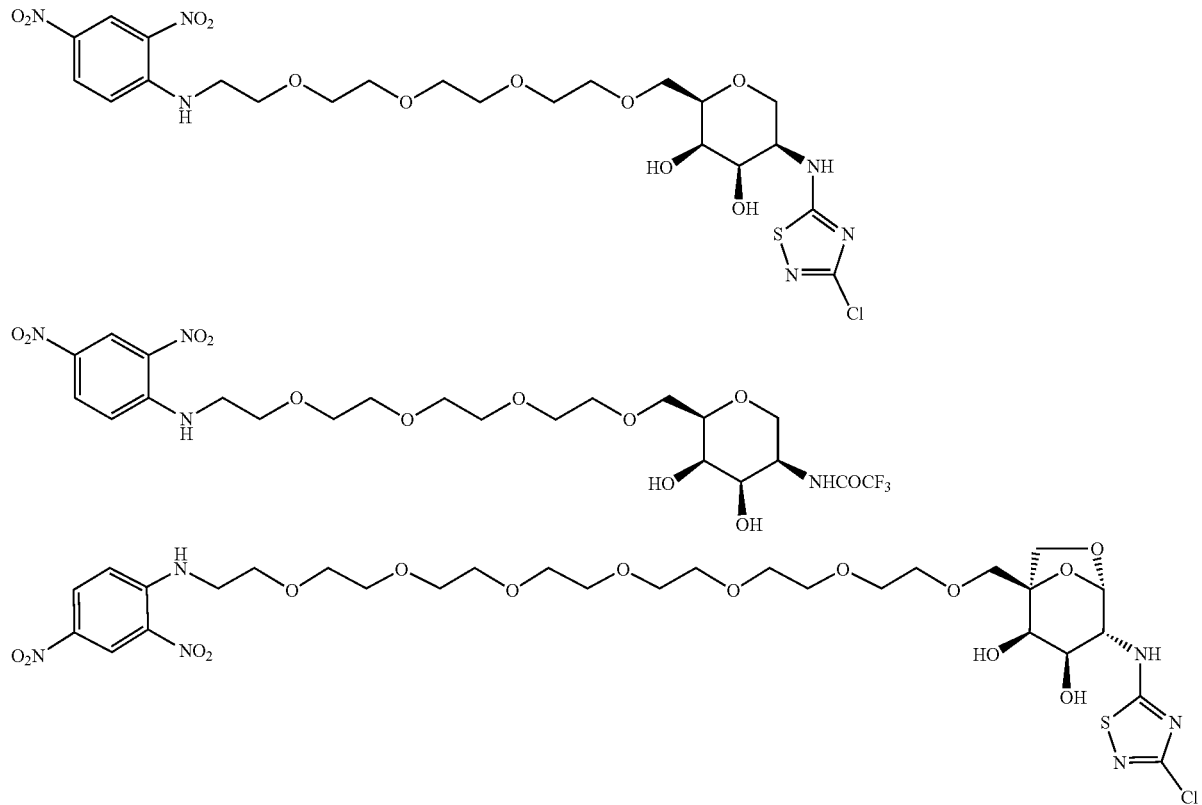

-continued

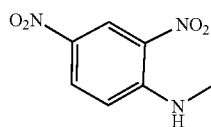 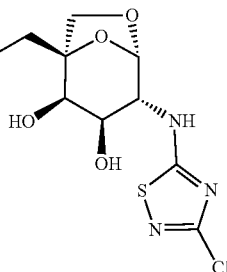

or a pharmaceutically acceptable salt thereof.

7. A pharmaceutical composition comprising a compound of any one of embodiments 1-6 and a pharmaceutically acceptable excipient.
8. A method to treat a disorder mediated by an immunoglobulin comprising administering an effective amount of compound of any one of embodiments 1-6 or a pharmaceutically acceptable salt thereof or a pharmaceutical composition of embodiment 7 to a patient in need thereof.
9. The method of embodiment 8, wherein the disorder is mediated by immunoglobulin G (IgG).
10. The method of embodiment 9, wherein the disorder is selected from type 1 autoimmune pancreatitis, interstitial nephritis, Riedel's thyroiditis, storiform fibrosis, Mikulicz's disease, Küttner's tumor, inflammatory pseudotumors, mediastinal fibrosis, retroperitoneal fibrosis (Ormond's disease), aortitis, periaortitis, proximal biliary strictures, idiopathic hypocomplementic tubulointerstitial nephritis, multifocal fibrosclerosis, pachymeningitis, pancreatic enlargement, tumefactive lesions, pericarditis, rheumatoid arthritis (RA), inflammatory bowel disease, multiple sclerosis, myasthenic gravis, thyroid eye disease, chronic inflammatory demyelinating polyneuropathy, warm autoimmune hemolytic anemia, ankylosing spondylitis, primary Sjögren's syndrome, psoriatic arthritis, and systemic lupus erythematosus (SLE), sclerosing cholangitis, and IgG monoclonal gammopathy, monoclonal gammopathy of undetermined significance (MGUS).
11. The method of embodiment 8, wherein the disorder is mediated by immunoglobulin A (IgA).
12. The method of embodiment 11, wherein the disorder is selected from IgA nephropathy (Berger's disease), celiac disease, Crohn's disease, Henoch-Sconiein purpura (HSP), liner IgA bullous dermatosis, IgA pemphigus, dermatitis herpetiformis, inflammatory bowel disease (IBD), Sjögren's syndrome, ankylosing spondylitis, alcoholic liver cirrhosis, acquired immunodeficiency syndrome, IgA multiple myeloma, α-chain disease, IgA monoclonal gammopathy, monoclonal gammopathy of undetermined significance (MGUS), and linear IgA bullous dermatosis.
13. The method of any one of embodiments 8-12, wherein the patient is a human.
14. In certain embodiments a compound of Table 2A or Table 2B or a salt thereof is provided.

III. Pharmaceutical Compositions and Dosage Forms for the Extracellular Protein Degraders of the Present Invention An extracellular protein degrader of the present invention or a pharmaceutically acceptable salt, solvate or prodrug thereof as disclosed herein can be administered as a neat chemical, but is more typically administered as a pharmaceutical composition that includes an effective amount for a host, typically a human, in need of such treatment to treat a disorder mediated by the Target Extracellular Protein as described herein or otherwise well-known for that Target Extracellular Protein.

In certain embodiments, the present invention provides pharmaceutical compositions comprising an extracellular protein degrader of the present invention or a pharmaceutically acceptable composition, salt, isotopic analog such as a deuterated derivative, or prodrug thereof, and a pharmaceutically acceptable excipient. In certain embodiments, the extracellular protein degrader is present in an effective amount, e.g., a therapeutically effective amount or a prophylactically effective amount.

The ASGPR-binding extracellular protein degraders of the present invention can be administered in any manner that allows the degrader to bind to the immunoglobulin, typically in the blood stream, and carry it to the ASGPR-bearing hepatocyte cells on the liver for endocytosis and degradation. As such, examples of methods to deliver the degraders of the present invention include, but are not limited to, oral, intravenous, sublingual, subcutaneous, parenteral, buccal, rectal, intra-aortal, intracranial, subdermal or transnasal, or by other means, in dosage unit formulations containing one or more conventional pharmaceutically acceptable carriers, as appropriate.

In certain embodiments the extracellular protein degrader of the present invention is administered intravenously. Typically, the extracellular protein degrader will be formulated in a liquid dosage form for intravenous injection, such as a buffered solution. Non-limiting examples of solutions for intravenous injection include phosphate buffered solution and saline buffered solution. In certain embodiments the solution is buffered with multiple salts.

In certain embodiments the extracellular protein degrader of the present invention is administered orally. Typically, the extracellular protein degrader will be formulated in a solid dosage form for oral administration or as a gel containing capsule. Non-limiting examples of solid dosage forms include capsules, tablets, and powders.

In certain embodiments the extracellular protein degrader of the present invention is administered subcutaneously. Typically, the extracellular protein degrader will be formulated in a liquid dosage form for subcutaneous injection, such as a buffered solution. Non-limiting examples of solutions for subcutaneous injection include phosphate buffered solution and saline buffered solution. In certain embodiments the solution is buffered with multiple salts.

Therefore, the disclosure provides pharmaceutical compositions comprising an effective amount of extracellular protein degrader or its pharmaceutically acceptable salt together with at least one pharmaceutically acceptable carrier for any appropriate use thereof. The pharmaceutical composition may contain an extracellular protein degrader or salt as the only active agent, or, in an alternative embodiment, the extracellular protein degrader and at least one additional active agent.

In certain embodiments the term pharmaceutically acceptable salt refers to a salt of the described extracellular protein degrader which is, within the scope of sound medical judgment, suitable for administration to a host such as a human without undue toxicity, irritation, allergic response, and the like, commensurate with a reasonable benefit/risk ratio, and effective for its intended use. Thus, the term "pharmaceutically acceptable salt" refers to the relatively non-toxic, inorganic and organic acid addition salts of the presently disclosed extracellular protein degraders. These salts can be prepared during the final isolation and purification of the extracellular protein degraders or by separately reacting the purified extracellular protein degrader in its free form with a suitable organic or inorganic acid and then isolating the salt thus formed. Basic extracellular protein degraders are capable of forming a wide variety of different salts with various inorganic and organic acids. Acid addition salts of the basic extracellular protein degraders are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic extracellular protein degraders are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

Pharmaceutically acceptable excipients include inert diluents, dispersing and/or granulating agents, surface active agents and/or emulsifiers, disintegrating agents, binding agents, preservatives, buffering agents, lubricating agents, and/or oils. Additional acceptable excipients include cocoa butter and suppository waxes, coloring agents, coating agents, sweetening, flavoring, perfuming agents, etc., and combinations thereof.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum 32 silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, etc., and/or combinations thereof.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Any dosage form can be used that achieves the desired results. In certain embodiments the pharmaceutical composition is in a dosage form that contains from about 0.1 mg to about 1500 mg, from about 10 mg to about 1000 mg, from about 100 mg to about 800 mg, or from about 200 mg to about 600 mg of the active extracellular protein degrader and optionally from about 0.1 mg to about 1500 mg, from about 10 mg to about 1000 mg, from about 100 mg to about 800 mg, or from about 200 mg to about 600 mg of an additional active agent in a unit dosage form. Examples are dosage forms with at least about 0.1, 1, 5, 10, 25, 50, 100, 200, 250, 300, 400, 500, 600, 700, 750, 800, 850, 900, 950, or 1,000 mg of active extracellular protein degrader, or its salt. In certain embodiments the dosage form has at most about 0.1, 1, 5, 10, 25, 50, 100, 200, 250, 300, 400, 500, 600, 700, 750, 800, 850, 900, 950, or 1,000 mg of active extracellular protein degrader, or its salt.

In certain embodiments the dose ranges from about 0.01-100 mg/kg of patient bodyweight, for example about 0.01 mg/kg, about 0.05 mg/kg, about 0.1 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg.

In some embodiments, extracellular protein degraders disclosed herein or used as described are administered once a day (QD), twice a day (BID), or three times a day (TID). In some embodiments, extracellular protein degraders disclosed herein or used as described are administered at least once a day for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer.

In certain embodiments the extracellular protein degrader of the present invention is administered once a day, twice a day, three times a day, or four times a day.

The pharmaceutical composition may be formulated as any pharmaceutically useful form, e.g., a pill, capsule, tablet, an injection or infusion solution, a syrup, an inhalation formulation, a suppository, a buccal or sublingual formulation, a parenteral formulation, or in a medical device. Some dosage forms, such as tablets and capsules, can be subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert, or it can possess pharmaceutical benefits of its own. The amount of carrier employed in conjunction with the extracellular protein degrader is sufficient to provide a practical quantity of material for administration per unit dose of the extracellular protein degrader. If provided as in a liquid, it can be a solution or a suspension.

Representative carriers include phosphate buffered saline, water, solvent(s), diluents, pH modifying agents, preservatives, antioxidants, suspending agents, wetting agent, viscosity agents, tonicity agents, stabilizing agents, and combinations thereof. In some embodiments, the carrier is an aqueous carrier. Examples of aqueous carries include, but are not limited to, an aqueous solution or suspension, such as saline, plasma, bone marrow aspirate, buffers, such as Hank's Buffered Salt Solution (HBSS), HEPES (4-(2-hydroxyethyl)-1-piperazineethanesulfonic acid), Ringers buffer, ProVisc®, diluted ProVisc®, Provisc® diluted with PBS, Krebs buffer, Dulbecco's PBS, normal PBS, sodium hyaluronate solution (HA, 5 mg/mL in PBS), citrate buffer, simulated body fluids, plasma platelet concentrate and tissue culture medium or an aqueous solution or suspension comprising an organic solvent. Acceptable solutions include, for example, water, Ringer's solution and isotonic sodium chloride solutions. The formulation may also be a sterile solution, suspension, or emulsion in a non-toxic diluent or solvent such as 1,3-butanediol.

Viscosity agents may be added to the pharmaceutical composition to increase the viscosity of the composition as desired. Examples of useful viscosity agents include, but are not limited to, hyaluronic acid, sodium hyaluronate, carbomers, polyacrylic acid, cellulosic derivatives, polycarbophil, polyvinylpyrrolidone, gelatin, dextin, polysaccharides, polyacrylamide, polyvinyl alcohol (including partially hydrolyzed polyvinyl acetate), polyvinyl acetate, derivatives thereof and mixtures thereof.

Solutions, suspensions, or emulsions for administration may be buffered with an effective amount necessary to maintain a pH suitable for the selected administration. Suitable buffers are well known by those skilled in the art. Some examples of useful buffers are acetate, borate, carbonate, citrate, and phosphate buffers. Solutions, suspensions, or emulsions for topical, for example, ocular administration may also contain one or more tonicity agents to adjust the isotonic range of the formulation. Suitable tonicity agents are well known in the art. Some examples include glycerin, mannitol, sorbitol, sodium chloride, and other electrolytes.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which do not substantially interfere with the activity of the extracellular protein degrader of the present invention.

The pharmaceutical compositions/combinations can be formulated for oral administration. These compositions can contain any amount of active extracellular protein degrader that achieves the desired result, for example between 0.1 and 99 weight % (wt. %) of the extracellular protein degrader and usually at least about 5 wt. % of the extracellular protein degrader. Some embodiments contain from about 25 wt. % to about 50 wt. % or from about 5 wt. % to about 75 wt. % of the extracellular protein degrader. Enteric coated oral tablets may also be used to enhance bioavailability of the extracellular protein degraders for an oral route of administration.

Formulations suitable for rectal administration are typically presented as unit dose suppositories. These may be prepared by admixing the active extracellular protein degrader with one or more conventional solid carriers, for example, cocoa butter, and then shaping the resulting mixture.

Extracellular protein degraders of the present invention and pharmaceutically acceptable composition, salts, isotopic analogs, or prodrugs thereof, may be formulated in dosage unit form for ease of administration and uniformity of dosage. It will be understood, however, that the total daily usage of the compositions comprising an extracellular protein degrader as described herein will be decided by the attending physician within the scope of sound medical judgment. The specific therapeutically effective dose level for any particular subject or organism will depend upon a variety of factors including the disease, disorder, or condition being treated and the severity of the disorder; the activity of the specific extracellular protein degrader employed; the specific composition employed; the age, body weight, general health, sex and diet of the subject; the time of administration, route of administration, and rate of excretion of the specific extracellular protein degrader employed; the duration of the treatment; drugs used in combination or coincidental with the specific extracellular protein degrader employed; and like factors well known in the medical arts.

The extracellular protein degraders and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), the condition of the subject (e.g., whether the subject is able to tolerate oral administration).

The exact amount of an extracellular protein degrader required to achieve an effective amount will vary from subject to subject, depending, for example, on species, age, and general condition of a subject, severity of the side effects or disorder, identity of the particular extracellular protein degrader (s), mode of administration, and the like. The desired dosage can be delivered using any frequency determined to be useful by the health care provider, including three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

It will be also appreciated that an extracellular protein degrader or composition, as described herein, can be administered in combination with one or more additional therapeutically active agents. The extracellular protein degraders or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder (for example, an extracellular protein degrader can be administered in combination with an anti-inflammatory agent, anti-cancer agent, immunosuppressant, etc.), and/or it may achieve different effects (e.g., control of adverse side-effects, e.g., emesis controlled by an antiemetic).

The extracellular protein degrader or composition can be administered concurrently with, prior to, or subsequent to, one or more additional therapeutically active agents. In general, each agent will be administered at a dose and/or on a time schedule determined for that agent. It will further be appreciated that the additional therapeutically active agent used in this combination can be administered together in a single composition or administered separately in different compositions. The particular combination to employ in a regimen will take into account compatibility of the inventive extracellular protein degrader with the additional therapeutically active agent and/or the desired therapeutic effect to be achieved. In general, it is expected that additional therapeutically active agents used in combination be used at levels that do not exceed the levels at which they are used individually. In some embodiments, the levels used in combination will be lower than those used individually.

Exemplary additional therapeutically active agents include, but are not limited to, small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells. In certain embodiments, the additional therapeutically active agent is an anti-cancer agent, e.g., radiation therapy and/or one or more chemotherapeutic agents.

In certain aspects, a treatment regimen is provided comprising the administration of an extracellular protein degrader of the present invention or a pharmaceutically acceptable composition, salt, isotopic analog (such as a deuterated derivative), or prodrug thereof in combination or in alternation with at least one additional therapeutic agent. The combinations and/or alternations can be administered for beneficial, additive, or synergistic effect in the treatment of Target Extracellular Protein-mediated disorders.

IV. Methods of Treatment

The Targeted Extracellular Proteins of the current invention may include, but are not limited to, immunoglobulins, cytokines, chemokines, growth factors, coagulation factors, extracellular matrix proteins and proteins involved in formation and/or degradation of the extracellular matrix, esterases, lipases, peptidases, convertases, among others. These proteins mediate a range of diseases that can be treated with an effective amount of the disclosed ASGPR-binding Extracellular Protein Degraders described herein.
Immunoglobulin Mediated Disorders In certain aspects, a treatment is provided comprising administering an effective amount of an immunoglobulin degrader of the present invention or a pharmaceutically acceptable composition, salt, isotopic analog, or prodrug thereof to a patient with an immunoglobulin-mediated disease.
Immunoglobulin G IgG Immunoglobulin G (IgG) is the main type of antibody found in all body fluids (for example, blood and extracellular fluid) and protects against bacterial and viral infections. It represents approximately 75% of serum antibodies in humans and is thus the most common type of antibody found in circulation. IgG antibodies are generated following class switching and maturation of the antibody response, thus they participate predominantly in the secondary immune response. (Vidarsson, Gestur; et al., "IgG subclasses and allotypes: from structure to effector functions". Frontiers in Immunology, 2014, 5: 520).

IgG can be divided into 4 distinct subclasses (IgG1, IgG2, IgG3, & IgG4). Within each of these two species, the IgG subclasses are 95% identical at the amino acid level. The relatively minor differences have important functional differences. The evolution of IgG subclass switches is regulated by interaction with T cells and follows a 1-way direction (IgG3→IgG1→IgG2→IgG4). (Valenzuela et al., "The Biology of IgG Subclasses and Their Clinical Relevance to Transplantation", Transplantation, 2018 January; 102(1S Suppl 1):S7-S13) The differences are mainly in the size and configuration of the hinge region, glycosylation sites, and structures, as well as a few key amino acid changes that impact the ability to interact with complement and Fc receptors. These changes, particularly the size of the hinge region, have an impact on the flexibility of the antibody at the hinge.

IgG1 and IgG3 are monomeric (2 heavy chains & 2 light chains) and bivalent (2 variable regions). IgG2 has a distinct disulfide bond pattern which allows for two monomeric IgG2 antibodies to form a dimeric (and tetravalent) structure through unique inter-molecule disulfide bonds. IgG4 has an even more unique structure (again dictated by the heavy chain intrachain disulfide bond). The intrachain disulfide bonds (there are two) can be reduced, which generates a monovalent structure. In addition, the monovalent structures can reform the disulfide bonds, but may not be the same IgG4 monovalent chain; meaning the resulting IgG4 will be a bivalent monomer but will have two different variable regions.

By binding many kinds of pathogens such as viruses, bacteria, and fungi, IgG helps protect the body from infection. However, aberrant IgG activity is associated with a variety of disorders, in these disorders the selective targeting of IgG can be particularly beneficial when the present invention is used in the treatment of a disease known to be caused primarily by IgG, such as thyroid eye disease, myasthenia gravis, chronic inflammatory demyelinating polyneuropathy, warm autoimmune hemolytic anemia, and type-1 autoimmune pancreatitis.

In certain aspects the treatment of a disorder mediated by IgG is provided comprising administering an effective amount of an IgG degrader or a pharmaceutically acceptable salt thereof to the patient. In certain embodiments the IgG disorder is selected from antiphospholipid Ab syndrome, Behcet syndrome, Hashimoto thyroiditis, MGUS, necrobiotic xanthogranuloma, rheumatoid arthritis, cancer, for example multiple myeloma or peripheral multiple myeloma, paraproteinemia, chronic urticaria, scleroderma, scleromyxedema, thrombocytopenia for example heparin-induced thrombocytopenia, cryoglobulinema, granulomatosis with polyanglitits, for example ANCA associated vasculitis, idiopathic thrombocytopenic purpura, thrombocytopenia, IgG4-RD, paroxysmal nocturnal hemoglobinuria (PNH), warm autoimmune hemolytic anemia, rhabdomyolysis, lupus nephritis, acute disseminated encephalomyelitis, Guillaine-Barre syndrome, chronic inflammatory demyelinating polyneuropathy, Miller Fisher syndrome, neuromyelitis optica spectrum disorder, opsoclonus-myoclonus syndrome, pediatric autoimmune neuropsychiatric disorder associated with streptococcal infection (PANDAS), peripheral neuropathy, transverse myelitis, fibrosis, IPF/fibrosis, and transplantation rejection.

In certain embodiments the disease is mediated by IgG.
Immunoglobulin G (IgG) mediates a range of autoimmune, infectious and metabolic diseases, including systemic fibroinflammatory disease. In addition, overexpression of IgG4 is associated with IgG4-related diseases, which generally include multiple organs, and disorders include type 1 autoimmune pancreatitis, interstitial nephritis, Riedel's thyroiditis, storiform fibrosis, Mikulicz's disease, Küttner's tumor, inflammatory pseudotumors (in various sites of the body), mediastinal fibrosis, retroperitoneal fibrosis (Ormond's disease), aortitis and periaortitis, proximal biliary strictures, idiopathic hypocomplementemic tubulointerstitial nephritis, multifocal fibrosclerosis, pachymeningitis, pancreatic enlargement, tumefactive lesions, pericarditis, rheumatoid arthritis (RA), inflammatory bowel disease, multiple sclerosis, myasthenia gravis, ankylosing spondylitis, primary Sjögren's syndrome, psoriatic arthritis, systemic lupus erythematosus (SLE), sclerosing cholangitis, IgG monoclonal gammopathy, monoclonal gammopathy of undetermined significance (MGUS), melanoma, bullous pemphigoid, Goodpasture disease, encephalitis, thrombotic thrombocytopenic purpura, chronic inflammatory polyneuropathy, limbic encephalitis, neuromyotonia, Morvan syndrome, pemphigus foliaceus, pemphigus vulgaris, REM and non-REM parasomnia, and membranous nephropathy, multiple sclerosis, hyperthyroid Grave's disease, epidermolysis bullosa acquisita, pemphigoid gestationis, anti-p200 pemphigoid, and paraneoplastic pemphigus, among others.

In certain embodiments the disease is mediated by IgA

Aberrant expression of immunoglobulin A (IgA) mediates a range of autoimmune and immune-mediated disorders, including IgA nephropathy (also known as Berger's disease), celiac disease, Crohn's disease, Henoch-Schonlein purpura (HSP) (also known as IgA vasculitis), IgA pemphigus, dermatitis herpetiformis, inflammatory bowel disease (IBD), Sjögren's syndrome, ankylosing spondylitis, alcoholic liver cirrhosis, acquired immunodeficiency syndrome, IgA multiple myeloma, α-chain disease, IgA monoclonal gammopathy, monoclonal gammopathy of undetermined significance (MGUS), linear IgA bullous dermatosis, rheumatoid arthritis, ulcerative colitis, and primary glomerulonephritis, among others.

Immunoglobulin E IgG

In certain embodiments the disease is mediated by IgE.

Immunoglobulin E (IgE) is a strong mediator of allergic disease, including but not limited to, atopic asthma, allergic rhinitis, atopic dermatitis, cutaneous contact hypersensitivity, IgE-mediated food allergy, IgE-mediated animal allergies, allergic conjunctivitis, allergic urticaria, anaphylactic shock, nasal polyposis, keratoconjunctivitis, mastocytosis, eosinophilic gastrointestinal disease, bullous pemphigoid, chemotherapy induced hypersensitivity reaction, seasonal allergic rhinitis, interstitial cystitis, eosinophilic esophagitis, angioedema, acute interstitial nephritis, atopic eczema, eosinophilic bronchitis, chronic obstructive pulmonary disease, gastroenteritis, hyper-IgE syndrome (Job's Syndrome), IgE monoclonal gammopathy, monoclonal gammopathy of undetermined significance (MGUS), pemphigus vulgaris, mucus membrane pemphigoid, chronic urticaria, autoimmune uveitis, rheumatoid arthritis, autoimmune pancreatitis, and allergic rhinoconjunctivitis among others.

Additional Immunoglobulin Disorders

In certain embodiments the disease is mediated by multiple immunoglobulins.

Non-limiting examples of immunoglobulin mediated diseases include: systemic fibroinflammatory disease, type 1 autoimmune pancreatitis, interstitial nephritis, Riedel's thyroiditis, storiform fibrosis, Mikulicz's disease, Küttner's tumor, inflammatory pseudotumors (in various sites of the body), mediastinal fibrosis, retroperitoneal fibrosis (Ormond's disease), aortitis and periaortitis, proximal biliary strictures, idiopathic hypocomplementemic tubulointerstitial nephritis, multifocal fibrosclerosis, pachymeningitis, pancreatic enlargement, tumefactive lesions, pericarditis, rheumatoid arthritis (RA), inflammatory bowel disease, multiple sclerosis, myasthenia gravis, ankylosing spondylitis, primary Sjögren's syndrome, psoriatic arthritis, systemic lupus erythematosus (SLE), sclerosing cholangitis, IgG monoclonal gammopathy, monoclonal gammopathy of undetermined significance (MGUS), melanoma, bullous pemphigoid, Goodpasture disease, encephalitis, thrombotic thrombocytopenic purpura, chronic inflammatory polyneuropathy, limbic encephalitis, neuromyotonia, Morvan syndrome, pemphigus foliaceus, pemphigus vulgaris, REM and non-REM parasomnia, and membranous nephropathy, multiple sclerosis, hyperthyroid Grave's disease, epidermolysis bullosa acquisita, pemphigoid gestationis, anti-p200 pemphigoid, paraneoplastic pemphigus, IgA nephropathy (also known as Berger's disease), celiac disease, Crohn's disease, Henoch-Schonlein purpura (HSP) (also known as IgA vasculitis), IgA pemphigus, dermatitis herpetiformis, inflammatory bowel disease (IBD), Sjögren's syndrome, ankylosing spondylitis, alcoholic liver cirrhosis, acquired immunodeficiency syndrome, IgA multiple myeloma, α-chain disease, IgA monoclonal gammopathy, monoclonal gammopathy of undetermined significance (MGUS), linear IgA bullous dermatosis, rheumatoid arthritis, ulcerative colitis, primary glomerulonephritis, atopic asthma, allergic rhinitis, atopic dermatitis, cutaneous contact hypersensitivity, IgE-mediated food allergy, IgE-mediated animal allergies, allergic conjunctivitis, allergic urticaria, anaphylactic shock, nasal polyposis, keratoconjunctivitis, mastocytosis, eosinophilic gastrointestinal disease, bullous pemphigoid, chemotherapy induced hypersensitivity reaction, seasonal allergic rhinitis, interstitial cystitis, eosinophilic esophagitis, angioedema, acute interstitial nephritis, atopic eczema, eosinophilic bronchitis, chronic obstructive pulmonary disease, gastroenteritis, hyper-IgE syndrome (Job's Syndrome), IgE monoclonal gammopathy, monoclonal gammopathy of undetermined significance (MGUS), pemphigus vulgaris, mucus membrane pemphigoid, chronic urticaria, autoimmune uveitis, rheumatoid arthritis, autoimmune pancreatitis, and allergic rhinoconjunctivitis among others.

Additional Disorders

Immunoglobulins are also associated with various complex protein signaling cascades, for example the complement cascade, and thus their degradation can treat diseases that are mediated by these protein signaling cascades. Additional examples of disorders that can be treated by compounds of the present invention include autoimmune, other immune dysfunctions, complement mediated disorders, abnormal cellular proliferation, cancer, tumors, hematology-related disorders, renal disorders and liver disorders. In certain embodiments the disorder is mediated by an extracellular protein other than an immunoglobulin and a compound of the present invention that degrades that extracellular protein is administered to a patient in need thereof.

In certain embodiments, the degrader or its salt or composition as described herein is used in the treatment of an autoimmune disorder. In some aspects, the extracellular protein is an Ig, such as IgA or IgG. IgG degradation can treat for example, thyroid eye disease, myasthenia gravis, chronic inflammatory demyelinating polyneuropathy, and warm autoimmune hemolytic anemia.

Non-limiting examples of autoimmune disorders include: lupus, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), diabetes, multiple sclerosis, pernicious anemia, psoriasis, rheumatoid arthritis, sarcoidosis, and scleroderma.

In an embodiment, the degrader or its salt or composition as described herein is used in the treatment of lupus. Non-limiting examples of lupus include lupus erythematosus, cutaneous lupus, discoid lupus erythematosus, chilblain lupus erythematosus, or lupus erythematosus-lichen planus overlap syndrome. Lupus erythematosus is a general category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Multiple Sclerosis is an autoimmune demyelinating disorder that is believed to be T lymphocyte dependent. MS generally exhibits a relapsing-remitting course or a chronic progressive course. The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+T lymphocytes are the predominant cell type present at these lesions. The hallmark of the MS lesion is plaque, an area of demyelination sharply demarcated from the usual white matter seen in MRI scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4+ T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed. Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood.

Diabetes can refer to either type 1 or type 2 diabetes. In some embodiments the degrader or its salt or composition as described herein is provided at an effective dose to treat a patient with type 1 diabetes. In certain aspects the degrader or its salt or composition as described herein is provided at an effective dose to treat a patient with type 2 diabetes.

Type 1 diabetes is an autoimmune disease. An autoimmune disease results when the body's system for fighting infection (the immune system) turns against a part of the body. Type 1 diabetes often occurs when the pancreas is damaged by the immune system. The damaged pancreas then produces little or no insulin.

As examples, the degrader or its salt or composition as described herein is useful for treating or preventing a disorder selected from autoimmune oophoritis, endometriosis, autoimmune orchitis, Ord's thyroiditis, autoimmune enteropathy, coeliac disease, Hashimoto's encephalopathy, antiphospholipid syndrome (APLS) (Hughes syndrome), aplastic anemia, autoimmune lymphoproliferative syndrome (Canale-Smith syndrome), autoimmune neutropenia, Evans syndrome, pernicious anemia, pure red cell aplasia, thrombocytopenia, adipose dolorosa (Dercum's disease), adult onset Still's disease, ankylosing spondylitis, CREST syndrome, drug-induced lupus, eosinophilic fasciitis (Shulman's syndrome), Felty syndrome, IgG4-related disease, mixed connective tissue disease (MCTD), palindromic rheumatism (Hench-Rosenberg syndrome), Parry-Romberg syndrome, Parsonage-Turner syndrome, relapsing polychondritis (Meyenburg-Altherr-Uehlinger syndrome), retroperitonial fibrosis, rheumatic fever, Schnitzler syndrome, fibromyalgia, neuromyotonia (Isaac's disease), paraneoplastic degeneration, autoimmune inner ear disease, Meniere's disease, interstitial cystitis, autoimmune pancreatitis, zika virus-related disorders, chikungunya virus-related disorders, subacute bacterial endocarditis (SBE), IgA nephropathy, IgA vasculitis, polymyalgia rheumatic, rheumatoid vasculitis, alopecia areata, autoimmune progesterone dermatitis, dermatitis herpetiformis, erythema nodosum, gestational pemphigoid, hidradenitis suppurativa, lichen sclerosus, linear IgA disease (LAD), morphea, myositis, pityriasis lichenoides et varioliformis acuta, vitiligo post-myocardial infarction syndrome (Dressler's syndrome), post-pericardiotomy syndrome, autoimmune retinopathy, Cogan syndrome, Graves opthalmopathy, ligneous conjunctivitis, Mooren's ulcer, opsoclonus myoclonus syndrome, optic neuritis, retinocochleocerebral vasculopathy (Susac's syndrome), sympathetic opthalmia, Tolosa-Hunt syndrome, interstitial lung disease, antisynthetase syndrome, Addison's disease, autoimmune polyendocrine syndrome (APS) type I, autoimmune polyendocrine syndrome (APS) type II, autoimmune polyendocrine syndrome (APS) type III, disseminated sclerosis (multiple sclerosis, pattern II), rapidly progressing glomerulonephritis (RPGN), juvenile rheumatoid arthritis, enthesitis-related arthritis, reactive arthritis (Reiter's syndrome), autoimmune hepatitis or lupoid hepatitis, primary biliary cirrhosis (PBS), primary sclerosing cholangitis, microscopic colitis, latent lupus (undifferentiated connective tissue disease (UCTD)), acute disseminated encephalomyelitis (ADEM), acute motor axonal neuropathy, anti-n-methyl-D-aspartate receptor encephalitis, Balo concentric sclerosis (Schilders disease), Bickerstaff's encephalitis, chronic inflammatory demyelinating polyneuropathy, idiopathic inflammatory demyelinating disease, Lambert-Eaton mysathenic syndrome, Oshtoran syndrome, pediatric autoimmune neuropsychiatric disorder associated with streptococcus (PANDAS), progressive inflammatory neuropathy, restless leg syndrome, stiff person syndrome, Sydenhem syndrome, transverse myelitis, lupus vasculitis, leukocytoclastic vasculitis, Microscopic Polyangiitis, polymyositis or ischemic-reperfusion injury of the eye.

In some aspects, the disorder treated by the degrader or its salt or composition as described herein is selected from fatty liver and conditions stemming from fatty liver, such as nonalcoholic steatohepatitis (NASH), liver inflammation, cirrhosis and liver failure.

In other embodiments, the degrader or its salt or composition as described herein is used to modulate an immune response prior to or during surgery or other medical procedure. Non-limiting examples are the use in connection with acute or chronic graft versus host disease, which is a common complication as a result of allogeneic tissue transplant, and can also occur as a result of a blood transfusion.

In certain embodiments, the present invention provides a method of treating or preventing dermatomyositis by administering to a subject in need thereof an effective amount of the degrader or its salt or composition as described herein.

In certain embodiments, the present invention provides a method of treating or preventing amyotrophic lateral sclerosis by administering to a subject in need thereof an effective amount of the degrader or its salt or composition as described herein.

In certain embodiments, the present invention provides a method of treating or preventing abdominal aortic aneurysm, hemodialysis complications, hemolytic anemia, or hemodialysis by administering to a subject in need thereof an effective amount of the degrader or its salt or composition as described herein.

In certain embodiments, a method is provided for the treatment or prevention of cytokine or inflammatory reactions in response to the administration of pharmaceutical or biotherapeutic (e.g. CAR T-cell therapy or monoclonal antibody therapy) in a host by administering an effective amount of the degrader or its salt or composition as described herein. Various types of cytokine or inflammatory reactions may occur in response to a number of factors, such as the administrations of biotherapeutics. In certain aspects, the cytokine or inflammatory reaction is cytokine release syndrome. In one embodiment, the cytokine or inflammatory reaction is tumor lysis syndrome (which also leads to cytokine release). Symptoms of cytokine release syndrome range from fever, headache, and skin rashes to bronchospasm, hypotension and even cardiac arrest. Severe cytokine release syndrome is described as cytokine storm, and can be fatal.

In another embodiment, the disorder is episcleritis, idiopathic episcleritis, anterior episcleritis, or posterior episcleritis. In one embodiment, the disorder is idiopathic anterior uveitis, HLA-B27 related uveitis, herpetic keratouveitis, Posner Schlossman syndrome, Fuch's heterochromic iridocyclitis, or cytomegalovirus anterior uveitis.

In another embodiment, the present invention provides a method of treating or preventing a C3 glomurenopathy by administering to a subject in need thereof an effective amount of the degrader or its salt or composition as described herein. In one embodiment, the disorder is selected from dense deposit disease (DDD) and C3 glomerulonephritis (C3GN).

In yet another embodiment, the present invention provides a method of treating or preventing a IC-MPGN by administering to a subject in need thereof an effective amount of the degrader or its salt or composition as described herein.

In a further embodiment, the present invention provides a method of treating or preventing a paroxysmal nocturnal hemoglobinuria (PNH) by administering to a subject in need thereof an effective amount of the degrader or its salt or composition as described herein.

In another embodiment, the present invention provides a method of treating or preventing age-related macular degeneration (AMD) by administering to a subject in need thereof an effective amount of the degrader or its salt or composition as described herein.

In one embodiment, the present invention provides a method of treating or preventing rheumatoid arthritis by administering to a subject in need thereof an effective amount of the degrader or its salt or composition as described herein.

In one embodiment, the present invention provides a method of treating or preventing multiple sclerosis by administering to a subject in need thereof an effective amount of the degrader or its salt or composition as described herein.

In one embodiment, the present invention provides a method of treating or preventing myasthenia gravis by administering to a subject in need thereof an effective amount of the degrader or its salt or composition as described herein.

In one embodiment, the present invention provides a method of treating or preventing atypical hemolytic uremic syndrome (aHUS) by administering to a subject in need thereof an effective amount of the degrader or its salt or composition as described herein.

In one embodiment, the present invention provides a method of treating or preventing neuromyelitis optica (NMO) by administering to a subject in need thereof an effective amount of the degrader or its salt or composition as described herein.

In yet other embodiments, the present invention provides a method of treating or preventing a disorder as described below by administering to a subject in need thereof an effective amount of the degrader or its salt or composition as described herein, including: for example: vitritis, sarcoidosis, syphilis, tuberculosis, or Lyme disease; retinal vasculitis, Eales disease, tuberculosis, syphilis, or toxoplasmosis; neuroretinitis, viral retinitis, or acute retinal necrosis; varicella zoster virus, herpes simplex virus, cytomegalovirus, Epstein-Barr virus, lichen planus, or Dengue-associated disease (e.g., hemorraghic Dengue Fever); Masquerade syndrome, contact dermatitis, trauma induced inflammation, UVB induced inflammation, eczema, granuloma annulare, or acne.

In additional embodiments, the disorder is selected from: acute myocardial infarction, aneurysm, cardiopulmonary bypass, dilated cardiomyopathy, complement activation during cardiopulmonary bypass operations, coronary artery disease, restenosis following stent placement, or percutaneous transluminal coronary angioplasty (PTCA); antibody-mediated transplant rejection, anaphylactic shock, anaphylaxis, allogenic transplant, humoral and vascular transplant rejection, graft dysfunction, graft-versus-host disease, Graves' disease, adverse drug reactions, or chronic graft vasculopathy; allergic bronchopulmonary aspergillosis, allergic neuritis, drug allergy, radiation-induced lung injury, eosinophilic pneumonia, radiographic contrast media allergy, bronchiolitis obliterans, or interstitial pneumonia; parkinsonism-dementia complex, sporadic frontotemporal dementia, frontotemporal dementia with Parkinsonism linked to chromosome 17, frontotemporal lobar degeneration, tangle only dementia, cerebral amyloid angiopathy, cerebrovascular disorder, certain forms of frontotemporal dementia, chronic traumatic encephalopathy (CTE), PD with dementia (PDD), argyrophilic grain dementia, dementia pugilistica, dementia with Lewy Bodies (DLB), or multi-infarct dementia; Creutzfeldt-Jakob disease, Huntington's disease, multifocal motor neuropathy (MMN), prion protein cerebral amyloid angiopathy, polymyositis, postencephalitic parkinsonism, subacute sclerosing panencephalitis, non-Guamanian motor neuron disease with neurofibrillary tangles, neural regeneration, or diffuse neurofibrillary tangles with calcification.

In further embodiments, the disorder is selected from: atopic dermatitis, dermatitis, dermatomyositis bullous pemphigoid, scleroderma, sclerodermatomyositis, psoriatic arthritis, pemphigus vulgaris, Discoid lupus erythematosus, cutaneous lupus, chilblain lupus erythematosus, or lupus erythematosus-lichen planus overlap syndrome; cryoglobulinemic vasculitis, mesenteric/enteric vascular disorder, peripheral vascular disorder, antineutrophil cytoplasm antibody (ANCA)-associated vasculitis (AAV), IL-2 induced vascular leakage syndrome, or immune complex vasculitis; angioedema, low platelets (HELLP) syndrome, sickle cell disease, platelet refractoriness, red cell casts, or typical or infectious hemolytic uremic syndrome (tHUS); hematuria, hemorrhagic shock, drug-induced thrombocytopenia, autoimmune hemolytic anemia (AIHA), azotemia, blood vessel and/or lymph vessel inflammation, rotational atherectomy, or delayed hemolytic transfusion reaction; British type amyloid angiopathy, Buerger's disease, bullous pemphigoid, C1q nephropathy, cancer, or catastrophic antiphospholipid syndrome.

In other embodiments, the disorder is selected from: wet (exudative) AMD, dry (non-exudative) AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, pathological myopia, or RPE degeneration; pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen; chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita; essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch-Schonlein purpura nephritis, or abnormal urinary sediments; hepatitis, hepatitis A, hepatitis B, hepatitis C or human immunodeficiency virus (HIV), a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae; *Neisseria meningitidis*, shiga toxin *E. coli*-related hemolytic uremic syndrome (STEC-HUS), hemolytic uremic syndrome (HUS); *Streptococcus*, or poststreptococcal glomerulonephritis.

In further embodiments, the disorder is selected from: hyperlipidemia, hypertension, hypoalbuminemia, hypobolemic shock, hypocomplementemic urticarial vasculitis syndrome, hypophosphastasis, hypovolemic shock, idiopathic pneumonia syndrome, or idiopathic pulmonary fibrosis; inclusion body myositis, intestinal ischemia, iridocyclitis, iritis, juvenile chronic arthritis, Kawasaki's disease (arteritis), or lipiduria; membranoproliferative glomerulonephritis (MPGN) I, microscopic polyangiitis, mixed cryoglobulinemia, molybdenum cofactor deficiency (MoCD) type A, pancreatitis, panniculitis, Pick's disease, polyarteritis nodosa (PAN), progressive subcortical gliosis, proteinuria, reduced glomerular filtration rate (GFR), or renovascular disorder; multiple organ failure, multiple system atrophy (MSA), myotonic dystrophy, Niemann-Pick disease type C, chronic demyelinating diseases, or progressive supranuclear palsy; spinal cord injury, spinal muscular atrophy, spondyloarthropathies, Reiter's syndrome, spontaneous fetal loss, recurrent fetal loss, pre-eclampsia, synucleinopathy, Takayasu's arteritis, post-partum thryoiditis, thyroiditis, Type I cryoglobulinemia, Type II mixed cryoglobulinemia, Type III mixed cryoglobulinemia, ulcerative colitis, uremia, urticaria, venous gas embolus (VGE), or Wegener's granulomatosis; von Hippel-Lindau disease, histoplasmosis of the eye, hard drusen, soft drusen, pigment clumping, or photoreceptor and/or retinal pigmented epithelia (RPE) loss.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

In other embodiments, the disorder is selected from glaucoma, diabetic retinopathy, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, diabetic macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, postoperative inflammation, and retinal vein occlusion, or central retinal vein occlusion (CVRO).

Disorders that may be treated or prevented by the degrader or its salt or composition as described herein also include, but are not limited to: hereditary angioedema, capillary leak syndrome, hemolytic uremic syndrome (HUS), neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome; inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, system lupus erythematosus (SLE), lupus nephritides, arthritis, immune complex disorders and autoimmune diseases, systemic lupus, or lupus erythematosus; ischemia/reperfusion injury (I/R injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes; Alzheimer's dementia, stroke, schizophrenia, traumatic brain injury, trauma, Parkinson's disease, epilepsy, transplant rejection, prevention of fetal loss, biomaterial reactions (e.g. in hemodialysis, implants), hyperacute allograft rejection, xenograft rejection, transplantation, psoriasis, burn injury, thermal injury including burns or frostbite, or crush injury; asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

In another embodiment, a method for the treatment of sickle cell in a host is provided that includes the administration of an effective amount of the degrader or its salt or composition as described herein. In one embodiment, a method for the treatment of immunothrombocytopenic purpura (ITP), thrombotic thrombocytopenic purpura (TTP), or idiopathic thrombocytopenic purpura (ITP) in a host is provided that includes the administration of an effective amount of the degrader or its salt or composition as described herein. In one embodiment, a method for the treatment of ANCA-vasculitis in a host is provided that includes the administration of an effective amount of the degrader or its salt or composition as described herein. In one embodiment, a method for the treatment of IgA nephropathy in a host is provided that includes the administration of an effective amount of the degrader or its salt or composition as described herein. In one embodiment, a method for the treatment of rapidly progressing glomerulonephritis (RPGN), in a host is provided that includes the administration of an effective amount of the degrader or its salt or composition as described herein. In one embodiment, a method for the treatment of lupus nephritis, in a host is provided that includes the administration of an effective amount of the degrader or its salt or composition as described herein. In one embodiment, a method for the treatment of hemorraghic dengue fever, in a host is provided that includes the administration of an effective amount of the degrader or its salt or composition as described herein.

In other aspects, an effective amount of the degrader or its salt or composition as described herein is used to treat an abnormal proliferation disorder such as a tumor or cancer.

Non-limiting examples of cancers that can be treated according to the present invention include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL)—also known as acute lymphoblastic leukemia or acute lymphoid leukemia (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt's lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CVL), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In another embodiment, the disorder is myelodysplastic syndrome (MDS).

In certain embodiments, the cancer is a hematopoietic cancer. In certain embodiments, the hematopoietic cancer is a lymphoma. In certain embodiments, the hematopoietic cancer is a leukemia. In certain embodiments, the leukemia is acute myelocytic leukemia (AML).

In certain embodiments, the proliferative disorder is a myeloproliferative neoplasm. In certain embodiments, the myeloproliferative neoplasm (MPN) is primary myelofibrosis (PMF).

In certain embodiments, the cancer is a solid tumor. A solid tumor, as used herein, refers to an abnormal mass of tissue that usually does not contain cysts or liquid areas. Different types of solid tumors are named for the type of cells that form them. Examples of classes of solid tumors include, but are not limited to, sarcomas, carcinomas, and lymphomas, as described above herein. Additional examples of solid tumors include, but are not limited to, squamous cell carcinoma, colon cancer, breast cancer, prostate cancer, lung cancer, liver cancer, pancreatic cancer, and melanoma.

Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic microangiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

In certain embodiments, the condition is associated with an immune response.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In other non-limiting embodiments, degraders of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

Exemplary cancers which may be treated by the present disclosed compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitt's lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

Nonlimiting general examples of disorders mediated by extracellular proteins also include, but are not limited to: AMD, macular edema, DME, diabetic retinopathy, mCNV; neurodegenerative disorders, metastatic colorectal cancer, non-squamous non-small-cell lung carcinoma, GMB, metastatic renal cell carcinoma, cervical cancer, AA amyloidosis, amyloid light chain (AL) amyloidosis, ankylosing spondylitis, antiphospholipid Ab syndrome, asthma, progression of parasite *Schistosoma mansoni* infection (IL-13), ATTR amyloidosis, Behcet syndrome, sepsis, inflammation, rheumatoid arthritis, atherosclerosis, ischemia/reperfusion injury; MGUS, Necrobiotic xanthogranuloma, JIA, psoriatic arthritis, plaque psoriasis, Crohn's disease, ulcerative colitis, Hidradenitis suppurativa uveitis; GvH disease; Castleman's disease, liver fibrosis, Still's Disease; cutaneous skin diseases including atopic dermatitis, transplant rejection, multiple myeloma, osteosclerotic multiple myeloma with peripheral neuropathy; pancreatic tumors; paraproteinemia (NR), prostate, gastric cancer; glioblastoma multiforme; acute coronary syndrome; hyperlipidemia (Rare/Broad), chronic urticaria, scleroderma, scleromyxedema, hereditary angioedema, clotting disorders, heparin-induced thrombocytopenia; Acquired Von Willebrand disease (AVWD), antiphospholipid antibody syndrome (APS or APLS); cryoglobulinemia; granulomatosis with polyangiitis (Wegener's)—sub-type of ANCA-associated vasculitis; idiopathic (Immune); thrombocytopenic purpura; IgG4-RD; Non-IgM MGUS; X-linked hypophosphatemia; Multiple System Atrophy (MSA), Parkinson's disease, Cachexia, Sarcopenia, Sporadic inclusion body myositis, muscular dystrophy, COPD; rhabdomyolysis; dialysis-related amyloidosis; focal segmental glomerulosclerosis (FSGS); IgA nephropathy (IgAN) and Henoch Schonlein Purpura (HSP); acute disseminated encephalomyelitis (ADEM); acute inflammatory demyelinating polyneuropathy (AIDP); Guillaine-Barre Syndrome; Alzheimer' disease & FTD; chronic inflammatory demyelinating polyneuropathy (CIDP); Creutzfeldt-Jakob disease (CJD); Huntington's disease; Miller Fisher Syndrome; Neuromyelitis optica spectrum disorder (NMOSD); Opsoclonus-myoclonus syndrome; PANDAS syndrome (pediatric autoimmune neuropsychiatric disorders associated with Streptococcal infections); Transverse myelitis; Emphysema, respiratory failure; Anthrax; Botulism; Sepsis; *Staph. aureus* toxic shock syndrome; Tetanus; Transplantation; Acromegaly; Cushing's disease; prion disease; secondary membranous nephropathy; and vasculitis.

Disorders Mediated by Other Extracellular Proteins

In certain embodiments the extracellular protein degrading compound of the present invention degrades a protein other than immunoglobulin to treat a disorder described above. Non-limiting examples of disorders and Extracellular Proteins include:

Cytokines/Chemokines
1) TNF-α mediates a number of disorders, including but not limited to rheumatoid arthritis, inflammatory bowel disease, graft-vs-host disease, ankylosing spondylitis, psoriasis, hidradenitis suppurativa, refractory asthma, systemic lupis erthyematosus, diabetes, and the induction of cachexia.
2) IL-2 mediates host versus graft rejection in transplants and autoimmune disorders, including, but not limited to, multiple sclerosis, idiopathic arthritis, iritis, anterior uveitis, IL-2 induced hypotension, psoriasis, and other autoimmune disorders 3) IL-1 mediates a number of auto-inflammatory and autoimmune disorders, including, but
not limited to, Blau syndrome, cryopyrin-associated periodic syndromes, familial Mediterranean fever, Majeed syndrome; mevalonate kinase deficiency syndrome, pyogenic arthritis-pyoderma gangrenosum-acne syndrome, tumor necrosis factor receptor-associated periodic syndrome, Behçet's Disease, Sjogren's Syndrome, gout and chondrocalcinosis, periodic fever, aphthous stomatitis, pharyngitis, and cervical adenitis (or PFAPA) syndrome, rheumatoid arthritis, Type 2 diabetes mellitus, acute pericarditis, Chronic interstitial lung diseases (ILDs), and Still's disease amongst others.
4) IFN-γ mediates a wide range of autoimmune disorders, including, but not limited to rheumatoid arthritis, multiple sclerosis (MS), corneal transplant rejection, and various autoimmune skin diseases such as psoriasis, alopecia areata, vitiligo, acne vulgaris, and others.
5) IL-21 mediates a number of autoimmune disorders, including Sjögren's syndrome, systemic lupus erythematosus, type 1 diabetes, multiple sclerosis, rheumatoid arthritis, and inflammatory bowel disease.
6) IL-22 mediates a number of autoimmune disorders, including, but not limited to, graft versus host disease (GVHD), psoriasis, rheumatoid arthritis, atopic dermatitis, and asthma.
7) IL-10 has been implicated in tumor survival and protection against cytotoxic chemotherapeutic drugs.
8) IL-5 has been implicated in a number of allergic disorders, including, but not limited to, asthma, nasal polyposis, atopic dermatitis, eosinophilic esophagitis, hypereosinophilic syndrome, and Churg-Strauss syndrome.
9) IL-6 has been implicated in a number of inflammatory diseases and cancers, including, but not limited to, Castleman's disease, metastatic castration-associated prostate cancer, renal cell carcinoma, large-cell lung carcinoma, ovarian cancer, rheumatoid arthritis, asthma.
10) IL-8 has been implicated in the promotion of tumor progression, immune escape, epithelial-mesenchymal transition, and recruitment of myeloid-derived suppressor cells. Studies have demonstrated that high serum IL-8 levels correlate with poor prognosis in many malignant tumors. Preclinical studies have shown that IL-8 blockade may reduce mesenchymal features in tumor cells, making them less resistant to treatment.
11) C—C motif chemokine ligand 2 (CCL2) has been implicated in the recruitment of monocytes into the arterial wall during the disease process of atherosclerosis.
12) Macrophage Migration Inhibitory Factor (MIF) is a mediator of tumor progression; systemic inflammation; atherosclerosis; rheumatoid arthritis; and systemic lupus erythematosus, among others.

Growth Factors
1) Fibroblast Growth Factor 1 (FGF1) can induce angiogenesis. FGF1 has been implicated in oncogenesis, cancer cell proliferation, resistance to anticancer therapies, and neoangiogenesis.
2) Fibroblast Growth Factor 2 (FGF2) has been implicated in oncogenesis, cancer cell proliferation, resistance to anticancer therapies, and neoangiogenesis.
3) Vascular Epithelial Growth Factor (VEGF-A) has been implicated in the vascularization and angiogenesis of tumors.
4) Transforming Growth Factor-β1 (TGF-β1) expression in the tumor microenvironment has been associated with a poor prognosis, and is implicated in TGF-β1 mediated tumor suppression via T-cell exclusion. TGF-β1 expression has also been implicated in hematological malignancies and fibrosis.
5) Transforming Growth Factor-β2 (TGF-β2) expression in the tumor microenvironment has been associated with a poor prognosis, and is implicated in TGF-β2 mediated tumor suppression via T-cell exclusion. TGF-β2 expression has also been implicated in hematological malignancies and fibrosis.
6) Placental Growth Factor (PGF) promotes cell tumor growth, and has been implicated in age-related macular degeneration (AMD) and choroidal neovascularization (CNV).

Esterase
1) Cholinesterase has been implicated in cognitive disorders such as dementia and Alzheimer's disease.

Coagulation Factors
1) Carboxypeptidase B2 has been implicated and targeted to inhibit thrombosis.
2) Coagulation Factor Xa is a mediator in the development of deep vein thrombosis and acute pulmonary embolism, and the risk of stroke and embolism in people with nonvalvular atrial fibrillation.
3) Coagulation Factor XI is a mediator in the development of deep vein thrombosis and acute pulmonary embolism, and the risk of stroke and embolism in people with nonvalvular atrial fibrillation.
4) Coagulation Factor XII has been implicated in the development of deep vein thrombosis and acute pulmonary embolism, and the risk of stroke and embolism in people with nonvalvular atrial fibrillation.
5) Coagulation Factor XIII has been implicated in the development of deep vein thrombosis and acute pulmonary embolism, and the risk of stroke and embolism in people with nonvalvular atrial fibrillation.
6) Prothrombin is involved in blood clot formation and arterial and venous thrombosis, and thromboembolism associated with atrial fibrillation.
7) Coagulation Factor VII is involved in blood clot formation and arterial and venous thrombosis, and thromboembolism associated with atrial fibrillation.
8) Coagulation Factor IX is involved in blood clot formation and arterial and venous thrombosis, and thromboembolism associated with atrial fibrillation.

Extracellular Matrix Proteins
1) Neutrophil Elastase—Neutrophil elastase has been implicated in a number of disorders, including lung disease, chronic obstructive pulmonary disease, pneumonia, respiratory distress, and acute lung injury (ALI), and cystic fibrosis, as well as chronic kidney disease.
2) Fibronectin-1—Interfering with FN polymerization may attenuate myofibroblasts and fibrosis and improve cardiac function after ischemia/reperfusion (I/R) injury.
3) Thrombospondin-1—TSP-1 has been implicated in a number of diseases, including in promoting certain cancers such as breast cancer, prostate cancer, melanoma, SCLC, osteosarcoma, cutaneous squamous cell carcinoma, oral squamous cell carcinoma, papillary thyroid carcinoma, thyroid cancer, medulloblastoma, and fibrotic disorders such as diabetes, liver fibrosis, and in multiple myeloma.
4) Urokinase-type Plasminogen Activator (UPA)—UPA has been implicated in vascular diseases and cancer progression. Elevated expression levels of urokinase and several other components of the plasminogen activation system are found to be correlated with tumor malignancy.
5) Plasminogen Activator, Tissue Type (TPA)—PLA has been shown activated in various cancers including oral malignancy.
6) Plasminogen (PLG)—PLG has been implicated in tumor invasion and inflammation.
7) Plasminogen Activator Inhibitor-1 (PAI-1)—PAI-1 has been implicated in angiogenesis, metastasis, and poor prognosis in tumors, including, but not limited to, oral cancers and breast cancers.

Peptidase
1) Kallikrein-1—Kallikrein has been implicated in adverse reactions in hereditary angioedema (HAE).
2) Plasma Kallikrein—Plasma kallikrein has been implicated in retinal dysfunction, the development of diabetic macular edema and hereditary angioedema (HAE).
3) Matrix Metallopeptidase-1—MMP-1 has been implicated in cardiovascular disease, development of fibrosis, and growth of certain cancers such as bladder cancer.
4) Phospholipase A2, Group IIA (PA2GA)—PA2GA has been implicated in a number of diseases, including cardiovascular diseases, atherosclerosis, immune disorders, and cancer.

Lipase
1) Lipoprotein Lipase—Lipoprotein lipase has been implicated in the development of cardiovascular disease and obesity.
2) Phospholipase A2, Group IB (PA21B)—PA21B has been implicated in a number of diseases, including cardiovascular diseases, atherosclerosis, immune disorders and cancer.

Convertase
1) Proprotein Convertase Subtilisin/Kexin Type 9 (PCSK-9)—PCSK-9 has been implicated in high blood cholesterol and the development of cardiovascular disease.

Certain targeted extracellular proteins include but are not limited to: SAA (serum amyloid A), amyloid light chains, antibodies to *Klebsiella* dipeptidase protein; Ig antibodies to anionic phospholipids and beta-2-glycoprotein-1; IL-13; MIF; Transthyretin (misfolded), IgG autoantibodies to thyroid peroxidase, thyroglobulin and TSH receptors; TNF-α; Protein arginine deiminase (PAD, PAD4); antibodies to citrullinated protein antibody (ACPA); anti-DNA antibodies; IL-17; Lysyl Oxidase 2 (LOXL2); IL-18; Blys; B cell activating factor (BAFF); CD40 (soluble); CXCL12; soluble PSMA; matrix metalloproteinase IX (MMP-9); hormone-sensitive lipase; lipoprotein-associated phospholipase A2; Factor Xa; DPP4; thrombin; PCSK9; ApoB-100; Complement component C3b; PKK (pre-kallikrein); Factor XI; PF4; Anti-vWF antibodies; anticardiolipin antibodies and lupus anticoagulant; FGF23 (fibroblast growth factor 23); Plasminogen activator inhibitor type 1 (PAI-1); Myeloperoxidase (MPO) extracellular; Myostatin; Beta2-m; suPAR (soluble urokinase plasminogen activator receptor), anti-ganglioside IgG; amyloid beta; Tau; CJD-associate prion; anti-ganglioside IgG; HTT; anti-ganglioside IgG; synuclein; elastase; PABA (protective antigen of *Bacillus anthracis*); edema factor; Botulinum toxin; *C. difficile* toxin B; hemolysin; tetanus toxin; IL-2; growth hormone and ACTH.

V. Combination Treatment

In certain aspects, a treatment regimen is provided comprising the administration of an effective amount of an extracellular protein degrader of the present invention or a pharmaceutically acceptable composition, salt, isotopic analog, or prodrug thereof in combination or in alternation with at least one additional therapeutic agent for the treatment of a disorder mediated by the Target Extracellular Protein, for example an immunoglobulin. The combinations and/or alternations disclosed herein can be administered for beneficial, additive, or synergistic effect in the treatment of extracellular protein mediated disorders.

In certain embodiments, a treatment regimen is provided for the treatment of IgA nephropathy comprising the administration of an immunoglobulin degrader of the present invention or a pharmaceutically acceptable composition, salt, isotopic analog, or prodrug thereof in combination or in alternation with at least one additional therapeutic agent. In certain embodiments, at least one of the additional therapeutic agents is an ACE inhibitor. In certain embodiments, at least one of the additional therapeutic agents is an AT1R antagonist. In certain embodiments, at least one of the additional therapeutic agents is an angiotensin receptor blocker. In certain embodiments, at least one of the additional therapeutic agents is an omega-3 fatty acid. In certain embodiments, at least one of the additional therapeutic agents is a corticosteroid. In certain embodiments, at least one of the additional therapeutic agents is a statin. In certain embodiments, at least one of the additional therapeutic agents is a diuretic. In certain embodiments, at least one of the additional therapeutic agents is an immunosuppressant. In certain embodiments, at least one of the additional therapeutic agents is selected from AVB-S6-500, iptacopan, atacicept, rituximab, BION-1301, mycophenolic acid, mycophenolate mofetil, allopurinol, blisibimod, bortezomib, paricalcitol, tacrolimus, aliskiren, enalapril, cemdisiran, irbesartan, rapamycin, calcitriol, and ravulizumab.

In certain embodiments, a treatment regimen is provided for the treatment of celiac disease comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a steroid. In certain embodiments, at least one of the additional therapeutic agents is a copper supplement. In certain embodiments, at least one of the additional therapeutic agents is a zinc supplement. In certain embodiments, at least one of the additional therapeutic agents is an iron supplement. In certain embodiments, at least one of the additional therapeutic agents is a folate supplement. In certain embodiments, at least one of the additional therapeutic agents is a vitamin B12 supplement. In certain embodiments, at least one of the additional therapeutic agents is a vitamin D supplement. In certain embodiments, at least one of the additional therapeutic agents is a vitamin K supplement. In certain embodiments, at least one of the additional therapeutic agents is selected from azathioprine, budesonide, and dapsone.

In certain embodiments, a treatment regimen is provided for the treatment of IgA vasculitis comprising the administration of an immunoglobulin degrader of the present invention or a pharmaceutically acceptable composition, salt, isotopic analog, or prodrug thereof in combination or in alternation with at least one additional therapeutic agent. In certain embodiments, at least one of the additional therapeutic agents is a steroid. In certain embodiments, at least one of the additional therapeutic agents is an anti-inflammatory.

In certain embodiments, a treatment regimen is provided for the treatment of IgA pemphigus comprising the administration of an immunoglobulin degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is a retinoid. In certain embodiments, at least one of the additional therapeutic agents is selected from dapsone, colchicine, mycophenolate mofetil, and adalimumab.

In certain embodiments, a treatment regimen is provided for the treatment of dermatitis herpetiformis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a steroid. In certain embodiments, at least one of the additional therapeutic agents is an immunosuppressant. In certain embodiments, at least one of the additional therapeutic agents is a tetracycline. In certain embodiments, at least one of the additional therapeutic agents is selected from dapsone, sulfasalazine, sulphapyridine, sulfamethoxypyridazine, cyclosporin A, azathioprine, colchicine, heparin, nicotinamide, mycophenolate, and rituximab.

In certain embodiments, a treatment regimen is provided for the treatment of inflammatory bowel disease comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is an aminosalicylate. In certain embodiments, at least one of the additional therapeutic agents is an immunosuppressant. In certain embodiments, at least one of the additional therapeutic agents is selected from mesalamine, balsalazide, olsalazine, azathioprine, mercaptopurine, methotrexate, infliximab, adalimumab, golimumab, certolizumab, vedolizumab, and ustekinumab.

In certain embodiments, a treatment regimen is provided for the treatment of Sjögren's syndrome comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a non-steroidal anti-inflammatory drug. In certain embodiments, at least one of the additional therapeutic agents is an immunosuppressant. In certain embodiments, at least one of the additional therapeutic agents is selected from cyclosporine, lifitegrast, pilocarpine, cevimeline, hydroxychloroquine, and methotrexate.

In certain embodiments, a treatment regimen is provided for the treatment of ankylosing spondylitis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a non-steroidal anti-inflammatory drug. In certain embodiments, at least one of the additional therapeutic agents is a TNF blocker. In certain embodiments, at least one of the additional therapeutic agents is an IL-17 inhibitor. In certain embodiments, at least one of the additional therapeutic agents is selected from naproxen, indomethacin, adalimumab, certolizumab pegol, etanercept, golimumab, infliximab, secukinumab, ixekizumab, and tofacitinib.

In certain embodiments, a treatment regimen is provided for the treatment of alcoholic liver cirrhosis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a glucocorticosteroid. In certain embodiments, at least one of the additional therapeutic agents is an antioxidant. In certain embodiments, at least one of the additional therapeutic agents is selected from pentoxifylline and infliximab.

In certain embodiments, a treatment regimen is provided for the treatment of acquired immunodeficiency syndrome comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a non-nucleoside reverse transcriptase inhibitor. In certain embodiments, at least one of the additional therapeutic agents is a nucleoside or nucleotide reverse transcriptase inhibitor. In certain embodiments, at least one of the additional therapeutic agents is a protease inhibitor. In certain embodiments, at least one of the additional therapeutic agents is an integrase inhibitor. In certain embodiments, at least one of the additional therapeutic agents is an entry or fusion inhibitor. In certain embodiments, at least one of the additional therapeutic agents is selected from efavirenz, rilpivirine, doravirine, abacavir, tenofovir, emtricitabine, lamivudine, zidovudine, atazanavir, darunavir, lopinavir, ritonavir, bictegravir, raltegravir, dolutegravir, enfuvirtide, and maraviroc.

In certain embodiments, a treatment regimen is provided for the treatment of IgA multiple myeloma comprising the administration of an immunoglobulin degrader of the present invention or a pharmaceutically acceptable composition, salt, isotopic analog, or prodrug thereof in combination or in alternation with at least one additional therapeutic agent. In certain embodiments, at least one of the additional therapeutic agents is an HDAC inhibitor. In certain embodiments, at least one of the additional therapeutic agents is an immunomodulatory drug. In certain embodiments, at least one of the additional therapeutic agents is a steroid. In certain embodiments, at least one of the additional therapeutic agents is an antibody drug. In certain embodiments, at least one of the additional therapeutic agents is a BCL2 inhibitor. In certain embodiments, at least one of the additional therapeutic agents is a proteasome inhibitor. In certain embodiments, at least one of the additional therapeutic agents is a selective inhibitor of nuclear export. In certain embodiments, at least one of the additional therapeutic agents is selected from prednisone, cyclophosphamide, melphalan, vincristine, doxorubicin, dexamethasone, thalidomide, bortezomib, lenalidomide, carfilzomib, pomalidomide, daratumumab, Panobinostat, elotuzumab, ixazomib, isatuximab, venetoclax, marizomib, oprozomib, and Selinexor.

In certain embodiments, a treatment regimen is provided for the treatment of IgA heavy chain disease comprising the administration of an immunoglobulin degrader of the present invention or a pharmaceutically acceptable composition, salt, isotopic analog, or prodrug thereof in combination or in alternation with at least one additional therapeutic agent. In certain embodiments, at least one of the additional therapeutic agents is an antibiotic. In certain embodiments, at least one of the additional therapeutic agents is a chemotherapeutic drug. In certain embodiments, at least one of the additional therapeutic agents is a steroid. In certain embodiments, at least one of the additional therapeutic agents is selected from doxorubicin, cyclophosphamide, vincristine, prednisone, teniposide, bleomycin, vinblastine, procarbazine, and prednisolone.

In certain embodiments, a treatment regimen is provided for the treatment of linear IgA bullous dermatosis comprising the administration of an immunoglobulin degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is a tetracycline. In certain embodiments, at least one of the additional therapeutic agents is an immunoglobulin. In certain embodiments, at least one of the additional therapeutic agents is selected from erythromycin, sulphapyridine, colchicine, and mycophenolate mofetil.

In certain embodiments, a treatment regimen is provided for the treatment of monoclonal gammopathy of undetermined significance (MGUS) comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is selected from alendronate, risedronate, ibandronate, and zoledronic acid.

In certain embodiments, a treatment regimen is provided for the treatment of systemic fibroinflammatory disease comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a glucocorticoid. In certain embodiments, at least one of the additional therapeutic agents is a calcineurin inhibitor. In certain embodiments, at least one of the additional therapeutic agents is selected from prednisolone, methotrexate, azathioprine, mycophenolate, mycophenolate mofetil, 6-mercaptopurine, cyclophosphamide, and rituximab.

In certain embodiments, a treatment regimen is provided for the treatment of Riedel's thyroiditis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a glucocorticoid. In certain embodiments, at least one of the additional therapeutic agents is an immunosuppressant. In certain embodiments, at least one of the additional therapeutic agents is selected from tamoxifen, prednisone, and mycophenolate mofetil.

In certain embodiments, a treatment regimen is provided for the treatment of inflammatory pseudotumors comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is a cyclooxygenase 2 inhibitor. In certain embodiments, at least one of the additional therapeutic agents is an anti-inflammatory. In certain embodiments, at least one of the additional therapeutic agents is thalidomide.

In certain embodiments, a treatment regimen is provided for the treatment of mediastinal fibrosis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is rituximab.

In certain embodiments, a treatment regimen is provided for the treatment of retroperitoneal fibrosis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is an immunosuppressant. In certain embodiments, at least one of the additional therapeutic agents is selected from mycophenolate mofetil, methotrexate, azathioprine, cyclophosphamide, tamoxifen, prednisone, and cyclosporin A.

In certain embodiments, a treatment regimen is provided for the treatment of aortitis or periaortitis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is glucocorticoid. In certain embodiments, at least one of the additional therapeutic agents is an immunosuppressant. In certain embodiments, at least one of the additional therapeutic agents is selected from prednisone, methotrexate, tocilizumab, cyclophosphamide, azathioprine, and cyclosporin A.

In certain embodiments, a treatment regimen is provided for the treatment of proximal biliary strictures comprising the administration of an extracellular protein degrader of the present invention or a pharmaceutically acceptable composition, salt, isotopic analog, or prodrug thereof in combination or in alternation with at least one additional therapeutic agent.

In certain embodiments, a treatment regimen is provided for the treatment of gastroenteritis comprising the administration of an extracellular protein degrader of the present invention or a pharmaceutically acceptable composition, salt, isotopic analog, or prodrug thereof in combination or in alternation with at least one additional therapeutic agent.

In certain embodiments, a treatment regimen is provided for the treatment of IgA monoclonal gammopathy comprising the administration of an immunoglobulin degrader of the present invention or a pharmaceutically acceptable composition, salt, isotopic analog, or prodrug thereof in combination or in alternation with at least one additional therapeutic agent.

In certain embodiments, a treatment regimen is provided for the treatment of IgG monoclonal gammopathy comprising the administration of an immunoglobulin degrader of the present invention or a pharmaceutically acceptable composition, salt, isotopic analog, or prodrug thereof in combination or in alternation with at least one additional therapeutic agent.

In certain embodiments, a treatment regimen is provided for the treatment of IgE monoclonal gammopathy comprising the administration of an immunoglobulin degrader of the present invention or a pharmaceutically acceptable composition, salt, isotopic analog, or prodrug thereof in combination or in alternation with at least one additional therapeutic agent.

In certain embodiments, a treatment regimen is provided for the treatment of idiopathic hypocomplementemic tubulointerstitial nephritis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a steroid. In certain embodiments, at least one of the additional therapeutic agents is selected from prednisone, rituximab, and mycophenolic acid.

In certain embodiments, a treatment regimen is provided for the treatment of multifocal fibrosclerosis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is an immunosuppressant. In certain embodiments, at least one of the additional therapeutic agents is selected from cyclosporine and prednisolone.

In certain embodiments, a treatment regimen is provided for the treatment of pachymeningitis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is selected from prednisone, azathioprine, cyclophosphamide, methotrexate, and rituximab.

In certain embodiments, a treatment regimen is provided for the treatment of pancreatic enlargement comprising the administration of an extracellular protein degrader of the present invention or a pharmaceutically acceptable composition, salt, isotopic analog, or prodrug thereof in combination or in alternation with at least one additional therapeutic agent.

In certain embodiments, a treatment regimen is provided for the treatment of tumefactive lesions comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is an immunosuppressant. In certain embodiments, at least one of the additional therapeutic agents is selected from rituximab and cyclophosphamide.

In certain embodiments, a treatment regimen is provided for the treatment of rheumatoid arthritis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is a non-steroidal anti-inflammatory.

In certain embodiments, at least one of the additional therapeutic agents is a disease-modifying antirheumatic drug. In certain embodiments, at least one of the additional therapeutic agents is a biologic drug. In certain embodiments, at least one of the additional therapeutic agents is a Janus-associated kinase inhibitor. In certain embodiments, at least one of the additional therapeutic agents is an opioid. In certain embodiments, at least one of the additional therapeutic agents is selected from ibuprofen, naproxen sodium, prednisone, methotrexate, leflunomide, hydroxychloroquine, sulfasalazine, abatacept, adalimumab, anakinra, baricitinib, certolizumab, etanercept, golimumab, infliximab, rituximab, sarilumab, tocilizumab, tofacitinib, minocycline, celecoxib, nabumetone, piroxicam, diclofenac, diflunisal, indomethacin, ketoprofen, etodolac, fenoprofen, flurbiprofen, ketorolac, meclofenamate, mefenamic acid, meloxicam, oxaprozin, sulindac, salsalate, tolmetin, codeine, fentanyl, hydrocodone, hydromorphone, morphine, meperidine, oxycodone, tramadol, betamethasone, dexamethasone, cortisone, hydrocortisone, methylprednisolone, and prednisolone.

In certain embodiments, a treatment regimen is provided for the treatment of multiple sclerosis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is an interferon beta drug. In certain embodiments, at least one of the additional therapeutic agents is a biologic drug. In certain embodiments, at least one of the additional therapeutic agents is a muscle relaxant. In certain embodiments, at least one of the additional therapeutic agents is selected from prednisone, methylprednisolone, ocrelizumab, glatiramer acetate, interferon beta-1a, interferon beta-1b, fingolimod, dimethyl fumarate, diroximel fumarate, teriflunomide, siponimod, cladribine, ocrelizumab, natalizumab, alemtuzumab, baclofen, tizanidine, cyclobenzaprine, amantadine, modafinil, methylphenidate, and dalfampridine.

In certain embodiments, a treatment regimen is provided for the treatment of myasthenic gravis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is a cholinesterase inhibitor. In certain embodiments, at least one of the additional therapeutic agents is an immunosuppressant. In certain embodiments, at least one of the additional therapeutic agents is a monoclonal antibody. In certain embodiments, at least one of the additional therapeutic agents is selected from pyridostigmine, neostigmine, azathioprine, mycophenolate mofetil, cyclosporine, methotrexate, tacrolimus, rituximab, and eculizumab.

In certain embodiments, a treatment regimen is provided for the treatment of psoriatic arthritis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a non-steroidal anti-inflammatory. In certain embodiments, at least one of the additional therapeutic agents is a disease-modifying antirheumatic drug. In certain embodiments, at least one of the additional therapeutic agents is an immunosuppressant. In certain embodiments, at least one of the additional therapeutic agents is a biologic drug. In certain embodiments, at least one of the additional therapeutic agents is selected from apremilast, ibuprofen, naproxen sodium, methotrexate, leflunomide, sulfasalazine, azathioprine, cyclosporine, abatacept, adalimumab, certolizumab, etanercept, golimumab, infliximab, ixekizumab, secukinumab, tofacitinib, and ustekinumab.

In certain embodiments, a treatment regimen is provided for the treatment of systemic lupus erythematosus (SLE) comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a non-steroidal anti-inflammatory. In certain embodiments, at least one of the additional therapeutic agents is an antimalarial drug. In certain embodiments, at least one of the additional therapeutic agents is a corticosteroid. In certain embodiments, at least one of the additional therapeutic agents is an immunosuppressant. In certain embodiments, at least one of the additional therapeutic agents is a biologic drug. In certain embodiments, at least one of the additional therapeutic agents is selected from voclosporin, abatacept, anifrolumab, naproxen sodium, ibuprofen, hydroxychloroquine, methylprednisolone, azathioprine, mycophenolate, methotrexate, cyclosporine, leflunomide, belimumab, and rituximab.

In certain embodiments, a treatment regimen is provided for the treatment of sclerosing cholangitis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a bile acid sequestrant. In certain embodiments, at least one of the additional therapeutic agents is an antibiotic. In certain embodiments, at least one of the additional therapeutic agents is an antihistamine. In certain embodiments, at least one of the additional therapeutic agents is an opioid antagonist. In certain embodiments, at least one of the additional therapeutic agents is selected from ursodeoxycholic acid, rifampin, naltrexone, cholestyramine, colestipol, and colesevelam.

In certain embodiments, a treatment regimen is provided for the treatment of atopic asthma comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a bronchodilator. In certain embodiments, at least one of the additional therapeutic agents is a corticosteroid. In certain embodiments, at least one of the additional therapeutic agents is a leukotriene modifier. In certain embodiments, at least one of the additional therapeutic agents is a beta agonist. In certain embodiments, at least one of the additional therapeutic agents is selected from omalizumab, fluticasone, budesonide, mometasone, ciclesonide, montelukast, zafirlukast, zileuton, salmeterol, and formoterol.

In certain embodiments, a treatment regimen is provided for the treatment of cutaneous contact hypersensitivity comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is an antihistamine. In certain embodiments, at least one of the additional therapeutic agents is a corticosteroid.

In certain embodiments, a treatment regimen is provided for the treatment of allergic conjunctivitis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is an antihistamine. In certain embodiments, at least one of the additional therapeutic agents is a steroid. In certain embodiments, at least one of the additional therapeutic agents is cromolyn.

In certain embodiments, a treatment regimen is provided for the treatment of allergic urticaria comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is an antihistamine. In certain embodiments, at least one of the additional therapeutic agents is a histamine blocker. In certain embodiments, at least one of the additional therapeutic agents is an antidepressant. In certain embodiments, at least one of the additional therapeutic agents is a monoclonal antibody. In certain embodiments, at least one of the additional therapeutic agents is an immunosuppressant. In certain embodiments, at least one of the additional therapeutic agents is a corticosteroid. In certain embodiments, at least one of the additional therapeutic agents is selected from tacrolimus, cyclosporine, omalizumab, zafirlukast, montelukast, doxepin, prednisone, cimetidine, famotidine, loratadine, fexofenadine, cetirizine, and desloratadine.

In certain embodiments, a treatment regimen is provided for the treatment of anaphylactic shock comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is an antihistamine. In certain embodiments, at least one of the additional therapeutic agents is a beta-agonist. In certain embodiments, at least one of the additional therapeutic agents is selected from epinephrine, cortisone, and albuterol.

In certain embodiments, a treatment regimen is provided for the treatment of nasal polyposis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is an antihistamine. In certain embodiments, at least one of the additional therapeutic agents is a corticosteroid. In certain embodiments, at least one of the additional therapeutic agents is selected from dupilumab, prednisone, fluticasone, budesonide, mometasone, triamcinolone, beclomethasone, and ciclesonide.

In certain embodiments, a treatment regimen is provided for the treatment of keratoconjunctivitis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is an antihistamine. In certain embodiments, at least one of the additional therapeutic agents is a mast cell stabilizer. In certain embodiments, at least one of the additional therapeutic agents is a non-steroidal anti-inflammatory. In certain embodiments, at least one of the additional therapeutic agents is a corticosteroid. In certain embodiments, at least one of the additional therapeutic agents is an antiviral. In certain embodiments, at least one of the additional therapeutic agents is selected from cidofovir, ganciclovir, cromolyn sodium, nedocromil, sodium, lodoxamide, cyclosporine A, tacrolimus, lifitegrast, doxycycline, and vitamin A.

In certain embodiments, a treatment regimen is provided for the treatment of mastocytosis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is an antihistamine. In certain embodiments, at least one of the additional therapeutic agents is a leukotriene modifier. In certain embodiments, at least one of the additional therapeutic agents is a mast cell stabilizer. In certain embodiments, at least one of the additional therapeutic agents is a corticosteroid. In certain embodiments, at least one of the additional therapeutic agents is a chemotherapeutic drug.

In certain embodiments, a treatment regimen is provided for the treatment of eosinophilic gastrointestinal disease comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a proton pump inhibitor. In certain embodiments, at least one of the additional therapeutic agents is a corticosteroid. In certain embodiments, at least one of the additional therapeutic agents is an immunomodulator. In certain embodiments, at least one of the additional therapeutic agents is a biologic drug. In certain embodiments, at least one of the additional therapeutic agents is a leukotriene D4 receptor antagonist. In certain embodiments, at least one of the additional therapeutic agents is selected from montelukast, cromolyn sodium, omeprazole, lansoprazole, dexlansoprazole, esomeprazole, pantoprazole, rabeprazole, ilaprazole, fluticasone propionate, budesonide, prednisone, azathioprine, 6-mercaptopurine, timapiprant, mepolizumab, dectrekumab, and cendakimab.

In certain embodiments, a treatment regimen is provided for the treatment of bullous pemphigoid comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is an immunosuppressant. In certain embodiments, at least one of the additional therapeutic agents is selected from azathioprine, mycophenolate mofetil, rituximab, methotrexate, and tetracycline.

In certain embodiments, a treatment regimen is provided for the treatment of chemotherapy induced hypersensitivity reaction comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a histamine 1 antagonist. In certain embodiments, at least one of the additional therapeutic agents is a histamine 2 antagonist. In certain embodiments, at least one of the additional therapeutic agents is a corticosteroid. In certain embodiments, at least one of the additional therapeutic agents is an anticonvulsant.

In certain embodiments, a treatment regimen is provided for the treatment of seasonal allergic rhinitis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is an antihistamine. In certain embodiments, at least one of the additional therapeutic agents is a decongestant. In certain embodiments, at least one of the additional therapeutic agents is a corticosteroid. In certain embodiments, at least one of the additional therapeutic agents is a leukotriene modifier. In certain embodiments, at least one of the additional therapeutic agents is selected from fexofenadine, diphenhydramine, desloratadine, loratadine, levocetirizine, cetirizine, oxymetazoline, pseudoephedrine, phenylephrine, cromolyn sodium, montelukast, and ipratropium.

In certain embodiments, a treatment regimen is provided for the treatment of interstitial cystitis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a non-steroidal anti-inflammatory. In certain embodiments, at least one of the additional therapeutic agents is a tricyclic antidepressant. In certain embodiments, at least one of the additional therapeutic agents is an antihistamine. In certain embodiments, at least one of the additional therapeutic agents is selected from pentosan polysulfate sodium, loratadine, amitriptyline, imipramine, ibuprofen, naproxen sodium, dimethyl sulfoxide, and heparin.

In certain embodiments, a treatment regimen is provided for the treatment of eosinophilic esophagitis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a proton pump inhibitor. In certain embodiments, at least one of the additional therapeutic agents is a corticosteroid. In certain embodiments, at least one of the additional therapeutic agents is an immunomodulator. In certain embodiments, at least one of the additional therapeutic agents is a biologic drug. In certain embodiments, at least one of the additional therapeutic agents is a leukotriene D4 receptor antagonist. In certain embodiments, at least one of the additional therapeutic agents is selected from montelukast, cromolyn sodium, omeprazole, lansoprazole, dexlansoprazole, esomeprazole, pantoprazole, rabeprazole, ilaprazole, fluticasone propionate, budesonide, prednisone, azathioprine, 6-mercaptopurine, timapiprant, mepolizumab, dectrekumab, and cendakimab.

In certain embodiments, a treatment regimen is provided for the treatment of angioedema comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is an antihistamine. In certain embodiments, at least one of the additional therapeutic agents is an immunosuppressant. In certain embodiments, at least one of the additional therapeutic agents is a corticosteroid.

In certain embodiments, a treatment regimen is provided for the treatment of acute interstitial nephritis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is selected from cyclophosphamide, cyclosporine, and mycophenolate mofetil.

In certain embodiments, a treatment regimen is provided for the treatment of atopic eczema comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is a calcineurin inhibitor. In certain embodiments, at least one of the additional therapeutic agents is a biologic drug. In certain embodiments, at least one of the additional therapeutic agents is selected from dupilumab, prednisone, tacrolimus, and pimecrolimus.

In certain embodiments, a treatment regimen is provided for the treatment of eosinophilic bronchitis comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is a leukotriene receptor antagonist. In certain embodiments, at least one of the additional therapeutic agents is selected from budesonide, fluticasone, and montelukast.

In certain embodiments, a treatment regimen is provided for the treatment of chronic obstructive pulmonary disease comprising the administration of an extracellular protein degrader of the present invention or a pharmaceutically acceptable composition, salt, isotopic analog, or prodrug thereof in combination or in alternation with at least one additional therapeutic agent. In certain embodiments, at least one of the additional therapeutic agents is a bronchodilator. In certain embodiments, at least one of the additional therapeutic agents is a corticosteroid. In certain embodiments, at least one of the additional therapeutic agents is a phosphodiesterase-4 inhibitor. In certain embodiments, at least one of the additional therapeutic agents is an antibiotic. In certain embodiments, at least one of the additional therapeutic agents is selected from theophylline, azithromycin, roflumilast, fluticasone, budesonide, albuterol, ipratropium, levalbuterol, aclidinium, arformoterol, formoterol, indacaterol, tiotropium, salmeterol, and umeclidinium.

In certain embodiments, a treatment regimen is provided for the treatment of hyper-IgE syndrome (Job's syndrome) comprising the administration of an immunoglobulin degrader of the present invention or a pharmaceutically acceptable composition, salt, isotopic analog, or prodrug thereof in combination or in alternation with at least one additional therapeutic agent. In certain embodiments, at least one of the additional therapeutic agents is a corticosteroid. In certain embodiments, at least one of the additional therapeutic agents is an antibiotic.

VI. Processes of Manufacture

The extracellular protein degraders of the present invention can be manufactured according to routes described in the Working Examples below or as otherwise known in the patent or scientific literature and if appropriate supported by the knowledge of the ordinary worker or common general knowledge.

Some of the carbons in the extracellular protein degraders described herein are drawn with designated stereochemistry. Other carbons are drawn without stereochemical designation. When drawn without designated stereochemistry, that carbon can be in any desired stereochemical configuration that achieves the desired purpose. One skilled in the art will recognize that pure enantiomers, enantiomerically enriched compounds, racemates and diastereomers can be prepared by methods known in the art as guided by the information provided herein. Examples of methods to obtain optically active materials include at least the following:

i) chiral liquid chromatography—a technique whereby diastereomers are separated in a liquid mobile phase by virtue of their differing interactions with a stationary phase (including vial chiral HPLC). The stationary phase can be made of chiral material or the mobile phase can contain an additional chiral material to provoke the differing interactions;

ii) non-chiral chromatography of diastereomers-Often diastereomers can be separated using normal non-chiral column conditions;

iii) chiral gas chromatography—a technique whereby the racemate is volatilized and enantiomers are separated by virtue of their differing interactions in the gaseous mobile phase with a column containing a fixed non-racemic chiral adsorbent phase;

iv) simultaneous crystallization—a technique whereby the individual diastereomers are separately crystallized from a solution;

v) enzymatic resolutions—a technique whereby partial or complete separation of diastereomers are separated by virtue of differing rates of reaction with an enzyme;

vi) chemical asymmetric synthesis—a synthetic technique whereby the desired diastereomer is synthesized from an achiral precursor under conditions that produce asymmetry (i.e. chirality) in the product, which may be achieved by chiral catalysts or chiral auxiliaries;

vii) diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer; and viii) extraction with chiral solvents—a technique whereby diastereomers are separated by virtue of preferential dissolution of one over the others in a particular chiral solvent.

General Procedures Applied to the Working Examples of Synthesis

All reagents were purchased from commercial suppliers (Sigma-Aldrich, Alfa, Acros etc.) and used without further purification unless otherwise stated. THF was continuously refluxed and freshly distilled from sodium and benzophenone under nitrogen, dichloromethane was continuously refluxed and freshly distilled from $CaH_2$ under nitrogen.

Reactions were monitored via TLC on silica gel 60 HSGF254 percolated plates (0.15-0.2 mm $SiO_2$) and visualized using UV light (254 nm or 365 nm) and/or staining with phosphomolybdic acid ethanol solution (10 g in 100 mL ethanol) and subsequent heating or monitored via LCMS.

LCMS were performed on SHIMADZU LCMS-2010EV (Chromolith SpeedROD, RP-18e, 50×4.6 mm, mobile phase: Solvent A: $CH_3CN/H_2O/HCOOH$=10/90/0.05, Solvent B: $CH_3CN/H_2O/HCOOH$=90/10/0.05, 0.8 min@10% B, 2.7 min gradient (10-95% B), then 0.8 min@95% B, Flow rate: 3 mL/min, temperature: 40° C.).

Preparative HPLC were performed either on Method A: SHIMADZU LC-8A (Column: YMC Pack ODS-A (150*30 mm, 10 m)) or Method B: LC-6AD (Column: Shim=Pack PREP-ODS-H (250*20 mm, 10 m)) with UV detection which were controlled by LC solution Chemstation software. $H_2O$ (0.1% HCOOH) and MeOH (MeCN) as mobile phase at the indicated flow rate.

Analytical HPLC were performed on SHIMADZU LC-2010A (Chromolith SpeedROD, RP-18e, 50×4.6 mm, mobile phase: Solvent A: $CH_3CN/H_2O/HCOOH$=10/90/0.05, Solvent B: $CH_3CN/H_2O/HCOOH$=90/10/0.05, 0.8 min@ 10% B, 2.7 min gradient (10-95% B), then 0.8 min@95% B, Flow rate: 3 mL/min, temperature: 40° C.).

Chiral HPLC were performed on SHIMADZU LC-2010A (Chiral column, mobile phase: Solvent A: hexane (or contained 0.1% diethylamine), Solvent B: Ethanol or Isopropanol; Flow rate: 0.8 mL/min, temperature: 30° C.).

$^1$H spectra were recorded on Bruker Avance II 400 MHz, Chemical shifts (δ) were reported in ppm relative to tetramethylsilane (δ=0.000 ppm) and the spectra were calibrated to the residual solvent signal of chloroform (δ=7.26), Dimethyl sulfoxide (δ=2.50), methanol (δ=3.30). Data for $^1$H NMR spectra were reported as following: chemical shift (multiplicity, number of hydrogens). Abbreviations were described as following: s (singlet), d (doublet), t (triplet), q (quartet), quant (quintet), m (multiple), br (broad).

The reagent OPT-Alkyne has the following structure:

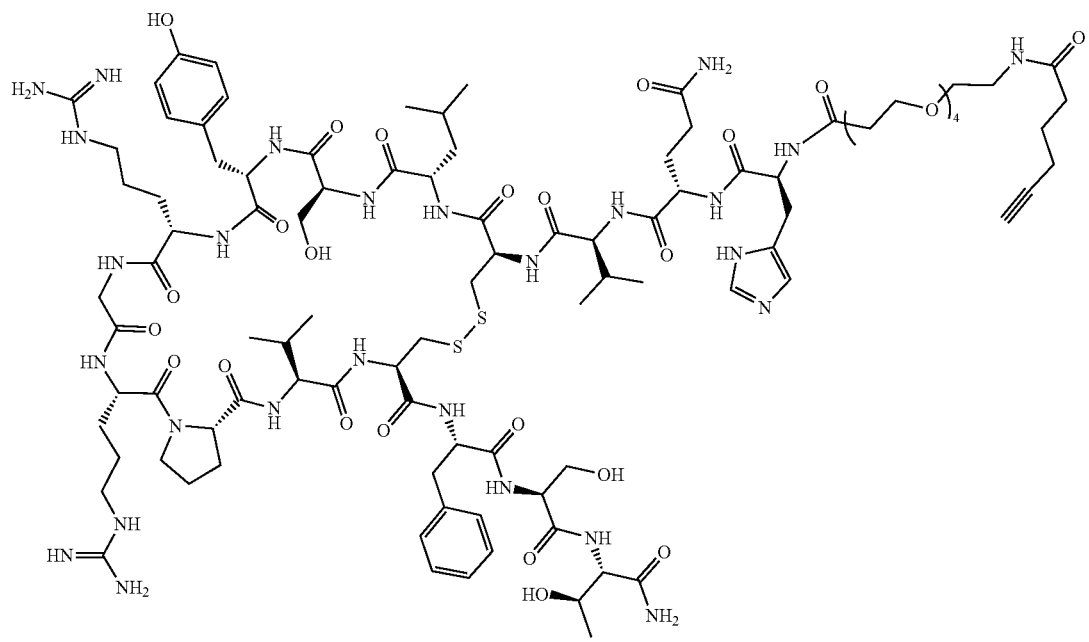

The reagent FC-III peptide-alkyne has the following structure:

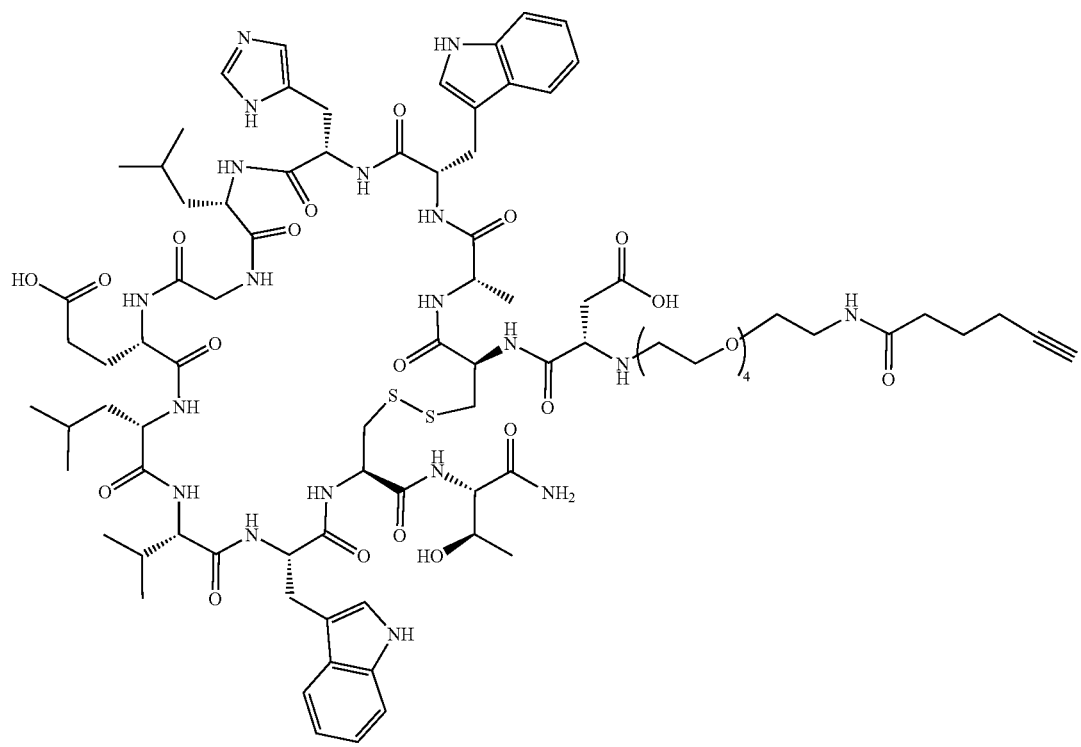

General Synthetic Methods

The extracellular protein degrading compounds of the present invention can be synthesized using a variety of techniques known to the skilled artisan. For example, starting with an Extracellular Protein Targeting Ligand with an amine the linker and ASGPR binding portion of the molecule can be installed with peptide coupling conditions.

725 726
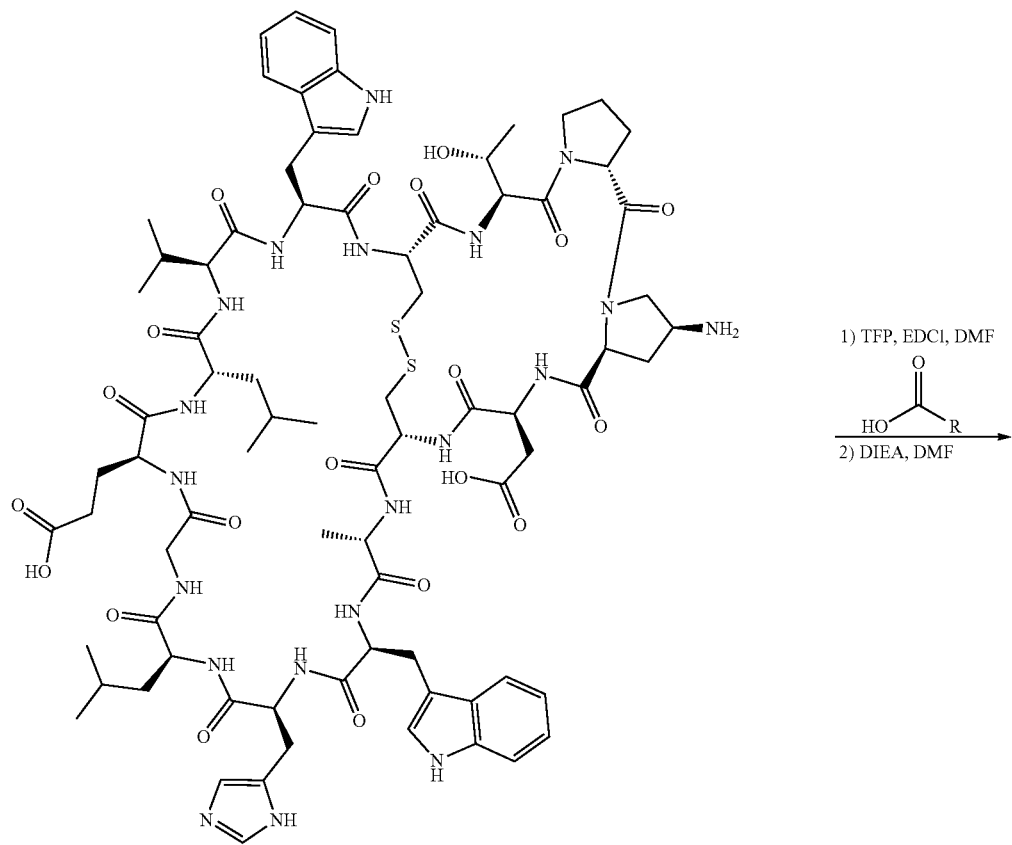
1) TFP, EDCl, DMF
2) DIEA, DMF
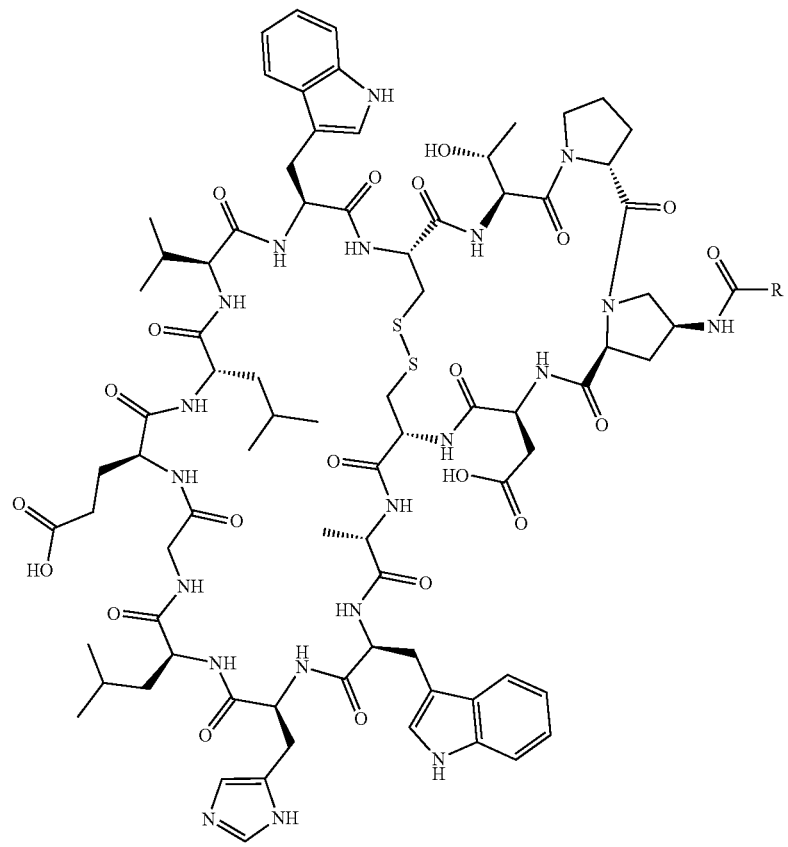

This technique can be used for the synthesis of various extracellular protein degrading compounds of the present invention including those that possess varied stereocenters.
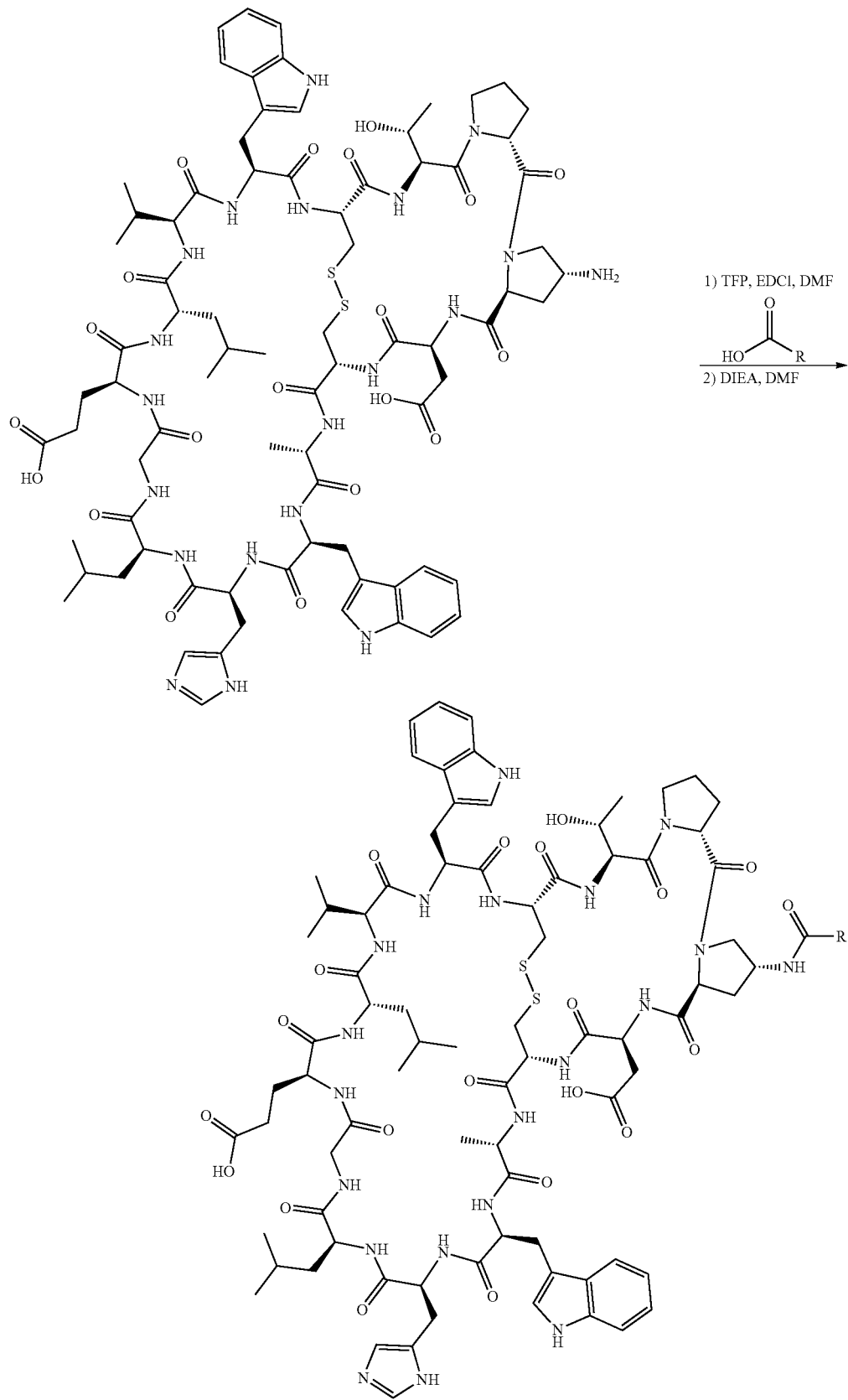

Synthesis of Targeting Ligands
Preparation of Intermediate 1, (S)-3-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(2-carboxyethyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)carbamoyl)-5,21-dioxo-8,11,14,17-tetraoxa-4,20-diazahexacos-25-yn-1-oic acid
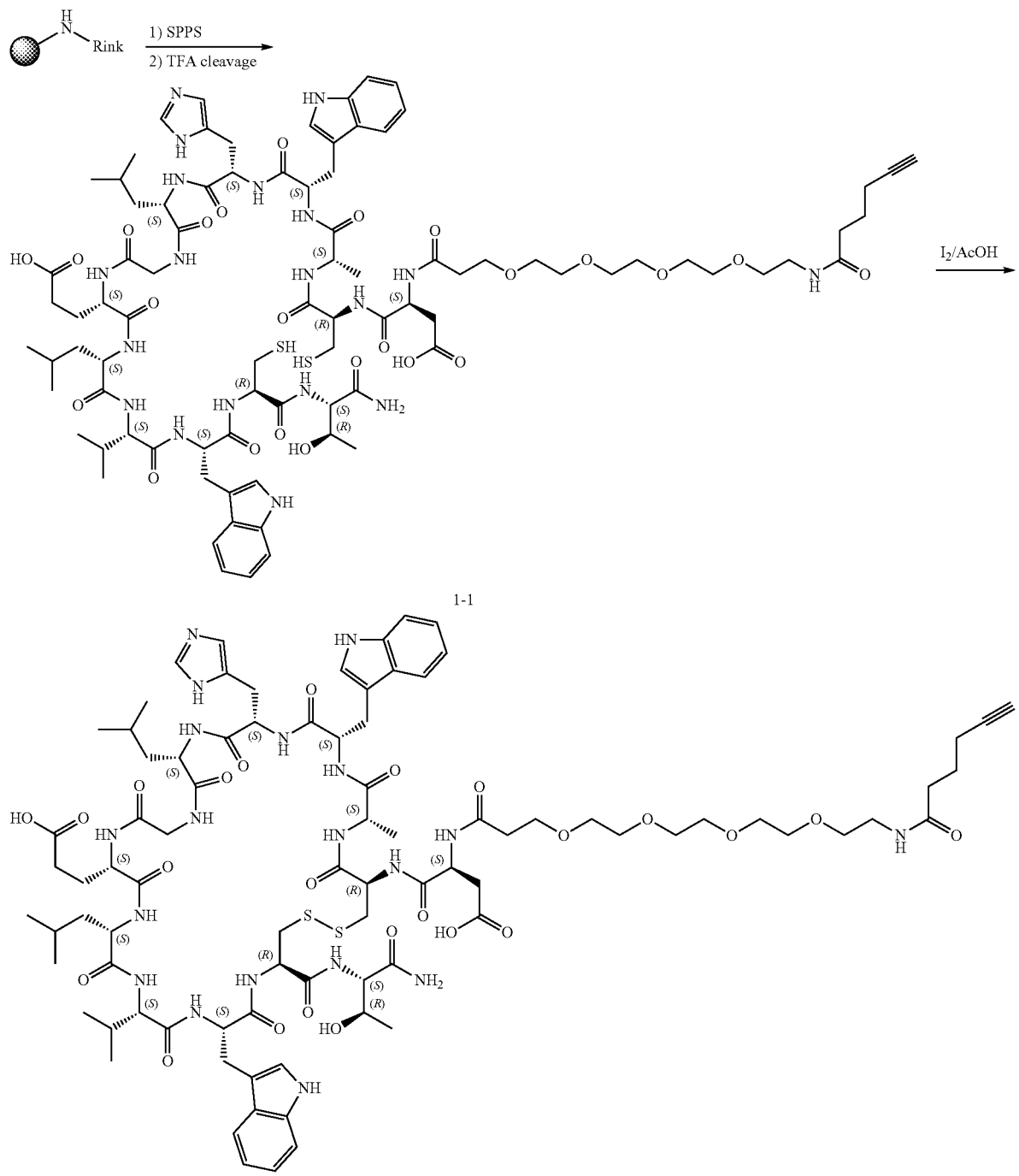
Intermediate 1

Step 1: Solid Phase Peptide Synthesis:

The peptide was synthesized using standard Fmoc chemistry.

1) Resin preparation: AM Resin (66.67 g, 20.00 mmol, 0.30 mmol/g) in DMF (600 mL) was mixed for 30 minutes with $N_2$ bubbling at 15° C. The resin was washed with DMF (600 mL)*5. Then 20% piperidine in DMF (600 mL) was added and the mixture was bubbled with $N_2$ for 30 minutes at 15° C. The mixture was filtered to obtain the resin. The resin was washed with DMF (600 mL)*5 before proceeding to next step.

2) Coupling: A solution of Fmoc-Thr(tBu)-OH (23.82 g, 60.00 mmol, 3.00 eq), HBTU (21.60 g, 57 mmol, 2.85 eq) in DMF (300 mL) was added to the resin with $N_2$ bubbling. Then DIEA (22.11 mL, 120 mmol, 6.00 eq) was added to the mixture dropwise and bubbled with $N_2$ for 30 minutes at 15° C. The coupling reaction was monitored by ninhydrin test, if it showed colorless, the coupling was completed. The resin was then washed with DMF (600 mL)*5.

3) Deprotection: 20% piperidine in DMF (600 mL) was added to the resin and the mixture was bubbled with $N_2$ for 30 minutes at 15° C. The resin was then washed with DMF (600 mL)*5. The Deprotection reaction was monitored by ninhydrin test, if it showed blue or other brownish red, the reaction was completed.

4) Step 2 and 3 were repeated for all other amino acids: (2-15 in the table below).

| # | Materials | Coupling reagents |
|---|---|---|
| 1 | Fmoc-Thr(tBu)-OH (3.00 eq) | HBTU (2.85 eq) and DIEA (6.00 eq) |
| 2 | Fmoc-Cys(Trt)-OH (3.00 eq) | HBTU (2.85 eq) and DIEA (6.00 eq) |
| 3 | Fmoc-Trp-OH (3.00 eq) | HBTU (2.85 eq) and DIEA (6.00 eq) |
| 4 | Fmoc-Val-OH (3.00 eq) | HBTU (2.85 eq) and DIEA (6.00 eq) |
| 5 | Fmoc-Leu-OH (3.00 eq) | HBTU (2.85 eq) and DIEA (6.00 eq) |
| 6 | Fmoc-Glu(OtBu)-OH (3.00 eq) | HATU (2.85 eq) and DIEA (6.00 eq) |
| 7 | Fmoc-Gly-OH (3.00 eq) | HATU (2.85 eq) and DIEA (6.00 eq) |
| 8 | Fmoc-Leu-OH (3.00 eq) | HATU (2.85 eq) and DIEA (6.00 eq) |
| 9 | Fmoc-His(Trt)-OH (2.00 eq) | HATU (2.85 eq) and DIEA (6.00 eq) |
| 10 | Fmoc-Trp-OH (3.00 eq) | HATU (2.85 eq) and DIEA (6.00 eq) |
| 11 | Fmoc-Ala-OH (3.00 eq) | HATU (2.85 eq) and DIEA (6.00 eq) |
| 12 | Fmoc-Cys(Trt)-OH (3.00 eq) | HATU (2.85 eq) and DIEA (6.00 eq) |
| 13 | Fmoc-Asp(OtBu)-OH (3.00 eq) | HATU (2.85 eq) and DIEA (6.00 eq) |
| 14 | Fmoc-Peg 4-OH (1.5 eq) | HATU (1.425 eq) and DIEA (3.00 eq) |
| 15 | hex-5-ynoic acid (1.5 eq) | HATU (1.425 eq) and DIEA (3.00 eq) |

Step 2: Peptide Cleavage and Purification:

1) Cleavage buffer (92.5% TFA/2.5% TIS/2.5% $1H_2O$/2.5% 3-mercaptopropanoic acid) was added to the flask containing the side chain protected peptide at room temperature and stir for 2 hrs.

2) The peptide was precipitated with cold isopropyl ether and centrifuged (3 mins at 3000 rpm).

3) Isopropyl ether washed two additional times.

4) Dried the crude peptide under vacuum 2 hrs.

5) A mixture of crude peptide in MeCN (10 L) and $H_2O$ (10 L), Iodine (0.1 M in AcOH) was added dropwise to vigorously stirring peptide solution until yellow color persists. After 2 minutes, Sodium thiosulfate (0.1 M in water) was added dropwise until yellow color disappears. The mixture was lyophilized to give the crude powder.

6) The crude peptide was purified by prep-HPLC (A: 0.075% TFA in $H_2O$, B: ACN) to give the Target 49 (5.9 g, 95.1% purity, 14.99% yield) as a white solid. Chemical Formula: $C_{86}H_{123}N_{19}O_{24}S_2$; LCMS found: $[M+H]^+=1871.00$; $[M+2H]^{2+}=936.10$; $[M+3H]^{3+}=624.38$;

Step 4: Purification Conditions.

The purification condition is described as the following table.

| | Separation condition |
|---|---|
| Dissolution condition | Dissolve in ACN/$H_2O$ |
| Instrument | HANBON |
| Mobile Phase | A: $H_2O$ (TFA0.075%) |
| | B: $CH_3CN$ |
| Gradient | 20-50%-60 min. Retention time: 42 min |
| Column | Luna 100*25 mm, C18, 10 um, 100 Å + Gemini ® 150*30 mm, C18, 5 um, 110 Å |
| Flow Rate | 20 mL/min |
| Wavelength | 220/254 nm |
| Oven Tem. | Room temperature |

The resulting compound is characterized as follows:

| Intermediate | Material | Structure and Analytical data |
|---|---|---|
| Intermediate 1 | AM Resin Fmoc amino acids | 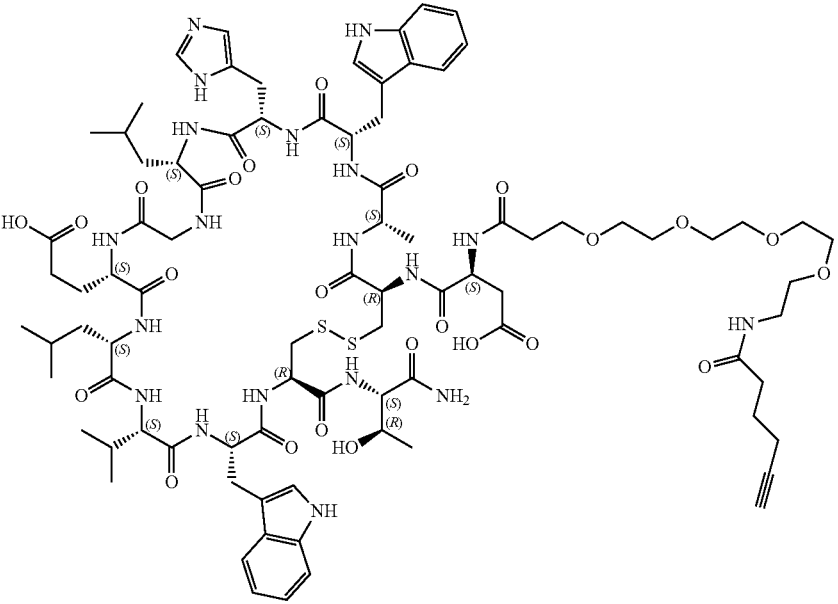<br>Yield: 5.9 g, 14.99%, 95.1% purity, white solid. LCMS found: $[M + H]^+ = 1871.00$; $[M + 2H]^{2+} = 936.10$; $[M + 3H]^{3+} = 624.38$; |

The following compounds were synthesized using the same procedure for Intermediate 1

| Intermediate | Material | Structure and Analytical data |
|---|---|---|
| Intermediate 2 | AM Resin Fmoc amino acids | 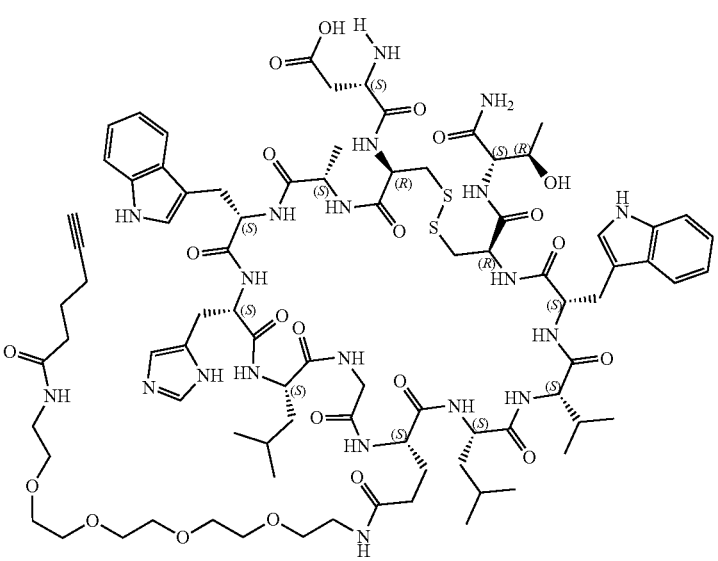<br>Yield: 367.2 mg, 19.03%, 95.5% purity, white solid. LCMS found: $[M + H]^+ = 1842.19$; $[M + 2H]^{2+} = 921.55$; $[M + 3H]^{3+} = 614.68$; |

| Intermediate | Material | Structure and Analytical data |
|---|---|---|
| Intermediate 3 | AM Resin Fmoc amino acids | 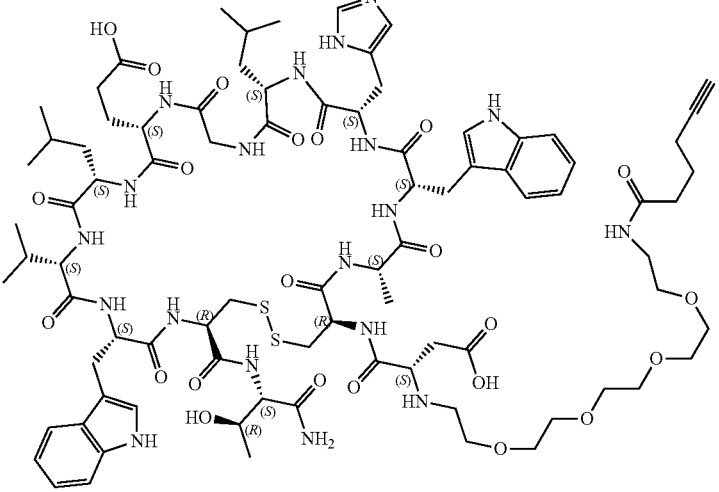<br>Building block:<br>Yield: 750 mg, 46.67%, 89.0% purity, white solid. LCMS found: $[M + H]^+ = 715.24$;<br>Yield: 259.3 mg, 19.13%, 95.2% purity, white solid. LCMS found: $[M + H]^+ = 1843.90$; $[M + 2H]^{2+} = 921.98$; $[M + 3H]^{3+} = 614.89$; |

Preparation of Intermediate 4, 3-((6S,9R,12S,15S,18S,21S,27S,30S,33S,36S,39R,42S,44aS,46S,49aR)-30-((1H-imidazol-5-yl)methyl)-12,33-bis((1H-indol-3-yl)methyl)-42-(carboxymethyl)-6-((R)-1-hydroxyethyl)-18,27-diisobutyl-15-isopropyl-36-methyl-5,8,11,14,17,20,23,26,29,32,35,38,41,44,49-pentadecaoxo-46-(17-oxo-4,7,10,13-tetraoxa-16-azadocos-21-ynamido)octatetracontahydro-1H-9,39-(methanodithiomethano)dipyrrolo[1,2-a:1',2'-d][1,4,7,10,13,16,19,22,25,28,31,34,37,40,43]pentadecaazacyclopentatetracontin-21-yl)propanoic acid

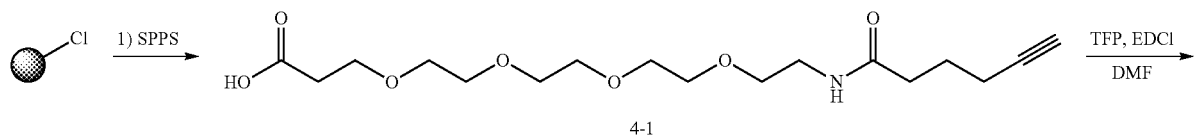

4-1

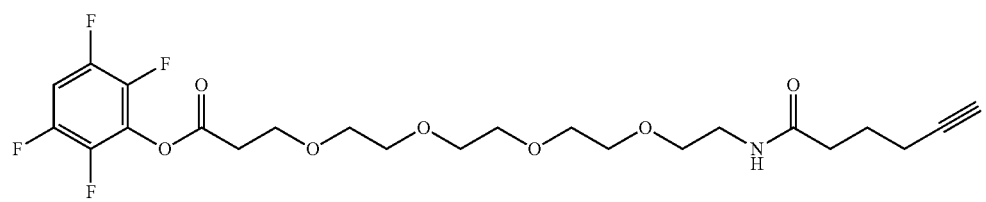

4-2

-continued
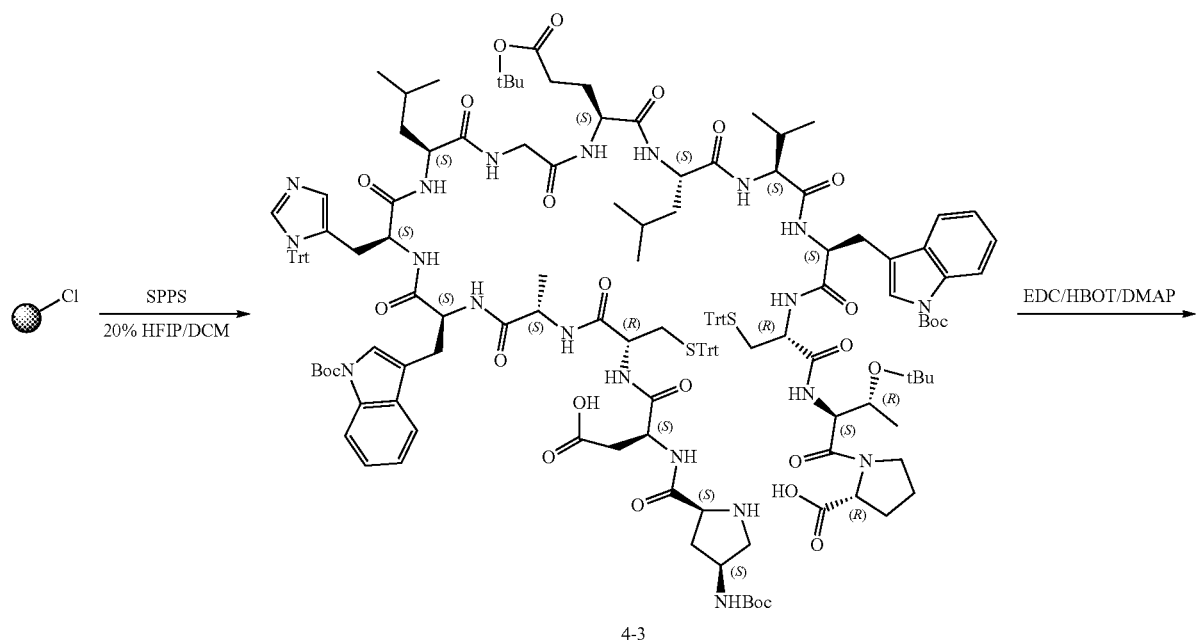
4-3
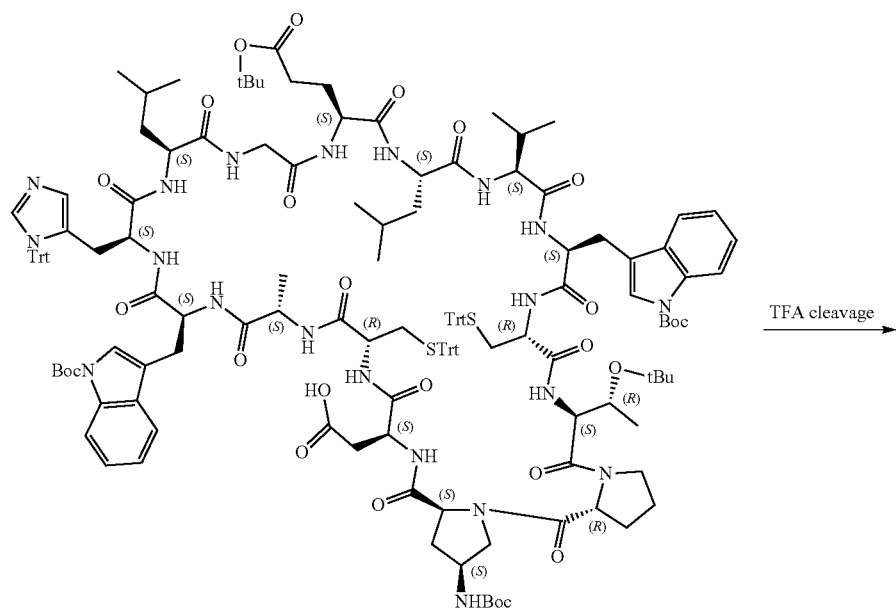
4-4

-continued
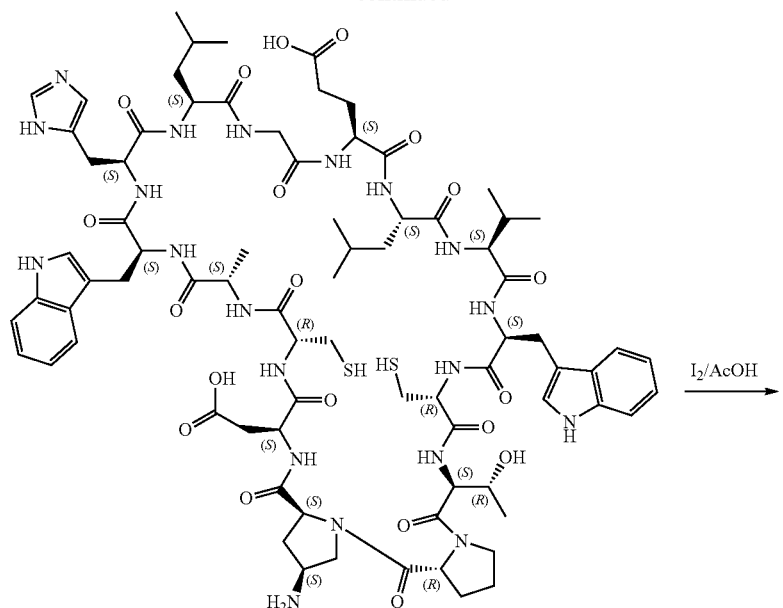
4-5
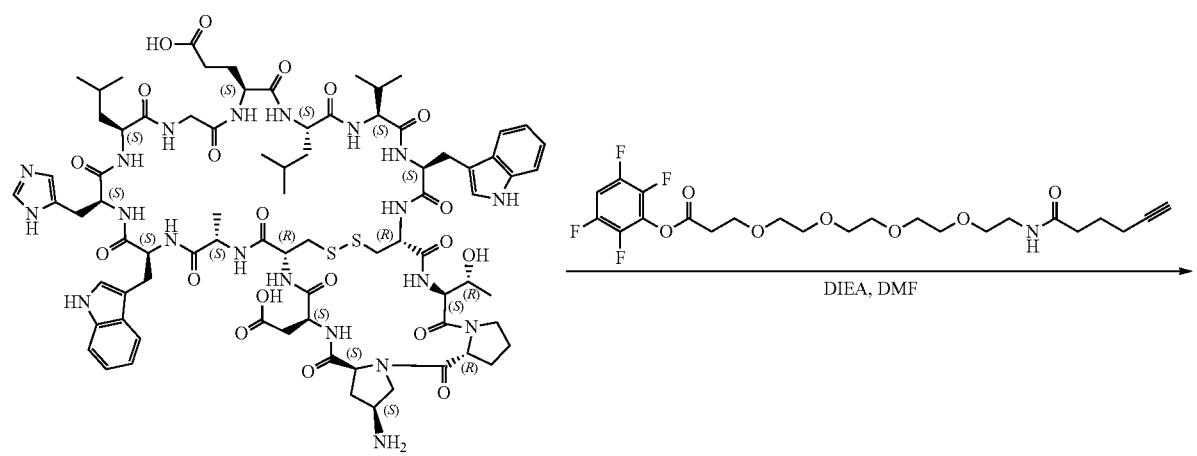
4-6

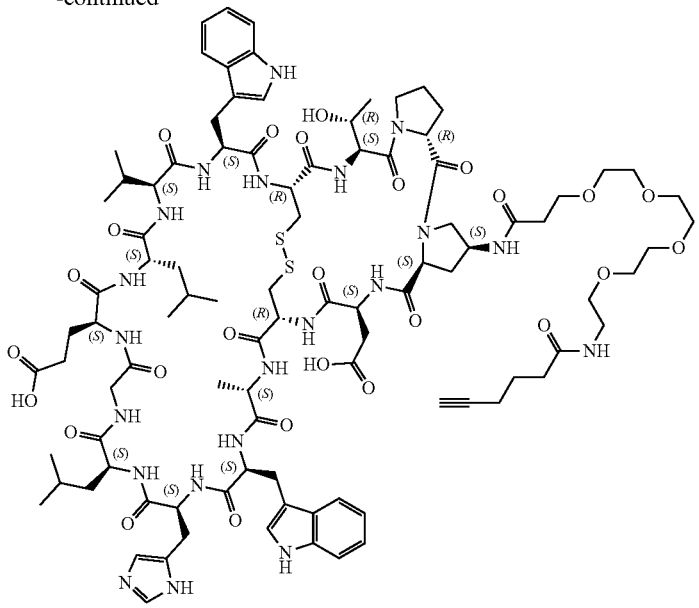

Intermediate 4

Step 1: General Procedure for Preparation of 4-4
Solid Phase Peptide Synthesis:
The peptide was synthesized using standard Fmoc chemistry.
1) Resin preparation: To the vessel containing CTC Resin (61.70 g, 50.00 mmol, 0.81 mmol/g) and Fmoc-D-Pro-OH (16.87 g, 50.00 mmol, 1.00 eq) in DCM (500 mL) was added DIEA (34.60 mL, 200.00 mmol, 4.00 eq) dropwise and mixed for 2 hrs with $N_2$ bubbling at 15° C. Then added MeOH (50.00 mL) and bubbled with $N_2$ for another 30 mins. The resin was washed with DMF (1 L)*5. Then 20% piperidine in DMF (1 L) was added and the mixture was bubbled with $N_2$ for 30 mins at 15° C. The mixture was filtered to obtain the resin. The resin was washed with DMF (1 L)*5 before proceeding to next step.
2) Coupling: A solution of Fmoc-Thr(tBu)-OH (59.63 g, 150.00 mmol, 3.00 eq), (BTU (16.11 g, 142.50 mmol, 2.85 eq) in DMF (500 mL) was added to the resin with $N_2$ bubbling. Then DIEA (51.60 mL, 300 mmol, 6.00 eq) was added to the mixture dropwise and bubbled with $N_2$ for 30 mins at 15° C. The coupling reaction was monitored by ninhydrin test, if it showed colorless, the coupling was completed. The resin was then washed with DMF (1 L)*5.
3) Deprotection: 200 piperidine in DMF (1 L) was added to the resin and the mixture was bubbled with $N_2$ for 30 mins at 15° C. The resin was then washed with DMF (1 L)*5 The Deprotection reaction was monitored by ninhydrin test, if it showed blue or other brownish red, the reaction was completed.
4) Step 2 and 3 were repeated for all other amino acids:

| # | Materials | Coupling reagents |
|---|---|---|
| 1 | Fmoc-D-Pro-OH (1.00 eq) | DIEA (4.00 eq) |
| 2 | Fmoc-Thr(tBu)-OH (3.00 eq) | HBTU (2.85 eq) and DIEA (6.00 eq) |
| 3 | Fmoc-Cys(Trt)-OH (3.00 eq) | HBTU (2.85 eq) and DIEA (6.00 eq) |
| 4 | Fmoc-Trp(Boc)-OH (3.00 eq) | HBTU (2.85 eq) and DIEA (6.00 eq) |
| 5 | Fmoc-Val-OH (3.00 eq) | HBTU (2.85 eq) and DIEA (6.00 eq) |
| 6 | Fmoc-Leu-OH (3.00 eq) | HBTU (2.85 eq) and DIEA (6.00 eq) |
| 7 | Fmoc-Glu(OtBu)-OH (3.00 eq) | HBTU (2.85 eq) and DIEA (6.00 eq) |
| 8 | Fmoc-Gly-OH (3.00 eq) | HBTU (2.85 eq) and DIEA (6.00 eq) |
| 9 | Fmoc-Leu-OH (3.00 eq) | HBTU (2.85 eq) and DIEA (6.00 eq) |
| 10 | Fmoc-His(Trt)-OH (2.00 eq) | HBTU (2.85 eq) and DIEA (6.00 eq) |
| 11 | Fmoc-Trp-OH (3.00 eq) | HBTU (2.85 eq) and DIEA (6.00 eq) |
| 12 | Fmoc-Ala-OH (3.00 eq) | HBTU (2.85 eq) and DIEA (6.00 eq) |
| 13 | Fmoc-Cys(Trt)-OH (3.00 eq) | HBTU (2.85 eq) and DIEA (6.00 eq) |
| 14 | Fmoc-Asp(OtBu)-OH (3.00 eq) | HBTU (2.85 eq) and DIEA (6.00 eq) |
| 15 | BOC-(2S,4S)-4-AMINO-1-FMOC-PYRROLIDINE-2-CARBOXYLIC ACID (1.00 eq) | HATU (0.95 eq) and DIEA (2.00 eq) |

Peptide Cleavage and Purification:
1) Cleavage buffer (20% HFIP/DCM, 1.2 L) was added into the flask containing the side chain protected crude peptide. The mixture was stirred for 1 hr at room temperature and the solution was collected after filtration. The cleavage step was repeated for another time.
2) The solution was combined after filtration.
3) The solution was concentrated by rotary evaporation.
4) The crude peptide was dried under lyophilization.
5) 4-3 (47.00 g, crude) was obtained as a white solid.
6) A mixture of 4-3 (47.00 g, 16.00 mmol, 1.00 eq), HOBT (6.49 g, 48.00 mmol, 3.00 eq), DMAP (5.80 g, 48.00 mmol, 3.00 eq), and EDCI (9.17 g, 48.00 mmol, 3.00 eq) in DMF (16 L) was stirred at 25° C. for 72 hrs.
7) The solution was combined after filtration.
8) The mixture was added to 0.50 M HCl (cold, 2 L) and white solid was precipitated. After filtered, the solid was dried under lyophilization to afford 4-4 (50.00 g, crude) as a white solid. Chemical Formula: $C_{159}H_{192}N_{20}O_{26}S_2$, LCMS found: $[M+2H]^{2+}=$ 1338.62;

Step 2: General Procedure for Preparation of Intermediate 5

A mixture of compound 4-4 (50.0 g, 16.83 mmol, 1.00 eq) in TFA/TIS/$H_2O$ (95%/2.5%2.5%, v/v/v, 600 mL) was stirred at 20° C. for 1 hr. The mixture was precipitated with cold isopropyl ether (3 L). After filtration, the solid was dried under vacuum for 2 hrs to get 3-5 (32.00 g). 3-5 (32.00 g), in ACN/$H_2O$ (1/1, v/v, 17 L). $I_2$/HOAc (0.1 M) was added to the mixture dropwise at 15° C. until the light yellow persisted, then the mixture was quenched with 0.1 M $Na_2S_2O_3$ dropwise until the light yellow disappeared. After filtration, the filtrate was purified by prep-HPLC (acid condition, TFA) directly to get Intermediate 5 (5.00 g, 2.15 mmol, 10.00% yield, 85% purity) as a white solid. Chemical Formula: $C_{79}H_{108}N_{20}O_{20}S_2$, LCMS found: $[M+H]^{1+}$= 1722.00, $[M+2H]^{2+}$=861.61.

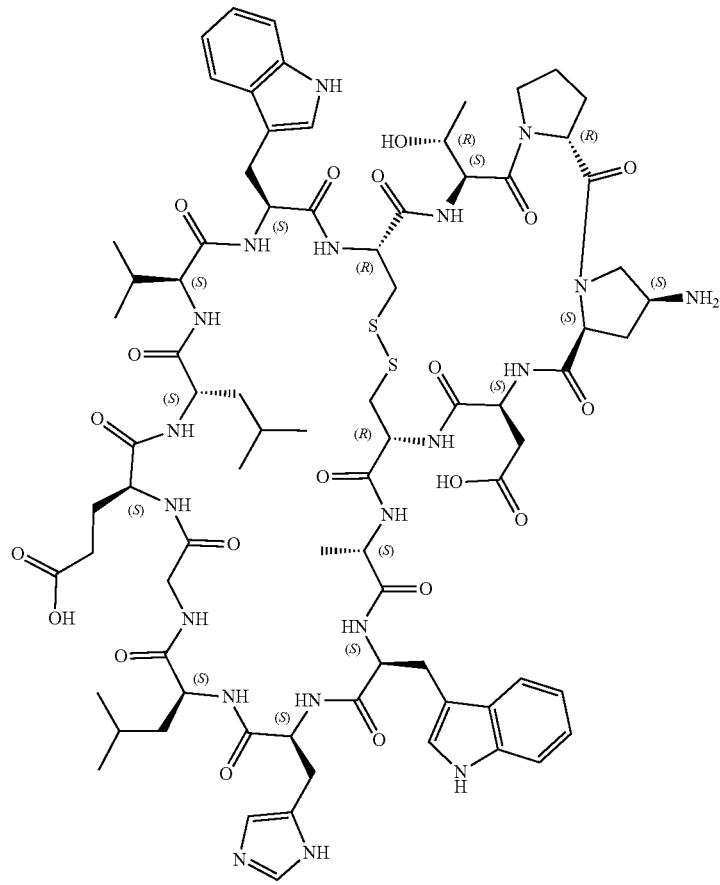

Yield; 5 g, 4.93%, 85.0% purity while solid. LC-MS (ESI) found: $[M + H]^{1+} = 1722.00$, $[M + 2H]^{2+} = 861.61$.

Step 3: General Procedure for Preparation of 4-2

A mixture of 4-1 (8.00 g, 22.25 mmol, 1.00 eq), 2,3,5,6-tetrafluorophenol (11.08 g, 66.75 mmol, 4.00 eq), and EDCI (9.52 g, 33.23 mmol, 2.00 eq) in DMF (224 mL) was stirred at 25° C. for 16 hrs. LCMS showed the reaction was completed. The mixture was purified by Flash (TFA condition) and lyophilization to afford 4-2 (9.00 g, 17.73 mmol, 79.69% yield) as a yellow oil. Chemical Formula: $C_{23}H_{29}F_4NO_7$, LCMS found: $[M+H]^{1+}$=508.15.

Step 4: General Procedure for Preparation of Intermediate 4

A mixture of compound 4-6 (705.61 mg, 0.4 mmol, 1.00 eq), compound 4-2 (416.12 mg, 0.80 mmol, 2.00 eq), and DIEA (0.725 ml, 4 mmol, 10.00 eq) in DMF (10 mL) was stirred at 0° C. for 8 hrs. LCMS showed the reaction was completed. The mixture was adjusted pH=5 and purified by prep-HPLC (TFA condition) directly to get Intermediate 4 (477.40 mg, 0.23 mmol, 57.50% yield, 97.900 purity) as a white solid. Chemical Formula: $C_{96}H_{135}N_{21}O_{26}S_2$, LCMS found: $[M+2H]^{2+}$=1032.14, $[M+3H]^{3+}$=688.41.

Step 5: Purification Conditions.
The purification condition is described as the following table.

| | Separation condition |
|---|---|
| Dissolution condition | Dissolve in ACN/H$_2$O |
| Instrument | GX-281 |
| Mobile Phase | A: H$_2$O (TFA0.075%) |
| | B: CH$_3$CN |
| Gradient | 31-51%-51 min. Retention time: 22 min |

| | Separation condition |
|---|---|
| Column | Luna 100*25 mm, C18, 10 um, 100 Å + Gemini ® 150*30 mm, C18, 5 um, 110 Å |
| Flow Rate | 20 mL/min |
| Wavelength | 220/254 nm |
| Oven Tem. | Room temperature |

The compounds Intermediate 6, Intermediate 7, Intermediate 8, and Intermediate 9, were prepared according to the same procedure as Intermediate 4.

| Starting acids | Intermediate ID | Structure and Analytical data |
|---|---|---|
| Related Fmoc amino acids | 4 | 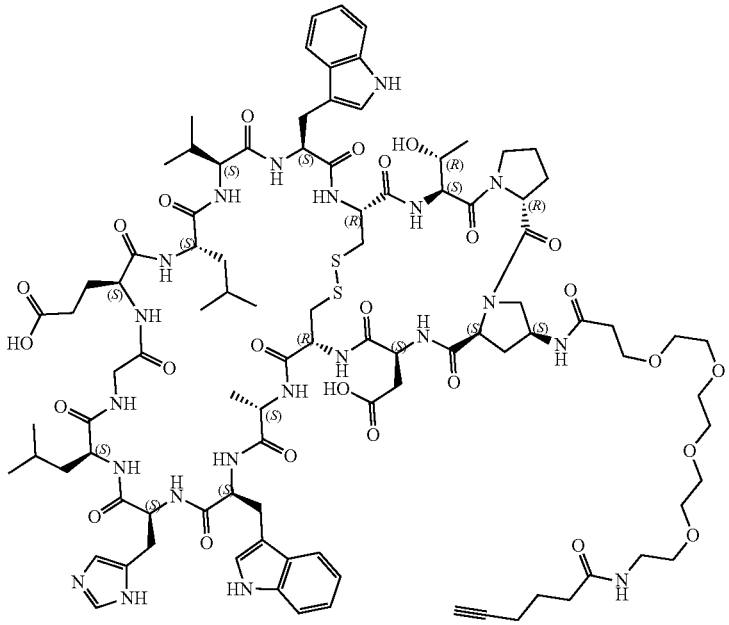 Yield: 477.4 mg, 2.73%, 97.9% purity white solid. LC-MS (ESI) found: 1032.14 [M + 2H]$^{2+}$, 688.41 [M + 3H]$^{3+}$ |
| Related Fmoc amino acids | 6 | 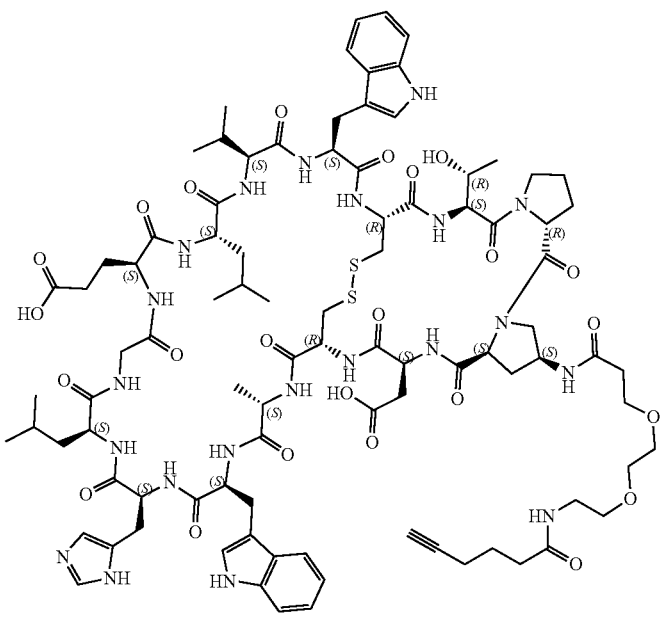 |

| Starting acids | Intermediate ID | Structure and Analytical data |
|---|---|---|
| | | Yield: 636.7 mg, 2.37%, 97.0% purity white solid. LC-MS (ESI) found: 988 [M + 2H]$^{2+}$, 659 [M + 3H]$^{3+}$ |
| Related Fmoc amino acids | 7 | 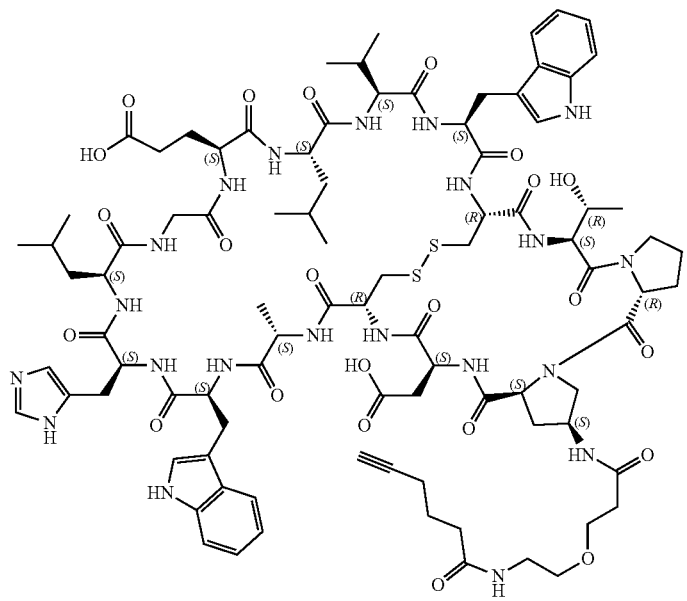 Yield: 363.1 mg, 2.20%, 95.1% purity white solid. LC-MS (ESI) found: 1931 [M + H]$^+$ 966 [M + 2H]$^{2+}$, 644 [M + 3H]$^{3+}$. |
| Related Fmoc amino acids | 8 | 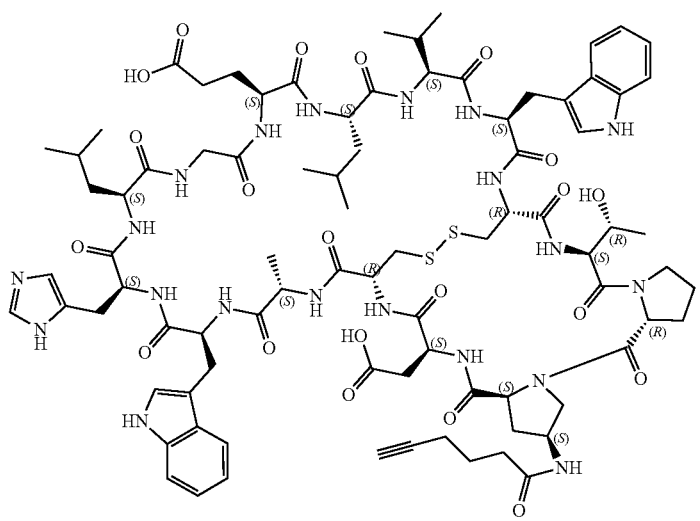 Yield: 312.8 mg, 2.19%, 96.1% purity white solid. LC-MS (ESI) found: 1815 [M]$^+$, 908 [M + 2H]$^{2+}$, 605 [M + 3H]$^{3+}$. |

| Starting acids | Intermediate ID | Structure and Analytical data |
|---|---|---|
| Related Fmoc amino acids | 9 | 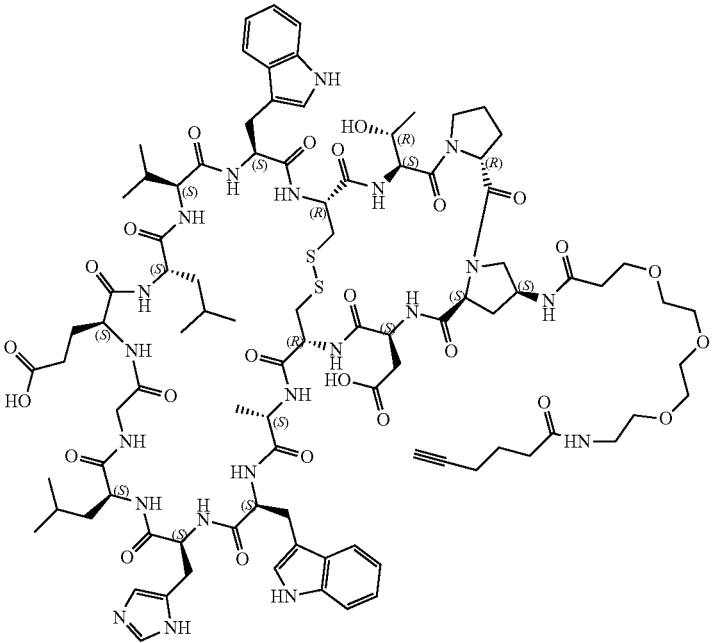<br>Yield: 296 mg, 1.74%, 95.1% purity white solid. LC-MS (ESI) found: 1010 $[M + 2H]^{2+}$, 673 $[M + 3H]^{3+}$ |

Preparation of Intermediate 10, 2-(2-(2-(2-((2,4-dinitrophenyl)amino)ethoxy)ethoxy)ethoxy)acetic acid

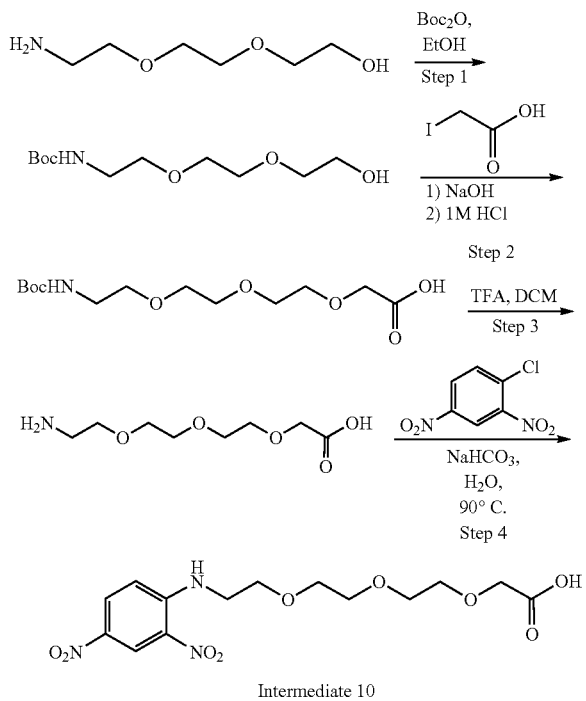

Intermediate 10

Step 1: To a solution of 2-(2-(2-aminoethoxy)ethoxy)ethan-1-ol (5.0 g, 33 mmol) in EtOH (60 mL) was added TEA (61.5 mL, 442 mmol) and di-tert-butyl dicarbonate (8.6 mL, 40 mmol) at 0° C. in portions. The mixture was vigorously stirred and allowed to warm up to room temperature slowly overnight (16 h). The solvents were evaporated under vacuum and the residue was purified by column chromatography ($SiO_2$, solvent gradient: DCM to 1:9 MeOH/DCM) to give tert-butyl (2-(2-(2-hydroxyethoxy)ethoxy)ethyl)carbamate as a colorless oil (4.5 g, 55% yield). LC-MS (ESI) found: 250 $[M+H]^+$.

Step 2: To a solution of tert-butyl (2-(2-(2-hydroxyethoxy)ethoxy)ethyl)carbamate as a colorless oil (72 g, 288 mmol) in THF (100 mL) was added 2-iodoacetic acid (160 g, 866 mmol) and NaOH (69 g, 1.7 mol) at 0° C. in portions. The mixture was stirred at rt for 2 days. The solvent was removed under vacuum, and then a solution of NaOH in water was added. DCM was used to wash the mixture. The aqueous phase was then acidified with 3 N HCl solution with vigorous stirring until pH 4. Extraction with DCM and concentration give 2,2-dimethyl-4-oxo-3,8,11,14-tetraoxa-5-azahexadecan-16-oic acid as a yellowish oil (80 g, 90% yield). LC-MS (ESI) found: 308 $[M+H]^+$.

Step 3: To a solution of 2,2-dimethyl-4-oxo-3,8,11,14-tetraoxa-5-azahexadecan-16-oic acid as a yellowish oil (42 g, 136 mmol) in DCM (250 mL) was added TFA (51 mL, 683 mmol) at 0° C. The mixture was stirred at rt for 2 h. The mixture was concentrated to give crude 2-(2-(2-(2-aminoethoxy)ethoxy)ethoxy)acetic acid (28 g, 99% yield) as a white solid. LC-MS (ESI) found: 208 $[M+H]^+$.

751

Step 4: To a solution of 2-(2-(2-(2-aminoethoxy)ethoxy)ethoxy)acetic acid (28 g, 135 mmol) in H$_2$O (300 mL) was added NaHCO$_3$ (34 g, 405 mmol) and 1-chloro-2,4-dinitrobenzene (41 g, 203 mmol) at 0° C. in portions. The mixture was stirred at 90° C. overnight. The mixture was adjust pH to 6, extracted with DCM, washed with brine, concentrated and purified by silica gel column to give 2-(2-(2-(2-((2,4-dinitrophenyl)amino)ethoxy)ethoxy)ethoxy)acetic acid (Intermediate 10, 20 g, 40% yield) as a yellow oil. LC-MS (ESI) found: 374 [M+H]$^+$. $^1$H NMR (400 MHz, MeOD): δ 9.03 (d, J=2.7 Hz, 1H), 8.28 (dd, J=9.6, 2.7 Hz, 1H), 7.22 (d, J=9.6 Hz, 1H), 4.10 (s, 2H), 3.81 (t, J=5.3 Hz, 2H), 3.75-3.61 (m, 10H).

752

Preparation of Intermediate 11: 3-((6S,9R,12S,15S,18S,21S,27S,30S,33S,36S,39R,42S,44aS,46S,49aR)-30-((1H-imidazol-5-yl)methyl)-12,33-bis((1H-indol-3-yl)methyl)-46-amino-42-(carboxymethyl)-6-((R)-1-hydroxyethyl)-18,27-diisobutyl-15-isopropyl-36-methyl 5,8,11,14,17,20,23,26,29,32,35,38,41,44,49-pentadecaoxooctatetracontahydro-1H-9,39-(methanodithiomethano)dipyrrolo[1,2-a:1',2'-d][1,4,7,10,13,16,19,22,25,28,31,34,37,40,43]pentadecaazacyclopentatetracontin-21-yl)propanoic acid

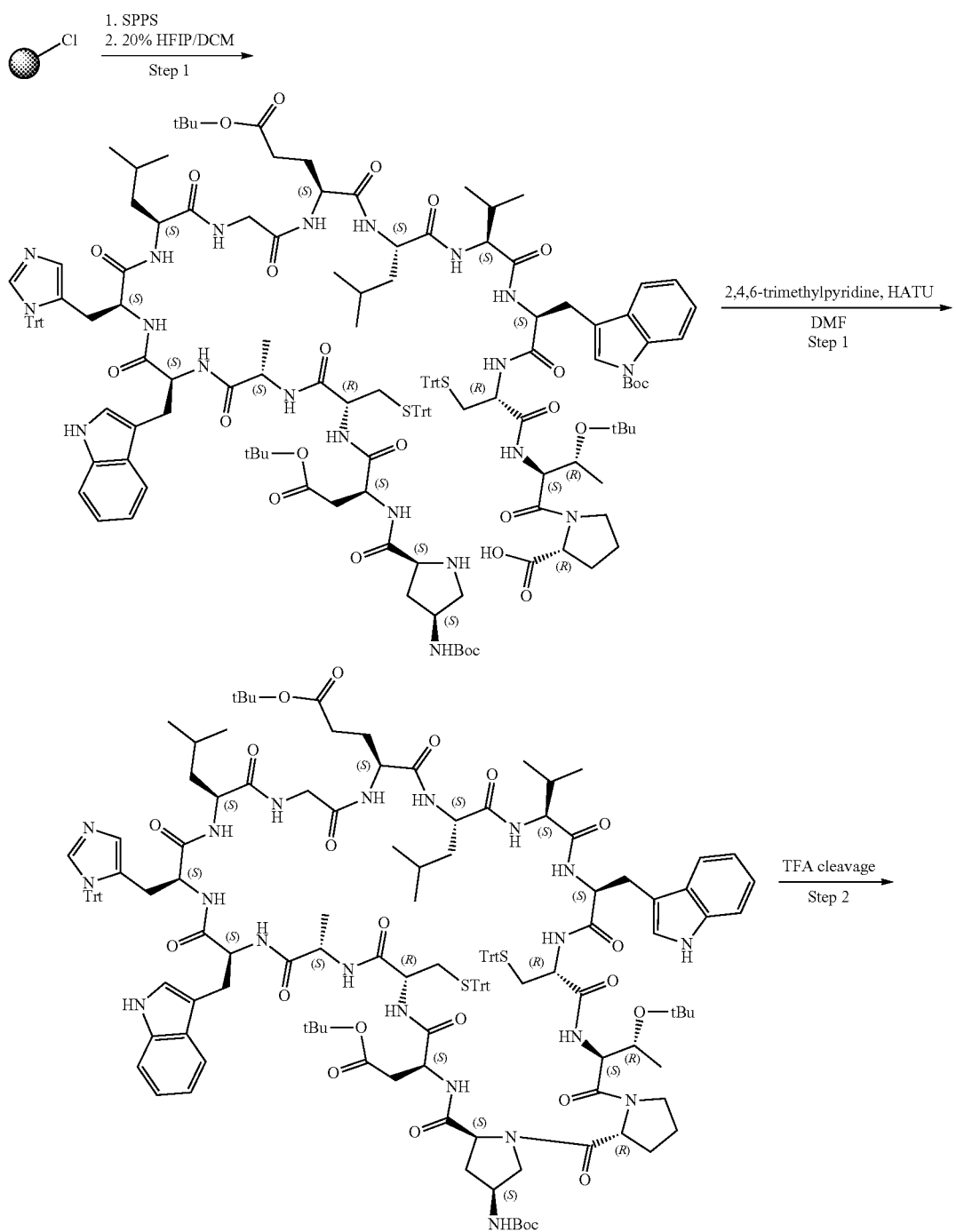

-continued

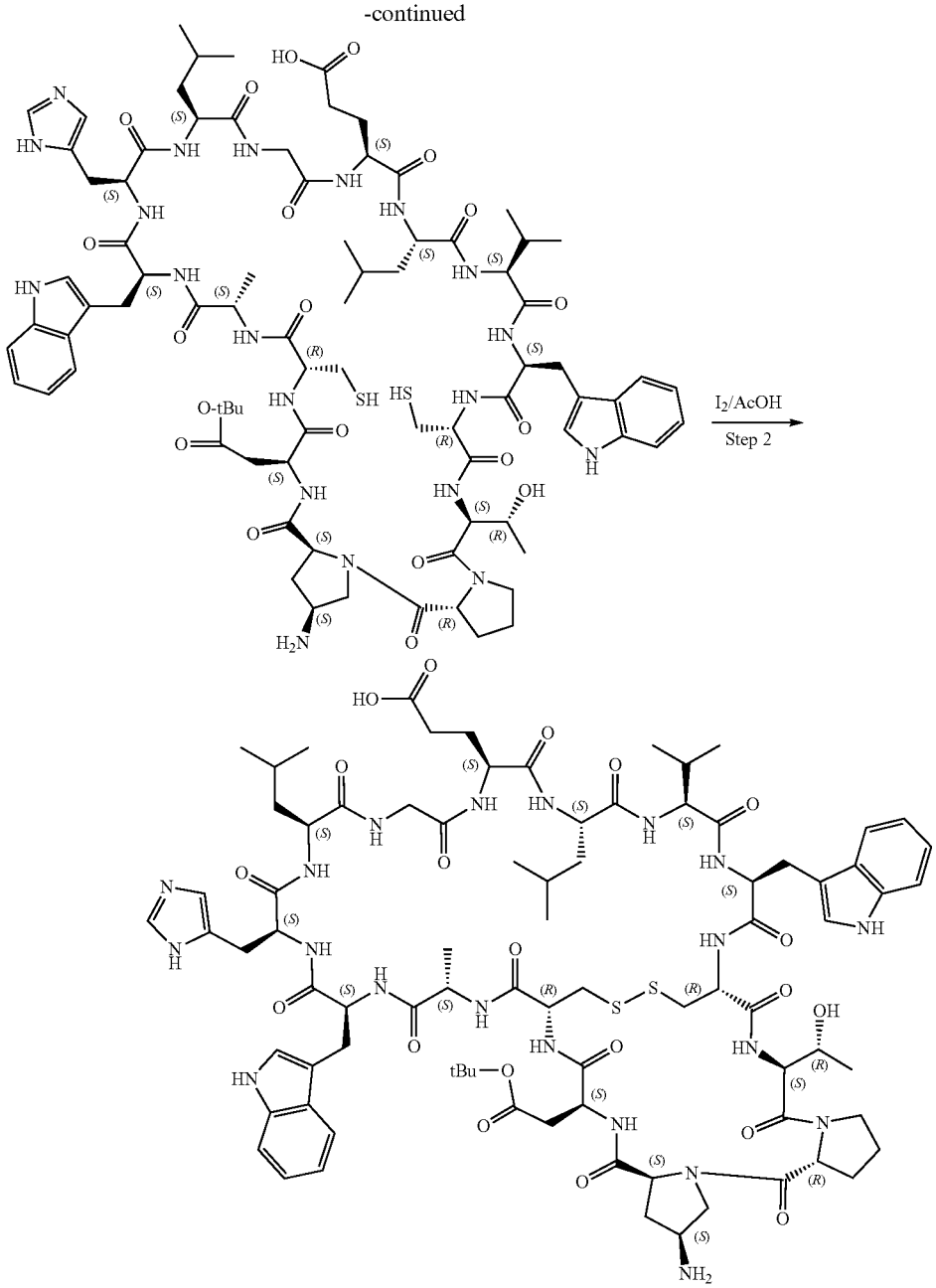

Intermediate 11

Step 1: Solid Phase Peptide Synthesis: The peptide was synthesized using standard Fmoc chemistry.
5) Resin preparation: To the vessel containing CTC Resin (200.00 g, 200.00 mmol, 1.00 mmol/g) and Fmoc-D-Pro-OH (67.40 g, 200.00 mmol, 1.00 eq) in DCM (3 L) was added DIEA (139.46 mL, 800.00 mmol, 4.00 eq) dropwise and mixed for 2 hrs with $N_2$ bubbling at 15° C. Then added MeOH (200.00 mL) and bubbled with $N_2$ for another 30 mins. The resin was washed with DMF (3 L)*5. Then 20% piperidine in DMF (5 L) was added and the mixture was bubbled with $N_2$ for 30 mins at 15° C. The mixture was filtered to obtain the resin. The resin was washed with DMF (3 L)*5 before proceeding to next step.

6) Coupling: A solution of Fmoc-Thr(tBu)-OH (238.20 g, 600.00 mmol, 3.00 eq), HBTU (216.03 g, 570.00 mmol, 2.85 eq) in DMF (500 mL) was added to the resin with $N_2$ bubbling. Then DIEA (209.18 mL, 1200.00 mmol, 6.00 eq) was added to the mixture dropwise and bubbled with $N_2$ for 30 mins at 15° C. The coupling reaction was monitored by ninhydrin test, if it showed colorless, the coupling was completed. The resin was then washed with DMF (3 L)*5.
7) De-protection: 20% piperidine in DMF (5 L) was added to the resin and the mixture was bubbled with $N_2$ for 30 mins at 15° C. The resin was then washed with DMF (3 L)*5. The De-protection reaction was monitored by ninhydrin test, if it showed blue or other brownish red, the reaction was completed.

8) Step 2 and 3 were repeated for all other amino acids: (2-15 in Table X).

TABLE X

| # | Materials | Coupling reagents |
|---|-----------|-------------------|
| 1 | Fmoc-D-Pro-OH (1.00 eq) | DIEA (4.00 eq) |
| 2 | Fmoc-Thr(tBu)-OH (3.00 eq) | HBTU (2.85 eq) and DIEA (6.00 eq) |
| 3 | Fmoc-Cys(Trt)-OH (3.00 eq) | HBTU (2.85 eq) and DIEA (6.00 eq) |
| 4 | Fmoc-Trp(Boc)-OH (3.00 eq) | HBTU (2.85 eq) and DIEA (6.00 eq) |
| 5 | Fmoc-Val-OH (3.00 eq) | HBTU (2.85 eq) and DIEA (6.00 eq) |
| 6 | Fmoc-Leu-OH (3.00 eq) | HBTU (2.85 eq) and DIEA (6.00 eq) |
| 7 | Fmoc-Glu(OtBu)-OH (3.00 eq) | HBTU (2.85 eq) and DIEA (6.00 eq) |
| 8 | Fmoc-Gly-OH (3.00 eq) | HBTU (2.85 eq) and DIEA (6.00 eq) |
| 9 | Fmoc-Leu-OH (3.00 eq) | HBTU (2.85 eq) and DIEA (6.00 eq) |
| 10 | Fmoc-His(Trt)-OH (2.00 eq) | HBTU (2.85 eq) and DIEA (6.00 eq) |
| 11 | Fmoc-Trp-OH (3.00 eq) | HBTU (2.85 eq) and DIEA (6.00 eg) |
| 12 | Fmoc-Ala-OH (3.00 eq) | HBTU (2.85 eq) and DIEA (6.00 eq) |
| 13 | Fmoc-Cys(Trt)-OH (3.00 eq) | HBTU (2.85 eq) and DIEA (6.00 eq) |
| 14 | Fmoc-Asp(OtBu)-OH (3.00 eq) | HBTU (2.85 eq) and DIEA (6.00 eq) |
| 15 | Boc-(2S,4S)-4-amino-1-Fmoc-pyrrolidine-2-carboxylic acid (1.00 eq) | HATU (0.95 eq) and DIEA (2.00 eq) |

Peptide Cleavage and Purification:

1) Cleavage buffer (20% HFIP/DCM, 8.0 L) was added into the flask containing the side chain protected crude peptide. The mixture was stirred for 1 hr at room temperature and the solution was collected after filtration. The cleavage step was repeated for another time.
2) The solution was combined after filtration.
3) The solution was concentrated by rotary evaporation.
4) The crude peptide was dried under lyophilization.
5) N—(N—((S)-5-(tert-butoxy)-2-(2-((S)-2-((S)-2-((S)-2-((S)-2-((R)-2-((S)-4-(tert-butoxy)-2-((2S,4S)-4-((tert-butoxycarbonyl)amino)pyrrolidine-2-carboxamido)-4-oxobutanamido)-3-(tritylthio)propanamido)propanamido)-3-(1H-indol-3-yl)propanamido)-3-(1-trityl-1H-imidazol-5-yl)propanamido)-4-methylpentanamido)acetamido)-5-oxopentanoyl)-L-leucyl-L-valyl-L-tryptophyl-S-trityl-L-cysteinyl)-O-(tert-butyl)-L-threonyl-D-proline (231.00 g, crude) was obtained as a white solid.
6) A mixture of N—(N—((S)-5-(tert-butoxy)-2-(2-((S)-2-((S)-2-((S)-2-((S)-2-((R)-2-((S)-4-(tert-butoxy)-2-((2S,4S)-4-((tert-butoxycarbonyl)amino)pyrrolidine-2-carboxamido)-4-oxobutanamido)-3-(tritylthio)propanamido)propanamido)-3-(1H-indol-3-yl)propanamido)-3-(1-trityl-1H-imidazol-5-yl)propanamido)-4-methylpentanamido)acetamido)-5-oxopentanoyl)-L-leucyl-L-valyl-L-tryptophyl-S-trityl-L-cysteinyl)-O-(tert-butyl)-L-threonyl-D-proline (13.58 g, 4.99 mmol, 1.00 eq), 2,4,6-trimethylpyridine (3.62 g, 29.98 mmol, 6.00 eq) in DMF (5.0 L) was added HATU (2.84 g, 7.49 mmol, 1.50 eq) at 25° C. Then the mixture was stirred at 25° C. for 3 hrs. Totally 17 batches were made one by one.
7) The solution was concentrated by rotary evaporation.
8) The residue was added to 0.50 M HCl (cold, 10 L) and white solid was precipitated. After filtered, the solid was dried under lyophilization to afford tert-butyl 3-((2S,5aR,11S,14R,17S,20S,23S,26S,32S,35S,38S,41S,44R,47S,49aS)-17,38-bis((1H-indol-3-yl)methyl)-47-(2-(tert-butoxy)-2-oxoethyl)-11-((R)-1-(tert-butoxy)ethyl)-2-((tert-butoxycarbonyl)amino)-23,32-diisobutyl-20-isopropyl-41-methyl-5,10,13,16,19,22,25,28,31,34,37,40,43,46,49-pentadecaoxo-35-((1-trityl-1H-imidazol-5-yl)methyl)-14,44-bis((tritylthio)methyl)octatetracontahydro-5H-dipyrrolo[1,2-a:1',2'-d][1,4,7,10,13,16,19,22,25,28,31,34,37,40,43]pentadecaazacyclopentatetracontin-26-yl)propanoate (245.00 g, crude, 17 batches) as a white solid. Chemical Formula: $C_{159}H_{192}N_{20}O_{26}S_2$, LCMS found: $[M+Na]^{2+}$=1370.88; $[M+H-242]^+$=1239.42;

Step 2: To a mixture of tert-butyl 3-((2S,5aR,11S,14R,17S,20S,23S,26S,32S,35S,38S,41S,44R,47S,49aS)-17,38-bis((1H-indol-3-yl)methyl)-47-(2-(tert-butoxy)-2-oxoethyl)-11-((R)-1-(tert-butoxy)ethyl)-2-((tert-butoxycarbonyl)amino)-23,32-diisobutyl-20-isopropyl-41-methyl-5,10,13,16,19,22,25,28,31,34,37,40,43,46,49-pentadecaoxo-35-((1-trityl-1H-imidazol-5-yl)methyl)-14,44-bis((tritylthio)methyl)octatetracontahydro-5H-dipyrrolo[1,2-a:1',2'-d][1,4,7,10,13,16,19,22,25,28,31,34,37,40,43]pentadecaazacyclopentatetracontin-26-yl)propanoate (245.00 g, crude) in TFA/TIS/H$_2$O/3-mercaptopropanoic acid (92.5%/2.5%/2.5%/2.5%, v/v/v, 5 L) was stirred at 20° C. for 1.5 hrs. The mixture was precipitated with cold isopropyl ether (30 L). After filtration, the solid was dried under vacuum for 2 hrs to afford 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-2-amino-47-(2-(tert-butoxy)-2-oxoethyl)-11-((R)-1-hydroxyethyl)-23,32-diisobutyl-20-isopropyl-14,44-bis(mercaptomethyl)-41-methyl-5,10,13,16,19,22,25,28,31,34,37,40,43,46,49-pentadecaoxooctatetracontahydro-5H-dipyrrolo[1,2-a:1',2'-d][1,4,7,10,13,16,19,22,25,28,31,34,37,40,43]pentadecaazacyclopentatetracontin-26-yl)propanoic acid (170.50 g, crude) which was dissolved in MeCN/H$_2$O (1/1, v/v, 100 L). 0.1 M I$_2$/HOAc was added to the mixture dropwise at 25° C. until the light yellow persisted, then the mixture was quenched with 0.1 M Na$_2$S$_2$O$_3$ dropwise until the light yellow disappeared. After filtration, the filtrate was purified by prep-HPLC (acid condition, TFA) directly to afford Intermediate 11 (21.10 g, 6.15% yield, 87.06% purity) as a white solid. Chemical Formula: $C_{79}H_{108}N_{20}O_{20}S_2$, LCMS found: $[M+H]^{1+}$=1722.70, $[M+2H]^{2+}$=861.50.

Preparation of Intermediate 12: 3-((6S,9R,12S,15S, 18S,21S,27S,30S,33S,36S,39R,42S,44aS,46S, 49aR)-30-((1H-imidazol-5-yl)methyl)-12,33-bis ((1H-indol-3-yl)methyl)-46-amino-6-((R)-1-hydroxyethyl)-18,27-diisobutyl-15-isopropyl-36,42-dimethyl-5,8,11,14,17,20,23,26,29,32,35,38,41,44, 49-pentadecaoxooctatetracontahydro-1H-9,39-(methanodithiomethano)dipyrrolo[1,2-a:1',2'-d][1,4, 7,10,13,16,19,22,25,28,31, 34,37,40,43] pentadecaazacyclopentatetracontin-21-yl)propanoic acid
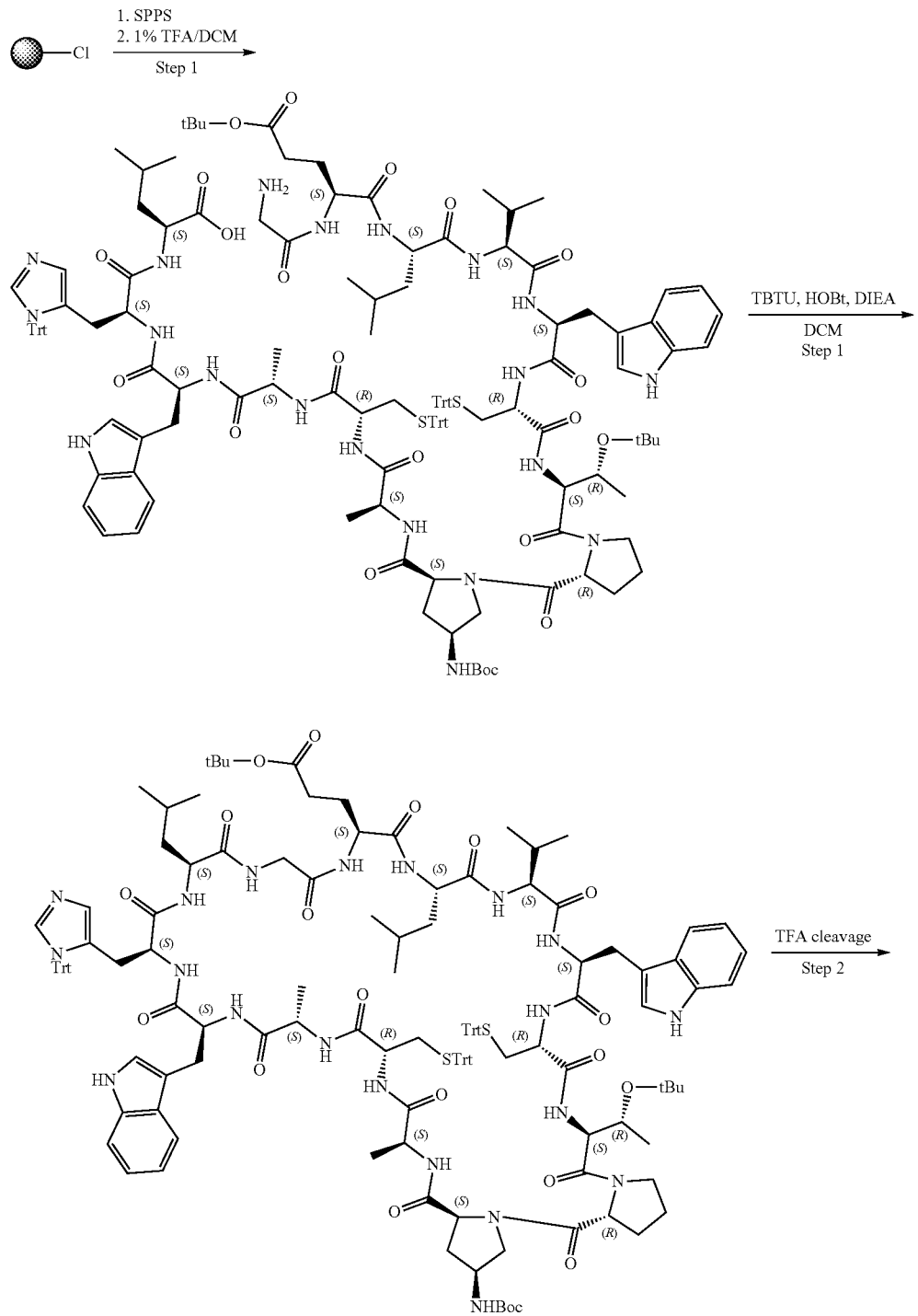

-continued
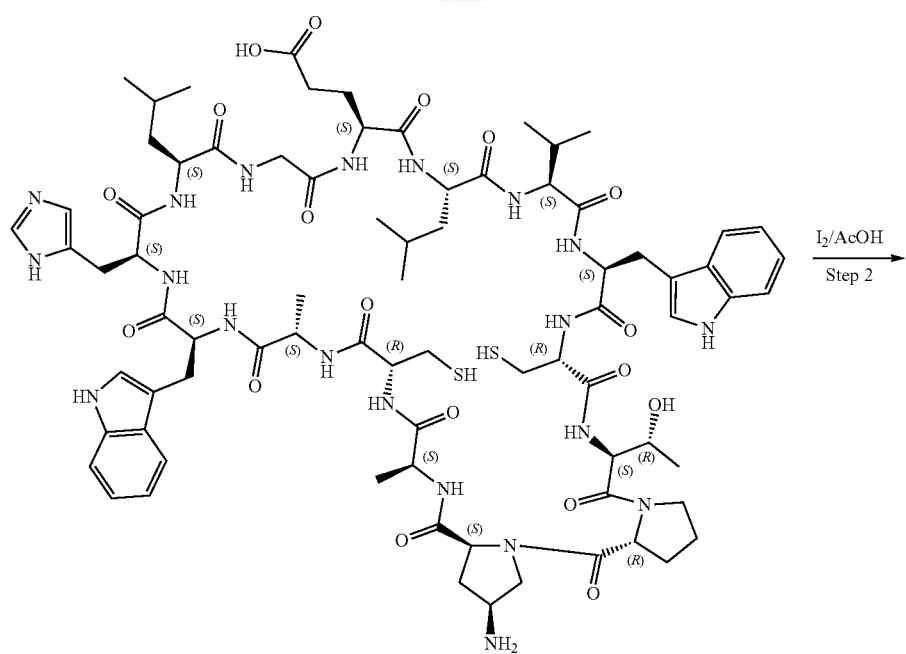
I₂/AcOH
Step 2
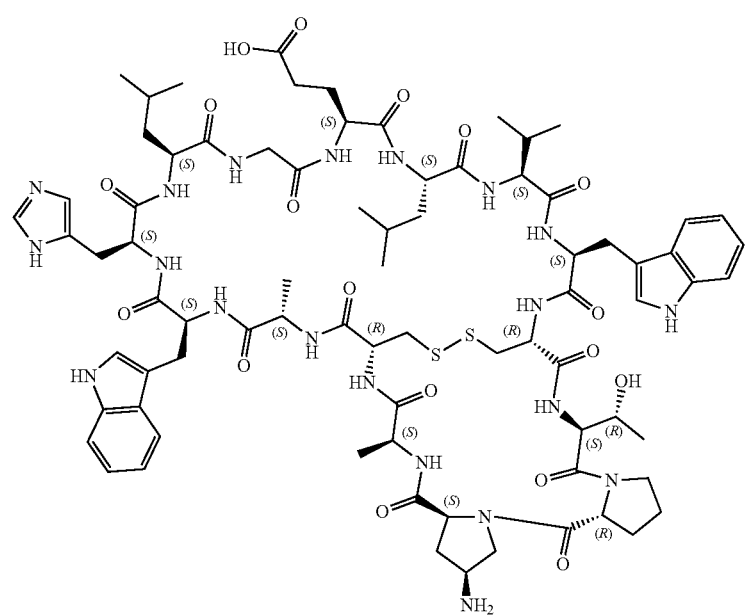
Intermediate 12

Step 1: Solid Phase Peptide Synthesis: The peptide was synthesized using standard Fmoc chemistry.

1) Resin preparation: To the vessel containing CTC Resin (0.50 g, 0.50 mmol, 1.00 mmol/g) and Fmoc-Gly-OH (148.50 mg, 0.50 mmol, 1.00 eq) in DCM (10 mL) was added DIEA (348.64 mL, 2.00 mmol, 4.00 eq) dropwise and mixed for 2 hrs with $N_2$ bubbling at 25° C. Then added MeOH (0.50 mL) and bubbled with $N_2$ for another 30 mins. The resin was washed with DMF (20 mL)*5. Then 20% piperidine in DMF (20 mL) was added and the mixture was bubbled with $N_2$ for 30 mins at 25° C. The mixture was filtered to obtain the resin. The resin was washed with DMF (20 mL)*5 before proceeding to next step.

2) Coupling: A solution of Fmoc-Glu(OtBu)-OH (637.5 mg, 1.50 mmol, 3.00 eq), HBTU (540.07 mg, 1.425 mmol, 2.85 eq) in DMF (10 mL) was added to the resin with $N_2$ bubbling. Then DIEA (522.97 mL, 3.00 mmol, 6.00 eq) was added to the mixture dropwise and bubbled with $N_2$ for 30 mins at 25° C. The coupling reaction was monitored by ninhydrin test, if it showed colorless, the coupling was completed. The resin was then washed with DMF (20 mL)*5.

3) De-protection: 20% piperidine in DMF (20 mL) was added to the resin and the mixture was bubbled with $N_2$ for 30 mins at 25° C. The resin was then washed with DMF (20 mL)*5. The De-protection reaction was monitored by ninhydrin test, if it showed blue or other brownish red, the reaction was completed.

4) Step 2 and 3 were repeated for all other amino acids: (2-15 in Table Y).

TABLE Y

| # | Materials | Coupling reagents |
|---|---|---|
| 1 | Fmoc-Gly-OH (1.00 eq) | DIEA (4.00 eq) |
| 2 | Fmoc-Glu(OtBu)-OH (3.00 eq) | HBTU (2.85 eq) and DIEA (6.00 eq) |
| 3 | Fmoc-Leu-OH (3.00 eq) | HBTU (2.85 eq) and DIEA (6.00 eq) |
| 4 | Fmoc-Val-OH (3.00 eq) | HBTU (2.85 eq) and DIEA (6.00 eq) |
| 5 | Fmoc-Trp-OH (3.00 eq) | HBTU (2.85 eq) and DIEA (6.00 eq) |
| 6 | Fmoc-Cys(Trt)-OH (3.00 eq) | HBTU (2.85 eq) and DIEA (6.00 eq) |
| 7 | Fmoc-Thr(tBu)-OH (3.00 eq) | HBTU (2.85 eq) and DIEA (6.00 eq) |
| 8 | Fmoc-D-Pro-OH (3.00 eq) | HBTU (2.85 eq) and DIEA (6.00 eq) |
| 9 | Boc-(2S,4S)-4-amino-1-Fmoc-pyrrolidine-2-carboxylic acid (1.00 eq) | HATU (0.95 eq) and DIEA (2.00 eq) |
| 10 | Fmoc-Ala-OH (3.00 eq) | HATU (2.85 eq) and DIEA (6.00 eq) |
| 11 | Fmoc-Cys(Trt)-OH (3.00 eq) | HBTU (2.85 eq) and DIEA (6.00 eq) |
| 12 | Fmoc-Ala-OH (3.00 eq) | HBTU (2.85 eq) and DIEA (6.00 eq) |
| 13 | Fmoc-Trp-OH (3.00 eq) | HBTU (2.85 eq) and DIEA (6.00 eq) |
| 14 | Fmoc-His(Trt)-OH (3.00 eq) | HBTU (2.85 eq) and DIEA (6.00 eq) |
| 15 | Fmoc-Leu-OH (3.00 eq) | HBTU (2.85 eq) and DIEA (6.00 eq) |

Peptide Cleavage and Purification:

1) Cleavage buffer (100 TFA/DCM, 30 mL) was added into the flask containing the side chain protected crude peptide. The mixture was stirred for 5 min at room temperature and the solution was collected after filtration. The cleavage step was repeated for another time.

2) The combined solution was diluted to 500 mL with DCM.

3) TBTU (321.00 mg, 1.00 mmol, 2.00 eq), and HOBt (135.00 mg, 1.00 mmol, 2.00 eq) were added and the mixture was stirred at 25° C. for 2 hrs.

4) The reaction mixture was washed with 1M HCl (200 mL), $H_2O$ (200 mL), brine (200 mL), dried over anhydrous $Na_2SO_4$, filtered and concentrated under vacuum to afford tert-butyl 3-((2S,5aR,11S,14R,17S,20S,23S,26S,32S,35S,38S,41S,44R,47S,49aS)-17,38-bis((1H-indol-3-yl)methyl)-11-((R)-1-(tert-butoxy)ethyl)-2-((tert-butoxycarbonyl)amino)-23,32-diisobutyl-20-isopropyl-41,47-dimethyl-5,10,13,16,19,22,25,28,31,34,37,40,43,46,49-pentadecaoxo-35-((1-trityl-1H-imidazol-5-yl)methyl)-14,44-bis((tritylthio)methyl)octatetracontahydro-5H-dipyrrolo[1,2-a:1',2'-d][1,4,7,10,13,16,19,22,25,28,31,34,37,40,43]pentadecaazacyclopentatetracontin-26-yl)propanoate (1.20 g, crude) as a white solid. Chemical Formula: $C_{148}H_{117}N_{20}O_{20}S_2$, LCMS found: $[M+Na]^{2+}=1320.77$.

Step 2: To a mixture of tert-butyl 3-((2S,5aR,11S,14R,17S,20S,23S,26S,32S,35S,38S,41S,44R,47S,49aS)-17,38-bis((1H-indol-3-yl)methyl)-11-((R)-1-(tert-butoxy)ethyl)-2-((tert-butoxycarbonyl)amino)-23,32-diisobutyl-20-isopropyl-41,47-dimethyl-5,10,13,16,19,22,25,28,31,34,37,40,43,46,49-pentadecaoxo-35-((1-trityl-1H-imidazol-5-yl)methyl)-14,44-bis((tritylthio)methyl)octatetracontahydro-5H-dipyrrolo[1,2-a:1',2'-d][1,4,7,10,13,16,19,22,25,28,31,34,37,40,43]pentadecaazacyclopentatetracontin-26-yl)propanoate (1.20 g, crude) in TFA/TIS/$H_2O$/3-mercaptopropanoic acid (92.5%/2.5%/2.5%/2.5%, v/v/v, 25 mL) was stirred at 25° C. for 1.5 hrs. The mixture was precipitated with cold isopropyl ether (150 mL) and centrifuged (3 min at 3000 rpm). The solid was washed with isopropyl ether twice, dried under vacuum for 2 hrs to afford compound 3 (900.0 mg, crude). Then compound 3 (900.0 mg, crude) was dissolved in MeCN/$H_2O$ (1/1, v/v, 500 mL). I2/HOAc (0.1 M) was added to the mixture dropwise at 25° C. until the light yellow persisted, then the mixture was quenched with 0.1 M $Na_2S_2O_3$ dropwise until the light yellow disappeared. After filtration, the filtrate was purified by prep-HPLC (acid condition, TFA) directly to afford 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-2-amino-11-((R)-1-hydroxyethyl)-23,32-diisobutyl-20-isopropyl-41,47-dimethyl-5,10,13,16,19,22,25,28,31,34,37,40,43,46,49-pentadecaoxoocta tetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Intermediate 12, 144.00 mg, 16.64% yield, 97.00% purity) as a white solid. Chemical Formula: $C_{78}H_{108}N_{20}O_{18}S_2$, LCMS found: $[M+H]1+=1677.79$, $[M+2H]2+=839.39$, $[M+3H]^{3+}=559.95$.

Intermediate 13—Intermediate 28 are Prepared as Described in the Preparation of Intermediate 12

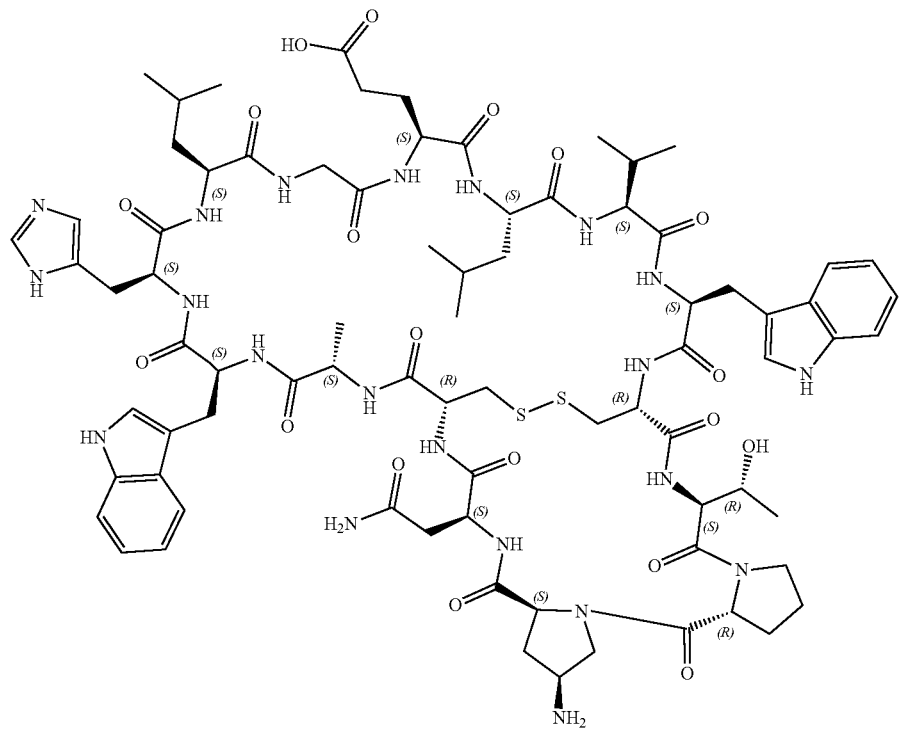

Intermediate 13

Intermediate 13: 3-((2S,5aR,11S,14R,17S,20S,23S, 26S,32S,35S,38S,41S,44R,47S,49aS)-35-((1H-imidazol-5-yl)methyl)-17,38-bis((1H-indol-3-yl)methyl)-2-amino-47-(2-amino-2-oxoethyl)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid Yield: 230.3 mg, 97.5% purity, 26.0%, white solid. LC-MS (ESI) found: [M+H]$^+$=1720.82, [M+2H]$^{2+}$=860.90, [M+3H]$^{3+}$=574.18.

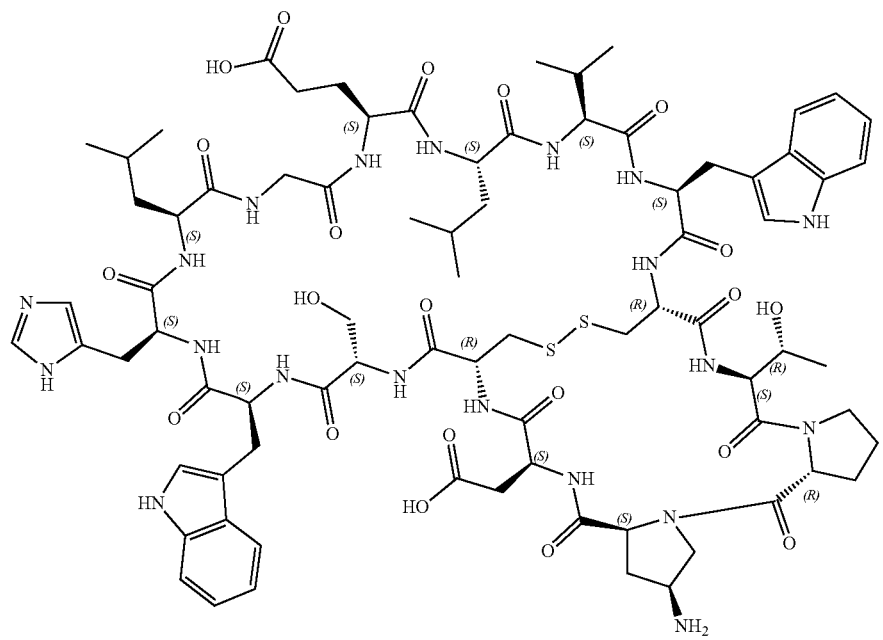

Intermediate 14

Intermediate 14: 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-2-amino-47-(carboxymethyl)-11-((R)-1-hydroxyethyl)-41-(hydroxymethyl)-23,32-diisobutyl-20-isopropyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid Yield: 252 mg, 95.4% purity, 27.6%, white solid. LC-MS (ESI) found: $[M+H]^+=1737.80$, $[M+2H]^{2+}=869.43$, $[M+3H]^{3+}=579.86$.

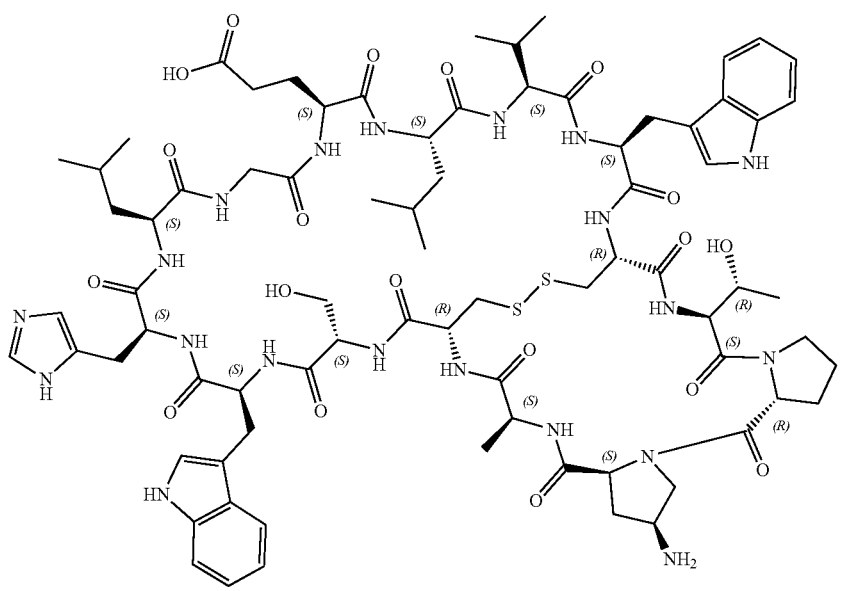

Intermediate 15

Intermediate 15: 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-2-amino-11-((R)-1-hydroxyethyl)-41-(hydroxymethyl)-23,32-diisobutyl-20-isopropyl-47-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid Yield: 144.7 mg, 96.1% purity. 16.4%, white solid. LC-MS (ESI) found: $[M+H]^+=1693.80$, $[M+2H]^{2+}=847.42$, $[M+3H]^{3+}=565.19$.

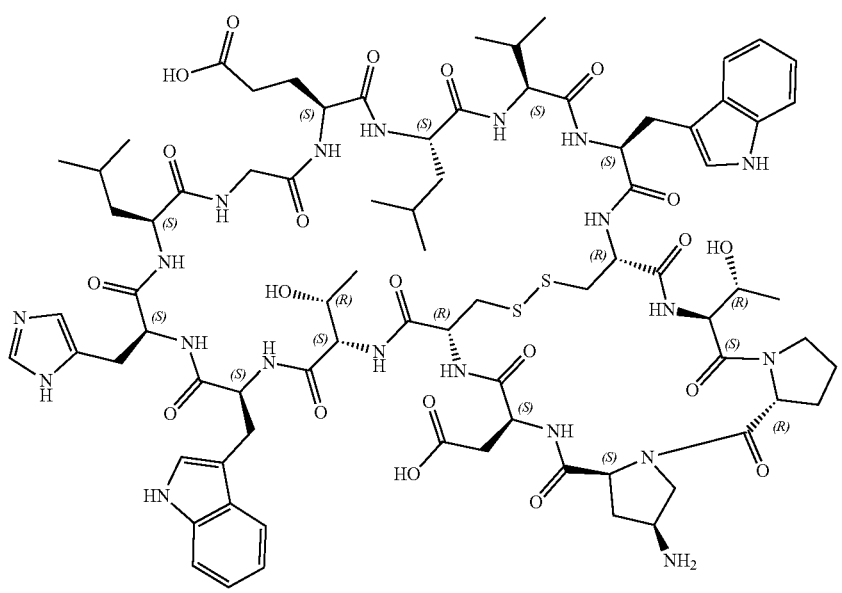

Intermediate 16

Intermediate 16: 3-((2S,5aR,11S,14R,17S,20S,23S, 26S,32S,35S,38S,41S,44R,47S,49aS)-35-((1H-imidazol-5-yl)methyl)-17,38-bis((1H-indol-3-yl)methyl)-2-amino-47-(carboxymethyl)-11,41-bis((R)-1-hydroxyethyl)-23,32-diisobutyl-20-isopropyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid Yield: 276.3 mg, 96.9% purity, 30.5%, white solid. LC-MS (ESI) found: [M+H]$^+$=1751.87, [M+2H]$^{2+}$=876.47, [M+3H]$^{3+}$=584.7.

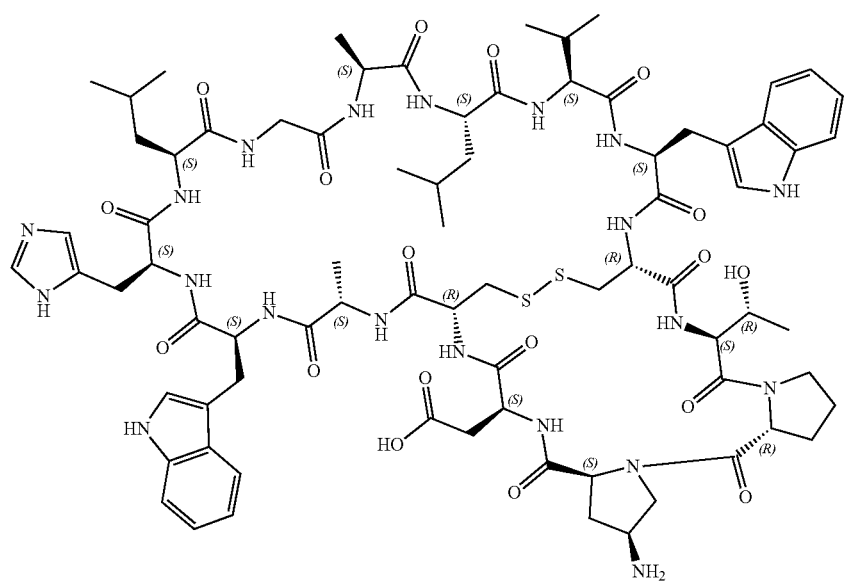

Intermediate 17

Intermediate 17: 2-((2S,5aR,11S,14R,17S,20S,23S, 26S,32S,35S,38S,41S,44R,47S,49aS)-35-((1H-imidazol-5-yl)methyl)-17,38-bis((1H-indol-3-yl)methyl)-2-amino-11-((R)-1-hydroxyethyl)-23,32-diisobutyl-20-isopropyl-26,41-dimethyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-47-yl)acetic acid
Yield: 223.4 mg, 95.0% purity, 25.5%, white solid. LC-MS (ESI) found: $[M+H]^+=1663.77$, $[M+2H]^{2+}=832.40$, $[M+3H]^{3+}=555.01$.
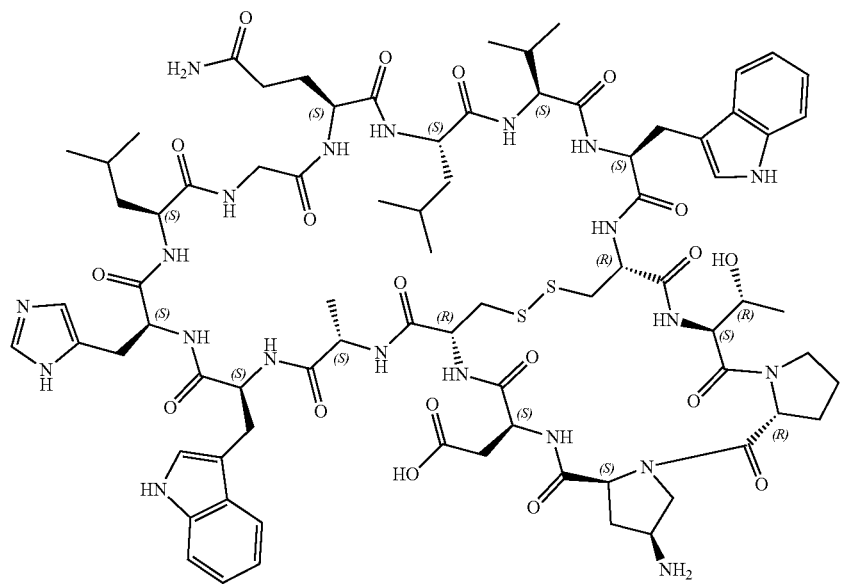
Intermediate 18

Intermediate 18: 2-((2S,5aR,11S,14R,17S,20S,23S, 26S,32S,35S,38S,41S,44R,47S,49aS)-35-((1H-imidazol-5-yl)methyl)-17,38-bis((1H-indol-3-yl) methyl)-2-amino-26-(3-amino-3-oxopropyl)-11-((R)-1-hydroxyethyl)-23,32-diisobutyl-20-isopropyl-41-methyl-5,10,13,16,19,22,25,28,31,34,37,40,43, 46,49-pentadecaoxooctatetracontahydro-5H-14,44-(methanodithiomethano)dipyrrolo[1,2-a:1',2'-d][1,4, 7,10,13,16,19,22,25,28,31,34,37,40,43] pentadecaazacyclopentatetracontin-47-yl)acetic acid Yield: 230.5 mg, 96.2% purity, 25.7%, white solid. LC-MS (ESI) found: $[M+H]^+=1720.89$, $[M+2H]^{2+}=861.00$, $[M+3H]^{3+}=574.29$.

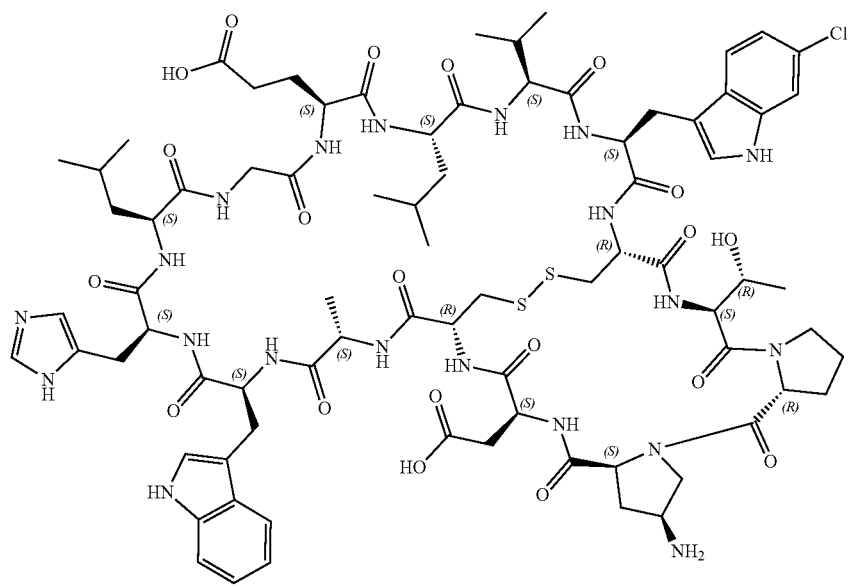

Intermediate 19

Intermediate 19: 3-((2S,5aR,11S,14R,17S,20S,23S, 26S,32S,35S,38S,41S,44R,47S,49aS)-35-((1H-imidazol-5-yl)methyl)-38-((1H-indol-3-yl)methyl)-2-amino-47-(carboxymethyl)-17-((6-chloro-1H-indol-3-yl)methyl)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid Yield: 215.7 mg, 95.1% purity, 23.3%, white solid. LC-MS (ESI) found: [M+H]$^+$=1755.81, [M+2H]$^{2+}$=878.50.

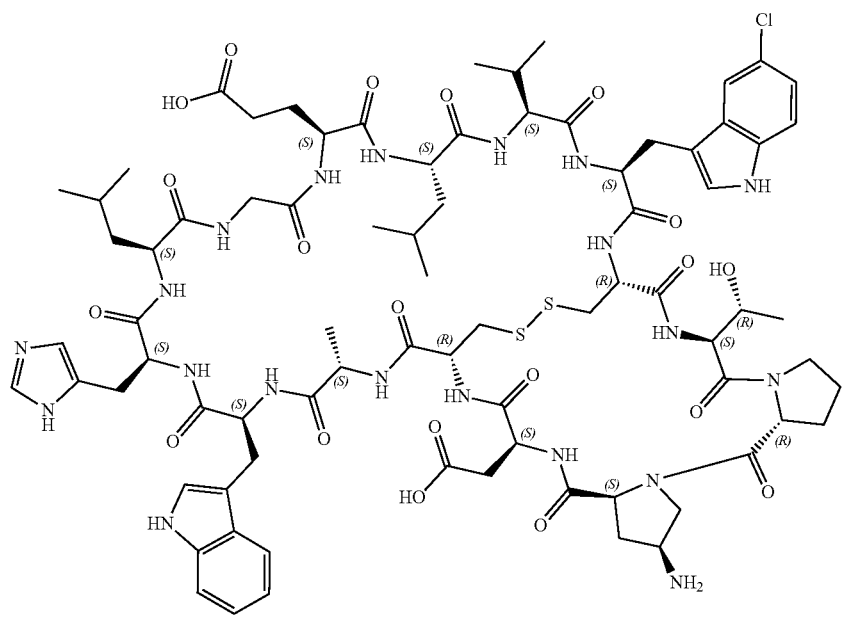

Intermediate 20

Intermediate 20: 3-((2S,5aR,11S,14R,17S,20S,23S,26S,32S,35S,38S,41S,44R,47S,49aS)-35-((1H-imidazol-5-yl)methyl)-38-((1H-indol-3-yl)methyl)-2-amino-47-(carboxymethyl)-17-((5-chloro-1H-indol-3-yl)methyl)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid Yield: 161.7 mg, 97.9% purity, 18.0%, white solid. LC-MS (ESI) found: [M+H]$^+$=1756.80, [M+2H]$^{2+}$=878.41, [M+3H]$^{3+}$=585.97.

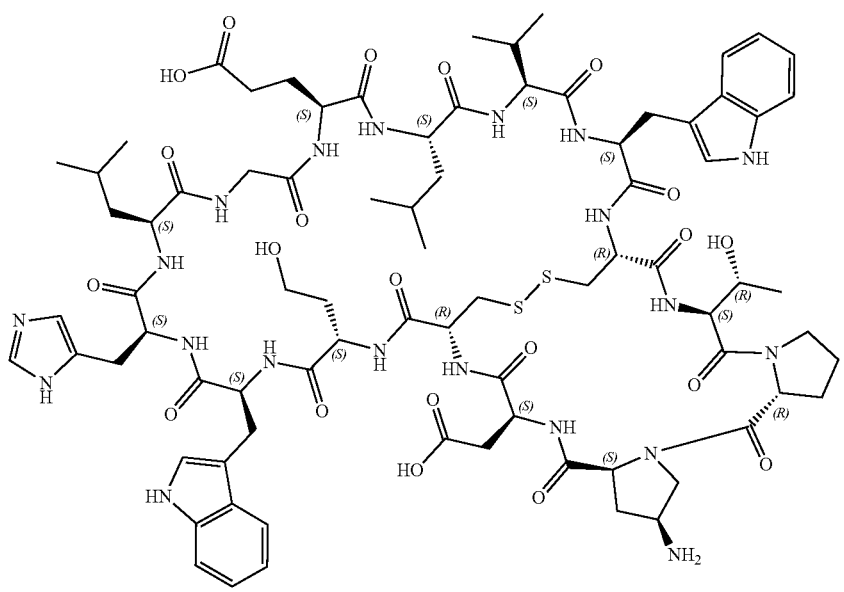

Intermediate 21

Intermediate 21: 3-((2S,5aR,11S,14R,17S,20S,23S, 26S,32S,35S,38S,41S,44R,47S,49aS)-35-((1H-imidazol-5-yl)methyl)-17,38-bis((1H-indol-3-yl)methyl)-2-amino-47-(carboxymethyl)-11-((R)-1-hydroxyethyl)-41-(2-hydroxyethyl)-23,32-diisobutyl-20-isopropyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid Yield: 163.7 mg, 98.0% purity, 18.3%, white solid. LC-MS (ESI) found: [M+H]$^+$=1751.81, [M+2H]$^{2+}$=876.41, [M+3H]$^{3+}$=584.62.

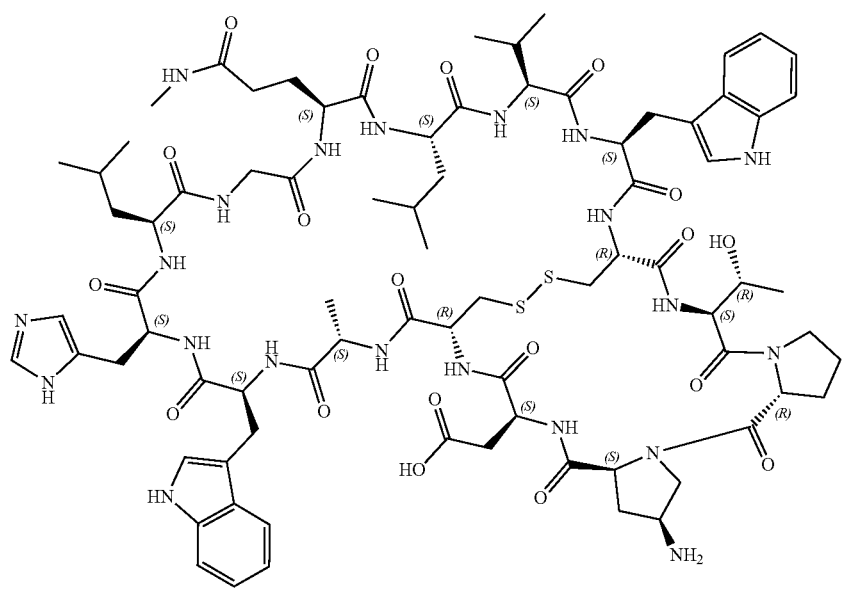

Intermediate 22

Intermediate 22: 2-((2S,5aR,11S,14R,17S,20S,23S, 26S,32S,35S,38S,41S,44R,47S,49aS)-35-((1H-imidazol-5-yl)methyl)-17,38-bis((1H-indol-3-yl)methyl)-2-amino-11-((R)-1-hydroxyethyl)-23,32-diisobutyl-20-isopropyl-41-methyl-26-(3-(methylamino)-3-oxopropyl)-5,10,13,16,19,22,25,28,31,34,37,40,43,46,49-pentadecaoxooctatetracontahydro-5H-14,44-(methanodithiomethano)dipyrrolo[1,2-a:1',2'-d] [1,4,7,10,13,16,19,22,25,28,31,34,37,40,43]pentadecaazacyclopentatetracontin-47-yl)acetic acid Yield: 153.3 mg, 95.4% purity, 16.8%, white solid. LC-MS (ESI) found: $[M+H]^+=1734.80$, $[M+2H]^{2+}=867.92$, $[M+3H]^{3+}=578.99$.

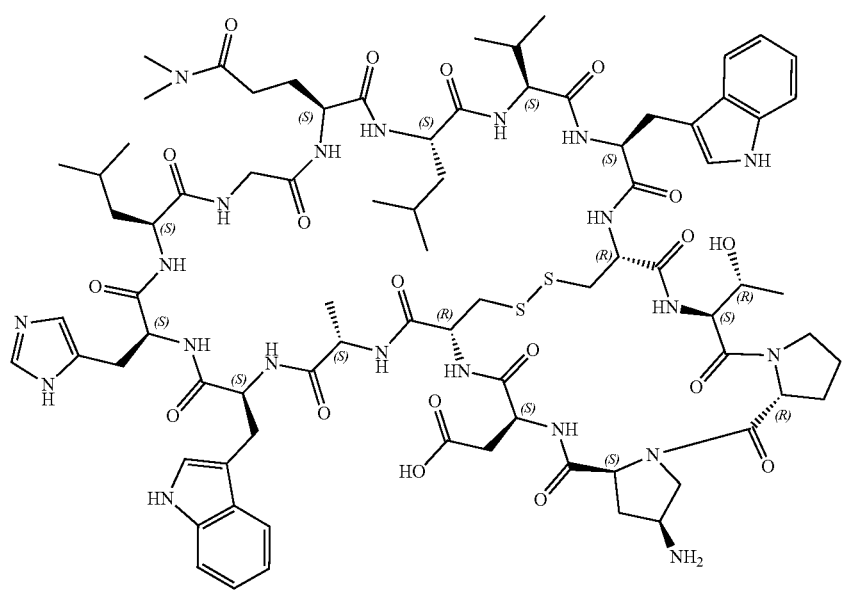

Intermediate 23

Intermediate 23: 2-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-2-amino-26-(3-(dimethylamino)-3-oxopropyl)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-47-yl)acetic acid Yield: 120.5 mg, 96.2% purity, 13.2%, white solid. LC-MS (ESI) found: $[M+H]^+=1748.90$, $[M+2H]^{2+}=874.96$, $[M+3H]^{3+}=583.60$ Intermediate 24

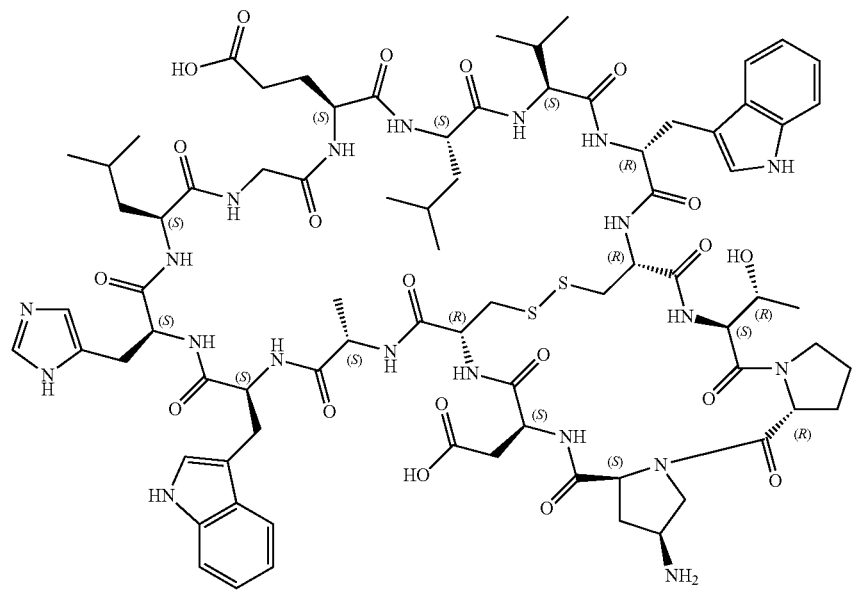

Intermediate 24: 3-((2S,5aR,11S,14R,17R,20S,23S, 26S,32S,35S,38S,41S,44R,47S,49aS)-35-((1H-imidazol-5-yl)methyl)-17,38-bis((1H-indol-3-yl) methyl)-2-amino-47-(carboxymethyl)-11-((R)-1-hydroxyethyl)-23,32-diisobutyl-20-isopropyl-41-methyl-5,10,13,16,19,22,25,28,31,34,37,40,43,46, 49-pentadecaoxooctatetracontahydro-5H-14,44-(methanodithiomethano)dipyrrolo[1,2-a:1',2'-d][1,4, 7,10,13,16,19,22,25,28,31,34,37,40,43] pentadecaazacyclopentatetracontin-26-yl)propanoic acid Yield: 188.5 mg, 95.6% purity, 20.9%, white solid. LC-MS (ESI) found: $[M+H]^+=1721.80$, $[M+2H]^{2+}=861.34$, $[M+3H]^{3+}=574.61$.

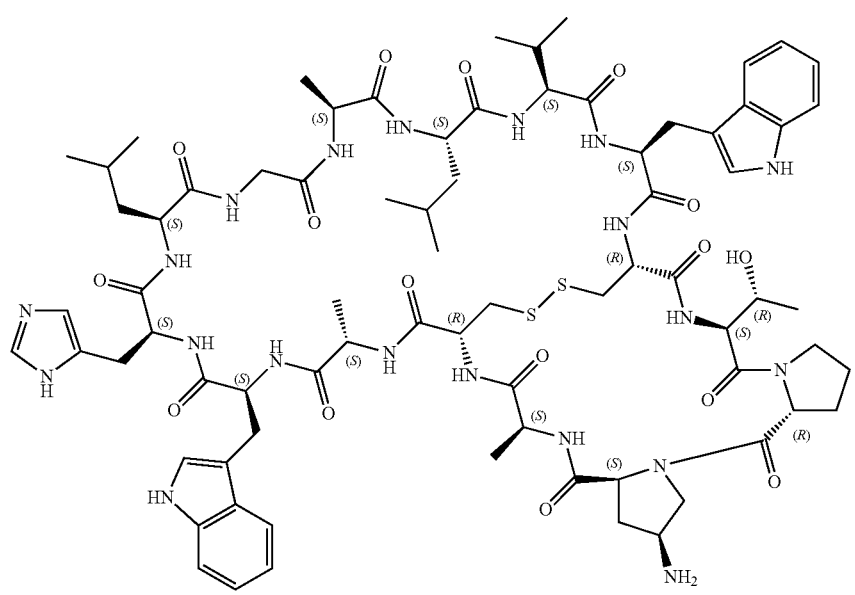

Intermediate 25

Intermediate 25: (2S,5aR,11S,14R,17S,20S,23S, 26S,32S,35S,38S,41S,44R,47S,49aS)-35-((1H-imi-dazol-5-yl)methyl)-17,38-bis((1H-indol-3-yl)methyl)-2-amino-11-((R)-1-hydroxyethyl)-23,32-diisobutyl-20-isopropyl-26,41,47-trimethyltetratriacontahydro-5H-14,44-(methanodithiomethano)dipyrrolo[1,2-a:1',2'-d][1,4,7,10,13,16,19,22,25,28,31,34,37,40,43]pentadecaazacyclopentatetracontine-5,10,13,16,19,22,25,28,31,34,37,40,43,46,49-pentadecaone
Yield: 163.5 mg, 95.9% purity, 19.1%, white solid. LC-MS (ESI) found: [M+H]$^+$=1619.60, [M+2H]$^{2+}$=810.50.
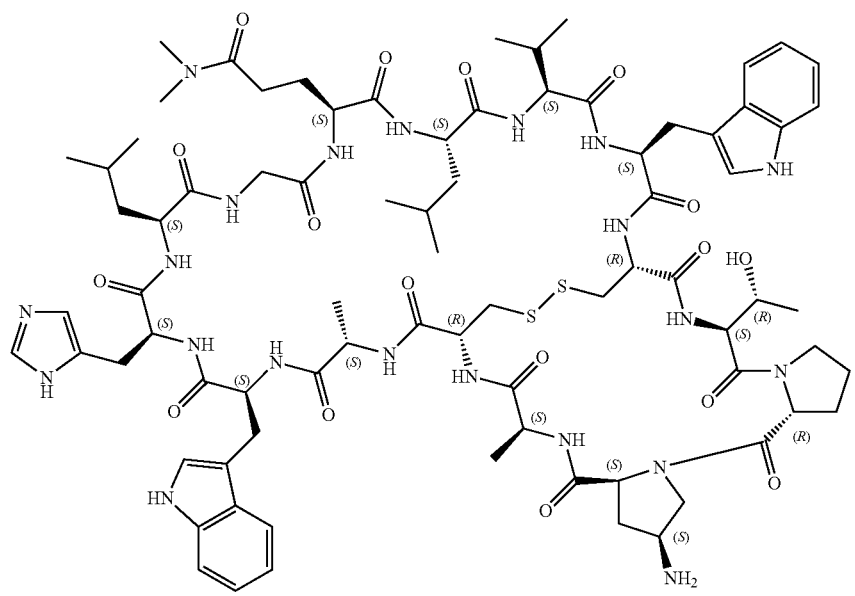
Intermediate 26

Intermediate 26: 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-2-amino-11-((R)-1-hydroxyethyl)-23,32-diisobutyl-20-isopropyl-41,47-dimethyl-5,10,13,16,19,22,25,28,31,34,37,40,43,46,49-pentadecaoxooctatetracontahydro-5H-14,44-(methanodithiomethano)dipyrrolo[1,2-a:1',2'd][1,4,7,10,13,16,19,22,25,28,31,34,37,40,43]pentadecaazacyclopentatetracontin-26-yl)-N,N-dimethylpropanamide
Yield: 34.9 mg, 94.4% purity, 6.4%, white solid. LC-MS (ESI) found: [M+H]$^+$=1704.60, [M+2H]$^{2+}$=853.00.
Intermediate 27
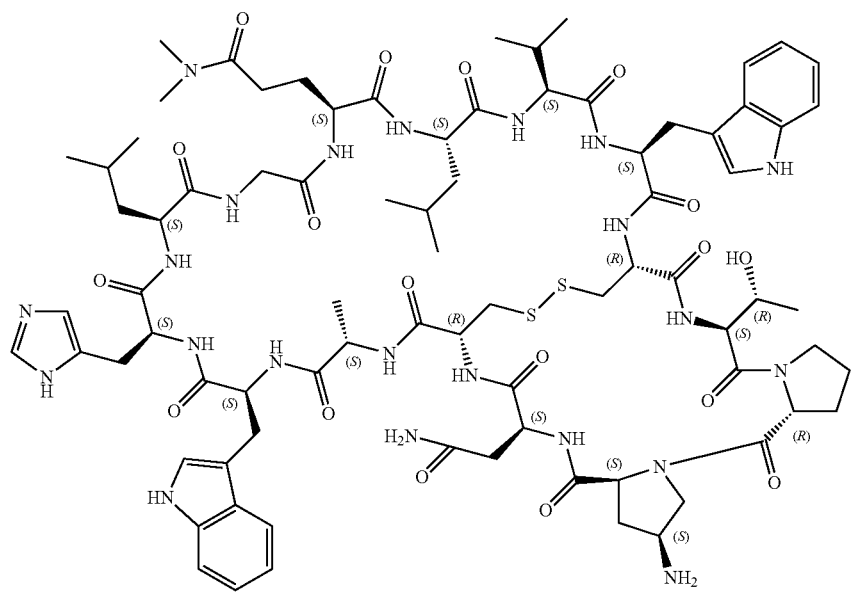

Intermediate 27: 3-((2S,5aR,11S,14R,17S,20S,23S, 26S,32S,35S,38S,41S,44R,47S,49aS)-35-((1H-imidazol-5-yl)methyl)-17,38-bis((1H-indol-3-yl) methyl)-2-amino-47-(2-amino-2-oxoethyl)-11-((R)-1-hydroxyethyl)-23,32-diisobutyl-20-isopropyl-41-methyl-5,10,13,16,19,22,25,28,31,34,37,40,43,46, 49-pentadecaoxooctatetracontahydro-5H-14,44-(methanodithiomethano)dipyrrolo[1,2-a:1',2'-d][1,4, 7,10,13,16,19,22,25,28,31,34,37,40,43] pentadecaazacyclopentatetracontin-26-yl)-N,N-dimethylpropanamide Yield: 119 mg, 96.9% purity, 22.0%, white solid. LC-MS (ESI) found: [M+H]$^+$=1747.70, [M+2H]$^{2+}$=874.60.

Intermediate 28

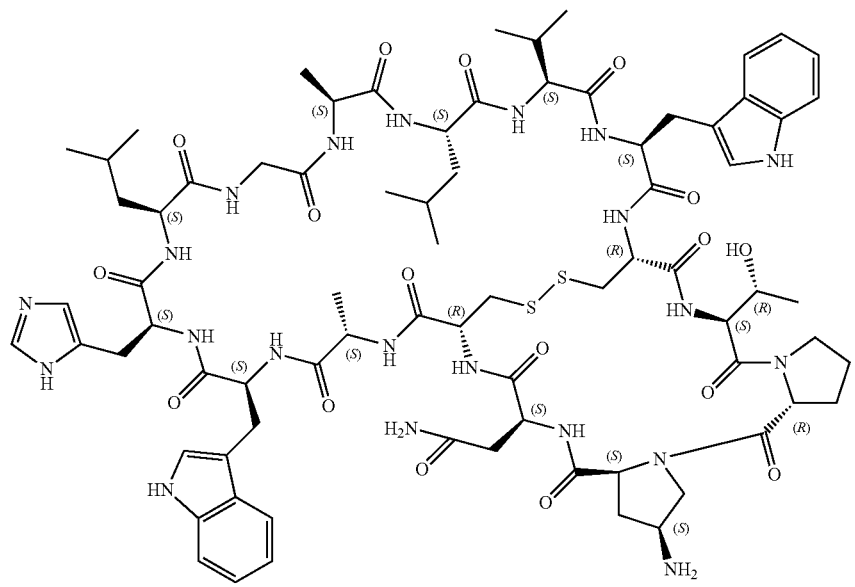

Intermediate 28: 2-((2S,5aR,11S,14R,17S,20S,23S, 26S,32S,35S,38S,41S,44R,47S,49aS)-35-((1H-imidazol-5-yl)methyl)-17,38-bis((1H-indol-3-yl) methyl)-2-amino-11-((R)-1-hydroxyethyl)-23,32-diisobutyl-20-isopropyl-26,41-dimethyl-5,10,13,16, 19,22,25,28,31,34,37,40,43,46,49-pentadecaoxooctatetracontahydro-5H-14,44-(methanodithiomethano)dipyrrolo[1,2-a:1',2'-d][1,4, 7,10,13,16,19,22,25,28,31,34,37,40,43] pentadecaazacyclopentatetracontin-47-yl)acetamide Yield: 159.8 mg, 97.0% purity, 18.6%, white solid. LC-MS (ESI) found: [M+H]$^+$=1662.60, [M+2H]$^{2+}$=832.10.

Preparation of (4-(isoquinolin-8-yl)-3-(4-(isoquinolin-8-yl)phenethoxy)phenyl)methanol

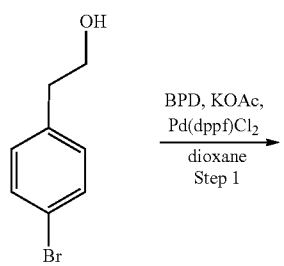

BPD, KOAc, Pd(dppf)Cl$_2$
dioxane
Step 1

-continued

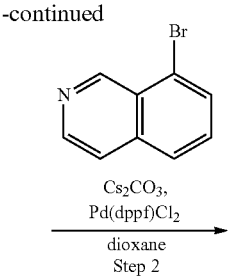

Cs$_2$CO$_3$,
Pd(dppf)Cl$_2$
dioxane
Step 2

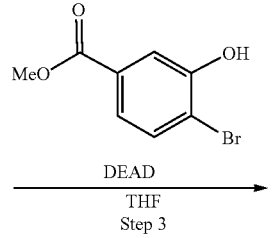

DEAD
THF
Step 3

-continued

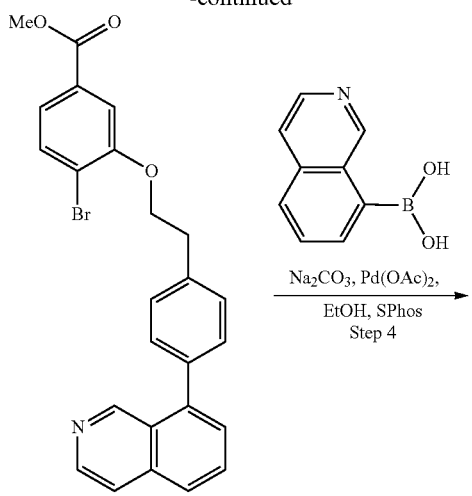

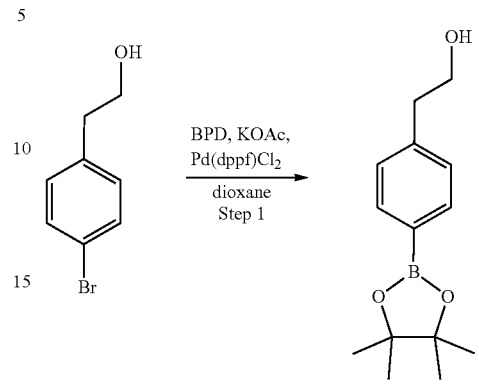

Na₂CO₃, Pd(OAc)₂,
EtOH, SPhos
Step 4

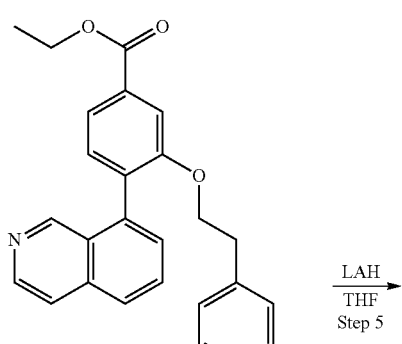

LAH
THF
Step 5

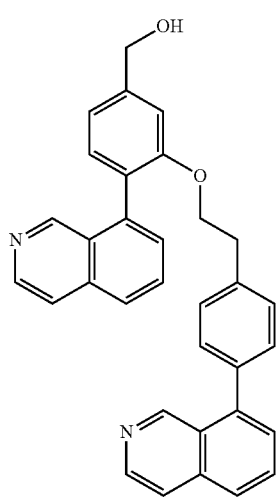

Preparation of 2-(4-(4,4,5,5-tetramethyl-1,3,2-dioxaborolan-2-yl)phenyl)ethan-1-ol

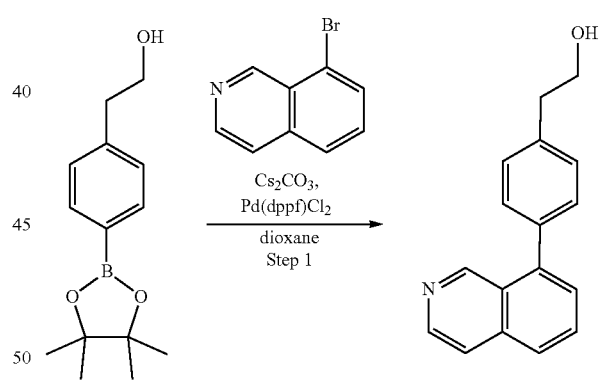

Step 1: To a solution of 2-(4-bromophenyl)ethan-1-ol (30 g, 149.21 mmol, 20.83 mL, 1 eq.) in dioxane (200 mL) was added BPD (45.47 g, 179.05 mmol, 1.2 eq.), KOAc (29.29 g, 298.42 mmol, 2 eq.) and Pd(dppf)Cl₂ (5.46 g, 7.46 mmol, 0.05 eq.). The reaction mixture was stirred for 85° C. for 12 h. The residue was diluted with water (200 mL) and extracted with EtOAc (300 mL×2). The combined organic layers were washed with brine (100 mL) and then dried over Na₂SO₄ filtered and concentrated under reduced pressure to give a residue. The residue was without purification use to next step reaction. (35 g, crude) was obtained as a black oil.

Preparation of
2-(4-(isoquinolin-8-yl)phenyl)ethan-1-ol

Step 1: To a solution of 2-(4-(4,4,5,5-tetramethyl-1,3,2-dioxaborolan-2-yl)phenyl)ethan-1-ol (35 g, 141.06 mmol, 1 eq.) and 8-bromoisoquinoline (32.28 g, 155.16 mmol, 1.1 eq.) in dioxane (300 mL) was added dicesium carbonate (91.92 g, 282.12 mmol, 2 eq.) and Pd(dppf)Cl₂ (2.06 g, 2.82 mmol, 0.02 eq.). The mixture was stirred at 95° C. for 2 hr. The reaction mixture was diluted with water (100 mL) and extracted with EtOAc (100 mL×3). The combined organic layers were washed with brine (100 mL), dried over Na₂SO₄, filtered, and concentrated under reduced pressure to give a residue. The residue was purified by flash silica gel chromatography (ISCO®; 220 g SepaFlash® Silica Flash Column, Eluent of 0-60% Ethyl acetate/Petroleum ether gradient @ 80 mL/min). (13 g, 52.14 mmol, 36.97% yield) was obtained as a white solid. ¹H NMR (400 MHz, chloroform-d) δ=9.33 (s, 1H), 8.55 (d, J=5.6 Hz, 1H), 7.81 (br s, 1H), 7.83 (d, J=8.3 Hz, 1H), 7.78-7.68 (m, 2H), 7.57-7.45 (m, 3H), 7.44-7.36 (m, 2H), 3.98 (t, J=6.6 Hz, 2H), 3.00 (t, J=6.6 Hz, 2H).

Preparation of methyl 4-bromo-3-(4-(isoquinolin-8-yl)phenethoxy)benzoate

Preparation of ethyl 4-(isoquinolin-8-yl)-3-(4-(isoquinolin-8-yl)phenethoxy)benzoate

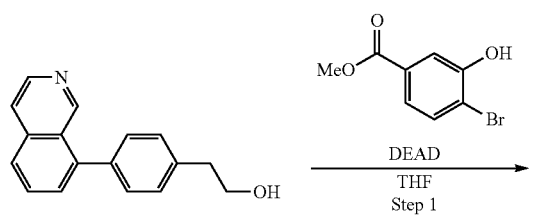

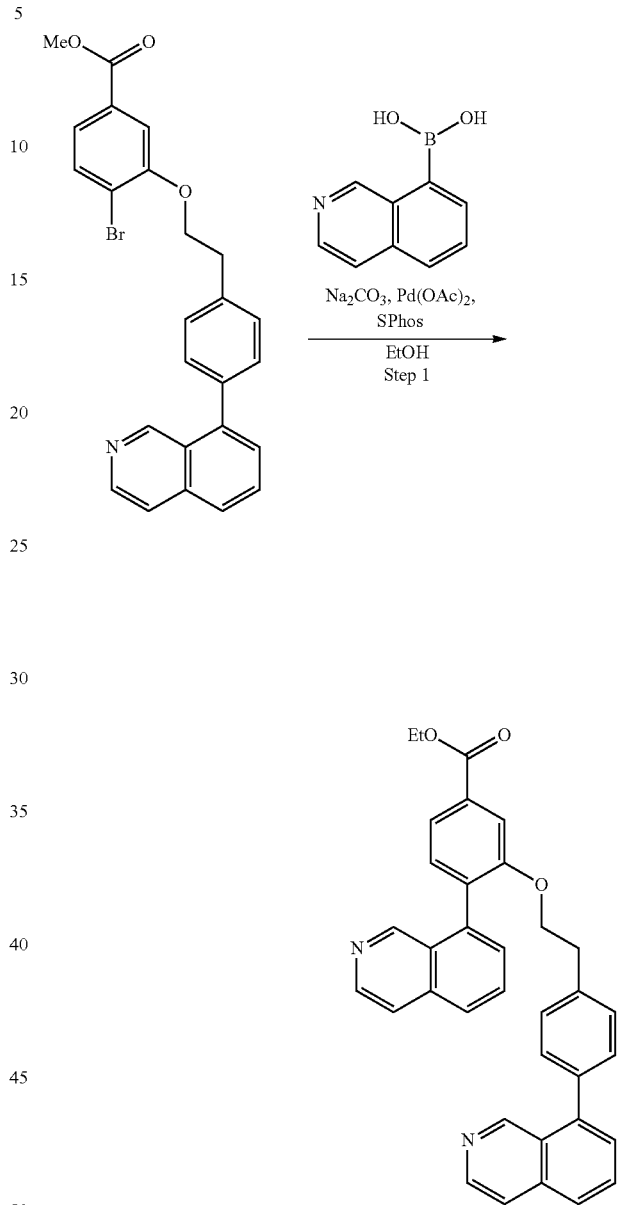

Step 1: To a mixture of 2-(4-(isoquinolin-8-yl)phenyl)ethan-1-ol (12.0 g, 48.13 mmol, 1 eq.), methyl 4-bromo-3-hydroxy-benzoate (13.35 g, 57.76 mmol, 1.2 eq.), triphenylphosphene (25.25 g, 96.27 mmol, 2 eq.) in THF (120 mL) was added DEAD (16.77 g, 96.27 mmol, 17.50 mL, 2 eq.) at 0° C., and then degassed and purged with N₂ for 3 times. The mixture was stirred at 15° C. for 12 hr under N₂ atmosphere. The reaction mixture was diluted with water (80 mL) and extracted with EtOAc 150 mL (50 mL×3). The combined organic layers were washed with brine 60 mL (20 mL×3), dried over Na₂SO₄, filtered, and concentrated under reduced pressure to give a residue. The residue was purified by flash silica gel chromatography (ISCO®; 120 g SepaFlash® Silica Flash Column, Eluent of 0~50% Ethyl acetate/Petroleum ether gradient@50 mL/min). (16 g, 34.61 mmol, 71.90% yield) was obtained as a white solid. ¹H NMR (400 MHz, chloroform-d) δ=9.34 (s, 1H), 8.55 (d, J=5.1 Hz, 1H), 7.87-7.80 (m, 1H), 7.78-7.68 (m, 2H), 7.66-7.60 (m, 1H), 7.59-7.47 (m, 7H), 4.32 (q, J=7.0 Hz, 2H), 3.92 (d, J=1.0 Hz, 3H), 3.30 (t, J=6.5 Hz, 2H).

Step 1: To a mixture of methyl 4-bromo-3-(4-(isoquinolin-8-yl)phenethoxy)benzoate (50 mg, 108.15 μmol, 1 eq.), 8-isoquinolylboronic acid (28.06 mg, 162.23 μmol, 1.5 eq.), Na₂CO₃ (28.66 mg, 270.38 μmol, 2.5 eq.), dicyclohexyl-[2-(2,6-dimethoxyphenyl)phenyl] phosphane (8.88 mg, 21.63 μmol, 0.2 eq.) and diacetoxypalladium (2.43 mg, 10.82 μmol, 0.1 eq.) in EtOH (4 mL) was degassed and purged with N₂ for 3 times, and then the mixture was stirred at 95° C. for 12 hr under N₂ atmosphere. The reaction mixture was diluted with water 1 mL and extracted with EtOAc 20 mL (10 mL×2). The combined organic layers were washed with brine (4 mL), dried over Na₂SO₄, filtered and concentrated under reduced pressure to give a residue. The residue was purified by prep-TLC (SiO₂, EtOAc). (30 mg, 58.76 μmol, 54.33% yield) was obtained as a white solid.

799
Preparation of (4-(isoquinolin-8-yl)-3-(4-(isoquinolin-8-yl)phenethoxy)phenyl)methanol

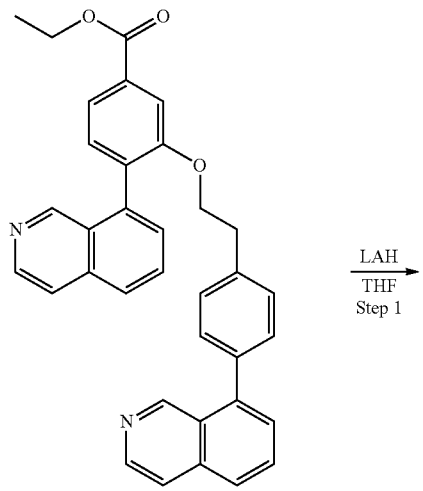

Step 1: To a mixture of ethyl 4-(isoquinolin-8-yl)-3-(4-(isoquinolin-8-yl)phenethoxy)benzoate (20 mg, 39.17 μmol, 1 eq.) in THF (1 mL) was added LAH (2.97 mg, 78.34 μmol, 2 eq.) at 0° C. The mixture was degassed and purged with $N_2$ for 3 times, and then the mixture was stirred at 20° C. for 1 h under $N_2$ atmosphere. The reaction mixture was quenched by addition solvent of $MgSO_4 \cdot 0.04$ mL at 0° C., and then the mixture was filtered through a Celite pad, and the filtrate was dried over $Na_2SO_4$, filtered, and concentrated under reduced pressure to give a residue. The residue was purified by prep-TLC ($SiO_2$, EtOAc) to afford Intermediate 25 (2 mg, 3.81 μmol, 9.73% yield, 92% purity) as a white solid. $^1$H NMR (400 MHz, chloroform-d) δ=9.18 (s, 1H), 9.07 (s, 1H), 8.58-8.47 (m, 2H), 7.89-7.73 (m, 6H), 7.54-7.46 (m, 2H), 7.31 (d, J=7.5 Hz, 1H), 7.18 (d, J=7.9 Hz, 2H), 7.13-7.08 (m, 2H), 6.88 (d, J=7.5 Hz, 2H), 4.82 (s, 2H), 4.32-4.14 (m, 2H), 2.91-2.78 (m, 2H), 2.91-2.78 (m, 1H).

800
Preparation of 2-(2-(2-((4-(isoquinolin-8-yl)-3-(4-(isoquinolin-8-yl)phenethoxy)benzyl)oxy)ethoxy)ethoxy)ethan-1-amine

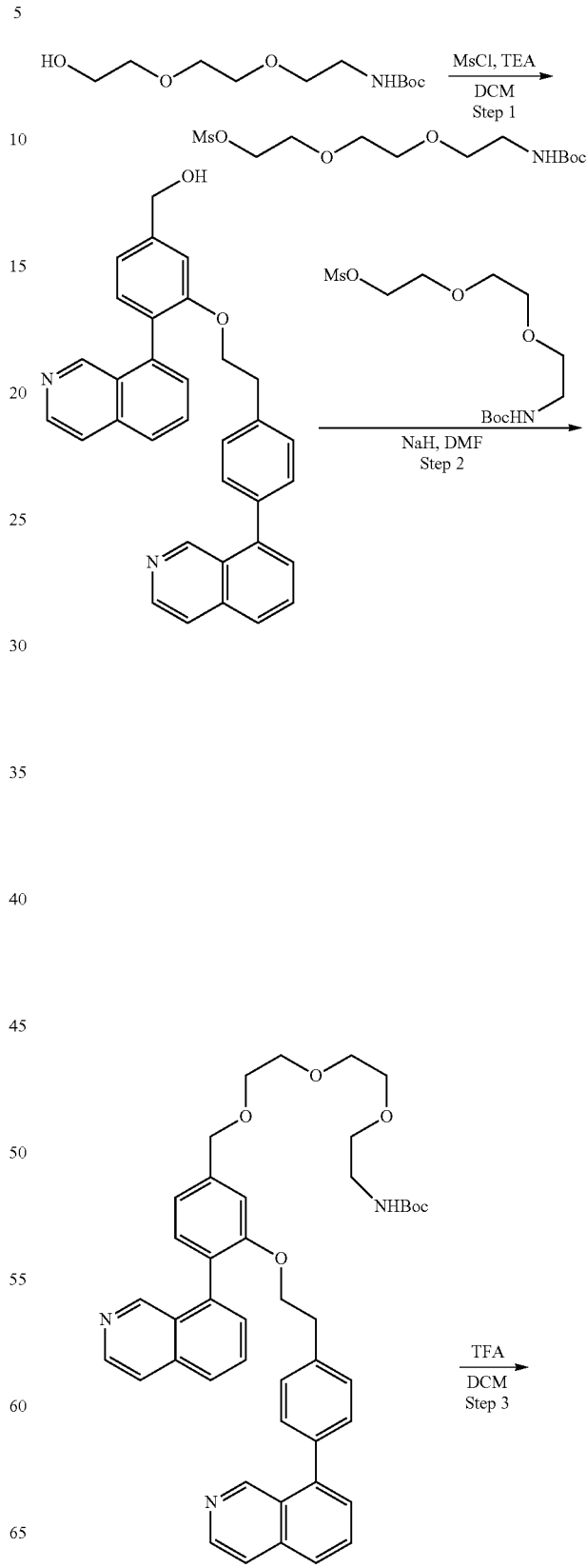

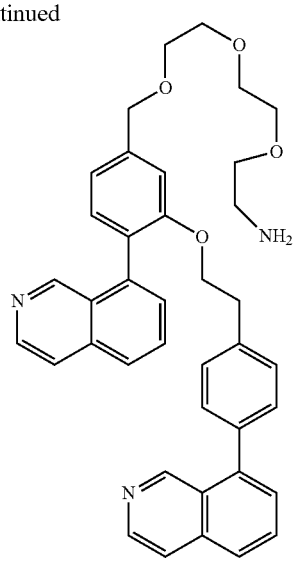

Step 1: To a solution of tert-butyl (2-(2-(2-hydroxyethoxy)ethoxy)ethyl)carbamate (1 g, 4.01 mmol, 1 eq) in DCM (10 mL) were added MsCl (689.23 mg, 6.02 mmol, 465.69 μL, 1.5 eq) and TEA (811.77 mg, 8.02 mmol, 1.12 mL, 2 eq) at 0° C. The mixture was degassed and purged with $N_2$ for 3 times, and then the mixture was stirred at 20° C. for 2 h under $N_2$ atmosphere. The reaction mixture was quenched with 5 mL of $NaHCO_3$ sat solution, and then extracted with EtOAc 20 mL (100 mL×2). The combined organic layers were dried over $Na_2SO_4$, filtered, and concentrated under reduced pressure to give the crude product. The crude product was used directly for the next step without purification. 2,2-dimethyl-4-oxo-3,8,11-trioxa-5-azatridecan-13-yl methanesulfonate (1.1 g, 3.36 mmol, 83.76% yield) was obtained as light-yellow oil. $^1$H NMR (400 MHz, chloroform-d) Shift=4.92 (br s, 1H), 4.46-4.35 (m, 2H), 3.78 (dd, J=3.6, 5.4 Hz, 2H), 3.72-3.65 (m, 2H), 3.65-3.59 (m, 2H), 3.54 (t, J=5.2 Hz, 2H), 3.33 (br s, 2H), 3.08 (s, 3H), 1.46 (s, 9H).

Step 2: To a mixture solution of (4-(isoquinolin-8-yl)-3-(4-(isoquinolin-8-yl)phenethoxy)phenyl)methanol (100 mg, 207.22 μmol, 1 eq) and 2,2-dimethyl-4-oxo-3,8,11-trioxa-5-azatridecan-13-yl methanesulfonate (135.69 mg, 414.44 μmol, 2 eq) in DMF (1 mL) was added NaH (33.15 mg, 828.88 μmol, 60% purity, 4 eq) at 0° C. The mixture was degassed and purged with $N_2$ for 3 times, and then the mixture was stirred at 20° C. for 12 h under $N_2$ atmosphere. The reaction mixture was quenched by addition of water (2 mL) at 0° C., and then diluted with water (4 mL) and extracted with EtOAc 30 mL (15 mL×2). The combined organic layers were washed with brine (5 mL), dried over $Na_2SO_4$, filtered and concentrated under reduced pressure to give a residue. The residue was purified by prep-TLC ($SiO_2$, EtOAc=1). The title tert-butyl (2-(2-(2-((4-(isoquinolin-8-yl)-3-(4-(isoquinolin-8-yl)phenethoxy)benzyl)oxy)ethoxy)ethoxy)ethyl)carbamate (80 mg, 112.07 μmol, 54.0% yield) was obtained as a yellow solid. 1H NMR (400 MHz, chloroform-d) δ=4.45-4.36 (m, 2H), 3.83-3.77 (m, 2H), 3.72-3.65 (m, 2H), 3.65-3.60 (m, 2H), 3.54 (t, J=5.3 Hz, 2H), 3.39-3.28 (m, 2H), 3.08 (s, 3H), 1.46 (s, 9H). LCMS: 714.5.

Step 3: To a solution of tert-butyl (2-(2-(2-((4-(isoquinolin-8-yl)-3-(4-(isoquinolin-8-yl)phenethoxy)benzyl)oxy)ethoxy)ethyl)carbamate (70 mg, 98.06 μmol, 1 eq) was added to TFA (4.62 g, 40.52 mmol, 3 mL, 413.21 eq). The mixture was degassed and purged with $N_2$ for 3 times, and then the mixture was stirred at 20° C. for 1 hr under $N_2$ atmosphere. The reaction mixture was filtered and concentrated under reduced pressure to give a residue. The residue was purified by prep-HPLC. The 2-(2-(2-((4-(isoquinolin-8-yl)-3-(4-(isoquinolin-8-yl)phenethoxy)benzyl)oxy)ethoxy)ethoxy)ethan-1-amine (10 mg, 16.29 μmol, 16.6% yield) was obtained as a white solid. $^1$H NMR (400 MHz, CHLOROFORM-d) Shift=9.36-9.36 (m, 1H), 9.36-9.34 (m, 1H), 9.36-9.34 (m, 1H), 9.42-9.29 (m, 1H), 8.65 (br d, J=6.3 Hz, 1H), 8.40 (br d, J=6.4 Hz, 1H), 8.25-8.06 (m, 7H), 7.85 (t, J=6.8 Hz, 2H), 7.34-7.29 (m, 2H), 7.18 (br d, J=7.6 Hz, 2H), 6.96 (br d, J=7.8 Hz, 2H), 4.73-4.61 (m, 2H), 4.47-4.38 (m, 1H), 4.43 (br d, J=8.3 Hz, 1H), 4.23 (br d, J=9.1 Hz, 1H), 3.79 (br d, J=9.8 Hz, 6H), 3.68 (br d, J=7.0 Hz, 4H), 3.17 (br s, 2H), 2.91-2.66 (m, 2H). LCMS: 614.2.

Preparation of 8-(4-(2-(5-(piperazin-1-ylmethyl)-2-(1H-pyrrolo[3,2-c]pyridin-3-yl)phenoxy)ethyl)phenyl)isoquinoline

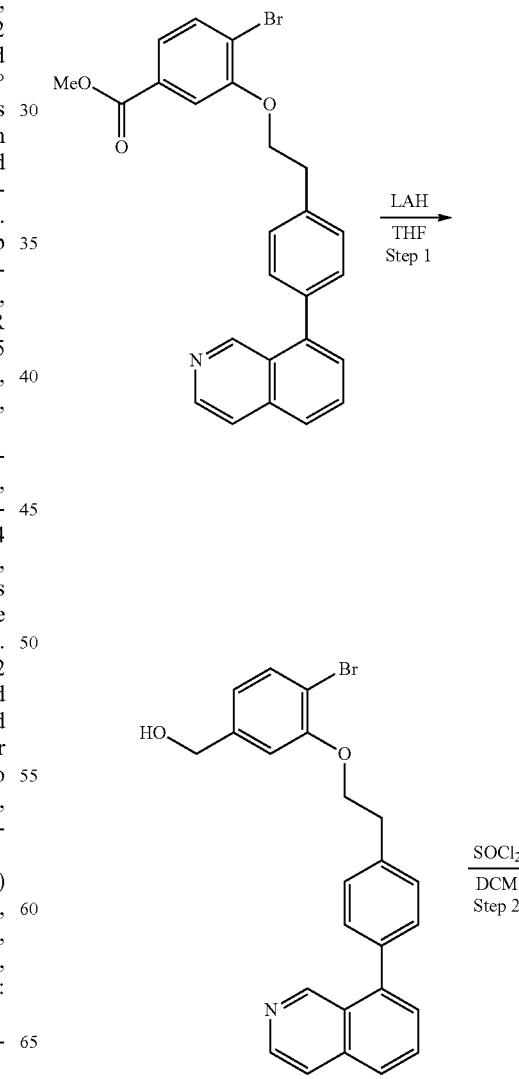

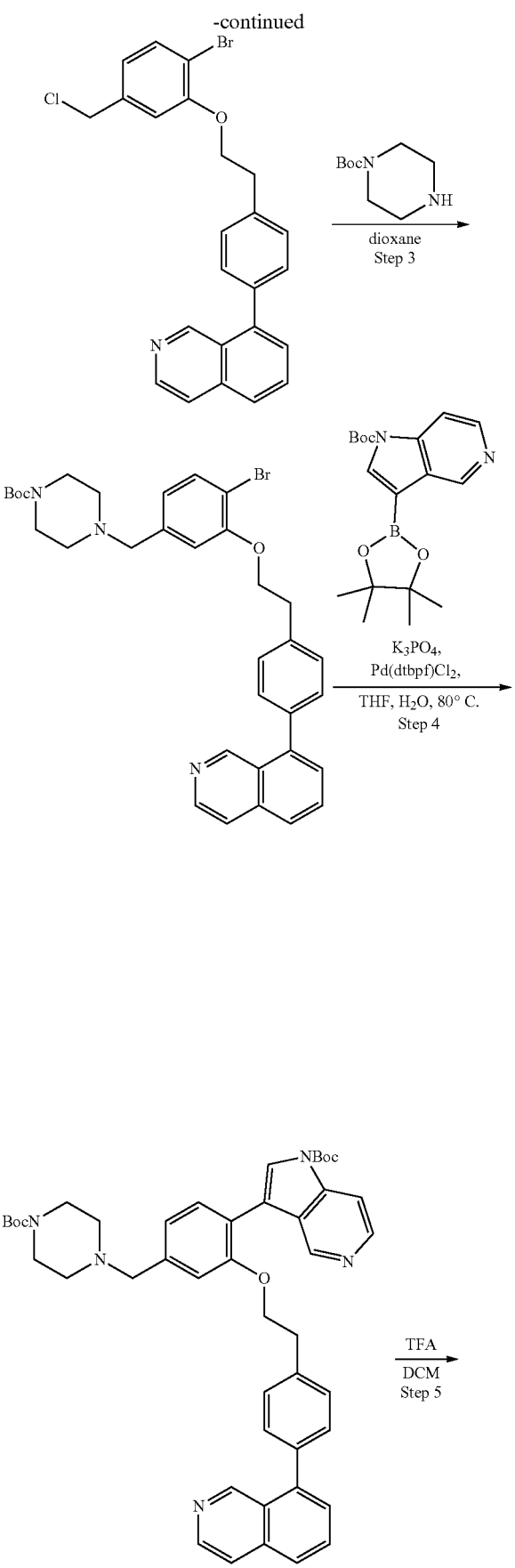

Step 1: To a solution of methyl 4-bromo-3-(4-(isoquinolin-8-yl)phenethoxy)benzoate (3 g, 6.49 mmol, 1 eq.) dissolved in THF (30 mL) was cooled to 0° C., then was added LAH (1 M, 7.14 mL, 1.1 eq.) at 0° C. The reaction mixture was stirred at 0° C. for 1 h. Several new peaks were shown on LC-MS (ET44471-11-P1A1, ET44471-11-P1X1) desired compound was detected. TLC (Petroleum ether:Ethyl acetate=0:1, Rf=0.32). The residue was purified by column chromatography (SiO$_2$, Petroleum ether:Ethyl acetate=0:1). (4-bromo-3-(4-(isoquinolin-8-yl)phenethoxy)phenyl) methanol (1.64 g, 3.78 mmol, 58.19% yield) was obtained as a white solid.

Step 2: To a solution of (4-bromo-3-(4-(isoquinolin-8-yl) phenethoxy)phenyl)methanol (200 mg, 460.49 μmol, 1 eq.) in DCM (5 mL) was added SOCl$_2$ (547.84 mg, 4.60 mmol, 334.05 μL, 10 eq.) at 0° C. The mixture was stirred at 20° C. for 12 hr. The residue was diluted with H$_2$O 5 mL and extracted with DCM (5 mL×3). The combined organic layers were concentrated under reduced pressure to give a residue. 8-(4-(2-(2-bromo-5-(chloromethyl)phenoxy)ethyl) phenyl)isoquinoline (200 mg, crude) was obtained as a yellow solid.

Step 3: To a solution of 8-(4-(2-(2-bromo-5-(chloromethyl)phenoxy)ethyl)phenyl)isoquinoline (200 mg, 441.73 μmol, 1 eq.) in dioxane (4 mL) was added tert-butyl piperazine-1-carboxylate (246.81 mg, 1.33 mmol, 3 eq.). The mixture was stirred at 80° C. for 12 hr. The residue was diluted with H$_2$O (10 mL) and extracted with EtOAc (20 mL×3). The combined organic layers were concentrated under reduced pressure to give a residue. The residue was purified by prep-TLC (SiO2, Petroleum ether:Ethyl acetate=0:1, Rf=0.28). Tert-butyl 4-(4-bromo-3-(4-(isoquinolin-8-yl)phenethoxy)benzyl)piperazine-1-carboxylate (200 mg, 331.92 μmol, 75.14% yield) was obtained as a yellow oil.

Step 4: To a mixture of Tert-butyl 4-(4-bromo-3-(4-(isoquinolin-8-yl)phenethoxy)benzyl)piperazine-1-carboxylate (133 mg, 220.72 μmol, 1 eq.), tert-butyl 3-(4,4,5,5-tetramethyl-1,3,2-dioxaborolan-2-yl)pyrrolo[3,2-c] pyridine-1-carboxylate (113.96 mg, 331.09 μmol, 1.5 eq.), ditert-butyl(cyclopentyl)phosphane; Pd(dtbpf)Cl$_2$ (14.39 mg, 22.07 μmol, 0.1 eq.), K$_3$PO$_4$ (93.70 mg, 441.45 μmol, 2 eq.) in THF (4 mL) and H$_2$O (1 mL) was degassed and purged with N$_2$ for 3 times, and then the mixture was stirred at 80° C. for 18 hr under N$_2$ atmosphere. The reaction mixture was diluted with H$_2$O (4 mL) and extracted with EtOAc (10 mL×3). The combined organic layers were concentrated under reduced pressure to give a residue. The residue was purified by prep-TLC (SiO$_2$, Petroleum ether: Ethyl acetate=0:1, Rf=0.47). tert-butyl 3-(4-((4-(tert-butoxycarbonyl)piperazin-1-yl)methyl)-2-(4-(isoquinolin-8-yl)phenethoxy)phenyl)-1H-pyrrolo[3,2-c]pyridine-1-carboxylate (160 mg, 216.25 μmol, 97.97% yield) was obtained as a Black Brown oil.

Step 5: To a mixture of 3-(4-((4-(tert-butoxycarbonyl)piperazin-1-yl)methyl)-2-(4-(isoquinolin-8-yl)phenethoxy)phenyl)-1H-pyrrolo[3,2-c]pyridine-1-carboxylate (150 mg, 202.73 μmol, 1 eq.), TFA (69.35 mg, 608.19 μmol, 45.03 μL, 3 eq.) in DCM (5 mL) was stirred at 20° C. for 12 hr. Worked up and the combined organic layers were concentrated under reduced pressure to give a residue. The residue was purified by prep-HPLC (TFA condition (column: Phenomenex luna C18 100*40 mm*5 μm; mobile phase: [water (0.1% TFA)-ACN]; B %: 5%-35%, 8 min)). 8-(4-(2-(5-(piperazin-1-ylmethyl)-2-(1H-pyrrolo[3,2-c]pyridin-3-yl)phenoxy)ethyl)phenyl)isoquinoline (14.55 mg, 22.26 μmol, 10.98% yield, TFA) was obtained as a white solid. $^1$H NMR (400 MHz, DMSO-d6) δ=13.18 (br s, 1H), 9.30 (s, 1H), 9.18 (s, 1H), 8.63 (d, J=6.0 Hz, 1H), 8.47 (d, J=6.6 Hz, 1H), 8.25-8.13 (m, 2H), 8.08-7.99 (m, 3H), 7.68 (dd, J=2.7, 7.1 Hz, 2H), 7.43 (t, J=7.9 Hz, 3H), 7.38-7.32 (m, 2H), 7.20 (d, J=7.6 Hz, 1H), 4.41 (br t, J=6.7 Hz, 2H), 4.22 (br s, 2H), 3.36 (br s, 3H), 3.27-3.07 (m, 5H), 1.33-1.18 (m, 1H).

Preparation of 8-[4-[2-[5-[(4-methylpiperazin-1-yl)methyl]-2-(1H-pyrrolo[3,2-c]pyridin-3-yl)phenoxy]ethyl]phenyl]isoquinoline

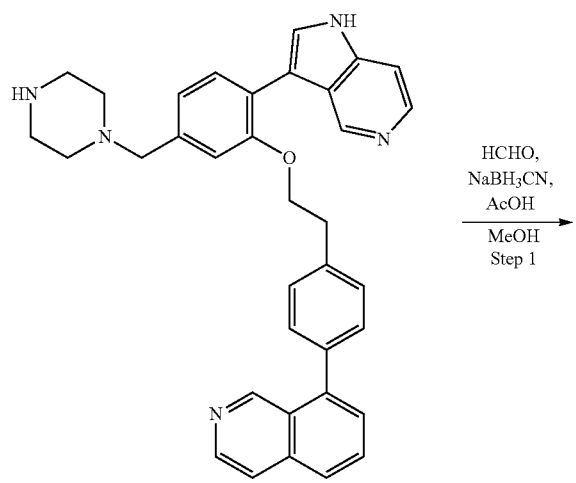

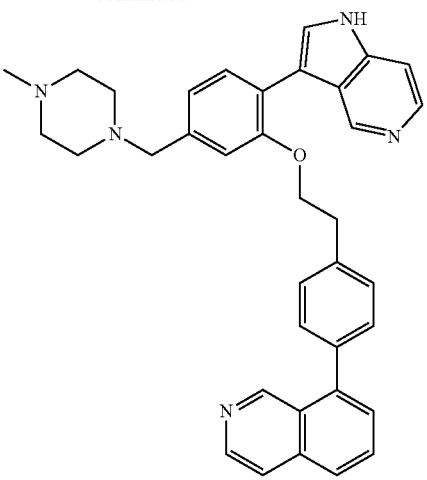

Step 1: To a solution of 8-[4-[2-[5-(piperazin-1-ylmethyl)-2-(1H-pyrrolo[3,2-c]Pyridine-3-yl)phenoxy] ethyl] phenyl]isoquinoline (50 mg, 92.65 μmol, 1 eq.) in MeOH (1 mL) was added formaldehyde (3.34 mg, 111.18 μmol, 3.06 uL, 1.2 eq.), then was added NaBH$_3$CN (17.47 mg, 277.95 μmol, 3 eq.) and AcOH (5.56 mg, 92.65 μmol, 5.30 μL, 1 eq.) at 0° C. The mixture was stirred at 20° C. for 12 hr. The reaction mixture was worked up and the combined organic layers were concentrated under reduced pressure to give a residue. The residue was purified by prep-HPLC. 8-[4-[2-[5-[(4-methylpiperazin-1-yl)methyl]-2-(1H-pyrrolo[3,2-c]pyridin-3-yl) phenoxy]ethyl] phenyl] isoquinoline (10.81 mg, 16.19 μmol, 17.4% yield, TFA salt) was obtained as a white solid. $^1$H NMR (400 MHz, DMSO-d6) δ=13.11 (br s, 1H), 9.31 (s, 1H), 9.19 (br s, 1H), 8.64 (br d, J=5.6 Hz, 1H), 8.48 (d, J=6.7 Hz, 1H), 8.20 (br d, J=5.1 Hz, 1H), 8.16 (d, J=8.2 Hz, 1H), 8.06 (d, J=2.0 Hz, 1H), 8.04 (s, 1H), 8.03-7.99 (m, 1H), 7.68 (br d, J=7.1 Hz, 1H), 7.64 (d, J=7.7 Hz, 1H), 7.45 (d, J=8.1 Hz, 2H), 7.40-7.34 (m, 3H), 7.32 (s, 1H), 7.14 (br d, J=7.5 Hz, 1H), 4.42 (br t, J=6.5 Hz, 5H), 3.94 (br s, 2H), 3.15 (br t, J=6.5 Hz, 4H), 2.83 (s, 4H).

Synthesis of Additional Extracellular Protein Targeting Ligands (3S)-4-(4-bromophenyl)-3-(4-(4-(1-hydroxyethyl)-2-methoxy-5-nitrophenoxy)butanamido)-N-(2-(2-(2-(methylamino)ethoxy)ethoxy)ethyl)butanamide

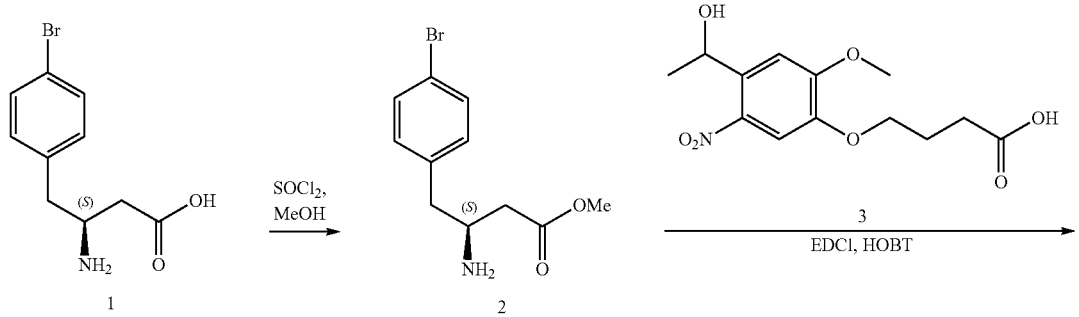

-continued
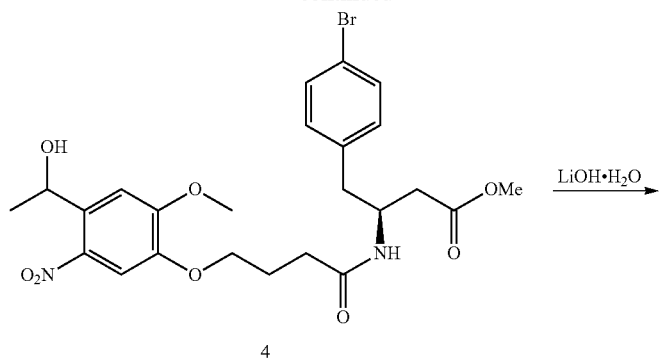
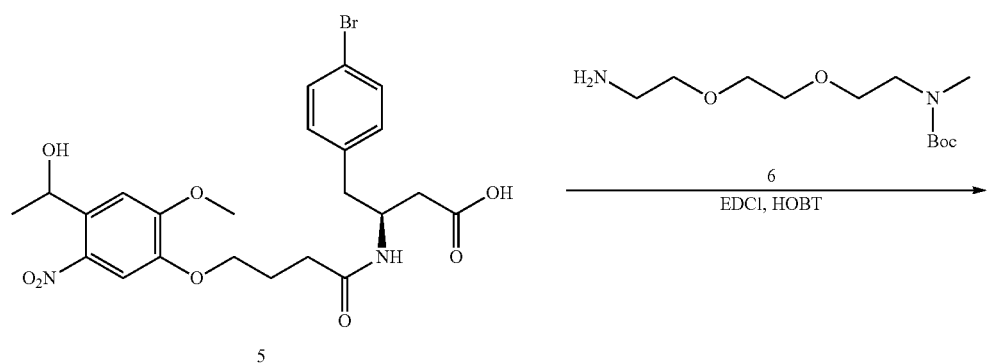
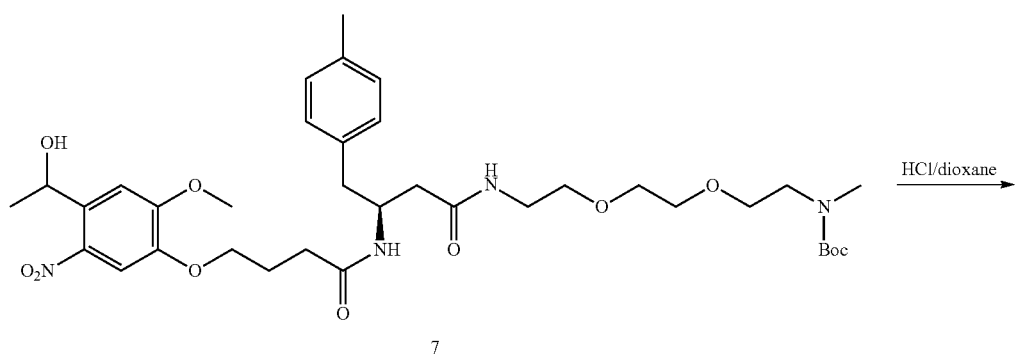
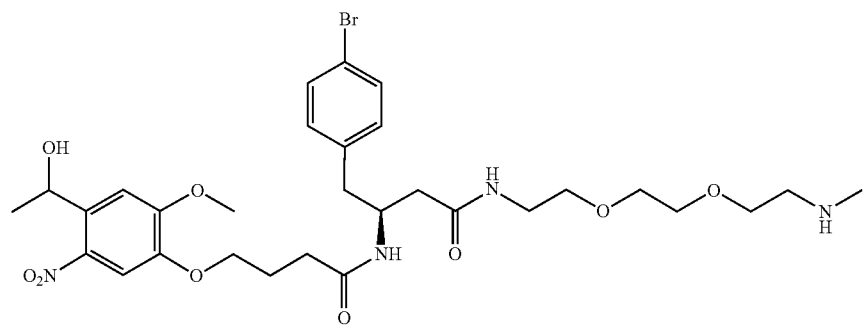

N-(2-(2-(2-aminoethoxy)ethoxy)ethyl)-4-(((4-(bicyclo[2.2.1]heptan-2-ylamino)-6-((cyclohexylmethyl)amino)-1,3,5-triazin-2-yl)amino)methyl)benzamide
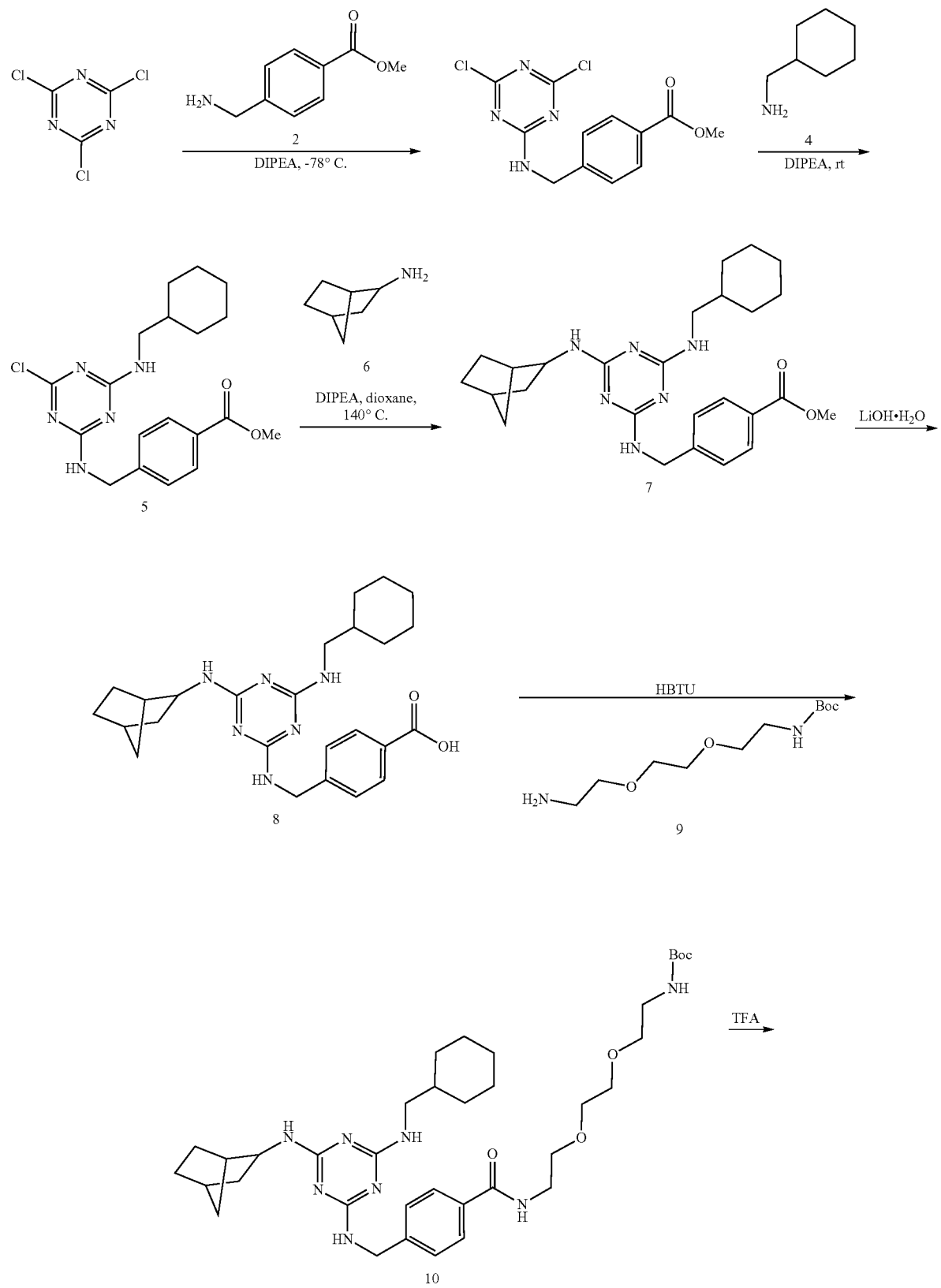

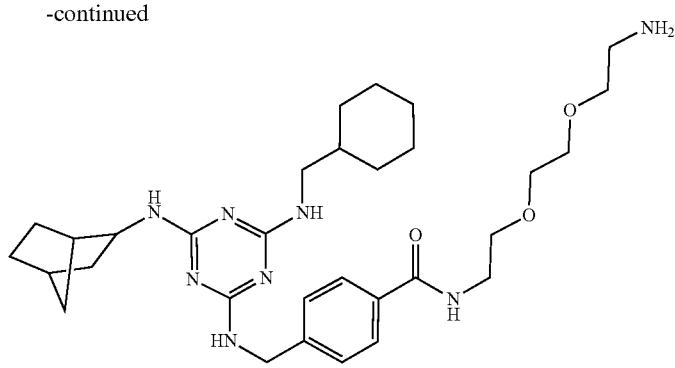
Synthesis of Degraders
Preparation of A1, (2R,3R,4R,5R)-2-(hydroxymethyl)-5-((6-(trifluoromethyl)pyrazin-2-yl)amino)tetrahydro-2H-pyran-3,4-diol
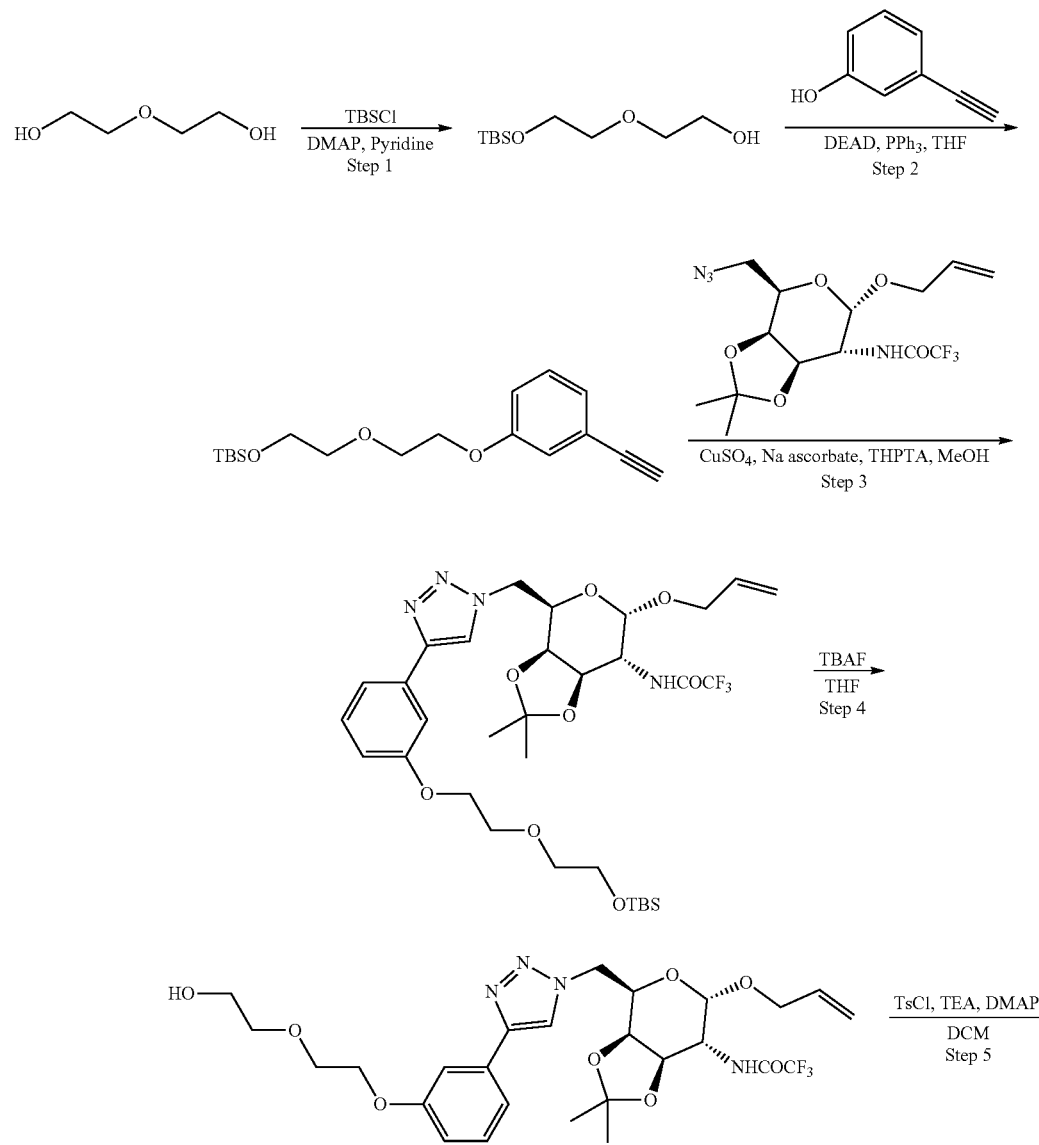

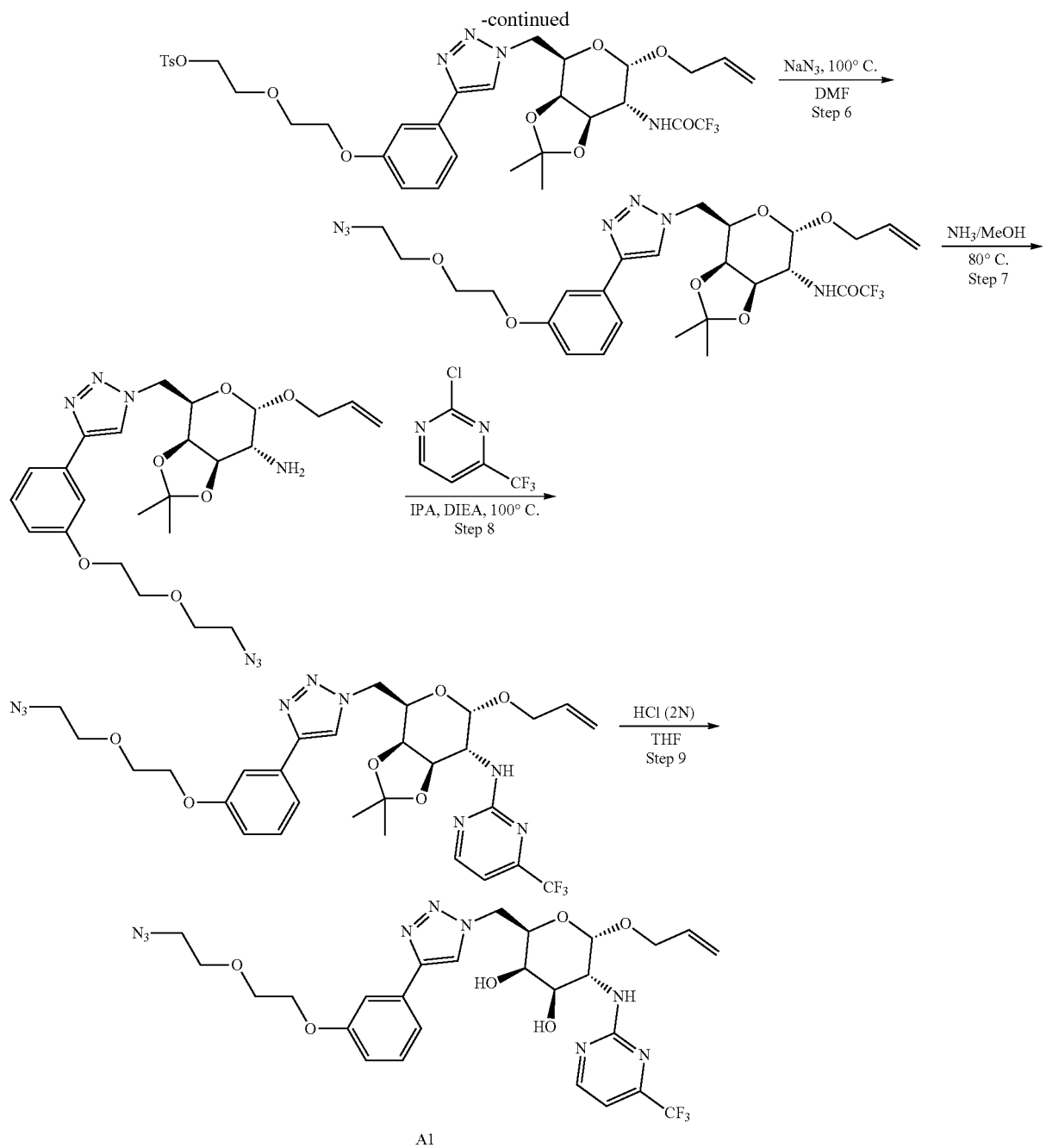

Step 1: To a solution of 2,2'-oxybis(ethan-1-ol) (10.0 g, 90 mmol) in pyridine (50 mL) was added DMAP (22.0 g, 180.0 mmol) and TBSCl (1.35 g, 9.0 mmol) at 0° C. The mixture was stirred at rt under $N_2$ for 16 h. The mixture was concentrated under reduced pressure to give a crude product, which was purified by column to give 2-(2-((tert-butyldimethylsilyl)oxy)ethoxy)ethan-1-ol (1.47 g, 7% yield), LC-MS (ESI) found: 221 [M+H]$^+$.

Step 2: To a solution of 2-(2-((tert-butyldimethylsilyl)oxy)ethoxy)ethan-1-ol (1.47 g, 6.7 mmol) in THF (50.0 mL) was added 3-ethynylphenol (790.6 mg, 6.7 mmol), PPh$_3$ (2.1 g, 8.0 mmol) and DEAD (1.4 g, 8.0 mmol) at 0° C. The mixture was stirred at the room temperature for 2 h. The mixture was concentrated under reduced pressure to give a crude product, which was purified by column to give tert-butyl(2-(2-(3-ethynylphenoxy)ethoxy)ethoxy)dimethylsilane (1.2 g, 60% yield). LC-MS (ESI) found: 321 [M+H]$^+$.

Step 3: To a solution of tert-butyl(2-(2-(3-ethynylphenoxy)ethoxy)dimethylsilane (1.2 g, 4.0 mmol) in MeOH (50 mL) was added N-((3aS,4R,6S,7R,7aR)-6-(allyloxy)-4-(azidomethyl)-2,2-dimethyltetrahydro-4H-[1,3]dioxolo[4,5-c]pyran-7-yl)-2,2,2-trifluoroacetamide (1.5 g, 4.0 mmol), CuSO$_4$ (64.0 mg, 0.4 mmol), Na ascorbate (72.0 mg, 0.4 mmol) and THPTA (144.0 mg, 0.4 mmol). The mixture was stirred at the room temperature under $N_2$ for 16 h. The mixture was concentrated to give a crude product, which was purified by column to give N-((3aS,4R,6S,7R,7aR)-6-(allyloxy)-4-((4-(3-(2-(2-((tert-butyldimethylsilyl)oxy)ethoxy)ethoxy)phenyl)-1H-1,2,3-triazol-1-yl)methyl)-2,2- dimethyltetrahydro-4H-[1,3]dioxolo[4,5-c]pyran-7-yl)-2,2,2-trifluoroacetamide (900.0 mg, 32% yield). LC-MS (ESI) found: 701 [M+H]+.

Step 4: To a solution of N-((3aS,4R,6S,7R,7aR)-6-(allyloxy)-4-((4-(3-(2-(2-((tert-butyldimethylsilyl)oxy)ethoxy)ethoxy)phenyl)-1H-1,2,3-triazol-1-yl)methyl)-2,2-dimethyltetrahydro-4H-[1,3]dioxolo[4,5-c]pyran-7-yl)-2,2,2-trifluoroacetamide (900.0 mg, 1.29 mmol) in THF (40.0 mL) was added TBAF (2.58 mL, 1 M in THF), the mixture was stirred at the room temperature for 16 h. The mixture was diluted with ethyl acetate (100 mL) and washed with water (60 mL×3). The organic layer was dried over sodium sulfate, filtered, concentrated under reduced pressure to give crude product, which was purified by column to afford N-((3aS,4R,6S,7R,7aR)-6-(allyloxy)-4-((4-(3-(2-(2-hydroxyethoxy)ethoxy)phenyl)-1H-1,2,3-triazol-1-yl)methyl)-2,2-dimethyltetrahydro-4H-[1,3]dioxolo[4,5-c]pyran-7-yl)-2,2,2-trifluoroacetamide (586 mg, 77% yield). LC-MS (ESI) found: 587 [M+H]+.

Step 5: To a solution of N-((3aS,4R,6S,7R,7aR)-6-(allyloxy)-4-((4-(3-(2-(2-hydroxyethoxy)ethoxy)phenyl)-1H-1,2,3-triazol-1-yl)methyl)-2,2-dimethyltetrahydro-4H-[1,3]dioxolo[4,5-c]pyran-7-yl)-2,2,2-trifluoroacetamide (586.0 mg, 1.0 mmol) in DCM (30.0 mL) was added TEA (303 mg, 3.0 mmol), DMAP (122.0 mg, 1.0 mmol), and TsCl (229.0 mg, 1.20 mmol). The mixture was stirred at the room temperature for 16 h. The mixture was diluted with ethyl acetate (100 mL) and washed with water (50 mL×3), the organic layer was concentrated under reduced pressure to give a crude product, which was purified by column to give 2-(2-(3-(1-(((3aS,4R,6S,7R,7aR)-6-(allyloxy)-2,2-dimethyl-7-(2,2,2-trifluoroacetamido)tetrahydro-4H-[1,3]dioxolo[4,5-c]pyran-4-yl)methyl)-1H-1,2,3-triazol-4-yl)phenoxy)ethoxy)ethyl 4-methylbenzenesulfonate (584 mg, 79% yield). LC-MS (ESI) found: 741 [M+H]+.

Step 6: To a solution of 2-(2-(3-(1-(((3aS,4R,6S,7R,7aR)-6-(allyloxy)-2,2-dimethyl-7-(2,2,2-trifluoroacetamido)tetrahydro-4H-[1,3]dioxolo[4,5-c]pyran-4-yl)methyl)-1H-1,2,3-triazol-4-yl)phenoxy)ethoxy)ethyl 4-methylbenzenesulfonate (584 mg, 0.79 mmol) in DMF (30.0 mL) was added NaN3 (513.0 mg, 7.9 mmol), the mixture was stirred at 100° C. for 16 h. The mixture was diluted with ethyl acetate (150.0 mL) and washed with water (100.0 mL×3), the organic layer was concentrated under reduced to give a crude product, which was purified by column to give N-((3aS,4R,6S,7R,7aR)-6-(allyloxy)-4-((4-(3-(2-(2-azidoethoxy)ethoxy)phenyl)-1H-1,2,3-triazol-1-yl)methyl)-2,2-dimethyltetrahydro-4H-[1,3]dioxolo[4,5-c]pyran-7-yl)-2,2,2-trifluoroacetamide (427 mg, 88% yield). LC-MS (ESI) found: 612 [M+H]+.

Step 7: A solution of N-((3aS,4R,6S,7R,7aR)-6-(allyloxy)-4-((4-(3-(2-(2-azidoethoxy)ethoxy)phenyl)-1H-1,2,3-triazol-1-yl)methyl)-2,2-dimethyltetrahydro-4H-[1,3]dioxolo[4,5-c]pyran-7-yl)-2,2,2-trifluoroacetamide (427.0 mg, 0.70 mmol) in NH3/MeOH (20 mL, 7 M), was stirred at 80° C. for 16 h. The mixture was concentrated under reduced pressure to give crude (3aS,4R,6S,7R,7aR)-6-(allyloxy)-4-((4-(3-(2-(2-azidoethoxy)ethoxy)phenyl)-1H-1,2,3-triazol-1-yl)methyl)-2,2-dimethyltetrahydro-4H-[1,3]dioxolo[4,5-c]pyran-7-amine (309 mg, 85% yield). LC-MS (ESI) found: 516 [M+H]+.

Step 8: To a solution of (3aS,4R,6S,7R,7aR)-6-(allyloxy)-4-((4-(3-(2-(2-azidoethoxy)ethoxy)phenyl)-1H-1,2,3-triazol-1-yl)methyl)-2,2-dimethyltetrahydro-4H-[1,3]dioxolo[4,5-c]pyran-7-amine (30.9 mg, 0.06 mmol) in i-PrOH (30.0 mL) was added 2-chloro-4-(trifluoromethyl)pyrimidine (10.9 mg, 0.06 mmol) and DIEA (23.6 mg, 1.8 mmol). The mixture was stirred at 100° C. for 16 h. The mixture was concentrated and purified by column to give N-((3aS,4R,6S,7R,7aR)-6-(allyloxy)-4-((4-(3-(2-(2-azidoethoxy)ethoxy)phenyl)-1H-1,2,3-triazol-1-yl)methyl)-2,2-dimethyltetrahydro-4H-[1,3]dioxolo[4,5-c]pyran-7-yl)-4-(trifluoromethyl)pyrimidin-2-amine (36.3 mg, 93% yield). LC-MS (ESI) found: 662 [M+H]+.

Step 9: To a solution of N-((3aS,4R,6S,7R,7aR)-6-(allyloxy)-4-((4-(3-(2-(2-azidoethoxy)ethoxy)phenyl)-1H-1,2,3-triazol-1-yl)methyl)-2,2-dimethyltetrahydro-4H-[1,3]dioxolo[4,5-c]pyran-7-yl)-4-(trifluoromethyl)pyrimidin-2-amine (36.3 mg, 0.056 mmol) in THF (2 mL) was added HCl (2 mL, 2 N in water). The mixture was stirred at the room temperature for 16 h. The mixture was concentrated and purified by column to give (2R,3R,4R,5R,6S)-6-(allyloxy)-2-((4-(3-(2-(2-azidoethoxy)ethoxy)phenyl)-1H-1,2,3-triazol-1-yl)methyl)-5-((4-(trifluoromethyl)pyrimidin-2-yl)amino)tetrahydro-2H-pyran-3,4-diol (A1, 3.0 mg, 10% yield). LC-MS (ESI) found: 662 [M+H]+. 1H NMR (400 MHz, CD3OD): δ 8.52 (d, J=4.5 Hz, 1H), 8.36 (s, 1H), 7.42 (dd, J=10.7, 5.0 Hz, 2H), 7.34 (t, J=7.9 Hz, 1H), 6.97-6.89 (m, 2H), 5.63 (m, 1H), 4.98 (dd, J=27.9, 14.3 Hz, 3H), 4.74-4.66 (m, 3H), 4.30 (dd, J=8.2, 4.5 Hz, 1H), 4.22-4.17 (m, 2H), 4.01 (d, J=2.6 Hz, 1H), 3.96 (dd, J=10.8, 3.1 Hz, 1H), 3.88 (dd, J=5.4, 3.8 Hz, 2H), 3.78-3.70 (m, 3H), 3.68 (d, J=5.6 Hz, 1H), 3.43-3.37 (m, 2H). 19F NMR (377 MHz, CD3OD): δ −72.34 (s).

Preparation of A2, 3,3'-((2-(6-azidohexanamido)propane-1,3-diyl)bis(oxy))bis(N-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-yl)propanamide)

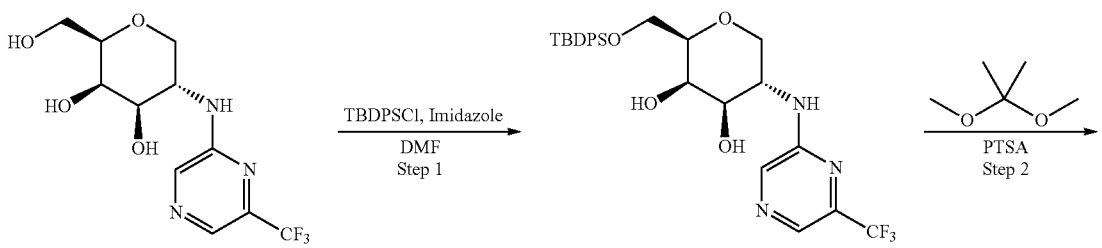

817 818
-continued
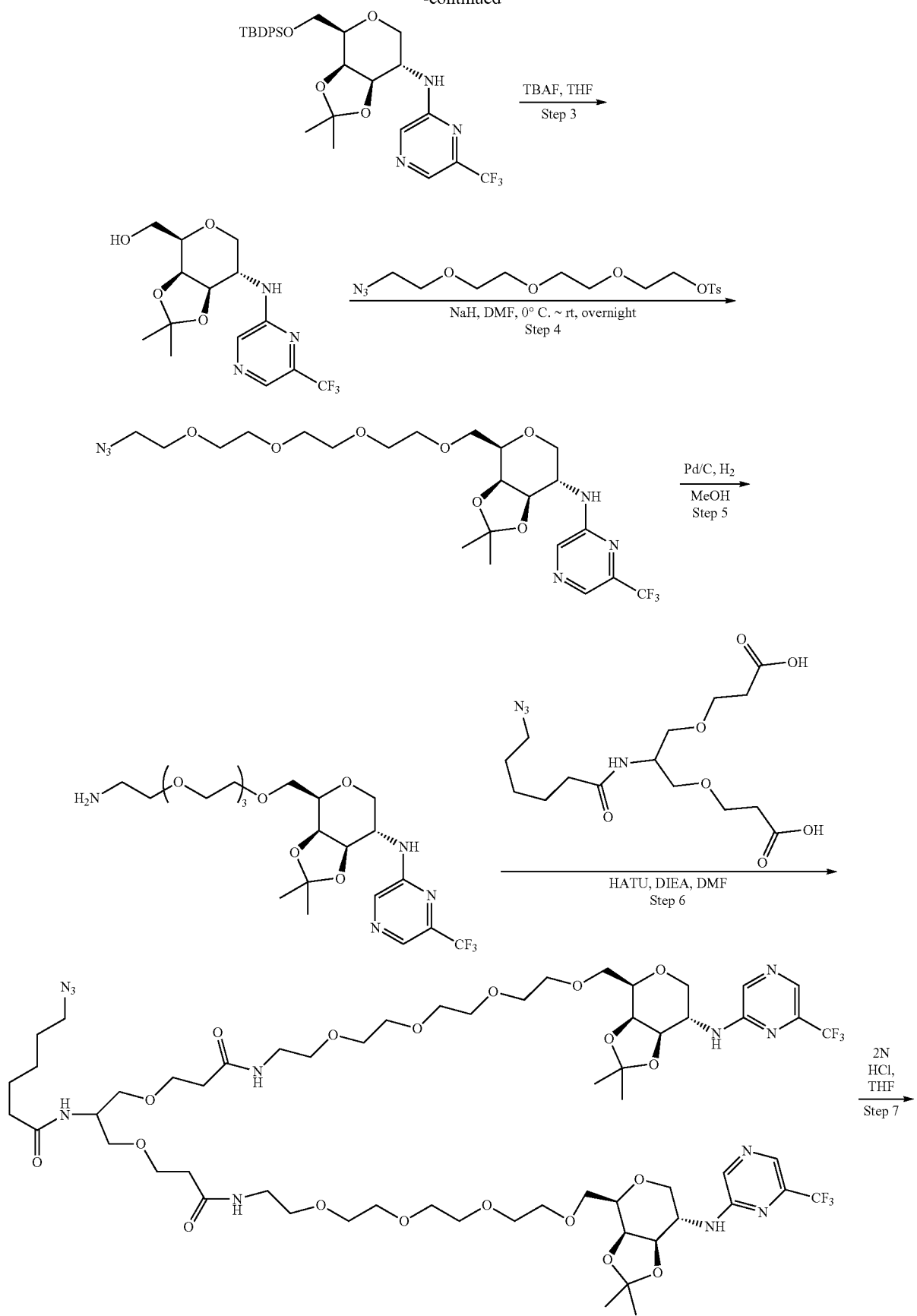

-continued

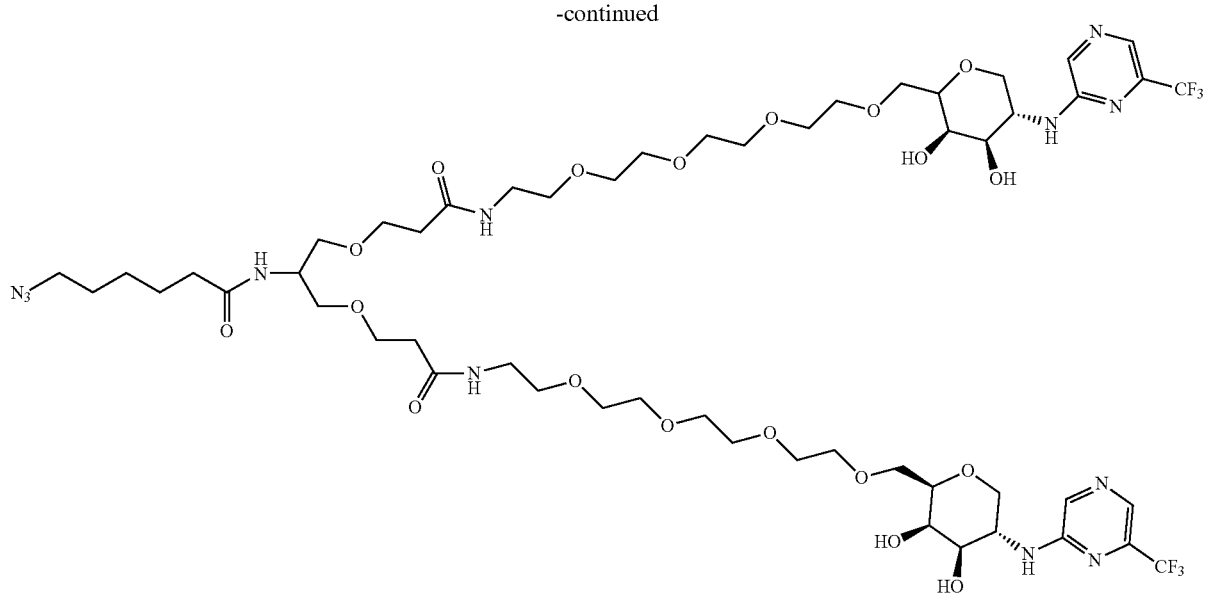

A2

Step 1: To the solution of (2R,3R,4R,5S)-2-(hydroxymethyl)-5-(((6-(trifluoromethyl)pyrazin-2-yl)amino)tetrahydro-2H-pyran-3,4-diol (800 mg, 2.6 mmol) in DMF (10 mL) was added imidazole (352 mg, 5.2 mmol) and TBDP-SCl (0.9 mL, 3.5 mmol). The reaction was stirred overnight, quenched with water, extracted by EA for three times. Combined organic layers were dried and concentrated to be purified by column with 80% EA in PE to get (2R,3R,4R,5S)-2-(((tert-butyldiphenylsilyl)oxy)methyl)-5-((6-(trifluoromethyl)pyrazin-2-yl)amino)tetrahydro-2H-pyran-3,4-diol (613 mg, 43% yield) as yellow solid. LC-MS (ESI) found: 548 [M+H]$^+$.

Step 2: To the solution of (2R,3R,4R,5S)-2-(((tert-butyldiphenylsilyl)oxy)methyl)-5-((6-(trifluoromethyl)pyrazin-2-yl)amino)tetrahydro-2H-pyran-3,4-diol (613 mg, 1.12 mmol) in 2,2-dimethoxypropane (10 mL) was added p-toluenesulfonic acid (20 mg, 0.11 mmol) and the reaction was stirred overnight at room temperature. The mixture was concentrated and purified by column with 30% EA in PE to get N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)-6-(trifluoromethyl)pyrazin-2-amine (570 mg, 87% yield) as light yellow oil. LC-MS (ESI) found: 588 [M+H]$^+$.

Step 3: To a solution of N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)-6-(trifluoromethyl)pyrazin-2-amine (1.4 g, 2.4 mmol) in THF (20 mL) was added TBAF (3 mL, 1 M in THF). The mixture was stirred at rt for 12 h. The mixture was concentrated and purified by chromatography on (silica gel, 0-10% methanol in dichloromethane) to give ((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)methanol (750 mg, 90% yield) as solid. LC-MS (ESI) found: 350 [M+H]$^+$.

Step 4: ((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)methanol (750 mg, 2.1 mmol) in DMF (10 mL) was added NaH (126 mg, 3.2 mmol, 60% wt. in mineral oil) at 0° C. After 1 h, 2-(2-(2-(2-azidoethoxy)ethoxy)ethoxy)ethyl 4-methylbenzenesulfonate (962 mg, 2.6 mmol) was added to the solution, the mixture was stirred at rt for 12 h. The mixture was quenched with H$_2$O and extracted with EA. The combined organic layer was washed with brine, dried over anhydrous Na$_2$SO$_4$, filtered. The filtrate was concentrated and purified by chromatography on (silica gel, 0-10% methanol in dichloromethane) to give N-((3aR,4R,7S,7aR)-4-(13-azido-2,5,8,11-tetraoxatridecyl)-2,2-dimethyltetrahydro-4H-[1,3]dioxolo[4,5-c]pyran-7-yl)-6-(trifluoromethyl)pyrazin-2-amine (200 mg, 87% yield) as solid. LC-MS (ESI) found: 551 [M+H]$^+$.

Step 5: A solution of N-((3aR,4R,7S,7aR)-4-(13-azido-2,5,8,11-tetraoxatridecyl)-2,2-dimethyltetrahydro-4H-[1,3]dioxolo[4,5-c]pyran-7-yl)-6-(trifluoromethyl)pyrazin-2-amine (200 mg, 0.4 mmol) in methanol (5 mL) was added Pd/C (20 mg, 10% wt, 60% wet). The mixture was stirred at rt under a H$_2$ balloon overnight. The mixture was concentrated to give crude N-((3aR,4R,7S,7aR)-4-(13-amino-2,5,8,11-tetraoxatridecyl)-2,2-dimethyltetrahydro-4H-[1,3]dioxolo[4,5-c]pyran-7-yl)-6-(trifluoromethyl)pyrazin-2-amine (191 mg, 100% yield) as a white solid. LC-MS (ESI) found: 525 [M+H]$^+$.

Step 6: To a solution of 3,3'-((2-(6-azidohexanamido)propane-1,3-diyl)bis(oxy))dipropionic acid (71 mg, 0.2 mmol), HATU (152 mg, 0.4 mmol) and DIEA (77 mg, 0.6 mmol) was added N-((3aR,4R,7S,7aR)-4-(13-amino-2,5,8,11-tetraoxatridecyl)-2,2-dimethyltetrahydro-4H-[1,3]dioxolo[4,5-c]pyran-7-yl)-6-(trifluoromethyl)pyrazin-2-amine (191 mg, 0.4 mmol) at 0° C. The mixture was stirred at rt overnight. The mixture was quenched with H$_2$O and extracted with EA. The combined organic layer was washed with brine, dried over anhydrous Na$_2$SO$_4$, filtered. The filtrate was concentrated and purified by chromatography on (silica gel, 0-20% methanol in dichloromethane) to give 3,3'-((2-(6-azidohexanamido)propane-1,3-diyl)bis(oxy))bis(N-(1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-2,5,8,11-tetraoxatridecan-13-yl)propanamide) (80 mg, 29% yield) as a white solid. LC-MS (ESI) found: 1387 [M+H]$^+$.

Step 7: To a solution of 3,3'-((2-(6-azidohexanamido)propane-1,3-diyl)bis(oxy))bis(N-(1-((3aR,4R,7S,7aR)-2,2- dimethyl-7-((6-(trifluoromethyl)pyrazin-2-yl)amino)tetrahydro-4H-[1,3]dioxolo[4,5-c]pyran-4-yl)-2,5,8,11-tetraoxatridecan-13-yl)propanamide) (80 mg, 0.05 mmol) in THF (5 mL) was added HCl (0.1 ml, 1 M), the mixture was stirred at rt overnight. The mixture was concentrated and purified by C18 to give 3,3'-((2-(6-azidohexanamido)propane-1,3-diyl)bis(oxy))bis(N-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-yl)propanamide) (A2, 60 mg, 80% yield) as a white solid. LC-MS (ESI) found: 1307 [M+H]$^+$. $^1$H NMR (400 MHz, CD$_3$OD): δ 8.11 (s, 2H), 8.00 (s, 2H), 4.33 (td, J=10.6, 5.1 Hz, 2H), 4.13-4.04 (m, 3H), 3.92 (d, J=2.9 Hz, 2H), 3.74-3.58 (m, 36H), 3.55 (t, J=5.5 Hz, 4H), 3.48 (ddd, J=19.2, 9.7, 5.5 Hz, 4H), 3.37 (dd, J=11.1, 5.7 Hz, 4H), 3.28 (d, J=6.8 Hz, 2H), 3.12 (t, J=10.8 Hz, 2H), 2.45 (dd, J=6.7, 5.5 Hz, 4H), 2.22 (t, J=7.4 Hz, 2H), 1.75-1.54 (m, 4H), 1.46-1.31 (m, 2H). $^{19}$F NMR (377 MHz, CD$_3$OD): δ −70.25.

Preparation of A3, 1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid

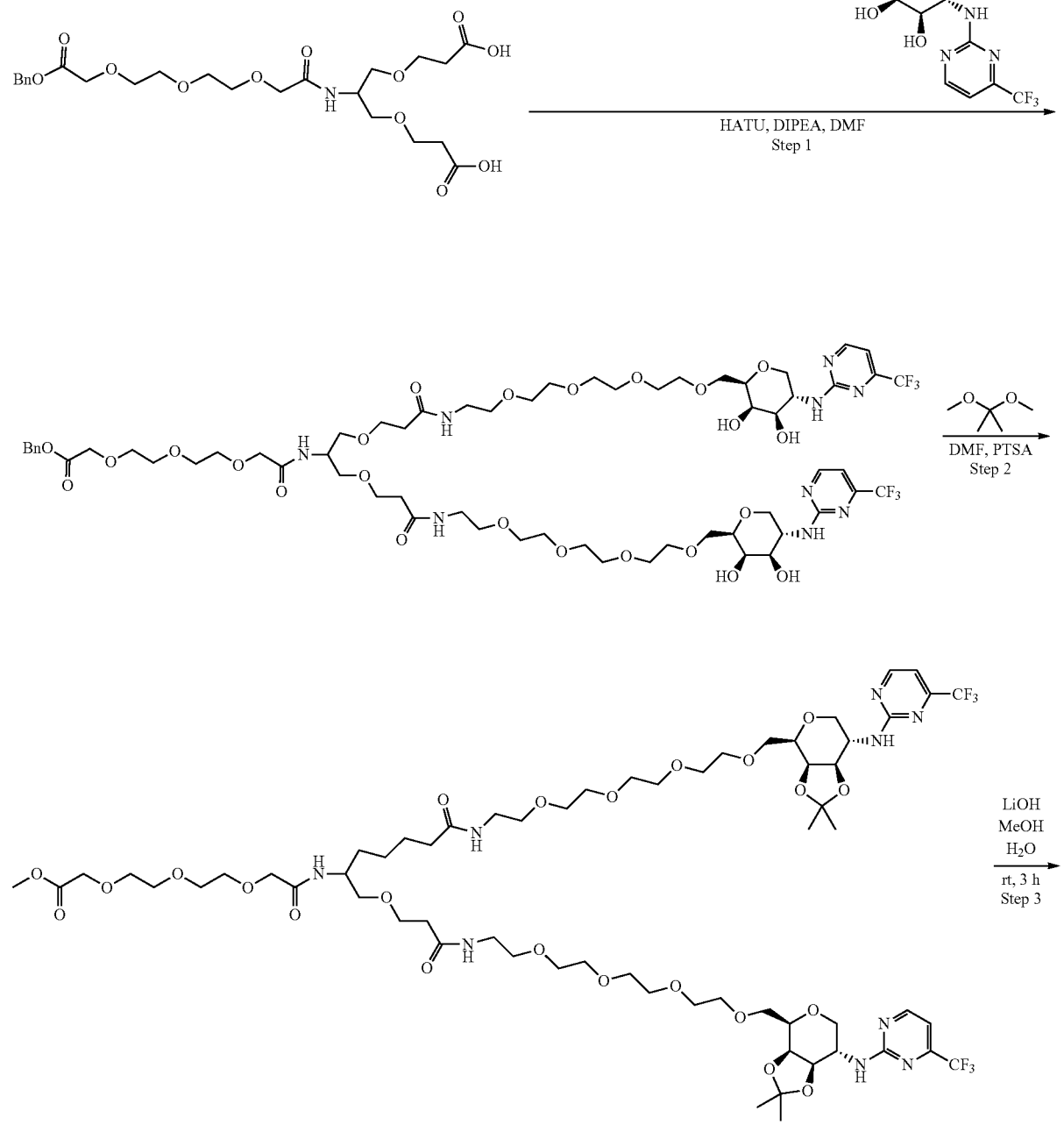

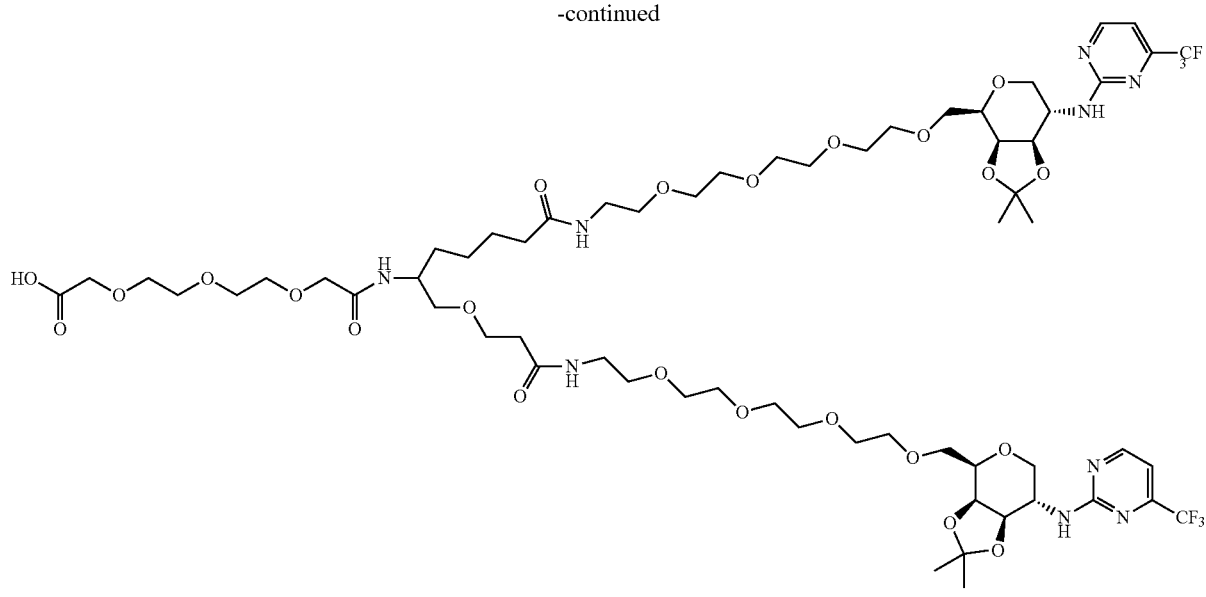

A3

Step 1: To a solution of 15-((2-carboxyethoxy)methyl)-3,13-dioxo-1-phenyl-2,5,8,11,17-pentaoxa-14-azaicosan-20-oic acid (0.56 g, 1.06 mmol) and HATU (1.2 g, 3.18 mmol) in DMF (10 mL) was added DIPEA (0.54 g, 4.24 mmol) and (2R,3R,4R,5S)-2-(13-amino-2,5,8,11-tetraoxatridecyl)-5-((4-(trifluoromethyl)pyrimidin-2-yl)amino)tetrahydro-2H-pyran-3,4-diol (1.07 g, 2.2 mmol) at rt. The reaction mixture was stirred at rt for overnight. The resulting mixture was separated and concentrated in vacuo. The crude product was purified by flash chromatography (C18, 0~80%, MeOH in H$_2$O) to give benzyl 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (1.1 g, 73% yield) as white solid. LC-MS (ESI) found: 1463 [M+H]$^+$.

Step 2: To a solution of benzyl 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (1.07 g, 0.75 mmol) in DMF (5 mL) were added p-TsOH (0.03 g, 0.14 mmol) and 2,2-dimethoxypropane (1.56 g, 15 mmol), and the reaction was stirred at room temperature overnight. The mixture was concentrated under reduced pressure to give a crude product, which was purified by flash chromatography (C18, 0~80%, MeOH in H$_2$O) to give methyl 1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (0.8 g, 72% yield) as white solid. LC-MS (ESI) found: 1467 [M+H]$^+$.

Step 3: To a solution of methyl 1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (0.8 g, 0.54 mmol) in MeOH (10 mL) were added lithium hydroxide monohydrate (20 mg, 0.82 mmol) and the reaction was stirred at room temperature overnight. The mixture was adjusted pH to 5 and diluted with ethyl acetate (50 mL) and then washed with water (50 mL×3). The organic layer was dried over sodium sulfate, filtered, concentrated under reduced pressure to give a crude product, which was purified by column to give 1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid (A3, 0.6 g, 75% yield) as a white solid. LC-MS (ESI) found: 1453 [M+H]$^+$. $^1$H NMR (400 MHz, CD$_3$OD): δ 8.51 (d, J=4.7 Hz, 2H), 6.90 (d, J=4.9 Hz, 2H), 4.31 (s, 2H), 4.23 (dt, J=6.2, 3.1 Hz, 2H), 4.21-4.15 (m, 2H), 4.13 (s, 2H), 4.00 (s, 2H), 3.91 (dd, J=10.9, 5.6 Hz, 4H), 3.78-3.59 (m, 41H), 3.52 (ddd, J=13.4, 10.2, 4.6 Hz, 8H), 3.37 (t, J=5.5 Hz, 4H), 3.16 (t, J=11.1 Hz, 2H), 2.45 (t, J=6.2 Hz, 4H), 1.50 (s, 6H), 1.30 (d, J=13.2 Hz, 6H).

Preparation of A5, (2R,3R,4R,5R,6S)-2-((1H-1,2,3-triazol-1-yl)methyl)-6-(allyloxy)-5-((4-(trifluoromethyl)pyrimidin-2-yl)amino)tetrahydro-2H-pyran-3,4-diol

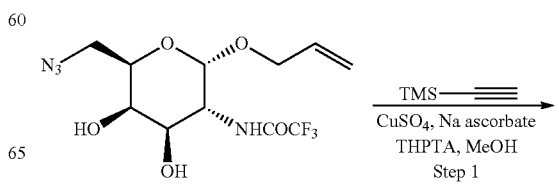

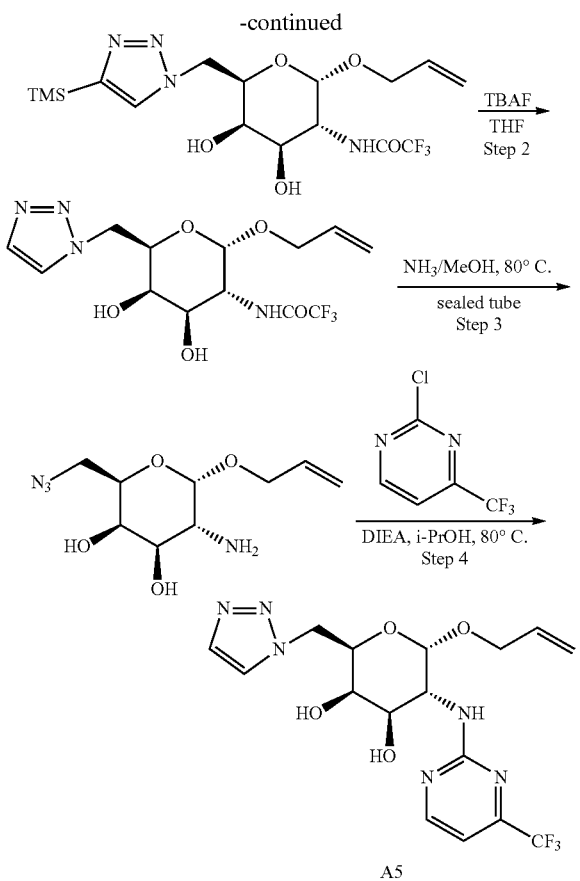

A5

Step 1: THPTA (20 mg) and CuSO₄ (3 mg) were dissolved in water (0.5 mL). The mixture was added into a solution of N-((2S,3R,4R,5R,6R)-2-(allyloxy)-6-(azidomethyl)-4,5-dihydroxytetrahydro-2H-pyran-3-yl)-2,2,2-trifluoroacetamide (50 mg, 0.15 mmol) and ethynyltrimethylsilane (29 mg, 0.3 mmol) in MeOH (4 mL). A freshly prepared solution of Na ascorbate (6 mg) in water (0.5 mL) was added. The reaction was stirred overnight. The resulting mixture was filtered. The crude product was purified by chromatography on (silica gel, 0-100% ethyl acetate in petroleum ether) to give N-((2S,3R,4R,5R,6R)-2-(allyloxy)-4,5-dihydroxy-6-((4-(trimethylsilyl)-1H-1,2,3-triazol-1-yl)methyl)tetrahydro-2H-pyran-3-yl)-2,2,2-trifluoroacetamide (40 mg, 61% yield) as a white solid. LC-MS (ESI) found: 439 [M+H]⁺.

Step 2: A solution of N-((2S,3R,4R,5R,6R)-2-(allyloxy)-4,5-dihydroxy-6-((4-(trimethylsilyl)-1H-1,2,3-triazol-1-yl)methyl)tetrahydro-2H-pyran-3-yl)-2,2,2-trifluoroacetamide (40 mg, 0.09 mmol) in THF (3 mL) was added TBAF (1 mL, 1 M in THF). The mixture was stirred at 40° C. overnight. The mixture was concentrated and the residue was purified by chromatography on (silica gel, 0-20% methanol in methylene chloride) to give N-((2S,3R,4R,5R,6R)-6-((1H-1,2,3-triazol-1-yl)methyl)-2-(allyloxy)-4,5-dihydroxytetrahydro-2H-pyran-3-yl)-2,2,2-trifluoroacetamide (25 mg, 76% yield) as a white solid. LC-MS (ESI) found: 367 [M+H]⁺. ¹H NMR (400 MHz, CD₃OD): δ 8.01 (s, 1H), 7.74 (s, 1H), 5.67 (ddd, J=22.5, 10.9, 5.9 Hz, 1H), 5.10 (dd, J=22.9, 5.8 Hz, 2H), 4.86 (s, 3H), 4.69 (d, J=2.3 Hz, 1H), 4.67 (s, 1H), 4.32 (dd, J=10.8, 3.7 Hz, 1H), 4.26-4.20 (m, 1H), 3.97 (dd, J=10.9, 3.3 Hz, 1H), 3.93 (d, J=3.0 Hz, 1H), 3.70 (dd, J=12.9, 5.4 Hz, 1H), 3.63 (dd, J=12.9, 6.2 Hz, 1H). ¹⁹F NMR (377 MHz, CD₃OD): δ −77.01.

Step 3: A solution of N-((2S,3R,4R,5R,6R)-6-((1H-1,2,3-triazol-1-yl)methyl)-2-(allyloxy)-4,5-dihydroxytetrahydro-2H-pyran-3-yl)-2,2,2-trifluoroacetamide (20 mg, 0.05 mmol) in NH₃/MeOH (3 mL, 7 mol/L) was stirred at 80° C. overnight in a sealed tube. The mixture was concentrated to give crude (2R,3R,4R,5R,6S)-2-((1H-1,2,3-triazol-1-yl)methyl)-6-(allyloxy)-5-aminotetrahydro-2H-pyran-3,4-diol (14 mg, 100% yield) as a white solid. LC-MS (ESI) found: 271 [M+H]⁺.

Step 4: A solution of (2R,3R,4R,5R,6S)-2-((1H-1,2,3-triazol-1-yl)methyl)-6-(allyloxy)-5-aminotetrahydro-2H-pyran-3,4-diol (14 mg, 0.05 mmol), 2-chloro-4-(trifluoromethyl)pyrimidine (18 mg, 0.1 mmol) and DIEA (26 mg, 0.2 mmol) in isopropanol (3 mL) was stirred at 80° C. overnight in a sealed tube. The mixture was concentrated and purified by chromatography on C18 to give (2R,3R,4R,5R,6S)-2-((1H-1,2,3-triazol-1-yl)methyl)-6-(allyloxy)-5-((4-(trifluoromethyl)pyrimidin-2-yl)amino)tetrahydro-2H-pyran-3,4-diol (A5, 8.8 mg, 42% yield) as a white solid. LC-MS (ESI) found: 417 [M+H]⁺. ¹H NMR (400 MHz, CD₃OD): δ 8.51 (d, J=4.6 Hz, 1H), 8.02 (d, J=0.8 Hz, 1H), 7.74 (d, J=0.9 Hz, 1H), 6.91 (d, J=4.9 Hz, 1H), 5.64 (dd, J=10.7, 5.7 Hz, 1H), 5.07 (d, J=17.2 Hz, 1H), 5.00 (d, J=10.4 Hz, 1H), 4.96 (s, 1H), 4.71 (d, J=2.7 Hz, 1H), 4.69 (s, 1H), 4.55 (s, 1H), 4.29-4.22 (m, 1H), 4.01-3.88 (m, 2H), 3.75-3.52 (m, 2H). ¹⁹F NMR (377 MHz, CD₃OD): δ −72.35.

Preparation of A6, (2R,3R,4R,5R,6S)-6-(allyloxy)-2-(azidomethyl)-5-((4-(trifluoromethyl)pyrimidin-2-yl)amino)tetrahydro-2H-pyran-3,4-diol

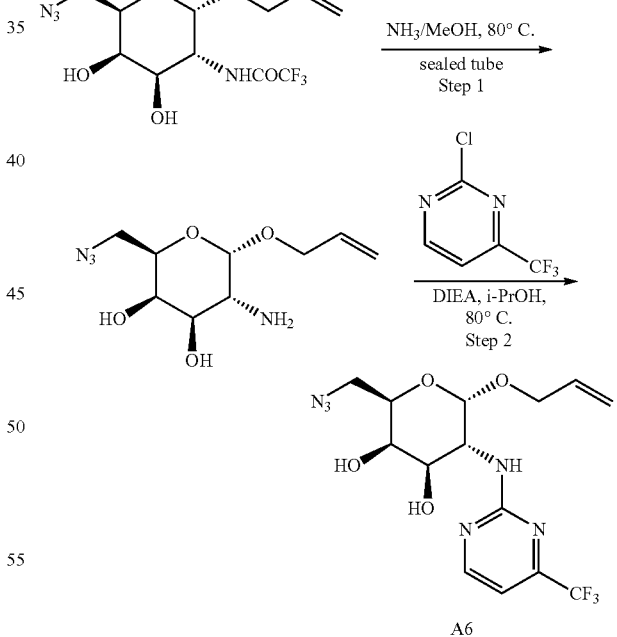

A6

Step 1: A solution of N-((2S,3R,4R,5R,6R)-2-(allyloxy)-6-(azidomethyl)-4,5-dihydroxytetrahydro-2H-pyran-3-yl)-2,2,2-trifluoroacetamide (40 mg, 0.11 mmol) in NH₃/MeOH (3 mL, 7 mol/L) was stirred at 80° C. overnight in a sealed tube. The mixture was concentrated to give crude (2R,3R,4R,5R,6S)-6-(allyloxy)-5-amino-2-(azidomethyl)tetrahydro-2H-pyran-3,4-diol (28 mg, 100% yield) as a white solid. LC-MS (ESI) found: 245 [M+H]⁺.

Step 2: A solution of (2R,3R,4R,5R,6S)-6-(allyloxy)-5-amino-2-(azidomethyl)tetrahydro-2H-pyran-3,4-diol (28 mg, 0.11 mmol), 2-chloro-4-(trifluoromethyl)pyrimidine (27 mg, 0.15 mmol) and DIEA (26 mg, 0.2 mmol) in isopropanol (3 mL) was stirred at 80° C. overnight in a sealed tube. The mixture was concentrated and purified by chromatography on C18 column to give (2R,3R,4R,5R,6S)-6-(allyloxy)-2-(azidomethyl)-5-((4-(trifluoromethyl)pyrimidin-2-yl)amino)tetrahydro-2H-pyran-3,4-diol (A6, 8.8 mg, 20% yield) as a white solid. LC-MS (ESI) found: 391 [M+H]$^+$. $^1$H NMR (400 MHz, CD$_3$OD): δ 8.52 (d, J=4.8 Hz, 1H), 6.91 (d, J=4.9 Hz, 1H), 5.89 (s, 1H), 5.28 (d, J=17.2 Hz, 1H), 5.12 (d, J=10.5 Hz, 1H), 5.04 (s, 1H), 4.52 (s, 1H), 4.22 (ddt, J=13.0, 5.0, 1.3 Hz, 1H), 4.08-3.97 (m, 2H), 3.92 (dd, J=10.8, 3.2 Hz, 1H), 3.86 (d, J=2.5 Hz, 1H), 3.62 (dd, J=12.8, 8.7 Hz, 1H), 3.33 (s, 1H). $^{19}$F NMR (377 MHz, CD$_3$OD): δ −72.35.

Preparation of A7, 4-(((3S,4R,5R,6R)-4,5-dihydroxy-6-(hydroxymethyl)tetrahydro-2H-pyran-3-yl)amino)-6-(trifluoromethyl)pyrimidine-2-carbonitrile

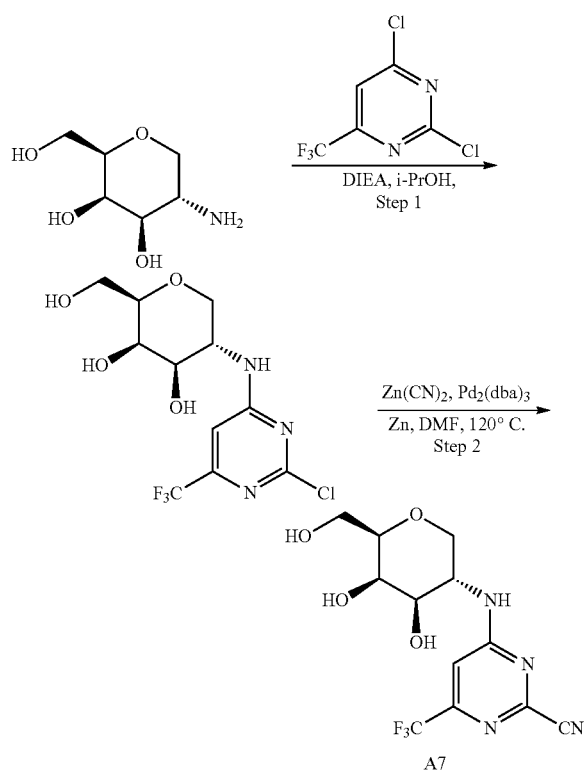

Step 1: To a mixture of (2R,3R,4R,5S)-5-amino-2-(hydroxymethyl)tetrahydro-2H-pyran-3,4-diol hydrochloride (500 mg, 3.1 mmol) in i-PrOH (3.0 mL) was added 2,4-dichloro-6-(trifluoromethyl)pyrimidine (0.84 mL, 6.1 mmol) and DIEA (1.5 mL, 9.2 mmol) at r.t under N$_2$. After stirring at r.t overnight, the mixture was concentrated and purified by chromatography on (silica gel, 0-30% methanol in DCM) to give (2R,3R,4R,5S)-5-((2-chloro-6-(trifluoromethyl)pyrimidin-4-yl)amino)-2-(hydroxymethyl)tetrahydro-2H-pyran-3,4-diol (160 mg, 15% yield) as a white solid. LC-MS (ESI) found: 344 [M+1]$^+$.

Step 2: To a mixture of (2R,3R,4R,5S)-5-((2-chloro-6-(trifluoromethyl)pyrimidin-4-yl)amino)-2-(hydroxymethyl)tetrahydro-2H-pyran-3,4-diol (20 mg, 0.058 mmol) in DMF (3.0 mL) was added Zn(CN)$_2$ (4.1 mg, 0.035 mmol), dppf (16.2 mg, 0.028 mmol), Zn (3.3 mg, 0.31 mmol) and Pd$_2$(dba)$_3$ (26.6 mg, 0.18 mmol) at rt under N$_2$. After stirring at 120° C. overnight, the reaction mixture was concentrated and purified by prep-TLC to give 4-(((3S,4R,5R,6R)-4,5-dihydroxy-6-(hydroxymethyl)tetrahydro-2H-pyran-3-yl)amino)-6-(trifluoromethyl)pyrimidine-2-carbonitrile (A7, 2.4 mg, 12% yield) as a white solid. LC-MS (ESI) found: 333 [M−H]$^−$. $^1$H NMR (400 MHz, CD$_3$OD): δ 6.97 (s, 1H), 4.57-4.48 (m, 1H), 4.08 (dd, J=11.1, 5.2 Hz, 1H), 3.92 (d, J=2.8 Hz, 1H), 3.76 (dd, J=11.3, 7.1 Hz, 1H), 3.69 (dd, J=11.4, 4.9 Hz, 1H), 3.62 (dd, J=10.6, 3.1 Hz, 1H), 3.48-3.44 (m, 1H), 3.14 (t, J=10.9 Hz, 1H).

Preparation of A8, (2R,3R,4R,5S)-5-((5-fluoro-6-(trifluoromethyl)pyridin-2-yl)amino)-2-(hydroxymethyl)tetrahydro-2H-pyran-3,4-diol

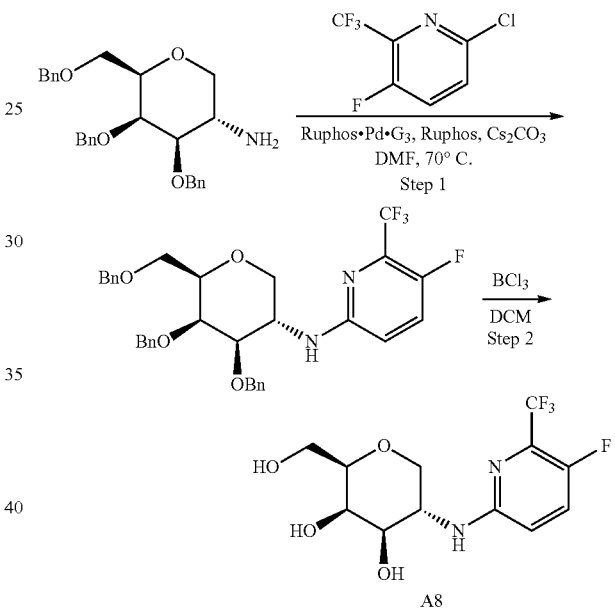

Step 1: To a solution of (3S,4R,5R,6R)-4,5-bis(benzyloxy)-6-((benzyloxy)methyl)tetrahydro-2H-pyran-3-amine (200.0 mg, 0.462 mmol) in DMF (10.0 mL) was added 6-chloro-3-fluoro-2-(trifluoromethyl)pyridine (91.9 mg, 0.462 mmol), Ruphos.Pd.G3 (38.0 mg, 0.046 mmol), Ruphos (21.5 mg, 0.046 mmol) and Cs$_2$CO$_3$ (450.5 mg, 1.386 mmol). The mixture was stirred at 70° C. under N$_2$ for 16 h. The mixture was concentrated under reduced pressure to give a crude product, which was purified by column to give N-((3S,4R,5R,6R)-4,5-bis(benzyloxy)-6-((benzyloxy)methyl)tetrahydro-2H-pyran-3-yl)-5-fluoro-6-(trifluoromethyl)pyridin-2-amine (100.1 mg, 36% yield). LC-MS (ESI) found: 597 [M+H]$^+$.

Step 2: To a solution of N-((3S,4R,5R,6R)-4,5-bis(benzyloxy)-6-((benzyloxy)methyl)tetrahydro-2H-pyran-3-yl)-5-fluoro-6-(trifluoromethyl)pyridin-2-amine (100.1 mg, 0.168 mmol) in DCM (20.0 mL) was added BCl$_3$ (1.68 mL, 1 N in DCM) at 0° C. The mixture was stirred at the room temperature for 2 h. The mixture was concentrated under reduced pressure to give a crude product, which was purified by column to give (2R,3R,4R,5S)-5-((5-fluoro-6-(trifluoromethyl)pyridin-2-yl)amino)-2-(hydroxymethyl)tetrahydro-2H-pyran-3,4-diol (A8, 6.0 mg, 11% yield). LC-MS (ESI) found: 327 [M+H]+. 1H NMR (400 MHz, CD3OD): δ 7.40 (t, J=9.5 Hz, 1H), 6.77 (dd, J=9.2, 2.7 Hz, 1H), 4.30-4.11 (m, 2H), 3.90 (d, J=2.7 Hz, 1H), 3.75 (dd, J=11.4, 7.1 Hz, 1H), 3.68 (dd, J=11.4, 5.0 Hz, 1H), 3.59 (dd, J=10.1, 3.2 Hz, 1H), 3.48-3.41 (m, 1H), 3.08 (dd, J=15.1, 5.7 Hz, 1H). 19F NMR (377 MHz, CD3OD): δ −66.95 (d, J=18.0 Hz), −141.07--145.72 (m).

Preparation of A9, (2R,3R,4R,5R)-2-(hydroxymethyl)-5-((6-(trifluoromethyl)pyrazin-2-yl)amino) tetrahydro-2H-pyran-3,4-diol

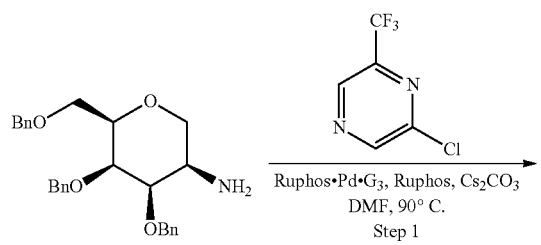

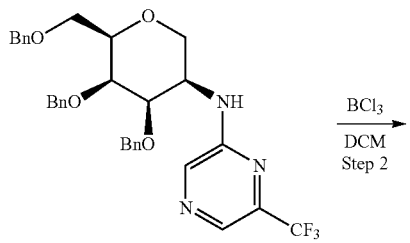

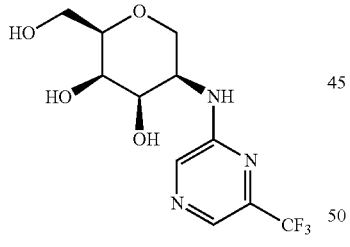

A9

Step 1: To a solution of (3S,4R,5R,6R)-4,5-bis(benzyloxy)-6-((benzyloxy)methyl)tetrahydro-2H-pyran-3-amine (200.0 mg, 0.462 mmol) in DMF (10.0 mL) was added 2-chloro-6-(trifluoromethyl)pyrazine (84.1 mg, 0.462 mmol), Ruphos.Pd.G3 (38.0 mg, 0.046 mmol), Ruphos (21.5 mg, 0.046 mmol) and Cs2CO3 (450.5 mg, 1.386 mmol). The mixture was stirred at 70° C. under N2 for 16 h. The mixture was concentrated under reduced pressure to give a crude product, which was purified by column to give N-((3R,4R,5R,6R)-4,5-bis(benzyloxy)-6-((benzyloxy)methyl)tetrahydro-2H-pyran-3-yl)-6-(trifluoromethyl)pyrazin-2-amine (95 mg, 34% yield). LC-MS (ESI) found: 580 [M+H]+.

Step 2: To a solution of N-((3R,4R,5R,6R)-4,5-bis(benzyloxy)-6-((benzyloxy)methyl)tetrahydro-2H-pyran-3-yl)-6-(trifluoromethyl)pyrazin-2-amine (95 mg, 0.168 mmol) in DCM (20.0 mL) was added BCl3 (1.68 mL, 1 N in DCM) at 0° C. The mixture was stirred at the room temperature for 2 h. The mixture was concentrated under reduced pressure to give a crude product, which was purified by column to give (2R,3R,4R,5R)-2-(hydroxymethyl)-5-((6-(trifluoromethyl) pyrazin-2-yl)amino)tetrahydro-2H-pyran-3,4-diol (A9, 2.0 mg, 4% yield). LC-MS (ESI) found: 310[M+H]+. 1H NMR (400 MHz, CD3OD): δ 8.14 (s, 1H), 7.98 (s, 1H), 4.33 (d, J=3.5 Hz, 1H), 4.04 (dd, J=12.0, 2.0 Hz, 1H), 3.98-3.90 (m, 1H), 3.86 (dd, J=4.6, 3.2 Hz, 1H), 3.80 (dd, J=11.5, 7.1 Hz, 1H), 3.70 (dd, J=11.5, 4.7 Hz, 1H), 3.59 (dd, J=12.1, 1.7 Hz, 1H), 3.49-3.41 (m, 1H). 19F NMR (377 MHz, CD3OD): δ −70.42 (s).

Preparation of A10, (1S,2R,3R,4R,5S)-1-(hydroxymethyl)-4-((5-(trifluoromethyl)pyrazin-2-yl) amino)-6,8-dioxabicyclo[3.2.1]octane-2,3-diol

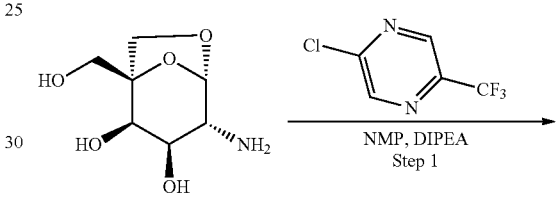

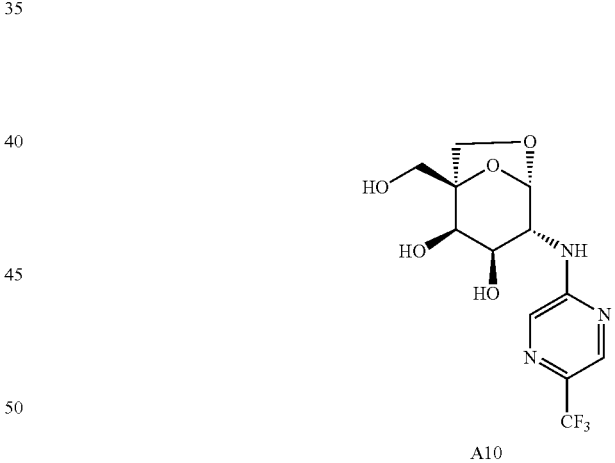

A10

Step 1: A solution of (1S,2R,3R,4R,5S)-4-amino-1-(hydroxymethyl)-6,8-dioxabicyclo[3.2.1]octane-2,3-diol (20 mg, 0.11 mmol), 2-chloro-5-(trifluoromethyl)pyrazine (19 mg, 0.11 mmol) and DIPEA (20 mg, 0.16 mmol) in NMP (1 mL) was stirred at 80° C. overnight. The mixture was purified by prep-HPLC to give (1S,2R,3R,4R,5S)-1-(hydroxymethyl)-4-((5-(trifluoromethyl)pyrazin-2-yl)amino)-6,8-dioxabicyclo[3.2.1]octane-2,3-diol (A10, 5.4 mg, 15% yield) as yellow solid. LC-MS (ESI) found: 338 [M+H]+. 1H NMR (400 MHz, CD3OD): δ 8.26 (s, 1H), 7.99 (d, J=1.2 Hz, 1H), 5.35 (d, J=1.4 Hz, 1H), 4.25 (d, J=9.9 Hz, 1H), 3.94 (t, J=8.2 Hz, 2H), 3.83 (dt, J=10.6, 6.5 Hz, 3H), 3.71 (d, J=7.9 Hz, 1H).

Preparation of A11, 1-((3aR,4S,7S,8R,8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)-2,5,8,11-tetraoxatridecan-13-ol

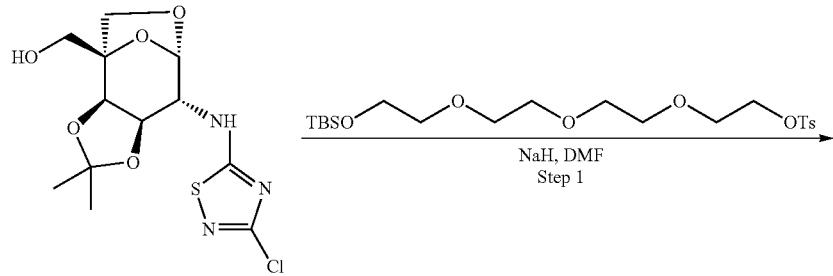

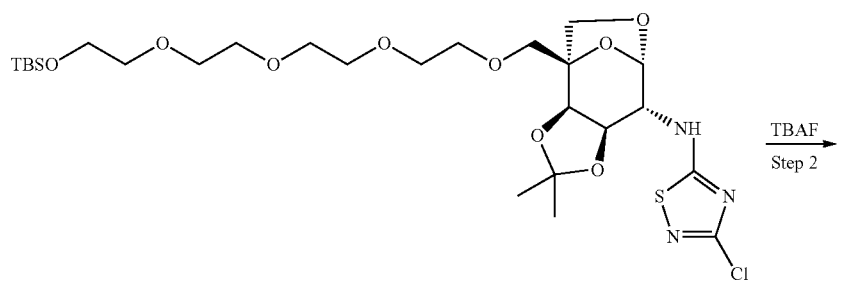

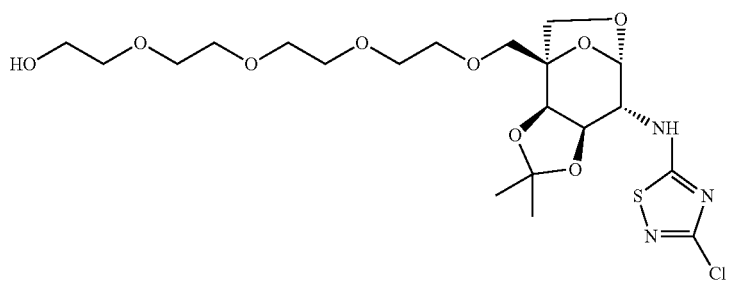

A11

Step 1: To a solution of ((3aR,4S,7S,8R,8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)methanol (100 mg, 0.29 mmol) in DMF (3 mL) was added NaH (23 mg, 0.58 mmol, 60% wt. in mineral oil) at 0° C. After stirring at 0° C. for 20 min, 2,2,3,3-tetramethyl-4,7,10,13-tetraoxa-3-silapentadecan-15-yl 4-methylbenzenesulfonate (145 mg, 0.31 mmol) was added. The mixture was stirred at rt overnight, then extracted with EA and H₂O. The organic layer was concentrated and the residue was purified by flash column to give 3-chloro-N-((3aR,4S,7S,8R,8aR)-2,2-dimethyl-4-(15,15,16,16-tetramethyl-2,5,8,11,14-pentaoxa-15-silaheptadecyl)hexahydro-4,7-epoxy[1,3]dioxolo[4,5-d]oxepin-8-yl)-1,2,4-thiadiazol-5-amine (80 mg, 43% yield) as colorless oil. LC-MS (ESI) found: 640 [M+H]$^+$.

Step 2: To a solution of 3-chloro-N-((3aR,4S,7S,8R,8aR)-2,2-dimethyl-4-(15,15,16,16-tetramethyl-2,5,8,11,14-pentaoxa-15-silaheptadecyl)hexahydro-4,7-epoxy[1,3]dioxolo[4,5-d]oxepin-8-yl)-1,2,4-thiadiazol-5-amine (80 mg, 0.12 mmol) in THF (3 mL) was added TBAF (0.1 mL, 1 N in THF) at 0° C. The mixture was stirred at 0° C. for 1 h, then concentrated. The residue was purified by prep-HPLC to give 1-((3aR,4S,7S,8R,8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)-2,5,8,11-tetraoxatridecan-13-ol (A11, 10.7 mg, 16% yield) as white solid. $^1$H NMR (400 MHz, CD$_3$OD): δ 5.38 (d, J=1.7 Hz, 1H), 4.33 (d, J=5.9 Hz, 1H), 4.22 (t, J=6.3 Hz, 1H), 3.92 (dd, J=18.4, 9.0 Hz, 2H), 3.83-3.77 (m, 2H), 3.73-3.63 (m, 15H), 3.56 (dd, J=6.2, 3.4 Hz, 2H), 1.53 (s, 3H), 1.35 (s, 3H).

Preparation of A12, 3,3'-((2-(2-(2-(2-(2-(phenylamino)ethoxy)ethoxy)ethoxy)acetamido)propane-1,3-diyl)bis(oxy))bis(N-(1-((1S,2R,3R,4R,5S)-2,3-dihydroxy-4-(2,2,2-trifluoroacetamido)-6,8-dioxabicyclo[3.2.1]octan-1-yl)-2,5,8,11-tetraoxatridecan-13-yl)propanamide)
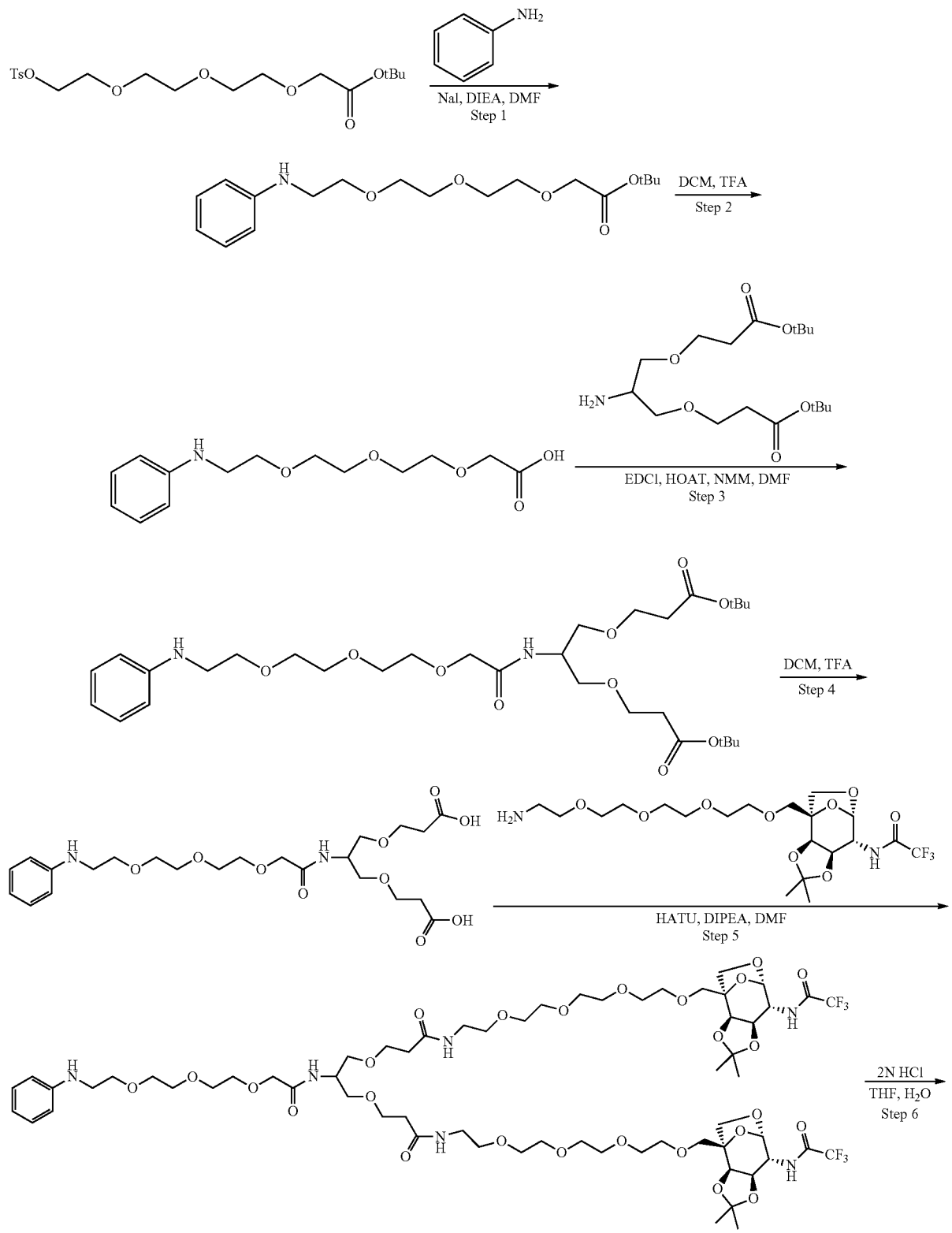

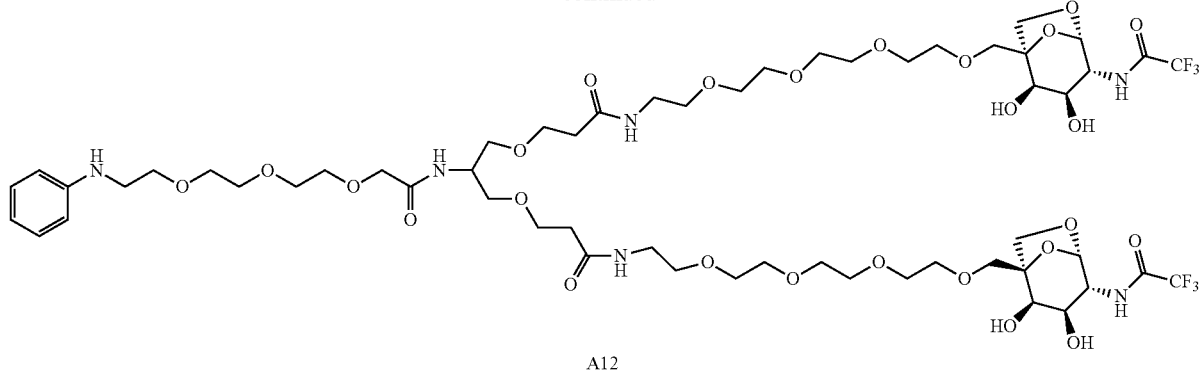

A12

Step 1: To a solution of tert-butyl 2-(2-(2-(2-(tosyloxy)ethoxy)ethoxy)ethoxy)acetate (550 mg, 1.32 mmol) in DMF (5 mL) were added aniline (368 mg, 3.95 mmol) and DIEA (0.87 mL, 5.26 mmol), and the reaction was stirred at 100° C. for 16 h. The reaction was diluted with EA and water. The organic layer was separated and concentrated in vacuo. The residue was purified using silica gel column chromatography eluting with ethyl acetate in petroleum ether (40%). The organic layer was collected, concentrated in vacuo, and dried to afford the title compound tert-butyl 2-(2-(2-(2-(phenylamino)ethoxy)ethoxy)ethoxy)acetate (380 mg, 85% yield). LC-MS (ESI) found: 340 [M+H]$^+$.

Step 2: To a solution of tert-butyl 2-(2-(2-(2-(phenylamino)ethoxy)ethoxy)ethoxy)acetate (380 mg, 1.12 mmol) in DCM (2 mL) was added TFA (1 mL), and the reaction was stirred at room temperature for 18 h. The reaction was concentrated in vacuo to afford the title compound 2-(2-(2-(2-(phenylamino)ethoxy)ethoxy)ethoxy)acetic acid (300 mg, 95% yield). LC-MS (ESI) found: 284 [M+H]$^+$.

Step 3: To a solution of 2-(2-(2-(2-(phenylamino)ethoxy)ethoxy)ethoxy)acetic acid (300 mg, 1.06 mmol) in DMF (3 mL) were added DIEA (0.5 mL, 3.18 mmol), and HATU (483 mg, 1.27 mmol), and the reaction was stirred at 0° C. for 30 min. Di-tert-butyl 3,3'-((2-aminopropane-1,3-diyl)bis(oxy))dipropionate (441 mg, 1.27 mmol) was added, the reaction was stirred at room temperature for 16 h. The reaction was diluted with EA and water. The organic layer was separated, and concentrated in vacuo. The residue was purified by flash to afford tert-butyl 13-((3-(tert-butoxy)-3-oxopropoxy)methyl)-11-oxo-1-(phenylamino)-3,6,9,15-tetraoxa-12-azaoctadecan-18-oate (400 mg, 62% yield). LC-MS (ESI) found: 613 [M+H]$^+$.

Step 4: To a solution of tert-butyl 13-((3-(tert-butoxy)-3-oxopropoxy)methyl)-11-oxo-1-(phenylamino)-3,6,9,15-tetraoxa-12-azaoctadecan-18-oate (120 mg, 0.20 mmol) in DCM (3 mL) was added TFA (1 mL, 13 mmol), and the reaction was stirred at room temperature for 18 h. The reaction was concentrated in vacuo to afford the title compound 13-((2-carboxyethoxy)methyl)-11-oxo-1-(phenylamino)-3,6,9,15-tetraoxa-12-azaoctadecan-18-oic acid (98 mg, 99% yield). LC-MS (ESI) found: 501 [M+H]$^+$.

Step 5: To a solution of 13-((2-carboxyethoxy)methyl)-11-oxo-1-(phenylamino)-3,6,9,15-tetraoxa-12-azaoctadecan-18-oic acid (113 mg, 0.226 mmol) in DMF (10 mL) were added HATU (197 mg, 0.52 mmol) and DIEA (0.26 mL, 1.58 mmol), and the reaction was stirred at 0° C. for 30 min. N-((3aR,4S,7S,8R,8aR)-4-(13-amino-2,5,8,11-tetraoxatridecyl)-2,2-dimethylhexahydro-4,7-epoxy[1,3]dioxolo[4,5-d]oxepin-8-yl)-2,2,2-trifluoroacetamide (250 mg, 0.50 mmol) was added and the reaction was stirred at rt for 18 h. The reaction was diluted with EA and water. The organic layer was separated and concentrated in vacuo. The residue was purified using silica gel column chromatography eluting with (DCM:MEOH=20:1) to afford the title compound 3,3'-((2-(2-(2-(2-(2-(phenylamino)ethoxy)ethoxy)ethoxy)acetamido)propane-1,3-diyl)bis(oxy))bis(N-(1-((3aR,4S,7S,8R,8aR)-2,2-dimethyl-8-(2,2,2-trifluoroacetamido)tetrahydro-4,7-epoxy[1,3]dioxolo[4,5-d]oxepin-4(5H)-yl)-2,5,8,11-tetraoxatridecan-13-yl)propanamide) (110 mg, 30% yield). LC-MS (ESI) found: 1470 [M+H]$^+$.

Step 6: To a solution of 3,3'-((2-(2-(2-(2-(2-(phenylamino)ethoxy)ethoxy)ethoxy)acetamido)propane-1,3-diyl)bis(oxy))bis(N-(1-((3aR,4S,7S,8R,8aR)-2,2-dimethyl-8-(2,2,2-trifluoroacetamido)tetrahydro-4,7-epoxy[1,3]dioxolo[4,5-d]oxepin-4(5H)-yl)-2,5,8,11-tetraoxatridecan-13-yl)propanamide) (100 mg, 0.068 mmol) in THF (3 mL) was added HCl (1.5 mL, 2 M in H$_2$O), and the reaction was stirred at room temperature for 18 h. The reaction was concentrated in vacuo. The residue was purified by prep-HPLC to afford the title compound 3,3'-((2-(2-(2-(2-(2-(phenylamino)ethoxy)ethoxy)ethoxy)acetamido)propane-1,3-diyl)bis(oxy))bis(N-(1-((1S,2R,3R,4R,5S)-2,3-dihydroxy-4-(2,2,2-trifluoroacetamido)-6,8-dioxabicyclo[3.2.1]octan-1-yl)-2,5,8,11-tetraoxatridecan-13-yl)propanamide) (A12, 11 mg, 12% yield). LC-MS (ESI) found: 1389[M+H]$^+$. $^1$H NMR (400 MHz, MeOD): δ 7.15-7.07 (m, 2H), 6.71-6.59 (m, 3H), 5.25 (d, J=1.3 Hz, 2H), 4.20 (p, J=5.6 Hz, 1H), 4.00 (dd, J=11.9, 9.4 Hz, 6H), 3.90 (q, J=4.0 Hz, 4H), 3.81 (d, J=8.1 Hz, 2H), 3.69 (dd, J=9.0, 4.1 Hz, 18H), 3.66-3.59 (m, 24H), 3.56-3.48 (m, 8H), 3.37 (t, J=5.5 Hz, 4H), 3.28 (t, J=5.5 Hz, 2H), 2.44 (t, J=6.2 Hz, 4H).

Preparation of A13 3,3'-((2-aminopropane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide)

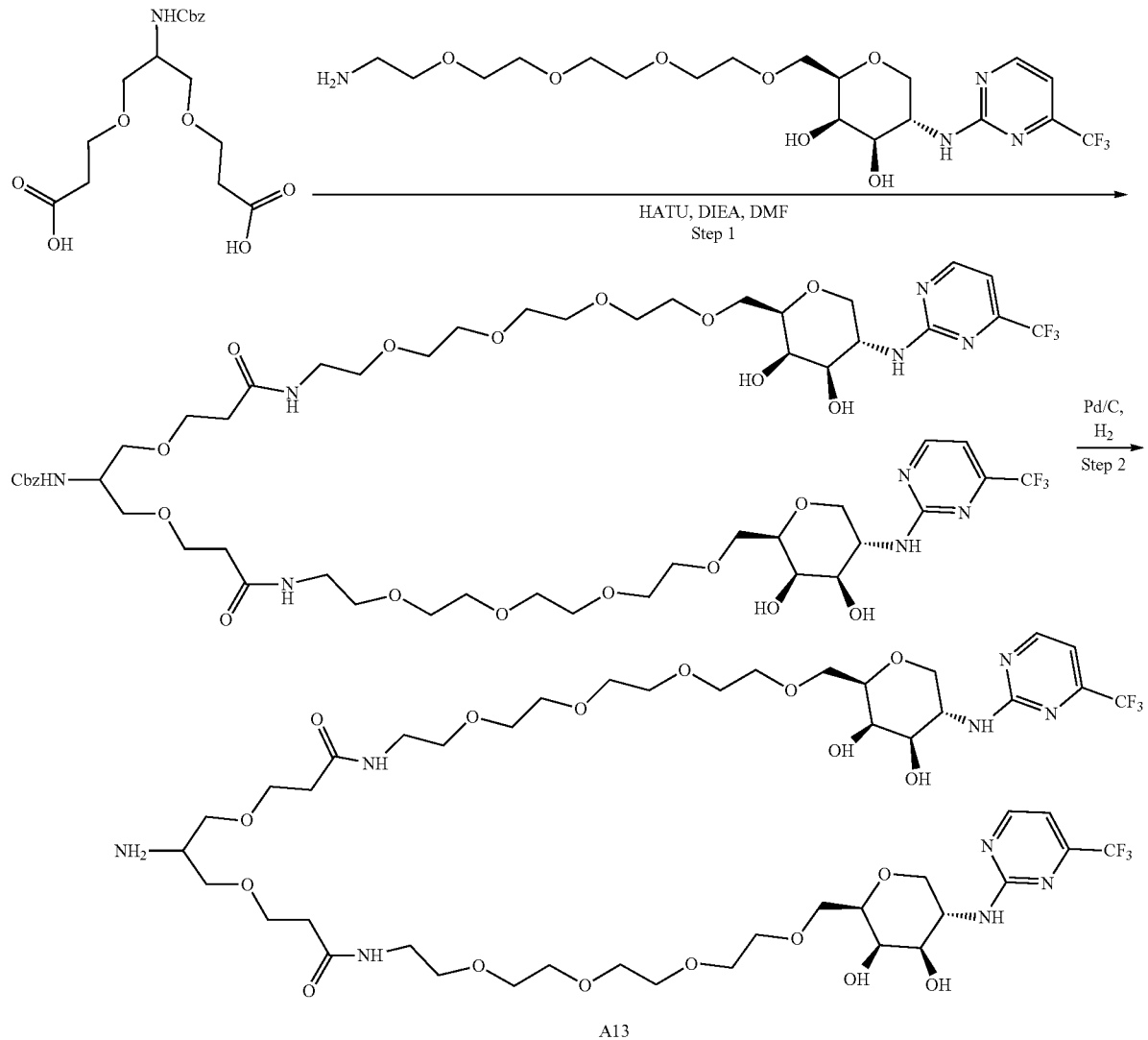

Step 1: To a solution of 3,3'-((2-(((benzyloxy)carbonyl)amino)propane-1,3-diyl)bis(oxy))dipropionic acid (0.72 g, 1.96 mmol) and HATU (2.23 g, 5.88 mmol) in DMF (20 mL) was added DIPEA (1.0 g, 7.84 mmol) and (2R,3R,4R,5S)-2-(13-amino-2,5,8,11-tetraoxatridecyl)-5-((4-(trifluoromethyl)pyrimidin-2-yl)amino)tetrahydro-2H-pyran-3,4-diol (2.1 g, 4.33 mmol) at rt. The reaction mixture was stirred at rt for overnight. The resulting mixture was separated and concentrated in vacuo. The crude product was purified by flash chromatography (C18, 0~80%, MeOH in H$_2$O) to give benzyl (1,39-bis((2R,3R,4R,5S)-3,4-dihydroxy-5-((4-(trifluoromethyl)pyrimidin-2-yl)amino)tetrahydro-2H-pyran-2-yl)-15,25-dioxo-2,5,8,11,18,22,29,32,35,38-decaoxa-14,26-diazanonatriacontan-20-yl)carbamate (1.2 g, 48% yield) as white solid. LC-MS (ESI) found: 1303[M+H]$^+$. $^1$H NMR (400 MHz, MeOD): δ 8.50 (d, J=4.8 Hz, 2H), 7.41-7.25 (m, 5H), 6.89 (d, J=4.9 Hz, 2H), 5.07 (s, 2H), 4.43-4.27 (m, 2H), 4.08 (dd, J=10.9, 5.2 Hz, 2H), 3.91 (d, J=3.0 Hz, 2H), 3.88-3.82 (m, 1H), 3.72-3.55 (m, 36H), 3.55-3.42 (m, 8H), 3.35 (t, J=5.5 Hz, 4H), 3.15 (t, J=10.9 Hz, 2H), 2.43 (t, J=6.1, 4H).

Step 2: To a solution of benzyl (1,39-bis((2R,3R,4R,5S)-3,4-dihydroxy-5-((4-(trifluoromethyl)pyrimidin-2-yl)amino)tetrahydro-2H-pyran-2-yl)-15,25-dioxo-2,5,8,11,18,22,29,32,35,38-decaoxa-14,26-diazanonatriacontan-20-yl)carbamate (1.2 g, 0.92 mmol) in MeOH (10 mL) was added Pd/C (120 mg, 10% wt, 60% wet) at rt. The reaction mixture was stirred at rt under a H$_2$ balloon overnight. The resulting mixture was separated and concentrated in vacuo. The crude product was purified by flash chromatography (C18, 0~40%, MeOH in H$_2$O) to give 3,3'-((2-aminopropane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (800 mg, 74% yield) as white solid. LC-MS (ESI) found: 1169[M+H]⁺. ¹H NMR (400 MHz, MeOD): δ 8.51 (d, J=4.7 Hz, 2H), 6.89 (d, J=4.9 Hz, 2H), 4.36 (d, J=5.0 Hz, 2H), 4.08 (dd, J=11.0, 5.1 Hz, 2H), 3.89 (t, J=17.0 Hz, 2H), 3.79-3.52 (m, 40H), 3.46 (dt, J=20.7, 10.3 Hz, 2H), 3.37 (td, J=8.5, 4.9 Hz, 6H), 3.13 (dt, J=10.3, 8.0 Hz, 3H), 2.46 (t, J=6.0 Hz, 4H).

Preparation of A14 3,3'-((2-(6-azidohexanamido)propane-1,3-diyl)bis(oxy))bis(N-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide)

Step 1: A solution of 3,3'-((2-(6-azidohexanamido)propane-1,3-diyl)bis(oxy))dipropionic acid (28 mg, 0.08 mmol) and HATU (62.7 mg, 0.17 mmol) in DMF (3 mL) was stirred at rt for 30 min. N-((3aR,4S,7S,8R,8aR)-4-(13-amino-2,5,8,11-tetraoxatridecyl)-2,2-dimethylhexahydro-4,7-epoxy[1,3]dioxolo[4,5-d]oxepin-8-yl)-3-chloro-1,2,4-thiadiazol-5-amine (98 mg, 0.19 mmol) and DIPEA (0.05 mL, 0.3 mmol) were added at rt. The reaction was stirred overnight. The resulting mixture was concentrated in vacuo. The crude product was purified by flash chromatography (silica gel, 0-10% MeOH in DCM) to give 3,3'-((2-(6-azidohexanamido)propane-1,3-diyl)bis(oxy))bis(N-(1-((3aR,4S,7S,8R,

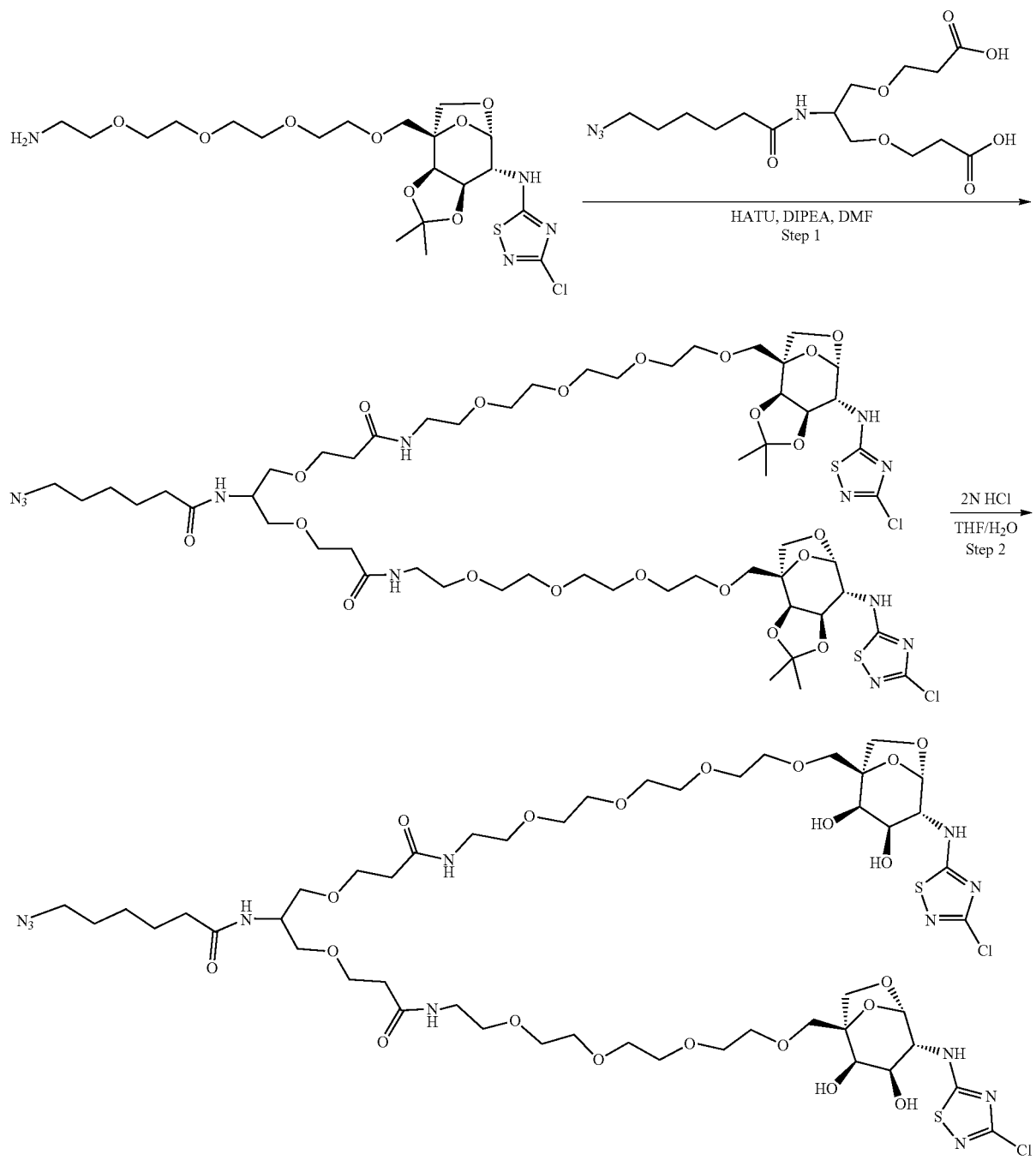

A14

8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)-2,5,8,11-tetraoxatridecan-13-yl)propanamide) (50 mg, 48% yield) as a colorless oil. LC-MS (ESI) found: 1389 [M+H]+.

Step 2: To a solution of 3,3'-((2-(6-azidohexanamido)propane-1,3-diyl)bis(oxy))bis(N-(1-((3aR,4S,7S,8R,8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)-2,5,8,11-tetraoxatridecan-13-yl)propanamide) (50 mg, 0.04 mmol) in THF (3 mL) was added HCl (1 mL, 2 M in H$_2$O). The reaction was stirred at rt overnight. The crude product was purified by flash chromatography (silica gel, 0-10% MeOH in DCM) to give 3,3'-((2-(6-azidohexanamido)propane-1,3-diyl)bis(oxy))bis(N-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide) (30 mg, 64% yield) as a white solid. LC-MS (ESI) found: 1309 [M+H]+. $^1$H NMR (400 MHz, MeOD): δ 5.39 (s, 2H), 4.14-4.09 (m, 1H), 4.00 (d, J=9.6 Hz, 2H), 3.93 (d, J=4.1 Hz, 2H), 3.83 (d, J=8.0 Hz, 2H), 3.77 (dd, J=9.6, 4.2 Hz, 2H), 3.73-3.60 (m, 35H), 3.56 (t, J=5.5 Hz, 4H), 3.52-3.45 (m, 4H), 3.39 (t, J=5.5 Hz, 4H), 3.28 (s, 1H), 2.46 (dd, J=6.6, 5.4 Hz, 4H), 2.23 (t, J=7.4 Hz, 2H), 1.67-1.57 (m, 4H), 1.44-1.36 (m, 2H).

Preparation of A15 6-azido-N-(1,3-bis((1-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)-1H-1,2,3-triazol-4-yl)methoxy)propan-2-yl)hexanamide

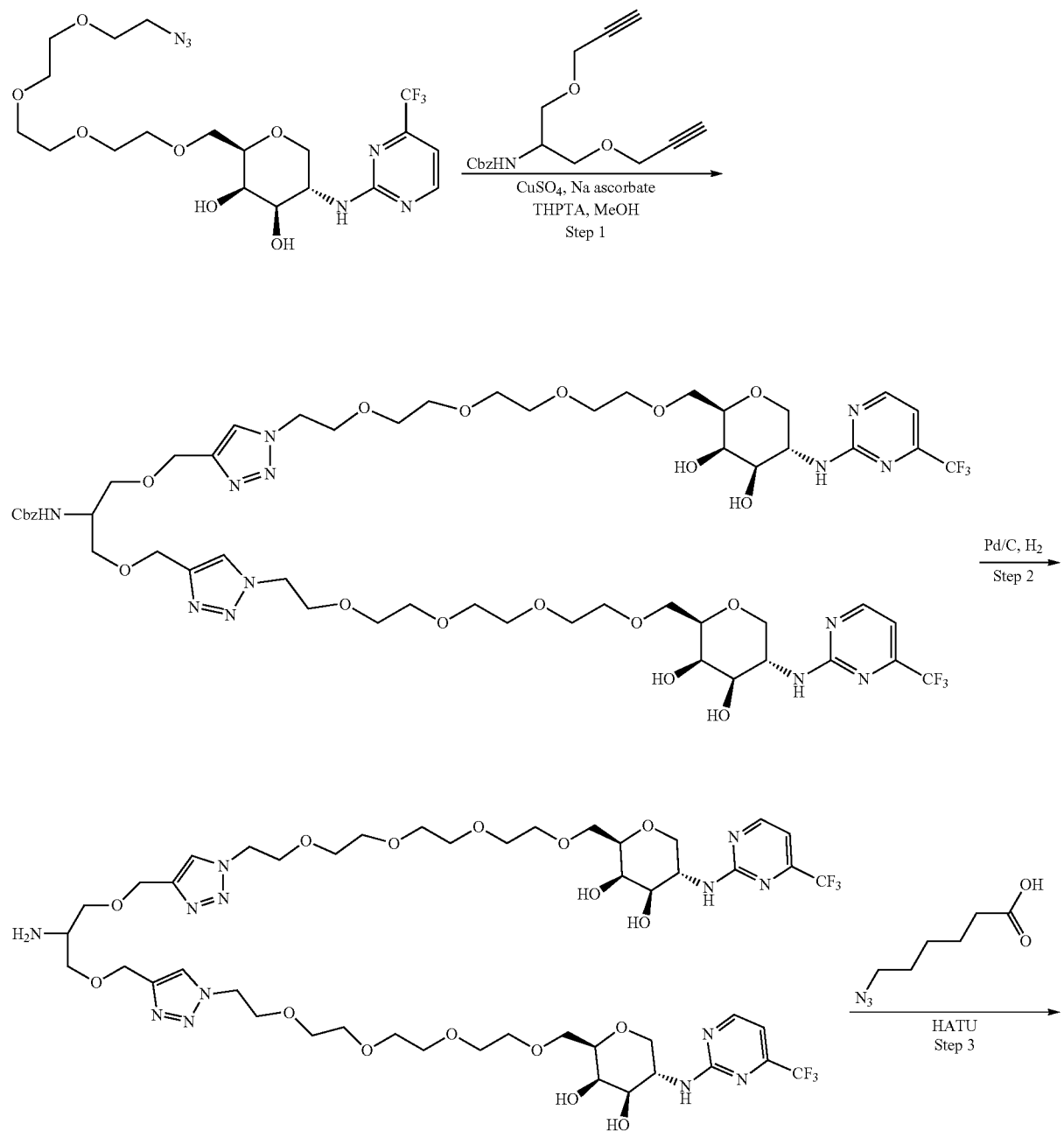

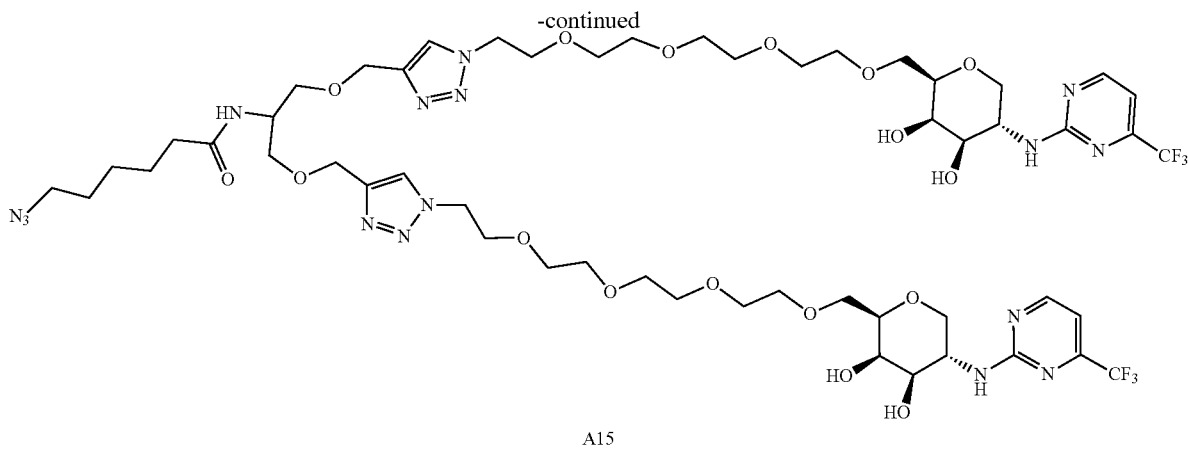

A15

Step 1: To a solution of benzyl (1,3-bis(prop-2-yn-1-yloxy)propan-2-yl)carbamate (80 mg, 0.27 mmol) and (2R,3R,4R,5S)-2-(13-azido-2,5,8,11-tetraoxatridecyl)-5-((4-(trifluoromethyl)pyrimidin-2-yl)amino)tetrahydro-2H-pyran-3,4-diol (300 mg, 0.58 mmol) in MeOH (3 mL) were added $CuSO_4$ (4.2 mg, 0.03 mmol) and THPTA (20 mg, 0.004 mmol) in $H_2O$ (0.5 mL) and Na ascorbate (11 mg, 0.05 mmol) in $H_2O$ (0.5 mL). The mixture was stirred at rt overnight and concentrated. The residue was purified by flash to give benzyl (1,3-bis((1-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)-1H-1,2,3-triazol-4-yl)methoxy)propan-2-yl)carbamate (320 mg, 91% yield) as colorless oil. LC-MS (ESI) found: 1322 $[M+H]^+$. $^1$H NMR (400 MHz, MeOD): δ 8.49 (d, J=4.8 Hz, 2H), 8.01 (s, 2H), 7.47-7.19 (m, 5H), 6.88 (d, J=4.9 Hz, 2H), 5.07 (s, 2H), 4.57 (dd, J=9.5, 4.6 Hz, 8H), 4.35 (d, J=5.1 Hz, 2H), 4.06 (dd, J=10.9, 5.2 Hz, 2H), 3.95-3.85 (m, 7H), 3.69-3.63 (m, 6H), 3.62-3.51 (m, 30H), 3.13 (t, J=10.9 Hz, 2H).

Step 2: A solution of benzyl (1,3-bis((1-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)-1H-1,2,3-triazol-4-yl)methoxy)propan-2-yl)carbamate (300 mg, 0.23 mmol) and Pd/C (30 mg, 10% wt, 60% wet) in MeOH (5 mL) was stirred at rt under a $H_2$ balloon overnight. The mixture was filtered through a Celite pad, and the filtrate was concentrated to give (2R,2'R,3R,3'R,4R,4'R,5S,5'S)-2,2'-(((((2-aminopropane-1,3-diyl)bis(oxy))bis(methylene))bis(1H-1,2,3-triazole-4,1-diyl))bis(2,5,8,11-tetraoxatridecane-13,1-diyl))bis(5-((4-(trifluoromethyl)pyrimidin-2-yl)amino)tetrahydro-2H-pyran-3,4-diol) (160 mg, 60% yield) as colorless oil. C-MS (ESI) found: 1188 $[M+H]^+$.

Step 3: To a solution of 6-azidohexanoic acid (13 mg, 0.08 mmol) in DMF (3 mL) was added HATU (35 mg, 0.09 mmol) and DIPEA (22 mg, 0.17 mmol). After stirring at rt for 30 min, (2R,2'R,3R,3'R,4R,4'R,5S,5'S)-2,2'-(((((2-aminopropane-1,3-diyl)bis(oxy))bis(methylene))bis(1H-1,2,3-triazole-4,1-diyl))bis(2,5,8,11-tetraoxatridecane-13,1-diyl))bis(5-((4-(trifluoromethyl)pyrimidin-2-yl)amino)tetrahydro-2H-pyran-3,4-diol) (147 mg, 0.12 mmol) was added. The mixture was stirred at rt under $N_2$ overnight. The mixture was concentrated and the residue was purified by prep-HPLC (Method A) to give 6-azido-N-(1,3-bis((1-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)-1H-1,2,3-triazol-4-yl)methoxy)propan-2-yl)hexanamide (36 mg, 33% yield) as white solid. LC-MS (ESI) found: 1327 $[M+H]^+$. $^1$H NMR (400 MHz, MeOD): δ 8.50 (d, J=4.8 Hz, 2H), 8.02 (s, 2H), 6.89 (d, J=4.9 Hz, 2H), 4.67-4.53 (m, 8H), 4.35 (td, J=10.4, 5.2 Hz, 2H), 4.19 (p, J=5.5 Hz, 1H), 4.07 (dd, J=10.9, 5.2 Hz, 2H), 3.89 (t, J=4.9 Hz, 5H), 3.69-3.50 (m, 37H), 3.26 (t, J=6.8 Hz, 2H), 3.14 (t, J=10.9 Hz, 2H), 2.21 (t, J=7.4 Hz, 2H), 1.66-1.52 (m, 4H), 1.45-1.27 (m, 2H).

Preparation of A18 3,3'-((2-(6-azidohexanamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide)

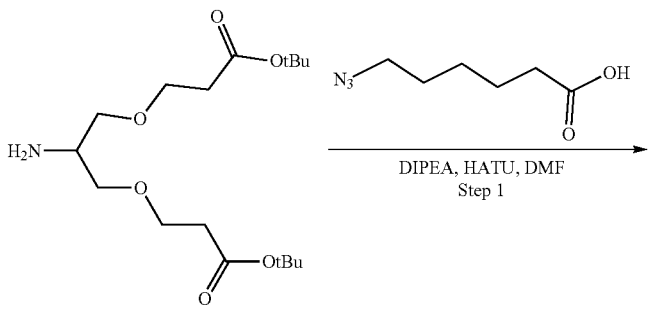

DIPEA, HATU, DMF
Step 1

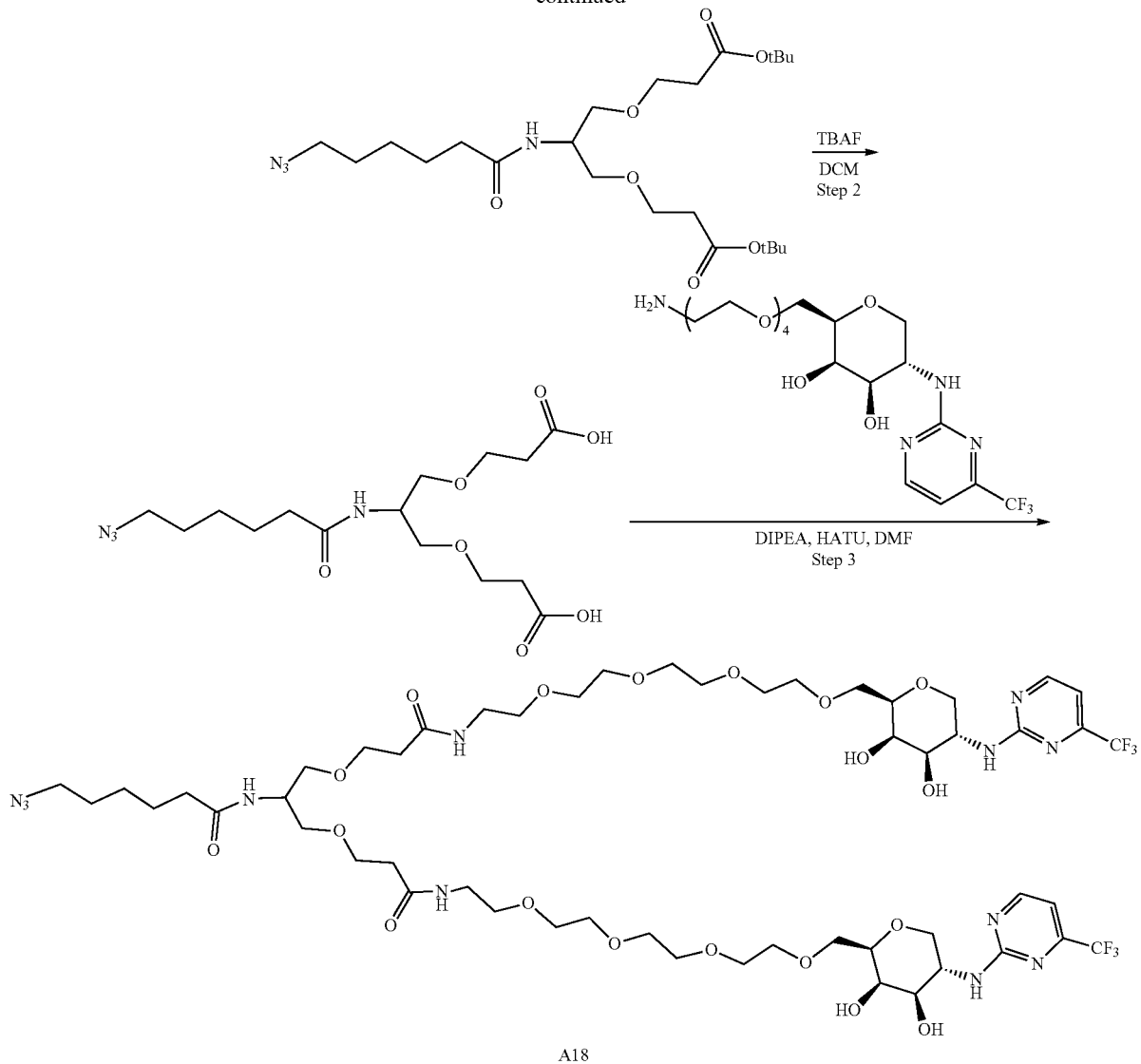

A18

Step 1: A solution of 6-azidohexanoic acid (0.54 g, 3.45 mmol) and HATU (1.3 g, 3.45 mmol) in DMF (10 mL) was stirred at rt for 30 min. Di-tert-butyl 3,3'-((2-aminopropane-1,3-diyl)bis(oxy))dipropionate (1 g, 2.88 mmol) and DIPEA (0.95 mL, 5.76 mmol) were added at rt. The reaction was stirred overnight. The resulting mixture was diluted with DCM (100 mL), washed with H$_2$O (50 mL×2) and brine (20 mL), dried over Na$_2$SO$_4$. The organic layer was separated and concentrated in vacuo. The crude product was purified by flash chromatography (silica gel, 0~80% EA in PE) to give di-tert-butyl 3,3'-((2-(6-azidohexanamido)propane-1,3-diyl)bis(oxy))dipropionate (800 mg, 93% yield) as colorless oil. LC-MS (ESI) found: 487 [M+H]$^+$.

$^1$H NMR (400 MHz, CDCl$_3$): δ 6.28 (d, J=8.2 Hz, 1H), 4.19-4.11 (m, 1H), 3.74-3.62 (m, 4H), 3.58 (dd, J=9.6, 4.0 Hz, 2H), 3.40 (dd, J=9.6, 6.1 Hz, 2H), 3.26 (t, J=6.9 Hz, 2H), 2.52-2.38 (m, 4H), 2.20 (t, J=7.5 Hz, 2H), 1.67-1.63 (m, 4H), 1.47-1.37 (m, 20H).

Step 2: A solution of 3,3'-((2-(6-azidohexanamido)propane-1,3-diyl)bis(oxy))dipropionate (800 mg, 1.64 mmol) in DCM (6 mL) was added TFA (2 mL, 26.93 mmol) dropwise at 0° C. The reaction was stirred at rt for 3 h. The resulting mixture was filtered and concentrated in vacuo. The crude 3,3'-((2-(6-azidohexanamido)propane-1,3-diyl)bis(oxy))dipropionic acid (470 mg, 76% yield) was used to next step with no further purification. LC-MS (ESI) found: 375 [M+H]$^+$. $^1$H NMR (400 MHz, DMSO-d$_6$): δ 12.14 (s, 2H), 7.64 (d, J=8.2 Hz, 1H), 4.00-3.86 (m, 1H), 3.57 (t, J=6.3 Hz, 4H), 3.34 (d, J=5.8 Hz, 4H), 3.29 (d, J=6.9 Hz, 2H), 2.43 (t, J=6.3 Hz, 4H), 2.07 (t, J=7.3 Hz, 2H), 1.56-1.43 (m, 4H), 1.33-1.23 (m, 2H).

Step 3: A solution of 3,3'-((2-(6-azidohexanamido)propane-1,3-diyl)bis(oxy))dipropionic acid (70 mg, 0.19 mmol) and HATU (163 mg, 0.43 mmol) in DMF (5 mL) was stirred at rt for 30 min. (2R,3R,4R,5S)-2-(13-amino-2,5,8,11-tetraoxatridecyl)-5-((4-(trifluoromethyl)pyrimidin-2-yl)amino)tetrahydro-2H-pyran-3,4-diol (208 mg, 0.43 mmol) and DIPEA (73 mg, 0.56 mmol) were added at rt. The reaction was stirred overnight. The resulting mixture was concentrated in vacuo. The crude product was purified by flash chromatography (silica gel, 0~10% MeOH in DCM) to give 3,3'-((2-(6-azidohexanamido)propane-1,3-diyl)bis (oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (65 mg, 28% yield) as white solid. LC-MS (ESI) found: 654 [M+2H]$^{2+}$. $^1$H NMR (400 MHz, MeOD): δ 8.51 (d, J=4.8 Hz, 2H), 6.90 (d, J=4.9 Hz, 2H), 4.36 (td, J=10.6, 5.3 Hz, 2H), 4.16-4.04 (m, 3H), 3.92 (d, J=2.9 Hz, 2H), 3.73-3.60 (m, 36H), 3.56 (dt, J=10.6, 3.0 Hz, 6H), 3.51-3.43 (m, 4H), 3.38 (t, J=5.5 Hz, 4H), 3.17 (t, J=10.9 Hz, 2H), 2.45 (dd, J=6.7, 5.4 Hz, 4H), 2.23 (t, J=7.5 Hz, 2H), 1.67-1.57 (m, 4H), 1.44-1.36 (m, 2H). $^{19}$F NMR (377 MHz, MeOD): δ −72.30 (s).

Preparation of A16: 1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-2,5,8,11-tetraoxatridecan-13-oic acid

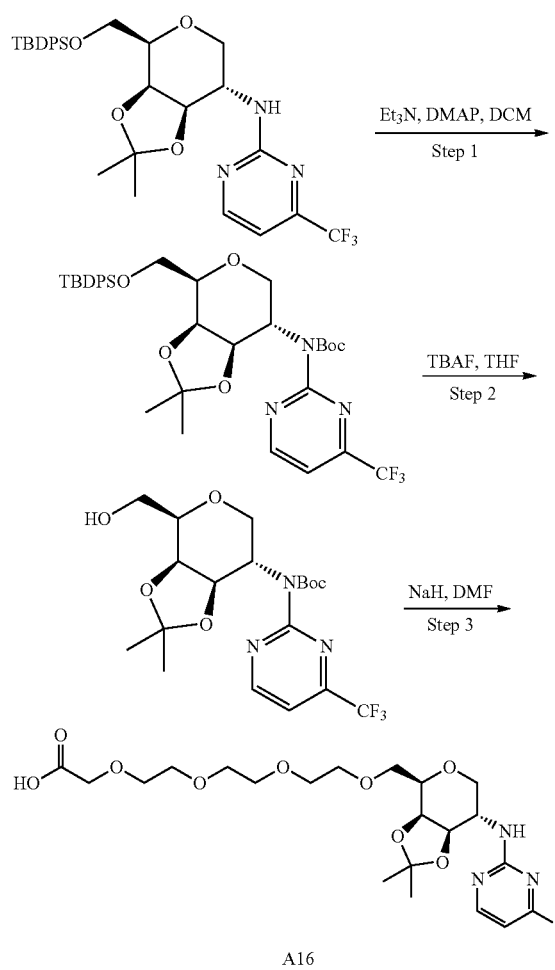

A16

Step 1: To a solution of N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)-4-(trifluoromethyl)pyrimidin-2-amine (2.7 g, 4.59 mmol) in DCM (50 mL) was added triethylamine (3.1 mL, 22.97 mmol) and DMAP (0.56 g, 4.59 mmol) at RT. Then the reaction was added di-tert-butyl decarbonate (4.91 mL, 22.97 mmol) and stirred at RT for 18 h. TLC (PE/EA=5/1) showed starting material was consumed and one main spot detected. The reaction was concentrated and purified by silica gel with PE/EA=5/1 to give tert-butyl ((3aR,4R,7S,7aR)-4-(((tert-butyldiphenylsilyl)oxy)methyl)-2,2-dimethyltetrahydro-4H-[1,3]dioxolo[4,5-c]pyran-7-yl)(4-(trifluoromethyl)pyrimidin-2-yl)carbamate (2.4 g, 76% yield) as colorless oil. LC-MS (ESI) found: 710 [M+Na]$^+$.

Step 2: To a solution of tert-butyl ((3aR,4R,7S,7aR)-4-(((tert-butyldiphenylsilyl)oxy)methyl)-2,2-dimethyltetrahydro-4H-[1,3]dioxolo[4,5-c]pyran-7-yl)(4-(trifluoromethyl)pyrimidin-2-yl)carbamate (2.4 g, 3.48 mmol) in THF (50 mL) was added TBAF (8.4 mL, 1 M in THF) at RT. The reaction was stirred at RT for 1 h. TLC showed starting material was consumed and one main spot detected. The reaction was concentrated and purified by silica gel with PE/EA=1/1 to give tert-butyl ((3aR,4R,7S,7aR)-4-(hydroxymethyl)-2,2-dimethyltetrahydro-4H-[1,3]dioxolo[4,5-c]pyran-7-yl)(4-(trifluoromethyl)pyrimidin-2-yl)carbamate (1.3 g, 93% yield) as colorless oil. LC-MS (ESI) found: 472 [M+Na]$^+$.

Step 3: To a solution of tert-butyl ((3aR,4R,7S,7aR)-4-(hydroxymethyl)-2,2-dimethyltetrahydro-4H-[1,3]dioxolo[4,5-c]pyran-7-yl)(4-(trifluoromethyl)pyrimidin-2-yl)carbamate (200 mg, 0.44 mmol) in DMF (6 mL) was added NaH (35.6 mg, 0.89 mmol, 60% wt. in mineral oil) at 0° C. Then the reaction was stirred at 0° C. for 30 min. Then methyl 2-(2-(2-(2-(tosyloxy)ethoxy)ethoxy)ethoxy)acetate (150.9 mg, 0.40 mmol) was added. The mixture was stirred at rt for 3 h. LCMS showed staring material was consumed and desire mass detected. Then the reaction was quenched with NH$_4$Cl and extracted with EA. The organic layer was dried over Na$_2$SO$_4$, filtered and concentrated and purified by silica gel with DCM/MeOH=7/3 to give crude product (60 mg). Then the crude was purified by prep-HPLC to afford 1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-2,5,8,11-tetraoxatridecan-13-oic acid (A16, 18.5 mg, 7% yield). LC-MS (ESI) found: 540 [M+H]$^+$. $^1$H NMR (400 MHz, DMSO-d$_6$): δ 8.60 (s, 1H), 7.96 (d, J=3.2 Hz, 1H), 6.99 (d, J=0.8 Hz, 1H), 4.10-4.17 (m, 3H), 3.50-3.80 (m, 17H), 3.00-3.20 (m, 2H), 1.41 (s, 3H), 1.25 (s, 3H).

Preparation of A17: 2-(4-(((((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)methoxy)methyl)phenoxy)acetic acid and A19: 2-(4-(((((2R,3R,4R,5S)-3,4-dihydroxy-5-((6-(trifluoromethyl)pyrazin-2-yl)amino)tetrahydro-2H-pyran-2-yl)methoxy)methyl)phenoxy)acetic acid

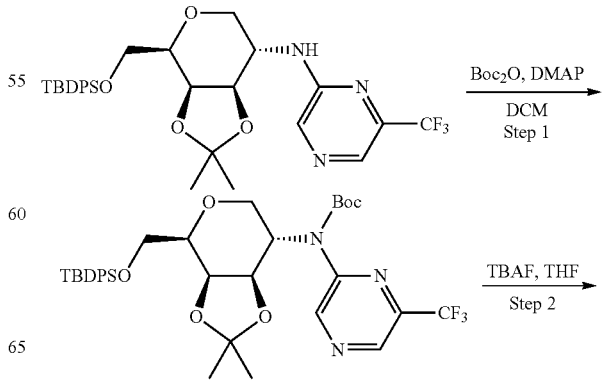

-continued

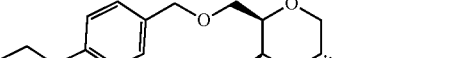

Step 1: To a solution of N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)-6-(trifluoromethyl)pyrazin-2-amine (4 g, 6.8 mmol) in DCM (40 mL) at rt were added TEA (137 mg, 13.6 mmol), DMAP (83 mg, 0.68 mmol) and Boc$_2$O (7.4 g, 34 mmol). The mixture was stirred at the room temperature overnight. The mixture was concentrated under reduced pressure to give a crude product, which was purified by flash chromatography to give tert-butyl ((3aR,4R,7S,7aR)-4-(((tert-butyldiphenylsilyl)oxy)methyl)-2,2-dimethyltetrahydro-4H-[1,3]dioxolo[4,5-c]pyran-7-yl)(6-(trifluoromethyl)pyrazin-2-yl)carbamate (4 g, 87% yield) as a colorless oil. LC-MS (ESI) found: 688 [M+H]$^+$.

Step 2: To a solution of tert-butyl ((3aR,4R,7S,7aR)-4-(((tert-butyldiphenylsilyl)oxy)methyl)-2,2-dimethyltetrahydro-4H-[1,3]dioxolo[4,5-c]pyran-7-yl)(6-(trifluoromethyl)pyrazin-2-yl)carbamate (4 g, 5.8 mmol) in THF (100 mL) was added TBAF (11.6 mL, 1 M in THF). The reaction was stirred at room temperature for 3 h. The mixture was concentrated under reduced pressure to give a crude product, which was purified by flash chromatography to tert-butyl ((3aR,4R,7S,7aR)-4-(hydroxymethyl)-2,2-dimethyltetrahydro-4H-[1,3]dioxolo[4,5-c]pyran-7-yl)(6-(trifluoromethyl)pyrazin-2-yl)carbamate (2 g, 77% yield) as white solid. LC-MS (ESI) found: 450 [M+H]$^+$.

Step 3: To a solution of tert-butyl ((3aR,4R,7S,7aR)-4-(hydroxymethyl)-2,2-dimethyltetrahydro-4H-[1,3]dioxolo[4,5-c]pyran-7-yl)(6-(trifluoromethyl)pyrazin-2-yl)carbamate (100 mg, 0.22 mmol) in DMF (10 mL) was added NaH (18 mg, 0.45 mmol, 60% wt. in mineral oil) at 0° C. After 1 h, methyl 2-(4-(bromomethyl)phenoxy)acetate (75 mg, 0.29 mmol) was added to the solution, and the mixture was stirred at rt for 12 h. The mixture was quenched with H$_2$O and extracted with EA. The combined organic layer was washed with brine, dried over anhydrous Na$_2$SO$_4$, filtered. The filtrate was concentrated and purified by C18 to afford 2-(4-(((((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)methoxy)methyl)phenoxy)acetic acid (A17, 15 mg, 13% yield) as solid. LC-MS (ESI) found: 514 [M+H]$^+$. $^1$H NMR (400 MHz, CD$_3$OD): δ 8.10 (s, 1H), 7.99 (s, 1H), 7.28 (d, J=8.5 Hz, 2H), 6.92 (d, J=8.6 Hz, 2H), 5.09 (s, 1H), 4.81 (d, J=17.6 Hz, 1H), 4.68 (t, J=11.0 Hz, 1H), 4.61-4.48 (m, 3H), 4.30 (d, J=5.0 Hz, 1H), 3.91-3.70 (m, 4H), 3.60 (t, J=11.3 Hz, 1H), 1.55 (s, 3H), 1.32 (s, 3H). $^{19}$F NMR (377 MHz, CD$_3$OD): δ −69.91.

Step 4: To a solution of 2-(4-(((((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)methoxy)methyl)phenoxy)acetic acid (9.2 mg, 0.02 mmol) in THF (2 mL) was added HCl (0.1 mL, 2 N). The mixture was stirred at rt overnight. The mixture was concentrated and purified by C18 to afford 2-(4-(((((2R,3R,4R,5S)-3,4-dihydroxy-5-((6-(trifluoromethyl)pyrazin-2-yl)amino)tetrahydro-2H-pyran-2-yl)methoxy)methyl)phenoxy)acetic acid (A19, 5 mg, 57% yield) as a white solid. LC-MS (ESI) found: 474 [M+H]$^+$. $^1$H NMR (400 MHz, CD$_3$OD): δ 8.24 (s, 1H), 8.10 (s, 1H), 7.24 (d, J=8.2 Hz, 2H), 6.89 (d, J=8.3 Hz, 2H), 4.93 (d, J=16.3 Hz, 1H), 4.68 (d, J=16.0 Hz, 1H), 4.52 (s, 2H), 4.20 (s, 1H), 3.97 (d, J=2.6 Hz, 1H), 3.89 (dd, J=10.8, 5.0 Hz, 1H), 3.73 (dd, J=11.4, 7.1 Hz, 1H), 3.66 (dd, J=11.4, 4.9 Hz, 1H), 3.45-3.41 (m, 1H). $^{19}$F NMR (377 MHz, CD$_3$OD): δ −70.04.

Preparation of A20: 1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-20-(1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid

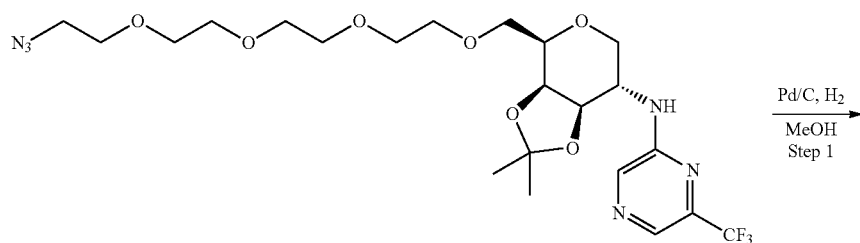

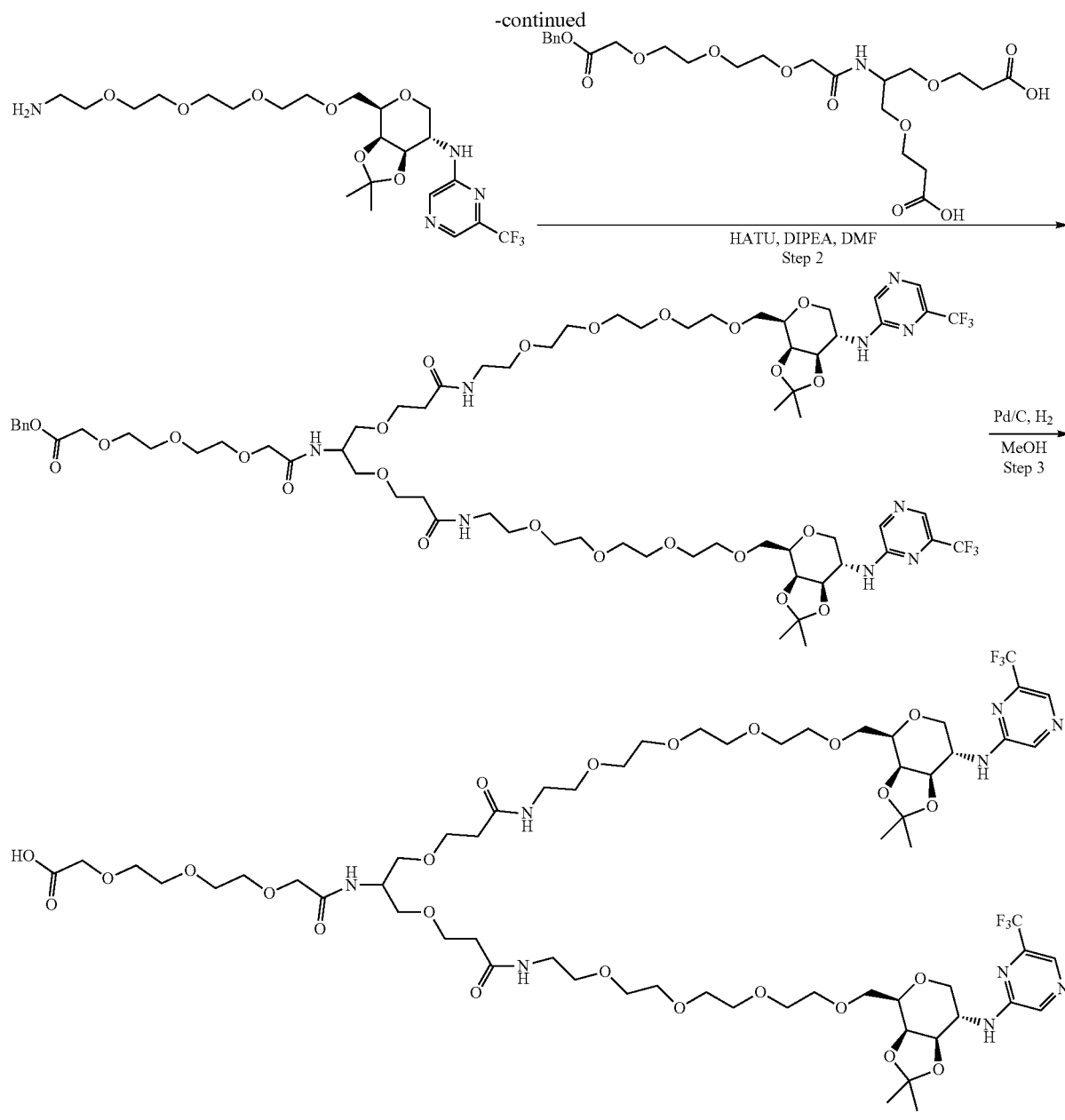

A20

Step 1: To a solution of N-((3aR,4R,7S,7aR)-4-(13-azido-2,5,8,11-tetraoxatridecyl)-2,2-dimethyltetrahydro-4H-[1,3]dioxolo[4,5-c]pyran-7-yl)-6-(trifluoromethyl)pyrazin-2-amine (230 mg, 0.42 mmol) in MeOH (10 mL) was added Pd/C 10% (20 mg, 10% wt., 60% wet) at rt under a $H_2$ balloon. The reaction was stirred at RT for 0.5 h. The resulting mixture was filtered and concentrated in vacuo. The crude product was used for next step without further purification. LC-MS (ESI) found: 525 [M+H]$^+$.

Step 2: To a solution of 15-((2-carboxyethoxy)methyl)-3,13-dioxo-1-phenyl-2,5,8,11,17-pentaoxa-14-azaicosan-20-oic acid (75 mg, 0.14 mmol), DIPEA (0.1 mL, 0.57 mmol) and HATU (118.5 mg, 0.31 mmol) in DMF (5 mL) was stirred at rt for 30 min. N-((3aR,4R,7S,7aR)-4-(13-amino-2,5,8,11-tetraoxatridecyl)-2,2-dimethyltetrahydro-4H-[1,3]dioxolo[4,5-c]pyran-7-yl)-6-(trifluoromethyl)pyrazin-2-amine (163.4 mg, 0.31 mmol) was added at rt. The reaction was stirred overnight. The resulting mixture was concentrated in vacuo. The crude product was purified by flash chromatography (silica gel, 0~10% MeOH in DCM) to give benzyl 1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-20-(1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (120 mg, 55% yield) as a colorless oil. LC-MS (ESI) found: 1543 [M+H]$^+$.

Step 3: To a solution of benzyl 1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-20-(1-((3aR,4R, 7S,7aR)-2,2-dimethyl-7-((6-(trifluoromethyl)pyrazin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (120 mg, 0.08 mmol) in MeOH (5 mL) was added Pd/C (12 mg, 10% wt., 60% wet) at rt under a $H_2$ balloon. The reaction was stirred at rt for 2 h. The resulting mixture was filtered and concentrated in vacuo. The crude product was purified by flash chromatography (silica gel, 0-15% MeOH in DCM) to afford 1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-20-(1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid (A20, 50 mg, 44% yield) as a white solid. LC-MS (ESI) found: 1453 [M+H]$^+$. $^1$H NMR (400 MHz, CD$_3$OD): δ 8.10 (s, 2H), 8.02 (s, 2H), 4.33-4.25 (m, 4H), 4.22-4.18 (m, 1H), 4.14 (dd, J=8.8, 5.0 Hz, 2H), 4.01 (s, 2H), 3.95 (dd, J=12.2, 6.5 Hz, 6H), 3.75-3.62 (m, 40H), 3.57-3.51 (m, 8H), 3.38 (t, J=5.5 Hz, 4H), 3.14 (t, J=11.2 Hz, 2H), 2.46 (t, J=6.1 Hz, 4H), 1.50 (s, 6H), 1.33 (s, 6H). $^{19}$F NMR (377 MHz, CD$_3$OD): δ −70.31 (s).

Preparation of A21: (2R,3R,4R,5S)-2-(13-azido-2,5,8,11-tetraoxatridecyl)-5-((6-(trifluoromethyl)pyrazin-2-yl)amino)tetrahydro-2H-pyran-3,4-diol

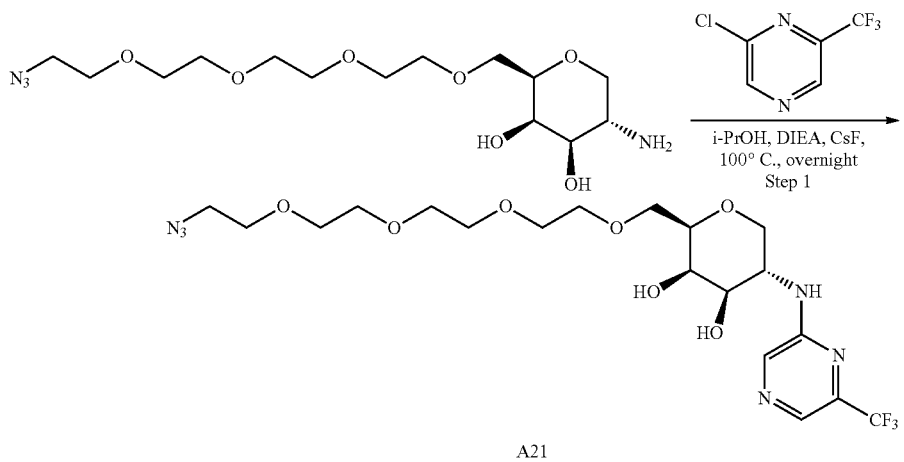

A21

Step 1: To a solution of (2R,3R,4R,5S)-5-amino-2-(13-azido-2,5,8,11-tetraoxatridecyl)tetrahydro-2H-pyran-3,4-diol (200 mg, 0.55 mmol) and DIPEA (209 mg, 1.65 mmol) in dry DMF (20 mL) was added 2-chloro-6-(trifluoromethyl)pyrazine (199 mg, 1.1 mmol) and CsF (166 mg, 1.1 mmol) at rt under N$_2$ atmosphere. After the addition was complete, the reaction was stirred at 100° C. overnight. On consumption of starting material (TLC monitoring), the reaction vessel was cooled to rt. The mixture was concentrated under reduced pressure. The crude product was purified by flash chromatography (silica gel, 0-10% MeOH in DCM) to afford (2R,3R,4R,5S)-2-(13-azido-2,5,8,11-tetraoxatridecyl)-5-((6-(trifluoromethyl)pyrazin-2-yl)amino)tetrahydro-2H-pyran-3,4-diol (A21, 150 mg, 54% yield) as white solid. LC-MS (ESI) found: 511 [M+H]$^+$. $^1$H NMR (400 MHz, CD$_3$OD): δ 8.11 (s, 1H), 8.00 (s, 1H), 4.33 (td, J=10.5, 5.1 Hz, 1H), 4.12 (dd, J=11.0, 5.2 Hz, 1H), 3.92 (d, J=2.6 Hz, 1H), 3.74-3.53 (m, 19H), 3.36 (dd, J=9.4, 4.6 Hz, 2H), 3.12 (t, J=10.8 Hz, 1H).

Preparation of A22: 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27-heptaoxa-14,21-diazanonacosan-29-oic acid

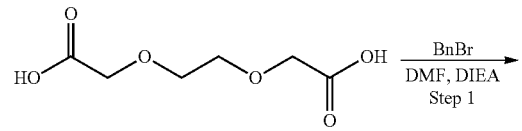

-continued
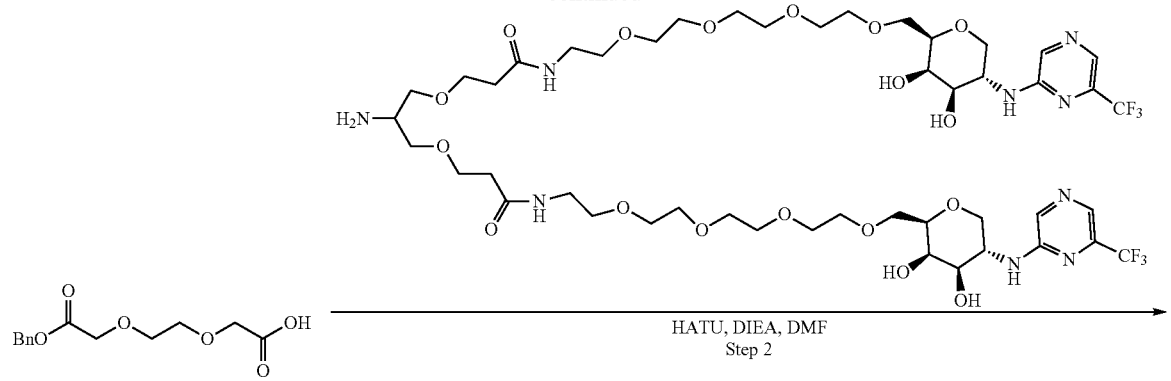
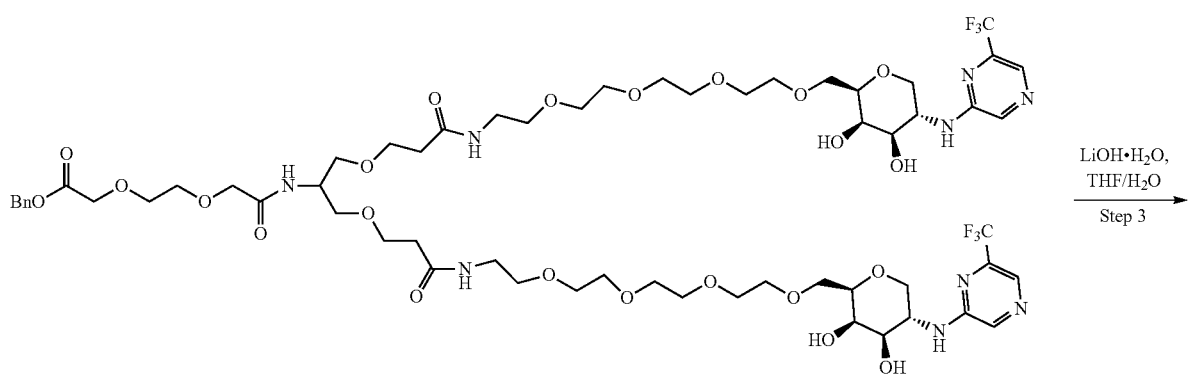
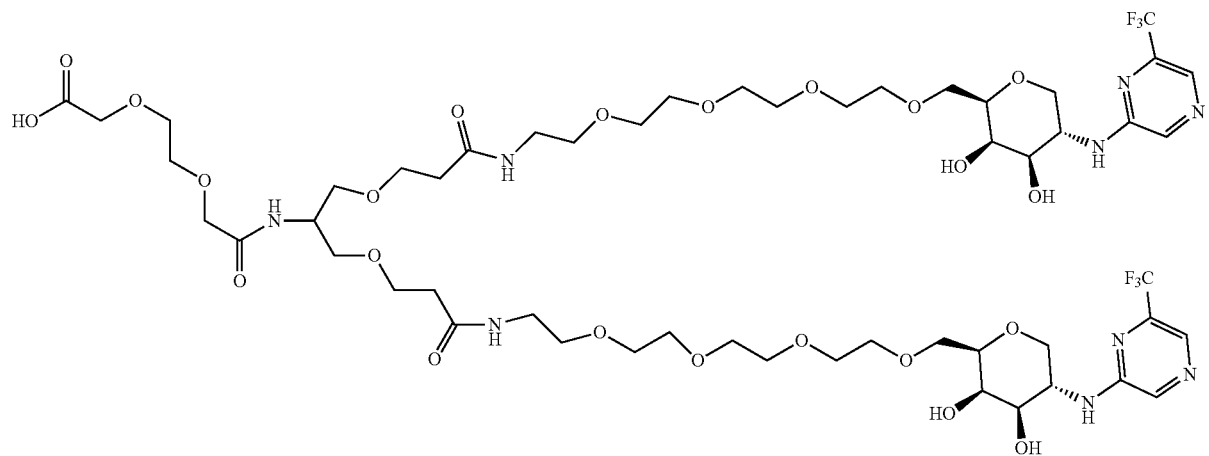
A22
Step 1: To a solution of 2,2'-(ethane-1,2-diylbis(oxy)) diacetic acid (1.0 g, 5.62 mmol) and TEA (1.0 g, 9.9 mmol) were dissolved in DMF (10 mL) and the mixture was cooled to 0° C. To this solution, benzyl bromide (860 mg, 5.03 mmol) dissolved in DMF (10 mL) was added. Then the mixture was stirred at RT for 16 h. The solvent was removed, the residue was dissolved in 1 M HCl and extracted by EA, dried over by Na₂SO₄. The residue was purified by silica gel (PE:EA=1:2) to give 2-(2-(2-(benzyloxy)-2-oxoethoxy) ethoxy)acetic acid (350 mg, 26% yield). LC-MS (ESI) found: 269 [M+H]⁺.

Step 2: To a solution of 2-(2-(2-(benzyloxy)-2-oxoethoxy) ethoxy)acetic acid (5.8 mg, 0.02 mmol) in DMF (1 mL) was added HATU (12.3 mg, 0.03 mmol) and DIPEA (39.42 mg, 0.06 mmol). The mixture was stirred at 0° C. for 0.5 h. Then 3,3'-((2-aminopropane-1,3-diyl)bis(oxy))bis(N-(1-((2R,3R, 4R,5S)-3,4-dihydroxy-5-((6-(trifluoromethyl)pyrazin-2-yl) amino)tetrahydro-2H-pyran-2-yl)-2,5,8,11-tetraoxatridecan-13-yl)propanamide) (21.2 mg, 0.02 mmol) in DMF (0.5 mL) was added. The mixture was stirred at rt for 16 h. The reaction mixture was directly purified by prep-HPLC to afford benzyl 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27-heptaoxa-14,21-diazanonacosan-29-oate (10 mg, 39% yield). LC-MS (ESI) found: 710 [M+2H]²⁺.

Step 3: To a solution of benzyl 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27-heptaoxa-14,21-diazanonacosan-29-oate (15 mg, 0.01 mmol) in THF/H₂O (3:1, 4 mL) was added LiOH·H₂O (3 mg, 0.07 mmol). Then the mixture was stirred at rt for 2 h. The solvent was removed, and the residue was purified by prep-HPLC to afford 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl) pyrazin-2-yl)amino)tetrahydro-2H-pyran-2-yl)-15-oxo-2,5, 8,11,18-pentaoxa-14-azanonadecan-19-yl)-15,22-dioxo-2,5, 8,11,18,24,27-heptaoxa-14,21-diazanonacosan-29-oic acid (A22, 7.2 mg, 51% yield). LC-MS (ESI) found: 665 [M+2H]²⁺. ¹H NMR (400 MHz, CDCl₃): δ 8.17 (s, 2H), 8.00 (s, 2H), 7.61 (s, 2H), 6.76 (s, 2H), 4.28 (d, J=10.4 Hz, 2H), 4.11 (d, J=52.9 Hz, 9H), 3.81-3.51 (m, 43H), 3.44 (d, J=26.8 Hz, 8H), 3.10 (t, J=10.5 Hz, 2H), 2.43 (s, 2H), 2.01 (s, 1H), 1.26 (s, 2H).

Preparation of A23: 1-((2R,3R,4R,5S)-3,4-dihydroxy-5-((4-(trifluoromethyl)pyrimidin-2-yl)amino) tetrahydro-2H-pyran-2-yl)-20-(1-((2R,3R,4R,5S)-3, 4-dihydroxy-5-((4-(trifluoromethyl)pyrimidin-2-yl) amino)tetrahydro-2H-pyran-2-yl)-15-oxo-2,5,8,11, 18-pentaoxa-14-azanonadecan-19-yl)-15,22-dioxo-2, 5,8,11,18,24,27,30-octaoxa-14,21-diazadotriacontan-32-oic acid

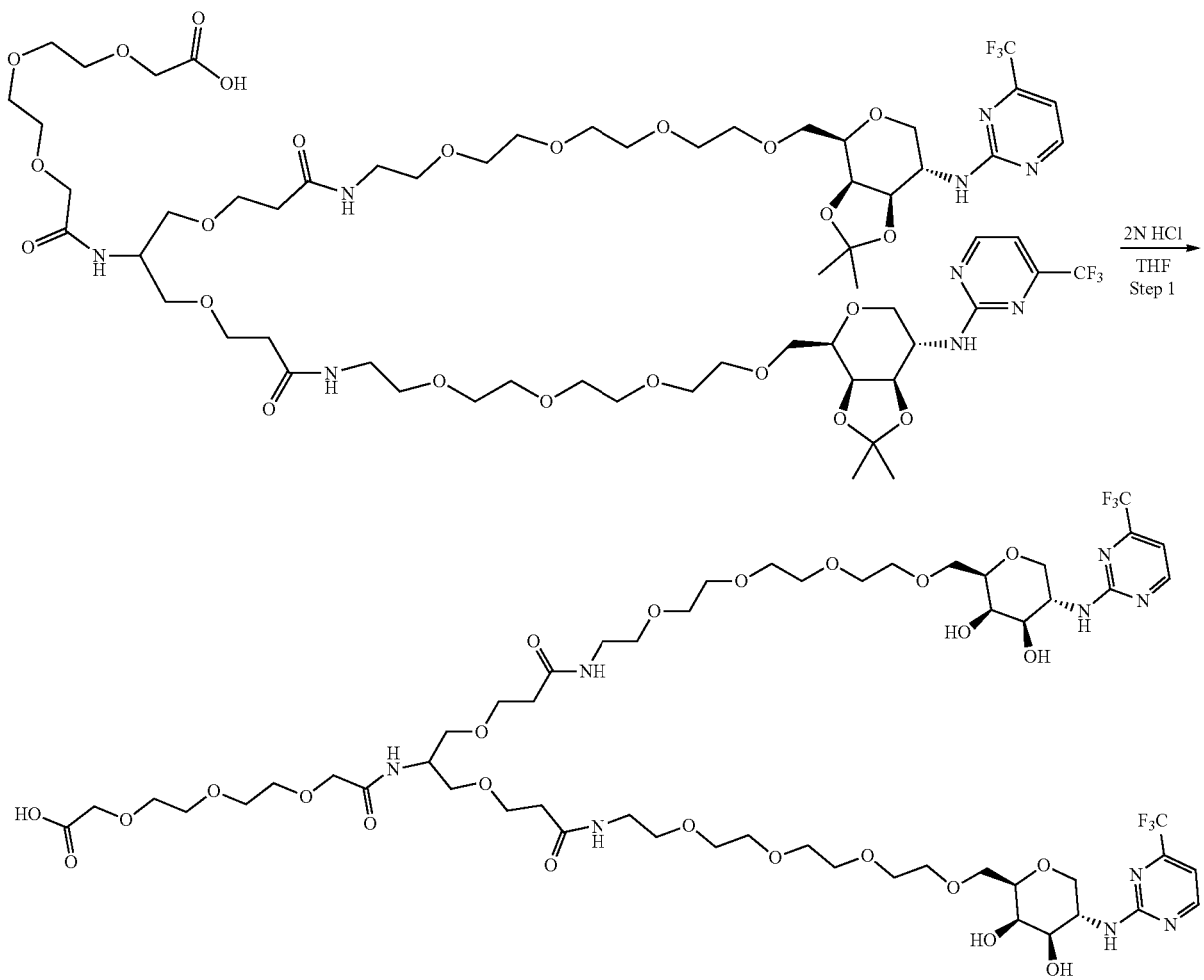

A23

Step 1: To a solution of 1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid (110 mg, 0.08 mmol) in THF (3 mL) was added HCl (1 mL, 2 N in H$_2$O). The reaction was stirred at rt for 3 h. The crude product was purified by prep-HPLC to afford 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid (A23, 53 mg, 51% yield) as a white solid. LC-MS (ESI) found: 1373 [M+H]$^+$. $^1$H NMR (400 MHz, CD$_3$OD): δ 8.51 (d, J=4.5 Hz, 2H), 6.90 (d, J=4.9 Hz, 2H), 4.36 (d, J=4.9 Hz, 2H), 4.23-4.18 (m, 1H), 4.14-4.06 (m, 4H), 4.01 (s, 2H), 3.92 (d, J=2.5 Hz, 2H), 3.74-3.60 (m, 44H), 3.57-3.50 (m, 8H), 3.38 (t, J=5.4 Hz, 4H), 3.17 (t, J=10.9 Hz, 2H), 2.46 (t, J=6.1 Hz, 4H). $^{19}$F NMR (377 MHz, CD$_3$OD): δ −72.30 (s).

Preparation of A24: 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27-heptaoxa-14,21-diazanonacosan-29-oic acid

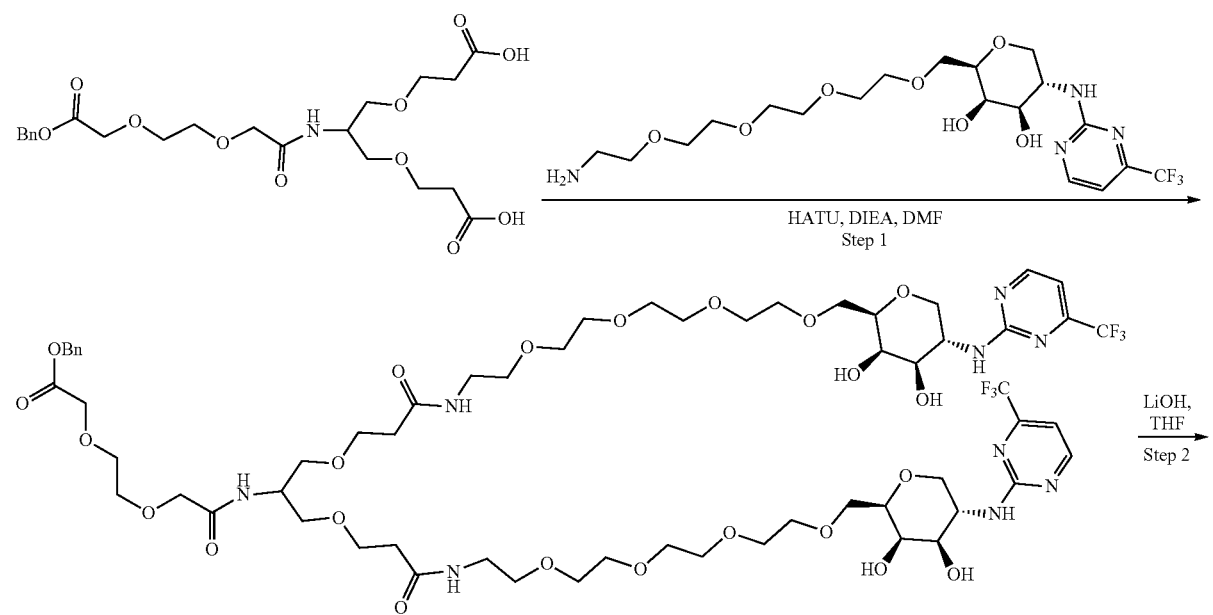

A24

Step 1: To a solution of 12-((2-carboxyethoxy)methyl)-3,10-dioxo-1-phenyl-2,5,8,14-tetraoxa-11-azaheptadecan-17-oic acid (200 mg, 0.41 mmol) and HATU (467 mg, 1.23 mmol) in DMF (20 mL) was added DIPEA (209 mg, 1.65 mmol) and (2R,3R,4R,5S)-2-(13-amino-2,5,8,11-tetraoxatridecyl)-5-((4-(trifluoromethyl)pyrimidin-2-yl)amino)tetrahydro-2H-pyran-3,4-diol (440 mg, 0.9 mmol) at rt. The reaction mixture was stirred at RT overnight. The resulting mixture was separated and concentrated in vacuo. The crude product was purified by flash chromatography (C18, 0~60%, MeOH in H₂O) to give benzyl 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27-heptaoxa-14,21-diazanonacosan-29-oate (400 mg, 68% yield) as white solid. LC-MS (ESI) found: 1419 [M+H]⁺.

Step 2: To a solution of benzyl 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27-heptaoxa-14,21-diazanonacosan-29-oate (400 mg, 0.28 mmol) in THF (10 mL) was added LiOH·H₂O (14 mg, 0.56 mmol) at RT. The reaction mixture was stirred at RT for 3 h. The resulting mixture was separated and concentrated in vacuo. The crude product was purified by flash chromatography (C18, 0~40%, MeOH in H₂O) to afford 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27-heptaoxa-14,21-diazanonacosan-29-oic acid (A24, 300 mg, 80% yield) as white solid. LC-MS (ESI) found: 1329 [M+H]⁺. ¹H NMR (400 MHz, CD₃OD): δ 8.11 (s, 2H), 8.00 (s, 2H), 4.33 (td, J=10.8, 5.4 Hz, 2H), 4.19 (dd, J=14.8, 9.5 Hz, 1H), 4.16-4.07 (m, 4H), 4.01 (s, 2H), 3.92 (d, J=2.3 Hz, 2H), 3.79-3.45 (m, 48H), 3.37 (t, J=5.4 Hz, 4H), 3.12 (t, J=10.8 Hz, 2H), 2.45 (t, J=6.1 Hz, 4H).

Preparation of A25: 1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-oic acid

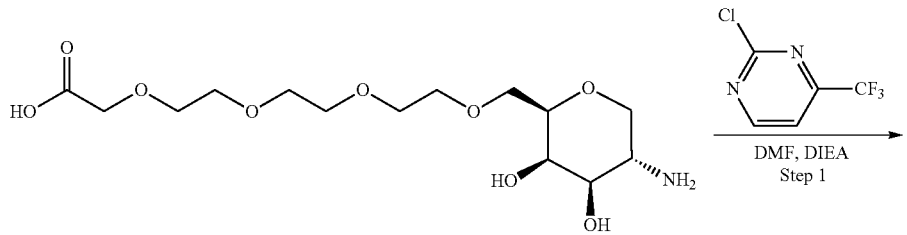

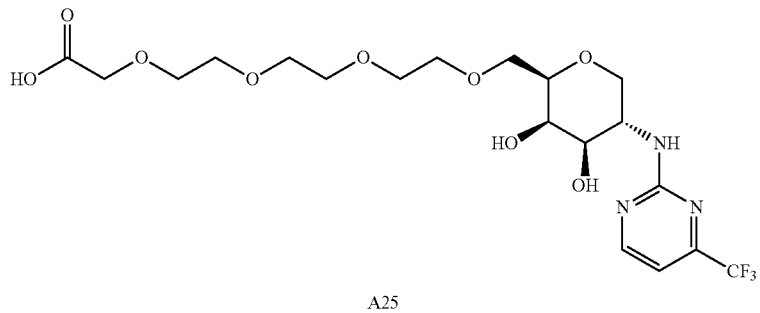

A25

Step 1: To a solution of 1-((2R,3R,4R,5S)-5-amino-3,4-dihydroxytetrahydro-2H-pyran-2-yl)-2,5,8,11-tetraoxatridecan-13-oic acid (100 mg, 0.28 mmol) in DMF (5 mL) was added 2-chloro-4-(trifluoromethyl)pyrimidine (52 mg, 0.28 mmol) and DIEA (0.14 mL, 0.85 mmol) at rt. The reaction was stirred at rt for 18 h. The reaction was concentrated directly and the residue was purified by prep-HPLC to afford 1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-oic acid (A25, 10 mg, 7% yield) as colorless oil. LC-MS (ESI) found: 450 [M+H]⁺. ¹H NMR (400 MHz, CD₃OD): δ 8.51 (d, J=4.8 Hz, 1H), 6.89 (d, J=4.8 Hz, 1H), 4.31-4.41 (m, 1H), 4.07-4.10 (m, 3H), 3.91 (d, J=2.4 Hz, 1H), 3.55-3.75 (m, 16H), 3.17 (t, J=11.2, 1H).

Preparation of A26: 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid
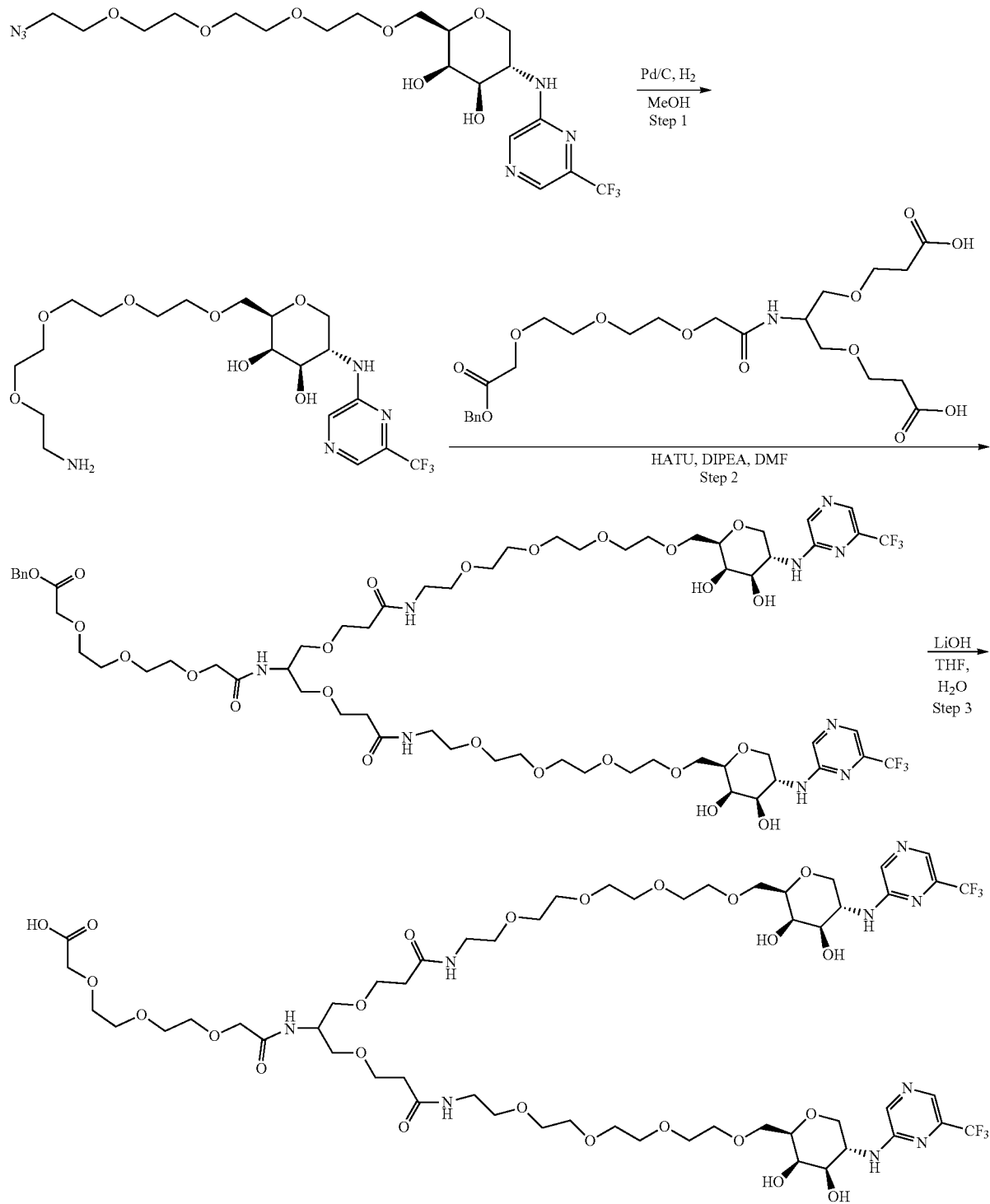
A26

Step 1: To a solution of (2R,3R,4R,5S)-2-(13-azido-2,5,8,11-tetraoxatridecyl)-5-((6-(trifluoromethyl)pyrazin-2-yl)amino)tetrahydro-2H-pyran-3,4-diol (300 mg, 0.59 mmol) in MeOH (10 mL) was added Pd/C (30 mg, 10% wt., 60% wet) at rt under a H$_2$ balloon. The reaction was stirred at RT for 0.5 h. The resulting mixture was filtered and concentrated in vacuo. The crude product was used for next step without further purification. LC-MS (ESI) found: 485 [M+H]$^+$.

Step 2: To a solution of 15-((2-carboxyethoxy)methyl)-3,13-dioxo-1-phenyl-2,5,8,11,17-pentaoxa-14-azaicosan-20-oic acid (125 mg, 0.24 mmol), DIPEA (0.16 mL, 0.94 mmol) and HATU (197 mg, 0.52 mmol) in DMF (10 mL) was stirred at rt for 30 min. (2R,3R,4R,5S)-2-(13-amino-2,5,8,11-tetraoxatridecyl)-5-((6-(trifluoromethyl)pyrazin-2-yl)amino)tetrahydro-2H-pyran-3,4-diol (296 mg, 0.52 mmol) was added at rt. The reaction was stirred overnight. The resulting mixture was concentrated in vacuo. The crude product was purified by prep-HPLC to give benzyl 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (250 mg, 0.17 mmol) as a colorless oil. LC-MS (ESI) found: 1463 [M+H]$^+$.

Step 3: To a solution of benzyl 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (250 mg, 0.17 mmol) in THF (5 mL) and H$_2$O (1.5 mL) was added LiOH (21.5 mg, 0.51 mmol) at rt. The reaction was stirred at RT for 2 h. The reaction was adjusted to acidic with 2 N HCl. The crude product was purified by prep-HPLC to afford 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid (A26, 160 mg, 68% yield) as a white solid. LC-MS (ESI) found: 1373 [M+H]$^+$. $^1$H NMR (400 MHz, CD$_3$OD): δ: 8.12 (s, 2H), 8.00 (s, 2H), 4.34 (td, J=10.6, 5.1 Hz, 2H), 4.23-4.18 (m, 1H), 4.14-4.09 (m, 4H), 4.00 (s, 2H), 3.93 (d, J=2.4 Hz, 2H), 3.73-3.61 (m, 44H), 3.57-3.50 (m, 8H), 3.38 (t, J=5.4 Hz, 4H), 3.12 (t, J=10.8 Hz, 2H), 2.45 (t, J=6.1 Hz, 4H). $^{19}$F NMR (377 MHz, CD$_3$OD): δ −70.26 (s).

Preparation of A27: 1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-oic acid

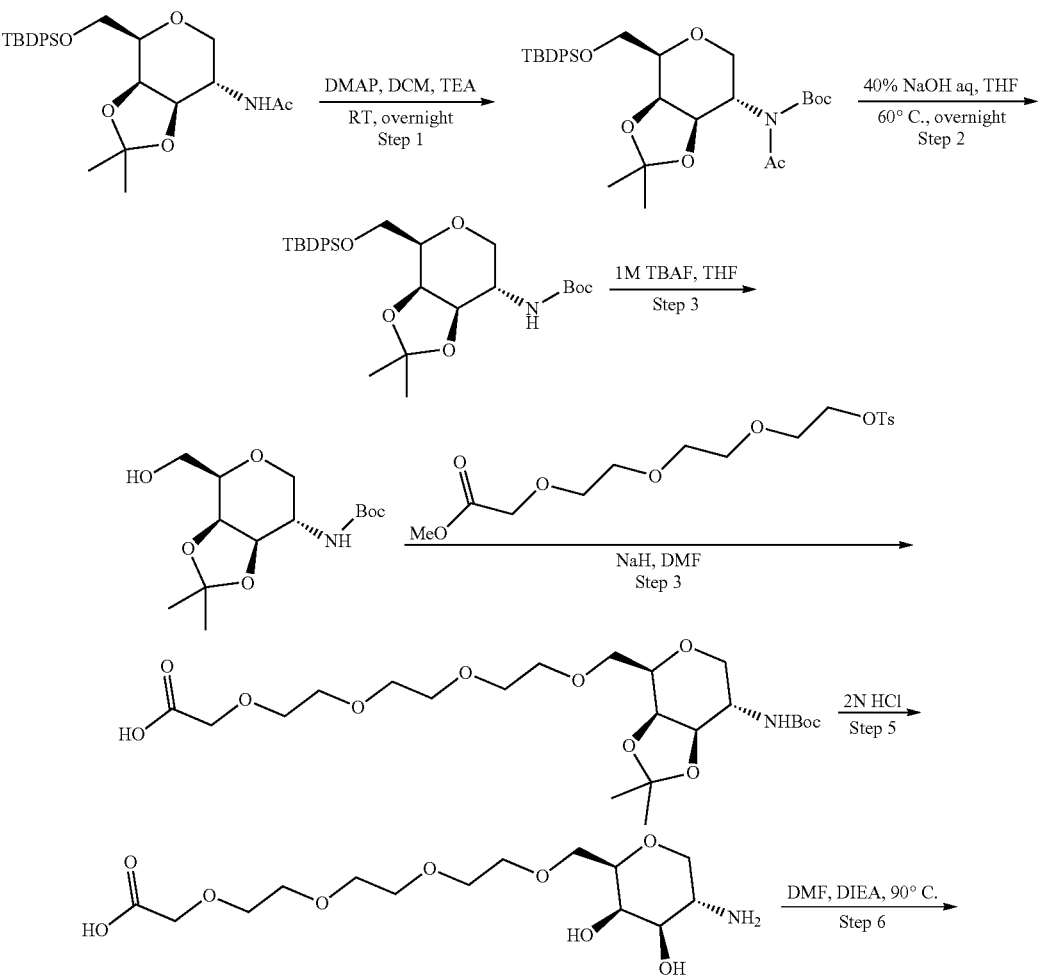

-continued

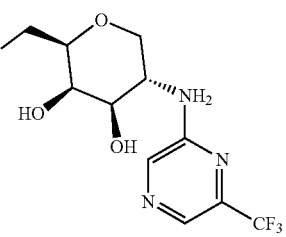

A27

Step 1: To a solution of N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)acetamide (7 g, 14.53 mmol) in DCM (70 mL) at rt was added TEA (2.06 mL, 14.83 mmol), DMAP (0.12 g, 0.98 mmol), and di-tert-butyl dicarbonate (3.17 mL, 14.83 mmol). The mixture was stirred at the room temperature overnight. On consumption of starting material (LCMS monitoring), the mixture was concentrated under reduced pressure to give a crude product, which was purified by flash chromatography to give tert-butyl acetyl((3aR,4R,7S,7aR)-4-(((tert-butyldiphenylsilyl)oxy)methyl)-2,2-dimethyltetrahydro-4H-[1,3]dioxolo[4,5-c]pyran-7-yl)carbamate (7 g, 83% yield) as a colorless oil. LC-MS (ESI) found: 584 [M+H]$^+$.

Step 2: To a solution of tert-butyl acetyl((3aR,4R,7S,7aR)-4-(((tert-butyldiphenylsilyl)oxy)methyl)-2,2-dimethyltetrahydro-4H-[1,3]dioxolo[4,5-c]pyran-7-yl)carbamate (7 g, 11.9 mmol) in THF (70 mL) at rt was added NaOH (40%, 10 mL, 59.9 mmol). The mixture was stirred at the room temperature for overnight. On consumption of starting material (LCMS monitoring), water (20 mL) was slowly added. The mixture was diluted with ethyl acetate (100 mL) and wash with water (20 mL×3). The organic layer was dried over sodium sulfate, filtered, concentrated under reduced pressure to give a crude product, which was purified by flash chromatography to give tert-butyl ((3aR,4R,7S,7aR)-4-(((tert-butyldiphenylsilyl)oxy)methyl)-2,2-dimethyltetrahydro-4H-[1,3]dioxolo[4,5-c]pyran-7-yl)carbamate (6 g, 93% yield) as a colorless oil. LC-MS (ESI) found: 542 [M+H]$^+$.

Step 3: To a solution of tert-butyl ((3aR,4R,7S,7aR)-4-(((tert-butyldiphenylsilyl)oxy)methyl)-2,2-dimethyltetrahydro-4H-[1,3]dioxolo[4,5-c]pyran-7-yl)carbamate (6 g, 11 mmol) in THF (100 mL) was added TBAF solution (22 mL, 1 M in THF). The reaction was stirred at room temperature for 3 h. The mixture was concentrated under reduced pressure to give a crude product, which was purified by flash chromatography (silica gel, 0-10% DCM in MeOH) to give tert-butyl ((3aR,4R,7S,7aR)-4-(hydroxymethyl)-2,2-dimethyltetrahydro-4H-[1,3]dioxolo[4,5-c]pyran-7-yl)carbamate (2.5 g, 76% yield) as white solid. LC-MS (ESI) found: 304 [M+H]$^+$.

Step 4: To a solution of tert-butyl ((3aR,4R,7S,7aR)-4-(hydroxymethyl)-2,2-dimethyltetrahydro-4H-[1,3]dioxolo[4,5-c]pyran-7-yl)carbamate (2.5 g, 8.2 mmol) in DMF (50 mL) at 0° C. was added NaH (0.47 g, 60% wt. in mineral oil, 12.3 mmol) and methyl 2-(2-(2-(2-(tosyloxy)ethoxy)ethoxy)ethoxy)acetate (2.6 g, 7.38 mmol). The mixture was stirred at the room temperature overnight. On consumption of starting material (LCMS monitoring), the reaction vessel was again cooled to 0° C., water (10 mL) was slowly added and the reaction mixture stirred for 15 min. The mixture was diluted with ethyl acetate (100 mL) and wash with water (20 mL×3). The organic layer was dried over sodium sulfate, concentrated under reduced pressure to give a crude product, which was purified by flash chromatography to give 1-((3aR,4R,7S,7aR)-7-((tert-butoxycarbonyl)amino)-2,2-dimethyltetrahydro-4H-[1,3]dioxolo[4,5-c]pyran-4-yl)-2,5,8,11-tetraoxatridecan-13-oic acid (2.0 g, 51%) as a colorless oil. LC-MS (ESI) found: 494 [M+H]$^+$.

Step 5: To a solution of 1-((3aR,4R,7S,7aR)-7-((tert-butoxycarbonyl)amino)-2,2-dimethyltetrahydro-4H-[1,3]dioxolo[4,5-c]pyran-4-yl)-2,5,8,11-tetraoxatridecan-13-oic acid (2.0 g, 4.0 mmol) in THF (20 mL) at RT was added HCl solution (4 mL, 2 N in H$_2$O). The mixture was stirred at the rt for 3 h. The mixture was concentrated under reduced pressure to give crude 1-((2R,3R,4R,5S)-5-amino-3,4-dihydroxytetrahydro-2H-pyran-2-yl)-2,5,8,11-tetraoxatridecan-13-oic acid (1.0 g, 71% yield) as a colorless oil. LC-MS (ESI) found: 354 [M+H]$^+$.

Step 6: To a solution of 1-((2R,3R,4R,5S)-5-amino-3,4-dihydroxytetrahydro-2H-pyran-2-yl)-2,5,8,11-tetraoxatridecan-13-oic acid (200 mg, 0.55 mmol) and DIPEA (209 mg, 1.65 mmol) in dry DMF (10 mL) at rt under N$_2$ atmosphere was added 2,4-dichloro-6-methoxypyrimidine (199 mg, 1.1 mmol). After the addition was complete, the reaction was stirred at 100° C. overnight. On consumption of starting material (TLC monitoring), the reaction vessel was again cooled to rt. The mixture was diluted with ethyl acetate (100 mL) and wash with water (20 mL×3). The organic layer was dried over sodium sulfate, concentrated under reduced pressure to give a crude product, which was purified by flash chromatography to afford 1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-oic acid (A27, 10 mg, 3.5% yield) as a colorless oil. LC-MS (ESI) found: 500 [M+H]$^+$. $^1$H NMR (400 MHz, CD$_3$OD): δ 8.11 (s, 1H), 7.99 (s, 1H), 4.33 (td, J=10.6, 5.2 Hz, 1H), 4.17-4.06 (m, 3H), 3.92 (d, J=3.0 Hz, 1H), 3.74-3.52 (m, 16H), 3.12 (t, J=10.8 Hz, 1H).

Preparation of A28: 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24-hexaoxa-14,21-diazahexacosan-26-oic acid
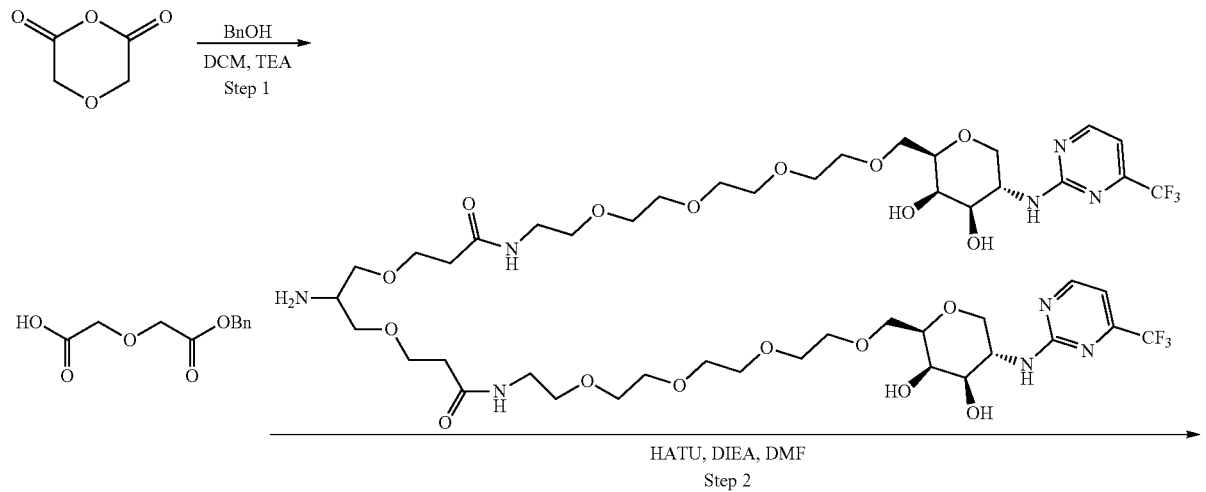
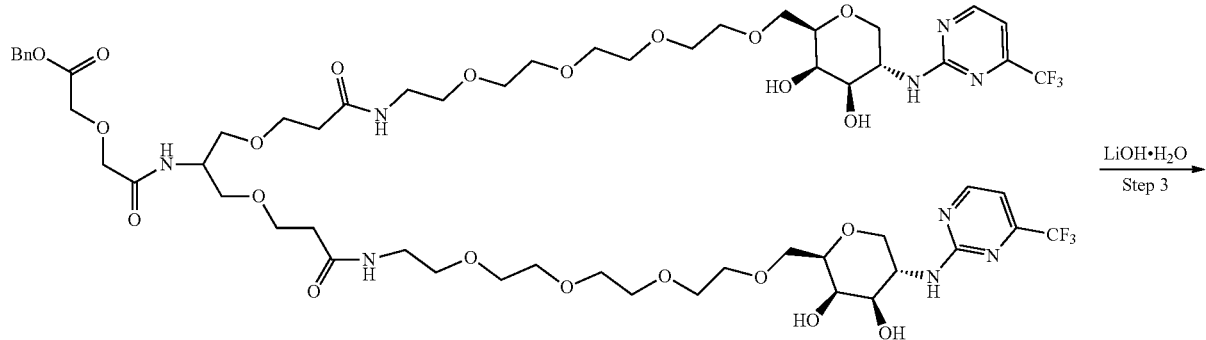
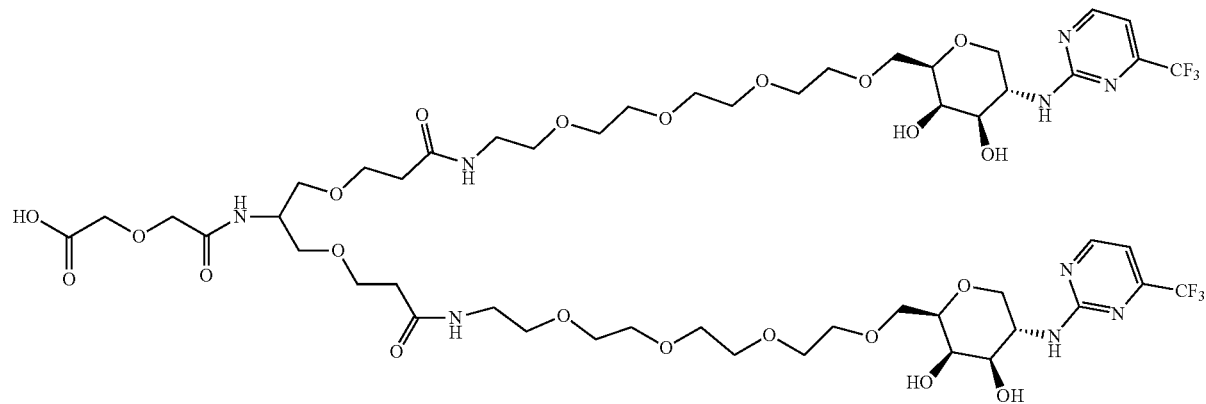
A28

Step 1: To a solution of 1,4-dioxane-2,6-dione (4.0 g, 34.5 mmol) was dissolved in DCM (40 mL) and BnOH (3.7 g, 34.5 mmol) was added, followed by TEA (3.48 g, 34.5 mmol). Then the mixture was stirred at rt for 4 h. The solvent was removed, and the residue was purified by silica gel column to give 2-(2-(benzyloxy)-2-oxoethoxy)acetic acid (3.5 g, 45% yield). LC-MS (ESI) found: 225 [M+H]+.

Step 2: To a solution of 2-(2-(benzyloxy)-2-oxoethoxy)acetic acid (42 mg, 0.19 mmol) in DMF (2 mL) was added HATU (107 mg, 0.28 mmol) and DIPEA (72 mg, 0.56 mmol). The mixture was stirred at 0° C. for 0.5 h. Then 3,3'-((2-aminopropane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (200 mg, 0.17 mmol) in DMF (0.5 mL) was added. The mixture was stirred at rt for 16 h. The reaction mixture was directly purified by C18 column to afford benzyl 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24-hexaoxa-14,21-diazahexacosan-26-oate (140 mg, 60% yield). LC-MS (ESI) found: 1375 [M+H]+.

Step 3: To a solution of benzyl 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24-hexaoxa-14,21-diazahexacosan-26-oate (140 mg, 0.10 mmol) in THF/H$_2$O (3:1, 4 mL) was added LiOH·H$_2$O (7 mg, 0.17 mmol). The mixture was stirred at rt for 2 h. The solvent was removed, and the residue was purified by prep-HPLC to afford 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24-hexaoxa-14,21-diazahexacosan-26-oic acid (A28, 65 mg, 50% yield). LC-MS (ESI) found: 1285 [M+H]+. $^1$H NMR (400 MHz, CD$_3$OD): δ 8.51 (d, J=4.5 Hz, 2H), 6.89 (d, J=4.9 Hz, 2H), 4.36 (d, J=4.9 Hz, 2H), 4.19 (d, J=9.6 Hz, 3H), 4.13-4.03 (m, 4H), 3.92 (d, J=2.8 Hz, 2H), 3.75-3.49 (m, 44H), 3.37 (t, J=5.3 Hz, 4H), 3.16 (t, J=10.9 Hz, 2H), 2.45 (t, J=6.0 Hz, 4H).

Preparation of A29: 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24-hexaoxa-14,21-diazahexacosan-26-oic acid

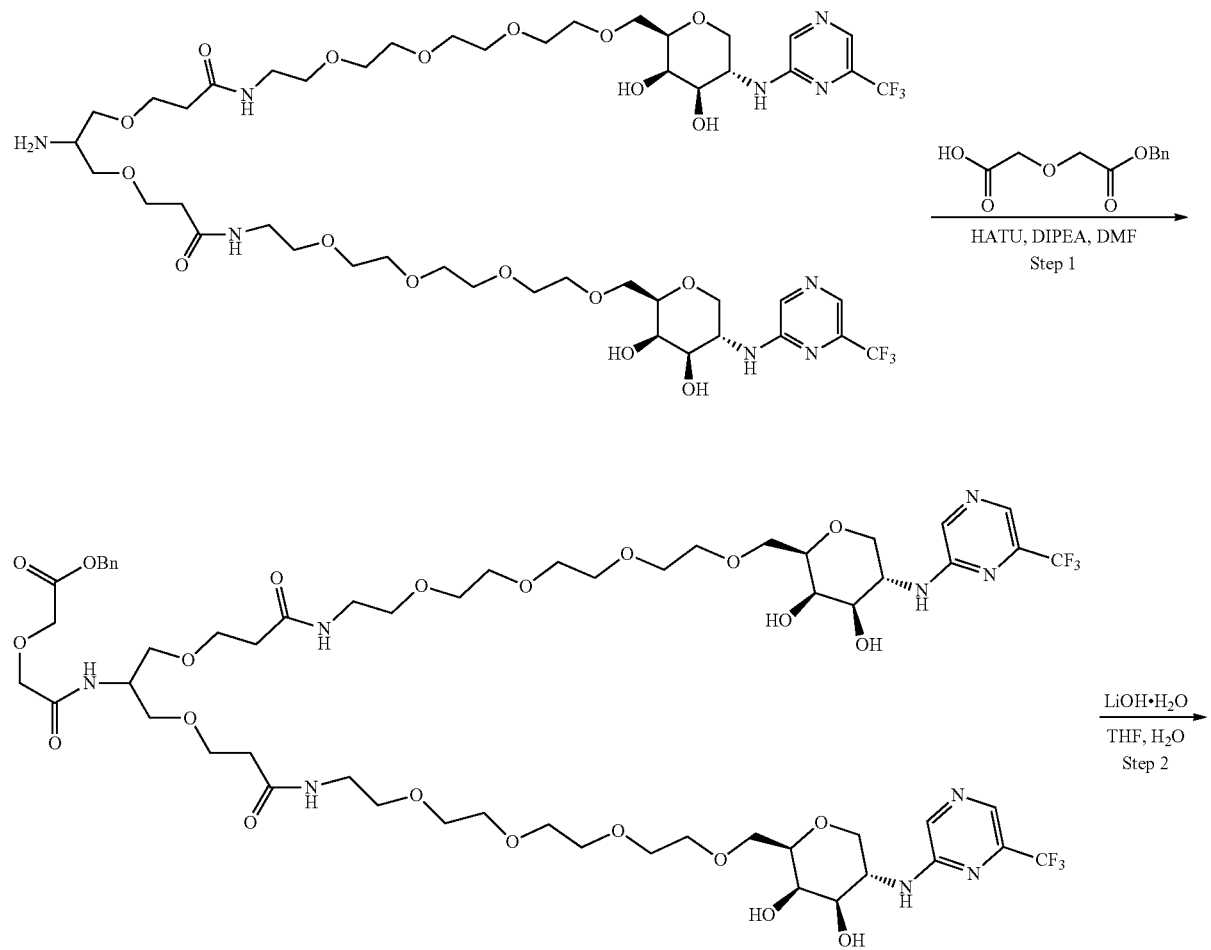

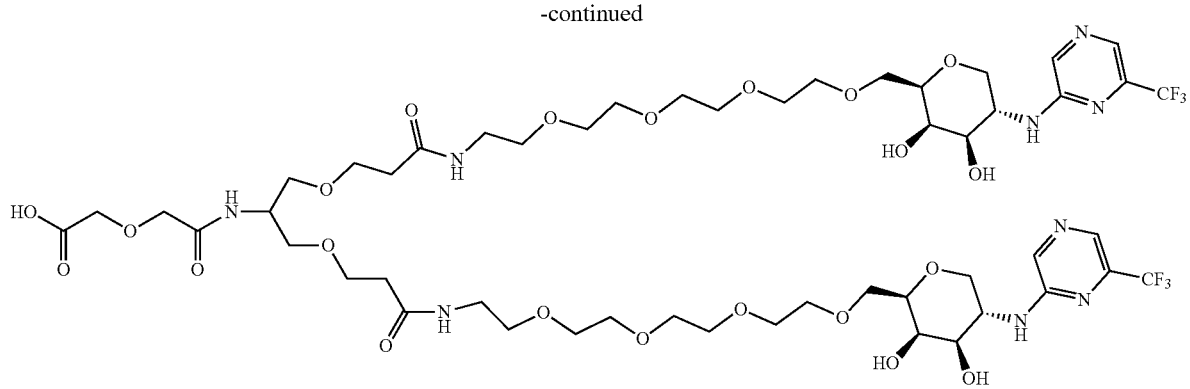

A29

Step 1: To a solution of 2-[2-(benzyloxy)-2-oxoethoxy]acetic acid (50 mg, 0.22 mmol), DIPEA (0.1 mL, 0.67 mmol) and HATU (101.8 mg, 0.27 mmol) in DMF (5 mL) was stirred at rt for 30 min. 3,3'-((2-aminopropane-1,3-diyl)bis(oxy))bis(N-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-yl)propanamide) (261 mg, 0.22 mmol) was added at rt. The reaction was stirred overnight. The resulting mixture was concentrated in vacuo. The crude product was purified by C18 column to afford benzyl 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24-hexaoxa-14,21-diazahexacosan-26-oate (160 mg, 0.12 mmol) as a colorless oil. LC-MS (ESI) found: 1375 [M+H]+.

Step 2: To a solution of benzyl 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24-hexaoxa-14,21-diazahexacosan-26-oate (160 mg, 0.12 mmol) in THF (4 mL) and H2O (2 mL) was added LiOH·H2O (15 mg, 0.35 mmol) at RT. The reaction was stirred at rt for 2 h. The reaction was adjusted to acidic with 2 N HCl. The mixture was concentrated and the crude product was purified by prep-HPLC to afford 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24-hexaoxa-14,21-diazahexacosan-26-oic acid (A29, 117 mg, 78% yield) as a white solid. LC-MS (ESI) found: 1285 [M+H]+. 1H NMR (400 MHz, CD3OD): δ 8.12 (s, 2H), 8.00 (s, 2H), 4.34 (td, J=10.6, 5.1 Hz, 2H), 4.19 (d, J=6.2 Hz, 3H), 4.14-4.08 (m, 4H), 3.93 (d, J=2.9 Hz, 2H), 3.72-3.61 (m, 36H), 3.53 (dt, J=12.2, 4.8 Hz, 8H), 3.37 (t, J=5.5 Hz, 4H), 3.12 (t, J=10.8 Hz, 2H), 2.45 (t, J=6.1 Hz, 4H). 19F NMR (377 MHz, CD3OD): δ −70.26 (s).

Preparation of A30: 2-(2-(2-((((2R,3R,4R,5S)-3,4-dihydroxy-5-((6-(trifluoromethyl)pyrazin-2-yl)amino)tetrahydro-2H-pyran-2-yl)methyl)amino)-2-oxoethoxy)ethoxy)acetic acid

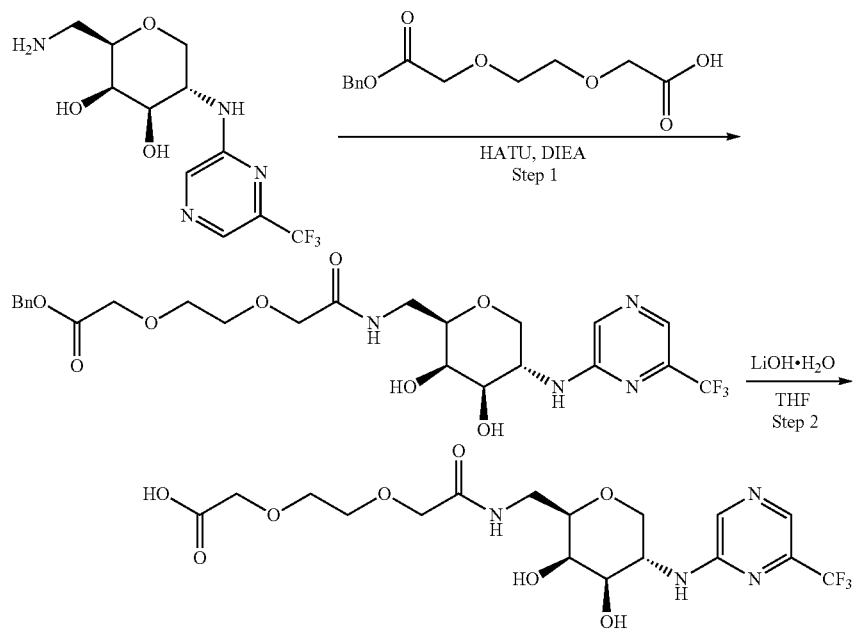

A30

Step 1: To a solution of 2-(2-(2-(benzyloxy)-2-oxoethoxy)ethoxy)acetic acid (69 mg, 0.26 mmol) in DMF (3 mL) were added HATU (148 mg, 0.39 mmol) and DIPEA (33 mg, 0.26 mmol) at rt. After stirring at rt for 20 min, (2R,3R,4R,5S)-2-(aminomethyl)-5-((6-(trifluoromethyl)pyrazin-2-yl)amino)tetrahydro-2H-pyran-3,4-diol (80 mg, 0.26 mmol) was added. The mixture was stirred at rt overnight, then concentrated. The residue was purified by flash to give benzyl 2-(2-(2-(((((2R,3R,4R,5S)-3,4-dihydroxy-5-((6-(trifluoromethyl)pyrazin-2-yl)amino)tetrahydro-2H-pyran-2-yl)methyl)amino)-2-oxoethoxy)ethoxy)acetate (100 mg, 69% yield) as yellow oil. LC-MS (ESI) found: 559 [M+H]$^+$.

Step 2: To a solution of benzyl 2-(2-(2-(((((2R,3R,4R,5S)-3,4-dihydroxy-5-((6-(trifluoromethyl)pyrazin-2-yl)amino)tetrahydro-2H-pyran-2-yl)methyl)amino)-2-oxoethoxy)ethoxy)acetate (100 mg, 0.18 mmol) in THF (2 mL) and H$_2$O (2 mL) was added LiOH·H$_2$O (15 mg, 0.36 mmol) at rt. The mixture was stirred at rt overnight, then acidified with HCl (1 N) to pH=3. The mixture was concentrated and the residue was purified by C18 column to afford 2-(2-(2-(((((2R,3R,4R,5S)-3,4-dihydroxy-5-((6-(trifluoromethyl)pyrazin-2-yl)amino)tetrahydro-2H-pyran-2-yl)methyl)amino)-2-oxoethoxy)ethoxy)acetic acid (A30, 54 mg, 66% yield) as white solid. LC-MS (ESI) found: 469 [M+H]$^+$. $^1$H NMR (400 MHz, CD$_3$OD): δ 8.10 (s, 1H), 8.00 (s, 1H), 4.32 (d, J=5.1 Hz, 1H), 4.16-4.08 (m, 3H), 4.02 (s, 2H), 3.86 (d, J=3.2 Hz, 1H), 3.75-3.70 (m, 4H), 3.64 (dd, J=10.6, 3.2 Hz, 1H), 3.55 (dd, J=14.8, 8.4 Hz, 2H), 3.43 (d, J=5.9 Hz, 1H), 3.11 (d, J=10.8 Hz, 1H).

Preparation of A31: (1,39-bis((2R,3R,4R,5S)-3,4-dihydroxy-5-((6-(trifluoromethyl)pyrazin-2-yl)amino)tetrahydro-2H-pyran-2-yl)-15,25-dioxo-2,5,8,11,18,22,29,32,35,38-decaoxa-14,26-diazanonatriacontan-20-yl)glycine

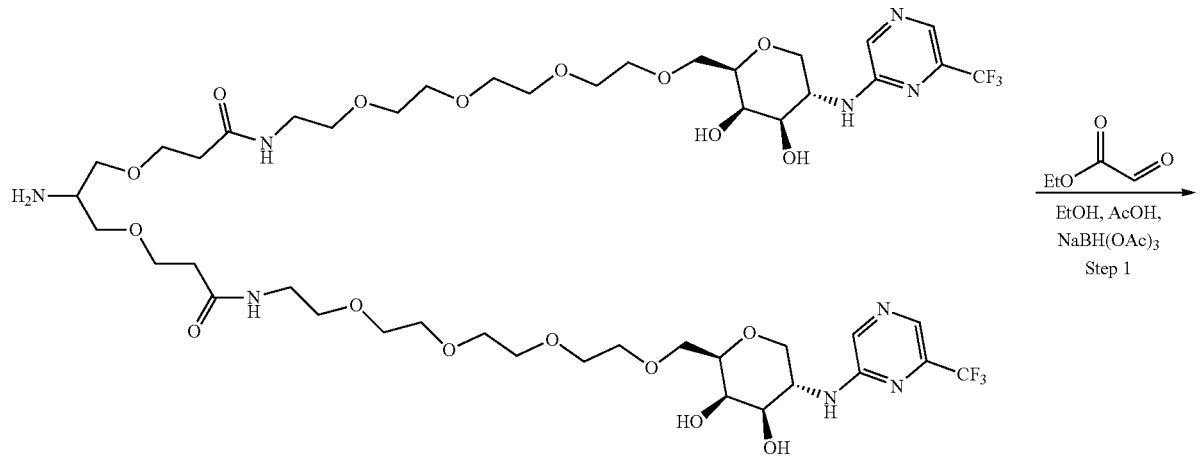

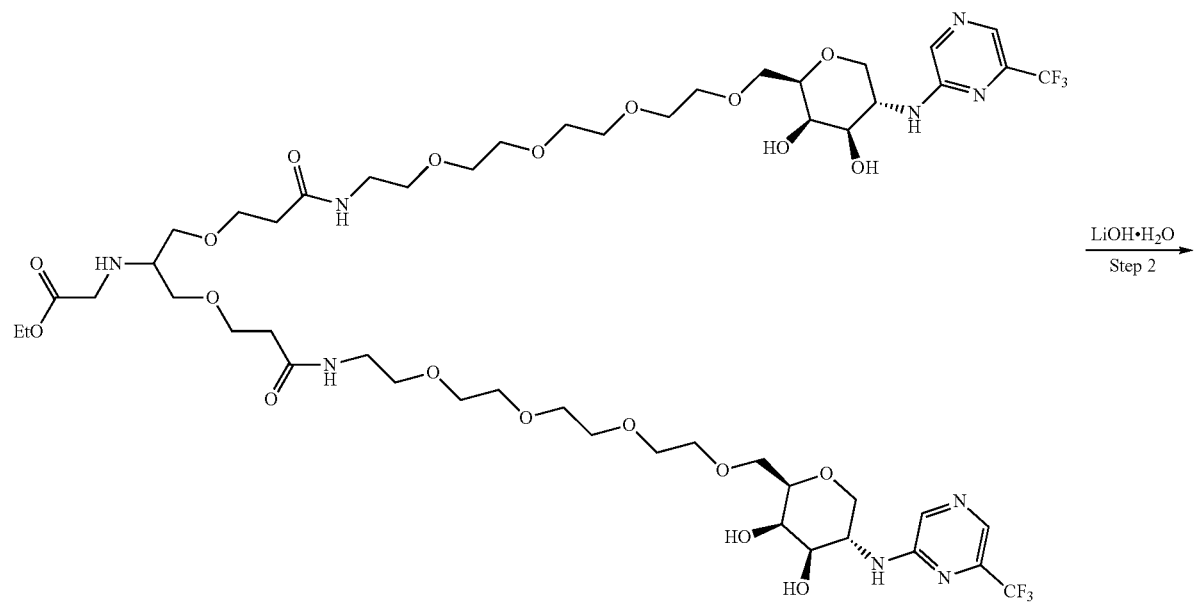

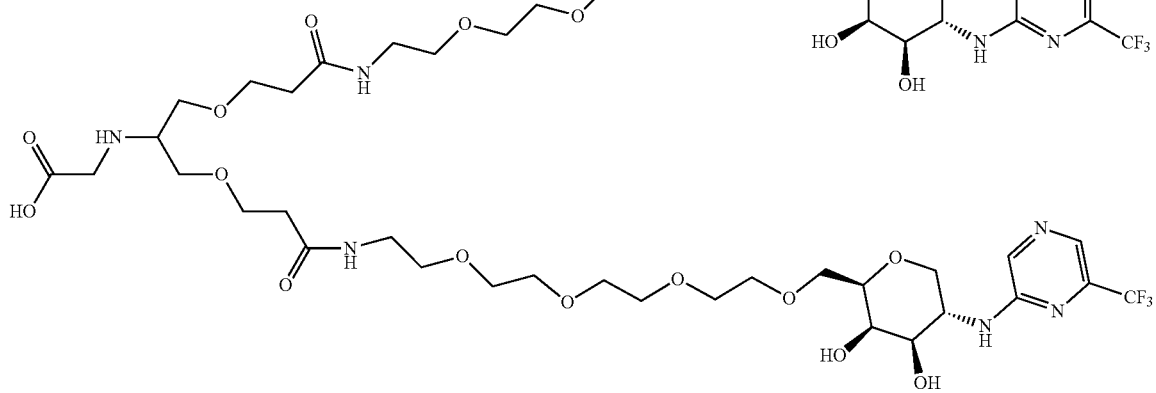

A31

Step 1: To a solution of 3,3'-((2-aminopropane-1,3-diyl)bis(oxy))bis(N-(1-((2R,3R,4R,5S)-3,4-dihydroxy-5-((6-(trifluoromethyl)pyrazin-2-yl)amino)tetrahydro-2H-pyran-2-yl)-2,5, 8,11-tetraoxatridecan-13-yl)propanamide) (1.1 g, 0.94 mmol) and ethyl 2-oxoacetate (0.56 mL, 2.83 mmol) in EtOH (8 mL) was added AcOH (0.03 mL, 0.47 mmol) at rt under N$_2$. The reaction was stirred at rt for 3 h. NaBH(OAc)$_3$ (595.9 mg, 2.83 mmol) was added at 0° C. The reaction was stirred overnight. The resulting mixture was filtered and concentrated in vacuo. The crude product was purified by prep-HPLC to give ethyl (1,39-bis((2R,3R,4R,5S)-3,4-dihydroxy-5-((6-(trifluoromethyl)pyrazin-2-yl)amino)tetrahydro-2H-pyran-2-yl)-15,25-dioxo-2,5,8,11,18,22,29,32,35,38-decaoxa-14,26-diazanonatriacontan-20-yl)glycinate (850 mg, 72% yield) as a colorless oil. LC-MS (ESI) found: 1255 [M+H]$^+$.

Step 2: To a solution of ethyl (1,39-bis((2R,3R,4R,5S)-3,4-dihydroxy-5-((6-(trifluoromethyl)pyrazin-2-yl)amino)tetrahydro-2H-pyran-2-yl)-15,25-dioxo-2,5,8,11,18,22,29,32,35,38-decaoxa-14,26-diazanonatriacontan-20-yl)glycinate (1 g, 0.8 mmol) in THF (6 mL) and H$_2$O (3 mL) was added LiOH·H$_2$O (0.1 g, 2.4 mmol) at rt. The reaction was stirred at rt for 2 h. The reaction was adjusted to pH=6 with 2 N HCL. The crude product was purified by prep-HPLC to afford (1,39-bis((2R,3R,4R,5S)-3,4-dihydroxy-5-((6-(trifluoromethyl)pyrazin-2-yl)amino)tetrahydro-2H-pyran-2-yl)-15,25-dioxo-2,5,8,11,18,22,29,32,35,38-decaoxa-14,26-diazanonatriacontan-20-yl)glycine (A31, 600 mg, 62% yield) as a white solid. LC-MS (ESI) found: 1227 [M+H]$^+$. $^1$H NMR (400 MHz, CD$_3$OD): δ 8.13 (s, 2H), 7.99 (s, 2H), 4.33 (td, J=10.5, 5.1 Hz, 2H), 4.12 (dd, J=11.0, 5.1 Hz, 2H), 3.88 (dd, J=3 8.8, 7.4 Hz, 2H), 3.79-3.49 (m, 43H), 3.44-3.35 (m, 4H), 3.12 (t, J=10.8 Hz, 2H), 2.49 (t, J=5.8 Hz, 4H). 19F NMR (377 MHz, CD$_3$OD): δ −70.20 (s).

Preparation of A32: 3-(((((2R,3R,4R,5S)-3,4-dihydroxy-5-((6-(trifluoromethyl)pyrazin-2-yl)amino)tetrahydro-2H-pyran-2-yl)methyl)amino)-3-oxopropanoic acid

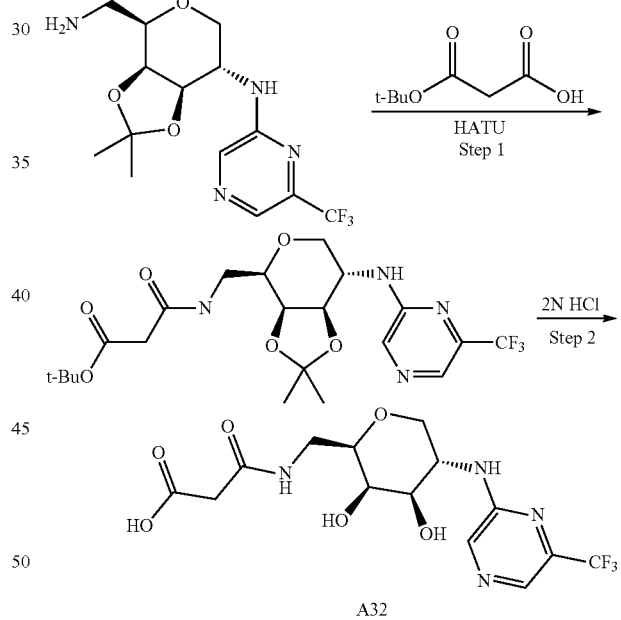

A32

Step 1: To a solution of 3-(tert-butoxy)-3-oxopropanoic acid (272.5 mg, 1.72 mmol) and HATU (818.7 mg, 2.15 mmol) in DMF (5 mL) was stirred at rt for 2 h. N-((3aS, 4R,7S,7aR)-4-(aminomethyl)-2,2-dimethyltetrahydro-4H-[1,3]dioxolo[4,5-c]pyran-7-yl)-6-(trifluoromethyl)pyrazin-2-amine (500 mg, 1.46 mmol) and DIEA (371.04 mg, 1.87 mmol) was added to above mixture. Reaction mixture was stirred at rt for 2 h. Reaction mixture was concentrated. Residue was purified by flash chromatography (EA/PE=1:1) to give tert-butyl 3-(((((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)amino)-3-oxopropanoate as a brown oil (600 mg, 85% yield). LC-MS (ESI) found: 489 [M+H]$^+$.

Step 2: To a solution of tert-butyl 3-((((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)amino)-3-oxopropanoate (800 mg, 1.64 mmol) and aqueous HCl (5 mL, 2 N in H$_2$O) in THF (3 mL) was stirred at rt overnight. Reaction mixture was concentrated. Residue was purified by flash chromatography reversed phase (MeOH in water from 5% to 30%) to give 3-((((2R,3R,4R,5S)-3,4-dihydroxy-5-((6-(trifluoromethyl)pyrazin-2-yl)amino)tetrahydro-2H-pyran-2-yl)methyl)amino)-3-oxopropanoic acid (A32, 274 mg, 42% yield). LC-MS (ESI) found: 395 [M+H]$^+$. $^1$H NMR (400 MHz, CD$_3$OD): δ 8.10 (s, 1H), 8.00 (s, 1H), 4.32 (td, J=10.5, 5.1 Hz, 1H), 4.12 (dd, J=11.0, 5.2 Hz, 1H), 3.87 (d, J=2.8 Hz, 1H), 3.64 (dd, J=10.6, 3.1 Hz, 1H), 3.59-3.50 (m, 2H), 3.37-3.33 (m, 1H), 3.29 (s, 2H), 3.10 (t, J=10.8 Hz, 1H).

Preparation of A33: 3-((1,15-bis((2R,3R,4R,5S)-3,4-dihydroxy-5-((6-(trifluoromethyl)pyrazin-2-yl)amino)tetrahydro-2H-pyran-2-yl)-3,13-dioxo-6,10-dioxa-2,14-diazapentadecan-8-yl)amino)-3-oxopropanoic acid

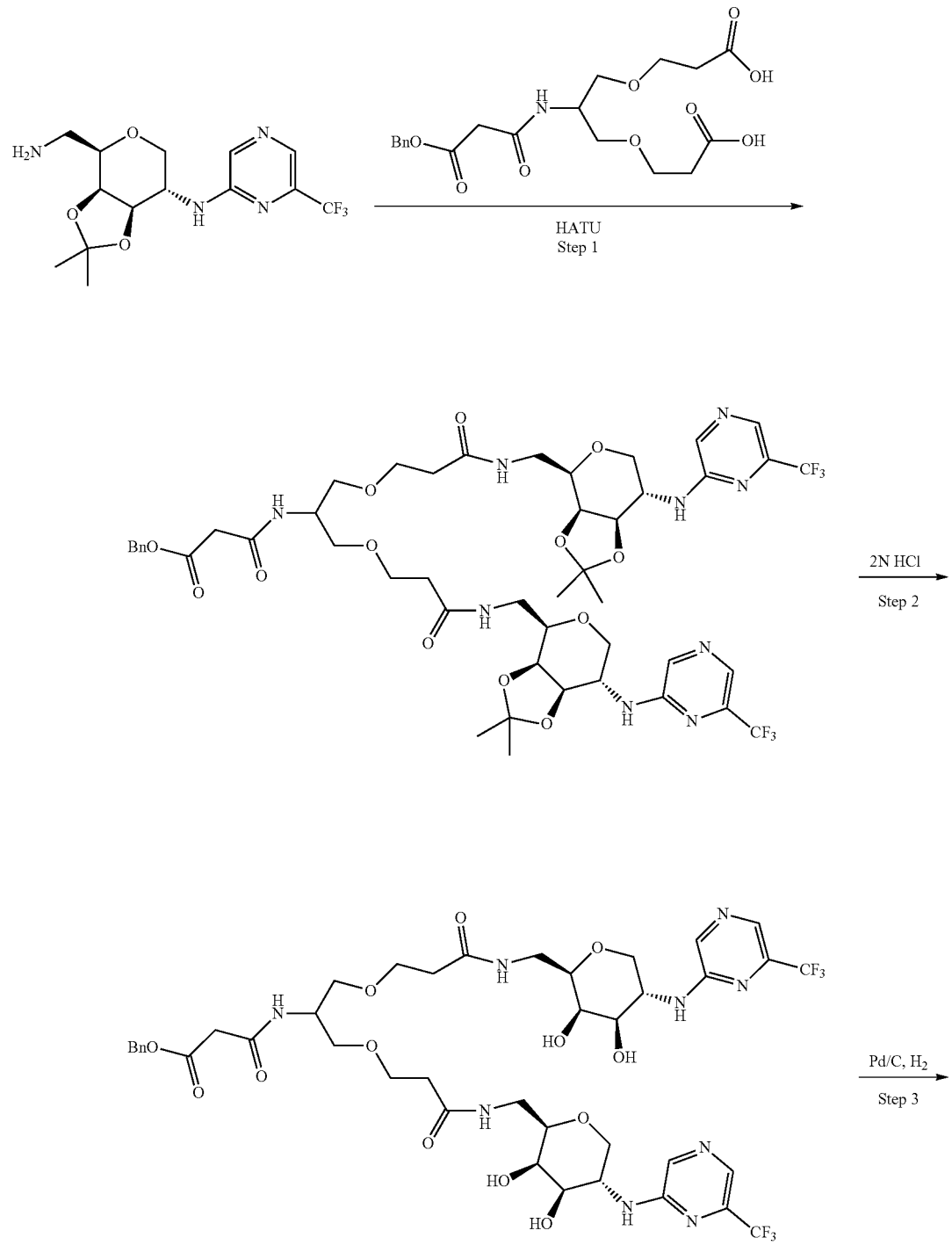

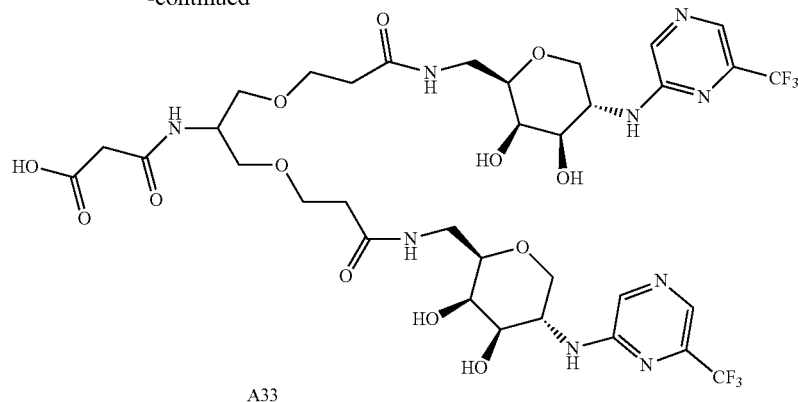

A33

Step 1: To a solution of 3,3'-((2-(3-(benzyloxy)-3-oxo-propanamido)propane-1,3-diyl)bis(oxy))dipropionic acid (100 mg, 0.24 mmol) in DMF (3 mL) were added HATU (277 mg, 0.73 mmol) and DIPEA (125 mg, 0.97 mmol) at rt. After stirring at rt for 20 min, N-((3aS,4R,7S,7aR)-4-(aminomethyl)-2,2-dimethyltetrahydro-4H-[1,3]dioxolo[4,5-c]pyran-7-yl)-6-(trifluoromethyl)pyrazin-2-amine (186 mg, 0.54 mmol) was added. The mixture was stirred at rt overnight, then concentrated. The residue was purified by flash to give benzyl 3-((1,15-bis((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)-3,13-dioxo-6,10-dioxa-2,14-diazapentadecan-8-yl)amino)-3-oxopropanoate (150 mg, 58% yield) as white solid. LC-MS (ESI) found: 1072 [M+H]⁺.

Step 2: To a solution of benzyl 3-((1,15-bis((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)-3,13-dioxo-6,10-dioxa-2,14-diazapentadecan-8-yl)amino)-3-oxopropanoate (150 mg, 0.14 mmol) in THF (3 mL) was added HCl (0.5 mL, 2 N in H$_2$O) at rt. The mixture was stirred at rt overnight, then concentrated. The residue was purified by flash to give benzyl 3-((1,15-bis((2R,3R,4R,5S)-3,4-dihydroxy-5-((6-(trifluoromethyl)pyrazin-2-yl)amino)tetrahydro-2H-pyran-2-yl)-3,13-dioxo-6,10-dioxa-2,14-diazapentadecan-8-yl)amino)-3-oxopropanoate (100 mg, 72% yield) as white solid. LC-MS (ESI) found: 992 [M+H]⁺.

Step 3: To a solution of benzyl 3-((1,15-bis((2R,3R,4R,5S)-3,4-dihydroxy-5-((6-(trifluoromethyl)pyrazin-2-yl)amino)tetrahydro-2H-pyran-2-yl)-3,13-dioxo-6,10-dioxa-2,14-diazapentadecan-8-yl)amino)-3-oxopropanoate (100 mg, 0.10 mmol), NH4OH (0.1 mL) and Pd/C (10 mg, 10% wt., 60% wet) in MeOH (3 mL) was stirred under a H$_2$ balloon at rt for 30 min. The mixture was filtered through a Celite pad, and the filtrate was concentrated to give the crude product. The crude product was purified by flash to give 3-((1,15-bis((2R,3R,4R,5S)-3,4-dihydroxy-5-((6-(trifluoromethyl)pyrazin-2-yl)amino)tetrahydro-2H-pyran-2-yl)-3,13-dioxo-6,10-dioxa-2,14-diazapentadecan-8-yl)amino)-3-oxopropanoic acid (A33, 27 mg, 30% yield) as white solid. LC-MS (ESI) found: 902 [M+H]⁺. ¹H NMR (400 MHz, CD$_3$OD): δ 8.11 (s, 2H), 7.98 (s, 2H), 4.32 (td, J=10.6, 5.2 Hz, 2H), 4.16-4.06 (m, 3H), 3.86 (s, 2H), 3.76-3.64 (m, 7H), 3.52 (t, J=7.0 Hz, 8H), 3.34 (s, 2H), 3.24 (s, 1H), 3.11 (s, 2H), 2.46 (d, J=5.4 Hz, 4H).

Preparation of A34: 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazatetracosan-24-oic acid

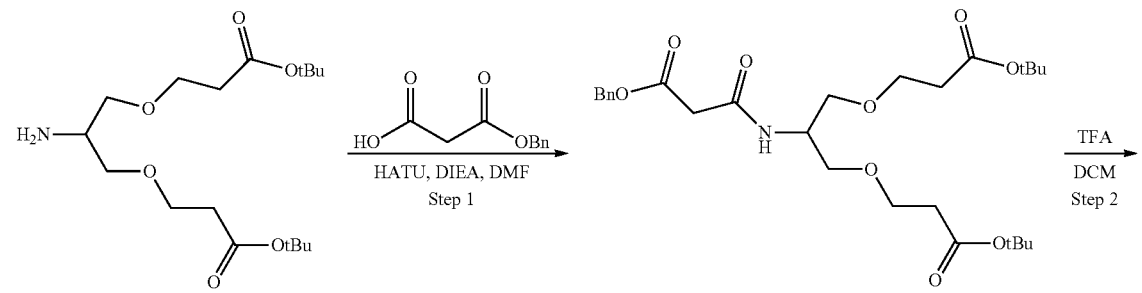

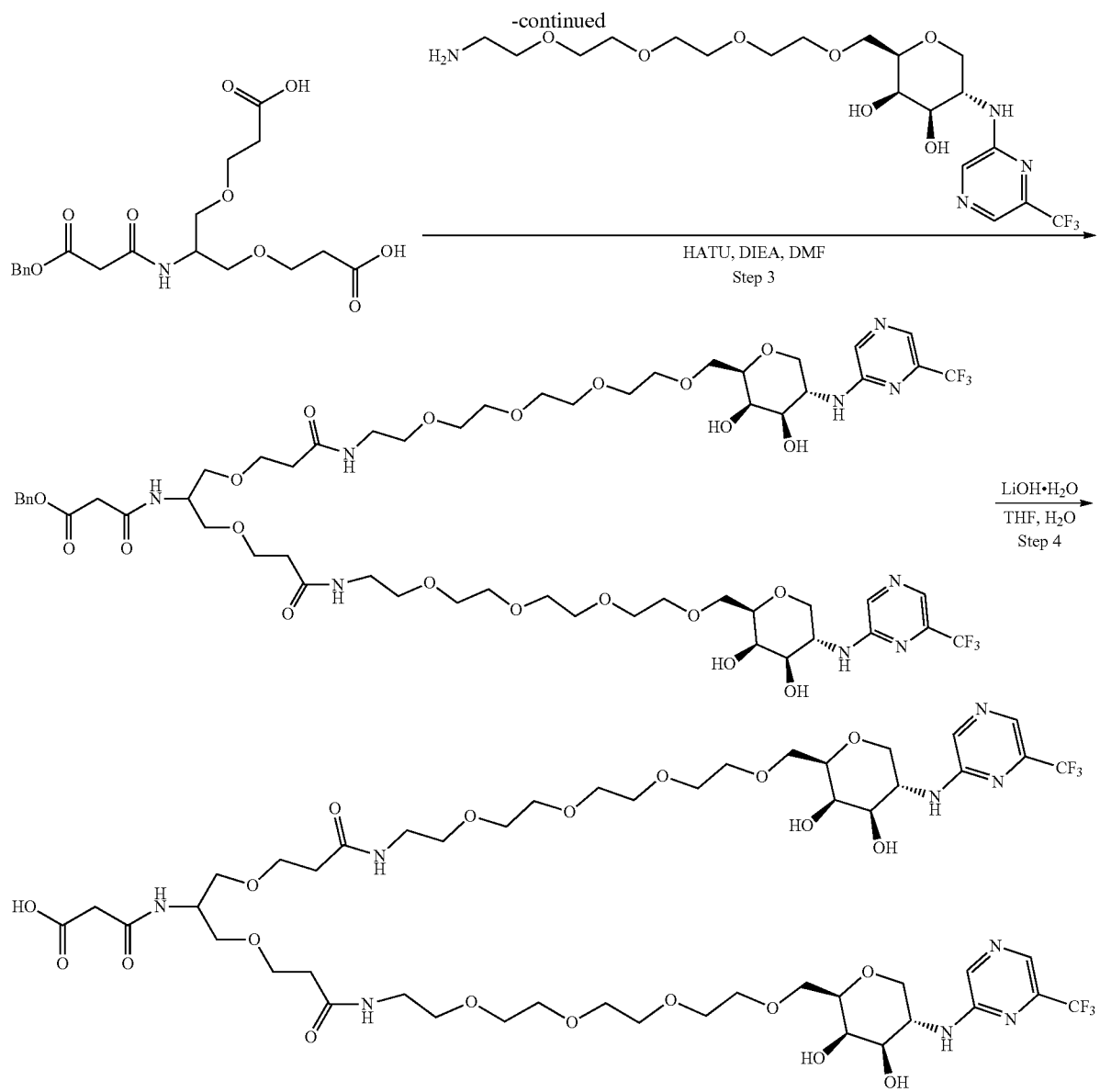

Step 1: To a solution of 3-(benzyloxy)-3-oxopropanoic acid (2.3 g, 11.8 mmol), DIPEA (5.9 mL, 35.5 mmol) and HATU (6.76 g, 17.8 mmol) in DMF (25 mL) was stirred at rt for 30 min. Di-tert-butyl 3,3'-((2-aminopropane-1,3-diyl)bis(oxy))dipropionate (4.12 g, 11.8 mmol) was added at rt. The reaction was stirred at rt overnight. The mixture was diluted with DCM (200 mL), washed with $H_2O$ (60 mL×2) and brine (60 mL), dried over $Na_2SO_4$. The mixture was concentrated in vacuo. The crude product was purified by flash chromatography (silica gel, 0-20% EA in PE) to give di-tert-butyl 3,3'-((2-(3-(benzyloxy)-3-oxopropanamido)propane-1,3-diyl)bis(oxy))dipropionate (850 mg, 14% yield) as a colorless oil. LC-MS (ESI) found: 525 [M+H]$^+$.

Step 2: To a solution of di-tert-butyl 3,3'-((2-(3-(benzyloxy)-3-oxopropanamido)propane-1,3-diyl)bis(oxy))dipropionate (850 mg, 1.6 mmol) in DCM (10 mL) was added TFA (3 mL, 40.4 mmol) at rt. The reaction was stirred at rt for 2 h. The resulting mixture was concentrated in vacuo. The crude product was purified by prep-HPLC to give 3,3'-((2-(3-(benzyloxy)-3-oxopropanamido)propane-1,3-diyl)bis(oxy))dipropionic acid (260 mg, 37% yield) as a colorless oil. LC-MS (ESI) found: 412 [M+H]$^+$.

Step 3: To a solution of 3,3'-((2-(3-(benzyloxy)-3-oxopropanamido)propane-1,3-diyl)bis(oxy))dipropionic acid (160 mg, 0.4 mmol), DIPEA (0.321 mL, 1.945 mmol) and HATU (443.6 mg, 1.2 mmol) in DMF (10 mL) was stirred at rt for 30 min. (2R,3R,4R,5S)-2-(13-amino-2,5,8,11-tetraoxatridecyl)-5-((6-(trifluoromethyl)pyrazin-2-yl)amino) tetrahydro-2H-pyran-3,4-diol (414.5 mg, 0.9 mmol) was added at rt. The reaction was stirred overnight. The resulting mixture was concentrated in vacuo. The crude product was purified by prep-HPLC to give benzyl 1-((2R,3R,4R,5S)-3, 4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino) tetrahydro-2H-pyran-2-yl)-15-oxo-2,5,8,11,18-pentaoxa-14-azanonadecan-19-yl)-15,22-dioxo-2,5,8,11,18-pentaoxa- 14,21-diazatetracosan-24-oate (210 mg, 50% yield) as a colorless oil. LC-MS (ESI) found: 1345 [M+H]⁺.

Step 4: To a solution of benzyl 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazatetracosan-24-oate (210 mg, 0.2 mmol) in THF (6 mL) and H₂O (2 mL) was added LiOH—H₂O (20 mg, 0.5 mmol) at rt. The reaction was stirred at rt for 2 h. The reaction was adjusted to acid with 2 N HCl. The crude product was purified by prep-HPLC to give 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazatetracosan-24-oic acid (A34, 96 mg, 49% yield) as a white solid. LC-MS (ESI) found: 1255 [M+H]⁺. ¹H NMR (400 MHz, CD₃OD): δ 8.12 (s, 2H), 8.00 (s, 2H), 4.34 (td, J=10.4, 5.1 Hz, 2H), 4.12 (dd, J=10.7, 5.0 Hz, 3H), 3.93 (d, J=2.6 Hz, 2H), 3.74-3.59 (m, 38H), 3.57-3.47 (m, 8H), 3.38 (t, J=5.3 Hz, 4H), 3.12 (t, J=10.8 Hz, 2H), 2.45 (t, J=5.9 Hz, 4H). ¹⁹F NMR (377 MHz, CD₃OD): δ −70.26 (s).

Preparation of A35: 2-(4-((4-(((2R,3R,4R,5S)-3,4-dihydroxy-5-((6-(trifluoromethyl)pyrazin-2-yl)amino)tetrahydro-2H-pyran-2-yl)methyl)piperazin-1-yl)methyl)phenoxy)acetic acid

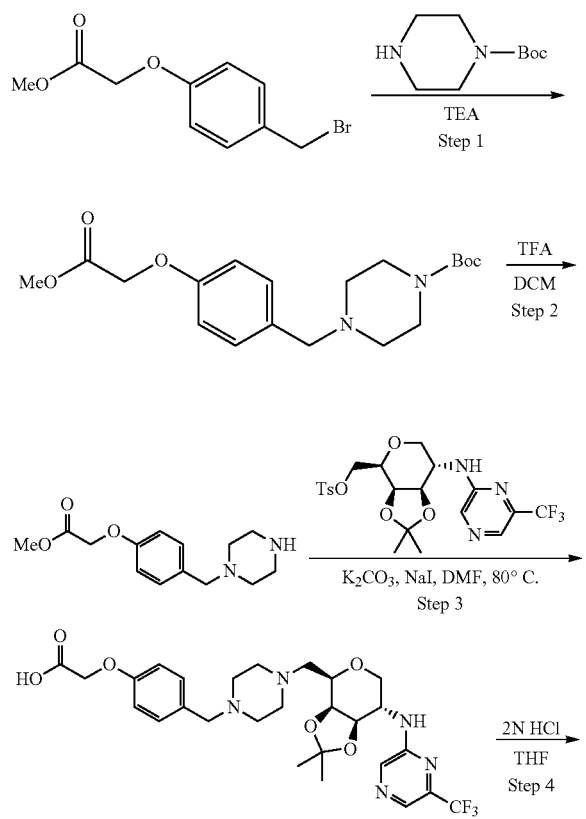

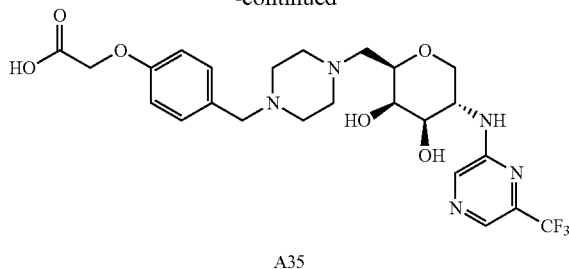

A35

Step 1: To the solution of methyl 2-(4-(bromomethyl)phenoxy)acetate (300 mg, 1.158 mmol) in CH₃CN (3 mL) were added tert-butyl piperazine-1-carboxylate (259 mg, 1.389 mmol) and TEA (0.5 mL, 3.597 mmol). The reaction was stirred at RT for 2 h and was ensured completion by LC-MS. Then it was concentrated and purified by 10% MeOH in DCM to get tert-butyl 4-(4-(2-methoxy-2-oxoethoxy)benzyl)piperazine-1-carboxylate (400 mg, 95% yield) as white solid. LC-MS (ESI) found: 365 [M+H]⁺.

Step 2: To the solution of tert-butyl 4-(4-(2-methoxy-2-oxoethoxy)benzyl)piperazine-1-carboxylate (400 mg, 1.098 mmol) in DCM (4 mL) was added TFA (80 μL, 1.077 mmol). The reaction was stirred at RT for 2 h. Then it was concentrated to get crude methyl 2-(4-(piperazin-1-ylmethyl)phenoxy)acetate (250 mg, 86% yield) as colorless oil. LC-MS (ESI) found: 265 [M+H]⁺.

Step 3: To the solution of methyl 2-(4-(piperazin-1-ylmethyl)phenoxy)acetate (250 mg, 0.946 mmol) in DMF (3 mL) were added ((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl 4-methylbenzenesulfonate (160 mg, 0.318 mmol), K₂CO₃ (44 mg, 0.318 mmol) and NaI (48 mg, 0.318 mmol). The reaction was stirred at 80° C. for 3 days. Solvent was removed and the residue was purified by 50% MeOH in DCM to get 2-(4-((4-(((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)piperazin-1-yl)methyl)phenoxy)acetic acid (100 mg, 54% yield) as colorless oil. LC-MS (ESI) found: 581 [M+H]⁺.

Step 4: To the solution of 2-(4-((4-(((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)piperazin-1-yl)methyl)phenoxy)acetic acid (100 mg, 0.172 mmol) in THF (2 mL) was added HCl (20 μL, 2 N in H₂O). The reaction was stirred for 2 h and ensured completion by LCMS. Then it was concentrated and the residue purified by prep-HPLC to get 2-(4-((4-(((2R,3R,4R,5S)-3,4-dihydroxy-5-((6-(trifluoromethyl)pyrazin-2-yl)amino)tetrahydro-2H-pyran-2-yl)methyl)piperazin-1-yl)methyl)phenoxy)acetic acid (A35, 45 mg, 48% yield) as white solid. LC-MS (ESI) found: 541 [M+H]⁺. ¹H NMR (400 MHz, CD₃OD): δ 8.11 (s, 1H), 8.01 (s, 1H), 7.30 (d, J=7.2 Hz, 2H), 6.95 (s, 2H), 4.47 (s, 2H), 4.32 (d, J=5.2 Hz, 2H), 4.14 (dd, J=11.0, 5.2 Hz, 2H), 3.87 (d, J=11.4 Hz, 2H), 3.86 (s, 1H), 3.70 (dd, J=30.3, 18.1 Hz, 3H), 3.13 (t, J=11.0 Hz, 3H), 2.92 (s, 8H).

Preparation of A36: 3-[[2-[3-[2-[2-[2-[2-[[(1S,2R,3R,4R,5S)-2,3-dihydroxy-4-[[6-(trifluoro methyl)pyrazin-2-yl]amino]-6,8-dioxabicyclo[3.2.1]octan-1-yl]methoxy]ethoxy]ethoxy]ethylamino]-3-oxo-propoxy]-1-[[3-[2-[2-[2-[2-[[(1S,2R,3R,4R,5S)-2,3-dihydroxy-4-[[6-(trifluoromethyl)pyrazin-2-yl]amino]-6,8-dioxabicyclo[3.2.1]octan-1-yl]methoxy]ethoxy]ethoxy]ethoxy]ethylamino]-3-oxo-propoxy]methyl]ethyl]amino]-3-oxo-propanoic acid
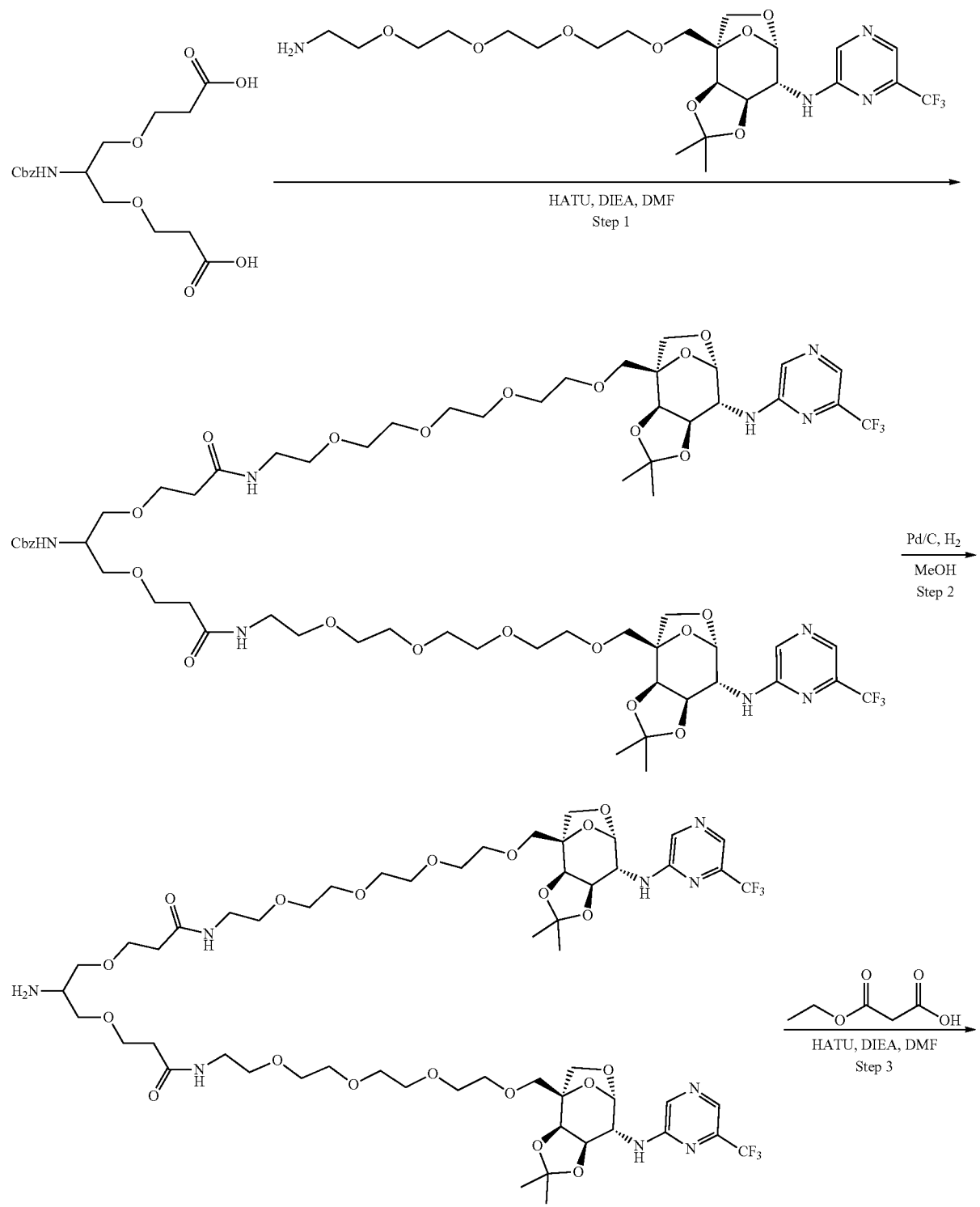

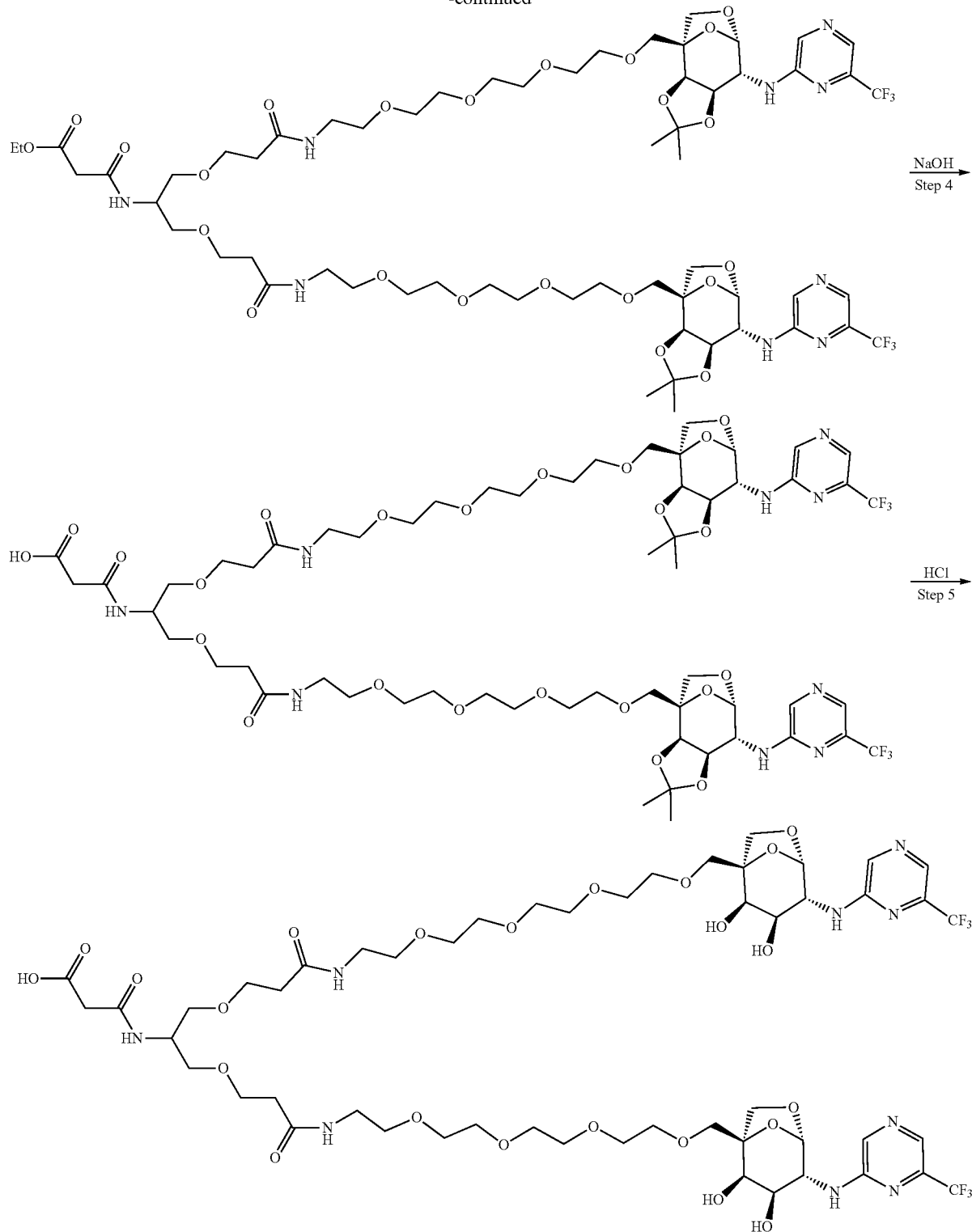

A36

Step 1: To a solution of HATU (617.65 mg, 1.62 mmol, 3 eq) was added to a mixture of 3-[2-(benzyloxycarbonylamino)-3-(2-carboxyethoxy)propoxy]propanoic acid (200 mg, 541.47 µmol, 1 eq), N-[(1S,2R,6R,7R,8S)-1-[2-[2-[2-(2-aminoethoxy)ethoxy]ethoxy] ethoxymethyl]-4,4-dimethyl-3,5,9,11-tetraoxatricyclo[6.2.1.0$^{2,6}$]undecan-7-yl]-6-(trifluoromethyl)pyrazin-2-amine (839.17 mg, 1.25 mmol, 82% purity, 2.3 eq) and DIPEA (279.92 mg, 2.17 mmol, 377.25 µL, 4 eq) in DMF (8 mL) at 20° C., then the mixture was stirred at 20° C. for 1 h. LCMS showed Compound 1 was consumed and desired mass was detected. The mixture was purified by prep-HPLC (FA condition; column: Phenomenex Luna C18 200*40 mm*10 μm; mobile phase: [water (FA)-ACN]; B %: 30%-70%, 8 min). Benzyl N-[2-[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy]ethoxy]ethoxy]ethylamino]-3-oxo-propoxy]-1-[[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy]ethoxy]ethoxy]ethylamino]-3-oxo-propoxy]methyl]ethyl]carbamate (250 mg, 173.80 umol, 32.10% yield) was obtained as a white solid. LC-MS (ESI) found: 720.0 [M/2+H]$^+$.

Step 2: To a solution of benzyl N-[2-[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy]ethoxy]ethoxy]ethylamino]-3-oxo-propoxy]-1-[[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy]ethoxy]ethoxy]ethylamino]-3-oxo-propoxy]methyl]ethyl]carbamate (250 mg, 173.80 μmol, 1 eq) in MeOH (20 mL) was added Pd/C (100 mg, 10% purity) under N$_2$. The suspension was degassed under vacuum and purged with H$_2$ several times. The mixture was stirred under H$_2$ (15 psi) at 20° C. for 4 hours. The mixture was filtered and the filtrated was concentrated to afford. 3-[2-amino-3-[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy] ethoxy]ethoxy] ethylamino]-3-oxo-propoxy]propoxy]-N-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy]ethoxy]ethoxy]ethyl]propanamide (200 mg, crude) was obtained as a white solid. LC-MS (ESI) found: 652.9 [M/2+H]$^+$.

Step 3: To a solution of HATU (64.14 mg, 168.68 μmol, 2 eq) was added to a mixture of 3-[2-amino-3-[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy]ethoxy]ethoxy]ethylamino]-3-oxo-propoxy]propoxy]-N-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy]ethoxy]ethoxy]ethyl]propanamide (110 mg, 84.34 μmol, 1 eq), 3-ethoxy-3-oxo-propanoic acid (13.37 mg, 101.21 μmol, 1.2 eq) and DIEA (21.80 mg, 168.68 μmol, 29.38 μL, 2 eq) in DMF (2 mL) at 20° C. Then the mixture was stirred at 20° C. for 1 h. LCMS showed Compound 4 was consumed and desired compound was detected. Water (10 ml) was added to the mixture, and extracted with EtOAc (10 mL×2). The combined organic layers were washed with brine (10 mL), dried over Na$_2$SO$_4$ and filtered. The filtrate was concentrated under reduced pressure to give a residue. The residue was purified by prep-TLC (SiO$_2$, EtOAc:MeOH=10:1). Ethyl 3-[[2-[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo [6.2.1.0$^{2,6}$] undecan-1-yl]methoxy]ethoxy]ethoxy]ethoxy]ethylamino]-3-oxo-propoxy]-1-[[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy]ethoxy]ethoxy]ethylamino]-3-oxo-propoxy]methyl]ethyl]amino]-3-oxo-propanoate (100 mg, 70.50 μmol, 83.60% yield) was obtained as a white solid. LC-MS (ESI) found: 710.0 [M/2+H]$^+$.

Step 4: To a solution of NaOH/H$_2$O (1 M, 112.80 μL, 2 eq) was added to a solution of ethyl 3-[[2-[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy]ethoxy]ethoxy]ethylamino]-3-oxo-propoxy]-1-[[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy] ethoxy]ethoxy] ethoxy]ethylamino]-3-oxo-propoxy]methyl]ethyl]amino]-3-oxo-propanoate (80 mg, 56.40 μmol, 1 eq) in THF (1 mL) at 20° C., then the mixture was stirred at 20° C. for 1 h. The mixture of 3-[[2-[3-[2-[2-[2-[2-[[(1S,2R,6R,7R,8S)-4,4-dimethyl-7-[[6-(trifluoromethyl) pyrazin-2-yl]amino]-3,5,9,11-tetraoxatricyclo[6.2.1.0$^{2,6}$]undecan-1-yl]methoxy]ethoxy]ethoxy]ethoxy]ethylamino]-3-oxo-propoxy]-1-[[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy]ethoxy] ethoxy]ethylamino]-3-oxo-propoxy]methyl]ethyl]amino]-3-oxo-propanoic acid (78 mg, crude) in THF (1 mL) (yellow liquid) was directly used for next step without work up. LC-MS (ESI) found: 696.0 [M/2+H]$^+$.

Step 5: To a solution of HCl (2 M, 1 mL, 35.65 eq) was added to the solution of 3-[[2-[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy]ethoxy]ethoxy]ethylamino]-3-oxo-propoxy]-1-[[3-[2-[2-[2-[2-[[(1S,2R,6R,7R,8S)-4,4-dimethyl-7-[[6-(trifluoromethyl)pyrazin-2-yl]amino]-3,5,9,11-tetraoxatricyclo[6.2.1.0$^{2,6}$]undecan-1-yl]methoxy]ethoxy]ethoxy]ethoxy]ethylamino]-3-oxo-propoxy]methyl]ethyl]amino]-3-oxo-propanoic acid (78 mg, 56.10 μmol, 1 eq) in THF (1 mL) at 20° C., and stirred for 2 h. The mixture was purified by prep-HPLC. 3-[[2-[3-[2-[2-[2-[2-[[(1S,2R,3R,4R,5S)-2,3-dihydroxy-4-[[6-(trifluoromethyl) pyrazin-2-yl]amino]-6,8-dioxabicyclo[3.2.1]octan-1-yl]methoxy] ethoxy]ethoxy]ethoxy]ethylamino]-3-oxo-propoxy]-1-[[3-[2-[2-[2-[2-[[(1S,2R,3R,4R,5S)-2,3-dihydroxy-4-[[6-(trifluoromethyl)pyrazin-2-yl]amino]-6,8-dioxabicyclo[3.2.1]octan-1-yl]methoxy]ethoxy]ethoxy]ethoxy]ethylamino]-3-oxo-propoxy]methyl]ethyl]amino]-3-oxo-propanoic acid (A36, 32 mg, 22.48 μmol, 40.08% yield, 92.06% purity) was obtained as colorless oil. $^1$H NMR (400 MHz, methanol-d$_4$) δ ppm 8.17 (s, 2H) 8.01 (s, 2H) 5.35 (d, J=1.22 Hz, 2H) 4.20 (d, J=9.90 Hz, 2H) 4.10-4.17 (m, 1H) 4.01 (d, J=9.54 Hz, 2H) 3.96 (d, J=4.28 Hz, 2H) 3.81-3.87 (m, 4H) 3.60-3.74 (m, 33H) 3.46-3.58 (m, 8H) 3.38 (t, J=5.38 Hz, 4H) 2.45 (t, J=6.05 Hz, 4H).

Preparation of A37: (1S,2R,3R,4R,5S)-1-(hydroxymethyl)-4-((3-(trifluoromethyl)-1H-pyrazolo[3,4-d]pyrimidin-6-yl)amino)-6,8-dioxabicyclo[3.2.1]octane-2,3-diol

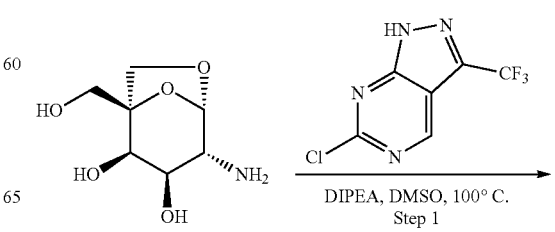

DIPEA, DMSO, 100° C.
Step 1

-continued

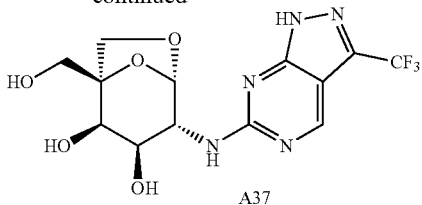

Step 1: To a solution of (1S,2R,3R,4R,5S)-4-amino-1-(hydroxymethyl)-6,8-dioxabicyclo[3.2.1]octane-2,3-diol (100 mg, 523.06 umol) and 6-chloro-3-(trifluoromethyl)-2H-pyrazolo[3,4-d]pyrimidine (174.62 mg, 784.60 umol) was added DIPEA (162.24 mg, 1.26 mmol, 218.65 uL, 2.4 eq) and ethyl 4-chloro-2-(trifluoromethyl)pyrimidine-5-carboxylate (199.75 mg, 784.60 umol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). A37, (1S,2R,3R,4R,5S)-1-(hydroxymethyl)-4-((3-(trifluoromethyl)-1H-pyrazolo[3,4-d]pyrimidin-6-yl)amino)-6,8-dioxabicyclo[3.2.1]octane-2,3-diol, Yield: 84 mg, 43.1%, white solid. LC-MS (ESI) found: 378 [M+H]⁺. 0.1H NMR (400 MHz, methanol-d4) δ=8.86 (s, 1H), 5.47 (br s, 1H), 4.27 (br s, 1H), 4.02-3.81 (m, 6H), 3.74 (d, J=7.9 Hz, 1H).

Preparation of A38: 2-[[(1S,2R,3R,4R,5S)-2,3-dihydroxy-1-(hydroxymethyl)-6,8-dioxabicyclo[3.2.1]octan-4-yl]amino]-6-methyl-pyrimidine-4-carbonitrile

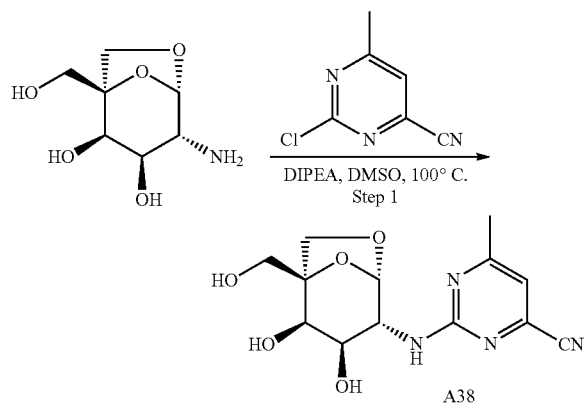

Step 1: To a solution of (1S,2R,3R,4R,5S)-4-amino-1-(hydroxymethyl)-6,8-dioxabicyclo[3.2.1]octane-2,3-diol (100 mg, 523.06 umol) and 2-chloro-6-methyl-pyrimidine-4-carbonitrile (120.49 mg, 784.60 umol) was added DIPEA (162.24 mg, 1.26 mmol, 218.65 uL, 2.4 eq) and ethyl 4-chloro-2-(trifluoromethyl)pyrimidine-5-carboxylate (199.75 mg, 784.60 umol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). A38, 2-[[(1S,2R,3R,4R,5S)-2,3-dihydroxy-1-(hydroxymethyl)-6,8-dioxabicyclo[3.2.1]octan-4-yl]amino]-6-methyl-pyrimidine-4-carbonitrile, Yield: 60.8 mg, 37.7%, white solid. LC-MS (ESI) found: 309 [M+H]⁺. 1H NMR (400 MHz, METHANOL-d4) δ=6.92 (br s, 1H), 5.37 (br s, 1H), 4.22 (br s, 2H), 4.04-3.65 (m, 7H), 2.40 (br s, 3H).

Preparation of A39: 3-[[(1S,2R,3R,4R,5S)-2,3-dihydroxy-1-(hydroxymethyl)-6,8-dioxabicyclo[3.2.1]octan-4-yl]amino]pyridazine-4-carbonitrile

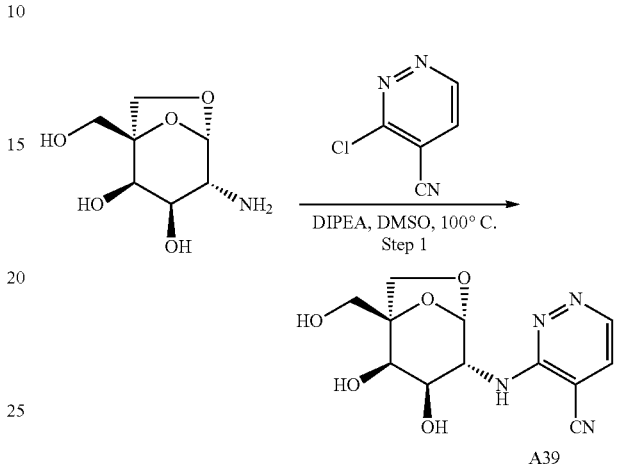

Step 1: To a solution of (1S,2R,3R,4R,5S)-4-amino-1-(hydroxymethyl)-6,8-dioxabicyclo[3.2.1]octane-2,3-diol (100 mg, 523.06 umol) and 3-chloropyridazine-4-carbonitrile (109.48 mg, 784.60 umol) was added DIPEA (162.24 mg, 1.26 mmol, 218.65 uL, 2.4 eq) and ethyl 4-chloro-2-(trifluoromethyl)pyrimidine-5-carboxylate (199.75 mg, 784.60 umol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). A39, 3-[[(1S,2R,3R,4R,5S)-2,3-dihydroxy-1-(hydroxymethyl)-6,8-dioxabicyclo[3.2.1]octan-4-yl]amino]pyridazine-4-carbonitrile, Yield: 28.5 mg, 18.5%, white solid. LC-MS (ESI) found: 295 [M+H]⁺. 1H NMR (400 MHz, methanol-d4) δ=8.67 (d, J=4.9 Hz, 1H), 7.74 (d, J=4.9 Hz, 1H), 5.50 (d, J=1.4 Hz, 1H), 4.56 (dd, J=1.4, 9.9 Hz, 1H), 4.07 (dd, J=4.3, 9.8 Hz, 1H), 4.01-3.95 (m, 2H), 3.91-3.85 (m, 2H), 3.76 (d, J=7.9 Hz, 1H).

Preparation of A40: 2-[[(1S,2R,3R,4R,5S)-2,3-dihydroxy-1-(hydroxymethyl)-6,8-dioxabicyclo[3.2.1]octan-4-yl]amino]-5-fluoro-pyridine-3-carbonitrile and A41: 2-chloro-5-[[(1S,2R,3R,4R,5S)-2,3-dihydroxy-1-(hydroxymethyl)-6,8-dioxabicyclo[3.2.1]octan-4-yl]amino]pyridine-3-carbonitrile

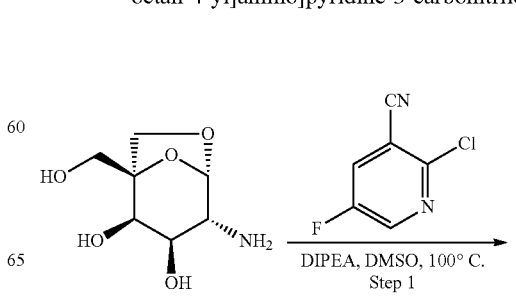

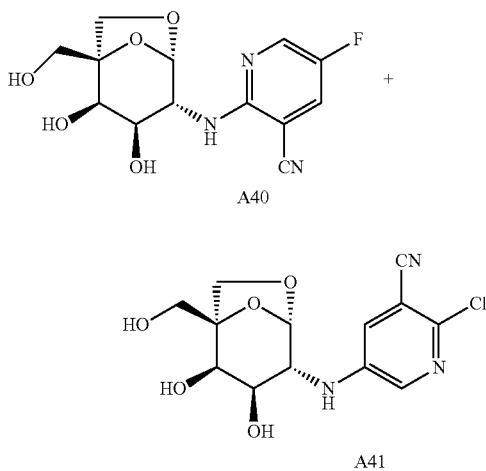

A40

A41

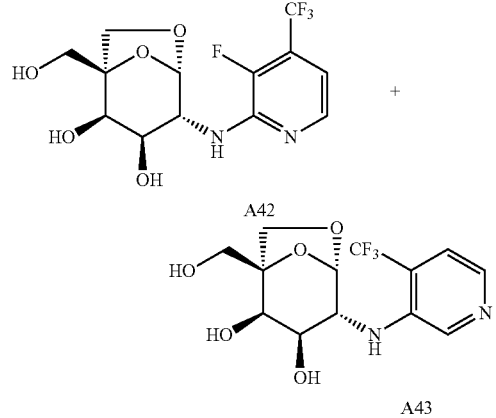

A42

A43

Step 1: To a solution of (1S,2R,3R,4R,5S)-4-amino-1-(hydroxymethyl)-6,8-dioxabicyclo[3.2.1]octane-2,3-diol (100 mg, 523.06 umol) and 2-chloro-5-fluoro-pyridine-3-carbonitrile (122.82 mg, 784.60 umol) was added DIPEA (162.24 mg, 1.26 mmol, 218.65 uL, 2.4 eq) and ethyl 4-chloro-2-(trifluoromethyl)pyrimidine-5-carboxylate (199.75 mg, 784.60 umol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). A40: 2-[[(1S,2R,3R,4R,5S)-2,3-dihydroxy-1-(hydroxymethyl)-6,8-dioxabicyclo[3.2.1]octan-4-yl]amino]-5-fluoro-pyridine-3-carbonitrile Yield: 20.13 mg, 12.36%, yellow solid. LC-MS (ESI) found: 312 [M+H]+. 1H NMR (400 MHz, methanol-d4) δ=8.23 (d, J=3.0 Hz, 1H), 7.78 (dd, J=3.1, 7.9 Hz, 1H), 5.40 (d, J=1.3 Hz, 1H), 4.34 (br d, J=8.1 Hz, 1H), 4.00-3.91 (m, 4H), 3.88-3.82 (m, 2H), 3.73 (d, J=8.0 Hz, 1H). A41: 2-chloro-5-[[(1S,2R,3R,4R,5S)-2,3-dihydroxy-1-(hydroxymethyl)-6,8-dioxabicyclo [3.2.1]octan-4-yl]amino]pyridine-3-carbonitrile Yield: 9.5 mg, 5.5%, white solid. LC-MS (ESI) found: 328 [M+H]+. 1H NMR (400 MHz, methanol-d4) δ=8.08 (d, J=3.1 Hz, 1H), 7.50 (d, J=3.1 Hz, 1H), 5.31 (d, J=1.4 Hz, 1H), 4.00-3.90 (m, 2H), 3.87-3.71 (m, 5H), 3.63-3.57 (m, 1H).

Preparation of A42: (1S,2R,3R,4R,5S)-4-[[3-fluoro-4-(trifluoromethyl)-2-pyridyl]amino]-1-(hydroxymethyl)-6,8-dioxabicyclo[3.2.1]octane-2,3-diol and A43: (1S,2R,3R,4R,5S)-4-[[2-chloro-4-(trifluoromethyl)-3-pyridyl]amino]-1-(hydroxymethyl)-6,8-dioxabicyclo[3.2.1]octane-2,3-diol

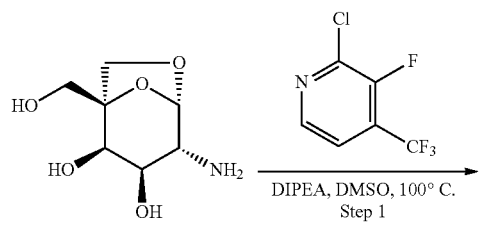

Step 1: To a solution of (1S,2R,3R,4R,5S)-4-amino-1-(hydroxymethyl)-6,8-dioxabicyclo[3.2.1]octane-2,3-diol (100 mg, 523.06 umol) and 2-chloro-3-fluoro-4-(trifluoromethyl)pyridine (156.13 mg, 784.60 umol) was added DIPEA (162.24 mg, 1.26 mmol, 218.65 uL, 2.4 eq) and ethyl 4-chloro-2-(trifluoromethyl)pyrimidine-5-carboxylate (199.75 mg, 784.60 umol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). A116: (1S,2R,3R,4R,5S)-4-[[3-fluoro-4-(trifluoromethyl)-2-pyridyl]amino]-1-(hydroxymethyl)-6,8-dioxabicyclo[3.2.1]octane-2,3-diol, Yield: 8 mg, 4.3%, yellow solid. LC-MS (ESI) found: 355 [M+H]+. 1H NMR (400 MHz, methanol-d4) δ=8.03 (d, J=5.0 Hz, 1H), 7.51 (d, J=5.1 Hz, 1H), 5.44 (d, J=1.1 Hz, 1H), 4.35 (br d, J=10.5 Hz, 1H), 3.97-3.91 (m, 1H), 3.86-3.74 (m, 6H). A117: (1S,2R,3R,4R,5S)-4-[[2-chloro-4-(trifluoromethyl)-3-pyridyl]amino]-1-(hydroxymethyl)-6,8-dioxabicyclo[3.2.1]octane-2,3-diol, Yield: 20 mg, 10.3%, yellow solid. LC-MS (ESI) found: 371 [M+H]+. 1H NMR (400 MHz, methanol-d4) δ=7.98 (d, J=5.3 Hz, 1H), 6.76 (t, J=4.8 Hz, 1H), 5.40 (d, J=1.4 Hz, 1H), 4.63 (s, 1H), 4.34 (br d, J=8.4 Hz, 1H), 4.00-3.93 (m, 3H), 3.88-3.82 (m, 2H), 3.73 (d, J=7.9 Hz, 1H).

Preparation of A44: (1S,2R,3R,4R,5S)-4-[(2,5-dichloro-3-pyridyl)amino]-1-(hydroxymethyl)-6,8-dioxabicyclo[3.2.1]octane-2,3-diol

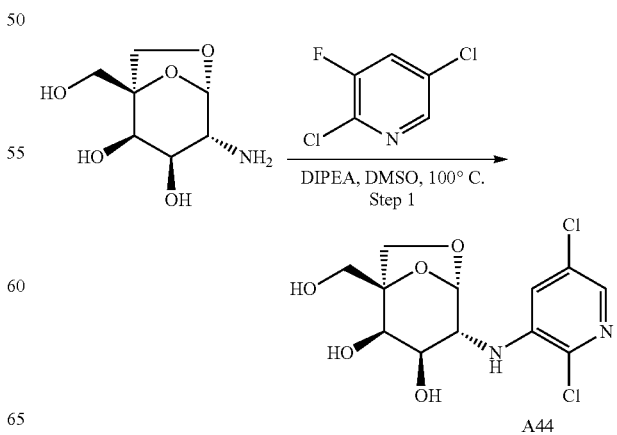

A44

Step 1: To a solution of (1S,2R,3R,4R,5S)-4-amino-1-(hydroxymethyl)-6,8-dioxabicyclo[3.2.1]octane-2,3-diol (100 mg, 523.06 umol) and 2,5-dichloro-3-fluoro-pyridine (130.23 mg, 784.60 umol) was added DIPEA (162.24 mg, 1.26 mmol, 218.65 uL, 2.4 eq) and ethyl 4-chloro-2-(trifluoromethyl)pyrimidine-5-carboxylate (199.75 mg, 784.60 umol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). A44: (1S,2R,3R,4R,5S)-4-[(2,5-dichloro-3-pyridyl)amino]-1-(hydroxymethyl)-6,8-dioxabicyclo[3.2.1]octane-2,3-diol, yield: 12.9 mg, 7.3%, white solid. LC-MS (ESI) found: 337 [M+H]⁺. 1H NMR (400 MHz, methanol-d4) δ=7.62 (d, J=2.3 Hz, 1H), 7.35 (d, J=2.1 Hz, 1H), 5.32 (d, J=1.3 Hz, 1H), 4.01-3.92 (m, 3H), 3.89-3.83 (m, 4H), 3.76 (d, J=8.0 Hz, 1H), 3.72-3.66 (m, 1H).

Preparation of A45: (1S,2R,3R,4R,5S)-4-(benzo[d]oxazol-2-ylamino)-1-(hydroxymethyl)-6,8-dioxabicyclo[3.2.1]octane-2,3-diol

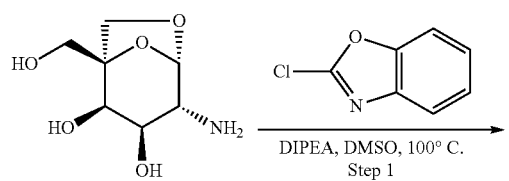

DIPEA, DMSO, 100° C.
Step 1

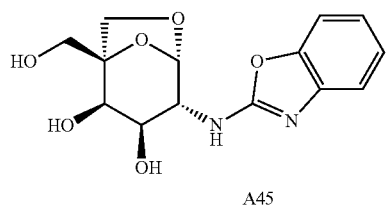

A45

Step 1: To a solution of 1S,2R,3R,4R,5S)-4-amino-1-(hydroxymethyl)-6,8-dioxabicyclo[3.2.1]octane-2,3-diol (100 mg, 523.06 umol) and 2-chloro-1,3-benzoxazole (120.49 mg, 784.60 umol, 89.25 uL) was added DIPEA (162.24 mg, 1.26 mmol, 218.65 uL, 2.4 eq) and ethyl 4-chloro-2-(trifluoromethyl)pyrimidine-5-carboxylate (199.75 mg, 784.60 umol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). A45: (1S,2R,3R,4R,5S)-4-(benzo[d]oxazol-2-ylamino)-1-(hydroxymethyl)-6,8-dioxabicyclo[3.2.1]octane-2,3-diol, Yield: 38.13 mg, 23.65% yield pale yellow solid. LC-MS (ESI) found: 309 [M+H]⁺. ¹H NMR (400 MHz, METHANOL-d4) δ=7.41 (d, J=7.9 Hz, 1H), 7.37-7.33 (m, 1H), 7.32-7.25 (m, 1H), 7.24-7.18 (m, 1H), 5.48 (s, 1H), 4.00-3.93 (m, 2H), 3.92 (d, J=1.8 Hz, 2H), 3.89-3.83 (m, 2H), 3.76 (d, J=8.1 Hz, 1H).

Preparation of A46: (1S,2R,3R,4R,5S)-1-(hydroxymethyl)-4-((4-methoxy-6-(trifluoromethyl)pyrimidin-2-yl)amino)-6,8-dioxabicyclo[3.2.1]octane-2,3-diol

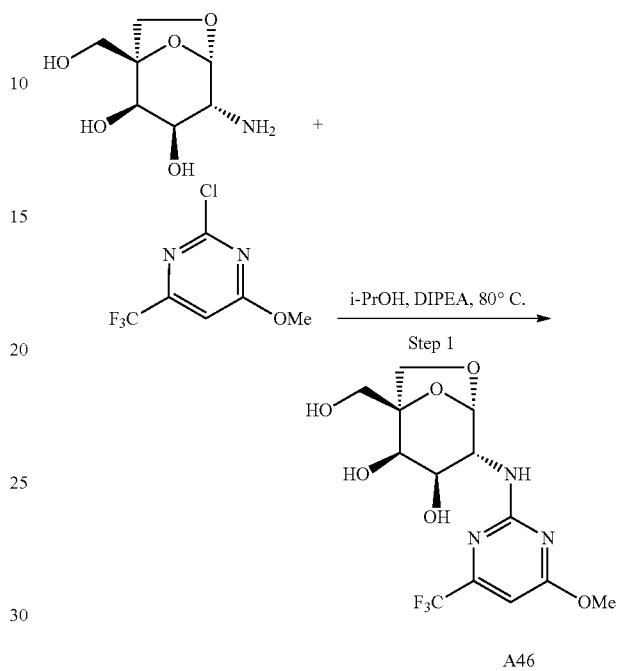

A46

Step 1: To a solution of (1S,2R,3R,4R,5S)-4-amino-1-(hydroxymethyl)-6,8-dioxabicyclo[3.2.1]octane-2,3-diol (50 mg, 0.26 mmol), 2-chloro-4-methoxy-6-(trifluoromethyl)pyrimidine (164 mg, 0.78 mmol) and DIPEA (169 mg, 1.3 mmol) in i-PrOH (1 mL) was stirred at 80° C. overnight. The mixture was concentrated and the residue was purified by prep-TLC to afford (1S,2R,3R,4R,5S)-1-(hydroxymethyl)-4-((4-methoxy-6-(trifluoromethyl)pyrimidin-2-yl)amino)-6,8-dioxabicyclo[3.2.1]octane-2,3-diol (A46, 12 mg, 13% yield) as a yellow solid. LC-MS (ESI) found: 368 [M+H]⁺. ¹H NMR (400 MHz, CD₃OD): δ 6.34 (s, 1H), 5.40 (s, 1H), 4.20 (d, J=6.8 Hz, 1H), 4.04-3.89 (m, 5H), 3.87-3.77 (m, 3H), 3.71 (d, J=7.9 Hz, 1H).

Preparation of A47: (1S,2R,3R,4R,5S)-1-(hydroxymethyl)-4-((6-methoxy-2-(trifluoromethyl)pyrimidin-4-yl)amino)-6,8-dioxabicyclo[3.2.1]octane-2,3-diol

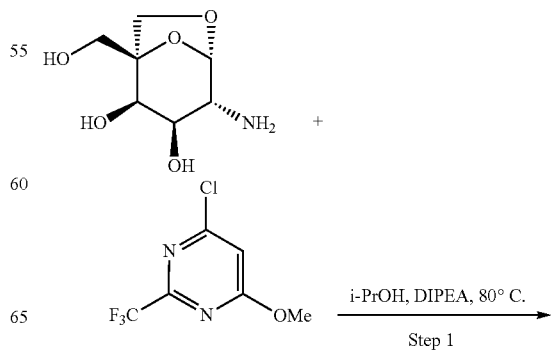

i-PrOH, DIPEA, 80° C.
Step 1

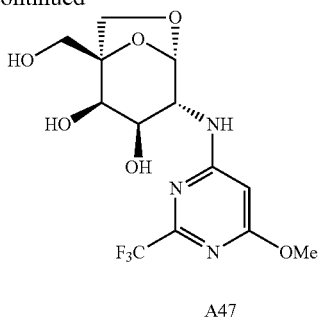

A47

Step 1: To a solution of (1S,2R,3R,4R,5S)-4-amino-1-(hydroxymethyl)-6,8-dioxabicyclo[3.2.1]octane-2,3-diol (50 mg, 0.26 mmol), 2-chloro-4-methoxy-6-(trifluoromethyl)pyrimidine (164 mg, 0.78 mmol) and DIPEA (169 mg, 1.3 mmol) in i-PrOH (1 mL) was stirred at 80° C. overnight. The mixture was concentrated and the residue was purified by prep-TLC to give (1S,2R,3R,4R,5S)-1-(hydroxymethyl)-4-((6-methoxy-2-(trifluoromethyl)pyrimidin-4-yl)amino)-6,8-dioxabicyclo[3.2.1]octane-2,3-diol (A47, 6 mg, 7% yield) as a yellow solid. LC-MS (ESI) found: 368 [M+H]$^+$. $^1$H NMR (400 MHz, CD$_3$OD): δ 5.97 (s, 1H), 5.32 (s, 1H), 4.24 (d, J=21.2 Hz, 1H), 3.96-3.88 (m, 5H), 3.85-3.76 (m, 3H), 3.71 (d, J=7.9 Hz, 1H).

Preparation of A48: methyl 2-(((3S,4R,5R,6R)-4,5-dihydroxy-6-(hydroxymethyl)tetrahydro-2H-pyran-3-yl)amino)-6-methoxypyrimidine-4-carbimidate

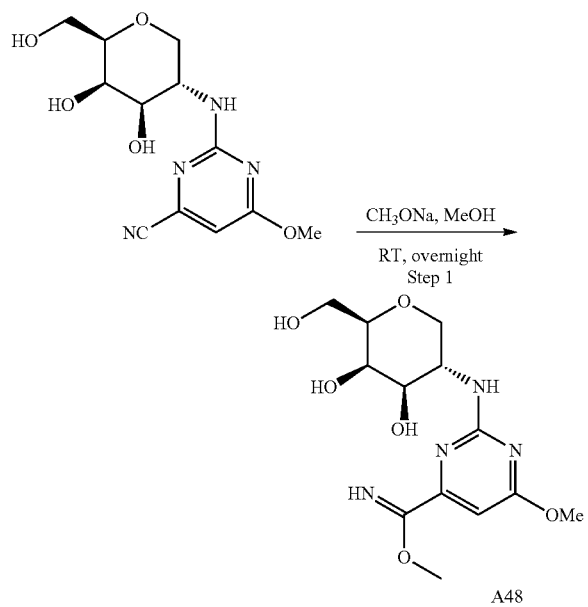

A48

Step 1: To a stirred solution of 2-(((3S,4R,5R,6R)-4,5-dihydroxy-6-(hydroxymethyl)tetrahydro-2H-pyran-3-yl)amino)-6-methoxypyrimidine-4-carbonitrile (30 mg, 0.01 mol) in MeOH (5 mL) at rt under N$_2$ atmosphere was added CH$_3$ONa (36 mg, 0.2 mmol). After the addition was complete, the reaction was stirred at rt overnight. On consumption of starting material (LCMS monitoring), the mixture was concentrated in vacuo. The crude product was directly purified by pre-HPLC under basic condition to give methyl 2-(((3S,4R,5R,6R)-4,5-dihydroxy-6-(hydroxymethyl)tetrahydro-2H-pyran-3-yl)amino)-6-methoxypyrimidine-4-carboxylate as a whit solid (A48, 1.5 mg, 5% yield). LC-MS (ESI) found: 329 [M+H]$^+$. $^1$H NMR (400 MHz, CD$_3$OD): δ 6.43 (s, 1H), 4.42 (s, 1H), 4.13 (dd, J=11.0, 5.3 Hz, 1H), 3.94 (d, J=23.7 Hz, 4H), 3.73 (ddd, J=16.4, 11.4, 6.1 Hz, 2H), 3.63 (dd, J=10.6, 3.2 Hz, 1H), 3.51-3.40 (m, 1H), 3.36-3.30 (m, 3H), 3.14 (dd, J=12.8, 9.0 Hz, 1H).

Preparation of A49: (2R,3R,4R,5S)-2-(hydroxymethyl)-5-(pyrrolo[2,1-f][1,2,4]triazin-4-ylamino)tetrahydro-2H-pyran-3,4-diol

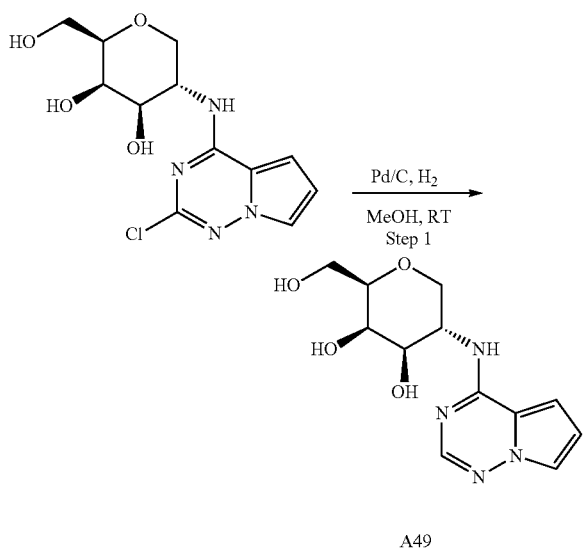

A49

Step 1: To a solution of (2R,3R,4R,5S)-5-((2-chloropyrrolo[2,1-f][1,2,4]triazin-4-yl)amino)-2-(hydroxymethyl)tetrahydro-2H-pyran-3,4-diol (50 mg, 0.20 mmol) in methanol (3 mL) was added Pd/C (5 mg, 10% wt, 60% wet). The mixture was stirred at RT under a H$_2$ balloon overnight. The After filtration, the solvent was concentrated and the residual was purified by chromatography on (silica gel, 0-20% methanol in methylene chloride) to give (2R,3R,4R,5S)-2-(hydroxymethyl)-5-(pyrrolo[2,1-f][1,2,4]triazin-4-ylamino)tetrahydro-2H-pyran-3,4-diol (A49, 7.1 mg, 16% yield) as a white solid. LC-MS (ESI) found: 281 [M+H]$^+$. $^1$H NMR (400 MHz, CD$_3$OD): δ 7.80 (s, 1H), 7.49 (dd, J=2.4, 1.5 Hz, 1H), 6.87 (dd, J=4.3, 1.2 Hz, 1H), 6.62 (dd, J=4.3, 2.7 Hz, 1H), 4.65 (td, J=10.7, 5.2 Hz, 1H), 4.12 (dd, J=11.0, 5.3 Hz, 1H), 3.94 (d, J=2.9 Hz, 1H), 3.75 (dtd, J=16.4, 11.4, 6.0 Hz, 3H), 3.58-3.44 (m, 1H), 3.26 (t, J=10.9 Hz, 1H).

Preparation of A50 (2R,3R,4R,5R,6S)-5-azido-2-(hydroxymethyl)-6-methyltetrahydro-2H-pyran-3,4-diol

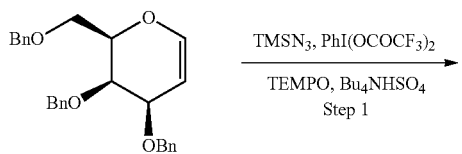

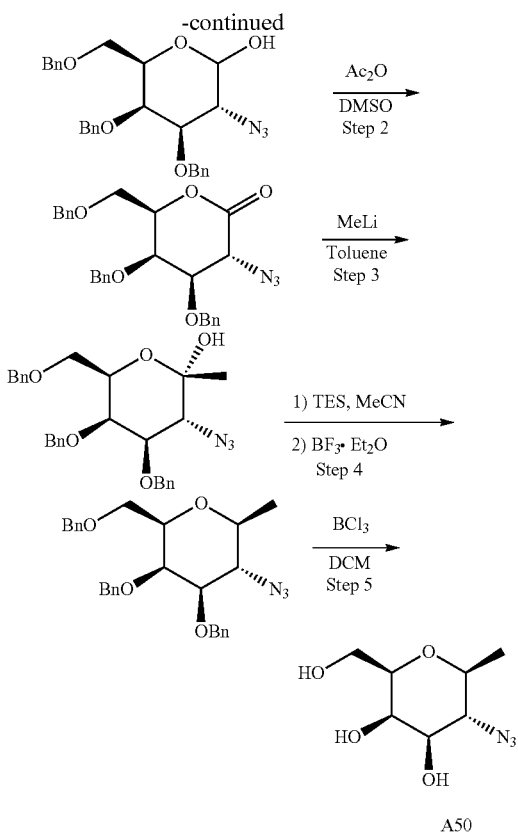

Step 1: To a stirred solution of (2R,3R,4R)-3,4-bis(benzyloxy)-2-((benzyloxy)methyl)-3,4-dihydro-2H-pyran (5 g, 12.00 mmol) and TMSN$_3$ (4.14 g, 36.01 mmol) in DCM (200 mL) was added PhI(OCOCF$_3$)$_2$ (10.32 g, 24.00 mmol), TEMPO (0.37 g, 2.40 mmol), Bu$_4$NHSO$_4$ (0.81 g, 2.40 mmol) and H$_2$O (10.81 mL, 600.21 mmol) sequentially at 0° C. After the addition was completed, the reaction mixture was stirred at 0° C. temperature for 35 min. Upon consumption of the starting material (TLC monitoring and scarlet color of the reaction mixture turning to pale yellow color), saturated aqueous NaHCO$_3$ was added and the reaction mixture further stirred for 15 min at 0° C. The reaction was extracted with CH$_2$Cl$_2$ (3×50 mL), and the combined organic extracts were washed with water (1×50 mL) and brine (1×50 mL), dried over Na$_2$SO$_4$ and the solvent evaporated. The crude product was purified by column chromatography to get the crude product (3.3 g, 37% yield). LC-MS (ESI) found: 498 [M+Na]$^+$.

Step 2: To a solution of (3R,4R,5R,6R)-3-azido-4,5-bis(benzyloxy)-6-((benzyloxy)methyl)tetrahydro-2H-pyran-2-ol (3.3 g, 6.95 mmol) in DMSO (16 mL) was added Ac$_2$O (16 mL). The reaction was stirred at room temperature for 18 h. The reaction was diluted with EA and water. The organic layer was separated concentrated in vacuo. The residue was purified using silica gel column chromatography eluting with [PE:EA=5:1] to afford the title compound (3R,4R,5R,6R)-3-azido-4,5-bis(benzyloxy)-6-((benzyloxy)methyl)tetrahydro-2H-pyran-2-ol (1.8 g, 53% yield). LC-MS (ESI) found: 496 [M+Na]$^+$.

Step 3: To a solution of (3R,4R,5R,6R)-3-azido-4,5-bis(benzyloxy)-6-((benzyloxy)methyl)tetrahydro-2H-pyran-2-ol (1.77 g, 3.74 mmol) in Toluene (10 mL) was cooled to −78° C. MeLi (3.27 mL, 1.6 M in THF) was added dropwise with vigorous stirring. The reaction mixture was stirred at rt for 1 h, and then quenched by addition of saturated NH$_4$Cl solution. The mixture was extracted with ether, and the organic layer was dried and concentrated to give crude product (1.8 g). LC-MS (ESI) found: 490 [M+H]$^+$.

Step 4: To a solution of (2S,3S,4R,5R,6R)-3-azido-4,5-bis(benzyloxy)-6-((benzyloxy)methyl)-2-methyltetrahydro-2H-pyran (1.82 g, 3.72 mmol) in MeCN (40 mL) was added triethylsilane (2.16 g, 18.60 mmol) slowly at −40° C. The reaction was stirred for 5 min, then BF$_3$OEt$_2$ (3.17 g, 22.33 mmol) was added. The mixture was stirred at rt for 18 h. The reaction was diluted with DCM and saturated aqueous NaHCO$_3$. The organic layer was separated and concentrated in vacuo. The residue was purified using silica gel column chromatography eluting with ethyl acetate in petroleum ether to afford the title compound (1.37 g, 78% yield). LC-MS (ESI) found: 496 [M+Na]$^+$.

Step 5: To a solution of (2S,3S,4R,5R,6R)-3-azido-4,5-bis(benzyloxy)-6-((benzyloxy)methyl)-2-methyltetrahydro-2H-pyran (10 mg, 0.021 mmol) in DCM (10 mL) was added BCl$_3$ (7.93 mL, 1 M in DCM) The reaction was stirred at 0° C. for 3 h. The reaction was diluted with saturated aqueous Na$_2$CO$_3$. The reaction was diluted with EA and water. The organic layer was separated and concentrated in vacuo. The residue was purified using silica gel column chromatography eluting with methanol in dichloromethane to afford the title compound (2R,3R,4R,5R,6S)-5-azido-2-(hydroxymethyl)-6-methyltetrahydro-2H-pyran-3,4-diol (A50, 120 mg, 0.59 mmol, 74% yield). LC-MS (ESI) found: 226 [M+Na]$^+$. $^1$H NMR (400 MHz, CD$_3$OD): δ 3.83 (d, J=2.7 Hz, 1H), 3.67 (qd, J=11.3, 6.1 Hz, 2H), 3.53 (dd, J=9.5, 3.3 Hz, 1H), 3.42 (ddd, J=6.6, 5.3, 1.0 Hz, 1H), 3.28-3.13 (m, 2H), 1.30 (d, J=5.9 Hz, 3H).

Preparation of A51: (2R,3R,4R,5R,6S)-5-amino-2-(hydroxymethyl)-6-methyloxane-3,4-diol

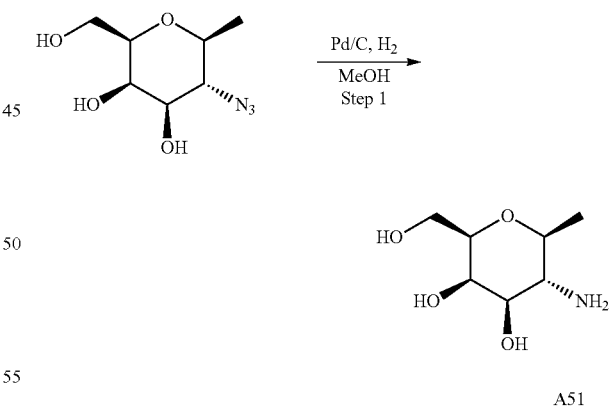

Step 1: To a solution of (2R,3R,4R,5R,6S)-5-azido-2-(hydroxymethyl)-6-methyltetrahydro-2H-pyran-3,4-diol (120 mg, 0.59 mmol) in MeOH (3 mL) was added Pd/C (12 mg, 10% wt., 60% wet). The reaction was stirred at room temperature under H$_2$ balloon for 1 h. The reaction was filtered. The residue was concentrated in vacuo to afford the title compound (2R,3R,4R,5R,6S)-5-amino-2-(hydroxymethyl)-6-methyloxane-3,4-diol (A51, 70 mg, 66% yield). LC-MS (ESI) found: 178 [M+H]$^+$.

Preparation of A52: (2R,3R,4R,5R,6S)-6-(allyloxy)-5-amino-2-(hydroxymethyl)tetrahydro-2H-pyran-3,4-diol and A53: (2R,3R,4R,5R,6S)-6-(allyloxy)-5-((3-chloro-1,2,4-thiadiazol-5-yl)amino)-2-(hydroxymethyl)tetrahydro-2H-pyran-3,4-diol

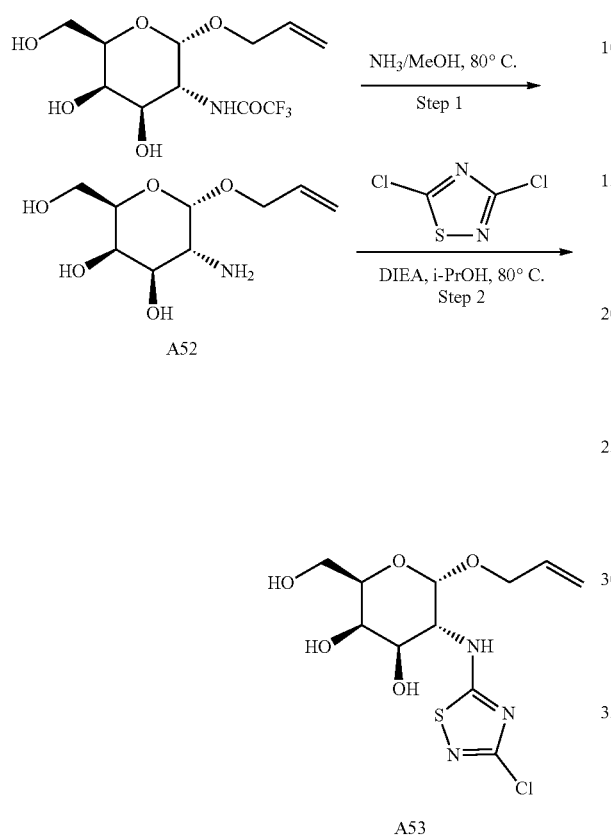

Step 1: To a solution of N-((2S,3R,4R,5R,6R)-2-(allyloxy)-4,5-dihydroxy-6-(hydroxymethyl)tetrahydro-2H-pyran-3-yl)-2,2,2-trifluoroacetamide (200 mg, 0.6 mmol) in NH₃/MeOH (6 mL, 7 M) was stirred at 80° C. overnight in a sealed tube. The mixture was concentrated and purified by C18 column to give (2R,3R,4R,5R,6S)-6-(allyloxy)-5-amino-2-(hydroxymethyl)tetrahydro-2H-pyran-3,4-diol (A52, 50 mg, 36% yield) as a white solid. LC-MS (ESI) found: 220 [M+H]⁺.

Step 2: To a mixture of (2R,3R,4R,5R,6S)-6-(allyloxy)-5-amino-2-(hydroxymethyl)tetrahydro-2H-pyran-3,4-diol (30 mg, 0.1 mmol), 3,5-dichloro-1,2,4-thiadiazole (31 mg, 0.2 mmol) and DIEA (39 mg, 0.3 mmol) in isopropanol (3 mL) was stirred at 80° C. overnight in a sealed tube. The mixture was concentrated and purified by silical gel column (0-20% methanol in methylene chloride) to give (2R,3R,4R,5R,6S)-6-(allyloxy)-5-((3-chloro-1,2,4-thiadiazol-5-yl)amino)-2-(hydroxymethyl)tetrahydro-2H-pyran-3,4-diol (A53, 1.1 mg, 2% yield) as a white solid. LC-MS (ESI) found: 338 [M+H]⁺. ¹H NMR (400 MHz, CD₃OD): δ 5.93 (ddd, J=21.9, 10.8, 5.7 Hz, 1H), 5.30 (dd, J=17.2, 1.7 Hz, 1H), 5.16 (dd, J=10.4, 1.6 Hz, 1H), 5.01 (d, J=3.6 Hz, 1H), 4.22 (dd, J=13.1, 5.1 Hz, 2H), 4.02 (dd, J=13.0, 6.2 Hz, 1H), 3.92 (d, J=2.8 Hz, 1H), 3.89-3.83 (m, 2H), 3.78-3.68 (m, 2H).

Preparation of A54: 2-(((3S,4R,5R,6R)-4,5-dihydroxy-6-(hydroxymethyl)tetrahydro-2H-pyran-3-yl)amino)-4-(trifluoromethyl)thiazole-5-carboxamide

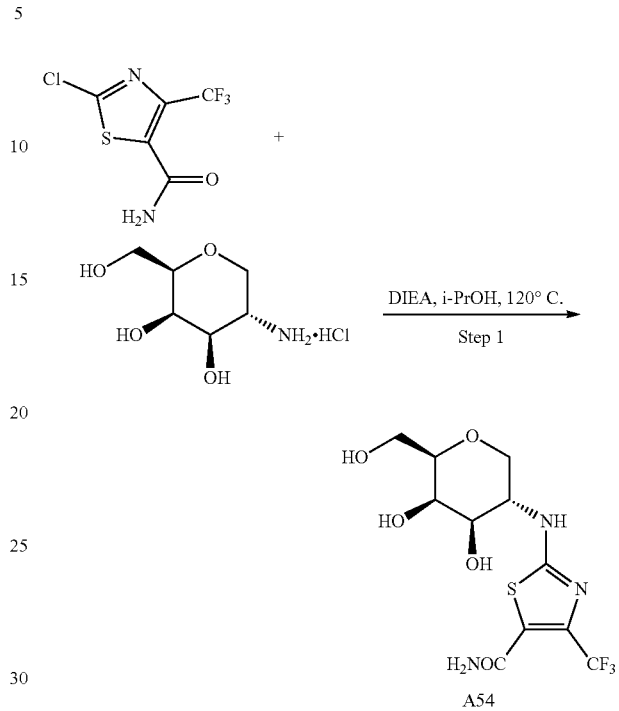

Step 1: To a solution of (2R,3R,4R,5R,6S)-6-(allyloxy)-5-amino-2-(hydroxymethyl)tetrahydro-2H-pyran-3,4-diol (100 mg, 0.60 mmol), 2-chloro-4-(trifluoromethyl)thiazole-5-carboxamide (206 mg, 0.90 mmol) and DIEA (232 mg, 1.8 mmol) in isopropanol (3 mL) was stirred at 120° C. overnight in tube. The mixture was concentrated and purified by chromatography on (silica gel, 0-20% methanol in methylene chloride) to give 2-(((3S,4R,5R,6R)-4,5-dihydroxy-6-(hydroxymethyl)tetrahydro-2H-pyran-3-yl)amino)-4-(trifluoromethyl)thiazole-5-carboxamide (A54, 1.7 mg, 1% yield) as a white solid. LC-MS (ESI) found: 358 [M+H]⁺. ¹H NMR (400 MHz, CD₃OD): δ 4.15 (dd, J=11.0, 5.2 Hz, 1H), 4.05 (td, J=10.4, 5.0 Hz, 1H), 3.89 (d, J=3.0 Hz, 1H), 3.74 (dd, J=11.4, 7.1 Hz, 1H), 3.67 (dd, J=11.4, 5.0 Hz, 1H), 3.57 (dd, J=10.3, 3.2 Hz, 1H), 3.43 (dd, J=6.2, 5.2 Hz, 1H), 3.14 (t, J=10.8 Hz, 1H).

Preparation of A55: (2R,3R,4R,5R,6S)-2-(hydroxymethyl)-6-methyl-5-((4-(trifluoromethyl)pyrimidin-2-yl)amino)tetrahydro-2H-pyran-3,4-diol

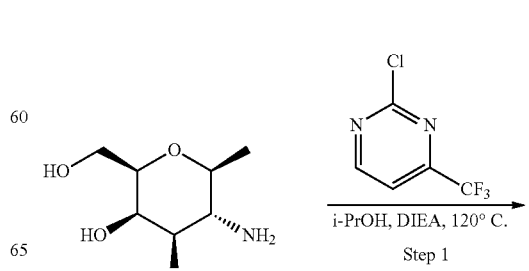

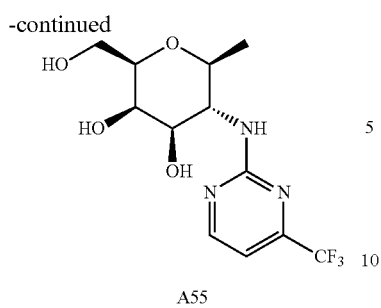

A55

Step 1: To a solution of (2R,3R,4R,5R,6S)-5-amino-2-(hydroxymethyl)-6-methyltetrahydro-2H-pyran-3,4-diol (35 mg, 0.20 mmol) in i-PrOH (2 mL) was added 2-chloro-4-(trifluoromethyl)pyrimidine (0.03 mL, 0.24 mmol) and DIEA (0.10 mL, 0.59 mmol) at rt, and the mixture was stirred at 120° C. overnight. The mixture was concentrated and the residue was purified by prep-TLC with 10% MeOH in DCM to get (2R,3R,4R,5R,6S)-2-(hydroxymethyl)-6-methyl-5-((4-(trifluoromethyl)pyrimidin-2-yl)amino)tetrahydro-2H-pyran-3,4-diol (A55, 10 mg, 16% yield) as white solid. LC-MS (ESI) found: 324 [M+H]$^+$. $^1$H NMR (400 MHz, CD$_3$OD): δ 8.49 (d, J=4.7 Hz, 1H), 6.86 (d, J=4.8 Hz, 1H), 4.18 (s, 1H), 3.90 (d, J=2.8 Hz, 1H), 3.90 (d, J=2.8 Hz, 1H), 3.78-3.69 (m, 2H), 3.72 (ddd, J=16.5, 11.3, 6.1 Hz, 2H), 3.67 (d, J=5.3 Hz, 1H), 3.51-3.48 (m, 1H), 3.45 (dd, J=12.4, 6.2 Hz, 1H), 1.22 (d, J=6.2 Hz, 3H).

Preparation of A56: (2R,3R,4R,5R,6S)-5-((3-chloro-1,2,4-thiadiazol-5-yl)amino)-2-(hydroxymethyl)-6-methyltetrahydro-2H-pyran-3,4-diol

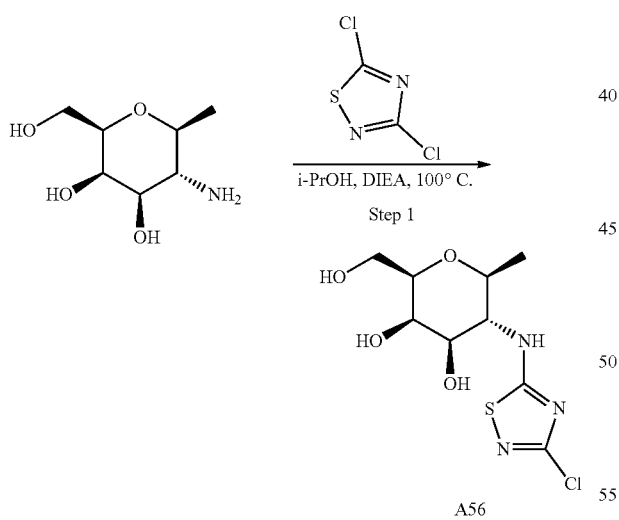

A56

Step 1: To the solution of (2R,3R,4R,5R,6S)-5-amino-2-(hydroxymethyl)-6-methyltetrahydro-2H-pyran-3,4-diol (35 mg, 0.20 mmol) of i-PrOH (2 mL) were added dichloro-1,2,4-thiadiazole (0.02 mL, 0.24 mmol) and DIEA (0.10 mL, 0.59 mmol) and the mixture was stirred at 100° C. overnight. The mixture was concentrated for column chromatography purified with 40% MeOH in H$_2$O to get (2R,3R,4R,5R,6S)-5-((3-chloro-1,2,4-thiadiazol-5-yl)amino)-2-(hydroxymethyl)-6-methyltetrahydro-2H-pyran-3,4-diol (A56, 6 mg, 11% yield) as white solid. LC-MS (ESI) found: 296 [M+H]$^+$. $^1$H NMR (400 MHz, CD$_3$OD): δ 3.88 (d, J=2.0 Hz, 1H), 3.73 (dd, J=11.3, 6.9 Hz, 1H), 3.69 (d, J=5.2 Hz, 1H), 3.63 (dd, J=22.4, 4.1 Hz, 1H), 3.59-3.53 (m, 1H), 3.48 (d, J=5.7 Hz, 1H), 3.44 (dd, J=8.8, 2.6 Hz, 1H), 1.26 (d, J=5.9 Hz, 3H).

Preparation of A57: N-((2S,3R,4R,5R,6R)-2-(allyloxy)-4,5-dihydroxy-6-((4-(3-methoxyphenyl)-1H-1,2,3-triazol-1-yl)methyl)tetrahydro-2H-pyran-3-yl)-2,2,2-trifluoroacetamide

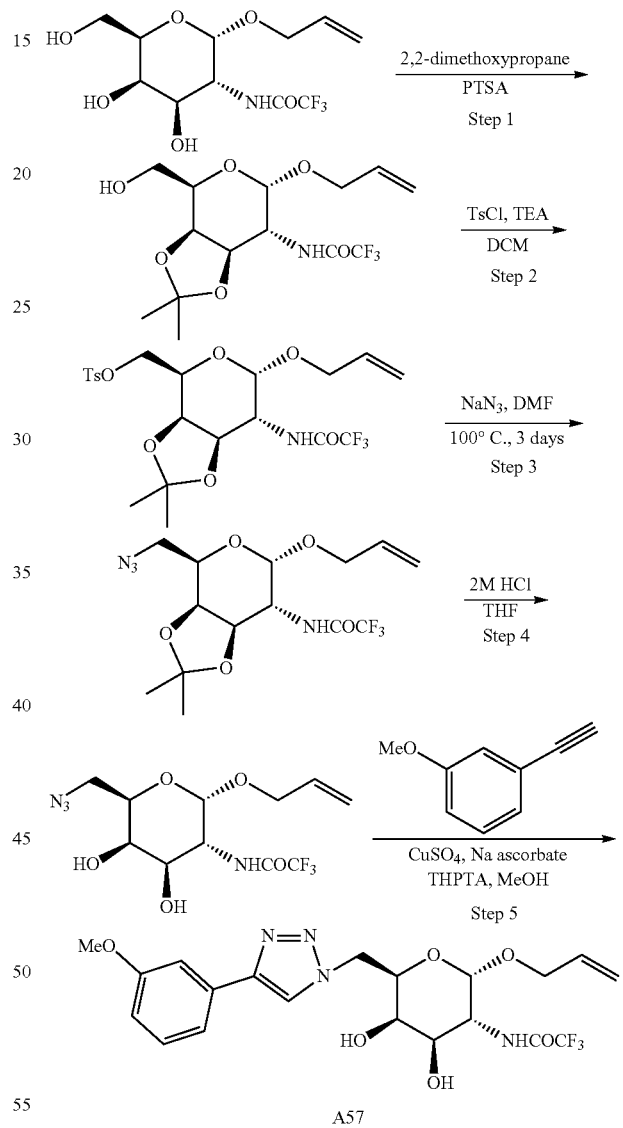

A57

Step 1: To a solution of N-((2S,3R,4R,5R,6R)-2-(allyloxy)-4,5-dihydroxy-6-(hydroxymethyl)tetrahydro-2H-pyran-3-yl)-2,2,2-trifluoroacetamide (2.5 g, 7.9 mmol) in 2,2-Dimethyoxypropane (40 mL) was added TsOH (0.14 g, 0.8 mmol) at 0° C. The mixture was stirred at rt for 3 h. The remained TsOH was neutralized by TEA. The mixture was concentrated and the residual was purified by chromatography on (silica gel, 0-100% ethyl acetate in petroleum ether) to give N-((3aR,4R,6S,7R,7aR)-6-(allyloxy)-4-(hydroxymethyl)-2,2-dimethyltetrahydro-4H-[1,3]dioxolo[4,5-c]

pyran-7-yl)-2,2,2-trifluoroacetamide (1.7 g, 60% yield) as solid. LC-MS (ESI) found: 354 [M–H]⁻.

Step 2: To a solution of N-((3aR,4R,6S,7R,7aR)-6-(allyloxy)-4-(hydroxymethyl)-2,2-dimethyltetrahydro-4H-[1,3]dioxolo[4,5-c]pyran-7-yl)-2,2,2-trifluoroacetamide (1.7 g, 4.8 mmol) in DCM (30 mL) was added TsCl (0.9 g, 4.8 mmol) and TEA (2 mL, 14.4 mmol) at 0° C. The mixture was stirred at rt for 12 h. The mixture was concentrated and the residual was purified by chromatography on (silica gel, 0-100% ethyl acetate in petroleum ether) to give ((3aR,4R,6S,7R,7aR)-6-(allyloxy)-2,2-dimethyl-7-(2,2,2-trifluoroacetamido)tetrahydro-4H-[1,3]dioxolo[4,5-c]pyran-4-yl)methyl 4-methylbenzenesulfonate (1.8 g, 74% yield) as solid. LC-MS (ESI) found: 509 [M–H]⁻.

Step 3: To a solution of ((3aR,4R,6S,7R,7aR)-6-(allyloxy)-2,2-dimethyl-7-(2,2,2-trifluoroacetamido)tetrahydro-4H-[1,3]dioxolo[4,5-c]pyran-4-yl)methyl 4-methylbenzenesulfonate (1.8 g, 3.5 mmol) in DMSO (10 mL) was added NaN₃ (2.3 g, 35 mmol) in H₂O (4 mL). The mixture was stirred at 100° C. for 36 h. The mixture was diluted with H₂O, extracted with EA, purified by chromatography on (silica gel, 0-100% ethyl acetate in petroleum ether) to give N-((3aS,4R,6S,7R,7aR)-6-(allyloxy)-4-(azidomethyl)-2,2-dimethyltetrahydro-4H-[1,3]dioxolo[4,5-c]pyran-7-yl)-2,2,2-trifluoroacetamide (640 mg, 48% yield) as solid. LC-MS (ESI) found: 379 [M–H]⁻.

Step 4: To a solution of N-((3aS,4R,6S,7R,7aR)-6-(allyloxy)-4-(azidomethyl)-2,2-dimethyltetrahydro-4H-[1,3]dioxolo[4,5-c]pyran-7-yl)-2,2,2-trifluoroacetamide (640 mg, 1.7 mmol) in THF (20 mL) was added HCl (1 mL, 2 M in H₂O), the mixture was stirred at rt for 12 h. The mixture was neutralized with saturated aqueous NaHCO₃, extracted with EA, dried over Na₂SO₄, purified by chromatography on (silica gel, 0-100% ethyl acetate in petroleum ether) to give N-((2S,3R,4R,5R,6R)-2-(allyloxy)-6-(azidomethyl)-4,5-dihydroxytetrahydro-2H-pyran-3-yl)-2,2,2-trifluoroacetamide (300 mg, 52% yield) as solid. LC-MS (ESI) found: 339 [M–H]⁻. ¹H NMR (400 MHz, DMSO-d₆): δ 9.38 (s, 1H), 5.86 (dddd, J=15.3, 10.5, 5.7, 4.8 Hz, 1H), 5.32 (ddd, J=17.3, 3.5, 1.7 Hz, 1H), 5.17 (dd, J=10.5, 1.7 Hz, 1H), 5.00 (d, J=4.4 Hz, 1H), 4.83 (t, J=4.9 Hz, 2H), 4.19-4.05 (m, 2H), 4.02-3.95 (m, 1H), 3.93-3.82 (m, 2H), 3.71 (s, 1H), 3.53 (dd, J=12.8, 9.0 Hz, 1H), 3.28 (dd, J=12.8, 3.6 Hz, 1H). ¹⁹F NMR (377 MHz, DMSO-d₆): δ −73.84.

Step 5: To a solution of THPTA (10 mg, 0.020 mmol) and CuSO₄ (1 mg, 0.0040 mmol) were dissolved in water (0.5 mL). The mixture was added to a solution of N-((2S,3R,4R,5R,6R)-2-(allyloxy)-6-(azidomethyl)-4,5-dihydroxytetrahydro-2H-pyran-3-yl)-2,2,2-trifluoroacetamide (20 mg, 0.060 mmol) and 1-ethynyl-3-methoxybenzene (12 mg, 0.090 mmol) in MeOH (4 mL). A freshly-prepared solution of Na ascorbate (2 mg, 0.010 mmol) in water (0.5 mL) was added. The reaction was stirred overnight. The resulting mixture was filtered. The crude product was purified by chromatography on (silica gel, 0-100% ethyl acetate in petroleum ether) to give N-((2S,3R,4R,5R,6R)-2-(allyloxy)-4,5-dihydroxy-6-((4-(3-methoxyphenyl)-1H-1,2,3-triazol-1-yl)methyl)tetrahydro-2H-pyran-3-yl)-2,2,2-trifluoroacetamide (A57, 18 mg, 67% yield) as a white solid. LC-MS (ESI) found: 473 [M+H]⁺. ¹H NMR (400 MHz, CD₃OD): δ 8.35 (s, 1H), 7.55-7.22 (m, 3H), 6.91 (ddd, J=7.9, 2.5, 1.3 Hz, 1H), 5.65 (ddt, J=16.6, 10.4, 5.8 Hz, 1H), 5.15-4.96 (m, 2H), 4.89 (d, J=3.7 Hz, 1H), 4.72-4.66 (m, 2H), 4.34 (dd, J=10.5, 3.7 Hz, 1H), 4.28 (dd, J=8.2, 4.8 Hz, 1H), 4.04-3.94 (m, 2H), 3.84 (s, 3H), 3.79-3.72 (m, 1H), 3.67 (dd, J=13.0, 6.2 Hz, 1H). ¹⁹F NMR (377 MHz, CD₃OD) δ −77.00.

Preparation of A58: N-((2S,3R,4R,5R,6R)-2-(allyloxy)-4,5-dihydroxy-6-((4-(3-methoxyphenyl)-1H-1,2,3-triazol-1-yl)methyl)tetrahydro-2H-pyran-3-yl)-2,2,2-trifluoroacetamide

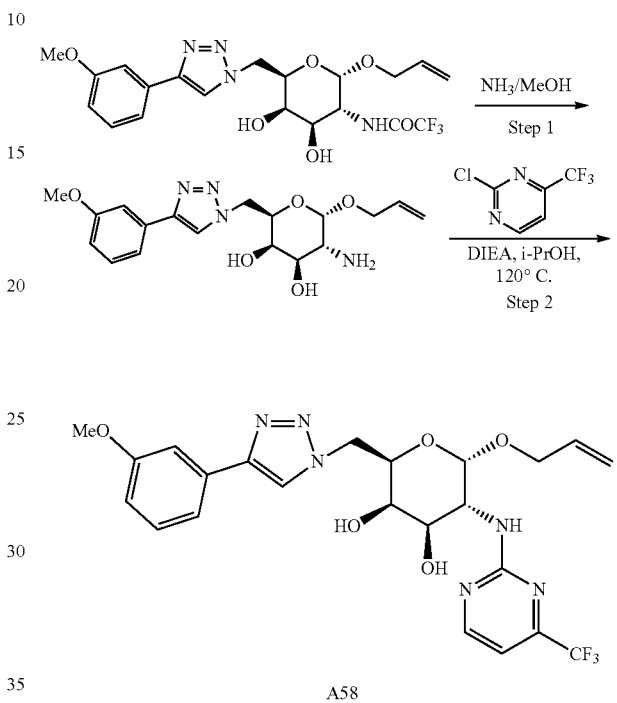

A58

Step 1: To a solution of N-((2S,3R,4R,5R,6R)-2-(allyloxy)-4,5-dihydroxy-6-((4-(3-methoxyphenyl)-1H-1,2,3-triazol-1-yl)methyl)tetrahydro-2H-pyran-3-yl)-2,2,2-trifluoroacetamide (15 mg, 0.030 mmol) in NH₃/MeOH solution (3 mL, 7 M). The mixture was stirred at 80° C. overnight in a sealed tube. The mixture was concentrated to give crude (2R,3R,4R,5R,6S)-6-(allyloxy)-5-amino-2-((4-(3-methoxyphenyl)-1H-1,2,3-triazol-1-yl)methyl)tetrahydro-2H-pyran-3,4-diol (12 mg) as a white solid. LC-MS (ESI) found: 377 [M+H]⁺.

Step 2: To a solution of (2R,3R,4R,5R,6S)-6-(allyloxy)-5-amino-2-((4-(3-methoxyphenyl)-1H-1,2,3-triazol-1-yl)methyl)tetrahydro-2H-pyran-3,4-diol (12 mg, 0.030 mmol), 2-chloro-4-(trifluoromethyl)pyrimidine (9 mg, 0.050 mmol) and DIEA (12 mg, 0.10 mmol) in isopropanol (3 mL) was stirred at 120° C. overnight in a sealed tube. The mixture was concentrated and purified by chromatography on (silica gel, 0-20% methanol in methylene chloride) to give (2R,3R,4R,5R,6S)-6-(allyloxy)-2-((4-(3-methoxyphenyl)-1H-1,2,3-triazol-1-yl)methyl)-5-((4-(trifluoromethyl)pyrimidin-2-yl)amino)tetrahydro-2H-pyran-3,4-diol (A58, 1.7 mg, 1% yield) as a white solid. LC-MS (ESI) found: 523 [M+H]⁺. ¹H NMR (400 MHz, CD₃OD): δ 8.51 (d, J=4.5 Hz, 1H), 8.36 (s, 1H), 7.48-7.18 (m, 3H), 7.02-6.78 (m, 2H), 5.63 (d, J=5.8 Hz, 1H), 4.98 (dd, J=28.5, 14.0 Hz, 3H), 4.74-4.69 (m, 2H), 4.56 (d, J=12.3 Hz, 1H), 4.30 (dd, J=8.2, 4.7 Hz, 1H), 4.01 (d, J=2.7 Hz, 1H), 3.96 (dd, J=10.8, 3.0 Hz, 1H), 3.84 (s, 3H), 3.74 (dd, J=12.9, 5.4 Hz, 1H), 3.66 (dd, J=12.7, 5.9 Hz, 1H). ¹⁹F NMR (377 MHz, CD₃OD) δ −72.34.

Preparation of A59: (2R,3R,4R,5S)-2-(azidomethyl)-5-((4-(trifluoromethyl)pyrimidin-2-yl)amino)tetrahydro-2H-pyran-3,4-diol

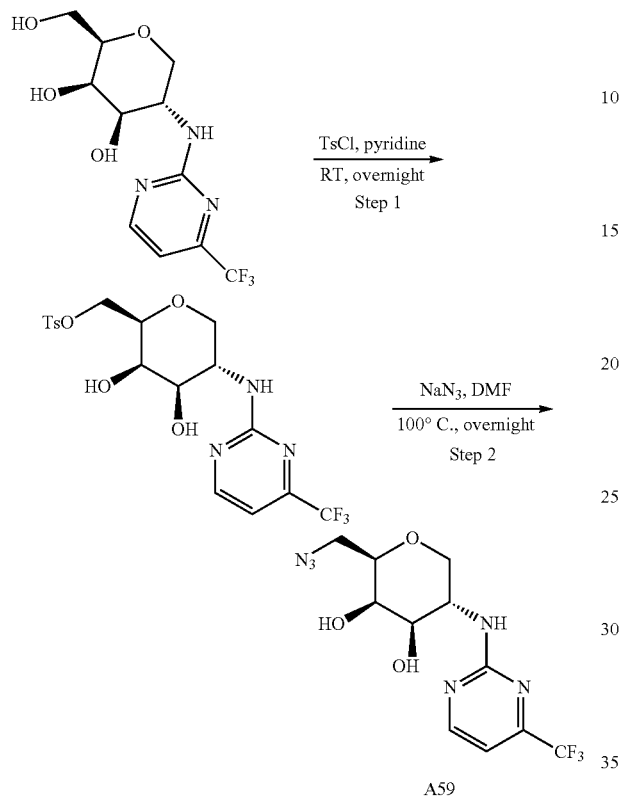

A59

Step 1: To a stirred solution of (2R,3R,4R,5S)-2-(hydroxymethyl)-5-((4-(trifluoromethyl)pyrimidin-2-yl)amino)tetrahydro-2H-pyran-3,4-diol (200 mg, 0.65 mol) in pyridine (20 mL) was added TsCl (123 mg, 0.65 mmol) at rt under $N_2$ atmosphere. After the addition was complete, the reaction was stirred at rt for overnight. On consumption of starting material (LCMS monitoring), the mixture was concentrated in vacuo. The crude product was purified by pre-HPLC to give (((2R,3R,4R,5S)-3,4-dihydroxy-5-((4-(trifluoromethyl)pyrimidin-2-yl)amino)tetrahydro-2H-pyran-2-yl)methyl 4-methylbenzenesulfonate as a white solid (100 mg, 33% yield). LC-MS (ESI) found: 464 [M+H]⁺.

Step 2: To a stirred solution of (((2R,3R,4R,5S)-3,4-dihydroxy-5-((4-(trifluoromethyl)pyrimidin-2-yl)amino)tetrahydro-2H-pyran-2-yl)methyl 4-methylbenzenesulfonate (200 mg, 0.22 mol) in DMF (2 mL) was added $NaN_3$ (140 mg, 2.2 mmol) at rt under $N_2$ atmosphere. After the addition was complete, the reaction was stirred at 100° C. overnight. On consumption of starting material (LCMS monitoring), the reaction vessel was again cooled to rt. The mixture was filtered and concentrated in vacuo. The crude product was purified by prep-HPLC to give (2R,3R,4R,5S)-2-(azidomethyl)-5-((4-(trifluoromethyl)pyrimidin-2-yl)amino)tetrahydro-2H-pyran-3,4-diol (A59, 10 mg, 14% yield). LC-MS (ESI) found: 335 [M+H]⁺. ¹H NMR (400 MHz, CD₃OD): δ 8.51 (d, J=4.8 Hz, 1H), 6.90 (d, J=4.9 Hz, 1H), 4.36 (td, J=10.6, 5.5 Hz, 1H), 4.11 (dd, J=11.0, 5.2 Hz, 1H), 3.83 (d, J=3.1 Hz, 1H), 3.67 (dd, J=10.5, 2.9 Hz, 1H), 3.63-3.52 (m, 2H), 3.34 (d, J=8.5 Hz, 1H), 3.26-3.08 (m, 1H).

Preparation of A60: (2R,3R,4R,5S)-2-(hydroxymethyl)-5-(methyl(4-(trifluoromethyl)pyrimidin-2-yl)amino)tetrahydro-2H-pyran-3,4-diol

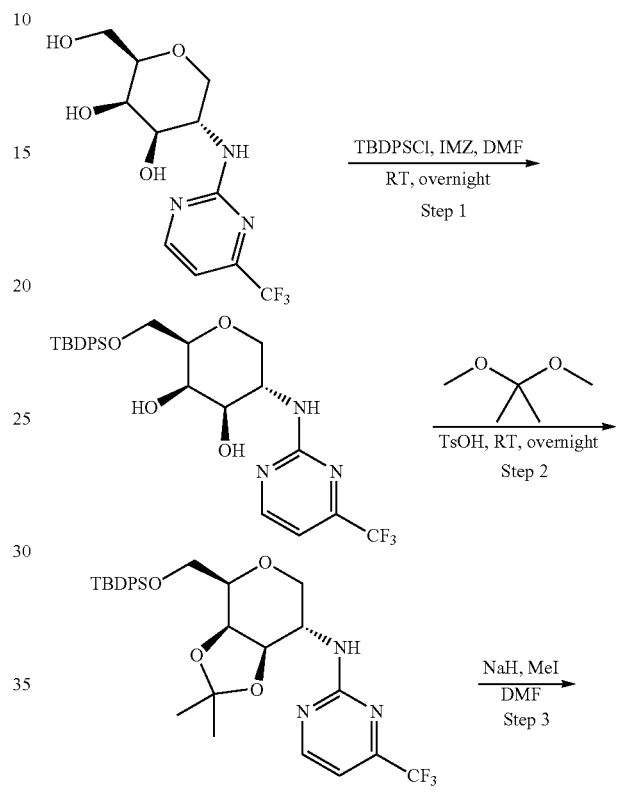

-continued

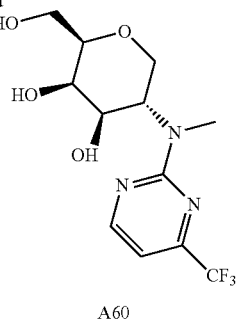

A60

Step 1: To a solution of (2R,3R,4R,5S)-2-(hydroxymethyl)-5-((4-(trifluoromethyl)pyrimidin-2-yl)amino)tetrahydro-2H-pyran-3,4-diol (1 g, 3.2 mmol) in DMF (20 mL) were added imidazole (0.44 g, 6.46 mmol) and TBDPSCl (1.26 g, 4.85 mmol). The reaction was stirred at room temperature overnight. The mixture was diluted with ethyl acetate (150 mL) and washed with water (50 mL×3). The organic layer was dried over sodium sulfate, filtered, concentrated under reduced pressure to give a crude product, which was purified by silica gel column to give (2R,3R,4R,5S)-2-(((tert-butyldiphenylsilyl)oxy)methyl)-5-((4-(trifluoromethyl)pyrimidin-2-yl)amino)tetrahydro-2H-pyran-3,4-diol (0.8 g, 45% yield) as a white solid. LC-MS (ESI) found: 548 [M+H]+.

Step 2: To a solution of (2R,3R,4R,5S)-2-(((tert-butyldiphenylsilyl)oxy)methyl)-5-((4-(trifluoromethyl)pyrimidin-2-yl)amino)tetrahydro-2H-pyran-3,4-diol (0.8 g, 1.46 mmol) in 2,2-dimethoxypropane (20 mL) was added TsOH (0.03 g, 0.14 mmol). The reaction was stirred at room temperature overnight. The mixture was concentrated under reduced pressure to give a crude product, which was purified by silica gel column to give N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)-4-(trifluoromethyl)pyrimidin-2-amine (0.6 g, 70% yield) as a colorless oil. LC-MS (ESI) found: 588 [M+H]+.

Step 3: To a solution of N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)-4-(trifluoromethyl)pyrimidin-2-amine (100.0 mg, 0.307 mmol) in DMF (10.0 mL) was added NaH (25.0 mg, 0.614 mmol, 60% wt. in mineral oil), MeI (52.0 mg, 0.368 mmol). The mixture was stirred at the room temperature for 1 h. The mixture was concentrated under reduced pressure to give a crude product, which was purified by column to give N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)-N-methyl-4-(trifluoromethyl)pyrimidin-2-amine (75 mg, 40% yield), LC-MS (ESI) found: 602 [M+H]+.

Step 4: To a solution of N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)-N-methyl-4-(trifluoromethyl)pyrimidin-2-amine (75.1 mg, 0.125 mmol) in THF (10 mL) was added TBAF (5 mL, 1 N in THF). The mixture was stirred at the room temperature for 16 h. The mixture was concentrated under reduced pressure to give a crude product, which was purified by column to give ((3aR,4R,7S,7aR)-2,2-dimethyl-7-(methyl(4-(trifluoromethyl)pyrimidin-2-yl)amino)tetrahydro-4H-[1,3]dioxolo[4,5-c]pyran-4-yl)methanol (36 mg, 80% yield). LC-MS (ESI) found: 364 [M+H]+.

Step 5: To a solution of ((3aR,4R,7S,7aR)-2,2-dimethyl-7-(methyl(4-(trifluoromethyl)pyrimidin-2-yl)amino)tetrahydro-4H-[1,3]dioxolo[4,5-c]pyran-4-yl)methanol (36.3 mg, 0.100 mmol) in THF (10 mL) was added HCl (5 mL, 2 N in H2O). The mixture was stirred rt for 16 h. The mixture was concentrated under reduced pressure, which was purified by column to give (2R,3R,4R,5S)-2-(hydroxymethyl)-5-(methyl(4-(trifluoromethyl)pyrimidin-2-yl)amino)tetrahydro-2H-pyran-3,4-diol (A60, 5 mg, 15% yield). LC-MS (ESI) found: 324[M+H]+. 1H NMR (400 MHz, D2O): δ 8.50 (d, J=5.0 Hz, 1H), 6.96 (d, J=5.0 Hz, 1H), 4.93 (s, 1H), 4.12 (d, J=9.4 Hz, 1H), 3.99 (d, J=3.2 Hz, 1H), 3.84 (dd, J=11.1, 5.2 Hz, 1H), 3.74-3.63 (m, 2H), 3.61-3.49 (m, 2H), 3.01 (s, 3H).

Preparation of A61: (2R,3R,4R,5S)-2-(1-(3-methoxyphenyl)-1H-1,2,3-triazol-4-yl)-5-((4-(trifluoromethyl)pyrimidin-2-yl)amino)tetrahydro-2H-pyran-3,4-diol

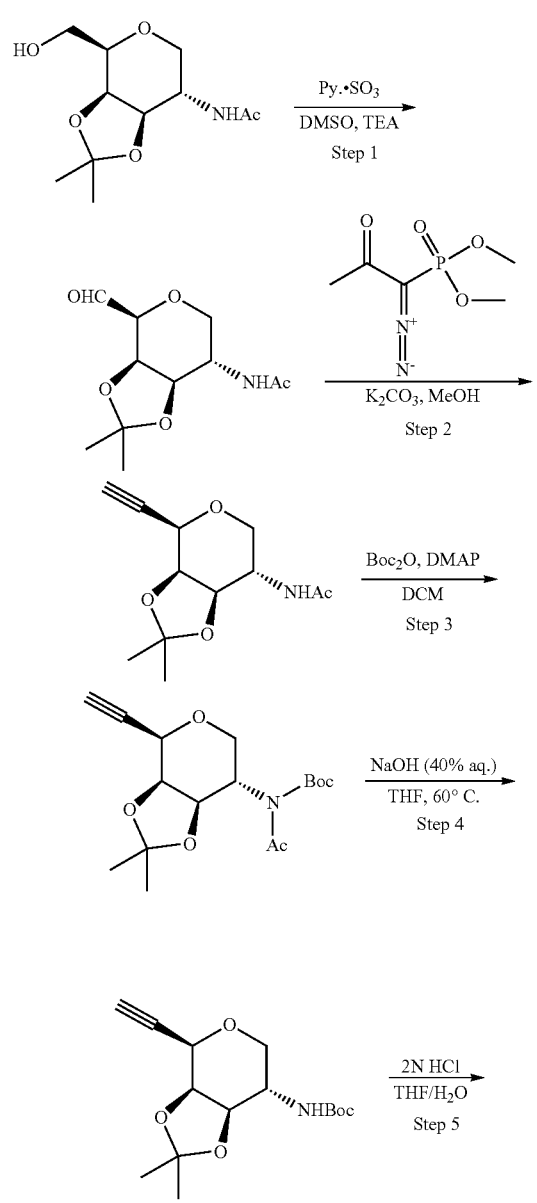

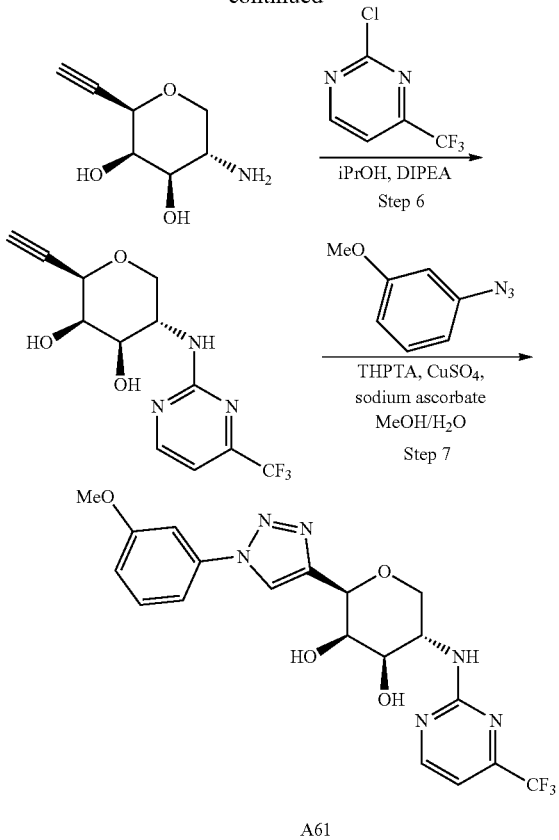

A61

Step 1: To a solution of N-((3aR,4R,7S,7aR)-4-(hydroxymethyl)-2,2-dimethyltetrahydro-4H-[1,3]dioxolo[4,5-c]pyran-7-yl)acetamide (300 mg, 1.2 mmol) in DCM (5 mL) were treated with DMSO (0.6 mL, 8.6 mmol and Et₃N (345 mg, 3.4 mmol). The mixture was cooled to 0° C. Pyridine sulfur trioxide (584 mg, 3.7 mmol) was added and the mixture was stirred at rt overnight. The reaction was quenched with brine and diluted with DCM. The aqueous phase was extracted three times with DCM and the combined organic layers were washed with brine, dried (Na₂SO₄), filtered, and evaporated to give crude N-((3aR, 4S,7S,7aR)-4-formyl-2,2-dimethyltetrahydro-4H-[1,3]dioxolo[4,5-c]pyran-7-yl)acetamide (160 mg, 54% yield) as yellow oil. LC-MS (ESI) found: 244 [M+H]⁺.

Step 2: To a solution of N-((3aR,4S,7S,7aR)-4-formyl-2,2-dimethyltetrahydro-4H-[1,3]dioxolo[4,5-c]pyran-7-yl)acetamide (160 mg, 0.66 mmol) in MeOH (3 mL) was added K₂CO₃ (109 mg, 0.79 mmol). After stirring at rt for 10 min, dimethyl (1-diazo-2-oxopropyl)phosphonate (189 mg, 0.98 mmol) was added. The mixture was stirred at rt overnight. The mixture was concentrated and the residue was purified by flash column to give N-((3aS,4R,7S,7aR)-4-ethynyl-2,2-dimethyltetrahydro-4H-[1,3]dioxolo[4,5-c]pyran-7-yl)acetamide (80 mg, 51% yield) as colorless oil. LC-MS (ESI) found: 240 [M+H]⁺.

Step 3: To a solution of N-((3aS,4R,7S,7aR)-4-ethynyl-2,2-dimethyltetrahydro-4H-[1,3]dioxolo[4,5-c]pyran-7-yl)acetamide (80 mg, 0.33 mmol) in DCM (5 mL) was added Et₃N (101 mg, 1.0 mmol), (Boc)₂O (0.715 mL, 3.344 mmol) and DMAP (4.08 mg, 0.033 mmol). The mixture was stirred at rt overnight, then concentrated. The residue was purified by flash column to give tert-butyl acetyl((3aS,4R,7S,7aR)-4-ethynyl-2,2-dimethyltetrahydro-4H-[1,3]dioxolo[4,5-c]pyran-7-yl)carbamate (80 mg, 70% yield) as colorless oil. LC-MS (ESI) found: 340 [M+H]⁺.

Step 4: To a solution of tert-butyl acetyl((3aS,4R,7S,7aR)-4-ethynyl-2,2-dimethyltetrahydro-4H-[1,3]dioxolo[4,5-c]pyran-7-yl)carbamate (80 mg, 0.23 mmol) in THF (3 mL) was added NaOH (24 mg, 0.59 mmol) in H₂O (1 mL). The mixture was stirred at 60° C. for 2 h, then extracted with EA and H₂O. The organic layer was concentrated to give crude tert-butyl ((3aS,4R,7S,7aR)-4-ethynyl-2,2-dimethyltetrahydro-4H-[1,3]dioxolo[4,5-c]pyran-7-yl)carbamate (60 mg, 68% yield) as colorless oil. LC-MS (ESI) found: 298 [M+H]⁺.

Step 5: To a solution of tert-butyl ((3aS,4R,7S,7aR)-4-ethynyl-2,2-dimethyltetrahydro-4H-[1,3]dioxolo[4,5-c]pyran-7-yl)carbamate (50 mg, 0.17 mmol) in THF (3 mL) was added HCl (1 mL, 2 N in H₂O). The mixture was stirred at rt overnight, then concentrated to give crude ((2R,3R,4R,5S)-5-amino-2-ethynyltetrahydro-2H-pyran-3,4-diol (10 mg, 38% yield) as colorless oil. LC-MS (ESI) found: 158 [M+H]⁺.

Step 6: To a solution of (2R,3R,4R,5S)-5-amino-2-ethynyltetrahydro-2H-pyran-3,4-diol (10 mg, 0.06 mmol), 2-chloro-4-(trifluoromethyl)pyrimidine (11 mg, 0.06 mmol) and DIPEA (9 mg, 0.07 mmol) in anhydrous i-PrOH (2 mL) was stirred at 80° C. overnight and then evaporated. The residue was purified by flash column to give (2R,3R,4R,5S)-2-ethynyl-5-((4-(trifluoromethyl)pyrimidin-2-yl)amino)tetrahydro-2H-pyran-3,4-diol (10 mg, 52% yield) as a colorless oil. LC-MS (ESI) found: 304 [M+H]⁺.

Step 7: To a solution of (2R,3R,4R,5S)-2-ethynyl-5-((4-(trifluoromethyl)pyrimidin-2-yl)amino)tetrahydro-2H-pyran-3,4-diol (10 mg, 0.03 mmol) and 1-azido-3-methoxybenzene (5 mg, 0.03 mmol) in MeOH (2 mL) were added CuSO₄ (1 mg, 0.003 mmol), THPTA (7 mg, 0.017 mmol) and Na ascorbate (A61, 1.3 mg, 0.007 mmol). The mixture was stirred at rt overnight, then purified by C18 column to give (2R,3R,4R,5S)-2-(1-(3-methoxyphenyl)-1H-1,2,3-triazol-4-yl)-5-((4-(trifluoromethyl)pyrimidin-2-yl)amino)tetrahydro-2H-pyran-3,4-diol (1.8 mg, 12% yield) as white solid. LC-MS (ESI) found: 453 [M+H]⁺. ¹H NMR (400 MHz, CD₃OD): δ 8.57 (s, 2H), 7.48 (t, J=8.1 Hz, 1H), 7.45-7.38 (m, 2H), 7.06 (dd, J=8.2, 1.5 Hz, 1H), 6.94 (d, J=4.9 Hz, 1H), 4.83 (d, J=9.8 Hz, 1H), 4.29 (s, 1H), 4.22 (dd, J=11.9, 2.3 Hz, 1H), 4.17 (s, 1H), 4.14-4.10 (m, 1H), 3.89 (s, 3H), 3.82 (d, J=11.8 Hz, 1H).

Preparation of A62: (2R,3R,4R,5S)-2-((4-(hydroxymethyl)-1H-pyrazol-1-yl)methyl)-5-((4-(trifluoromethyl)pyrimidin-2-yl)amino)tetrahydro-2H-pyran-3,4-diol

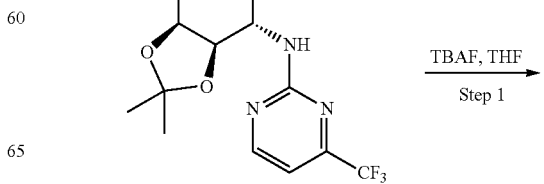

TBAF, THF
Step 1

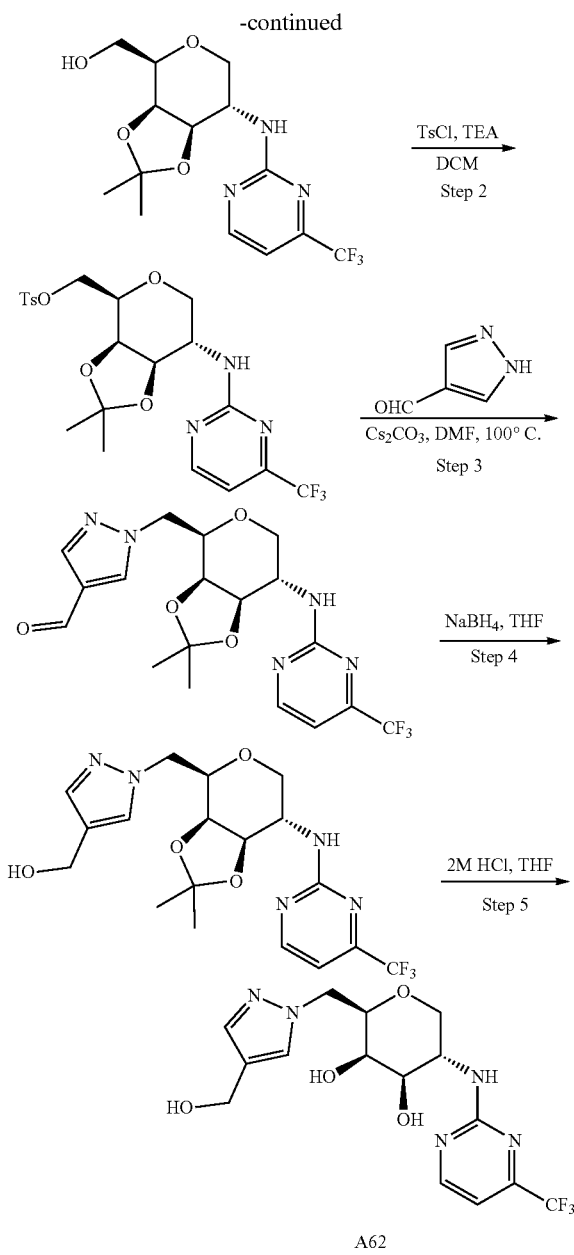

Step 1: To a solution of N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)-4-(trifluoromethyl)pyrimidin-2-amine (2.2 g, 3.7 mmol) in THF (20 mL) was added TBAF (5.6 mL, 1 M in THF). The reaction was stirred at room temperature for 3 h. The mixture was concentrated under reduced pressure to give a crude product, which was purified by flash chromatography (silica gel, 0-10% DCM in MeOH) to give ((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)methanol (1.1 g, 85% yield) as white solid. LC-MS (ESI) found: 350 [M+H]⁺.

Step 2: To a solution of ((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)methanol (1.1 g, 3.1 mmol) in pyridine (100 mL) was added TsCl (0.83 g, 4.6 mmol) at rt. The mixture was stirred at room temperature overnight. On consumption of starting material (LCMS monitoring), the mixture was concentrated under reduced pressure to give a crude product, which was purified by flash chromatography to give ((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)methyl 4-methylbenzenesulfonate (1.1 g, 73% yield) as a colorless oil. LC-MS (ESI) found: 504 [M+H]⁺.

Step 3: To a solution of ((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)methyl 4-methylbenzenesulfonate (120 mg, 0.2 mmol), 1H-pyrazole-4-carbaldehyde (28 mg, 0.3 mmol) and Cs₂CO₃ (196 mg, 0.6 mmol) in DMF (5 mL) was stirred at 100° C. overnight. The mixture was quenched with H₂O and extracted with EA. The combined organic layer was washed with brine, dried over anhydrous Na₂SO₄, filtered. The mixture was concentrated and purified by chromatography on (silica gel, 0-100% ethyl acetate in petroleum ether) to give 1-(((3aS,4R,7S,7aR)-2,2-dimethyl-7-((4-(trifluoromethyl)pyrimidin-2-yl)amino)tetrahydro-4H-[1,3]dioxolo[4,5-c]pyran-4-yl)methyl)-1H-pyrazole-4-carbaldehyde (90 mg, 89% yield) as a white solid. LC-MS (ESI) found: 428 [M+H]⁺.

Step 4: To a solution of 1-(((3aS,4R,7S,7aR)-2,2-dimethyl-7-((4-(trifluoromethyl)pyrimidin-2-yl)amino)tetrahydro-4H-[1,3]dioxolo[4,5-c]pyran-4-yl)methyl)-1H-pyrazole-4-carbaldehyde (80 mg, 0.19 mmol) in THF (5 mL) was added NaBH₄ (80 mg, 0.19 mmol) at 0° C. The mixture was stirred at rt overnight. The mixture was quenched with H₂O and extracted with EA. The combined organic layer was washed with brine, dried over anhydrous Na₂SO₄, filtered. The mixture was concentrated and purified by chromatography on (silica gel, 0-100% ethyl acetate in petroleum ether) to give (1-(((3aS,4R,7S,7aR)-2,2-dimethyl-7-((4-(trifluoromethyl)pyrimidin-2-yl)amino)tetrahydro-4H-[1,3]dioxolo[4,5-c]pyran-4-yl)methyl)-1H-pyrazol-4-yl)methanol (50 mg, 63% yield) as a white solid. LC-MS (ESI) found: 430 [M+H]⁺.

Step 5: To a solution of (1-(((3aS,4R,7S,7aR)-2,2-dimethyl-7-((4-(trifluoromethyl)pyrimidin-2-yl)amino)tetrahydro-4H-[1,3]dioxolo[4,5-c]pyran-4-yl)methyl)-1H-pyrazol-4-yl)methanol (50 mg, 0.12 mmol) in THF (5 mL) was added HCl (0.5 mL, 2 M in H₂O) at 0° C. The mixture was stirred at rt overnight. The mixture was concentrated and purified by chromatography on C18 to give (2R,3R,4R,5S)-2-((4-(hydroxymethyl)-1H-pyrazol-1-yl)methyl)-5-((4-(trifluoromethyl)pyrimidin-2-yl)amino)tetrahydro-2H-pyran-3,4-diol (A62, 2.5 mg, 5% yield) as a white solid. LC-MS (ESI) found: 390 [M+H]⁺. ¹H NMR (400 MHz, CD₃OD): δ 8.50 (d, J=4.7 Hz, 1H), 7.61 (s, 1H), 7.48 (s, 1H), 6.89 (d, J=4.9 Hz, 1H), 4.49 (s, 2H), 4.41-4.23 (m, 3H), 4.05 (dd, J=11.1, 5.2 Hz, 1H), 3.82-3.73 (m, 2H), 3.66 (dd, J=10.5, 3.0 Hz, 1H), 3.07 (t, J=10.9 Hz, 1H). ¹⁹F NMR (377 MHz, CD₃OD) δ -72.39.

Preparation of A63: N-((2S,3R,4R,5R,6R)-2-(allyloxy)-4,5-dihydroxy-6-((4-(hydroxymethyl)-1H-1,2,3-triazol-1-yl)methyl)tetrahydro-2H-pyran-3-yl)-2,2,2-trifluoroacetamide

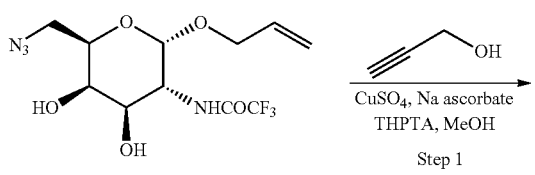

Step 1

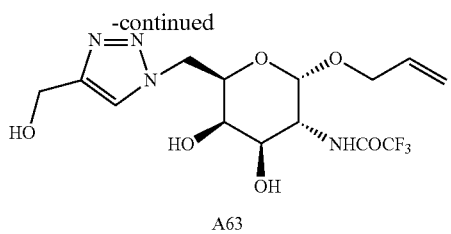

A63

Step 1: To a solution of THPTA (10 mg) and CuSO₄ (1 mg) were dissolved in water (0.5 mL). The mixture was added to a solution of N-((2S,3R,4R,5R,6R)-2-(allyloxy)-6-(azidomethyl)-4,5-dihydroxytetrahydro-2H-pyran-3-yl)-2,2,2-trifluoroacetamide (20 mg, 0.06 mmol) and prop-2-yn-1-ol (5 mg, 0.09 mmol) in MeOH (4 mL). A freshly-prepared solution of Na ascorbate (2 mg) in water (0.5 mL) was added. The reaction was stirred overnight. The resulting mixture was filtered. The crude product was purified by chromatography on (silical gel, 0-100% ethyl acetate in petroleum ether) to give N-((2S,3R,4R,5R,6R)-2-(allyloxy)-4,5-dihydroxy-6-((4-(hydroxymethyl)-1H-1,2,3-triazol-1-yl)methyl)tetrahydro-2H-pyran-3-yl)-2,2,2-trifluoroacetamide (A63, 18 mg, 78% yield) as a white solid. LC-MS (ESI) found: 397 [M+H]⁺.

¹H NMR (400 MHz, CD₃OD): δ 7.92 (s, 1H), 5.77-5.59 (m, 1H), 5.14 (ddd, J=17.3, 3.2, 1.6 Hz, 1H), 5.08 (ddd, J=10.4, 2.8, 1.2 Hz, 1H), 4.87 (d, J=3.8 Hz, 1H), 4.67 (s, 2H), 4.65-4.62 (m, 2H), 4.32 (dd, J=11.0, 3.7 Hz, 1H), 4.26-4.21 (m, 1H), 3.97 (dd, J=11.0, 3.2 Hz, 1H), 3.92 (d, J=2.6 Hz, 1H), 3.81-3.72 (m, 1H), 3.67 (ddt, J=13.1, 6.2, 1.3 Hz, 1H). ¹⁹F NMR (377 MHz, CD₃OD) δ –77.01.

Preparation of A64: (2R,3R,4R,5R,6S)-6-(allyloxy)-2-((4-(hydroxymethyl)-1H-1,2,3-triazol-1-yl)methyl)-5-((4-(trifluoromethyl)pyrimidin-2-yl)amino)tetrahydro-2H-pyran-3,4-diol

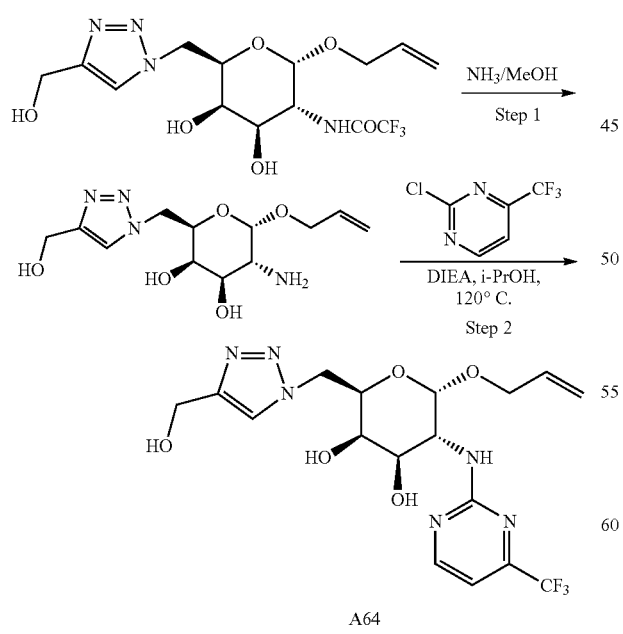

A64

Step 1: To a solution of N-((2S,3R,4R,5R,6R)-2-(allyloxy)-4,5-dihydroxy-6-((4-(hydroxymethyl)-1H-1,2,3-triazol-1-yl)methyl)tetrahydro-2H-pyran-3-yl)-2,2,2-trifluoroacetamide (15 mg, 0.03 mmol) in NH₃/MeOH (3 mL, 7 M in MeOH) was stirred at 80° C. overnight in a sealed tube. The mixture was concentrated to give crude (2R,3R,4R,5R,6S)-6-(allyloxy)-5-amino-2-((4-(hydroxymethyl)-1H-1,2,3-triazol-1-yl)methyl)tetrahydro-2H-pyran-3,4-diol (11 mg) as a white solid. LC-MS (ESI) found: 301 [M+H]⁺.

Step 2: To a solution of (2R,3R,4R,5R,6S)-6-(allyloxy)-5-amino-2-((4-(hydroxymethyl)-1H-1,2,3-triazol-1-yl)methyl)tetrahydro-2H-pyran-3,4-diol (11 mg, 0.03 mmol), 2-chloro-4-(trifluoromethyl)pyrimidine (9 mg, 0.05 mmol) and DIEA (12 mg, 0.1 mmol) in isopropanol (3 mL) was stirred at 120° C. overnight in a sealed tube. The mixture was concentrated and purified by chromatography on C18 to give (2R,3R,4R,5R,6S)-6-(allyloxy)-2-((4-(hydroxymethyl)-1H-1,2,3-triazol-1-yl)methyl)-5-((4-(trifluoromethyl)pyrimidin-2-yl)amino)tetrahydro-2H-pyran-3,4-diol (A64, 8.8 mg, 68% yield) as a white solid. LC-MS (ESI) found: 447 [M+H]⁺. ¹H NMR (400 MHz, CD₃OD): δ 8.51 (d, J=4.7 Hz, 1H), 7.94 (s, 1H), 6.91 (d, J=4.9 Hz, 1H), 5.66 (s, 1H), 5.10 (d, J=17.9 Hz, 1H), 5.04-4.95 (m, 2H), 4.69-4.64 (m, 4H), 4.55 (s, 1H), 4.29-4.22 (m, 1H), 3.97-3.91 (m, 2H), 3.74 (dd, J=13.0, 5.1 Hz, 1H), 3.67 (d, J=5.3 Hz, 1H). ¹⁹F NMR (377 MHz, CD₃OD): δ –72.36.

Preparation of A65: (2R,3R,4R,5S)-2-((4-(3-methoxyphenyl)-1H-1,2,3-triazol-1-yl)methyl)-5-((4-(trifluoromethyl)pyrimidin-2-yl)amino)tetrahydro-2H-pyran-3,4-diol

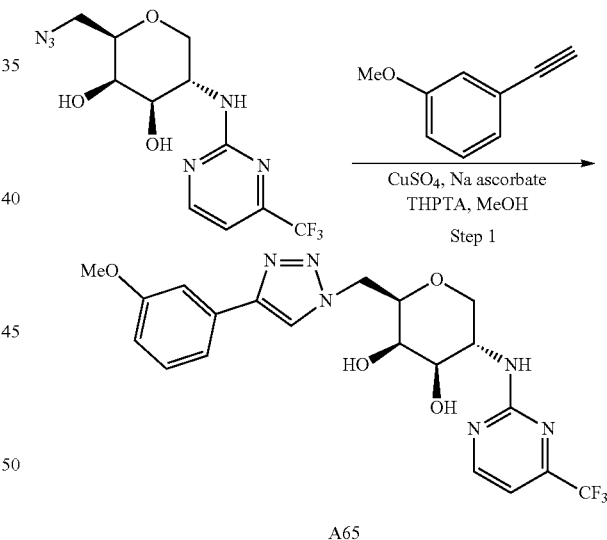

A65

Step 1: To a solution of THPTA (35 mg, 0.081 mmol) and CuSO₄ (4 mg, 0.025 mmol) were dissolved in water (0.3 mL) and then added to a solution of (2R,3R,4R,5S)-2-(azidomethyl)-5-((4-(trifluoromethyl)pyrimidin-2-yl)amino)tetrahydro-2H-pyran-3,4-diol (25 mg, 0.081 mmol) and 1-ethynyl-3-methoxybenzene (13 mg, 0.01 mmol) in MeOH (2.0 mL). A freshly-prepared solution of sodium ascorbate (32 mg, 0.162 mmol) in water (0.1 mL) was added and the reaction mixture was stirred at rt overnight. Solvent was evaporated and the residue was purified by column chromatography with 20% MeOH in DCM to get (2R,3R,4R,5S)-2-((4-(3-methoxyphenyl)-1H-1,2,3-triazol-1-yl)methyl)-5-((4-(trifluoromethyl)pyrimidin-2-yl)amino)tetrahydro-2H-pyran-3,4-diol (A65, 13 mg, 34% yield) as white solid. LC-MS (ESI) found: 467 [M+H]⁺. ¹H NMR (400 MHz, CD₃OD): δ 8.51 (d, J=4.3 Hz, 1H), 8.30 (s, 1H), 7.41-7.29 (m, 3H), 6.93-6.88 (m, 2H), 4.69 (d, J=6.1 Hz, 2H), 4.41 (td, J=10.6, 4.9 Hz, 1H), 4.10 (dd, J=11.1, 5.2 Hz, 1H), 3.93 (s, 2H), 3.77 (s, 1H), 3.72 (t, J=2.2 Hz, 1H), 3.12 (t, J=10.9 Hz, 1H).

Preparation of A66: (2R,3R,4R,5S)-5-((4-(trifluoromethyl)pyrimidin-2-yl)amino)-2-((4-(trimethylsilyl)-1H-1,2,3-triazol-1-yl)methyl)tetrahydro-2H-pyran-3,4-diol and A67: (2R,3R,4R,5S)-2-((1H-1,2,3-triazol-1-yl)methyl)-5-((4-(trifluoromethyl)pyrimidin-2-yl)amino)tetrahydro-2H-pyran-3,4-diol

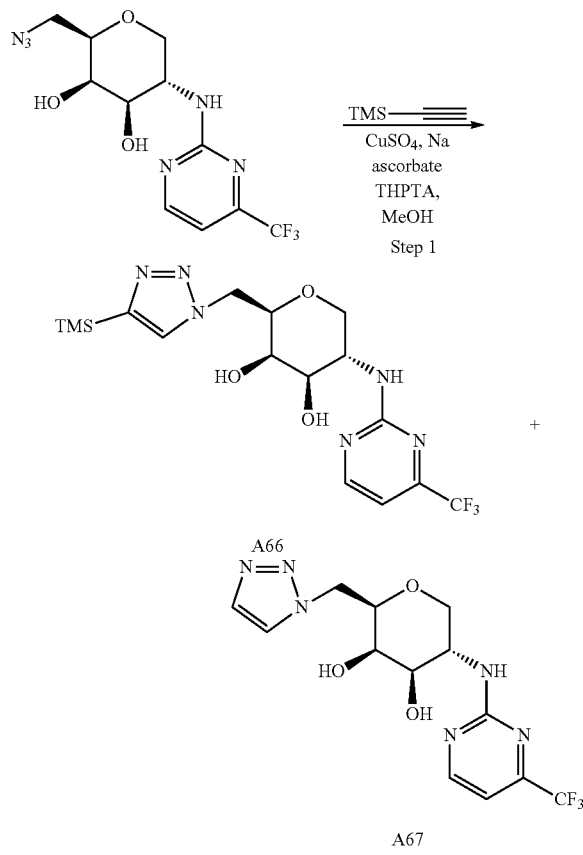

Step 1: To a solution of THPTA (5.20 mg, 0.012 mmol) and CuSO₄ (0.59 mg, 0.006 mmol) were dissolved in water (0.1 mL) and then added to a solution of (2R,3R,4R,5S)-2-(azidomethyl)-5-((4-(trifluoromethyl)pyrimidin-2-yl)amino)tetrahydro-2H-pyran-3,4-diol (20 mg, 0.060 mmol) and ethynyltrimethylsilane (7.1 mg, 0.072 mmol) in MeOH (2 mL). A freshly-prepared solution of sodium ascorbate (5.94 mg, 0.03 mmol) in water (0.1 mL) was added and the reaction mixture was stirred at rt overnight. Solvent was evaporated and the product was purified by prep-HPLC to give (2R,3R,4R,5S)-5-((4-(trifluoromethyl)pyrimidin-2-yl)amino)-2-((4-(trimethylsilyl)-1H-1,2,3-triazol-1-yl)methyl)tetrahydro-2H-pyran-3,4-diol (A66, 6 mg, 26% yield) and (2R,3R,4R,5S)-2-((1H-1,2,3-triazol-1-yl)methyl)-5-((4-(trifluoromethyl)pyrimidin-2-yl)amino)tetrahydro-2H-pyran-3,4-diol (A67, 3 mg, 13% yield) as white solid. A66: LC-MS (ESI) found: 433 [M+H]⁺. ¹H NMR (400 MHz, CD₃OD): δ 8.51 (d, J=4.7 Hz, 1H), 7.97 (s, 1H), 6.90 (d, J=4.9 Hz, 1H), 4.63 (t, J=17.9 Hz, 2H), 4.39 (d, J=4.7 Hz, 1H), 4.07 (dd, J=11.2, 5.3 Hz, 1H), 3.87 (t, J=4.4 Hz, 2H), 3.78-3.67 (m, 1H), 3.09 (t, J=10.9 Hz, 1H), 0.40-0.17 (m, 9H). A67: LC-MS (ESI) found: 361 [M+H]⁺. ¹H NMR (400 MHz, CD₃OD): δ 8.51 (d, J=4.5 Hz, 1H), 7.98 (s, 1H), 7.71 (s, 1H), 6.90 (d, J=4.9 Hz, 1H), 4.67 (d, J=6.3 Hz, 2H), 4.40 (s, 1H), 4.07 (dd, J=11.0, 5.2 Hz, 1H), 3.93-3.79 (m, 2H), 3.69 (dd, J=10.5, 3.2 Hz, 1H), 3.09 (dd, J=19.9, 9.0 Hz, 1H).

Preparation of A68: 6-(((3S,4R,5R,6R)-4,5-dihydroxy-6-(hydroxymethyl)tetrahydro-2H-pyran-3-yl)amino)-2-methoxypyrimidine-4-carboxamide

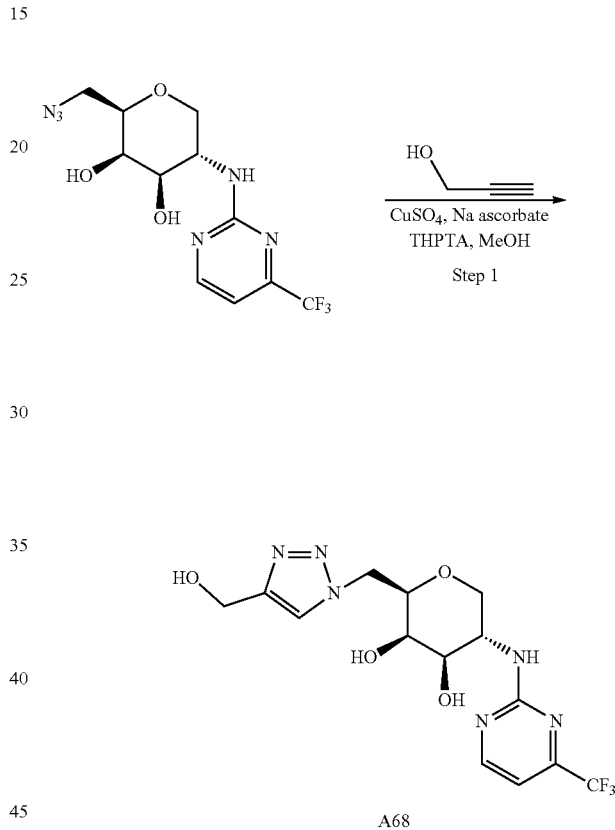

Step 1: To a solution of THPTA (5.20 mg, 0.012 mmol) and CuSO₄ (0.59 mg, 0.006 mmol) were dissolved in water (0.1 mL) and then added to a solution of (2R,3R,4R,5S)-2-(azidomethyl)-5-((4-(trifluoromethyl)pyrimidin-2-yl)amino)tetrahydro-2H-pyran-3,4-diol (20 mg, 0.060 mmol) and prop-2-yn-1-ol (4.0 mg, 0.072 mmol) in MeOH (2 mL). A freshly-prepared solution of sodium ascorbate (5.94 mg, 0.03 mmol) in water (0.1 mL) was added and the reaction mixture was stirred at rt overnight. Solvent was evaporated and the product was purified by prep-HPLC to give (2R,3R,4R,5S)-2-((4-(hydroxymethyl)-1H-1,2,3-triazol-1-yl)methyl)-5-((4-(trifluoromethyl)pyrimidin-2-yl)amino)tetrahydro-2H-pyran-3,4-diol (A68, 10 mg, 43% yield) as a white solid. LC-MS (ESI) found: 391 [M+H]⁺. ¹H NMR (400 MHz, CD₃OD): δ 8.51 (d, J=4.7 Hz, 1H), 7.90 (s, 1H), 6.90 (d, J=4.9 Hz, 1H), 4.67 (s, 2H), 4.63 (d, J=6.4 Hz, 2H), 4.39 (d, J=4.6 Hz, 1H), 4.06 (dd, J=11.2, 5.2 Hz, 1H), 3.90 (d, J=2.7 Hz, 1H), 3.85 (dd, J=6.9, 5.9 Hz, 1H), 3.69 (dd, J=10.5, 3.1 Hz, 1H), 3.08 (t, J=10.9 Hz, 1H).

Preparation of A69: (2R,3R,4R,5R,6S)-2-((1H-1,2,3-triazol-1-yl)methyl)-6-(allyloxy)-5-((4-(trifluoromethyl)pyrimidin-2-yl)amino)tetrahydro-2H-pyran-3,4-diol

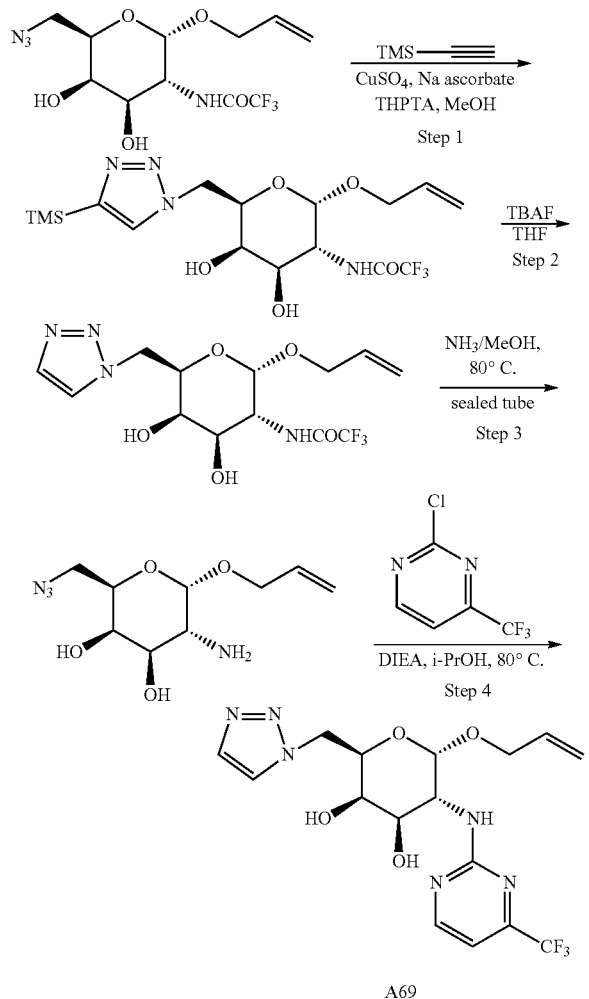

A69

Step 1: To a solution of THPTA (20 mg) and CuSO$_4$ (3 mg) were dissolved in water (0.5 mL). The mixture was added into a solution of N-((2S,3R,4R,5R,6R)-2-(allyloxy)-6-(azidomethyl)-4,5-dihydroxytetrahydro-2H-pyran-3-yl)-2,2,2-trifluoroacetamide (50 mg, 0.15 mmol) and ethynyltrimethylsilane (29 mg, 0.3 mmol) in MeOH (4 mL). A freshly-prepared solution of Na ascorbate (6 mg) in water (0.5 mL) was added. The reaction was stirred overnight. The resulting mixture was filtered. The crude product was purified by chromatography on (silical gel, 0-100% ethyl acetate in petroleum ether) to give N-((2S,3R,4R,5R,6R)-2-(allyloxy)-4,5-dihydroxy-6-((4-(trimethylsilyl)-1H-1,2,3-triazol-1-yl)methyl)tetrahydro-2H-pyran-3-yl)-2,2,2-trifluoroacetamide (40 mg, 61% yield) as a white solid. LC-MS (ESI) found: 439 [M+H]$^+$.

Step 2: To a solution of N-((2S,3R,4R,5R,6R)-2-(allyloxy)-4,5-dihydroxy-6-((4-(trimethylsilyl)-1H-1,2,3-triazol-1-yl)methyl)tetrahydro-2H-pyran-3-yl)-2,2,2-trifluoroacetamide (40 mg, 0.09 mmol) in THF (3 mL) was added TBAF (1 mL, 1 M in THF). The mixture was stirred at 40° C. overnight. The mixture was concentrated and the residue was purified by chromatography on (silical gel, 0-20% methanol in methylene chloride) to give N-((2S,3R,4R,5R,6R)-6-((1H-1,2,3-triazol-1-yl)methyl)-2-(allyloxy)-4,5-dihydroxytetrahydro-2H-pyran-3-yl)-2,2,2-trifluoroacetamide (25 mg, 76% yield) as a white solid. LC-MS (ESI) found: 367 [M+H]$^+$. $^1$H NMR (400 MHz, CD$_3$OD): δ 8.01 (s, 1H), 7.74 (s, 1H), 5.67 (ddd, J=22.5, 10.9, 5.9 Hz, 1H), 5.10 (dd, J=22.9, 5.8 Hz, 2H), 4.86 (s, 3H), 4.69 (d, J=2.3 Hz, 1H), 4.67 (s, 1H), 4.32 (dd, J=10.8, 3.7 Hz, 1H), 4.26-4.20 (m, 1H), 3.97 (dd, J=10.9, 3.3 Hz, 1H), 3.93 (d, J=3.0 Hz, 1H), 3.70 (dd, J=12.9, 5.4 Hz, 1H), 3.63 (dd, J=12.9, 6.2 Hz, 1H). $^{19}$F NMR (377 MHz, CD$_3$OD): δ -77.01.

Step 3: To a solution of N-((2S,3R,4R,5R,6R)-6-((1H-1,2,3-triazol-1-yl)methyl)-2-(allyloxy)-4,5-dihydroxytetrahydro-2H-pyran-3-yl)-2,2,2-trifluoroacetamide (20 mg, 0.05 mmol) in NH$_3$/MeOH (3 mL, 7 mol/L) was stirred at 80° C. overnight in a sealed tube. The mixture was concentrated to give crude (2R,3R,4R,5R,6S)-2-((1H-1,2,3-triazol-1-yl)methyl)-6-(allyloxy)-5-aminotetrahydro-2H-pyran-3,4-diol (14 mg, 100% yield) as a white solid. LC-MS (ESI) found: 271 [M+H]$^+$.

Step 4: To a solution of (2R,3R,4R,5R,6S)-2-((1H-1,2,3-triazol-1-yl)methyl)-6-(allyloxy)-5-aminotetrahydro-2H-pyran-3,4-diol (14 mg, 0.05 mmol), 2-chloro-4-(trifluoromethyl)pyrimidine (18 mg, 0.1 mmol) and DIEA (26 mg, 0.2 mmol) in isopropanol (3 mL) was stirred at 80° C. overnight in a sealed tube. The mixture was concentrated and purified by chromatography on C18 to give (2R,3R,4R,5R,6S)-2-((1H-1,2,3-triazol-1-yl)methyl)-6-(allyloxy)-5-((4-(trifluoromethyl)pyrimidin-2-yl)amino)tetrahydro-2H-pyran-3,4-diol (A69, 8.8 mg, 42% yield) as a white solid. LC-MS (ESI) found: 417 [M+H]$^+$. $^1$H NMR (400 MHz, CD$_3$OD): δ 8.51 (d, J=4.6 Hz, 1H), 8.02 (d, J=0.8 Hz, 1H), 7.74 (d, J=0.9 Hz, 1H), 6.91 (d, J=4.9 Hz, 1H), 5.64 (dd, J=10.7, 5.7 Hz, 1H), 5.07 (d, J=17.2 Hz, 1H), 5.00 (d, J=10.4 Hz, 1H), 4.96 (s, 1H), 4.71 (d, J=2.7 Hz, 1H), 4.69 (s, 1H), 4.55 (s, 1H), 4.29-4.22 (m, 1H), 4.01-3.88 (m, 2H), 3.75-3.52 (m, 2H). $^{19}$F NMR (377 MHz, CD$_3$OD): δ -72.35.

Preparation of A70: N-((2S,3R,4R,5R,6R)-6-((1H-1,2,3-triazol-1-yl)methyl)-2-(allyloxy)-4,5-dihydroxytetrahydro-2H-pyran-3-yl)-2,2,2-trifluoroacetamide and A71: (2R,3R,4R,5R,6S)-2-((1H-1,2,3-triazol-1-yl)methyl)-6-(allyloxy)-5-aminotetrahydro-2H-pyran-3,4-diol

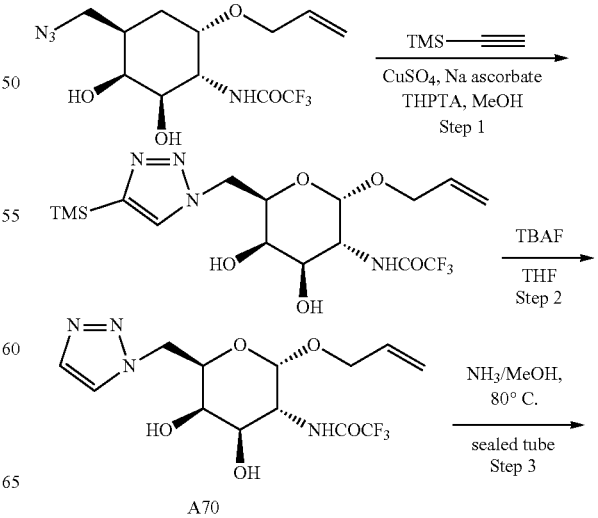

A70

-continued

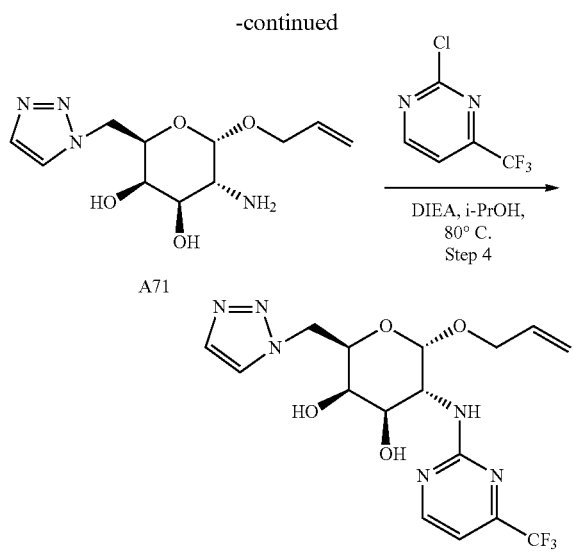

Step 1: To a solution of THPTA (20 mg) and CuSO₄ (3 mg) were dissolved in water (0.5 mL). The mixture was added into a solution of N-((2S,3R,4R,5R,6R)-2-(allyloxy)-6-(azidomethyl)-4,5-dihydroxytetrahydro-2H-pyran-3-yl)-2,2,2-trifluoroacetamide (50 mg, 0.15 mmol) and ethynyltrimethylsilane (29 mg, 0.3 mmol) in MeOH (4 mL). A freshly-prepared solution of Na ascorbate (6 mg) in water (0.5 mL) was added. The reaction was stirred overnight. The resulting mixture was filtered. The crude product was purified by chromatography on (silical gel, 0-100% ethyl acetate in petroleum ether) to give N-((2S,3R,4R,5R,6R)-2-(allyloxy)-4,5-dihydroxy-6-((4-(trimethylsilyl)-1H-1,2,3-triazol-1-yl)methyl)tetrahydro-2H-pyran-3-yl)-2,2,2-trifluoroacetamide (40 mg, 61% yield) as a white solid. LC-MS (ESI) found: 439 [M+H]⁺.

Step 2: To a solution of N-((2S,3R,4R,5R,6R)-2-(allyloxy)-4,5-dihydroxy-6-((4-(trimethylsilyl)-1H-1,2,3-triazol-1-yl)methyl)tetrahydro-2H-pyran-3-yl)-2,2,2-trifluoroacetamide (40 mg, 0.09 mmol) in THF (3 mL) was added TBAF (1 mL, 1 M in THF). The mixture was stirred at 40° C. overnight. The mixture was concentrated and purified by chromatography on (silical gel, 0-20% methanol in methylene chloride) to give N-((2S,3R,4R,5R,6R)-6-((1H-1,2,3-triazol-1-yl)methyl)-2-(allyloxy)-4,5-dihydroxytetrahydro-2H-pyran-3-yl)-2,2,2-trifluoroacetamide (A70, 25 mg, 76% yield) as a white solid. LC-MS (ESI) found: 367 [M+H]⁺. ¹H NMR (400 MHz, CD₃OD): δ 8.01 (s, 1H), 7.74 (s, 1H), 5.67 (ddd, J=22.5, 10.9, 5.9 Hz, 1H), 5.10 (dd, J=22.9, 5.8 Hz, 2H), 4.86 (s, 3H), 4.69 (d, J=2.3 Hz, 1H), 4.67 (s, 1H), 4.32 (dd, J=10.8, 3.7 Hz, 1H), 4.26-4.20 (m, 1H), 3.97 (dd, J=10.9, 3.3 Hz, 1H), 3.93 (d, J=3.0 Hz, 1H), 3.70 (dd, J=12.9, 5.4 Hz, 1H), 3.63 (dd, J=12.9, 6.2 Hz, 1H). ¹⁹F NMR (377 MHz, CD₃OD): δ -77.01.

Step 3: To a solution of N-((2S,3R,4R,5R,6R)-6-((1H-1,2,3-triazol-1-yl)methyl)-2-(allyloxy)-4,5-dihydroxytetrahydro-2H-pyran-3-yl)-2,2,2-trifluoroacetamide (20 mg, 0.05 mmol) in NH₃/MeOH (3 mL, 7 mol/L) was stirred at 80° C. overnight in a sealed tube. The mixture was concentrated to give crude (2R,3R,4R,5R,6S)-2-((1H-1,2,3-triazol-1-yl)methyl)-6-(allyloxy)-5-aminotetrahydro-2H-pyran-3,4-diol (14 mg, 100% yield) as a white solid. LC-MS (ESI) found: 271 [M+H]⁺.

Step 4: To a solution of (2R,3R,4R,5R,6S)-2-((1H-1,2,3-triazol-1-yl)methyl)-6-(allyloxy)-5-aminotetrahydro-2H-pyran-3,4-diol (14 mg, 0.05 mmol), 2-chloro-4-(trifluoromethyl)pyrimidine (18 mg, 0.1 mmol) and DIEA (26 mg, 0.2 mmol) in isopropanol (3 mL) was stirred at 80° C. overnight in a sealed tube. The mixture was concentrated and purified by chromatography on C18 to give (2R,3R,4R,5R,6S)-2-((1H-1,2,3-triazol-1-yl)methyl)-6-(allyloxy)-5-((4-(trifluoromethyl)pyrimidin-2-yl)amino)tetrahydro-2H-pyran-3,4-diol (8.8 mg, 42% yield) as a white solid. LC-MS (ESI) found: 417 [M+H]⁺. ¹H NMR (400 MHz, CD₃OD): δ 8.51 (d, J=4.6 Hz, 1H), 8.02 (d, J=0.8 Hz, 1H), 7.74 (d, J=0.9 Hz, 1H), 6.91 (d, J=4.9 Hz, 1H), 5.64 (dd, J=10.7, 5.7 Hz, 1H), 5.07 (d, J=17.2 Hz, 1H), 5.00 (d, J=10.4 Hz, 1H), 4.96 (s, 1H), 4.71 (d, J=2.7 Hz, 1H), 4.69 (s, 1H), 4.55 (s, 1H), 4.29-4.22 (m, 1H), 4.01-3.88 (m, 2H), 3.75-3.52 (m, 2H). ¹⁹F NMR (377 MHz, CD₃OD): δ -72.35.

Preparation of A72: (2R,3R,4R,5R,6S)-6-(allyloxy)-2-(azidomethyl)-5-((4-(trifluoromethyl)pyrimidin-2-yl)amino)tetrahydro-2H-pyran-3,4-diol

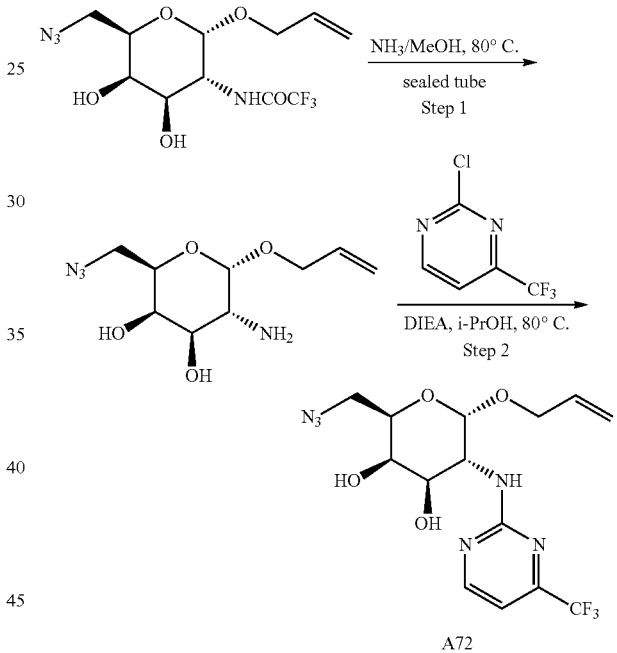

Step 1: To a solution of N-((2S,3R,4R,5R,6R)-2-(allyloxy)-6-(azidomethyl)-4,5-dihydroxytetrahydro-2H-pyran-3-yl)-2,2,2-trifluoroacetamide (40 mg, 0.11 mmol) in NH₃/MeOH (3 mL, 7 mol/L) was stirred at 80° C. overnight in a sealed tube. The mixture was concentrated to give crude (2R,3R,4R,5R,6S)-6-(allyloxy)-5-amino-2-(azidomethyl)tetrahydro-2H-pyran-3,4-diol (28 mg, 100% yield) as a white solid. LC-MS (ESI) found: 245 [M+H]⁺.

Step 2: To a solution of (2R,3R,4R,5R,6S)-6-(allyloxy)-5-amino-2-(azidomethyl)tetrahydro-2H-pyran-3,4-diol (28 mg, 0.11 mmol), 2-chloro-4-(trifluoromethyl)pyrimidine (27 mg, 0.15 mmol) and DIEA (26 mg, 0.2 mmol) in isopropanol (3 mL) was stirred at 80° C. overnight in a sealed tube. The mixture was concentrated and purified by chromatography on C18 column to give (2R,3R,4R,5R,6S)-6-(allyloxy)-2-(azidomethyl)-5-((4-(trifluoromethyl)pyrimidin-2-yl)amino)tetrahydro-2H-pyran-3,4-diol (A72, 8.8 mg, 20% yield) as a white solid. LC-MS (ESI) found: 391 [M+H]⁺. ¹H NMR (400 MHz, CD₃OD): δ 8.52 (d, J=4.8 Hz, 1H), 6.91

(d, J=4.9 Hz, 1H), 5.89 (s, 1H), 5.28 (d, J=17.2 Hz, 1H), 5.12 (d, J=10.5 Hz, 1H), 5.04 (s, 1H), 4.52 (s, 1H), 4.22 (ddt, J=13.0, 5.0, 1.3 Hz, 1H), 4.08-3.97 (m, 2H), 3.92 (dd, J=10.8, 3.2 Hz, 1H), 3.86 (d, J=2.5 Hz, 1H), 3.62 (dd, J=12.8, 8.7 Hz, 1H), 3.33 (s, 1H). $^{19}$F NMR (377 MHz, CD$_3$OD): δ −72.35

Preparation of A73: 1-((3S,4R,5R,6R)-4,5-bis(benzyloxy)-6-((benzyloxy)methyl)tetrahydro-2H-pyran-3-yl) guanidine

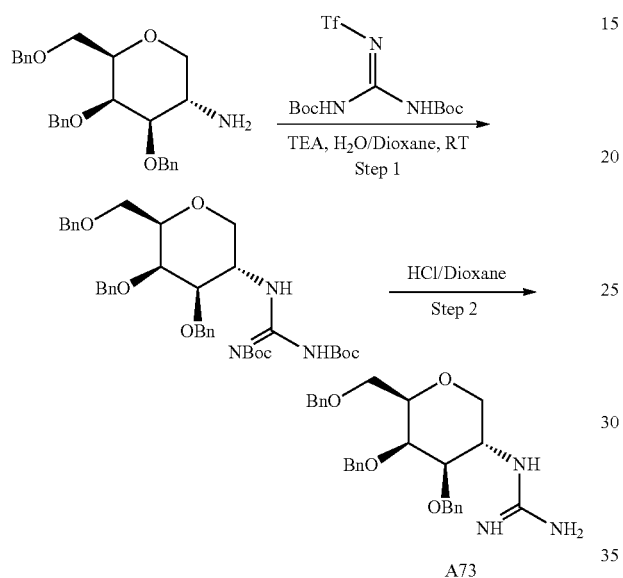

Step 1: To a solution of (3S,4R,5R,6R)-4,5-bis(benzyloxy)-6-((benzyloxy)methyl)tetrahydro-2H-pyran-3-amine (400.0 mg, 0.923 mmol) in dioxane (10.0 mL) and H$_2$O (1.0 mL) was added tert-butyl N-({[(tert-butoxy)carbonyl]amino}(trifluoromethanesulfonylimino)methyl)carbamate (360.9 mg, 0.923 mmol), TEA (932.2 mg, 9.23 mmol). The mixture was stirred at the room temperature for 16 h. The mixture was concentrated under reduced pressure to give a crude product, which was purified by column to give tert-butyl N-[(1Z)-{[(1S,2R,3S,4R)-2,3-bis(benzyloxy)-4-[(benzyloxy)methyl]cyclohexyl]amino}({[(tertbutoxy)carbonyl]imino}) methyl] carbamate (200.0 mg, 0.296 mmol). LC-MS (ESI) found: 676[M+H]$^+$.

Step 2: To tert-butyl N-[(1Z)-{[(1S,2R,3S,4R)-2,3-bis(benzyloxy)-4-[(benzyloxy)methyl]cyclohexyl]amino}({[(tertbutoxy)carbonyl]imino})methyl]carbamate (200.0 mg, 0.296 mmol) in flask (50 mL) was added HCl/Dioxane (10 mL, 1 M). The mixture was stirred at the room temperature for 16 h. The mixture was concentrated under reduced pressure to give a crude product, which was purified by column to give 1-((3S,4R,5R,6R)-4,5-bis(benzyloxy)-6-((benzyloxy)methyl)tetrahydro-2H-pyran-3-yl)guanidine (A73, 20.0 mg, 0.042 mmol). LC-MS (ESI) found: 476 [M+H]$^+$. $^1$H NMR (400 MHz, DMSO-d$_6$): δ 9.03 (s, 1H), 7.60 (s, 3H), 7.43-7.17 (m, 15H), 4.77 (dd, J=11.2, 3.9 Hz, 2H), 4.60 (d, J=11.1 Hz, 1H), 4.47 (dd, J=18.7, 12.5 Hz, 3H), 4.06 (d, J=1.8 Hz, 1H), 3.92-3.75 (m, 2H), 3.71-3.58 (m, 2H), 3.52 (d, J=6.1 Hz, 2H), 3.11 (t, J=10.3 Hz, 1H).

Preparation of A74: (1S,2R,3R,4R,5S)-1-(azidomethyl)-4-((3-chloro-1,2,4-thiadiazol-5-yl)amino)-6,8-dioxabicyclo[3.2.1]octane-2,3-diol

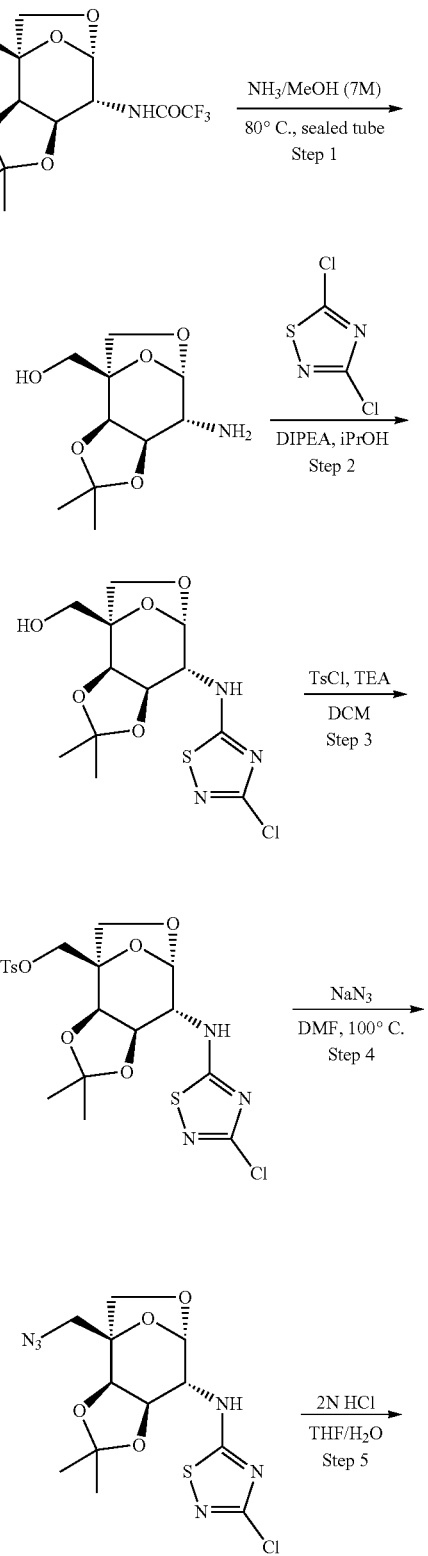

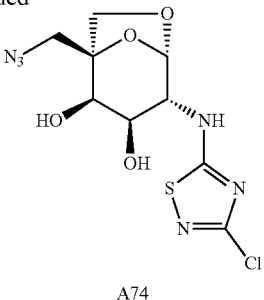

A74

Step 1: To a solution of 2,2,2-trifluoro-N-((3aR,4S,7S,8R,8aR)-4-(hydroxymethyl)-2,2-dimethylhexahydro-4,7-epoxy[1,3]dioxolo[4,5-d]oxepin-8-yl)acetamide (300 mg, 0.92 mmol) in Ammonia methanol solution (5 mL, 7 M) was stirred at 60° C. overnight. The resulting mixture was concentrated in vacuo. The crude ((3aR,4S,7S,8R,8aR)-8-amino-2,2-dimethyltetrahydro-4,7-epoxy[1,3]dioxolo[4,5-d]oxepin-4(5H)-yl)methanol (270 mg, 76% yield) was used for next step without further purification. LC-MS (ESI) found: 232 [M+H]+.

Step 2: To a solution of ((3aR,4S,7S,8R,8aR)-8-amino-2,2-dimethyltetrahydro-4,7-epoxy[1,3]dioxolo[4,5-d]oxepin-4(5H)-yl)methanol (270 mg, 1.2 mmol) in i-PrOH (5 mL) was added DIPEA (0.4 mL, 2.3 mmol) at rt under N₂. The reaction was stirred at 80° C. overnight. The resulting mixture was concentrated in vacuo. The crude product was purified by flash chromatography (silica gel, 0-10% MeOH in DCM) to give ((3aR,4S,7S,8R,8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)methanol (130 mg, 32% yield) as a colorless oil. LC-MS (ESI) found: 350 [M+H]+. ¹H NMR (400 MHz, CD₃OD): δ 5.42 (d, J=1.9 Hz, 1H), 4.35 (d, J=5.8 Hz, 1H), 4.21 (t, J=6.3 Hz, 1H), 3.95-3.83 (m, 4H), 3.80 (d, J=7.8 Hz, 1H), 1.53 (s, 3H), 1.36 (s, 3H).

Step 3: To a solution of ((3aR,4S,7S,8R,8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)methanol (120 mg, 0.3 mmol) in TEA (0.1 mL, 0.7 mmol) and dry DCM (5 mL) at 0° C. under N₂ atmosphere was added tosyl chloride (85 mg, 0.5 mmol). The reaction was stirred at rt overnight. The resulting mixture was filtered and diluted with DCM (50 mL), washed with H₂O (10 mL×2) and brine (10 mL), dried over Na₂SO₄. The organic layer was separated and concentrated in vacuo. The crude product was purified by flash chromatography (silica gel, 0~80% EA in PE) to give ((3aR,4R,7S,8R,8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)methyl 4-methylbenzenesulfonate (120 mg, 70% yield) as a colorless solid. LC-MS (ESI) found: 504 [M+H]+.

Step 4: To a solution of ((3aR,4R,7S,8R,8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)methyl 4-methylbenzenesulfonate (120 mg, 0.24 mmol) in DMF (5 mL) was added sodium azide (0.1 mL, 2.4 mmol) at rt under N₂. The reaction was stirred at 100° C. for 24 h. The resulting mixture was diluted with EA (100 mL), washed with H₂O (30 mL×2) and brine (10 mL), dried over Na₂SO₄. The organic layer was separated and concentrated in vacuo. The crude product was purified by flash chromatography (silica gel, 0~80% EA in PE) to give N-((3aR,4S,7S,8R,8aR)-4-(azidomethyl)-2,2-dimethylhexahydro-4,7-epoxy[1,3]dioxolo[4,5-d]oxepin-8-yl)-3-chloro-1,2,4-thiadiazol-5-amine (75 mg, 84% yield) as a colorless solid. LC-MS (ESI) found: 375 [M+H]+.

Step 5: To a solution of N-((3aR,4S,7S,8R,8aR)-4-(azidomethyl)-2,2-dimethylhexahydro-4,7-epoxy[1,3]dioxolo[4,5-d]oxepin-8-yl)-3-chloro-1,2,4-thiadiazol-5-amine (75 mg, 0.2 mmol) in THF (4 mL) was added HCl solution (1 mL, 2 M in H₂O). The reaction was stirred at rt overnight. The crude product was purified by prep-HPLC to afford (1S,2R,3R,4R,5S)-1-(azidomethyl)-4-((3-chloro-1,2,4-thiadiazol-5-yl)amino)-6,8-dioxabicyclo[3.2.1]octane-2,3-diol (A74, 40 mg, 60% yield) as a white solid. LC-MS (ESI) found: 335 [M+H]+. ¹H NMR (400 MHz, CD₃OD): δ 5.41 (s, 1H), 3.86 (d, J=12.9 Hz, 2H), 3.82-3.76 (m, 3H), 3.69 (d, J=8.1 Hz, 1H), 3.64 (d, J=12.9 Hz, 1H).

Preparation of A75: (2R,3R,4R,5S)-2-(hydroxymethyl)-5-((4-(trifluoromethoxy)pyrimidin-2-yl)amino)tetrahydro-2H-pyran-3,4-diol

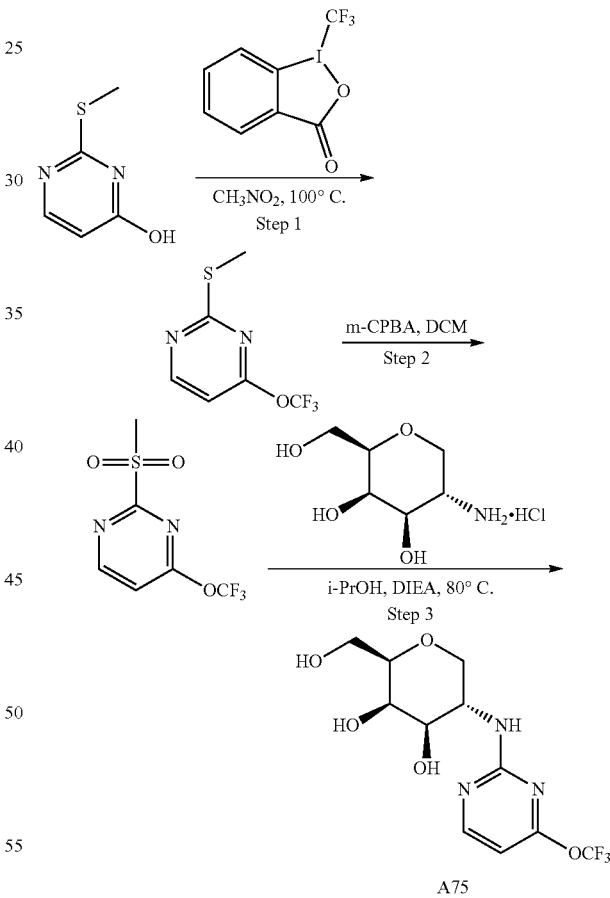

A75

Step 1: To a dried glass reaction tube equipped with a magnetic stir bar was charged with 2-(methylthio)pyrimidin-4-ol (2.0 g, 14.1 mmol), 1-(trifluoromethyl)-1l3-benzo[d][1,2]iodaoxol-3(1H)-one (1.5 g, 4.7 mmol) and CH₃NO₂ (20.0 mL). The reaction mixture was then stirred at 100° C. for 5 h. The reaction was monitored by TLC. After completion, the reaction mixture was cooled to room temperature and filtered through a pad of celite and washed with ethyl acetate. The combined organic solvent was concentrated in vacuo. The residue was purified by chromatography on (silical gel, 0-100% ethyl acetate in petroleum ether) to give 2-(methylthio)-4-(trifluoromethoxy)pyrimidine (80 mg, 3% yield) as solid. LC-MS (ESI) found: 211 [M+H]$^+$.

Step 2: To a solution of 2-(methylthio)-4-(trifluoromethoxy)pyrimidine (40 mg, 0.2 mmol) in DCM (8 mL) was added m-CPBA (69 mg, 0.4 mmol) at 0° C., the mixture was stirred at rt for 12 h. The mixture was concentrated and purified by chromatography on (silical gel, 0-100% ethyl acetate in petroleum ether) to give 2-(methylsulfonyl)-4-(trifluoromethoxy)pyrimidine (40 mg, 87% yield) as solid. LC-MS (ESI) found: 243 [M+H]$^+$.

Step 3: To a solution of (2R,3R,4R,5S)-5-amino-2-(hydroxymethyl)tetrahydro-2H-pyran-3,4-diol (50 mg, 0.3 mmol), 2-(methylsulfonyl)-4-(trifluoromethoxy)pyrimidine (20 mg, 0.1 mmol) and DIEA (39 mg, 0.3 mmol) in isopropanol (3 mL) was stirred at 80° C. overnight in a sealed tube. The mixture was concentrated and purified by chromatography on C18 to give (2R,3R,4R,5S)-2-(hydroxymethyl)-5-((4-(trifluoromethoxy)pyrimidin-2-yl)amino)tetrahydro-2H-pyran-3,4-diol (A75, 1.7 mg, 5% yield) as a white solid. LC-MS (ESI) found: 326 [M+H]$^+$. $^1$H NMR (400 MHz, CD$_3$OD): δ 8.27 (d, J=5.5 Hz, 1H), 6.28 (d, J=5.5 Hz, 1H), 4.28 (dd, J=28.4, 16.0 Hz, 1H), 4.10 (dd, J=10.7, 5.3 Hz, 1H), 3.90 (d, J=2.9 Hz, 1H), 3.75 (dd, J=11.4, 7.1 Hz, 1H), 3.68 (dd, J=11.4, 5.0 Hz, 1H), 3.64 (d, J=4.2 Hz, 1H), 3.46-3.41 (m, 1H), 3.16 (t, J=10.9 Hz, 1H). $^{19}$F NMR (377 MHz, CD$_3$OD): δ −57.54.

Preparation of A76: (2R,3R,4R,5R,6S)-2-(hydroxymethyl)-6-(oxiran-2-ylmethoxy)-5-((4-(trifluoromethyl)pyrimidin-2-yl)amino)tetrahydro-2H-pyran-3,4-diol

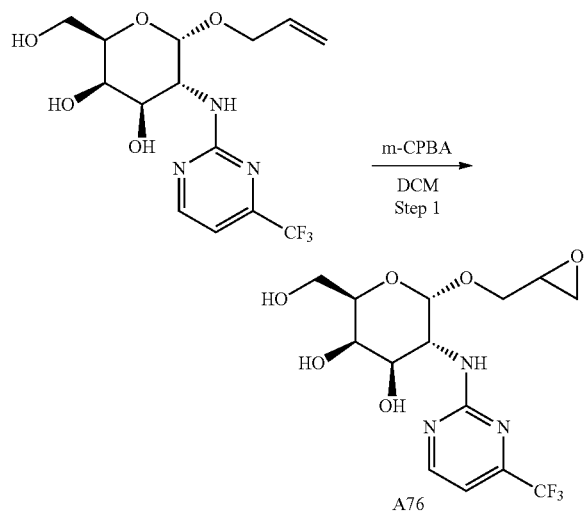

Step 1: To a solution of (2R,3R,4R,5R,6S)-6-(allyloxy)-2-(hydroxymethyl)-5-((4-(trifluoromethyl)pyrimidin-2-yl)amino)tetrahydro-2H-pyran-3,4-diol (200.0 mg, 0.548 mmol) in DCM (20.0 mL) was added m-CPBA (177.6 mg, 1.096 mmol). The mixture was stirred at the room temperature for 2 h. The mixture was concentrated under reduced pressure to give a crude product, which was purified by column to give (2R,3R,4R,5R,6S)-2-(hydroxymethyl)-6-(oxiran-2-ylmethoxy)-5-((4-(trifluoromethyl)pyrimidin-2-yl)amino)tetrahydro-2H-pyran-3,4-diol (A76, 20.0 mg, 9% yield). LC-MS (ESI) found: 382[M+H]$^+$. $^1$H NMR (400 MHz, CD$_3$OD): δ 8.57 (d, J=6.5 Hz, 1H), 7.13 (d, J=6.5 Hz, 1H), 5.90 (m, 1H), 5.28 (dd, J=17.2, 1.6 Hz, 1H), 5.13 (dd, J=10.5, 1.3 Hz, 1H), 5.03 (d, J=3.7 Hz, 1H), 4.56 (dd, J=9.9, 3.6 Hz, 1H), 4.24 (dd, J=13.1, 5.1 Hz, 1H), 4.07-3.96 (m, 3H), 3.91 (t, J=6.1 Hz, 1H), 3.79-3.69 (m, 2H). $^{19}$F NMR (377 MHz, CD$_3$OD): δ −70.68 (s).

Preparation of A77: (2R,3R,4R,5S)-5-((3-fluoro-6-(trifluoromethyl)pyridin-2-yl)amino)-2-(hydroxymethyl)tetrahydro-2H-pyran-3,4-diol

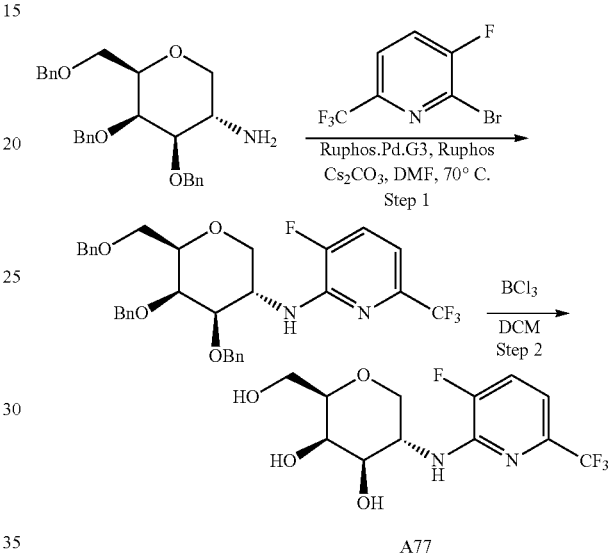

Step 1: To a solution of (3S,4R,5R,6R)-4,5-bis(benzyloxy)-6-((benzyloxy)methyl)tetrahydro-2H-pyran-3-amine (200.0 mg, 0.462 mmol) in DMF (10.0 mL) was added 2-bromo-3-fluoro-6-(trifluoromethyl)pyridine (112.2 mg, 0.462 mmol), Ruphos.Pd.G3 (38.0 mg, 0.046 mmol), Ruphos (21.5 mg, 0.046 mmol), Cs$_2$CO$_3$ (450.5 mg, 1.386 mmol). The mixture was stirred at 70° C. under N$_2$ for 16 h. The mixture was concentrated under reduced pressure to give a crude product, which was purified by column to give N-((3S,4R,5R,6R)-4,5-bis(benzyloxy)-6-((benzyloxy)methyl)tetrahydro-2H-pyran-3-yl)-3-fluoro-6-(trifluoromethyl)pyridin-2-amine (100.0 mg, 41% yield). LC-MS (ESI) found: 597[M+H]$^+$.

Step 2: To a solution of N-((3S,4R,5R,6R)-4,5-bis(benzyloxy)-6-((benzyloxy)methyl)tetrahydro-2H-pyran-3-yl)-3-fluoro-6-(trifluoromethyl)pyridin-2-amine (100.0 mg, 0.168 mmol) in DCM (20.0 mL) was added BCl$_3$ (1.68 mL, 1 N in DCM) at 0° C. The mixture was stirred at the room temperature for 2 h. The mixture was concentrated under reduced pressure to give a crude product, which was purified by column to give (2R,3R,4R,5S)-5-((3-fluoro-6-(trifluoromethyl)pyridin-2-yl)amino)-2-(hydroxymethyl)tetrahydro-2H-pyran-3,4-diol (A77, 10.0 mg, 18% yield). LC-MS (ESI) found: 327[M+H]$^+$. $^1$H NMR (400 MHz, CD$_3$OD): δ 7.35 (dd, J=10.7, 8.1 Hz, 1H), 6.94 (dd, J=8.0, 2.9 Hz, 1H), 4.47 (td, J=10.6, 5.2 Hz, 1H), 4.17 (dd, J=10.9, 5.2 Hz, 1H), 3.92 (d, J=2.9 Hz, 1H), 3.81-3.62 (m, 3H), 3.50-3.42 (m, 1H), 3.17 (t, J=10.8 Hz, 1H). $^{19}$F NMR (377 MHz, CD$_3$OD): δ −69.34 (s), −137.35 (s).

Preparation of A78: (2R,3R,4R,5S)-5-((2-chloro-6-(trifluoromethyl)pyrimidin-4-yl)amino)-2-(hydroxymethyl)tetrahydro-2H-pyran-3,4-diol and A79: 4-(((3S,4R,5R,6R)-4,5-dihydroxy-6-(hydroxymethyl)tetrahydro-2H-pyran-3-yl)amino)-6-(trifluoromethyl)pyrimidine-2-carbonitrile

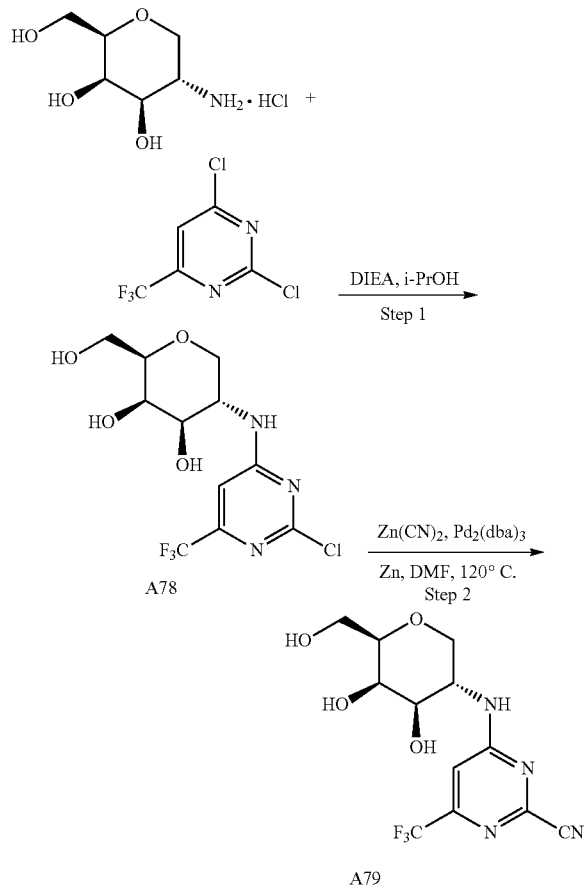

Step 1: To a mixture of (2R,3R,4R,5S)-5-amino-2-(hydroxymethyl)tetrahydro-2H-pyran-3,4-diol hydrochloride (500 mg, 3.1 mmol) in i-PrOH (3.0 mL) was added 2,4-dichloro-6-(trifluoromethyl)pyrimidine (0.84 mL, 6.1 mmol) and DIEA (1.5 mL, 9.2 mmol) at r.t under $N_2$. After stirring at r.t overnight, the mixture was concentrated and purified by chromatography on (silical gel, 0-30% methanol in DCM) to give (2R,3R,4R,5S)-5-((2-chloro-6-(trifluoromethyl)pyrimidin-4-yl)amino)-2-(hydroxymethyl)tetrahydro-2H-pyran-3,4-diol (A78, 160 mg, 15% yield) as a white solid. LC-MS (ESI) found: 344 $[M+1]^+$.

Step 2: To a mixture of (2R,3R,4R,5S)-5-((2-chloro-6-(trifluoromethyl)pyrimidin-4-yl)amino)-2-(hydroxymethyl)tetrahydro-2H-pyran-3,4-diol (20 mg, 0.058 mmol) in DMF (3.0 mL) was added $Zn(CN)_2$ (4.1 mg, 0.035 mmol), dppf (16.2 mg, 0.028 mmol), Zn (3.3 mg, 0.31 mmol) and $Pd_2(dba)_3$ (26.6 mg, 0.18 mmol) at r.t under $N_2$. After stirring at 120° C. overnight, the reaction mixture was concentrated and purified by prep-TLC to give 4-(((3S,4R,5R,6R)-4,5-dihydroxy-6-(hydroxymethyl)tetrahydro-2H-pyran-3-yl)amino)-6-(trifluoromethyl)pyrimidine-2-carbonitrile (A79, 2.4 mg, 12% yield) as a white solid. LC-MS (ESI) found: 333 $[M-H]^-$. $^1$H NMR (400 MHz, MeOD): δ 6.97 (s, 1H), 4.57-4.48 (m, 1H), 4.08 (dd, J=11.1, 5.2 Hz, 1H), 3.92 (d, J=2.8 Hz, 1H), 3.76 (dd, J=11.3, 7.1 Hz, 1H), 3.69 (dd, J=11.4, 4.9 Hz, 1H), 3.62 (dd, J=10.6, 3.1 Hz, 1H), 3.48-3.44 (m, 1H), 3.14 (t, J=10.9 Hz, 1H).

Preparation of A80: ((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)methanol

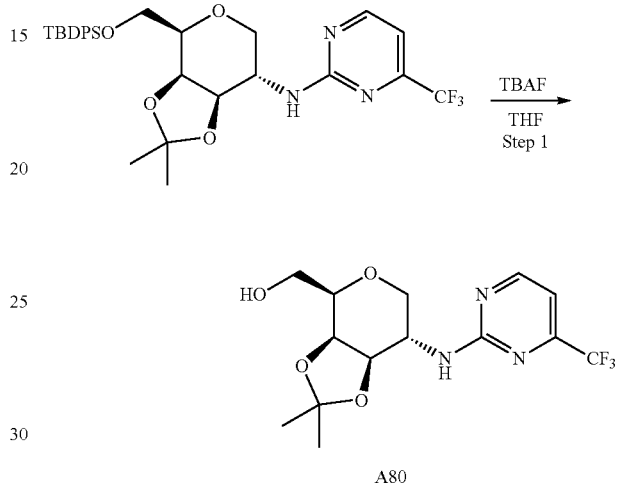

Step 1: To the solution of N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)-4-(trifluoromethyl)pyrimidin-2-amine (50 mg, 0.085 mmol) in THF (1 mL) was added TBAF (108 μL, 1 M in THF). The reaction was stirred at rt for three hours and was ensured completion by LCMS. Then the reaction was concentrated and purified by column chromatography with 20% methanol in DCM to get ((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)methanol (A80, 18 mg, 61% yield) as white solid. LC-MS (ESI) found: 350 $[M+H]^+$.

$^1$H NMR (400 MHz, $CD_3OD$): δ 8.51 (d, J=4.8 Hz, 1H), 6.90 (d, J=4.9 Hz, 1H), 4.31 (s, 1H), 4.28-4.11 (m, 2H), 3.91 (dt, J=44.5, 22.2 Hz, 1H), 3.76 (dt, J=13.7, 6.7 Hz, 3H), 3.16 (t, J=11.2 Hz, 1H), 1.50 (s, 2H), 1.32 (s, 2H).

Preparation of A79: 4-(((3S,4R,5R,6R)-4,5-dihydroxy-6-(hydroxymethyl)tetrahydro-2H-pyran-3-yl)amino)-6-(trifluoromethyl)pyrimidine-2-carbonitrile

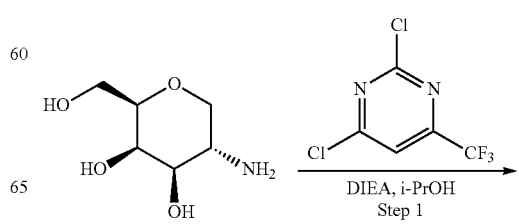

933

-continued

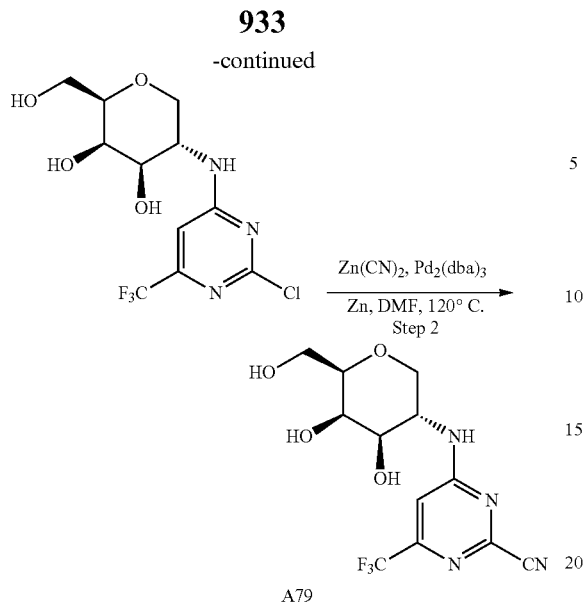

A79

Step 1: To a mixture of (2R,3R,4R,5S)-5-amino-2-(hydroxymethyl)tetrahydro-2H-pyran-3,4-diol hydrochloride (500 mg, 3.1 mmol) in i-PrOH (3.0 mL) was added 2,4-dichloro-6-(trifluoromethyl)pyrimidine (0.84 mL, 6.1 mmol) and DIEA (1.5 mL, 9.2 mmol) at r.t under $N_2$. After stirring at r.t overnight, the mixture was concentrated and purified by chromatography on (silical gel, 0-30% methanol in DCM) to give (2R,3R,4R,5S)-5-((2-chloro-6-(trifluoromethyl)pyrimidin-4-yl)amino)-2-(hydroxymethyl)tetrahydro-2H-pyran-3,4-diol (160 mg, 15% yield) as a white solid. LC-MS (ESI) found: 344 [M+1]+.

Step 2: To a mixture of (2R,3R,4R,5S)-5-((2-chloro-6-(trifluoromethyl)pyrimidin-4-yl)amino)-2-(hydroxymethyl)tetrahydro-2H-pyran-3,4-diol (20 mg, 0.058 mmol) in DMF (3.0 mL) was added $Zn(CN)_2$ (4.1 mg, 0.035 mmol), dppf (16.2 mg, 0.028 mmol), Zn (3.3 mg, 0.31 mmol) and $Pd_2(dba)_3$ (26.6 mg, 0.18 mmol) at rt under $N_2$. After stirring at 120° C. overnight, the reaction mixture was concentrated and purified by prep-TLC to give 4-(((3S,4R,5R,6R)-4,5-dihydroxy-6-(hydroxymethyl)tetrahydro-2H-pyran-3-yl)amino)-6-(trifluoromethyl)pyrimidine-2-carbonitrile (A81, 2.4 mg, 12% yield) as a white solid. LC-MS (ESI) found: 333 [M−H]−. $^1$H NMR (400 MHz, $CD_3OD$): δ 6.97 (s, 1H), 4.57-4.48 (m, 1H), 4.08 (dd, J=11.1, 5.2 Hz, 1H), 3.92 (d, J=2.8 Hz, 1H), 3.76 (dd, J=11.3, 7.1 Hz, 1H), 3.69 (dd, J=11.4, 4.9 Hz, 1H), 3.62 (dd, J=10.6, 3.1 Hz, 1H), 3.48-3.44 (m, 1H), 3.14 (t, J=10.9 Hz, 1H).

Preparation of A82: (2R,3R,4R,5S)-5-((5-fluoro-6-(trifluoromethyl)pyridin-2-yl)amino)-2-(hydroxymethyl)tetrahydro-2H-pyran-3,4-diol

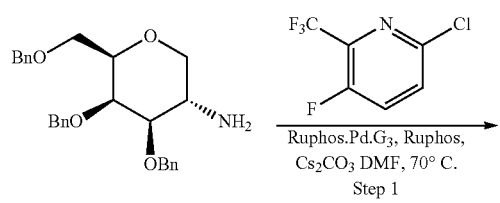

934

-continued

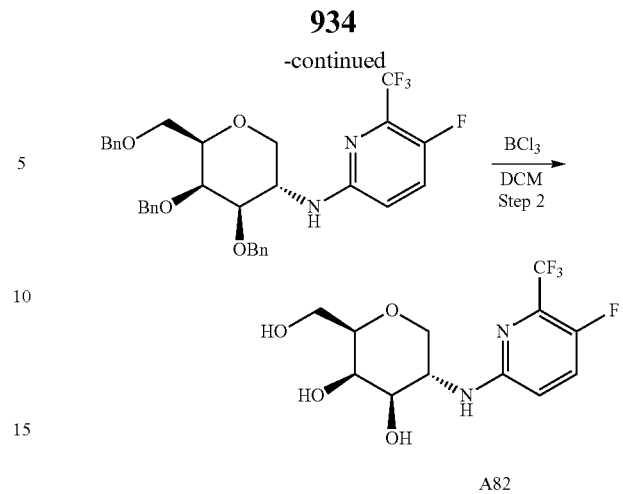

A82

Step 1: To a solution of (3S,4R,5R,6R)-4,5-bis(benzyloxy)-6-((benzyloxy)methyl)tetrahydro-2H-pyran-3-amine (200.0 mg, 0.462 mmol) in DMF (10.0 mL) was added 6-chloro-3-fluoro-2-(trifluoromethyl)pyridine (91.9 mg, 0.462 mmol), Ruphos.Pd.G3 (38.0 mg, 0.046 mmol), Ruphos (21.5 mg, 0.046 mmol) and $Cs_2CO_3$ (450.5 mg, 1.386 mmol). The mixture was stirred at 70° C. under $N_2$ for 16 h. The mixture was concentrated under reduced pressure to give a crude product, which was purified by column to give N-((3S,4R,5R,6R)-4,5-bis(benzyloxy)-6-((benzyloxy)methyl)tetrahydro-2H-pyran-3-yl)-5-fluoro-6-(trifluoromethyl)pyridin-2-amine (100.1 mg, 36% yield). LC-MS (ESI) found: 597 [M+H]+.

Step 2: To a solution of N-((3S,4R,5R,6R)-4,5-bis(benzyloxy)-6-((benzyloxy)methyl)tetrahydro-2H-pyran-3-yl)-5-fluoro-6-(trifluoromethyl)pyridin-2-amine (100.1 mg, 0.168 mmol) in DCM (20.0 mL) was added $BCl_3$ (1.68 mL, 1 N in DCM) at 0° C. The mixture was stirred at the room temperature for 2 h. The mixture was concentrated under reduced pressure to give a crude product, which was purified by column to give (2R,3R,4R,5S)-5-((5-fluoro-6-(trifluoromethyl)pyridin-2-yl)amino)-2-(hydroxymethyl)tetrahydro-2H-pyran-3,4-diol (A82, 6.0 mg, 11% yield). LC-MS (ESI) found: 327 [M+H]+. $^1$H NMR (400 MHz, $CD_3OD$): δ 7.40 (t, J=9.5 Hz, 1H), 6.77 (dd, J=9.2, 2.7 Hz, 1H), 4.30-4.11 (m, 2H), 3.90 (d, J=2.7 Hz, 1H), 3.75 (dd, J=11.4, 7.1 Hz, 1H), 3.68 (dd, J=11.4, 5.0 Hz, 1H), 3.59 (dd, J=10.1, 3.2 Hz, 1H), 3.48-3.41 (m, 1H), 3.08 (dd, J=15.1, 5.7 Hz, 1H). $^{19}$F NMR (377 MHz, $CD_3OD$): δ −66.95 (d, J=18.0 Hz), −141.07--145.72 (m).

Preparation of A83: (2R,3R,4R,5R)-2-(hydroxymethyl)-5-((6-(trifluoromethyl)pyrazin-2-yl)amino)tetrahydro-2H-pyran-3,4-diol

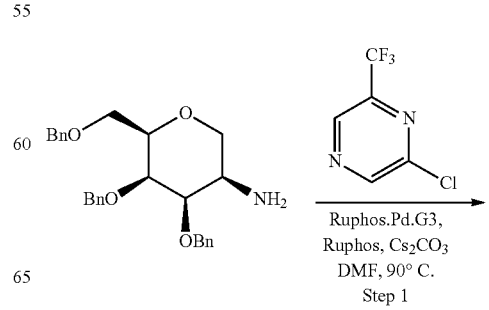

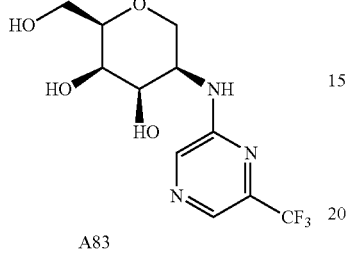

1H), 3.70 (dd, J=11.5, 4.7 Hz, 1H), 3.59 (dd, J=12.1, 1.7 Hz, 1H), 3.49-3.41 (m, 1H). ¹⁹F NMR (377 MHz, CD₃OD): δ −70.42 (s).

Preparation of A84: (1S,2R,3R,4R,5S)-1-(hydroxymethyl)-4-((5-(trifluoromethyl)pyrazin-2-yl)amino)-6,8-dioxabicyclo[3.2.1]octane-2,3-diol

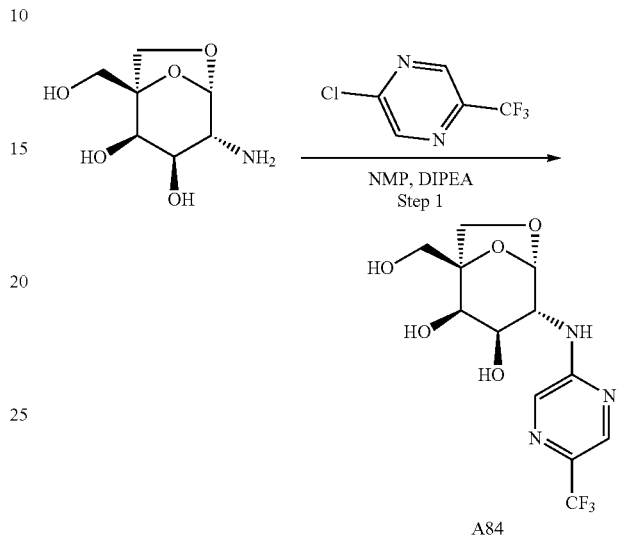

Step 1: To a solution of (3S,4R,5R,6R)-4,5-bis(benzyloxy)-6-((benzyloxy)methyl)tetrahydro-2H-pyran-3-amine (200.0 mg, 0.462 mmol) in DMF (10.0 mL) was added 2-chloro-6-(trifluoromethyl)pyrazine (84.1 mg, 0.462 mmol), Ruphos.Pd.G3 (38.0 mg, 0.046 mmol), Ruphos (21.5 mg, 0.046 mmol) and Cs₂CO₃ (450.5 mg, 1.386 mmol). The mixture was stirred at 70° C. under N₂ for 16 h. The mixture was concentrated under reduced pressure to give a crude product, which was purified by column to give N-((3R,4R,5R,6R)-4,5-bis(benzyloxy)-6-((benzyloxy)methyl)tetrahydro-2H-pyran-3-yl)-6-(trifluoromethyl)pyrazin-2-amine (95 mg, 34% yield). LC-MS (ESI) found: 580 [M+H]⁺.

Step 2: To a solution of N-((3R,4R,5R,6R)-4,5-bis(benzyloxy)-6-((benzyloxy)methyl)tetrahydro-2H-pyran-3-yl)-6-(trifluoromethyl)pyrazin-2-amine (95 mg, 0.168 mmol) in DCM (20.0 mL) was added BCl₃ (1.68 mL, 1 N in DCM) at 0° C. The mixture was stirred at the room temperature for 2 h. The mixture was concentrated under reduced pressure to give a crude product, which was purified by column to give (2R,3R,4R,5R)-2-(hydroxymethyl)-5-((6-(trifluoromethyl)pyrazin-2-yl)amino)tetrahydro-2H-pyran-3,4-diol (A83, 2.0 mg, 4% yield). LC-MS (ESI) found: 310[M+H]⁺. ¹H NMR (400 MHz, CD₃OD): δ 8.14 (s, 1H), 7.98 (s, 1H), 4.33 (d, J=3.5 Hz, 1H), 4.04 (dd, J=12.0, 2.0 Hz, 1H), 3.98-3.90 (m, 1H), 3.86 (dd, J=4.6, 3.2 Hz, 1H), 3.80 (dd, J=11.5, 7.1 Hz, Step 1: To a solution of (1S,2R,3R,4R,5S)-4-amino-1-(hydroxymethyl)-6,8-dioxabicyclo[3.2.1]octane-2,3-diol (20 mg, 0.11 mmol), 2-chloro-5-(trifluoromethyl)pyrazine (19 mg, 0.11 mmol) and DIPEA (20 mg, 0.16 mmol) in NMP (1 mL) was stirred at 80° C. overnight. The mixture was purified by prep-HPLC to give (1S,2R,3R,4R,5S)-1-(hydroxymethyl)-4-((5-(trifluoromethyl)pyrazin-2-yl)amino)-6,8-dioxabicyclo[3.2.1]octane-2,3-diol (A84, 5.4 mg, 15% yield) as yellow solid. LC-MS (ESI) found: 338 [M+H]⁺. ¹H NMR (400 MHz, CD₃OD): δ 8.26 (s, 1H), 7.99 (d, J=1.2 Hz, 1H), 5.35 (d, J=1.4 Hz, 1H), 4.25 (d, J=9.9 Hz, 1H), 3.94 (t, J=8.2 Hz, 2H), 3.83 (dt, J=10.6, 6.5 Hz, 3H), 3.71 (d, J=7.9 Hz, 1H).

Preparation of A85: (2R,3R,4R,5R)-2-(hydroxymethyl)-5-((6-(trifluoromethyl)pyrazin-2-yl)amino)tetrahydro-2H-pyran-3,4-diol

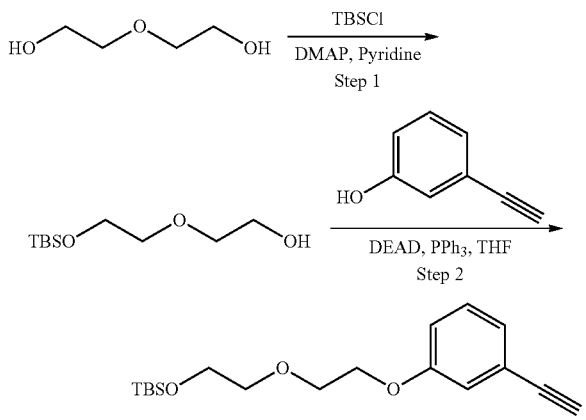

-continued
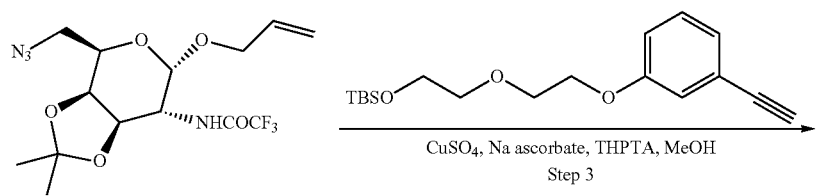
CuSO₄, Na ascorbate, THPTA, MeOH
Step 3
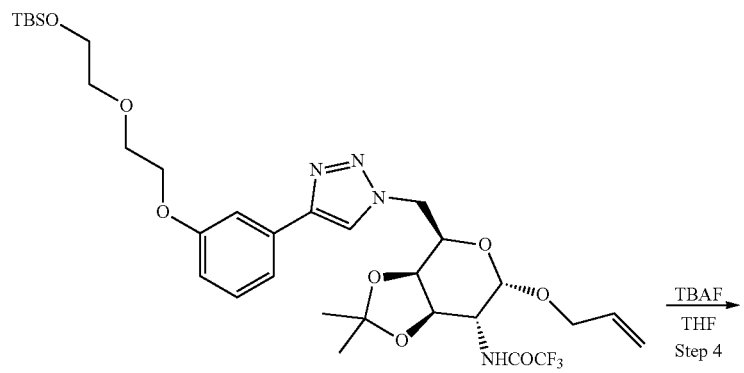
TBAF
THF
Step 4
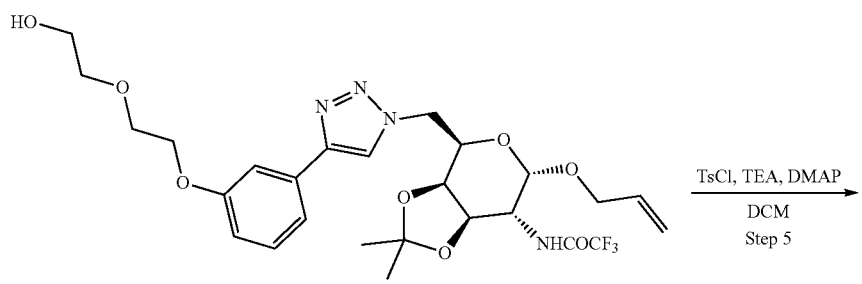
TsCl, TEA, DMAP
DCM
Step 5
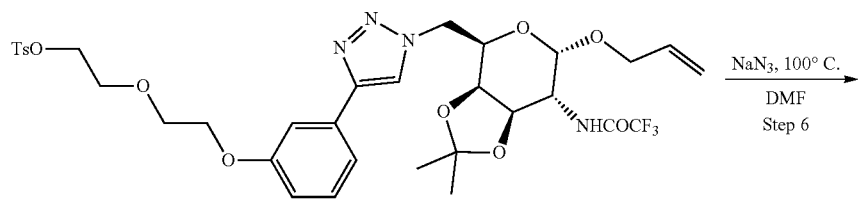
NaN₃, 100° C.
DMF
Step 6
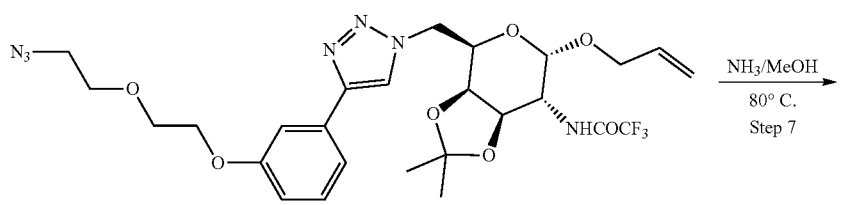
NH₃/MeOH
80° C.
Step 7
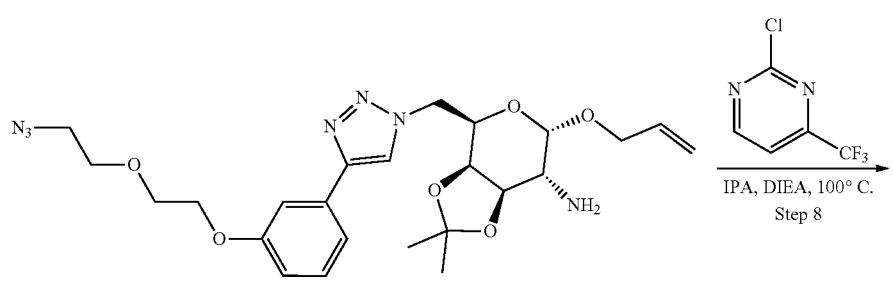
IPA, DIEA, 100° C.
Step 8

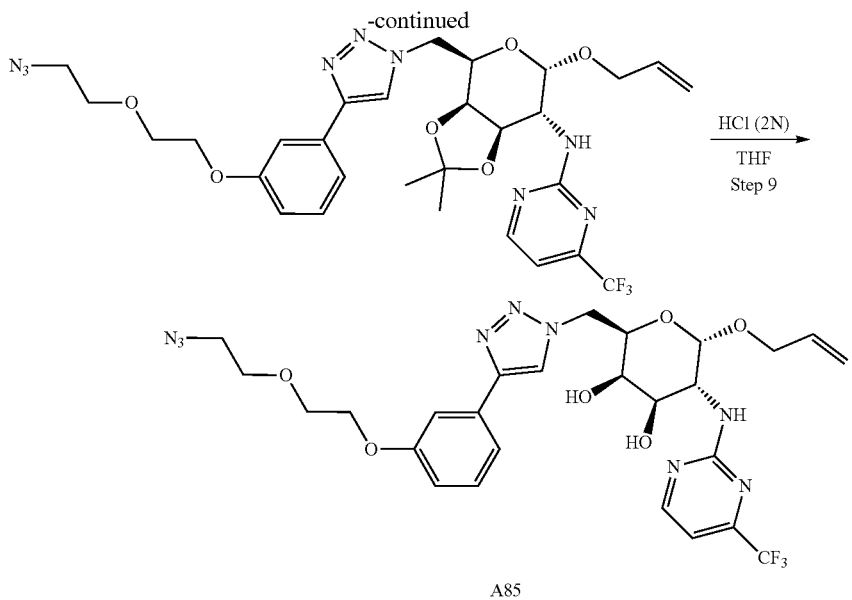

A85

Step 1: To a solution of 2,2'-oxybis(ethan-1-ol) (10.0 g, 90 mmol) in pyridine (50 mL) was added DMAP (22.0 g, 180.0 mmol) and TBSCl (1.35 g, 9.0 mmol) at 0° C. The mixture was stirred at rt under $N_2$ for 16 h. The mixture was concentrated under reduced pressure to give a crude product, which was purified by column to give 2-(2-((tert-butyldimethylsilyl)oxy)ethoxy)ethan-1-ol (1.47 g, 7% yield), LC-MS (ESI) found: 221 [M+H]$^+$.

Step 2: To a solution of 2-(2-((tert-butyldimethylsilyl)oxy)ethoxy)ethan-1-ol (1.47 g, 6.7 mmol) in THF (50.0 mL) was added 3-ethynylphenol (790.6 mg, 6.7 mmol), PPh$_3$ (2.1 g, 8.0 mmol) and DEAD (1.4 g, 8.0 mmol) at 0° C. The mixture was stirred at the room temperature for 2 h. The mixture was concentrated under reduced pressure to give a crude product, which was purified by column to give tert-butyl(2-(2-(3-ethynylphenoxy)ethoxy)ethoxy)dimethylsilane (1.2 g, 60% yield). LC-MS (ESI) found: 321 [M+H]$^+$.

Step 3: To a solution of tert-butyl(2-(2-(3-ethynylphenoxy)ethoxy)ethoxy)dimethylsilane (1.2 g, 4.0 mmol) in MeOH (50 mL) was added N-((3aS,4R,6S,7R,7aR)-6-(allyloxy)-4-(azidomethyl)-2,2-dimethyltetrahydro-4H-[1,3]dioxolo[4,5-c]pyran-7-yl)-2,2,2-trifluoroacetamide (1.5 g, 4.0 mmol), CuSO$_4$ (64.0 mg, 0.4 mmol), Na ascorbate (72.0 mg, 0.4 mmol) and THPTA (144.0 mg, 0.4 mmol). The mixture was stirred at the room temperature under $N_2$ for 16 h. The mixture was concentrated to give a crude product, which was purified by column to give N-((3aS,4R,6S,7R,7aR)-6-(allyloxy)-4-((4-(3-(2-(2-((tert-butyldimethylsilyl)oxy)ethoxy)ethoxy)phenyl)-1H-1,2,3-triazol-1-yl)methyl)-2,2-dimethyltetrahydro-4H-[1,3]dioxolo[4,5-c]pyran-7-yl)-2,2,2-trifluoroacetamide (900.0 mg, 32% yield). LC-MS (ESI) found: 701 [M+H]$^+$.

Step 4: To a solution of N-((3aS,4R,6S,7R,7aR)-6-(allyloxy)-4-((4-(3-(2-(2-((tert-butyldimethylsilyl)oxy)ethoxy)ethoxy)phenyl)-1H-1,2,3-triazol-1-yl)methyl)-2,2-dimethyltetrahydro-4H-[1,3]dioxolo[4,5-c]pyran-7-yl)-2,2,2-trifluoroacetamide (900.0 mg, 1.29 mmol) in THF (40.0 mL) was added TBAF (2.58 mL, 1 M in THF), the mixture was stirred at the room temperature for 16 h. The mixture was diluted with ethyl acetate (100 mL) and washed with water (60 mL×3). The organic layer was dried over sodium sulfate, filtered, concentrated under reduced pressure to give crude product, which was purified by column to afford N-((3aS,4R,6S,7R,7aR)-6-(allyloxy)-4-((4-(3-(2-(2-hydroxyethoxy)ethoxy)phenyl)-1H-1,2,3-triazol-1-yl)methyl)-2,2-dimethyltetrahydro-4H-[1,3]dioxolo[4,5-c]pyran-7-yl)-2,2,2-trifluoroacetamide (586 mg, 77% yield). LC-MS (ESI) found: 587 [M+H]$^+$.

Step 5: To a solution of N-((3aS,4R,6S,7R,7aR)-6-(allyloxy)-4-((4-(3-(2-(2-hydroxyethoxy)ethoxy)phenyl)-1H-1,2,3-triazol-1-yl)methyl)-2,2-dimethyltetrahydro-4H-[1,3]dioxolo[4,5-c]pyran-7-yl)-2,2,2-trifluoroacetamide (586.0 mg, 1.0 mmol) in DCM (30.0 mL) was added TEA (303 mg, 3.0 mmol), DMAP (122.0 mg, 1.0 mmol), and TsCl (229.0 mg, 1.20 mmol). The mixture was stirred at the room temperature for 16 h. The mixture was diluted with ethyl acetate (100 mL) and washed with water (50 mL×3), the organic layer was concentrated under reduced pressure to give a crude product, which was purified by column to give 2-(2-(3-(1-(((3aS,4R,6S,7R,7aR)-6-(allyloxy)-2,2-dimethyl-7-(2,2,2-trifluoroacetamido)tetrahydro-4H-[1,3]dioxolo[4,5-c]pyran-4-yl)methyl)-1H-1,2,3-triazol-4-yl)phenoxy)ethoxy)ethyl 4-methylbenzenesulfonate (584 mg, 79% yield). LC-MS (ESI) found: 741 [M+H]$^+$.

Step 6: To a solution of 2-(2-(3-(1-(((3aS,4R,6S,7R,7aR)-6-(allyloxy)-2,2-dimethyl-7-(2,2,2-trifluoroacetamido)tetrahydro-4H-[1,3]dioxolo[4,5-c]pyran-4-yl)methyl)-1H-1,2,3-triazol-4-yl)phenoxy)ethoxy)ethyl 4-methylbenzenesulfonate (584 mg, 0.79 mmol) in DMF (30.0 mL) was added NaN$_3$ (513.0 mg, 7.9 mmol), the mixture was stirred at 100° C. for 16 h. The mixture was diluted with ethyl acetate (150.0 mL) and washed with water (100.0 mL×3), the organic layer was concentrated under reduced to give a crude product, which was purified by column to give N-((3aS,4R,6S,7R,7aR)-6-(allyloxy)-4-((4-(3-(2-(2-azidoethoxy)ethoxy)phenyl)-1H-1,2,3-triazol-1-yl)methyl)-2,2-dimethyltetrahydro-4H-[1,3]dioxolo[4,5-c]pyran-7-yl)-2,2,2-trifluoroacetamide (427 mg, 88% yield). LC-MS (ESI) found: 612 [M+H]$^+$.

Step 7: To a solution of N-((3aS,4R,6S,7R,7aR)-6-(allyloxy)-4-((4-(3-(2-(2-azidoethoxy)ethoxy)phenyl)-1H-1,2,3-triazol-1-yl)methyl)-2,2-dimethyltetrahydro-4H-[1,3]dioxolo[4,5-c]pyran-7-yl)-2,2,2-trifluoroacetamide (427.0 mg, 0.70 mmol) in NH$_3$/MeOH (20 mL, 7 M), was stirred at 80° C. for 16 h. The mixture was concentrated under reduced pressure to give crude (3aS,4R,6S,7R,7aR)-6-(allyloxy)-4-((4-(3-(2-(2-azidoethoxy)ethoxy)phenyl)-1H-1,2,3-triazol-1-yl)methyl)-2,2-dimethyltetrahydro-4H-[1,3]dioxolo[4,5-c]pyran-7-amine (309 mg, 85% yield). LC-MS (ESI) found: 516 [M+H]⁺.

Step 8: To a solution of (3aS,4R,6S,7R,7aR)-6-(allyloxy)-4-((4-(3-(2-(2-azidoethoxy)ethoxy)phenyl)-1H-1,2,3-triazol-1-yl)methyl)-2,2-dimethyltetrahydro-4H-[1,3]dioxolo[4,5-c]pyran-7-amine (30.9 mg, 0.06 mmol) in i-PrOH (30.0 mL) was added 2-chloro-4-(trifluoromethyl)pyrimidine (10.9 mg, 0.06 mmol) and DIEA (23.6 mg, 1.8 mmol). The mixture was stirred at 100° C. for 16 h. The mixture was concentrated and purified by column to give N-((3aS,4R,6S,7R,7aR)-6-(allyloxy)-4-((4-(3-(2-(2-azidoethoxy)ethoxy)phenyl)-1H-1,2,3-triazol-1-yl)methyl)-2,2-dimethyltetrahydro-4H-[1,3]dioxolo[4,5-c]pyran-7-yl)-4-(trifluoromethyl)pyrimidin-2-amine (36.3 mg, 93% yield). LC-MS (ESI) found: 662 [M+H]⁺.

Step 9: To a solution of N-((3aS,4R,6S,7R,7aR)-6-(allyloxy)-4-((4-(3-(2-(2-azidoethoxy)ethoxy)phenyl)-1H-1,2,3-triazol-1-yl)methyl)-2,2-dimethyltetrahydro-4H-[1,3]dioxolo[4,5-c]pyran-7-yl)-4-(trifluoromethyl)pyrimidin-2-amine (36.3 mg, 0.056 mmol) in THF (2 mL) was added HCl (2 mL, 2 N in water). The mixture was stirred at the room temperature for 16 h. The mixture was concentrated and purified by column to give (2R,3R,4R,5R,6S)-6-(allyloxy)-2-((4-(3-(2-(2-azidoethoxy)ethoxy)phenyl)-1H-1,2,3-triazol-1-yl)methyl)-5-((4-(trifluoromethyl)pyrimidin-2-yl)amino)tetrahydro-2H-pyran-3,4-diol (A85, 3.0 mg, 10% yield). LC-MS (ESI) found: 662 [M+H]⁺. ¹H NMR (400 MHz, CD₃OD): δ 8.52 (d, J=4.5 Hz, 1H), 8.36 (s, 1H), 7.42 (dd, J=10.7, 5.0 Hz, 2H), 7.34 (t, J=7.9 Hz, 1H), 6.97-6.89 (m, 2H), 5.63 (m, 1H), 4.98 (dd, J=27.9, 14.3 Hz, 3H), 4.74-4.66 (m, 3H), 4.30 (dd, J=8.2, 4.5 Hz, 1H), 4.22-4.17 (m, 2H), 4.01 (d, J=2.6 Hz, 1H), 3.96 (dd, J=10.8, 3.1 Hz, 1H), 3.88 (dd, J=5.4, 3.8 Hz, 2H), 3.78-3.70 (m, 3H), 3.68 (d, J=5.6 Hz, 1H), 3.43-3.37 (m, 2H). ¹⁹F NMR (377 MHz, CD₃OD): δ −72.34 (s).

Preparation of A86: (2R,3R,4R,5S)-2-(azidomethyl)-5-((6-(trifluoromethyl)pyrazin-2-yl)amino)tetrahydro-2H-pyran-3,4-diol

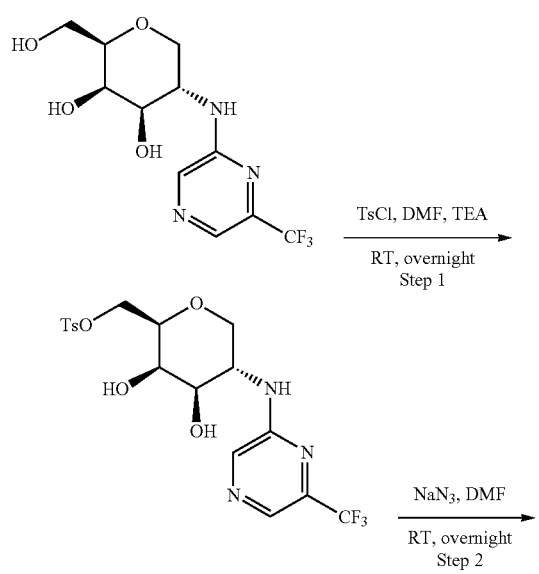

-continued

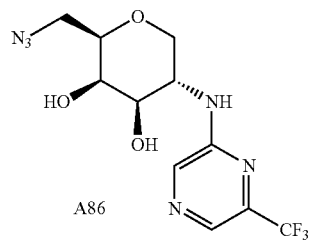

Step 1: To a solution of (2R,3R,4R,5S)-2-(hydroxymethyl)-5-((6-(trifluoromethyl)pyrazin-2-yl)amino)tetrahydro-2H-pyran-3,4-diol (300 mg, 0.97 mmol) and TEA (196 mg, 1.94 mmol) in DMF (5 mL) was added TsCl (276 mg, 1.5 mmol) at rt. The reaction mixture was stirred at rt overnight. The resulting mixture was concentrated in vacuo. The crude product was purified by prep-HPLC to give benzyl 3,3'-((2-(2-(2-(2-(2-(2,5-dioxopyrrolidin-1-yl)-2-oxoethoxy)ethoxy) ((2R,3R,4R,5S)-3,4-dihydroxy-5-((6-(trifluoromethyl)pyrazin-2-yl)amino)tetrahydro-2H-pyran-2-yl)methyl 4-methylbenzenesulfonate (150 mg, 43% yield) as white solid. LC-MS (ESI) found: 464 [M+H]⁺.

Step 2: To a solution of benzyl 3,3'-((2-(2-(2-(2-(2-(2,5-dioxopyrrolidin-1-yl)-2-oxoethoxy)ethoxy) ((2R,3R,4R,5S)-3,4-dihydroxy-5-((6-(trifluoromethyl)pyrazin-2-yl)amino)tetrahydro-2H-pyran-2-yl)methyl 4-methylbenzenesulfonate (150 mg, 0.32 mmol) in DMF (5 mL) was added NaN₃ (208 mg, 3.2 mmol) at rt. The reaction mixture was stirred at 120° C. overnight. The resulting mixture was filtered and the filtrate was purified by C18 directly. Then the crude product was further purified by prep-HPLC to give (2R,3R,4R,5S)-2-(azidomethyl)-5-((6-(trifluoromethyl)pyrazin-2-yl)amino)tetrahydro-2H-pyran-3,4-diol (A86, 7 mg, 5.7% yield) as white solid. LC-MS (ESI) found: 375 [M+H]⁺. ¹H NMR (400 MHz, CD₃OD): δ 8.11 (s, 1H), 8.00 (s, 1H), 4.33 (td, J=10.4, 4.9 Hz, 1H), 4.14 (dd, J=11.0, 5.2 Hz, 1H), 3.84 (d, J=3.2 Hz, 1H), 3.66 (dd, J=10.6, 3.3 Hz, 1H), 3.58 (q, J=5.4 Hz, 2H), 3.34 (d, J=8.0 Hz, 1H), 3.14 (dd, J=13.8, 7.8 Hz, 1H).

Preparation of A87: (1S,2R,3R,4R,5S)-1-(hydroxymethyl)-4-((6-(trifluoromethylpyridine-2-yl)amino)-6,8-dioxabicyclo[3.2.1]octane-2,3-diol

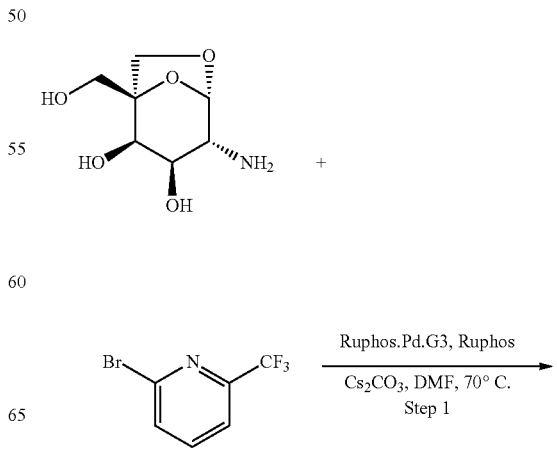

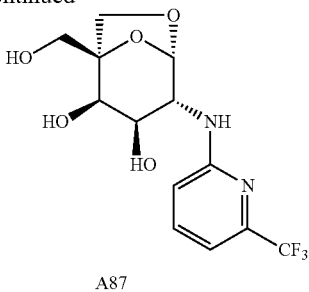

A87

Step 1: To a solution of (1S,2R,3R,4R,5S)-4-amino-1-(hydroxymethyl)-6,8-dioxabicyclo[3.2.1]octane-2,3-diol (100 mg, 0.523 mmol) and 2-bromo-6-(trifluoromethyl)pyridine (177 mg, 0.785 mmol) in DMF (5 mL) were added RuPhos Pd G3 (43 mg, 0.05 mmol), Ruphos (24 mg, 0.052 mmol) and $Cs_2CO_3$ (507 mg, 1.59 mmol). The reaction was stirred at 70° C. for 18 h. The reaction mixture was filtered through Celite and the filtrate was concentrated and purified by prep-HPLC to give (1S,2R,3R,4R,5S)-1-(hydroxymethyl)-4-((6-(trifluoromethyl)pyridin-2-yl)amino)-6,8-dioxabicyclo[3.2.1]octane-2,3-diol (A87, 6 mg, 3% yield). LC-MS (ESI) found: 337 [M+H]+. 1H NMR (400 MHz, $CD_3OD$): δ 8.52 (s, 1H), 7.53 (t, J=7.9 Hz, 1H), 6.89 (d, J=7.2 Hz, 1H), 6.77 (d, J=8.5 Hz, 1H), 5.41 (s, 1H), 4.18 (d, J=9.8 Hz, 1H), 3.93 (dd, J=11.8, 7.8 Hz, 2H), 3.87-3.76 (m, 3H), 3.71 (d, J=7.9 Hz, 1H).

Preparation of A88: (2R,3R,4R,5S)-2-((dimethylamino)methyl)-5-((6-(trifluoromethyl)pyrazin-2-yl)amino)tetrahydro-2H-pyran-3,4-diol

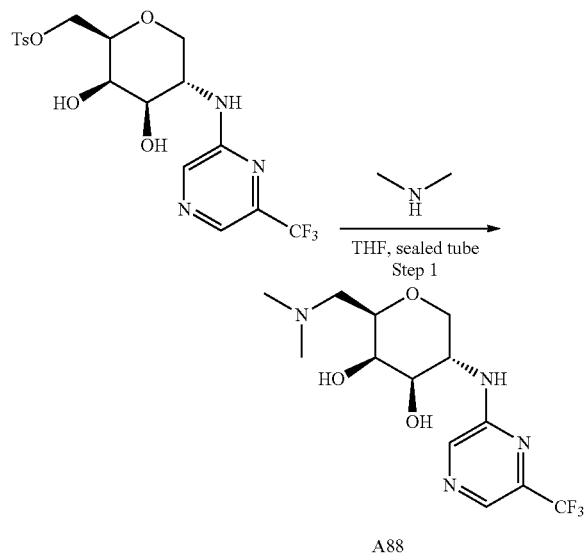

A88

Step 1: To a solution of ((2R,3R,4R,5S)-3,4-dihydroxy-5-((6-(trifluoromethyl)pyrazin-2-yl)amino)tetrahydro-2H-pyran-2-yl)methyl 4-methylbenzenesulfonate (200 mg, 0.43 mmol) in dimethylamine (2 mL, 2 M in THF) was stirred at 80° C. for 2 h. The mixture was concentrated and the residue was purified by prep-HPLC to give (2R,3R,4R,5S)-2-((dimethylamino)methyl)-5-((6-(trifluoromethyl)pyrazin-2-yl)amino)tetrahydro-2H-pyran-3,4-diol (A88, 11 mg, 8% yield) as white solid. LC-MS (ESI) found: 337 [M+H]+. 1H NMR (400 MHz, $CD_3OD$): δ 8.11 (s, 1H), 8.00 (s, 1H), 4.32 (td, J=10.5, 5.1 Hz, 1H), 4.13 (dd, J=11.0, 5.1 Hz, 1H), 3.82 (d, J=2.4 Hz, 1H), 3.63 (ddd, J=10.2, 9.3, 2.6 Hz, 2H), 3.12 (t, J=10.8 Hz, 1H), 2.87 (dd, J=13.3, 8.3 Hz, 1H), 2.63 (dd, J=13.3, 2.9 Hz, 1H), 2.40 (s, 6H).

Preparation of A89: (2R,3R,4R,5S)-2-(aminomethyl)-5-((6-(trifluoromethyl)pyrazin-2-yl)amino)tetrahydro-2H-pyran-3,4-diol and A90: N-(((2R,3R,4R,5S)-3,4-dihydroxy-5-((6-(trifluoromethyl)pyrazin-2-yl)amino)tetrahydro-2H-pyran-2-yl)methyl)acetamide Step 1: To a solution of (2R,3R,4R,5S)-2-(azidomethyl)-5-((6-(trifluoromethyl)pyrazin-2-yl)amino)tetrahydro-2H-pyran-3,4-diol (10 mg, 0.03 mmol) and Pd/C (3 mg, 10% wt., 60% wet) in MeOH (3 mL) was stirred at rt under a $H_2$ balloon overnight. The mixture was filtered through a Celite pad, and the filtrate was concentrated to give crude product, which was purified by prep-HPLC to give (2R,3R,4R,5S)-2-(aminomethyl)-5-((6-(trifluoromethyl)pyrazin-2-yl)amino)tetrahydro-2H-pyran-3,4-diol (A89, 6 mg, 65% yield) as white solid. LC-MS (ESI) found: 309 [M+H]+. 1H NMR (400 MHz, $CD_3OD$): δ 8.11 (s, 1H), 8.00 (s, 1H), 4.33 (d, J=5.1 Hz, 1H), 4.16 (dd, J=11.0, 5.2 Hz, 1H), 3.87 (d, J=2.5 Hz, 1H), 3.66 (dd, J=10.5, 3.1 Hz, 1H), 3.44 (dd, J=7.4, 4.2 Hz, 1H), 3.13 (t, J=10.8 Hz, 1H), 3.02 (dd, J=13.2, 7.9 Hz, 1H), 2.84 (dd, J=13.2, 4.1 Hz, 1H).

Step 2: To a solution of (2R,3R,4R,5S)-2-(aminomethyl)-5-((6-(trifluoromethyl)pyrazin-2-yl)amino)tetrahydro-2H-pyran-3,4-diol (2.6 mg, 0.008 mmol), $Et_3N$ (1.2 mg, 0.01 mmol) and N-acetoxysuccinimidec (2 mg, 0.012 mmol) in MeOH (3 mL) was stirred at rt overnight. The mixture was directly purified by prep-HPLC to give N-(((2R,3R,4R,5S)-3,4-dihydroxy-5-((6-(trifluoromethyl)pyrazin-2-yl)amino)tetrahydro-2H-pyran-2-yl)methyl)acetamide (A90, 1.2 mg, 41% yield) as white solid. LC-MS (ESI) found: 351 [M+H]$^+$. $^1$H NMR (400 MHz, CD$_3$OD): δ 8.10 (s, 1H), 8.00 (s, 1H), 4.31 (td, J=10.6, 5.0 Hz, 1H), 4.12 (dd, J=11.0, 5.1 Hz, 1H), 3.83 (d, J=2.8 Hz, 1H), 3.63 (dd, J=10.5, 3.1 Hz, 1H), 3.49 (dd, J=12.4, 7.6 Hz, 2H), 3.27 (d, J=10.6 Hz, 1H), 3.09 (t, J=10.9 Hz, 1H), 1.95 (s, 3H).

Preparation of A91: (2R,3R,4R,5S)-2-(hydroxymethyl)-5-(pyridin-2-ylamino)tetrahydro-2H-pyran-3,4-diol

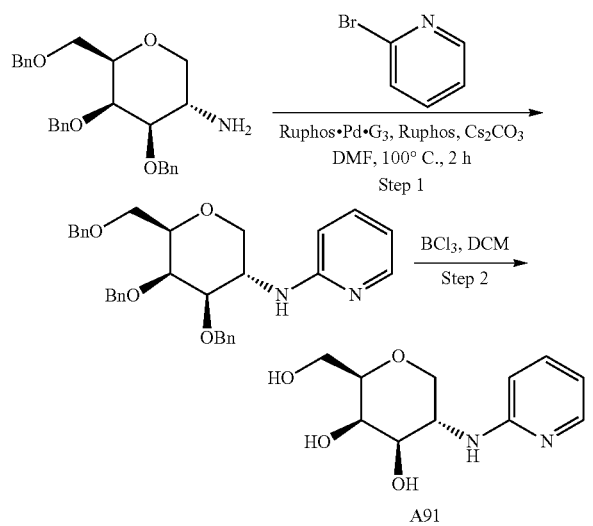

Step 1: To a solution of (3S,4R,5R,6R)-4,5-bis(benzyloxy)-6-((benzyloxy)methyl)tetrahydro-2H-pyran-3-amine (200 mg, 0.462 mmol) in DMF (10 mL) was added Ruphos-.Pd.G3 (38.5 mg, 0.046 mmol), Ruphos (21.5 mg, 0.046 mmol), Cs$_2$CO$_3$ (452 mg, 1.386 mmol). The mixture was stirred at 80° C. under N$_2$ for 16 h. The mixture was diluted with ethyl acetate (40 mL) and washed with water (50 mL×3). The organic layer was dried over sulfate sodium, filtered, concentrated under reduced pressure to give a crude product, which was purified by column to give N-((3S,4R,5R,6R)-4,5-bis(benzyloxy)-6-((benzyloxy)methyl)tetrahydro-2H-pyran-3-yl)pyridin-2-amine (50 mg, 21% yield). LC-MS (ESI) found: 511 [M+H]$^+$.

Step 2: To a solution of N-((3S,4R,5R,6R)-4,5-bis(benzyloxy)-6-((benzyloxy)methyl)tetrahydro-2H-pyran-3-yl)pyridin-2-amine (50 mg, 0.098 mmol) in DCM (5 mL) at 0° C. was added BCl$_3$ (0.98 mL, 1 M in DCM). The mixture was stirred at room temperature for 1 h. The mixture was quenched with NH$_3$·H$_2$O (0.5 mL). The mixture was concentrated under reduced pressure to give a crude product, which was purified by prep-HPLC to give (2R,3R,4R,5S)-2-(hydroxymethyl)-5-(pyridin-2-ylamino)tetrahydro-2H-pyran-3,4-diol (A91, 5 mg, 21% yield). LC-MS (ESI) found: 241 [M+H]$^+$. $^1$H NMR (400 MHz, CD$_3$OD): δ 7.93 (d, J=8.3 Hz, 2H), 7.63 (d, J=2.8 Hz, 1H), 4.28 (td, J=10.5, 5.2 Hz, 1H), 4.10 (dd, J=11.0, 5.3 Hz, 1H), 3.92 (d, J=2.5 Hz, 1H), 3.73 (m, 2H), 3.62 (dd, J=10.5, 2.9 Hz, 1H), 3.50-3.42 (m, 1H), 3.13 (t, J=10.9 Hz, 1H).

Preparation of A92: benzyl (2R,3R,4R,5S)-2-((4-methylpiperazin-1-yl)methyl)-5-((6-(trifluoromethyl)pyrazin-2-yl)amino)tetrahydro-2H-pyran-3,4-diol

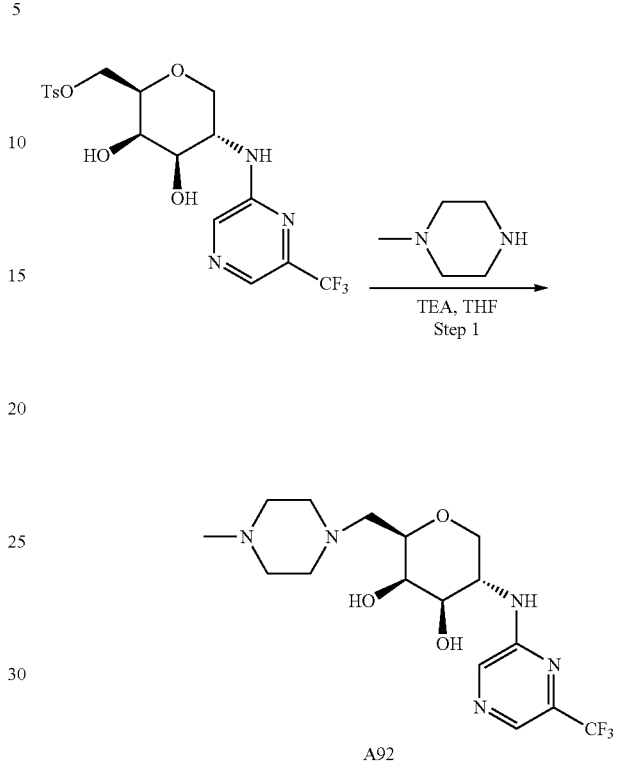

Step 1: To a solution of ((2R,3R,4R,5S)-3,4-dihydroxy-5-((6-(trifluoromethyl)pyrazin-2-yl)amino)tetrahydro-2H-pyran-2-yl)methyl 4-methylbenzenesulfonate (120 mg, 0.26 mmol), 1-methylpiperazine (78 mg, 0.78 mmol), and TEA (101 mg, 1 mmol) in THF (3 mL) was stirred at 80° C. overnight in a sealed tube. The mixture was concentrated in vacuo. The crude product was purified by C18 to give (2R,3R,4R,5S)-2-((4-methylpiperazin-1-yl)methyl)-5-((6-(trifluoromethyl)pyrazin-2-yl)amino)tetrahydro-2H-pyran-3,4-diol (A92, 4 mg, 4% yield) as a white solid. LC-MS (ESI) found: 392 [M+H]$^+$. $^1$H NMR (400 MHz, CD$_3$OD): δ 8.11 (s, 1H), 7.99 (s, 1H), 4.42-4.26 (m, 1H), 4.11 (dd, J=11.0, 5.2 Hz, 1H), 3.86 (d, J=2.3 Hz, 1H), 3.68-3.53 (m, 2H), 3.09 (t, J=10.8 Hz, 1H), 2.76 (dd, J=13.6, 7.2 Hz, 2H), 2.68-2.49 (m, 8H), 2.29 (s, 3H). $^{19}$F NMR (377 MHz, CD$_3$OD): δ −70.34.

Preparation of A93: (2R,3R,4R,5S)-2-(hydroxymethyl)-5-((5-(trifluoromethyl)-1H-pyrazol-3-yl)amino)tetrahydro-2H-pyran-3,4-diol

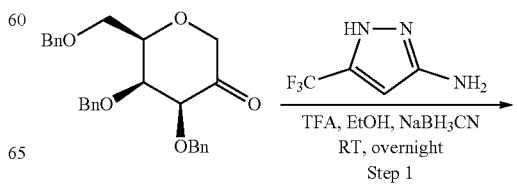

-continued

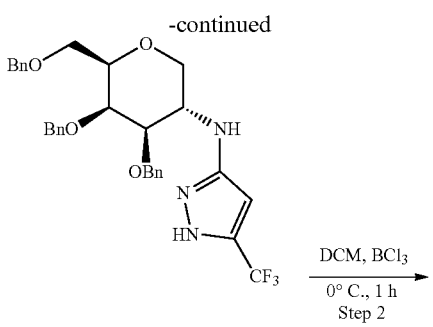

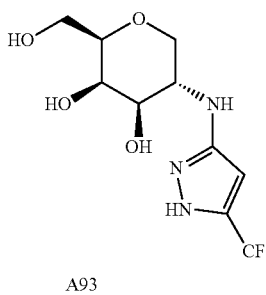

A93

Step 1: To a solution of (4S,5S,6R)-4,5-bis(benzyloxy)-6-((benzyloxy)methyl)dihydro-2H-pyran-3(4H)-one (200 mg, 0.46 mmol) in EtOH (5 mL) at rt was added TFA (5.7 mg, 0.05 mmol), 5-(trifluoromethyl)-1H-pyrazol-3-amine (83 mg, 0.56 mmol) and NaBH$_3$CN (57 mg, 0.92 mmol). The mixture was stirred at the room temperature overnight. On consumption of starting material (LCMS monitoring), water (5 mL) was slowly added and the reaction mixture stirred for 15 min. The mixture was diluted with ethyl acetate (50 mL) and washed with water (5 mL×3). The organic layer was dried over sodium sulfate, concentrated under reduced pressure to give a crude product, which was purified by prep-HPLC to give N-((3S,4R,5R,6R)-4,5-bis (benzyloxy)-6-((benzyloxy)methyl)tetrahydro-2H-pyran-3-yl)-5-(trifluoromethyl)-1H-pyrazol-3-amine (20 mg, 7.6% yield) as a colorless oil. LC-MS (ESI) found: 568 [M+H]$^+$.

Step 2: To a solution of N-((3S,4R,5R,6R)-4,5-bis(benzyloxy)-6-((benzyloxy)methyl)tetrahydro-2H-pyran-3-yl)-5-(trifluoromethyl)-1H-pyrazol-3-amine (20 mg, 0.035 mmol) in DCM (5 mL) was added BCl$_3$ (41 mg, 0.35 mmol) at 0° C. The reaction was stirred at 0° C. for 1 h. The mixture was concentrated under reduced pressure to give a crude product, which was purified by prep-HPLC to afford (2R, 3R,4R,5S)-2-(hydroxymethyl)-5-((5-(trifluoromethyl)-1H-pyrazol-3-yl)amino)tetrahydro-2H-pyran-3,4-diol (6 mg, 60% yield) as white solid. LC-MS (ESI) found: 298 [M+H]$^+$. $^1$H NMR (400 MHz, MeOD): δ 5.70 (s, 1H), 4.02 (d, J=11.0 Hz, 1H), 3.88 (s, 1H), 3.83-3.74 (m, 2H), 3.67 (dd, J=11.5, 4.7 Hz, 1H), 3.58-3.47 (m, 2H), 3.44-3.39 (m, 1H).

Preparation of A94: (2R,3R,4R,5S)-2-(6-bromo-1H-benzo[d]imidazol-2-yl)-5-((4-(trifluoromethyl)pyrimidin-2-yl)amino)tetrahydro-2H-pyran-3,4-diol

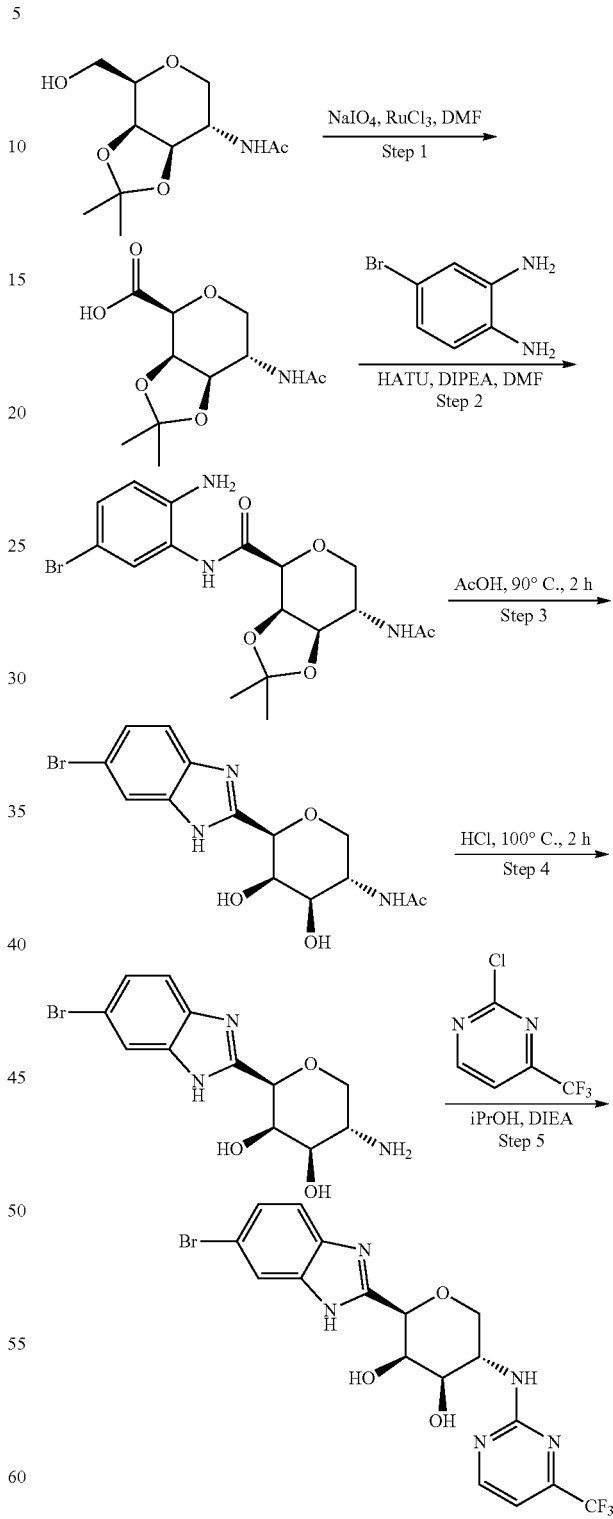

A94

Step 1: To a solution of N-((3aR,4R,7S,7aR)-4-(hydroxymethyl)-2,2-dimethyltetrahydro-4H-[1,3]dioxolo[4,5-c]pyran-7-yl)acetamide (2 g, 8.15 mmol) in DMF (25 mL)

were added RuCl₃ (0.17 g, 0.81 mmol) and NaIO₄ (3.6 g, 16.3 mmol) at rt. The mixture was stirred at rt overnight, The mixture was concentrated and the residue was purified by flash to give (3aR,4S,7S,7aR)-7-acetamido-2,2-dimethyltetrahydro-4H-[1,3]dioxolo[4,5-c]pyran-4-carboxylic acid (1 g, 47% yield) as brown oil. LC-MS (ESI) found: 260 [M+H]⁺.

Step 2: To a solution of (3aR,4S,7S,7aR)-7-acetamido-2,2-dimethyltetrahydro-4H-[1,3]dioxolo[4,5-c]pyran-4-carboxylic acid (200 mg, 0.77 mmol) in DMF (2 mL) were added HATU (440 mg, 1.16 mmol) and DIPEA (199 mg, 1.54 mmol) at rt. After stirring at rt for 20 min, 4-bromobenzene-1,2-diamine (144 mg, 0.77 mmol) was added. The mixture was stirred at rt overnight. The mixture was concentrated and the residue was purified by flash to give (3aR,4S,7S,7aR)-7-acetamido-N-(2-amino-5-bromophenyl)-2,2-dimethyltetrahydro-4H-[1,3]dioxolo[4,5-c]pyran-4-carboxamide (91 mg, 28% yield) as yellow oil. LC-MS (ESI) found: 428 & 430 [M+H]⁺.

Step 3: To a solution of (3aR,4S,7S,7aR)-7-acetamido-N-(2-amino-5-bromophenyl)-2,2-dimethyltetrahydro-4H-[1,3]dioxolo[4,5-c]pyran-4-carboxamide (90 mg, 0.21 mmol) in AcOH (2 mL) was stirred at 90° C. for 2 h, then concentrated. The residue was purified by flash to give N-((3S,4R,5R,6R)-6-(6-bromo-1H-benzo[d]imidazol-2-yl)-4,5-dihydroxytetrahydro-2H-pyran-3-yl)acetamide (30 mg, 39% yield) as yellow oil. LC-MS (ESI) found: 370 & 372 [M+H]⁺.

Step 4: To a solution of N-((3S,4R,5R,6R)-6-(6-bromo-1H-benzo[d]imidazol-2-yl)-4,5-dihydroxytetrahydro-2H-pyran-3-yl)acetamide (30 mg, 0.08 mmol) in HCl (4 mL, 4 N in H₂O) was stirred at 100° C. for 2 h. The mixture was concentrated to give cude (2R,3R,4R,5S)-5-amino-2-(6-bromo-1H-benzo[d]imidazol-2-yl)tetrahydro-2H-pyran-3,4-diol (10 mg, 38% yield) as yellow oil. LC-MS (ESI) found: 328 & 330 [M+H]⁺.

Step 5: To a solution of (2R,3R,4R,5S)-5-amino-2-(6-bromo-1H-benzo[d]imidazol-2-yl)tetrahydro-2H-pyran-3,4-diol (10 mg, 0.03 mmol), 2-chloro-4-(trifluoromethyl)pyrimidinen (8 mg, 0.04 mmol) and DIPEA (8 mg, 0.06 mmol) in i-PrOH (1 mL) was stirred at 80° C. overnight. The mixture was concentrated and the residue was purified by prep-HPLC to give (2R,3R,4R,5S)-2-(6-bromo-1H-benzo[d]imidazol-2-yl)-5-((4-(trifluoromethyl)pyrimidin-2-yl)amino)tetrahydro-2H-pyran-3,4-diol (A94, 1.2 mg, 8% yield) as white solid. LC-MS (ESI) found: 328 & 330 [M+H]⁺. ¹H NMR (400 MHz, MeOD): δ 8.54 (d, J=4.6 Hz, 1H), 7.71 (s, 1H), 7.47 (d, J=8.4 Hz, 1H), 7.34 (dd, J=8.6, 1.8 Hz, 1H), 6.92 (d, J=4.9 Hz, 1H), 4.88 (s, 1H), 4.52 (s, 1H), 4.31 (s, 2H), 3.92 (d, J=10.4 Hz, 1H), 3.40 (t, J=11.0 Hz, 1H).

Preparation of A95: (2R,3R,4R,5S)-2-((phenylamino)methyl)-5-((6-(trifluoromethyl)pyrazin-2-yl)amino)tetrahydro-2H-pyran-3,4-diol

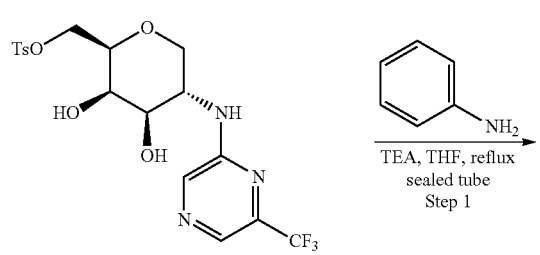

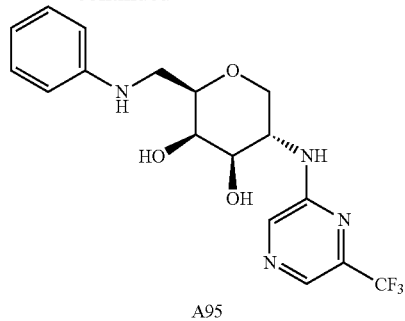

A95

Step 1: To a solution of ((2R,3R,4R,5S)-3,4-dihydroxy-5-((6-(trifluoromethyl)pyrazin-2-yl)amino)tetrahydro-2H-pyran-2-yl)methyl 4-methylbenzenesulfonate (50 mg, 0.11 mmol), aniline (20 mg, 0.22 mmol) and TEA (23 mg, 0.22 mmol) in THF was stirred at 80° C. overnight. The mixture was concentrated and the residue was purified by prep-HPLC to give (2R,3R,4R,5S)-2-((phenylamino)methyl)-5-((6-(trifluoromethyl)pyrazin-2-yl)amino)tetrahydro-2H-pyran-3,4-diol (A95, 1 mg, 2% yield) as white solid. LC-MS (ESI) found: 385 [M+H]⁺. ¹H NMR (400 MHz, CD₃OD): δ 8.10 (s, 1H), 8.00 (s, 1H), 7.11 (dd, J=8.5, 7.4 Hz, 2H), 6.70-6.57 (m, 3H), 4.36 (td, J=10.7, 5.3 Hz, 1H), 4.15 (dd, J=11.0, 5.2 Hz, 1H), 3.93 (d, J=3.0 Hz, 1H), 3.66-3.58 (m, 2H), 3.36 (dd, J=6.3, 3.2 Hz, 2H), 3.11 (t, J=10.8 Hz, 1H).

Preparation of A96: (2R,3R,4R,5S)-2-(piperidin-1-ylmethyl)-5-((6-(trifluoromethyl)pyrazin-2-yl)amino)tetrahydro-2H-pyran-3,4-diol

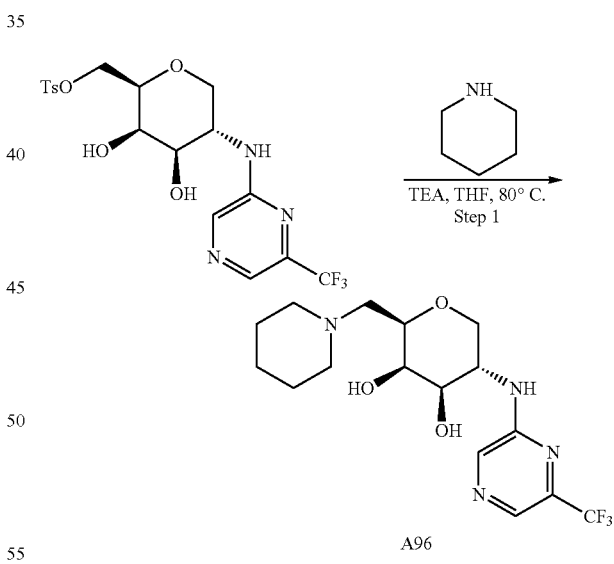

A96

Step 1: To the solution of ((2R,3R,4R,5S)-3,4-dihydroxy-5-((6-(trifluoromethyl)pyrazin-2-yl)amino)tetrahydro-2H-pyran-2-yl)methyl 4-methylbenzenesulfonate (70 mg, 0.08 mmol) in THF (1 mL) was added piperidine (80 μL, 0.80 mmol) and TEA (115 μL, 0.80 mmol). The reaction was stirred at 80° C. overnight in a sealed tube. It was concentrated and purified by prep-HPLC to afford (2R,3R,4R,5S)-2-(piperidin-1-ylmethyl)-5-((6-(trifluoromethyl)pyrazin-2-yl)amino)tetrahydro-2H-pyran-3,4-diol (A96, 2 mg, 4% yield) as white solid. LC-MS (ESI) found: 377 [M+H]⁺. ¹H NMR (400 MHz, CD₃OD): δ 8.10 (d, J=27.8 Hz, 1H), 8.02

(s, 1H), 4.34 (d, J=4.2 Hz, 1H), 4.25-4.13 (m, 1H), 3.92 (d, J=8.4 Hz, 1H), 3.87 (s, 1H), 3.72 (d, J=10.4 Hz, 1H), 3.50-3.40 (m, 2H), 3.22 (d, J=10.7 Hz, 3H), 3.16 (s, 1H), 1.86 (s, 4H), 1.67 (s, 2H).

Preparation of A97: (2R,3R,4R,5S)-2-(pyrrolidin-1-ylmethyl)-5-((6-(trifluoromethyl)pyrazin-2-yl)amino)tetrahydro-2H-pyran-3,4-diol

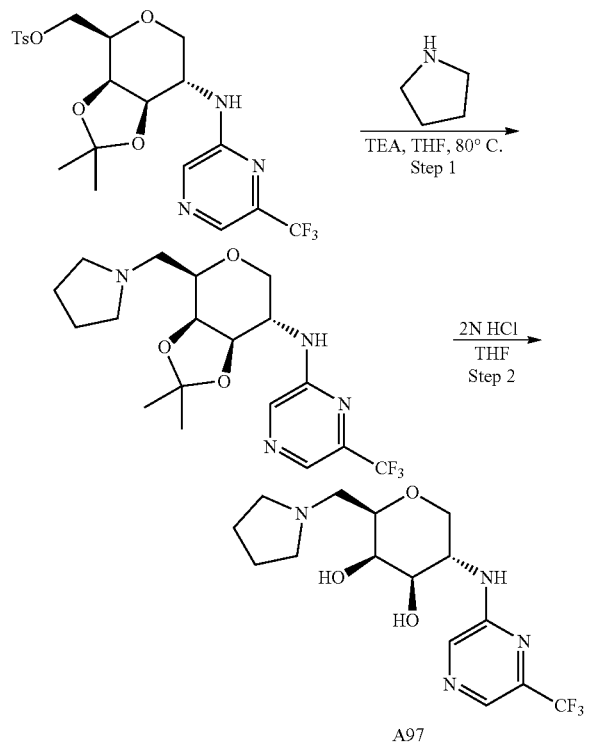

A97

Step 1: To a solution of ((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl 4-methylbenzenesulfonate (130 mg, 0.258 mmol) in THF (2 mL) was added TEA (179 μL, 1.290 mmol) and pyrrolidine (106 μL, 1.290 mmol) in the sealed tube. The reaction was stirred at 80° C. overnight. The mixture was concentrated to get crude N-((3aS,4R,7S,7aR)-2,2-dimethyl-4-(pyrrolidin-1-ylmethyl)tetrahydro-4H-[1,3]dioxolo[4,5-c]pyran-7-yl)-6-(trifluoromethyl)pyrazin-2-amine (100 mg, 96% yield) as yellow oil. LC-MS (ESI) found: 403 [M+H]+.

Step 2: To a solution of N-((3aS,4R,7S,7aR)-2,2-dimethyl-4-(pyrrolidin-1-ylmethyl)tetrahydro-4H-[1,3]dioxolo[4,5-c]pyran-7-yl)-6-(trifluoromethyl)pyrazin-2-amine (100 mg, 0.248 mmol) in THF (1 mL) was added HCl (372 μL, 2 N in H₂O). The reaction was stirred overnight and concentrated. The crude product was purified by prep-HPLC to give (2R,3R,4R,5S)-2-(pyrrolidin-1-ylmethyl)-5-((6-(trifluoromethyl)pyrazin-2-yl)amino)tetrahydro-2H-pyran-3,4-diol (A97, 75 mg, 84% yield) as white solid. LC-MS (ESI) found: 363 [M+H]+. ¹H NMR (400 MHz, CD₃OD): δ 8.11 (s, 1H), 8.00 (s, 1H), 4.35-4.23 (m, 1H), 4.16 (dd, J=11.1, 5.1 Hz, 1H), 3.86 (d, J=2.8 Hz, 1H), 3.67 (dd, J=10.5, 3.3 Hz, 1H), 3.13 (t, J=10.9 Hz, 1H), 2.91 (s, 1H), 2.88 (s, 1H), 1.90 (s, 1H).

Preparation of A98: benzyl (2R,3R,4R,5S)-2-((methylamino)methyl)-5-((6-(trifluoromethyl)pyrazin-2-yl)amino)tetrahydro-2H-pyran-3,4-diol

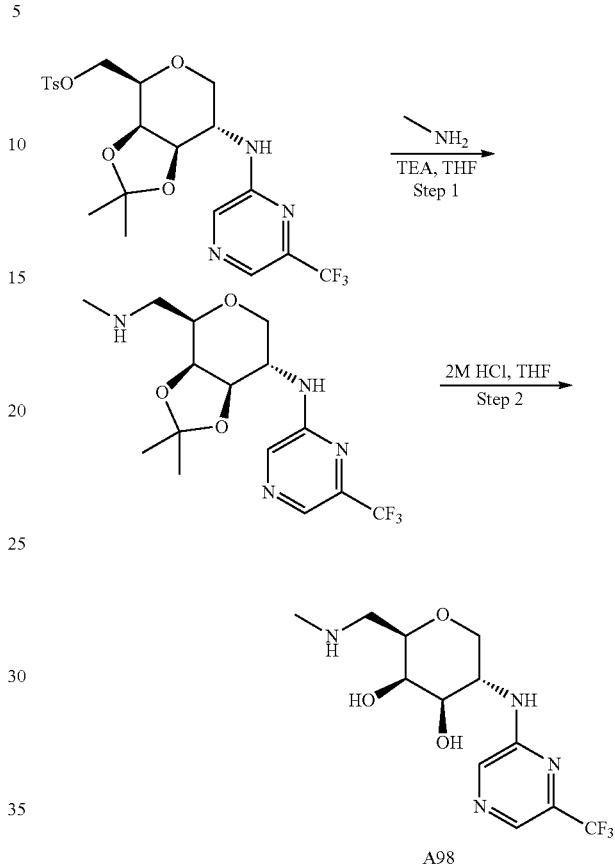

A98

Step 1: To a solution of ((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl 4-methylbenzenesulfonate (100 mg, 0.2 mmol), methanamine (1 mL, 1 mmol, 1 M in THF), and TEA (101 mg, 1 mmol) in THF (2 mL) was stirred at 80° C. overnight in a sealed tube. The mixture was concentrated in vacuo. The crude product was purified by C18 to give N-((3aS,4R,7S,7aR)-2,2-dimethyl-4-((methylamino)methyl)tetrahydro-4H-[1,3]dioxolo[4,5-c]pyran-7-yl)-6-(trifluoromethyl)pyrazin-2-amine (10 mg, 14% yield) as a white solid. LC-MS (ESI) found: 363 [M+H]+.

Step 2: To a solution of N-((3aS,4R,7S,7aR)-2,2-dimethyl-4-((methylamino)methyl)tetrahydro-4H-[1,3]dioxolo[4,5-c]pyran-7-yl)-6-(trifluoromethyl)pyrazin-2-amine (10 mg, 0.03 mmol) in THF (2 mL) was added HCl (0.1 mL, 1 N in H₂O). The mixture was stirred at rt overnight. The mixture was concentrated and purified by C18 to give (2R,3R,4R,5S)-2-((methylamino)methyl)-5-((6-(trifluoromethyl)pyrazin-2-yl)amino)tetrahydro-2H-pyran-3,4-diol (A98, 2.2 mg, 25% yield) as a white solid. LC-MS (ESI) found: 323 [M+H]+. ¹H NMR (400 MHz, CD₃OD): δ 8.11 (s, 1H), 8.00 (s, 1H), 4.33 (td, J=10.4, 5.0 Hz, 1H), 4.15 (dd, J=11.0, 5.2 Hz, 1H), 3.86 (d, J=2.7 Hz, 1H), 3.67 (dd, J=10.6, 3.1 Hz, 1H), 3.60 (dd, J=7.7, 3.2 Hz, 1H), 3.13 (t, J=10.8 Hz, 1H), 3.04 (dd, J=12.7, 8.2 Hz, 1H), 2.83 (dd, J=12.7, 3.6 Hz, 1H), 2.48 (s, 3H). ¹⁹F NMR (377 MHz, CD₃OD): δ −70.35.

Preparation of A99: (2R,3R,4R,5S)-2-((methyl(phenyl)amino)methyl)-5-((6-(trifluoromethyl)pyrazin-2-yl)amino)tetrahydro-2H-pyran-3,4-diol

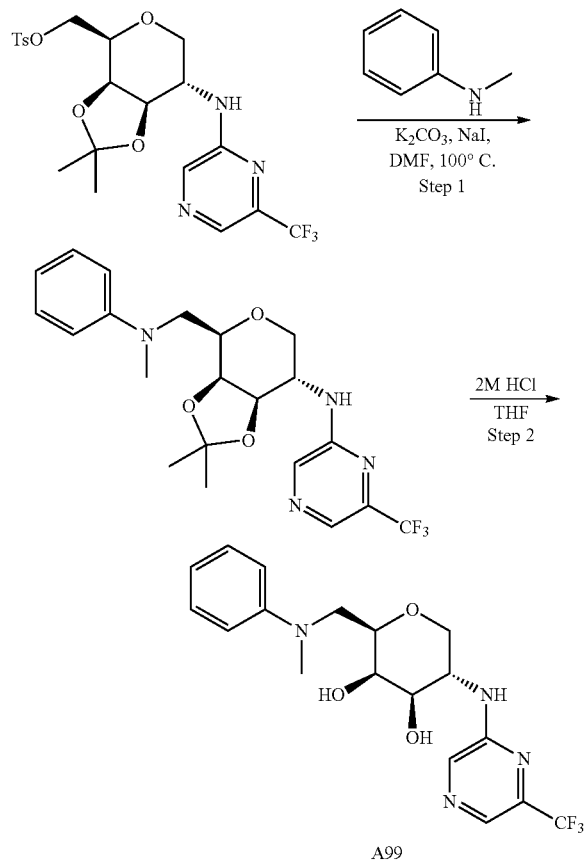

Step 1: To a suspension of ((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl 4-methylbenzenesulfonate (100 mg, 0.2 mmol), N-methylaniline (0.032 mL, 0.3 mmol), NaI (45 mg, 0.3 mmol) and K₂CO₃ (82.35 mg, 0.6 mmol) in DMF (1 mL) was stirred at 100° C. overnight. Reaction mixture was cooled, diluted with water (2 mL) and extracted with DCM (2 mL×3). Combined organic layers were dried over anhydrous Na₂SO₄, filtrated and concentrated. Residue was purified by prep-TLC (EA/PE=1:1) to give N-((3aS,4R,7S,7aR)-2,2-dimethyl-4-((methyl(phenyl)amino) methyl)tetrahydro-4H-[1,3]dioxolo[4,5-c]pyran-7-yl)-6-(trifluoromethyl)pyrazin-2-amine as a yellow oil (40 mg, 46% yield). LC-MS (ESI) found: 439 [M+H]⁺.

Step 2: To a solution of N-((3aS,4R,7S,7aR)-2,2-dimethyl-4-((methyl(phenyl)amino)methyl)tetrahydro-4H-[1,3]dioxolo[4,5-c]pyran-7-yl)-6-(trifluoromethyl)pyrazin-2-amine (40 mg, 0.09 mmol) in THF (2 mL) was added diluted HCl (0.5 mL, 2 N in H₂O). Reaction mixture was stirred at rt for 30 min. Reaction mixture was concentrated and purified by prep-TLC (MeOH/DCM=1:10) to give (2R,3R,4R,5S)-2-((methyl(phenyl)amino)methyl)-5-((6-(trifluoromethyl)pyrazin-2-yl)amino)tetrahydro-2H-pyran-3,4-diol as a white solid (A99, 2.5 mg, 7% yield). LC-MS (ESI) found: 399 [M+H]⁺. ¹H NMR (400 MHz, CD₃OD): δ 8.09 (s, 1H), 7.99 (s, 1H), 7.17 (t, J=8.0 Hz, 2H), 6.76 (d, J=8.2 Hz, 2H), 6.64 (t, J=7.3 Hz, 1H), 4.58 (s, 1H), 4.36 (td, J=10.5, 5.2 Hz, 1H), 4.12 (dd, J=11.0, 5.2 Hz, 1H), 3.86 (d, J=2.8 Hz, 1H), 3.69-3.58 (m, 3H), 3.56-3.49 (m, 1H), 3.06 (t, J=10.9 Hz, 1H), 2.99 (s, 3H).

Preparation of A100: benzyl tert-butyl (2R,3R,4R,5R,6S)-6-(allyloxy)-2-(hydroxymethyl)-5-((6-(trifluoromethyl)pyrazin-2-yl)amino)tetrahydro-2H-pyran-3,4-diol

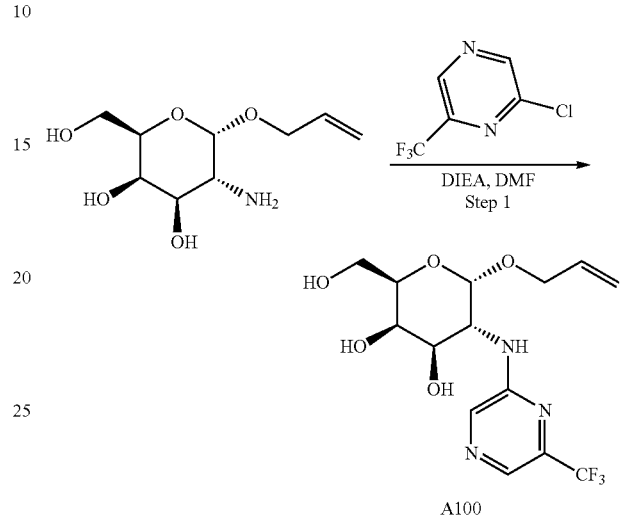

Step 1: To a solution of (2R,3R,4R,5R,6S)-6-(allyloxy)-5-amino-2-(hydroxymethyl)tetrahydro-2H-pyran-3,4-diol (50 mg, 0.22 mmol), 2-chloro-6-(trifluoromethyl)pyrazine (80 mg, 0.44 mmol) and DIEA (85 mg, 0.66 mmol) in DMF (3 mL) was stirred at 100° C. overnight in a sealed tube. The mixture was concentrated and purified by chromatography on C18 to give (2R,3R,4R,5R,6S)-6-(allyloxy)-2-(hydroxymethyl)-5-((6-(trifluoromethyl)pyrazin-2-yl)amino) tetrahydro-2H-pyran-3,4-diol (A100, 31.8 mg, 40% yield) as a white solid. LC-MS (ESI) found: 366 [M+H]⁺. ¹H NMR (400 MHz, CD₃OD): δ 8.18 (s, 1H), 7.98 (s, 1H), 5.88 (ddd, J=22.2, 10.8, 5.6 Hz, 1H), 5.26 (d, J=17.2 Hz, 1H), 5.10 (d, J=10.4 Hz, 1H), 5.03 (d, J=3.6 Hz, 1H), 4.50 (dd, J=10.5, 3.6 Hz, 1H), 4.20 (dd, J=13.2, 5.0 Hz, 1H), 3.93 (ddd, J=16.1, 13.0, 6.0 Hz, 4H), 3.80-3.67 (m, 2H). ¹⁹F NMR (377 MHz, CD₃OD): δ −70.32.

Preparation of A101: (2R,3R,4R,5S)-2-(hydroxymethyl)-5-((3-(trifluoromethyl)pyrazin-2-yl)amino)tetrahydro-2H-pyran-3,4-diol

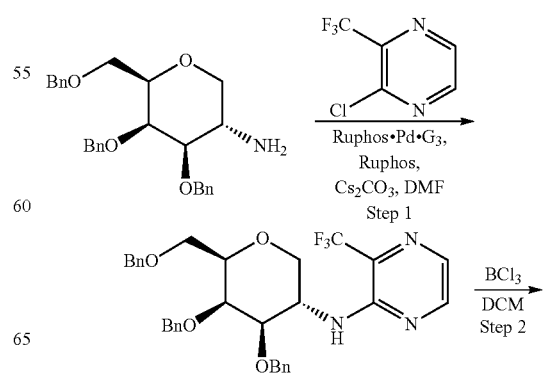

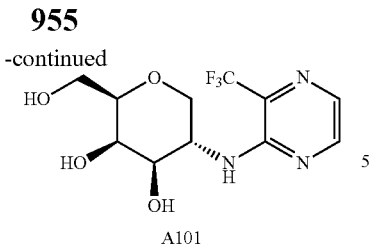

A101

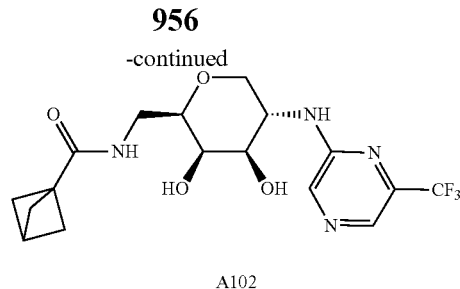

A102

Step 1: To a solution of (3S,4R,5R,6R)-4,5-bis(benzyloxy)-6-((benzyloxy)methyl)tetrahydro-2H-pyran-3-amine (200 mg, 0.462 mmol) in DMF (10 mL) was added 2-chloro-3-(trifluoromethyl)pyrazine (84.1 mg, 0.462 mmol), Ruphos.Pd.G3 (38.4 mg), Ruphos (21.5 mg, 0.046 mmol), Cs$_2$CO$_3$ (1.35 g. 4.158 mmol). The mixture was stirred at 100° C. under N$_2$ for 2 h. The mixture was diluted with ethyl acetate (15 mL) and washed with water (15 mL×3). The organic layer was concentrated under reduced pressure to give a crude product, which was purified by column to give N-((3S,4R,5R,6R)-4,5-bis(benzyloxy)-6-((benzyloxy)methyl)tetrahydro-2H-pyran-3-yl)-3-(trifluoromethyl)pyrazin-2-amine (70 mg, 26% yield). LC-MS (ESI) found: 580 [M+H]$^+$.

Step 2: To a solution of N-((3S,4R,5R,6R)-4,5-bis(benzyloxy)-6-((benzyloxy)methyl)tetrahydro-2H-pyran-3-yl)-3-(trifluoromethyl)pyrazin-2-amine (70 mg, 0.121 mmol) in DCM (20 mL) was added BCl$_3$ (1.2 mL, 1 M in DCM). The mixture was stirred at room temperature for 3 h. The mixture was quenched by NH$_3$·H$_2$O (1 mL) and concentrated to give a crude product, which was purified by column to give (2R,3R,4R,5S)-2-(hydroxymethyl)-5-((3-(trifluoromethyl)pyrazin-2-yl)amino)tetrahydro-2H-pyran-3,4-diol (A101, 7 mg, 18% yield). LC-MS (ESI) found: 310 [M+H]$^+$. $^1$H NMR (400 MHz, CD$_3$OD): δ 8.27 (s, 1H), 7.85 (d, J=2.2 Hz, 1H), 4.56 (td, J=10.5, 5.2 Hz, 1H), 4.15 (dd, J=10.9, 5.2 Hz, 1H), 3.91 (d, J=2.6 Hz, 1H), 3.76 (dd, J=14.3, 4.8 Hz, 2H), 3.69 (dd, J=11.4, 5.0 Hz, 1H), 3.48 (t, J=5.9 Hz, 1H), 3.21 (t, J=10.8 Hz, 1H). $^{19}$F NMR (377 MHz, CD$_3$OD): δ −68.82 (s).

Preparation of A102: N-(((2R,3R,4R,5S)-3,4-dihydroxy-5-((6-(trifluoromethyl)pyrazin-2-yl)amino)tetrahydro-2H-pyran-2-yl)methyl)bicyclo[1.1.1]pentane-1-carboxamide Step 1: To a solution of bicyclo[1.1.1]pentane-1-carboxylic acid (4.83 mg, 0.043 mmol) and HATU (24.56 mg, 0.07 mmol) in DMF (1 mL) was stirred at rt for 2 h. To the reaction mixture was added DIEA (11.1 mg, 0.09 mmol) and N-((3aS,4R,7S,7aR)-4-(aminomethyl)-2,2-dimethyltetrahydro-4H-[1,3]dioxolo[4,5-c]pyran-7-yl)-6-(trifluoromethyl)pyrazin-2-amine (15 mg, 0.043 mmol). Resulting mixture was stirred at rt for 2 h. Reaction mixture was concentrated. Residue was purified by prep-TLC (EA/PE=2:1) to give N-(((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)bicyclo[1.1.1]pentane-1-carboxamide as a colorless oil (15 mg, 79% yield). LC-MS (ESI) found: 433 [M+H]$^+$.

Step 2: To a solution of N-(((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)bicyclo[1.1.1]pentane-1-carboxamide (20 mg, 0.045 mmol) and diluted aqueous HCl (1 mL, 2 N in H$_2$O) in THF (2 mL) was stirred at RT for 30 min. Reaction mixture was concentrated. Residue was purified by flash chromatography reversed phase (C18, MeOH in water, from 10% to 70%) to give N-(((2R,3R,4R,5S)-3,4-dihydroxy-5-((6-(trifluoromethyl)pyrazin-2-yl)amino)tetrahydro-2H-pyran-2-yl)methyl)bicyclo[1.1.1]pentane-1-carboxamide as a white solid (A102, 7.9 mg, 43% yield). LC-MS (ESI) found: 401 [M+H]$^+$. $^1$H NMR (400 MHz, CD$_3$OD): δ 8.10 (s, 1H), 8.00 (s, 1H), 4.31 (td, J=10.7, 5.2 Hz, 1H), 4.11 (dd, J=11.0, 5.2 Hz, 1H), 3.81 (d, J=2.9 Hz, 1H), 3.63 (dd, J=10.6, 3.2 Hz, 1H), 3.52-3.44 (m, 2H), 3.30-3.24 (m, 2H), 3.08 (t, J=10.8 Hz, 1H), 2.43 (s, 1H), 2.05 (s, 6H).

Preparation of A103: benzyl tert-butyl 4-((((2R,3R,4R,5S)-3,4-dihydroxy-5-((6-(trifluoromethyl)pyrazin-2-yl)amino)tetrahydro-2H-pyran-2-yl)methyl)carbamoyl)piperazine-1-carboxylate

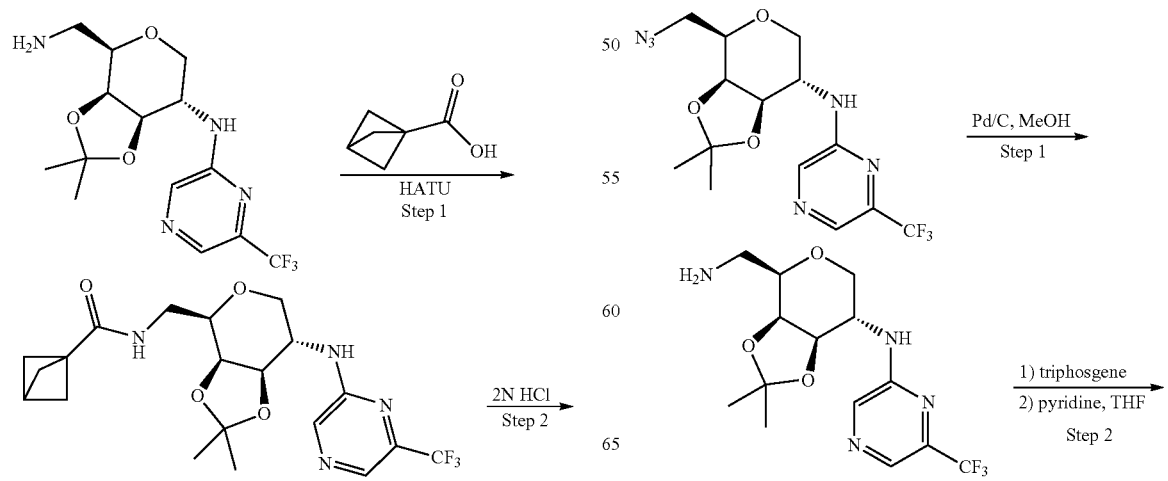

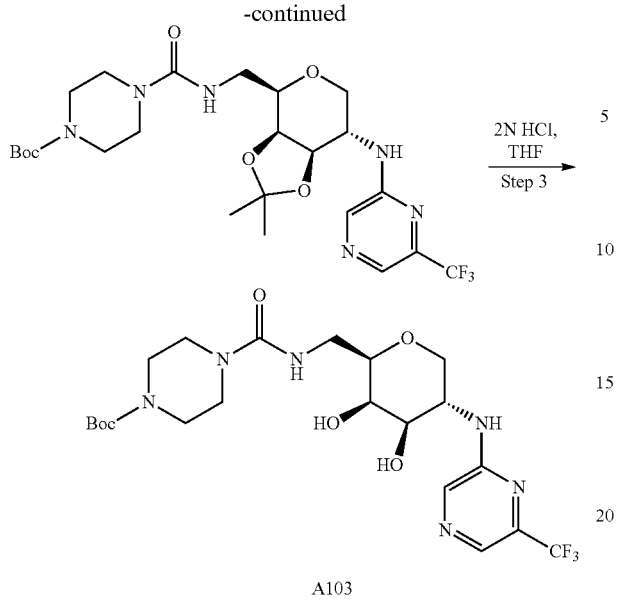

A103

Step 1: To a solution of N-((3aS,4R,7S,7aR)-4-(azidomethyl)-2,2-dimethyltetrahydro-4H-[1,3]dioxolo[4,5-c]pyran-7-yl)-6-(trifluoromethyl)pyrazin-2-amine (20 mg, 0.05 mmol) in MeOH (3 mL) was added Pd/C (4 mg, 10% wt., 60% wet). The mixture was stirred at rt for 1 h under a $H_2$ balloon. The mixture was filtered and concentrated to give crude N-((3aS,4R,7S,7aR)-4-(aminomethyl)-2,2-dimethyltetrahydro-4H-[1,3]dioxolo[4,5-c]pyran-7-yl)-6-(trifluoromethyl)pyrazin-2-amine (18 mg) as a white solid. LC-MS (ESI) found: 349 [M+H]+.

Step 2: To the solution of triphosgene (15 mg, 0.05 mmol) and pyridine (7.9 mg, 0.1 mmol) in THF (3 mL) was added N-((3aS,4R,7S,7aR)-4-(aminomethyl)-2,2-dimethyltetrahydro-4H-[1,3]dioxolo[4,5-c]pyran-7-yl)-6-(trifluoromethyl)pyrazin-2-amine (18 mg, 0.05 mmol) at 0° C. After 1 h, tert-butyl piperazine-1-carboxylate (9 mg, 0.05 mmol) was added to the reaction, the mixture was stirred at rt for 12 h. The mixture was concentrated and purified by silica to give tert-butyl 4-(((((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)carbamoyl)piperazine-1-carboxylate (15 mg, 54% yield) as solid. LC-MS (ESI) found: 561 [M+H]+.

Step 3: To a solution of tert-butyl 4-((((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)carbamoyl)piperazine-1-carboxylate (15 mg, 0.03 mmol) in THF (5 mL) was added HCl (one drop, 2 N in $H_2O$). The mixture was stirred at rt for 4 h. The mixture was neutralized with $NH_3 \cdot H_2O$, concentrated and purified by C18 to give tert-butyl 4-((((2R,3R,4R,5S)-3,4-dihydroxy-5-((6-(trifluoromethyl)pyrazin-2-yl)amino)tetrahydro-2H-pyran-2-yl)methyl)carbamoyl)piperazine-1-carboxylate (A103, 4.3 mg, 31% yield) as a white solid. LC-MS (ESI) found: 521 [M+H]+. 1H NMR (400 MHz, CD3OD): δ 8.10 (s, 1H), 7.99 (s, 1H), 4.32 (td, J=10.4, 5.1 Hz, 1H), 4.11 (dd, J=10.9, 5.2 Hz, 1H), 3.84 (d, J=3.0 Hz, 1H), 3.63 (dd, J=10.5, 3.1 Hz, 1H), 3.53-3.35 (m, 11H), 3.08 (t, J=10.8 Hz, 1H), 1.46 (s, 9H). 19F NMR (377 MHz, CD3OD): δ -70.33.

Preparation of A104: N-((2R,3R,4R,5R,6R)-4,5-dihydroxy-6-(hydroxymethyl)-2-(2-methoxyethoxy)tetrahydro-2H-pyran-3-yl)-2,2,2-trifluoroacetamide

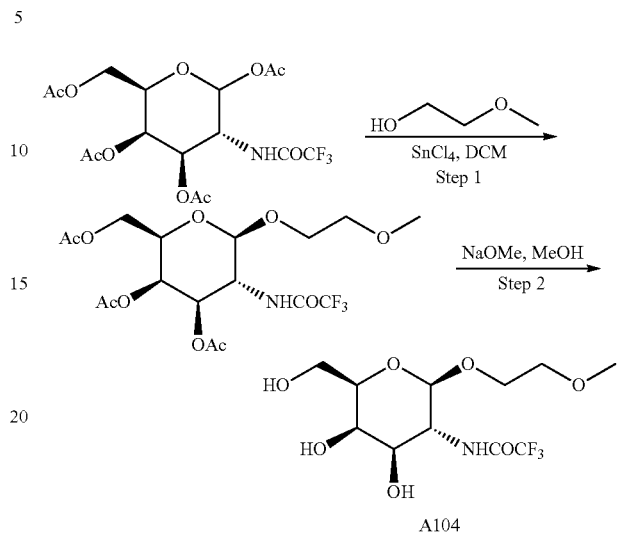

A104

Step 1: To the solution (3R,4R,5R,6R)-6-(acetoxymethyl)-3-(2,2,2-trifluoroacetamido)tetrahydro-2H-pyran-2,4,5-triyl triacetate (1 g, 2.3 mmol) in DCM (30 mL) was added 2-methoxyethan-1-ol (515 mg, 6.9 mmol) and tin tetrachloride (1.5 g, 5.8 mmol) at 0° C. The mixture was stirred at rt overnight. The mixture was slowly poured into ice-cold water, and the organic layer was separated and washed with $NaHCO_3$, dried and concentrated, purified by silica to give (2R,3R,4R,5R,6R)-2-(acetoxymethyl)-6-(2-methoxyethoxy)-5-(2,2,2-trifluoroacetamido)tetrahydro-2H-pyran-3,4-diyl diacetate (500 mg, 47% yield) as solid. LC-MS (ESI) found: 458 [M−H]−.

Step 2: To the solution of (2R,3R,4R,5R,6R)-2-(acetoxymethyl)-6-(2-methoxyethoxy)-5-(2,2,2-trifluoroacetamido)tetrahydro-2H-pyran-3,4-diyl diacetate (500 mg, 1.1 mmol) in MeOH (10 ml) was added NaOMe (1 mL, 5 M in MeOH) at 0° C. The mixture was stirred at rt for 3 h. The mixture was acidified with Amberlite IR120 (H+) form, ion-exchange resin and concentrated to give crude N-((2R,3R,4R,5R,6R)-4,5-dihydroxy-6-(hydroxymethyl)-2-(2-methoxyethoxy)tetrahydro-2H-pyran-3-yl)-2,2,2-trifluoroacetamide (A104, 200 mg, 55% yield) as solid. LC-MS (ESI) found: 332 [M−H]−. 1H NMR (400 MHz, CD3OD): δ 4.50 (d, J=8.4 Hz, 1H), 3.96 (ddd, J=14.0, 11.2, 7.5 Hz, 2H), 3.85 (d, J=2.8 Hz, 1H), 3.82-3.63 (m, 4H), 3.51 (dd, J=9.9, 5.5 Hz, 3H), 3.32 (s, 3H). 19F NMR (377 MHz, CD3OD): δ −77.31.

Preparation of A105: benzyl tert-butyl (2R,3R,4R,5R,6R)-2-(hydroxymethyl)-6-(2-methoxyethoxy)-5-((6-(trifluoromethyl)pyrazin-2-yl)amino)tetrahydro-2H-pyran-3,4-diol

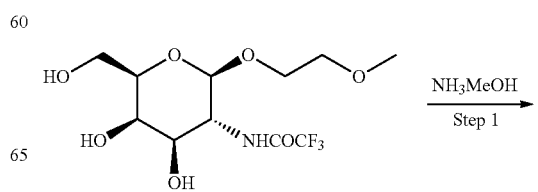

-continued

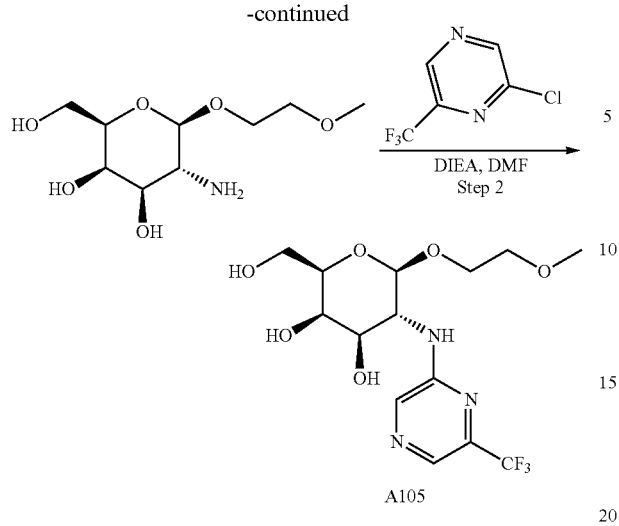

A105

Step 1: To a solution of N-((2R,3R,4R,5R,6R)-4,5-dihydroxy-6-(hydroxymethyl)-2-(2-methoxyethoxy)tetrahydro-2H-pyran-3-yl)-2,2,2-trifluoroacetamide (150 mg, 0.45 mmol) in $NH_3$/MeOH (3 mL, 7 M) was stirred at 80° C. overnight in tube. The mixture was concentrated to give crude (2R,3R,4R,5R,6R)-5-amino-2-(hydroxymethyl)-6-(2-methoxyethoxy)tetrahydro-2H-pyran-3,4-diol (107 mg) as a white solid. LC-MS (ESI) found: 238 [M+H]$^+$.

Step 2: To a solution of (2R,3R,4R,5R,6R)-5-amino-2-(hydroxymethyl)-6-(2-methoxyethoxy)tetrahydro-2H-pyran-3,4-diol (50 mg, 0.21 mmol), 2-chloro-6-(trifluoromethyl)pyrazine (76 mg, 0.42 mmol) and DIEA (81 mg, 0.63 mmol) in DMF (3 mL) was stirred at 100° C. overnight in tube. The mixture was concentrated and purified by chromatography on C18 to give (2R,3R,4R,5R,6R)-2-(hydroxymethyl)-6-(2-methoxyethoxy)-5-((6-(trifluoromethyl)pyrazin-2-yl)amino)tetrahydro-2H-pyran-3,4-diol (A105, 5.7 mg, 7% yield) as a white solid. LC-MS (ESI) found: 384 [M+H]$^+$. $^1$H NMR (400 MHz, $CD_3OD$): $^1$H NMR (400 MHz, $CD_3OD$) δ 8.15 (s, 1H), 7.99 (s, 1H), 4.53 (d, J=8.3 Hz, 1H), 4.17-4.07 (m, 1H), 3.93 (ddd, J=16.9, 10.5, 3.1 Hz, 2H), 3.84-3.71 (m, 3H), 3.67-3.51 (m, 2H), 3.46-3.34 (m, 2H), 3.14 (s, 3H). $^{19}$F NMR (377 MHz, $CD_3OD$): δ −70.19.

Preparation of A106: (2R,3R,4R,5S)-2-(((3-methoxyphenyl)(methyl)amino)methyl)-5-((6-(trifluoromethyl)pyrazin-2-yl)amino)tetrahydro-2H-pyran-3,4-diol

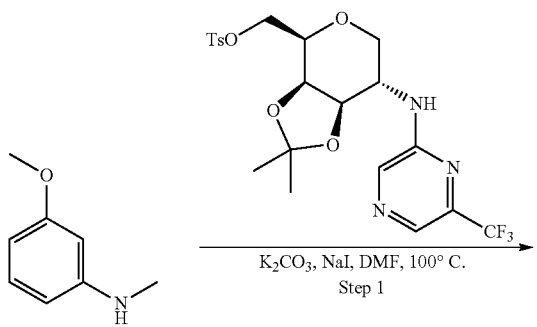

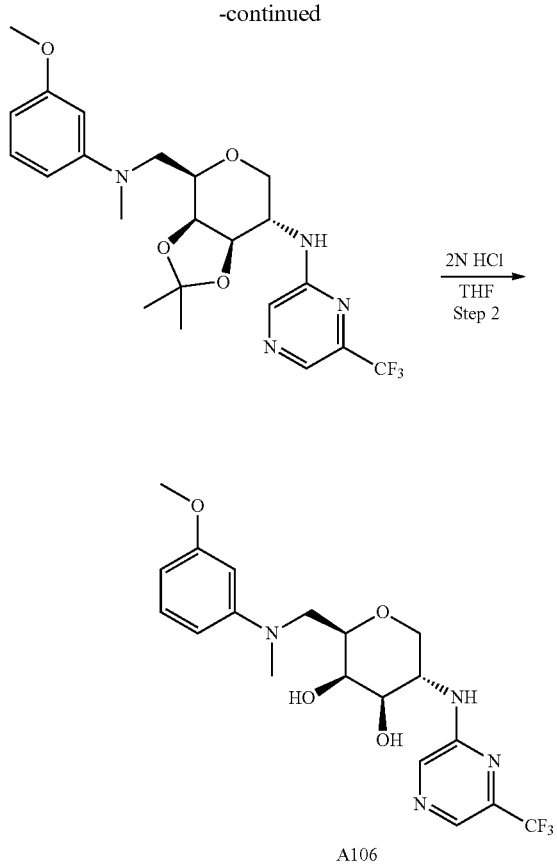

A106

Step 1: To a suspension of ((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl 4-methylbenzenesulfonate (500 mg, 0.99 mmol), 3-methoxy-N-methylaniline (204 mg, 1.49 mmol), $K_2CO_3$ (411 mg, 2.98 mmol) and NaI (224 mg, 1.49 mmol) in DMF (5 mL) was stirred at 100° C. overnight. Reaction mixture was cooled and concentrated. Residue was purified by prep-TLC (MeOH/DCM=1:10) to give N-((3aS,4R,7S,7aR)-4-(((3-methoxyphenyl)(methyl)amino)methyl)-2,2-dimethyltetrahydro-4H-[1,3]dioxolo[4,5-c]pyran-7-yl)-6-(trifluoromethyl)pyrazin-2-amine as a white solid (40 mg, 9% yield). LC-MS (ESI) found: 469 [M+H]$^+$.

Step 2: To a solution of N-((3aS,4R,7S,7aR)-4-(((3-methoxyphenyl)(methyl)amino)methyl)-2,2-dimethyltetrahydro-4H-[1,3]dioxolo[4,5-c]pyran-7-yl)-6-(trifluoromethyl)pyrazin-2-amine (40 mg, 0.085 mmol) and diluted aqueous HCl (1 mL, 2 N in $H_2O$) in THF (2 mL) was stirred at rt for 30 min. Reaction mixture was concentrated. Residue was purified by prep-TLC (MeOH/DCM=1:10) and flash chromatography reversed phase (C18, MeOH in water from 10% to 80%) to give (2R,3R,4R,5S)-2-(((3-methoxyphenyl)(methyl)amino)methyl)-5-((6-(trifluoromethyl)pyrazin-2-yl)amino)tetrahydro-2H-pyran-3,4-diol as a white solid (A106, 0.8 mg, 2% yield). LC-MS (ESI) found: 439 [M+H]$^+$. $^1$H NMR (400 MHz, $CD_3OD$): δ 8.09 (s, 1H), 7.99 (s, 1H), 7.08 (t, J=8.2 Hz, 1H), 6.38 (d, J=7.8 Hz, 1H), 6.32-6.19 (m, 2H), 4.36 (td, J=10.4, 5.2 Hz, 1H), 4.12 (dd, J=11.1, 5.1 Hz, 1H), 3.85 (d, J=2.8 Hz, 1H), 3.75 (s, 3H), 3.67-3.59 (m, 3H), 3.55-3.48 (m, 1H), 3.06 (t, J=10.8 Hz, 1H), 2.98 (s, 3H).

Preparation of A107: (2R,3R,4R,5S)-2-((pyrazin-2-ylamino)methyl)-5-((6-(trifluoromethyl)pyrazin-2-yl)amino)tetrahydro-2H-pyran-3,4-diol

Preparation of A108: (1R,2R)—N-(((2R,3R,4R,5S)-3,4-dihydroxy-5-((6-(trifluoromethyl)pyrazin-2-yl)amino)tetrahydro-2H-pyran-2-yl)methyl)-2-fluoro-cyclopropane-1-carboxamide

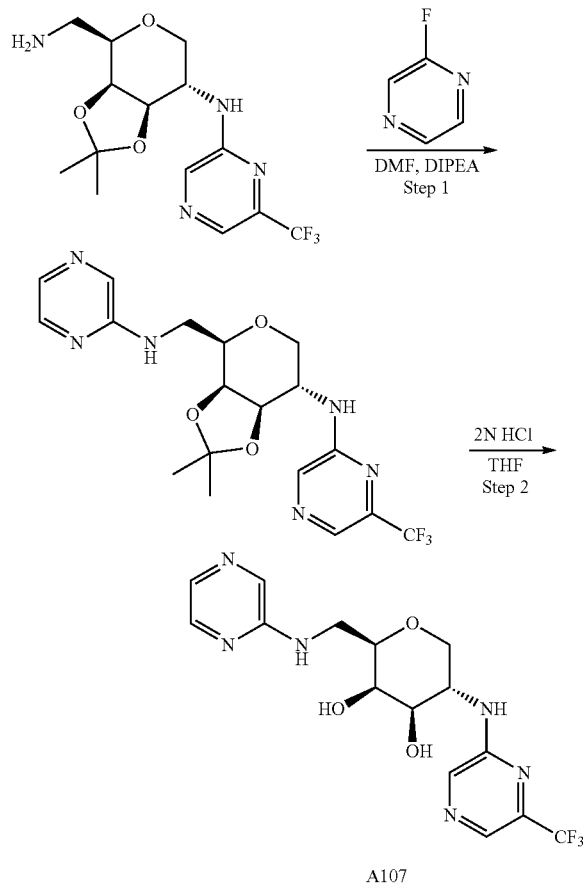

A107

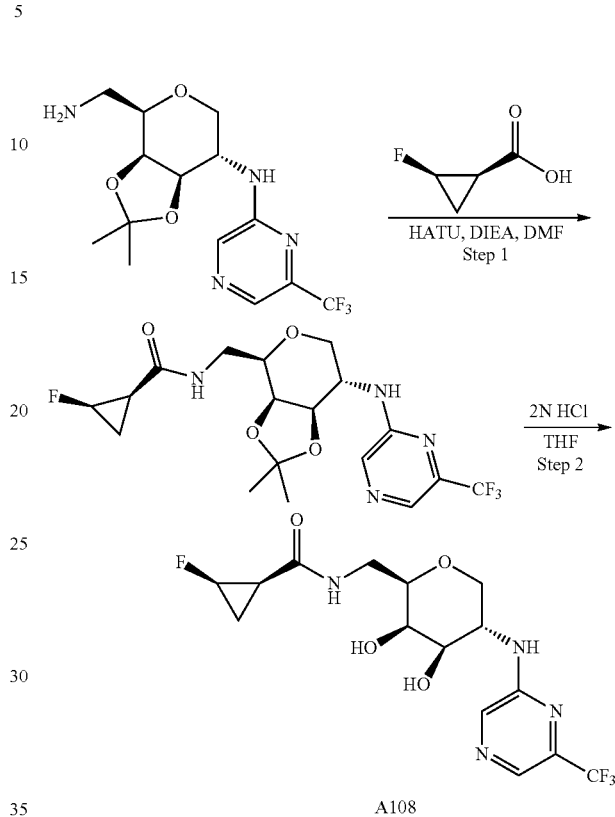

A108

Step 1: To a solution of N-((3aS,4R,7S,7aR)-4-(aminomethyl)-2,2-dimethyltetrahydro-4H-[1,3]dioxolo[4,5-c]pyran-7-yl)-6-(trifluoromethyl)pyrazin-2-amine (50 mg, 0.14 mmol), 2-fluoropyrazine (21 mg, 0.21 mmol) and DIPEA (37 mg, 0.28 mmol) in DMF (2 mL) was stirred at 100° C. overnight. The mixture was concentrated and the residue was purified by flash to give N-((3aS,4R,7S,7aR)-2,2-dimethyl-4-((pyrazin-2-ylamino)methyl)tetrahydro-4H-[1,3]dioxolo[4,5-c]pyran-7-yl)-6-(trifluoromethyl)pyrazin-2-amine (30 mg, 49% yield) as yellow solid. LC-MS (ESI) found: 427 [M+H]$^+$.

Step 2: To a solution of N-((3aS,4R,7S,7aR)-2,2-dimethyl-4-((pyrazin-2-ylamino)methyl)tetrahydro-4H-[1,3]dioxolo[4,5-c]pyran-7-yl)-6-(trifluoromethyl)pyrazin-2-amine (30 mg, 0.07 mmol) in THF (3 mL) was added HCl (0.5 mL, 2 N in H$_2$O) at rt. The mixture was stirred at rt overnight, then concentrated. The residue was purified by flash to give (2R,3R,4R,5S)-2-((pyrazin-2-ylamino)methyl)-5-((6-(trifluoromethyl)pyrazin-2-yl)amino)tetrahydro-2H-pyran-3,4-diol (A107, 14.5 mg, 53% yield) as yellow solid. LC-MS (ESI) found: 387 [M+H]$^+$. $^1$H NMR (400 MHz, CD$_3$OD): δ 8.10 (s, 1H), 8.00 (s, 1H), 7.93 (d, J=5.2 Hz, 2H), 7.64 (d, J=2.9 Hz, 1H), 4.34 (s, 1H), 4.14 (dd, J=11.0, 5.3 Hz, 1H), 3.89 (d, J=2.8 Hz, 1H), 3.69-3.58 (m, 3H), 3.54-3.48 (m, 1H), 3.11 (t, J=10.9 Hz, 1H).

Step 1: To the solution of N-((3aS,4R,7S,7aR)-4-(aminomethyl)-2,2-dimethyltetrahydro-4H-[1,3]dioxolo[4,5-c]pyran-7-yl)-6-(trifluoromethyl)pyrazin-2-amine (100 mg, 0.287 mmol) in DMF (2 mL) were added (1R,2R)-2-fluorocyclopropane-1-carboxylic acid (60 mg, 0.574 mmol), HATU (131 mg, 0.345 mmol) and DIEA (150 µL, 0.861 mmol). The solution was stirred at rt overnight and concentrated to be purified by 5% MeOH in DCM to get (1R,2R)—N-(((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)-2-fluorocyclopropane-1-carboxamide (100 mg, 80% yield) as light yellow oil. LC-MS (ESI) found: 435 [M+H]$^+$ Step 2: To the solution of (1R,2R)—N-(((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)-2-fluorocyclopropane-1-carboxamide (100 mg, 0.230 mmol) in THF (2 mL) was added HCl (20 µL, 2 N in H$_2$O). The reaction was stirred for 2 hrs and ensured completion of the reaction by LC-MS. Then it was concentrated and the residue was purified by prep-HPLC to get (1R,2R)—N-(((2R,3R,4R,5S)-3,4-dihydroxy-5-((6-(trifluoromethyl)pyrazin-2-yl)amino)tetrahydro-2H-pyran-2-yl)methyl)-2-fluorocyclopropane-1-carboxamide (A108, 53 mg, 58% yield) as white solid. LC-MS (ESI) found: 395 [M+H]$^+$. $^1$H NMR (400 MHz, CD$_3$OD): δ 8.10 (s, 1H), 7.99 (s, 1H), 4.83-4.62 (m, 1H), 4.36-4.25 (m, 1H), 4.13 (dd, J=11.0, 5.2 Hz, 1H), 3.85 (d, J=2.8 Hz, 1H), 3.64 (dd, J=10.6, 3.0 Hz, 1H), 3.58 (dd, J=13.4, 4.9 Hz, 1H), 3.54-

3.49 (m, 1H), 3.35 (s, 1H), 3.10 (t, J=10.8 Hz, 1H), 1.80 (dt, J=9.2, 6.9 Hz, 1H), 1.64 (dtd, J=23.0, 7.1, 3.7 Hz, 1H), 1.14-1.01 (m, 1H).

Preparation of A109: (1S,2S)—N-(((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)-2-fluorocyclopropane-1-carboxamide

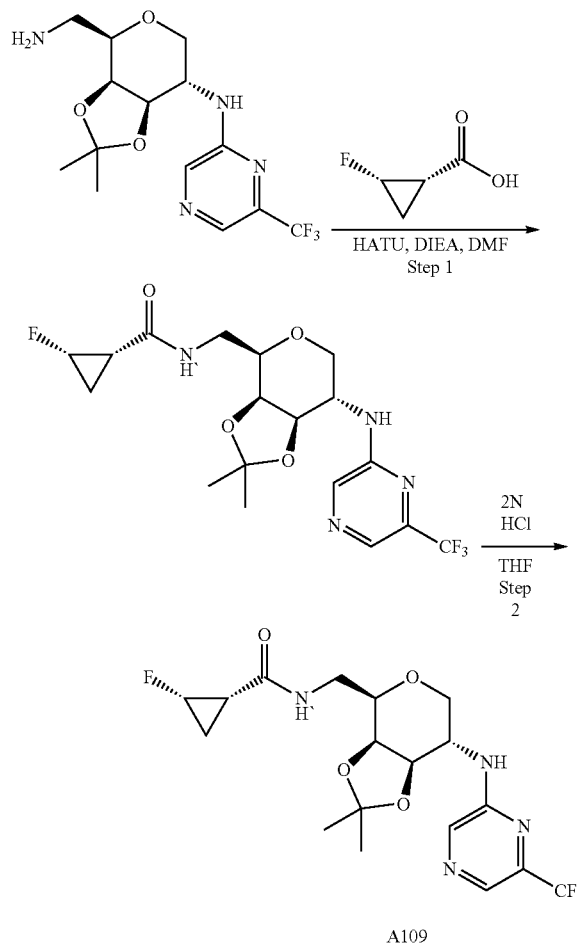

A109

Step 1: To a solution of (1S,2S)-2-fluorocyclopropane-1-carboxylic acid (5.98 mg, 0.06 mmol) and HATU (32.75 mg, 0.08 mmol) in DMF (0.5 mL) was stirred at rt for 2 h. N-((3aS,4R,7S,7aR)-4-(aminomethyl)-2,2-dimethyltetrahydro-4H-[1,3]dioxolo[4,5-c]pyran-7-yl)-6-(trifluoromethyl)pyrazin-2-amine (20 mg, 0.06 mmol) and DIEA (15 mg, 0.12 mmol) was added to above solution. The reaction mixture was stirred at rt for 2 h. Reaction was concentrated. The residue was purified by prep-TLC (MeOH/DCM=1:10) to give (1S,2S)—N-(((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)-2-fluorocyclopropane-1-carboxamide as a colorless oil (20 mg, 80% yield). LC-MS (ESI) found: 435 [M+H]$^+$.

Step 2: To a solution of (1S,2S)—N-(((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)-2-fluorocyclopropane-1-carboxamide (20 mg, 0.046 mmol) and diluted aqueous HCl (1 mL, 2 N in H$_2$O) in THF (2 mL) was stirred at rt for 30 min. Reaction mixture was concentrated. Residue was purified by flash chromatography reversed phase (C18, MeOH in water from 10% to 70%) to give (1S,2S)—N-(((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)-2-fluorocyclopropane-1-carboxamide as a white solid (A109, 6.1 mg, 34% yield). LC-MS (ESI) found: 395 [M+H]$^+$. $^1$H NMR (400 MHz, CD$_3$OD): δ 8.10 (s, 1H), 7.99 (s, 1H), 4.82-4.63 (m, 1H), 4.32 (td, J=10.5, 5.1 Hz, 1H), 4.13 (dd, J=11.0, 5.2 Hz, 1H), 3.84 (d, J=2.8 Hz, 1H), 3.66-3.55 (m, 2H), 3.50-3.47 (m, 1H), 3.34 (d, J=7.9 Hz, 1H), 3.09 (t, J=10.9 Hz, 1H), 1.85-1.77 (m, 1H), 1.70-1.60 (m, 1H), 1.12-1.01 (m, 1H).

Preparation of A110: ethyl 4-(((1S,2R,3R,4R,5S)-2,3-dihydroxy-1-(hydroxymethyl)-6,8-dioxabicyclo[3.2.1]octan-4-yl)amino)-2-(trifluoromethyl)pyrimidine-5-carboxylate

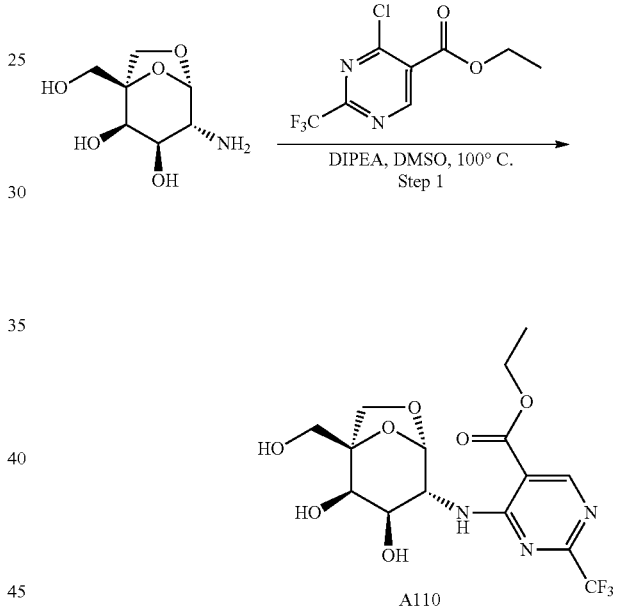

A110

Step 1: To a solution of (1S,2R,3R,4R,5S)-4-amino-1-(hydroxymethyl)-6,8-dioxabicyclo[3.2.1]octane-2,3-diol (100 mg, 523.06 μmol, 1 eq) in DMSO (1 mL) was added DIPEA (162.24 mg, 1.26 mmol, 218.65 μL, 2.4 eq) and ethyl 4-chloro-2-(trifluoromethyl)pyrimidine-5-carboxylate (199.75 mg, 784.60 μmol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). Ethyl 4-[[(1S,2R,3R,4R,5S)-2,3-dihydroxy-1-(hydroxymethyl)-6,8-dioxabicyclo[3.2.1]octan-4-yl]amino]-2-(trifluoromethyl)pyrimidine-5-carboxylate (A110, 74 mg, 160.72 μmol, 30.73% yield, 88.9% purity) was obtained as a white solid. LC-MS (ESI) found: 410 [M+H]$^+$. 1H NMR (ET44412-94-P1P2) 1H NMR (400 MHz, DMSO-d6) δ=8.93 (s, 1H), 8.48 (d, J=8.4 Hz, 1H), 5.32 (d, J=1.3 Hz, 1H), 4.38 (q, J=7.0 Hz, 3H), 4.34-4.23 (m, 2H), 3.87-3.78 (m, 3H), 3.74 (dd, J=4.2, 9.6 Hz, 1H), 3.66-3.55 (m, 2H), 1.35 (s, 3H).

Preparation of A111: (1S,2R,3R,4R,5S)-4-amino-1-(hydroxymethyl)-6,8-dioxabicyclo[3.2.1]octane-2,3-diol

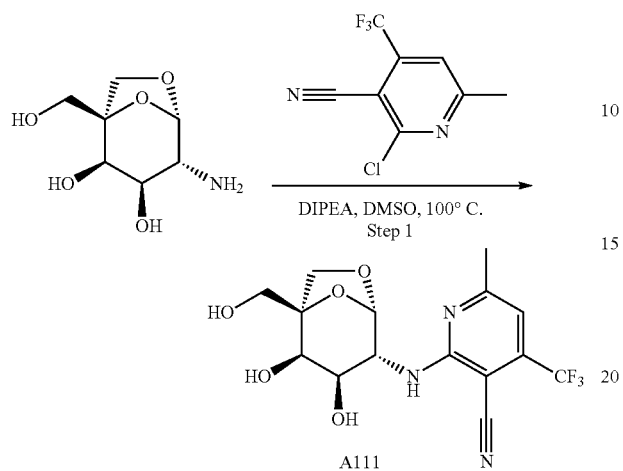

A111

Step 1: To a solution of (1S,2R,3R,4R,5S)-4-amino-1-(hydroxymethyl)-6,8-dioxabicyclo[3.2.1]octane-2,3-diol (100 mg, 523.06 umol) and 2-chloro-6-methyl-4-(trifluoromethyl)nicotinonitrile (173.07 mg, 784.60 umol, 1.5 eq) was added DIPEA (162.24 mg, 1.26 mmol, 218.65 uL, 2.4 eq) and ethyl 4-chloro-2-(trifluoromethyl)pyrimidine-5-carboxylate (199.75 mg, 784.60 umol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). A111: (1S,2R,3R,4R,5S)-4-amino-1-(hydroxymethyl)-6,8-dioxabicyclo[3.2.1] octane-2,3-diol Yield: 5.28 mg, 2.69% yield yellow solid. LC-MS (ESI) found: 376 [M+H]$^+$. 0.1H NMR (400 MHz, METHANOL-d4) δ=6.92 (s, 1H), 5.40 (d, J=1.3 Hz, 1H), 4.88 (s, 8H), 3.99-3.94 (m, 2H), 3.88-3.82 (m, 1H), 3.73 (d, J=7.9 Hz, 1H), 2.50 (s, 2H).

Preparation of A112: ethyl 6-chloro-2-(((1S,2R,3R,4R,5S)-2,3-dihydroxy-1-(hydroxymethyl)-6,8-dioxabicyclo[3.2.1]octan-4-yl)amino)nicotinate

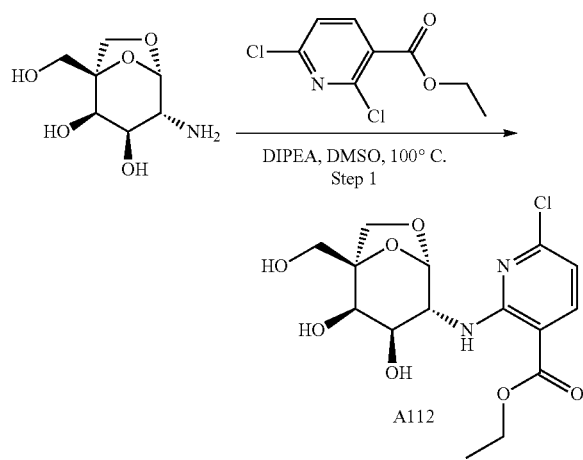

A112

Step 1: To a solution of 1S,2R,3R,4R,5S)-4-amino-1-(hydroxymethyl)-6,8-dioxabicyclo[3.2.1]octane-2,3-diol (100 mg, 523.06 umol) and ethyl 2,6-dichloronicotinate (172.65 mg, 784.60 umol) was added DIPEA (162.24 mg, 1.26 mmol, 218.65 uL, 2.4 eq) and ethyl 4-chloro-2-(trifluoromethyl)pyrimidine-5-carboxylate (199.75 mg, 784.60 umol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). A112: ethyl 6-chloro-2-(((1S,2R,3R,4R,5S)-2,3-dihydroxy-1-(hydroxymethyl)-6,8-dioxabicyclo[3.2.1] octan-4-yl)amino)nicotinate, Yield: 11.31 mg, 5.77% yield yellow solid. LC-MS (ESI) found: 375 [M+H]$^+$. 1H NMR (400 MHz, METHANOL-d4) δ=8.10 (d, J=8.2 Hz, 1H), 6.61 (d, J=8.1 Hz, 1H), 5.39 (d, J=1.3 Hz, 1H), 4.54-4.12 (m, 3H), 3.97-3.91 (m, 2H), 3.87-3.78 (m, 3H), 3.72 (d, J=7.9 Hz, 1H), 3.31 (s, 1H), 1.36 (t, J=7.1 Hz, 3H).

Preparation of A113: (1S,2R,3R,4R,5S)-4-amino-1-(hydroxymethyl)-6,8-dioxabicyclo[3.2.1]octane-2,3-diol

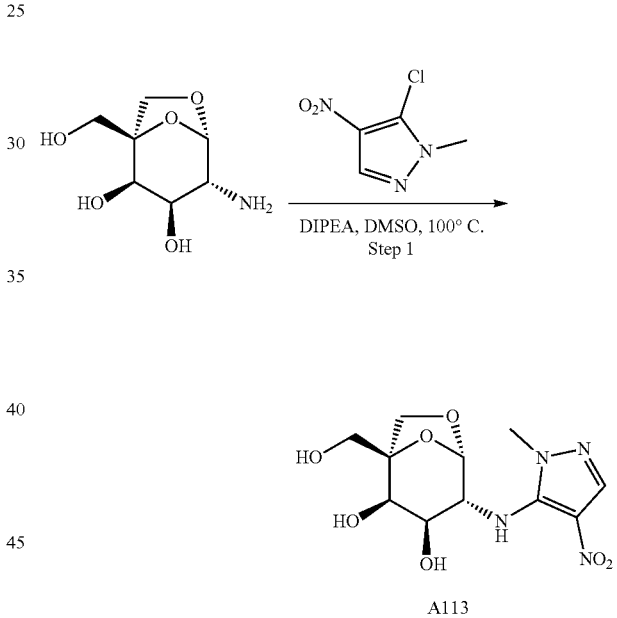

A113

Step 1: To a solution of (1S,2R,3R,4R,5S)-4-amino-1-(hydroxymethyl)-6,8-dioxabicyclo[3.2.1]octane-2,3-diol (100 mg, 523.06 umol) and 5-chloro-1-methyl-4-nitro-1H-pyrazole (126.75 mg, 784.60 umol) was added DIPEA (162.24 mg, 1.26 mmol, 218.65 uL, 2.4 eq) and ethyl 4-chloro-2-(trifluoromethyl)pyrimidine-5-carboxylate (199.75 mg, 784.60 umol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). A113: (1S,2R,3R,4R,5S)-4-amino-1-(hydroxymethyl)-6,8-dioxabicyclo[3.2.1] octane-2,3-diol Yield: 5.41 mg, 3.27% yield yellow solid. LC-MS (ESI) found: 317 [M+H]$^+$. $^1$H NMR (400 MHz, METHANOL-d4) δ=7.91 (s, 1H), 5.44 (d, J=1.2 Hz, 1H), 3.97-3.92 (m, 1H), 3.91-3.87 (m, 1H), 3.87-3.81 (m, 6H), 3.80-3.75 (m, 2H).

Preparation of A114: (1S,2R,3R,4R,5S)-4-((2-chloro-5-(trifluoromethyl)pyrimidin-4-yl)amino)-1-(hydroxymethyl)-6,8-dioxabicyclo[3.2.1]octane-2,3-diol and A115: (1S,2R,3R,4R,5S)-4-((4-chloro-5-(trifluoromethyl)pyrimidin-2-yl)amino)-1-(hydroxymethyl)-6,8-dioxabicyclo[3.2.1]octane-2,3-diol Preparation of (1S,2R,3R,4R,5S)-4-((3-chloro-1,2,4-thiadiazol-5-yl)amino)-1-(hydroxymethyl)-6,8-dioxabicyclo[3.2.1]octane-2,3-diol and A116: (1R,2R,3R,4R,5S)-4-((3-chloro-1,2,4-thiadiazol-5-yl)amino)-1-(((3-chloro-1,2,4-thiadiazol-5-yl)oxy)methyl)-6,8-dioxabicyclo[3.2.1]octane-2,3-diol

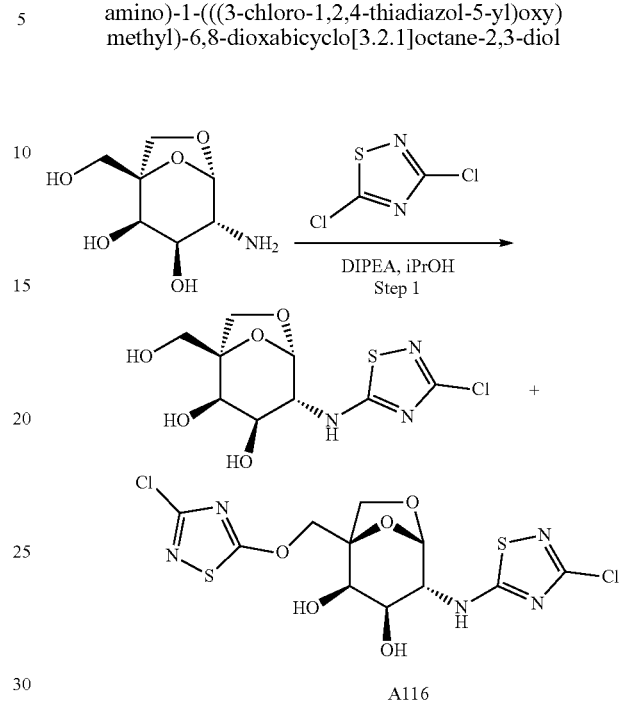

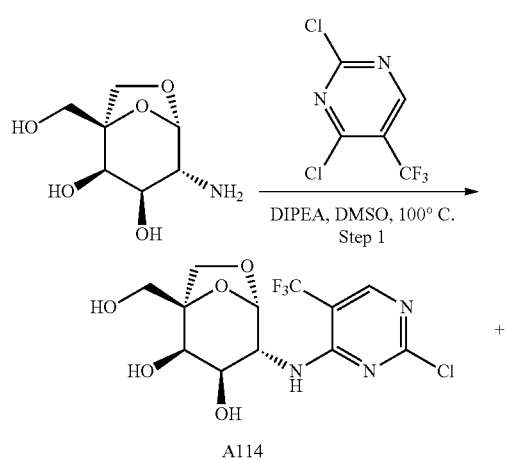

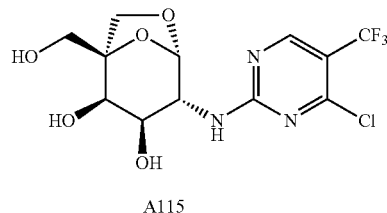

Step 1: To a solution of (1S,2R,3R,4R,5S)-4-amino-1-(hydroxymethyl)-6,8-dioxabicyclo[3.2.1]octane-2,3-diol (100 mg, 523.06 umol) and 2,4-dichloro-5-(trifluoromethyl)pyrimidine (170.24 mg, 784.60 umol) was added DIPEA (162.24 mg, 1.26 mmol, 218.65 uL, 2.4 eq) and ethyl 4-chloro-2-(trifluoromethyl)pyrimidine-5-carboxylate (199.75 mg, 784.60 umol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). A114: (1S,2R,3R,4R,5S)-4-((2-chloro-5-(trifluoromethyl)pyrimidin-4-yl)amino)-1-(hydroxymethyl)-6,8-dioxabicyclo[3.2.1]octane-2,3-diol Yield: 5.25 mg, 2.7% yield yellow solid LC-MS (ESI) found: 372 [M+H]$^+$. $^1$H NMR (400 MHz, methanol-d4) δ=8.48 (d, J=10.4 Hz, 1H), 5.42-5.28 (m, 1H), 4.23 (br t, J=9.5 Hz, 1H), 4.00-3.66 (m, 7H). A115: (1S,2R,3R,4R,5S)-4-((4-chloro-5-(trifluoromethyl)pyrimidin-2-yl)amino)-1-(hydroxymethyl)-6,8-dioxabicyclo[3.2.1]octane-2,3-diol yield: 19.99 mg, 10.28% yield yellow solid LC-MS (ESI) found: 372 [M+H]$^+$. $^1$H NMR (400 MHz, METHANOL-d4) δ=8.35 (s, 1H), 5.37 (d, J=1.2 Hz, 1H), 4.51 (d, J=9.9 Hz, 1H), 4.06 (dd, J=4.3, 9.9 Hz, 1H), 3.97-3.90 (m, 2H), 3.86-3.80 (m, 2H), 3.72 (d, J=7.9 Hz, 1H).

Step 1: To a solution of (1S,2R,3R,4R,5S)-4-amino-1-(hydroxymethyl)-6,8-dioxabicyclo[3.2.1]octane-2,3-diol (100 mg, 523.06 umol) and 3,5-dichloro-1,2,4-thiadiazole (243.23 mg, 1.57 mmol) was added DIPEA (162.24 mg, 1.26 mmol, 218.65 uL, 2.4 eq) and ethyl 4-chloro-2-(trifluoromethyl)pyrimidine-5-carboxylate (199.75 mg, 784.60 umol, 1.5 eq) stirred 100° C. for 15 hrs. The reaction mixture was filtered. The filtrate was purified by prep-HPLC (TFA condition; column: Phenomenex Luna C18 150*30 mm*5 um; mobile phase: [water (0.1% TFA)-ACN]; B %: 15%-45%, 8 min). (1S,2R,3R,4R,5S)-4-((3-chloro-1,2,4-thiadiazol-5-yl)amino)-1-(hydroxymethyl)-6,8-dioxabicyclo [3.2.1]octane-2,3-diol, Yield: 11.1 mg, white solid. LC-MS (ESI) found: 310 [M+H]$^+$. $^1$H NMR (400 MHz, METHANOL-d4) δ=5.49 (s, 1H), 5.38 (s, 1H), 3.96-3.89 (m, 2H), 3.84 (s, 1H), 3.82-3.75 (m, 2H), 3.74-3.70 (m, 1H). A116: (1R,2R,3R,4R,5S)-4-((3-chloro-1,2,4-thiadiazol-5-yl)amino)-1-(((3-chloro-1,2,4-thiadiazol-5-yl)oxy)methyl)-6,8-dioxabicyclo[3.2.1]octane-2,3-diol Yield: 8.8 mg, 8.2% yield white solid. LC-MS (ESI) found: 310 [M+H]$^+$. $^1$H NMR (400 MHz, METHANOL-d4) δ=5.44 (s, 1H), 4.92 (s, 2H), 3.96-3.92 (m, 2H), 3.91 (s, 1H), 3.85-3.79 (m, 2H).

Preparation of A117: (2R,3R,4R,5S)-2-(hydroxymethyl)-5-((2-(methylsulfonyl)-6-(trifluoromethyl)pyrimidin-4-yl)amino)tetrahydro-2H-pyran-3,4-diol

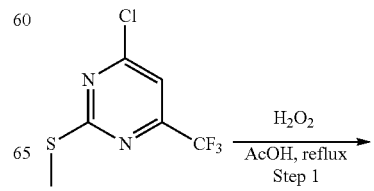

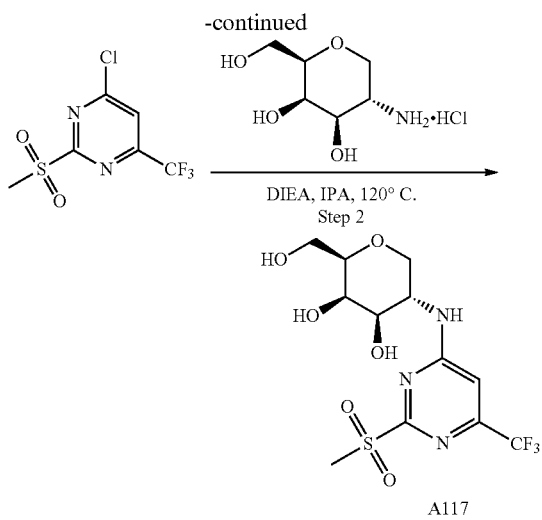

A117

Step 1: To a solution of 4-chloro-2-(methylsulfanyl)-6-(trifluoromethyl)pyrimidine (330 mg, 1.44 mmol) in AcOH (1 mL) was added $H_2O_2$ (0.5 mL, 30% wt. in $H_2O$) and the solution was heated at 100° C. for 3 h. The mixture was quenched with $NaHCO_3$ and extracted with EA. The combined organic layer was dried and concentrated for further purification by column chromatography with 20% EtOAc in hexanes to get 4-chloro-2-methanesulfonyl-6-(trifluoromethyl)pyrimidine (300 mg, 80% yield) as white solid. LC-MS (ESI) found: 261 [M+H]$^+$.

Step 2: To a solution of (2R,3R,4R,5S)-5-amino-2-(hydroxymethyl)tetrahydro-2H-pyran-3,4-diol hydrochloride (50 mg, 0.34 mmol) in i-PrOH (3 mL) was added 4-chloro-2-methanesulfonyl-6-(trifluoromethyl)pyrimidine (88 mg, 0.34 mmol) and DIEA (0.17 mL, 1.02 mmol). The mixture was stirred and heated at 120° C. overnight. Then the mixture was concentrated and purified by column chromatography with 10% DCM in methanol to get (2R,3R,4R,5S)-2-(hydroxymethyl)-5-((2-(methylsulfonyl)-6-(trifluoromethyl)pyrimidin-4-yl)amino)tetrahydro-2H-pyran-3,4-diol (A117, 7 mg, 5% yield) as white solid. LC-MS (ESI) found: 388 [M+H]$^+$. $^1$H NMR (400 MHz, $CD_3OD$): δ 6.97 (s, 1H), 4.55 (td, J=10.6, 5.1 Hz, 1H), 4.12 (dd, J=11.0, 5.2 Hz, 1H), 3.92 (d, J=3.1 Hz, 1H), 3.76 (dd, J=11.3, 7.1 Hz, 1H), 3.69 (dd, J=11.4, 5.0 Hz, 1H), 3.64 (dd, J=10.6, 3.2 Hz, 1H), 3.48-3.44 (m, 1H), 3.33 (s, 3H), 3.16 (t, J=10.9 Hz, 1H).

Preparation of Compound 1, (S)-3-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(2-carboxyethyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)carbamoyl)-23-(1-(20-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)-20-oxo-7,10,13,16-tetraoxa-4,19-diazatricosanoic acid

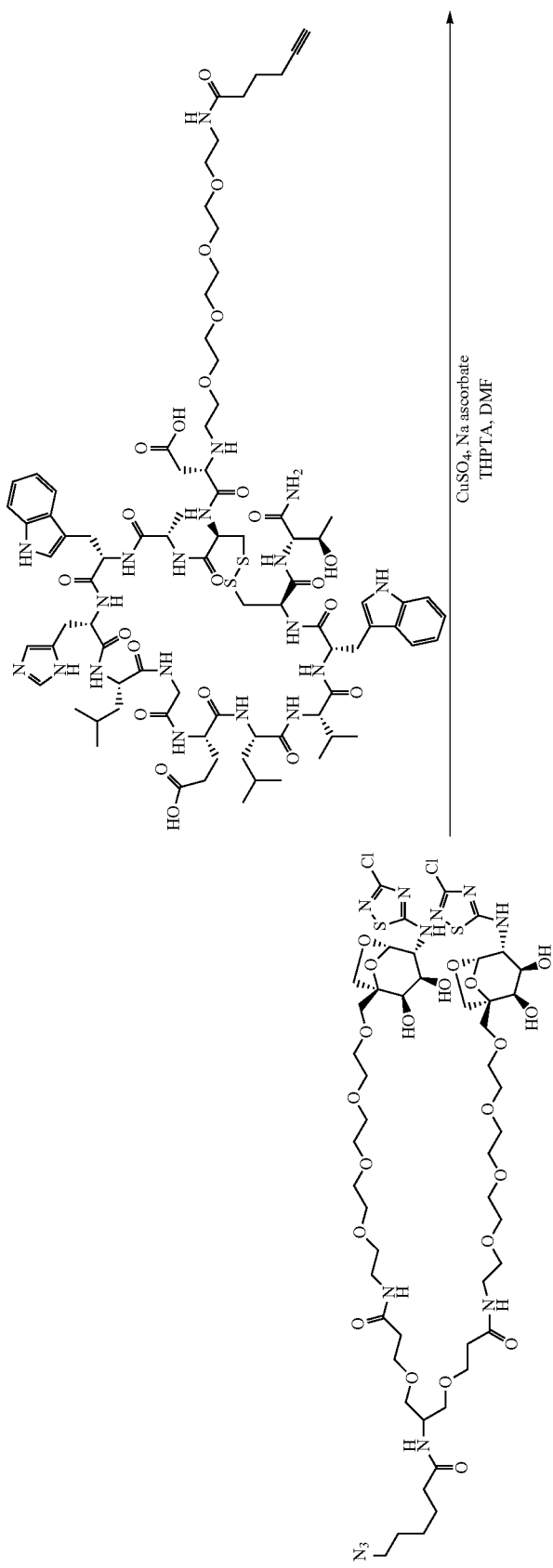
CuSO₄, Na ascorbate
THPTA, DMF

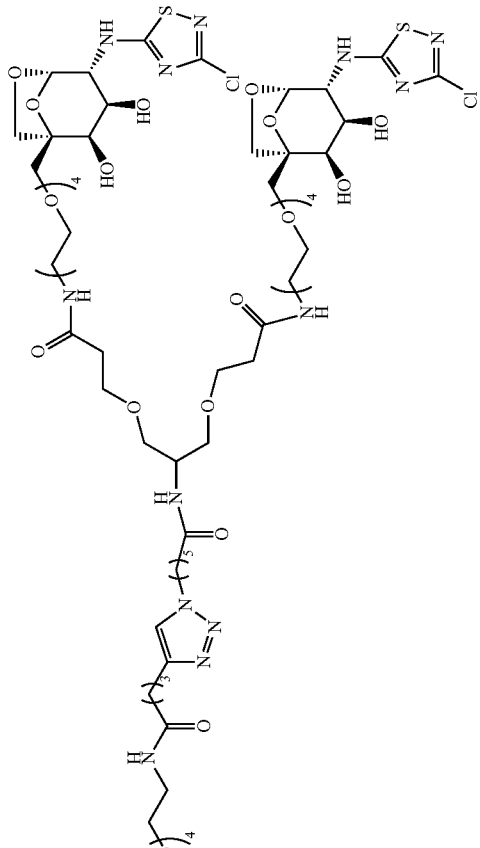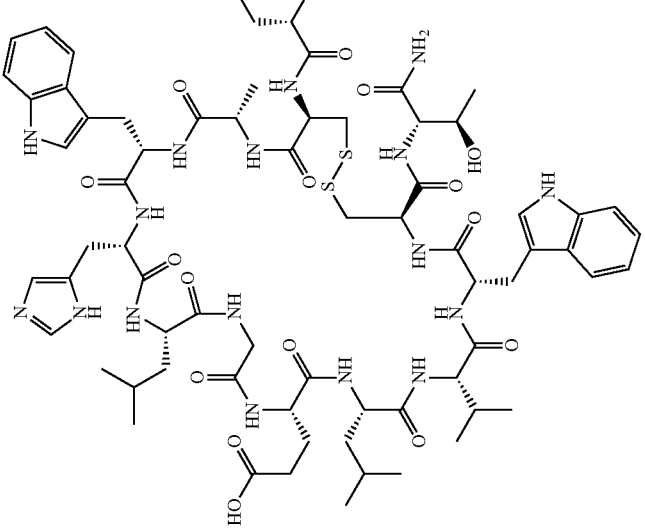

Step 1 THPTA (13 mg, 0.03 mmol) and CuSO$_4$ (0.38 mg, 0.0015 mmol) were dissolved in water (0.1 mL) and then added to a solution of 3,3'-((2-(6-azidohexanamido)propane-1,3-diyl)bis(oxy))bis(N-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide) (A14, 20 mg, 0.015 mmol) and (S)-3-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(2-carboxyethyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)carbamoyl)-20-oxo-7,10,13,16-tetraoxa-4,19-diazapentacos-24-ynoic acid (Intermediate 3, 27.6 mg, 0.015 mmol) in DMF (2 mL). A freshly prepared solution of Sodium ascorbate (2.64 mg, 0.015 mmol) in water (0.1 mL) was added and the reaction mixture was stirred at rt overnight. Solvent was evaporated and the product was purified by prep-HPLC to give (S)-3-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(2-carboxyethyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)carbamoyl)-23-(1-(20-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)-20-oxo-7,10,13,16-tetraoxa-4,19-diazatricosanoic acid (Compound 1, 7 mg, 14.5% yield) as a white solid. LC-MS (ESI) found: 1052 [M+3H]$^{3+}$. $^1$H NMR (400 MHz, CD3OD): δ 8.69 (s, 1H), 7.74 (s, 1H), 7.49-7.38 (m, 2H), 7.34-7.26 (m, 2H), 7.08 (s, 2H), 6.98 (s, 5H), 5.38 (s, 2H), 3.99 (d, J=9.6 Hz, 2H), 3.93 (d, J=4.4 Hz, 3H), 3.81 (d, J=8.2 Hz, 6H), 3.73-3.57 (m, 58H), 3.51 (d, J=24.6 Hz, 20H), 3.36 (dd, J=11.3, 5.8 Hz, 15H), 3.13 (s, 5H), 2.70-2.64 (m, 1H), 2.44 (s, 5H), 2.22 (d, J=18.1 Hz, 4H), 2.02-1.82 (m, 5H), 1.66-1.53 (m, 6H), 1.29 (s, 4H), 1.23 (s, 3H), 1.15 (d, J=6.3 Hz, 4H), 0.93 (dd, J=18.0, 6.5 Hz, 18H).

Preparation of Compound 2, (S)-4-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(23-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14,21-diazaheptacosan-27-yl)-1H-1,2,3-triazol-4-yl)-3,20-dioxo-7,10,13,16-tetraoxa-4,19-diazatricosyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)amino)-3-amino-4-oxobutanoic acid

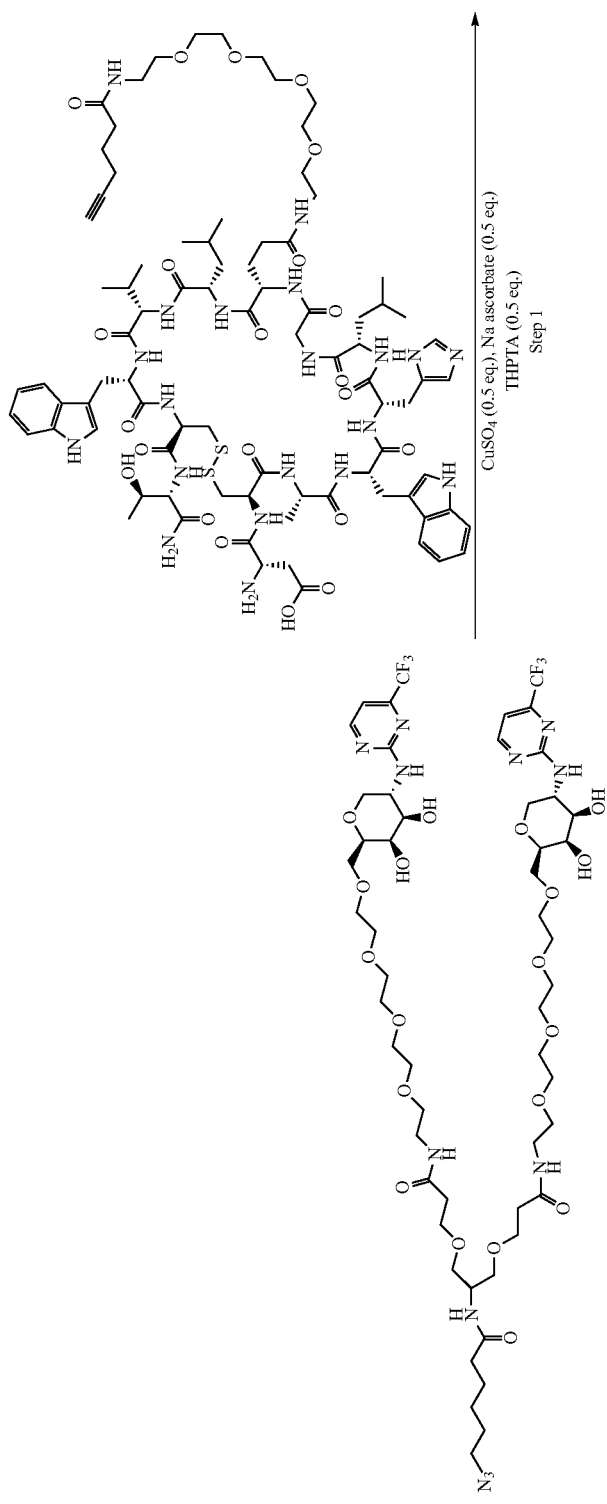

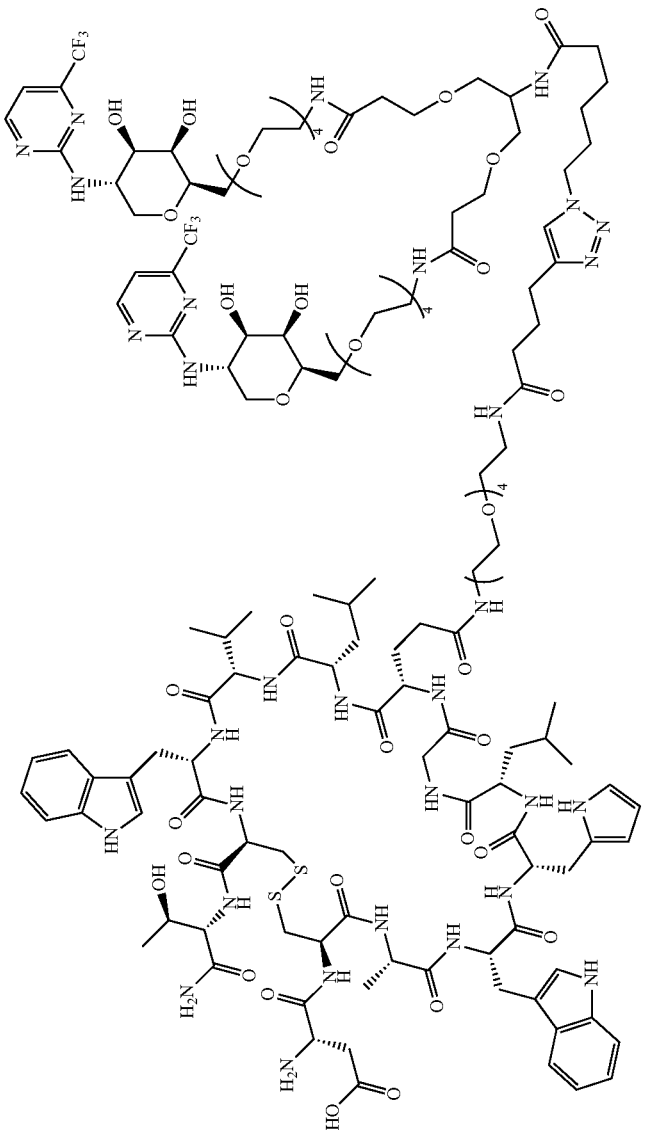

Step 1: THPTA (3.15 mg, 0.007 mmol) and CuSO₄ (1.16 mg, 0.007 mmol) were dissolved in water (0.5 mL) and then added to a solution of 3,3'-((2-(6-azidohexanamido)propane-1,3-diyl)bis(oxy))bis(N-(1-(((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (19 mg, 0.015 mmol) and (S)-4-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(3,20-dioxo-7,10,13,16-tetraoxa-4,19-diazapentacos-24-yn-1-yl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)amino)-3-amino-4-oxobutanoic acid (30.0 mg, 0.015 mmol) in MeOH (5 mL). A freshly prepared solution of Na ascorbate (1.44 mg, 0.007 mmol) in water (0.5 mL) was added and the reaction mixture was stirred at 35° C. for 16 hours. The reaction was purified by prep-HPLC to give (S)-4-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(23-(1-(1-(((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-3,20-dioxo-7,10,13,16-tetraoxa-4,19-diazatricosyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)amino)-3-amino-4-oxobutanoic acid (Compound 2, 15.1 mg, 33% yield). LC-MS (ESI) found: 1051 [M+3H]³⁺. ¹H NMR (400 MHz, CD₃OD): δ 8.71 (s, 1H), 8.50 (d, J=4.8 Hz, 2H), 7.73 (s, 1H), 7.46 (d, J=7.9 Hz, 1H), 7.41 (d, J=6.7 Hz, 1H), 7.32 (d, J=7.9 Hz, 2H), 7.24 (d, J=8.0 Hz, 1H), 7.07-6.86 (m, 8H), 4.51 (d, J=30.6 Hz, 4H), 4.34 (dd, J=12.8, 5.9 Hz, 7H), 4.17 (d, J=16.7 Hz, 2H), 4.08 (dd, J=10.0, 4.5 Hz, 3H), 3.91 (d, J=3.0 Hz, 3H), 3.70-3.47 (m, 60H), 3.38-3.31 (m, 9H), 3.14 (dd, J=20.4, 9.4 Hz, 7H), 2.93 (dd, J=38.3, 12.3 Hz, 7H), 2.70 (t, J=7.5 Hz, 2H), 2.44 (t, J=6.1 Hz, 4H), 2.30-2.17 (m, 7H), 2.08 (s, 1H), 2.00-1.76 (m, 6H), 1.72-1.42 (m, 9H), 1.30 (s, 3H), 1.20 (s, 6H), 0.98-0.80 (m, 15H), 0.74 (d, J=5.4 Hz, 3H).

Preparation of Compound 3, (S)-4-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(23-(1-(20-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)-3,20-dioxo-7,10,13,16-tetraoxa-4,19-diazatricosyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)amino)-3-amino-4-oxobutanoic acid

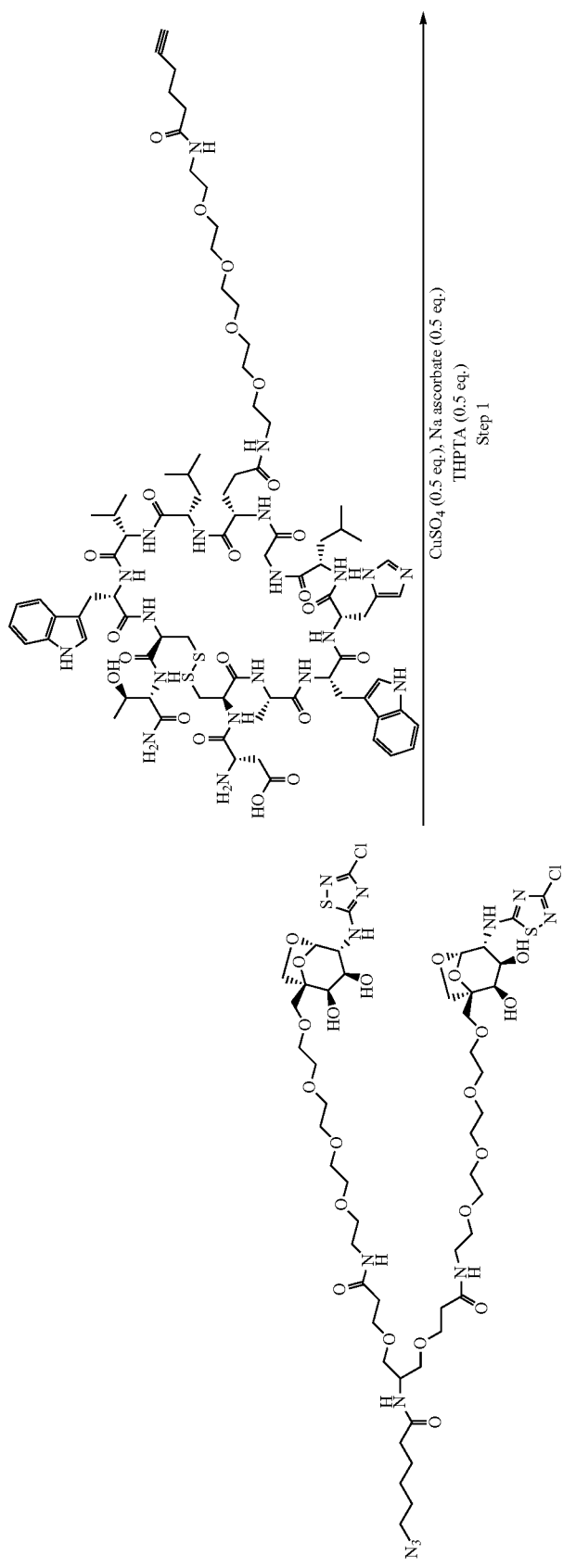

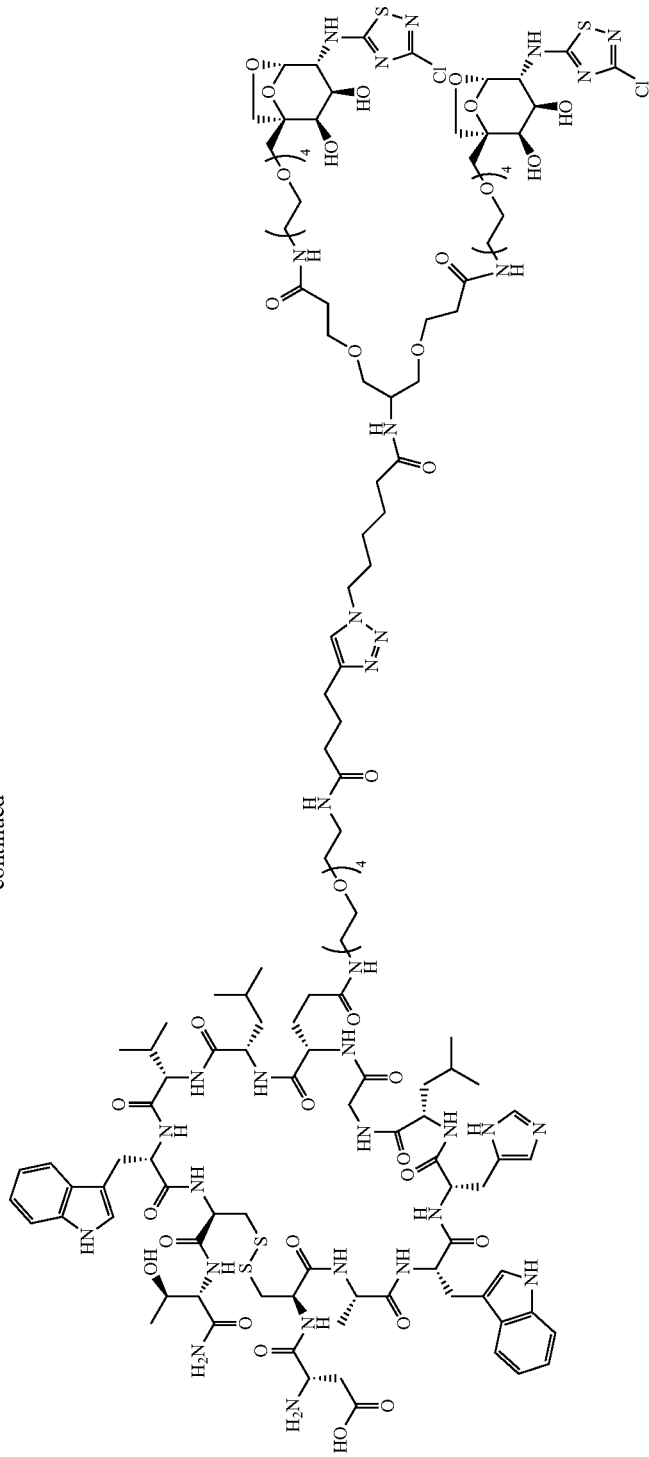

Step 1: THPTA (3.15 mg, 0.007 mmol) and CuSO$_4$ (1.16 mg, 0.007 mmol) were dissolved in water (0.5 mL) and then added to a solution of 3,3'-((2-(6-azidohexanamido)propane-1,3-diyl)bis(oxy))bis(N-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide) (A14, 19 mg, 0.015 mmol) and (S)-4-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(3,20-dioxo-7,10,13,16-tetraoxa-4,19-diazapentacos-24-yn-1-yl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)amino)-3-amino-4-oxobutanoic acid (26.76 mg, 0.015 mmol) in MeOH (5 mL). A freshly prepared solution of Na ascorbate (1.44 mg, 0.007 mmol) in water (0.5 mL) was added and the reaction mixture was stirred at 35° C. for 24 hours. The reaction was purified by prep-HPLC to give (S)-4-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(23-(1-(20-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)-3,20-dioxo-7,10,13,16-tetraoxa-4,19-diazatricosyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)amino)-3-amino-4-oxobutanoic acid (Compound 3, 13.8 mg, 30% yield). LC-MS (ESI) found: 1051 [M+3H]$^{3+}$. $^1$H NMR (400 MHz, CD$_3$OD): δ 8.17 (s, 1H), 7.73 (s, 1H), 7.46 (d, J=7.7 Hz, 1H), 7.36 (dd, J=33.3, 7.8 Hz, 3H), 7.24 (d, J=8.1 Hz, 1H), 6.99-6.95 (m, 6H), 5.38 (s, 2H), 4.70-4.43 (m, 4H), 4.43-4.30 (m, 4H), 4.24-4.06 (m, 3H), 3.96 (dd, J=23.4, 6.8 Hz, 7H), 3.84-3.74 (m, 5H), 3.73-3.41 (m, 60H), 3.36 (dd, J=12.1, 6.3 Hz, 8H), 3.28-3.20 (m, 1H), 3.18-3.06 (m, 4H), 3.05-2.89 (m, 5H), 2.85 (d, J=7.1 Hz, 2H), 2.70 (t, J=7.5 Hz, 2H), 2.51-2.40 (m, 4H), 2.32-2.15 (m, 7H), 2.09 (s, 1H), 2.00-1.80 (m, 5H), 1.67-1.49 (m, 7H), 1.41-1.28 (m, 4H), 1.20 (d, J=6.3 Hz, 6H), 0.98-0.69 (m, 18H).

Preparation of Compound 4, 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(20-(1-(1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-17-oxo-4,7,10,13-tetraoxa-16-azaicosanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanioic acid

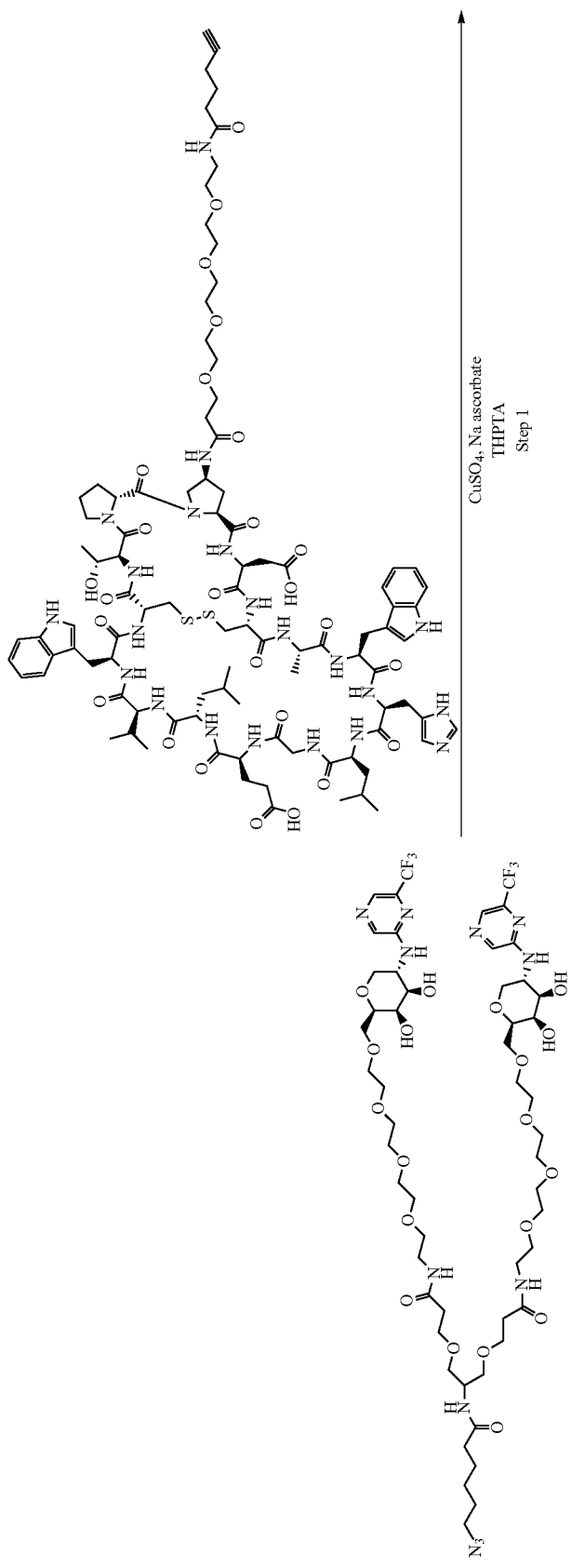

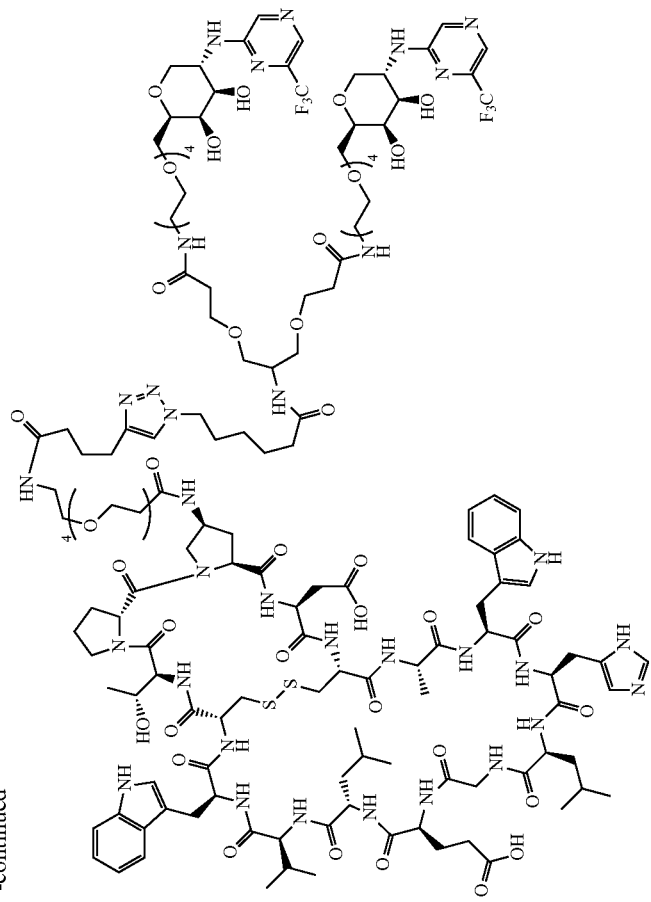

Step 1: THPTA (2 mg) and CuSO₄ (1 mg) were dissolved in water (0.5 mL). The mixture was added to a solution of 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-11-((R)-1-hydroxyethyl)-23,32-diisobutyl-20-isopropyl-41-methyl-5,10,13,16,19,22,25,28,31,34,37,40,43,46,49-pentadecaoxo-2-(17-oxo-4,7,10,13-tetraoxa-16-azadocos-21-ynamido)octatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (15 mg) and 3,3'-((2-(6-azidohexanamido)propane-1,3-diyl)bis(oxy))bis(N-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-yl)propanamide) (A2, 9 mg) in DMSO (3 mL). A freshly prepared solution of Na ascorbate (2 mg) in water (0.5 mL) was added. The reaction was stirred overnight. The resulting mixture was filtered. The crude product was purified by prep-HPLC to give 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(20-(1-(1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-17-oxo-4,7,10,13-tetraoxa-16-azaicosanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Compound 4, 5.2 mg, 37% yield) as white solid. LC-MS (ESI) found: 843 [M+4H]⁴⁺. ¹H NMR (400 MHz, CD₃OD): δ 8.72 (s, 1H), 8.29 (s, 1H), 8.11 (s, 2H), 7.99 (s, 2H), 7.75 (s, 1H), 7.68 (d, J=8.7 Hz, 1H), 7.48 (d, J=9.2 Hz, 1H), 7.41 (s, 1H), 7.30 (d, J=8.0 Hz, 1H), 7.18-7.10 (m, 2H), 7.05 (t, J=7.1 Hz, 1H), 6.98 (t, J=7.5 Hz, 1H), 6.90 (dd, J=15.2, 7.4 Hz, 1H), 6.85 (d, J=4.8 Hz, 1H), 5.81 (d, J=17.0 Hz, 1H), 5.49 (d, J=8.6 Hz, 1H), 5.35 (d, J=3.1 Hz, 1H), 4.69-4.57 (m, 3H), 4.48 (d, J=21.3 Hz, 2H), 4.41-4.25 (m, 9H), 4.15-4.02 (m, 7H), 3.92 (d, J=2.9 Hz, 2H), 3.78-3.55 (m, 56H), 3.56-3.39 (m, 12H), 3.36 (t, J=4.7 Hz, 7H), 3.27-3.15 (m, 4H), 3.12 (dd, J=13.6, 8.0 Hz, 3H), 3.06-2.67 (m, 8H), 2.45 (dd, J=13.8, 6.7 Hz, 8H), 2.22 (dt, J=19.2, 7.5 Hz, 6H), 2.10-1.85 (m, 10H), 1.75-1.51 (m, 8H), 1.43-1.27 (m, 3H), 1.15 (dd, J=11.4, 6.6 Hz, 6H), 1.05-0.78 (m, 18H). ¹⁹F NMR (377 MHz, CD₃OD): δ −70.21, −77.13, −77.18.

Preparation of Compound 5, 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(17-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)methyl)-1H-1,2,3-triazol-4-yl)-14-oxo-4,7,10-trioxa-13-azaheptadecanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

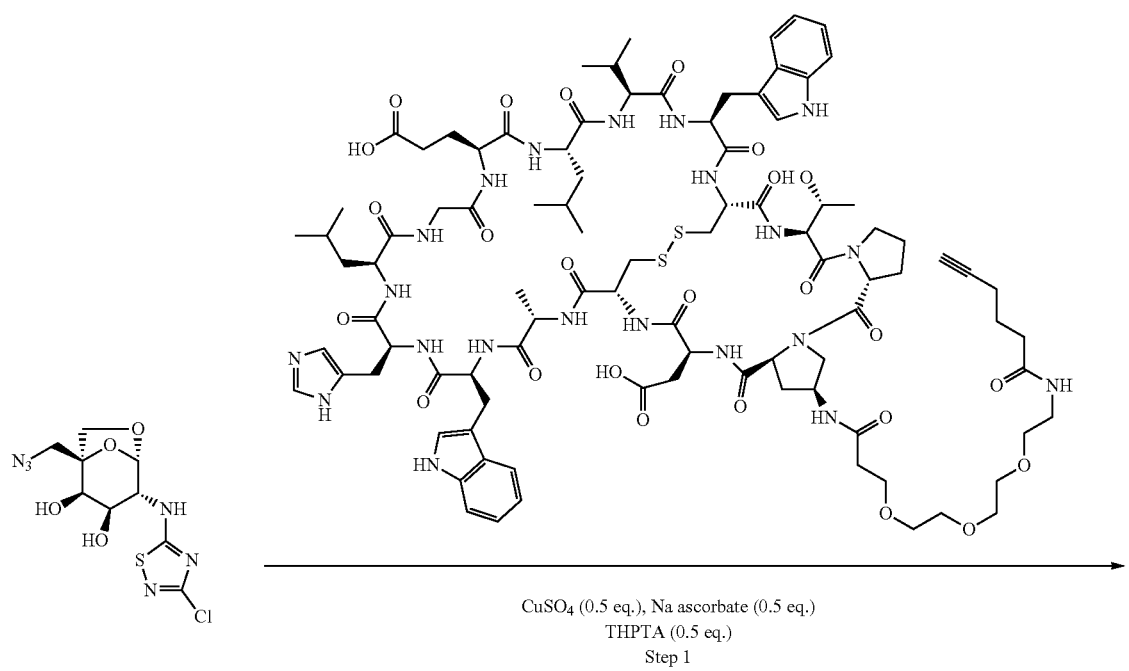

CuSO₄ (0.5 eq.), Na ascorbate (0.5 eq.)
THPTA (0.5 eq.)
Step 1

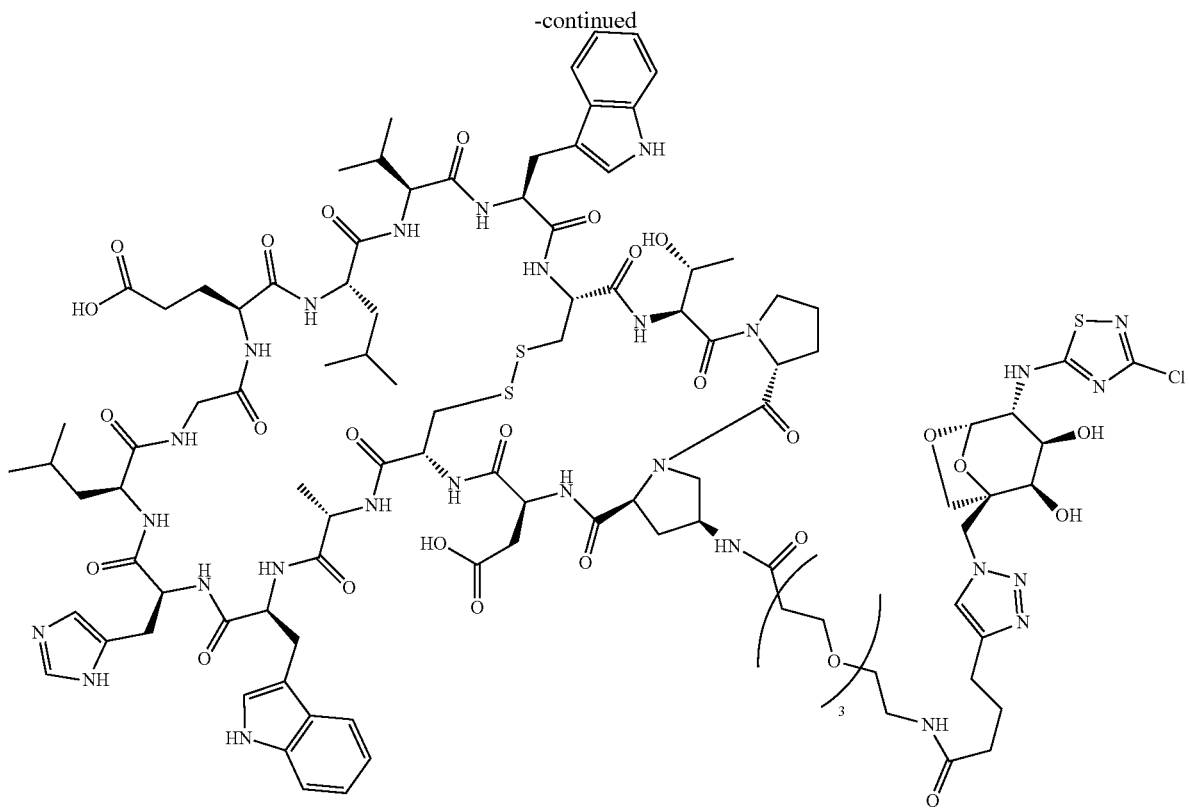

Step 1: THPTA (1.94 mg, 0.004 mmol) and CuSO₄ (0.72 mg, 0.004 mmol) were dissolved in water (0.5 mL) and then added to a solution of (1S,2R,3R,4R,5S)-1-(azidomethyl)-4-((3-chloro-1,2,4-thiadiazol-5-yl)amino)-6,8-dioxabicyclo [3.2.1]octane-2,3-diol (3 mg, 0.009 mmol) and 3-((2S,5aR, 11S,14R,17S,20S,23S,26S,32S,35S,38S,41S,44R,47S, 49aS)-35-((1H-imidazol-5-yl)methyl)-17,38-bis((1H-indol-3-yl)methyl)-47-(carboxymethyl)-11-((R)-1-hydroxyethyl)-23,32-diisobutyl-20-isopropyl-41-methyl-5,10,13,16,19,22, 25,28,31,34,37,40,43,46,49-pentadecaoxo-2-(14-oxo-4,7, 10-trioxa-13-azanonadec-18-ynamido)octatetracontahydro-5H-14,44-(methanodithiomethano)dipyrrolo[1,2-a:1',2'-d] [1,4,7,10,13,16,19,22,25,28,31,34,37,40,43]pentadec- aazacyclopentatetracontin-26-yl)propanoic acid (Intermediate 9, 20.0 mg, 0.009 mmol) in MeOH (5 mL). A freshly prepared solution of Na ascorbate (0.35 mg, 0.002 mmol) in water (0.5 mL) was added and the reaction mixture was stirred at room temperature for 24 hours. The solvent was evaporated and the crude material was purified by prep-HPLC (TFA/MeOH) to afford 3-((2S,5aR,11S,14R,17S, 20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(17-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)methyl)-1H-1,2,3-triazol-4-yl)-14-oxo-4,7,10-trioxa-13-azaheptadecanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34, 37,40,43]pentadecaazacyclopentatetracontin-26-yl)propanoic acid (Compound 5, 6 mg, 28% yield). LC-MS (ESI) found: 1178 [M+2H]²⁺. ¹H NMR (400 MHz, CD₃OD): δ 7.78 (s, 1H), 7.68 (d, J=8.2 Hz, 1H), 7.47 (d, J=8.6 Hz, 1H), 7.41 (s, 1H), 7.32 (dd, J=17.8, 7.7 Hz, 2H), 7.18-7.10 (m, 2H), 7.05 (t, J=7.5 Hz, 1H), 6.98 (t, J=7.4 Hz, 1H), 6.94-6.82 (m, 3H), 5.38 (d, J=0.9 Hz, 1H), 4.89 (d, J=5.5 Hz, 4H), 4.76 (d, J=7.7 Hz, 2H), 4.69-4.63 (m, 1H), 4.59 (dd, J=8.8, 4.3 Hz, 1H), 4.48 (ddd, J=14.5, 5.2, 3.2 Hz, 2H), 4.32 (ddd, J=22.3, 11.5, 5.5 Hz, 5H), 4.13-4.02 (m, 2H), 3.90 (dd, J=36.3, 5.6 Hz, 2H), 3.80-3.70 (m, 6H), 3.61 (dt, J=7.6, 4.3 Hz, 11H), 3.54 (t, J=5.4 Hz, 2H), 3.46 (s, 1H), 3.36 (t, J=5.3 Hz, 3H), 3.26-3.11 (m, 4H), 3.08-2.84 (m, 4H), 2.73 (t, J=7.6 Hz, 3H), 2.49 (dd, J=24.6, 18.4 Hz, 6H), 2.25 (t, J=7.4 Hz, 6H), 2.13 (dd, J=13.2, 6.2 Hz, 1H), 2.04-1.89 (m, 7H), 1.85-1.71 (m, 3H), 1.69-1.54 (m, 2H), 1.29 (s, 2H), 1.19-1.10 (m, 6H), 1.00-0.90 (m, 15H), 0.85 (d, J=6.9 Hz, 3H).

Preparation of Compound 6, 3-((2S,5aR,11S,14R, 17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(4-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11, 18-pentaoxa-14-azanonadecan-19-yl)-15,22-dioxo-2, 5,8,11,18-pentaoxa-14,21-diazaheptacosan-27-yl)-1H-1,2,3-triazol-4-yl)butanamido)ethoxy) propanamido)-11-((R)-1-hydroxyethyl)-23,32-diisobutyl-20-isopropyl-41-methyl-5,10,13,16,19,22, 25,28,31,34,37,40,43,46,49-pentadecaoxooctatetracontahydro-5H-14,44-(methanodithiomethano)dipyrrolo[1,2-a:1',2'-d][1,4, 7,10,13,16,19,22,25,28,31,34,37,40,43] pentadecaazacyclopentatetracontin-26-yl)propanoic acid

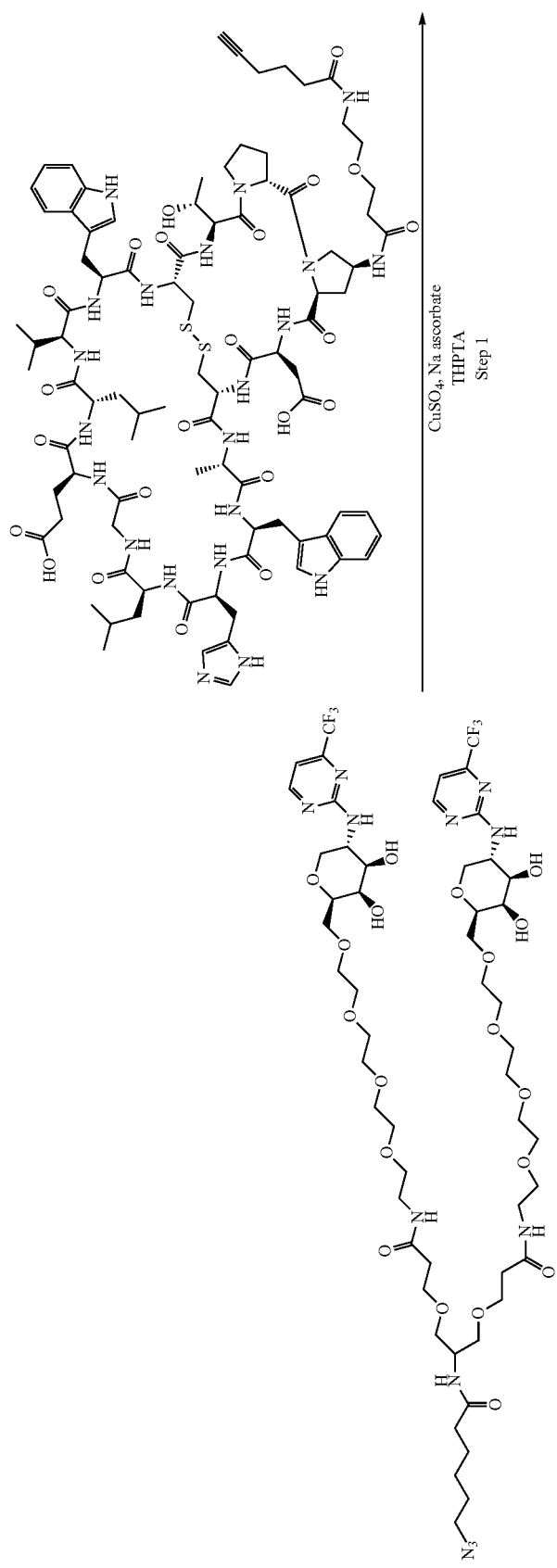

1007 1008
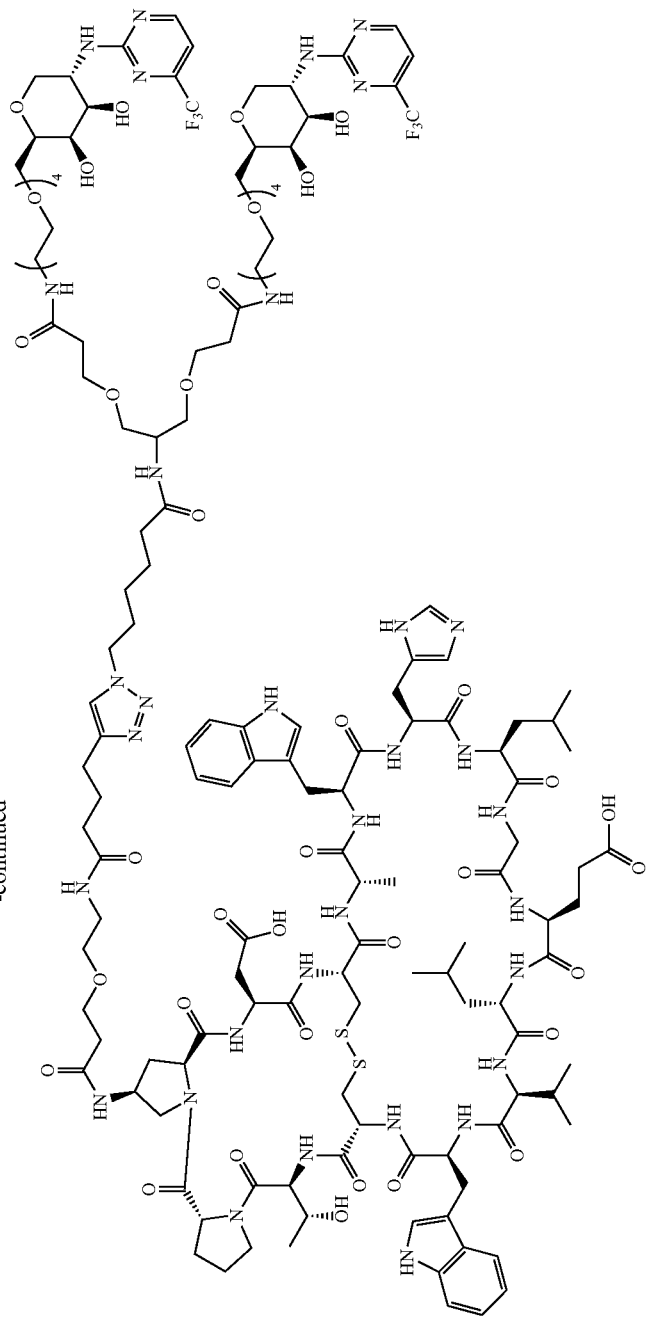
-continued

Step 1: THPTA (13 mg, 0.03 mmol) and CuSO₄ (0.38 mg, 0.0015 mmol) were dissolved in water (0.1 mL) and then added to a solution of 3,3'-((2-(6-azidohexanamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (20 mg, 0.015 mmol) and 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(hex-5-ynamido)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Intermediate 7, 28.9 mg, 0.015 mmol) in MeOH (2 mL). A freshly prepared solution of Sodium ascorbate (2.64 mg, 0.015 mmol) in water (0.1 mL) was added and the reaction mixture was stirred at rt overnight. Solvent was evaporated and the product was purified by Prep-HPLC to give 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(4-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)butanamido)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43] pentadecaazacyclopentatetracontin-26-yl)propanoic acid (Compound 6, 7 mg, 14.3% yield) as a white solid. LC-MS (ESI) found: 1081 [M+3H]³⁺. ¹H NMR (400 MHz, CD₃OD): δ 8.50 (d, J=4.6 Hz, 2H), 7.75 (s, 1H), 7.69 (d, J=8.3 Hz, 1H), 7.48 (d, J=7.6 Hz, 1H), 7.41 (s, 1H), 7.34 (s, 1H), 7.30 (d, J=8.0 Hz, 1H), 7.19-7.10 (m, 2H), 7.04 (d, J=8.0 Hz, 1H), 6.98 (d, J=7.4 Hz, 1H), 6.94-6.80 (m, 5H), 4.69-4.44 (m, 4H), 4.35 (t, J=6.9 Hz, 9H), 4.06 (d, J=6.8 Hz, 5H), 3.91 (d, J=3.2 Hz, 2H), 3.76-3.50 (m, 49H), 3.49-3.40 (m, 5H), 3.36 (t, J=5.4 Hz, 9H), 3.20-3.11 (m, 4H), 3.09-2.78 (m, 5H), 2.72 (t, J=7.6 Hz, 3H), 2.44 (t, J=6.0 Hz, 11H), 2.33-2.12 (m, 8H), 2.04-1.85 (m, 12H), 1.63 (s, 4H), 1.30 (s, 6H), 1.20-1.09 (m, 6H), 0.94-0.90 (m, 18H).

Preparation of Compound 7, 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(4-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)methyl)-1H-1,2,3-triazol-4-yl)butanamido)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43] pentadecaazacyclopentatetracontin-26-yl)propanoic acid

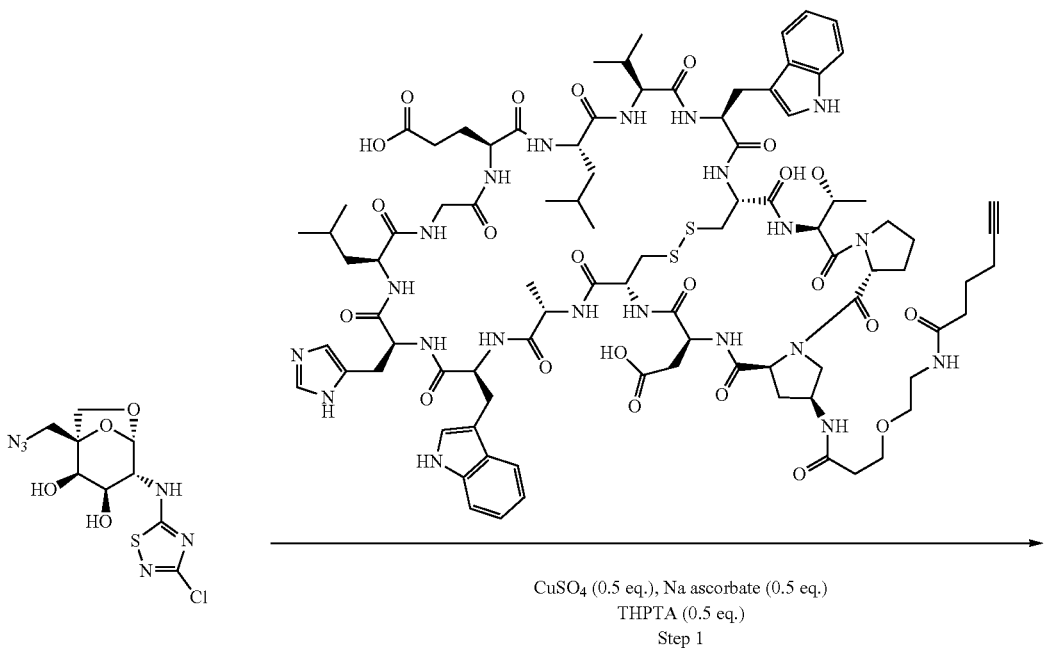 [SMILES: [N-]=[N+]=NC[C@@]12CO[C@@H](O1)[C@H](Nc1nc(Cl)ns1)[C@@H](O)[C@H]2O ; C#CCCCC(=O)NCCOCCC(=O)N[C@H]1C[C@H]2C(=O)N[C@@H](CC(=O)O)C(=O)N[C@H]3CSSC[C@H](NC(=O)[C@H](Cc4c[nH]c5ccccc45)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc4cnc[nH]4)NC(=O)[C@H](Cc4c[nH]c5ccccc45)NC(=O)[C@H](C)NC3=O)C(=O)N[C@@H]([C@@H](C)O)C(=O)N3CCC[C@@H]3C(=O)N2C1]

CuSO₄ (0.5 eq.), Na ascorbate (0.5 eq.)
THPTA (0.5 eq.)
Step 1

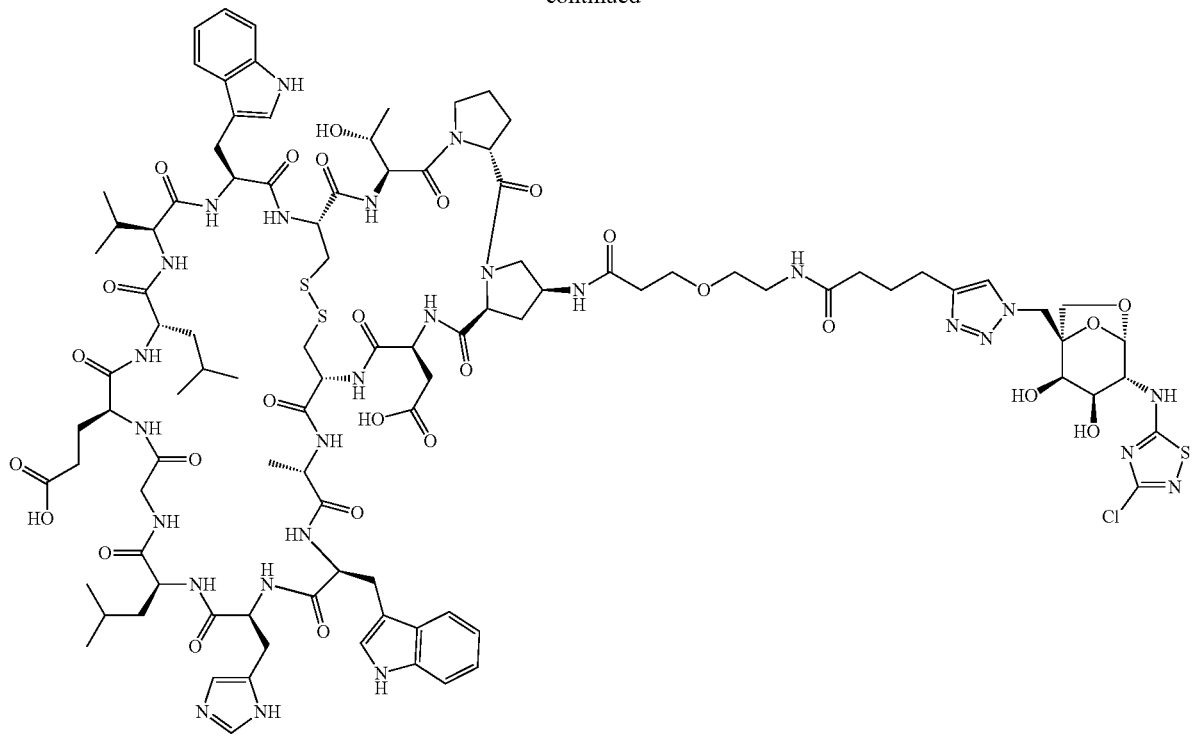 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)CCOCCNC(=O)CCCc3cn(C[C@@]45CO[C@@H](O4)[C@H](Nc4nc(Cl)ns4)[C@@H](O)[C@H]5O)nn3)C[C@H]1C(=O)N[C@@H](CC(=O)O)C(=O)N2]

Step 1: THPTA (2 mg) and CuSO$_4$ (1 mg) were dissolved in water (0.5 mL). The mixture was added to a solution of 3-((2S,5aR,11S,14R,17S,20S,23S,26S,32S,35S,38S,41S, 44R,47S,49aS)-35-((1H-imidazol-5-yl)methyl)-17,38-bis ((1H-indol-3-yl)methyl)-47-(carboxymethyl)-2-(3-(2-(hex-5-ynamido)ethoxy)propanamido)-11-((R)-1-hydroxyethyl)-23,32-diisobutyl-20-isopropyl-41-methyl-5,10,13,16,19,22, 25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Intermediate 7, 30 mg) and (1S,2R,3R,4R,5S)-1-(azidomethyl)-4-((3-chloro-1,2,4-thiadiazol-5-yl)amino)-6,8-dioxabicyclo [3.2.1]octane-2,3-diol (5 mg) in DMSO (3 mL). A freshly prepared solution of Na ascorbate (2 mg) in water (0.5 mL) was added. The reaction was stirred overnight. The resulting mixture was filtered. The crude product was purified by prep-HPLC to give 3-((2S,5aR,11S,14R,17S,20S,23S,26S, 32S,35S,38S,41S,44R,47S,49aS)-35-((1H-imidazol-5-yl) methyl)-17,38-bis((1H-indol-3-yl)methyl)-47-(carboxymethyl)-2-(3-(2-(4-(1-(((1S,2R,3R,4R,5S)-4-((3-chloro-1,2,4-thiadiazol-5-yl)amino)-2,3-dihydroxy-6,8-dioxabicyclo [3.2.1]octan-1-yl)methyl)-1H-1,2,3-triazol-4-yl)butanamido)ethoxy)propanamido)-11-((R)-1-hydroxyethyl)-23, 32-diisobutyl-20-isopropyl-41-methyl-5,10,13,16,19,22,25, 28,31,34,37,40,43,46,49-pentadecaoxooctatetracontahydro-5H-14,44-(methanodithiomethano)dipyrrolo[1,2-a:1',2'-d] [1,4,7,10,13,16,19,22,25,28,31,34,37,40,43]pentadecaazacyclopentatetracontin-26-yl)propanoic acid (Compound 7, 5.2 mg, 37% yield) as white solid. LC-MS (ESI) found: 1133 [M+2H]$^{2+}$. $^1$H NMR (400 MHz, CD$_3$OD): δ 8.72 (s, 1H), 8.20 (s, 2H), 7.78 (s, 1H), 7.71 (d, J=8.1 Hz, 1H), 7.41 (t, J=18.1 Hz, 2H), 7.30 (d, J=8.1 Hz, 1H), 7.14 (s, 1H), 7.05 (t, J=7.2 Hz, 1H), 6.98 (t, J=7.4 Hz, 1H), 6.91 (dd, J=14.5, 6.8 Hz, 1H), 6.86 (s, 1H), 5.82 (s, 1H), 5.51 (s, 1H), 5.35 (d, J=24.0 Hz, 2H), 5.03-4.86 (m, 5H), 4.85-4.74 (m, 2H), 4.70-4.58 (m, 2H), 4.43 (d, J=34.4 Hz, 4H), 4.26 (d, J=6.0 Hz, 2H), 4.16-3.99 (m, 2H), 3.89 (d, J=32.2 Hz, 2H), 3.82-3.58 (m, 8H), 3.55-3.34 (m, 8H), 3.22 (dd, J=14.9, 6.2 Hz, 4H), 3.08-2.63 (m, 8H), 2.58-2.38 (m, 6H), 2.27 (dd, J=13.8, 6.4 Hz, 4H), 2.18-2.08 (m, 1H), 2.06-1.86 (m, 6H), 1.83-1.48 (m, 5H), 1.16 (d, J=6.1 Hz, 6H), 1.02-0.75 (m, 18H). $^{19}$F NMR (377 MHz, CD$_3$OD): δ −77.099 (s).

Preparation of Compound 8, 3-((2S,5aR,11S,14R, 17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(17-(1-(20-(1-(((1S,2R,3R,4R,5S)-4-((3-chloro-1,2,4-thiadiazol-5-yl)amino)-2,3-dihydroxy-6,8-dioxabicyclo[3.2.1] octan-1-yl)-15-oxo-2,5,8,11,18-pentaoxa-14-azanonadecan-19-yl)-1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5, 8,11,18-pentaoxa-14,21-diazaheptacosan-27-yl)-1H-1,2,3-triazol-4-yl)-14-oxo-4,7,10-trioxa-13-azaheptadecanamido)-11-((R)-1-hydroxyethyl)-23, 32-diisobutyl-20-isopropyl-41-methyl-5,10,13,16,19, 22,25,28,31,34,37,40,43,46,49-pentadecaoxooctatetracontahydro-5H-14,44-(methanodithiomethano) dipyrrolo[1,2-a:1',2'-d][1,4, 7,10,13,16,19,22,25,28,31,34,37,40,43] pentadecaazacyclo pentatetracontin-26-yl)propanoic acid

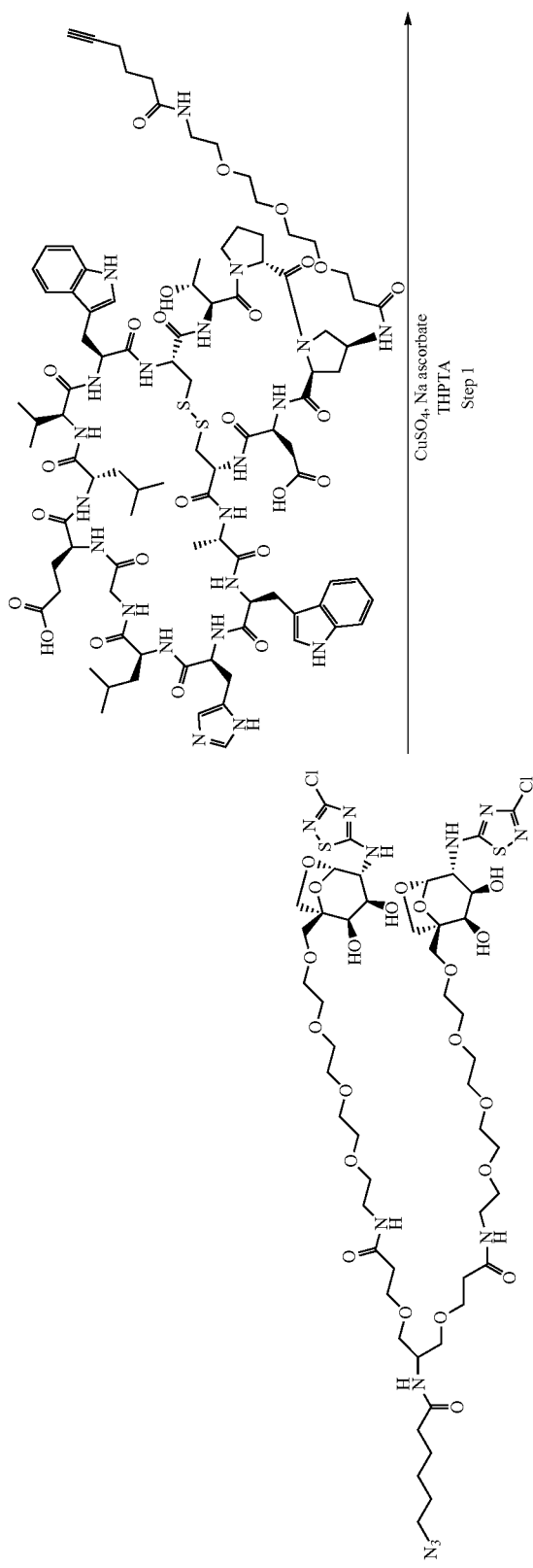

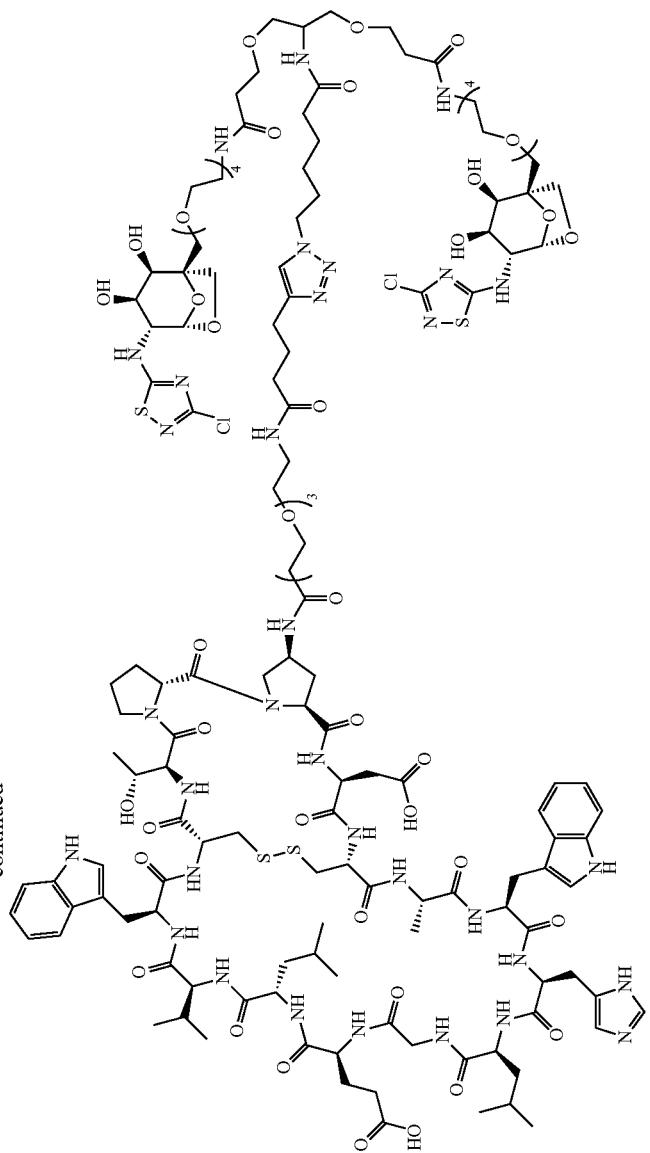

Step 1: THPTA (2 mg) and CuSO₄ (1 mg) were dissolved in water (0.5 mL). The mixture was added to a solution of 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-11-((R)-1-hydroxyethyl)-23,32-diisobutyl-20-isopropyl-41-methyl-5,10,13,16,19,22,25,28,31,34,37,40,43,46,49-pentadecaoxo-2-(14-oxo-4,7,10-trioxa-13-azanonadec-18-ynamido)octatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Intermediate 9, 30 mg) and 3,3'-((2-(6-azidohexanamido)propane-1,3-diyl)bis(oxy))bis(N-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide) (A14, 20 mg) in DMSO (3 mL). A freshly prepared solution of Na ascorbate (2 mg) in water (0.5 mL) was added. The reaction was stirred overnight. The resulting mixture was filtered. The crude product was purified by prep-HPLC to give 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(17-(1-(20-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)-14-oxo-4,7,10-trioxa-13-azaheptadecanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Compound 8, 21.7 mg, 44% yield) as white solid. LC-MS (ESI) found: 832 [M+4H]⁴⁺. ¹H NMR (400 MHz, CD₃OD): δ 8.73 (s, 2H), 8.20 (s, 1H), 7.76 (s, 1H), 7.69 (s, 1H), 7.44 (d, J=19.0 Hz, 2H), 7.30 (d, J=8.1 Hz, 1H), 7.14 (s, 1H), 7.05 (t, J=7.5 Hz, 1H), 6.98 (t, J=7.4 Hz, 1H), 6.88 (s, 2H), 5.81 (s, 1H), 5.50 (s, 1H), 5.38 (s, 2H), 4.89 (d, J=1.7 Hz, 5H), 4.81 (d, J=1.9 Hz, 5H), 4.69-4.19 (m, 11H), 4.08 (dd, J=15.3, 9.9 Hz, 3H), 3.99 (d, J=9.6 Hz, 2H), 3.93 (d, J=4.1 Hz, 2H), 3.87 (s, 2H), 3.80 (dd, J=12.3, 6.2 Hz, 3H), 3.74 (dd, J=14.5, 5.3 Hz, 4H), 3.71-3.57 (m, 40H), 3.54-3.46 (m, 11H), 3.36 (dd, J=10.2, 4.9 Hz, 7H), 3.28-3.20 (m, 2H), 3.14-2.62 (m, 8H), 2.45 (dd, J=14.0, 7.6 Hz, 10H), 2.23 (dt, J=19.8, 7.4 Hz, 8H), 2.04-1.47 (m, 16H), 1.31 (s, 2H), 1.16 (s, 5H), 0.92 (dd, J=28.9, 22.5 Hz, 18H). ¹⁹F NMR (377 MHz, CD₃OD): δ −77.379 (s).

Preparation of Compound 9, 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(4-(1-(20-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)butanamido)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

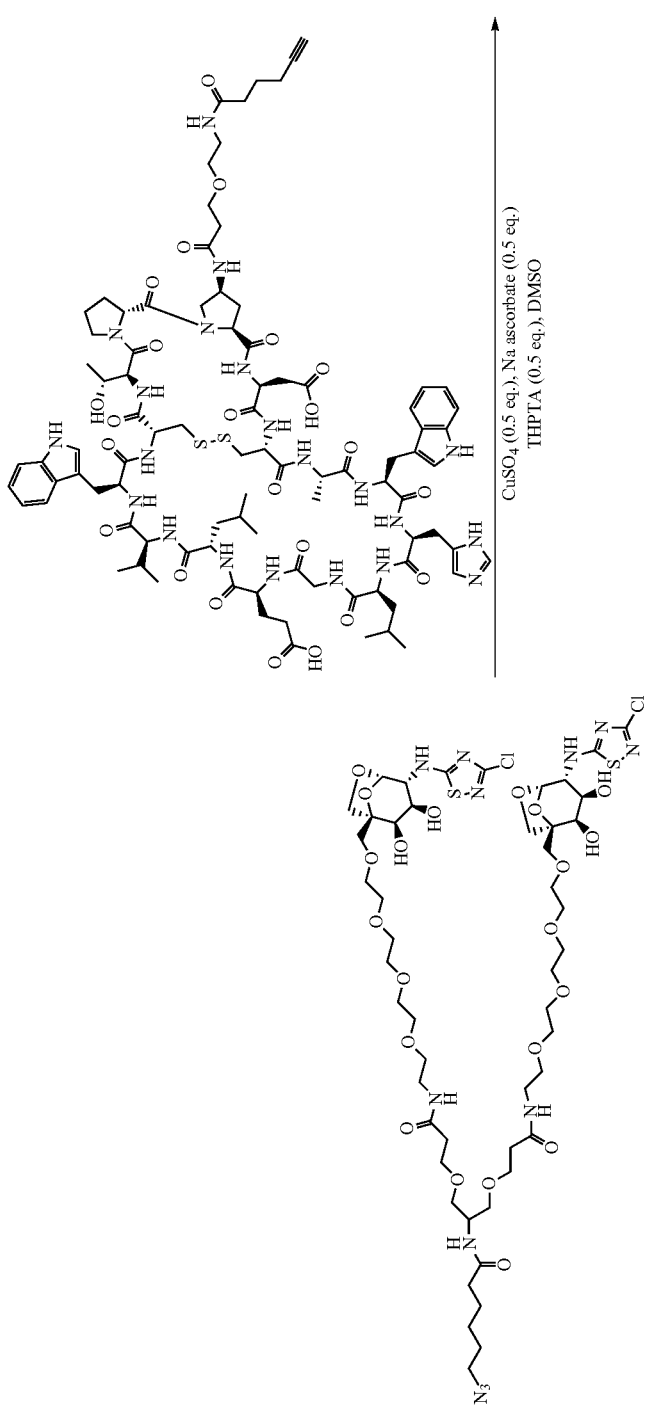

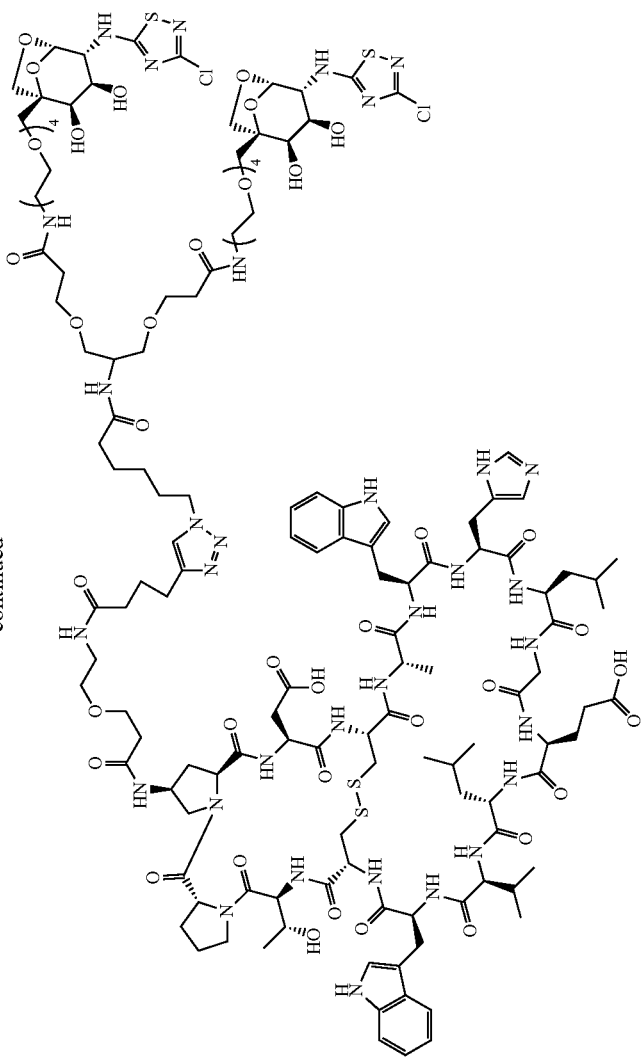

Step 1: To a solution of 3,3'-((2-(6-azidohexanamido)propane-1,3-diyl)bis(oxy))bis(N-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide) (A14, 15 mg, 0.01 mmol) and 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(hex-5-ynamido)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentade- caazacyclopentatetracontin-26-yl)propanoic acid (Intermediate 7, 25 mg, 0.01 mmol) in DMSO (2 mL) were added CuSO$_4$ (2 mg), THPTA (3 mg) in H$_2$O (0.1 mL) and Na ascorbate (2 mg) in H$_2$O (0.1 mL). The mixture was stirred at 40° C. overnight. The solution was purified by C18 column directly to give 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(4-(1-(20-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)butanamido)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Compound 9, 10 mg, 25% yield) as white solid. LC-MS (ESI) found: 1080 [M+3H]$^{3+}$. $^1$H NMR (400 MHz, CD$_3$OD): δ 7.75 (s, 1H), 7.69 (d, J=8.4 Hz, 1H), 7.48 (d, J=7.8 Hz, 1H), 7.41 (s, 1H), 7.38-7.28 (m, 2H), 7.21-6.76 (m, 7H), 5.38 (d, J=1.3 Hz, 2H), 4.70-4.28 (m, 12H), 4.15-3.59 (m, 54H), 3.57-3.35 (m, 18H), 3.23-2.69 (m, 10H), 2.55-2.09 (m, 20H), 2.08-1.74 (m, 12H), 1.63 (s, 4H), 1.39-1.07 (m, 10H), 1.04-0.80 (m, 18H).

Preparation of Compound 10, (S)-3-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(2-carboxyethyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)carbamoyl)-23-(1-(1-(((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-20-oxo-7,10,13,16-tetraoxa-4,19-diazatricosanoic acid

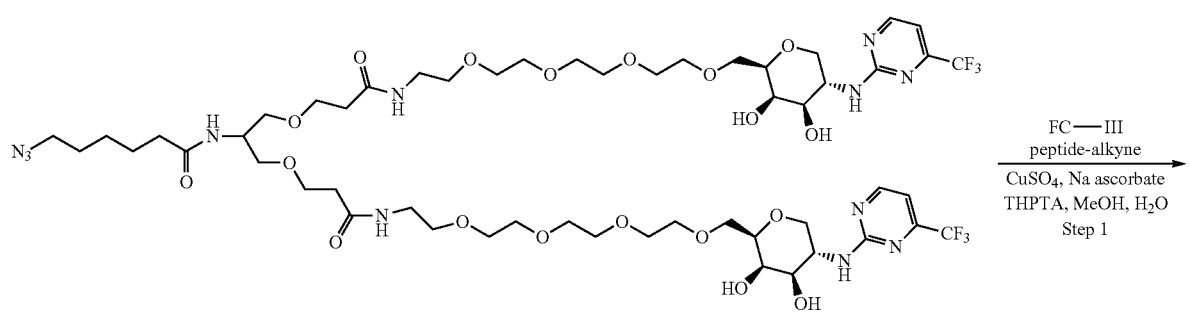

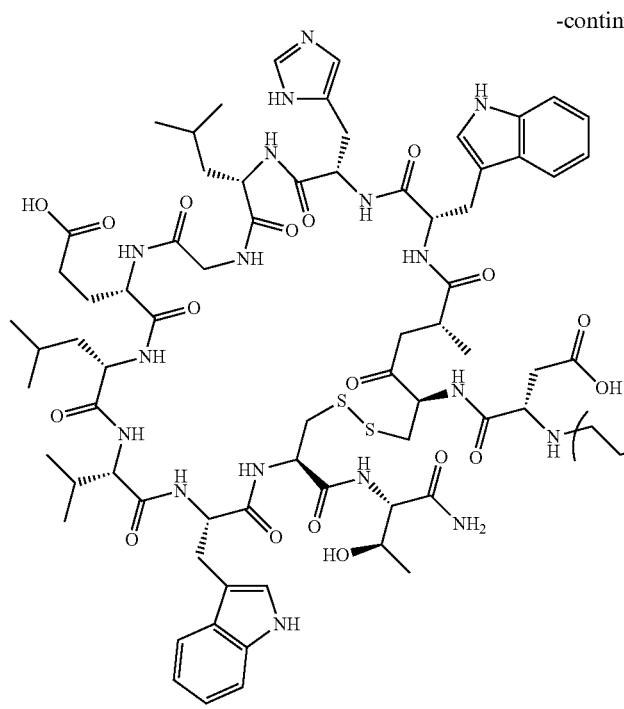
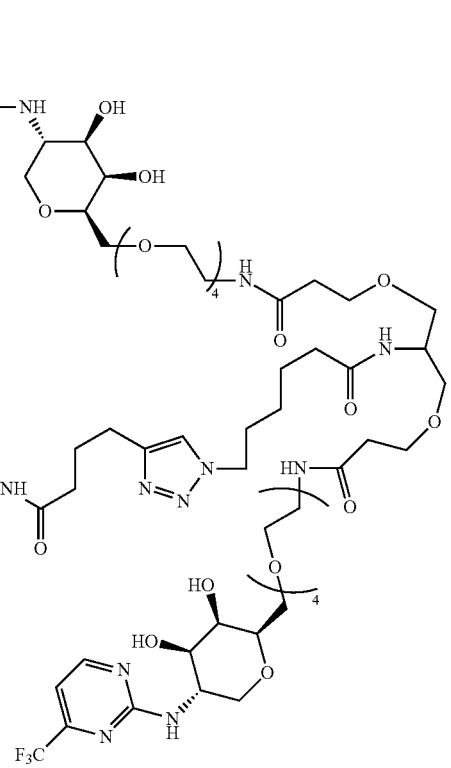

-continued

Step 1: THPTA (3.4 mg) and CuSO₄ (0.3 mg) were dissolved in water (0.2 mL). The mixture was added to a solution of 3,3'-((2-(6-azidohexanamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (21 mg) and FC-III peptide-alkyne (29.6 mg) in MeOH (5 mL). A freshly prepared solution of Na ascorbate (0.6 mg) in water (0.2 mL) was added. The reaction was stirred overnight. The resulting mixture was filtered. The crude product was purified by prep-HPLC to give (S)-3-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(2-carboxyethyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)carbamoyl)-23-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-20-oxo-7,10,13,16-tetraoxa-4,19-diazatricosanoic acid (Compound 10, 11.8 mg, 23.2% yield) as white solid. LC-MS (ESI) found: 788 [M+4H]⁴⁺. ¹H NMR (400 MHz, DMSO): δ 10.71 (s, 2H), 8.50 (d, J=61.1 Hz, 8H), 8.05 (s, 2H), 7.89 (dd, J=14.6, 8.9 Hz, 4H), 7.82 (s, 1H), 7.65-7.50 (m, 5H), 7.41 (d, J=7.7 Hz, 1H), 7.27 (d, J=7.7 Hz, 2H), 7.13 (t, J=24.1 Hz, 4H), 7.03-6.97 (m, 2H), 6.95 (d, J=4.9 Hz, 2H), 6.91 (t, J=7.4 Hz, 2H), 6.81 (s, 1H), 4.56 (d, J=82.6 Hz, 10H), 4.26 (t, J=7.1 Hz, 5H), 4.07 (d, J=23.3 Hz, 3H), 3.93 (s, 2H), 3.83 (s, 3H), 3.69 (s, 2H), 3.58-3.46 (m, 54H), 3.38 (dd, J=5.8, 3.1 Hz, 14H), 3.21-3.17 (m, 8H), 3.03-2.89 (m, 8H), 2.59 (dd, J=28.4, 20.7 Hz, 4H), 2.31 (t, J=6.5 Hz, 6H), 2.09 (dt, J=14.1, 7.4 Hz, 7H), 1.88-1.70 (m, 7H), 1.55-1.32 (m, 8H), 1.24-1.11 (m, 6H), 1.03 (d, J=6.1 Hz, 3H), 0.93-0.50 (m, 21H). ¹⁹F NMR (377 MHz, DMSO): δ −69.47 (s), −73.41 (s).

Preparation of Compound 11, 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(17-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-14-oxo-4,7,10-trioxa-13-azaheptadecanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic 1033 1034
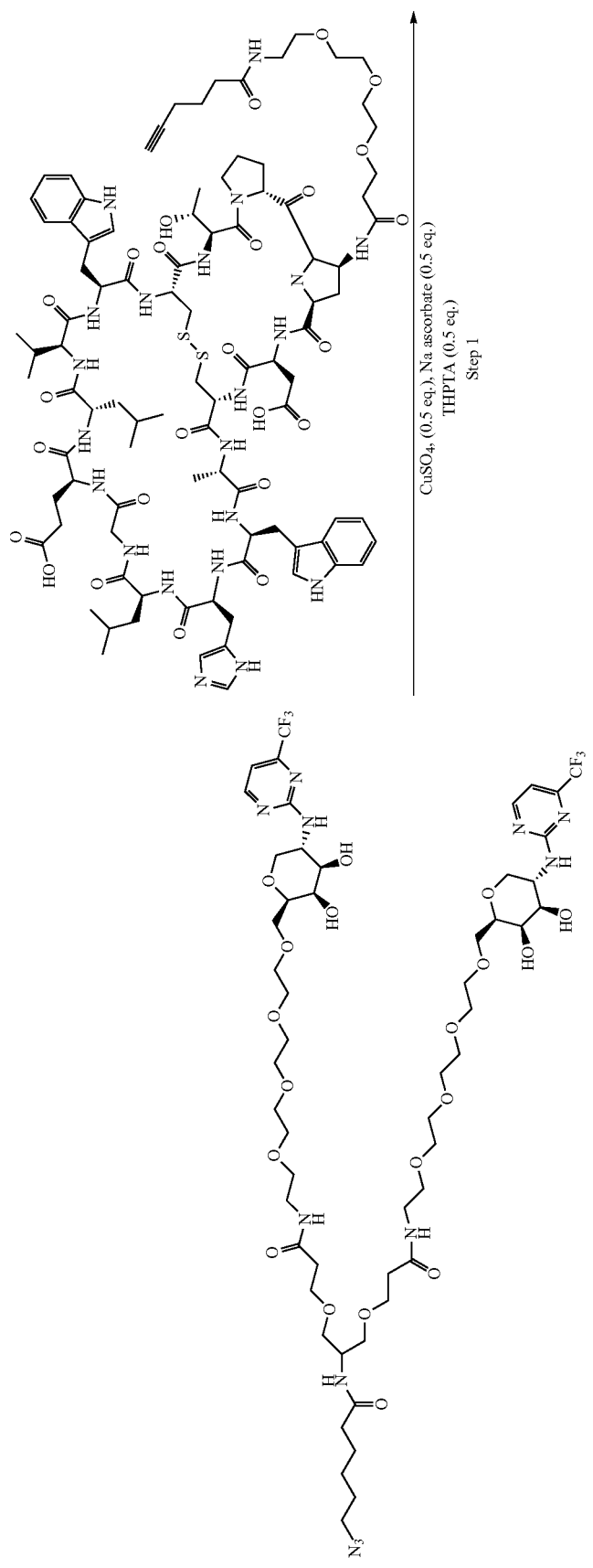

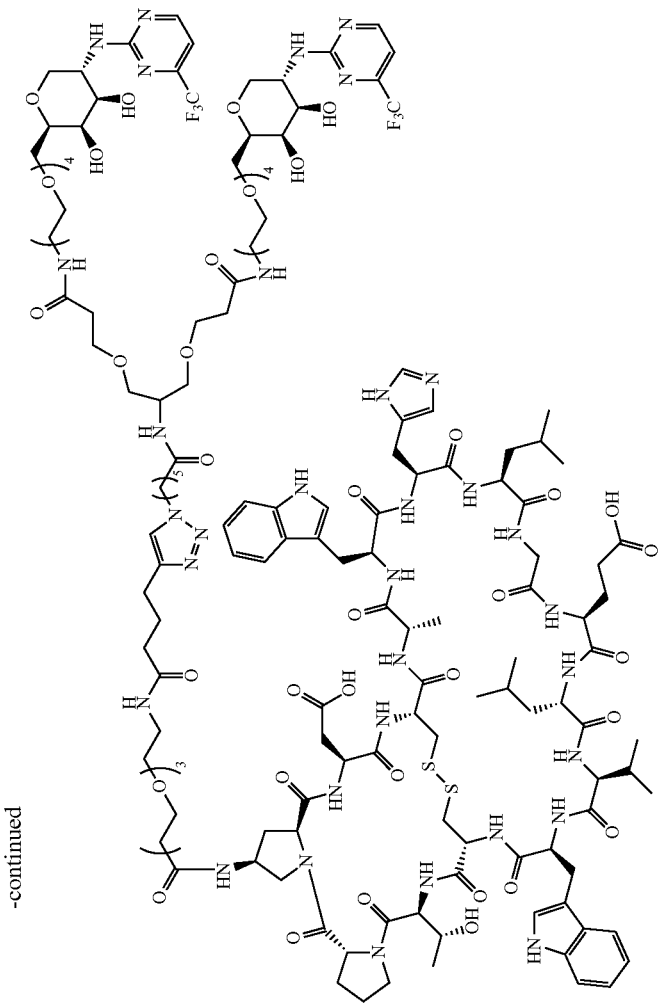

Step 1: THPTA (1.99 mg, 0.005 mmol) and CuSO$_4$ (0.73 mg, 0.005 mmol) were dissolved in water (0.5 mL) and then added to a solution of 3,3'-((2-(6-azidohexanamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (12 mg, 0.009 mmol) and 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-11-((R)-1-hydroxyethyl)-23,32-diisobutyl-20-isopropyl-41-methyl-5,10,13,16,19,22,25,28,31,34,37,40,43,46,49-pentadecaoxo-2-(14-oxo-4,7,10-trioxa-13-azanonadec-18-ynamido)octatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Intermediate 9, 20 mg, 0.009 mmol) in MeOH (10 mL). A freshly prepared solution of Na ascorbate (0.69 mg, 0.004 mmol) in water (0.5 mL) was added and the reaction mixture was stirred at 35° C. for 16 hours. The solvent was removed and purified by prep-HPLC to give 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(17-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-14-oxo-4,7,10-trioxa-13-azaheptadecanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Compound 11, 4.3 mg, 13% yield). LC-MS (ESI) found: 1110 [M+3H]$^{3+}$. $^1$H NMR (400 MHz, CD$_3$OD): δ 8.50 (d, J=4.6 Hz 2H), 8.39 (s, 1H), 7.73 (s, 1H), 7.53 (s, 1H), 7.33-7.53 (m, 2H), 7.16 (s, 1H), 7.10-6.91 (m, 6H), 6.88 (d, J=4.9 Hz, 3H), 4.62 (s, 3H), 4.49 (s, 4H), 4.40-4.31 (m, 6H), 4.13-4.02 (m, 6H), 3.91 (d, J=2.6 Hz, 3H), 3.75 (s, 3H), 3.67 (d, J=7.9 Hz, 9H), 3.61 (dt, J=13.4, 4.3 Hz, 39H), 3.52 (dd, J=11.8, 6.4 Hz, 9H), 3.49-3.42 (m, 6H), 3.37 (d, J=5.4 Hz, 6H), 3.19-3.11 (m, 6H), 2.74-2.67 (m, 3H), 2.54 (s, 3H), 2.44 (t, J=5.7 Hz, 6H), 2.29-2.16 (m, 10H), 2.03 (d, J=5.5 Hz, 5H), 1.97-1.84 (m, 8H), 1.60 (s, 9H), 1.21 (s, 6H), 0.92-0.72 (m, 18H).

Preparation of Compound 12, 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(2-(4-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)butanamido)ethoxy)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

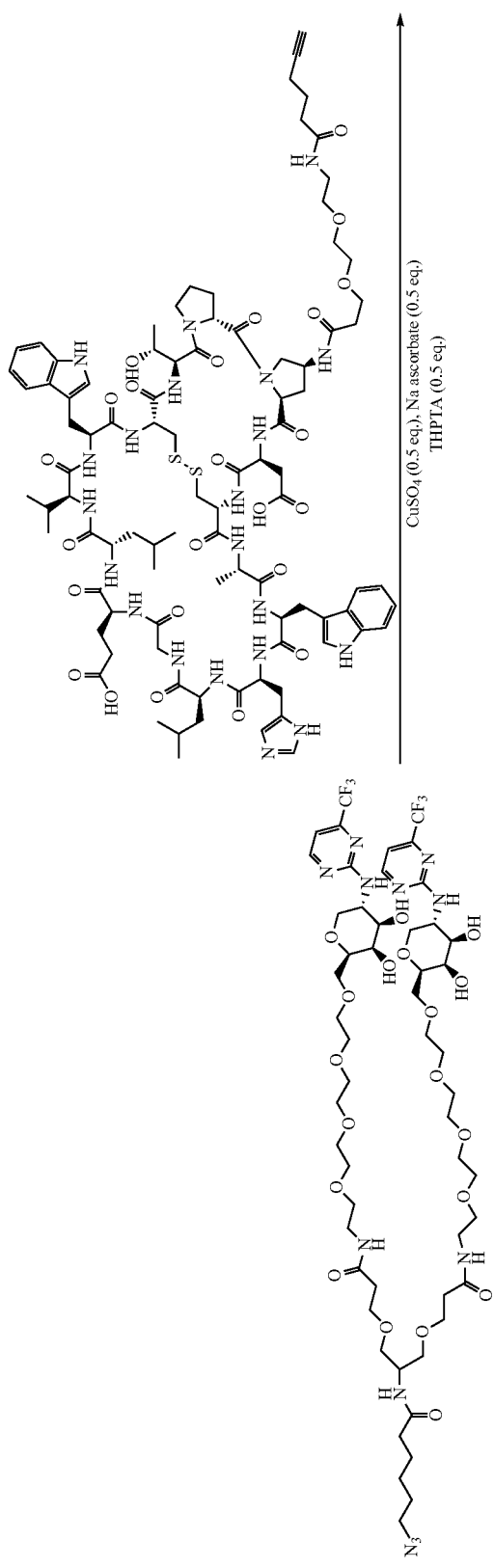

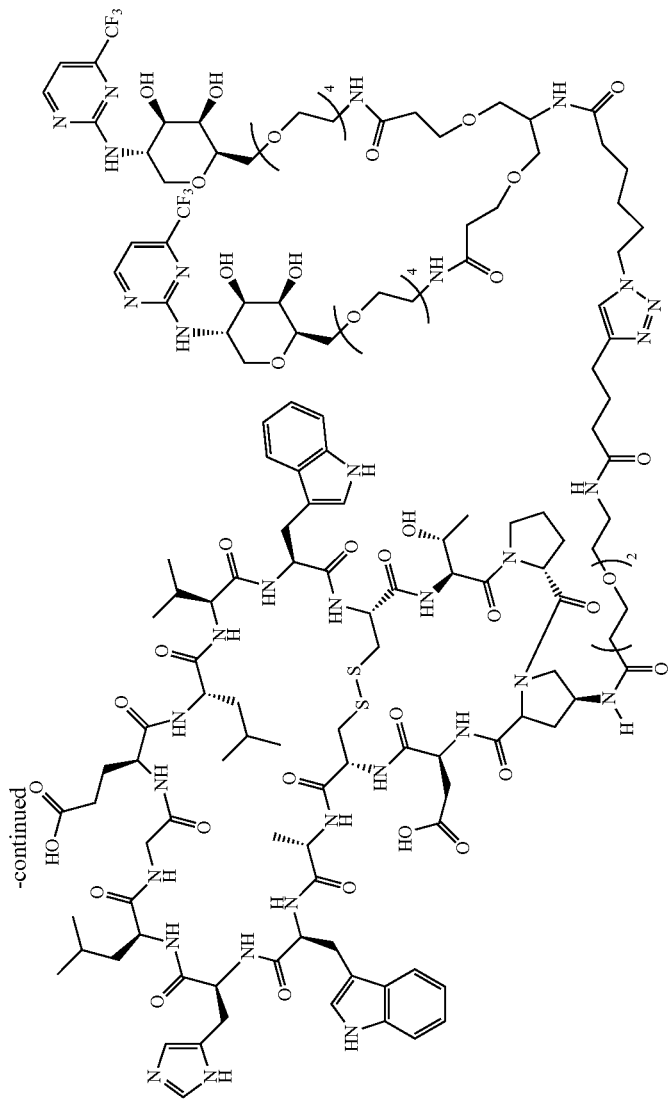
-continued

Step 1: To a solution of 3,3'-((2-(6-azidohexanamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (12.5 mg, 0.01 mmol) and 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(2-(hex-5-ynamido)ethoxy)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Intermediate 6, 20 mg, 0.01 mmol) in MeOH (5 mL) were added CuSO$_4$ (2 mg) and THPTA (3 mg) in H$_2$O (0.1 mL) and Na ascorbate (2 mg) in H$_2$O (0.1 mL). The mixture was stirred at 35° C. overnight, then concentrated. The residue was purified by prep-HPLC to give 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(2-(4-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)butanamido)ethoxy)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Compound 12, 10.8 mg, 33% yield) as white solid. LC-MS (ESI) found: 1095 [M+3H]$^{3+}$. $^1$H NMR (400 MHz, CD$_3$OD): δ 8.50 (d, J=5.2 Hz, 2H), 8.26 (s, 1H), 7.73 (s, 1H), 7.55-7.48 (m, 1H), 7.24 (s, 4H), 6.95 (s, 6H), 6.88 (d, J=4.9 Hz, 1H), 6.87 (s, 1H), 4.62 (s, 3H), 4.53-4.49 (m, 2H), 4.34 (t, J=7.3 Hz, 6H), 4.08 (d, J=9.2 Hz, 5H), 3.91 (d, J=2.9 Hz, 2H), 3.75 (s, 3H), 3.70-3.66 (m, 12H), 3.61 (dd, J=11.3, 6.3 Hz, 36H), 3.54 (dd, J=10.6, 5.1 Hz, 9H), 3.48 (d, J=3.2 Hz, 2H), 3.46-3.42 (m, 3H), 3.36 (t, J=5.4 Hz, 6H), 3.16 (d, J=10.8 Hz, 3H), 3.13 (d, J=1.8 Hz, 2H), 3.01-2.92 (m, 3H), 2.86-2.76 (m, 4H), 2.70 (t, J=7.5 Hz, 3H), 2.56-2.51 (m, 3H), 2.44 (t, J=6.0 Hz, 6H), 2.23 (dt, J=25.8, 7.4 Hz, 8H), 2.02 (d, J=8.5 Hz, 1H), 1.97-1.84 (m, 8H), 1.62 (s, 5H), 1.30 (s, 3H), 1.21 (s, 6H), 0.87 (s, 14H), 0.75 (s, 6H).

Preparation of Compound 13, 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(2-(4-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)methyl)-1H-1,2,3-triazol-4-yl)butanamido)ethoxy)ethoxy) propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

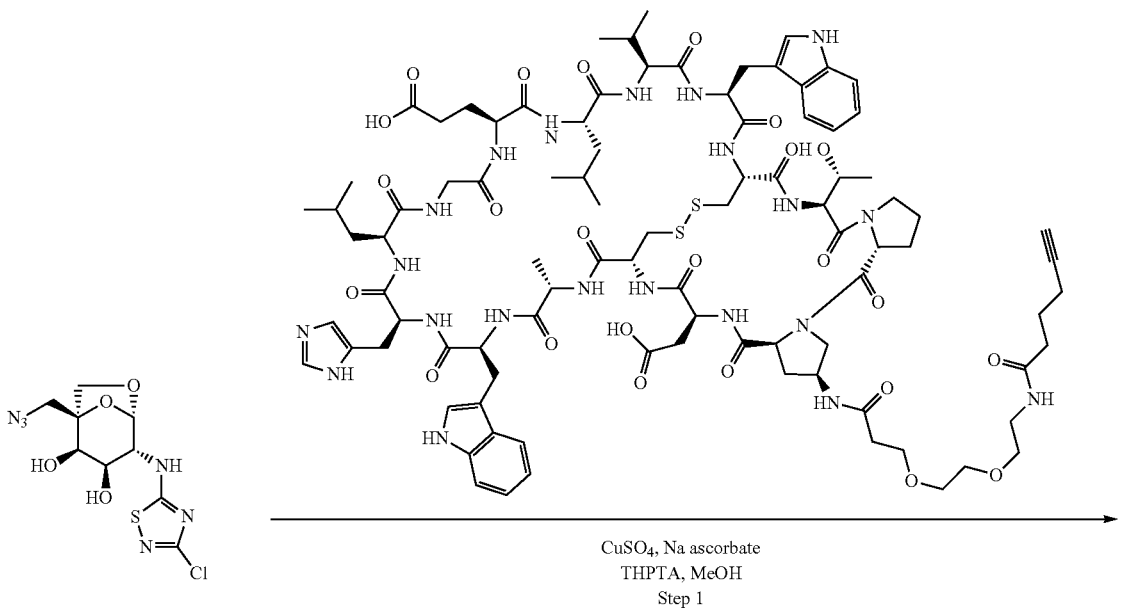 [SMILES: [N-]=[N+]=NC[C@@]12CO[C@@H](O1)[C@H](Nc1nc(Cl)ns1)[C@@H](O)[C@H]2O ; C#CCCCC(=O)NCCOCCOCCC(=O)N[C@H]1C[C@H]2C(=O)N[C@@H](CC(=O)O)C(=O)N[C@H]3CSSC[C@H](NC(=O)[C@H](Cc4c[nH]c5ccccc45)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc4cnc[nH]4)NC(=O)[C@H](Cc4c[nH]c5ccccc45)NC(=O)[C@H](C)NC3=O)C(=O)N[C@@H]([C@@H](C)O)C(=O)N3CCC[C@@H]3C(=O)N2C1]

CuSO$_4$, Na ascorbate
THPTA, MeOH
Step 1

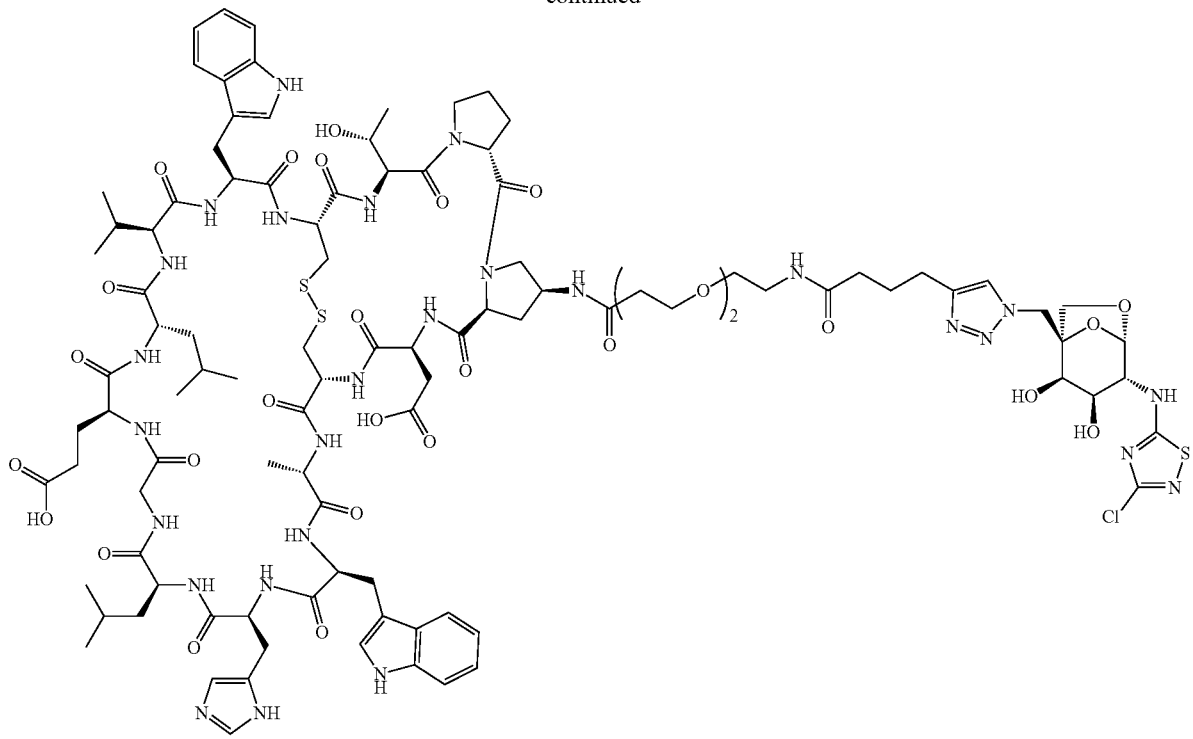

Step 1: THPTA (1.94 mg, 0.004 mmol) and CuSO₄ (0.14 mg, 0.001 mmol) were dissolved in water (0.5 mL) and then added to a solution of (1S,2R,3R,4R,5S)-1-(azidomethyl)-4-((3-chloro-1,2,4-thiadiazol-5-yl)amino)-6,8-dioxabicyclo[3.2.1]octane-2,3-diol (3 mg, 0.009 mmol) and 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(2-(hex-5-ynamido)ethoxy)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Intermediate 6, 15 mg, 0.009 mmol) in MeOH (10 mL). A freshly prepared solution of Na ascorbate (0.35 mg, 0.002 mmol) in water (0.5 mL) was added and the reaction mixture was stirred at 35° C. for 12 hours. The solvent was evaporated and the crude material was purified by prep-HPLC to afford 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(2-(4-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)methyl)-1H-1,2,3-triazol-4-yl)butanamido)ethoxy)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Compound 13, 2.6 mg, 13% yield). LC-MS (ESI) found: 1156 [M+2H]⁺. ¹H NMR (400 MHz, CD₃OD): δ 7.78 (s, 1H), 7.68 (d, J=8.4 Hz, 1H), 7.47 (d, J=7.6 Hz, 1H), 7.41 (s, 1H), 7.33 (s, 1H), 7.30 (d, J=8.0 Hz, 1H), 7.15 (s, 1H), 7.12 (d, J=7.8 Hz, 1H), 7.05 (t, J=7.6 Hz, 1H), 6.98 (t, J=7.2 Hz, 1H), 6.91 (s, 1H), 6.88-6.82 (m, 2H), 5.38 (s, 1H), 4.70-4.56 (m, 3H), 4.48 (s, 2H), 4.33 (d, J=45.2 Hz, 6H), 4.07 (dd, J=21.1, 9.4 Hz, 2H), 3.95 (s, 1H), 3.87-3.71 (m, 8H), 3.66 (s, 1H), 3.62 (s, 5H), 3.54 (t, J=5.7 Hz, 2H), 3.50-3.42 (m, 2H), 3.13 (d, J=1.7 Hz, 1H), 2.94 (d, J=65.8 Hz, 3H), 2.83-2.77 (m, 1H), 2.76-2.67 (m, 3H), 2.55 (s, 1H), 2.46 (t, J=6.0 Hz, 5H), 2.28-2.12 (m, 6H), 2.06-1.88 (m, 9H), 1.70 (d, J=81.3 Hz, 6H), 1.30 (s, 9H), 1.20-1.11 (m, 6H), 1.00-0.90 (m, 15H), 0.85 (d, J=6.7 Hz, 3H).

Preparation of Compound 14, 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(20-(1-(20-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)-17-oxo-4,7,10,13-tetraoxa-16-azaicosanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

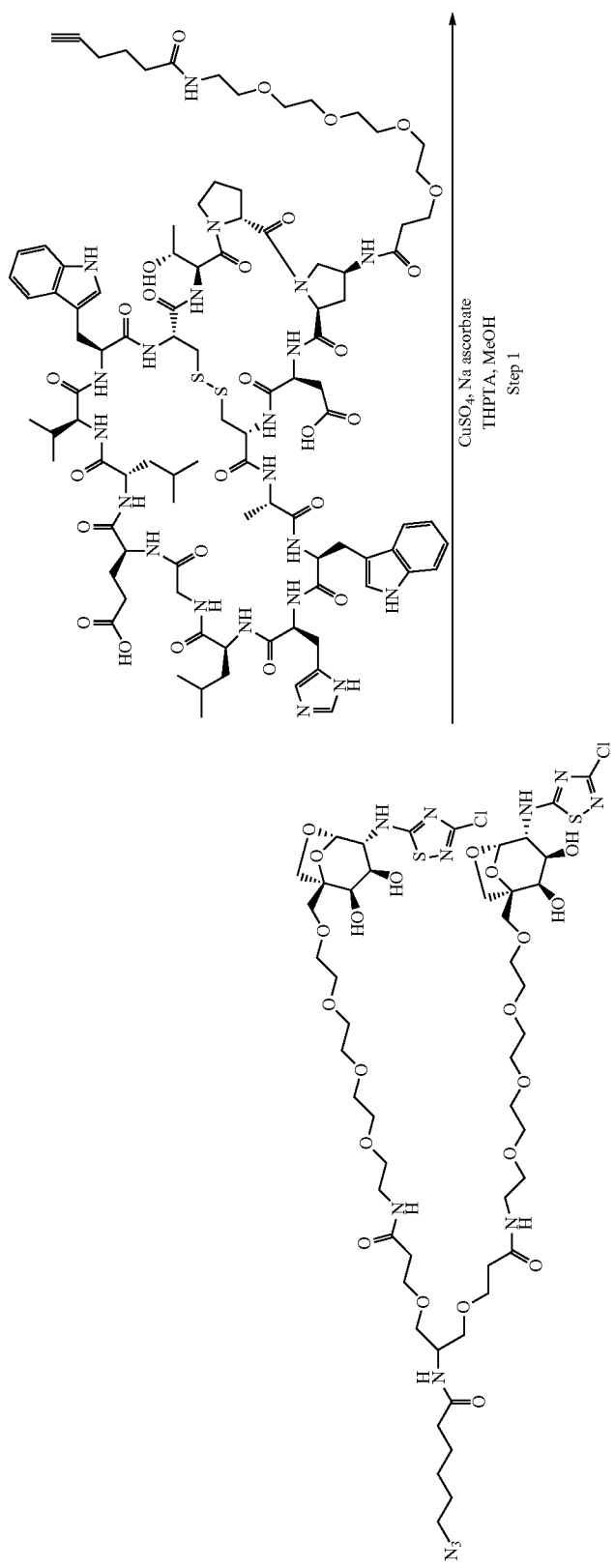

-continued
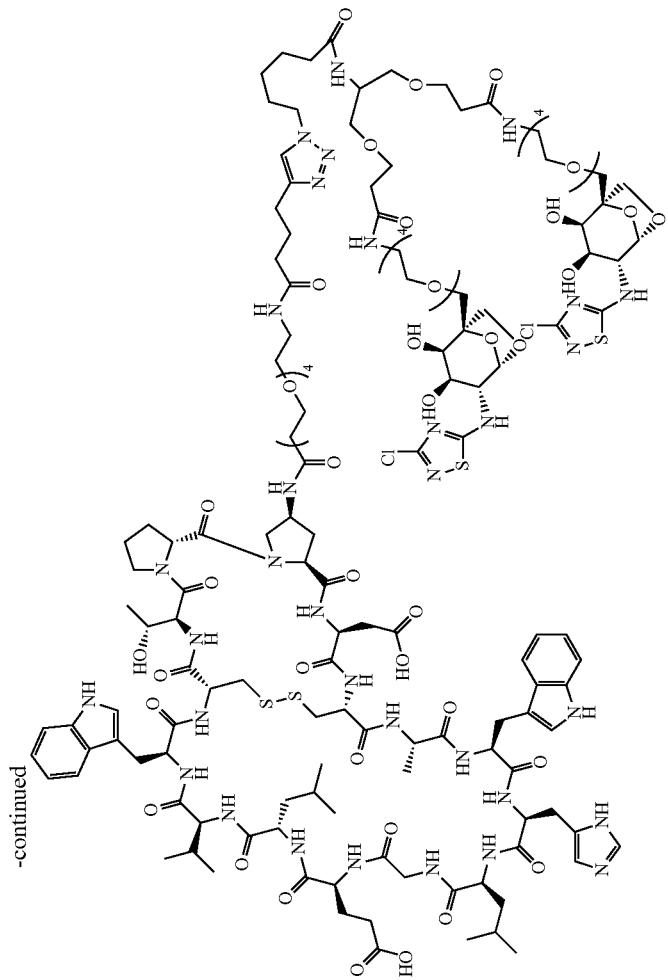

Step 1: THPTA (1.52 mg, 0.004 mmol) and CuSO₄ (0.56 mg, 0.004 mmol) were dissolved in water (0.5 mL) and then added to a solution of 3,3'-((2-(6-azidohexanamido)propane-1,3-diyl)bis(oxy))bis(N-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide) (A14, 9.5 mg, 0.007 mmol) and 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-11-((R)-1-hydroxyethyl)-23,32-diisobutyl-20-isopropyl-41-methyl-5,10,13,16,19,22,25,28,31,34,37,40,43,46,49-pentadecaoxo-2-(17-oxo-4,7,10,13-tetraoxa-16-azadocos-21-ynamido)octatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Intermediate 4, 15 mg, 0.007 mmol) in MeOH (10 mL). A freshly prepared solution of Na ascorbate (0.69 mg, 0.004 mmol) in water (0.5 mL) was added and the reaction mixture was stirred at 35° C. for 16 hours. Solvent was evaporated and the crude material was purified by prep-HPLC to afford 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(20-(1-(20-(1-((1S,2R,3R,4R,5S)-4-((3-chloro-1,2,4-thiadiazol-5-yl) amino)-2,3-dihydroxy-6,8-dioxabicyclo[3.2.1]octan-1-yl)-15-oxo-2,5,8,11,18-pentaoxa-14-azanonadecan-19-yl)-1-((1S,2R,3R,4R,5S)-4-((3-chloro-1,2,4-thiadiazol-5-yl) amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)-17-oxo-4,7,10,13-tetraoxa-16-azaicosanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Compound 14, 1.7 mg, 6.9% yield). LC-MS (ESI) found: 1125 [M+3H]$^{3+}$.

Preparation of Compound 15, 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(20-(1-(((1S,2R,3R,4R,5S)-4-((3-chloro-1,2,4-thiadiazol-5-yl) amino)-2,3-dihydroxy-6,8-dioxabicyclo[3.2.1]octan-1-yl)methyl)-1H-1,2,3-triazol-4-yl)-17-oxo-4,7,10,13-tetraoxa-16-azaicosanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

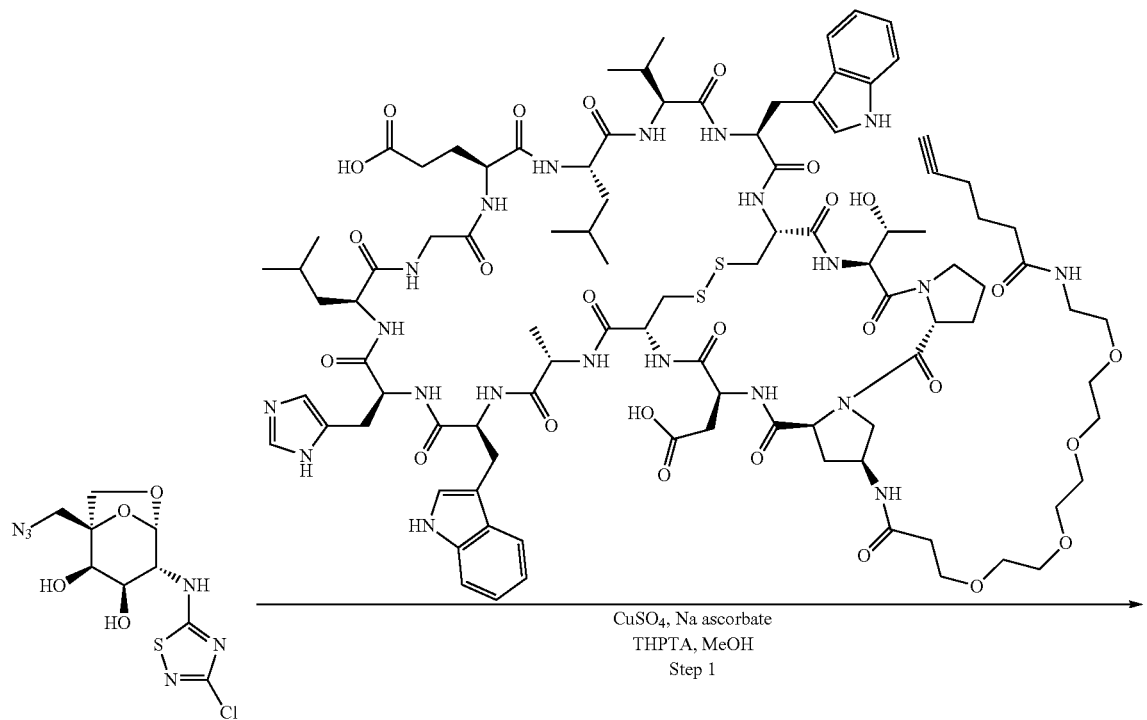

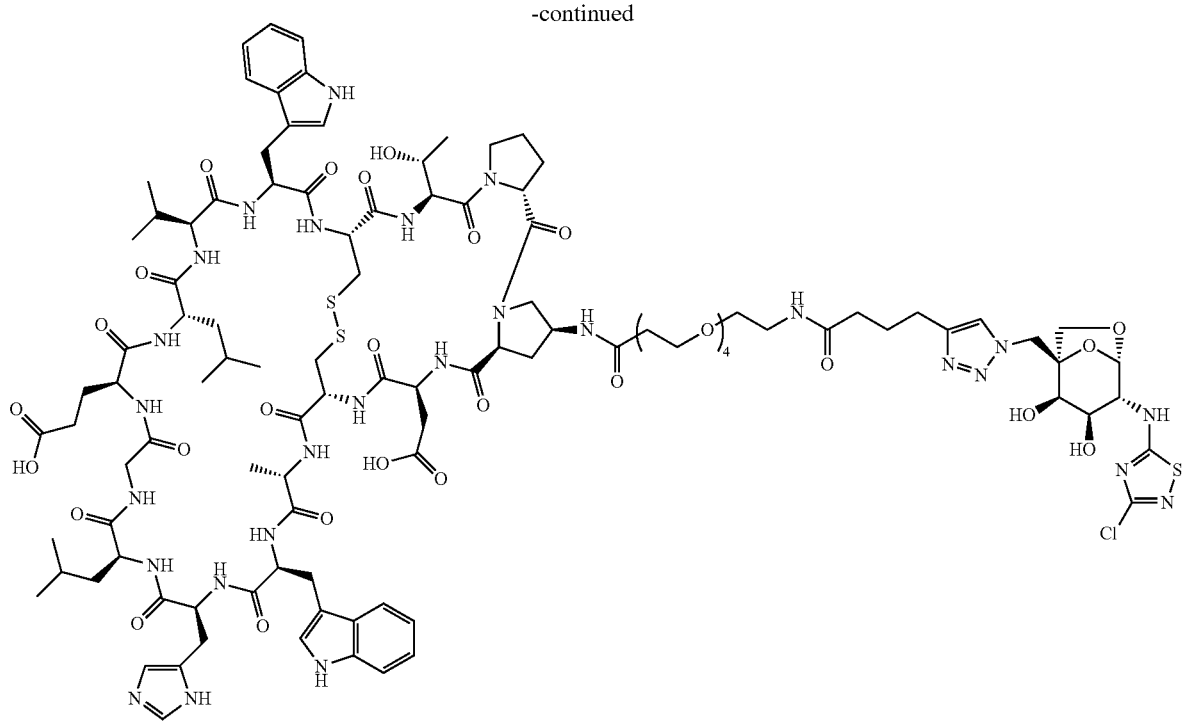

Step 1: THPTA (3.25 mg, 0.007 mmol) and CuSO₄ (0.24 mg, 0.002 mmol) were dissolved in water (0.5 mL) and then added to a solution of (1S,2R,3R,4R,5S)-1-(azidomethyl)-4-((3-chloro-1,2,4-thiadiazol-5-yl)amino)-6,8-dioxabicyclo[3.2.1]octane-2,3-diol (5 mg, 0.015 mmol) and 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-11-((R)-1-hydroxyethyl)-23,32-diisobutyl-20-isopropyl-41-methyl-5,10,13,16,19,22,25,28,31,34,37,40,43,46,49-pentadecaoxo-2-(17-oxo-4,7,10,13-tetraoxa-16-azadocos-21-ynamido)octatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (30.80 mg, 0.015 mmol) in MeOH (10 mL). A freshly prepared solution of Na ascorbate (0.59 mg, 0.002 mmol) in water (0.5 mL) was added and the reaction mixture was stirred at 35° C. for 16 hours. Solvent was evaporated and the crude material was purified by prep-HPLC to afford 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(20-(1-(((1S,2R,3R,4R,5S)-4-((3-chloro-1,2,4-thiadiazol-5-yl)amino)-2,3-dihydroxy-6,8-dioxabicyclo[3.2.1]octan-1-yl)methyl)-1H-1,2,3-triazol-4-yl)-17-oxo-4,7,10,13-tetraoxa-16-azaicosanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano) dipyrrolo[1,2-a:1',2'-d][1,4,7,10,13,16,19,22,25,28,31,34,37,40,43]pentadecaazacyclopentatetracontin-26-yl)propanoic acid (Compound 15, 4.7 mg, 13% yield). LC-MS (ESI) found: 1200 [M+2H]²⁺. ¹H NMR (400 MHz, CD₃OD): δ 7.78 (s, 1H), 7.66 (s, 1H), 7.48 (d, J=7.8 Hz, 1H), 7.41 (s, 1H), 7.34 (s, 1H), 7.30 (d, J=7.8 Hz, 1H), 7.19-7.09 (m, 2H), 7.05 (t, J=7.8 Hz, 1H), 6.98 (t, J=7.2 Hz, 1H), 6.90 (d, J=7.5 Hz, 1H), 6.84 (s, 1H), 5.38 (s, 1H), 4.95-4.86 (m, 5H), 4.77 (dd, J=13.6, 2.6 Hz, 3H), 4.71-4.56 (m, 3H), 4.54-4.43 (m, 2H), 4.42-4.22 (m, 5H), 4.08 (t, J=13.1 Hz, 2H), 3.93 (dd, J=10.9, 6.0 Hz, 1H), 3.88-3.66 (m, 8H), 3.63 (s, 13H), 3.53 (t, J=5.5 Hz, 2H), 3.51-3.41 (m, 2H), 3.35 (t, J=5.5 Hz, 3H), 3.29-3.10 (m, 6H), 3.07-2.89 (m, 3H), 2.87-2.69 (m, 4H), 2.63-2.05 (m, 14H), 2.03-1.90 (m, 6H), 1.88-1.49 (m, 6H), 1.15 (dd, J=13.8, 7.2 Hz, 6H), 1.02-0.90 (m, 12H), 0.85 (d, J=6.5 Hz, 3H).

Preparation of Compound 16, 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxy methyl)-2-(20-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-17-oxo-4,7,10,13-tetraoxa-16-azaicosanamido)-11-((R)-1-hydroxyethyl)-23,32-diisobutyl-20-isopropyl-41-methyl-5,10,13,16,19,22,25,28,31,34,37,40,43,46,49-pentadecaoxo octatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

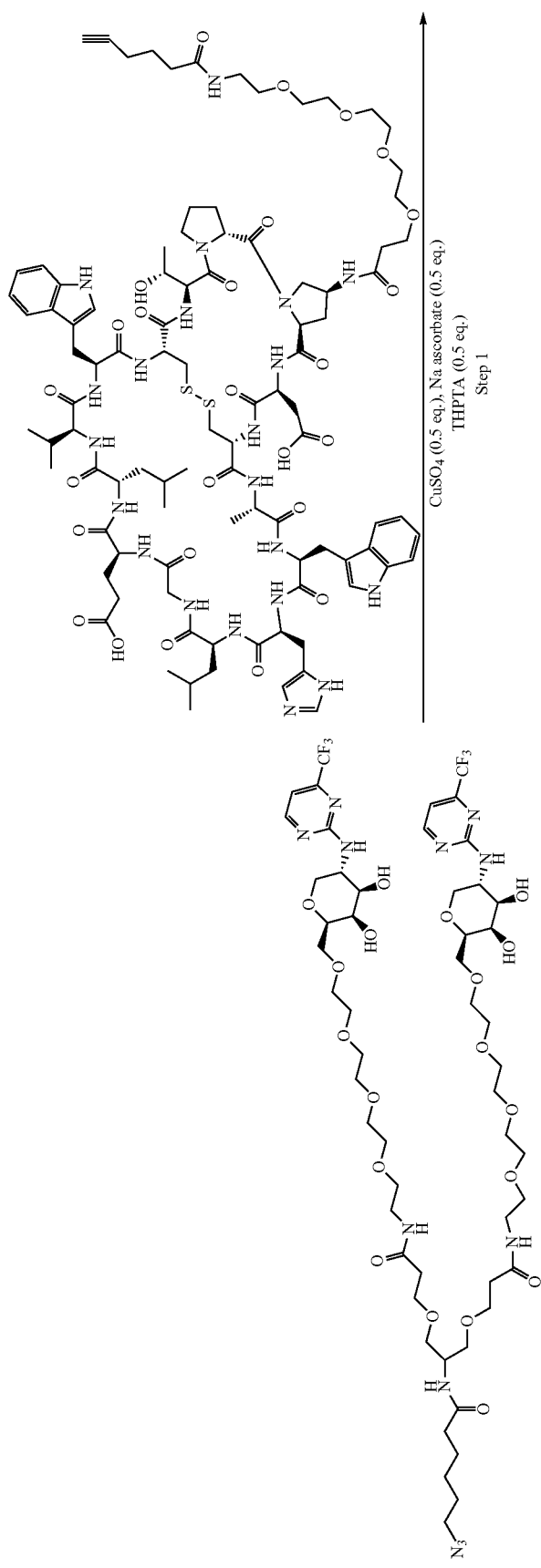

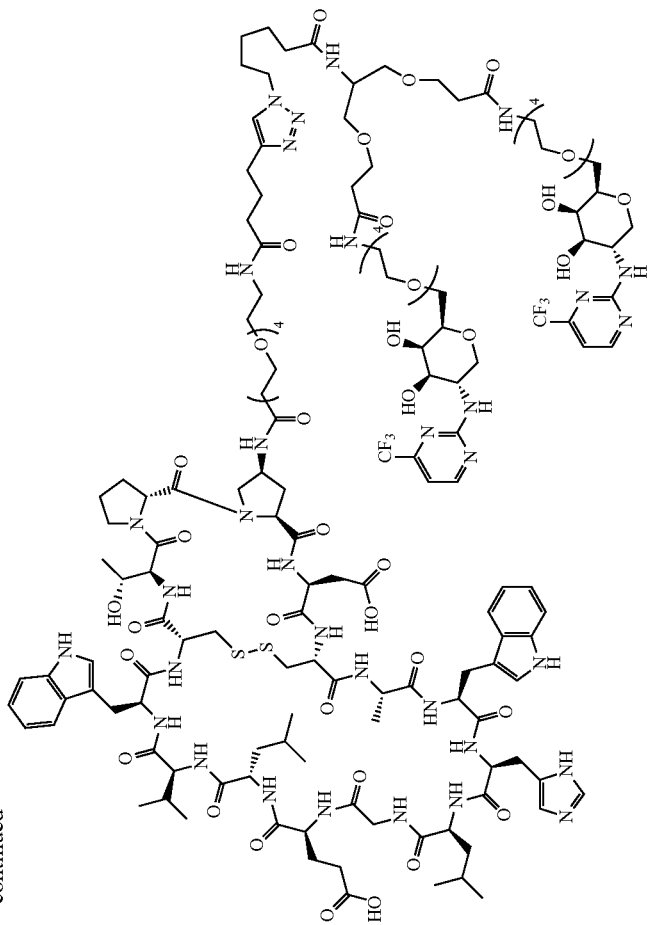

Step 1: To a solution of 3,3'-((2-(6-azidohexanamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (15 mg, 0.01 mmol) and 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-11-((R)-1-hydroxyethyl)-23,32-diisobutyl-20-isopropyl-41-methyl-5,10,13,16,19,22,25,28,31,34,37,40,43,46,49-pentadecaoxo-2-(17-oxo-4,7,10,13-tetraoxa-16-azadocos-21-ynamido)octatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Intermediate 4, 25 mg, 0.01 mmol) in MeOH (5 mL) were added CuSO₄ (2 mg), THPTA (3 mg) in H₂O (0.1 mL) and Na ascorbate (2 mg) in H₂O (0.1 mL). The mixture was stirred at 35° C. overnight, then concentrated. The residue was purified by flash column to give 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(20-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-17-oxo-4,7,10,13-tetraoxa-16-azaicosanamido)-11-((R)-1-hydroxyethyl)-23,32-diisobutyl-20-isopropyl-41-methyl-5,10,13,16,19,22,25,28,31,34,37,40,43,46,49-pentadecaoxo-octatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Compound 16, 8.2 mg, 20% yield) as white solid. LC-MS (ESI) found: 1125 [M+3H]³⁺. ¹H NMR (400 MHz, CD₃OD): δ 8.72 (s, 1H), 8.69-8.64 (m, 1H), 8.50 (d, J=4.8 Hz, 2H), 7.76 (s, 1H), 7.69-7.64 (m, 1H), 7.47 (s, 1H), 7.41 (s, 1H), 7.33 (d, J=9.6 Hz, 1H), 7.30 (d, J=8.1 Hz, 1H), 7.17-7.10 (m, 2H), 7.04 (d, J=8.1 Hz, 1H), 6.98 (d, J=7.7 Hz, 1H), 6.89 (s, 1H), 6.88 (s, 1H), 6.85 (s, 1H), 4.35 (t, J=7.1 Hz, 7H), 4.13-4.03 (m, 6H), 3.91 (d, J=2.8 Hz, 2H), 3.74 (d, J=6.0 Hz, 2H), 3.71-3.66 (m, 14H), 3.64-3.58 (m, 46H), 3.53 (t, J=5.3 Hz, 7H), 3.45 (dd, J=12.7, 6.9 Hz, 4H), 3.36 (t, J=4.6 Hz, 8H), 3.18-3.12 (m, 4H), 2.70 (d, J=9.9 Hz, 3H), 2.44 (t, J=6.6 Hz, 9H), 2.23 (dt, J=19.1, 7.5 Hz, 6H), 2.01-1.82 (m, 10H), 1.63 (s, 5H), 1.49 (s, 3H), 1.46 (d, J=2.0 Hz, 9H), 1.31 (s, 5H), 1.14 (d, J=6.1 Hz, 5H), 1.00-0.94 (m, 5H), 0.97-0.89 (m, 9H), 0.85 (d, J=6.7 Hz, 3H).

Preparation of Compound 17, 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(2-(4-(1-(20-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)butanamido)ethoxy)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

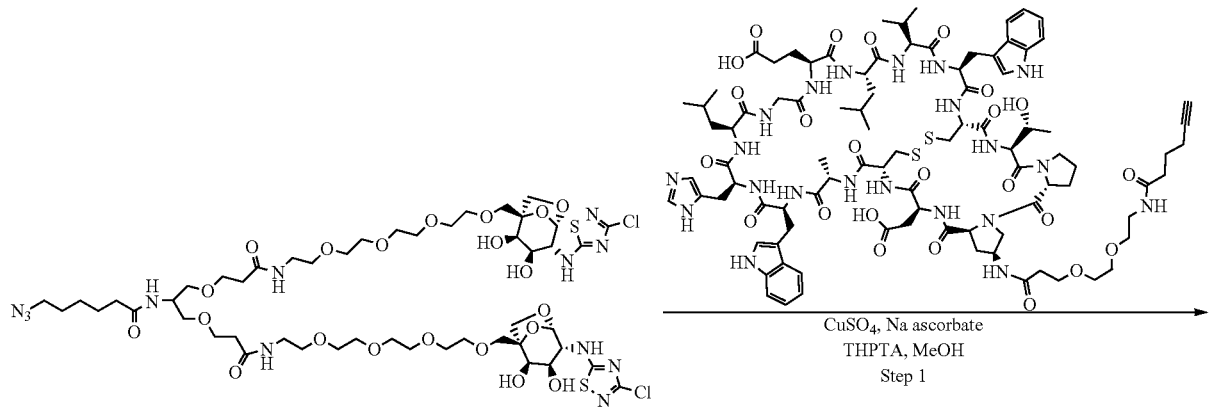

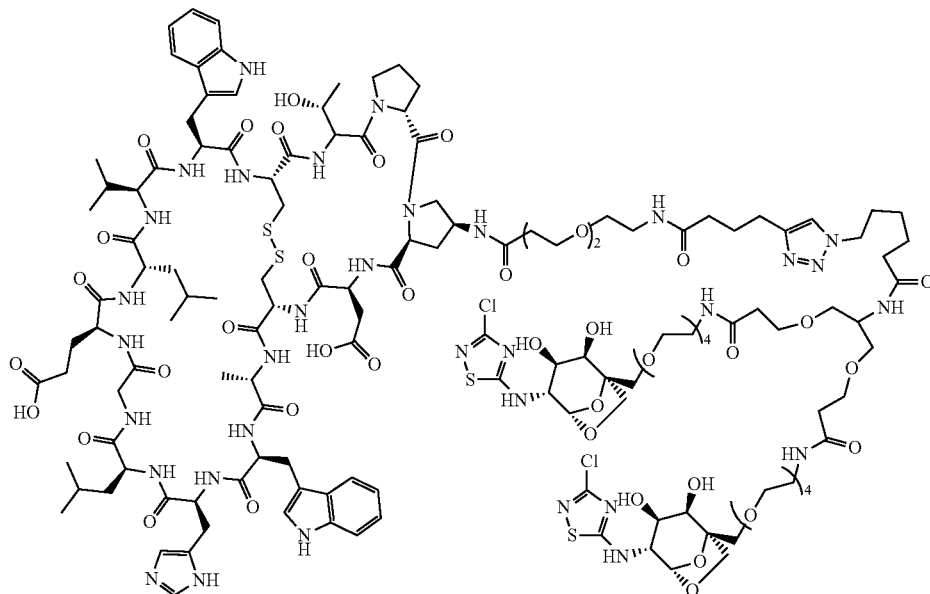

Step 1: THPTA (0.51 mg, 0.01 mmol) and CuSO₄ (0.04 mg, 0.0002 mmol) were dissolved in water (0.5 mL). Then the mixture was added into a solution of 3,3'-((2-(6-azido-hexanamido)propane-1,3-diyl)bis(oxy))bis(N-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide) (A14, 3.1 mg, 0.002 mmol) and 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(2-(hex-5-ynamido)ethoxy)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (5 mg, 0.002 mmol) in MeOH (5 mL). A freshly prepared solution of Na ascorbate (0.09 mg, 0.0004 mmol) in water (0.5 mL) was added and the reaction mixture was stirred at 35° C. for 16 hours. Solvent was evaporated and the crude material was purified by prep-HPLC (Method A) to afford 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(3-(2-(2-(4-(1-(20-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)butanamido)ethoxy)ethoxy)propanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Compound 17, 4.7 mg, 60% yield). LC-MS (ESI) found: 1642 [M+2H]²⁺. ¹H NMR (400 MHz, CD₃OD): δ 7.75 (s, 1H), 7.69 (d, J=9.4 Hz, 1H), 7.46 (s, 1H), 7.35 (s, 1H), 7.30 (d, J=8.0 Hz, 1H), 7.13 (d, J=9.7 Hz, 2H), 7.05 (t, J=7.7 Hz, 1H), 6.98 (t, J=7.3 Hz, 1H), 6.94-6.83 (m, 3H), 5.38 (s, 2H), 4.66 (d, J=6.7 Hz, 1H), 4.59 (dd, J=9.1, 4.3 Hz, 1H), 4.49 (s, 1H), 4.36 (dd, J=14.1, 7.0 Hz, 4H), 4.26 (s, 1H), 4.15-3.96 (m, 6H), 3.92-3.73 (m, 12H), 3.71-3.58 (m, 40H), 3.57-3.49 (m, 7H), 3.46 (dt, J=9.7, 4.3 Hz, 5H), 3.36 (dd, J=10.0, 4.9 Hz, 7H), 3.24 (d, J=16.8 Hz, 4H), 3.03 (dd, J=42.9, 32.9 Hz, 4H), 2.83 (s, 1H), 2.72 (t, J=7.5 Hz, 3H), 2.63-2.39 (m, 11H), 2.37-2.09 (m, 10H), 2.07-1.67 (m, 13H), 1.62 (dd, J=15.5, 7.8 Hz, 4H), 1.38-1.26 (m, 4H), 1.15 (d, J=6.0 Hz, 6H), 1.01-0.80 (m, 18H).

Preparation of Compound 18, (S)-2-((S)-2-((1H-imidazol-5-yl)methyl)-23-(1-(((2R,3R,4R,5S)-3,4-dihydroxy-5-((4-(trifluoromethyl)pyrimidin-2-yl)amino)tetrahydro-2H-pyran-2-yl)methyl)-1H-1,2,3-triazol-4-yl)-4,20-dioxo-7,10,13,16-tetraoxa-3,19-diazatricosanamido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide fied by prep-HPLC to give (S)-2-((S)-2-((1H-imidazol-5-yl)methyl)-23-(1-(((2R,3R,4R,5S)-3,4-dihydroxy-5-((4-(trifluoromethyl)pyrimidin-2-yl)amino)tetrahydro-2H-pyran-2-yl)methyl)-1H-1,2,3-triazol-4-yl)-4,20-dioxo-7,10,13,16-tetraoxa-3,19-diazatricosanamido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (Compound 18, 8 mg, 11% yield) as white solid. LC-MS (ESI) found: 632 [M+4H]$^{4+}$. $^1$H NMR (400 MHz, CD$_3$OD): δ 8.51 (d, J=4.5 Hz, 1H), 8.35 (s, 4H), 7.98

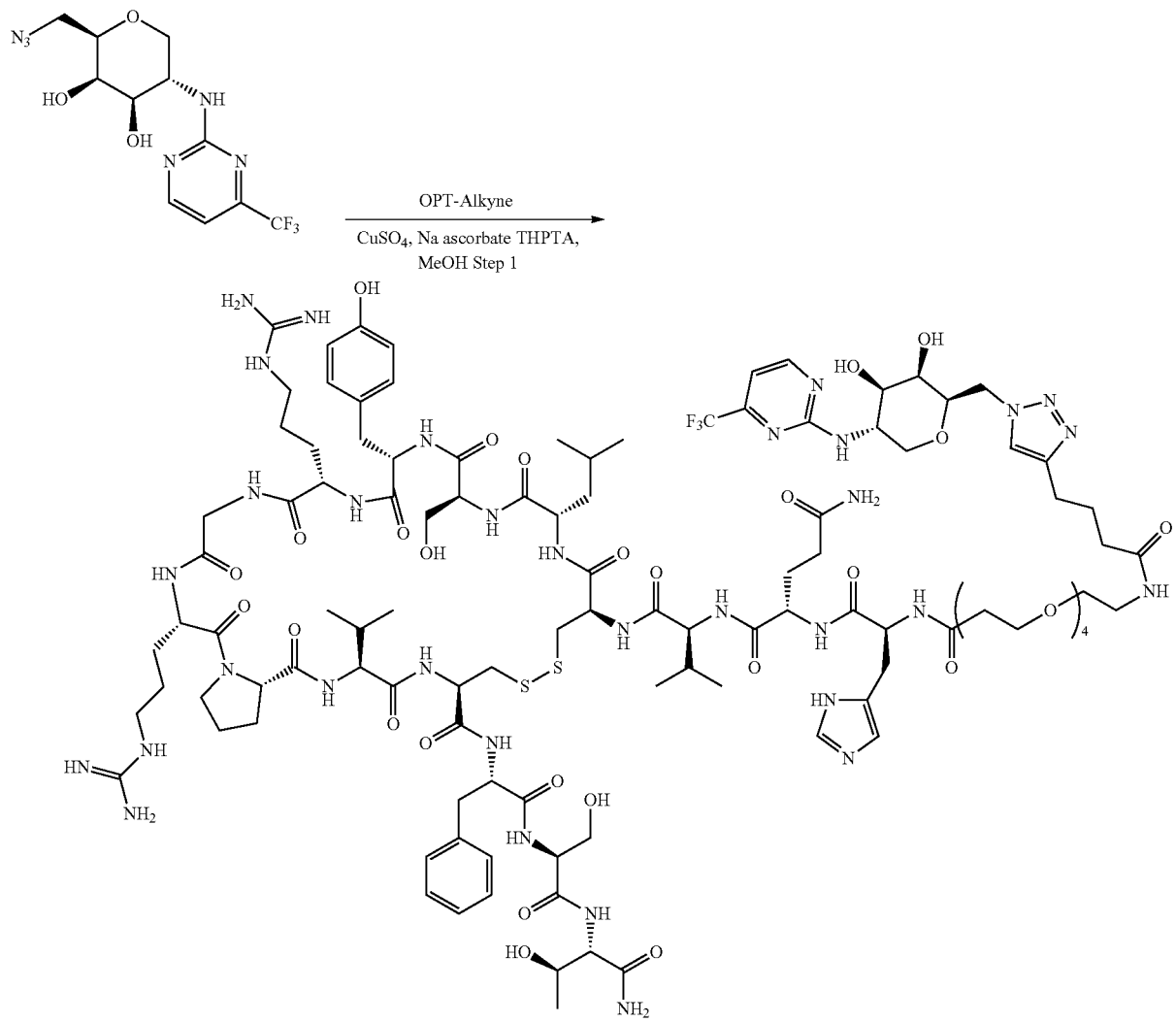

Step 1: THPTA (6.5 mg) and CuSO$_4$ (0.5 mg) were dissolved in water (0.1 mL). The mixture was added to a solution of (2R,3R,4R,5S)-2-(azidomethyl)-5-((4-(trifluoromethyl)pyrimidin-2-yl)amino)tetrahydro-2H-pyran-3,4-diol (10 mg) and OPT-alkyne (59 mg) in MeOH (3 mL). A freshly prepared solution of Na ascorbate (1.2 mg) in water (0.1 mL) was added. The reaction was stirred overnight. The resulting mixture was filtered. The crude product was puri- (s, 1H), 7.77 (s, 1H), 7.10 (dt, J=13.3, 5.8 Hz, 8H), 6.90 (d, J=4.9 Hz, 1H), 6.74 (d, J=8.4 Hz, 2H), 5.79 (dd, J=43.7, 10.3 Hz, 2H), 5.27-5.08 (m, 3H), 4.61 (d, J=5.6 Hz, 2H), 4.50 (s, 2H), 4.42-4.33 (m, 3H), 4.18 (d, J=17.2 Hz, 1H), 4.10-4.05 (m, 1H), 3.95-3.67 (m, 11H), 3.62-3.50 (m, 17H), 3.24 (t, J=7.2 Hz, 2H), 3.15-2.81 (m, 12H), 2.70 (dd, J=15.9, 8.7 Hz, 3H), 2.51 (d, J=5.4 Hz, 2H), 2.32-2.15 (m, 6H), 1.96 (ddd, J=21.1, 13.1, 5.9 Hz, 12H), 1.74 (s, 6H), 1.36-1.19 (m, 8H), 0.97 (ddd, J=46.2, 22.9, 5.2 Hz, 21H). $^{19}$F NMR (377 MHz, CD$_3$OD): δ −72.28 (s), −76.92 (s).

Preparation of Compound 19, (S)-2-((S)-2-((1H-imidazol-5-yl)methyl)-23-(1-(20-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)-4,20-dioxo-7,10,13,16-tetraoxa-3,19-diazatricosanamido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide solution of 3,3'-((2-(6-azidohexanamido)propane-1,3-diyl)bis(oxy))bis(N-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide) (A14, 110 mg) and OPT-alkyne (140 mg) in MeOH (5 mL). A freshly prepared solution of Na ascorbate (3.3 mg) in water (0.25 mL) was added. The reaction was stirred overnight. The resulting mixture was filtered. The crude product was purified by prep-HPLC to give (S)-2-((S)-2-((1H-imidazol-5-yl)methyl)-23-(1-(20-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)-4,20-dioxo-7,10,13,16-tetraoxa-3,19-diazatricosanamido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,

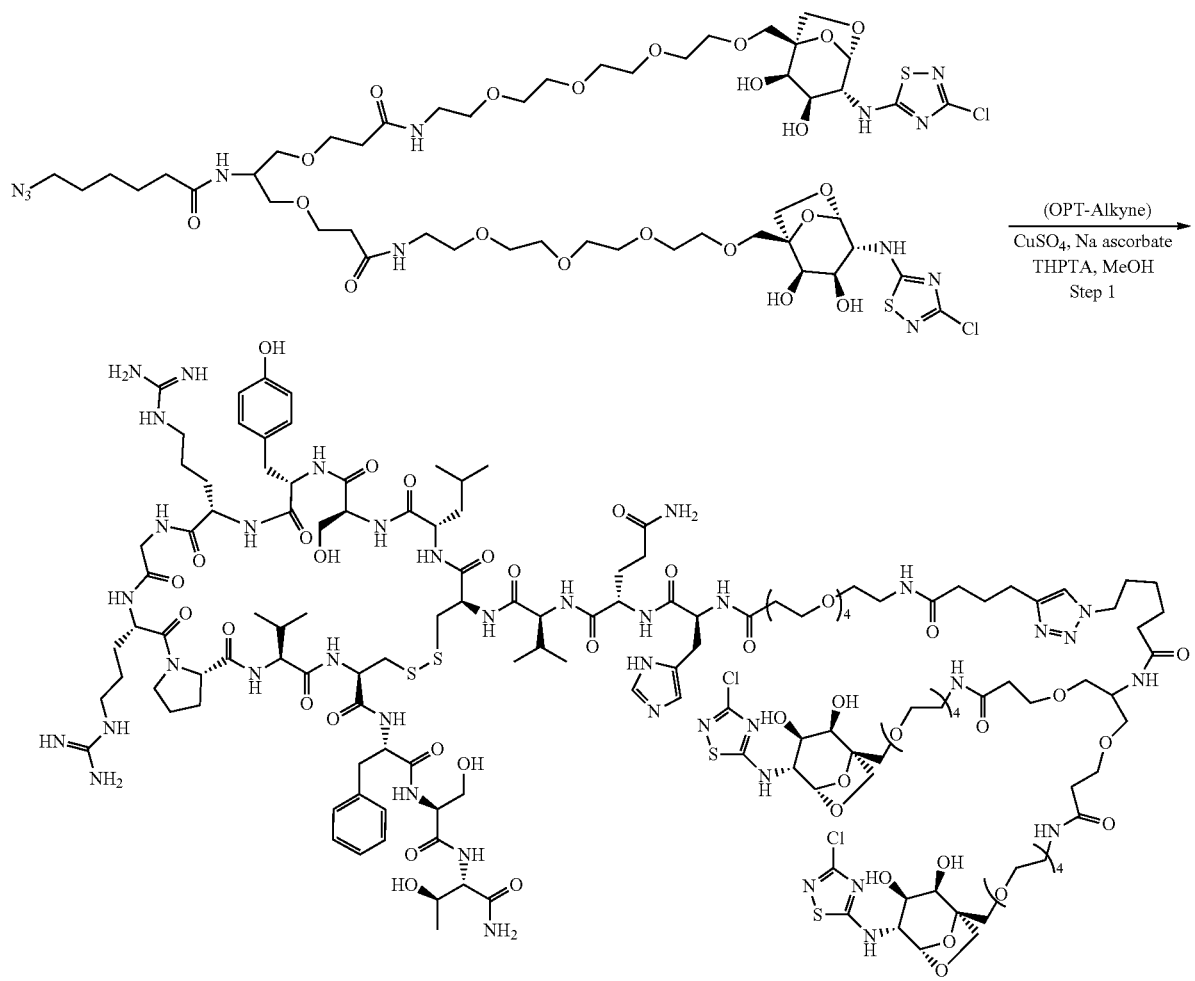

Step 1: THPTA (18.3 mg) and CuSO$_4$ (1.3 mg) were dissolved in water (0.25 mL). The mixture was added to a 24,27,30-nonaoxotriacontahydro-1H,10H-pyrrolo[2,1-j][1,2]dithia[5,8,11,14,17,20,23,26,29]

nonaazacyclodotriacontin-11-yl)amino)-3-methyl-1-oxobutan-2-yl)pentanediamide (Compound 19, 13 mg, 4% yield) as white solid. LC-MS (ESI) found: 701 [M+5H]$^{5+}$. $^1$H NMR (400 MHz, CD$_3$OD): δ 8.48 (s, 2H), 7.76 (s, 1H), 7.65 (s, 1H), 7.16-7.07 (m, 7H), 6.93 (s, 1H), 6.74 (d, J=8.4 Hz, 2H), 5.76 (d, J=34.0 Hz, 2H), 5.39 (s, 2H), 5.24-5.06 (m, 3H), 4.94 (s, 2H), 4.75 (s, 6H), 4.44-4.33 (m, 6H), 4.29 (d, J=8.3 Hz, 1H), 4.19 (d, J=17.0 Hz, 1H), 4.10 (d, J=5.3 Hz, 1H), 4.00 (d, J=9.6 Hz, 2H), 3.94 (d, J=4.0 Hz, 2H), 3.83 (d, J=8.1 Hz, 3H), 3.71-3.54 (m, 58H), 3.46 (dd, J=9.6, 3.7 Hz, 4H), 3.37 (dd, J=10.0, 5.3 Hz, 7H), 3.23 (s, 2H), 3.13 (d, J=5.0 Hz, 4H), 2.98 (dd, J=26.6, 11.0 Hz, 8H), 2.72 (s, 2H), 2.46 (dd, J=13.9, 8.0 Hz, 6H), 2.22 (dt, J=24.6, 7.5 Hz, 8H), 2.02-1.89 (m, 12H), 1.72 (s, 4H), 1.68-1.59 (m, 4H), 1.32 (s, 3H), 1.23 (d, J=6.2 Hz, 4H), 1.03-0.94 (m, 12H), 0.87 (t, J=5.9 Hz, 9H).

Preparation of Compound 20, (S)-2-((S)-34-((1H-imidazol-5-yl)methyl)-1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22,32-trioxo-2,5,8,11,18,24,27,30-octaoxa-14,21,33-triazapentatriacontan-35-amido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide

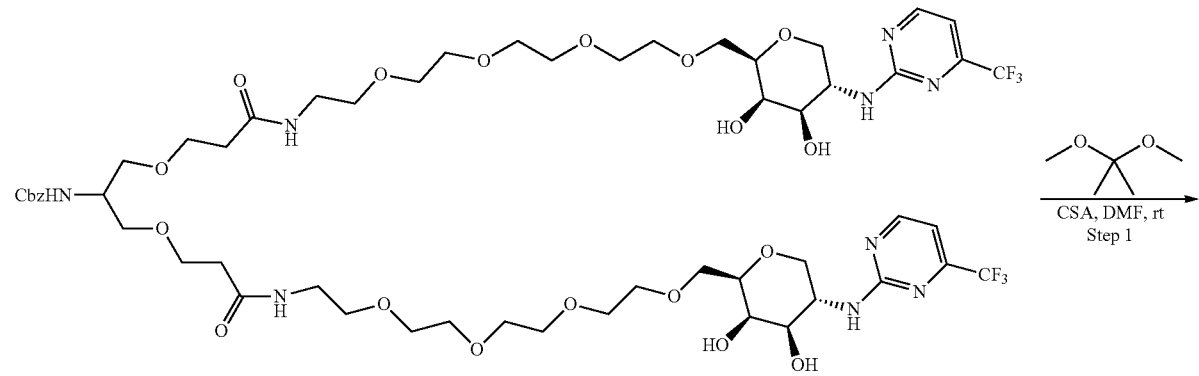

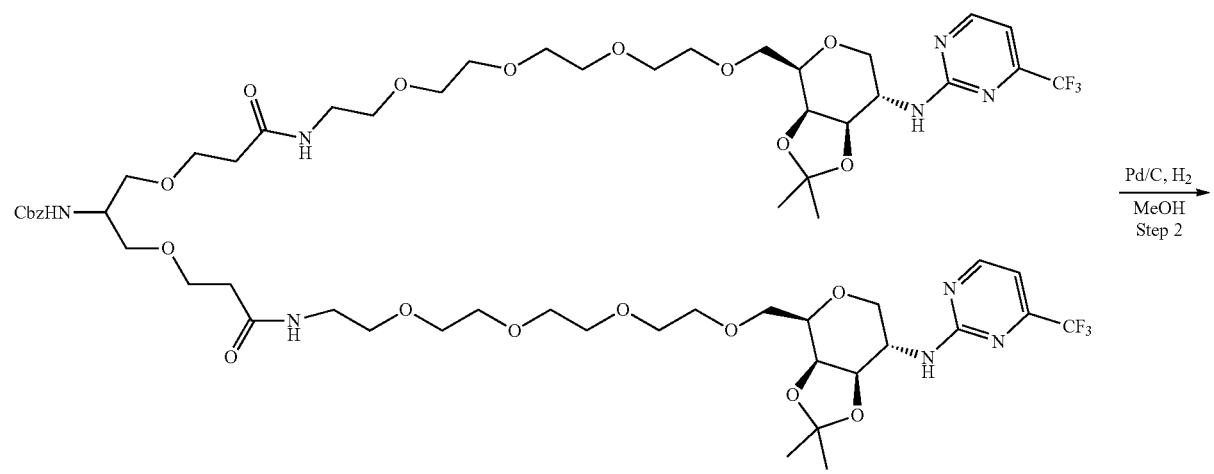

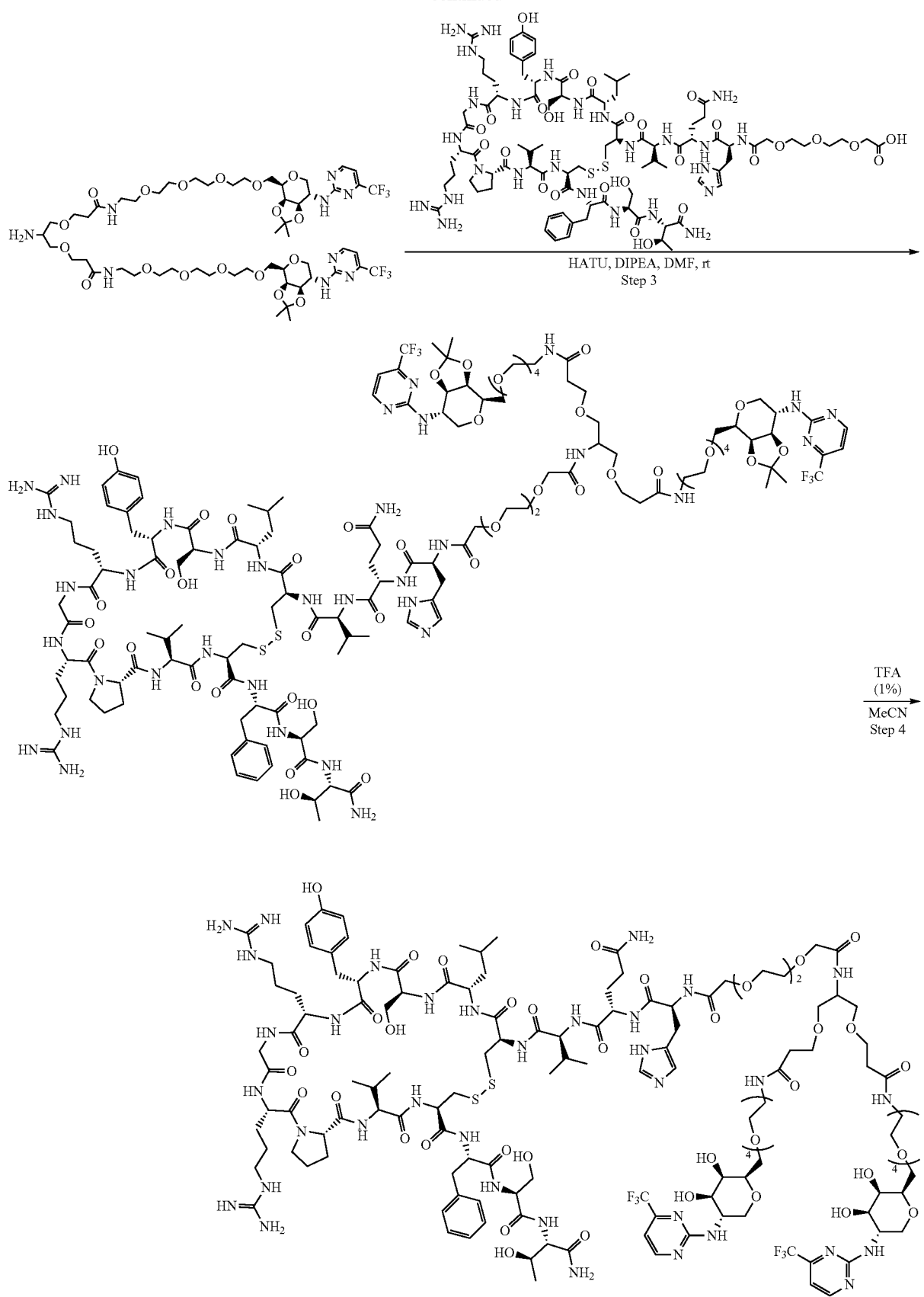

Step 1: A solution of benzyl (1,39-bis((2R,3R,4R,5S)-3,4-dihydroxy-5-((4-(trifluoromethyl)pyrimidin-2-yl)amino)tetrahydro-2H-pyran-2-yl)-15,25-dioxo-2,5,8,11,18,22,29,32,35,38-decaoxa-14,26-diazanonatriacontan-20-yl)carbamate (400 mg, 0.31 mmol) and CSA (7.0 mg, 0.03 mmol) in DMF (5 mL) was added 2,2-dimethoxypropane (161.1 mg, 1.55 mmol) at rt. The reaction mixture was stirred at rt for overnight. The resulting mixture was diluted with EA (20 mL), washed with $H_2O$ (5 mL×2) and brine (5 mL), dried over $Na_2SO_4$. The organic layer was separated and concentrated in vacuo. The crude product was purified by flash chromatography (MeOH in DCM) to give benzyl (1,39-bis((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15,25-dioxo-2,5,8,11,18,22,29,32,35,38-decaoxa-14,26-diazanonatriacontan-20-yl)carbamate (300 mg, 71% yield) as white solid. LC-MS (ESI) found: 1382 $[M+H]^+$.

Step 2: A solution of benzyl (1,39-bis((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15,25-dioxo-2,5,8,11,18,22,29,32,35,38-decaoxa-14,26-diazanonatriacontan-20-yl)carbamate (200 mg, 0.15 mmol) in MeOH (5 mL) was added Pd/C (20 mg, 10% wt., 60% wet) at rt and the reaction mixture was stirred at rt for overnight. The mixture concentrated fitter and reduced pressure to give a crude product. The crude product was purified by flash chromatography (MeOH in DCM) to give 3,3'-((2-aminopropane-1,3-diyl)bis(oxy))bis(N-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-2,5,8,11-tetraoxatridecan-13-yl)propanamide) (150 mg, 83% yield) as white solid. LC-MS (ESI) found: 1247 $[M+H]^+$.

Step 3: To a solution of (13S,16S,19S)-13-((1H-imidazol-5-yl)methyl)-19-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)carbamoyl)-16-(3-amino-3-oxopropyl)-20-methyl-11,14,17-trioxo-3,6,9-trioxa-12,15,18-triazahenicosanoic acid (69 mg, 0.029 mmol) in DMF (2 mL) was added HATU (13 mg, 0.035 mmol), DIEA (0.029 mL, 0.173 mmol) at 0° C. The reaction was stirred at 0° C. for 30 min. 3,3'-((2-aminopropane-1,3-diyl)bis(oxy))bis(N-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-2,5,8,11-tetraoxatridecan-13-yl)propanamide) (40 mg, 0.032 mmol) was added, and the mixture was stirred at rt for 16 h. The mixture was purified by prep-HPLC to give (S)-2-((S)-34-((1H-imidazol-5-yl)methyl)-1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22,32-trioxo-2,5,8,11,18,24,27,30-octaoxa-14,21,33-triazapentatriacontan-35-amido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (25 mg, 26% yield). LC-MS (ESI) found: 822 $[M+4H]^{4+}$.

Step 4: (S)-2-((S)-34-((1H-imidazol-5-yl)methyl)-1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22,32-trioxo-2,5,8,11,18,24,27,30-octaoxa-14,21,33-triazapentatriacontan-35-amido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (20 mg, 0.006 mmol) was dissolved in TFA/MeCN solution (2 mL, 1% wt.). The reaction was stirred at room temperature for 18 h. The reaction was concentrated in vacuo. The residue was purified by prep-HPLC to afford the title compound (S)-2-((S)-34-((1H-imidazol-5-yl)methyl)-1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22,32-trioxo-2,5,8,11,18,24,27,30-octaoxa-14,21,33-triazapentatriacontan-35-amido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (Compound 20, 6 mg, 31% yield). LC-MS (ESI) found: 802 $[M+4H]^{4+}$. $^1$H NMR (400 MHz, MeOD): δ 8.81 (d, J=1.2 Hz, 1H), 8.51 (d, J=4.9 Hz, 2H), 7.38 (s, 1H), 7.11 (ddd, J=18.2, 14.7, 8.3 Hz, 7H), 6.89 (d, J=4.9 Hz, 2H), 6.74 (d, J=8.5 Hz, 2H), 5.74 (d, J=28.6 Hz, 2H), 5.12 (d, J=6.3 Hz, 2H), 5.03 (d, J=8.1 Hz, 1H), 4.94 (d, J=6.4 Hz, 1H), 4.77-4.65 (m, 3H), 4.48 (d, J=2.8 Hz, 1H), 4.36 (d, J=9.0 Hz, 4H), 4.29-4.16 (m, 3H), 4.14-3.98 (m, 6H), 3.91 (t, J=6.4 Hz, 3H), 3.83 (d, J=7.7 Hz, 2H), 3.71-3.59 (m, 42H), 3.51 (ddd, J=9.4, 8.1, 3.6 Hz, 11H), 3.37 (t, J=5.5 Hz, 5H), 3.25-3.12 (m, 6H), 3.05-2.85 (m, 7H), 2.78 (t, J=12.5 Hz, 2H), 2.67 (d, J=12.0 Hz, 1H), 2.45 (t, J=6.1 Hz, 4H), 2.18 (dd, J=29.7, 22.2 Hz, 4H), 2.07-1.84 (m, 9H), 1.69 (t, J=27.4 Hz, 7H), 1.30 (s, 4H), 1.20 (d, J=6.4 Hz, 4H), 1.05-0.92 (m, 10H), 0.90-0.80 (m, 9H).

Preparation of Compound 21, (S)-3-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(2-carboxyethyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)carbamoyl)-24-(1-(20-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)-5,21-dioxo-8,11,14,17-tetraoxa-4,20-diazatetracosanoic acid The crude product was purified by prep-HPLC to give (S)-3-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(2-carboxyethyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)carbamoyl)-24-(1-(20-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15-oxo-2,5,8,11,18-pentaoxa-14-azanonadecan-19-yl)-1-((1S,2R,3R,4R,5S)-4-((3-chloro-1,2,4-thiadiazol-5-yl)amino)-2,3-dihydroxy-6,8-dioxabicyclo[3.2.1]octan-1-yl)-15,22-dioxo-2,5,8,11,18-pentaoxa-14,21-diazaheptacosan-27-yl)-1H-1,2,3-triazol-4-yl)-5,21-dioxo-8,11,14,17-tetraoxa-4,20-diazatetracosanoic acid (Compound 21, 14 mg, 28% yield) as white solid. LC-MS (ESI) found: 1591 [M+2H]$^{2+}$. $^1$H

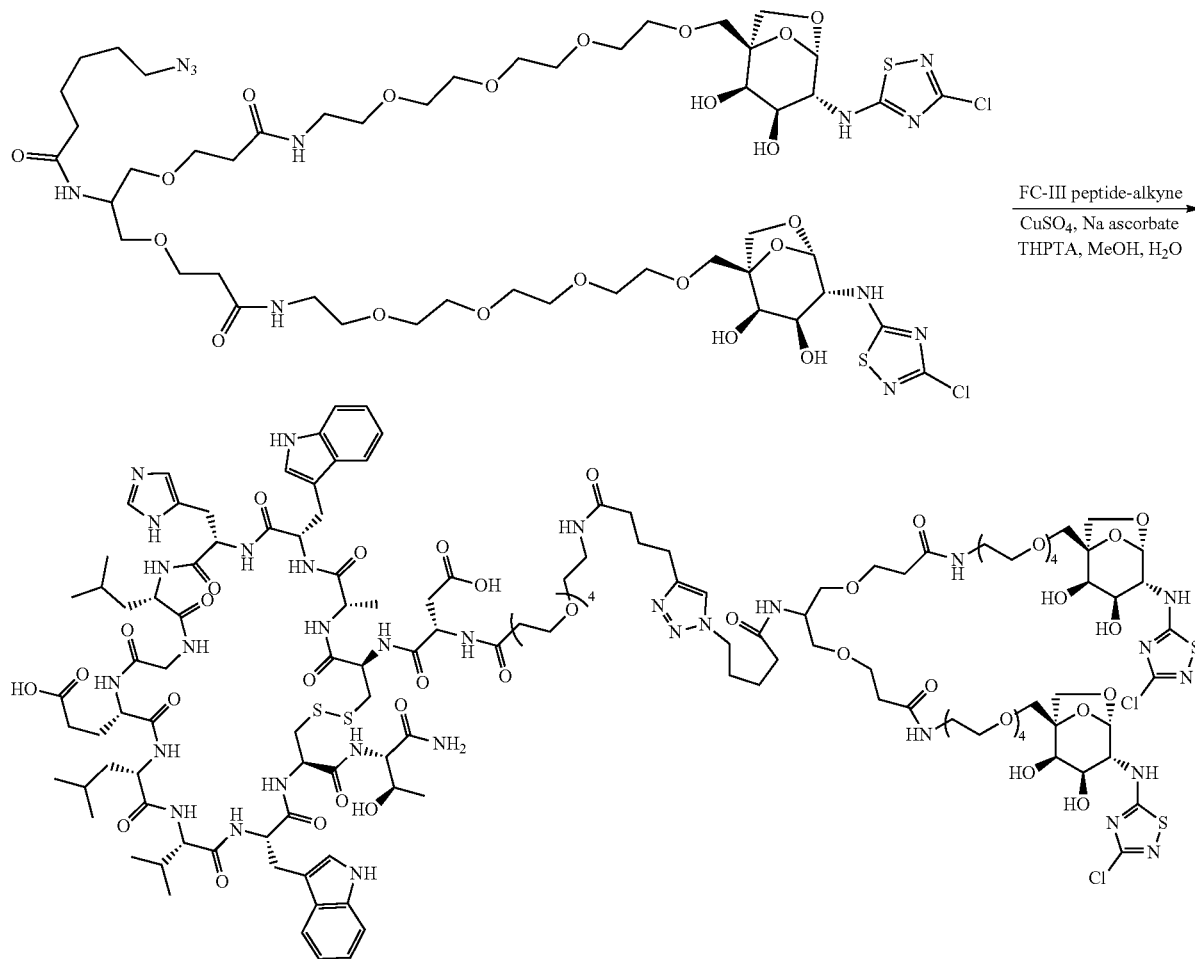

Step 1: THPTA (3.3 mg, 0.0076 mmol) and CuSO$_4$ (0.3 mg, 0.0012 mmol) were dissolved in water (0.1 mL). The mixture was added to a solution of 3,3'-((2-(6-azidohexanamido)propane-1,3-diyl)bis(oxy))bis(N-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide) (A14, 20 mg, 0.015 mmol) and FC-III peptide-alkyne (25.7 mg) in MeOH (2 mL). A freshly prepared solution of Na ascorbate (0.6 mg, 0.0030 mmol) in water (0.1 mL) was added. The reaction was stirred overnight. The resulting mixture was filtered.

NMR (400 MHz, CD$_3$OD): δ 7.70 (s, 1H), 7.51 (d, J=7.7 Hz, 1H), 7.27 (s, 2H), 7.20 (s, 2H), 6.99 (d, J=25.8 Hz, 7H), 5.38 (s, 2H), 4.34 (dd, J=22.4, 15.1 Hz, 6H), 4.11-4.08 (m, 1H), 3.99 (d, J=9.6 Hz, 2H), 3.92 (d, J=4.1 Hz, 2H), 3.82-3.75 (m, 5H), 3.70-3.66 (m, 12H), 3.64-3.56 (m, 40H), 3.53 (t, J=5.6 Hz, 6H), 3.49 (d, J=5.7 Hz, 2H), 3.46 (d, J=3.8 Hz, 2H), 3.37 (t, J=5.5 Hz, 6H), 3.04 (ddd, J=79.3, 27.9, 5.4 Hz, 14H), 2.68 (t, J=7.6 Hz, 4H), 2.44 (t, J=6.1 Hz, 8H), 2.25-2.17 (m, 6H), 1.96-1.84 (m, 6H), 1.67-1.52 (m, 6H), 1.29 (s, 8H), 0.84 (s, 21H).

Preparation of Compound 22, (S)-3-(((4R,7S,10S, 13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl) carbamoyl)-16-(2-carboxyethyl)-13,22-diisobutyl-10-isopropyl-31-methyl-6,9,12,15,18,21,24,27,30, 33-decaoxo-1,2-dithia-5,8,11,14,17,20,23,26,29,32-decaazacyclopentatriacontan-34-yl)carbamoyl)-24-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl) amino)tetrahydro-2H-pyran-2-yl)-15-oxo-2,5,8,11, 18-pentaoxa-14-azanonadecan-19-yl)-15,22-dioxo-2, 5,8,11,18-pentaoxa-14,21-diazaheptacosan-27-yl)-1H-1,2,3-triazol-4-yl)-5,21-dioxo-8,11,14,17-tetraoxa-4,20-diazatetracosanoic acid

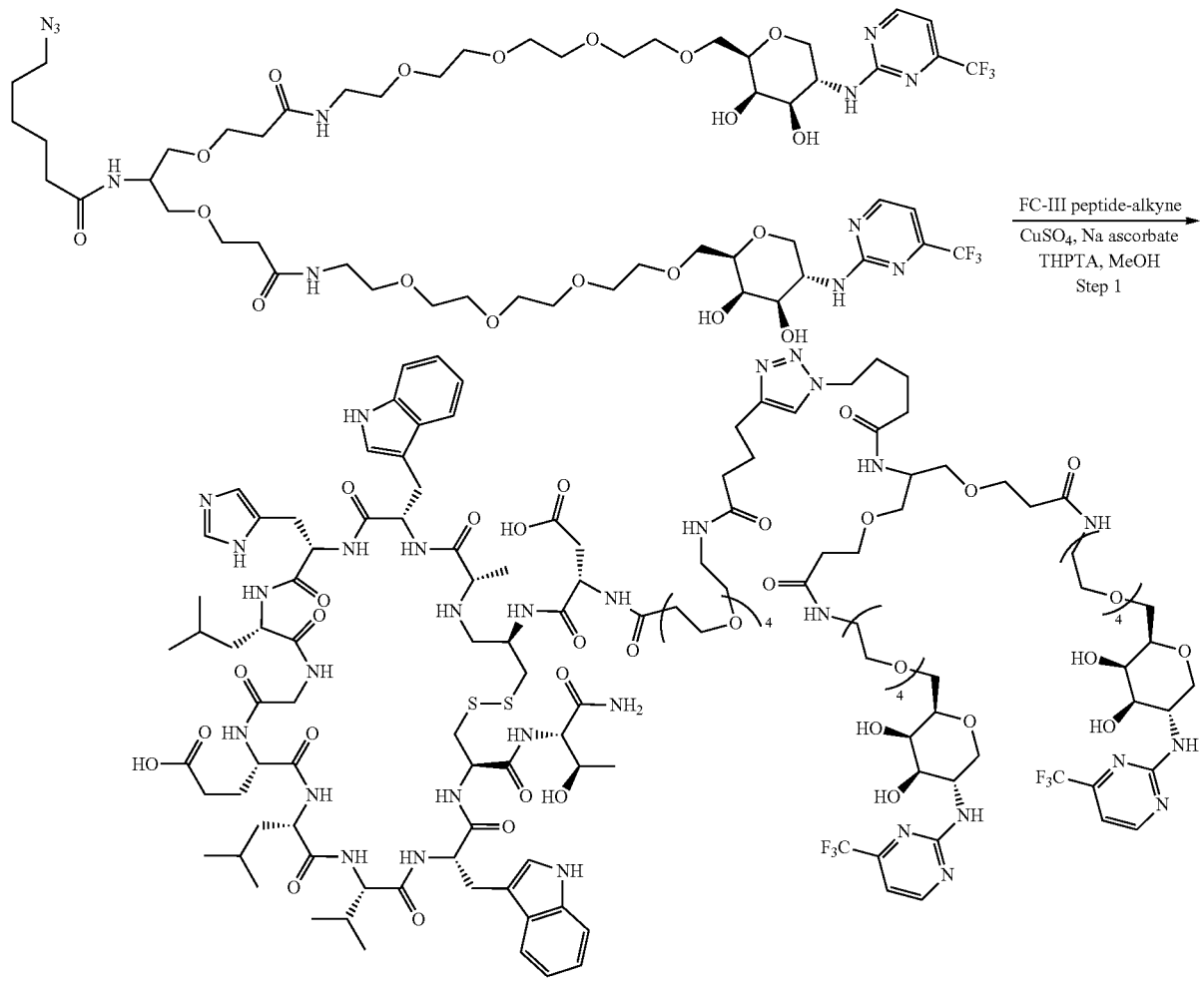

Step 1: THPTA (1.7 mg, 0.0040 mmol) and CuSO₄ (0.3 mg, 0.0010 mmol) were dissolved in water (0.05 mL). The mixture was added to a solution of 3,3'-((2-(6-azidohexana-mido)propane-1,3-diyl)bis(oxy))bis(N-(1-((2R,3R,4R,5S)-3,4-dihydroxy-5-((4-(trifluoromethyl)pyrimidin-2-yl) amino)tetrahydro-2H-pyran-2-yl)-2,5,8,11-tetraoxatridec-an-13-yl)propanamide) (15 mg, 0.015 mmol) and FC-III peptide-alkyne (10 mg) in MeOH (1 mL). A freshly prepared solution of Na ascorbate (0.4 mg, 0.0020 mmol) in water (0.05 mL) was added. The reaction was stirred overnight. The resulting mixture was filtered. The crude product was purified by prep-HPLC to give (S)-3-(((4R,7S,10S,13S,16S, 22S,25S,28S,31S,34R)-25-((1H-imi, dazol-5-yl)methyl)-7, 28-bis((1H-indol-3-yl)methyl)-4-(((2S,3R)-1-amino-3-hydroxy-1-oxobutan-2-yl)carbamoyl)-16-(2-carboxyethyl)-13,22-diisobutyl-10-isopropyl-31-methyl-6,9,12,15,18,21, 24,27,30,33-decaoxo-1,2-dithia-5,8,11,14,17,20,23,26,29, 32-decaazacyclopentatriacontan-34-yl)carbamoyl)-24-(1-(1-((2R,3R,4R,5S)-3,4-dihydroxy-5-((4-(trifluoromethyl) pyrimidin-2-yl)amino)tetrahydro-2H-pyran-2-yl)-20-(1-

((2R,3R,4R,5S)-3,4-dihydroxy-5-((4-(trifluoromethyl)py-rimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-5,21-dioxo-8,11,14,17-tetraoxa-4,20-diazatetracosanoic acid (Compound 22, 2.5 mg, 10% yield) as white solid. LC-MS (ESI) found: 795 [M+4H]$^{4+}$. $^1$H NMR (400 MHz, D$_2$O): δ 8.42 (d, J=4.6 Hz, 2H), 8.37 (s, 14H), 7.55 (s, 1H), 7.41 (dd, J=12.5, 8.8 Hz, 2H), 7.33 (t, J=8.3 Hz, 4H), 7.07 (d, J=14.5 Hz, 4H), 6.98 (d, J=11.5 Hz, 2H), 6.94 (d, J=5.1 Hz, 2H), 4.27-4.12 (m, 4H), 4.06-3.93 (m, 4H), 3.90 (d, J=2.9 Hz, 2H), 3.77-3.45 (m, 70H), 3.38 (dd, J=7.1, 1.7 Hz, 4H), 3.32-3.21 (m, 6H), 3.22-3.08 (m, 5H), 2.97 (d, J=8.9 Hz, 4H), 2.82 (dd, J=21.3, 9.1 Hz, 3H), 2.68-2.52 (m, 4H), 2.48 (d, J=6.5 Hz, 3H), 2.39 (t, J=5.6 Hz, 4H), 2.22-2.05 (m, 5H), 1.87-1.76 (m, 3H), 1.71 (d, J=11.9 Hz, 3H), 1.54-1.41 (m, 4H), 1.32-1.17 (m, 6H), 1.16-1.04 (m, 7H), 0.79 (d, J=6.0 Hz, 3H), 0.75-0.65 (m, 10H), 0.63-0.57 (m, 5H). $^{19}$F NMR (377 MHz, D$_2$O) δ −70.54, −75.60.

Preparation of Compound 23 ((S)-2-((S)-2-((1H-imidazol-5-yl)methyl)-23-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-4,20-dioxo-7,10,13,16-tetraoxa-3,19-diazatricosanamido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide)

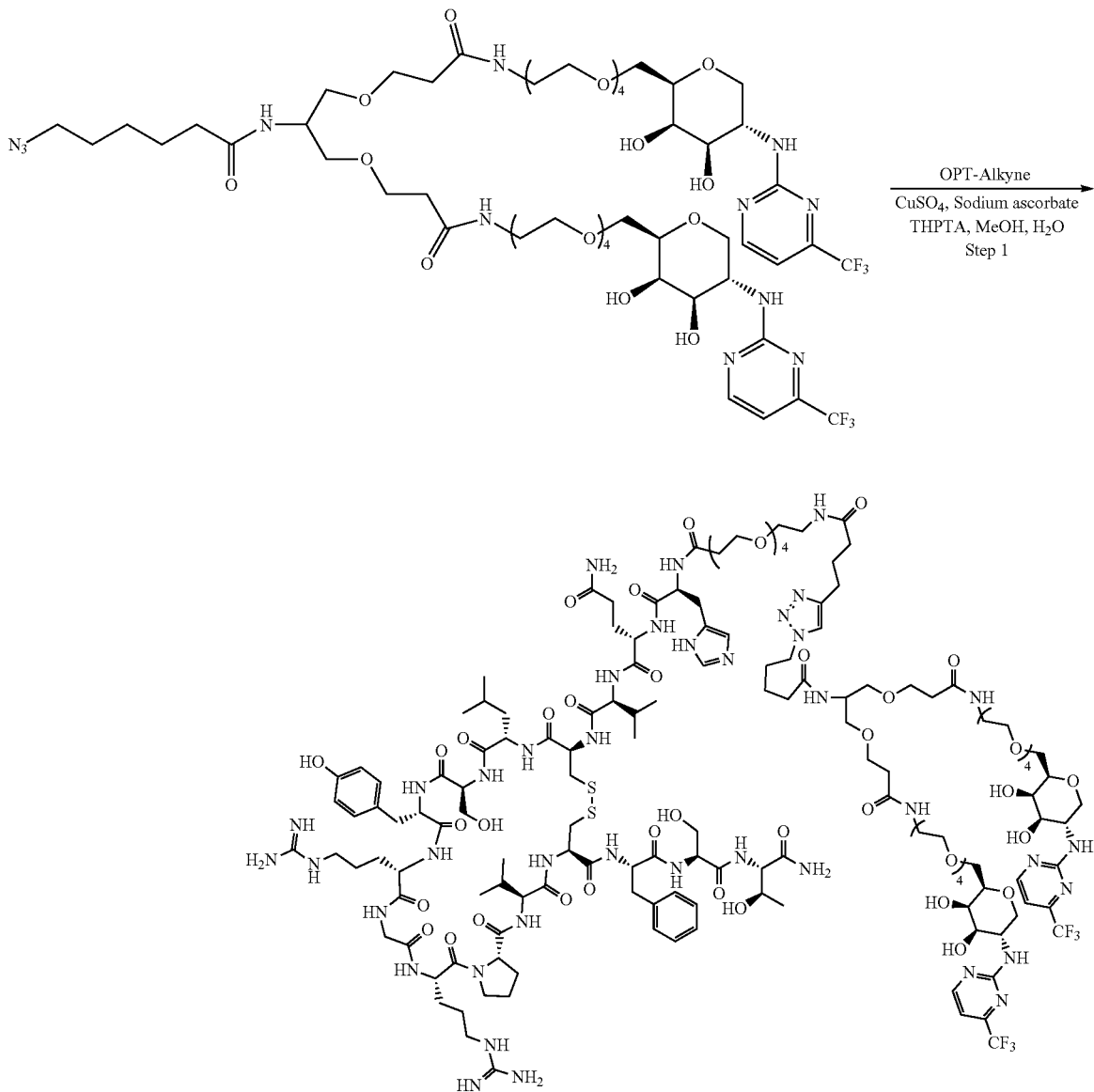

Step 1: THPTA (1.7 mg, 0.0007 mmol) and CuSO$_4$ (0.3 mg, 0.002 mmol) were dissolved in water (0.05 mL). The mixture was added to a solution of 3,3'-((2-(6-azidohexanamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (5 mg, 0.003 mmol) and OPT-Alkyne (8.4 mg, 0.003 mmol) in MeOH (1 mL). A solution of Na ascorbate (0.4 mg, 0.002 mmol) in water (0.05 mL) was added. The reaction was stirred overnight. The resulting mixture was filtered. The crude product was purified by prep-HPLC (Method A) to give (S)-2-((S)-2-((1H-imidazol-5-yl)methyl)-23-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-4,20-dioxo-7,10,13,16-tetraoxa-3,19-diazatricosanamido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (Compound 23, 2.5 mg, 18% yield) as white solid. LC-MS (ESI) found: 701 [M+5H]$^{5+}$. $^1$H NMR (400 MHz, MeOD): δ 8.55 (s, 1H), 8.51 (d, J=4.8 Hz, 2H), 7.76 (s, 1H), 7.57 (s, 1H), 7.16-7.07 (m, 7H), 6.89 (d, J=4.9 Hz, 2H), 6.74 (d, J=8.5 Hz, 2H), 5.75 (d, J=48.2 Hz, 2H), 5.26-5.05 (m, 3H), 4.91 (d, J=17.5 Hz, 2H), 4.76 (s, 6H), 4.58 (s, 2H), 4.45-4.28 (m, 9H), 4.16 (s, 1H), 4.08 (dd, J=10.2, 4.6 Hz, 3H), 3.92 (d, J=3.0 Hz, 2H), 3.69-3.53 (m, 58H), 3.48-3.43 (m, 4H), 3.38-3.33 (m, 7H), 3.22 (d, J=6.7 Hz, 2H), 3.19-3.07 (m, 6H), 3.05-2.94 (m, 6H), 2.71 (s, 2H), 2.46 (dd, J=14.5, 8.5 Hz, 6H), 2.22 (dt, J=13.3, 7.0 Hz, 8H), 2.05-1.87 (m, 14H), 1.73 (d, J=6.2 Hz, 4H), 1.66-1.57 (m, 4H), 1.35-1.28 (m, 4H), 1.23 (d, J=6.4 Hz, 3H), 1.04-0.92 (m, 12H), 0.87 (t, J=5.9 Hz, 9H). $^{19}$F NMR (377 MHz, MeOD): δ −72.26 (s).

Preparation of Compound 24, (2R,3R,4R,5R)-5-((3-chloro-1,2,4-thiadiazol-5-yl)amino)-2-(13-((2,4-dinitrophenyl)amino)-2,5,8,11-tetraoxatridecyl)tetrahydro-2H-pyran-3,4-diol

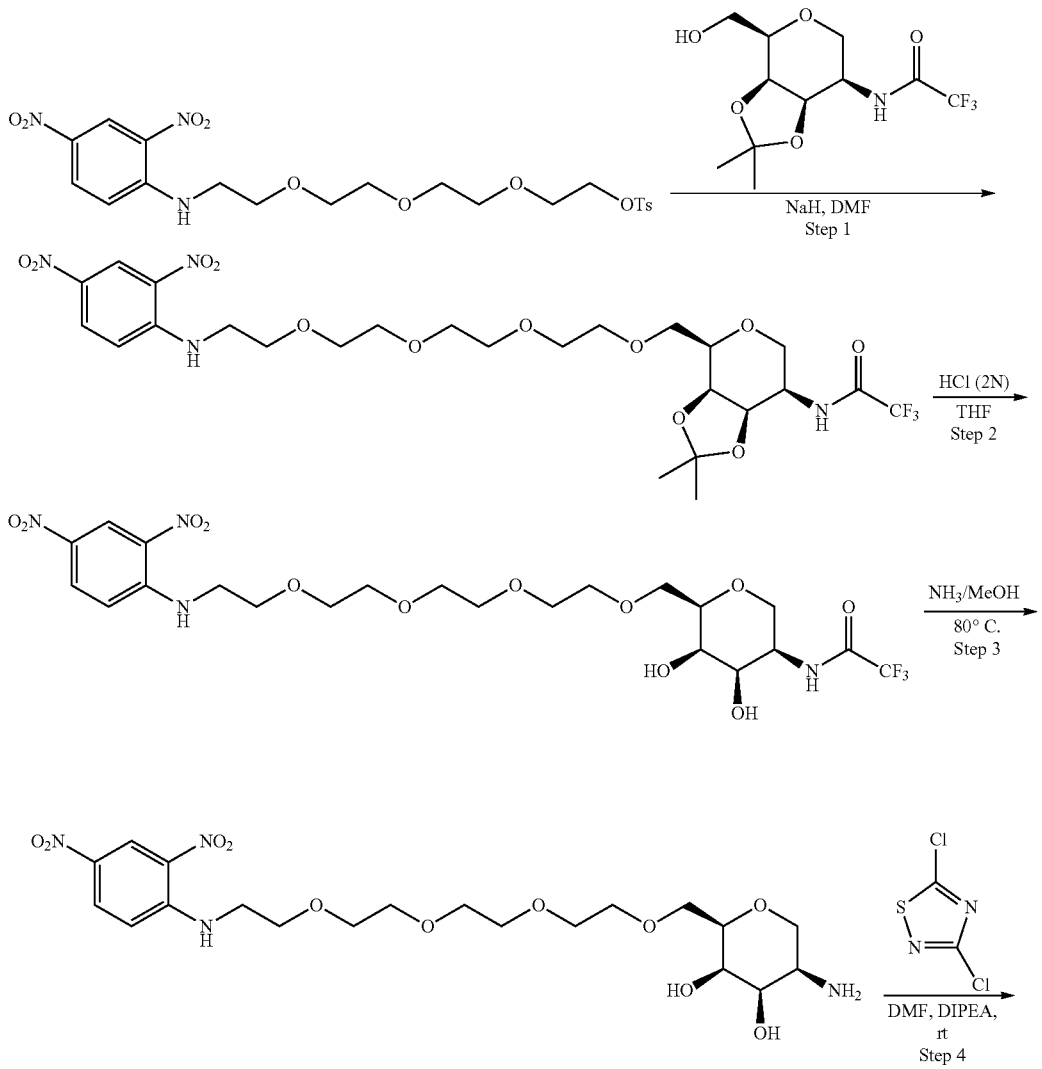

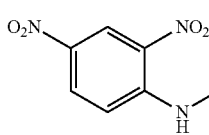
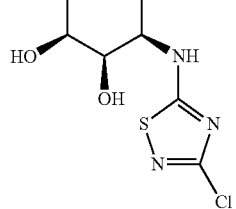

Step 1: To a solution of 2-(2-(2-(2-((2,4-dinitrophenyl)amino)ethoxy)ethoxy)ethoxy)ethyl 4-methylbenzenesulfonate (100 mg, 0.31 mmol) in DMF (10.0 mL) was added NaH (25.0 mg, 0.61 mmol, 60% wt. in mineral oil), 2,2,2-trifluoro-N-((3aR,4R,7R,7aR)-4-(hydroxymethyl)-2,2-dimethyltetrahydro-4H-[1,3]dioxolo[4,5-c]pyran-7-yl)acetamide (110 mg, 0.37 mmol). The mixture was stirred at the room temperature for 16 h. The mixture was concentrated under reduced pressure to give a crude product, which was purified by column to give N-((3aR,4R,7R,7aR)-4-(13-((2,4-dinitrophenyl)amino)-2,5,8,11-tetraoxatridecyl)-2,2-dimethyltetrahydro-4H-[1,3]dioxolo[4,5-c]pyran-7-yl)-2,2,2-trifluoroacetamide (80 mg, 0.13 mmol), LC-MS (ESI) found: 641 [M+H]+.

Step 2: To a solution of N-((3aR,4R,7R,7aR)-4-(13-((2,4-dinitrophenyl)amino)-2,5,8,11-tetraoxatridecyl)-2,2-dimethyltetrahydro-4H-[1,3]dioxolo[4,5-c]pyran-7-yl)-2,2,2-trifluoroacetamide (80 mg, 0.13 mmol) in THF (10 mL) was added HCl (2 N in water) (5 mL). The mixture was stirred at the room temperature for 16 h. The mixture was concentrated under reduced pressure to give a crude product, which was purified by column to give N-((3R,4R,5R,6R)-6-(13-((2,4-dinitrophenyl)amino)-2,5,8,11-tetraoxatridecyl)-4,5-dihydroxytetrahydro-2H-pyran-3-yl)-2,2,2-trifluoroacetamide (Compound 25, 60 mg, 0.10 mmol). LC-MS (ESI) found: 601 [M+H]+.

Step 3: A mixture of N-((3R,4R,5R,6R)-6-(13-((2,4-dinitrophenyl)amino)-2,5,8,11-tetraoxatridecyl)-4,5-dihydroxytetrahydro-2H-pyran-3-yl)-2,2,2-trifluoroacetamide (60 mg, 0.10 mmol) and NH₃/MeOH (10 mL, 7 N) was stirred at 80° C. for 16 h. The mixture was concentrated under reduced pressure and the residual was purified by column to give (2R,3R,4R,5R)-5-amino-2-(13-((2,4-dinitrophenyl)amino)-2,5,8,11-tetraoxatridecyl)tetrahydro-2H-pyran-3,4-diol (40 mg, 0.079 mmol). LC-MS (ESI) found: 505 [M+H]+.

Step 4: To a solution of (2R,3R,4R,5R)-5-amino-2-(13-((2,4-dinitrophenyl)amino)-2,5,8,11-tetraoxatridecyl)tetrahydro-2H-pyran-3,4-diol (40 mg, 0.079 mmol) in DMF (5 mL) was added DIEA (31 mg, 0.24 mmol) and 3,5-dichloro-1,2,4-thiadiazole (16 mg, 0.10 mmol). The mixture was stirred at the room temperature for 2 h. The mixture was concentrated under reduced pressure and the residual was purified by prep-HPLC to give (2R,3R,4R,5R)-5-((3-chloro-1,2,4-thiadiazol-5-yl)amino)-2-(13-((2,4-dinitrophenyl)amino)-2,5,8,11-tetraoxatridecyl)tetrahydro-2H-pyran-3,4-diol (Compound 24, 5.0 mg, 10% yield). LC-MS (ESI) found: 623 [M+H]+. ¹H NMR (400 MHz, CD₃OD): δ 9.04 (d, J=2.7 Hz, 1H), 8.29 (dd, J=9.6, 2.7 Hz, 1H), 7.23 (d, J=9.6 Hz, 1H), 4.11 (d, J=2.7 Hz, 1H), 3.93-3.86 (m, 2H), 3.81 (dd, J=6.6, 3.7 Hz, 3H), 3.72-3.53 (m, 18H).

Preparation of Compound 27, (1S,2R,3R,4R,5S)-4-((3-chloro-1,2,4-thiadiazol-5-yl)amino)-1-(13-((2,4-dinitrophenyl)amino)-2,5,8,11-tetraoxatridecyl)-6,8-dioxabicyclo[3.2.1]octane-2,3-diol

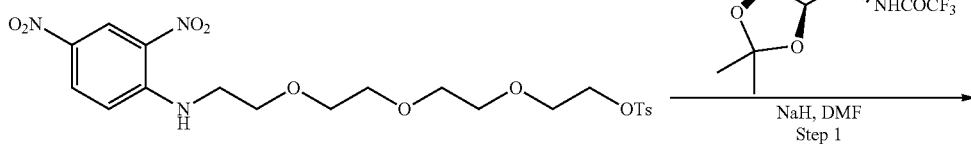
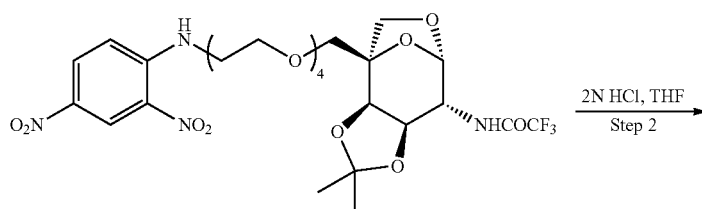

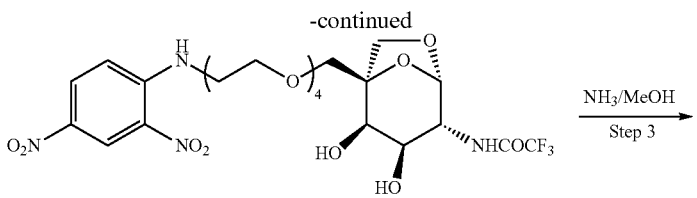

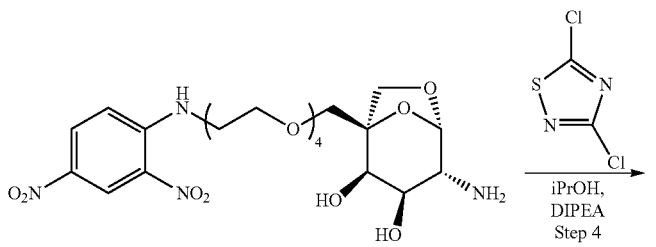

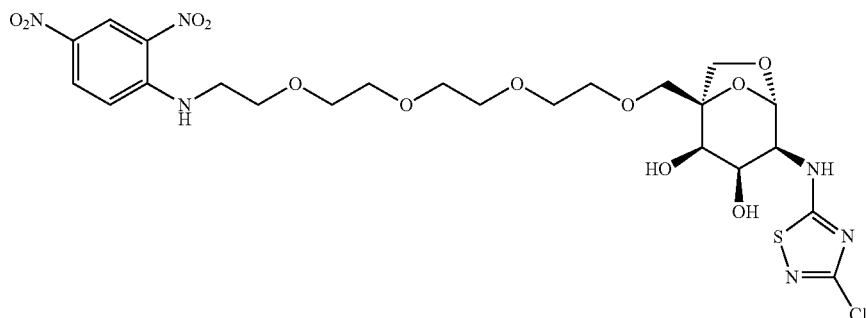

Step 1: NaH (49 mg, 60% wt. in mineral oil) was added to a suspension of 2,2,2-trifluoro-N-((3aR,4S,7S,8R,8aR)-4-(hydroxymethyl)-2,2-dimethylhexahydro-4,7-epoxy[1,3]dioxolo[4,5-d]oxepin-8-yl)acetamide (200 mg, 0.61 mmol) in dry DMF (5 mL). The mixture was stirred at rt for 1.5 h. Then 2-(2-(2-(2-((2,4-dinitrophenyl)amino)ethoxy)ethoxy)ethoxy)ethyl 4-methylbenzenesulfonate (267 mg, 0.52 mmol) was added to the above solution. The mixture was further stirred at rt for 16 h. The mixture was added NH$_4$Cl (aq) and the solvent was removed. Then the residual was purified by flash (DCM:MeOH=15:1) to give N-((3aR,4S,7S,8R,8aR)-4-(13-((2,4-dinitrophenyl)amino)-2,5,8,11-tetraoxatridecyl)-2,2-dimethylhexahydro-4,7-epoxy[1,3]dioxolo[4,5-d]oxepin-8-yl)-2,2,2-trifluoroacetamide (215 mg, 53% yield). LC-MS (ESI) found: 670 [M+H]$^+$.

Step 2: A solution of N-((3aR,4S,7S,8R,8aR)-4-(13-((2,4-dinitrophenyl)amino)-2,5,8,11-tetraoxatridecyl)-2,2-dimethylhexahydro-4,7-epoxy[1,3]dioxolo[4,5-d]oxepin-8-yl)-2,2,2-trifluoroacetamide (215 mg, 0.322 mmol) in THF (2 mL) was added HCl (1 mL, 2 M in H$_2$O). The reaction was stirred at rt for 18 h. The solvent was removed and purified by prep-HPLC (MEOH/water) to afford N-((1S,2R,3R,4R,5S)-1-(13-((2,4-dinitrophenyl)amino)-2,5,8,11-tetraoxatridecyl)-2,3-dihydroxy-6,8-dioxabicyclo[3.2.1]octan-4-yl)-2,2,2-trifluoroacetamide (120 mg, 59% yield). LC-MS (ESI) found: 629 [M+H]$^+$. $^1$H NMR (400 MHz, MeOD): δ 9.04 (d, J=2.7 Hz, 1H), 8.29 (dd, J=9.6, 2.7 Hz, 1H), 7.23 (d, J=9.6 Hz, 1H), 5.22 (d, J=1.5 Hz, 1H), 3.98 (t, J=9.7 Hz, 2H), 3.91-3.84 (m, 2H), 3.83-3.77 (m, 3H), 3.67 (ddd, J=7.8, 4.1, 2.2 Hz, 8H), 3.65-3.60 (m, 8H).

Step 3: A solution of N-((1S,2R,3R,4R,5S)-1-(13-((2,4-dinitrophenyl)amino)-2,5,8,11-tetraoxatridecyl)-2,3-dihydroxy-6,8-dioxabicyclo[3.2.1]octan-4-yl)-2,2,2-trifluoroacetamide (100 mg, 0.159 mmol) in NH$_3$/MeOH solution (5 mL, 7 M), and the reaction was stirred at 70° C. for 18 h. The reaction was concentrated in vacuo to afford (1S,2R,3R,4R,5S)-4-amino-1-(13-((2,4-dinitrophenyl)amino)-2,5,8,11-tetraoxatridecyl)-6,8-dioxabicyclo[3.2.1]octane-2,3-diol (74 mg, 87% yield). LC-MS (ESI) found: 533 [M+H]$^+$.

Step 4: To a solution of (1S,2R,3R,4R,5S)-4-amino-1-(13-((2,4-dinitrophenyl)amino)-2,5,8,11-tetraoxatridecyl)-6,8-dioxabicyclo[3.2.1]octane-2,3-diol (74 mg, 0.139 mmol) in i-PrOH (3 mL) was added DIEA (0.14 mL, 0.834 mmol) and dichloro-1,2,4-thiadiazole (108 mg, 0.695 mmol), and the reaction was stirred at 80° C. for 18 h. The reaction was concentrated in vacuo. The residue was purified by prep-HPLC to afford (1S,2R,3R,4R,5S)-4-((3-chloro-1,2,4-thiadiazol-5-yl)amino)-1-(13-((2,4-dinitrophenyl)amino)-2,5,8,11-tetraoxatridecyl)-6,8-dioxabicyclo[3.2.1]octane-2,3-diol (Compound 27, 36 mg, 40% yield). LC-MS (ESI) found: 651 [M+H]$^+$. $^1$H NMR (400 MHz, MeOD): δ 9.03 (d, J=2.7 Hz, 1H), 8.28 (dd, J=9.6, 2.7 Hz, 1H), 7.23 (d, J=9.6 Hz, 1H), 5.35 (d, J=0.9 Hz, 1H), 3.97 (d, J=9.6 Hz, 1H), 3.91 (d, J=4.1 Hz, 1H), 3.88-3.78 (m, 4H), 3.75 (dd, J=9.6, 4.3 Hz, 1H), 3.71-3.65 (m, 9H), 3.64-3.60 (m, 7H).

Preparation of Compound 34, N-((1S,2R,3R,4R,5S)-1-(22-((2,4-dinitrophenyl)amino)-2,5,8,11,14,17,20-heptaoxadocosyl)-2,3-dihydroxy-6,8-dioxabicyclo[3.2.1]octan-4-yl)-2,2,2-trifluoroacetamide and Compound 26, (1S,2R,3R,4R,5S)-4-((3-chloro-1,2,4-thiadiazol-5-yl)amino)-1-(22-((2,4-dinitrophenyl)amino)-2,5,8,11,14,17,20-heptaoxadocosyl)-6,8-dioxabicyclo[3.2.1]octane-2,3-diol

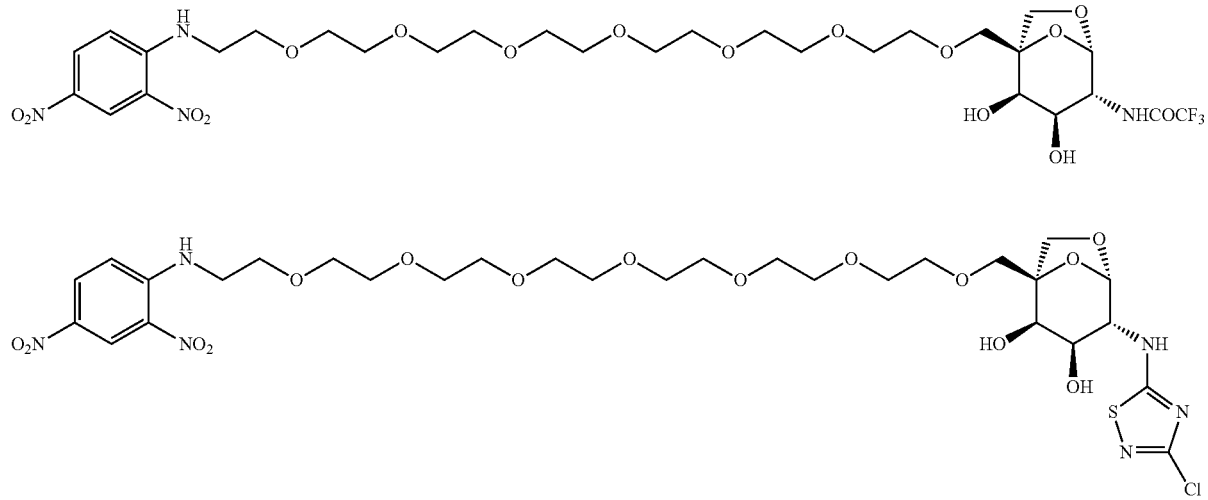

Compounds were prepared according to the same procedures as that for Compound 27 by using 20-((2,4-dinitrophenyl)amino)-3,6,9,12,15,18-hexaoxaicosyl 4-methylbenzenesulfonate as the starting material.

Compound 34: LC-MS (ESI) found: 761 [M+H]$^+$. $^1$H NMR (400 MHz, MeOD): δ 9.11-8.81 (m, 1H), 8.28 (dd, J=9.6, 2.7 Hz, 1H), 7.23 (d, J=9.6 Hz, 1H), 5.23 (d, J=1.3 Hz, 1H), 3.99 (t, J=9.2 Hz, 2H), 3.92-3.86 (m, 2H), 3.81 (dd, J=6.4, 4.3 Hz, 3H), 3.70-3.64 (m, 10H), 3.61 (d, J=2.4 Hz, 18H).

Compound 26: LC-MS (ESI) found: 783 [M+H]$^+$. $^1$H NMR (400 MHz, MeOD): δ 9.03 (d, J=2.7 Hz, 1H), 8.29 (dd, J=9.6, 2.7 Hz, 1H), 7.23 (d, J=9.6 Hz, 1H), 5.37 (s, 1H), 3.99 (d, J=9.6 Hz, 1H), 3.92 (d, J=4.1 Hz, 1H), 3.81 (dd, J=9.5, 4.6 Hz, 3H), 3.78-3.74 (m, 1H), 3.71-3.64 (m, 10H), 3.62 (d, J=2.9 Hz, 19H).

Preparation of Compound 28, 3,3'-((2-(2-(2-(2-(2-((2,4-dinitrophenyl)amino)ethoxy)ethoxy)ethoxy)acetamido)propane-1,3-diyl)bis(oxy))bis(N-(1-((2R,3R,4R,5R)-5-((3-chloro-1,2,4-thiadiazol-5-yl)amino)-3,4-dihydroxytetrahydro-2H-pyran-2-yl)-2,5,8,11-tetraoxatridecan-13-yl)propanamide)

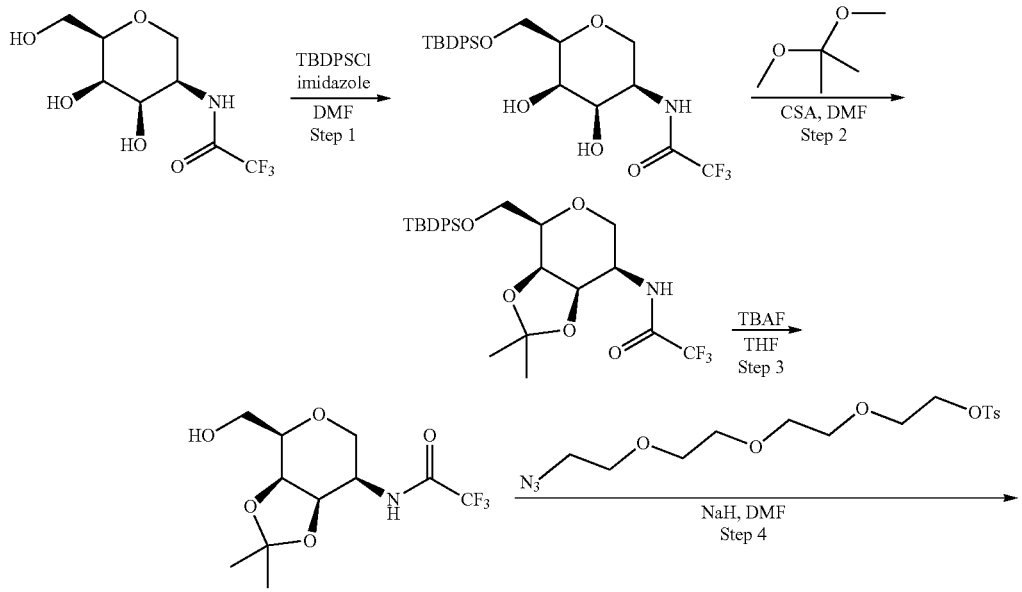

1093
1094
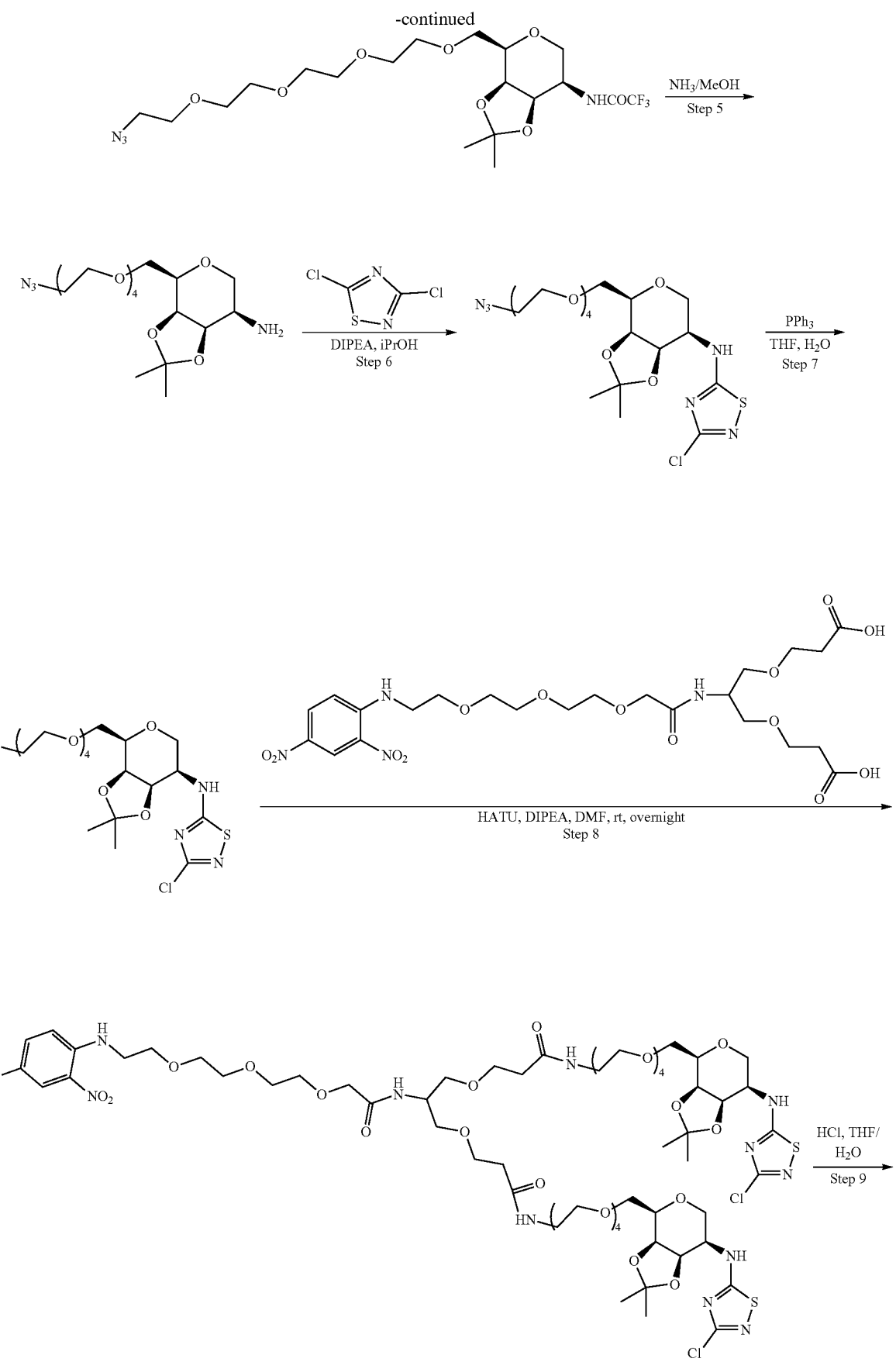

-continued

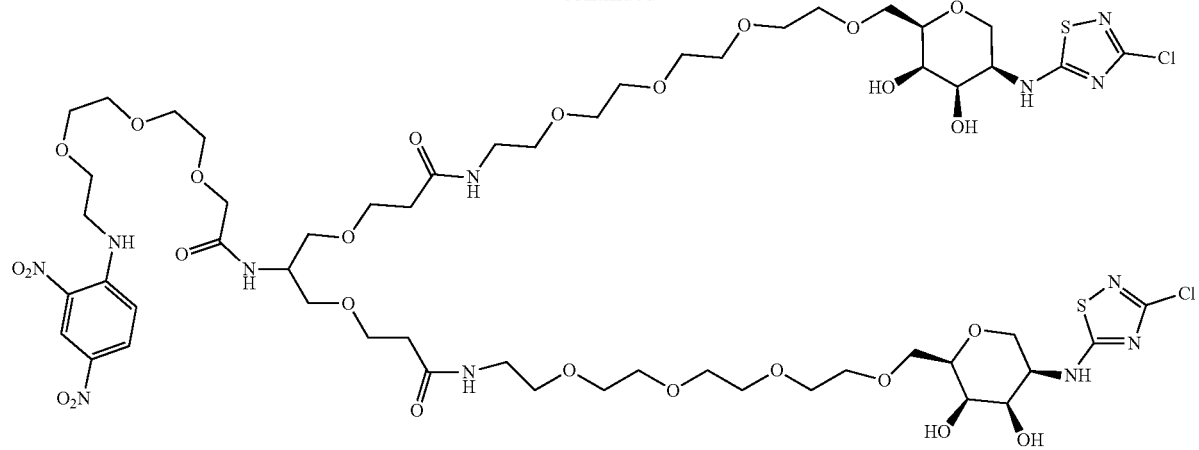

Step 1: To a solution of N-((3R,4R,5R,6R)-4,5-dihydroxy-6-(hydroxymethyl)tetrahydro-2H-pyran-3-yl)-2,2,2-trifluoroacetamide (2.8 g, 10.8 mmol) in DMF (30 mL) was added imidazole (1.46 mL, 21.6 mmol) and tert-Butylchlorodiphenylsilane (4.45 g, 16.2 mmol) at 0° C. The mixture was stirred at rt overnight. The resulting mixture was diluted with DCM (100 mL), washed with H$_2$O (30 mL×2) and brine (50 mL), dried over Na$_2$SO$_4$. The organic layer was separated and concentrated in vacuo. The crude product was purified by flash chromatography (silica gel, 0~80% EA in PE) to give N-((3R,4R,5R,6R)-6-(((tert-butyldiphenylsilyl)oxy)methyl)-4,5-dihydroxytetrahydro-2H-pyran-3-yl)-2,2,2-trifluoroacetamide (5.2 g, 96% yield) as a colorless oil. LC-MS (ESI) found: 520 [M+Na]$^+$. $^1$H NMR (400 MHz, CDCl$_3$): δ 8.17 (d, J=8.4 Hz, 1H), 7.72-7.62 (m, 4H), 7.49-7.36 (m, 6H), 4.28 (dd, J=8.3, 4.0 Hz, 1H), 4.23 (d, J=1.3 Hz, 1H), 4.16 (d, J=1.4 Hz, 1H), 4.06-3.91 (m, 3H), 3.80 (s, 1H), 3.51 (dd, J=12.4, 1.5 Hz, 1H), 3.34-3.29 (m, 1H), 3.01 (d, J=7.6 Hz, 1H), 1.06 (s, 9H). $^{19}$F NMR (377 MHz, CDCl$_3$): δ −76.16 (s).

Step 2: To a solution of N-((3R,4R,5R,6R)-6-(((tert-butyldiphenylsilyl)oxy)methyl)-4,5-dihydroxytetrahydro-2H-pyran-3-yl)-2,2,2-trifluoroacetamide (5.4 g, 10.9 mmol) in 2,2-dimethoxypropane (20 mL, 161.3 mmol) was added PTSA (0.19 g, 1.1 mmol) at rt under N$_2$. The reaction was stirred at rt overnight. The resulting mixture was diluted with DCM (150 mL), washed with H$_2$O (50 mL×2) and brine (30 mL), dried over Na$_2$SO$_4$. The organic layer was separated and concentrated in vacuo. The crude product was purified by flash chromatography (silica gel, 0~80% EA in PE) to give N-((3aR,4R,7R,7aR)-4-(((tert-butyldiphenylsilyl)oxy)methyl)-2,2-dimethyltetrahydro-4H-[1,3]dioxolo[4,5-c]pyran-7-yl)-2,2,2-trifluoroacetamide (4.6 g, 78% yield) as a colorless oil. LC-MS (ESI) found: 538 [M+H]$^+$. $^1$H NMR (400 MHz, CDCl$_3$): δ 7.72-7.64 (m, 4H), 7.46-7.35 (m, 6H), 6.69 (d, J=8.6 Hz, 1H), 4.42-4.36 (m, 2H), 4.35-4.28 (m, 1H), 3.92-3.77 (m, 4H), 3.54 (dd, J=11.4, 2.9 Hz, 1H), 1.47 (s, 3H), 1.36 (s, 3H), 1.05 (s, 9H).

Step 3: To a solution of N-((3aR,4R,7R,7aR)-4-(((tert-butyldiphenylsilyl)oxy)methyl)-2,2-dimethyltetrahydro-4H-[1,3]dioxolo[4,5-c]pyran-7-yl)-2,2,2-trifluoroacetamide (4.6 g, 8.6 mmol) in THF (50 mL) was added TBAF (17 mL, 1 M in THF) at rt and stirred for 3 h. The resulting mixture was diluted with DCM (100 mL), washed with H$_2$O (30 mL×2) and brine (50 mL), dried over Na$_2$SO$_4$. The organic layer was separated and concentrated in vacuo. The crude product was purified by flash chromatography (silica gel, 0~10% MeOH in DCM) to give 2,2,2-trifluoro-N-((3aR,4R,7R,7aR)-4-(hydroxymethyl)-2,2-dimethyltetrahydro-4H-[1,3]dioxolo[4,5-c]pyran-7-yl)acetamide (2.2 g, 85% yield) as a colorless oil. LC-MS (ESI) found: 300 [M+H]$^+$. $^1$H NMR (400 MHz, DMSO-d$_6$): δ 9.05 (s, 1H), 4.71 (t, J=5.6 Hz, 1H), 4.48 (dd, J=7.6, 3.6 Hz, 1H), 4.30 (ddd, J=12.8, 8.3, 3.5 Hz, 2H), 3.81 (t, J=9.7 Hz, 1H), 3.64 (ddd, J=16.0, 8.4, 3.7 Hz, 2H), 3.44 (td, J=6.2, 4.5 Hz, 2H), 1.41 (s, 3H), 1.28 (s, 3H).

Step 4: To a solution of 2,2,2-trifluoro-N-((3aR,4R,7R,7aR)-4-(hydroxymethyl)-2,2-dimethyltetrahydro-4H-[1,3]dioxolo[4,5-c]pyran-7-yl)acetamide (300 mg, 1 mmol) in DMF (8 mL) was added NaH (80 mg, 2 mmol) at 0° C. and stirred for 1 h under N$_2$. 2-(2-(2-(2-azidoethoxy)ethoxy)ethoxy)ethyl 4-methylbenzenesulfonate (664 mg, 2 mmol) was added at 0° C. and stirred at rt for 2 h under N$_2$. The resulting mixture was diluted with DCM (80 mL) and water (10 mL). The aqueous phase was extracted with DCM (50 mL×2). The organic layer was separated, dried over Na$_2$SO$_4$ and concentrated in vacuo. The crude product was purified by flash chromatography (silica gel, 0~10% MeOH in DCM) to give N-((3aR,4R,7R,7aR)-4-(13-azido-2,5,8,11-tetraoxatridecyl)-2,2-dimethyltetrahydro-4H-[1,3]dioxolo[4,5-c]pyran-7-yl)-2,2,2-trifluoroacetamide (250 mg, 54% yield) as a colorless oil. LC-MS (ESI) found: 501 [M+H]$^+$. $^1$H NMR (400 MHz, DMSO-d$_6$): δ 9.09 (d, J=6.9 Hz, 1H), 4.48 (dd, J=7.5, 3.6 Hz, 1H), 4.36-4.25 (m, 2H), 3.88-3.76 (m, 2H), 3.65 (dd, J=10.1, 5.8 Hz, 1H), 3.62-3.58 (m, 2H), 3.58-3.46 (m, 13H), 3.44-3.36 (m, 3H), 1.41 (s, 3H), 1.28 (s, 3H).

Step 5: A solution of N-((3aR,4R,7R,7aR)-4-(13-azido-2,5,8,11-tetraoxatridecyl)-2,2-dimethyltetrahydro-4H-[1,3]dioxolo[4,5-c]pyran-7-yl)-2,2,2-trifluoroacetamide (900 mg, 1.8 mmol) in ammonia methanol solution (6 mL, 7 M in MeOH) was stirred at 70° C. overnight. The resulting mixture was concentrated in vacuo. The crude product was purified by flash chromatography (silica gel, 0~10% MeOH in DCM) to give (3aR,4R,7R,7aR)-4-(13-azido-2,5,8,11-tetraoxatridecyl)-2,2-dimethyltetrahydro-4H-[1,3]dioxolo[4,5-c]pyran-7-amine (400 mg, 55% yield) as a colorless oil. LC-MS (ESI) found: 405 [M+H]$^+$.

Step 6: To a solution of 3aR,4R,7R,7aR)-4-(13-azido-2,5,8,11-tetraoxatridecyl)-2,2-dimethyltetrahydro-4H-[1,3]dioxolo[4,5-c]pyran-7-amine (420 mg, 1.0 mmol) and dichloro-1,2,4-thiadiazole (322 mg, 2.1 mmol) in i-PrOH (6 mL) was added DIPEA (0.5 mL, 3.1 mmol) at rt under N$_2$.

The reaction was stirred at 80° C. overnight. The resulting mixture was concentrated in vacuo. The crude product was purified by flash chromatography (silica gel, 0-10% MeOH in DCM) to give N-((3aR,4R,7R,7aR)-4-(13-azido-2,5,8,11-tetraoxatridecyl)-2,2-dimethyltetrahydro-4H-[1,3]dioxolo[4,5-c]pyran-7-yl)-3-chloro-1,2,4-thiadiazol-5-amine (480 mg, 88% yield) as a colorless oil. LC-MS (ESI) found: 524 [M+H]+. 1H NMR (400 MHz, MeOD): δ 5.49 (s, 1H), 4.52 (dd, J=6.8, 4.7 Hz, 1H), 4.36-4.19 (m, 2H), 3.95 (ddd, J=7.2, 5.0, 2.3 Hz, 1H), 3.85 (dd, J=10.9, 6.4 Hz, 1H), 3.75 (dd, J=10.9, 4.0 Hz, 1H), 3.71-3.67 (m, 4H), 3.66-3.63 (m, 12H), 3.40-3.35 (m, 2H), 1.43 (s, 3H), 1.33 (s, 3H).

Step 7: To a solution of N-((3aR,4R,7R,7aR)-4-(13-azido-2,5,8,11-tetraoxatridecyl)-2,2-dimethyltetrahydro-4H-[1,3]dioxolo[4,5-c]pyran-7-yl)-3-chloro-1,2,4-thiadiazol-5-amine (480 mg, 0.92 mmol) in THF (9 mL) and H2O (3 mL) was added PPh3 (481 mg, 1.84 mmol). The mixture was stirred at 80° C. overnight. The resulting mixture was concentrated in vacuo. The crude product was purified by flash chromatography (silica gel, 0-10% MeOH in DCM) to give N-((3aR,4R,7R,7aR)-4-(13-amino-2,5,8,11-tetraoxatridecyl)-2,2-dimethyltetrahydro-4H-[1,3]dioxolo[4,5-c]pyran-7-yl)-3-chloro-1,2,4-thiadiazol-5-amine (330 mg, 72% yield) as a colorless oil. LC-MS (ESI) found: 497 [M+H]+.

Step 8: A solution of 13-((2-carboxyethoxy)methyl)-1-((2,4-dinitrophenyl)amino)-11-oxo-3,6,9,15-tetraoxa-12-azaoctadecan-18-oic acid (120 mg, 0.2 mmol) and HATU (170 mg, 0.45 mmol) in DMF (5 mL) was stirred at rt for 30 min. Then N-((3aR,4R,7R,7aR)-4-(13-amino-2,5,8,11-tetraoxatridecyl)-2,2-dimethyltetrahydro-4H-[1,3]dioxolo[4,5-c]pyran-7-yl)-3-chloro-1,2,4-thiadiazol-5-amine (303 mg, 0.6 mmol) and DIPEA (0.12 mL, 0.7 mmol) were added at rt. The reaction was stirred overnight. The resulting mixture was diluted with DCM (100 mL), washed with H2O (50 mL×2) and brine (20 mL), dried over Na2SO4. The organic layer was separated and concentrated in vacuo. The crude product was purified by flash chromatography (silica gel, 0~10% MeOH in DCM) to give 3,3'-((2-(2-(2-(2-(2-((2,4-dinitrophenyl)amino)ethoxy)ethoxy)ethoxy)acetamido)propane-1,3-diyl)bis(oxy))bis(N-(1-((3aR,4R,7R,7aR)-7-((3-chloro-1,2,4-thiadiazol-5-yl)amino)-2,2-dimethyltetrahydro-4H-[1,3]dioxolo[4,5-c]pyran-4-yl)-2,5,8,11-tetraoxatridecan-13-yl)propanamide) (250 mg, 79% yield) as yellow oil. LC-MS (ESI) found: 775 [M+2H]2+.

Step 9: To a solution of 3,3'-((2-(2-(2-(2-(2-((2,4-dinitrophenyl)amino)ethoxy)ethoxy)ethoxy)acetamido)propane-1,3-diyl)bis(oxy))bis(N-(1-((3aR,4R,7R,7aR)-7-((3-chloro-1,2,4-thiadiazol-5-yl)amino)-2,2-dimethyltetrahydro-4H-[1,3]dioxolo[4,5-c]pyran-4-yl)-2,5,8,11-tetraoxatridecan-13-yl)propanamide) (250 mg, 0.16 mmol) in THF (6 mL) was added HCl (3 mL, 2 M in H2O). The reaction was stirred at rt for 3 h. The crude product was purified by flash chromatography (silica gel, 0-10% MeOH in DCM) to give 3,3'-((2-(2-(2-(2-(2-((2,4-dinitrophenyl)amino)ethoxy)ethoxy)ethoxy)acetamido)propane-1,3-diyl)bis(oxy))bis(N-(1-((2R,3R,4R,5R)-5-((3-chloro-1,2,4-thiadiazol-5-yl)amino)-3,4-dihydroxytetrahydro-2H-pyran-2-yl)-2,5,8,11-tetraoxatridecan-13-yl)propanamide) (Compound 28, 105 mg, 44% yield) as a yellow solid. LC-MS (ESI) found: 735 [M+2H]2+. 1H NMR (400 MHz, MeOD): δ 9.04 (d, J=2.7 Hz, 1H), 8.30 (dd, J=9.6, 2.7 Hz, 1H), 7.23 (d, J=9.6 Hz, 1H), 4.21-4.17 (m, 1H), 4.06 (d, J=1.9 Hz, 1H), 4.03 (d, J=1.8 Hz, 1H), 3.99 (s, 2H), 3.90 (d, J=3.1 Hz, 2H), 3.85-3.80 (m, 4H), 3.75-3.46 (m, 56H), 3.36 (t, J=5.5 Hz, 4H), 2.44 (t, J=6.2 Hz, 4H).

Preparation of Compound 29, (N-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)-3-((14-((2,4-dinitrophenyl)amino)-4-oxo-6,9,12-trioxa-3-azatetradecyl)oxy)propenamide)

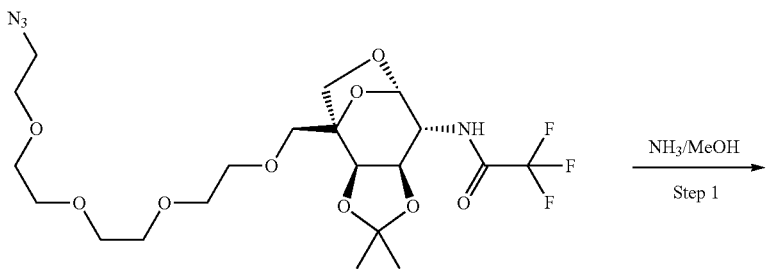

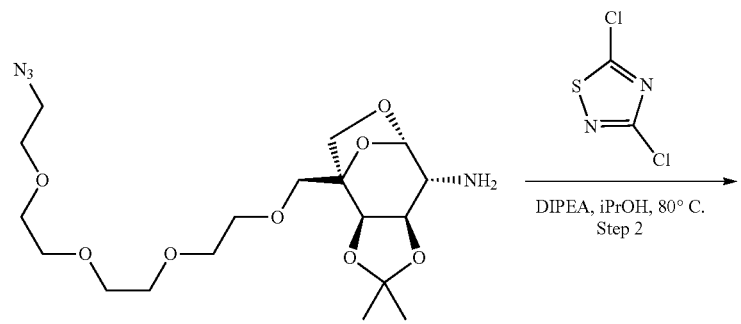

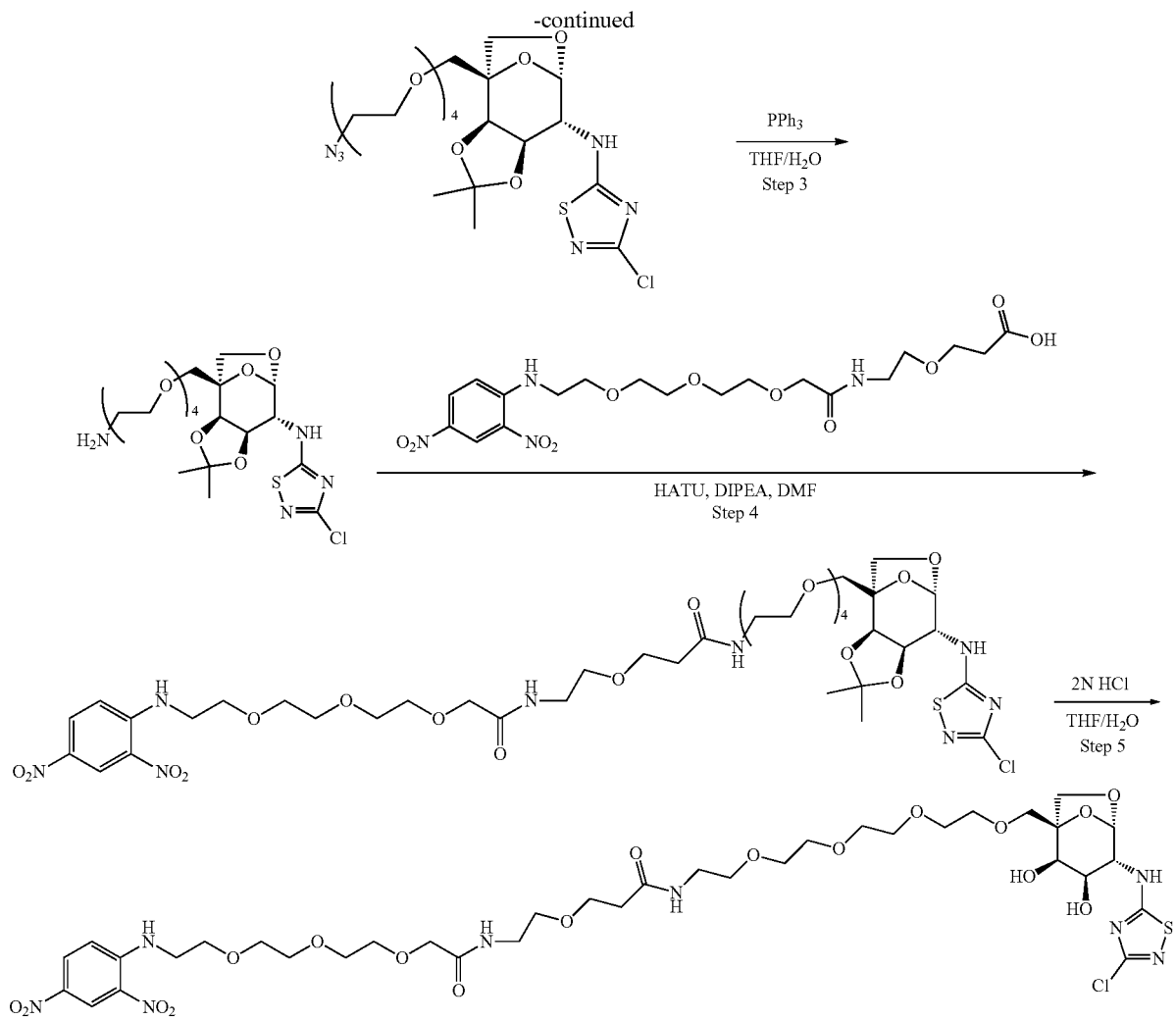

Step 1: A solution of N-((3aR,4S,7S,8R,8aR)-4-(13-azido-2,5,8,11-tetraoxatridecyl)-2,2-dimethylhexahydro-4,7-epoxy[1,3]dioxolo[4,5-d]oxepin-8-yl)-2,2,2-trifluoroacetamide (100 mg, 0.19 mmol) in methanolic NH₃ solution (5 mL, 7 M) was stirred at 70° C. overnight. The mixture was concentrated to give crude (3aR,4S,7S,8R,8aR)-4-(13-azido-2,5,8,11-tetraoxatridecyl)-2,2-dimethylhexahydro-4,7-epoxy[1,3]dioxolo[4,5-d]oxepin-8-amine (70 mg, 86% yield) as colorless oil. LC-MS (ESI) found: 341 [M+H]⁺.

Step 2: A solution of (3aR,4S,7S,8R,8aR)-4-(13-azido-2,5,8,11-tetraoxatridecyl)-2,2-dimethylhexahydro-4,7-epoxy[1,3]dioxolo[4,5-d]oxepin-8-amine (70 mg, 0.16 mmol), 3,5-dichloro-1,2,4-thiadiazole (35 mg, 0.22 mmol) and DIPEA (48 mg, 0.37 mmol) in i-PrOH (2 mL) was stirred at 80° C. overnight and then evaporated. The residue was purified by prep-TLC to give N-((3aR,4S,7S,8R,8aR)-4-(13-azido-2,5,8,11-tetraoxatridecyl)-2,2-dimethylhexahydro-4,7-epoxy[1,3]dioxolo[4,5-d]oxepin-8-yl)-3-chloro-1,2,4-thiadiazol-5-amine (90 mg, 88% yield) as colorless oil. LC-MS (ESI) found: 551 [M+H]⁺.

Step 3: To a solution of N-((3aR,4S,7S,8R,8aR)-4-(13-azido-2,5,8,11-tetraoxatridecyl)-2,2-dimethylhexahydro-4,7-epoxy[1,3]dioxolo[4,5-d]oxepin-8-yl)-3-chloro-1,2,4-thiadiazol-5-amine (90 mg, 0.16 mmol) in THF (3 mL) and H₂O (1 mL) was added PPh₃ (86 mg, 0.33 mmol). The mixture was stirred at 70° C. overnight and then evaporated. The residue was purified by prep-TLC to give N-((3aR,4S,7S,8R,8aR)-4-(13-amino-2,5,8,11-tetraoxatridecyl)-2,2-dimethylhexahydro-4,7-epoxy[1,3]dioxolo[4,5-d]oxepin-8-yl)-3-chloro-1,2,4-thiadiazol-5-amine (70 mg, 82% yield) as colorless oil. LC-MS (ESI) found: 525 [M+H]⁺.

Step 4: To a solution of 1-((2,4-dinitrophenyl)amino)-11-oxo-3,6,9,15-tetraoxa-12-azaoctadecan-18-oic acid (72 mg, 0.15 mmol) in DMF (2 mL) were treated with HATU (158 mg, 0.42 mmol) and DIPEA (52 mg, 0.40 mmol). The mixture was cooled to 0° C. for 30 min. N-((3aR,4S,7S,8R,8aR)-4-(13-amino-2,5,8,11-tetraoxatridecyl)-2,2-dimethylhexahydro-4,7-epoxy[1,3]dioxolo[4,5-d]oxepin-8-yl)-3-chloro-1,2,4-thiadiazol-5-amine (70 mg, 0.13 mmol) was added and the mixture was stirred at rt overnight. The mixture was purified by prep-TLC followed by C18 to give N-(1-((3aR,4S,7S,8R,8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)-2,5,8,11-tetraoxatridecan-13-yl)-3-((14-((2,4-dinitrophenyl)amino)-4-oxo-6,9,12-trioxa-3-azatetradecyl)oxy)propanamide (70 mg, 53% yield) as yellow oil. LC-MS (ESI) found: 995 [M+H]⁺.

Step 5: To a solution of N-(1-((3aR,4S,7S,8R,8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)-2,5,8, 11-tetraoxatridecan-13-yl)-3-((14-((2,4-dinitrophenyl)amino)-4-oxo-6,9,12-trioxa-3-azatetradecyl)oxy)propanamide (70 mg, 0.07 mmol) in THF (3 mL) was added HCl (0.3 mL, 2 M in H$_2$O) at rt. The mixture was stirred at rt overnight, the mixture was purified by prep-HPLC (Method A) to give N-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)-3-((14-((2,4-dinitrophenyl)amino)-4-oxo-6,9,12-trioxa-3-azatetradecyl)oxy)propanamide (Compound 29, 43 mg, 65% yield) as yellow solid. LC-MS (ESI) found: 955 [M+H]$^+$. $^1$H NMR (400 MHz, MeOD): δ 9.03 (d, J=2.7 Hz, 1H), 8.29 (dd, J=9.6, 2.7 Hz, 1H), 7.23 (d, J=9.6 Hz, 1H), 5.37 (d, J=1.0 Hz, 1H), 3.98 (d, J=9.7 Hz, 3H), 3.92 (d, J=4.1 Hz, 1H), 3.81 (dd, J=6.6, 4.7 Hz, 3H), 3.76 (dd, J=9.6, 4.2 Hz, 1H), 3.72-3.66 (m, 16H), 3.65-3.61 (m, 11H), 3.53 (dt, J=10.9, 5.5 Hz, 4H), 3.38 (dt, J=8.4, 5.5 Hz, 4H), 2.44 (t, J=6.2 Hz, 2H).

Preparation of Compound 30, (3,3'-((2-(2-(2-(2-(2-((2,4-dinitrophenyl)amino)ethoxy)ethoxy)ethoxy)acetamido)propane-1,3-diyl)bis(oxy))bis(N-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide))

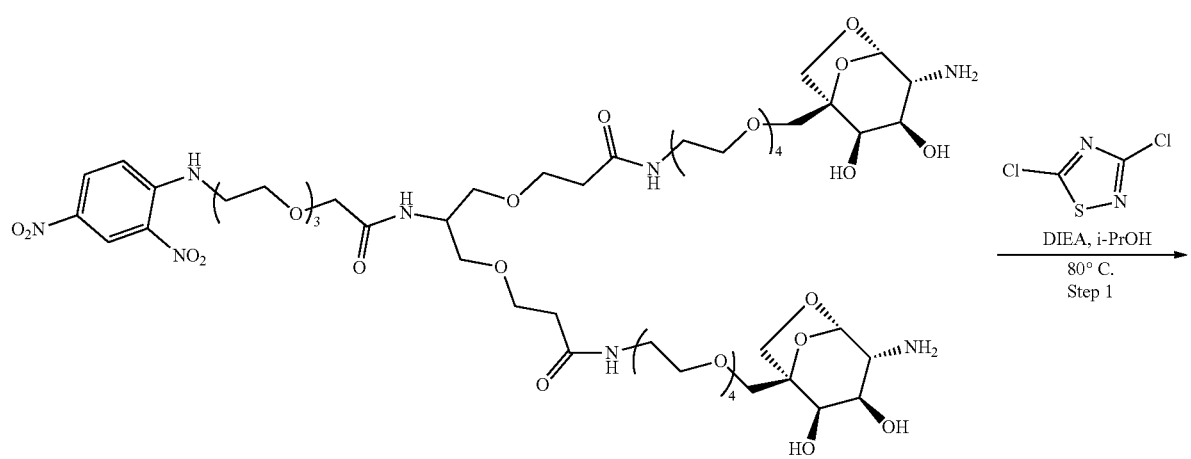

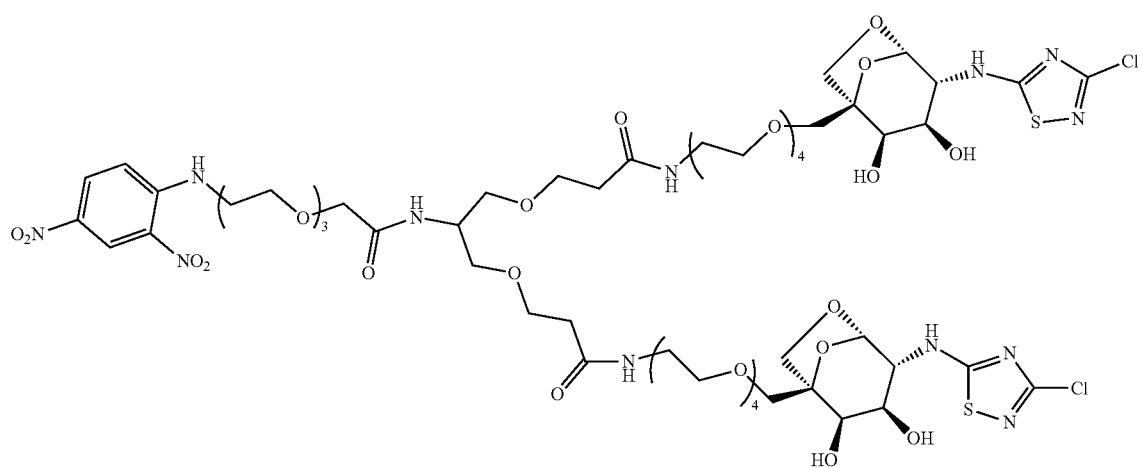

Step 1: To a solution of 3,3'-((2-(2-(2-(2-(2-((2,4-dinitrophenyl)amino)ethoxy)ethoxy) ethoxy)acetamido)propane-1,3-diyl)bis(oxy))bis(N-(1-((1S,2R,3R,4R,5S)-4-amino-2,3-dihydroxy-6,8-dioxabicyclo[3.2.1]octan-1-yl)-2,5,8,11-tetraoxatridecan-13-yl)propanamide) (20 mg, 0.016 mmol) in i-PrOH (3 mL) was added DIEA (0.003 mL, 0.016 mmol) and 3,5-dichloro-1,2,4-thiadiazole (19 mg, 0.124 mmol). The reaction was stirred at 80° C. for 18 h. The reaction was concentrated in vacuo. The residue was purified by prep-TLC and prep-HPLC (Method A) to afford 3,3'-((2-(2-(2-(2-(2-((2,4-dinitrophenyl)amino)ethoxy)ethoxy)ethoxy)acetamido)propane-1,3-diyl)bis(oxy))bis(N-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide) (Compound 30, 2.7 mg, 11% yield). LC-MS (ESI) found: 1525 [M+H]$^+$. $^1$H NMR (400 MHz, MeOD): δ 9.04 (d, J=2.7 Hz, 1H), 8.29 (dd, J=9.6, 2.7 Hz, 1H), 7.23 (d, J=9.6 Hz, 1H), 5.38 (s, 2H), 4.19 (t, J=5.5 Hz, 1H), 3.99 (t, J=4.8 Hz, 4H), 3.92 (d, J=4.1 Hz, 2H), 3.82 (dd, J=9.2, 3.1 Hz, 6H), 3.76 (dd, J=9.6, 4.2 Hz, 2H), 3.68 (ddd, J=6.4, 4.1, 1.5 Hz, 22H), 3.64-3.60 (m, 20H), 3.52 (ddd, J=15.2, 10.4, 4.9 Hz, 8H), 3.37 (t, J=5.5 Hz, 4H), 2.44 (t, J=6.2 Hz, 4H).

Preparation of Compound 31, (3,3'-((2-(2-(2-(2-(2-((2,4-dinitrophenyl)amino)ethoxy)ethoxy)ethoxy)acetamido)propane-1,3-diyl)bis(oxy))bis(N-(1-((1S,2R,3R,4R,5S)-2,3-dihydroxy-4-((4-(trifluoromethyl)pyrimidin-2-yl)amino)-6,8-dioxabicyclo[3.2.1]octan-1-yl)-2,5,8,11-tetraoxatridecan-13-yl)propanamide))

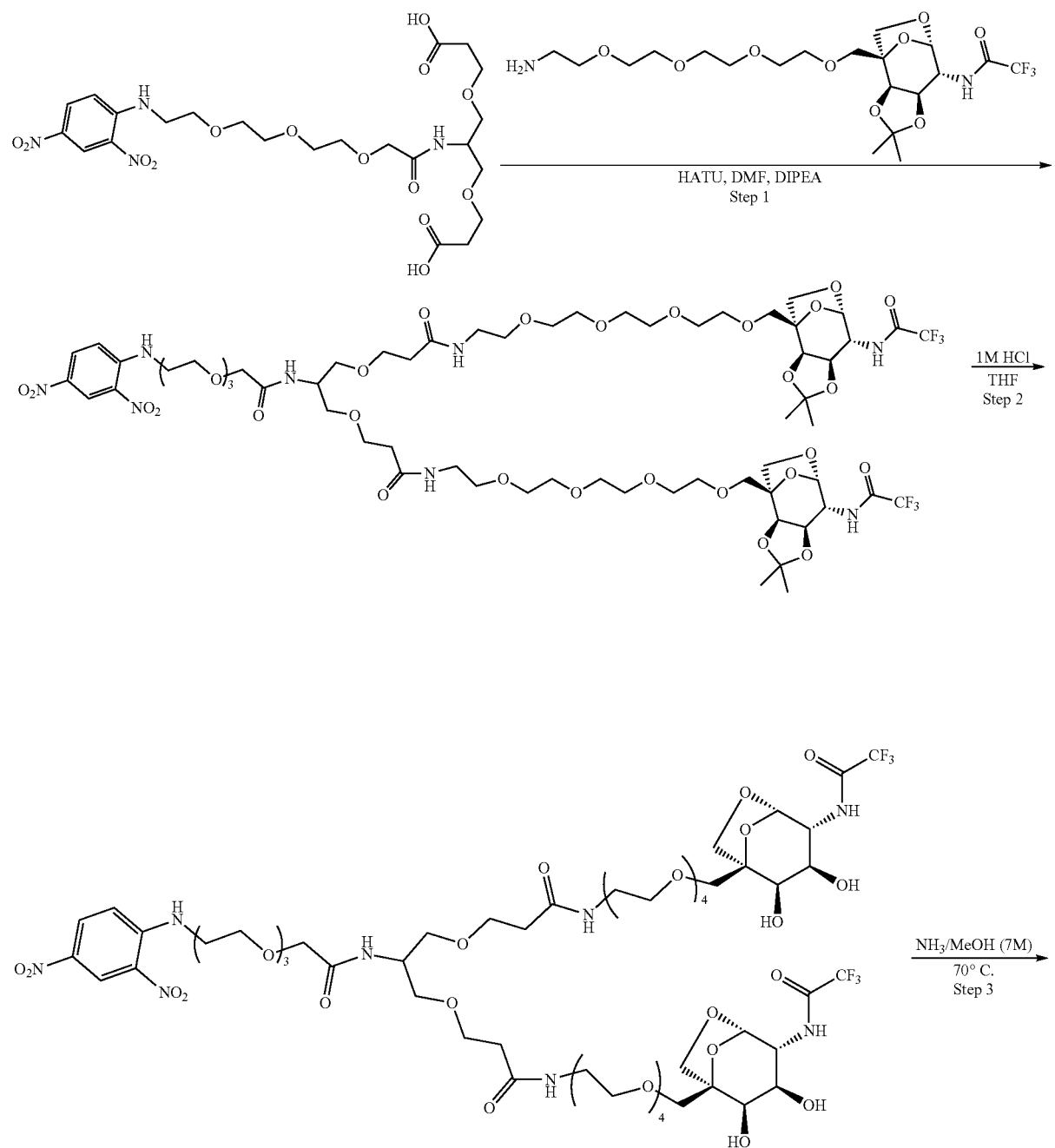

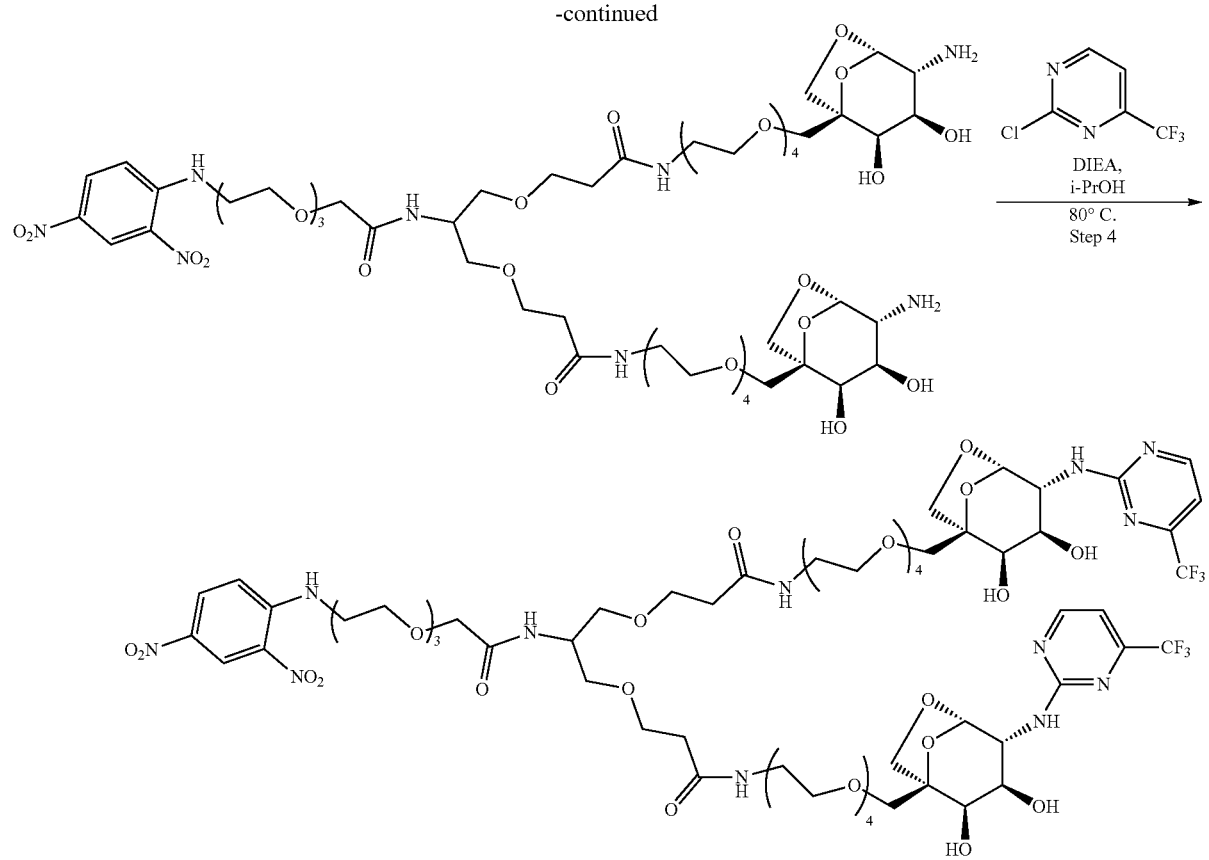

Step 1: To a solution of 13-((2-carboxyethoxy)methyl)-1-((2,4-dinitrophenyl)amino)-11-oxo-3,6,9,15-tetraoxa-12-azaoctadecan-18-oic acid (914 mg, 1.548 mmol) in DMF (10 mL) were added HATU (1.5 g, 3.869 mmol) and DIPEA (1.0 g, 7.739 mmol). The reaction mixture was stirred at ice water for 0.5 h. N-((3aR,4S,7S,8R,8aR)-4-(13-amino-2,5,8,11-tetraoxatridecyl)-2,2-dimethylhexahydro-4,7-epoxy[1,3]dioxolo[4,5-d]oxepin-8-yl)-2,2,2-trifluoroacetamide (1.7 g, 3.405 mmol) was added, the reaction mixture was stirred at room temperature for 16 h. EA was added, the mixture was washed by water. The organic phase was separated, concentrated and purified by flash (DCM:MeOH=20:1) to give 3,3'-((2-(2-(2-(2-(2-((2,4-dinitrophenyl)amino)ethoxy)ethoxy)ethoxy)acetamido)propane-1,3-diyl)bis(oxy))bis(N-(1-((3aR,4S,7S,8R,8aR)-2,2-dimethyl-8-(2,2,2-trifluoroacetamido)tetrahydro-4,7-epoxy[1,3]dioxolo[4,5-d]oxepin-4(5H)-yl)-2,5,8,11-tetraoxatridecan-13-yl)propanamide) (600 mg, 25% yield). LC-MS (ESI) found: 1560 [M+H]$^+$.

Step 2: 3,3'-((2-(2-(2-(2-(2-((2,4-dinitrophenyl) amino) ethoxy) ethoxy)ethoxy) acetamido) propane-1,3-diyl)bis(oxy))bis(N-(1-((3aR,4S,7S,8R,8aR)-2,2-dimethyl-8-(2,2,2-trifluoroacetamido)tetrahydro-4,7-epoxy[1,3]dioxolo[4,5-d]oxepin-4(5H)-yl)-2,5,8,11-tetraoxatridecan-13-yl)propanamide) (50 mg, 0.032 mmol) was dissolved in a mixture of HCl (0.5 ml, 2 M in H$_2$O) and THF (1 mL). The mixture was stirred at rt for 14 h. The solvent was evaporated, and the residue was co-evaporated twice with toluene. The crude material was purified by prep-HPLC (Method A) to give 3,3'-((2-(2-(2-(2-(2-((2,4-dinitrophenyl)amino)ethoxy)ethoxy)ethoxy)acetamido)propane-1,3-diyl)bis(oxy))bis(N-(1-((1S,2R,3R,4R,5S)-2,3-dihydroxy-4-(2,2,2-trifluoroacetamido)-6,8-dioxabicyclo[3.2.1]octan-1-yl)-2,5,8,11-tetraoxatridecan-13-yl)propanamide) (30 mg, 63% yield). LC-MS (ESI) found: 1480 [M+H]$^+$.

Step 3: 3,3'-((2-(2-(2-(2-(2-((2,4-dinitrophenyl)amino) ethoxy) ethoxy)ethoxy) acetamido) propane-1,3-diyl)bis (oxy))bis(N-(1-((1S,2R,3R,4R,5S)-2,3-dihydroxy-4-(2,2,2-trifluoroacetamido)-6,8-dioxabicyclo[3.2.1]octan-1-yl)-2,5,8,11-tetraoxatridecan-13-yl)propanamide) (30 mg, 0.020 mmol) were dissolved in NH$_3$ solution (3 mL, 7 M in MeOH), and the reaction was stirred at 70° C. for 18 h. The reaction was concentrated in vacuo, affording the crude 3,3'-((2-(2-(2-(2-(2-((2,4-dinitrophenyl)amino)ethoxy) ethoxy)acetamido) propane-1,3-diyl)bis(oxy))bis(N-(1-((1S,2R,3R,4R,5S)-4-amino-2,3-dihydroxy-6,8-dioxa bicyclo[3.2.1]octan-1-yl)-2,5,8,11-tetraoxatridecan-13-yl) propanamide) (26 mg, 99% yield). LC-MS (ESI) found: 1288 [M+H]$^+$.

Step 4: To a solution of 3,3'-((2-(2-(2-(2-(2-((2,4-dinitrophenyl)amino)ethoxy)ethoxy) ethoxy)acetamido)propane-1,3-diyl)bis(oxy))bis(N-(1-((1S,2R,3R,4R,5S)-4-amino-2,3-dihydroxy-6,8-dioxabicyclo[3.2.1]octan-1-yl)-2,5,8,11-tetraoxatridecan-13-yl)propanamide) (20 mg, 0.016 mmol) in i-PrOH (3 mL) was added DIEA (0.021 mL, 0.124 mmol) and 2-chloro-4-(trifluoromethyl)pyrimidine (23 mg, 0.124 mmol). The reaction was stirred at 80° C. for 18 h. The reaction was concentrated in vacuo. The residue was purified by prep-TLC and prep-HPLC (Method A) to afford 3,3'-((2-(2-(2-(2-(2-((2,4-dinitrophenyl)amino)ethoxy)ethoxy) ethoxy)acetamido)propane-1,3-diyl)bis(oxy))bis(N-(1-((1S,2R,3R,4R,5S)-2,3-dihydroxy-4-((4-(trifluoromethyl)pyrimidin-2-yl)amino)-6,8-dioxabicyclo[3.2.1]octan-1-yl)-2,5,8,11-tetraoxatridecan-13-yl)propanamide) (Compound 31, 3.1 mg, 13% yield). LC-MS (ESI) found: 1580 [M+H]$^+$. $^1$H NMR (400 MHz, MeOD): δ 9.03 (d, J=2.7 Hz, 1H), 8.52 (d, J=4.9 Hz, 2H), 8.28 (dd, J=9.6, 2.7 Hz, 1H), 7.22 (d, J=9.6 Hz, 1H), 6.91 (d, J=4.9 Hz, 2H), 5.36 (d, J=1.3 Hz, 2H), 4.23-4.14 (m, 3H), 4.03-3.96 (m, 4H), 3.94 (d, J=4.3 Hz, 2H), 3.90-3.79 (m, 6H), 3.72-3.65 (m, 22H), 3.64-3.58 (m, 20H), 3.52 (ddd, J=15.2, 10.3, 4.8 Hz, 8H), 3.36 (t, J=5.5 Hz, 4H), 2.44 (t, J=6.2 Hz, 4H).
Preparation of Compound 32, (3,3'-((2-(2-(2-(2-(2-((2,4-dinitrophenyl) amino)ethoxy) ethoxy) ethoxy) acetamido)propane-1,3-diyl)bis(oxy))bis(N-(1-((2R, 3R,4R,5S)-3,4-dihydroxy-5-((4-(trifluoromethyl) pyrimidin-2-yl)amino)tetrahydro-2H-pyran-2-yl)-2, 5,8,11-tetraoxatridecan-13-yl)propenamide))
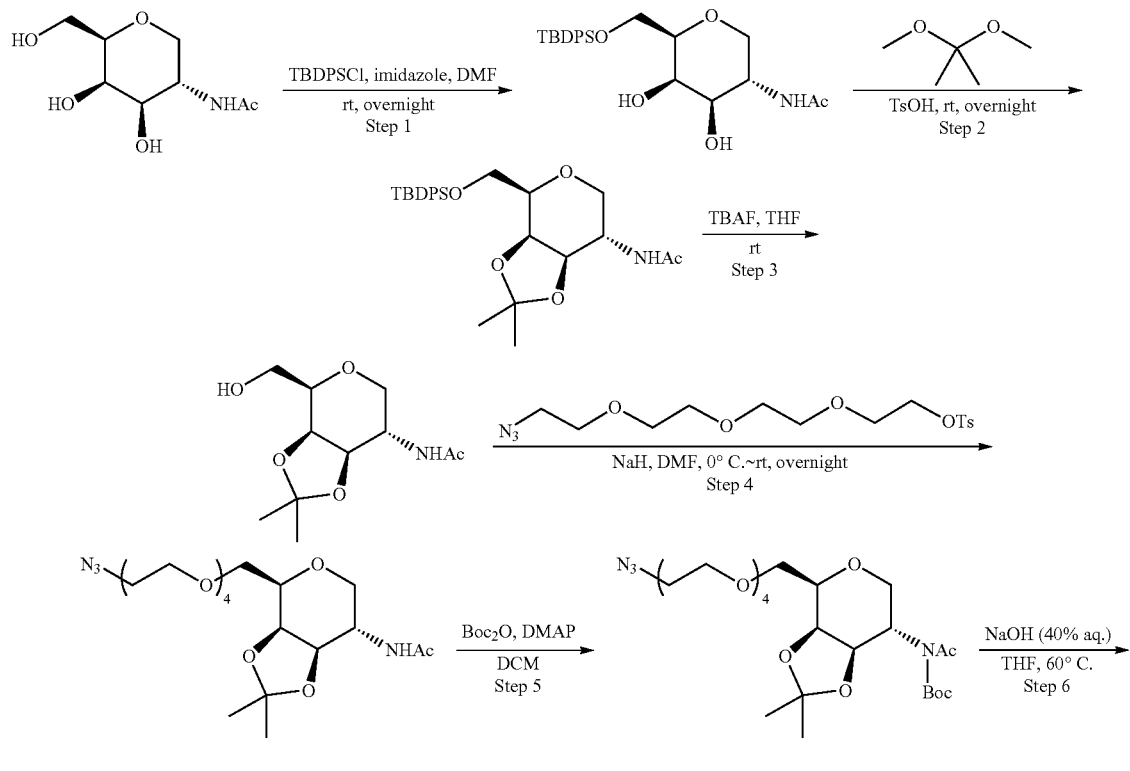
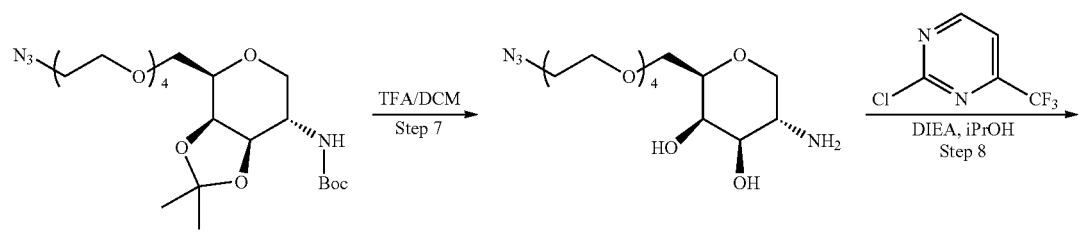
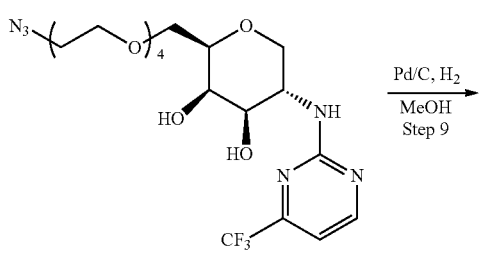

-continued

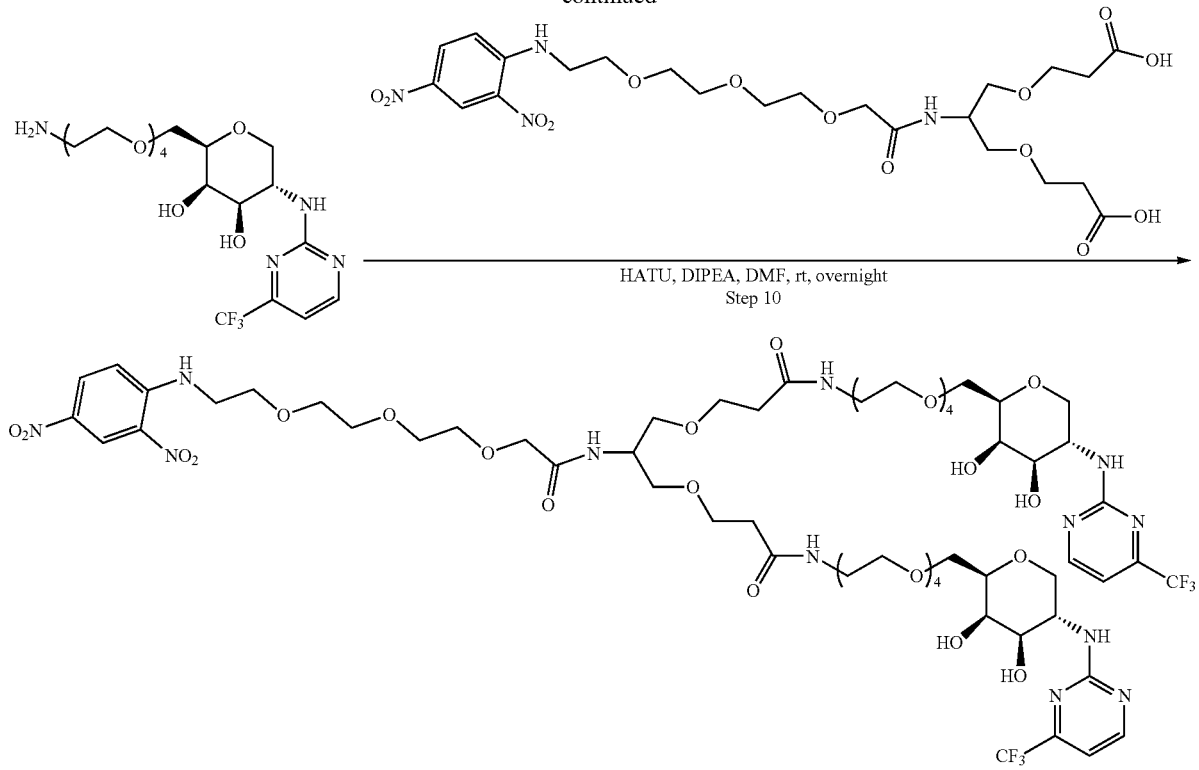

HATU, DIPEA, DMF, rt, overnight
Step 10

Step 1: To a solution of N-[(3S,4R,5R,6R)-4,5-dihydroxy-6-(hydroxymethyl)oxan-3-yl]acetamide (10 g, 48.7 mmol) in DMF (100 mL) was added imidazole (6.6 g, 97.5 mmol) and TBDPS chloride (19 g, 73.1 mmol), and the reaction was stirred at room temperature overnight. The mixture was diluted with ethyl acetate (300 mL) and washed with water (100 mL×3). The organic layer was dried over sodium sulfate and concentrated under reduced pressure to give a crude product, which was purified by flash chromatography (silica gel, 0-10% DCM in MeOH) to give N-((3S,4R,5R,6R)-6-(((tert-butyldiphenylsilyl)oxy)methyl)-4,5-dihydroxytetrahydro-2H-pyran-3-yl)acetamide (15 g, 69% yield) as white solid. LC-MS (ESI) found: 444 [M+H]⁺.

Step 2: To a solution of N-((3S,4R,5R,6R)-6-(((tert-butyldiphenylsilyl)oxy)methyl)-4,5-dihydroxytetrahydro-2H-pyran-3-yl)acetamide (15 g, 33.8 mmol) in 2,2-dimethoxypropane (100 mL) was added TsOH (0.58 g, 3.38 mmol), and the reaction was stirred at room temperature overnight. The mixture was concentrated under reduced pressure to give a crude product N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)acetamide (15 g, 93% yield) as a yellow oil. LC-MS (ESI) found: 484 [M+H]⁺.

Step 3: To a solution of N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)acetamide (15 g, 31 mmol) in THF (100 mL) was added TBAF solution (20 mL, 2 M in THF), and the reaction was stirred at room temperature overnight. The mixture was concentrated under reduced pressure to give a crude product, which was purified by flash chromatography (silica gel, 0-10% DCM in MeOH) to give N-((3aR,4R,7S,7aR)-4-(hydroxymethyl)-2,2-dimethyltetrahydro-4H-[1,3]dioxolo[4,5-c]pyran-7-yl)acetamide (7 g, 92% yield) as white solid. LC-MS (ESI) found: 246 [M+H]⁺.

Step 4: To a solution of N-((3aR,4R,7S,7aR)-4-(hydroxymethyl)-2,2-dimethyltetrahydro-4H-[1,3]dioxolo[4,5-c]pyran-7-yl)acetamide (3.5 g, 14.3 mmol) in DMF (100 mL) at 0° C. was added NaH (0.68 g, 60% wt. in mineral oil), then the mixture was stirred at room temperature overnight. On consumption of starting material (LCMS monitoring), the reaction vessel was again cooled to 0° C., water (10 mL) was slowly added and the reaction mixture stirred for 15 min. The mixture was diluted with ethyl acetate (200 mL) and washed with water (200 mL×3). The organic layer was dried over sodium sulfate, concentrated under reduced pressure to give a crude product, which was purified by flash chromatography to give N-((3aR,4R,7S,7aR)-4-(13-azido-2,5,8,11-tetraoxatridecyl)-2,2-dimethyltetrahydro-4H-[1,3]dioxolo[4,5-c]pyran-7-yl)acetamide (3.5 g, 58% yield) as a colorless oil. LC-MS (ESI) found: 447 [M+H]⁺.

Step 5: To a solution of N-((3aR,4R,7S,7aR)-4-(13-azido-2,5,8,11-tetraoxatridecyl)-2,2-dimethyltetrahydro-4H-[1,3]dioxolo[4,5-c]pyran-7-yl)acetamide (4 g, 14.5 mmol) in THF (200 mL) at 0° C. was added TEA (2.1 mL, 14.8 mmol), DMAP (0.12 g, 0.98 mmol), and di-tert-butyl dicarbonate (3.2 mL, 14.8 mmol), then the mixture was stirred at room temperature overnight. On consumption of starting material (LCMS monitoring), the reaction vessel was again cooled to 0° C., water (20 mL) was slowly added and the reaction mixture stirred for 15 min. The mixture was diluted with ethyl acetate (200 mL) and wash with water (200 mL×3). The organic layer was dried over sodium sulfate and concentrated under reduced pressure to give a crude product, which was purified by flash chromatography to give tert-butyl acetyl((3aR,4R,7S,7aR)-4-(13-azido-2,5,8,11-tetraoxatridecyl)-2,2-dimethyltetrahydro-4H-[1,3]dioxolo[4,5-c]pyran-7-yl)carbamate (4.0 g, 82% yield) as a colorless oil. LC-MS (ESI) found: 547 [M+H]⁺.

Step 6: To a solution of tert-butyl acetyl((3aR,4R,7S,7aR)-4-(13-azido-2,5,8,11-tetraoxatridecyl)-2,2-dimethyltetrahydro-4H-[1,3]dioxolo[4,5-c]pyran-7-yl)carbamate (4 g, 8.9 mmol) in THF (200 mL) at rt was added NaOH (40% wt. in H₂O, 12 mL), then the mixture was stirred at the room temperature overnight. On consumption of starting material (LCMS monitoring), water (20 mL) was slowly added. The mixture was diluted with ethyl acetate (200 mL) and wash with water (200 mL×3). The organic layer was dried over sodium sulfate, filtered, concentrated under reduced pressure to give a crude product, which was purified by flash chromatography to give tert-butyl ((3aR,4R,7S,7aR)-4-(13-azido-2,5,8,11-tetraoxatridecyl)-2,2-dimethyltetrahydro-4H-[1,3]dioxolo[4,5-c]pyran-7-yl)carbamate (3.2 g, 89% yield) as a colorless oil. LC-MS (ESI) found: 505 [M+H]⁺.

Step 7: To a solution of tert-butyl ((3aR,4R,7S,7aR)-4-(13-azido-2,5,8,11-tetraoxatridecyl)-2,2-dimethyltetrahydro-4H-[1,3]dioxolo[4,5-c]pyran-7-yl)carbamate (3.2 g, 6.9 mmol) in DCM (100 mL) at rt was added TFA (10 mL), then the mixture was stirred at the 60° C. overnight. The mixture was concentrated under reduced pressure to give a crude product, which was purified by flash chromatography to give (2R,3R,4R,5S)-5-amino-2-(13-azido-2,5,8,11-tetraoxatridecyl)tetrahydro-2H-pyran-3,4-diol (1.5 g, 65% yield) as a white solid. LC-MS (ESI) found: 365 [M+H]⁺.

Step 8: To a solution of (2R,3R,4R,5S)-5-amino-2-(13-azido-2,5,8,11-tetraoxatridecyl)tetrahydro-2H-pyran-3,4-diol (200 mg, 0.55 mmol) and DIPEA (209 mg, 1.65 mmol) in dry i-PrOH (2 mL) at rt under N₂ atmosphere was added 2-chloro-4-(trifluoromethyl)pyrimidine (199 mg, 1.1 mmol). After the addition was complete, the reaction was stirred at 80° C. for overnight. On consumption of starting material (TLC monitoring), the reaction vessel was again cooled to rt. The mixture was concentrated under reduced pressure. The crude product was purified by flash chromatography (silica gel, 0-10% MeOH in DCM) to give (2R,3R,4R,5S)-2-(13-azido-2,5,8,11-tetraoxatridecyl)-5-((4-(trifluoromethyl)pyrimidin-2-yl)amino)tetrahydro-2H-pyran-3,4-diol (150 mg, 54% yield) as a white solid. LC-MS (ESI) found: 365 [M+H]⁺.

Step 9: To a solution of (2R,3R,4R,5S)-2-(13-azido-2,5,8,11-tetraoxatridecyl)-5-((4-(trifluoromethyl)pyrimidin-2-yl)amino)tetrahydro-2H-pyran-3,4-diol (14 mg, 0.027 mmol) in MeOH (2 mL) was added Pd/C (4 mg, 10% wt, 60% wet). The mixture was stirred at rt for 0.5 h under a H₂ balloon. The mixture was filtered and concentrated to give crude (2R,3R,4R,5S)-2-(13-amino-2,5,8,11-tetraoxatridecyl)-5-((4-(trifluoromethyl)pyrimidin-2-yl)amino)tetrahydro-2H-pyran-3,4-diol (13 mg, 97% yield) as yellow oil. LC-MS (ESI) found: 459 [M+H]⁺.

Step 10: To a solution of (2R,3R,4R,5S)-2-(13-amino-2,5,8,11-tetraoxatridecyl)-5-((4-(trifluoromethyl)pyrimidin-2-yl)amino)tetrahydro-2H-pyran-3,4-diol (13.1 mg, 0.027 mmol) and 6-((2-carboxyethoxy)methyl)-19-(2,4-dinitrophenyl)-8-oxo-4,10,13,16-tetraoxa-7-azanonadecanoic acid (7.0 mg, 0.012 mmol) in DMF (1 mL) was added HATU (6.7 mg, 0.018 mmol) and DIPEA (4.6 mg, 0.036 mmol) at 0° C. The mixture was stirred at rt for 12 h. The mixture was concentrated and purified by HPLC (Method A) to give 3,3'-((2-(2-(2-(2-(2-((2,4-dinitrophenyl)amino)ethoxy)ethoxy)ethoxy)acetamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (Compound 32, 6.1 mg, 34% yield) as a yellow oil. LC-MS (ESI) found: 1523 [M+H]⁺. ¹H NMR (400 MHz, MeOD): δ 9.03 (d, J=2.7 Hz, 1H), 8.50 (d, J=4.7 Hz, 2H), 8.29 (dd, J=9.6, 2.7 Hz, 1H), 7.23 (d, J=9.6 Hz, 1H), 6.89 (d, J=4.9 Hz, 2H), 4.35 (d, J=5.0 Hz, 2H), 4.23-4.13 (m, 1H), 4.08 (dd, J=10.9, 5.2 Hz, 2H), 3.99 (s, 2H), 3.91 (d, J=3.0 Hz, 2H), 3.81 (t, J=5.2 Hz, 2H), 3.74-3.48 (m, 54H), 3.36 (t, J=5.5 Hz, 4H), 3.16 (t, J=10.9 Hz, 2H), 2.44 (t, J=6.2 Hz, 4H).

Preparation of Compound 33, (3,3'-((2-(2-(2-(2-(2-((2,4-dinitrophenyl)amino)ethoxy)ethoxy)ethoxy)acetamido)propane-1,3-diyl)bis(oxy))bis(N-(1-((2R,3R,4R,5R)-5-acetamido-3,4-dihydroxytetrahydro-2H-pyran-2-yl)-2,5,8,11-tetraoxatridecan-13-yl)propanamide))

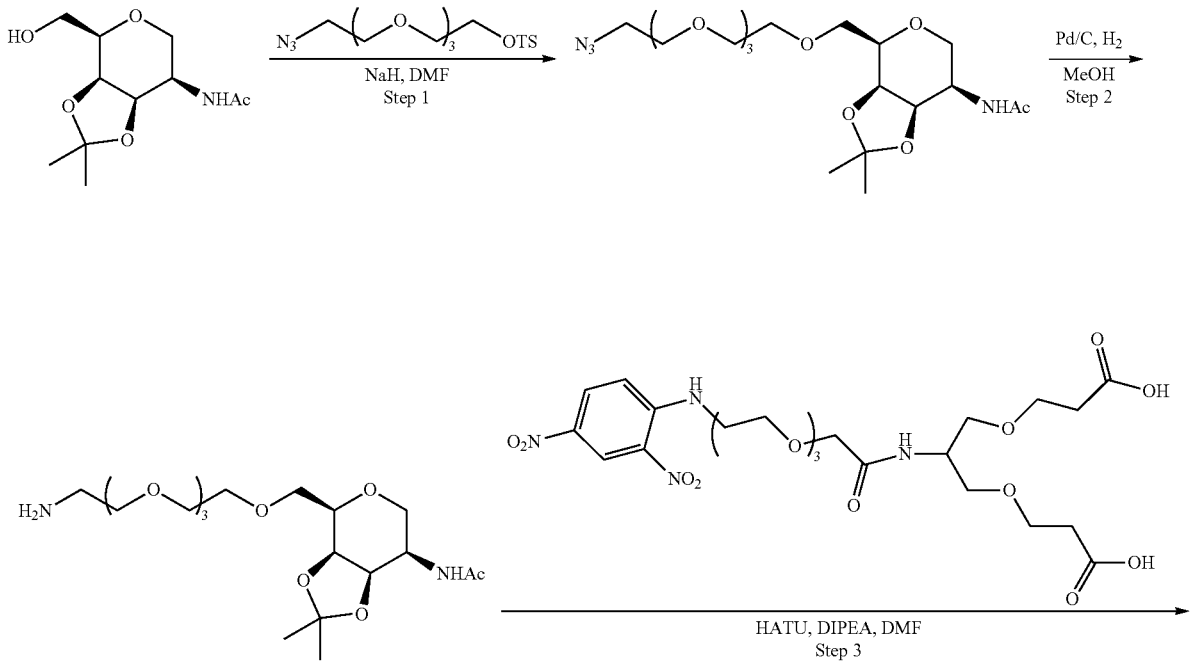

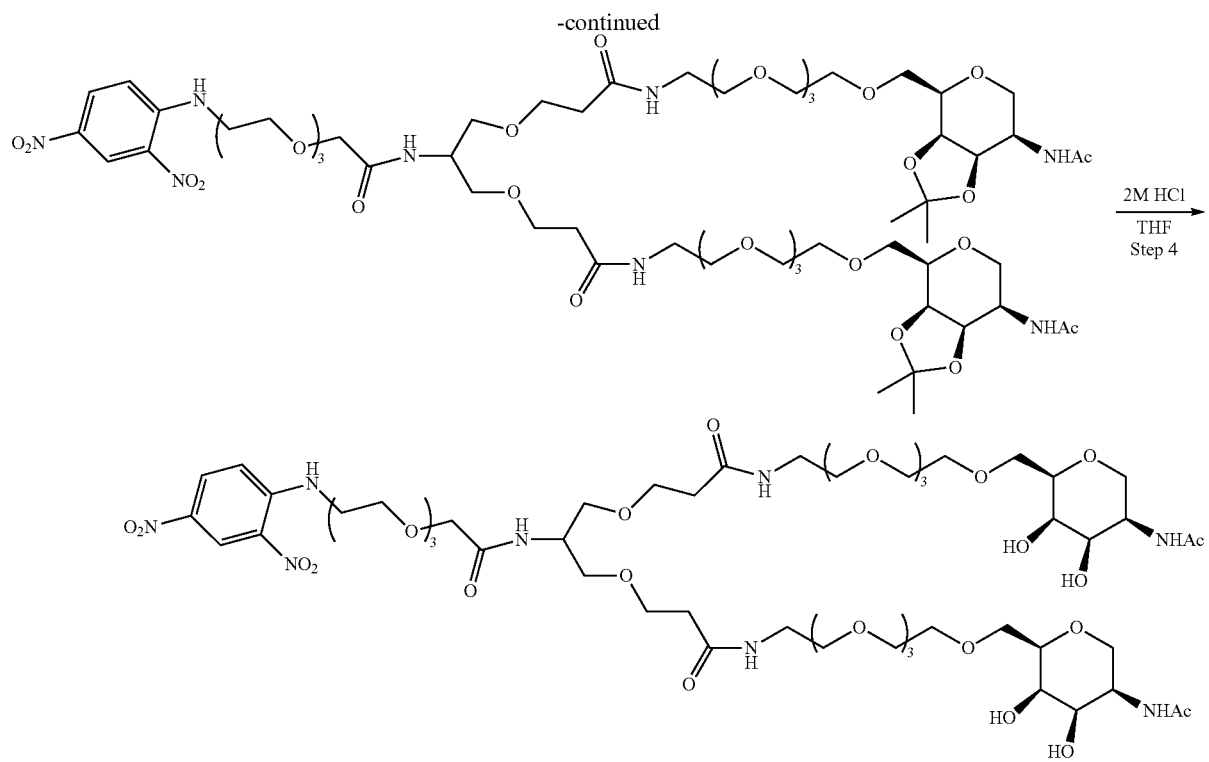

Step 1: To a solution of N-((3aR,4R,7R,7aR)-4-(hydroxymethyl)-2,2-dimethyltetrahydro-4H-[1,3]dioxolo[4,5-c]pyran-7-yl)acetamide (120 mg, 0.49 mmol) in DMF (3 mL) was added NaH (23.5 mg, 0.98 mmol) at 0° C. and stirred for 1 h under $N_2$. Then 2-(2-(2-(2-azidoethoxy)ethoxy)ethoxy)ethyl 4-methylbenzenesulfonate (274.04 mg, 0.73 mmol) was added at 0° C. and stirred at rt for 2 h under $N_2$. The resulting mixture was diluted with DCM (30 mL) and water (10 mL). The aqueous phase was extracted with DCM (10 mL×2). The organic layer was separated, dried over $Na_2SO_4$ and concentrated in vacuo. The crude product was purified by flash chromatography (silica gel, 0~10% MeOH in DCM) to give N-((3aR,4R,7R,7aR)-4-(13-azido-2,5,8,11-tetraoxatridecyl)-2,2-dimethyltetrahydro-4H-[1,3]dioxolo[4,5-c]pyran-7-yl)acetamide (90 mg, 45% yield) as a colorless oil. LC-MS (ESI) found: 447 [M+H]$^+$.

Step 2: To a solution of N-((3aR,4R,7R,7aR)-4-(13-azido-2,5,8,11-tetraoxatridecyl)-2,2-dimethyltetrahydro-4H-[1,3]dioxolo[4,5-c]pyran-7-yl)acetamide (90 mg, 0.2 mmol) in MeOH (5 mL) was added Pd/C (10 mg, 10% wt, 60% wet) at rt under a $H_2$ balloon. The reaction was stirred at rt for 1.5 h. The resulting mixture was filtered and concentrated in vacuo. The crude product N-((3aR,4R,7R,7aR)-4-(13-amino-2,5,8,11-tetraoxatridecyl)-2,2-dimethyltetrahydro-4H-[1,3]dioxolo[4,5-c]pyran-7-yl)acetamide (60 mg, 71% yield) was used in the next step with no further purification. LC-MS (ESI) found: 421 [M+H]$^+$.

Step 3: A solution of 13-((2-carboxyethoxy)methyl)-1-((2,4-dinitrophenyl)amino)-11-oxo-3,6,9,15-tetraoxa-12-azaoctadecan-18-oic acid (10 mg, 0.02 mmol) and HATU (16.2 mg, 0.043 mmol) in DMF (2 mL) was stirred at rt for 30 min, then N-((3aR,4R,7R,7aR)-4-(13-amino-2,5,8,11-tetraoxatridecyl)-2,2-dimethyltetrahydro-3aH-[1,3]dioxolo[4,5-c]pyran-7-yl)acetamide (21.4 mg, 0.05 mmol) and N,N-Diisopropylethylamine (0.01 mL, 0.07 mmol) were added at rt. The reaction was stirred overnight. The residue was purified by prep-HPLC (Method A) to give 3,3'-((2-(2-(2-(2-(2-(((2,4-dinitrophenyl)amino)ethoxy)ethoxy)ethoxy)acetamido)propane-1,3-diyl)bis(oxy))bis(N-(1-((3aR,4R,7R,7aR)-7-acetamido-2,2-dimethyltetrahydro-3aH-[1,3]dioxolo[4,5-c]pyran-4-yl)-2,5,8,11-tetraoxatridecan-13-yl)propanamide) (15 mg, 64% yield) as a yellow oil. LC-MS (ESI) found: 1396 [M+H]$^+$. $^1$H NMR (400 MHz, CDCl$_3$): δ 9.12 (d, J=2.7 Hz, 1H), 8.81 (s, 1H), 8.27 (dd, J=9.4, 2.6 Hz, 1H), 7.12 (d, J=8.8 Hz, 1H), 7.07 (t, J=5.3 Hz, 2H), 6.98 (d, J=9.5 Hz, 1H), 5.94 (dd, J=8.2, 4.4 Hz, 2H), 4.38 (dd, J=7.8, 3.0 Hz, 4H), 4.25 (dd, J=7.1, 2.0 Hz, 2H), 3.99 (s, 2H), 3.87 (d, J=2.0 Hz, 2H), 3.82 (d, J=5.4 Hz, 2H), 3.70 (dd, J=8.1, 4.5 Hz, 15H), 3.65-3.61 (m, 30H), 3.54 (dd, J=6.8, 3.8 Hz, 6H), 3.46-3.40 (m, 6H), 2.43 (dd, J=12.7, 6.7 Hz, 4H), 2.00 (s, 6H), 1.49 (s, 6H), 1.33 (s, 6H).

Step 4: To a solution of 3,3'-((2-(2-(2-(2-(2-(((2,4-dinitrophenyl)amino)ethoxy)ethoxy)ethoxy)acetamido)propane-1,3-diyl)bis(oxy))bis(N-(1-((3aR,4R,7R,7aR)-7-acetamido-2,2-dimethyltetrahydro-3aH-[1,3]dioxolo[4,5-c]pyran-4-yl)-2,5,8,11-tetraoxatridecan-13-yl)propanamide) (15 mg, 0.01 mmol) in THF (3 mL) was added HCl (0.1 mL, 1 M in $H_2O$). The reaction was stirred at rt for 3 h. The crude product was purified by prep-HPLC (Method A) to give 3,3'-((2-(2-(2-(2-(2-(((2,4-dinitrophenyl)amino)ethoxy)ethoxy)ethoxy)acetamido)propane-1,3-diyl)bis(oxy))bis(N-(1-((2R,3R,4R,5R)-5-acetamido-3,4-dihydroxytetrahydro-2H-pyran-2-yl)-2,5,8,11-tetraoxatridecan-13-yl)propanamide) (Compound 33, 2.9 mg, 21% yield) as a yellow oil. LC-MS (ESI) found: 1316 [M+H]$^+$. $^1$H NMR (400 MHz, MeOD): δ 9.05 (d, J=2.7 Hz, 1H), 8.31 (dd, J=9.6, 2.7 Hz, 1H), 7.24 (d, J=9.6 Hz, 1H), 4.19 (t, J=5.6 Hz, 1H), 4.07 (d, J=3.5 Hz, 2H), 3.99 (s, 2H), 3.89-3.85 (m, 4H), 3.82 (t, J=5.2 Hz, 2H), 3.76-3.74 (m, 2H), 3.71-3.66 (m, 16H), 3.65-3.61 (m, 26H), 3.56-3.50 (m, 12H), 3.37 (t, J=5.5 Hz, 4H), 2.44 (t, J=6.2 Hz, 4H), 2.00 (s, 6H).

Preparation of Compound 36: 3,3'-((2-(2-(2-(2-(2-(4-(3-(4-(isoquinolin-8-yl)phenethoxy)-4-(1H-pyrrolo[3,2-c]pyridin-3-yl)benzyl)piperazin-1-yl)-2-oxoethoxy)ethoxy)ethoxy)acetamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide)

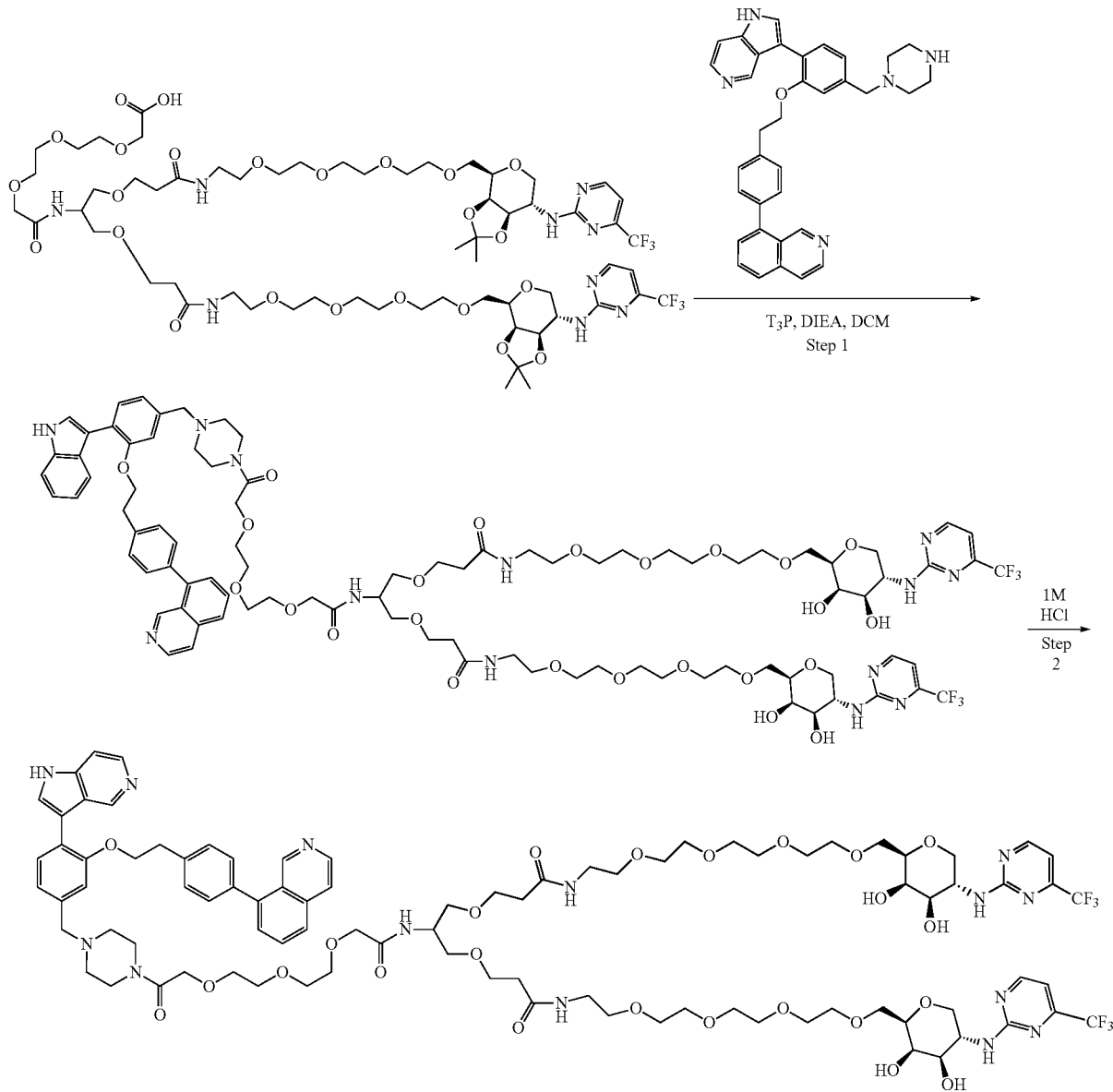

Compound 36

Step 1: To a mixture of 1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid (20 mg, 13.77 μmol, 1 eq.), 8-[4-[2-[5-(piperazin-1-ylmethyl)-2-(1H-pyrrolo[3,2-c]pyridin-3-yl)phenoxy]ethyl]phenyl]isoquinoline (8.17 mg, 15.15 μmol, 1.1 eq.) and DIEA (3.56 mg, 27.54 μmol, 4.80 μL, 2 eq.) in DCM (1 mL) then was added T₃P (13.14 mg, 41.31 μmol, 12.28 μL, 3 eq.), the mixture was stirred at 20° C. for 10.5 hr. Worked up and the combined organic layers were concentrated under reduced pressure to give a residue of 3,3'-((2-(2-(2-(2-(2-(4-(3-(4-(isoquinolin-8-yl)phenethoxy)-4-(1H-pyrrolo[3,2-c]pyridin-3-yl)benzyl)piperazin-1-yl)-2-oxoethoxy)ethoxy)acetamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H- pyran-2-yl)-2,5,8,11-tetraoxatridecan-13-yl)propanamide) (25 mg, crude) as a yellow oil.

Step 2: To a mixture of 3,3'-((2-(2-(2-(2-(2-(4-(3-(4-(iso-quinolin-8-yl)phenethoxy)-4-(1H-pyrrolo[3,2-c]pyridin-3-yl)benzyl)piperazin-1-yl)-2-oxoethoxy)ethoxy)ethoxy)acet-amido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (23 mg, 11.65 µmol, 1 eq.) in HCl (2 mL) was stirred at 20° C. for 3 hr. The reaction mixture was concentrated under reduced pressure to give a residue. The residue was purified by prep-HPLC (FA condition (column: Phenomenex Luna C18 150*30 mm*5 µm; mobile phase: [water (0.2% F A)-ACN]; B %: 20%-60%, 8 min)) to afford 3,3'-((2-(2-(2-(2-(2-(4-(3-(4-(isoquinolin-8-yl)phenethoxy)-4-(1H-pyrrolo[3,2-c]pyridin-3-yl)benzyl)piperazin-1-yl)-2-oxoethoxy)ethoxy)ethoxy)acetamido)propane-1,3-diyl)bis(oxy))bis(N-(1-((2R,3R,4R,5S)-3,4-dihydroxy-5-((4-(trifl-uoromethyl)pyrimidin-2-yl)amino)tetrahydro-2H-pyran-2-yl)-2,5,8,11-tetraoxatridecan-13-yl)propanamide) (Compound 36, 1.5 mg, 7.92e-1 µmol, 6.80% yield) was obtained as a white solid. $^1$H NMR (400 MHz, methanol-d4) δ=8.89 (br s, 1H), 8.38 (br s, 3H), 8.03-7.60 (m, 6H), 7.43 (br s, 3H), 7.29-6.91 (m, 6H), 6.77 (br d, J=4.5 Hz, 2H), 4.26 (br s, 3H), 4.20-4.14 (m, 2H), 4.14-4.03 (m, 2H), 3.95 (br s, 3H), 3.88 (br s, 2H), 3.81 (br s, 3H), 3.58 (br d, J=5.6 Hz, 21H), 3.52 (br s, 27H), 3.41 (br d, J=5.0 Hz, 10H), 3.25 (br s, 7H), 3.10-2.98 (m, 3H), 2.33 (br s, 5H).

Preparation of Compound 37: 3-((4-(isoquinolin-8-yl)-3-(4-(isoquinolin-8-yl)phenethoxy) benzyl)oxy) propanoic acid and 3,3'-((2-(3-((4-(isoquinolin-8-yl)-3-(4-(isoquinolin-8-yl)phenethoxy)benzyl)oxy) propanamido) propane-1,3-diyl)bis(oxy))bis(N-(1-((2R,3R,4R,5 S)-3,4-dihydroxy-5-((4-(trifluoromethyl) pyrimidin-2-yl)amino)tetrahydro-2H-pyran-2-yl)-2,5,8,11-tetraoxatridecan-13-yl) propanamide)

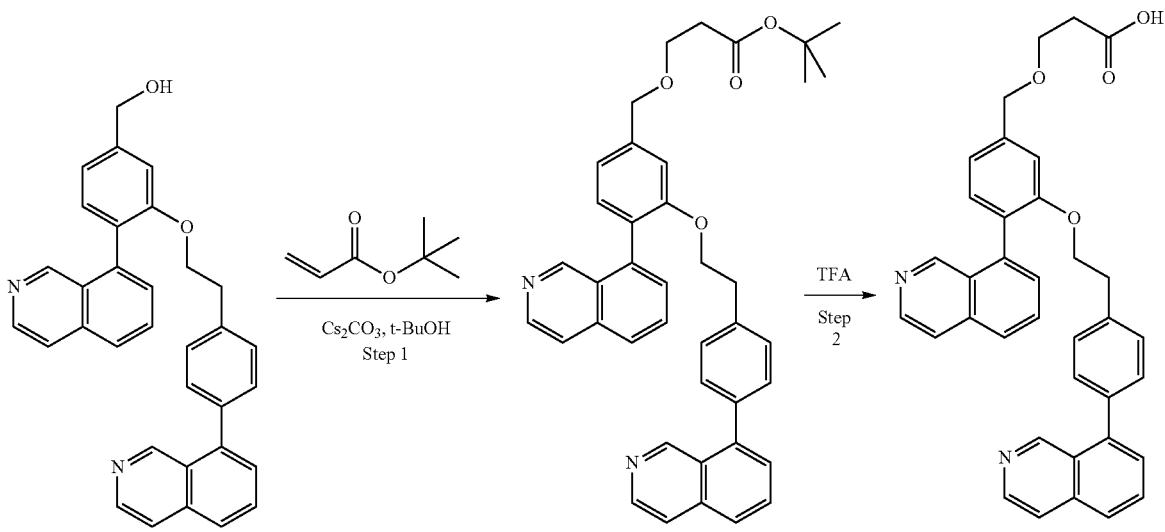

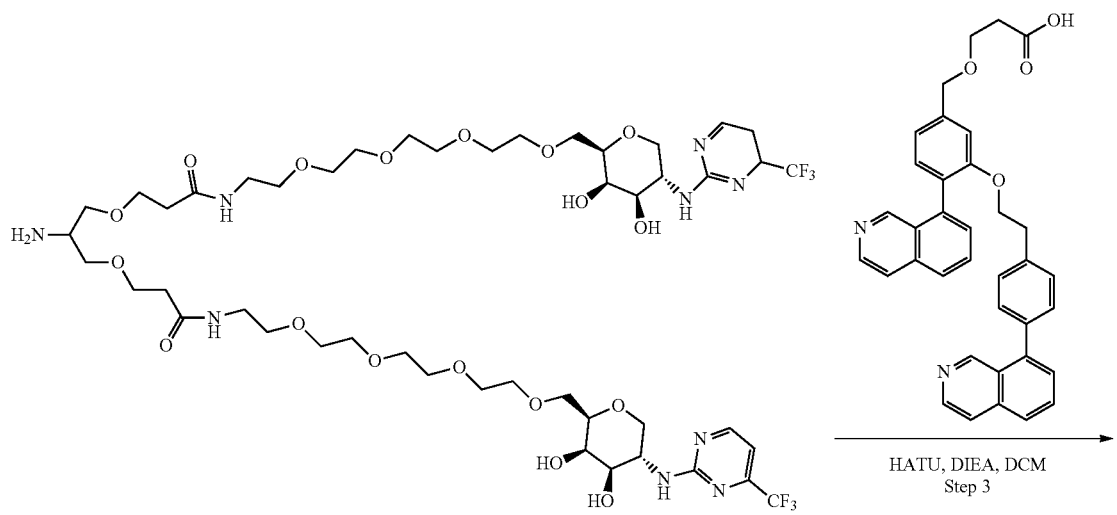

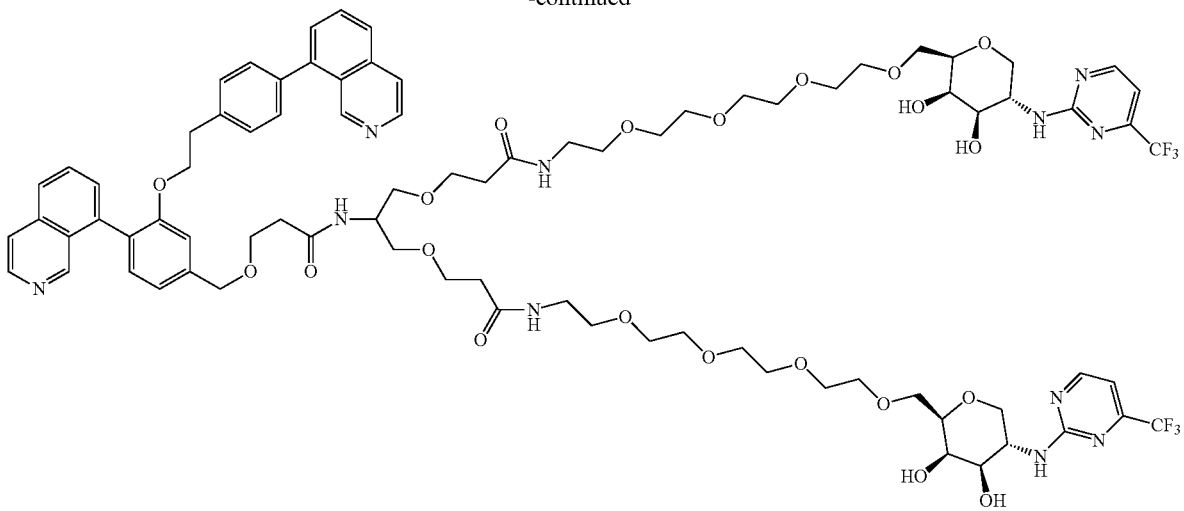

Compound 37

Step 1: To a solution of (4-(isoquinolin-8-yl)-3-(4-(isoquinolin-8-yl)phenethoxy)phenyl)methanol (200 mg, 414.45 µmol, 1 eq) and tert-butyl prop-2-enoate (159.36 mg, 1.24 mmol, 180.47 µL, 3 eq) in t-BuOH (5 mL) was added $Cs_2CO_3$ (270.07 mg, 828.89 µmol, 2 eq). The mixture was stirred at 55° C. for 5 hrs. The reaction mixture was diluted with $H_2O$ 10 mL and extracted with Ethyl acetate 10 mL*3. The combined organic layers were dried over by $Na_2SO_4$, filtered and concentrated under reduced pressure to give a residue. The residue was purified by prep-TLC ($SiO_2$, Petroleum ether: Ethyl acetate=1:1). tert-butyl 3-((4-(isoquinolin-8-yl)-3-(4-(isoquinolin-8-yl)phenethoxy)benzyl)oxy)propanoate (130 mg, 212.86 µmol, 51.36% yield) was obtained as a white solid.

Step 2: To a solution of tert-butyl 3-((4-(isoquinolin-8-yl)-3-(4-(isoquinolin-8-yl)phenethoxy)benzyl)oxy)propanoate (130 mg, 212.86 µmol, 1 eq) in DCM (2 mL) was added TFA (1.05 g, 9.24 mmol, 684.21 µL, 43.42 eq). The mixture was stirred at 15° C. for 1 hr. LCMS: The reaction mixture was concentrated under reduced pressure to give a residue. The crude product was purified by reversed-phase HPLC (column: Waters Xbridge BEH C18 100*30 mm*10 µm; mobile phase: [water (0.05% $NH_3H_2O$+10 mM $NH_4HCO_3$)-ACN]; B %: 15%-65%, 8 min @100 mL/min). 3-((4-(isoquinolin-8-yl)-3-(4-(isoquinolin-8-yl)phenethoxy)benzyl)oxy)propanoic acid (3.52 mg, 6.28 µmol, 2.95% yield, 98.9% purity) was obtained as a white solid. $^1$H NMR (400 MHz, methanol-$d_4$) δ=9.03 (s, 1H), 8.85 (s, 1H), 8.46 (br d, J=5.6 Hz, 1H), 8.35 (d, J=5.6 Hz, 1H), 7.96-7.79 (m, 6H), 7.52 (br d, J=7.0 Hz, 1H), 7.48 (br d, J=7.0 Hz, 1H), 7.28 (d, J=7.6 Hz, 1H), 7.23 (s, 1H), 7.13-7.05 (m, 3H), 6.79 (d, J=7.8 Hz, 2H), 4.65 (s, 2H), 4.34-4.28 (m, 1H), 4.21 (br dd, J=5.3, 7.8 Hz, 1H), 3.85 (t, J=6.9 Hz, 2H), 2.87-2.73 (m, 2H), 2.55 (t, J=6.9 Hz, 2H), 1.32 (br d, J=6.6 Hz, 1H).

Step 3: To a solution of 3-((4-(isoquinolin-8-yl)-3-(4-(isoquinolin-8-yl)phenethoxy)benzyl)oxy)propanoic acid (6 mg, 10.82 µmol, 1 eq) in DCM (1 mL) was added DIEA (4.19 mg, 32.45 µmol, 5.65 µL, 3 eq) and HATU (6.17 mg, 16.23 µmol, 1.5 eq). Then 3-[2-amino-3-[3-[2-[2-[2-[2-[[(2R,3R,4R,5S)-3,4-dihydroxy-5-[[4-(trifluoromethyl)pyrimidin-2-yl]amino]tetrahydropyran-2-yl]methoxy]ethoxy]ethoxy]ethoxy]ethylamino]-3-oxopropoxy]propoxy]-N-[2-[2-[2-[2-[[(2R,3R,4R,5S)-3,4-dihydroxy-5-[[4-(trifluoromethyl)pyrimidin-2-yl]amino]tetrahydropyran-2-yl]methoxy]ethoxy]ethoxy]ethoxy]ethyl]propanamide (16.43 mg, 14.06 µmol, 1.3 eq) was added, The mixture was stirred at 15° C. for 2 hrs. The reaction mixture was concentrated under reduced pressure to give a residue. The crude product was purified by reversed-phase HPLC (column: Phenomenex Luna 80*30 mm*3 um; mobile phase: [water (0.1% TFA)-ACN]; B %: 15%-50%, 8 min @100 mL/min). 3,3'-((2-(3-((4-(isoquinolin-8-yl)-3-(4-(isoquinolin-8-yl)phenethoxy)benzyl)oxy)propanamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) (Compound 37, 3.13 mg, 1.67 µmol, 15.47% yield, 91.12% purity) was obtained as a white solid. $^1$H NMR (400 MHz, METHANOL-$d_4$) δ=9.31-9.21 (m, 1H), 9.18-9.06 (m, 1H), 8.65-8.43 (m, 4H), 8.40-8.31 (m, 2H), 8.27-8.09 (m, 3H), 7.89-7.70 (m, 1H), 7.46-7.32 (m, 1H), 7.31-7.09 (m, 3H), 6.97-6.77 (m, 3H), 4.72-4.60 (m, 4H), 4.46-3.97 (m, 13H), 3.95-3.81 (m, 7H), 3.74-3.54 (m, 45H), 3.20-2.78 (m, 8H), 2.66-2.33 (m, 7H).

Preparation of Compound 38: 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano) dipyrrolo[1,2-a:1',2'-d][1,4,7,10,13,16,19,22,25,28,31,34,37,40,43]pentadecaazacyclopentatetracontin-26-yl)propanoic acid 1123 1124
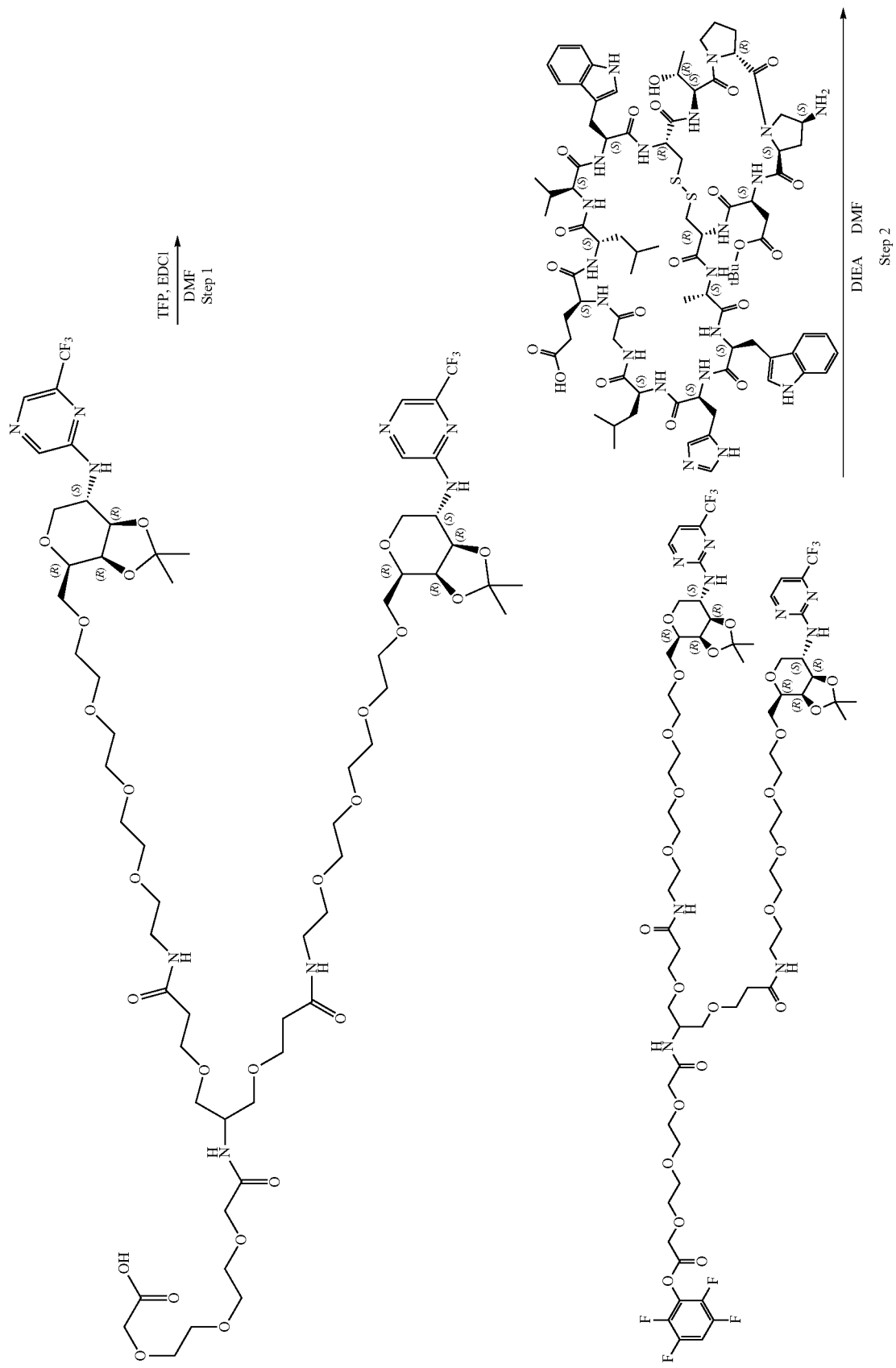

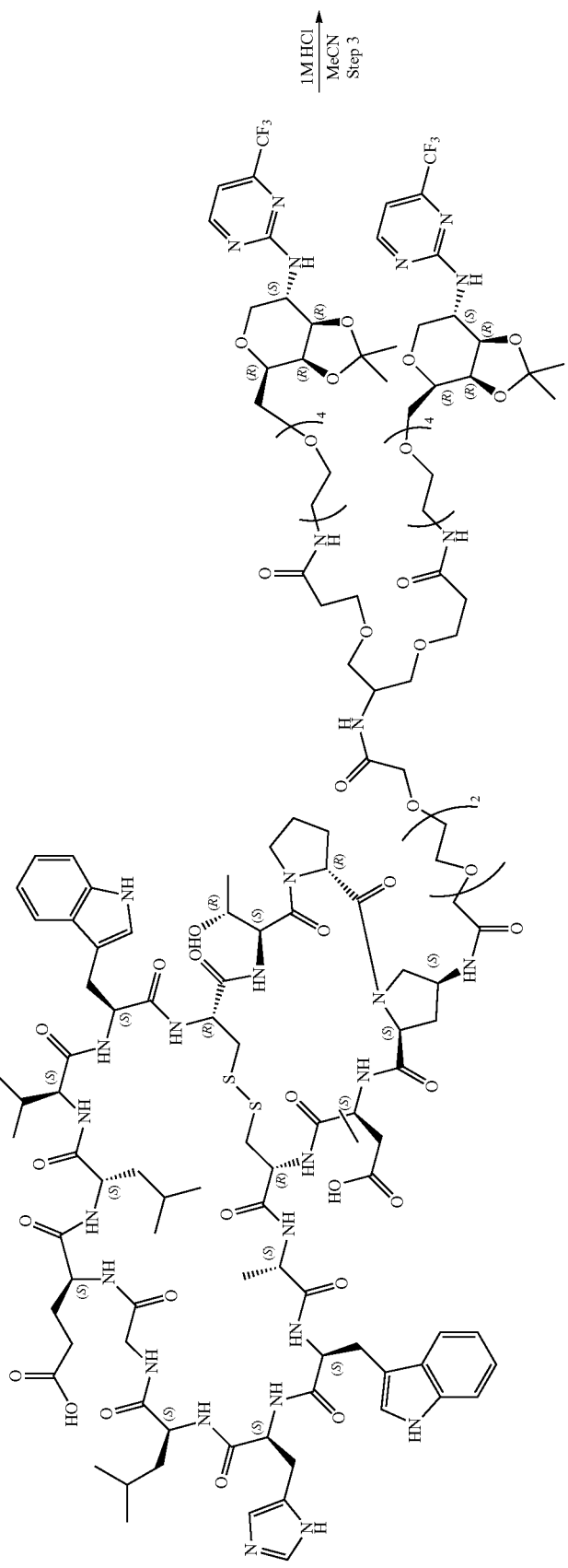

-continued
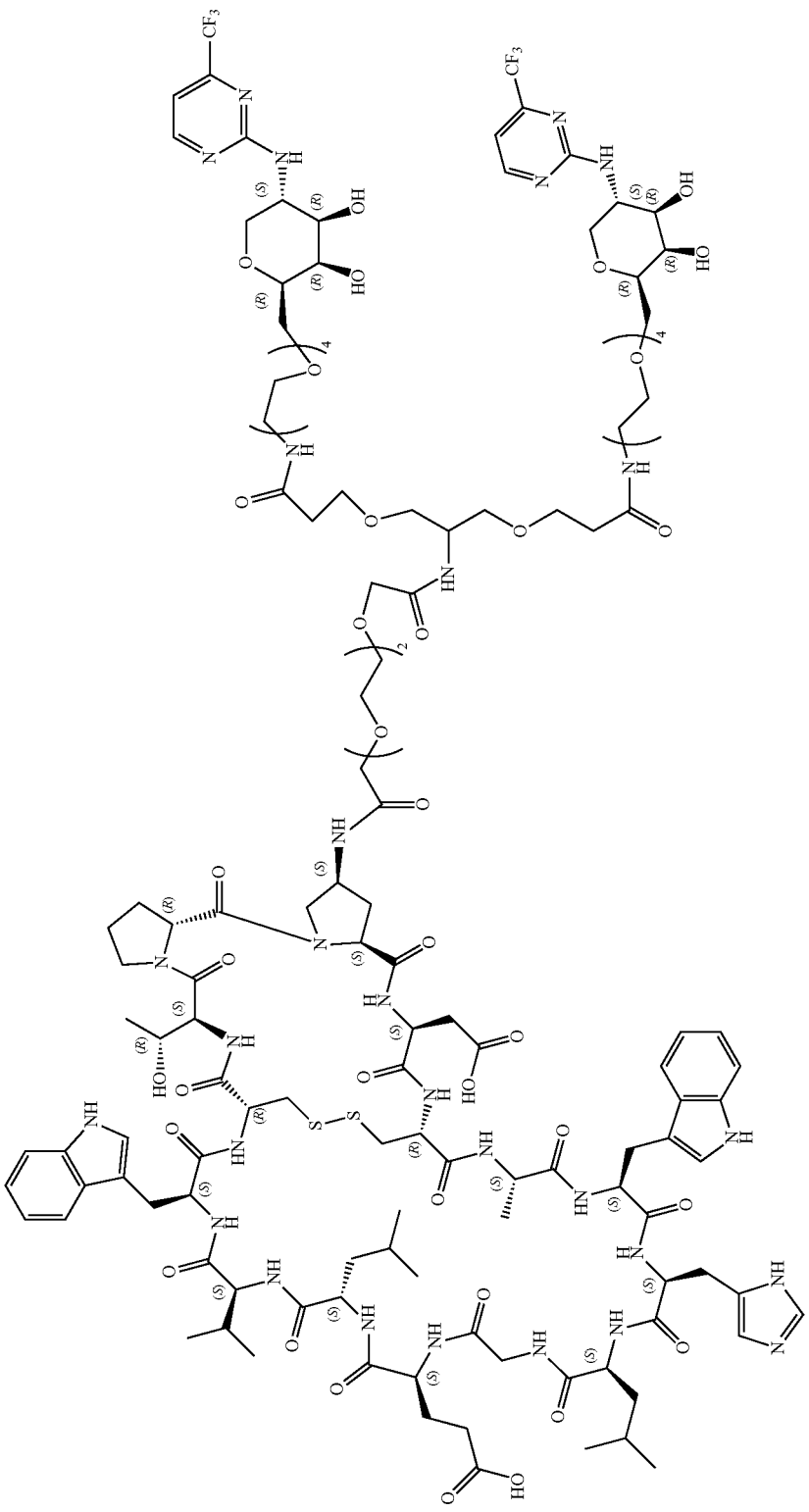
Compound 38

Step 1: To a mixture of 2,3,5,6-tetrafluorophenol (45.74 mg, 275.40 µmol, 4.00 eq), 1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid (100 mg, 68.85 µmol, 1 eq) in DMF (2.0 mL) was cooled to 0° C. Then the mixture was added EDCI (39.60 mg, 206.55 µmol, 3.00 eq) at 0° C. and stirred at 0° C. for 2 hrs. The reaction mixture was purified by prep-HPLC (acid condition, TFA) to afford TFP ester 2,3,5,6-tetrafluorophenyl 1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (50 mg, 31.24 umol, 45.37% yield) as a colorless oil. Chemical Formula: $C_{67}H_{95}F_{10}N_9O_{24}$, LCMS found: $[M+H]^{1+}=1600.70$, $[M+2H]^{2+}=801.00$, $[M+3H]^{3+}=534.40$.

Step 2: To a mixture of 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-2-amino-47-(2-(tert-butoxy)-2-oxoethyl)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (53.7 mg, 31.24 µmol, 1.00 eq), 2,3,5,6-tetrafluorophenyl 1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (50.0 mg, 31.24 µmol, 1.00 eq), DIEA (16.1 mg, 124.96 µmol, 21.77 µL, 4.00 eq) in DMF (0.5 mL) was stirred at 25° C. for 1 hr. The reaction mixture was purified by prep-HPLC (acid condition, TFA) to afford 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (70.0 mg, 19.74 µmol, 63.1% yield, 90.0% purity) as a white solid. Chemical Formula: $C_{140}H_{201}F_6N_{29}O_{43}S_2$, LCMS found: $[M+2H]^{2+}=1578.60$, $[M+3H]^{3+}=1052.90$, $[M+4H]^{4+}=727.00$.

Step 3: To a mixture of 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-20-(1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (70.0 mg, 22.18 µmol, 1.00 eq) in HCl (0.1 M, 0.7 mL, 3.16 eq) and MeCN (0.7 mL) was stirred at 25° C. for 0.5 hr. The mixture was purified by prep-HPLC (acid condition, TFA) directly to afford Compound 38 (57.0 mg, 99.3% purity, 82.96% yield) as a white solid. Chemical Formula: $C_{134}H_{193}F_6N_{29}O_{43}S_2$, LCMS found: $[M+2H]^{2+}=1538.7$, $[M+H+Na]^{2+}=1549.7$, $[M+3H]^{3+}=1026.3$, $[M+4H]^{4+}=769.6$.

Preparation of Compound 39: 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,23-dioxo-2,5,8,11,18,24-hexaoxa-14,21-diazaheptacosan-27-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

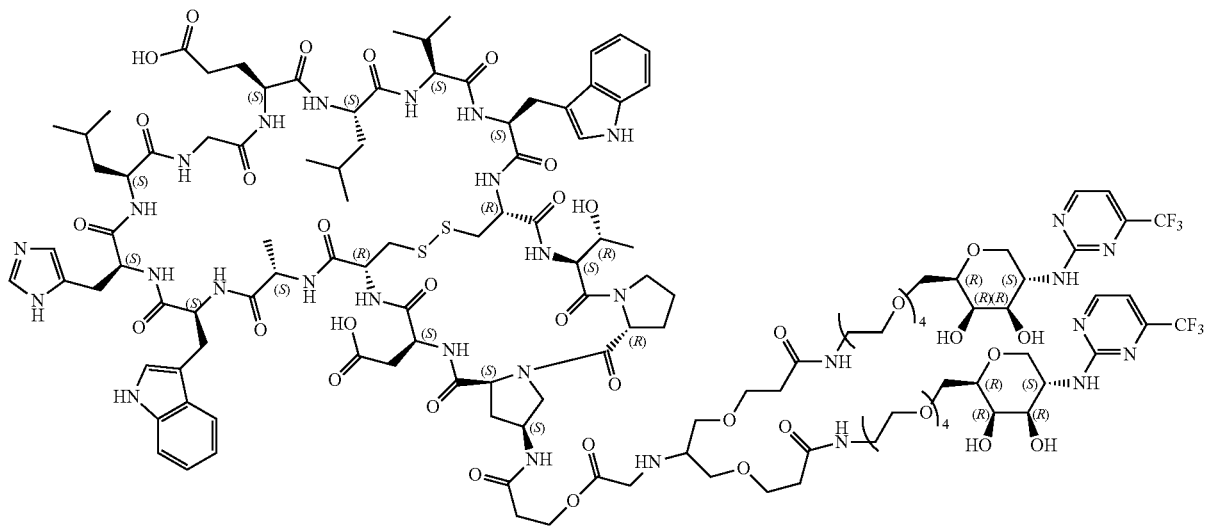

Compound 39

Compound 39 was prepared according to the procedures described in the preparation of Compound 38, wherein the starting material for the preparation of Compound 39 is 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,23-dioxo-2,5,8,11,18,24-hexaoxa-14,21-diazaheptacosan-27-oic acid. Yield: 2.7 mg, 83.0% purity, 9.0%, white solid. LC-MS (ESI) found: $[M+2H]^{2+}=1502.10$, $[M+H+Na]^{2+}=1513.60$, $[M+3H]^{3+}=1002.00$.

Preparation of Compound 40: 3-((2S,5aR,11S,14R, 17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

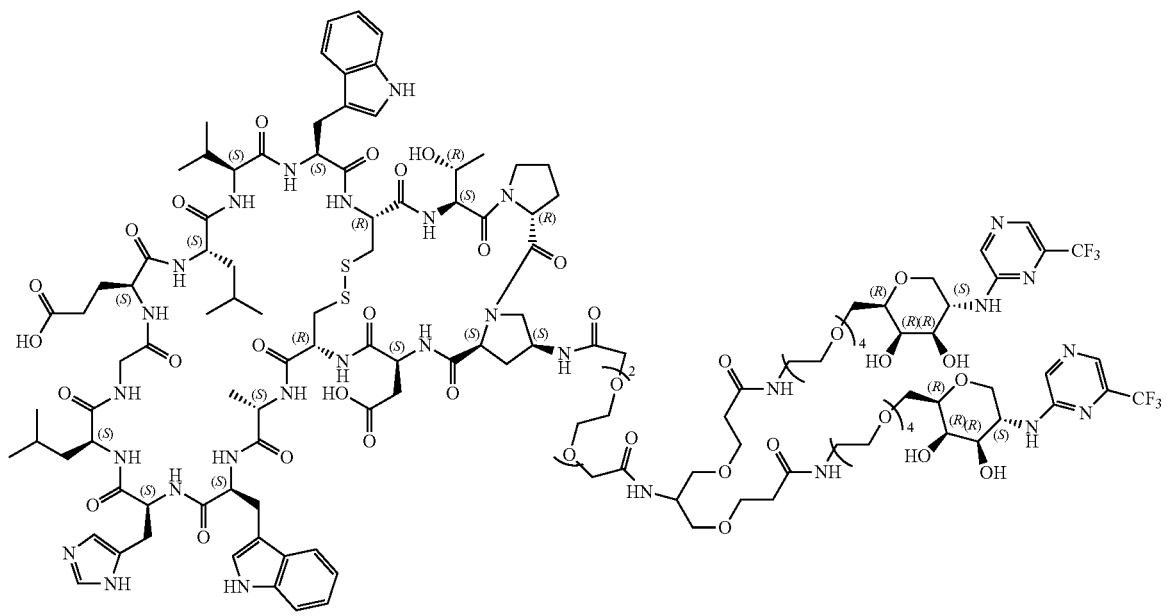

Compound 40

Compound 40 was prepared according to the procedures described in the preparation of Compound 38, wherein the starting material for the preparation of Compound 40 is 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid. Yield: 4.1 mg, 95.8% purity, 16.6% white solid. LC-MS (ESI) found: $[M+2Na]^{2+}=1562.10$, $[M+H+Na]^{2+}=1550.50$, $[M+2H]^{2+}=1539.00$, $[M+3H]^{3+}=1026.70$.

Preparation of Compound 41: 3-((2S,5aR,11S,14R, 17S,20S,23S,26S,32S,35S,38S,41S,44R,47S,49aS)- 35-((1H-imidazol-5-yl)methyl)-17,38-bis((1H-indol- 3-yl)methyl)-47-(carboxymethyl)-2-(1-((2R,3R,4R, 5S)-3,4-dihydroxy-5-((6-(trifluoromethyl)pyrazin-2- yl)amino)tetrahydro-2H-pyran-2-yl)-20-(1-((2R,3R, 4R,5S)-3,4-dihydroxy-5-((6-(trifluoromethyl) pyrazin-2-yl)amino)tetrahydro-2H-pyran-2-yl)-15- oxo-2,5,8,11,18-pentaoxa-14-azanonadecan-19-yl)- 15,22-dioxo-2,5,8,11,18,24,27-heptaoxa-14,21- diazanonacosan-29-amido)-11-((R)-1-hydroxyethyl)- 23,32-diisobutyl-20-isopropyl-41-methyl-5,10,13,16, 19,22,25,28,31,34,37,40,43,46,49- pentadecaoxooctatetracontahydro-5H-14,44- (methanodithiomethano)dipyrrolo[1,2-a:1',2'-d][1,4, 7,10,13,16,19,22,25,28,31,34,37,40,43] pentadecaazacyclopentatetracontin-26-yl)propanoic acid

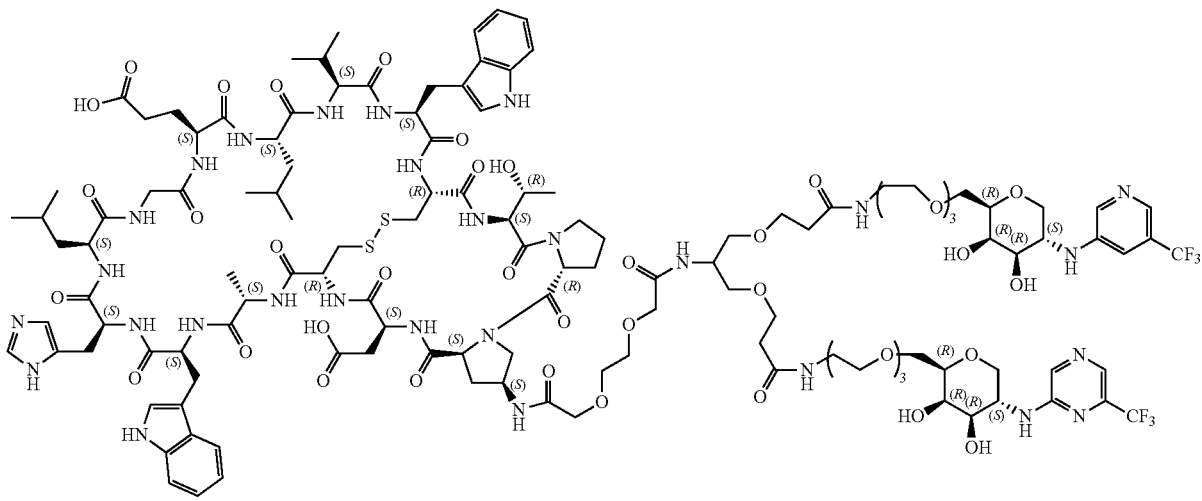

Compound 41

Compound 41 was prepared according to the procedures described in the preparation of Compound 38, wherein the starting material for the preparation of Compound 41 is 1-((2R,3R,4R,5S)-3,4-dihydroxy-5-((6-(trifluoromethyl) pyrazin-2-yl)amino)tetrahydro-2H-pyran-2-yl)-20-(1-((2R, 3R,4R,5S)-3,4-dihydroxy-5-((6-(trifluoromethyl)pyrazin-2- yl)amino)tetrahydro-2H-pyran-2-yl)-15-oxo-2,5,8,11,18- pentaoxa-14-azanonadecan-19-yl)-15,22-dioxo-2,5,8,11,18, 24,27-heptaoxa-14,21-diazanonacosan-29-oic acid. Yield: 14.2 mg, 98.2% purity, 13.5% white solid. LC-MS (ESI) found: $[M+H+Na]^{2+}=1527.4$, $[M+2H]^{2+}=1516.3$, $[M+3H]^{3+}=1011.3$.

Preparation of Compound 42: 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(2-(2-(2-((((2R,3R,4R,5S)-3,4-dihydroxy-5-(((6-(trifluoromethyl)pyrazin-2-yl)amino)tetrahydro-2H-pyran-2-yl)methyl)amino)-2-oxoethoxy)ethoxy)acetamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid Compound 42

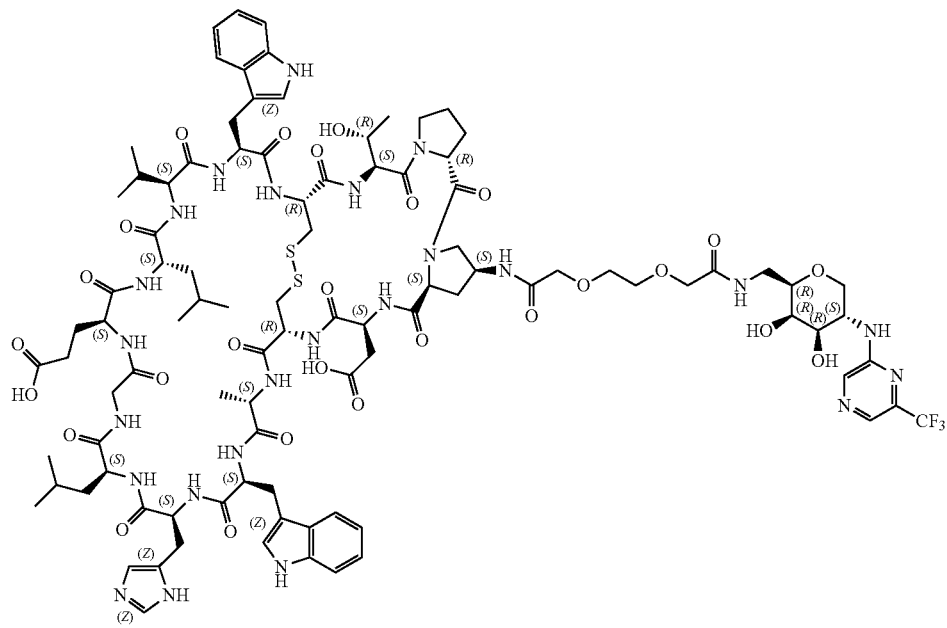

Compound 42 was prepared according to the procedures described in the preparation of Compound 38, wherein the starting material for the preparation of Compound 42 is 2-(2-(2-((((2R,3R,4R,5S)-3,4-dihydroxy-5-((6-(trifluoromethyl)pyrazin-2-yl)amino)tetrahydro-2H-pyran-2-yl)methyl)amino)-2-oxoethoxy)ethoxy)acetic acid. Yield: 17.9 mg, 99.1% purity, 33.5% white solid. LC-MS (ESI) found: $[M+2H]^{2+}=1086.6$, $[M+3H]^{3+}=725.1$.

Preparation of Compound 43: 3-((2S,5aR,11S,14R, 17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24-hexaoxa-14,21-diazahexacosan-26-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

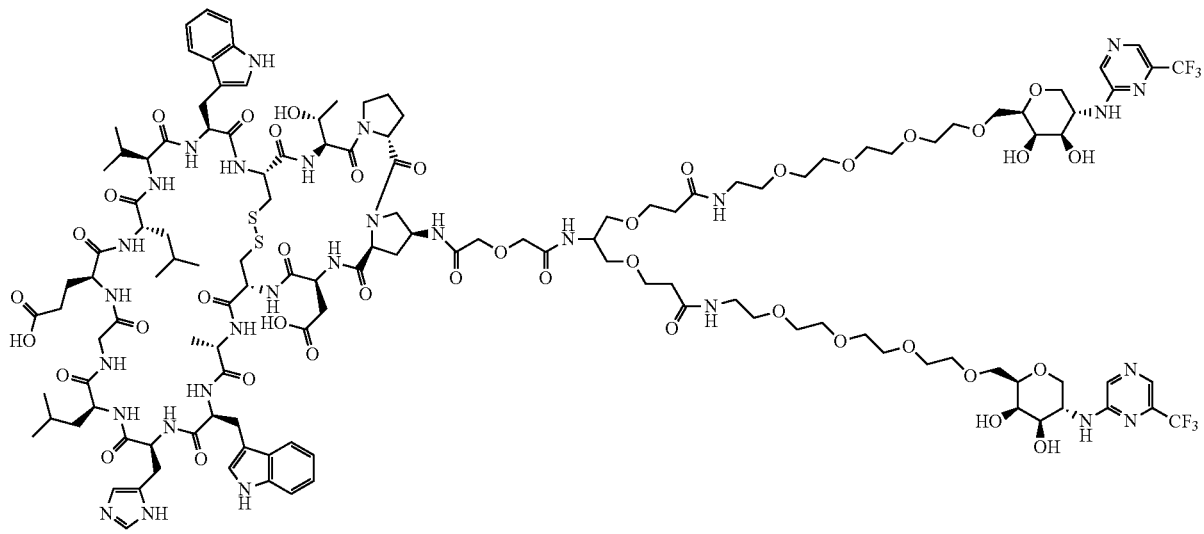

Compound 43

Compound 43 was prepared according to the procedures described in the preparation of Compound 38, wherein the starting material for the preparation of Compound 43 is 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24-hexaoxa-14,21-diazahexacosan-26-oic acid. Yield: 19.7 mg, 96.9% purity, 30.5% white solid. LC-MS (ESI) found: $[M+2H]^{2+}=1086.6$, $[M+3H]^{3+}=725.1$.

Preparation of Compound 44: 3-((2S,5aR,11S,14R, 17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(2-(4-((4-(((2R, 3R,4R,5S)-3,4-dihydroxy-5-((6-(trifluoromethyl) pyrazin-2-yl)amino)tetrahydro-2H-pyran-2-yl) methyl)piperazin-1-yl)methyl)phenoxy)acetamido)-11-((R)-1-hydroxyethyl)-23,32-diisobutyl-20-isopropyl-41-methyl-5,10,13,16,19,22,25,28,31,34, 37,40,43,46,49-pentadecaoxooctatetracontahydro-5H-14,44-(methanodithiomethano)dipyrrolo[1,2-a:1', 2'-d][1,4,7,10,13,16,19,22,25,28,31,34,37,40,43] pentadecaazacyclopentatetracontin-26-yl)propanoic acid

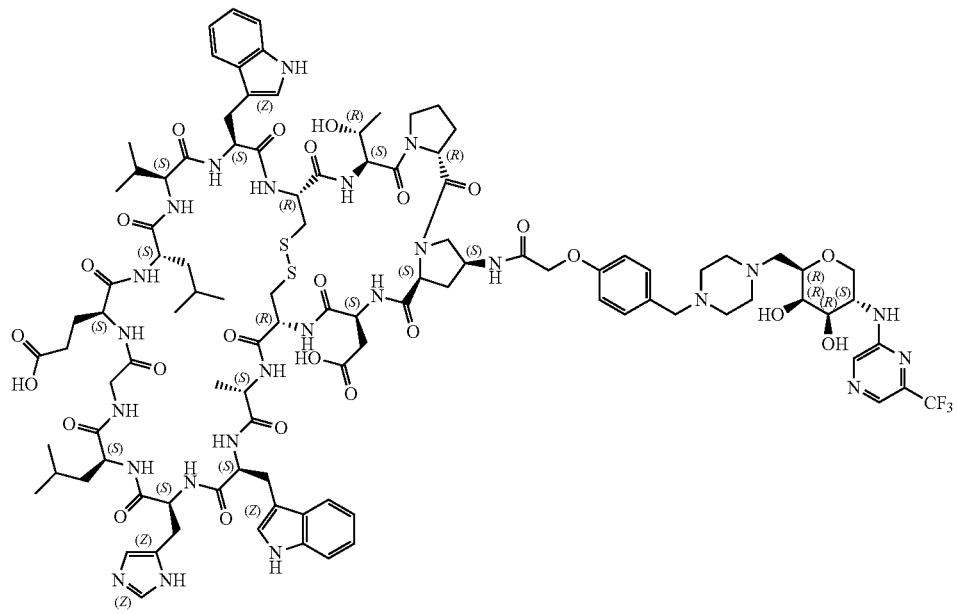

Compound 44

Compound 44 was prepared according to the procedures described in the preparation of Compound 38, wherein the starting material for the preparation of Compound 44 is 2-(4-((4-(((2R,3R,4R,5S)-3,4-dihydroxy-5-((6-(trifluoromethyl)pyrazin-2-yl)amino)tetrahydro-2H-pyran-2-yl)methyl)piperazin-1-yl)methyl)phenoxy)acetic acid. Yield: 7.7 mg, 96.6% purity, 22.8% white solid. LC-MS (ESI) found: $[M+H+Na]^{2+}=1134.7$, $[M+2H]^{2+}=1123.1$, $[M+3H]^{3+}=749.1$.

Preparation of Compound 48: (3S,6R,11R,14S,17S, 20S,23S,29S,34aS)-11-((S)-2-((S)-2-((S)-2-amino-3-(1H-imidazol-5-yl)propanamido)-4-(methylthio) butanamido)-3-methylbutanamido)-N—((S)-1-(((S)-1-(((S)-1-amino-4-methyl-1-oxopentan-2-yl)amino)-3-hydroxy-1-oxopropan-2-yl)amino)-1-oxo-3-phenylpropan-2-yl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxodotria contahydropyrrolo[2,1-j][1,2,5,8,11, 14,17,20,23,26,29]dithianonaaza cyclodotriacontine-6-carboxamide

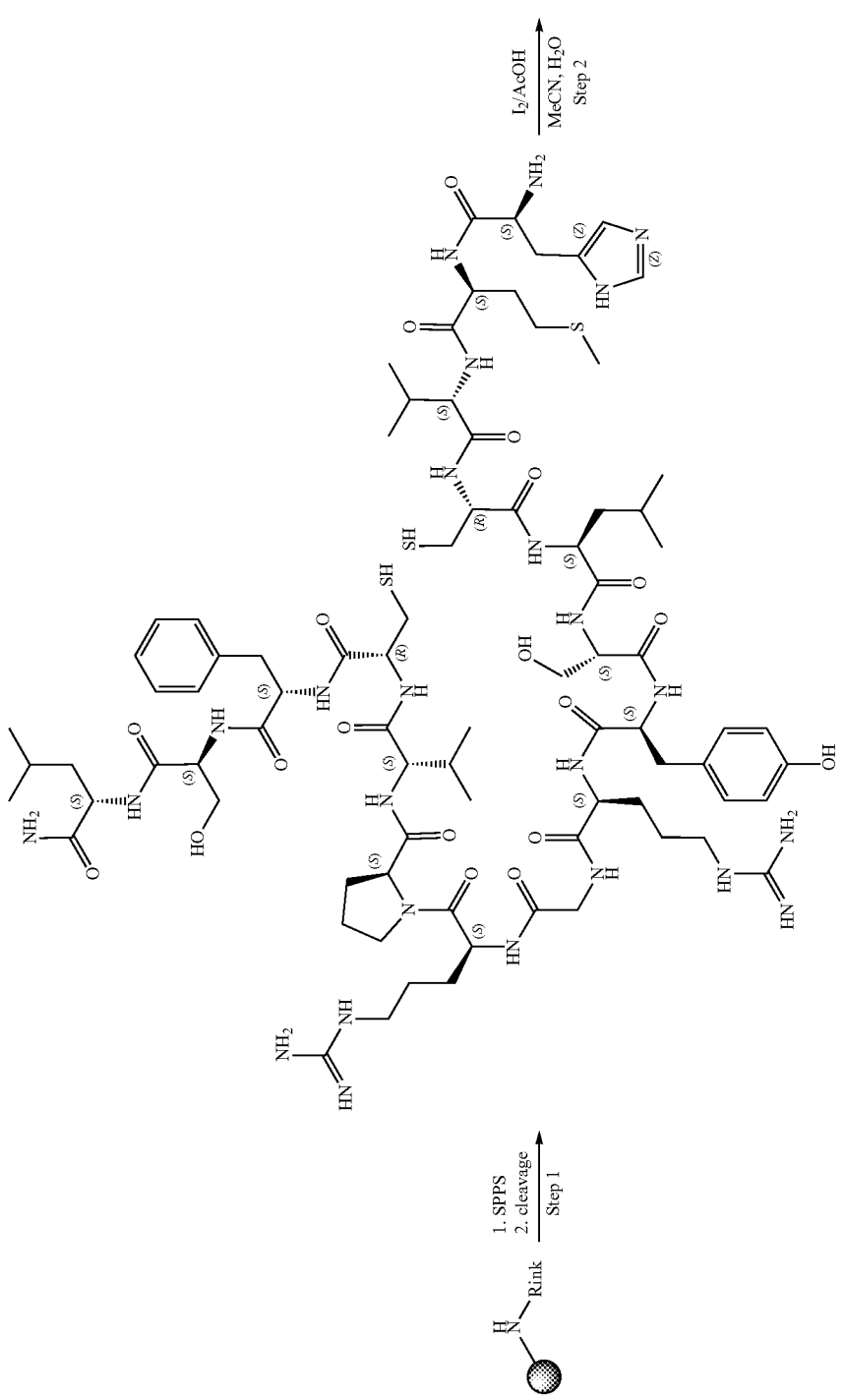

-continued
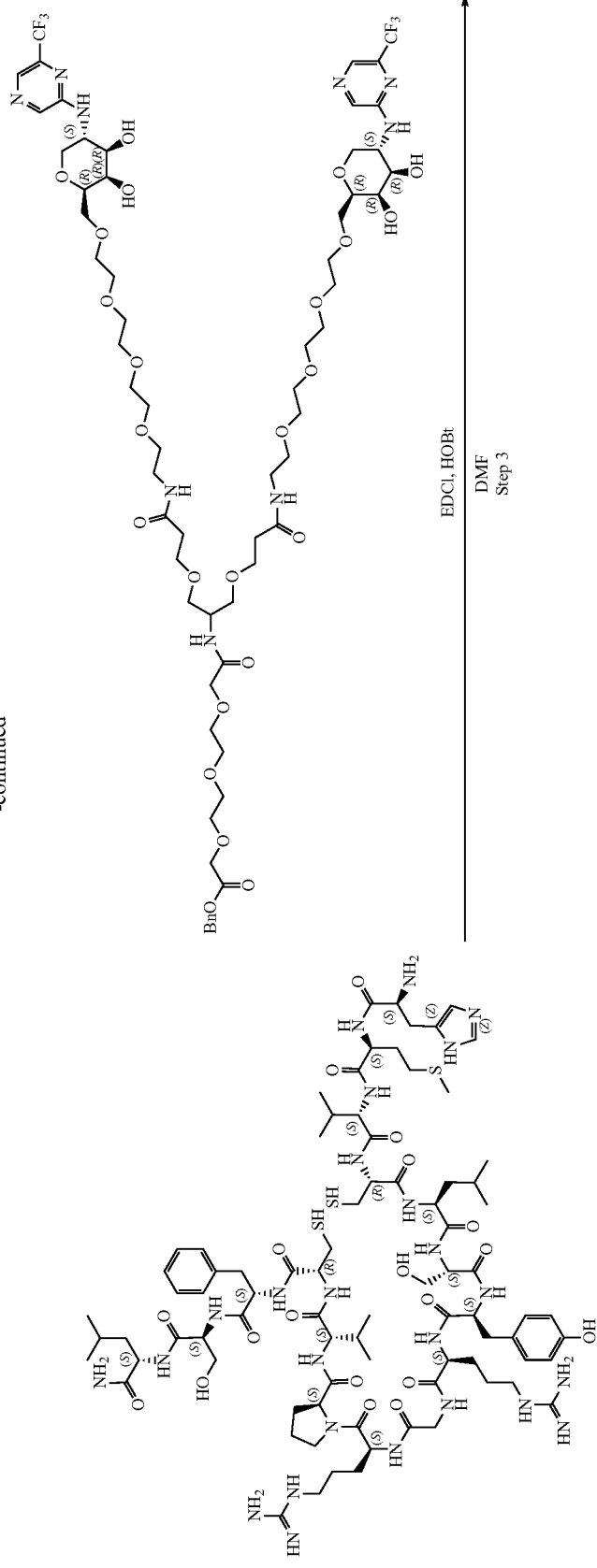

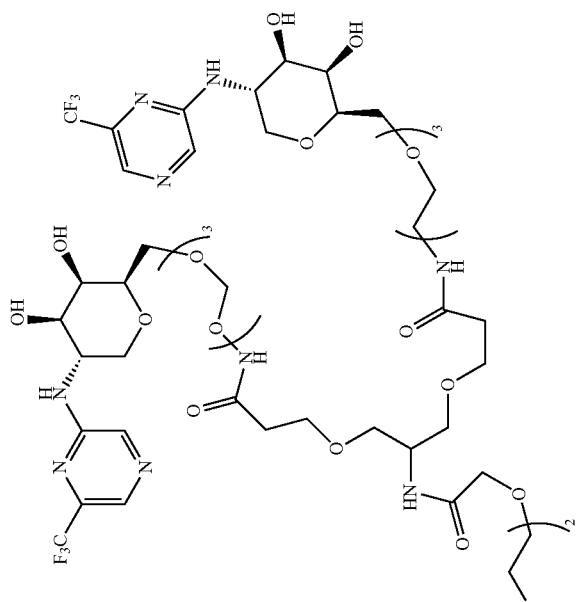
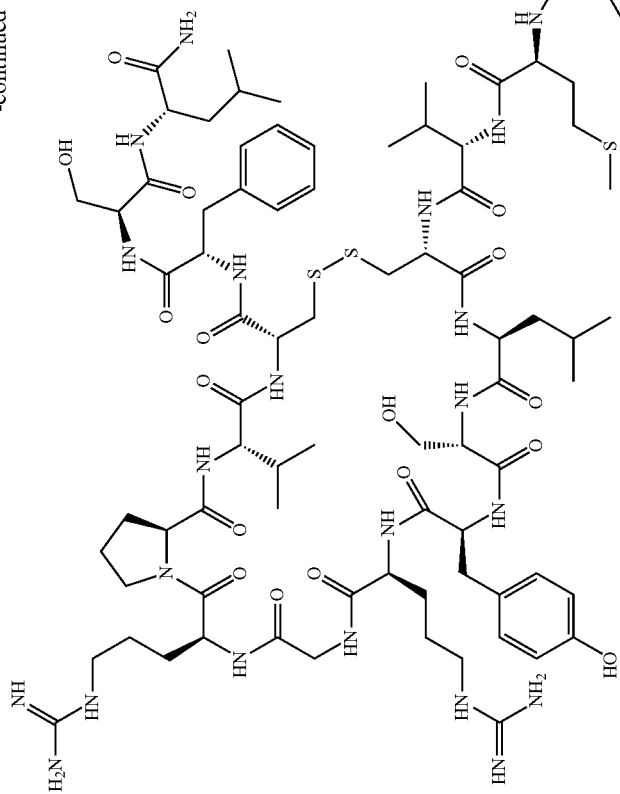
Compound 48
-continued

Step 1: Solid Phase Peptide Synthesis:

The peptide was synthesized using standard Fmoc chemistry.

1) Resin preparation: To the vessel containing AM Resin (3.33 g, 1.00 mmol, 0.30 mmol/g) in DMF (30 mL) mixed for 30 mins with $N_2$ bubbling at 25° C. The resin was washed with DMF (30 mL)*5. Then 20% piperidine in DMF (30 mL) was added and the mixture was bubbled with $N_2$ for 30 mins at 25° C. The mixture was filtered to obtain the resin. The resin was washed with DMF (30 mL)*5 before proceeding to next step.

2) Coupling: To a solution of Fmoc-Leu-OH (1.06 g, 3.00 mmol, 3.00 eq), HBTU (1.08 g, 2.85 mmol, 2.85 eq) in DMF (15 mL) was added to the resin with $N_2$ bubbling. Then DIEA (1.05 mL, 6.00 mmol, 6.00 eq) was added to the mixture dropwise and bubbled with $N_2$ for 30 mins at 25° C. The coupling reaction was monitored by ninhydrin test, if it showed colorless, the coupling was completed. The resin was then washed with DMF (30 mL)*5.

3) De-protection: To a solution of 20% piperidine in DMF (30 mL) was added to the resin and the mixture was bubbled with $N_2$ for 30 mins at 25° C. The resin was then washed with DMF (30 mL)*5. The De-protection reaction was monitored by ninhydrin test, if it showed blue or other brownish red, the reaction was completed.

4) Step 2 and 3 were repeated for all other amino acids: (2-16 in Table Z).

TABLE Z

| # | Materials | Coupling reagents |
|---|---|---|
| 1 | Fmoc-Leu-OH (3.00 eq) | HBTU (2.85 eq) and DIEA (6.00 eq) |
| 2 | Fmoc-Ser(tBu)-OH (3.00 eq) | HBTU (2.85 eq) and DIEA (6.00 eq) |
| 3 | Fmoc-Phe-OH (3.00 eq) | HBTU (2.85 eq) and DIEA (6.00 eq) |
| 4 | Fmoc-Cys(Trt)-OH (3.00 eq) | HBTU (2.85 eq) and DIEA (6.00 eq) |
| 5 | Fmoc-Val-OH (3.00 eq) | HBTU (2.85 eq) and DIEA (6.00 eq) |
| 6 | Fmoc-Pro-OH (3.00 eq) | HBTU (2.85 eq) and DIEA (6.00 eq) |
| 7 | Fmoc-Arg(Pbf)-OH (3.00 eq) | HBTU (2.85 eq) and DIEA (6.00 eq) |
| 8 | Fmoc-Gly-OH (3.00 eq) | HBTU (2.85 eq) and DIEA (6.00 eq) |
| 9 | Fmoc-Arg(Pbf)-OH (3.00 eq) | HBTU (2.85 eq) and DIEA (6.00 eq) |
| 10 | Fmoc-Tyr(tBu)-OH (3.00 eq) | HBTU (2.85 eq) and DIEA (6.00 eq) |
| 11 | Fmoc-Ser(tBu)-OH (3.00 eq) | HBTU (2.85 eq) and DIEA (6.00 eq) |
| 12 | Fmoc-Leu-OH (3.00 eq) | HBTU (2.85 eq) and DIEA (6.00 eq) |
| 13 | Fmoc-Cys(Trt)-OH (3.00 eq) | HBTU (2.85 eq) and DIEA (6.00 eq) |
| 14 | Fmoc-Val-OH (3.00 eq) | HBTU (2.85 eq) and DIEA (6.00 eq) |
| 15 | Fmoc-Met-OH (3.00 eq) | HBTU (2.85 eq) and DIEA (6.00 eq) |
| 16 | Fmoc-His(Trt)-OH (3.00 eq) | HBTU (2.85 eq) and DIEA (6.00 eq) |

Step 2: Peptide Cleavage and Purification:

7) Cleavage buffer (92.5% TFA/2.5% TIS/2.5% $H_2O$/2.5% 3-mercaptopropanoic acid) was added to the flask containing the side chain protected peptide at room temperature (25° C.) and stir for 2 hrs.

8) The peptide was precipitated with cold isopropyl ether and centrifuged (3 mins at 3000 rpm).

9) Isopropyl ether washed two additional times.

10) Dried the crude peptide under vacuum 2 hrs.

11) To a mixture of crude peptide in MeCN (500 mL) and $H_2O$ (500 mL), $I_2$ (0.1 M in AcOH) was added dropwise to vigorously stirring peptide solution until yellow color persists. After 2 minutes, sodium thiosulfate (0.1 M in water) was added dropwise until yellow color disappears. The mixture was lyophilized to give the crude powder.

12) The crude peptide was purified by prep-HPLC (A: 0.075% TFA in $H_2O$, B: ACN) to afford (3S,6R,11R,14S,17S,20S,23S,29S,34aS)-11-((S)-2-((S)-2-((S)-2-amino-3-(1H-imidazol-5-yl)propanamido)-4-(methylthio)butanamido)-3-methylbutanamido)-N—((S)-1-(((S)-1-(((S)-1-amino-4-methyl-1-oxopentan-2-yl)amino)-3-hydroxy-1-oxopropan-2-yl)amino)-1-oxo-3-phenylpropan-2-yl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontine-6-carboxamide (1.40 g, 91.4% purity, 68.60% yield) as a white solid. Chemical Formula: $C_{82}H_{129}N_{25}O_{19}S_3$; LCMS found: $[M+2H]^{2+}=933.17$; $[M+3H]^{3+}=622.5$.

Step 3: To a solution of (3S,6R,11R,14S,17S,20S,23S,29S,34aS)-11-((S)-2-((S)-2-((S)-2-amino-3-(1H-imidazol-5-yl)propanamido)-4-(methylthio)butanamido)-3-methylbutanamido)-N—((S)-1-(((S)-1-(((S)-1-amino-4-methyl-1-oxopentan-2-yl)amino)-3-hydroxy-1-oxopropan-2-yl)amino)-1-oxo-3-phenylpropan-2-yl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontine-6-carboxamide (520.0 mg, 278.78 umol, 1.00 eq) and benzyl 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (382.58 mg, 278.78 umol, 1.00 eq) in DMF (10.0 mL) was added HOBt (113.01 mg, 836.35 umol, 3.00 eq) and EDCI (160.33 mg, 836.35 umol, 3.00 eq) at 25° C. The mixture was stirred at 25° C. for 1 hr. The mixture was purified by prep-HPLC (acid condition, TFA) to afford 3,3'-((2-((13S,16S,19S)-13-((1H-imidazol-5-yl)methyl)-19-(((3S,6R,11R,14S,17S,20S,23S,29S,34aS)-6-(((S)-1-(((S)-1-(((S)-1-amino-4-methyl-1-oxopentan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)carbamoyl)-20-methyl-16-(2-(methylthio)ethyl)-11,14,17-trioxo-3,6,9-trioxa-12,15,18-triazahenicosanamido)propane-1,3-diyl)bis(oxy))bis(N-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-yl)propanamide) (Compound 48, 388.1 mg, 96.5% purity, 43.2% yield) as a white solid. Chemical Formula: $C_{137}H_{214}F_6N_{34}O_{42}S_3$; LCMS found: $[M+H+Na]^{2+}=1621.3$; $[M+2H]^{2+}=1609.7$; $[M+3H]^{3+}=1074.0$, $[M+4H]^{4+}=805.7$.

Preparation of Compound 49: 3-((6S,9R,12S,15S,18S,21S,27S,30S,33S,36S,39R,42S,44aS,46S,49aR)-30-((1H-imidazol-5-yl)methyl)-12,33-bis((1H-indol-3-yl)methyl)-42-(carboxymethyl)-46-(20-(1-(1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-17-oxo-4,7,10,13-tetraoxa-16-azaicosanamido)-6-((R)-1-hydroxyethyl)-18,27-diisobutyl-15-isopropyl-36-methyl-5,8,11,14,17,20,23,26,29,32,35,38,41,44,49-pentade caoxo octatetracontahydro-1H-9,39-(methanodithiomethano)dipyrrolo[1,2-a:1',2'-d][1,4,7,10,13,16,19,22,25,28,31,34,37,40,43]pentadecaazacyclopentatetracontin-21-yl)propanoic acid

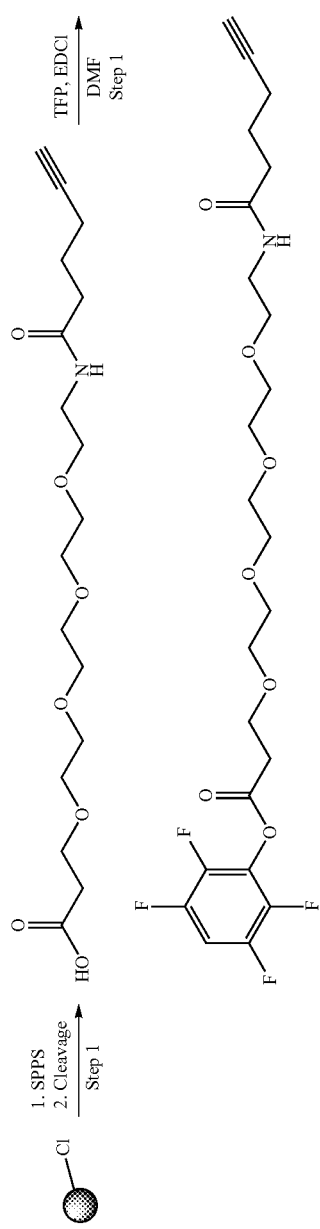

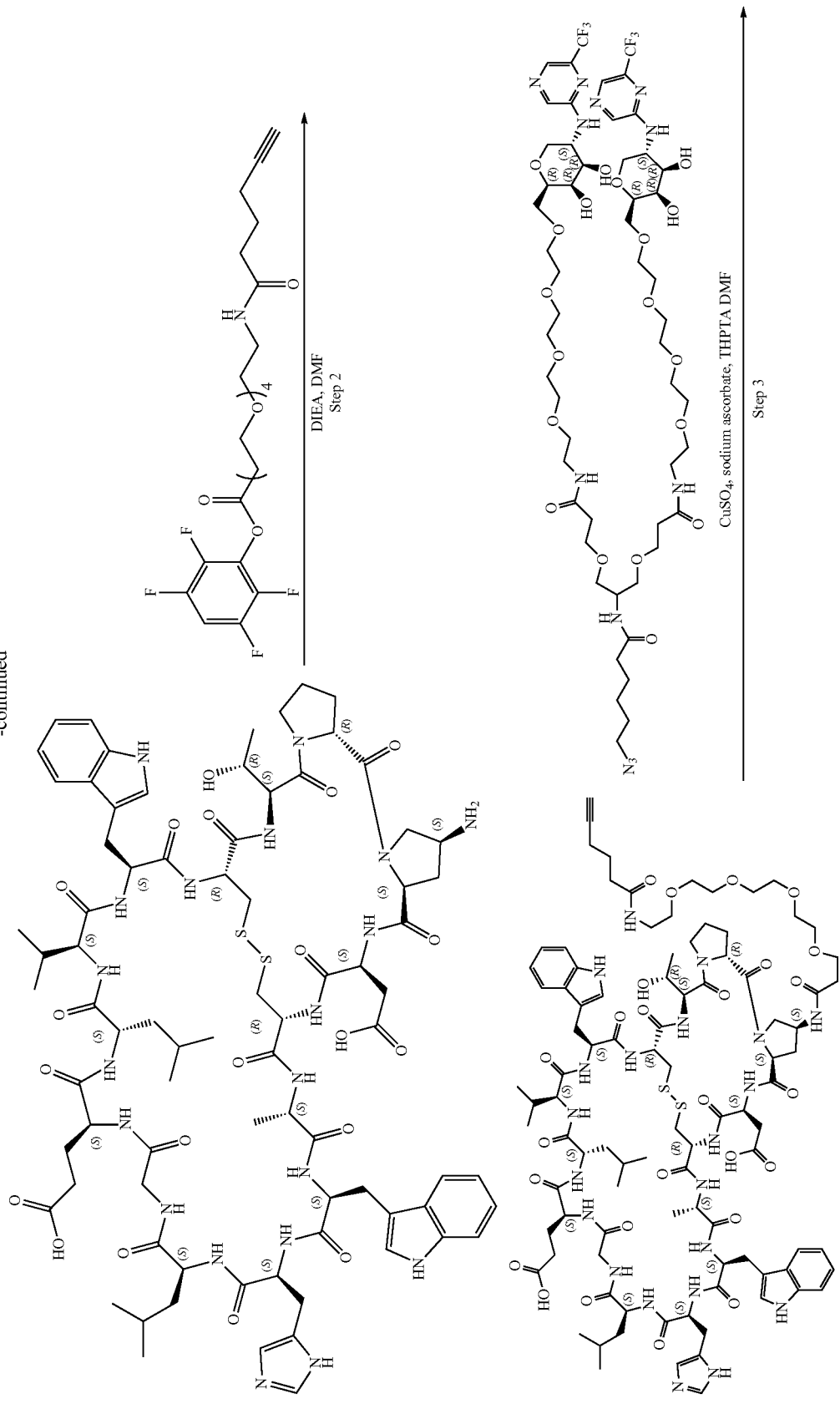

-continued
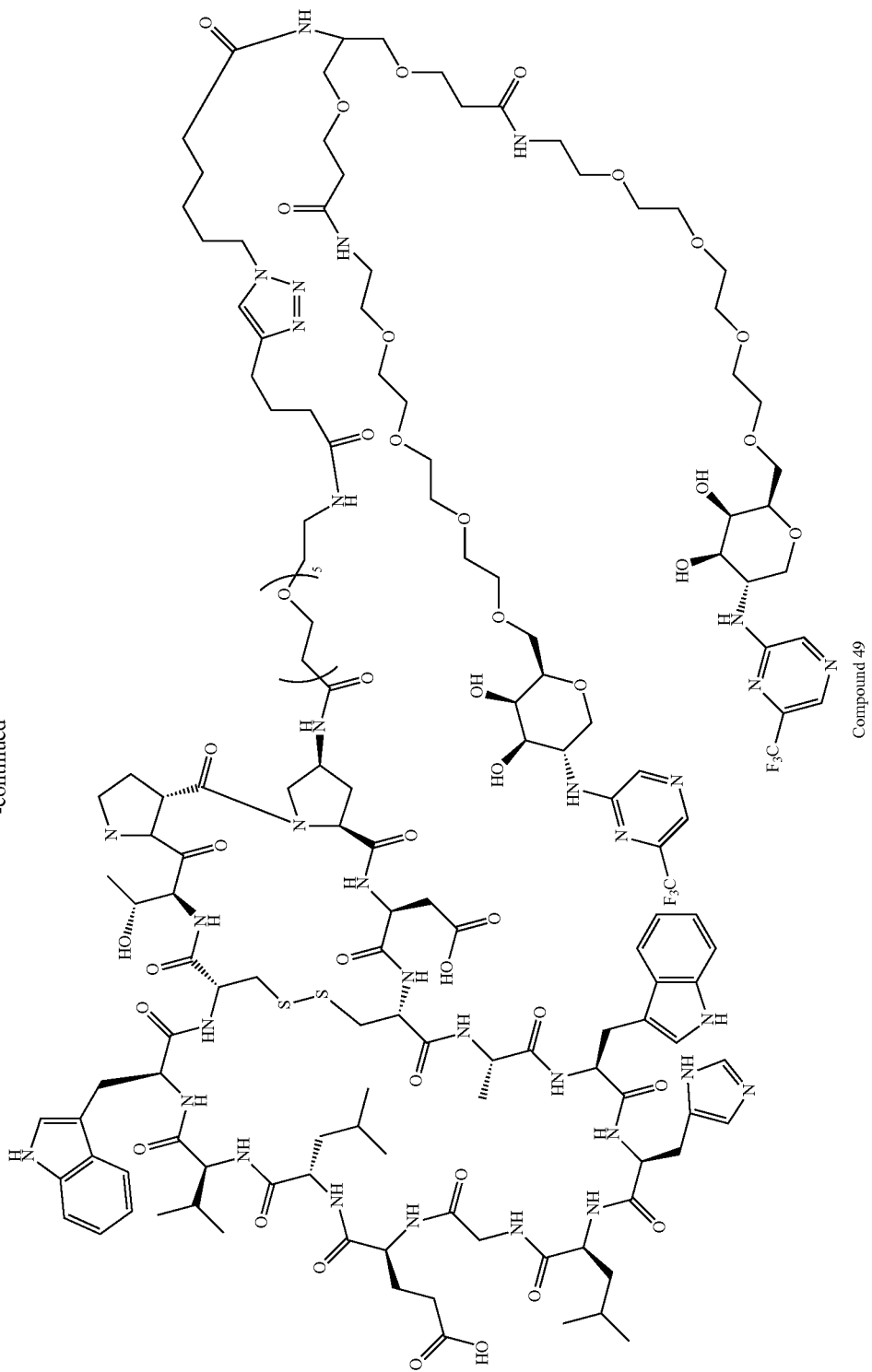
Compound 49

Step 1: To a mixture of 17-oxo-4,7,10,13-tetraoxa-16-azadocos-21-ynoic acid (8.00 g, 22.25 mmol, 1.00 eq), 2,3,5,6-tetrafluorophenol (11.08 g, 66.75 mmol, 4.00 eq), and EDCI (9.52 g, 33.23 mmol, 2.00 eq) in DMF (224 mL) was stirred at 25° C. for 16 hrs. LCMS showed reactant 1 was consumed completely, and on main peak was desired MS. The mixture was purified by Flash (C18, TFA condition) and lyophilized to afford 2,3,5,6-tetrafluorophenyl 17-oxo-4,7,10,13-tetraoxa-16-azadocos-21-ynoate (9.00 g, 17.73 mmol, 79.6% yield) as a yellow oil. Chemical Formula: $C_{23}H_{29}F_4NO_7$, LCMS found: $[M+H]^+=508.15$.

Step 2: To a solution of 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-2-amino-47-(carboxymethyl)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (3.00 g, 1.74 mmol, 1.00 eq), 2,3,5,6-tetrafluorophenyl 17-oxo-4,7,10,13-tetraoxa-16-azadocos-21-ynoate (1.77 g, 3.48 mmol, 2.00 eq), and DIEA (3.03 mL, 17.42 mmol, 10.00 eq) in DMF (30 mL) was stirred at 0° C. for 8 hrs. The mixture was adjusted pH=5 and purified by prep-HPLC (TFA condition) directly to afford 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-11-((R)-1-hydroxyethyl)-23,32-diisobutyl-20-isopropyl-41-methyl-5,10,13,16,19,22,25,28,31,34,37,40,43,46,49-pentadecaoxo-2-(17-oxo-4,7,10,13-tetraoxa-16-azadocos-21-ynamido)octatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (1.30 g, 95.1% purity, 34.3% yield) as a white solid. Chemical Formula: $C_{96}H_{135}N_{21}O_{26}S_2$, LCMS found: $[M+2H]^{2+}=1032.10$, $[M+3H]^{3+}=688.40$.

Step 3: To a solution of 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-11-((R)-1-hydroxyethyl)-23,32-diisobutyl-20-isopropyl-41-methyl-5,10,13,16,19,22,25,28,31,34,37,40,43,46,49-pentadecaoxo-2-(17-oxo-4,7,10,13-tetraoxa-16-azadocos-21-ynamido)octatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (402.1 mg, 194.9 umol, 1.00 eq), 3,3'-((2-(6-azidohexanamido)propane-1,3-diyl)bis(oxy))bis(N-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-yl)propanamide) (254.8 mg, 194.91 umol, 1.00 eq) in DMF (8 mL) was cooled to 0° C., degassed and purged with $N_2$ for 3 times. Then a freshly prepared mixture of $CuSO_4$ (0.4 M, 487.27 uL, 1.00 eq), sodium ascorbate (0.5 M, 1.56 mL, 4.00 eq) and THPTA (86.34 mg, 194.91 umol, 1.00 eq) was added to the reaction mixture at 0° C. The mixture was degassed and purged with $N_2$ for 3 times, stirred at 0° C. for 2 hrs under $N_2$ atmosphere. The mixture was purified by prep-HPLC (acid condition, TFA) directly and lyophilized to afford 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(20-(1-(1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-17-oxo-4,7,10,13-tetraoxa-16-azaicosanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (495.0 mg, 92.0% purity, 71.70% yield) as a light-yellow solid. Chemical Formula: $C_{149}H_{219}F_6N_{33}O_{45}S_2$, LCMS found: $[M+2H]^{2+}=1686.80$, $[M+3H]^{3+}=1125.00$, $[M+4H]^{4+}=843.90$, $[M+5H]^{5+}=675.40$.

Preparation of Compound 53: 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(4-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)butanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

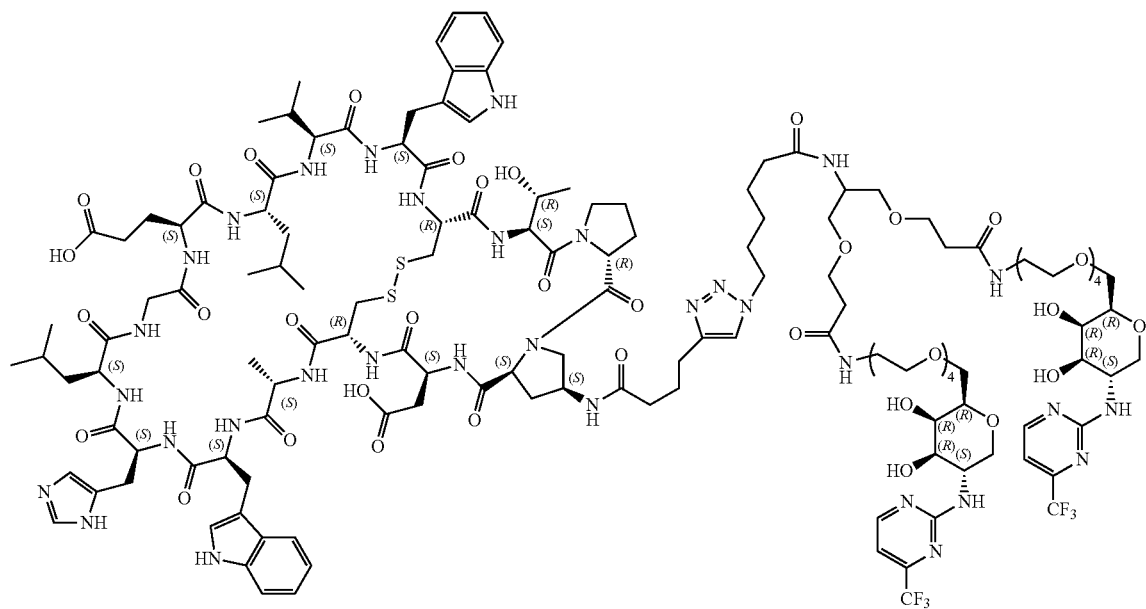

Compound 53

Compound 53 was prepared according to the procedures described in the preparation of Compound 49, wherein the starting material for the preparation of Compound 53 is 3,3'-((2-(6-azidohexanamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide) Yield: 49.1 mg, 97.5% purity, 66.7% yield, white solid. LC-MS (ESI) found: $[M+2H]^{2+}$=1562.17, $[M+3H]^{3+}$=1041.65, $[M+4H]^{4+}$=781.50, $[M+5H]^{5+}$=625.30.

Preparation of Compound 52: 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(4-(1-(1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)butanamido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano) dipyrrolo[1,2-a:1',2'-d][1,4,7,10,13,16,19,22,25,28,31,34,37,40,43]pentadecaazacyclopenta tetracontin-26-yl)propanoic acid

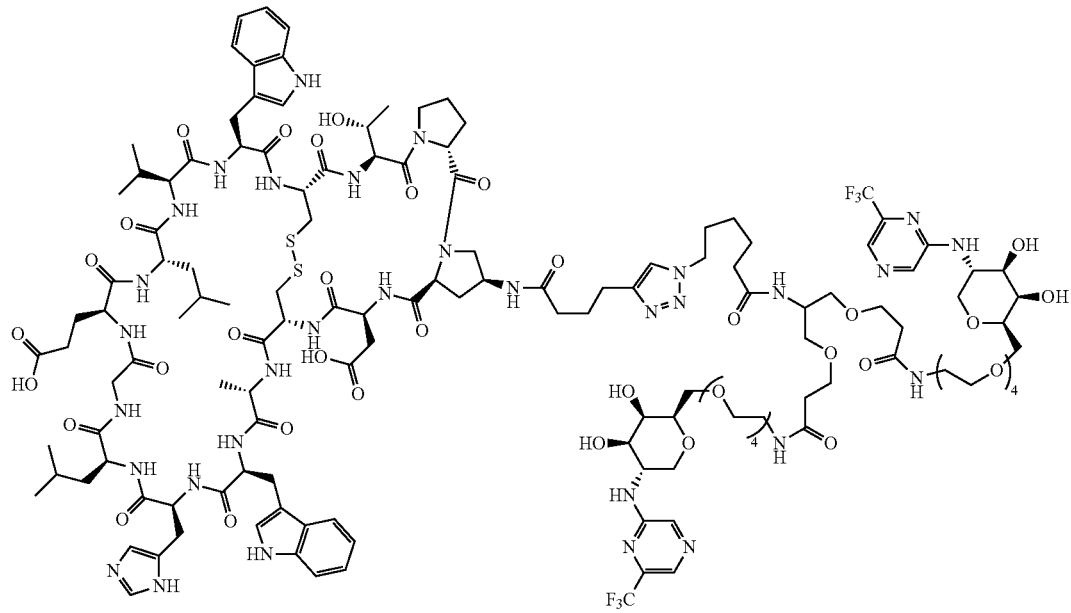

Compound 52

Compound 52 was prepared according to the procedures described in the preparation of Compound 49, wherein the starting material for the preparation of Compound 52 is 3,3'-((2-(6-azidohexanamido)propane-1,3-diyl)bis(oxy))bis(N-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-yl)propanamide), Yield: 7.6 mg, 90.9% purity, 26.29% yield, white solid. LC-MS (ESI) found: $[M+2H]^{2+}=1562.00$, $[M+3H]^{3+}=1041.71$, $[M+4H]^{4+}=781.49$, $[M+5H]^{5+}=625.51$.

Preparation of Compound 51: 3-((2S,5aR,11S,14R, 17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(4-(1-(((2R,3R, 4R,5S)-3,4-dihydroxy-5-((6-(trifluoromethyl) pyrazin-2-yl)amino)tetrahydro-2H-pyran-2-yl) methyl)-1H-1,2,3-triazol-4-yl)butanamido)-11-((R)-1-hydroxyethyl)-23,32-diisobutyl-20-isopropyl-41-methyl-5,10,13,16,19,22,25,28,31,34,37,40,43,46, 49-pentadecaoxooctatetracontahydro-5H-14,44-(methanodithiomethano)dipyrrolo [1,2-a:1',2'-d][1,4, 7,10,13,16,19,22,25,28,31,34,37,40,43] pentadecaazacyclopentatetracontin-26-yl)propanoic acid

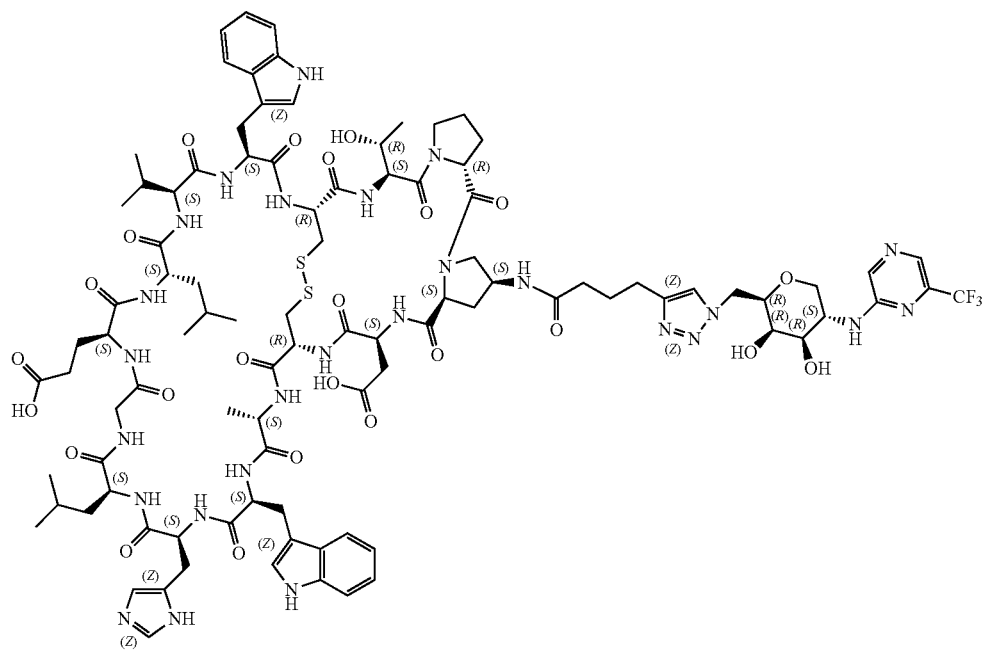

Compound 51 was prepared according to the procedures described in the preparation of Compound 49, wherein the starting material for the preparation of Compound 51 is (2R,3R,4R,5S)-2-(azidomethyl)-5-((6-(trifluoromethyl) pyrazin-2-yl)amino)tetrahydro-2H-pyran-3,4-diol, Yield: 38.7 mg, 98.5% purity, 58.5% yield, white solid. LC-MS (ESI) found: $[M+2H]^{2+}=1075.60$, $[M+3H]^{3+}=717.45$.

Preparation of Compound 40: 3-((2S,5aR,11S,14R, 17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

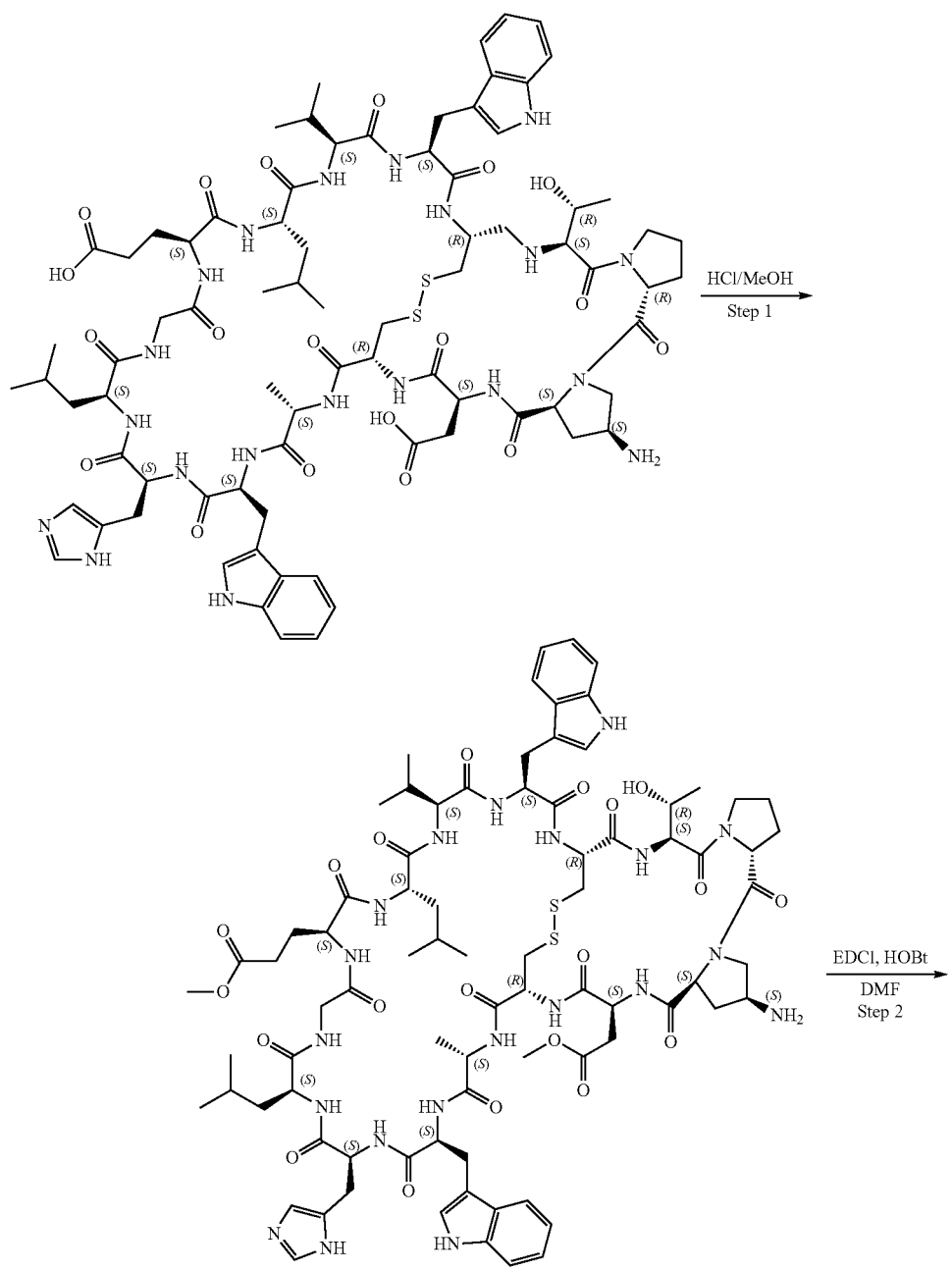

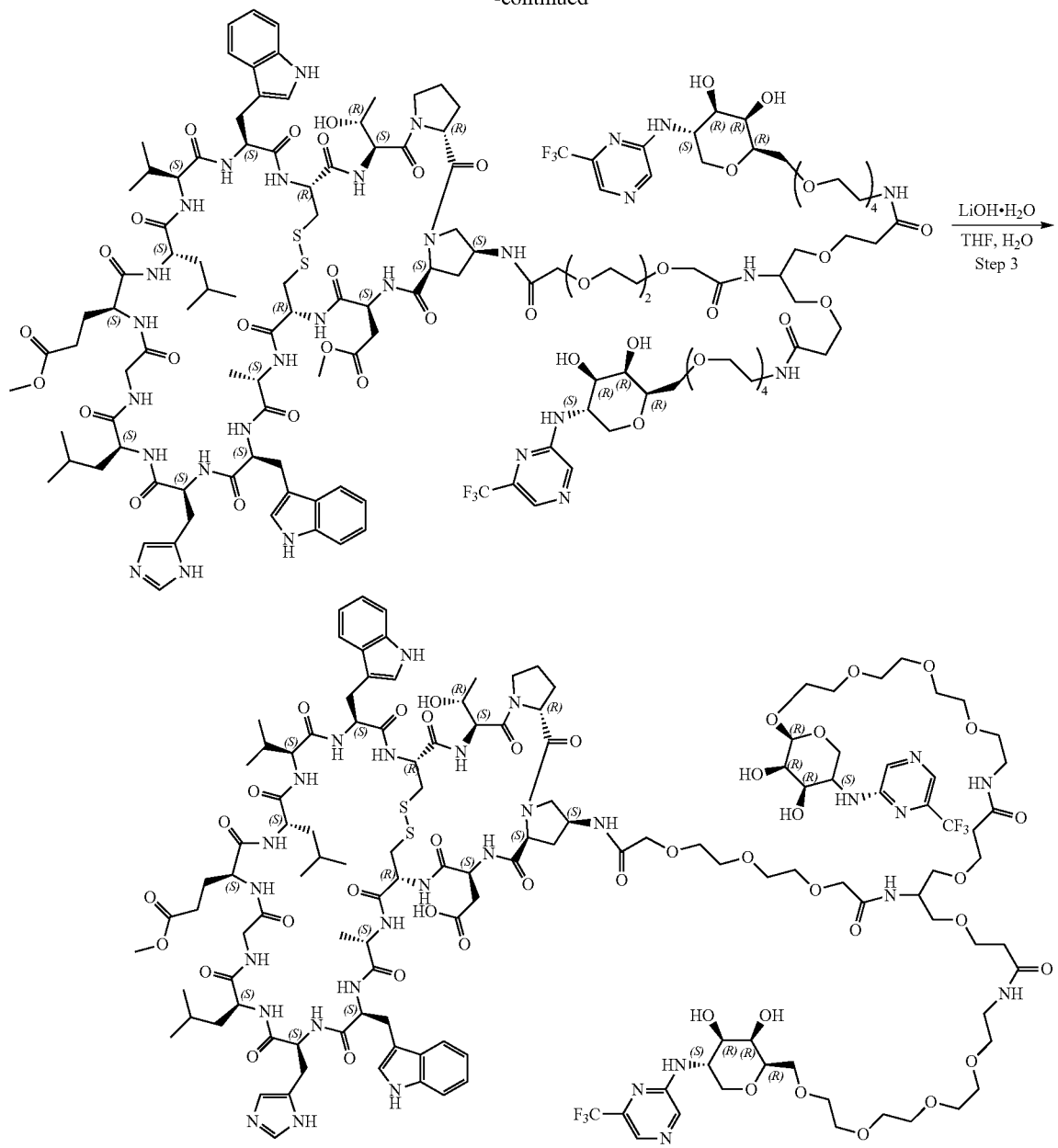

Compound 40

Step 1: To a solution of 3-((2S,5aR,11S,14R,17S,20S, 23S,26S,32S,35S,38S,41S,44R,47S,49aS)-35-((1H-imidazol-5-yl)methyl)-17,38-bis((1H-indol-3-yl)methyl)-2-amino-47-(carboxymethyl)-11-((R)-1-hydroxyethyl)-23,32-diisobutyl-20-isopropyl-41-methyl-5,10,13,16,19,22,25,28, 31,34,37,40,43,46,49-pentadecaoxooctatetracontahydro-5H-14,44-(methanodithiomethano) dipyrrolo[1,2-a:1',2'-d][1,4,7,10,13,16,19,22,25,28,31,34,37,40,43]pentadecaazacyclo pentatetracontin-26-yl)propanoic acid (3.0 g, 87.0% purity) in HCl/MeOH (4 M, 60 mL) was stirred at 25° C. for 2 hrs. The solvent was removed under reduced pressure. The residue was purified by prep-HPLC (acid condition, TFA) to afford methyl 3-((2S,5aR,11S,14R,17S,20S,23S,26S,32S, 35S,38S,41S,44R,47S,49aS)-35-((1H-imidazol-5-yl)methyl)-17,38-bis((1H-indol-3-yl)methyl)-2-amino-11-((R)-1-hydroxyethyl)-23,32-diisobutyl-20-isopropyl-47-(2-methoxy-2-oxoethyl)-41-methyl-5,10,13,16,19,22,25,28,31,34, 37,40,43,46,49-pentadecaoxooctatetracontahydro-5H-14, 44-(methanodithiomethano) dipyrrolo[1,2-a:1',2'-d][1,4,7, 10,13,16,19,22,25,28,31,34,37,40,43]pentadecaazacyclo pentatetracontin-26-yl)propanoate (1.5 g, 95.7% purity, 53.8% yield) as a white solid. Chemical Formula: $C_{81}H_{112}N_{20}O_{20}S_2$, LCMS found: $[M+H]^{1+}=1749.88$, $[M+2H]^{2+}=875.59$.

Step 2: To a solution of methyl 3-((2S,5aR,11S,14R,17S, 20S,23S,26S,32S,35S,38S,41S,44R,47S,49aS)-35-((1H-imidazol-5-yl)methyl)-17,38-bis((1H-indol-3-yl)methyl)-2-amino-11-((R)-1-hydroxyethyl)-23,32-diisobutyl-20-isopropyl-47-(2-methoxy-2-oxoethyl)-41-methyl-5,10,13,16, 19,22,25,28,31,34,37,40,43,46,49-pentadecaoxooctatetracontahydro-5H-14,44-(methanodithiomethano)dipyrrolo [1,2-a:1',2'-d][1,4,7,10,13,16,19,22,25,28,31,34,37,40,43] pentadecaazacyclopentatetracontin-26-yl)propanoate), (58.81 mg, 42.86 umol, 1.00 eq), EDCI (16.43 mg, 85.71 umol, 2.00 eq), HOBt (11.58 mg, 85.71 umol, 2.00 eq) in DMF (0.5 mL) was stirred at 0° C. for 1 hr. The mixture was purified by prep-HPLC (acid condition, TFA) to afford methyl 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-2-(1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-amido)-11-((R)-1-hydroxyethyl)-23,32-diisobutyl-20-isopropyl-47-(2-methoxy-2-oxoethyl)-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoate (60.0 mg, 98.8% purity, 44.5% yield) as a white solid. Chemical Formula: $C_{136}H_{197}F_6N_{29}O_{43}S_2$, LCMS found: $[M+H+Na]^{2+}=1564.20$, $[M+2H]^{2+}=1552.70$, $[M+3H]^{3+}=1035.4$, $[M+4H]^{4+}=777.00$.

Step 3: To a solution of methyl 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-2-(1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-amido)-11-((R)-1-hydroxyethyl)-23,32-diisobutyl-20-isopropyl-47-(2-methoxy-2-oxoethyl)-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoate (55.0 mg, 17.72 umol, 1.00 eq) in THF (0.5 mL), H$_2$O (0.3 mL) was added LiOH·H$_2$O (1 M, 70.87 uL, 4.00 eq) and the mixture was stirred at 25° C. for 1 hr. The mixture was acidified by 1 M HCl to pH=3, then purified by prep-HPLC (acid condition, TFA) directly to afford 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid (Compound 40, 11.7 mg, 96.6% purity, 20.7% yield) as a white solid. Chemical Formula: $C_{134}H_{193}F_6N_{29}O_{43}S_2$, LCMS found: $[M+H+Na]^{2+}=1549.8$, $[M+2H]^{2+}=1538.7$, $[M+3H]^{3+}=1026.2$, $[M+4H]^{4+}=769.8$.

Preparation of Compound 50: 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15-oxo-2,5,8,11,18-pentaoxa-14,21-diazatricosan-23-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid Compound 50

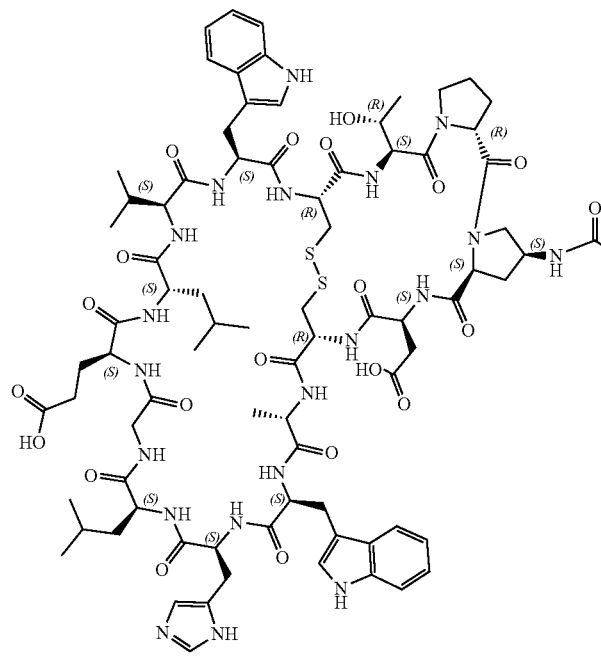
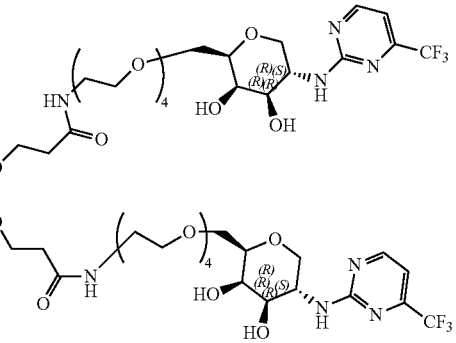

Compound 50 was prepared according to the procedures described above wherein the starting material for the preparation of Compound 50 is (1,39-bis((2R,3R,4R,5S)-3,4-dihydroxy-5-((4-(trifluoromethyl)pyrimidin-2-yl)amino)tetrahydro-2H-pyran-2-yl)-15,25-dioxo-2,5,8,11,18,22,29,32,35,38-decaoxa-14,26-diazanonatriacontan-20-yl)glycine, Yield: 2.7 mg, 97.4% purity, 20.5% yield, white solid. LC-MS (ESI) found: [M+2H]$^{2+}$=1465.59, [M+3H]$^{3+}$=977.25.

Preparation of Compound 47: 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27-heptaoxa-14,21-diazanonacosan-29-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid Compound 47

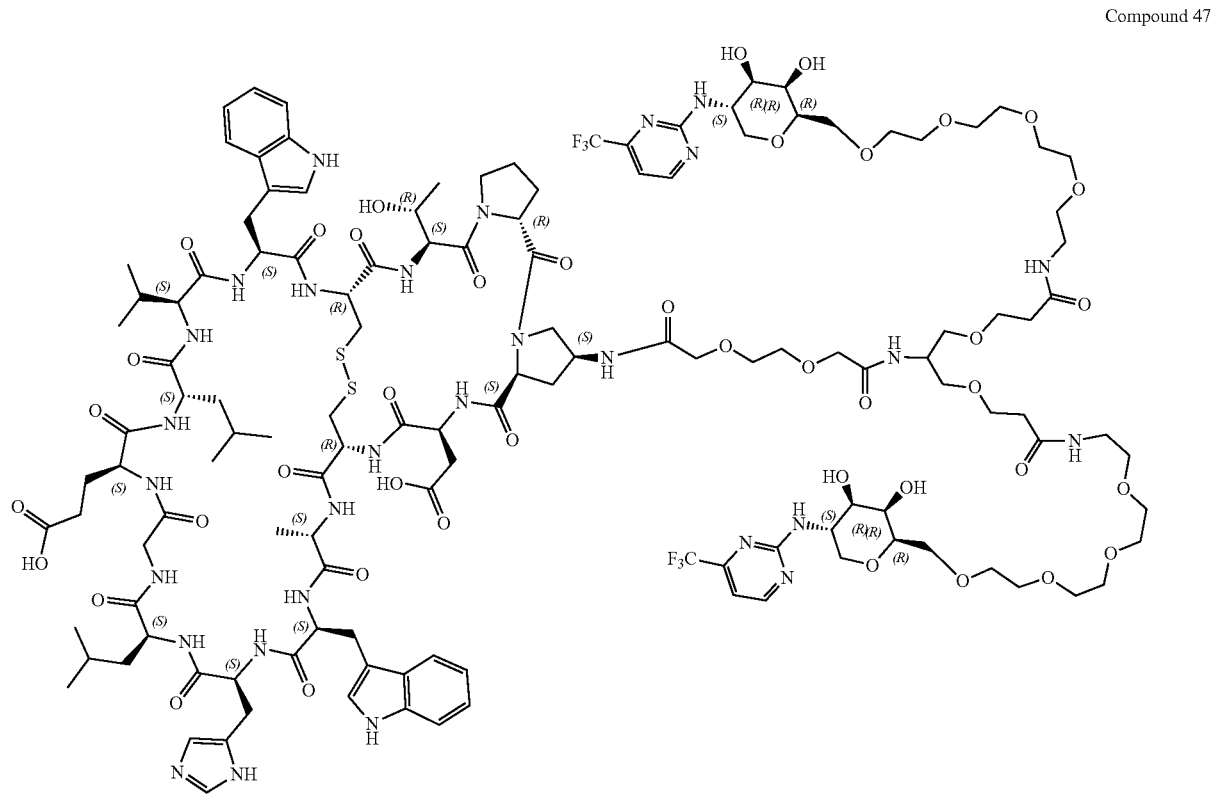

Compound 47 was prepared according to the procedures described in above, wherein the starting material for the preparation of Compound 47 is 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27-heptaoxa-14,21-diazanonacosan-29-oic acid, Yield: 2.8 mg, 96.8% purity, 23.4% yield, white solid. LC-MS (ESI) found: [M+2Na]$^{2+}$=1562.10, [M+H+Na]$^{2+}$=1550.50, [M+2H]$^{2+}$=1539.00, [M+3H]$^{3+}$=1026.70.

Preparation of Compound 46: 3-((2S,5aR,11S,14R, 17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24-hexaoxa-14,21-diazahexacosan-26-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid Compound 46

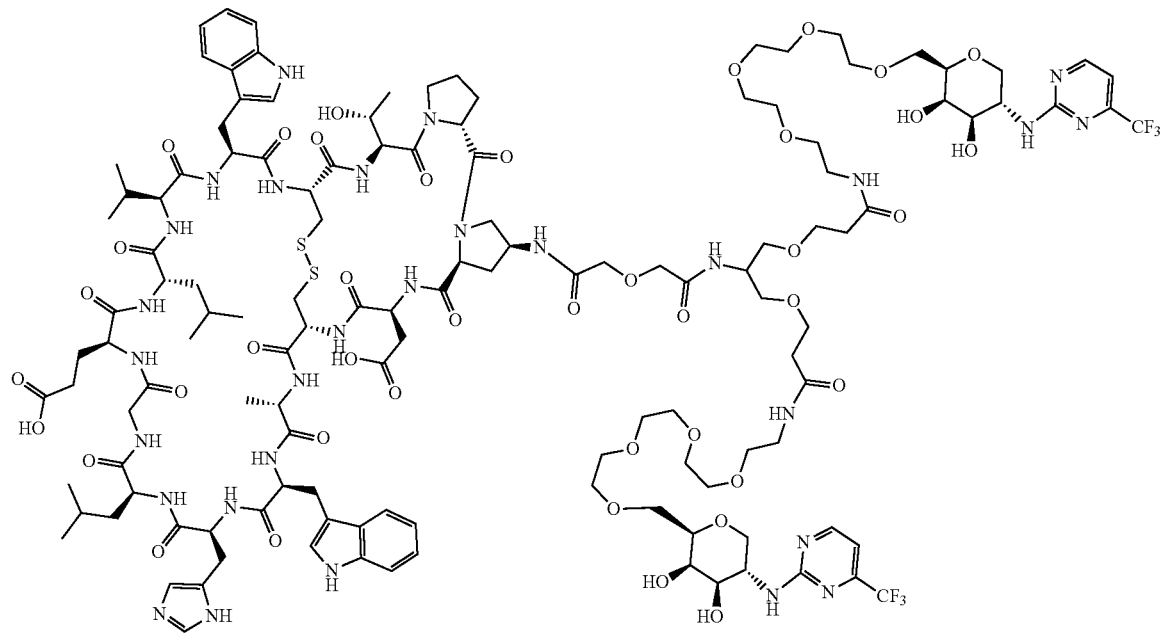

Compound 46 was prepared according to the procedures described above, wherein the starting material for the preparation of Compound 46 is 1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24-hexaoxa-14,21-diazahexacosan-26-oic acid, Yield: 5.8 mg, 93.2% purity, 35.0% yield, white solid. LC-MS (ESI) found: $[M+H+Na]^{2+}=$ 1505.7, $[M+2H]^{2+}=1494.7$, $[M+3H]^{3+}=996.7$, $[M+4H]^{3+}=747.9$.

Preparation of Compound 45: 3-((2S,5aR,11S,14R, 17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15-oxo-2,5,8,11,18-pentaoxa-14,21-diazatricosan-23-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

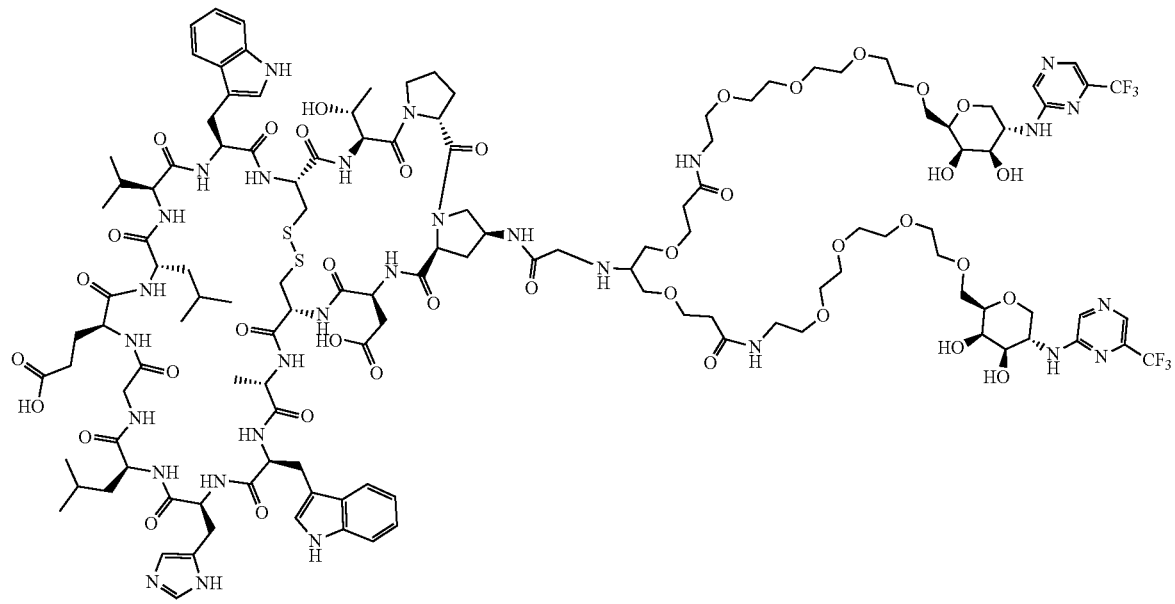

Compound 45

Compound 45 was prepared according to the procedures described above, wherein the starting material for the preparation of Compound 45 is (1,39-bis((2R,3R,4R,5S)-3,4-dihydroxy-5-((6-(trifluoromethyl)pyrazin-2-yl)amino)tetrahydro-2H-pyran-2-yl)-15,25-dioxo-2,5,8,11,18,22,29,32,35,38-decaoxa-14,26-diazanonatriacontan-20-yl)glycine, Yield: 63.0 mg, 94.1% purity, 66.5% white solid. LC-MS (ESI) found: $[M+H+Na]^{2+}=1476.7$, $[M+2H]^{2+}=1465.3$, $[M+3H]^{3+}=977.3$.

Preparation of Compound 60: 3-((2S,5aR,11S,14R,17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano)dipyrrolo[1,2-a:1',2'-d][1,4,7,10,13,16,19,22,25,28,31,34,37,40,43]pentadecaazacyclopentatetracontin-26-yl)propanoic acid

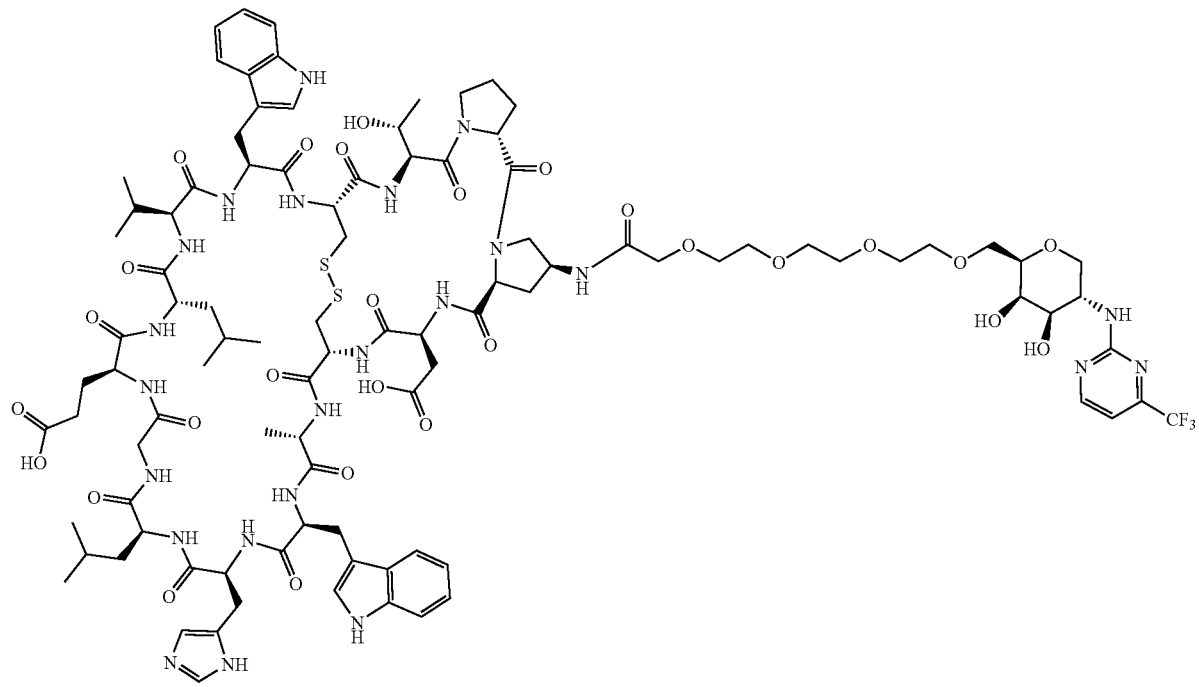 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)COCCOCCOCCOC[C@H]3OC[C@H](Nc4nccc(C(F)(F)F)n4)[C@@H](O)[C@H]3O)C[C@H]1C(=O)N[C@@H](CC(=O)O)C(=O)N2]

Compound 60 was prepared according to the procedures described in the preparation of Compound 38, wherein the starting material for the preparation of Compound 60 is 1-((3aR,4R,7S,7aR)-2,2-dimethyl-7-((4-(trifluoromethyl)pyrimidin-2-yl)amino)tetrahydro-4H-[1,3]dioxolo[4,5-c]pyran-4-yl)-2,5,8,11-tetraoxatridecan-13-oic acid. Yield: 8.8 mg, 93.1% purity, 59.7% white solid. LC-MS (ESI) found: $[M+H+Na]^{2+}$=1550.50, $[M+2H]^{2+}$=1102.70, $[M+3H]^{3+}$=735.80.

Preparation of Intermediate 11: 3-((6S,9R,12S,15S, 18S,21S,27S,30S,33S,36S,39R,42S,44aS,46S, 49aR)-30-((1H-imidazol-5-yl)methyl)-12,33-bis ((1H-indol-3-yl)methyl)-46-amino-42- (carboxymethyl)-6-((R)-1-hydroxyethyl)-18,27- diisobutyl-15-isopropyl-36-methyl 5,8,11,14,17,20, 23,26,29,32,35,38,41,44,49- pentadecaoxooctatetracontahydro-1H-9,39- (methanodithiomethano)dipyrrolo[1,2-a:1',2'-d][1,4, 7,10,13,16,19,22,25,28,31,34,37,40,43] pentadecaazacyclopentatetracontin-21-yl)propanoic acid
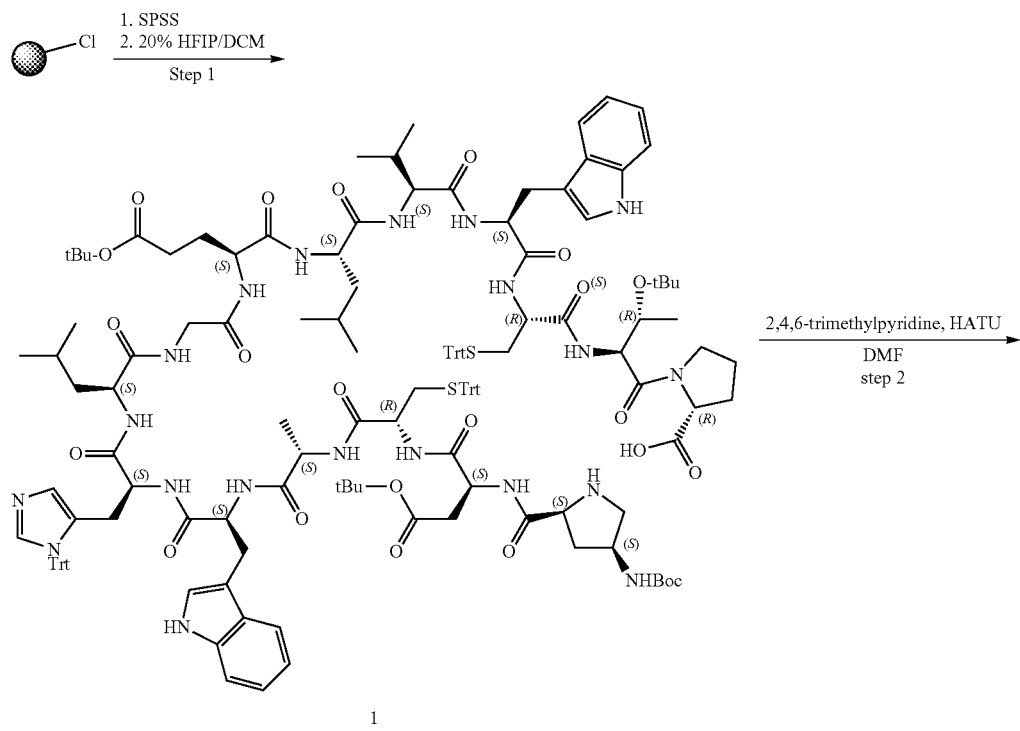
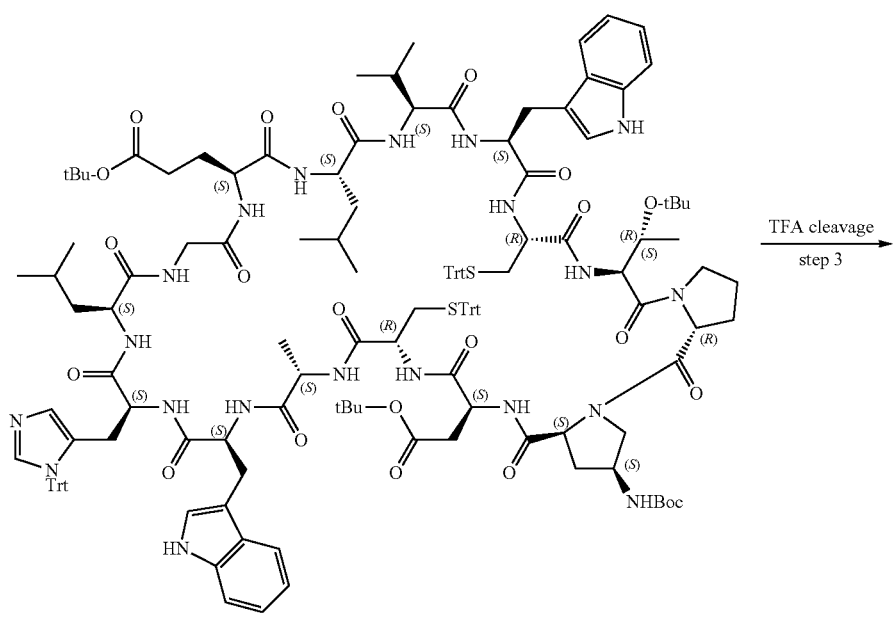

-continued

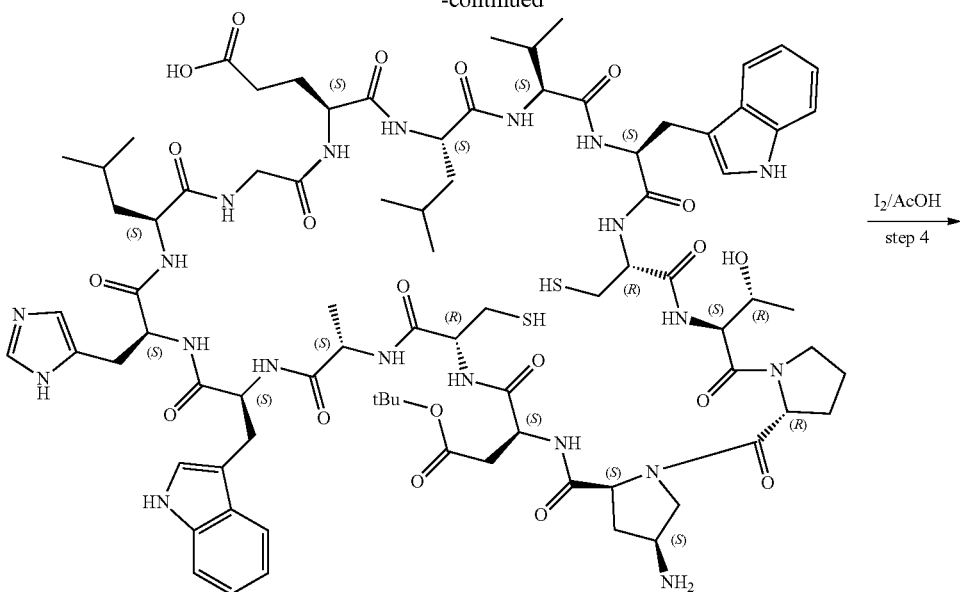

I₂/AcOH
step 4 →

3

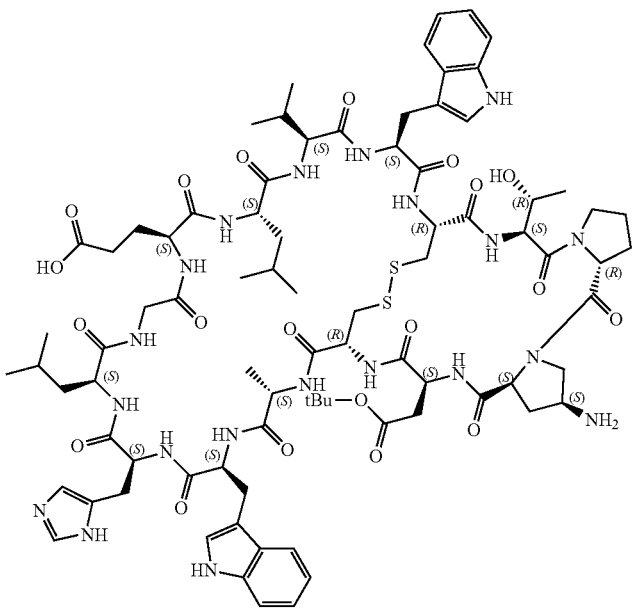

Intermediate 11

Solid Phase Peptide Synthesis:

The peptide was synthesized using standard Fmoc chemistry.

1) Resin preparation: To the vessel containing CTC Resin (200.00 g, 200.00 mmol, 1.00 mmol/g) and Fmoc-D-Pro-OH (67.40 g, 200.00 mmol, 1.00 eq) in DCM (3 L) was added DIEA (139.46 mL, 800.00 mmol, 4.00 eq) dropwise and mixed for 2 hrs with N₂ bubbling at 15° C. Then added MeOH (200.00 mL) and bubbled with N₂ for another 30 mins. The resin was washed with DMF (3 L)*5. Then 20% piperidine in DMF (5 L) was added and the mixture was bubbled with $N_2$ for 30 mins at 15° C. The mixture was filtered to obtain the resin. The resin was washed with DMF (3 L)*5 before proceeding to next step.

2) Coupling: A solution of Fmoc-Thr(tBu)-OH (238.20 g, 600.00 mmol, 3.00 eq), HBTU (216.03 g, 570.00 mmol, 2.85 eq) in DMF (500 mL) was added to the resin with $N_2$ bubbling. Then DIEA (209.18 mL, 1200.00 mmol, 6.00 eq) was added to the mixture dropwise and bubbled with $N_2$ for 30 mins at 15° C. The coupling reaction was monitored by ninhydrin test, if it showed colorless, the coupling was completed. The resin was then washed with DMF (3 L)*5.

3) De-protection: 20% piperidine in DMF (5 L) was added to the resin and the mixture was bubbled with $N_2$ for 30 mins at 15° C. The resin was then washed with DMF (3 L)*5. The De-protection reaction was monitored by ninhydrin test, if it showed blue or other brownish red, the reaction was completed.

4) Step 2 and 3 were repeated for all other amino acids: (2-15 in Table 1).

TABLE 1

| # | Materials | Coupling reagents |
|---|---|---|
| 1 | Fmoc-D-Pro-OH (1.00 eq) | DIEA (4.00 eq) |
| 2 | Fmoc-Thr(tBu)-OH (3.00 eq) | HBTU (2.85 eq) and DIEA (6.00 eq) |
| 3 | Fmoc-Cys(Trt)-OH (3.00 eq) | HBTU (2.85 eq) and DIEA (6.00 eq) |
| 4 | Fmoc-Trp(Boc)-OH (3.00 eq) | HBTU (2.85 eq) and DIEA (6.00 eq) |
| 5 | Fmoc-Val-OH (3.00 eq) | HBTU (2.85 eq) and DIEA (6.00 eq) |
| 6 | Fmoc-Leu-OH (3.00 eq) | HBTU (2.85 eq) and DIEA (6.00 eq) |
| 7 | Fmoc-Glu(OtBu)-OH (3.00 eq) | HBTU (2.85 eq) and DIEA (6.00 eq) |
| 8 | Fmoc-Gly-OH (3.00 eq) | HBTU (2.85 eq) and DIEA (6.00 eq) |
| 9 | Fmoc-Leu-OH (3.00 eq) | HBTU (2.85 eq) and DIEA (6.00 eq) |
| 10 | Fmoc-His(Trt)-OH (2.00 eq) | HBTU (2.85 eq) and DIEA (6.00 eq) |
| 11 | Fmoc-Trp-OH (3.00 eq) | HBTU (2.85 eq) and DIEA (6.00 eq) |
| 12 | Fmoc-Ala-OH (3.00 eq) | HBTU (2.85 eq) and DIEA (6.00 eq) |
| 13 | Fmoc-Cys(Trt)-OH (3.00 eq) | HBTU (2.85 eq) and DIEA (6.00 eq) |
| 14 | Fmoc-Asp(OtBu)-OH (3.00 eq) | HBTU (2.85 eq) and DIEA (6.00 eq) |
| 15 | Boc-(2S,4S)-4-amino-1-Fmoc-pyrrolidine-2-carboxylic acid (1.00 eq) | HATU (0.95 eq) and DIEA (2.00 eq) |

Peptide Cleavage and Purification:

1) Cleavage buffer (20% TIP/DCM, 8.0 L) was added into the flask containing the side chain protected crude peptide. The mixture was stirred for 1 hr at room temperature and the solution was collected after filtration. The cleavage step was repeated for another time.
2) The solution was combined after filtration.
3) The solution was concentrated by rotary evaporation.
4) The crude peptide was dried under lyophilization.
5) Compound 1 (231.00 g, crude) was obtained as a white solid.
6) A mixture of compound 1 (13.58 g, 4.99 mmol, 1.00 eq), 2,4,6-trimethylpyridine (3.62 g, 29.98 mmol, 6.00 eq) in DMF (5.0 L) was added HATU (2.84 g, 7.49 mmol, 1.50 eq) at 25° C. Then the mixture was stirred at 25° C. for 3 hrs. Totally 17 batches were made one by one.
7) The solution was concentrated by rotary evaporation.
8) The residue was added to 0.50 M HCl (cold, 10 L) and white solid was precipitated. After filtered, the solid was dried under lyophilization to afford compound 2 (245.00 g, crude, 17 batches) as a white solid. Chemical Formula: $C_{159}H_{192}N_{20}O_{26}S_2$, LCMS found: $[M+H+Na]^{2+}=1370.88$; $[M+2H-242]^{2+}=1239.42$;

Step 3-4: Preparation of Intermediate 11

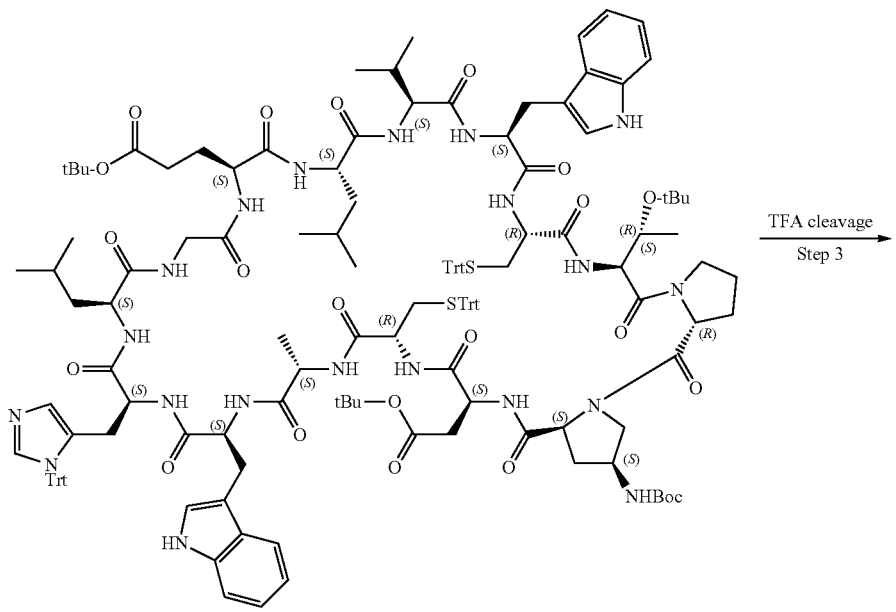

-continued

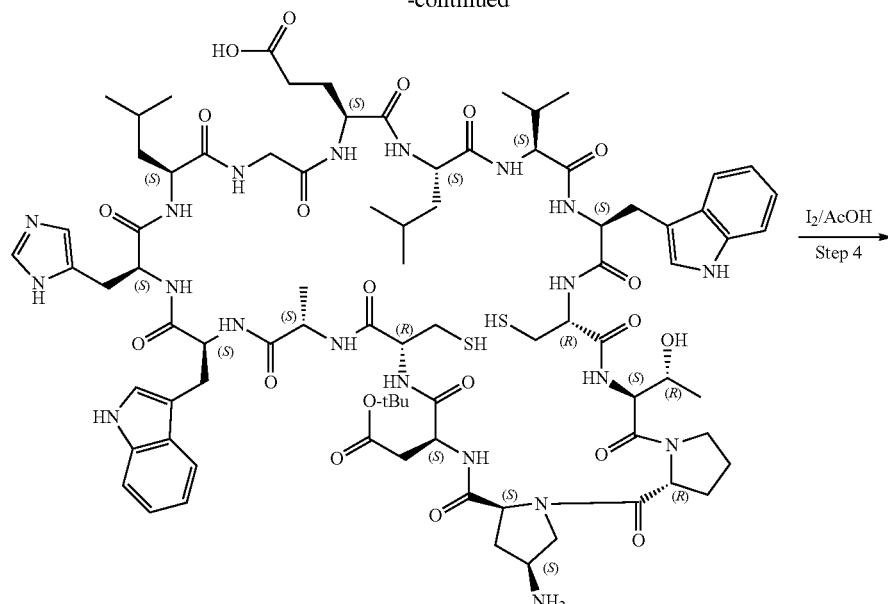

3

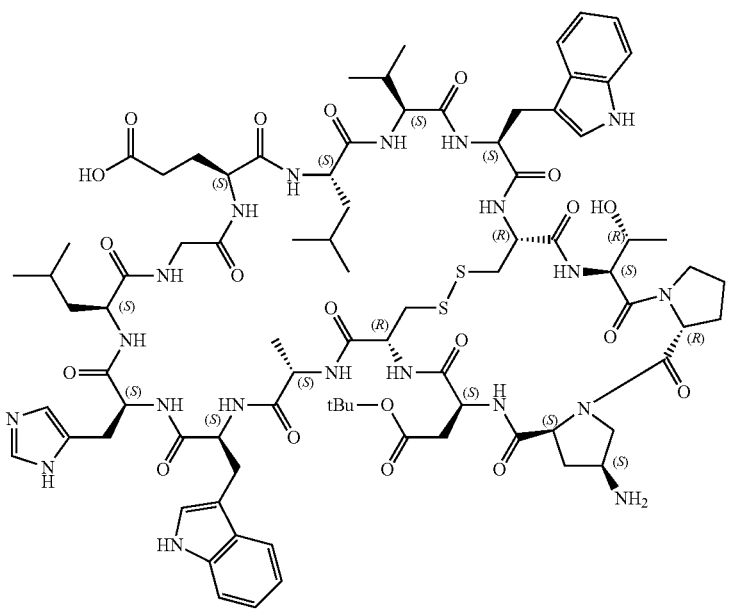

Intermediate 11

A mixture of compound 2 (245.00 g, crude) in TFA/TIS/ H₂O/3-mercaptopropanoic acid (92.5%/2.5%/2.5%/2.5%, v/v/v, 5 L) was stirred at 20° C. for 1.5 hrs. The mixture was precipitated with cold isopropyl ether (30 L). After filtration, the solid was dried under vacuum for 2 hrs to get compound 3 (170.50 g, crude). Compound 3 (170.50 g, crude) was dissolved in MeCN/H₂O (1/1, v/v, 100 L). 0.1 M I₂/HOAc was added to the mixture dropwise at 25° C. until the light yellow persisted, then the mixture was quenched with 0.1 M Na₂S₂O₃ dropwise until the light yellow disappeared. After filtration, the filtrate was purified by prep-HPLC (acid condition, TFA) directly to afford Intermediate 11 (21.10 g, 6.15% yield, 87.06% purity) as a white solid. Chemical Formula: $C_{79}H_{108}N_{20}O_{20}S_2$, LCMS found: $[M+H]^{1+}=$ 1722.70, $[M+2H]^{2+}=861.50$.

Preparation of Compound 61: 3-((2S,5aR,11S,14R, 17S,20S,23S,26S,32S,35S,38S,41S,44R,47S,49aS)-35-((1H-imidazol-5-yl)methyl)-17,38-bis((1H-indol-3-yl)methyl)-47-(carboxymethyl)-2-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-amido)-11-((R)-1-hydroxyethyl)-23,32-diisobutyl-20-isopropyl-41-methyl-5,10,13,16,19,22,25,28,31,34,37,40,43,46,49-pentadecaoxooctatetracontahydro-5H-14,44-(methanodithiomethano) dipyrrolo[1,2-a:1',2'-d][1,4,7,10,13,16,19,22,25,28,31,34,37,40,43]pentadecaazacyclopentatetracontin-26-yl)propanoic acid

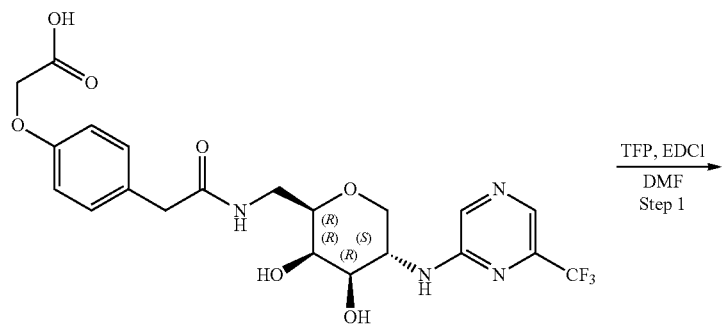

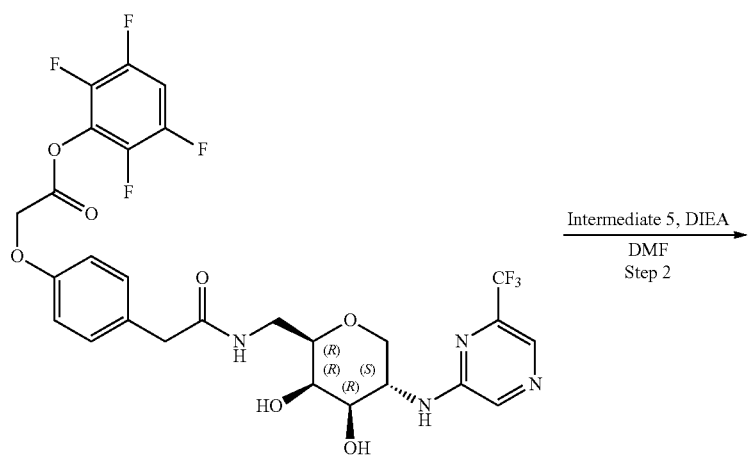

-continued

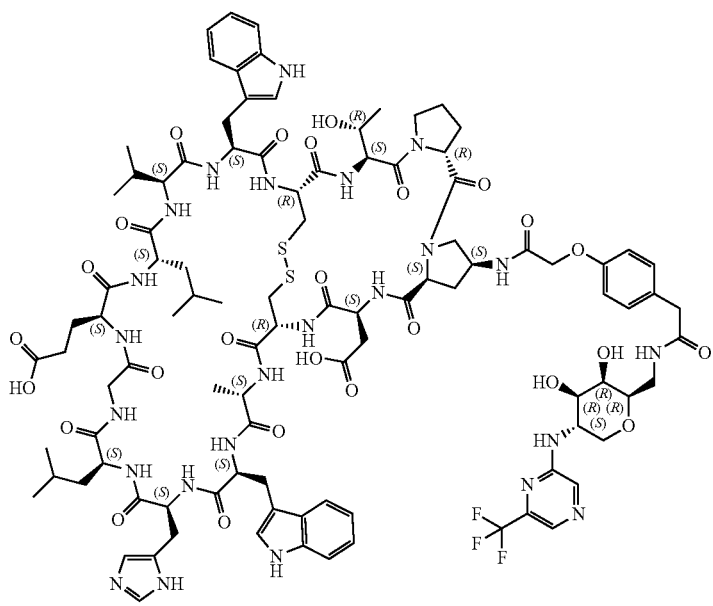

Compound 61

Step 1: Preparation of TFP ester (Compound 4)

A mixture of 2,3,5,6-tetrafluorophenol (105.50 mg, 639.44 umol, 4.00 eq), 2-(4-(2-((((2R,3R,4R,5S)-3,4-dihydroxy-5-((6-(trifluoromethyl)pyrazin-2-yl)amino)tetrahydro-2H-pyran-2-yl)methyl)amino)-2-oxoethyl)phenoxy)acetic acid (80.0 mg, 159.86 umol, 1.00 eq) in DMF (1.0 mL) was cooled to 0° C. Then the mixture was added EDCI (61.29 mg, 319.73 umol, 2.00 eq) at 0° C. and stirred at 0° C. for 2 hrs. The reaction mixture was purified by prep-HPLC (acid condition, TFA) to afford TFP ester 4 (15 mg, 23.13 umol, 14.47% yield) as a colorless oil. Chemical Formula: $C_{27}H_{23}F_7N_4O_7$, LCMS found: $[M+H]^+=649.10$.

Step 2: Preparation of Compound 61

A mixture of Intermediate 11 (27.72 mg, 16.10 umol, 1.20 eq), compound 4 (8.7 mg, 13.42 umol, 1.00 eq), DIEA (5.20 mg, 40.25 umol, 7.01 uL, 3.00 eq) in DMF (0.3 mL) was stirred at 25° C. for 1 hr. The reaction mixture was purified by prep-HPLC (acid condition, TFA) to afford Compound 61 (14.6 mg, 6.55 umol, 98.9% purity, 48.8% yield) as a white solid. Chemical Formula: $C_{100}H_{129}F_3N_{24}O_{26}S_2$, LCMS found: $[M+2H]^{2+}=1103.1$, $[M+H+Na]^{2+}=1114.5$, $[M+3H]^{3+}=735.6$ The compounds Compound 62, Compound 63, Compound 64, Compound 65, Compound 66, Compound 67, Compound 68, Compound 69, Compound 45, Compound 70, Compound 71, Compound 72, Compound 42, Compound 73, Compound 74, Compound 75 were prepared according to the procedure same as that of Compound 61 using the starting material listed in the table below.

| Compound | Starting material | Analytical data |
|---|---|---|
| Compound 62 | 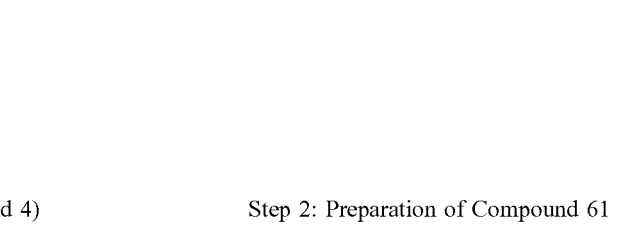 | Yield: 30.0 mg, 96.0% purity, 43.6% yield, white solid. LC-MS found: $[M + 2H]^{2+} = 1050.0$, $[M + H + Na]^{2+} = 106.5$, $[M + 3H]^{3+} = 700.1$ |

-continued

| Compound | Starting material | Analytical data |
|---|---|---|
| Compound 63 | 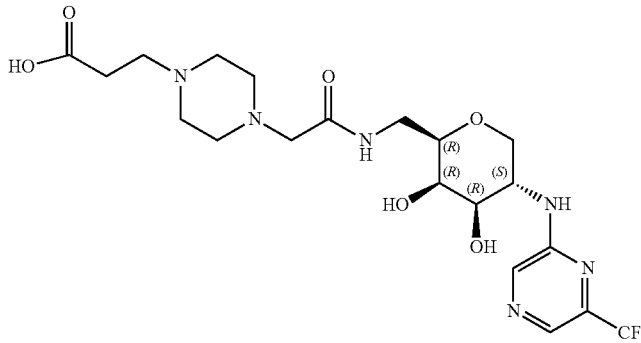<br>A40 | Yield: 26.5 mg, 97.1% purity, 39.3% yield, white solid. LC-MS found: $[M + 2Na]^{2+} = 1128.2$, $[M + H + Na]^{2+} = 1117.5$, $[M + 2H]^{2+} = 1106.1$, $[M + 3H]^{3+} = 737.4$. |
| Compound 64 | 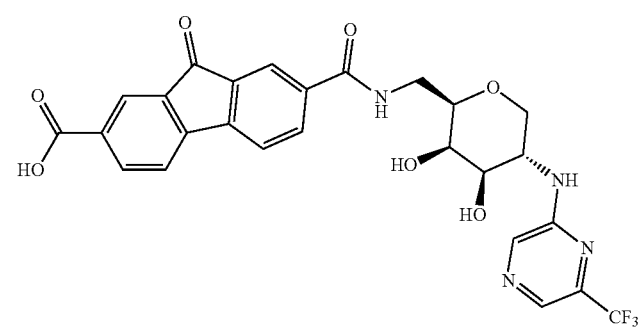 [SMILES: O=C(O)c1ccc2c(c1)C(=O)c1cc(C(=O)NC[C@H]3OC[C@H](Nc4cncc(C(F)(F)F)n4)[C@@H](O)[C@H]3O)ccc1-2]<br>A125 | Yield: 29.7 mg, 96.4% purity, 42.5% yield, white solid. LC-MS found: $[M + 2H]^{2+} = 1132.6$, $[M + 3H]^{3+} = 755.4$. |
| Compound 65 | 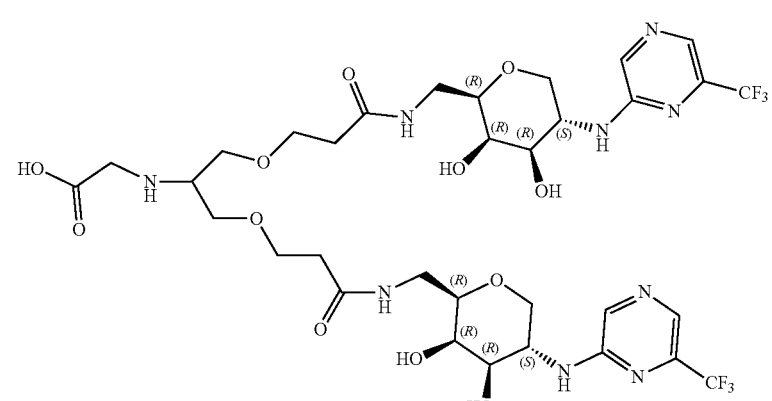<br>A137 | Yield: 3.5 mg, 97.1% purity, 4.4% yield, white solid. LC-MS found: $[M + H + Na]^{2+} = 1300.7$, $[M + 2H]^{2+} = 1289.7$, $[M + 3H]^{3+} = 860.1$. |
| Compound 66 | 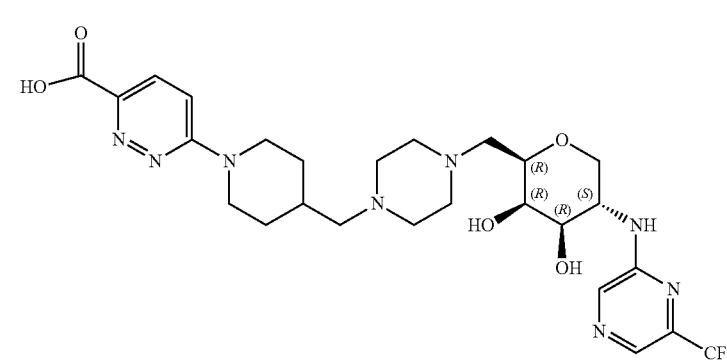<br>A138 | Yield: 33 mg, 96.4% purity, 34.3% yield, white solid. LC-MS found: $[M + 2H]^{2+} = 1151.2$, $[M + 3H]^{3+} = 767.7$. |

-continued

| Compound | Starting material | Analytical data |
|---|---|---|
| Compound 67 | 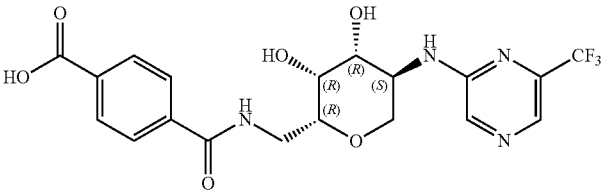<br>A139 | Yield: 74.3 mg, 98.7% purity, 45.6% yield, white solid. LC-MS found: [M + 2H]$^{2+}$ = 1081.1, [M + 3H]$^{3+}$ = 721.0. |
| Compound 68 | 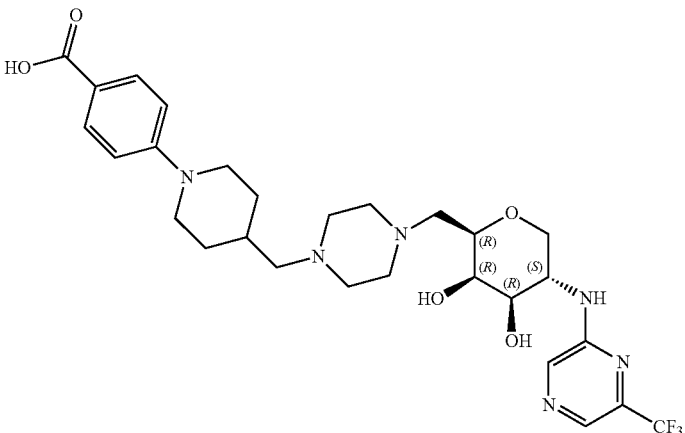<br>A140 | Yield: 112 mg, 93.3% purity, 18.45% yield, white solid. LC-MS (ESI) found: [M + 2H]$^{2+}$ = 1150.3, [M + 3H]$^{3+}$ = 767.6. |
| Compound 69 | 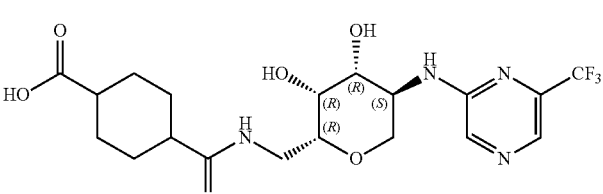<br>A141 | Yield: 26.4 mg, 97.1% purity, 37.2% yield, white solid. LC-MS found: [M + 2H]$^{2+}$ = 1084.2, [M + 3H]$^{3+}$ = 722.9 |
| Compound 45 | 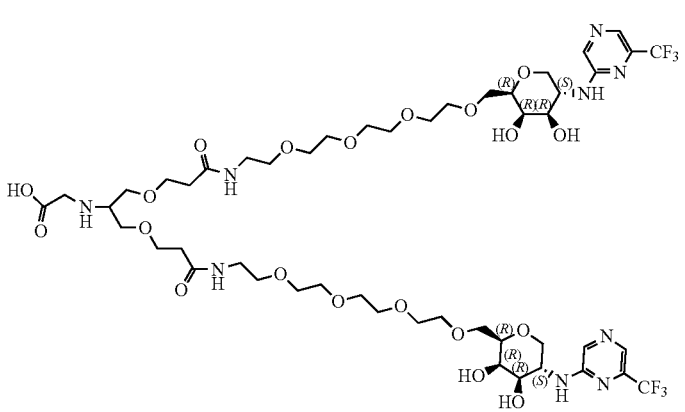<br>A31 | Yield: 1.54 g, 95.6% purity, 35.4% yield, white solid. LC-MS found: [M + H + Na]$^{2+}$ = 1476.7, [M + 2H]$^{2+}$ = 1465.8, [M + 3H]$^{3+}$ = 977.5. |

-continued

| Compound | Starting material | Analytical data |
|---|---|---|
| Compound 70 | 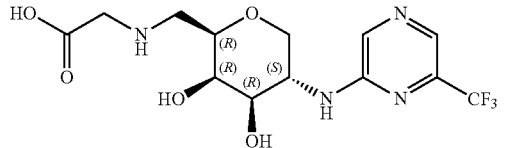<br>A142 | Yield: 1.0 mg, 66.9% purity, 7.65% yield, white solid. LC-MS found: [M + H + Na]$^{2+}$ = 1044.6, [M + 2H]$^{2+}$ = 1036.0, [M + 3H]$^{3+}$ = 690.8. |
| Compound 71 | 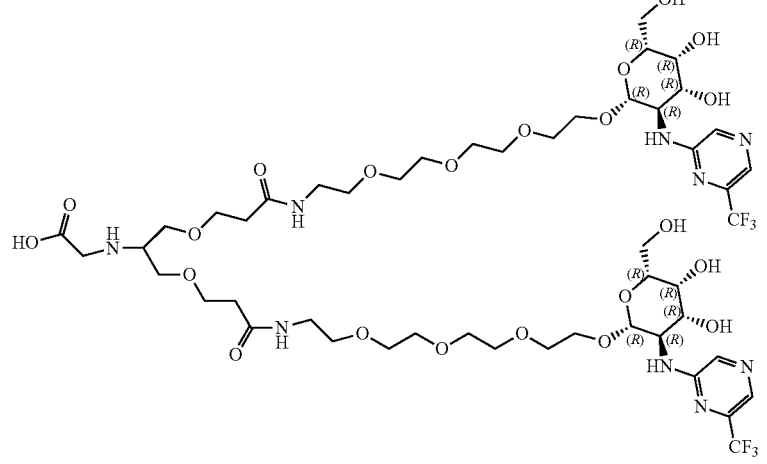<br>A143 | Yield: 17.0 mg, 95.2% purity, 24.5% yield, white solid. LC-MS found: [2M + 3H]$^{3+}$ = 1975.8, [M + 2Na]$^{2+}$ = 1505.0, [M + H + Na]$^{2+}$ = 1493.2, [M + 2H]$^{2+}$ = 1482.0, [M − sugar + 2H]$^{2+}$ = 1328.5, [M + 3H]$^{3+}$ = 988.2. |
| Compound 72 | 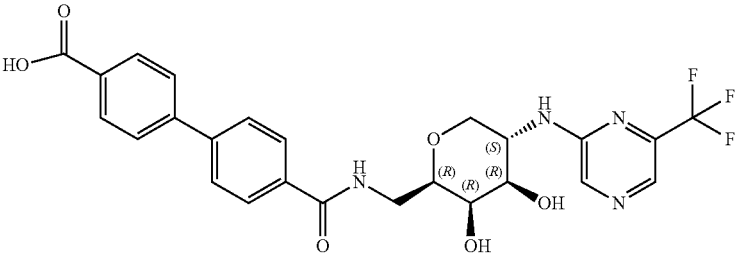<br>A144 | Yield: 39.0 mg, 95.6% purity, 45.3% yield, white solid. LC-MS found: [M + 2H]$^{2+}$ = 1118.9, [M + 3H]$^{3+}$ = 746.5. |
| Compound 42 | 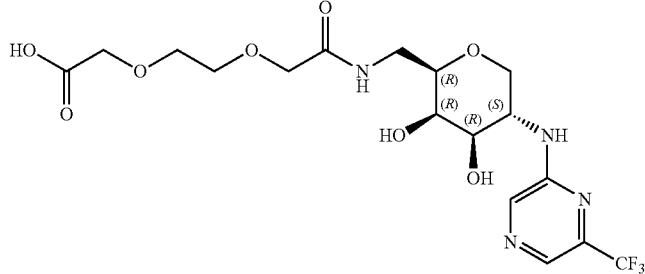<br>A30 | Yield: 2.6 g, 97.9% purity, 60.1% yield, white solid. LC-MS found: [M + 2H]$^{2+}$ = 1087.3, [M + 3H]$^{3+}$ = 725.5. |

-continued

| Compound | Starting material | Analytical data |
|---|---|---|
| Compound 73 | A145 | Yield: 2.0 mg, 93.2% purity, 5.95% yield, white solid. LC-MS found: [M + 2Na]$^{2+}$ = 1516.5, [M + H + Na]$^{2+}$ = 1505.2, [M + 2H]$^{2+}$ = 1494.1, [M + 3H]$^{3+}$ = 996.5. |
| Compound 74 | A31 | Yield: 21.0 mg, 99.0% purity, 26.0% yield, white solid. LC-MS found: [M + H + Na]$^{2+}$ = 1476.4, [M + 2H]$^{2+}$ = 1465.8, [M + 3H]$^{3+}$ = 977.2. |
| Compound 75 | A31 | Yield: 25.9 mg, 98.8% purity, 29.7% yield, white solid. LC-MS found: [M + H + Na]$^{2+}$ = 1490.6, [M + 2H]$^{2+}$ = 1479.4, [M + 3H]$^{3+}$ = 986.6. |

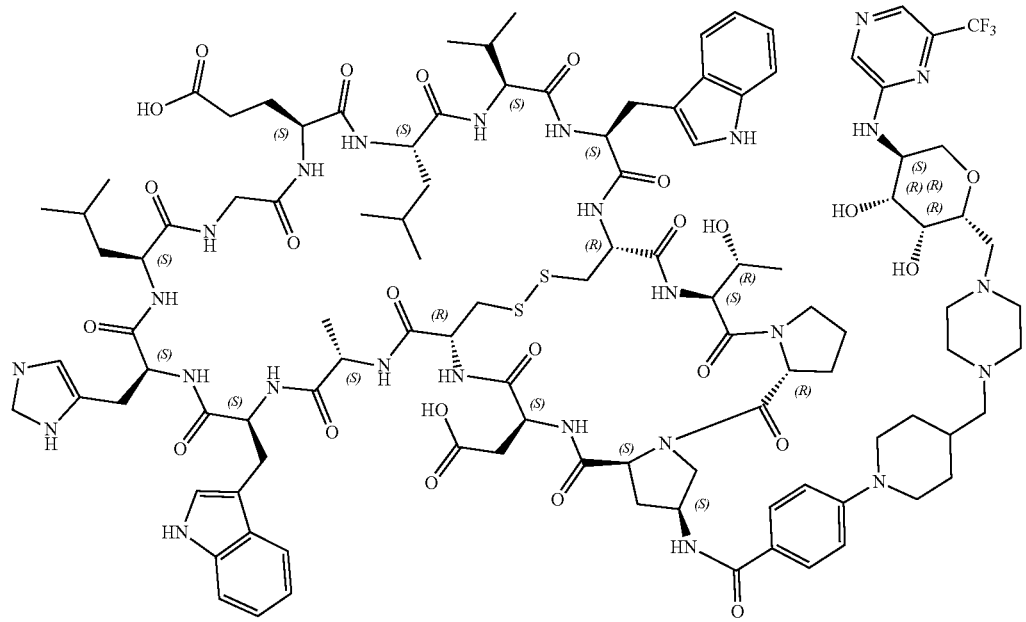

Compound 68

Preparation of Compound 68: 3-((6S,9R,12S,15S, 18S,21S,27S,30S,33S,36S,39R,42S,44aS,46S, 49aR)-30-((1H-imidazol-5-yl)methyl)-12,33-bis ((1H-indol-3-yl)methyl)-42-(carboxymethyl)-46-(4-(4-((4-(((2R,3R,4R,5S)-3,4-dihydroxy-5-((6-(trifluoromethyl) pyrazin-2-yl)amino)tetrahydro-2H-pyran-2-yl)methyl)piperazin-1-yl)methyl)piperidin-1-yl)benzamido)-6-((R)-1-hydroxyethyl)-18,27-diisobutyl-15-isopropyl-36-methyl-5,8,11,14,17,20, 23,26,29,32,35,38,41,44,49-pentadecaoxooctatetra-contahydro-1H-9,39-(methanodithiomethano) dipyr-rolo[1,2-a:1',2' d][1,4,7,10,13,16,19,22,25,28,31,34, 37,40,43]pentadecaazacyclo pentatetracontin-21-yl) propanoic acid Synthesis of Protein Target Ligand

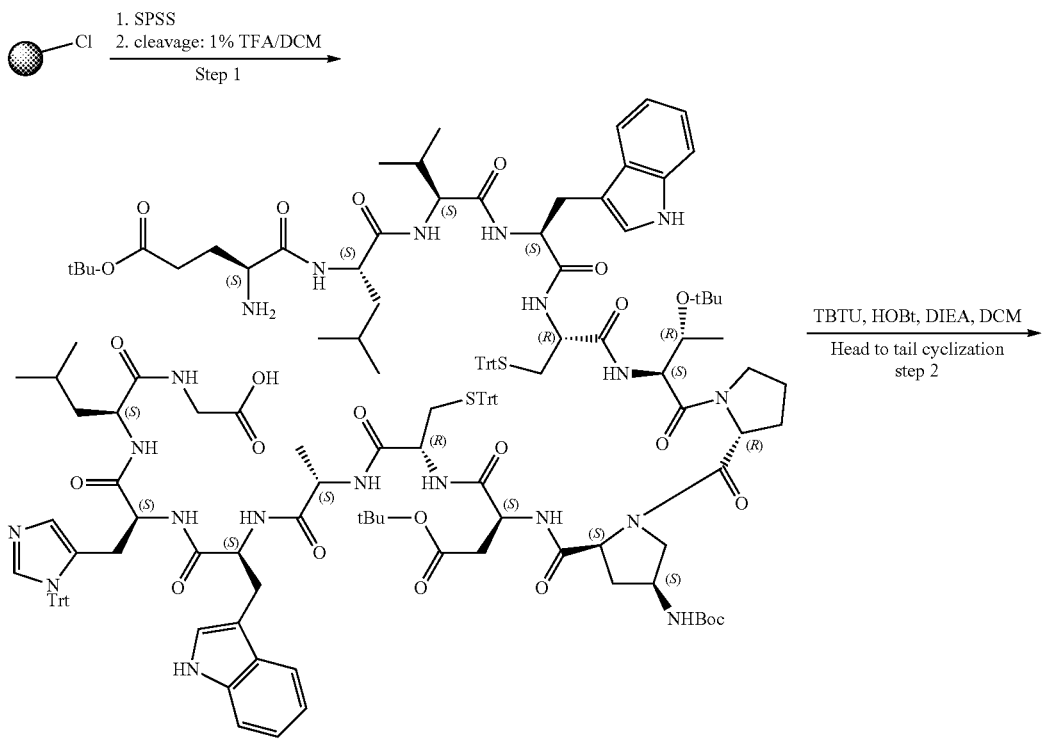

-continued
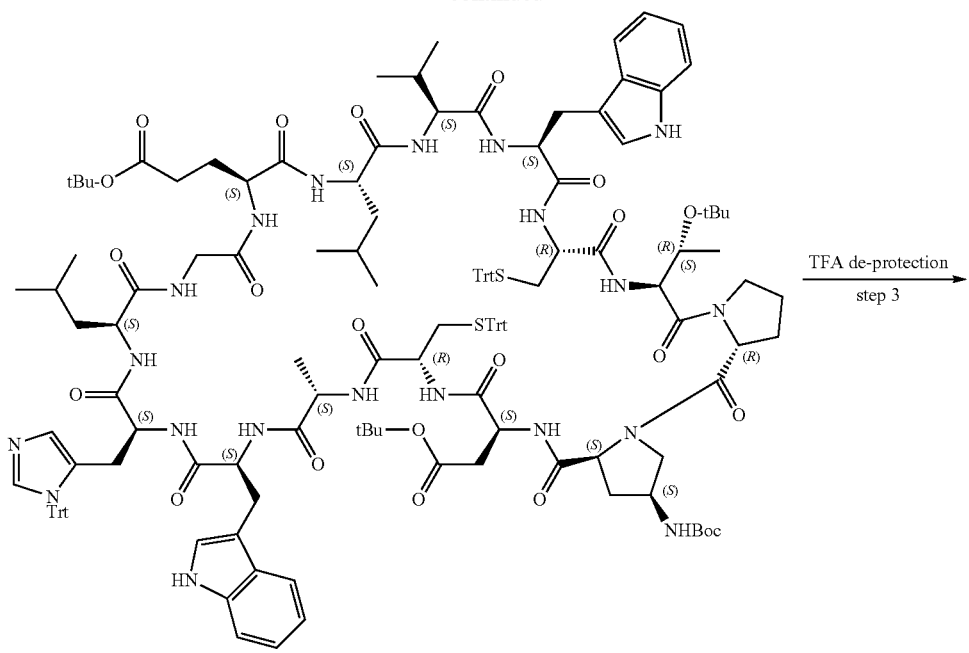
TFA de-protection
step 3
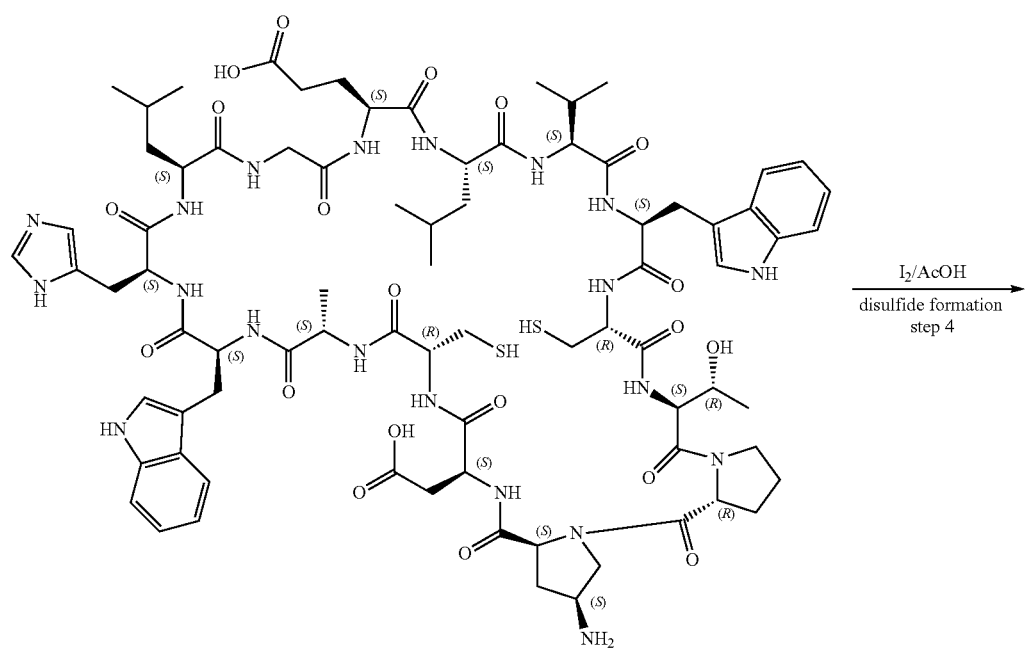
I₂/AcOH
disulfide formation
step 4

-continued

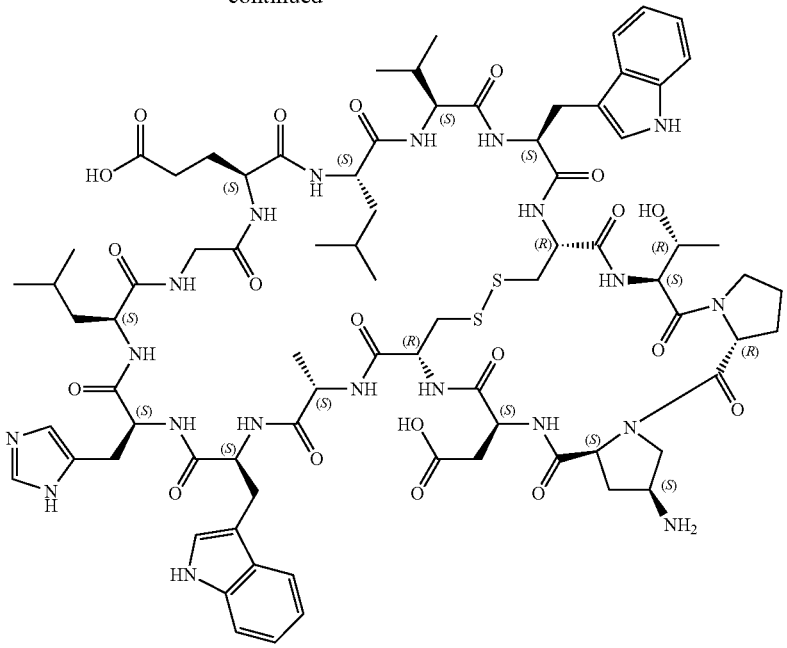

Solid Phase Peptide Synthesis:

The peptide was synthesized using standard Fmoc chemistry.

1) Resin preparation: To the vessel containing CTC Resin (100.00 g, 100.00 mmol, 1.00 mmol/g) and Fmoc-Gly-OH (29.70 g, 100.00 mmol, 1.00 eq) in DCM (1.5 L) was added DIEA (51.60 g, 69.73 mL, 400.00 mmol, 4.00 eq) dropwise and mixed for 2 hrs with $N_2$ bubbling at 15° C. Then added MeOH (100.00 mL) and bubbled with $N_2$ for another 30 mins. The resin was washed with DMF (3 L)*5. Then 20% piperidine in DMF (3 L) was added and the mixture was bubbled with $N_2$ for 30 mins at 15° C. The mixture was filtered to obtain the resin. The resin was washed with DMF (3 L)*5 before proceeding to next step.

2) Coupling: A solution of Fmoc-Leu-OH (105.90 g, 300.00 mmol, 3.00 eq), HBTU (108.15 g, 285.00 mmol, 2.85 eq) in DMF (1.5 L) was added to the resin with $N_2$ bubbling. Then DIEA (77.40 g, 104.58 mL, 600.00 mmol, 6.00 eq) was added to the mixture dropwise and bubbled with $N_2$ for 30 mins at 15° C. The coupling reaction was monitored by ninhydrin test, if it showed colorless, the coupling was completed. The resin was then washed with DMF (3 L)*5.

3) De-protection: 20% piperidine in DMF (3 L) was added to the resin and the mixture was bubbled with $N_2$ for 30 mins at 15° C. The resin was then washed with DMF (3 L)*5. The de-protection reaction was monitored by ninhydrin test, if it showed blue or other brownish red, the reaction was completed.

4) Step 2 and 3 were repeated for all other amino acids: Number #2-15 in Table 1.

5) After all steps were completed, the resin was washed with DMF (3 L)*5, MeOH (3 L)*5 then dried under reduced pressure to afford resin-bound peptide resin (100 mmol).

TABLE 1

| # | Materials | Coupling reagents |
|---|---|---|
| 1 | Fmoc-Gly-OH (3.00 eq) | HBTU (2.85 eq) and DIEA (6.00 eq) |
| 2 | Fmoc-Leu-OH (3.00 eq) | HBTU (2.85 eq) and DIEA (6.00 eq) |
| 3 | Fmoc-His(Trt)-OH (2.00 eq) | HBTU (2.85 eq) and DIEA (6.00 eq) |
| 4 | Fmoc-Trp-OH (3.00 eq) | HBTU (2.85 eq) and DIEA (6.00 eq) |
| 5 | Fmoc-Ala-OH (3.00 eq) | HBTU (2.85 eq) and DIEA (6.00 eq) |
| 6 | Fmoc-Cys(Trt)-OH (3.00 eq) | HBTU (2.85 eq) and DIEA (6.00 eq) |
| 7 | Fmoc-Asp(OtBu)-OH (3.00 eq) | HBTU (2.85 eq) and DIEA (6.00 eq) |
| 8 | Boc-(2S,4S)-4-amino-1-Fmoc-pyrrolidine-2-carboxylic acid (1.50 eq) | HATU (1.42 eq) and DIEA (3.00 eq) |
| 9 | Fmoc-D-Pro-OH (1.00 eq) | DIEA (4.00 eq) |
| 10 | Fmoc-Thr(tBu)-OH (3.00 eq) | HBTU (2.85 eq) and DIEA (6.00 eq) |
| 11 | Fmoc-Cys(Trt)-OH (3.00 eq) | HBTU (2.85 eq) and DIEA (6.00 eq) |
| 12 | Fmoc-Trp-OH (3.00 eq) | HBTU (2.85 eq) and DIEA (6.00 eq) |
| 13 | Fmoc-Val-OH (3.00 eq) | HBTU (2.85 eq) and DIEA (6.00 eq) |
| 14 | Fmoc-Leu-OH (3.00 eq) | HBTU (2.85 eq) and DIEA (6.00 eq) |
| 15 | Fmoc-Glu(OtBu)-OH (3.00 eq) | HBTU (2.85 eq) and DIEA (6.00 eq) |

Peptide Cleavage, Head to Tail Cyclization, TFA De-Protection, Disulfide Formation and Purification:

5) Cleavage: Cleavage solution (1% TFA/DCM, v/v, 1.0 L) was added into the flask containing the side chain protected crude peptide resin (20 mmol). The mixture was stirred for 10 mins at room temperature and the solution was collected after filtration. The cleavage step was repeated for another time. The combined solution afforded compound 1 (20 mmol) in cleavage solution.

6) Head to tail cyclization: The combined solution (compound 1, 20 mmol) was diluted to 20 L with DCM. Then TBTU (12.84 g, 40.00 mmol, 2.00 eq), and HOBt (5.40 mg, 40.00 mmol, 2.00 eq) were added and the mixture at 25° C., based by DIEA to pH=8. The reaction mixture was stirred at 15° C. for 2 hrs. LCMS indicated one main peak with desired MS. The mixture was washed with 1M HCl (5 L), H$_2$O (5 L), brine (5 L), dried over anhydrous Na$_2$SO$_4$, filtered and concentrated under vacuum to afford compound 2 (38.10 g, crude) as a white solid. Chemical Formula: C$_{153}$H$_{184}$N$_{20}$O$_{22}$S$_2$, LCMS found: [M+2H]$^{2+}$=1360.77;

7) TFA de-protection: A mixture of compound 2 (38.10 g, crude) in TFA/TIS/H$_2$O/3-mercaptopropanoic acid (92.5/2.5/2.5/2.5, v/v/v/v, 400 mL) was stirred at 15° C. for 1.5 hrs. The mixture was precipitated with cold isopropyl ether (2 L). After filtration, the solid was dried under vacuum for 2 hrs to afford compound 3 (28.40 g, crude, TFA salt) as a white solid.

8) Disulfide formation: Compound 3 (28.40 g, crude, TFA salt) was dissolved in MeCN/H$_2$O (1/1, v/v, 70 L). 0.1 M I$_2$/HOAc was added to the mixture dropwise at 15° C. until the light yellow persisted, then the mixture was quenched with 0.1 M Na$_2$S$_2$O$_3$ dropwise until the light yellow disappeared.

9) Purification: After filtration, the filtrate was purified by prep-HPLC (acid condition, TFA) directly and followed by lyophilization to afford Intermediate 5 (6.25 g, 88.3% purity, 18.1% yield, TFA salt) as a white solid. Chemical Formula: C$_{79}$H$_{108}$N$_{20}$O$_{20}$S$_2$, LCMS found: [M+H]$^+$=1722.8, [M+2H]$^{2+}$=861.6.

10) Repeat step 1-5 above, total 4 batches (20 mmol*4) were performed to afford the title compound (25.00 g, TFA salt) as a white solid.

Preparation of ASGPR Binding Ligand: 2,3,5,6-tetrafluorophenyl 4-(4-((4-(((2R,3R,4R,5S)-3,4-dihydroxy-5-((6-(trifluoromethyl)pyrazin-2-yl)amino) tetrahydro-2H-pyran-2-yl)methyl)piperazin-1-yl) methyl)piperidin-1-yl)benzoate

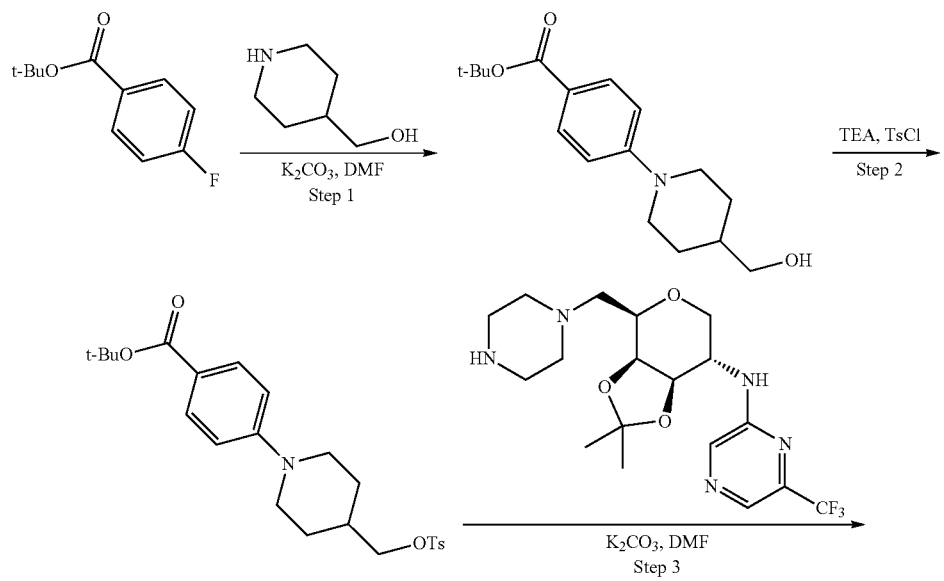

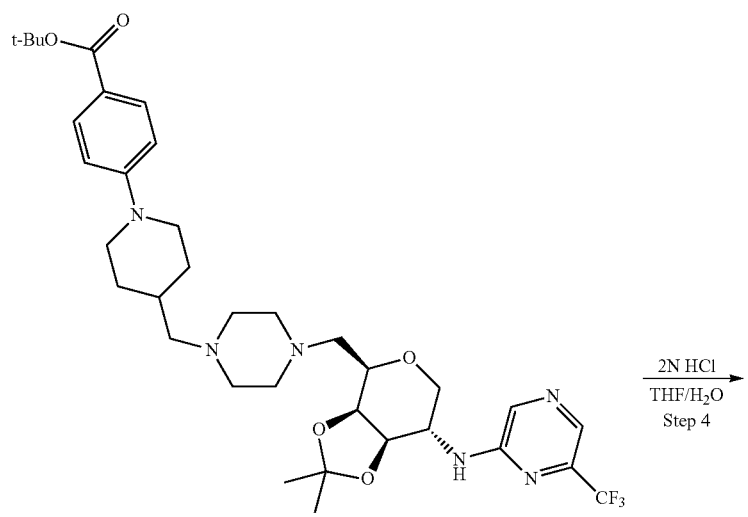

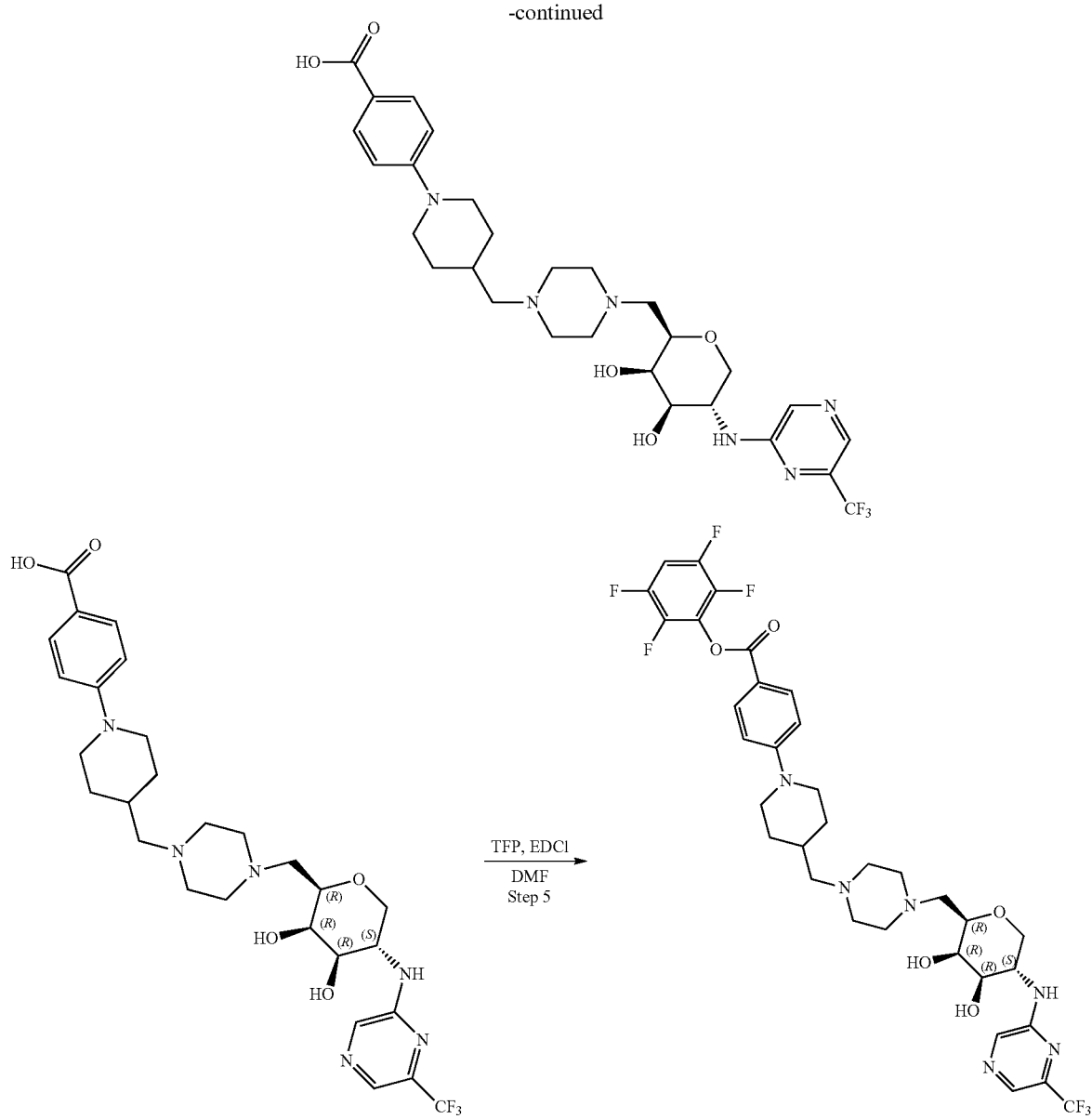

Step 1: A suspension of tert-butyl 4-fluorobenzoate (1 g, 4.7 mmol), piperidin-4-ylmethanol (0.65 mg, 5.6 mmol) and K₂CO₃ (0.65 g, 4.7 mmol) in DMF (5 mL) was stirred at 100° C. overnight. The reaction mixture was cooled and concentrated. The residue was purified by flash chromatography (EA/PE=1:2) to give tert-butyl 4-(4-(hydroxymethyl)piperidin-1-yl)benzoate (1 g, 70% yield) as pink solid. LC-MS (ESI) found: 291 [M+H]⁺.

Step 2: To a solution of tert-butyl 4-(4-(hydroxymethyl)piperidin-1-yl)benzoate (200 mg, 0.7 mmol) and TEA (0.19 mL, 1.4 mmol) in DCM (3 mL) was added TsCl (140 mg, 1.4 mmol). The reaction mixture was stirred at RT for 2h. Then the reaction was concentrated to give crude tert-butyl 4-(4-((tosyloxy)methyl)piperidin-1-yl)benzoate (306 mg) as brown oil.

Step 3: A suspension of N-((3aS,4R,7S,7aR)-2,2-dimethyl-4-(piperazin-1-ylmethyl)tetrahydro-4H-[1,3]dioxolo[4,5-c]pyran-7-yl)-6-(trifluoromethyl)pyrazin-2-amine (200 mg, 0.48 mmol), tert-butyl 4-(4-((tosyloxy)methyl)piperidin-1-yl)benzoate (255 mg, 0.6 mmol) and K₂CO₃ (198 mg, 1.4 mmol) in DMF (3 mL) was stirred at 100° C. for 3h. The reaction was cooled and concentrated. The residue was purified by flash chromatography (DCM/MeOH=10:1) to give tert-butyl 4-(4-((4-(((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)piperazin-1-yl)methyl)piperidin-1-yl)benzoate (120 mg, 36% yield) as yellow oil. LC-MS (ESI) found: 691 [M+H]⁺.

Step 4: A solution of tert-butyl 4-(4-((4-(((3aS,4R,7S,7aR)-2,2-dimethyl-7-((6-(trifluoromethyl)pyrazin-2-yl)amino)tetrahydro-4H-[1,3]dioxolo[4,5-c]pyran-4-yl)methyl)piperazin-1-yl)methyl)piperidin-1-yl)benzoate (100 mg, 0.14 mmol) in diluted aqueous HCl (3 mL, 3M in water) was stirred at 50° C. for 1 h. The reaction solution was cooled, neutralized with NH₃·H₂O and concentrated to give crude mixture. The crude mixture was purified by prep-HPLC to give 4-(4-((4-(((2R,3R,4R,5S)-3,4-dihydroxy-5-((6-(trifluoromethyl)pyrazin-2-yl)amino)tetrahydro-2H- pyran-2-yl)methyl)piperazin-1-yl)methyl)piperidin-1-yl)benzoic acid (30 mg, 34% yield) as white solid. LC-MS (ESI) found: 595[M+H]$^+$. $^1$H NMR (400 MHz, CD$_3$OD): δ 8.11 (s, 1H), 8.00 (s, 1H), 7.82 (d, J=8.6 Hz, 2H), 6.52 (d, J=8.7 Hz, 2H), 4.32 (td, J=10.3, 5.0 Hz, 1H), 4.12 (dd, J=10.9, 5.1 Hz, 1H), 3.87 (d, J=2.7 Hz, 1H), 3.68-3.60 (m, 2H), 3.56-3.51 (m, 1H), 3.44 (t, J=7.6 Hz, 1H), 3.37-3.33 (m, 1H), 3.11 (t, J=10.8 Hz, 1H), 2.98 (t, J=8.7 Hz, 1H), 2.87-2.54 (m, 12H), 2.35-2.27 (m, 1H), 2.25-2.16 (m, 1H), 1.79-1.66 (m, 3H).

Step 5: Preparation of TFP Ester

To a mixture of 4-(4-((4-(((2R,3R,4R,5S)-3,4-dihydroxy-5-((6-(trifluoromethyl)pyrazin-2-yl)amino)tetrahydro-2H-pyran-2-yl)methyl)piperazin-1-yl)methyl)piperidin-1-yl)benzoic acid (250.00 mg, 420.43 umol, 1.00 eq), 2,3,5,6-tetrafluorophenol (418.94 mg, 2.52 mmol, 6.00 eq) in DMF (0.5 mL) was added EDCI (201.49 mg, 1.05 mmol, 2.5 eq) at 0° C. Then the mixture was stirred at 0° C. for 3 hrs. The reaction mixture was purified by prep-HPLC (acid condition, TFA) directly and followed by lyophilization to afford compound 4 (TFP ester, 183.00 mg, 90% purity, 73.2% yield) as a white solid. Chemical Formula: C$_{34}$H$_{37}$F$_7$N$_6$O$_5$, LCMS found: [M+H]$^+$=743.29.

Step 6: Coupling of ASGPR Binding Ligand and Protein Target Ligand

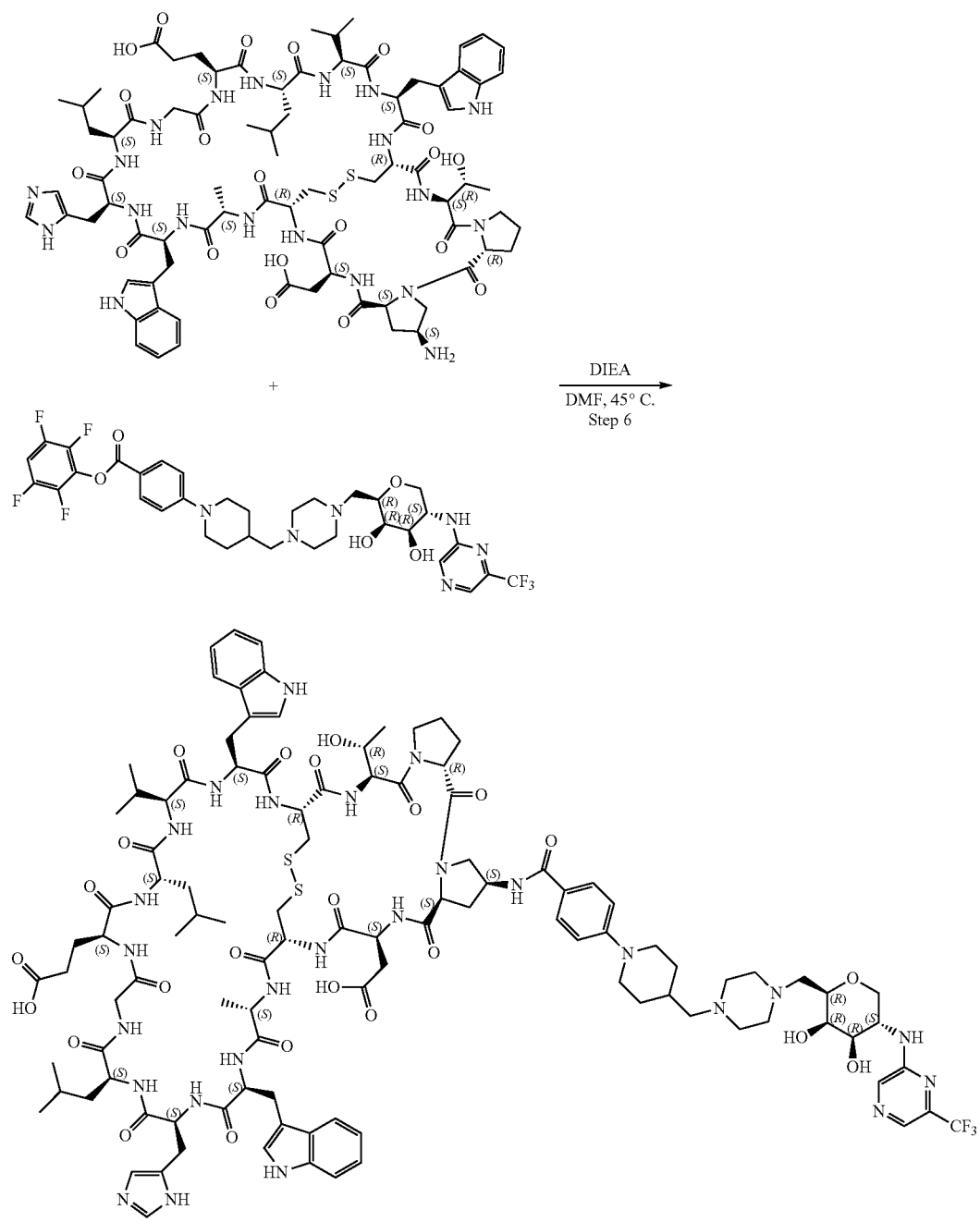

A mixture of 3-((2S,5aR,11S,14R,17S,20S,23S,26S,32S, 35S,38S,41S,44R,47S,49aS)-35-((1H-imidazol-5-yl)methyl)-17,38-bis((1H-indol-3-yl)methyl)-2-amino-47-(carboxymethyl)-11-((R)-1-hydroxyethyl)-23,32-diisobutyl-20-isopropyl-41-methyl-5,10,13,16,19,22,25,28,31,34,37,40, 43,46,49-pentadecaoxooctatetracontahydro-5H-14,44-(methanodithiomethano)dipyrrolo[1,2-a:1',2'-d][1,4,7,10,13,16, 19,22,25,28,31,34,37,40,43]pentadecaazacyclopentatetracontin-26-yl)propanoic acid (183.00 mg, 246.40 umol, 1.00 eq), 2,3,5,6-tetrafluorophenyl 4-(4-((4-(((2R,3R,4R,5S)-3,4-dihydroxy-5-((6-(trifluoromethyl)pyrazin-2-yl)amino)tetrahydro-2H-pyran-2-yl)methyl)piperazin-1-yl)methyl)piperidin-1-yl)benzoate (466.73 mg, 271.04 umol, 1.10 eq), DIEA (159.23 mg, 214.60 uL, 1.23 mmol, 5.00 eq) in DMF (5.0 mL) was stirred at 45° C. for 16 hrs. The reaction mixture was cooled to room temperature, acidified by 1 M HCl to pH=5, purified by prep-HPLC (acid condition, TFA) directly and followed by lyophilization to afford Compound 68 (112.00 mg, 18.4% yield, 93.3% purity) as a white solid. Chemical Formula: $C_{107}H_{143}F_3N_{26}O_{24}S_2$, LCMS found: $[M+2H]^{2+}=1150.3$, $[M+3H]^{3+}=767.6$ Preparation of Intermediate 12: 3-((6S,9R,12S,15S, 18S,21S,27S,30S,33S,36S,39R,42S,44aS,46S, 49aR)-30-((1H-imidazol-5-yl)methyl)-12,33-bis ((1H-indol-3-yl)methyl)-46-amino-6-((R)-1-hydroxyethyl)-18,27-diisobutyl-15-isopropyl-36,42-dimethyl-5,8,11,14,17,20,23,26,29,32,35,38,41,44, 49-pentadecaoxooctatetracontahydro-1H-9,39-(methanodithiomethano)dipyrrolo[1,2-a:1',2'-d][1,4, 7,10,13,16,19,22,25,28,31,34,37,40,43] pentadecaazacyclopentatetracontin-21-yl)propanoic acid

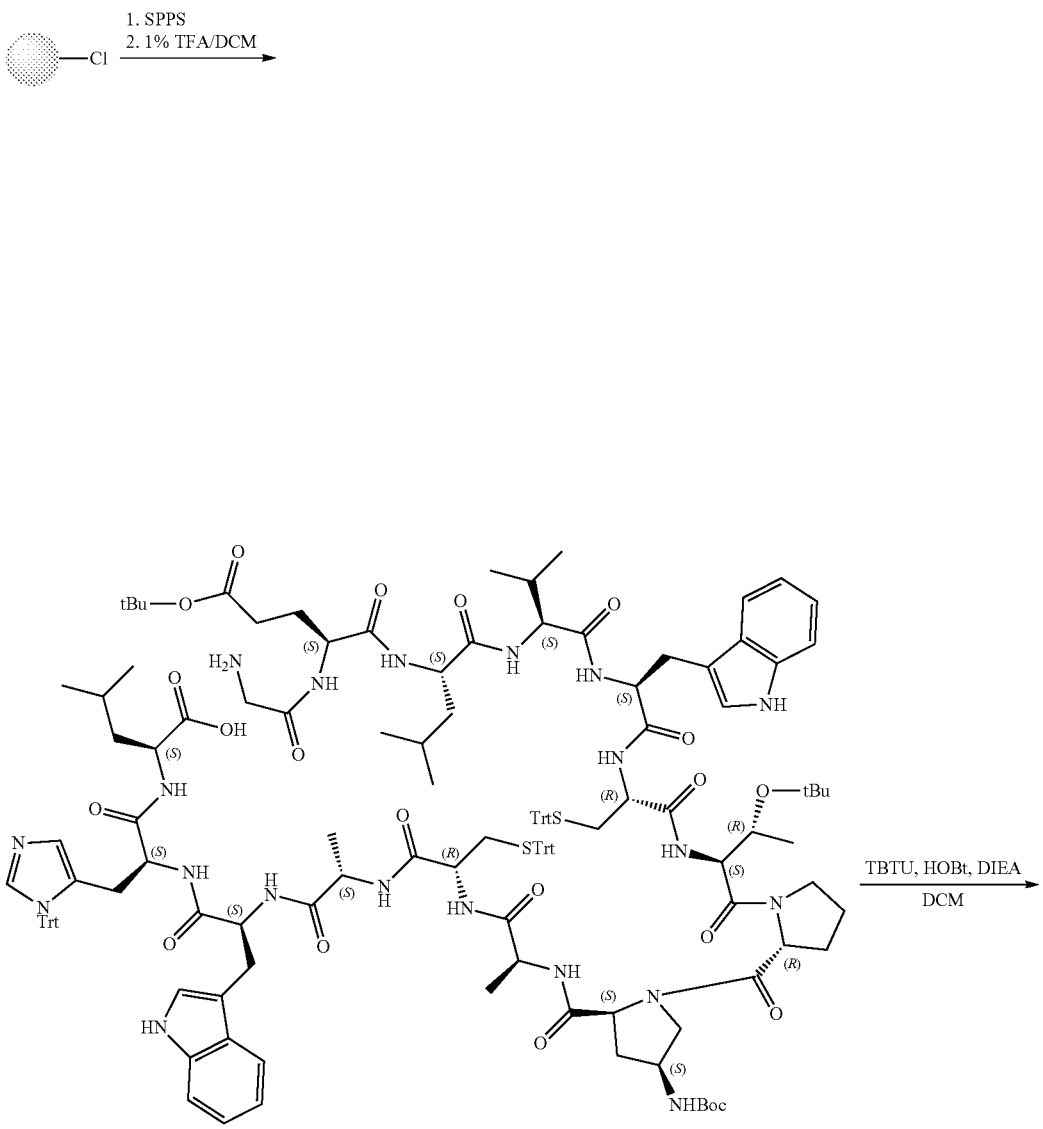

-continued
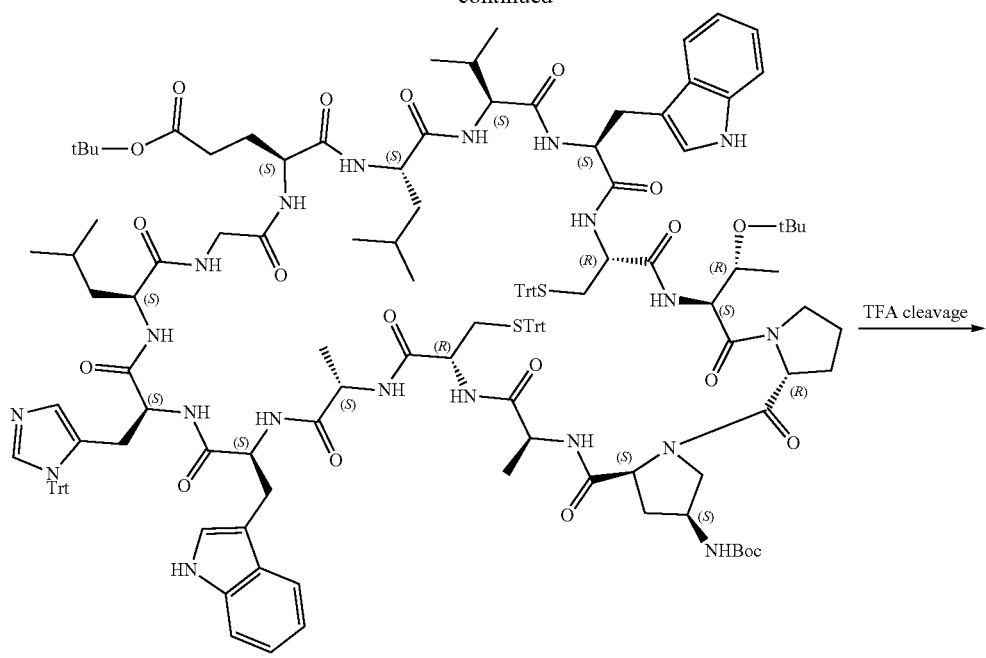
2
TFA cleavage →
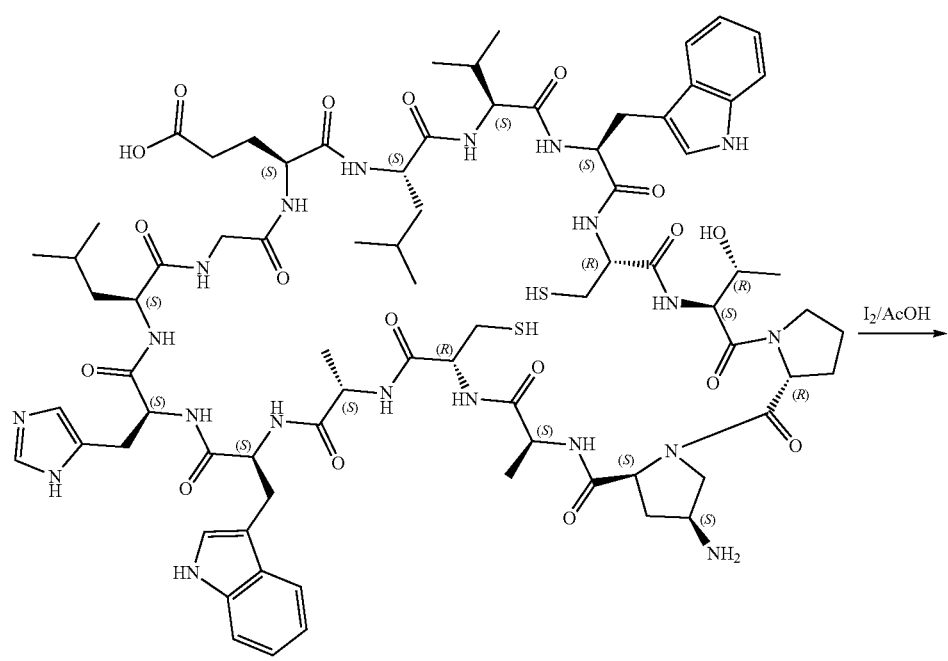
3
I₂/AcOH →

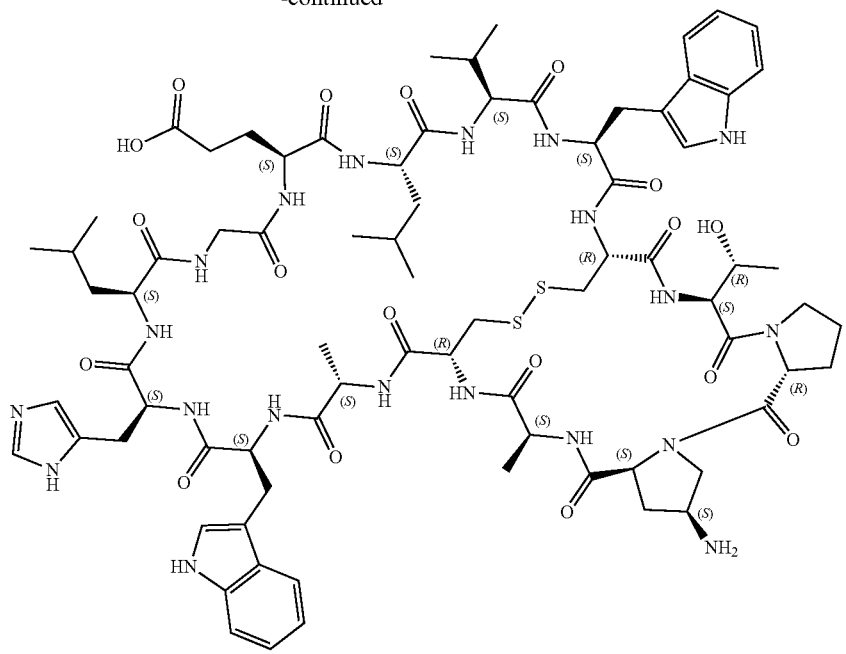

Intermediate 12

Step 1: Preparation of (2)

Solid Phase Peptide Synthesis:

The peptide was synthesized using standard Fmoc chemistry.

1) Resin preparation: To the vessel containing CTC Resin (0.50 g, 0.50 mmol, 1.00 mmol/g) and Fmoc-Gly-OH (148.50 mg, 0.50 mmol, 1.00 eq) in DCM (10 mL) was added DIEA (348.64 mL, 2.00 mmol, 4.00 eq) dropwise and mixed for 2 hrs with $N_2$ bubbling at 25° C. Then added MeOH (0.50 mL) and bubbled with $N_2$ for another 30 mins. The resin was washed with DMF (20 mL)*5. Then 20% piperidine in DMF (20 mL) was added and the mixture was bubbled with N2 for 30 mins at 25° C. The mixture was filtered to obtain the resin. The resin was washed with DMF (20 mL)*5 before proceeding to next step.

2) Coupling: A solution of Fmoc-Glu(OtBu)-OH (637.5 mg, 1.50 mmol, 3.00 eq), HBTU (540.07 mg, 1.425 mmol, 2.85 eq) in DMF (10 mL) was added to the resin with $N_2$ bubbling. Then DIEA (522.97 mL, 3.00 mmol, 6.00 eq) was added to the mixture dropwise and bubbled with $N_2$ for 30 mins at 25° C. The coupling reaction was monitored by ninhydrin test, if it showed colorless, the coupling was completed. The resin was then washed with DMF (20 mL)*5

3) De-protection: 20% piperidine in DMF (20 mL) was added to the resin and the mixture was bubbled with $N_2$ for 30 mins at 25° C. The resin was then washed with DMF (20 mL)*5 The De-protection reaction was monitored by ninhydrin test, if it showed blue or other brownish red, the reaction was completed.

4) Step 2 and 3 were repeated for all other amino acids: (2-15 in Table 2).

TABLE 2

| # | Materials | Coupling reagents |
|---|-----------|-------------------|
| 1 | Fmoc-Gly-OH (1.00 eq) | DIEA (4.00 eq) |
| 2 | Fmoc-Glu(OtBu)-OH (3.00 eq) | HBTU (2.85 eq) and DIEA (6.00 eq) |
| 3 | Fmoc-Leu-OH (3.00 eq) | HBTU (2.85 eq) and DIEA (6.00 eq) |
| 4 | Fmoc-Val-OH (3.00 eq) | HBTU (2.85 eq) and DIEA (6.00 eq) |
| 5 | Fmoc-Trp-OH (3.00 eq) | HBTU (2.85 eq) and DIEA (6.00 eq) |
| 6 | Fmoc-Cys(Trt)-OH (3.00 eq) | HBTU (2.85 eq) and DIEA (6.00 eq) |
| 7 | Fmoc-Thr(tBu)-OH (3.00 eq) | HBTU (2.85 eq) and DIEA (6.00 eq) |
| 8 | Fmoc-D-Pro-OH (3.00 eq) | HBTU (2.85 eq) and DIEA (6.00 eq) |
| 9 | Boc-(2S,4S)-4-amino-1-Fmoc-pyrrolidine-2-carboxylicacid (1.00 eq) | HATU (0.95 eq) and DIEA (2.00 eq) |
| 10 | Fmoc-Ala-OH (3.00 eq) | HATU (2.85 eq) and DIEA (6.00 eq) |
| 11 | Fmoc-Cys(Trt)-OH (3.00 eq) | HBTU (2.85 eq) and DIEA (6.00 eq) |
| 12 | Fmoc-Ala-OH (3.00 eq) | HBTU (2.85 eq) and DIEA (6.00 eq) |
| 13 | Fmoc-Trp-OH (3.00 eq) | HBTU (2.85 eq) and DIEA (6.00 eq) |
| 14 | Fmoc-His(Trt)-OH (3.00 eq) | HBTU (2.85 eq) and DIEA (6.00 eq) |
| 15 | Fmoc-Leu-OH (3.00 eq) | HBTU (2.85 eq) and DIEA (6.00 eq) |

Peptide Cleavage and Purification:

1) Cleavage buffer (1% TFA/DCM, 30 mL) was added into the flask containing the side chain protected crude peptide. The mixture was stirred for 5 min at room temperature and the solution was collected after filtration. The cleavage step was repeated for another time.

2) The combined solution was diluted to 500 mL with DCM.

3) TBTU (321.00 mg, 1.00 mmol, 2.00 eq), and HOBt (135.00 mg, 1.00 mmol, 2.00 eq) were added and the mixture was stirred at 25° C. for 2 hrs.

4) The reaction mixture was washed with 1M HCl (200 mL), $H_2O$ (200 mL), brine (200 mL), dried over anhydrous $Na_2SO_4$, filtered and concentrated under vacuum to afford compound 2 (1.20 g, crude) as a white solid. Chemical Formula: $C_{148}H_{176}N_{20}O_{20}S_2$, LCMS found: $[M+Na]^{2+}=1320.77$;

Preparation of Intermediate 12

A mixture of compound 2 (1.20 g, crude) in TFA/TIS/H$_2$O/3-mercaptopropanoic acid (92.5%/2.5%/2.5%/2.5%, v/v/v, 25 mL) was stirred at 25° C. for 1.5 hrs. The mixture was precipitated with cold isopropyl ether (150 mL) and centrifuged (3 min at 3000 rpm). The solid was washed with isopropyl ether twice, dried under vacuum for 2 hrs to afford compound 3 (900.0 mg, crude). Then compound 3 (900.0 mg, crude) was dissolved in MeCN/H$_2$O (1/1, v/v, 500 mL). I$_2$/HOAc (0.1 M) was added to the mixture dropwise at 25° C. until the light yellow persisted, then the mixture was quenched with 0.1 M Na$_2$S$_2$O$_3$ dropwise until the light yellow disappeared. After filtration, the filtrate was purified by prep-HPLC (acid condition, TFA) directly to afford Intermediate 12 (144.00 mg, 16.640% yield, 97.00% purity) as a white solid. Chemical Formula: $C_{78}H_{108}N_{20}O_{18}S_2$, LCMS found: $[M+H]^{1+}=1677.79$, $[M+2H]^{2+}=839.39$, $[M+3H]^{3+}=559.95$.

The intermediates Intermediate 13-Intermediate 28 were prepared according to the procedure same as that of Intermediate 12.

| Compound ID | structure | Analytical data |
|---|---|---|
| Intermediate 13 | 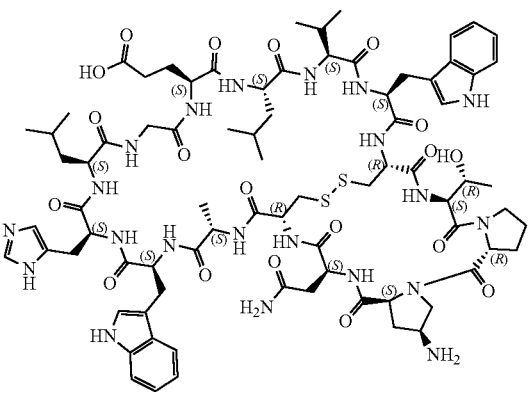 | Yield: 230.3 mg, 97.5% purity, 26.0% yield, white solid. LC-MS (ESI) found: $[M + H]^+ = 1720.82$, $[M + 2H]^{2+} = 860.90$, $[M + 3H]^{3+} = 574.18$. |
| Intermediate 14 | 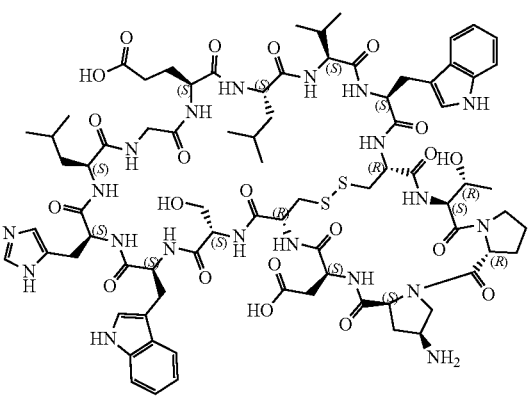 | Yield: 252 mg, 95.4% purity, 27.6% yield, white solid. LC-MS (ESI) found: $[M + H]^+ = 1737.80$, $[M + 2H]^{2+} = 869.43$, $[M + 3H]^{3+} = 579.86$. |
| Intermediate 15 | 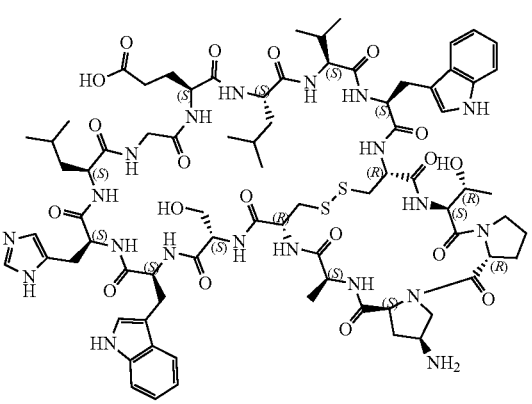 | Yield: 144.7 mg, 96.1% purity. 16.4% yield, white solid. LC-MS (ESI) found: $[M + H]^+ = 1693.80$, $[M + 2H]^{2+} = 847.42$, $[M + 3H]^{3+} = 565.19$. |

-continued

| Compound ID | structure | Analytical data |
|---|---|---|
| Intermediate 16 | 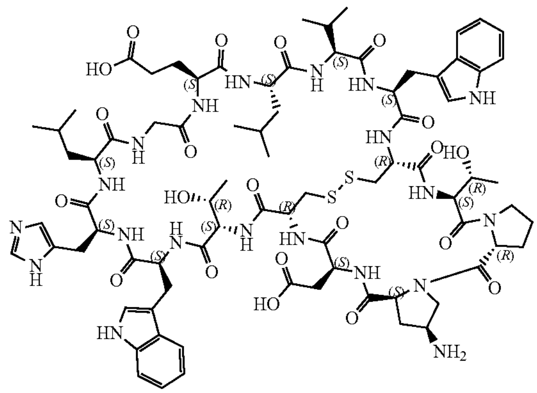 | Yield: 276.3 mg, 96.9% purity, 30.5% yield, white solid. LC-MS (ESI) found: [M + H]$^+$ = 1751.87, [M + 2H]$^{2+}$ = 876.47, [M + 3H]$^{3+}$ = 584.7. |
| Intermediate 17 | 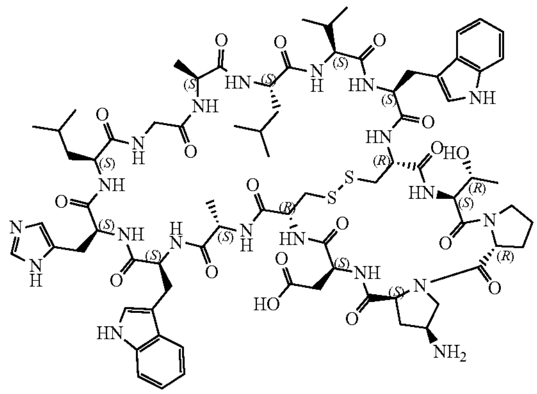 | Yield: 223.4 mg, 95.0% purity, 25.5% yield, white solid. LC-MS (ESI) found: [M + H]$^+$ = 1663.77, [M + 2H]$^{2+}$ = 832.40, [M + 3H]$^{3+}$ = 555.01. |
| Intermediate 18 | 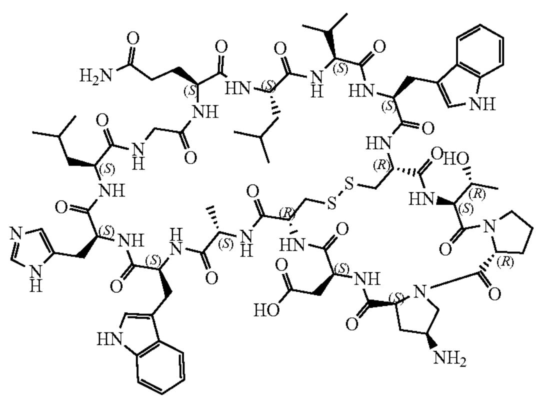 | Yield: 230.5 mg, 96.2% purity, 25.7% yield, white solid. LC-MS (ESI) found: [M + H]$^+$ = 1720.89, [M + 2H]$^{2+}$ = 861.00, [M + 3H]$^{3+}$ = 574.29. |
| Intermediate 19 | 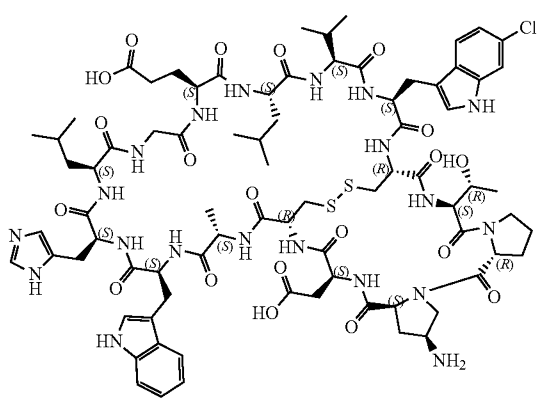 | Yield: 215.7 mg, 95.1% purity, 23.3% yield, white solid. LC-MS (ESI) found: [M + H]$^+$ = 1755.81, [M + 2H]$^{2+}$ = 878.50. |

-continued

| Compound ID | structure | Analytical data |
|---|---|---|
| Intermediate 20 | 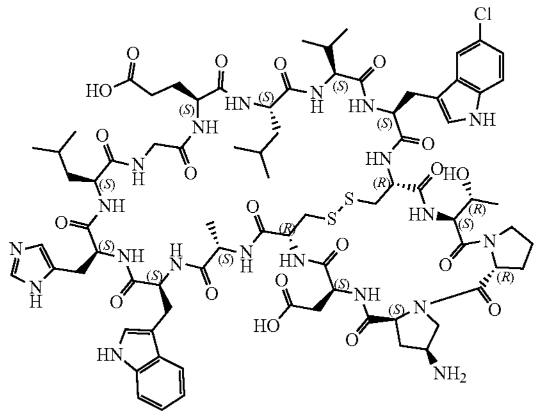 | Yield: 161.7 mg, 97.9% purity, 18.0% yield, white solid. LC-MS (ESI) found: [M + H]⁺ = 1756.80, [M + 2H]²⁺ = 878.41, [M + 3H]³⁺ = 585.97. |
| Intermediate 21 | 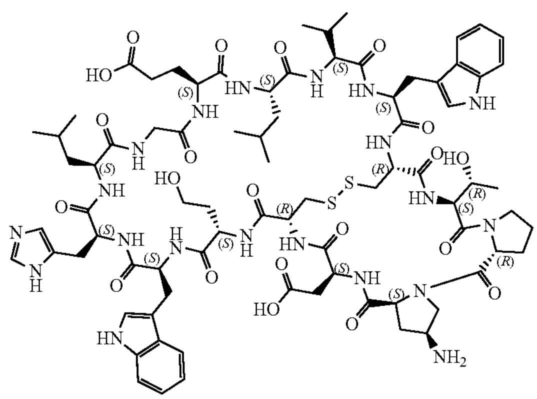 | Yield: 163.7 mg, 98.0% purity, 18.3% yield, white solid. LC-MS (ESI) found: [M + H]⁺ = 1751.81, [M + 2H]²⁺ = 876.41, [M + 3H]³⁺ = 584.62. |
| Intermediate 22 | 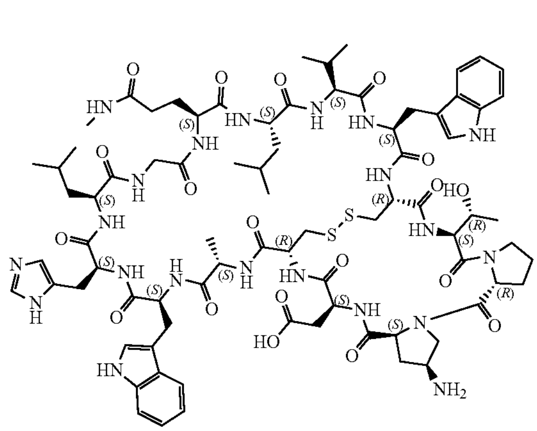 | Yield: 153.3 mg, 95.4% purity, 16.8% yield, white solid. LC-MS (ESI) found: [M + H]⁺ = 1734.80, [M + 2H]²⁺ = 867.92, [M + 3H]³⁺ = 578.99. |

| Compound ID | structure | Analytical data |
|---|---|---|
| Intermediate 23 | 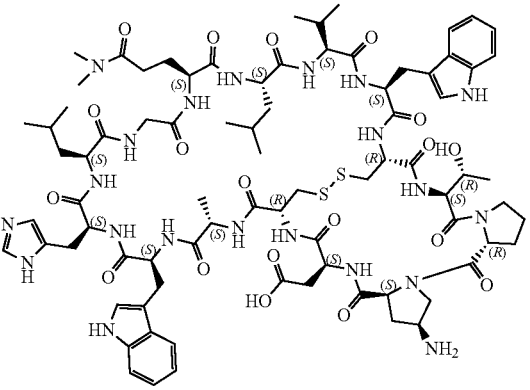 | Yield: 120.5 mg, 96.2% purity, 13.2% yield, white solid. LC-MS (ESI) found: [M + H]$^+$ = 1748.90, [M + 2H]$^{2+}$ = 874.96, [M + 3H]$^{3+}$ = 583.60. |
| Intermediate 24 | 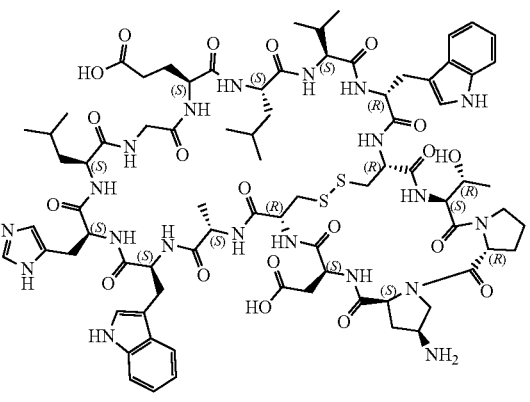 | Yield: 188.5 mg, 95.6% purity, 20.9% yield, white solid. LC-MS (ESI) found: [M + H]$^+$ = 1721.80, [M + 2H]$^{2+}$ = 861.34, [M + 3H]$^{3+}$ = 574.61. |
| Intermediate 25 | 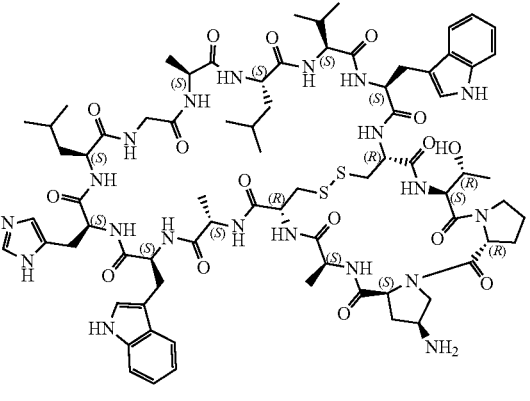 | Yield: 163.5 mg, 95.9% purity, 19.1% yield, white solid. LC-MS (ESI) found: [M + H]$^+$ = 1619.60, [M + 2H]$^{2+}$ = 810.50. |
| Intermediate 26 | 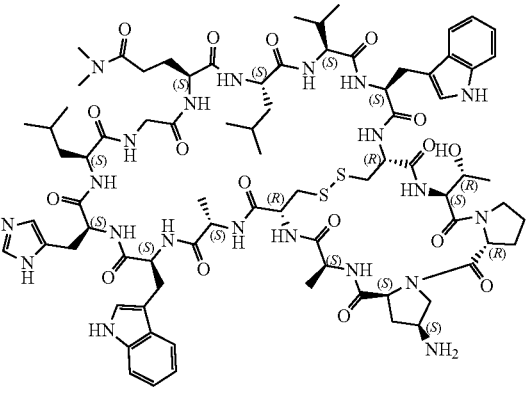 | Yield: 34.9 mg, 94.4% purity, 6.4% yield, white solid632. LC-MS (ESI) found: [M + H]$^+$ = 1704.60, [M + 2H]$^{2+}$ = 853.00. |

| Compound ID | structure | Analytical data |
| --- | --- | --- |
| Intermediate 27 | 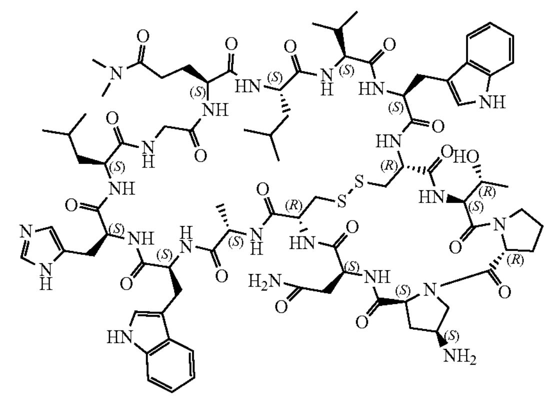 | Yield: 119 mg, 96.9% purity, 22.0% yield, white solid. LC-MS (ESI) found: [M + H]⁺ = 1747.70, [M + 2H]²⁺ = 874.60. |
| Intermediate 28 | 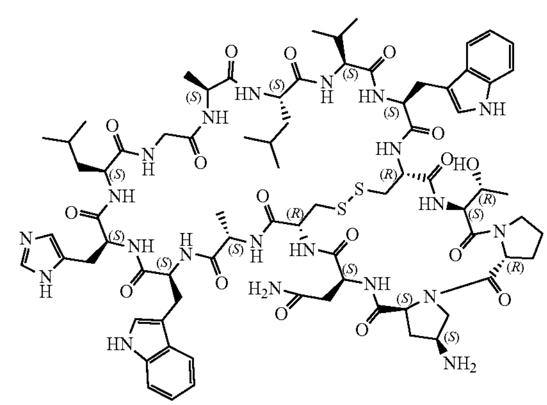 | Yield: 159.8 mg, 97.0% purity, 18.6% yield, white solid. LC-MS (ESI) found: [M + H]⁺ = 1662.60, [M + 2H]²⁺ = 832.10. |

Preparation of Compound 76: 3,3'-((2-((2-((((6S,9R, 12S,15S,18S,21S,27S,30S,33S,36S,39R,42S,44aS, 46S,49aR)-30-((1H-imidazol-5-yl)methyl)-12,33-bis ((1H-indol-3-yl)methyl)-6-((R)-1-hydroxyethyl)-18, 27-diisobutyl-15-isopropyl-21,36,42-trimethyl-5,8, 11,14,17,20,23,26,29,32,35,38,41,44,49-pentadecaoxooctatetracontahydro-1H-9,39-(methanodithiomethano) dipyrrolo[1,2-a:1',2'-d][1,4, 7,10,13,16,19,22,25,28,31,34,37,40,43] pentadecaazacyclopenta tetracontin-46-yl)amino)-2-oxoethyl)amino)propane-1,3-diyl)bis(oxy))bis(N-(1-((2R,3R, 4R,5S)-3,4-dihydroxy-5-((6-(trifluoromethyl)pyrazin-2-yl)amino)tetrahydro-2H-pyran-2-yl)-2,5,8,11-tetraoxatridecan-13-yl) propanamide)

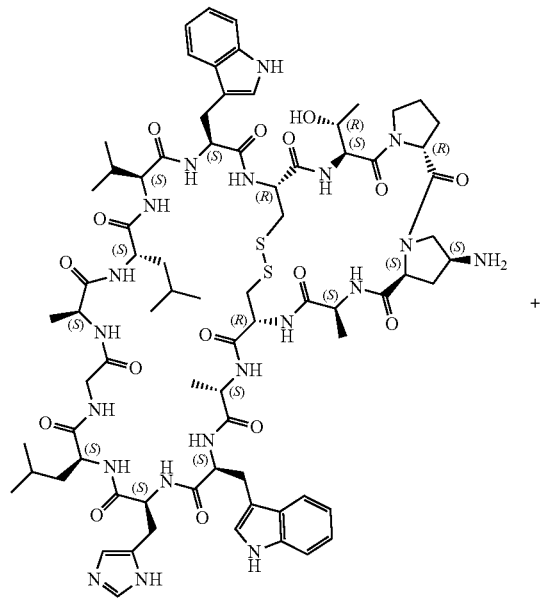

Intermediate 25

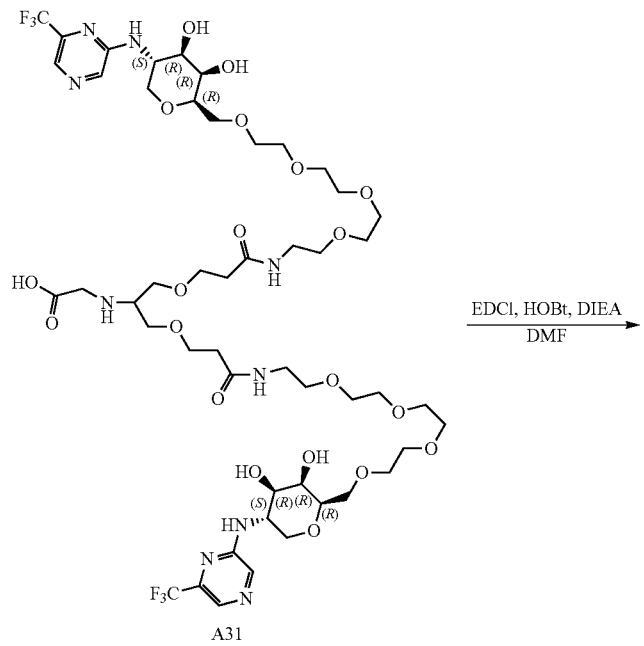

A31

EDCl, HOBt, DIEA
———————→
DMF

-continued

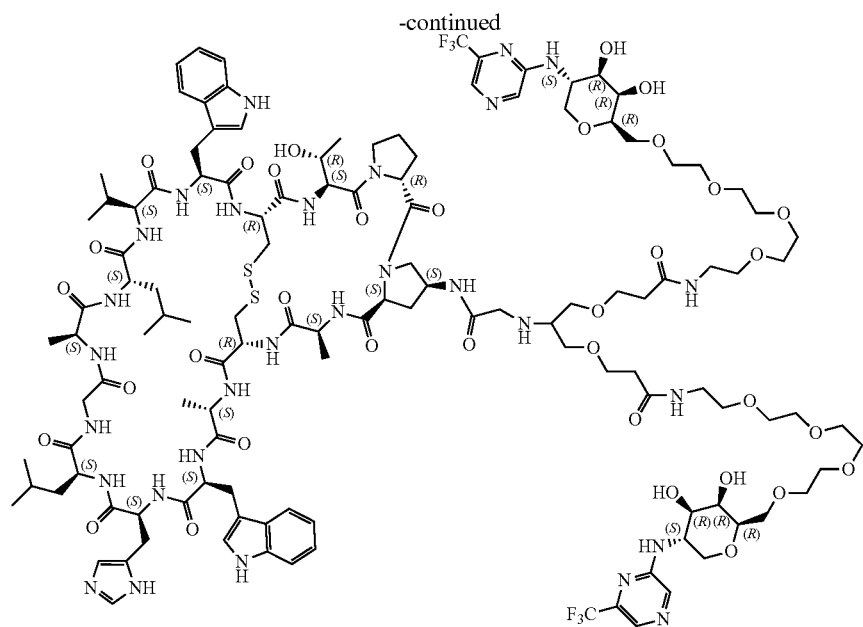

Compound 76

Preparation of Compound 76

To a stirred solution of Intermediate 25 (50.0 mg, 30.87 umol, 1.00 eq), A31 (41.6 mg, 33.95 umol, 1.10 eq), HOBt (6.26 mg, 46.30 umol, 1.50 eq) and DIEA (3.9 mg, 30.87 umol, 5.38 uL, 1.00 eq) in DMF (0.5 mL) was added EDCI (8.8 mg, 46.30 umol, 1.50 eq) at 0° C. Then the mixture was stirred at 0° C. for 2 hrs. The mixture was purified by prep-HPLC (acid condition, TFA) directly to afford Compound 76 (38.4 mg, 95.2% purity, 41.8% yield) as a white solid. Chemical Formula: $C_{125}H_{181}F_6N_{29}O_{35}S_2$; LCMS found: $[M+H+Na]^{2+}=1426.3$, $[M+2H]^{2+}=1415.1$; $[M+3H]^{3+}=943.4$.

The compounds Compound 77, Compound 78, Compound 79 were prepared according to the procedure same as that of Compound 76.

| Compound | Starting material Peptide | Analytical data |
|---|---|---|
| Compound 77 | Intermediate 26 | Yield: 11.7 mg, 98% purity, 29.8% yield, white solid. LC-MS found: $[M + H + Na]^{2+} = 1468.5$, $[M + 2H]^{2+} = 1458.0$, $[M + 3H]^{3+} = 971.9$. |

-continued
| Compound | Starting material Peptide | Analytical data |
|---|---|---|
| Compound 78 | 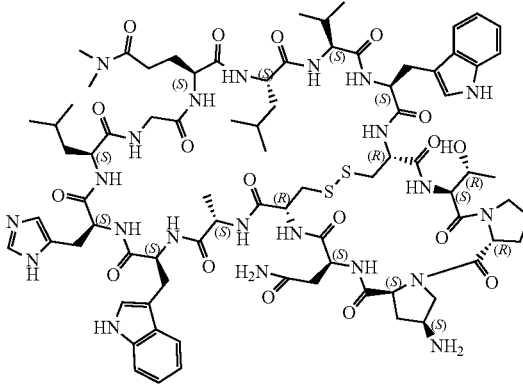
Intermediate 27 | Yield: 44.3 mg, 97.5% purity, 47.3% yield, white solid. LC-MS found: $[M + H + Na]^{2+}$ = 1490.8, $[M + 2H]^{2+}$ = 1479.3, $[M + 3H]^{3+}$ = 986.3. |
| Compound 79 | 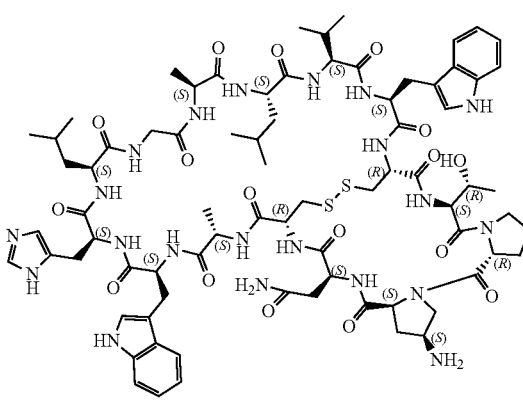
Intermediate 28 | Yield: 69.0 mg, 68.0% purity, 66.5% yield, white solid. LC-MS found: $[M + 2H]^{2+}$ = 1436.3, $[M + 3H]^{3+}$ = 957.8 |

Preparation of Intermediate 48: 3-((6S,9R,12S,15S,18S,21S,27S,30S,33S,36S,39R,42S,44aS, 46S, 49aR)-30-((1H-imidazol-5-yl)methyl)-12,33-bis((1H-indol-3-yl)methyl)-42-(carboxy methyl)-46-(hex-5-ynamido)-6-((R)-1-hydroxyethyl)-18,27-diisobutyl-15-isopropyl-36-methyl-5,8,11,14,17,20,23,26,29,32,35,38,41,44,49-pentadecaoxooctatetracontahydro-1H-9,39-(methanodithiomethano)dipyrrolo[1,2-a:1',2'-d][1,4,7,10,13,16,19,22,25,28,31,34,37,40,43]pentadecaazacyclopentatetracontin-21-yl)propanoic acid

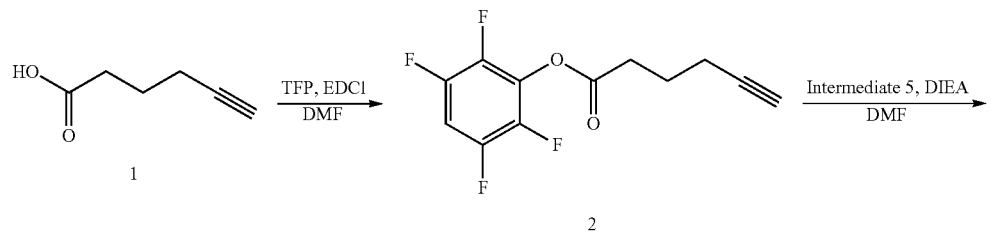

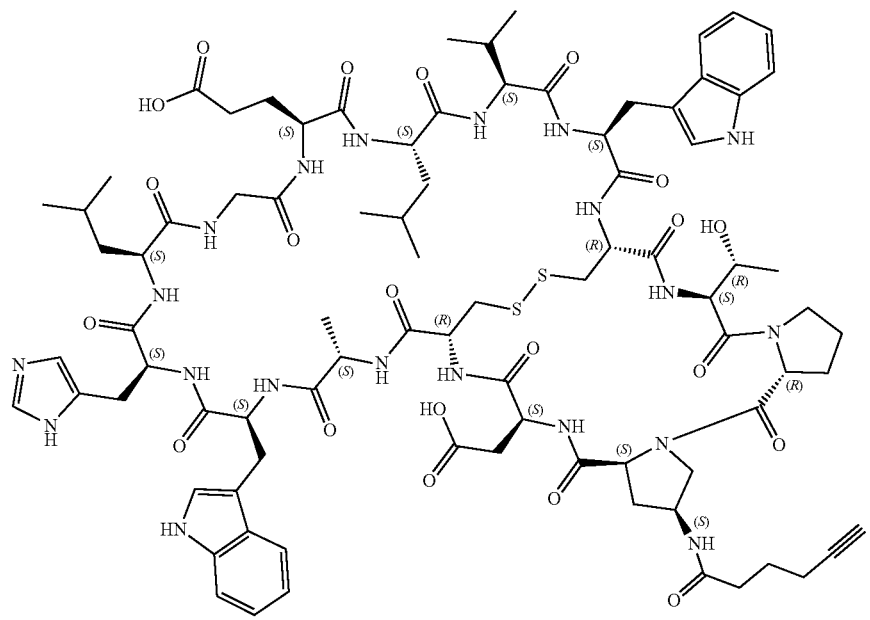

Intermediate 48

Step 1: Preparation of 2,3,5,6-tetrafluorophenyl hex-5-ynoate (compound 2)

A mixture of compound 1 (2.00 g, 17.84 mmol, 1.94 mL, 1.00 eq) and TFP (5.92 g, 35.67 mmol, 2.00 eq) in DMF (15.0 mL) was added EDCI (6.84 g, 35.67 mmol, 2.00 eq). The mixture was stirred at 20° C. for 2 hrs. LCMS showed compound 1 was consumed completely, and on main peak was desired MS. The mixture was purified by Flash (C18, TFA condition) and lyophilized to afford compound 2 (1.2 g, 24.1% yield) as a colorless oil. Chemical Formula: $C_{12}H_8F_4O_2$, LCMS found: $[M+H]^+=260.92$.

Step 2: Preparation of Intermediate 48

A mixture of Intermediate 5 (5 g, 2.90 mmol, 1.00 eq), compound 2 (1.13 g, 4.36 mmol, 1.50 eq), and DIEA (1.50 g, 11.61 mmol, 2.02 mL, 4.00 eq) in DMF (50 mL) was stirred at 0° C. for 8 hrs. The mixture was acidified by 0.1 M HCl to pH=5 and purified by prep-HPLC (TFA condition) directly to afford Intermediate 48 (1.97 g, 97.8% purity, 36.54% yield) as a white solid. Chemical Formula: $C_{85}H_{14}N_{20}O_{21}S_2$, LCMS found: $[M+H]^+=1817.1$, $[M+2H]^{2+}=908.7$.

1233

Preparation of 3-((6S,9R,12S,15S,18S,21S,27S,30S, 33S,36S,39R,42S,44aS,46S,49aR)-30-((1H-imida-zol-5-yl)methyl)-12,33-bis((1H-indol-3-yl)methyl)-46-(4-(1-(((2R,3R,4R,5R)-5-acetamido-3,4-dihydroxy-6-methoxytetrahydro-2H-pyran-2-yl) methyl)-1H-1,2,3-triazol-4-yl)butanamido)-42-(carboxymethyl)-6-((R)-1-hydroxyethyl)-18,27-

1234 diisobutyl-15-isopropyl-36-methyl-5,8,11,14,17,20, 23,26,29,32,35,38,41,44,49-pentadecaoxooctatetra-contahydro-1H-9,39-(methanodithiomethano)dipyr-rolo[1,2-a:1',2'-d][1,4,7,10,13,16,19,22,25,28,31,34, 37,40,43]pentadecaazacyclopentatetracontin-21-yl) propanoic acid

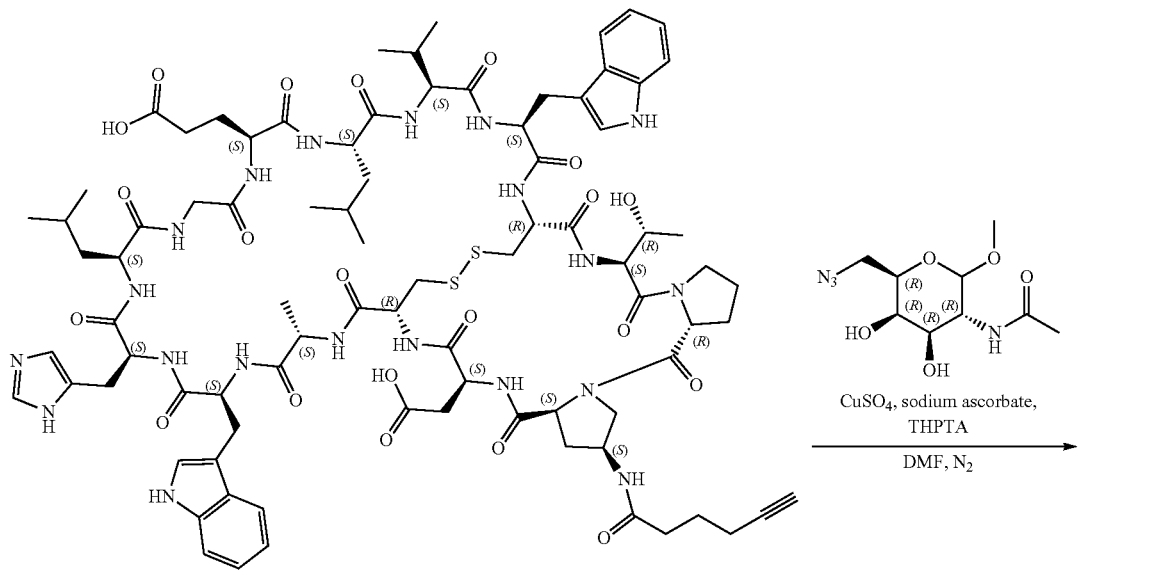

Intermediate 48

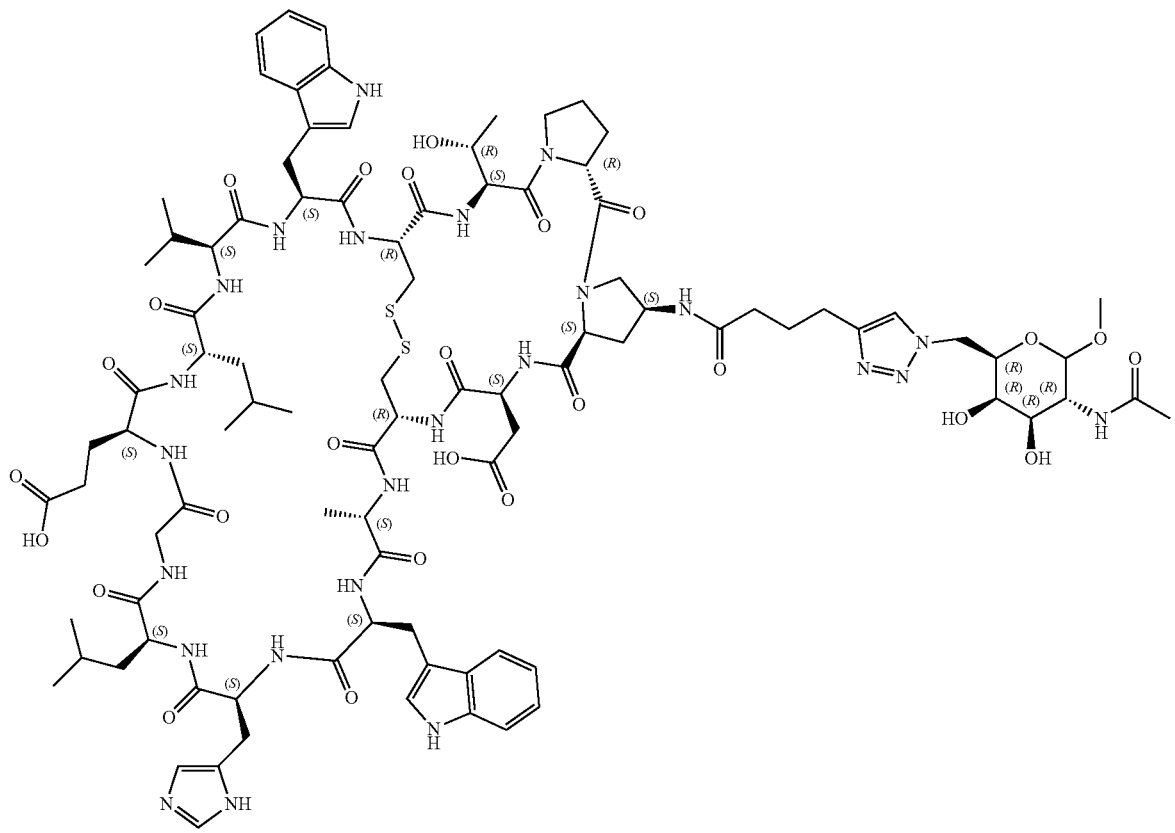

Compound 81

A mixture of Intermediate 48 (97.7 mg, 53.80 umol, 1.00 eq)), N-((3R,4R,5R,6R)-6-(azidomethyl)-4,5-dihydroxy-2-methoxytetrahydro-2H-pyran-3-yl)acetamide (A146 (14.0 mg, 53.80 umol, 1 eq) in DMF (0.5 mL) was cooled to 0° C., degassed and purged with $N_2$ for 3 times. Then a freshly prepared mixture of $CuSO_4$ (0.4 M, 134.49 uL, 1.00 eq), sodium ascorbate (0.5 M, 430.36 uL, 4.00 eq) and THPTA (23.83 mg, 53.80 umol, 1.00 eq) was added to the reaction mixture at 0° C. The mixture was degassed and purged with $N_2$ for 3 times, stirred at 0° C. for 2 hrs under $N_2$ atmosphere. The mixture was purified by prep-HPLC (acid condition, TFA) directly and lyophilized to afford Compound 81 (74.8 mg, 97.7% purity, 66.8% yield) as a white solid. Chemical Formula: $C_{94}H_{130}N_{24}O_{26}S_2$, LCMS found: $[M+2H]^{2+}= 1039.2$, $[M+3H]^{3+}=693.1$.

The compounds Compound 53, Compound 52, Compound 51, and Compound 80 were prepared according to the procedure same as Compound 81, replacing N-((3R,4R,5R,6R)-6-(azidomethyl)-4,5-dihydroxy-2-methoxytetrahydro-2H-pyran-3-yl)acetamide with the starting material listed in the table below.

| Compound | Starting material | Analytical data |
|---|---|---|
| Compound 53 | A18 | Yield: 49.1 mg, 97.5% purity, 66.7% yield, white solid. LC-MS found: $[M + 2H]^{2+} = 1562.17$, $[M + 3H]^{3+} = 1041.65$, $[M + 4H]^{4+} = 781.50$, $[M + 5H]^{5+} = 625.30$ |
| Compound 52 | A2 | Yield: 7.6 mg, 90.9% purity, 26.29% yield, white solid. LC-MS found: $[M + 2H]^{2+} = 1562.00$, $[M + 3H]^{3+} = 1041.71$, $[M + 4H]^{4+} = 781.49$, $[M + 5H]^{5+} = 625.51$ |
| Compound 51 | A87 | Yield: 38.7 mg, 98.5% purity, 58.5% yield, white solid. LC-MS found: $[M + 2H]^{2+} = 1075.60$, $[M + 3H]^{3+} = 717.45$ |

| Compound | Starting material | Analytical data |
|---|---|---|
| Compound 80 | 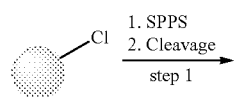

A59 | Yield: 45.7 mg, 98.4% purity, 75.9% yield, white solid. LC-MS found: $[M + 2H]^{2+} = 1075.8$, $[M + 3H]^{3+} = 718.0$. |

Preparation of Intermediate 4: 3-((6S,9R,12S,15S, 18S,21S,27S,30S,33S,36S,39R,42S,44aS,46S, 49aR)-30-((1H-imidazol-5-yl)methyl)-12,33-bis ((1H-indol-3-yl)methyl)-42-(carboxymethyl)-46-(20- (1-(1-((2R,3R,4R,5S)-3,4-dihydroxy-5-((6- (trifluoromethyl)pyrazin-2-yl)amino)tetrahydro-2H- pyran-2-yl)-20-(1-((2R,3R,4R,5S)-3,4-dihydroxy-5- ((6-(trifluoro methyl)pyrazin-2-yl)amino)tetrahydro- 2H-pyran-2-yl)-15-oxo-2,5,8,11,18-pentaoxa-14-aza nonadecan-19-yl)-15,22-dioxo-2,5,8,11,18-pentaoxa- 14,21-diazaheptacosan-27-yl)-1H-1,2,3-triazol-4-yl)- 17-oxo-4,7,10,13-tetraoxa-16-azaicosanamido)-6- ((R)-1-hydroxyethyl)-18,27-diisobutyl-15-isopropyl- 36-methyl-5,8,11,14,17,20,23,26,29,32,35,38,41,44, 49-pentadecaoxo octatetracontahydro-1H-9,39- (methanodithiomethano)dipyrrolo[1,2-a:1',2'-d][1,4, 7,10,13,16,19,22,25,28,31,34,37,40,43] pentadecaazacyclopentatetracontin-21-yl)propanoic acid

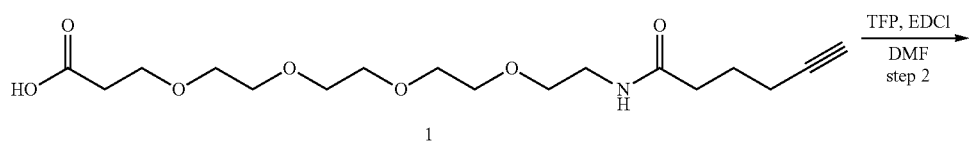

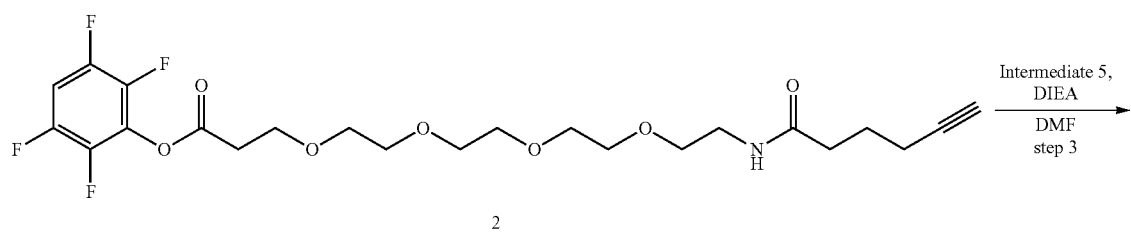

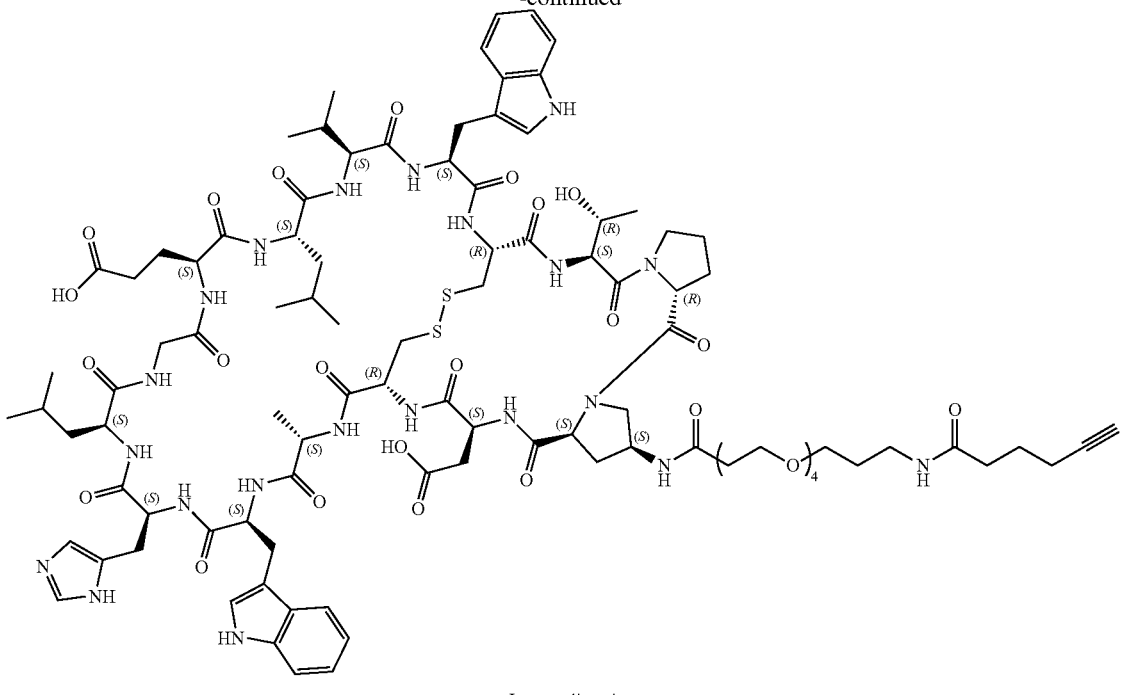

Intermediate 4

Step 1: Preparation of Compound 1

Solid Phase Peptide Synthesis:

The peptide was synthesized using standard Fmoc chemistry.
5) Resin preparation: To the vessel containing CTC Resin (37.00 g, 30.00 mmol, 0.81 mmol/g) and Fmoc-NH$_2$—PEG$_4$-CH$_2$CH$_2$COOH (14.61 g, 30.00 mmol, 1.00 eq) in DCM (300 mL) was added DIEA (20.91 mL, 120.00 mmol, 4.00 eq) dropwise and mixed for 2 hrs with N$_2$ bubbling at 15° C. Then added MeOH (30.00 mL) and bubbled with N$_2$ for another 30 mins. The resin was washed with DMF (600 mL)*5. Then 20% piperidine in DMF (600 mL) was added and the mixture was bubbled with N$_2$ for 30 mins at 15° C. The mixture was filtered to obtain the resin. The resin was washed with DMF (600 mL)*5 before proceeding to next step.
6) Coupling: A solution of hex-5-ynoic acid (6.72 g, 60.00 mmol, 2.00 eq), HBTU (21.94 g, 57.00 mmol, 1.90 eq) in DMF (300 mL) was added to the resin with N$_2$ bubbling. Then DIEA (20.91 mL, 120.00 mmol, 4.00 eq) was added to the mixture dropwise and bubbled with N$_2$ for 30 mins at 15° C. The coupling reaction was monitored by ninhydrin test, if it showed colorless, the coupling was completed. The resin was then washed with DMF (600 mL)*5, MeOH (600 mL)*5, dried under reduced pressure.

TABLE 1

| # | Materials | Coupling reagents |
|---|-----------|-------------------|
| 1 | Fmoc-NH$_2$-PEG$_4$-CH$_2$CH$_2$COOH (1.00 eq) | DIEA (4.00 eq) |
| 2 | hex-5-ynoic acid (2.00 eq) | HBTU (1.90 eq) and DIEA (4.00 eg) |

Peptide Cleavage and Purification:
1) Cleavage buffer (20% HFIP/DCM, 500 mL) was added into the flask containing the side chain protected crude peptide. The mixture was stirred for 1 hr at room temperature and the solution was collected after filtration. The cleavage step was repeated for another time.
2) The solution was combined after filtration.
3) The solution was concentrated by rotary evaporation.
4) The crude peptide was lyophilized to afford compound 1 (8.00 g, crude) as a colorless oil. Chemical Formula: $C_{17}H_{29}NO_7$, LCMS found: $[M+H]^+=360.40$;

Step 2: Preparation of 2,3,5,6-tetrafluorophenyl 17-oxo-4,7,10,13-tetraoxa-16-azadocos-21-ynoate (compound 2)

A mixture of compound 1 (8.00 g, 22.25 mmol, 1.00 eq), 2,3,5,6-tetrafluorophenol (11.08 g, 66.75 mmol, 4.00 eq), and EDCI (9.52 g, 33.23 mmol, 2.00 eq) in DMF (224 mL) was stirred at 25° C. for 16 hrs. LCMS showed reactant 1 was consumed completely, and on main peak was desired MS. The mixture was purified by Flash (C18, TFA condition) and lyophilized to afford compound 2 (9.00 g, 17.73 mmol, 79.6% yield) as a yellow oil. Chemical Formula: $C_{23}H29F_4NO_7$, LCMS found: $[M+H]^+=508.15$.

Step 3: Preparation of Intermediate 4

A mixture of Intermediate 5 (3.00 g, 1.74 mmol, 1.00 eq), compound 2 (1.77 g, 3.48 mmol, 2.00 eq), and DIEA (3.03 mL, 17.42 mmol, 10.00 eq) in DMF (30 mL) was stirred at 0° C. for 8 hrs. The mixture was adjusted pH=5 and purified by prep-HPLC (TFA condition) directly to afford Intermediate 4 (1.30 g, 95.1% purity, 34.3% yield) as a white solid. Chemical Formula: $C_{96}H_{135}N_{21}O_{26}S_2$, LCMS found: $[M+2H]^{2+}=1032.10$, $[M+3H]^{3+}=688.40$.

Preparation of Compound 4: 3-((6S,9R,12S,15S, 18S,21S,27S,30S,33S,36S,39R,42S,44aS, 46S, 49aR)-30-((1H-imidazol-5-yl)methyl)-12,33-bis ((1H-indol-3-yl)methyl)-42-(carboxy methyl)-46- (20-(1-(1-(((2R,3R,4R,5S)-3,4-dihydroxy-5-((6- (trifluoromethyl)pyrazin-2-yl)amino)tetrahydro-2H- pyran-2-yl)-20-(1-((2R,3R,4R,5S)-3,4-dihydroxy-5- ((6-(trifluoro methyl)pyrazin-2-yl)amino)tetrahydro- 2H-pyran-2-yl)-15-oxo-2,5,8,11,18-pentaoxa-14- azanonadecan-19-yl)-15,22-dioxo-2,5,8,11,18-pen- taoxa-14,21-diazaheptacosan-27-yl)-1H-1,2,3-tri- azol-4-yl)-17-oxo-4,7,10,13-tetraoxa-16-azaicosana- mido)-6-((R)-1-hydroxyethyl)-18,27-diisobutyl-15- isopropyl-36-methyl-5,8,11,14,17,20,23,26,29,32,35, 38,41,44,49-pentadecaoxo octatetracontahydro-1H- 9,39-(methanodithiomethano)dipyrrolo[1,2-a:1',2'-d] [1,4,7,10,13,16,19,22,25,28,31,34,37,40,43] pentadecaazacyclopentatetracontin-21-yl)propanoic acid

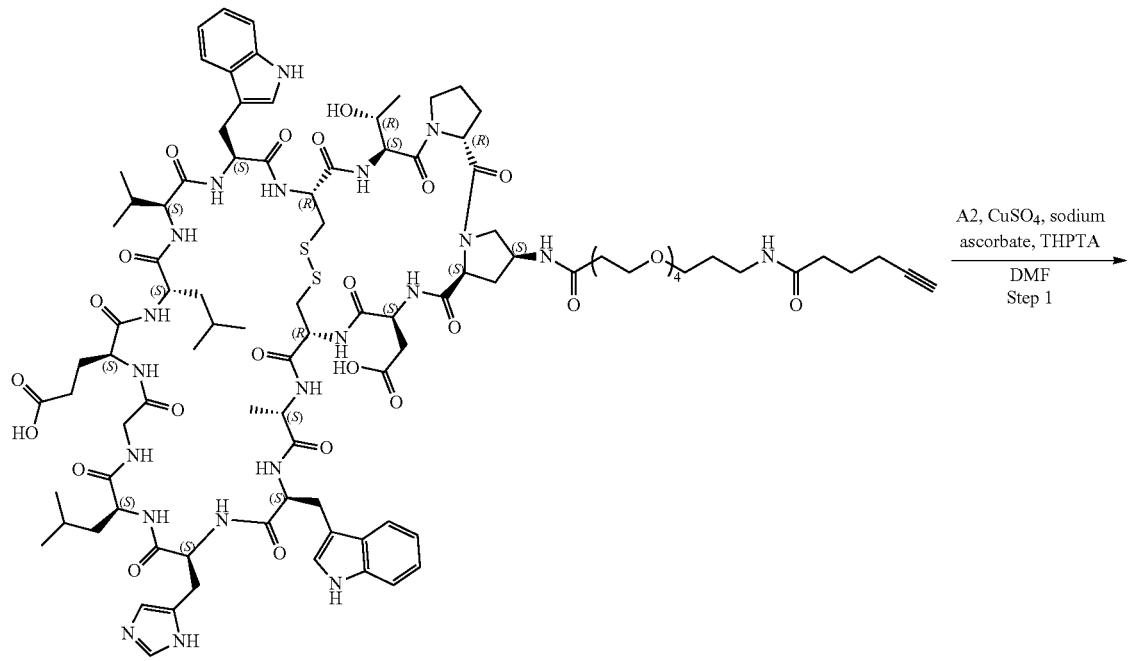

Intermediate 4

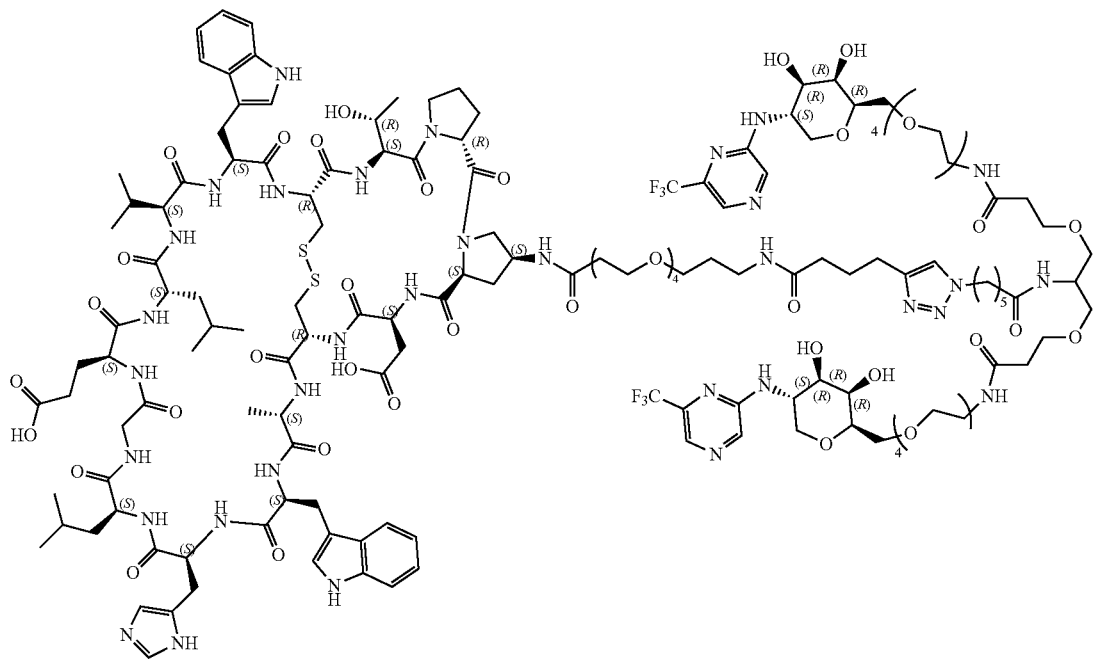

Compound 4

A mixture of Intermediate 4 (402.1 mg, 194.9 umol, 1.00 eq), A2 (254.8 mg, 194.91 umol, 1.00 eq) in DMF (8 mL) was cooled to 0° C., degassed and purged with N$_2$ for 3 times. Then a freshly prepared mixture of CuSO$_4$ (0.4 M, 487.27 uL, 1.00 eq), sodium ascorbate (0.5 M, 1.56 mL, 4.00 eq) and THPTA (86.34 mg, 194.91 umol, 1.00 eq) was added to the reaction mixture at 0° C. The mixture was degassed and purged with N$_2$ for 3 times, stirred at 0° C. for 2 hrs under N$_2$ atmosphere. The mixture was purified by prep-HPLC (acid condition, TFA) directly and lyophilized to afford Compound 4 (495.0 mg, 92.0% purity, 71.70% yield) as a light yellow solid. Chemical Formula: $C_{149}H_{219}F_6N_{33}O_{45}S_2$, LCMS found: [M+2H]$^{2+}$=1686.80, [M+3H]$^{3+}$=1125.00, [M+4H]$^{4+}$=843.90, [M+5H]$^{5+}$=675.40.

The compounds Compound 16, Compound 82, Compound 83, Compound 84, Compound 85, and Compound 86 were prepared according to the procedure same as Compound 4 using the starting material in the table below.

| Compound | Starting material | Analytical data |
| --- | --- | --- |
| Compound 16 | A18 | Yield: 798 mg, 95.8% purity, 78.4% yield, white solid. LC-MS found: [M + 2H]$^{2+}$ = 1686.60, [M + 3H]$^{3+}$ = 1124.70, [M + 4H]$^{4+}$ = 843.80, [M + 5H]$^{5+}$ = 675.30. |
| Compound 82 | A147 | Yield: 34.4 mg, 98.3% purity, 58.5% yield, white solid. LC-MS (ESI) found: [M + H + Na]$^{2+}$ = 1713.2, [M + 2H]$^{2+}$ = 1702.2, [M + 2H − sugar]$^{2+}$ = 1548.6, [M + 2H − 2sugar]$^{2+}$ = 1394.4, [M + 3H]$^{3+}$ = 1135.2. |

| Compound | Starting material | Analytical data |
|---|---|---|
| Compound 83 | A148 | Yield: 34.8 mg, 97.3% purity, 50.6% yield, white solid. TOF found: [M + H]$^+$ = 1970.8, [M + 2H]$^{2+}$ = 1314.1, [M + 3H]$^{3+}$ = 985.9. |
| Compound 84 | A149 | Yield: 18.2 mg, 97.2% purity, 27.4% yield, white solid. LC-MS (ESI) found: [M + H + Na]$^{2+}$ = 1609.7, [M + 2H]$^{2+}$ = 1598.1, [M + 2H − sugar]$^{2+}$ = 1496.6, [M + 2H − 2sugar]$^{2+}$ = 1394.5, [M + 3H]$^{3+}$ = 1067.7. |

| Compound | Starting material | Analytical data |
|---|---|---|
| Compound 85 | A150 | Yield: 17.9 mg, 97.9% purity, 49.2% yield, white solid. LC-MS found: [M + H + Na]$^{2+}$ = 1849.4, [M + 2H]$^{2+}$ = 1838.8, [M + 2H − sugar]$^{2+}$ = 1736.9, [M + 2H − 2sugar]$^{2+}$ = 1635.3, [M + 3H]$^{3+}$ = 1225.8. |
| Compound 86 | A151 | Yield: 34.2 mg, 95.4% purity, 53.9% yield, white solid. LC-MS found: [M + 2H]$^{2+}$ = 1970.2, [M + 3H]$^{3+}$ = 1313.8. |

Preparation of Intermediate 1 (S)-3-(((4R,7S,10S, 13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl) carbamoyl)-16-(2-carboxyethyl)-13,22-diisobutyl-10-isopropyl-31-methyl-6,9,12,15,18,21,24,27,30, 33-decaoxo-1,2-dithia-5,8,11,14,17,20,23,26,29,32-decaazacyclopentatriacontan-34-yl)carbamoyl)-24-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl) amino)tetrahydro-2H-pyran-2-yl)-15-oxo-2,5,8,11, 18-pentaoxa-14-azanonadecan-19-yl)-15,22-dioxo-2, 5,8,11,18-pentaoxa-14,21-diazaheptacosan-27-yl)-1H-1,2,3-triazol-4-yl)-5,21-dioxo-8,11,14,17-tetraoxa-4,20-diazatetracosan-1-oic acid

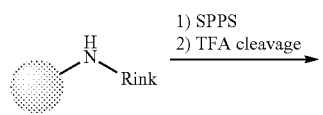

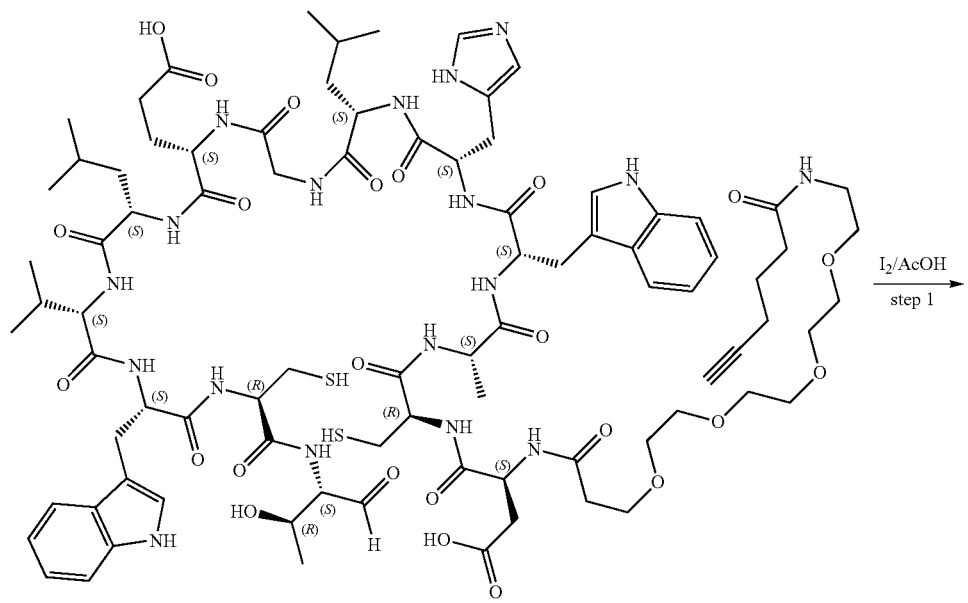

-continued

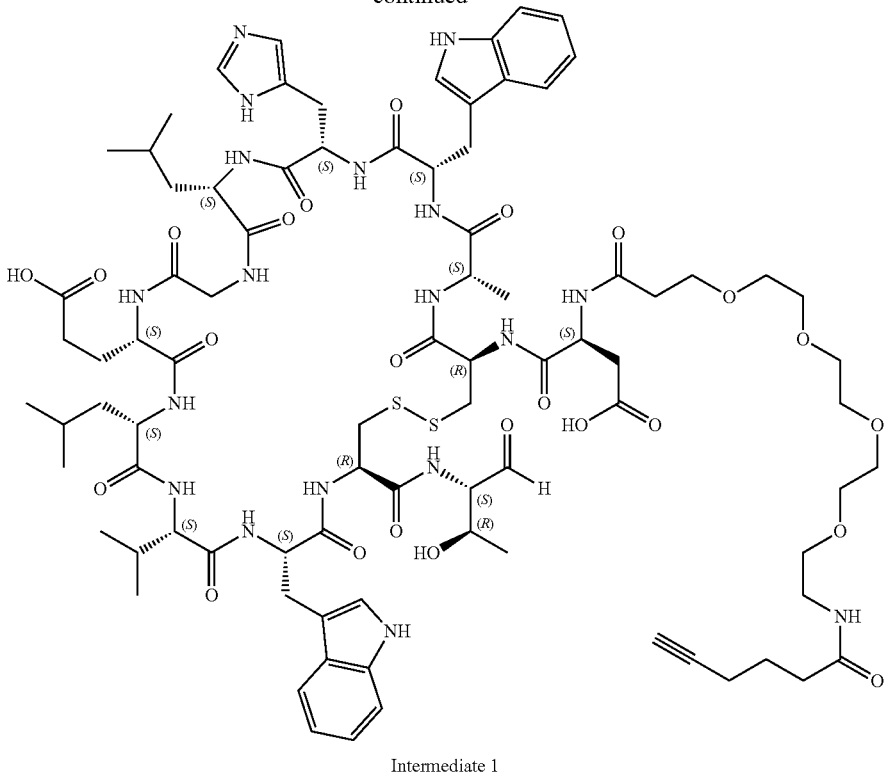

Intermediate 1

Step 1: General Procedure for Preparation of Intermediate 1

Solid Phase Peptide Synthesis

The peptide was synthesized using standard Fmoc chemistry.

1) Resin preparation: To the vessel containing AM Resin (66.67 g, 20.00 mmol, 0.30 mmol/g) in DMF (600 mL) mixed for 30 mins with $N_2$ bubbling at 15° C. The resin was washed with DMF (600 mL)*5. Then 20% piperidine in DMF (600 mL) was added and the mixture was bubbled with $N_2$ for 30 mins at 15° C. The mixture was filtered to obtain the resin. The resin was washed with DMF (600 mL)*5 before proceeding to next step.

2) Coupling: A solution of Fmoc-Thr(tBu)-OH (23.82 g, 60.00 mmol, 3.00 eq), HBTU (21.60 g, 57 mmol, 2.85 eq) in DMF (300 mL) was added to the resin with $N_2$ bubbling. Then DIEA (22.11 mL, 120 mmol, 6.00 eq) was added to the mixture dropwise and bubbled with $N_2$ for 30 mins at 15° C. The coupling reaction was monitored by ninhydrin test, if it showed colorless, the coupling was completed. The resin was then washed with DMF (600 mL)*5.

3) De-protection: 20% piperidine in DMF (600 mL) was added to the resin and the mixture was bubbled with $N_2$ for 30 mins at 15° C. The resin was then washed with DMF (600 mL)*5. The De-protection reaction was monitored by ninhydrin test, if it showed blue or other brownish red, the reaction was completed.

4) Step 2 and 3 were repeated for all other amino acids: (2-15 in Table 4).

TABLE 4

| # | Materials | Coupling reagents |
|---|---|---|
| 1 | Fmoc-Thr(tBu)-OH (3.00 eq) | HBTU (2.85 eq) and DIEA (6.00 eq) |
| 2 | Fmoc-Cys(Trt)-OH (3.00 eq) | HBTU (2.85 eq) and DIEA (6.00 eq) |
| 3 | Fmoc-Trp-OH (3.00 eq) | HBTU (2.85 eq) and DIEA (6.00 eq) |
| 4 | Fmoc-Val-OH (3.00 eq) | HBTU (2.85 eq) and DIEA (6.00 eq) |
| 5 | Fmoc-Leu-OH (3.00 eq) | HBTU (2.85 eq) and DIEA (6.00 eq) |
| 6 | Fmoc-Glu(OtBu)-OH (3.00 eq) | HATU (2.85 eq) and DIEA (6.00 eq) |
| 7 | Fmoc-Gly-OH (3.00 eq) | HATU (2.85 eq) and DIEA (6.00 eq) |
| 8 | Fmoc-Leu-OH (3.00 eq) | HATU (2.85 eq) and DIEA (6.00 eq) |
| 9 | Fmoc-His(Trt)-OH (2.00 eq) | HATU (2.85 eq) and DIEA (6.00 eq) |
| 10 | Fmoc-Trp-OH (3.00 eq) | HATU (2.85 eq) and DIEA (6.00 eq) |
| 11 | Fmoc-Ala-OH (3.00 eq) | HATU (2.85 eq) and DIEA (6.00 eq) |
| 12 | Fmoc-Cys(Trt)-OH (3.00 eq) | HATU (2.85 eq) and DIEA (6.00 eq) |
| 13 | Fmoc-Asp(OtBu)-OH (3.00 eq) | HATU (2.85 eq) and DIEA (6.00 eq) |
| 14 | Fmoc-Peg 4-OH (1.50 eq) | HATU (1.42 eq) and DIEA (3.00 eq) |
| 15 | hex-5-ynoic acid (1.50 eq) | HATU (1.42 eq) and DIEA (3.00 eq) |

Peptide Cleavage and Purification:
1) Cleavage buffer (TFA/TIS/H$_2$O/3-mercaptopropanoic acid, 92.5/2.5/2.5/2.5, v/v/v/v, 1 L) was added to the flask containing the side chain protected peptide at room temperature and stir for 2 hrs.
2) The peptide was precipitated with cold isopropyl ether.
3) After filtered, the solid was washed with isopropyl ether two additional times.
4) Dried the crude peptide under vacuum 2 hrs.
5) The crude peptide was dissolved in MeCN (10 L) and H$_2$O (10 L), then Iodine (0.1 M in AcOH) was added dropwise to the vigorously stirring mixture until yellow color persists. After 2 minutes, sodium thiosulfate (0.1 M in water) was added dropwise until yellow color disappears. The mixture was lyophilized to afford the crude powder.
6) The crude power was purified by prep-HPLC (A: 0.075% TFA in H$_2$O, B: ACN) to afford Intermediate 1 (5.90 g, 95.1% purity, 14.9% yield) as a white solid. Chemical Formula: C$_{86}$H$_{123}$N$_{19}$O$_{24}$S$_2$; LCMS found: [M+H]$^+$=1871.00, [M+2H]$^{2+}$=936.10, [M+3H]$^{3+}$=624.38.

Intermediate 32 was prepared according to the procedure same as that of Intermediate

| Compound | structure | Analytical data |
|---|---|---|
| Intermediate 32 | 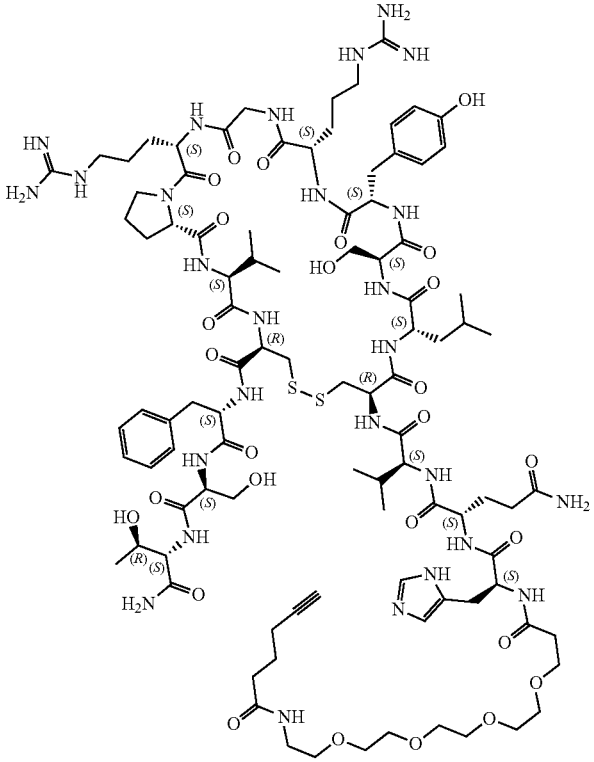 | Yield: 3.40 g, 95.0% purity, 23.4% yield, white solid. LC-MS found: [M + 2H]$^{2+}$ = 1096.12, [M + 3H]$^{3+}$ = 731.11. |

Preparation of Compound 22: (S)-3-(((4R,7S,10S,13S,16S,22S,25S,28S,31S,34R)-25-((1H-imidazol-5-yl)methyl)-7,28-bis((1H-indol-3-yl)methyl)-4-(((2S,3R)-1-amino-3-hydroxy-1-oxobutan-2-yl)carbamoyl)-16-(2-carboxyethyl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)carbamoyl)-24-(1-(1-((2R,3R,4R,5S)-3,4-dihydroxy-5-((4-(trifluoromethyl)pyrimidin-2-yl)amino)tetrahydro-2H-pyran-2-yl)-20-(1-((2R,3R,4R,5S)-3,4-dihydroxy-5-((4-(trifluoromethyl)pyrimidin-2-yl)amino)tetrahydro-2H-pyran-2-yl)-15-oxo-2,5,8,11,18-pentaoxa-14-azanonadecan-19-yl)-15,22-dioxo-2,5,8,11,18-pentaoxa-14,21-diazaheptacosan-27-yl)-1H-1,2,3-triazol-4-yl)-5,21-dioxo-8,11,14,17-tetraoxa-4,20-diazatetracosan-1-oic acid

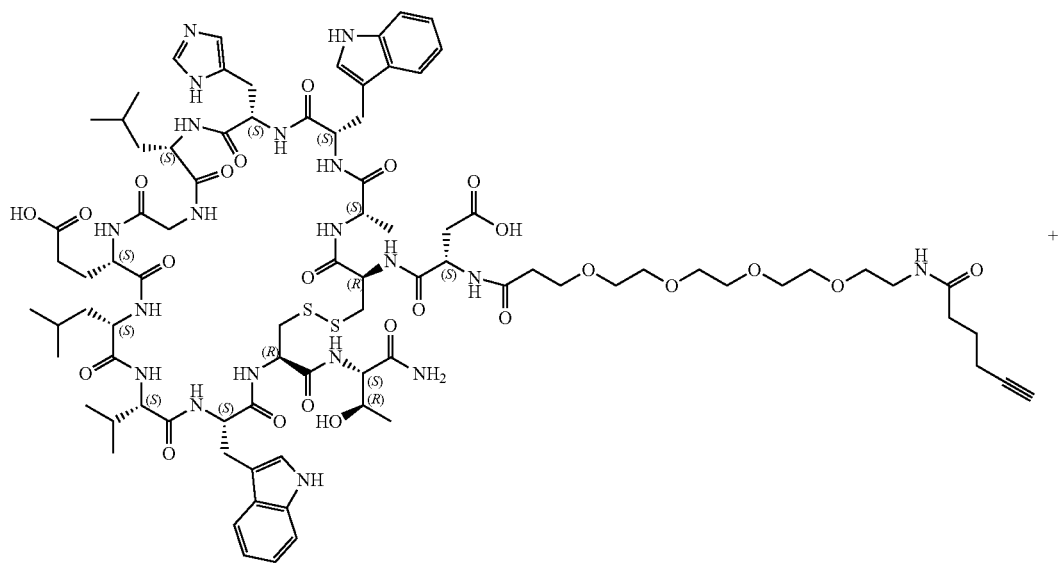

Intermediate 1

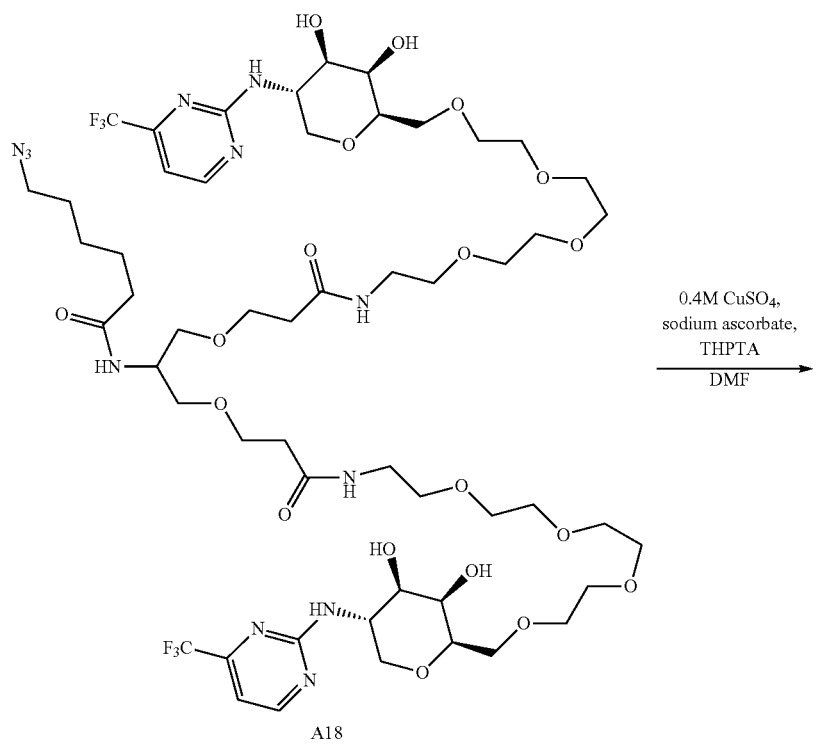

A18

-continued

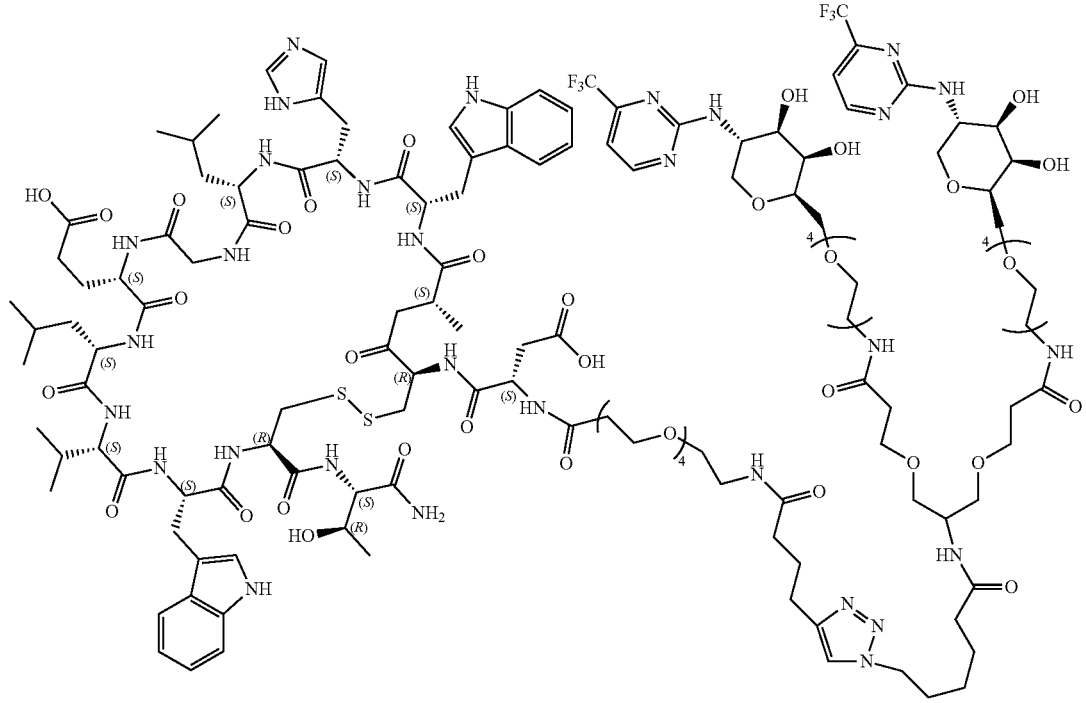

Compound 22

A mixture of Intermediate 1 (3.53 g, 1.79 mmol, 1.00 eq), A18 (2.34 g, 1.79 mmol, 1.00 eq), sodium ascorbate (1.42 g, 7.16 mmol, 4.00 eq), CuSO$_4$ (0.40 M, 4.47 mL, 1.00 eq) and THPTA (792.95 mg, 1.79 mmol, 1.00 eq) in DMF (30 mL) was degassed and purged with N$_2$ for 3 times, and then the mixture was stirred at 15° C. for 2 hrs under N$_2$ atmosphere. LCMS showed Intermediate 1 was consumed completely and one main peak with desired m/z. The mixture was purified by Prep-HPLC (TFA condition) directly to afford Compound 22 (4.31 g, 97.3% purity, 73.7% yield) as a white solid. Chemical Formula: $C_{86}H_{123}N_{19}O_{24}S_2$; LCMS found: $[M+2H]^{2+}$=1590.0, $[M+3H]^{3+}$=1060.4, $[M+4H]^{4+}$=795.7.

The compounds Compound 87, Compound 88, Compound 89, Compound 90 and Compound 23 were synthesized according to the procedure same as that of Compound 22.

| Compound | Starting material | Analytical data |
|---|---|---|
| 87 | | Yield: 661.0 mg, 95.5% purity, 72.0% yield, white solid. LC-MS found: $[M + 2H]^{2+}$ = 1558.0, $[M + 3H]^{3+}$ = 1039.1, $[M + 4H]^{4+}$ = 779.7 |

-continued
| Compound | Starting material | Analytical data |
|---|---|---|
| Compound 88 | 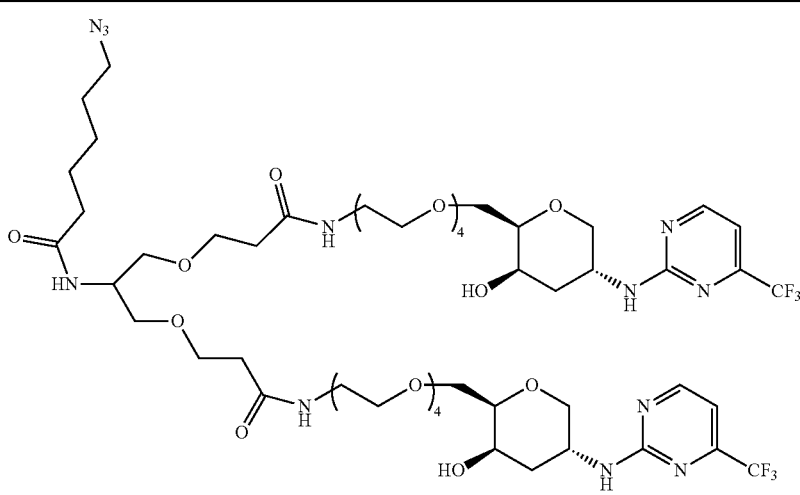 | Yield: 141.0 mg, 96.7% purity, 79.3% yield, white solid. LC-MS found: $[M + 2H]^{2+} = 1573.9$, $[M + 3H]^{3+} = 1049.6$, $[M + 4H]^{4+} = 787.5$, $[M + 5H]^{5+} = 630.0$ |
| Compound 89 | 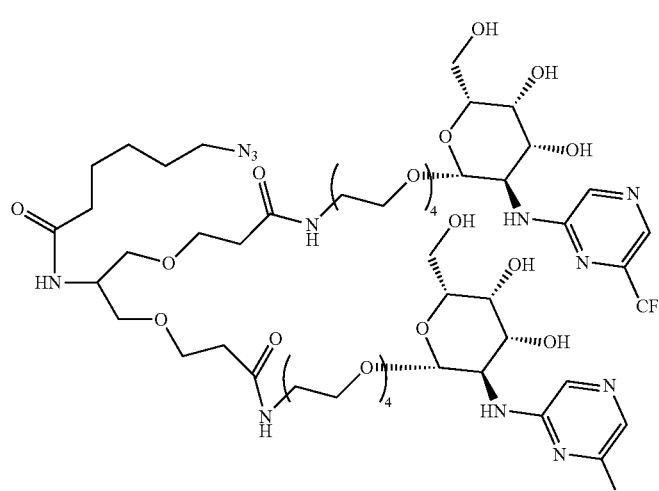<br>A147 | Yield: 23.0 mg, 99.6% purity, 33.2% yield, white solid. TOF found: $[M + H]^{+} = 3210.1$, $[M + 2H]^{2+} = 1605.71$, $[M + 3H]^{3+} = 1070.47$. |
| Compound 90 | 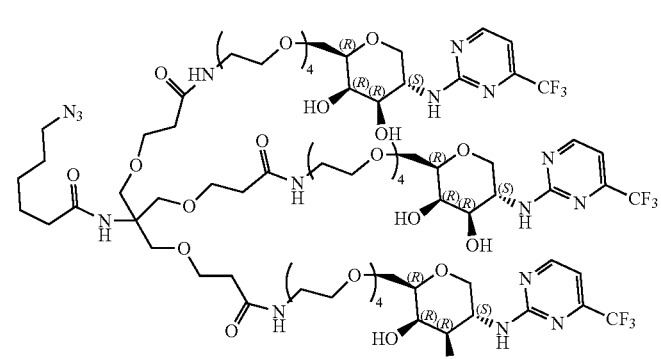<br>A151 | Yield: 31.5 mg, 97.2% purity, 50.5% yield, white solid. LC-MS (ESI) found: $[M + H + Na]^{2+} = 1885.9$, $[M + 2H]^{2+} = 1874.5$, $[M + 3H]^{3+} = 1250.1$, $[M + 4H]^{4+} = 937.5$ |

| Compound | Starting material | Analytical data |
|---|---|---|
| Compound 23 | 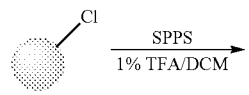 | Yield: 136.0 mg, 97.8% purity, 49.7% yield, white solid. LC-MS found: $[M + 2H]^{2+}$ = 1749.97 $[M + 3H]^{3+}$ = 1167.00, $[M + 4H]^{4+}$ = 875.42, $[M + 5H]^{5+}$ = 700.50, $[M + 6H]^{6+}$ = 583.87. |

Preparation of Intermediate 30 3-[(1R,4S,7S,10S,13S,19S,22S,25S,28S,31R,34S,40R,44R,46S,49S)-44-amino-49-(carboxymethyl)-34-[(1R)-1-hydroxyethyl]-10-(1H-imidazol-5-ylmethyl)-7,28-bis(1H-indol-3-ylmethyl)-13,22-diisobutyl-25-isopropyl-4-methyl-2,5,8,11,14,17,20,23,26,29,32,35,41,47,50-pentadecaoxo-53,54-dithia-3,6,9,12,15,18,21,24,27,30,33,36,42,48,51-pentadecazatetracyclo[29.20.4.0³⁶,⁴⁰.0⁴²,⁴⁶]pentapentacontan-19-yl]propanoic acid

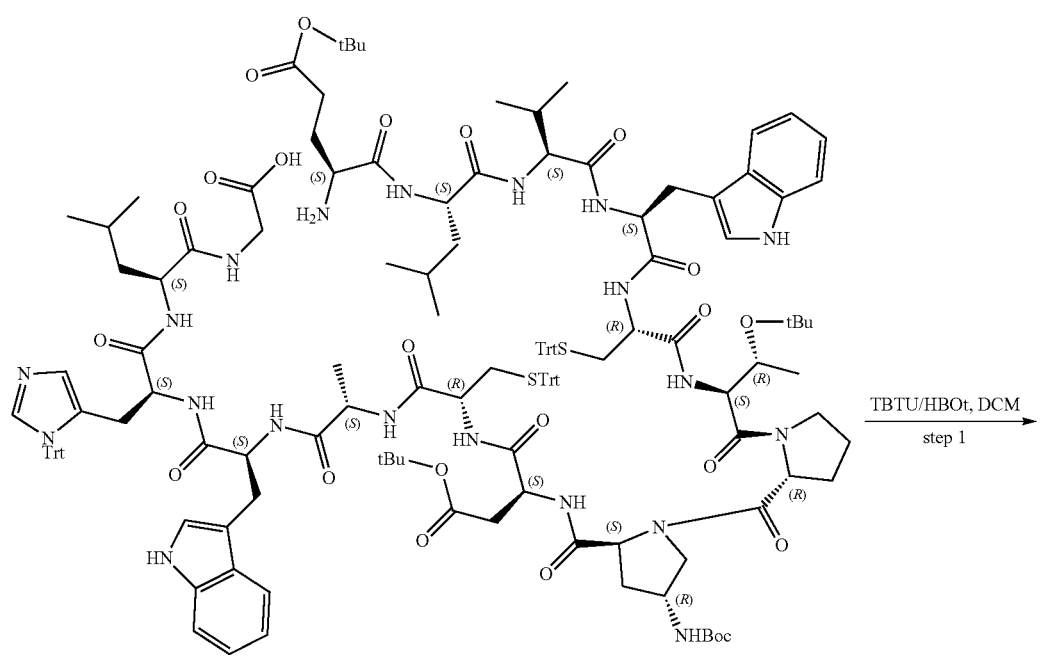

-continued
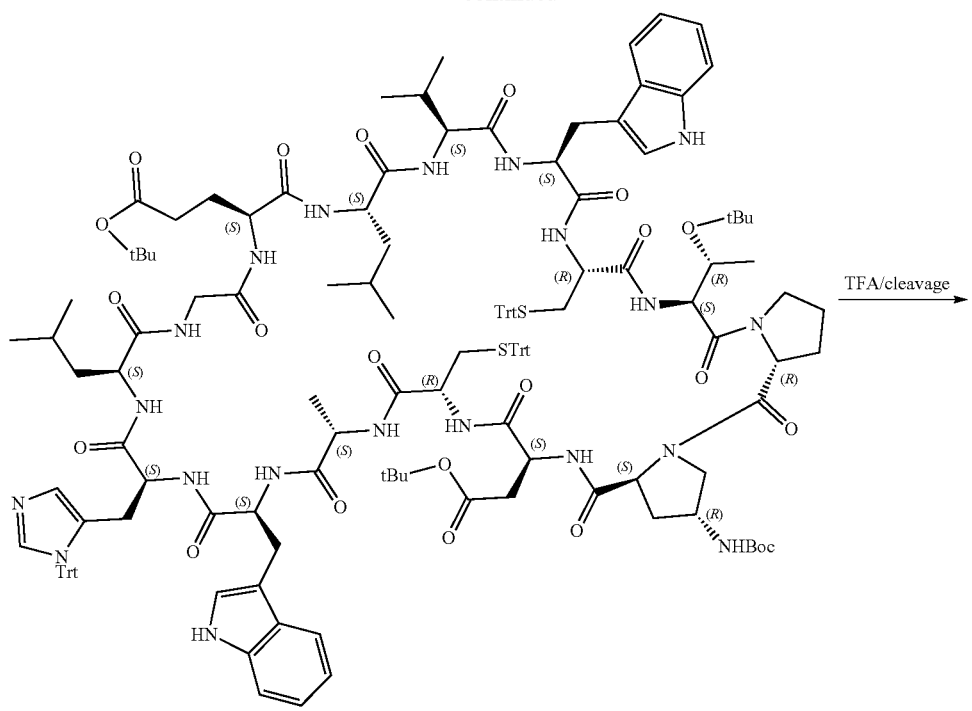
TFA/cleavage →
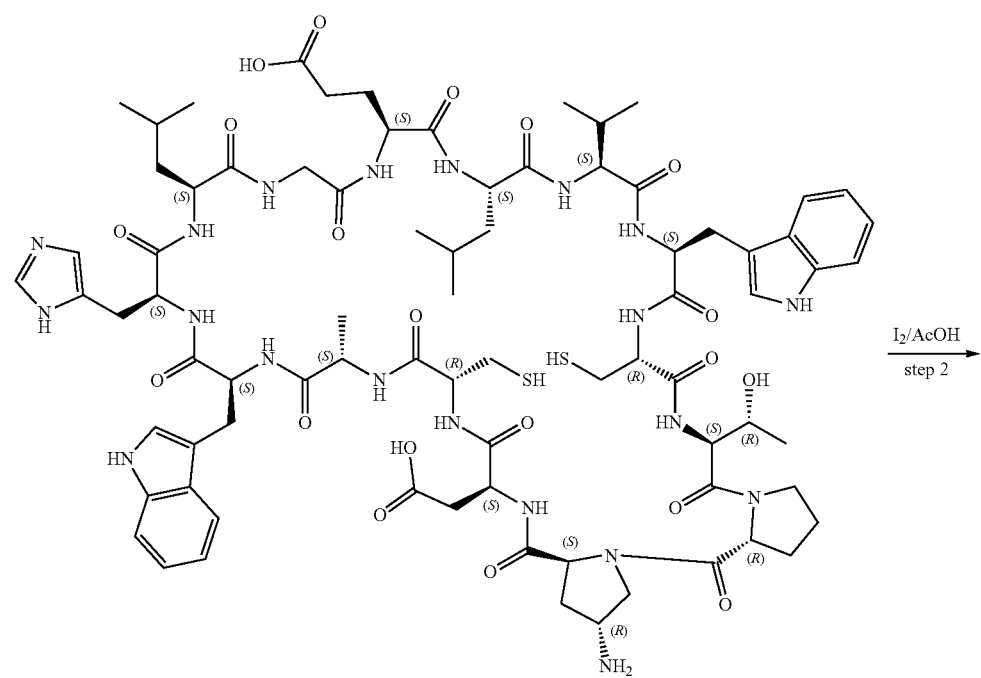
I₂/AcOH
step 2 →

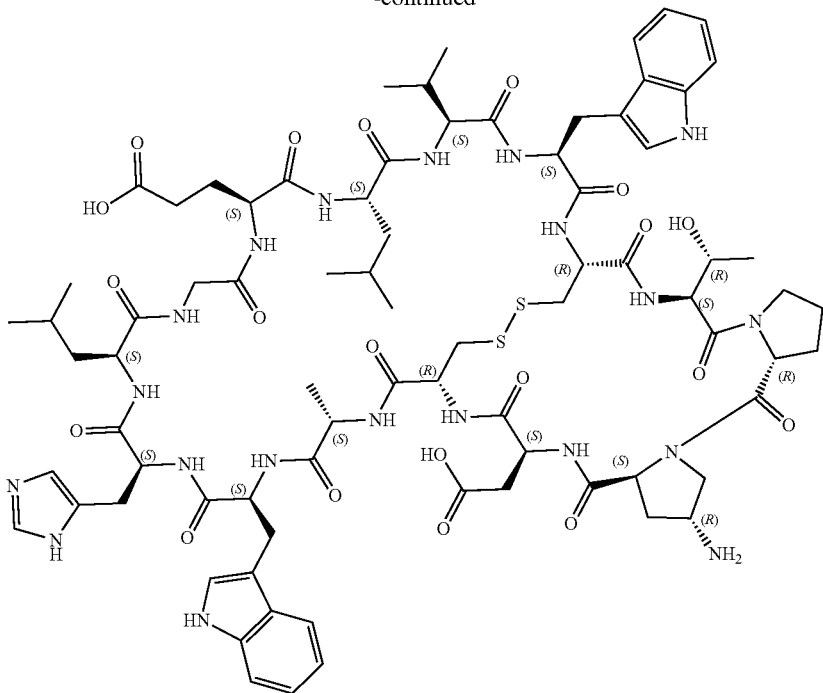

Intermediate 30

Step 1: Preparation of (2)

Solid Phase Peptide Synthesis

The peptide was synthesized using standard Fmoc chemistry.
1) Resin preparation: To the vessel containing CTC Resin (76.92 g, 40.00 mmol, 0.65 mmol/g) and Fmoc-Gly-OH (11.88 g, 40.00 mmol, 1.00 eq) in DCM (500 mL) was added DIEA (26.46 mL, 160.00 mmol, 4.00 eq) dropwise and mixed for 2 hrs with $N_2$ bubbling at 15 TC. Then added MeOH (76.00 mL) and bubbled with $N_2$ for another 30 mins. The resin was washed with DMF (1.00 L)*5. Then 20% piperidine in DMF (1.00 L) was added and the mixture was bubbled with $N_2$ for 30 mins at 15° C. The mixture was filtered to obtain the resin. The resin was washed with DMF (1.00 L)*5 before proceeding to next step.
2) Coupling: A solution of Fmoc-Leu-OH (42.36 g, 120.00 mmol, 3.00 eq), HBTU (43.32 g, 114.00 mmol, 2.85 eq) in DMF (500 mL) was added to the resin with $N_2$ bubbling. Then DIEA (39.69 mL, 240 mmol, 6.00 eq) was added to the mixture dropwise and bubbled with $N_2$ for 30 mins at 15 TC. The coupling reaction was monitored by ninhydrin test, if it showed colorless, the coupling was completed. The resin was then washed with DMF (1 L)*5.
3) De-protection: 2000 piperidine in DMF (1 L) was added to the resin and the mixture was bubbled with $N_2$ for 30 mins at 15° C. The resin was then washed with DMF (1 L)*5. The De-protection reaction was monitored by ninhydrin test, if it showed blue or other brownish red, the reaction was completed.
4) Step 2 and 3 were repeated for all other amino acids: (2-15 in Table 5).

TABLE 5

| # | Materials | Coupling reagents |
|---|---|---|
| 1 | Fmoc-Gly-OH (1.00 eq) | DIEA (4.00 eq) |
| 2 | Fmoc-Leu-OH (3.00 eq) | HBTU (2.85 eq) and DIEA (6.00 eq) |
| 3 | Fmoc-His(Trt)-OH (2.00 eq) | HBTU (2.85 eq) and DIEA (6.00 eq) |
| 4 | Fmoc-Trp-OH (3.00 eq) | HBTU (2.85 eq) and DIEA (6.00 eq) |
| 5 | Fmoc-Ala-OH (3.00 eq) | HBTU (2.85 eq) and DIEA (6.00 eq) |
| 6 | Fmoc-Cys(Trt)-OH (3.00 eq) | HBTU (2.85 eq) and DIEA (6.00 eq) |
| 7 | Fmoc-Asp(OtBu)-OH (3.00 eq) | HBTU (2.85 eq) and DIEA (6.00 eq) |
| 8 | Boc-(2S,4R)-4-amino-1-Fmoc-pyrrolidine-2-carboxylic acid (2.00 eq) | HATU (1.85 eq) and DIEA (4.00 eq) |
| 9 | Fmoc-D-Pro-OH (3.00 eq) | HATU (2.85 eq) and DIEA (3.00 eq) |
| 10 | Fmoc-Thr(tBu)-OH (3.00 eq) | HATU (2.85 eq) and DIEA (3.00 eq) |
| 11 | Fmoc-Cys(Trt)-OH (3.00 eq) | HATU (2.85 eq) and DIEA (3.00 eq) |
| 12 | Fmoc-Trp-OH (3.00 eq) | HATU (2.85 eq) and DIEA (3.00 eq) |
| 13 | Fmoc-Val-OH (3.00 eq) | HATU (2.85 eq) and DIEA (3.00 eq) |
| 14 | Fmoc-Leu-OH (3.00 eq) | HATU (2.85 eq) and DIEA (3.00 eq) |
| 15 | Fmoc-Glu(OtBu)-OH (3.00 eq) | HATU (2.85 eq) and DIEA (3.00 eq) |

Peptide Cleavage and Purification

1) Cleavage solution (100 TFA/DCM, 300 mL) was added into the flask containing the side chain protected crude peptide (5.0 mmol). The mixture was stirred for 5 mins at room temperature.

2) After filtration, the solution was collected.

3) Step 1-2 were repeated for another time.

4) The solution (contain compound 1) was combined.

5) The combined solution was diluted with DCM (4.50 L), then added HOBT (1.35 g, 10.0 mmol, 2.00 eq), TBTU (3.21 g, 10.0 mmol, 2.00 eq) and adjusted pH to 8 by DIEA. The mixture was stirred at 15° C. for 2 hrs.

6) The mixture was concentrated under reduced pressure to remove solvent.

7) The residue was added to 0.50 M HCl (cold, 2 L) and white solid was precipitated. After filtered, the solid was dried under lyophilization to afford compound 2 (9.37 g, crude) as a white solid. Chemical Formula: $C_{153}H_{184}N_{20}O_{22}S_2$, LCMS found: [M+H+Na]2+=1370.4;

8) Note: another 7 batches were synthesized using the same procedure as step 1-7. Total 8 batches afforded compound 2 (75.0 g, crude) as a white solid.

Step 2-3: General Procedure for Preparation of Intermediate 30

A mixture of compound 2 (75.0 g, 27.58 mmol) in TFA/TIS/H$_2$O (95/2.5/2.5, v/v/v, 1.5 L) was stirred at 15° C. for 2 hrs. The mixture was precipitated with cold isopropyl ether (15 L). After filtration, the solid was dried under vacuum for 2 hrs to afford compound 3 (51.72 g, crude). The compound 3 (25.00 g, crude) was dissolved in MeCN/H$_2$O (1/1, v/v, 5 L). I$_2$/HOAc (0.1 M) was added to the mixture dropwise at 15° C. until the light yellow persisted, and stirred at 15° C. for 5 mins. Then the mixture was quenched with 0.1 M Na$_2$S$_2$O$_3$ dropwise until the light yellow disappeared. 2 batches were performed used the same process. After filtration, the filtrate was purified by prep-HPLC (acid condition, TFA) directly to afford Intermediate 30 (10.2 g, 91.06% purity, 19.7% yield, 2 batches) as a white solid. Chemical Formula: $C_{79}H_{108}N_{20}O_{20}S_2$, LCMS found: [M+H]$^+$=1722.00, [M+2H]$^{2+}$=861.61.

Preparation of 3-((6S,9R,12S,15S,18S,21S,27S,30S,33S,36S,39R,42S,44aS,46R,49aR)-30-((1H-imidazol-5-yl)methyl)-12,33-bis((1H-indol-3-yl)methyl)-42-(carboxymethyl)-46-(2-(2-(2-((((2R,3R,4R,5S)-3,4-dihydroxy-5-((6-(trifluoromethyl)pyrazin-2-yl)amino)tetrahydro-2H-pyran-2-yl)methyl)amino)-2-oxoethoxy)ethoxy)acetamido)-6-((R)-1-hydroxyethyl)-18,27-diisobutyl-15-isopropyl-36-methyl-5,8,11,14,17,20,23,26,29,32,35,38,41,44,49-pentadecaoxooctatetracontahydro-1H-9,39-(methanodithiomethano)dipyrrolo[1,2-a:1',2'-d][1,4,7,10,13,16,19,22,25,28,31,34,37,40,43]pentadecaazacyclopentatetracontin-21-yl)propanoic acid

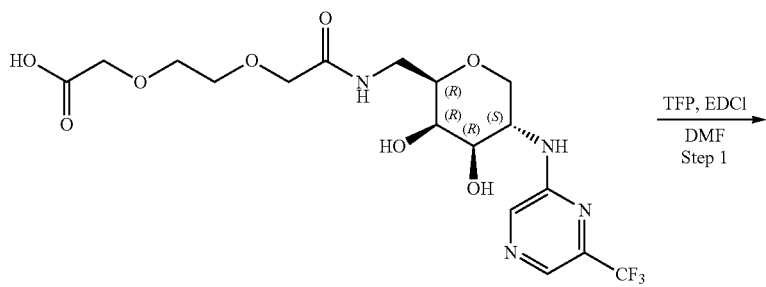

A30

1269

-continued

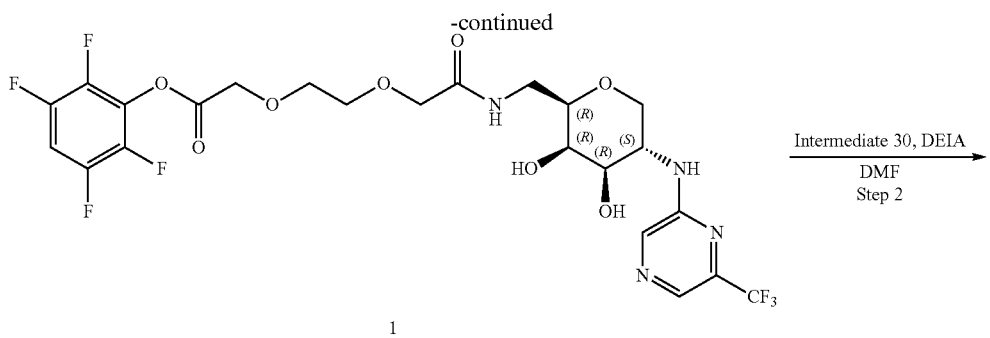

Intermediate 30, DEIA
DMF
Step 2

1

1270

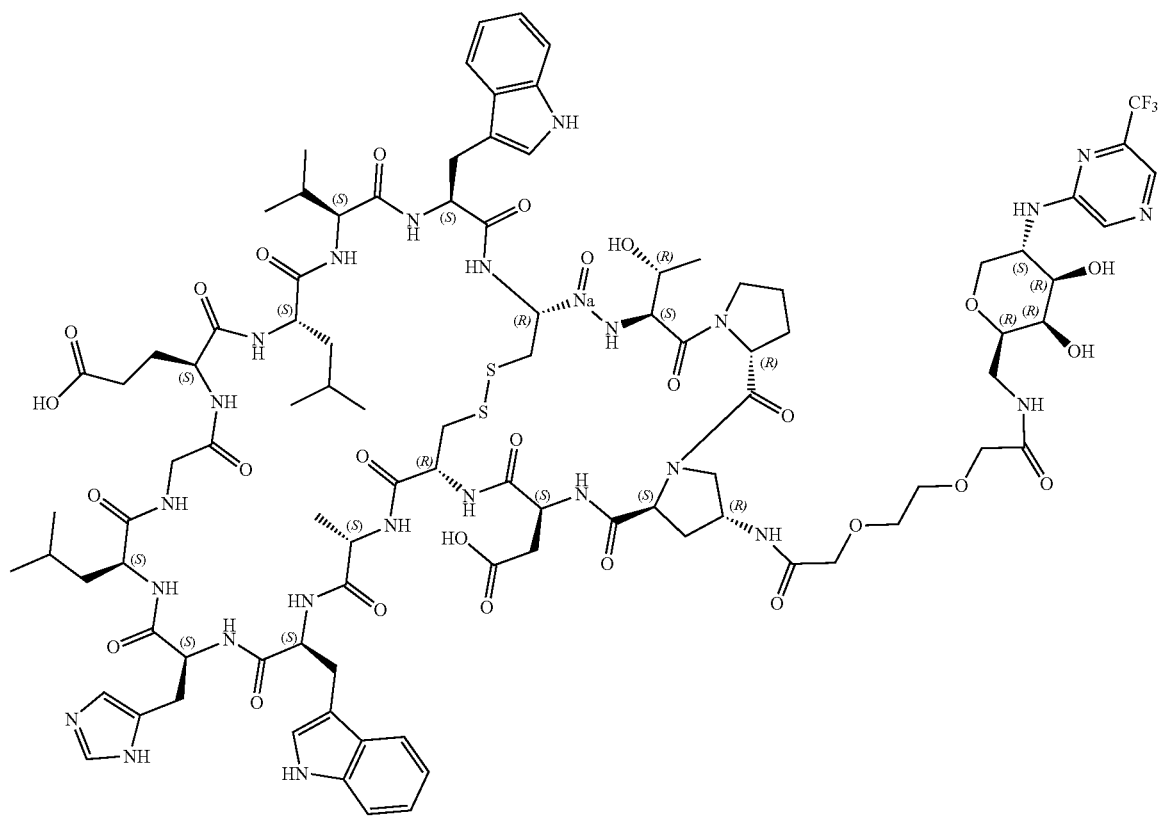

Compound 91

Step 1: Preparation of TFP Ester (Compound 1)

A mixture of A30 (60.0 mg, 128.10 umol, 1.00 eq), 2,3,5,6-tetrafluorophenol (85.1 mg, 512.40 umol, 4.00 eq) in DMF (1.0 mL) was cooled to 0° C. Then the mixture was added EDCI (49.1 mg, 256.20 umol, 2.00 eq) at 0° C. and stirred at 0° C. for 2 hrs. The reaction mixture was purified by prep-HPLC (acid condition, TFA) and lyophilized to afford TFP ester compound 1 (68.0 mg, ~70% purity, containing 2,3,5,6-tetrafluorophenol) as a colorless oil. Chemical Formula: $C_{23}H_{23}F_7N_4O_8$, LCMS found: $[M+H]^+= 617.20$.

Step 2: Preparation of Compound 91

A mixture of Intermediate 30 (208.9 mg, 121.34 umol, 1.10 eq), compound 4 (68.0 mg, 110.31 umol, 1.00 eq), DIEA (57.0 mg, 441.24 umol, 76.86 uL, 4.00 eq) in DMF (3.00 mL) was stirred at 15° C. for 1 hr. The reaction mixture was purified by prep-HPLC (acid condition, TFA) and lyophilized to afford Compound 91 (125.2 mg, 99.5% purity, 51.9% yield) as a white solid. Chemical Formula: $C_{96}H_{129}F_3N_{24}O_{27}S_2$, LCMS found: $[M+2H]^{2+}=1086.8$, $[M+3H]^{3+}=724.9$.

Compound 92 and Compound 93 was prepared according to the procedure same as that of Compound 91.

| Name | Starting material | Analytical data |
|---|---|---|
| Compound 92 | A31 | Yield: 19.5 mg, 98.7% purity, 40.27% yield, white solid. LC-MS found: [M + 2Na]$^{2+}$ = 1488.0, [M + H + Na]$^{2+}$ = 1477.0, [M + 2H]$^{2+}$ = 1466.00, [M + 3H]$^{3+}$ = 977.5, [M + 4H]$^{4+}$ = 733.3. |
| Compound 93 | | Yield: 8.3 mg, 95.9% purity, 22.36% yield, white solid. LC-MS found:, [2M + 3H]$^{3+}$ = 1533.5, [M + 2H]$^{2+}$ = 1150.3, [M + 3H]$^{3+}$ = 767.0. |

Preparation of Intermediate 31: 3-[(1R,4S,7S,10S,13S,19S,22S,25S,28S,31R,34S,40R,44R,46S,49S)-44-amino-49-(carboxymethyl)-34-[(1R)-1-hydroxyethyl]-10-(1H-imidazol-5-ylmethyl)-7,28-bis(1H-indol-3-ylmethyl)-13,22-diisobutyl-25-isopropyl-4-methyl-2,5,8,11,14,17,20,23,26,29,32,35,41,47,50-pentadecaoxo-53,54-dithia-3,6,9,12,15,18,21,24,27,30,33,36,42,48,51-pentadecazatetracyclo[29.20.4.0³⁶,⁴⁰.0⁴²,⁴⁶]pentapentacontan-19-yl]propanoic acid
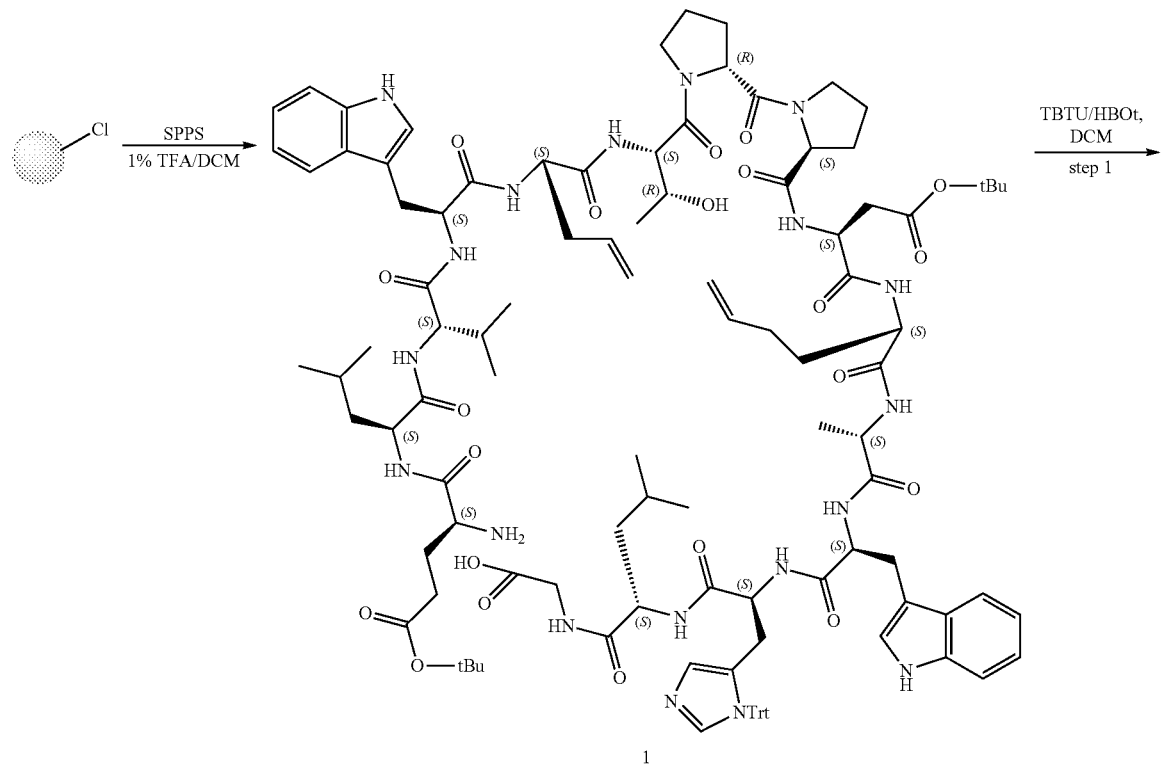
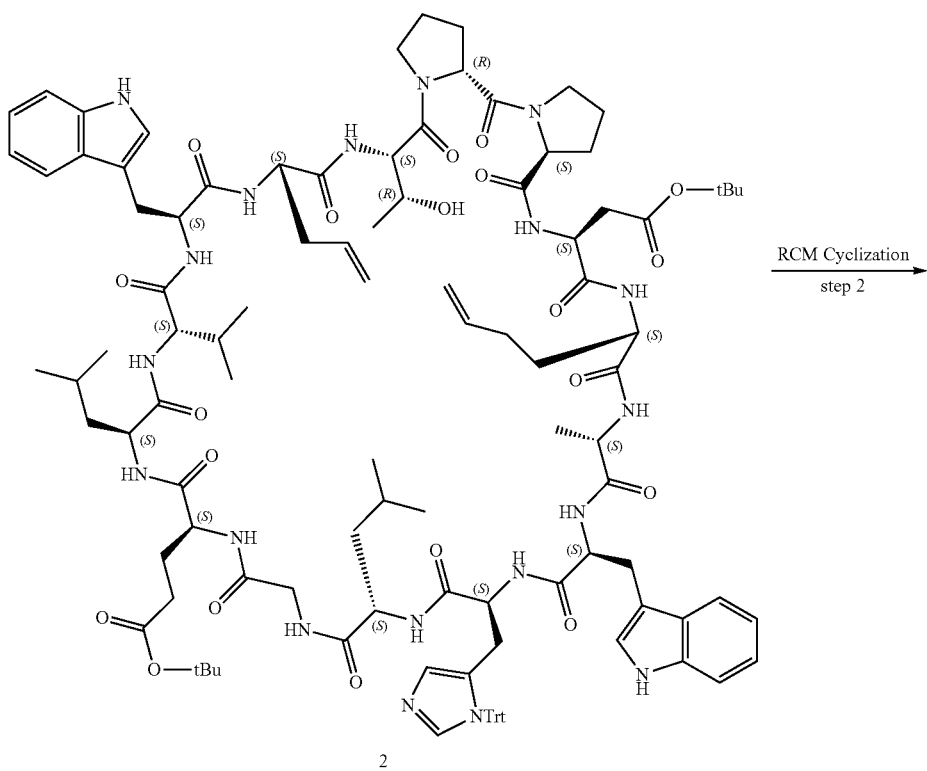

-continued
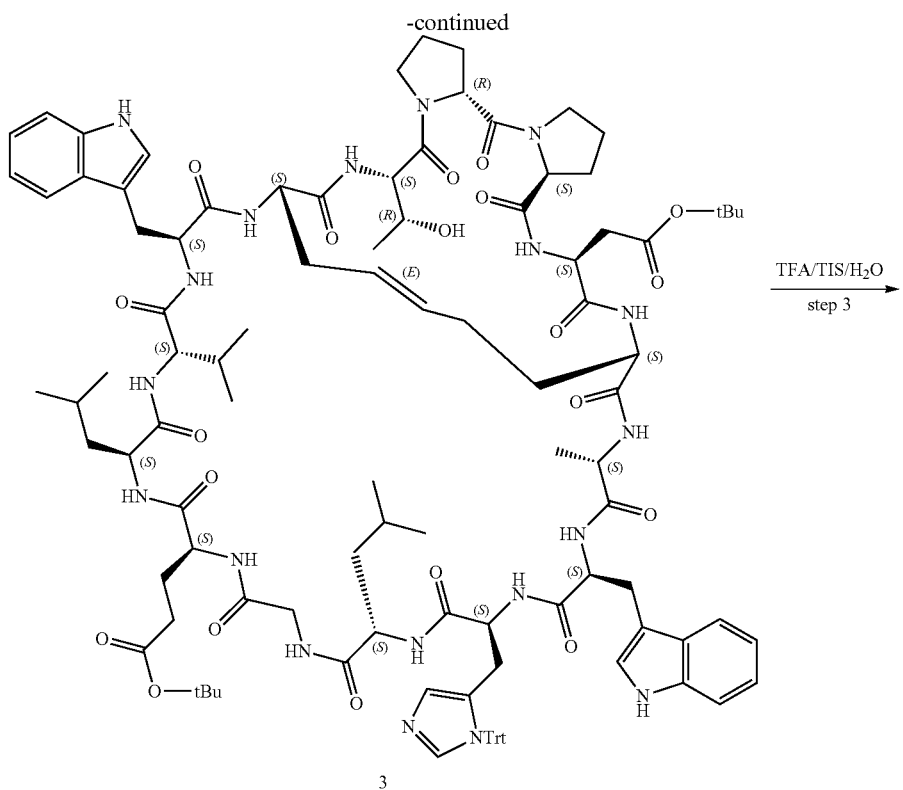
$\xrightarrow{\text{TFA/TIS/H}_2\text{O}}$ step 3
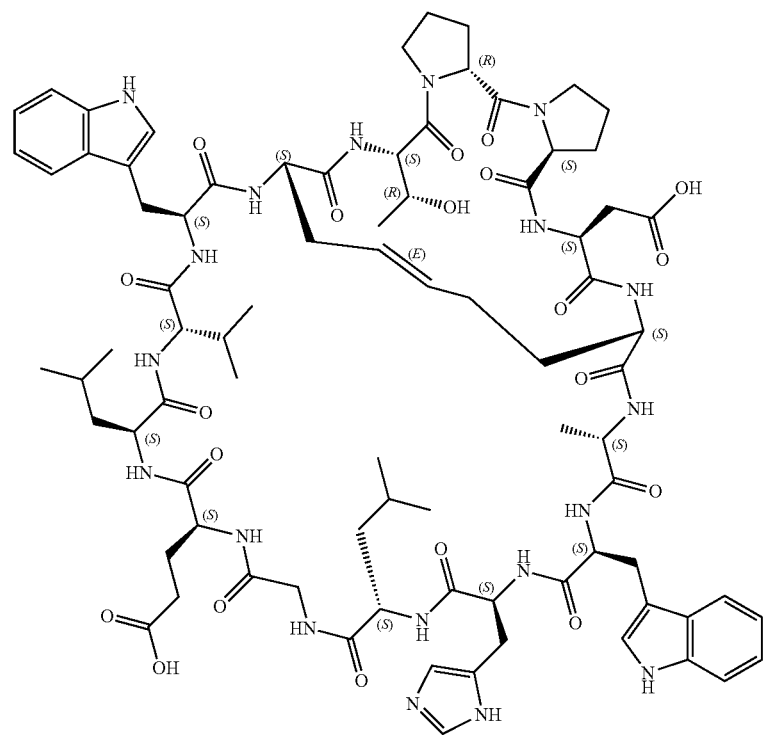
Intermediate 31

Step 1: Preparation of (2)

Solid Phase Peptide Synthesis

The peptide was synthesized using standard Fmoc chemistry.

1) Resin preparation: To the vessel containing CTC Resin (0.77 g, 0.50 mmol, 0.65 mmol/g) and Fmoc-Gly-OH (0.15 g, 0.50 mmol, 1.00 eq) in DCM (0.5 mL) was added DIEA (0.33 mL, 2.00 mmol, 4.00 eq) dropwise and mixed for 2 hrs with $N_2$ bubbling at 15° C. Then added MeOH (0.50 mL) and bubbled with $N_2$ for another 30 mins. The resin was washed with DMF (10 mL)*5. Then 20% piperidine in DMF (10 mL) was added and the mixture was bubbled with $N_2$ for 30 mins at 15° C. The mixture was filtered to obtain the resin. The resin was washed with DMF (10 mL)*5 before proceeding to next step.

2) Coupling: A solution of Fmoc-Leu-OH (0.53 g, 1.50 mmol, 3.00 eq), HBTU (0.54 g, 1.42 mmol, 2.85 eq) in DMF (5 mL) was added to the resin with $N_2$ bubbling. Then DIEA (0.50 mL, 3.0 mmol, 6.00 eq) was added to the mixture dropwise and bubbled with $N_2$ for 30 mins at 15° C. The coupling reaction was monitored by ninhydrin test, if it showed colorless, the coupling was completed. The resin was then washed with DMF (10 mL)*5.

3) De-protection: 20% piperidine in DMF (10 mL) was added to the resin and the mixture was bubbled with $N_2$ for 30 mins at 15° C. The resin was then washed with DMF (10 mL)*5. The De-protection reaction was monitored by ninhydrin test, if it showed blue or other brownish red, the reaction was completed.

4) Step 2 and 3 were repeated for all other amino acids: (2-15 in Table 5).

TABLE 5

| # | Materials | Coupling reagents |
|---|---|---|
| 1 | Fmoc-Gly-OH (1.00 eq) | DIEA (4.00 eq) |
| 2 | Fmoc-Leu-OH (3.00 eq) | HBTU (2.85 eq) and DIEA (6.00 eq) |
| 3 | Fmoc-His(Trt)-OH (2.00 eq) | HBTU (2.85 eq) and DIEA (6.00 eq) |
| 4 | Fmoc-Trp-OH (3.00 eq) | HBTU (2.85 eq) and DIEA (6.00 eq) |
| 5 | Fmoc-Ala-OH (3.00 eq) | HATU (2.85 eq) and DIEA (6.00 eq) |
| 6 | (S)-2-((((9H-fluoren-9-yl)methoxy)carbonyl)amino)hex-5-enoic acid (2.00 eq) | HATU (1.90 eq) and DIEA (4.00 eq) |
| 7 | Fmoc-Asp(OtBu)-OH (3.00 eq) | HBTU (2.85 eq) and DIEA (6.00 eq) |
| 8 | Fmoc-Pro-OH (2.00 eq) | HATU (1.85 eq) and DIEA (4.00 eq) |
| 9 | Fmoc-D-Pro-OH (3.00 eq) | HATU (2.85 eq) and DIEA (3.00 eq) |
| 10 | Fmoc-Thr(Bu)-OH (3.00 eq) | HATU (2.85 eq) and DIEA (3.00 eq) |
| 11 | (S)-2-((((9H-fluoren-9-4-yl)methoxy)carbonyl)amino)pentenoic acid (2.00 eq) | HATU (1.90 eq) and DIEA (4.00 eq) |
| 12 | Fmoc-Trp-OH (3.00 eq) | HATU (2.85 eq) and DIEA (3.00 eq) |
| 13 | Fmoc-Val-OH (3.00 eq) | HATU (2.85 eq) and DIEA (3.00 eq) |
| 14 | Fmoc-Leu-OH (3.00 eq) | HATU (2.85 eq) and DIEA (3.00 eq) |
| 15 | Fmoc-Glu(OfBu)-OH (3.00 eq) | HATU (2.85 eq) and DIEA (3.00 eq) |

Peptide Cleavage and Cyclization:
1) Cleavage solution (20% HFIP/DCM, 20 mL) was added into the flask containing the side chain protected crude peptide (0.5 mmol). The mixture was stirred for 1 h at room temperature.
2) After filtration, the solution was collected.
3) Step 1-2 were repeated for another time.
4) The combined solution (containing 0.5 mmol crude peptide) was diluted with DCM (500 mL), then added HOBT (135 mg, 1.00 mmol, 2.00 eq), TBTU (321 mg, 1.00 mmol, 2.00 eq) and adjusted pH to 8 by DIEA. The mixture was stirred at 15° C. for 2 hrs.
5) The mixture was concentrated under reduced pressure to remove solvent.
6) The residue was added to 0.50 M HCl (cold, 50 mL) and white solid was precipitated. After filtered, the solid was dried under lyophilization to afford compound 2 (190.0 mg, crude) as a white solid. Chemical Formula: $C_{111}H_{145}N_{19}O_{20}$, LCMS found: $[M+2H]^{2+}=1033.62$;

Step 2: Preparation of (3)

A mixture of (2) (190.0 mg, crude, 1.00 eq), Grubbs' 1$^{st}$ (75.6 mg, 1.00 eq) in dry DCM (50 mL) was stirred under microwave at 60° C. for 4 hrs. Then the mixture was washed with 0.5 M HCl, $H_2O$, brine, dried over anhydrous $Na_2SO_4$, concentrated under reduced pressure to afford compound 3 (160.5 mg, crude) as a brown solid. Chemical Formula: $C_{109}H_{141}N_{19}O_{20}$, LCMS found: $[M+2H]^{2+}=1019.35$;

Step 2: Preparation of Intermediate 31

A mixture of (3) (160.0 mg, crude) in TFA/TIS/$H_2O$ (95/2.5/2.5, v/v/v, 5 mL) at 15° C. for 1 h. Then the mixture was precipitated with isopropyl ether (50 mL) and centrifuged (3 min at 3000 rpm). The solid was washed with isopropyl ether twice, dried under vacuum for 2 hrs. The residue was purified by prep-HPLC (TFA condition) to afford Intermediate 31 (42.7 mg, 95.2% purity, total yield 5.0%) as a white solid. Chemical Formula: $C_{82}H_{111}N_{19}O_{20}$, LCMS found: $[M+2H]^{2+}=1684.0$, $[M+2H]^{2+}=843.2$;

Preparation of A134: 3,3'-((2-(6-azidohexanamido)propane-1,3-diyl)bis(oxy))bis(N-(1-((3aR,4S,7S,8R,8aR)-2,2-dimethyl-8-(2,2,2-trifluoroacetamido)hexahydro-4,7-epoxy[1,3]dioxolo[4,5-d]oxepin-4-yl)-2,5,8,11-tetraoxatridecan-13-yl)propanamide)

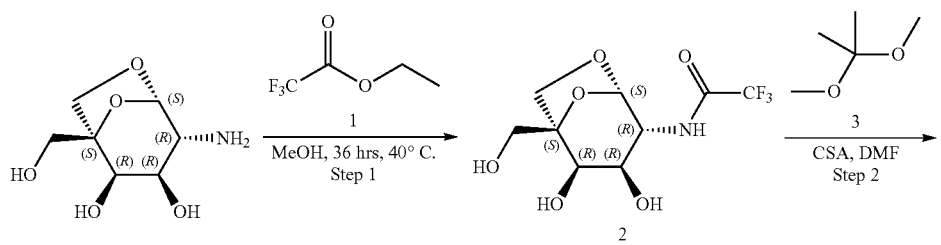

-continued
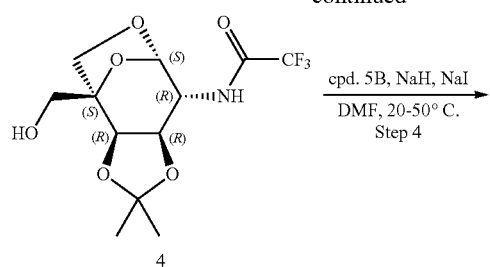
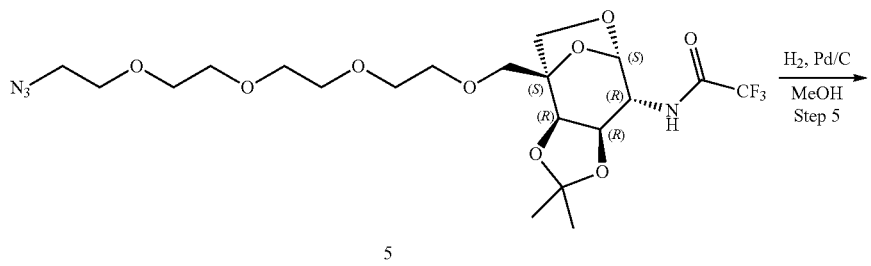
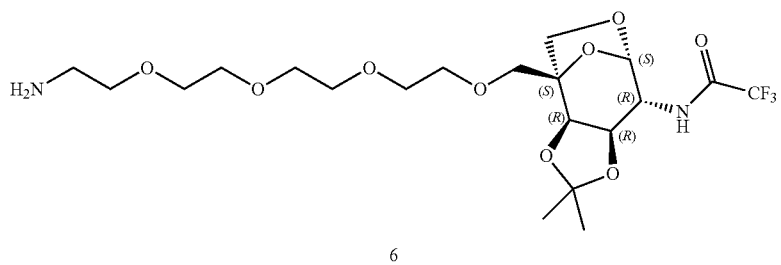
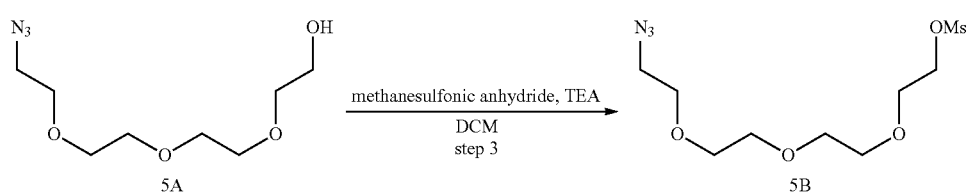
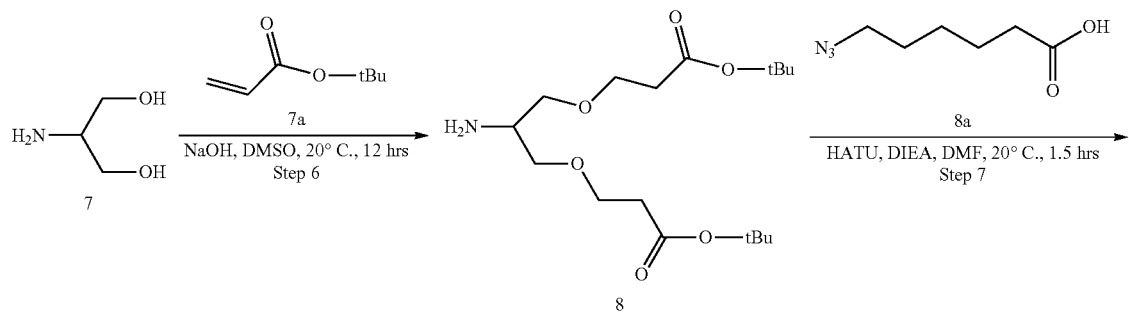
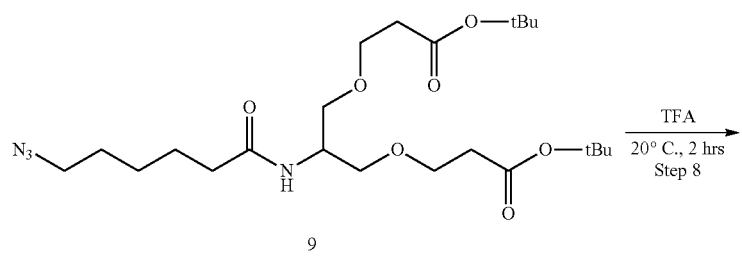

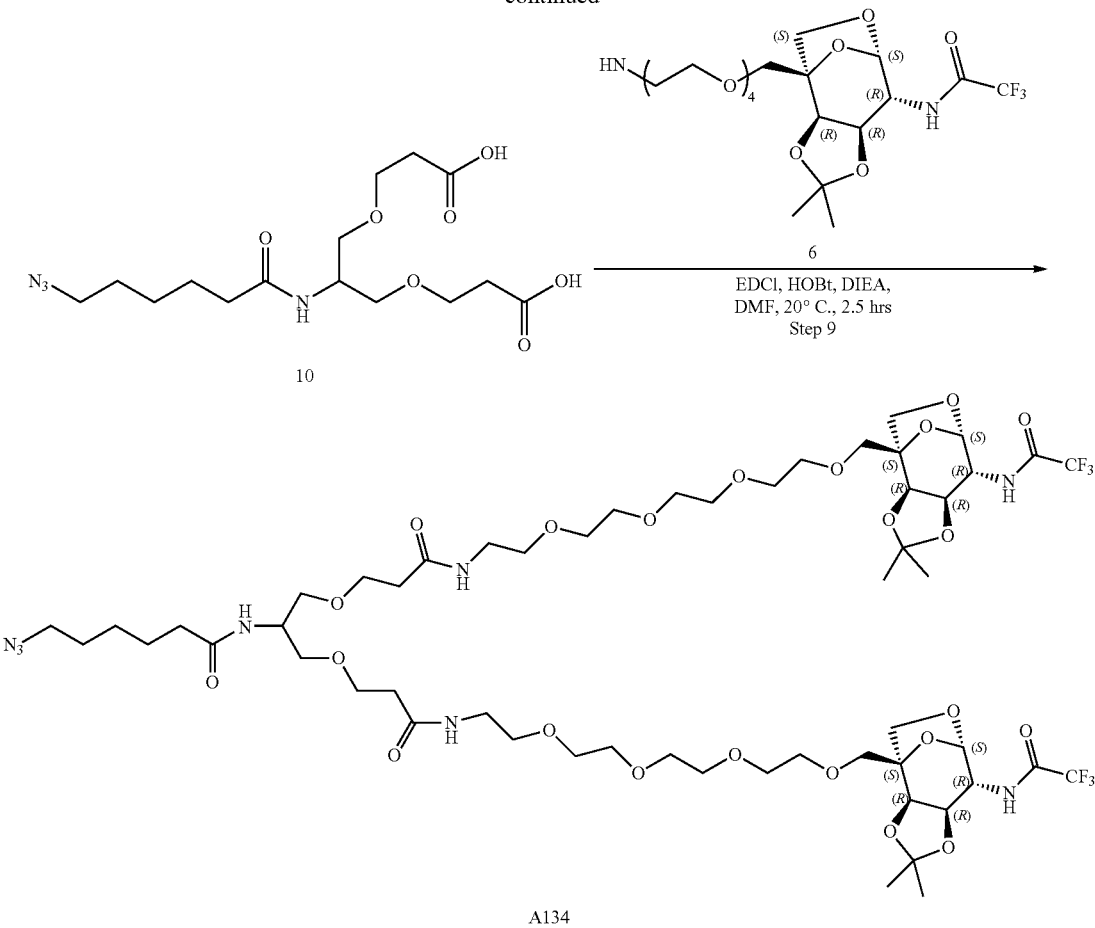

Step 1: Preparation of (2)

To a solution of (1S,2R,3R,4R,5S)-4-amino-1-(hydroxymethyl)-6,8-dioxabicyclo[3.2.1]octane-2,3-diol (5.00 g, 26.1 mmol, 1.00 eq) in MeOH (50.0 mL) was added compound 1 (48.30 g, 339 mmol, 46.9 mL, 13.00 eq). The mixture was stirred at 40° C. for 36 hrs. TLC (Dichloromethane/Methanol=7/1) indicated (1S,2R,3R,4R,5S)-4-amino-1-(hydroxymethyl)-6,8-dioxabicyclo[3.2.1]octane-2,3-diol (Rf=0) was not remaining, and one major new spot was detected (Rf=0.30). The reaction mixture was concentrated under reduced pressure to give a residue. The residue was purified by column chromatography (SiO2, Petroleum ether/Ethyl acetate=1/0 to 0/1, Dichloromethane/Methanol=7/1, Rf=0.30) directly to afford compound 2 (4.50 g, 15.6 mmol, 59.9% yield) as colorless oil. Chemical Formula: $C_9H_{12}F_3NO_6$. $^1$HNMR: 400 MHz, DMSO-$d_6$δ: 9.50 (d, J=7.2 Hz, 1H), 4.92-4.72 (m, 3H), 3.83-3.72 (m, 4H), 3.65-3.57 (m, 3H).

Step 2: Preparation of (4)

To a solution of compound 2 (4.50 g, 15.6 mmol, 1.00 eq) in DMF (45.0 mL) was added CSA (1.96 g, 7.83 mmol, 0.50 eq) and compound 3 (8.16 g, 78.35 mmol, 9.60 mL, 5.00 eq). The mixture was stirred at 80° C. for 12 hrs. LC-MS showed desired mass was detected ($R_t$=0.39 min). The reaction mixture concentrated under reduced pressure to give a residue. The residue was purified by column chromatography (SiO$_2$, Petroleum ether/Ethyl acetate=1/0 to 0/1, Dichloromethane:Methanol=7/1, $R_f$=0.66). The residue was purified by column chromatography (SiO$_2$, Petroleum ether/Ethyl acetate=1/0 to 0/1, Dichloromethane/Methanol=7/1, $R_f$=0.66) to afford compound 4 (4.50 g, 13.7 mmol, 87.7% yield) as yellow oil. Chemical Formula: $C_{12}H_{16}F_3NO_6$, LCMS found: [M+H]$^+$=328.0. $^1$H NMR: 400 MHz, DMSO-$d_6$δ: 9.72 (d, J=8.4 Hz, 1H), 5.26 (s, 1H), 5.16-5.13 (m, 1H), 4.41-4.38 (m, 1H), 4.32 (d, J=6.0 Hz, 1H), 3.81-3.66 (m, 5H), 1.40 (s, 3H), 1.28 (s, 3H).

Step 3: Preparation of (5B)

To a solution of compound 5A (5.00 g, 22.8 mmol, 1.00 eq) in DCM (50.0 mL) was added TEA (2.77 g, 27.3 mmol, 3.81 mL, 1.20 eq) and methylsulfonyl methanesulfonate (5.16 g, 29.6 mmol, 1.30 eq). The mixture was stirred at 25° C. for 12 hrs. TLC (Petroleum ether/Ethyl acetate=0/1) indicated compound 5A ($R_f$=0.20) was remained, and one major new spot was detected (Rf=0.50). The reaction mixture was quenched by addition H$_2$O (50.0 mL), and then extracted with DCM (30.0 mL*2). The combined organic layers were washed with brine (50.0 mL*3), dried over Na$_2$SO$_4$, filtered and concentrated under reduced pressure to give a residue. The residue was purified by column chromatography (SiO2, Petroleum ether/Ethyl acetate=100/1 to 0/1, Petroleum ether/Ethyl acetate=0/1, Rf=0.50) to afford compound 5B (4.80 g, 16.1 mmol, 70.7% yield) as colorless oil. Chemical Formula: $C_9H_{19}N_3O_6S$. $^1$H NMR: 400 MHz, CDCl$_3$ δ: 4.39-4.36 (m, 2H), 3.78-3.75 (m, 2H), 3.69-3.65 (m, 10H), 3.40-3.37 (m, 2H), 3.07 (s, 3H).

Step 4: Preparation of (5)

To a solution of compound 4 (2.00 g, 6.11 mmol, 1.00 eq) in DMF (20.0 mL) was added NaH (977 mg, 24.4 mmol, 60.0% purity, 4.00 eq). The mixture was stirred at 25° C. for 1.5 hrs. Then compound 5B (2.00 g, 6.72 mmol, 1.10 eq) and NaI (183 mg, 1.22 mmol, 0.200 eq) was added and the mixture was stirred at 60° C. for 14.5 hrs. LC-MS (EC492-348-P1A) showed desired compound was detected (Rt=0.64 min). The reaction mixture was quenched by addition saturated NH4Cl 25.0 mL, and then extracted with EtOAc (25.0 mL*3). The combined organic layers were washed with brine (20.0 mL*3), dried over Na2SO4, filtered and concentrated under reduced pressure to give a residue. The residue was purified by column chromatography (SiO2, Petroleum ether/Ethyl acetate=1/0 to 0/1, Petroleum ether/Ethyl acetate=3/1, Rf=0.50) to afford compound 5 (3.00 g, 5.68 mmol, 92.8% yield, 100% purity) as light yellow oil. Chemical Formula: $C_{20}H_{31}F_3N_4O_9$, LCMS found: [M+Na]$^+$= 551.1; $^1$H NMR: 400 MHz, CDCl$_3$ δ: 7.03 (s, 1H), 4.24 (d, J=6.0 Hz, 1H), 4.18-4.15 (m, 1H), 4.05 (d, J=1.6 Hz, 1H), 3.95 (d, J=10.0 Hz, 1H), 3.83-3.77 (m, 3H), 3.73-3.61 (m, 15H), 3.38-3.36 (m, 2H), 1.53 (s, 3H), 1.34 (s, 3H).

Step 5: Preparation of (6)

A mixture of compound 5 (2.50 g, 4.73 mmol, 1.00 eq), Pd/C (250 mg, 4.73 mmol, 10.0% purity, 1.00 eq) in MeOH (25.0 mL) was degassed and purged with H$_2$ for 3 times, and then the mixture was stirred at 25° C. for 2 hrs under H$_2$ (15.0 psi) atmosphere. LC-MS showed desired mass was detected (R$_t$=0.50 min). The reaction mixture was filtered and concentrated under reduced pressure to remove MeOH to afford compound 6 (1.60 g, 3.18 mmol, 67.3% yield) as colorless oil. Chemical Formula: $C_{20}H_{33}F_3N_2O_9$, LCMS found: [M+H]$^+$=503.1. $^1$H NMR: 400 MHz, CD$_3$OD δ: 8.52 (s, 1H), 5.29 (s, 1H), 4.92 (S, 1H), 4.37-4.30 (m, 2H), 3.95 (d, J=6.8 Hz, 1H), 3.88 (d, J=8.4 Hz, 3H), 3.81 (d, J=7.6 Hz, 1H), 3.74-3.61 (m, 15H), 3.13-3.11 (m, 2H), 1.49 (s, 3H), 1.34 (s, 3H).

Step 6: Preparation of (8)

A mixture of compound 7 (3.87 g, 42.4 mmol, 1.00 eq), compound 7a (15.7 g, 123 mmol, 17.8 mL, 2.90 eq), NaOH (5.00 M, 849 uL, 0.100 eq) in DMSO (40.0 mL) was stirred at 20° C. for 12 hrs. TLC (Dichloromethane/Methanol=10/1) showed compound 7 (R$_f$=0.050) was consumed completely and one major new spot (R$_f$=0.600) formed. The mixture was washed with H$_2$O (2.50 mL) and extracted with EtOAc (10.0 mL*3). The combined organic layers were washed with brine (10.0 mL*3), dried over Na$_2$SO$_4$, filtered and concentrated under reduced pressure to give a residue. The residue was purified by column chromatography (SiO$_2$, Dichloromethane/Methanol=1/0 to 10/1, Dichloromethane/Methanol=10/1, R$_f$=0.600) to afford compound 8 (14.7 g, crude) as a yellow solid.

Step 7: Preparation of (9)

To a solution of compound 8a (1.00 g, 6.36 mmol, 1.00 eq) in DMF (10.0 mL) was added HATU (5.44 g, 14.3 mmol, 2.25 eq). The mixture was stirred at 20° C. for 0.5 hr. DIEA (3.29 g, 25.4 mmol, 4.43 mL, 4.00 eq) and compound 8 (2.65 g, 7.64 mmol, 1.20 eq) was added. The mixture was stirred at 20° C. for 1 hr. LCMS showed compound 8a was consumed completely and desired mass (R$_t$=0.66 min) was detected. The reaction mixture was washed with 1 M HCl (10.0 M1) and extracted with EtOAc (10.0 mL*3). The combined organic layers were washed with H$_2$O (10.0 mL*3), brine (10.0 mL*3), dried over Na$_2$SO$_4$, filtered and concentrated under reduced pressure to give a residue. The residue was purified by column chromatography (SiO$_2$, Petroleum ether/Ethyl acetate=1/0 to 1/1, Petroleum ether/Ethyl acetate=1/1, R$_f$=0.350) to afford compound 9 (2.58 g, 5.30 mmol, 83.3% yield) as yellow oil. Chemical Formula: $C_{23}H_{42}N_4O_7$, LCMS found: [M+H]$^+$=487.2. $^1$H NMR: 400 MHz, CDCl$_3$ δ: 6.27 (d, J=8.0 Hz, 1H), 4.19-4.14 (m, 1H), 3.73-3.63 (m, 4H), 3.61-3.57 (m, 2H), 3.42-3.38 (m, 2H), 3.29-3.25 (t, J=8.0 Hz, 2H), 2.53-2.41 (m, 4H), 2.22-2.19 (t, J=8.0 Hz, 2H), 1.71-1.58 (m, 5H), 1.46 (s, 18H)

Step 8: Preparation of (10)

To a solution of compound 9 (2.00 g, 4.11 mmol, 1.00 eq) was added TFA (15.48 g, 135 mmol, 10.0 mL, 33.0 eq). The mixture was stirred at 20° C. for 2 hrs. LCMS showed compound 8 was consumed completely and desired mass (R$_t$=0.50 min). The mixture was concentrated under reduced pressure to remove TFA to give a residue. The residue was purified by prep-HPLC (FA condition) to afford compound 10 (84.0 mg, 220 umol, 5.36% yield, 98.2% purity) as yellow oil. Chemical Formula: $C_{15}H_{26}N_4O_7$, LCMS found: [M+H]$^+$=375.1. $^1$H NMR: 400 MHz, CDCl$_3$ δ: 6.16 (d, J=8.0 Hz, 1H), 4.22-4.20 (m, 1H), 3.75-3.73 (m, 4H), 3.61-3.58 (m, 2H), 3.48-3.44 (m, 2H), 3.30-3.27 (t, J=12.0 Hz, 2H), 2.61-2.58 (m, 4H), 2.23-2.19 (t, J=16.0 Hz, 2H), 1.70-1.59 (m, 4H), 1.46-1.37 (m, 2H)

Step 9: Preparation of A134

To a solution of compound 10 (81.0 mg, 212 umol, 98.2% purity, 1.00 eq) in DMF (1.00 mL) was added HATU (181 mg, 478 umol, 2.25 eq). The mixture was stirred at 20° C. for 0.5 hr. DIEA (109 mg, 849 umol, 148 uL, 4.00 eq) and compound 6 (241.0 mg, 478 umol, 99.3% purity, 2.25 eq) was added. The mixture was stirred at 20° C. for 2 hrs. LCMS showed compound 10 was consumed completely and found one main peak with desired mass. The reaction mixture was quenched by addition FA (0.500 mL). The reaction mixture was purified by prep-HPLC (FA condition) to afford A134 (129.0 mg, 98.0% purity, 44.3% yield) as brown oil. Chemical Formula: $C_{55}H_{88}F_6N_8O_{23}$, LCMS found: [M+H]$^+$=1343.9.

Preparation of Compound 94: 3-((6S,9R,12S,15S, 18S,21S,27S,30S,33S,36S,39R,42S,44aS,46S, 49aR)-30-((1H-imidazol-5-yl)methyl)-12,33-bis ((1H-indol-3-yl)methyl)-42-(carboxymethyl)-46-(20-(1-(20-(1-((1S,2R,3R,4R,5S)-2,3-dihydroxy-4-(2,2,2-trifluoroacetamido)-6,8-dioxabicyclo[3.2.1]octan-1-yl)-15-oxo-2,5,8,11,18-pentaoxa-14-azanonadecan-19-yl)-1-((1S,2R,3R,4R,5S)-2,3-dihydroxy-4-(2,2,2-trifluoroacetamido)-6,8-dioxabicyclo[3.2.1]octan-1-yl)-15,22-dioxo-2,5,8,11, 18-pentaoxa-14,21-diazaheptacosan-27-yl)-1H-1,2,3-triazol-4-yl)-17-oxo-4,7,10,13-tetraoxa-16-azai-cosanamido)-6-((R)-1-hydroxyethyl)-18,27-di-isobutyl-15-isopropyl-36-methyl-5,8,11,14,17,20,23, 26,29,32,35,38,41,44,49-pentadecaoxooctatetracontahydro-1H-9,39-(methanodithiomethano) dipyrrolo[1,2-a:1',2'-d][1,4,7,10,13,16,19,22,25,28,31,34,37,40,43] pentadecaazacyclo pentatetracontin-21-yl)propanoic acid

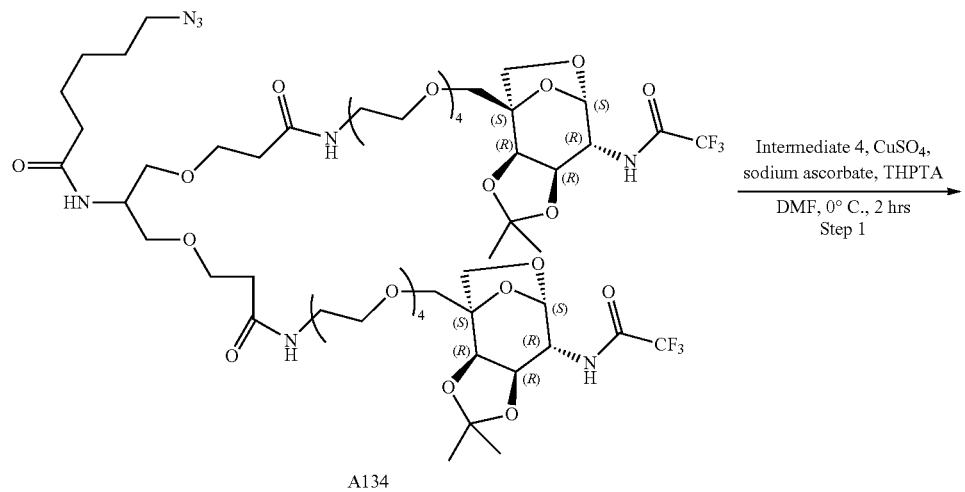

A134

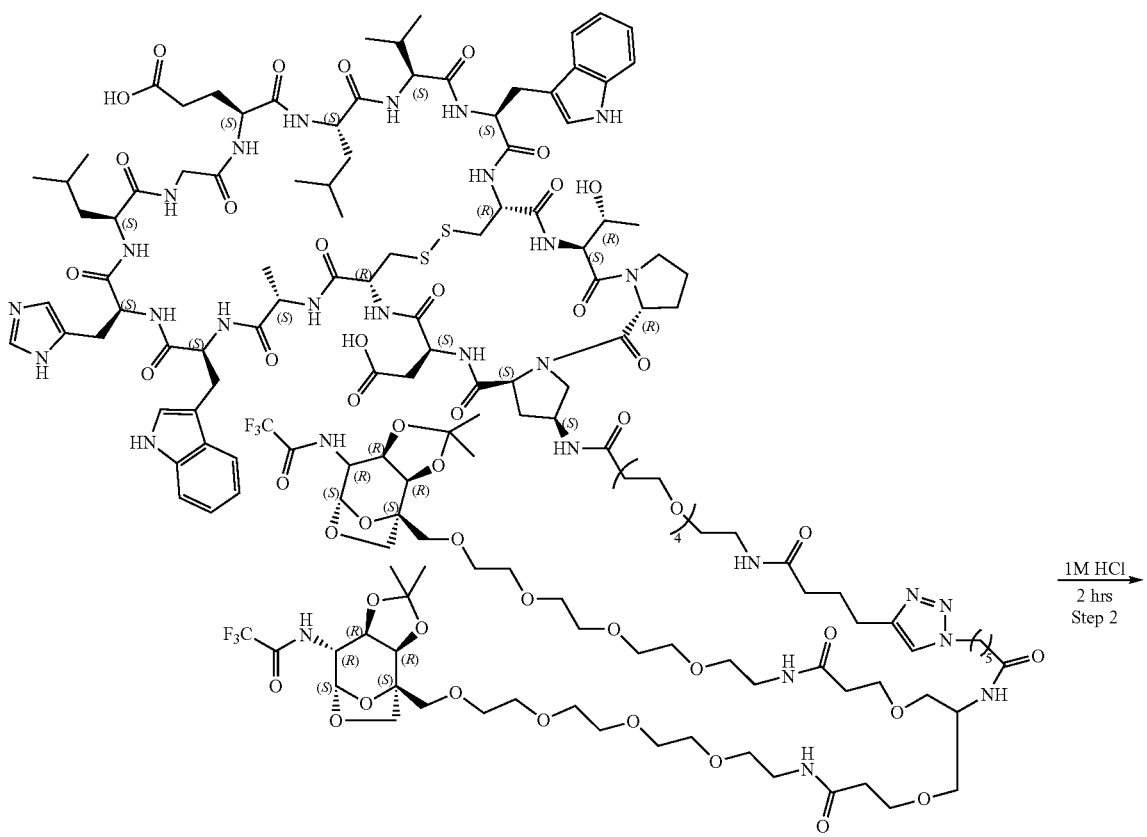

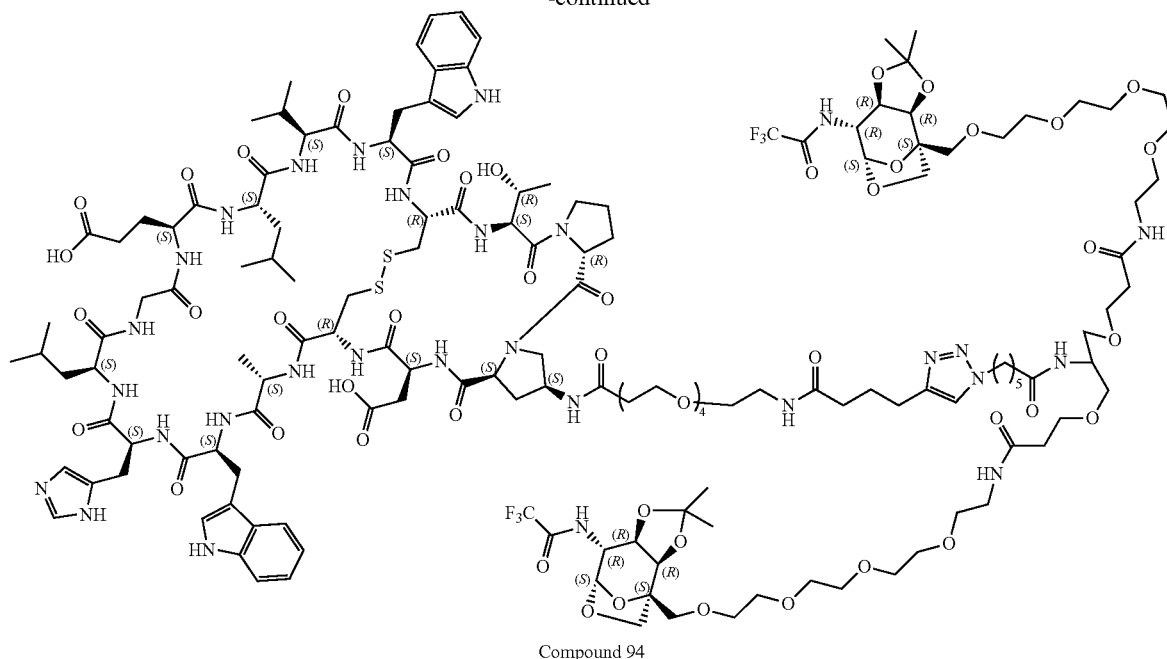

Compound 94

Step 1: Preparation of Compound 11

To a solution of Intermediate 4 (20.0 mg, 9.69 umol, 1.00 eq), A134 (13.2 mg, 9.69 umol, 98.0% purity, 1.00 eq) in DMF (0.50 mL) was added a fresh solution of $CuSO_4$ (0.40 M, 24.2 uL, 1.00 eq), sodium ascorbate (0.40 M, 96.9 uL, 4.00 eq) and THPTA (4.21 mg, 9.69 umol, 1.00 eq) under $N_2$ at 0° C. The mixture was stirred at 0° C. for 2 hrs. LCMS showed one main peak was desired mass. The reaction mixture was purified by prep-HPLC (HCl condition) directly to afford compound 11 (26.0 mg, crude) as a white solid. Chemical Formula: $C_{151}H_{223}F_6N_{29}O_{49}S_2$, LCMS found: $[M+3H]^{3+}=1136.3$.

Step 2: Preparation of Compound 94

A solution of compound 11 (20.0 mg, 5.87 umol, 1.00 eq) in HCl (1 M, 2.00 mL, 340.67 eq) was stirred at 20° C. for 2 hrs. LCMS showed compound 11 was consumed completely and found one main peak with desired mass. The reaction mixture was purified by prep-HPLC (HCl condition) to afford Compound 94 (10.0 mg, 2.93 umol, 97.4% purity, 49.8% yield) as brown oil. Chemical Formula: $C_{145}H_{215}F_6N_{29}O_{49}S_2$, LCMS found: $[M+3H]^{3+}=1109.6$. $^1H$ NMR: 400 MHz, MeOD δ: 8.21-8.20 (m, 1H), 7.74 (s, 1H), 7.49-6.89 (m, 10H), 5.29-5.25 (m, 2H), 4.66-4.55 (m, 3H), 4.50-4.41 (m, 2H), 4.40-4.32 (m, 3H), 4.26-4.19 (m, 2H), 4.14-3.97 (m, 8H), 3.92-3.88 (m, 4H), 3.81-3.79 (m, 3H), 3.77-3.58 (m, 52H), 3.55-3.51 (m, 7H), 3.48-3.42 (m, 5H), 3.38-3.34 (m, 11H), 3.27-3.12 (m, 4H), 3.04-2.83 (m, 4H), 2.75-2.69 (m, 2H), 2.60-2.38 (m, 11H), 2.35-2.18 (m, 7H), 2.15-2.06 (m, 2H), 2.05-1.55 (m, 16H), 1.35-1.16 (m, 8H), 1.06-0.79 (m, 18H)

Preparation of A136: 3,3'-((2-(6-azidohexanamido)-2-(1-((3aR,4S,7S,8R,8aR)-2,2-dimethyl-8-(2,2,2-trifluoroacetamido)hexahydro-4,7-epoxy[1,3]dioxolo[4,5-d]oxepin-4-yl)-15-oxo-2,5,8,11,18-pentaoxa-14-azanonadecan-19-yl)propane-1,3-diyl)bis(oxy))bis(N-(1-((3aR,4S,7S,8R,8aR)-2,2-dimethyl-8-(2,2,2-trifluoroacetamido)hexahydro-4,7-epoxy[1,3]dioxolo[4,5-d]oxepin-4-yl)-2,5,8,11-tetraoxatridecan-13-yl)propanamide)

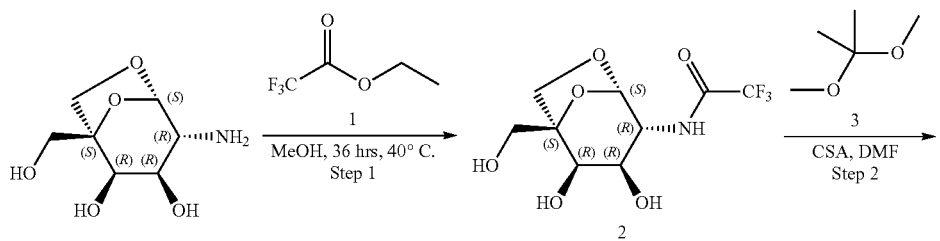

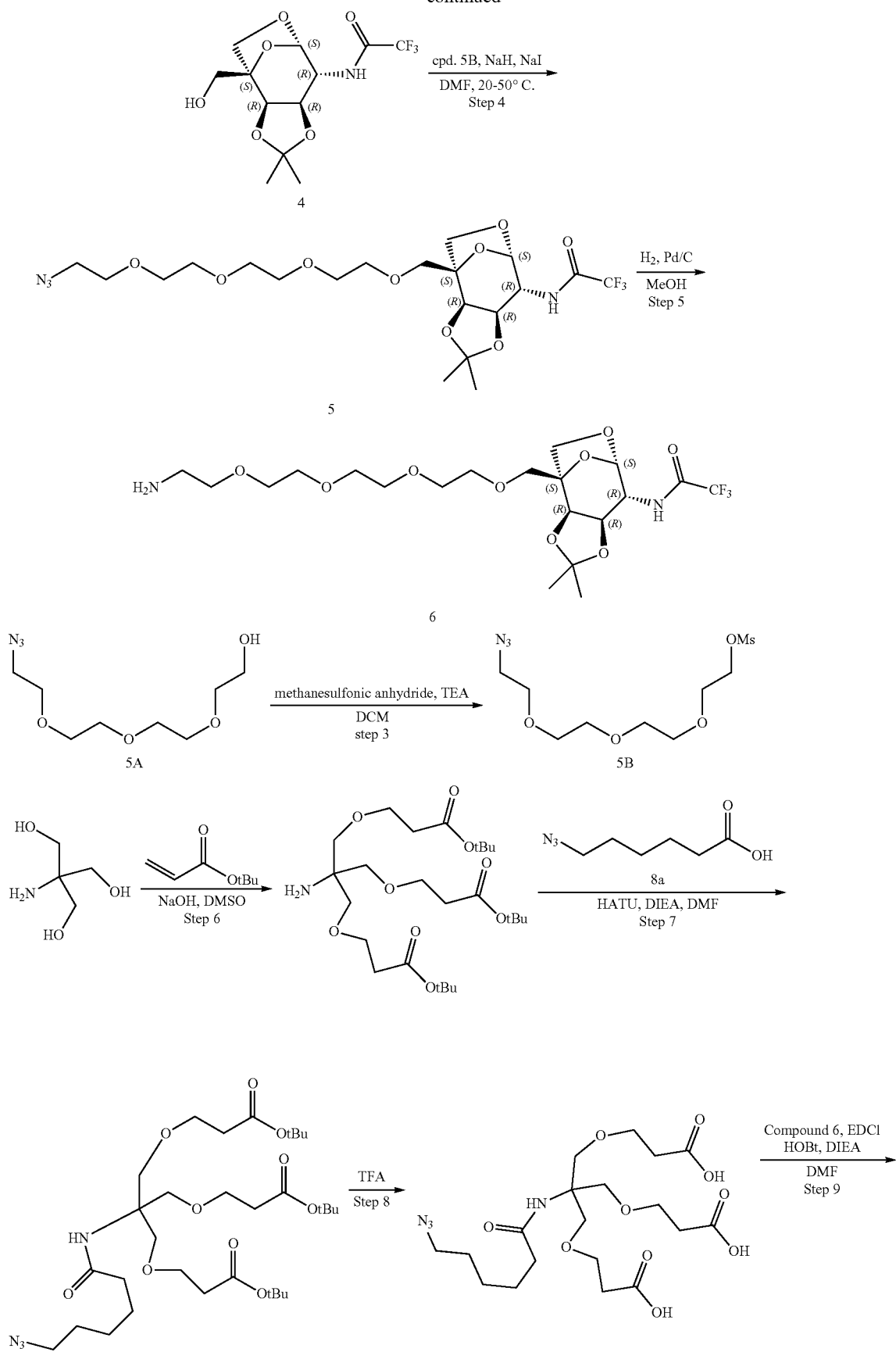

-continued

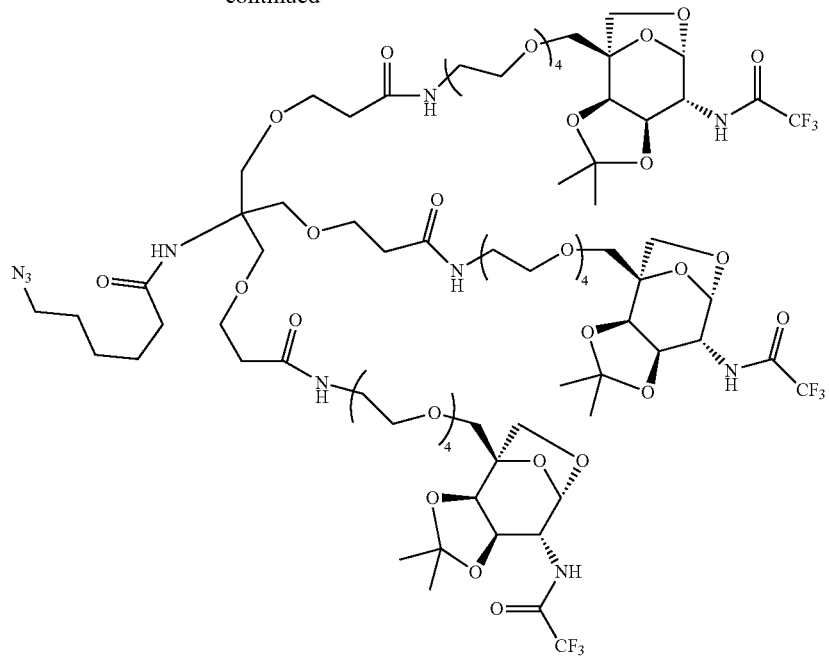

Step 6: Preparation of Compound 8

A mixture of compound 7 (10.0 g, 82.5 mmol, 11.9 mL, 1.00 eq), compound 7a (47.6 g, 371 mmol, 53.9 mL, 4.50 eq) and NaOH (5 M, 1.65 mL, 0.100 eq) in DMSO (25.0 mL) was stirred at 20° C. for 16 hrs. LCMS showed desired mass was detected ($R_f$=0.524 min). The reaction mixture was quenched by addition $H_2O$ (30.0 mL), then extracted with EtOAc (30.0 mL*3). The combined organic layers were washed with brine (30.0 mL*3), dried over $Na_2SO_4$, filtered and concentrated under reduced pressure to give a residue. The residue was purified by column chromatography (SiO2, Petroleum ether/Ethyl acetate=100/1 to 0/1, Dichloromethane/Methanol=10/1, Rf=0.30) to afford compound 8 (22.0 g, 43.5 mmol, 52.7% yield) as colorless oil. Chemical Formula: $C_{25}H_{47}NO_9$, LCMS found: $[M+H]^+$=506.2. $^1$H NMR: 400 MHz, DMSO-$d_6$δ: 3.58-3.53 (m, 6H), 3.17 (s, 6H), 2.40-2.37 (s, 6H), 1.39 (s, 27H).

Step 7: Preparation of Compound 9

To a solution of compound 8a (300.0 mg, 1.91 mmol, 1.00 eq) in DCM (10.0 mL) was added HATU (2.25 g, 5.92 mmol, 3.10 eq) and stirred at 20° C. for 0.5 hr. Then DIEA (1.23 g, 9.54 mmol, 1.66 mL, 5.00 eq) and compound 8 (1.16 g, 2.29 mmol, 1.20 eq) was added. The mixture was stirred at 20° C. for 1.5 hrs. LCMS showed one main peak was desired compound. The reaction mixture was quenched by addition 1 N HCl (10.0 mL), then extracted with EtOAc (10.0 mL*3). The combined organic layers were washed with brine (10 mL*2), dried over $Na_2SO_4$, filtered and concentrated under reduced pressure to give a residue. The residue was purified by column chromatography (SiO2, Petroleum ether/Ethyl acetate=1/0 to 0/1, Petroleum ether/Ethyl acetate=3/1, $R_f$=0.65) afford compound 9 (960.0 mg, 99.7% purity, 76.1% yield) as colorless oil. Chemical Formula: $C_{31}H_{56}N_4O_{10}$, LCMS found: $[M+H]^+$=645.3

Step 8: Preparation of Compound 10

A solution of compound 9 (960.0 mg, 1.48 mmol, 99.7% purity) in DCM (10.0 mL) and TFA (68.3 mg, 1.48 mmol, 56.0 uL, 1.00 eq) was stirred at 20° C. for 12 hrs. LCMS showed one main peak was desired mass. The reaction mixture was concentrated under reduced pressure to give a residue. The residue was purified by prep-HPLC (FA condition) and lyophilized to afford compound 10 (281.0 mg, 98.7% purity, 39.2% yield) as colorless oil. Chemical Formula: $C_{19}H_{32}N_4O_{10}$, LCMS found: $[M+H]^+$=477.1. $^1$H NMR: 400 MHz, DMSO-$d_6$δ: 6.94 (s, 1H), 3.57-3.53 (m, 12H), 3.31-3.28 (m, 2H), 2.43-2.40 (m, 6H), 2.07-2.03 (m, 2H), 1.55-1.42 (m, 4H), 1.31-1.23 (m, 2H).

Step 9: Preparation of A136

To a solution of compound 10 (190 mg, 398 umol, 1.00 eq) in DCM (10.0 mL) was added DIEA (257 mg, 1.99 mmol, 347 uL, 5.00 eq) and stirred at 20° C. for 10 min, then HATU (470 mg, 1.24 mmol, 3.10 eq) and compound 6 (651 mg, 1.30 mmol, 3.25 eq) was added. The mixture was stirred at 20° C. for 2 hrs. LCMS showed desired mass was detected (Rt=0.64 min). The reaction mixture was quenched by addition 1 M HCl (5.00 mL), then extracted with DCM (5.00 mL*3). The combined organic layers were washed with brine (5.00 mL*3), dried over $Na_2SO_4$, filtered and concentrated under reduced pressure to give a residue. The residue was purified by prep-HPLC (FA condition) to afford compound A136 (122.0 mg, 97.2% purity, 15.41% yield) as brown oil. Chemical Formula: $C_{79}H_{125}F_9N_{10}O_{34}$, LCMS found: $[M+H]^+$=1930.4. $^1$H NMR: 400 MHz, DMSO-$d_6$δ: 9.72 (s, 2H), 7.91-7.88 (m, 3H), 7.00 (s, 1H), 4.41-4.38 (m, 3H), 4.31 (d, J=5.6 Hz, 3H), 3.84-3.66 (m, 14H), 3.64-3.51 (m, 44H), 3.42-3.37 (m, 6H), 3.29-3.28 (m, 4H), 3.24-3.17 (m, 5H), 2.34-2.28 (m, 5H), 2.09-2.05 (m, 2H), 1.55-1.43 (m, 4H), 3.64-3.51 (m, 44H), 1.40 (s, 9H), 1.28 (s, 9H).

Preparation of Compound 95: 3-((6S,9R,12S,15S, 18S,21S,27S,30S,33S,36S,39R,42S,44aS, 46S, 49aR)-30-((1H-imidazol-5-yl)methyl)-12,33-bis ((1H-indol-3-yl)methyl)-46-(20-(1-(20,20-bis(1-((1S,2R,3R,4R,5S)-2,3-dihydroxy-4-(2,2,2-trifluoroacetamido)-6,8-dioxabicyclo[3.2.1]octan-1-yl)-15-oxo-2,5,8,11,18-pentaoxa-14-azanonadecan-19-yl)-1-((1S,2R,3R,4R,5S)-2,3-dihydroxy-4-(2,2,2-trifluoroacetamido)-6,8-dioxabicyclo[3.2.1]octan-1-yl)-15,22-dioxo-2,5,8,11,18-pentaoxa-14,21-diazahexacosan-26-yl)-1H-1,2,3-triazol-4-yl)-17-oxo-4,7,10,13-tetraoxa-16-azaicosanamido)-42-(carboxymethyl)-6-((R)-1-hydroxyethyl)-18,27-diisobutyl-15-isopropyl-36-methyl-5,8,11,14,17,20,23, 26,29,32,35,38,41,44,49-pentadecaoxooctatetracontahydro-1H-9,39-(methanodithiomethano)dipyrrolo[1,2-a:1',2'-d][1,4, 7,10,13,16,19,22,25,28,31,34,37,40,43] pentadecaazacyclopentatetracontin-21-yl)propanoic acidg

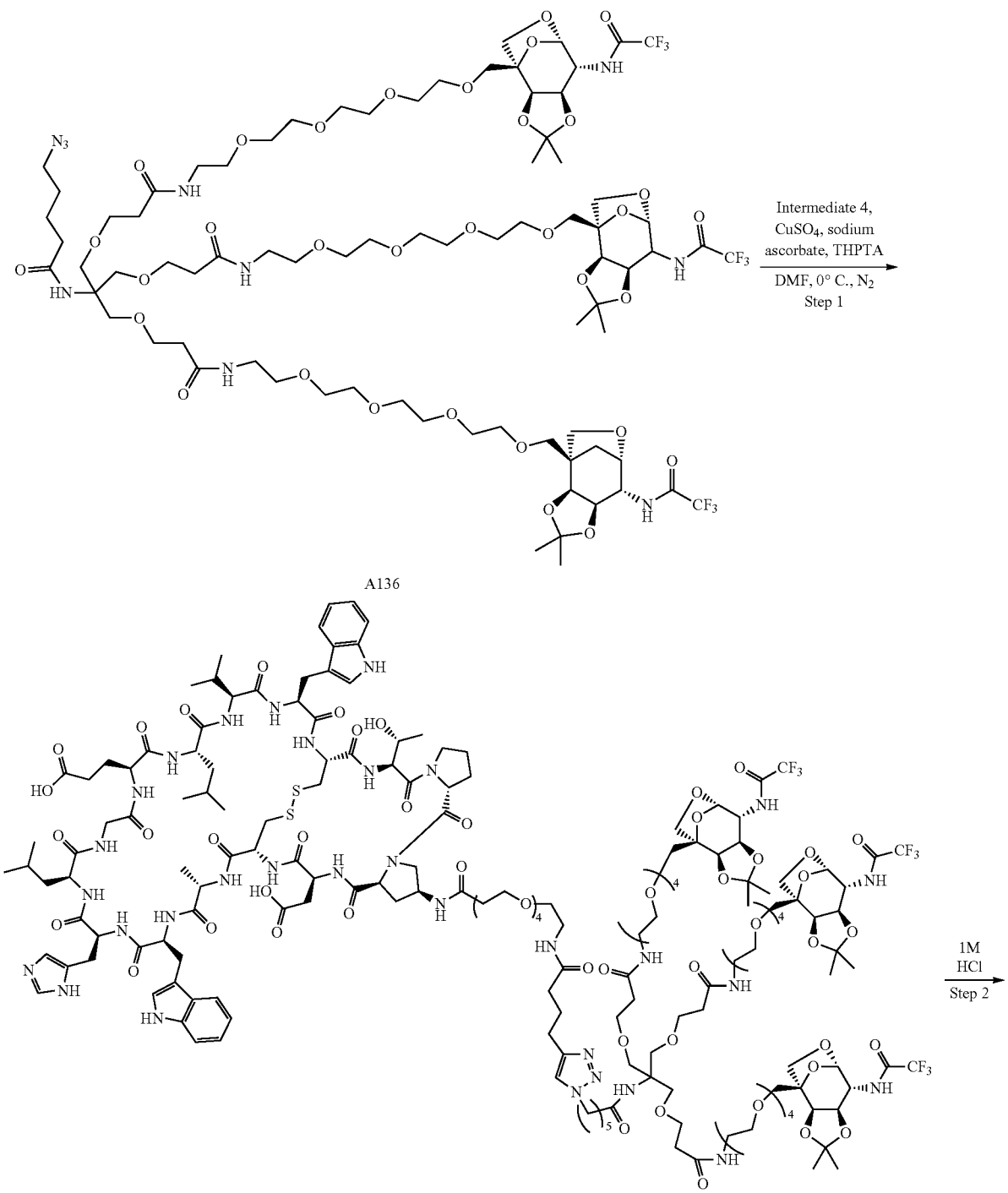

Compound 95

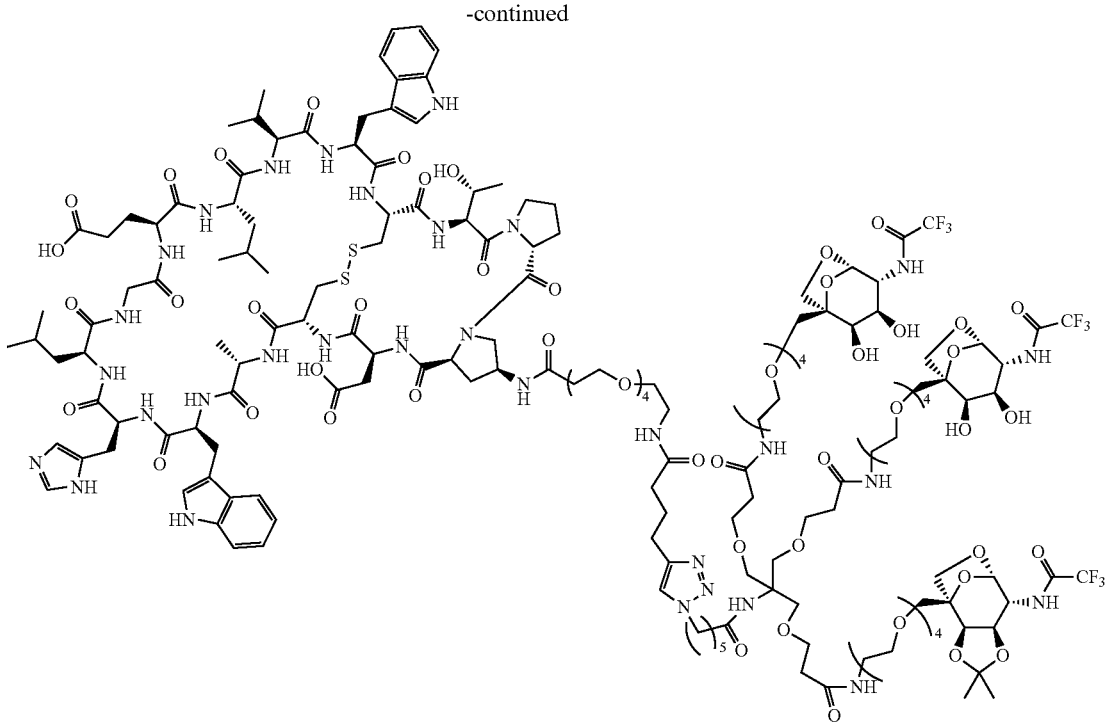

Compound 95

Step 1: Preparation of Compound 11

To a solution of compound Intermediate 4 (20.0 mg, 9.69 umol, 1.00 eq), A136 (19.25 mg, 9.69 umol, 1.00 eq) in DMF (0.50 mL) was added $CuSO_4$ (0.4 M, 24.2 uL, 1.00 eq), sodium ascorbate (0.4 M, 96.9 uL, 4.00 eq) and THPTA (4.21 mg, 9.69 umol, 1.00 eq) under $N_2$ at 0° C. The mixture was stirred at 0° C. for 2 hrs. LCMS showed one main peak was desired mass. The reaction mixture was purified by prep-HPLC to afford compound 11 (13.0 mg, 2.63 umol, 80.8% purity, 27.1% yield) as a white solid. Chemical Formula: $C_{175}H_{260}F_9N_{31}O_{60}S_2$, LCMS found: $[M+3H]^{3+}=$ 1331.6.

Step 2: Preparation of Compound 95

A solution of compound 11 (11.0 mg, 2.23 umol, 80.8% purity, 1.00 eq) in HCl (1 M, 0.2 mL) was stirred at 20° C. for 2 hrs. LCMS showed one main peak was desired mass. The reaction mixture was purified by prep-HPLC (FA condition) to afford Compound 95 (7.00 mg, 94.7% purity, 81.2% yield) as brown oil. Chemical Formula: $C_{166}H_{248}F_9N_{31}O_{60}S_2$, LCMS found: $[M+3H]^{3+}=1291.6$.

Preparation of Compound 96: 3-((6S,9R,12S,15S, 18S,21S,27S,30S,33S,36S,39R,42S,44aS,46S, 49aR)-30-((1H-imidazol-5-yl)methyl)-12,33-bis ((1H-indol-3-yl)methyl)-42-(carboxymethyl)-46-(4- (1-(((1S,2R,3R,4R,5S)-2,3-dihydroxy-4-(2,2,2- trifluoroacetamido)-6,8-dioxabicyclo[3.2.1]octan-1- yl)methyl)-1H-1,2,3-triazol-4-yl)butanamido)-6- ((R)-1-hydroxyethyl)-18,27-diisobutyl-15-isopropyl- 36-methyl-5,8,11,14,17,20,23,26,29,32,35,38,41,44, 49-pentadecaoxooctatetracontahydro-1H-9,39- (methanodithiomethano) dipyrrolo[1,2-a:1',2'-d][1,4, 7,10,13,16,19,22,25,28,31,34,37,40,43] pentadecaazacyclo pentatetracontin-21-yl)propanoic acid

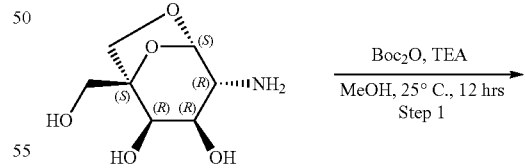

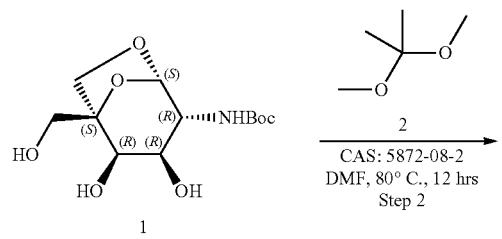

1297

-continued

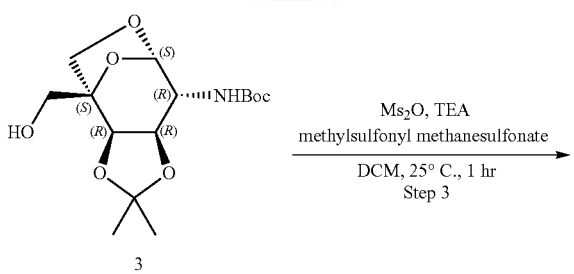

3

Ms₂O, TEA
methylsulfonyl methanesulfonate
―――――――――――――――――→
DCM, 25° C., 1 hr
Step 3

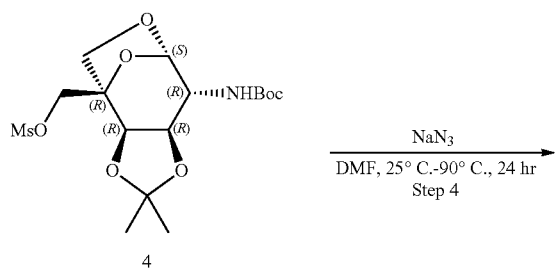

4

NaN₃
―――――――――――――――→
DMF, 25° C.-90° C., 24 hr
Step 4

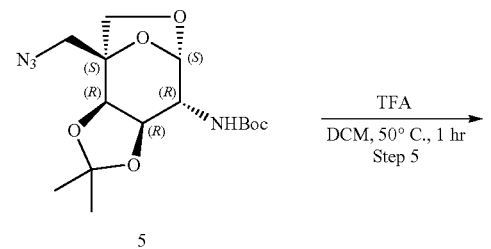

5

TFA
――――――――→
DCM, 50° C., 1 hr
Step 5

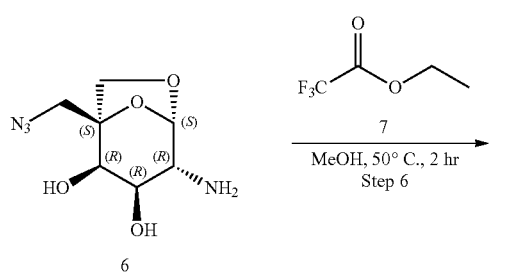

6

7

―――――――――→
MeOH, 50° C., 2 hr
Step 6

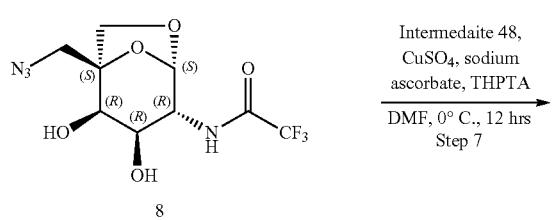

8

Intermedaite 48,
CuSO₄, sodium
ascorbate, THPTA
―――――――――――――→
DMF, 0° C., 12 hrs
Step 7

1298

-continued

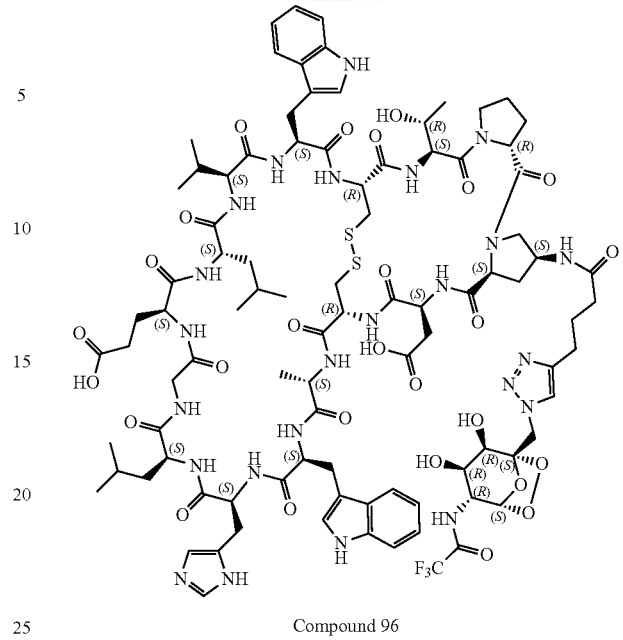

Compound 96

Step 1: Preparation of Compound 1

To a solution of (1S,2R,3R,4R,5S)-4-amino-1-(hydroxymethyl)-6,8-dioxabicyclo[3.2.1]octane-2,3-diol (500.0 mg, 1.64 mmol, 1.00 eq) in MeOH (5.00 mL) was added TEA (497 mg, 4.91 mmol, 684 uL, 3.00 eq) and (Boc)₂O (536 mg, 2.46 mmol, 564 uL, 1.50 eq). The mixture was stirred at 20° C. for 12 hrs. LC-MS showed (1S,2R,3R,4R,5S)-4-amino-1-(hydroxymethyl)-6,8-dioxabicyclo[3.2.1]octane-2,3-diol was consumed and one main peak was desired mass. The crude product was purified by prep-HPLC (TFA condition) to afford compound 1 (300.0 mg, crude) as a white solid. Chemical Formula: $C_{12}H_{21}NO_7$, LCMS found: [M+Na]⁺=314.0. ¹H NMR: 400 MHz, DMSO-d₆δ: 6.73 (d, J=7.6 Hz, 1H), 5.07 (s, 1H), 4.87 (s, 1H), 4.65 (s, 1H), 4.48 (s, 1H), 3.75-3.72 (m, 1H), 3.65 (s, 1H), 3.58-3.49 (m, 4H), 3.40-3.37 (m, 1H), 1.38 (s, 9H).

Step 2: Preparation of Compound 3

To a solution of compound 1 (300.0 mg, 1.03 mmol, 1.00 eq) and compound 2 (536.0 mg, 5.15 mmol, 630 uL, 5.00 eq) in DMF (3.00 mL) was added CAS: 5872-08-2 (128.0 mg, 514.0 umol, 0.50 eq). The mixture was stirred at 80° C. for 12 hrs. LC-MS showed compound 1 was consumed and desired mass (R_t=0.54 min) was detected. The crude product was purified by prep-HPLC (TFA condition) to afford compound 3 (300.0 mg, 87.91% yield) as a yellow solid. Chemical Formula: $C_{15}H_{25}NO_7$, LCMS found: [M+Na]⁺= 354.1. ¹H NMR: 400 MHz, DMSO-d₆δ: 7.08 (d, J=8.0 Hz, 1H), 5.14 (s, 1H), 5.06 (t, J=5.6 Hz, 1H), 4.21-4.20 (m, 1H), 4.13 (t, J=5.6 Hz, 1H), 3.74-3.61 (m, 4H), 3.37 (t, J=5.6 Hz, 1H), 1.38 (s, 12H), 1.26 (s, 3H).

Step 3: Preparation of Compound 4

To a solution of compound 3 (200.0 mg, 603.0 umol, 1.00 eq) in DCM (0.50 mL) was added TEA (79.4 mg, 784 umol, 109 uL, 1.30 eq) and methylsulfonyl methanesulfonate (126.0 mg, 724.0 umol, 1.20 eq). The mixture was stirred at 20° C. for 1 hr. LC-MS showed compound 3 was consumed and desired mass was detected. The mixture was poured to H$_2$O (2.0 mL). The aqueous mixture was extracted with DCM (10.00 mL*3), the combined organic layers were washed with brine (3.00 mL*3), dried over Na$_2$SO$_4$, filtered and concentrated under reduced pressure to give a residue. The residue was purified by prep-TLC (SiO$_2$, DCM:MeOH=10: 1, R$_f$=0.40) to afford compound 4 (140 mg, crude) as a white solid. Chemical Formula: C$_{16}$H$_{27}$NO$_9$S, LCMS found: [M+Na]$^+$=432.0. $^1$H NMR: 400 MHz, CDCl$_3$ δ: 5.40 (s, 1H), 4.75-4.77 (m, 1H), 4.61-4.53 (m, 2H), 4.15 (d, J=6.4 Hz, 1H), 4.04 (t, J=6.4 Hz, 1H), 3.86-3.84 (m, 1H), 3.79-3.77 (m, 1H), 3.09 (s, 3H), 1.56 (s, 3H), 1.45 (s, 9H), 1.36 (s, 3H).

Step 4: Preparation of Compound 5

To a solution of compound 4 (140 mg, 341 umol, Crude purity, 1.00 eq) in DMF (1.40 mL) was added NaN$_3$ (70.0 mg, 1.08 mmol, 3.15 eq) at 20° C. under N$_2$. The mixture was stirred at 90° C. for 24 hrs under N$_2$. LC-MS showed compound 4 was remained and desired mass was detected. The mixture was cooled to 20° C. and poured to saturation Na$_2$CO$_3$ (2.00 mL). The aqueous mixture was extracted with EtOAc (10.00 mL*3), the combined organic layers were washed with saturation Na$_2$CO$_3$ (2.00 mL*5), brine (3.00 mL*3), dried over Na$_2$SO$_4$, filtered and concentrated under reduced pressure to give a residue. The crude product was purified by prep-HPLC (FA condition) to afford compound 5 (60.0 mg, crude) as a white solid. Chemical Formula: C$_{15}$H$_{24}$N$_4$O$_6$, LCMS found: [M+Na]$^+$=379.1. $^1$H NMR: EC6537-20-P1B, 400 MHz, CDCl$_3$ δ: 5.37 (s, 1H), 4.79-4.77 (m, 1H), 4.12-4.10 (d, J=6.0 Hz, 1H), 4.00 (t, J=6.0 Hz, 1H), 3.77-3.67 (m, 5H), 1.55 (s, 3H), 1.43 (s, 9H), 1.35 (s, 3H).

Step 5: Preparation of Compound 6

A solution of compound 5 (30.0 mg, 84.1 umol, 1.00 eq) in DCM (0.01 mL) and TFA (1.50 mL) was stirred at 50° C. for 1 hr. LC-MS showed desired mass was detected. The mixture was concentrated under reduced pressure to give a residue. The crude product was purified by prep-HPLC (FA condition) to afford compound 6 (16.0 mg, crude) as a white solid. Chemical Formula: C$_7$H$_{12}$N$_4$O$_4$, LCMS found: [M+Na]$^+$=217.1. $^1$H NMR: 400 MHz, CD$_3$OD δ: 5.48 (s, 1H), 3.89-3.82 (m, 4H), 3.74 (d, J=8.4 Hz, 1H), 3.62 (d, J=13.2 Hz, 1H), 3.19 (d, J=8.8 Hz, 1H).

Step 6: Preparation of Compound 8

To a solution of compound 6 (16.0 mg, 74.0 umol, 1.00 eq) in MeOH (0.10 mL) was added compound 7 (31.5 mg, 222 umol, 30.6 uL, 3.00 eq). The mixture was stirred at 50° C. for 2 hrs. LC-MS showed compound 6 was consumed and desired mass was detected. The mixture was concentrated under reduced pressure to afford compound 8 (10.0 mg, 43.28% yield) as a white solid. Chemical Formula: C$_9$H$_{11}$F$_3$N$_4$O$_5$, LCMS found: [M−96]$^+$=217.1. $^1$H NMR: 400 MHz, DMSO-d$_6$δ: 5.48 (s, 1H), 3.89-3.82 (m, 4H), 3.74 (d, J=8.4 Hz, 1H), 3.62 (d, J=13.2 Hz, 1H), 3.19 (d, J=8.8 Hz, 1H).

Step 7: Preparation of Compound 96

To a solution of compound 8 (5.00 mg, 16.0 umol, 1.10 eq) and Intermediate 48 (12.6 mg, 29.1 umol, 2.00 eq) in DMF (0.05 mL) was added CuSO$_4$ (0.40 M, 72.8 uL, 2.00 eq), sodium ascorbate (0.40 M, 145 uL, 4.00 eq) and THPTA (12.6 mg, 29.1 umol, 2.00 eq) at 0° C. under N$_2$. The mixture was stirred at 0° C. for 12 hrs. LC-MS showed compound 8 was consumed and desired mass was detected. The crude product was purified by prep-HPLC (FA condition) to afford Compound 96 (15.0 mg, 98.2% purity, 46.53% yield, FA) as a white solid. Chemical Formula: C$_{94}$H$_{125}$F$_3$N$_{24}$O$_{26}$S$_2$, LCMS found: [M−96]=1016.7.

Preparation of Intermediate 32: 3-((6S,9R,12S,15S,18S,21S,27S,30S,33S,36S,39S,42S,44aS,49aR)-30-((1H-imidazol-5-yl)methyl)-12,33-bis((1H-indol-3-yl)methyl)-42-(carboxy methyl)-6-((R)-1-hydroxyethyl)-18,27-diisobutyl-15-isopropyl-36-methyl-5,8,11,14,17,20,23,26,29,32,35,38,41,44,49-pentadecaoxooctatetracontahydro-1H-39,9-(ethanothiomethano) dipyrrolo[1,2-a:1',2'-d][1,4,7,10,13,16,19,22,25,28,31,34,37,40,43]pentadecaazacyclopenta tetracontin-21-yl)propanoic acid

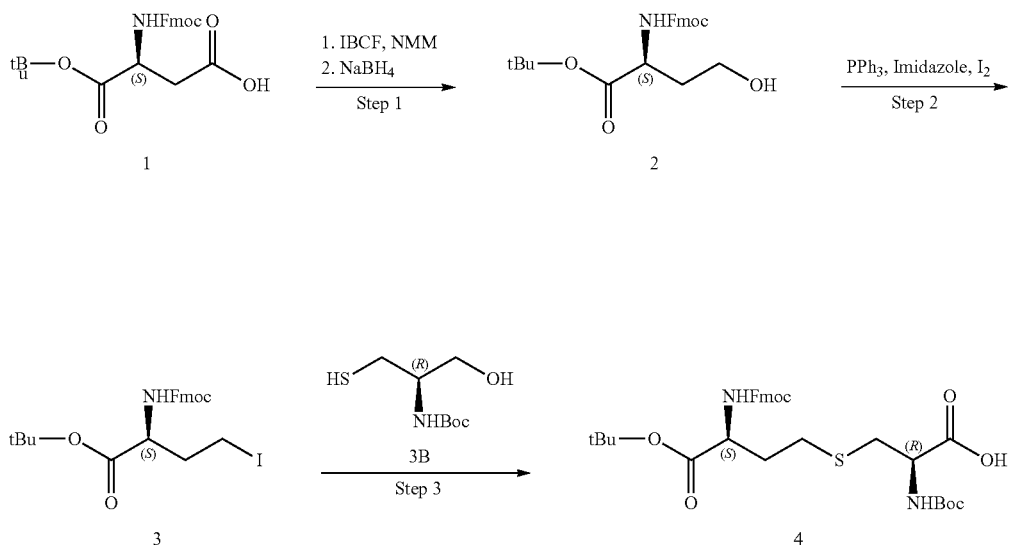

-continued
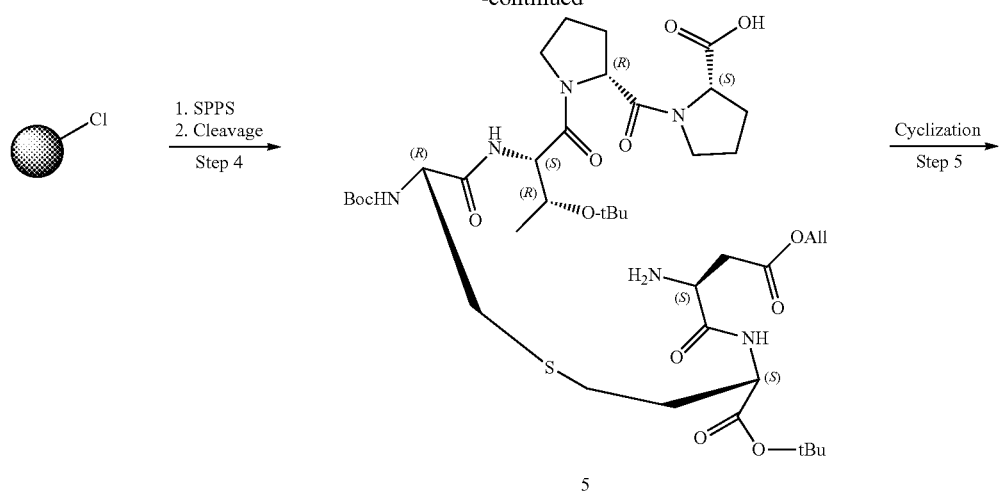
5
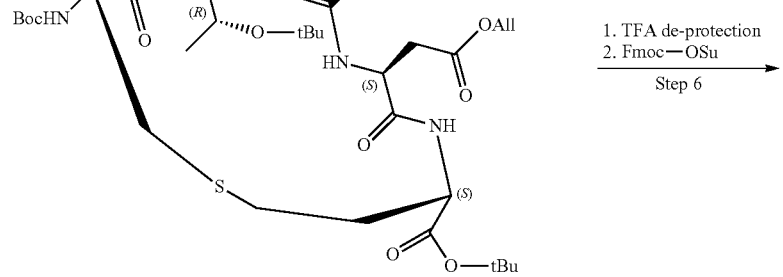
6
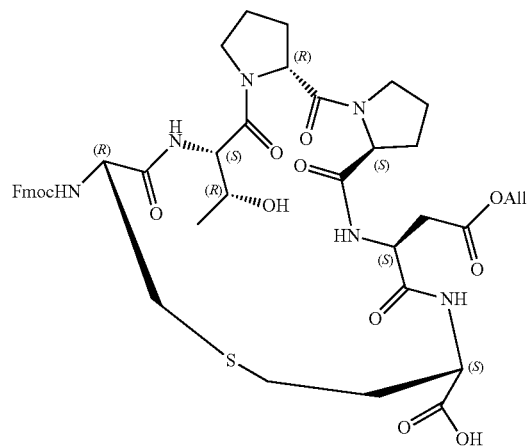
7
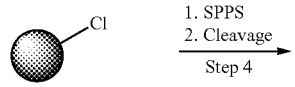

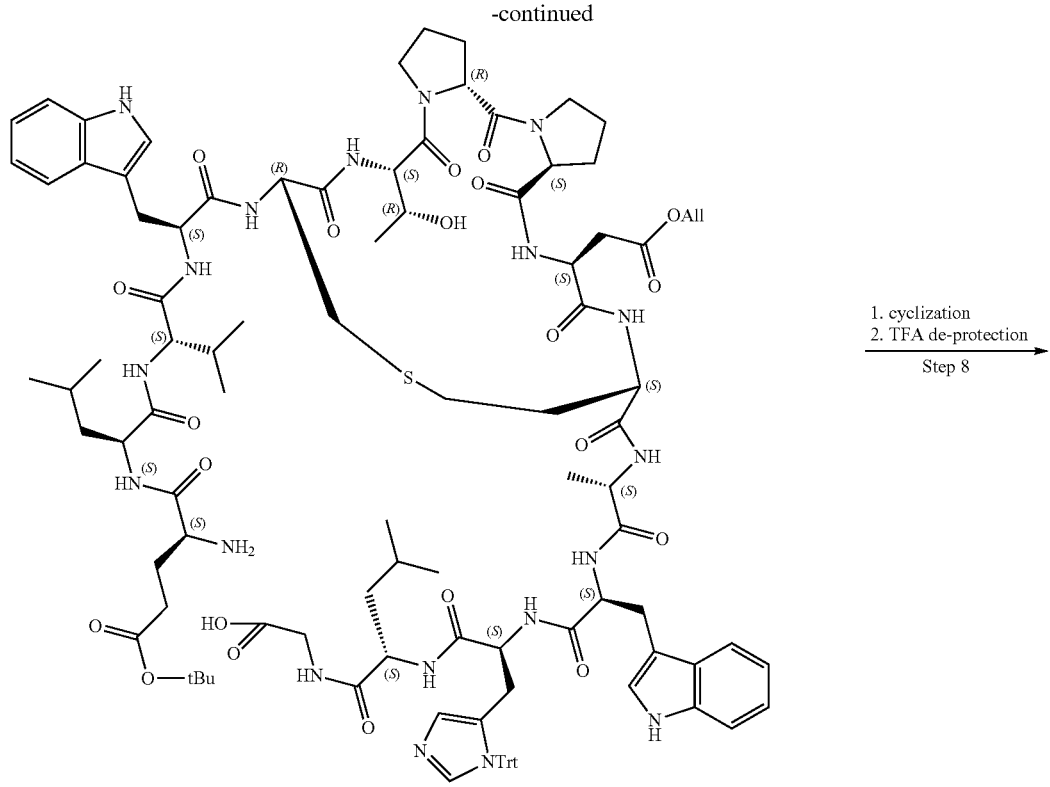
8
1. cyclization
2. TFA de-protection
Step 8
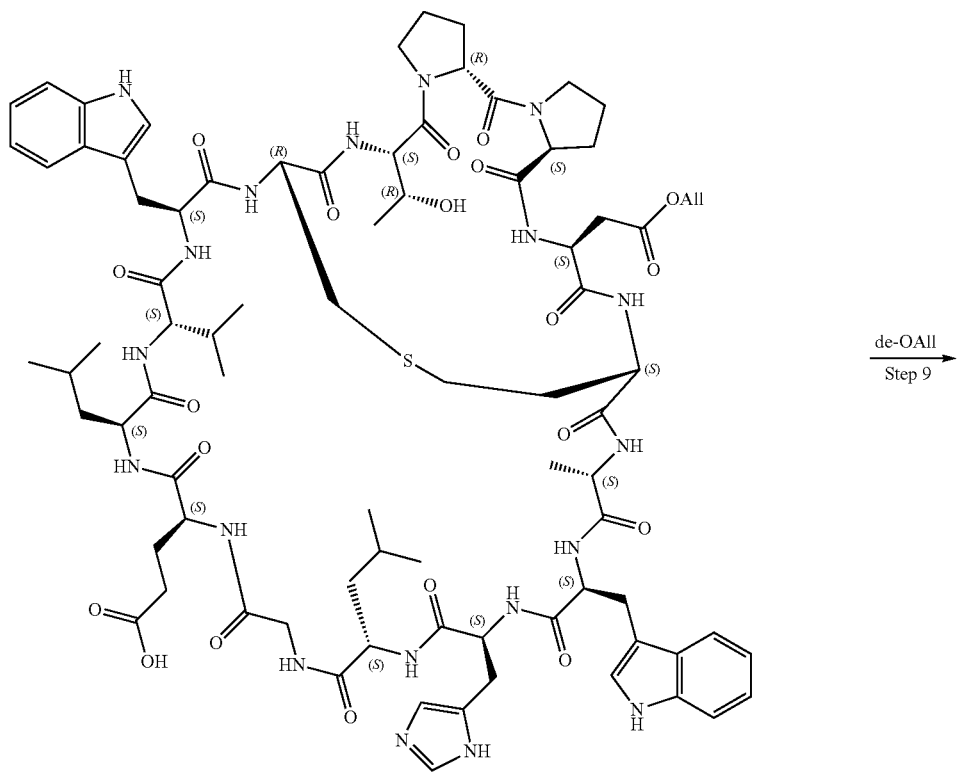
9
de-OAll
Step 9

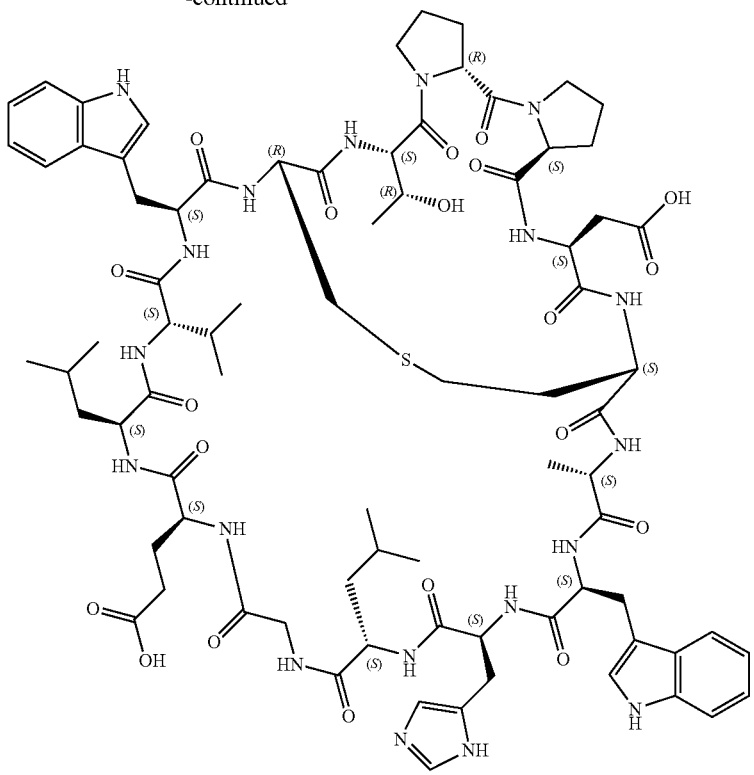

Intermediate 32

Step 1: Preparation of Compound 2

To a solution of compound 1 (20.0 g, 48.61 mmol, 1.00 eq), NMM (5.90 g, 58.33 mmol, 6.41 mL, 1.20 eq) in THF (200 mL) was cooled to 0° C., then the mixture was added IBCF (7.97 g, 58.33 mmol, 7.66 mL, 1.20 eq) dropwise at 0° C. The reaction mixture was stirred at 20° C. for 1 h. The mixture was filtered and the filtrate was cooled to 0° C. Then a solution of NaBH4 (2.88 g, 76.13 mmol, 1.57 eq) in H$_2$O (20 mL) was added slowly. The reaction mixture was stirred at 0° C. for 0.5 h. The reaction mixture was concentrated under reduced pressure and the residue was diluted with EtOAc (200 mL), washed with 1 M HCl (50 mL), H$_2$O (50 mL), brine (50 mL), dried over Na$_2$SO$_4$, concentrated under reduced pressure to afford compound 2 (16.53 g, crude) as white solid. Chemical Formula: C$_{23}$H$_{27}$NO$_5$, LCMS found: [M+Na]=420.2.

Step 2: Preparation of Compound 3

To a solution of compound 2 (16.53 g, 41.59 mmol, 1.00 eq), PPh$_3$ (16.36 g, 62.38 mmol, 1.50 eq) and imidazole (4.25 g, 62.38 mmol, 1.50 eq) in THE (500 mL) was added a solution of I$_2$ (15.83 g, 62.38 mmol, 12.57 mL, 1.50 eq) in THE (200 mL)$_0$ dropwise at 0° C. Then the reaction mixture was allowed to warm to 20° C. and stirred for 4 hrs. LC-MS showed compound 2 was consumed completely and one main peak was desired m/z. The mixture was filtered and concentrated under reduced pressure. The residue was purified by column chromatography (SiO2, Petroleum ether/Ethyl acetate=50/1 to 5/1) to afford compound 3 (18.35 g, 86.96% yield) as white solid. Chemical Formula: C$_{23}$H$_{26}$INO$_4$, LCMS found: [M+Na]=530.09.

Step 3: Preparation of Compound 4

A mixture of compound 3 (1.20 g, 2.37 mmol, 1.00 eq), Boc-Cys-OH (785.03 mg, 3.55 mmol, 1.50 eq), NaOMe (5.4 M, 875.99 uL, 2.00 eq) in MeOH (50 mL) was stirred at 15° C. for 2 hrs. LCMS found desired MS. The mixture was acidified by 1 M HCl to pH=5. Then the mixture was purified by Flash (C18, TFA condition) directly to afford compound 4 (1.10 g, 77.42% yield) as a white solid. Chemical Formula: C$_{31}$H$_{40}$N$_2$O$_8$S, LCMS found: [M+H−Boc]$^+$=501.3, [M+H−Boc-tBu]$^+$=445.2.

Step 4-5: Preparation of Compound 6

Solid Phase Peptide Synthesis

The peptide was synthesized using standard Fmoc chemistry.
1) Resin preparation: To the vessel containing CTC Resin (3.08 g, 2.00 mmol, 0.65 mmol/g) and Fmoc-Pro-OH (674.0 g, 2.00 mmol, 1.00 eq) in DCM (20.0 mL) was added DIEA (1.39 mL, 8.00 mmol, 4.00 eq) dropwise and mixed for 2 hrs with N$_2$ bubbling at 20° C. Then added MeOH (2.00 mL) and bubbled with N$_2$ for another 30 mins. The resin was washed with DMF (40 mL)*5. Then 20% piperidine in DMF (40 mL) was added and the mixture was bubbled with N$_2$ for 30 mins at 20° C. The mixture was filtered to obtain the resin. The resin was washed with DMF (400 mL)*5 before proceeding to next step.
2) Coupling: A solution of Fmoc-D-Pro-OH (2.02 g, 6.00 mmol, 3.00 eq), HBTU (2.19 g, 5.70 mmol, 2.85 eq) in DMF (20.0 mL) was added to the resin with N$_2$ bubbling. Then DIEA (2.09 mL, 12.0 mmol, 6.00 eq) was added to the mixture dropwise and bubbled with $N_2$ for 30 mins at 20° C. The coupling reaction was monitored by ninhydrin test, if it showed colorless, the coupling was completed. The resin was then washed with DMF (40 mL)*5.

3) De-protection: 20% piperidine in DMF (40 mL) was added to the resin and the mixture was bubbled with $N_2$ for 30 mins at 20° C. The resin was then washed with DMF (40 mL)*5. The De-protection reaction was monitored by ninhydrin test, if it showed blue or other brownish red, the reaction was completed.

4) Step 2 and 3 were repeated for all other amino acids: (2-4 in Table 5).

TABLE 5

| # Materials | Coupling reagents |
| --- | --- |
| 1 Fmoc-Pro-OH (1.00 eq) | DIEA (4.00 eq) |
| 2 Fmoc-D- Pro-OH (3.00 eq) | HBTU (2.85 eq) and DIEA (6.00 eq) |
| 3 Compound 4 (2.00 eq) | HATU (1.90 eq) and DIEA (4.00 eq) |
| 4 Fmoc-Asp(OAll)-OH (3.00 eq) | HBTU (2.85 eq) and DIEA (6.00 eq) |

Peptide Cleavage and Cyclization:
1) Cleavage solution (1% TFA/DCM, 40 mL) was added into the flask containing the side chain protected crude peptide (2.00 mmol). The mixture was stirred for 3 min at room temperature.
2) After filtration, the solution was collected.
3) Step 1-2 were repeated for another time.
4) The combined solution (containing 2.00 mmol crude peptide) was diluted with DCM (200 mL), then added HOBT (540.0 mg, 4.00 mmol, 2.00 eq), TBTU (1.28 g, 4.00 mmol, 2.00 eq) and adjusted pH to 8 by DIEA. The mixture was stirred at 20° C. for 2 hrs.
5) The mixture was washed with 1 M HCl (50 mL), brine (50 mL), dried over anhydrous $Na_2SO_4$, and concentrated under reduced pressure to afford compound 6 (1.78 g, crude) as a white solid. Chemical Formula: $C_{41}H_{66}N_6O_{12}S$, LCMS found: $[M+H]^+=868.03$.

Step 6: Preparation of Compound 7

A mixture of compound 6 (1.78 g, crude) in $TFA/H_2O$ (95/5, v/v, 30 mL) was stirred at 20° C. for 2 hrs. Then solvent was removed under reduced pressure. The residue was dissolved in THF (20 mL), $H_2O$ (10 mL), based by saturated aqueous $NaHCO_3$ to pH=8, then the mixture was added Fmoc-OSu (1.38 g, 2.00 eq) at 20° C. The mixture was stirred at 20° C. for 2 hrs. LCMS showed compound 6 was consumed completely and one main peak was desired MS. THE was removed under reduced pressure. The residue was acidified by 1 M HCl to pH=5, extracted with DCM (50 mL), washed with brine (10 mL), dried over anhydrous $Na_2SO_4$, concentrated under reduced pressure. The residue was purified by prep-HPLC (TFA condition) to afford compound 7 (716.0 mg, 90% purity, total yield 40.8%) as a white solid. Chemical Formula: $C_{43}H_{52}N_6O_{12}S$, LCMS found: $[M+H]^+=877.53$.

Step 7-8: Preparation of Compound 9

Solid Phase Peptide Synthesis

The peptide was synthesized using standard Fmoc chemistry.
1) Resin preparation: To the vessel containing CTC Resin (0.77 g, 0.50 mmol, 0.65 mmol/g) and Fmoc-Gly-OH (148.0 mg, 0.50 mmol, 1.00 eq) in DCM (5.0 mL) was added DIEA (348.6 uL, 2.00 mmol, 4.00 eq) dropwise and mixed for 2 hrs with $N_2$ bubbling at 20° C. Then added MeOH (2.00 mL) and bubbled with $N_2$ for another 30 mins. The resin was washed with DMF (40 mL)*5. Then 20% piperidine in DMF (100 mL) was added and the mixture was bubbled with $N_2$ for 30 mins at 20° C. The mixture was filtered to obtain the resin. The resin was washed with DMF (10 mL)*5 before proceeding to next step.

2) Coupling: A solution of Fmoc-Leu-OH (529.5 mg, 1.50 mmol, 3.00 eq), HBTU (548.6 mg, 1.42 mmol, 2.85 eq) in DMF (5.0 mL) was added to the resin with $N_2$ bubbling. Then DIEA (0.53 mL, 3.0 mmol, 6.00 eq) was added to the mixture dropwise and bubbled with $N_2$ for 30 mins at 20° C. The coupling reaction was monitored by ninhydrin test, if it showed colorless, the coupling was completed. The resin was then washed with DMF (10 mL)*5.

3) De-protection: 20% piperidine in DMF (10 mL) was added to the resin and the mixture was bubbled with $N_2$ for 30 mins at 20° C. The resin was then washed with DMF (10 mL)*5. The De-protection reaction was monitored by ninhydrin test, if it showed blue or other brownish red, the reaction was completed.

4) Step 2 and 3 were repeated for all other amino acids: (2-15 in Table 5).

TABLE 5

| # Materials | Coupling reagents |
| --- | --- |
| 1 Fmoc-Gly-OH (1.00 eq) | DIEA (4.00 eq) |
| 2 Fmoc-Leu-OH (3.00 eq) | HBTU (2.85 eq) and DIEA (6.00 eq) |
| 3 Fmoc-His(Trt)-OH (3.00 eq) | HBTU (2.85 eq) and DIEA (6.00 eq) |
| 4 Fmoc-Trp-OH (3.00 eq) | HBTU (2.85 eq) and DIEA (6.00 eq) |
| 5 Fmoc-Ala-OH (3.00 eq) | HBTU (2.85 eq) and DIEA (6.00 eq) |
| 6 Compound 7 (1.50 eq) | HATU (1.42 eq) and DIEA (3.00 eq) |
| 7 Fmoc-Trp-OH (3.00 eq) | HBTU (2.85 eq) and DIEA (6.00 eq) |
| 8 Fmoc-Val-OH (3.00 eq) | HBTU (2.85 eq) and DIEA (6.00 eq) |
| 9 Fmoc-Leu-OH (3.00 eq) | HBTU (2.85 eq) and DIEA (6.00 eq) |
| 10 Fmoc-Glu(OfBu)-OH (3.00 eq) | HBTU (2.85 eq) and DIEA (6.00 eq) |

Peptide Cleavage, Cyclization and De-Protection:
1) Cleavage solution (1% TFA/DCM, 20 mL) was added into the flask containing the side chain protected crude peptide (0.50 mmol). The mixture was stirred for 3 min at room temperature.
2) After filtration, the solution was collected.
3) Step 1-2 were repeated for another time.
4) The combined solution (containing 0.50 mmol crude peptide) was diluted with DCM (50 mL), then added HOBT (135.0 mg, 1.00 mmol, 2.00 eq), TBTU (320 mg, 1.00 mmol, 2.00 eq) and adjusted pH to 8 by DIEA. The mixture was stirred at 20° C. for 2 hrs.
5) The mixture was washed with 1 M HCl (20 mL), brine (20 mL), dried over anhydrous $Na_2SO_4$, and concentrated under reduced pressure to afford compound 7 (0.50 mmol, crude) as a white solid.
6) A mixture of compound 7 (0.50 mmol, crude) in $TFA/TIS/H_2O$ (95/2.5/2.5, 20 mL) was stirred at 20° C. for 1 hrs.
7) The mixture was precipitated with isopropyl ether (cod, 100 mL) and centrifuged (3 min at 3000 rpm). The solid was washed with isopropyl ether twice, dried under vacuum for 2 hrs.

8) The residue was purified by prep-HPLC (TFA condition) to afford compound 9 (53.0 mg, 90% purity, total yield 6.1%). Chemical Formula: $C_{83}H_{113}N_{19}O_{20}S$, LCMS found: $[M+2H]^{2+}=865.9$.

Step 9: Preparation of Compound Intermediate 32.

A mixture of compound 9 (53.0 mg, 30.65 umol, 1.00 eq), Pd(PPh$_3$)$_4$ (14.1 mg, 12.26 umol, 0.40 eq), phenylsilane (66.3 mg, 613.08 umol, 75.65 uL, 20.00 eq) in DMF (0.50 mL) was degassed and purged with N$_2$ for 3 times, then the mixture was stirred at 20° C. for 1 h under N$_2$ atmosphere. The mixture was purified by prep-HPLC (TFA condition) directly to afford Intermediate 32 (21.8 mg, 94.4% purity, 42.1% yield) as a white solid. Chemical Formula: $C_{83}H_{113}N_{19}O_{20}S$, LCMS found: $[M+H]^+=1690.0$, $[M+2H]^{2+}=845.6$.

Additional Synthetic Schemes

Preparation of Compound 97: N—((S)-1-cycloheptyl-2-((4-((R)-1-((2R,3R,4R,5S)-3,4-dihydroxy-5-((6-(trifluoromethyl)pyrazin-2-yl)amino)tetrahydro-2H-pyran-2-yl)-15-(4-methylpiperazine-1-carbonyl)-13-oxo-2,5,8,11-tetraoxa-14-azahexadecan-16-yl)phenyl)amino)-2-oxoethyl)-1-ethyl-1H-pyrazole-5-carboxamide

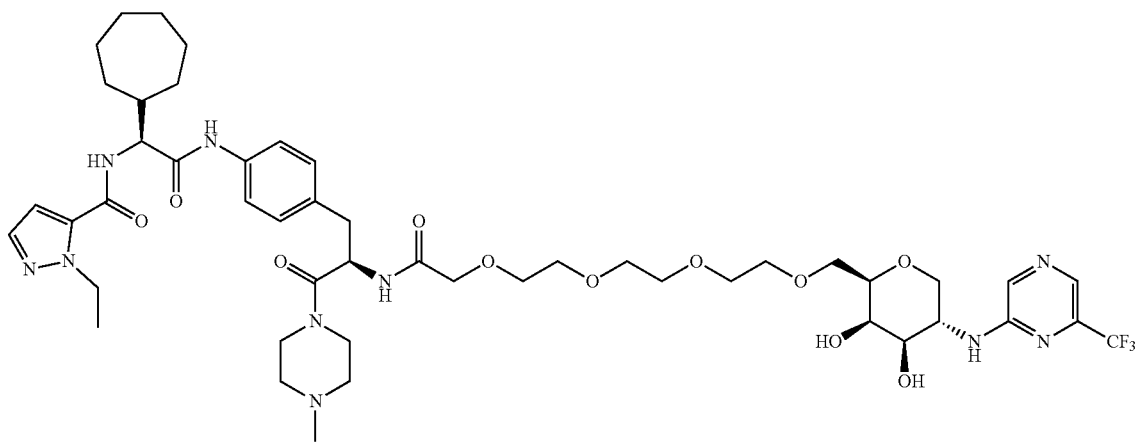 [SMILES: CCn1nccc1C(=O)N[C@H](C(=O)Nc1ccc(C[C@@H](NC(=O)COCCOCCOCCOC[C@H]2OC[C@H](Nc3cncc(C(F)(F)F)n3)[C@@H](O)[C@H]2O)C(=O)N2CCN(C)CC2)cc1)C1CCCCCC1]

Preparation of 1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-oic acid

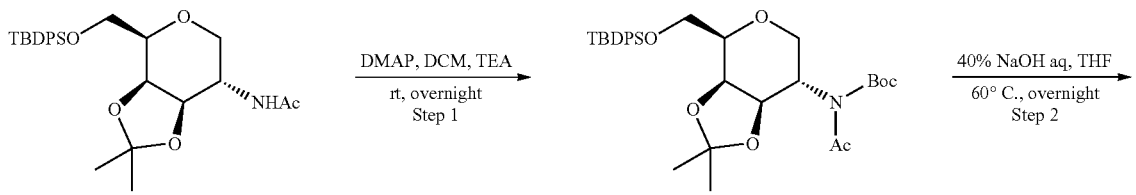

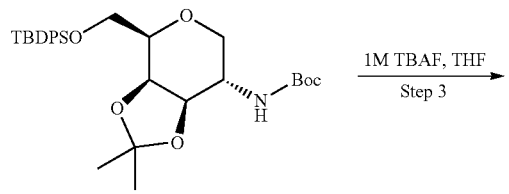

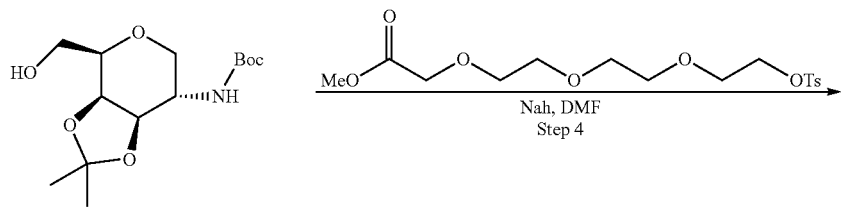

-continued

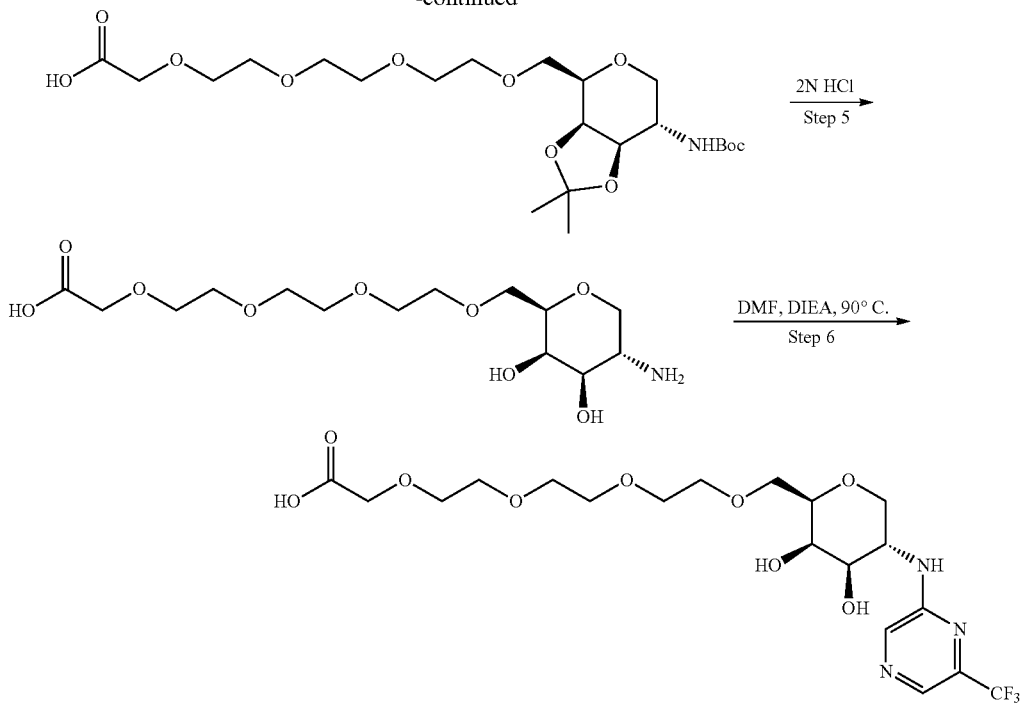

Step 1: To a solution of N-((3aR,4R,7S,7aR)-4-(((tert-butyldiphenylsilyl)oxy)methyl)-2,2-dimethyltetrahydro-4H-[1,3]dioxolo[4,5-c]pyran-7-yl)acetamide (7 g, 14.53 mmol) in DCM (70 mL) at rt was added TEA (2.06 mL, 14.83 mmol), DMAP (0.12 g, 0.98 mmol), and di-tert-butyl dicarbonate (3.17 mL, 14.83 mmol). The mixture was stirred at the room temperature overnight. On consumption of starting material (LCMS monitoring), the mixture was concentrated under reduced pressure to give a crude product, which was purified by flash chromatography to give tert-butyl acetyl((3aR,4R,7S,7aR)-4-(((tert-butyldiphenylsilyl)oxy)methyl)-2,2-dimethyltetrahydro-4H-[1,3]dioxolo[4,5-c]pyran-7-yl)carbamate (7 g, 83% yield) as a colorless oil. LC-MS (ESI) found: 584 [M+H]$^+$.

Step 2: To a solution of tert-butyl acetyl((3aR,4R,7S,7aR)-4-(((tert-butyldiphenylsilyl)oxy)methyl)-2,2-dimethyltetrahydro-4H-[1,3]dioxolo[4,5-c]pyran-7-yl)carbamate (7 g, 11.9 mmol) in THF (70 mL) at rt was added NaOH (40%, 10 mL, 59.9 mmol). The mixture was stirred at the room temperature for overnight. On consumption of starting material (LCMS monitoring), water (20 mL) was slowly added. The mixture was diluted with ethyl acetate (100 mL) and wash with water (20 mL×3). The organic layer was dried over sodium sulfate, filtered, concentrated under reduced pressure to give a crude product, which was purified by flash chromatography to give tert-butyl ((3aR,4R,7S,7aR)-4-(((tert-butyldiphenylsilyl)oxy)methyl)-2,2-dimethyltetrahydro-4H-[1,3]dioxolo[4,5-c]pyran-7-yl)carbamate (6 g, 93% yield) as a colorless oil. LC-MS (ESI) found: 542 [M+H]$^+$.

Step 3: To a solution of tert-butyl ((3aR,4R,7S,7aR)-4-(((tert-butyldiphenylsilyl)oxy)methyl)-2,2-dimethyltetrahydro-4H-[1,3]dioxolo[4,5-c]pyran-7-yl)carbamate (6 g, 11 mmol) in THF (100 mL) was added TBAF solution (22 mL, 1 M in THF). The reaction was stirred at room temperature for 3 h. The mixture was concentrated under reduced pressure to give a crude product, which was purified by flash chromatography (silica gel, 0-10% DCM in MeOH) to give tert-butyl ((3aR,4R,7S,7aR)-4-(hydroxymethyl)-2,2-dimethyltetrahydro-4H-[1,3]dioxolo[4,5-c]pyran-7-yl)carbamate (2.5 g, 76% yield) as white solid. LC-MS (ESI) found: 304 [M+H]$^+$.

Step 4: To a solution of tert-butyl ((3aR,4R,7S,7aR)-4-(hydroxymethyl)-2,2-dimethyltetrahydro-4H-[1,3]dioxolo[4,5-c]pyran-7-yl)carbamate (2.5 g, 8.2 mmol) in DMF (50 mL) at 0° C. was added NaH (0.47 g, 60% wt. in mineral oil, 12.3 mmol) and methyl 2-(2-(2-(2-(tosyloxy)ethoxy)ethoxy)ethoxy)acetate (2.6 g, 7.38 mmol). The mixture was stirred at the room temperature overnight. On consumption of starting material (LCMS monitoring), the reaction vessel was again cooled to 0° C., water (10 mL) was slowly added and the reaction mixture stirred for 15 min. The mixture was diluted with ethyl acetate (100 mL) and wash with water (20 mL×3). The organic layer was dried over sodium sulfate, concentrated under reduced pressure to give a crude product, which was purified by flash chromatography to give 1-((3aR,4R,7S,7aR)-7-((tert-butoxycarbonyl)amino)-2,2-dimethyltetrahydro-4H-[1,3]dioxolo[4,5-c]pyran-4-yl)-2,5,8,11-tetraoxatridecan-13-oic acid (2.0 g, 51%) as a colorless oil. LC-MS (ESI) found: 494 [M+H]$^+$.

Step 5: To a solution of 1-((3aR,4R,7S,7aR)-7-((tert-butoxycarbonyl)amino)-2,2-dimethyltetrahydro-4H-[1,3]dioxolo[4,5-c]pyran-4-yl)-2,5,8,11-tetraoxatridecan-13-oic acid (2.0 g, 4.0 mmol) in THF (20 mL) at rt was added HCl solution (4 mL, 2 N in H$_2$O). The mixture was stirred at the rt for 3 h. The mixture was concentrated under reduced pressure to give crude 1-((2R,3R,4R,5S)-5-amino-3,4-dihydroxytetrahydro-2H-pyran-2-yl)-2,5,8,11-tetraoxatridecan-13-oic acid (1.0 g, 71% yield) as a colorless oil. LC-MS (ESI) found: 354 [M+H]$^+$.

Step 6: To a solution of 1-((2R,3R,4R,5S)-5-amino-3,4-dihydroxytetrahydro-2H-pyran-2-yl)-2,5,8,11-tetraoxatridecan-13-oic acid (200 mg, 0.55 mmol) and DIPEA (209 mg, 1.65 mmol) in dry DMF (10 mL) at rt under N$_2$ atmosphere was added 2,4-dichloro-6-methoxypyrimidine (199 mg, 1.1 mmol). After the addition was complete, the reaction was stirred at 100° C. overnight. On consumption of starting material (TLC monitoring), the reaction vessel was again cooled to rt. The mixture was diluted with ethyl acetate (100 mL) and wash with water (20 mL×3). The organic layer was dried over sodium sulfate, concentrated under reduced pressure to give a crude product, which was purified by flash chromatography to give 1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-oic acid (10 mg, 3.5% yield) as a colorless oil. LC-MS (ESI) found: 500 [M+H]$^+$. $^1$H NMR (400 MHz, CD$_3$OD): δ 8.11 (s, 1H), 7.99 (s, 1H), 4.33 (td, J=10.6, 5.2 Hz, 1H), 4.17-4.06 (m, 3H), 3.92 (d, J=3.0 Hz, 1H), 3.74-3.52 (m, 16H), 3.12 (t, J=10.8 Hz, 1H).

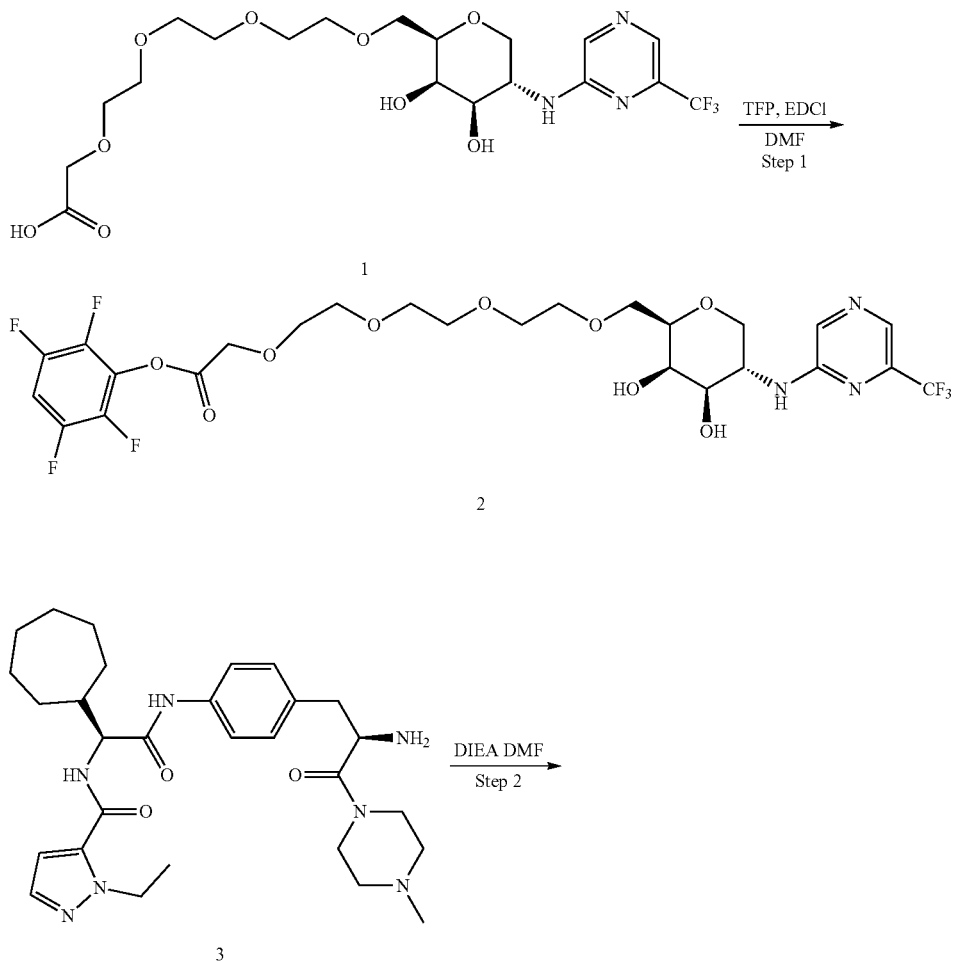

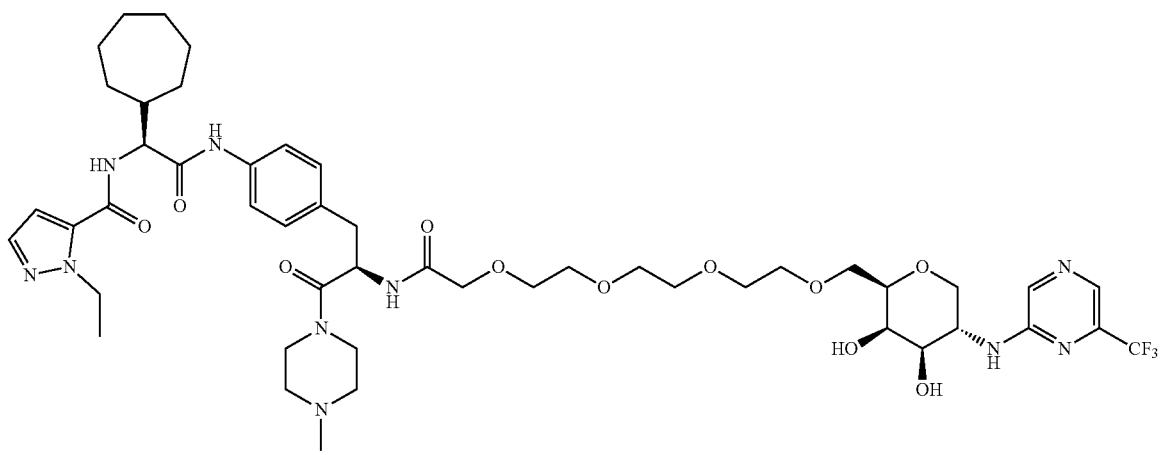

Compound 97

Step 1: Preparation of TFP Ester (Compound 4)

A mixture of 2,3,5,6-tetrafluorophenol, acid 1 in DMF was cooled to 0° C. Then the mixture was added EDCI at 0° C. and stirred at 0° C. for 2 hrs. The reaction mixture was purified by prep-HPLC to afford TFP ester 2.

Step 2: Preparation of Intermediate (3)

Methyl (S)-2-cycloheptyl-2-(1-ethyl-1H-pyrazole-5-carboxamido)acetate

To a solution of methyl (S)-2-amino-2-cycloheptylacetate (1.0 mmol) in DMF (10 mL) is added 1-ethyl-1H-pyrazole-5-carboxylic acid (1.15 mmol, 1.15 eq). Next, 2 mmol DIPEA and 1.2 mmol HATU is added. The reaction is stirred for 1 hour, then water is added. Ethyl acetate (3×25 mL) is used to extract the product from the aqueous layer and then the organics are combined and concentrated. The crude material is purified by silica chromatography (100% ethyl acetate) and visualized by UV.

(S)-2-cycloheptyl-2-(1-ethyl-1H-pyrazole-5-carboxamido)acetic acid

Methyl (S)-2-cycloheptyl-2-(1-ethyl-1H-pyrazole-5-carboxamido)acetate (1 mmol) is dissolved in 10 mL THF and 10 mL water. Next, 10 mmol of lithium hydroxide is added and the reaction stirred at room temperature until the starting material is consumed (LC-MS). The reaction is acidified with 1M HCl to pH 2, and then extracted with ethyl acetate. The organics are combined and concentrated and then used in the next step without further purification.

tert-butyl (R)-(3-(4-(benzylamino)phenyl)-1-(4-methylpiperazin-1-yl)-1-oxopropan-2-yl)carbamate To a solution of (R)-3-(4-(benzylamino)phenyl)-2-((tert-butoxycarbonyl)amino)propanoic acid (1.0 mmol) in DMF (10 mL) is added N-methyl piperazine (1.15 mmol, 1.15 eq). Next, 2 mmol DIPEA and 1.2 mmol HATU is added. The reaction is stirred for 1 hour, then water is added. Ethyl acetate (3×25 mL) is used to extract the product from the aqueous layer and then the organics are combined and concentrated. The crude material is purified by silica chromatography (100% ethyl acetate) and visualized by UV.

tert-butyl (R)-(3-(4-aminophenyl)-1-(4-methylpiperazin-1-yl)-1-oxopropan-2-yl)carbamate A three neck round bottom flask is charged with tert-butyl (R)-(3-(4-(benzylamino)phenyl)-1-(4-methylpiperazin-1-yl)-1-oxopropan-2-yl)carbamate (1 mmol), 0.1 mmol palladium on carbon (5%, Degussa), 5 mL ethanol and 5 mL THF. Next, the headspace of the flask is evacuated by vacuum and refilled with hydrogen gas. A hydrogen balloon is fitted to one of the necks of the flask. The reaction is stirred under hydrogen for 12 hours, then filtered through Celite. The solvent is removed by rotary evaporation and used without further purification.

tert-butyl ((R)-3-(4-((S)-2-cycloheptyl-1H-pyrazole-5-carboxamido)acetamido)phenyl)-1-(4-methylpiperazin-1-yl)-1-oxopropan-2-yl)carbamate To a solution of tert-butyl (R)-(3-(4-aminophenyl)-1-(4-methylpiperazin-1-yl)-1-oxopropan-2-yl)carbamate (1.0 mmol) in DMF (10 mL) is added (S)-2-cycloheptyl-2-(1-ethyl-1H-pyrazole-5-carboxamido)acetic acid (1.15 mmol, 1.15 eq). Next, 2 mmol DIPEA and 1.2 mmol HATU is added. The reaction is stirred for 1 hour, then water is added. Ethyl acetate (3×25 mL) is used to extract the product from the aqueous layer and then the organics are combined and concentrated. The crude material is purified by silica chromatography (100% ethyl acetate) and visualized by UV.

N—((S)-2-((4-((R)-2-amino-3-(4-methylpiperazin-1-yl)-3-oxopropyl)phenyl)amino)-1-cycloheptyl-2-oxoethyl)-1-ethyl-1H-pyrazole-5-carboxamide tert-butyl ((R)-3-(4-((S)-2-cycloheptyl-2-(1-ethyl-¹H-pyrazole-5-carboxamido)acetamido) phenyl)-1-(4-methylpiperazin-1-yl)-1-oxopropan-2-yl)carbamate (1.0 mmol) is dissolved in 10 mL DCM and then 20 mmol trifluoroacetic acid is added. The reaction is stirred at room temperature for four hours and then concentrated to a crude solid. The solid is purified by HPLC to afford the title compound.

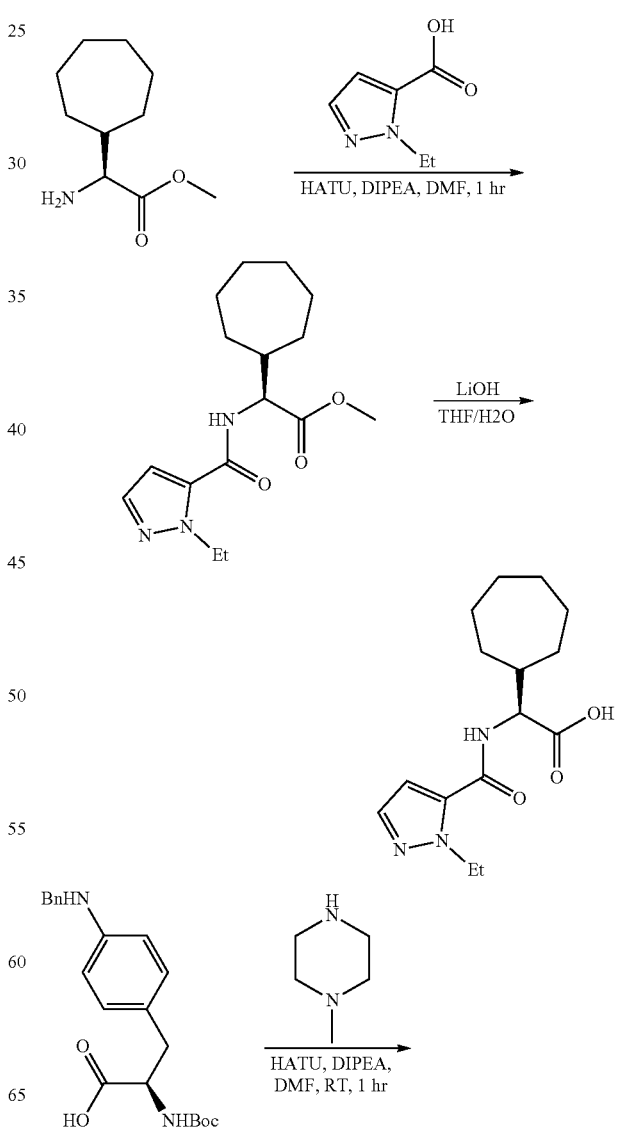

1317
-continued

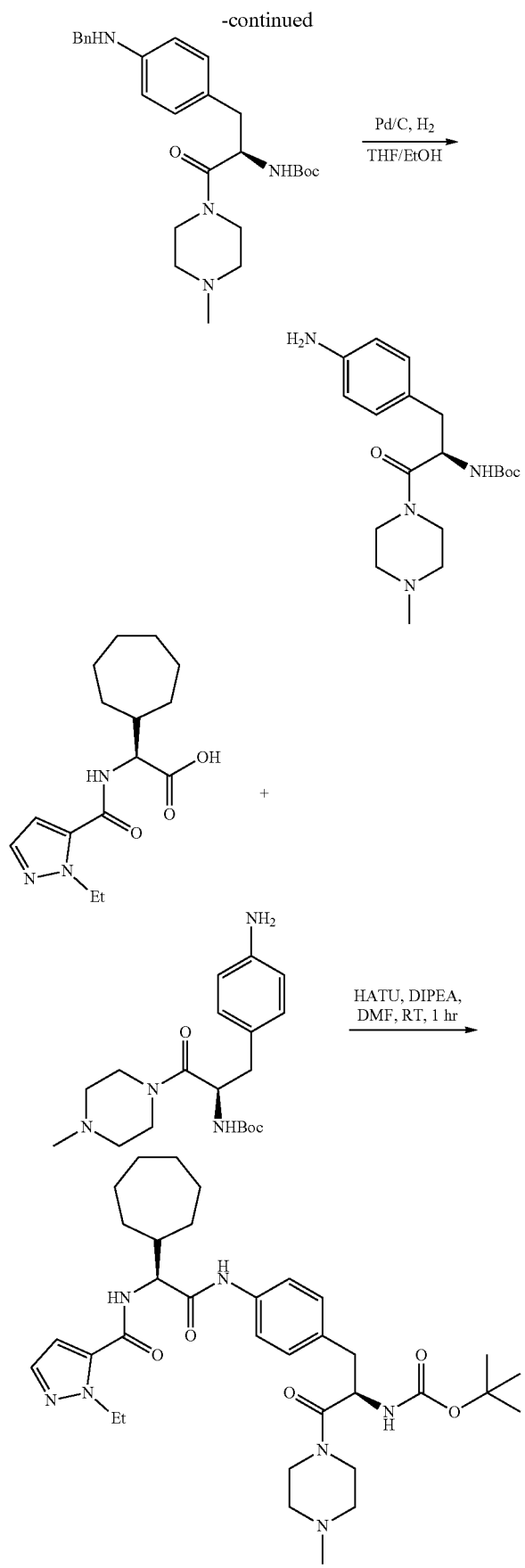

1318
-continued

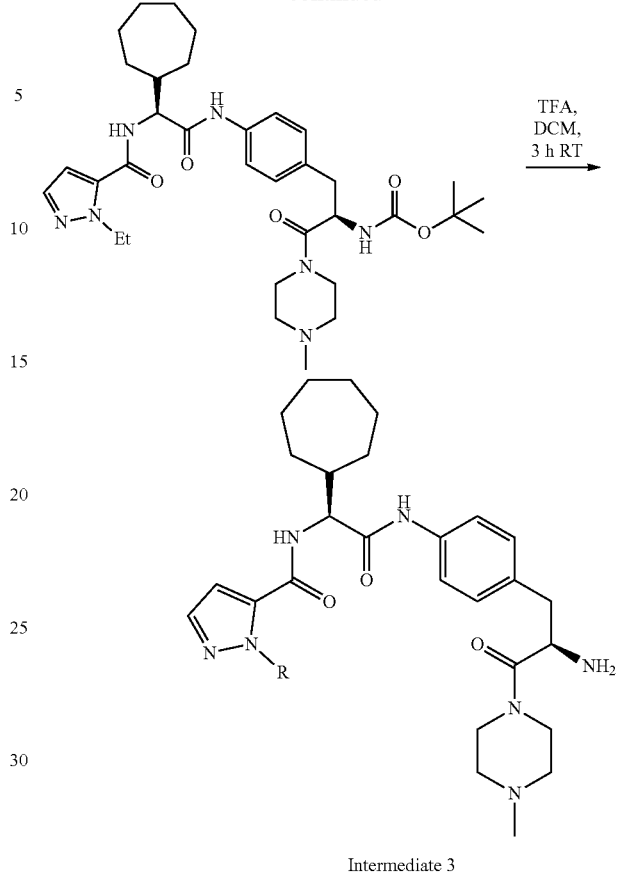

Intermediate 3

Step 3 Preparation of Compound 97: A mixture of amino intermediate 3, TFP ester 2, DIEA in DMF was stirred at 25° C. for 1 hr. The reaction mixture was purified by HPLC to get the title compound.

Preparation of N—((S)-1-cycloheptyl-2-((4-((R)-1-((2R,3R,4R,5S)-3,4-dihydroxy-5-((6-(trifluoromethyl)pyrazin-2-yl)amino)tetrahydro-2H-pyran-2-yl)-15-(4-methylpiperazine-1-carbonyl)-13-oxo-2,5,8,11-tetraoxa-14-azahexadecan-16-yl)phenyl)amino)-2-oxoethyl)-1-isopropyl-1H-pyrazole-5-carboxamide (Compound 98), N—((S)-2-((4-((R)-2-acetamido-3-(4-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-oyl)piperazin-1-yl)-3-oxopropyl)phenyl)amino)-1-cycloheptyl-2-oxoethyl)-1-ethyl-1H-pyrazole-5-carboxamide (Compound 99) and N—((S)-2-((4-((R)-2-acetamido-3-(4-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-oyl)piperazin-1-yl)-3-oxopropyl)phenyl)amino)-1-cycloheptyl-2-oxoethyl)-1-isopropyl-1H-pyrazole-5-carboxamide (Compound 100)

The following compounds Compound 98, Compound 99, and Compound 100 were prepared according to the procedure same as that of Compound 97 using with acid intermediate 1 and the corresponding amino intermediates, N—((S)-2-((4-((R)-2-amino-3-(4-methylpiperazin-1-yl)-3-oxopropyl)phenyl)amino)-1-cycloheptyl-2-oxoethyl)-1-isopropyl-1H-pyrazole-5-carboxamide, (N—((S)-2-((4-((R)-2-acetamido-3-oxo-3-(piperazin-1-yl)propyl)phenyl)amino)-1-cycloheptyl-2-oxoethyl)-1-ethyl-1H-pyrazole-5-carboxamide and N—((S)-2-((4-((R)-2-acetamido-3-oxo-3-(412- piperazin-1-yl)propyl)phenyl)amino)-1-cycloheptyl-2-oxo-ethyl)-1-isopropyl-1H-pyrazole-5-carboxamide.
Compound 98
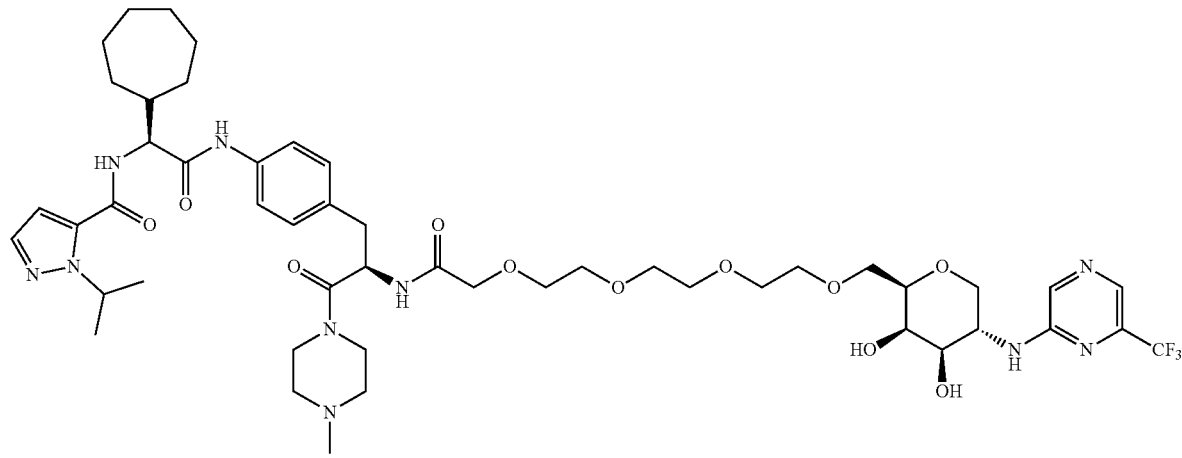
Compound 99
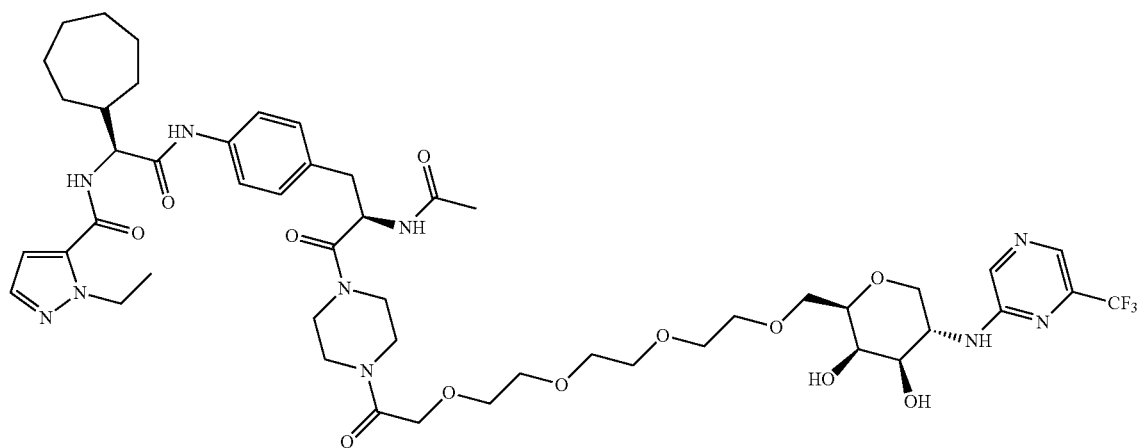
Compound 100
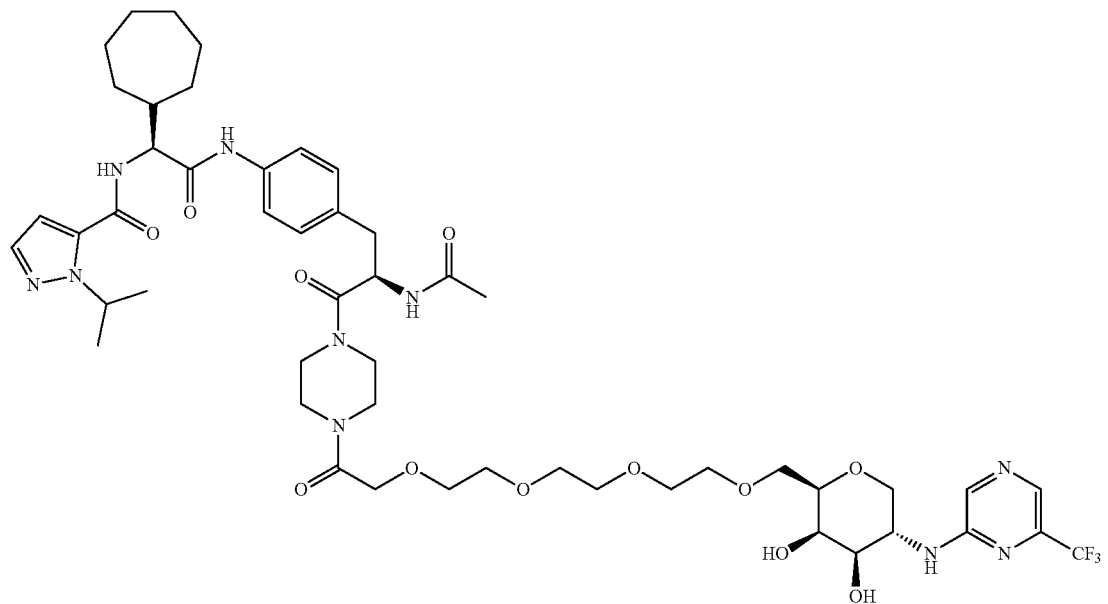

-continued
1321
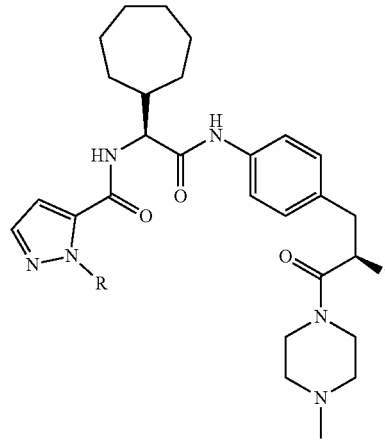
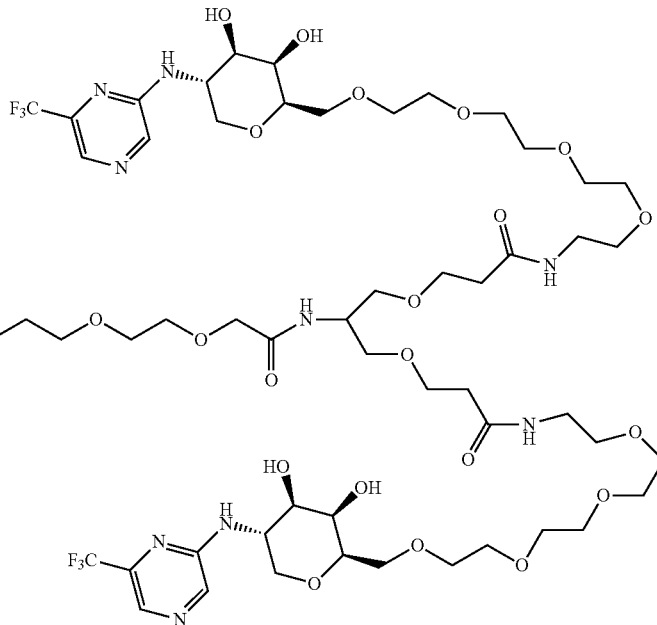
1322
R = Et, iPr
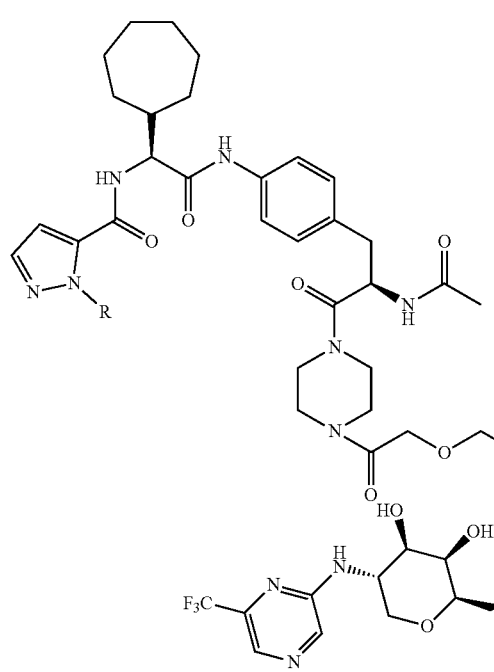
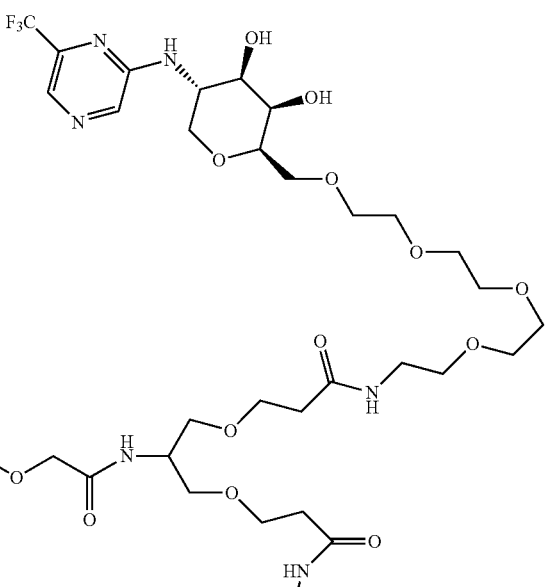
R = Et, iPr Preparation of 3,3'-((2-((R)-2-(4-((S)-2-cycloheptyl-2-(1-ethyl-1H-pyrazole-5-carboxamido)acetamido)benzyl)-1-(4-methylpiperazin-1-yl)-1,4-dioxo-6,9,12-trioxa-3-azatetradecan-14-amido)propane-1,3-diyl)bis(oxy))bis(N-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-yl)propanamide) (Compound 101)

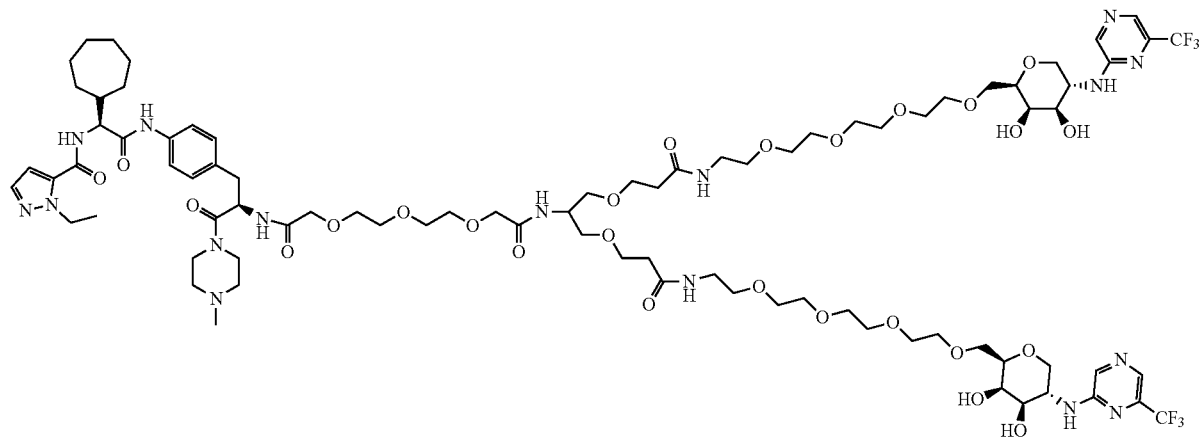 [SMILES: CCn1nccc1C(=O)N[C@H](C(=O)Nc1ccc(C[C@@H](NC(=O)COCCOCCOCC(=O)NC(COCCC(=O)NCCOCCOCCOCCOC[C@H]2OC[C@H](Nc3cncc(C(F)(F)F)n3)[C@@H](O)[C@H]2O)COCCC(=O)NCCOCCOCCOCCOC[C@H]2OC[C@H](Nc3cncc(C(F)(F)F)n3)[C@@H](O)[C@H]2O)C(=O)N2CCN(C)CC2)cc1)C1CCCCCC1]

Preparation of 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid

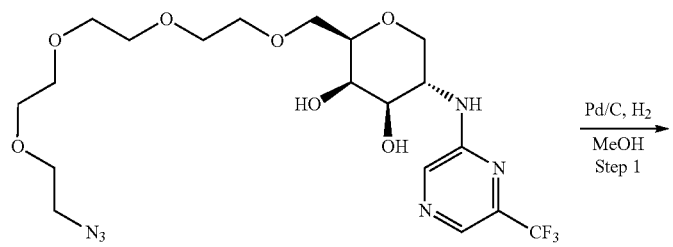

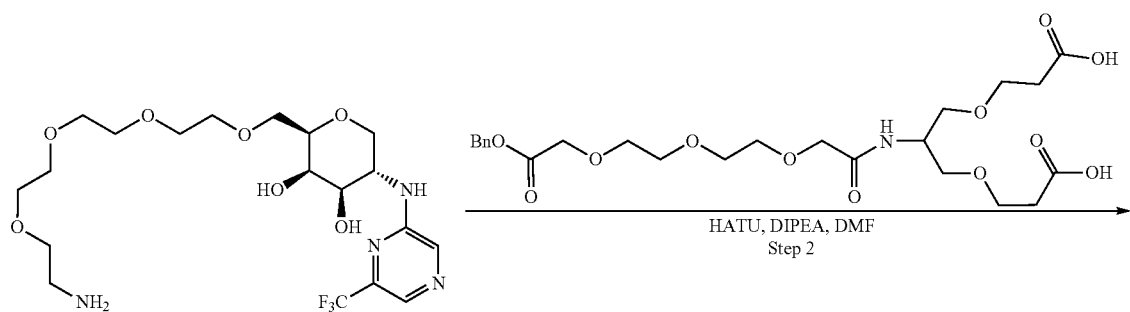

-continued

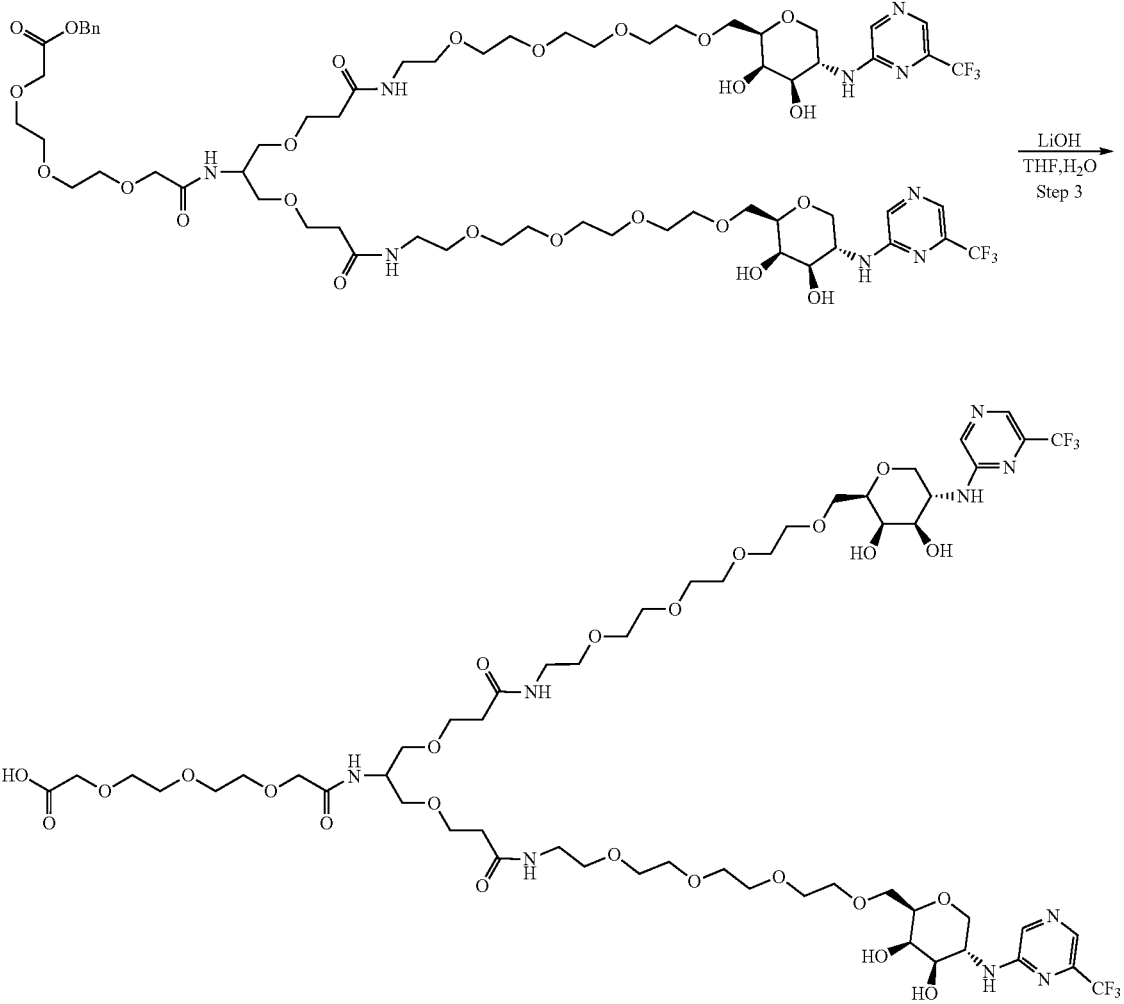

Step 1: To a solution of (2R,3R,4R,5S)-2-(13-azido-2,5,8,11-tetraoxatridecyl)-5-((6-(trifluoromethyl)pyrazin-2-yl)amino)tetrahydro-2H-pyran-3,4-diol (300 mg, 0.59 mmol) in MeOH (10 mL) was added Pd/C (30 mg, 10% wt., 60% wet) at rt under a $H_2$ balloon. The reaction was stirred at rt for 0.5 h. The resulting mixture was filtered and concentrated in vacuo. The crude product was used for next step without further purification. LC-MS (ESI) found: 485 $[M+H]^+$.

Step 2: A solution of 15-((2-carboxyethoxy)methyl)-3,13-dioxo-1-phenyl-2,5,8,11,17-pentaoxa-14-azaicosan-20-oic acid (125 mg, 0.24 mmol), DIPEA (0.16 mL, 0.94 mmol) and HATU (197 mg, 0.52 mmol) in DMF (10 mL) was stirred at rt for 30 min. (2R,3R,4R,5S)-2-(13-amino-2,5,8,11-tetraoxatridecyl)-5-((6-(trifluoromethyl)pyrazin-2-yl)amino)tetrahydro-2H-pyran-3,4-diol (296 mg, 0.52 mmol) was added at rt. The reaction was stirred overnight. The resulting mixture was concentrated in vacuo. The crude product was purified by prep-HPLC to give benzyl 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (250 mg, 0.17 mmol) as a colorless oil. LC-MS (ESI) found: 1463 $[M+H]^+$.

Step 3: To a solution of benzyl 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (250 mg, 0.17 mmol) in THF (5 mL) and $H_2O$ (1.5 mL) was added LiOH (21.5 mg, 0.51 mmol) at rt. The reaction was stirred at rt for 2 h. The reaction was adjusted to acidic with 2 N HCl. The crude product was purified by prep-HPLC to give 1-((2R,3R,4R,5S)-3,4-dihydroxy-5-((6-(trifluoromethyl)pyrazin-2-yl)amino)tetrahydro-2H-pyran-2-yl)-20-(1-((2R,3R,4R,5S)-3,4-dihydroxy-5-((6-(trifluoromethyl)pyrazin-2-yl)amino)tetrahydro-2H-pyran-2-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid (160 mg, 68% yield) as a white solid. LC-MS (ESI) found: 1373 $[M+H]^+$. $^1$H NMR (400 MHz, $CD_3OD$): δ: 8.12 (s, 2H), 8.00 (s, 2H), 4.34 (td, J=10.6, 5.1 Hz, 2H), 4.23-4.18 (m, 1H), 4.14-4.09 (m, 4H), 4.00 (s, 2H), 3.93 (d, J=2.4 Hz, 2H), 3.73-3.61 (m, 44H), 3.57-3.50 (m, 8H), 3.38 (t, J=5.4 Hz, 4H), 3.12 (t, J=10.8 Hz, 2H), 2.45 (t, J=6.1 Hz, 4H). $^{19}$F NMR (377 MHz, $CD_3OD$): δ −70.26 (s).

1327
1328
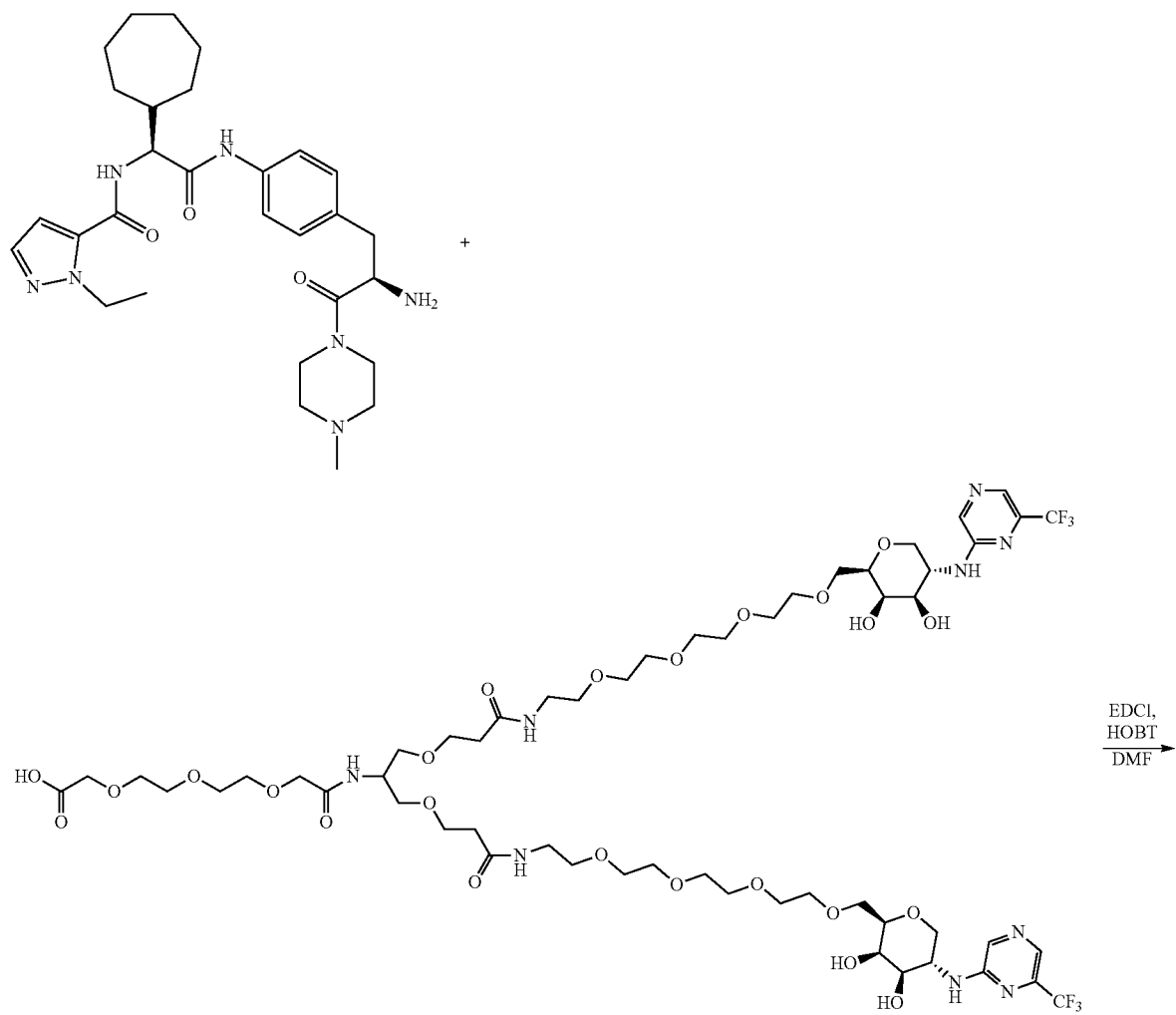
EDCl, HOBT / DMF →
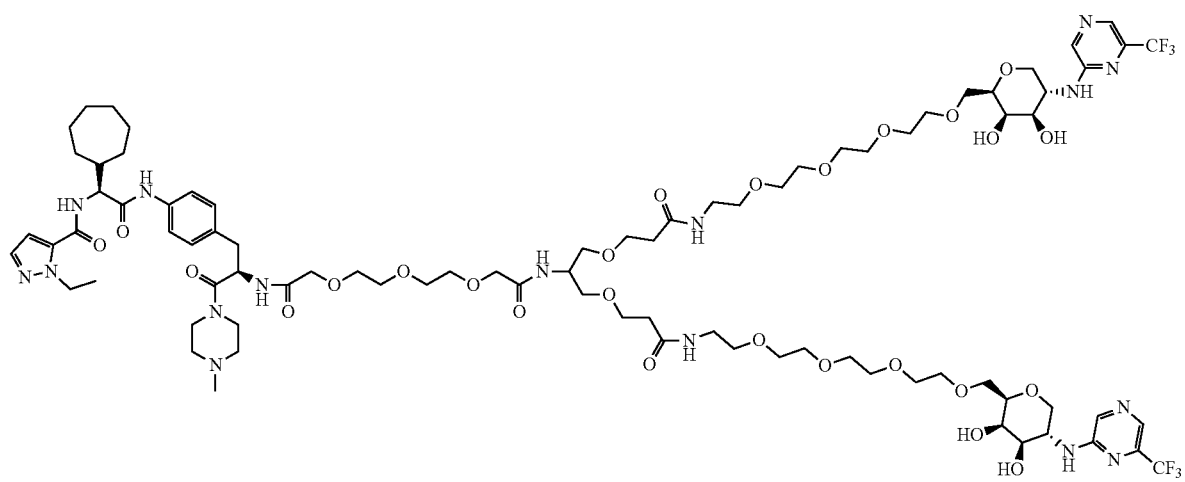

Preparation of Compound 101

A mixture of N—((S)-2-((4-((R)-2-amino-3-(4-methylpiperazin-1-yl)-3-oxopropyl)phenyl)amino)-1-cycloheptyl-2-oxoethyl)-1-ethyl-¹H-pyrazole-5-carboxamide, EDCI, HOBt in DMF was stirred at 0° C. for 1 hr. The mixture was purified by prep-HPLC (acid condition, TFA) to afford Dice 5.

The following compounds Compound 102, Compound 103 and Compound 104 were prepared according to the procedure same as that of Compound 101 using the corresponding the corresponding amino intermediates, N—((S)-2-((4-((R)-2-amino-3-(4-methylpiperazin-1-yl)-3-oxopropyl)phenyl)amino)-1-cycloheptyl-2-oxoethyl)-1-isopropyl-1H-pyrazole-5-carboxamide, (N—((S)-2-((4-((R)-2-acetamido-3-oxo-3-(piperazin-1-yl)propyl)phenyl)amino)-1-cycloheptyl-2-oxoethyl)-1-ethyl-¹H-pyrazole-5-carboxamide and N—((S)-2-((4-((R)-2-acetamido-3-oxo-3-(412-piperazin-1-yl)propyl)phenyl)amino)-1-cycloheptyl-2-oxoethyl)-1-isopropyl-1H-pyrazole-5-carboxamide.

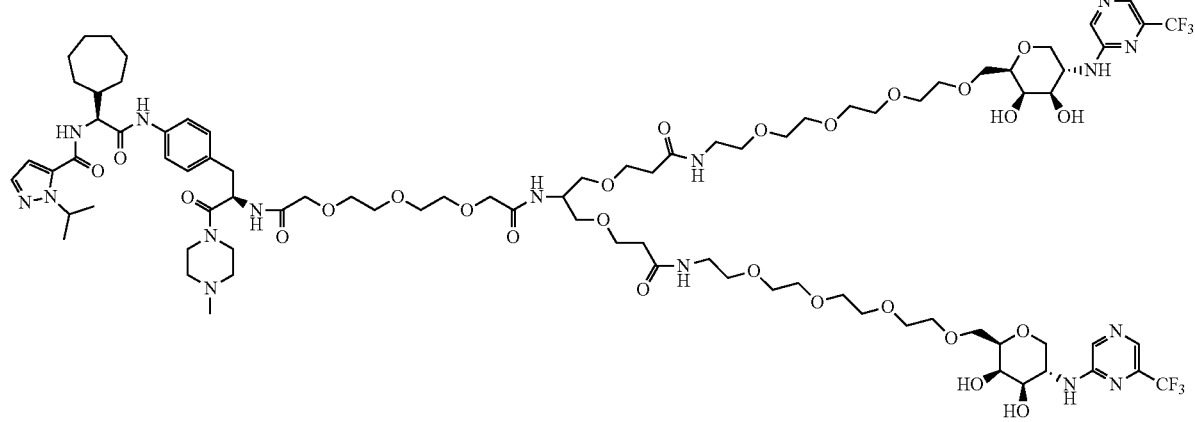

Compound 102

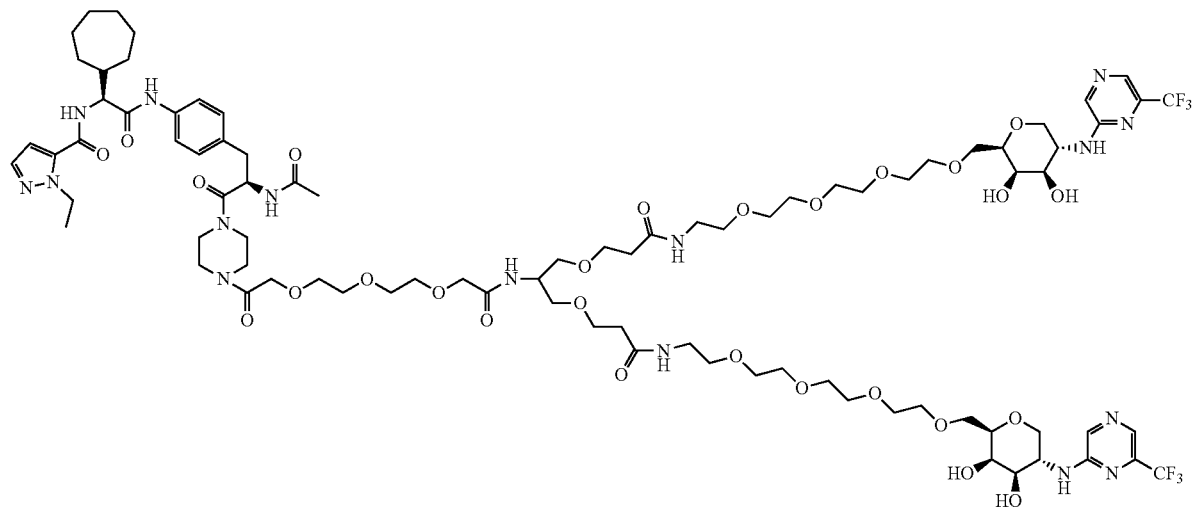

Compound 103

Compound 104
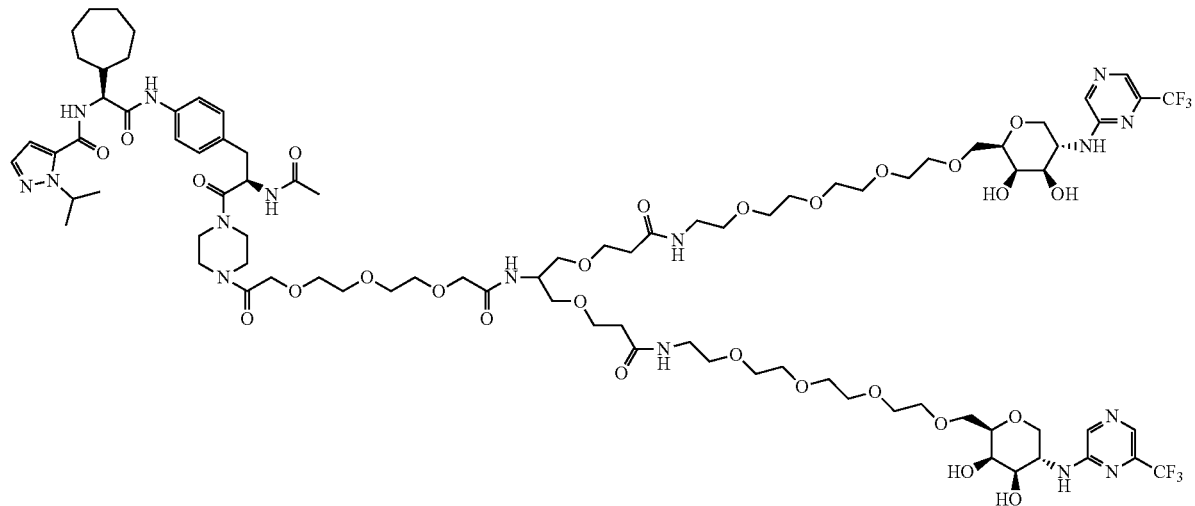
Synthesis of Compound 105: N-((2S)-1,1-dicyclopropyl-3-((4-(1-(1-((4R,7S)-2,2-dimethyl-7-((6-(trifluoromethyl)pyrazin-2-yl)amino)tetrahydro-4H-[1,3]dioxolo[4,5-c]pyran-4-yl)-2,5,8,11-tetraoxatridecan-13-yl)-3,5-dimethyl-1H-pyrazol-4-yl)phenyl)amino)-3-oxopropan-2-yl)-1-isopropyl-1H-pyrazole-5-carboxamide
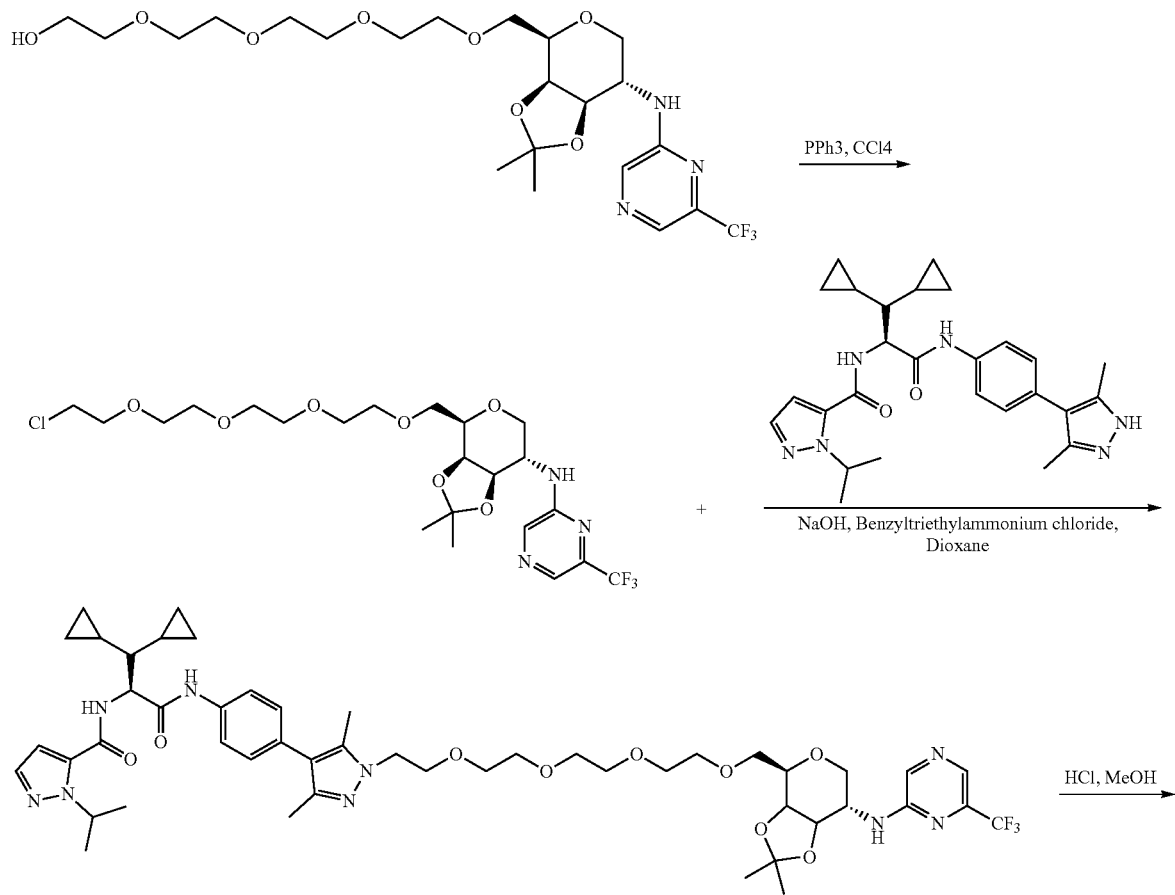

1333 1334
-continued
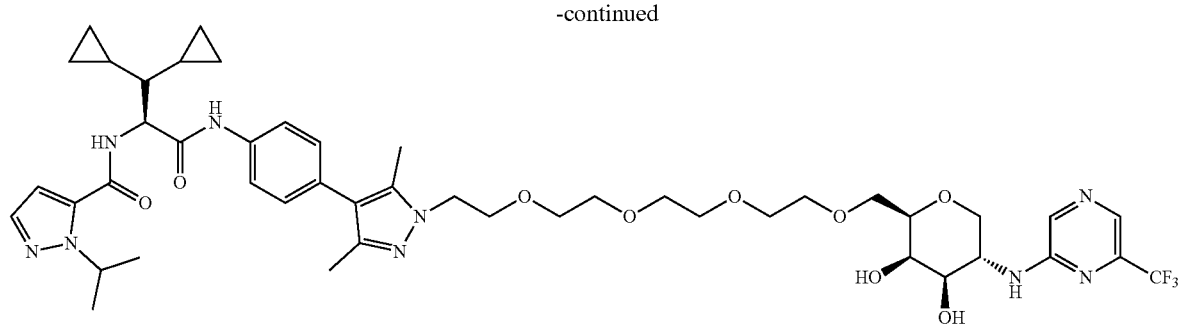
Compound 105
Synthesis of compound 106: 3,3'-((2-(2-(2-(2-(2-(4-(4-((S)-3,3-dicyclopropyl-2-(1-isopropyl-1H-pyrazole-5-carboxamido)propanamido)phenyl)-3,5-dimethyl-1H-pyrazol-1-yl)ethoxy)ethoxy)ethoxy)acetamido)propane-1,3-diyl)bis(oxy))bis(N-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-yl)propanamide)
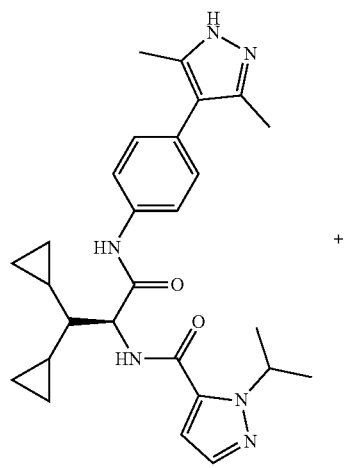
+
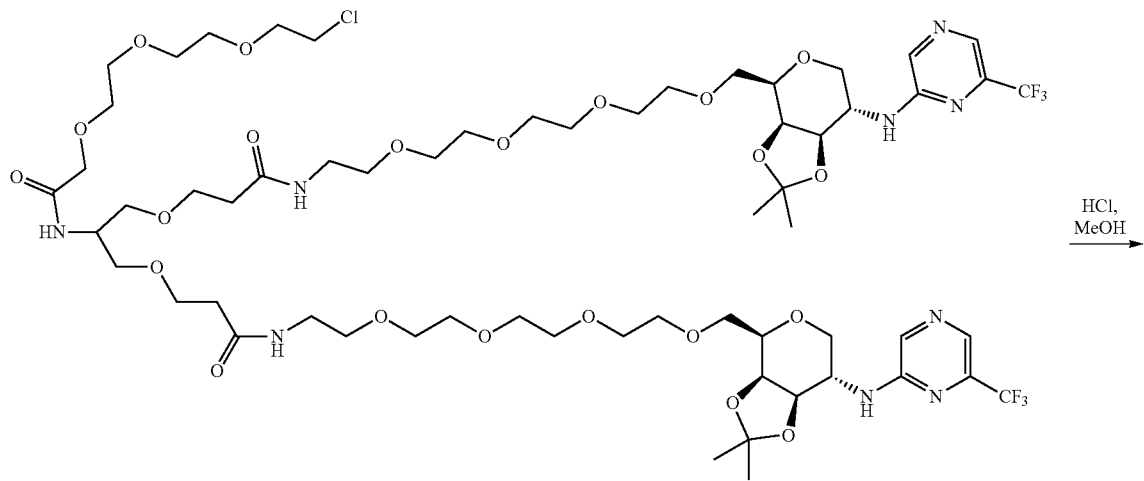
HCl, MeOH 1335 1336
-continued
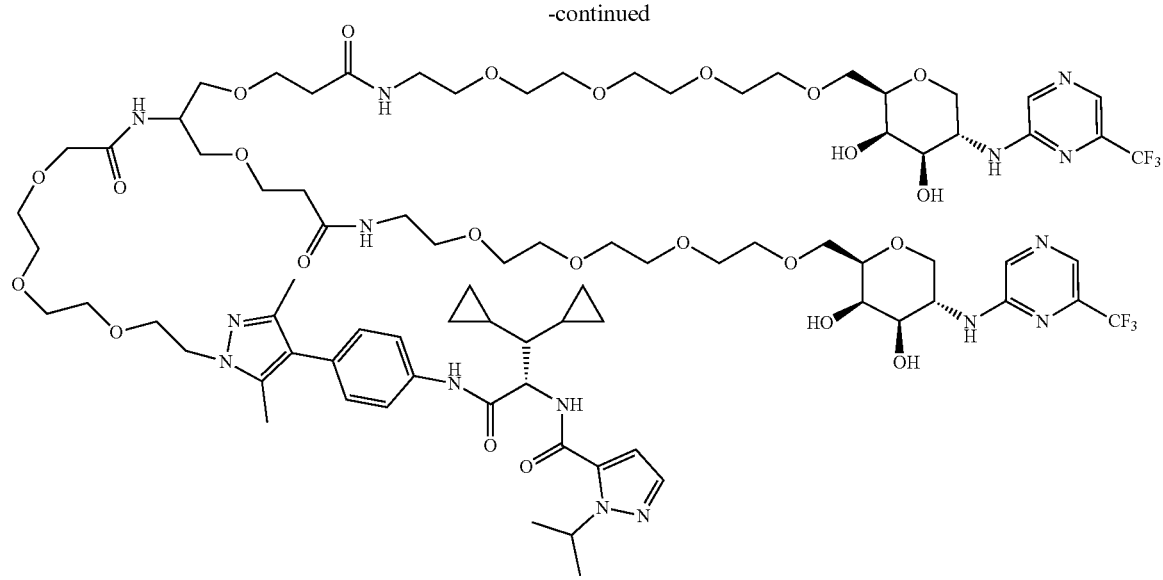
Synthesis of Compound 107: N—((S)-(4,4-difluoro-cyclohexyl)(7-((S)-1-((S)-3-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-yl)-2-oxo-4-(trifluoromethyl)imidazolidin-1-yl)-2-methoxyethyl)imidazo[1,2-b]pyridazin-2-yl)methyl)-4-methyl-1,2,5-oxadiazole-3-carboxamide
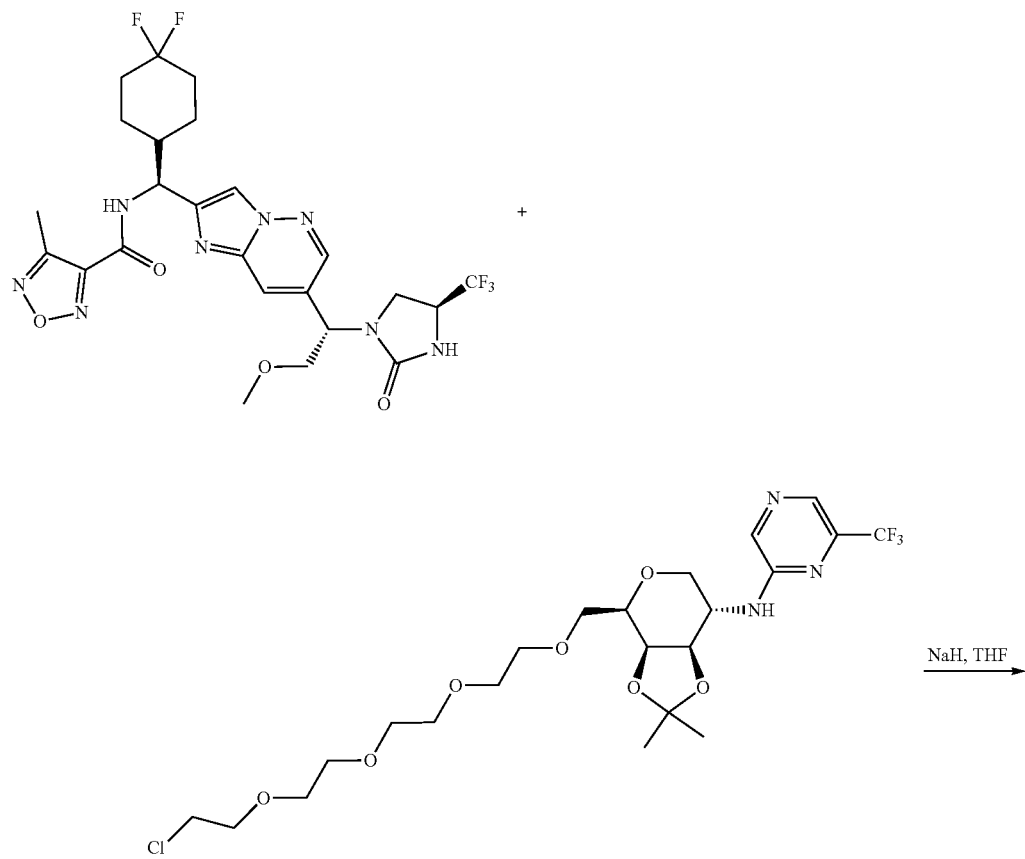

1337
-continued
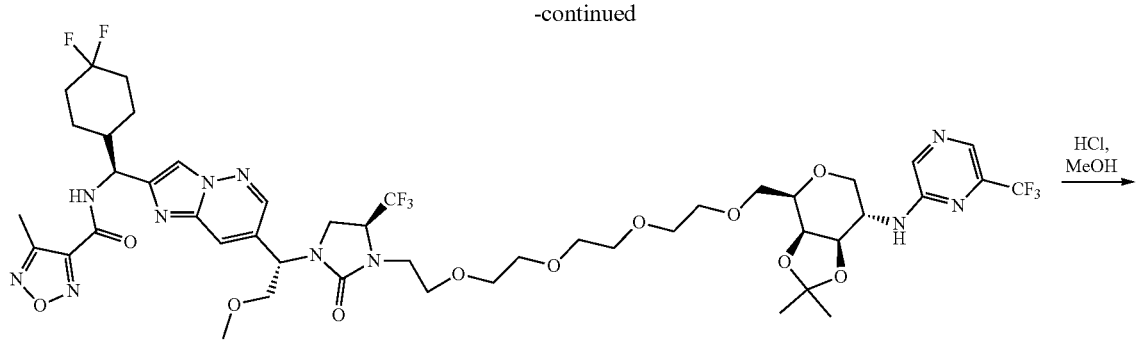
1338
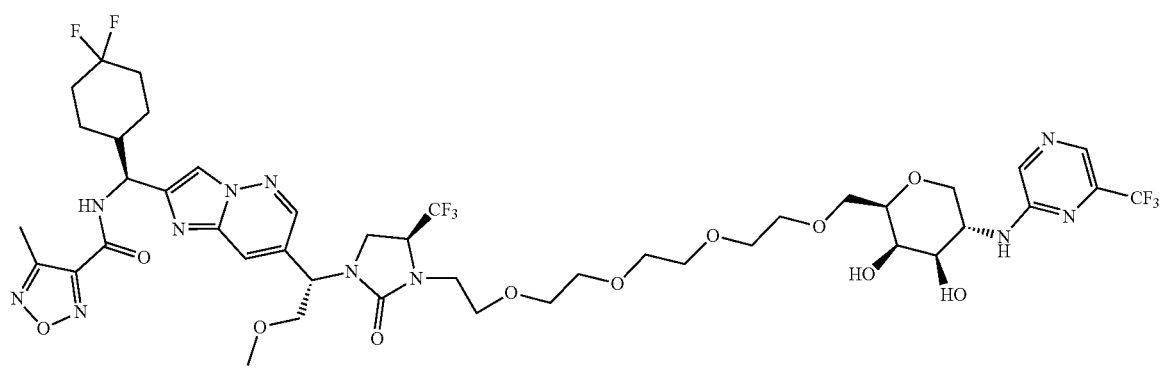
Synthesis of Compound 108: 3,3'-((2-(2-(2-(2-(2-((S)-3-((S)-1-(2-((S)-(4,4-difluorocyclohexyl)(4-methyl-1,2,5-oxadiazole-3-carboxamido)methyl)imidazo[1,2-b]pyridazin-7-yl)-2-methoxyethyl)-2-oxo-5-(trifluoromethyl)imidazolidin-1-yl)ethoxy)ethoxy)ethoxy)acetamido)propane-1,3-diyl)bis(oxy))bis(N-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-yl)propanamide)
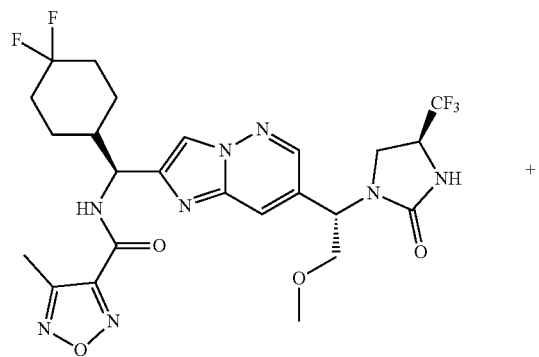
+

1339  1340
-continued
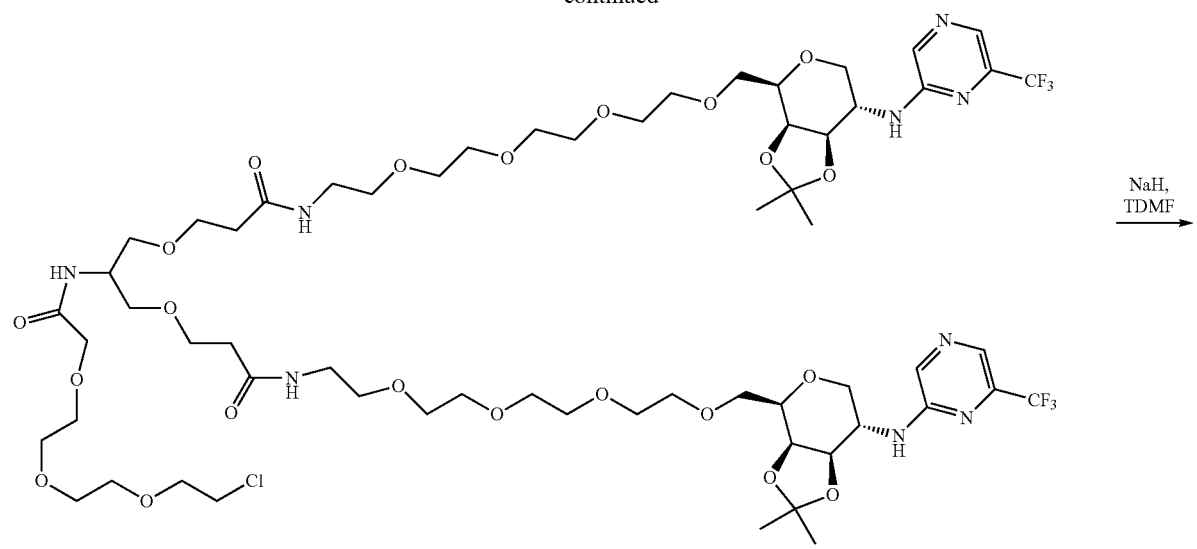
NaH,
TDMF
→
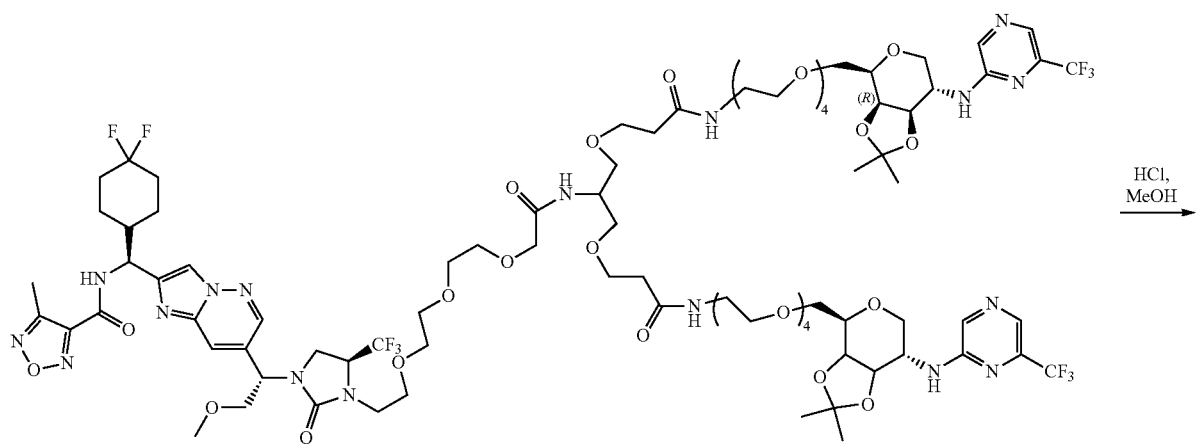
HCl,
MeOH
→
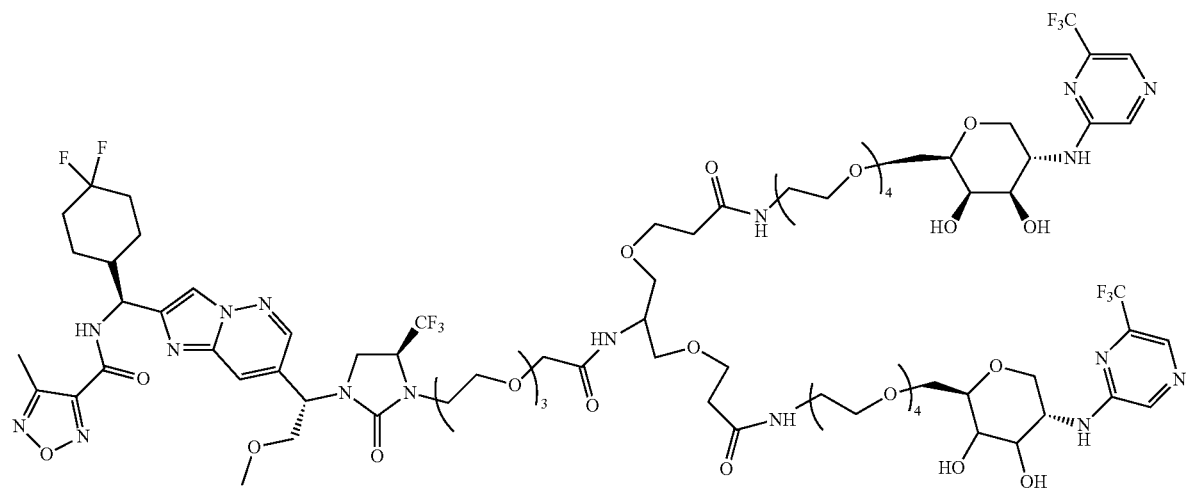

Compound 109: N—((S)-(4,4-difluorocyclohexyl)(7-((S)-1-((2R,3R,4R,5S)-3,4-dihydroxy-5-((6-(trifluoromethyl)pyrazin-2-yl)amino)tetrahydro-2H-pyran-2-yl)-16-((S)-2-oxo-4-(trifluoromethyl)imidazolidin-1-yl)-2,5,8,11,14-pentaoxahexadecan-16-yl)imidazo[1,2-b]pyridazin-2-yl)methyl)-4-methyl-1,2,5-oxadiazole-3-carboxamide

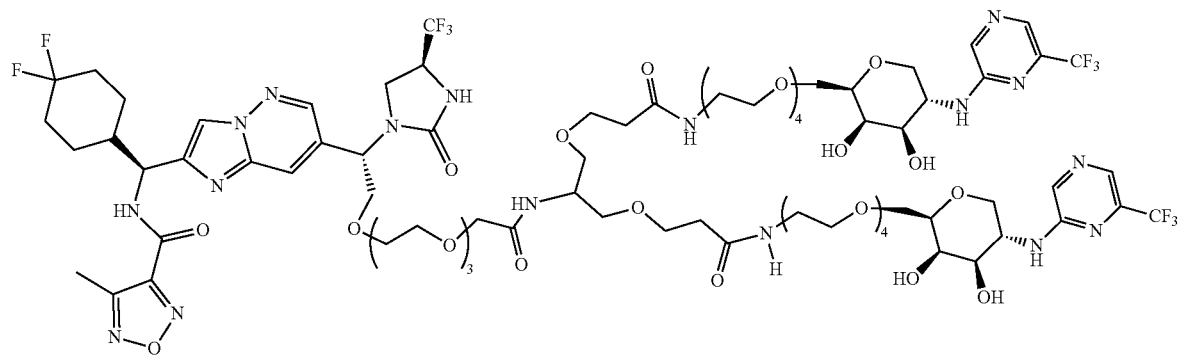

Preparation of 1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-20-(1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid

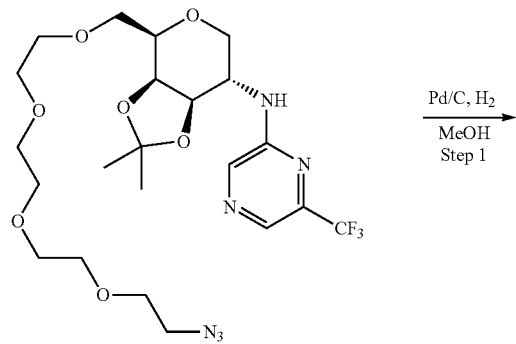

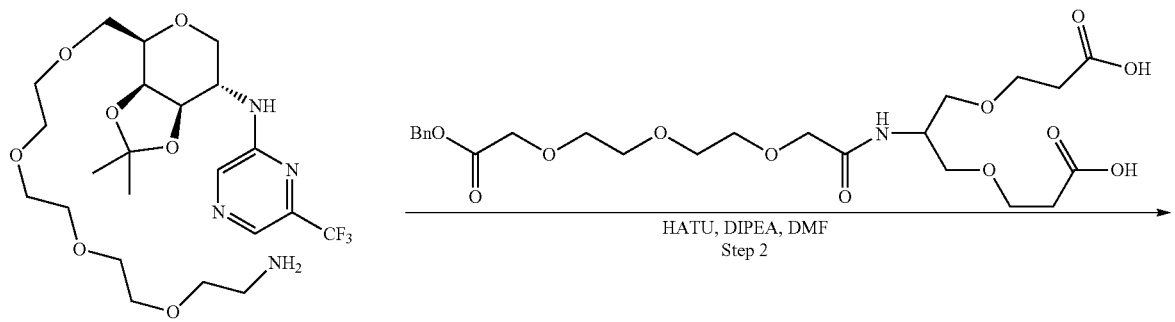

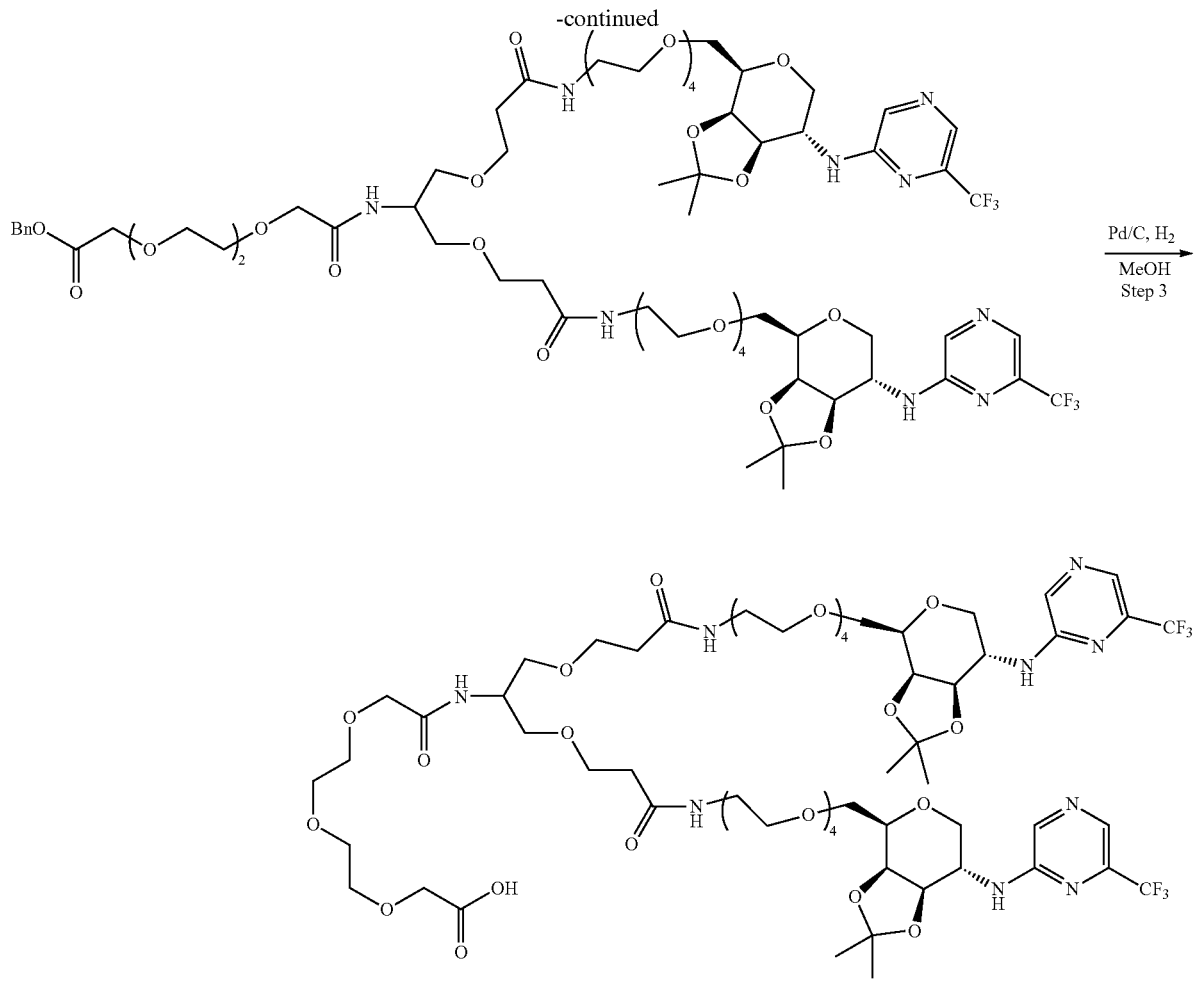

Step 1: To a solution of N-((3aR,4R,7S,7aR)-4-(13-azido-2,5,8,11-tetraoxatridecyl)-2,2-dimethyltetrahydro-4H-[1,3]dioxolo[4,5-c]pyran-7-yl)-6-(trifluoromethyl)pyrazin-2-amine (230 mg, 0.42 mmol) in MeOH (10 mL) was added Pd/C 10% (20 mg, 10% wt., 60% wet) at rt under a $H_2$ balloon. The reaction was stirred at rt for 0.5 h. The resulting mixture was filtered and concentrated in vacuo. The crude product was used for next step without further purification. LC-MS (ESI) found: 525 [M+H]$^+$.

Step 2: A solution of 15-((2-carboxyethoxy)methyl)-3,13-dioxo-1-phenyl-2,5,8,11,17-pentaoxa-14-azaicosan-20-oic acid (75 mg, 0.14 mmol), DIPEA (0.1 mL, 0.57 mmol) and HATU (118.5 mg, 0.31 mmol) in DMF (5 mL) was stirred at rt for 30 min. N-((3aR,4R,7S,7aR)-4-(13-amino-2,5,8,11-tetraoxatridecyl)-2,2-dimethyltetrahydro-4H-[1,3]dioxolo[4,5-c]pyran-7-yl)-6-(trifluoromethyl)pyrazin-2-amine (163.4 mg, 0.31 mmol) was added at rt. The reaction was stirred overnight. The resulting mixture was concentrated in vacuo. The crude product was purified by flash chromatography (silica gel, 0~10% MeOH in DCM) to give benzyl 1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-20-(1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (120 mg, 55% yield) as a colorless oil. LC-MS (ESI) found: 1543 [M+H]$^+$.

Step 3: To a solution of benzyl 1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-20-(1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (120 mg, 0.08 mmol) in MeOH (5 mL) was added Pd/C (12 mg, 10% wt., 60% wet) at rt under a $H_2$ balloon. The reaction was stirred at rt for 2 h. The resulting mixture was filtered and concentrated in vacuo. The crude product was purified by flash chromatography (silica gel, 0-15% MeOH in DCM) to give 1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-20-(1-((3aR,4R,7S,7aR)-2,2-dimethyl-7-((6-(trifluoromethyl)pyrazin-2-yl)amino)tetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid (50 mg, 44% yield) as a white solid. LC-MS (ESI) found: 1453 [M+H]$^+$. $^1$H NMR (400 MHz, CD$_3$OD): δ 8.10 (s, 2H), 8.02 (s, 2H), 4.33-4.25 (m, 4H), 4.22-4.18 (m, 1H), 4.14 (dd, J=8.8, 5.0 Hz, 2H), 4.01 (s, 2H), 3.95 (dd, J=12.2, 6.5 Hz, 6H), 3.75-3.62 (m, 40H), 3.57-3.51 (m, 8H), 3.38 (t, J=5.5 Hz, 4H), 3.14 (t, J=11.2 Hz, 2H), 2.46 (t, J=6.1 Hz, 4H), 1.50 (s, 6H), 1.33 (s, 6H). $^{19}$F NMR (377 MHz, CD$_3$OD): δ −70.31 (s).

Synthesis of Intermediate 33 (S)-4-(((4R,7S,10S, 13S,16S,22S,25S,28S,31S,34R)-25-((1H-imidazol-5-yl)methyl)-7,28-bis((1H-indol-3-yl)methyl)-4-(((2S,3R)-1-acetamido-3-hydroxy-1-oxobutan-2-yl)carbamoyl)-16-(3,17-dioxo-7,10,13-trioxa-4,16-diazadocos-21-yn-1-yl)-13,22-diisobutyl-10-isopropyl-31-methyl-6,9,12,15,18,21,24,27,30,33-decaoxo-1,2-dithia-5,8,11,14,17,20,23,26,29,32-decaazacyclopentatriacontan-34-yl)amino)-3-amino-4-oxobutanoic acid

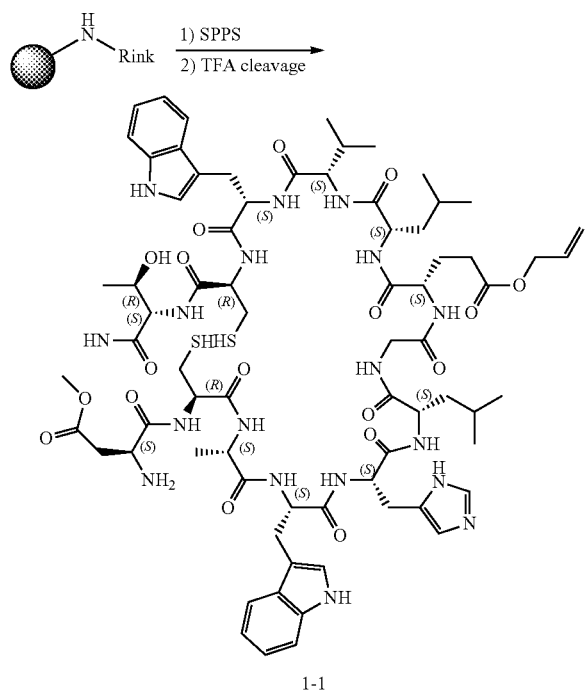

1-1

Step 1: Solid Phase Peptide Synthesis

The peptide is synthesized using standard Fmoc chemistry.

6) Resin preparation: AM Resin (66.67 g, 20.00 mmol, 0.30 mmol/g) in DMF (600 mL) is mixed for 30 minutes with $N_2$ bubbling at 15° C. The resin is washed with DMF (600 mL)*5. Then 20% piperidine in DMF (600 mL) is added and the mixture is bubbled with $N_2$ for 30 minutes at 15° C. The mixture is filtered to obtain the resin. The resin is washed with DMF (600 mL)*5 before proceeding to next step.

7) Coupling: A solution of Fmoc-Thr(tBu)-OH (23.82 g, 60.00 mmol, 3.00 eq), HBTU (21.60 g, 57 mmol, 2.85 eq) in DMF (300 mL) is added to the resin with $N_2$ bubbling. Then DIEA (22.11 mL, 120 mmol, 6.00 eq) is added to the mixture dropwise and bubbled with $N_2$ for 30 minutes at 15° C. The coupling reaction is monitored by ninhydrin test, if it showed colorless, the coupling is completed. The resin is then washed with DMF (600 mL)*5.

8) Deprotection: 20% piperidine in DMF (600 mL) is added to the resin and the mixture is bubbled with $N_2$ for 30 minutes at 15° C. The resin is then washed with DMF (600 mL)*5.

The Deprotection reaction is monitored by ninhydrin test, if it showed blue or other brownish red, the reaction is completed.

9) Step 2 and 3 were repeated for all other amino acids: (2-15 in the table below).

| # | Materials | Coupling reagents |
|---|---|---|
| 1 | Fmoc-Thr((Bu)-OH (3.00 eq) | HBTU (2.85 eq) and DIEA (6.00 eq) |
| 2 | Fmoc-Cys(Trt)-OH (3.00 eq) | HBTU (2.85 eq) and DIEA (6.00 eg) |
| 3 | Fmoc-Trp-OH (3.00 eq) | HBTU (2.85 eq) and DIEA (6.00 eq) |
| 4 | Fmoc-Val-OH (3.00 eq) | HBTU (2.85 eq) and DIEA (6.00 eq) |
| 5 | Fmoc-Leu-OH (3.00 eq) | HBTU (2.85 eq) and DIEA (6.00 eq) |
| 6 | Fmoc-Glu(OAll)-OH (3.00 eq) | HATU (2.85 eq) and DIEA (6.00 eq) |
| 7 | Fmoc-Gly-OH (3.00 eq) | HATU (2.85 eq) and DIEA (6.00 eq) |
| 8 | Fmoc-Leu-OH (3.00 eq) | HATU (2.85 eq) and DIEA (6.00 eq) |
| 9 | Fmoc-His(Trt)-OH (2.00 eq) | HATU (2.85 eq) and DIEA (6.00 eq) |
| 10 | Fmoc-Trp-OH (3.00 eq) | HATU (2.85 eq) and DIEA (6.00 eq) |
| 11 | Fmoc-Ala-OH (3.00 eq) | HATU (2.85 eq) and DIEA (6.00 eq) |
| 12 | Fmoc-Cys(Trt)-OH (3.00 eq) | HATU (2.85 eq) and DIEA (6.00 eq) |
| 13 | Fmoc-Asp(OMe)-OH (3.00 eq) | HATU (2.85 eq) and DIEA (6.00 eq) |
| 14 | Acetyl chloride (1.15 eq) | DIEA (3.00 eq) |

Step 2: Peptide Cleavage and Purification

7) Cleavage buffer (92.5% TFA/2.5% TIS/2.5% $1H_2O$/2.5% 3-mercaptopropanoic acid) is added to the flask containing the side chain protected peptide at room temperature and stir for 2 hrs.

8) The peptide is precipitated with cold isopropyl ether and centrifuged (3 mins at 3000 rpm).

9) Isopropyl ether washed two additional times.

10) Dried the crude peptide under vacuum 2 hrs.

11) A mixture of crude peptide in MeCN (10 L) and $H_2O$ (10 L), Iodine (0.1 M in AcOH) is added dropwise to vigorously stirring peptide solution until yellow color persists. After 2 minutes, Sodium thiosulfate (0.1 M in water) is added dropwise until yellow color disappears. The mixture is lyophilized to give the crude powder.

12) The crude peptide is purified by prep-HPLC (A: 0.075% TFA in $H_2O$, B: ACN) to give the title compound as a white solid.

Step 3: Coupling of Alkyne to Peptide
1347
1348
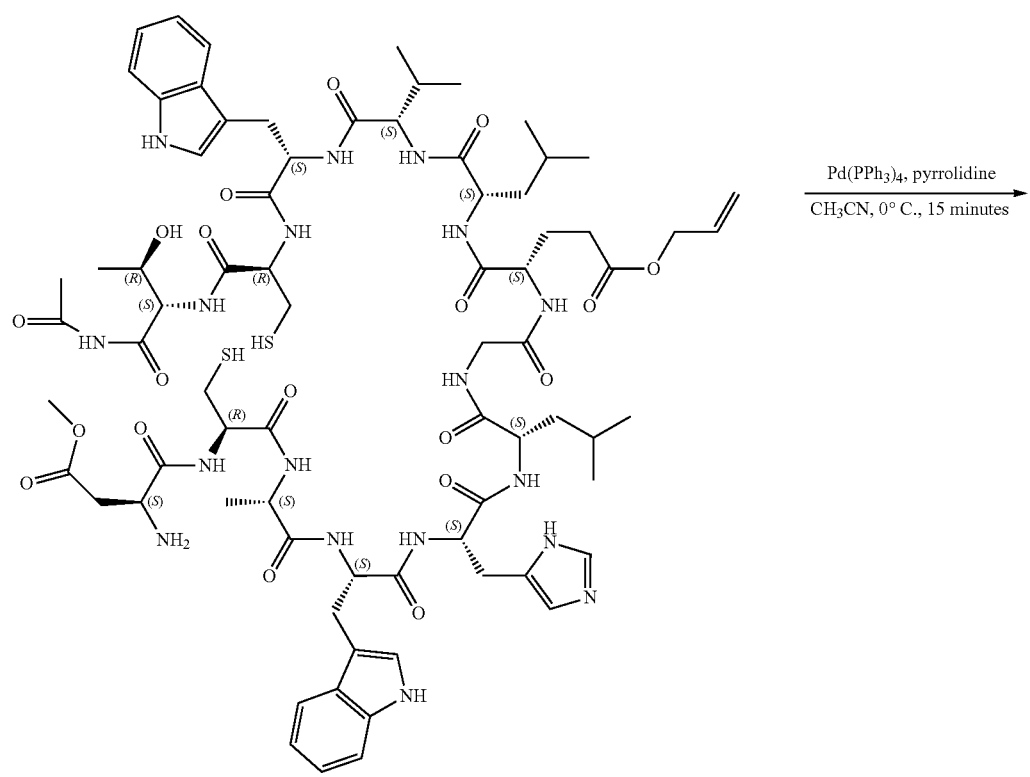
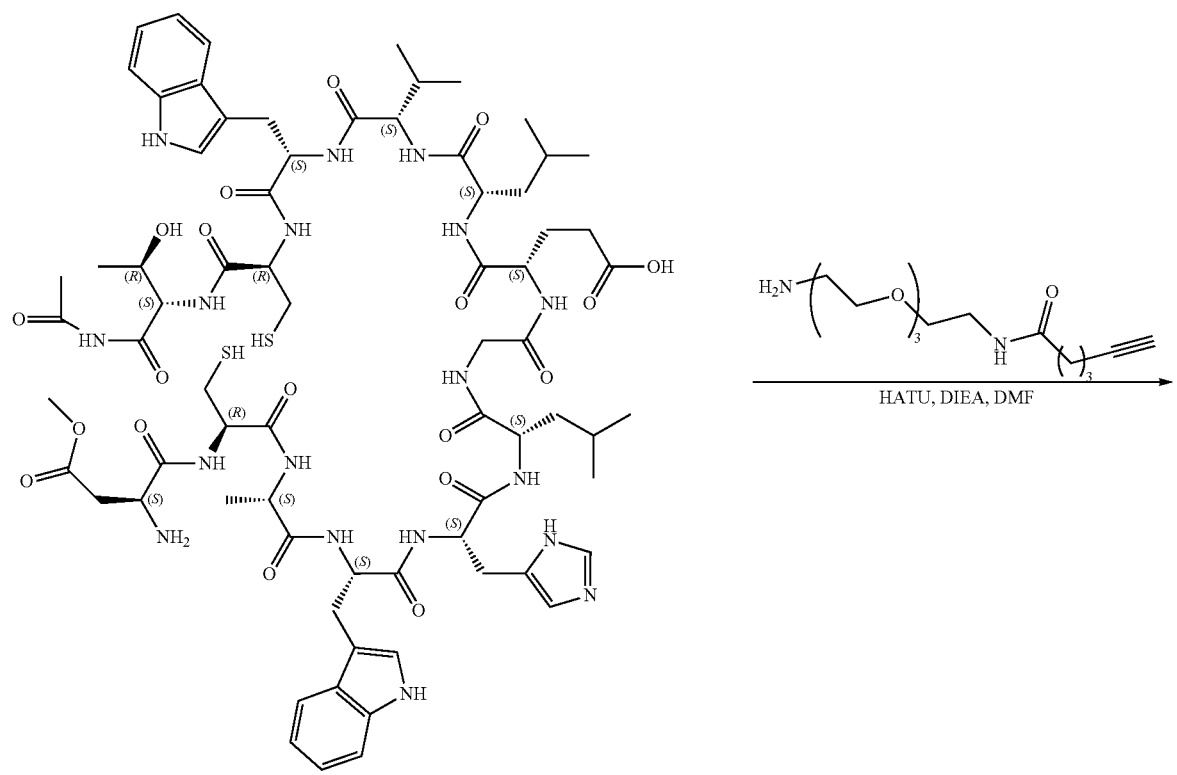

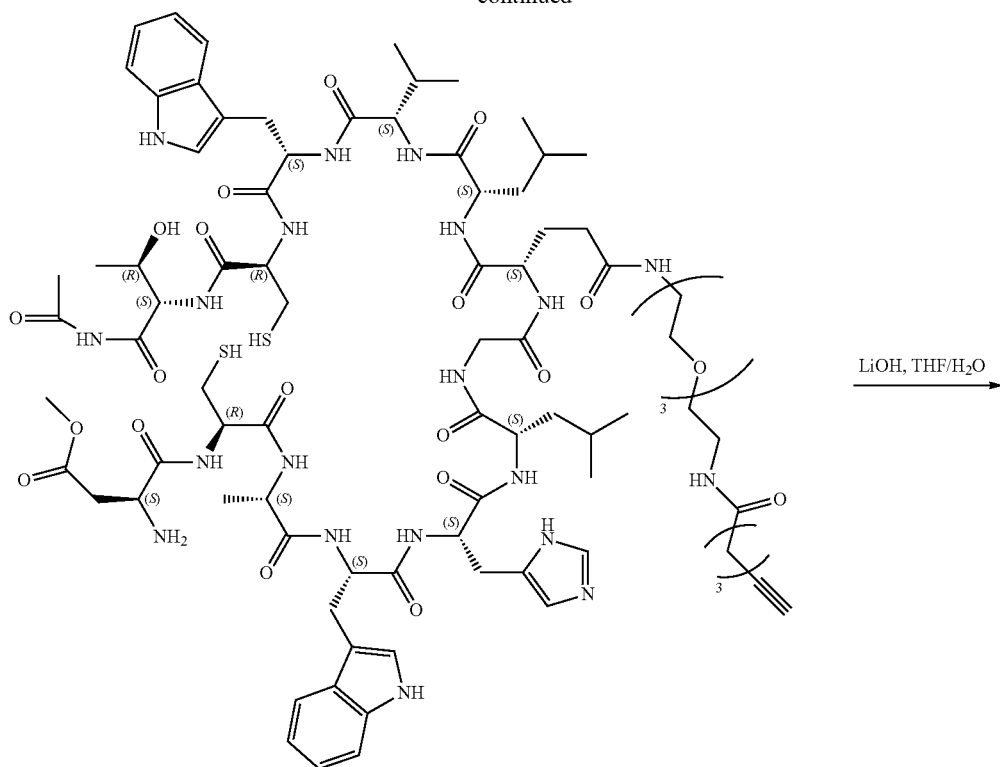
LiOH, THF/H₂O →
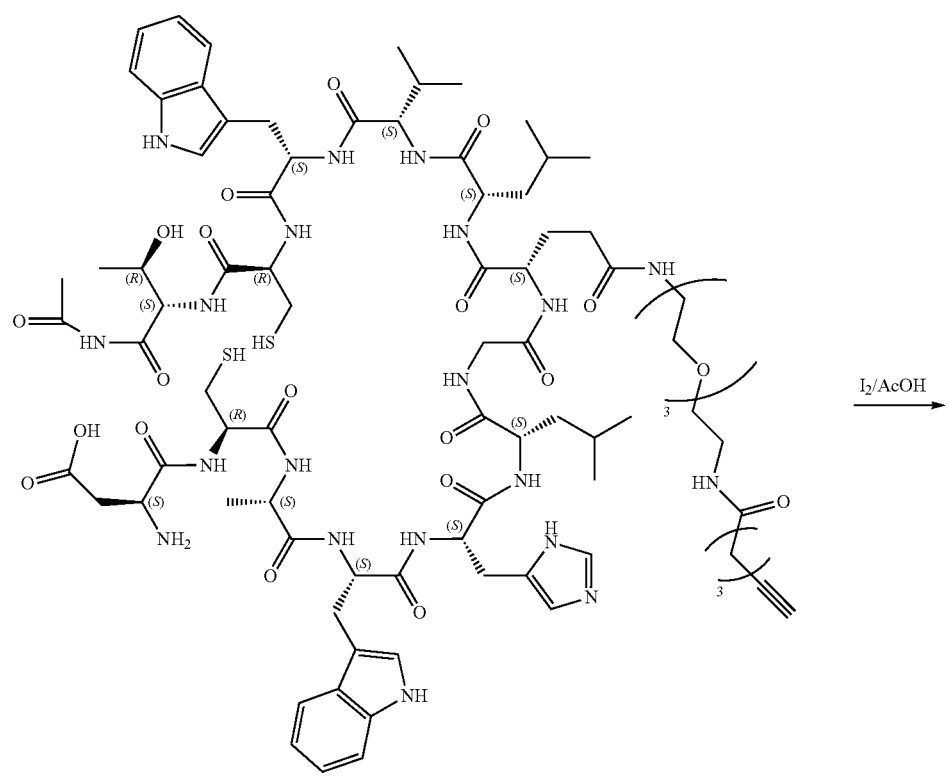
I₂/AcOH →

-continued
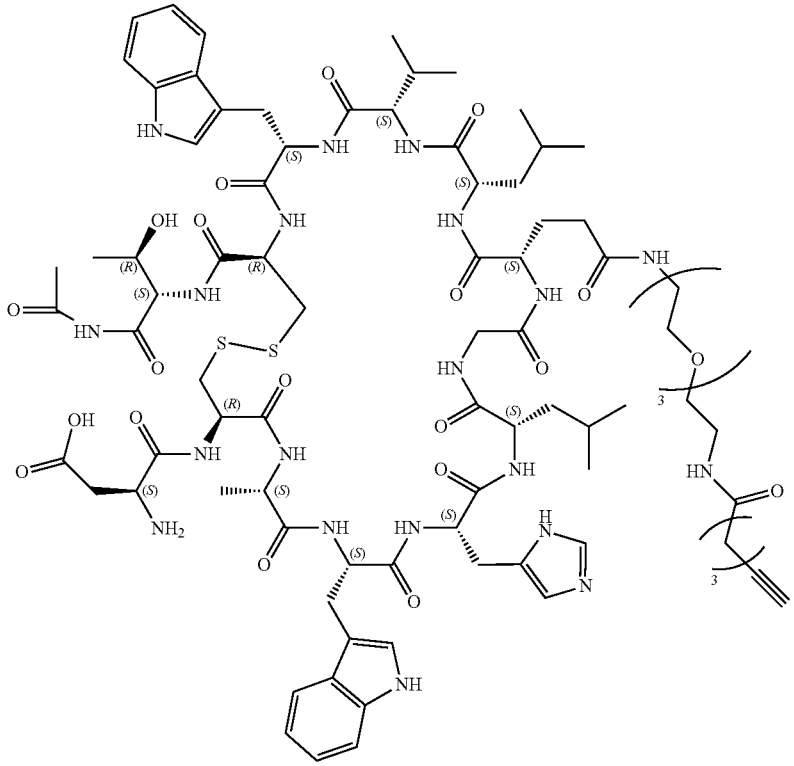
Intermediate 33
The resulting compound is characterized as follows:
| Intermediate 34 | AM Resin Fmoc amino acids |
|---|---|
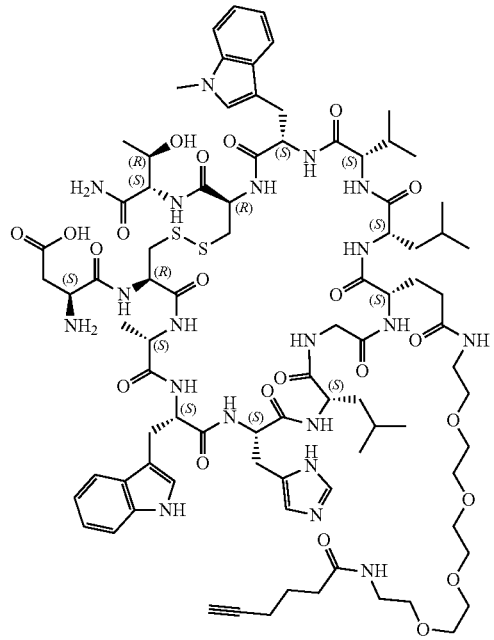
Intermediate 34 is synthesized using the same procedure for Intermediate 33, substituting Fmoc-Trp(1-Me)-OH for Fmoc-Trp-OH in step 3 of the solid phase peptide synthesis.

Synthesis of Intermediate 35: (S)-4-(((4R,7S,10S,13S,16S,22S,25S,28S,31S,34R)-25-((1H-imidazol-5-yl)methyl)-7-((1H-indol-3-yl)methyl)-4-(((2S,3R)-1-acetamido-3-hydroxy-1-oxobutan-2-yl)carbamoyl)-16-(2-carboxyethyl)-13,22-diisobutyl-10-isopropyl-31-methyl-6,9,12,15,18,21,24,27,30,33-decaoxo-28-((1-(2-(2-(2-(prop-2-yn-1-yloxy)ethoxy)ethoxy)ethyl)-1H-indol-3-yl)methyl)-1,2-dithia-5,8,11,14,17,20,23,26,29,32-decaazacyclopentatriacontan-34-yl)amino)-3-acetamido-4-oxobutanoic acid
Part 1: Synthesis of Functionalized Tryptophan:
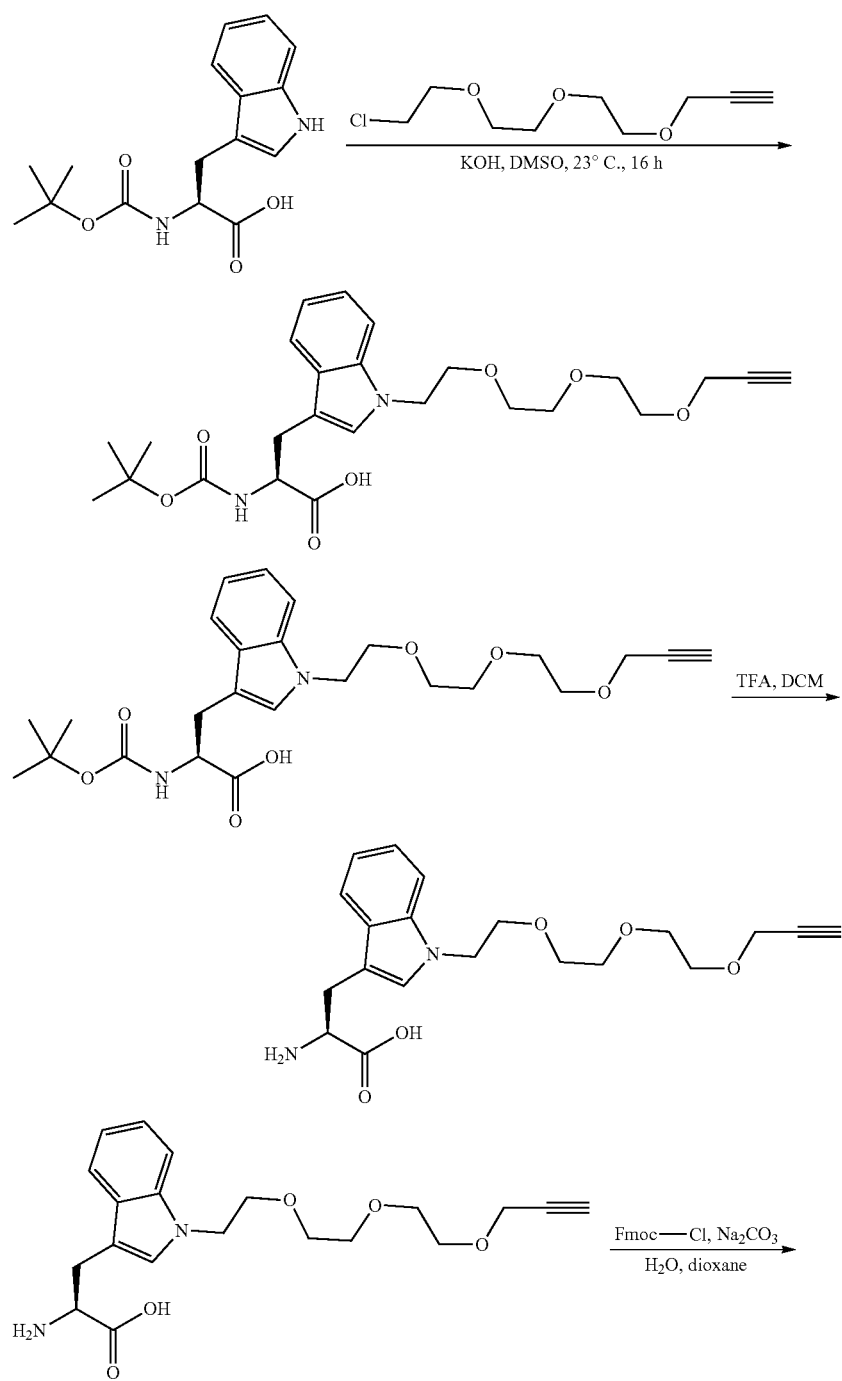

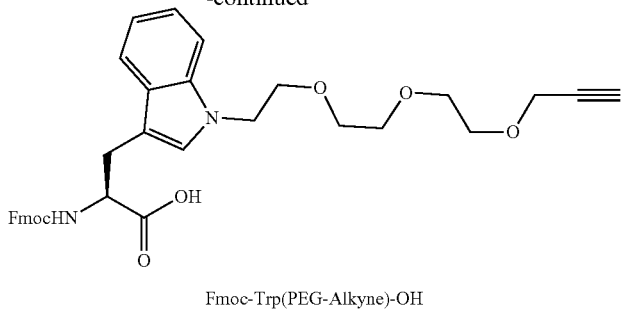

Fmoc-Trp(PEG-Alkyne)-OH

Part 2: Solid Phase Peptide Synthesis

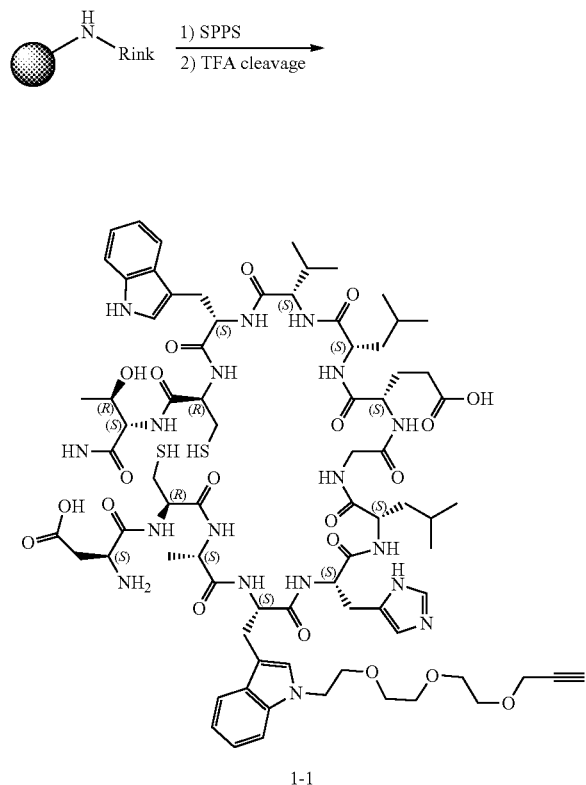

Step 1: Solid Phase Peptide Synthesis

The peptide is synthesized using standard Fmoc chemistry.

10) Resin preparation: AM Resin (66.67 g, 20.00 mmol, 0.30 mmol/g) in DMF (600 mL) is mixed for 30 minutes with $N_2$ bubbling at 15° C. The resin is washed with DMF (600 mL)*5. Then 20% piperidine in DMF (600 mL) is added and the mixture is bubbled with $N_2$ for 30 minutes at 15 FC. The mixture is filtered to obtain the resin. The resin is washed with DMF (600 mL)*5 before proceeding to next step.

11) Coupling: A solution of Fmoc-Thr(tBu)-OH (23.82 g, 60.00 mmol, 3.00 eq), HBTU (21.60 g, 57 mmol, 2.85 eq) in DMF (300 mL) is added to the resin with $N_6$ bubbling. Then DIEA (22.11 mL, 120 mmol, 6.00 eq) is added to the mixture dropwise and bubbled with $N_2$ for 30 minutes at 15 TC. The coupling reaction is monitored by ninhydrin test, if it showed colorless, the coupling is completed. The resin is then washed with DMF (600 mL)*5D 12) Deprotection: 20% piperidine in DMF (600 mL) is added to the resin and the mixture is bubbled with $N_2$ for 30 minutes at 15° C. The resin is then washed with DMF (600 mL)*5 The Deprotection reaction is monitored by ninhydrin test, if it showed blue or other brownish red, the reaction is completed.

13) Step 2 and 3 were repeated for all other amino acids: (2-15 in the table below).

| # | Materials | Coupling reagents |
|---|---|---|
| 1 | Fmoc-Thr((Bu)-OH (3.00 eq) | HBTU (2.85 eq) and DIEA (6.00 eq) |
| 2 | Fmoc-Cys(Trt)-OH (3.00 eq) | HBTU (2.85 eq) and DIEA (6.00 eq) |
| 3 | Fmoc-Trp(PEG-alkyne)-OH (3.00 eq) | HBTU (2.85 eq) and DIEA (6.00 eq) |
| 4 | Fmoc-Val-OH (3.00 eq) | HBTU (2.85 eq) and DIEA (6.00 eq) |
| 5 | Fmoc-Leu-OH (3.00 eq) | HBTU (2.85 eq) and DIEA (6.00 eq) |
| 6 | Fmoc-Glu(OtBu)-OH (3.00 eq) | HATU (2.85 eq) and DIEA (6.00 eq) |
| 7 | Fmoc-Gly-OH (3.00 eq) | HATU (2.85 eq) and DIEA (6.00 eg) |
| 8 | Fmoc-Leu-OH (3.00 eq) | HATU (2.85 eq) and DIEA (6.00 eq) |
| 9 | Fmoc-His(Trt)-OH (2.00 eg) | HATU (2.85 eq) and DIEA (6.00 eq) |
| 10 | Fmoc-Trp-OH (3.00 eq) | HATU (2.85 eq) and DIEA (6.00 eq) |
| 11 | Fmoc-Ala-OH (3.00 eq) | HATU (2.85 eq) and DIEA (6.00 eq) |
| 12 | Fmoc-Cys(Trt)-OH (3.00 eq) | HATU (2.85 eq) and DIEA (6.00 eq) |
| 13 | Fmoc-Asp(OtBu)-OH (3.00 eq) | HATU (2.85 eq) and DIEA (6.00 eq) |
| 14 | Acetyl chloride (1.15 eq) | DIEA (3.00 eq) |

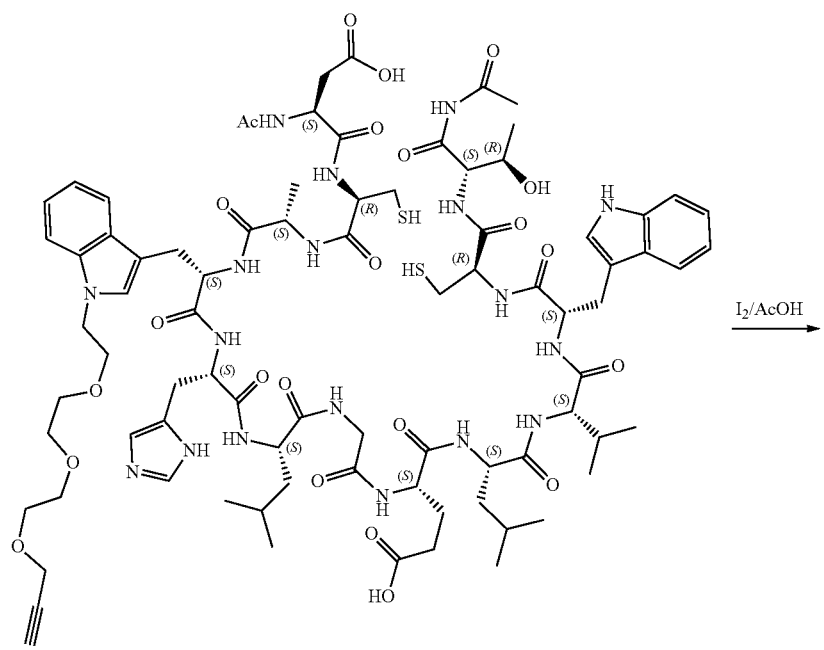

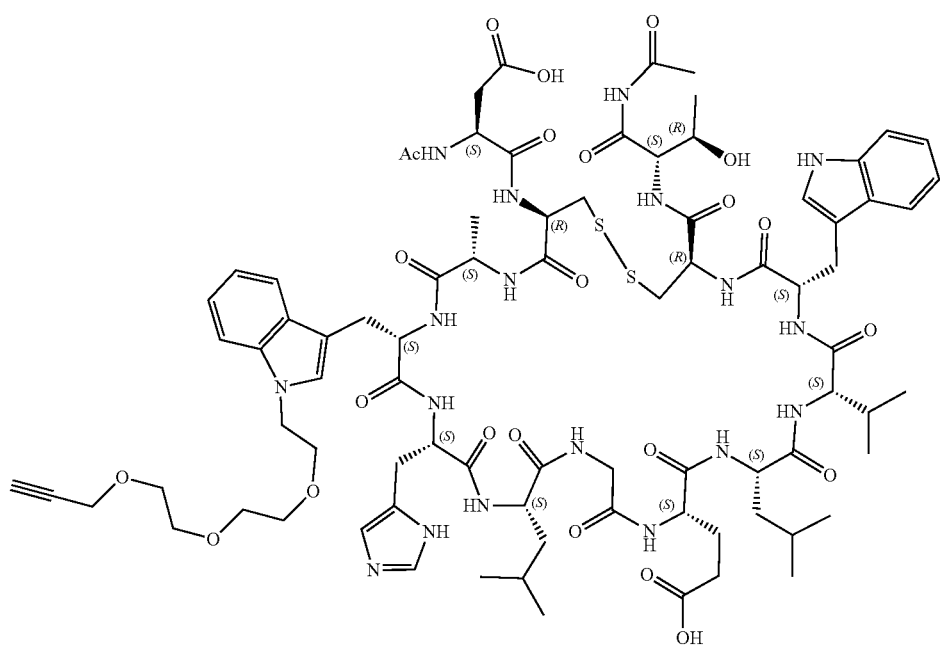

Step 2: Peptide Cleavage and Purification

13) Cleavage buffer (92.5% TFA/2.5% TIS/2.5%1H$_2$O/ 2.5% 3-mercaptopropanoic acid) is added to the flask containing the side chain protected peptide at room temperature and stir for 2 hrs.
14) The peptide is precipitated with cold isopropyl ether and centrifuged (3 mins at 3000 rpm).
15) Isopropyl ether washed two additional times.
16) Dried the crude peptide under vacuum 2 hrs.

17) A mixture of crude peptide in MeCN (10 L) and H$_2$O (10 L), Iodine (0.1 M in AcOH) is added dropwise to vigorously stirring peptide solution until yellow color persists. After 2 minutes, Sodium thiosulfate (0.1 M in water) is added dropwise until yellow color disappears. The mixture is lyophilized to give the crude powder.

18) The crude peptide is purified by prep-HPLC (A: 0.075% TFA in H$_2$O, B: ACN) to give the title compound as a white solid.

Preparation of Intermediate 36, 2-((6S,9R,12S,15S,18S,21S,27S,30S,33S,36S,39R,42S,44aS,46S,49aR)-30-((1H-imidazol-5-yl)methyl)-12,33-bis((1H-indol-3-yl)methyl)-46-amino-21-(3,17-dioxo-7,10,13-trioxa-4,16-diazadocos-21-yn-1-yl)-6-((R)-1-hydroxyethyl)-18,27-diisobutyl-15-isopropyl-36-methyl-5,8,11,14,17,20,23,26,29,32,35,38,41,44,49-pentadecaoxooctatetracontahydro-1H-9,39-(methanodithiomethano)dipyrrolo[1,2-a:1',2'-d][1,4,7,10,13,16,19,22,25,28,31,34,37,40,43]pentadecaazacyclopentatetracontin-42-yl)acetic acid
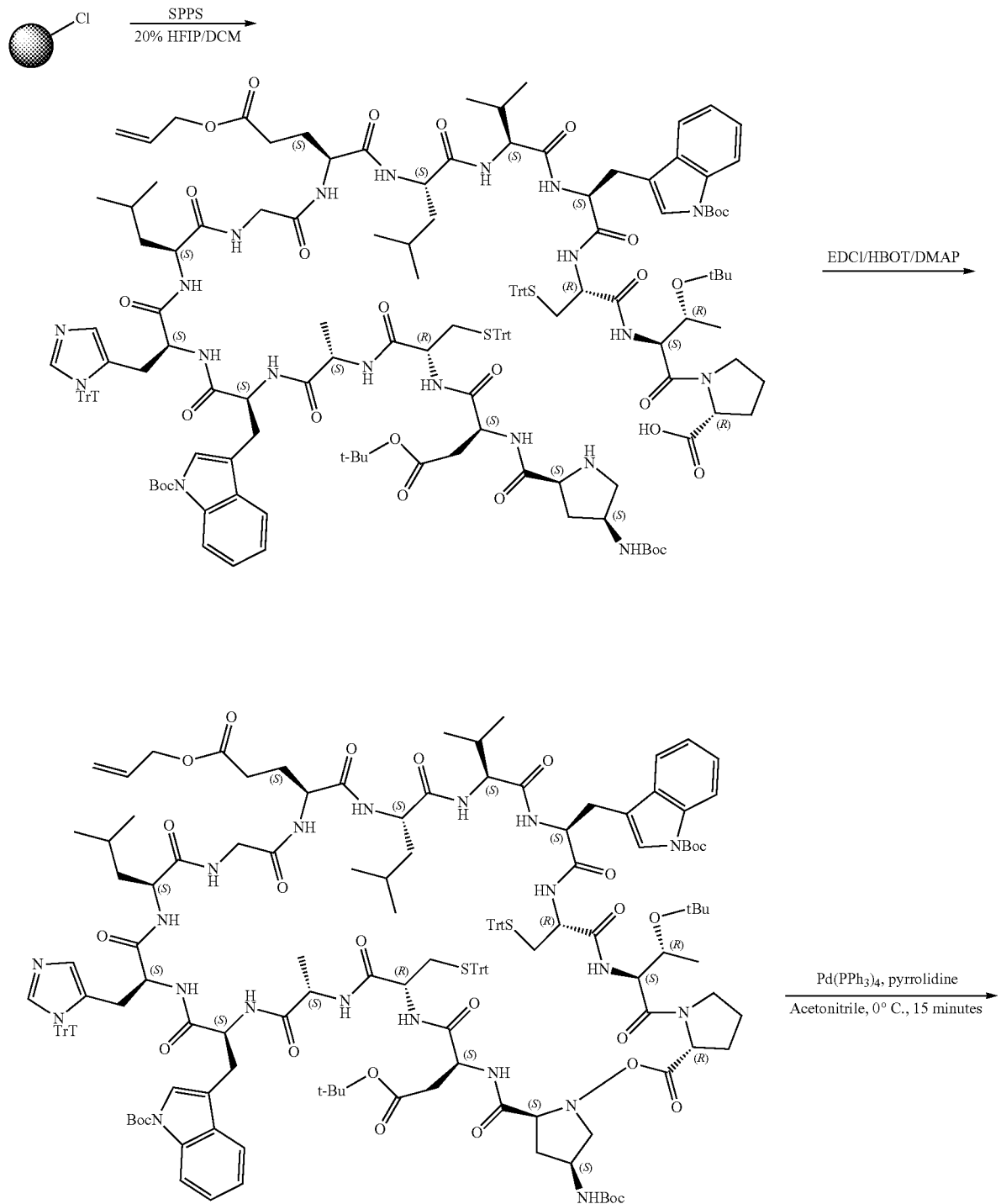

-continued
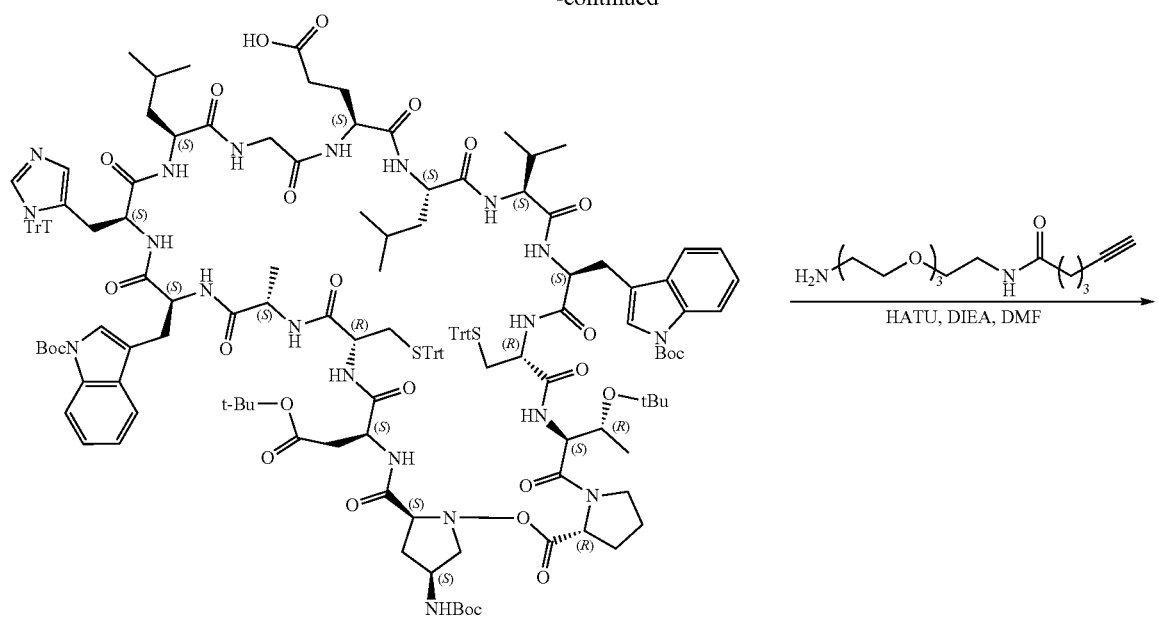
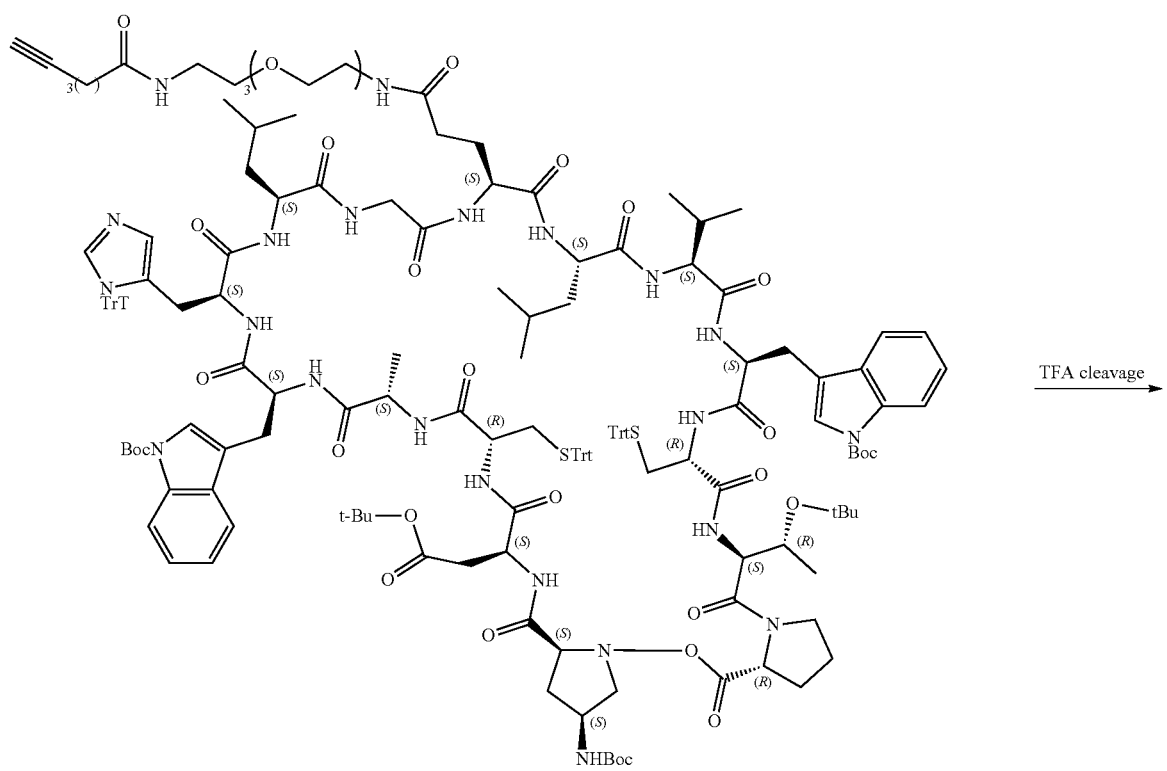

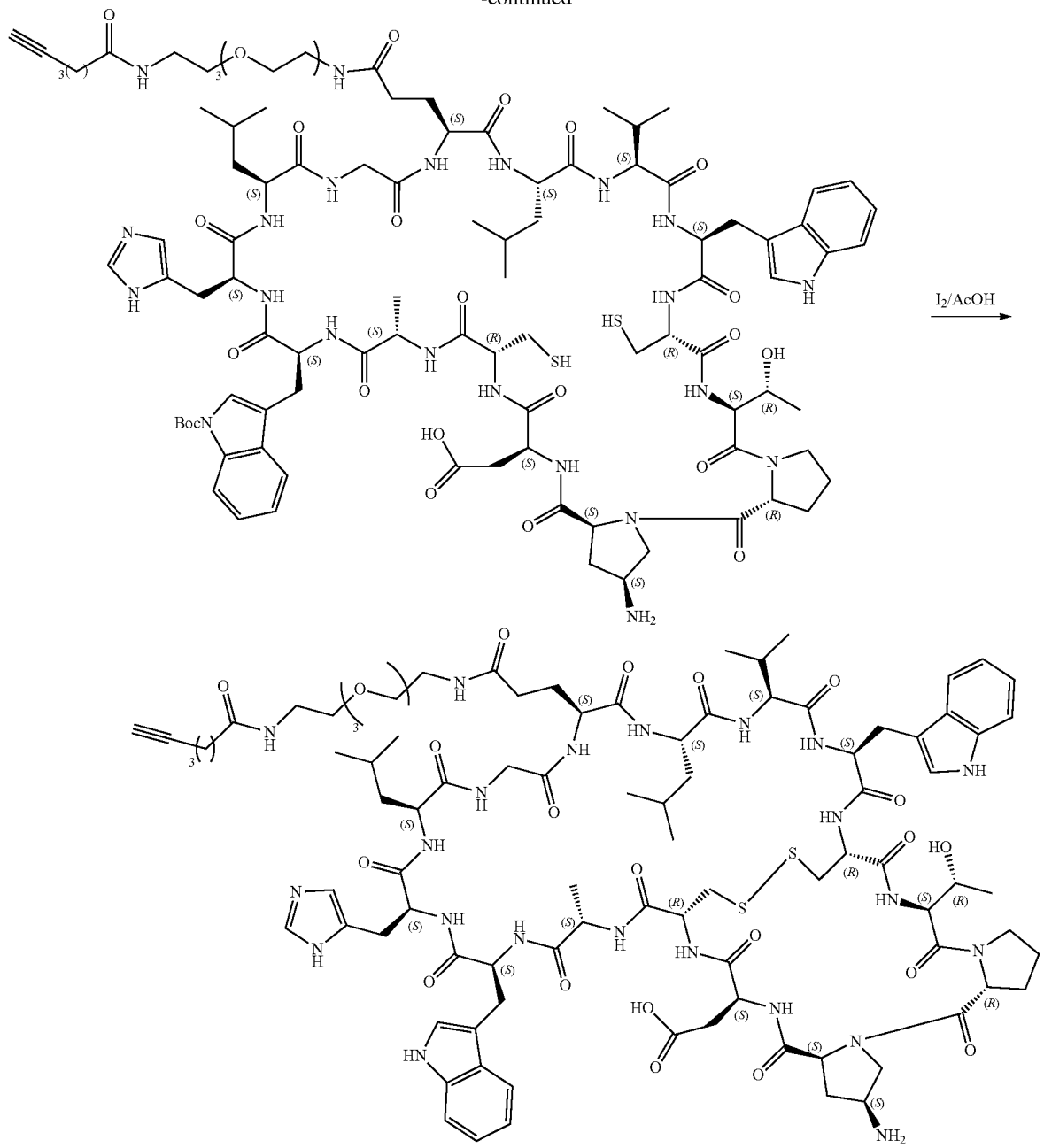

Solid Phase Peptide Synthesis of Intermediate 36

| # | Materials | Coupling reagents |
|---|---|---|
| 1 | Fmoc-D-Pro-OH (1.00 eq) | DIEA (4.00 eq) |
| 2 | Fmoc-Thr(tBu)-OH (3.00 eq) | HBTU (2.85 eq) and DIEA (6.00 eq) |
| 3 | Fmoc-Cys(Trt)-OH (3.00 eq) | HBTU (2.85 eq) and DIEA (6.00 eq) |
| 4 | Fmoc-Trp(Boc)-OH (3.00 eq) | HBTU (2.85 eq) and DIEA (6.00 eq) |
| 5 | Fmoc-Val-OH (3.00 eq) | HBTU (2.85 eq) and DIEA (6.00 eq) |
| 6 | Fmoc-Leu-OH (3.00 eq) | HBTU (2.85 eq) and DIEA (6.00 eq) |
| 7 | Fmoc-Glu(OAll)-OH (3.00 eq) | HBTU (2.85 eq) and DIEA (6.00 eq) |
| 8 | Fmoc-Gly-OH (3.00 eq) | HBTU (2.85 eq) and DIEA (6.00 eq) |
| 9 | Fmoc-Leu-OH (3.00 eq) | HBTU (2.85 eq) and DIEA (6.00 eq) |
| 10 | Fmoc-His(Trt)-OH (2.00 eq) | HBTU (2.85 eq) and DIEA (6.00 eq) |
| 11 | Fmoc-Trp-OH (3.00 eq) | HBTU (2.85 eq) and DIEA (6.00 eq) |
| 12 | Fmoc-Ala-OH (3.00 eq) | HBTU (2.85 eq) and DIEA (6.00 eq) |
| 13 | Fmoc-Cys(Trt)-OH (3.00 eq) | HBTU (2.85 eq) and DIEA (6.00 eq) |
| 14 | Fmoc-Asp(OtBu)-OH (3.00 eq) | HBTU (2.85 eq) and DIEA (6.00 eq) |
| 15 | BOC-(2S,4S)-4-AMINO-1-FMOC-PYRROLIDINE-2-CARBOXYLIC ACID (1.00 eq) | HATU (0.95 eq) and DIEA (2.00 eq) |

Preparation of Intermediate 37: 3-((6S,9R,12S,15S,18S,21S,27S,30S,33S,36S,39R,42S,44aS,46S,50aR)-30-((1H-imidazol-5-yl)methyl)-12,33-bis((1H-indol-3-yl)methyl)-46-amino-42-(2,16-dioxo-6,9,12-trioxa-3,15-diazahenicos-20-yn-1-yl)-6-((R)-1-hydroxyethyl)-18,27-diisobutyl-15-isopropyl-36-methyl-5,8,11,14,17,20,23,26,29,32,35,38,41,44,50-pentadecaoxooctatetracontahydro-1H-9,39-(methanodithiomethano)dipyrrolo[1,2-b:1',2'-r1][1]oxa[2,5,8,11,14,17,20,23,26,29,32,35,38,41,44]pentadecaazacyclohexatetracontin-21-yl)propanoic acid
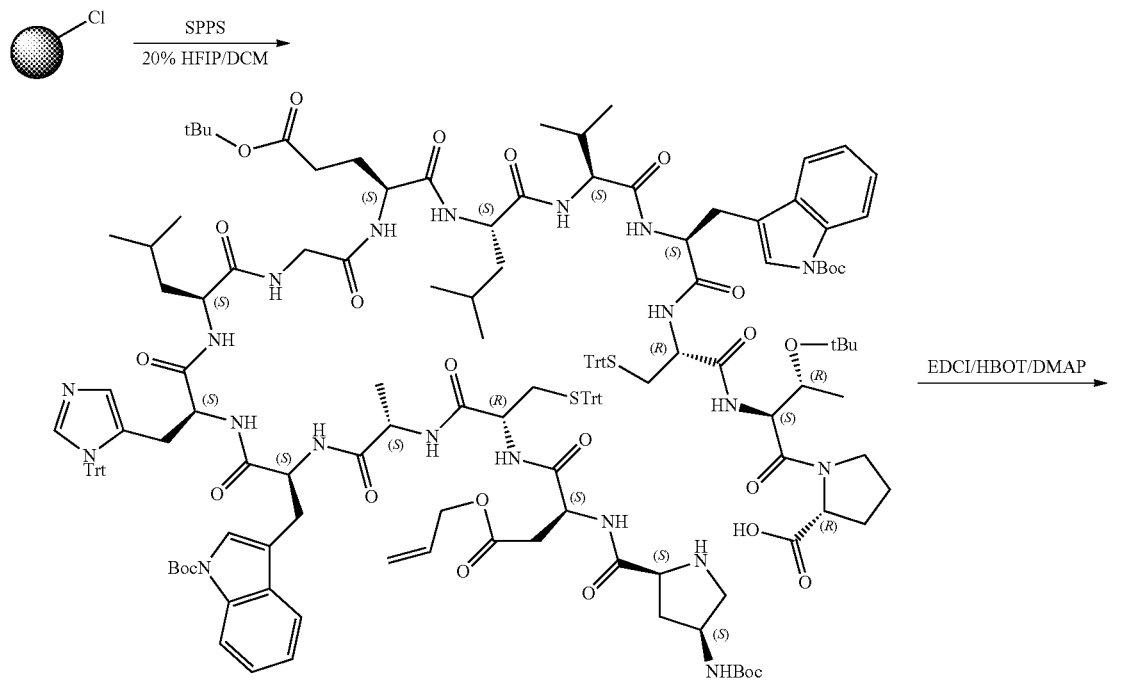
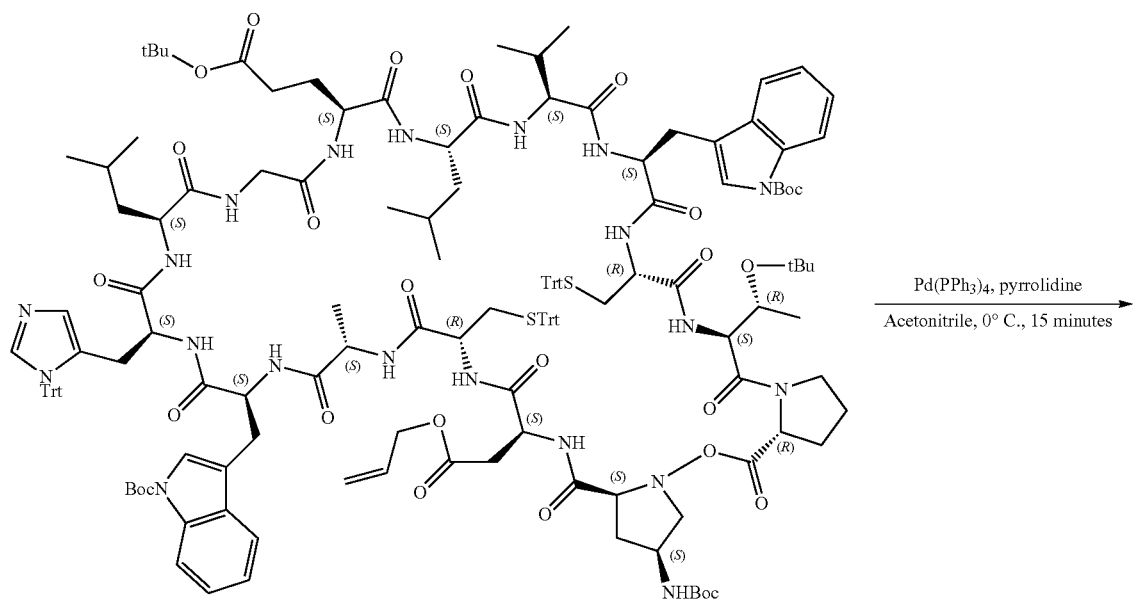

1367
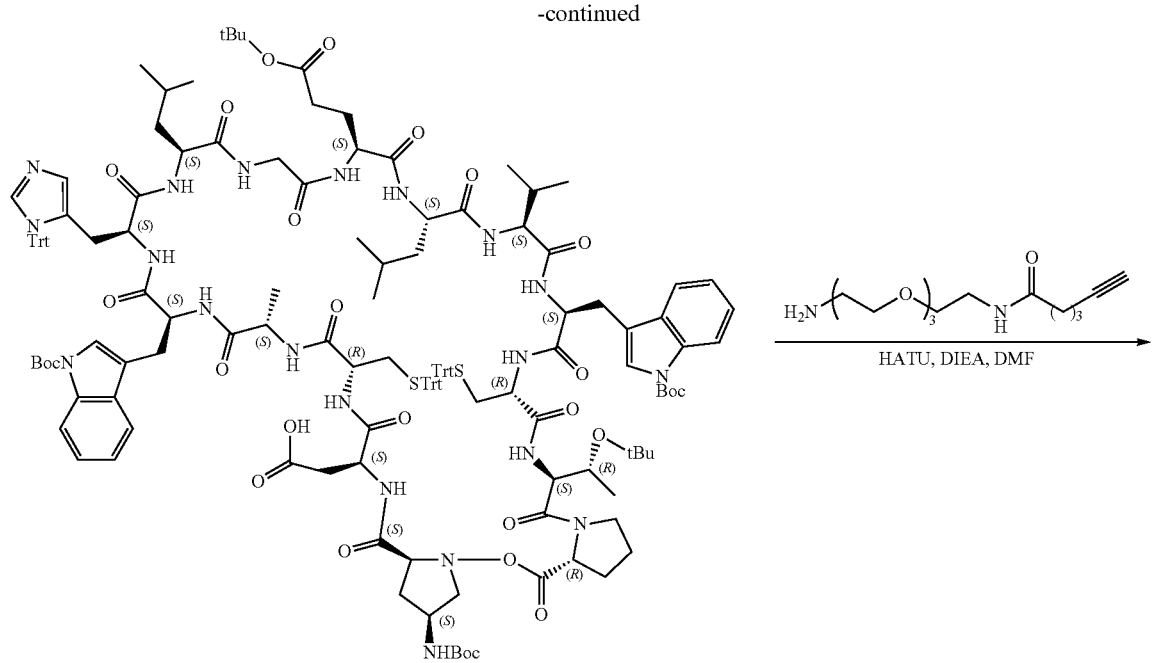
1368
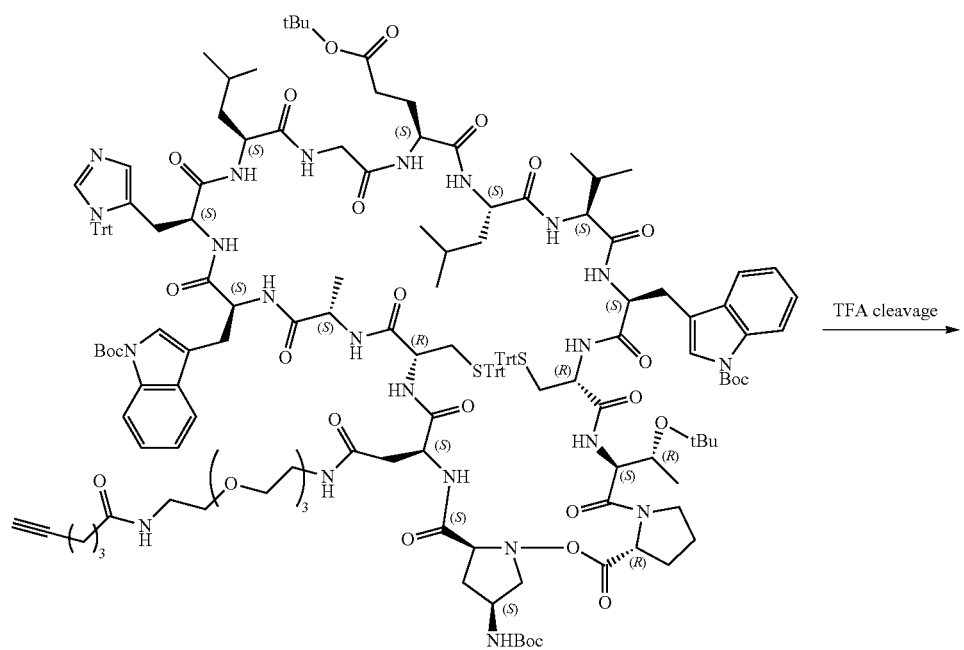

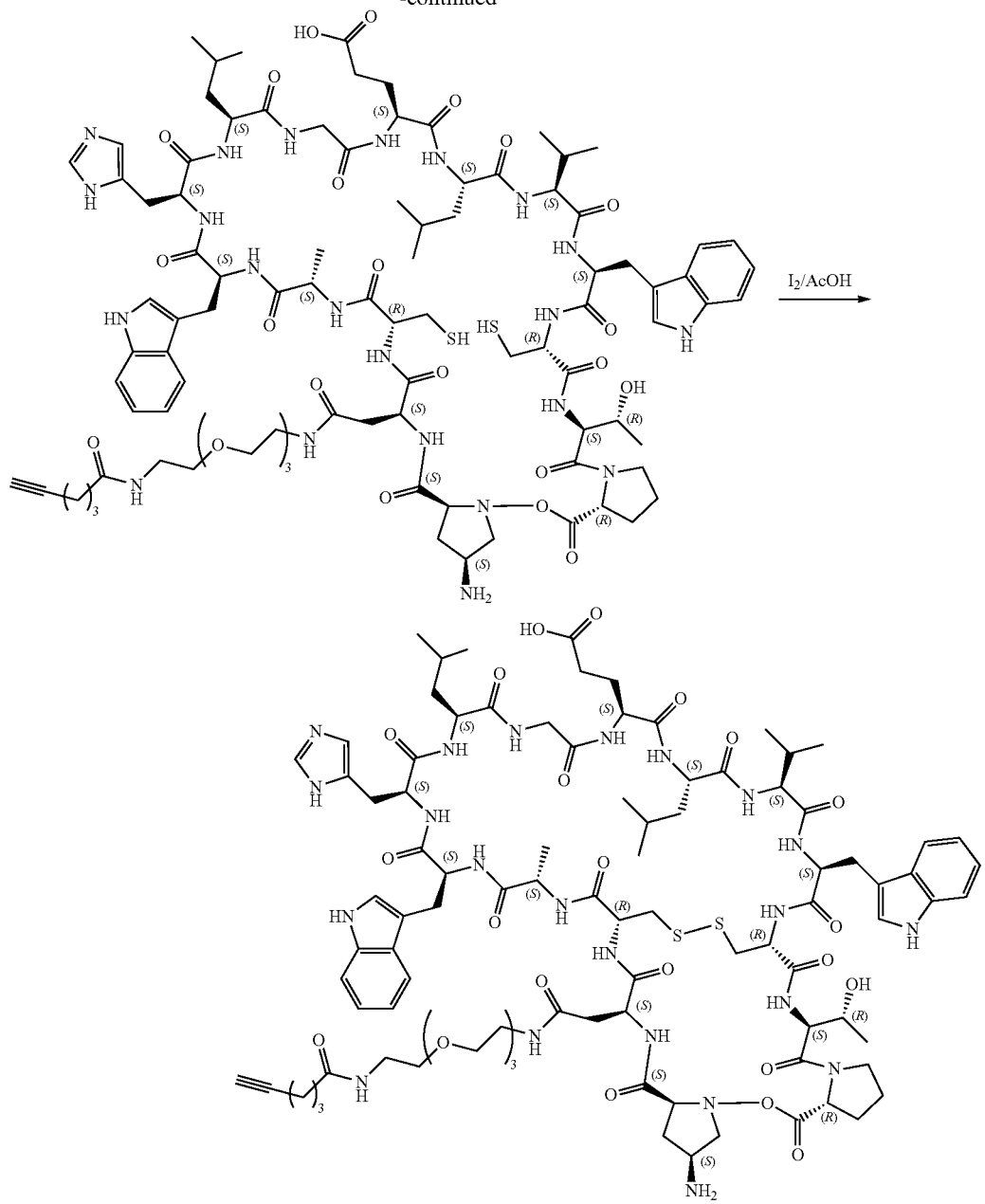

Solid Phase Peptide Synthesis for Intermediate 37

| # | Materials | Coupling reagents |
|---|---|---|
| 1 | Fmoc-D-Pro-OH (1.00 eq) | DIEA (4.00 eq) |
| 2 | Fmoc-Thr((Bu)-OH (3.00 eq) | HBTU (2.85 eq) and DIEA (6.00 eq) |
| 3 | Fmoc-Cys(Trt)-OH (3.00 eq) | HBTU (2.85 eq) and DIEA (6.00 eq) |
| 4 | Fmoc-Trp(Boc)-OH (3.00 eq) | HBTU (2.85 eq) and DIEA (6.00 eq) |
| 5 | Fmoc-Val-OH (3.00 eq) | HBTU (2.85 eq) and DIEA (6.00 eq) |
| 6 | Fmoc-Leu-OH (3.00 eq) | HBTU (2.85 eq) and DIEA (6.00 eq) |
| 7 | Fmoc-Glu(OtBu)-OH (3.00 eq) | HBTU (2.85 eq) and DIEA (6.00 eq) |
| 8 | Fmoc-Gly-OH (3.00 eq) | HBTU (2.85 eq) and DIEA (6.00 eq) |
| 9 | Fmoc-Leu-OH (3.00 eq) | HBTU (2.85 eq) and DIEA (6.00 eq) |
| 10 | Fmoc-His(Trt)-OH (2.00 eq) | HBTU (2.85 eq) and DIEA (6.00 eq) |
| 11 | Fmoc-Trp-OH (3.00 eq) | HBTU (2.85 eq) and DIEA (6.00 eq) |
| 12 | Fmoc-Ala-OH (3.00 eq) | HBTU (2.85 eq) and DIEA (6.00 eq) |
| 13 | Fmoc-Cys(Trt)-OH (3.00 eq) | HBTU (2.85 eq) and DIEA (6.00 eq) |
| 14 | Fmoc-Asp(OAll)-OH (3.00 eq) | HBTU (2.85 eq) and DIEA (6.00 eg) |
| 15 | BOC-(2S,4S)-4-AMINO-1-FMOC-PYRROLIDINE-2-CARBOXYLIC ACID (1.00 eq) | HATU (0.95 eq) and DIEA (2.00 eq) |

Preparation of Intermediate 38: 3-((6S,9R,12S,15S, 18S,21S,27S,30S,33S,36S,39R,42S,44aS,46S, 50aR)-30-((1H-imidazol-5-yl)methyl)-12-((1H-indol-3-yl)methyl)-46-amino-42-(carboxymethyl)-6-((R)-1-hydroxyethyl)-18,27-diisobutyl-15-isopropyl-36-methyl-5,8,11,14,17,20,23,26,29,32,35,38,41,44, 50-pentadecaoxo-33-((1-(2-(2-(2-(prop-2-yn-1-yloxy)ethoxy)ethoxy)ethyl)-1H-indol-3-yl)methyl) octatetracontahydro-1H-9,39-(methanodithiomethano)dipyrrolo[1,2-b:1',2'-r1][1] oxa[2,5,8,11,14,17,20,23,26,29,32,35,38,41,44] pentadecaazacyclohexatetracontin-21-yl)propanoic acid
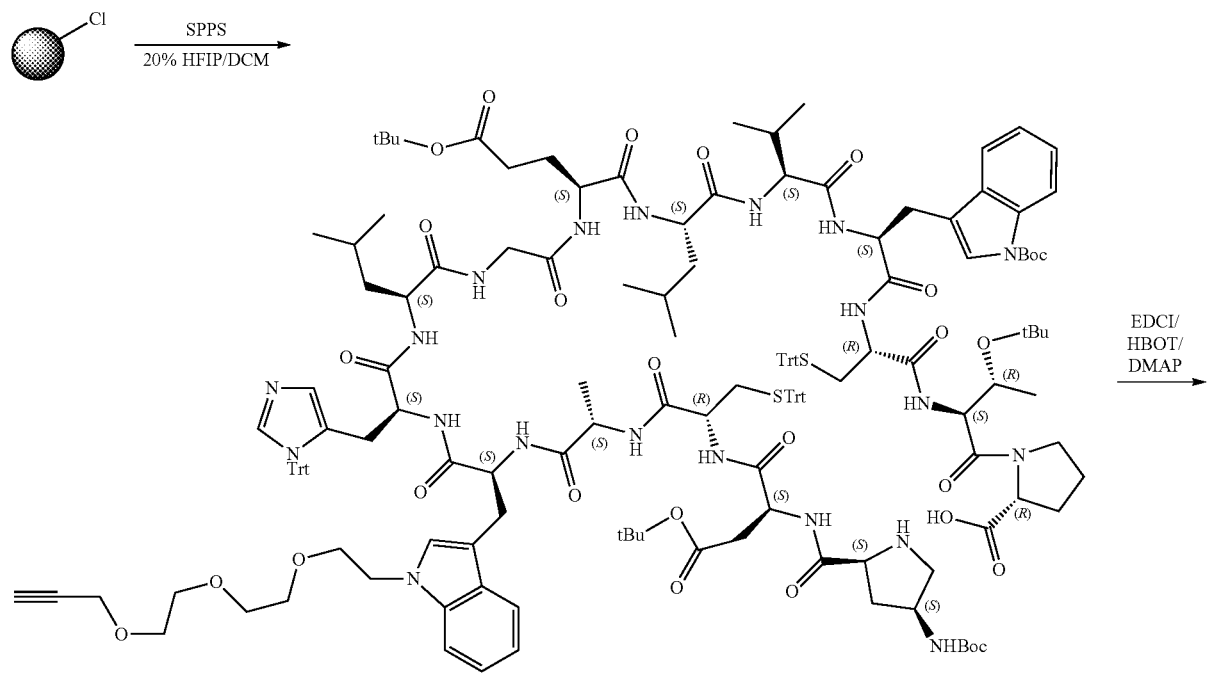
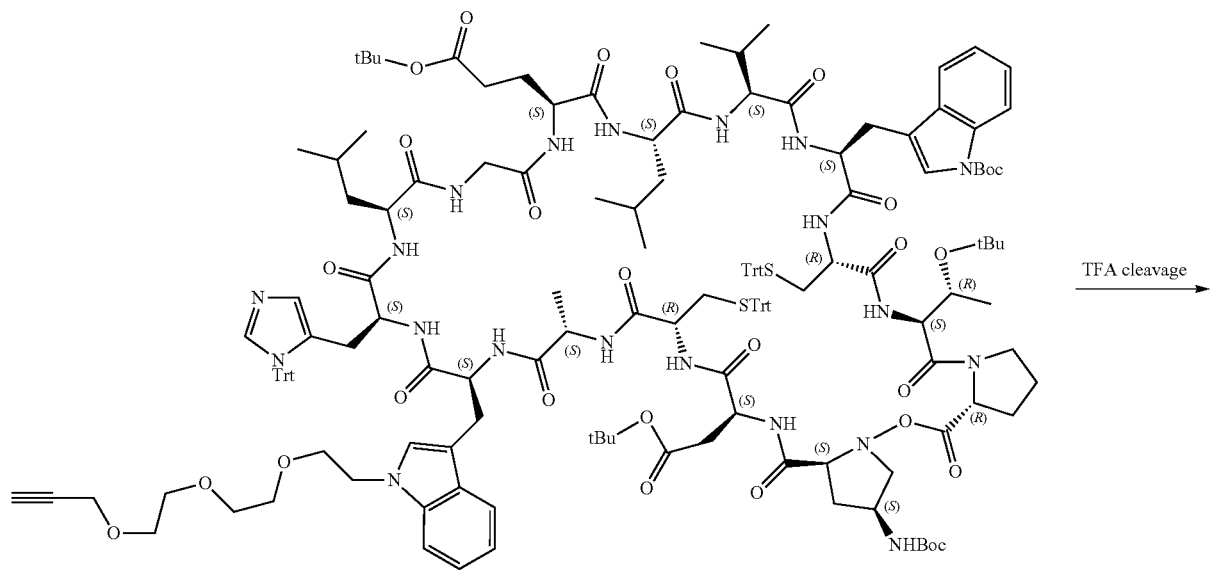

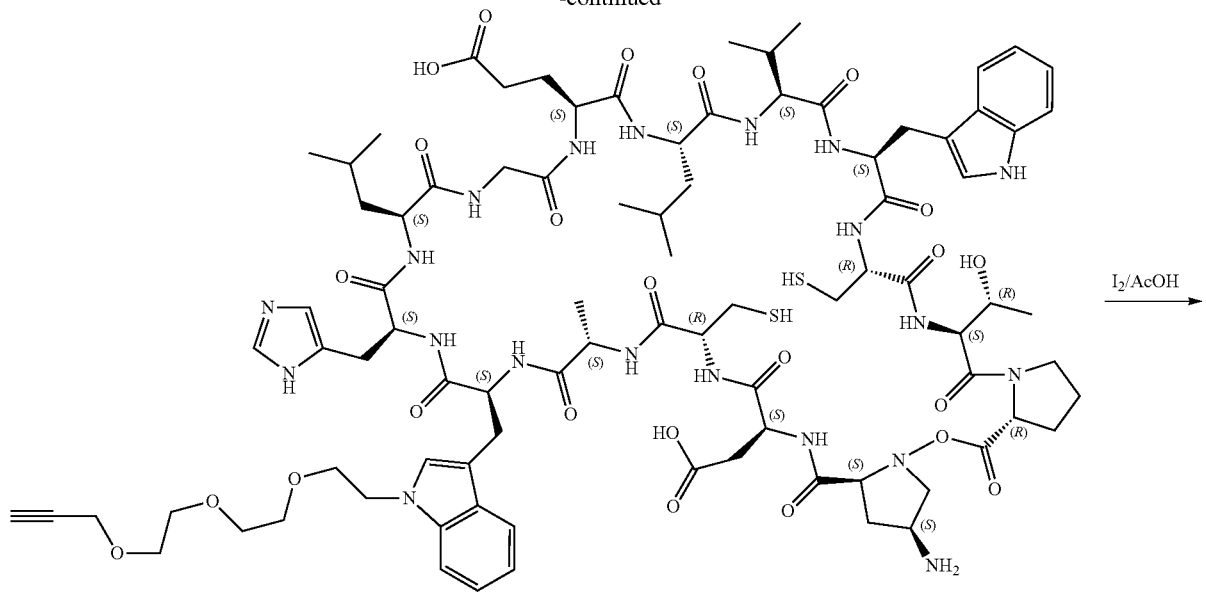

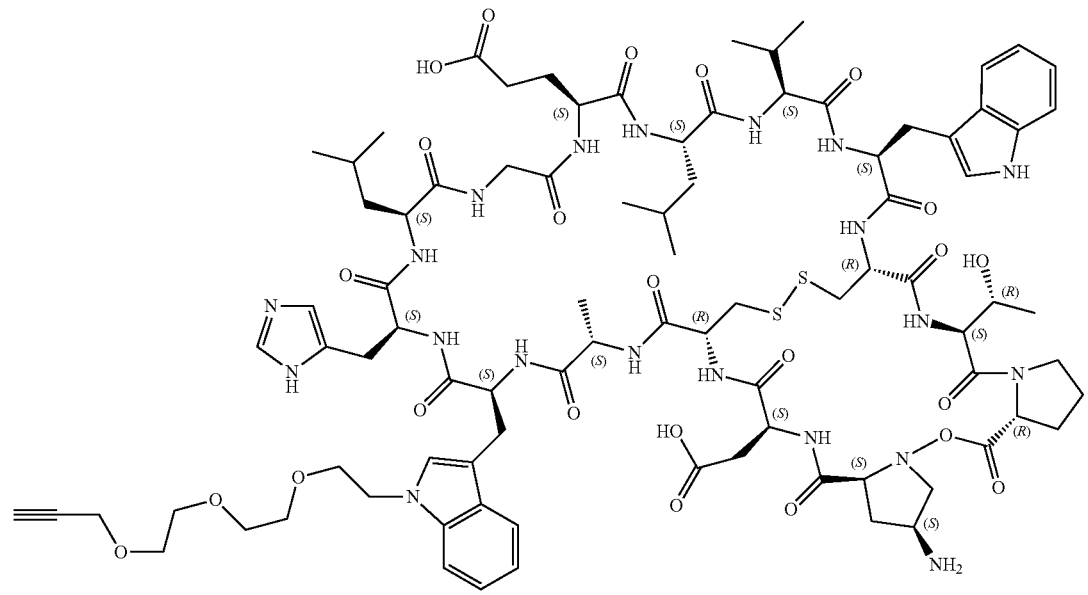

Solid Phase Peptide Synthesis of Intermediate 38

| # | Materials | Coupling reagents |
|---|---|---|
| 1 | Fmoc-D-Pro-OH (1.00 eq) | DIEA (4.00 eq) |
| 2 | Fmoc-Thr((Bu)-OH (3.00 eq) | HBTU (2.85 eq) and DIEA (6.00 eq) |
| 3 | Fmoc-Cys(Trt)-OH (3.00 eq) | HBTU (2.85 eq) and DIEA (6.00 eq) |
| 4 | Fmoc-Trp(Boc)-OH (3.00 eq) | HBTU (2.85 eq) and DIEA (6.00 eq) |
| 5 | Fmoc-Val-OH (3.00 eq) | HBTU (2.85 eq) and DIEA (6.00 eq) |
| 6 | Fmoc-Leu-OH (3.00 eq) | HBTU (2.85 eq) and DIEA (6.00 eq) |
| 7 | Fmoc-Glu(OtBu)-OH (3.00 eq) | HBTU (2.85 eq) and DIEA (6.00 eq) |
| 8 | Fmoc-Gly-OH (3.00 eq) | HBTU (2.85 eq) and DIEA (6.00 eq) |
| 9 | Fmoc-Leu-OH (3.00 eq) | HBTU (2.85 eq) and DIEA (6.00 eq) |
| 10 | Fmoc-His(Trt)-OH (2.00 eq) | HBTU (2.85 eq) and DIEA (6.00 eq) |

-continued

| # | Materials | Coupling reagents |
|---|---|---|
| 11 | Fmoc-Trp(PEG-alkyne)-OH (3.00 eq) | HBTU (2.85 eq) and DIEA (6.00 eq) |
| 12 | Fmoc-Ala-OH (3.00 eq) | HBTU (2.85 eq) and DIEA (6.00 eq) |
| 13 | Fmoc-Cys(Trt)-OH (3.00 eq) | HBTU (2.85 eq) and DIEA (6.00 eq) |
| 14 | Fmoc-Asp(OtBu)-OH (3.00 eq) | HBTU (2.85 eq) and DIEA (6.00 eq) |
| 15 | BOC-(2S,4S)-4-AMINO-1-FMOC-PYRROLIDINE-2-CARBOXYLIC ACID (1.00 eq) | HATU (0.95 eq) and DIEA (2.00 eq) |

Preparation of Intermediate 39: N-(15-((6S,9R,12S,15S,18S,21S,27S,30S,33S,36S,39R,42S,44aS,46S,49aR)-30-((1H-imidazol-5-yl)methyl)-12,33-bis((1H-indol-3-yl)methyl)-46-amino-6-((R)-1-hydroxyethyl)-18,27-diisobutyl-15-isopropyl-36,42-dimethyl-5,8,11,14,17,20,23,26,29,32,35,38,41,44,49-pentadecaoxooctatetracontahydro-1H-9,39-(methanodithiomethano)dipyrrolo[1,2-a:1',2'-d][1,4,7,10,13,16,19,22,25,28,31,34,37,40,43]pentadecaazacyclopentatetracontin-21-yl)-13-oxo-3,6,9-trioxa-12-azapenta decyl)hex-5-ynamide
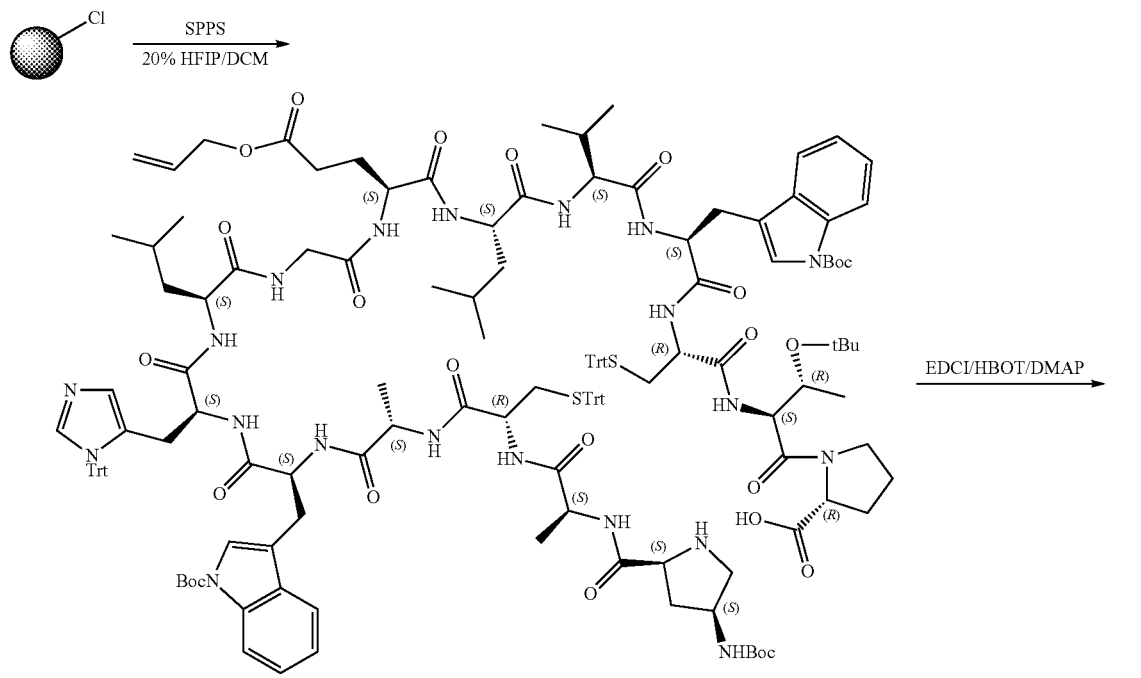
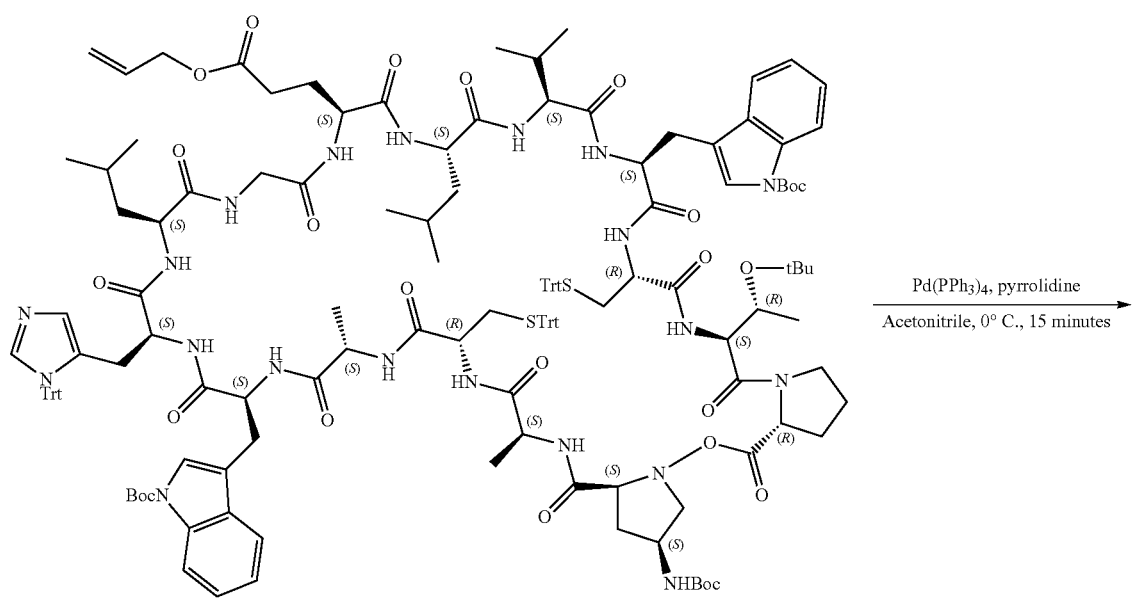

1377
-continued
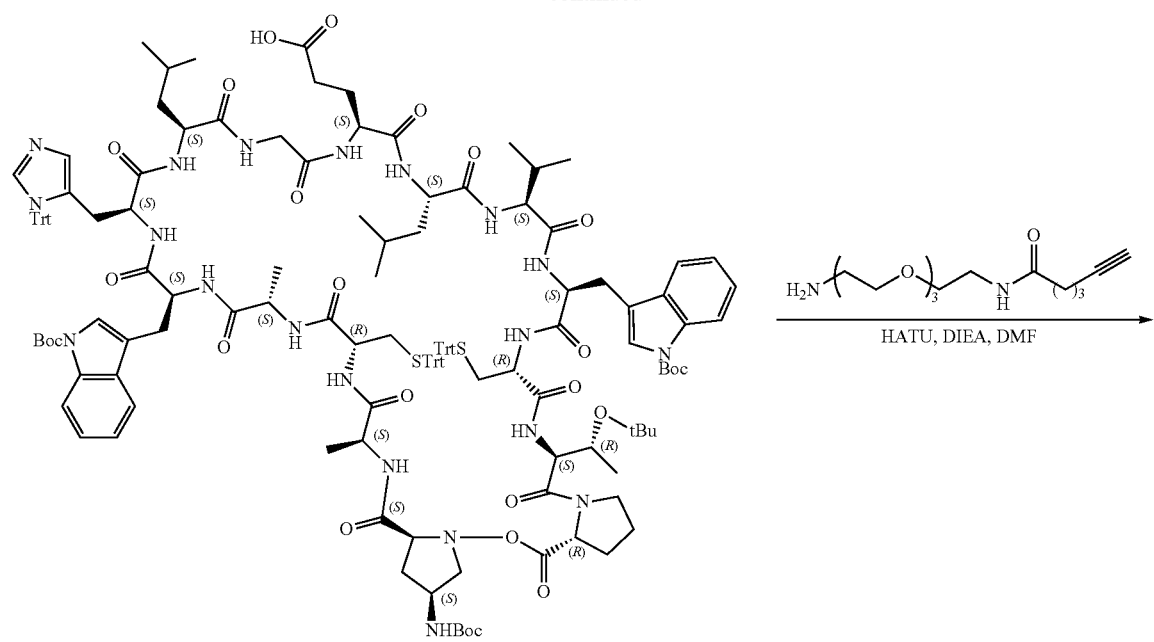
1378
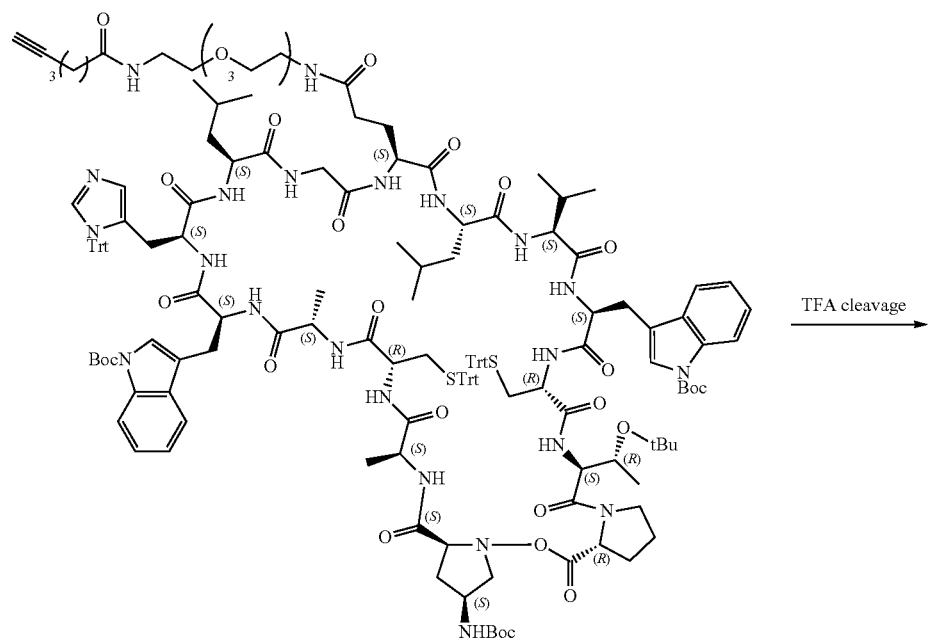
TFA cleavage →

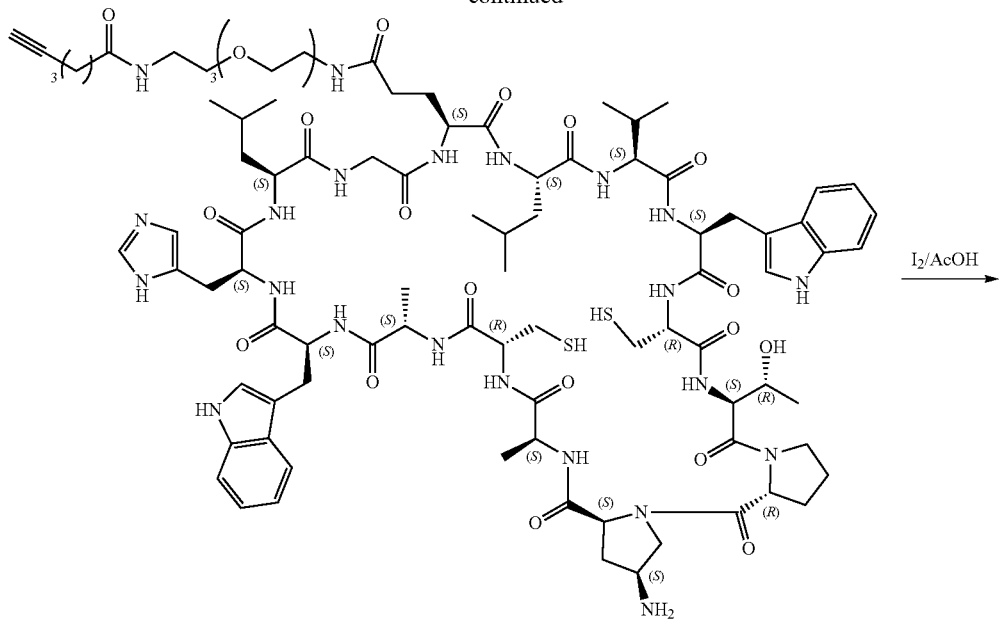

I₂/AcOH

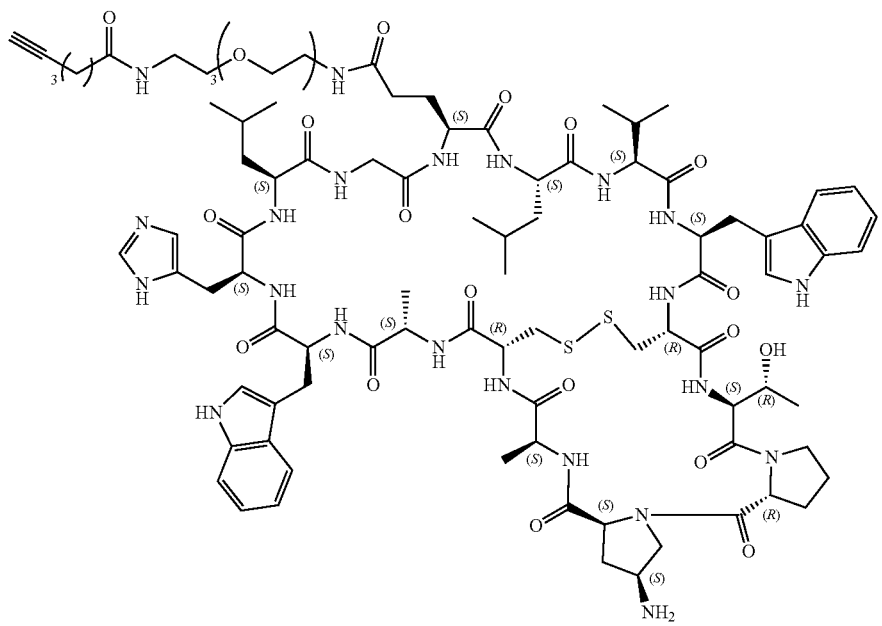

Solid Phase Peptide Synthesis of Intermediate 39

| # | Materials | Coupling reagents |
|---|---|---|
| 1 | Fmoc-D-Pro-OH (1.00 eq) | DIEA (4.00 eq) |
| 2 | Fmoc-Thr((Bu)-OH (3.00 eq) | HBTU (2.85 eq) and DIEA (6.00 eq) |
| 3 | Fmoc-Cys(Trt)-OH (3.00 eq) | HBTU (2.85 eq) and DIEA (6.00 eq) |
| 4 | Fmoc-Trp(Boc)-OH (3.00 eq) | HBTU (2.85 eq) and DIEA (6.00 eq) |
| 5 | Fmoc-Val-OH (3.00 eq) | HBTU (2.85 eq) and DIEA (6.00 eq) |
| 6 | Fmoc-Leu-OH (3.00 eq) | HBTU (2.85 eq) and DIEA (6.00 eq) |
| 7 | Fmoc-Glu(OAll)-OH (3.00 eq) | HBTU (2.85 eq) and DIEA (6.00 eq) |
| 8 | Fmoc-Gly-OH (3.00 eq) | HBTU (2.85 eq) and DIEA (6.00 eq) |
| 9 | Fmoc-Leu-OH (3.00 eq) | HBTU (2.85 eq) and DIEA (6.00 eq) |
| 10 | Fmoc-His(Trt)-OH (2.00 eq) | HBTU (2.85 eq) and DIEA (6.00 eq) |
| 11 | Fmoc-Trp-OH (3.00 eq) | HBTU (2.85 eq) and DIEA (6.00 eq) |
| 12 | Fmoc-Ala-OH (3.00 eq) | HBTU (2.85 eq) and DIEA (6.00 eq) |
| 13 | Fmoc-Cys(Trt)-OH (3.00 eq) | HBTU (2.85 eq) and DIEA (6.00 eq) |
| 14 | Fmoc-Ala-OH (3.00 eq) | HBTU (2.85 eq) and DIEA (6.00 eq) |
| 15 | BOC-(2S,4S)-4-AMINO-1-FMOC-PYRROLIDINE-2-CARBOXYLIC ACID (1.00 eq) | HATU (0.95 eq) and DIEA (2.00 eq) |

Preparation of Intermediate 40
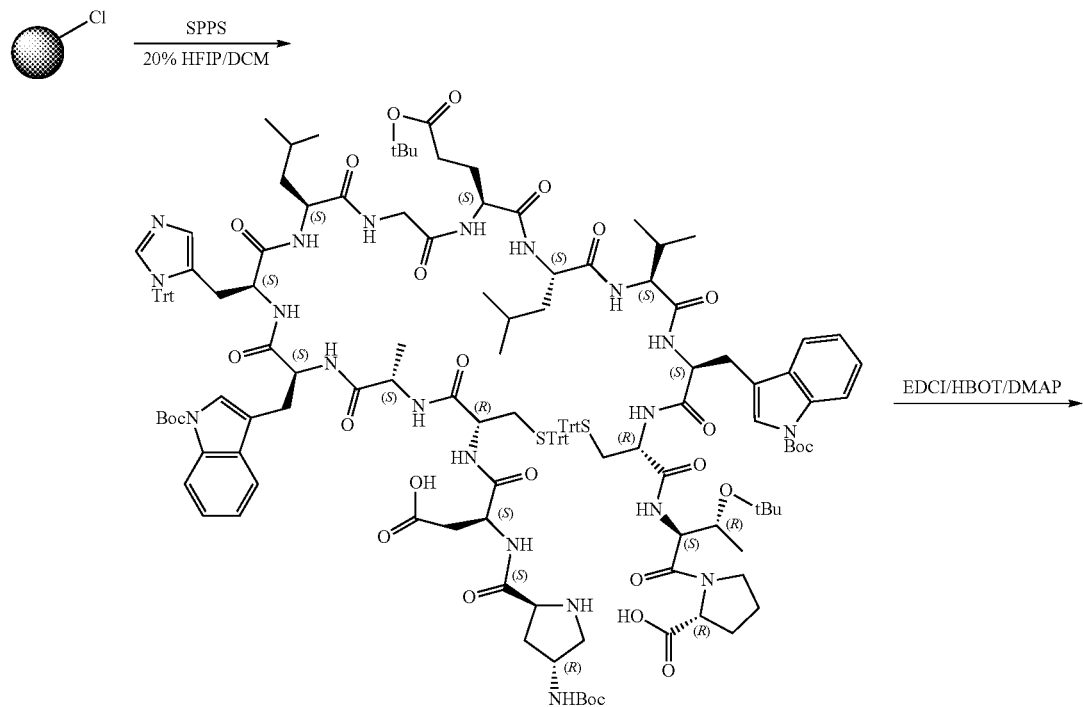
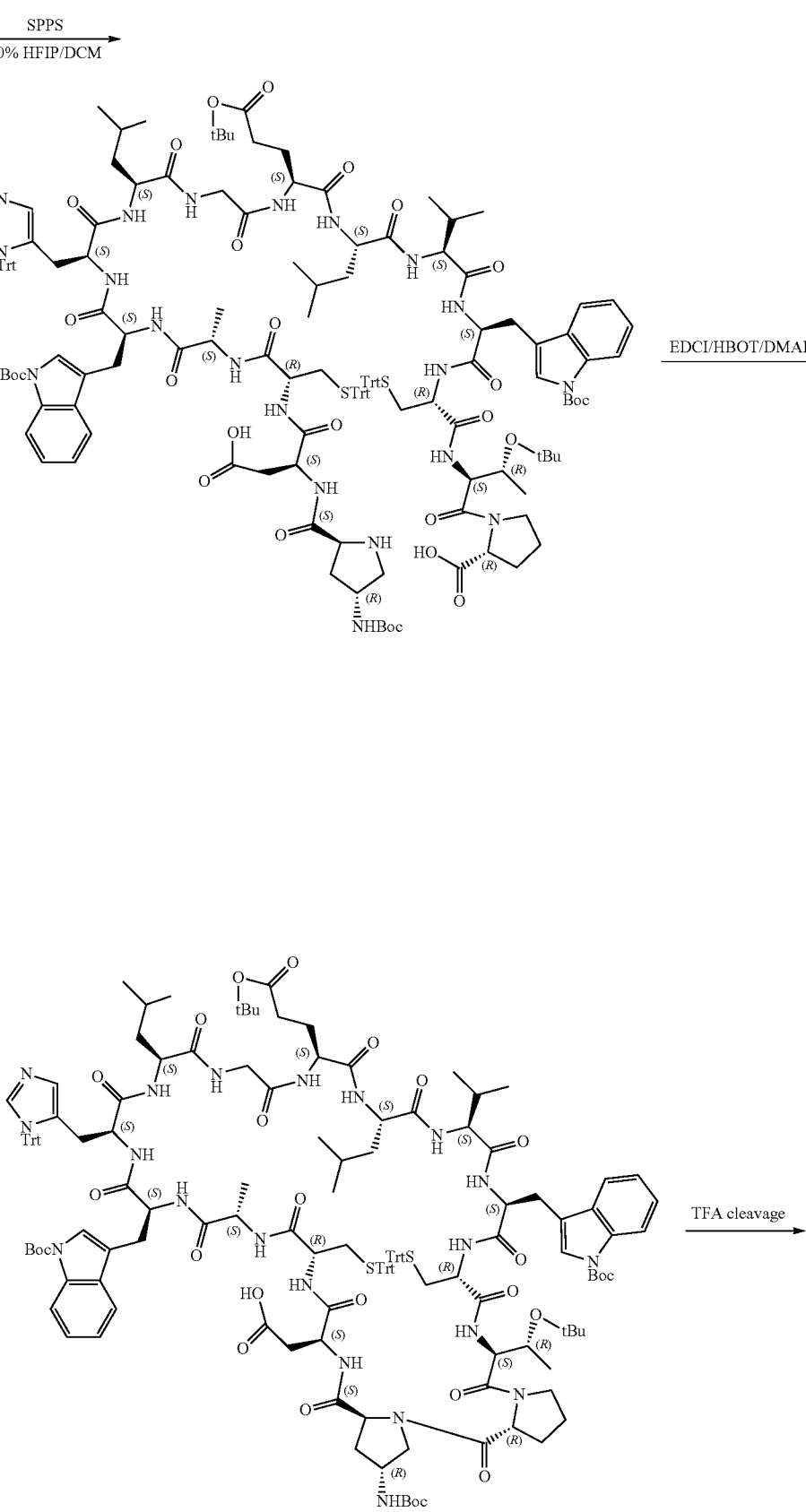

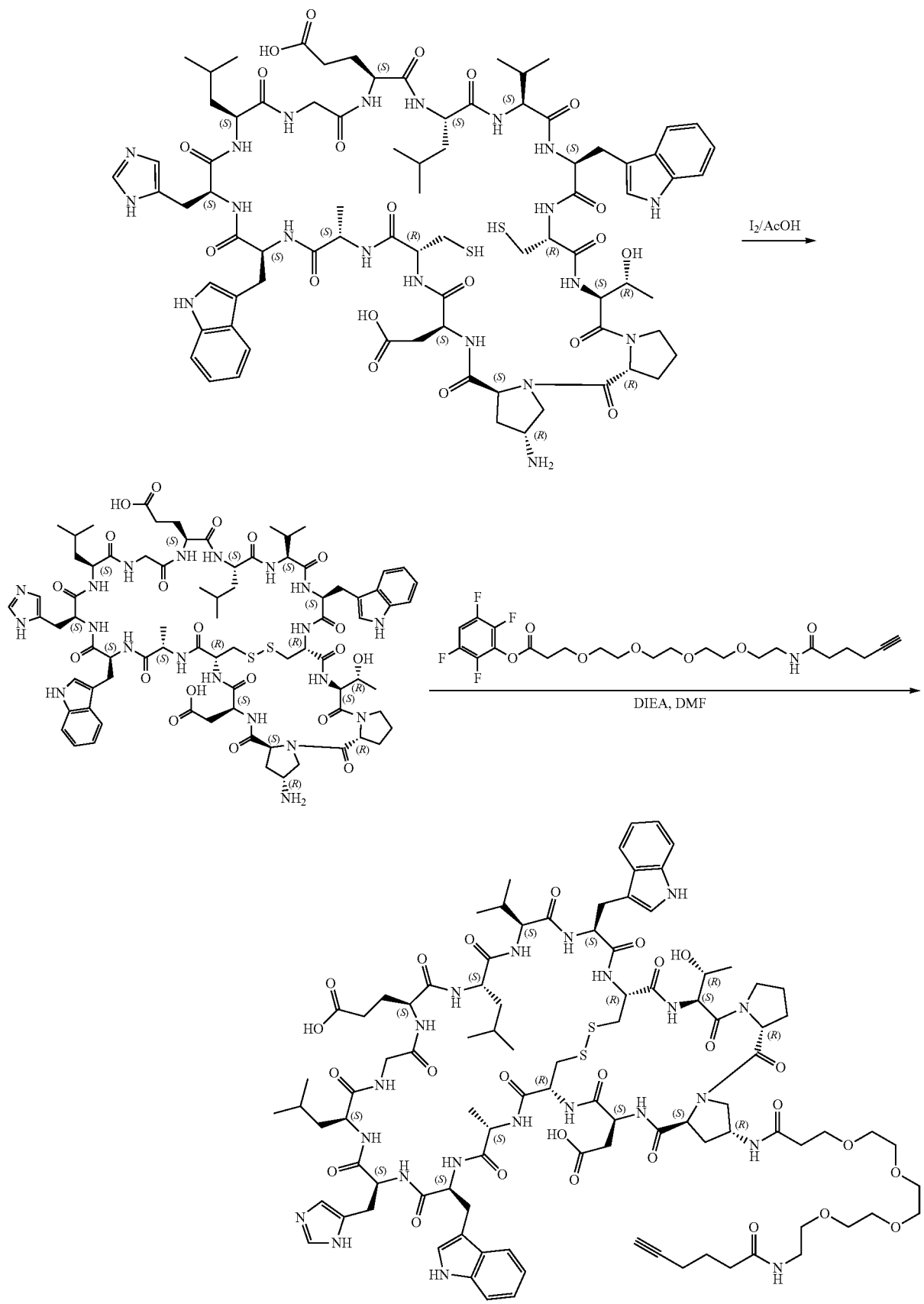

Solid Phase Peptide Synthesis of Intermediate 40

| # | Materials | Coupling reagents |
|---|---|---|
| 1 | Fmoc-D-Pro-OH (1.00 eq) | DIEA (4.00 eq) |
| 2 | Fmoc-Thr(tBu)-OH (3.00 eq) | HBTU (2.85 eq) and DIEA (6.00 eq) |
| 3 | Fmoc-Cys(Trt)-OH (3.00 eq) | HBTU (2.85 eq) and DIEA (6.00 eq) |
| 4 | Fmoc-Trp(Boc)-OH (3.00 eq) | HBTU (2.85 eq) and DIEA (6.00 eq) |
| 5 | Fmoc-Val-OH (3.00 eq) | HBTU (2.85 eq) and DIEA (6.00 eq) |
| 6 | Fmoc-Leu-OH (3.00 eq) | HBTU (2.85 eq) and DIEA (6.00 eq) |
| 7 | Fmoc-Glu(OfBu)-OH (3.00 eq) | HBTU (2.85 eq) and DIEA (6.00 eq) |
| 8 | Fmoc-Gly-OH (3.00 eq) | HBTU (2.85 eq) and DIEA (6.00 eq) |
| 9 | Fmoc-Leu-OH (3.00 eq) | HBTU (2.85 eq) and DIEA (6.00 eq) |
| 10 | Fmoc-His(Trt)-OH (2.00 eq) | HBTU (2.85 eq) and DIEA (6.00 eq) |
| 11 | Fmoc-Trp-OH (3.00 eq) | HBTU (2.85 eq) and DIEA (6.00 eq) |
| 12 | Fmoc-Ala-OH (3.00 eq) | HBTU (2.85 eq) and DIEA (6.00 eq) |
| 13 | Fmoc-Cys(Trt)-OH (3.00 eq) | HBTU (2.85 eq) and DIEA (6.00 eq) |
| 14 | Fmoc-Asp(OfBu)-OH (3.00 eq) | HBTU (2.85 eq) and DIEA (6.00 eq) |
| 15 | BOC-(2S,4R)-4-AMINO-1-FMOC-PYRROLIDINE-2-CARBOXYLIC ACID (1.00 eq) | HATU (0.95 eq) and DIEA (2.00 eq) |

Synthesis of 3,3'-((2-(2-(2-(2-(2-((S)-7-(5-(1-((2-cyanopyridin-3-yl)methyl)-2,2-dimethyl-3-oxo-2,3-dihydro-1H-pyrrolo[2,3-b]pyridin-6-yl)pyrimidin-2-yl)-3-oxohexahydroimidazo[1,5-a]pyrazin-2(3H)-yl)ethoxy)ethoxy)ethoxy)acetamido)propane-1,3-diyl)bis(oxy))bis(N-(1-((2R,3R,4R,5S)-3,4-dihydroxy-5-((6-(trifluoromethyl)pyrazin-2-yl)amino)tetrahydro-2H-pyran-2-yl)-2,5,8,11-tetraoxatridecan-13-yl)propanamide)

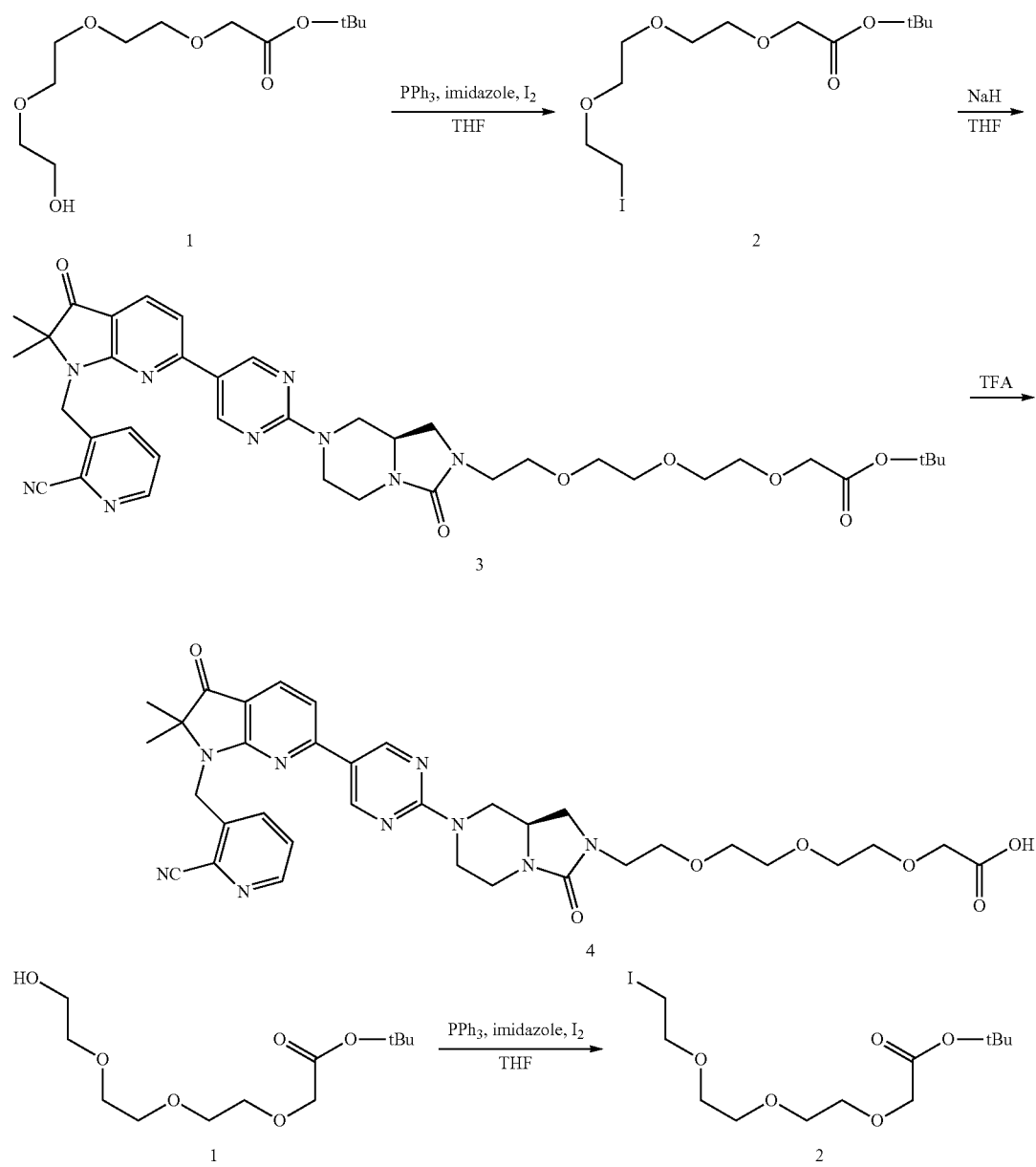

1387 -continued 1388
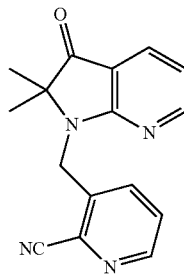
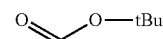
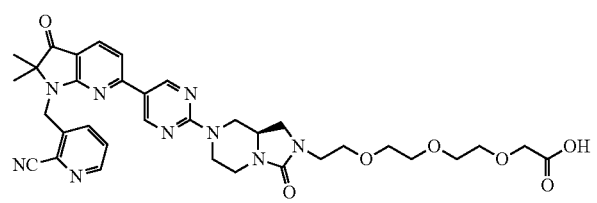
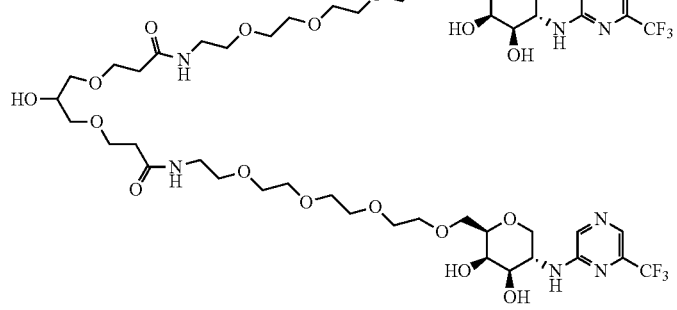
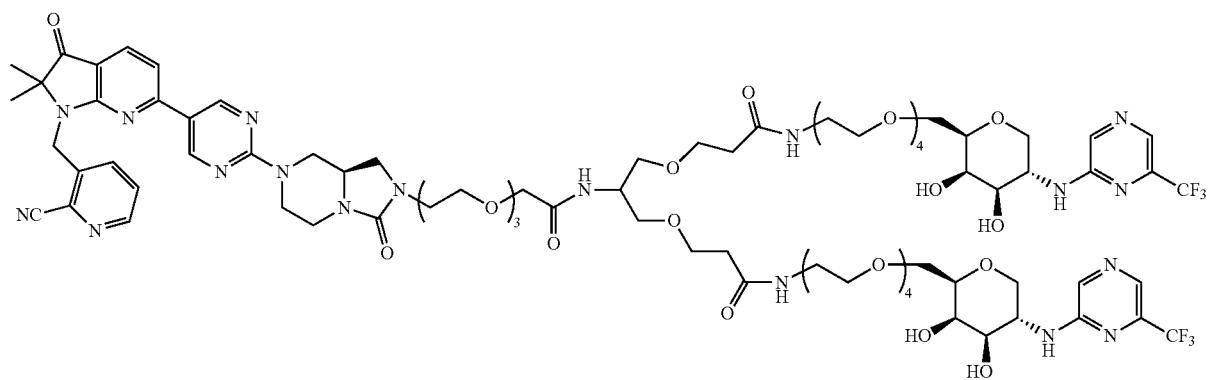

3,3'-((2-(6-(4-(1-((S)-7-(5-(1-((2-cyanopyridin-3-yl)methyl)-2,2-dimethyl-3-oxo-2,3-dihydro-1H-pyrrolo[2,3-b]pyridin-6-yl)pyrimidin-2-yl)-3-oxohexahydroimidazo[1,5-a]pyrazin-2(3H)-yl)-15-oxo-4,7,10-trioxa-14-azaoctadecan-18-yl)-1H-1,2,3-triazol-1-yl)hexanamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide)
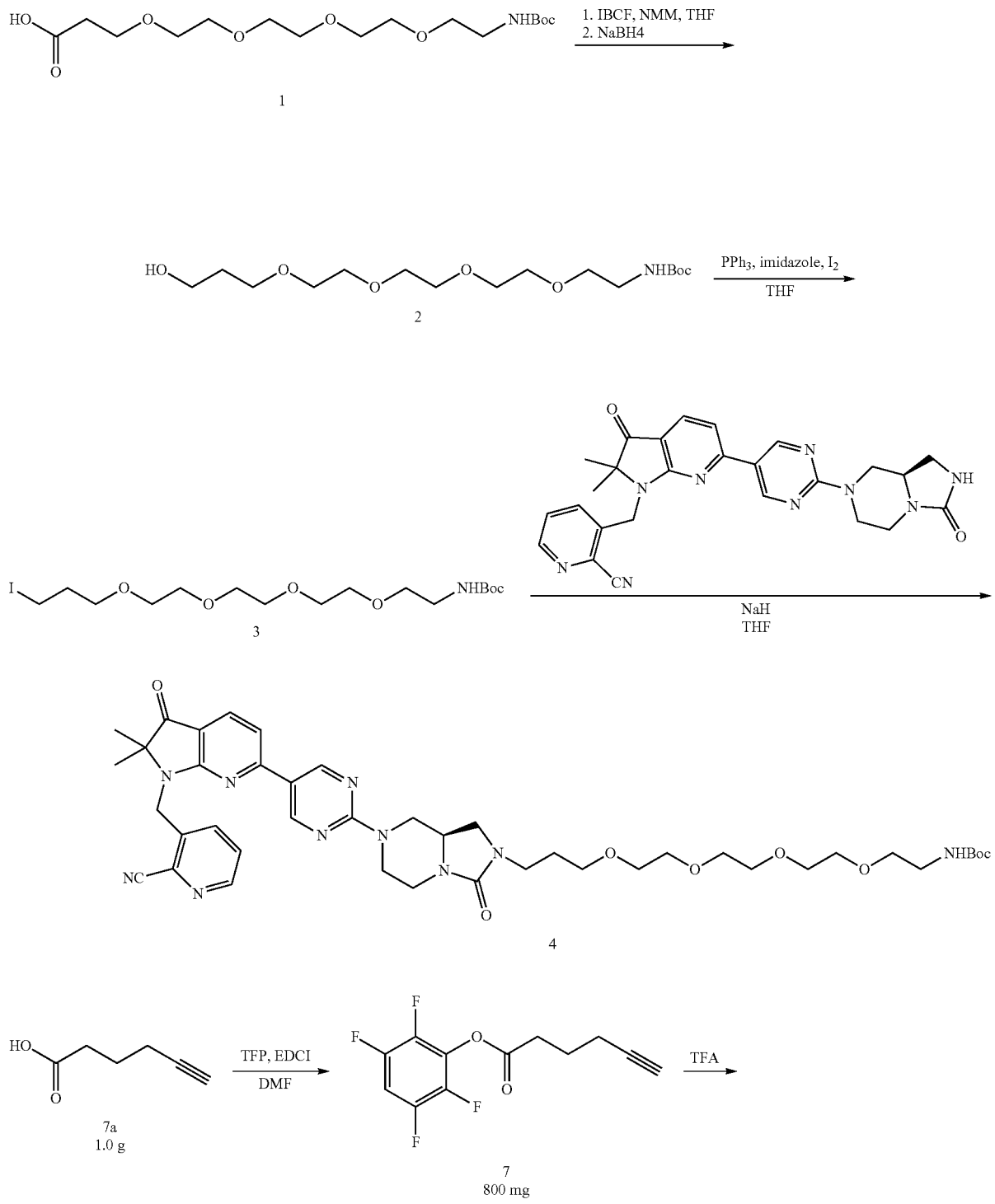

1391　　　　　　　　　　　　　　　　　　　　　　　1392
-continued
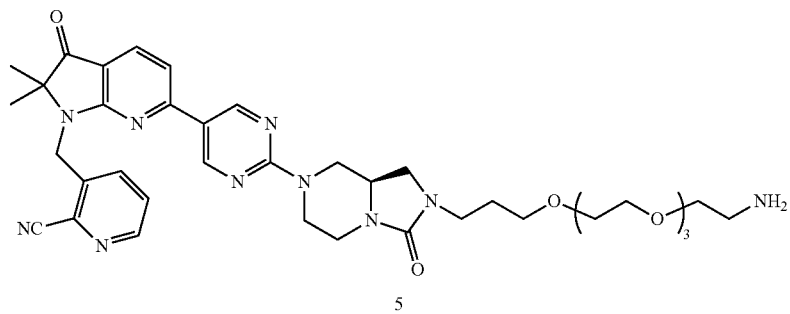 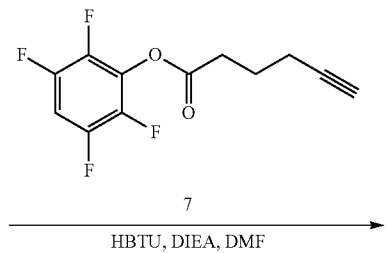
HBTU, DIEA, DMF
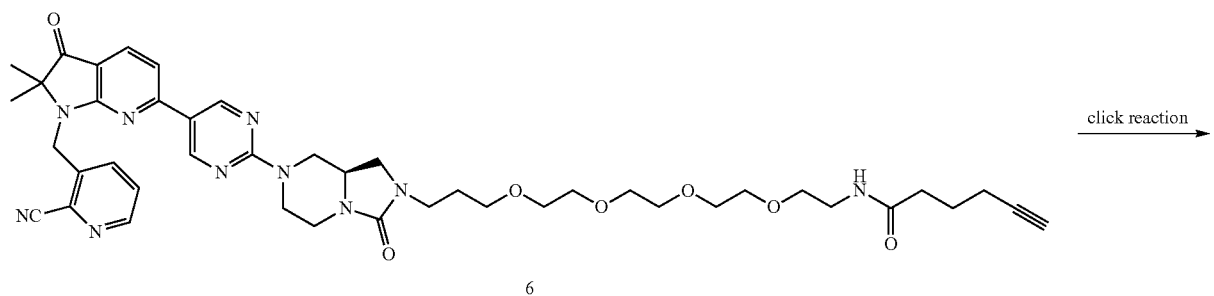
click reaction
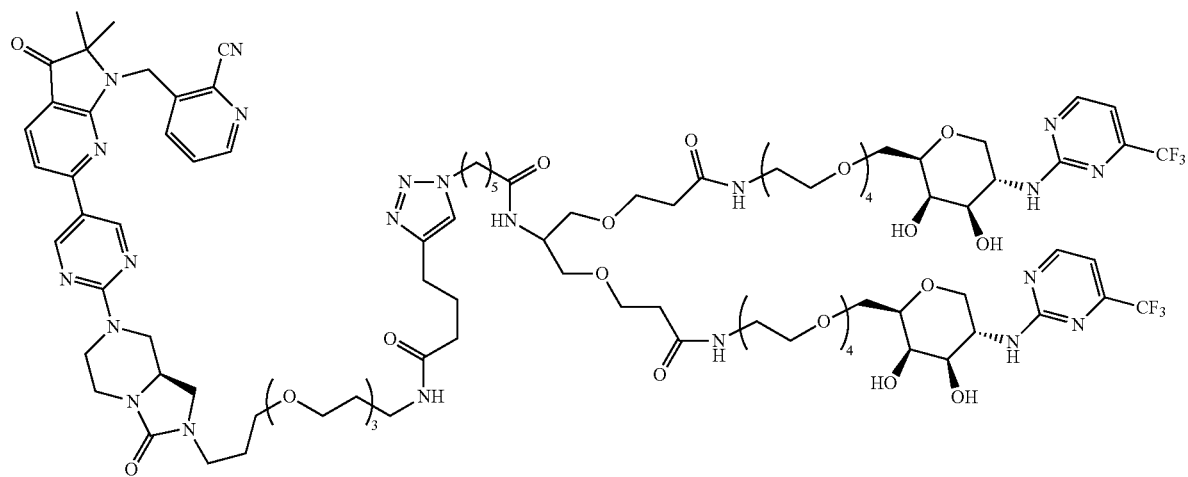

N-(3-((S)-7-(5-(1-((2-cyanopyridin-3-yl)methyl)-2,2-dimethyl-3-oxo-2,3-dihydro-1H-pyrrolo[2,3-b]pyridin-6-yl)pyrimidin-2-yl)-3-oxohexahydroimidazo[1,5-a]pyrazin-2(3H)-yl)propyl)-2-(4-((4-(((2R,3R,4R,5S)-3,4-dihydroxy-5-((6-(trifluoromethyl)pyrazin-2-yl)amino)tetrahydro-2H-pyran-2-yl)methyl)piperazin-1-yl)methyl)phenoxy)acetamide
5
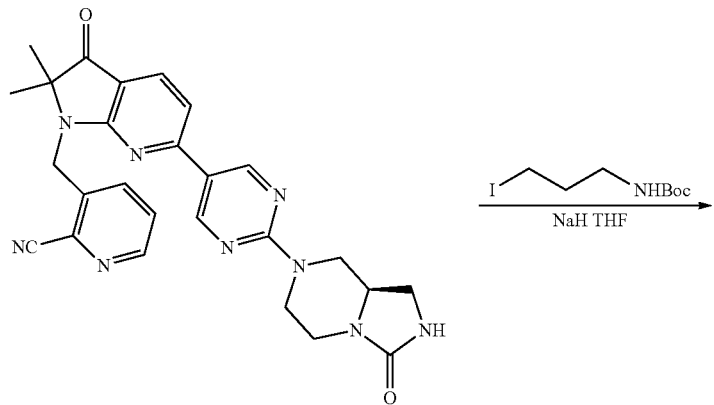
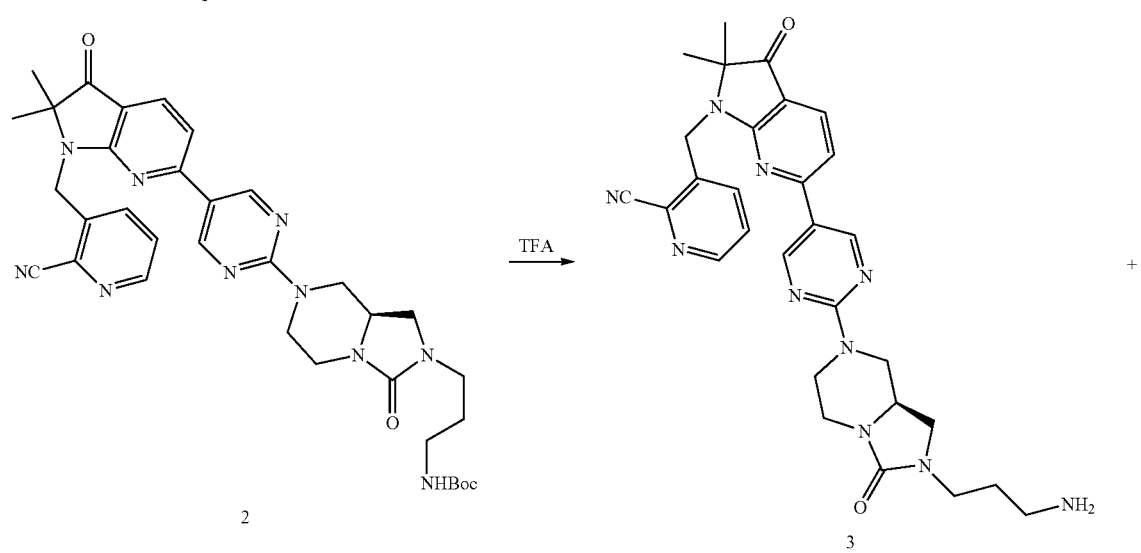
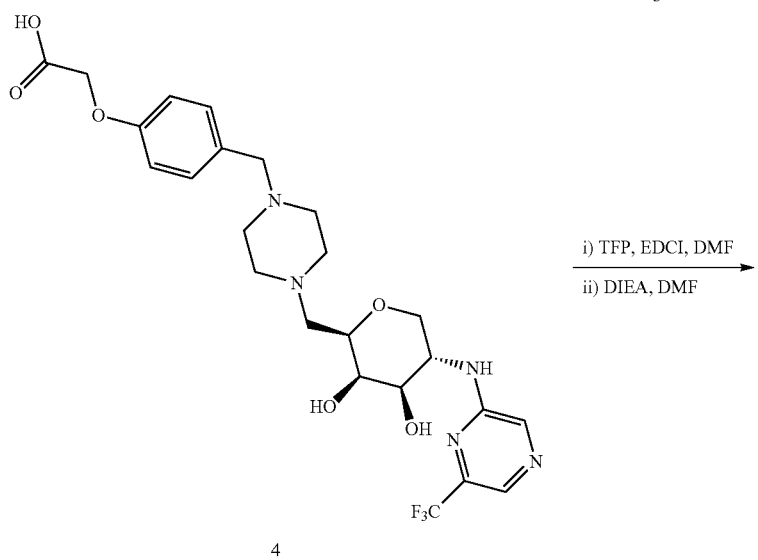

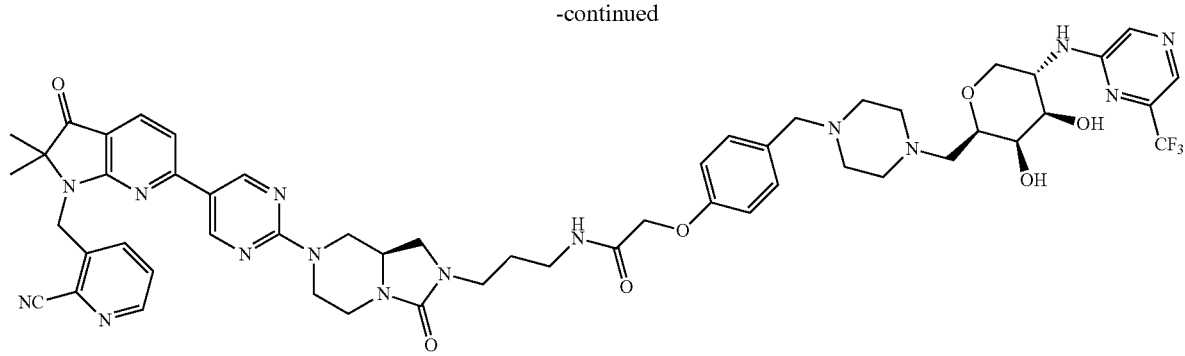
5
N1-(2-(2-((S)-7-(5-(1-((2-cyanopyridin-3-yl)methyl)-2,2-dimethyl-3-oxo-2,3-dihydro-1H-pyrrolo[2,3-b]pyridin-6-yl)pyrimidin-2-yl)-3-oxohexahydroimidazo[1,5-a]pyrazin-2(3H)-yl)ethoxy)ethyl)-N4-(((2R,3R,4R,5S)-3,4-dihydroxy-5-((6-(trifluoromethyl)pyrazin-2-yl)amino)tetrahydro-2H-pyran-2-yl)methyl)terephthalamide
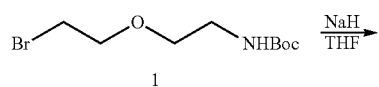
1
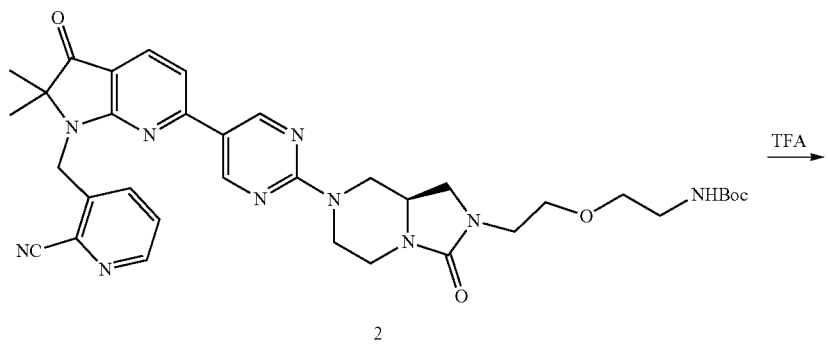
2
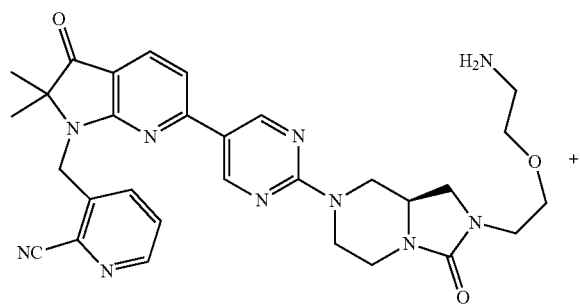
3

1397

-continued

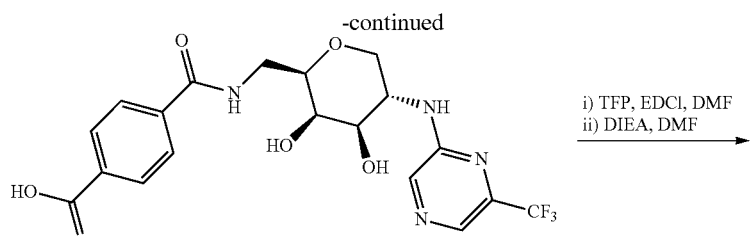

4 i) TFP, EDCl, DMF
ii) DIEA, DMF

1398

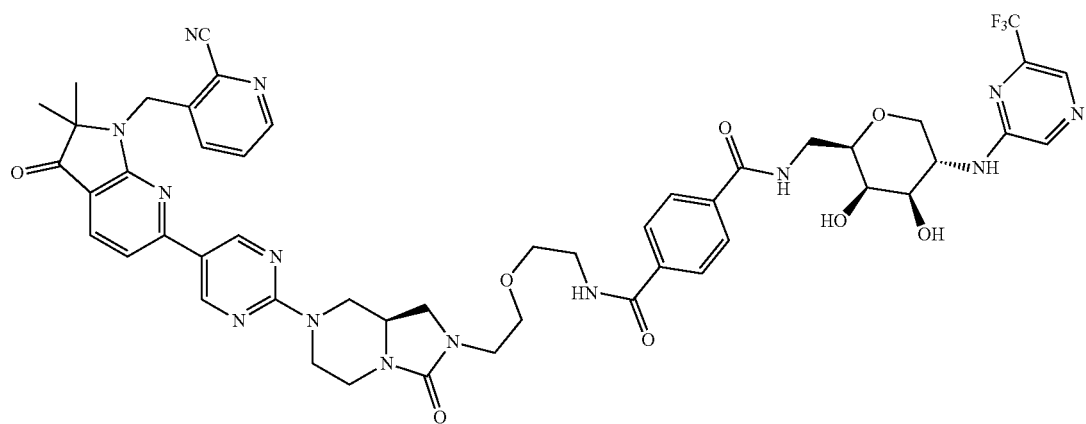

3-((11-((11-oxidaneyl)methyl)-1-((2R,3R,4R,5S)-3,
4-dihydroxy-5-((6-(trifluoromethyl)pyrazin-2-yl)
amino)tetrahydro-2H-pyran-2-yl)-18-(2-(2-(2-(2-(4-
(3-(4-(isoquinolin-8-yl)phenethoxy)-4-(1H-pyrrolo
[3,2-c]pyridin-3-yl)benzyl)piperazin-1-yl)-2-
oxoethoxy)ethoxy)ethoxy)acetamido)-13-oxo-2,5,8,
16-tetraoxa-12-azanonadecan-19-yl)oxy)-N-(1-((2R,
3R,4R,5S)-3,4-dihydroxy-5-((6-(trifluoromethyl)
pyrazin-2-yl)amino)tetrahydro-2H-pyran-2-yl)-2,5,8,
11-tetraoxatridecan-13-yl)propanamide

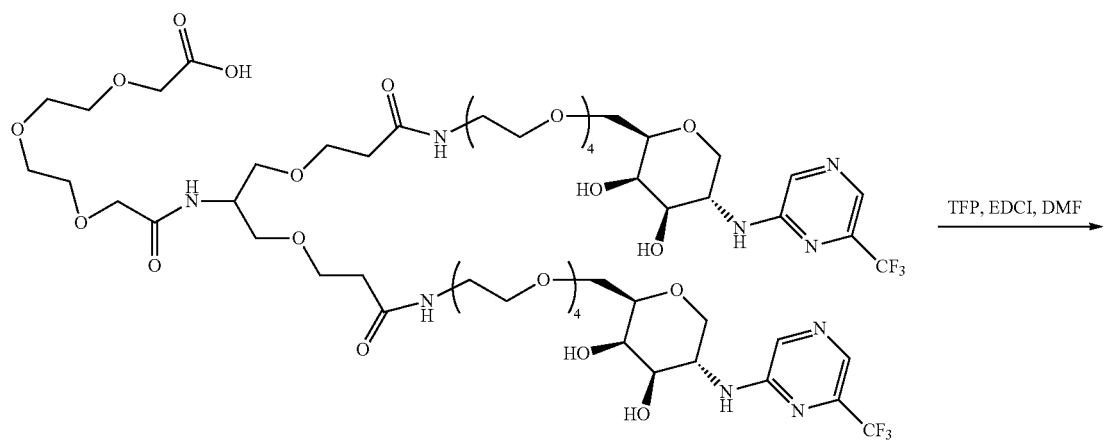

TFP, EDCI, DMF

1399
-continued
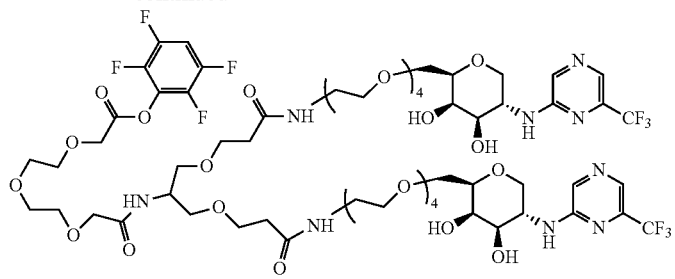
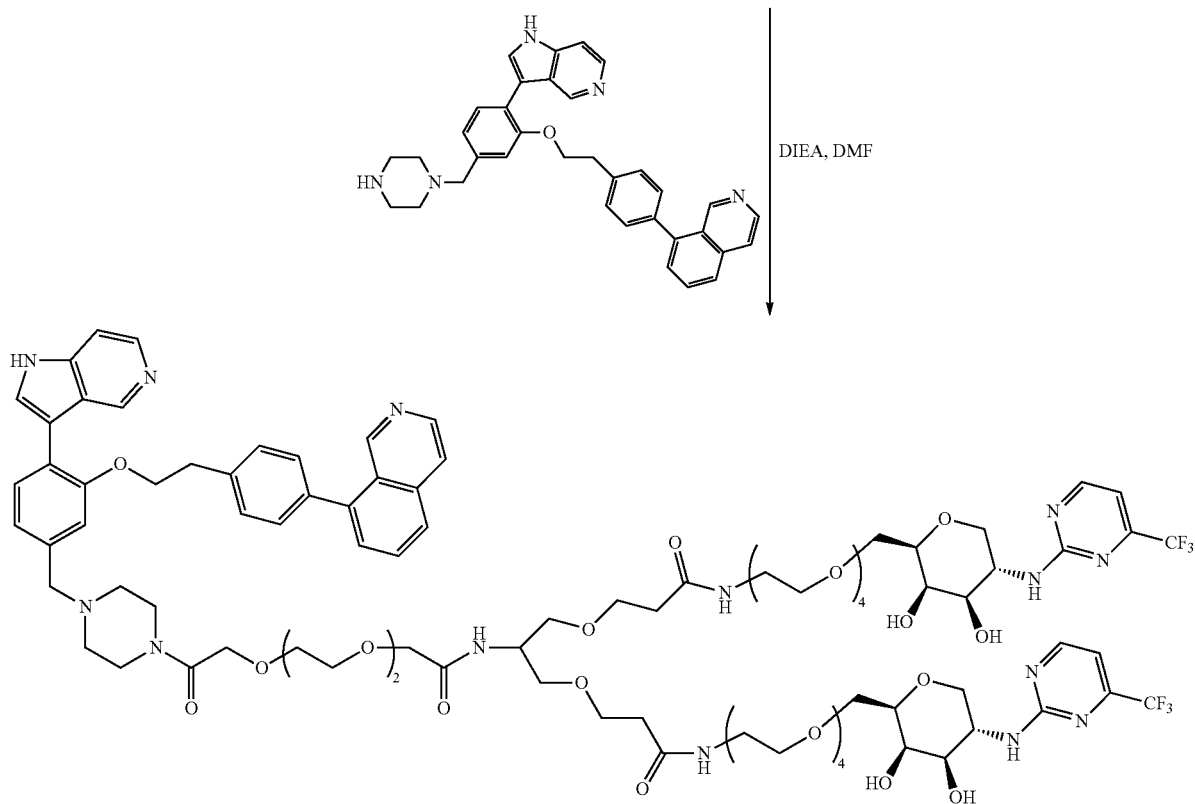
TABLE 1A
Extracellular Protein Degrading Compounds of the Present Invention
Compound 1
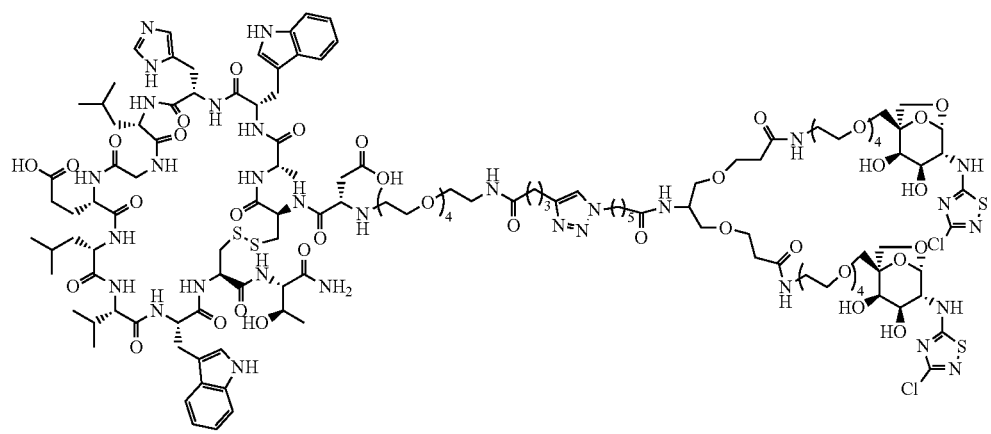

TABLE 1A-continued
Extracellular Protein Degrading Compounds of the Present Invention
Compound 2
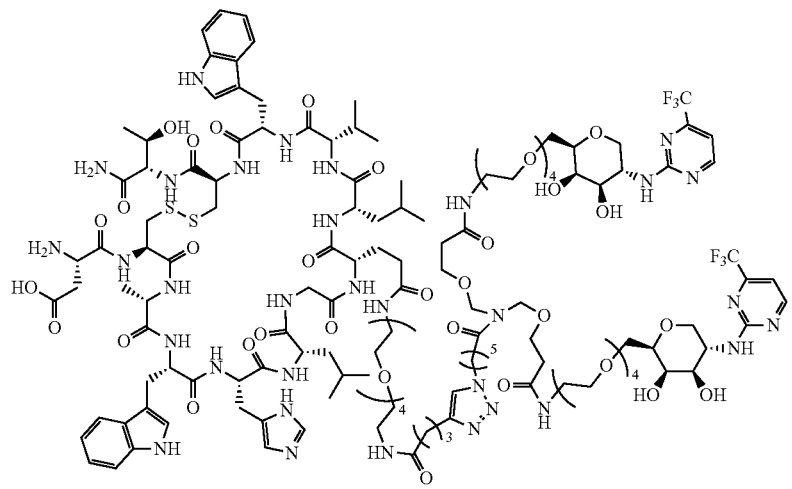
Compound 3
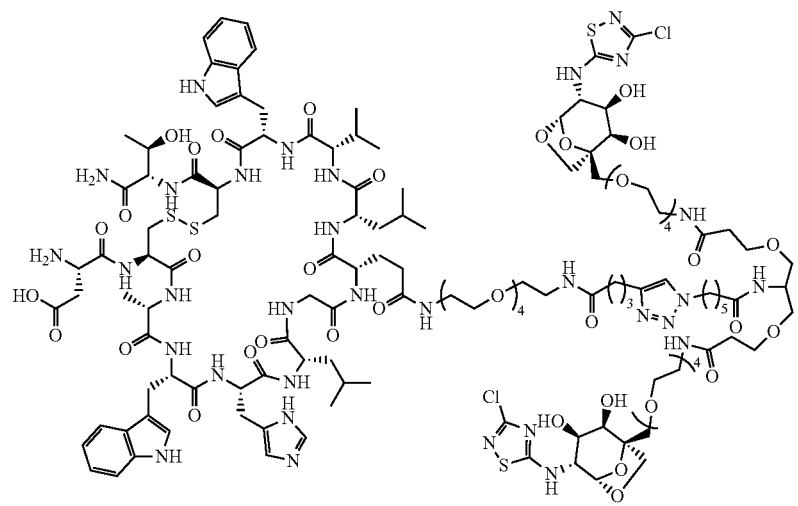

TABLE 1A-continued
Extracellular Protein Degrading Compounds of the Present Invention
Compound 4
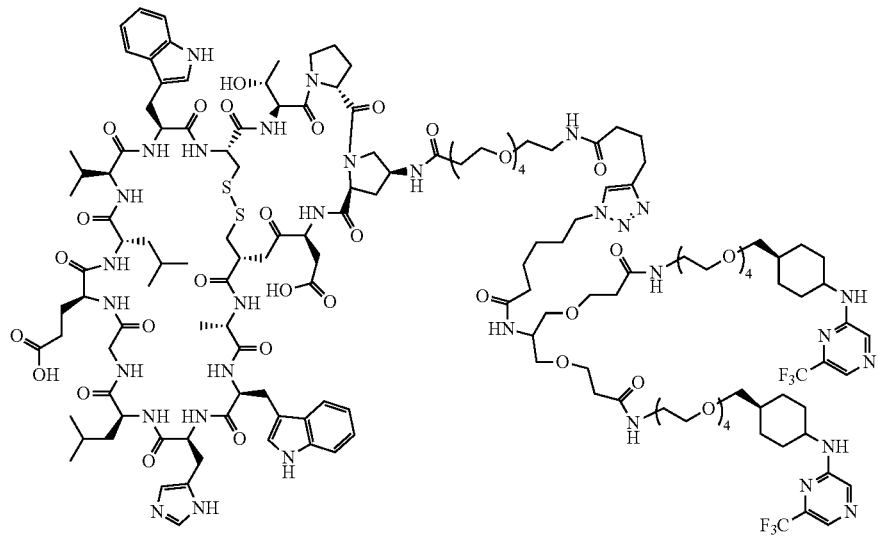
Compound 5
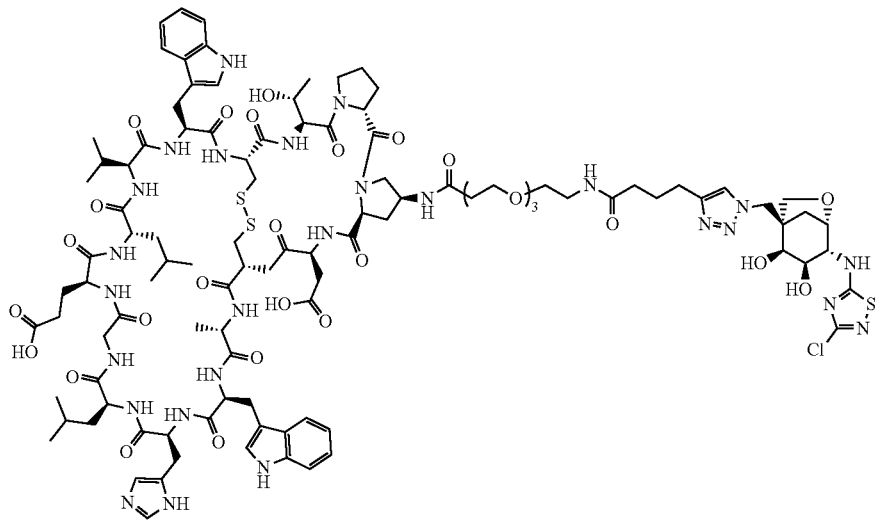

TABLE 1A-continued
Extracellular Protein Degrading Compounds of the Present Invention
Compound 6
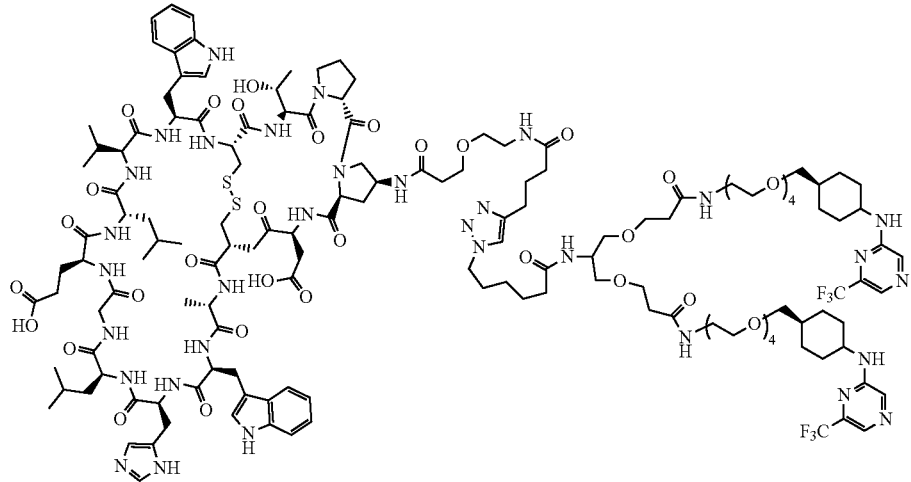
Compound 7
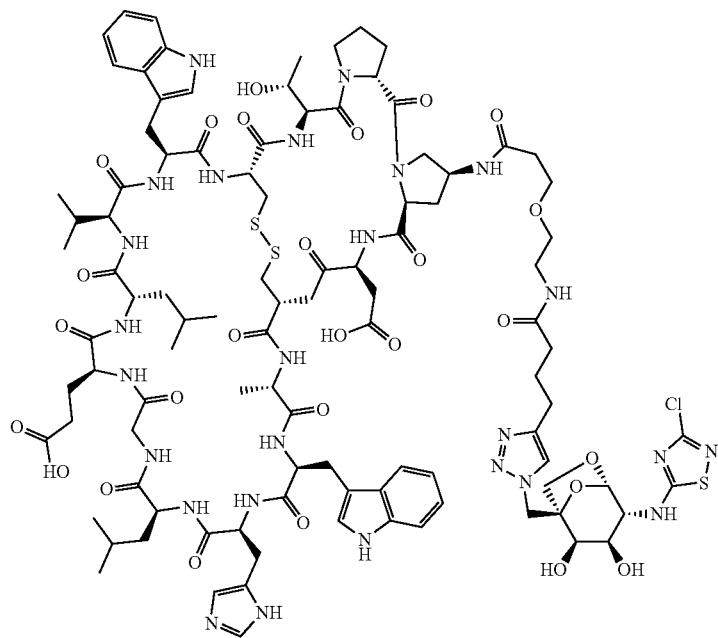 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)CCOCCNC(=O)CCCc3cn(C[C@@]45CO[C@@H](O4)[C@H](Nc4nc(Cl)ns4)[C@@H](O)[C@H]5O)nn3)C[C@H]1C(=O)N[C@@H](CC(=O)O)C(=O)C2]

TABLE 1A-continued
Extracellular Protein Degrading Compounds of the Present Invention
Compound 8
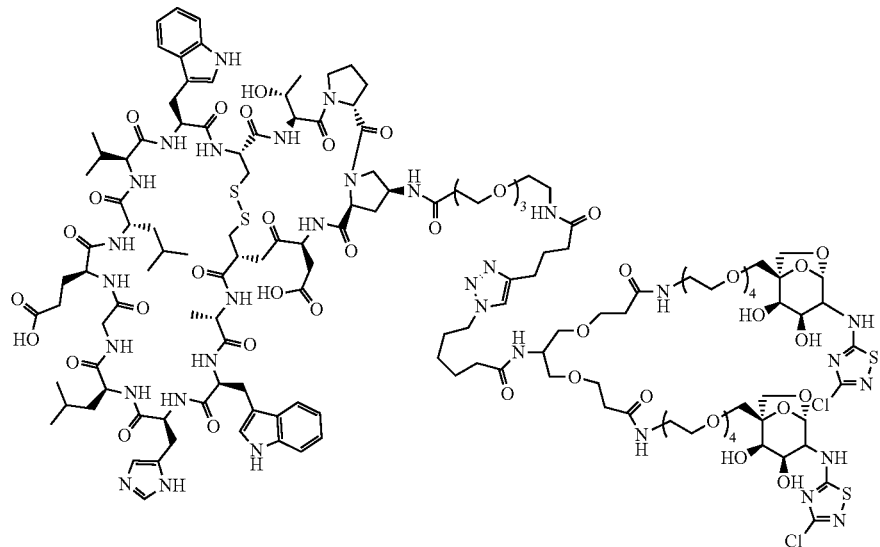
Compound 9
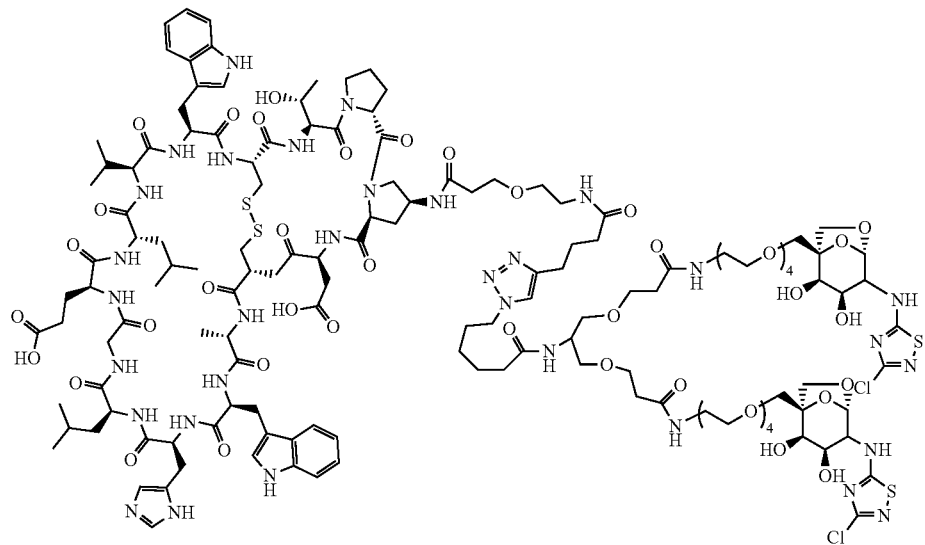

TABLE 1A-continued
Extracellular Protein Degrading Compounds of the Present Invention
Compound 10
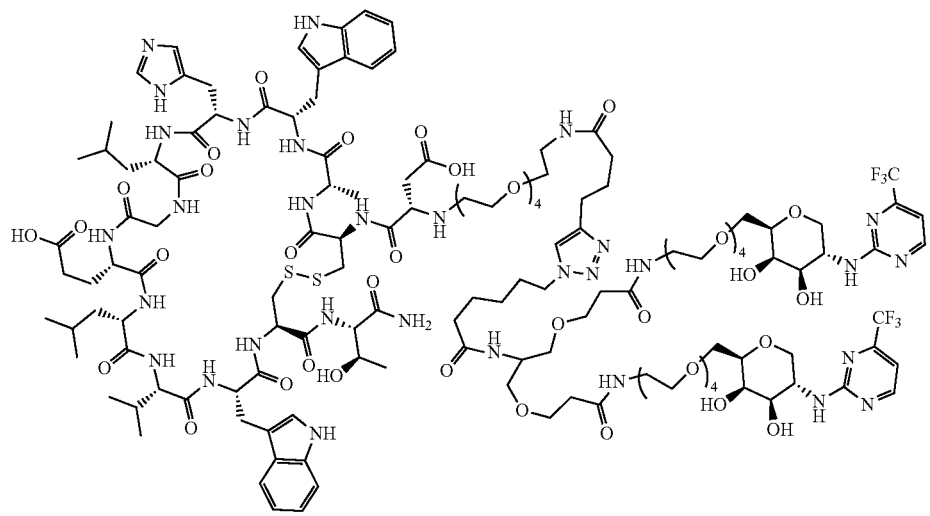
Compound 11
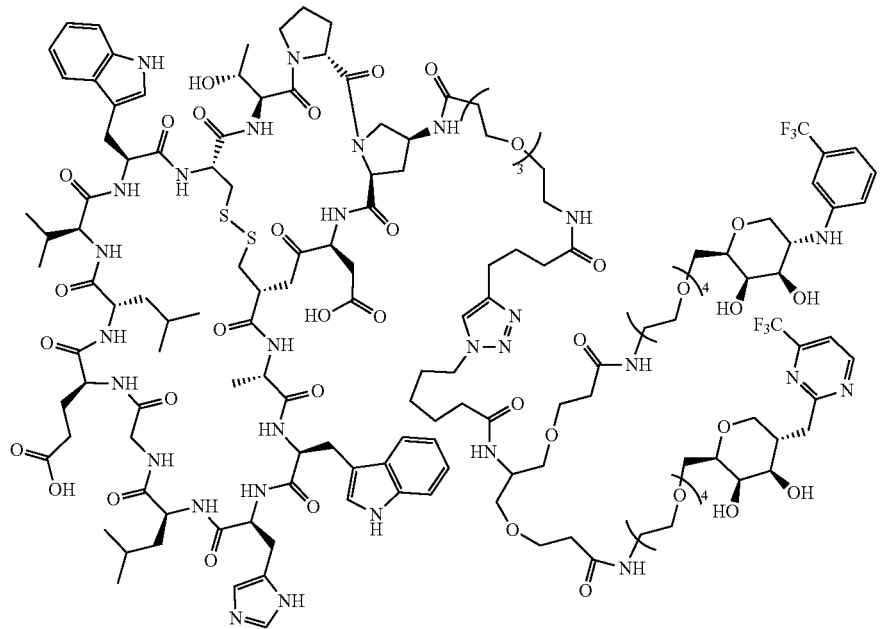

TABLE 1A-continued
Extracellular Protein Degrading Compounds of the Present Invention
Compound 12
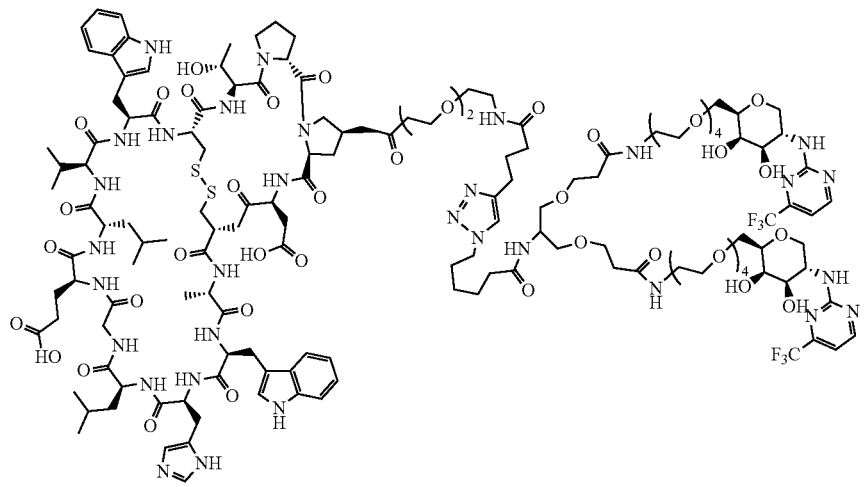
Compound 13
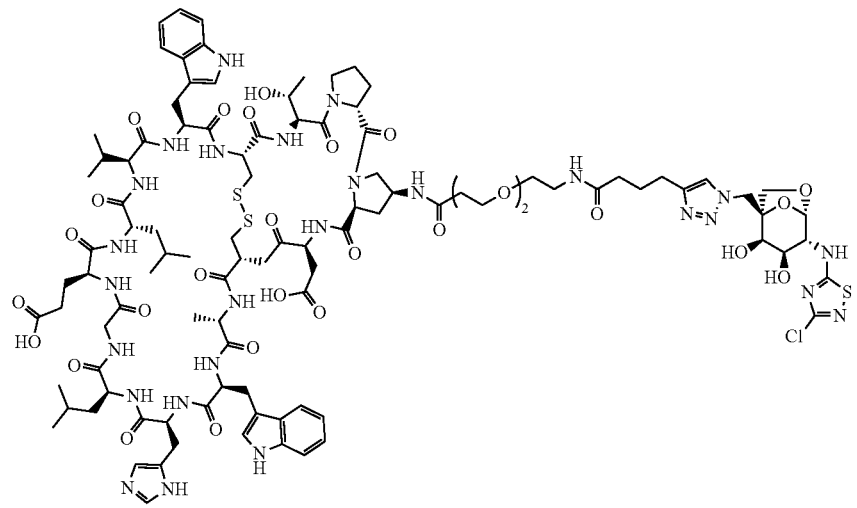

TABLE 1A-continued
Extracellular Protein Degrading Compounds of the Present Invention
Compound 14
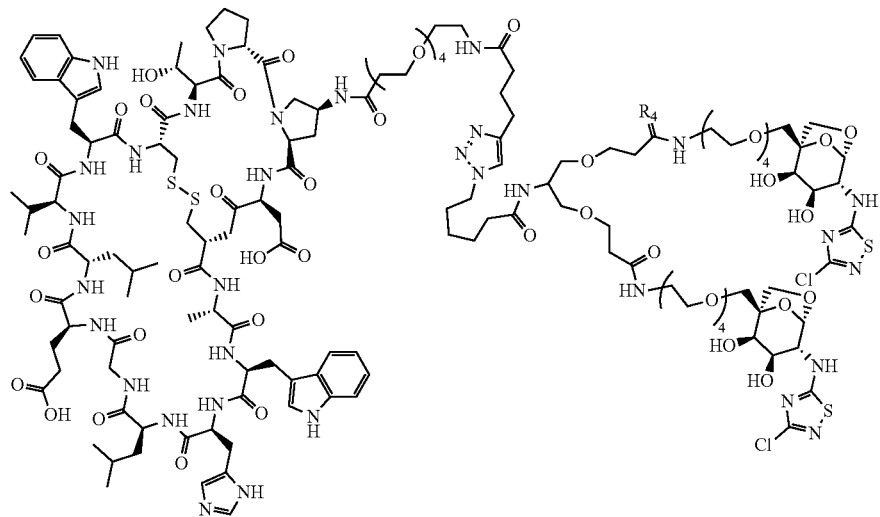
Compound 15
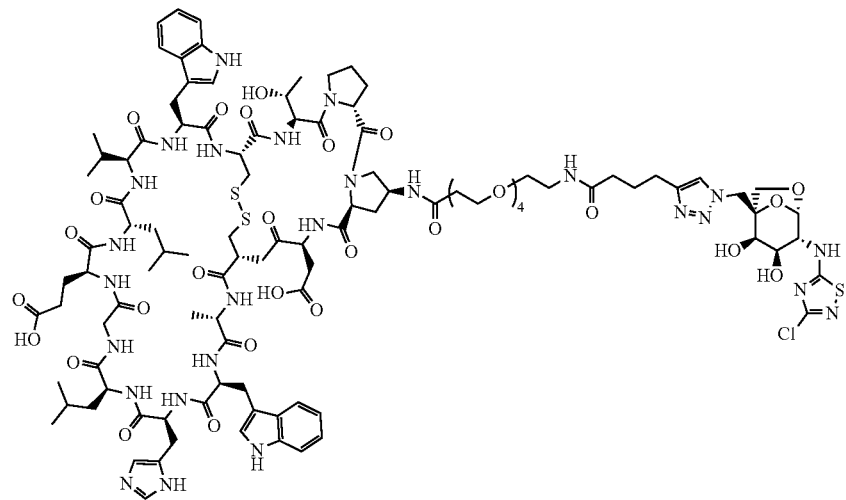

TABLE 1A-continued
Extracellular Protein Degrading Compounds of the Present Invention
Compound 16
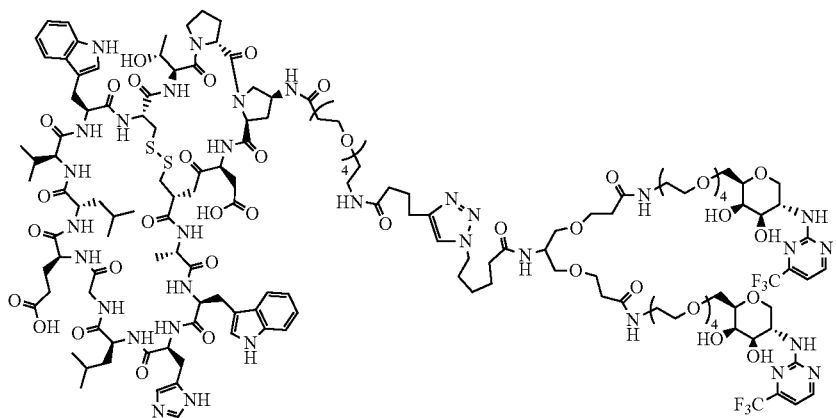
Compound 17
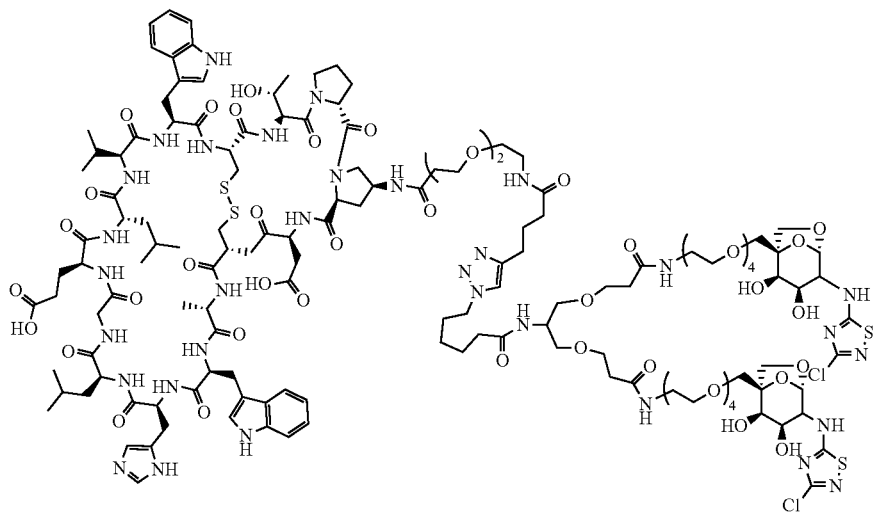
Compound 18
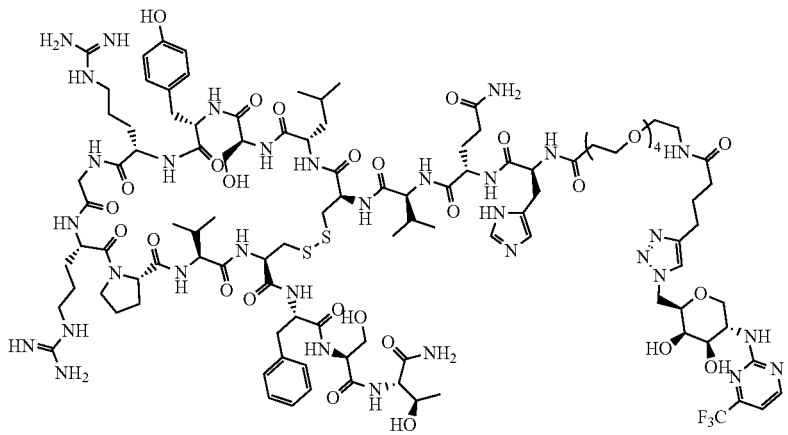

TABLE 1A-continued
Extracellular Protein Degrading Compounds of the Present Invention
Compound 19
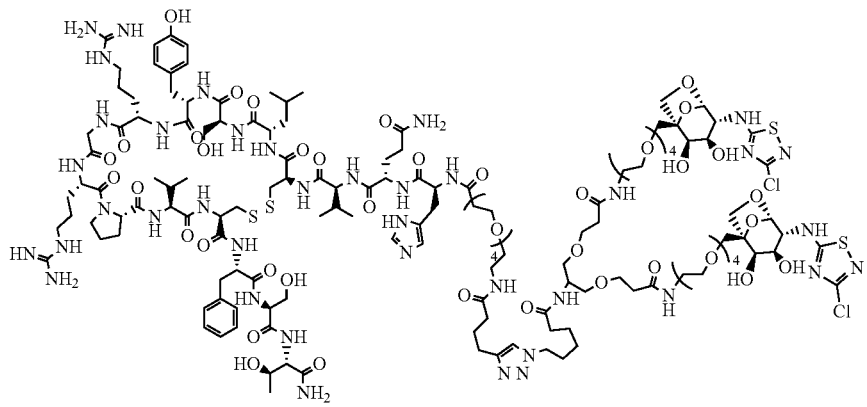
Compound 20
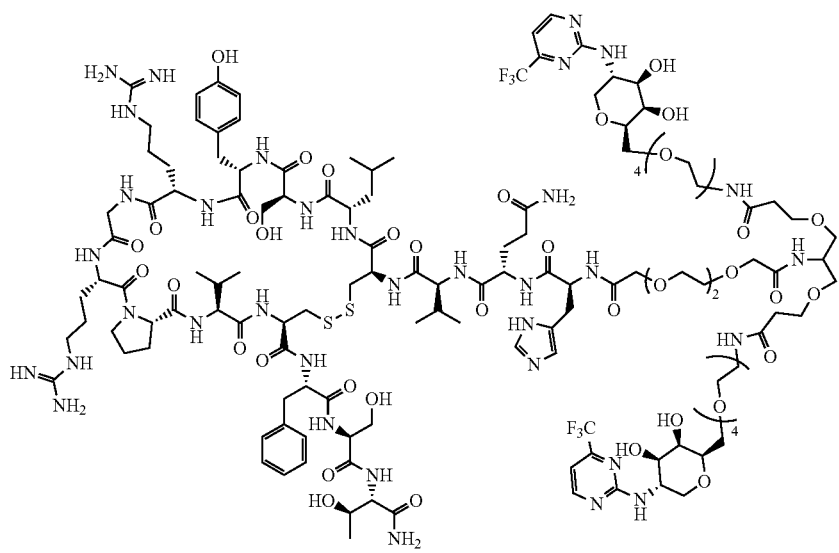
Compound 21
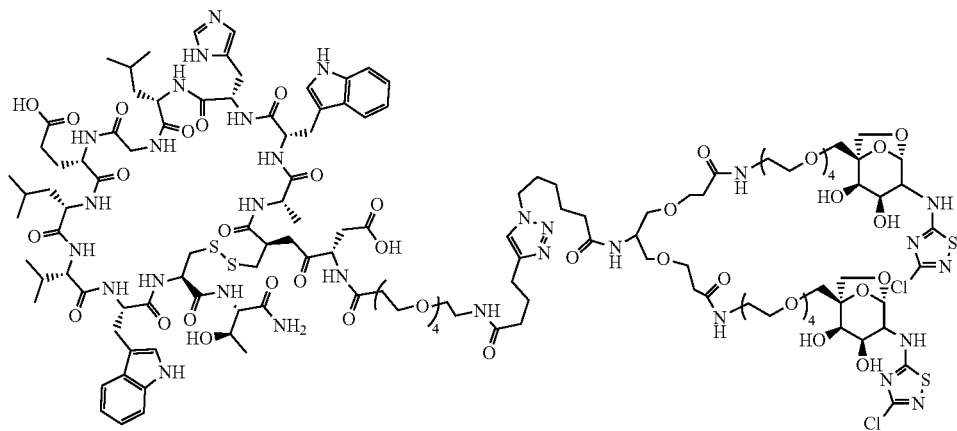

TABLE 1A-continued
Extracellular Protein Degrading Compounds of the Present Invention
Compound 22
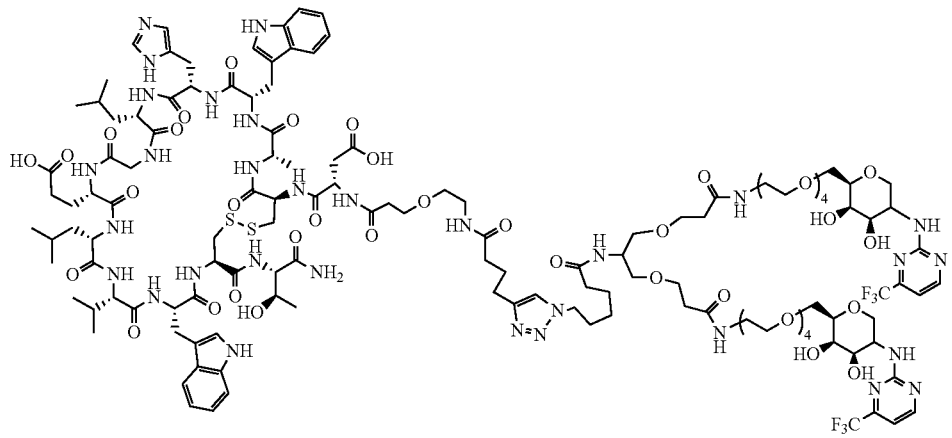
Compound 23
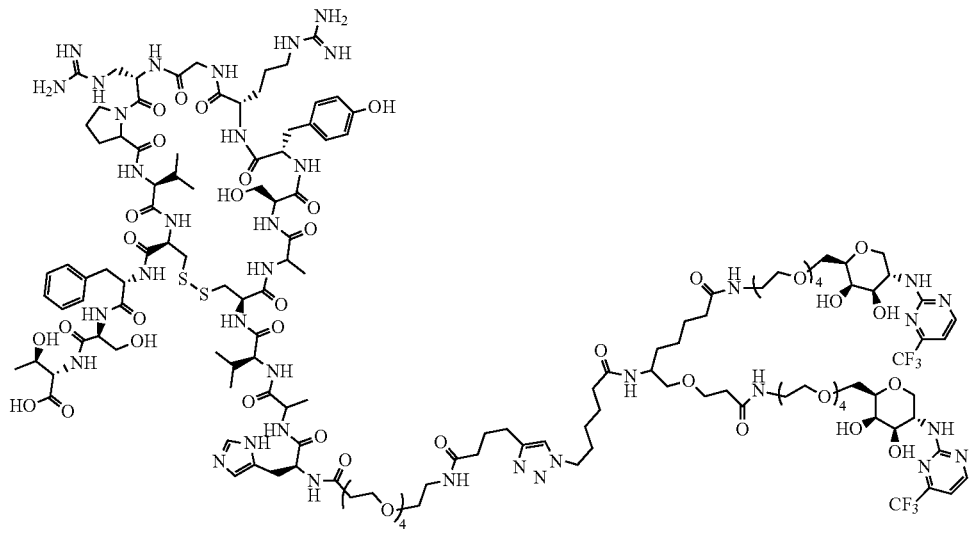
Compound 24
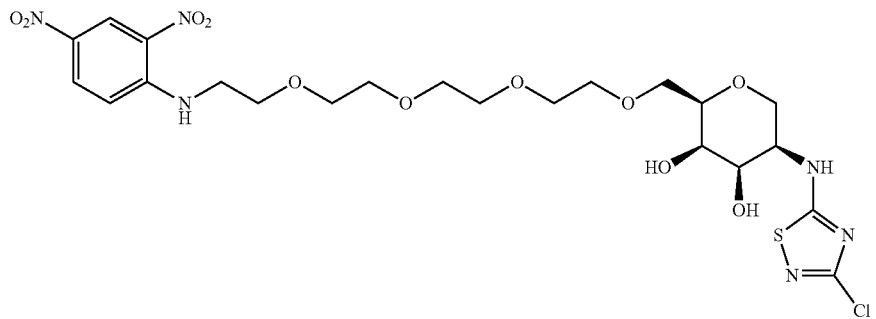 [SMILES: O=[N+]([O-])c1ccc(NCCOCCOCCOCCOC[C@H]2OC[C@@H](Nc3nc(Cl)ns3)[C@@H](O)[C@H]2O)c([N+](=O)[O-])c1]

TABLE 1A-continued
Extracellular Protein Degrading Compounds of the Present Invention
Compound 25
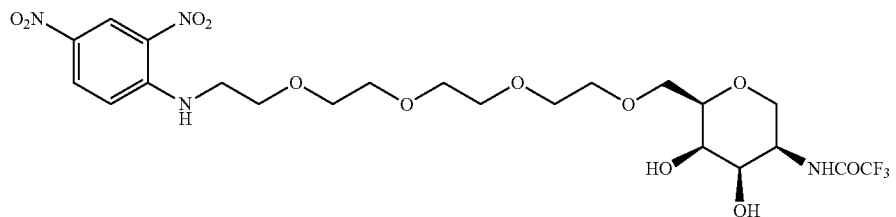
Compound 26
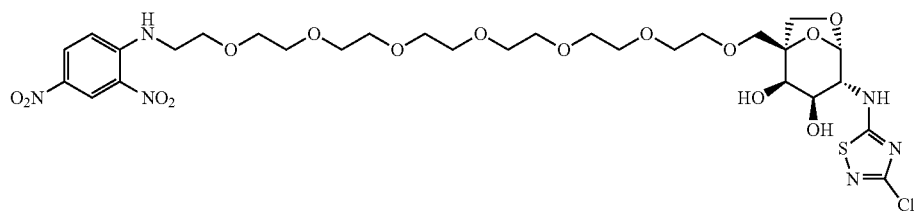 [SMILES: O=[N+]([O-])c1ccc(NCCOCCOCCOCCOCCOCCOCCOC[C@@]23CO[C@@H](O2)[C@H](Nc2nc(Cl)ns2)[C@@H](O)[C@H]3O)c([N+](=O)[O-])c1]
Compound 27
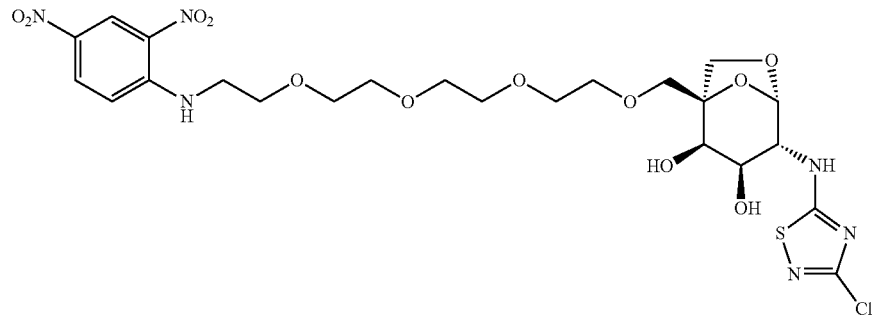 [SMILES: O=[N+]([O-])c1ccc(NCCOCCOCCOCCOC[C@@]23CO[C@@H](O2)[C@H](Nc2nc(Cl)ns2)[C@@H](O)[C@H]3O)c([N+](=O)[O-])c1]
Compound 28
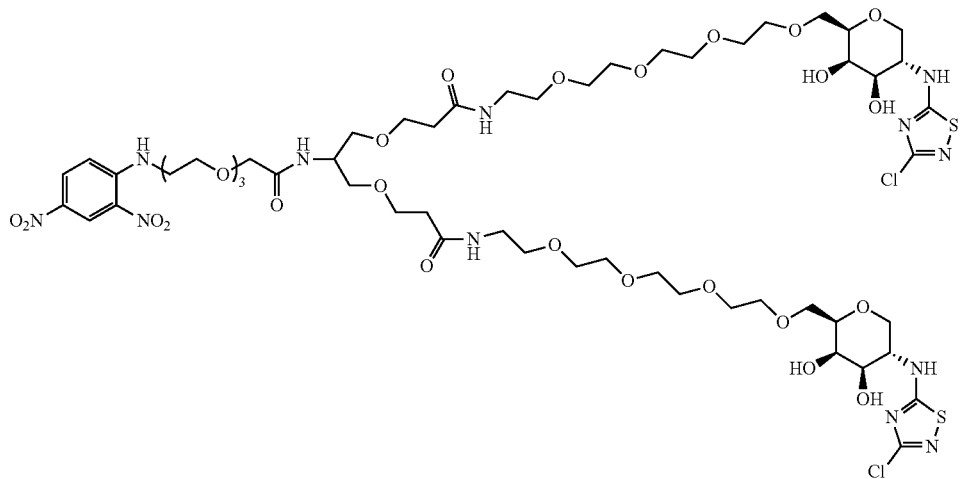

TABLE 1A-continued
Extracellular Protein Degrading Compounds of the Present Invention
Compound 29
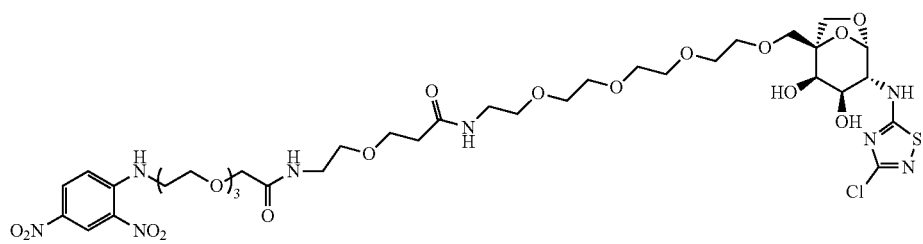
Compound 30
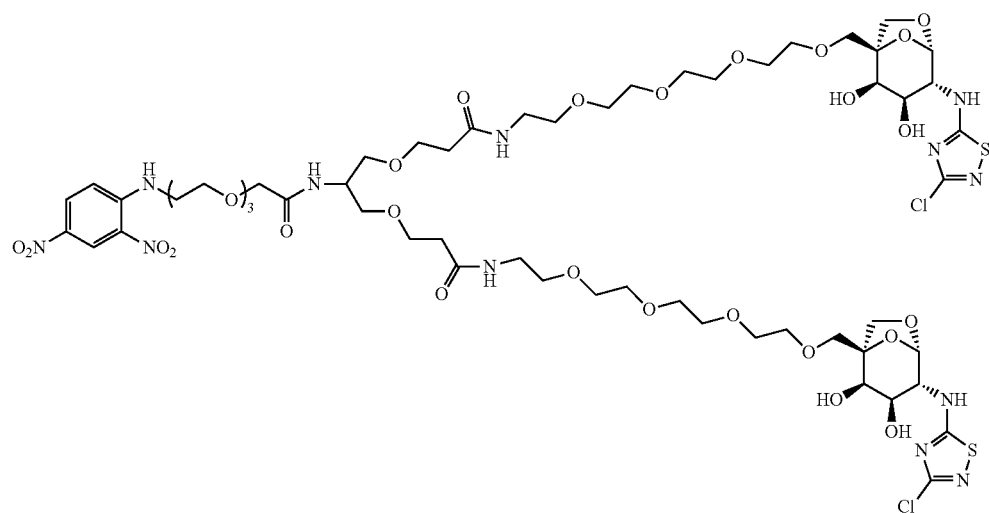
Compound 31
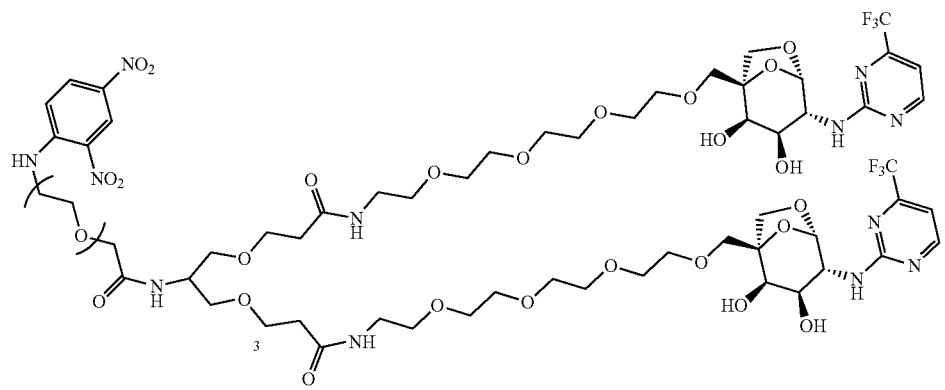

TABLE 1A-continued
Extracellular Protein Degrading Compounds of the Present Invention
Compound 32
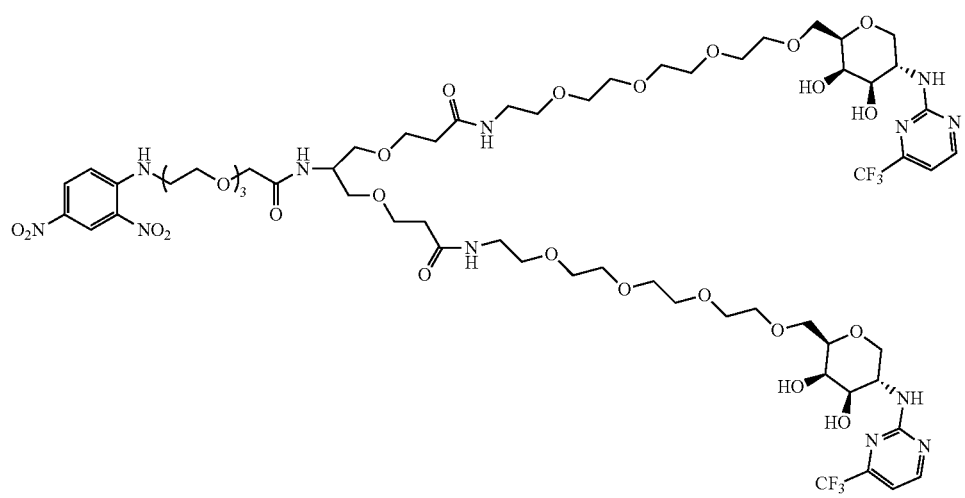
Compound 33
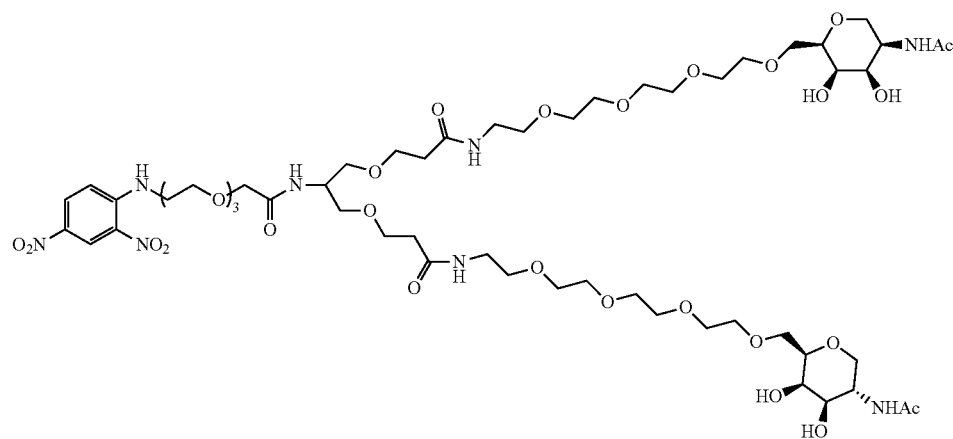
Compound 34
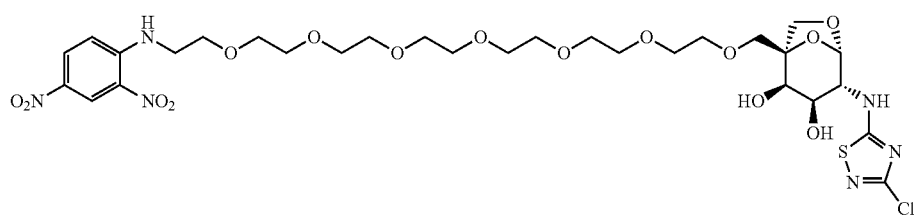 [SMILES: O=[N+]([O-])c1ccc(NCCOCCOCCOCCOCCOCCOCCOC[C@@]23CO[C@@H](O2)[C@H](Nc2nc(Cl)ns2)[C@@H](O)[C@H]3O)c([N+](=O)[O-])c1]

TABLE 1B
Extracellular Protein Degrading Compounds of the Present Invention
Compound 36
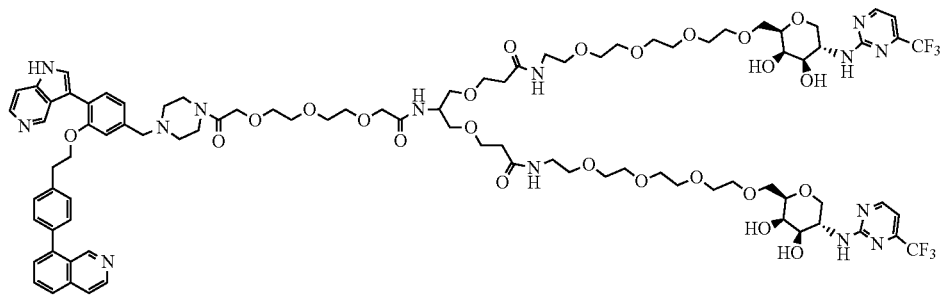 [SMILES: O=C(CCOCC(COCCC(=O)NCCOCCOCCOCCOC[C@H]1OC[C@H](Nc2nccc(C(F)(F)F)n2)[C@@H](O)[C@H]1O)NC(=O)COCCOCCOCC(=O)N1CCN(Cc2ccc(-c3c[nH]c4ccncc34)c(OCCc3ccc(-c4cccc5ccncc45)cc3)c2)CC1)NCCOCCOCCOCCOC[C@H]1OC[C@H](Nc2nccc(C(F)(F)F)n2)[C@@H](O)[C@H]1O]
Compound 37
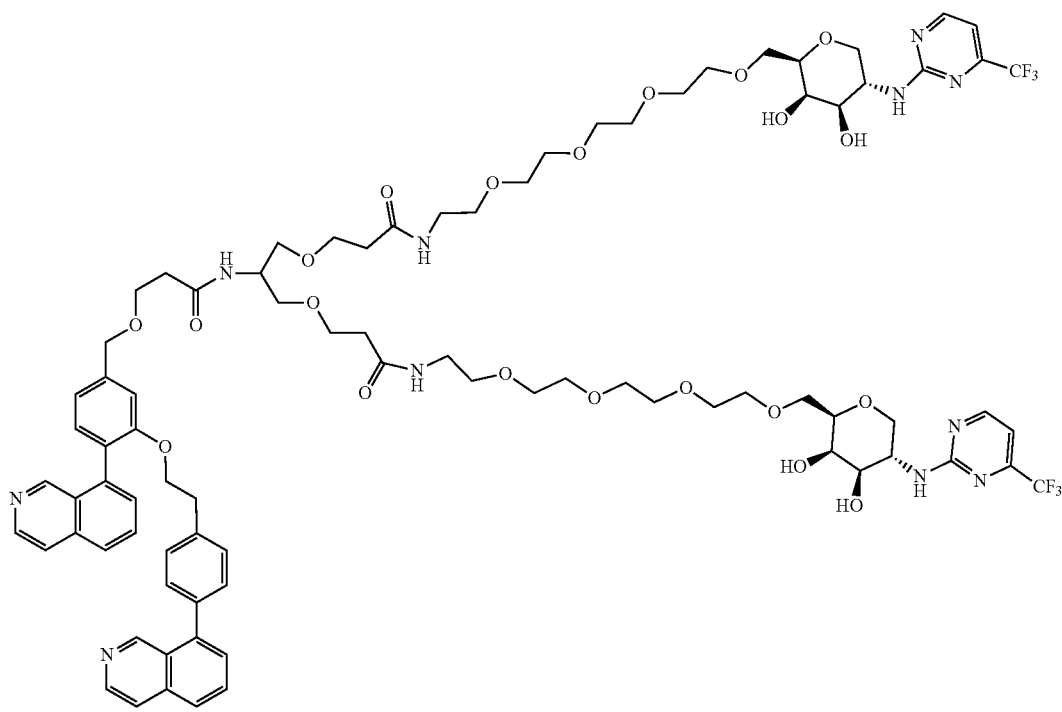 [SMILES: O=C(CCOCC(COCCC(=O)NCCOCCOCCOCCOC[C@H]1OC[C@H](Nc2nccc(C(F)(F)F)n2)[C@@H](O)[C@H]1O)NC(=O)CCOCc1ccc(-c2cccc3ccncc23)c(OCCc2ccc(-c3cccc4ccncc34)cc2)c1)NCCOCCOCCOCCOC[C@H]1OC[C@H](Nc2nccc(C(F)(F)F)n2)[C@@H](O)[C@H]1O]
Compound 38
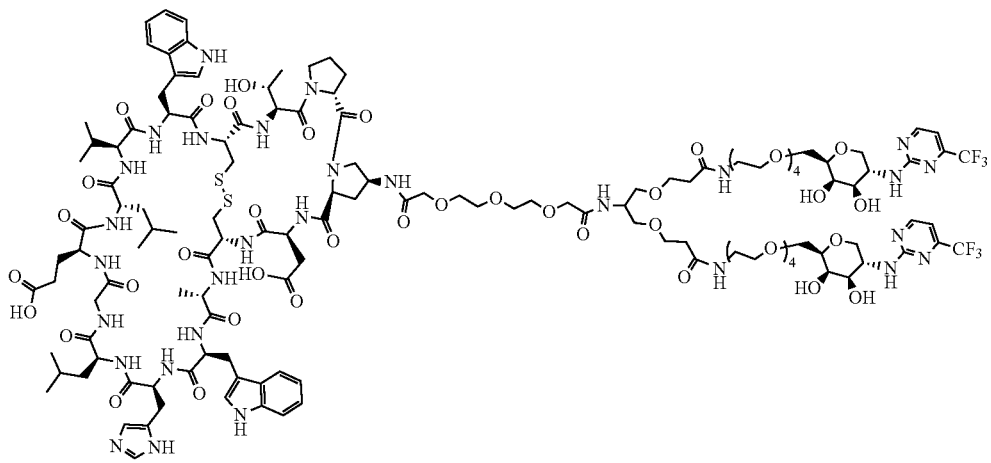

TABLE 1B-continued
Extracellular Protein Degrading Compounds of the Present Invention
Compound 39
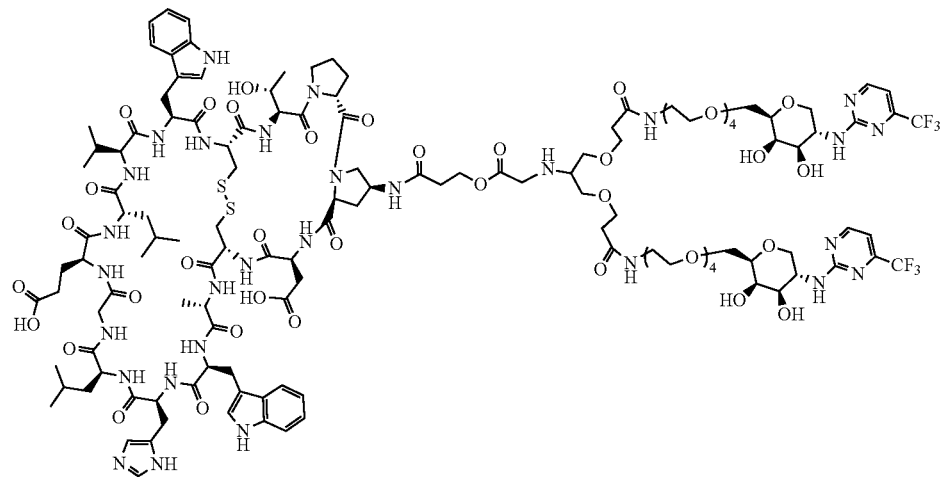
Compound 40
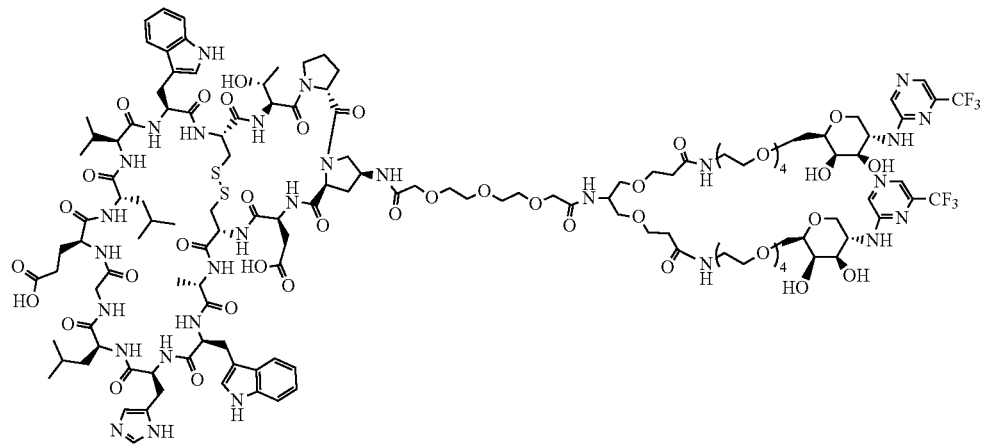

TABLE 1B-continued
Extracellular Protein Degrading Compounds of the Present Invention
Compound 41
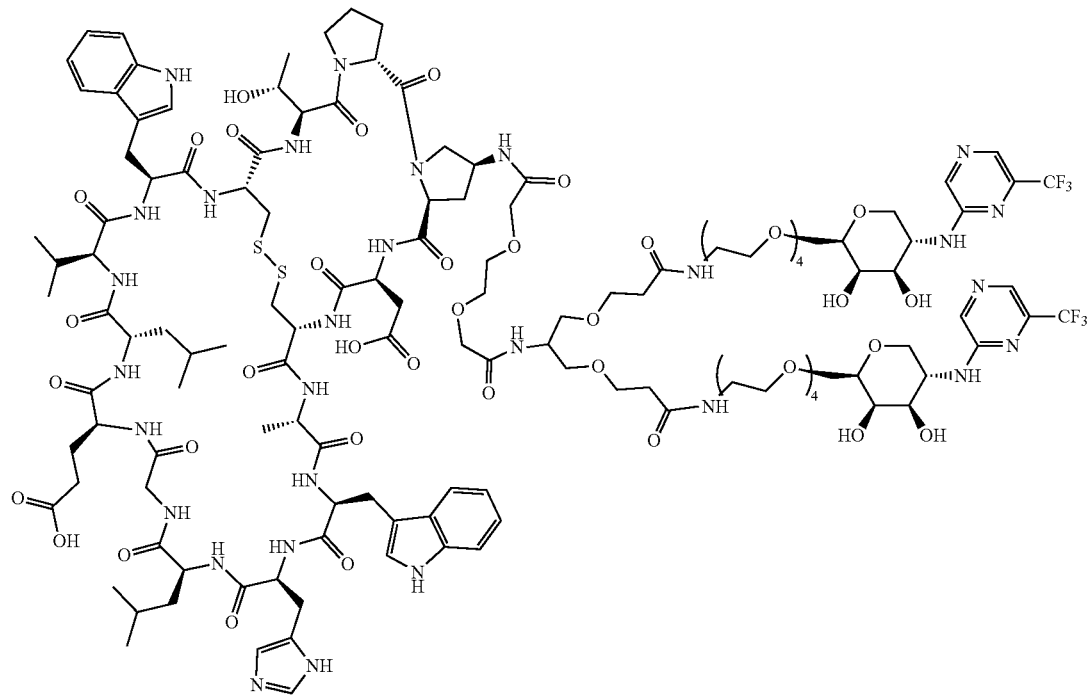
Compound 42
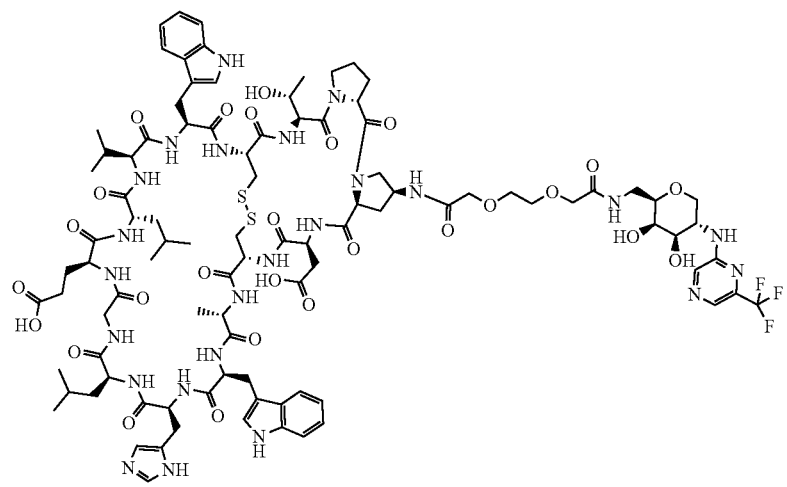 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)COCCOCC(=O)NC[C@H]3OC[C@H](Nc4cncc(C(F)(F)F)n4)[C@@H](O)[C@H]3O)C[C@H]1C(=O)N[C@@H](CC(=O)O)C(=O)N2]

TABLE 1B-continued
Extracellular Protein Degrading Compounds of the Present Invention
Compound 43
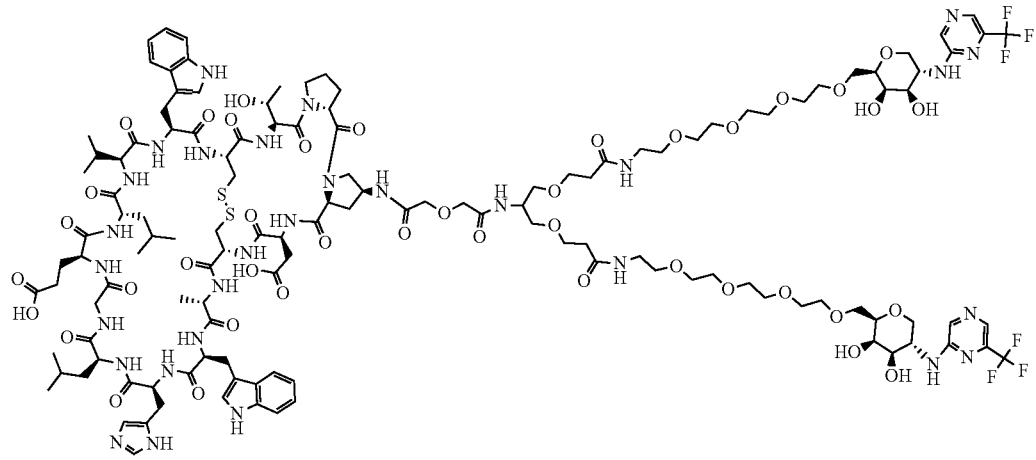 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](CC3=CCNc4ccccc43)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)COCC(=O)NC(COCCC(=O)NCCOCCOCCOCCOC[C@H]3OC[C@H](Nc4cncc(C(F)(F)F)n4)[C@@H](O)[C@H]3O)COCCC(=O)NCCOCCOCCOCCOC[C@H]3OC[C@H](Nc4cncc(C(F)(F)F)n4)[C@@H](O)[C@H]3O)C[C@H]1C(=O)N[C@@H](CC(=O)O)C(=O)N2]
Compound 44
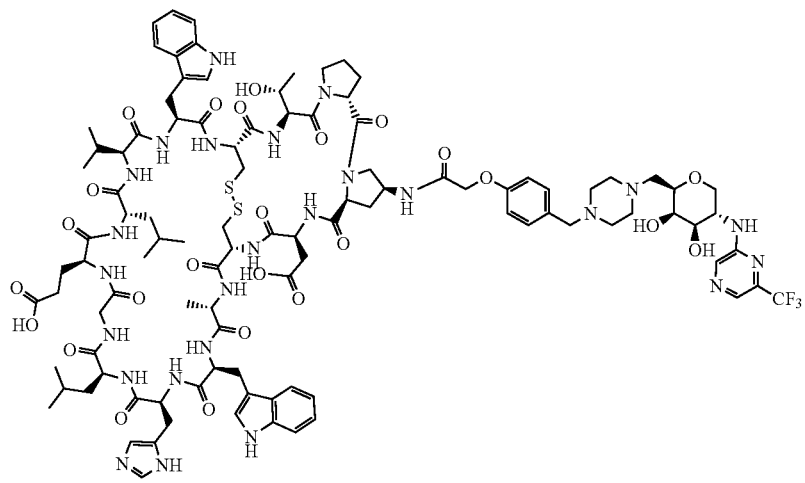
Compound 45
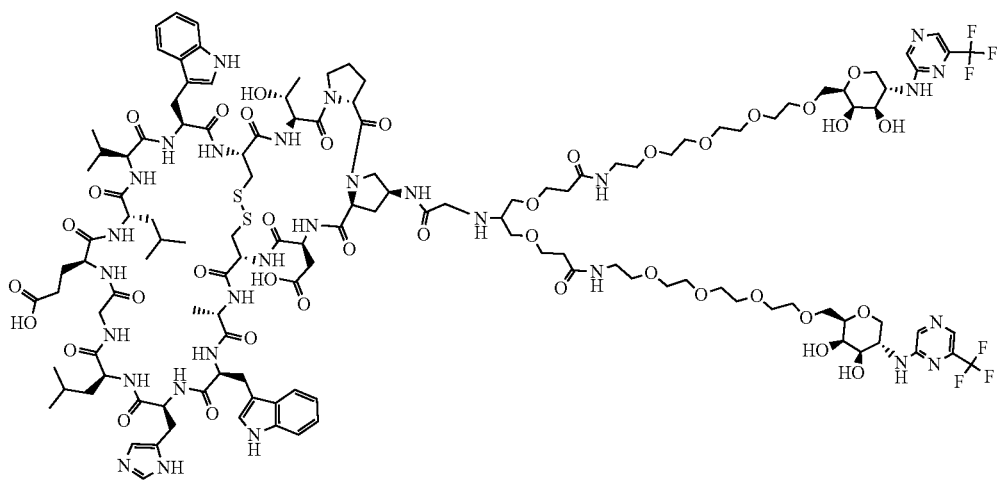 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)CNC(COCCC(=O)NCCOCCOCCOCCOC[C@H]3OC[C@H](Nc4cncc(C(F)(F)F)n4)[C@@H](O)[C@H]3O)COCCC(=O)NCCOCCOCCOCCOC[C@H]3OC[C@H](Nc4cncc(C(F)(F)F)n4)[C@@H](O)[C@H]3O)C[C@H]1C(=O)N[C@@H](CC(=O)O)C(=O)N2]

TABLE 1B-continued
Extracellular Protein Degrading Compounds of the Present Invention
Compound 46
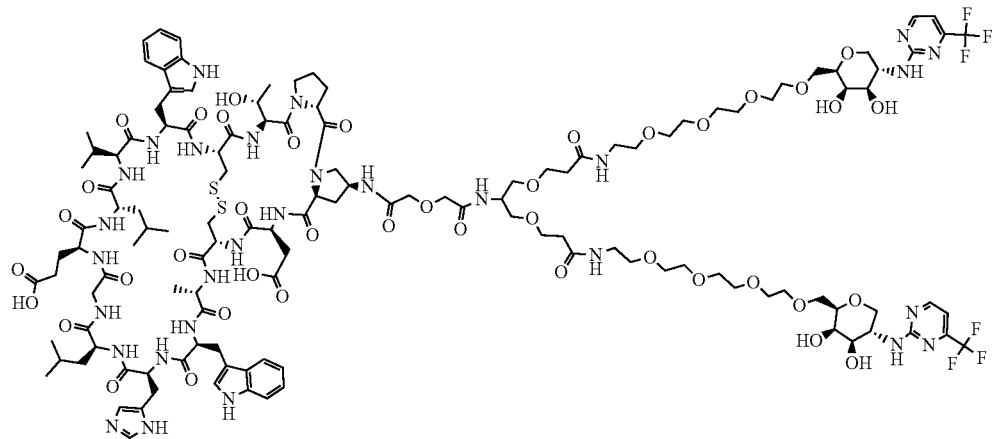 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](CC3=CCNc4ccccc43)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)COCC(=O)NC(COCCC(=O)NCCOCCOCCOCCOC[C@H]3OC[C@H](Nc4nccc(C(F)(F)F)n4)[C@@H](O)[C@H]3O)COCCC(=O)NCCOCCOCCOCCOC[C@H]3OC[C@H](Nc4nccc(C(F)(F)F)n4)[C@@H](O)[C@H]3O)C[C@H]1C(=O)N[C@@H](CC(=O)O)C(=O)N2]
Compound 47
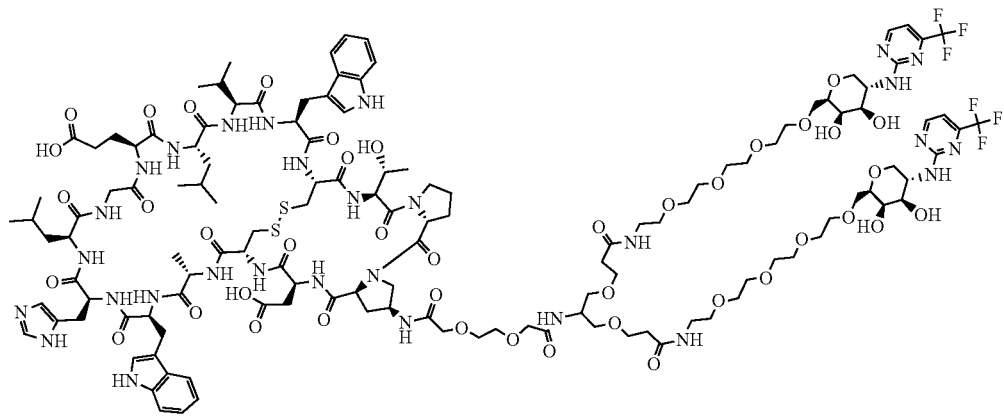 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)COCCOCC(=O)NC(COCCC(=O)NCCOCCOCCOCCOC[C@H]3OC[C@H](Nc4nccc(C(F)(F)F)n4)[C@@H](O)[C@H]3O)COCCC(=O)NCCOCCOCCOCCOC[C@H]3OC[C@H](Nc4nccc(C(F)(F)F)n4)[C@@H](O)[C@H]3O)C[C@H]1C(=O)N[C@@H](CC(=O)O)C(=O)N2]

TABLE 1B-continued
Extracellular Protein Degrading Compounds of the Present Invention
Compound 48
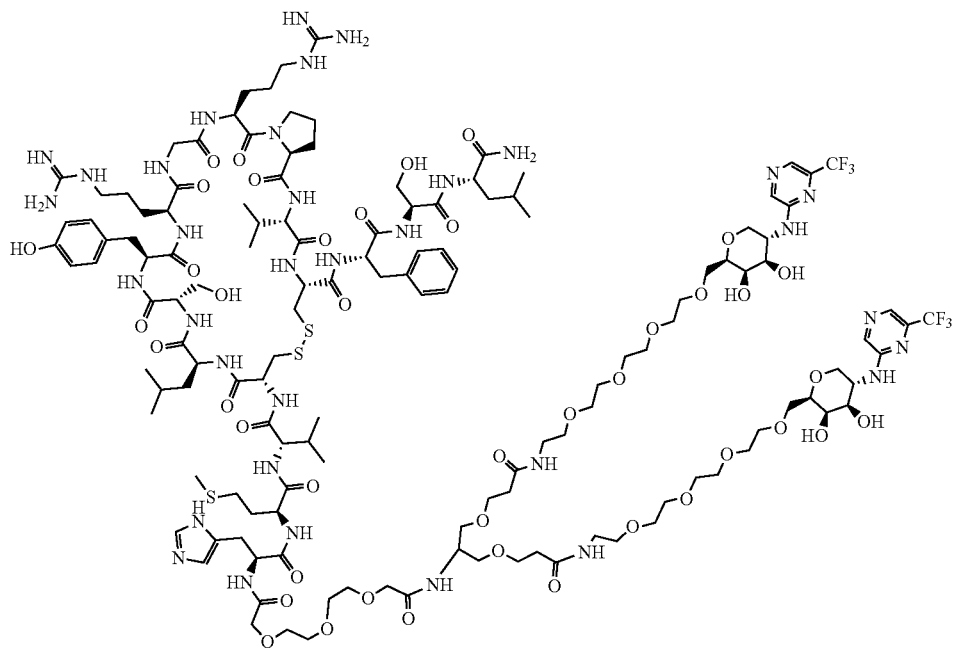 [SMILES: CSCC[C@H](NC(=O)[C@H](Cc1cnc[nH]1)NC(=O)COCCOCCOCC(=O)NC(COCCC(=O)NCCOCCOCCOCCOC[C@H]1OC[C@H](Nc2cncc(C(F)(F)F)n2)[C@@H](O)[C@H]1O)COCCC(=O)NCCOCCOCCOCCOC[C@H]1OC[C@H](Nc2cncc(C(F)(F)F)n2)[C@@H](O)[C@H]1O)C(=O)N[C@H](C(=O)N[C@H]1CSSC[C@@H](C(=O)N[C@@H](Cc2ccccc2)C(=O)N[C@@H](CO)C(=O)N[C@@H](CC(C)C)C(N)=O)NC(=O)[C@H](C(C)C)NC(=O)[C@@H]2CCCN2C(=O)[C@H](CCCNC(=N)N)NC(=O)CNC(=O)[C@H](CCCNC(=N)N)NC(=O)[C@H](Cc2ccc(O)cc2)NC(=O)[C@H](CO)NC(=O)[C@H](CC(C)C)NC1=O)C(C)C]
Compound 49
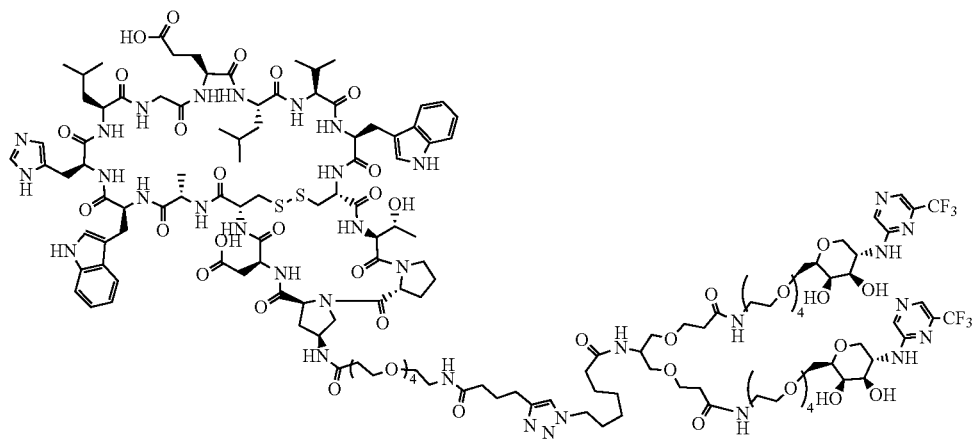

TABLE 1B-continued
Extracellular Protein Degrading Compounds of the Present Invention
Compound 50
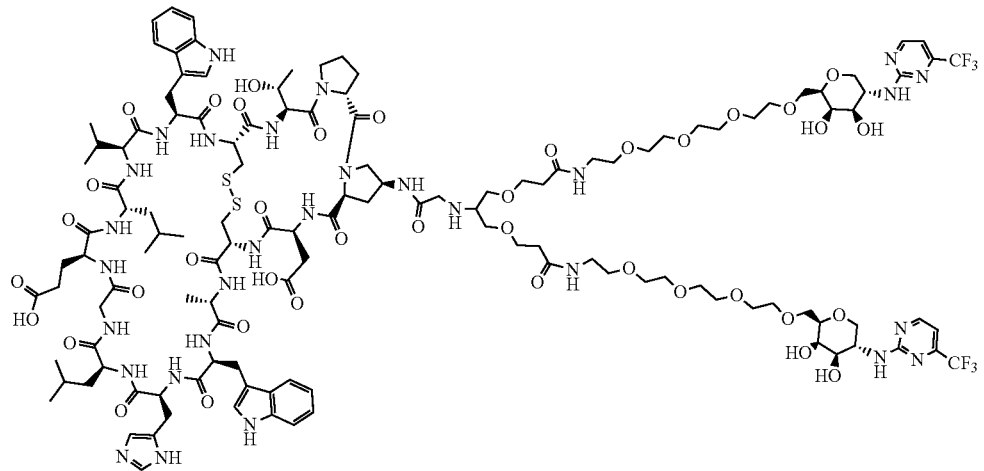 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)CNC(COCCC(=O)NCCOCCOCCOCCOC[C@H]3OC[C@H](Nc4nccc(C(F)(F)F)n4)[C@@H](O)[C@H]3O)COCCC(=O)NCCOCCOCCOCCOC[C@H]3OC[C@H](Nc4nccc(C(F)(F)F)n4)[C@@H](O)[C@H]3O)C[C@H]1C(=O)N[C@@H](CC(=O)O)C(=O)N2]
Compound 51
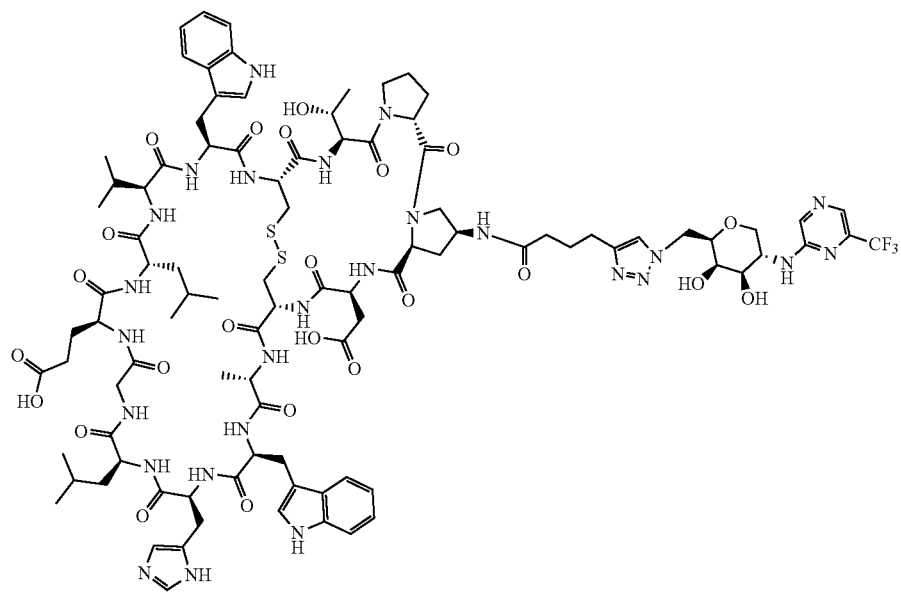 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)CCCc3cn(C[C@H]4OC[C@H](Nc5cncc(C(F)(F)F)n5)[C@@H](O)[C@H]4O)nn3)C[C@H]1C(=O)N[C@@H](CC(=O)O)C(=O)N2]

US 12,091,402 B2
TABLE 1B-continued
Extracellular Protein Degrading Compounds of the Present Invention
Compound 52
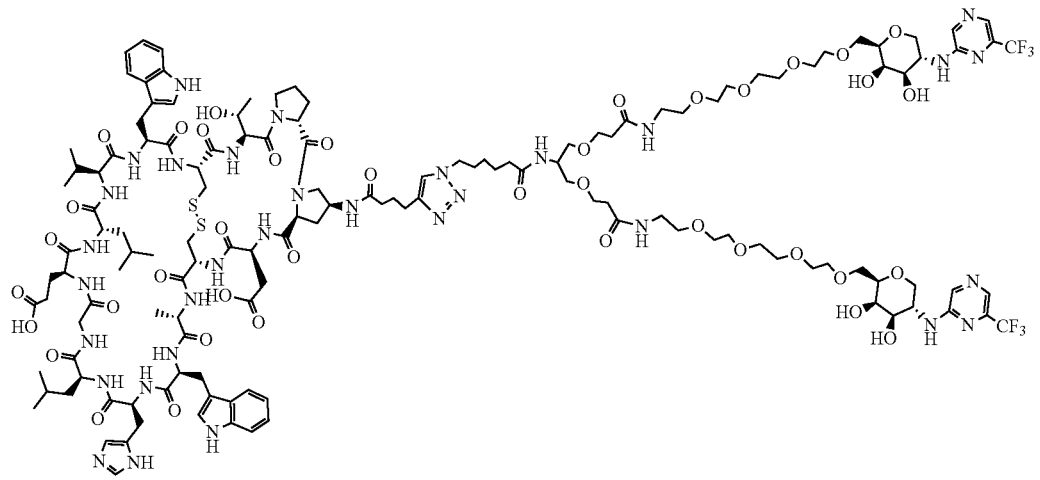 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)CCCc3cn(CCCCCC(=O)NC(COCCC(=O)NCCOCCOCCOCCOC[C@H]4OC[C@H](Nc5cncc(C(F)(F)F)n5)[C@@H](O)[C@H]4O)COCCC(=O)NCCOCCOCCOCCOC[C@H]4OC[C@H](Nc5cncc(C(F)(F)F)n5)[C@@H](O)[C@H]4O)nn3)C[C@H]1C(=O)N[C@@H](CC(=O)O)C(=O)N2]
Compound 53
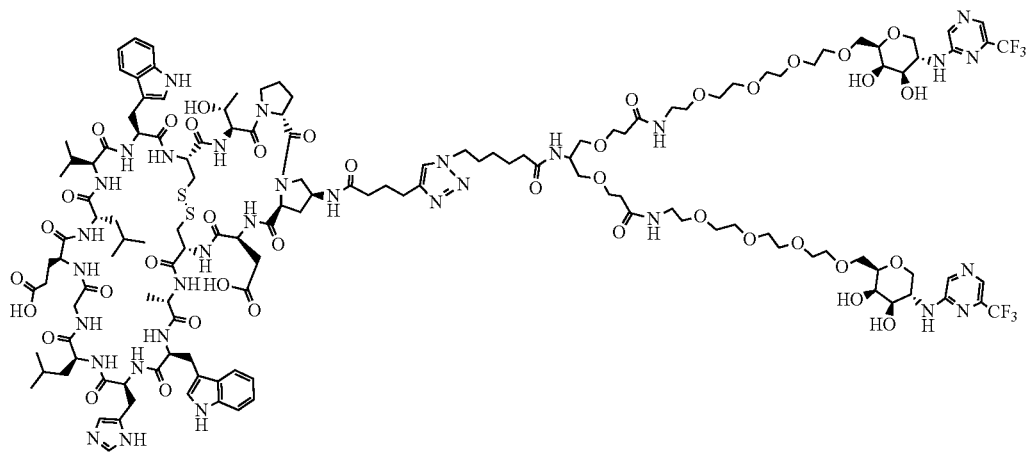 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)CCCc3cn(CCCCCC(=O)NC(COCCC(=O)NCCOCCOCCOCCOC[C@H]4OC[C@H](Nc5cncc(C(F)(F)F)n5)[C@@H](O)[C@H]4O)COCCC(=O)NCCOCCOCCOCCOC[C@H]4OC[C@H](Nc5cncc(C(F)(F)F)n5)[C@@H](O)[C@H]4O)nn3)C[C@H]1C(=O)N[C@@H](CC(=O)O)C(=O)N2]
Compound 54
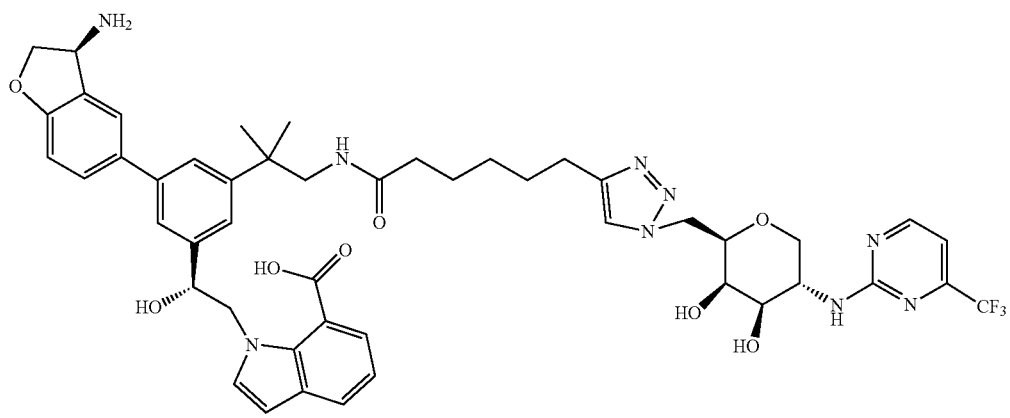

TABLE 1B-continued
Extracellular Protein Degrading Compounds of the Present Invention
Compound 55
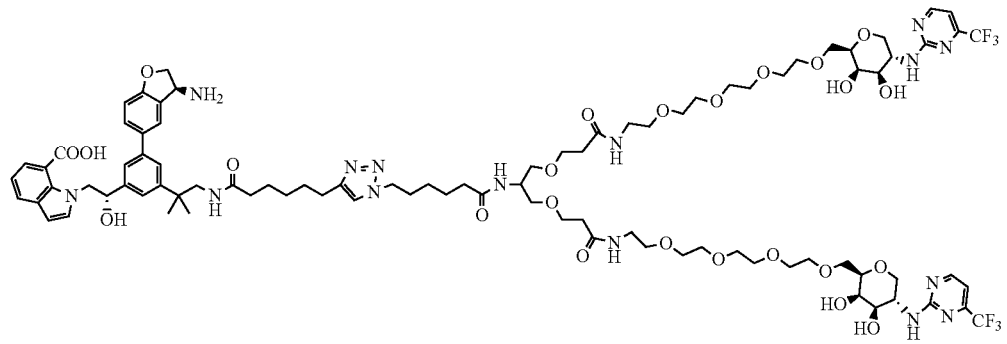 [SMILES: CC(C)(CNC(=O)CCCCCc1cn(CCCCCC(=O)NC(COCCC(=O)NCCOCCOCCOCCOC[C@H]2OC[C@H](Nc3nccc(C(F)(F)F)n3)[C@@H](O)[C@H]2O)COCCC(=O)NCCOCCOCCOCCOC[C@H]2OC[C@H](Nc3nccc(C(F)(F)F)n3)[C@@H](O)[C@H]2O)nn1)c1cc(-c2ccc3c(c2)[C@H](N)CO3)cc([C@H](O)Cn2ccc3cccc(C(=O)O)c32)c1]
Compound 56
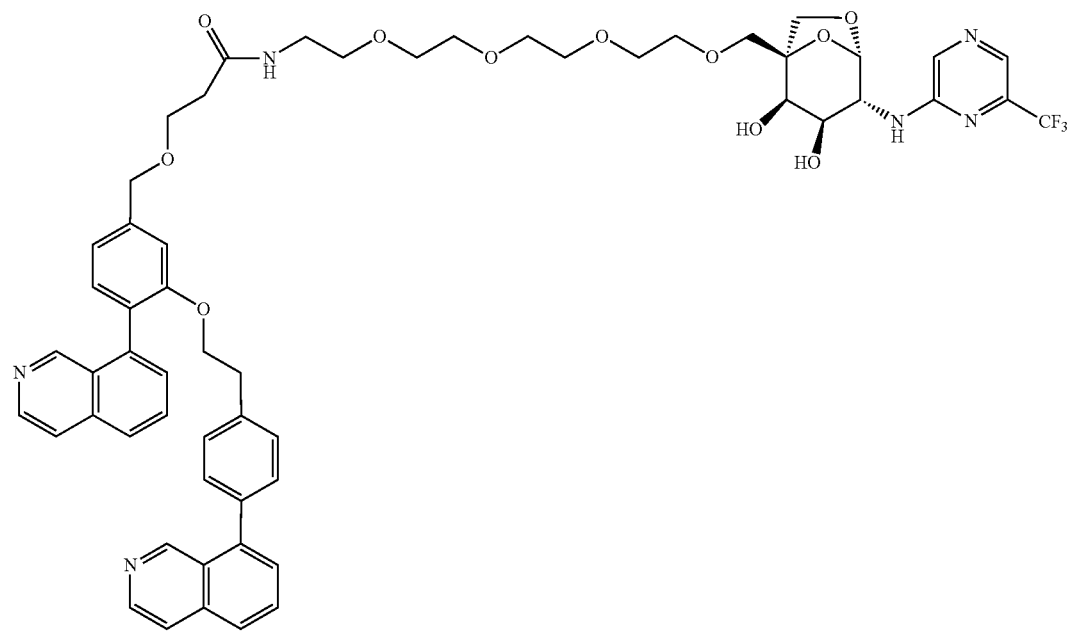 [SMILES: O=C(CCOCc1ccc(-c2cccc3ccncc23)c(OCCc2ccc(-c3cccc4ccncc34)cc2)c1)NCCOCCOCCOCCOC[C@@]12CO[C@@H](O1)[C@H](Nc1cncc(C(F)(F)F)n1)[C@@H](O)[C@H]2O]

TABLE 1B-continued
Extracellular Protein Degrading Compounds of the Present Invention
Compound 57
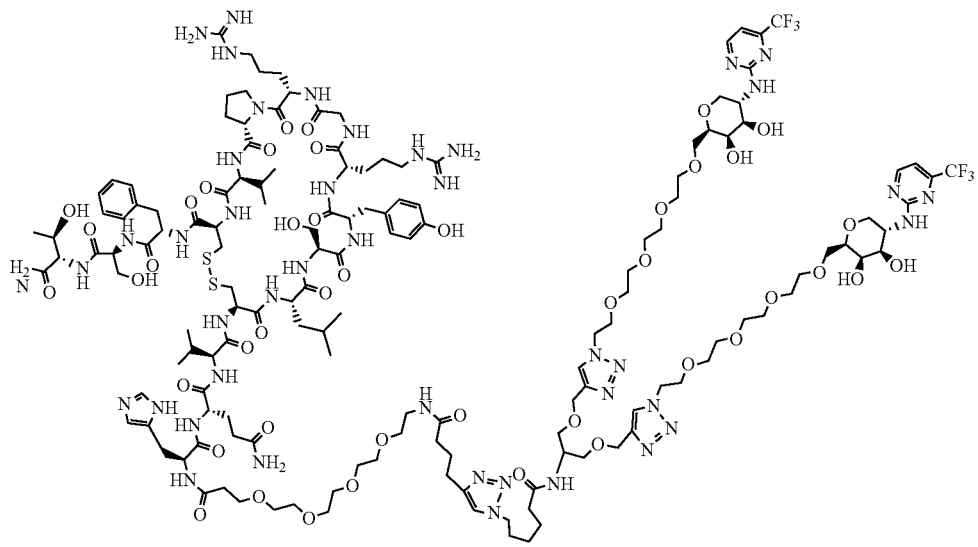
Compound 58
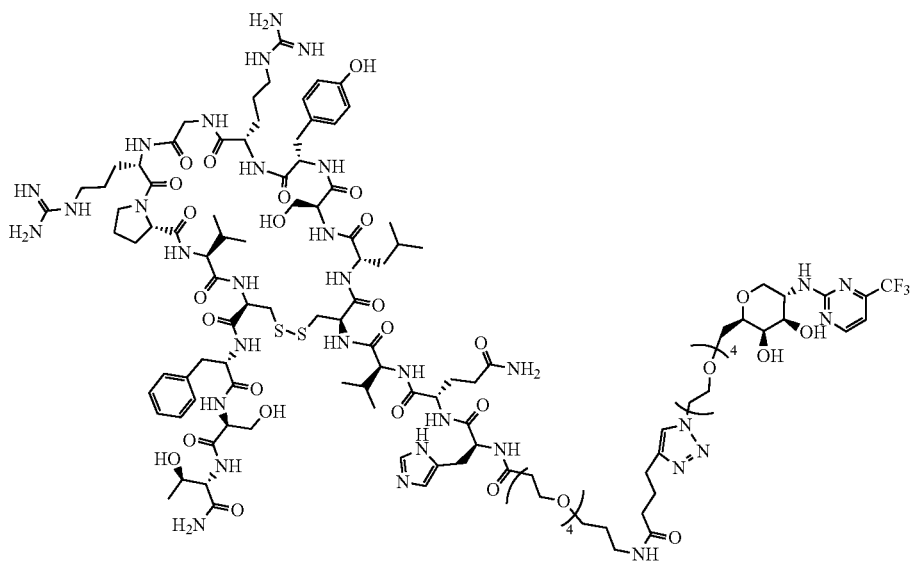

TABLE 1B-continued
Extracellular Protein Degrading Compounds of the Present Invention
Compound 59
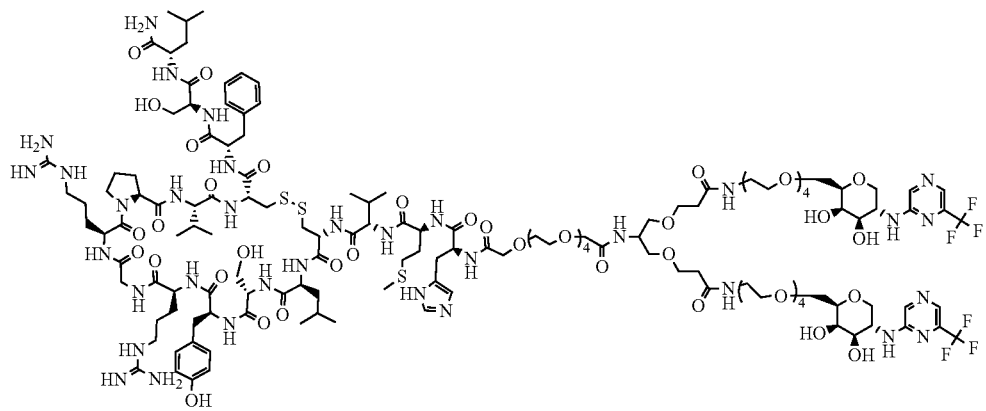
Compound 60
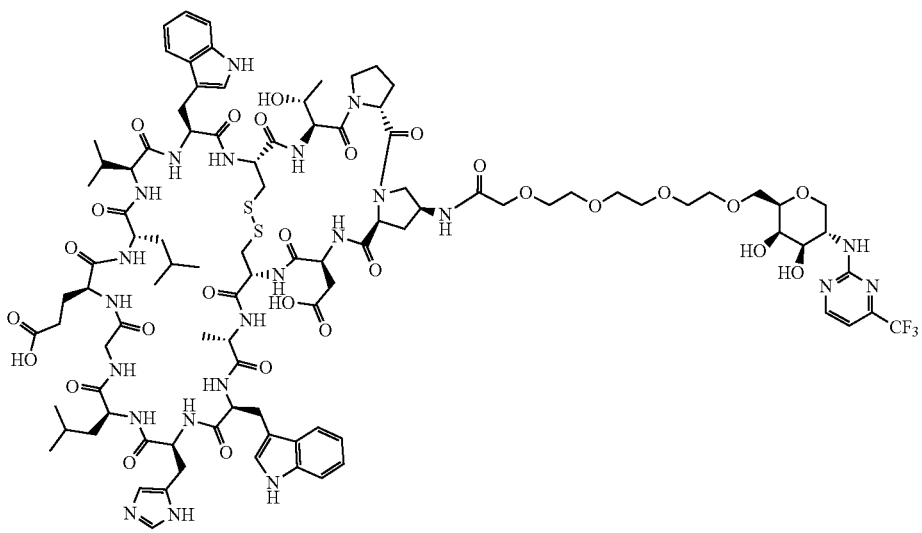 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)COCCOCCOCCOC[C@H]3OC[C@H](Nc4nccc(C(F)(F)F)n4)[C@@H](O)[C@H]3O)C[C@H]1C(=O)N[C@@H](CC(=O)O)C(=O)N2]
45
Additional Representative Immunoglobulin Degraders

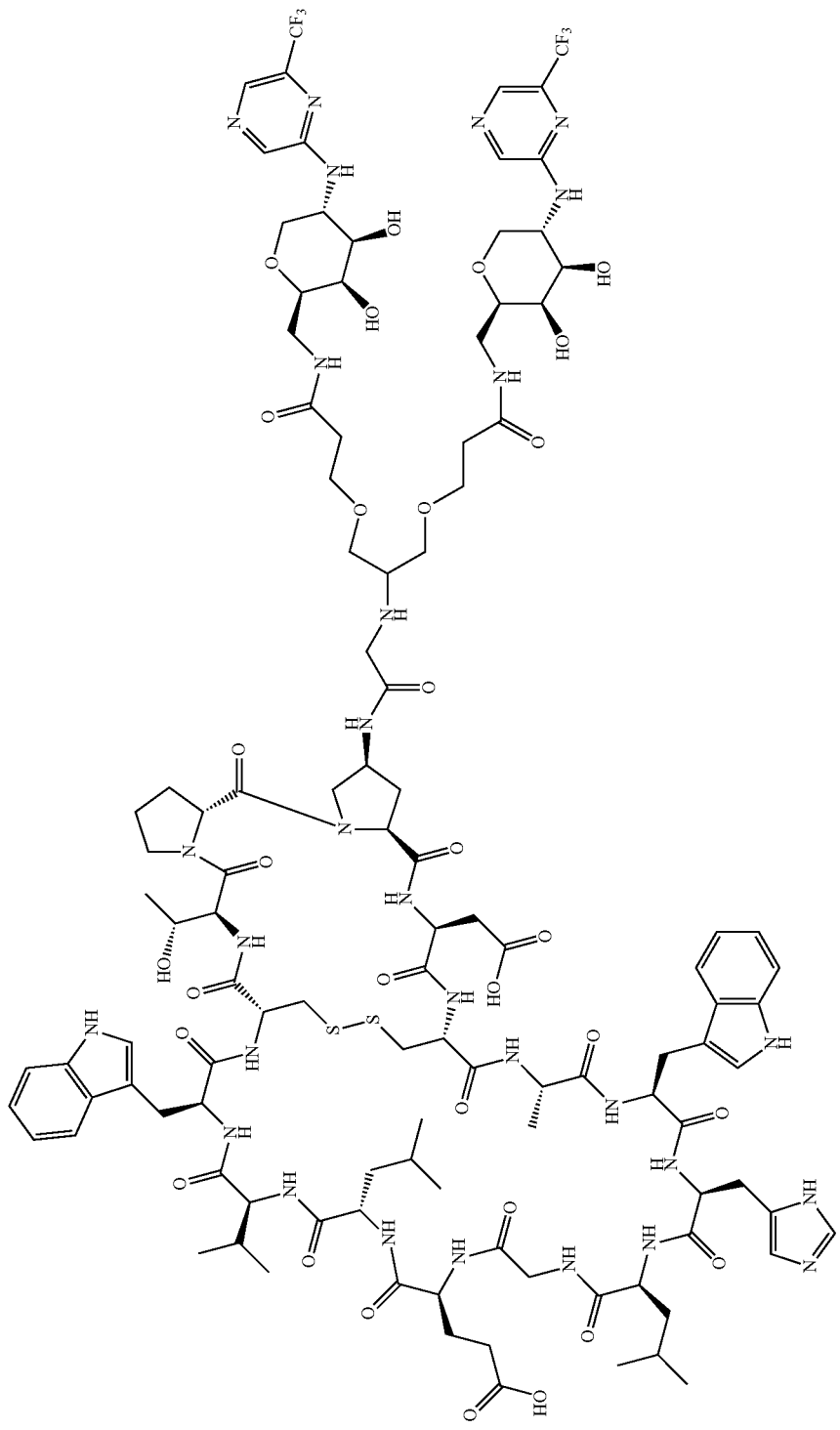

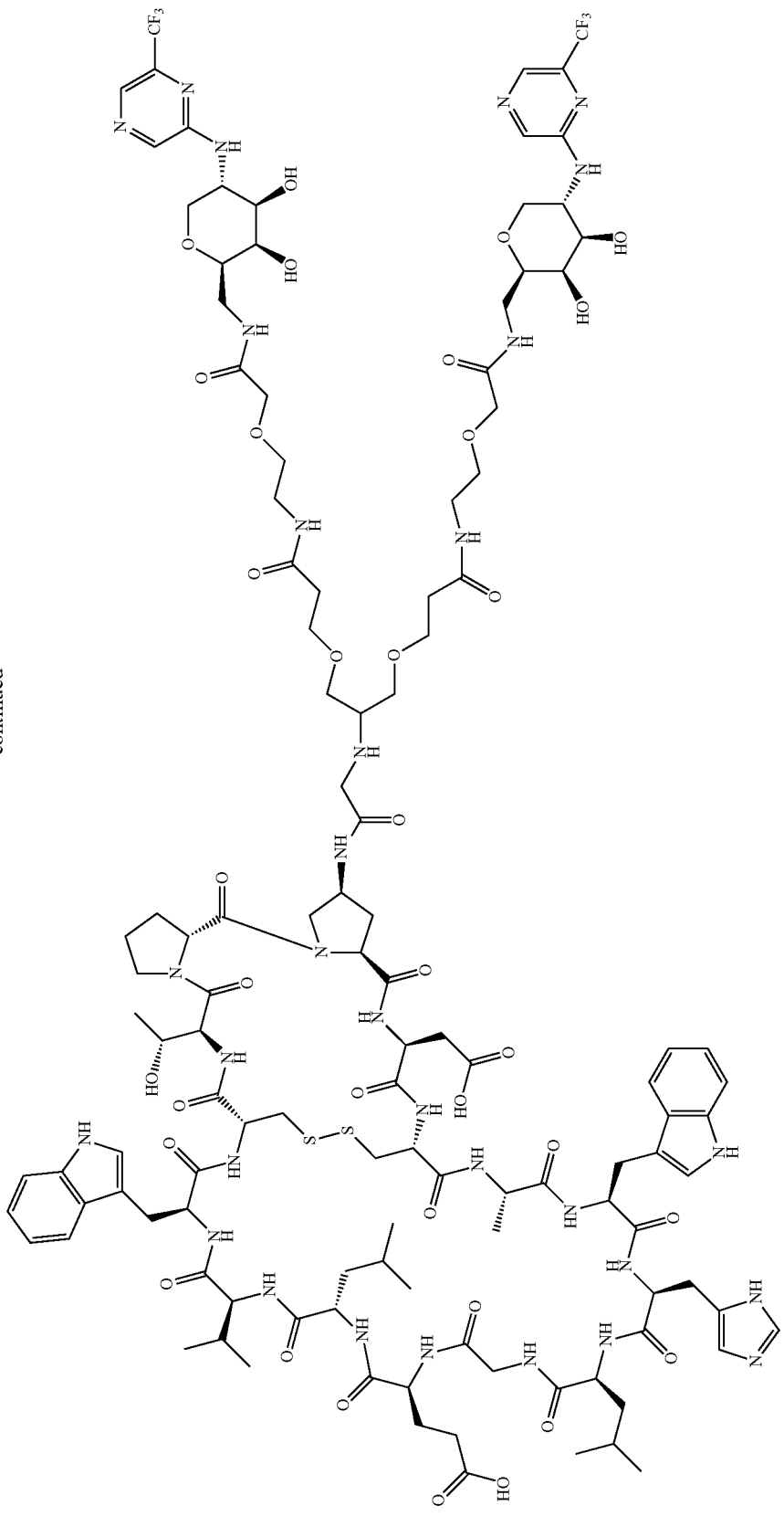

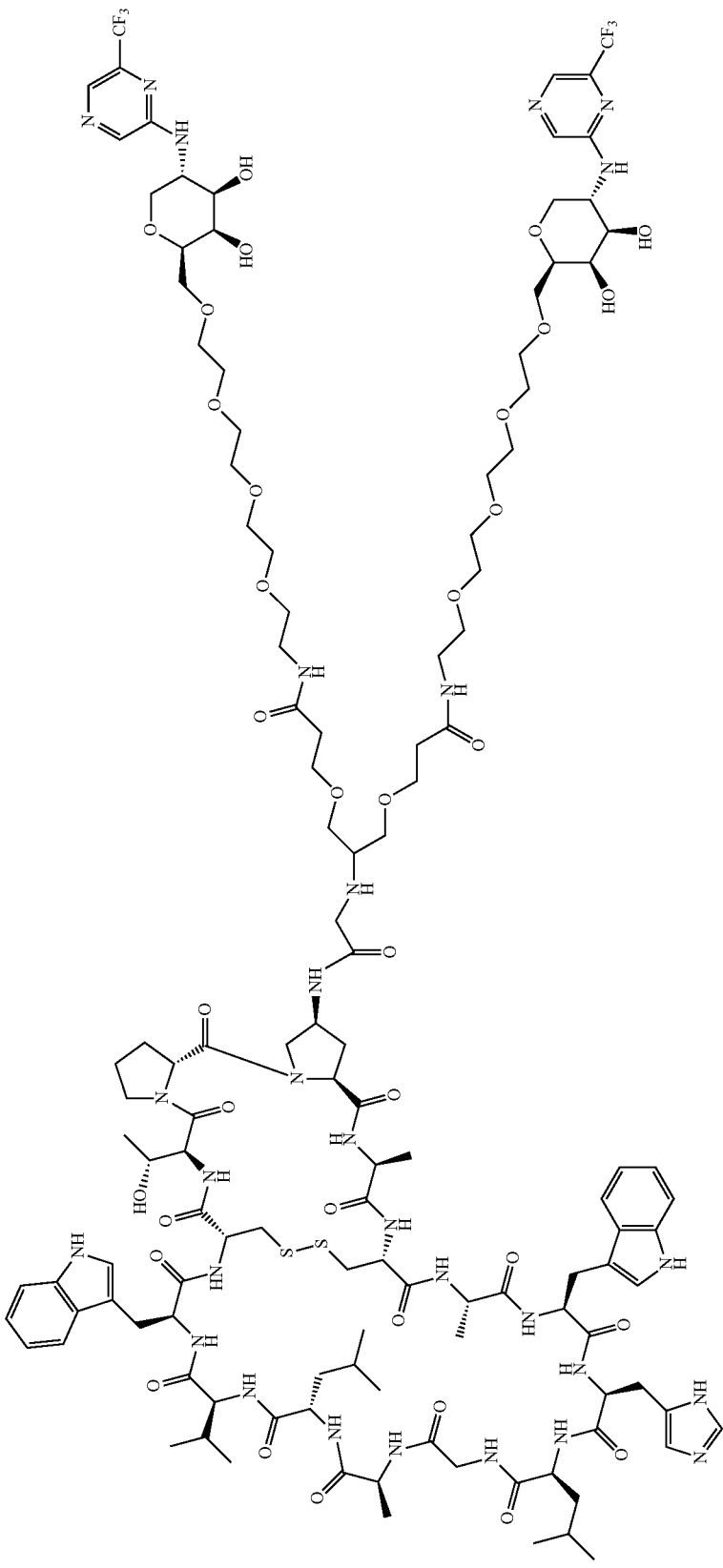

-continued
1455 1456
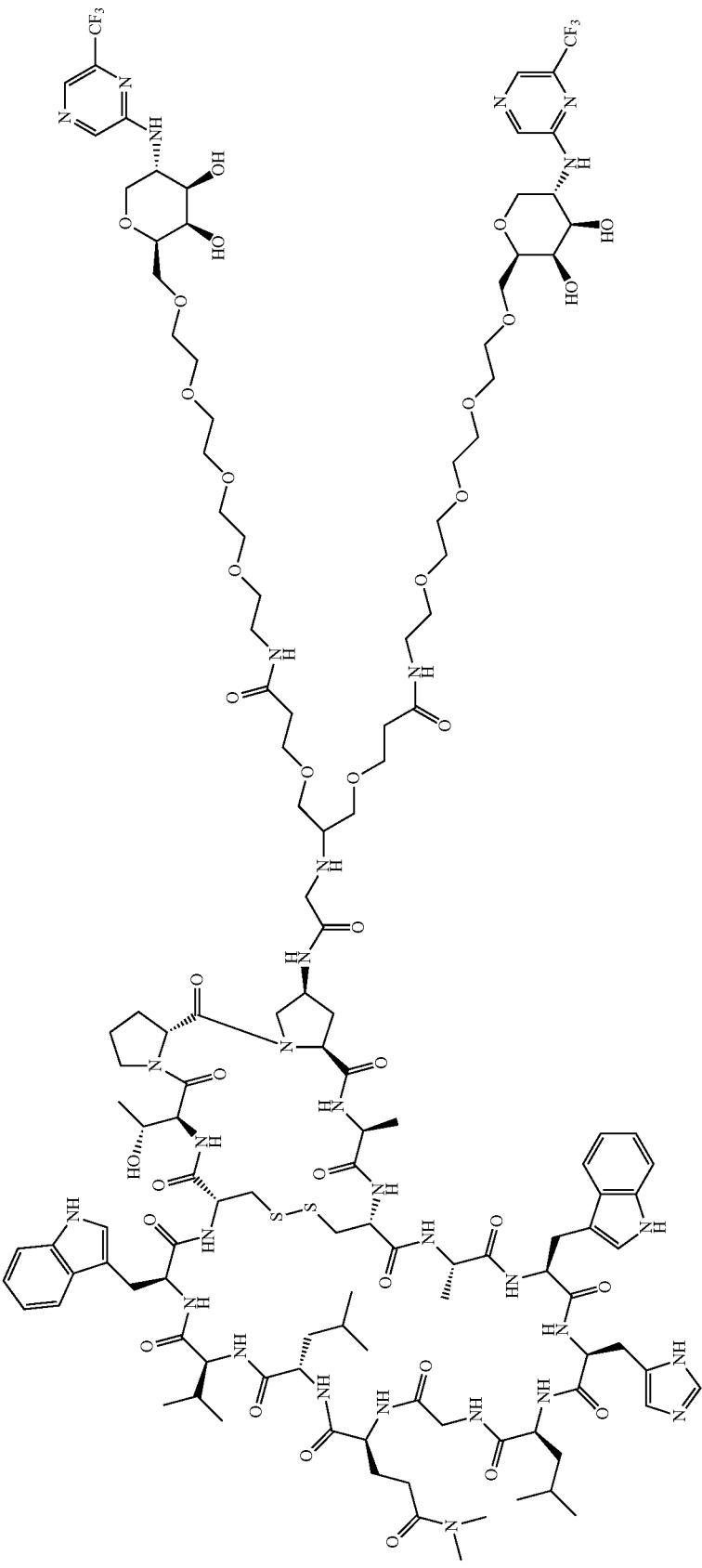

1457 1458
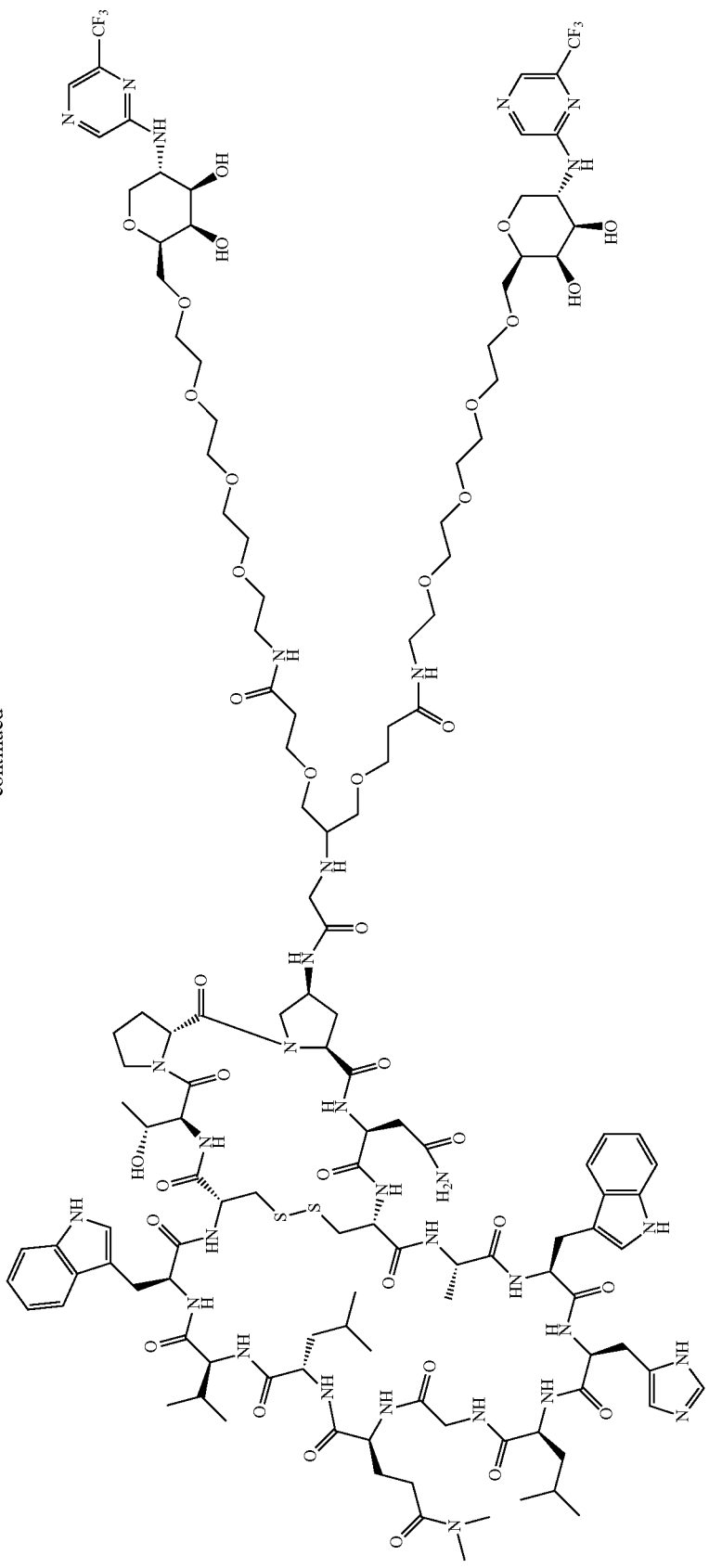

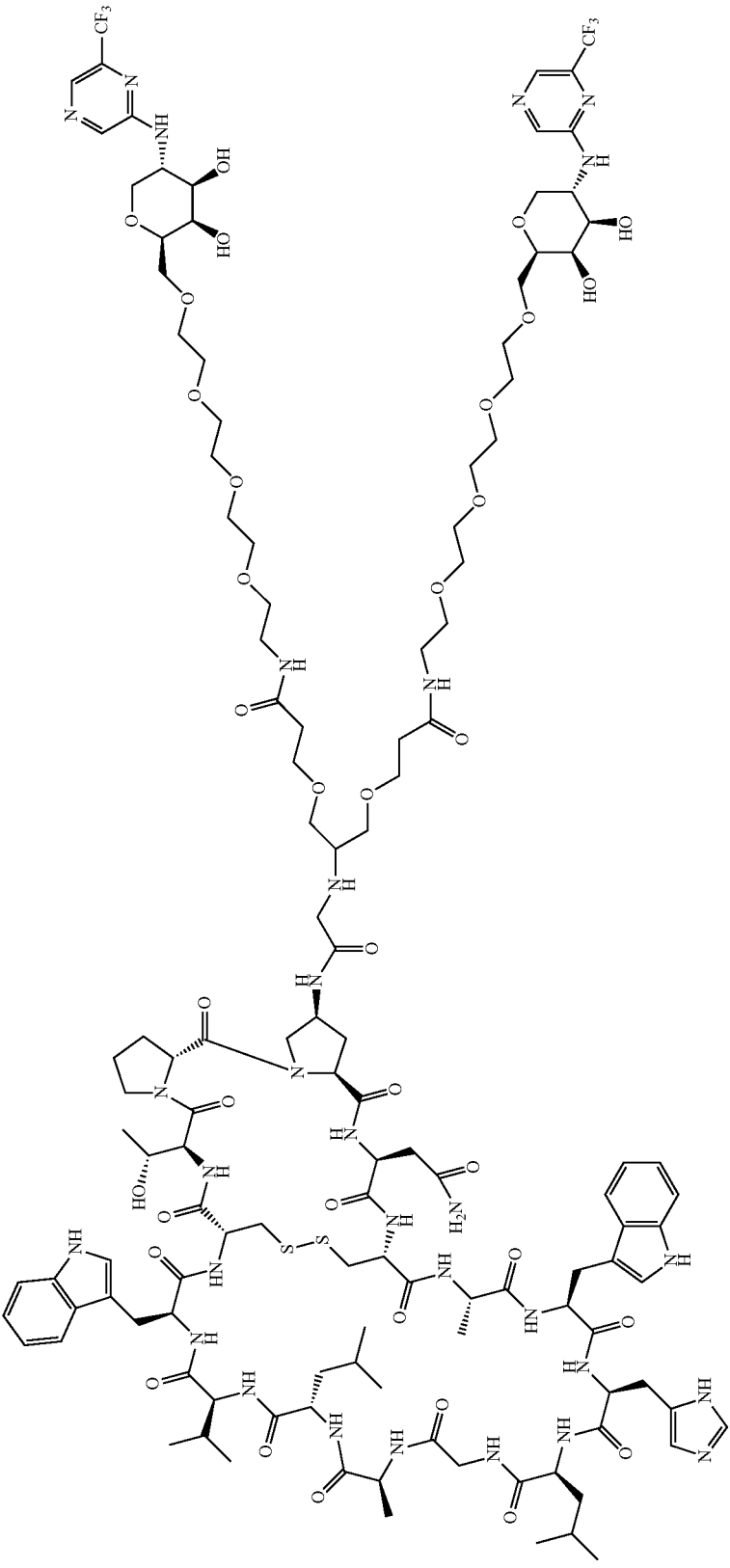

1461 1462
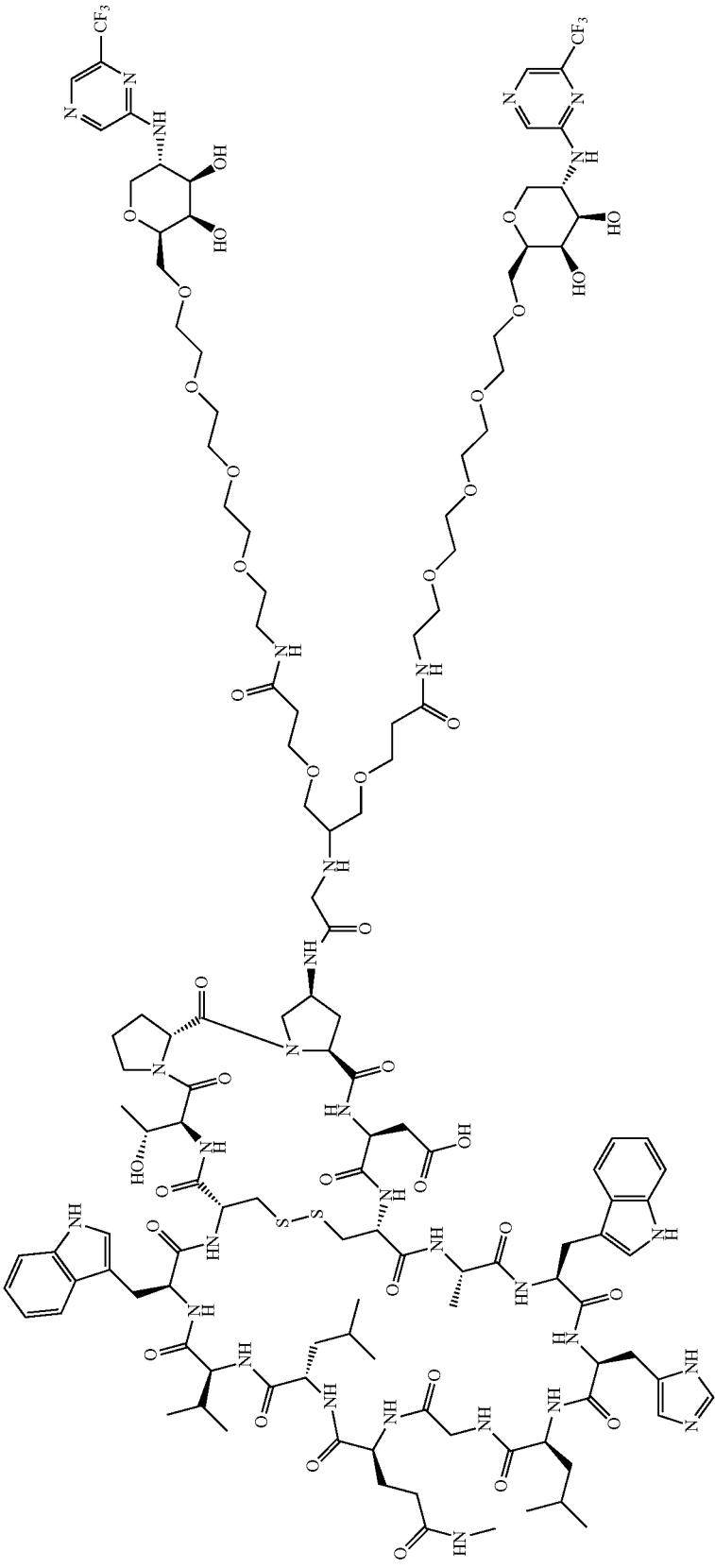

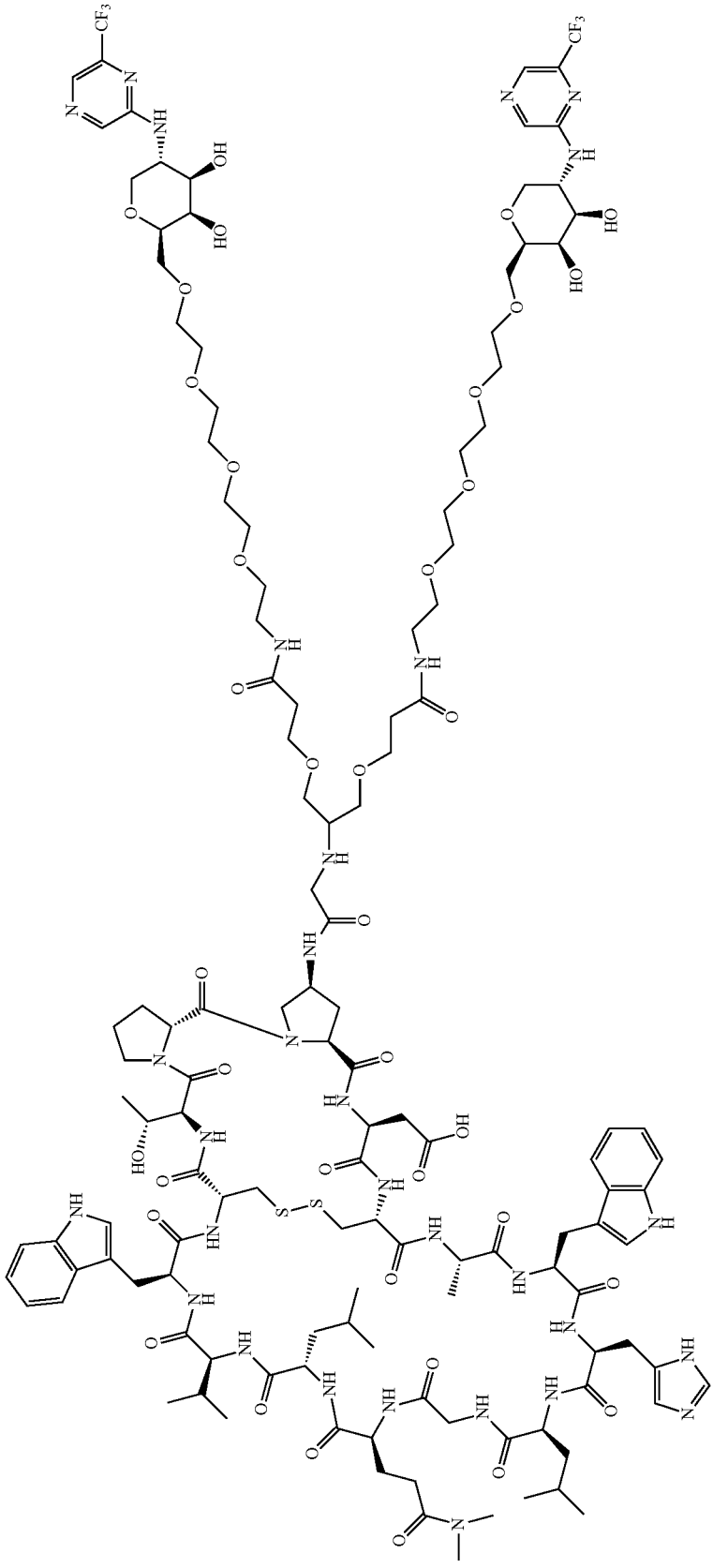

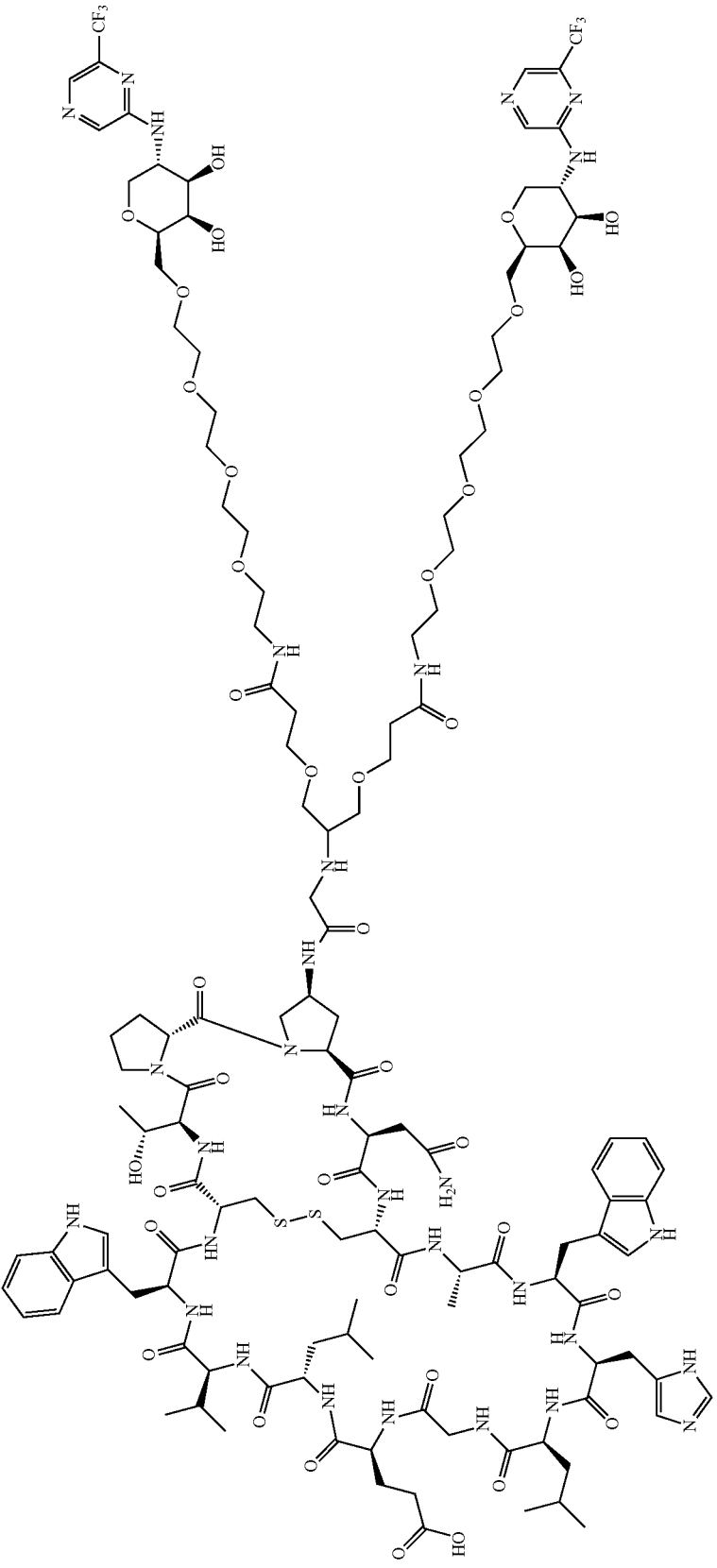

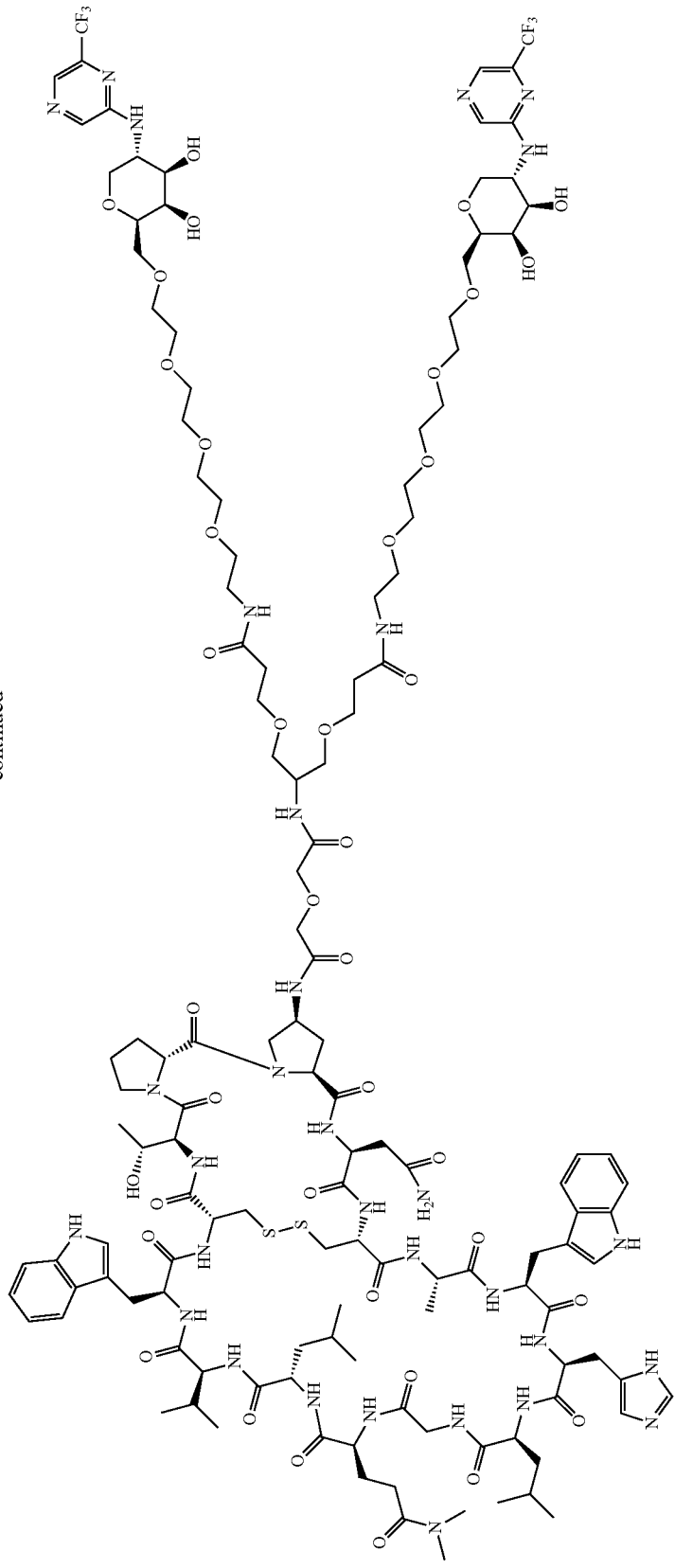

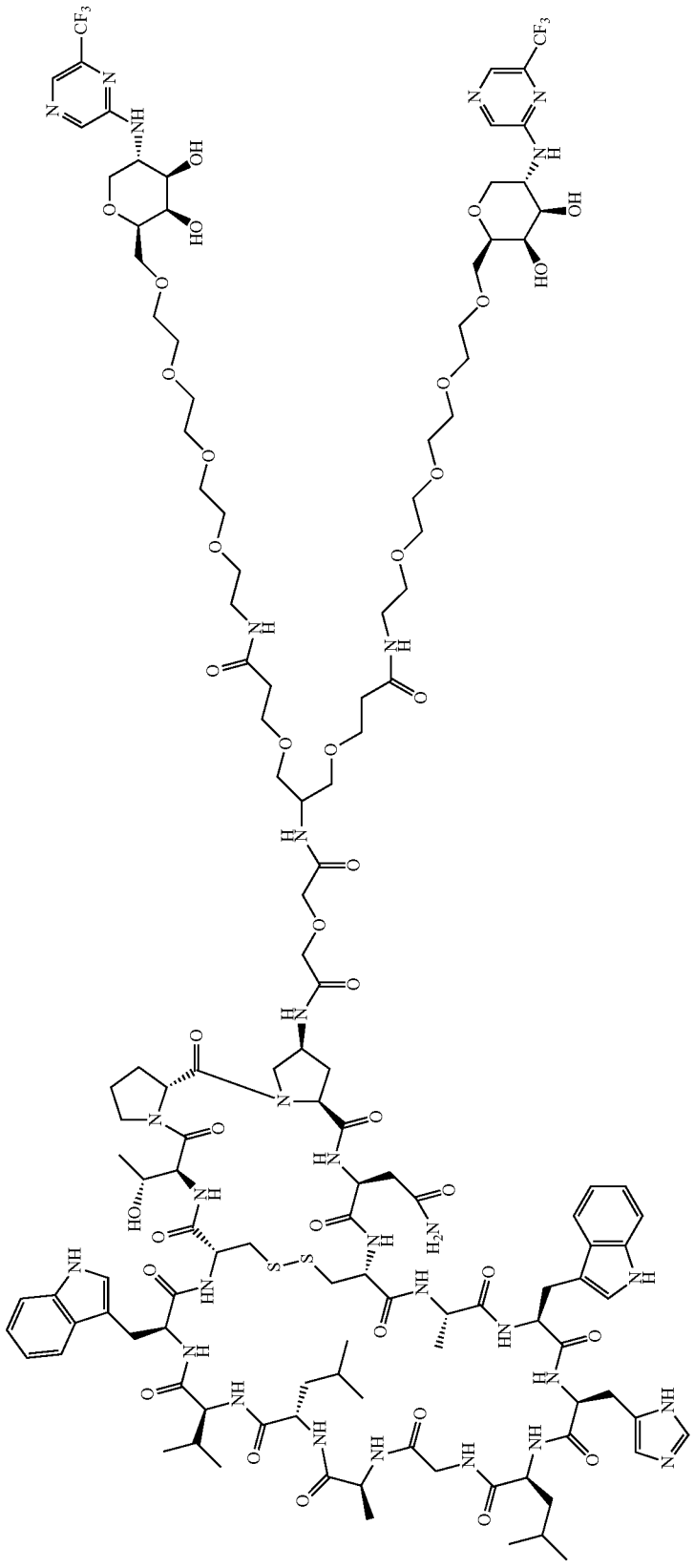

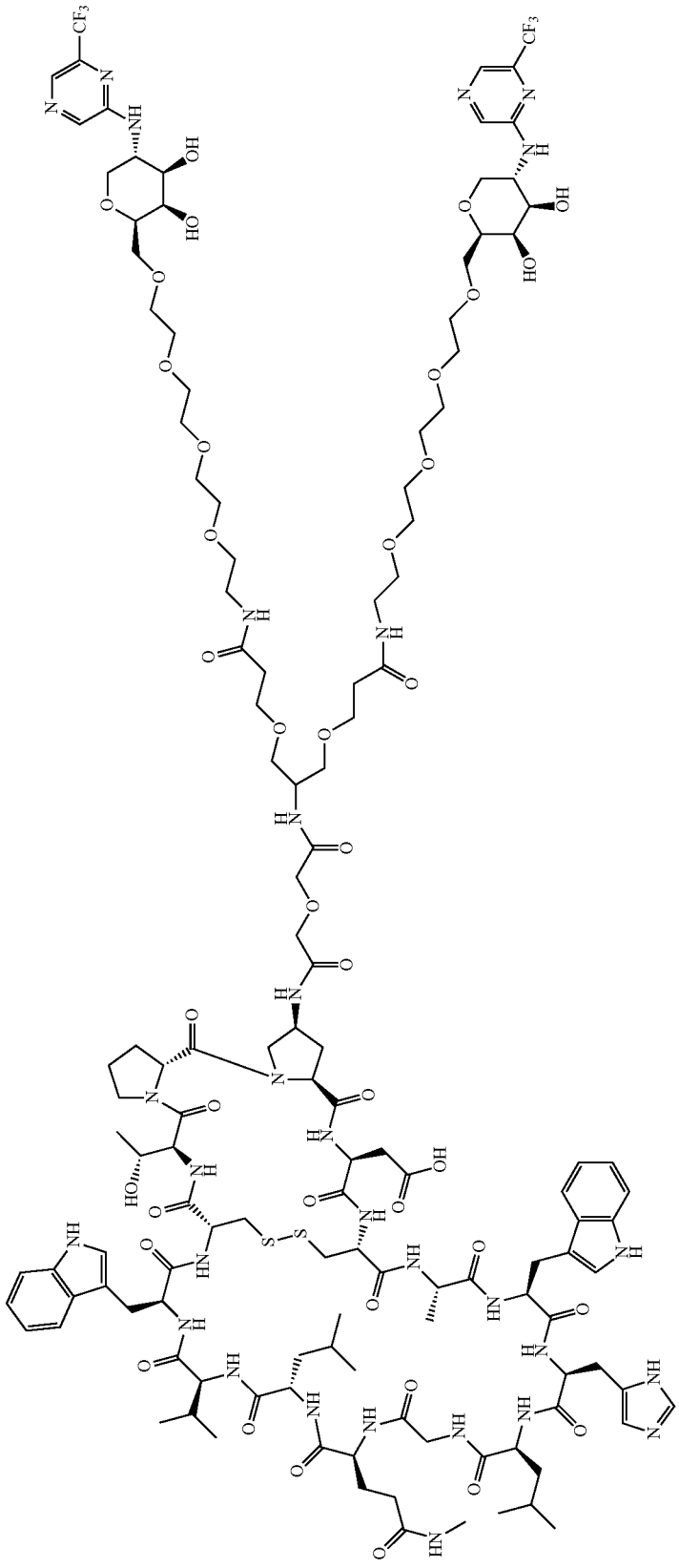

1473 1474
-continued
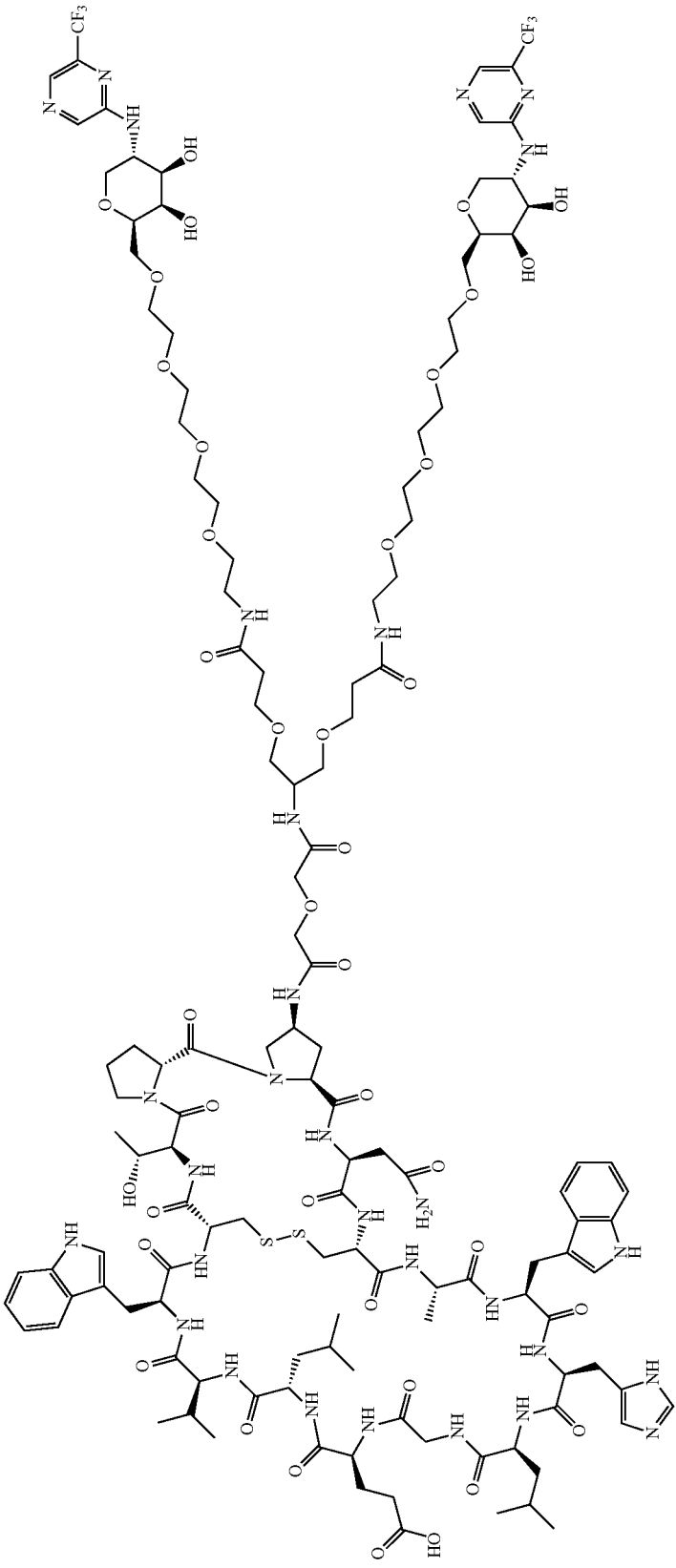

-continued
1475
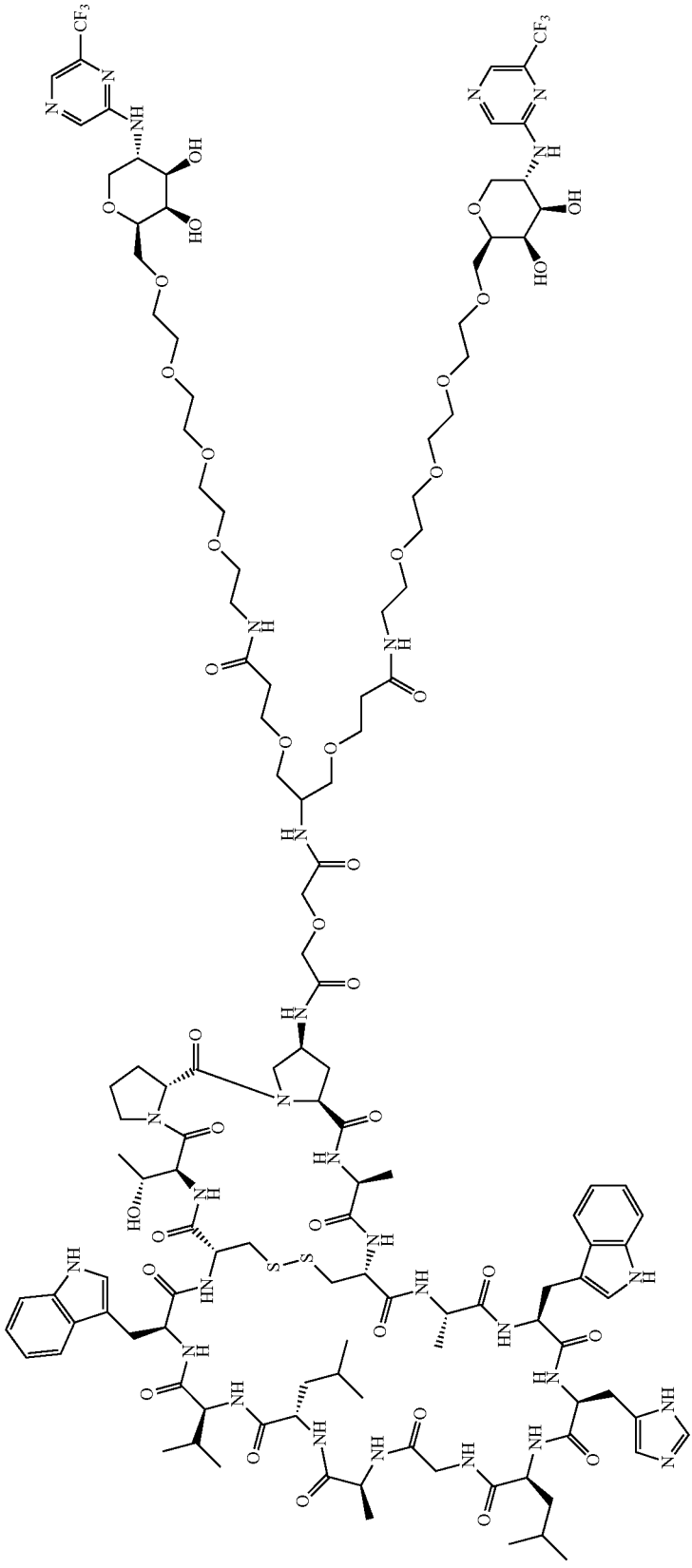

-continued
1477 1478
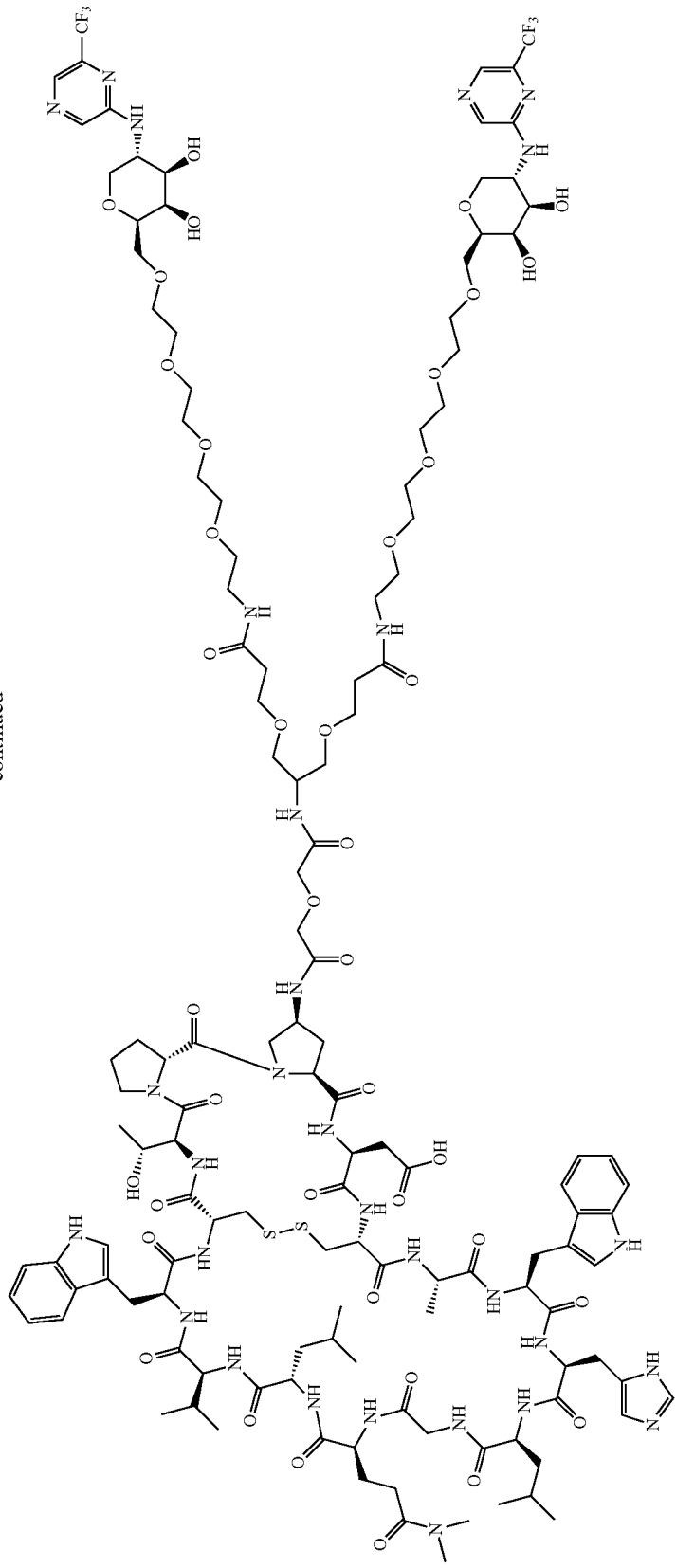

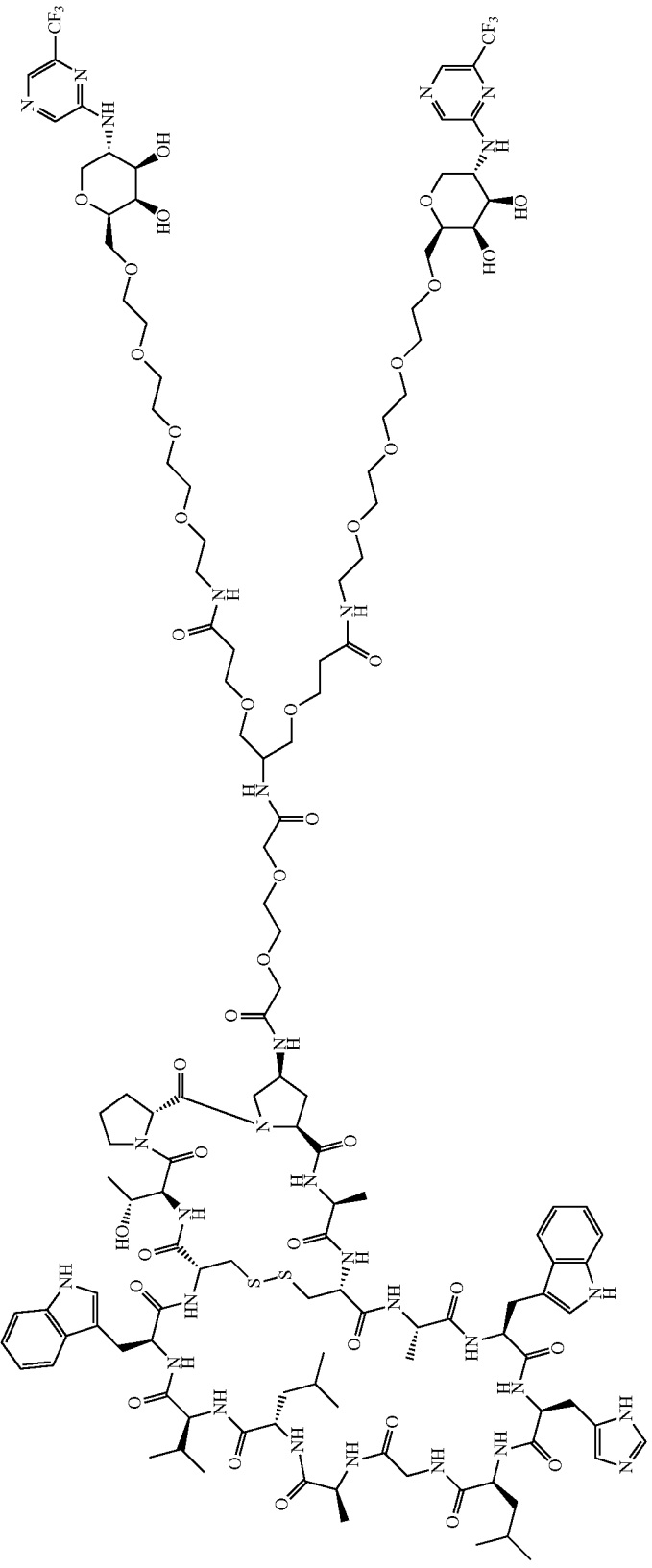

1481 1482
-continued
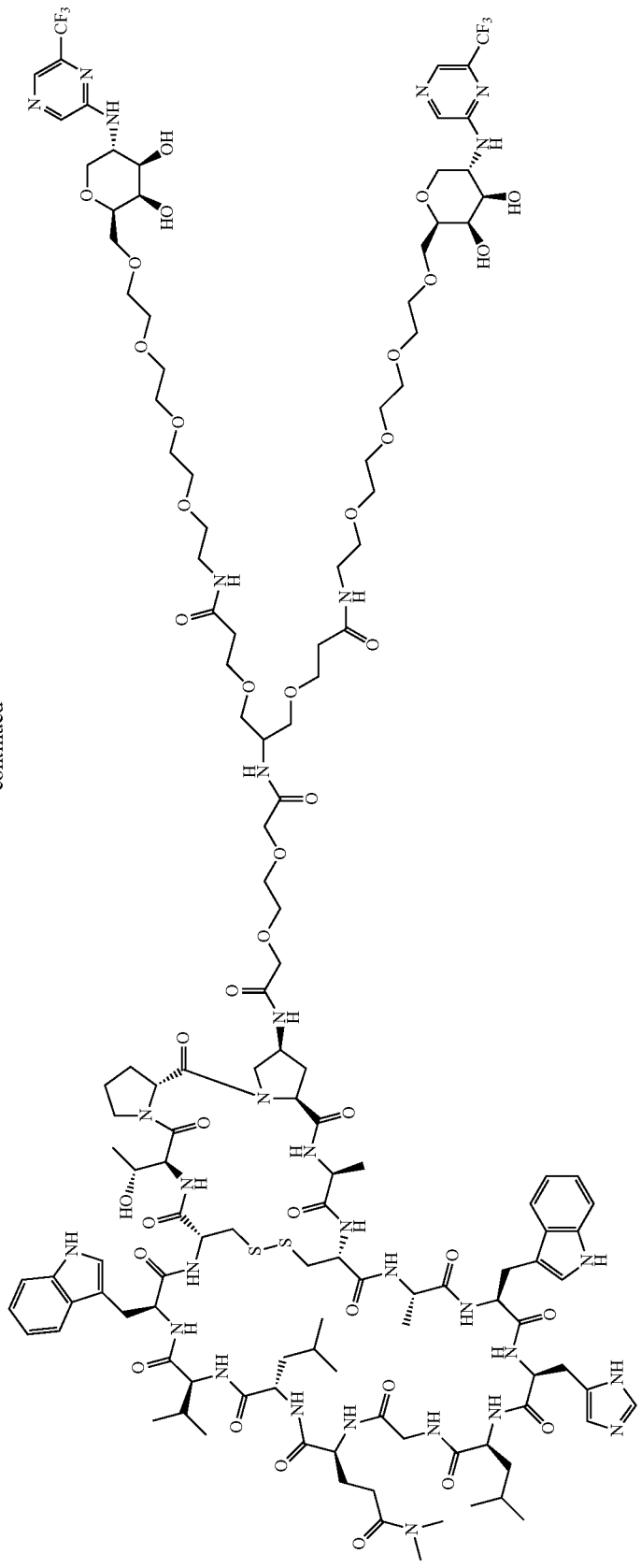

-continued
1484
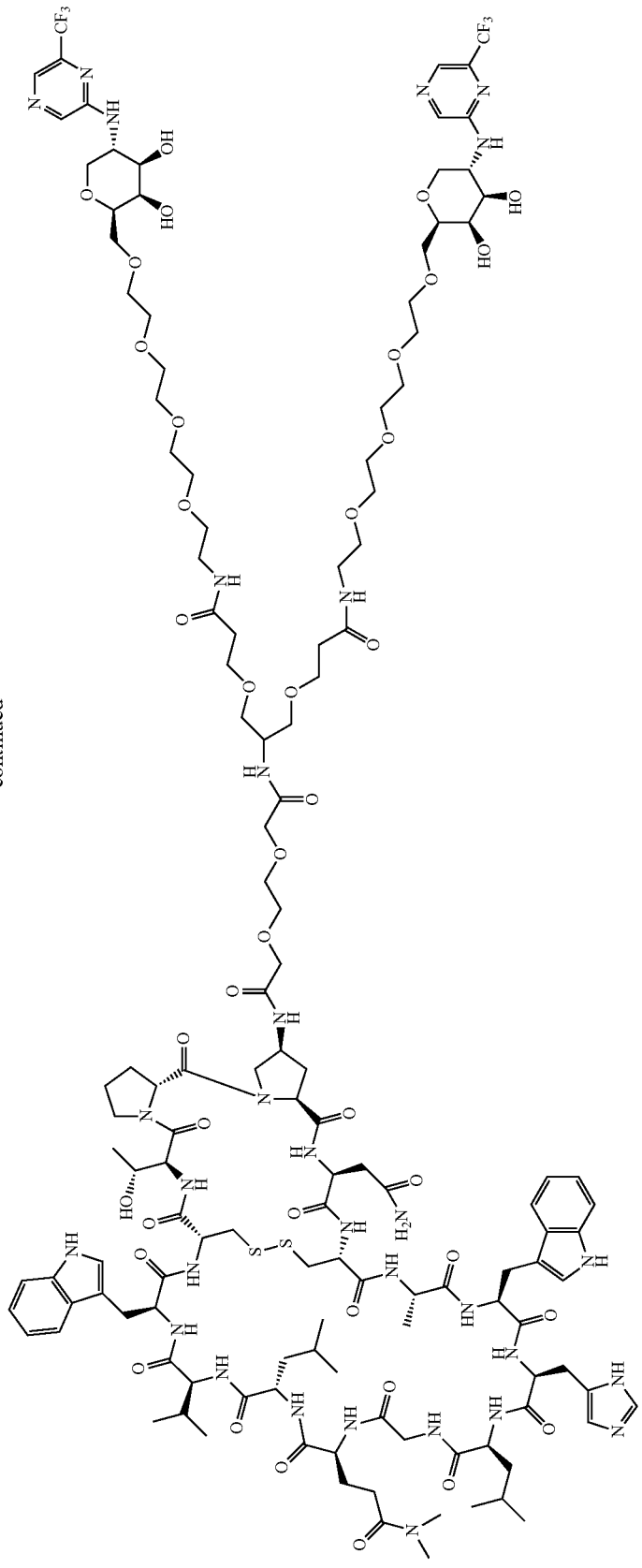

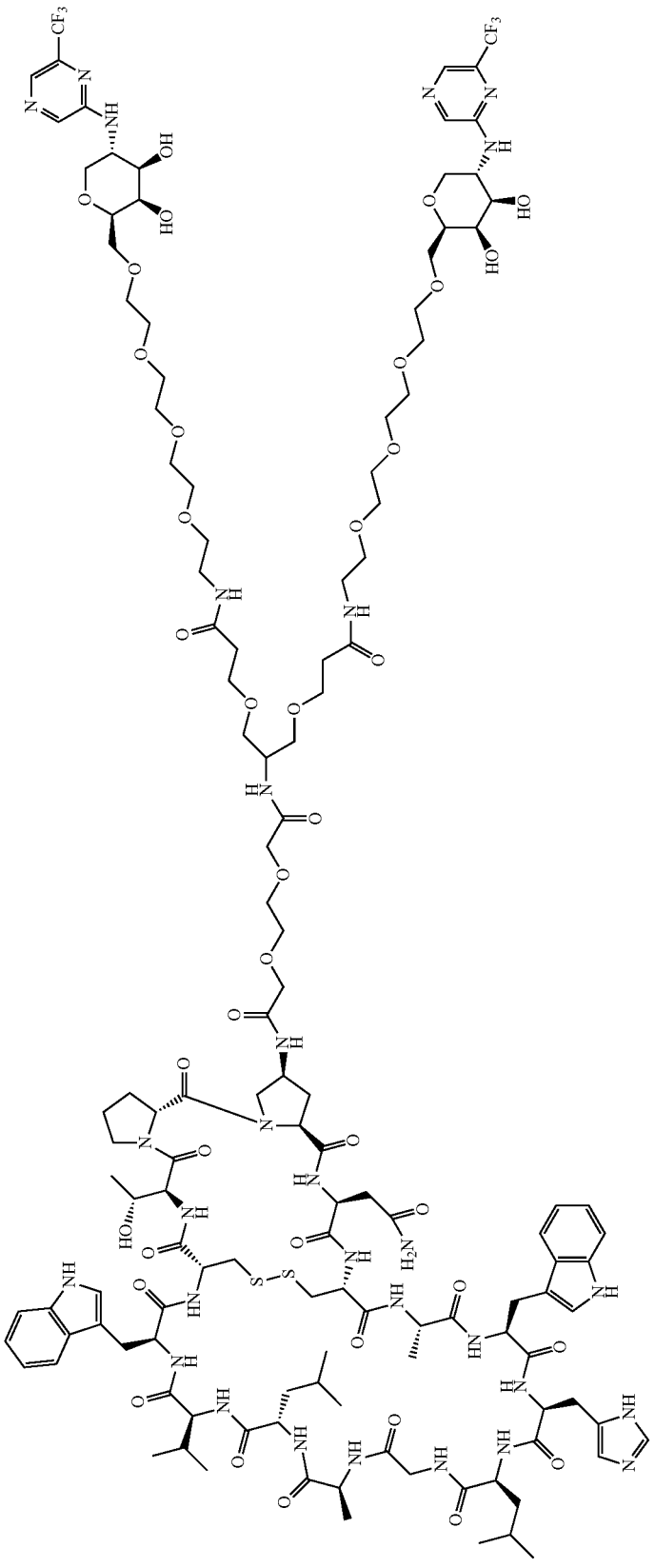

-continued
1487 1488
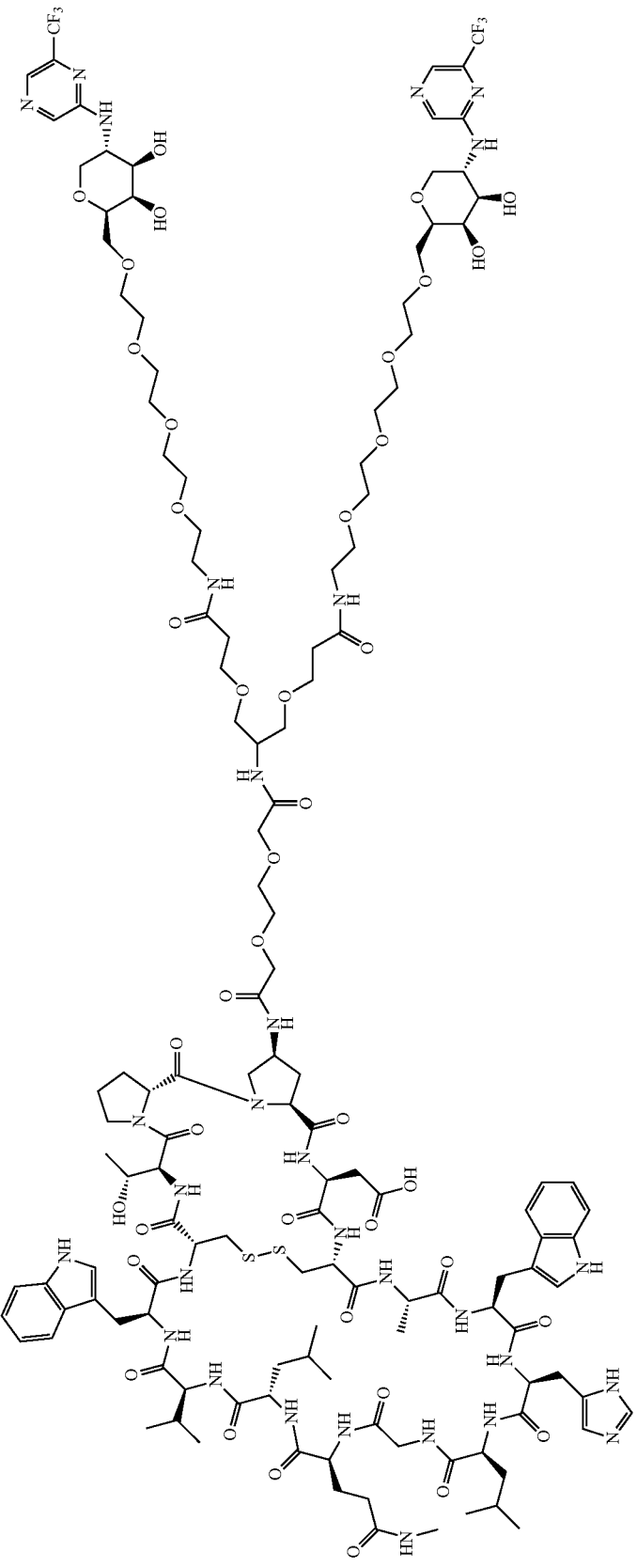

-continued
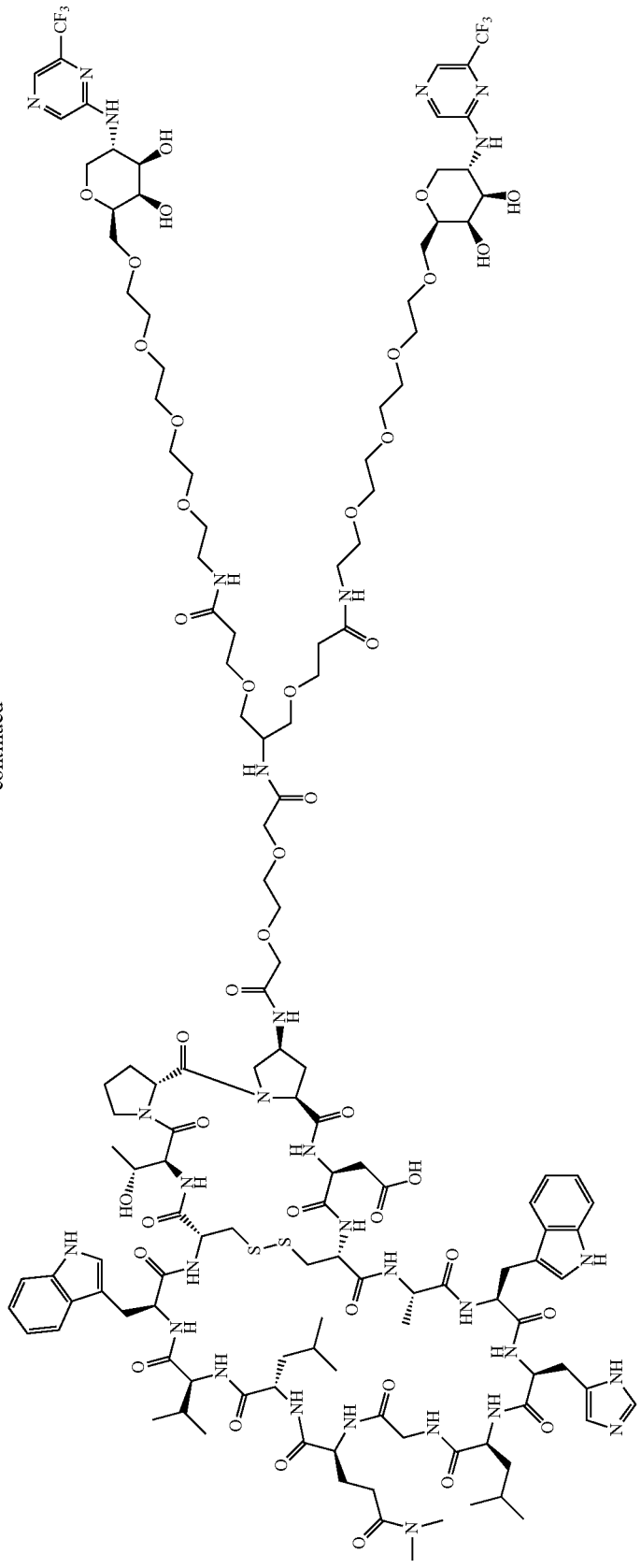

1491 1492
-continued
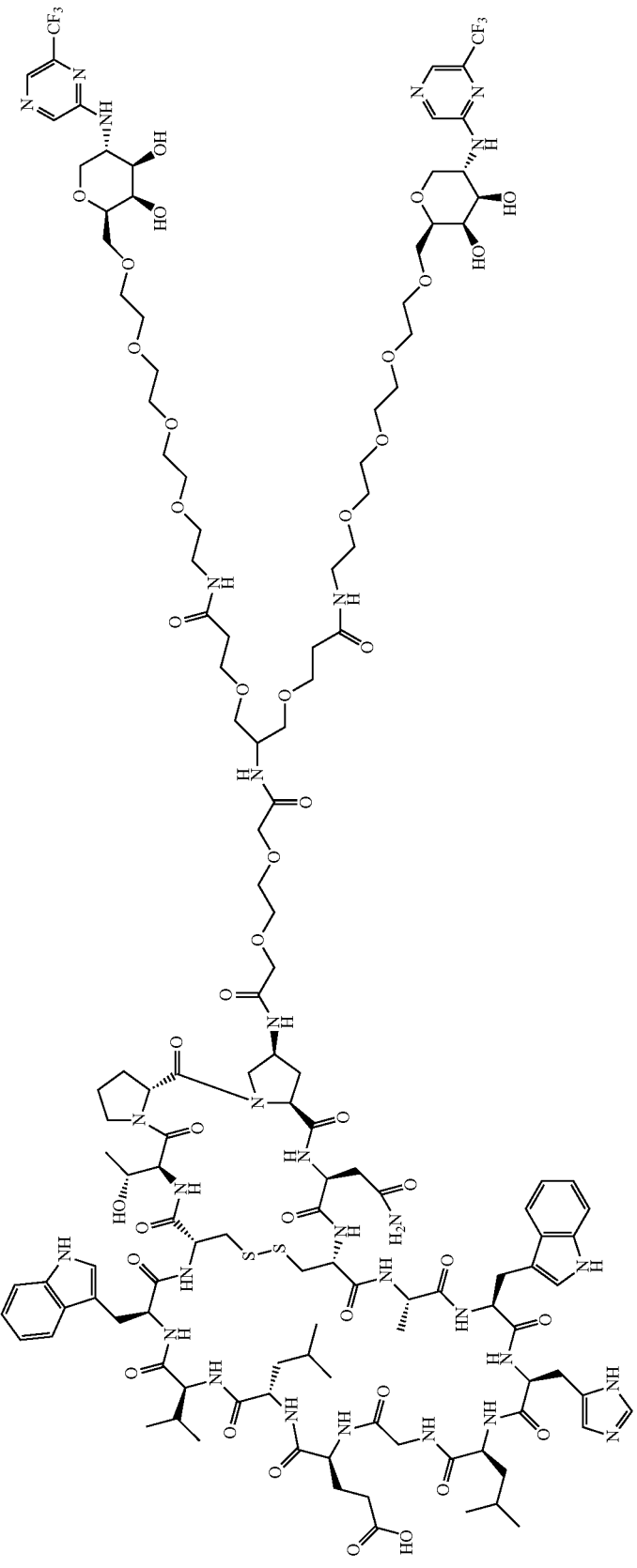

1493 1494
-continued
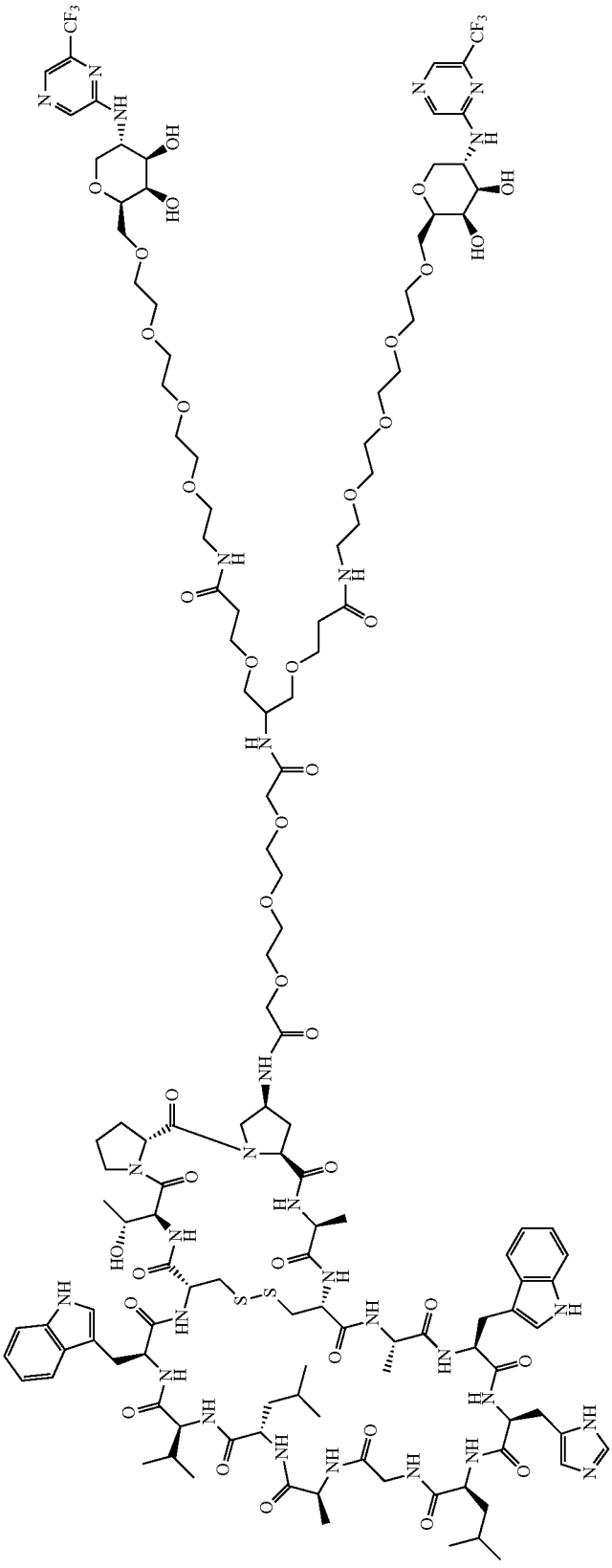

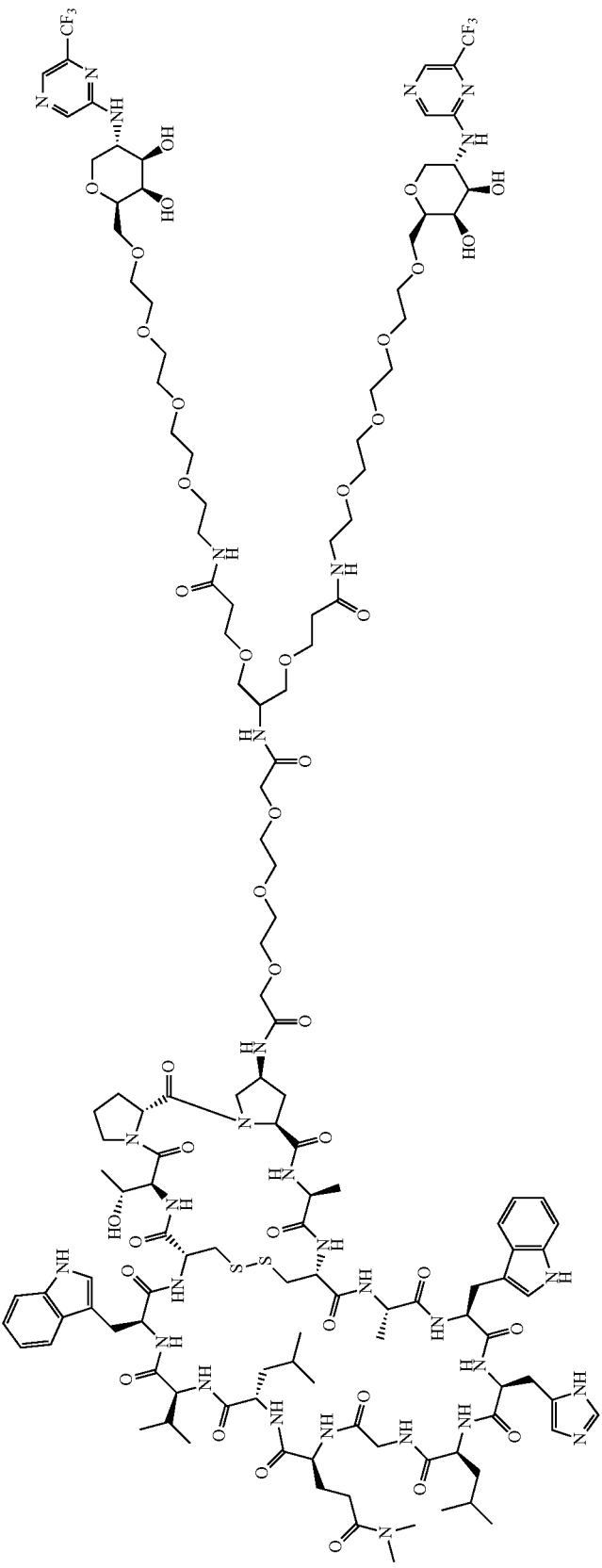

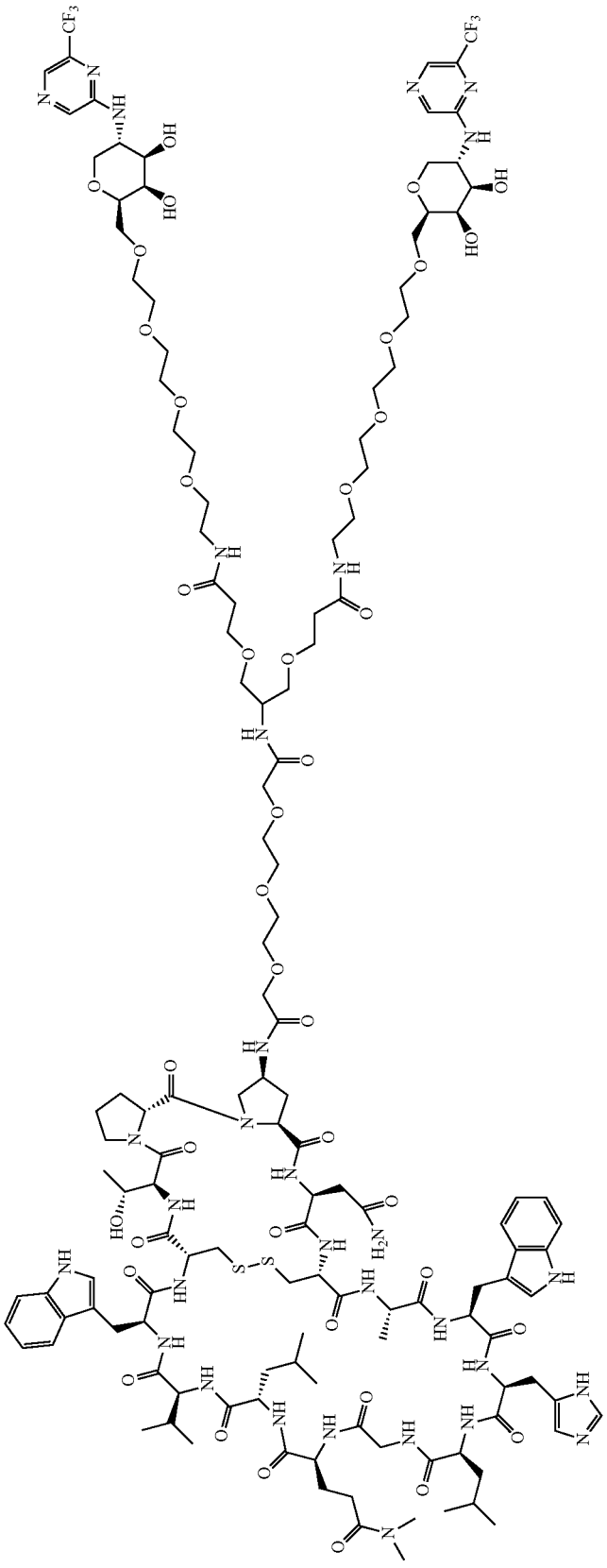

-continued
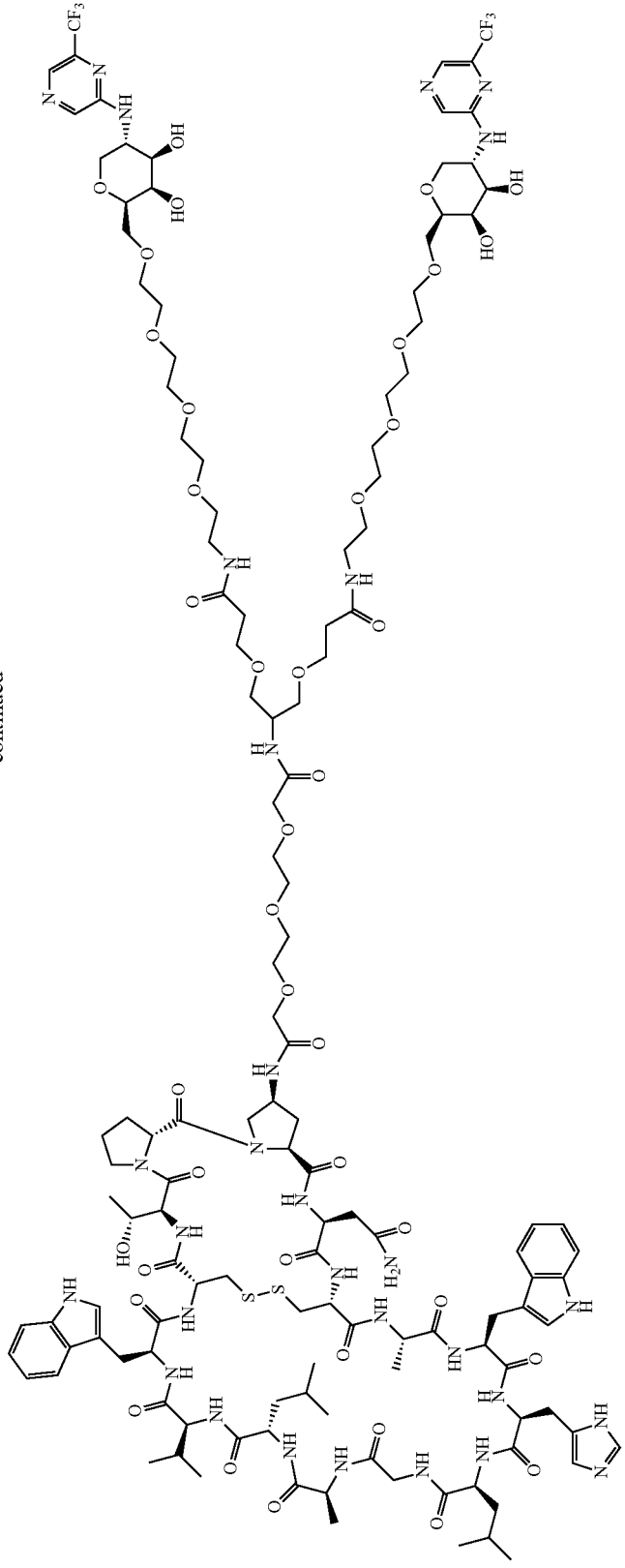

1501 1502
-continued
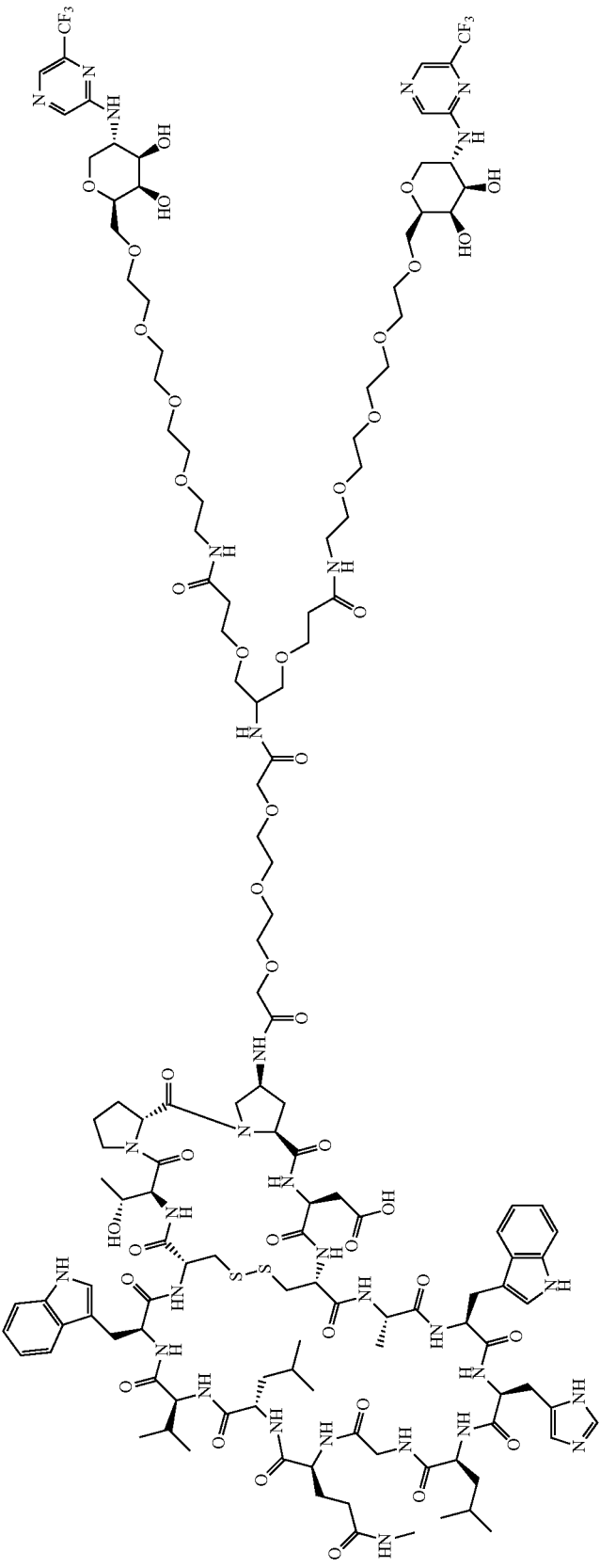

1503 1504
-continued
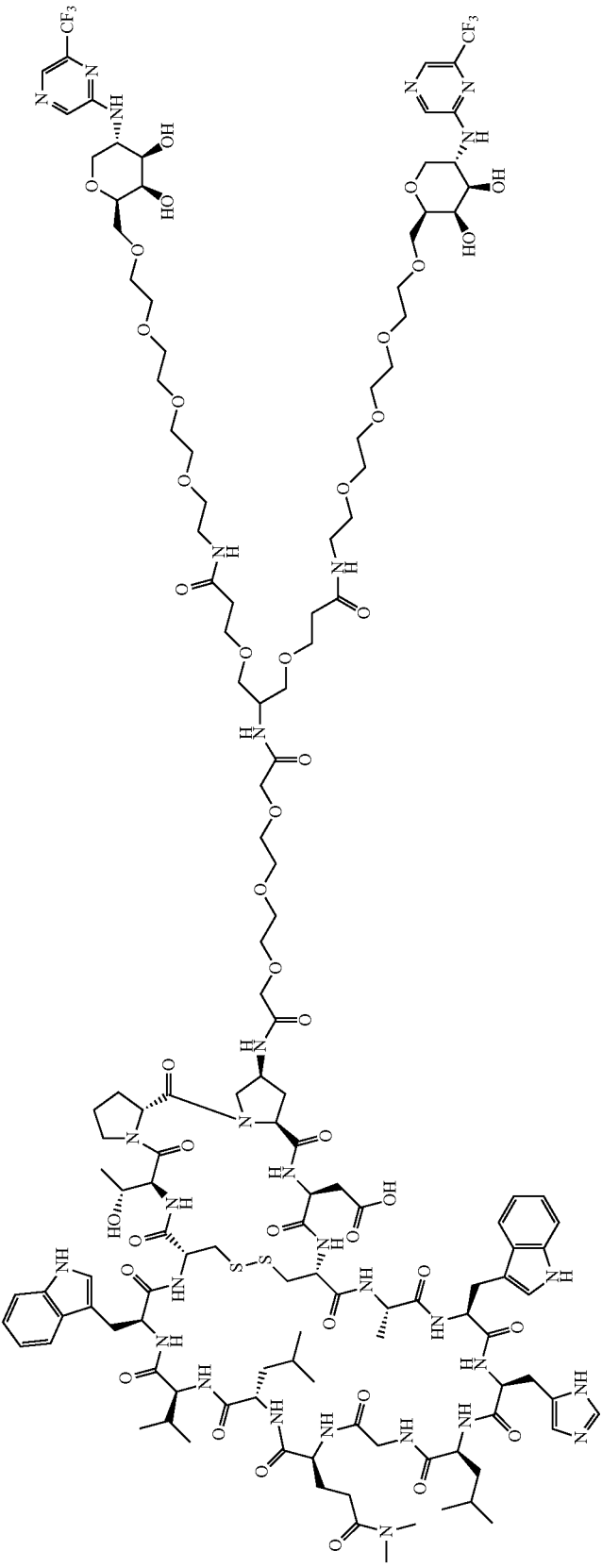

1505 1506
-continued
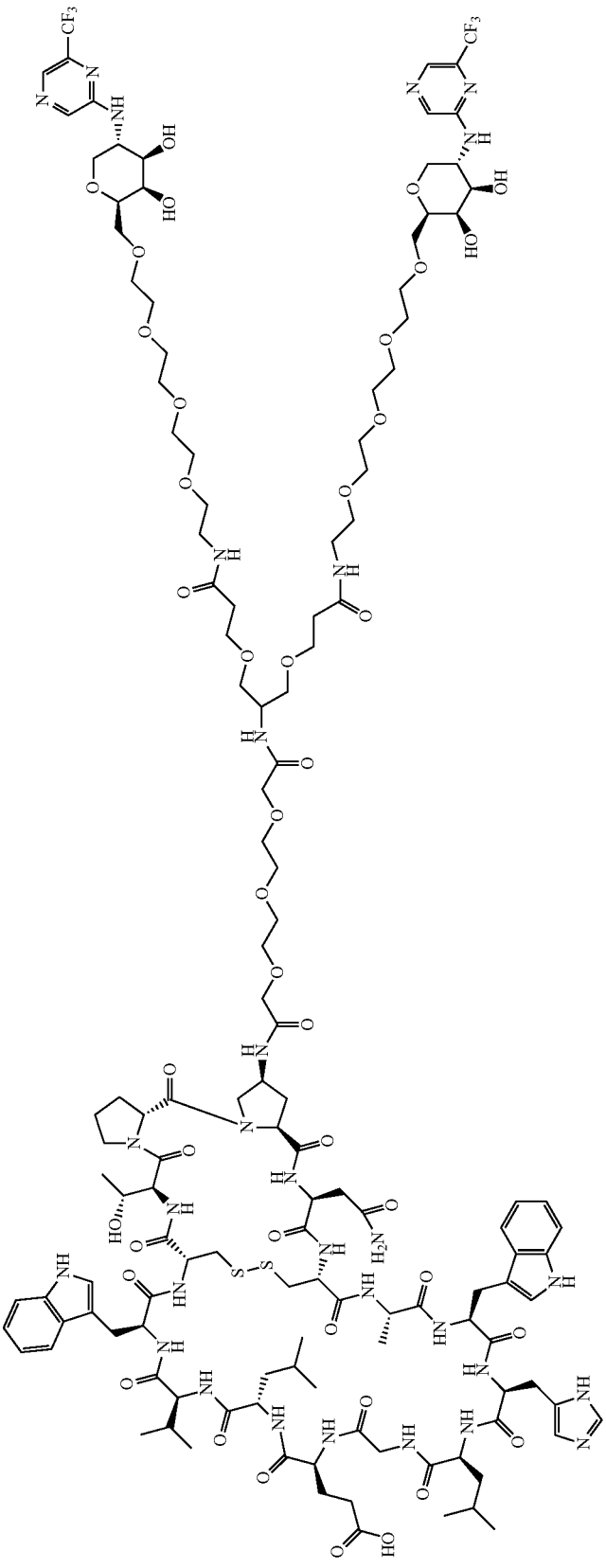

1507 1508
-continued
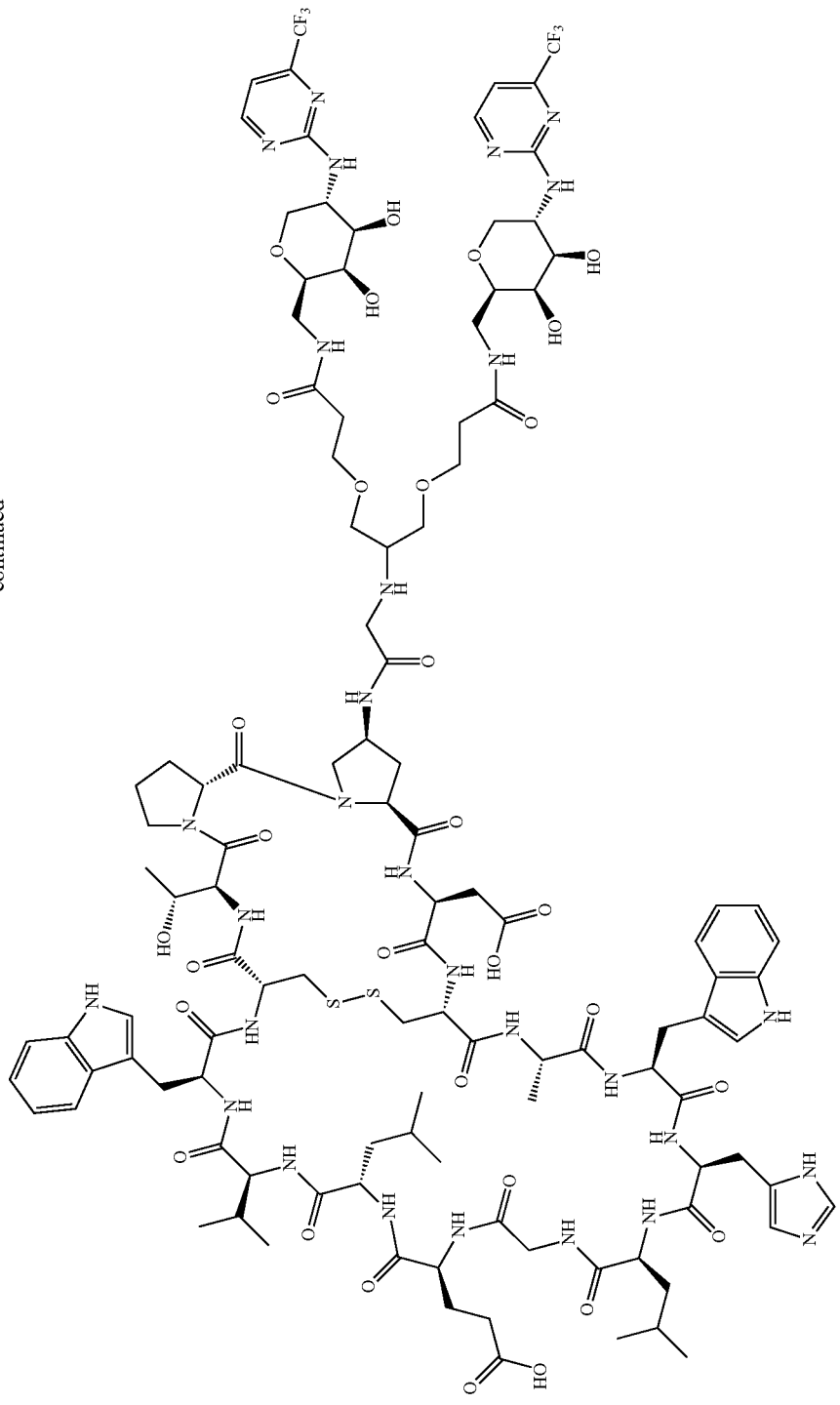

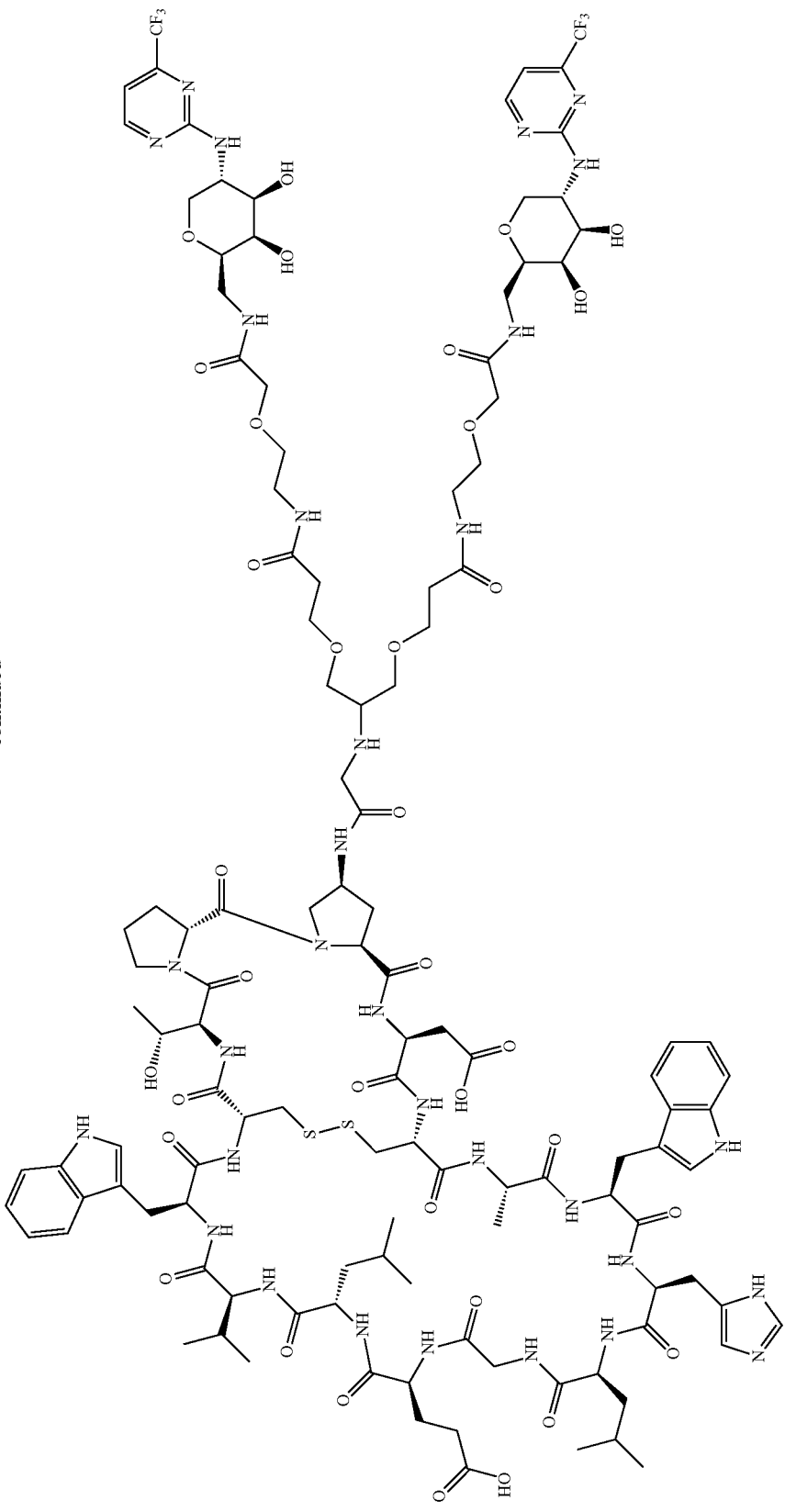

1511 1512
-continued
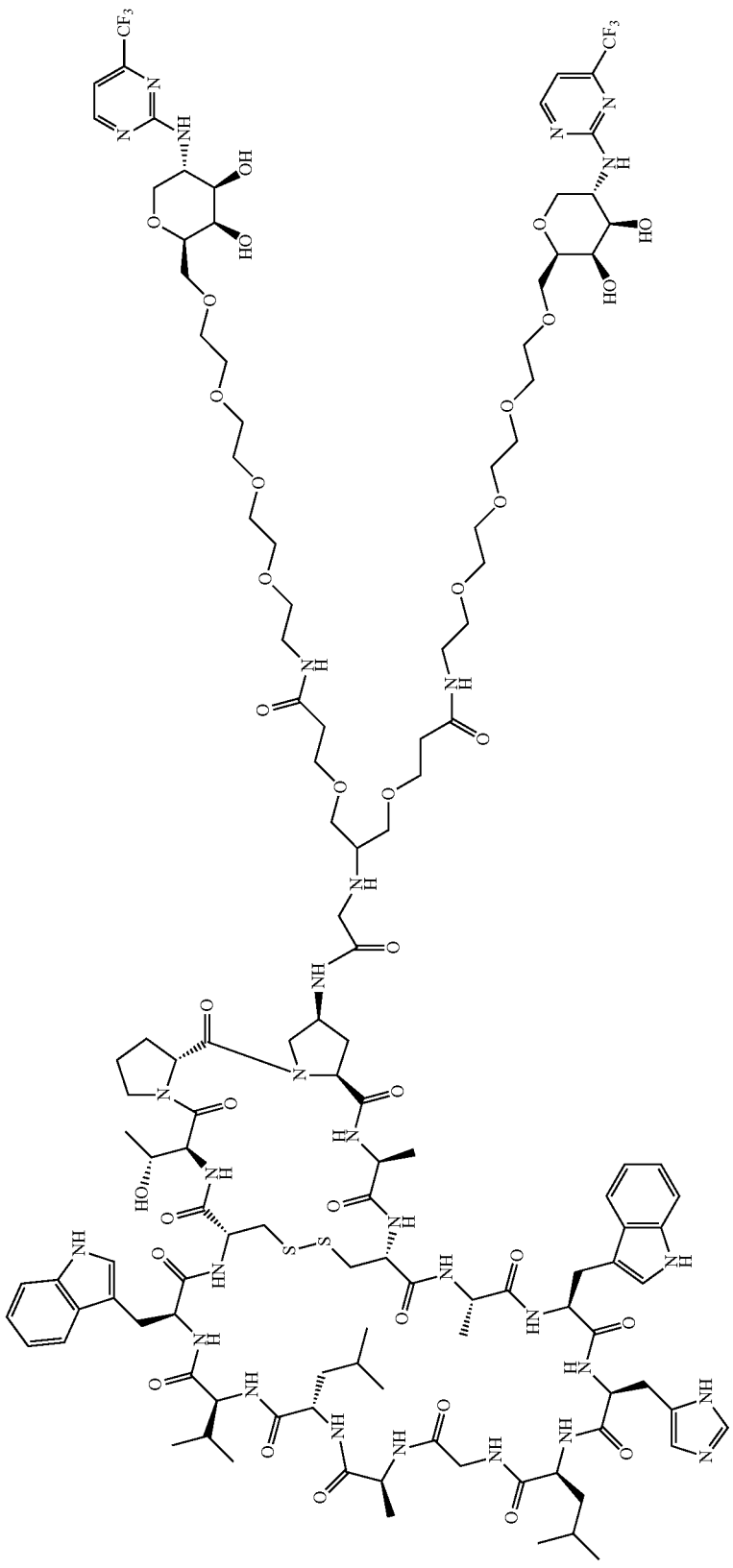

1513 1514
-continued
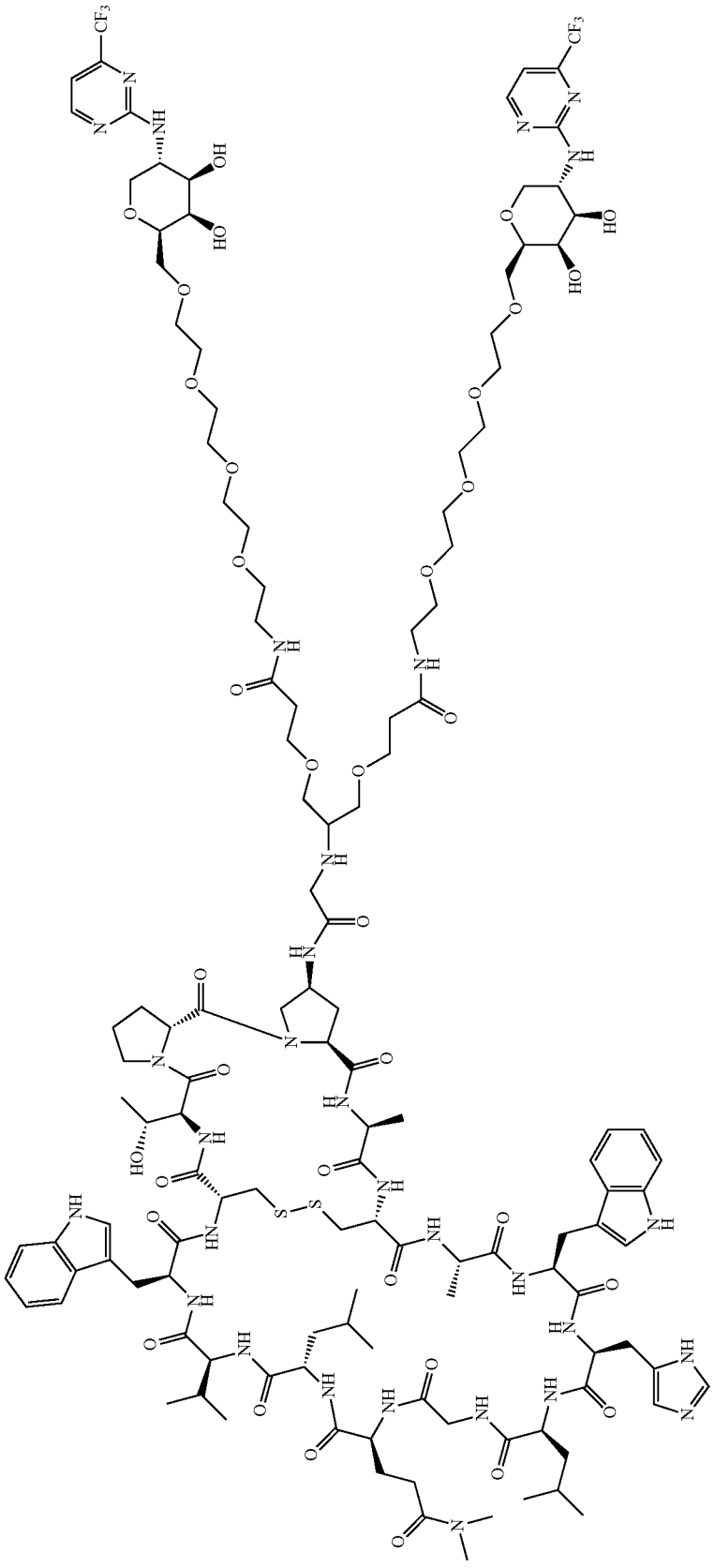

-continued
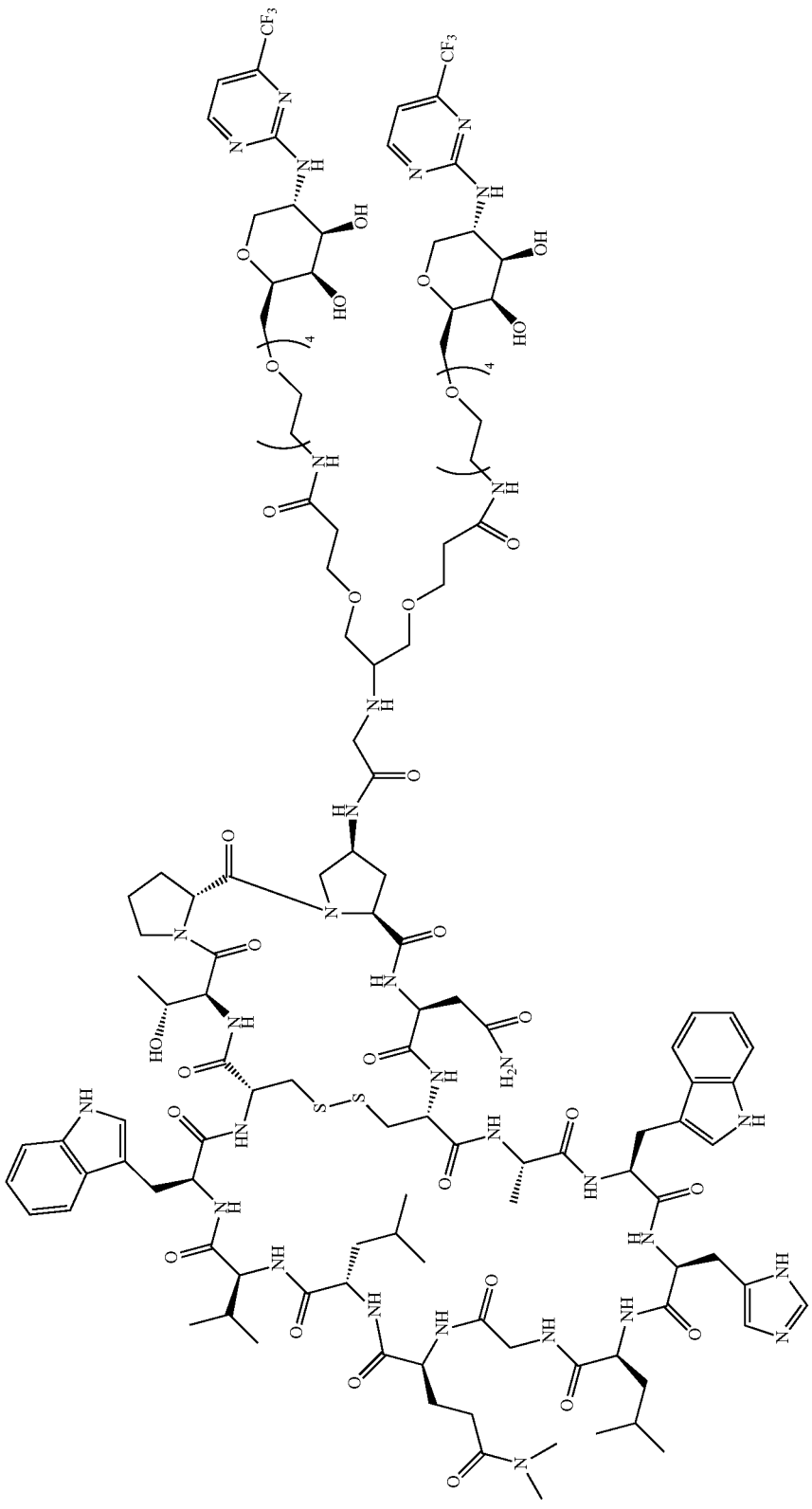

-continued
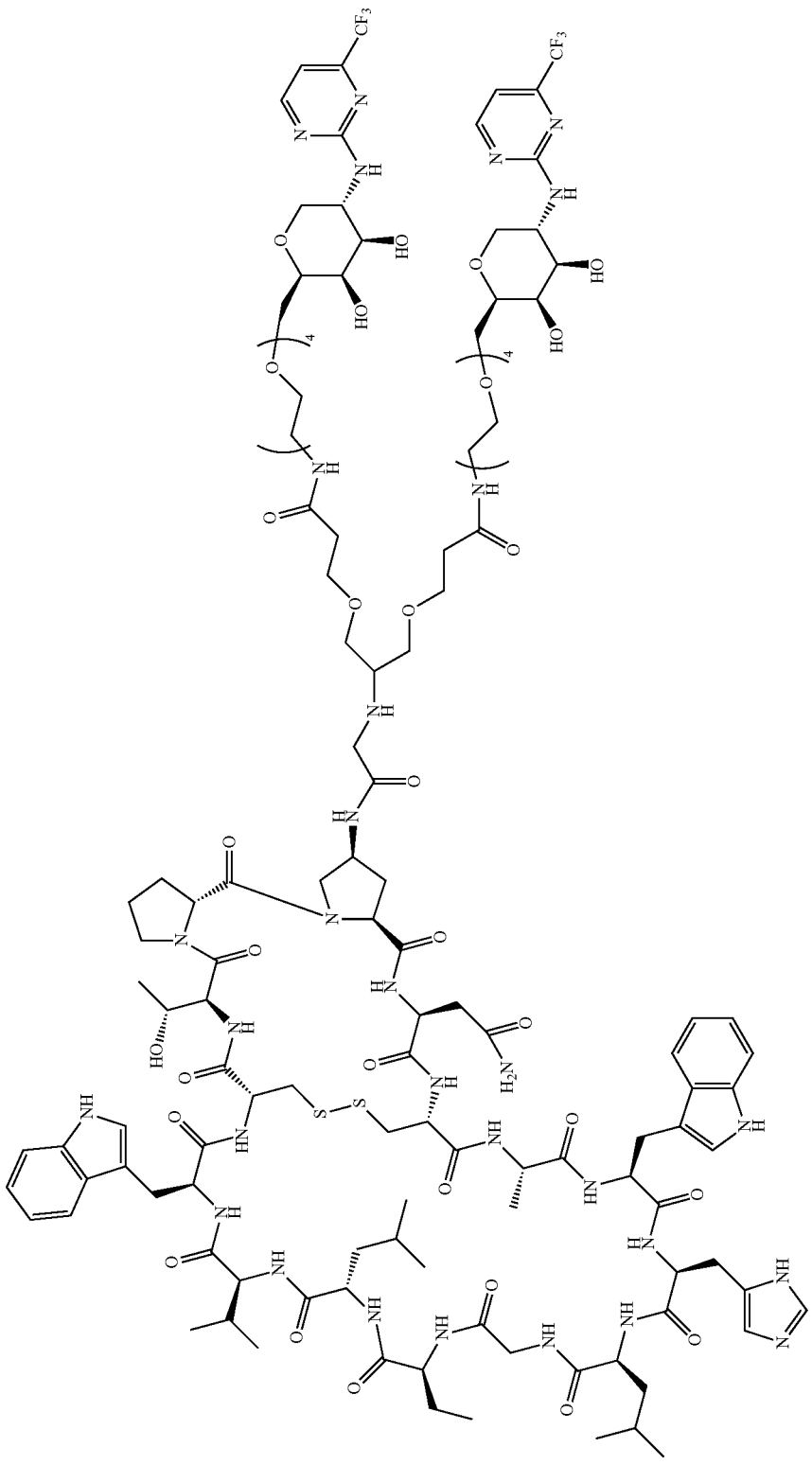

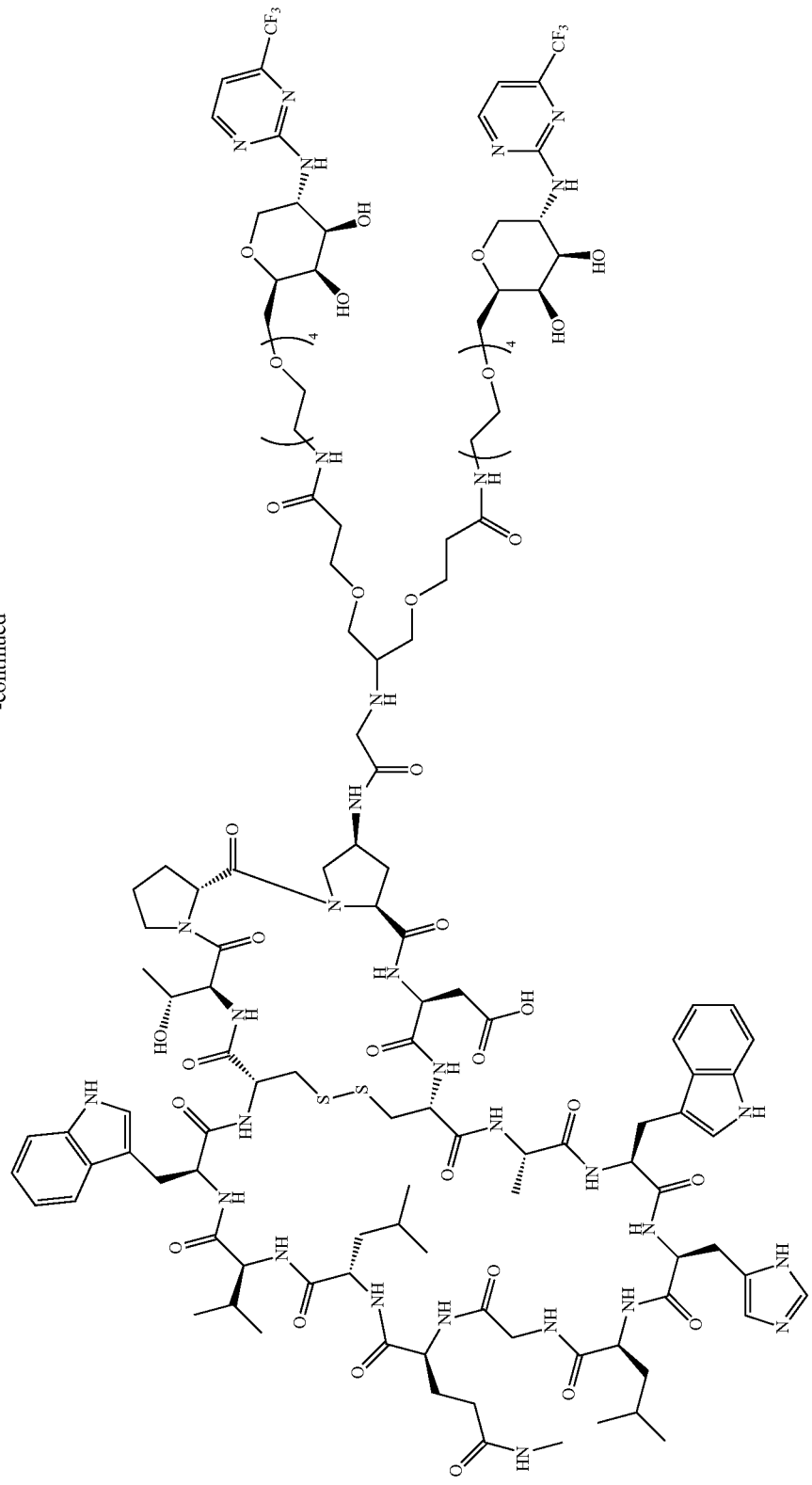

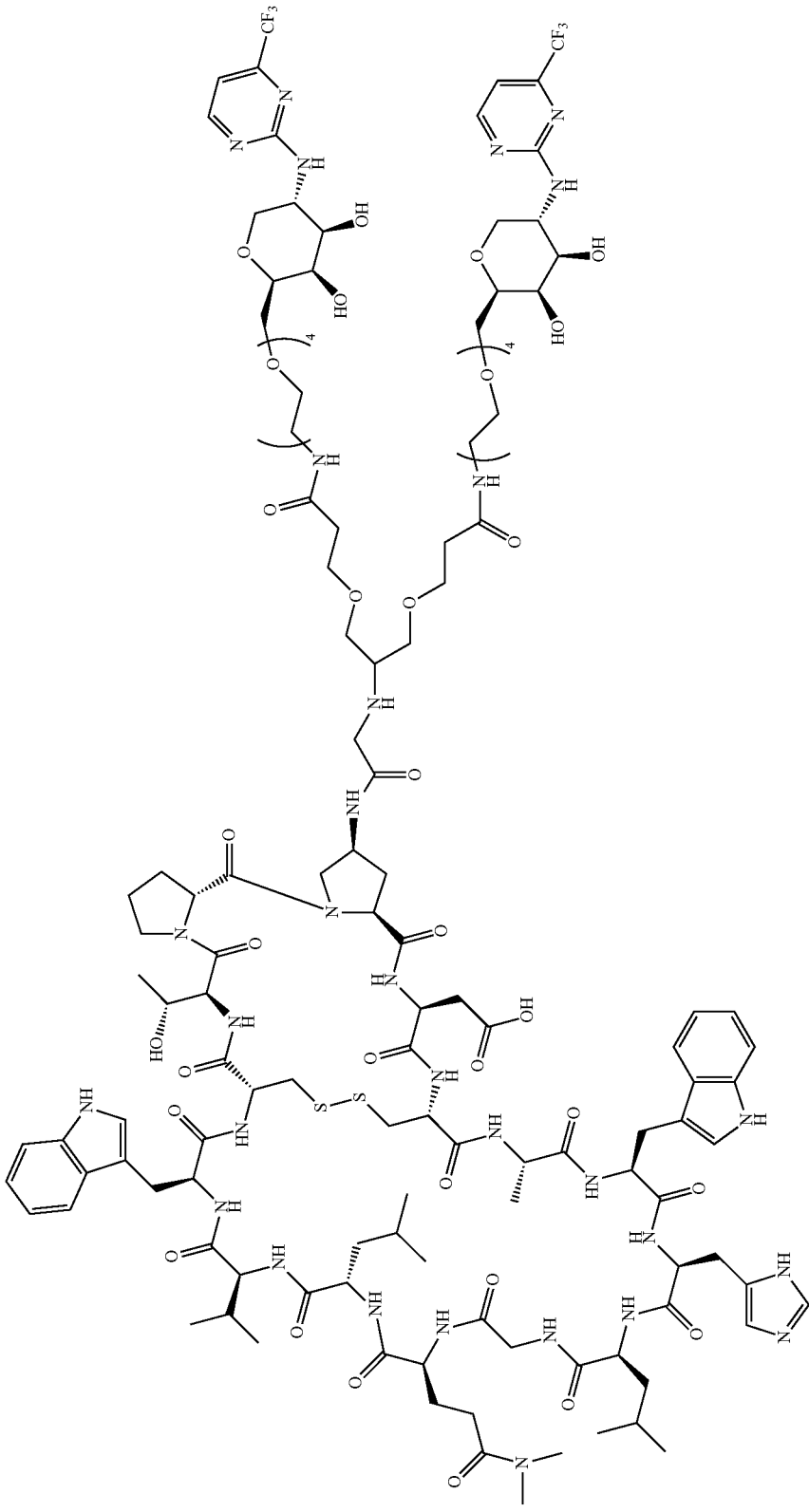

1523    1524
-continued
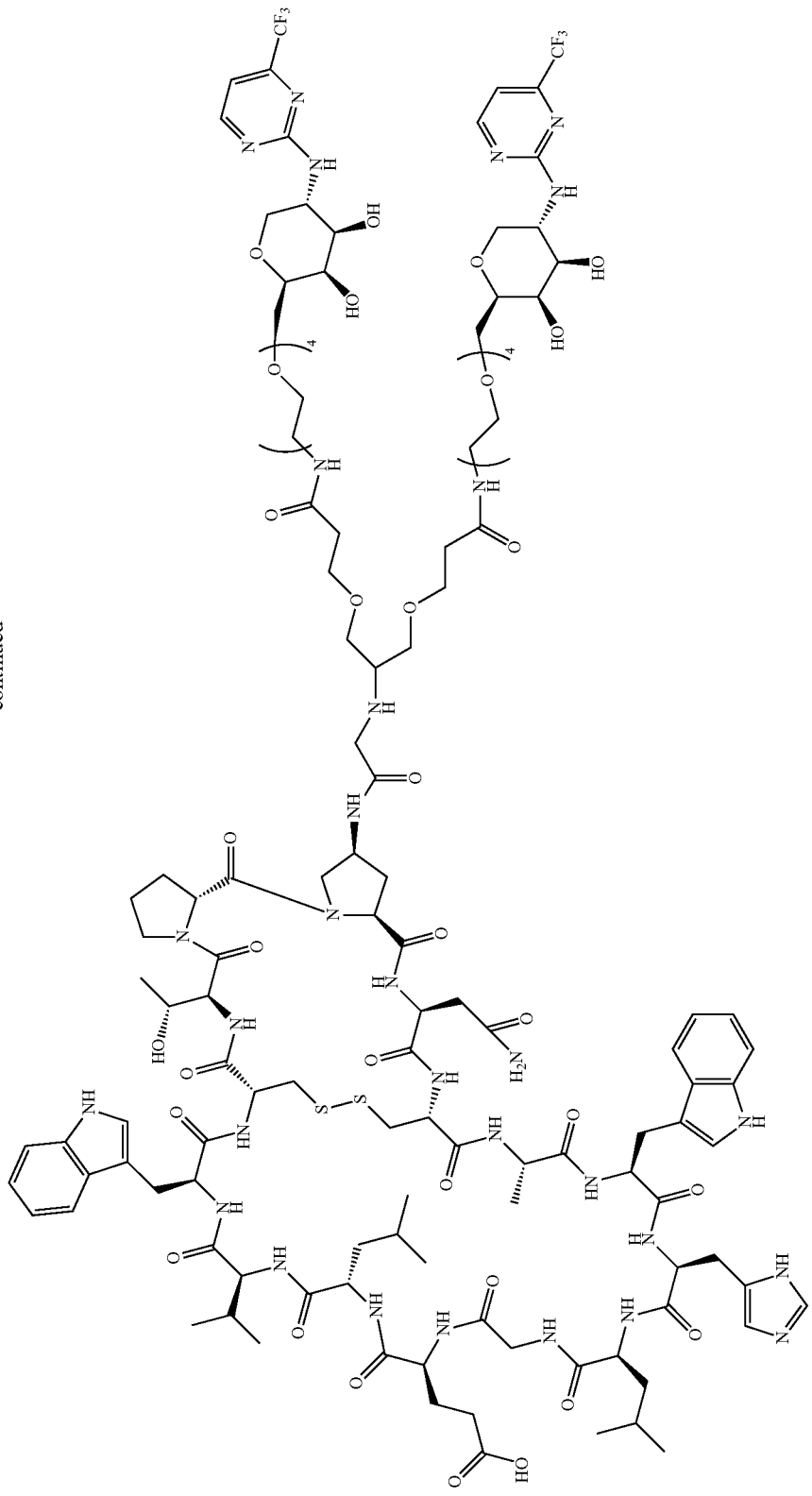

-continued
1525 1526
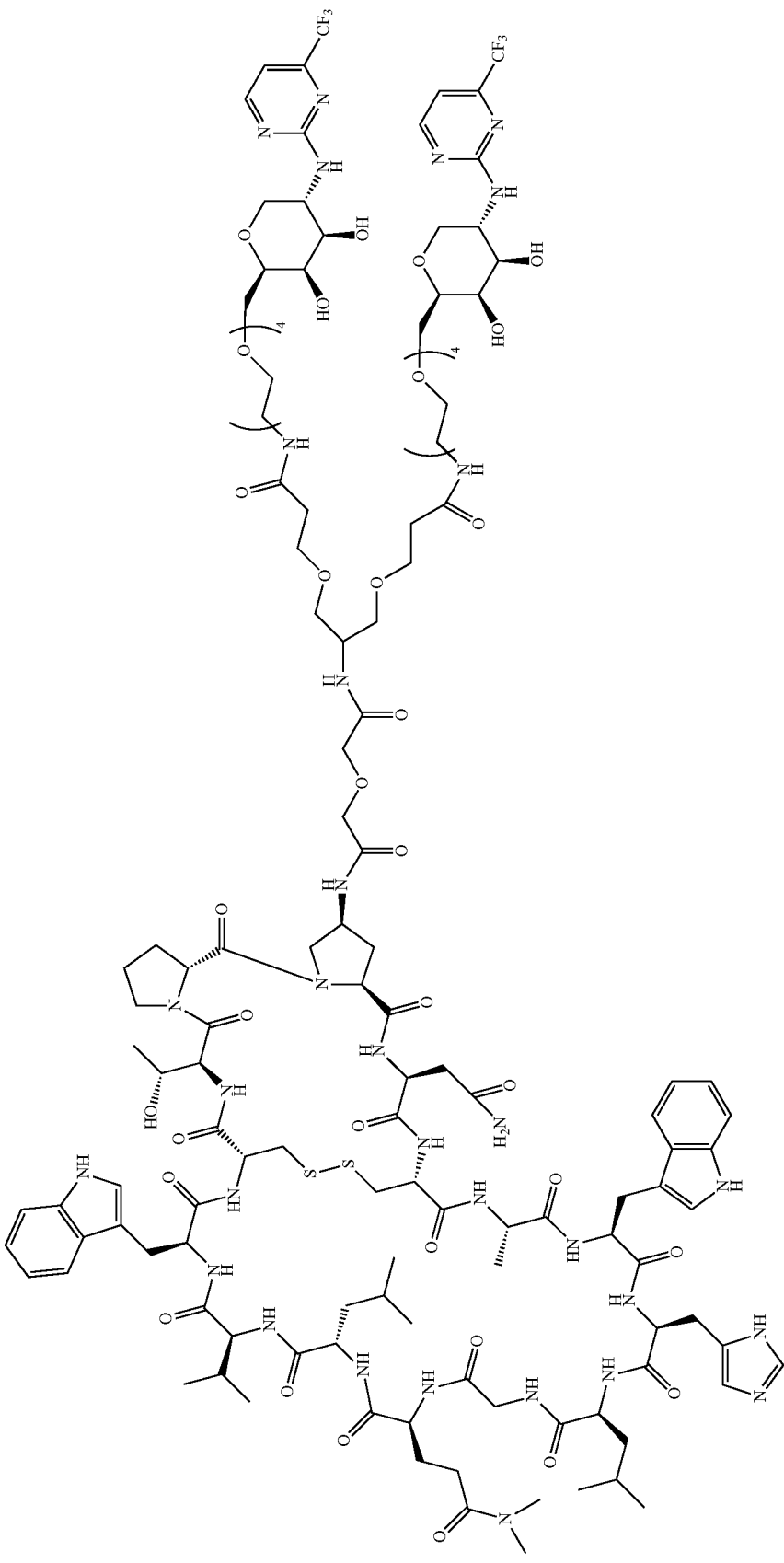

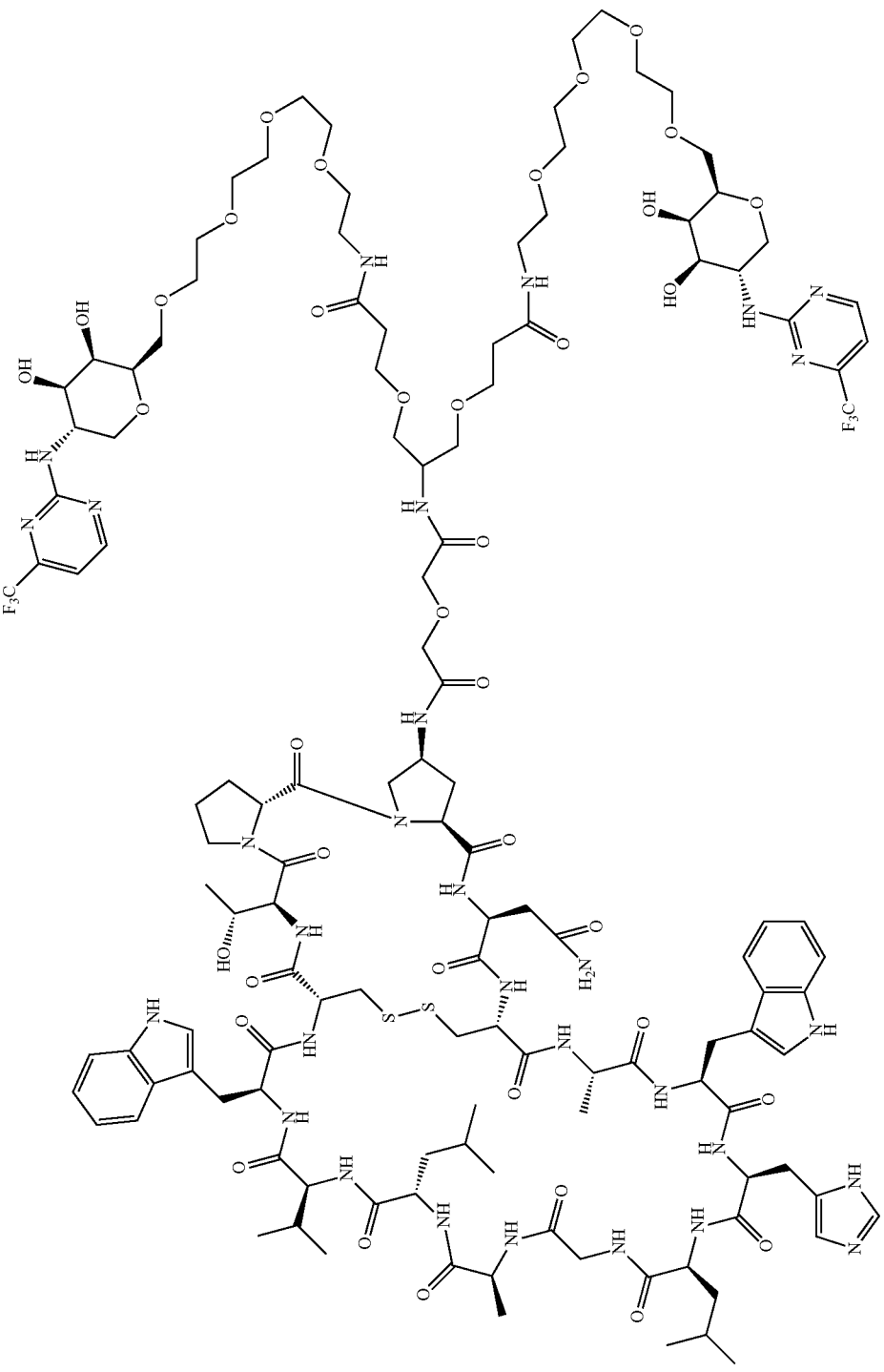

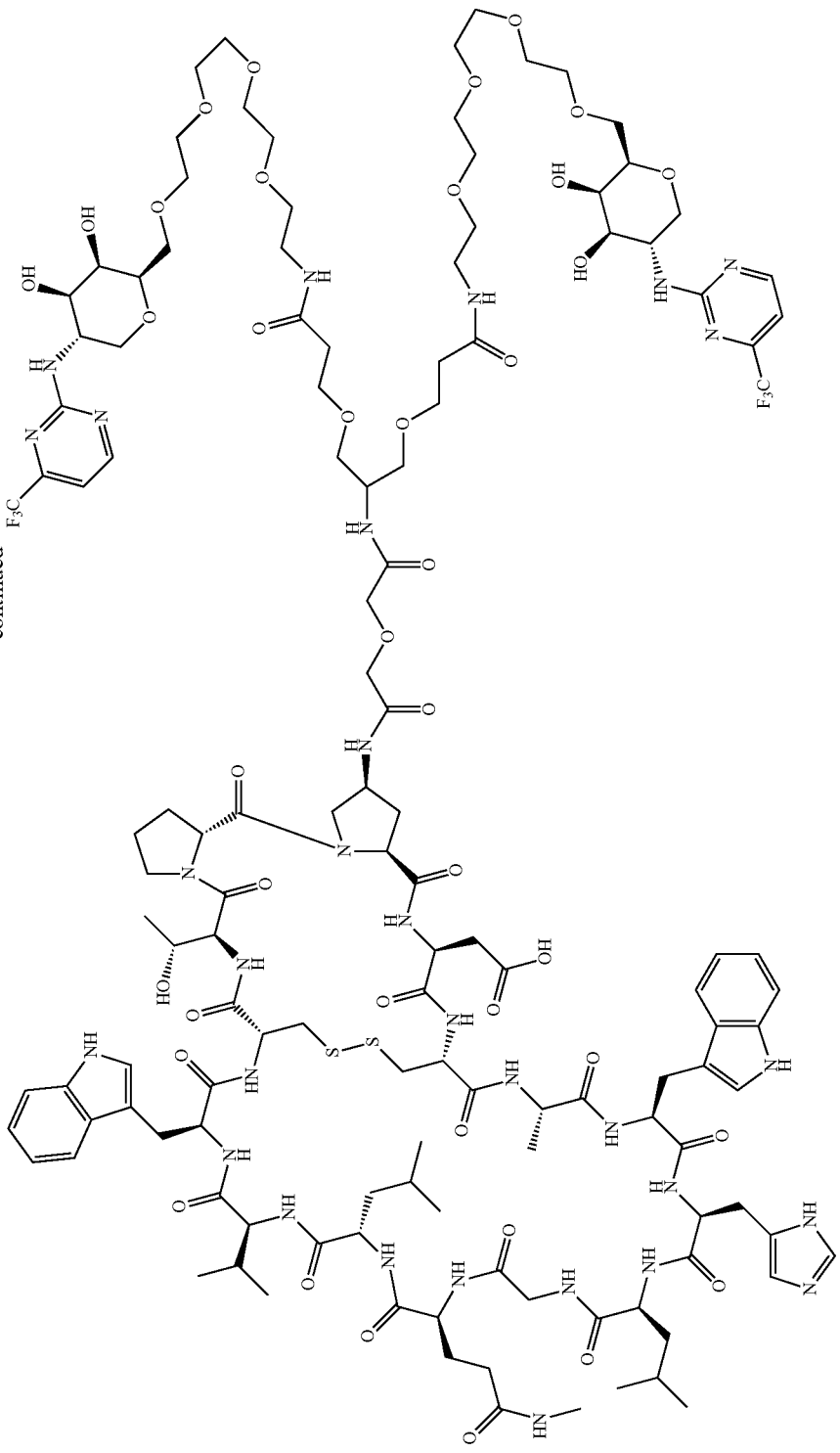

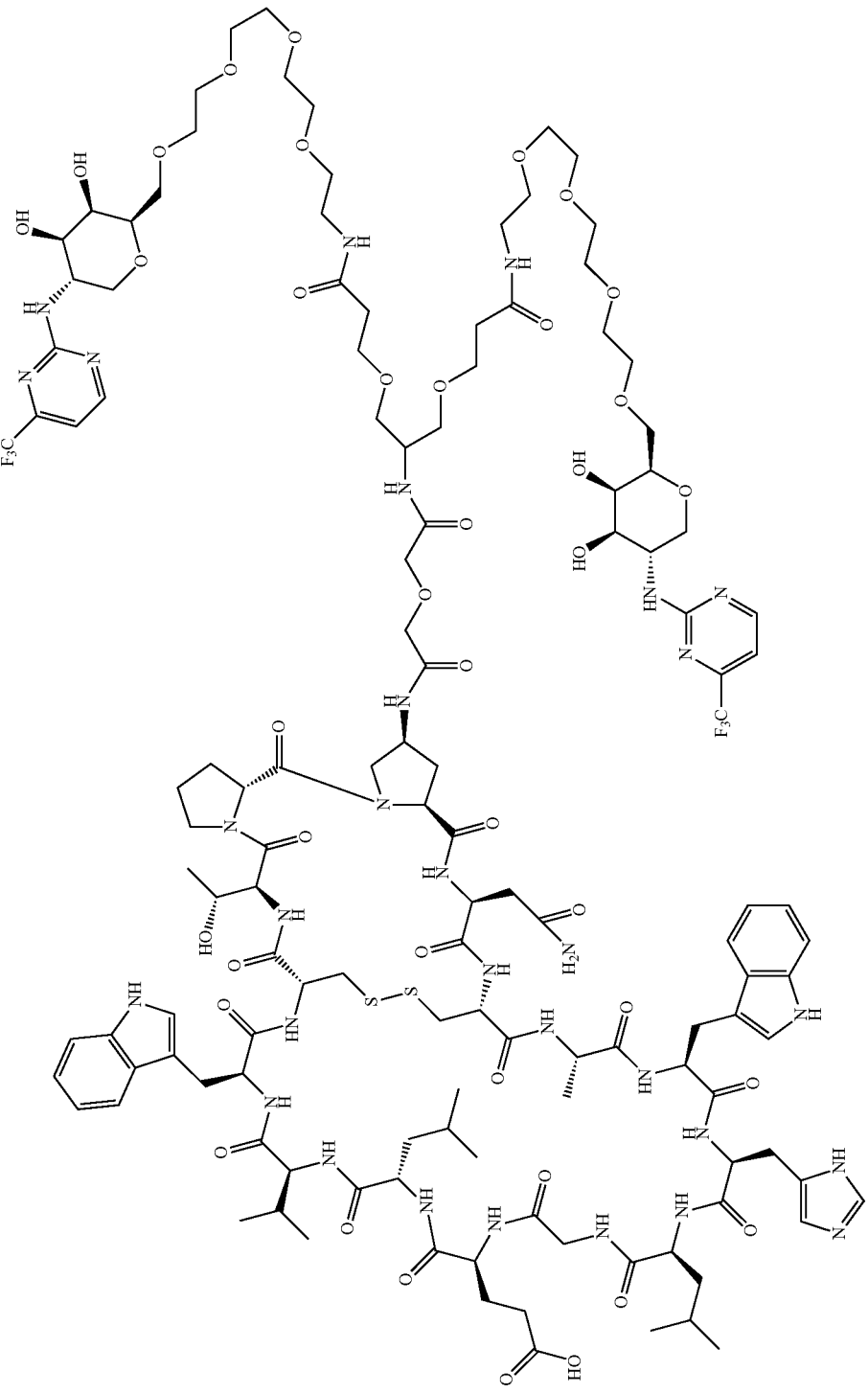

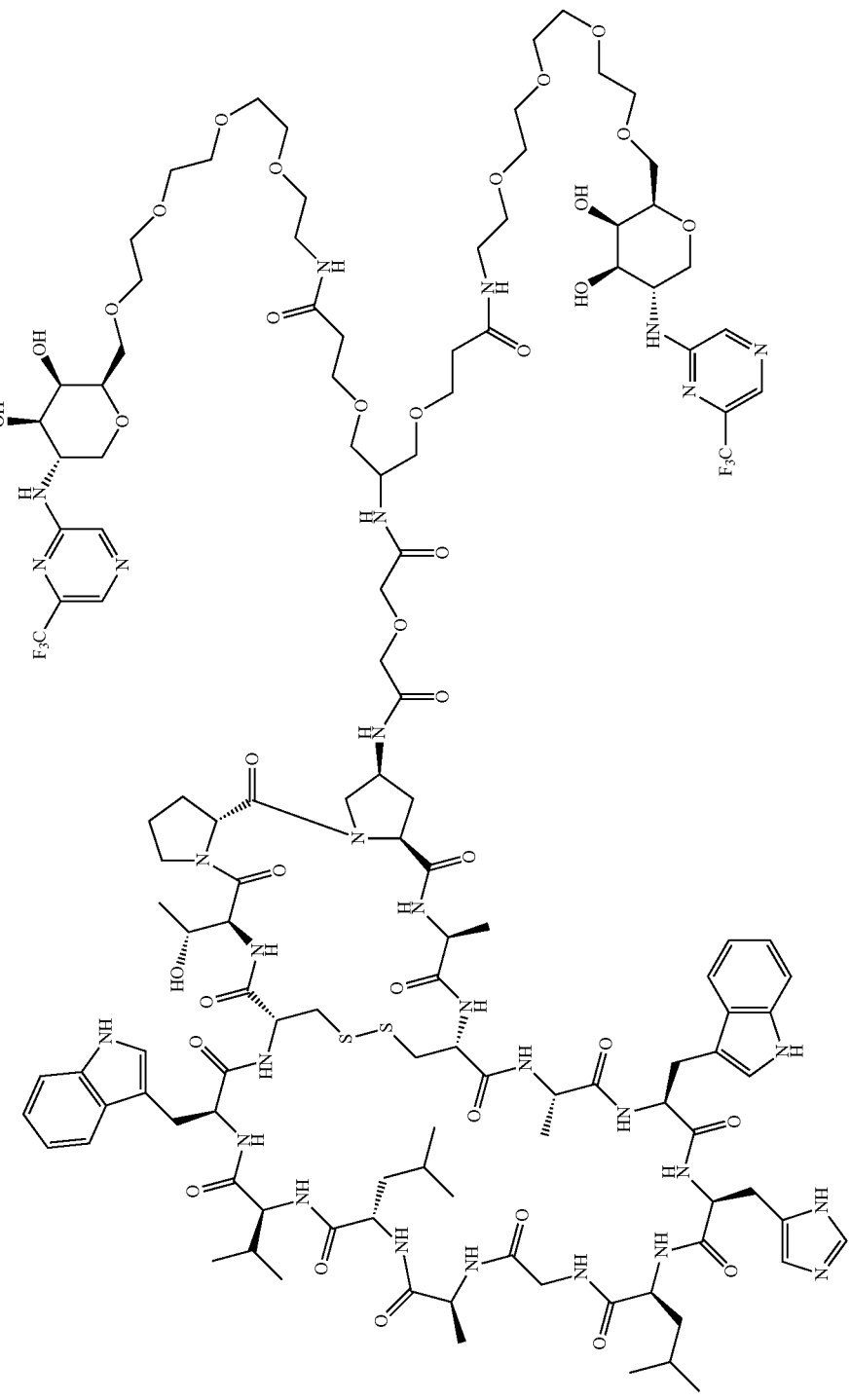

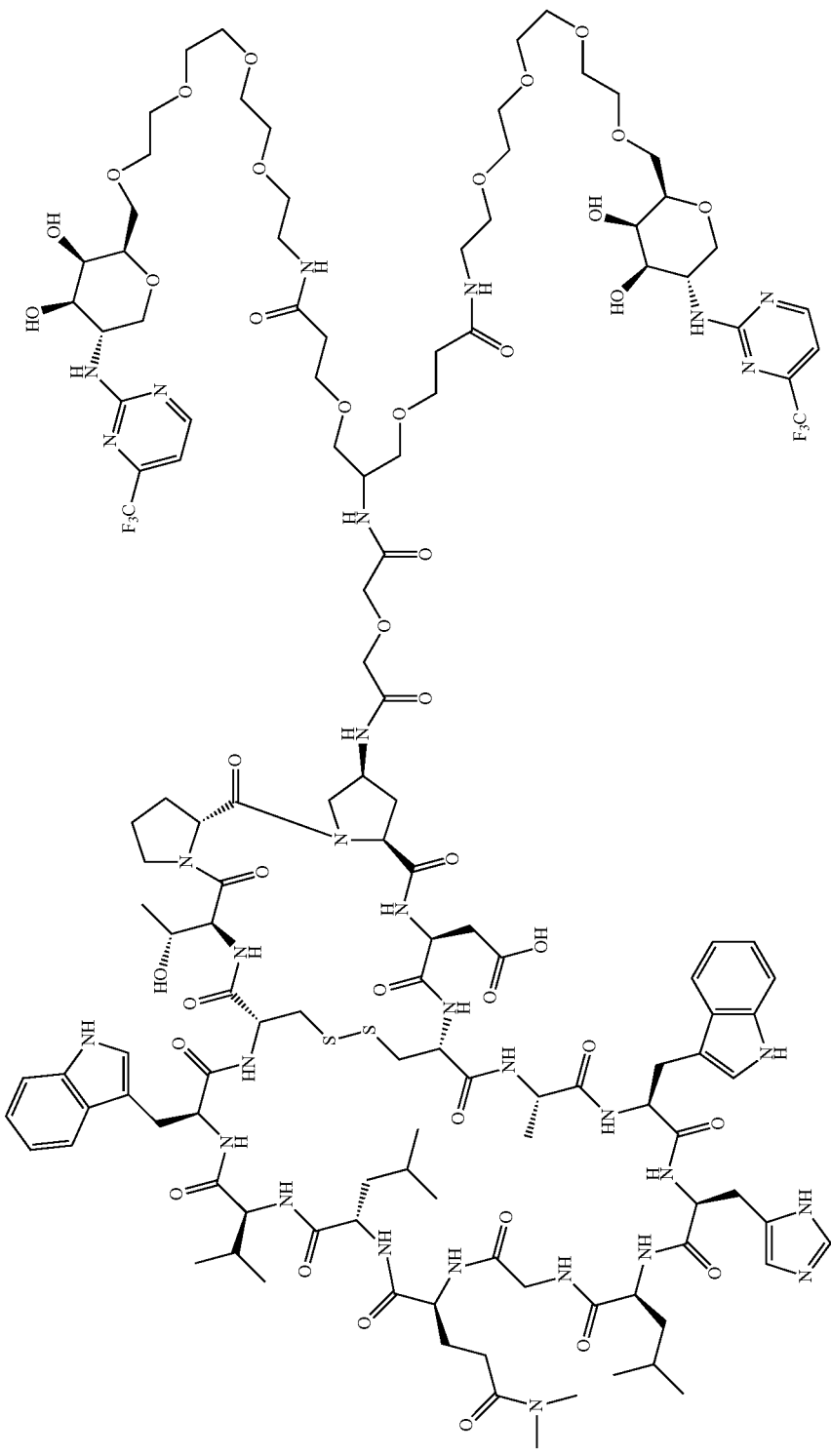

-continued
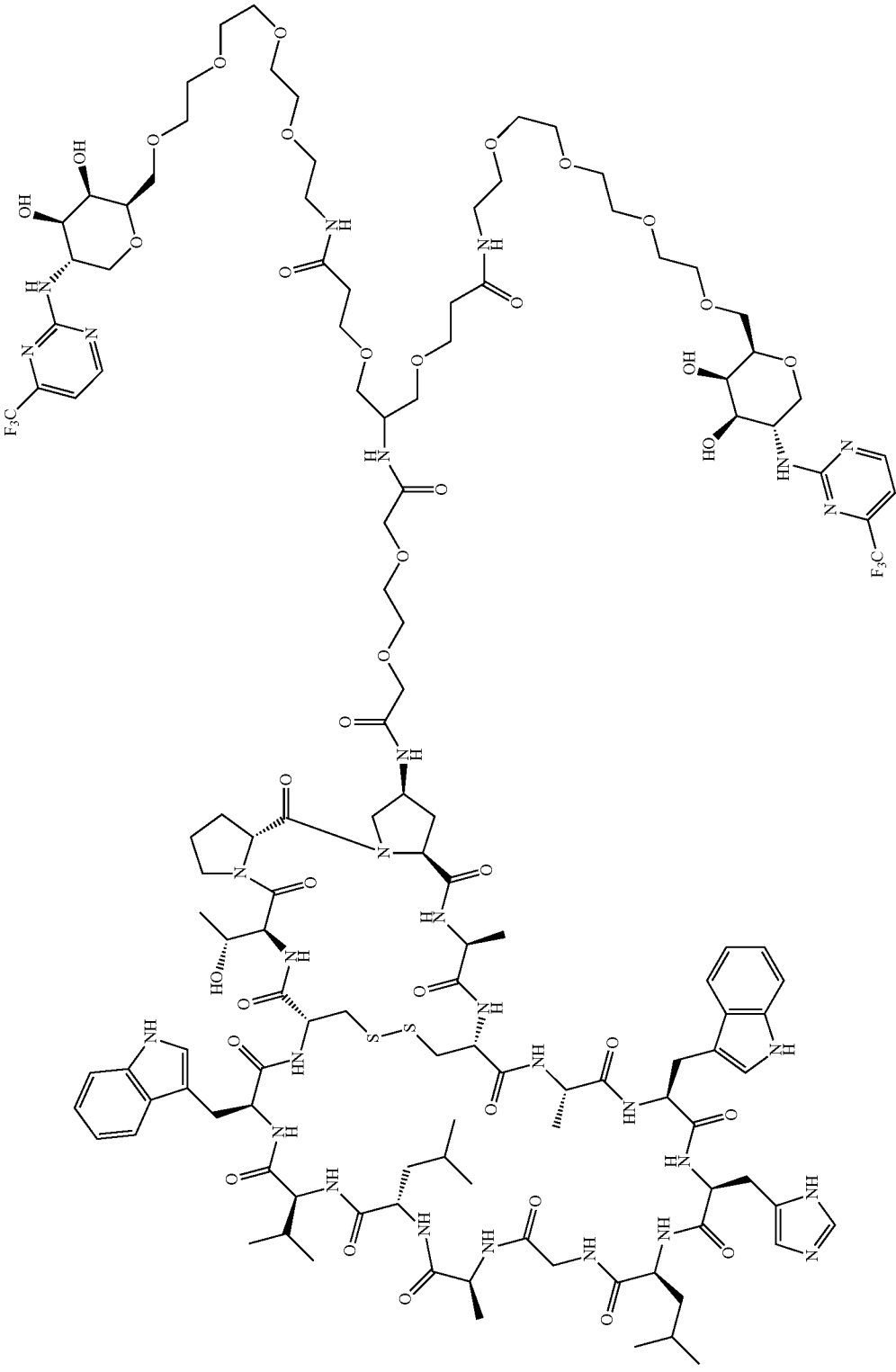

1539 1540
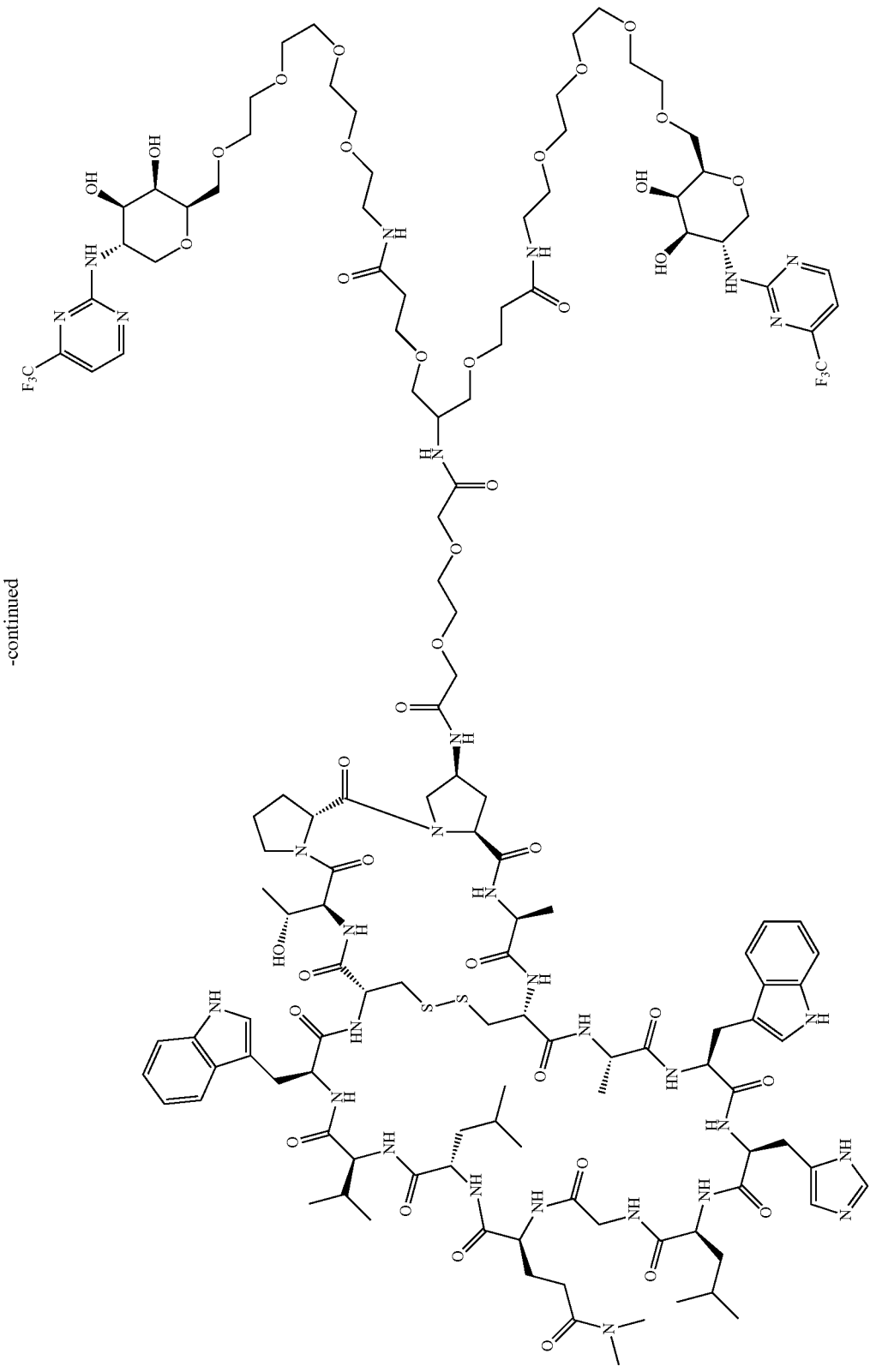

1541 1542
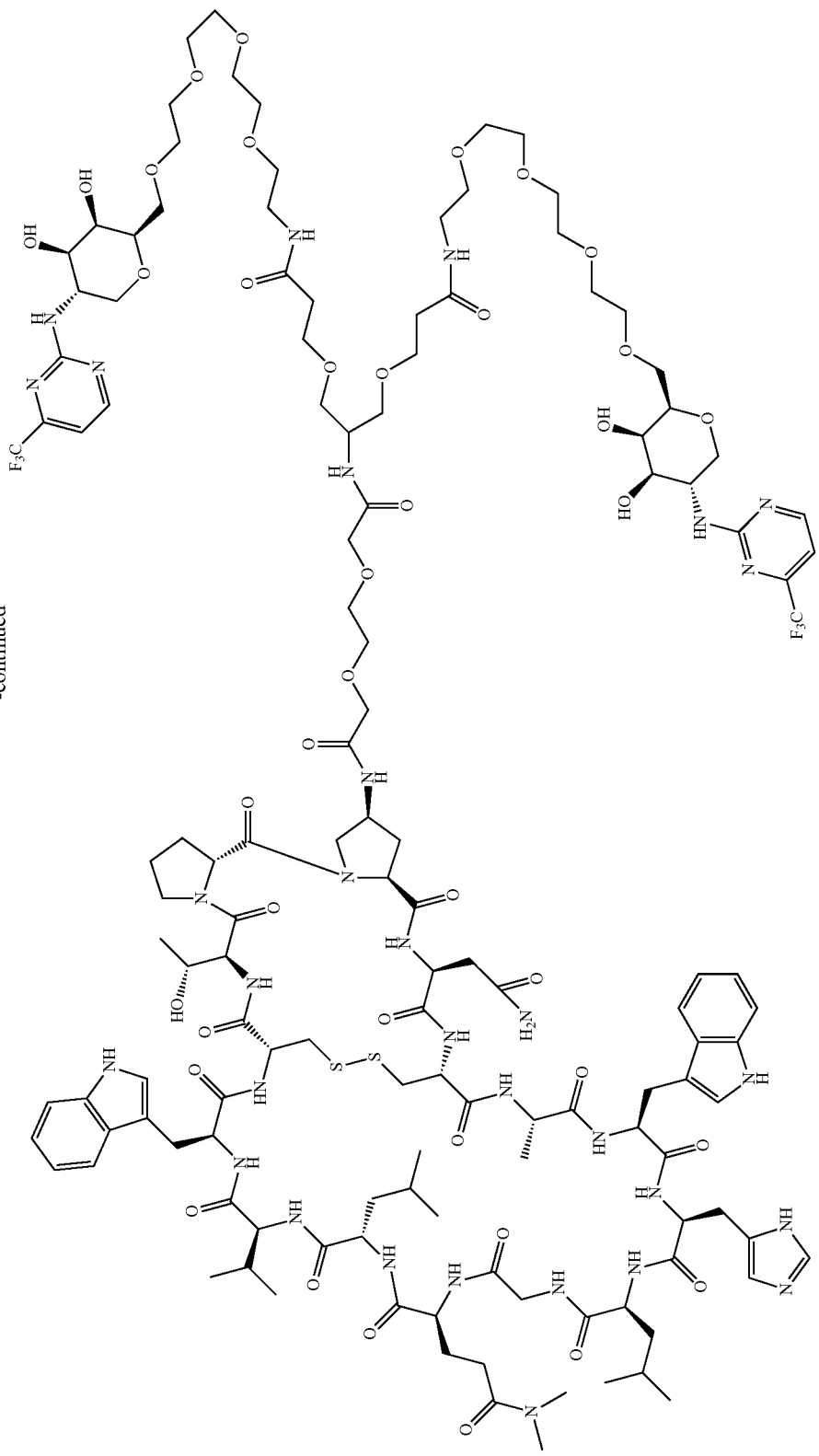

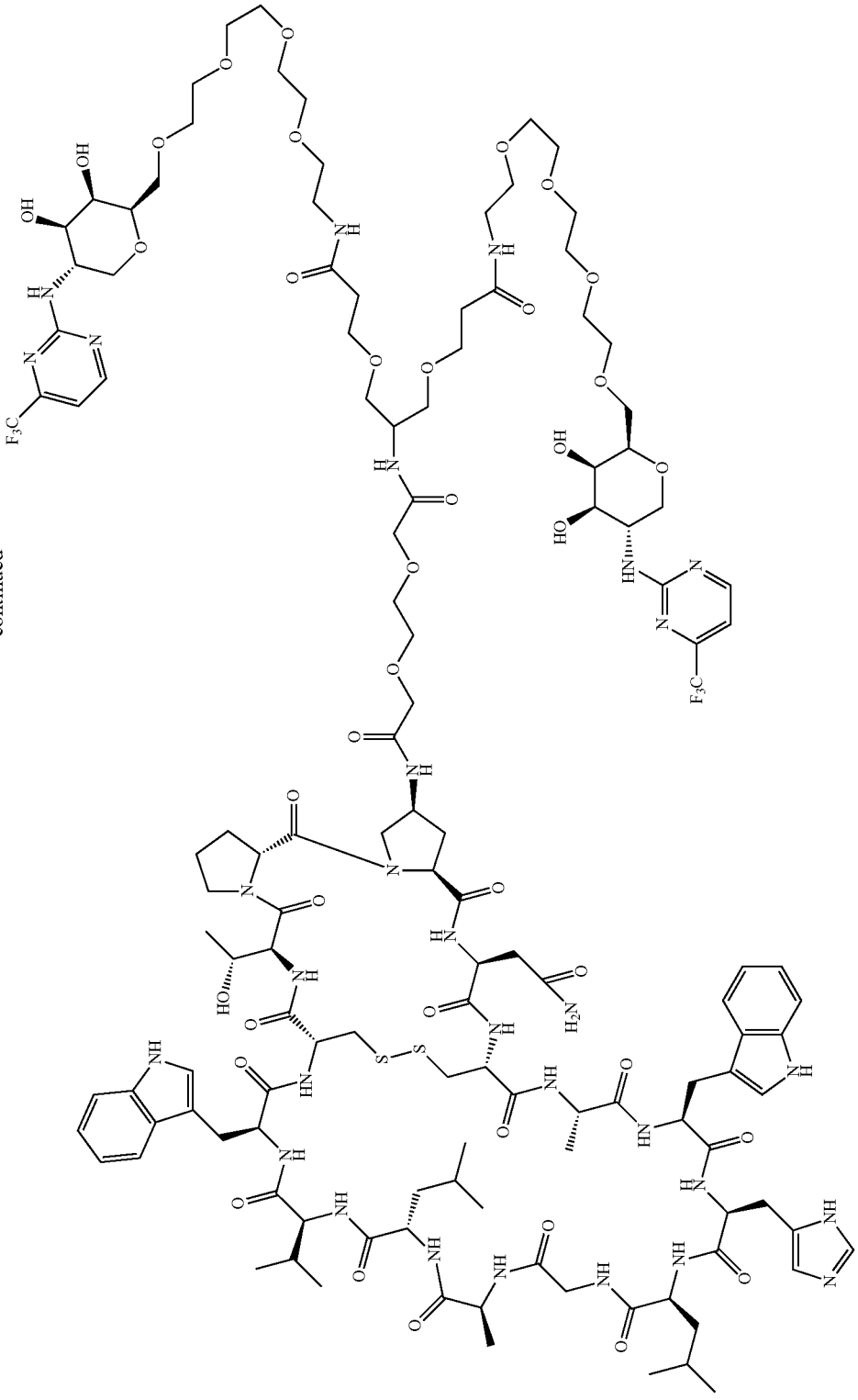

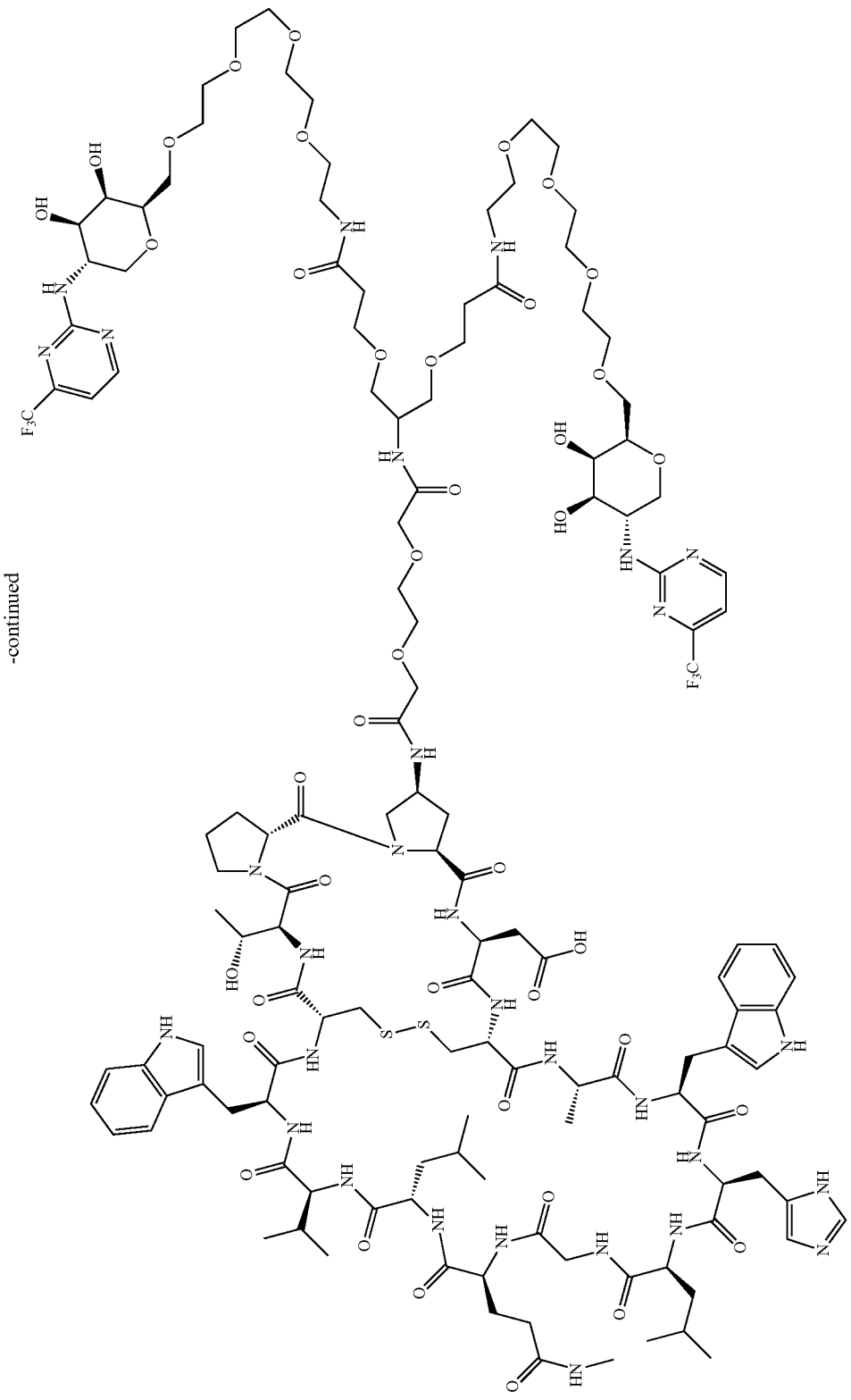

-continued
1547
1548
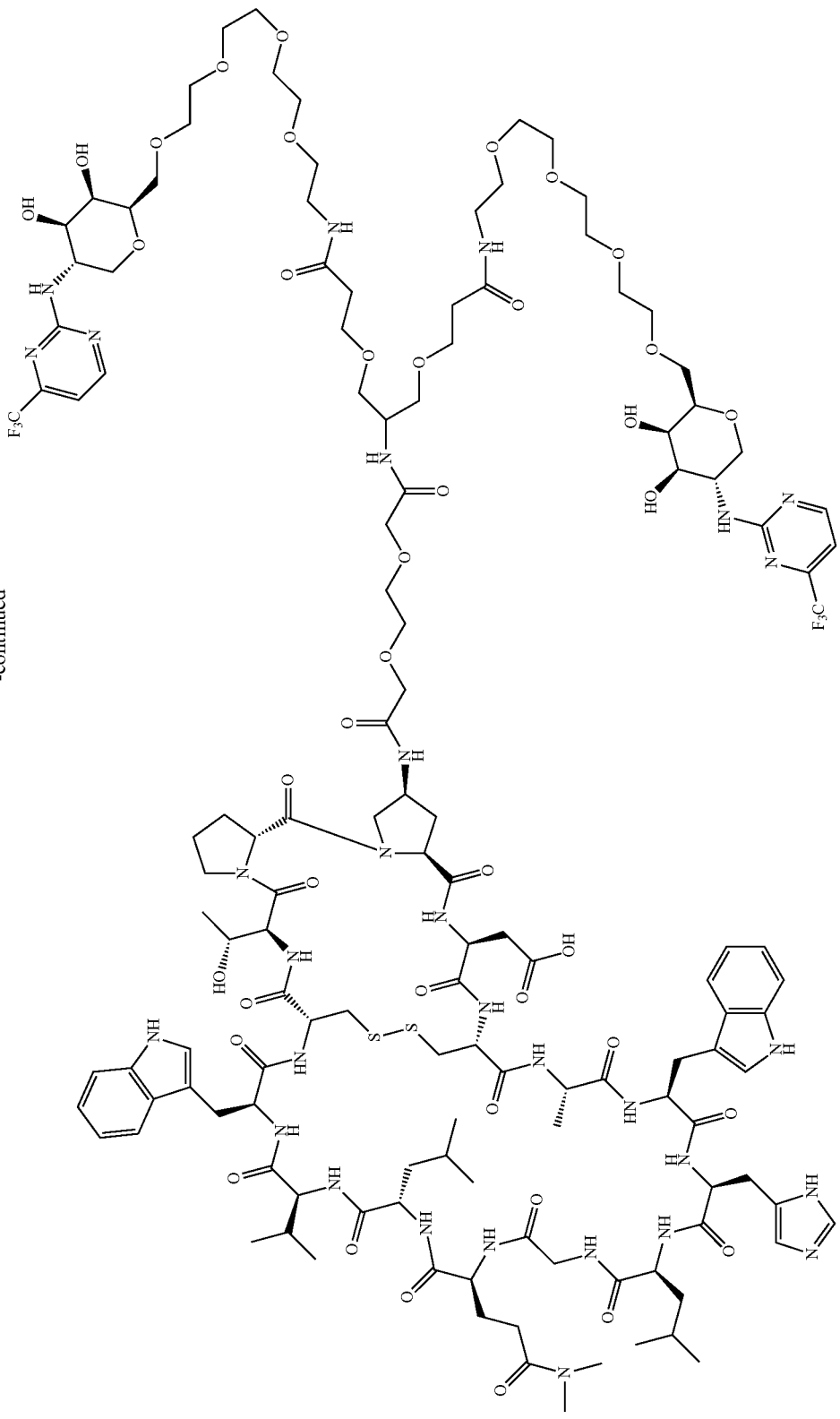

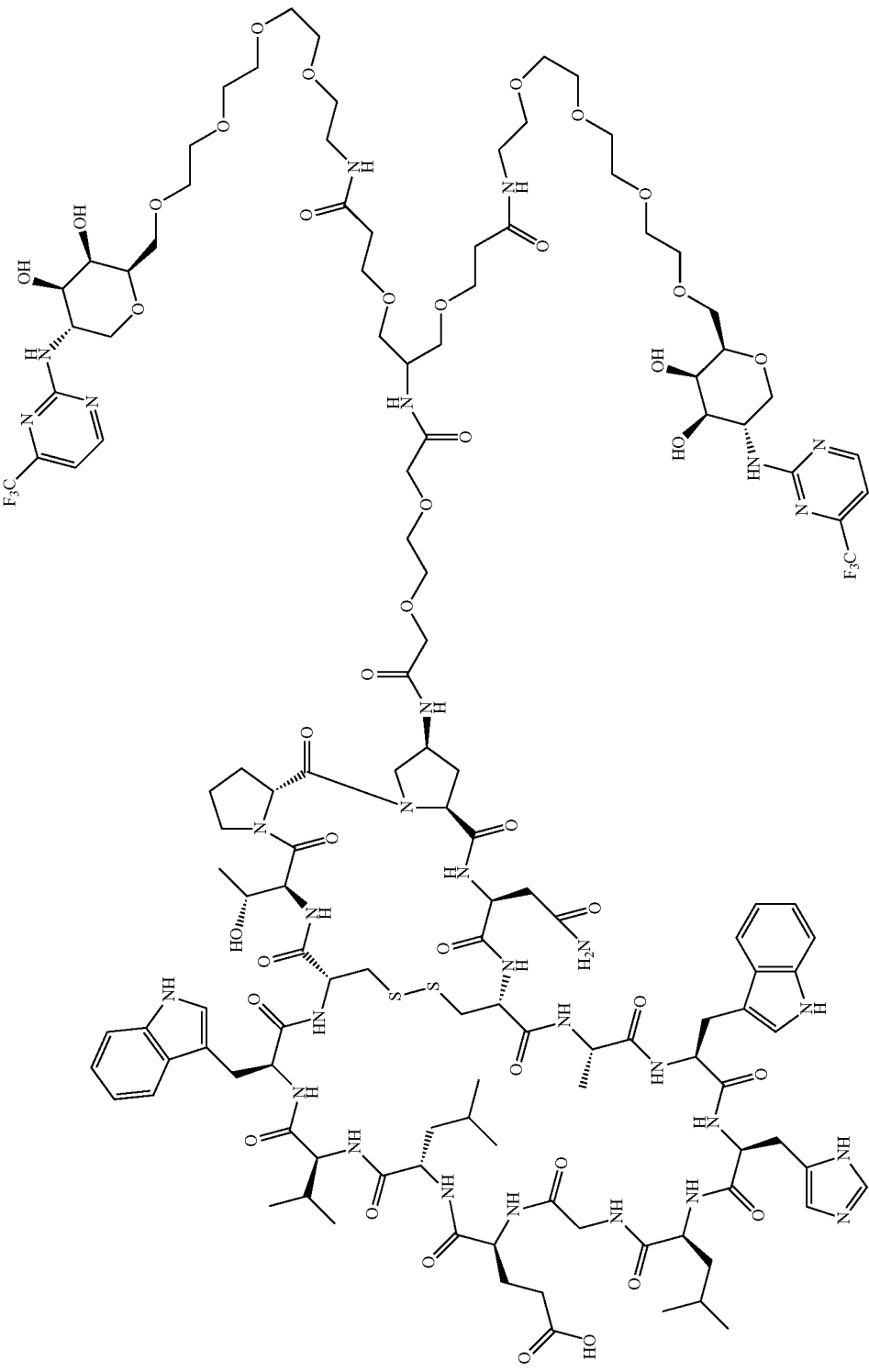

-continued
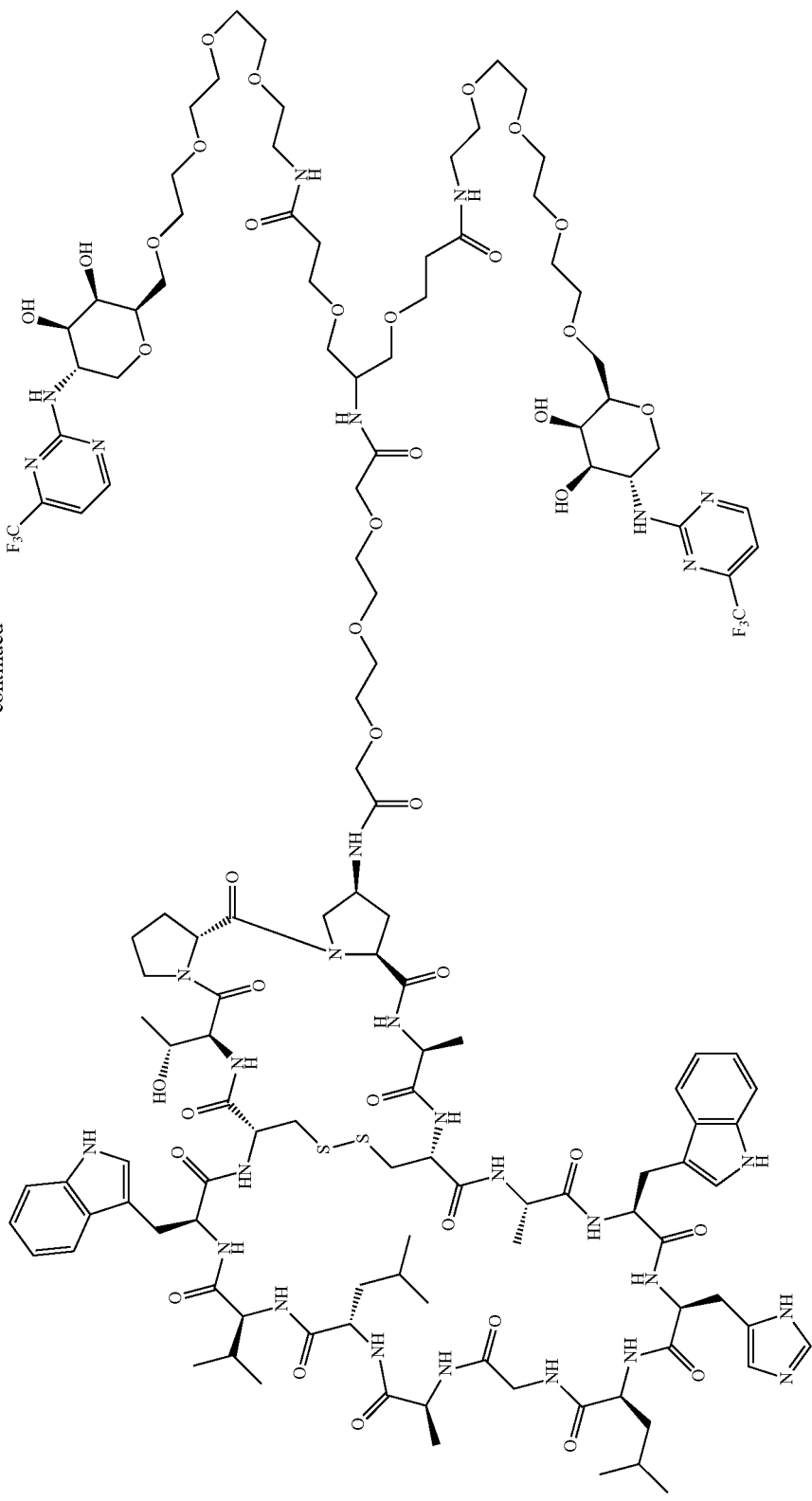

1553 1554
-continued
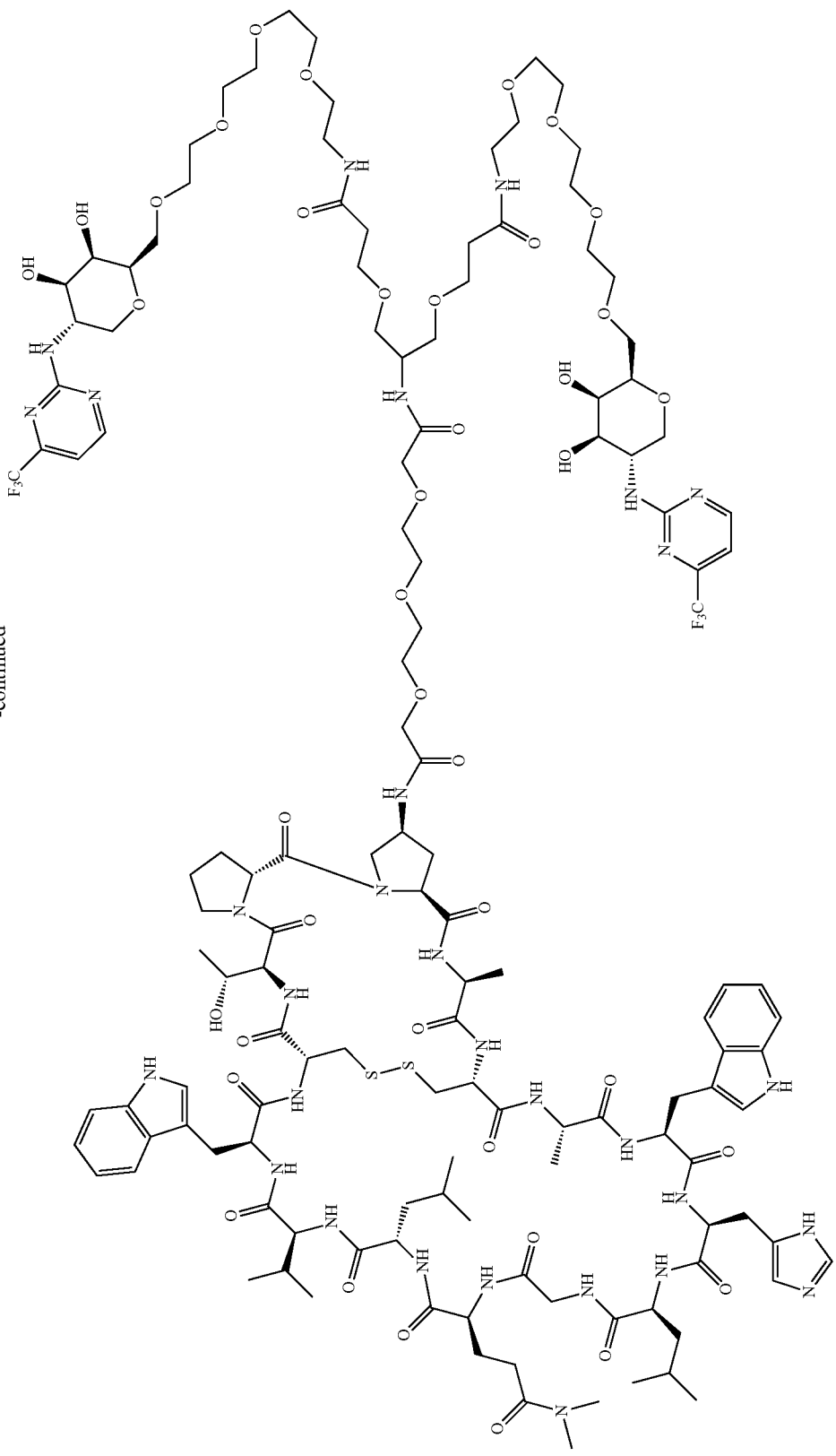

1555 1556
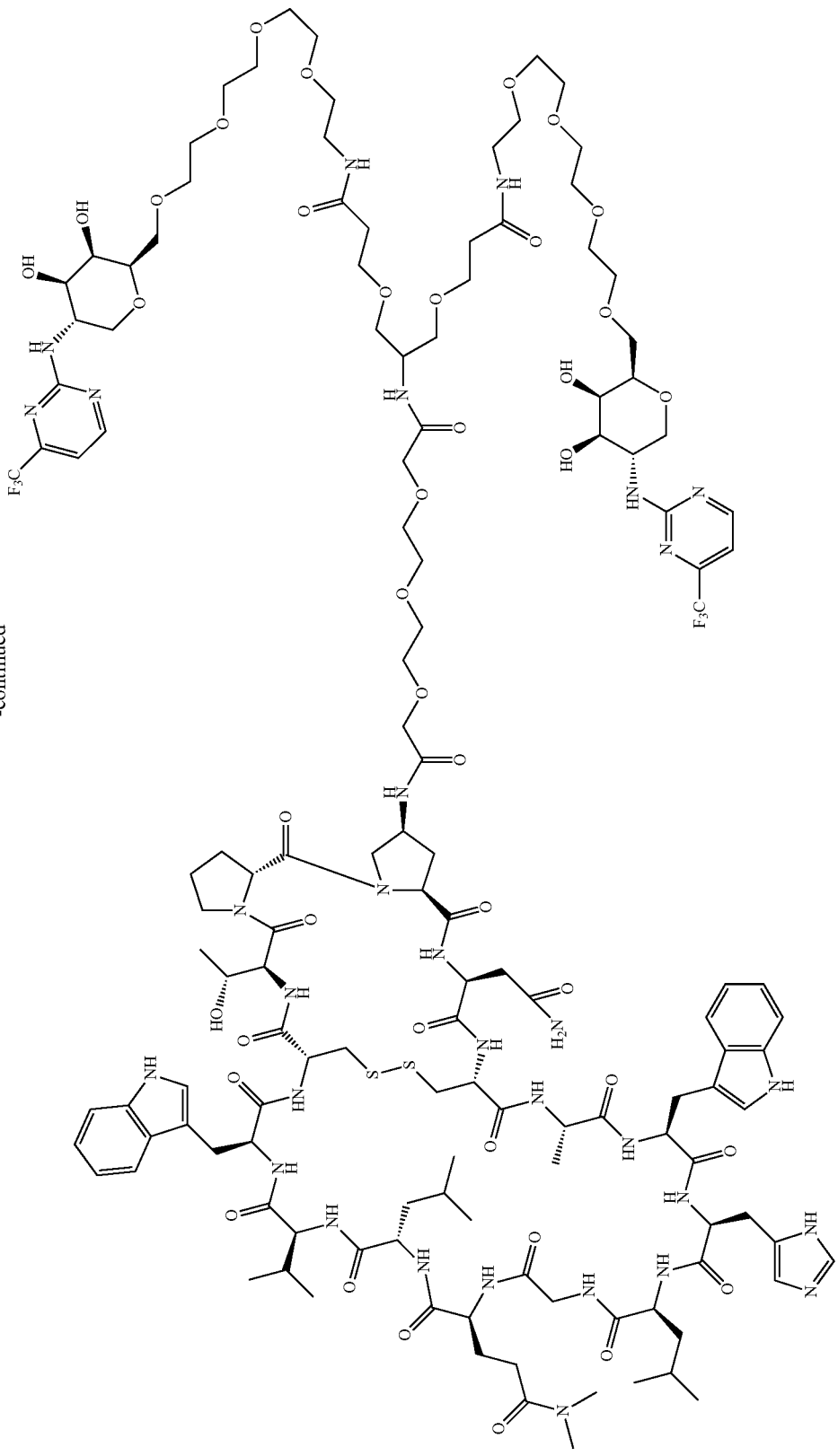

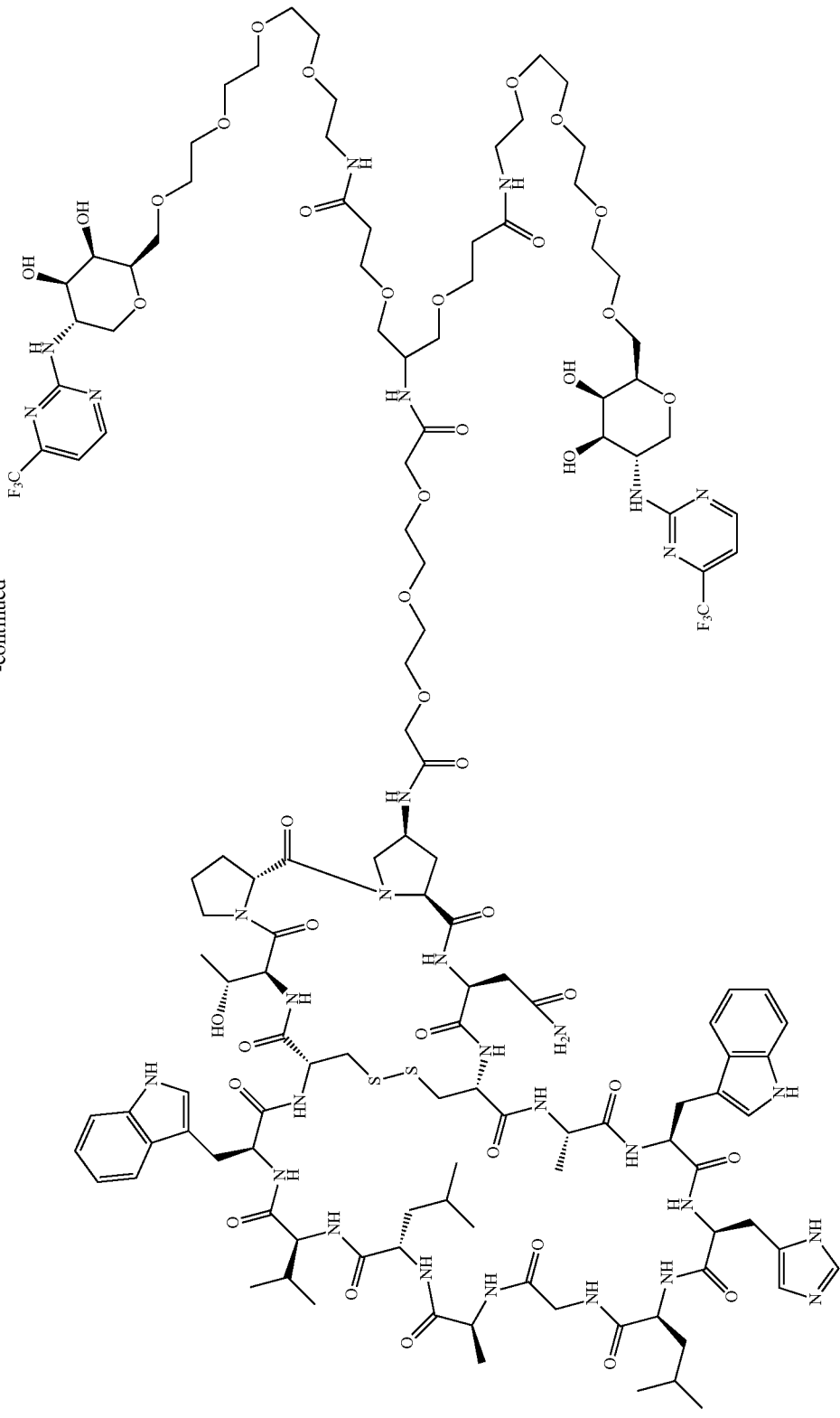

1559     1560
-continued
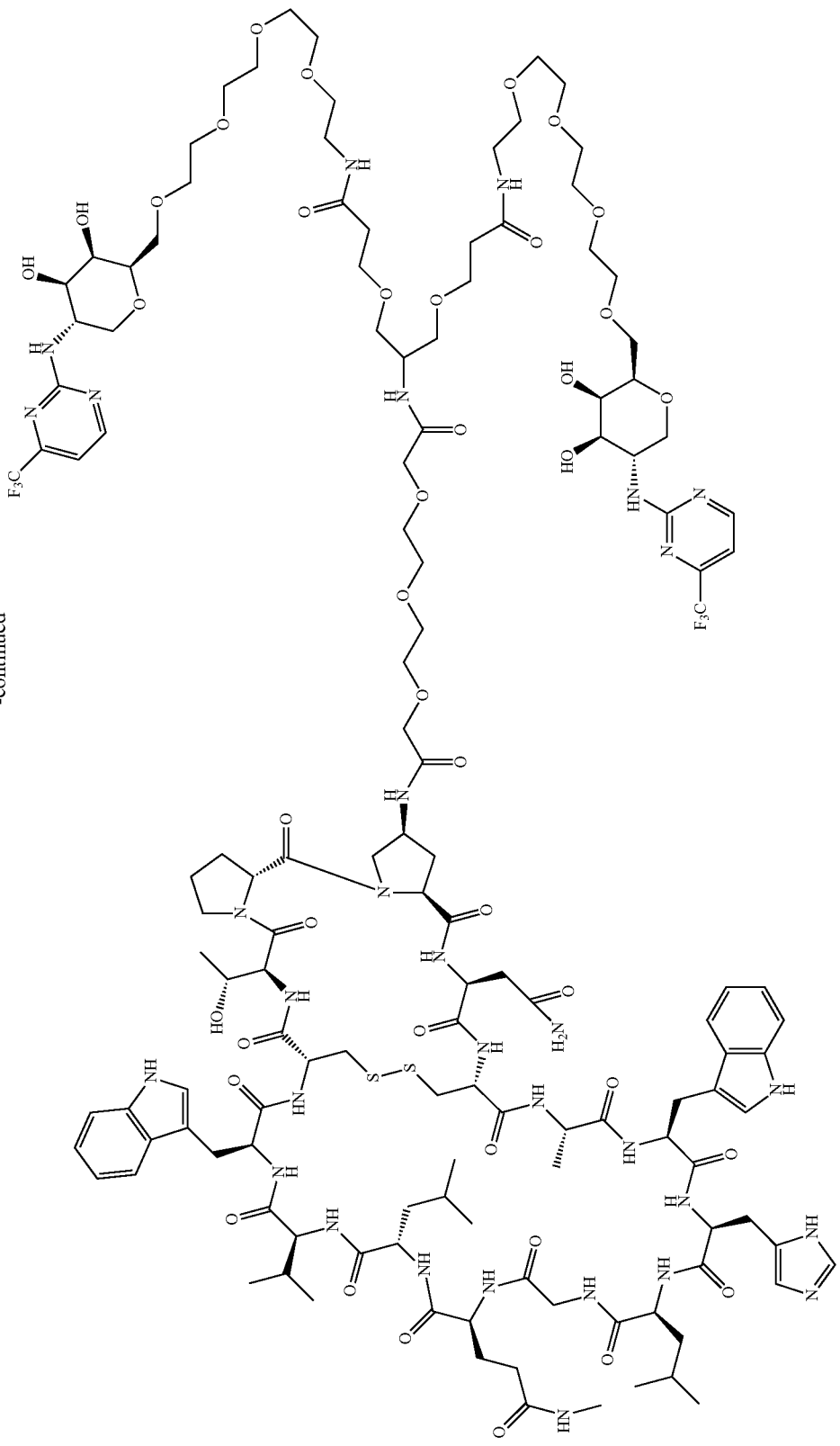

1561 1562
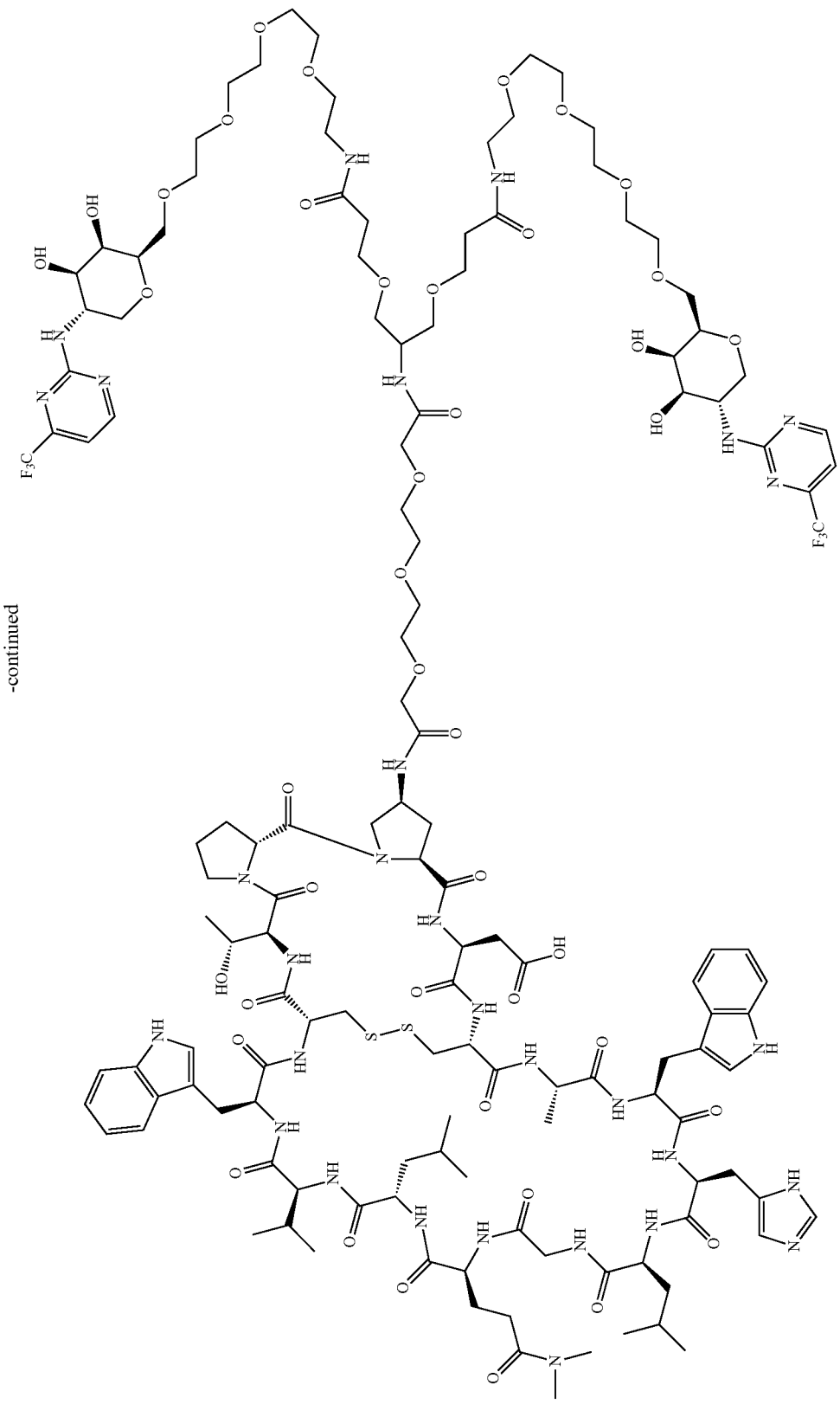

1563 1564
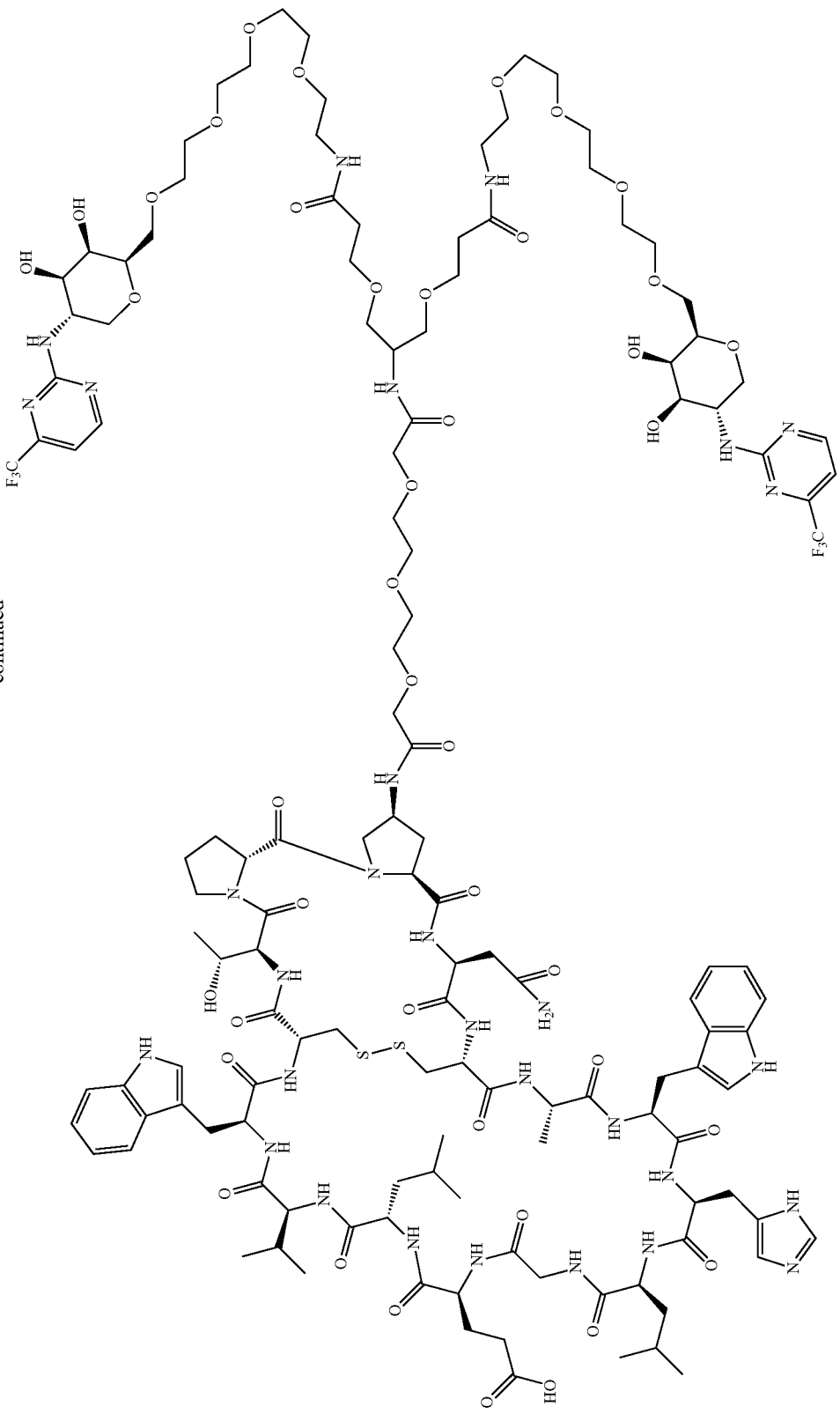

1565 1566
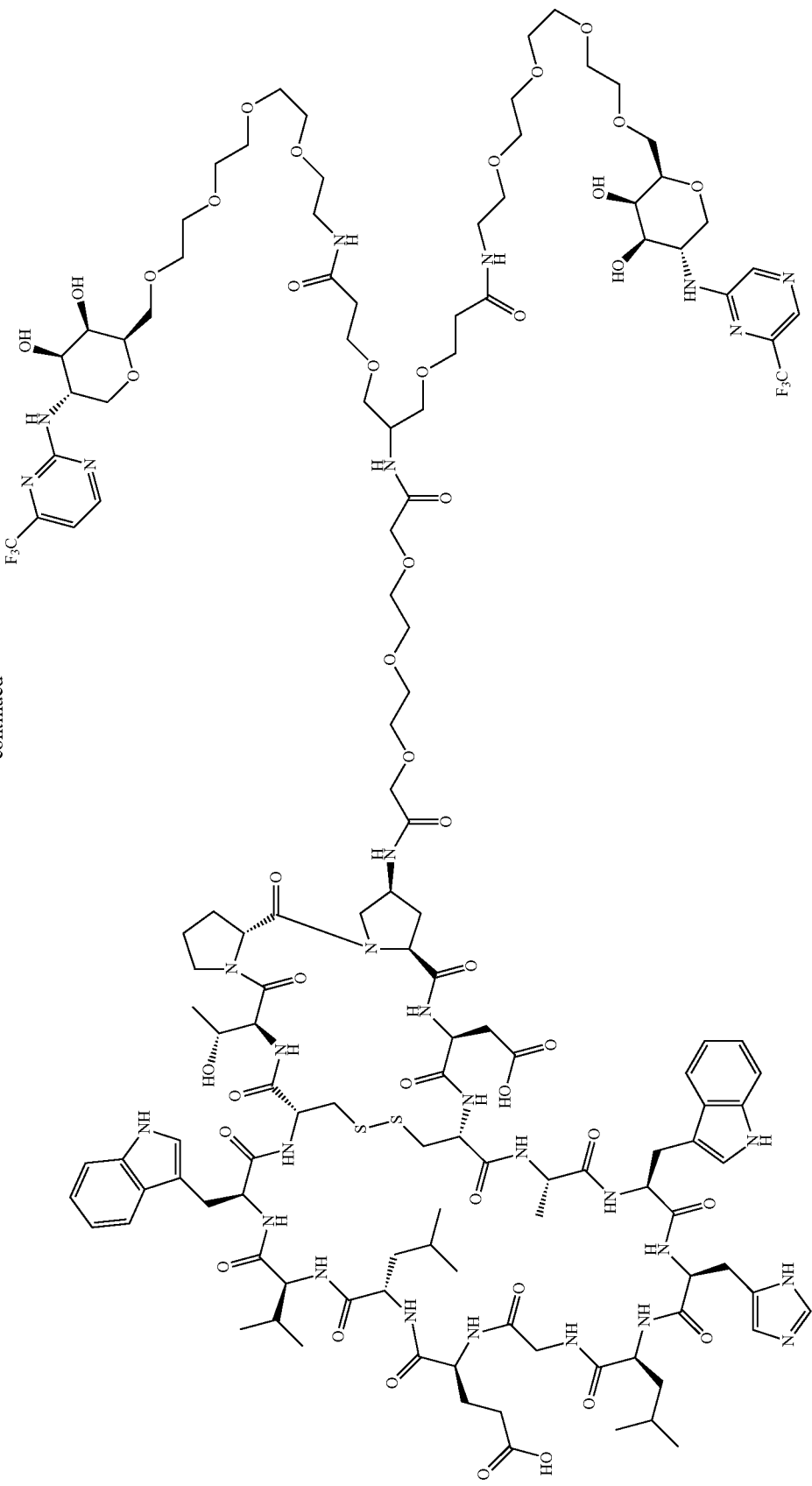
-continued

-continued
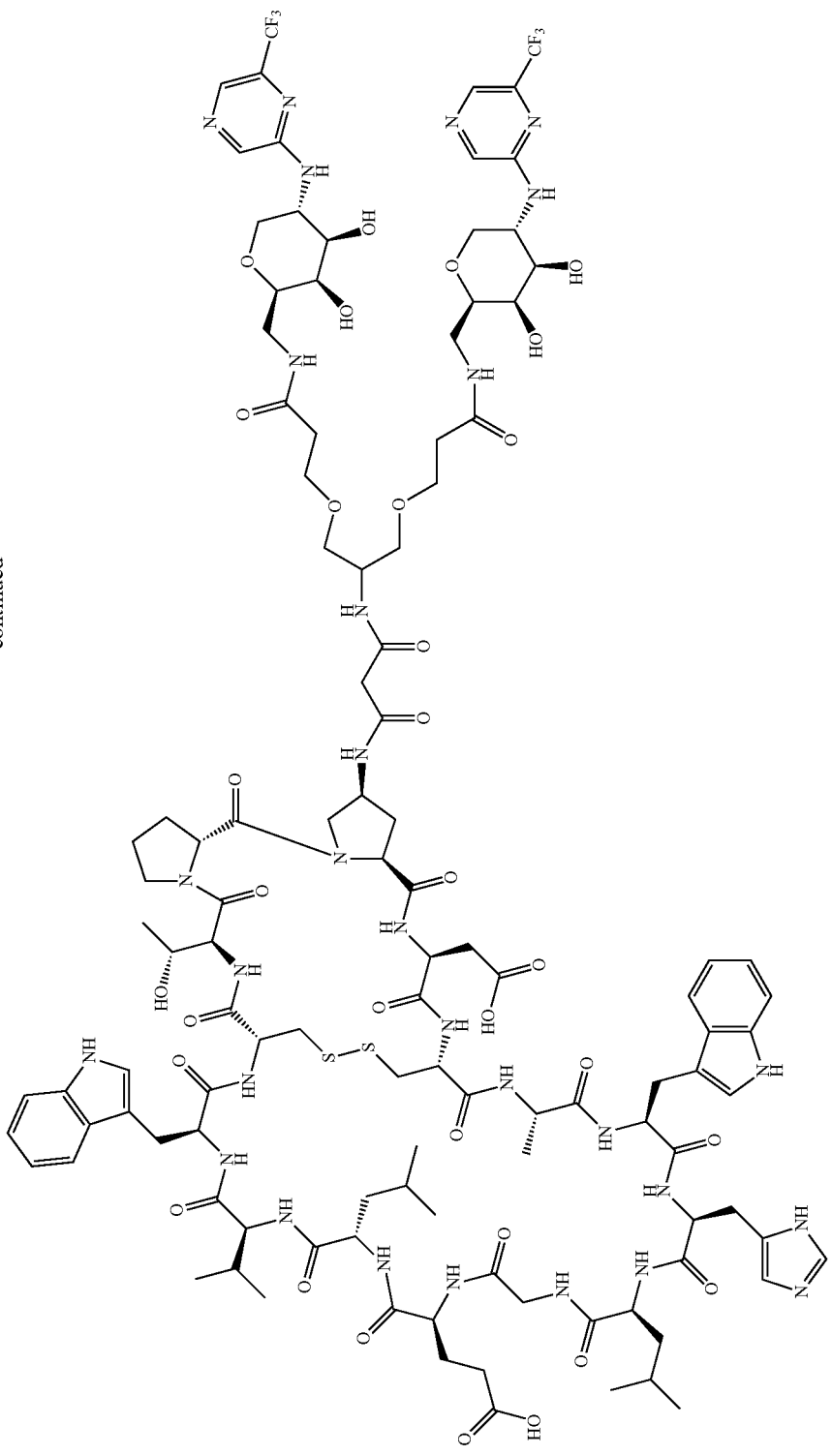

-continued
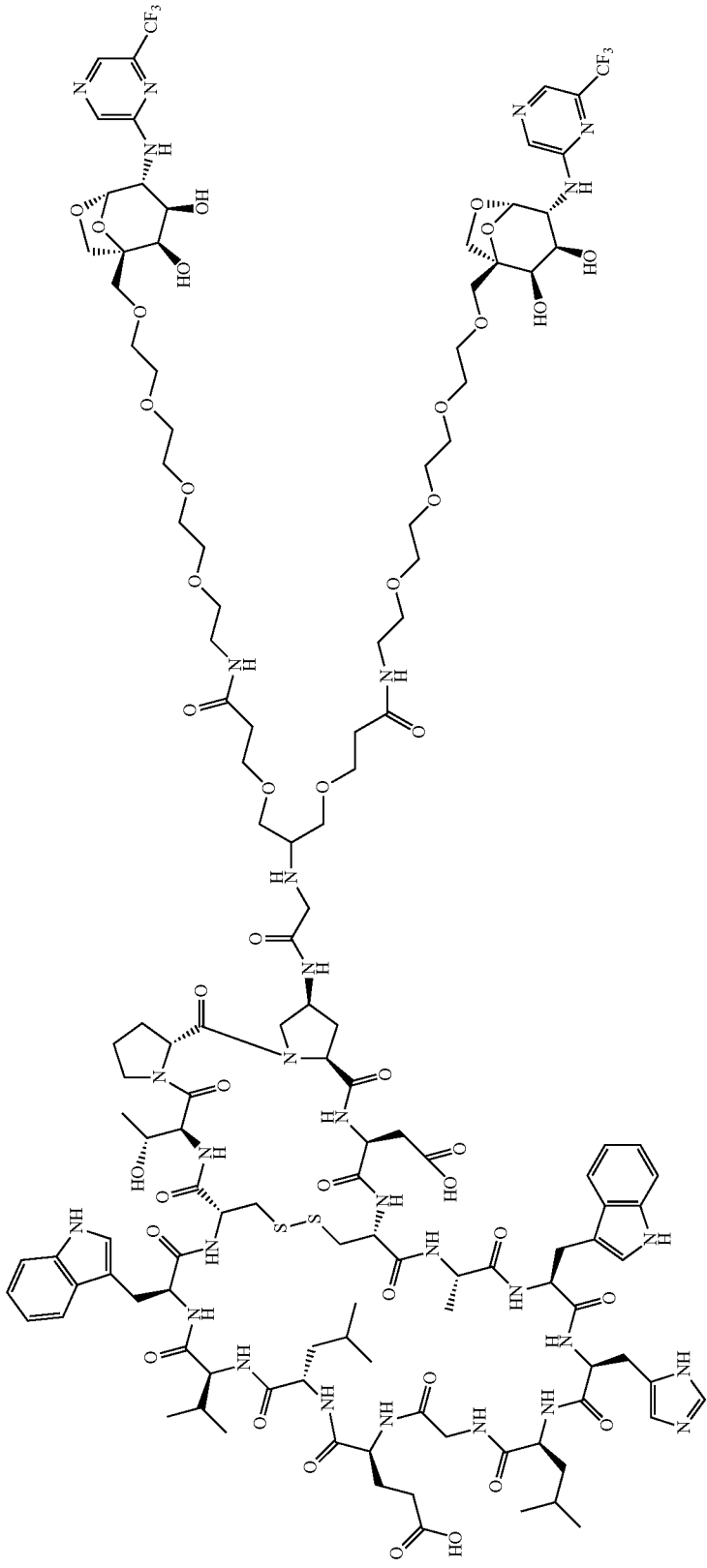

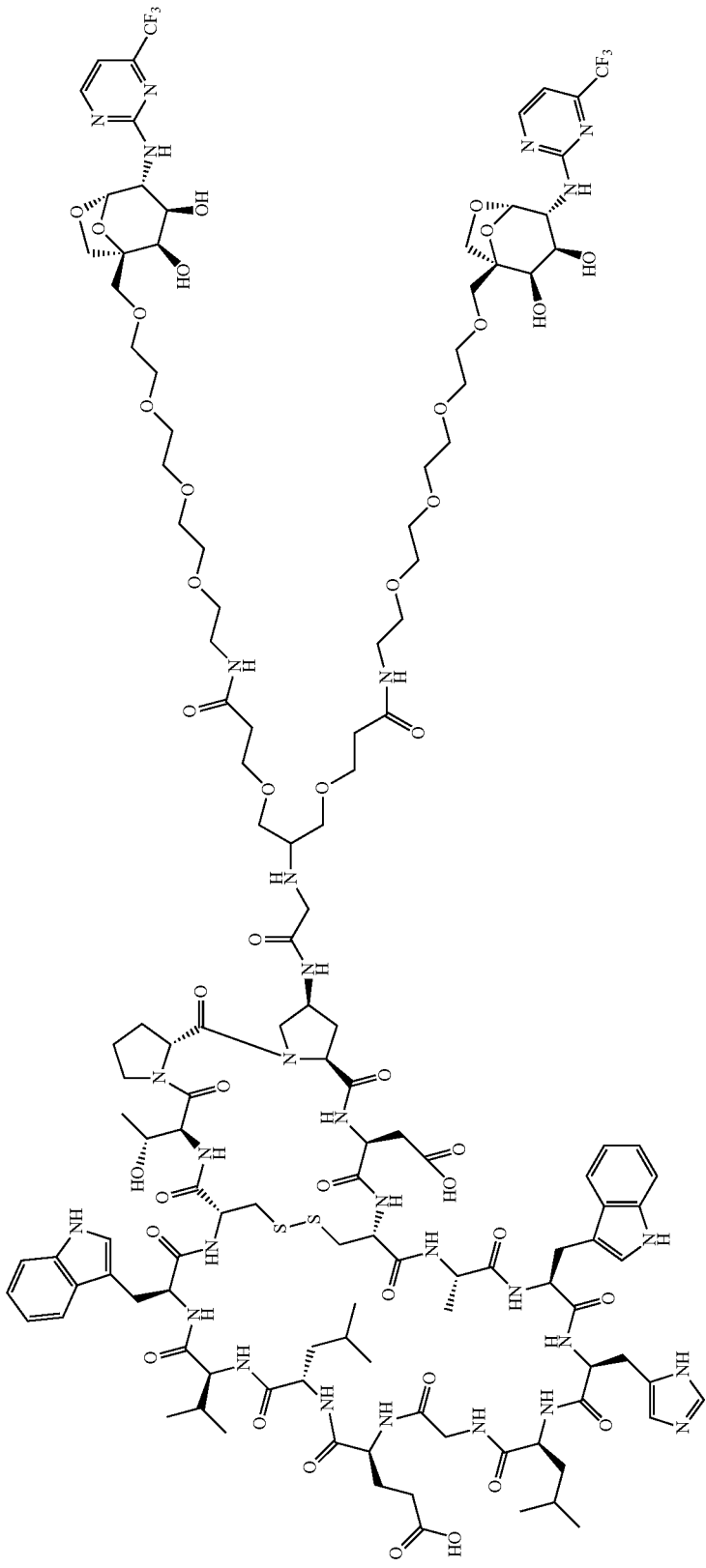

1573 1574
-continued
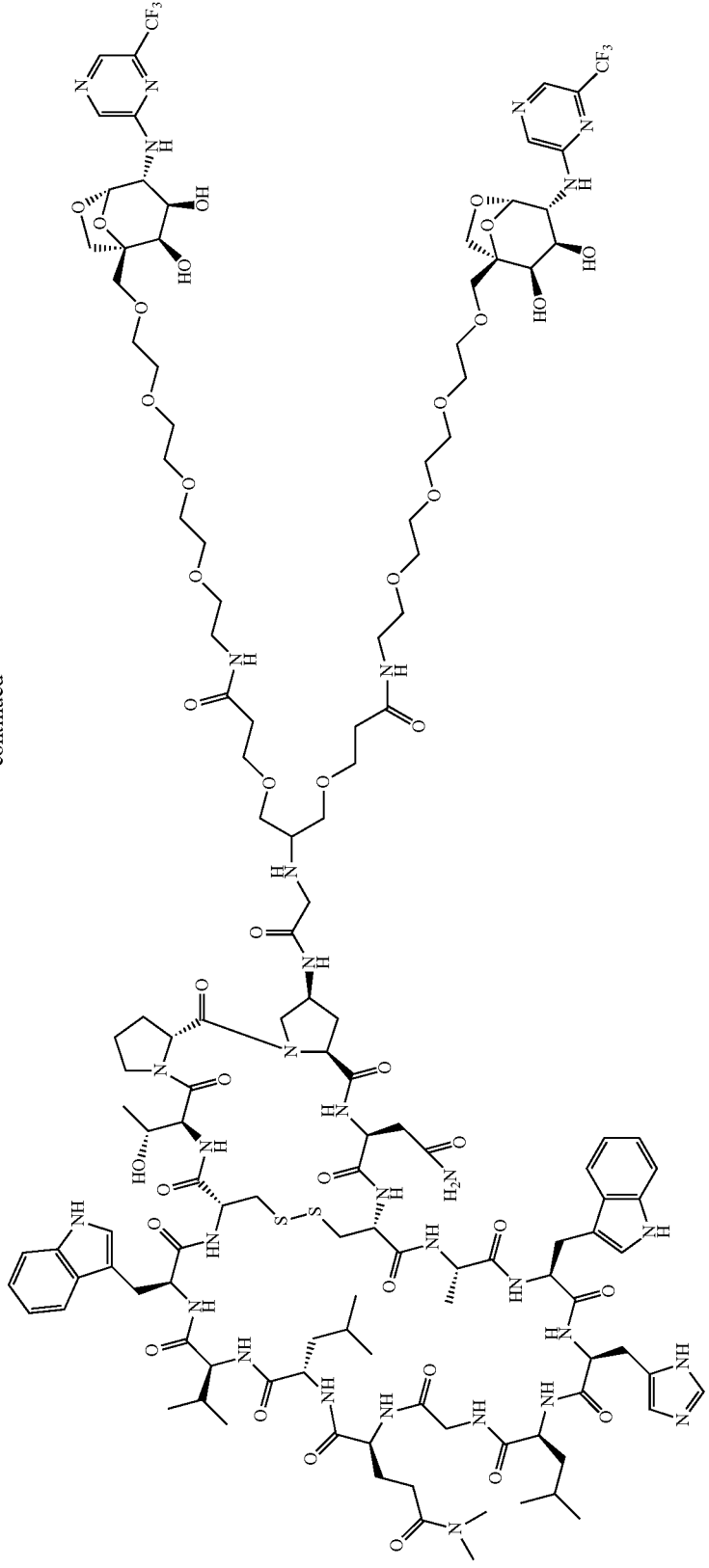

-continued
1575 1576
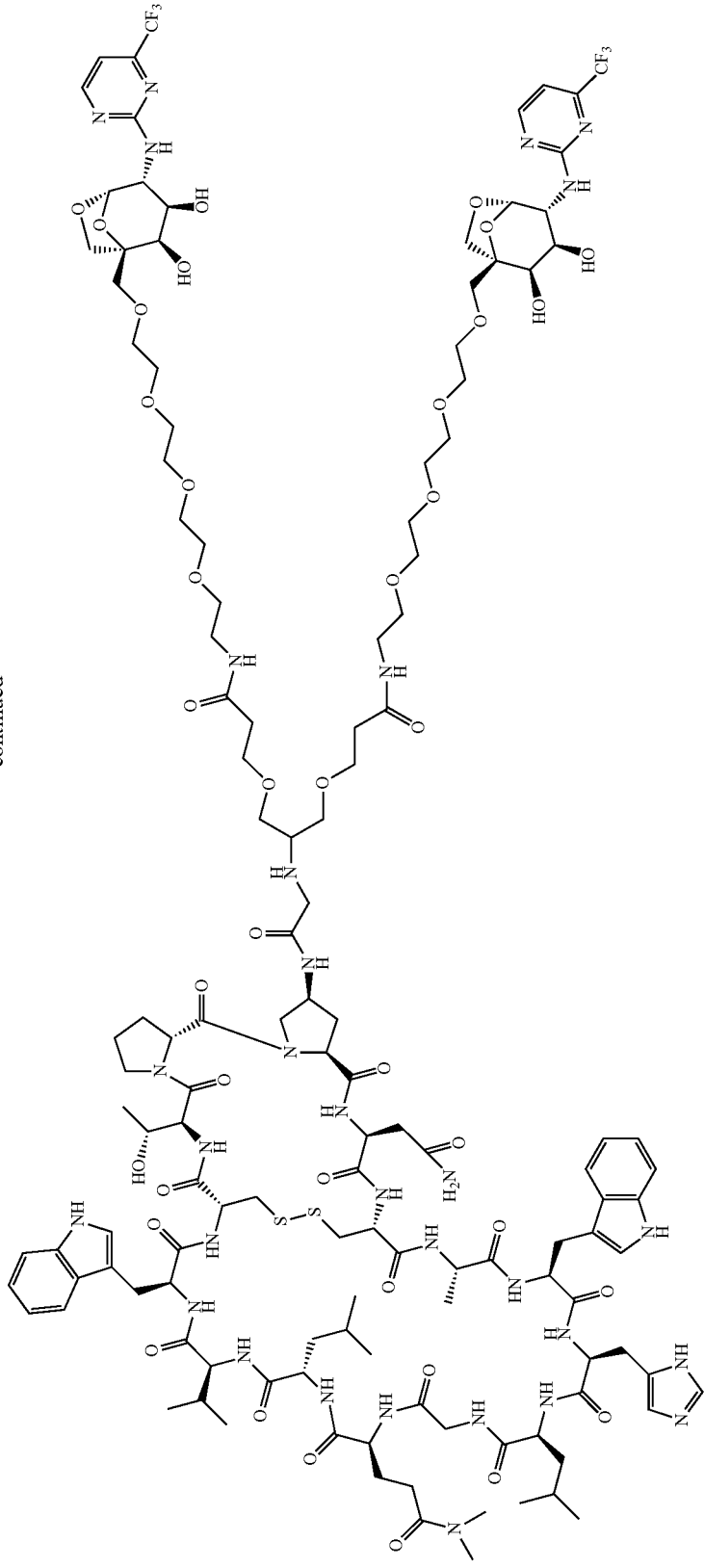

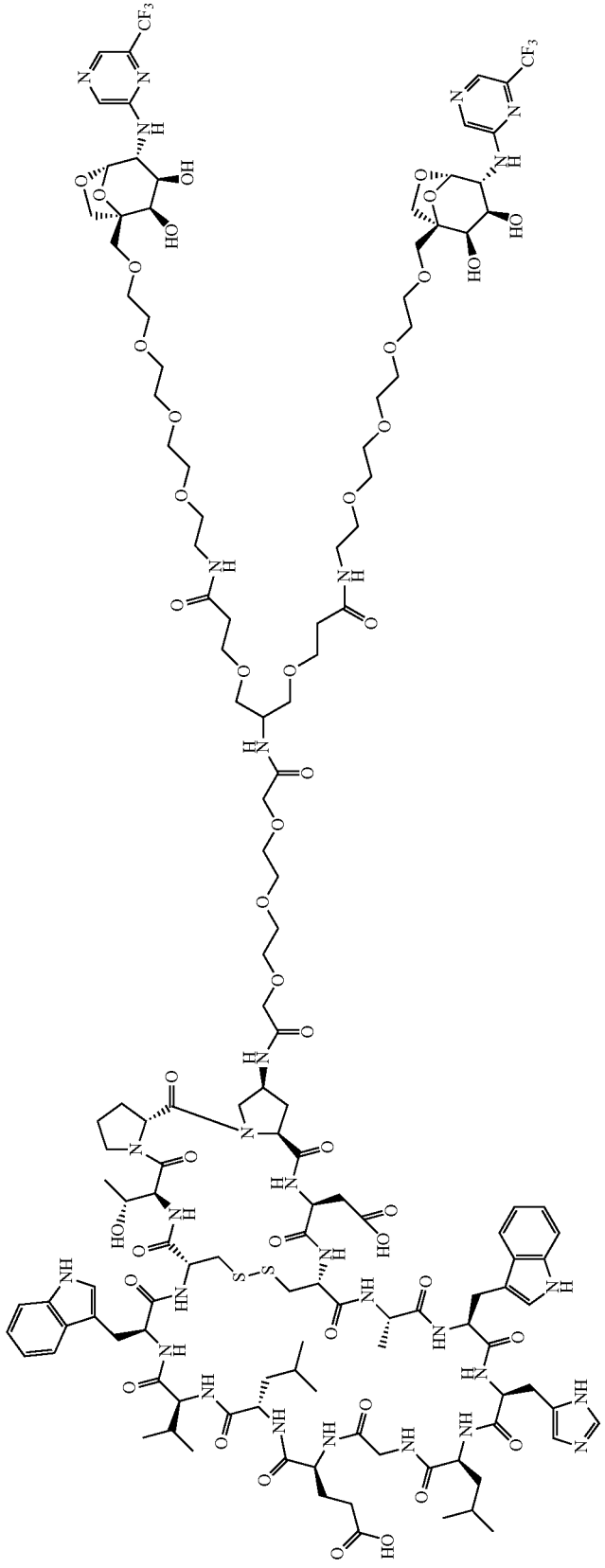

1579 1580
-continued
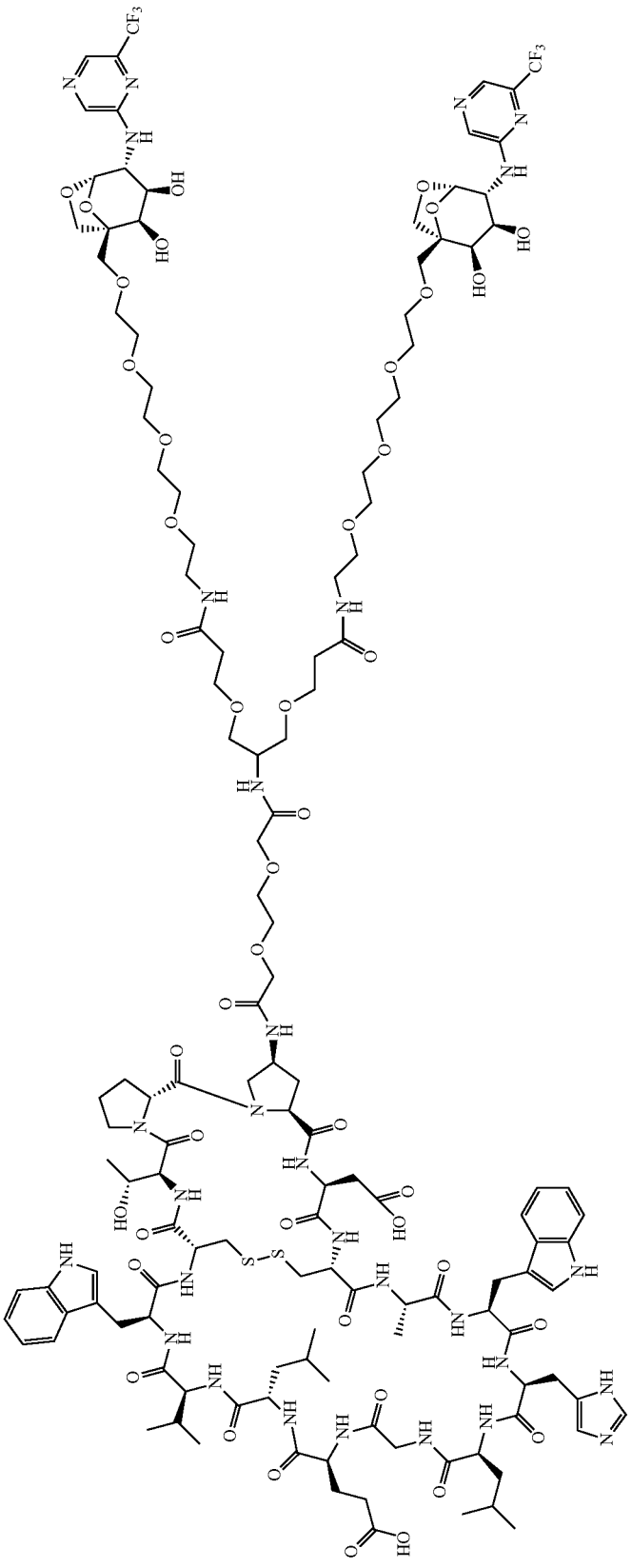

1581 1582
-continued
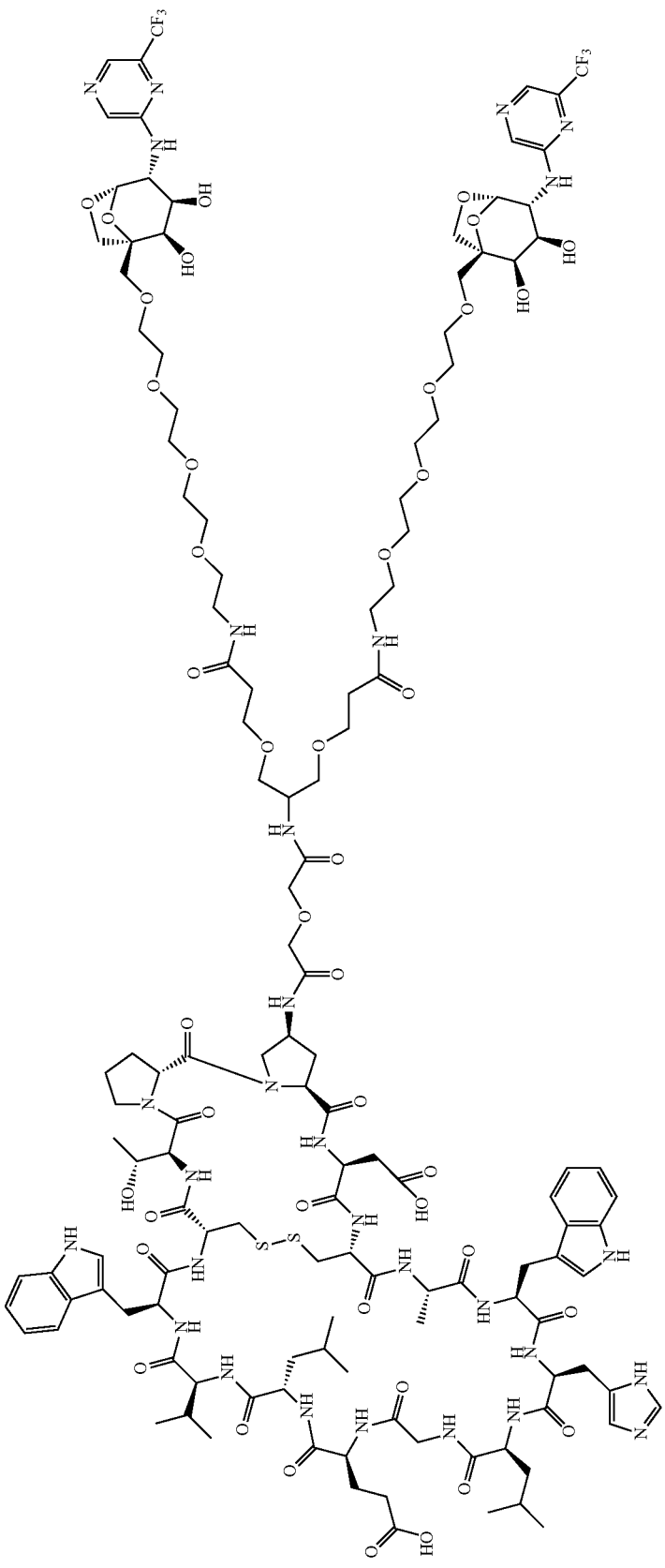

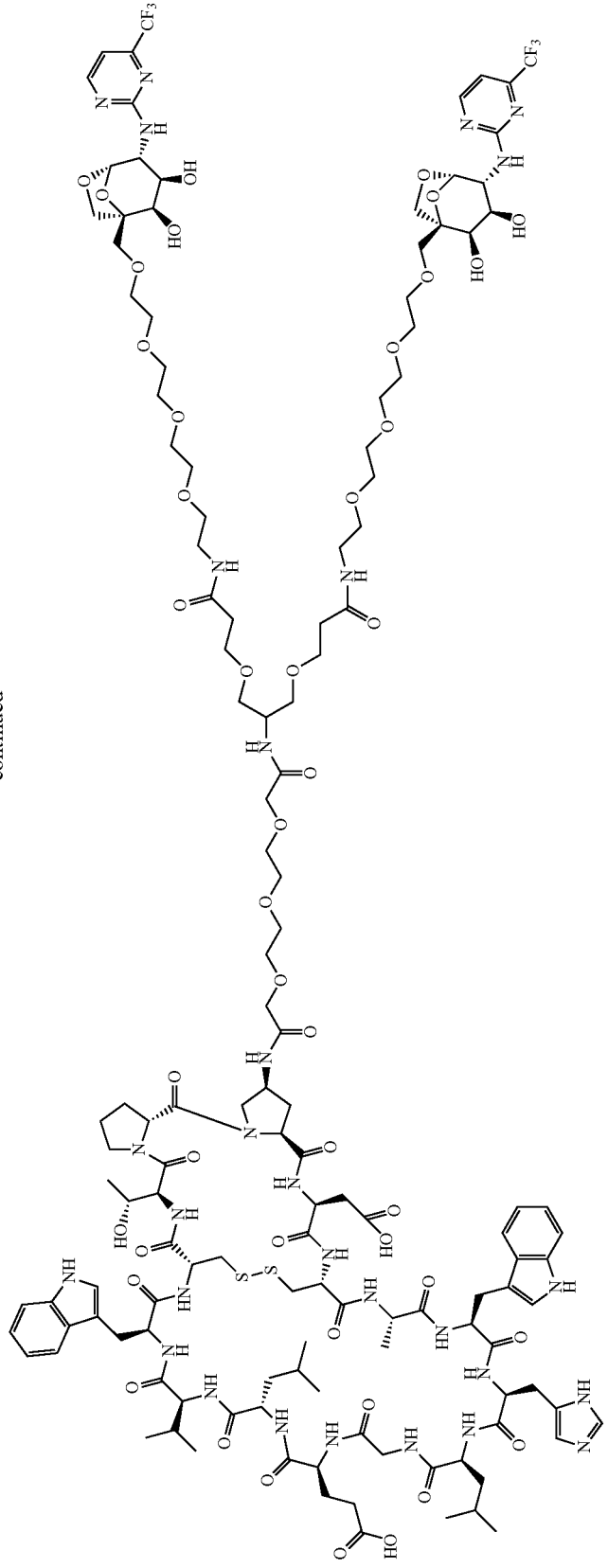

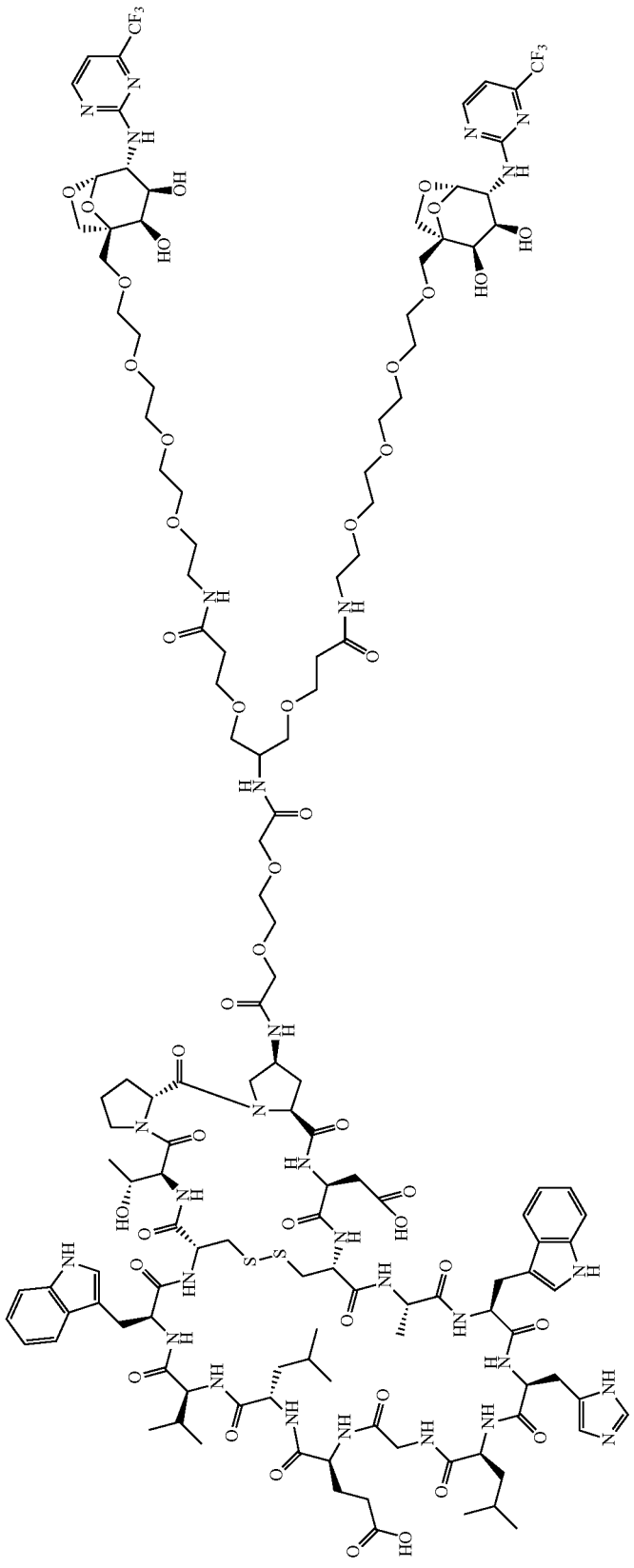

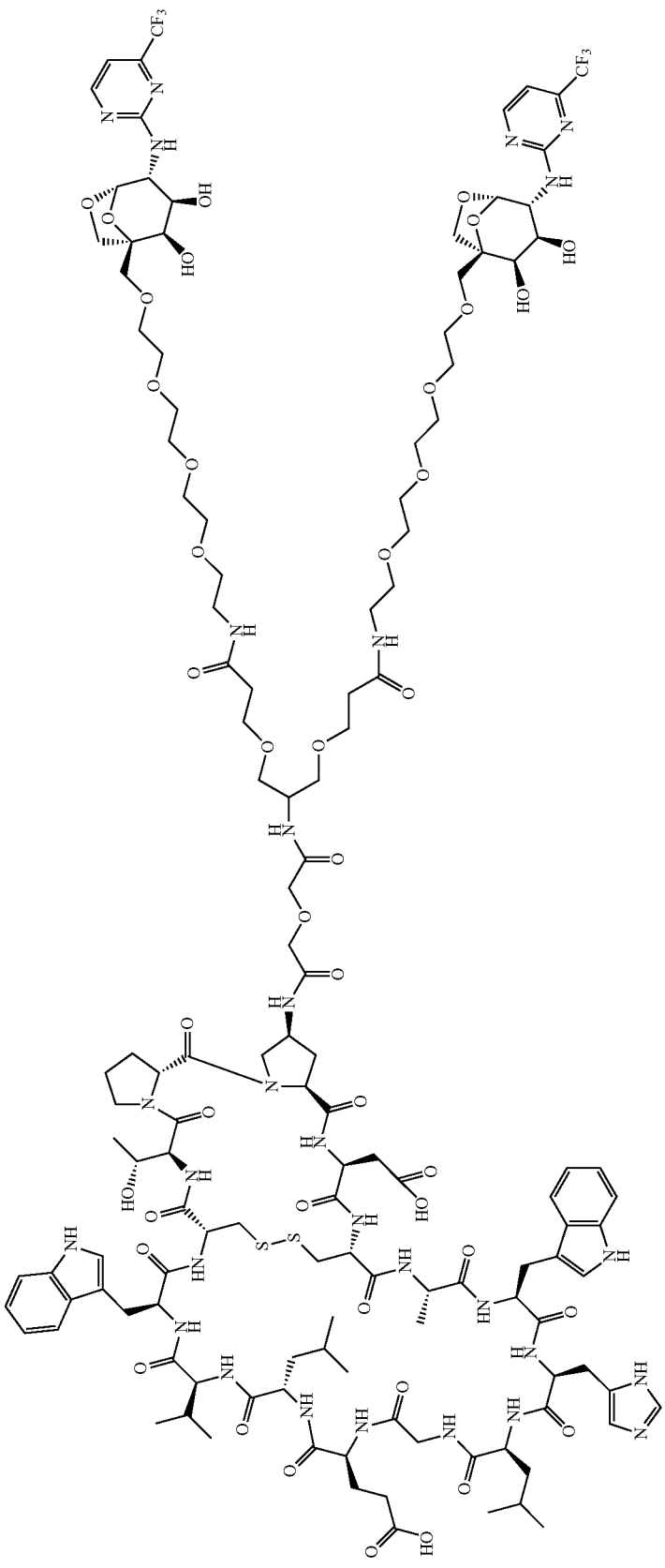

-continued
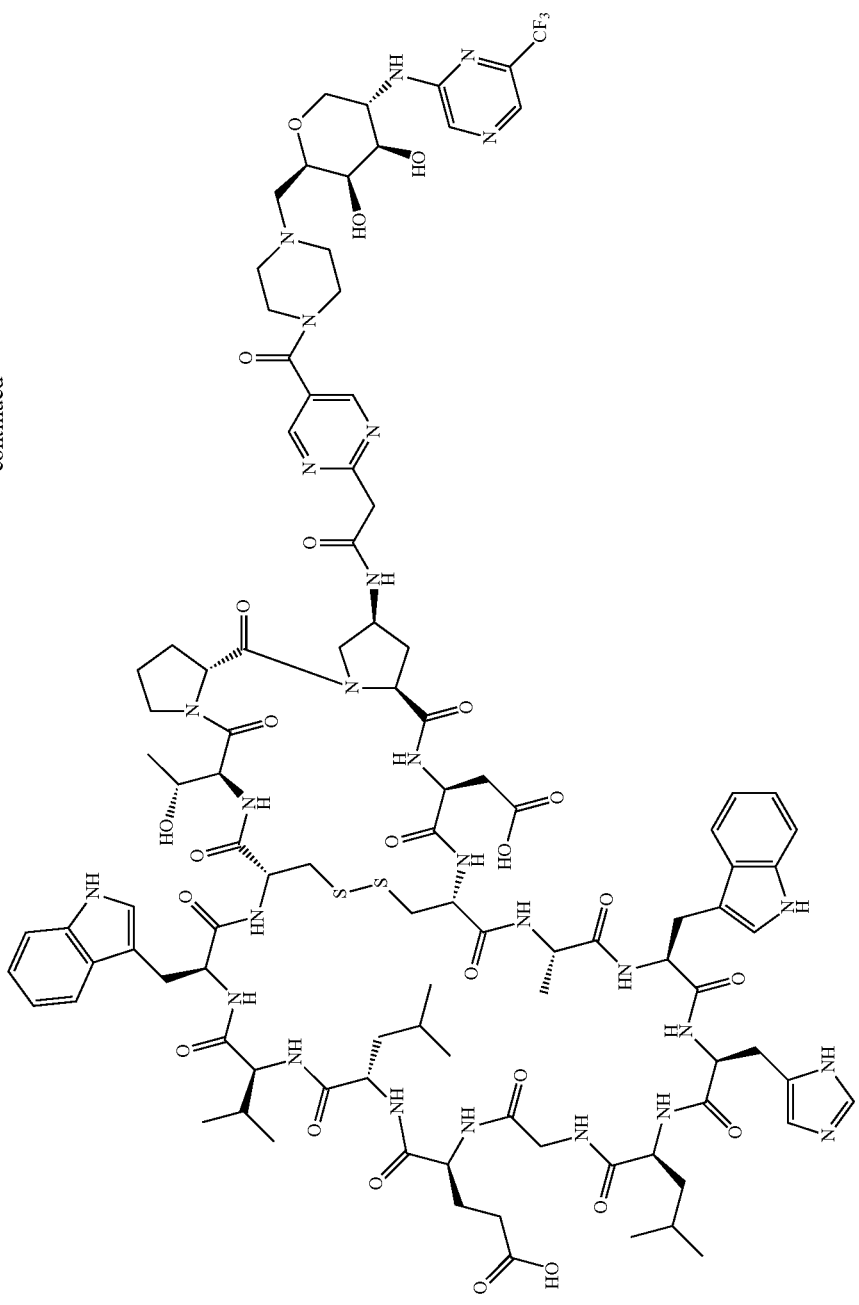

-continued
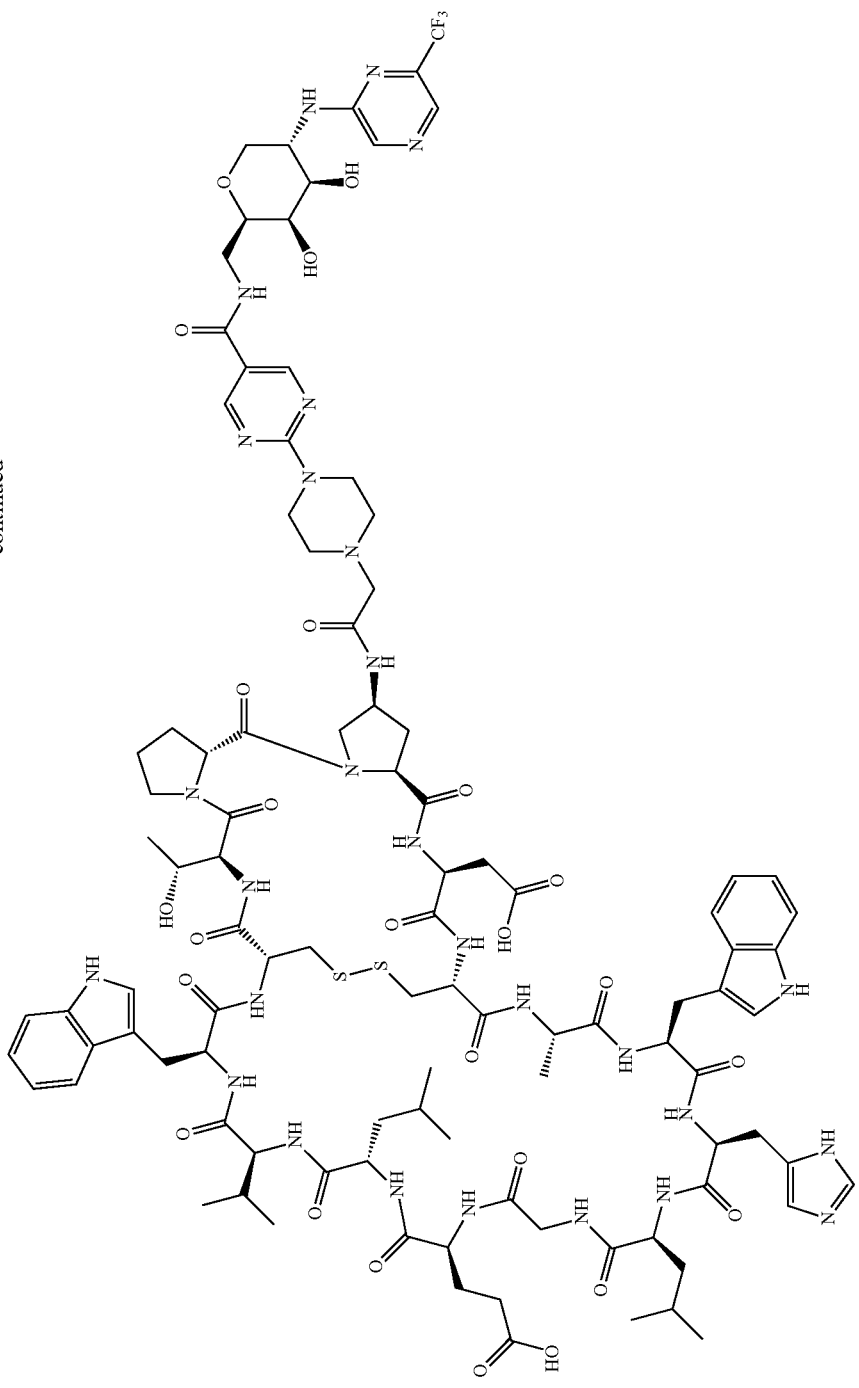

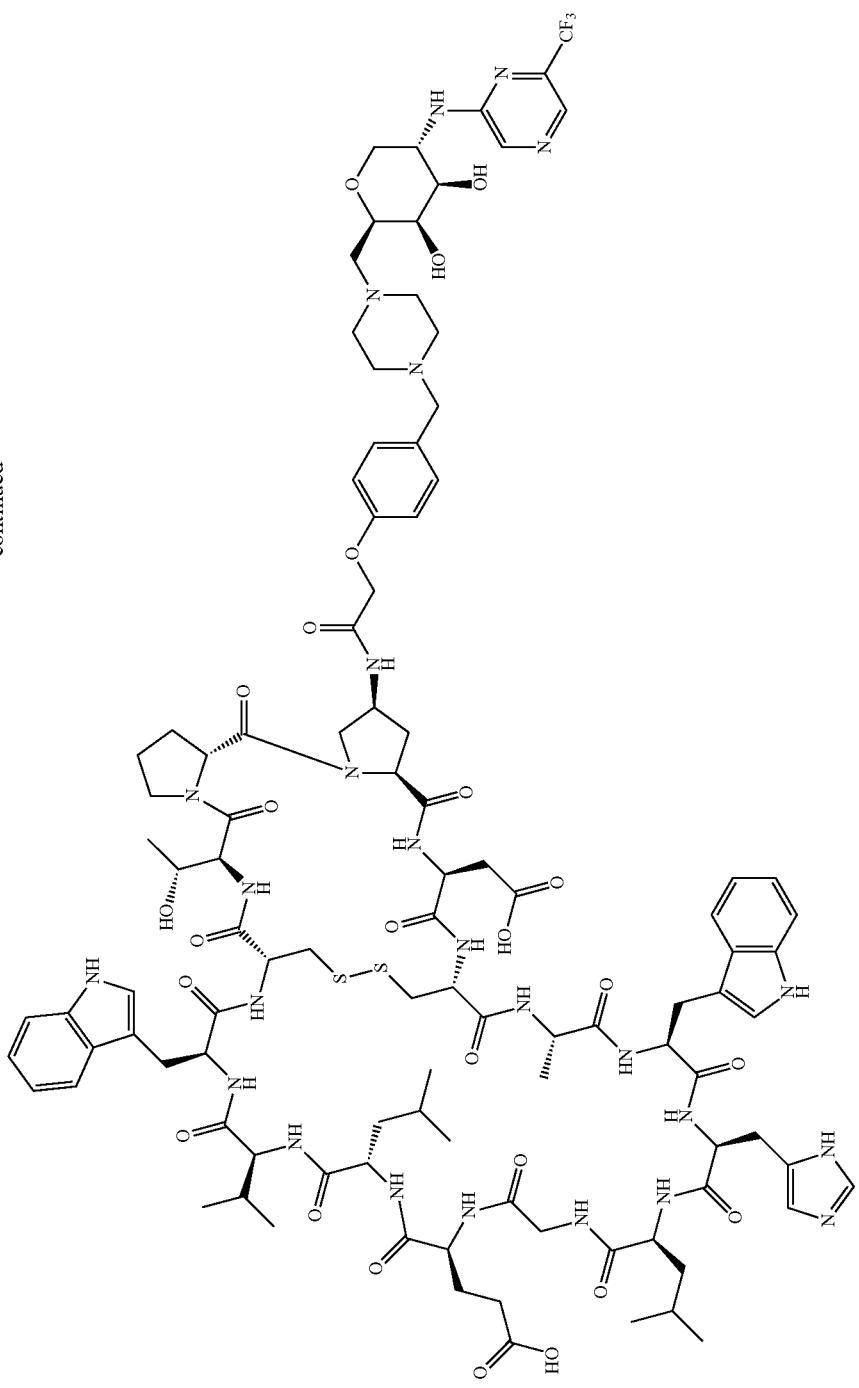

-continued
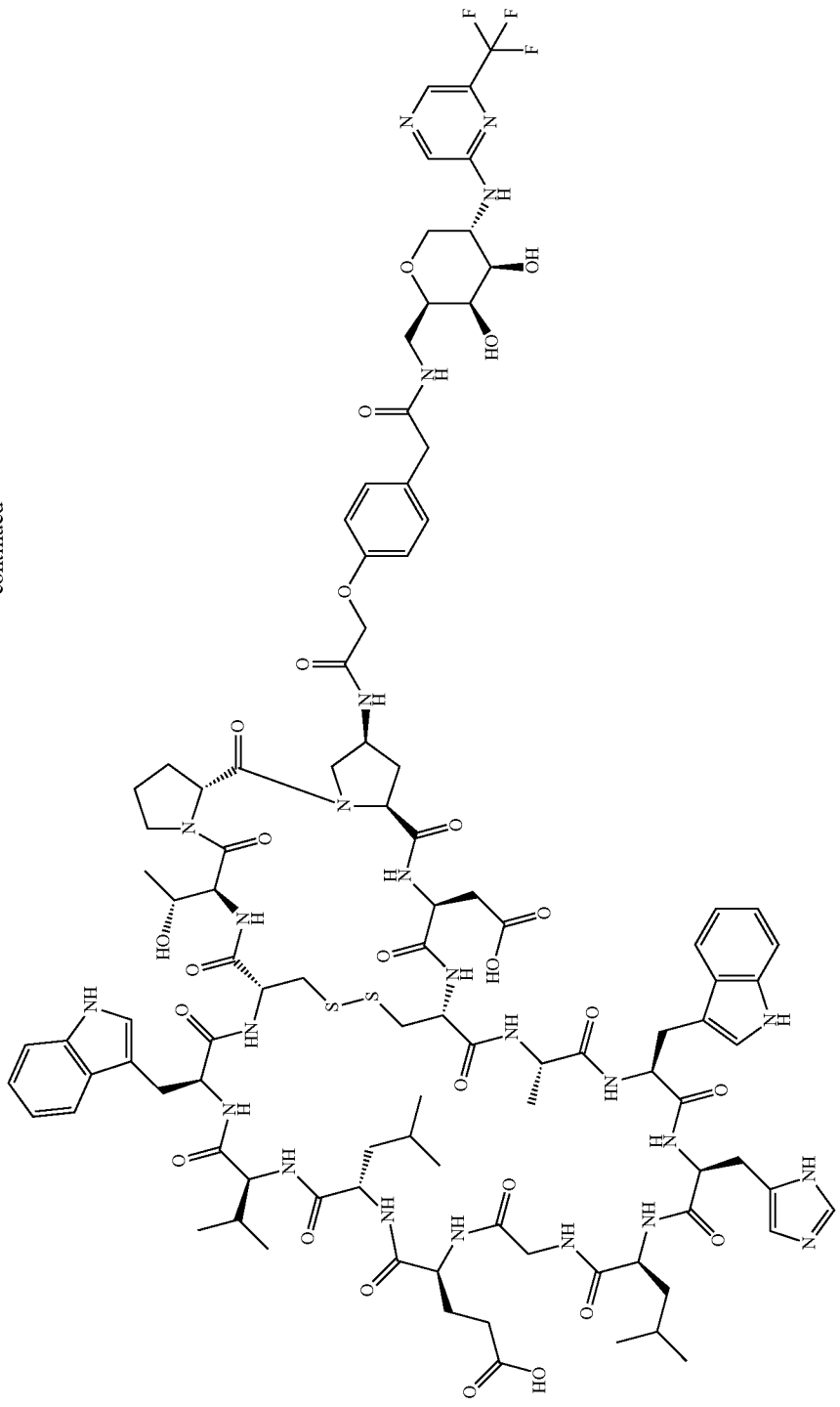

-continued
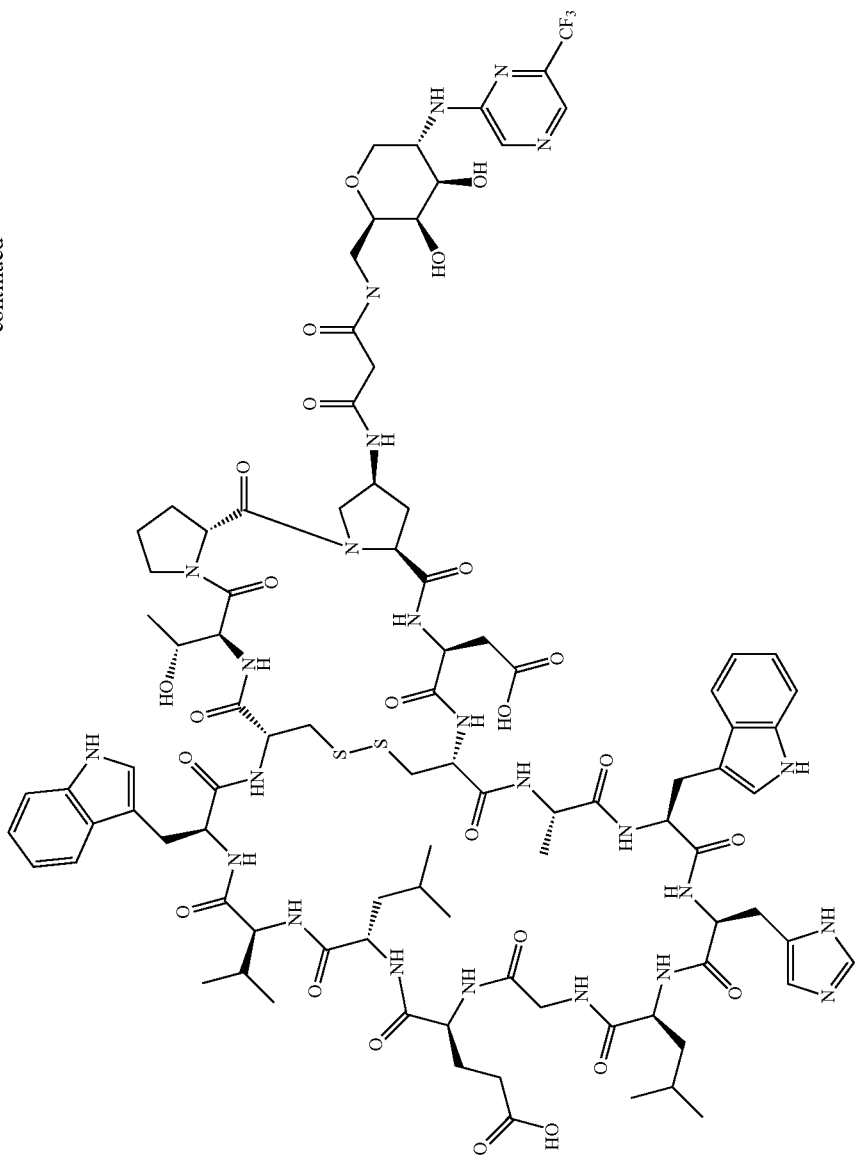

-continued
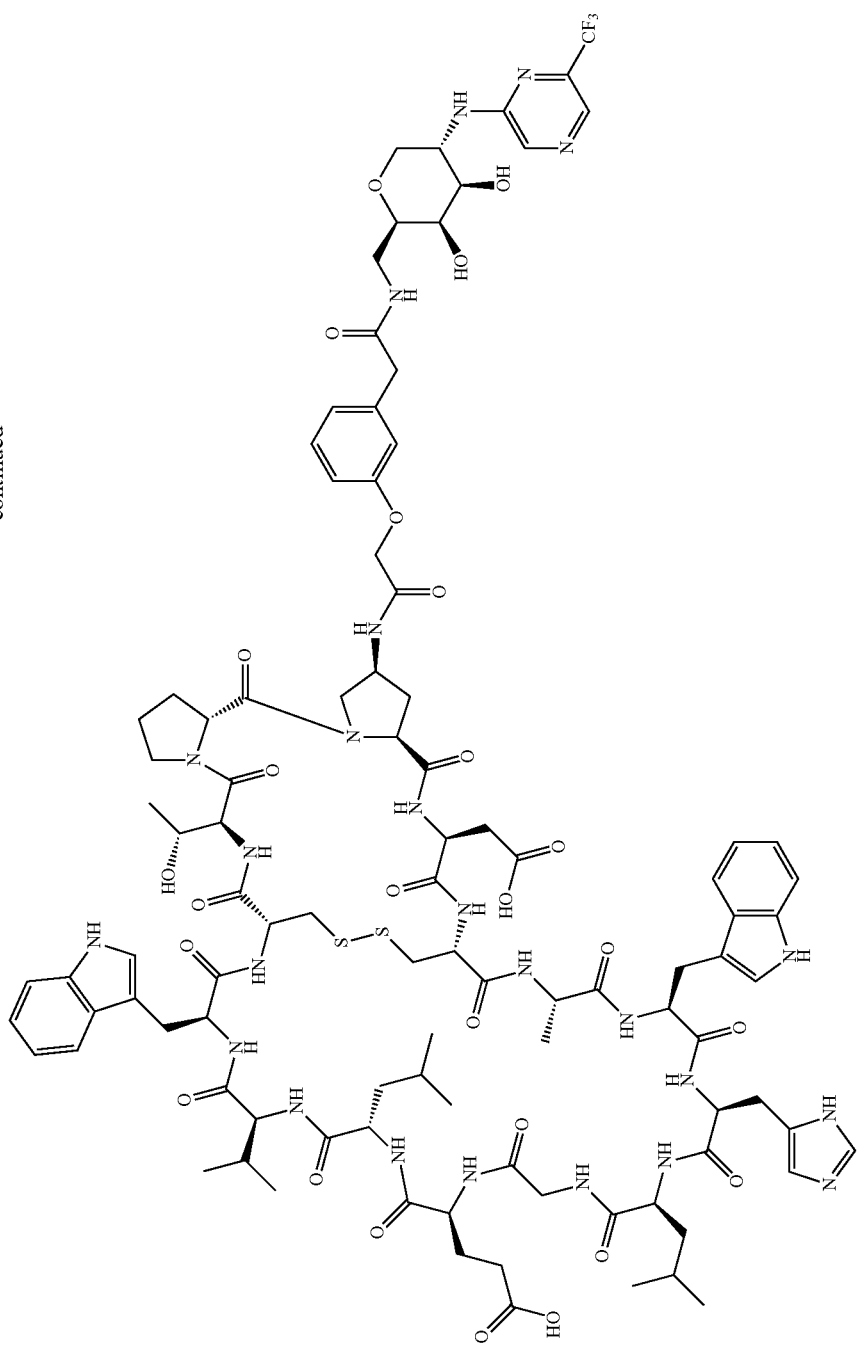

-continued
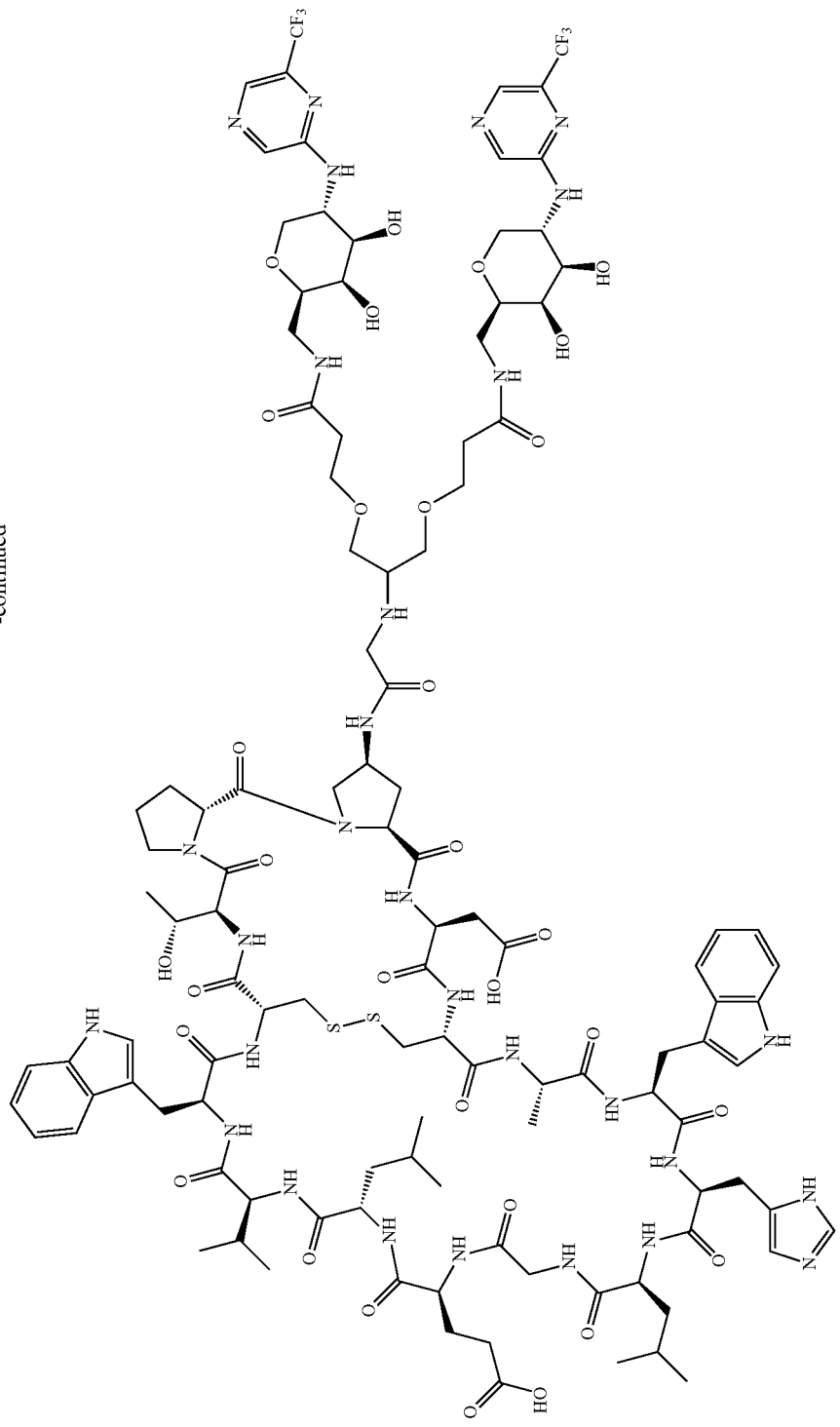

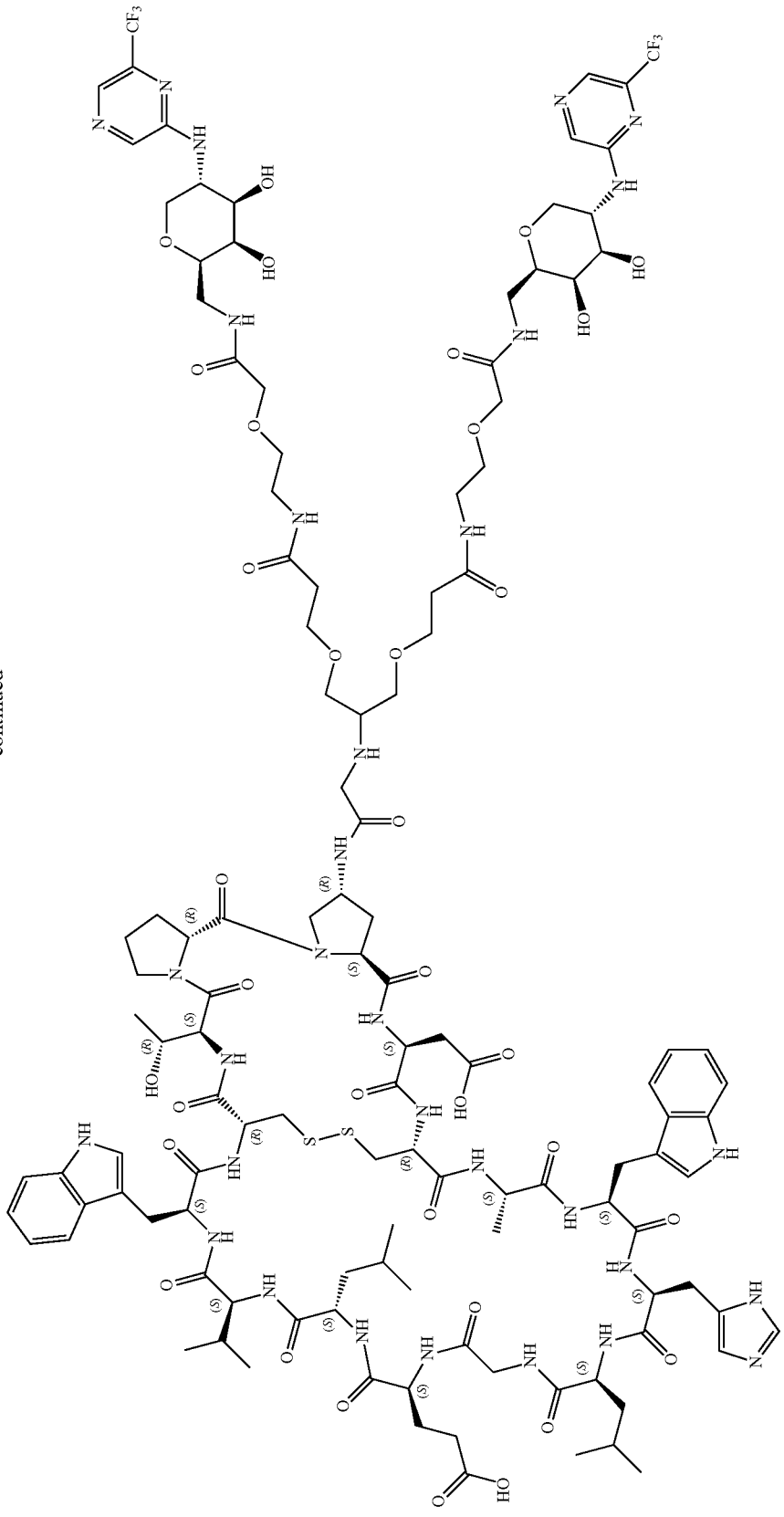

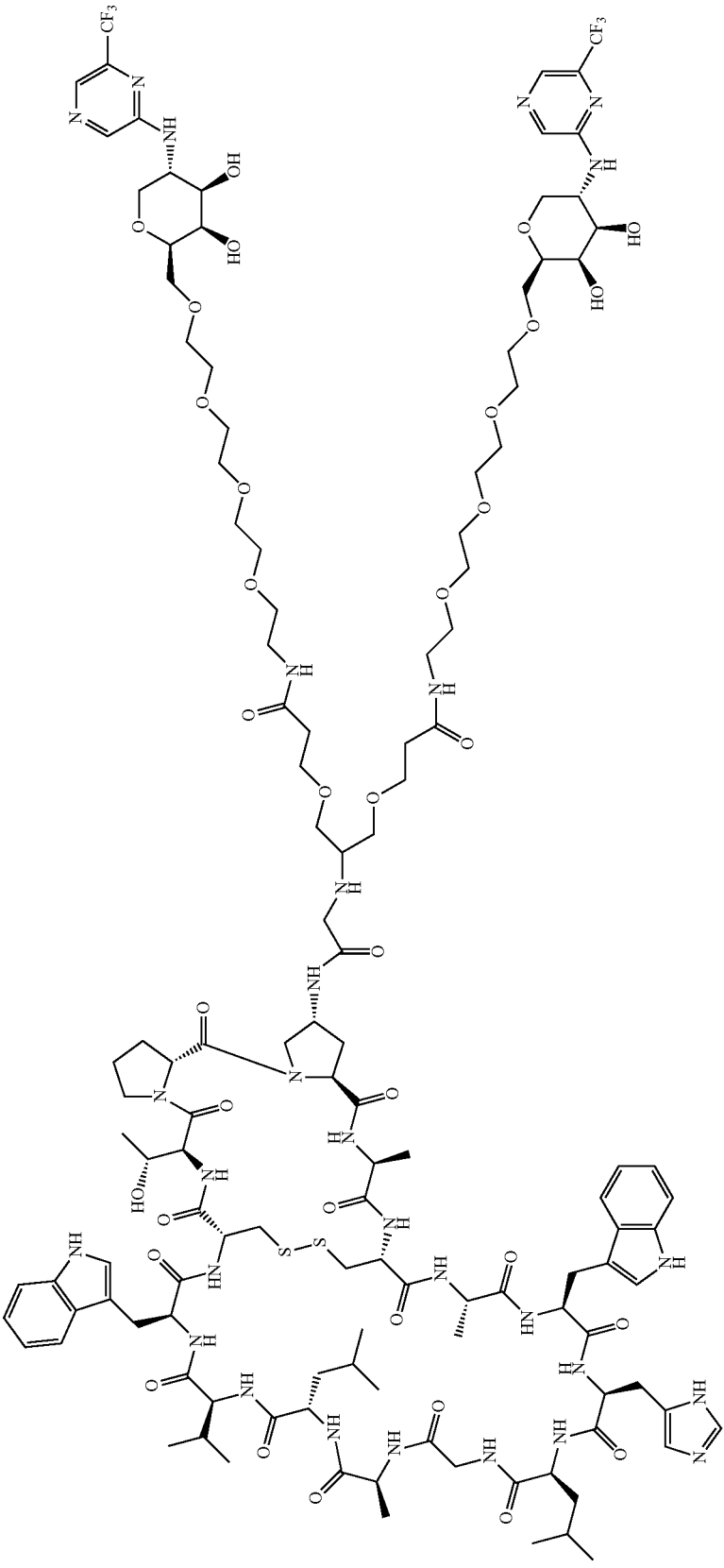

-continued
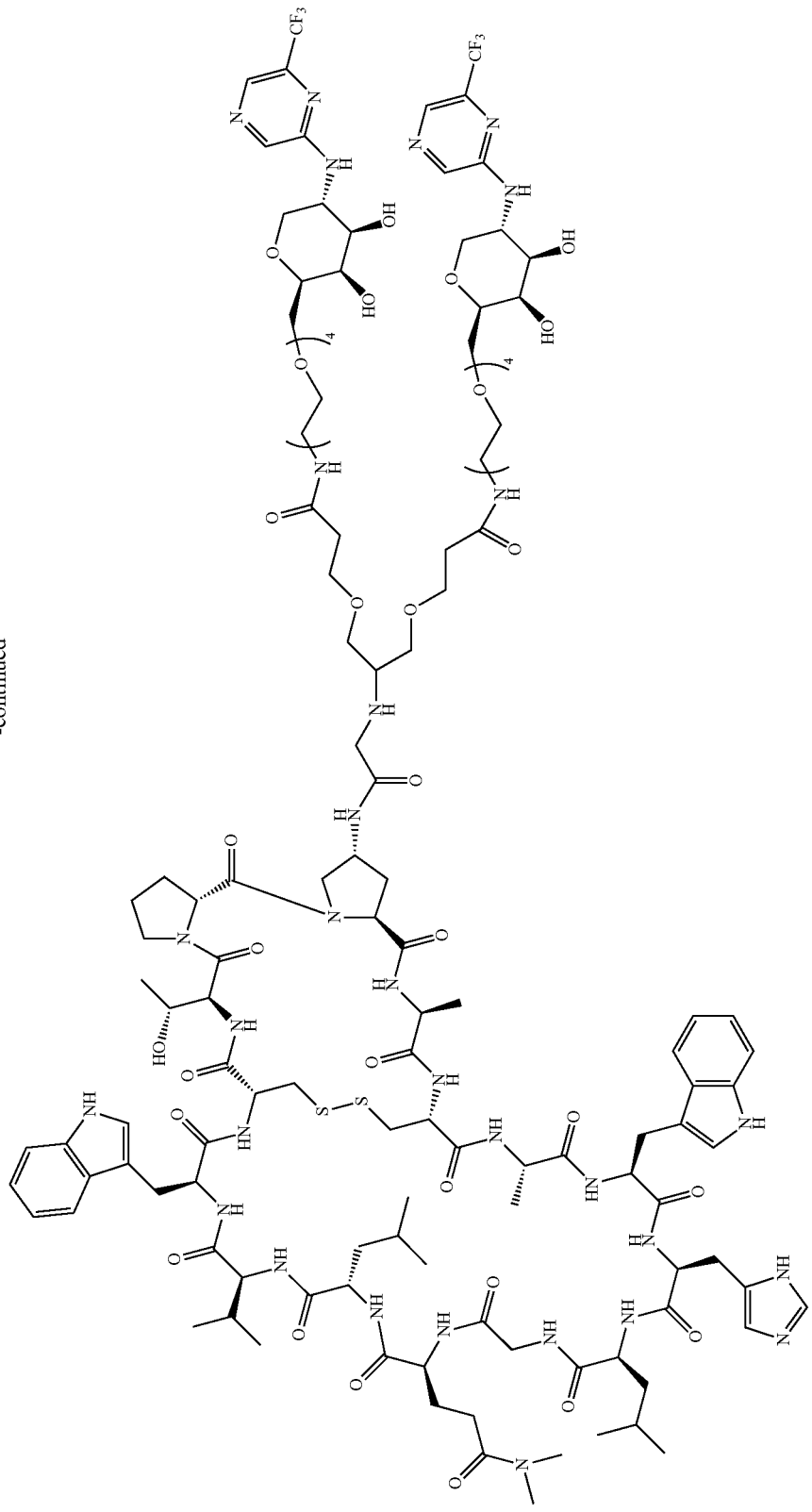

-continued
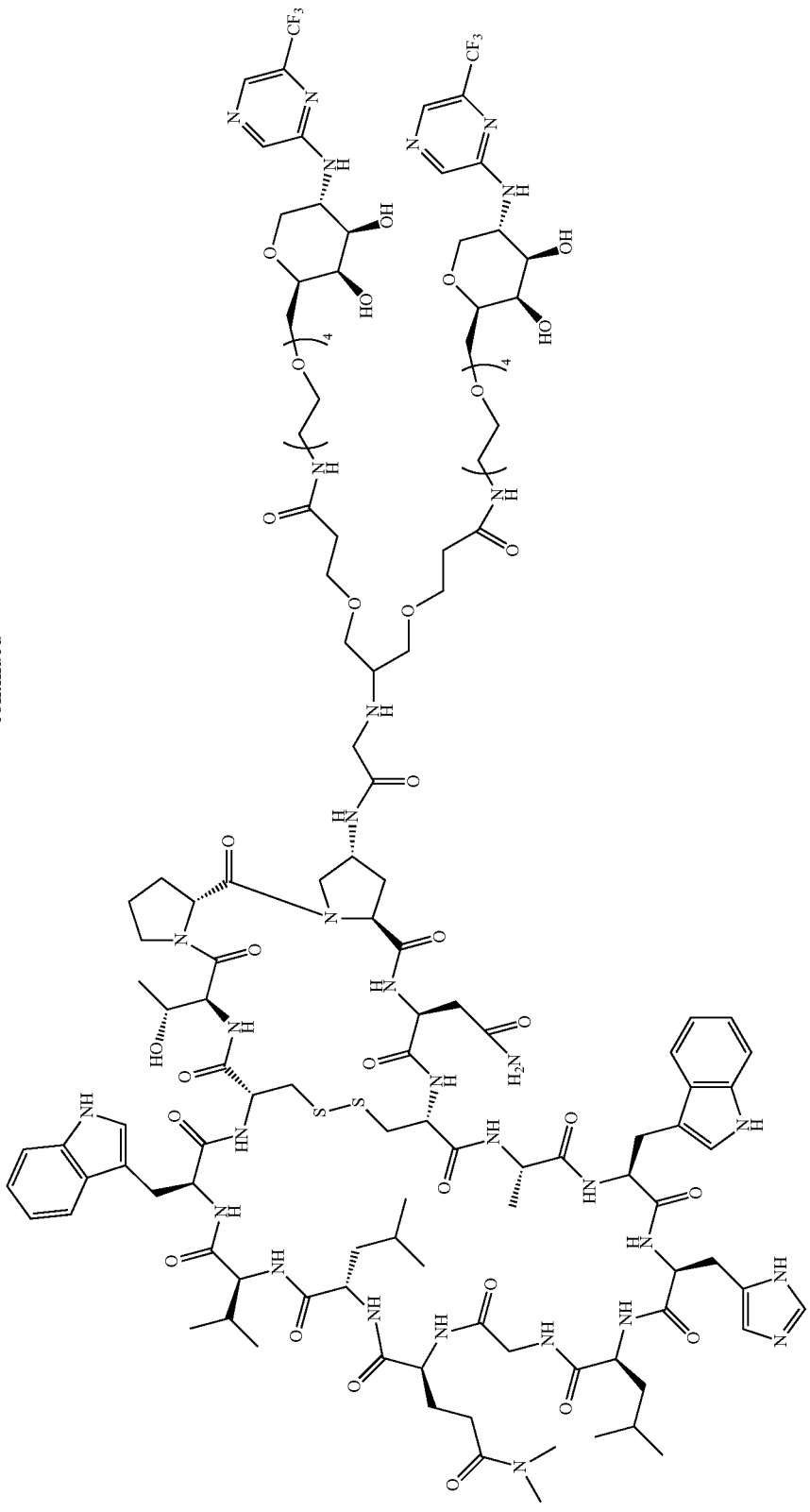

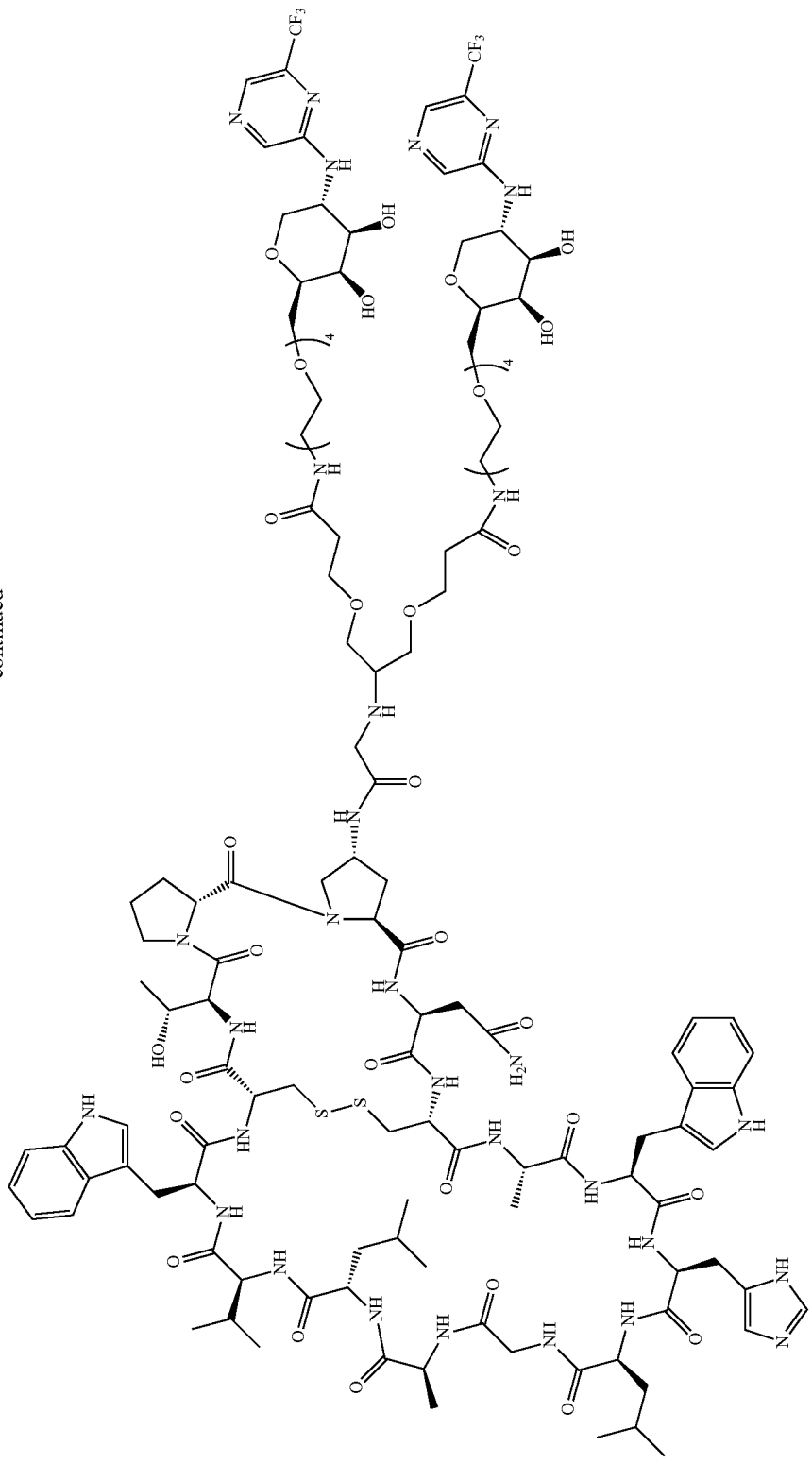

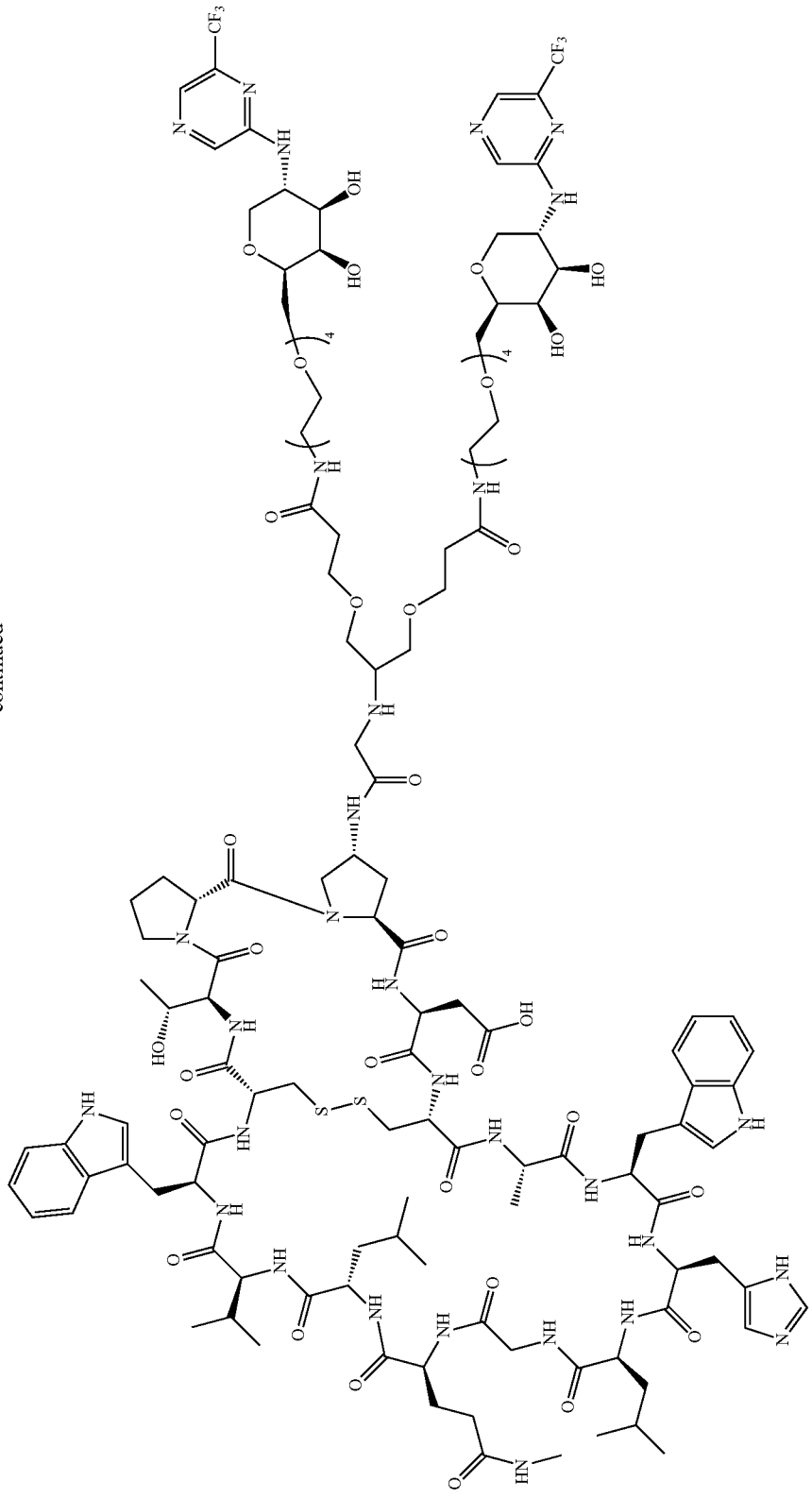

1615 1616
-continued
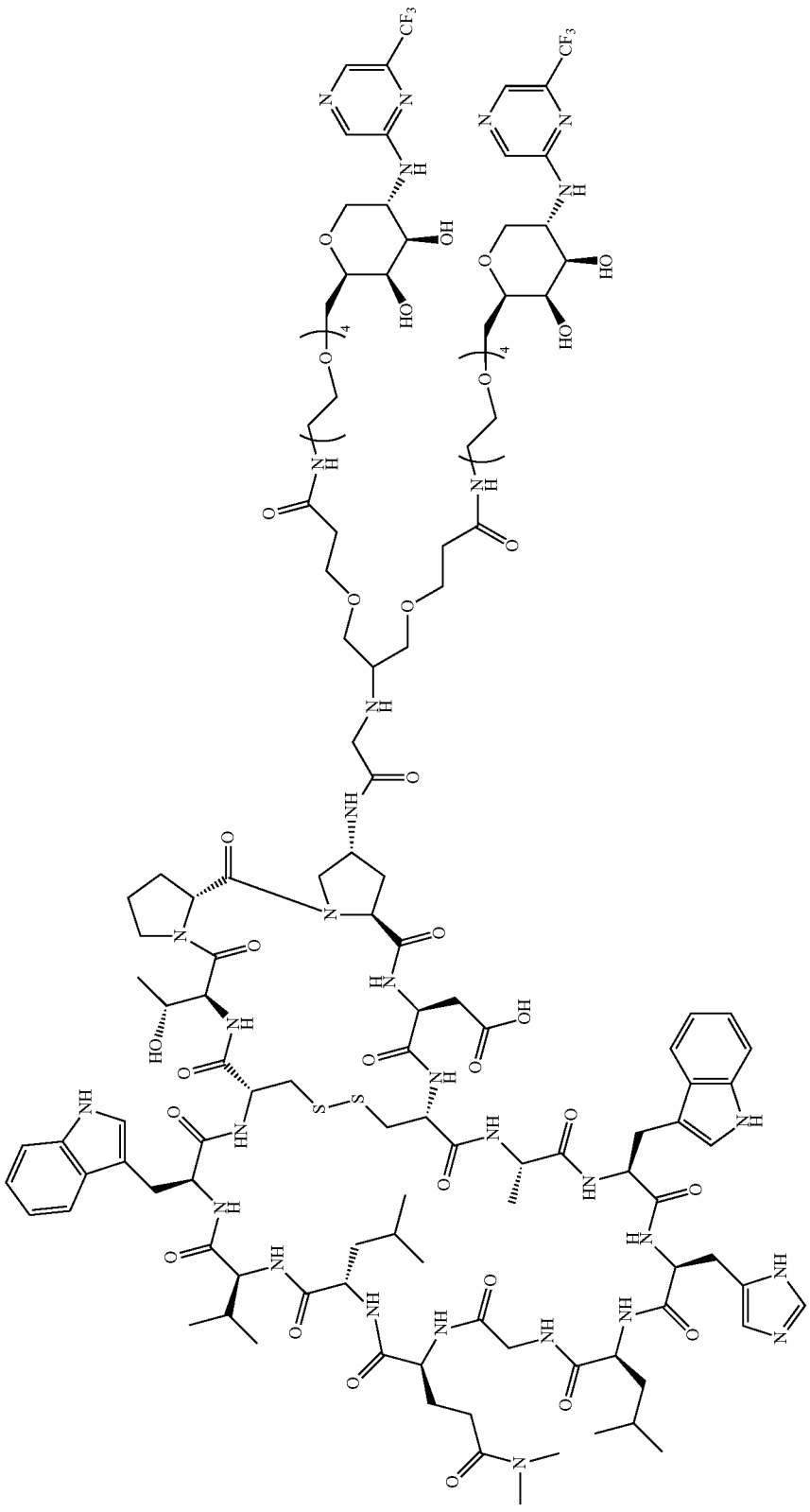

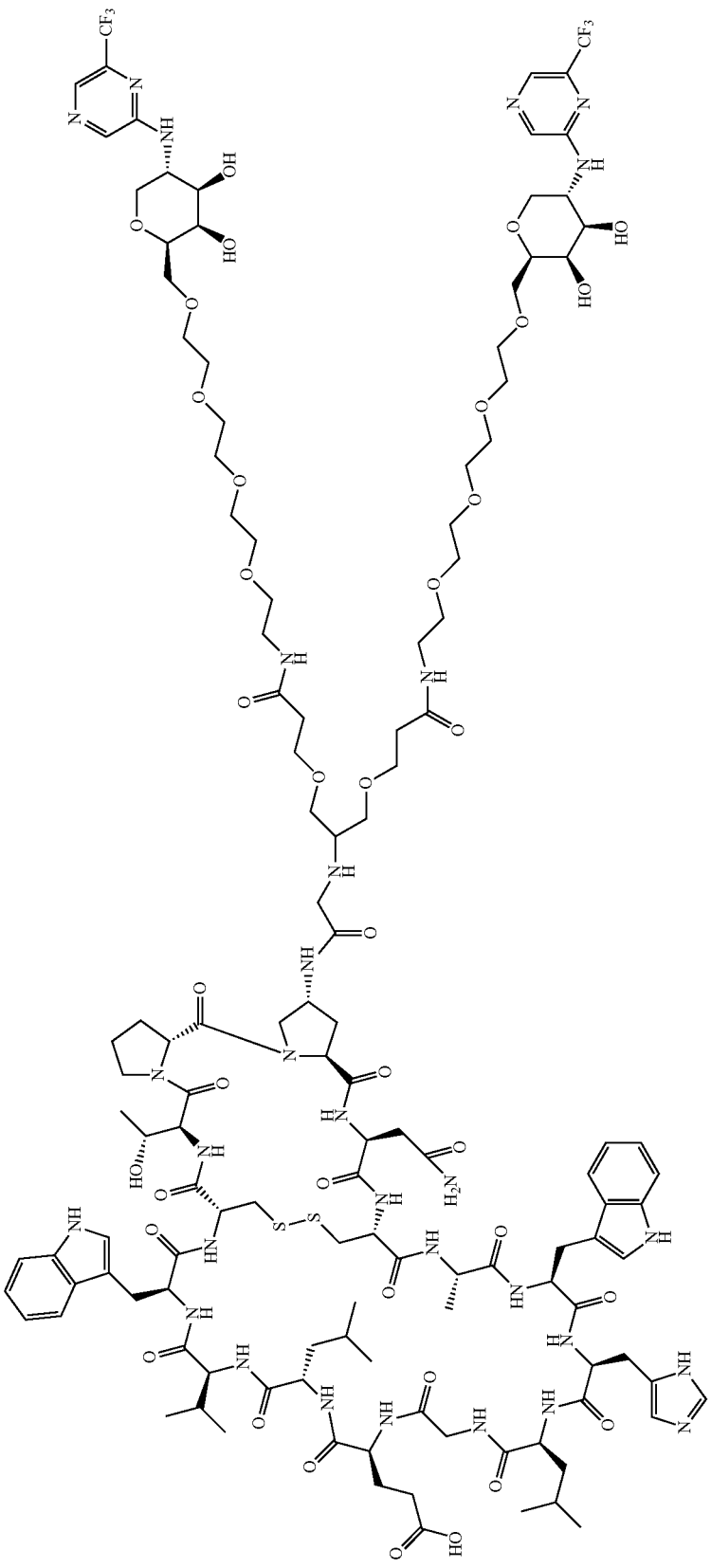

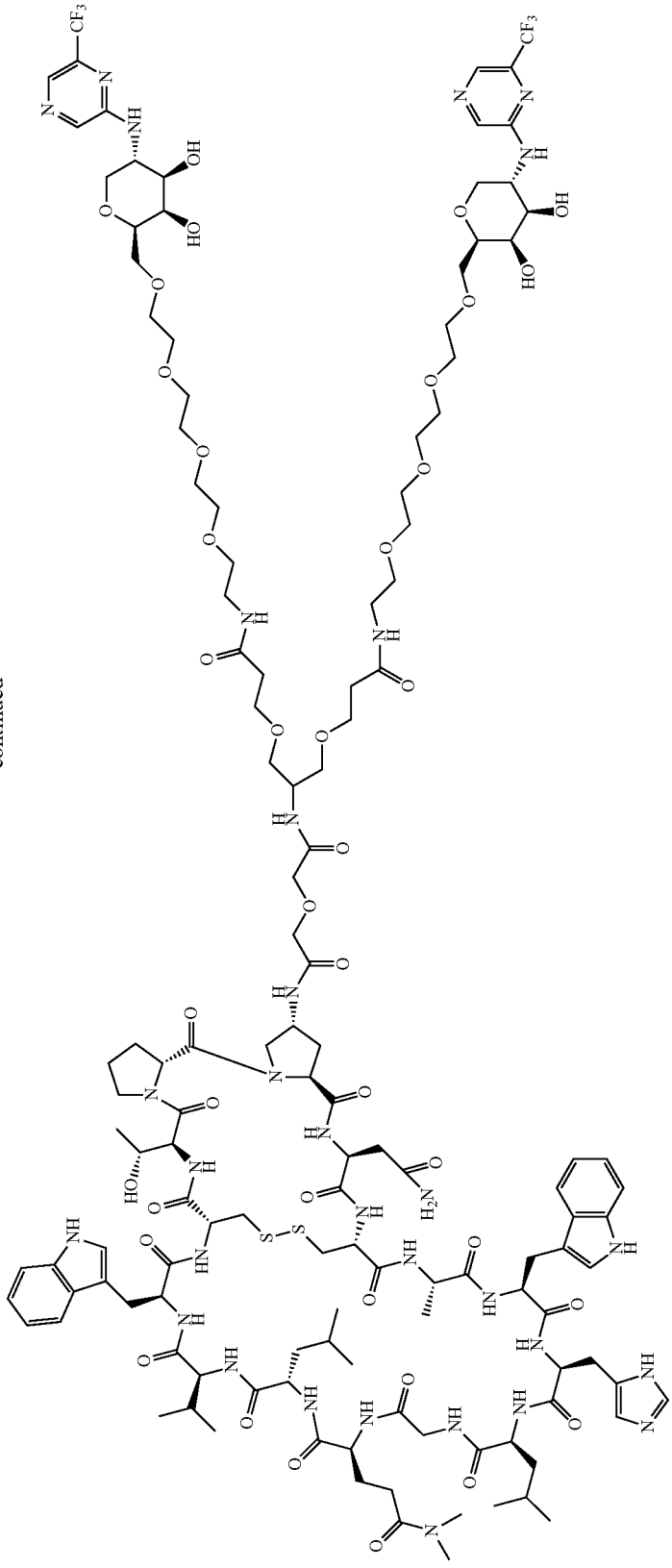

-continued
1621    1622
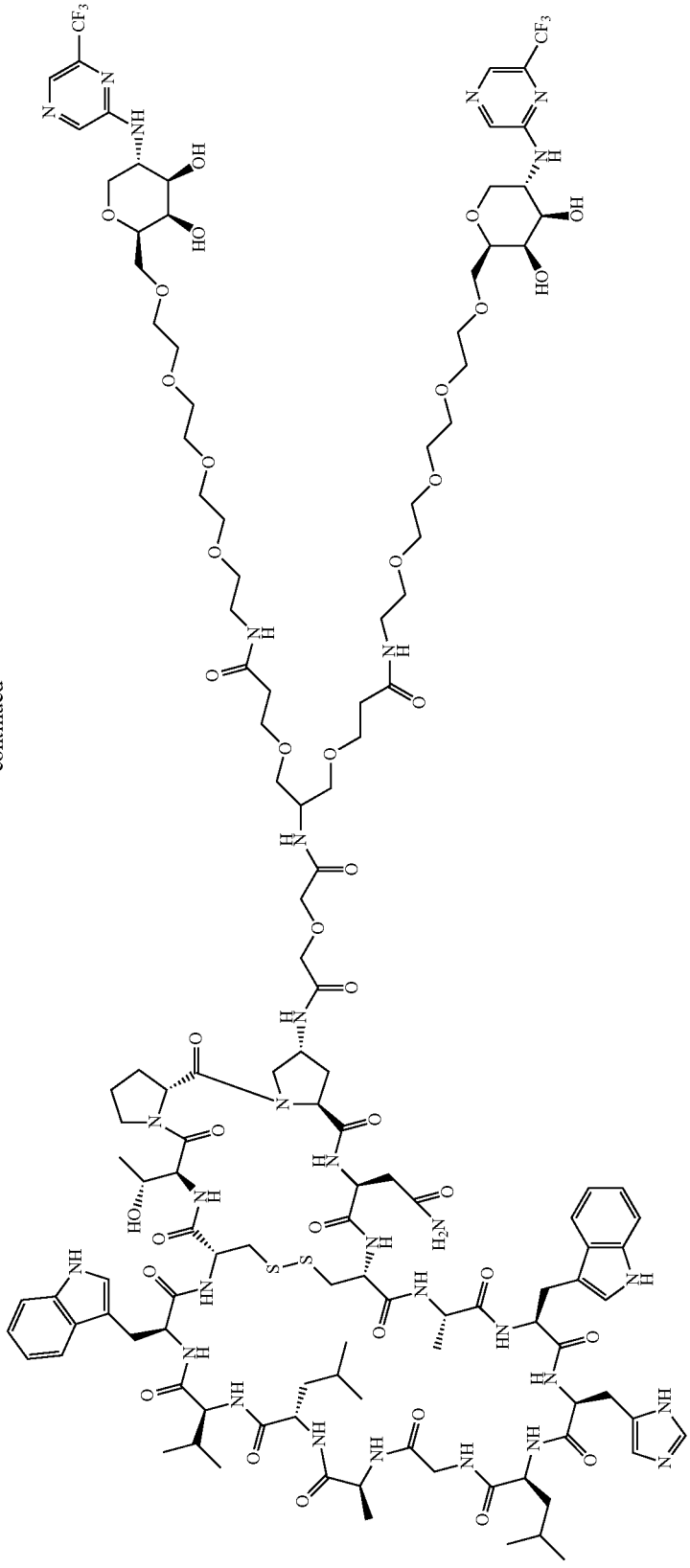

1623 1624
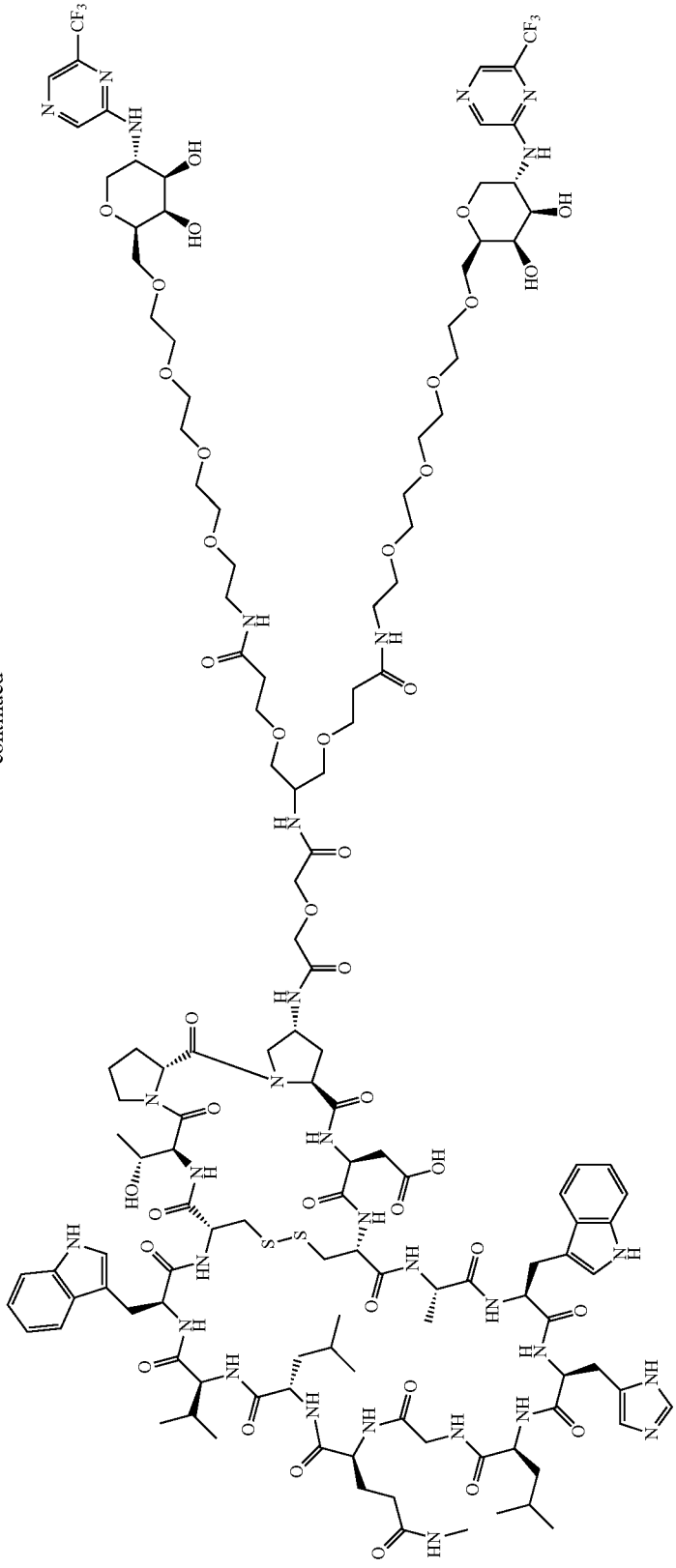
-continued

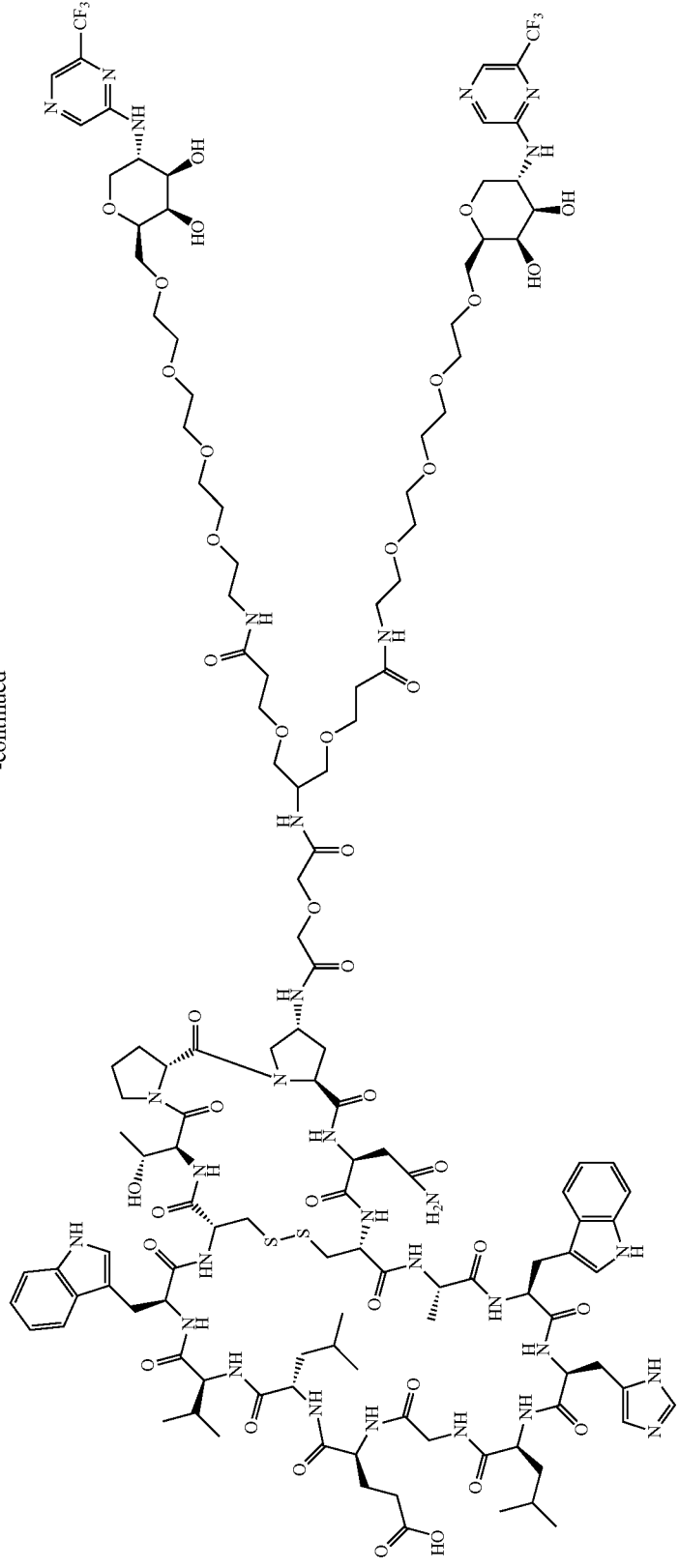

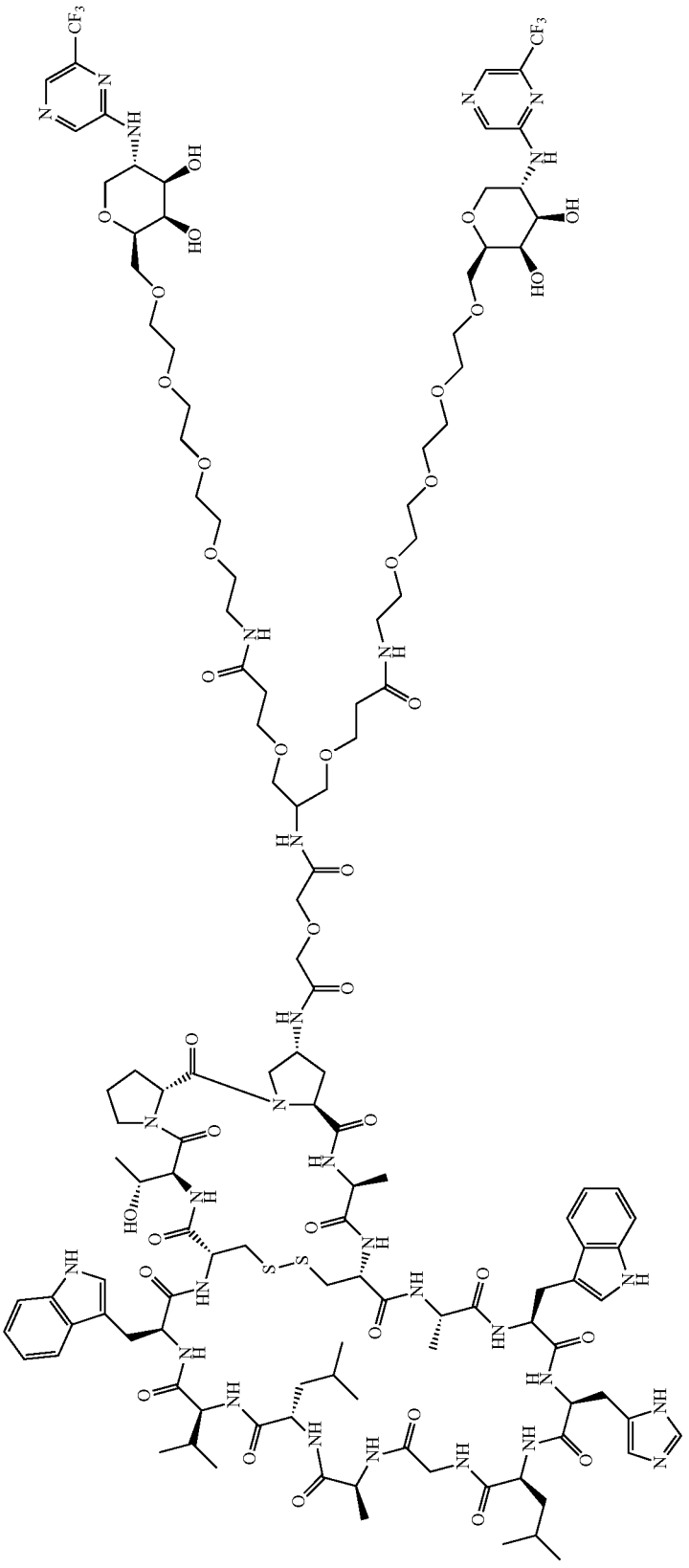

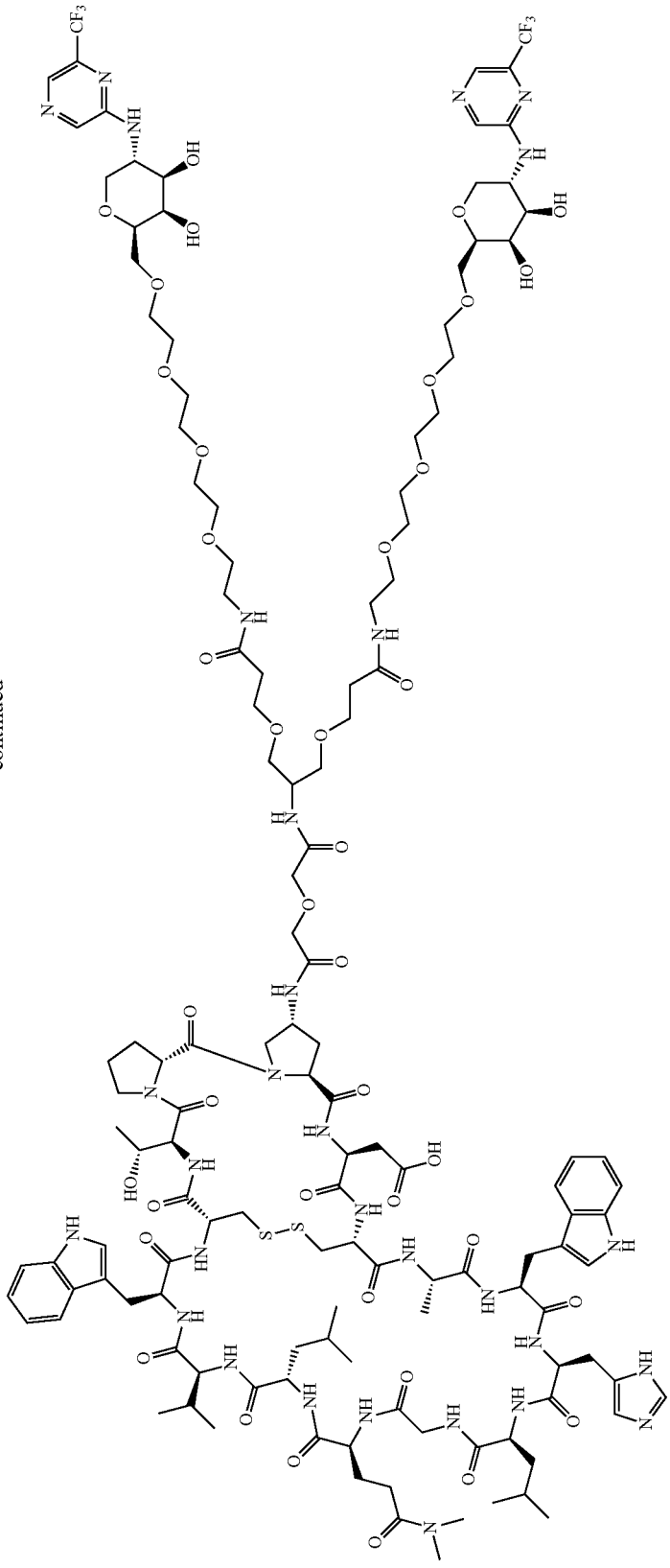

1631 1632
-continued
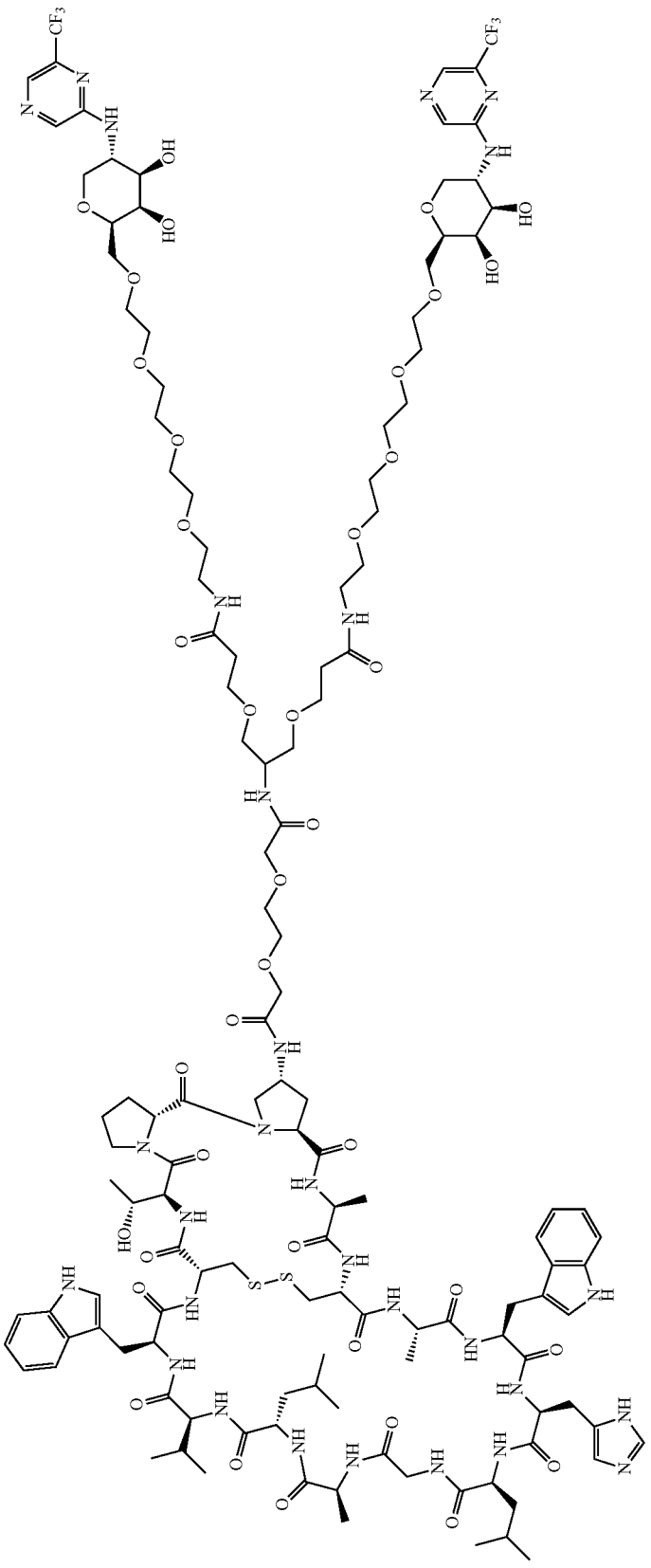

1633 1634
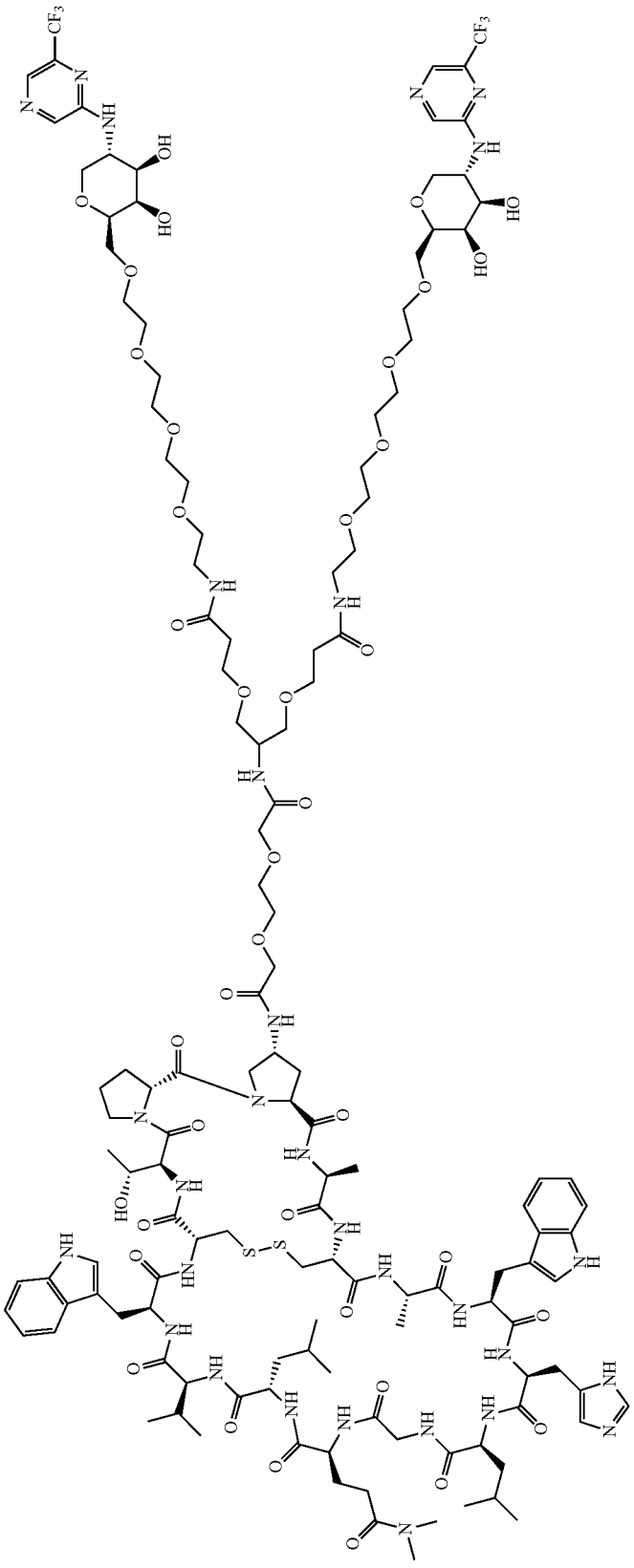

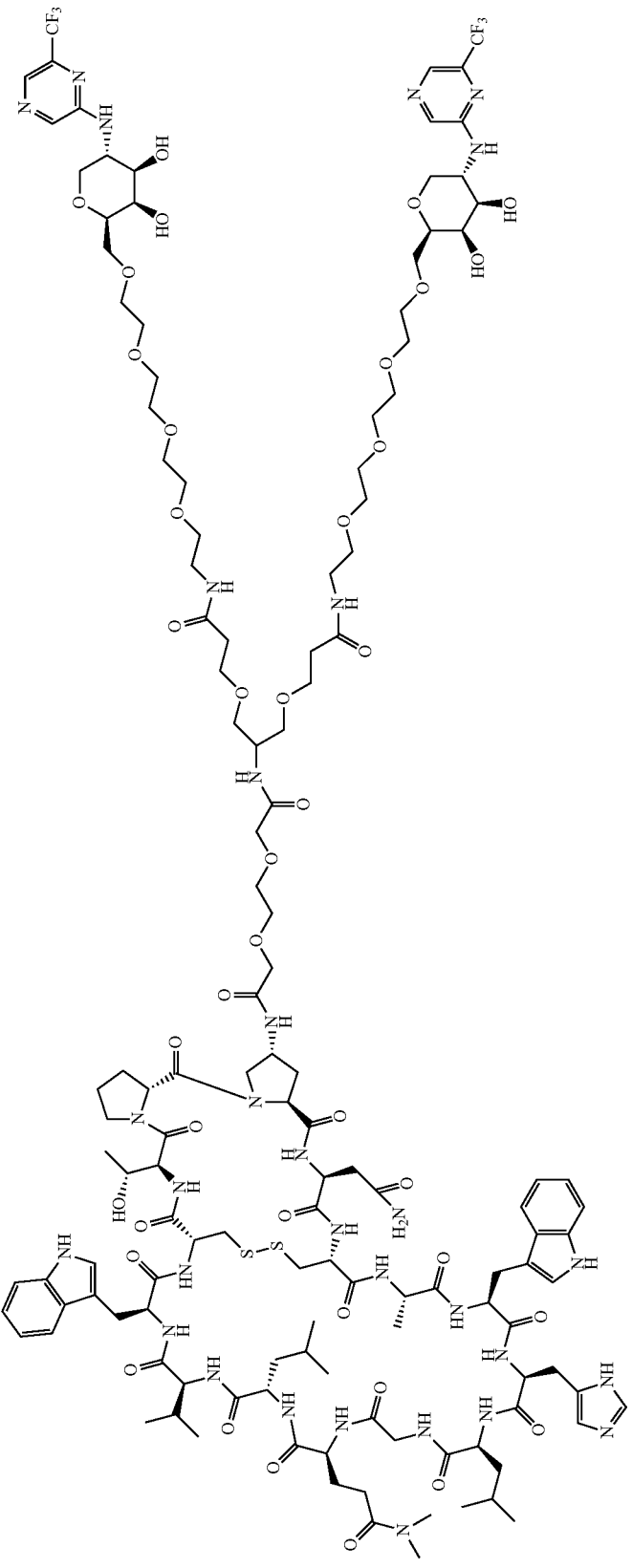

-continued
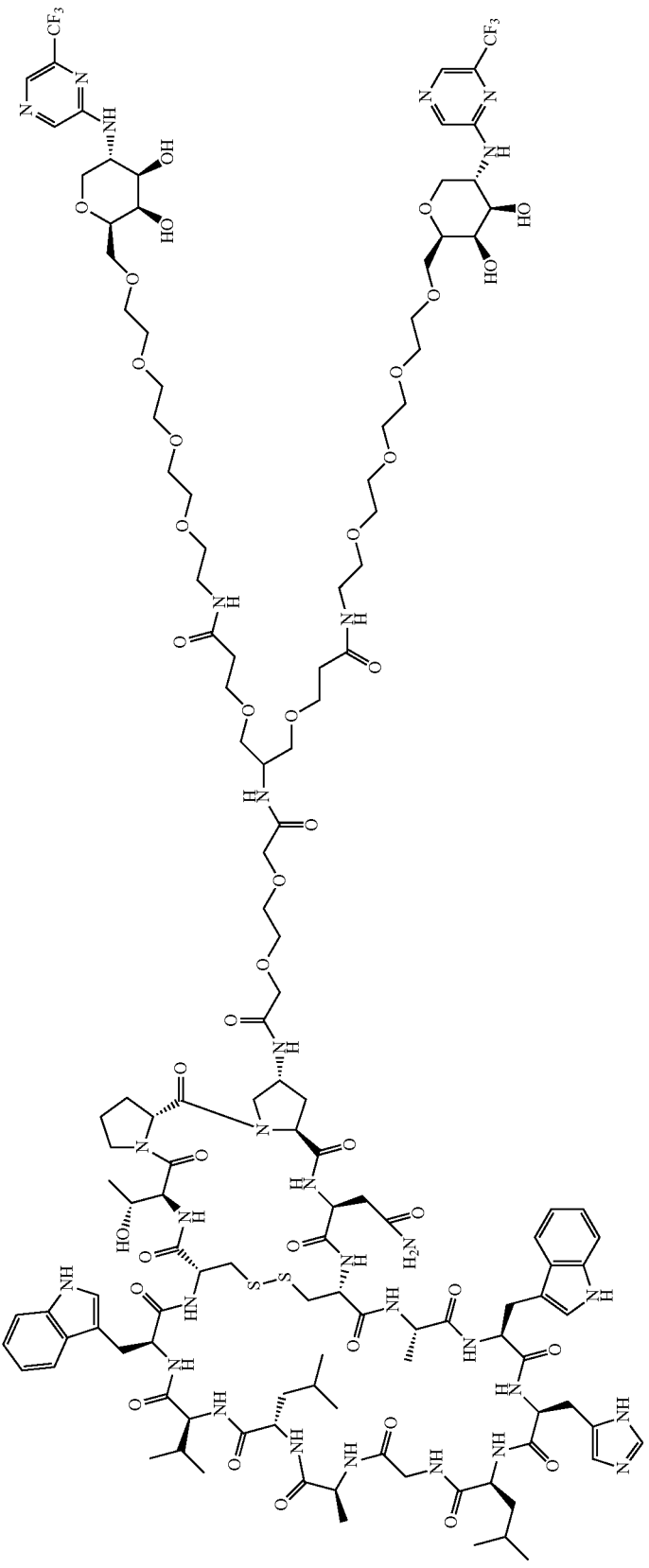

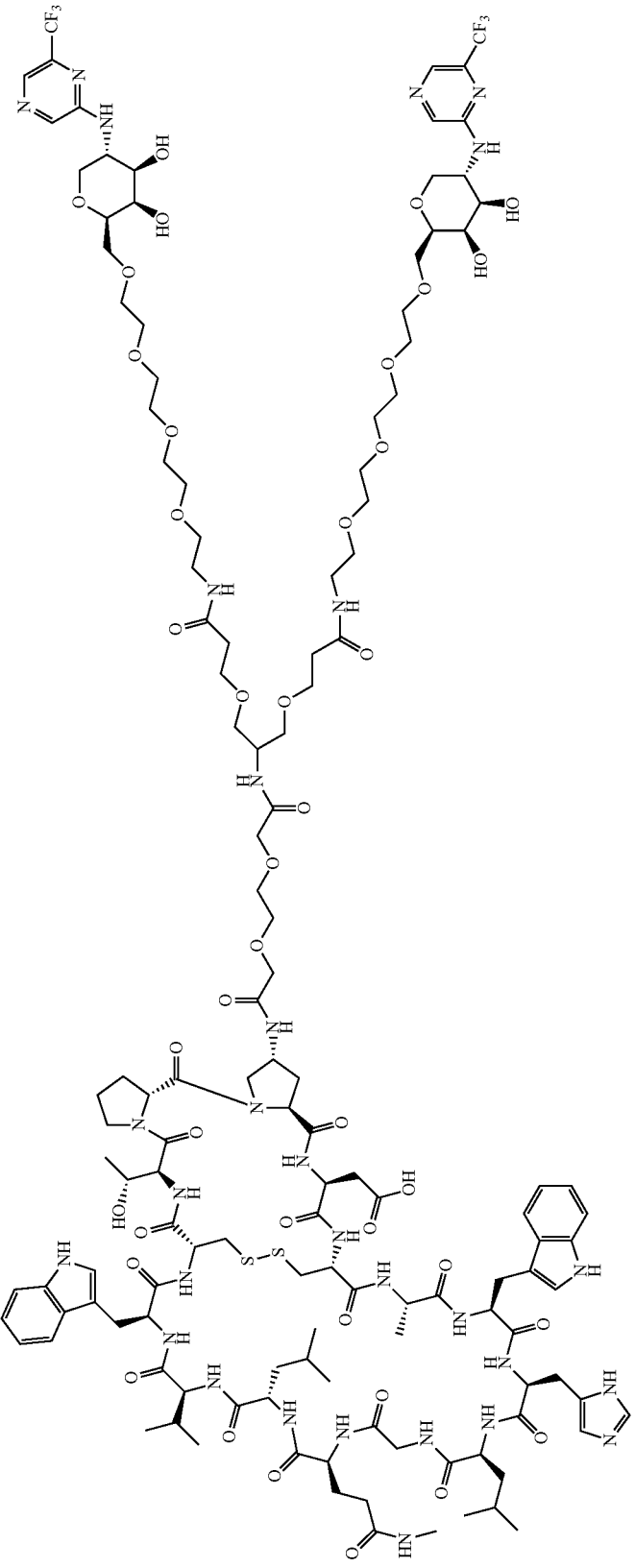

1641 1642
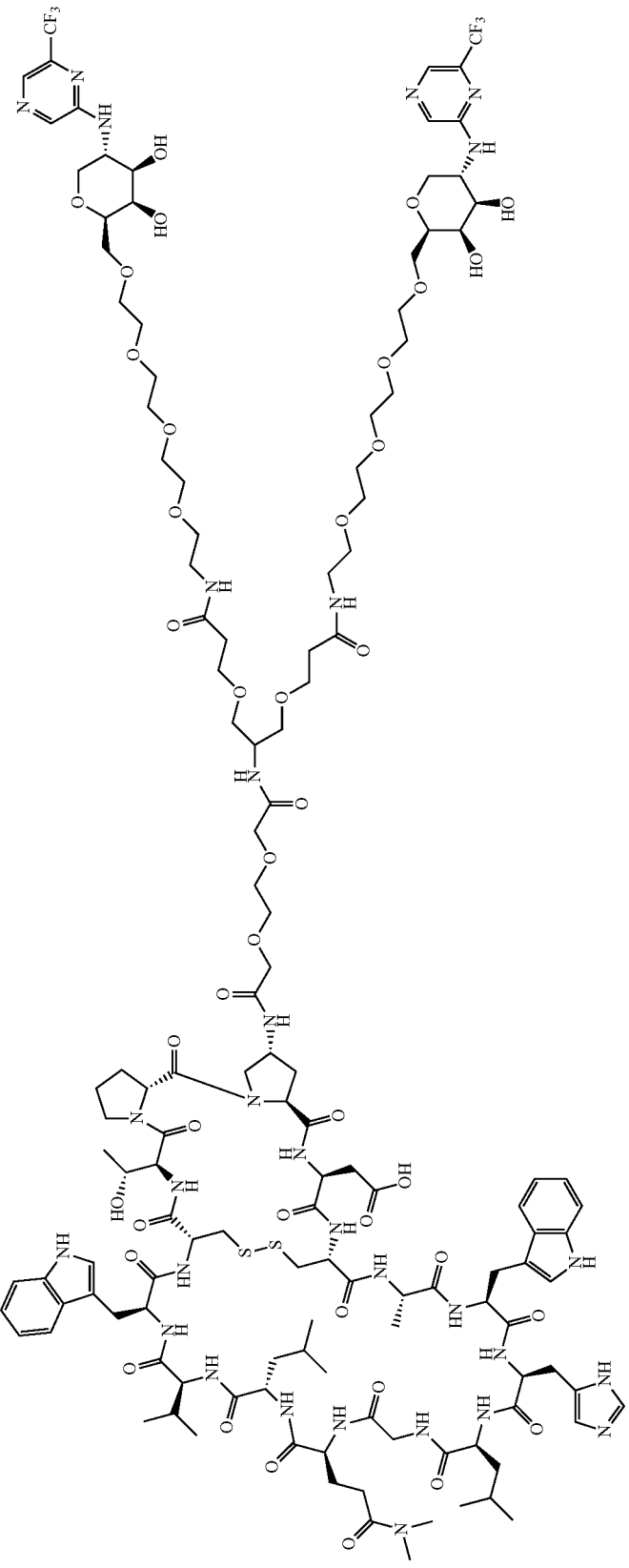

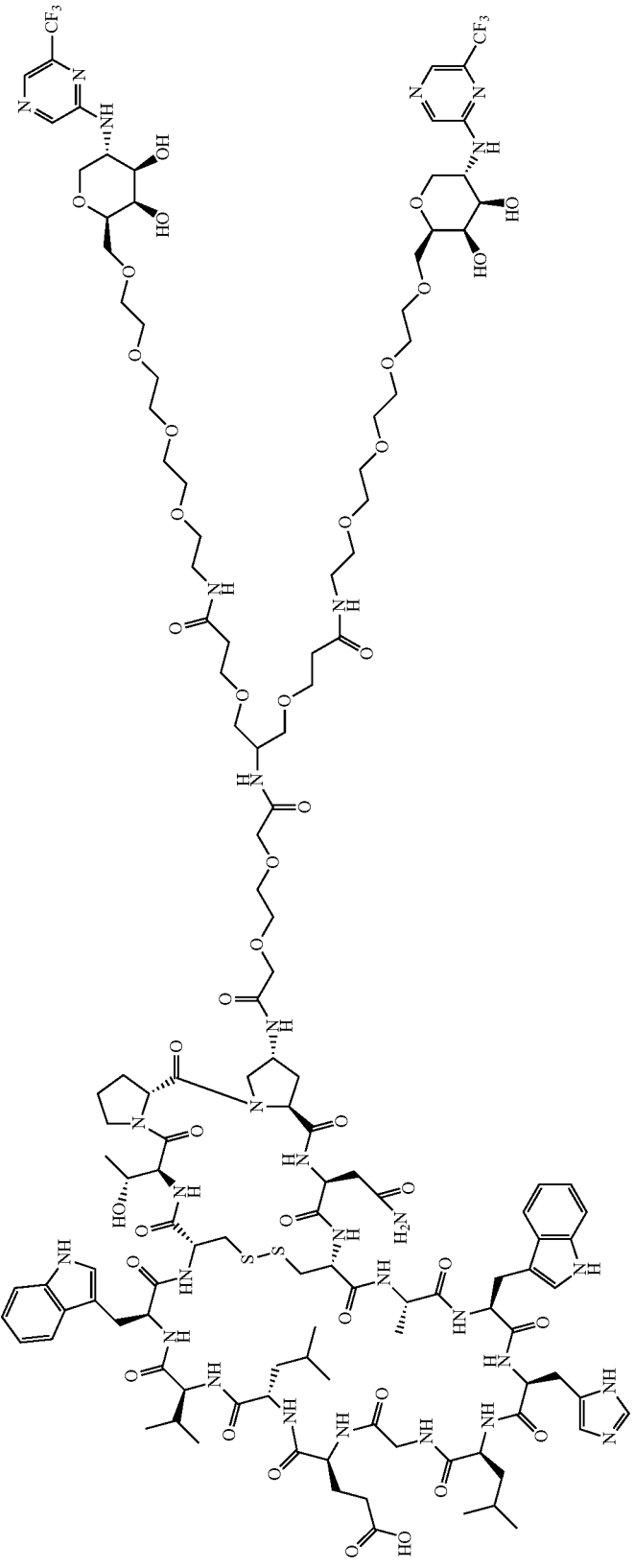

-continued
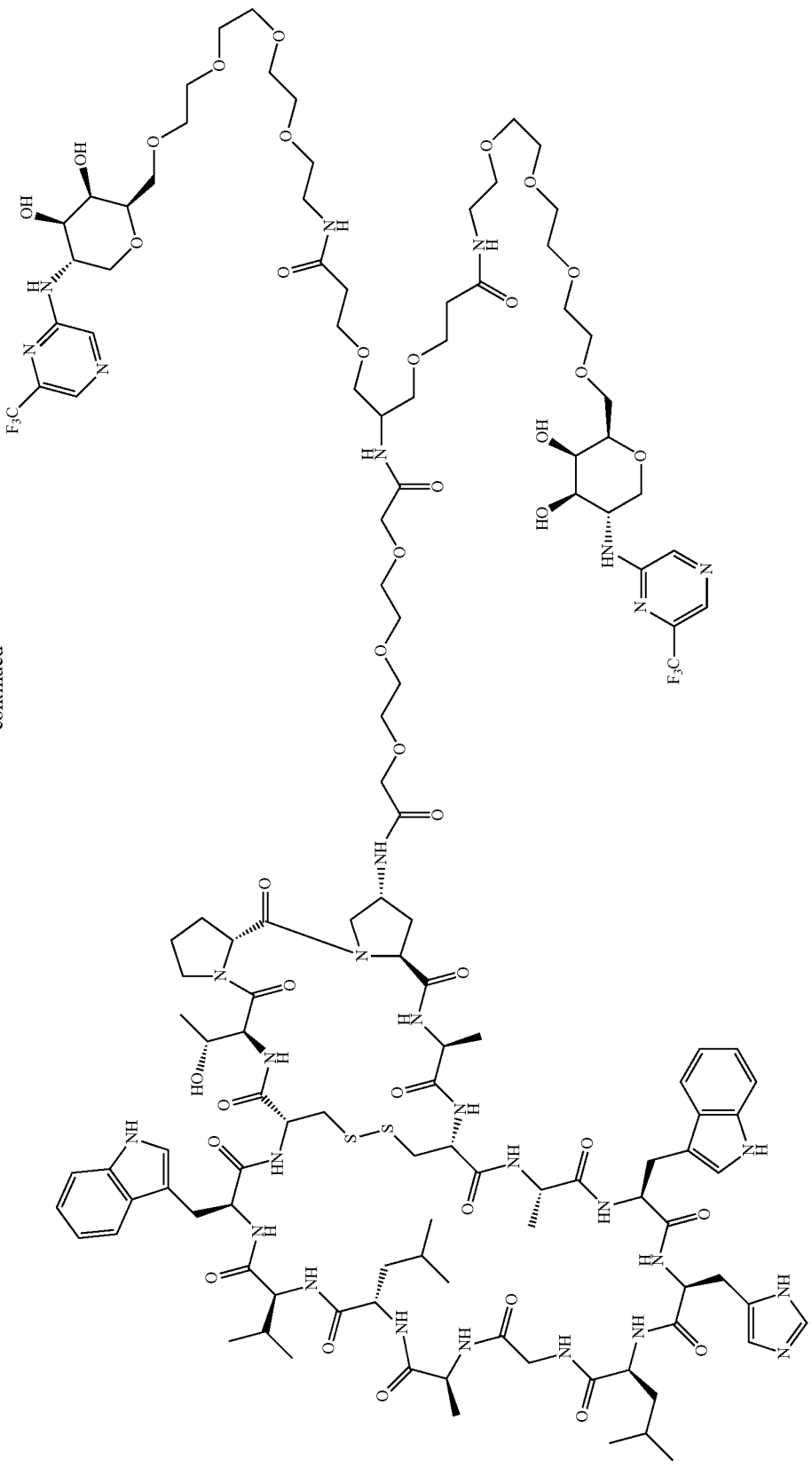

-continued
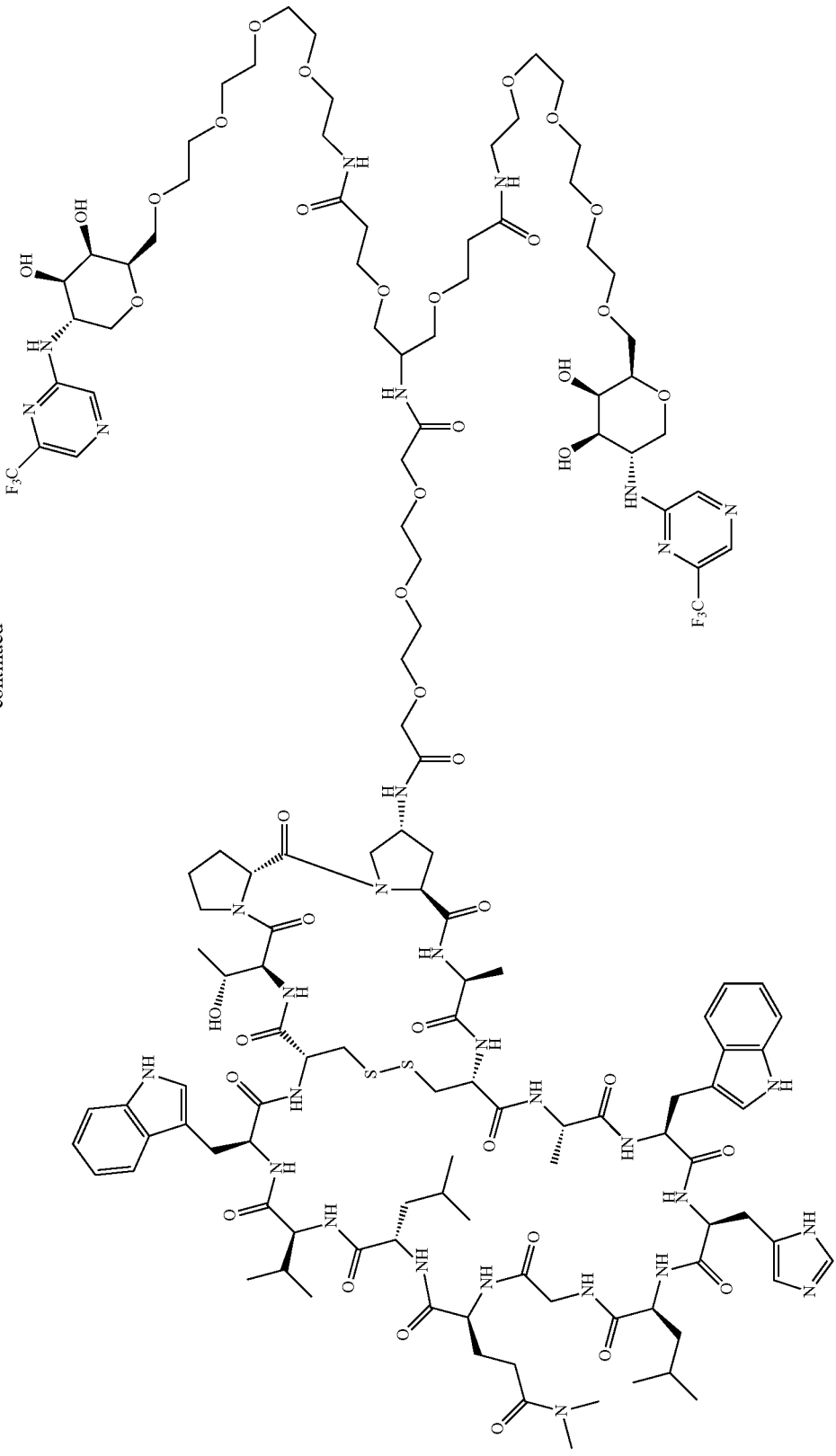

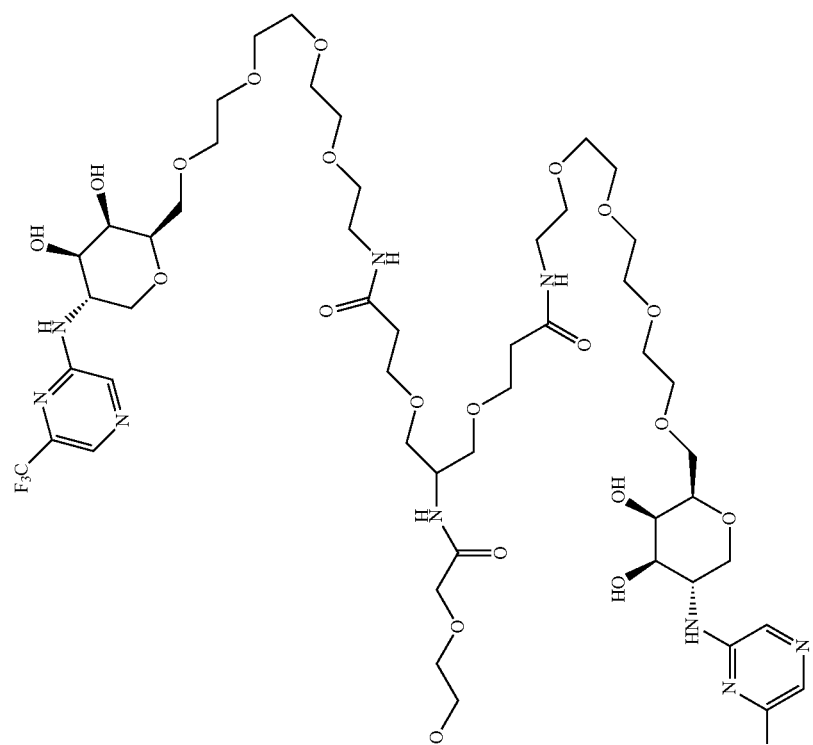
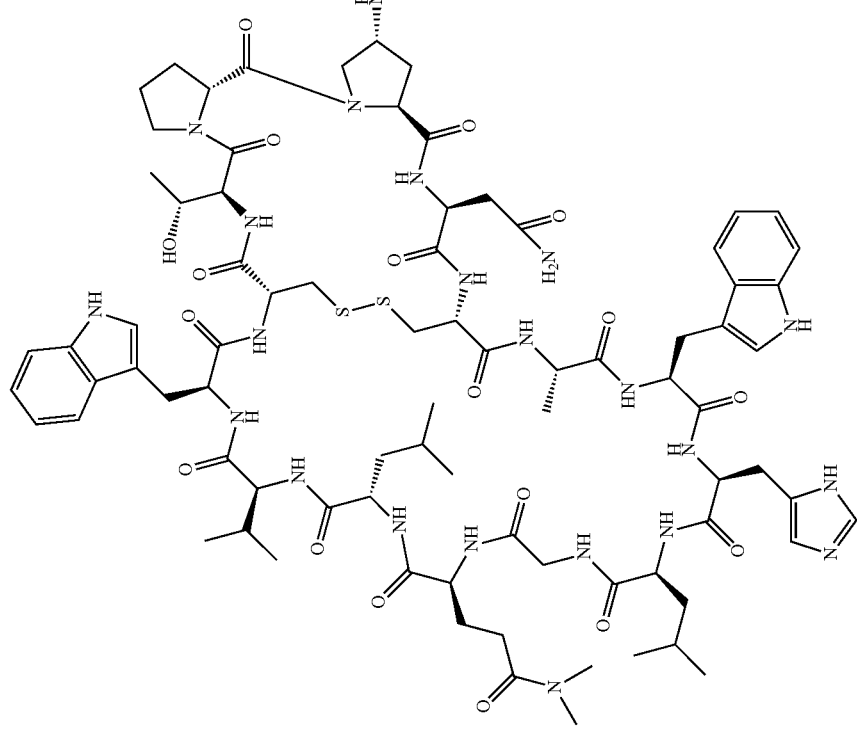

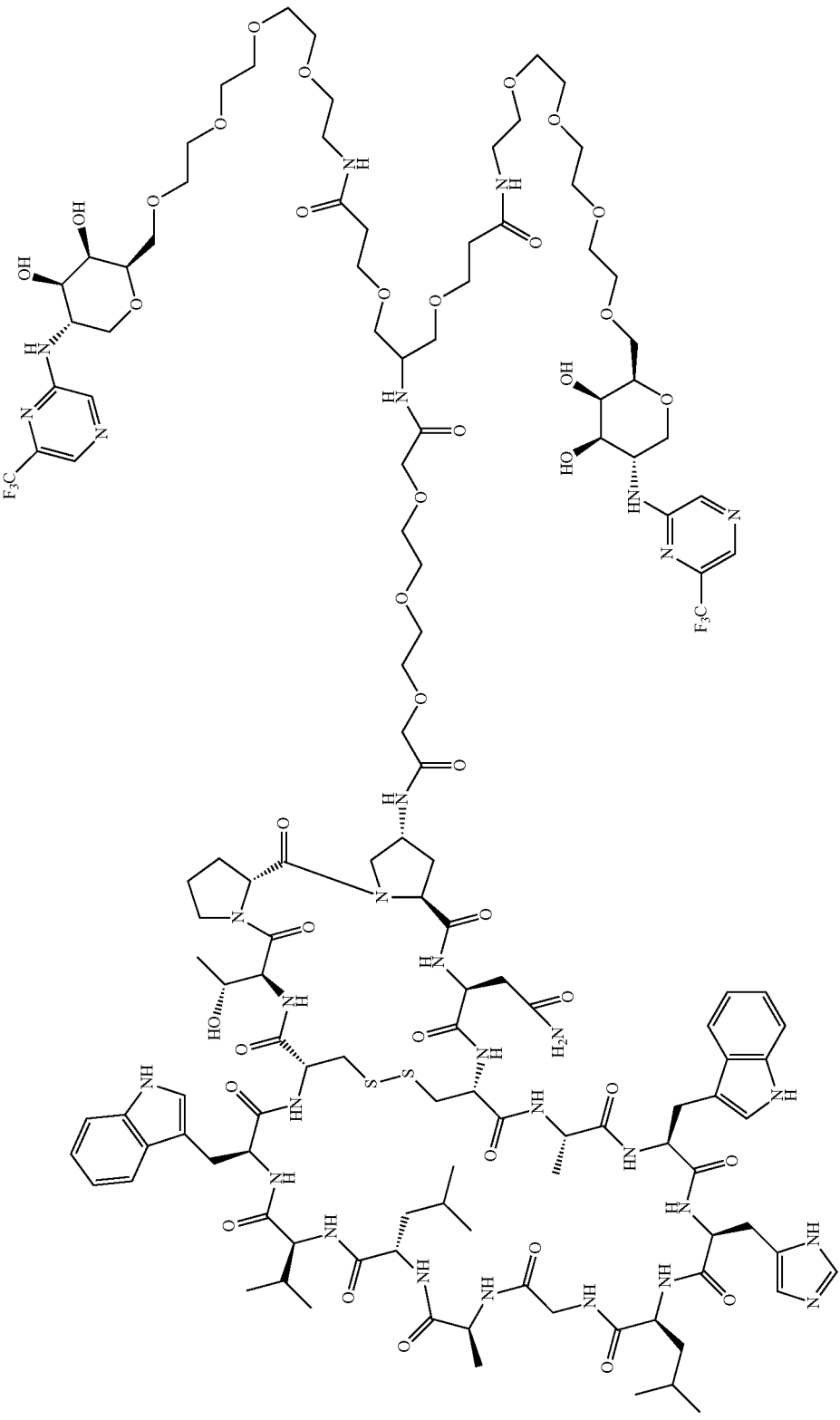

-continued
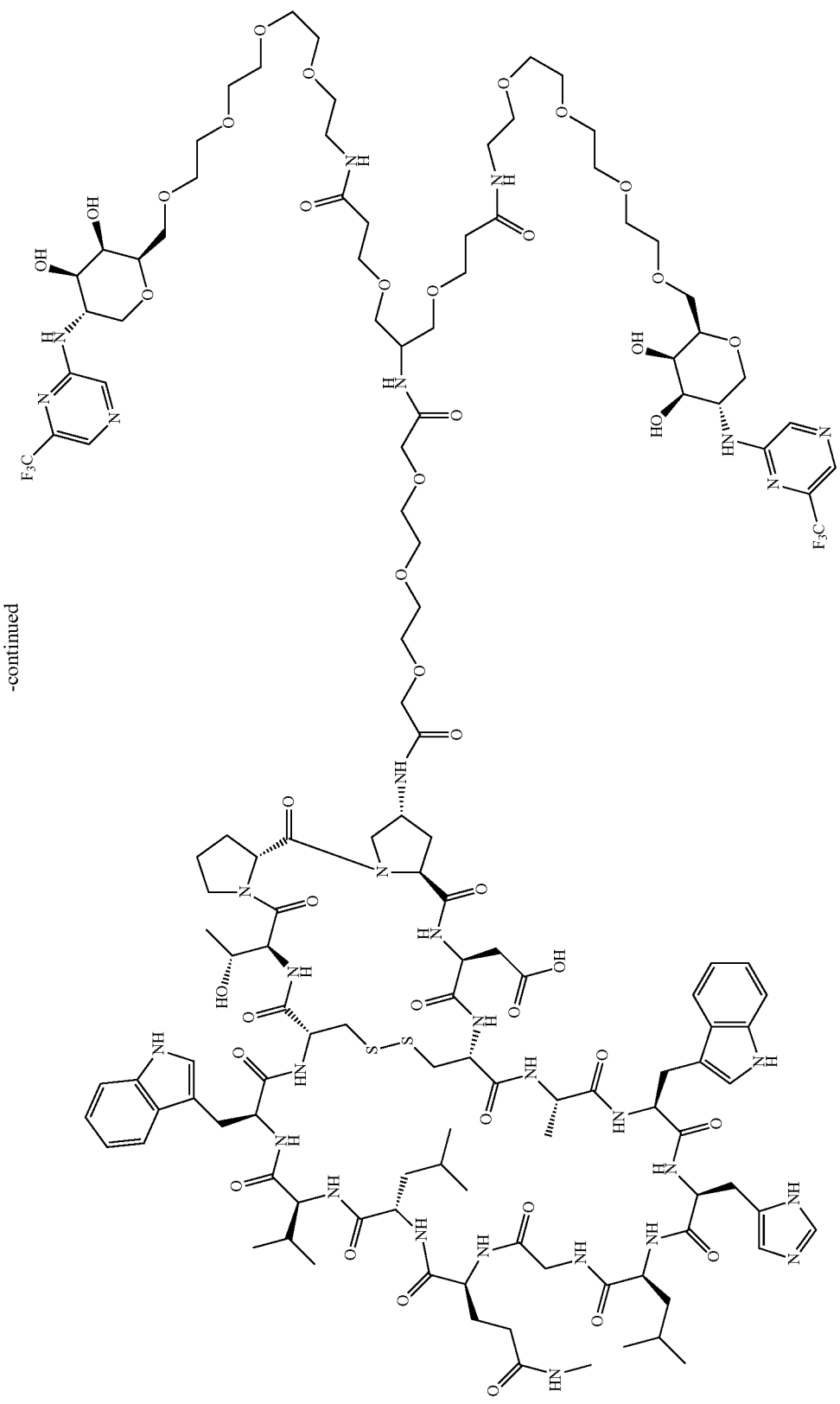

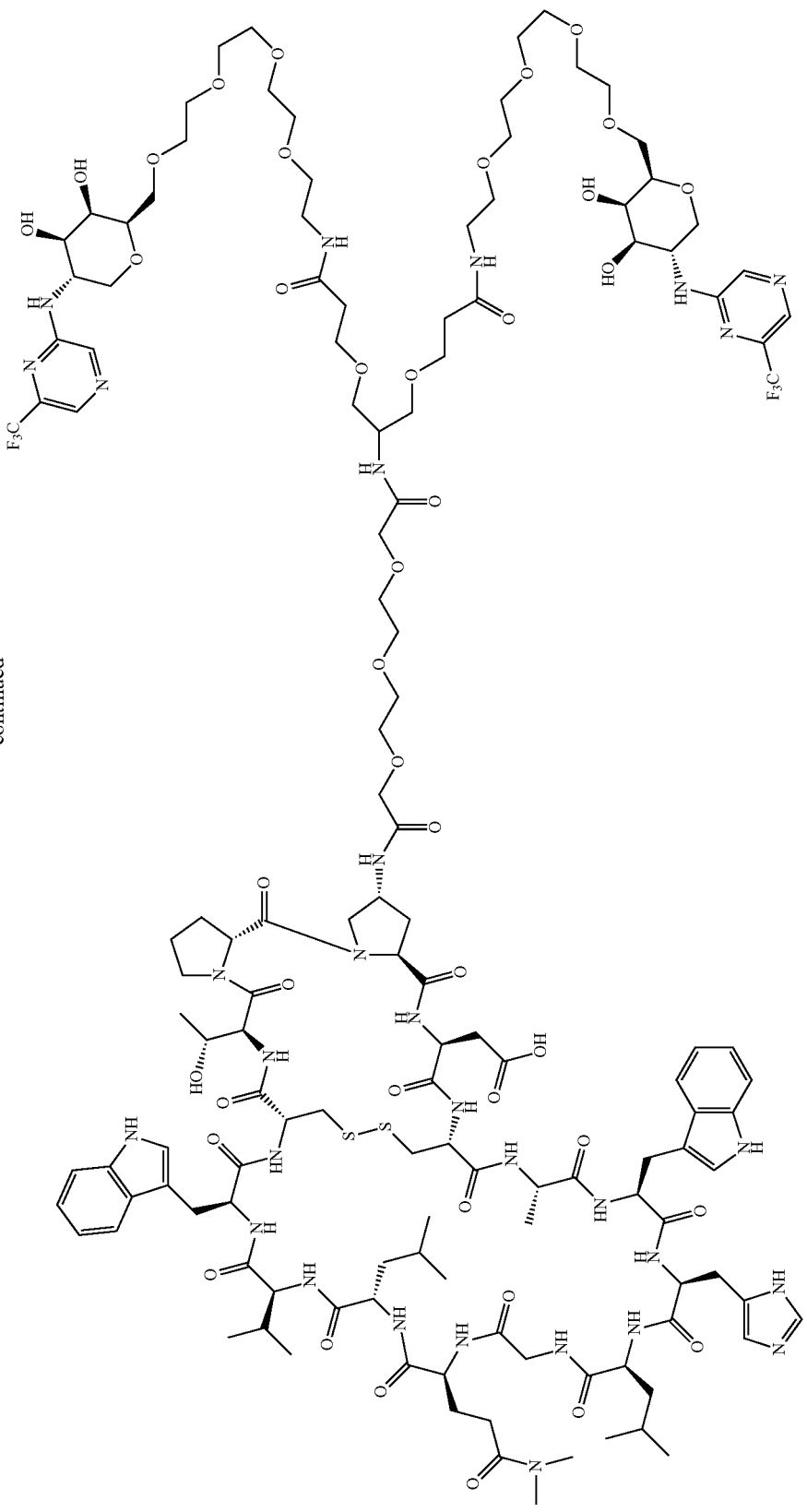

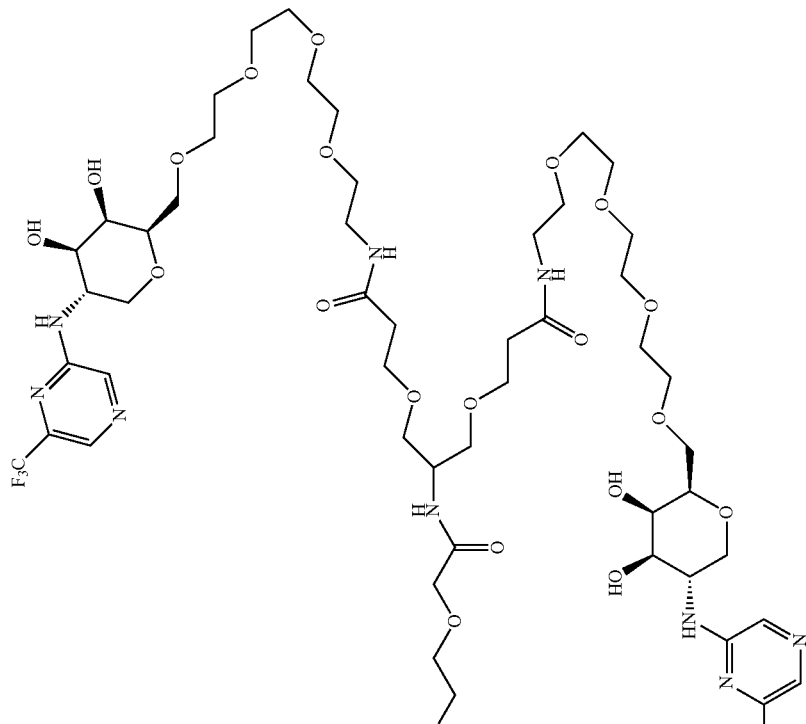
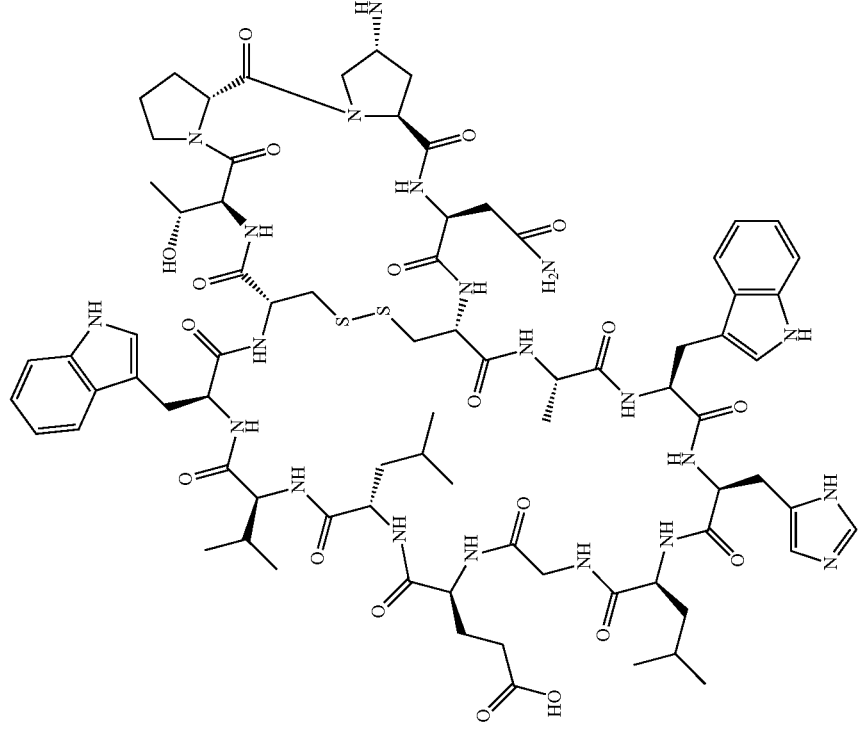

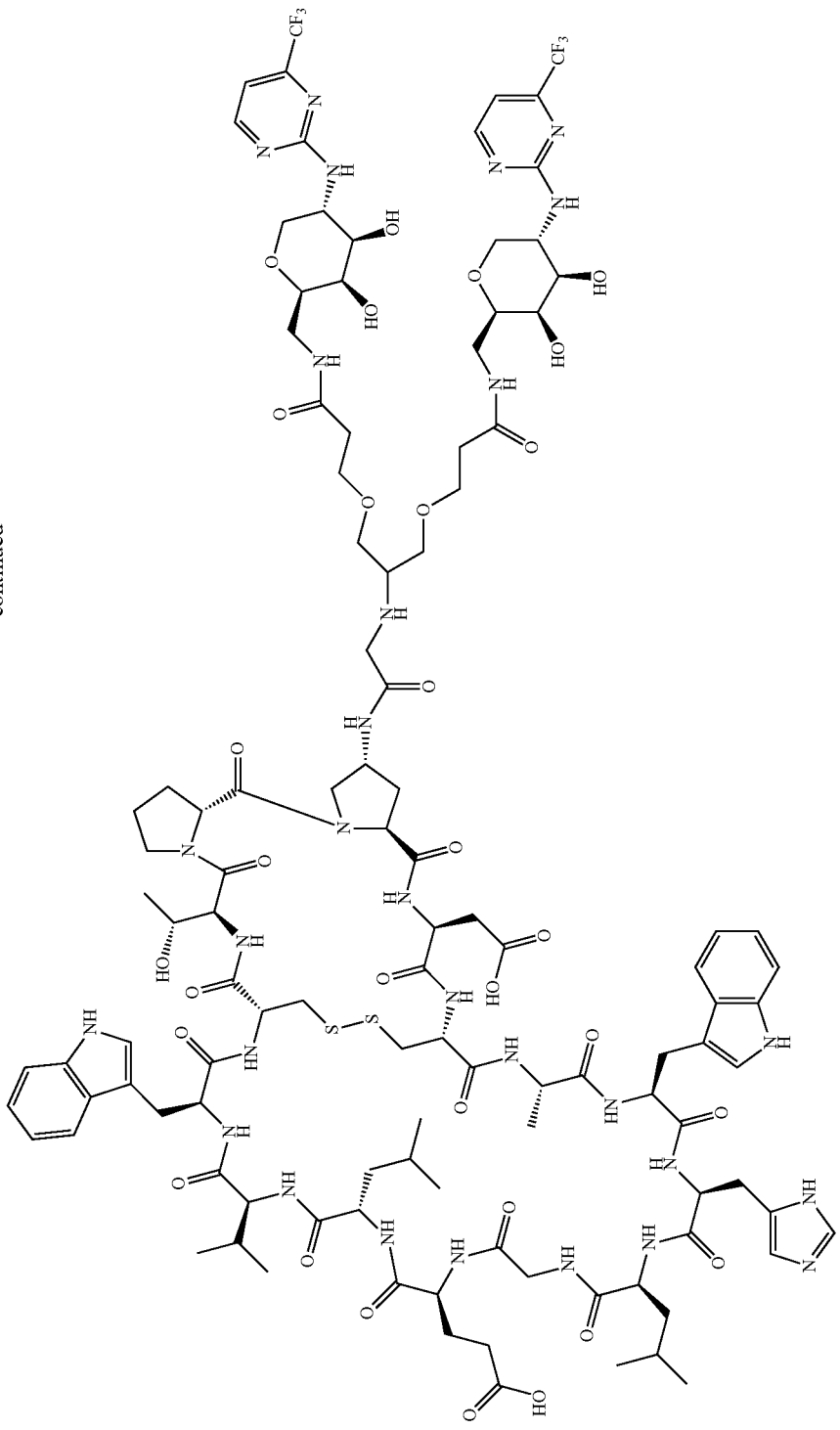

-continued
1661 1662
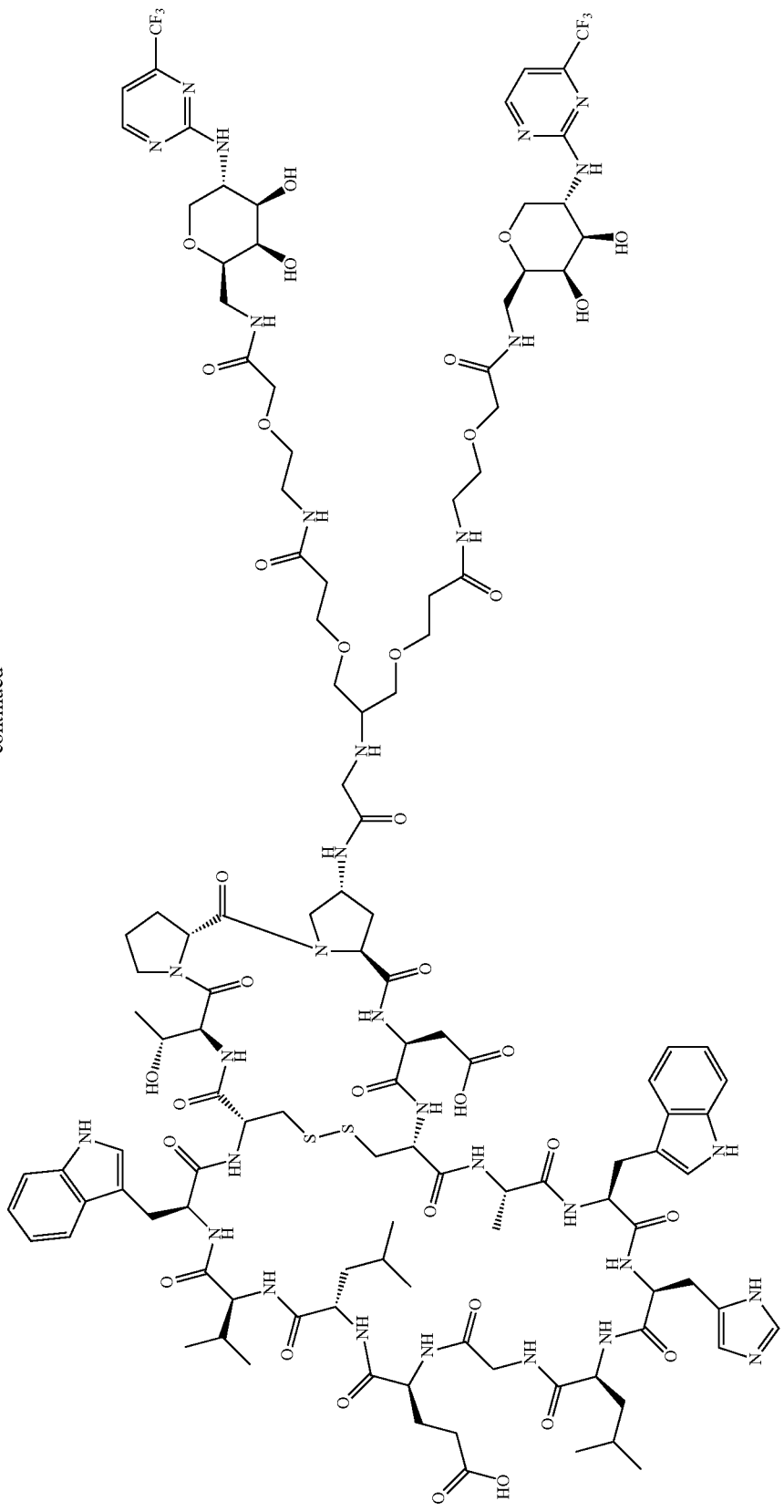

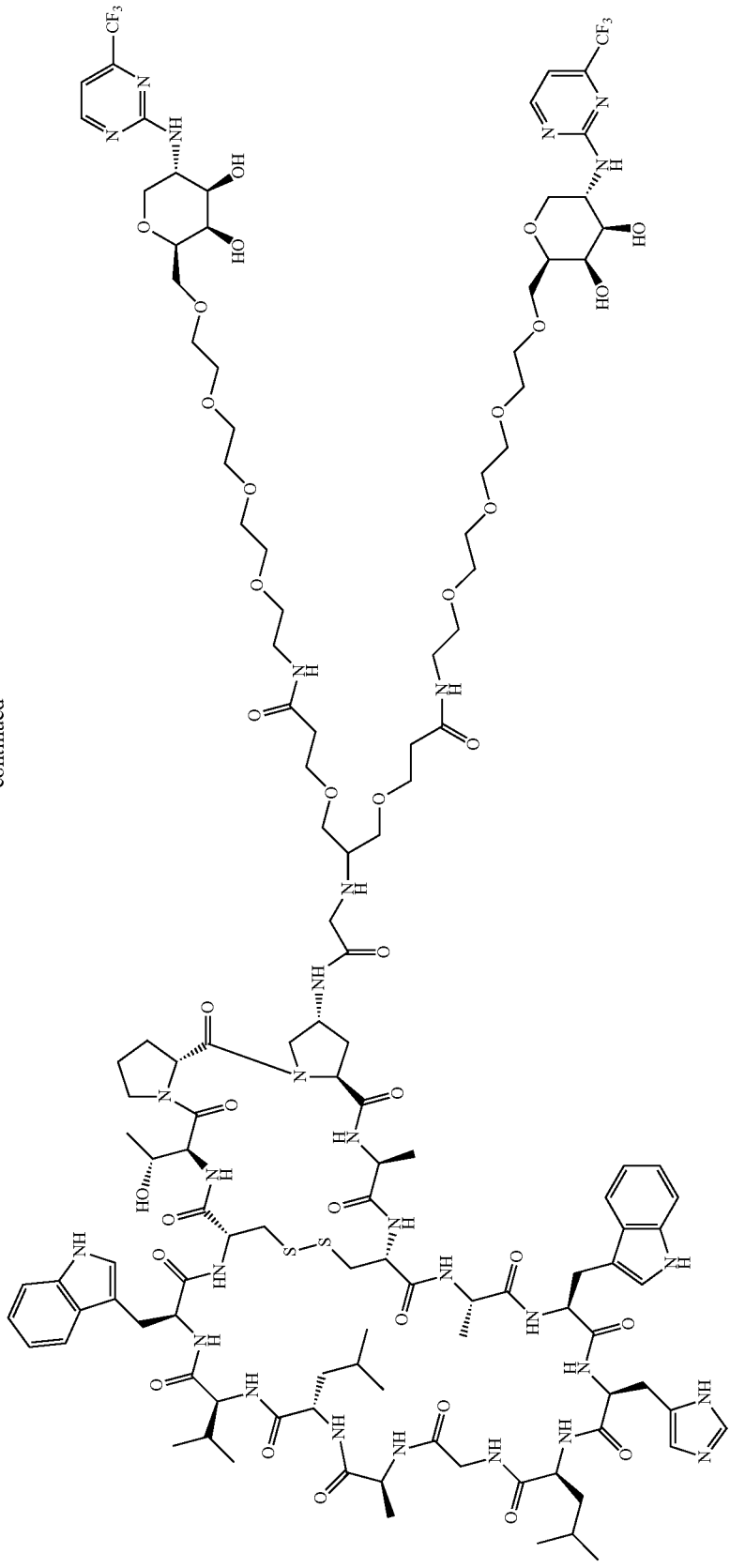

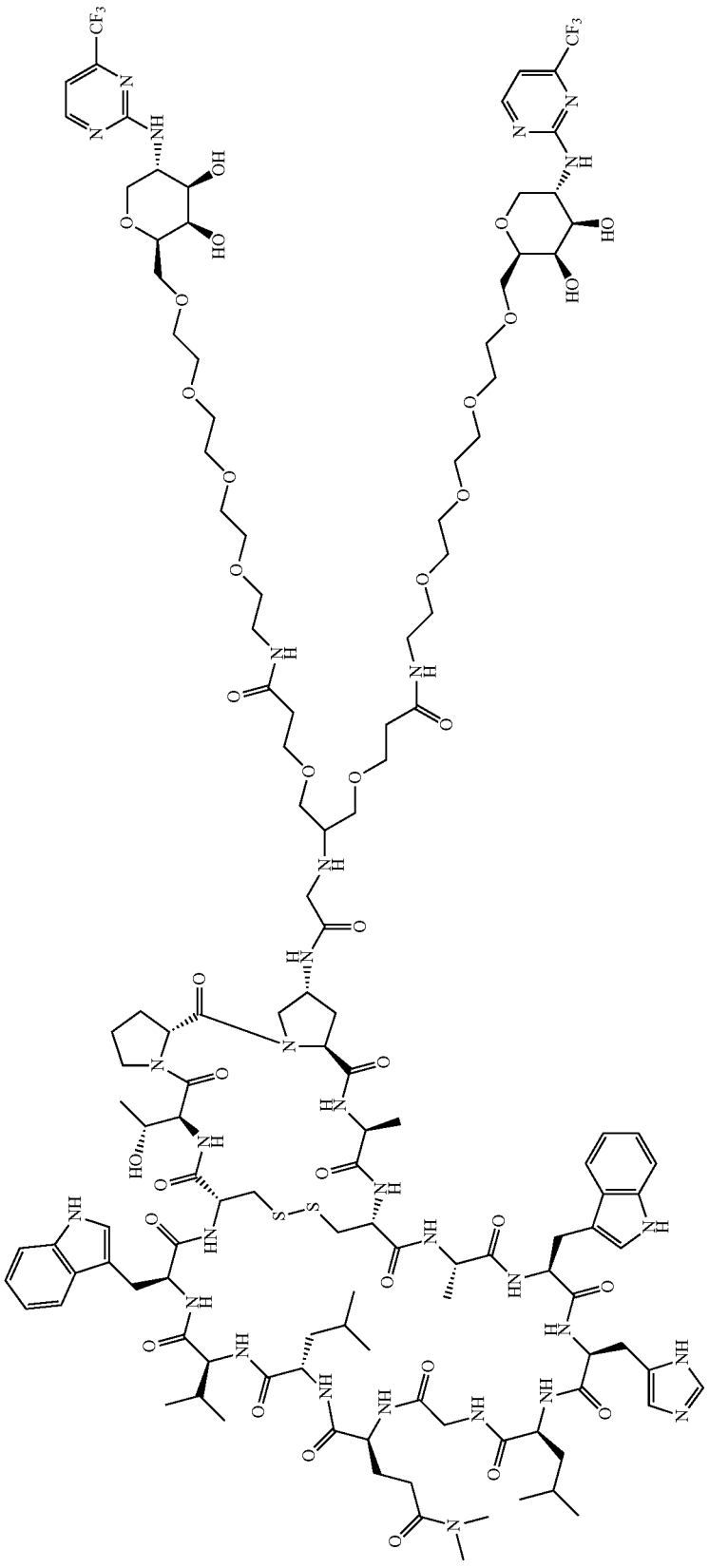

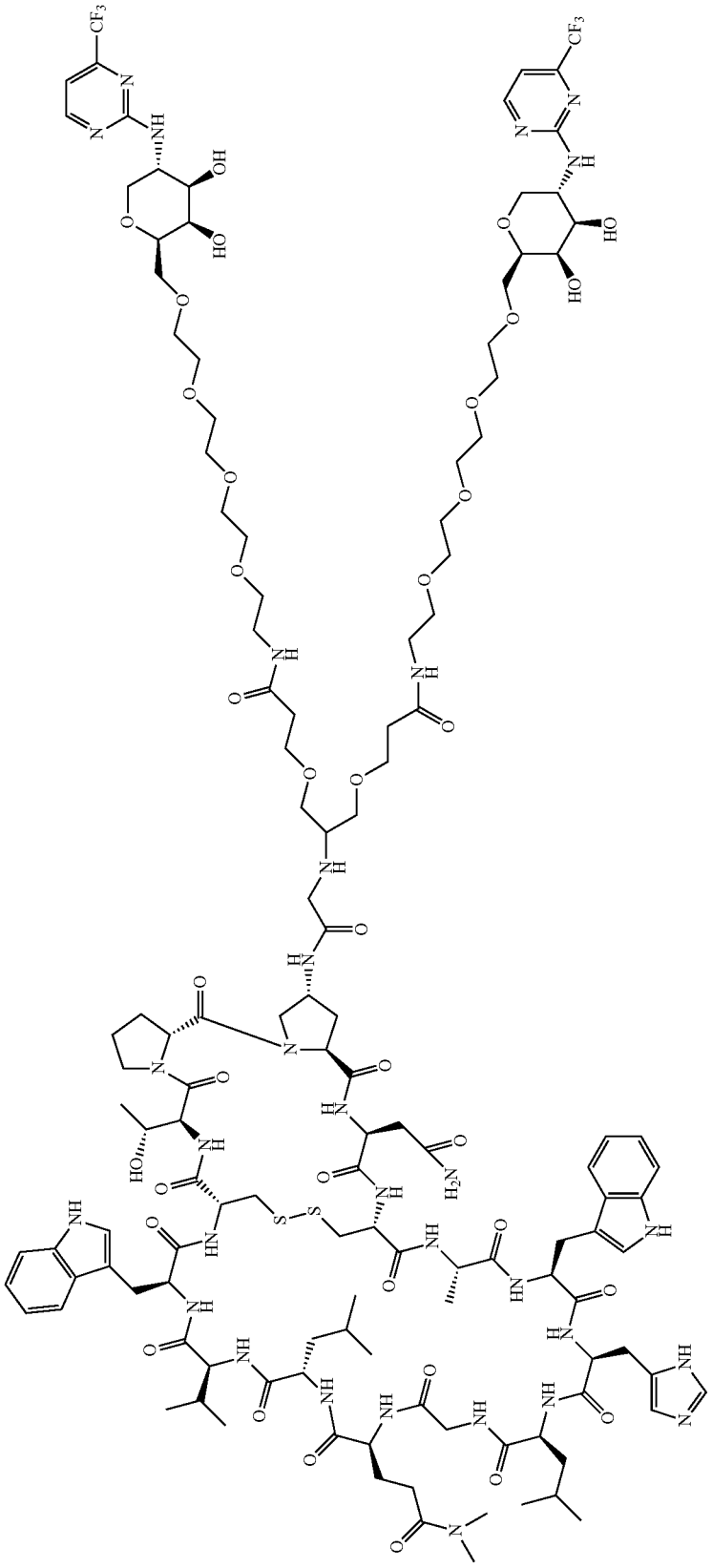

-continued
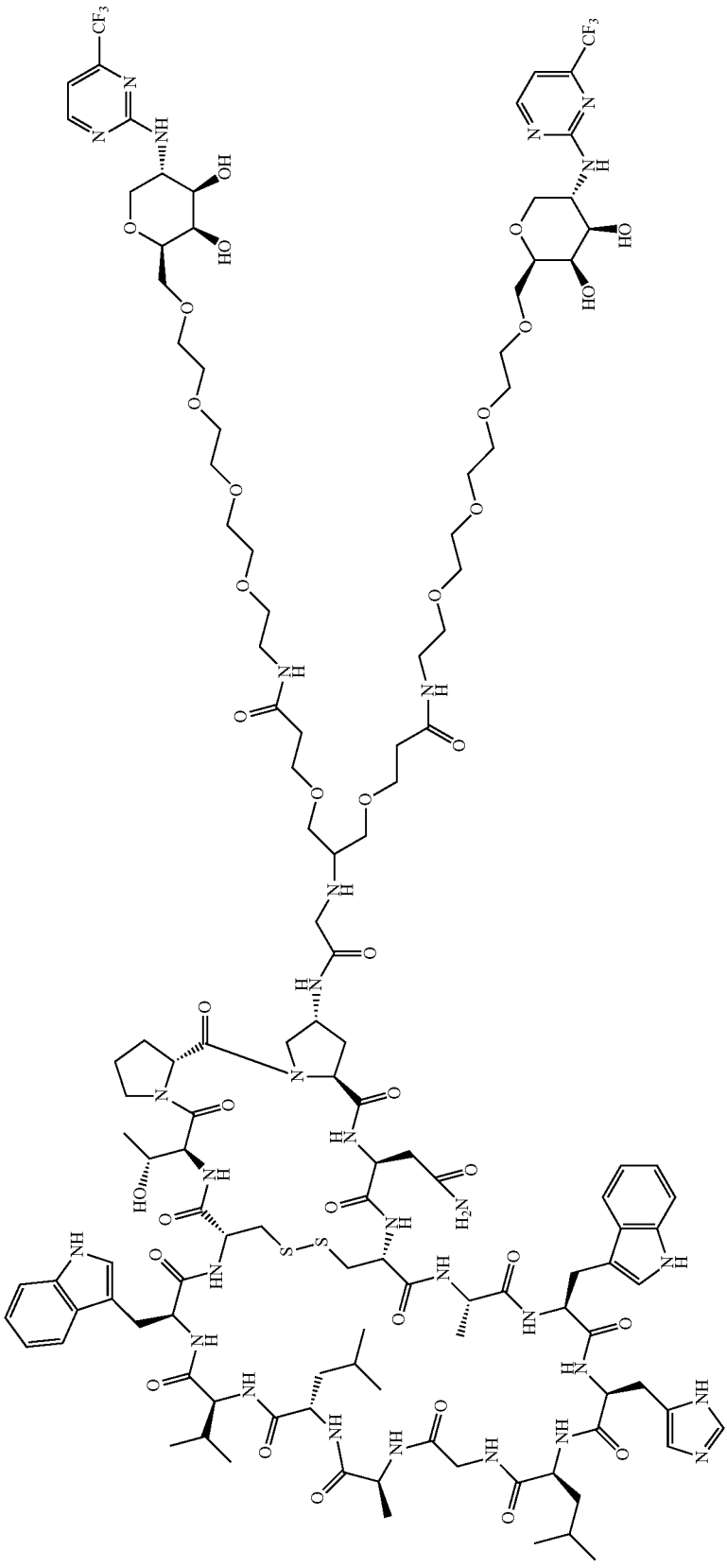

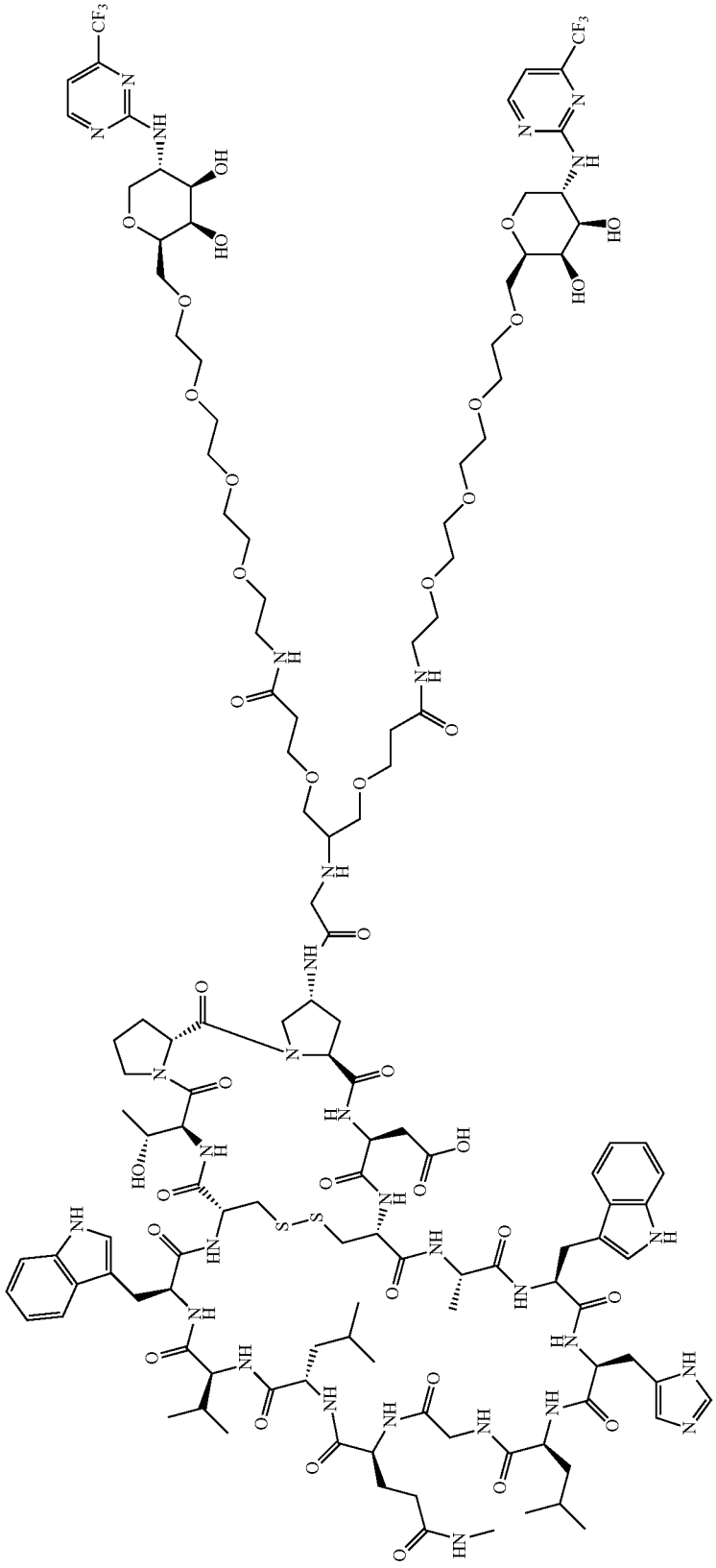

-continued
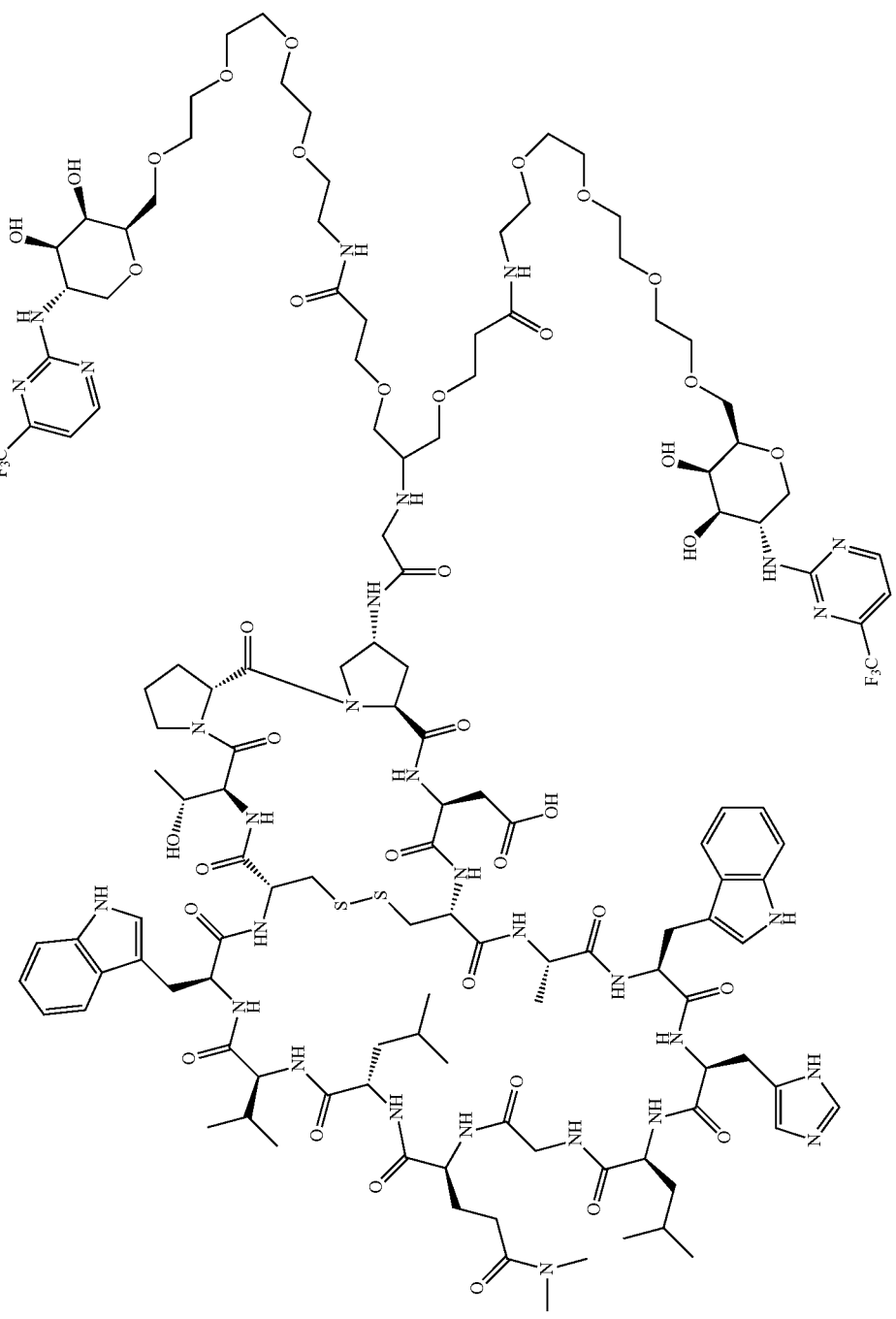

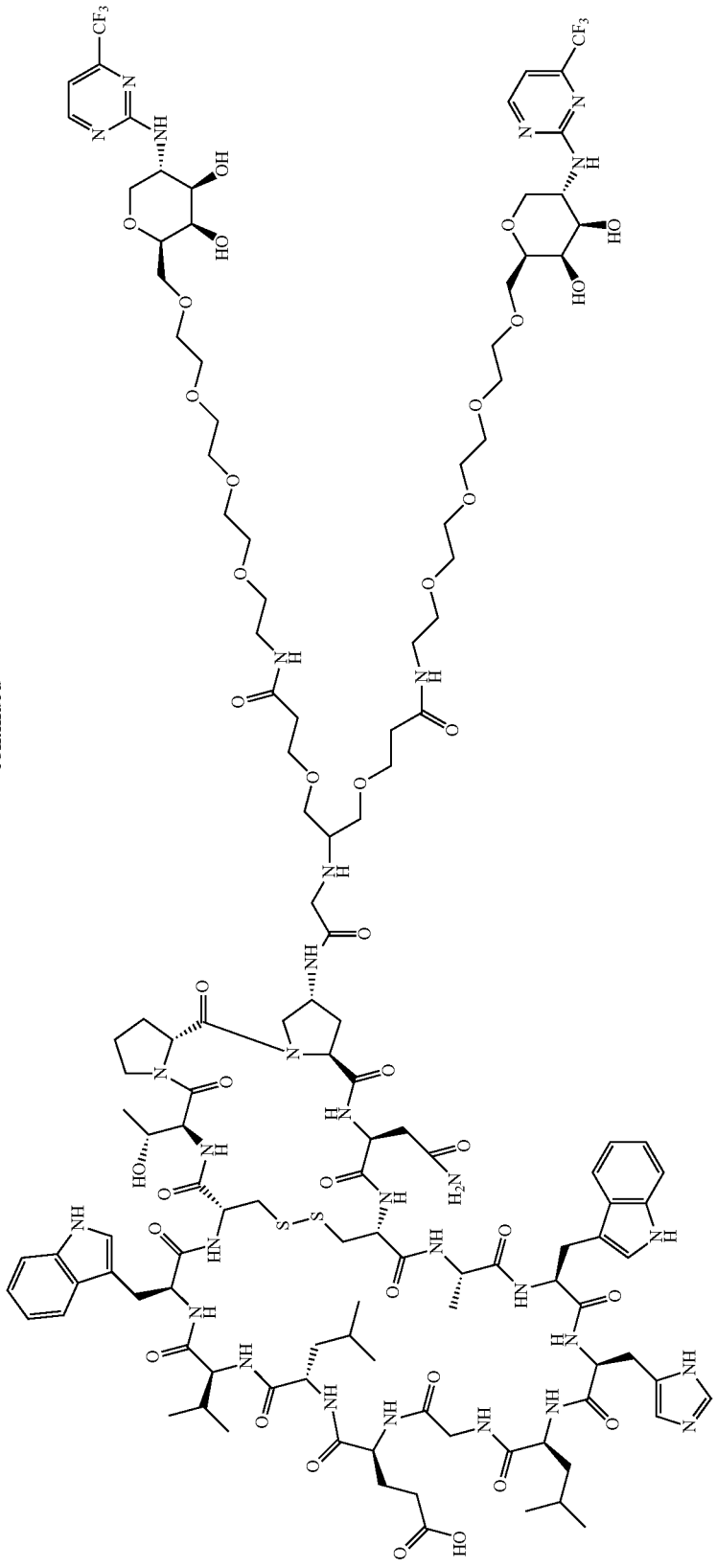

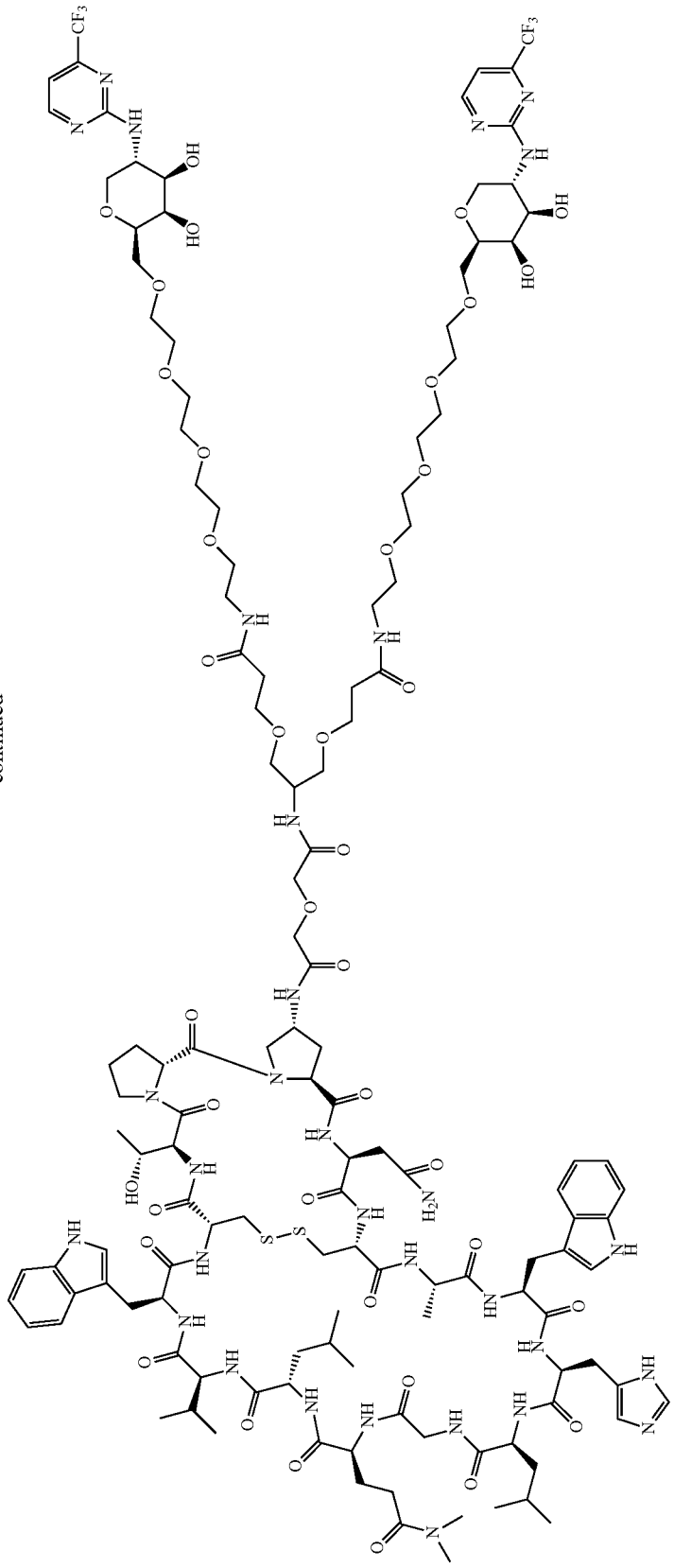

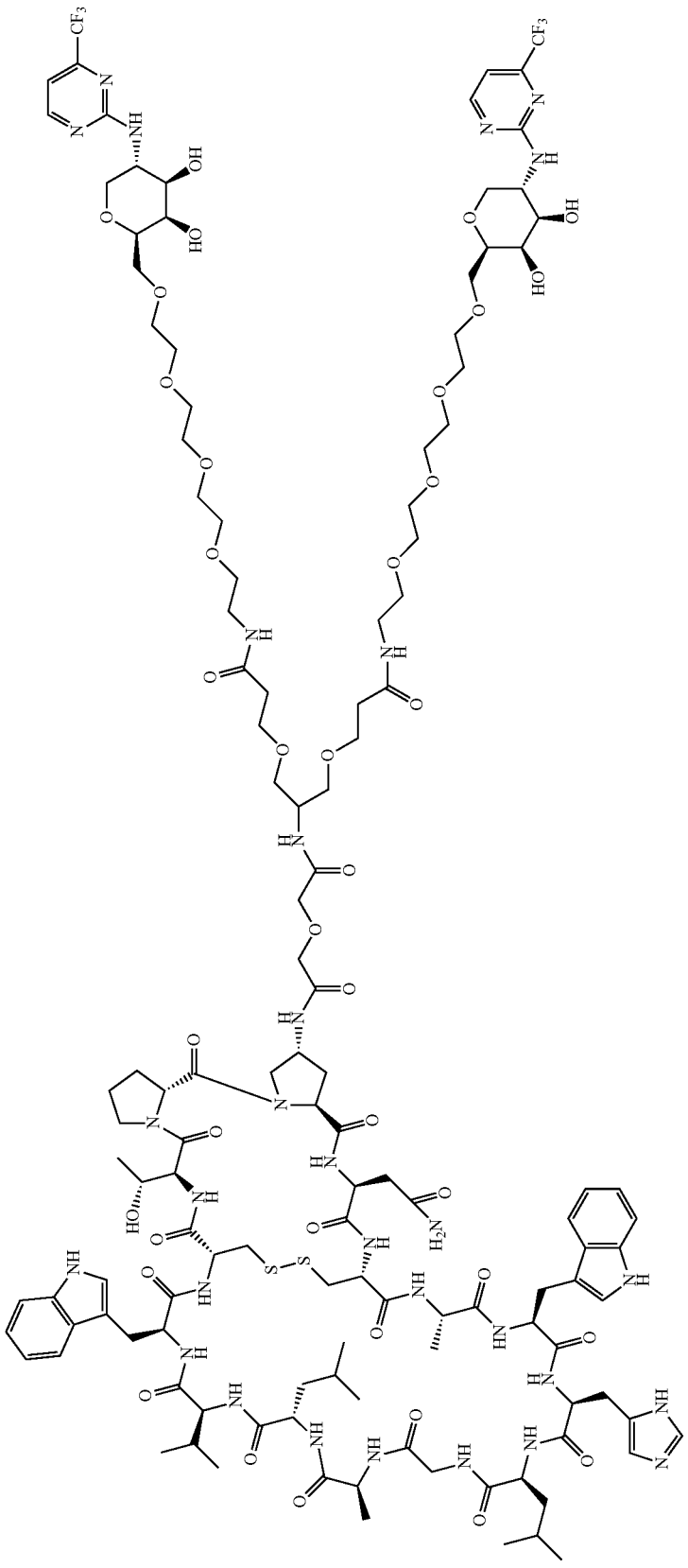

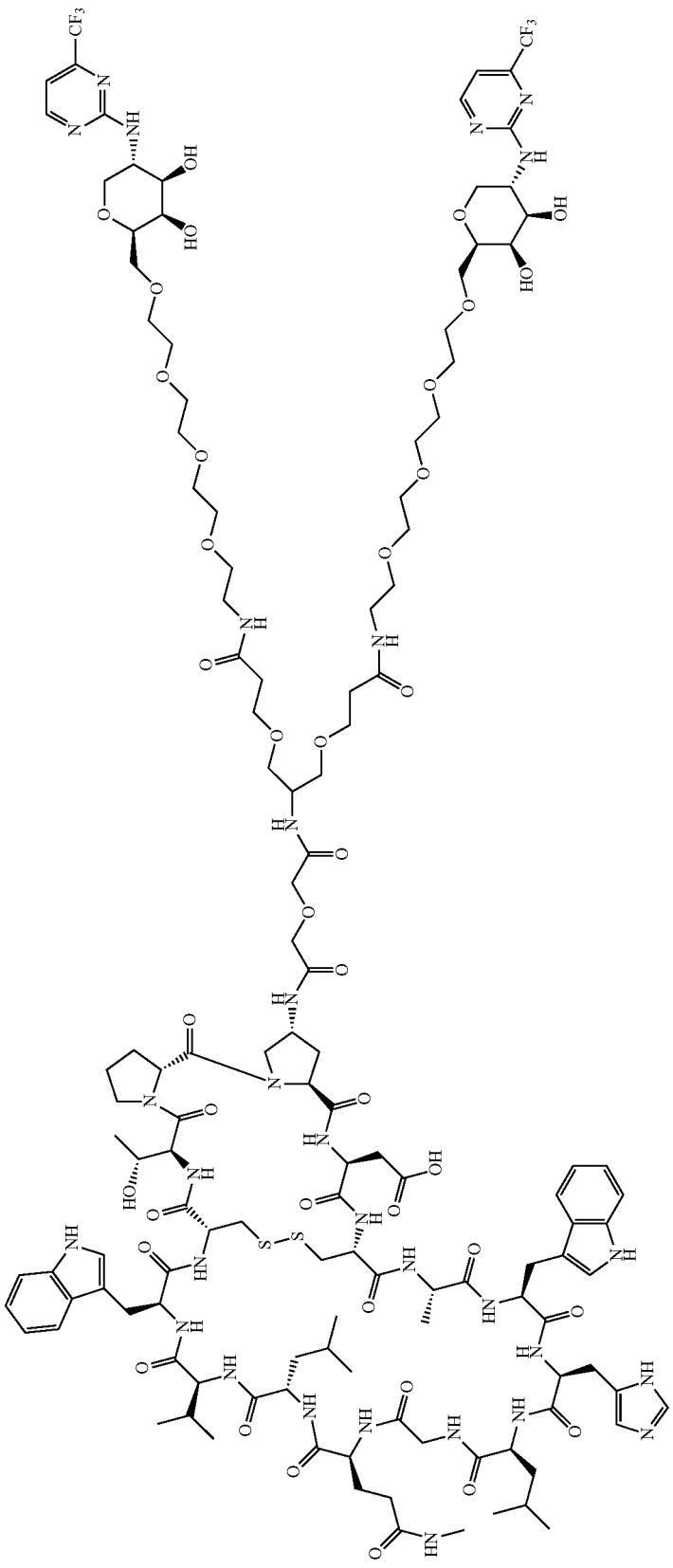

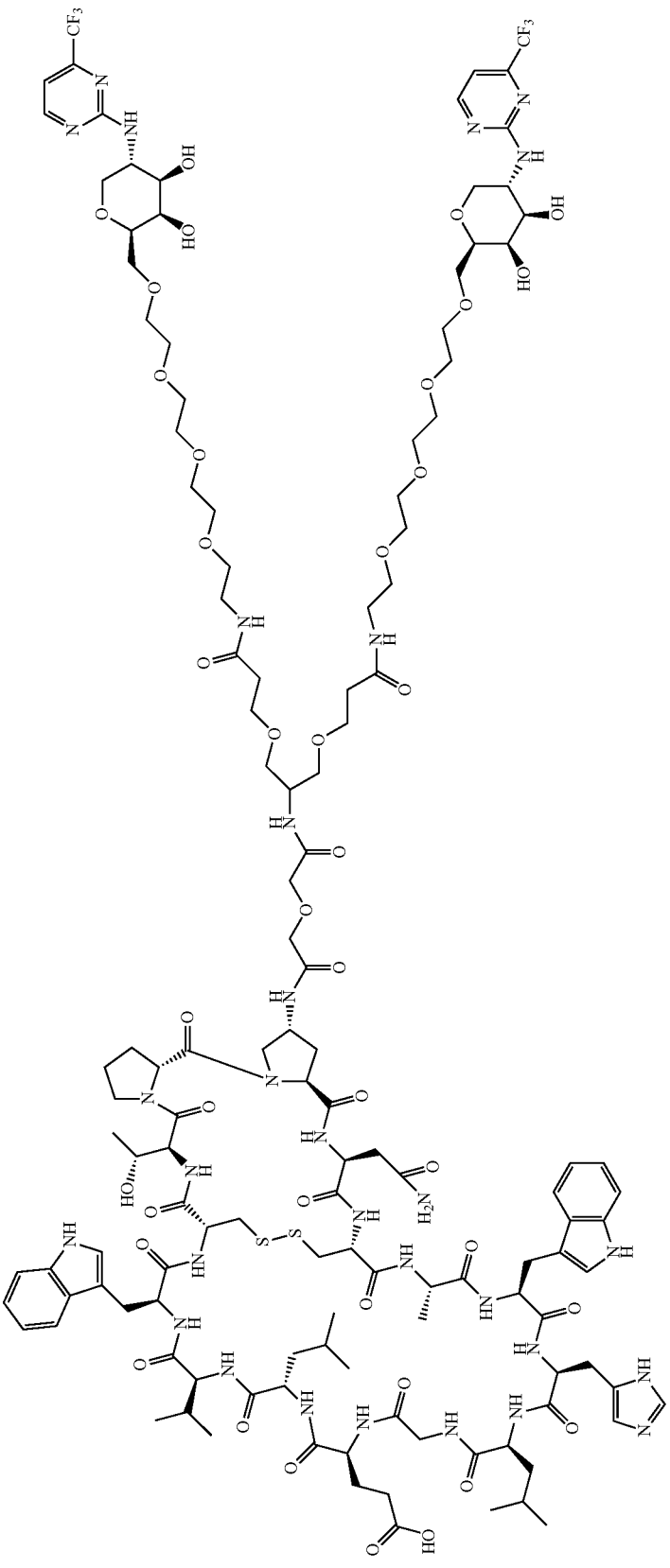

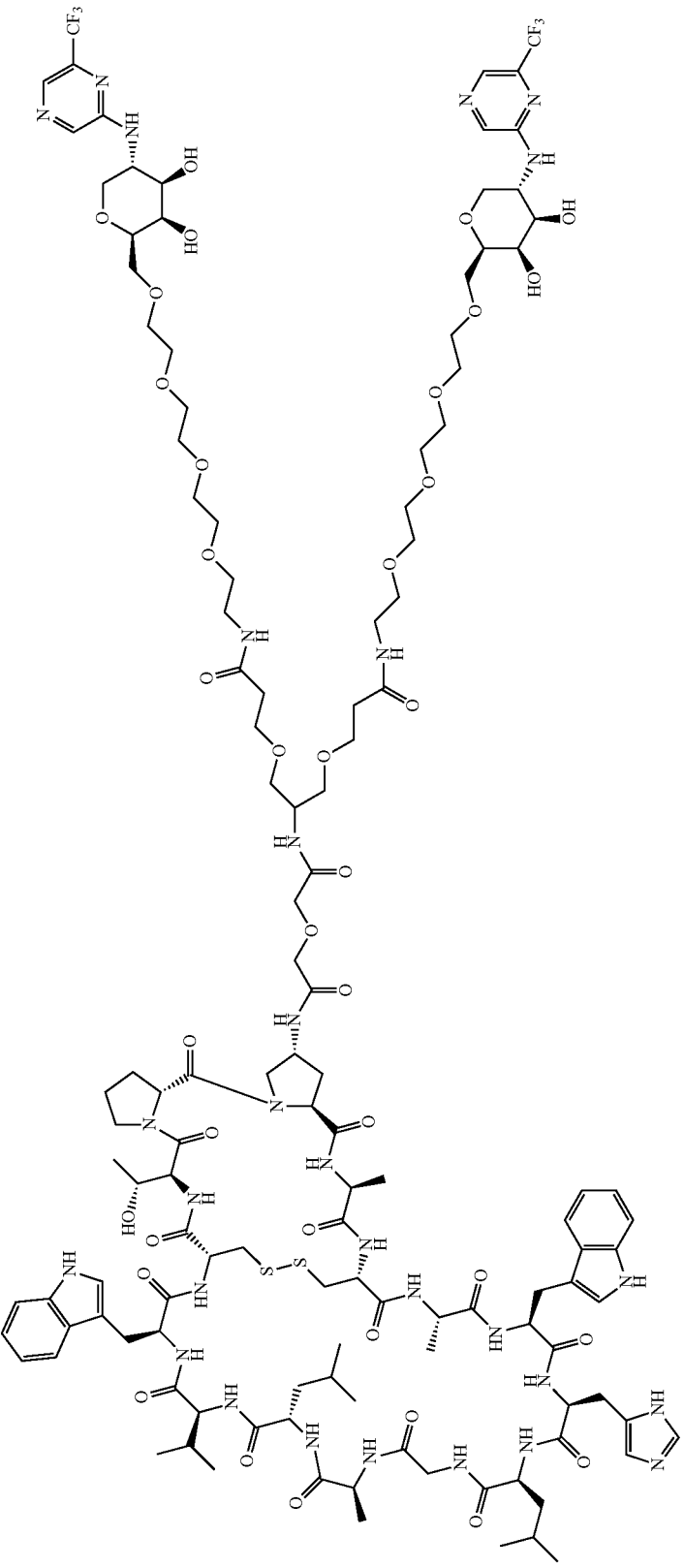

1687 1688
-continued
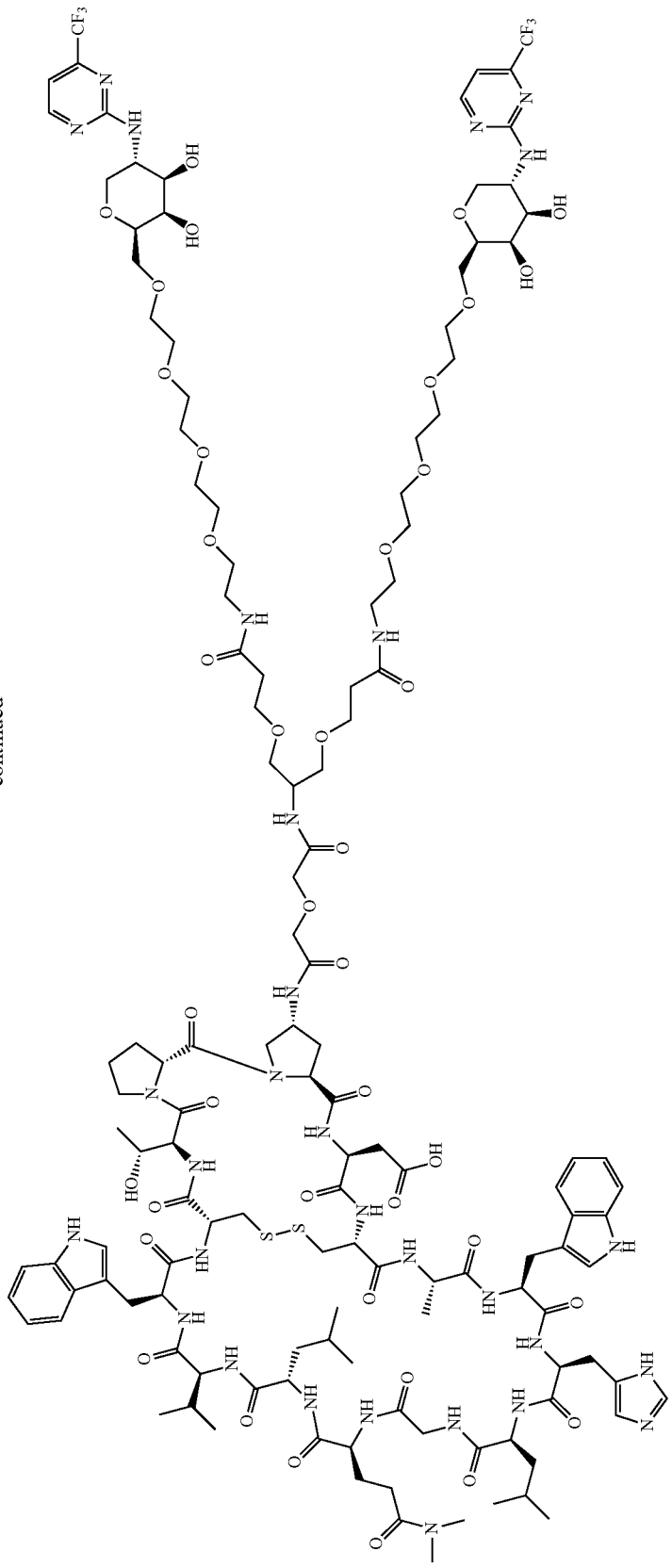

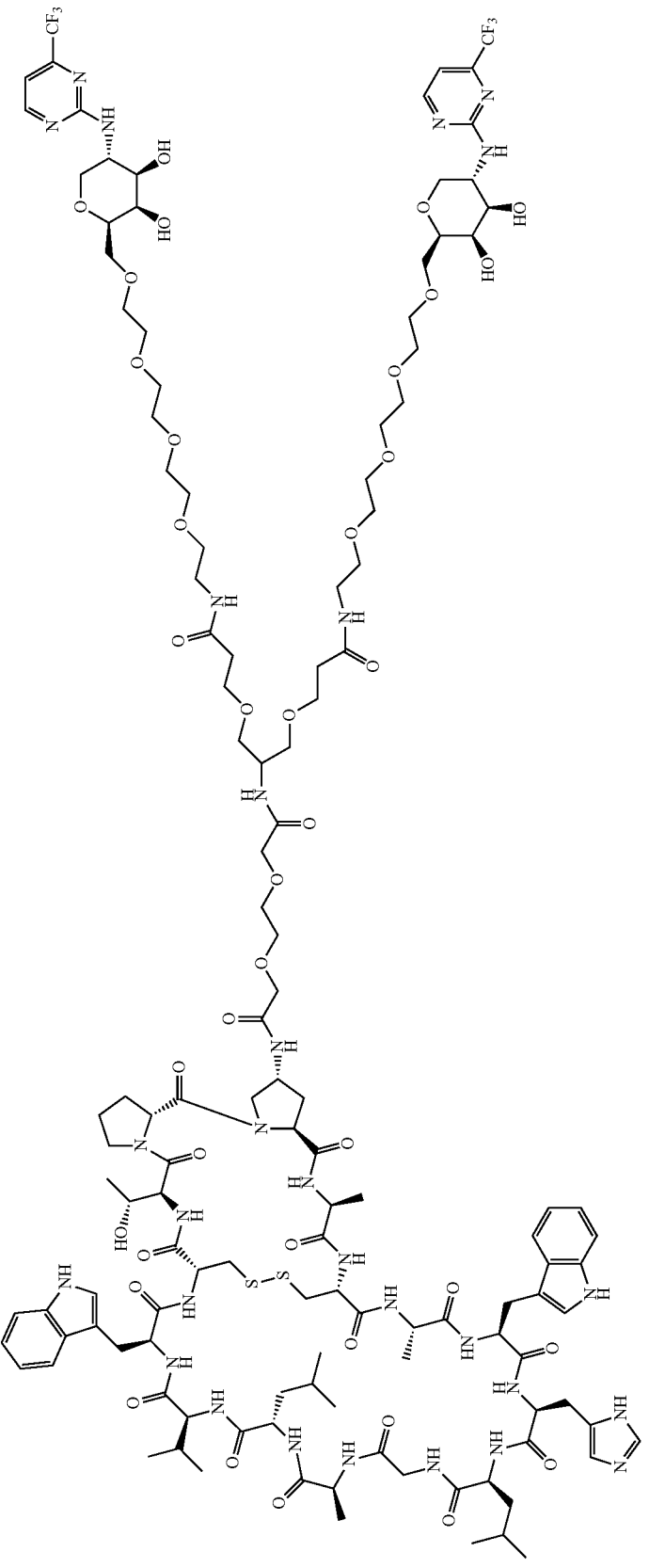

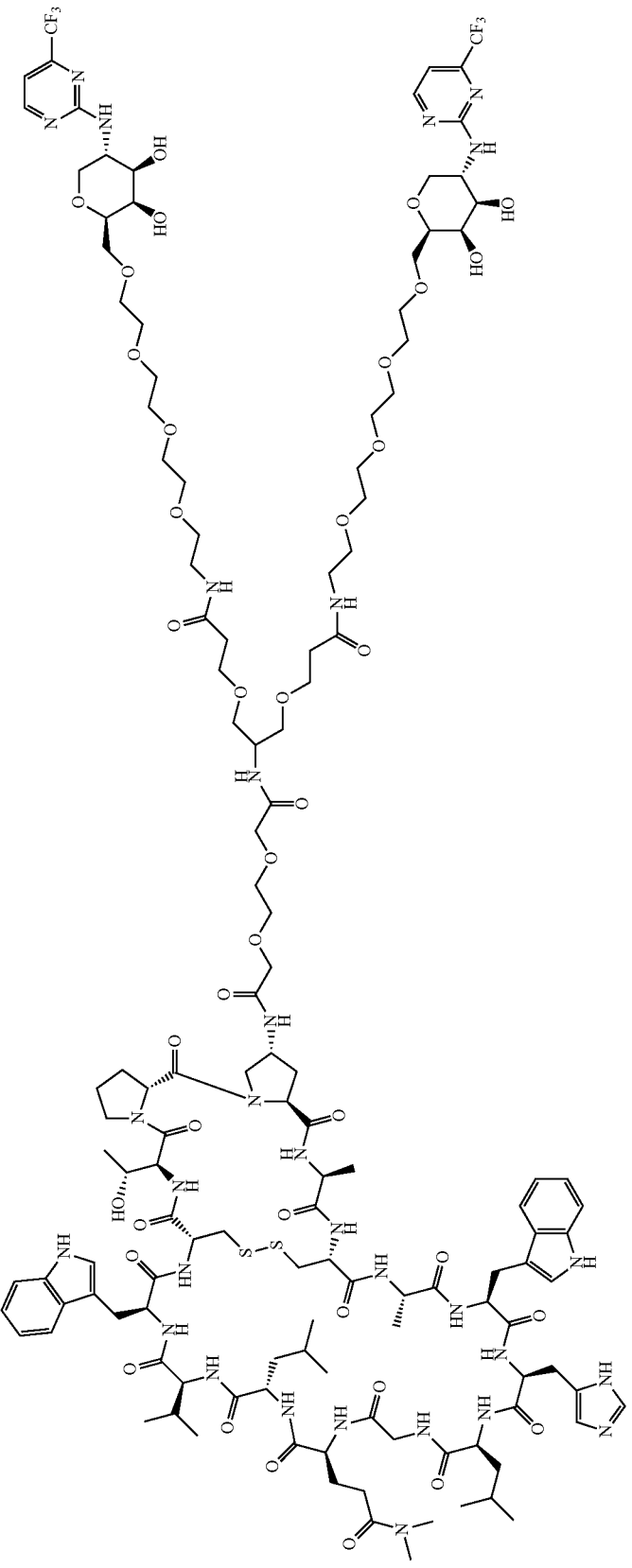

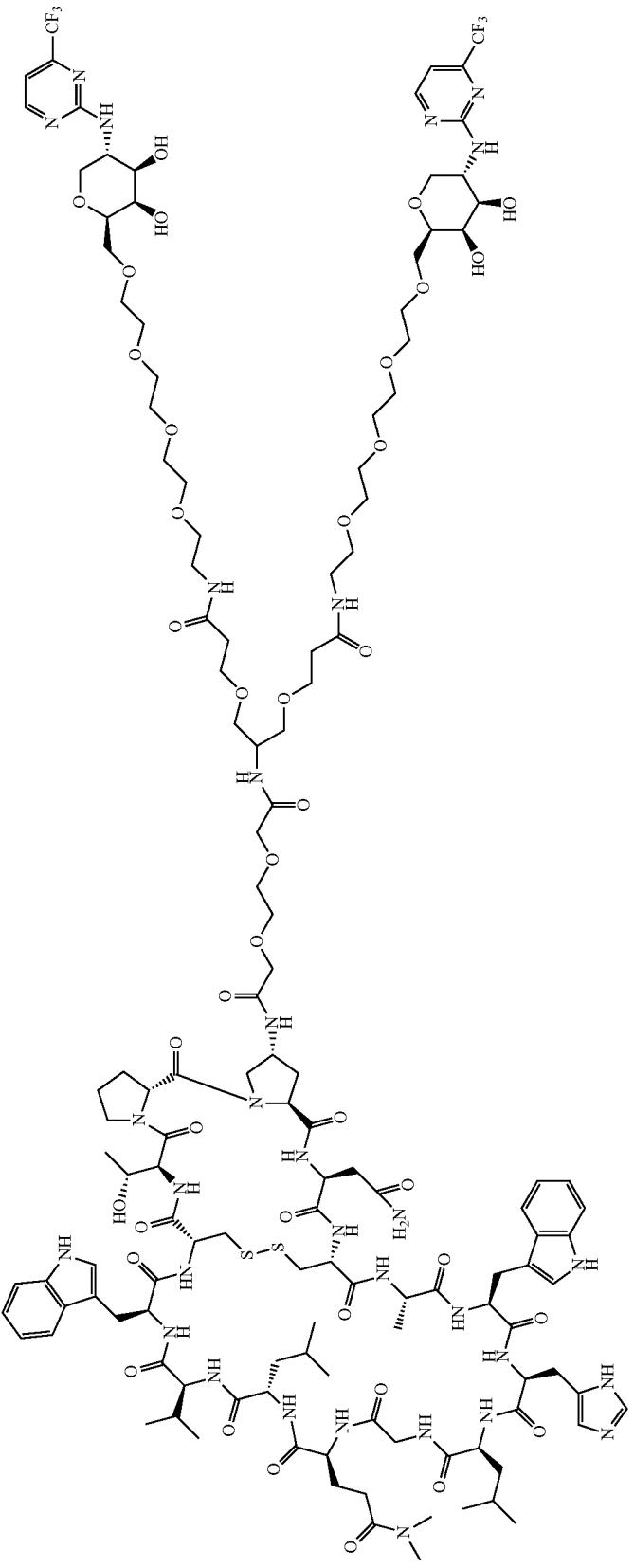

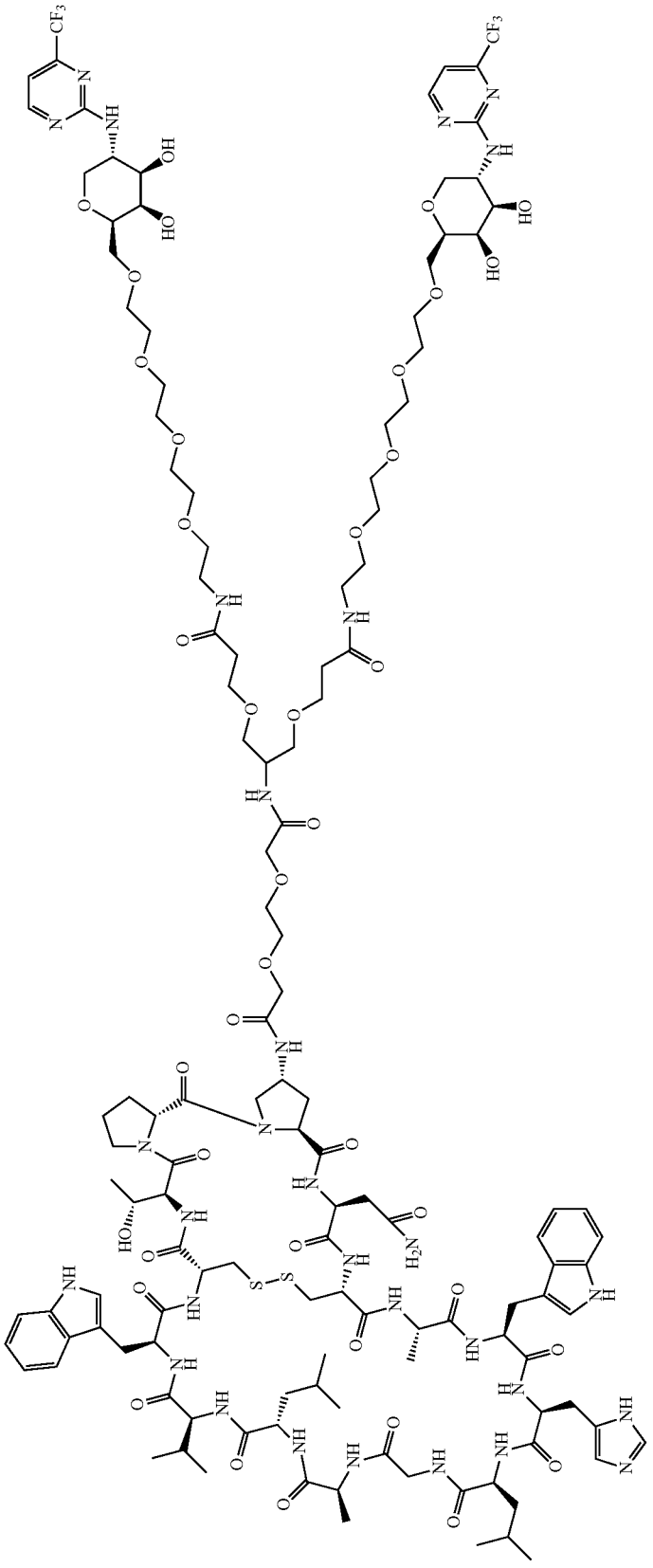

-continued
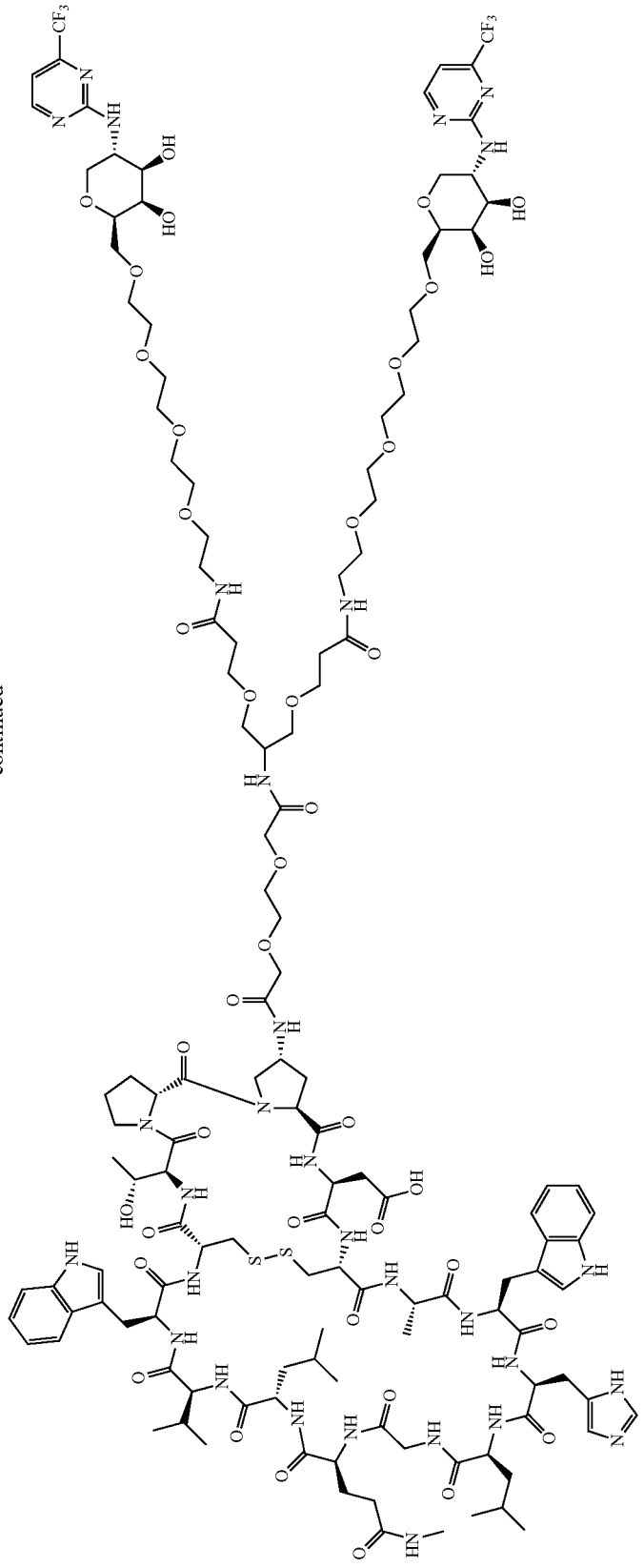

-continued
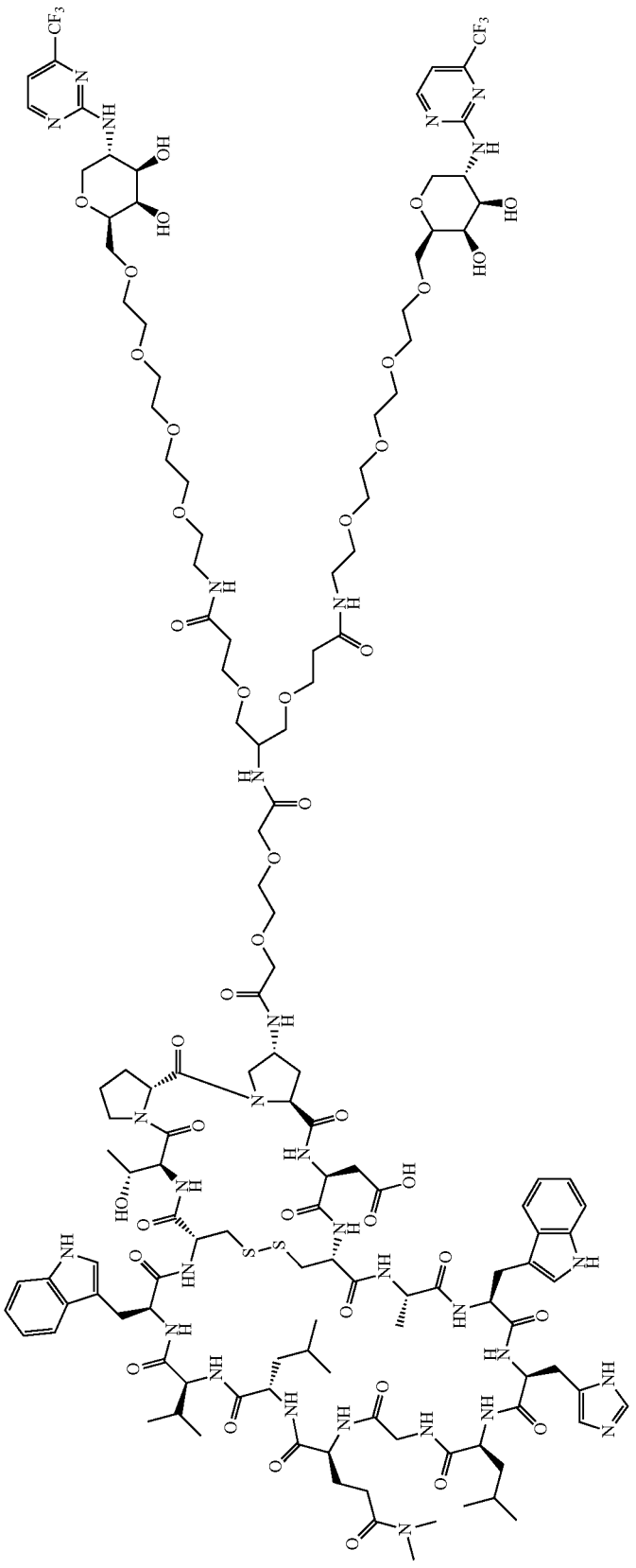

1701 1702
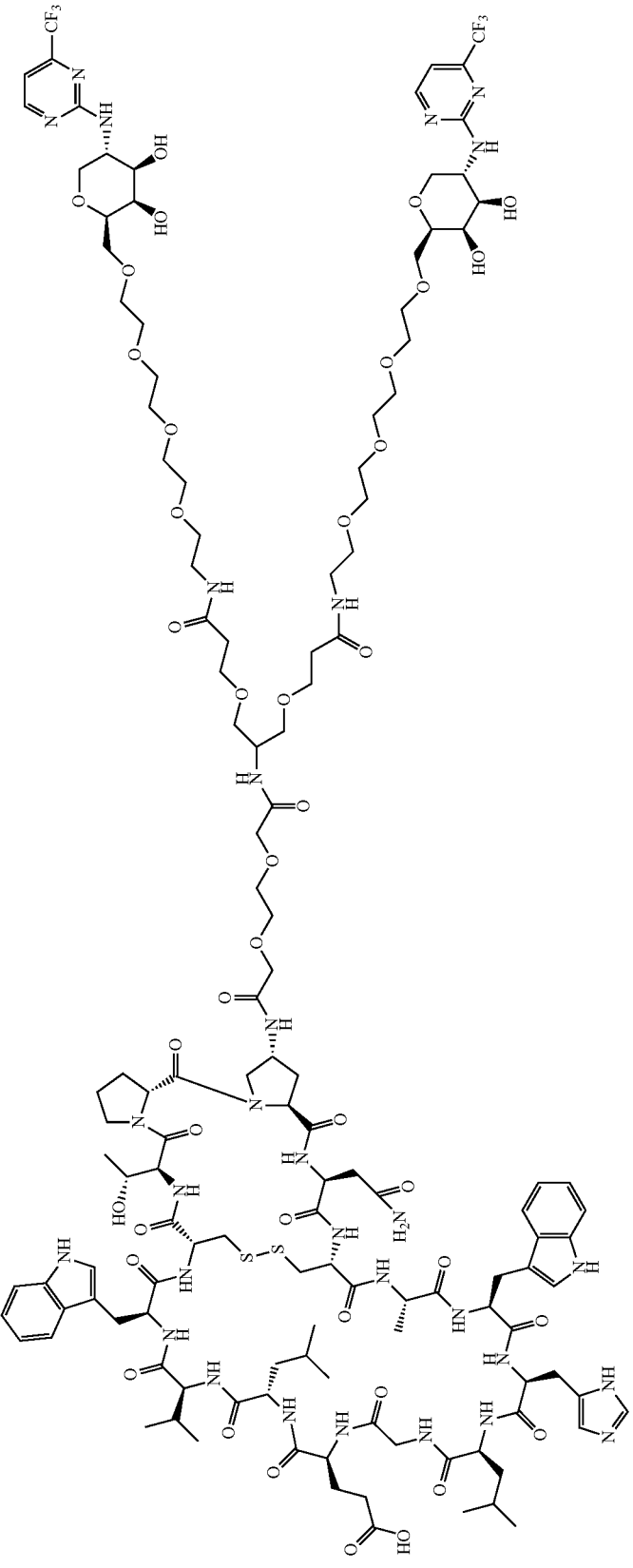

-continued
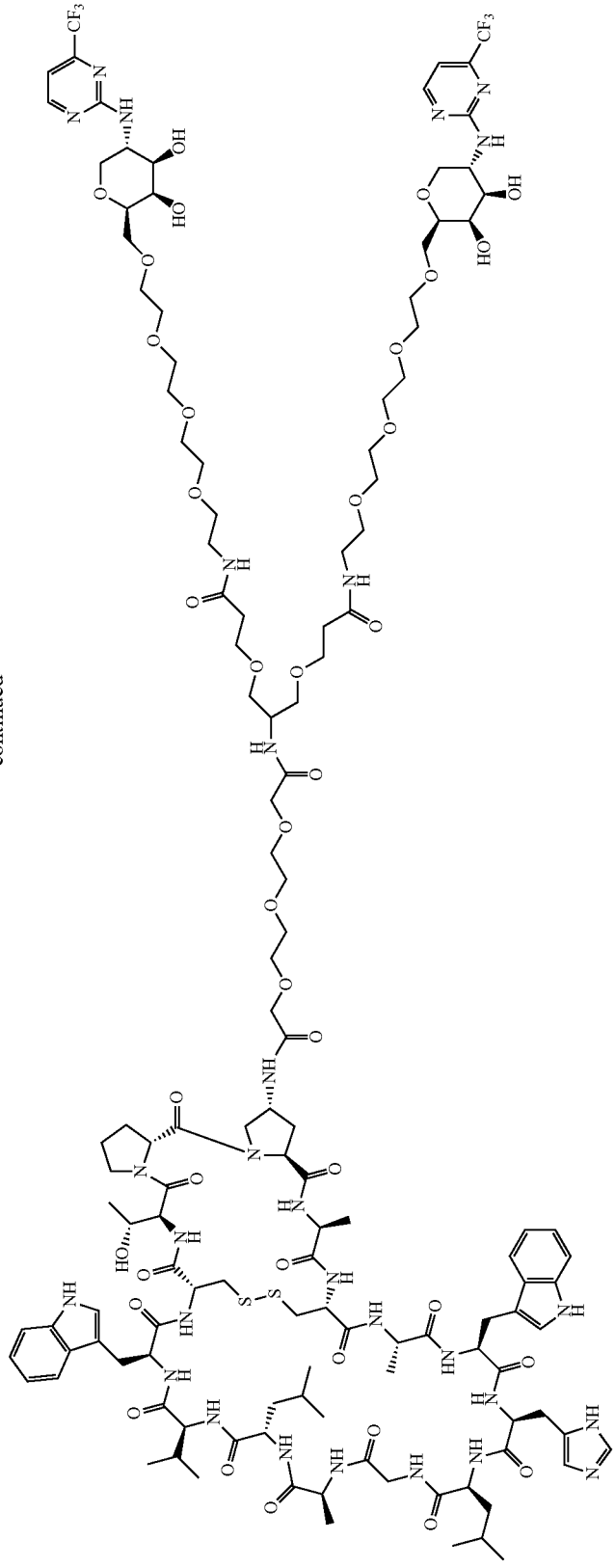

1705 1706
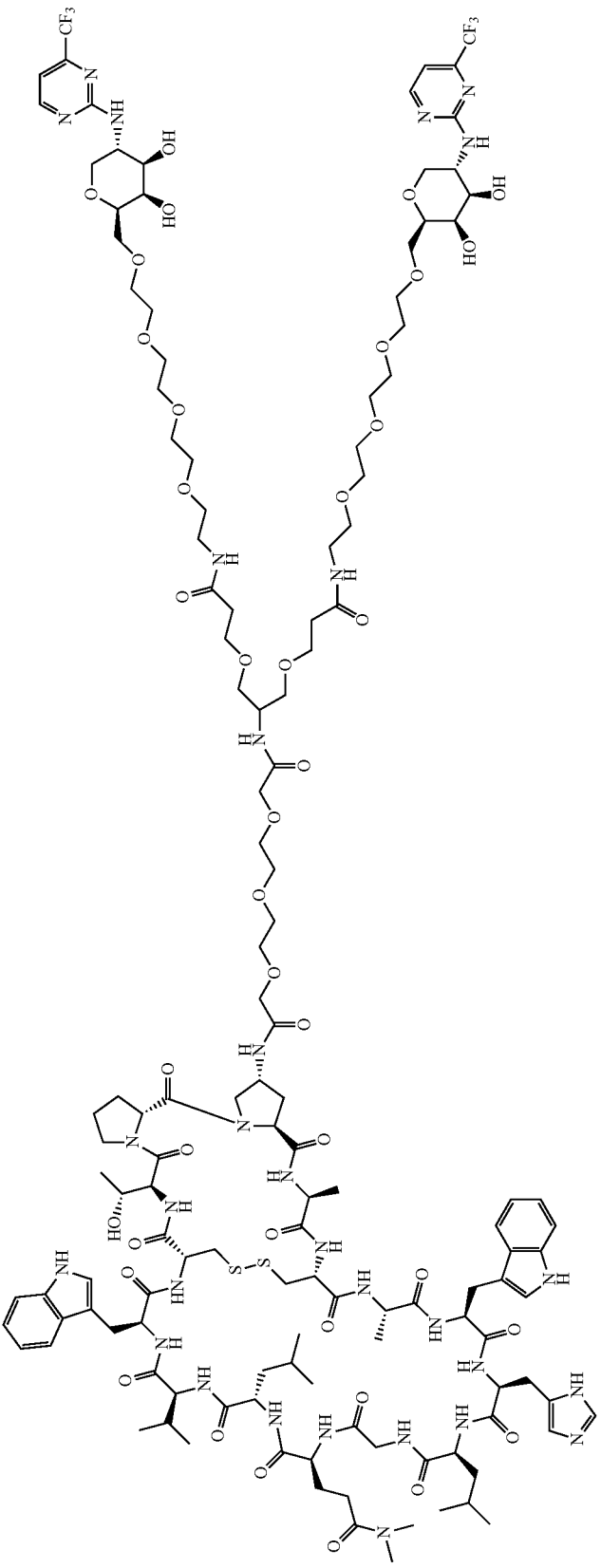

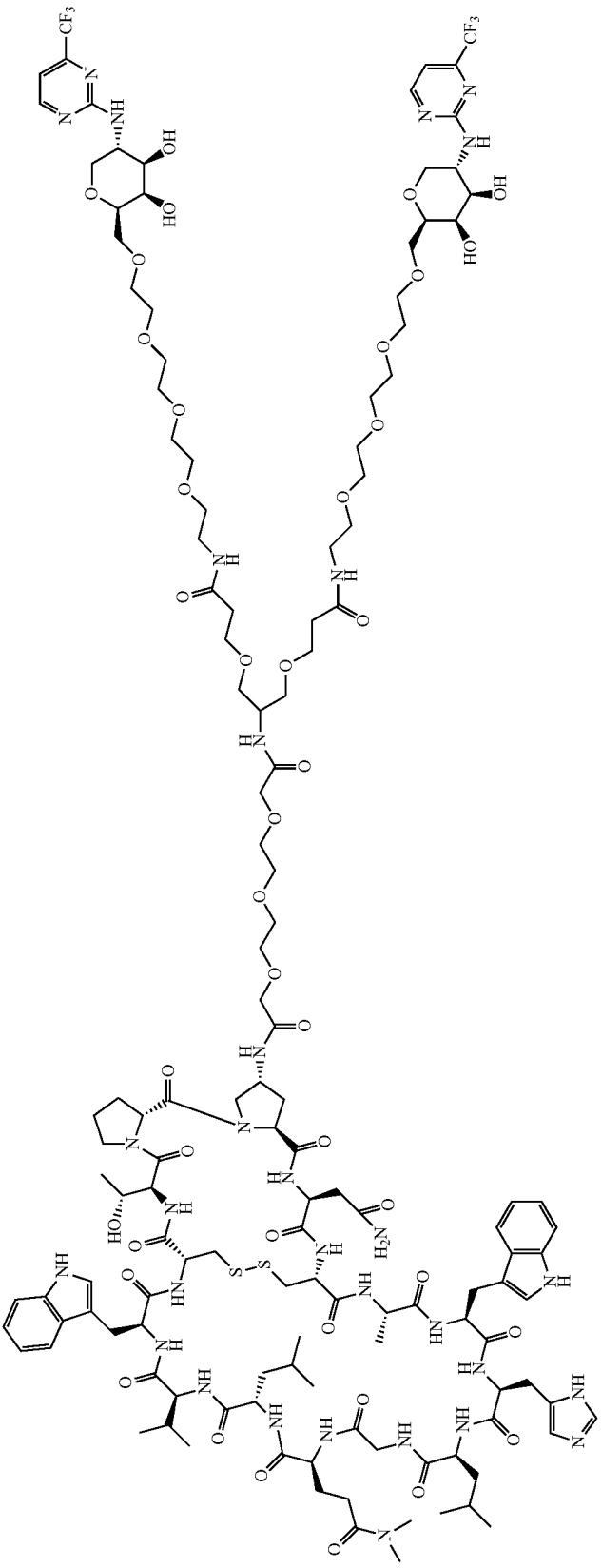

-continued
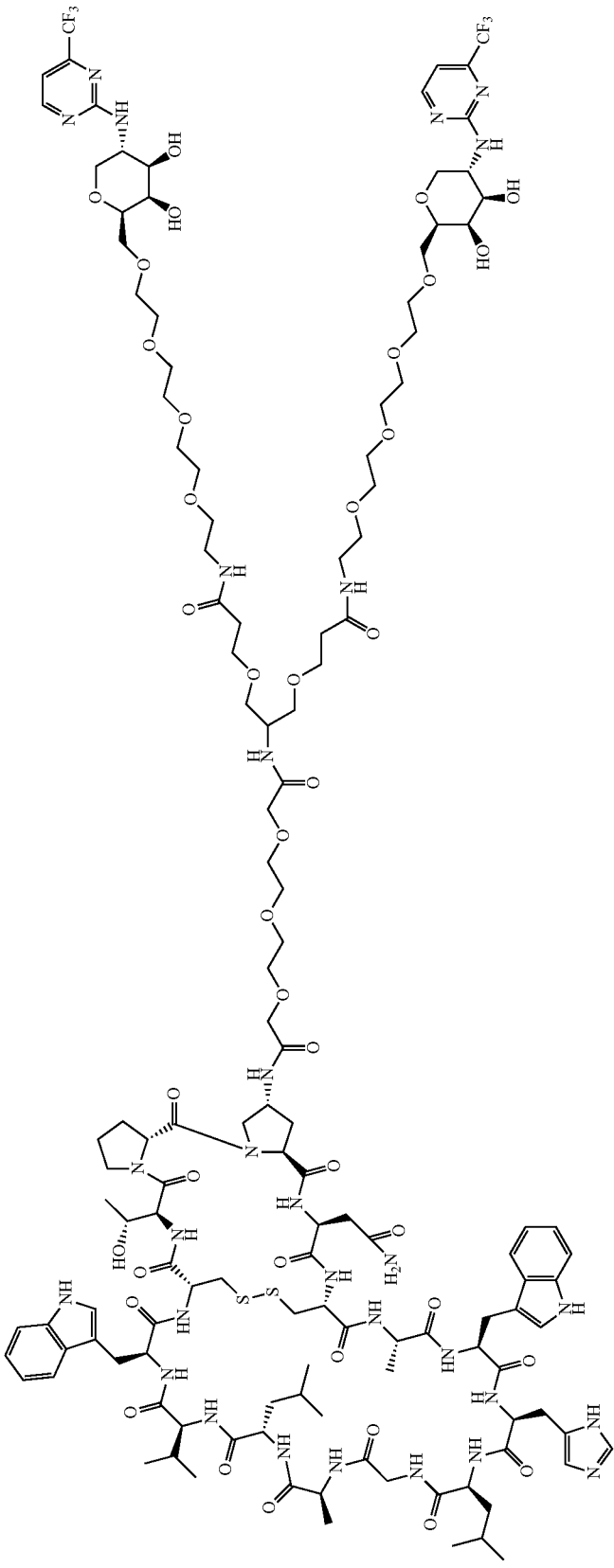

-continued
1711
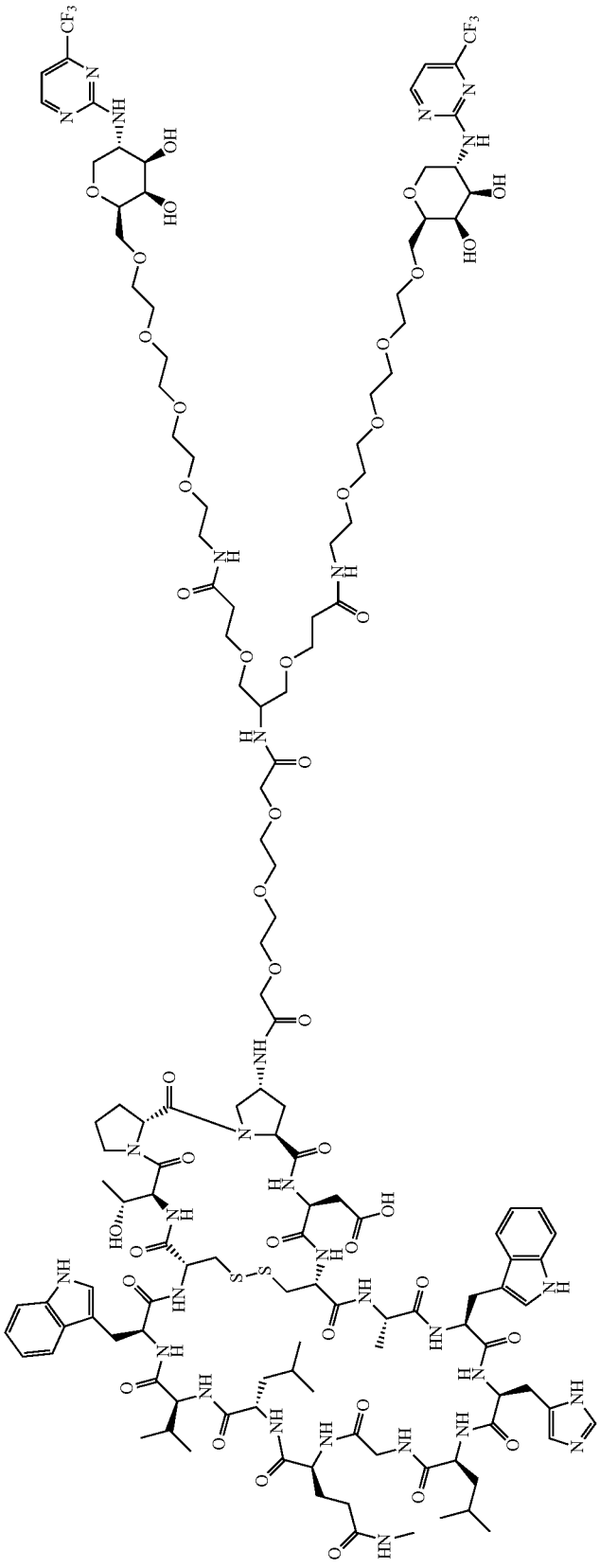
1712

-continued
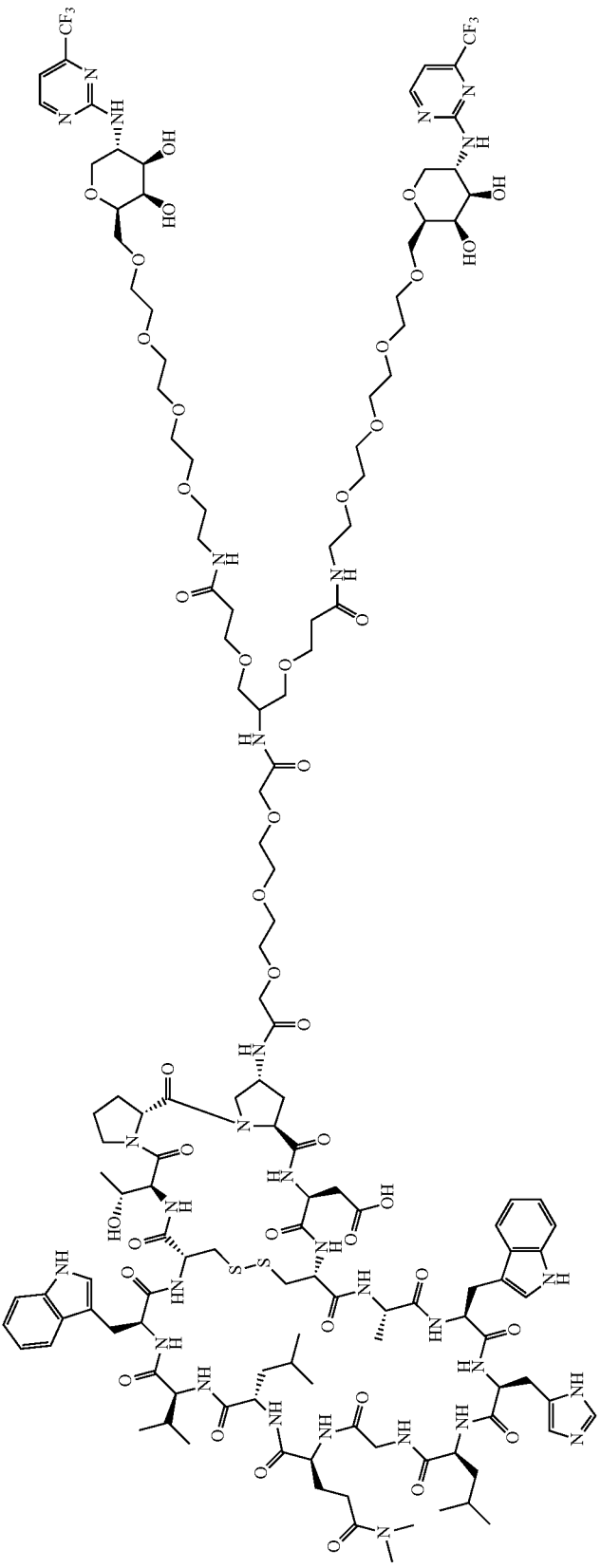

1715 1716
-continued
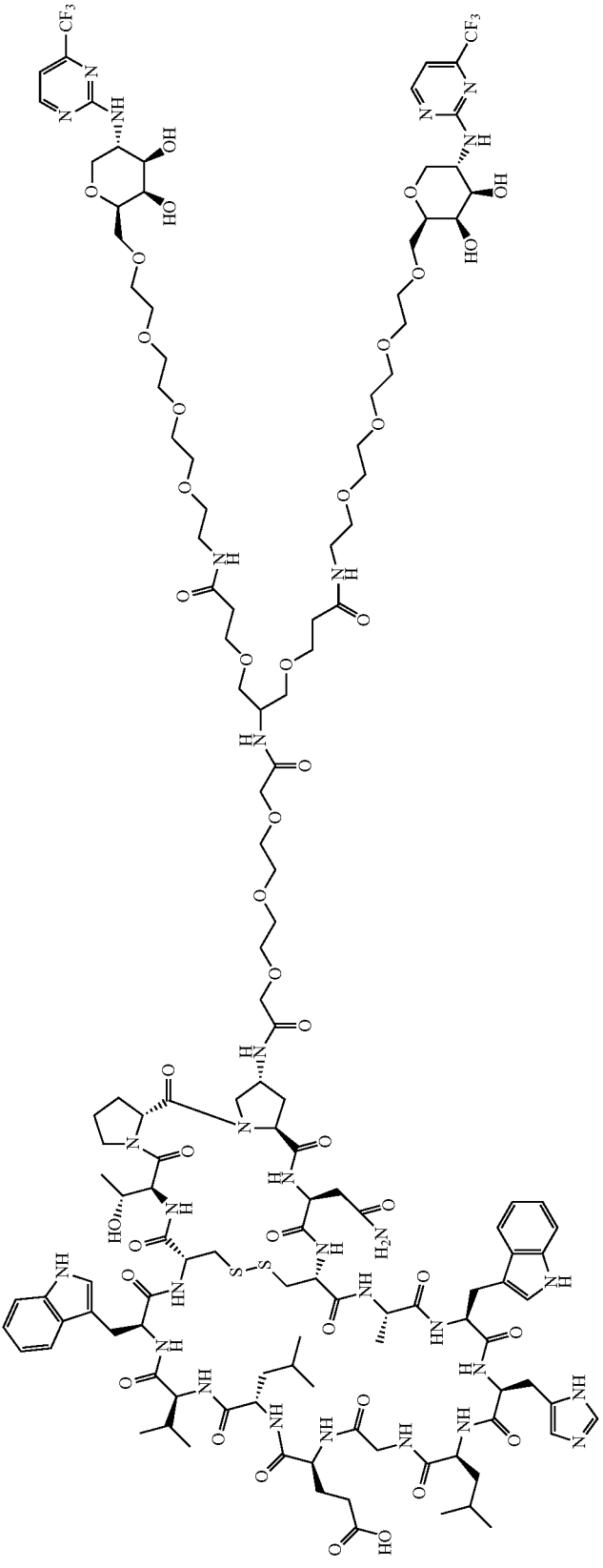

-continued
1717 1718
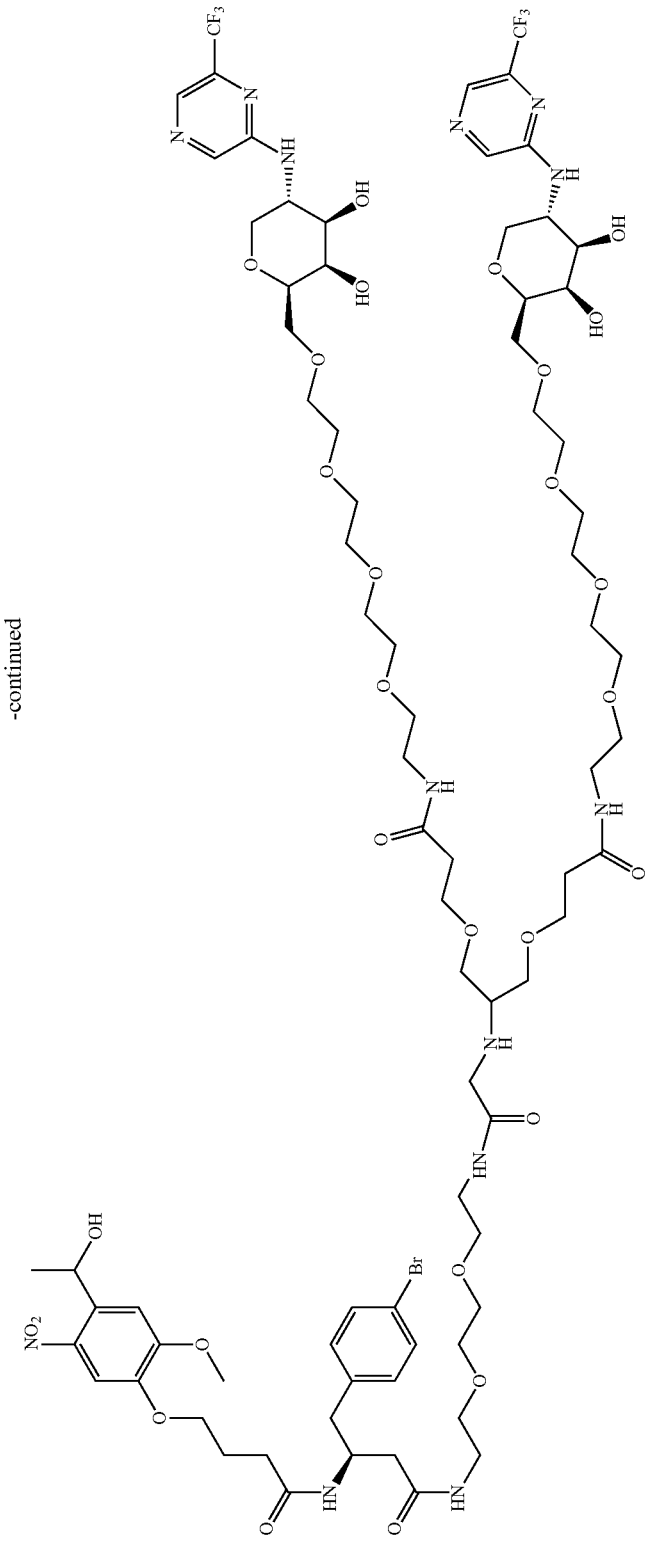

1719 1720
-continued
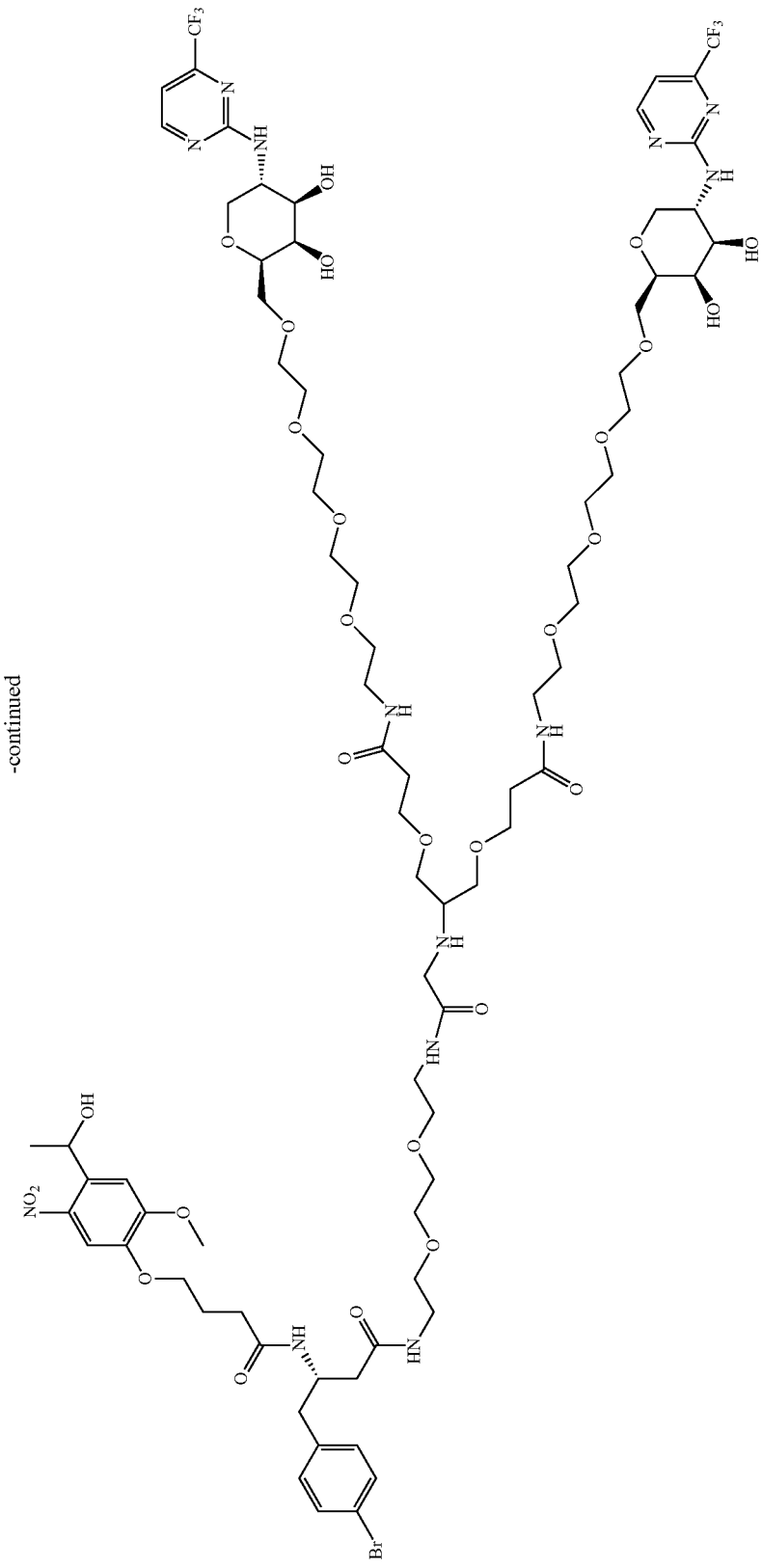

1721 1722
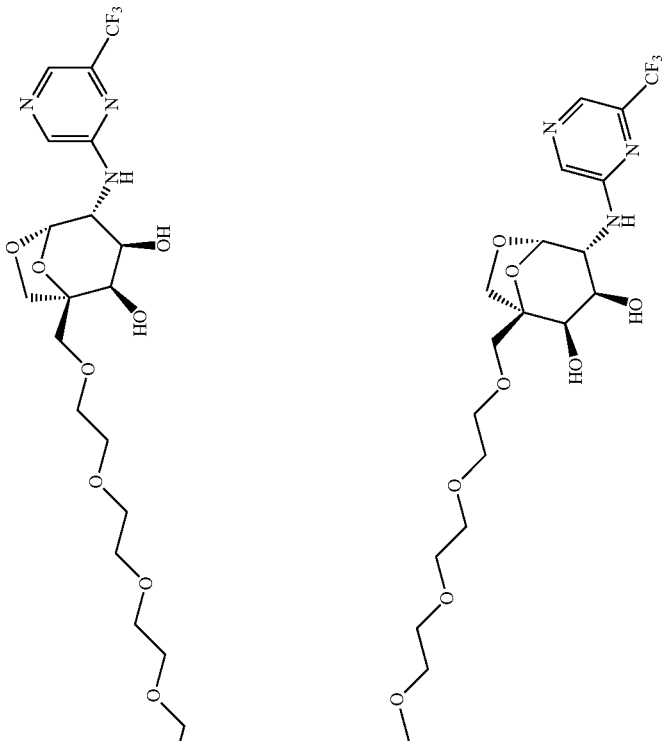

1723 1724
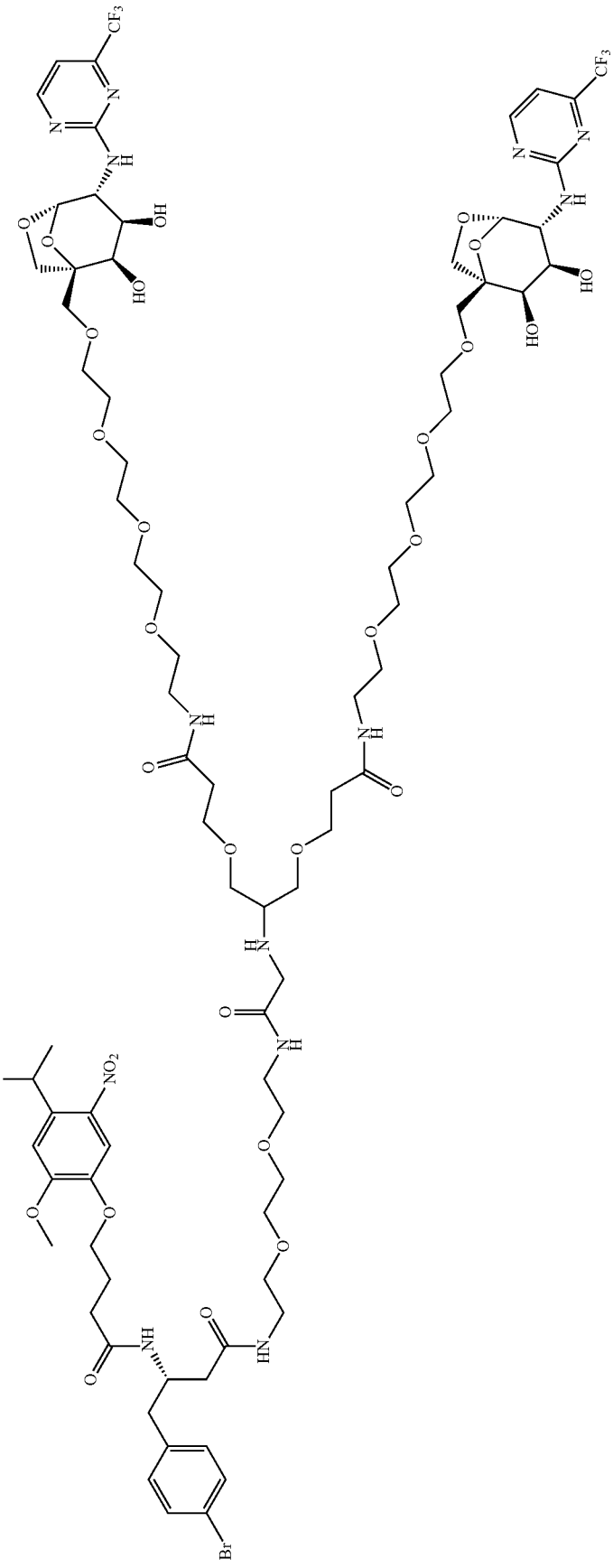

1725 1726
-continued
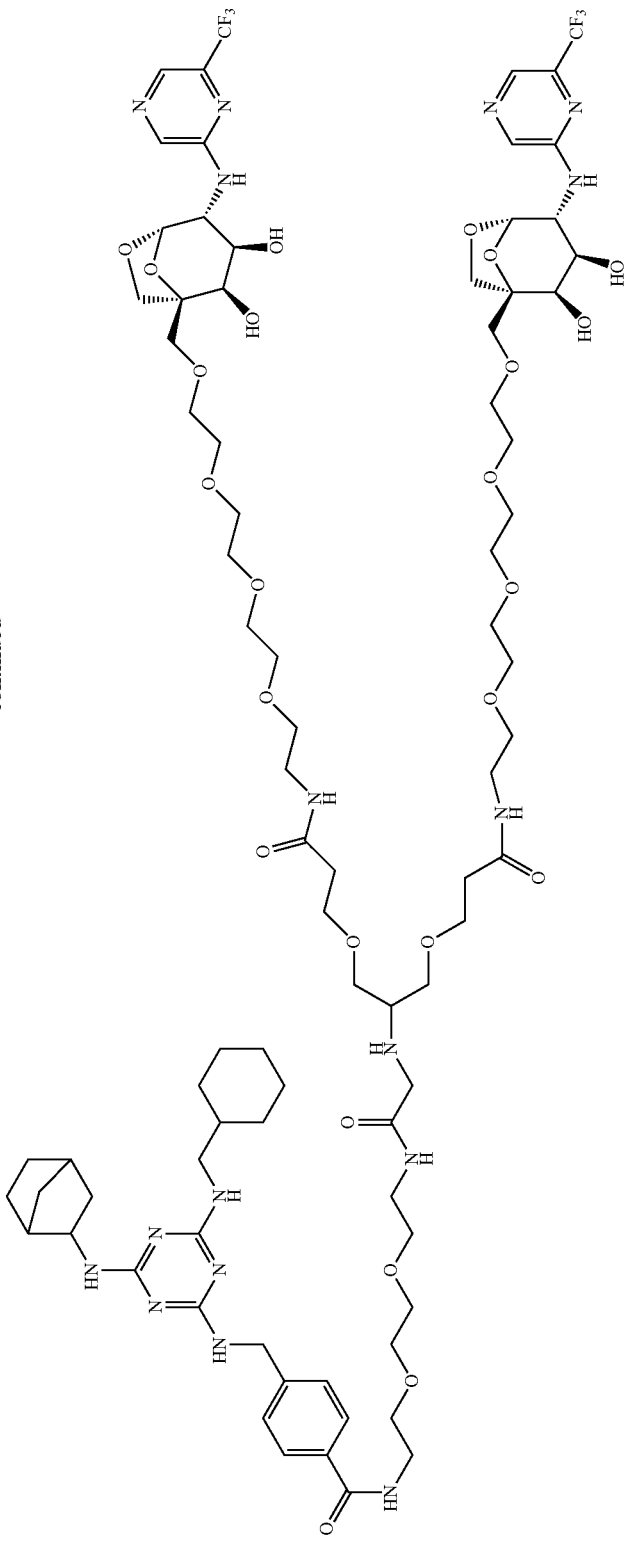

1727 1728
-continued
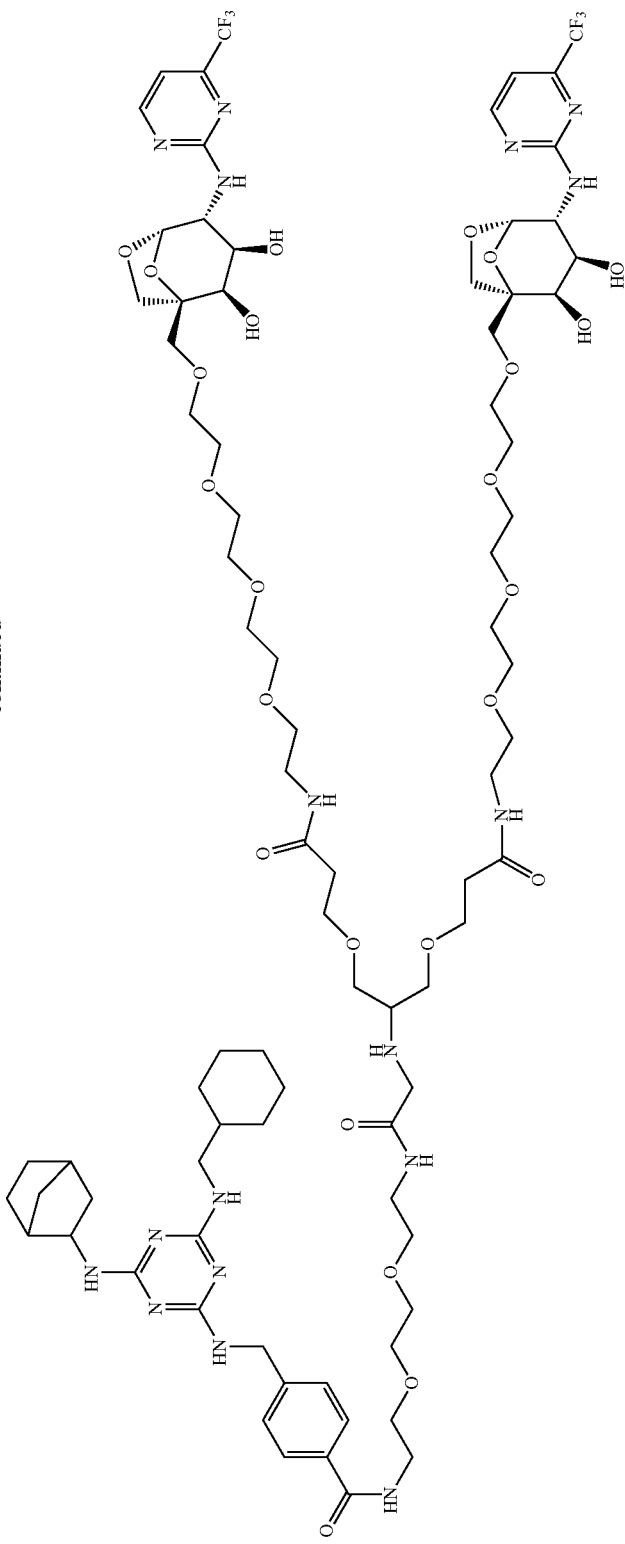

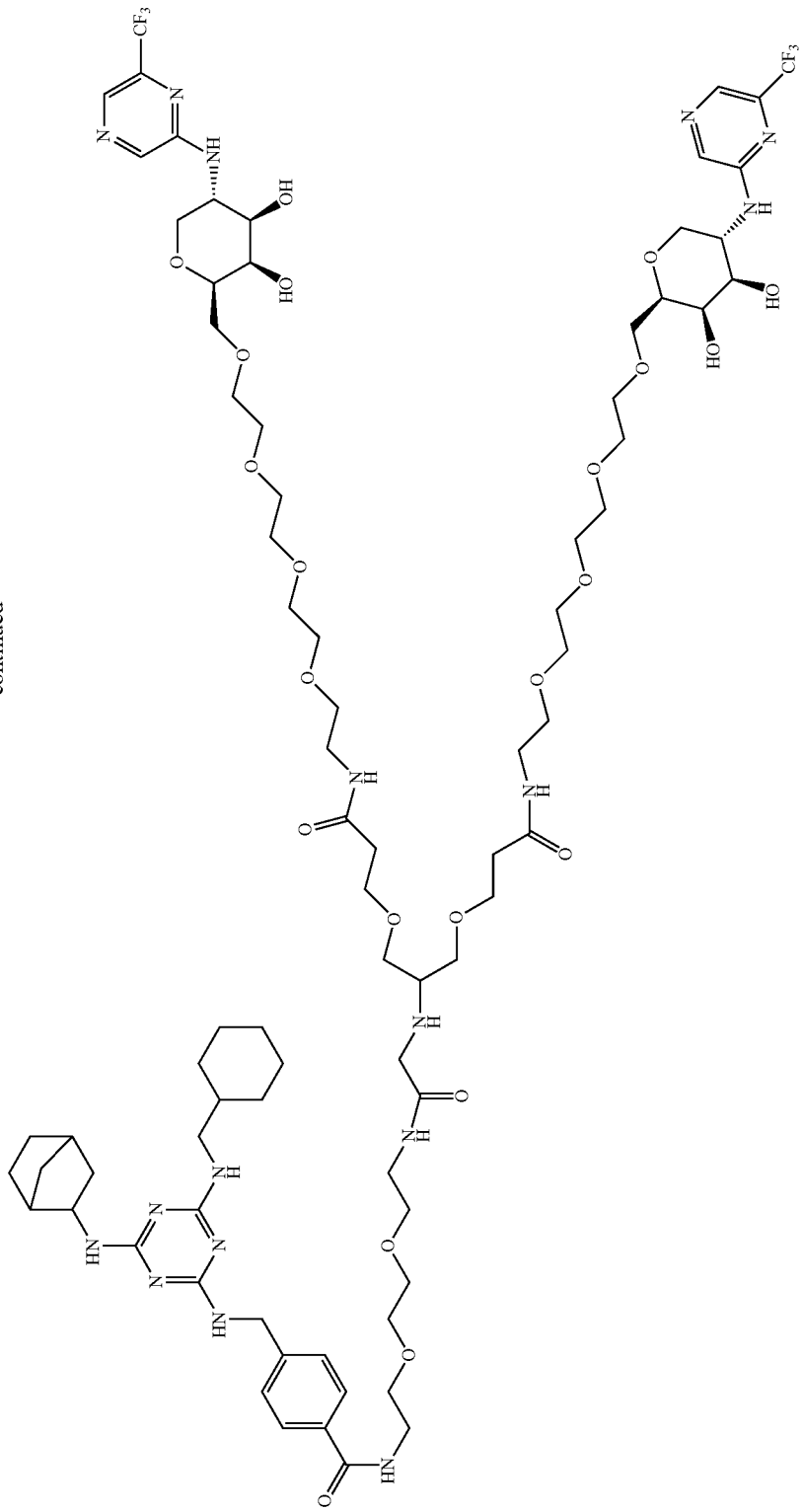

1731 1732
-continued
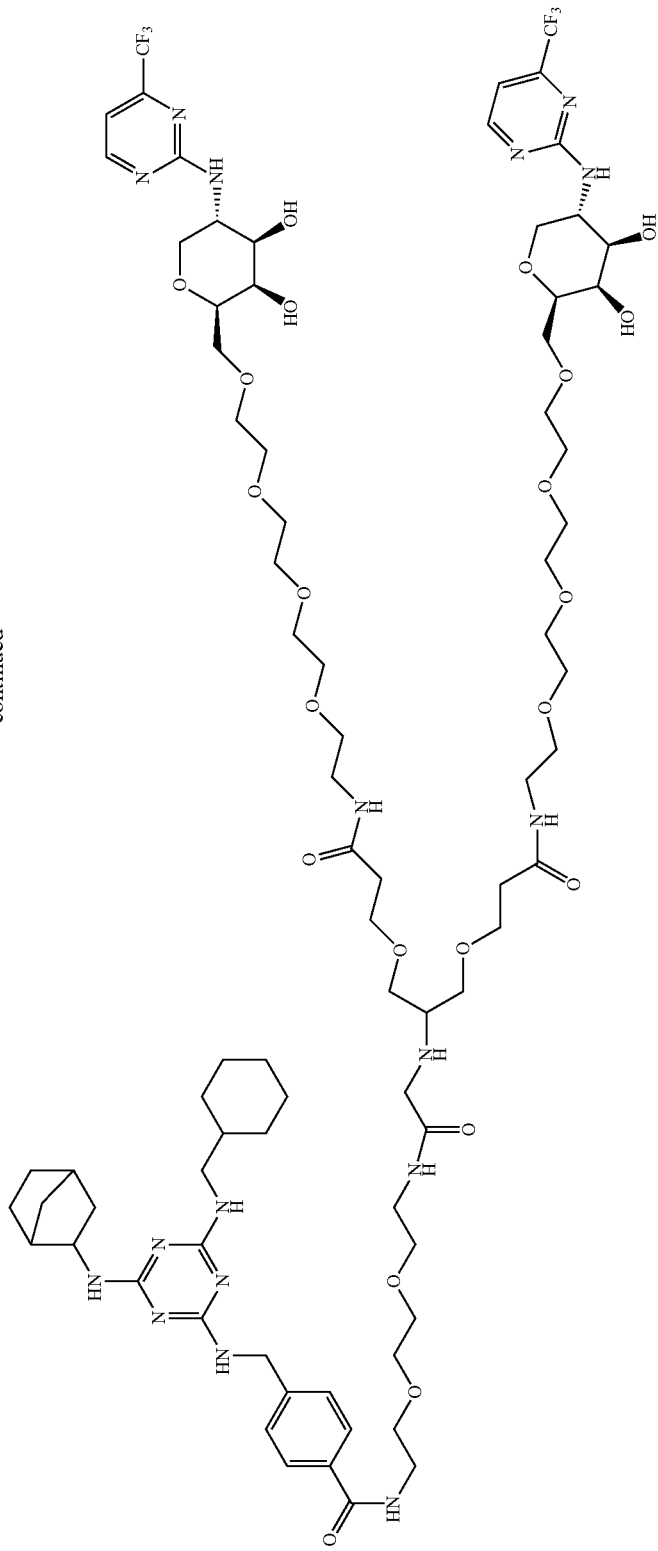

TABLE 2A
ASGPR Ligands of the Present Invention
A1
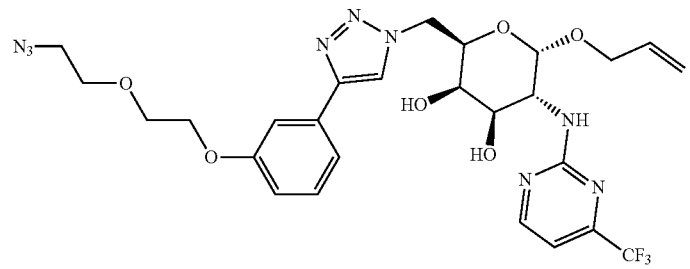 [SMILES: C=CCO[C@H]1O[C@H](Cn2cc(-c3cccc(OCCOCCN=[N+]=[N-])c3)nn2)[C@H](O)[C@H](O)[C@H]1Nc1nccc(C(F)(F)F)n1]
A2
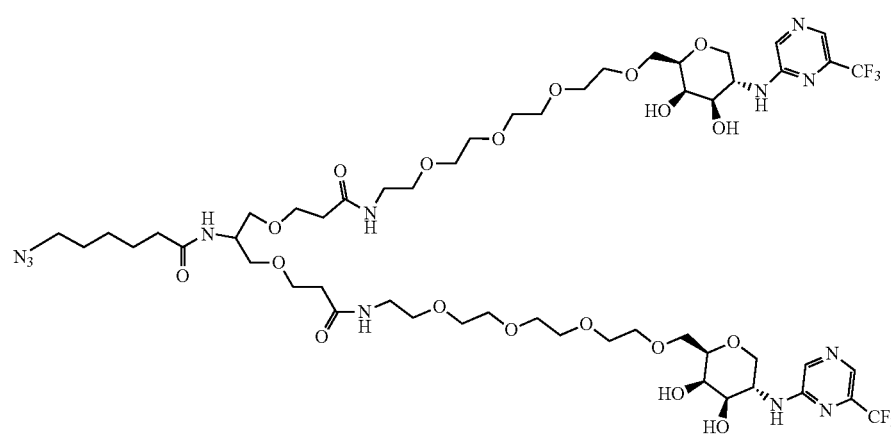 [SMILES: [N-]=[N+]=NCCCCCC(=O)NC(COCCC(=O)NCCOCCOCCOCCOC[C@H]1OC[C@H](Nc2cncc(C(F)(F)F)n2)[C@@H](O)[C@H]1O)COCCC(=O)NCCOCCOCCOCCOC[C@H]1OC[C@H](Nc2cncc(C(F)(F)F)n2)[C@@H](O)[C@H]1O]
A3
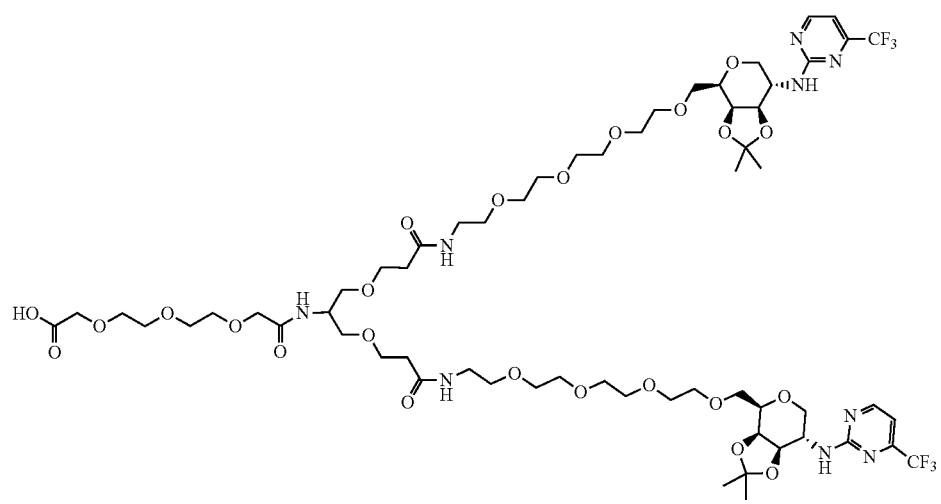 [SMILES: CC1(C)O[C@@H]2[C@H](O1)[C@@H](Nc1nccc(C(F)(F)F)n1)CO[C@@H]2COCCOCCOCCOCCNC(=O)CCOCC(COCCC(=O)NCCOCCOCCOCCOC[C@H]1OC[C@H](Nc2nccc(C(F)(F)F)n2)[C@H]2OC(C)(C)O[C@H]21)NC(=O)COCCOCCOCC(=O)O]
A5
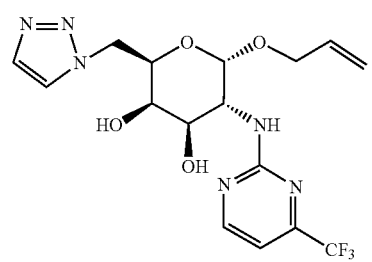 [SMILES: C=CCO[C@H]1O[C@H](Cn2ccnn2)[C@H](O)[C@H](O)[C@H]1Nc1nccc(C(F)(F)F)n1]

TABLE 2A-continued
ASGPR Ligands of the Present Invention
A6
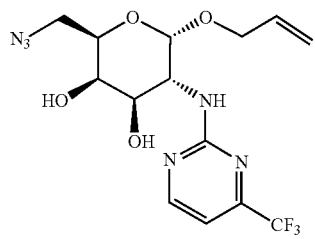 [SMILES: C=CCO[C@H]1O[C@H](CN=[N+]=[N-])[C@H](O)[C@H](O)[C@H]1Nc1nccc(C(F)(F)F)n1]
A7
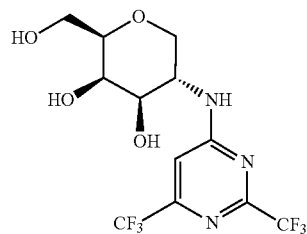
A8
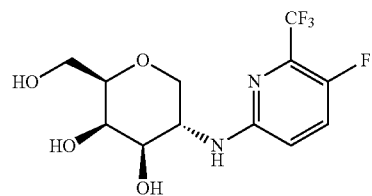 [SMILES: OC[C@H]1OC[C@H](Nc2ccc(F)c(C(F)(F)F)n2)[C@@H](O)[C@H]1O]
A9
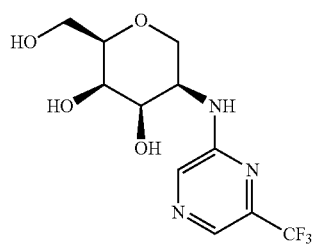 [SMILES: OC[C@H]1OC[C@@H](Nc2cncc(C(F)(F)F)n2)[C@@H](O)[C@H]1O]
A10
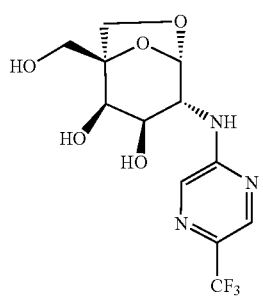 [SMILES: OC[C@@]12CO[C@@H](O1)[C@H](Nc1cnc(C(F)(F)F)cn1)[C@@H](O)[C@H]2O]

TABLE 2A-continued
ASGPR Ligands of the Present Invention
A11
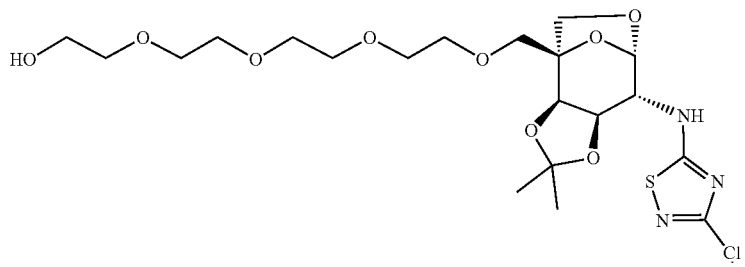
TABLE 2B
ASGPR Ligands of the Present Invention
A16
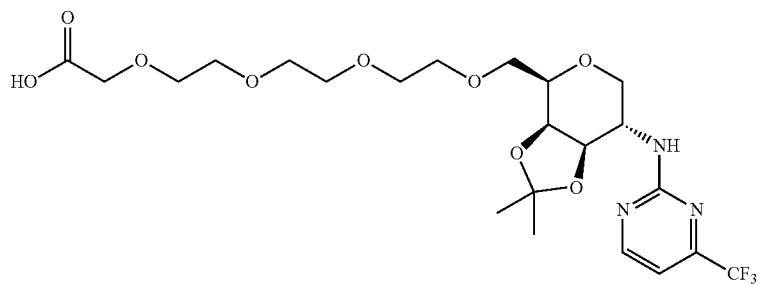 [SMILES: CC1(C)O[C@@H]2[C@H](O1)[C@@H](Nc1nccc(C(F)(F)F)n1)CO[C@@H]2COCCOCCOCCOCC(=O)O]
A18
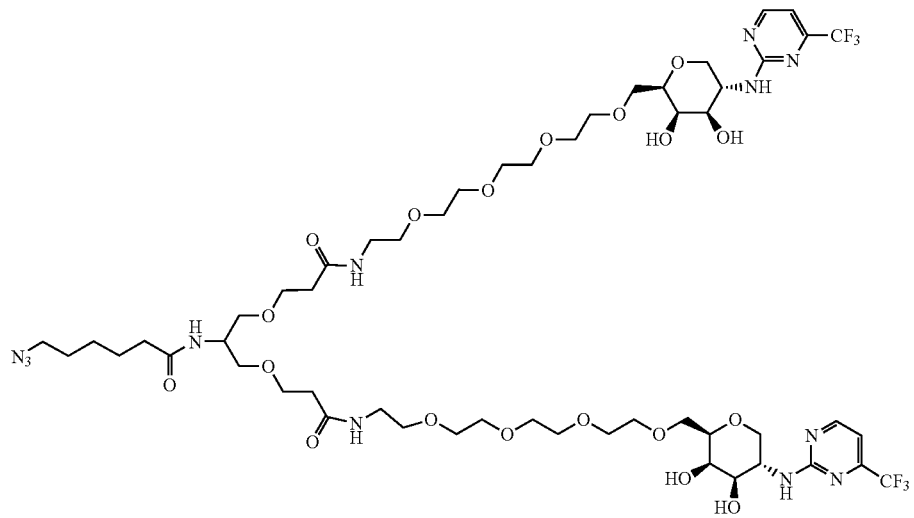 [SMILES: [N-]=[N+]=NCCCCCC(=O)NC(COCCC(=O)NCCOCCOCCOCCOC[C@H]1OC[C@H](Nc2nccc(C(F)(F)F)n2)[C@@H](O)[C@H]1O)COCCC(=O)NCCOCCOCCOCCOC[C@H]1OC[C@H](Nc2nccc(C(F)(F)F)n2)[C@@H](O)[C@H]1O]

TABLE 2B-continued
ASGPR Ligands of the Present Invention
A19
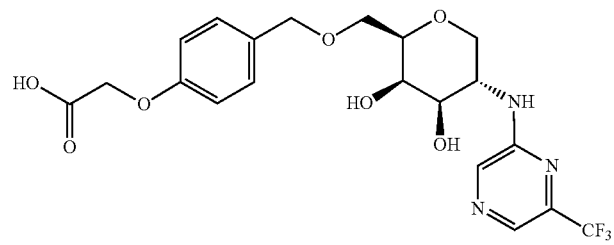 [SMILES: O=C(O)COc1ccc(COC[C@H]2OC[C@H](Nc3cncc(C(F)(F)F)n3)[C@@H](O)[C@H]2O)cc1]
A20
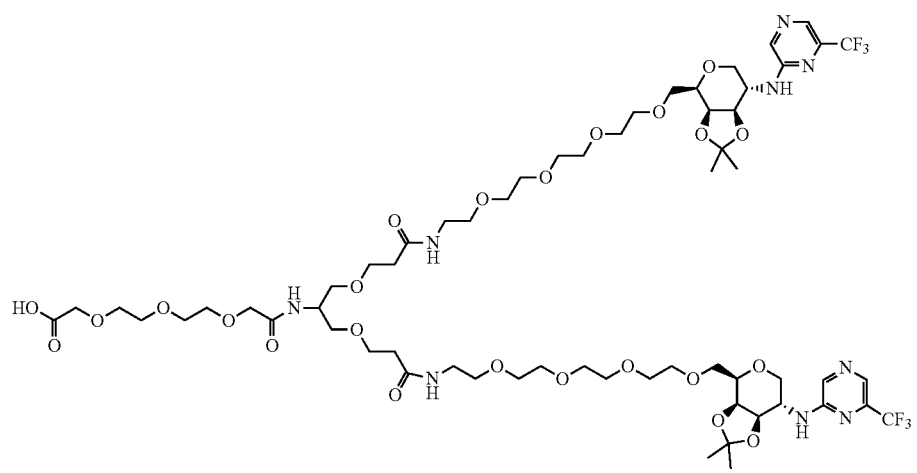 [SMILES: CC1(C)O[C@@H]2[C@H](O1)[C@@H](Nc1cncc(C(F)(F)F)n1)CO[C@@H]2COCCOCCOCCOCCNC(=O)CCOCC(COCCC(=O)NCCOCCOCCOCCOC[C@H]1OC[C@H](Nc2cncc(C(F)(F)F)n2)[C@H]2OC(C)(C)O[C@H]21)NC(=O)COCCOCCOCC(=O)O]
A21
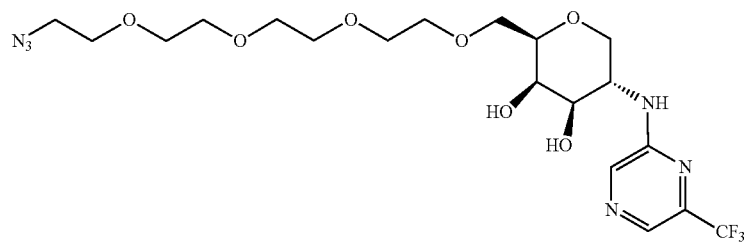 [SMILES: [N-]=[N+]=NCCOCCOCCOCCOC[C@H]1OC[C@H](Nc2cncc(C(F)(F)F)n2)[C@@H](O)[C@H]1O]

TABLE 2B-continued
ASGPR Ligands of the Present Invention
A22
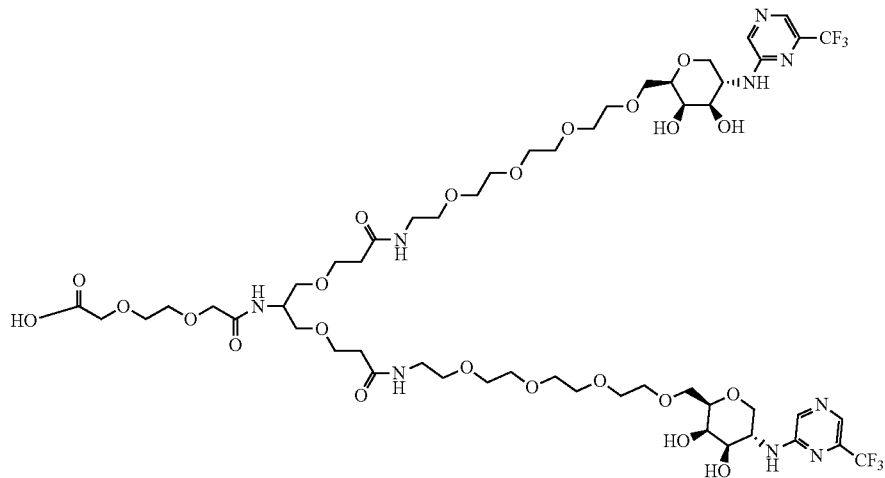 [SMILES: O=C(O)COCCOCC(=O)NC(COCCC(=O)NCCOCCOCCOCCOC[C@H]1OC[C@H](Nc2cncc(C(F)(F)F)n2)[C@@H](O)[C@H]1O)COCCC(=O)NCCOCCOCCOCCOC[C@H]1OC[C@H](Nc2cncc(C(F)(F)F)n2)[C@@H](O)[C@H]1O]
A23
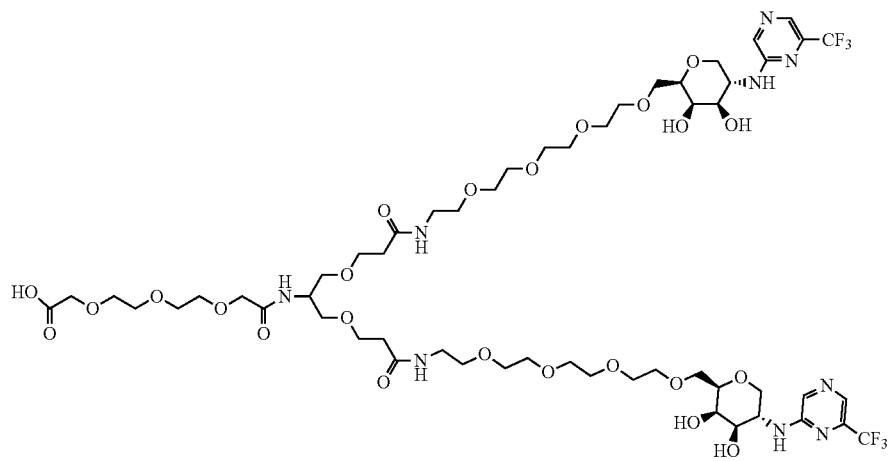 [SMILES: O=C(O)COCCOCCOCC(=O)NC(COCCC(=O)NCCOCCOCCOCCOC[C@H]1OC[C@H](Nc2cncc(C(F)(F)F)n2)[C@@H](O)[C@H]1O)COCCC(=O)NCCOCCOCCOCCOC[C@H]1OC[C@H](Nc2cncc(C(F)(F)F)n2)[C@@H](O)[C@H]1O]
A24
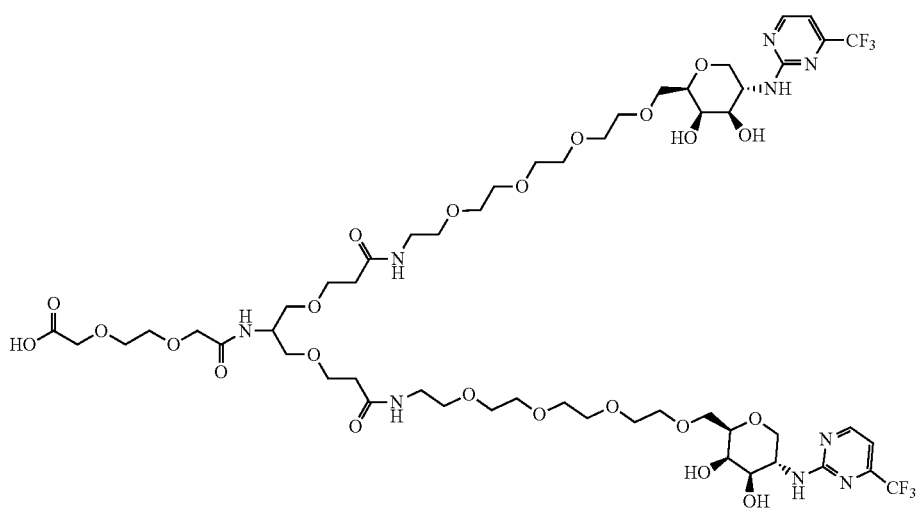 [SMILES: O=C(O)COCCOCC(=O)NC(COCCC(=O)NCCOCCOCCOCCOC[C@H]1OC[C@H](Nc2nccc(C(F)(F)F)n2)[C@@H](O)[C@H]1O)COCCC(=O)NCCOCCOCCOCCOC[C@H]1OC[C@H](Nc2nccc(C(F)(F)F)n2)[C@@H](O)[C@H]1O]

TABLE 2B-continued
ASGPR Ligands of the Present Invention
A25
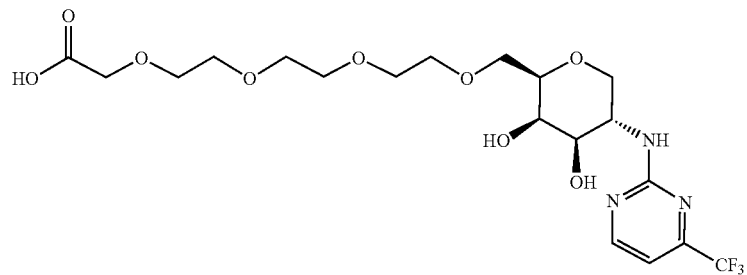 [SMILES: O=C(O)COCCOCCOCCOC[C@H]1OC[C@H](Nc2nccc(C(F)(F)F)n2)[C@@H](O)[C@H]1O]
A26
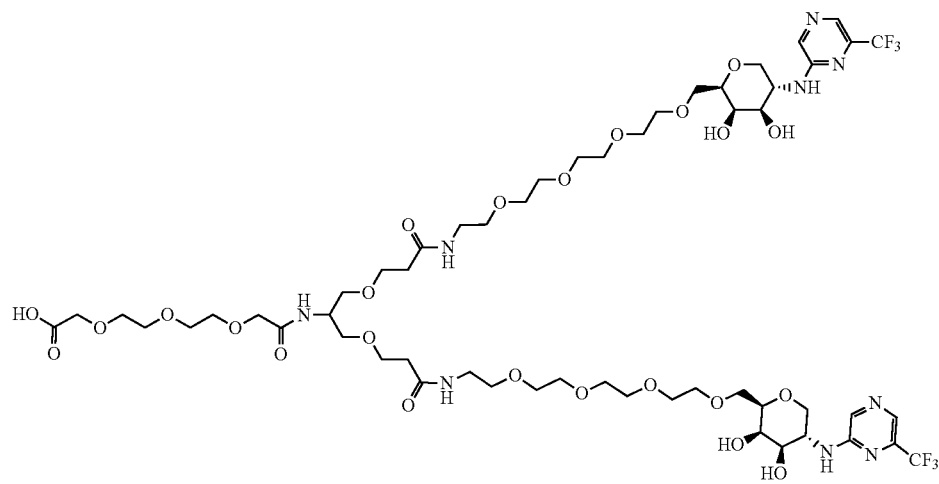 [SMILES: O=C(O)COCCOCCOCC(=O)NC(COCCC(=O)NCCOCCOCCOCCOC[C@H]1OC[C@H](Nc2cncc(C(F)(F)F)n2)[C@@H](O)[C@H]1O)COCCC(=O)NCCOCCOCCOCCOC[C@H]1OC[C@H](Nc2cncc(C(F)(F)F)n2)[C@@H](O)[C@H]1O]
A27
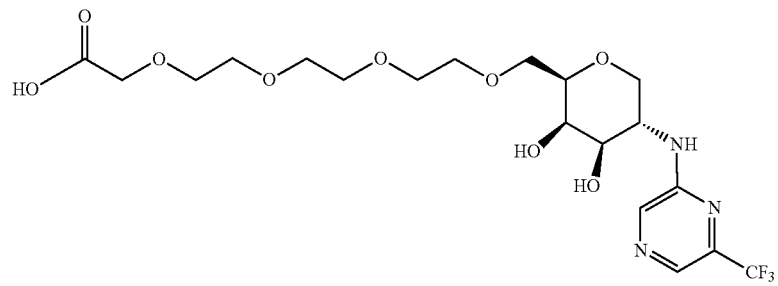 [SMILES: O=C(O)COCCOCCOCCOC[C@H]1OC[C@H](Nc2cncc(C(F)(F)F)n2)[C@@H](O)[C@H]1O]

TABLE 2B-continued
ASGPR Ligands of the Present Invention
A28
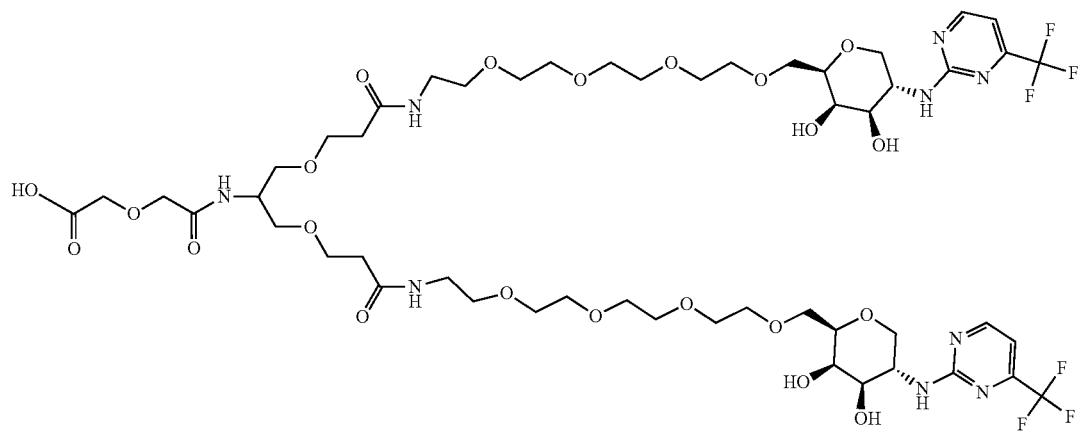 [SMILES: O=C(O)COCC(=O)NC(COCCC(=O)NCCOCCOCCOCCOC[C@H]1OC[C@H](Nc2nccc(C(F)(F)F)n2)[C@@H](O)[C@H]1O)COCCC(=O)NCCOCCOCCOCCOC[C@H]1OC[C@H](Nc2nccc(C(F)(F)F)n2)[C@@H](O)[C@H]1O]
A29
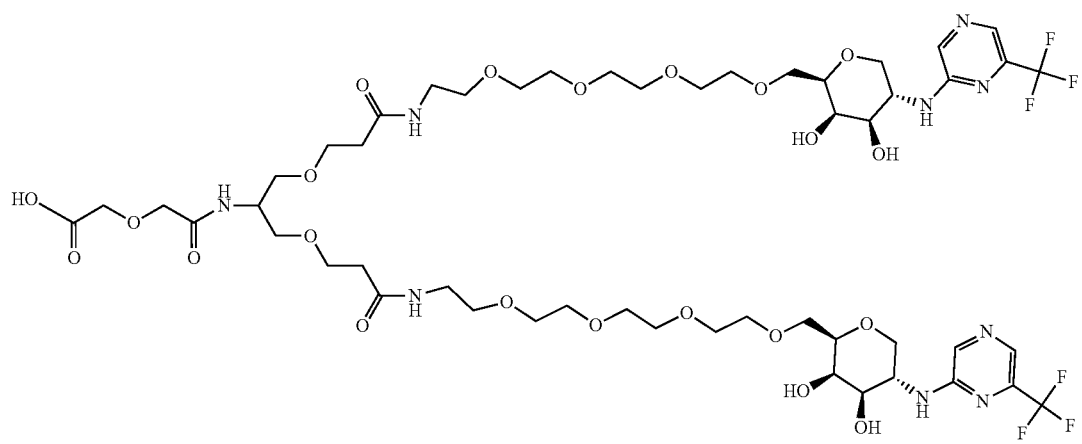 [SMILES: O=C(O)COCC(=O)NC(COCCC(=O)NCCOCCOCCOCCOC[C@H]1OC[C@H](Nc2cncc(C(F)(F)F)n2)[C@@H](O)[C@H]1O)COCCC(=O)NCCOCCOCCOCCOC[C@H]1OC[C@H](Nc2cncc(C(F)(F)F)n2)[C@@H](O)[C@H]1O]
A30
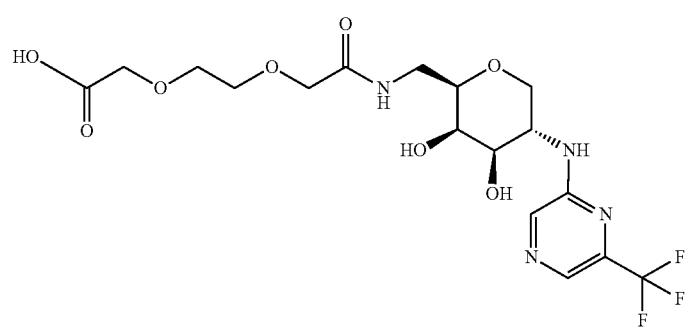 [SMILES: O=C(O)COCCOCC(=O)NC[C@H]1OC[C@H](Nc2cncc(C(F)(F)F)n2)[C@@H](O)[C@H]1O]
A31
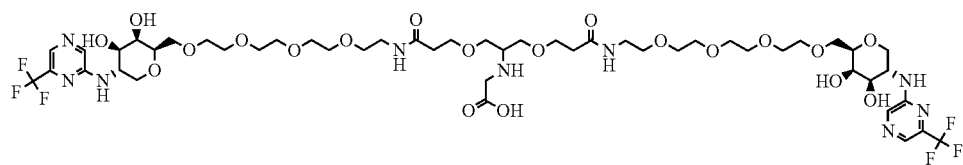 [SMILES: O=C(O)CNC(COCCC(=O)NCCOCCOCCOCCOC[C@H]1OC[C@H](Nc2cncc(C(F)(F)F)n2)[C@@H](O)[C@H]1O)COCCC(=O)NCCOCCOCCOCCOC[C@H]1OC[C@H](Nc2cncc(C(F)(F)F)n2)[C@@H](O)[C@H]1O]

TABLE 2B-continued
ASGPR Ligands of the Present Invention
A32
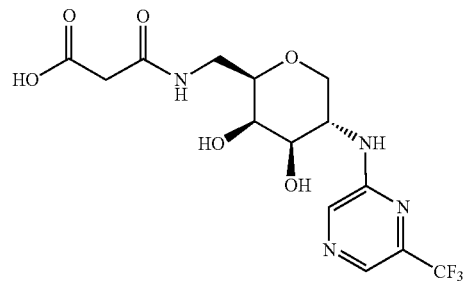 [SMILES: O=C(O)CC(=O)NC[C@H]1OC[C@H](Nc2cncc(C(F)(F)F)n2)[C@@H](O)[C@H]1O]
A33
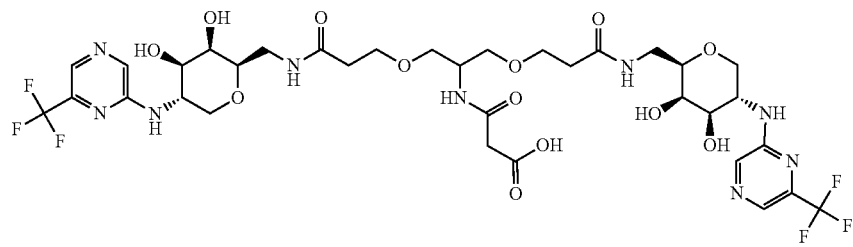 [SMILES: O=C(O)CC(=O)NC(COCCC(=O)NC[C@H]1OC[C@H](Nc2cncc(C(F)(F)F)n2)[C@@H](O)[C@H]1O)COCCC(=O)NC[C@H]1OC[C@H](Nc2cncc(C(F)(F)F)n2)[C@@H](O)[C@H]1O]
A34
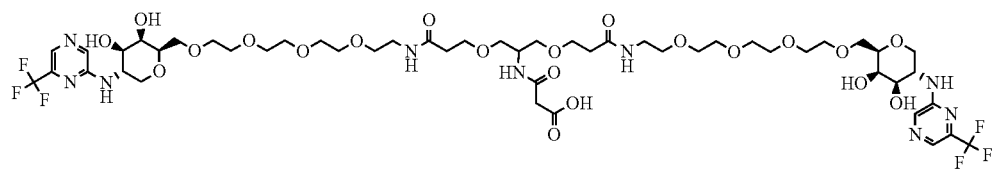 [SMILES: O=C(O)CC(=O)NC(COCCC(=O)NCCOCCOCCOCCOC[C@H]1OC[C@H](Nc2cncc(C(F)(F)F)n2)[C@@H](O)[C@H]1O)COCCC(=O)NCCOCCOCCOCCOC[C@H]1OC[C@H](Nc2cncc(C(F)(F)F)n2)[C@@H](O)[C@H]1O]
A35
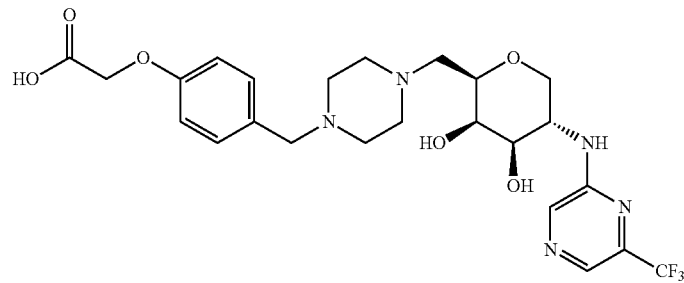 [SMILES: O=C(O)COc1ccc(CN2CCN(C[C@H]3OC[C@H](Nc4cncc(C(F)(F)F)n4)[C@@H](O)[C@H]3O)CC2)cc1]

TABLE 2B-continued
ASGPR Ligands of the Present Invention
A36
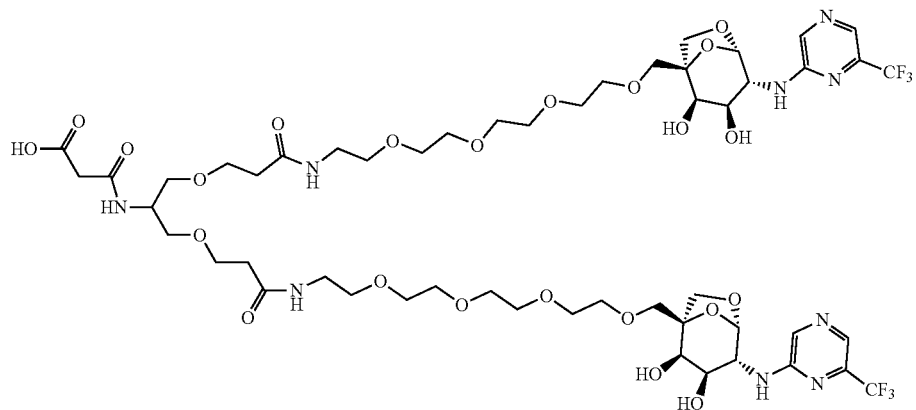 [SMILES: O=C(O)CC(=O)NC(COCCC(=O)NCCOCCOCCOCCOC[C@@]12CO[C@@H](O1)[C@H](Nc1cncc(C(F)(F)F)n1)[C@@H](O)[C@H]2O)COCCC(=O)NCCOCCOCCOCCOC[C@@]12CO[C@@H](O1)[C@H](Nc1cncc(C(F)(F)F)n1)[C@@H](O)[C@H]2O]
A127
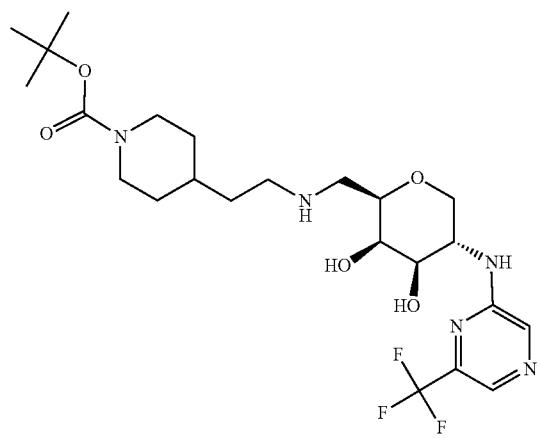 [SMILES: CC(C)(C)OC(=O)N1CCC(CCNC[C@H]2OC[C@H](Nc3cncc(C(F)(F)F)n3)[C@@H](O)[C@H]2O)CC1]
A128
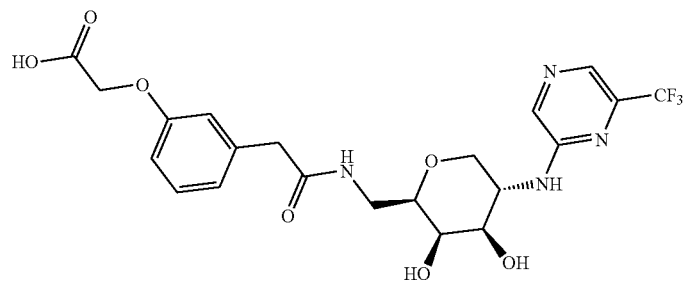 [SMILES: O=C(O)COc1cccc(CC(=O)NC[C@H]2OC[C@H](Nc3cncc(C(F)(F)F)n3)[C@@H](O)[C@H]2O)c1]
A129
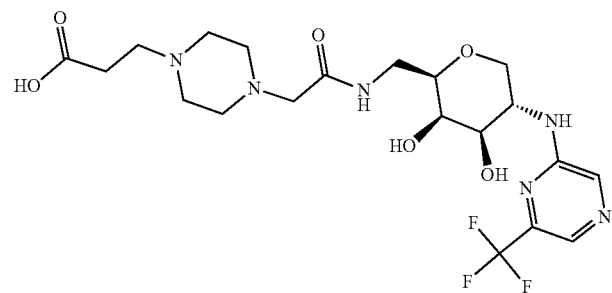 [SMILES: O=C(O)CCN1CCN(CC(=O)NC[C@H]2OC[C@H](Nc3cncc(C(F)(F)F)n3)[C@@H](O)[C@H]2O)CC1]

TABLE 2B-continued
ASGPR Ligands of the Present Invention
A130
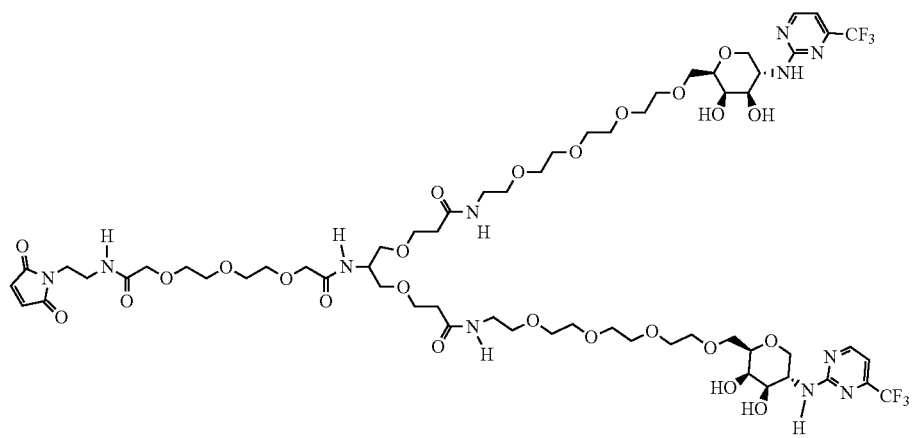 [SMILES: O=C(CCOCC(COCCC(=O)NCCOCCOCCOCCOC[C@H]1OC[C@H](Nc2nccc(C(F)(F)F)n2)[C@@H](O)[C@H]1O)NC(=O)COCCOCCOCC(=O)NCCN1C(=O)C=CC1=O)NCCOCCOCCOCCOC[C@H]1OC[C@H](Nc2nccc(C(F)(F)F)n2)[C@@H](O)[C@H]1O]
A131
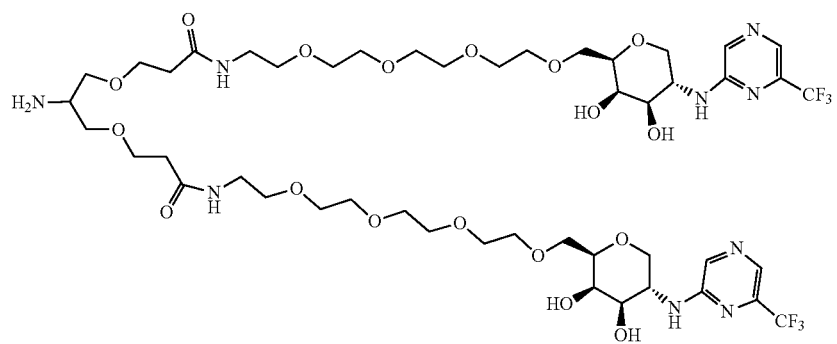 [SMILES: NC(COCCC(=O)NCCOCCOCCOCCOC[C@H]1OC[C@H](Nc2cncc(C(F)(F)F)n2)[C@@H](O)[C@H]1O)COCCC(=O)NCCOCCOCCOCCOC[C@H]1OC[C@H](Nc2cncc(C(F)(F)F)n2)[C@@H](O)[C@H]1O]
A132
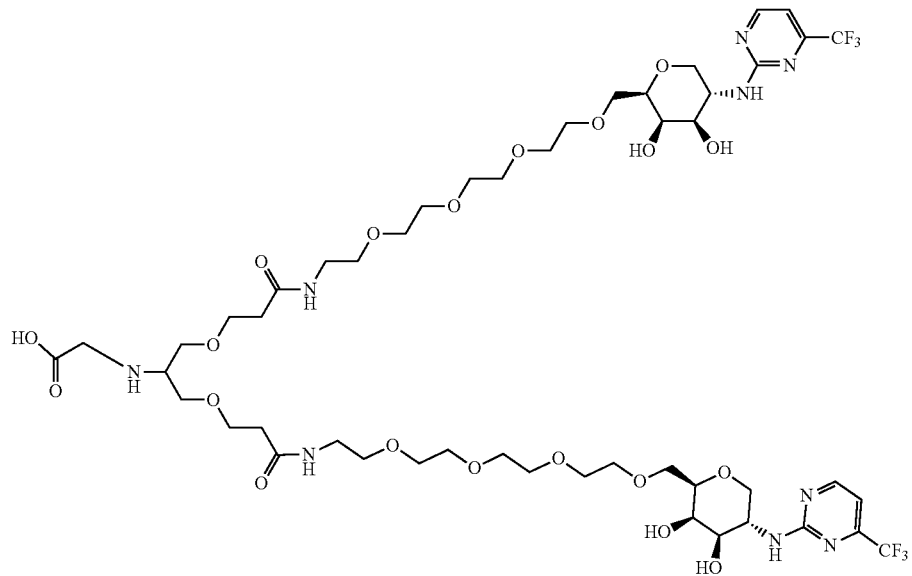 [SMILES: O=C(O)CNC(COCCC(=O)NCCOCCOCCOCCOC[C@H]1OC[C@H](Nc2nccc(C(F)(F)F)n2)[C@@H](O)[C@H]1O)COCCC(=O)NCCOCCOCCOCCOC[C@H]1OC[C@H](Nc2nccc(C(F)(F)F)n2)[C@@H](O)[C@H]1O]

TABLE 2B-continued
ASGPR Ligands of the Present Invention
A133
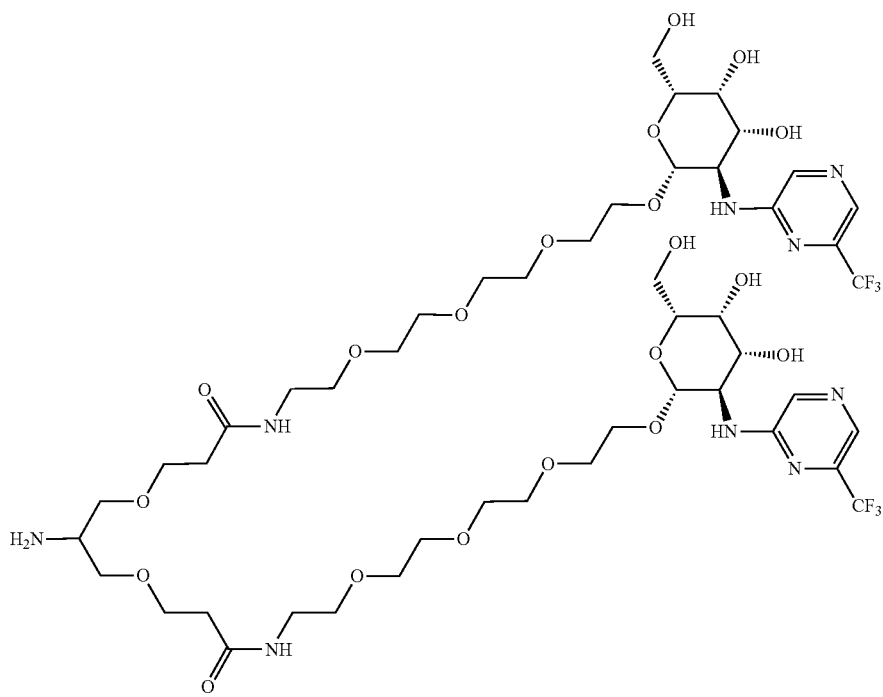 [SMILES: NC(COCCC(=O)NCCOCCOCCOCCO[C@@H]1O[C@H](CO)[C@H](O)[C@H](O)[C@H]1Nc1cncc(C(F)(F)F)n1)COCCC(=O)NCCOCCOCCOCCO[C@@H]1O[C@H](CO)[C@H](O)[C@H](O)[C@H]1Nc1cncc(C(F)(F)F)n1]
40
TABLE 3A
Tested Intermediates
Intermediate 1
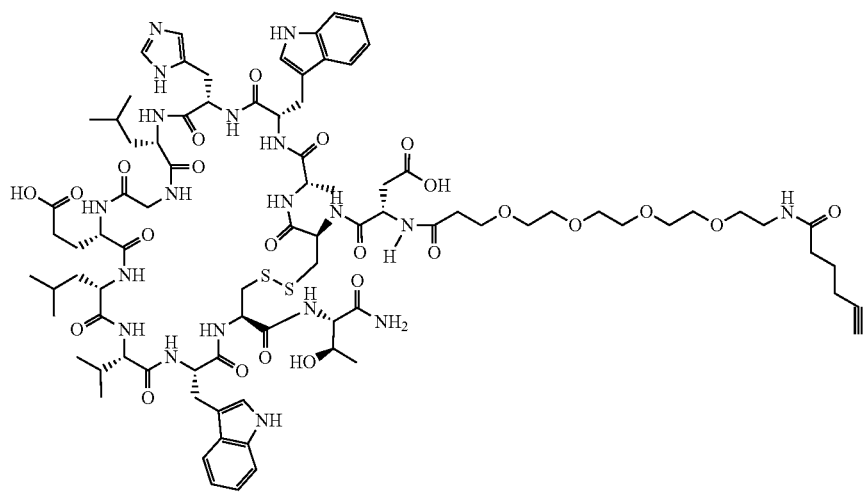 [SMILES: C#CCCCC(=O)NCCOCCOCCOCCOCCC(=O)N[C@@H](CC(=O)O)C(=O)N[C@H]1CSSC[C@@H](C(=O)N[C@H](C(N)=O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc2cnc[nH]2)NC(=O)[C@H](Cc2c[nH]c3ccccc23)NC(=O)[C@H](C)NC1=O]

TABLE 3A-continued
Tested Intermediates
Intermediate 2
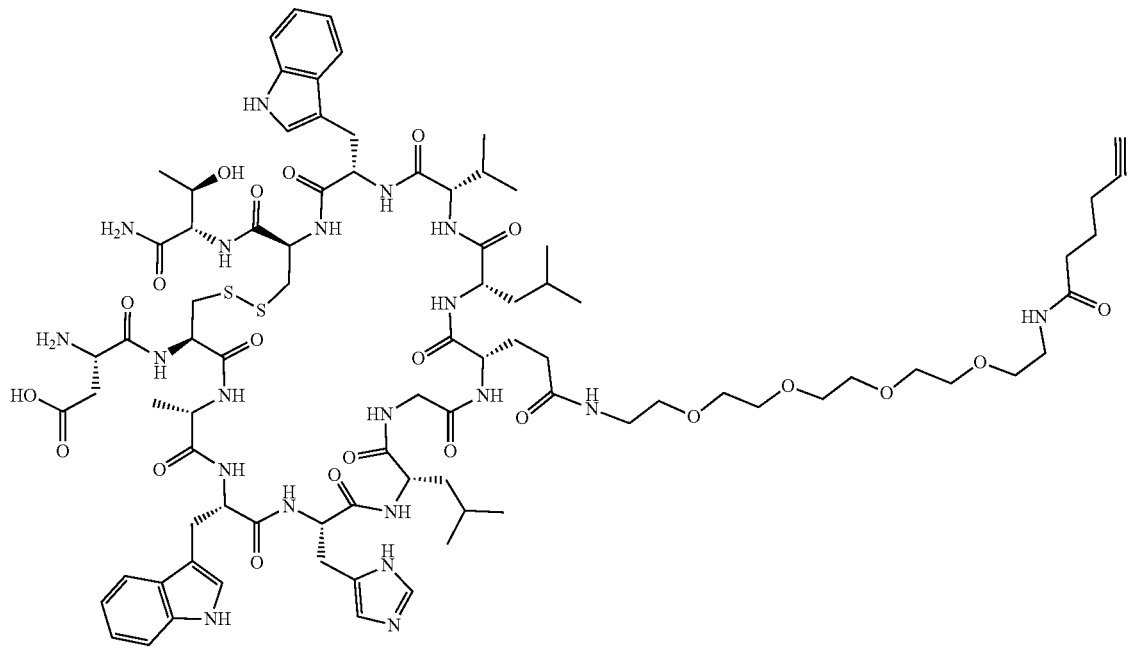 [SMILES: C#CCCCC(=O)NCCOCCOCCOCCOCCNC(=O)CC[C@@H]1NC(=O)CNC(=O)[C@H](CC(C)C)NC(=O)[C@H](Cc2cnc[nH]2)NC(=O)[C@H](Cc2c[nH]c3ccccc23)NC(=O)[C@H](C)NC(=O)[C@@H](NC(=O)[C@@H](N)CC(=O)O)CSSC[C@@H](C(=O)N[C@H](C(N)=O)[C@@H](C)O)NC(=O)[C@H](Cc2c[nH]c3ccccc23)NC(=O)[C@H](C(C)C)NC(=O)[C@H](CC(C)C)NC1=O]
Intermediate 3
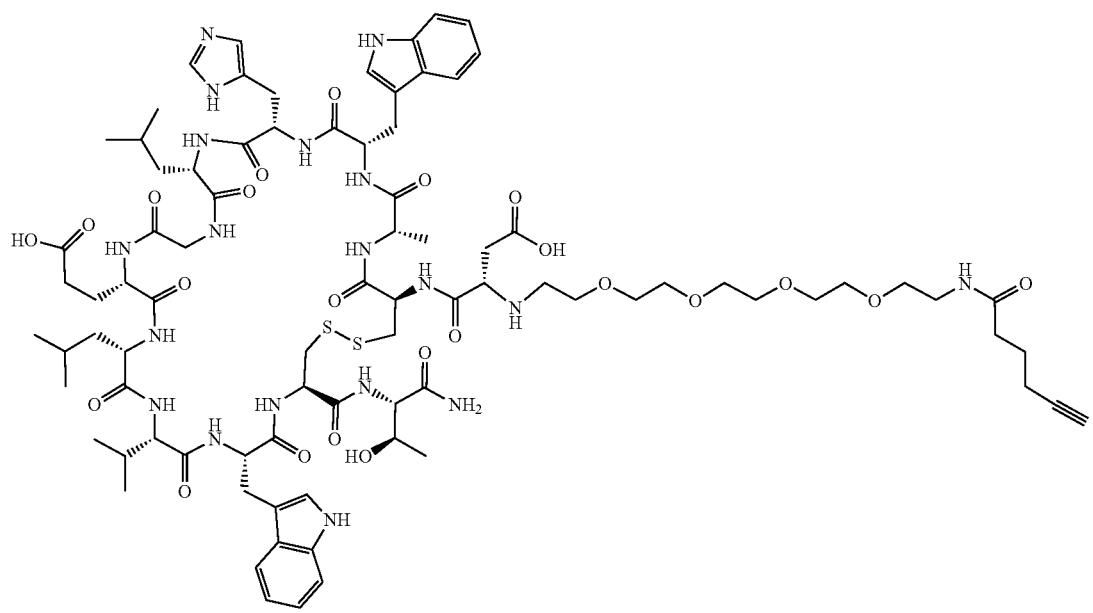 [SMILES: C#CCCCC(=O)NCCOCCOCCOCCOCCN[C@@H](CC(=O)O)C(=O)N[C@H]1CSSC[C@@H](C(=O)N[C@H](C(N)=O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc2cnc[nH]2)NC(=O)[C@H](Cc2c[nH]c3ccccc23)NC(=O)[C@H](C)NC1=O]

TABLE 3A-continued
Tested Intermediates
Intermediate 4
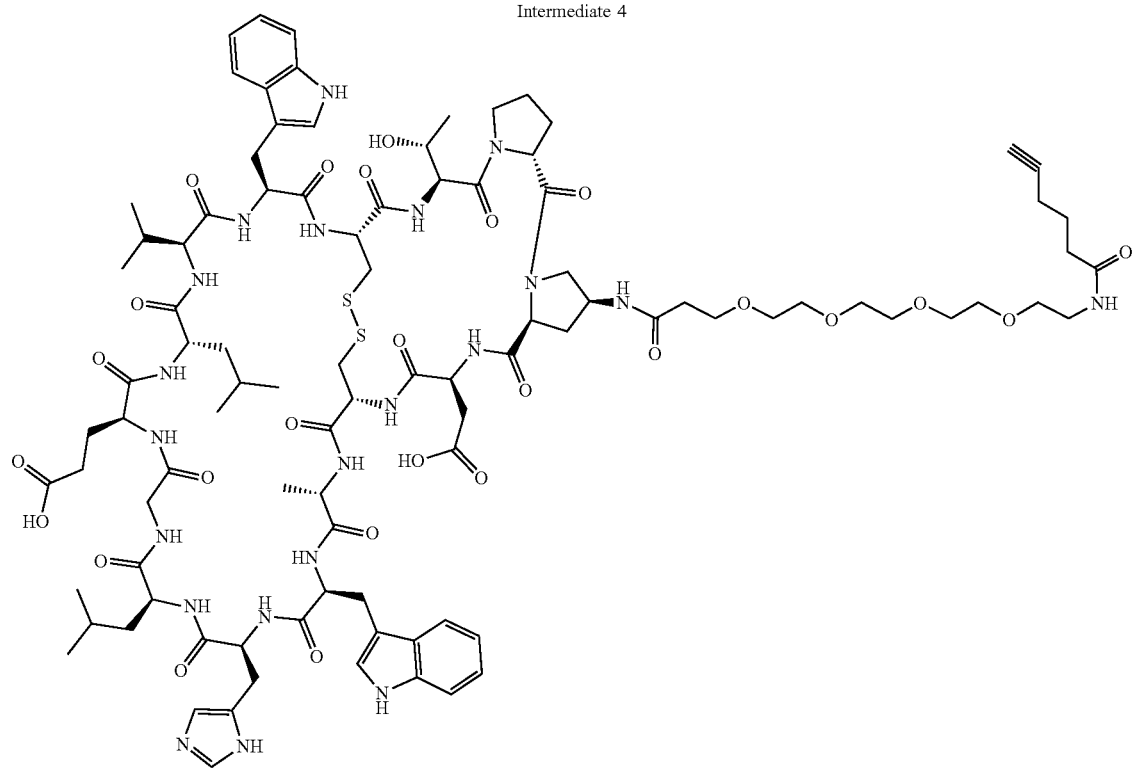
Intermediate 5
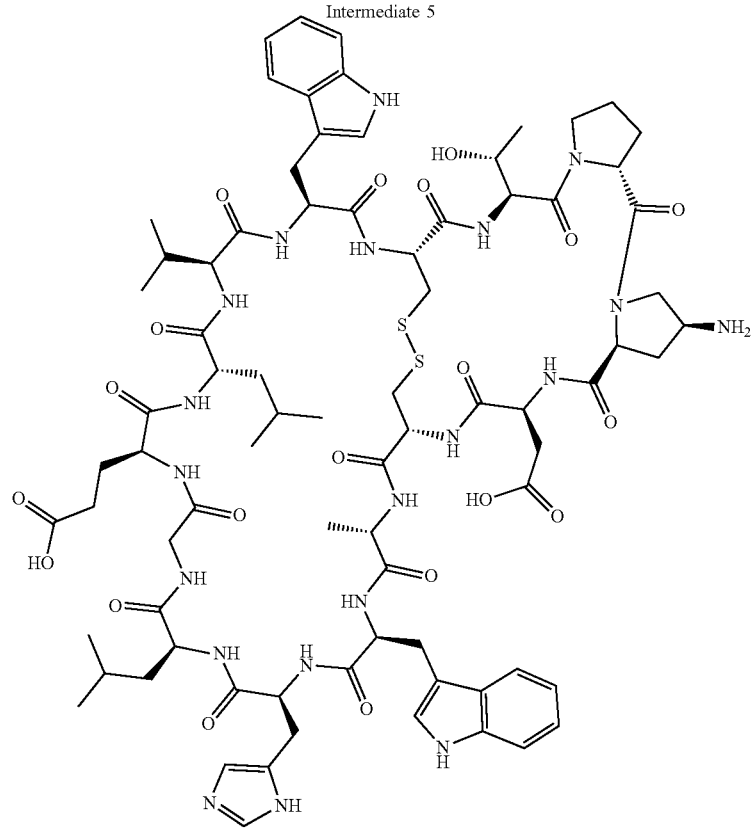

TABLE 3A-continued
Tested Intermediates
Intermediate 6
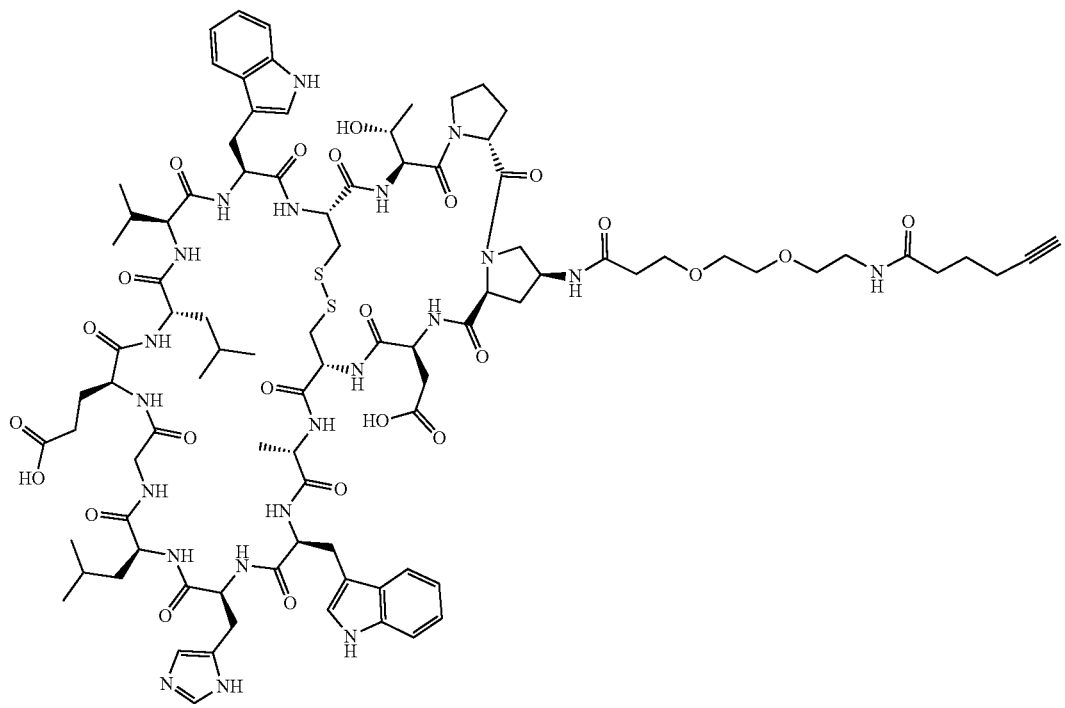 [SMILES: C#CCCCC(=O)NCCOCCOCCC(=O)N[C@H]1C[C@H]2C(=O)N[C@@H](CC(=O)O)C(=O)N[C@H]3CSSC[C@H](NC(=O)[C@H](Cc4c[nH]c5ccccc45)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc4cnc[nH]4)NC(=O)[C@H](Cc4c[nH]c5ccccc45)NC(=O)[C@H](C)NC3=O)C(=O)N[C@@H]([C@@H](C)O)C(=O)N3CCC[C@@H]3C(=O)N2C1]
Intermediate 7
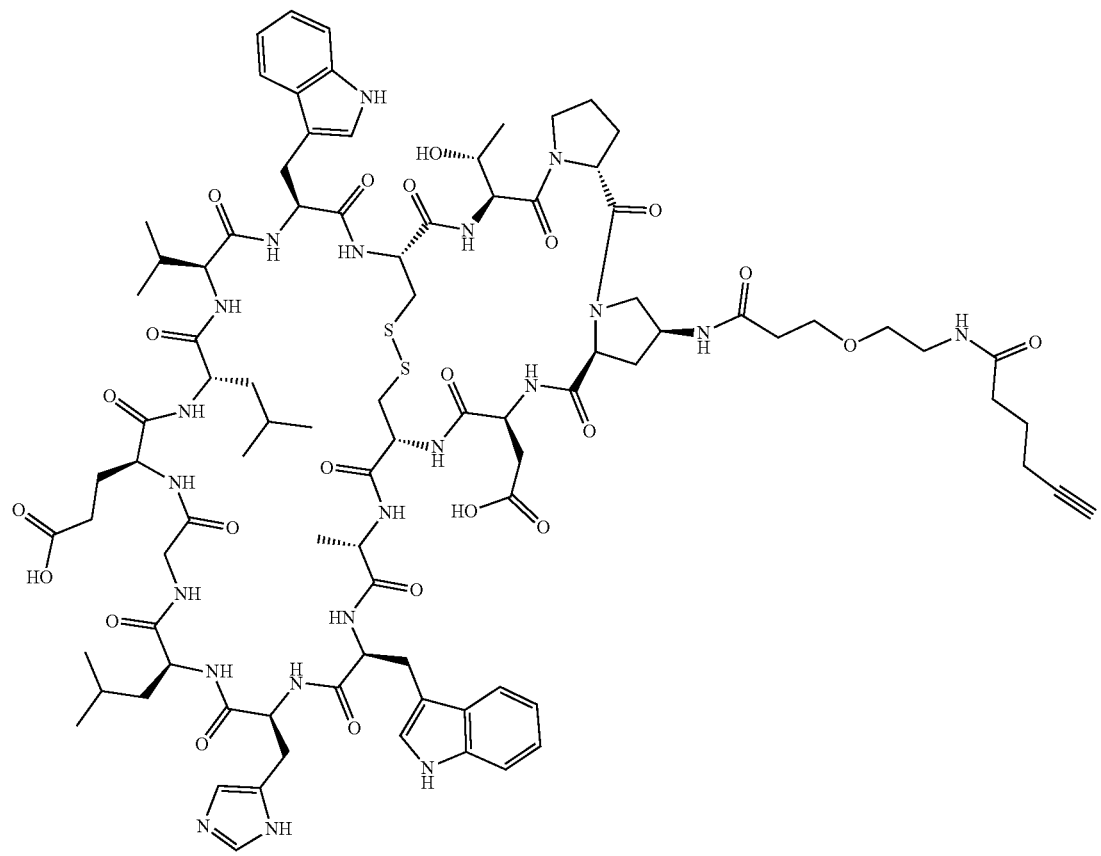 [SMILES: C#CCCCC(=O)NCCOCCC(=O)N[C@H]1C[C@H]2C(=O)N[C@@H](CC(=O)O)C(=O)N[C@H]3CSSC[C@H](NC(=O)[C@H](Cc4c[nH]c5ccccc45)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc4cnc[nH]4)NC(=O)[C@H](Cc4c[nH]c5ccccc45)NC(=O)[C@H](C)NC3=O)C(=O)N[C@@H]([C@@H](C)O)C(=O)N3CCC[C@@H]3C(=O)N2C1]

TABLE 3A-continued
Tested Intermediates
Intermediate 9
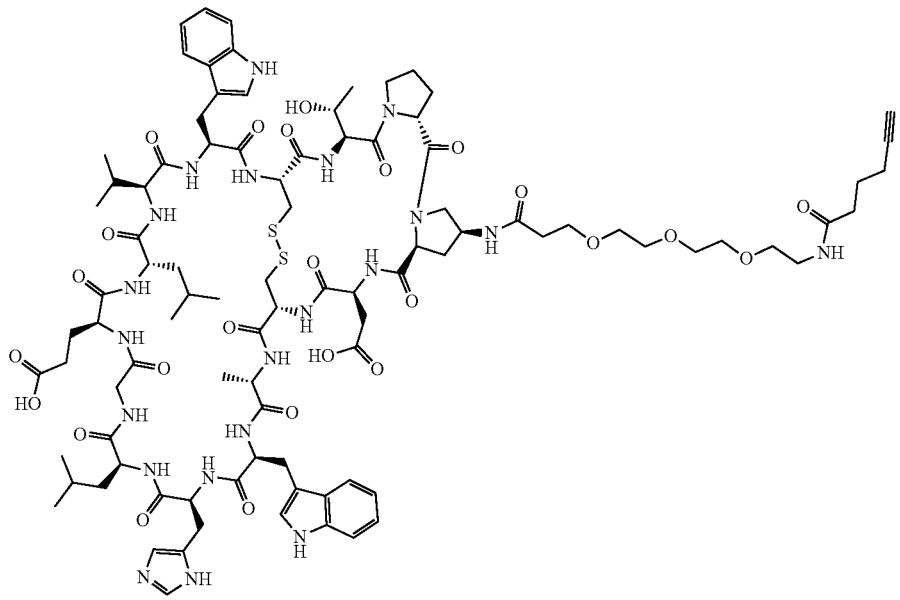 [SMILES: C#CCCCC(=O)NCCOCCOCCOCCC(=O)N[C@H]1C[C@H]2C(=O)N[C@@H](CC(=O)O)C(=O)N[C@H]3CSSC[C@H](NC(=O)[C@H](Cc4c[nH]c5ccccc45)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc4cnc[nH]4)NC(=O)[C@H](Cc4c[nH]c5ccccc45)NC(=O)[C@H](C)NC3=O)C(=O)N[C@@H]([C@@H](C)O)C(=O)N3CCC[C@@H]3C(=O)N2C1]
Intermediate 10
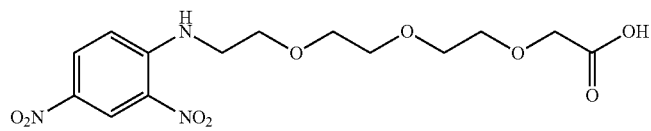 [SMILES: O=C(O)COCCOCCOCCNc1ccc([N+](=O)[O-])cc1[N+](=O)[O-]]
TABLE 3B
Tested Intermediates
Intermediate 11
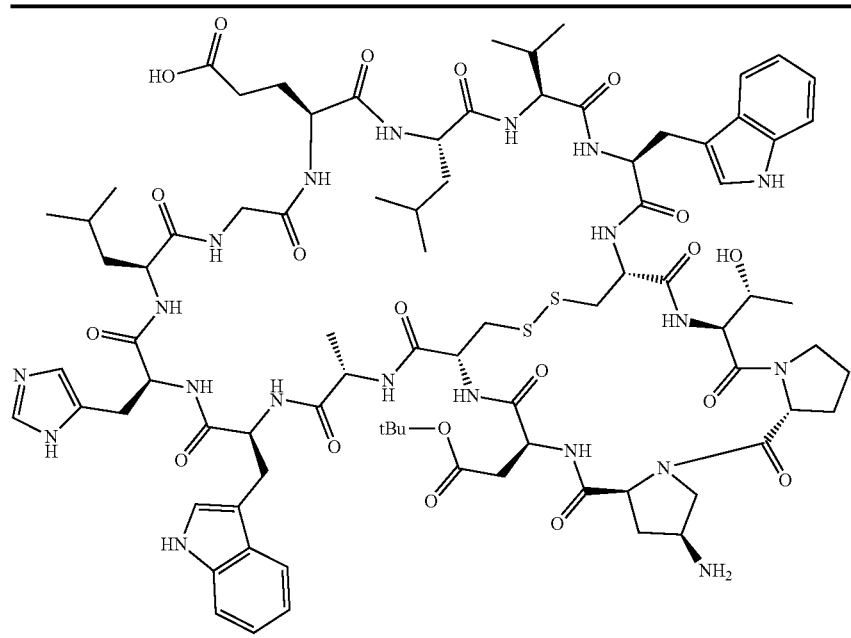

TABLE 3B-continued
Tested Intermediates
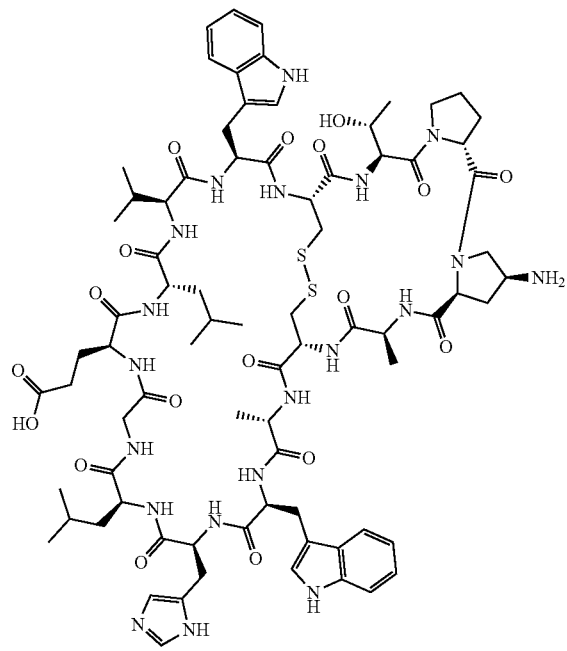 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](N)C[C@H]1C(=O)N[C@@H](C)C(=O)N2]
Intermediate 12
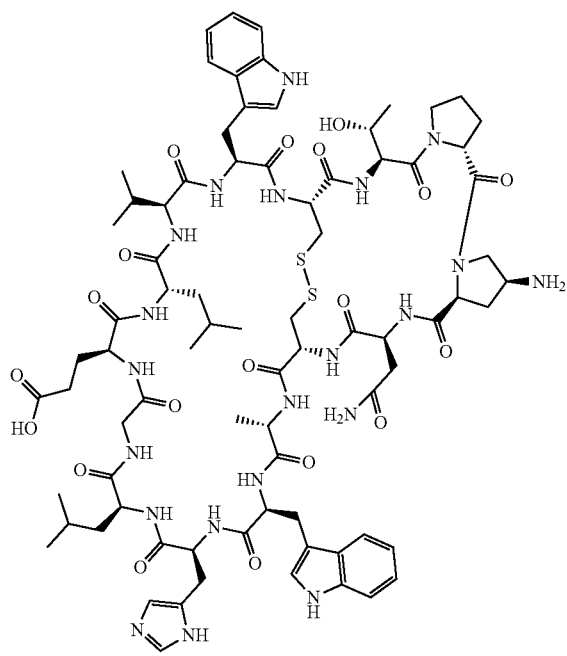 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](N)C[C@H]1C(=O)N[C@@H](CC(N)=O)C(=O)N2]
Intermediate 13

TABLE 3B-continued
Tested Intermediates
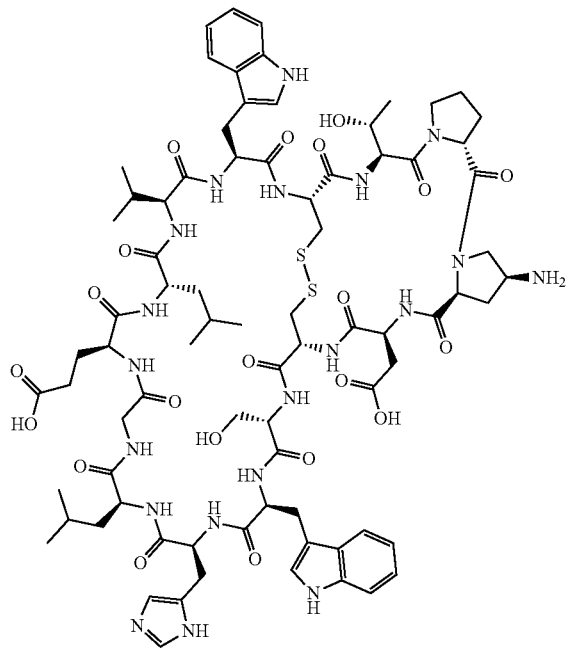 [SMILES: CC(C)C[C@@H]1NC(=O)[C@H](Cc2cnc[nH]2)NC(=O)[C@H](Cc2c[nH]c3ccccc23)NC(=O)[C@H](CO)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](N)C[C@H]1C(=O)N[C@@H](CC(=O)O)C(=O)N2]
Intermediate 14
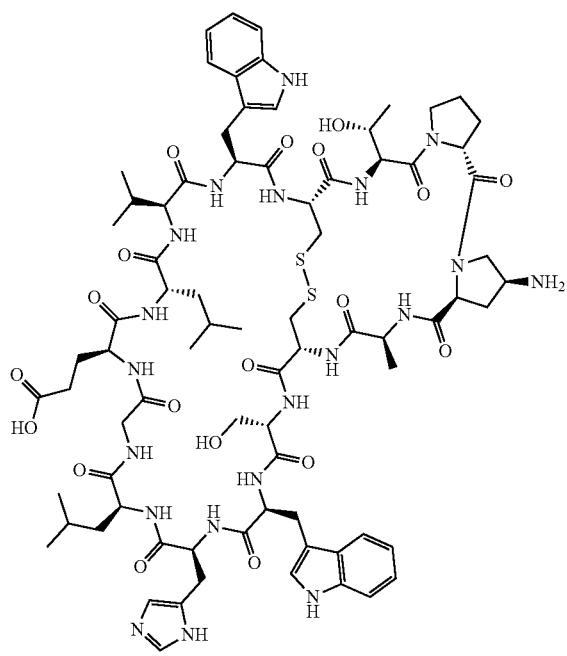 [SMILES: CC(C)C[C@@H]1NC(=O)[C@H](Cc2cnc[nH]2)NC(=O)[C@H](Cc2c[nH]c3ccccc23)NC(=O)[C@H](CO)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](N)C[C@H]1C(=O)N[C@@H](C)C(=O)N2]
Intermediate 15

TABLE 3B-continued
Tested Intermediates
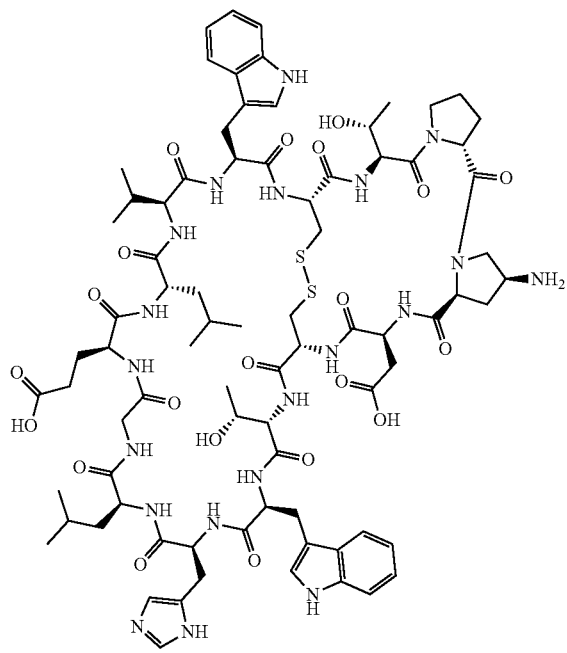
Intermediate 16
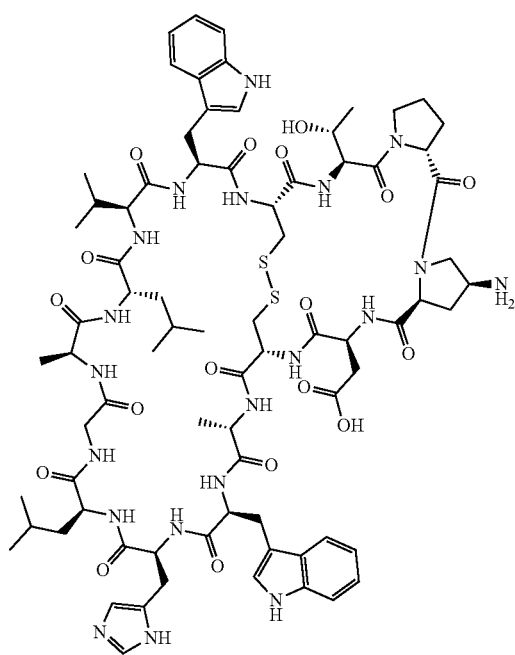 [SMILES: CC(C)C[C@@H]1NC(=O)[C@H](C)NC(=O)CNC(=O)[C@H](CC(C)C)NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC1=O)C(=O)N[C@@H]([C@@H](C)O)C(=O)N1CCC[C@@H]1C(=O)N1C[C@@H](N)C[C@H]1C(=O)N[C@@H](CC(=O)O)C(=O)N2]
Intermediate 17

TABLE 3B-continued
Tested Intermediates
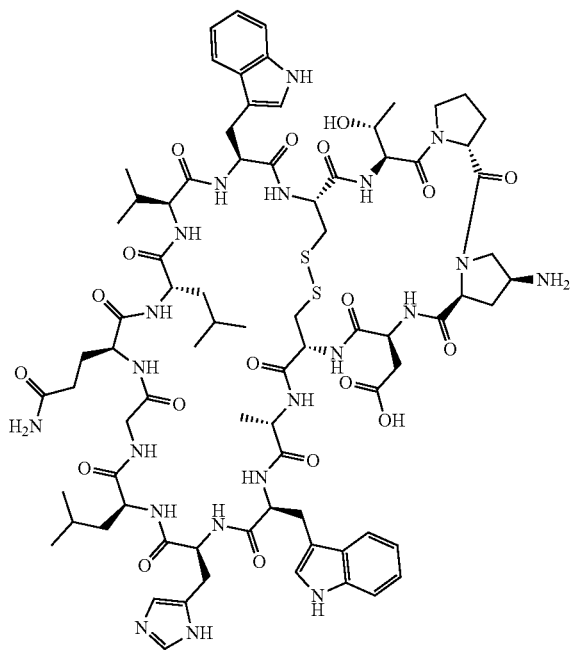 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(N)=O)NC(=O)CNC1=O)C(=O)N[C@@H]([C@@H](C)O)C(=O)N1CCC[C@@H]1C(=O)N1C[C@@H](N)C[C@H]1C(=O)N[C@@H](CC(=O)O)C(=O)N2]
Intermediate 18
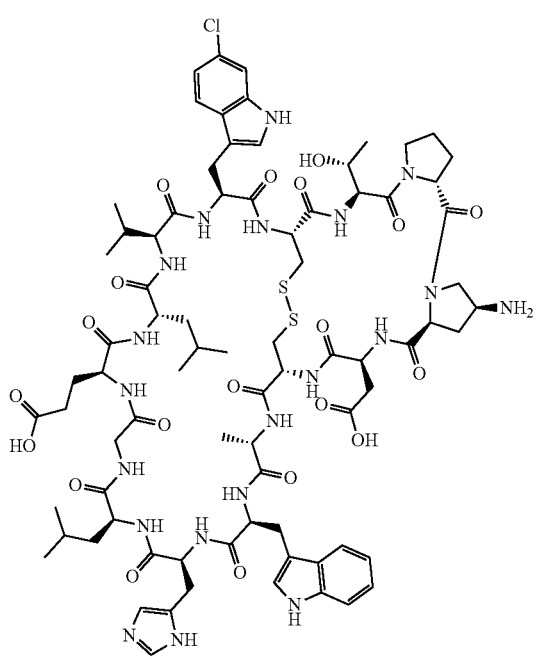 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4cc(Cl)ccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](N)C[C@H]1C(=O)N[C@@H](CC(=O)O)C(=O)N2]
Intermediate 19

TABLE 3B-continued
Tested Intermediates
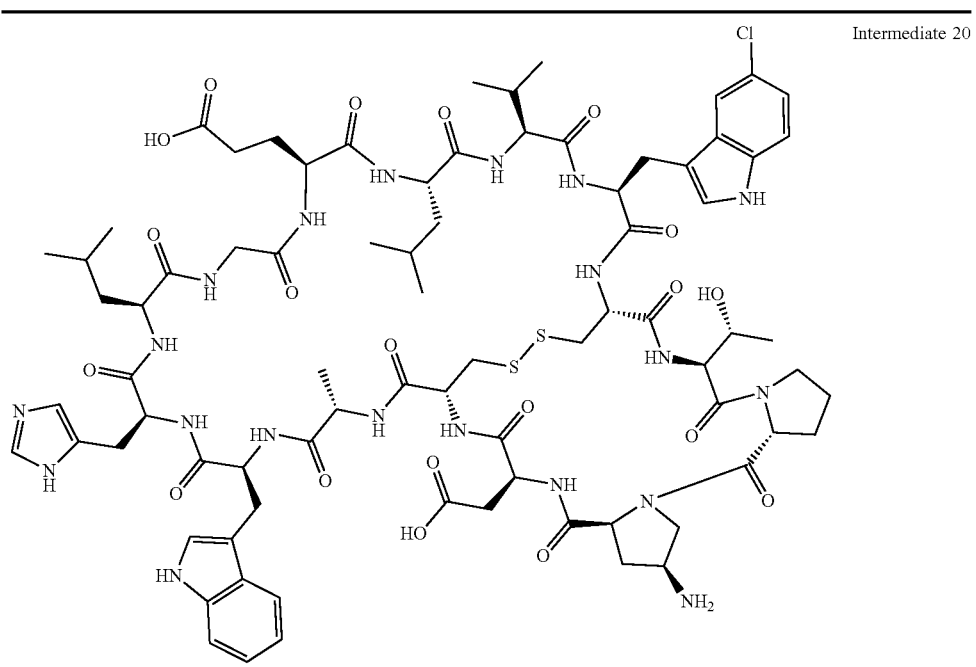
Intermediate 20
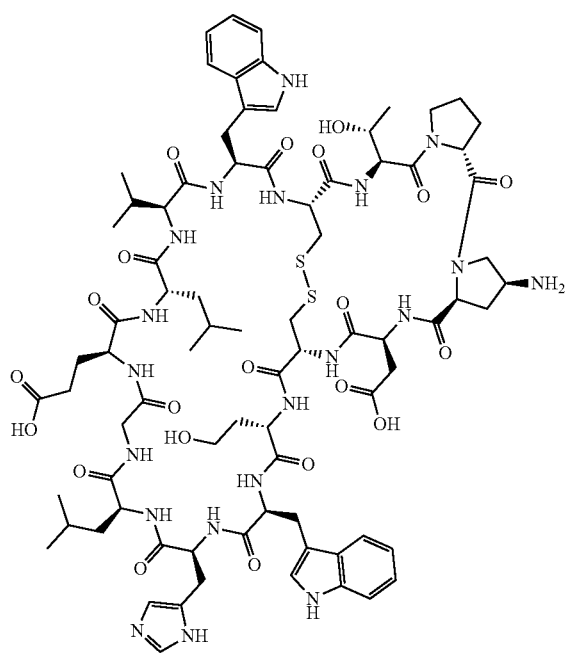 [SMILES: CC(C)C[C@@H]1NC(=O)[C@H](Cc2cnc[nH]2)NC(=O)[C@H](Cc2c[nH]c3ccccc23)NC(=O)[C@H](CCO)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](N)C[C@H]1C(=O)N[C@@H](CC(=O)O)C(=O)N2]
Intermediate 21

TABLE 3B-continued
Tested Intermediates
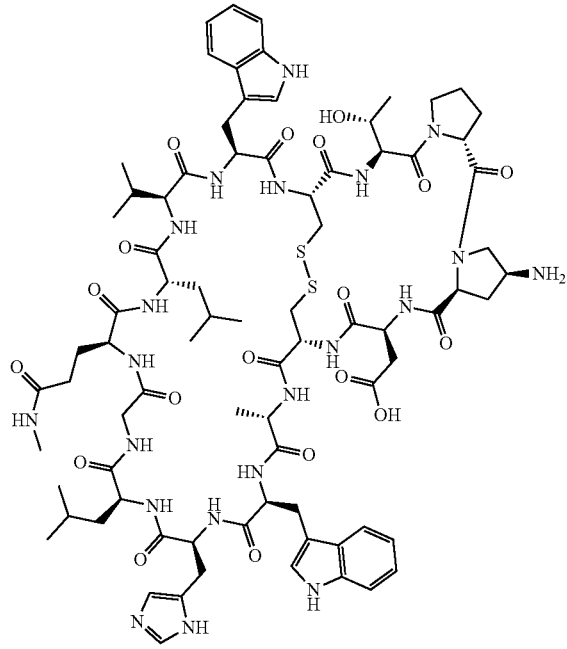 [SMILES: CNC(=O)CC[C@@H]1NC(=O)CNC(=O)[C@H](CC(C)C)NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC1=O)C(=O)N[C@@H]([C@@H](C)O)C(=O)N1CCC[C@@H]1C(=O)N1C[C@@H](N)C[C@H]1C(=O)N[C@@H](CC(=O)O)C(=O)N2]
Intermediate 22
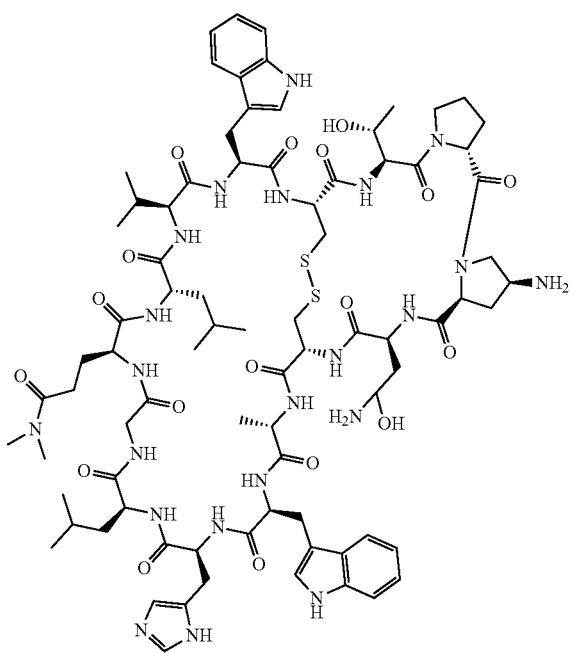 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)N(C)C)NC(=O)CNC1=O)C(=O)N[C@@H]([C@@H](C)O)C(=O)N1CCC[C@@H]1C(=O)N1C[C@@H](N)C[C@H]1C(=O)N[C@@H](CC(N)O)C(=O)N2]
Intermediate 23

TABLE 3B-continued
Tested Intermediates
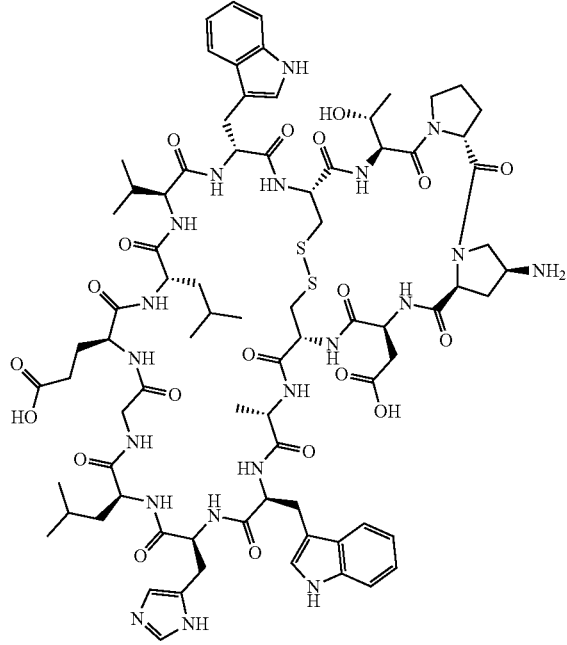 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](N)C[C@H]1C(=O)N[C@@H](CC(=O)O)C(=O)N2]
Intermediate 24
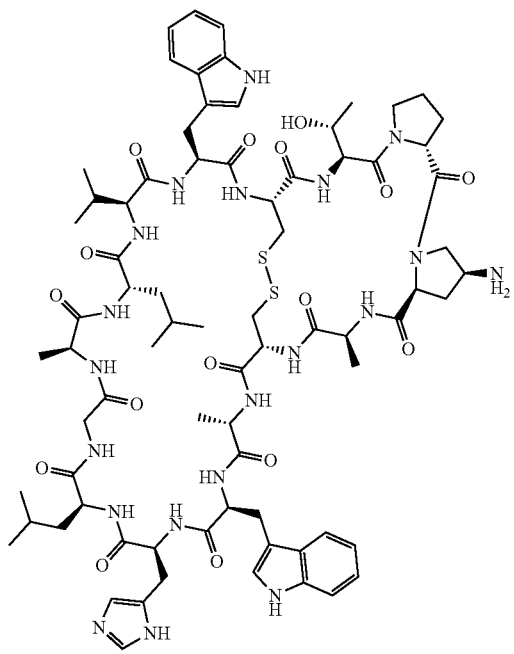 [SMILES: CC(C)C[C@@H]1NC(=O)[C@H](C)NC(=O)CNC(=O)[C@H](CC(C)C)NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC1=O)C(=O)N[C@@H]([C@@H](C)O)C(=O)N1CCC[C@@H]1C(=O)N1C[C@@H](N)C[C@H]1C(=O)N[C@@H](C)C(=O)N2]
Intermediate 25

TABLE 3B-continued
Tested Intermediates
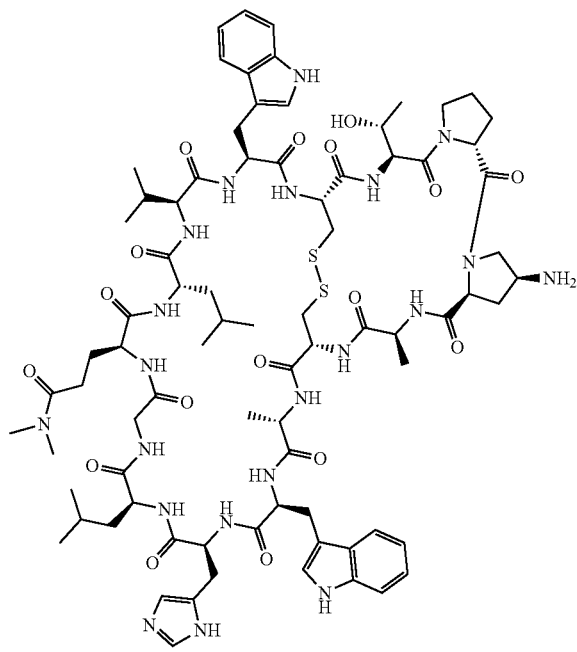 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)N(C)C)NC(=O)CNC1=O)C(=O)N[C@@H]([C@@H](C)O)C(=O)N1CCC[C@@H]1C(=O)N1C[C@@H](N)C[C@H]1C(=O)N[C@@H](C)C(=O)N2]
Intermediate 26
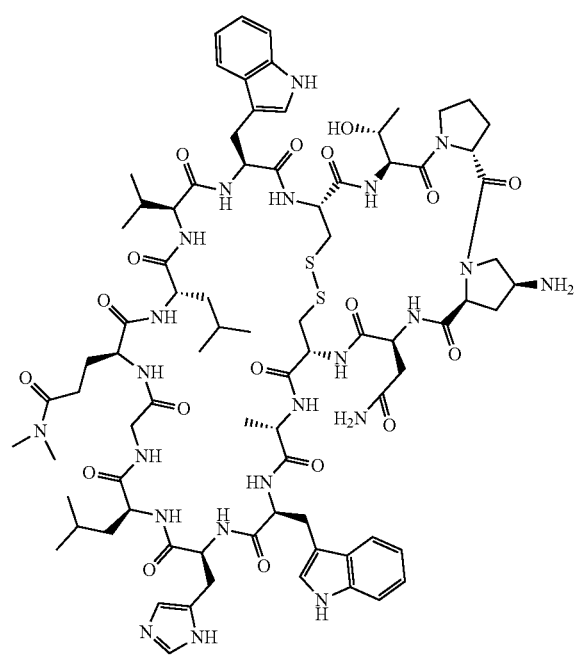 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)N(C)C)NC(=O)CNC1=O)C(=O)N[C@@H]([C@@H](C)O)C(=O)N1CCC[C@@H]1C(=O)N1C[C@@H](N)C[C@H]1C(=O)N[C@@H](CC(N)=O)C(=O)N2]
Intermediate 27

TABLE 3B-continued

Tested Intermediates

Intermediate 28

[Chemical structure of Intermediate 28]

Intermediate 29

[Chemical structure of Intermediate 29]

Example 1. Affinity of Immunoglobulin Degraders to ASGPR Measured Using Surface Plasmon Resonance (SPR)

The dissociation constants (Kd) of compounds described herein to the ASGP receptor were measured by surface plasmon resonance using a Biacore 8K instrument (GE Healthcare) at 25° C. Biotinylated ASGPR (20 μg/ml) was immobilized on SA sensor chips (GE Healthcare) at flow rate of 5 μl/min for 90 sec reaching an immobilization level ranging from 500-3000 resonance units (RU). The running buffer was 50 mM HEPES, pH7.5, 150 mM NaCl, 50 mM CaCl$_2$), 0.01% P20, 3% DMSO. The concentration of compounds vary from 2 mM to 5 nM depending on Kd values. The compounds are diluted 2 or 3-fold with 8 concentration points. Solutions containing serially diluted compounds are injected at a flow rate of 40 μL/min for 150-300 sec followed by a 90-300 sec dissociation phase for each concentration. The surface was regenerated using 50 mM HEPES, pH 7.5, 150 mM NaCl, 5 mM EDTA, 0.01% P20, 3% DMSO.

Figure 21:
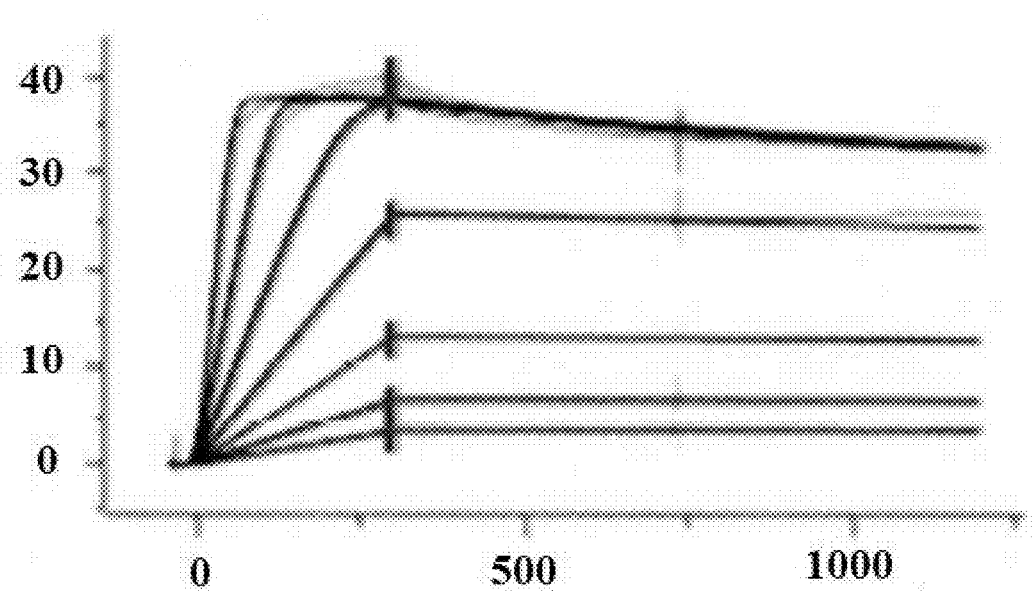
FIG. 21 is a line graph showing the ASGPR binding of Compound 4 measured by SPR as described in Example 1. The y-axis is response measured in units and the x-axis is time measured in seconds.

Data was processed using the analysis software in Biacore 8K to perform background subtraction, double referencing, and solvent correction. Values of affinity expressed as the dissociation constants (Kd) were determined by fitting the steady state binding responses (RUs) as a function of the concentration ([Compound]) using the following equation: RU=RUmax/(KD+[Compound]), where RU max is the calculated maximal response. Where appropriate double-referenced data were fit to using a 1:1 binding model for kinetic analysis. Obtained data is summarized in Table 4 below. This assay was also used to generate the data in FIG. 21.

TABLE 4A

ASGPR Binding of Select Compounds

| Compound Number | ASGPR SPR Binding $K_d$ (nM) |
|---|---|
| Compound 6 | ++++ |
| Compound 7 | ++++ |
| Compound 8 | ++++ |
| Compound 9 | ++++ |
| Compound 10 | ++++ |
| Compound 16 | ++++ |
| Compound 17 | ++++ |
| Compound 18 | ++ |
| Compound 19 | ++++ |
| Compound 20 | ++++ |
| Compound 21 | ++++ |
| Compound 22 | ++++ |
| Compound 23 | ++++ |
| Compound 24 | ++++ |
| Compound 27 | ++++ |
| Compound 28 | ++++ |
| Compound 29 | +++ |

TABLE 4A-continued

ASGPR Binding of Select Compounds

| Compound Number | ASGPR SPR Binding $K_d$ (nM) |
|---|---|
| Compound 30 | ++++ |
| Compound 31 | ++++ |
| Compound 32 | ++++ |
| Compound 38 | ++++ |
| Compound 51 | ++++ |
| Compound 56 | ++++ |
| Compound 57 | ++++ |
| Compound 58 | +++ |
| A2 | ++++ |
| A13 | ++++ |
| A14 | +++ |
| A15 | ++++ |
| A19 | ++++ |
| A21 | +++ |
| A23 | ++++ |
| A24 | ++++ |
| A25 | +++ |
| A26 | ++++ |
| A31 | ++++ |
| A33 | ++++ |
| A34 | ++++ |
| A130 | ++++ |
| A131 | ++++ |
| A132 | ++++ |

In the table above $K_d$ values that are >=1000 nM = +, <1000 nM = ++, <500 nM = +++, and <100 nM = ++++.

TABLE 4B

ASGPR Binding of Additional ASGPR Binding Ligands

| Compound ID | Structure | ASGPR SPR Binding: $K_D$ (μM) |
|---|---|---|
| A46 | 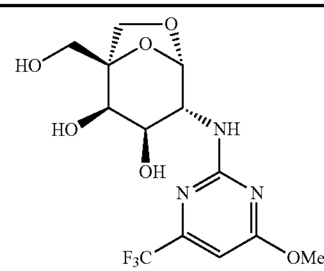 | ++++ |
| A47 | 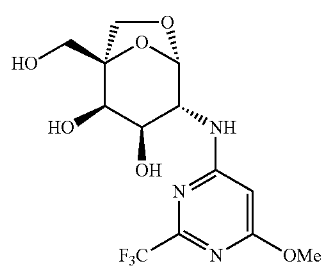 [SMILES: COc1cc(N[C@H]2[C@H]3OC[C@](CO)(O3)[C@H](O)[C@@H]2O)nc(C(F)(F)F)n1] | ++++ |
| A48 | 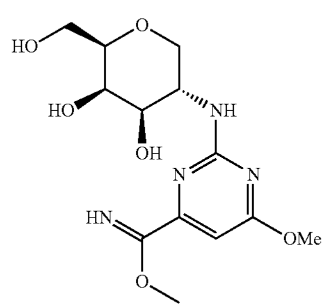 [SMILES: COC(=N)c1cc(OC)nc(N[C@H]2CO[C@H](CO)[C@H](O)[C@@H]2O)n1] | +++ |

TABLE 4B-continued
ASGPR Binding of Additional ASGPR Binding Ligands
| Compound ID | Structure | ASGPR SPR Binding: $K_D$ (μM) |
|---|---|---|
| A49 | 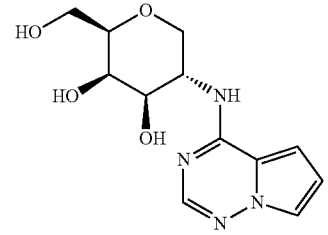 [SMILES: OC[C@H]1OC[C@H](Nc2ncnn3cccc23)[C@@H](O)[C@H]1O] | +++ |
| A50 | 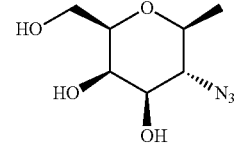 | >20 |
| A51 | 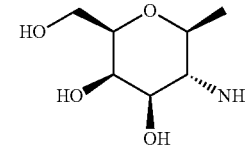 | |
| A52 | 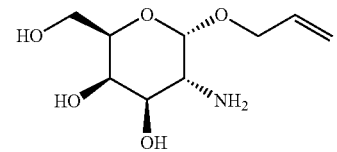 | >20 |
| A53 | 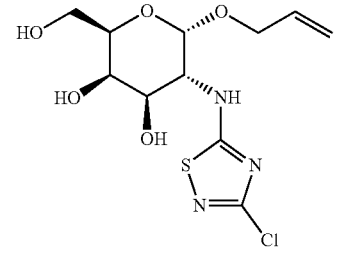 [SMILES: C=CCO[C@H]1O[C@H](CO)[C@H](O)[C@H](O)[C@H]1Nc1nc(Cl)ns1] | |
| A117 | 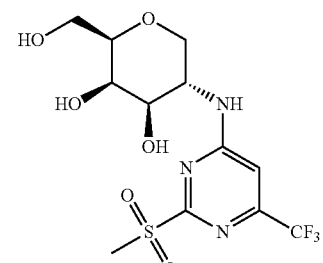 | >20 |

TABLE 4B-continued

ASGPR Binding of Additional ASGPR Binding Ligands

| Compound ID | Structure | ASGPR SPR Binding: $K_D$ (µM) |
|---|---|---|
| A54 | 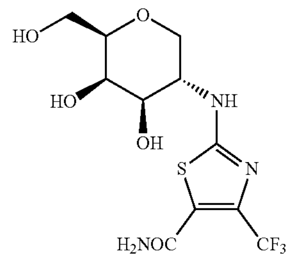 [SMILES: NC(=O)c1sc(N[C@H]2CO[C@H](CO)[C@H](O)[C@@H]2O)nc1C(F)(F)F] | >20 |
| A55 | 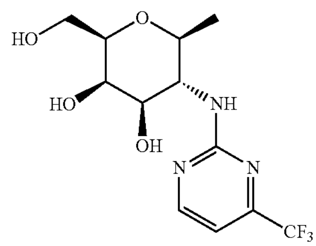 [SMILES: C[C@@H]1O[C@H](CO)[C@H](O)[C@H](O)[C@H]1Nc1nccc(C(F)(F)F)n1] | ++ |
| A56 | 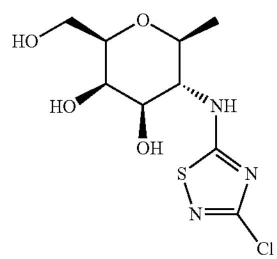 [SMILES: C[C@@H]1O[C@H](CO)[C@H](O)[C@H](O)[C@H]1Nc1nc(Cl)ns1] | +++ |
| A57 | 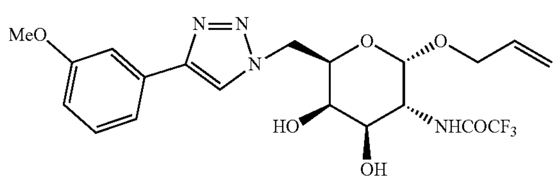 | +++ |
| A58 | 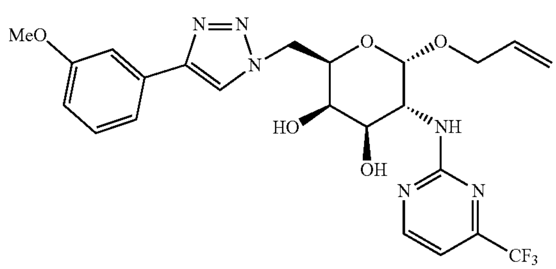 [SMILES: C=CCO[C@H]1O[C@H](Cn2cc(-c3cccc(OC)c3)nn2)[C@H](O)[C@H](O)[C@H]1Nc1nccc(C(F)(F)F)n1] | +++ |
| A59 | 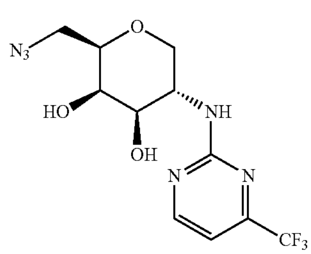 [SMILES: [N-]=[N+]=NC[C@H]1OC[C@H](Nc2nccc(C(F)(F)F)n2)[C@@H](O)[C@H]1O] | ++++ |

TABLE 4B-continued

ASGPR Binding of Additional ASGPR Binding Ligands

| Compound ID | Structure | ASGPR SPR Binding: $K_D$ (μM) |
|---|---|---|
| A60 | 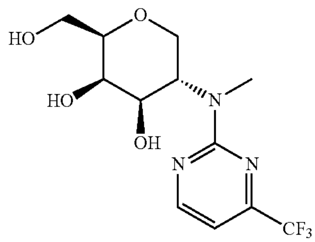 [SMILES: CN(c1nccc(C(F)(F)F)n1)[C@H]1CO[C@H](CO)[C@H](O)[C@@H]1O] | +++ |
| A61 | 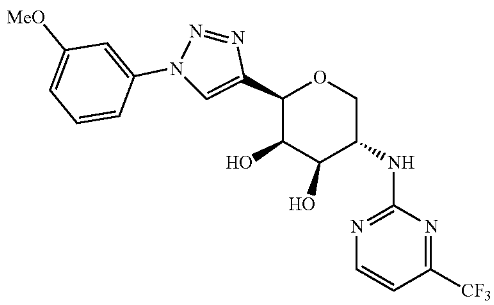 [SMILES: COc1cccc(-n2cc([C@H]3OC[C@H](Nc4nccc(C(F)(F)F)n4)[C@@H](O)[C@H]3O)nn2)c1] | ++ |
| A62 | 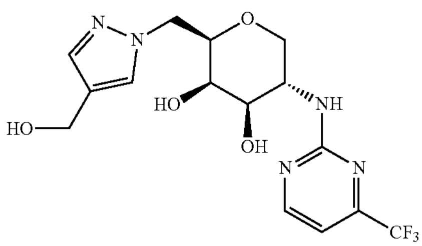 [SMILES: OCc1cnn(C[C@H]2OC[C@H](Nc3nccc(C(F)(F)F)n3)[C@@H](O)[C@H]2O)c1] | +++ |
| A63 | 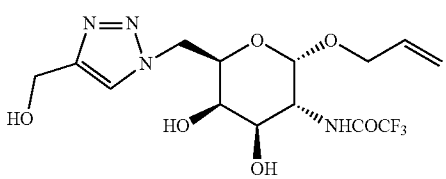 | +++ |
| A64 | 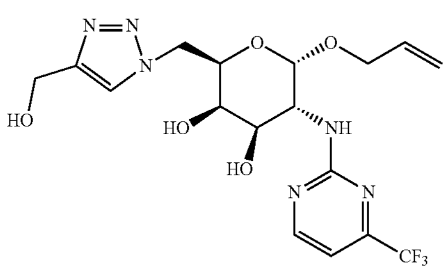 [SMILES: C=CCO[C@H]1O[C@H](Cn2cc(CO)nn2)[C@H](O)[C@H](O)[C@H]1Nc1nccc(C(F)(F)F)n1] | +++ |
| A65 | 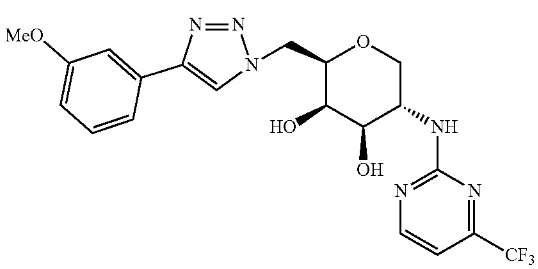 [SMILES: COc1cccc(-c2cn(C[C@H]3OC[C@H](Nc4nccc(C(F)(F)F)n4)[C@@H](O)[C@H]3O)nn2)c1] | ++++ |

TABLE 4B-continued

ASGPR Binding of Additional ASGPR Binding Ligands

| Compound ID | Structure | ASGPR SPR Binding: $K_D$ (μM) |
|---|---|---|
| A66 | 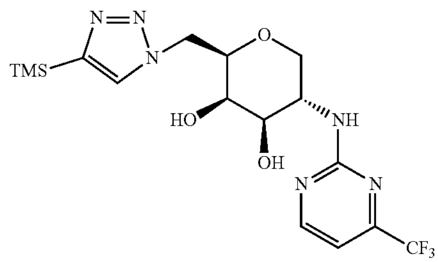 [SMILES: C[Si](C)(C)c1cn(C[C@H]2OC[C@H](Nc3nccc(C(F)(F)F)n3)[C@@H](O)[C@H]2O)nn1] | +++ |
| A67 | 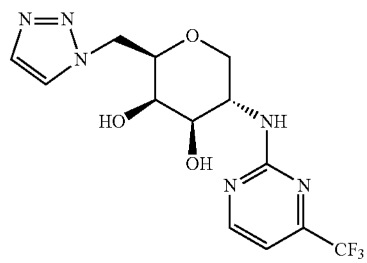 [SMILES: O[C@@H]1[C@H](O)[C@@H](Nc2nccc(C(F)(F)F)n2)CO[C@@H]1Cn1ccnn1] | ++++ |
| A68 | 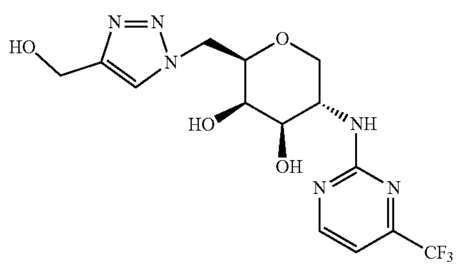 [SMILES: OCc1cn(C[C@H]2OC[C@H](Nc3nccc(C(F)(F)F)n3)[C@@H](O)[C@H]2O)nn1] | ++++ |
| A69 | 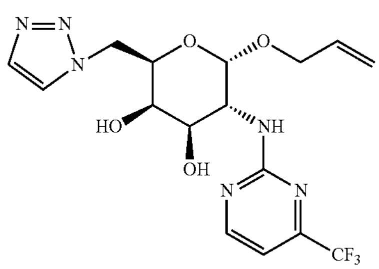 [SMILES: C=CCO[C@H]1O[C@H](Cn2ccnn2)[C@H](O)[C@H](O)[C@H]1Nc1nccc(C(F)(F)F)n1] | ++++ |
| A72 | 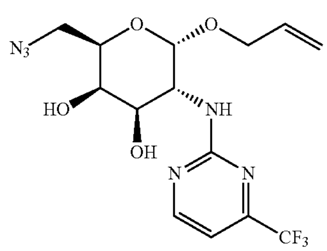 [SMILES: C=CCO[C@H]1O[C@H](CN=[N+]=[N-])[C@H](O)[C@H](O)[C@H]1Nc1nccc(C(F)(F)F)n1] | ++++ |
| A70 | 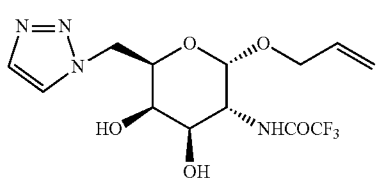 | ++++ |

TABLE 4B-continued

ASGPR Binding of Additional ASGPR Binding Ligands

| Compound ID | Structure | ASGPR SPR Binding: $K_D$ (μM) |
|---|---|---|
| A71 | 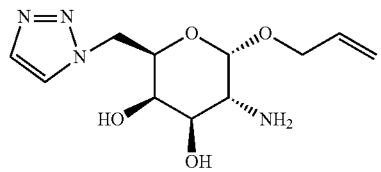 [SMILES: C=CCO[C@H]1O[C@H](Cn2ccnn2)[C@H](O)[C@H](O)[C@H]1N] | |
| A73 | 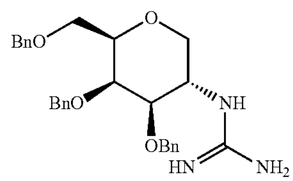 [SMILES: N=C(N)N[C@H]1CO[C@H](COCc2ccccc2)[C@H](OCc2ccccc2)[C@@H]1OCc1ccccc1] | >20 |
| A74 | 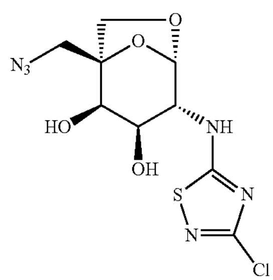 [SMILES: [N-]=[N+]=NC[C@@]12CO[C@@H](O1)[C@H](Nc1nc(Cl)ns1)[C@@H](O)[C@H]2O] | ++++ |
| A75 | 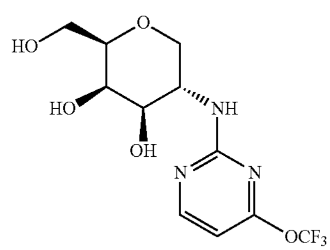 [SMILES: OC[C@H]1OC[C@H](Nc2nccc(OC(F)(F)F)n2)[C@@H](O)[C@H]1O] | |
| A76 | 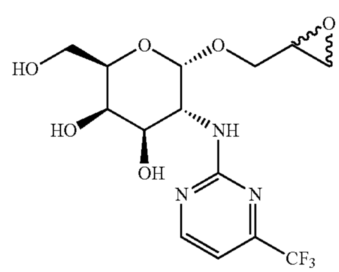 | ++++ |
| A77 | 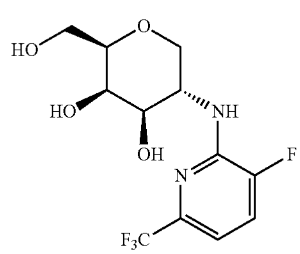 [SMILES: OC[C@H]1OC[C@H](Nc2nc(C(F)(F)F)ccc2F)[C@@H](O)[C@H]1O] | ++++ |

TABLE 4B-continued

ASGPR Binding of Additional ASGPR Binding Ligands

| Compound ID | Structure | ASGPR SPR Binding: $K_D$ (μM) |
|---|---|---|
| A78 | 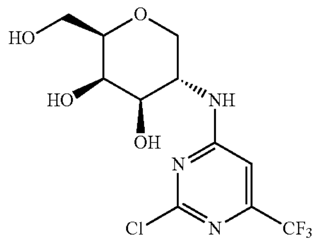 [SMILES: OC[C@H]1OC[C@H](Nc2cc(C(F)(F)F)nc(Cl)n2)[C@@H](O)[C@H]1O] | >20 |
| A79 | 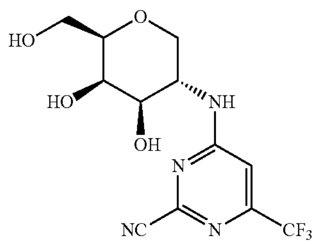 [SMILES: N#Cc1nc(N[C@H]2CO[C@H](CO)[C@H](O)[C@@H]2O)cc(C(F)(F)F)n1] | >20 |
| A82 | 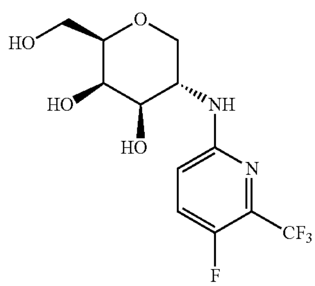 [SMILES: OC[C@H]1OC[C@H](Nc2ccc(F)c(C(F)(F)F)n2)[C@@H](O)[C@H]1O] | +++ |
| A83 | 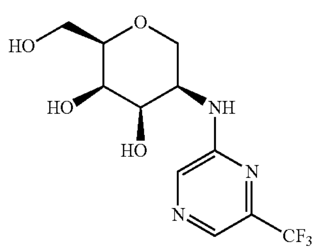 [SMILES: OC[C@H]1OC[C@@H](Nc2cncc(C(F)(F)F)n2)[C@@H](O)[C@H]1O] | |
| A84 | 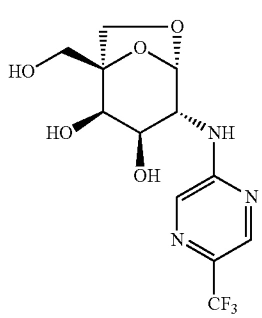 [SMILES: OC[C@@]12CO[C@@H](O1)[C@H](Nc1cnc(C(F)(F)F)cn1)[C@@H](O)[C@H]2O] | |

TABLE 4B-continued

ASGPR Binding of Additional ASGPR Binding Ligands

| Compound ID | Structure | ASGPR SPR Binding: $K_D$ (μM) |
|---|---|---|
| A86 | 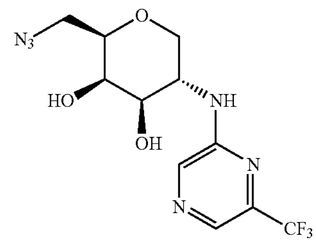 [SMILES: [N-]=[N+]=NC[C@H]1OC[C@H](Nc2cncc(C(F)(F)F)n2)[C@@H](O)[C@H]1O] | ++++ |
| A87 | 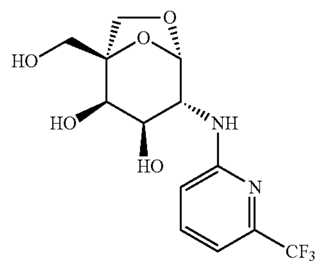 [SMILES: OC[C@@]12CO[C@@H](O1)[C@H](Nc1cccc(C(F)(F)F)n1)[C@@H](O)[C@H]2O] | ++++ |
| A89 | 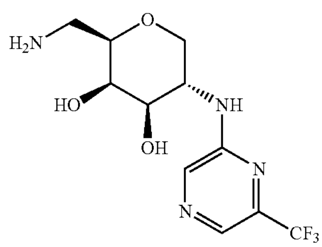 [SMILES: NC[C@H]1OC[C@H](Nc2cncc(C(F)(F)F)n2)[C@@H](O)[C@H]1O] | ++++ |
| A90 | 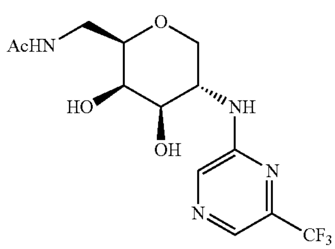 [SMILES: CC(=O)NC[C@H]1OC[C@H](Nc2cncc(C(F)(F)F)n2)[C@@H](O)[C@H]1O] | ++++ |
| A91 | 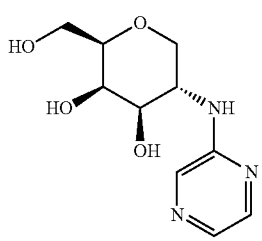 [SMILES: OC[C@H]1OC[C@H](Nc2cnccn2)[C@@H](O)[C@H]1O] | +++ |
| A92 | 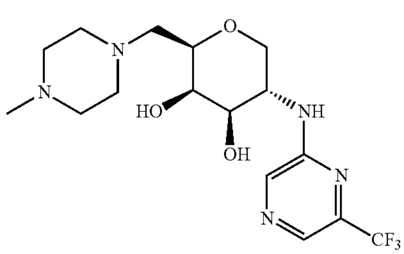 [SMILES: CN1CCN(C[C@H]2OC[C@H](Nc3cncc(C(F)(F)F)n3)[C@@H](O)[C@H]2O)CC1] | |

TABLE 4B-continued

ASGPR Binding of Additional ASGPR Binding Ligands

| Compound ID | Structure | ASGPR SPR Binding: $K_D$ (μM) |
|---|---|---|
| A93 | 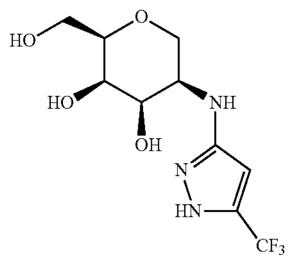 [SMILES: OC[C@H]1OC[C@@H](Nc2cc(C(F)(F)F)[nH]n2)[C@@H](O)[C@H]1O] | >0.1 |
| A94 | 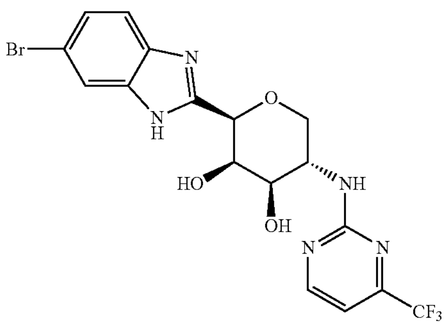 [SMILES: O[C@@H]1[C@H](O)[C@@H](Nc2nccc(C(F)(F)F)n2)CO[C@@H]1c1nc2ccc(Br)cc2[nH]1] | >20 |
| A95 | 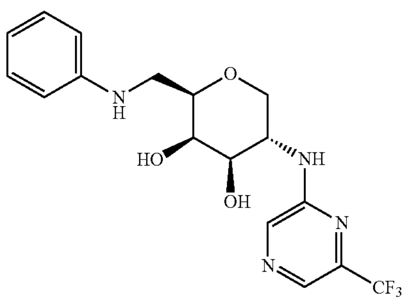 [SMILES: O[C@@H]1[C@H](O)[C@@H](Nc2cncc(C(F)(F)F)n2)CO[C@@H]1CNc1ccccc1] | +++ |
| A96 | 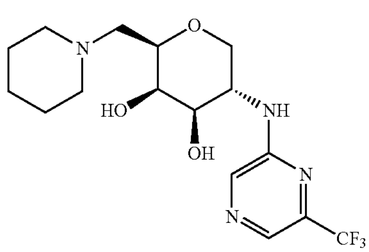 [SMILES: O[C@@H]1[C@H](O)[C@@H](Nc2cncc(C(F)(F)F)n2)CO[C@@H]1CN1CCCCC1] | +++ |
| A97 | 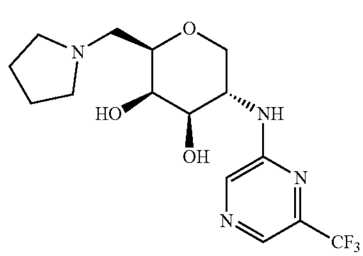 [SMILES: O[C@@H]1[C@H](O)[C@@H](Nc2cncc(C(F)(F)F)n2)CO[C@@H]1CN1CCCC1] | |

TABLE 4B-continued

ASGPR Binding of Additional ASGPR Binding Ligands

| Compound ID | Structure | ASGPR SPR Binding: $K_D$ (μM) |
|---|---|---|
| A98 | 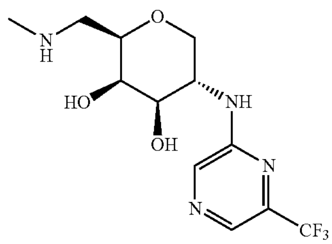 [SMILES: CNC[C@H]1OC[C@H](Nc2cncc(C(F)(F)F)n2)[C@@H](O)[C@H]1O] | |
| A99 | 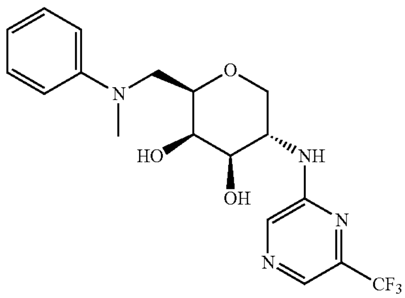 [SMILES: CN(C[C@H]1OC[C@H](Nc2cncc(C(F)(F)F)n2)[C@@H](O)[C@H]1O)c1ccccc1] | ++++ |
| A100 | 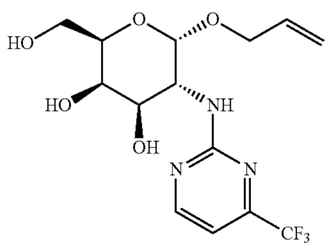 [SMILES: C=CCO[C@H]1O[C@H](CO)[C@H](O)[C@H](O)[C@H]1Nc1nccc(C(F)(F)F)n1] | ++++ |
| A104 | 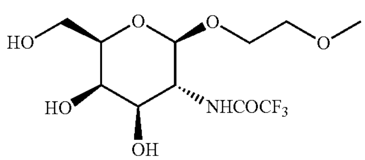 | +++ |
| A101 | 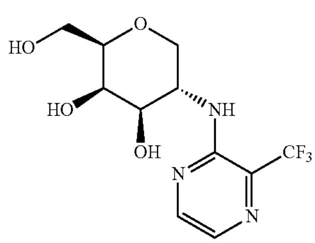 [SMILES: OC[C@H]1OC[C@H](Nc2nccnc2C(F)(F)F)[C@@H](O)[C@H]1O] | +++ |
| A102 | 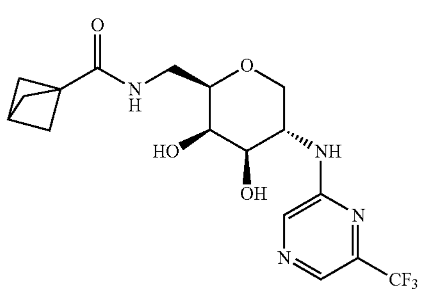 [SMILES: O=C(NC[C@H]1OC[C@H](Nc2cncc(C(F)(F)F)n2)[C@@H](O)[C@H]1O)C12CC(C1)C2] | ++++ |

TABLE 4B-continued

ASGPR Binding of Additional ASGPR Binding Ligands

| Compound ID | Structure | ASGPR SPR Binding: $K_D$ (µM) |
|---|---|---|
| A103 | 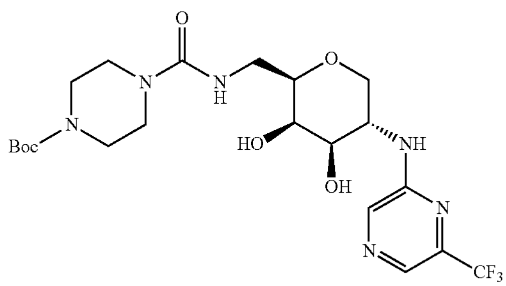 [SMILES: CC(C)(C)OC(=O)N1CCN(C(=O)NC[C@H]2OC[C@H](Nc3cncc(C(F)(F)F)n3)[C@@H](O)[C@H]2O)CC1] | ++++ |
| A105 | 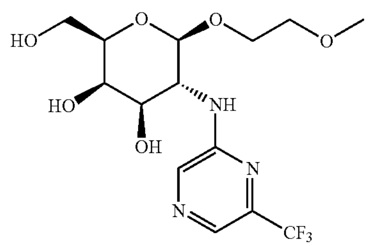 [SMILES: COCCO[C@@H]1O[C@H](CO)[C@H](O)[C@H](O)[C@H]1Nc1cncc(C(F)(F)F)n1] | +++ |
| A106 | 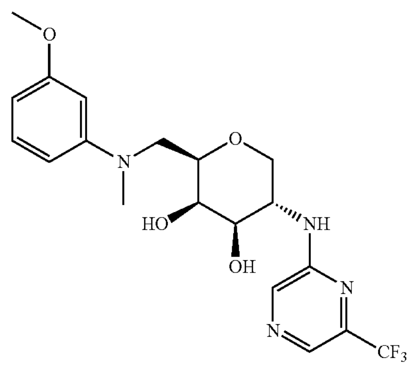 [SMILES: COc1cccc(N(C)C[C@H]2OC[C@H](Nc3cncc(C(F)(F)F)n3)[C@@H](O)[C@H]2O)c1] | ++++ |
| A107 | 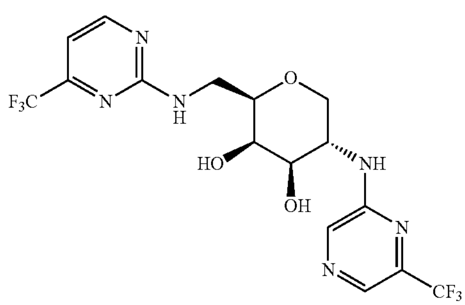 [SMILES: O[C@@H]1[C@H](O)[C@@H](Nc2cncc(C(F)(F)F)n2)CO[C@@H]1CNc1nccc(C(F)(F)F)n1] | ++++ |
| A108 | 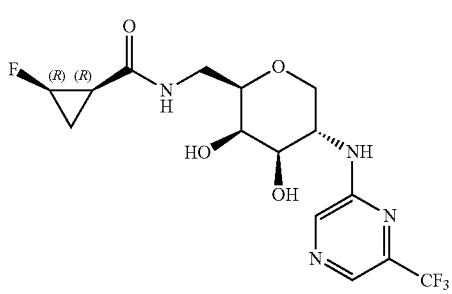 | >20 |

TABLE 4B-continued

ASGPR Binding of Additional ASGPR Binding Ligands

| Compound ID | Structure | ASGPR SPR Binding: $K_D$ (μM) |
|---|---|---|
| A109 | 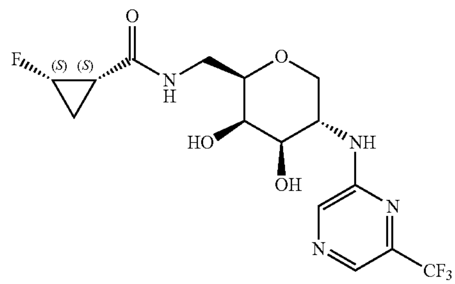 | >20 |
| A32 | 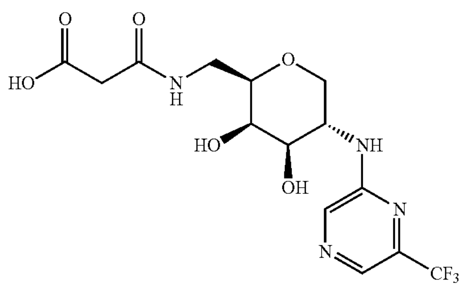 [SMILES: O=C(O)CC(=O)NC[C@H]1OC[C@H](Nc2cncc(C(F)(F)F)n2)[C@@H](O)[C@H]1O] | ++++ |
| A117 | 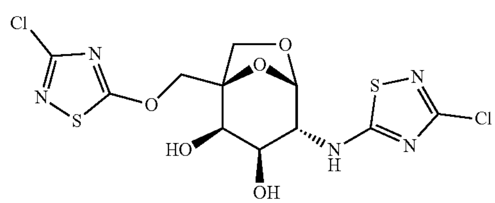 [SMILES: O[C@@H]1[C@@H](Nc2nc(Cl)ns2)[C@H]2OC[C@](COc3nc(Cl)ns3)(O2)[C@@H]1O] | ++++ |
| A37 | 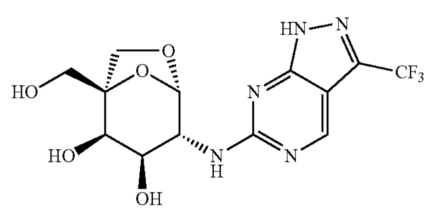 [SMILES: OC[C@@]12CO[C@@H](O1)[C@H](Nc1ncc3c(C(F)(F)F)n[nH]c3n1)[C@@H](O)[C@H]2O] | >20 |
| A38 | 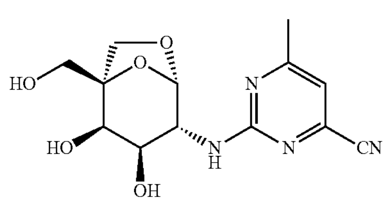 [SMILES: Cc1cc(C#N)nc(N[C@H]2[C@H]3OC[C@](CO)(O3)[C@H](O)[C@@H]2O)n1] | +++ |
| A40 | 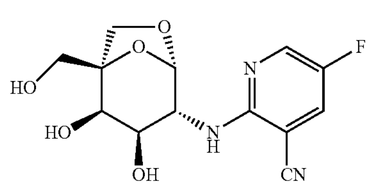 [SMILES: N#Cc1cc(F)cnc1N[C@H]1[C@H]2OC[C@](CO)(O2)[C@H](O)[C@@H]1O] | +++ |

TABLE 4B-continued

ASGPR Binding of Additional ASGPR Binding Ligands

| Compound ID | Structure | ASGPR SPR Binding: $K_D$ (μM) |
|---|---|---|
| A110 | 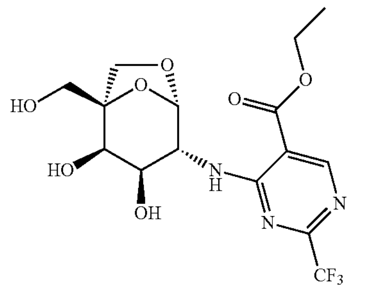 [SMILES: CCOC(=O)c1cnc(C(F)(F)F)nc1N[C@H]1[C@H]2OC[C@](CO)(O2)[C@H](O)[C@@H]1O] | +++ |
| A44 | 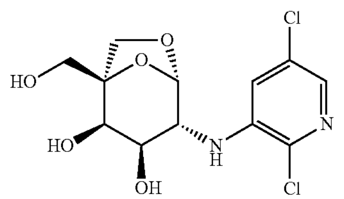 [SMILES: OC[C@@]12CO[C@@H](O1)[C@H](Nc1cc(Cl)cnc1Cl)[C@@H](O)[C@H]2O] | ++++ |
| A41 | 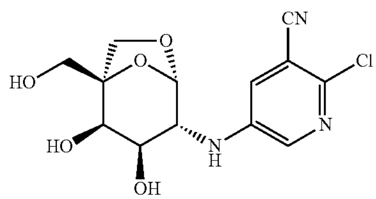 [SMILES: N#Cc1cc(N[C@H]2[C@H]3OC[C@](CO)(O3)[C@H](O)[C@@H]2O)cnc1Cl] | +++ |
| A43 | 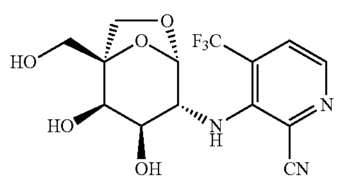 [SMILES: N#Cc1nccc(C(F)(F)F)c1N[C@H]1[C@H]2OC[C@](CO)(O2)[C@H](O)[C@@H]1O] | ++ |
| A39 | 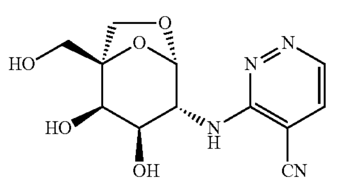 [SMILES: N#Cc1ccnnc1N[C@H]1[C@H]2OC[C@](CO)(O2)[C@H](O)[C@@H]1O] | +++ |
| A42 | 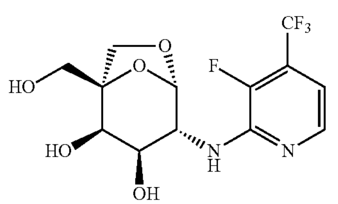 [SMILES: OC[C@@]12CO[C@@H](O1)[C@H](Nc1nccc(C(F)(F)F)c1F)[C@@H](O)[C@H]2O] | ++ |
| A111 | 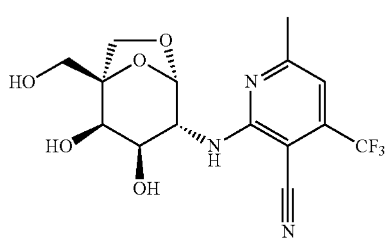 [SMILES: Cc1cc(C(F)(F)F)c(C#N)c(N[C@H]2[C@H]3OC[C@](CO)(O3)[C@H](O)[C@@H]2O)n1] | ++ |

TABLE 4B-continued

ASGPR Binding of Additional ASGPR Binding Ligands

| Compound ID | Structure | ASGPR SPR Binding: $K_D$ (μM) |
|---|---|---|
| A112 | 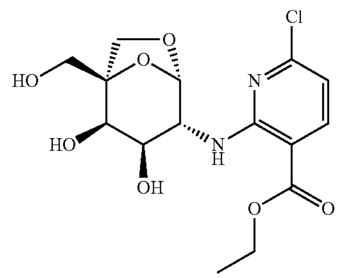 [SMILES: CCOC(=O)c1ccc(Cl)nc1N[C@H]1[C@H]2OC[C@](CO)(O2)[C@H](O)[C@@H]1O] | +++ |
| A113 | 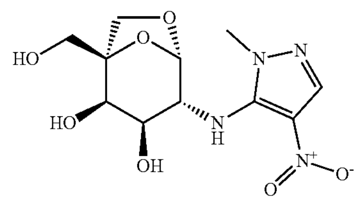 [SMILES: Cn1ncc([N+](=O)[O-])c1N[C@H]1[C@H]2OC[C@](CO)(O2)[C@H](O)[C@@H]1O] | ++++ |
| A45 | 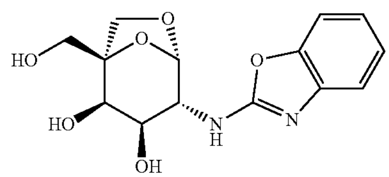 [SMILES: OC[C@@]12CO[C@@H](O1)[C@H](Nc1nc3ccccc3o1)[C@@H](O)[C@H]2O] | +++ |
| A115 | 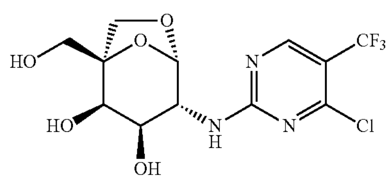 [SMILES: OC[C@@]12CO[C@@H](O1)[C@H](Nc1ncc(C(F)(F)F)c(Cl)n1)[C@@H](O)[C@H]2O] | ++++ |
| A114 | 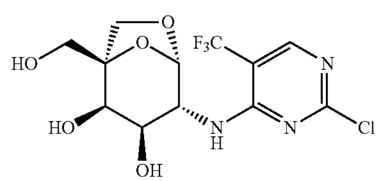 [SMILES: OC[C@@]12CO[C@@H](O1)[C@H](Nc1nc(Cl)ncc1C(F)(F)F)[C@@H](O)[C@H]2O] | ++++ |
| A126 | 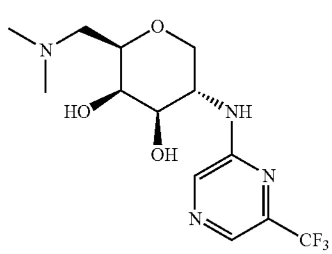 [SMILES: CN(C)C[C@H]1OC[C@H](Nc2cncc(C(F)(F)F)n2)[C@@H](O)[C@H]1O] | ++++ |

TABLE 4B-continued

ASGPR Binding of Additional ASGPR Binding Ligands

| Compound ID | Structure | ASGPR SPR Binding: $K_D$ (μM) |
|---|---|---|
| A118 | 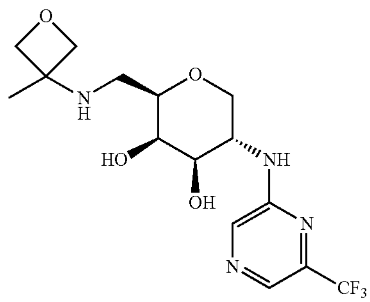 [SMILES: CC1(NC[C@H]2OC[C@H](Nc3cncc(C(F)(F)F)n3)[C@@H](O)[C@H]2O)COC1] | |
| A119 | 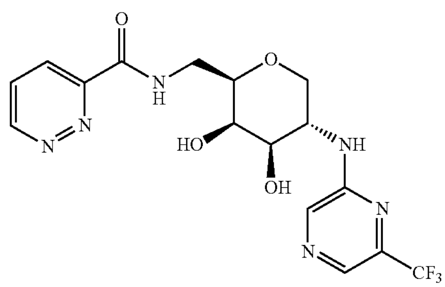 [SMILES: O=C(NC[C@H]1OC[C@H](Nc2cncc(C(F)(F)F)n2)[C@@H](O)[C@H]1O)c1cccnn1] | |
| A120 | 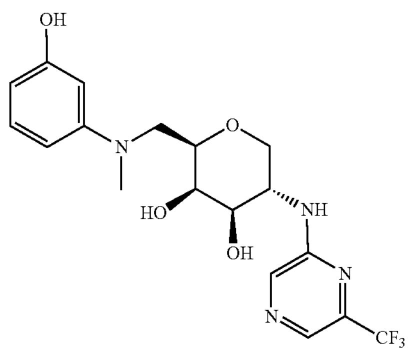 [SMILES: CN(C[C@H]1OC[C@H](Nc2cncc(C(F)(F)F)n2)[C@@H](O)[C@H]1O)c1cccc(O)c1] | |
| A121 | 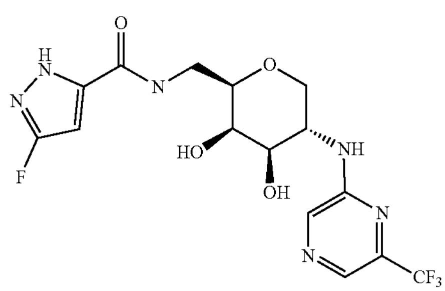 [SMILES: O=C(NC[C@H]1OC[C@H](Nc2cncc(C(F)(F)F)n2)[C@@H](O)[C@H]1O)c1cc(F)n[nH]1] | |
| A122 | 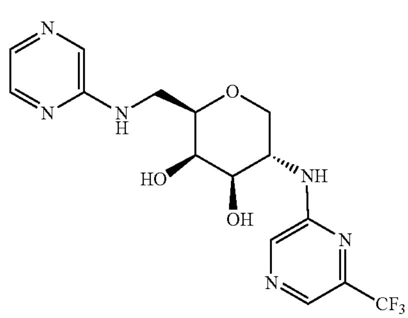 [SMILES: O[C@@H]1[C@H](O)[C@@H](Nc2cncc(C(F)(F)F)n2)CO[C@@H]1CNc1cnccn1] | ++++ |

TABLE 4B-continued

ASGPR Binding of Additional ASGPR Binding Ligands

| Compound ID | Structure | ASGPR SPR Binding: $K_D$ (μM) |
|---|---|---|
| A123 | 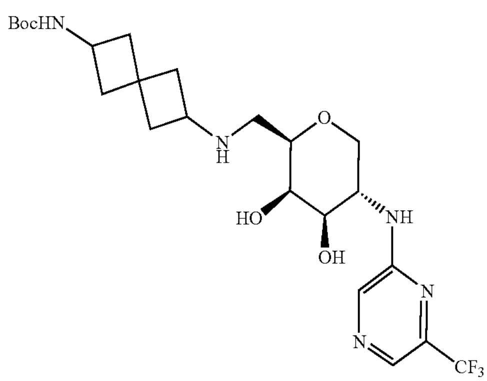 [SMILES: CC(C)(C)OC(=O)NC1CC2(CC(NC[C@H]3OC[C@H](Nc4cncc(C(F)(F)F)n4)[C@@H](O)[C@H]3O)C2)C1] | |
| A124 | 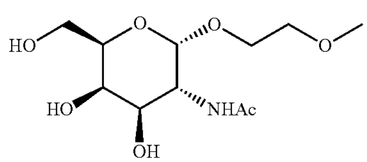 [SMILES: COCCO[C@H]1O[C@H](CO)[C@H](O)[C@H](O)[C@H]1NC(C)=O] | |
| A125 | 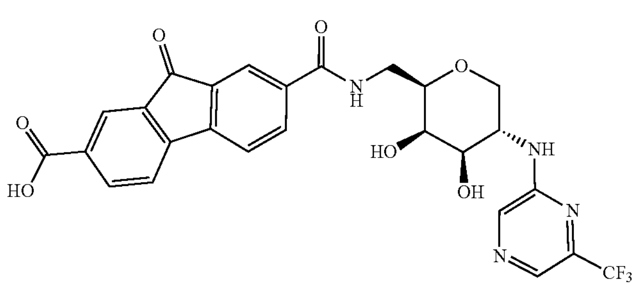 [SMILES: O=C(O)c1ccc2c(c1)C(=O)c1cc(C(=O)NC[C@H]3OC[C@H](Nc4cncc(C(F)(F)F)n4)[C@@H](O)[C@H]3O)ccc1-2] | |

In the table above $K_d$ values that are >= 100 μM = +, <100 μM = ++, <10 μM = +++, and <1 μM = ++++

TABLE 4C
ASGPR and IgG Affinity of selected compounds
| Name | Structure | ASGPR $K_D$ (nM) | IgG $K_D$ (nM) | TCF $EC_{50}$ | Uptake $EC_{50}$ |
|---|---|---|---|---|---|
| Compound 61 | 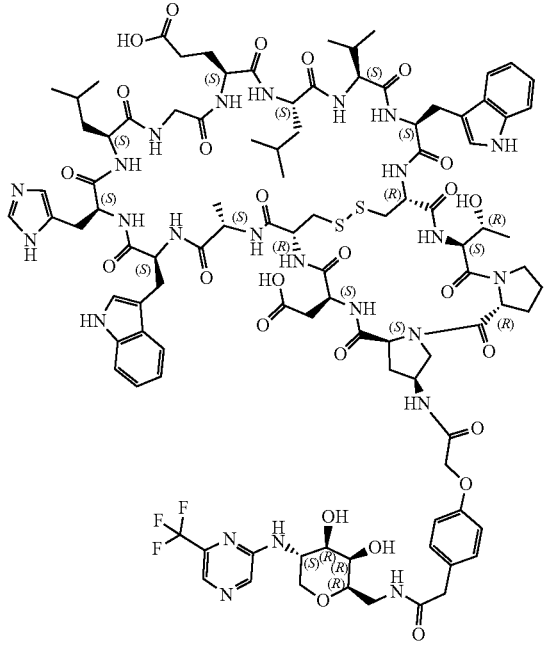 | ** |  |  | ** |
| Compound 62 | 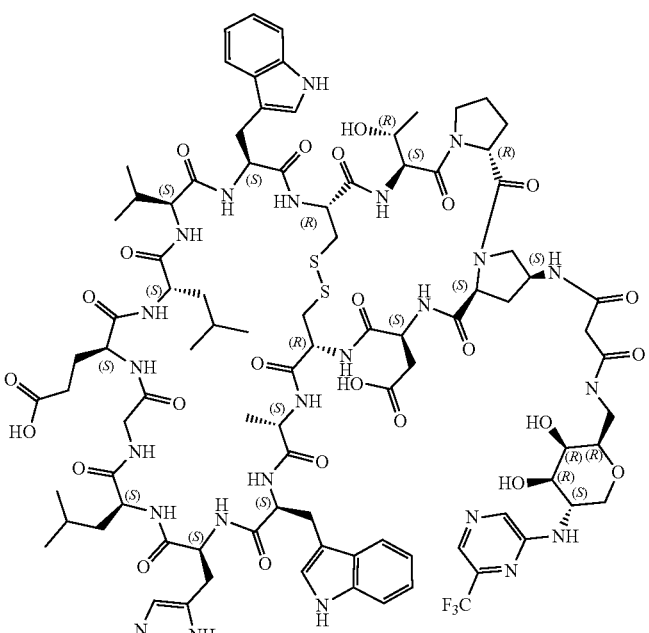 | ** |  |  | ** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 63 | 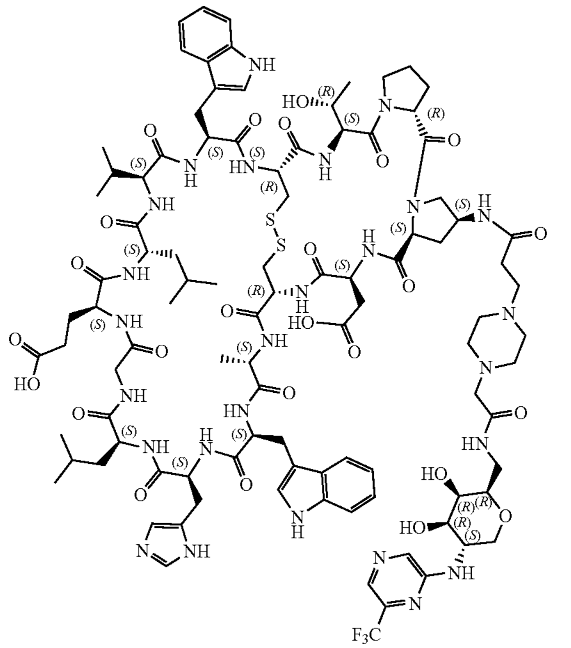 | * |  |  | ** |
| Compound 64 | 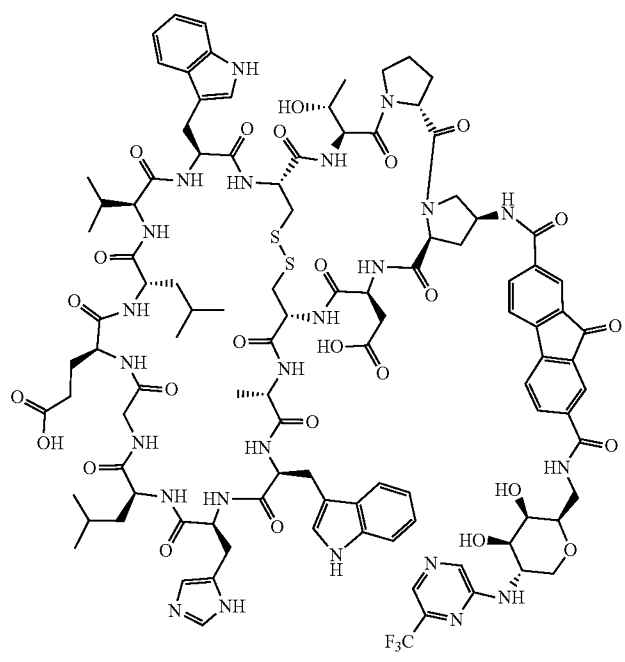 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC1=O)C(=O)N[C@@H]([C@@H](C)O)C(=O)N1CCC[C@@H]1C(=O)N1C[C@@H](NC(=O)c3ccc4c(c3)C(=O)c3cc(C(=O)NC[C@H]5OC[C@H](Nc6cncc(C(F)(F)F)n6)[C@@H](O)[C@H]5O)ccc3-4)C[C@H]1C(=O)N[C@@H](CC(=O)O)C(=O)N2] | ** |  |  | * |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 65 | 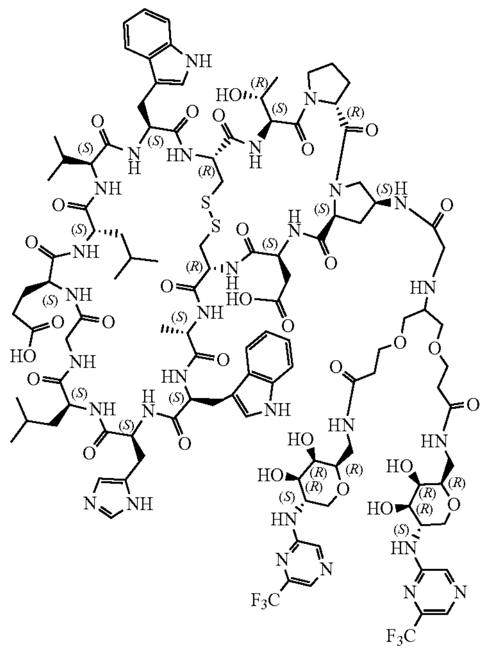 | ** |  |  | ** |
| Compound 66 | 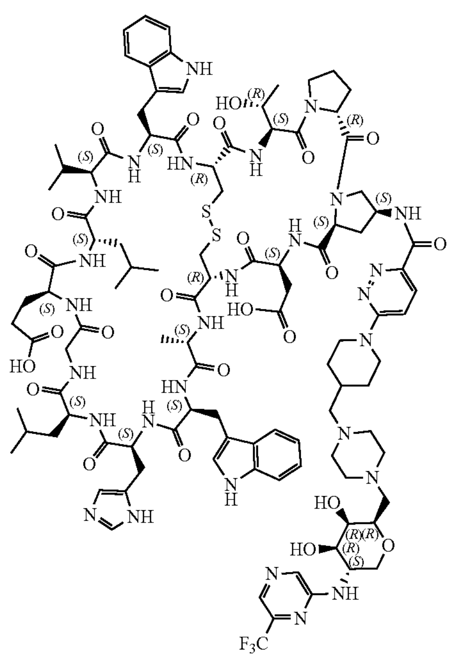 | ** |  |  | ** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 67 | 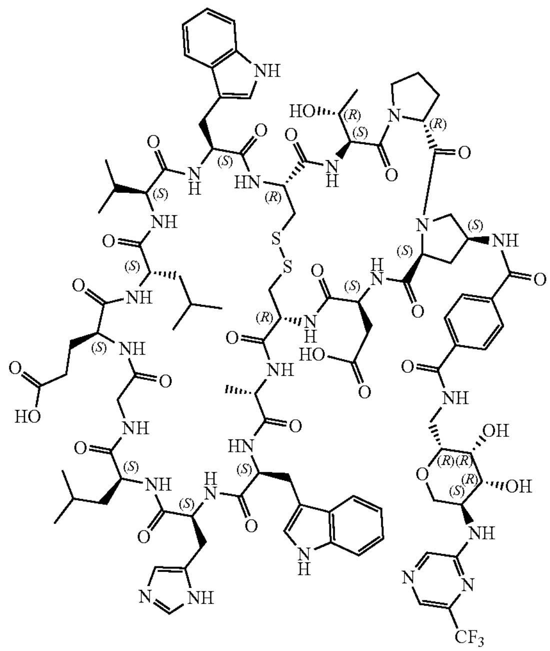 | ** | ** | * | * |
| Compound 68 | 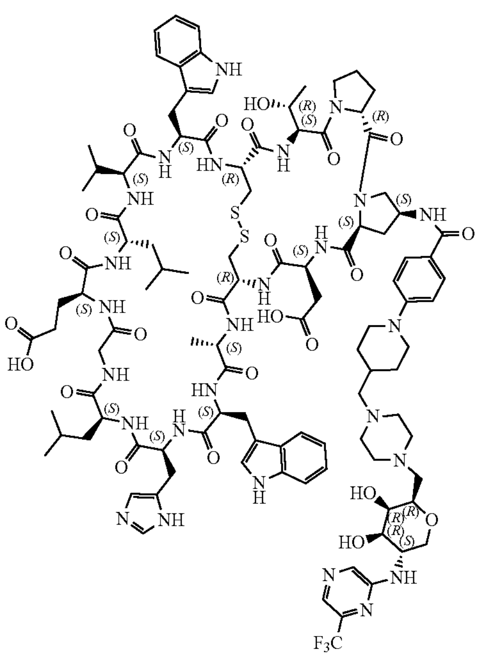 | ** |  |  | ** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 69 | 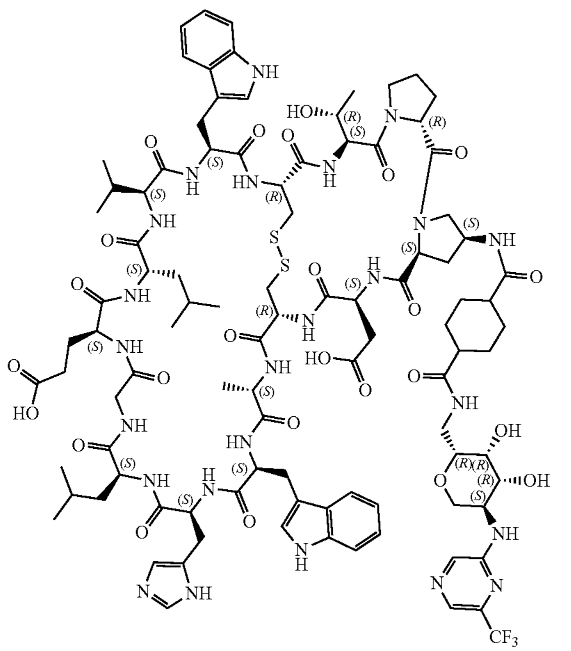 | * | ** | * | * |
| Compound 45 | 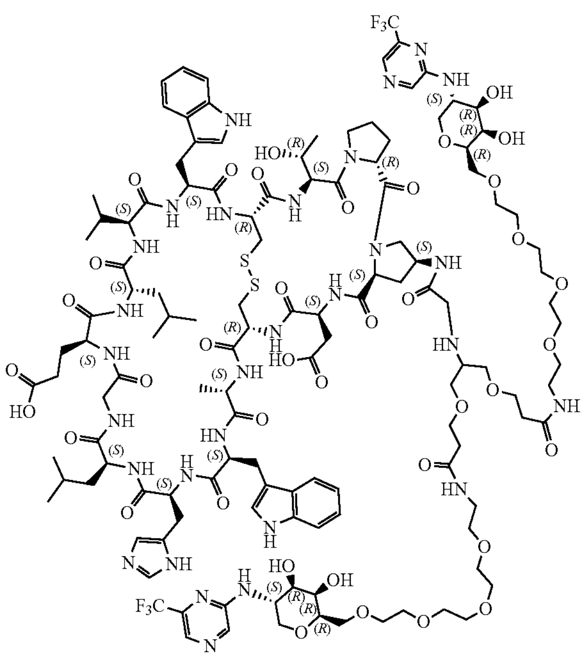 | ** |  |  | ** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 70 | 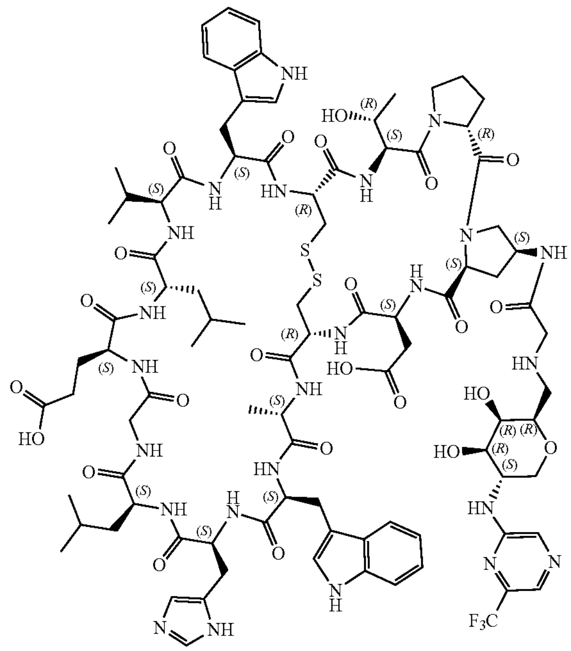 | | | | |
| Compound 71 | 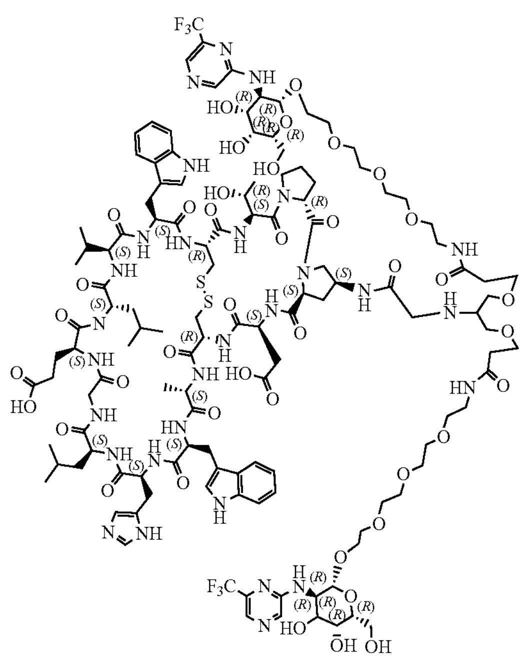 | ** |  | ** | |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 72 | 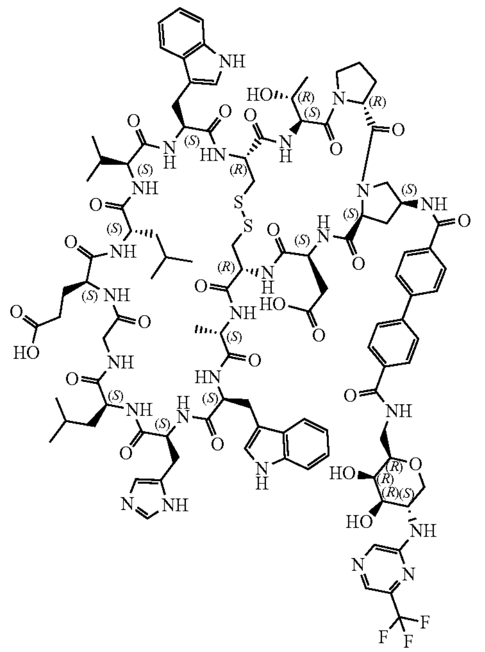 | ** |  |  | **** |
| Compound 42 | 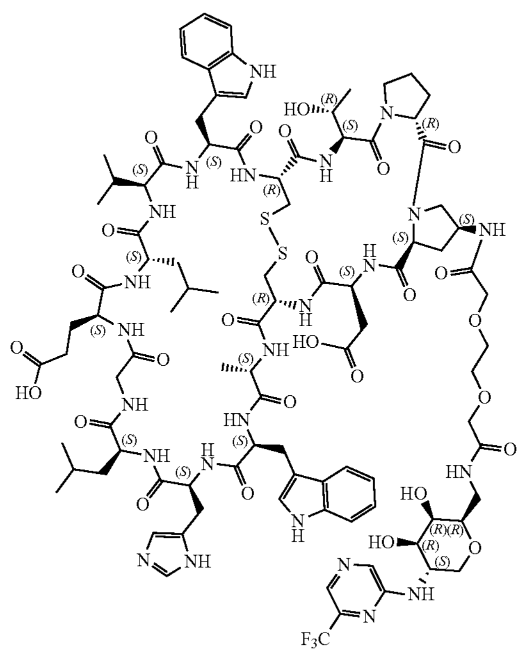 | ** |  |  | ** |

TABLE 4C-continued

ASGPR and IgG Affinity of selected compounds

| Name | Structure | ASGPR K_D (nM) | IgG K_D (nM) | TCF EC_{50} | Uptake EC_{50} |
|---|---|---|---|---|---|
| Compound 73 | 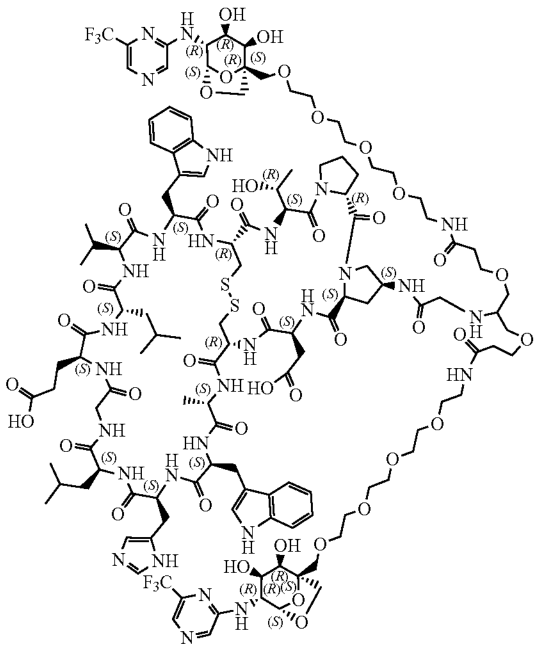 | | | ** |  |
| Compound 74 | 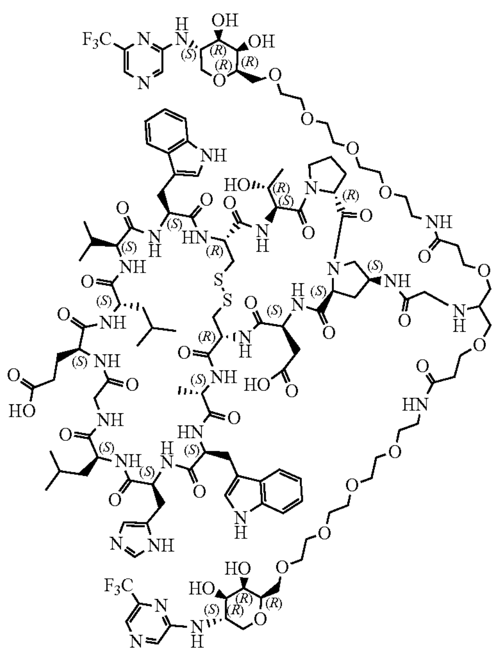 | ** |  |  | ** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 75 | 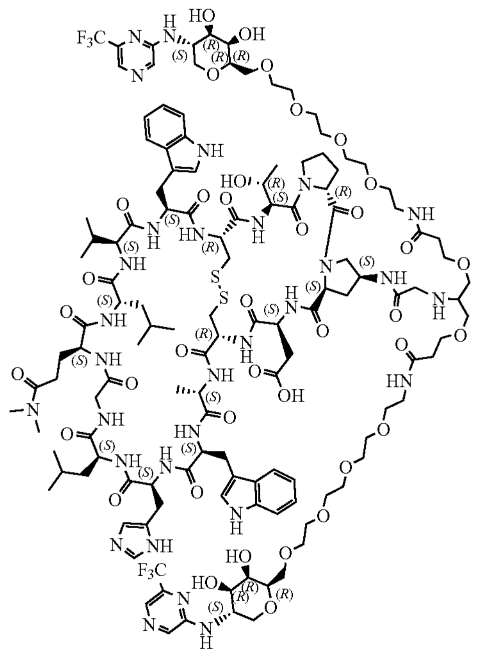 | ** |  |  | ** |
| Intermediate 12 | 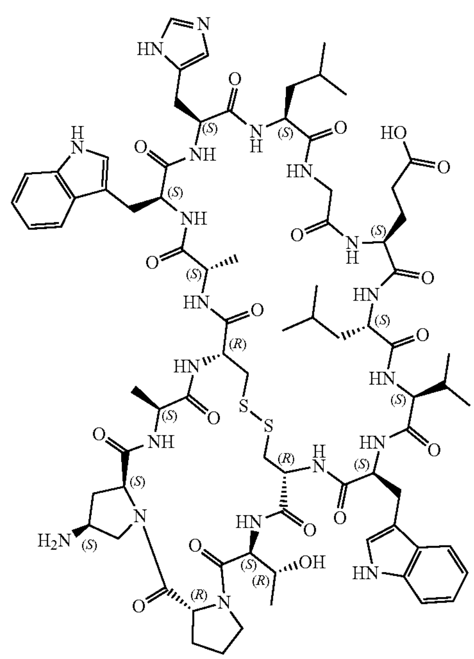 | | | | **** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Intermediate 13 | | | **** | | |
| Intermediate 14 | | | **** | | |

TABLE 4C-continued
ASGPR and IgG Affinity of selected compounds
| Name | Structure | ASGPR $K_D$ (nM) | IgG $K_D$ (nM) | TCF $EC_{50}$ | Uptake $EC_{50}$ |
|---|---|---|---|---|---|
| Intermediate 15 | 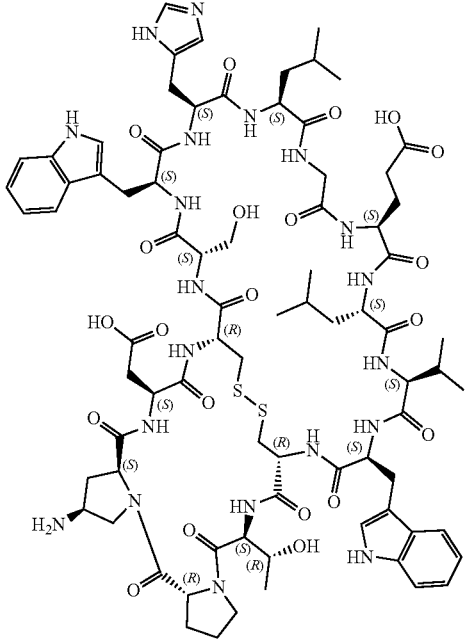 | **** | | | |
| Intermediate 16 | 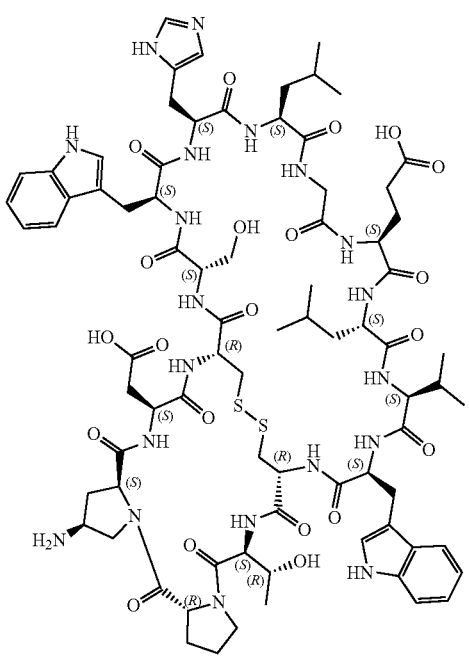 | **** | | | |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Intermediate 17 | 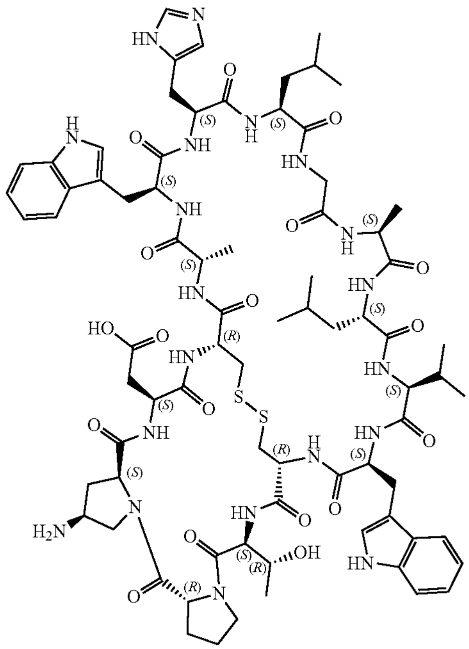 | | | | **** |
| Intermediate 18 | 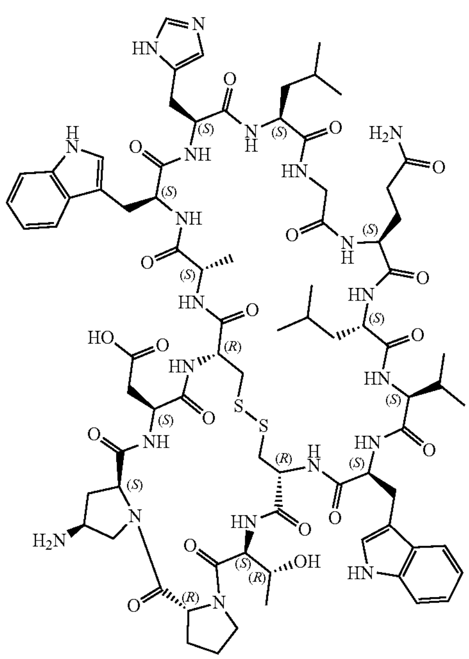 | | | | **** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Intermediate 19 | | | | | **** |
| Intermediate 29 | | | | | **** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Intermediate 21 | 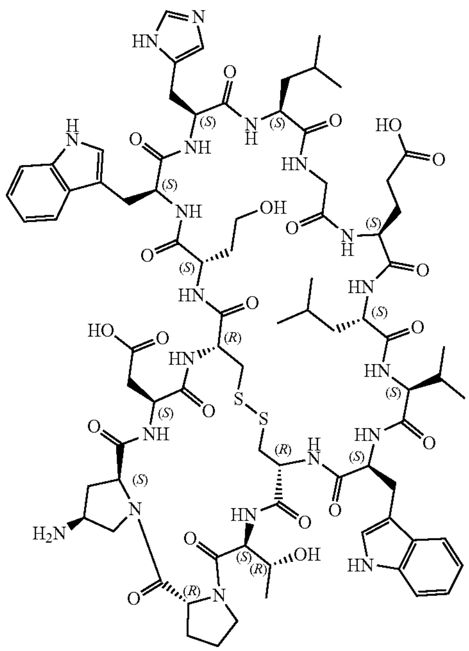 | | | | **** |
| Intermediate 22 | 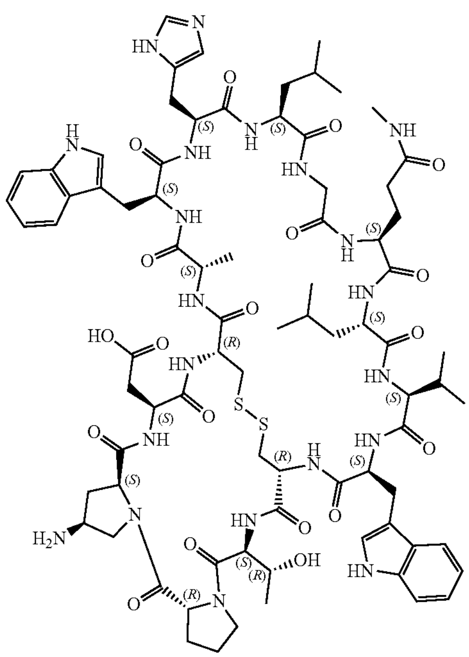 | | | | **** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Intermediate 23 | 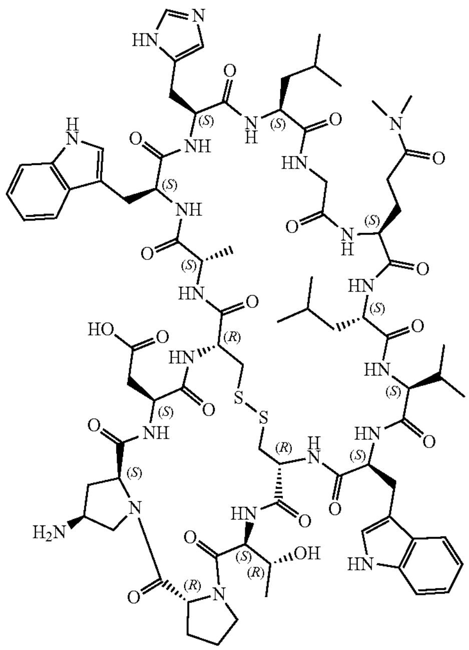 | | **** | | |
| Intermediate 24 | 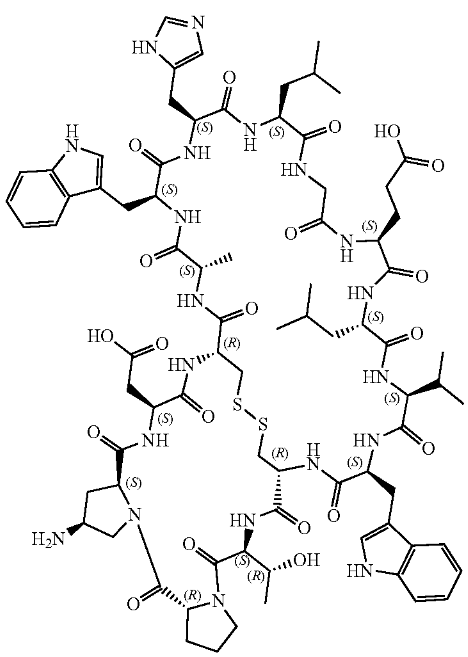 | | **** | | |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Intermediate 25 | 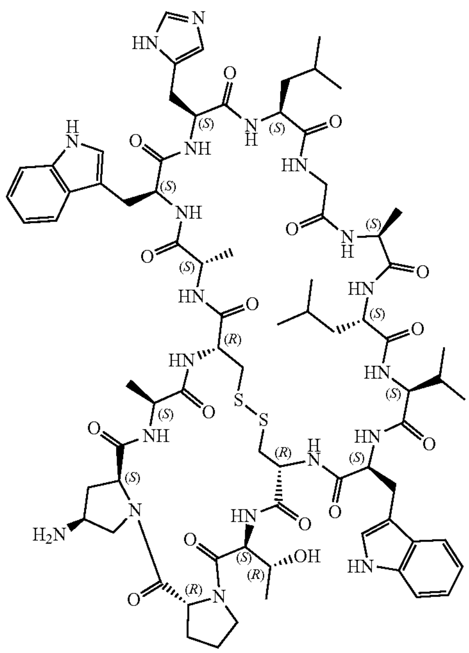 | | | | **** |
| Intermediate 26 | 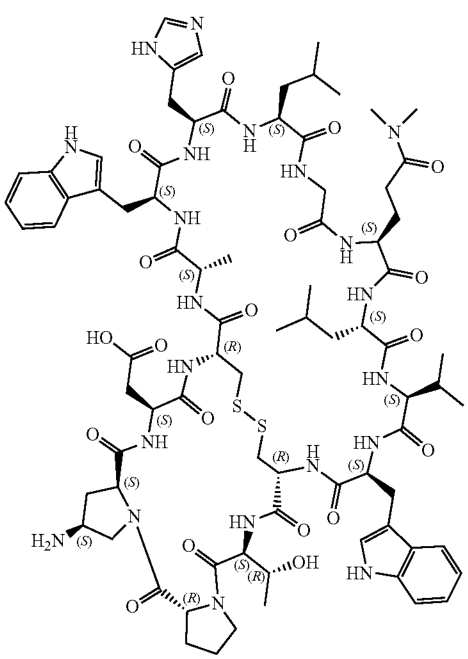 | | | | **** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Intermediate 27 | 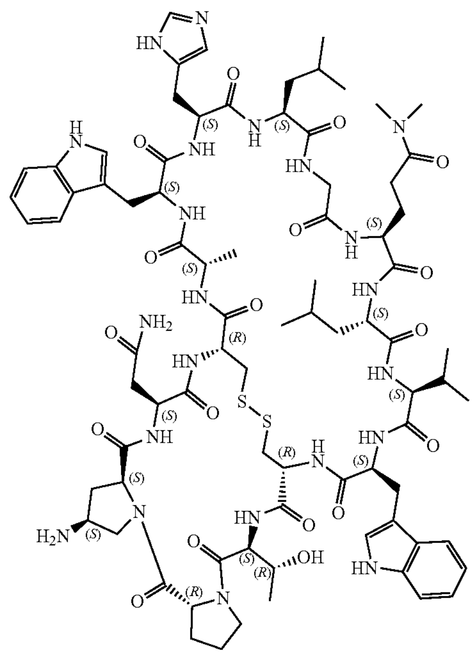 | | **** | | |
| Intermediate 28 | 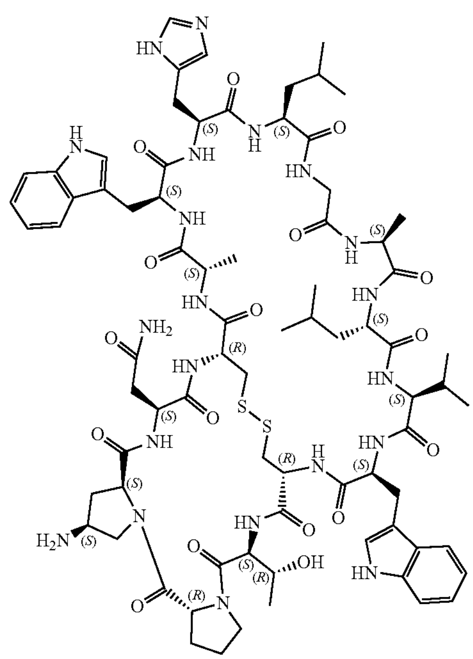 | | **** | | |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 76 | 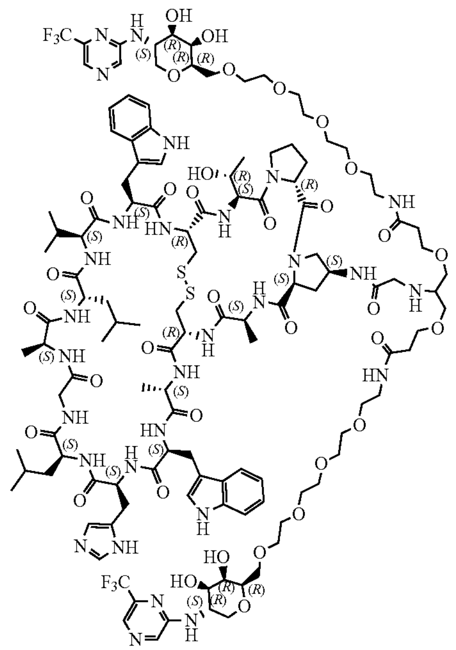 | ** |  |  | ** |
| Compound 77 | 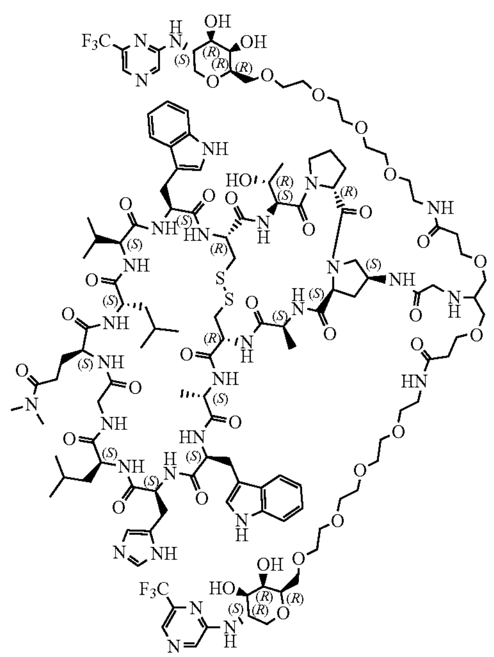 | ** |  |  | ** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 78 | 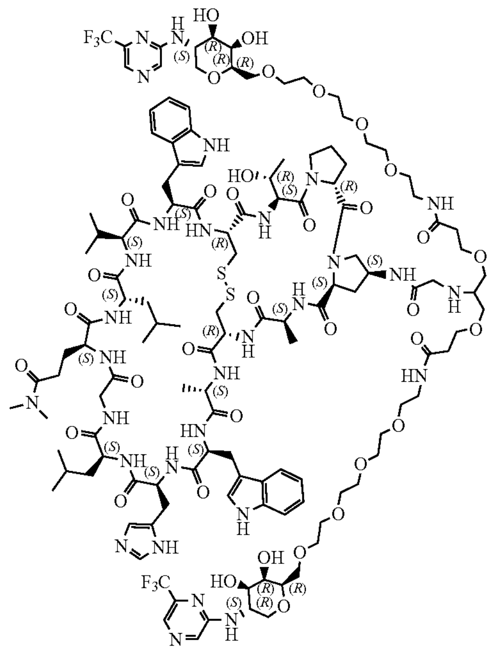 | ** |  |  | ** |
| Compound 79 | 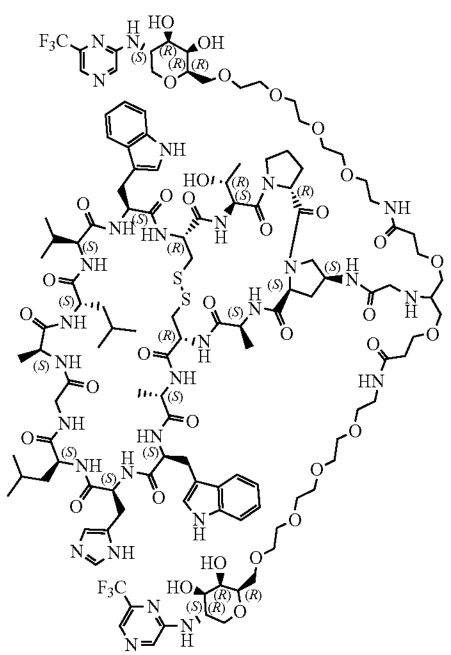 | ** |  |  | ** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Intermediate 8 | 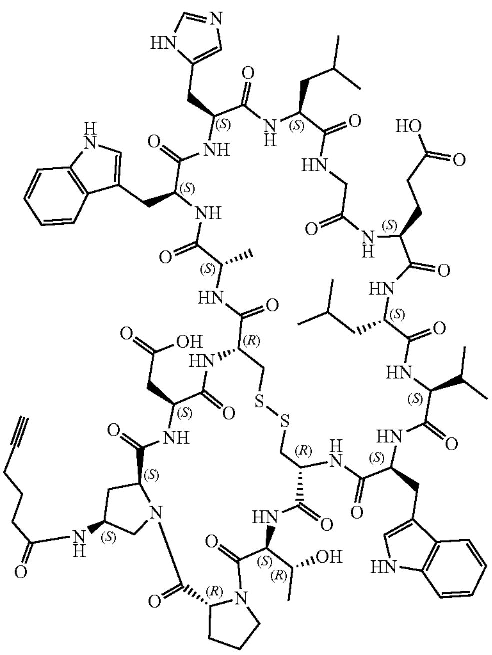 | | | | **** |
| Compound 53 | 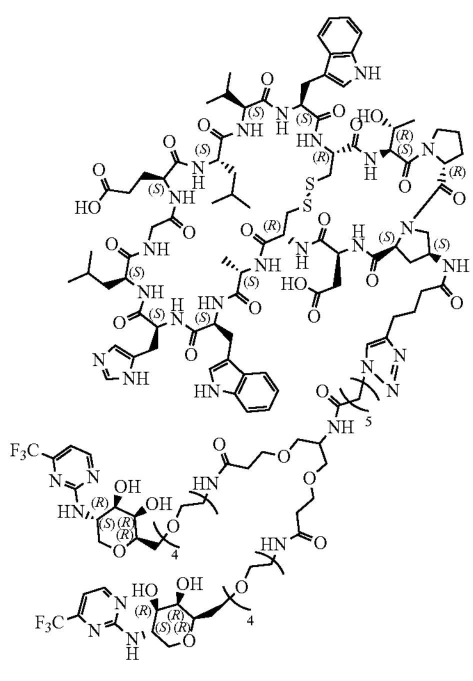 | ** |  |  | ** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|------|-----------|------------------|----------------|---------------|------------------|
| Compound 32 | 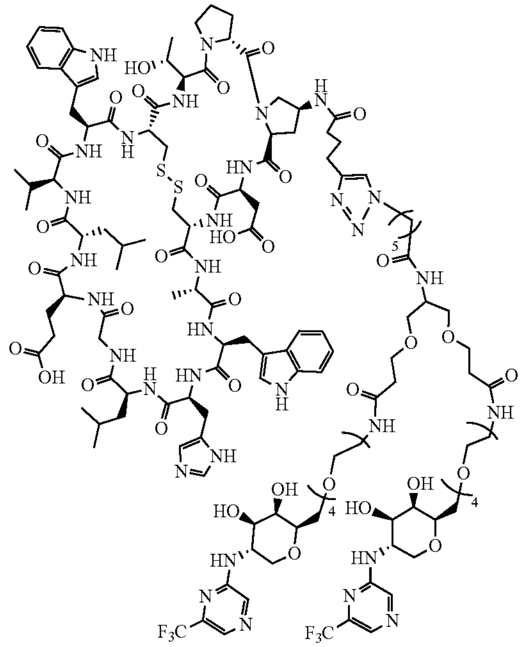 | ** |  | ** | |
| Compound 51 | 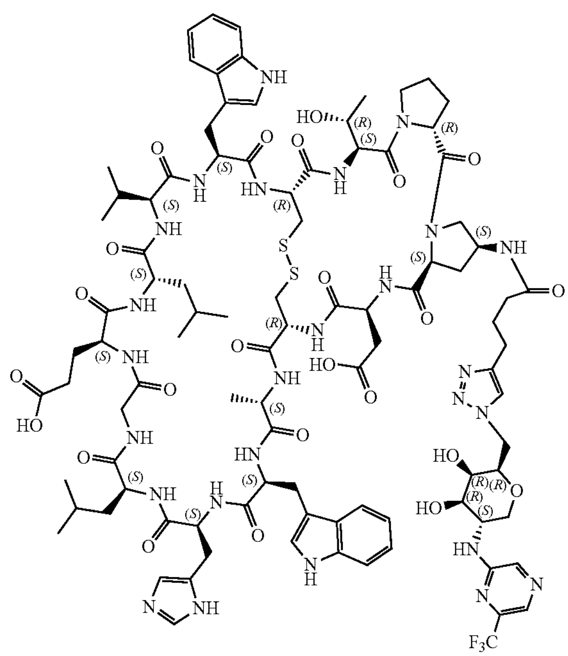 | ** |  |  | ** |

TABLE 4C-continued

*ASGPR and IgG Affinity of selected compounds*

| Name | Structure | ASGPR $K_D$ (nM) | IgG $K_D$ (nM) | TCF $EC_{50}$ | Uptake $EC_{50}$ |
|---|---|---|---|---|---|
| Compound 80 | 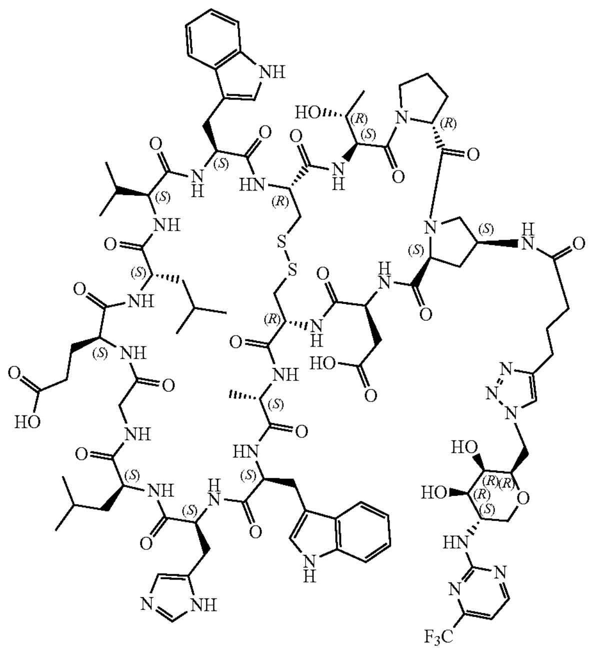 | * | **** | | |
| Compound 81 | 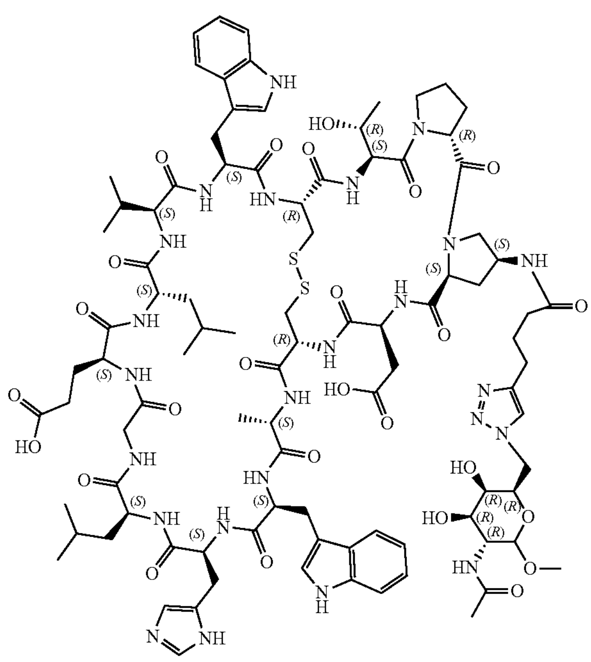 | | | | |

TABLE 4C-continued
ASGPR and IgG Affinity of selected compounds
| Name | Structure | ASGPR $K_D$ (nM) | IgG $K_D$ (nM) | TCF $EC_{50}$ | Uptake $EC_{50}$ |
|---|---|---|---|---|---|
| Intermediate 4 | 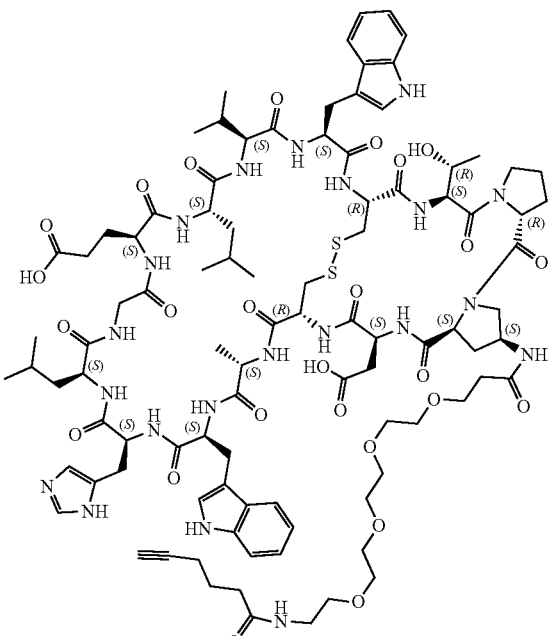 | | | | **** |
| Compound 4 | 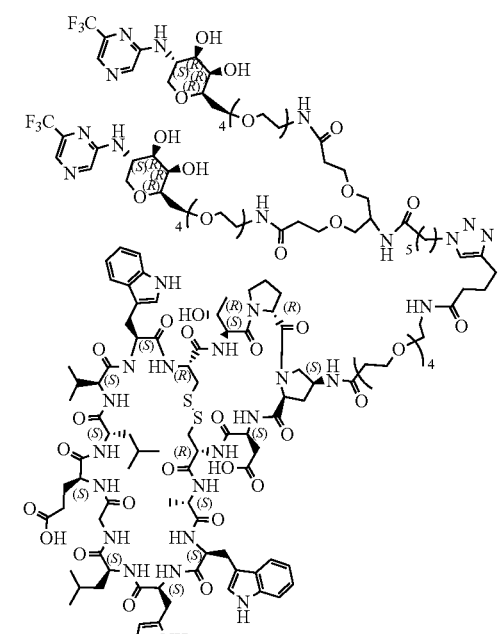 | ** |  |  | ** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 16 | 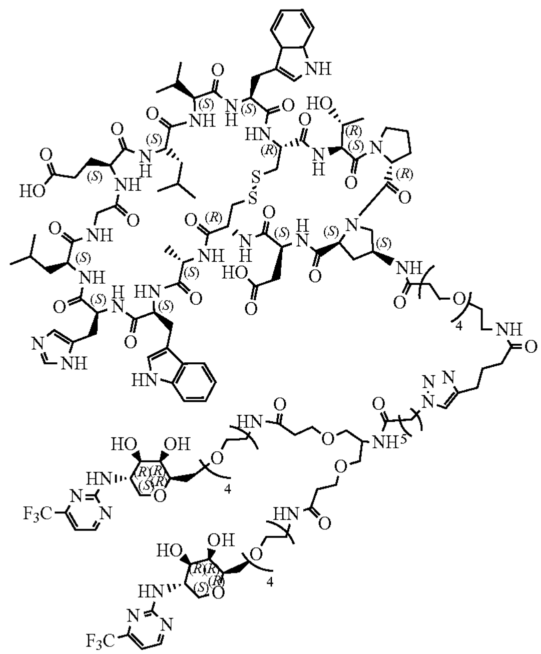 | ** |  |  | ** |
| Compound 82 | 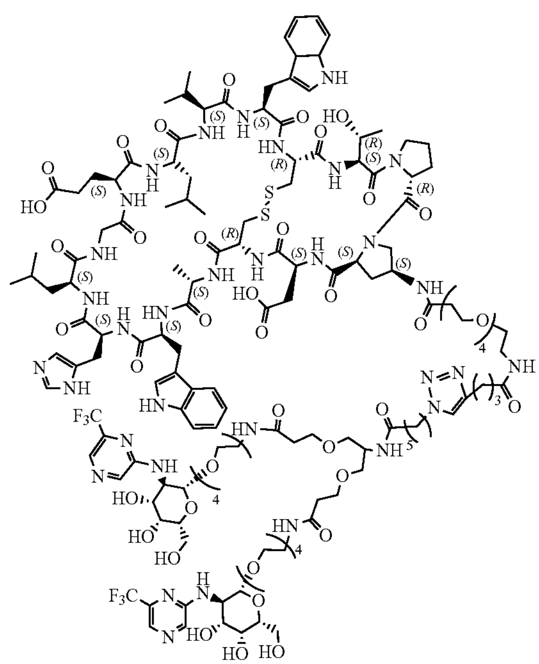 | | | ** | ** |

TABLE 4C-continued
ASGPR and IgG Affinity of selected compounds
| Name | Structure | ASGPR $K_D$ (nM) | IgG $K_D$ (nM) | TCF $EC_{50}$ | Uptake $EC_{50}$ |
|---|---|---|---|---|---|
| Compound 3 | 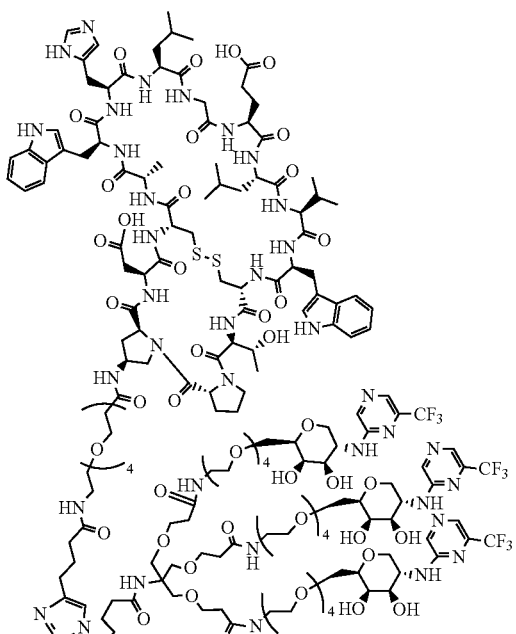 | | | ** | ** |
| Compound 84 | 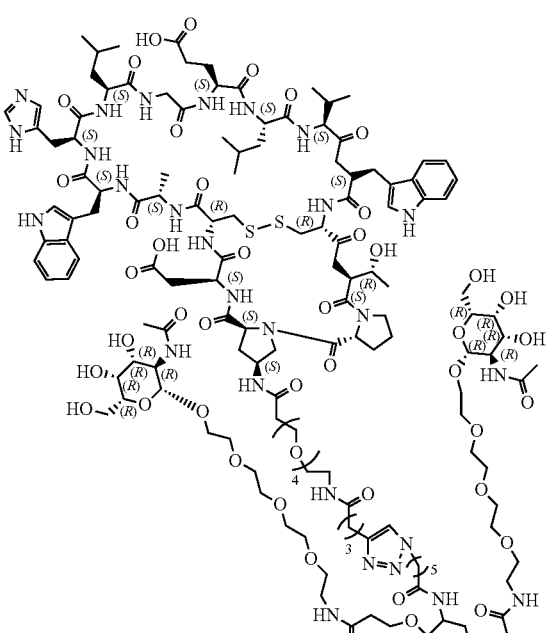 | * | **** | * | * |

TABLE 4C-continued
ASGPR and IgG Affinity of selected compounds
| Name | Structure | ASGPR $K_D$ (nM) | IgG $K_D$ (nM) | TCF $EC_{50}$ | Uptake $EC_{50}$ |
|---|---|---|---|---|---|
| Compound 85 | 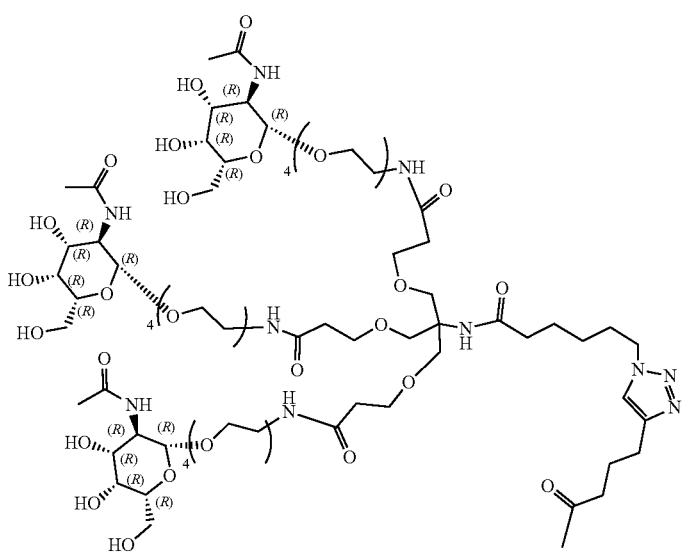 |  | ** | * | * |
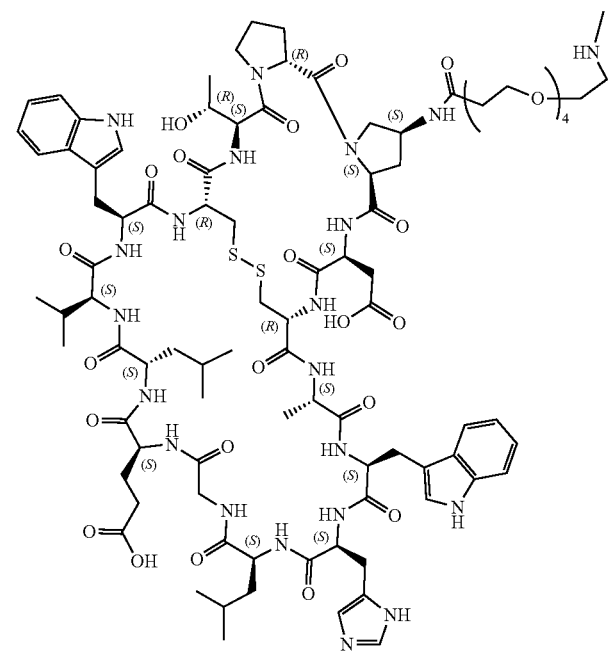

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 86 | 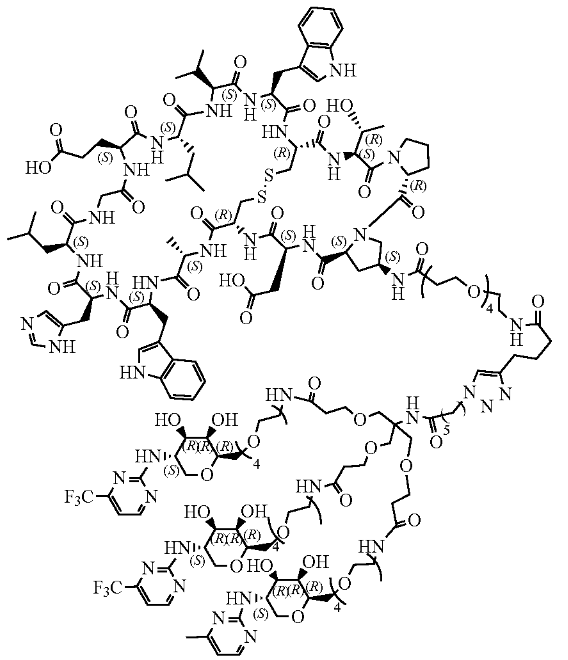 | ** |  |  | ** |
| Intermediate 1 | 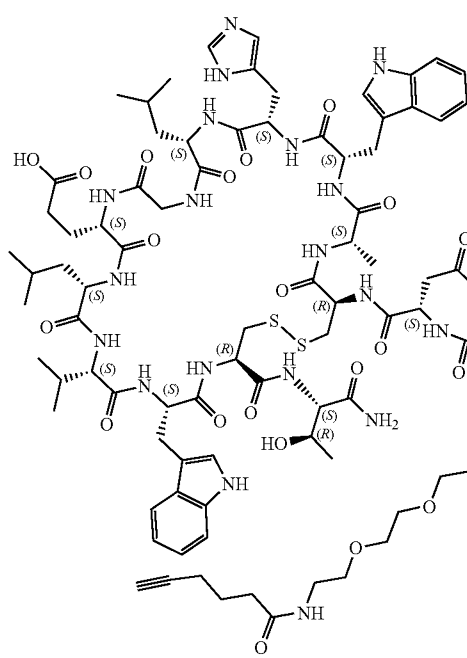 | | | | **** |

TABLE 4C-continued

ASGPR and IgG Affinity of selected compounds

| Name | Structure | ASGPR K$_D$ (nM) | IgG K$_D$ (nM) | TCF EC$_{50}$ | Uptake EC$_{50}$ |
|---|---|---|---|---|---|
| Compound 22 | 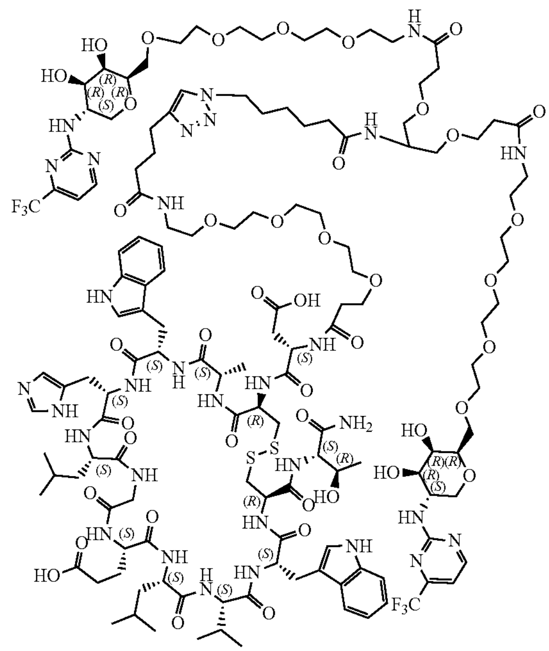 | ** |  |  | ** |
| Compound 87 | 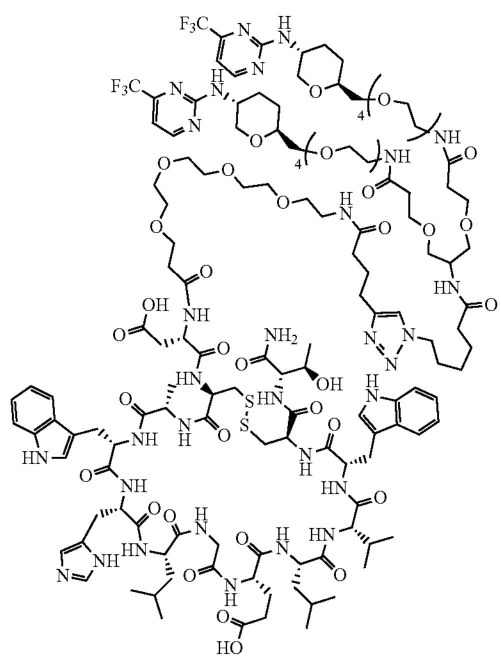 | * | | * | * |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 88 | 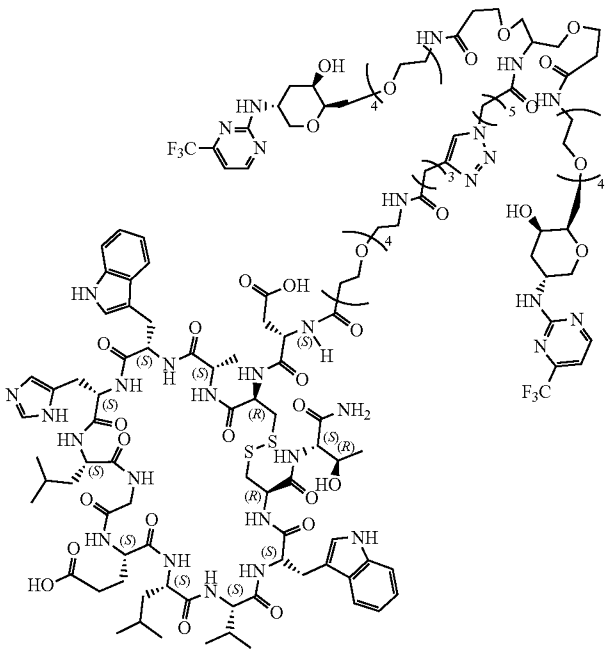 | * | | * | * |
| Compound 89 | 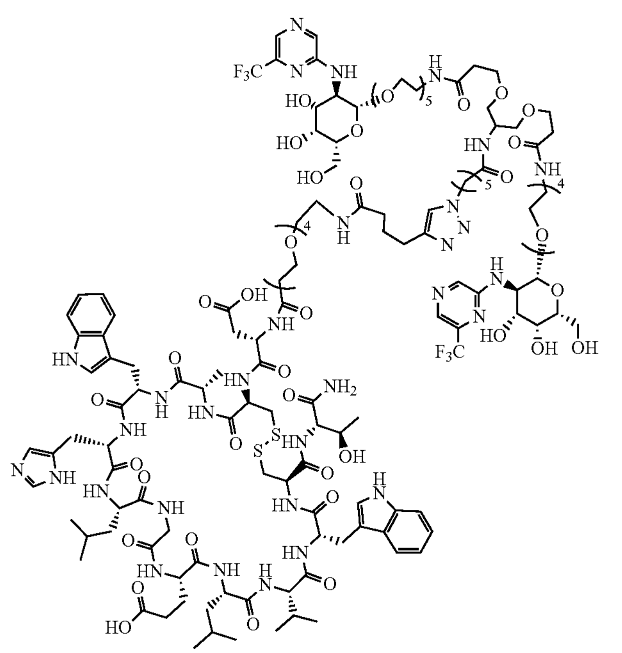 | ** | | | ** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|------|-----------|------------------|-----------------|----------------|------------------|
| Compound 90 | 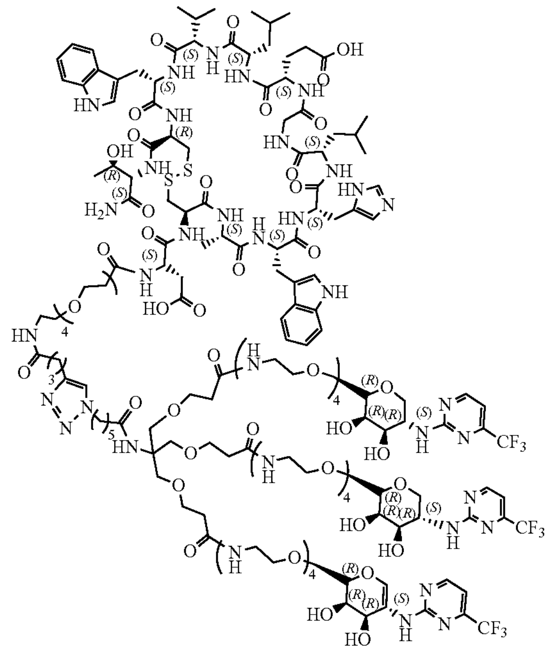 | ** | |  | ** |
| Intermediate 30 | 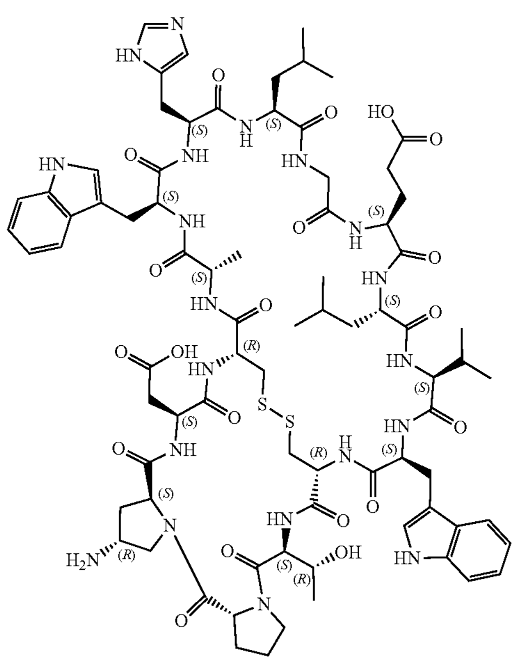 | **** | | | |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 91 | 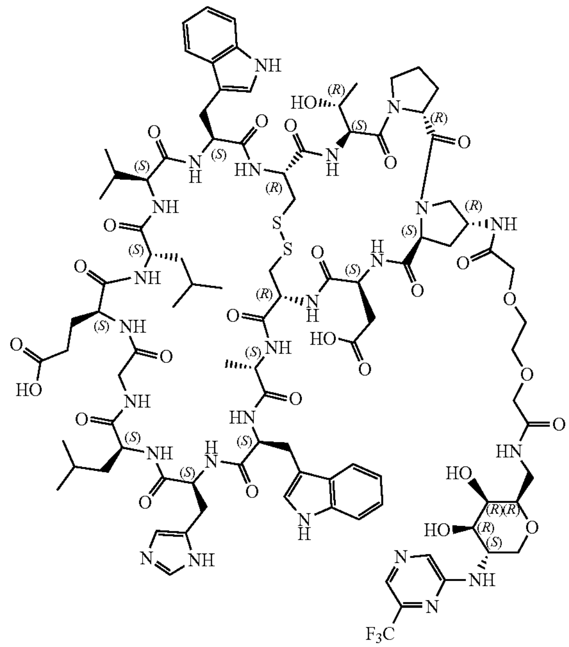 | ** |  | ** | |
| Compound 92 | 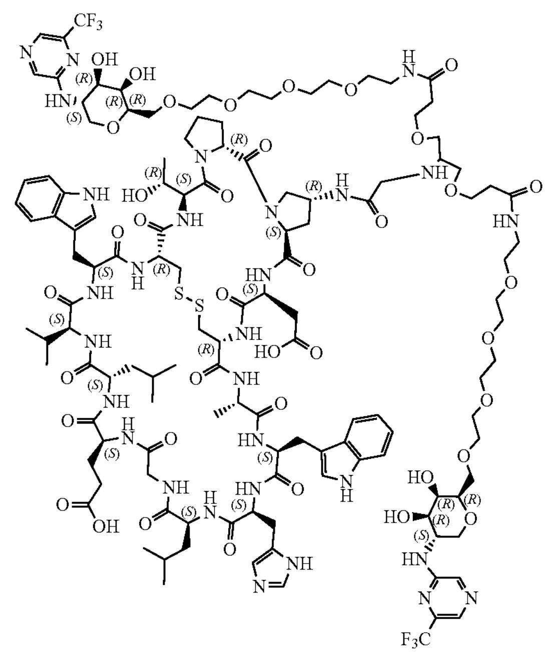 | ** |  |  | ** |

TABLE 4C-continued
ASGPR and IgG Affinity of selected compounds
| Name | Structure | ASGPR $K_D$ (nM) | IgG $K_D$ (nM) | TCF $EC_{50}$ | Uptake $EC_{50}$ |
|---|---|---|---|---|---|
| Compound 93 | 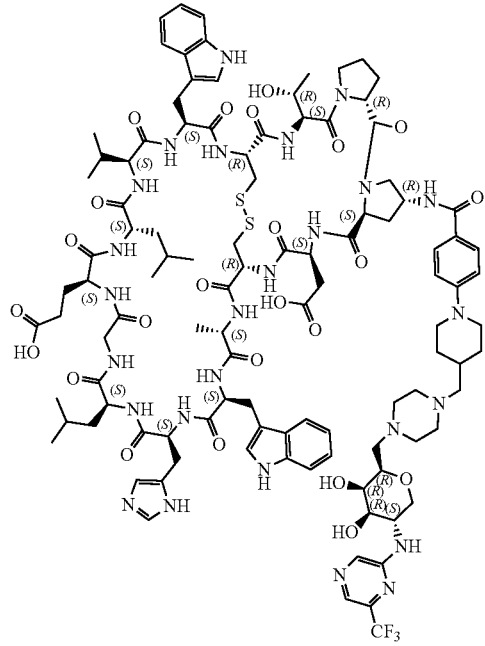 | | | ** | ** |
| Intermediate 31 | 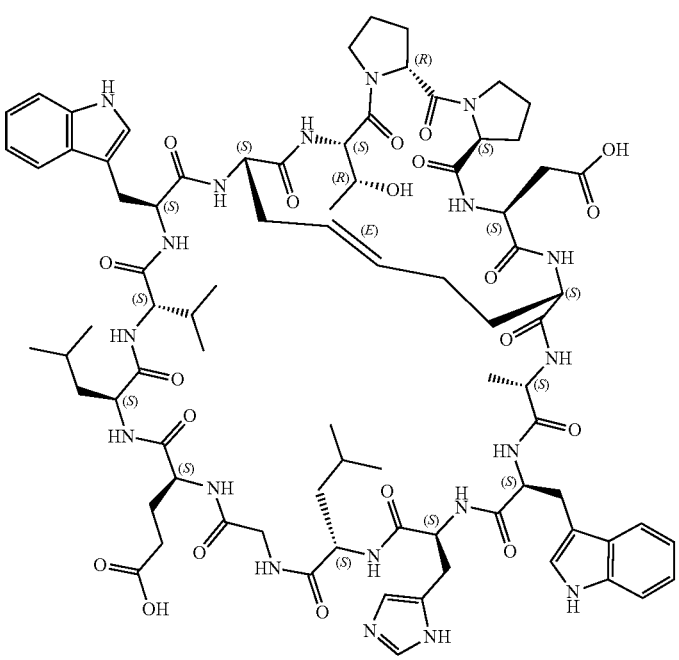 | | | | **** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| A134 | 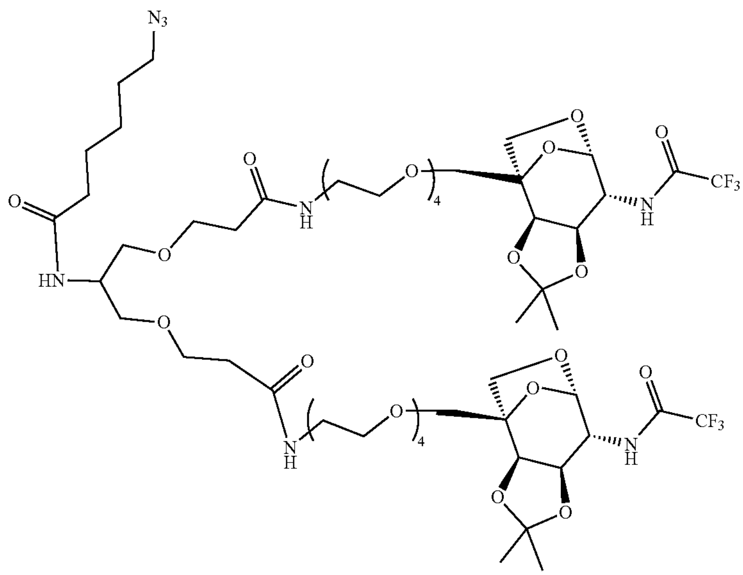 | | | | |
| Compound 94 | 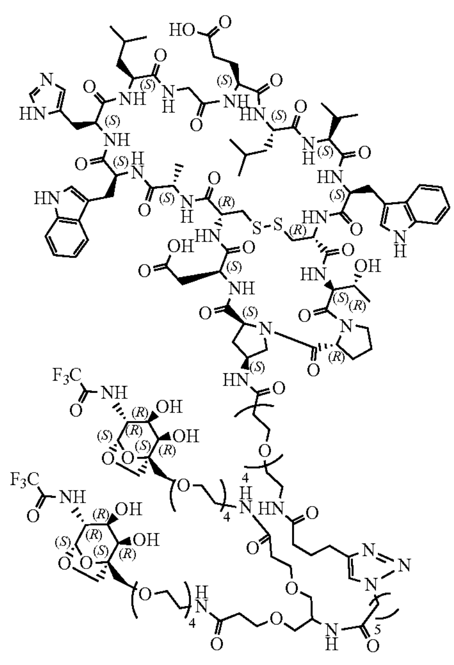 | ** |  |  | ** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| A136 | 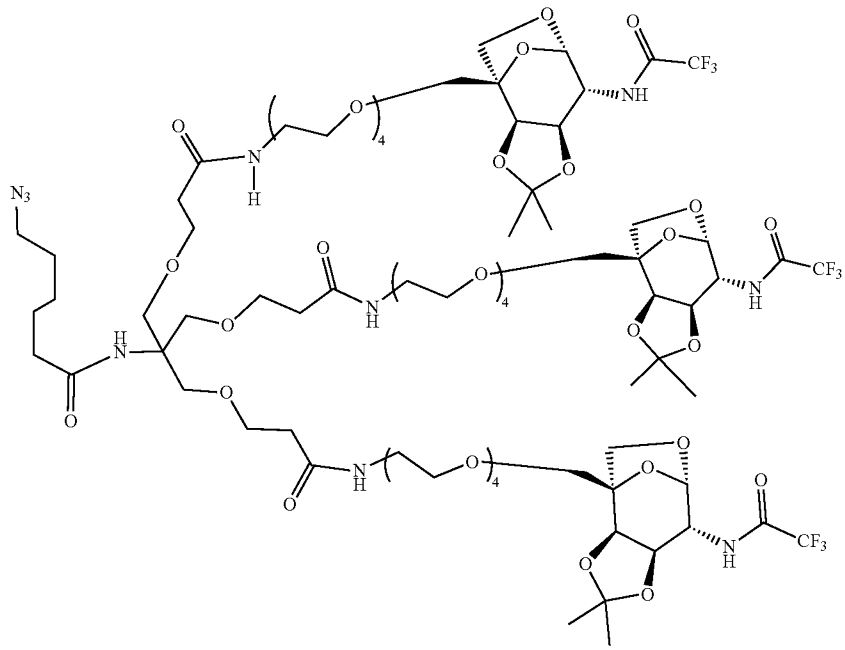 | | | | |
| Compound 95 | 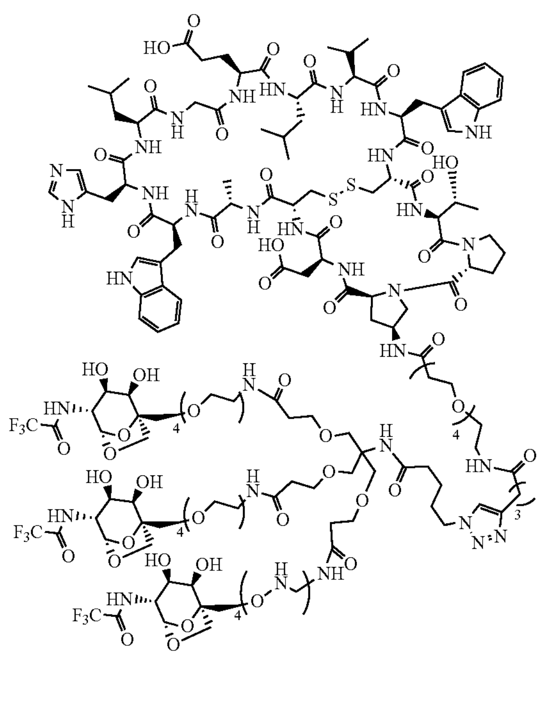 | ** |  |  | ** |

TABLE 4C-continued

ASGPR and IgG Affinity of selected compounds

| Name | Structure | ASGPR $K_D$ (nM) | IgG $K_D$ (nM) | TCF $EC_{50}$ | Uptake $EC_{50}$ |
|---|---|---|---|---|---|
| Compound 96 | 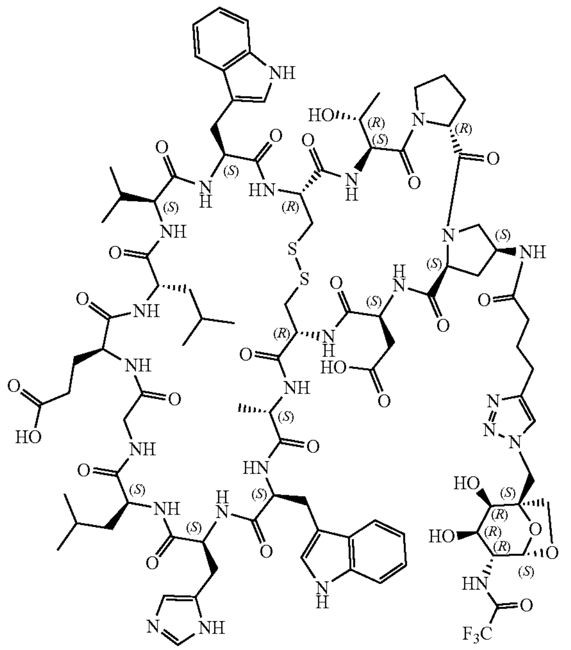 | | | | |
| Intermediate 32 | 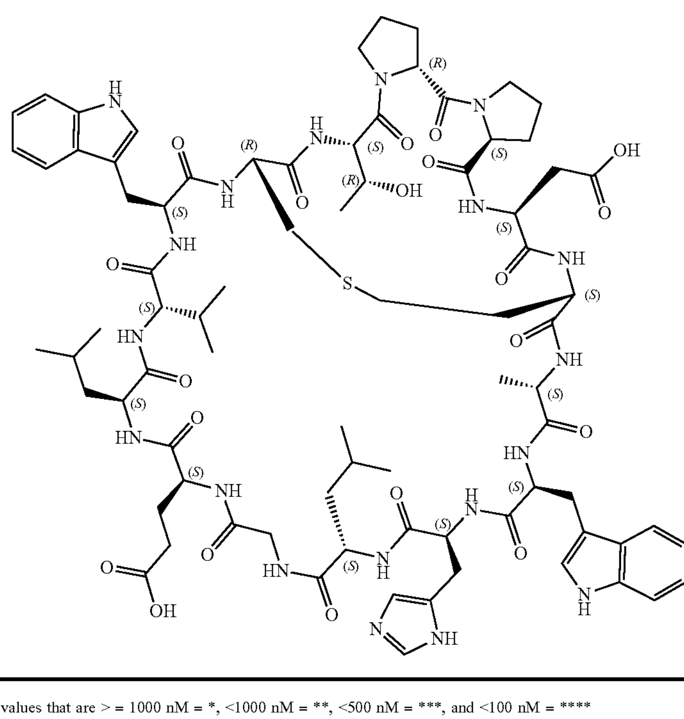 | | | | |

In the table above $K_d$ values that are $>= 1000$ nM = *, <1000 nM = , <500 nM = *, and <100 nM = ****

Example 2 Affinity of Compounds to IgG Measured Using Surface Plasmon Resonance (SPR)

The dissociation constants (Kd) of compounds described herein to IgG were measured by surface plasmon resonance (SPR) using a Biacore 8K instrument (GE Healthcare) at 25° C. IgG (2 µg/ml) is immobilized on CM5 sensor chips (GE Healthcare) at flow rate of 5 µl/min for 290 sec using NHS/EDC chemistry in NaAcetate pH 5.5. Immobilization levels ranging from 1000-1300 resonance units (RU) are obtained. The running buffer is 10 mM HEPES, pH 7.4, 400 mM NaCl, 0.005% P20, 30 DMSO. The initial concentration of compounds varies from 500 nM to 100 nM depending on $K_d$ values. The compounds are diluted 2 or 3-fold with 8 concentration points. Solutions containing serially diluted compounds are injected at a flow rate of 50 µL/min for 90 sec followed by a 500 sec dissociation phase for each concentration.

Figure 22:
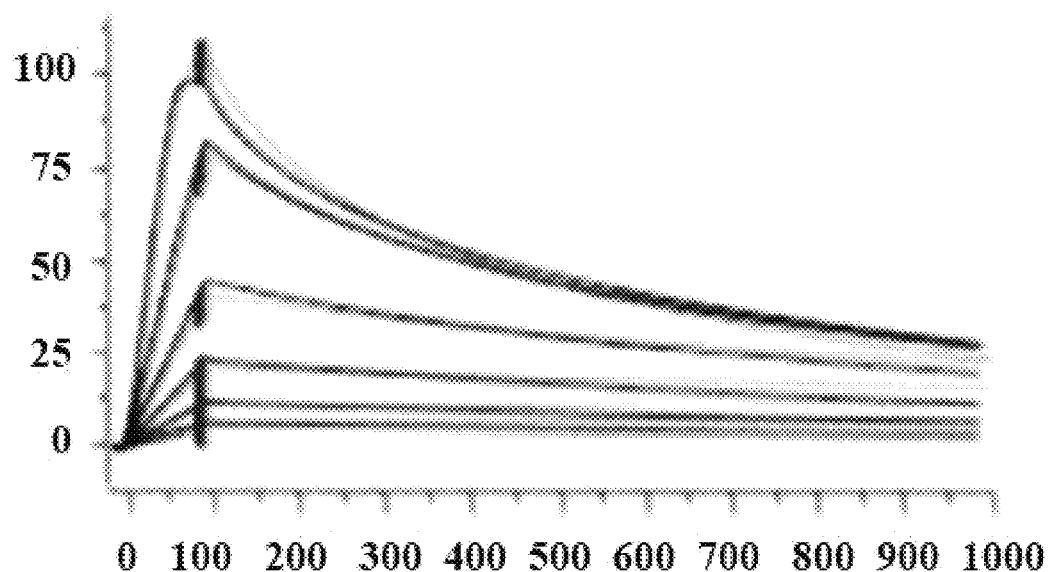
FIG. 22 is a line graph showing the IgG binding of Compound 4 measured by SPR as described in Example 2. The y-axis is response measured in units and the x-axis is time measured in seconds.
Figure 23:
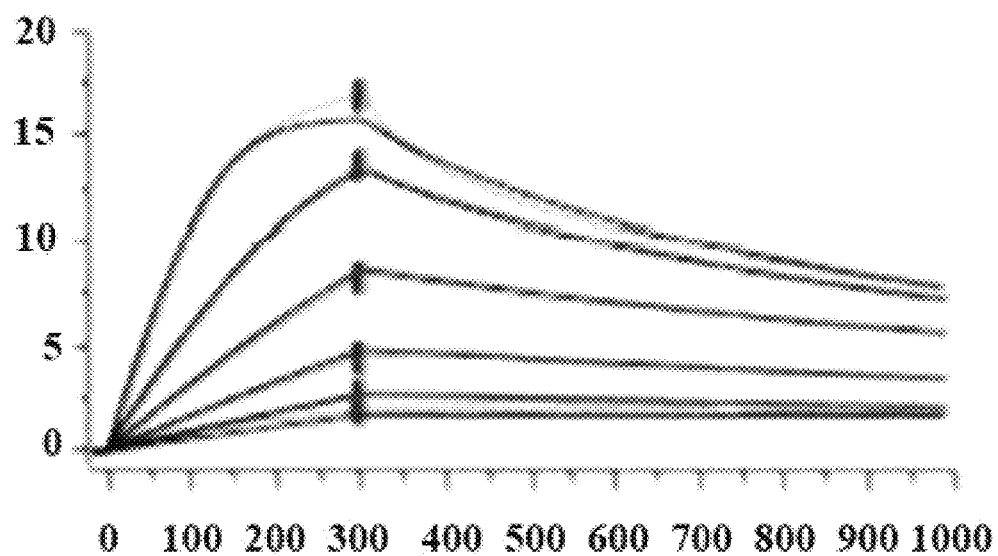
FIG. 23 is a line graph showing the TNFa binding of Compound 36 measured by SPR as described in Example 2. The y-axis is response measured in units and the x-axis is time measured in seconds.

Data was processed using the analysis software in Biacore 8K to perform background subtraction, double referencing, and solvent correction. Double-referenced data were fit using a 1:1 binding model for kinetic analysis or using a steady state binding responses (RUs) as a function of the concentration ([Compound]) using the following equation: RU=RUmax/(KD+[Compound]), where RU max is the calculated maximal response. This assay was also used to generate the data in FIG. 22 and adapted to generate the data in FIG. 23.

TABLE 5

IgG binding of Select Compounds

| Compound Number | IgG SPR Binding $K_d$ (nM) |
| --- | --- |
| Compound 6 | ++++ |
| Compound 7 | ++++ |
| Compound 8 | ++++ |
| Compound 9 | ++++ |
| Compound 10 | ++++ |
| Compound 15 | ++++ |
| Compound 16 | ++++ |
| Compound 17 | ++++ |
| Compound 21 | ++++ |
| Compound 22 | ++++ |
| Compound 41 | ++++ |
| Compound 52 | ++++ |
| Compound 53 | ++++ |
| Compound 60 | ++++ |
| Intermediate 1 | ++++ |
| Intermediate 2 | ++++ |
| Intermediate 3 | ++++ |
| Intermediate 4 | ++++ |
| Intermediate 5 | ++++ |
| Intermediate 6 | ++++ |
| Intermediate 7 | ++++ |
| Intermediate 9 | ++++ |
| Intermediate 12 | ++++ |
| Intermediate 13 | ++++ |
| Intermediate 15 | ++++ |
| Intermediate 16 | ++++ |
| Intermediate 17 | ++++ |
| Intermediate 18 | ++++ |
| Intermediate 19 | ++++ |
| Intermediate 21 | ++++ |
| Intermediate 22 | ++++ |
| Intermediate 23 | ++++ |
| Intermediate 24 | ++++ |
| Intermediate 25 | ++++ |
| Intermediate 26 | ++++ |
| Intermediate 27 | ++++ |
| Intermediate 28 | ++++ |
| Intermediate 29 | ++++ |

In the table above $K_d$ values that are >=1000 nM = +, <1000 nM = ++, <500 nM = +++, and <100 nM = ++++

Example 3 Ternary Complex Formation and HepG2 Cellular Uptake

Ternary Complex Formation Assay

The ternary complex formation assay is designed to identify the concentration of Degrader required to form a complex between the degrader, a constant concentration of fluorescently-labeled antibody and the ASGPR receptor on the cell surface. The peak mean fluorescence intensity (MFI) occurs at the optimal degrader concentration for ternary complex formation. Sub-optimal concentrations of degrader (too much or too little) results in fewer complexes formed and a reduced MFR.

Figure 12:
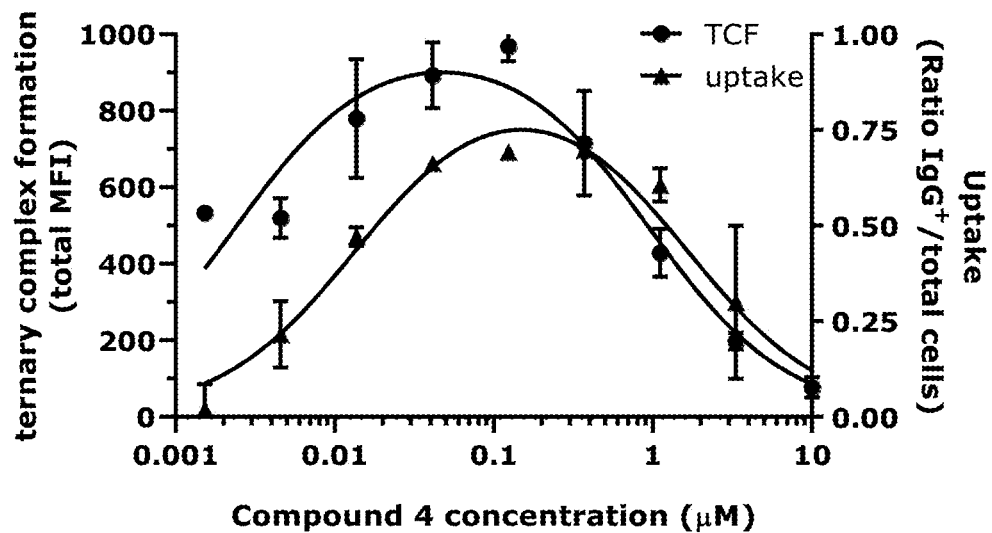
FIG. 12 is a graph of the ternary complex formation of Compound 4, IgG, and ASGPR and cellular uptake of IgG at various concentrations of Compound 4. The y-axis is the concentration of ternary complex formation shown by total mean fluorescence intensity (MFI) (for ternary complex formation) or ratio of IgG+ to total cells (for uptake) and the x-axis is concentration of Compound 4 measured in micromolar. The experimental procedure is described in Example 3.
Figure 13:
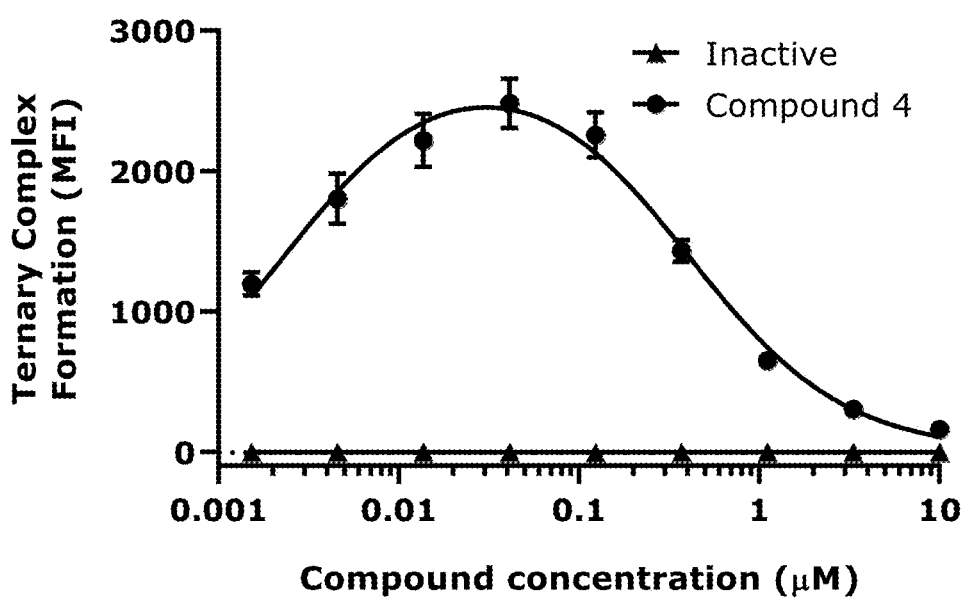
FIG. 13 is a graph of the ternary complex formation of Compound 4 or Inactive Compound, IgG, and ASGPR at various concentrations of Compound 4 or Inactive Compound. The y-axis is the concentration of ternary complex formation shown by total mean fluorescence intensity (MFI) and the x-axis is concentration of Compound 4 or Inactive Compound measured in micromolar. The experimental procedure is described in Example 3.
Figure 15:
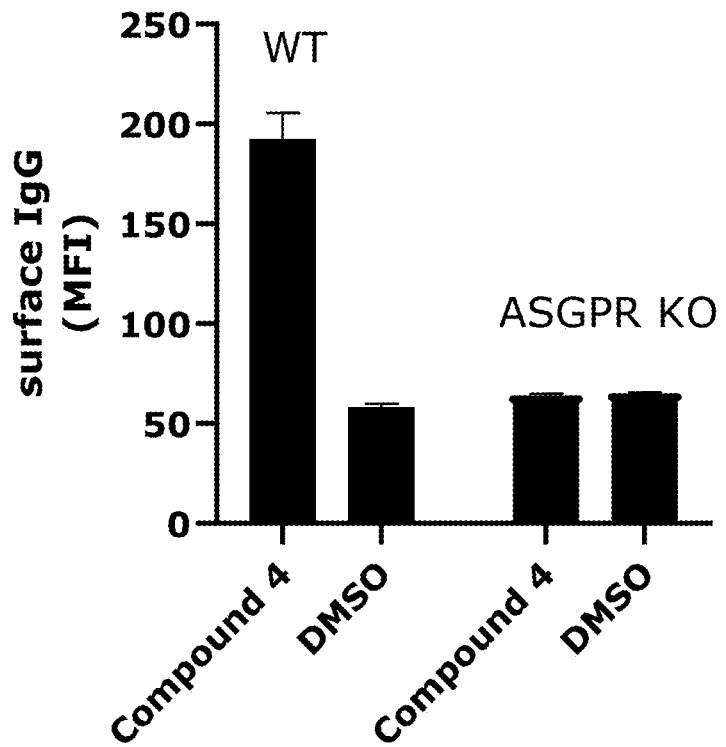
FIG. 15 is a bar graph of the surface IgG concentration resulting from the ternary complex formation of Compound 4, IgG, and ASGPR in the presence or absence of Compound 4 with wild-type cells and ASGPR knock out cells. The y-axis is the concentration of surface IgG shown by total mean fluorescence intensity (MFI) and the x-axis is the presence or absence of Compound 4. The experimental procedure is described in Example 3.

Human IgG (Sigma-Aldrich, 14506) was covalently labeled with Alexa Fluor 488 using the Alexa Fluor™ 488 Protein Labeling Kit (Thermo Fisher, A10235) following the manufacturer's instructions. HepG2 cells (ATCC, HIB-8065) were cultured to about 70% confluence and harvested by trypsinization. Single cell suspensions of HepG2 cells were plated in 96 well plates at $1 \times 10^5$ cells/well in cell culture media (DMEM supplemented with 1000 FBS) and placed at 4° C. For studies using human IgG, cells were incubated with 100 nM AF488-labeled anti-human IgG and serial dilutions of IgG-based degrader for 1 hour at 4° C. For studies using DNP, cells were incubated with 100 nM AF488-labeled polyclonal rabbit anti-dinitrophenyl (DNP) antibodies (ThermoFisher) and serial dilutions of DNP-based degrader for 1 hour at 4° C. After washing once with ice-cold PBS containing 0.1% BSA and 0.1% sodium azide, cells were resuspended in 150 uL PBS+0.1% BSA and cell-associated AF488 fluorescence was measured by flow cytometry using the iQue® Screener PLUS Flow Cytometer (IntelliCyt). Data shows measured MFI. FIG. 1 shows the ternary complex formation of bound AF488-labeled DNP antibody on the cell surface of HepG2 cells with increasing concentrations of Compound 28. The $EC_{50}$ is measured as the half-maximal concentration of Compound 28 with respect to the peak MFI (0.0047 µM). The $EC_{50}$ results of the tested compounds are summarized in Table 6 below. This procedure was also used to produce the data in FIG. 12 Compound 4 and FIG. 13 (Compound 4 vs inactive compound). The inactive compound does not have C3 and C4 hydroxyl substituents. When the assay was repeated with ASGPR knocked out cells ternary complex formation did not occur in appreciable concentrations (see FIG. 15).

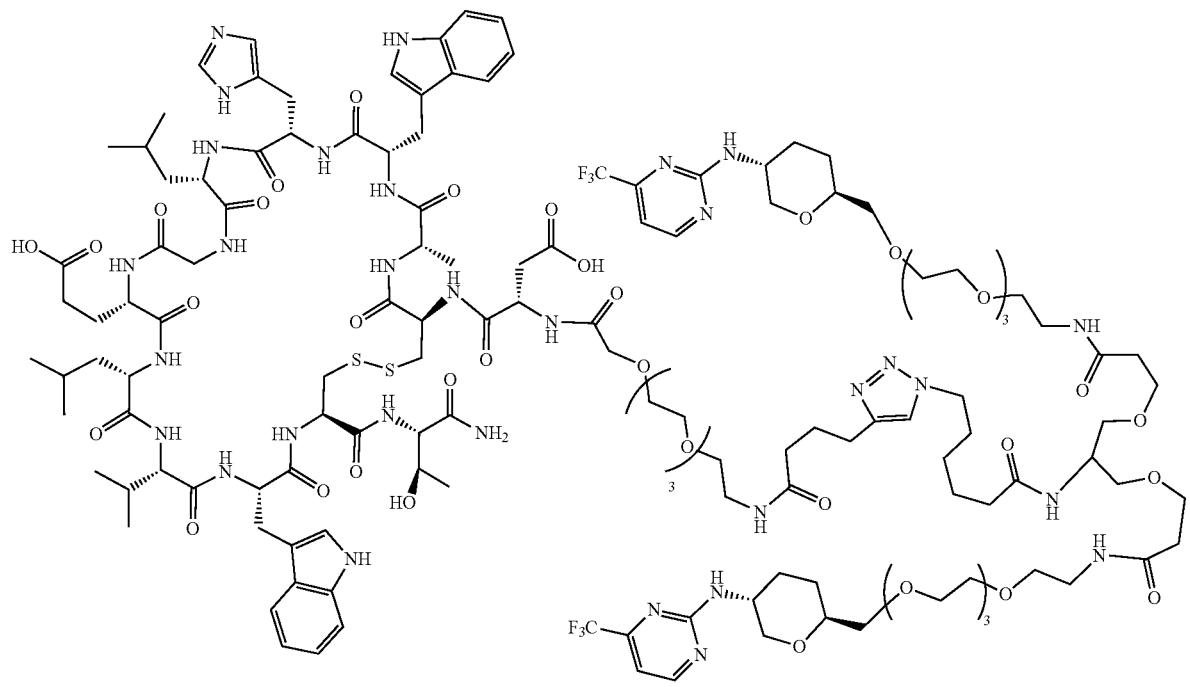

Inactive Compound

Cellular Uptake Assay

The cellular uptake assay is designed to measure compound-mediated cellular uptake of fluorescently labeled antibody following ternary complex formation with the ASGPR receptor and endocytosis of the entire complex into cells. The optimal concentration of compound will result in the maximum number of cells with intracellular antibody and is represented as the peak ratio of antibody-positive cells over the total number of cells. As with the ternary complex formation assay, too much or too little compound will result in suboptimal complex formation and fewer cells will have measurable intracellular fluorescence.

Figure 2:
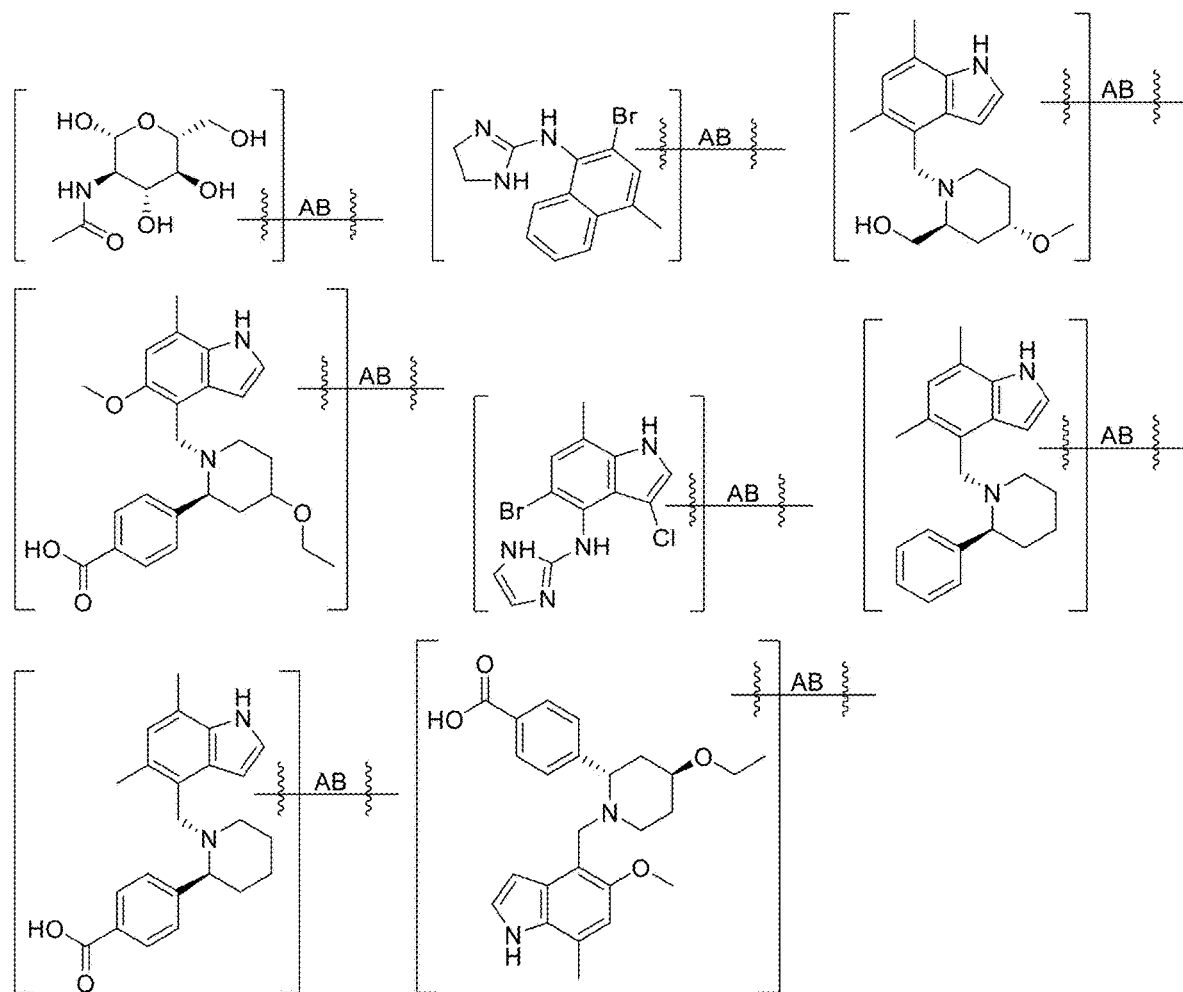
FIG. 2 provides a non-limiting list of exemplary Extracellular Protein Targeting Ligands that target complement factor B.

Human IgG (Sigma-Aldrich, 14506) was covalently labeled with Alexa Fluor 488 using the Alexa Fluor™ 488 Protein Labeling Kit (Thermo Fisher, A10235) following the manufacturer's instructions. HepG2 cells were plated in DMEM supplemented with 10% FBS at 5,000 cells per well in a 96-well microtiter plate and incubated for approximately 18 hours at 37° C./5% $CO_2$. For studies using human IgG, 100 nM AF488-labeled human IgG antibodies and serial dilutions of IgG-based degrader (0.1% DMSO final concentration) were added to the cells and the mixture was incubated at 37° C. for 6 hours. For studies using DNP, 100 nM AF488-labeled DNP antibodies and serial dilutions of DNP-based degrader (0.1% DMSO final concentration) were added to the cells and the mixture was incubated at 37° C. for 6 hours. HepG2 cells were fixed in 100% methanol at −20° C. for 20 min, washed 3× with PBS, then stained with DAPI (Thermo, Cat #H3570). HepG2 cells were imaged for DAPI and Alexa Fluor 488 using the Operetta CLS, high-content analysis system (PerkinElmer). Data is presented as the ratio of the number of cells positive for hIgG or DNP (AF-488 fluorescence) over the total cell number (measured by DAPI). FIG. 2 shows the cellular uptake of DNP-antibody with increasing concentrations of Compound 28.

Figure 14:
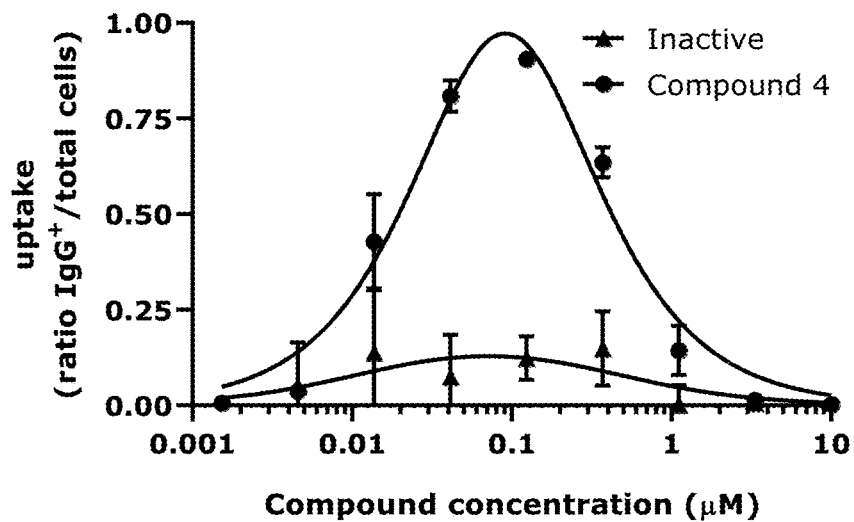
FIG. 14 is a graph of cellular uptake of IgG at various concentrations of Compound 4 or Inactive Compound. The y-axis is the ratio of IgG+ to total cells and the x-axis is concentration of Compound 4 or Inactive Compound measured in micromolar. The experimental procedure is described in Example 3.
Figure 16:
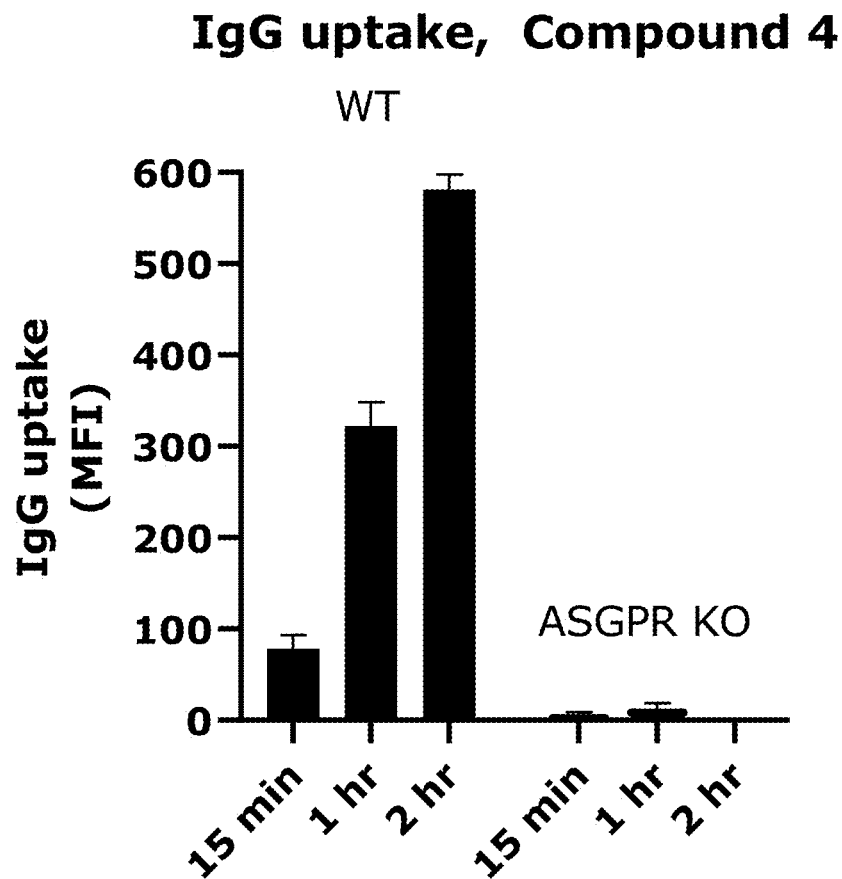
FIG. 16 is a bar graph of the cellular uptake of IgG over time in the presence of Compound 4 in either wild-type or ASGPR knock-out cells. The y-axis is the concentration or IgG shown by total mean fluorescence intensity (MFI) and the x-axis is time measured in minutes and hours. The experimental procedure is described in Example 3.

The $EC_{50}$ is measured as the half-maximal concentration of Compound 28 with respect to the peak ratio of antibody-positive cells (0.0038 μM). The EC50 results of the tested compounds are summarized in Table 6 below. This procedure was used to produce the data in FIG. 12 (Compound 4) and FIG. 14 (Compound 4 vs inactive compound). When the assay was repeated with ASGPR knocked out cells IgG uptake was significantly decreased (see FIG. 16).

TABLE 6

Ternary Complex Formation and Uptake of Select Compounds

| Compound Number | Ternary Complex $EC_{50}$ (nM) | Uptake Assay $EC_{50}$ (nM) |
|---|---|---|
| Compound 1 | ++++ | ++++ |
| Compound 2 | ++++ | +++ |
| Compound 3 | ++++ | ++ |
| Compound 4 | ++++ | ++++ |
| Compound 5 | ++++ | ++++ |
| Compound 6 | ++++ | ++++ |
| Compound 7 | ++++ | +++ |
| Compound 8 | ++++ | ++++ |
| Compound 9 | ++++ | ++++ |
| Compound 10 | ++++ | ++++ |
| Compound 11 | ++++ | ++++ |
| Compound 12 | ++++ | ++++ |
| Compound 13 | ++++ | +++ |
| Compound 14 | ++++ | ++++ |
| Compound 15 | ++++ | +++ |
| Compound 16 | ++++ | ++++ |
| Compound 17 | ++++ | ++++ |
| Compound 21 | ++++ | ++++ |
| Compound 22 | >87 | ++++ |
| Compound 26 | ++++ | ++++ |
| Compound 27 | ++++ | ++++ |
| Compound 28 | ++++ | ++++ |
| Compound 29 | ++++ | ++++ |
| Compound 30 | ++++ | ++++ |
| Compound 31 | ++++ | ++++ |

TABLE 6-continued

Ternary Complex Formation and Uptake of Select Compounds

| Compound Number | Ternary Complex EC$_{50}$ (nM) | Uptake Assay EC$_{50}$ (nM) |
|---|---|---|
| Compound 32 | ++++ | ++++ |
| Compound 34 | >10000 | >10000 |
| Compound 35 | ++++ | >10000 |
| Compound 38 | ++++ | ++++ |
| Compound 40 | ++++ | ++++ |
| Compound 41 | ++++ | ++++ |
| Compound 42 | ++++ | ++++ |
| Compound 43 | ++++ | ++++ |
| Compound 45 | ++++ | ++++ |
| Compound 46 | ++++ | ++++ |
| Compound 47 | ++++ | ++++ |
| Compound 50 | ++++ | ++++ |
| Compound 51 | ++++ | ++++ |
| Compound 52 | ++++ | ++++ |
| Compound 53 | ++++ | ++++ |
| Compound 60 | ++++ | |
| A12 | >10000 | |

In the table above EC$_{50}$ values that are >=1000 nM = +, <1000 M = ++, <500 M = +++, and <100 nM = ++++

Example 4 Cellular Co-Localization Studies

To confirm that DNP-IgG was trafficked to the lysosome following uptake by the HepG2 cells, cells were stained with the lysosomal marker LAMP2, and the subcellular location of AF488-labeled DNP-IgG was visualized by immunofluorescence microscopy.

HepG2 cells were plated in DMEM supplemented with 10% FBS incubated for approximately 18 hours at 37° C./5% CO$_2$. AF488-labeled DNP antibodies (100 nM) and either DMSO or 100 nM of Compound 28 were added to the cells and incubated at 37° C. for an additional 8 hours. Cells were fixed with 100% methanol for 20 minutes at −20° C. followed by incubation with blocking buffer (1×PBS containing 5% normal goat serum and 0.1% Triton X-100) for 1 hour at room temperature. Cells were stained with anti-LAMP2 (Abcam) at 4° C. for about 18 hours followed by treatment with goat anti-mouse IgG-AF647 for 2 hours at room temperature. Nuclei were stained with DAPI. Pictures were taken on a Leica fluorescence microscope at 40× magnification.

Figure 4:
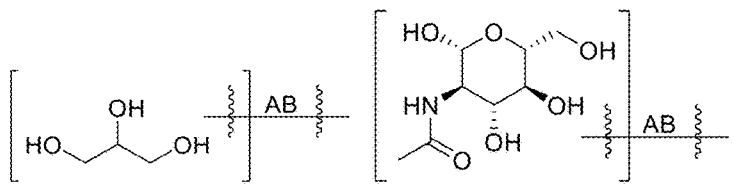
FIG. 4 provides a non-limiting list of exemplary Extracellular Protein Targeting Ligands that target complement factor H.

In HepG2 cells treated with DNP-IgG and 100 nM Compound 28, DNP-IgG was taken up into the cells and co-localized with the lysosomal marker LAMP2 (FIG. 4, Compound 28, bottom panels). In contrast, DNP-IgG added to HepG2 cells in the absence of a Compound 28 (DMSO) did not show cellular uptake as no AF488 fluorescence was detected in the HepG2 cells (FIG. 4, DMSO, top panels).

Example 5 Cellular Degradation Assay

To observe degradation of IgG in cells, a mixture of fluorescently labeled DNP antibody and compound are added to HepG2 cells and cellular uptake occurs over 16 hours. Cells are then washed to remove extracellular antibody and compound and samples are taken at various time points after uptake to detect levels of intact and/or proteolytic fragments of the antibody heavy and light chains over time as a kinetic measurement of antibody degradation.

Figure 3A:
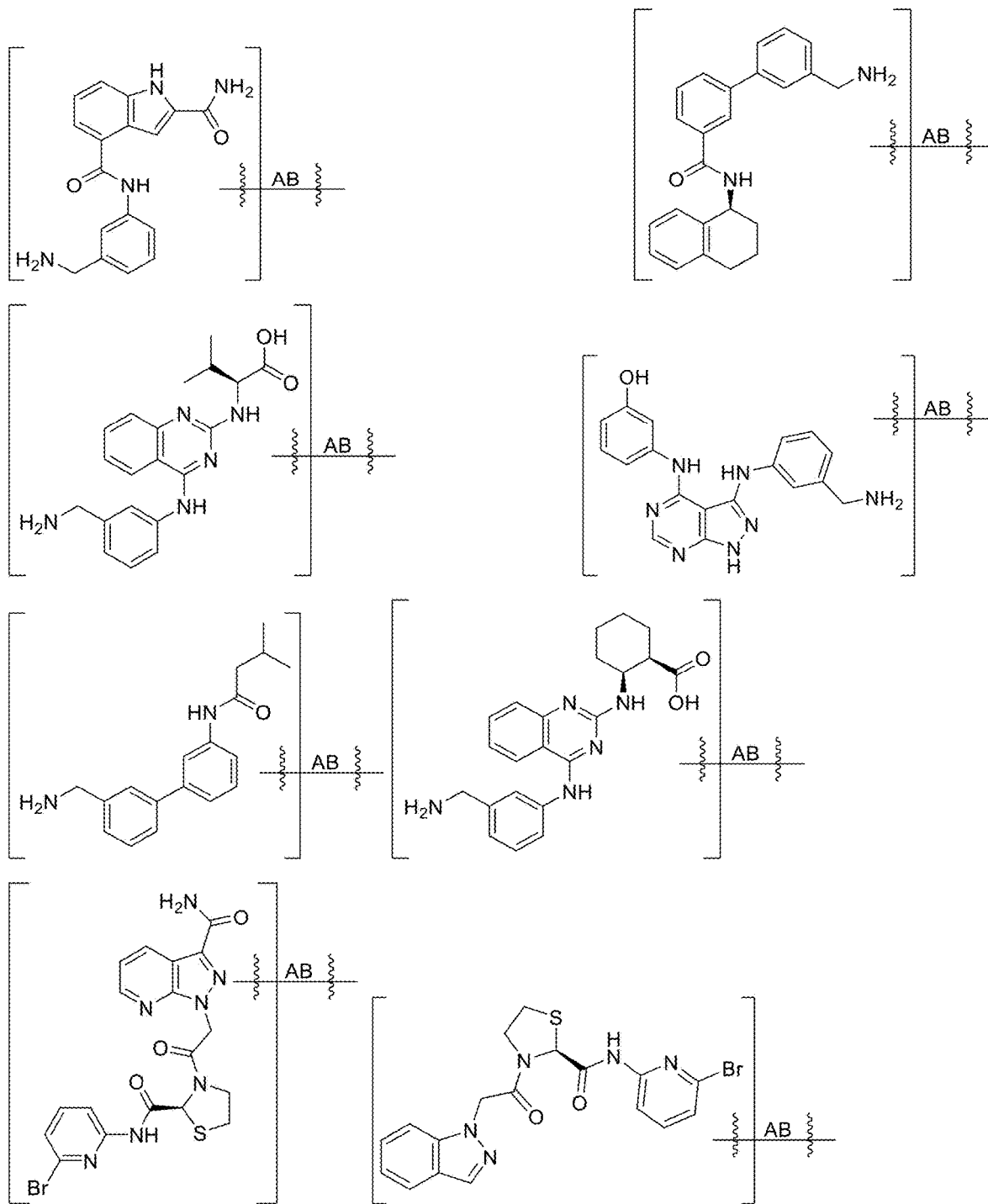
FIGS. 3A and 3B provides a non-limiting list of exemplary Extracellular Protein Targeting Ligands that target complement factor D.
Figure 3B:
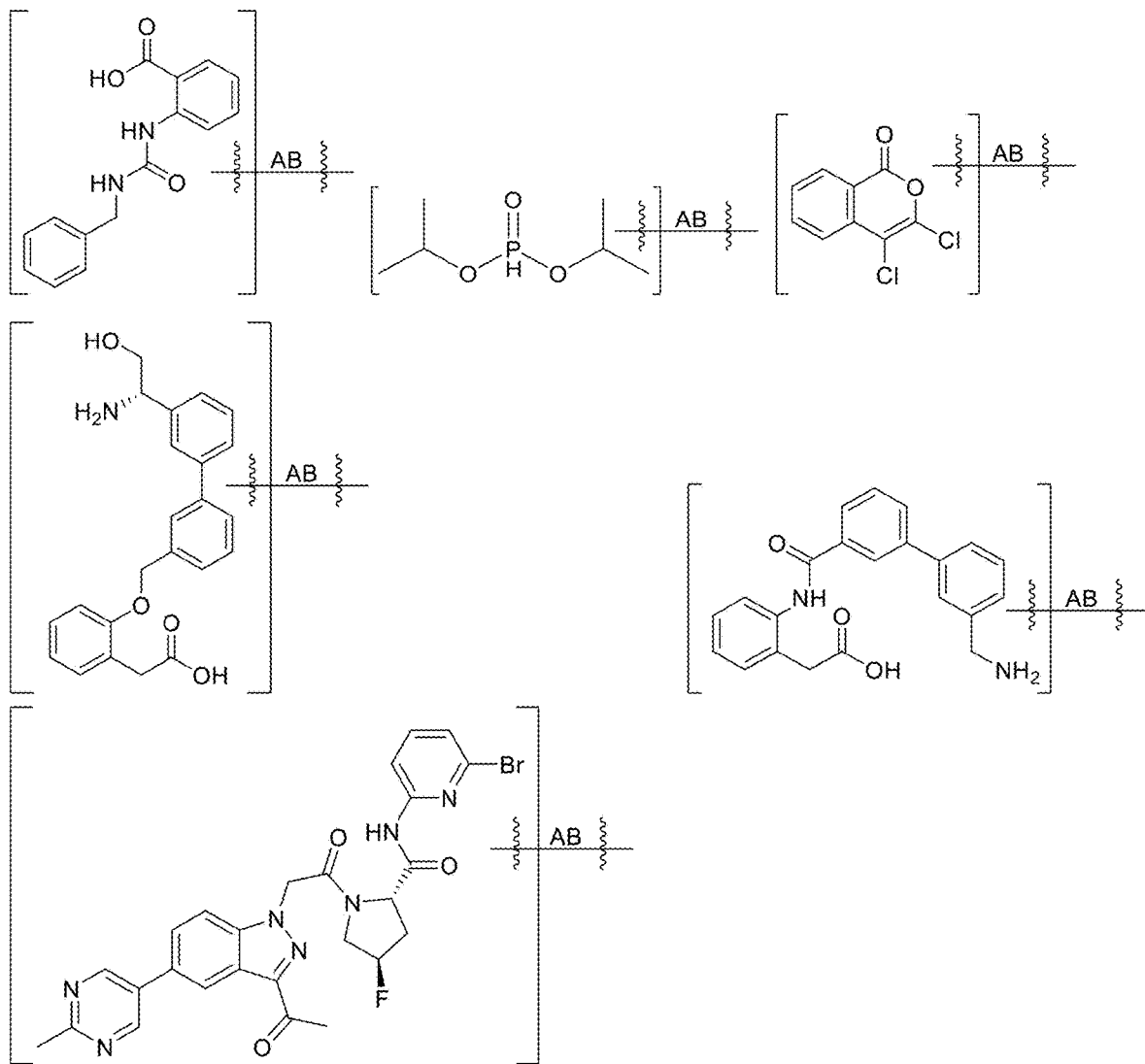

HepG2 cells were seeded in DMEM supplemented with 10% FBS into a 12-well plate at a final amount of 20,000 cells per well. After about 18 hours incubation, 1 µM anti-DNP-AF488 antibody and/or 0.2 µM Compound 28 was added to the cells and incubated for 16 hours. The next day, cells were washed once with cell culture media and replaced with cell culture medium lacking anti-DNP-AF488 antibody or Compound 28 and incubated for 0, 1, 2, 4, and 8 hours, respectively. Cells were washed and lysed in RIPA buffer with protease inhibitors. Cell lysates were separated by SDS-PAGE and the fluorescent anti-DNP-AF488 antibody degradation products were visualized by the iBright 1500 gel reader (ThermoFisher). The resulting data is shown in FIG. 3. Intracellular heavy and light chains of DNP-IgG are observed after 16 hours of uptake into HepG2 cells. Loss of intact heavy and light chains is observed after 1 hour and 8 hours respectively, indicating the intracellular DNP-IgG is being degraded by HepG2 cells.

Example 6 Additional IgG Cellular Degradation Assay

Figure 17:
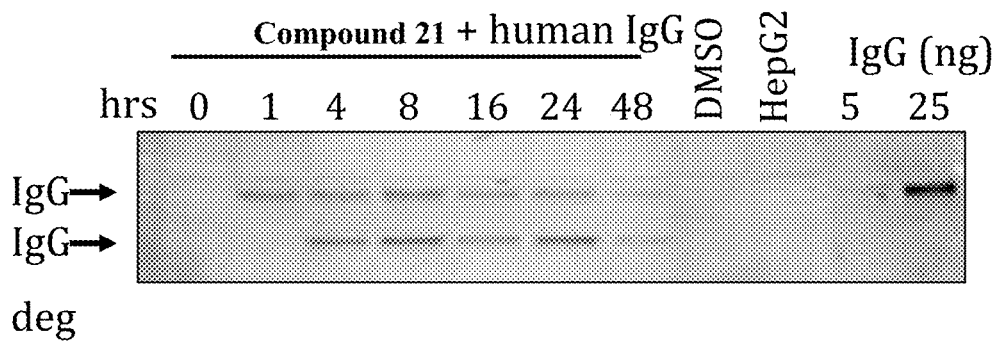
FIG. 17 is a western blot showing the concentration of IgG degradation products in the presence of Compound 21 over time. The experimental procedure is described in Example 6.

HepG2 cells were seeded in DMEM supplemented with 10% FBS into a 6-well plate at a final amount of 1×10$^6$ cells per well. After about 18 hours incubation, 1 mg/mL human IgG and/or 1 µM Compound 21 were added to the cells and incubated for 0, 1, 4, 8, 16, 24 and 48 hours. Cells were washed twice with PBS and were lysed in RIPA buffer with protease inhibitors. Cell lysates were separated by SDS-PAGE and the IgG degradation products were visualized by western blot using anti-human IgG antibody and visualized with a LiCOR imager. Human IgG (5 and 25 ng) was also separated on SDS-PAGE as a positive control for full length IgG. This assay was used to produce the data in FIG. 17.

Figure 18:
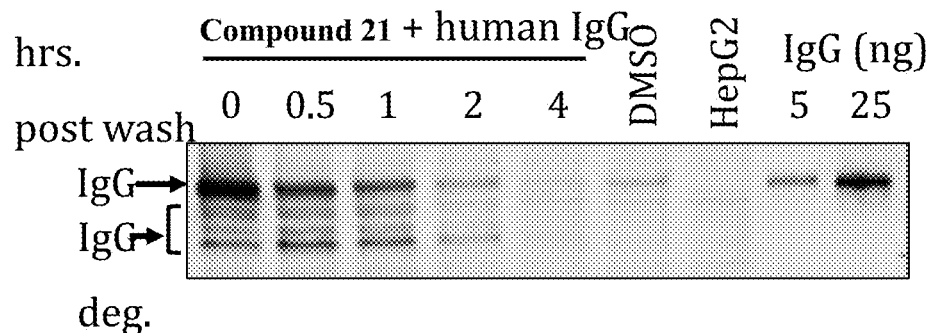
FIG. 18 is a western blot showing the concentration of full-length IgG in the presence of Compound 21 over time. The experimental procedure is described in Example 7.

Example 7 Detection of Full Length IgG and IgG Degradation Products by Immunoblot HepG2 cells were seeded in DMEM supplemented with 10% FBS into a 6-well plate at a final amount of 1×10$^6$ cells per well. After about 18 hours incubation, 1 mg/mL human IgG and/or 1 µM Compound 21 was added to the cells and incubated for 1 hour. Cells were washed once with cell culture media and replaced with fresh cell culture media and incubated for 0, 0.5, 1, 2, or 4 hours. Cells were lysed in RIPA buffer with protease inhibitors. Cell lysates were separated by SDS-PAGE and the IgG degradation products were visualized by western blot using anti-human IgG antibody and visualized with a LiCOR imager. Human IgG (5 and 25 ng) was also separated on SDS-PAGE as a positive control for full length IgG. This assay was used to produce the data in FIG. 18.

Example 8 IgG Degradation in Rat Hepatocytes

Figure 19:
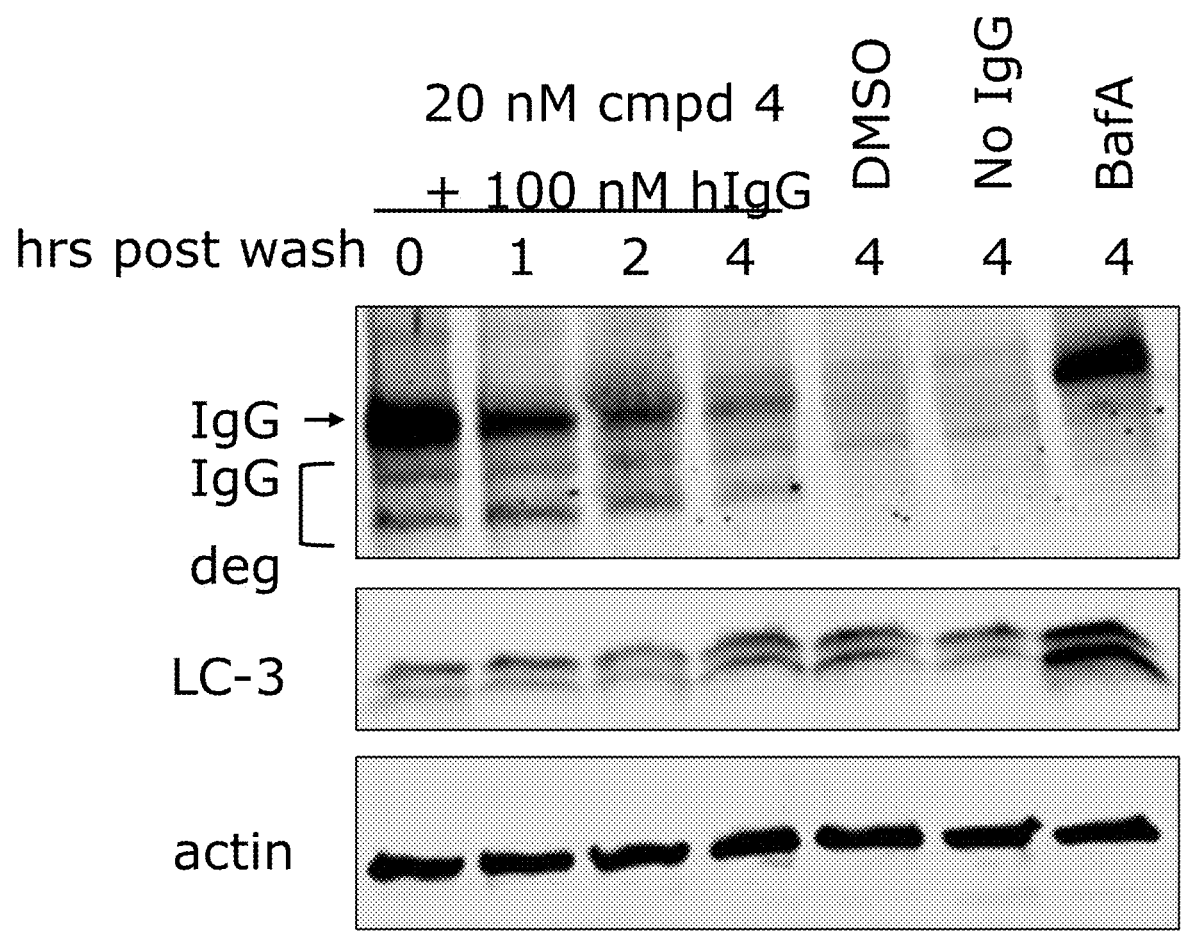
FIG. 19 is a western blot taken from the lysate of rat hepatocytes showing the concentration of IgG in the presence of Compound 4 over time. The experimental procedure is described in Example 8.

Rat hepatocytes cells were seeded in OptiPlate media into a collagen-coated 6-well plate at 1×10$^6$ cells per well. After 4 hours, media was replaced with OptiCulture media. After about 18 hours incubation, 100 nM human IgG and/or 20 nM Compound 4 were added to the cells and incubated for 1 hour. Cells were washed once with OptiCulture media and replaced with fresh media and incubated for 0, 1, 2, or 4 hours. Cells were washed 3 times with PBS and lysed in RIPA buffer with protease inhibitors. Bafilomycin A treated sample: hepatocytes were pre-treated with 150 nM Bafilomycin A for 1 hour, then incubated with 20 nM Compound 4+100 nM human IgG and 150 nM BafA for 1 hour, cells were washed, incubated for 4 hours and then lysed. Cell lysates were separated by SDS-PAGE and the IgG degradation products were visualized by western blot using anti-human IgG antibody or Actin antibody or antibody to LC3 and visualized with a LiCOR imager. This assay was used to produce the data in FIG. 19.

Example 9 Additional Cellular Co-Localization Studies

To confirm that IgG was trafficked to the lysosome following uptake by the HepG2 cells, cells were stained with the lysosomal marker LAMP2, and the subcellular location of AF488-labeled DNP-IgG was visualized by immunofluorescence microscopy.

Figure 20:
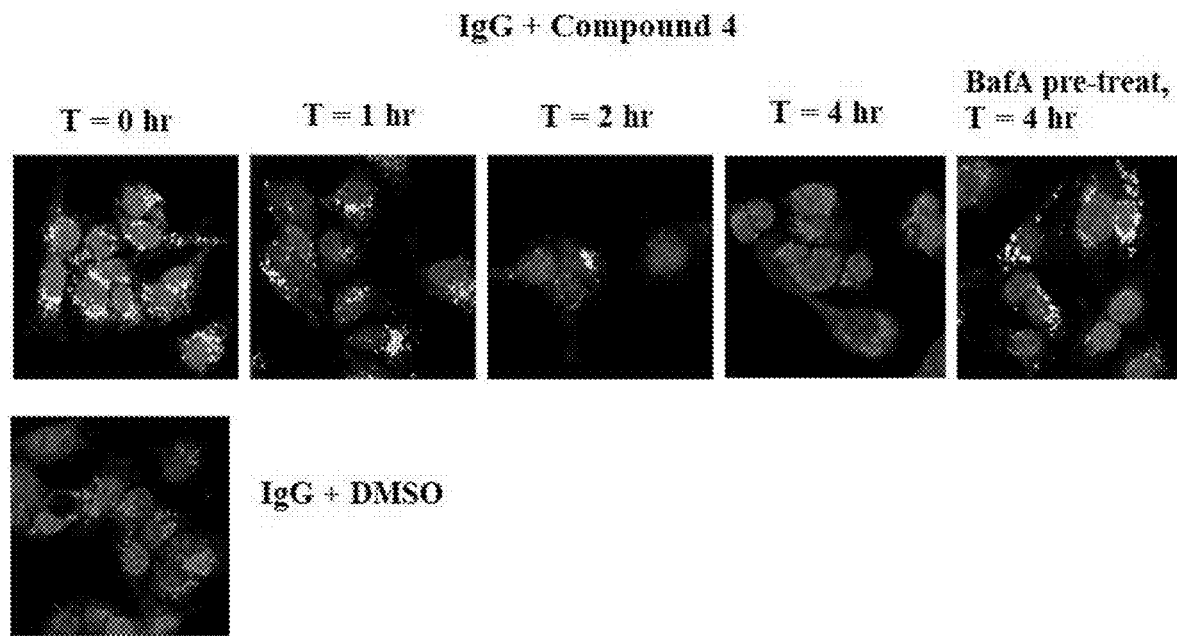
FIG. 20 is a colocalization image showing the uptake of DNP-IgG in the presence of Compound 4. The experimental procedure is described in Example 9.

HepG2 cells were seeded 10,000 cells/well in 96 well collagen-coated black plate. Cells were Pre-treated with 30 nM BafA for 1 hr, or not. HepG2 cells were incubated with 100 nM IgG, 20 nM Compound 4/DMSO for 1 hr. Cells were washed with PBS then samples at T=0, 1 hr, 2 hr, 4 hr after wash were fixed with 4% PFA for 15 min at RT then stained for IgG, DAPI, Lamp2 (endo-lysosome marker). This assay was used to produce the data in FIG. 20.

Example 10 TNF Cellular Assays

TNF FP Assay

TNF (20 nM) and Compound 36 in 47 mM HEPES pH 6.5, 47 mM NaCl, 0.9 mM EDTA, 0.007% Triton X-100 were incubated at 25° C. for 2 hours. Fluorescence data was read with an Envision and plotted versus Compound 36 concentration and fit to a single-site binding model. This assay was used to calculate the FP data in Table 7.
TNF Ternary Complex Assay His-tagged TNF (300 nM), biotinylated ASGPR (25 nM) and test compound in 50 mM Tris, pH 7.5, 150 mM NaCl, 0.01% Tween-20 are incubated at 25° C. for 4 hours. Streptavidin-Tb cryptate (PerkinElmer 610SATLA) and anti-His-d2 (Perkin Elmer 61HISDLA) are then added and incubated for 2 hour or overnight. Fluorescence data is read with an Envision and the ratio of the 655 nm/615 nm signals plotted versus test compound concentration.

TABLE 7

Compound 36 Biochemical and Cellular Attributes

| Biochemical/cellular attributes | Compound 36 |
|---|---|
| ASGPR $K_D$ (nM) | <1 |
| ASGPR $k_d$ (s$^{-1}$) | <10 × 10$^{-3}$ |
| TNFα FP IC$_{50}$ KD (nM) | <500 |

Example 11 TNF Degradation by Compound 36 in HepG2 Cells

Figure 24:
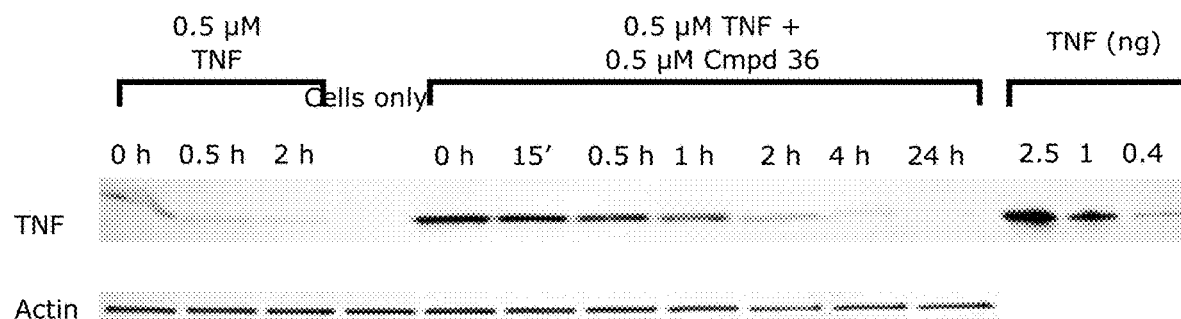
FIG. 24 is a western blot showing the degradation of TNF by 0.5 µM Compound 36 over time. The experimental procedure is described in Example 11.

Compound 36 and human TNF were pre-incubated in phosphate-buffered saline, pH 7.4 (ThermoFisher 10010023) for 18 hours to allow formation of binary complexes. Compound 36/TNF complexes or TNF alone were incubated for 2 hours on HepG2 cells grown in Dulbecco's Modified Eagle Medium for 16-24 hours to near confluence. Cells were washed with Dulbecco's Modified Eagle Medium, 10% fetal bovine serum. Cells were then incubated with cell media without reagents for 0-3 hours. Cells were washed and lysed for Western blot analysis using phosphate-buffered saline containing RIPA (Sigma R0278) and protease inhibitors (ThermoScientific 1861279). Samples were run on 4-20% gradient SDS-PAGE gel (Biorad 5678094) and transferred to PVDF and blocked for 1 hour with LI-COR blocking solution. TNF and actin were detected with anti-IgG and anti-actin antibodies, respectively, and 800cw-conjugated secondary antibody and read with a LI-COR. Compound 36 and human TNF were pre-incubated for 18 h to allow formation of binary complexes. Compound 36 TNF complexes or TNF alone were incubated for 2 h on HepG2 cells. Cells were washed, incubated with cell media without reagents for 0-24 h and subsequently washed and lysed for Western blot analysis. TNF and actin were detected with anti-IgG and anti-actin antibodies, respectively, and 800cw-conjugated secondary antibody. This assay was used to produce the data in FIG. 24.

Example 12 ASGPR Mediated TNF Uptake by Compound 36 in HepG2 Cells

Compound 36 and human TNF were pre-incubated in phosphate-buffered saline, pH 7.4 (ThermoFisher 10010023) for 18 hours to allow formation of binary complexes. Compound 36/TNF complexes or TNF alone were incubated for 0-3 hour on HepG2 cells grown in Dulbecco's Modified Eagle Medium for 16-24 hours to near confluence. Cells were washed and lysed for Western blot analysis using phosphate-buffered saline containing RIPA (Sigma R0278) and protease inhibitors (ThermoScientific 1861279). Samples were run on 4-20% gradient SDS-PAGE gel (Biorad 5678094) and transferred to PVDF and blocked for 1 hour with LI-COR blocking solution. TNF and actin were detected with anti-IgG and anti-actin antibodies, respectively, and 800cw-conjugated secondary antibody and read with a LI-COR. TNF and actin were detected with anti-IgG and anti-actin antibodies, respectively, and 800cw-conjugated secondary antibody.

Figure 25:
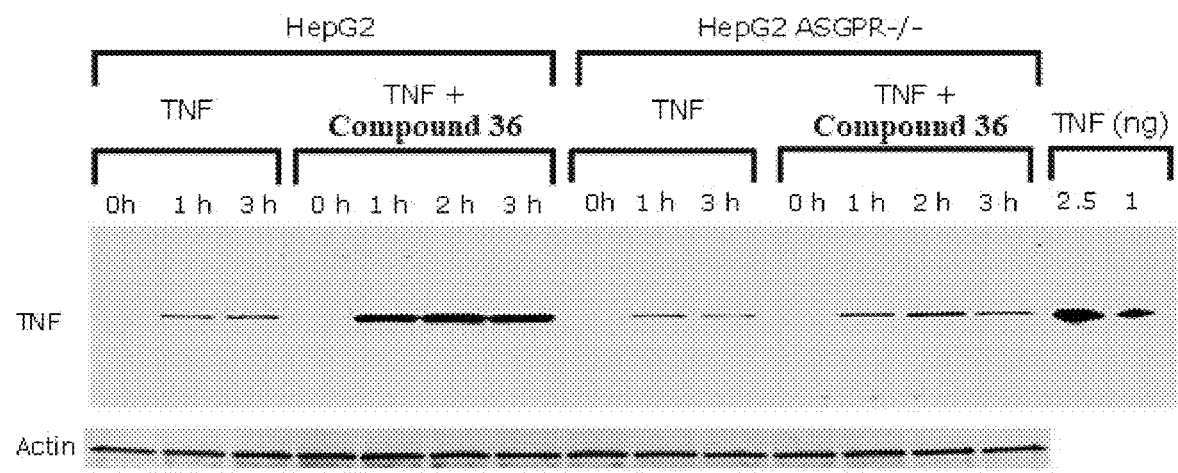
FIG. 25 is a western blot showing the ASGPR mediated uptake of TNF in the presence of Compound 36. The experimental procedure is described in Example 12.
Figure 26:
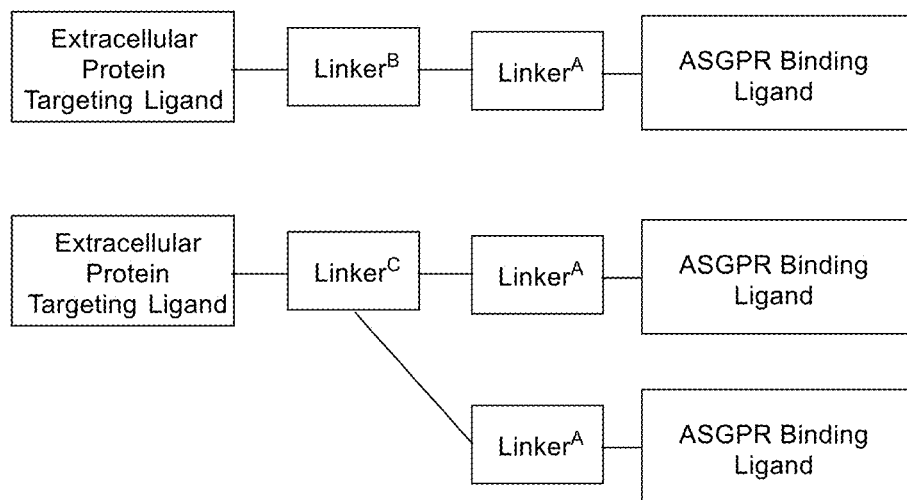
FIG. 26 provides non-limiting examples of formulas of the present invention.

0.5 μM Compound 36 and 0.5 μM human TNF were pre-incubated for 18 h to allow formation of stable complexes. Compound 36 TNF complexes or TNF alone were incubated for 0-3 h on HepG2 cells. Cells were washed and lysed for Western blot analysis. TNF and actin were detected with anti-IgG and anti-actin antibodies, respectively, and 800cw-conjugated secondary antibody. This assay was used to produce the data in FIG. 25.

All publications and patent applications cited in this specification are herein incorporated by reference as if each individual publication or patent application were specifically and individually indicated to be incorporated by reference.

Although the foregoing invention has been described in some detail by way of illustration and example for the purpose of clarity of understanding, it will be readily apparent to one of ordinary skill in the art in light of the teaching of this invention that certain changes or modifications may be made thereto without departing from the spirit or scope of the invention. Additionally, those skilled in the art will recognize, or be able to ascertain using no more than routine experimentation, many equivalents to the specific embodiments and methods described herein. Such equivalents are intended to be encompassed by the scope of the present application.

We claim:

1. A compound of formula:

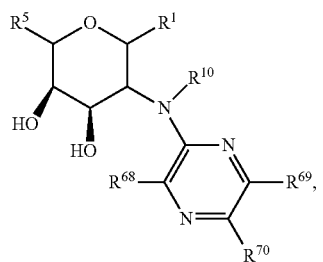

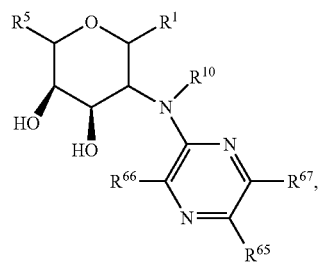

-continued

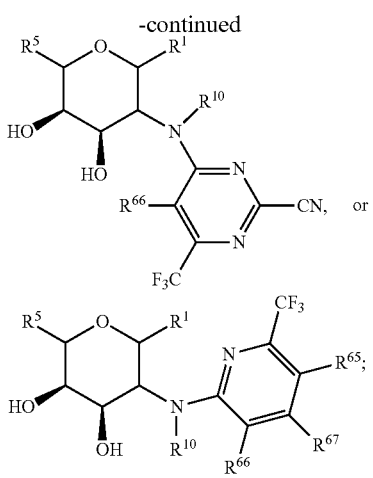

or a pharmaceutically acceptable salt thereof;
wherein:
- $R^1$ and $R^5$ are independently selected from hydrogen, $C_0\text{-}C_6$alkyl-cyano, alkyl, alkenyl, alkynyl, haloalkyl, F, Cl, Br, I, aryl, arylalkyl, heteroaryl, heteroarylalkyl, heterocycle, heterocycloalkyl, haloalkoxy, $C_0\text{-}C_6$alkyl-$OR^6$, $C_0\text{-}C_6$alkyl-$SR^6$, $C_0\text{-}C_6$alkyl-$NR^6R^7$, $C_0\text{-}C_6$alkyl-$C(O)R^3$, $C_0\text{-}C_6$alkyl-$S(O)R^3$, $C_0\text{-}C_6$alkyl-$S(O)_2R^3$, $C_0\text{-}C_6$alkyl-$N(R^8)$—$C(O)R^3$, $C_0\text{-}C_6$alkyl-$O$—$C(O)R^3$, $C_0\text{-}C_6$alkyl$N_3$, and $C_0\text{-}C_6$alkyl-$O$—$S(O)_2R^3$;
- $R^3$ at each occurrence is independently selected from hydrogen, alkyl, haloalkyl, arylalkyl, heteroarylalkyl, alkynyl, aryl, heteroaryl, heterocycle, —$OR^8$, and —$NR^8R^9$;
- $R^6$ and $R^7$ are independently selected at each occurrence from hydrogen, alkyl, arylalkyl, heteroarylalkyl, alkynyl, aryl, haloalkyl, heteroaryl, heterocycle, -alkyl-$OR^8$, and $C(O)R^3$;
- $R^8$ and $R^9$ are independently selected at each occurrence from hydrogen, heteroalkyl, alkyl, arylalkyl, heteroarylalkyl, alkenyl, alkynyl, aryl, heteroaryl, and heterocycle;
- $R^{10}$ is selected from hydrogen, alkyl, arylalkyl, heteroarylalkyl, aryl, heteroaryl, and heterocycle;
- $R^{65}$, $R^{66}$, and $R^{67}$ are independently selected from hydrogen, $C_0\text{-}C_6$alkyl-cyano, alkyl, haloalkyl, F, Cl, Br, I, $C_0\text{-}C_6$alkyl-$OR^6$, $C_0\text{-}C_6$alkyl-$NR^6R^7$, $C_0\text{-}C_6$alkyl-$C(O)R^3$, and $C_0\text{-}C_6$alkyl$N_3$;
- $R^{68}$, $R^{69}$, and $R^{70}$ are independently selected from hydrogen, alkyl, F, Cl, Br, I, $C_0\text{-}C_6$alkyl-$OR^6$, $C_0\text{-}C_6$alkyl-$NR^6R^7$, $C_0\text{-}C_6$alkyl-$C(O)R^3$, $C_0\text{-}C_6$alkyl-$S(O)R^3$, $C_0\text{-}C_6$alkyl-$N(R^8)$—$C(O)R^3$, $C_0\text{-}C_6$alkyl$N_3$, heteroaryl, and aryl.

2. The compound of claim 1, selected from

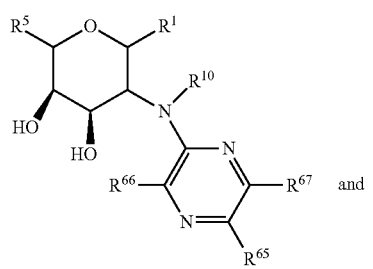

-continued

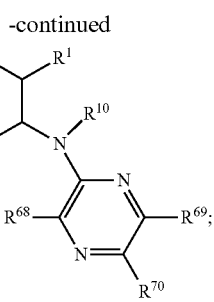

or a pharmaceutically acceptable salt thereof.

3. The compound of claim 2, of the formula

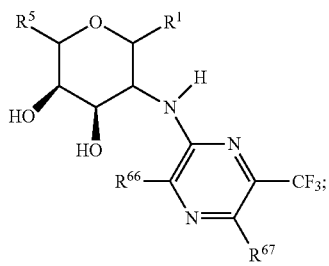

or a pharmaceutically acceptable salt thereof.

4. The compound of claim 2, selected from is selected from

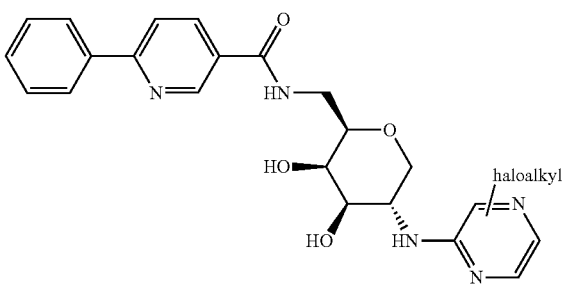

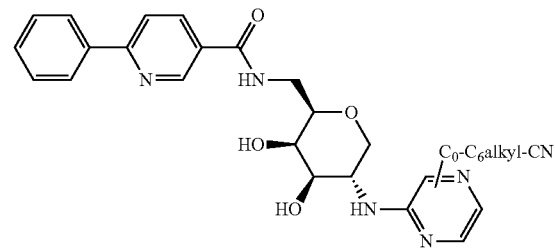

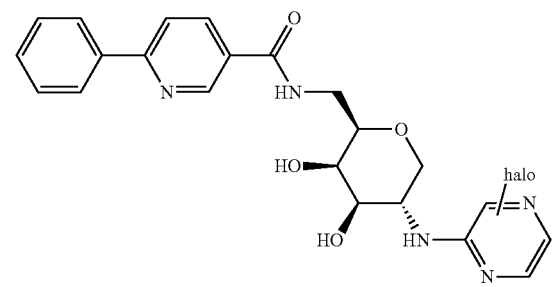

-continued

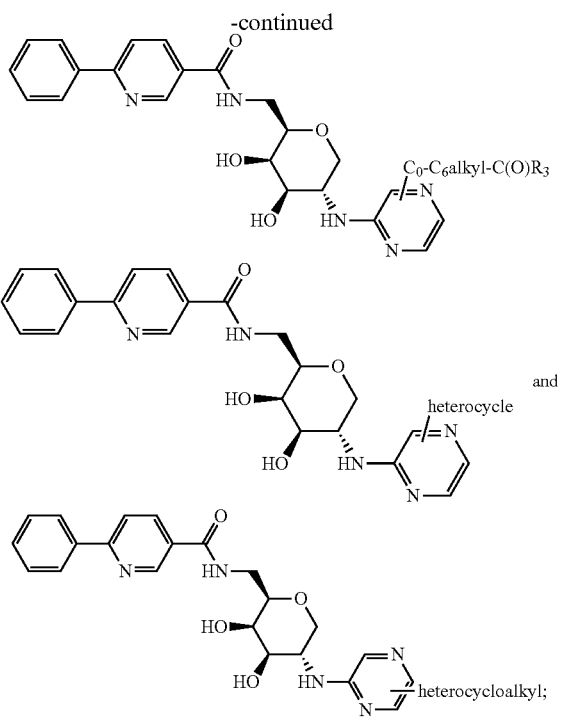

or a pharmaceutically acceptable salt thereof.

5. The compound of claim 3, wherein $R^{66}$ and $R^{67}$ are hydrogen.

6. The compound of claim 1, wherein $R^{65}$ is selected from hydrogen, $CF_3$, cyano, F, Cl, Br, haloalkyl, heterocycle, haloalkoxy, $C_0$-$C_6$alkyl-$OR^6$, and $C_0$-$C_6$alkyl-$NR^6R^7$.

7. The compound of claim 6, wherein $R^{65}$ is hydrogen.

8. The compound of claim 6, wherein $R^{66}$ is selected from hydrogen, $CF_3$, cyano, F, Cl, Br, haloalkyl, heterocycle, haloalkoxy, $C_0$-$C_6$alkyl-$OR^6$, and $C_0$-$C_6$alkyl-$NR^6R^7$.

9. The compound of claim 8, wherein $R^{66}$ is hydrogen.

10. The compound of claim 8, wherein $R^{67}$ is selected from hydrogen, $CF_3$, cyano, F, Cl, Br, haloalkyl, heterocycle, haloalkoxy, $C_0$-$C_6$alkyl-$OR^6$, and $C_0$-$C_6$alkyl-$NR^6R^7$.

11. The compound of claim 10, wherein $R^{67}$ is hydrogen.

12. The compound of claim 1, wherein $R^{68}$ is selected from hydrogen, $CF_3$, cyano, F, Cl, Br, haloalkyl, heterocycle, haloalkoxy, $C_0$-$C_6$alkyl-$OR^6$, and $C_0$-$C_6$alkyl-$NR^6R^7$.

13. The compound of claim 12, wherein $R^{68}$ is hydrogen.

14. The compound of claim 12, wherein $R^{69}$ is selected from hydrogen, $CF_3$, cyano, F, Cl, Br, haloalkyl, heterocycle, haloalkoxy, $C_0$-$C_6$alkyl-$OR^6$, and $C_0$-$C_6$alkyl-$NR^6R^7$.

15. The compound of claim 14 wherein $R^{69}$ is hydrogen.

16. The compound of claim 14, wherein $R^{70}$ is selected from hydrogen, $CF_3$, cyano, F, Cl, Br, haloalkyl, heterocycle, haloalkoxy, $C_0$-$C_6$alkyl-$OR^6$, and $C_0$-$C_6$alkyl-$NR^6R^7$.

17. The compound of claim 16, wherein $R^{70}$ is hydrogen.

18. The compound of claim 1, wherein $C_0$-$C_6$alkyl is bond, $C_1$alkyl, or $C_2$alkyl.

19. The compound of claim 1, wherein $R^{10}$ is hydrogen, alkyl, arylalkyl, heteroarylalkyl, heterocycle, $C(O)R^3$, $S(O)R^3$, or $S(O)_2R^3$.

20. The compound of claim 1, wherein $R^{10}$ is hydrogen.

21. The compound of claim 1, wherein $R^1$ is selected from hydrogen, $C_0$-$C_6$alkyl-cyano, alkyl, alkynyl, haloalkyl, F, Cl, Br, I, aryl, arylalkyl, heteroaryl, heteroarylalkyl, heterocycle, heterocycloalkyl, haloalkoxy, $C_0$-$C_6$alkyl-$OR^6$, $C_0$-$C_6$alkyl-$NR^6R^7$, $C_0$-$C_6$alkyl-$C(O)R^3$, $C_0$-$C_6$alkyl-$N(R^8)$—$C(O)R^3$, and $C_0$-$C_6$alkyl$N_3$.

22. The compound of claim 21, wherein $R^1$ is selected from Cl, Br, haloalkoxy, $C_0$-$C_6$alkyl-$OR^6$, $C_0$-$C_6$alkyl-$NR^6R^7$, $C_0$-$C_6$alkyl-$C(O)R^3$, $C_0$-$C_6$alkyl-$N(R^8)$—$C(O)R^3$, and $C_0$-$C_6$alkyl$N_3$.

23. The compound of claim 22, wherein $R^6$ is selected from hydrogen, arylalkyl, heteroarylalkyl, alkynyl, -alkyl-$OR^8$, and $C(O)R^3$.

24. The compound of claim 1, of the formula

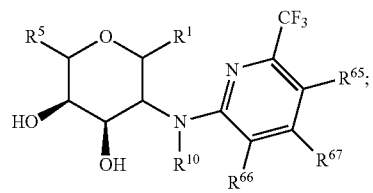

or a pharmaceutically acceptable salt thereof.

25. The compound of claim 24, wherein $R^{10}$ is hydrogen.

26. The compound of claim 25, wherein $R^{65}$, $R^{66}$, and $R^{67}$ are hydrogen.

27. A compound selected from:

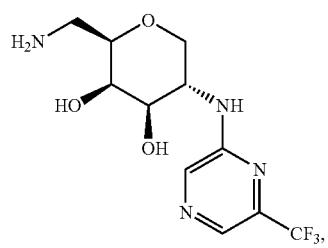

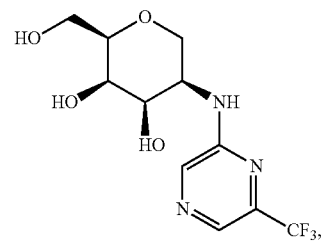

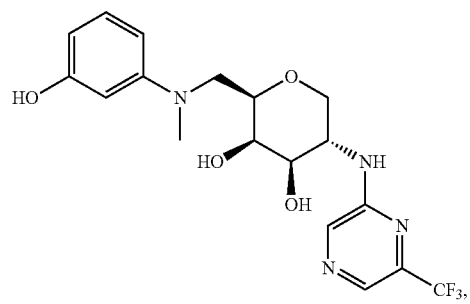

1983
-continued
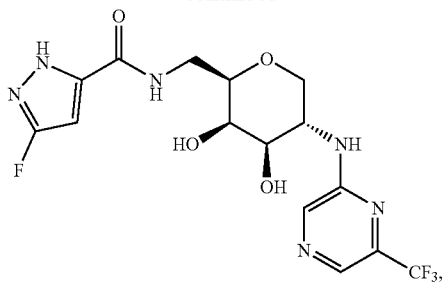
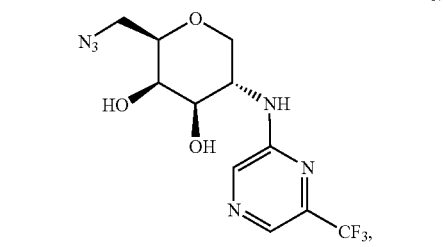
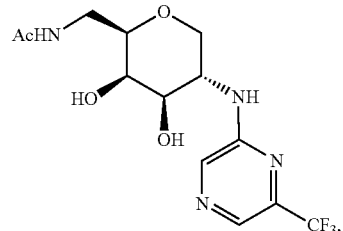
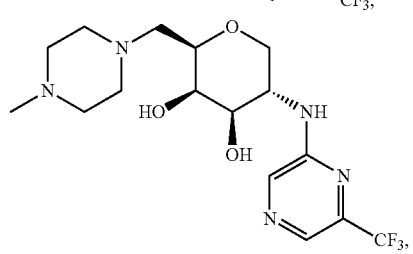
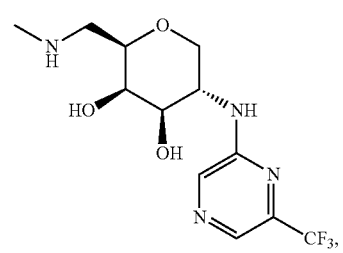
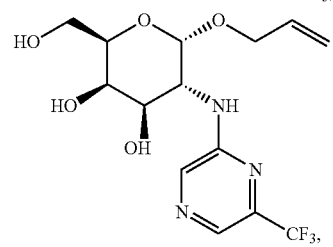
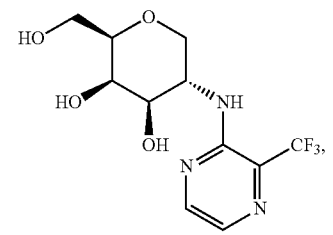
1984
-continued
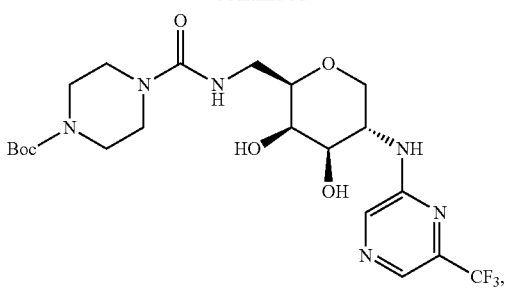
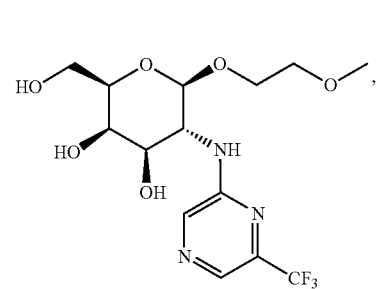
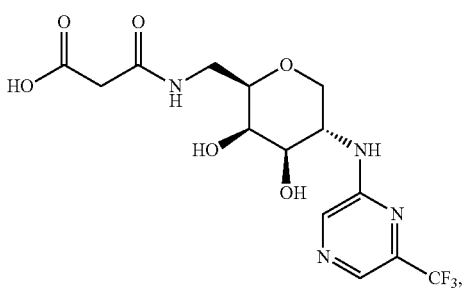
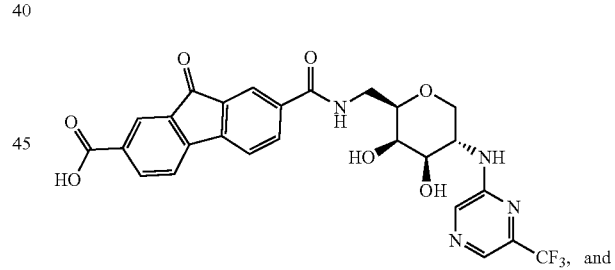
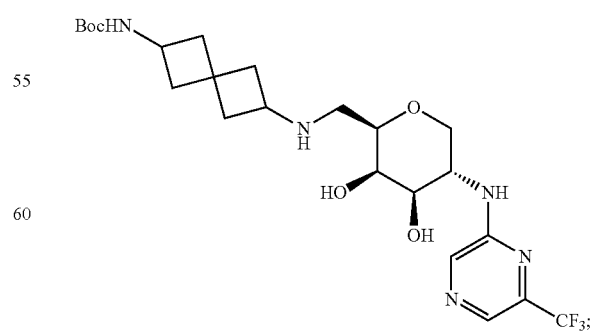
or a pharmaceutically acceptable salt thereof.

28. A compound selected from:
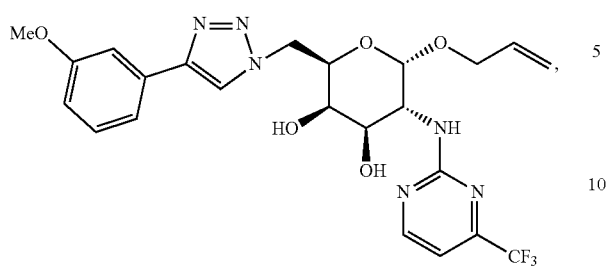
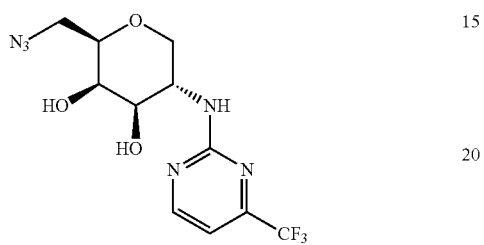
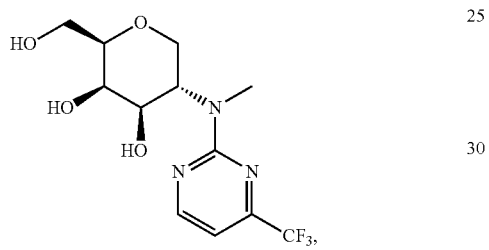
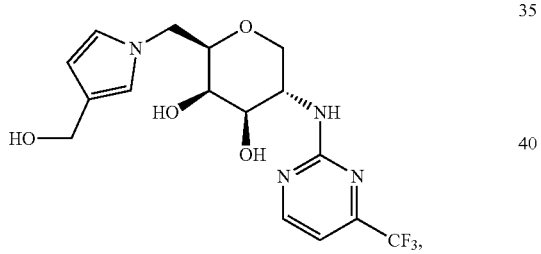
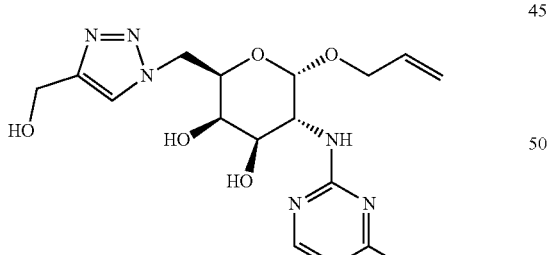
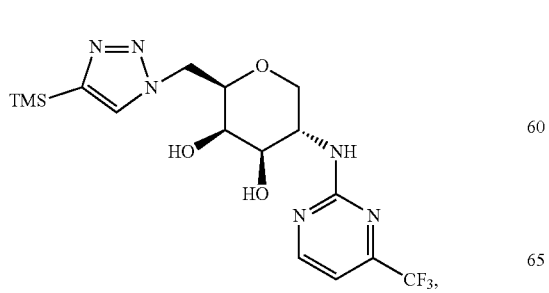
-continued
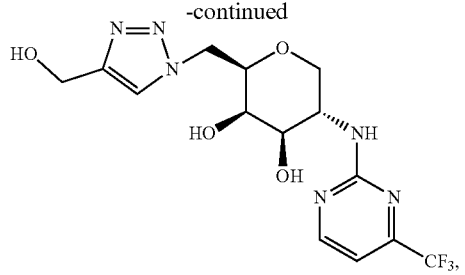
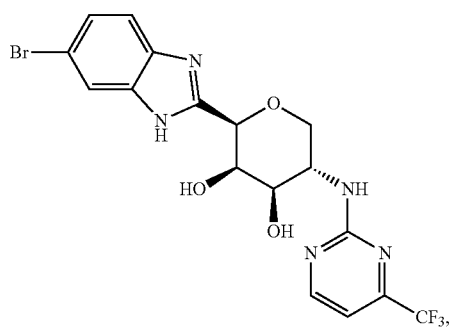
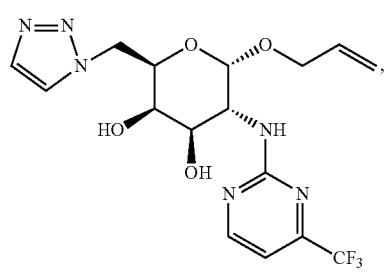
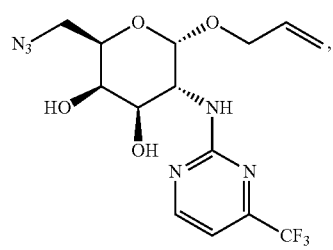
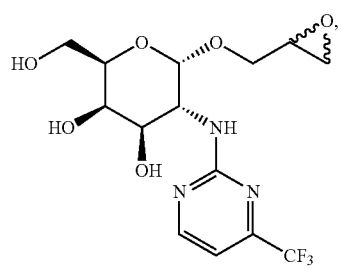
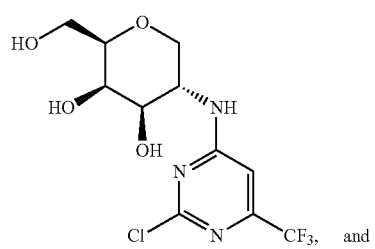
and 1987
-continued
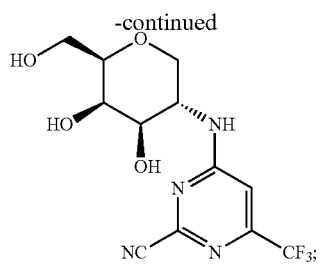
or a pharmaceutically acceptable salt thereof.
29. A compound selected from
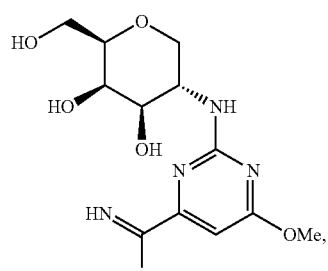
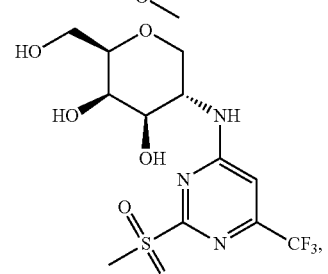
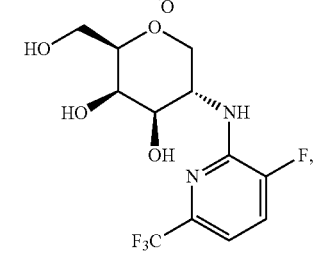
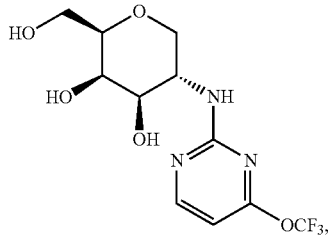
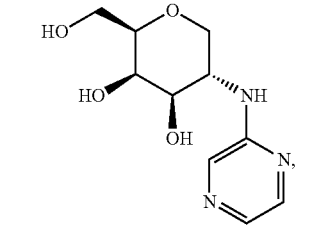
1988
-continued
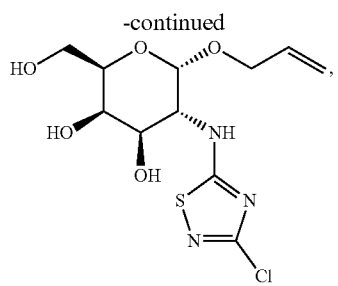
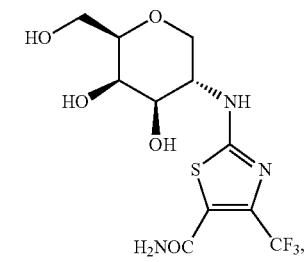
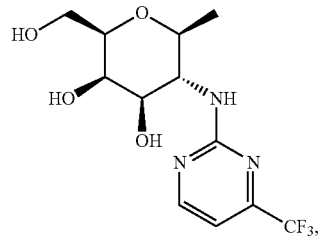
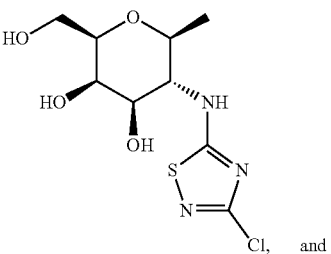
, and
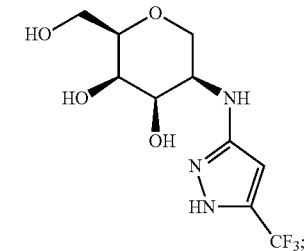
or a pharmaceutically acceptable salt thereof.
* * * * *

SEQUENCE LISTING

```
Sequence total quantity: 360
SEQ ID NO: 1                moltype = AA   length = 6
FEATURE                     Location/Qualifiers
source                      1..6
                            mol_type = protein
                            organism = synthetic construct
SEQUENCE: 1
MLKKIE                                                                        6

SEQ ID NO: 2                moltype = AA   length = 16
FEATURE                     Location/Qualifiers
source                      1..16
                            mol_type = protein
                            organism = synthetic construct
SEQUENCE: 2
HMVCLAYRGR PVCFAL                                                            16

SEQ ID NO: 3                moltype = AA   length = 16
FEATURE                     Location/Qualifiers
source                      1..16
                            mol_type = protein
                            organism = synthetic construct
SEQUENCE: 3
HMVCLSYRGR PVCFSL                                                            16

SEQ ID NO: 4                moltype = AA   length = 16
FEATURE                     Location/Qualifiers
source                      1..16
                            mol_type = protein
                            organism = synthetic construct
SEQUENCE: 4
HQVCLSYRGR PVCFST                                                            16

SEQ ID NO: 5                moltype = AA   length = 16
FEATURE                     Location/Qualifiers
source                      1..16
                            mol_type = protein
                            organism = synthetic construct
SEQUENCE: 5
QMRCLSYKGR RVCLWL                                                            16

SEQ ID NO: 6                moltype = AA   length = 16
FEATURE                     Location/Qualifiers
source                      1..16
                            mol_type = protein
                            organism = synthetic construct
SEQUENCE: 6
KRLCLQYKGS KVCFRL                                                            16

SEQ ID NO: 7                moltype = AA   length = 16
FEATURE                     Location/Qualifiers
source                      1..16
                            mol_type = protein
                            organism = synthetic construct
SEQUENCE: 7
RMRCLTYRGR RVCLEL                                                            16

SEQ ID NO: 8                moltype = AA   length = 16
FEATURE                     Location/Qualifiers
source                      1..16
                            mol_type = protein
                            organism = synthetic construct
SEQUENCE: 8
SMRCLQYRGS RVCLTL                                                            16

SEQ ID NO: 9                moltype = AA   length = 16
FEATURE                     Location/Qualifiers
source                      1..16
                            mol_type = protein
                            organism = synthetic construct
SEQUENCE: 9
HLRCLRYKGT RVCFSL                                                            16

SEQ ID NO: 10               moltype = AA   length = 16
FEATURE                     Location/Qualifiers
source                      1..16
                            mol_type = protein
                            organism = synthetic construct
```

```
SEQUENCE: 10
HVRCLSYKGR EVCVQL                                                              16

SEQ ID NO: 11           moltype = AA  length = 16
FEATURE                 Location/Qualifiers
source                  1..16
                        mol_type = protein
                        organism = synthetic construct
SEQUENCE: 11
PRMCLFIYKG RRVCIP                                                              16

SEQ ID NO: 12           moltype = AA  length = 16
FEATURE                 Location/Qualifiers
source                  1..16
                        mol_type = protein
                        organism = synthetic construct
SEQUENCE: 12
HMRCLHYKGR RVCFLL                                                              16

SEQ ID NO: 13           moltype = AA  length = 16
FEATURE                 Location/Qualifiers
source                  1..16
                        mol_type = protein
                        organism = synthetic construct
SEQUENCE: 13
HKRCLHYRGR MVCFLI                                                              16

SEQ ID NO: 14           moltype = AA  length = 16
FEATURE                 Location/Qualifiers
source                  1..16
                        mol_type = protein
                        organism = synthetic construct
SEQUENCE: 14
QKRCLKYKGS RVCFFL                                                              16

SEQ ID NO: 15           moltype = AA  length = 16
FEATURE                 Location/Qualifiers
source                  1..16
                        mol_type = protein
                        organism = synthetic construct
SEQUENCE: 15
HVRCLRYRGK NVCFLL                                                              16

SEQ ID NO: 16           moltype = AA  length = 16
FEATURE                 Location/Qualifiers
source                  1..16
                        mol_type = protein
                        organism = synthetic construct
SEQUENCE: 16
SDVCLRYRGR PVCFQV                                                              16

SEQ ID NO: 17           moltype = AA  length = 16
FEATURE                 Location/Qualifiers
source                  1..16
                        mol_type = protein
                        organism = synthetic construct
SEQUENCE: 17
RDVCLRYRGR PVCFQV                                                              16

SEQ ID NO: 18           moltype = AA  length = 16
FEATURE                 Location/Qualifiers
source                  1..16
                        mol_type = protein
                        organism = synthetic construct
SEQUENCE: 18
HDVCLRYRGR PVCFQV                                                              16

SEQ ID NO: 19           moltype = AA  length = 16
FEATURE                 Location/Qualifiers
source                  1..16
                        mol_type = protein
                        organism = synthetic construct
SEQUENCE: 19
SMVCLRYRGR PVCFQV                                                              16

SEQ ID NO: 20           moltype = AA  length = 16
FEATURE                 Location/Qualifiers
source                  1..16
                        mol_type = protein
```

```
-continued

SEQUENCE: 20
SAVCLRYRGR PVCFQV                                                    16

SEQ ID NO: 21          moltype = AA  length = 16
FEATURE                Location/Qualifiers
source                 1..16
                       mol_type = protein
                       organism = synthetic construct
SEQUENCE: 21
SDVCLNYRGR PVCFQV                                                    16

SEQ ID NO: 22          moltype = AA  length = 16
FEATURE                Location/Qualifiers
source                 1..16
                       mol_type = protein
                       organism = synthetic construct
SEQUENCE: 22
SDVCLHYRGR PVCFQV                                                    16

SEQ ID NO: 23          moltype = AA  length = 16
FEATURE                Location/Qualifiers
source                 1..16
                       mol_type = protein
                       organism = synthetic construct
SEQUENCE: 23
SDVCLAYRGR PVCFQV                                                    16

SEQ ID NO: 24          moltype = AA  length = 16
FEATURE                Location/Qualifiers
source                 1..16
                       mol_type = protein
                       organism = synthetic construct
SEQUENCE: 24
SDVCLRYRGR PVCFAV                                                    16

SEQ ID NO: 25          moltype = AA  length = 16
FEATURE                Location/Qualifiers
source                 1..16
                       mol_type = protein
                       organism = synthetic construct
SEQUENCE: 25
SDVCLRYRGR PVCFQL                                                    16

SEQ ID NO: 26          moltype = AA  length = 16
FEATURE                Location/Qualifiers
source                 1..16
                       mol_type = protein
                       organism = synthetic construct
SEQUENCE: 26
SDVCLRYRGR PVCFQA                                                    16

SEQ ID NO: 27          moltype = AA  length = 14
FEATURE                Location/Qualifiers
source                 1..14
                       mol_type = protein
                       organism = synthetic construct
SEQUENCE: 27
HMVCLSYRGR PVCF                                                      14

SEQ ID NO: 28          moltype = AA  length = 15
FEATURE                Location/Qualifiers
source                 1..15
                       mol_type = protein
                       organism = synthetic construct
SEQUENCE: 28
HMVCLSYRGR PVCFS                                                     15

SEQ ID NO: 29          moltype = AA  length = 16
FEATURE                Location/Qualifiers
source                 1..16
                       mol_type = protein
                       organism = synthetic construct
SEQUENCE: 29
HQVCLSYRGQ PVCFSL                                                    16

SEQ ID NO: 30          moltype = AA  length = 16
FEATURE                Location/Qualifiers
source                 1..16
```

```
                          mol_type = protein
                          organism = synthetic construct
SEQUENCE: 30
HQVCLSYRGR PTCFSL                                                             16

SEQ ID NO: 31             moltype = AA   length = 16
FEATURE                   Location/Qualifiers
source                    1..16
                          mol_type = protein
                          organism = synthetic construct
SEQUENCE: 31
HQVCLSYRGR PVCYSL                                                             16

SEQ ID NO: 32             moltype = AA   length = 16
FEATURE                   Location/Qualifiers
source                    1..16
                          mol_type = protein
                          organism = synthetic construct
SEQUENCE: 32
HQVCLSYRGQ PVCFST                                                             16

SEQ ID NO: 33             moltype = AA   length = 16
FEATURE                   Location/Qualifiers
source                    1..16
                          mol_type = protein
                          organism = synthetic construct
SEQUENCE: 33
HQVCLSYRGR PTCFST                                                             16

SEQ ID NO: 34             moltype = AA   length = 16
FEATURE                   Location/Qualifiers
source                    1..16
                          mol_type = protein
                          organism = synthetic construct
SEQUENCE: 34
HQVCLSYRGQ PTCFST                                                             16

SEQ ID NO: 35             moltype = AA   length = 16
FEATURE                   Location/Qualifiers
source                    1..16
                          mol_type = protein
                          organism = synthetic construct
CROSSLNK                  3..7
                          note = Tyr-Lys
CROSSLNK                  7..12
                          note = Lys-Lys
CROSSLNK                  11..16
                          note = Lys-Tyr
SEQUENCE: 35
RTYRTYKRTY KKGRTY                                                             16

SEQ ID NO: 36             moltype = AA   length = 16
FEATURE                   Location/Qualifiers
source                    1..16
                          mol_type = protein
                          organism = synthetic construct
SITE                      1..16
                          note = D-amino acids
CROSSLNK                  3..7
                          note = Tyr-Lys
CROSSLNK                  11..16
                          note = Lys-Tyr
CROSSLNK                  7..12
                          note = Lys-Lys
SEQUENCE: 36
RTYRTYKRTY KKGRTY                                                             16

SEQ ID NO: 37             moltype = AA   length = 16
FEATURE                   Location/Qualifiers
source                    1..16
                          mol_type = protein
                          organism = synthetic construct
SITE                      1..16
                          note = D-Amino Acids
CROSSLNK                  3..7
                          note = Tyr-Lys
CROSSLNK                  11..16
                          note = Lys-Tyr
CROSSLNK                  7..12
```

|  |  |  |
|---|---|---|
| MOD_RES | note = Lys-Lys<br>1 | |
| MOD_RES | note = Phenylacetic acid<br>4 | |
| MOD_RES | note = Phenylacetic acid<br>8 | |
| MOD_RES | note = Phenylacetic acid<br>14 | |
|  | note = Phenylacetic acid | |
| SEQUENCE: 37 | | |
| RTYRTYKRTY KKGRTY | | 16 |
| SEQ ID NO: 38<br>FEATURE<br>source | moltype = AA  length = 10<br>Location/Qualifiers<br>1..10<br>mol_type = protein<br>organism = synthetic construct | |
| SEQUENCE: 38 | | |
| TWKTSRISIF | | 10 |
| SEQ ID NO: 39<br>FEATURE<br>source | moltype = AA  length = 10<br>Location/Qualifiers<br>1..10<br>mol_type = protein<br>organism = synthetic construct | |
| SEQUENCE: 39 | | |
| FGRLVSSIRY | | 10 |
| SEQ ID NO: 40<br>FEATURE<br>source | moltype = AA  length = 13<br>Location/Qualifiers<br>1..13<br>mol_type = protein<br>organism = synthetic construct | |
| CROSSLNK | 2..12<br>note = Cys-Cys | |
| SEQUENCE: 40 | | |
| DCAWHLGELV WCT | | 13 |
| SEQ ID NO: 41<br>FEATURE<br>source | moltype = AA  length = 12<br>Location/Qualifiers<br>1..12<br>mol_type = protein<br>organism = synthetic construct | |
| SEQUENCE: 41 | | |
| DSAWHLGELW ST | | 12 |
| SEQ ID NO: 42<br>FEATURE<br>source | moltype = AA  length = 13<br>Location/Qualifiers<br>1..13<br>mol_type = protein<br>organism = synthetic construct | |
| SEQUENCE: 42 | | |
| DCHKRSFWAD NCT | | 13 |
| SEQ ID NO: 43<br>FEATURE<br>source | moltype = AA  length = 13<br>Location/Qualifiers<br>1..13<br>mol_type = protein<br>organism = synthetic construct | |
| SEQUENCE: 43 | | |
| DCRTQFRPNQ TCT | | 13 |
| SEQ ID NO: 44<br>FEATURE<br>source | moltype = AA  length = 13<br>Location/Qualifiers<br>1..13<br>mol_type = protein<br>organism = synthetic construct | |
| SEQUENCE: 44 | | |
| DCQLCDFWRT RCT | | 13 |
| SEQ ID NO: 45<br>FEATURE<br>source | moltype = AA  length = 13<br>Location/Qualifiers<br>1..13<br>mol_type = protein<br>organism = synthetic construct | |
| SEQUENCE: 45 | | |
| DCFEDFNEQR TCT | | 13 |
| SEQ ID NO: 46 | moltype = AA  length = 13 | |

-continued

```
FEATURE              Location/Qualifiers
source               1..13
                     mol_type = protein
                     organism = synthetic construct
SEQUENCE: 46
DCLAKFLKGK DCT                                                          13

SEQ ID NO: 47        moltype = AA  length = 13
FEATURE              Location/Qualifiers
source               1..13
                     mol_type = protein
                     organism = synthetic construct
SEQUENCE: 47
DCWHRRTHKT FCT                                                          13

SEQ ID NO: 48        moltype = AA  length = 11
FEATURE              Location/Qualifiers
source               1..11
                     mol_type = protein
                     organism = synthetic construct
SEQUENCE: 48
DCRTIQTRSC T                                                            11

SEQ ID NO: 49        moltype = AA  length = 13
FEATURE              Location/Qualifiers
source               1..13
                     mol_type = protein
                     organism = synthetic construct
SEQUENCE: 49
DCIKLAQLHS VCT                                                          13

SEQ ID NO: 50        moltype = AA  length = 13
FEATURE              Location/Qualifiers
source               1..13
                     mol_type = protein
                     organism = synthetic construct
SEQUENCE: 50
DCWRHRNATE WCT                                                          13

SEQ ID NO: 51        moltype = AA  length = 13
FEATURE              Location/Qualifiers
source               1..13
                     mol_type = protein
                     organism = synthetic construct
SEQUENCE: 51
DCQNWIKDVH KCT                                                          13

SEQ ID NO: 52        moltype = AA  length = 13
FEATURE              Location/Qualifiers
source               1..13
                     mol_type = protein
                     organism = synthetic construct
SEQUENCE: 52
DCAWHLGELV WCT                                                          13

SEQ ID NO: 53        moltype = AA  length = 13
FEATURE              Location/Qualifiers
source               1..13
                     mol_type = protein
                     organism = synthetic construct
SEQUENCE: 53
DCAFHLGELV WCT                                                          13

SEQ ID NO: 54        moltype = AA  length = 13
FEATURE              Location/Qualifiers
source               1..13
                     mol_type = protein
                     organism = synthetic construct
SEQUENCE: 54
DCAYHLGELV WCT                                                          13

SEQ ID NO: 55        moltype = AA  length = 11
FEATURE              Location/Qualifiers
source               1..11
                     mol_type = protein
                     organism = synthetic construct
CROSSLNK             1..11
                     note = Pro-Pro
SITE                 11
```

```
                         note = D-Phenylalanine
SEQUENCE: 55
PAWHLGELVW P                                                        11

SEQ ID NO: 56            moltype = AA   length = 15
FEATURE                  Location/Qualifiers
source                   1..15
                         mol_type = protein
                         organism = synthetic construct
CROSSLNK                 1..15
                         note = Pro-Pro
CROSSLNK                 3..13
                         note = Cys-Cys
SITE                     15
                         note = D-Amino Acid
SEQUENCE: 56
PDCAWHLGEL VWCTP                                                    15

SEQ ID NO: 57            moltype = AA   length = 15
FEATURE                  Location/Qualifiers
source                   1..15
                         mol_type = protein
                         organism = synthetic construct
CROSSLNK                 3..13
                         note = Cys-Cys
CROSSLNK                 1..15
                         note = Cys-Cys
SEQUENCE: 57
CDCAWHLGEL VWCTC                                                    15

SEQ ID NO: 58            moltype = AA   length = 12
FEATURE                  Location/Qualifiers
source                   1..12
                         mol_type = protein
                         organism = synthetic construct
SEQUENCE: 58
EPIHRSTLTA LL                                                       12

SEQ ID NO: 59            moltype = AA   length = 4
FEATURE                  Location/Qualifiers
source                   1..4
                         mol_type = protein
                         organism = synthetic construct
SEQUENCE: 59
APAR                                                                 4

SEQ ID NO: 60            moltype = AA   length = 6
FEATURE                  Location/Qualifiers
source                   1..6
                         mol_type = protein
                         organism = synthetic construct
REPEAT                   1..4
                         note = repeated twice
CROSSLNK                 4..5
                         note = His-Lys
CROSSLNK                 1
                         note = Cys-Cys
SEQUENCE: 60
CFHHKG                                                               6

SEQ ID NO: 61            moltype = AA   length = 6
FEATURE                  Location/Qualifiers
source                   1..6
                         mol_type = protein
                         organism = synthetic construct
SEQUENCE: 61
HWRGWV                                                               6

SEQ ID NO: 62            moltype = AA   length = 6
FEATURE                  Location/Qualifiers
source                   1..6
                         mol_type = protein
                         organism = synthetic construct
SEQUENCE: 62
HYFKFD                                                               6

SEQ ID NO: 63            moltype = AA   length = 6
FEATURE                  Location/Qualifiers
source                   1..6
```

```
                            mol_type = protein
                            organism = synthetic construct
SEQUENCE: 63
HFRRHL                                                                        6

SEQ ID NO: 64               moltype = AA  length = 6
FEATURE                     Location/Qualifiers
source                      1..6
                            mol_type = protein
                            organism = synthetic construct
NON_STD                     3
                            note = Citrulline
SEQUENCE: 64
HWXGWV                                                                        6

SEQ ID NO: 65               moltype = AA  length = 6
FEATURE                     Location/Qualifiers
source                      1..6
                            mol_type = protein
                            organism = synthetic construct
NON_STD                     3
                            note = Citrulline
MOD_RES                     2
                            note = MeTrp
MOD_RES                     5
                            note = MeTrp
SEQUENCE: 65
HWXGWV                                                                        6

SEQ ID NO: 66               moltype = AA  length = 4
FEATURE                     Location/Qualifiers
source                      1..4
                            mol_type = protein
                            organism = synthetic construct
REPEAT                      1
                            note = repeated twice
CROSSLNK                    1..2
                            note = Asp-Ala
SEQUENCE: 66
DAAG                                                                          4

SEQ ID NO: 67               moltype = AA  length = 4
FEATURE                     Location/Qualifiers
source                      1..4
                            mol_type = protein
                            organism = synthetic construct
SEQUENCE: 67
DAAG                                                                          4

SEQ ID NO: 68               moltype = AA  length = 9
FEATURE                     Location/Qualifiers
source                      1..9
                            mol_type = protein
                            organism = synthetic construct
CROSSLNK                    1..9
                            note = N(alpha)acetyl Linker (Ser-Glu)
CROSSLNK                    8..9
                            note = Lactic acid Linker (Lys-Glu)
SEQUENCE: 68
SARWHYFKE                                                                     9

SEQ ID NO: 69               moltype = AA  length = 9
FEATURE                     Location/Qualifiers
source                      1..9
                            mol_type = protein
                            organism = synthetic construct
CROSSLNK                    1..9
                            note = N(alpha)acetyl Linker (Dpr-Glu)
CROSSLNK                    8..9
                            note = Lactic acid Linker (Lys-Glu)
MOD_RES                     1
                            note = Dpr
SEQUENCE: 69
XARWHYFKE                                                                     9

SEQ ID NO: 70               moltype = AA  length = 7
FEATURE                     Location/Qualifiers
source                      1..7
                            mol_type = protein
```

```
                           -continued

CROSSLNK                organism = synthetic construct
                        1..7
                        note = Link M-Lys
NON_STD                 1
                        note = Link M
SEQUENCE: 70
XWFRHYK                                                              7

SEQ ID NO: 71           moltype = AA   length = 8
FEATURE                 Location/Qualifiers
source                  1..8
                        mol_type = protein
                        organism = synthetic construct
SEQUENCE: 71
NKFRGKYK                                                             8

SEQ ID NO: 72           moltype = AA   length = 8
FEATURE                 Location/Qualifiers
source                  1..8
                        mol_type = protein
                        organism = synthetic construct
SEQUENCE: 72
NARKFYKG                                                             8

SEQ ID NO: 73           moltype = AA   length = 8
FEATURE                 Location/Qualifiers
source                  1..8
                        mol_type = protein
                        organism = synthetic construct
SEQUENCE: 73
FYWHCLDE                                                             8

SEQ ID NO: 74           moltype = AA   length = 8
FEATURE                 Location/Qualifiers
source                  1..8
                        mol_type = protein
                        organism = synthetic construct
SEQUENCE: 74
FYCHWALE                                                             8

SEQ ID NO: 75           moltype = AA   length = 8
FEATURE                 Location/Qualifiers
source                  1..8
                        mol_type = protein
                        organism = synthetic construct
SEQUENCE: 75
FYCHTIDE                                                             8

SEQ ID NO: 76           moltype = AA   length = 16
FEATURE                 Location/Qualifiers
source                  1..16
                        mol_type = protein
                        organism = synthetic construct
SEQUENCE: 76
FYWHCLDEFY CHTIDE                                                   16

SEQ ID NO: 77           moltype = AA   length = 4
FEATURE                 Location/Qualifiers
source                  1..4
                        mol_type = protein
                        organism = synthetic construct
SEQUENCE: 77
RRGW                                                                 4

SEQ ID NO: 78           moltype = AA   length = 7
FEATURE                 Location/Qualifiers
source                  1..7
                        mol_type = protein
                        organism = synthetic construct
SEQUENCE: 78
KHRFNKD                                                              7

SEQ ID NO: 79           moltype = AA   length = 7
FEATURE                 Location/Qualifiers
source                  1..7
                        mol_type = protein
                        organism = synthetic construct
SEQUENCE: 79
CPSTHWK                                                              7
```

-continued

```
SEQ ID NO: 80            moltype = AA   length = 7
FEATURE                  Location/Qualifiers
source                   1..7
                         mol_type = protein
                         organism = synthetic construct
SEQUENCE: 80
NVQYFAV                                                                  7

SEQ ID NO: 81            moltype = AA   length = 7
FEATURE                  Location/Qualifiers
source                   1..7
                         mol_type = protein
                         organism = synthetic construct
SEQUENCE: 81
ASHTQKS                                                                  7

SEQ ID NO: 82            moltype = AA   length = 7
FEATURE                  Location/Qualifiers
source                   1..7
                         mol_type = protein
                         organism = synthetic construct
SEQUENCE: 82
QPQMSHM                                                                  7

SEQ ID NO: 83            moltype = AA   length = 7
FEATURE                  Location/Qualifiers
source                   1..7
                         mol_type = protein
                         organism = synthetic construct
SEQUENCE: 83
TNIESLK                                                                  7

SEQ ID NO: 84            moltype = AA   length = 7
FEATURE                  Location/Qualifiers
source                   1..7
                         mol_type = protein
                         organism = synthetic construct
SEQUENCE: 84
NCHKCWN                                                                  7

SEQ ID NO: 85            moltype = AA   length = 7
FEATURE                  Location/Qualifiers
source                   1..7
                         mol_type = protein
                         organism = synthetic construct
SEQUENCE: 85
SHLSKNF                                                                  7

SEQ ID NO: 86            moltype = AA   length = 8
FEATURE                  Location/Qualifiers
source                   1..8
                         mol_type = protein
                         organism = synthetic construct
SEQUENCE: 86
FDLLEHFY                                                                 8

SEQ ID NO: 87            moltype = AA   length = 9
FEATURE                  Location/Qualifiers
source                   1..9
                         mol_type = protein
                         organism = synthetic construct
SEQUENCE: 87
DLLHHFDYF                                                                9

SEQ ID NO: 88            moltype = AA   length = 13
FEATURE                  Location/Qualifiers
source                   1..13
                         mol_type = protein
                         organism = synthetic construct
SEQUENCE: 88
GIFVIQSESL KKC                                                          13

SEQ ID NO: 89            moltype = AA   length = 9
FEATURE                  Location/Qualifiers
source                   1..9
                         mol_type = protein
                         organism = synthetic construct
SEQUENCE: 89
```

```
-continued

SVLTLENCK                                                                  9

SEQ ID NO: 90        moltype = AA  length = 8
FEATURE              Location/Qualifiers
source               1..8
                     mol_type = protein
                     organism = synthetic construct SEQUENCE: 90
SVLTLENC                                                                   8

SEQ ID NO: 91        moltype = AA  length = 9
FEATURE              Location/Qualifiers
source               1..9
                     mol_type = protein
                     organism = synthetic construct SEQUENCE: 91
SVLTLDNCK                                                                  9

SEQ ID NO: 92        moltype = AA  length = 8
FEATURE              Location/Qualifiers
source               1..8
                     mol_type = protein
                     organism = synthetic construct SEQUENCE: 92
SVLTEENC                                                                   8

SEQ ID NO: 93        moltype = AA  length = 8
FEATURE              Location/Qualifiers
source               1..8
                     mol_type = protein
                     organism = synthetic construct SEQUENCE: 93
SVLTEENS                                                                   8

SEQ ID NO: 94        moltype = AA  length = 8
FEATURE              Location/Qualifiers
source               1..8
                     mol_type = protein
                     organism = synthetic construct SEQUENCE: 94
SVLTDENC                                                                   8

SEQ ID NO: 95        moltype = AA  length = 8
FEATURE              Location/Qualifiers
source               1..8
                     mol_type = protein
                     organism = synthetic construct SEQUENCE: 95
SVLTDENS                                                                   8

SEQ ID NO: 96        moltype = AA  length = 9
FEATURE              Location/Qualifiers
source               1..9
                     mol_type = protein
                     organism = unidentified SEQUENCE: 96
PIQSESLKK                                                                  9

SEQ ID NO: 97        moltype = AA  length = 9
FEATURE              Location/Qualifiers
source               1..9
                     mol_type = protein
                     organism = synthetic construct SEQUENCE: 97
VIDSESLKK                                                                  9

SEQ ID NO: 98        moltype = AA  length = 9
FEATURE              Location/Qualifiers
source               1..9
                     mol_type = protein
                     organism = synthetic construct SEQUENCE: 98
PIDSESLKK                                                                  9

SEQ ID NO: 99        moltype = AA  length = 9
FEATURE              Location/Qualifiers
source               1..9
                     mol_type = protein
                     organism = synthetic construct
```

-continued

```
SEQUENCE: 99
VIQSESLKK                                                            9

SEQ ID NO: 100          moltype = AA   length = 21
FEATURE                 Location/Qualifiers
source                  1..21
                        mol_type = protein
                        organism = synthetic construct
SEQUENCE: 100
PIESESPEGK PEGSVLTEEN C                                             21

SEQ ID NO: 101          moltype = AA   length = 21
FEATURE                 Location/Qualifiers
source                  1..21
                        mol_type = protein
                        organism = synthetic construct
SEQUENCE: 101
VIQSESPEGK PEGSVLTLEN C                                             21

SEQ ID NO: 102          moltype = AA   length = 21
FEATURE                 Location/Qualifiers
source                  1..21
                        mol_type = protein
                        organism = synthetic construct
SEQUENCE: 102
VIQSESPEGK PEGSVLTEEN C                                             21

SEQ ID NO: 103          moltype = AA   length = 21
FEATURE                 Location/Qualifiers
source                  1..21
                        mol_type = protein
                        organism = synthetic construct
SEQUENCE: 103
PIDDESPEGK PEGSVLTLEN C                                             21

SEQ ID NO: 104          moltype = AA   length = 21
FEATURE                 Location/Qualifiers
source                  1..21
                        mol_type = protein
                        organism = synthetic construct
SEQUENCE: 104
PIDDESPEGK PEGSVLTEEN C                                             21

SEQ ID NO: 105          moltype = AA   length = 19
FEATURE                 Location/Qualifiers
source                  1..19
                        mol_type = protein
                        organism = synthetic construct
SEQUENCE: 105
VIQSESLKKC KSVLTLENC                                                19

SEQ ID NO: 106          moltype = AA   length = 19
FEATURE                 Location/Qualifiers
source                  1..19
                        mol_type = protein
                        organism = synthetic construct
SEQUENCE: 106
PIQSESLKKC KSVLTLENC                                                19

SEQ ID NO: 107          moltype = AA   length = 19
FEATURE                 Location/Qualifiers
source                  1..19
                        mol_type = protein
                        organism = synthetic construct
SEQUENCE: 107
VIESESLKKC KSVLTLENC                                                19

SEQ ID NO: 108          moltype = AA   length = 19
FEATURE                 Location/Qualifiers
source                  1..19
                        mol_type = protein
                        organism = synthetic construct
SEQUENCE: 108
VIDSESLKKC KSVLTLENC                                                19

SEQ ID NO: 109          moltype = AA   length = 19
FEATURE                 Location/Qualifiers
source                  1..19
                        mol_type = protein
```

```
                        organism = synthetic construct
SEQUENCE: 109
PIESESLKKC KSVLTLENC                                                   19

SEQ ID NO: 110          moltype = AA   length = 19
FEATURE                 Location/Qualifiers
source                  1..19
                        mol_type = protein
                        organism = synthetic construct
SEQUENCE: 110
VIQSESLKKC IQAGKLENC                                                   19

SEQ ID NO: 111          moltype = AA   length = 19
FEATURE                 Location/Qualifiers
source                  1..19
                        mol_type = protein
                        organism = synthetic construct
SEQUENCE: 111
PIQSESLKKC IQAGKLENC                                                   19

SEQ ID NO: 112          moltype = AA   length = 19
FEATURE                 Location/Qualifiers
source                  1..19
                        mol_type = protein
                        organism = synthetic construct
SEQUENCE: 112
VIESESLKKC IQAGKLENC                                                   19

SEQ ID NO: 113          moltype = AA   length = 19
FEATURE                 Location/Qualifiers
source                  1..19
                        mol_type = protein
                        organism = synthetic construct
SEQUENCE: 113
VIDSESLKKC IQAGKLENC                                                   19

SEQ ID NO: 114          moltype = AA   length = 19
FEATURE                 Location/Qualifiers
source                  1..19
                        mol_type = protein
                        organism = synthetic construct
SEQUENCE: 114
PIESESLKKC IQAGKLENC                                                   19

SEQ ID NO: 115          moltype = AA   length = 19
FEATURE                 Location/Qualifiers
source                  1..19
                        mol_type = protein
                        organism = synthetic construct
SEQUENCE: 115
PIQSESLKKC KSVLTLENK                                                   19

SEQ ID NO: 116          moltype = AA   length = 19
FEATURE                 Location/Qualifiers
source                  1..19
                        mol_type = protein
                        organism = synthetic construct
SEQUENCE: 116
VIESESLKKC KSVLTLENK                                                   19

SEQ ID NO: 117          moltype = AA   length = 19
FEATURE                 Location/Qualifiers
source                  1..19
                        mol_type = protein
                        organism = synthetic construct
SEQUENCE: 117
VIDSESLKKC KSVLTLENK                                                   19

SEQ ID NO: 118          moltype = AA   length = 19
FEATURE                 Location/Qualifiers
source                  1..19
                        mol_type = protein
                        organism = synthetic construct
SEQUENCE: 118
PIESESLKKC KSVLTLENK                                                   19

SEQ ID NO: 119          moltype = AA   length = 19
FEATURE                 Location/Qualifiers
source                  1..19
```

```
                              -continued mol_type = protein
                         organism = synthetic construct
SEQUENCE: 119
VIQSESLKKC IQAGKLENK                                          19

SEQ ID NO: 120           moltype = AA   length = 19
FEATURE                  Location/Qualifiers
source                   1..19
                         mol_type = protein
                         organism = synthetic construct
SEQUENCE: 120
PIQSESLKKC IQAGKLENK                                          19

SEQ ID NO: 121           moltype = AA   length = 19
FEATURE                  Location/Qualifiers
source                   1..19
                         mol_type = protein
                         organism = synthetic construct
SEQUENCE: 121
VIESESLKKC IQAGKLENK                                          19

SEQ ID NO: 122           moltype = AA   length = 19
FEATURE                  Location/Qualifiers
source                   1..19
                         mol_type = protein
                         organism = synthetic construct
SEQUENCE: 122
VIDSESLKKC IQAGKLENK                                          19

SEQ ID NO: 123           moltype = AA   length = 19
FEATURE                  Location/Qualifiers
source                   1..19
                         mol_type = protein
                         organism = synthetic construct
SEQUENCE: 123
PIESESLKKC IQAGKLENK                                          19

SEQ ID NO: 124           moltype = AA   length = 16
FEATURE                  Location/Qualifiers
source                   1..16
                         mol_type = protein
                         organism = synthetic construct
SEQUENCE: 124
PIESESGSVL TLENCK                                             16

SEQ ID NO: 125           moltype = AA   length = 17
FEATURE                  Location/Qualifiers
source                   1..17
                         mol_type = protein
                         organism = synthetic construct
SEQUENCE: 125
PIESESGGSV LTLENCK                                            17

SEQ ID NO: 126           moltype = AA   length = 18
FEATURE                  Location/Qualifiers
source                   1..18
                         mol_type = protein
                         organism = synthetic construct
SEQUENCE: 126
PIESESGGGS VLTLENCK                                           18

SEQ ID NO: 127           moltype = AA   length = 19
FEATURE                  Location/Qualifiers
source                   1..19
                         mol_type = protein
                         organism = synthetic construct
SEQUENCE: 127
PIESESGGGG SVLTLENCK                                          19

SEQ ID NO: 128           moltype = AA   length = 20
FEATURE                  Location/Qualifiers
source                   1..20
                         mol_type = protein
                         organism = synthetic construct
SEQUENCE: 128
PIESESGGGG GSVLTLENCK                                         20

SEQ ID NO: 129           moltype = AA   length = 16
FEATURE                  Location/Qualifiers
```

-continued

```
source                  1..16
                        mol_type = protein
                        organism = synthetic construct
SEQUENCE: 129
VIQSESGSVL TLENCK                                                           16

SEQ ID NO: 130          moltype = AA   length = 17
FEATURE                 Location/Qualifiers
source                  1..17
                        mol_type = protein
                        organism = synthetic construct
SEQUENCE: 130
VIQSESGGSV LTLENCK                                                          17

SEQ ID NO: 131          moltype = AA   length = 18
FEATURE                 Location/Qualifiers
source                  1..18
                        mol_type = protein
                        organism = synthetic construct
SEQUENCE: 131
VIQSESGGGS VLTLENCK                                                         18

SEQ ID NO: 132          moltype = AA   length = 19
FEATURE                 Location/Qualifiers
source                  1..19
                        mol_type = protein
                        organism = synthetic construct
SEQUENCE: 132
VIQSESGGGG SVLTLENCK                                                        19

SEQ ID NO: 133          moltype = AA   length = 20
FEATURE                 Location/Qualifiers
source                  1..20
                        mol_type = protein
                        organism = synthetic construct
SEQUENCE: 133
VIQSESGGGG GSVLTLENCK                                                       20

SEQ ID NO: 134          moltype = AA   length = 28
FEATURE                 Location/Qualifiers
source                  1..28
                        mol_type = protein
                        organism = synthetic construct
SEQUENCE: 134
KGCFVIQSES LKKSIQAGKS VLTLENCK                                              28

SEQ ID NO: 135          moltype = AA   length = 21
FEATURE                 Location/Qualifiers
source                  1..21
                        mol_type = protein
                        organism = synthetic construct
SEQUENCE: 135
LKKCIQAGKS VLTLENCKQA N                                                     21

SEQ ID NO: 136          moltype = AA   length = 22
FEATURE                 Location/Qualifiers
source                  1..22
                        mol_type = protein
                        organism = synthetic construct
SEQUENCE: 136
WQDKGIFVIQ SESLKKCIQA GK                                                    22

SEQ ID NO: 137          moltype = AA   length = 28
FEATURE                 Location/Qualifiers
source                  1..28
                        mol_type = protein
                        organism = synthetic construct
SEQUENCE: 137
KGIFVIQSES LKKCIQAGKS VLTLENCK                                              28

SEQ ID NO: 138          moltype = AA   length = 13
FEATURE                 Location/Qualifiers
source                  1..13
                        mol_type = protein
                        organism = synthetic construct
SEQUENCE: 138
GIFVIQSESL KKC                                                              13

SEQ ID NO: 139          moltype = AA   length = 10
```

-continued

```
FEATURE                 Location/Qualifiers
source                  1..10
                        mol_type = protein
                        organism = synthetic construct
SEQUENCE: 139
WSVLTLENCK                                                                      10

SEQ ID NO: 140          moltype = AA   length = 31
FEATURE                 Location/Qualifiers
source                  1..31
                        mol_type = protein
                        organism = synthetic construct
SEQUENCE: 140
WQDKGIFVIQ SESLKKCIQA GKSVLTLENC K                                               31

SEQ ID NO: 141          moltype = AA   length = 9
FEATURE                 Location/Qualifiers
source                  1..9
                        mol_type = protein
                        organism = synthetic construct
SEQUENCE: 141
YDWIPSSAW                                                                        9

SEQ ID NO: 142          moltype = AA   length = 9
FEATURE                 Location/Qualifiers
source                  1..9
                        mol_type = protein
                        organism = synthetic construct
SEQUENCE: 142
AGAIWQRDW                                                                        9

SEQ ID NO: 143          moltype = AA   length = 9
FEATURE                 Location/Qualifiers
source                  1..9
                        mol_type = protein
                        organism = synthetic construct
SEQUENCE: 143
AGAIWQKDW                                                                        9

SEQ ID NO: 144          moltype = AA   length = 8
FEATURE                 Location/Qualifiers
source                  1..8
                        mol_type = protein
                        organism = synthetic construct
SEQUENCE: 144
VIQSESLK                                                                         8

SEQ ID NO: 145          moltype = AA   length = 8
FEATURE                 Location/Qualifiers
source                  1..8
                        mol_type = protein
                        organism = synthetic construct
SEQUENCE: 145
PIQSESLK                                                                         8

SEQ ID NO: 146          moltype = AA   length = 8
FEATURE                 Location/Qualifiers
source                  1..8
                        mol_type = protein
                        organism = synthetic construct
SEQUENCE: 146
PIESESLK                                                                         8

SEQ ID NO: 147          moltype = AA   length = 9
FEATURE                 Location/Qualifiers
source                  1..9
                        mol_type = protein
                        organism = synthetic construct
SEQUENCE: 147
SVLTEENCK                                                                        9

SEQ ID NO: 148          moltype = AA   length = 8
FEATURE                 Location/Qualifiers
source                  1..8
                        mol_type = protein
                        organism = synthetic construct
SITE                    5
                        note = Any Naturally-Occurring Amino Acid
SITE                    8
```

```
                        note = Any Naturally-Occurring Amino Acid
SEQUENCE: 148
SVLTXENX                                                                8

SEQ ID NO: 149          moltype =    length =
SEQUENCE: 149
000

SEQ ID NO: 150          moltype =    length =
SEQUENCE: 150
000

SEQ ID NO: 151          moltype = AA   length = 9
FEATURE                 Location/Qualifiers
source                  1..9
                        mol_type = protein
                        organism = synthetic construct
SITE                    5
                        note = Any Naturally-Occurring Amino Acid
SEQUENCE: 151
SVLTXENCK                                                               9

SEQ ID NO: 152          moltype = AA   length = 8
FEATURE                 Location/Qualifiers
source                  1..8
                        mol_type = protein
                        organism = synthetic construct
SITE                    1
                        note = Any Naturally-Occurring Amino Acid
SITE                    3
                        note = Any Naturally-Occurring Amino Acid
SITE                    4
                        note = Any Naturally-Occurring Amino Acid
SITE                    6
                        note = Any Naturally-Occurring Amino Acid
SEQUENCE: 152
XIXXEXLK                                                                8

SEQ ID NO: 153          moltype = AA   length = 14
FEATURE                 Location/Qualifiers
source                  1..14
                        mol_type = protein
                        organism = synthetic construct
MOD_RES                 5
                        note = MeTrp
MOD_RES                 14
                        note = MeIle
DISULFID                3..13
                        note = Cys-Cys
SITE                    1
                        note = D-Amino Acid
MOD_RES                 9
                        note = MeGly
SEQUENCE: 153
YICVWQDWGA HRCI                                                        14

SEQ ID NO: 154          moltype = AA   length = 26
FEATURE                 Location/Qualifiers
source                  1..26
                        mol_type = protein
                        organism = synthetic construct
DISULFID                2..12
                        note = Cys-Cys
SEQUENCE: 154
ICVVQDWGHH RCTAGMANLT SHASAI                                           26

SEQ ID NO: 155          moltype = AA   length = 13
FEATURE                 Location/Qualifiers
source                  1..13
                        mol_type = protein
                        organism = synthetic construct
DISULFID                2..12
                        note = Cys-Cys
SEQUENCE: 155
ICVVQDWGHH RCT                                                         13

SEQ ID NO: 156          moltype = AA   length = 11
FEATURE                 Location/Qualifiers
source                  1..11
```

-continued

```
                        mol_type = protein
                        organism = synthetic construct
DISULFID                1..11
                        note = Cys-Cys
SEQUENCE: 156
CVVQDWGHHA C                                                                  11

SEQ ID NO: 157          moltype = AA   length = 13
FEATURE                 Location/Qualifiers
source                  1..13
                        mol_type = protein
                        organism = synthetic construct
MOD_RES                 1
                        note = AcIle
DISULFID                2..12
                        note = Cys-Cys
SEQUENCE: 157
ICVVQDWGHH RCT                                                                13

SEQ ID NO: 158          moltype = AA   length = 12
FEATURE                 Location/Qualifiers
source                  1..12
                        mol_type = protein
                        organism = synthetic construct
DISULFID                1..11
                        note = Cys-Cys
SEQUENCE: 158
CVVQDWGHHR CT                                                                 12

SEQ ID NO: 159          moltype = AA   length = 11
FEATURE                 Location/Qualifiers
source                  1..11
                        mol_type = protein
                        organism = synthetic construct
DISULFID                1..11
                        note = Cys-Cys
SEQUENCE: 159
CVVQDWGHHR C                                                                  11

SEQ ID NO: 160          moltype = AA   length = 13
FEATURE                 Location/Qualifiers
source                  1..13
                        mol_type = protein
                        organism = synthetic construct
MOD_RES                 1
                        note = AcIle
DISULFID                2..12
                        note = Cys-Cys
SEQUENCE: 160
ICVVGDWGHH RCT                                                                13

SEQ ID NO: 161          moltype = AA   length = 13
FEATURE                 Location/Qualifiers
source                  1..13
                        mol_type = protein
                        organism = synthetic construct
MOD_RES                 1
                        note = AcIle
DISULFID                2..12
                        note = Cys-Cys
SEQUENCE: 161
ICVVQPWGHH RCT                                                                13

SEQ ID NO: 162          moltype = AA   length = 17
FEATURE                 Location/Qualifiers
source                  1..17
                        mol_type = protein
                        organism = synthetic construct
DISULFID                6..16
                        note = Cys-Cys
SEQUENCE: 162
KYSSICVVQD WGHHRCT                                                            17

SEQ ID NO: 163          moltype = AA   length = 27
FEATURE                 Location/Qualifiers
source                  1..27
                        mol_type = protein
                        organism = synthetic construct
MOD_RES                 1
```

```
                        note = AcIle
DISULFID                2..12
                        note = Cys-Cys
SEQUENCE: 163
ICVVQDWGHH RCTAGHMANL TSHASAK                                            27

SEQ ID NO: 164          moltype = AA   length = 13
FEATURE                 Location/Qualifiers
source                  1..13
                        mol_type = protein
                        organism = synthetic construct
MOD_RES                 1
                        note = AcIle
MOD_RES                 4
                        note = MeTrp
SEQUENCE: 164
ICVWQDWGAH RCT                                                           13

SEQ ID NO: 165          moltype = AA   length = 13
FEATURE                 Location/Qualifiers
source                  1..13
                        mol_type = protein
                        organism = synthetic construct
MOD_RES                 1
                        note = vIle
MOD_RES                 8
                        note = MeGly
MOD_RES                 13
                        note = MeIle
MOD_RES                 4
                        note = MeTrp
SEQUENCE: 165
ICVWQDWGAH RCI                                                           13

SEQ ID NO: 166          moltype = AA   length = 13
FEATURE                 Location/Qualifiers
source                  1..13
                        mol_type = protein
                        organism = synthetic construct
MOD_RES                 1
                        note = vIle
MOD_RES                 4
                        note = MeTrp
MOD_RES                 8
                        note = MeGly
MOD_RES                 13
                        note = MeIle
SEQUENCE: 166
ICVWQDWGAH RCI                                                           13

SEQ ID NO: 167          moltype = AA   length = 13
FEATURE                 Location/Qualifiers
source                  1..13
                        mol_type = protein
                        organism = synthetic construct
DISULFID                2..12
                        note = Cys-Cys
MOD_RES                 1
                        note = AcIle
SEQUENCE: 167
ICVWQDWGAH RCT                                                           13

SEQ ID NO: 168          moltype = AA   length = 13
FEATURE                 Location/Qualifiers
source                  1..13
                        mol_type = protein
                        organism = synthetic construct
DISULFID                2..12
                        note = Cys-Cys
MOD_RES                 1
                        note = MeIle
MOD_RES                 4
                        note = MeTrp
MOD_RES                 8
                        note = MeGly
SEQUENCE: 168
ICVWQDWGAH RCI                                                           13

SEQ ID NO: 169          moltype = AA   length = 13
```

```
FEATURE                 Location/Qualifiers
source                  1..13
                        mol_type = protein
                        organism = synthetic construct
MOD_RES                 1
                        note = AcIle
MOD_RES                 4
                        note = MeTrp
MOD_RES                 8
                        note = MeGly
MOD_RES                 13
                        note = MeIle
DISULFID                2..12
                        note = Cys-Cys
SEQUENCE: 169
ICVWQDWGAH RCI                                                              13

SEQ ID NO: 170          moltype = AA  length = 13
FEATURE                 Location/Qualifiers
source                  1..13
                        mol_type = protein
                        organism = synthetic construct
DISULFID                2..12
                        note = Cys-Cys
MOD_RES                 1
                        note = AcIle
MOD_RES                 4
                        note = MeTrp
SEQUENCE: 170
ICVWQDWGAH RCT                                                              13

SEQ ID NO: 171          moltype = AA  length = 13
FEATURE                 Location/Qualifiers
source                  1..13
                        mol_type = protein
                        organism = synthetic construct
DISULFID                2..13
                        note = Cys-Cys
MOD_RES                 1
                        note = AcXaa
SEQUENCE: 171
XCVXQDWGXX XCT                                                              13

SEQ ID NO: 172          moltype = AA  length = 13
FEATURE                 Location/Qualifiers
source                  1..13
                        mol_type = protein
                        organism = synthetic construct
DISULFID                2..12
                        note = Cys-Cys
MOD_RES                 1
                        note = AcIle
SEQUENCE: 172
ICVVQDWGHH RCT                                                              13

SEQ ID NO: 173          moltype = AA  length = 13
FEATURE                 Location/Qualifiers
source                  1..13
                        mol_type = protein
                        organism = synthetic construct
MOD_RES                 1
                        note = AcIle
DISULFID                2..12
                        note = Cys-Cys
SEQUENCE: 173
ICVVQDWGAH RCT                                                              13

SEQ ID NO: 174          moltype = AA  length = 13
FEATURE                 Location/Qualifiers
source                  1..13
                        mol_type = protein
                        organism = synthetic construct
MOD_RES                 1
                        note = AcIle
DISULFID                2..12
                        note = Cys-Cys
SEQUENCE: 174
ICVTQDWGHH RCT                                                              13
```

-continued

```
SEQ ID NO: 175            moltype = AA  length = 13
FEATURE                   Location/Qualifiers
source                    1..13
                          mol_type = protein
                          organism = synthetic construct
MOD_RES                   1
                          note = AcIle
DISULFID                  2..12
                          note = Cys-Cys
SEQUENCE: 175
ICVSQDWGHH RCT                                                                     13

SEQ ID NO: 176            moltype = AA  length = 13
FEATURE                   Location/Qualifiers
source                    1..13
                          mol_type = protein
                          organism = synthetic construct
MOD_RES                   1
                          note = AcIle
DISULFID                  2..12
                          note = Cys-Cys
SEQUENCE: 176
ICVHQDWGHH RCT                                                                     13

SEQ ID NO: 177            moltype = AA  length = 13
FEATURE                   Location/Qualifiers
source                    1..13
                          mol_type = protein
                          organism = synthetic construct
MOD_RES                   1
                          note = AcIle
DISULFID                  2..12
                          note = Cys-Cys
SEQUENCE: 177
ICVFQDWGHH RCT                                                                     13

SEQ ID NO: 178            moltype = AA  length = 13
FEATURE                   Location/Qualifiers
source                    1..13
                          mol_type = protein
                          organism = unidentified
MOD_RES                   1
                          note = AcIle
DISULFID                  2..12
                          note = Cys-Cys
SEQUENCE: 178
ICVYQDWGAH RCT                                                                     13

SEQ ID NO: 179            moltype = AA  length = 13
FEATURE                   Location/Qualifiers
source                    1..13
                          mol_type = protein
                          organism = synthetic construct
MOD_RES                   1
                          note = AcIle
DISULFID                  2..12
                          note = Cys-Cys
SEQUENCE: 179
ICVWQDWGWH RCT                                                                     13

SEQ ID NO: 180            moltype = AA  length = 13
FEATURE                   Location/Qualifiers
source                    1..13
                          mol_type = protein
                          organism = synthetic construct
MOD_RES                   1
                          note = AcIle
DISULFID                  2..12
                          note = Cys-Cys
SEQUENCE: 180
ICVWQDWGHH RCT                                                                     13

SEQ ID NO: 181            moltype = AA  length = 13
FEATURE                   Location/Qualifiers
source                    1..13
                          mol_type = protein
                          organism = synthetic construct
MOD_RES                   1
                          note = AcIle
```

-continued

```
DISULFID                  2..12
                          note = Cys-Cys
SEQUENCE: 181
ICVWQDWGAH RCT                                                                 13

SEQ ID NO: 182            moltype = AA   length = 13
FEATURE                   Location/Qualifiers
source                    1..13
                          mol_type = protein
                          organism = synthetic construct
MOD_RES                   1
                          note = AcIle
DISULFID                  2..12
                          note = Cys-Cys
SEQUENCE: 182
ICVWQDWGAH RCT                                                                 13

SEQ ID NO: 183            moltype = AA   length = 13
FEATURE                   Location/Qualifiers
source                    1..13
                          mol_type = protein
                          organism = synthetic construct
MOD_RES                   1
                          note = AcIle
DISULFID                  2..12
                          note = Cys-Cys
SITE                      10
                          note = D-Amino Acid
SEQUENCE: 183
ICVWQDWGAH RCT                                                                 13

SEQ ID NO: 184            moltype = AA   length = 13
FEATURE                   Location/Qualifiers
source                    1..13
                          mol_type = protein
                          organism = synthetic construct
MOD_RES                   1
                          note = AcIle
DISULFID                  2..12
                          note = Cys-Cys
SITE                      9
                          note = D-Amino Acid
SEQUENCE: 184
ICVWQDWGAH RCT                                                                 13

SEQ ID NO: 185            moltype = AA   length = 13
FEATURE                   Location/Qualifiers
source                    1..13
                          mol_type = protein
                          organism = synthetic construct
MOD_RES                   1
                          note = AcIle
SITE                      1
                          note = D-Amino Acid
DISULFID                  2..12
                          note = Cys-Cys
SEQUENCE: 185
ICVWQDWGAH RCT                                                                 13

SEQ ID NO: 186            moltype = AA   length = 13
FEATURE                   Location/Qualifiers
source                    1..13
                          mol_type = protein
                          organism = synthetic construct
DISULFID                  2..12
                          note = Cys-Cys
MOD_RES                   1
                          note = AcIle
SITE                      13
                          note = D-Amino Acid
SEQUENCE: 186
ICVWQDWGAH RCT                                                                 13

SEQ ID NO: 187            moltype = AA   length = 13
FEATURE                   Location/Qualifiers
source                    1..13
                          mol_type = protein
                          organism = synthetic construct
DISULFID                  2..12
```

-continued

```
                     note = Cys-Cys
MOD_RES              1
                     note = Ac-Ile
SEQUENCE: 187
ICVWQDWGAH RCT                                                        13

SEQ ID NO: 188       moltype = AA  length = 13
FEATURE              Location/Qualifiers
source               1..13
                     mol_type = protein
                     organism = synthetic construct
DISULFID             2..12
                     note = Cys-Cys
SEQUENCE: 188
WCVWQDWGTN RCW                                                        13

SEQ ID NO: 189       moltype = AA  length = 13
FEATURE              Location/Qualifiers
source               1..13
                     mol_type = protein
                     organism = synthetic construct
MOD_RES              1
                     note = Ac-Asp
DISULFID             2..12
                     note = Cys-Cys
SEQUENCE: 189
DCVWQDWGTN KCW                                                        13

SEQ ID NO: 190       moltype = AA  length = 13
FEATURE              Location/Qualifiers
source               1..13
                     mol_type = protein
                     organism = synthetic construct
DISULFID             2..12
                     note = Cys-Cys
SEQUENCE: 190
QCVWQDWGQN QCW                                                        13

SEQ ID NO: 191       moltype = AA  length = 13
FEATURE              Location/Qualifiers
source               1..13
                     mol_type = protein
                     organism = synthetic construct
DISULFID             2..12
                     note = Cys-Cys
MOD_RES              1
                     note = AcIle
SEQUENCE: 191
ICVWQDWGAH RCW                                                        13

SEQ ID NO: 192       moltype = AA  length = 13
FEATURE              Location/Qualifiers
source               1..13
                     mol_type = protein
                     organism = synthetic construct
MOD_RES              1
                     note = AcTrp
DISULFID             2..12
                     note = Cys-Cys
SEQUENCE: 192
WCVWQDWGAH RCT                                                        13

SEQ ID NO: 193       moltype = AA  length = 13
FEATURE              Location/Qualifiers
source               1..13
                     mol_type = protein
                     organism = synthetic construct
MOD_RES              1
                     note = AcTrp
DISULFID             2..12
                     note = Cys-Cys
SEQUENCE: 193
WCVWQDWGAH RCW                                                        13

SEQ ID NO: 194       moltype = AA  length = 13
FEATURE              Location/Qualifiers
source               1..13
                     mol_type = protein
                     organism = synthetic construct
```

```
SITE                    12
                        note = Homocysteine
MOD_RES                 1
                        note = AcIle
CROSSLNK                2..12
                        note = Ala-Hcy
SEQUENCE: 194
IAVWQDWGAH RXT                                                              13

SEQ ID NO: 195          moltype = AA  length = 13
FEATURE                 Location/Qualifiers
source                  1..13
                        mol_type = protein
                        organism = synthetic construct
MOD_RES                 1
                        note = AcIle
DISULFID                2..12
                        note = Cys-Cys
MOD_RES                 13
                        note = MeIle
SEQUENCE: 195
ICVWQDWGAH RCI                                                              13

SEQ ID NO: 196          moltype = AA  length = 13
FEATURE                 Location/Qualifiers
source                  1..13
                        mol_type = protein
                        organism = synthetic construct
MOD_RES                 1
                        note = AcIle
DISULFID                2..12
                        note = Ala-Hcy
MOD_RES                 13
                        note = MeIle
SITE                    12
                        note = Homocysteine
SEQUENCE: 196
IAVWQDWGAH RXI                                                              13

SEQ ID NO: 197          moltype = AA  length = 13
FEATURE                 Location/Qualifiers
source                  1..13
                        mol_type = protein
                        organism = synthetic construct
MOD_RES                 1
                        note = AcIle
MOD_RES                 4
                        note = 5fTrp
SEQUENCE: 197
ICVWQDWGAH RCT                                                              13

SEQ ID NO: 198          moltype = AA  length = 13
FEATURE                 Location/Qualifiers
source                  1..13
                        mol_type = protein
                        organism = synthetic construct
MOD_RES                 1
                        note = AcIle
MOD_RES                 4
                        note = m5Trp
SEQUENCE: 198
ICVWQDWGAH RCT                                                              13

SEQ ID NO: 199          moltype = AA  length = 13
FEATURE                 Location/Qualifiers
source                  1..13
                        mol_type = protein
                        organism = synthetic construct
SITE                    4
                        note = Naphthylalanine
MOD_RES                 1
                        note = AcIle
SEQUENCE: 199
ICVXQDWGAH RCT                                                              13

SEQ ID NO: 200          moltype = AA  length = 13
FEATURE                 Location/Qualifiers
source                  1..13
                        mol_type = protein
```

-continued

```
                    organism = synthetic construct
MOD_RES             1
                    note = AcIle
MOD_RES             7
                    note = 5fTrp
SEQUENCE: 200
ICVWQDWGAH RCT                                                              13

SEQ ID NO: 201      moltype = AA   length = 13
FEATURE             Location/Qualifiers
source              1..13
                    mol_type = protein
                    organism = synthetic construct
MOD_RES             1
                    note = AcIle
MOD_RES             7
                    note = m5Trp
SEQUENCE: 201
ICVWQDWGAH RCT                                                              13

SEQ ID NO: 202      moltype = AA   length = 13
FEATURE             Location/Qualifiers
source              1..13
                    mol_type = protein
                    organism = synthetic construct
MOD_RES             1
                    note = AcIle
MOD_RES             7
                    note = MeTrp
SEQUENCE: 202
ICVWQDWGAH RCT                                                              13

SEQ ID NO: 203      moltype = AA   length = 13
FEATURE             Location/Qualifiers
source              1..13
                    mol_type = protein
                    organism = synthetic construct
MOD_RES             1
                    note = AcIle
SEQUENCE: 203
ICVYQDWGAH RCT                                                              13

SEQ ID NO: 204      moltype = AA   length = 13
FEATURE             Location/Qualifiers
source              1..13
                    mol_type = protein
                    organism = synthetic construct
MOD_RES             1
                    note = AcIle
SEQUENCE: 204
ICVWQDWGAH RCT                                                              13

SEQ ID NO: 205      moltype = AA   length = 13
FEATURE             Location/Qualifiers
source              1..13
                    mol_type = protein
                    organism = synthetic construct
MOD_RES             1
                    note = AcIle
SEQUENCE: 205
ICVWQDWGAH RCT                                                              13

SEQ ID NO: 206      moltype = AA   length = 13
FEATURE             Location/Qualifiers
source              1..13
                    mol_type = protein
                    organism = synthetic construct
MOD_RES             1
                    note = AcIle
SITE                13
                    note = D-Amino Acid
SEQUENCE: 206
ICVWQDWGAH RCT                                                              13

SEQ ID NO: 207      moltype = AA   length = 13
FEATURE             Location/Qualifiers
source              1..13
                    mol_type = protein
                    organism = synthetic construct
```

-continued

```
MOD_RES            1
                   note = AcIle
SITE               4
                   note = Naphthylalanine
SEQUENCE: 207
ICVXQDWGAH RCT                                                              13

SEQ ID NO: 208     moltype = AA  length = 13
FEATURE            Location/Qualifiers
source             1..13
                   mol_type = protein
                   organism = synthetic construct
MOD_RES            1
                   note = AcIle
SITE               4
                   note = Naphthylalanine
SEQUENCE: 208
ICVXQDWGAH RCT                                                              13

SEQ ID NO: 209     moltype = AA  length = 13
FEATURE            Location/Qualifiers
source             1..13
                   mol_type = protein
                   organism = synthetic construct
MOD_RES            1
                   note = AcIle
SITE               4
                   note = Naphthylalanine
SEQUENCE: 209
ICVXQDWGAH RCT                                                              13

SEQ ID NO: 210     moltype = AA  length = 13
FEATURE            Location/Qualifiers
source             1..13
                   mol_type = protein
                   organism = synthetic construct
MOD_RES            1
                   note = AcIle
SITE               4
                   note = Lysoalanine
SEQUENCE: 210
ICVXQDWGAH RCT                                                              13

SEQ ID NO: 211     moltype = AA  length = 13
FEATURE            Location/Qualifiers
source             1..13
                   mol_type = protein
                   organism = synthetic construct
MOD_RES            1
                   note = AcIle
SITE               4
                   note = Lysoalanine
SEQUENCE: 211
ICVXQDWGAH RCT                                                              13

SEQ ID NO: 212     moltype = AA  length = 13
FEATURE            Location/Qualifiers
source             1..13
                   mol_type = protein
                   organism = synthetic construct
MOD_RES            1
                   note = AcIle
MOD_RES            5
                   note = htQ
SEQUENCE: 212
ICVDQDWGAH RCT                                                              13

SEQ ID NO: 213     moltype = AA  length = 13
FEATURE            Location/Qualifiers
source             1..13
                   mol_type = protein
                   organism = synthetic construct
MOD_RES            1
                   note = AcIle
SITE               4
                   note = Boa
SEQUENCE: 213
ICVXQDWGAH RCT                                                              13
```

```
SEQ ID NO: 214          moltype = AA  length = 13
FEATURE                 Location/Qualifiers
source                  1..13
                        mol_type = protein
                        organism = synthetic construct
MOD_RES                 1
                        note = AcIle
SITE                    4
                        note = 4-Benzoylphenylalanine
SEQUENCE: 214
ICVXQDWGAH RCT                                                              13

SEQ ID NO: 215          moltype = AA  length = 13
FEATURE                 Location/Qualifiers
source                  1..13
                        mol_type = protein
                        organism = synthetic construct
MOD_RES                 1
                        note = AcIle
SITE                    4
                        note = L-3-Benzothienylalanine
SEQUENCE: 215
ICVXQDWGAH RCT                                                              13

SEQ ID NO: 216          moltype = AA  length = 13
FEATURE                 Location/Qualifiers
source                  1..13
                        mol_type = protein
                        organism = synthetic construct
MOD_RES                 1
                        note = AcIle
SITE                    4
                        note = L-3-Benzothienylalanine
SEQUENCE: 216
ICVXQDWGAH RCT                                                              13

SEQ ID NO: 217          moltype = AA  length = 13
FEATURE                 Location/Qualifiers
source                  1..13
                        mol_type = protein
                        organism = synthetic construct
MOD_RES                 1
                        note = AcIle
SITE                    9
                        note = Abu
SEQUENCE: 217
ICVWQDWGXH RCT                                                              13

SEQ ID NO: 218          moltype = AA  length = 16
FEATURE                 Location/Qualifiers
source                  1..16
                        mol_type = protein
                        organism = synthetic construct
MOD_RES                 1
                        note = H-Gly
SEQUENCE: 218
GICVWQDWGA HRCTAN                                                           16

SEQ ID NO: 219          moltype = AA  length = 13
FEATURE                 Location/Qualifiers
source                  1..13
                        mol_type = protein
                        organism = synthetic construct
MOD_RES                 1
                        note = AcIle
MOD_RES                 4
                        note = 5fTrp
SEQUENCE: 219
ICVWQDWGAH RCT                                                              13

SEQ ID NO: 220          moltype = AA  length = 13
FEATURE                 Location/Qualifiers
source                  1..13
                        mol_type = protein
                        organism = synthetic construct
MOD_RES                 1
                        note = AcIle
MOD_RES                 4
                        note = m5Trp
```

-continued

```
SEQUENCE: 220
ICVWQDWGAH RCT                                                           13

SEQ ID NO: 221          moltype = AA  length = 13
FEATURE                 Location/Qualifiers
source                  1..13
                        mol_type = protein
                        organism = synthetic construct
MOD_RES                 1
                        note = AcIle
MOD_RES                 4
                        note = MeTrp
SEQUENCE: 221
ICVWQDWGAH RCT                                                           13

SEQ ID NO: 222          moltype = AA  length = 13
FEATURE                 Location/Qualifiers
source                  1..13
                        mol_type = protein
                        organism = synthetic construct
MOD_RES                 1
                        note = AcIle
MOD_RES                 4
                        note = 5fTrp
SEQUENCE: 222
ICVWQDWGAH RCT                                                           13

SEQ ID NO: 223          moltype = AA  length = 13
FEATURE                 Location/Qualifiers
source                  1..13
                        mol_type = protein
                        organism = synthetic construct
MOD_RES                 1
                        note = AcIle
MOD_RES                 4
                        note = 5fTrp
MOD_RES                 7
                        note = 5fTrp
SEQUENCE: 223
ICVWQDWGAH RCT                                                           13

SEQ ID NO: 224          moltype = AA  length = 13
FEATURE                 Location/Qualifiers
source                  1..13
                        mol_type = protein
                        organism = synthetic construct
MOD_RES                 1
                        note = AcIle
MOD_RES                 4
                        note = m5Trp
MOD_RES                 7
                        note = 5fTrp
SEQUENCE: 224
ICVWQDWGAH RCT                                                           13

SEQ ID NO: 225          moltype = AA  length = 13
FEATURE                 Location/Qualifiers
source                  1..13
                        mol_type = protein
                        organism = synthetic construct
MOD_RES                 1
                        note = AcIle
MOD_RES                 4
                        note = MeTrp
MOD_RES                 7
                        note = 5fTrp
SEQUENCE: 225
ICVWQDWGAH RCT                                                           13

SEQ ID NO: 226          moltype = AA  length = 15
FEATURE                 Location/Qualifiers
source                  1..15
                        mol_type = protein
                        organism = synthetic construct
MOD_RES                 1
                        note = H-Gly
MOD_RES                 4
                        note = 6fTrp
MOD_RES                 7
```

-continued

```
                        note = 6fTrp
SEQUENCE: 226
GICVWQDWGA HRCTN                                                15

SEQ ID NO: 227          moltype = AA   length = 13
FEATURE                 Location/Qualifiers
source                  1..13
                        mol_type = protein
                        organism = synthetic construct
MOD_RES                 1
                        note = AcIle
MOD_RES                 4
                        note = 1-formylTrp
SEQUENCE: 227
ICVWQDWGAH RCT                                                  13

SEQ ID NO: 228          moltype = AA   length = 13
FEATURE                 Location/Qualifiers
source                  1..13
                        mol_type = protein
                        organism = synthetic construct
MOD_RES                 1
                        note = AcIle
MOD_RES                 4
                        note = 1-methyoxyTrp
SEQUENCE: 228
ICVWQDWGAH RCT                                                  13

SEQ ID NO: 229          moltype = AA   length = 15
FEATURE                 Location/Qualifiers
source                  1..15
                        mol_type = protein
                        organism = synthetic construct
MOD_RES                 1
                        note = H-Gly
MOD_RES                 5
                        note = 5fTrp
MOD_RES                 7
                        note = 5fTrp
SEQUENCE: 229
GICVWQDWGA HRCTN                                                15

SEQ ID NO: 230          moltype = AA   length = 7
FEATURE                 Location/Qualifiers
source                  1..7
                        mol_type = protein
                        organism = synthetic construct
MOD_RES                 1
                        note = AcAla
SEQUENCE: 230
AEAKAKA                                                         7

SEQ ID NO: 231          moltype = AA   length = 15
FEATURE                 Location/Qualifiers
source                  1..15
                        mol_type = protein
                        organism = synthetic construct
SEQUENCE: 231
IALILEPICC QERAA                                                15

SEQ ID NO: 232          moltype = AA   length = 15
FEATURE                 Location/Qualifiers
source                  1..15
                        mol_type = protein
                        organism = synthetic construct
SEQUENCE: 232
IALILEPICC QERAA                                                15

SEQ ID NO: 233          moltype = AA   length = 15
FEATURE                 Location/Qualifiers
source                  1..15
                        mol_type = protein
                        organism = synthetic construct
SEQUENCE: 233
IALILEPICC QERAA                                                15

SEQ ID NO: 234          moltype = AA   length = 15
FEATURE                 Location/Qualifiers
source                  1..15
```

```
                        mol_type = protein
                        organism = synthetic construct
SEQUENCE: 234
RALILEPICC QERAA                                                           15

SEQ ID NO: 235          moltype = AA  length = 15
FEATURE                 Location/Qualifiers
source                  1..15
                        mol_type = protein
                        organism = synthetic construct
SEQUENCE: 235
IRLILEPICC QERAA                                                           15

SEQ ID NO: 236          moltype = AA  length = 15
FEATURE                 Location/Qualifiers
source                  1..15
                        mol_type = protein
                        organism = synthetic construct
SEQUENCE: 236
IARILEPICC QERAA                                                           15

SEQ ID NO: 237          moltype = AA  length = 15
FEATURE                 Location/Qualifiers
source                  1..15
                        mol_type = protein
                        organism = synthetic construct
SEQUENCE: 237
IALIREPICC QERAA                                                           15

SEQ ID NO: 238          moltype = AA  length = 15
FEATURE                 Location/Qualifiers
source                  1..15
                        mol_type = protein
                        organism = synthetic construct
SEQUENCE: 238
IALILEPICC RERAA                                                           15

SEQ ID NO: 239          moltype = AA  length = 15
FEATURE                 Location/Qualifiers
source                  1..15
                        mol_type = protein
                        organism = synthetic construct
SEQUENCE: 239
IALILEPICC QRRAA                                                           15

SEQ ID NO: 240          moltype = AA  length = 15
FEATURE                 Location/Qualifiers
source                  1..15
                        mol_type = protein
                        organism = synthetic construct
SEQUENCE: 240
IELILEPICC QERAA                                                           15

SEQ ID NO: 241          moltype = AA  length = 15
FEATURE                 Location/Qualifiers
source                  1..15
                        mol_type = protein
                        organism = synthetic construct
SEQUENCE: 241
IAEILEPICC QERAA                                                           15

SEQ ID NO: 242          moltype = AA  length = 15
FEATURE                 Location/Qualifiers
source                  1..15
                        mol_type = protein
                        organism = synthetic construct
SEQUENCE: 242
IALILEPICC QEEAA                                                           15

SEQ ID NO: 243          moltype = AA  length = 15
FEATURE                 Location/Qualifiers
source                  1..15
                        mol_type = protein
                        organism = synthetic construct
SEQUENCE: 243
IALILEPICC QEREA                                                           15

SEQ ID NO: 244          moltype = AA  length = 15
FEATURE                 Location/Qualifiers
```

```
source                        1..15
                              mol_type = protein
                              organism = synthetic construct
SEQUENCE: 244
IALILEEICC QERAA                                                               15

SEQ ID NO: 245                moltype = AA   length = 15
FEATURE                       Location/Qualifiers
source                        1..15
                              mol_type = protein
                              organism = synthetic construct
SEQUENCE: 245
IALILEPECC QERAA                                                               15

SEQ ID NO: 246                moltype = AA   length = 30
FEATURE                       Location/Qualifiers
source                        1..30
                              mol_type = protein
                              organism = synthetic construct
SEQUENCE: 246
PAICQRATAT LGTVGSNTSG TTAIEACILL                                                30

SEQ ID NO: 247                moltype = AA   length = 15
FEATURE                       Location/Qualifiers
source                        1..15
                              mol_type = protein
                              organism = synthetic construct
DISULFID                      1..12
                              note = Cys-Cys
SEQUENCE: 247
CEGPFGPRHD LTFCW                                                               15

SEQ ID NO: 248                moltype = AA   length = 15
FEATURE                       Location/Qualifiers
source                        1..15
                              mol_type = protein
                              organism = synthetic construct
SITE                          1
                              note = Xb
DISULFID                      1..12
                              note = Xb-Cys
SEQUENCE: 248
XEGPFGPRHD LTFCW                                                               15

SEQ ID NO: 249                moltype = AA   length = 7
FEATURE                       Location/Qualifiers
source                        1..7
                              mol_type = protein
                              organism = synthetic construct
SEQUENCE: 249
QYYPFSX                                                                         7

SEQ ID NO: 250                moltype = AA   length = 7
FEATURE                       Location/Qualifiers
source                        1..7
                              mol_type = protein
                              organism = synthetic construct
SEQUENCE: 250
NPFNLAR                                                                         7

SEQ ID NO: 251                moltype = AA   length = 12
FEATURE                       Location/Qualifiers
source                        1..12
                              mol_type = protein
                              organism = synthetic construct
SEQUENCE: 251
QLQDMTSSPF WL                                                                  12

SEQ ID NO: 252                moltype = AA   length = 12
FEATURE                       Location/Qualifiers
source                        1..12
                              mol_type = protein
                              organism = synthetic construct
SEQUENCE: 252
NPFVIGRWHP PH                                                                  12

SEQ ID NO: 253                moltype = AA   length = 12
FEATURE                       Location/Qualifiers
source                        1..12
```

-continued

```
                        mol_type = protein
                        organism = synthetic construct
SEQUENCE: 253
SLAKFLNPFL YR                                                           12

SEQ ID NO: 254          moltype = AA   length = 12
FEATURE                 Location/Qualifiers
source                  1..12
                        mol_type = protein
                        organism = synthetic construct
SEQUENCE: 254
ASTPRFEPFQ LD                                                           12

SEQ ID NO: 255          moltype = AA   length = 12
FEATURE                 Location/Qualifiers
source                  1..12
                        mol_type = protein
                        organism = synthetic construct
SEQUENCE: 255
SLHSQPYSPF ML                                                           12

SEQ ID NO: 256          moltype = AA   length = 12
FEATURE                 Location/Qualifiers
source                  1..12
                        mol_type = protein
                        organism = synthetic construct
SEQUENCE: 256
NILSSWSSPF VF                                                           12

SEQ ID NO: 257          moltype = AA   length = 12
FEATURE                 Location/Qualifiers
source                  1..12
                        mol_type = protein
                        organism = synthetic construct
SEQUENCE: 257
NLPSSWTNPF YL                                                           12

SEQ ID NO: 258          moltype = AA   length = 7
FEATURE                 Location/Qualifiers
source                  1..7
                        mol_type = protein
                        organism = synthetic construct
SEQUENCE: 258
SPFMLHP                                                                  7

SEQ ID NO: 259          moltype = AA   length = 7
FEATURE                 Location/Qualifiers
source                  1..7
                        mol_type = protein
                        organism = synthetic construct
SEQUENCE: 259
PSPFMLT                                                                  7

SEQ ID NO: 260          moltype = AA   length = 7
FEATURE                 Location/Qualifiers
source                  1..7
                        mol_type = protein
                        organism = synthetic construct
SEQUENCE: 260
IGPFHLH                                                                  7

SEQ ID NO: 261          moltype = AA   length = 7
FEATURE                 Location/Qualifiers
source                  1..7
                        mol_type = protein
                        organism = synthetic construct
SEQUENCE: 261
TNPFMLN                                                                  7

SEQ ID NO: 262          moltype = AA   length = 7
FEATURE                 Location/Qualifiers
source                  1..7
                        mol_type = protein
                        organism = synthetic construct
SEQUENCE: 262
NTTFLYP                                                                  7

SEQ ID NO: 263          moltype = AA   length = 7
FEATURE                 Location/Qualifiers
```

-continued

```
source                  1..7
                        mol_type = protein
                        organism = synthetic construct
SEQUENCE: 263
SHYTQYL                                                                   7

SEQ ID NO: 264          moltype = AA   length = 7
FEATURE                 Location/Qualifiers
source                  1..7
                        mol_type = protein
                        organism = synthetic construct
SEQUENCE: 264
NHHPNYW                                                                   7

SEQ ID NO: 265          moltype = AA   length = 7
FEATURE                 Location/Qualifiers
source                  1..7
                        mol_type = protein
                        organism = synthetic construct
SEQUENCE: 265
VHYPLSW                                                                   7

SEQ ID NO: 266          moltype = AA   length = 12
FEATURE                 Location/Qualifiers
source                  1..12
                        mol_type = protein
                        organism = synthetic construct
SEQUENCE: 266
HHLKYSDTSP PI                                                            12

SEQ ID NO: 267          moltype = AA   length = 13
FEATURE                 Location/Qualifiers
source                  1..13
                        mol_type = protein
                        organism = synthetic construct
SEQUENCE: 267
SHMHERWDTS PPI                                                           13

SEQ ID NO: 268          moltype = AA   length = 12
FEATURE                 Location/Qualifiers
source                  1..12
                        mol_type = protein
                        organism = synthetic construct
SEQUENCE: 268
SHMHERWDTS YQ                                                            12

SEQ ID NO: 269          moltype = AA   length = 12
FEATURE                 Location/Qualifiers
source                  1..12
                        mol_type = protein
                        organism = synthetic construct
SEQUENCE: 269
SHIHSNAAWR IT                                                            12

SEQ ID NO: 270          moltype = AA   length = 7
FEATURE                 Location/Qualifiers
source                  1..7
                        mol_type = protein
                        organism = synthetic construct
SEQUENCE: 270
WHYPHWQ                                                                   7

SEQ ID NO: 271          moltype = AA   length = 7
FEATURE                 Location/Qualifiers
source                  1..7
                        mol_type = protein
                        organism = synthetic construct
SEQUENCE: 271
SHYLYTQ                                                                   7

SEQ ID NO: 272          moltype = AA   length = 7
FEATURE                 Location/Qualifiers
source                  1..7
                        mol_type = protein
                        organism = synthetic construct
SEQUENCE: 272
AHYSFTQ                                                                   7

SEQ ID NO: 273          moltype = AA   length = 7
```

```
                            -continued
FEATURE              Location/Qualifiers
source               1..7
                     mol_type = protein
                     organism = synthetic construct
SEQUENCE: 273
THYPTFY                                                              7

SEQ ID NO: 274       moltype = AA  length = 7
FEATURE              Location/Qualifiers
source               1..7
                     mol_type = protein
                     organism = synthetic construct
SEQUENCE: 274
EHNTSFW                                                              7

SEQ ID NO: 275       moltype = AA  length = 7
FEATURE              Location/Qualifiers
source               1..7
                     mol_type = protein
                     organism = synthetic construct
SEQUENCE: 275
NHYKLTW                                                              7

SEQ ID NO: 276       moltype = AA  length = 7
FEATURE              Location/Qualifiers
source               1..7
                     mol_type = protein
                     organism = synthetic construct
SEQUENCE: 276
NHSPYFQ                                                              7

SEQ ID NO: 277       moltype = AA  length = 7
FEATURE              Location/Qualifiers
source               1..7
                     mol_type = protein
                     organism = synthetic construct
SEQUENCE: 277
SHYQHYQ                                                              7

SEQ ID NO: 278       moltype = AA  length = 30
FEATURE              Location/Qualifiers
source               1..30
                     mol_type = protein
                     organism = synthetic construct
SEQUENCE: 278
PAICQRATAT LGTVGSNTSG TTEIEACILL                                    30

SEQ ID NO: 279       moltype = AA  length = 10
FEATURE              Location/Qualifiers
source               1..10
                     mol_type = protein
                     organism = synthetic construct
SEQUENCE: 279
WLGLGGGYGW                                                          10

SEQ ID NO: 280       moltype = AA  length = 15
FEATURE              Location/Qualifiers
source               1..15
                     mol_type = protein
                     organism = synthetic construct
SEQUENCE: 280
FYGPPFLNDS LRGIW                                                    15

SEQ ID NO: 281       moltype = AA  length = 15
FEATURE              Location/Qualifiers
source               1..15
                     mol_type = protein
                     organism = synthetic construct
SEQUENCE: 281
LRFLNPFSLD GSGFW                                                    15

SEQ ID NO: 282       moltype = AA  length = 15
FEATURE              Location/Qualifiers
source               1..15
                     mol_type = protein
                     organism = synthetic construct
SEQUENCE: 282
HSPFCLGVLE CFGLV                                                    15
```

-continued

| | | |
|---|---|---|
| SEQ ID NO: 283<br>FEATURE<br>source | moltype = AA   length = 15<br>Location/Qualifiers<br>1..15<br>mol_type = protein<br>organism = synthetic construct | |
| SEQUENCE: 283<br>TCGAFYLYHD PFICG | | 15 |
| SEQ ID NO: 284<br>FEATURE<br>source | moltype = AA   length = 15<br>Location/Qualifiers<br>1..15<br>mol_type = protein<br>organism = synthetic construct | |
| SEQUENCE: 284<br>MQHCLASHEL YLPWC | | 15 |
| SEQ ID NO: 285<br>FEATURE<br>source | moltype = AA   length = 15<br>Location/Qualifiers<br>1..15<br>mol_type = protein<br>organism = synthetic construct | |
| SEQUENCE: 285<br>FFVFGSGDAF AFSDM | | 15 |
| SEQ ID NO: 286<br>FEATURE<br>source | moltype = AA   length = 15<br>Location/Qualifiers<br>1..15<br>mol_type = protein<br>organism = synthetic construct | |
| SEQUENCE: 286<br>PCVIIDTGSS RWCYL | | 15 |
| SEQ ID NO: 287<br>FEATURE<br>source | moltype = AA   length = 15<br>Location/Qualifiers<br>1..15<br>mol_type = protein<br>organism = synthetic construct | |
| SEQUENCE: 287<br>HSPFCLGVLE CFGLV | | 15 |
| SEQ ID NO: 288<br>FEATURE<br>source | moltype = AA   length = 15<br>Location/Qualifiers<br>1..15<br>mol_type = protein<br>organism = synthetic construct | |
| SEQUENCE: 288<br>HAAFEPRGDV RHTLL | | 15 |
| SEQ ID NO: 289<br>FEATURE<br>source | moltype = AA   length = 12<br>Location/Qualifiers<br>1..12<br>mol_type = protein<br>organism = synthetic construct | |
| SEQUENCE: 289<br>CRWDGSWGEV RC | | 12 |
| SEQ ID NO: 290<br>FEATURE<br>source | moltype = AA   length = 12<br>Location/Qualifiers<br>1..12<br>mol_type = protein<br>organism = synthetic construct | |
| SEQUENCE: 290<br>CYWVGTWGEA VC | | 12 |
| SEQ ID NO: 291<br>FEATURE<br>source | moltype = AA   length = 16<br>Location/Qualifiers<br>1..16<br>mol_type = protein<br>organism = synthetic construct | |
| SEQUENCE: 291<br>RWFPCPNKEG CCSISV | | 16 |
| SEQ ID NO: 292<br>FEATURE<br>source | moltype = AA   length = 16<br>Location/Qualifiers<br>1..16<br>mol_type = protein<br>organism = synthetic construct | |
| SEQUENCE: 292<br>RSTYCNKNKD SCHIPE | | 16 |

-continued

```
SEQ ID NO: 293            moltype = AA  length = 16
FEATURE                   Location/Qualifiers
source                    1..16
                          mol_type = protein
                          organism = synthetic construct
SEQUENCE: 293
QPPQCIKDGG FVICRV                                                          16

SEQ ID NO: 294            moltype = AA  length = 16
FEATURE                   Location/Qualifiers
source                    1..16
                          mol_type = protein
                          organism = synthetic construct
SEQUENCE: 294
KGKKCKPEEH PCNEPM                                                          16

SEQ ID NO: 295            moltype = AA  length = 16
FEATURE                   Location/Qualifiers
source                    1..16
                          mol_type = protein
                          organism = synthetic construct
SEQUENCE: 295
NKMTCSDDGK LCWEHL                                                          16

SEQ ID NO: 296            moltype = AA  length = 14
FEATURE                   Location/Qualifiers
source                    1..14
                          mol_type = protein
                          organism = synthetic construct
SEQUENCE: 296
PLGRPCPTCP LAPS                                                            14

SEQ ID NO: 297            moltype = AA  length = 14
FEATURE                   Location/Qualifiers
source                    1..14
                          mol_type = protein
                          organism = synthetic construct
SEQUENCE: 297
QRMRPCPSCP LAPW                                                            14

SEQ ID NO: 298            moltype = AA  length = 14
FEATURE                   Location/Qualifiers
source                    1..14
                          mol_type = protein
                          organism = synthetic construct
SEQUENCE: 298
WPSRPCPSCP EVPP                                                            14

SEQ ID NO: 299            moltype = AA  length = 14
FEATURE                   Location/Qualifiers
source                    1..14
                          mol_type = protein
                          organism = synthetic construct
SEQUENCE: 299
SCTKDCPTCP LVPV                                                            14

SEQ ID NO: 300            moltype = AA  length = 15
FEATURE                   Location/Qualifiers
source                    1..15
                          mol_type = protein
                          organism = synthetic construct
SEQUENCE: 300
IALILEPICC QERAA                                                           15

SEQ ID NO: 301            moltype = AA  length = 30
FEATURE                   Location/Qualifiers
source                    1..30
                          mol_type = protein
                          organism = synthetic construct
SEQUENCE: 301
PAICQRATAT LGTVGSNTSG TTEIEACILL                                           30

SEQ ID NO: 302            moltype = AA  length = 30
FEATURE                   Location/Qualifiers
source                    1..30
                          mol_type = protein
                          organism = synthetic construct
SEQUENCE: 302
```

-continued

```
PAIAQRATAT LGTVGSNTSG TTEIEACILL                                              30

SEQ ID NO: 303          moltype = AA  length = 30
FEATURE                 Location/Qualifiers
source                  1..30
                        mol_type = protein
                        organism = synthetic construct
SEQUENCE: 303
PAICQRATAT LGTVGSNTSG TTEIEAAILL                                              30

SEQ ID NO: 304          moltype = AA  length = 30
FEATURE                 Location/Qualifiers
source                  1..30
                        mol_type = protein
                        organism = synthetic construct
SEQUENCE: 304
PAICQRATAT LGTVGSNTSG TTAIEACILL                                              30

SEQ ID NO: 305          moltype = AA  length = 30
FEATURE                 Location/Qualifiers
source                  1..30
                        mol_type = protein
                        organism = synthetic construct
SEQUENCE: 305
PAICQRATAT LGTVGSNTSG TTEIAACILL                                              30

SEQ ID NO: 306          moltype = AA  length = 15
FEATURE                 Location/Qualifiers
source                  1..15
                        mol_type = protein
                        organism = synthetic construct
SEQUENCE: 306
PAICQRAEIE ACILL                                                              15

SEQ ID NO: 307          moltype = AA  length = 15
FEATURE                 Location/Qualifiers
source                  1..15
                        mol_type = protein
                        organism = synthetic construct
SEQUENCE: 307
PAICQRAEIE ACILL                                                              15

SEQ ID NO: 308          moltype = AA  length = 15
FEATURE                 Location/Qualifiers
source                  1..15
                        mol_type = protein
                        organism = synthetic construct
SEQUENCE: 308
PAIAQRAEIE AAILL                                                              15

SEQ ID NO: 309          moltype = AA  length = 15
FEATURE                 Location/Qualifiers
source                  1..15
                        mol_type = protein
                        organism = synthetic construct
SEQUENCE: 309
IALILEPICC QERAA                                                              15

SEQ ID NO: 310          moltype = AA  length = 27
FEATURE                 Location/Qualifiers
source                  1..27
                        mol_type = protein
                        organism = synthetic construct
SEQUENCE: 310
PAICQRATAT LGTNTSGTTE IEACILL                                                 27

SEQ ID NO: 311          moltype = AA  length = 23
FEATURE                 Location/Qualifiers
source                  1..23
                        mol_type = protein
                        organism = synthetic construct
SEQUENCE: 311
PAICQRATAT LSGTTEIEAC ILL                                                     23

SEQ ID NO: 312          moltype = AA  length = 19
FEATURE                 Location/Qualifiers
source                  1..19
                        mol_type = protein
                        organism = synthetic construct
```

-continued

```
SEQUENCE: 312
PAICQRATAT TEIEACILL                                              19

SEQ ID NO: 313          moltype = AA  length = 15
FEATURE                 Location/Qualifiers
source                  1..15
                        mol_type = protein
                        organism = synthetic construct
SEQUENCE: 313
PAICQRAEIE ACILL                                                  15

SEQ ID NO: 314          moltype = AA  length = 29
FEATURE                 Location/Qualifiers
source                  1..29
                        mol_type = protein
                        organism = synthetic construct
SEQUENCE: 314
AICQRATATL GTVGSNTSGT TEIEACILL                                   29

SEQ ID NO: 315          moltype = AA  length = 28
FEATURE                 Location/Qualifiers
source                  1..28
                        mol_type = protein
                        organism = synthetic construct
SEQUENCE: 315
ICQRATATLG TVGSNTSGTT EIEACILL                                    28

SEQ ID NO: 316          moltype = AA  length = 27
FEATURE                 Location/Qualifiers
source                  1..27
                        mol_type = protein
                        organism = synthetic construct
SEQUENCE: 316
CQRATATLGT VGSNTSGTTE IEACILL                                     27

SEQ ID NO: 317          moltype = AA  length = 29
FEATURE                 Location/Qualifiers
source                  1..29
                        mol_type = protein
                        organism = synthetic construct
SEQUENCE: 317
PAICQRATAT LGTVGSNTSG TTEIEACIL                                   29

SEQ ID NO: 318          moltype = AA  length = 28
FEATURE                 Location/Qualifiers
source                  1..28
                        mol_type = protein
                        organism = synthetic construct
SEQUENCE: 318
PAICQRATAT LGTVGSNTSG TTEIEACI                                    28

SEQ ID NO: 319          moltype = AA  length = 27
FEATURE                 Location/Qualifiers
source                  1..27
                        mol_type = protein
                        organism = synthetic construct
SEQUENCE: 319
PAICQRATAT LGTVGSNTSG TTEIEAC                                     27

SEQ ID NO: 320          moltype = AA  length = 15
FEATURE                 Location/Qualifiers
source                  1..15
                        mol_type = protein
                        organism = synthetic construct
MOD_RES                 1
                        note = AcIle
SEQUENCE: 320
IALILEPICC QERAA                                                  15

SEQ ID NO: 321          moltype = AA  length = 30
FEATURE                 Location/Qualifiers
source                  1..30
                        mol_type = protein
                        organism = synthetic construct
MOD_RES                 1
                        note = AcPro
SEQUENCE: 321
PAICQRATAT LGTVGSNTSG TTEIEACILL                                  30
```

```
SEQ ID NO: 322          moltype = AA   length = 30
FEATURE                 Location/Qualifiers
source                  1..30
                        mol_type = protein
                        organism = synthetic construct
MOD_RES                 1
                        note = AcPro
SEQUENCE: 322
PAIAQRATAT LGTVGSNTSG TTEIEACILL                                      30

SEQ ID NO: 323          moltype = AA   length = 30
FEATURE                 Location/Qualifiers
source                  1..30
                        mol_type = protein
                        organism = synthetic construct
MOD_RES                 1
                        note = AcPro
SEQUENCE: 323
PAICQRATAT LGTVGSNTSG TTEIEAAILL                                      30

SEQ ID NO: 324          moltype = AA   length = 30
FEATURE                 Location/Qualifiers
source                  1..30
                        mol_type = protein
                        organism = synthetic construct
MOD_RES                 1
                        note = AcPro
SEQUENCE: 324
PAICQRATAT LGTVGSNTSG TTAIEACILL                                      30

SEQ ID NO: 325          moltype = AA   length = 30
FEATURE                 Location/Qualifiers
source                  1..30
                        mol_type = protein
                        organism = synthetic construct
MOD_RES                 1
                        note = AcPro
SEQUENCE: 325
PAICQRATAT LGTVGSNTSG TTEIAACILL                                      30

SEQ ID NO: 326          moltype = AA   length = 15
FEATURE                 Location/Qualifiers
source                  1..15
                        mol_type = protein
                        organism = synthetic construct
MOD_RES                 1
                        note = AcPro
SEQUENCE: 326
PAICQRAEIE ACILL                                                      15

SEQ ID NO: 327          moltype = AA   length = 15
FEATURE                 Location/Qualifiers
source                  1..15
                        mol_type = protein
                        organism = synthetic construct
MOD_RES                 1
                        note = AcPro
SEQUENCE: 327
PAICQRAEIE ACILL                                                      15

SEQ ID NO: 328          moltype = AA   length = 15
FEATURE                 Location/Qualifiers
source                  1..15
                        mol_type = protein
                        organism = synthetic construct
MOD_RES                 1
                        note = AcPro
SEQUENCE: 328
PAIAQRAEIE AAILL                                                      15

SEQ ID NO: 329          moltype = AA   length = 15
FEATURE                 Location/Qualifiers
source                  1..15
                        mol_type = protein
                        organism = synthetic construct
MOD_RES                 1
                        note = AcIle
SEQUENCE: 329
IALILEPICC QERAA                                                      15
```

```
SEQ ID NO: 330         moltype = AA  length = 27
FEATURE                Location/Qualifiers
source                 1..27
                       mol_type = protein
                       organism = synthetic construct
MOD_RES                1
                       note = AcPro
SEQUENCE: 330
PAICQRATAT LGTNTSGTTE IEACILL                                          27

SEQ ID NO: 331         moltype = AA  length = 23
FEATURE                Location/Qualifiers
source                 1..23
                       mol_type = protein
                       organism = synthetic construct
MOD_RES                1
                       note = AcPro
SEQUENCE: 331
PAICQRATAT LSGTTEIEAC ILL                                              23

SEQ ID NO: 332         moltype = AA  length = 19
FEATURE                Location/Qualifiers
source                 1..19
                       mol_type = protein
                       organism = synthetic construct
MOD_RES                1
                       note = AcPro
SEQUENCE: 332
PAICQRATAT TEIEACILL                                                   19

SEQ ID NO: 333         moltype = AA  length = 15
FEATURE                Location/Qualifiers
source                 1..15
                       mol_type = protein
                       organism = synthetic construct
MOD_RES                1
                       note = AcPro
SEQUENCE: 333
PAICQRAEIE ACILL                                                       15

SEQ ID NO: 334         moltype = AA  length = 29
FEATURE                Location/Qualifiers
source                 1..29
                       mol_type = protein
                       organism = synthetic construct
MOD_RES                1
                       note = AcAla
SEQUENCE: 334
AICQRATATL GTVGSNTSGT TEIEACILL                                        29

SEQ ID NO: 335         moltype = AA  length = 28
FEATURE                Location/Qualifiers
source                 1..28
                       mol_type = protein
                       organism = synthetic construct
MOD_RES                1
                       note = AcIle
SEQUENCE: 335
ICQRATATLG TVGSNTSGTT EIEACILL                                         28

SEQ ID NO: 336         moltype = AA  length = 27
FEATURE                Location/Qualifiers
source                 1..27
                       mol_type = protein
                       organism = synthetic construct
MOD_RES                1
                       note = AcCys
SEQUENCE: 336
CQRATATLGT VGSNTSGTTE IEACILL                                          27

SEQ ID NO: 337         moltype = AA  length = 29
FEATURE                Location/Qualifiers
source                 1..29
                       mol_type = protein
                       organism = synthetic construct
MOD_RES                1
                       note = AcPro
SEQUENCE: 337
```

-continued

```
PAICQRATAT LGTVGSNTSG TTEIEACIL                                      29

SEQ ID NO: 338          moltype = AA   length = 28
FEATURE                 Location/Qualifiers
source                  1..28
                        mol_type = protein
                        organism = synthetic construct
MOD_RES                 1
                        note = AcPro
SEQUENCE: 338
PAICQRATAT LGTVGSNTSG TTEIEACI                                       28

SEQ ID NO: 339          moltype = AA   length = 27
FEATURE                 Location/Qualifiers
source                  1..27
                        mol_type = protein
                        organism = synthetic construct
MOD_RES                 1
                        note = AcPro
SEQUENCE: 339
PAICQRATAT LGTVGSNTSG TTEIEAC                                        27

SEQ ID NO: 340          moltype = AA   length = 15
FEATURE                 Location/Qualifiers
source                  1..15
                        mol_type = protein
                        organism = synthetic construct
SEQUENCE: 340
IVVTAPADLW DWIRA                                                     15

SEQ ID NO: 341          moltype = AA   length = 15
FEATURE                 Location/Qualifiers
source                  1..15
                        mol_type = protein
                        organism = synthetic construct
SEQUENCE: 341
ITVTMPADLW DWIRA                                                     15

SEQ ID NO: 342          moltype = AA   length = 15
FEATURE                 Location/Qualifiers
source                  1..15
                        mol_type = protein
                        organism = synthetic construct
SEQUENCE: 342
IVVTIPADLW DWIRA                                                     15

SEQ ID NO: 343          moltype = AA   length = 15
FEATURE                 Location/Qualifiers
source                  1..15
                        mol_type = protein
                        organism = synthetic construct
SEQUENCE: 343
IVVTLPADLW DWIRA                                                     15

SEQ ID NO: 344          moltype = AA   length = 15
FEATURE                 Location/Qualifiers
source                  1..15
                        mol_type = protein
                        organism = synthetic construct
SEQUENCE: 344
IVVTVPADLW DWIRA                                                     15

SEQ ID NO: 345          moltype = AA   length = 15
FEATURE                 Location/Qualifiers
source                  1..15
                        mol_type = protein
                        organism = synthetic construct
SEQUENCE: 345
IVVTMPADLW DWIMA                                                     15

SEQ ID NO: 346          moltype = AA   length = 15
FEATURE                 Location/Qualifiers
source                  1..15
                        mol_type = protein
                        organism = synthetic construct
SEQUENCE: 346
IVVTMPADLW DWINA                                                     15

SEQ ID NO: 347          moltype = AA   length = 15
```

```
FEATURE               Location/Qualifiers
source                1..15
                      mol_type = protein
                      organism = synthetic construct
SEQUENCE: 347
IVVTMPADLW DWIQA                                                              15

SEQ ID NO: 348        moltype = AA  length = 15
FEATURE               Location/Qualifiers
source                1..15
                      mol_type = protein
                      organism = synthetic construct
SEQUENCE: 348
IHVTIPADLW DWINK                                                              15

SEQ ID NO: 349        moltype = AA  length = 14
FEATURE               Location/Qualifiers
source                1..14
                      mol_type = protein
                      organism = synthetic construct
SEQUENCE: 349
IHVTIPADLW DWIN                                                               14

SEQ ID NO: 350        moltype = AA  length = 36
FEATURE               Location/Qualifiers
source                1..36
                      mol_type = protein
                      organism = synthetic construct
SITE                  4
                      note = cyclohexyl-L-alanine
SITE                  14
                      note = 4-fluoro-L-phenylalanine
SITE                  29
                      note = gamma-carboxyglutamic acid
SEQUENCE: 350
QSDXDCIHRL LEAXLDPNLT EEQRWEKIXK INDECE                                       36

SEQ ID NO: 351        moltype = AA  length = 37
FEATURE               Location/Qualifiers
source                1..37
                      mol_type = protein
                      organism = synthetic construct
SITE                  4
                      note = cyclohexyl-L-alanine
SITE                  14
                      note = 4-fluoro-L-phenylalanine
SITE                  29
                      note = gamma-carboxyglutamic acid
SITE                  31
                      note = PEG30L
SEQUENCE: 351
QSDXDCIHRL LEAXLDPNLT EEQRWERIXK XINDECE                                      37

SEQ ID NO: 352        moltype = AA  length = 37
FEATURE               Location/Qualifiers
source                1..37
                      mol_type = protein
                      organism = synthetic construct
SITE                  4
                      note = cyclohexyl-L-alanine
SITE                  14
                      note = 4-fluoro-L-phenylalanine
SITE                  29
                      note = gamma-carboxyglutamic acid
SITE                  31
                      note = PEG20Br
SEQUENCE: 352
QSDXDCIHRL LEAXLDPNLT EEQRWERIXK XINDECE                                      37

SEQ ID NO: 353        moltype = AA  length = 37
FEATURE               Location/Qualifiers
source                1..37
                      mol_type = protein
                      organism = synthetic construct
SITE                  4
                      note = cyclohexyl-L-alanine
SITE                  14
                      note = 4-fluoro-L-phenylalanine
SITE                  29
```

-continued

```
                        note = gamma-carboxyglutamic acid
SITE                    31
                        note = PEG40Br
SEQUENCE: 353
QSDXDCIHRL LEAXLDPNLT EEQRWERIXK XINDECE                              37

SEQ ID NO: 354          moltype = AA  length = 35
FEATURE                 Location/Qualifiers
source                  1..35
                        mol_type = protein
                        organism = synthetic construct
SITE                    3
                        note = homoleucine
SEQUENCE: 354
FDXDCIHRLL EAFLDPNLTE QQRWEKIDKI NDECE                                35

SEQ ID NO: 355          moltype = AA  length = 36
FEATURE                 Location/Qualifiers
source                  1..36
                        mol_type = protein
                        organism = synthetic construct
SITE                    4
                        note = cyclohexyl-L-alanine
SITE                    14
                        note = 4-fluoro-L-phenylalanine
SITE                    29
                        note = gamma-carboxyglutamic acid
SEQUENCE: 355
QSDXDCIHRL LEAXLDPNLT EEQRWERIXK INDECE                               36

SEQ ID NO: 356          moltype = AA  length = 38
FEATURE                 Location/Qualifiers
source                  1..38
                        mol_type = protein
                        organism = synthetic construct
SITE                    6
                        note = cyclohexyl-L-alanine
SITE                    19
                        note = N-epsilon-acetyl-L-Lys
SEQUENCE: 356
SWQSDXDCIH RLLEAFLDXN LTEEQRWERI DKINDECE                             38

SEQ ID NO: 357          moltype = AA  length = 38
FEATURE                 Location/Qualifiers
source                  1..38
                        mol_type = protein
                        organism = synthetic construct
SITE                    6
                        note = cyclohexyl-L-alanine
MOD_RES                 19
                        note = 40 kDa branched PEG-Lys
SEQUENCE: 357
SWQSDXDCIH RLLEAFLDKN LTEEQRWERI DKINDECE                             38

SEQ ID NO: 358          moltype = AA  length = 29
FEATURE                 Location/Qualifiers
source                  1..29
                        mol_type = protein
                        organism = synthetic construct
VAR_SEQ                 3
                        note = note = selected from A, F, H, K, Q, R, S, W and Y
VAR_SEQ                 4
                        note = note = selected from A, D, E, F, H, I, K, L, M, N,
                         Q, R, S, T, V and Y
VAR_SEQ                 7
                        note = note = selected from F, H, I, K, L, M, N, R, S, T,
                         V, W and Y
VAR_SEQ                 11
                        note = note = selected from A, I, K, L, M, N, R, S, T and V
VAR_SEQ                 16
                        note = note = selected from N and T
VAR_SEQ                 17
                        note = note = selected from A, I, T and V
VAR_SEQ                 18
                        note = note = selected from D, E, G, H, K, N, Q, R, S and T
VAR_SEQ                 20
                        note = note = selected from I, L, M, R, T and V
VAR_SEQ                 21
                        note = note = selected from A, S, T and V
```

```
VAR_SEQ                 25
                        note = note = selected from I, M, Q, S, T, V and W
VAR_SEQ                 26
                        note = note = selected from K and S
VAR_SEQ                 28
                        note = note = selected from F, L, M and Y
VAR_SEQ                 29
                        note = note = selected from D and R
SEQUENCE: 358
EEXXAWXEIH XLPNLXXXQX XAFIXXLXX                                              29

SEQ ID NO: 359          moltype = AA  length = 29
FEATURE                 Location/Qualifiers
source                  1..29
                        mol_type = protein
                        organism = synthetic construct
VAR_SEQ                 3
                        note = note = selected from A, F, H, K, Q, R, S, W and Y
VAR_SEQ                 4
                        note = note = selected from A, D, E, F, H, I, K, L, M, N,
                        Q, R, S, T, V and Y
VAR_SEQ                 7
                        note = note = selected from F, H, I, K, L, M, N, R, S, T,
                        V, W and Y
VAR_SEQ                 11
                        note = note = selected from A, I, K, L, M, N, R, S, T and V
VAR_SEQ                 16
                        note = note = selected from N and T
VAR_SEQ                 17
                        note = note = selected from A, I, T and V
VAR_SEQ                 18
                        note = note = selected from D, E, G, H, K, N, Q, R, S and T
VAR_SEQ                 20
                        note = note = selected from I, L, M, R, T and V
VAR_SEQ                 21
                        note = note = selected from A, S, T and V
VAR_SEQ                 25
                        note = note = selected from I, M, Q, S, T, V and W
VAR_SEQ                 26
                        note = note = selected from K and S
VAR_SEQ                 28
                        note = note = selected from F, L, M and Y
VAR_SEQ                 29
                        note = note = selected from D and R
SEQUENCE: 359
EEXXAWXEIH XLPNLXXXQX XAFIXXLXX                                              29

SEQ ID NO: 360          moltype = AA  length = 49
FEATURE                 Location/Qualifiers
source                  1..49
                        mol_type = protein
                        organism = synthetic construct
SEQUENCE: 360
YYALSDAKEE EPRYKALRGE NQDLREKERK YQDKIKKLEE KEKNLEKKS                        49
```